US012448388B2

(12) United States Patent
Armstrong et al.

(10) Patent No.: US 12,448,388 B2
(45) Date of Patent: Oct. 21, 2025

(54) PRMT5 INHIBITORS AND USES THEREOF

(71) Applicant: Gilead Sciences, Inc., Foster City, CA (US)

(72) Inventors: Megan K. Armstrong, San Francisco, CA (US); Elbert Chin, San Mateo, CA (US); Chienhung Chou, Dublin, CA (US); Laurent P. Debien, San Francisco, CA (US); Yifan Deng, Milpitas, CA (US); Joshua D. Farr, Mountain View, CA (US); Pancham Lal Gupta, Foster City, CA (US); Chao-I Hung, San Mateo, CA (US); Benjamin J. June, San Francisco, CA (US); Prasenjit K. Mukherjee, South San Francisco, CA (US); Shaina V. Nguyen, Yorba Linda, CA (US); Gregory T. Notte, Redwood City, CA (US); Daniel Roa, Foster City, CA (US); Adam J. Schrier, Redwood City, CA (US); Katie A. Spence, San Francisco, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/663,952

(22) Filed: May 14, 2024

(65) Prior Publication Data

US 2024/0376110 A1 Nov. 14, 2024

Related U.S. Application Data

(63) Continuation of application No. 18/641,180, filed on Apr. 19, 2024, now abandoned.

(60) Provisional application No. 63/551,246, filed on Feb. 8, 2024, provisional application No. 63/497,683, filed on Apr. 21, 2023.

(51) Int. Cl.

| | |
|---|---|
| ***C07D 487/04*** | (2006.01) |
| ***A61K 31/4985*** | (2006.01) |
| ***A61K 31/506*** | (2006.01) |
| ***A61K 31/519*** | (2006.01) |
| ***A61K 31/5377*** | (2006.01) |
| ***A61K 31/538*** | (2006.01) |
| ***A61K 31/5383*** | (2006.01) |
| ***A61K 31/5386*** | (2006.01) |
| ***A61K 31/55*** | (2006.01) |
| ***A61K 45/06*** | (2006.01) |
| ***A61P 35/00*** | (2006.01) |
| ***C07D 487/14*** | (2006.01) |
| ***C07D 519/00*** | (2006.01) |

(52) U.S. Cl.

CPC ........ *C07D 487/04* (2013.01); *A61K 31/4985* (2013.01); *A61K 31/506* (2013.01); *A61K 31/519* (2013.01); *A61K 31/5377* (2013.01); *A61K 31/538* (2013.01); *A61K 31/5383* (2013.01); *A61K 31/5386* (2013.01); *A61K 31/55* (2013.01); *A61K 45/06* (2013.01); *A61P 35/00* (2018.01); *C07D 487/14* (2013.01); *C07D 519/00* (2013.01)

(58) Field of Classification Search

CPC .. C07D 487/04; C07D 487/14; C07D 519/00; A61P 35/00; A61K 31/4985; A61K 31/506; A61K 31/519; A61K 31/5377; A61K 31/538; A61K 31/5383; A61K 31/5386; A61K 31/55; A61K 45/06

See application file for complete search history.

(56) References Cited

U.S. PATENT DOCUMENTS

2024/0254118 A1 8/2024 Armstrong et al.

FOREIGN PATENT DOCUMENTS

| | | | |
|---|---|---|---|
| CN | 116178347 | A | 5/2023 |
| CN | 116462676 | A | 7/2023 |
| CN | 116462677 | A | 7/2023 |
| CN | 116854668 | A | 10/2023 |
| CN | 117924277 | A | 4/2024 |
| CN | 117986262 | A | 5/2024 |
| CN | 118047776 | A | 5/2024 |
| CN | 118103373 | A | 5/2024 |
| CN | 118221579 | A | 6/2024 |
| CN | 118221682 | A | 6/2024 |
| CN | 118359603 | A | 7/2024 |
| CN | 118359604 | A | 7/2024 |
| CN | 118359617 | A | 7/2024 |
| CN | 118580225 | A | 9/2024 |
| CN | 118619959 | A | 9/2024 |
| CN | 118772164 | A | 10/2024 |
| CN | 118908939 | A | 11/2024 |

(Continued)

OTHER PUBLICATIONS

Intl. Search Report—Written Opinion dated Jul. 9, 2024 for Intl. Appl. No. PCT/US2024/025562.

(Continued)

*Primary Examiner* — Clinton A Brooks
*Assistant Examiner* — Jerica Katlynn Wilson

(57) ABSTRACT

The present disclosure relates generally to compounds that inhibit PRMT5. The disclosure further relates to the use of the compounds for the preparation of a medicament for the treatment of diseases and/or conditions through inhibiting PRMT5. The disclosure further relates to the use of the compounds for the treatment of a disease or condition associated with chromosome 9p21 deletion, MTAP null, or any other MTAP deficiency. The disclosure further relates to the use of the compounds for the treatment of cancers.

18 Claims, 1 Drawing Sheet

(56) References Cited

FOREIGN PATENT DOCUMENTS

| | | | |
|---|---|---|---|
| CN | 118930582 | A | 11/2024 |
| CN | 119060035 | A | 12/2024 |
| CN | 119143752 | A | 12/2024 |
| CN | 119176814 | A | 12/2024 |
| CN | 119219608 | A | 12/2024 |
| CN | 119306742 | A | 1/2025 |
| CN | 119431378 | A | 2/2025 |
| CN | 119462695 | A | 2/2025 |
| CN | 119490500 | A | 2/2025 |
| CN | 119504710 | A | 2/2025 |
| CN | 119552167 | A | 3/2025 |
| CN | 119661432 | A | 3/2025 |
| CN | 119661516 | A | 3/2025 |
| CN | 119684280 | A | 3/2025 |
| CN | 119707931 | A | 3/2025 |
| CN | 119552175 | B | 4/2025 |
| CN | 119751486 | A | 4/2025 |
| CN | 119823103 | A | 4/2025 |
| CN | 119823149 | A | 4/2025 |
| CN | 119859155 | A | 4/2025 |
| CN | 119552151 | B | 5/2025 |
| CN | 119977947 | A | 5/2025 |
| WO | WO-2021050915 | A1 | 3/2021 |
| WO | WO-2021086879 | A1 | 5/2021 |
| WO | WO-2021163344 | A1 | 8/2021 |
| WO | WO-2022115377 | A1 | 6/2022 |
| WO | WO-2022132914 | A1 | 6/2022 |
| WO | WO-2022169948 | A1 | 8/2022 |
| WO | WO-2022192745 | A1 | 9/2022 |
| WO | WO-2023025540 | A1 | 3/2023 |
| WO | WO-2023036974 | A1 | 3/2023 |
| WO | WO-2023081367 | A2 | 5/2023 |
| WO | WO-2023098439 | A1 | 6/2023 |
| WO | WO-2023125540 | A1 | 7/2023 |
| WO | WO-2023143210 | A1 | 8/2023 |
| WO | WO-2023146987 | A1 | 8/2023 |
| WO | WO-2023146989 | A1 | 8/2023 |
| WO | WO-2023146991 | A1 | 8/2023 |
| WO | WO-2023174250 | A1 | 9/2023 |
| WO | WO-2023202626 | A1 | 10/2023 |
| WO | WO-2023207556 | A1 | 11/2023 |
| WO | WO-2023246873 | A1 | 12/2023 |
| WO | WO-2024002263 | A1 | 1/2024 |
| WO | WO-2024002376 | A1 | 1/2024 |
| WO | WO-2024002377 | A1 | 1/2024 |
| WO | WO-2024008113 | A1 | 1/2024 |
| WO | WO-2024008176 | A1 | 1/2024 |
| WO | WO-2024012308 | A1 | 1/2024 |
| WO | WO-2024021957 | A1 | 2/2024 |
| WO | WO-2024027370 | A1 | 2/2024 |
| WO | WO-2024027703 | A1 | 2/2024 |
| WO | WO-2024032572 | A1 | 2/2024 |
| WO | WO-2024037459 | A1 | 2/2024 |
| WO | WO-2024037607 | A1 | 2/2024 |
| WO | WO-2024037608 | A1 | 2/2024 |
| WO | WO-2024038004 | A1 | 2/2024 |
| WO | WO-2024051816 | A1 | 3/2024 |
| WO | WO-2024067433 | A1 | 4/2024 |
| WO | WO-2024067445 | A1 | 4/2024 |
| WO | WO-2024123740 | A1 | 6/2024 |
| WO | WO-2024131901 | A1 | 6/2024 |
| WO | WO-2024140923 | A1 | 7/2024 |
| WO | WO-2024153128 | A1 | 7/2024 |
| WO | WO-2024174980 | A1 | 8/2024 |
| WO | WO-2024177416 | A1 | 8/2024 |
| WO | WO-2024182466 | A1 | 9/2024 |
| WO | WO-2024188999 | A1 | 9/2024 |
| WO | WO-2024199255 | A1 | 10/2024 |
| WO | WO-2024213044 | A1 | 10/2024 |
| WO | WO-2024220917 | A1 | 10/2024 |
| WO | WO-2024222660 | A1 | 10/2024 |
| WO | WO-2024222914 | A2 | 10/2024 |
| WO | WO-2024234821 | A1 | 11/2024 |
| WO | WO-2024238628 | A1 | 11/2024 |
| WO | WO-2024240894 | A1 | 11/2024 |
| WO | WO-2024245412 | A1 | 12/2024 |
| WO | WO-2024249763 | A2 | 12/2024 |
| WO | WO-2024249931 | A1 | 12/2024 |
| WO | WO-2024255863 | A1 | 12/2024 |
| WO | WO-2025011574 | A1 | 1/2025 |
| WO | WO-2025016323 | A1 | 1/2025 |
| WO | WO-2025026381 | A1 | 2/2025 |
| WO | WO-2025031468 | A1 | 2/2025 |
| WO | WO-2025034640 | A1 | 2/2025 |
| WO | WO-2025036472 | A1 | 2/2025 |
| WO | WO-2025039979 | A1 | 2/2025 |
| WO | WO-2025051157 | A1 | 3/2025 |
| WO | WO-2025061102 | A1 | 3/2025 |
| WO | WO-2025064286 | A1 | 3/2025 |
| WO | WO-2025068985 | A1 | 4/2025 |
| WO | WO-2025076500 | A1 | 4/2025 |
| WO | WO-2025077856 | A1 | 4/2025 |
| WO | WO-2025077857 | A1 | 4/2025 |
| WO | WO-2025092818 | A1 | 5/2025 |
| WO | WO-2025098450 | A1 | 5/2025 |
| WO | WO-2025113499 | A1 | 6/2025 |
| WO | WO-2025113703 | A1 | 6/2025 |
| WO | WO-2025119326 | A1 | 6/2025 |
| WO | WO-2025149009 | A1 | 7/2025 |
| WO | WO-2025149020 | A1 | 7/2025 |
| WO | WO-2025157284 | A1 | 7/2025 |
| WO | WO-2025157286 | A1 | 7/2025 |
| WO | WO-2025157287 | A1 | 7/2025 |
| WO | WO-2025157288 | A1 | 7/2025 |
| WO | WO-2025157289 | A1 | 7/2025 |
| WO | WO-2025166215 | A1 | 8/2025 |
| WO | WO-2025166229 | A1 | 8/2025 |
| WO | WO-2025166257 | A1 | 8/2025 |
| WO | WO-2025166260 | A1 | 8/2025 |
| WO | WO-2025166274 | A1 | 8/2025 |

OTHER PUBLICATIONS

U.S. Appl. No. 18/641,180, filed Apr. 19, 2024, Megan K. Armstrong et al.

U.S. Appl. No. 18/391,258, filed Dec. 20, 2023, Megan K. Armstrong et al.

PRMT5 INHIBITORS AND USES THEREOF

CROSS REFERENCE TO RELATED APPLICATIONS

This application is a Continuation of application Ser. No. 18/641,180 filed on Apr. 19, 2024, which claims priority to U.S. Provisional Application No. 63/497,683, filed Apr. 21, 2023, and U.S. Provisional Application No. 63/551,246, filed Feb. 8, 2024, both of which are incorporated herein in their entireties for all purposes.

FIELD

The present disclosure relates to compounds that inhibit PRMT5. The disclosure further relates to the use of the compounds for the treatment and/or prophylaxis of diseases and/or conditions responsive to PRMT5 inhibition.

BACKGROUND

Protein arginine methyltransferase (PRMT) enzymes catalyze methylation of arginine residues on proteins involved in chromatin organization, gene expression, RNA splicing, protein translation, and signal transduction. Diverse substrates for PRMTs localize to various subcellular compartments including nucleus, nucleolus, cytosol and enable many biological processes critical to mammalian cell function and survival.

Among the nine members of the PRMT family, PRMT5 is responsible for generating the majority of symmetric dimethyl arginines on protein substrates. Methylation by PRMT5 is distributive, implying that PRMT5 produces and releases mono-methyl arginines before the second methylation event. PRMT5 functions as a homo-tetramer in complex with a homo-tetramer of MEP50/WDR77 protein. MEP50/WDR77 is indispensable for PRMT5 enzymatic activity, substrate recognition and interaction with numerous binding partners (S. Antonysamy, et al. PNAS 109, 2012).

PRMT5 expression is frequently upregulated in leukemia, lymphoma, and solid tumors and its expression may inversely correlate with patient survival. (Greenblatt, et al. Exp. Hematol. 2016, Chen, H., et al. Oncogene 2016, Lattouf, et al. Oncotarget, 2019). In normal tissues, PRMT5 is required for hematopoiesis and potentiates both hematopoietic stem cell pluripotency and progenitor expansion, suggesting that its inhibition could have myelosuppressive effects (Liu et al. J. Clin. Invest., 2015).

During past few years, several PRMT5 inhibitors have entered clinical trials with the goal of treating tumors addicted to PRMT5 activity and/or particularly sensitive to PRMT5 inhibition. A narrow therapeutic window and myelosuppression were consistently observed in patients enrolled in these trials, suggesting that inhibition of PRMT5 in normal tissues was undesirable. The inhibition of PRMT5 activity in tumors, while sparing normal cells, can presumably mitigate adverse effects of these first generation PRMT5 inhibitors.

Human cancers frequently acquire homozygous deletion of chromosome 9p21 locus carrying tumor suppressor CDKN2A (cyclin dependent kinase inhibitor 2A). MTAP (methylthioadenosine phosphorylase) gene, located in close proximity to CDKN2A, co-deleted in 90% of tumors with CDKN2A loss. It is estimated that 10-15% of all cancers carry homozygous deletion of the MTAP gene. Pancreatic, bladder, NSCLC, head and neck, esophageal cancer, and glioblastoma are among cancers having a significant portion of patients with MTAP loss.

MTAP loss/null/deletion leads to accumulation of its substrate methylthioadenosine (MTA), which is structurally similar to SAM (S-adenosyl-L-methionine) utilized by PRMT5 as a methyl donating cofactor for catalyzing arginine di-methylation. MTA accumulating in MTAP-deleted cancer cells competes with SAM for binding to the catalytic site of PRMT5 and partially suppresses its enzymatic activity. Tumor cells growing under the pressure of reduced PRMT5 activity become especially vulnerable to further PRMT5 loss, such as knockdown with shRNA or siRNA.

Accumulation of PRMT5-MTA complexes in MTAP deleted cancer can be exploited therapeutically. It is attractive to design MTA-cooperative small molecule inhibitors of PRMT5, which would selectively elicit their inhibitory effects in cancer cells with elevated MTA levels and accumulation of MTA-bound PRMT5.

A need remains for PRMT5 inhibitors with desirable selectivity, potency, metabolic stability, or reduced detrimental effects.

SUMMARY

The present disclosure provides compounds useful as PRMT5 inhibitors. The disclosure further relates to the use of the compounds for the treatment and/or prophylaxis of diseases and/or conditions through inhibiting PRMT5 by said compounds. The disclosure further relates to the use of the compounds for the treatment and/or prophylaxis of diseases and/or conditions through inhibiting PRMT5 in tumors associated with MTAP null or chromosome 9p21 deletion by said compounds.

In one embodiment, provided herein is a compound of Formula (I), (I)

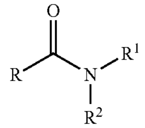

or a pharmaceutically acceptable salt thereof, wherein

R is

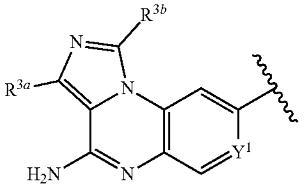

or

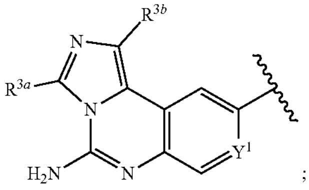

;

each $R^{3a}$ is independently H, —CN, $C_{1-3}$ alkyl, $C_{1-3}$ haloalkyl, $C_{1-3}$ alkoxy, $C_{1-3}$ haloalkoxy, $C_{3-4}$ cycloalkyl, or halo;

each $R^{3b}$ is independently H, —CN, $C_{1-3}$ alkyl, $C_{1-3}$ haloalkyl, $C_{1-3}$ alkoxy, $C_{1-3}$ haloalkoxy, $C_{3-4}$ cycloalkyl, or halo;

$Y^1$ is N, or $CR^{Y1}$; wherein $R^{Y1}$ is H, F, Cl, Br, CN, $C_{1-3}$ alkyl, $C_{1-3}$ haloalkyl, $C_{1-3}$ alkoxy, —$CH_2OCH_3$, or $C_{1-3}$ haloalkoxy;

$R^1$ is $C_{1-3}$ alkyl, $C_{3-10}$ cycloalkyl, $C_{6-12}$ aryl, heterocyclyl, or heteroaryl; wherein the cycloalkyl, heterocyclyl, heteroaryl, or aryl of $R^1$ is optionally substituted with 1 to 4 $Z^1$, which may be the same or different; the alkyl of $R^1$ is optionally substituted with one to four $R^{1a}$, which may be the same or different; each $R^{1a}$ is independently —CN, $C_{2-6}$ alkynyl, $C_{3-10}$ cycloalkyl, $C_{1-6}$ haloalkyl, $C_{6-12}$ aryl, heterocyclyl, or heteroaryl; wherein the cycloalkyl, aryl, heterocyclyl, or heteroaryl of Ra is optionally substituted with 1 to 4 $Z^7$, which may be the same or different;

$R^2$ is $C_{1-3}$ alkyl, $C_{3-10}$ cycloalkyl, $C_{6-12}$ aryl, heterocyclyl, heteroaryl, or —$NR^{2a}R^{2b}$; wherein the alkyl, cycloalkyl, aryl, heterocyclyl, or heteroaryl of $R^2$ is optionally substituted with 1 to 4 $Z^2$, which may be the same or different;

$R^{2a}$ is H, $C_{1-6}$ alkyl, $C_{1-6}$ haloalkyl, —$COR^{2a1}$, —$COOR^{2a1}$, —$CONR^{2a1}R^{2b1}$, —$SO_2R^{2a1}$, —$SO_2NR^{2a1}R^{2b1}$, $C_{6-10}$ aryl, $C_{3-10}$ cycloalkyl, heterocyclyl, or heteroaryl; wherein the alkyl, aryl, cycloalkyl, heterocyclyl, or heteroaryl of $R^{2a}$ is each optionally substituted with 1 to 4 $Z^3$, which may be the same or different, $R^{2b}$ is H, $C_{1-6}$ alkyl, $C_{1-6}$ haloalkyl, $C_{6-10}$ aryl, $C_{3-10}$ cycloalkyl, heterocyclyl, or heteroaryl; wherein the alkyl, aryl, cycloalkyl, heterocyclyl, or heteroaryl of $R^{2b}$ is each optionally substituted with 1 to 4 $Z^4$, which may be the same or different, or $R^{2a}$ and $R^{2b}$ together with the nitrogen to which they are attached form a heterocyclyl or heteroaryl, wherein the heterocyclyl or heteroaryl formed from $R^{2a}$ and $R^{2b}$ together with the nitrogen to which they are attached is optionally substituted with 1 to 4 $Z^5$, which may be the same or different, wherein the heterocyclyl formed from $R^{2a}$ and $R^{2b}$ is 3 to 10 membered heterocyclyl having 0 to 3 additional heteroatoms each independently N, O, or S; the heteroaryl formed from $R^{2a}$ and $R^{2b}$ is 3 to 10 membered heteroaryl having 0 to 3 additional heteroatoms each independently N, O, or S;

or $R^1$ and $R^2$ together with the N to which they are attached form a heterocyclyl; wherein the heterocyclyl formed from $R^1$ and $R^2$ together with the N to which they are attached is optionally substituted with one to four $Z^6$, which may be the same or different, wherein the heterocyclyl formed from $R^1$ and $R^2$ is 3 to 20 membered heterocyclyl having 0 to 3 additional heteroatoms each independently N, O, or S;

each $Z^1$, $Z^2$, $Z^3$, $Z^4$, $Z^5$, $Z^6$, or $Z^7$ is independently $C_{1-9}$ alkyl, $C_{1-8}$ haloalkyl, $C_{1-6}$ alkoxy, $C_{1-6}$ haloalkoxy, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$) N($R^{12a}$)($R^{12b}$), —N($R^{12a}$)$_2$($R^{12b}$)+, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —$NR^{12a}$S(O)$_2$N($R^{12b}$)($R^{12c}$), $NR^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —$SF_5$, —S(O)$R^{12a}$, —S(O)(NH)$R^{12a}$, —S(O)$_2R^{12a}$, —S(O)$_2$N($R^{12a}$)($R^{12b}$), or —S(O)($NR^{12a}$)$R^{12b}$; wherein the alkyl, haloalkyl, alkenyl, alkynyl, cycloalkyl, heterocyclyl, aryl, or heteroaryl of each $Z^1$, $Z^2$, $Z^3$, $Z^4$, $Z^5$, $Z^6$, or $Z^7$ is each optionally substituted with 1 to 4 $Z^{1a}$, which may be the same or different; each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$)—N($R^{12a}$)$_2$($R^{12b}$)+, —N($R^{12a}$)—C(O)$R^{12b}$, —N($R^{12a}$)C(O)O($R^{12b}$), —N($R^{12a}$)C(O)N($R^{12b}$)($R^{12c}$) N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$—S(O)$R^{12a}$, —S(O)(NH)$R^{12a}$, —S(O)$_2R^{12a}$, —S(O)$_2$N($R^{12a}$)($R^{12b}$), or —S(O)($NR^{12a}$)$R^{12b}$; wherein the alkyl, haloalkyl, alkenyl, alkynyl, cycloalkyl, heterocyclyl, aryl, or heteroaryl of $Z^{1a}$ is each optionally substituted with 1 to 4 $Z^{1b}$, which may be the same or different;

each $Z^{1b}$ is independently $C_{1-9}$ alkyl, $C_{1-9}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —NH$_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{2a1}$, $R^{2b1}$, $R^{12a}$, $R^{12b}$, or $R^{12c}$ is independently H, $C_{1-6}$ alkyl, $C_{3-10}$ cycloalkyl, heterocyclyl, $C_{6-10}$ aryl, or heteroaryl, wherein the alkyl, cycloalkyl, heterocyclyl, aryl, or heteroaryl of each of $R^{2a}$, $R^{2b1}$, $R^{12a}$, $R^{12b}$, or $R^{12c}$ is each optionally substituted 1 to 4 $Z^{1b}$, which may be the same or different;

wherein each heteroaryl of the compound of Formula (I) unless otherwise specified is 5 to 14 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O or S.

In some embodiments, provided herein are pharmaceutical compositions comprising a compound provided herein, or pharmaceutically acceptable salt thereof, and a pharmaceutically acceptable excipient or carrier. In some embodiments, the pharmaceutical compositions comprise a therapeutically effective amount of a compound provided herein, or pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or pharmaceutically acceptable salts thereof. In some embodiments, the pharmaceutical compositions further comprise a therapeutically effective amount of the one or more (e.g., one, two, three, four, one or two, one to three, or one to four) additional therapeutic agents, or pharmaceutically acceptable salts thereof.

In some embodiments, the present disclosure provides methods of inhibiting PRMT5 in a subject in need thereof, comprising administering to the subject a therapeutically effective amount of a compound provided herein (e.g., a compound of Formula (I), (Ia), (Ib), or (Ic)), or pharmaceutically acceptable salt thereof, or a pharmaceutical composition provided herein.

In some embodiments, the present disclosure provides methods of treating a patient having a condition associated with chromosome 9p21 deletion or MTAP-null, comprising administering to the patient a therapeutically effective amount of a compound provided herein (e.g., a compound of Formula (I), (Ia), (Ib), or (Ic)), or pharmaceutically acceptable salt thereof, or a pharmaceutical composition provided herein.

In some embodiments, the present disclosure provides methods of treating a cancer patient, comprising administering to the cancer patient a therapeutically effective amount of a compound provided herein (e.g., a compound of Formula (I), (Ia), (Ib), or (Ic)), or pharmaceutically acceptable salt thereof, or a pharmaceutical composition provided herein.

In some embodiments, the present disclosure provides uses of a compound provided herein (e.g., a compound of Formula (I), (Ia), (Ib), or (Ic)), or pharmaceutically acceptable salt thereof, for the manufacture of a medicament for the treatment of chromosome 9p21 deletion or MTAP-null associated disease or condition.

In some embodiments, the present disclosure provides uses of a compound provided herein (e.g., a compound of Formula (I), (Ia), (Ib), or (Ic)), or pharmaceutically acceptable salt thereof, for the manufacture of a medicament for the treatment of cancer.

In some embodiments, the present disclosure provides a compound provided herein (e.g., a compound of Formula (I), (Ia), (Ib), or (Ic)), or pharmaceutically acceptable salt thereof, or a pharmaceutical composition comprising a compound provided herein for pharmaceutical use.

In some embodiments, the present disclosure provides a compound provided herein (e.g., a compound of Formula (I), (Ia), (Ib), or (Ic)), or pharmaceutically acceptable salt thereof, or a pharmaceutical composition comprising a compound provided herein for the treatment of chromosome 9p21 deletion or MTAP-null associated disease or condition.

In some embodiments, the present disclosure provides a compound provided herein (e.g., a compound of Formula (I), (Ia), (Ib), or (Ic)), or pharmaceutically acceptable salt thereof, or a pharmaceutical composition comprising a compound provided herein for the treatment of cancer.

DETAILED DESCRIPTION

Figure 1:
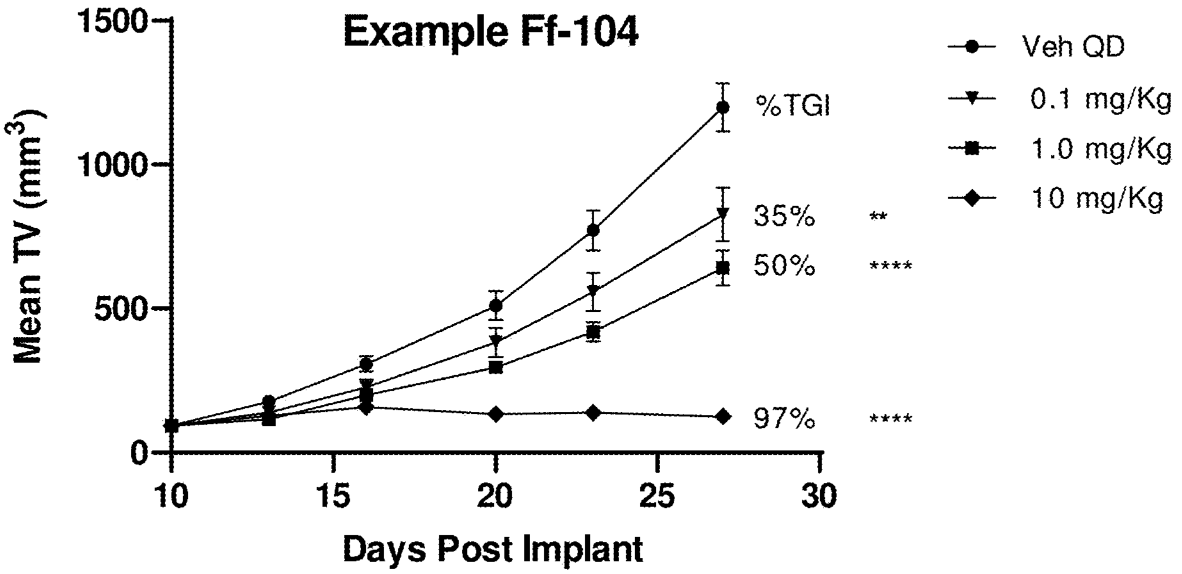
FIGS. 1 and 2 show efficacy data of Examples Ff-104 and Fg-53 respectively. MTAP-deleted NSCLC, LU99 xenograft was established in NSG mice by implanting 3 million cells in a 1:1 ratio of media and Geltrex. Animals were randomized for dosing after the tumor volume reached 60-120 $mm^3$. Animals were treated orally once daily with the designated compound at the indicated doses for 18 days. Tumor volume and body weight were measured bi-weekly. Data represents group mean +/−SEM, n=10 for each group. P values were determined by TWO-way ANOVA with a Dunnett's multiple comparisons to Vehicle.
Figure 2:
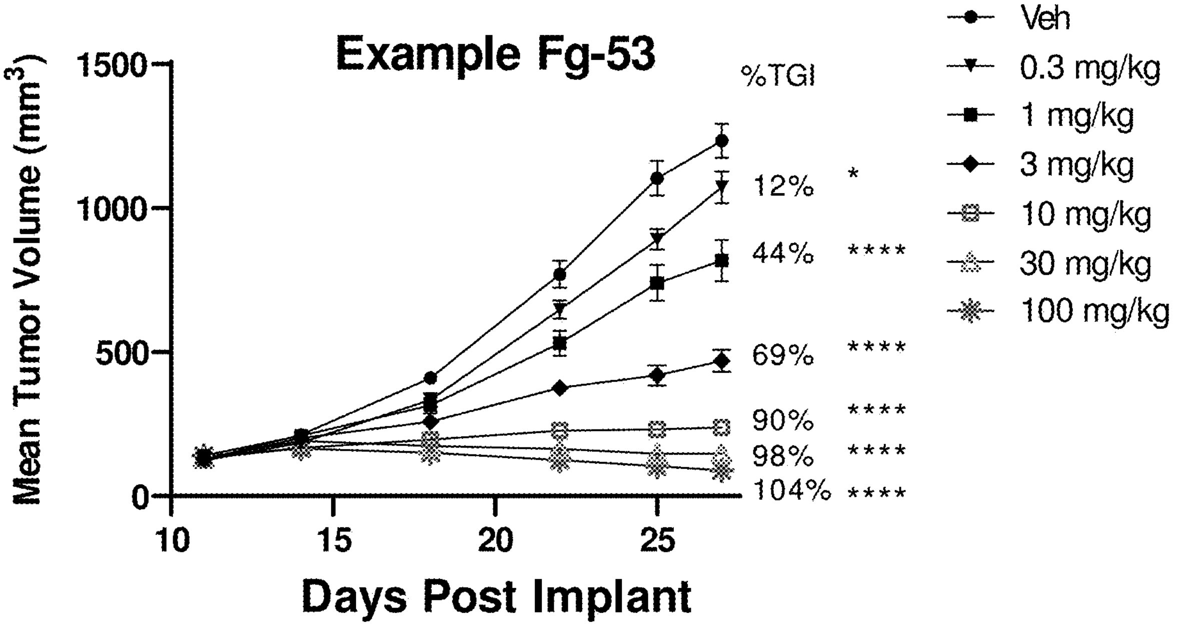

The present disclosure relates to inhibitors of PRMT5. The disclosure also relates to compositions and methods relating to PRMT5 inhibitors and the use of such compounds for treatment and/or prophylaxis of diseases and conditions. The disclosure also relates to compositions and methods of treating and/or preventing cancer or viral infections that include a PRMT5 inhibitor in combination with one or more additional therapeutic agents.

Definitions and General Parameters

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms “a”, “and”, and “the” include plural referents unless the context clearly dictates otherwise. Thus, e.g., reference to “the compound” includes a plurality of such compounds and reference to “the assay” includes reference to one or more assays and equivalents thereof known to those skilled in the art, and so forth.

As used in the present specification, the following terms and phrases are generally intended to have the meanings as set forth below, except to the extent that the context in which they are used indicates otherwise.

A dash (“-”) that is not between two letters or symbols is used to indicate a point of attachment for a substituent. For example, $—CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, Ra in the below structure can be attached to any of the five carbon ring atoms or Ra can replace the hydrogen attached to the nitrogen ring atom:

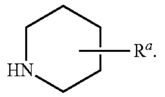

The prefix “$C_{u-v}$” indicates that the following group has from u to v carbon atoms. For example, “$C_{1-6}$ alkyl” indicates that the alkyl group has from 1 to 6 carbon atoms. Likewise, the term “x-y membered” rings, wherein x and y are numerical ranges, such as “3 to 12-membered heterocyclyl”, refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent “alkyl” group, a divalent “aryl” group, etc., may also be referred to as an “alkylene” group or an “alkylenyl” group, or alkylyl group, an “arylene” group or an “arylenyl” group, or arylyl group, respectively.

“A compound disclosed herein” or “a compound of the present disclosure” or “a compound provided herein” or “a compound described herein” refers to the compounds of Formula (I), (Ia), (Ib), or (Ic). Also included are the specific compounds of Examples 1 to 52 provided herein.

Reference to “about” a value or parameter herein includes (and describes) embodiments that are directed to that value or parameter per se. In certain embodiments, the term “about” includes the indicated amount ±10%. In other embodiments, the term “about” includes the indicated amount ±5%. In certain other embodiments, the term “about” includes the indicated amount ±1%. Also, to the term “about X” includes description of “X”. Also, the singular forms “a” and “the” include plural references unless the context clearly dictates otherwise. Thus, e.g., reference to “the compound” includes a plurality of such compounds and reference to “the assay” includes reference to one or more assays and equivalents thereof known to those skilled in the art.

“Alkyl” refers to an unbranched or branched saturated hydrocarbon chain. As used herein, alkyl has 1 to 20 carbon atoms (i.e., $C_1$-20 alkyl), 1 to 8 carbon atoms (i.e., $C_1$-8 alkyl), 1 to 6 carbon atoms (i.e., $C_{1-6}$ alkyl), 1 to 4 carbon atoms (i.e., $C_{1-4}$ alkyl), or 1 to 3 carbon atoms (i.e., $C_{1-3}$ alkyl). Examples of alkyl groups include methyl, ethyl, n-propyl, isopropyl, n-butyl, sec-butyl, iso-butyl, tert-butyl, n-pentyl, 2-pentyl, isopentyl, neopentyl, n-hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, “butyl” includes n-butyl (i.e., $—(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)_3$); and “propyl” includes n-propyl (i.e., $—(CH_2)_2CH_3$) and isopropyl (i.e., $—CH(CH_3)_2$).

“Alkenyl” refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

“Alkynyl” refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term “alkynyl” also includes those groups having one triple bond and one double bond.

“Acyl” refers to a group $—C(=O)R$, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

“Alkoxy” refers to an alkyl group having an oxygen atom that connects the alkyl group to the point of attachment: alkyl-O—. As for alkyl group, alkoxy groups will have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

“Alkoxyalkyl” refers an alkoxy group linked to an alkyl group which is linked to the remainder of the compound. Alkoxyalkyl have any suitable number of carbon, such as from 2 to 6 ($C_{2-6}$ alkoxyalkyl), 2 to 5 ($C_{2-5}$ alkoxyalkyl), 2 to 4 ($C_{2-4}$ alkoxyalkyl), or 2 to 3 ($C_{2-3}$ alkoxyalkyl). The number of carbons refers to the total number of carbons in the alkoxy and the alkyl group. For example, in some embodiments, $C_6$ alkoxyalkyl refers to ethoxy ($C_2$ alkoxy) linked to a butyl ($C_4$ alkyl), and in other embodiments, n-propoxy ($C_3$ alkoxy) linked to isopropyl ($C_3$ alkyl). Alkoxy and alkyl are as defined above where the alkyl is divalent, and can include, but is not limited to, methoxymethyl ($CH_3OCH_2$—), methoxyethyl ($CH_3OCH_2CH_2$—) and others.

"Amino" refers to the group —$NR^yR^z$ wherein $R^y$ and $R^z$ are independently selected from the group consisting of hydrogen, alkyl, haloalkyl, aryl, heteroaryl, cycloalkyl, or heterocyclyl; each of which may be optionally substituted.

"Aryl" as used herein refers to a single all carbon aromatic ring or a multicyclic all carbon ring system wherein at least one of the rings is aromatic. For example, in some embodiments, an aryl group has 6 to 20 carbon atoms, 6 to 14 carbon atoms, or 6 to 12 carbon atoms. Aryl includes a phenyl radical. Aryl also includes multicyclicring systems (e.g., ring systems comprising 2, 3 or 4 rings) having 9 to 20 carbon atoms, e.g., 9 to 16 carbon atoms, in which at least one ring is aromatic and wherein the other rings may be aromatic or not aromatic (i.e., carbocycle). Such multicyclicring systems are optionally substituted with one or more (e.g., 1, 2 or 3) oxo groups on any carbocycle portion of the multicyclic ring system. The rings of the multicyclic ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Fused" refers to a ring which is bound to an adjacent ring. In some embodiments, the fused ring system is a heterocyclyl. In some embodiments, the fused rimg system is an oxabicyclohexanyl. In some embodiments, the fused ring system is

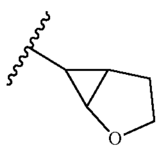

or

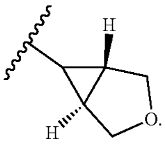

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems. In some embodiments, the bridged ring is a bicyclopentyl (e.g., bicyclo[1.1.1]pentyl), bicycloheptyl (e.g., bicyclo[2.2.1]heptyl, bicyclo[3.1.1]heptyl), or bicyclooctyl (e.g., bicyclo[2.2.2]octyl). In some embodiments, the bridged ring

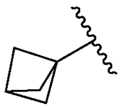,

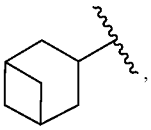,

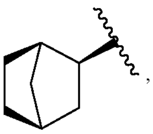,

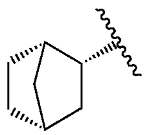, or

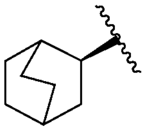.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. In some embodiments the spiro substituent is a spiropentanyl (spiro[a.b]pentanyl), spirohexanyl, spiroheptanyl, spirooctyl (e.g., spiro[2.5]octyl), spirononanyl (e.g., spiro[3.5]nonanyl), spirodecanyl (e.g., spiro[4.5]decanyl), or spiroundecanyl (e.g., spiro[5.5]undecanyl). In some embodiments the spiro substituent is

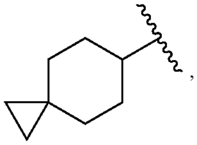,

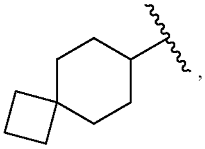,

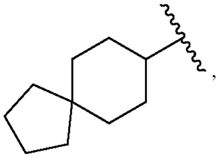, or

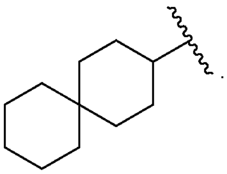.

"Halogen" or "halo" includes fluoro, chloro, bromo, and iodo.

"Haloalkyl" as used herein refers to an alkyl as defined herein, wherein one or more hydrogen atoms of the alkyl are independently replaced by a halo substituent, which may be the same or different. For example, $C_{1-4}$ haloalkyl is a $C_{1-4}$ alkyl wherein one or more of the hydrogen atoms of the $C_{1-4}$ alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Haloalkoxy" refers to an alkoxy group where some or all of the hydrogen atoms are substituted with halogen atoms.

As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

The term "heteroaryl" as used herein refers to a single aromatic ring or a multicyclic ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multicyclic ring systems (e.g., ring systems comprising 2 or 3 rings) wherein a heteroaryl group, as defined above, can be fused with one or more heteroaryls (e.g., naphthyridinyl), carbocycles (e.g., 5,6,7,8-tetrahydroquinolyl) or aryls (e.g., indazolyl) to form a multicyclic ring. Such multicyclic rings may be optionally substituted with one or more (e.g., 1, 2 or 3) oxo groups on the carbocycle portions of the multicyclic ring. It is to be understood that the point of attachment of a heteroaryl multicyclic ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

"Heterocyclyl" or "heterocyclic ring" or "heterocycle" as used herein refers to a single saturated or partially unsaturated ring or a multicyclic ring. The term includes single saturated or partially unsaturated ring (e.g., 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term also includes multicyclic ring systems (e.g., ring systems comprising 2 or 3 rings) wherein a heterocycle group (as defined above) can be connected to two adjacent atoms (fused heterocycle) with one or more heterocycles (e.g., decahydronapthyridinyl), heteroaryls (e.g., 1,2,3,4-tetrahydronaphthyridinyl), carbocycles (e.g., decahydroquinolyl) or aryls. It is to be understood that the point of attachment of a heterocycle multicyclic ring, as defined above, can be at any position of the ring including a heterocyle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl. Exemplary fused bicyclic heterocycles include, but are not limited to

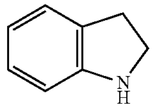,
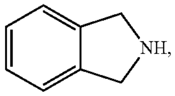
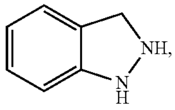

-continued

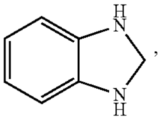,
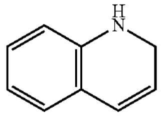,
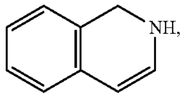

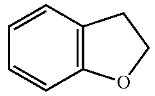,
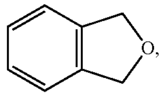
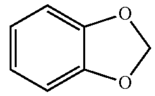,

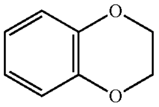,
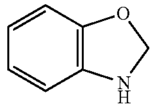,
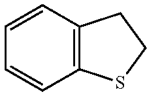,

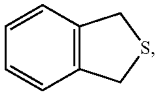
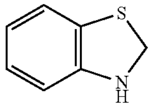,
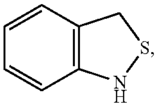

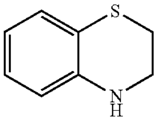,
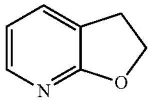.

"Hydroxy" or "hydroxyl" refers to the group —OH.

"Oxo" refers to the group (=O) or (O).

"Sulfonyl" refers to the group $—S(O)_2R^c$, where $R^c$ is alkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an $—NH_2$ group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, CN, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, CN, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, CN, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —$S(O)_2R$, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

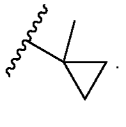 [SMILES: *C1(C)CC1]

The disclosures illustratively described herein may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e., groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to persons skilled in the art.

If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts.

The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

Furthermore, compounds disclosed herein may be subject to tautomerism. Where tautomerism, e.g., keto-enol tautomerism, of compounds or their prodrugs may occur, the individual forms, like, e.g., the keto and enol form, are each within the scope of the disclosure as well as their mixtures in any ratio. The same applies for stereoisomers, like, e.g., enantiomers, cis/trans isomers, diastereomers, conformers, and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof (e.g., scalemic mixtures) of the compounds described herein or a pharmaceutically acceptable salt or a mixture thereof. If desired, isomers can be separated by methods well known in the art, e.g., by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley and Sons, New York, 1992).

Compounds disclosed herein and their pharmaceutically acceptable salts may, in some embodiments, include an asymmetric center and may thus give rise to enantiomers, diastereomers, and other stereoisomeric forms that may be defined, in terms of absolute stereochemistry, as (R)- or (S)- or, as (D)- or (L)- for amino acids. Some embodiments include all such possible isomers, as well as their racemic, scalemic, and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein, in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g., a human. See, e.g., Foster, "Deuterium Isotope Effects in Studies of Drug Metabolism," Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have beneficial DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising a compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, PA 17th Ed. (1985); and Modern Pharmaceutics, Marcel Dekker, Inc. 3rd Ed. (G. S. Banker & C. T. Rhodes, Eds.).

"$IC_{50}$" or "$EC_{50}$" refers to the inhibitory concentration required to achieve 50% of the maximum desired effect.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, the term "treatment" or "treating" means administering a compound or pharmaceutically acceptable salt of Formula (I) for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to PRMT5 inhibitors. The therapeutically effective amount may vary depending on the subject, and disease or condition being treated, the weight and age of the subject, the severity of the disease or condition, and the manner of administering, which can readily be determined by one or ordinary skill in the art.

List of Abbreviations and Acronyms

| Abbreviation | Meaning |
|---|---|
| ° C. | degrees Celsius |
| Ac | acetate |
| AcOH | acetic acid |
| Boc | tert-butoxycarbonyl |
| CBz | benzyloxycarbonyl |
| d | doublet |
| DCE | 1,2-dichloroethane |
| DCM | dichloromethane |
| dd | doublet of doublets |
| DMAc | dimethylacetoamide |
| DMF | Dimethylformamide |
| DMSO | Dimethylsulfoxide |
| equiv or eq. | equivalents |
| ES/MS | electron spray mass spectrometry |
| Et | ethyl |
| EtOH | ethanol |
| g | gram |
| glyme | 1,2-dimethoxyethane |
| H NMR | proton nuclear magnetic resonance |
| h or hr | hour |
| LC/MS | liquid chromatography/mass spectrometry |
| M | molar |
| m | milli |
| m/z | mass to charge ratio |
| M+ | mass peak |
| M + H | mass peak plus hydrogen |
| Me | methyl |
| MeCN or ACN | acetonitrile |
| MeOH | methanol |
| mg | milligram |
| MHz | megahertz |
| mL or ml | milliliter |
| mol | mole |
| mw | microwave |
| nM | nanomolar |
| $Pd(PPh_3)_4$ | Tetrakis(triphenylphosphine)palladium(0) |
| Pg | protecting group |
| Ph | phenyl |
| r.t. | room temperature |
| RP-HPLC | reversed-phase high perfomance liquid chromatography |
| s | singlet |
| SFC | For chiral separation |
| t | triplet |
| tBu | tert-butyl |
| TEA | triethylamine |
| Tf | trifluoromethanesulfonate |
| TFA | trifluoroacetic acid |
| THF | tetrahydrofuran |

-continued

| Abbreviation | Meaning |
|---|---|
| Ts | toluenesufonyl |
| δ | parts per million referenced to residual solvent peak |
| μL | microliter |
| μmol | micromole |

Compounds

In one embodiment, the present disclosure provides a compound of Formula (I), (I)

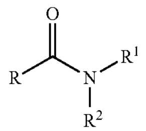

or a pharmaceutically acceptable salt thereof, wherein

R is

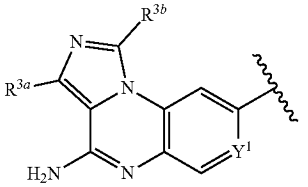

or

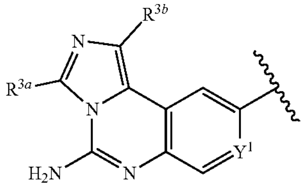

;

each $R^{3a}$ is independently H, —CN, $C_{1-3}$ alkyl, $C_{1-3}$ haloalkyl, $C_{1-3}$ alkoxy, $C_{1-3}$ haloalkoxy, $C_{3-4}$ cycloalkyl, or halo;

each $R^{3b}$ is independently H, —CN, $C_{1-3}$ alkyl, $C_{1-3}$ haloalkyl, $C_{1-3}$ alkoxy, $C_{1-3}$ haloalkoxy, $C_{3-4}$ cycloalkyl, or halo;

$Y^1$ is N, or $CR^{Y1}$; wherein $R^{Y1}$ is H, F, Cl, Br, CN, $C_{1-3}$ alkyl, $C_{1-3}$ haloalkyl, $C_{1-3}$ alkoxy, —$CH_2OCH_3$, or $C_{1-3}$ haloalkoxy;

$R^1$ is $C_{1-3}$ alkyl, $C_{3-10}$ cycloalkyl, $C_{6-12}$ aryl, heterocyclyl, or heteroaryl; wherein the cycloalkyl, heterocyclyl, heteroaryl, or aryl of $R^1$ is optionally substituted with 1 to 4 $Z^1$, which may be the same or different; the alkyl of $R^1$ is optionally substituted with one to four $R^{1a}$, which may be the same or different; each $R^{1a}$ is independently —CN, $C_{2-6}$ alkynyl, $C_{3-10}$ cycloalkyl, $C_{1-6}$ haloalkyl, $C_{6-12}$ aryl, heterocyclyl, or heteroaryl; wherein the cycloalkyl, aryl, heterocyclyl, or heteroaryl of Ra is optionally substituted with 1 to 4 $Z^7$, which may be the same or different;

$R^2$ is $C_{1-3}$ alkyl, $C_{3-10}$ cycloalkyl, $C_{6-12}$ aryl, heterocyclyl, heteroaryl, or —$NR^{2a}R^{2b}$; wherein the alkyl, cycloalkyl, aryl, heterocyclyl, or heteroaryl of $R^2$ is optionally substituted with 1 to 4 $Z^2$, which may be the same or different;

$R^{2a}$ is H, $C_{1-6}$ alkyl, $C_{1-6}$ haloalkyl, —$COR^{2a1}$, —$COOR^{2a1}$, —$CONR^{2a1}R^{2b1}$, —$SO_2R^{2a}$, $SO_2NR^{2a1}R^{2b1}$, $C_{6-10}$ aryl, $C_{3-10}$ cycloalkyl, heterocyclyl, or heteroaryl; wherein the alkyl, aryl, cycloalkyl, heterocyclyl, or heteroaryl of $R^{2a}$ is each optionally substituted with 1 to 4 $Z^3$, which may be the same or different, $R^{2b}$ is H, $C_{1-6}$ alkyl, $C_{1-6}$ haloalkyl, $C_{6-10}$ aryl, $C_{3-10}$ cycloalkyl, heterocyclyl, or heteroaryl; wherein the alkyl, aryl, cycloalkyl, heterocyclyl, or heteroaryl of $R^{2b}$ is each optionally substituted with 1 to 4 $Z^4$, which may be the same or different, or $R^{2a}$ and $R^{2b}$ together with the nitrogen to which they are attached form a heterocyclyl or heteroaryl, wherein the heterocyclyl or heteroaryl formed from $R^{2a}$ and $R^{2b}$ together with the nitrogen to which they are attached is optionally substituted with 1 to 4 $Z^5$, which may be the same or different, wherein the heterocyclyl or heteroaryl formed from $R^{2a}$ and $R^{2b}$ is 3 to 10 membered heterocyclyl or heteroaryl having 0 to 3 additional heteroatoms each independently N, O, or S;

or $R^1$ and $R^2$ together with the N to which they are attached form a heterocyclyl; wherein the heterocyclyl formed from $R^1$ and $R^2$ together with the N to which they are attached is optionally substituted with one to four $Z^6$, which may be the same or different, wherein the heterocyclyl formed from $R^1$ and $R^2$ is 3 to 20 membered heterocyclyl having 0 to 3 additional heteroatoms each independently N, O, or S;

each $Z^1$, $Z^2$, $Z^3$, $Z^4$, $Z^5$, $Z^6$, or $Z^7$ is independently $C_{1-9}$ alkyl, $C_{1-8}$ haloalkyl, $C_{1-6}$ alkoxy, $C_{1-6}$ haloalkoxy, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$) N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —$NR^{12a}$S(O)$_2$N($R^{12b}$)($R^{12c}$), $NR^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —$SF_5$, —S(O)$R^{12a}$, —S(O)(NH)$R^{12a}$, —S(O)$_2R^{12a}$, —S(O)$_2$N($R^{12a}$)($R^{12b}$), or —S(O)($NR^{12a}$)$R^{12b}$; wherein the alkyl, haloalkyl, alkenyl, alkynyl, cycloalkyl, heterocyclyl, aryl, or heteroaryl of each $Z^1$, $Z^2$, $Z^3$, $Z^4$, $Z^5$, $Z^6$, or $Z^7$ is each optionally substituted with 1 to 4 $Z^{1a}$, which may be the same or different;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$) +, —N($R^{12a}$)—C(O)$R^{12b}$, —N($R^{12a}$)C(O)O($R^{12b}$), —N($R^{12a}$)C(O)N($R^{12b}$)($R^{12c}$)—N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$—S(O)$R^{12a}$, —S(O)(NH)$R^{12a}$, —S(O)$_2R^{12a}$, —S(O)$_2$N($R^{12a}$)($R^{12b}$), or —S(O)($NR^{12a}$)$R^{12b}$; wherein the alkyl, haloalkyl, alkenyl, alkynyl, cycloalkyl, heterocyclyl, aryl, or heteroaryl of $Z^{1a}$ is each optionally substituted with 1 to 4 $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —N3, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{2a1}$, $R^{2b1}$, $R^{12a}$, $R^{12b}$, or $R^{12c}$ is independently H, $C_{1-6}$ alkyl, $C_{3-10}$ cycloalkyl, heterocyclyl, $C_{6-10}$ aryl, or heteroaryl, wherein the alkyl, cycloalkyl, heterocyclyl, aryl, or heteroaryl of each of $R^{2a}$, $R^{2b1}$, $R^{12a}$, $R^{12b}$, or $R^{12c}$ is each optionally substituted 1 to 4 $Z^{1b}$, which may be the same or different;

wherein each heteroaryl of the compound of Formula (I) unless otherwise specified is 5 to 14 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O or S.

In some embodiments, the compound of Formula (I) is a compound of Formula (Ia), (Ia)

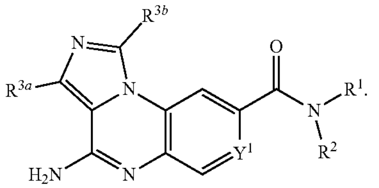

In some embodiments, the compound of Formula (I) is a compound of Formula (Ib), (Ib)

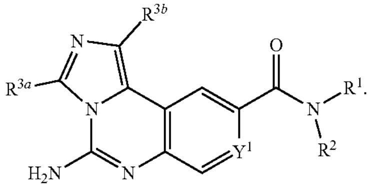

In some embodiments, the compound of Formula (I) is a compound of Formula (Ic), (Ic)

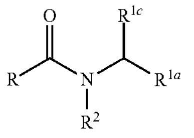

$R^{1a}$ is $C_{6-12}$ aryl, 3 to 10 membered heterocyclyl, or 5 to 10 membered heteroaryl, the aryl, heterocyclyl, or heteroaryl of Ria is optionally substituted with 1 to 4 $Z^7$, which may be the same or different;

$R^{1c}$ is H, —$CH_3$, or cyclopropyl;

the heteroaryl of $R^{1a}$ is a heteroaryl having one to three heteroatoms each independently N, O, or S; and the heterocyclyl of $R^{1a}$ is a heterocyclyl having one to three heteroatoms each independently N, O or S.

In some embodiments, the compound of Formula (I), (Ia), (Ib), or (Ic), or a pharmaceutically acceptable salt thereof, is the compound wherein $R^{3a}$ is H, $CH_3$, F, or $C_1$. In some embodiments, $R^{3a}$ is $CH_3$. In some embodiments, $R^{3a}$ is H.

In some embodiments, the compound of Formula (I), (Ia), (Ib), or (Ic), or a pharmaceutically acceptable salt thereof, is the compound wherein $R^{3b}$ is H, $CH_3$, F, Cl, $OCH_3$, $CF_2H$, or $CF_3$. In some embodiments, $R^{3b}$ is $CH_3$. In some embodiments, $R^{3b}$ is H.

In some embodiments, the compound of Formula (I), (Ia), (Ib), or (Ic), or a pharmaceutically acceptable salt thereof, is the compound wherein $Y^1$ is N. In some embodiments, $Y^1$ is $CR^{Y1}$; $R^{Y1}$ is H, $CH_3$, F, Cl, or CN. In some embodiments, $Y^1$ is $CR^{Y1}$; $R^{Y1}$ is H, $CH_3$, or F. In some embodiments, $Y^1$ is —CF. In some embodiments, $Y^1$ is —CH.

In some embodiments, the compound of Formula (I), (Ia), or (Ib), or a pharmaceutically acceptable salt thereof, is the compound wherein $R^1$ is $C_{1-3}$ alkyl optionally substituted with 1 to 3 $R^{1a}$;

each $R^{1a}$ is independently —CN, OH, $C_{2-6}$ alkynyl, $C_{3-10}$ cycloalkyl, $C_{1-6}$ haloalkyl, $C_{1-6}$ alkoxy, $C_{6-12}$ aryl, 3 to 10 membered heterocyclyl, or 5 to 10 membered heteroaryl; the cycloalkyl, aryl, heterocyclyl, or heteroaryl of $R^{1a}$ is optionally substituted with 1 to 4 $Z^7$, which may be the same or different;

the heteroaryl of $R^1$ is a heteroaryl having one to three heteroatoms each independently N, O, or S; and the heterocyclyl of $R^{1a}$ is a heterocyclyl having one to three heteroatoms each independently N, O, or S.

In some embodiments, the compound of Formula (I), (Ia), or (Ib), or a pharmaceutically acceptable salt thereof, is the compound wherein $R^1$ is $C_{1-3}$ alkyl optionally substituted with $R^{1a}$, wherein $R^{1a}$ is $C_{6-12}$ aryl, 3 to 16 membered heterocyclyl, or 5 to 10 membered heteroaryl; the aryl, heterocyclyl, or heteroaryl of $R^{1a}$ is optionally substituted with 1 to 4 $Z^7$, which may be the same or different;

the heteroaryl of $R^{1a}$ is a heteroaryl having one to three heteroatoms each independently N, O, or S; and the heterocyclyl of $R^{1a}$ is a heterocyclyl having one to three heteroatoms each independently N, O or S.

In some embodiments, the compound of Formula (Ic), or a pharmaceutically acceptable salt thereof, is the compound wherein $R^{1c}$ is H.

In some embodiments, the compound of Formula (I), (Ia), (Ib), or (Ic), or a pharmaceutically acceptable salt thereof, is the compound wherein $R^{1a}$ is phenyl, pyridyl, pyrimidinyl, pyrazinyl, pyridazinyl, benzofuranyl, benzothiazolyl, benzoimidazolyl, benzodioxolyl, or benzoxazolyl; each $R^{1a}$ is optionally substituted with 1 to 3 $Z^7$, which may be the same or different.

In some embodiments, the compound of Formula (I), (Ia), (Ib), or (Ic), or a pharmaceutically acceptable salt thereof, is the compound wherein $R^{1a}$ is phenyl optionally substituted with 1 to 3 $Z^7$, which may be the same or different.

In some embodiments, the compound of Formula (I), (Ia), (Ib), or (Ic), or a pharmaceutically acceptable salt thereof, is the compound wherein $R^{1a}$ is phenyl,

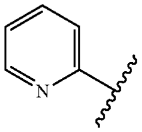
,
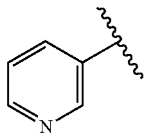
,
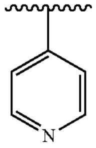
,

-continued

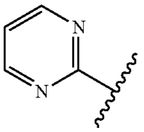
,
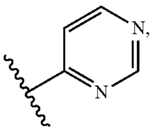
,
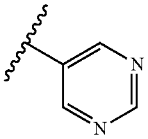
,
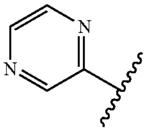
,
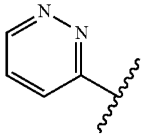
,
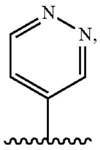
,
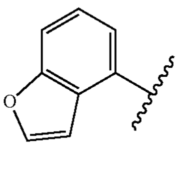
,
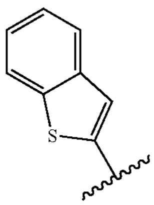
,
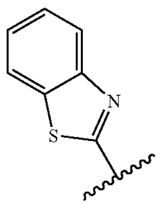
,
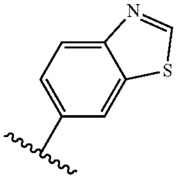
,
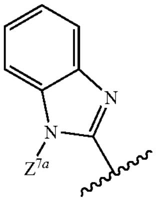
,
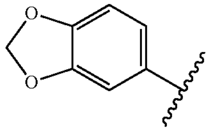
,
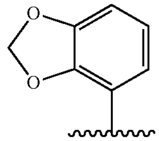
,
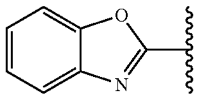
, or
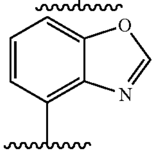
;

each $R^{1a}$ is optionally substituted with 1 to 3 $Z^7$; and $Z^{7a}$ is H, $C_{1-6}$ alkyl, or $C_{1-6}$ haloalkyl.

In some embodiments, the compound of Formula (I), (Ia), (Ib), or (Ic), or a pharmaceutically acceptable salt thereof, is the compound wherein each $Z^7$ is independently halo, —OH, $C_{1-6}$ alkyl, $C_{1-6}$ haloalkyl, $C_{3-6}$ cycloalkyl, $C_{2-6}$ alkynyl, CN, $C_{1-6}$ alkoxy, $C_{1-6}$ haloalkoxy, 5 to 10 membered heteroaryl, $C_{6-10}$ aryl, or 5 to 10 membered heterocyclyl; the alkyl, cycloalkyl, alkynyl, heteroaryl, aryl, or heterocyclyl of $Z^1$ is optionally substituted with 1 to 3 $Z^{1a}$, which may be the same or different; each $Z^{1a}$ is independently halo, —OH, $C_{1-6}$ alkyl, $C_1$. 6haloalkyl, $C_{3-6}$ cycloalkyl, $C_{2-6}$ alkynyl, CN, $C_{1-6}$ alkoxy, $C_{1-6}$ haloalkoxy, 5 to 10 membered heteroaryl, $C_{6-10}$ aryl, or 5 to 10 membered heterocyclyl, wherein each alkyl, cycloalkyl, alkynyl, heteroaryl, aryl, or heterocyclyl of $Z^{1a}$ is optionally substituted with one to three substituents selected from halo, —OH, $C_{1-6}$ alkyl, $C_{1-6}$ haloalkyl, CN, $C_{1-6}$ alkoxy, $C_{1-6}$ haloalkoxy, and $C_{3-6}$ cycloalkyl.

In some embodiments, the compound of Formula (I), (Ia), (Ib), or (Ic), or a pharmaceutically acceptable salt thereof, is the compound wherein each $Z^7$ is independently halo, CN, $C_{1-6}$ alkoxy, $C_{1-6}$ alkyl, $C_{1-6}$ haloalkyl, or 5 to 6 membered heteroaryl, wherein the heteroaryl of $Z^7$ is optionally substituted with one to four $Z^{1a}$, which may be the same or different; and each $Z^{1a}$ is independently halo or $C_{1-6}$ haloalkyl.

In some embodiments, the compound of Formula (I), (Ia), (Ib), or (Ic), or a pharmaceutically acceptable salt thereof, is the compound wherein each $Z^7$ is independently F, Cl, CN, —$CF_3$, —$OCHF_2$, —$CF_3$, —$OCH_3$,

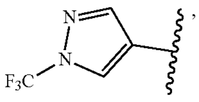,
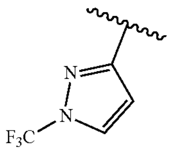,
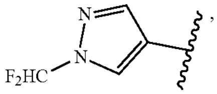,
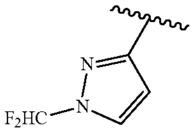,
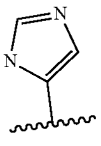, or 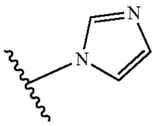.

In some embodiments, the compound of Formula (I), (Ia), (Ib), or (Ic), or a pharmaceutically acceptable salt thereof, is the compound wherein each $Z^7$ is independently F, $C_1$, —$OCH_3$, CN, or phenyl.

In some embodiments, the compound of Formula (I), (Ia), or (Ib), or a pharmaceutically acceptable salt thereof, is the compound wherein $R^1$ is $C_{3-6}$ cycloalkyl, 3 to 16 membered heterocyclyl, 5 to 10 membered heteroaryl, or $C_{6-12}$ aryl; wherein the cycloalkyl, heterocyclyl, heteroaryl, or aryl of $R^1$ is optionally substituted with 1 to 4 $Z^1$, which may be the same or different.

In some embodiments, the compound of Formula (I), (Ia), or (Ib), or a pharmaceutically acceptable salt thereof, is the compound wherein $R^1$ is

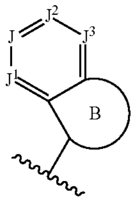;

each of J, $J^1$, $J^2$, and $J^3$, is independently N, or C optionally substituted with $Z^1$, provided that not more than two of J, $J^1$, $J^2$, and $J^3$ are N; and Ring B is $C_{5-8}$ cycloalkyl, or 5 to 8 membered heterocycloalkyl having 1 to 2 O, and optionally Ring B is substituted with 1 or 2 $Z^1$.

In some embodiments, the compound of Formula (I), (Ia), or (Ib), or a pharmaceutically acceptable salt thereof, is the compound wherein $R^1$ is 3 to 16 membered heterocyclyl optionally substituted with 1 to 4 $Z^1$, which may be the same or different.

In some embodiments, the compound of Formula (I), (Ia), or (Ib), or a pharmaceutically acceptable salt thereof, is the compound wherein $R^1$ is a heterocyclyl selected from

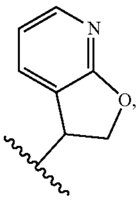,
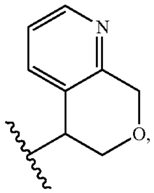,
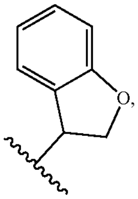, and 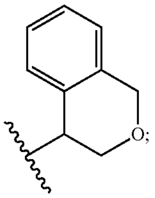;

the heterocyclyl of $R^1$ is optionally substituted with 1 to 4 $Z^1$, which may be the same or different.

In some embodiments, the compound of Formula (I), (Ia), or (Ib), or a pharmaceutically acceptable salt thereof, is the compound wherein $R^1$ is 5 to 10 membered heteroaryl optionally substituted with 1 to 4 $Z^1$.

In some embodiments, the compound of Formula (I), (Ia), or (Ib), or a pharmaceutically acceptable salt thereof, is the compound wherein $R^1$ is a heteroaryl selected from

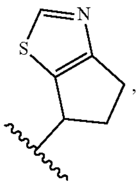,
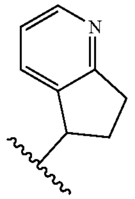,
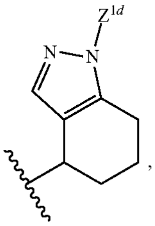, and 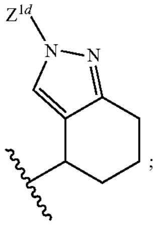;

the heteroaryl of $R^1$ is optionally substituted with 1 to 4 $Z^1$, which may be the same or different; and $Z^{1d}$ is H, $C_{1-6}$ alkyl, or $C_{1-6}$ haloalkyl.

In some embodiments, the compound of Formula (I), (Ia), or (Ib), or a pharmaceutically acceptable salt thereof, is the compound wherein $R^1$ is $C_{6-12}$ aryl optionally substituted with 1 to 4 $Z^1$, which may be the same or different. In some embodiments, the aryl of $R^1$ is monocyclic. In some embodiments, the aryl of $R^1$ is bicyclic. In some embodiments, the aryl of $R^1$ is tricyclic.

In some embodiments, the compound of Formula (I), (Ia), or (Ib), or a pharmaceutically acceptable salt thereof, is the compound wherein $R^1$ is $C_{6-12}$ aryl selected from

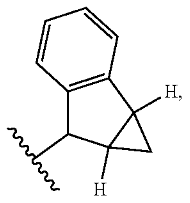

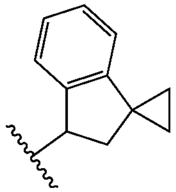, and

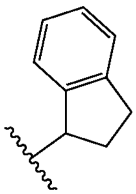;

the aryl of $R^1$ is optionally substituted with 1 to 4 $Z^1$, which may be the same or different.

In some embodiments, the compound of Formula (I), (Ia), or (Ib), or a pharmaceutically acceptable salt thereof, is the compound wherein $R^1$ is

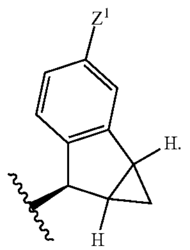

In some embodiments, $R^1$ is

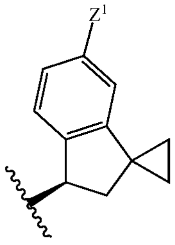.

In some embodiments, $R^1$ is

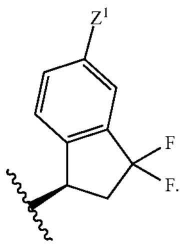

In some embodiments, the compound of Formula (I), (Ia), (Ib), or (Ic), or a pharmaceutically acceptable salt thereof, is the compound wherein each $Z^1$ is independently halo, —OH, $C_{1-6}$ alkyl, $C_{1-6}$ haloalkyl, $C_{2-6}$ alkynyl, CN, $C_{1-6}$ alkoxy, $C_{1-6}$ haloalkoxy, $C_{3-6}$ cycloalkyl, 5 to 10 membered heteroaryl, $C_{6-10}$ aryl, or 4 to 10 membered heterocyclyl; the alkyl, alkynyl, cycloalkyl, heteroaryl, aryl, or heterocyclyl of $Z^1$ is optionally substituted with 1 to 3 $Z^{1a}$; each $Z^{1a}$ is independently halo, —OH, $C_{1-6}$ alkyl, $C_{1-6}$ haloalkyl, $C_{2-6}$ alkynyl, CN, $C_{1-6}$ alkoxy, $C_{1-6}$ haloalkoxy, $C_{3-6}$ cycloalkyl, 5 to 10 membered heteroaryl, $C_{6-10}$ aryl, or 5 to 10 membered heterocyclyl; wherein each alkyl, alkynyl, cycloalkyl, heteroaryl, aryl, or heterocyclyl of $Z^{1a}$ is optionally substituted with one to three substituents selected from halo, —OH, $C_{1-6}$ alkyl, $C_{1-6}$ haloalkyl, CN, $C_{1-6}$ alkoxy, $C_{1-6}$ haloalkoxy, and $C_{3-6}$ cycloalkyl.

In some embodiments, the compound of Formula (I), (Ia), (Ib), or (Ic), or a pharmaceutically acceptable salt thereof, is the compound wherein each $Z^1$ is independently halo, —OH, $C_{1-6}$ alkyl, $C_{1-6}$ haloalkyl, $C_{2-6}$ alkynyl, CN, $C_{1-6}$ alkoxy, $C_{1-6}$ haloalkoxy, $C_{3-6}$ cycloalkyl, 5 to 6 membered heteroaryl, $C_{6-10}$ aryl, or 4 to 10 membered heterocyclyl;

the alkynyl of $Z^1$ is optionally substituted with 1 to 3 $Z^{1a}$; each $Z^{1a}$ is independently halo, —OH, $C_{1-6}$ haloalkyl, CN, $C_{1-6}$ alkoxy, $C_{1-6}$ haloalkoxy, 5 to 6 membered heteroaryl, $C_{3-6}$ cycloalkyl, phenyl, or 4 to 6 membered heterocyclyl; the heteroaryl, cycloalkyl, phenyl or heterocyclyl of is $Z^{1a}$ is optionally substituted with one to three substituents selected from halo, —OH, $C_{1-6}$ alkyl, $C_{1-6}$haloalkyl, CN, $C_{1-6}$ alkoxy, $C_{1-6}$ haloalkoxy, and $C_{3-6}$ cycloalkyl; and the cycloalkyl, heteroaryl, aryl, or heterocyclyl of $Z^1$ is optionally substituted with 1 to 3 substituents selected from halo, —OH, $C_{1-6}$ haloalkyl, CN, $C_{1-6}$ alkoxy, $C_{1-6}$ haloalkoxy, 5 to 6 membered heteroaryl, $C_{3-6}$ cycloalkyl, phenyl, and 4 to 6 membered heterocyclyl.

In some embodiments, the compound of Formula (I), (Ia), (Ib), or (Ic), or a pharmaceutically acceptable salt thereof, is the compound wherein each $Z^1$ is independently halo, $C_{1-6}$ alkyl, $C_{1-6}$ haloalkyl, $C_{1-6}$ haloalkoxy, cyclopropyl, CN, —OH,

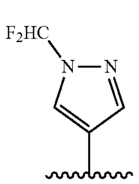, 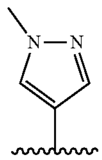, 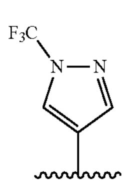, 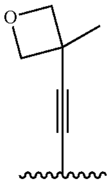,

-continued

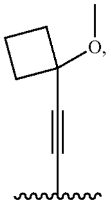 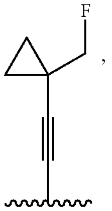 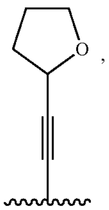 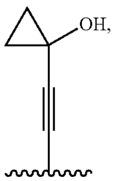

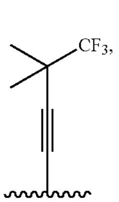 or 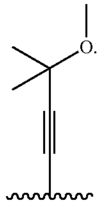

In some embodiments, the compound of Formula (I), (Ia), (Ib), or (Ic), or a pharmaceutically acceptable salt thereof, is the compound wherein each $Z^1$ is independently $C_{1-3}$ alkyl, F, Cl, Br, —$CF_2H$, —$OCF_2H$, cyclopropyl, or —$CF_3$.

In some embodiments, the compound of Formula (I), (Ia), or (Ib), or a pharmaceutically acceptable salt thereof, is the compound wherein $R^1$ is

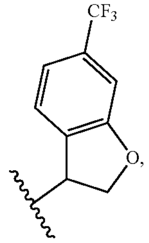 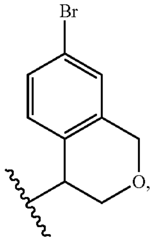 or 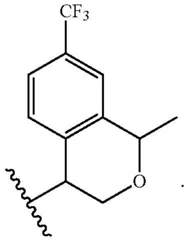

In some embodiments, $R^1$ is

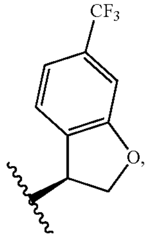 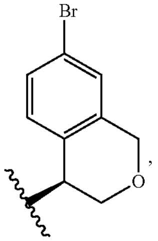 or

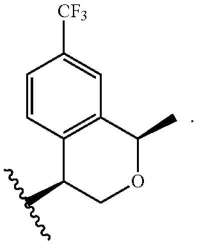

In some embodiments, $R^1$ is

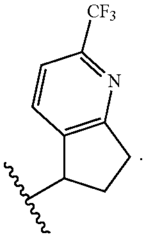 [SMILES: *C1CCc2nc(C(F)(F)F)ccc21]

In some embodiments, $R^1$ is

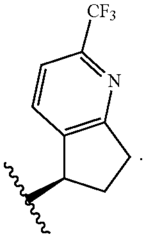 [SMILES: *[C@@H]1CCc2nc(C(F)(F)F)ccc21]

In some embodiments, the compound of Formula (I), (Ia), (Ib), or (Ic), or a pharmaceutically acceptable salt thereof, is the compound wherein $R^2$ is $C_{1-3}$ alkyl, $C_{3-10}$ cycloalkyl, 3 to 10 membered heterocyclyl, 5 to 10 membered heteroaryl, $C_{6-12}$ aryl, or —$NR^{2a}R^{2b}$, wherein the alkyl, cycloalkyl, heterocyclyl, heteroaryl, aryl of $R^2$ is optionally substituted with 1 to 3 $Z^2$, which may be the same or different.

In some embodiments, the compound of Formula (I), (Ia), (Ib), or (Ic), or a pharmaceutically acceptable salt thereof, is the compound wherein $R^2$ is —$NR^{2a}R^{2b}$;

$R^{2a}$ is H, $C_{1-6}$ alkyl, $C_{1-6}$ haloalkyl, —$COR^{2a1}$, —$COOR^{2a1}$, —$CONR^{2a1}R^{2b1}$, —$SO_2R^{2a1}$, —$SO_2NR^{2a1}R^{2b1}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^{2a}$ is each optionally substituted with one to four $Z^3$, which may be the same or different, and $R^{2b}$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^4$ is each optionally substituted with one to four $Z^4$, which may be the same or different;

or $R^{2a}$ and $R^{2b}$ together with the nitrogen to which they are attached form a 3 to 10 membered heterocyclyl or heteroaryl; wherein the heterocyclyl or heteroaryl formed from $R^{2a}$ and $R^{2b}$ is optionally substituted with one to four $Z^5$, which may be the same or different.

In some embodiments, the compound of Formula (I), (Ia), (Ib), or (Ic), or a pharmaceutically acceptable salt thereof, is the compound wherein $R^{2a}$ is —$COR^{2a1}$ or —$COOR^{2a1}$; $R^{2a1}$ is $C_{1-6}$ alkyl, $C_{1-6}$ haloalkyl, or $C_{3-6}$ cycloalkyl; and $R^{2b}$ is $C_{1-6}$ alkyl or $C_{1-6}$ haloalkyl;

or $R^{2a}$ and $R^{2b}$ together with the nitrogen to which they are attached form a 3 to 8 membered heterocyclyl; wherein the heterocyclyl formed from $R^{2a}$ and $R^{2b}$ is optionally substituted with one to three $Z^5$, which may be the same or different; each $Z^5$ is independently oxo, halo, $C_{1-6}$ alkyl or $C_{1-6}$ haloalkyl.

In some embodiments, the compound of Formula (I), (Ia), (Ib), or (Ic), or a pharmaceutically acceptable salt thereof, is the compound wherein $R^2$ is

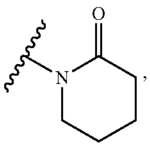, 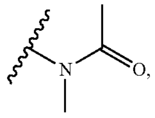 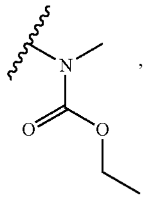, or

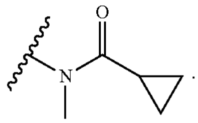.

In some embodiments, the compound of Formula (I), (Ia), (Ib), or (Ic), or a pharmaceutically acceptable salt thereof, is the compound wherein $R^2$ is 5 or 6 membered heteroaryl optionally substituted with 1 to 3 $Z^2$, which may be the same or different;

each $Z^2$ is independently halo or $C_{1-3}$ alkyl; and the heteroaryl of $R^2$ is a heteroaryl having one to three heteroatoms independently N, O, or S.

In some embodiments, the compound of Formula (I), (Ia), (Ib), or (Ic), or a pharmaceutically acceptable salt thereof, is the compound wherein $R^2$ is 5 or 6 membered heteroaryl optionally substituted with 1 to 3 $Z^2$, which may be the same or different;

each $Z^2$ is independently halo or $C_{1-3}$ alkyl; and the heteroaryl of $R^2$ is a heteroaryl having one to two heteroatoms independently N or O.

In some embodiments, the compound of Formula (I), (Ia), (Ib), or (Ic), or a pharmaceutically acceptable salt thereof, is the compound wherein $R^2$ is 5 membered heteroaryl optionally substituted with 1 to 2 $Z^2$, which may be the same or different;

each $Z^2$ is independently halo or $C_{1-3}$ alkyl; and the heteroaryl of $R^2$ is a heteroaryl having one to two N.

In some embodiments, the compound of Formula (I), (Ia), or (Ib), or a pharmaceutically acceptable salt thereof, is the compound wherein $R^1$ and $R^2$ together with the N to which they are attached form a 5 to 18 membered heterocyclyl; wherein the heterocyclyl formed from $R^1$ and $R^2$ together with the N to which they are attached is optionally substituted with 1 to 4 $Z^6$, which may be the same or different. In some embodiments, the heterocyclyl formed from $R^1$ and $R^2$ together with the N to which they are attached is monocycle, bicycle, tricycle, or tetracycle, wherein each of monocycle, bicycle, tricycle, or tetracycle formed from $R^1$ and $R^2$ is optionally substituted with 1 to 4 $Z^6$, which may be the same or different.

In some embodiments, the compound of Formula (I), (Ia), or (Ib), or a pharmaceutically acceptable salt thereof, is the compound wherein $—NR^1R^2$ is

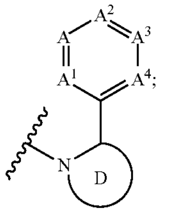

each of A, $A^1$, $A^2$, $A^3$, and $A^4$, is independently N, or C optionally substituted with $Z^{1a}$, provided that not more than two of A, $A^1$, $A^2$, $A^3$, and $A^4$ are N; and Ring D is a 5 to 10 membered heterocyclyl optionally additionally substituted with 1 to 3 $Z^6$, which may be the same or different; Ring D may optionally have an additional heteroatom selected from N, S, and O.

In some embodiments, the compound of Formula (I), (Ia), or (Ib), or a pharmaceutically acceptable salt thereof, is the compound wherein $—NR^1R^2$ is

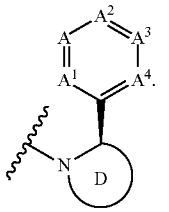

In some embodiments, the compound of Formula (I), (Ia), or (Ib), or a pharmaceutically acceptable salt thereof, is the compound wherein Ring D is a monocycle optionally additionally substituted with 1 to 2 $Z^6$, which may be the same or different.

In some embodiments, the compound of Formula (I), (Ia), or (Ib), or a pharmaceutically acceptable salt thereof, is the compound wherein Ring D is piperidinyl, piperazinyl, pyrrolidinyl or morpholinyl; wherein each of the piperidinyl, piperazinyl, pyrrolidinyl, and morpholinyl of Ring D is optionally additionally substituted with 1 or 2 $Z^6$.

In some embodiments, the compound of Formula (I), (Ia), or (Ib), or a pharmaceutically acceptable salt thereof, is the compound wherein Ring D is a bridged bicycle optionally additionally substituted with 1 to 2 $Z^6$, which may be the same or different.

In some embodiments, the compound of Formula (I), (Ia), or (Ib), or a pharmaceutically acceptable salt thereof, is the compound wherein Ring D is a bridged morpholinyl optionally additionally substituted with 1 or 2 $Z^6$, which may be the same or different.

In some embodiments, the compound of Formula (I), (Ia), or (Ib), or a pharmaceutically acceptable salt thereof, is the compound wherein Ring D is a fused bicycle optionally additionally substituted with 1 or 2 $Z^6$, which may be the same or different.

In some embodiments, the compound of Formula (I), (Ia), or (Ib), or a pharmaceutically acceptable salt thereof, is the compound wherein the heterocyclyl formed from $R^1$ and $R^2$ together with the N to which they are attached is tricycle, wherein any two joined rings of the tricycle may be fused or bridged, wherein the heterocyclyl formed from $R^1$ and $R^2$ may be optionally substituted with 1 to 4 $Z^6$. In some embodiments, the heterocyclyl is 13-16 membered tricycle.

In some embodiments, the compound of Formula (I), (Ia), or (Ib), or a pharmaceutically acceptable salt thereof, is the compound wherein the heterocyclyl formed from $R^1$ and $R^2$ together with the N to which they are attached is tricycle, wherein any two joined rings of the tricycle may be fused or spiro, wherein the heterocyclyl formed from $R^1$ and $R^2$ may be optionally substituted with 1 to 4 $Z^6$. In some embodiments, the heterocyclyl is 13-16 membered tricycle.

In some embodiments, the compound of Formula (I), (Ia), or (Ib), or a pharmaceutically acceptable salt thereof, is the compound wherein the heterocyclyl formed from $R^1$ and $R^2$ together with the N to which they are attached is a tetracycle, wherein the heterocyclyl formed from $R^1$ and $R^2$ may be optionally substituted with 1 to 4 $Z^6$. In some embodiments, the heterocyclyl is 13-18 membered tetracycle. In some embodiments, any two joined rings of the tetracycle may be fused or spiro.

In some embodiments, the compound of Formula (I), (Ia), or (Ib), or a pharmaceutically acceptable salt thereof, is the compound wherein $—NR^1R^2$ is

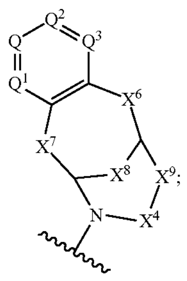

each of Q, $Q^1$, $Q^2$, and $Q^3$, is independently N, or C optionally substituted with $Z^6$, provided that not more than two of Q, $Q^1$, $Q^2$, and $Q^3$ are N;

$X^4$ is $CH_2$ optionally substituted with one or two $Z^6$;

$X^6$ is a bond, O, $CH_2$, $CH_2O$, $CH_2CH_2$, or $OCH_2$, wherein each of $CH_2$, $CH_2O$, $CH_2CH_2$, and $OCH_2$ of $X^6$ is optionally substituted with one or two $Z^6$;

$X^7$ is a bond or $CH_2$ optionally substituted with one or two $Z^6$;

$X^8$ is a bond, $CH_2$, or $CH_2O$, wherein each of $CH_2$ and $CH_2O$ of $X^8$ is optionally substituted with one or two $Z^6$; and $X^9$ is $CH_2$, $CH_2O$, or $CH_2CH_2$, wherein each of $CH_2$, $CH_2O$, and $CH_2CH_2$ of $X^9$ is optionally substituted with one or two $Z^6$.

In some embodiments, the compound of Formula (I), (Ia), or (Ib), or a pharmaceutically acceptable salt thereof, is the compound wherein $—NR^1R^2$ is

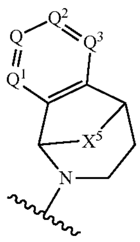

or

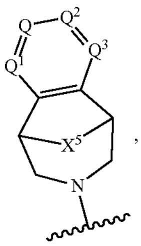

, wherein $—NR^1R^2$ is optionally substituted with 1 to 4 $Z^6$, which may be the same or different;

each of Q, $Q^1$, $Q^2$, and $Q^3$, is independently N, or C optionally substituted with $Z^6$, provided that not more than two of Q, $Q^1$, $Q^2$, and $Q^3$ are N; and $X^5$ is $—OCH_2—$, $—CH_2—$, $—CH_2CH_2—$, or $—CF_2—$.

In some embodiments, the compound of Formula (I), (Ia), or (Ib), or a pharmaceutically acceptable salt thereof, is the compound wherein $—NR^1R^2$ is

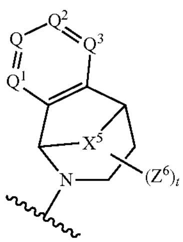

or

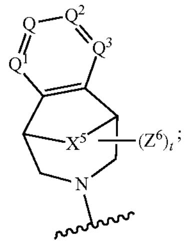

each of Q, $Q^1$, $Q^2$, and $Q^3$, is independently N, or C optionally substituted with $Z^6$, provided that not more than two of Q, $Q^1$, $Q^2$, and $Q^3$ are N;

$X^5$ is $—OCH_2—$, $—CH_2—$, $—CH_2CH_2—$, or $—CF_2—$; and t is 0, 1, or 2.

In some embodiments, the compound of Formula (I), (Ia), or (Ib), or a pharmaceutically acceptable salt thereof, is the compound wherein $—NR^1R^2$ is a heterocyclyl of

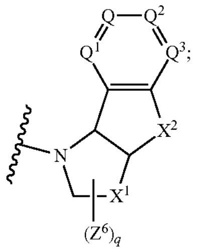

each of Q, $Q^1$, $Q^2$, and $Q^3$, is independently N, or C optionally substituted with $Z^6$, provided that not more than two of Q, $Q^1$, $Q^2$, and $Q^3$ are N;

$X^1$ is $—OCF_2—$, $—OCH_2—$, $—CH_2—$, $—CH_2CH_2—$, $—OCH_2CH_2—$, $—CF_2—$, or $—CH_2NR^{1b}—$; wherein $R^{1b}$ is $C_{1-6}$ alkyl, $C_{1-6}$ haloalkyl, oxetanyl, $—C(O)—R^{12a}$, $—S(O)R^{12a}$, or $C_{3-6}$ cycloalkyl;

$X^2$ is O, $—OCH_2—$, $—CF_2—$, or $—CH_2—$; and q is 0, 1, or 2.

In some embodiments, the compound of Formula (I), (Ia), or (Ib), or a pharmaceutically acceptable salt thereof, is the compound wherein —$NR^1R^2$ is

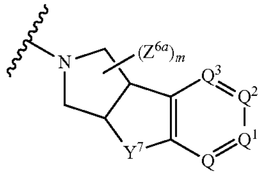

or

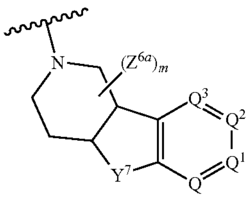

;

$Y^7$ is O, —$OCH_2$—, or —$CH_2CH_2$—; each of is —$OCH_2$— and —$CH_2CH_2$— of $Y^7$ is optionally substituted with one or two $Z^6$;

each of Q, $Q^1$, $Q^2$, and $Q^3$, is independently N, or C optionally substituted with $Z^6$, provided that not more than two of Q, $Q^1$, $Q^2$, and $Q^3$ are N;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and m is 0, 1, or 2.

In some embodiments, the compound of Formula (I), (Ia), or (Ib), or a pharmaceutically acceptable salt thereof, is the compound wherein —$NR^1R^2$ is

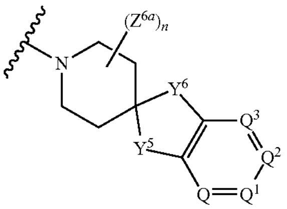

or

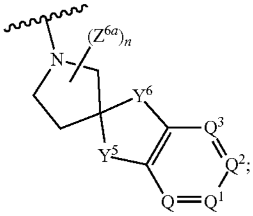

;

each of Q, $Q^1$, $Q^2$, and $Q^3$, is independently N, or C optionally substituted with $Z^6$, provided that not more than two of Q, $Q^1$, $Q^2$, and $Q^3$ are N;

$Y^5$ is O, $NR^{1d}$, $CH_2$, $CH_2CH_2$, $CH_2O$, $CONR^{1d}$, $CH_2NR^{1d}$, wherein each of $CH_2$, $CH_2CH_2$, and $CH_2O$ of $Y^5$ is optionally substituted with one or two $Z^6$;

$Y^6$ is a bond, O, $NR^{1d}$, $CH_2$, $CH_2CH_2$, $CH_2O$, $CONR^{1d}$, or $CH_2NR^{1d}$; wherein each of $CH_2$, $CH_2CH_2$, and $CH_2O$ of $Y^6$ is optionally substituted with one or two $Z^6$; and $R^{1d}$ is H, $C_{1-6}$ alkyl, or $C_{1-6}$ haloalkyl;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and n is 0, 1, or 2.

In some embodiments, the compound of Formula (I), (Ia), or (Ib), or a pharmaceutically acceptable salt thereof, is the compound wherein —$NR^1R^2$ is

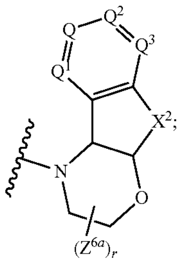

;

each of Q, $Q^1$, $Q^2$, and $Q^3$, is independently N, or C optionally substituted with $Z^6$, provided that not more than two of Q, $Q^1$, $Q^2$, and $Q^3$ are N; and $X^2$ is O, —$OCH_2$—, —$CF_2$—, or —$CH_2$—;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and r is 0, 1, or 2.

In some embodiments, the compound of Formula (I), (Ia), or (Ib), or a pharmaceutically acceptable salt thereof, is the compound wherein —$NR^1R^2$ is

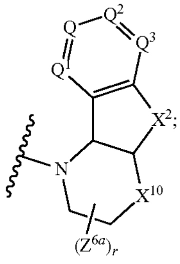

;

each of Q, $Q^1$, $Q^2$, and $Q^3$, is independently N, or C optionally substituted with $Z^6$, provided that not more than one of Q, $Q^1$, $Q^2$, and $Q^3$ is N; and $X^2$ is O or —$CH_2$—;

$X^{10}$ is O or —$CH_2$—;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and r is 0, 1, or 2.

In some embodiments, the compound of Formula (I), (Ia), or (Ib), or a pharmaceutically acceptable salt thereof, is the compound wherein $-NR^1R^2$ is

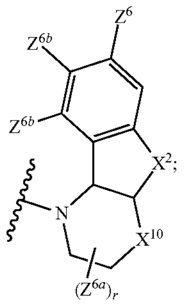

$X^2$ is O or $-CH_2-$;

$X^{10}$ is O or $-CH_2-$;

each $Z^{6b}$ is independently H or $Z^6$;

each $Z^{6a}$ is independently $Z^6$, or two $Z^{6a}$ are attached to one carbon, and the two $Z^{6a}$ together with the carbon to which they attached form a cyclopropyl; and r is 0, 1, or 2.

In some embodiments, the compound of Formula (I), (Ia), or (Ib), or a pharmaceutically acceptable salt thereof, is the compound wherein $-NR^1R^2$ is

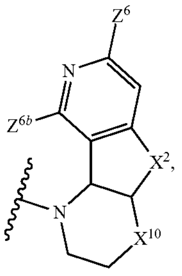

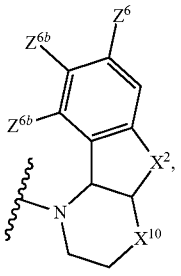

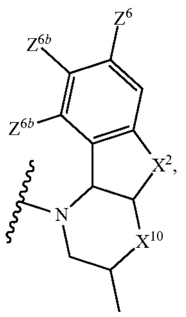

or

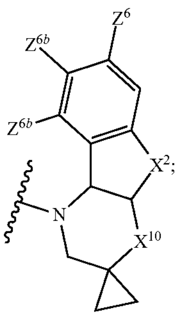

$X^2$ is O or $-CH_2-$;

$X^{10}$ is O or $-CH_2-$; and each $Z^{6b}$ is independently H or $Z^6$.

In some embodiments, the compound of Formula (I), (Ia), or (Ib), or a pharmaceutically acceptable salt thereof, is the compound wherein $-NR^1R^2$ is

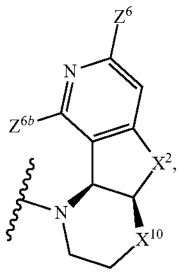

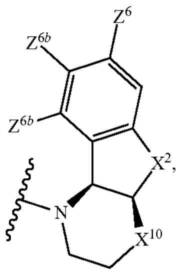

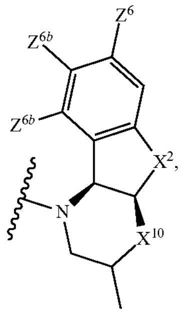

or

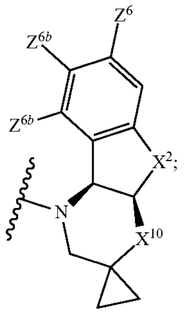

$X^2$ is O or $-CH_2-$;

$X^{10}$ is O or $-CH_2-$; and each $Z^{6b}$ is independently H or $Z^6$.

In some embodiments, the compound of Formula (I), (Ia), or (Ib), or a pharmaceutically acceptable salt thereof, is the compound wherein $-NR^1R^2$ is

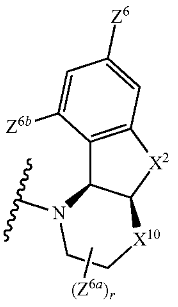

or

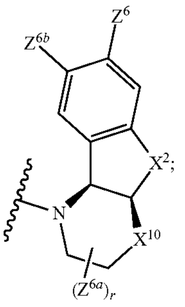

$X^2$ is O or $-CH_2-$;

$X^{10}$ is O or $-CH_2-$; and each $Z^{6b}$ is independently H or $Z^6$.

r is 0, 1, or 2.

In some embodiments, the compound of Formula (I), (Ia), or (Ib), or a pharmaceutically acceptable salt thereof, is the compound wherein $-NR^1R^2$ is

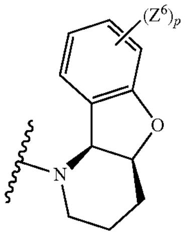

or

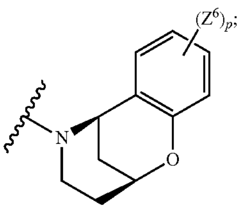

and p is 1 or 2. In some embodiments, p is 1. In some embodiments, p is 2. In some embodiments, each $Z^6$ is independently F, $CF_3$ or $OCF_3$.

In some embodiments, the compound of Formula (I), or (Ia), or a pharmaceutically acceptable salt thereof, is the compound wherein —$NR^1R^2$ is

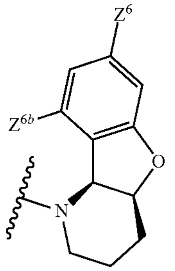

or

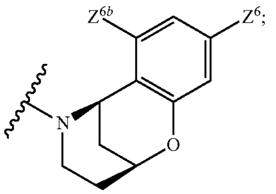

and $Z^{6b}$ is H or $Z^6$. In some embodiments, $Z^{6b}$ is F. In some embodiments, $Z^6$ is $CF_3$ or $OCF_3$.

In some embodiments, the compound of Formula (I), (Ia), or (Ib), or a pharmaceutically acceptable salt thereof, is the compound wherein each $Z^{6b}$ is independently H or F.

In some embodiments, the compound of Formula (I), (Ia), or (Ib), or a pharmaceutically acceptable salt thereof, is the compound wherein at least one $Z^{6b}$ is F.

In some embodiments, the compound of Formula (I), (Ia), or (Ib), or a pharmaceutically acceptable salt thereof, is the compound wherein $Z^{6b}$ is H.

In some embodiments, the compound of Formula (I), (Ia), or (Ib), or a pharmaceutically acceptable salt thereof, is the compound wherein $X^2$ is O; and $X^{10}$ is —$CH_2$—.

In some embodiments, the compound of Formula (I), (Ia), or (Ib), or a pharmaceutically acceptable salt thereof, is the compound wherein $X^2$ is —$CH_2$—; and $X^{10}$ is O.

In some embodiments, the compound of Formula (I), (Ia), or (Ib), or a pharmaceutically acceptable salt thereof, is the compound wherein each $Z^6$ is independently $C_{1-6}$ alkyl, —OH, CN, halo, $C_{1-6}$ haloalkyl, $C_{1-6}$ alkoxy, $C_{1-6}$ haloalkoxy, $C_{2-6}$ alkynyl, $C_{3-15}$ cycloalkyl, 3-18 membered heterocyclyl, $C_{6-10}$ aryl, 5 to 10 membered heteroaryl, —C(O)—$R^{12a}$, —C(O)O—$R^{12a}$; wherein the alkyl, alkynyl, cycloalkyl, heterocyclyl, or heteroaryl is optionally substituted with one to four $Z^{1a}$, which may be the same or different;

each $Z^{1a}$ is independently —OH, CN, $C_{1-6}$ alkyl, halo, $C_{1-6}$ haloalkyl, $C_{1-6}$ alkoxy, $C_{1-6}$ haloalkoxy, $C_{3-10}$ cycloalkyl, 5-18 membered heterocyclyl, $C_{6-10}$ aryl, or 5 to 10 membered heteroaryl, wherein the cycloalkyl, heterocyclyl, aryl, or heteroaryl, is each optionally substituted with one to four $Z^{1b}$, which may be the same or different;

each $Z^{1b}$ is independently CN, —OH, $C_{1-6}$ alkyl, halo, $C_{1-6}$ haloalkyl, $C_{1-6}$ alkoxy, or $C_{1-6}$ haloalkoxy; and each $R^{12a}$ is independently H, $C_{1-6}$ alkyl, or $C_{3-10}$ cycloalkyl.

In some embodiments, the compound of Formula (I), (Ia), or (Ib), or a pharmaceutically acceptable salt thereof, is the compound wherein each $Z^6$ is independently —OH, CN, $C_{1-6}$ alkyl, halo, $C_{1-6}$ haloalkyl, $C_{1-6}$ alkoxy, $C_{1-6}$haloalkoxy, phenyl, or 5 to 6 membered heteroaryl, wherein the phenyl or heteroaryl of $Z^6$ is optionally substituted with 1 to 3 $Z^{1a}$, which may be the same or different; each $Z^{1a}$ is independently halo or $C_{1-6}$ haloalkyl.

In some embodiments, the compound of Formula (I), (Ia), or (Ib), or a pharmaceutically acceptable salt thereof, is the compound wherein each $Z^6$ is independently $C_{1-3}$ alkyl, halo, $C_{1-3}$ haloalkyl, $C_{1-3}$ alkoxy, $C_{1-3}$ haloalkoxy, phenyl, or pyridyl, wherein the phenyl or pyridyl is optionally substituted with one to three substituents independently selected from halo and $C_{1-3}$ haloalkyl.

In some embodiments, the compound of Formula (I), (Ia), or (Ib), or a pharmaceutically acceptable salt thereof, is the compound wherein each $Z^6$ is independently —$CF_3$, F, Cl, —$OCHF_2$, or Br.

In some embodiments, the compound of Formula (I), (Ia), or (Ib), or a pharmaceutically acceptable salt thereof, is the compound wherein each $Z^6$ is independently $CF_3$ or Br.

In some embodiments, the compound of Formula (I), (Ia), or (Ib), or a pharmaceutically acceptable salt thereof, is the compound wherein each $Z^6$ is independently F, $C_{1-3}$ alkyl, $C_{1-3}$ haloalkyl, $C_{1-3}$ alkoxy, or $C_{1-3}$ haloalkoxy.

In some embodiments, the compound of Formula (I), (Ia), or (Ib), or a pharmaceutically acceptable salt thereof, is the compound wherein each $Z^6$ is independently F, —$CH_3$, —$CF_3$, —$C_2F_5$, or —$OCF_3$.

In some embodiments, the present disclosure provides a compound in Table 1A, Tablel 1B, Table 1C, or Table 1D, or a pharmaceutically acceptable salt thereof.

In some embodiments, the compound of Formula (I) or (Ic), or a pharmaceutically acceptable salt thereof, is the compound wherein R is

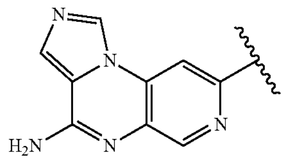

.

In some embodiments, the compound of Formula (I) or (Ic), or a pharmaceutically acceptable salt thereof, is the compound wherein R is

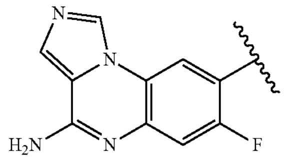

.

In some embodiments, the present disclosure provides a racemic mixture comprising the compound of Formula (I), (Ia), (Ib), or (Ic), or a pharmaceutically acceptable salt thereof. In some embodiments, the present disclosure provides a racemic mixture comprising the compound disclosed herein, or a pharmaceutically acceptable salt thereof. In some embodiments, the present disclosure provides a scalemic mixture comprising the compound of Formula (I), (Ia), (Ib), or (Ic), or a pharmaceutically acceptable salt thereof. In some embodiments, the present disclosure provides a scalemic mixture comprising the compound disclosed herein, or a pharmaceutically acceptable salt thereof.

One of skill in the art is aware that each and every embodiment of a group (e.g., $R^1$) disclosed herein may be combined with any other embodiment of each of the remaining groups (e.g., $R^2$, $R^{3a}$, $R^{3b}$, $Z^1$, $Z^2$, $Z^3$, etc.) to generate a complete compound of Formula (I), (Ia), (Ib), or (Ic), or any Formula described herein or a pharmaceutically acceptable salt, stereoisomer, mixture of stereoisomers, or tautomer thereof, each of which is deemed within the ambit of the present disclosure.

The present disclosure further includes the following embodiments:

Embodiment 1. A compound of Formula (I)

(I)

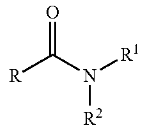

or a pharmaceutically acceptable salt thereof, wherein

R is

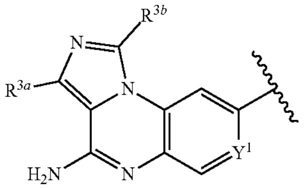

or

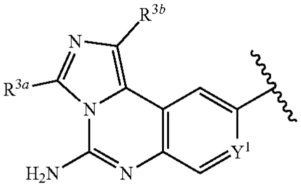

;

each $R^{3a}$ is independently H, —CN, $C_{1-3}$ alkyl, $C_{1-3}$ haloalkyl, $C_{1-3}$ alkoxy, $C_{1-3}$ haloalkoxy, $C_{3-4}$ cycloalkyl, or halo;

each $R^{3b}$ is independently H, —CN, $C_{1-3}$ alkyl, $C_{1-3}$ haloalkyl, $C_{1-3}$ alkoxy, $C_{1-3}$ haloalkoxy, $C_{3-4}$ cycloalkyl, or halo;

$Y^1$ is N, or $CR^{Y1}$; wherein $R^{Y1}$ is H, F, Cl, Br, CN, $C_{1-3}$ alkyl, $C_{1-3}$ haloalkyl, $C_{1-3}$ alkoxy, —$CH_2OCH_3$, or $C_{1-3}$ haloalkoxy;

$R^1$ is $C_{1-3}$ alkyl, $C_{3-10}$ cycloalkyl, $C_{6-12}$ aryl, heterocyclyl, or heteroaryl; wherein the cycloalkyl, heterocyclyl, heteroaryl, or aryl of $R^1$ is optionally substituted with 1 to 4 $Z^1$, which may be the same or different; the alkyl of $R^1$ is optionally substituted with one to four $R^{1a}$, which may be the same or different; each $R^{1a}$ is independently —CN, $C_{2-6}$ alkynyl, $C_{3-10}$ cycloalkyl, $C_{1-6}$ haloalkyl, $C_{6-12}$ aryl, heterocyclyl, or heteroaryl; wherein the cycloalkyl, aryl, heterocyclyl, or heteroaryl of Ra is optionally substituted with 1 to 4 $Z^7$, which may be the same or different;

$R^2$ is $C_{1-3}$ alkyl, $C_{3-10}$ cycloalkyl, $C_{6-12}$ aryl, heterocyclyl, heteroaryl, or —$NR^{2a}R^{2b}$; wherein the alkyl, cycloalkyl, aryl, heterocyclyl, or heteroaryl of $R^2$ is optionally substituted with 1 to 4 $Z^2$, which may be the same or different;

$R^{2a}$ is H, $C_{1-6}$ alkyl, $C_{1-6}$ haloalkyl, —$COR^{2a1}$, —$COOR^{2a1}$, —$CONR^{2a1}R^{2b1}$, —$SO_2$Ra, —$SO_2NR^{2a1}R^{2b1}$, $C_{6-10}$ aryl, $C_{3-10}$ cycloalkyl, heterocyclyl, or heteroaryl; wherein the alkyl, aryl, cycloalkyl, heterocyclyl, or heteroaryl of $R^{2a}$ is each optionally substituted with 1 to 4 $Z^3$, which may be the same or different, $R^{2b}$ is H, $C_{1-6}$ alkyl, $C_{1-6}$ haloalkyl, $C_{6-10}$ aryl, $C_{3-10}$ cycloalkyl, heterocyclyl, or heteroaryl; wherein the alkyl, aryl, cycloalkyl, heterocyclyl, or heteroaryl of $R^{2b}$ is each optionally substituted with 1 to 4 $Z^4$, which may be the same or different, or $R^{2a}$ and $R^{2b}$ together with the nitrogen to which they are attached form a heterocyclyl or heteroaryl, wherein the heterocyclyl or heteroaryl formed from $R^{2a}$ and $R^{2b}$ together with the nitrogen to which they are attached is optionally substituted with 1 to 4 $Z^5$, which may be the same or different; wherein the heterocyclyl formed from $R^{2a}$ and $R^{2b}$ is 3 to 10 membered heterocyclyl having 0 to 3 additional heteroatoms each independently N, O, or S; wherein the heteroaryl formed from $R^{2a}$ and $R^{2b}$ is 3 to 10 membered heteroaryl having 0 to 3 additional heteroatoms each independently N, O, or S;

or $R^1$ and $R^2$ together with the N to which they are attached form a heterocyclyl; wherein the heterocyclyl formed from $R^1$ and $R^2$ together with the N to which they are attached is optionally substituted with one to four $Z^6$, which may be the same or different, wherein the heterocyclyl formed from $R^1$ and $R^2$ is 3 to 20 membered heterocyclyl having 0 to 3 additional heteroatoms each independently N, O, or S;

each $Z^1$, $Z^2$, $Z^3$, $Z^4$, $Z^5$, $Z^6$, or $Z^7$ is independently $C_{1-9}$ alkyl, $C_{1-8}$ haloalkyl, $C_{1-6}$ alkoxy, $C_{1-6}$ haloalkoxy, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$) N($R^{12a}$)($R^{12b}$), —N($R^{12a}$)$_2$($R^{12b}$)+, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —$NR^{12a}$S(O)$_2$N($R^{12b}$)($R^{12c}$), $NR^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —$SF_5$, —S(O)$R^{12a}$, —S(O)(NH)$R^{12a}$, —S(O)$_2R^{12a}$, —S(O)$_2$N($R^{12a}$)($R^{12b}$), or —S(O)($NR^{12a}$)$R^{12b}$; wherein the alkyl, haloalkyl, alkenyl, alkynyl, cycloalkyl, heterocyclyl, aryl, or heteroaryl of each $Z^1$, $Z^2$, $Z^3$, $Z^4$, $Z^5$, $Z^6$, or $Z^7$ is each optionally substituted with 1 to 4 $Z^{1a}$, which may be the same or different;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)+, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$—S(O)$R^{12a}$, —S(O)(NH)$R^{12a}$, —S(O)$_2R^{12a}$, —S(O)$_2$N($R^{12a}$)($R^{12b}$), or —S(O)($NR^{12a}$)$R^{12b}$; wherein the alkyl, haloalkyl, alkenyl, alkynyl, cycloalkyl, heterocyclyl, aryl, or heteroaryl of $Z^{1a}$ is each optionally substituted with 1 to 4 $Z^{1b}$, which may be the same or different;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; wherein the alkyl, cycloalkyl, heterocyclyl, aryl, or heteroaryl of $Z^{1b}$ is optionally substituted with one to three $C_{1-9}$ alkyl, $C_{1-8}$ haloalkyl, halogen, —OH, —NH$_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O (aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{2a1}$, $R^{2b1}$, $R^{12a}$, $R^{12b}$, or $R^{12c}$ is independently H, $C_{1-6}$ alkyl, $C_{3-10}$ cycloalkyl, heterocyclyl, $C_{6-10}$ aryl, or heteroaryl; wherein the alkyl, cycloalkyl, heterocyclyl, aryl, or heteroaryl of each of $R^{2a}$, $R^{2b1}$, $R^{12a}$, $R^{12b}$, or $R^{12c}$ is each optionally substituted 1 to 4 $Z^{1b}$, which may be the same or different;

wherein each heteroaryl of the compound of Formula (I) unless otherwise specified is 5 to 14 membered heteroaryl having one to four heteroatoms each independently N, O, or S;

wherein each heterocyclyl of the compound of Formula (I) unless otherwise specified is 3 to 20 membered heterocyclyl having one to four heteroatoms each independently N, O or S.

Embodiment 2. The compound of embodiment 1, or a pharmaceutically acceptable salt thereof, having the structure of Formula (Ia)

(Ia)

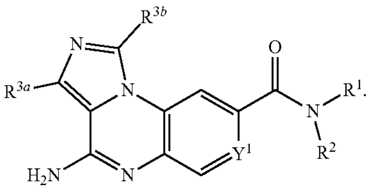

Embodiment 3. The compound of embodiment 1, or a pharmaceutically acceptable salt thereof, having the structure of Formula (Ib)

(Ib)

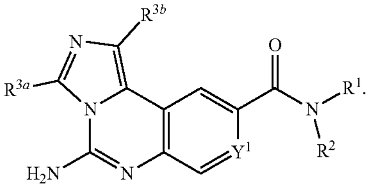

Embodiment 4. The compound of any one of embodiments 1-3, or a pharmaceutically acceptable salt thereof, wherein $R^{3a}$ is H, $CH_3$, F, or Cl.

Embodiment 5. The compound of any one of embodiments 1-3, or a pharmaceutically acceptable salt thereof, wherein $R^{3a}$ is $CH_3$.

Embodiment 6. The compound of any one of embodiments 1-3, or a pharmaceutically acceptable salt thereof, wherein $R^{3a}$ is H.

Embodiment 7. The compound of any one of embodiments 1-6, or a pharmaceutically acceptable salt thereof, wherein $R^{3b}$ is H, $CH_3$, F, Cl, $OCH_3$, $CF_2H$, or $CF_3$.

Embodiment 8. The compound of any one of embodiments 1-6, or a pharmaceutically acceptable salt thereof, wherein $R^{3b}$ is $CH_3$.

Embodiment 9. The compound of any one of embodiments 1-6, or a pharmaceutically acceptable salt thereof, wherein $R^{3b}$ is H.

Embodiment 10. The compound of any one of embodiments 1-9, or a pharmaceutically acceptable salt thereof, wherein $Y^1$ is N.

Embodiment 11. The compound of any one of embodiments 1-9, or a pharmaceutically acceptable salt thereof, wherein $Y^1$ is $CR^{Y1}$; $R^{Y1}$ is H, $CH_3$, F, Cl, or CN.

Embodiment 12. The compound of any one of embodiments 1-9, or a pharmaceutically acceptable salt thereof, wherein $Y^1$ is $CR^{Y1}$; $R^{Y1}$ is H, $CH_3$, or F.

Embodiment 13. The compound of any one of embodiments 1-9, or a pharmaceutically acceptable salt thereof, wherein $Y^1$ is —CF.

Embodiment 14. The compound of any one of embodiments 1-9, or a pharmaceutically acceptable salt thereof, wherein $Y^1$ is —CH.

Embodiment 15. The compound of any one of embodiments 1-14, or a pharmaceutically acceptable salt thereof, wherein $R^1$ is $C_{1-3}$ alkyl optionally substituted with 1 to 3 $R^{1a}$;

each $R^{1a}$ is independently —CN, OH, $C_{2-6}$ alkynyl, $C_{3-10}$ cycloalkyl, $C_{1-6}$ haloalkyl, $C_{1-6}$ alkoxy, $C_{6-12}$ aryl, 3 to 10 membered heterocyclyl, or 5 to 10 membered heteroaryl; the cycloalkyl, aryl, heterocyclyl, or heteroaryl of $R^{1a}$ is optionally substituted with 1 to 4 $Z^7$, which may be the same or different;

the heteroaryl of $R^{1a}$ is a heteroaryl having one to three heteroatoms each independently N, O, or S; and the heterocyclyl $R^{1a}$ is a heterocyclyl having one to three heteroatoms each independently N, O, or S.

Embodiment 16. The compound of any one of embodiments 1-15, or a pharmaceutically acceptable salt thereof, wherein $R^1$ is $C_{1-3}$ alkyl optionally substituted with $R^{1a}$, $R^{1a}$ is $C_{6-12}$ aryl, 3 to 16 membered heterocyclyl, or 5 to 10 membered heteroaryl, the aryl, heterocyclyl, or heteroaryl of $R^{1a}$ is optionally substituted with 1 to 4 $Z^7$, which may be the same or different;

the heteroaryl of $R^{1a}$ is a heteroaryl having one to three heteroatoms each independently N, O, or S; and the heterocyclyl of $R^{1a}$ is a heterocyclyl having one to three heteroatoms each independently N, O or S.

Embodiment 17. The compound of any one of embodiments 1-16, or a pharmaceutically acceptable salt thereof, having the structure of Formula (Id)

(Ic)

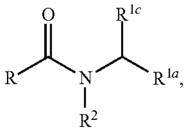

wherein $R^{1a}$ is $C_{6-12}$ aryl, 3 to 10 membered heterocyclyl, or 5 to 10 membered heteroaryl, the aryl, heterocyclyl, or heteroaryl of $R^{1a}$ is optionally substituted with 1 to 4 $Z^7$, which may be the same or different;

$R^{1c}$ is H, —$CH_3$, or cyclopropyl;

the heteroaryl of $R^{1a}$ is heteroaryl having one to three heteroatoms each independently N, O, or S; and the heterocyclyl of $R^{1a}$ is heterocyclyl having one to three heteroatoms each independently N, O or S.

Embodiment 18. The compound of embodiment 17, or a pharmaceutically acceptable salt thereof, wherein $R^{1c}$ is H.

Embodiment 19. The compound of any one of embodiments 1-18, or a pharmaceutically acceptable salt thereof, wherein $R^{1a}$ is phenyl, pyridyl, pyrimidinyl, pyrazinyl, pyridazinyl, benzofuranyl, benzothiazolyl, benzoimidazolyl, benzodioxolyl, or benzoxazolyl; each $R^{1a}$ is optionally substituted with 1 to 3 $Z^7$, which may be the same or different.

Embodiment 20. The compound of any one of embodiments 1-19, or a pharmaceutically acceptable salt thereof, wherein $R^{1a}$ is phenyl optionally substituted with 1 to 3 $Z^7$, which may be the same or different.

Embodiment 21. The compound of any one of embodiments 1-18, or a pharmaceutically acceptable salt thereof, wherein $R^{1a}$ is phenyl,

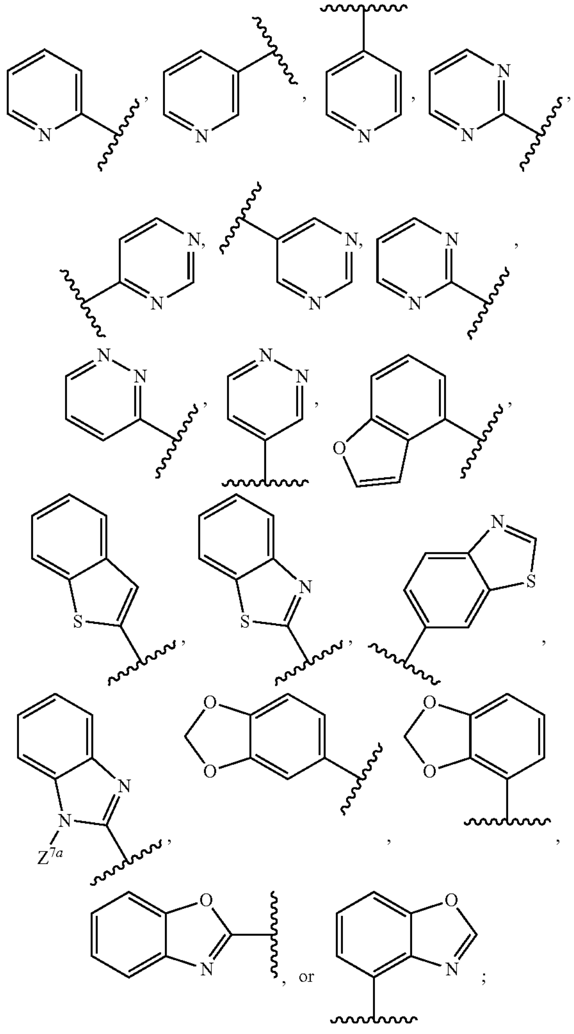

, or ;

each $R^{1a}$ is optionally substituted with 1 to 3 $Z^7$; and $Z^{7a}$ is H, $C_{1-6}$ alkyl, or $C_{1-6}$ haloalkyl.

Embodiment 22. The compound of any one of embodiments 1-21, or a pharmaceutically acceptable salt thereof, wherein each $Z^7$ is independently halo, —OH, $C_{1-6}$ alkyl, $C_{1-6}$ haloalkyl, $C_{3-6}$ cycloalkyl, $C_{2-6}$ alkynyl, CN, $C_{1-6}$ alkoxy, $C_{1-6}$ haloalkoxy, 5 to 10 membered heteroaryl, $C_{6-10}$ aryl, or 5 to 10 membered heterocyclyl; the alkyl, cycloalkyl, alkynyl, heteroaryl, aryl, or heterocyclyl of $Z^1$ is optionally substituted with 1 to 3

$Z^{1a}$, which may be the same or different; each $Z^{1a}$ is independently halo, —OH, $C_{1-6}$ alkyl, $C_{1-6}$ haloalkyl, $C_{3-6}$ cycloalkyl, $C_{2-6}$ alkynyl, CN, $C_{1-6}$ alkoxy, $C_{1-6}$ haloalkoxy, 5 to 10 membered heteroaryl, $C_{6-10}$ aryl, or 5 to 10 membered heterocyclyl, wherein each alkyl, cycloalkyl, alkynyl, heteroaryl, aryl, or heterocyclyl of $Z^{1a}$ is optionally substituted with one to three substituents selected from halo, —OH, $C_{1-6}$ alkyl, $C_{1-6}$haloalkyl, CN, $C_{1-6}$ alkoxy, $C_{1-6}$ haloalkoxy, and $C_{3-6}$ cycloalkyl.

Embodiment 23. The compound of any one of embodiments 1-21, or a pharmaceutically acceptable salt thereof, wherein each $Z^7$ is independently halo, CN, $C_{1-6}$ alkoxy, $C_{1-6}$ alkyl, $C_{1-6}$ haloalkyl, or 5 to 6 membered heteroaryl, wherein the heteroaryl of $Z^7$ is optionally substituted with one to four $Z^{1a}$, which may be the same or different; each $Z^{1a}$ is independently halo or $C_{1-6}$ haloalkyl.

Embodiment 24. The compound of any one of embodiments 1-23, or a pharmaceutically acceptable salt thereof, wherein each $Z^7$ is independently F, Cl, CN, —$CF_3$, —$OCHF_2$, —$CF_3$, —$OCH_3$,

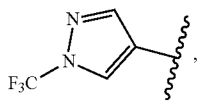,
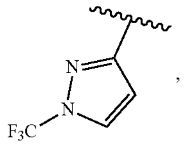,
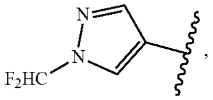,
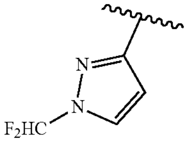,
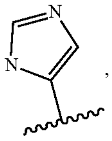, or 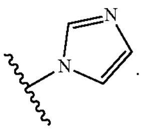.

Embodiment 25. The compound of any one of embodiments 1-21, or a pharmaceutically acceptable salt thereof, wherein each $Z^7$ is independently F, Cl, —$OCH_3$, CN, or phenyl.

Embodiment 26. The compound of any one of embodiments 1-14, or a pharmaceutically acceptable salt thereof, wherein $R^1$ is $C_{3-6}$ cycloalkyl, 3 to 16 membered heterocyclyl, 5 to 10 membered heteroaryl, or $C_{6-12}$ aryl; wherein the cycloalkyl, heterocyclyl, heteroaryl, or aryl of $R^1$ is optionally substituted with 1 to 4 $Z^1$, which may be the same or different.

Embodiment 27. The compound of any one of embodiments 1-14, or a pharmaceutically acceptable salt thereof, wherein $R^1$ is

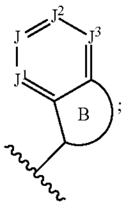;

each of J, $J^1$, $J^2$, and $J^3$, is independently N, or C optionally substituted with $Z^1$, provided that not more than two of J, $J^1$, $J^2$, and $J^3$ are N; and Ring B is $C_{5-8}$ cycloalkyl, or 5 to 8 membered heterocycloalkyl having 1 to 2 O, and optionally Ring B is substituted with 1 or 2 $Z^1$.

Embodiment 28. The compound of any one of embodiments 1-14, or a pharmaceutically acceptable salt thereof, wherein $R^1$ is 3 to 16 membered heterocyclyl optionally substituted with 1 to 4 $Z^1$, which may be the same or different.

Embodiment 29. The compound of any one of embodiments 1-14, 27, and 28, or a pharmaceutically acceptable salt thereof, wherein $R^1$ is a heterocyclyl selected from

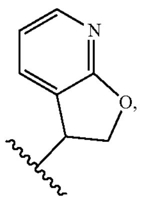,
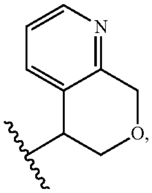,
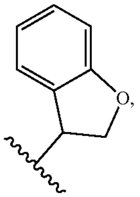, and
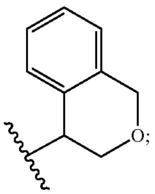;

the heterocyclyl of $R^1$ is optionally substituted with 1 to 4 $Z^1$, which may be the same or different.

Embodiment 30. The compound of any one of embodiments 1-14 and 26, or a pharmaceutically acceptable salt thereof, wherein $R^1$ is 5 to 10 membered heteroaryl optionally substituted with 1 to 4 $Z^1$.

Embodiment 31. The compound of any one of embodiments 1-14, 26, and 30, or a pharmaceutically acceptable salt thereof, wherein $R^1$ is a heteroaryl selected from

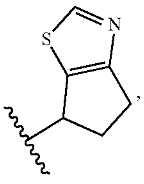,
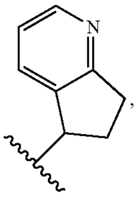,
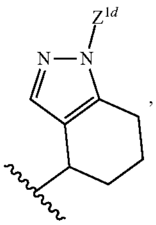, and
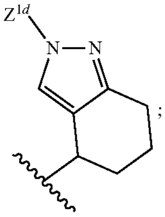;

the heteroaryl of $R^1$ is optionally substituted with 1 to 4 $Z^1$, which may be the same or different; and $Z^{1d}$ is H, $C_{1-6}$ alkyl, or $C_{1-6}$ haloalkyl.

Embodiment 32. The compound of any one of embodiments 1-14 and 26, or a pharmaceutically acceptable salt thereof, wherein $R^1$ is $C_{6-12}$ aryl optionally substituted with 1 to 4 $Z^1$, which may be the same or different.

Embodiment 33. The compound of any one of embodiments 1-14, 26, and 32, or a pharmaceutically acceptable salt thereof, wherein the aryl of $R^1$ is bicyclic or tricyclic.

Embodiment 34. The compound of any one of embodiments 1-14, 26, 32, and 33, or a pharmaceutically acceptable salt thereof, wherein $R^1$ is $C_{6-12}$ aryl selected from

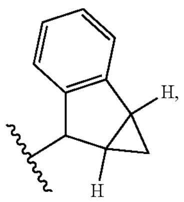 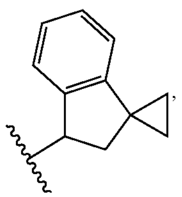, and 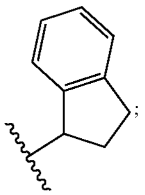;

the aryl of $R^1$ is optionally substituted with 1 to 4 $Z^1$, which may be the same or different.

Embodiment 35. The compound of any one of embodiments 1-14, 26, and 32-34, or a pharmaceutically acceptable salt thereof, wherein $R^1$ is

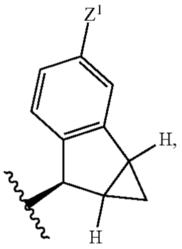 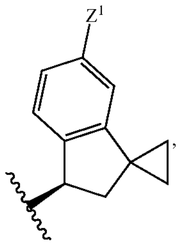, or

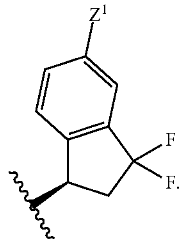

Embodiment 36. The compound of any one of embodiments 1-14 and 26-35, or a pharmaceutically acceptable salt thereof, wherein each $Z^1$ is independently halo, —OH, $C_{1-6}$ alkyl, $C_{1-6}$ haloalkyl, $C_{2-6}$ alkynyl, CN, $C_{1-6}$ alkoxy, $C_{1-6}$ haloalkoxy, $C_{3-6}$ cycloalkyl, 5 to 10 membered heteroaryl, $C_{6-10}$ aryl, or 4 to 10 membered heterocyclyl; the alkyl, alkynyl, cycloalkyl, heteroaryl, aryl, or heterocyclyl of $Z^1$ is optionally substituted with 1 to 3 $Z^{1a}$, each $Z^{1a}$ is independently halo, —OH, $C_{1-6}$ alkyl, $C_{1-6}$ haloalkyl, $C_{2-6}$ alkynyl, CN, $C_{1-6}$ alkoxy, $C_{1-6}$ haloalkoxy, $C_{3-6}$ cycloalkyl, 5 to 10 membered heteroaryl, $C_{6-10}$ aryl, or 5 to 10 membered heterocyclyl, wherein each alkyl, alkynyl, cycloalkyl, heteroaryl, aryl, or heterocyclyl of $Z^{1a}$ is optionally substituted with one to three substituents selected from halo, —OH, $C_{1-6}$ alkyl, $C_{1-6}$ haloalkyl, CN, $C_{1-6}$ alkoxy, $C_{1-6}$ haloalkoxy, and $C_{3-6}$ cycloalkyl.

Embodiment 37. The compound of any one of embodiments 1-14 and 26-36, or a pharmaceutically acceptable salt thereof, wherein each $Z^1$ is independently halo, —OH, $C_{1-6}$ alkyl, $C_{1-6}$ haloalkyl, $C_{2-6}$ alkynyl, CN, $C_{1-6}$ alkoxy, $C_{1-6}$ haloalkoxy, $C_{3-6}$ cycloalkyl, 5 to 6 membered heteroaryl, $C_{6-10}$ aryl, or 4 to 10 membered heterocyclyl;

the alkynyl of $Z^1$ is optionally substituted with 1 to 3 $Z^{1a}$; each $Z^{1a}$ is independently halo, —OH, $C_{1-6}$ haloalkyl, CN, $C_{1-6}$ alkoxy, $C_{1-6}$ haloalkoxy, 5 to 6 membered heteroaryl, $C_{3-6}$ cycloalkyl, phenyl, or 4 to 6 membered heterocyclyl; the heteroaryl, cycloalkyl, phenyl or heterocyclyl of is $Z^{1a}$ is optionally substituted with one to three substituents selected from halo, —OH, $C_{1-6}$ alkyl, $C_{1-6}$haloalkyl, CN, $C_{1-6}$ alkoxy, $C_{1-6}$ haloalkoxy, and $C_{3-6}$ cycloalkyl; and the cycloalkyl, heteroaryl, aryl, or heterocyclyl of $Z^1$ is optionally substituted with 1 to 3 substituents selected from halo, —OH, $C_{1-6}$ haloalkyl, CN, $C_{1-6}$ alkoxy, $C_{1-6}$ haloalkoxy, 5 to 6 membered heteroaryl, $C_{3-6}$ cycloalkyl, phenyl, and 4 to 6 membered heterocyclyl.

Embodiment 38. The compound of any one of embodiments 1-14 and 26-37, or a pharmaceutically acceptable salt thereof, wherein each $Z^1$ is independently halo, $C_{1-6}$ alkyl, $C_{1-6}$ haloalkyl, $C_{1-6}$ haloalkoxy, cyclopropyl, CN, —OH,

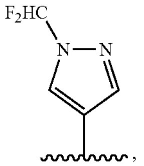, 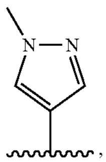, 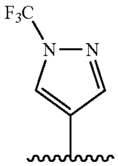, 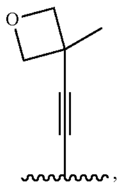,

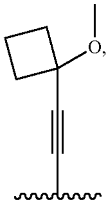 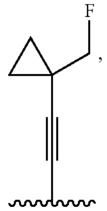 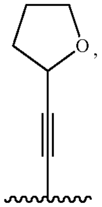 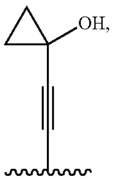

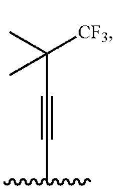 or 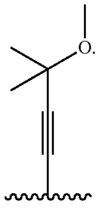

Embodiment 39. The compound of any one of embodiments 1-14 and 26-38, or a pharmaceutically acceptable salt thereof, wherein each $Z^1$ is independently $C_{1-3}$ alkyl, F, Cl, Br, —$CF_2H$, —$OCF_2H$, cyclopropyl, or —$CF_3$.

Embodiment 40. The compound of any one of embodiments 1-14, and 26-29, or a pharmaceutically acceptable salt thereof, wherein $R^1$ is

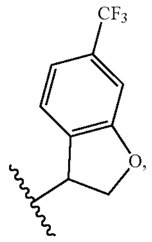 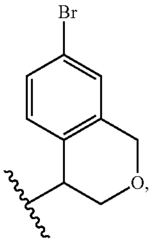 or 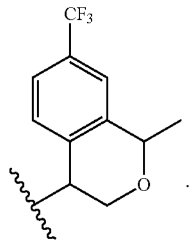

Embodiment 41. The compound of any one of embodiments 1-14, 26-29, and 40, or a pharmaceutically acceptable salt thereof, wherein $R^1$ is

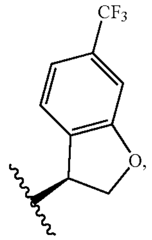 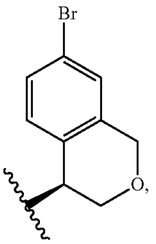 or 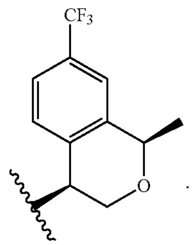

Embodiment 42. The compound of any one of embodiments 1-14, 26, 30, and 31, or a pharmaceutically acceptable salt thereof, wherein $R^1$ is

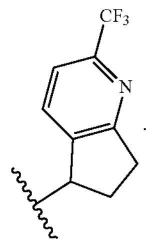 [SMILES: *C1CCc2nc(C(F)(F)F)ccc21]

Embodiment 43. The compound of any one of embodiments 1-15, 26, 30, 31, and 42, or a pharmaceutically acceptable salt thereof, wherein $R^1$ is

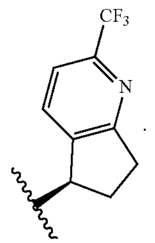 [SMILES: *[C@@H]1CCc2nc(C(F)(F)F)ccc21]

Embodiment 44. The compound of any one of embodiments 1-43, or a pharmaceutically acceptable salt thereof, wherein $R^2$ is $C_{1-3}$ alkyl, $C_{3-10}$ cycloalkyl, 3 to 10 membered heterocyclyl, 5 to 10 membered heteroaryl, $C_{6-12}$ aryl, or —$NR^{2a}R^{2b}$, wherein the alkyl, cycloalkyl, heterocyclyl, heteroaryl, aryl of $R^2$ is optionally substituted with 1 to 3 $Z^2$, which may be the same or different.

Embodiment 45. The compound of any one of embodiments 1-44, or a pharmaceutically acceptable salt thereof, wherein $R^2$ is —$NR^{2a}R^{2b}$;

$R^{2a}$ is H, $C_{1-6}$ alkyl, $C_{1-6}$ haloalkyl, —$COR^{2a1}$, —$COOR^{2a1}$, —$CONR^{2a1}R^{2b1}$, —$SO_2R^{2a1}$, —$SO_2NR^{2a1}R^{2b1}$, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^{2a}$ is each optionally substituted with one to four $Z^3$, which may be the same or different, and $R^{2b}$ is H, $C_{1-6}$ alkyl, $C_{1-6}$ haloalkyl, $C_{6-10}$ aryl, $C_{3-10}$ cycloalkyl, 3 to 10 membered heterocyclyl, or 5 to 10 membered heteroaryl; wherein the alkyl, aryl, cycloalkyl, heterocyclyl, or heteroaryl of $R^4$ is each optionally substituted with one to four $Z^4$, which may be the same or different;

or $R^{2a}$ and $R^{2b}$ together with the nitrogen to which they are attached form a 3 to 10 membered heterocyclyl or heteroaryl; wherein the heterocyclyl or heteroaryl formed from $R^{2a}$ and $R^{2b}$ is optionally substituted with one to four $Z^5$, which may be the same or different.

Embodiment 46. The compound of any one of embodiments 1-45, or a pharmaceutically acceptable salt thereof, wherein $R^{2a}$ is —$COR^{2a1}$ or —$COOR^{2a1}$; $R^{2a1}$ is $C_{1-6}$ alkyl, $C_{1-6}$ haloalkyl, or $C_{3-6}$ cycloalkyl; and $R^{2b}$ is $C_{1-6}$ alkyl or $C_{1-6}$ haloalkyl;

or $R^{2a}$ and $R^{2b}$ together with the nitrogen to which they are attached form a 3 to 8 membered heterocyclyl; wherein the heterocyclyl formed from $R^{2a}$ and $R^{2b}$ is optionally substituted with one to three $Z^5$, which may be the same or different; each $Z^5$ is independently oxo, halo, $C_{1-6}$ alkyl or $C_{1-6}$ haloalkyl.

Embodiment 47. The compound of any one of embodiments 1-46, or a pharmaceutically acceptable salt thereof, wherein $R^2$ is

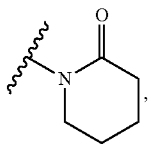, 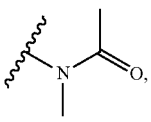 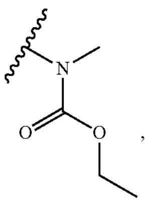, or

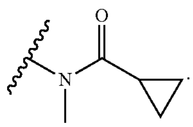

Embodiment 48. The compound of any one of embodiments 1-44, or a pharmaceutically acceptable salt thereof, wherein $R^2$ is $C_{1-3}$ alkyl, $C_{3-10}$ cycloalkyl, 3 to 10 membered heterocyclyl, 5 to 10 membered heteroaryl, or $C_{6-12}$ aryl, wherein the alkyl, cycloalkyl, heterocyclyl, heteroaryl, aryl of $R^2$ is optionally substituted with 1 to 3 $Z^2$, which may be the same or different, wherein each $Z^2$ is independently —OH, CN, halo, $C_{1-6}$ alkyl, $C_{1-6}$ haloalkyl, $C_{2-6}$ alkynyl, CN, $C_{1-6}$ alkoxy, or $C_{1-6}$ haloalkoxy, wherein $C_{1-6}$ alkyl of $Z^2$ is optionally substituted with one to three substituents independently selected from —OH and halo.

Embodiment 49. The compound of any one of embodiments 1-44, or a pharmaceutically acceptable salt thereof, wherein $R^2$ is $C_2H_5$, isopropyl, bicyclo[1.1.1]pentanyl, $—CH_2CHF_2$, $—CH_2CF_3$, cyclopropyl, cyclobutyl, oxetanyl, or $CH_3$;

$CH_3$ of $R^2$ is optionally substituted with phenyl or 5 to 6 membered heteroaryl; and cyclopropyl or cyclobutyl of $R^2$ is optionally substituted with one to three substituents independently selected from halo, —OH and $—CH_2OH$.

Embodiment 50. The compound of any one of embodiments 1-44, 48, and 49, or a pharmaceutically acceptable salt thereof, wherein $R^2$ is $CD_3$.

Embodiment 51. The compound of any one of embodiments 1-44 and 48, or a pharmaceutically acceptable salt thereof, wherein $R^2$ is 5 or 6 membered heteroaryl optionally substituted with 1 to 3 $Z^2$, which may be the same or different;

each $Z^2$ is independently halo or $C_{1-3}$ alkyl; and the heteroaryl of $R^2$ is a heteroaryl having one to three heteroatoms independently N, O, or S.

Embodiment 52. The compound of any one of embodiments 1-44 and 48, or a pharmaceutically acceptable salt thereof, wherein $R^2$ is 5 or 6 membered heteroaryl optionally substituted with 1 to 3 $Z^2$, which may be the same or different;

each $Z^2$ is independently halo or $C_{1-3}$ alkyl; and the heteroaryl of $R^2$ is a heteroaryl having one to two heteroatoms independently N or O.

Embodiment 53. The compound of any one of embodiments 1-44 and 48, or a pharmaceutically acceptable salt thereof, wherein $R^2$ is 5 membered heteroaryl optionally substituted with 1 to 2 $Z^2$, which may be the same or different;

each $Z^2$ is independently halo or $C_{1-3}$ alkyl; and the heteroaryl of $R^2$ is a heteroaryl having one to two N.

Embodiment 54. The compound of any one of embodiments 1-14, or a pharmaceutically acceptable salt thereof, wherein $R^1$ and $R^2$ together with the N to which they are attached form a 5 to 18 membered heterocyclyl; wherein the heterocyclyl formed from $R^1$ and $R^2$ together with the N to which they are attached is optionally substituted with 1 to 4 $Z^6$, which may be the same or different.

Embodiment 55. The compound of any one of embodiments 1-14 and 54, or a pharmaceutically acceptable salt thereof, wherein the heterocyclyl formed from $R^1$ and $R^2$ together with the N to which they are attached is monocycle, bicycle, tricycle, or tetracycle, wherein each of monocycle, bicycle, tricycle, or tetracycle formed from $R^1$ and $R^2$ is optionally substituted with 1 to 4 $Z^6$, which may be the same or different.

Embodiment 56. The compound of any one of embodiments 1-14, 54, and 55, or a pharmaceutically acceptable salt thereof, wherein $—NR^1R^2$ is

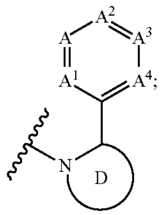

;

each of A, $A^1$, $A^2$, $A^3$, and $A^4$, is independently N, or C optionally substituted with $Z^{1a}$, provided that not more than two of A, $A^1$, $A^2$, $A^3$, and $A^4$ are N; and Ring D is a 5 to 10 membered heterocyclyl optionally additionally substituted with 1 to 3 $Z^6$, which may be the same or different; Ring D may optionally have an additional heteroatom selected from N, S, and O.

Embodiment 57. The compound of embodiment 56, or a pharmaceutically acceptable salt thereof, wherein $—NR^1R^2$ is

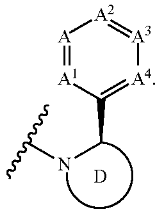

.

Embodiment 58. The compound of any one of embodiments 56 and 57, or a pharmaceutically acceptable salt thereof, wherein Ring D is a monocycle optionally additionally substituted with 1 to 2 $Z^6$, which may be the same or different.

Embodiment 59. The compound of any one of embodiments 56-58, or a pharmaceutically acceptable salt thereof, wherein Ring D is piperidinyl, piperazinyl, pyrrolidinyl or morpholinyl; wherein each of the piperidinyl, piperazinyl, pyrrolidinyl, and morpholinyl of Ring D is optionally additionally substituted with 1 or 2 $Z^6$.

Embodiment 60. The compound of any one of embodiments 56-58, or a pharmaceutically acceptable salt thereof, wherein Ring D is a bridged bicycle optionally additionally substituted with 1 to 2 $Z^6$, which may be the same or different.

Embodiment 61. The compound of any one of embodiments 56, 57, and 60, or a pharmaceutically acceptable salt thereof, wherein Ring D is a bridged morpholinyl optionally additionally substituted with 1 or 2 $Z^6$, which may be the same or different.

Embodiment 62. The compound of any one of embodiments 56 and 57, or a pharmaceutically acceptable salt thereof, wherein Ring D is a fused bicycle optionally additionally substituted with 1 or 2 $Z^6$, which may be the same or different.

Embodiment 63. The compound of any one of embodiments 1-14, 54, and 55, or a pharmaceutically acceptable salt thereof, wherein the heterocyclyl formed from $R^1$ and $R^2$ together with the N to which they are attached is tricycle, wherein any two joined rings of the tricycle may be fused or bridged, wherein the heterocyclyl formed from $R^1$ and $R^2$ may be optionally substituted with 1 to 4 $Z^6$.

Embodiment 64. The compound of any one of embodiments 1-14, 54, and 55, or a pharmaceutically acceptable salt thereof, wherein the heterocyclyl formed from $R^1$ and $R^2$ together with the N to which they are attached is tricycle, wherein any two joined rings of the tricycle may be fused or spiro, wherein the heterocyclyl formed from $R^1$ and $R^2$ may be optionally substituted with 1 to 4 $Z^6$.

Embodiment 65. The compound of any one of embodiments 1-14, 54, 55, and 63, or a pharmaceutically acceptable salt thereof, wherein —$NR^1R^2$ is

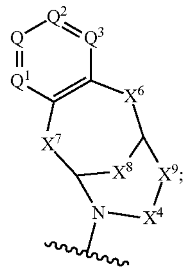

each of Q, $Q^1$, $Q^2$, and $Q^3$, is independently N, or C optionally substituted with $Z^6$, provided that not more than two of Q, $Q^1$, $Q^2$, and $Q^3$ are N;

$X^4$ is $CH_2$ optionally substituted with one or two $Z^6$;

$X^6$ is a bond, O, $CH_2$, $CH_2O$, $CH_2CH_2$, or $OCH_2$, wherein each of $CH_2$, $CH_2O$, $CH_2CH_2$, and $OCH_2$ of $X^6$ is optionally substituted with one or two $Z^6$;

$X^7$ is a bond or $CH_2$ optionally substituted with one or two $Z^6$;

$X^8$ is a bond, $CH_2$, or $CH_2O$, wherein each of $CH_2$ and $CH_2O$ of $X^8$ is optionally substituted with one or two $Z^6$; and $X^9$ is $CH_2$, $CH_2O$, or $CH_2CH_2$, wherein each of $CH_2$, $CH_2O$, and $CH_2CH_2$ of $X^9$ is optionally substituted with one or two $Z^6$.

Embodiment 66. The compound of any one of embodiments 1-14, 54, 55, and 63, or a pharmaceutically acceptable salt thereof, wherein —$NR^1R^2$ is

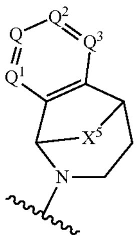

or

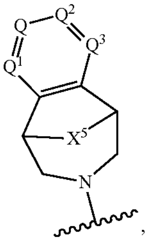

, wherein —$NR^1R^2$ is optionally substituted with 1 to 4 $Z^6$, which may be the same or different;

each of Q, $Q^1$, $Q^2$, and $Q^3$, is independently N, or C optionally substituted with $Z^6$, provided that not more than two of Q, $Q^1$, $Q^2$, and $Q^3$ are N; and $X^5$ is —$OCH_2$—, —$CH_2$—, —$CH_2CH_2$—, or —$CF_2$—.

Embodiment 67. The compound of any one of embodiments 1-14, 54, 55, and 63, or a pharmaceutically acceptable salt thereof, wherein —$NR^1R^2$ is a heterocyclyl of

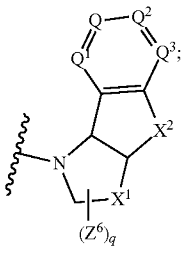

each of Q, $Q^1$, $Q^2$, and $Q^3$, is independently N, or C optionally substituted with $Z^6$, provided that not more than two of Q, $Q^1$, $Q^2$, and $Q^3$ are N;

$X^1$ is —$OCF_2$—, —$OCH_2$—, —$CH_2$—, —$CH_2CH_2$—, —$OCH_2CH_2$—, —$CF_2$—, or —$CH_2NR^{1b}$—; wherein $R^{1b}$ is $C_{1-6}$ alkyl, $C_{1-6}$ haloalkyl, oxetanyl, —C(O)—$R^{12a}$, —S(O)$R^{12a}$, or $C_{3-6}$ cycloalkyl;

$X^2$ is O, —$OCH_2$—, —$CF_2$—, or —$CH_2$—; and q is 0, 1, or 2.

Embodiment 68. The compound of any one of embodiments 1-14, 54, and 55, or a pharmaceutically acceptable salt thereof, wherein —$NR^1R^2$ is

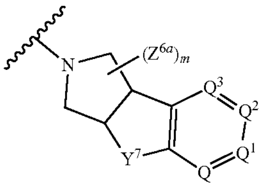

or

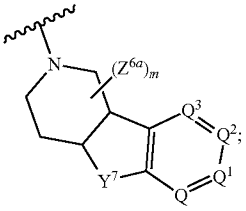

$Y^7$ is O, —$OCH_2$—, or —$CH_2CH_2$—; each of is —$OCH_2$— and —$CH_2CH_2$— of $Y^7$ is optionally substituted with one or two $Z^6$;

each of Q, $Q^1$, $Q^2$, and $Q^3$, is independently N, or C optionally substituted with $Z^6$, provided that not more than two of Q, $Q^1$, $Q^2$, and $Q^3$ are N;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and m is 0, 1, or 2.

Embodiment 69. The compound of any one of embodiments 1-14, 54, and 55, or a pharmaceutically acceptable salt thereof, wherein —$NR^1R^2$ is

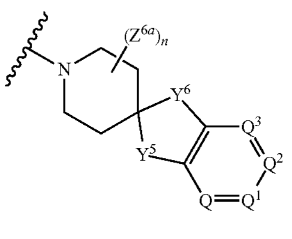

or

-continued

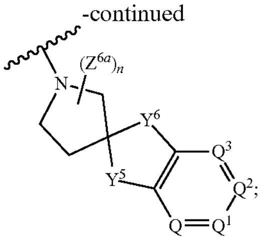

each of Q, $Q^1$, $Q^2$, and $Q^3$, is independently N, or C optionally substituted with $Z^6$, provided that not more than two of Q, $Q^1$, $Q^2$, and $Q^3$ are N;

$Y^5$ is O, $NR^{1d}$, $CH_2$, $CH_2CH_2$, $CH_2O$, $CONR^{1d}$, $CH_2NR^{1d}$, wherein each of $CH_2$, $CH_2CH_2$, and $CH_2O$ of $Y^5$ is optionally substituted with one or two $Z^6$;

$Y^6$ is a bond, O, $NR^{1d}$, $CH_2$, $CH_2CH_2$, $CH_2O$, $CONR^{1d}$, or $CH_2NR^{1d}$; wherein each of $CH_2$, $CH_2CH_2$, and $CH_2O$ of $Y^6$ is optionally substituted with one or two $Z^6$; and $R^{1d}$ is H, $C_{1-6}$ alkyl, or $C_{1-6}$ haloalkyl;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and n is 0, 1, or 2.

Embodiment 70. The compound of any one of embodiments 1-14, 54, and 55, or a pharmaceutically acceptable salt thereof, wherein —$NR^1R^2$ is

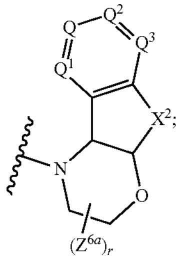

each of Q, $Q^1$, $Q^2$, and $Q^3$, is independently N, or C optionally substituted with $Z^6$, provided that not more than two of Q, $Q^1$, $Q^2$, and $Q^3$ are N; and $X^2$ is O, —$OCH_2$—, —$CF_2$—, or —$CH_2$—;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and r is 0, 1, or 2.

Embodiment 71. The compound of any one of embodiments 1-14, and 54-70, or a pharmaceutically acceptable salt thereof, wherein each $Z^6$ is independently $C_{1-6}$ alkyl, —OH, CN, halo, $C_{1-6}$ haloalkyl, $C_{1-6}$ alkoxy, $C_{1-6}$ haloalkoxy, $C_{2-6}$ alkynyl, $C_{3-15}$ cycloalkyl, 3-18 membered heterocyclyl, $C_{6-10}$ aryl, 5 to 10 membered heteroaryl, —C(O)—$R^{12a}$, —C(O)O—$R^{12a}$; wherein the alkyl, alkynyl, cycloalkyl, heterocyclyl, or heteroaryl is optionally substituted with one to four $Z^{1a}$, which may be the same or different;

each $Z^{1a}$ is independently —OH, CN, $C_{1-6}$ alkyl, halo, $C_{1-6}$ haloalkyl, $C_{1-6}$ alkoxy, $C_{1-6}$ haloalkoxy, $C_{3-10}$ cycloalkyl, 5-18 membered heterocyclyl, $C_{6-10}$ aryl, or 5 to 10 membered heteroaryl, wherein the cycloalkyl, heterocyclyl, aryl, or heteroaryl, is each optionally substituted with one to four $Z^{1b}$, which may be the same or different;

each $Z^{1b}$ is independently CN, —OH, $C_{1-6}$ alkyl, halo, $C_{1-6}$ haloalkyl, $C_{1-6}$ alkoxy, or $C_{1-6}$ haloalkoxy; and each $R^{12a}$ is independently H, $C_{1-6}$ alkyl, or $C_{3-10}$ cycloalkyl.

Embodiment 72. The compound of any one of embodiments 1-14, and 54-71, or a pharmaceutically acceptable salt thereof, wherein each $Z^6$ is independently —OH, CN, $C_{1-6}$ alkyl, halo, $C_{1-6}$ haloalkyl, $C_{1-6}$ alkoxy, $C_{1-6}$ haloalkoxy, phenyl, or 5 to 6 membered heteroaryl, wherein the phenyl or heteroaryl of $Z^6$ is optionally substituted with 1 to 3 $Z^{1a}$, which may be the same or different; each $Z^{1a}$ is independently halo or $C_{1-6}$ haloalkyl.

Embodiment 73. The compound of any one of embodiments 1-14, and 54-71, or a pharmaceutically acceptable salt thereof, wherein each $Z^6$ is independently $C_{1-3}$ alkyl, halo, $C_{1-3}$ haloalkyl, $C_{1-3}$ alkoxy, $C_{1-3}$ haloalkoxy, phenyl, or pyridyl, wherein the phenyl or pyridyl is optionally substituted with one to three substituents independently selected from halo and $C_{1-3}$ haloalkyl.

Embodiment 74. The compound of any one of embodiments 1-14, and 54-71, or a pharmaceutically acceptable salt thereof, wherein each $Z^6$ is independently —$CF_3$, F, Cl, —$OCHF_2$, or Br.

Embodiment 75. The compound of any one of embodiments 1-14, and 54-71, or a pharmaceutically acceptable salt thereof, wherein each $Z^6$ is independently $CF_3$ or Br.

Embodiment 76. The compound of any one of embodiments 1-14, 54, and 55, or a pharmaceutically acceptable salt thereof, wherein —$NR^1R^2$ is

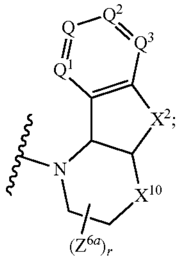

each of Q, $Q^1$, $Q^2$, and $Q^3$, is independently N, or C optionally substituted with $Z^6$, provided that not more than one of Q, $Q^1$, $Q^2$, and $Q^3$ is N; and $X^2$ is O or —$CH_2$—;

$X^{10}$ is O or —$CH_2$—;

each $Z^{6a}$ is independently $Z^6$, or two $Z^{6a}$ are attached to one carbon, and the two $Z^{6a}$ together with the carbon to which they attached form a $C_{3-5}$ cycloalkyl or 3-6 membered heterocyclyl, wherein the heterocyclyl formed from the two $Z^{6a}$ together with the carbon to which they attached has one to two heteroatoms each independently N, O or S; and r is 0, 1, or 2.

Embodiment 77. The compound of any one of embodiments 1-14, 54, 55, and 76, or a pharmaceutically acceptable salt thereof, wherein —$NR^1R^2$ is

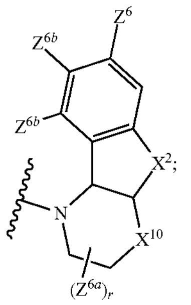

$X^2$ is O or —$CH_2$—;

$X^{10}$ is O or —$CH_2$—;

each $Z^{6b}$ is independently H or $Z^6$;

each $Z^{6a}$ is independently $Z^6$, or two $Z^{6a}$ are attached to one carbon, and the two $Z^{6a}$ together with the carbon to which they attached form a cyclopropyl; and r is 0, 1, or 2.

Embodiment 78. The compound of any one of embodiments 1-14, 54, 55, 76, and 77, or a pharmaceutically acceptable salt thereof, wherein —$NR^1R^2$ is

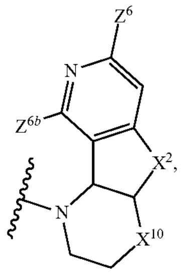
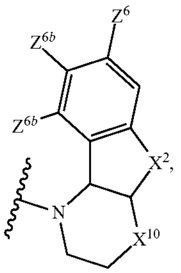
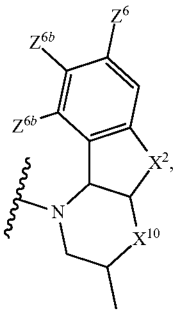
or

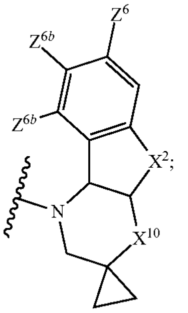

$X^2$ is O or —$CH_2$—;

$X^{10}$ is O or —$CH_2$—; and each $Z^{6b}$ is independently H or $Z^6$.

Embodiment 79. The compound of any one of embodiments 1-14, 54, 55, and 76-78, or a pharmaceutically acceptable salt thereof, wherein —$NR^1R^2$ is

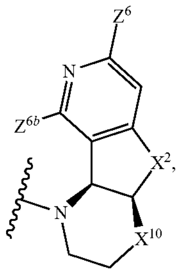
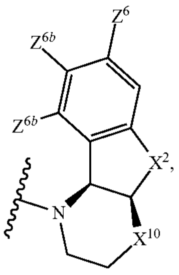
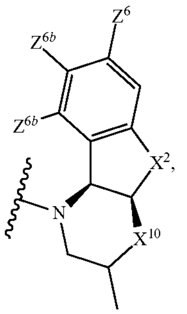
or

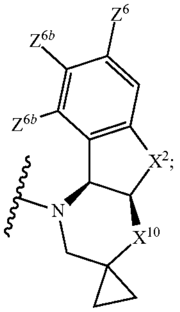

$X^2$ is O or —$CH_2$—;

$X^{10}$ is O or —$CH_2$—; and each $Z^{6b}$ is independently H or $Z^6$.

Embodiment 80. The compound of any one of embodiments 1-14, 54, 55, 76, and 77, or a pharmaceutically acceptable salt thereof, wherein —$NR^1R^2$ is

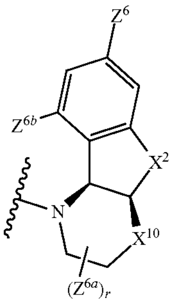
or
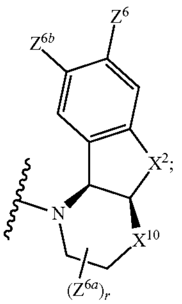

$X^2$ is O or —$CH_2$—;

$X^{10}$ is O or —$CH_2$—; and each $Z^{6b}$ is independently H or $Z^6$.

r is 0, 1, or 2.

Embodiment 81. The compound of any one of embodiments 1-14, 54-71, and 76-80, or a pharmaceutically acceptable salt thereof, wherein each $Z^6$ is independently F, $C_{1-3}$ alkyl, $C_{1-3}$ haloalkyl, $C_{1-3}$ alkoxy, or $C_{1-3}$ haloalkoxy.

Embodiment 82. The compound of any one of embodiments 1-14, 54-71, and 76-81, or a pharmaceutically acceptable salt thereof, wherein each $Z^6$ is independently F, —$CH_3$, —$CF_3$, —$C_2F_5$, or —$OCF_3$.

Embodiment 83. The compound of any one of embodiments 77-82, or a pharmaceutically acceptable salt thereof, wherein each $Z^{6b}$ is independently H or F.

Embodiment 84. The compound of any one of embodiments 77-82, or a pharmaceutically acceptable salt thereof, wherein at least one $Z^{6b}$ is F.

Embodiment 85. The compound of any one of embodiments 77-82, or a pharmaceutically acceptable salt thereof, wherein $Z^{6b}$ is H.

Embodiment 86. The compound of any one of embodiments 76-85, or a pharmaceutically acceptable salt thereof, wherein $X^2$ is O; and $X^{10}$ is $—CH_2—$.

Embodiment 87. The compound of any one of embodiments 76-85, or a pharmaceutically acceptable salt thereof, wherein $X^2$ is $—CH_2—$; and $X^{10}$ is O.

Embodiment 88. The compound of any one of embodiments 1, 2, 4, 6, 7, 9, 10, and 15-87, or a pharmaceutically acceptable salt thereof, wherein R is

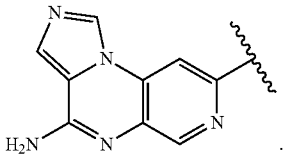

Embodiment 89. The compound of any one of embodiments 1, 2, 4, 6, 7, 9, 11-13, and 15-87, or a pharmaceutically acceptable salt thereof, wherein R is

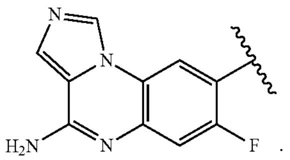 [SMILES: *c1cc2c(cc1F)nc(N)c1cncn12]

Embodiment 90. A compound disclosed herein, or a pharmaceutically acceptable salt thereof.

Pharmaceutical Compositions and Modes of Administration

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

In some embodiments, the pharmaceutical composition of the present disclosure may additionally comprise one or more other compounds as active ingredients like a prodrug compound or other enzyme inhibitors.

In some embodiments, the pharmaceutical composition of the present disclosure may comprise an additional therapeutic agent or therapeutic modality. In some embodiments, the additional therapeutic agent comprises one, two, three, or four additional therapeutic agents and/or therapeutic modalities. In some embodiments, the additional therapeutic agent or therapeutic modalities are selected from an immune checkpoint modulator, an antibody-drug conjugate (ADC), an antiapoptotic agent, a targeted anticancer therapeutic, a chemotherapeutic agent, surgery, or radiation therapy. In some embodiments, the immune checkpoint modulator is selected from an anti-PD-$(L)_1$ antibody, an anti-TIGIT antibody, an anti-CTLA4 antibody, an anti-CCR8 antibody, an anti-TREM1 antibody, an anti-TREM2 antibody, a CD47 inhibitor, a DGKα inhibitor, an HPK1 inhibitor, a FLT3 agonist, an adenosine pathway inhibitor, and a CAR-T cell therapy.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

In some embodiments, the compounds of the present disclosure may also be used as salts with various countercations to yield an orally available formulation.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

The disclosure further relates to the use of compounds disclosed herein for the treatment and/or prophylaxis of diseases and/or conditions through inhibiting PRMT5 by said compounds. The disclosure further relates to the use of compounds disclosed herein for the treatment and/or prophylaxis of diseases and/or conditions through inhibiting PRMT5 by said compounds. The disclosure further relates to the use of compounds disclosed herein for the treatment and/or prophylaxis of diseases and/or conditions through inhibiting PRMT5 in MTAP-null cells by said compounds. Further, the present disclosure relates to the use of said compounds for the preparation of a medicament for the treatment and/or prophylaxis of a chromosome 9p21 deletion or MTAP-null associated disease and/or condition through inhibiting PRMT5 in MTAP-null cells by said compounds. In some embodiments the chromosome 9p21 deletion or MTAP-null associated disease or condition is alleviated by inhibition of PRMT5 in MTAP-null cells.

Medicaments as referred to herein can be prepared by conventional processes, including the combination of a compound according to the present disclosure and a pharmaceutically acceptable carrier.

In some embodiments, provided herein is a method of treating and/or preventing a MTAP-null or chromosome 9p21 deletion associated disease or condition in a patient in need thereof, comprising administering to the patient a therapeutically effective amount of a compound of Formula (I), (Ia), (Ib), or (Ic), or pharmaceutically acceptable salt thereof, or a composition comprising a compound of Formula (I), (Ia), (Ib), or (Ic), or a pharmaceutically acceptable salt thereof.

In some embodiments, the chromosome 9p21 deletion or MTAP-null associated disease or condition includes a solid tumor in or arising from a tissue or organ, such as:

bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma);

lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors);

esophagus (e.g., Barrett's esophagus, dysplasia and adenocarcinoma);

gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus;

pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma);

gall bladder (e.g., carcinoma of the gallbladder and extrahepatic bile ducts, intrahepatic cholangiocarcinoma);

neuro-endocrine (e.g., adrenal cortical carcinoma, carcinoid tumors, phaeochromocytoma, pituitary adenomas);

thyroid (e.g., anaplastic (undifferentiated) carcinoma, medullary carcinoma, oncocytic tumors, papillary carcinoma, adenocarcinoma);

liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor);

kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma);

breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma;

peritoneum (e.g., mesothelioma; primary peritoneal cancer);

female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, Müllerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina;

male sex organ tissues, including prostate, testis (e.g., germ cell tumors, spermatocytic seminoma), penis;

bladder (e.g., squamous cell carcinoma, urothelial carcinoma, bladder urothelial carcinoma);

brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas (NHLs), indolent non-Hodgkin's lymphoma (iNHL), refractory iNHL, pituitary tumors;

eye (e.g., retinoma, retinoblastoma, ocular melanoma, posterior uveal melanoma, iris hamartoma);

head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal);

thymus (e.g., thymoma);

heart (e.g., cardiac myxoma);

lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma);

lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis);

central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumours (including without limitation neuroblastoma, ganglioneuroblastoma, ganglioneuroma), trisomy 19 ependymoma);

neuroendocrine tissues (e.g., paraganglionic system including adrenal medulla (pheochromocytomas) and extra-adrenal paraganglia ((extra-adrenal) paragangliomas);

skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, nonrhabdomyosarcoma soft tissue sarcoma (NRSTS), soft tissue leiomyosarcoma, undifferentiated sarcoma, well-differentiated liposarcoma.

In some embodiments, the chromosome 9p21 deletion or MTAP-null associated disease or condition is a cancer selected from lung cancer, urothelial cancer, pancreatic cancer, esophageal cancer, bladder cancer, melanoma, mature B-cell neoplasms, head and neck cancer, bile duct cancer, esophagus cancer, glioblastoma, stomach cancer, adrenal cancer, breast cancer, ovarian cancer, thymic epithelial tumor, liver cancer, renal cancer, colorectal cancer, prostate cancer, leukemia, and cervical cancer.

In some embodiments, the chromosome 9p21 deletion or MTAP-null associated disease or condition is a cancer is selected from ovarian, lung, lymphoid, glioblastoma, colon, melanoma, gastric, pancreatic, and bladder cancer.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing a chromosome 9p21 deletion or MTAP-null associated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combinations

In some embodiments, a compound of Formula (I), (Ia), (Ib), or (Ic), provided herein, or pharmaceutically acceptable salt thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula (I), (Ia), (Ib), or (Ic) provided herein, or pharmaceutically acceptable salt thereof, and one or more additional therapeutic agents. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments the one or more additional therapeutic agents include, e.g., an inhibitory immune checkpoint blocker or inhibitor, a stimulatory immune checkpoint stimulator, agonist or activator, a chemotherapeutic agent, an anti-cancer agent, a radiotherapeutic agent, an anti-neoplastic agent, an anti-proliferation agent, an anti-angiogenic agent, an anti-inflammatory agent, an immunotherapeutic agent, a therapeutic antigen-binding molecule (e.g., a mono- and multi-specific antibody, or fragment thereof, in any format, such as DART@, Duobody®, BiTE®, BiKE, TriKE, XmAb®, TandAb®, scFv, Fab, Fab derivative), a bi-specific antibody, a non-immunoglobulin antibody mimetic (e.g., including adnectin, affibody, affilin, affimer, affitin, alphabody, anticalin, peptide aptamer, armadillo repeat protein (ARM), atrimer, avimer, designed ankyrin repeat protein (DARPin®), fynomer, knottin, Kunitz domain peptide, monobody, and nanoCLAMPs), an antibody-drug conjugate (ADC), antibody-peptide conjugate), an oncolytic virus, a gene modifier or editor, a cell comprising a chimeric antigen receptor (CAR), e.g., including a T-cell immunotherapeutic agent, an NK-cell immunotherapeutic agent, or a macrophage immunotherapeutic agent, a cell comprising an engineered T-cell receptor (TCR-T), or any combination thereof.

Illustrative Targets

In some embodiments, the one or more additional therapeutic agents include, e.g., an inhibitor, agonist, antagonist, ligand, modulator, stimulator, blocker, activator or suppressor of a target (e.g., polypeptide or polynucleotide), such as: 2'-5'-oligoadenylate synthetase (OAS1; NCBI Gene ID: 4938); 5'-3' exoribonuclease 1 (XRN1; NCBI Gene ID: 54464); 5'-nucleotidase ecto (NT5E, CD73; NCBI Gene ID: 4907); ABL proto-oncogene 1, non-receptor tyrosine kinase (ABL1, BCR-ABL, c-ABL, v-ABL; NCBI Gene ID: 25); absent in melanoma 2 (AIM2; NCBI Gene ID: 9447); acetyl-CoA acyltransferase 2 (ACAA2; NCBI Gene ID: 10499); acid phosphatase 3 (ACP3; NCBI Gene ID: 55); adenosine deaminase (ADA, ADAl; NCBI Gene ID: 100); adenosine receptors (e.g., ADORA1 (A1), ADORA2A (A2a, A2AR), ADORA2B (A2b, A2BR), ADORA3 (A3); NCBI Gene IDs: 134, 135, 136, 137); AKT serine/threonine kinase 1 (AKT1, AKT, PKB; NCBI Gene ID: 207); alanyl aminopeptidase, membrane (ANPEP, CD13; NCBI Gene ID: 290); ALK receptor tyrosine kinase (ALK, CD242; NCBI Gene ID: 238); alpha fetoprotein (AFP; NCBI Gene ID: 174); amine oxidase copper containing (e.g., AOC1 (DAO1), AOC2, AOC3 (VAP1); NCBI Gene IDs: 26, 314, 8639); androgen receptor (AR; NCBI Gene ID: 367); angiopoietins (ANGPT1, ANGPT2; NCBI Gene IDs: 284, 285); angiotensin II receptor type 1 (AGTR1; NCBI Gene ID: 185); angiotensinogen (AGT; NCBI Gene ID: 183); apolipoprotein A1 (APOA1; NCBI Gene ID: 335); apoptosis inducing factor mitochondria associated 1 (AIFM1, AIF; NCBI Gene ID: 9131); arachidonate 5-lipoxygenase (ALOX5; NCBI Gene ID: 240); asparaginase (ASPG; NCBI Gene ID: 374569); asteroid homolog 1 (ASTE1; NCBI Gene ID: 28990); ATM serine/threonine kinase (ATM; NCBI Gene ID: 472); ATP binding cassette subfamily B member 1 (ABCB1, CD243, GP170; NCBI Gene ID: 5243); ATP-dependent Clp-protease (CLPP; NCBI Gene ID: 8192); ATR serine/threonine kinase (ATR; NCBI Gene ID: 545); AXL receptor tyrosine kinase (AXL; NCBI Gene ID: 558); B and T lymphocyte associated (BTLA, CD272; NCBI Gene ID: 151888); baculoviral IAP repeat containing proteins (BIRC2 (cIAP1), BIRC3 (cIAP2), XIAP (BIRC4, IAP3), BIRC5 (survivin); NCBI Gene IDs: 329, 330, 331, 332); basigin (Ok blood group) (BSG, CD147; NCBI Gene ID: 682); B-cell lymphoma 2 (BCL2; NCBI Gene ID: 596); BCL2 binding component 3 (BBC3, PUMA; NCBI Gene ID: 27113); BCL2 like (e.g., BCL2L1 (Bcl-x), BCL2L2 (BIM); Bcl-x; NCBI Gene IDs: 598, 10018); beta 3-adrenergic receptor (ADRB3; NCBI Gene ID: 155); bone gamma-carboxyglutamate protein (BGLAP; NCBI Gene ID: 632); bone morphogenetic protein-10 ligand (BMP10; NCBI Gene ID: 27302); bradykinin receptors (e.g., BDKRB1, BDKRB2; NCBI Gene IDs: 623, 624); B-RAF (BRAF; NCBI Gene ID: 273); breakpoint cluster region (BCR; NCBI Gene ID: 613); bromodomain and external domain (BET) bromodomain containing proteins (e.g., BRD2, BRD3, BRD4, BRDT; NCBI Gene IDs: 6046, 8019, 23476, 676); Bruton's tyrosine kinase (BTK; NCBI Gene ID: 695); cadherins (e.g., CDH3 (p-cadherin), CDH6 (k-cadherin); NCBI Gene IDs: 1001, 1004); cancer/testis antigens (e.g., CTAG1A, CTAG1B, CTAG2; NCBI Gene IDs: 1485, 30848, 246100); cannabinoid receptors (e.g., CNR1 (CB1), CNR2 (CB2); NCBI Gene IDs: 1268, 1269); carbohydrate sulfotransferase 15 (CHST15; NCBI Gene ID: 51363); carbonic anhydrases (e.g., CA1, CA2, CA3, CA4, CA5A, CA5B, CA6, CA7, CA8, CA9, CA10, CA11, CA12, CA13, CA14; NCBI Gene IDs: 759, 760, 761, 762, 763, 765, 766, 767, 768, 770, 771, 11238, 23632, 56934, 377677); carcinoembryonic antigen related cell adhesion molecules (e.g., CEACAM3 (CD66d), CEACAM5 (CD66e), CEACAM6 (CD66c); NCBI Gene IDs: 1048, 1084, 4680); casein kinases (e.g., CSNK1A1 (CK1), CSNK2A1 (CK2); NCBI Gene IDs: 1452, 1457); caspases (e.g., CASP3, CASP7, CASP8; NCBI Gene IDs: 836, 840, 841, 864); catenin beta 1 (CTNNB1; NCBI Gene ID: 1499); cathepsin G (CTSG; NCBI Gene ID: 1511); Cbl proto-oncogene B (CBLB, Cbl-b; NCBI Gene ID: 868); C-C motif chemokine ligand 21 (CCL21; NCBI Gene ID: 6366); C-C motif chemokine receptor 2 (CCR2; NCBI Gene ID: 729230); C-C motif chemokine receptors (e.g., CCR3 (CD193), CCR4 (CD194), CCR5 (CD195), CCR8 (CDw198); NCBI Gene IDs: 1232, 1233, 1234, 1237); CCAAT enhancer binding protein alpha (CEBPA, CEBP; NCBI Gene ID: 1050); cell adhesion molecule 1 (CADM1; NCBI Gene ID: 23705); cell division cycle 7 (CDC7; NCBI Gene ID: 8317); cellular communication network factor 2 (CCN2; NCBI Gene ID: 1490); cereblon (CRBN; NCBI Gene ID: 51185); checkpoint kinases (e.g., CHEK1 (CHK1), CHEK2 (CHK2); NCBI Gene IDs: 1111, 11200); cholecystokinin B receptor (CCKBR; NCBI Gene ID: 887); chorionic somatomammotropin hormone 1 (CSH1; NCBI Gene ID: 1442); claudins (e.g., CLDN6, CLDN18; NCBI Gene IDs: 9074, 51208); cluster of differentiation markers (e.g., CD1A, CD1C, CD1D, CD1E, CD2, CD3 alpha (TRA), CD beta (TRB), CD gamma (TRG), CD delta (TRD), CD4, CD8A, CD8B, CD19, CD20 (MS4A1), CD22, CD24, CD25 (IL2RA, TCGFR), CD28, CD33 (SIGLEC3), CD37, CD38, CD39 (ENTPD1), CD40 (TNFRSF5), CD44 (MIC4, PGP1), CD47 (IAP), CD48 (BLASTI), CD52, CD55 (DAF), CD58 (LFA3), CD74, CD79a, CD79b, CD80 (B7-1), CD84, CD86 (B7-2), CD96 (TACTILE), CD99 (MIC2), CD115 (CSF1R), CD116 (GMCSFR, CSF2RA), CD122 (IL2RB), CD123 (IL3RA), CD128 ($IL8R^1$), CD132 (IL2RG), CD135 (FLT3), CD137 (TNFRSF9, 4-1BB), CD142 (TF, TFA), CD152 (CTLA4), CD160, CD182 ($IL8R^2$), CD193 (CCR3), CD194 (CCR4), CD195 (CCR5), CD207, CD221 (IGF1R), CD222 (IGF2R), CD223 (LAG3), CD226 (DNAM1), CD244, CD247, CD248, CD276 (B7-H3), CD331 (FGFR1), CD332 (FGFR2), CD333 (FGFR3), CD334 (FGFR4); NCBI Gene IDs: 909, 911, 912, 913, 914, 919, 920, 923, 925, 926, 930, 931, 933, 940, 941, 942, 945, 951, 952, 953, 958,960, 961, 962, 965, 972, 973, 974, 1043, 1232, 1233, 1234, 1237, 1436, 1438, 1493, 1604, 2152, 2260, 2261, 2263, 2322, 3480, 3482, 3559, 3560, 3561, 3563, 3577, 3579, 3604, 3902, 4267, 6955, 6957, 6964, 6965, 8832, 10666, 11126, 50489, 51744, 80381, 100133941); clusterin (CLU; NCBI Gene ID: 1191); coagulation factors (e.g., F7, FXA,; NCBI Gene IDs: 2155, 2159); collagen type IV alpha chains (e.g., COL4A1, COL4A2, COL4A3, COL4A4, COL4A5; NCBI Gene IDs: 1282, 1284, 1285, 1286, 1287); collectin subfamily member 10 (COLEC10; NCBI Gene ID: 10584); colony stimulating factors (e.g., CSF1 (MCSF), CSF2 (GMCSF), CSF3 (GCSF); NCBI Gene IDs: 1435, 1437, 1440); complement factors (e.g., $C_3$, $C_5$; NCBI Gene IDs: 718, 727); COP9 signalosome subunit 5 (COPSS; NCBI Gene ID: 10987); C-type lectin domain family member (e.g., CLEC4C (CD303), CLEC9A (CD370), CLEC12A (CD371); CD371; NCBI Gene ID: 160364, 170482, 283420); C-X-C motif chemokine ligand 12 (CXCL12; NCBI Gene ID: 6387); C-X-C motif chemokine receptors (CXCR1 ($IL8R^1$, CD128), CXCR2 ($IL8R^2$, CD182), CXCR3 (CD182, CD183, IP-10R), CXCR4 (CD184); NCBI Gene ID: 2833, 3577, 3579, 7852); cyclin D1 (CCND1, BCL1; NCBI Gene ID: 595); cyclin dependent kinases (e.g., CDK1, CDK2, CDK3, CDK4, CDK5, CDK6, CDK7, CDK8, CDK9, CDK10, CDK12; NCBI Gene ID: 983, 1017, 1018, 1019, 1020, 1021, 1022, 1024, 1025, 8558, 51755); cyclin G1 (CCNG1; NCBI Gene ID: 900); cytochrome P450 family members (e.g., CYP2D6, CYP3A4, CYP11A1, CYP11B2, CYP17A1, CYP19A1, CYP51A1; NCBI Gene IDs: 1565, 1576, 1583, 1585, 1586, 1588, 1595); cytochrome P450 oxidoreductase (POR; NCBI Gene ID: 5447); cytokine inducible SH2 containing protein (CISH; NCBI Gene ID: 1154); cytotoxic T-lymphocyte associated protein 4 (CTLA4, CD152; NCBI Gene ID: 1493); DEAD-box helicases (e.g., DDX5, DDX6, DDX58; NCBI Gene IDs: 1655, 1656, 23586); delta like canonical Notch ligands (e.g., DLL3, DLL4; NCBI Gene IDs: 10683, 54567); diablo IAP-binding mitochondrial protein (DIABLO, SMAC; NCBI Gene ID: 56616); diacylglycerol kinases (e.g., DGKA, DGKZ; NCBI Gene IDs: 1606, 8525); dickkopf WNT signaling pathway inhibitors (e.g., DKK1, DKK3; NCBI Gene ID: 22943, 27122); dihydrofolate reductase (DHFR; NCBI Gene ID: 1719); dihydropyrimidine dehydrogenase (DPYD; NCBI Gene ID: 1806); dipeptidyl peptidase 4 (DPP4; NCBI Gene ID: 1803); discoidin domain receptor tyrosine kinases (e.g., DDR1 (CD167), DDR2; CD167; NCBI Gene ID: 780, 4921); DNA dependent protein kinase (PRKDC; NCBI Gene ID: 5591); DNA topoisomerases (e.g., TOP1, TOP2A, TOP2B, TOP3A, TOP3B; NCBI Gene ID: 7150, 7153, 7155, 7156, 8940); dopachrome tautomerase (DCT; NCBI Gene ID: 1638); dopamine receptor D2 (DRD2; NCBI Gene ID: 1318); DOT1 like histone lysine methyltransferase (DOT1L; NCBI Gene ID: 84444); ectonucleotide pyrophosphatase/phosphodiesterase 3 (ENPP3, CD203c; NCBI Gene ID: 5169); EMAP like 4 (EML4; NCBI Gene ID: 27436); endoglin (ENG; NCBI Gene ID: 2022); endoplasmic reticulum aminopeptidases (e.g., ERAP1, ERAP2; NCBI Gene ID: 51752, 64167); enhancer of zeste 2 polycomb repressive complex 2 subunit (EZH2; NCBI Gene ID: 2146); ephrin receptors (e.g., EPHA1, EPHA2EPHA3, EPHA4, EPHA5, EPHA7, EPHB4; NCBIGene ID:1969, 2041, 2042, 2043, 2044, 2045, 2050); ephrins (e.g., EFNA1, EFNA4, EFNB2; NCBI Gene ID: 1942, 1945, 1948); epidermal growth factor receptors (e.g., ERBB1 (HER1, EGFR), ERBB1 variant III (EGFRvIII), ERBB2 (HER2, NEU, CD340), ERBB3 (HER3), ERBB4 (HER4); NCBI Gene ID: 1956, 2064, 2065, 2066); epithelial cell adhesion molecule (EPCAM; NCBI Gene ID: 4072); epithelial mitogen (EPGN; NCBI Gene ID: 255324); eukaryotic translation elongation factors (e.g., EEF1A2, EEF2; NCBI Gene ID: 1917, 1938); eukaryotic translation initiation factors (e.g., EIF4A1, EIF5A; NCBI Gene ID: 1973, 1984); exportin-1 (XPO1; NCBI Gene ID: 7514); farnesoid X receptor (NR1H4, FXR; NCBI Gene ID: 9971); Fas ligand (FASLG, FASL, CD95L, CD178, TNFSF6; NCBI Gene ID: 356); fatty acid amide hydrolase (FAAH; NCBI Gene ID: 2166); fatty acid synthase (FASN; FAS; NCBI Gene ID: 2194); Fc fragment of Ig receptors (e.g., FCER1A, FCGRT, FCGR3A (CD16); NCBI Gene IDs: 2205, 2214, 2217); Fc receptor like 5 (FCRL5, CD307; NCBI Gene ID: 83416); fibroblast activation protein alpha (FAP; NCBI Gene ID: 2191); fibroblast growth factor receptors (e.g., FGFR1 (CD331), FGFR2 (CD332), FGFR3 (CD333), FGFR4 (CD334); NCBI Gene IDs: 2260, 2261, 2263, 2264); fibroblast growth factors (e.g., FGF1 (FGF alpha), FGF2 (FGF beta), FGF4, FGF5; NCBI Gene IDs: 2246, 2247, 2249, 2250); fibronectin 1 (FN1, MSF; NCBI Gene ID: 2335); fms related receptor tyrosine kinases (e.g., FLT1 (VEGFR1), FLT3 (STK1, CD135), FLT4 (VEGFR2); NCBI Gene IDs: 2321, 2322, 2324); fms related receptor tyrosine kinase 3 ligand (FLT3LG; NCBI Gene ID: 2323); focal adhesion kinase 2 (PTK2, FAK1; NCBI Gene ID: 5747); folate hydrolase 1 (FOLH1, PSMA; NCBI Gene ID: 2346); folate receptor 1 (FOLR1; NCBI Gene ID: 2348); forkhead box protein M1 (FOXM1; NCBI Gene ID: 2305); FURIN (FURIN, PACE; NCBI Gene ID: 5045); FYN tyrosine kinase (FYN, SYN; NCBI Gene ID: 2534); galectins (e.g., LGALS3, LGALS8 (PCTA1), LGALS9; NCBI Gene ID: 3958, 3964, 3965); glucocorticoid receptor ($NR3C_1$, GR; NCBI Gene ID: 2908); glucuronidase beta (GUSB; NCBI Gene ID: 2990); glutamate metabotropic receptor 1 (GRM1; NCBI Gene ID: 2911); glutaminase (GLS; NCBI Gene ID: 2744); glutathione S-transferase Pi (GSTP1; NCBI Gene ID: 2950); glycogen synthase kinase 3 beta (GSK3B; NCBI Gene ID: 2932); glypican 3 (GPC3; NCBI Gene ID: 2719); gonadotropin releasing hormone 1 (GNRH1; NCBI Gene ID: 2796); gonadotropin releasing hormone receptor (GNRHR; NCBI Gene ID: 2798); GPNMB glycoprotein nmb (GPNMB, osteoactivin; NCBI Gene ID: 10457); growth differentiation factor 2 (GDF2, BMP9; NCBI Gene ID: 2658); growth factor receptor-bound protein 2 (GRB2, ASH; NCBI Gene ID: 2885); guanylate cyclase 2C (GUCY2C, STAR, MECIL, MUCIL, NCBI Gene ID: 2984); H19 imprinted maternally expressed transcript (H19; NCBI Gene ID: 283120); HCK proto-oncogene, Src family tyrosine kinase (HCK; NCBI Gene ID: 3055); heat shock proteins (e.g., HSPA5 (HSP70, BIP, GRP78), HSPB1 (HSP27), HSP90B1 (GP96); NCBI Gene IDs: 3309, 3315, 7184); heme oxygenases (e.g., HMOX1 (HO1), HMOX2 (HO1); NCBI Gene ID: 3162, 3163); heparanase (HPSE; NCBI Gene ID: 10855); hepatitis A virus cellular receptor 2 (HAVCR2, TIM3, CD366; NCBI Gene ID: 84868); hepatocyte growth factor (HGF; NCBI Gene ID: 3082); HERV-H LTR-associating 2 (HHLA2, B7-H7; NCBI Gene ID: 11148); histamine receptor H2 (HRH2; NCBI Gene ID: 3274); histone deacetylases (e.g., HDAC1, HDAC7, HDAC9; NCBI Gene ID: 3065, 9734, 51564); HRas proto-oncogene, GTPase (HRAS; NCBI Gene ID: 3265); hypoxia-inducible factors (e.g., HIF1A, HIF2A (EPAS1); NCBI Gene IDs: 2034, 3091); I-Kappa-B kinase (IKK beta; NCBI Gene IDs: 3551, 3553); IKAROS family zinc fingers (IKZF1 (LYF1), IKZF3; NCBI Gene ID: 10320, 22806); immunoglobulin superfamily member 11 (IGSF11; NCBI Gene ID: 152404); indoleamine 2,3-dioxygenases (e.g., IDO1, ID02; NCBI Gene IDs: 3620, 169355); inducible T cell costimulator (ICOS, CD278; NCBI Gene ID: 29851); inducible T cell costimulator ligand (ICOSLG, B7-H2; NCBI Gene ID: 23308); insulin like growth factor receptors (e.g., IGF1R, IGF2R; NCBI Gene ID: 3480, 3482); insulin like growth factors (e.g., IGF1, IGF2; NCBI Gene IDs: 3479, 3481); insulin receptor (INSR, CD220; NCBI Gene ID: 3643); integrin subunits (e.g., ITGA5 (CD49e), ITGAV (CD51), ITGB1 (CD29), ITGB2 (CD18, LFA1, MAC1), ITGB7; NCBI Gene IDs: 3678, 3685, 3688, 3695, 3698); intercellular adhesion molecule 1 (ICAM1, CD54; NCBI Gene ID: 3383); interleukin 1 receptor associated kinase 4 (IRAK4; NCBI Gene ID: 51135); interleukin receptors (e.g., IL2RA (TCGFR, CD25), IL2RB (CD122), IL2RG (CD132), IL3RA, IL6R, IL13RA2 (CD213A2), IL22RA1; NCBI Gene IDs: 3598, 3559, 3560, 3561, 3563, 3570, 58985); interleukins (e.g., IL1A, IL1B, IL2, IL3, IL6 (HGF), IL7, IL8 (CXCL8), IL10 (TGIF), IL12A, IL12B, IL15, IL17A (CTLA8), IL18, IL23A, IL24, IL-29 (IFNL1); NCBI Gene IDs: 3552, 3553, 3558, 3562, 3565, 3569, 3574, 3586, 3592, 3593, 3600, 3605, 3606, 11009, 51561, 282618); isocitrate dehydrogenases ($NADP(+)_1$) (e.g., IDH1, IDH2; NCBI Gene IDs: 3417, 3418); Janus kinases (e.g., JAK1, JAK2, JAK3; NCBI Gene IDs: 3716, 3717, 3718); kallikrein related peptidase 3 (KLK3; NCBI Gene ID: 354); killer cell immunoglobulin like receptor, Ig domains and long cytoplasmic tails (e.g., KIR2DL1 (CD158A), KIR2DL2 (CD158B1), KIR2DL3 (CD158B), KIR2DL4 (CD158D), KIR2DL5A (CD158F), KIR2DL5B, KIR3DL1 (CD158E1), KIR3DL2 (CD158K), KIR3DP1 (CD158c), KIR2DS2 (CD158J); NCBI Gene IDs: 3802, 3803, 3804, 3805, 3811, 3812, 57292, 553128, 548594, 100132285); killer cell lectin like receptors (e.g., KLRC1 (CD159A), KLRC2 (CD159c), KLRC3, KLRRC4, KLRD1 (CD94), KLRG1, KLRK1 (NKG2D, CD314); NCBI Gene IDs: 3821, 3822, 3823, 3824, 8302, 10219, 22914); kinase insert domain receptor (KDR, CD309, VEGFR2; NCBI Gene ID: 3791); kinesin family member 11 (KIF11; NCBI Gene ID: 3832); KiSS-1 metastasis suppressor (KISS1; NCBI Gene ID: 3814); KIT proto-oncogene, receptor tyrosine kinase (KIT, C-KIT, CD117; NCBI Gene ID: 3815); KRAS proto-oncogene, GTPase (KRAS; NCBI Gene ID: 3845); lactotransferrin (LTF; NCBI Gene ID: 4057); LCK proto-oncogene, Src family tyrosine kinase (LCK; NCBI Gene ID: 3932); LDL receptor related protein 1 (LRP1, CD91, IGFBP3R; NCBI Gene ID: 4035); leucine rich repeat containing 15 (LRRC15; NCBI Gene ID: 131578); leukocyte immunoglobulin like receptors (e.g., LILRB1 (ILT2, CD85J), LILRB2 (ILT4, CD85D); NCBI Gene ID: 10288, 10859); leukotriene A4 hydrolase (LTA4H; NCBI Gene ID: 4048); linker for activation of T-cells (LAT; NCBI Gene ID: 27040); luteinizing hormone/choriogonadotropin receptor (LHCGR; NCBI Gene ID: 3973); LY6/PLAUR domain containing 3 (LYPD3; NCBI Gene ID: 27076); lymphocyte activating 3 (LAG3; CD223; NCBI Gene ID: 3902); lymphocyte antigens (e.g., LY9 (CD229), LY75 (CD205); NCBI Gene IDs: 4063, 17076); LYN proto-oncogene, Src family tyrosine kinase (LYN; NCBI Gene ID: 4067); lypmphocyte cytosolic protein 2 (LCP2; NCBI Gene ID: 3937); lysine demethylase 1A (KDM1A; NCBI Gene ID: 23028); lysophosphatidic acid receptor 1 (LPAR1, EDG2, LPA1, GPR26; NCBI Gene ID: 1902); lysyl oxidase (LOX; NCBI Gene ID: 4015); lysyl oxidase like 2 (LOXL2; NCBI Gene ID: 4017); macrophage migration inhibitory factor (MIF, GIF; NCBI Gene ID: 4282); macrophage stimulating 1 receptor (MST1R, CD136; NCBI Gene ID: 4486); MAGE family members (e.g., MAGEA1, MAGEA2, MAGEA2B, MAGEA3, MAGEA4, MAGEA5, MAGEA6, MAGEA10, MAGEA11, MAGEC1, MAGEC2, MAGED1, MAGED2; NCBI Gene IDs: 4100, 4101, 4102, 4103, 4104, 4105, 4109, 4110, 9500, 9947, 10916, 51438, 266740); major histocompatibility complexes (e.g., HLA-A, HLA-E, HLA-F, HLA-G; NCBI Gene IDs: 3105, 3133, 3134, 3135); major vault protein (MVP, VAULTI; NCBI Gene ID: 9961); MALT1 paracaspase (MALT1; NCBI Gene ID: 10892); MAPK activated protein kinase 2 (MAPKAPK2; NCBI Gene ID: 9261); MAPK interacting serine/threonine kinases (e.g., MKNK1, MKNK2; NCBI Gene IDs: 2872, 8569); matrix metallopeptidases (e.g., MMP1, MMP2, MMP3, MMP7, MMP8, MMP9, MMP10, MMP11, MMP12, MMP13, MMP14, MMP15, MMP16, MMP17, MMP19, MMP20, MMP21, MMP24, MMP25, MMP26, MMP27, MMP28; NCBI Gene IDs: 4312, 4313, 4314, 4316, 4317, 4318, 4319, 4320, 4321, 4322, 4323, 4324, 4325, 4326, 4327, 9313, 10893, 56547, 64066, 64386, 79148, 118856); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; BMFS6; NCBI Gene ID: 4194); mechanistic target of rapamycin kinase (MTOR, FRAP1; NCBI Gene ID: 2475); melan-A (MLANA; NCBI Gene ID: 2315); melanocortin receptors (MC1R, MC2R; NCBI Gene IDs: 4157, 4148); MER proto-oncogene, tyrosine kinase (MERTK; NCBI Gene ID: 10461); mesothelin (MSLN; NCBI Gene ID: 10232); MET proto-oncogene, receptor tyrosine kinase (MET, c-Met, HGFR; NCBI Gene ID: 4233); methionyl aminopeptidase 2 (METAP2, MAP2; NCBI Gene ID: 10988); MHC class I polypeptide-related sequences (e.g., MICA, MICB; NCBI Gene IDs: 4277, 100507436); mitogen activated protein kinases (e.g., MAPK1 (ERK2), MAPK3 (ERK1), MAPK8 (JNK1), MAPK9 (JNK2), MAPK10 (JNK3), MAPK11 ($p^{38}$ beta), MAPK12; NCBI Gene IDs: 5594, 5595, 5599, 5600, 5601, 5602, 819251); mitogen-activated protein kinase kinase kinases (e.g., MAP3K5 (ASK1), MAP3K8 (TPL2, AURA2); NCBI Gene IDs: 4217, 1326); mitogen-activated protein kinase kinase kinase kinase 1 (MAP4K1, HPK1; NCBI Gene ID: 11184); mitogen-activated protein kinase kinases (e.g., MAP2K1 (MEK1), MAP2K2 (MEK2), MAP2K7 (MEK7); NCBI Gene IDs: 5604, 5605, 5609); MPL proto-oncogene, thrombopoietin receptor (MPL; NCBI Gene ID: 4352); mucins (e.g., MUC1 (including splice variants thereof (e.g., including MUC1/A, C, D, X, Y, Z and REP)), MUC5AC, MUC16 (CA125); NCBI Gene IDs: 4582, 4586, 94025); MYC proto-oncogene, bHLH transcription factor (MYC; NCBI Gene ID: 4609); myostatin (MSTN, GDF8; NCBI Gene ID: 2660); myristoylated alanine rich protein kinase C substrate (MARCKS; NCBI Gene ID: 4082); natriuretic peptide receptor 3 (NPR3; NCBI Gene ID: 4883); natural killer cell cytotoxicity receptor 3 ligand 1 (NCR3LG1, B7-H6; NCBI Gene ID: 374383); necdin, MAGE family member (NDN; NCBI Gene ID: 4692); nectin cell adhesion molecules (e.g., NECTIN2 (CD112, PVRL2), NECTIN4 (PVRL4); NCBI Gene IDs: 5819, 81607); neural cell adhesion molecule 1 (NCAM1, CD56; NCBI Gene ID: 4684); neuropilins (e.g., NRP1 (CD304, VEGF165R), NRP2 ($VEGF165R^2$); NCBI Gene IDs: 8828, 8829); neurotrophic receptor tyrosine kinases (e.g., NTRK1 (TRKA), NTRK2 (TRKB), NTRK3 (TRKC); NCBI Gene IDs: 4914, 4915, 4916); NFKB activating protein (NKAP; NCBI Gene ID: 79576); NIMA related kinase 9 (NEK9; NCBI Gene ID: 91754); NLR family pyrin domain containing 3 (NLRP3, NALP3; NCBI Gene ID: 114548); notch receptors (e.g., NOTCH1, NOTCH2, NOTCH3, NOTCH4; NCBI Gene IDs: 4851, 4853, 4854, 4855); NRAS proto-oncogene, GTPase (NRAS; NCBI Gene ID: 4893); nuclear factor kappa B (NFKB1, NFKB2; NCBI Gene IDs: 4790, 4791); nuclear factor, erythroid 2 like 2 (NFE2L2; NRF2; NCBI Gene ID: 4780); nuclear receptor subfamily 4 group A member 1 (NR4A1; NCBI Gene ID: 3164); nucleolin (NCL; NCBI Gene ID: 4691); nucleophosmin 1 (NPM1; NCBI Gene ID: 4869); nucleotide binding oligomerization domain containing 2 (NOD2; NCBI Gene ID: 64127); nudix hydrolase 1 (NUDT1; NCBI Gene ID: 4521); O-6-methylguanine-DNA methyltransferase (MGMT; NCBI Gene ID: 4255); opioid receptor delta 1 (OPRD1; NCBI Gene ID: 4985); ornithine decarboxylase 1 (ODC1; NCBI Gene ID: 4953); oxoglutarate dehydrogenase (OGDH; NCBI Gene ID: 4967); parathyroid hormone (PTH; NCBI Gene ID: 5741); PD-L1 (CD274; NCBI Gene ID: 29126); periostin (POSTN; NCBI Gene ID: 10631); peroxisome proliferator activated receptors (e.g., PPARA (PPAR alpha), PPARD (PPAR delta), PPARG (PPAR gamma); NCBI Gene IDs: 5465, 5467, 5468); phosphatase and tensin homolog (PTEN; NCBI Gene ID: 5728); phosphatidylinositol-4,5-bisphosphate 3-kinases (PIK3CA (PI3K alpha), PIK3CB (PI3K beta), PIK3CD (PI3K delta), PIK3CG (PI3K gamma); NCBI Gene IDs: 5290, 5291, 5293, 5294); phospholipases (e.g., PLA2G1B, PLA2G2A, PLA2G2D, PLA2G3, PLA2G4A, PLA2G5, PLA2G7, PLA2G10, PLA2G12A, PLA2G12B, PLA2G15; NCBI Gene IDs: 5319, 5320, 5321, 5322, 7941, 8399, 50487, 23659, 26279, 81579, 84647); Pim proto-oncogene, serine/threonine kinases (e.g., PIM1, PIM2, PIM3; NCBI Gene IDs: 5292, 11040, 415116); placenta growth factor (PGF; NCBI Gene ID: 5228); plasminogen activator, urokinase (PLAU, u-PA, ATF; NCBI Gene ID: 5328); platelet derived growth factor receptors (e.g., PDGFRA (CD140A, PDGFR2), FDGFRB (CD140B, PDGFR1); NCBI Gene IDs: 5156, 5159); plexin B1 (PLXNB1; NCBI Gene ID: 5364); poliovirus receptor (PVR) cell adhesion molecule (PVR, CD155; NCBI Gene ID: 5817); polo like kinase 1 (PLK1; NCBI Gene ID: 5347); poly(ADP-ribose) polymerases (e.g., PARP1, PARP2, PARP3; NCBI Gene IDs: 142, 10038, 10039); polycomb protein EED (EED; NCBI Gene ID: 8726); porcupine O-acyltransferase (PORCN; NCBI Gene ID: 64840); PRAME nuclear receptor transcriptional regulator (PRAME; NCBI Gene ID: 23532); premelanosome protein (PMEL; NCBI Gene ID: 6490); progesterone receptor (PGR; NCBI Gene ID: 5241); programmed cell death 1 (PDCD1, PD-1, CD279; NCBI Gene ID: 5133); programmed cell death 1 ligand 2 (PDCD1LG2, CD273, PD-L2; NCBI Gene ID: 80380); prominin 1 (PROM1, CD133; NCBI Gene ID: 8842); promyelocytic leukemia (PML; NCBI Gene ID: 5371); prosaposin (PSAP; NCBI Gene ID: 5660); prostaglandin E receptor 4 (PTGER4; NCBI Gene ID: 5734); prostaglandin E synthase (PTGES; NCBI Gene ID: 9536); prostaglandin-endoperoxide synthases (PTGS1 (COX1), PTGS2 (COX2); NCBI Gene ID: 5742, 5743); proteasome 20S subunit beta 9 (PSMB9; NCBI Gene ID: 5698); protein arginine methyltransferases (e.g., PRMT1; NCBI Gene ID: 3276); protein kinase N3 (PKN3; NCBI Gene ID: 29941); protein phosphatase 2A (PPP2CA; NCBI Gene ID: 5515); protein tyrosine kinase 7 (inactive) (PTK7; NCBI Gene ID: 5754); protein tyrosine phosphatase receptors (PTPRB (PTPB), PTPRC (CD45R); NCBI Gene ID: 5787, 5788); prothymosin alpha (PTMA; NCBI Gene ID: 5757); purine nucleoside phosphorylase (PNP; NCBI Gene ID: 4860); purinergic receptor P2X 7 (P2RX7; NCBI Gene ID: 5027); PVR related immunoglobulin domain containing (PVRIG, CD112R; NCBI Gene ID: 79037); Raf-1 proto-oncogene, serine/threonine kinase (RAF1, c-Raf; NCBI Gene ID: 5894); RAR-related orphan receptor gamma (RORC; NCBI Gene ID: 6097); ras homolog family member C (RHOC); NCBI Gene ID: 389); Ras homolog, mTORC1 binding (RHEB; NCBI Gene ID: 6009); RB transcriptional corepressor 1 (RB1; NCBI Gene ID: 5925); receptor-interacting serine/threonine protein kinase 1 (RIPK1; NCBI Gene ID: 8737); ret proto-oncogene (RET; NCBI Gene ID: 5979); retinoic acid early transcripts (e.g., RAET1E, RAET1G, RAET1L; NCBI Gene IDs: 135250, 154064, 353091); retinoic acid receptors alpha (e.g., RARA, RARG; NCBI Gene IDs: 5914, 5916); retinoid X receptors (e.g., RXRA, RXRB, RXRG; NCBI Gene IDs: 6256, 6257, 6258); Rho associated coiled-coil containing protein kinases (e.g., ROCK1, ROCK2; NCBI Gene IDs: 6093, 9475); ribosomal protein S6 kinase B1 (RPS6KB1, S6K-beta 1; NCBI Gene ID: 6198); ring finger protein 128 (RNF128, GRAIL; NCBI Gene ID: 79589); ROS proto-oncogene 1, receptor tyrosine kinase (ROS1; NCBI Gene ID: 6098); roundabout guidance receptor 4 (ROBO4; NCBI Gene ID: 54538); RUNX family transcription factor 3 (RUNX3; NCBI Gene ID: 864); S100 calcium binding protein A9 (S100A9; NCBI Gene ID: 6280); secreted frizzled related protein 2 (SFRP2; NCBI Gene ID: 6423); secreted phosphoprotein 1 (SPP1; NCBI Gene ID: 6696); secretoglobin family 1A member 1 (SCGB1A1; NCBI Gene ID: 7356); selectins (e.g., SELE, SELL (CD62L), SELP (CD62); NCBI Gene IDs: 6401, 6402, 6403); semaphorin 4D (SEMA4D; CD100; NCBI Gene ID: 10507); sialic acid binding Ig like lectins (SIGLEC7 (CD328), SIGLEC9 (CD329), SIGLEC10; NCBI Gene ID: 27036, 27180, 89790); signal regulatory protein alpha (SIRPA, CD172A; NCBI Gene ID: 140885); signal transducer and activator of transcription (e.g., STAT1, STAT3, STAT5A, STAT5B; NCBI Gene IDs: 6772, 6774, 6776, 6777); sirtuin-3 (SIRT3; NCBI Gene ID: 23410); signaling lymphocytic activation molecule (SLAM) family members (e.g., SLAMFI (CD150), SLAMF6 (CD352), SLAMF7 (CD319), SLAMF8 (CD353), SLAMF9; NCBI Gene IDs: 56833, 57823, 89886, 114836); SLIT and NTRK like family member 6 (SLITRK6; NCBI Gene ID: 84189); smoothened, frizzled class receptor (SMO; NCBI Gene ID: 6608); soluble epoxide hydrolase 2 (EPHX2; NCBI Gene ID: 2053); solute carrier family members (e.g., SLC3A2 (CD98), SLC5A5, SLC6A2, SLC10A3, SLC34A2, SLC39A6, SLC43A2 (LAT4), SLC44A4; NCBI Gene IDs: 6520, 6528, 6530, 8273, 10568, 25800, 80736, 124935); somatostatin receptors (e.g., SSTR1, SSTR2, SSTR3, SSTR4, SSTR5; NCBI Gene IDs: 6751, 6752, 6753, 6754, 6755); sonic hedgehog signaling molecule (SHH; NCBI Gene ID: 6469); Spl transcription factor (SP1; NCBI Gene ID: 6667); sphingosine kinases (e.g., SPHK1, SPHK2; NCBI Gene IDs: 8877, 56848); sphingosine-1-phosphate receptor 1 (S1PR1, CD363; NCBI Gene ID: 1901); spleen associated tyrosine kinase (SYK; NCBI Gene ID: 6850); splicing factor 3B factor 1 (SF3B1; NCBI Gene ID: 23451); SRC proto-oncogene, non-receptor tyrosine kinase (SRC; NCBI Gene ID: 6714); stabilin 1 (STAB1, CLEVER-1; NCBI Gene ID: 23166); STEAP family member 1 (STEAP1; NCBI Gene ID: 26872); steroid sulfatase (STS; NCBI Gene ID: 412); stimulator of interferon response cGAMP interactor 1 (STING1; NCBI Gene ID: 340061); superoxide dismutase 1 (SOD1, ALS1; NCBI Gene ID: 6647); suppressors of cytokine signaling (SOCS1 (CISH1), SOCS3 (CISH3); NCBI Gene ID: 8651, 9021); synapsin 3 (SYN3; NCBI Gene ID: 8224); syndecan 1 (SDC1, CD138, syndecan; NCBI Gene ID: 6382); synuclein alpha (SNCA, PARK1; NCBI Gene ID: 6622); T cell immunoglobulin and mucin domain containing 4 (TIMD4, SMUCKLER; NCBI Gene ID: 91937); T cell immunoreceptor with Ig and ITIM domains (TIGIT; NCBI Gene ID: 201633); tachykinin receptors (e.g., TACR1, TACR3; NCBI Gene ID: 6869, 6870); TANK binding kinase 1 (TBK1; NCBI Gene ID: 29110); tankyrase (TNKS; NCBI Gene ID: 8658); TATA-box binding protein associated factor, RNA polymerase I subunit B (TAF1B; NCBI Gene ID: 9014); T-box transcription factor T (TBXT; NCBI Gene ID: 6862); TCDD inducible poly(ADP-ribose) polymerase (TIPARP, PAPR7; NCBI Gene ID: 25976); tec protein tyrosine kinase (TEC; NCBI Gene ID: 7006); TEK receptor tyrosine kinase (TEK, CD202B, TIE2; NCBI Gene ID: 7010); telomerase reverse transcriptase (TERT; NCBI Gene ID: 7015); tenascin C (TNC; NCBI Gene ID: 3371); three prime repair exonucleases (e.g., TREX1, TREX2; NCBI Gene ID: 11277, 11219); thrombomodulin (THBD, CD141; NCBI Gene ID: 7056); thymidine kinases (e.g., TK1, TK2; NCBI Gene IDs: 7083, 7084); thymidine phosphorylase (TYMP; NCBI Gene ID: 1890); thymidylate synthase (TYMS; NCBI Gene ID: 7298); thyroid hormone receptor (THRA, THRB; NCBI Gene IDs: 7606, 7608); thyroid stimulating hormone receptor (TSHR; NCBI Gene ID: 7253); TNF superfamily members (e.g., TNFSF4 (OX40L, CD252), TNFSF5 (CD40L), TNFSF7 (CD70), TNFSF8 (CD153, CD30L), TNFSF9 (4-1BB-L, CD137L), TNFSF10 (TRAIL, CD253, APO2L), TNFSF11 (CD254, RANKL2, TRANCE), TNFSF13 (APRIL, CD256, TRAIL2), TNFSF13b (BAFF, BLYS, CD257), TNFSF14 (CD258, LIGHT), TNFSF18 (GITRL); NCBI Gene IDs: 944, 959, 970, 7292, 8600, 8740, 8741, 8743, 8744, 8995); toll like receptors (e.g., TLR1 (CD281), TLR2 (CD282), TLR3 (CD283), TLR4 (CD284), TLR5, TLR6 (CD286), TLR7, TLR8 (CD288), TLR9 (CD289), TLR10 (CD290); NCBI Gene IDs: 7096, 7097, 7098, 7099, 10333, 51284, 51311, 54106, 81793); transferrin (TF; NCBI Gene ID: 7018); transferrin receptor (TFRC, CD71; NCBI Gene ID: 7037); transforming growth factors (e.g., TGFA, TGFB1; NCBI Gene ID: 7039, 7040); transforming growth factor receptors (e.g., TGFBR1, TGFBR2, TGFBR3; NCBI Gene ID: 7046, 7048, 7049); transforming protein E7 (E7; NCBI Gene ID: 1489079); transglutaminase 5 (TGM5; NCBI Gene ID: 9333); transient receptor potential cation channel subfamily V member 1 (TRPV1, VR1; NCBI Gene ID: 7442); transmembrane and immunoglobulin domain containing 2 (TMIGD2, CD28H, IGPR1; NCBI Gene ID: 126259); triggering receptors expressed on myeloid cells (e.g., TREM1 (CD354), TREM2; NCBI Gene ID: 54209, 54210); trophinin (TRO, MAGED3; NCBI Gene ID: 7216); trophoblast glycoprotein (TPBG; NCBI Gene ID: 7162); tryptophan 2,3-dioxygenase (TDO2; NCBI Gene ID: 6999); tryptophan hydroxylases (e.g., TPH1, TPH2; NCBI Gene ID: 7166, 121278); tumor associated calcium signal transducer 2 (TACSTD2, TROP2, EGP1; NCBI Gene ID: 4070); tumor necrosis factor (TNF; NCBI Gene ID: 7124); tumor necrosis factor (TNF) receptor superfamily members (e.g., TNFRSFlA (CD120a), TNFRSFlB (CD120b), TNFRSF4 (OX40), TNFRSF5 (CD40), TNFRSF6 (CD95, FAS receptor), TNFRSF7 (CD27), TNFRSF8 (CD30), TNFRSF9 (CD137, 4-1BB), TNFRSF10A (CD261), TNFRSF10B (TRAIL, DRS, CD262), TNFRSF10C, TNFRSF10D, TNFRSF11A, TNFRSF11B (OPG), TNFRSF12A, TNFRSF13B, TNFR13C (, CD268, BAFFR), TNFRSF14 (CD270, LIGHTR), TNFRSF16, TNFRSF17 (CD269, BCMA), TNFRSF18 (GITR, CD357), TNFRSF19, TNFRSF21, TNFRSF25,; NCBI Gene IDs: 355, 608, 939, 943, 958, 3604, 4804, 4982, 7132, 7133, 7293, 8718, 8764, 8784, 8792, 8793, 8794, 8795, 8797, 23495, 27242, 51330, 55504); tumor protein p53 (TP53; NCBI Gene ID: 7157); tumor suppressor 2, mitochondrial calcium regulator (TUSC2; NCBI Gene ID: 11334); TYRO3 protein tyrosine kinase (TYRO3; BYK; NCBI Gene ID: 7301); tyrosinase (TYR; NCBI Gene ID: 7299); tyrosine hydroxylase (TH; NCBI Gene ID: 7054); tyrosine kinase with immunoglobulin like and EGF like domains 1 (e.g., TIEl, TIEl; NCBI Gene ID: 7075); tyrosine-protein phosphatase non-receptor type 11 (PTPN11, SHP2; NCBI Gene ID: 5781); ubiquitin conjugating enzyme E2 I (UBE2I, UBC9; NCBI Gene ID: 7329); ubiquitin C-terminal hydrolase L5 (UCHL5; NCBI Gene ID: 51377); ubiquitin specific peptidase 7 (USP7; NCBI Gene ID: 7874); ubiquitin-like modifier activating enzyme 1 (UBA1; NCBI Gene ID: 7317); UL16 binding proteins (e.g., ULBP1, ULBP2, ULBP3; NCBI Gene ID: 79465, 80328, 80328); valosin-containing protein (VCP, CDC48; NCBI Gene ID: 7415); vascular cell adhesion molecule 1 (VCAM1, CD106; NCBI Gene ID: 7412); vascular endothelial growth factors (e.g., VEGFA, VEGFB; NCBI Gene ID: 7422, 7423); vimentin (VIM; NCBI Gene ID: 7431); vitamin D receptor (VDR; NCBI Gene ID: 7421); V-set domain containing T cell activation inhibitor 1 (VTCN1, B7-H4; NCBI Gene ID: 79679); V-set immunoregulatory receptor (VSIR, VISTA, B7-H5; NCBI Gene ID: 64115); WEEl G2 checkpoint kinase (WEE; NCBI Gene ID: 7465); WRN RecQ like helicase (WRN; RECQ3; NCBI Gene ID: 7486); WT1 transcription factor (WT1; NCBI Gene ID: 7490); WW domain containing transcription regulator 1 (WWTR1; TAZ; NCBI Gene ID: 25937); X—C motif chemokine ligand 1 (XCL1, ATAC; NCBI Gene ID: 6375); X—C motif chemokine receptor 1 (XCR1, GPR5, CCXCR1; NCBI Gene ID: 2829); Yesl associated transcriptional regulator (YAP1; NCBI Gene ID: 10413); or zeta chain associated protein kinase 70 (ZAP70; NCBI Gene ID: 7535).

In some embodiments, the one or more additional therapeutic agents include, e.g., an agent targeting 5'-nucleotidase ecto (NT5E or CD73; NCBI Gene ID: 4907); adenosine A2A receptor (ADORA2A; NCBI Gene ID: 135); adenosine $A2_B$ receptor (ADORA2B; NCBI Gene ID: 136); C-C motif chemokine receptor 8 (CCR8, CDwl98; NCBI Gene ID: 1237); cytokine inducible SH2 containing protein (CISH; NCBI Gene ID: 1154); diacylglycerol kinase alpha (DGKA, DAGK, DAGK1 or DGK-alpha; NCBI Gene ID: 1606); fms like tyrosine kinase 3 (FLT3, CD135; NCBI Gene ID: 2322); integrin associated protein (IAP, CD47; NCBI Gene ID: 961); interleukine-2 (IL2; NCBI Gene ID:3558); interleukine 2 receptor (IL2RA, IL2RB, IL2RG; NCBI Gene IDs: 3559, 3560, 3561); Kirsten rat sarcoma virus (KRAS; NCBI Gene ID: 3845; including mutations, such as KRAS G12C or G12D); mitogen-activated protein kinase kinase kinase kinase 1 (MAP4K1) (also called Hematopoietic Progenitor Kinase 1 (HPK1), NCBI Gene ID: 11184); myeloid cell leukemia sequence 1 apoptosis regulator (MCL1; NCBI Gene ID: 4170); phosphatidylinositol-4,5-bisphosphate 3-kinase, catalytic subunit delta (PIK3CD; NCBI Gene ID: 5293); programmed death-ligand 1 (PD-L1, CD274; NCBI Gene ID 29126); programmed cell death protein 1 (PD-1, CD279; NCBI Gene ID: 5133); proto-oncogen c-KIT (KIT, CD117; NCBI Gene ID: 3815); signal-regulatory protein alpha (SIRPA, CD172A; NCBI Gene ID: 140885); TCDD inducible poly(ADP-ribose) polymerase (TIPARP, PARP7; NCBI Gene ID: 25976); T cell immunoreceptor with Ig and ITIM domains (TIGIT; NCBI Gene ID: 201633); triggering receptor expressed on myeloid cells 1 (TREM1; NCBI Gene ID: 54210); triggering receptor expressed on myeloid cells 2 (TREM2; NCBI Gene ID: 54209); tumor-associated calcium signal transducer 2 (TACSTD2, TROP2, EGP1; NCBI Gene ID: 4070); tumor necrosis factor receptor superfamily, member 4 (TNFRSF4, CD134, OX40; NCBI Gene ID:7293); tumor necrosis factor receptor superfamily, member 9 (TNFRSF9, 4-1BB, CD137; NCBI Gene ID: 3604); tumor necrosis factor receptor superfamily, member 18 (TNFRSF18, CD357, GITR; NCBI Gene ID: 8784); WRN RecQ like helicase (WRN; NCBI Gene ID: 7486); or zinc finger protein Helios (IKZF2; NCBI Gene ID: 22807).

Illustrative Mechanisms of Action

Immune Checkpoint Modulators

In some embodiments a compound of Formula (I), (Ia), (Ib), or (Ic) provided herein, or pharmaceutically acceptable salt thereof, is administered with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of cancer cells within the tumor microenvironment. Activation or stimulation of stimulatory immune check points can augment the effect of immune checkpoint inhibitors in cancer therapeutics. In some embodiments, the immune checkpoint proteins or receptors regulate T cell responses (e.g., reviewed in Xu, et al., *J Exp Clin Cancer Res.* (2018) 37:110). In some embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688). Inhibition of regulatory T-cells (Treg) or Treg depletion can alleviate their suppression of antitumor immune responses and have anti-cancer effects (e.g., reviewed in Plitas and Rudensky, *Annu. Rev. Cancer Biol.* (2020) 4:459-77; Tanaka and Sakaguchi, *Eur. J. Immunol.* (2019) 49:1140-1146).

Examples of immune checkpoint proteins or receptors that can be combined with a compound provided herein, or pharmaceutically acceptable salt thereof, include CD27 (NCBI Gene ID: 939), CD70 (NCBI Gene ID: 970); CD40 (NCBI Gene ID: 958), CD40LG (NCBI Gene ID: 959); CD47 (NCBI Gene ID: 961), SIRPA (NCBI Gene ID: 140885); CD48 (SLAMF2; NCBI Gene ID: 962), transmembrane and immunoglobulin domain containing 2 (TMIGD2, CD28H; NCBI Gene ID: 126259), CD84 (LY9B, SLAMF5; NCBI Gene ID: 8832), CD96 (NCBI Gene ID: 10225), CD160 (NCBI Gene ID: 11126), MS4A1 (CD20; NCBI Gene ID: 931), CD244 (SLAMF4; NCBI Gene ID: 51744); CD276 (B7H3; NCBI Gene ID: 80381); V-set domain containing T cell activation inhibitor 1 (VTCN1, B7H4); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943), TNFSF8 (CD30L; NCBI Gene ID: 944); TNFRSF10A (CD261, DR4, TRAILR1; NCBI Gene ID: 8797), TNFRSF9 (CD137; NCBI Gene ID: 3604), TNFSF9 (CD137L; NCBI Gene ID: 8744); TNFRSF10B (CD262, DR5, TRAILR2; NCBI Gene ID: 8795), TNFRSF10 (TRAIL; NCBI Gene ID: 8743); TNFRSF14 (HVEM, CD270; NCBI Gene ID: 8764), TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608), TNFSF13B (BAFF; NCBI Gene ID: 10673); TNFRSF18 (GITR; NCBI Gene ID: 8784), TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941), CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; NCBI Gene ID: 84868); galectin 9 (LGALS9; NCBI Gene ID: 3965); lymphocyte activating 3 (LAG3, CD223; NCBI Gene ID: 3902); signaling lymphocytic activation molecule family member 1 (SLAMFI, SLAM, CD150; NCBI Gene ID: 6504); lymphocyte antigen 9 (LY9, CD229, SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAETIE; ULBP4; NCBI Gene ID: 135250); retinoic acid early transcript 1G (RAETIG; ULBP5; NCBI Gene ID: 353091); retinoic acid early transcript 1L (RAETIL; ULBP6; NCBI Gene ID: 154064); killer cell immunoglobulin like receptor, three Ig domains and long cytoplasmic tail 1 (KIR, CD158E1; NCBI Gene ID: 3811, e.g., lirilumab (IPH-2102, IPH-4102)); killer cell lectin like receptor $C_1$ (KLRC1, NKG2A, CD159A; NCBI Gene ID: 3821); killer cell lectin like receptor K1 (KLRK1, NKG2D, CD314; NCBI Gene ID: 22914); killer cell lectin like receptor $C_2$ (KLRC2, CD159c, NKG2C; NCBI Gene ID: 3822); killer cell lectin like receptor $C_3$ (KLRC3, NKG2E; NCBI Gene ID: 3823); killer cell lectin like receptor $C_4$ (KLRC4, NKG2F; NCBI Gene ID: 8302); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); killer cell immunoglobulin like receptor, three Ig domains and long cytoplasmic tail 1 (KIR3DL1); killer cell lectin like receptor D1 (KLRD1; NCBI Gene ID: 3824); killer cell lectin like receptor G1 (KLRG1; CLECISA, MAFA, 2F1; NCBI Gene ID: 10219); sialic acid binding Ig like lectin 7 (SIGLEC7; NCBI Gene ID: 27036); and sialic acid binding Ig like lectin 9 (SIGLEC9; NCBI Gene ID: 27180).

In some embodiments a compound of Formula (I), (Ia), (Ib), or (Ic) provided herein, or pharmaceutically acceptable salt thereof, is administered with one or more blockers or inhibitors of one or more T-cell inhibitory immune checkpoint proteins or receptors. Illustrative T-cell inhibitory immune checkpoint proteins or receptors include CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the compound or pharmaceutically acceptable salt thereof provided herein is administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., *J Exp Clin Cancer Res*. (2018) 37:110.

In some embodiments a compound of Formula (I), (Ia), (Ib), or (Ic) provided herein, or pharmaceutically acceptable salt thereof, is administered with one or more blockers or inhibitors of one or more NK-cell inhibitory immune checkpoint proteins or receptors. Illustrative NK-cell inhibitory immune checkpoint proteins or receptors include killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor $C_1$ (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments the compound or pharmaceutically acceptable salt thereof provided herein is administered with one or more agonist or activators of one or more NK-cell stimulatory immune checkpoint proteins or receptors. Illustrative NK-cell stimulatory immune checkpoint proteins or receptors include CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., *Semin Immunol*. (2017) 31:64-75; Fang, et al., *Semin Immunol*. (2017) 31:37-54; and Chiossone, et al., *Nat Rev Immunol*. (2018) 18(11):671-688.

In some embodiments the one or more immune checkpoint inhibitors comprise a proteinaceous (e.g., antibody or fragment thereof, or antibody mimetic) inhibitor of PD-L1 (CD274), PD-1 (PDCD1), CTLA4, or TIGIT. In some embodiments the one or more immune checkpoint inhibitors comprise a small organic molecule inhibitor of PD-L1 (CD274), PD-1 (PDCD1), CTLA4, or TIGIT. In some embodiments the one or more immune checkpoint inhibitors comprise a proteinaceous (e.g., antibody or fragment thereof, or antibody mimetic) inhibitor of LAG3.

Examples of inhibitors of CTLA4 that can be co-administered include ipilimumab, tremelimumab, BMS-986218, AGEN1181, zalifrelimab (AGEN1884), BMS-986249, MK-1308, REGN-4659, ADU-1604, CS-1002 (ipilimumab biosimilar), BCD-145, APL-509, JS-007, BA-3071, ONC-392, AGEN-2041, HBM-4003, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include pembrolizumab, nivolumab, cemiplimab, pidilizumab, AMP-224, MEDIO680 (AMP-514), spartalizumab, atezolizumab, avelumab, durvalumab, BMS-936559, cosibelimab (CK-301), sasanlimab (PF-06801591), tislelizumab (BGB-A317), GLS-010 (WBP-3055), AK-103 (HX-008), AK-105, CS-1003, HLX-10, retifanlimab (MGA-012), BI-754091, balstilimab (AGEN-2034), AMG-404, toripalimab (JS-001), cetrelimab (JNJ-63723283), genolimzumab (CBT-501), LZM-009, prolgolimab (BCD-100), lodapolimab (LY-3300054), SHR-1201, camrelizumab (SHR-1210), Sym-021, budigalimab (ABBV-181), PD1-PIK, BAT-1306, avelumab (MSB0010718C), CX-072, CBT-502, dostarlimab (TSR-042), MSB-2311, JTX-4014, BGB-A333, SHR-1316, CS-1001 (WBP-3155, envafolimab (KN-035), sintilimab (IBI-308), HLX-20, KL-A167, STI-A1014, STI-A1015 (IMC-001), BCD-135, FAZ-053, TQB-2450, MDX1105-01, GS-4224, GS-4416, INCB086550, MAX10181, zimberelimab (AB122), spartalizumab (PDR-001), and compounds disclosed in WO2018195321, WO2020014643, WO2019160882, or WO2018195321, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1), RO-7247669 (PD-1/LAG-3), MGD-019 (PD-1/CTLA4), KN-046 (PD-1/CTLA4), MEDI-5752 (CTLA4/PD-1), RO-7121661 (PD-1/TIM-3), RG7769 (PD-1/TIM-3), TAK-252 (PD-1/OX40L), XmAb-20717 (PD-1/CTLA4), AK-104 (CTLA4/PD-1), FS-118 (LAG-3/PD-L1), FPT-155 (CTLA4/PD-L1/CD28), GEN-1046 (PD-L1/4-1BB), bintrafusp alpha (M7824; PD-L1/TGFP-EC domain), CA-170 (PD-L1/VISTA), CDX-527 (CD27/PD-L1), LY-3415244 (TIM3/PDL1), and INBRX-105 (4-1BB/PDL1). In some embodiments the PD-L1 inhibitor is a small molecule inhibitor, such as CA-170, GS-4224, GS-4416 and lazertinib (GNS-1480; PD-L1/EGFR).

Examples of inhibitors of TIGIT that can be co-administered include tiragolumab (RG-6058), vibostolimab, domvanalimab (AB154), AB308, BMS-986207, AGEN-1307, COM-902, or etigilimab.

Examples of inhibitors of LAG3 that can be co-administered include leramilimab (LAG525).

Inhibition of regulatory T-cell (Treg) activity or Treg depletion can alleviate their suppression of antitumor immune responses and have anticancer effects. See, e.g., Plitas and Rudensky, *Annu. Rev. Cancer Biol*. (2020) 4:459-77; Tanaka and Sakaguchi, *Eur. J. Immunol*. (2019) 49:1140-1146. In some embodiments, a compound of Formula (I), (Ia), (Ib), or (Ic) provided herein, or pharmaceutically acceptable salt thereof, provided herein is administered with one or more inhibitors of Treg activity or a Treg depleting agent. Treg inhibition or depletion can augment the effect of immune checkpoint inhibitors in cancer therapeutics.

In some embodiments compound or pharmaceutically acceptable salt thereof provided herein is administered with one or more Treg inhibitors. In some embodiments the Treg inhibitor can suppress the migration of Tregs into the tumor microenvironment. In some embodiments Treg inhibitor can reduce the immunosuppressive function of Tregs. In some embodiments, the Treg inhibitor can modulate the cellular phenotype and induce production of proinflammatory cytokines. Exemplary Treg inhibitors include, without limitation, CCR4 (NCBI Gene ID: 1233) antagonists and degraders of Ikaros zinc-finger proteins (e.g., Ikaros (IKZF1; NCBI Gene ID: 10320), Helios (IKZF2; NCBI Gene ID: 22807), Aiolos (IKZF3; NCBI Gene ID: 22806), and Eos (IKZF4; NCBI Gene ID: 64375).

Examples of Helios degraders that can be co-administered include without limitation I-57 (Novartis) and compounds disclosed in WO2019038717, WO2020012334, WO20200117759, and WO2021101919.

In some embodiments a compound or pharmaceutically acceptable salt thereof provided herein is administered with one or more Treg depleting agents. In some embodiments the Treg depleting agent is an antibody. In some embodiments the Treg depleting antibody has antibody-dependent cytotoxic (ADCC) activity. In some embodiments, the Treg depleting antibody is Fc-engineered to possess an enhanced ADCC activity. In some embodiments the Treg depleting antibody is an antibody-drug conjugate (ADC). Illustrative targets for Treg depleting agents include without limitation CD25 (IL2RA; NCBI Gene ID: 3559), CTLA4 (CD152; NCBI Gene ID: 1493); GITR (TNFRSF18; NCBI Gene ID: 8784); 4-1BB (CD137; NCBI Gene ID: 3604), OX-40 (CD134; NCBI Gene ID: 7293), LAG3 (CD223; NCBI Gene ID: 3902), TIGIT (NCBI Gene ID: 201633), CCR4 (NCBI Gene ID: 1233), and CCR8 (NCBI Gene ID: 1237).

In some embodiments the Treg inhibitor or Treg depleting agent that can be co-administered comprises an antibody or antigen-binding fragment thereof that selectively binds to a cell surface receptor selected from the group consisting of C-C motif chemokine receptor 4 (CCR4), C-C motif chemokine receptor 7 (CCR7), C-C motif chemokine receptor 8 (CCR8), C-X-C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ectonucleoside triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL2RA (CD25) or a combination thereof.

Examples of Treg depleting anti-CCR8 antibodies that can be administered include without limitation JTX-1811 (GS-1811) (Jounce Therapeutics, Gilead Sciences), BMS-986340 (Bristol Meyers Squibb), S-531011 (Shionogi), FPA157 (Five Prime Therapeutics), SRF-114 (Surface Oncology), HBM1022 (Harbor BioMed), IO-1 (Oncurious), and antibodies disclosed in WO2021163064, WO2020138489, and WO2021152186.

Examples of Treg depleting anti-CCR4 antibodies that can be administered include mogamulizumab.

Inhibiting, depleting, or reprogramming of non-stimulatory myeloid cells in the tumor microenvironment can enhance anti-cancer immune responses (see, e.g., Binnewies et al., *Nat. Med.* (2018) 24(5): 541-550; WO2016049641). Illustrative targets for depleting or reprogramming non-stimulatory myeloid cells include triggering receptors expressed on myeloid cells, TREM-1 (CD354, NCBI Gene ID: 54210) and TREM-2 (NCBI Gene ID: 54209). In some embodiments a compound or pharmaceutically acceptable salt thereof provided herein is administered with one or more myeloid cell depleting or reprogramming agents, such as an anti-TREM-1 antibody (e.g., PY159; antibodies disclosed in WO2019032624) or an anti-TREM-2 antibody (e.g., PY314; antibodies disclosed in WO2019118513).

Cluster of Differentiation Agonists or Activators

In some embodiments, a compound of Formula (I), (Ia), (Ib), or (Ic) provided herein, or pharmaceutically acceptable salt thereof, is administered with agents targeting a cluster of differentiation (CD) marker. Exemplary CD marker targeting agents that can be co-administered include without limitation A6, AD-IL24, neratinib, tucatinib (ONT 380), mobocertinib (TAK-788), tesevatinib, trastuzumab (HERCEPTIN®), trastuzumab biosimimar (HLX-02), margetuximab, BAT-8001, pertuzumab (Perjeta), pegfilgrastim, RG6264, zanidatamab (ZW25), cavatak, AIC-100, tagraxofusp (SL-401), HLA-A2402/HLA-A0201 restricted epitope peptide vaccine, dasatinib, imatinib, nilotinib, sorafenib, lenvatinib mesylate, ofranergene obadenovec, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, olverembatinib dimesylate (HQP-1351), cabozantinib, ponatinib, and famitinib L-malate, CX-2029 (ABBV-2029), SCB-313, CA-170, COM-701, CDX-301, GS-3583, asunercept (APG-101), APO-010, and compounds disclosed in WO2016196388, WO2016033570, WO2015157386, WO199203459, WO199221766, WO2004080462, WO2005020921, WO2006009755, WO2007078034, WO2007092403, WO2007127317, WO2008005877, WO2012154480, WO2014100620, WO2014039714, WO2015134536, WO2017167182, WO2018112136, WO2018112140, WO2019155067, WO2020076105, PCT/US2019/063091, WO19173692, WO2016179517, WO2017096179, WO2017096182, WO2017096281, WO2018089628, WO2017096179, WO2018089628, WO2018195321, WO2020014643, WO2019160882, WO2018195321, WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170, WO2020068752, Cancer Discov. 2019 Jan. 9(1):8; and Gariepy J., et al. 106th Annu Meet Am Assoc Immunologists (AAI) (May 9-13, San Diego, 2019, Abst 71.5).

In some embodiments the CD marker targeting agents that can be co-administered include small molecule inhibitors, such as PBF-1662, BLZ-945, pemigatinib (INCB-054828), rogaratinib (BAY-1163877), AZD4547, roblitinib (FGF-401), quizartinib dihydrochloride, SX-682, AZD-5069, PLX-9486, avapritinib (BLU-285), ripretinib (DCC-2618), imatinib mesylate, JSP-191, BLU-263, CD117-ADC, AZD3229, telatinib, vorolanib, GO-203-2C, AB-680, PSB-12379, PSB-12441, PSB-12425, CB-708, HM-30181A, motixafortide (BL-8040), LY2510924, burixafor (TG-0054), X4P-002, mavorixafor (X4P-001-IO), plerixafor, CTX-5861, and REGN-5678 (PSMA/CD28).

In some embodiments the CD marker targeting agent that can be co-administered include small molecule agonists, such as interleukin 2 receptor subunit gamma, eltrombopag, rintatolimod, poly-ICLC (NSC-301463), Riboxxon, Apoxxim, RIBOXXIM®, MCT-465, MCT-475, G100, PEPA-10, eftozanermin alfa (ABBV-621), E-6887, motolimod, resiquimod, selgantolimod (GS-9688), VTX-1463, NKTR-262, AST-008, CMP-001, cobitolimod, tilsotolimod, litenimod, MGN-1601, BB-006, IMO-8400, IMO-9200, agatolimod, DIMS-9054, DV-1079, lefitolimod (MGN-1703), CYT-003, and PUL-042.

In some embodiments the CD marker targeting agent that can be co-administered include antibodies, such as tafasitamab (MOR208; MorphoSys AG), Inebilizumab (MEDI-551), obinutuzumab, IGN-002, rituximab biosimilar (PF-05280586), varlilumab (CDX-1127), AFM-13 (CD16/CD30), AMG330, otlertuzumab (TRU-016), isatuximab, felzartamab (MOR-202), TAK-079, TAK573, daratumumab (DARZALEX®), TTX-030, selicrelumab (RG7876), APX-005M, ABBV-428, ABBV-927, mitazalimab (JNJ-64457107), lenziluma, alemtuzuma, emactuzumab, AMG-820, FPA-008 (cabiralizumab), PRS-343 (CD-137/Her2), AFM-13 (CD16/CD30), belantamab mafodotin (GSK-2857916), AFM26 (BCMA/CD16A), simlukafusp alfa (RG7461), urelumab, utomilumab (PF-05082566), AGEN2373, ADG-106, BT-7480, PRS-343 (CD-137/HER2), FAP-4-IBBL (4-1BB/FAP), ramucirumab, CDX-0158, CDX-0159 and FSI-174, relatlimab (ONO-4482), LAG-525, MK-4280, fianlimab (REGN-3767), INCAGN2385, encelimab (TSR-033), atipotuzumab, BrevaRex (Mab-AR-20.5), MEDI-9447 (oleclumab), CPX-006, IPH-53, BMS-986179, NZV-930, CPI-006, PAT-SC1, lirilumab (IPH-2102), lacutamab (IPH-4102), monalizumab, BAY-1834942, NEO-201 (CEACAM 5/6), Iodine (131I) apamistamab (131I—BC8 (lomab-B)), MEDI0562 (tavolixizumab), GSK-3174998, INCAGN1949, BMS-986178, GBR-8383, ABBV-368, denosumab, BION-1301, MK-4166, INCAGN-1876, TRX-518, BMS-986156, MK-1248, GWN-323, CTB-006, INBRX-109, GEN-1029, pepinemab (VX-15), vopratelimab (JTX-2011), GSK3359609, cobolimab (TSR-022), MBG-453, INCAGN-2390, and compounds disclosed in WO 2017096179, WO2017096276, WO2017096189, and WO2018089628.

In some embodiments the CD marker targeting agent that can be co-administered include cell therapies, such as CD19-ARTEMIS, TBI-1501, CTL-119 huCART-19 T cells, 1 iso-cel, lisocabtagene maraleucel (JCAR-017), axicabtagene ciloleucel (KTE-$C_{19}$, Yescarta®), axicabtagene ciloleucel (KTE-X19), U.S. Pat. Nos. 7,741,465, 6,319,494, UCART-19, tabelecleucel (EBV-CTL), T tisagenlecleucel-T (CTL019), CD19CAR-CD28-CD3zeta-EGFRt-expressing T cells, CD19/4-1BBL armored CAR T cell therapy, C-CAR-011, CIK-CAR.CD19, CDI9CAR-28-zeta T cells, PCAR-019, MatchCART, DSCAR-01, IM19 CAR-T, TC-110, anti-CD19 CAR T-cell therapy (B-cell acute lymphoblastic leukemia, Universiti Kebangsaan Malaysia), anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem, UCAR-011, ICTCAR-014, GC-007F, PTG-01, CC-97540, GC-007G, TC-310, GC-197, tisagenlecleucel-T, CART-19, tisagenlecleucel (CTL-019)), anti-CD20 CAR T-cell therapy (non-Hodgkin's lymphoma), MB-CART2019.1 (CD19/CD20), WZTL-002 dual anti-CD19/anti-CD20 CAR-T cells, ICG-132 (CD19/CD20), ACTR707 ATTCK-20, PBCAR-20A, LB-1905, CIK-CAR.CD33, CD33CART, dual anti-BCMA/anti-CD38 CAR T-cell therapy, CART-ddBCMA, MB-102, IM-23, JEZ-567, UCART-123, PD-1 knockout T cell therapy (esophageal cancer/NSCLC), ICT-CAR-052, Tn MUC-1 CAR-T, ICTCAR-053, PD-1 knockout T cell therapy (esophageal cancer/NSCLC), AUTO-2, anti-BCMA CAR T-cell therapy, Descartes-011, anti-BCMA/anti-CD38 CAR T-cell therapy, CART-ddBCMA, BCMA-CS1 cCAR, CYAD-01 (NKG2D LIGAND MODULATOR), KD-045, PD-L1 t-haNK, BCMA-CS1 cCAR, MEDI5083, anti-CD276 CART, and therapies disclosed in WO2012079000 or WO2017049166.

Cluster of Differentiation 47 (CD47) Inhibitors

In some embodiments a compound of Formula (I), (Ia), (Ib), or (Ic) provided herein, or pharmaceutically acceptable salt thereof, is administered with an inhibitor of CD47 (IAP, MER6, OA3; NCBI Gene ID: 961). Examples of CD47 inhibitors include anti-CD47 mAbs (Vx-1004), anti-human CD47 mAbs (CNTO-7108), CC-90002, CC-90002-ST-001, humanized anti-CD47 antibody or a CD47-blocking agent, NI-1701, NI-1801, RCT-1938, ALX148, SG-404, SRF-231, and TTI-621. Additional exemplary anti-CD47 antibodies include CC-90002, magrolimab (Hu5F9-G4), AO-176 (Vx-1004), letaplimab (IBI-188) (letaplimab), lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, ALX-148, AK-117, TTI-621, TTI-622, or compounds disclosed in WO199727873, WO199940940, WO2002092784, WO2005044857, WO2009046541, WO2010070047, WO2011143624, WO2012170250, WO2013109752, WO2013119714, WO2014087248, WO2015191861, WO2016022971, WO2016023040, WO2016024021, WO2016081423, WO2016109415, WO2016141328, WO2016188449, WO2017027422, WO2017049251, WO2017053423, WO2017121771, WO2017194634, WO2017196793, WO2017215585, WO2018075857, WO2018075960, WO2018089508, WO2018095428, WO2018137705, WO2018233575, WO2019027903, WO2019034895, WO2019042119, WO2019042285, WO2019042470, WO2019086573, WO2019108733, WO2019138367, WO2019144895, WO2019157843, WO2019179366, WO2019184912, WO2019185717, WO2019201236, WO2019238012, WO2019241732, WO2020019135, WO2020036977, WO2020043188, and WO2020009725. In some embodiments, the CD47 inhibitor is RRx-001, DSP-107, VT-1021, IMM-02, SGN-CD47M, or SIRPa-Fc-CD40L (SL-172154). In some embodiments the CD47 inhibitor is magrolimab.

In some embodiments, the CD47 inhibitor is a bispecific antibodies targeting CD47, such as IBI-322 (CD47/PD-L1), IMM-0306 (CD47/CD20), TJ-L1$C_4$ (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801.

SIRPα Targeting Agents

In some embodiments a compound of Formula (I), (Ia), (Ib), or (Ic) provided herein, or pharmaceutically acceptable salt thereof, is administered with a SIRPca targeting agent (NCBI Gene ID: 140885; UniProt P78324). Examples of SIRPca targeting agents that can be co-administered include SIRPα inhibitors, such as AL-008, RRx-001, and CTX-5861, and anti-SIRPca antibodies, such as FSI-189 (GS-0189), ES-004, BI-765063, ADU1805, CC-95251, Q-1801 (SIRPu/PD-L1). Additional SIRPa-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

FLT3R Agonists

In some embodiments a compound of Formula (I), (Ia), (Ib), or (Ic) provided herein, or pharmaceutically acceptable salt thereof, is administered with a FLT3R agonist. In some embodiments, the compound provided herein, or pharmaceutically acceptable salt thereof, is administered with a FLT3 ligand. In some embodiments, the compound provided herein, or pharmaceutically acceptable salt thereof, is administered with a FLT3L-Fc fusion protein, e.g., as described in WO2020263830. In some embodiments the compound provided herein, or pharmaceutically acceptable salt thereof, is administered with GS-3583 or CDX-301. In some embodiments the compound provided herein, or pharmaceutically acceptable salt thereof, is administered with GS-3583.

TNF Receptor Superfamily (TNFRSF) Member Agonists or Activators

In some embodiments, a compound of Formula (I), (Ia), (Ib), or (Ic) provided herein, or pharmaceutically acceptable salt thereof, is administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include MEDI6469, MEDI6383, tavolixizumab (MEDI0562), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include RG7876, SEA-CD40, APX-005M, and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include urelumab, utomilumab (PF-05082566), AGEN-2373, and ADG-106.

In some embodiments the anti-TNFRSF17 (BCMA) antibody GSK-2857916 is co-administered.

Example anti-TNFRSF18 (GITR) antibodies that can be co-administered include MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi-specific antibodies targeting TNFRSF family members that can be co-administered include PRS-343 (CD-137/HER2), AFM26 (BCMA/CD16A), AFM-13 (CD16/CD30), odronextamab (REGN-1979; CD20/CD3), AMG-420 (BCMA/CD3), INHIBRX-105 (4-1BB/PDL1), FAP-4-IBBL (4-1BB/FAP), plamotamab (XmAb-13676; CD3/CD20), RG-7828 (CD20/CD3), CC-93269 (CD3/BCMA), REGN-5458 (CD3/BCMA), and IMM-0306 (CD47/CD20).

TGFβ Antagonists

In some embodiments, a compound of Formula (I), (Ia), (Ib), or (Ic) provided herein, or pharmaceutically acceptable salt thereof, is administered with a TGFβ antagonist. In some embodiments, the TGFβ antagonist is a TGFβ-specific antibody. TGFβ-specific antibodies can be prepared and characterized using methods known to those of skill in the art, such as those described in PCT International Application Publication No. WO 2018/129329 and in U.S. Pat. No. 9,518,112. In some embodiments, the TGFβ antagonist binds to a TGFβ latency-associated peptide (LAP), e.g., TGFβ 1-LAP. TGFβ 1-LAP-specific antibodies can be prepared and characterized using methods known to those of skill in the art, such as those described in U.S. Pat. No. 8,198,412 or U.S. Pat. No. 10,017,567. In some embodiments, the TGFβ antagonist binds to TGFβ (e.g., TGFβ 1) in a context independent manner (e.g., independent of the presentation of TGF β in a specific tissue or organ). In some embodiments, the TGFβ antagonist binds to TGFβ (e.g., TGFβ 1) in a context-dependent manner. In some embodiments, the TGFβ antagonist blocks activation of latent TGFβ (e.g., latent TGFβ 1) that is localized in extracellular matrix, e.g., in connective tissue of the liver. In some embodiments, the TGFβ antagonist blocks activation of latent TGFβ (e.g., latent TGFβ 1) that is localized in the thymus, a lymph node, or in a tumor microenvironment (e.g., in a patient having liver cancer). In some embodiments, the TGFβ antagonist blocks activation of latent TGFβ (e.g., latent TGFβ 1) by Latent TGFβ Binding Protein (LTBP). In some embodiments, the TGFβ antagonist blocks activation of latent TGFβ (e.g., latent TGFβ 1) by Glycoprotein-A Repetitions Predominant protein (GARP), as described, e.g., in U.S. Pat. No. 10,000,572. In some embodiments, the TGFβ antagonist is ARGX-115. In some embodiments, the TGFβ antagonist is SK-181. In some embodiments, the TGFβ antagonist is an anti-latency-associated peptide (LAP) antibody that specifically binds to a LAP-TGFβ complex. In some embodiments, the anti-LAP antibody specifically binds to LAP-TGFβ complexes in extracellular matrix (ECM), e.g., of connective tissue in the liver. In some embodiments, the anti-LAP antibody specifically binds to LAP-TGFβ complexes on the surfaces of certain immunosuppressive cell types, such as regulatory T cells (Tregs), tumor-associated macrophages, or myeloid-derived suppressor cells, e.g., in a tumor microenvironment. In some embodiments, the anti-LAP antibody is a TLS-01 antibody. In some embodiments, the anti-LAP antibody specifically binds to LAP-TGFβ complexes in any context. In some embodiments, the anti-LAP antibody is a TLS-02 antibody. In some embodiments, the TGFβ antagonist comprises a TGFβ receptor. In some embodiments, the TGFβ antagonist is a TGFβ receptor-Fc fusion protein. In some embodiments, the TGFβ antagonist is an antibody comprising a TGFβ receptor. TGFβ antagonists comprising a TGFβ receptor that can be useful in connection with the compositions and methods provided herein have been described, e.g., in PCT International Publication Nos. WO 2019/113123 A1 and WO 2019/113464 A1.

Bi-Specific T-Cell Engagers

In some embodiments a compound of Formula (I), (Ia), (Ib), or (Ic) provided herein, or pharmaceutically acceptable salt thereof, is administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include duvortuxizumab (JNJ-64052781; CD19/CD3), AMG-211 (CEA/CD3), AMG-160 (PSMA/CD3), RG7802 (CEA/CD3), ERY-974 (CD3/GPC3), PF-06671008 (Cadherins/CD3), APV0436 (CD123/CD3), flotetuzumab (CD123/CD3), odronextamab (REGN-1979; CD20/CD3), MCLA-117 (CD3/CLEC12A), JNJ-0819 (heme/CD3), JNJ-7564 (CD3/heme), AMG-757 (DLL3-CD3), AMG-330 (CD33/CD3), AMG-420 (BCMA/CD3), AMG-427 (FLT3/CD3), AMG-562 (CD19/CD3), AMG-596 (EGFRvIII/CD3), AMG-673 (CD33/CD3), AMG-701 (BCMA/CD3), AMG-757 (DLL3/CD3), AMG-211 (CEA/CD3), blinatumomab (CD19/CD3), huGD2-BsAb (CD3/GD2), ERY974 (GPC3/CD3), GEMoab (CD3/PSCA), RG6026 (CD20/CD3), RG6194 (HER2/CD3), PF-06863135 (BCMA/CD3), SAR440234 (CD3/CDwl23), JNJ-9383 (MGD-015), AMG-424 (CD38/CD3), tidutamab (XmAb-18087 (SSTR2/CD3)), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), tidutamab (XmAb-18087; SSTR2/CD3), catumaxomab (CD3/EpCAM), REGN-4018 (MUC16/CD3), mosunetuzumab (RG-7828; CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology*. (2017) May 17; 6(7): e1326437); PD-L1 (Horn, et al., *Oncotarget*. 2017 Aug. 3; 8(35):57964-57980); and EGFRvIII (Yang, et al., *Cancer Lett*. 2017 Sep. 10; 403:224-230).

Bi- and Tri-Specific Natural Killer (NK)-Cell Engagers

In some embodiments a compound of Formula (I), (Ia), (Ib), or (Ic) provided herein, or pharmaceutically acceptable salt thereof, is administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcTR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol*. (2016) 1441:333-346; Fang, et al., *Semin Immunol*. (2017) 31:37-54.

MCL1 apoptosis regulator, BCL2 family member (MCL1) Inhibitors

In some embodiments a compound of Formula (I), (Ia), (Ib), or (Ic) provided herein, or pharmaceutically acceptable salt thereof, is administered with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include tapotoclax (AMG-176), AMG-397, S-64315, AZD-5991, 483-LM, A-1210477, UMI-77, JKY-5-037, PRT-1419, GS-9716, and those described in WO2018183418, WO2016033486, and WO2017147410.

SHP2 Inhibitors

In some embodiments a compound of Formula (I), (Ia), (Ib), or (Ic) provided herein, or pharmaceutically acceptable salt thereof, is administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, and those described in WO2018172984 and WO2017211303.

Hematopoietic Progenitor Kinase 1 (HPK1) Inhibitors and Degraders

In some embodiments a compound of Formula (I), (Ia), (Ib), or (Ic) provided herein, or pharmaceutically acceptable salt thereof, is administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation, those described in WO2020092621, WO2018183956, WO2018183964, WO2018167147, WO2018049152, WO2020092528, WO2016205942, WO2016090300, WO2018049214, WO2018049200, WO2018049191, WO2018102366, WO2018049152, and WO2016090300.

Apoptosis Signal-Regulating Kinase (ASK) Inhibitors

In some embodiments a compound of Formula (I), (Ia), (Ib), or (Ic) provided herein, or pharmaceutically acceptable salt thereof, is administered with an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include those described in WO2011008709 (Gilead Sciences) and WO 2013112741 (Gilead Sciences).

Bruton Tyrosine Kinase (BTK) Inhibitors

In some embodiments a compound of Formula (I), (Ia), (Ib), or (Ic) provided herein, or pharmaceutically acceptable salt thereof, is administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include (S)-6-amino-9-(1-(but-2-ynoyl)pyrrolidin-3-yl)-7-(4-phenoxyphenyl)-7H-purin-8(9H)-one, acalabrutinib (ACP-196), zanubrutinib (BGB-3111), CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, PCI-32765, and TAS-5315.

Cyclin-dependent Kinase (CDK) Inhibitors

In some embodiments a compound of Formula (I), (Ia), (Ib), or (Ic) provided herein, or pharmaceutically acceptable salt thereof, is administered with an inhibitor of cyclin dependent kinase 1 (CDK1, CDC2; CDC28A; P34CDC2;

NCBI Gene ID: 983); cyclin dependent kinase 2 (CDK2, CDKN2; p33(CDK2); NCBI Gene ID: 1017); cyclin dependent kinase 3 (CDK3,; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022), or cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include abemaciclib, alvocidib (HMR-1275, flavopiridol), AT-7519, dinaciclib, ibrance, FLX-925, LEE001, palbociclib, samuraciclib, ribociclib, rigosertib, selinexor, UCN-01, SY1365, CT-7001, SY-1365, G1T38, milciclib, trilaciclib, simurosertib hydrate (TAK931), and TG-02.

Discoidin Domain Receptor (DDR) Inhibitors

In some embodiments a compound of Formula (I), (Ia), (Ib), or (Ic) provided herein, or pharmaceutically acceptable salt thereof, is combined with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In some embodiments a compound of Formula (I), (Ia), (Ib), or (Ic) provided herein, or pharmaceutically acceptable salt thereof, is administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In some embodiments the targeted E3 ligase ligand conjugates comprise a targeting or binding moiety that targets or binds a protein described herein, and an E3 ligase ligand or binding moiety. In some embodiments the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In some embodiments the targeted E3 ligase ligand conjugates comprise a kinase inhibitor (e.g., a small molecule kinase inhibitor, e.g., of BTK and an E3 ligase ligand or binding moiety. See, e.g., WO2018098280. In some embodiments the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208, and WO2018144649.

Histone Deacetylase (HDAC) Inhibitors

In some embodiments a compound of Formula (I), (Ia), (Ib), or (Ic) provided herein, or pharmaceutically acceptable salt thereof, is administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

Indoleamine-pyrrole-2,3-dioxygenase (IDO1) inhibitors

In some embodiments a compound of Formula (I), (Ia), (Ib), or (Ic) provided herein, or pharmaceutically acceptable salt thereof, is administered with an inhibitor of indoleamine 2,3-dioxygenase 1 (IDO1; NCBI Gene ID: 3620). Examples of IDO1 inhibitors include BLV-0801, epacadostat, linrodostat (F-001287, BMS-986205), GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST, EOS-200271, KHK-2455, and LY-3381916.

Janus Kinase (JAK) Inhibitors

In some embodiments, a compound of Formula (I), (Ia), (Ib), or (Ic) provided herein, or pharmaceutically acceptable salt thereof, is administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, LJAK; NCBI Gene ID: 3718). Examples of JAK inhibitors include AT9283, AZD1480, baricitinib, BMS-911543, fedratinib, filgotinib (GLPG0634), gandotinib (LY2784544), INCB039110 (itacitinib), lestaurtinib, momelotinib (CYT0387), ilginatinib maleate (NS-018), pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In some embodiments a compound of Formula (I), (Ia), (Ib), or (Ic) provided herein, or pharmaceutically acceptable salt thereof, is administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL2 inhibitors include the antibodies described in WO 2009017833 (Arresto Biosciences), WO 2009035791 (Arresto Biosciences), and WO 2011097513 (Gilead Biologics).

Matrix Metalloprotease (MMP) Inhibitors

In some embodiments a compound of Formula (I), (Ia), (Ib), or (Ic), provided herein, or pharmaceutically acceptable salt thereof, is administered with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID:

56547), MMP27 (NCBI Gene ID: 64066) and/or MMP28 (NCBI Gene ID: 79148). Examples of MMP9 inhibitors include marimastat (BB-2516), cipemastat (Ro 32-3555), GS-5745 (andecaliximab), and those described in WO 2012027721 (Gilead Biologics).

RAS and RAS Pathway Inhibitors

In some embodiments a compound of Formula (I), (Ia), (Ib), or (Ic) provided herein, or pharmaceutically acceptable salt thereof, is administered with an inhibitor of KRAS proto-oncogene, GTPase (KRAS; a.k.a., NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893) or HRAS proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include sotorasib (AMG-510), COTI-219, ARS-3248, WDB-178, BI-3406, BI-1701963, SML-8-73-1 (G12C), adagrasib (MRTX-849), ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 and KRpep-2d. Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered include BGB-283, HM-95573, LXH-254, LY-3009120, RG7304 and TAK-580. Illustrative ERK inhibitors that can be co-administered include LTT-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, inavolisib (RG6114), ASN-003. Illustrative AKT inhibitors that can be co-administered include capivasertib and GSK2141795. Illustrative PI3K/mTOR inhibitors that can be co-administered include dactolisib, omipalisib, voxtalisib. gedatolisib, GSK2141795, GSK-2126458, inavolisib (RG6114), sapanisertib, ME-344, sirolimus (oral nanoamorphous formulation, cancer), racemetyrosine (TYME-88 (mTOR/cytochrome P450 3A4)), temsirolimus (TORISEL®, CCI-779), CC-115, onatasertib (CC-223), SF-1126, and PQR-309 (bimiralisib). In some embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

Mitogen-activated Protein Kinase (MEK) Inhibitors

In some embodiments a compound of Formula (I), (Ia), (Ib), or (Ic) provided herein, or pharmaceutically acceptable salt thereof, is administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, and refametinib.

Phosphatidylinositol 3-kinase (PI3K) Inhibitors

In some embodiments a compound of Formula (I), (Ia), (Ib), or (Ic) provided herein, or pharmaceutically acceptable salt thereof, is administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments the PI3K inhibitor is a pan-PI3K inhibitor. Examples of PI3K inhibitors include ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO2005113556 (ICOS), WO 2013/052699 (Gilead Calistoga), WO2013116562 (Gilead Calistoga), WO2014100765 (Gilead Calistoga), WO2014100767 (Gilead Calistoga), and WO2014201409 (Gilead Sciences).

Spleen Tyrosine Kinase (SYK) Inhibitors

In some embodiments a compound of Formula (I), (Ia), (Ib), or (Ic) provided herein, or pharmaceutically acceptable salt thereof, is administered with an inhibitor of spleen associated tyrosine kinase (SYK, p72-Syk, NCBI Gene ID: 6850). Examples of SYK inhibitors include 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), gusacitinib (ASN-002), and those described in U.S. Pat. No. 8,450,321 (Gilead Connecticut) and US20150175616.

Toll-Like Receptor (TLR) Agonists

In some embodiments a compound of Formula (I), (Ia), (Ib), or (Ic) provided herein, or pharmaceutically acceptable salt thereof, is administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include DS-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, BDB-001, DSP-0509, and the compounds disclosed in US20100143301 (Gilead Sciences), US20110098248 (Gilead Sciences), and US20090047249 (Gilead Sciences), US20140045849 (Janssen), US20140073642 (Janssen), WO2014056953 (Janssen), WO2014076221 (Janssen), WO2014128189 (Janssen), US20140350031 (Janssen), WO2014023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262. Example TLR8 agonists that can be co-administered include E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include AST-008, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, leftolimod (MGN-1703), CYT-003, CYT-003-QbG10 and PUL-042. Examples of TLR3 agonist include rintatolimod, poly-ICLC, RIBOXXON®, Apoxxim, RIBOXXIM®, IPH-33, MCT-465, MCT-475, and ND-1.1.

Tyrosine-Kinase Inhibitors (TKIs)

In some embodiments a compound of Formula (I), (Ia), (Ib), or (Ic) provided herein, or pharmaceutically acceptable salt thereof, is administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). Exemplary EGFR targeting agents include neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596 (EGFRvIII/CD3), lifirafenib (BGB-283), vectibix, lazertinib (LECLAZA®), and compounds disclosed in Booth, et al., Cancer Biol Ther. 2018 Feb. 1; 19(2):132-137. Antibodies targeting EGFR include without limitation modotuximab, cetuximab sarotalocan (RM-1929), seribantumab, necitumumab, depatuxizumab mafodotin (ABT-414), tomuzotuximab, depatuxizumab (ABT-806), and cetuximab.

Chemotherapeutic Agents

In some embodiments a compound of Formula (I), (Ia), (Ib), or (Ic) provided herein, or pharmaceutically acceptable salt thereof, is administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; sabizabulin (Veru-111); platinum analogs such as cisplatin and carboplatin, NC-6004 nanoplatin; aceglatone;

aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204, enobosarm (GTX-024), darolutamide, and IONIS-AR-2.5Rx (antisense).

An example progesterone receptor antagonist includes onapristone. Additional progesterone targeting agents include TRI-CYCLEN LO (norethindrone+ethinyl estradiol), norgestimate+ethinylestradiol (Tri-Cyclen) and levonorgestrel.

Anti-Angiogenic Agents

In some embodiments a compound of Formula (I), (Ia), (Ib), or (Ic) provided herein, or pharmaceutically acceptable salt thereof, is administered with an anti-angiogenic agent. Anti-angiogenic agents that can be co-administered include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2. Examples for anti-VEGFA antibodies that can be co-administered include bevacizumab, vanucizumab, faricimab, dilpacimab (ABT-165; DLL4/VEGF), or navicixizumab (OMP-305B83; DLL4/VEGF).

Anti-fibrotic Agents

In some embodiments a compound of Formula (I), (Ia), (Ib), or (Ic) provided herein, or pharmaceutically acceptable salt thereof, is administered with an anti-fibrotic agent. Anti-fibrotic agents that can be co-administered include the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 20040248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio) butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In some embodiments a compound of Formula (I), (Ia), (Ib), or (Ic) provided herein, or pharmaceutically acceptable salt thereof, is administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include mofezolac, GLY-230, and TRK-700.

Examples of inhibitors of prostaglandin-endoperoxide synthase 2 (PTGS2, COX-2; NCBI Gene ID: 5743) that can be co-administered include diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, NS-398, pamicogrel, parecoxib, robenacoxib, rofecoxib, rutecarpine, tilmacoxib, and zaltoprofen. Examples of dual COX1/COX2 inhibitors that can be co-administered include HP-5000, lornoxicam, ketorolac tromethamine, bromfenac sodium, ATB-346, HP-5000. Examples of dual COX-2/carbonic anhydrase (CA) inhibitors that can be co-administered include polmacoxib and imrecoxib.

Examples of inhibitors of secreted phospholipase A2, prostaglandin E synthase (PTGES, PGES; Gene ID: 9536) that can be co-administered include LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett*. (2017) 389:23-32; and Liu, et al., *Oncotarget*. (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include meclofenamate sodium, zileuton.

Examples of inhibitors of soluble epoxide hydrolase 2 (EPHX2, SEH; NCBI Gene ID: 2053) that can be co-administered include compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include GS-4875, GS-5290, BHM-078 and those described in WO2006124944, WO2006124692, WO2014064215, WO2018005435, Teli, et al., *J Enzyme Inhib Med Chem*. (2012) 27(4):558-70; Gangwall, et al., *Curr Top Med Chem*. (2013) 13(9):1015-35; Wu, et al., *Bioorg Med Chem Lett*. (2009) 19(13):3485-8; Kaila, et al., *Bioorg Med Chem*. (2007) 15(19):6425-42; and Hu, et al., *Bioorg Med Chem Lett*. (2011) 21(16):4758-61.

Tumor Oxygenation Agents

In some embodiments a compound of Formula (I), (Ia), (Ib), or (Ic) provided herein, or pharmaceutically acceptable salt thereof, is administered with an agent that promotes or increases tumor oxygenation or reoxygenation, or prevents or reduces tumor hypoxia. Illustrative agents that can be co-administered include, e.g., Hypoxia inducible factor-1 alpha (HIF-1a) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO2007137767, WO2007139791, WO2014107171, and WO2016149562.

Immunotherapeutic Agents

In some embodiments a compound of Formula (I), (Ia), (Ib), or (Ic) provided herein, or pharmaceutically acceptable salt thereof, is administered with an immunotherapeutic agent. In some embodiments the immunotherapeutic agent is an antibody. Example immunotherapeutic agents that can be co-administered include abagovomab, AB308, ABP-980, adecatumumab, afutuzumab, alemtuzumab, altumomab, amatuximab, anatumomab, arcitumomab, atezolizumab, bavituximab, bectumomab, bevacizumab, bivatuzumab, blinatumomab, brentuximab, camidanlumab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab, and 3F8. Rituximab can be used for treating indolent B-cell cancers, including marginal-zone lymphoma, WM, CLL, and small lymphocytic lymphoma. A combination of rituximab and chemotherapy agents is especially effective.

The exemplified therapeutic antibodies can be further labeled or combined with a radioisotope particle such as indium-111, yttrium-90 (90Y-clivatuzumab), or iodine-131.

In some embodiments, the immunotherapeutic agent that can be co-administered is an antibody-drug conjugate (ADC). Illustrative ADCs that can be co-administered include without limitation drug-conjugated antibodies, fragments thereof, or antibody mimetics targeting the proteins or antigens listed above and herein. Example ADCs that can be co-administered include gemtuzumab, brentuximab, belantamab (e.g., belantamab mafodotin), camidanhirnab (e.g., camidanlumab tesirine), trastuzumab (e.g., trastuzumab deruxtecan; trasuzumab emtansine), inotuzumab, glembatumumab, anetumab, mirvetuximab (e.g., mirvetuximab soravtansine), depatuxizumab, vadastuximab, labetuzumab, ladiratuzumab (e.g., ladiratuzumab vedotin), loncastuximab (e.g., loncastuximab tesirine), sacituzumab (e.g., sacituzumab govitecan), datopotamab (e.g., datopotamab deruxtecan; DS-1062; Dato-DXd), patritumab (e.g., patritumab deruxtecan), lifastuzumab, indusatumab, polatuzumab (e.g., polatuzumab vedotin), pinatuzumab, coltuximab, upifitaiab (e.g., upifiamrnab rilsodotin), indatuximab, milatuzumab, rovalpituzumab (e.g., rovalpituzumab tesirine), enfortumab (e.g., enfortumab vedotin), tisotumab (e.g., tisotumab vedotin), tusamnitamab (e., tusamitamab ravtaisine), disitamab (e.g., disitamab vedotin), telisotuzumab vedotin (ABBV-399), AGS-16C3F, ASG-22ME, AGS67E, AMG172, AMG575, BAY1129980, BAY1187982, BAY94-9343, GSK2857916, Humax-TF-ADC, IMGN289, IMGN151, IMGN529, IMGN632, IMGN853, IMGC936, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A, SYD985, DS-7300, XMT-1660, IMMU-130, and IMMU-140. ADCs that can be co-administered are described, e.g., in Lambert, et al., Adv Ther (2017) 34:1015-1035 and in de Goeij, *Current Opinion in Immunology* (2016) 40:14-23.

Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a *vinca* alkaloid, an epothilone), a pyrrolobenzodiazepine (PBD) or dimer thereof, a duocarmycin (A, B1, B2, C1, C2, D, SA, CC-1065), and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38). In some embodiments, the therapeutic agents (e.g., anticancer or antineoplastic agents) that can be conjugated to the drug-conjugated antibodies, fragments thereof, or antibody mimetics include an immune checkpoint inhibitor. In some embodiments the conjugated immune checkpoint inhibitor is a conjugated small molecule inhibitor of CD274 (PDL1, PD-L1), programmed cell death 1 (PDCD1, PD1, PD-1) or CTLA4. In some embodiments the conjugated small molecule inhibitor of CD274 or PDCD1 is selected from the group consisting of GS-4224, GS-4416, INCB086550 and MAX10181. In some embodiments the conjugated small molecule inhibitor of CTLA4 comprises BPI-002.

In some embodiments the ADCs that can be co-administered include an antibody targeting tumor-associated calcium signal transducer 2 (TROP-2; TACSTD2; EGP-1; NCBI Gene ID: 4070). Illustrative anti-TROP-2 antibodies include without limitation TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Klus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (*Mediterranea* Theranostic, LegoChem Biosciences), KD-065 (Nanjing KAEDI Biotech), and those described in WO2020016662 (Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585

(Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464 (LivTech/Chiome), U.S. Ser. No. 10/501,555 (Abruzzo Theranostic/Oncoxx), WO2018036428 (Sichuan Kelun Pharma), WO2013068946 (Pfizer), WO2007095749 (Roche), and WO2020094670 (SynAffix). In some embodiments, the anti-Trop-2 antibody is selected from hRS7, Trop-2-XPAT, and BAT-8003. In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. In some embodiments, the antibody-drug conjugate comprises an anti-Trop-2 antibody and an anticancer agent linked by a linker. In some embodiments, the linker includes the linkers disclosed in U.S. Pat. No. 7,999,083. In some embodiments, the linker is CL2A. In some embodiments, the drug moiety of antibody-drug conjugate is a chemotherapeutic agent. In some embodiments, the chemotherapeutic agent is selected from doxorubcin (DOX), epirubicin, morpholinodoxorubicin (morpholino-DOX), cyanomorpholino-doxorubicin (cyanomorpholinoDOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38. In some embodiments the antibody and/or fusion protein provided herein is administered with sacituzumab govitecan.

In some embodiments the ADCs that can be co-administered include an antibody targeting carcinoembryonic antigen-related cell adhesion molecule 5 (CEACAM5; CD66a; NCBI Gene ID: 634). In some embodiments the CEACAM5 antibody is hMN-14 (e.g., as described in WO1996011013). In some embodiments the CEACAM5-ADC is as described in WO2010093395 (anti-CEACAM-5-CL2A-SN38). In some embodiments the antibody and/or fusion protein provided herein is administered with the CEACAM5-ADC IMMU-130.

In some embodiments the ADCs that can be co-administered include an antibody targeting MHC class II cell surface receptor encoded by the human leukocyte antigen complex (HLA-DR). In some embodiments the HLA-DR antibody is hL243 (e.g., as described in WO2006094192). In some embodiments the HLA-DR-ADC is as described in WO2010093395 (anti-HLA-DR-CL2A-SN38). In some embodiments the antibody and/or fusion protein provided herein is administered with the HLA-DR-ADC IMMU-140.

Cancer Gene Therapy and Cell Therapy

In some embodiments a compound of Formula (I), (Ia), (Ib), or (Ic) provided herein, or pharmaceutically acceptable salt thereof, is administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In some embodiments a compound of Formula (I), (Ia), (Ib), or (Ic) provided herein, or pharmaceutically acceptable salt thereof, is administered with one or more cellular therapies. Illustrative cellular therapies include without limitation co-administration of one or more of a population of natural killer (NK) cells, NK-T cells, T cells, cytokine-induced killer (CIK) cells, macrophage (MAC) cells, tumor infiltrating lymphocytes (TILs) and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments the cellular therapy entails co-administering cells comprising chimeric antigen receptors (CARs). In such therapies, a population of immune effector cells engineered to express a CAR, wherein the CAR comprises a tumor antigen-binding domain. In T cell therapies, the T cell receptors (TCRs) are engineered to target tumor derived peptides presented on the surface of tumor cells.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12.

In some embodiments, the costimulatory domain comprises a functional domain of one or more proteins selected from the group consisting of CD27, CD28, 4-1BB(CD137), OX40, CD30, CD40, PD-1, ICOS, CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD160, CD19, IL2R beta, IL2R gamma, IL7R, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, CD29, ITGB2 (LFA-1, CD18), ITGB7, TNFR2, DNAM1 (CD226), SLAMF4 (CD244, 2B4), CD84, CD96 (TACTILE), CEACAMI, CRTAM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKp44, NKp30, NKp46, NKG2D, and NKG2C.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (αNeuSAc(2-8)αNeuSAc(2-3)βDGaip(1-4)bDGIcp(1-1) Cer); ganglioside GM3 (αNeuSAc(2-3)βDGalp(1-4) βDGlcp(1-1)Cer); TNF receptor superfamily member 17 (TNFRSF17, BCMA); Tn antigen ((Tn Ag) or (GaINAcu-Ser/Thr)); prostate-specific membrane antigen (PSMA); receptor tyrosine kinase-like orphan receptor 1 (RORI); tumor-associated glycoprotein 72 (TAG72); CD38; CD44v6; Carcinoembryonic antigen (CEA); epithelial cell adhesion molecule (EPCAM); B7H3 (CD276); KIT (CD117); interleukin-13 receptor subunit alpha-2 (IL-13Ra2 or CD213A2); mesothelin; interleukin 11 receptor alpha (IL-11Ra); prostate stem cell antigen (PSCA); protease serine 21 (Testisin or PRSS21); vascular endothelial growth factor receptor 2 (VEGFR2); Lewis(Y)antigen; CD24; platelet-derived growth factor receptor beta (PDGFR-beta); stage-specificembryonic antigen-4 (SSEA-4); CD20; delta like 3 (DLL3); folate receptor alpha; receptor tyrosine-protein kinase, ERBB2 (Her2/neu); mucin 1, cell surface associated (MUC1); epidermal growth factor receptor (EGFR); neural cell adhesion molecule (NCAM); prostase; prostatic acid phosphatase (PAP); elongation factor 2 mutated (ELF2M); ephrin B2; fibroblast activation protein alpha (FAP); insulin-like growth factor 1 receptor (IGF-I receptor), carbonic anhydrase IX (CAIX); proteasome (Prosome, Macropain) subunit, beta type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); fucosyl GM1; sialyl Lewis adhesion molecule (sLe); transglutaminase 5 (TGS5); high molecular weight-melanomaassociatedantigen (HMW-MAA); o-acetyl-GD2 ganglioside (OAcGD2); folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CX-ORF61); CD97; CD179a; anaplastic lymphoma kinase (ALK); polysialic acid; placenta-specific 1 (PLAC1); hexasaccharide portion of globoH glycoceramide (GloboH); mammary gland differentiation antigen (NY-BR-1); uroplakin 2 (UPK2); hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); olfactory receptor 51E2 (ORS IE2); TCR Gamma Alternate Reading Frame Protein (TARP); Wilms tumor protein (WTi); cancer/testis antigen 1 (NY-ESO-1); cancer/testis antigen 2 (LAGE-la); melanoma associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); rat sarcoma (Ras) mutant; human telomerase reverse transcriptase (hTERT); sarcoma translocation breakpoints; melanoma inhibitor of apoptosis (ML-IAP); ERG (transmembrane protease, serine 2 (TM-PRSS2) ETS fusion gene); N-Acetyl glucosaminyl-transferase V (NA17); paired box protein Pax-3 (PAX3); androgen receptor; cyclin B1;v-myc avian myelocytomatosis viral oncogene neuroblastoma derived homolog (MYCN); ras homolog family member C (RhoC); tyrosinase-related protein 2 (TRP-2); cytochrome P450 1B1(CYP IBI); CCCTC-Binding Factor (Zinc Finger Protein)-Like (BORIS or Brother of the Regulator of Imprinted Sites), squamous cell carcinoma antigen recognized by T-cells 3 (SART3); paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); receptor for advanced glycation endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; leukocyte-associated immunoglobulin-like receptor 1 (LAIRI); Fc fragment of IgA receptor (FCAR or CD89); leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; $C_{10}$orf3, CT111, MARCH, URCC6; NCBI Gene ID: 55165), cancer/testis antigen 1A (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMADI; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPS1L1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., *Proc Natl Acad Sci USA*. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Examples of cell therapies include: Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, and CSG-005.

In some embodiments the one or more additional co-administered therapeutic agents can be categorized by their mechanism of action, e.g., into the following groups:

- agents targeting adenosine deaminase, such as pentostatin or cladribine;
- agents targeting ATM, such as AZD1390;
- agents targeting MET, such as savolitinib, capmatinib, tepotinib, ABT-700, AG213, JNJ-38877618 (OMO-1), merestinib, HQP-8361, BMS-817378, or TAS-115;
- agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4): 558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;
- agents targeting thymidine kinase, such as aglatimagene besadenovec (ProstAtak, PancAtak, GliAtak, GMCI, or AdV-tk);
- agents targeting targeting an interleukin pathway, such as pegilodecakin (AM-0010) (pegylated IL10), CA-4948 (IRAK4 inhibitor);
- agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);
- agents targeting CD73, such as a CD73 inhibitor (e.g., quemliclustat (AB680)) or an anti-CD73 antibody (e.g., oleclumab);
- agents targeting DKK3, such as MTG-201;
- agents targeting EEF1A2, such as plitidepsin;
- agents targeting EIF4A1, such as rohinitib;
- agents targeting endoglin, such as TRC105 (carotuximab);
- agents targeting exportin-1, such as eltanexor;
- agents targeting fatty acid amide hydrolase, such as compounds disclosed in WO2017160861;
- agents targeting heat shock protein 90 beta family member 1, such as anlotinib;
- agents targeting lactotransferrin, such as ruxotemitide (LTX-315);
- agents targeting lysyl oxidase, such as compounds disclosed in U.S. Pat. Nos. 4,965,288, 4,997,854, 4,943,593, 5,021,456, 5,059,714, 5,120,764, 5,182,297, 5,252,608, or US20040248871;
- agents targeting MAGE family members, such as KITE-718, MAGE-A10C796T, or MAGE-A10 TCR;
- agents targeting MDM2, such as ALRN-6924, CMG-097, milademetan monotosylate monohydrate (DS-3032b), or AMG-232;
- agents targeting MDM4, such as ALRN-6924;
- agents targeting melan-A, such as MART-1 F5 TCR engineered PBMCs;
- agents targeting mesothelin, such as CSG-MESO or TC-210;
- agents targeting METAP2, such as M8891 or APL-1202;
- agents targeting NLRP3, such as BMS-986299;
- agents targeting oxoglutarate dehydrogenase, such as devimistat (CPI-613);
- agents targeting placenta growth factor, such as aflibercept;
- agents targeting SLC10A3, such as compounds disclosed in WO2015148954, WO2012082647, or WO2017160861;
- agents targeting transforming growth factor alpha (TGFα), such as compounds disclosed in WO2019103203;
- agents targeting tumor protein p53, such as kevetrin (stimulator);
- agents targeting vascular endothelial growth factor A, such as aflibercept;
- agents targeting vascular endothelial growth factor receptor, such as fruquintinib or MP0250;
- agents targeting VISTA, such as CA-170, or HMBD-002;
- agents targeting WEEl, such as adavosertib (AZD-1775);
- small molecule inhibitors targeting ABL1, such as imatinib, rebastinib, asciminib, or ponatinib (ICLUSIG®);
- small molecule antagonists targeting adenosine receptor, such as CPI-444, AZD-4635, preladenant, etrumadenant (AB928), or PBF-509;
- small molecule inhibitors targeting arachidonate 5-lipoxygenase, such as meclofenamate sodium or zileuton;
- small molecule inhibitors targeting ATR serine/threonine kinase, such as BAY-937, ceralasertib (AZD6738), AZD6783, VX-803, or VX-970 (berzosertib);
- small molecule inhibitors targeting AXL receptor tyrosine kinase, such as bemcentinib (BGB-324), SLC-0211, or gilteritinib (Axl/Flt3);
- small molecule inhibitors targeting Bruton's tyrosine kinase (BTK), such as (S)-6-amino-9-(1-(but-2-ynoyl) pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;
- small molecule inhibitors targeting neurotrophic receptor tyrosine kinase such as larotrectinib, entrectinib, or selitrectinib (LOXO-195);
- small molecule inhibitors targeting ROS proto-oncogene 1, receptor tyrosine kinase, such as entrectinib, repotrectinib (TPX-0005), or lorlatinib;

- small molecule inhibitors targeting SRC proto-oncogene, non-receptor tyrosine kinase, such as VAL-201, tirbanibulin (KX2-391), or ilginatinib maleate (NS-018);
- small molecule inhibitors targeting B-cell lymphoma 2, such as navitoclax (ABT-263), venetoclax (ABT-199, RG-7601), or AT-101 (gossypol);
- small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;
- small molecule inhibitors targeting carbohydrate sulfotransferase 15, such as STNM-01;
- small molecule inhibitors targeting carbonic anhydrase, such as polmacoxib, acetazolamide, or methazolamide;
- small molecule inhibitors targeting catenin beta 1, such as CWP-291, or PRI-724;
- small molecule antagonists targeting a C-C motif chemokine receptor, such as CCX-872, BMS-813160 (CCR2/CCR5) or MK-7690 (vicriviroc);
- small molecule antagonists targeting a C-X-C motif chemokine receptor (e.g., CXCR4), blixafortide;
- small molecule inhibitors targeting cereblon, such as avadomide (CC-122), CC-92480, CC-90009, or iberdomide;
- small molecule inhibitors targeting checkpoint kinase 1, such as SRA737;
- small molecule inhibitors targeting a complement component, such as Imprime PGG (Biothera Pharmaceuticals);
- small molecule inhibitor targeting a C-X-C motif chemokine ligand (e.g., CXCL12), such as olaptesed pegol (NOX-A12);
- small molecule inhibitors targeting cytochrome P450 family, such as ODM-209, LAE-201, seviteronel (VT-464), CFG920, abiraterone, or abiraterone acetate;
- small molecule inhibitors targeting DEAD-box helicase 5, such as supinoxin (RX-5902);
- small molecule inhibitors targeting DGKa, e.g., such as described in WO2021130638;
- small molecule inhibitors targeting diablo IAP-binding mitochondrial protein, such as BI-891065;
- small molecule inhibitors targeting dihydrofolate reductase, such as pralatrexate or pemetrexed disodium;
- small molecule inhibitors targeting DNA dependent protein kinase, such as MSC2490484A (nedisertib), VX-984, AsiDNA (DT-01), LXS-196, or sotrastaurin;
- small molecule inhibitors targeting MARCKS, such as BIO-11006;
- small molecule inhibitors targeting RIPK1, such as GSK-3145094;
- small molecule inhibitors targeting Rho associated coiled-coil containing protein kinase, such as AT13148 or KD025;
- small molecule inhibitors targeting DNA topoisomerase, such as irinotecan, firtecan pegol, or amrubicin;
- small molecule inhibitors targeting dopamine receptor D2, such as ONC-201;
- small molecule inhibitors targeting DOT1 like histone lysine methyltransferase, such as pinometostat (EPZ-5676);
- small molecule inhibitors targeting EZH2, such as tazemetostat, CPI-1205, or PF-06821497;
- small molecule inhibitors targeting fatty acid synthase, such as TVB-2640 (Sagimet Biosciences);
- small molecule inhibitors targeting fibroblast growth factor receptor 2 (FGFR2), such as bemarituzumab (FPA144);
- small molecule inhibitors targeting focal adhesion kinase (FAK, PTK2), such as VS-4718, defactinib, or GSK2256098;
- small molecule inhibitors targeting folate receptor 1, such as pralatrexate;
- small molecule inhibitors targeting FOXM1, such as thiostrepton;
- small molecule inhibitors targeting galectin 3, such as belapectin (GR-MD-02);
- small molecule antagonists targeting glucocorticoid receptor, such as relacorilant (CORT-125134);
- small molecule inhibitors targeting glutaminase include without limitation CB-839 (telaglenastat), or bis-2-(5-phenylacetamido-1,3,4-thiadiazol-2-yl)ethyl sulfide (BPTES);
- small molecule inhibitors targeting GNRHR, such as elagolix, relugolix, or degarelix;
- small molecule inhibitors targeting EPAS1, such as belzutifan (PT-2977 (Merck & Co.));
- small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);
- small molecule inhibitors targeting lysine demethylase 1A, such as CC-90011;
- small molecule inhibitors targeting MAPK interacting serine/threonine kinase, such as tomivosertib (eFT-508);
- small molecule inhibitors targeting notch receptor, such as AL-101 (BMS-906024);
- small molecule inhibitors targeting polo like kinase 1 (PLK1), such as volasertib or onvansertib;
- small molecule inhibitors targeting poly(ADP-ribose) polymerase (PARP), such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, CEP 9722, CEP-8983, E7016, 3-aminobenzamide, or CK-102;
- small molecule inhibitors targeting polycomb protein EED, such as MAK683;
- small molecule inhibitors targeting porcupine O-acyltransferase, such as WNT-974;
- small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;
- small molecule inhibitors targeting protein arginine N methyltransferase, such as MS203, PF-06939999, GSK3368715, or GSK3326595;
- small molecule inhibitors targeting PTPN11, such as TNO155 (SHP-099), RMC-4550, JAB-3068, RMC- 4630 (SAR442720), or compounds disclosed in WO2018172984 or WO2017211303;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S (DSP-7888);

small molecule agonists targeting adenosine receptor, such as namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cytochrome P450 family, such as mitotane;

small molecule agonists targeting DExD/H-box helicase 58, such as RGT-100;

small molecule agonists targeting GNRHR, such as leuprorelin acetate, leuprorelin acetate sustained release depot (ATRIGEL), triptorelin pamoate, or goserelin acetate;

small molecule agonists targeting GRB2, such as prexigebersen (BP1001);

small molecule agonists targeting NFE2L2, such as omaveloxolone (RTA-408);

small molecule agonists targeting NOD2, such as mifamurtide (liposomal);

small molecule agonists targeting RAR-related orphan receptor gamma, such as cintirorgon (LYC-55716);

small molecule agonists targeting retinoic acid receptor (RAR), such as tretinoin;

small molecule agonists targeting STING1, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;

small molecule agonists targeting thyroid hormone receptor beta, such as levothyroxine sodium;

small molecule agonists targeting tumor necrosis factor, such as tasonermin;

antisense agents targeting baculoviral IAP repeat containing 5, such as EZN-3042;

antisense agents targeting GRB2, such as prexigebersen;

antisense agents targeting heat shock protein 27, such as apatorsen;

antisense agents targeting STAT3, such as danvatirsen (IONIS-STAT3-2.5Rx);

gene therapies targeting a C-C motif chemokine receptor, such as SB-728-T;

gene therapies targeting an interleukin, such as EGENE-001, tavokinogene telseplasmid, nogapendekin alfa (ALT-803), NKTR-255, NIZ-985 (hetIL-15), SAR441000, or MDNA-55;

antibodies targeting claudin 18, such as claudiximab;

antibodies targeting clusterin, such as AB-16B5;

antibodies targeting a complement component, such as ravulizumab (ALXN-1210);

antibodies targeting a C-X-C motif chemokine ligand, such as BMS-986253 (HuMax-Inflam);

antibodies targeting delta like canonical Notch ligand 4 (DLL4), such as demcizumab, navicixizumab (DLL4/VEGF);

antibodies targeting EPH receptor A3, such as fibatuzumab (KB-004);

antibodies targeting epithelial cell adhesion molecule, such as oportuzumab monatox (VB4-845);

antibodies targeting fibroblast growth factor, such as GAL-F2, B-701 (vofatamab);

antibodies targeting hepatocyte growth factor, such as MP-0250;

antibodies targeting an interleukin, such as canakinumab (ACZ885), gevokizumab (VPM087), CJM-112, guselkumab, talacotuzumab (JNJ-56022473), siltuximab, or tocilizumab;

antibodies targeting LRRC15, such as ABBV-085 or cusatuzumab (ARGX-110);

antibodies targeting mesothelin, such as BMS-986148, SEL-403, or anti-MSLN-MMAE;

antibodies targeting myostatin, such as landogrozumab;

antibodies targeting notch receptor, such as tarextumab;

antibodies targeting TGFB1 (TGFP1), such as SAR439459, ABBV-151, NIS793, SRK-181, XOMA089, or compounds disclosed in WO2019103203;

vaccines targeting fms related receptor tyrosine kinase, such as HLA-A2402/HLA-A0201 restricted epitope peptide vaccine;

vaccines targeting heat shock protein 27, such as PSV-AML (PhosphoSynVax);

vaccines targeting PD-L1, such as IO-120+IO-103 (PD-L1/PD-L2 vaccines) or IO-103;

vaccines targeting tumor protein p53, such as MVA-p53;

vaccines targeting WT1, such as WT-1 analog peptide vaccine (WT1-CTL);

cell therapies targeting baculoviral IAP repeat containing 5, such as tumor lysate/MUC1/survivin PepTivator-loaded dendritic cell vaccine;

cell therapies targeting carbonic anhydrase, such as DC-Ad-GMCAIX;

cell therapies targeting C-C motif chemokine receptor, such as CCR5-SBC-728-HSPC;

cell therapies targeting folate hydrolase 1, such as CIK-CAR.PSMA or CART-PSMA-TGFORDN;

cell therapies targeting GSTP1, such as CPG3-CAR (GLYCAR);

- cell therapies targeting HLA-A, such as FH-MCVA2TCR or NeoTCR-P1;
- cell therapies targeting an interleukin, such as CST-101;
- cell therapies targeting KRAS, such as anti-KRAS G12D mTCR PBL;
- cell therapies targeting MET, such as anti-cMet RNA CAR T;
- cell therapies targeting MUC16, such as JCAR-020;
- cell therapies targeting PD-1, such as PD-1 knockout T cell therapy (esophageal cancer/NSCLC);
- cell therapies targeting PRAME, such as BPX-701;
- cell therapies targeting transforming protein E7, such as KITE-439;
- cell therapies targeting WT1, such as WT1-CTL, ASP-7517, or JTCR-016.

Exemplified Combination Therapies

Lymphoma or Leukemia Combination Therapy

Some chemotherapy agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CC1-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP.

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCl-779), everolimus (RAD001), BMS-345541, curcumin, SAHA, thalidomide, lenalidomide (REVLIMID®, CC-5013), and geldanamycin (17 AAG).

Waldenstrom's Macroglobulinemia Combination Therapy

Therapeutic agents used to treat Waldenstrom's Macroglobulinemia (WM) include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma (DLBCL) Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE. In some embodiments therapeutic agents used to treat DLBCL include rituximab (Rituxan®), cyclophosphamide, doxorubicin hydrochloride (hydroxydaunorubicin), vincristine sulfate (Oncovin®), prednisone, bendamustine, ifosfamide, carboplatin, etoposide, ibrutinib, polatuzumab vedotin piiq, bendamustine, copanlisib, lenalidomide (Revlimid®), dexamethasone, cytarabine, cisplatin, Yescarta®, Kymriah®, Polivy® (polatuzumab vedotin), BR (bendamustine (Treanda®), gemcitabine, oxiplatin, oxaliplatin, tafasitamab, polatuzumab, cyclophosphamide, or combinations thereof. In some embodiments therapeutic agents used to treat DLBCL include R-CHOP (rituximab+cyclophosphamide+doxorubicin hydrochloride (hydroxydaunorubicin)+vincristine sulfate (Oncovin®), +prednisone), rituximab+bendamustine, R-ICE (Rituximab+Ifosfamide+Carboplatin+Etoposide), rituximab+lenalomide, R-DHAP (rituximab+dexamethasone+high-dose cytarabine (Ara C)+cisplatin), Polivy® (polatuzumab vedotin)+BR (bendamustine (Treanda®) and rituximab (Rituxan®), R-GemOx (Gemcitabine+oxaliplatin+rituximab), Tafa-Len (tafasitamab+lenalidomide), Tafasitamab+Revlimid®, polatuzumab+bendamustine, Gemcitabine+oxaliplatin, R-EPOCH (rituximab+etoposide phosphate+prednisone+vincristine sulfate (Oncovin®)+cyclophosphamide+doxorubicin hydrochloride (hydroxydaunorubicin)), or CHOP (cyclophosphamide+doxorubicin hydrochloride (hydroxydaunorubicin)+vincristine sulfate (Oncovin®)+prednisone). In some embodiments therapeutic agents used to treat DLBCL include tafasitamab, glofitamab, epcoritamab, Lonca-T (loncastuximab tesirine), Debio-1562, polatuzumab, Yescarta, JCAR017, ADCT-402, brentuximab vedotin, MT-3724, odronextamab, Auto-03, Allo-501A, or TAK-007.

Chronic Lymphocytic Leukemia Combination Therapy

Therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

High Risk Myelodysplastic Syndrome (HR MDS) Combination Therapy

Therapeutic agents used to treat HR MDS include azacitidine (Vidaza®), decitabine (Dacogen®), lenalidomide (Revlimid®), cytarabine, idarubicin, daunorubicin, and combinations thereof. In some embodiments, combinations include cytarabine+daunorubicin and cytarabine +idarubicin. In some embodiments therapeutic agents used to treat HR MDS include pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments therapeutic agents used to treat LR MDS include roxadustat, luspatercept, imetelstat, LB-100, or rigosertib.

Acute Myeloid Leukemia (AML) Combination Therapy

Therapautic agents used to treat AML include cytarabine, idarubicin, daunorubicin, midostaurin (Rydapt®), venetoclax, azacitidine, ivasidenib, gilteritinib, enasidenib, low-dose cytarabine (LoDAC), mitoxantrone, fludarabine, granulocyte-colony stimulating factor, idarubicin, gilteritinib (Xospata®), enasidenib (Idhifa®), ivosidenib (Tibsovo®), decitabine (Dacogen®), mitoxantrone, etoposide, Gemtuzumab ozogamicin (Mylotarg®), glasdegib (Daurismo®), and combinations thereof. In some embodiments therapeutic agents used to treat AML include FLAG1Ida (fludarabine, cytarabine (Ara-C), granulocyte-colony stimulating factor (G-CSF) and idarubicin), cytarabine+idarubicin, cytarabine+daunorubicin+midostaurin, venetoclax+azacitidine, cytarabine+daunorubicin, or MEC (mitoxantrone, etoposide, and cytarabine). In some embodiments, therapeutic agents used to treat AML include pevonedistat, venetoclax, sabatolimab, eprenetapopt, or lemzoparlimab.

Multiple Myeloma (MM) Combination Therapy

Therapeutic agents used to treat MM include lenalidomide, bortezomib, dexamethasone, daratumumab (Darzalex®), pomalidomide, Cyclophosphamide, Carfilzomib (Kyprolis®), Elotuzumab (Empliciti), and combinations thereof. In some embodiments therapeutic agents used to treat MM include RVS (lenalidomide+bortezomib+dexamethasone), RevDex (lenalidomide plus dexamethasone), CYBORD (Cyclophosphamide+Bortezomib+Dexamethasone), Vel/Dex (bortezomib plus dexamethasone), or PomDex (Pomalidomide+low-dose dexamethasone). In some embodiments therapeutic agents used to treat MM include JCARH125, TAK-573, belantamab-m, ide-cel (CAR-T).

Breast Cancer Combination Therapy

Therapeutic agents used to treat breast cancer include albumin-bound paclitaxel, anastrozole, atezolizumab, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, letrozole, methotrexate, mitoxantrone, paclitaxel, pegylated liposomal doxorubicin, pertuzumab, tamoxifen, toremifene, trastuzumab, vinorelbine, and any combinations thereof. In some embodiments therapeutic agents used to treat breast cancer (e.g., HR+/−/HER2+/−) include trastuzumab (Herceptin®), pertuzumab (Perjeta®), docetaxel, carboplatin, palbociclib (Ibrance®), letrozole, trastuzumab emtansine (Kadcyla®), fulvestrant (Faslodex®), olaparib (Lynparza®), eribulin, tucatinib, capecitabine, lapatinib, everolimus (Afinitor®), exemestane, eribulin mesylate (Halaven®), and combinations thereof. In some embodiments therapeutic agents used to treat breast cancer include trastuzumab+pertuzumab+docetaxel, trastuzumab+pertuzumab+docetaxel+carboplatin, palbociclib+letrozole, tucatinib+capecitabine, lapatinib+capecitabine, palbociclib+fulvestrant, or everolimus+exemestane. In some embodiments therapeutic agents used to treat breast cancer include trastuzumab deruxtecan (Enhertu®), datopotamab deruxtecan (DS-1062), enfortumab vedotin (Padcev®), balixafortide, elacestrant, or a combination thereof. In some embodiments therapeutic agents used to treat breast cancer include balixafortide+eribulin. Triple Negative Breast Cancer (TNBC) Combination Therapy Therapeutic agents used to treat TNBC include atezolizumab, cyclophosphamide, docetaxel, doxorubicin, epirubicin, fluorouracil, paclitaxel, and combinations thereof. In some embodiments therapeutic agents used to treat TNBC include olaparib (Lynparza®), atezolizumab (Tecentriq®), paclitaxel (Abraxane®), eribulin, bevacizumab (Avastin®), carboplatin, gemcitabine, eribulin mesylate (Halaven®), sacituzumab govitecan (Trodelvy®), pembrolizumab (Keytruda®), cisplatin, doxorubicin, epirubicin, or a combination thereof. In some embodiments therapeutic agents to treat TNBC include atezolizumab+paclitaxel, bevacizumab+paclitaxel, carboplatin+paclitaxel, carboplatin+gemcitabine, or paclitaxel+gemcitabine. In some embodiments therapeutic agents used to treat TNBC include eryaspase, capivasertib, alpelisib, rucaparib+nivolumab, atezolumab+paclitaxel+gemcitabine+capecitabine+carboplatin, ipatasertib+paclitaxel, ladiratuzumab vedotin+pembrolimab, durvalumab+DS-8201a, trilaciclib+gemcitabine+carboplatin. In some embodiments therapeutic agents used to treat TNBC include trastuzumab deruxtecan (Enhertu®), datopotamab deruxtecan (DS-1062), enfortumab vedotin (Padcev®), balixafortide, adagloxad simolenin, nelipepimut-s (NeuVax®), nivolumab (Opdivo®), rucaparib, toripalimab (Tuoyi®), camrelizumab, capivasertib, durvalumab (Imfinzi®), and combinations thereof. In some embodiments therapeutic agents use to treat TNBC include nivolumab+rucaparib, bevacizumab (Avastin®)+chemotherapy, toripalimab+paclitaxel, toripalimab+albumin-bound paclitaxel, camrelizumab+chemotherapy, pembrolizumab+chemotherapy, balixafortide+eribulin, durvalumab+trastuzumab deruxtecan, durvalumab+paclitaxel, or capivasertib+paclitaxel.

Bladder Cancer Combination Therapy

Therapeutic agents used to treat bladder cancer include datopotamab deruxtecan (DS-1062), trastuzumab deruxtecan (Enhertu©), erdafitinib, eganelisib, lenvatinib, bempegaldesleukin (NKTR-214), or a combination thereof. In some embodiments therapeutic agents used to treat bladder cancer include eganelisib+nivolumab, pembrolizumab (Keytruda®) +enfortumab vedotin (Padcev©), nivolumab+ipilimumab, duravalumab+tremelimumab, lenvatinib+pembrolizumab, enfortumab vedotin (Padcev©)+pembrolizumab, and bempegaldesleukin+nivolumab.

Colorectal Cancer (CRC) Combination Therapy

Therapeutic agents used to treat CRC include bevacizumab, capecitabine, cetuximab, fluorouracil, irinotecan, leucovorin, oxaliplatin, panitumumab, ziv-aflibercept, and any combinations thereof. In some embodiments therapeutic agents used to treat CRC include bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, or a combination thereof. In some embodiments therapeutic agents used to treat CRC include bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, bevacizumab+XELOX, and bevacizumab+FOLFOXIRI. In some embodiments therapeutic agents used to treat CRC include binimetinib+encorafenib+cetuximab, trametinib+dabrafenib+panitumumab, trastuzumab+pertuzumab, napabucasin+FOLFIRI+bevacizumab, nivolumab+ipilimumab.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof. In some embodiments therapeutic agents used to treat gastroesophageal junction cancer (GEJ) include herceptin, cisplatin, 5-FU, ramicurimab, or paclitaxel. In some embodiments therapeutic agents used to treat GEJ cancer include ALX-148, AO-176, or IBI-188.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head & neck cancer include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Therapeutic agents used to treat head and neck squamous cell carcinoma (HNSCC) include pembrolizumab, carboplatin, 5-FU, docetaxel, cetuximab (Erbitux®), cisplatin, nivolumab (Opdivo®), and combinations thereof. In some embodiments therapeutic agents used to treat HNSCC include pembrolizumab+carboplatin+5-FU, cetuximab+cisplatin+5-FU, cetuximab+carboplatin+5-FU, cisplatin+5-FU, and carboplatin+5-FU. In some embodiments therapeutic agents used to treat HNSCC include durvalumab, durvalumab+tremelimumab, nivolumab+ipilimumab, rovaluecel, pembrolizumab, pembrolizumab+epacadostat, GSK3359609+pembrolizumab, lenvatinib+pembrolizumab, retifanlimab, retifanlimab+enobituzumab, ADU-S100+pembrolizumab, epacadostat+nivolumab+ipilimumab/lirilumab.

Non-Small Cell Lung Cancer Combination Therapy

Therapeutic agents used to treat non-small cell lung cancer (NSCLC) include afatinib, albumin-bound paclitaxel, alectinib, atezolizumab, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof. In some embodiments therapeutic agents used to treat NSCLC include alectinib (Alecensa®), dabrafenib (Tafinlar®), trametinib (Mekinist®), osimertinib (Tagrisso®), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), and combinations thereof. In some embodiments therapeutic agents used to treat NSCLC include dabrafenib+trametinib, pembrolizumab+carboplatin+pemetrexed, pembrolizumab+carboplatin+nab-paclitaxel, ramucirumab+docetaxel, bevacizumab+carboplatin+pemetrexed, pembrolizumab+pemetrexed+carboplatin, cisplatin+pemetrexed, bevacizumab +carboplatin+nab-paclitaxel, cisplatin+gemcitabine, nivolumab+docetaxel, carboplatin+pemetrexed, carboplatin+nab-paclitaxel, or pemetrexed+cisplatin+carboplatin. In some embodiments therapeutic agents used to NSCLC include datopotamab deruxtecan (DS-1062), trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, or a combination thereof. In some embodiments therapeutic agents used to treat NSCLC include datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

Small Cell Lung Cancer Combination Therapy

Therapeutic agents used to treat small cell lung cancer (SCLC) include atezolizumab, bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof. In some embodiments therapeutic agents used to treat SCLC include atezolizumab, carboplatin, cisplatin, etoposide, paclitaxel, topotecan, nivolumab, durvalumab, trilaciclib, or combinations thereof. In some embodiments therapeutic agents used to treat SCLC include atezolizumab+carboplatin+etoposide, atezolizumab+carboplatin, atezolizumab+etoposide, or carboplatin+paclitaxel.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, pazopanib, pemetrexed, tamoxifen, topotecan, vinorelbine, and any combinations thereof.

Pancreatic Cancer Combination Therapies

Therapeutic agents used to treat pancreatic cancer include 5-FU, leucovorin, oxaliplatin, irinotecan, gemcitabine, nab-paclitaxel (Abraxane®), FOLFIRINOX, and combinations thereof. In some embodiments therapeutic agents used to treat pancreatic cancer include 5-FU+leucovorin+oxaliplatin+irinotecan, 5-FU+nanoliposomal irinotecan, leucovorin+nanoliposomal irinotecan, and gemcitabine+nab-paclitaxel.

Prostate Cancer Combination Therapies

Therapeutic agents used to treat prostate cancer include enzalutamide (Xtandi©), leuprolide, trifluridine, tipiracil (Lonsurf), cabazitaxel, prednisone, abiraterone (Zytiga®), docetaxel, mitoxantrone, bicalutamide, LHRH, flutamide, ADT, sabizabulin (Veru-111), and combinations thereof. In some embodiments therapeutic agents used to treat prostate cancer include enzalutamide+leuprolide, trifluridine+tipiracil (Lonsurf), cabazitaxel+prednisone, abiraterone+prednisone, docetaxel+prednisone, mitoxantrone+prednisone, bicalutamide+LHRH, flutamide+LHRH, leuprolide+flutamide, and abiraterone+prednisone+ADT.

Additional Exemplified Combination Therapies

In some embodiments the antibody and/or fusion protein provided herein is administered with one or more therapeutic agents selected from a PI3K inhibitor, a Trop-2 binding agent, CD47 antagonist, a SIRPα antagonist, a FLT3R agonist, a PD-1 antagonist, a PD-L1 antagonist, an MCL1 inhibitor, a CCR8 binding agent, an HPK1 antagonist, a DGKa6 inhibitor, a CISH inhibitor, a PARP-7 inhibitor, a Cbl-b inhibitor, a KRAS inhibitor (e.g., a KRAS G12C or G12D inhibitor), a KRAS degrader, a beta-catenin degrader, a helios degrader, a CD73 inhibitor, an adenosine receptor antagonist, a TIGIT antagonist, a TREM1 binding agent, a TREM2 binding agent, a CD137 agonist, a GITR binding agent, an OX40 binding agent, and a CAR-T cell therapy.

In some embodiments the antibody and/or fusion protein provided herein is administered with one or more therapeutic agents selected from a PI3K6 inhibitor (e.g., idealisib), an anti-Trop-2 antibody drug conjugate (e.g., sacituzumab govitecan, datopotamab deruxtecan (DS-1062)), an anti-CD47 antibody or a CD47-blocking agent (e.g., magrolimab, DSP-107, AO-176, ALX-148, letaplimab (IBI-188), lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab, avelumab), a small molecule MCL1 inhibitor (e.g., GS-9716), a small molecule HPK1 inhibitor (e.g., GS-6451), a HPK1 degrader (PROTAC; e.g., ARV-766), a small molecule DGKα inhibitor, a small molecule CD73 inhibitor (e.g., quemliclustat (AB680)), an anti-CD73 antibody (e.g., oleclumab), a dual $A_{2a}/A_{2b}$ adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a CD137 agonist (e.g., AGEN-2373), a GITR/OX40 binding agent (e.g., AGEN-1223) and a CAR-T cell therapy (e.g., axicabtagene ciloleucel, brexucabtagene autoleucel, tisagenlecleucel).

In some embodiments the antibody and/or fusion protein provided herein is administered with one or more therapeutic agents selected from idealisib, sacituzumab govitecan, magrolimab, GS-0189, GS-3583, zimberelimab, GS-4224, GS-9716, GS-6451, quemliclustat (AB680), etrumadenant (AB928), domvanalimab, AB308, PY159, PY314, AGEN-1223, AGEN-2373, axicabtagene ciloleucel and brexucabtagene autoleucel.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Compounds disclosed herein can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. In some cases, the identity of the final product can render apparent the identity of the necessary starting materials by a process of inspection, given the examples herein. Compounds can be isolated in the form of their pharmaceutically acceptable salts, such as those described above. Compounds described herein are typically stable and isolatable at room temperature and pressure.

An illustration of the preparation of compounds disclosed herein is shown below. Unless otherwise indicated, variables have the same meaning as described above. The examples presented below are intended to illustrate particular embodiments of the disclosure. Suitable starting materials, building blocks and reagents employed in the synthesis as described below are commercially available from AbovChem, Acros Organics, Astatech, Combi Blocks, Oakwood Chemical, or Sigma-Aldrich, for example, or can be routinely prepared by procedures described in the literature, for example in "March's Advanced Organic Chemistry: Reactions, Mechanisms, and Structure", 5th Edition; John Wiley & Sons or T. Eicher, S. Hauptmann "The Chemistry of Heterocycles; Structures, Reactions, Synthesis and Application", 2nd edition, Wiley-VCH 2003; Fieser et al. "Fiesers' Reagents for organic Synthesis" John Wiley & Sons 2000.

Synthesis of Intermediates A

General Procedure I-A for the Synthesis of Acids Aa

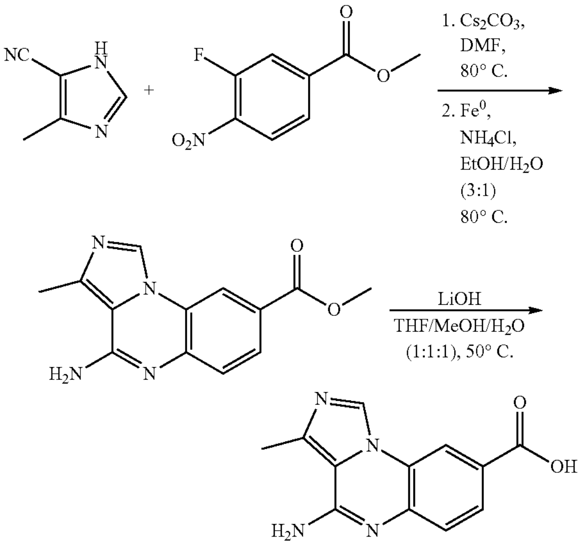

Aa-1

Step 1. methyl 3-(5-cyano-4-methyl-1H-imidazol-1-yl)-4-nitrobenzoate. A solution of 4-methyl-1H-imidazole-5-carbonitrile (3.78 g, 35.3 mmol), methyl 3-fluoro-4-nitrobenzoate (6.70 g, 33.6 mmol), and $Cs_2CO_3$ (13.1 g, 40.4 mmol) in DMF (100 mL) was stirred at 80° C. for 30 minutes. The reaction mixture was then cooled and diluted with water, EtOAc and transferred to a separatory funnel. The organic layer was separated and the aqueous layer was washed with a further portion of EtOAc. The combined organic layers were dried over $MgSO_4$, filtered, and concentrated under reduced pressure.

Step 2. methyl 4-amino-3-methylimidazo[1,5-a]quinoxaline-8-carboxylate. The crude product was then resuspended in $EtOH/H_2O$ (3:1, 10 mL) and $NH_4Cl$ (10.8 g, 202 mmol) and iron powder (11.2 g, 202 mmol) were added. The reaction mixture was heated to 80° C. with stirring for a further 3 hours, then filtered over Celite, washing with EtOAc. The filtrate was diluted with water, transferred to a separatory funnel, and the organic layer was separated. The aqueous layer was washed with a further portion of EtOAc and the combined organic layers were dried over $MgSO_4$, filtered, and concentrated. The crude residue was then purified by silica gel column chromatography to afford methyl 4-amino-3-methylimidazo[1,5-a]quinoxaline-8-carboxylate. ES/MS: m/z=257.0 $[M+H]^+$. $^1H$ NMR (400 MHz, DMSO-d6) δ 9.18 (s, 1H), 8.68 (d, J=1.9 Hz, 1H), 7.91 (dd, J=8.4, 1.9 Hz, 1H), 7.45 (d, J=8.4 Hz, 1H), 7.14 (s, 2H), 3.92 (s, 3H), 2.67 (s, 3H).

Step 3. 4-amino-3-methylimidazo[1,5-a]quinoxaline-8-carboxylic acid (Aa-1). To a suspension of methyl 4-amino-3-methylimidazo[1,5-a]quinoxaline-8-carboxylate (130 mg, 0.51 mmol) in THF/MeOH/$H_2O$ (1:1:1, 3 mL) was added LiOH·$H_2O$ (43 mg, 1 mmol). The mixture was heated to 50° C. for 1 hour, then cooled to room temperature and concentrated. The crude solid was then suspended in MeCN and 1 N HCl was added until pH 5. The resulting solid was collected and dried under reduced pressure to afford 4-amino-3-methylimidazo[1,5-a]quinoxaline-8-carboxylic acid Aa-1. ES/MS: m/z=243.0 $[M+H]^+$. $^1H$ NMR (400 MHz, DMSO-d6) δ 9.12 (s, 1H), 8.62 (d, J=1.8 Hz, 1H), 7.88 (dd, J=8.4, 1.8 Hz, 1H), 7.42 (d, J=8.5 Hz, 1H), 7.02 (s, 2H), 2.66 (s, 3H).

General Procedure II-A for the Synthesis of Acids Ab:

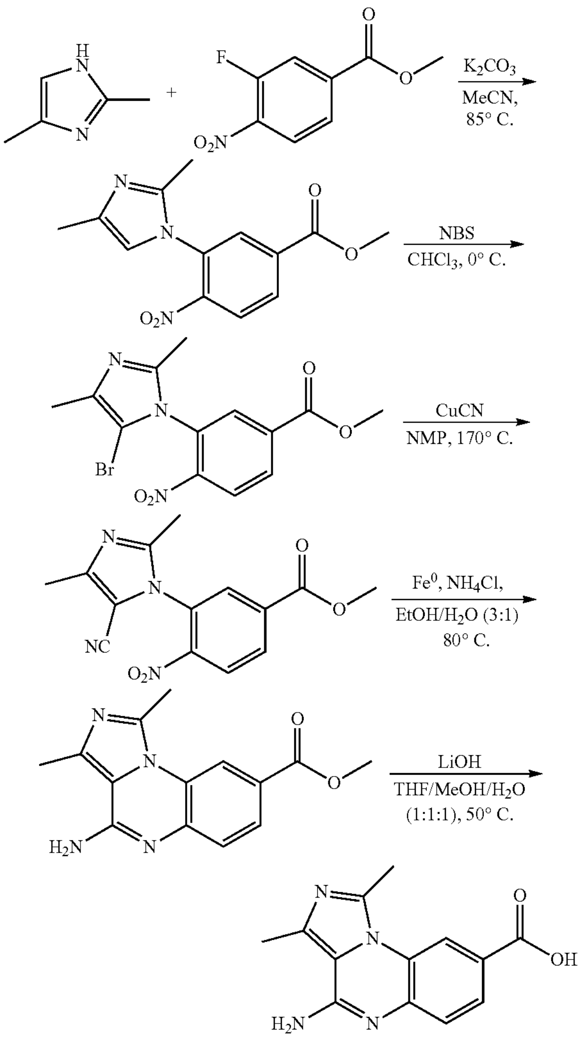

Ab-1

Step 1. Methyl 3-(2,4-dimethyl-1H-imidazol-1-yl)-4-nitrobenzoate. A stirred solution of 2,4-dimethyl-1H-imidazole (1.0 g, 10.5 mmol), methyl 3-fluoro-4-nitro-benzoate (2.0 g, 10.0 mmol), and $K_2CO_3$ (3.47 g, 25.1 mmol) in acetonitrile (12 mL) was stirred at 85° C. overnight. The reaction mixture was cooled and diluted with water, DCM. The organic layer was separated, washed with brine, dried over $MgSO_4$, filtered, and concentrated under reduced pressure. The resulting crude solid was used in the subsequent step without further purification. ES/MS: m/z=276.0 $[M+H]^+$.

Step 2. Methyl 3-(5-bromo-2,4-dimethyl-1H-imidazol-1-yl)-4-nitrobenzoate. To a stirred solution of crude methyl 3-(2,4-dimethylimidazol-1-yl)-4-nitro-benzoate (1.05 g, ca. 3.83 mmol) in $CHCl_3$ (38 mL) at 0° C. was added NBS (715 mg, 4.02 mmol). The reaction mixture was allowed to stir for 1 hour, then was quenched via addition of 10% aq. $Na_2S_2O_4$ at 0° C. The mixture was transferred to a separatory funnel and the organic layer was separated, washed with brine, dried over $MgSO_4$, filtered, and concentrated under reduced pressure. The resulting residue was purified by silica gel column chromatography to afford methyl 3-(5-bromo-2,4-dimethyl-imidazol-1-yl)-4-nitro-benzoate. ES/MS: m/z=353.9 $[M+H]^+$. $^1H$ NMR (400 MHz, Chloroform-d) δ 8.52 (d, J=8.5 Hz, 1H), 8.38 (d, J=8.9 Hz, 1H), 8.12 (d, J=1.7 Hz, 1H), 4.04 (s, 3H), 2.60 (s, 3H), 2.45 (s, 3H).

Step 3. Methyl 3-(5-cyano-2,4-dimethyl-1H-imidazol-1-yl)-4-nitrobenzoate. A suspension of methyl 3-(5-bromo-2,4-dimethyl-imidazol-1-yl)-4-nitro-benzoate (930 mg, 2.63 mmol) and CuCN (353 mg, 3.94 mmol) was heated in NMP (5 mL) at 170° C. overnight. After cooling to room temperature, the reaction mixture was diluted with EtOAc and sat. aq. $NaHCO_3$ and filtered over Celite. The resulting filtrate was transferred to a separatory funnel and the organic layer was washed with water followed by brine. The organic layer was then dried over $MgSO_4$, filtered, and concentrated under reduced pressure. The resulting residue was purified by silica gel column chromatography to afford methyl 3-(5-cyano-2,4-dimethyl-imidazol-1-yl)-4-nitro-benzoate. ES/MS: m/z=300.9 $[M+H]^+$. $^1H$ NMR (400 MHz, DMSO-d6) δ 8.54-8.42 (m, 3H), 3.97 (s, 3H), 3.38 (s, 3H), 2.34 (s, 3H).

Step 4. Methyl 4-amino-1,3-dimethylimidazo[1,5-a]quinoxaline-8-carboxylate. To a solution of methyl 3-(5-cyano-2,4-dimethyl-imidazol-1-yl)-4-nitro-benzoate (580 mg, 1.93 mmol) in EtOH/$H_2O$ (3:1, 10 mL) and $NH_4Cl$ (620 mg, 11.6 mmol) and iron powder (647 mg, 11.6 mmol) were added. The reaction mixture was heated to 80° C. with stirring for 3 hours, then filtered over Celite, washing with EtOAc. The filtrate was diluted with water, transferred to a separatory funnel, and the organic layer was separated. The aqueous layer was washed with a further portion of EtOAc and the combined organic layers were dried over $MgSO_4$, filtered, and concentrated. The crude residue was then purified by silica gel column chromatography to afford methyl 4-amino-1,3-dimethyl-imidazo[1,5-a]quinoxaline-8-carboxylate. ES/MS: m/z=271.0 $[M+H]^+$. $^1H$ NMR (400 MHz, DMSO-d6) δ 8.59 (d, J=1.8 Hz, 1H), 7.90 (dd, J=8.5, 1.7 Hz, 1H), 7.45 (d, J=8.4 Hz, 1H), 7.06 (s, 2H), 3.91 (s, 3H), 2.95 (s, 3H), 2.62 (s, 3H).

Step 5. 4-amino-1,3-dimethylimidazo[1,5-a]quinoxaline-8-carboxylic acid (Ab-1). Prepared following step 3. of general procedure I-A starting with methyl 4-amino-1,3-dimethyl-imidazo[1,5-a]quinoxaline-8-carboxylate (230 mg, 0.85 mmol). ES/MS: m/z=257.0 $[M+H]^+$. $^1H$ NMR (400 MHz, DMSO-d6) δ 8.65-8.58 (m, 1H), 7.87 (d, J=8.4 Hz, 1H), 7.32 (d, J=8.2 Hz, 1H), 6.63 (s, 2H), 2.91 (s, 3H), 2.59 (s, 3H).

General Procedure III-A for the Synthesis of Acids Ac:

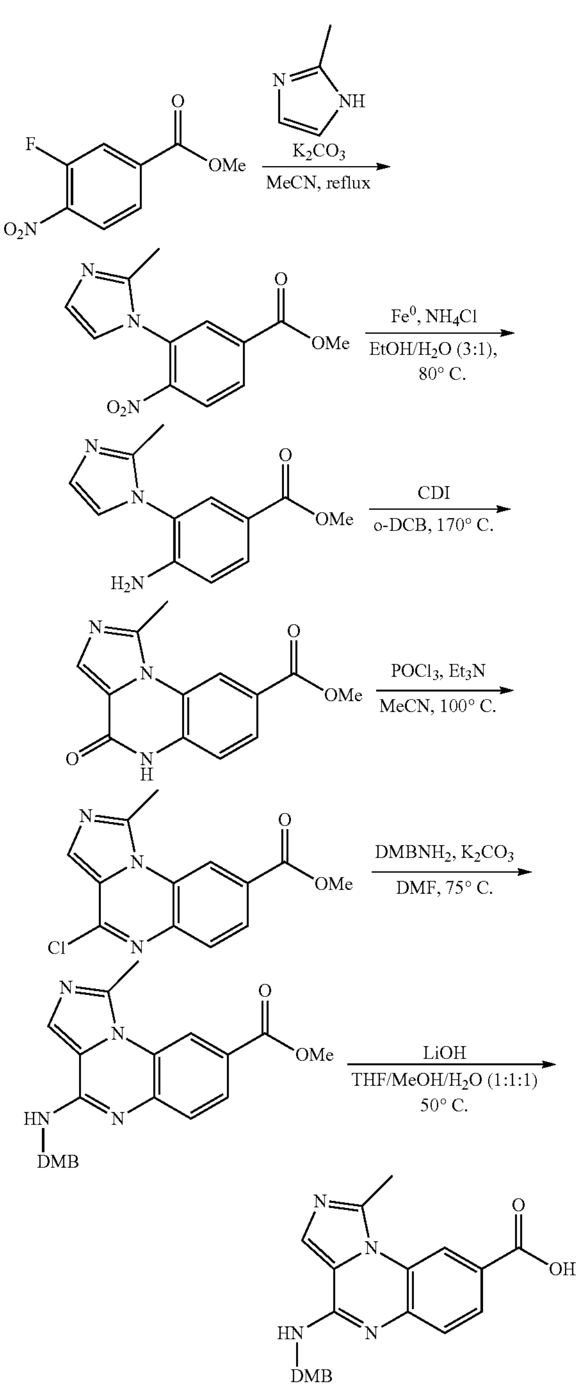

Ac-1

Step 1. Methyl 3-(2-methylimidazol-1-yl)-4-nitro-benzoate. To a stirred suspension of methyl 3-fluoro-4-nitrobenzoate (3.0 g, 15.1 mmol) and 2-methylimidazole (1.22 g, 14.9 mmol) in acetonitrile (30 mL) in a round bottom flask was added potassium carbonate (5.2 g, 37.7 mmol). The flask was fitted with a reflux condenser and refluxed overnight. After cooling to room temperature, the mixture was diluted with dichloromethane (30 mL) and sat. aq. sodium chloride (30 mL) and transferred to a separatory funnel. The organic layer was separated, and the aqueous layer extracted with a further portion of dichloromethane (30 mL). The combined organic extracts were dried over anhydrous magnesium sulfate, filtered, and concentrated under reduced pressure to afford the desired product. ES/MS: m/z=262.0 $[M+H]^+$. $^1H$ NMR (400 MHz, DMSO-d6) δ 8.41-8.29 (m, 2H), 8.15 (d, J=1.7 Hz, 1H), 7.30 (d, J=1.4 Hz, 1H), 6.98 (d, J=1.5 Hz, 1H), 3.96 (s, 3H), 2.16 (s, 3H).

Step 2. Methyl 4-amino-3-(2-methylimidazol-1-yl)benzoate. A mixture of 3-(2-methylimidazol-1-yl)-4-nitro-benzoate (1.7 g, 6.5 mmol), iron powder (−325 mesh, 4.36 g, 78.1 mmol), and ammonium chloride (4.18 g, 78.1 mmol) in ethanol/water (3:1, 50 mL) in a round bottom flask was fitted with a reflux condenser and brought to 80° C. with vigorous stirring. After 30 minutes, the mixture was cooled to room temperature and diluted with ethyl acetate (30 mL) and sat. aq. sodium chloride (30 mL). The reaction mixture was filtered over celite, rinsing with ethyl acetate, and the filtrate was transferred to a separatory funnel. The organic layer was separated, and the aqueous layer was extracted with a further portion of ethyl acetate (30 mL). The combined organic extracts were dried over anhydrous magnesium sulfate, filtered, and concentrated under reduced pressure to afford the desired product. ES/MS: m/z=232.0 $[M+H]^+$. $^1H$ NMR (400 MHz, Chloroform-d) δ 7.97 (dd, J=8.6, 1.8 Hz, 1H), 7.77 (t, J=2.1 Hz, 1H), 7.31 (s, 1H), 7.05 (dd, J=6.8, 2.8 Hz, 1H), 6.91-6.84 (m, 1H), 3.89 (s, 3H), 2.58-2.43 (m, 3H).

Step 3. Methyl 1-methyl-4-oxo-5H-imidazo[1,5-a]quinoxaline-8-carboxylate (X) A mixture of methyl 4-amino-3-(2-methylimidazol-1-yl)benzoate (1.5 g, 6.5 mmol) and 1,1'-carbonyldiimidazole (1.89 g, 11.7 mmol) in 1,2-dichlorobenzene (70 mL) in a round bottom flask was fitted with a reflux condenser and brought to 170° C. with vigorous stirring. After stirring at this temperature overnight, the mixture was cooled to room temperature and filtered. The solid was rinsed with diethyl ether, then dried under vacuum to afford the desired product. ES/MS: m/z=257.954 $[M+H]^+$. $^1H$ NMR (400 MHz, DMSO-d6) δ 11.72 (s, 1H), 8.58 (d, J=1.7 Hz, 1H), 7.96 (dd, J=8.5, 1.7 Hz, 1H), 7.80 (s, 1H), 7.42 (d, J=8.5 Hz, 1H), 3.90 (s, 3H), 2.97 (s, 3H).

Step 4. Methyl 4-chloro-1-methyl-imidazo[1,5-a]quinoxaline-8-carboxylate. A round bottom flask was charged with methyl 1-methyl-4-oxo-5H-imidazo[1,5-a]quinoxaline-8-carboxylate (600 mg, 2.33 mmol) and the atmosphere was flushed with argon. Acetonitrile (2.5 mL) was added, and the wet solid was sonicated until a brown slurry was obtained. Triethylamine (0.325 mL, 2.33 mmol) and phosphorus oxychloride (0.872 mL, 9.33 mmol) were added and the flask was fitted with a reflux condenser and brought to 100° C. with vigorous stirring overnight. The reaction mixture was cooled to room temperature the quenched by dropwise addition into acetonitrile/triethylamine/methanol (2:2:1, 12.5 mL) at 0° C., rinsing the flask with additional acetonitrile. The brown slurry was then diluted with water (20 mL) and ethyl acetate (30 mL). The mixture was transferred to a separatory funnel and the organic layer was separated. The aqueous layer was further extracted with ethyl acetate (3x30 mL) and the combined organic layers were washed with sat. aq. sodium chloride, dried over anhydrous magnesium sulfate, and concentrated under reduced pressure to afford the desired product. ES/MS: m/z=275.9 $[M+H]^+$. $^1H$ NMR (400 MHz, DMSO-d6) δ 8.79 (d, J=1.7 Hz, 1H), 8.13 (dd, J=8.4, 1.7 Hz, 1H), 8.06-7.93 (m, 2H), 3.96 (s, 3H), 3.10 (s, 3H).

Step 5. Methyl 4-[(2,4-dimethoxyphenyl)methylamino]-1-methyl-imidazo[1,5-a]quinoxaline-8-carboxylate. To a stirred suspension of methyl 4-chloro-1-methyl-imidazo[1,5-a]quinoxaline-8-carboxylate (600 mg, 2.18 mmol) and 2,4-dimethoxybenzylamine (1.64 mL, 10.9 mmol) in DMF (10 mL) was added potassium carbonate (900 mg, 6.53 mmol). The mixture was brought to 75° C. and stirred for 1 hour. The mixture was then cooled to room temperate and diluted with ethyl acetate (30 mL) and transferred to a separatory funnel. The mixture was washed with sat. aq. lithium chloride, separated, and the aqueous layer was extracted with a further portion of ethyl acetate (20 mL). The combined organic extracts were dried over anhydrous magnesium sulfate, filtered, and concentrated. The residue was purified by column chromatography (silica gel, 0-20% methanol in DCM) to afford the desired product. ES/MS: m/z=406.9 $[M+H]^+$. $^1$H NMR (400 MHz, DMSO-d6) δ 8.62 (d, J=1.8 Hz, 1H), 8.30 (t, J=5.7 Hz, 1H), 7.97 (s, 1H), 7.89 (dd, J=8.4, 1.9 Hz, 1H), 7.52 (d, J=8.5 Hz, 1H), 7.23 (d, J=8.4 Hz, 1H), 6.62 (d, J=2.4 Hz, 1H), 6.50 (dd, J=8.4, 2.4 Hz, 1H), 4.70 (d, J=5.6 Hz, 2H), 3.91 (s, 3H), 3.87 (s, 3H), 3.77 (s, 3H), 3.00 (s, 3H).

Step 6. 4-[(2,4-dimethoxyphenyl)methylamino]-1-methyl-imidazo[1,5-a]quinoxaline-8-carboxylic acid (Ac-1) To a stirred suspension of methyl 4-[(2,4-dimethoxyphenyl)methylamino]-1-methyl-imidazo[1,5-a]quinoxaline-8-carboxylate (800 mg, 1.97 mmol) in THF/MeOH/$H_2O$ (1:1:1, 6 mL) was added lithium hydroxide monohydrate (248 mg, 5.91 mmol). The reaction mixture was heated to 50° C. for 2 hours, then cooled to room temperature. The mixture was concentrated under reduced pressure to remove the organic solvents, then resuspended in acetonitrile (4 mL). 1N HCl was then added until pH 5 was reached, resulting in an off-white suspension. The suspension was filtered and the resulting solid was washed with acetonitrile to afford the desired product. ES/MS: m/z=392.9 $[M+H]^+$, $^1$H NMR (400 MHz, DMSO-d6) δ 8.67 (d, J=1.8 Hz, 1H), 8.17 (s, 1H), 7.95 (s, 1H), 7.89 (dd, J=8.4, 1.8 Hz, 1H), 7.50 (d, J=8.4 Hz, 1H), 7.23 (d, J=8.4 Hz, 1H), 6.62 (d, J=2.4 Hz, 1H), 6.51 (dd, J=8.4, 2.4 Hz, 1H), 4.70 (d, J=5.6 Hz, 2H), 3.87 (s, 3H), 3.77 (s, 3H), 3.01 (s, 3H).

4-amino-1-methylimidazo[1,5-a]quinoxaline-8-carboxylic acid (Ac-2). Prepared using intermediate 4-[(2,4-dimethoxyphenyl)methylamino]-1-methyl-imidazo[1,5-a]quinoxaline-8-carboxylate reported in general procedure III-A.

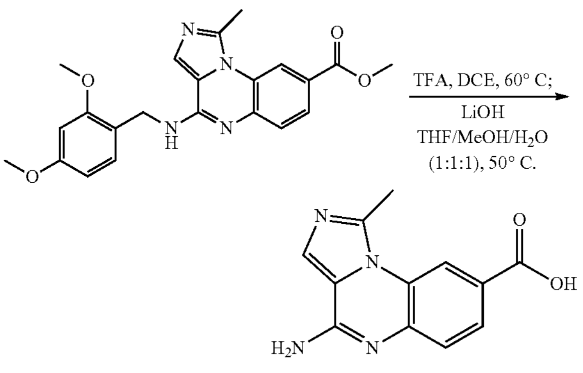

Ac-2

A suspension of methyl 4-[(2,4-dimethoxyphenyl)methylamino]-1-methyl-imidazo[1,5-a]quinoxaline-8-carboxylate (300 mg, 0.74 mmol) in DCE/TFA (5:1, 3.75 mL) was heated to 60° C. overnight. The mixture was concentrated under reduced pressure then resuspended in THF/MeOH/$H_2O$ (1:1:1, 3 mL). $LiOH{\cdot}H_2O$ (31 mg, 0.74 mmol) was added and the mixture was heated to 50° C. for 1 hour, then cooled to room temperature and concentrated. The crude solid was then suspended in MeCN and 1 N HCl was added until pH 5. The resulting solid was collected and dried under reduced pressure to afford 4-amino-1-methyl-imidazo[1,5-a]quinoxaline-8-carboxylic acid Ac-2. ES/MS: m/z=243.0 $[M+H]^+$. $^1$H NMR (400 MHz, DMSO-d6) δ 8.70 (d, J=1.7 Hz, 1H), 8.52 (s, 1H), 8.11 (dd, J=8.4, 1.6 Hz, 1H), 7.79 (d, J=8.4 Hz, 1H), 3.10 (s, 3H).

General Procedure IV-A for the Synthesis of Acids Ad:

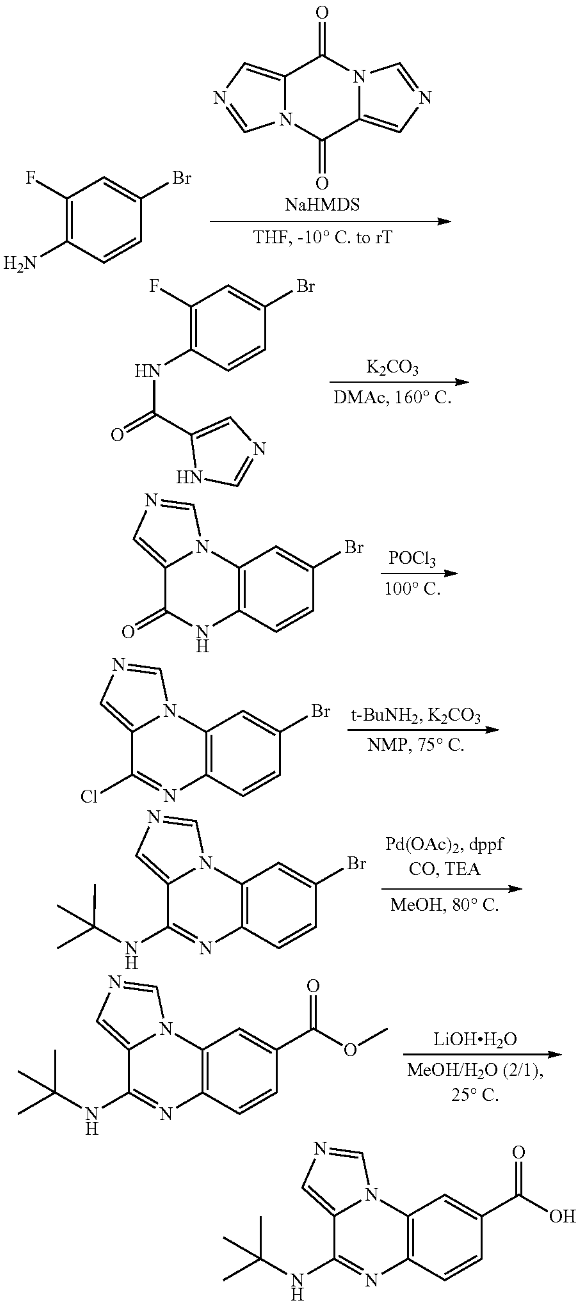

Ad-1

Step 1. N-(4-bromo-2-fluorophenyl)-1H-imidazole-5-carboxamide. A solution of 4-bromo-2-fluoroaniline (40.4 g, 213 mmol) in THF (120 mL) was cooled to −10° C. and NaHMDS (1M, 244 mL) was added dropwise. The resulting solution was stirred 1 hour at −10° C. before 5H,10H-diimidazo[1,5-a:1',5'-d]pyrazine-5,10-dione (20.0 g, 106 mmol) was added in portions. The reaction mixture was warmed to 25° C. and stirred for an additional 2 hours. AcOH (30.0 mL) was added to the reaction and the pH was adjusted to pH=6. $H_2O$ (200 mL) was added to the reaction mixture and it was extracted with ethyl acetate (200 mL×3). The organic layer was washed with brine (200 mL), dried over $Na_2SO_4$ and concentrate the mixture under reduced pressure. The crude product was triturated with n-heptane (100 mL) at 25° C. for 30 mins the filtered and the solid was collected to deliver the desired product. ES/MS: m/z=285.0 $[M+H]^+$. $^1H$ NMR (400 MHz, DMSO-$d_6$) δ=12.8-12.5 (m, 1H), 9.49 (s, 1H), 8.07 (t, J=8.8 Hz, 1H), 7.86 (d, J=7.6 Hz, 2H), 7.64 (dd, J=2.4, 10.4 Hz, 1H), 7.43 (br d, J=8.8 Hz, 1H).

Step 2. 8-bromoimidazo[1,5-a]quinoxalin-4(5H)-one. N-(4-bromo-2-fluorophenyl)-1H-imidazole-5-carboxamide (25.0 g, 62.5 mmol) was dissolved in DMAc (150 mL). $K_2CO_3$ (25.9 g, 187 mmol) was added to the mixture and the reaction was then stirred at 160° C. for 3 hrs. The reaction was cooled to room temperature and poured into $H_2O$ (750 mL) slowly. The mixture was filtered, and the solids were dried to afford the desired compound. ES/MS: m/z=265.0 $[M+H]^+$. $^1H$ NMR (400 MHz, DMSO-$d_6$) δ 8.72 (s, 1H), 8.10 (d, J=2.4 Hz, 1H), 7.26 (s, 1H), 7.19 (dd, J=2.4, 8.6 Hz, 1H), 6.98 (d, J=8.8 Hz, 1H).

Step 3. 8-bromo-4-chloroimidazo[1,5-a]quinoxaline. 8-bromoimidazo[1,5-a]quinoxalin-4(5H)-one (10.0 g, 37.9 mmol) was added to $POCl_3$ (60.0 mL) and the mixture was stirred at 100° C. for 3.5 hrs. The mixture was then concentrated under reduced pressure and the crude product was triturated with ethyl acetate (20.0 mL) at 25° C. for 30 mins. The solids were then filtered and dried to afford the desired product. ES/MS: m/z=283.9 $[M+H]^+$. $^1H$ NMR (400 MHz, DMSO-$d_6$) δ 9.44 (s, 1H), 8.78 (s, 1H), 7.99 (s, 1H), 7.80 (q, J=8.8 Hz, 2H).

Step 4. 8-bromo-N-(tert-butyl)imidazo[1,5-a]quinoxalin-4-amine. 8-bromo-4-chloroimidazo[1,5-a]quinoxaline (4.0 g, 14.2 mmol) was dissolved in NMP (24 mL) and $K_2CO_3$ (5.87 g, 42.5 mmol) was added to the mixture followed by t-$BuNH_2$ (5.18 g, 70.8 mmol). The reaction was then stirred at 75° C. for 12 hours then cooled to room temperature and poured into water (80 mL). The solids were then filtered, dried and purified by column chromatography ($SiO_2$, n-heptane/Ethyl acetate 30/1 to 1/1) to afford the desired product. ES/MS: m/z=320.9 $[M+H]^+$. $^1H$ NMR (400 MHz, DMSO-$d_6$) δ 9.08 (s, 1H), 8.44 (d, J=1.6 Hz, 1H), 8.03 (s, 1H), 7.49-7.44 (m, 1H), 7.42-7.38 (m, 1H), 7.02 (s, 1H), 1.54 (s, 9H).

Step 5. Methyl 4-(tert-butylamino)imidazo[1,5-a]quinoxaline-8-carboxylate. 8-bromo-N-(tert-butyl)imidazo[1,5-a]quinoxalin-4-amine (2.0 g, 6.27 mmol) was dissolved in MeOH (24 mL) and triethylamine (2.62 mL, 18.8 mmol) followed by $Pd(OAc)_2$ (703 mg, 3.13 mmol) and dppf (1.74 g, 3.13 mmol). The suspension was degassed under vacuum and purged with $CO_{(g)}$ three times. The reaction was then stirred at 80° C. for 16 hours under $CO_{(g)}$ (50 psi), cooled to room temperature, filtered, and dried to afford the desired product. The crude material was used without further purification in the next step. ES/MS: m/z=299.1 $[M+H]^+$.

Step 6. 4-(tert-butylamino)imidazo[1,5-a]quinoxaline-8-carboxylic acid (Ad-1). A solution of methyl 4-(tert-butylamino)imidazo[1,5-a]quinoxaline-8-carboxylate (1.60 g, 3.43 mmol) in $MeOH/H_2O$ (2/1, 9.6 mL) and $LiOH{\cdot}H_2O$ (216 mg, 5.15 mmol) was stirred at room temperature for 12 hours. Water (10 mL) and EtOAc (10 mL) were added to the mixture and the pH was adjusted to pH=5 2.00 M HCl. The solids were filtered and triturated in MTBE for 30 minutes then purified by preparative-HPLC ($NH_4HCO_3$, Column: 120 g Agela C18, 10-40% 20 mins; 40% 5 mins; Solvent for sample dissolution about 0.50 grams of sample dissolved in 10.0 mL THF) to afford the desired product Ad-1. ES/MS: m/z=285.0 $[M+H]^+$. $^1H$ NMR (400 MHz, DMSO-$d_6$) δ 13.0-12.8 (m, 1H), 9.20 (s, 1H), 8.66 (s, 1H), 8.07 (s, 1H), 7.91-7.86 (m, 1H), 7.51 (d, J=8.4 Hz, 1H), 7.23 (s, 1H), 1.57 (s, 9H).

General Procedure V-A for Intermediate Ae

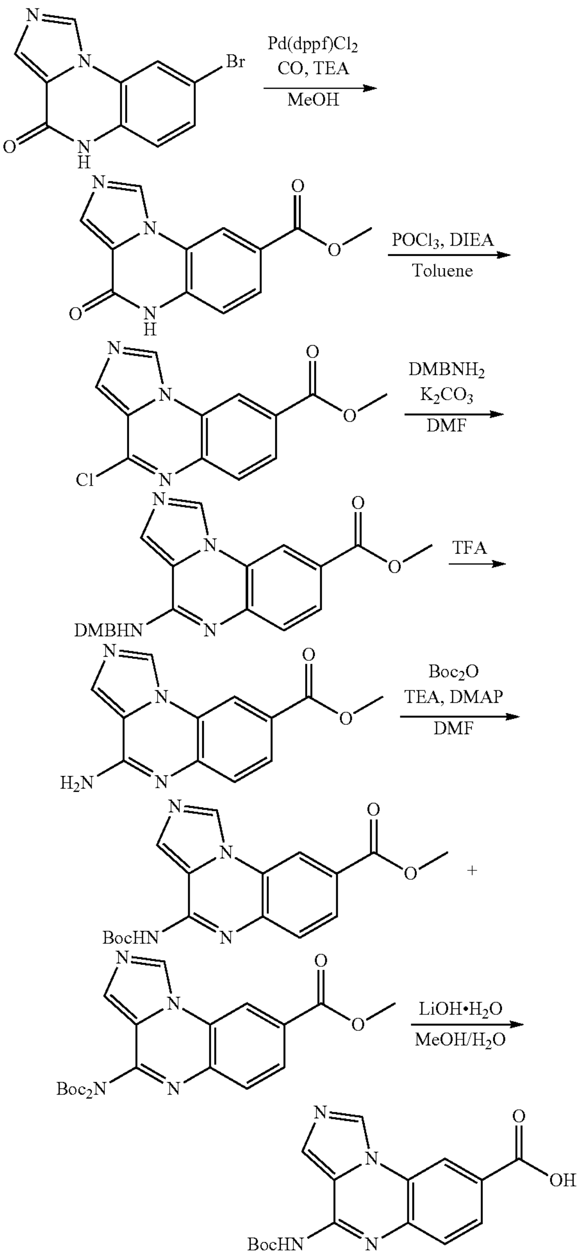

Ae-1

Step 1. Methyl 4-oxo-4,5-dihydroimidazo[1,5-a]quinoxaline-8-carboxylate. 8-bromoimidazo[1,5-a]quinoxalin-4(5H)-one (190 g, 0.72 mol reported in general procedure IV-A step 2) was dissolved in MeOH (1.14 L) and triethylamine (300 mL, 3 equiv.) was added followed by Pd(dppf)

$Cl_2$ (52.6 g, 0.10 equiv.). The mixture was stirred under a CO (g) at 50 Psi at 80° C. for 16 hours. The reaction mixture was cooled to room temperature and the suspension was filtered and dried under reduced pressure to deliver the desired compound. ES/MS: m/z=244.0 $[M+H]^+$.

Step 2. Methyl 4-chloroimidazo[1,5-a]quinoxaline-8-carboxylate. Methyl 4-oxo-4,5-dihydroimidazo[1,5-a]quinoxaline-8-carboxylate (150 g, 0.616 mol) was added to a solution of diisopropylethylamine (79.7 g, 1 equiv.) and $POCl_3$ (378 g, 4.00 equiv.) in toluene (900 mL). The mixture was stirred at 130° C. for 12 hours. The mixture was then evaporated to dryness and triturated in EtOAc (500 mL) for 30 minutes. The solids were filtered and dried to afford the desired product. ES/MS: m/z=263.0 $[M+H]^+$.

Step 3. Methyl 4-((3,4-dimethylbenzyl)amino)imidazo[1,5-a]quinoxaline-8-carboxylate. Methyl 4-chloroimidazo[1,5-a]quinoxaline-8-carboxylate (100 g, 382 mmol) was dissolved in DMF (600 mL) and $K_2CO_3$ (105 g, 2.0 equiv.) followed by $DMBNH_2$ (76.7 g, 1.20 equiv.). The reaction mixture was then stirred at 80° C. for 3 hours. The reaction was cooled to room temperature and poured into $H_2O$ (2.0 L). The solids were filtered and dried under reduced pressure to deliver the desired compound. ES/MS: m/z=393.1 $[M+H]^+$. $^1H$ NMR (400 MHz, DMSO-$d_6$) δ=9.28 (s, 1H), 8.72-8.68 (m, 1H), 8.40 (br t, J=5.2 Hz, 1H), 8.04 (s, 1H), 7.88 (dd, J=1.6, 8.4 Hz, 1H), 7.52 (d, J=8.4 Hz, 1H), 7.20 (d, J=8.4 Hz, 2H), 6.60 (d, J=2.0 Hz, 1H), 6.52-6.40 (m, 1H), 4.68 (br d, J=5.6 Hz, 2H), 3.92-3.88 (m, 3H), 3.84 (s, 3H), 3.72 (s, 3H).

Step 4. Methyl 4-aminoimidazo[1,5-a]quinoxaline-8-carboxylate. Methyl 4-((3,4-dimethylbenzyl)amino)imidazo[1,5-a]quinoxaline-8-carboxylate (140 g, 356 mmol) was dissolved in TFA (700 mL) and stirred at 80° C. for 3 hours. The reaction mixture was concentrated under reduced pressure and the pH was adjusted to pH=7 with $NaHCO_3$ (2.0 M). The solids were filtered and dried under vacuum. ES/MS: m/z=243.0 $[M+H]^+$.

Step 5. Methyl 4-((tert-butoxycarbonyl)amino)imidazo[1,5-a]quinoxaline-8-carboxylate. Methyl 4-aminoimidazo[1,5-a]quinoxaline-8-carboxylate (85 g, 350 mmol) was dissolved in DMF (510 mL) and DMAP (42.8 g, 351 mmol) and triethylamine (177 g, 1.75 mol) were added followed by $Boc_2O$ (765 g, 5.0 equiv.). The mixture was stirred at 50° C. for 3 hours. Water (1.0 L) was added to the reaction mixture at room temperature and the mixture was evaporated with EtOAc (300 mL×3). The combined organic layers were washed with brine (100 mL) and dried over $Na_2SO_4$ then filtered. The residue was purified by column chromatography ($SiO_2$, Petroleum ether/Ethyl acetate=30/1 to 0/1) to give the desired product. ES/MS: m/z=343.0 $[M+H]^+$. $^1H$ NMR (400 MHz, DMSO-$d_6$) δ=10.40 (s, 1H), 9.44 (s, 1H), 8.88 (d, J=1.2 Hz, 1H), 8.12 (s, 1H), 8.04 (dd, J=1.2, 8.4 Hz, 1H), 7.76 (d, J=8.4 Hz, 1H), 3.92 (s, 3H), 3.40-3.20 (m, 2H), 1.52 (s, 9H).

Step 6. 4-((tert-butoxycarbonyl)amino)imidazo[1,5-a]quinoxaline-8-carboxylic acid (Ae-1). To a solution of methyl 4-((tert-butoxycarbonyl)amino)imidazo[1,5-a]quinoxaline-8-carboxylate (18.0 g, 52.6 mmol) in MeOH (72 mL), was added a solution of LiOH (3.78 g, 157 mmol) in water (36 mL). The reaction was stirred at room temperature for 12 hours. The aqueous was adjusted to pH=5 with 2.00 M HCl, then extracted with DCM (50 mL×2). The organic extract was washed with brine (30 mL), dried over sodium sulfate, and concentrated to afford the desired product (Ae-1). ES/MS: m/z=329.1 $[M+H]^+$. $^1H$ NMR (400 MHz, DMSO-$d_6$) δ 9.39 (s, 1H), 8.81 (d, J=1.2 Hz, 1H), 8.10 (s, 1H), 8.01 (dd, J=1.6, 8.4 Hz, 1H), 7.73 (d, J=8.4 Hz, 1H), 1.53 (s, 9H).

General Procedure VI-A for the Synthesis of Acid Intermediates Af

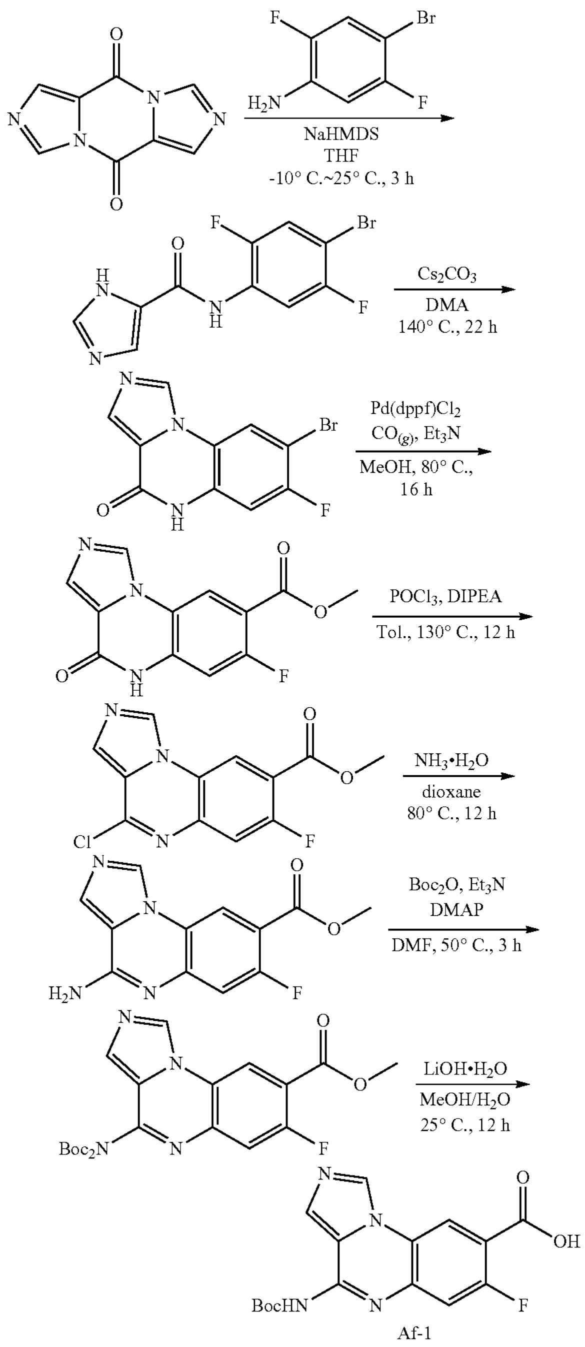

Af-1

Step 1: N-(4-bromo-2,5-difluorophenyl)-1H-imidazole-5-carboxamide. To a solution of 4-bromo-2,5-difluoroaniline (99.5 g, 478 mmol) in THF (270 mL) at −10° C. was added NaHMDS (1M, 550 mL, 550 mmol). The reaction was stirred at −10° C. for 1 hr. 5H,10H-diimidazo[1,5-a:1',5'-d]pyrazine-5,10-dione (45.0 g, 239 mmol) was added to the mixture in batches, and the mixture was stirred at 25° C. for 2 hrs. AcOH was added until pH=7, followed by water (300 mL). The mixture was extracted with EtOAc (300 mL×3), washed with brine (300 mL), and dried over sodium sulfate. The crude residue was purified by flash chromatography to give desired product. ES/MS: m/z=304.0 $[M+H]^+$. $^1H$ NMR (400 MHz, DMSO-$d_6$) δ 7.87-7.80 (m, 2H) 7.90 (s, 1H) 8.17 (dd, J=12.0, 6.8 Hz, 1H) 9.54 (s, 1H) 9.57-9.54 (m, 1H) 13.0-12.6 (m, 1H).

Step 2: 8-bromo-7-fluoroimidazo[1,5-a]quinoxalin-4(5H)-one. To a solution of N-(4-bromo-2,5-difluorophenyl)-1H-imidazole-5-carboxamide (95.0, 310 mmol) in DMA (570 mL) was added $Cs_2CO_3$ (326 g, 1065 mmol). The mixture was stirred at 140° C. for 22 hrs. The reaction was poured into water (1.0 L), filtered, and concentrated to give the desired product. ES/MS: m/z=283.9 $[M+H]^+$. $^1H$ NMR (400 MHz, DMSO-$d_6$) δ 7.18 (d, J=9.6 Hz, 1H) 7.86 (s, 1H) 8.65 (s, 1H) 9.04 (s, 1H) 11.8-11.3 (m, 1H).

Step 3: Methyl 7-fluoro-4-oxo-4,5-dihydroimidazo[1,5-a]quinoxaline-8-carboxylate. To a mixture of 8-bromo-7-fluoroimidazo[1,5-a]quinoxalin-4(5H)-one (65.0 g, 230 mmol) in MeOH (390 mL) was added triethylamine (69.9 g, 691 mmol) and Pd(dppf)$Cl_2$ (8.42, 11.5 mmol). The suspension was degassed under the vacuum and purged with CO three times. The resulting mixture was stirred at 80° C. for 16 hrs under CO (50 psi). Upon completion, the mixture was filtered and concentrated to yield the desired product. ES/MS: m/z=262.0 $[M+H]^+$. $^1H$ NMR (400 MHz, DMSO-$d_6$) δ 3.89 (s, 3H) 7.11 (d, J=12.0 Hz, 1H) 7.89 (s, 1H) 8.68 (s, 1H) 9.20 (s, 1H) 11.7 (s, 1H).

Step 4: Methyl 4-chloro-7-fluoroimidazo[1,5-a]quinoxaline-8-carboxylate. DIPEA (19.8 g, 153 mmol) and $POCl_3$ (93.9 g, 612 mmol) in Toluene (240 mL) was added methyl 7-fluoro-4-oxo-4,5-dihydroimidazo[1,5-a]quinoxaline-8-carboxylate (40.0 g, 153 mmol). The mixture of stirred at 130° C. for 12 hrs. Upon completion, the mixture was cooled to 25° C. and concentrated under reduced pressure. Trituration of the crude product with EtOAc (100 mL) at 25° C. for 30 mins yield to desired product. ES/MS: m/z=280.0 $[M+H]^+$. $^1H$ NMR (400 MHz, DMSO-$d_6$) δ=9.58 (s, 1H), 8.93 (d, J=6.8 Hz, 1H), 8.06 (s, 1H), 7.89 (d, J=11.2 Hz, 1H), 3.96 (s, 3H).

Step 5: Methyl 4-amino-7-fluoroimidazo[1,5-a]quinoxaline-8-carboxylate. To a mixture of methyl 4-chloro-7-fluoroimidazo[1,5-a]quinoxaline-8-carboxylate (25.0 g, 89.4 mmol) in dioxane (150 mL) was added $NH_3{\cdot}H_2O$ (44.7 g, 357 mmol). The reaction was stirred at 80° C. for 12 hrs before concentrating under reduce pressure. Trituration of the crude product with EtOAc (450 mL) at 25° C. for 30 mins yield to desired product. ES/MS: m/z=262.1 $[M+H]^+$. $^1H$ NMR (400 MHz, DMSO-$d_6$) δ=9.24 (s, 1H), 8.65 (d, J=7.2 Hz, 1H), 7.95 (s, 1H), 7.84 (s, 2H), 7.20 (d, J=12.8 Hz, 1H), 3.88 (s, 3H).

Step 6: Methyl 4-(bis(tert-butoxycarbonyl)amino)-7-fluoroimidazo[1,5-a]quinoxaline-8-carboxylate. To a mixture of methyl 4-amino-7-fluoroimidazo[1,5-a]quinoxaline-8-carboxylate (20.0 g, mmol, 76.9 mmol) in DMF (120 mL) was added DMAP (9.38 g, 76.9 mmol), triethylamine (46.7 g, 461 mmol), and $Boc_2O$ (83.8 g, 125 mmol), respectively. The reaction was stirred at 50° C. for 3 hrs. Water (100 mL) was added, and the mixture was extracted with DCM (100 mL×3). The combined organic extract was washed with brine (300 mL), dried over sodium sulfate, and concentrated. The crude residue was purified by flash chromatography to give desired product. ES/MS: m/z=461.2 $[M+H]^+$. $^1H$ NMR (400 MHz, DMSO-$d_6$) δ=9.55 (s, 1H), 8.98 (d, J=6.4 Hz, 1H), 7.93 (s, 1H), 7.91 (s, 1H), 3.96 (s, 3H), 1.38 (s, 18H).

Step 7: 4-((tert-butoxycarbonyl)amino)-7-fluoroimidazo[1,5-a]quinoxaline-8-carboxylic acid (Af-1). methyl 4-(bis(tert-butoxycarbonyl)amino)-7-fluoroimidazo[1,5-a]quinoxaline-8-carboxylate (10.0 g, mmol, 21.7 mmol) in MeOH (40 mL) and water (20 mL) was added $LiOH{\cdot}H_2O$ (1.37 g, 32.5 mmol). The reaction was stirred at 25° C. for 12 hrs before adjusting to pH=6 with 5 mL aq. HCl (6.00 M). The mixture was filtered and concentrated under reduce pressure to give the desired product Af-1. ES/MS: m/z=347.1 $[M+H]^+$. $^1H$ NMR (400 MHz, DMSO-$d_6$) δ 1.53 (s, 9H) 7.48 (d, J=12.0 Hz, 1H) 8.14 (s, 1H) 8.74 (d, J=6.8 Hz, 1H) 9.36 (s, 1H) 10.4 (s, 1H).

Af-2

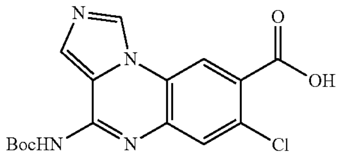

4-((tert-butoxycarbonyl)amino)-7-chloroimidazo[1,5-a]quinoxaline-8-carboxylic acid (Af-2). Prepared following general procedure VI-A starting with 4-bromo-5-chloro-2-fluoroaniline. ES/MS: m/z 362 $[M+H]^+$. $^1H$ NMR (400 MHz, MeOD) δ 9.11 (s, 1H), 8.24 (s, 1H), 8.07 (s, 1H), 7.89 (s, 1H), 1.60 (s, 9H).

Af-3

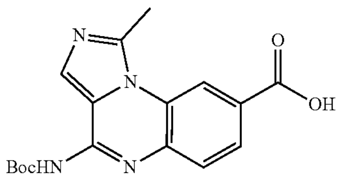

4-((tert-butoxycarbonyl)amino)-1-methylimidazo[1,5-a]quinoxaline-8-carboxylic acid (Af-3). Prepared following general procedure VI-A using 3,8-dimethyl-5H,10H-diimidazo[1,5-a:1',5'-d]pyrazine-5,10-dione and 4-bromo-2-fluoroaniline in step 1. ES/MS: m/z =343 $[M+H]^+$. $^1H$ NMR (400 MHz, MeOD-$d_4$) δ 8.85 (s, 1H), 8.09 (d, J=7.60 Hz, 1H), 7.94 (s, 1H), 7.86 (br d, J=8.4 Hz, 1H), 3.14 (s, 3H), 1.60 (s, 9H).

Af-4

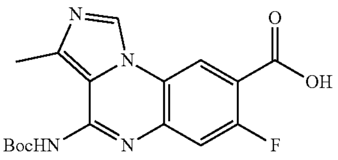

4-((tert-butoxycarbonyl)amino)-7-fluoro-3-methylimidazo[1,5-a]quinoxaline-8-carboxylic acid (Af-4). Prepared following general procedure VI-A using 1,6-dimethyl-5H,10H-diimidazo[1,5-a:1',5'-d]pyrazine-5,10-dione and 4-bromo-2,5-difluoroaniline in step 1. ES/MS: m/z 316.9 $[M-3{\times}Me+H]^+$. $^1H$ NMR (DMSO-$d_6$ 400 MHz) δ 8.98-8.82 (m, 1H), 8.66-8.49 (m, 1H), 7.25-6.96 (m, 1H), 2.56-2.52 (m, 4H).

Af-5

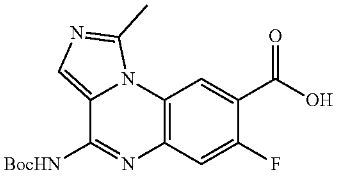

4-((tert-butoxycarbonyl)amino)-7-fluoro-1-methylimidazo[1,5-a]quinoxaline-8-carboxylic acid (Af-5). Prepared following general procedure VI-A using 3,8-dimethyl-5H, 10H-diimidazo[1,5-a:1',5'-d]pyrazine-5,10-dione and 4-bromo-2,5-difluoroaniline in step 1. ES/MS: m/z=305.1 $[M-tBu]^+$. $^1H$ NMR: (DMSO-$d_6$ 400 MHz): δ 13.5-13.4 (m, 1H), 10.3 (s, 1H), 8.64-8.62 (d, J=6.8 Hz, 1H), 8.06 (s, 1H), 7.50-7.47 (d, J=11.6 Hz, 1H), 2.99 (s, 3H), 1.52 (s, 9H).

Af-6

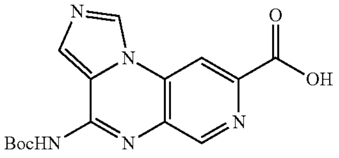

4-((tert-butoxycarbonyl)amino)imidazo[1,5-a]pyrido[3,4-e]pyrazine-8-carboxylic acid (Af-6). Prepared following general procedure VI-A starting with 4,6-dichloropyridin-3-amine. ES/MS: m/z=330.1 $[M+H]^+$. $^1H$ NMR (DMSO-d, 400 MHz): δ 10.5 (br s, 1H), 9.52 (s, 1H), 8.94 (s, 2H), 8.22 (s, 1H), 1.54 (s, 9H).

Af-7

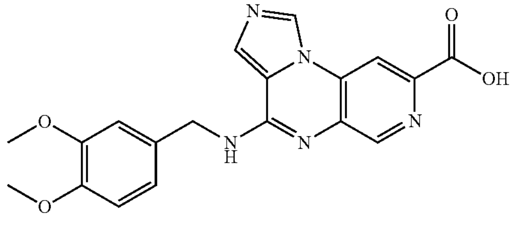

4-((3,4-dimethoxybenzyl)amino)imidazo[1,5-a]pyrido[3,4-e]pyrazine-8-carboxylic acid (Af-7). Prepared following general procedure VI-A starting with 4,6-dichloropyridin-3-amine ($DMBNH_2$ was used in step 5 instead of ammonia and the product of step 5 was hydrolyzed using the conditions reported for step 7). ES/MS: m/z=380.1 $[M+H]^+$. $^1H$ NMR (400 MHz, DMSO-$d_6$) δ 9.45 (s, 1H), 8.93 (br s, 1H), 8.85 (s, 1H), 8.80 (s, 1H), 8.11 (s, 1H), 7.12 (d, J=1.6 Hz, 1H), 6.98-6.88 (m, 2H), 4.76 (d, J=5.6 Hz, 2H), 3.74 (s, 3H), 3.72 (s, 3H).

General Procedure VII-A for the Synthesis of Acid Intermediates Ag

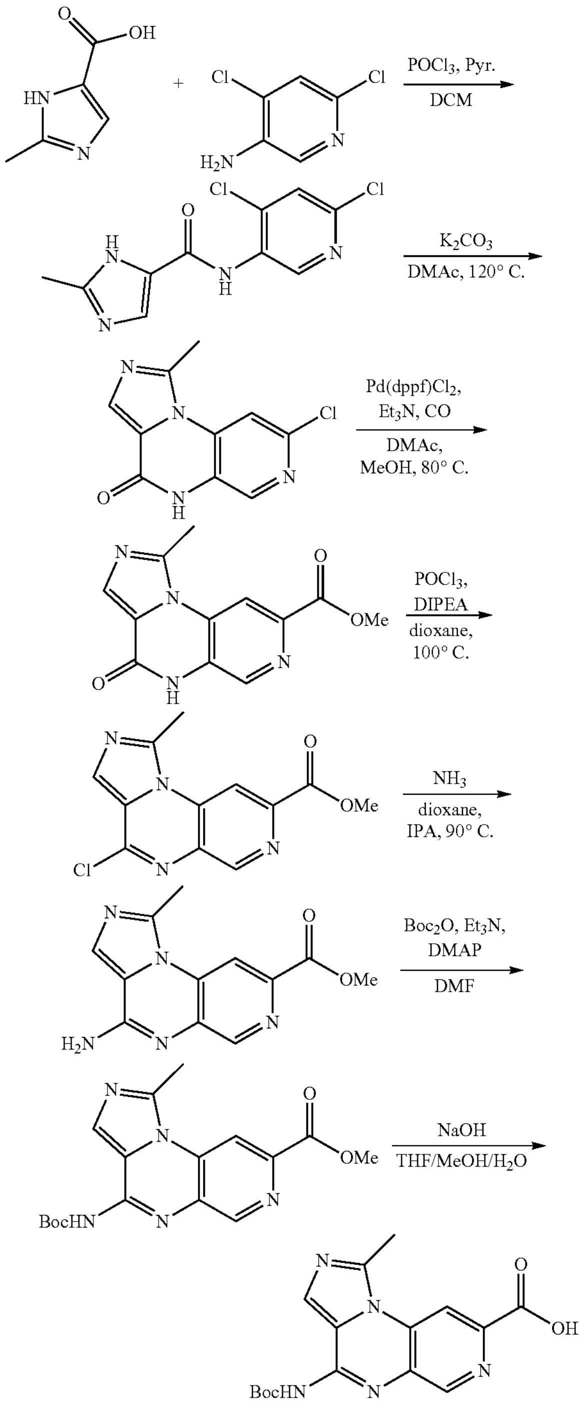

Ag-1

Step 1: N-(4,6-dichloropyridin-3-yl)-2-methyl-1H-imidazole-5-carboxamide. To a solution of 2-methyl-1H-imidazole-5-carboxylic acid (100 g, 790 mmol) and 4,6-dichloropyridin-3-amine (129 g, 790 mmol) in DCM (1.0 L) was added $POCl_3$ (147 mL, 1.59 mol) at 0° C. followed by pyridine (320 mL, 3.96 mol). The mixture was stirred at room temperature for 2 hours then concentrated. The resulting residue was poured into sat. aq. $NaHCO_3$ (1.0 L) then filtered to afford N-(4,6-dichloropyridin-3-yl)-2-methyl-1H-imidazole-5-carboxamide. ES/MS: m/z=271.0 $[M+H]^+$.

Step 2: 8-chloro-1-methylimidazo[1,5-a]pyrido[3,4-e]pyrazin-4(5H)-one. N-(4,6-dichloropyridin-3-yl)-2-methyl-1H-imidazole-5-carboxamide (113 g, 420 mmol) and $K_2CO_3$ (172 g, 1.25 mol) were stirred in DMAc (1.2 L) at 120° C. for 12 hours. After cooling to room temperature, the mixture was poured into 1N HCl (2.0 L) and filtered to afford 8-chloro-1-methylimidazo[1,5-a]pyrido[3,4-e]pyrazin-4(5H)-one. ES/MS: m/z=235.0 $[M+H]^+$.

Step 3: Methyl 1-methyl-4-oxo-4,5-dihydroimidazo[1,5-a]pyrido[3,4-e]pyrazine-8-carboxylate. To a solution of 8-chloro-1-methylimidazo[1,5-a]pyrido[3,4-e]pyrazin-4(5H)-one (65 g, 280 mmol) in DMAc/MeOH (2:1, 900 mL) was added triethylamine (115 mL, 830 mmol) and Pd(dppf)$Cl_2$ (20.2 g, 28 mmol). The mixture was degassed with CO and allowed to stir under CO atmosphere (1 Mpa) at 80° C. for 12 hours. The mixture was then filtered and the resulting residue was purified by recrystallization from DCM/Petroleum ether to afford methyl 1-methyl-4-oxo-4,5-dihydroimidazo[1,5-a]pyrido[3,4-e]pyrazine-8-carboxylate. ES/MS: m/z=259.0 $[M+H]^+$.

Step 4: Methyl 4-chloro-1-methylimidazo[1,5-a]pyrido[3,4-e]pyrazine-8-carboxylate. To methyl 1-methyl-4-oxo-4,5-dihydroimidazo[1,5-a]pyrido[3,4-e]pyrazine-8-carboxylate (56 g, 220 mmol) in 1,4-dioxane (600 mL) was added $POCl_3$ (161 mL, 1.73 mol) followed by DIPEA (75.5 mL, 430 mmol). The atmosphere was flushed with $N_2$ and the mixture was heated to 100° C. with stirring for 24 hours. After cooling to room temperature, the mixture was concentrated then triturated with EtOAc to afford methyl 4-chloro-1-methylimidazo[1,5-a]pyrido[3,4-e]pyrazine-8-carboxylate (60 g, 86%). ES/MS: m/z=277.0 $[M+H]^+$ Step 5: Methyl 4-amino-1-methylimidazo[1,5-a]pyrido[3,4-e]pyrazine-8-carboxylate. To methyl 4-amino-1-methylimidazo[1,5-a]pyrido[3,4-e]pyrazine-8-carboxylate (60 g, 190 mmol) in 1,4-dioxane (300 mL) was added $NH_3$ (3.5 M in iPrOH, 300 mL, 1.1 mol). The mixture was stirred at 90° C. for 12 hours, then concentrated to afford methyl 4-amino-1-methylimidazo[1,5-a]pyrido[3,4-e]pyrazine-8-carboxylate (50 g, 99%). ES/MS: m/z=258.0 $[M+H]^+$=

Step 6: Methyl 4-((tert-butoxycarbonyl)amino)-1-methylimidazo[1,5-a]pyrido[3,4-e]pyrazine-8-carboxylate. To methyl 4-amino-1-methylimidazo[1,5-a]pyrido[3,4-e]pyrazine-8-carboxylate (54 g, 200 mmol) in DMF (540 mL) was added triethylamine (83.9 mL, 600 mmol), $Boc_2O$ (219 g, 1.0 mol) and DMAP (36.8 g, 300 mmol). After stirring for 1 hour, the mixture was diluted with water, EtOAc. The mixture was transferred to a separatory funnel and the organic layer was extracted. The aqueous layer was washed with EtOAc three additional times, and the combined organic extracts were washed with brine, dried over $Na_2SO_4$, filtered, and concentrated. Trituration of the resulting residue with MTBE afforded methyl 4-((tert-butoxycarbonyl)amino)-1-methylimidazo[1,5-a]pyrido[3,4-e]pyrazine-8-carboxylate (44 g, 50%). ES/MS: m/z=358.1 $[M+H]^+$.

Step 7: 4-((tert-butoxycarbonyl)amino)-1-methylimidazo[1,5-a]pyrido[3,4-e]pyrazine-8-carboxylic acid (Ag-1). To a solution of methyl 4-((tert-butoxycarbonyl)amino)-1-methylimidazo[1,5-a]pyrido[3,4-e]pyrazine-8-carboxylate (44 g, 123 mmol) in THF/MeOH/$H_2O$ (1:1:1, 450 mL) was added NaOH (12 g, 300 mmol). After stirring for 1 hour, the mixture was concentrated. Purification by reversed-phase HPLC afforded 4-((tert-butoxycarbonyl)amino)-1-methylimidazo[1,5-a]pyrido[3,4-e]pyrazine-8-carboxylic acid (8.17 g, 24%). ES/MS: m/z=344.1 $[M+H]^+$. $^1$H NMR (DMSO-d6 400 MHz): δ 8.61-8.54 (m, 2H), 7.53 (s, 1H), 2.92 (s, 3H), 1.45 (s, 9H).

Ag-2

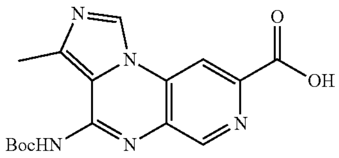

4-((tert-butoxycarbonyl)amino)-3-methylimidazo[1,5-a]pyrido[3,4-e]pyrazine-8-carboxylic acid (Ag-2). Prepared according to general procedure VII-A starting from 4-methyl-1H-imidazole-5-carboxylic acid. ES/MS: m/z=344.0 $[M+H]^+$. $^1$H NMR (DMSO-d6 400 MHz): δ 9.32 (s, 1H), 8.77 (s, 1H), 8.67 (s, 1H), 2.53 (s, 3H), 1.48 (s, 9H).

General Procedure VIII-A for the Synthesis of Acid Intermediates Ah.

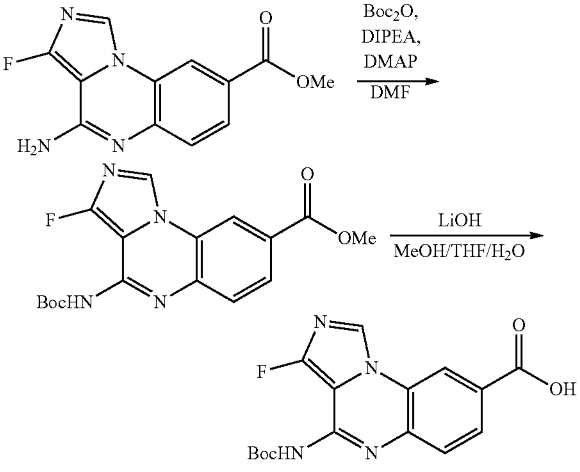

Ah-1

Step 1: Methyl 4-((tert-butoxycarbonyl)amino)-3-fluoroimidazo[1,5-a]quinoxaline-8-carboxylate. To a solution of methyl 4-amino-3-fluoroimidazo[1,5-a]quinoxaline-8-carboxylate (prepared according to general procedure II-A (Hypoboric acid and 4-(4-pyridyl)pyridine in DMF were used in place of $Fe^{(0)}$ starting with 4-fluoro-1H-imidazole) (6.2 g, 22.9 mmol) in DCM (620 mL) was added DIPEA (13.7 mL, 79 mmol), $Boc_2O$ (17.2 g, 79 mmol), and DMAP (2.42 g, 19.7 mmol). After stirring overnight, the mixture was poured into water and extracted with DCM. The organic extract was washed with brine, dried over $Na_2SO_4$, filtered, and concentrated. Purification by silica gel flash column chromatography afforded methyl 4-((tert-butoxycarbonyl)amino)-3-fluoroimidazo[1,5-a]quinoxaline-8-carboxylate (5.8 g, 75%). ES/MS: m/z=360.9 $[M+H]^+$.

Step 2: 4-((tert-butoxycarbonyl)amino)-3-fluoroimidazo[1,5-a]quinoxaline-8-carboxylic acid (Ah-1). To a solution of methyl 4-((tert-butoxycarbonyl)amino)-3-fluoroimidazo[1,5-a]quinoxaline-8-carboxylate (5.8 g, 14.8 mmol) in THF/MeOH/$H_2O$ (1:1:1, 90 mL) was added LiOH (1.86 g, 44 mmol). After one hour, the mixture was concentrated, then the pH was adjusted to 5 with formic acid to afford 4-((tert-butoxycarbonyl)amino)-3-fluoroimidazo[1,5-a]quinoxaline-8-carboxylic acid (4.14 g, 80%). ES/MS:

m/z=290.8.0 [M-tBu+H]$^+$. $^1$H NMR (DMSO-$d_6$ 400 MHz): δ 10.1-10.0 (m, 1H), 9.09 (s, 1H), 8.74 (s, 1H), 8.40 (s, 1H), 8.01 (t, J=7.20 Hz, 1H), 7.67 (d, J=8.40 Hz, 1H), 1.46 (s, 9H).

General Procedure IX-A for the Synthesis of Acid Intermediates Ai.

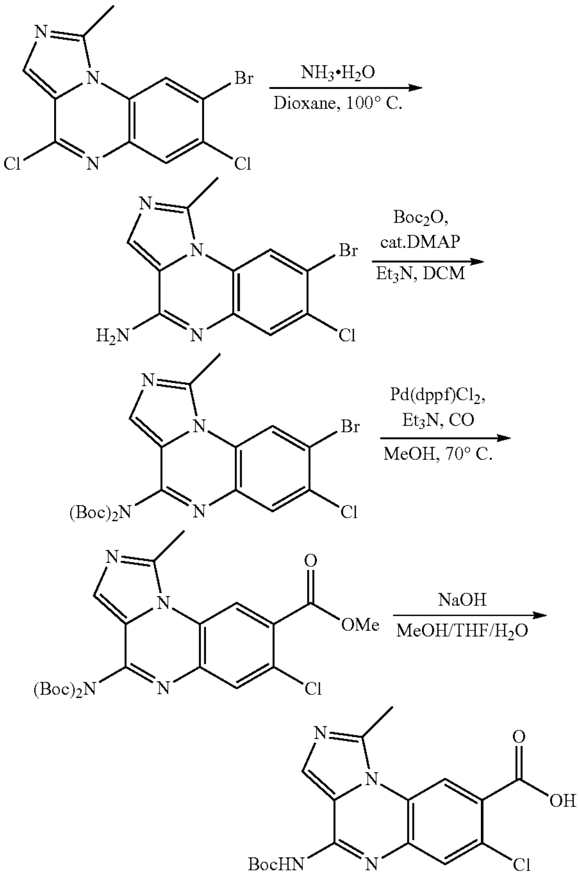

Ai-1

Step 1. 8-bromo-4,7-dichloro-1-methylimidazo[1,5-a]quinoxaline. 8-bromo-4-chloro-1,7-dimethylimidazo[1,5-a]quinoxaline (prepared following steps 1-4 from general procedure III-A starting with 1-bromo-2-chloro-5-fluoro-4-nitrobenzene and 2-methyl-1H-imidazole, 3.70 g, 10.2 mmol) was charged in an autoclave. It was dissolved in dioxane (15 mL) and $NH_3 \cdot H_2O$ (15.0 mL) was added. The mixture was stirred at 100° C. for 12 h then cooled to room temperature and filtered. The solids were triturated with EtOAc at 25° C. for 30 mins, then filtered and the solids were dried under vacuum to afford the desired product. ES/MS: m/z=312.3 [M+H]$^+$.

Step 2. tert-butyl (8-bromo-7-chloro-1-methylimidazo[1,5-a]quinoxalin-4-yl)(tert-butoxycarbonyl)carbamate. 8-bromo-4,7-dichloro-1-methylimidazo[1,5-a]quinoxaline (2.80 g, 8.81 mmol) was suspended in DCM (70 mL) and $Boc_2O$ (4.23 g, 19.4 mmol), DMAP (538 mg, 4.40 mmol) and triethylamine (2.67 g, 26.4 mmol) were successively added. The mixture was stirred at 40° C. for 12 h, then cooled to room temperature and filtered. The filtered organics were concentrated to dryness and then triturated with ethyl acetate at 25° C. for 30 mins. The solids were filtered and dried under vacuum to afford the desired product. ES/MS: m/z=513.1 [M+H]$^+$.

Step 3. Methyl 4-(bis(tert-butoxycarbonyl)amino)-7-chloro-1-methylimidazo[1,5-a]quinoxaline-8-carboxylate. To a solution of tert-butyl (8-bromo-7-chloro-1-methylimidazo[1,5-a]quinoxalin-4-yl)(tert-butoxycarbonyl)carbamate (2.0 g, 3.60 mmol) in MeOH (20 mL) was added triethylamine (1.09 g, 10.8 mmol) and Pd(dppf)$Cl_2$ (526 mg, 0.72 mmol). The suspension was degassed under the vacuum and purged with CO three times. The resulting mixture was stirred at 80° C. for 16 hrs under CO (50 psi). Upon completion, the mixture was filtered and the organics were concentrated in vacuo. The crude material was triturated with ethyl acetate at 25° C. for 30 mins, then filtered and the solids were dried under vacuum to afford the desired product. ES/MS: m/z=491.2 [M+H]$^+$.

Step 4. 4-((tert-butoxycarbonyl)amino)-7-chloro-1-methylimidazo[1,5-a]quinoxaline-8-carboxylic acid (Ai-1). To a solution of methyl 4-(bis(tert-butoxycarbonyl)amino)-7-chloro-1-methylimidazo[1,5-a]quinoxaline-8-carboxylate (2.25 g, 4.58 mmol) in MeOH (4.80 mL), THF (16.0 mL) and water (4.80 mL) was added NaOH (733 mg, 18.3 mmol). The reaction was stirred at 25° C. for 2 hrs and the organics were evaporated under reduced pressure. The pH was adjusted to pH=6 using a solution of HCOOH (1.00 M) and the solids were filtered. The solids were redissolved in 20 mL of NaOH (1M) and the suspension was filtered. The aqueous were purified by prep-HPLC (Column 330 g Flash Column Welch Ultimate XB_C18 20-40 m; 120 A.; Flow rate: 100 ml/min; Mobile phase: $H_2O$+ACN; Gradient B %: 10-60% 18 mins; % min; Instrument: ISCO). The desired product Ai-1 was obtained. ES/MS: m/z=377.3 [M+H]$^+$. $^1$H NMR (DMSO-$d_6$400 MHz) δ 8.19 (s, 1H), 7.27 (d, J=6.0 Hz, 2H), 2.83 (s, 3H), 1.41 (s, 9H).

General Procedure X-A for the Synthesis of Acid Intermediates Aj.

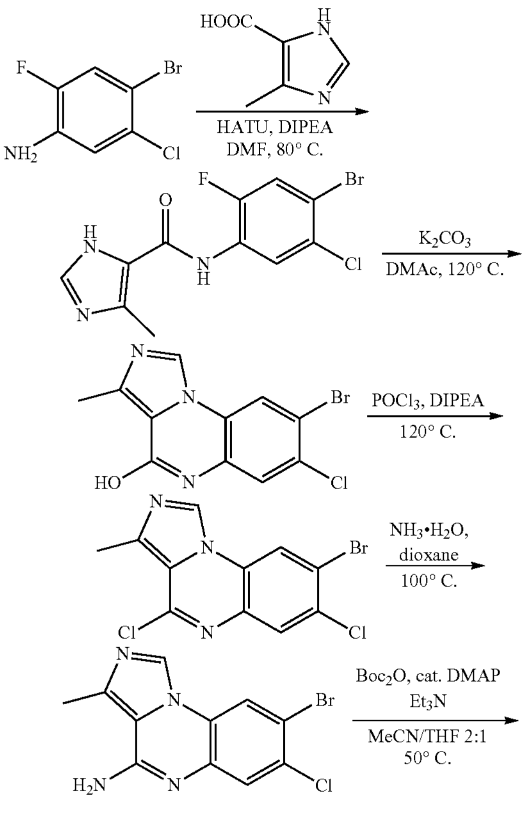

-continued

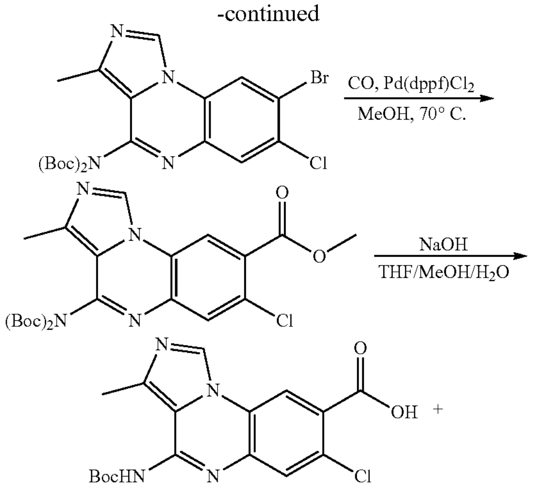

Aj-1

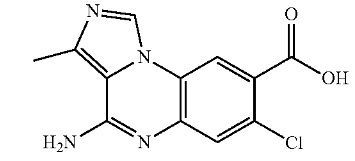

Aj-2

Step 1. N-(4-bromo-5-chloro-2-fluorophenyl)-4-methyl-1H-imidazole-5-carboxamide. 4-bromo-5-chloro-2-fluoroaniline (50 g, 223 mol), 4-methyl-1H-imidazole-5-carboxylic acid (50.5 g, 401 mmol), HATU (127 g, 334 mmol) and DIPEA (86.3 g, 334 mmol) were charged in the reaction vessel and DMF (500 mL) was added. The mixture was stirred at 80° C. for 16 h under $N_2$ before it was cooled down to room temperature and poured into water (3 L). The mixture was extracted with EtOAc (5×500 mL). The combined organics were washed with brine (2×700 mL), dried over $Na_2SO_4$, filtered, and evaporated to dryness. The residue was purified by silica gel column chromatography to afford the desired product. ES/MS: m/z=333.9 $[M+H]^+$.

Step 2. 8-bromo-7-chloro-3-methylimidazo[1,5-a]quinoxalin-4-ol. Prepared following step 2 of general procedure VII-A starting with N-(4-bromo-5-chloro-2-fluorophenyl)-4-methyl-1H-imidazole-5-carboxamide. ES/MS: m/z=313.9 $[M+H]^+$.

Step 3. 8-bromo-4,7-dichloro-3-methylimidazo[1,5-a]quinoxaline. Prepared following step 4 of general procedure VII-A (expect the reaction was run at 120° C.) starting with 8-bromo-7-chloro-3-methylimidazo[1,5-a]quinoxalin-4-ol. ES/MS: m/z=331.8 $[M+H]^+$.

Step 4. 8-bromo-7-chloro-3-methylimidazo[1,5-a]quinoxalin-4-amine. Prepared following step 1 of general procedure IX-A starting with 8-bromo-4,7-dichloro-3-methylimidazo[1,5-a]quinoxaline. ES/MS: m/z=312.9 $[M+H]^+$.

Step 5. tert-butyl (8-bromo-7-chloro-3-methylimidazo[1,5-a]quinoxalin-4-yl)(tert-butoxycarbonyl)carbamate. Prepared following step 2 of general procedure IX-A (except MeCN/THF 2:1 was used as the solvent) starting with 8-bromo-7-chloro-3-methylimidazo[1,5-a]quinoxalin-4-amine. ES/MS: m/z=513.1 $[M+H]^+$.

Step 6. Methyl 4-(bis(tert-butoxycarbonyl)amino)-7-chloro-3-methylimidazo[1,5-a]quinoxaline-8-carboxylate. Prepared following step 3 of general procedure IX-A starting with tert-butyl (8-bromo-7-chloro-3-methylimidazo[1,5-a]quinoxalin-4-yl)(tert-butoxycarbonyl)carbamate. ES/MS: m/z=491.2 $[M-Me+H]^+$.

Step 7. 4-((tert-butoxycarbonyl)amino)-7-chloro-3-methylimidazo[1,5-a]quinoxaline-8-carboxylic acid (Aj-1) and 4-amino-7-chloro-3-methylimidazo[1,5-a]quinoxaline-8-carboxylic acid (Aj-2). Prepared following step 4 of general procedure IX-A starting with methyl 4-(bis(tert-butoxycarbonyl)amino)-7-chloro-3-methylimidazo[1,5-a]quinoxaline-8-carboxylate.

4-((tert-butoxycarbonyl)amino)-7-chloro-3-methylimidazo[1,5-a]quinoxaline-8-carboxylic acid (Aj-1). ES/MS: m/z=377.0 $[M+H]^+$. $^1H$ NMR (DMSO-$d_6$400 MHz) δ 9.17 (br s, 1H), 8.38 (s, 1H), 7.77-7.63 (m, 1H), 2.55 (s, 3H), 1.49 (s, 9H).

4-amino-7-chloro-3-methylimidazo[1,5-a]quinoxaline-8-carboxylic acid (Aj-2). ES/MS: m/z=276.8 $[M+H]^+$. $^1H$ NMR (DMSO-$d_6$400 MHz) c 9.01 (br s, 1H), 8.31 (s, 1H), 7.28 (s, 1H), 6.95 (s, 2H), 2.61 (s, 3H).

General Procedure XI-A for the Synthesis of Acid Intermediates Ak.

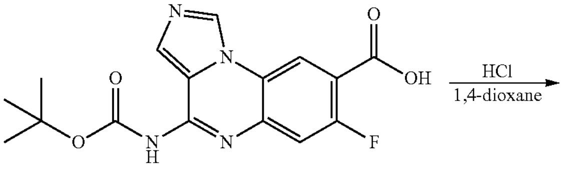

Af-1

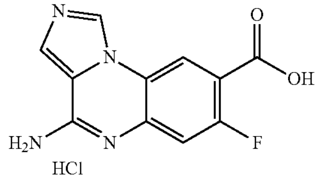

Ak-1

4-amino-7-fluoroimidazo[1,5-a]quinoxaline-8-carboxylic acid hydrochloride (Ak-1). 4-(tert-butoxycarbonylamino)-7-fluoro-imidazo[1,5-a]quinoxaline-8-carboxylic acid (Af-1, 10.0 g, 28.9 mmol) was suspended in 1,4-dioxane (50 mL) and hydrochloric acid (4.0 M in 1,4-dioxane, 22 mL, 88 mmol) was added slowly. The suspension was allowed to stir overnight, then filtered, washing with tetrahydrofuran (50 mL), to afford the product after drying under vacuum. ES/MS: m/z=246.9 $[M+H]^+$. $^1H$ NMR (400 MHz, DMSO-$d_6$) δ 10.00 (brs, 1H), 9.57 (s, 1H), 9.19 (brs, 1H), 8.81 (d, J=6.6 Hz, 1H), 8.48 (s, 1H), 7.53 (d, J=11.2 Hz, 1H).

Ak-2

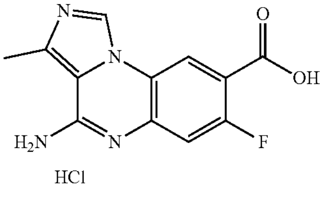

4-amino-7-fluoro-3-methylimidazo[1,5-a]quinoxaline-8-carboxylic acid hydrochloride (Ak-2). Prepared according to general procedure XI-A starting with 4-((tert-butoxycarbonyl)amino)-7-fluoro-3-methylimidazo[1,5-a]quinoxaline-8-carboxylic acid Af-4. ES/MS: m/z=261.0 $[M+H]^+$.

Ak-3

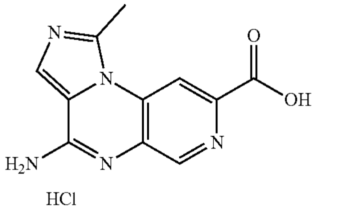

4-amino-7-chloro-3-methylimidazo[1,5-a]quinoxaline-8-carboxylic acid hydrochloride (Ak-3). Prepared according to general procedure XI-A starting with 4-((tert-butoxycarbonyl)amino)-1-methylimidazo[1,5-a]pyrido[3,4-e]pyrazine-8-carboxylic acid Ag-1. ES/MS: m/z=244.0 [M+H]$^+$.

Ak-4

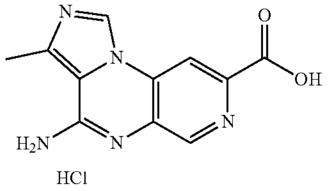

4-amino-3-methylimidazo[1,5-a]pyrido[3,4-e]pyrazine-8-carboxylic acid hydrochloride (Ak-4). Prepared according to general procedure XI-A starting with 4-((tert-butoxycarbonyl)amino)-3-methylimidazo[1,5-a]pyrido[3,4-e]pyrazine-8-carboxylic acid (Ag-2). ES/MS: m/z=244.2 [M+H]$^+$.

Ak-5

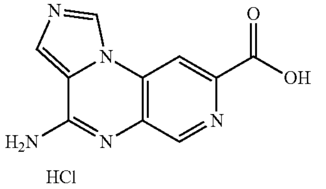

4-aminoimidazo[1,5-a]pyrido[3,4-e]pyrazine-8-carboxylic acid hydrochloride (Ak-5). Prepared according to general procedure XI-A starting with 4-((tert-butoxycarbonyl)amino)imidazo[1,5-a]pyrido[3,4-e]pyrazine-8-carboxylic acid (Af-6). ES/MS: m/z=230.2 [M+H]$^+$.

Ak-6

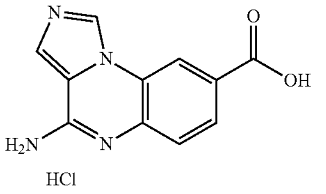

4-aminoimidazo[1,5-a]quinoxaline-8-carboxylic acid hydrochloride (Ak-6). Prepared according to general procedure XI-A starting with 4-((tert-butoxycarbonyl)amino)imidazo[1,5-a]quinoxaline-8-carboxylic acid Ae-1. ES/MS: m/z=229.2 [M+H]$^+$.

General Procedure XII-A for the Synthesis of Acid Intermediates Al

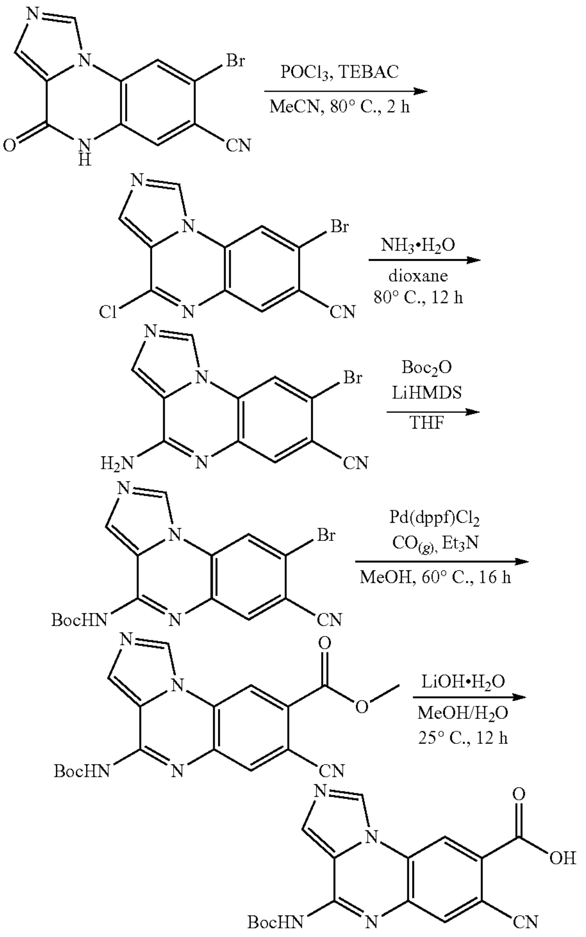

Al-1

Step 1. 8-bromo-4-chloroimidazo[1,5-a]quinoxaline-7-carbonitrile. 8-bromo-4-oxo-4,5-dihydroimidazo[1,5-a]quinoxaline-7-carbonitrile (prepared following steps 1-2 from general procedure VI-A starting with 5-amino-2-bromo-4-fluorobenzonitrile and 5H,10H-diimidazo[1,5-a:1',5'-d]pyrazine-5,10-dione ES/MS: m/z=289.9 [M+H]$^+$, 3 g, 10.3 mmol) was suspended in MeCN (30 mL) and $POCl_3$ (9.67 mL, 10 equiv.) followed by TEBAC (7.09 g, 3 equiv.) were charged at 20° C. The mixture was stirred at 80° C. for 2 hours. The mixture was then cooled to room temperature and poured into water (170 mL); it was then filtered and the cake was washed with water (170 mL). The solids were dried and triturated in EtOAc (100 mL) followed by filtration to afford the desired product. ES/MS: m/z=308.8 [M+H]$^+$.

Step 2. 4-amino-8-bromoimidazo[1,5-a]quinoxaline-7-carbonitrile. Prepared following the procedure reported in general procedure VI-A for step 5 starting with 8-bromo-4-chloroimidazo[1,5-a]quinoxaline-7-carbonitrile. ES/MS: m/z=287.9 [M+H]$^+$.

Step 3. tert-butyl (8-bromo-7-cyanoimidazo[1,5-a]quinoxalin-4-yl)carbamate. 4-amino-8-bromoimidazo[1,5-a]quinoxaline-7-carbonitrile (1 g, 305 mmol) was dissolved into THF (30 mL) and cooled to −78° C. and LiHMDS (1M in THF, 7.64 mL, 3 equiv.) was added. The mixture was warmed up to room temperature and $Boc_2O$ (0.80 g, 1.2 equiv.) was added. The mixture was stirred for 1 hour and then quenched with $NH_4Cl$ aqueous solution (60 mL). After usual work up (EtOAc, brine), the combined organics were dried over $Na_2SO_4$, filtered and concentrated. The crude material was purified by HPLC (column: Phenomenex luna C18 (250*70 mm, 10 m); mobile phase: [water ($NH_4HCO_3$)-ACN]; gradient: 50%-80% B over 22 min). ES/MS: m/z=388.0 $[M+H]^+$.

Step 4. methyl 4-((tert-butoxycarbonyl)amino)-7-cyanoimidazo[1,5-a]quinoxaline-8-carboxylate. Prepared following the procedure reported in general procedure VI-A for step 3 (except the reaction was run at 60° C.) starting with tert-butyl (8-bromo-7-cyanoimidazo[1,5-a]quinoxalin-4-yl) carbamate. ES/MS: m/z=368.0 $[M+H]^+$.

Step 5. 4-((tert-butoxycarbonyl)amino)-7-cyanoimidazo [1,5-a]quinoxaline-8-carboxylic acid (Al-1). Prepared following the procedure reported in general procedure VI-A for step 7 starting with methyl 4-((tert-butoxycarbonyl)amino)-7-cyanoimidazo[1,5-a]quinoxaline-8-carboxylate. ES/MS: m/z=354.1 $[M+H]^+$. $^1H$ NMR (DMSO-$d_6$ 400 MHz) δ 9.41 (s, 1H), 8.77 (s, 1H), 8.12 (s, 1H), 7.95 (s, 1H), 1.53 (s, 9H).

General Procedure XIII-A for the Synthesis of Acid Intermediates am

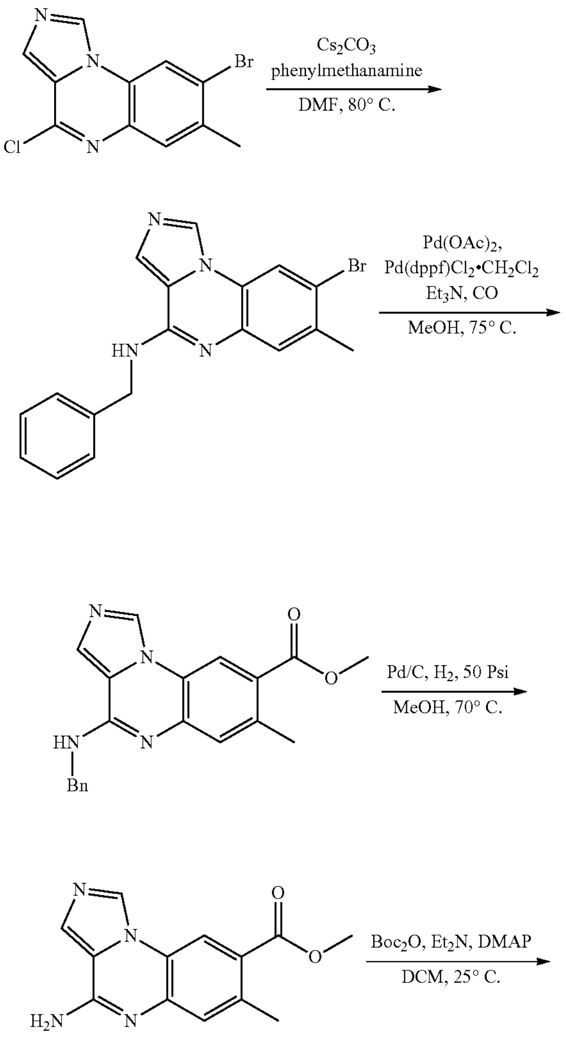

-continued

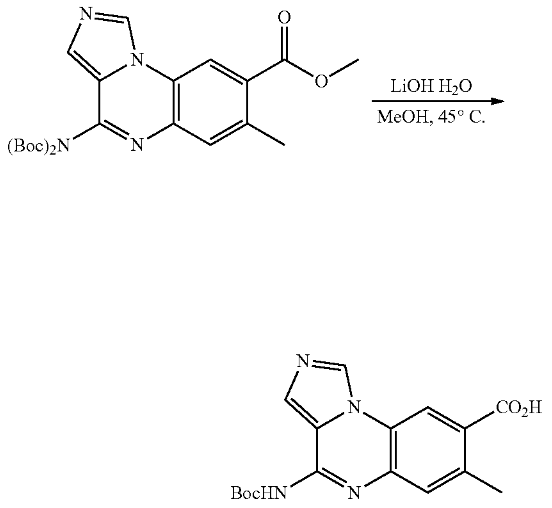

Am-1

Step 1. N-benzyl-8-bromo-7-methylimidazo[1,5-a]quinoxalin-4-amine. Prepared following the procedure reported in general procedure III-A for step 5 starting with 8-bromo-4-chloro-7-methylimidazo[1,5-a]quinoxaline and phenylmethanamine. ES/MS: m/z=368.1 $[M+H]^+$.

Step 2. Methyl 4-(benzylamino)-7-methylimidazo[1,5-a] quinoxaline-8-carboxylate. Prepared following the procedure reported in general procedure IX-A for step 3 starting with N-benzyl-8-bromo-7-methylimidazo[1,5-a]quinoxalin-4-amine. ES/MS: m/z=347.1 $[M+H]^+$.

Step 3. Methyl 4-amino-7-methylimidazo[1,5-a]quinoxaline-8-carboxylate. Pd/C (1.61 g, 1.5 mmol) was charged into a flask and MeOH (160 mL) followed by methyl 4-(benzylamino)-7-methylimidazo[1,5-a]quinoxaline-8-carboxylate (1.1 g, 3 mmol) were added. The mixture was degassed with argon 3 times followed by $H_{2(g)}$ 3 times. The mixture was stirred at 70° C. under an atmosphere of $H_{2(g)}$ (50 psi) for 24 hours. The mixture was the cooled to room temperature degassed with argon 3 times and filtered to afford the desired product. ES/MS: m/z =257.1 $[M+H]^+$.

Step 4. Methyl 4-(bis(tert-butoxycarbonyl)amino)-7-methylimidazo[1,5-a]quinoxaline-8-carboxylate. Prepared following the procedure reported in general procedure IX-A for step 2 starting with methyl 4-(bis(tert-butoxycarbonyl) amino)-7-methylimidazo[1,5-a]quinoxaline-8-carboxylate. Methyl 4-amino-7-methylimidazo[1,5-a]quinoxaline-8-carboxylate. ES/MS: m/z=457.0 $[M+H]^+$.

Step 5. 4-((tert-butoxycarbonyl)amino)-7-methylimidazo [1,5-a]quinoxaline-8-carboxylic acid (Am-1). Prepared following the procedure reported in general procedure VI-A for step 6 starting with methyl 4-(bis(tert-butoxycarbonyl) amino)-7-methylimidazo[1,5-a]quinoxaline-8-carboxylate. ES/MS: m/z=343.0 $[M+H]^+$. $^1H$ NMR (400 MHz, DMSO-d6) δ 10.32 (br s, 1H), 9.32 (s, 1H), 8.70 (s, 1H), 8.08 (s, 1H), 7.60 (s, 1H), 2.61 (s, 3H), 1.53 (s, 9H).

General Procedure XIV-A for the Synthesis of Acid Intermediates an

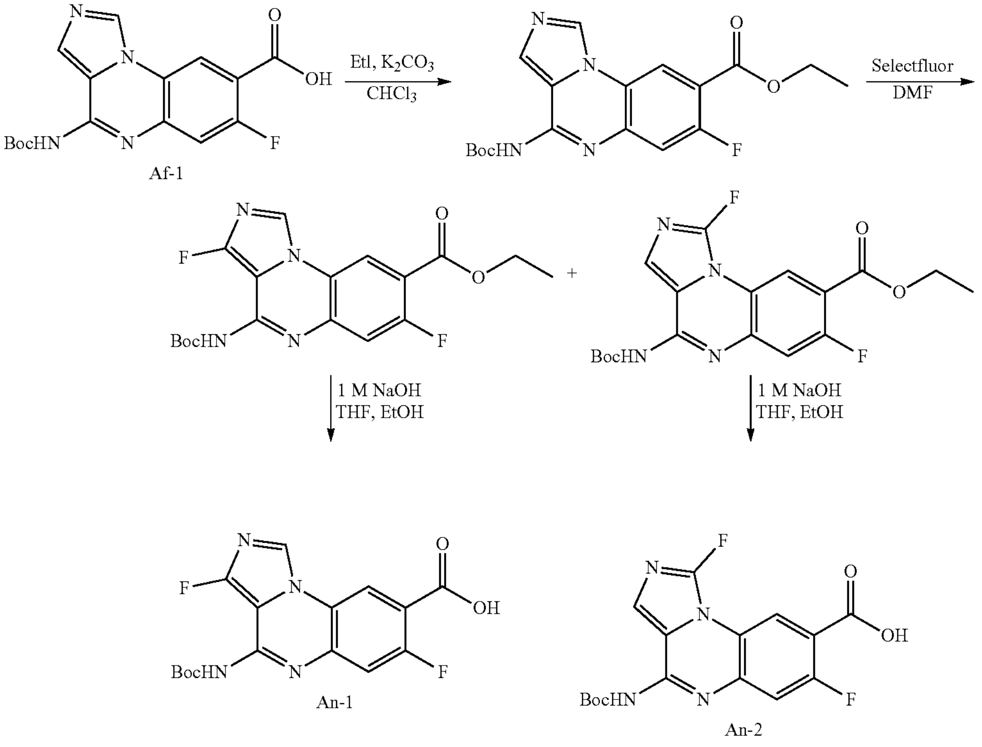

Step 1. Ethyl 4-(tert-butoxycarbonylamino)-7-fluoro-imidazo[1,5-a]quinoxaline-8-carboxylate. To a solution of 4-(tert-butoxycarbonylamino)-7-fluoro-imidazo[1,5-a]quinoxaline-8-carboxylic acid (Af-1, 500 mg, 1.44 mmol) in DMF (4.86 mL) was added potassium carbonate (600 mg, 4.3 mmol, 3.0 equiv) and ethyliodide (0.348 mL, 4.3 mmol, 3.0 equiv) at 0° C. The mixture was warmed to 23° C. and stirred for about 16 h. The reaction was then diluted with 10 mL of saturated $NaHCO_3$ and 10 mL of methylene chloride. The layers were separated and the aqueous layer was extracted with methylene chloride (2×10 mL). The combined organics were then dried over $MgSO_4$, filtered and concentrated under reduced pressure. The resulting product was purified via silica gel column chromatography to afford ethyl 4-(tert-butoxycarbonylamino)-7-fluoro-imidazo[1,5-a]quinoxaline-8-carboxylate. ES/MS: m/z=375.1 $[M+H]^+$.

Step 2. Ethyl 4-(tert-butoxycarbonylamino)-3,7-difluoro-5a,9a-dihydroimidazo[1,5-a]quinoxaline-8-carboxylate (Ks-4) and ethyl 4-(tert-butoxycarbonylamino)-1,7-difluoro-5a,9a-dihydroimidazo[1,5-a]quinoxaline-8-carboxylate (Ks-5). A vial was charged with ethyl 4-(tert-butoxycarbonylamino)-7-fluoro-5a,9a-dihydroimidazo[1,5-a]quinoxaline-8-carboxylate (Af-1, 50.0 mg, 0.133 mmol) and Selectfluor (47.1 mg, 0.133 mmol), then suspended in DMF (1.00 mL). The vial was stirred overnight at room temperature. After the allotted time, saturated ammonium chloride (10 mL) was carefully added to the mixture. The resulting mixture was transferred to a separatory funnel and extracted with ethyl acetate (2×10 mL). The combined organic layers were then dried over magnesium sulfate, filtered and concentrated under reduced pressure to afford crude product, which was purified via silica gel column chromatography to afford Ethyl 4-(tert-butoxycarbonylamino)-3,7-difluoro-5a,9a-dihydroimidazo[1,5-a]quinoxaline-8-carboxylate. First peak. ES/MS: m/z=337.0 $[M+H\text{-tert-butyl}]^+$. $^1H$ NMR (400 MHz, Methanol-d4) δ 8.59 (dd, J=6.7, 1.7 Hz, 1H), 7.86 (d, J=1.2 Hz, 1H), 7.65 (d, J=11.8 Hz, 1H), 4.46 (q, J=7.1 Hz, 2H), 1.63 (s, 9H), 1.44 (t, J=7.1 Hz, 3H). Ethyl 4-(tert-butoxycarbonylamino)-1,7-difluoro-5a,9a-dihydroimidazo[1,5-a]quinoxaline-8-carboxylate. Second peak. ES/MS: m/z=337.0. $^1H$ NMR (400 MHz, Methanol-d4) δ 8.86 (d, J=1.1 Hz, 1H), 8.71 (d, J=6.6 Hz, 1H), 7.61 (d, J=11.5 Hz, 1H), 4.47 (q, J=7.1 Hz, 2H), 1.60 (s, 9H), 1.45 (t, J=7.1 Hz, 3H).

An-1

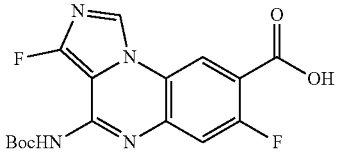

Step 3. 4-((tert-butoxycarbonyl)amino)-3,7-difluoroimidazo[1,5-a]quinoxaline-8-carboxylic acid (An-1). A vial was charged with Ks-4 (15 mg, 0.038 mmol, 1.0 equiv), and suspended in 1 M NaOH (0.3 mL), THF (0.3 mL) and ethanol (0.3 mL). The reaction was stirred at room temperature for 1 hour. The mixture was then neutralized with HCl until a pH of 7 was obtained. The reaction mixture was then concentrated under reduced pressure to afford 4-((tert-butoxycarbonyl)amino)-3,7-difluoroimidazo[1,5-a]quinoxaline-8-carboxylic acid which was used without further purification. ES/MS: m/z=365.1 $[M+H]^+$.

An-2

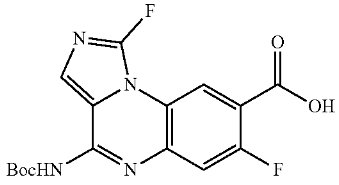

4-((tert-butoxycarbonyl)amino)-1,7-difluoroimidazo[1,5-a]quinoxaline-8-carboxylic acid (An-2). Prepared following step 3. starting with ethyl 4-(tert-butoxycarbonylamino)-1,7-difluoro-5a,9a-dihydroimidazo[1,5-a]quinoxaline-8-carboxylate. ES/MS: m/z=365.1 $[M+H]^+$.

General Procedure XV-A for the Synthesis of Acid Intermediates Ao

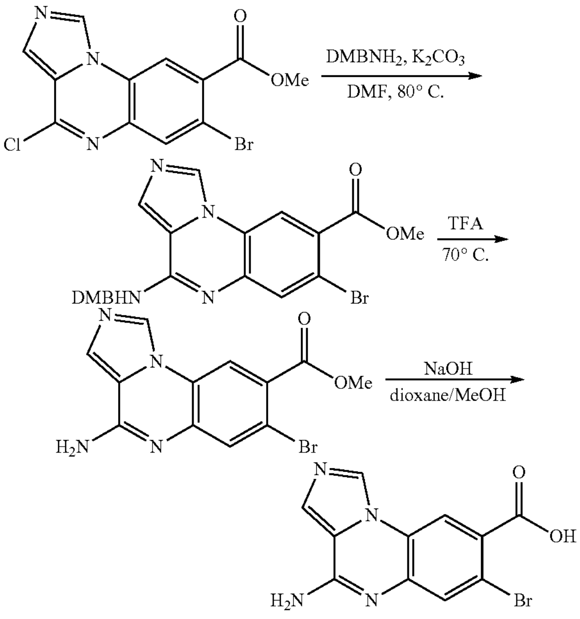

Ao-1

Step 1. Methyl 7-bromo-4-((3,4-dimethylbenzyl)amino)imidazo[1,5-a]quinoxaline-8-carboxylate. Methyl 7-bromo-4-chloroimidazo[1,5-a]quinoxaline-8-carboxylate (prepared following steps 1, 2 and 4 of general procedure VI-A starting with methyl 4-amino-2-bromo-5-fluorobenzoate and 5H,10H-diimidazo[1,5-a:1',5'-d]pyrazine-5,10-dione) (32.0 g, 1 equiv.) was dissolved in DMF (192 mL) and $K_2CO_3$ (25.9 g, 2.0 equiv.) was added followed by and $DMBNH_2$ (18.8 g, 1.20 equiv.). The mixture was stirred at 80° C. for 3 hours; then cooled to room temperature and poured in $H_2O$ (600 mL). The suspension was filtered and dried to obtain the title compound.

Step 2. Methyl 4-amino-7-bromoimidazo[1,5-a]quinoxaline-8-carboxylate. TFA (130 mL) was added to methyl 7-bromo-4-((3,4-dimethylbenzyl)amino)imidazo[1,5-a]quinoxaline-8-carboxylate (26 g, 1 equiv.) and the mixture was stirred at 70° C. for 3 hours. It was the cooled to room temperature and evaporated under reduced pressure. The mixture was poured into $H_2O$ (100 mL) and the Ph was adjusted to pH=8 with a saturated aqueous solution of $Na_2CO_3$. The suspension was filtered and dried to obtain the title compound.

Step 3. 4-amino-7-bromoimidazo[1,5-a]quinoxaline-8-carboxylic acid (Ao-1). Methyl 4-amino-7-bromoimidazo[1,5-a]quinoxaline-8-carboxylate (10 g, 1 equiv.), methanol (30 mL) and dioxanne (60 mL) were charged into a reactor. NaOH (4.0 M, 14.4 mL, 1.28 equiv.) was added, and the mixture was stirred at room temperature for 3 hours. The pH was then adjusted to pH=5 with HCl (1.0 M). The suspension was filtered, and the crude mixture was triturated with MeOH (30.0 mL) at 25° C. for 30 minutes and the solids were filtered and dried to afford the desired product Ao-1. ES/MS: m/z=308.9 $[M+H]^+$. tH NMR (400 MHz, DMSO-$d_6$) δ=9.21 (s, 1H), 8.59 (s, 1H), 7.94 (s, 1H), 7.72 (s, 2H), 7.62 (s, 1H).

Synthesis of Acid Intermediates B

General Procedure I-B for the Synthesis of Acids Ba:

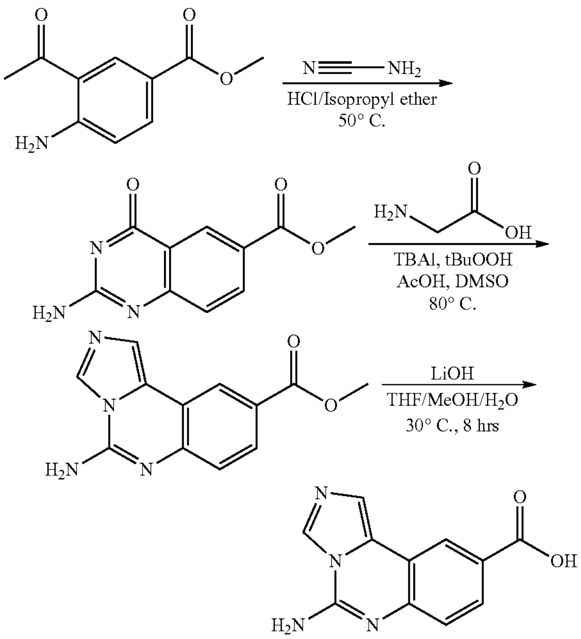

Ba-1

Step 1: Methyl 2-amino-4-methylquinazoline-6-carboxylate. A solution of methyl 3-acetyl-4-aminobenzoate (5.0 g, 25.8 mmol) in HCl in isopropyl ether (2M, 100 mL) was stirred at 30° C. for one hour before cyanamide (37.5 g, 892 mmol) was added. The resulting mixture was stirred at 50° C. for 12 hours then poured into water (20 mL) and the PH was adjusted to 8 using $NaHCO_3$. The mixture was extracted with EtOAc (20 mL×4) and the combined organic layers were dried over $Na_2SO_4$, filtered, and concentrated to dryness to deliver methyl 2-amino-4-methylquinazoline-6-carboxylate. ES/MS: m/z=218.1 $[M+H]^+$. $^1H$ NMR (DMSO-$d_6$ 400 MHz) δ 8.50 (d, J=1.6 Hz, 1H), 8.09 (dd, $J_1$=1.6 Hz, $J_2$=8.8 Hz, 1H), 7.42 (d, J=8.8 Hz, 1H), 7.14 (brs, 2H), 3.83 (s, 3H), 2.75 (s, 3H).

Step 2: Methyl 5-aminoimidazo[1,5-c]quinazoline-9-carboxylate. n-$Bu_4NI$ (850 mg, 2.30 mmol), TBHP (4.15 g, 46.0 mmol) and acetic acid (2.07 g, 34.5 mmol) were successively added to a solution of methyl 2-amino-4-methylquinazoline-6-carboxylate (2.50 g, 11.5 mmol) and glycine (1.73 g, 23 mmol) in DMSO (17.5 mmol). The resulting mixture was stirred for 4 hours at 80° C. then cooled to room temperature and filtered. The resulting solution was evaporated to dryness to afford the titled compound. ES/MS: m/z=243.1 $[M+H]^+$. $^1H$ NMR (DMSO-$d_6$ 400 MHz) δ 8.66 (s, 1H), 8.55 (d, J=2.0 Hz, 1H), 8.03 (s, 1H), 8.00 (brs, 2H), 7.93 (dd, $J_1$=2.0 Hz, $J_2$=8.4 Hz, 1H), 7.43 (d, J=8.4 Hz, 1H), 3.83 (s, 3H).

Step 3: 5-aminoimidazo[1,5-c]quinazoline-9-carboxylic acid (Ba-1). LiOH (1.04 g, 24.7 mmol) was added to a solution of methyl 5-aminoimidazo[1,5-c]quinazoline-9-carboxylate (2.0 g, 8.26 mmol) in THF (8 mL), MeOH (4 mL) and water (4 mL). The resulting solution was stirred at 30° C. for 8 hours then concentrated and water (10 mL) was added followed by a solution of HCl (2N) to adjust the pH to 5. The suspension was then filtered and evaporated to dryness. MeOH (10 mL) was added and the mixture was stirred for 2 hours then filtered and concentrated to deliver the desired product Ba-1. ES/MS: m/z=227.2 $[M+H]^+$. $^1H$ NMR (DMSO-$d_6$ 400 MHz) 8.15 (s, 1H), 8.54 (s, 1H), 8.00-7.90 (m, 4H), 7.41 (d, J=8.4 Hz, 1H).

Ba-2

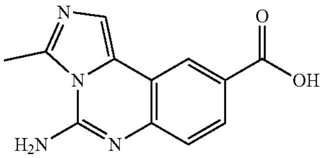

5-amino-3-methylimidazo[1,5-c]quinazoline-9-carboxylic acid (Ba-2). Prepared following general procedure D-1 using alanine in step 2. ES/MS: m/z=243.1 $[M+H]^+$. $^1H$ NMR (DMSO-$d_6$ 400 MHz): δ 8.53-8.28 (m, 1H), 7.84 (br d, J=8.0 Hz, 1H), 7.80-7.68 (m, 1H), 7.48-6.72 (m, 3H), 3.05-2.83 (m, 3H).

General Procedure II-B for the Synthesis of Acids Bb

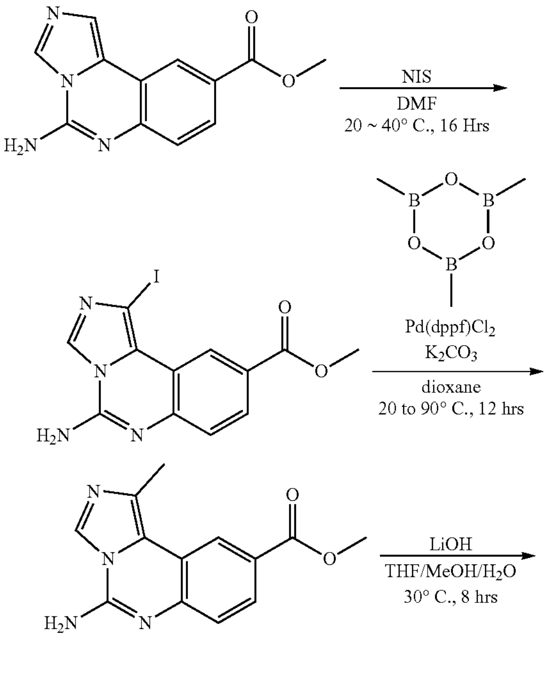

-continued

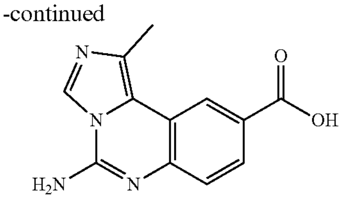

Bb-1

Step 1: Methyl 5-amino-1-iodoimidazo[1,5-c]quinazoline-9-carboxylate. To a solution of methyl 5-aminoimidazo[1,5-c]quinazoline-9-carboxylate (10.0 g, 41.2 mmol reported in general procedure I-B step 2.) in DMF (60 mL), was added NIS (10.2 g, 45.4 mmol) at 20° C. The reaction was stirred at 40° C. for 1 hour. The reaction was poured into 200 mL water to give a precipitate, which filtered and dried to give title compound.

Step 2: methyl 5-amino-1-methylimidazo[1,5-c]quinazoline-9-carboxylate. To a solution of methyl 5-amino-1-iodoimidazo[1,5-c]quinazoline-9-carboxylate (7.0 g, 19.0 mmol) and 2,4,6-trimethyl-1,3,5,2,4,6-trioxatriborinane (47.7 g, 190 mmol) in dioxane (70 mL), was added potassium carbonate (7.91 g, 57 mmol) and Pd(dppf)$Cl_2$ (1.39 g, 1.90 mmol). The reaction was heated at 90 deg for 12 hr, then poured into water (150 mL) to give precipitate, which was filtered and dried to give title compound. ES/MS: m/z=257.1 $[M+H]^+$.

Step 3: 5-amino-1-methylimidazo[1,5-c]quinazoline-9-carboxylic acid (Bb-1). LiOH (1.47 g, 35.1 mmol) was added to a solution of methyl 5-amino-1-methylimidazo[1,5-c]quinazoline-9-carboxylate (3.0 g, 11.7 mmol) in THF (12 mL), MeOH (6 mL) and water (6 mL). The resulting solution was stirred at 30° C. for 8 hours then concentrated and water (30 mL) was added followed by a solution of HCl (2N) to adjust the pH to 5. The suspension was then filtered and evaporated to dryness. Purification by prep-HPLC gave title compound. ES/MS: m/z=243.0 $[M+H]^+$. $^1H$ NMR (DMSO-$d_6$ 400 MHz): δ 8.52 (s, 1H), 8.47 (d, J=1.6 Hz, 1H), 7.88 (dd, J=1.6, 8.4 Hz, 1H), 7.70 (br s, 2H), 7.34 (d, J=8.4 Hz, 1H), 2.66 (s, 3H).

Bb-2

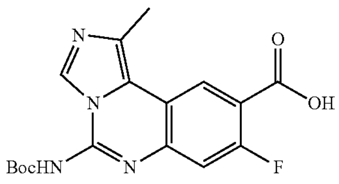

5-((tert-butoxycarbonyl)amino)-8-fluoro-1-methylimidazo[1,5-c]quinazoline-9-carboxylic acid (Bb-2). Prepared following general procedure II-B starting with methyl 2-amino-7-fluoro-4-methylquinazoline-6-carboxylate (reported in general procedure III-B step 3). Ester intermediate was Boc-protected using $Boc_2O$, DMF, DMAP, 50° C. prior to hydrolysis. ES/MS: m/z=361.1 $[M+H]^+$. $^1H$ NMR (400 MHz, DMSO-$d_6$) δ=8.47 (s, 1H), 8.28 (br d, J=7.6 Hz, 1H), 7.69 (br d, J=11.6 Hz, 1H), 2.59 (s, 3H), 1.52 (s, 9H).

General Procedure III-B for the Synthesis of Acids Bc

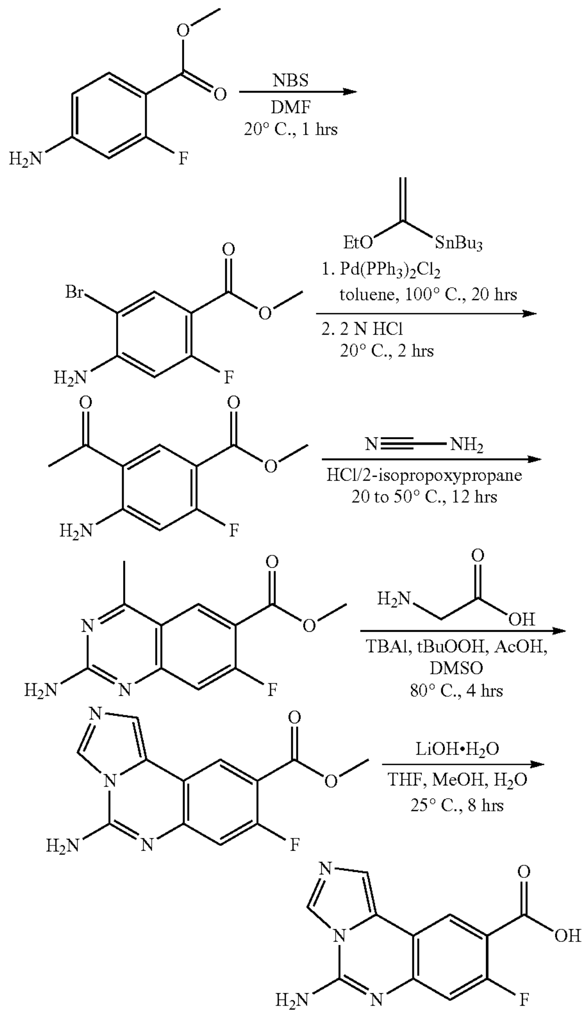

Bc-1

Step 1. Methyl 4-amino-5-bromo-2-fluorobenzoate. To a solution of methyl 4-amino-2-fluorobenzoate (44.5 g, 263 mmol) in DMF (312 mL) at 0° C. to, was added NBS (46.8 g, 263 mmol) in portions. The reaction was stirred at 20° C. for 1 hr. The reaction was poured into brine (500 mL), and the extracted with EtOAc (500 mL×2). The organic extracts were dried over sodium sulfate. The crude residue was purified by flash chromatography to give desired product.

Step 2. Methyl 5-acetyl-4-amino-2-fluorobenzoate. To a solution of methyl 4-amino-5-bromo-2-fluorobenzoate (25.0 g, 100 mmol) in toluene (175 mL), was added tributyl(1-ethoxyvinyl)stannane (61.8 g, 171 mmol, 57.7 mL) and Pd(PPh$_3$)$_2$Cl$_2$ (1.41 g, 2.02 mmol). The reaction was heated at 100° C. for 20 hrs. The reaction was cooled to 20° C. and HCl solution (2N, 175 mL) was added to the reaction mixture slowly, and stirred 20° C. for 2 hrs. The reaction was quenched with water (200 mL), and the aqueous phase was adjusted to pH=8 with Na$_2$CO$_3$ solid. The reaction mixture was extracted with EtOAc (300 mL×2), dried over Na$_2$SO$_4$, and concentrated to give desired product. ES/MS: m/z=212 [M+H]$^+$. $^1$H NMR (400 MHz, CDCl$_3$-d) δ 8.46 (d, J=8.0 Hz, 1H), 6.31 (d, J=12.8 Hz, 1H), 3.90 (s, 3H), 2.61 (s, 3H)

Step 3. Methyl 2-amino-7-fluoro-4-methylquinazoline-6-carboxylate. A solution of methyl 5-acetyl-4-amino-2-fluorobenzoate (9.15 g, 43.3 mmol) in HCl in isopropyl ether (4N, 183 mL) was stirred at 20° C. for one hour before cyanamide (123 g, 1.47 mol) was added. The resulting mixture was stirred at 50° C. for 11 hours then poured into water (20 mL) and the PH was adjusted to 8 using NaHCO$_3$. The mixture was extracted with EtOAc (200 mL×3) and the combined organic layers were dried over Na$_2$SO$_4$, filtered, and concentrated to dryness to give desired product. ES/MS: m/z=236 [M+H]$^+$. $^1$H NMR (400 MHz, DMSO-d$_6$) δ 8.48 (d, J=8.2 Hz, 1H), 7.30 (s, 2H), 7.12 (d, J=13.2 Hz, 1H), 3.87 (s, 3H), 2.73 (s, 3H)

Step 4. Methyl 5-amino-8-fluoroimidazo[1,5-c]quinazoline-9-carboxylate. n-Bu$_4$NI (1.6 g, 4.34 mmol), TBHP (11.1 g, 86.7 mmol) and acetic acid (3.91 g, 65 mmol) were successively added to a solution of Methyl 2-amino-7-fluoro-4-methylquinazoline-6-carboxylate (5.1 g, 21.6 mmol) and glycine (3.26 g, 43.3 mmol) in DMSO (35.7 mmol). The resulting mixture was stirred for 4 hours at 80° C. then cooled to room temperature and filtered. The resulting solid was recrystallized from MeOH (40 mL) and filtered to give title compound. ES/MS: m/z=261 [M+H]$^+$. $^1$H NMR (400 MHz, DMSO-d$_6$) δ ppm 8.65 (s, 1H), 8.48 (d, J=8.0 Hz, 1H), 8.16 (s, 2H), 7.97 (s, 1H), 7.16 (d, J=12.8 Hz, 1H), 3.87 (s, 3H)

Step 5. 5-amino-8-fluoroimidazo[1,5-c]quinazoline-9-carboxylic acid (Bc-1). LiOH (638 mg, 14.9 mmol) was added to a solution of methyl 5-amino-8-fluoroimidazo[1,5-c]quinazoline-9-carboxylate (1.3 g, 5.0 mmol) in THF (5.2 mL), MeOH (3.6 mL) and water (3.6 mL). The resulting solution was stirred at 25° C. for 8 hours then concentrated and water (10 mL) was added followed by a solution of HCl (2N) to adjust the pH to 5. The suspension was then filtered and triturated with water (5 mL) for 30 min, then filtered and dried to give title compound (Bc-1). ES/MS: m/z=247 [M+H]$^+$. $^1$H NMR (400 MHz, DMSO-d$_6$) δ 8.80 (s, 1H), 8.50 (d, J=8.0 Hz, 1H), 8.25 (s, 2H), 8.04 (s, 1H), 7.16 (d, J=12.4 Hz, 1H).

Bc-2

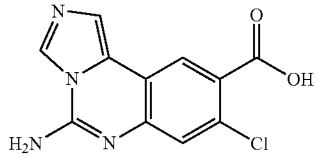

5-amino-8-chloroimidazo[1,5-c]quinazoline-9-carboxylic acid (Bc-2). Prepared following general procedure III-B starting with methyl 4-amino-2-chlorobenzoate. ES/MS: m/z =263.0 [M+H]$^+$. $^1$H NMR (DMSO-d$_6$, 400 MHz): δ 8.65 (s, 1H), 8.22 (s, 1H), 7.96-7.81 (m, 3H), 7.30 (s, 1H)

Bc-3

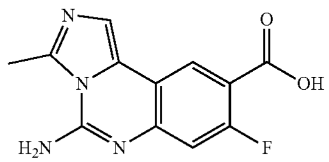

5-amino-8-fluoro-3-methylimidazo[1,5-c]quinazoline-9-carboxylic acid (Bc-3). Prepared following general procedure III-B using alanine in step 4. ES/MS: m/z=262.1

[M+H]$^+$. $^1$H NMR (DMSO-$d_6$, 400 MHz): δ 8.20 (d, J=7.6 Hz, 1H), 7.62 (s, 1H), 7.17 (brs, 2H), 2.90 (s, 3H).

General Procedure I-D for the Synthesis of Hydrazides Da

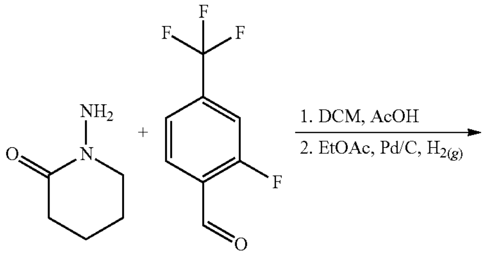

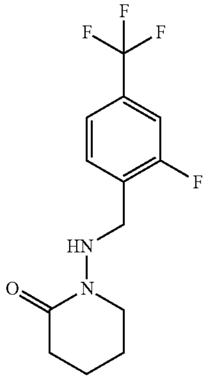

Da-1

1-((2-fluoro-4-(trifluoromethyl)benzyl)amino)piperidin-2-one Da-1 To a solution of 2-fluoro-4-(trifluoromethyl) benzaldehyde (192 mg, 1.0 mmol) and 1-aminopiperidin-2-one (114 mg, 1.0 mmol) in DCM (3 mL) was added acetic acid (0.035 mL, 0.74 mmol). The mixture was stirred at room temperature until full consumption of the starting aldehyde as judged by LCMS analysis. The crude mixture was then evaporated to dryness to give rise to (E)-1-((2-fluoro-4-(trifluoromethyl)benzylidene)amino)piperidin-2-one (ES/MS: m/z=289.1 [M+H]$^+$) which was used directly in the hydrogenation step without further purification.

The crude oil was dissolved in EtOAc (15 mL) and Pd/C (10% w/w, 192 mg) was added. The heterogenous mixture was then stirred vigorously at room temperature under an atmosphere of hydrogen (1 atm) until full conversion of the starting imine as determined by LCMS analysis. The crude mixture was then filtered over a pad of celite and evaporated to dryness to afford the desired product Da-1. ES/MS: m/z=291.0 [M+H]$^+$; $^1$H NMR (400 MHz, DMSO-$d_6$) δ 7.69 (t, J=7.6 Hz, 1H), 7.63 (dd, J=10.0, 1.7 Hz, 1H), 7.56 (dd, J=7.6, 1.7 Hz, 1H), 4.02 (s, 2H), 3.27 (t, J=6.0 Hz, 2H), 2.21 (t, J=6.5 Hz, 2H), 1.79-1.58 (m, 4H).

Da-2

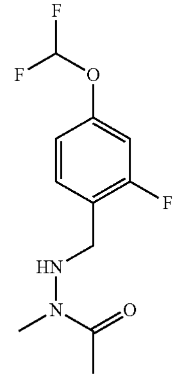

N'-(4-(difluoromethoxy)-2-fluorobenzyl)-N-methylacetohydrazide (Da-2). Prepared using general procedure I-D starting with N-methylacetohydrazide and 4-(difluoromethoxy)-2-fluorobenzaldehyde. ES/MS: m/z=263.0 [M+H]$^+$.

Da-3

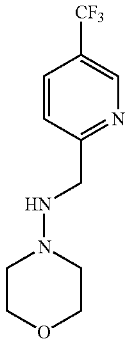

N-((5-(trifluoromethyl)pyridin-2-yl)methyl)morpholin-4-amine (Da-3). Prepared following procedure I-D starting with morpholin-4-amine and 5-(trifluoromethyl)pyridine-2-carbaldehyde. ES/MS: m/z=261.2 [M+H]$^+$.

Da-4

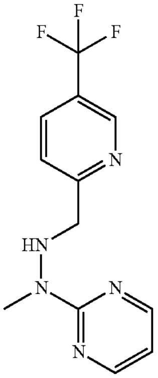

2-(1-methyl-2-((5-(trifluoromethyl)pyridin-2-yl)methyl) hydrazineyl)pyrimidine (Da-4). Prepared using general procedure I-D starting with 2-(1-methylhydrazineyl)pyrimidine and 5-(trifluoromethyl)picolinaldehyde. ES/MS: m/z=284.1 [M+H]$^+$.

Da-5

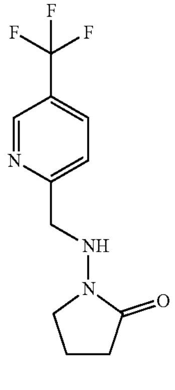

1-(((5-(trifluoromethyl)pyridin-2-yl)methyl)amino)pyrrolidin-2-one (Da-5). Prepared using general procedure I-D starting with 1-aminopyrrolidin-2-one and 5-(trifluoromethyl)picolinaldehyde. ES/MS: m/z=260.1 $[M+H]^+$.

Da-6

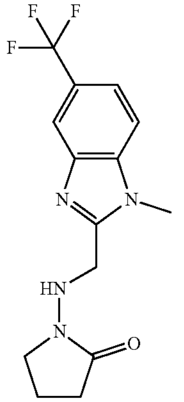

1-(((1-methyl-5-(trifluoromethyl)-1H-benzo[d]imidazol-2-yl)methyl)amino)pyrrolidin-2-one (Da-6). Prepared general procedure I-D starting with 5-(trifluoromethyl)benzo[d]thiazole-2-carbaldehyde and 1-aminopyrrolidin-2-one. ES/MS: m/z=313.2 $[M+H]^+$.

Da-7

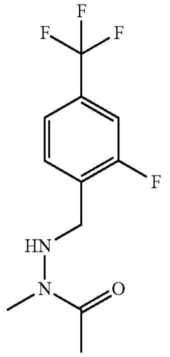

N'-(2-fluoro-4-(trifluoromethyl)benzyl)-N-methylacetohydrazide (Da-7). Prepared using general procedure I-D starting with N-methylacetohydrazide and 2-fluoro-4-(trifluoromethyl)benzaldehyde. ES/MS: m/z=265.1 $[M+H]^+$.

General Procedure II-D for the Synthesis of Hydrazides db

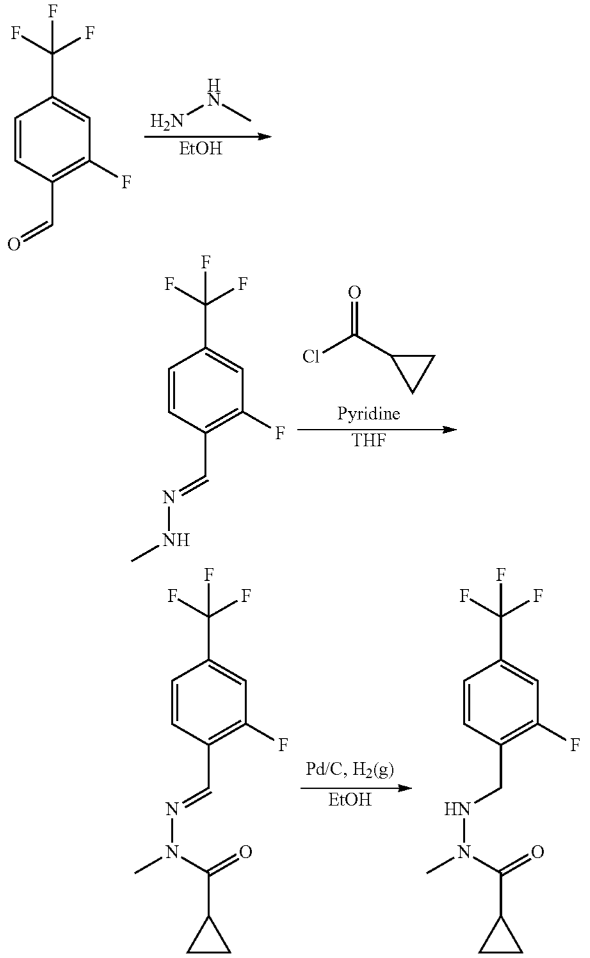

Db-1

Step 1: (E)-1-(2-fluoro-4-(trifluoromethyl)benzylidene)-2-methylhydrazine. 2-fluoro-4-(trifluoromethyl)benzaldehyde (545 mg, 2.84 mmol) and methylhydrazide (137 mg, 2.98 mmol) were dissolved in EtOH (10 mL). The mixture was left to stir at room temperature for 1 hour. The solution was reduced under pressure and purified by flash silica gel chromatography to yield the desired imine. ES/MS: m/z=221.0 $[M+H]^+$.

Step 2: (E)-N'-(2-fluoro-4-(trifluoromethyl)benzylidene)-N-methylcyclopropanecarbohydrazide. To a solution of (E)-1-(2-fluoro-4-(trifluoromethyl)benzylidene)-2-methylhydrazine (160 mg, 0.73 mmol) and cyclopropanecarbonyl chloride (85 mg, 0.81 mmol) in THF (3 mL), pyridine (117 mg, 1.48 mmol) was added. The mixture was stirred at room temperature for 12 hours and upon completion by LCMS, dissolved in EtOAc and the organic layer was washed with water twice and brine. The organic solvent was removed under pressure and the resulting residue was purified by flash silica gel chromatography desired product. ES/MS: m/z=289.0 $[M+H]^+$.

Step 3: N'-(2-fluoro-4-(trifluoromethyl)benzyl)-N-methylcyclopropanecarbohydrazide (Db-1). (E)-N'-(2-fluoro-4-(trifluoromethyl)benzylidene)-N-methylcyclopropanecarbohydrazide (130 mg, 0.45 mmol) was dissolved in EtOH (10 mL) and Pd/C (10% w/w, 130 mg) was added. The heterogeneous mixture was stirred vigorously at room temperature under hydrogen gas (1 atm). The reaction was left to stir until LCMS showed full conversion of the imine. The mixture was filtered through a pad of celite and the organic solvent was removed under pressure and purified by flash silica gel chromatography yield the desired product. ES/MS: m/z=291.2 $[M+H]^+$. $^1H$ NMR (400 MHz, $CDCl_3$) δ 7.61-7.31 (m, 3H), 4.19 (s, 1.2H, major rotamer), 4.06 (s, 0.8H, minor rotamer), 3.30 (s, 1.2H, minor rotamer), 3.23 (s, 1.8H, major rotamer), 2.46 (tt, J=8.3, 4.7 Hz, 0.6H, major rotamer), 1.66 (d, J=4.3 Hz, 0.4H, minor rotamer), 0.98 (s, 1H), 0.89-0.79 (m, 1H), 0.76 (d, J=4.2 Hz, 1H), 0.61-0.52 (m, 1H).

General Procedure III-D for the Synthesis of Intermediate Dc

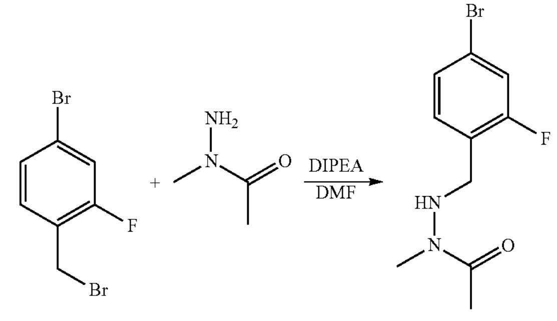

Dc-1

N'-(4-bromo-2-fluorobenzyl)-N-methylacetohydrazide (Dc-1). N-Methylacetohydrazide (54 mg, 0.6 mmol) was added to 4-bromo-1-(bromomethyl)-2-fluorobenzene (134 mg, 0.5 mmol) and N,N-Diisopropylethylamine (164 mg, 1.27 mmol) in DMF (2.5 mL). The mixture was stirred overnight at 85° C. The mixture was filtered through Celite and concentrated by rotary evaporation. The crude material was purified by chromatography (DCM/MeOH) to provide the titled compound. ES/MS: 276.0 $[M+H]^+$. $^1H$ NMR (400 MHz, Methanol-$d_4$) δ 7.62-7.06 (m, 3H), 4.02 (d, J=1.2 Hz, 2H), 3.15 (d, J=4.8 Hz, 3H), 1.99 (d, J=53.7 Hz, 3H).

Dc-2

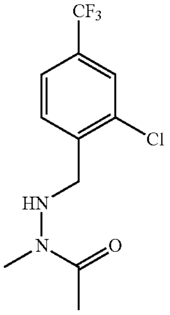

N'-(2-chloro-4-(trifluoromethyl)benzyl)-N-methylacetohydrazide (Dc-2). Prepared general procedure III-D starting with N-Methylacetohydrazide and 1-(bromomethyl)-2-chloro-4-(trifluoromethyl)benzene. ES/MS: m/z 281.0 $[M+H]^+$.

Dc-3

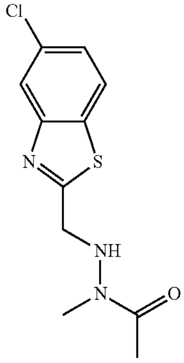

N'-[(5-chloro-1,3-benzothiazol-2-yl)methyl]-N-methylacetohydrazide (Dc-3). Prepared general procedure III-D starting with 5-chloro-2-(chloromethyl)-1,3-benzothiazole and N-methylacetohydrazide. ES/MS: m/z=270 $[M+H]^+$.

Dc-4

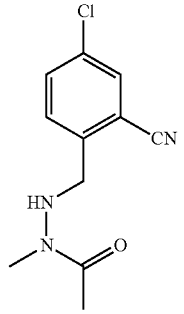

N'-(4-chloro-2-cyanobenzyl)-N-methylacetohydrazide (Dc-4). Prepared general procedure III-D starting with 2-(bromomethyl)-5-chlorobenzonitrile and N-methylacetohydrazide. ES/MS: m/z=238.0 $[M+H]^+$.

Dc-5

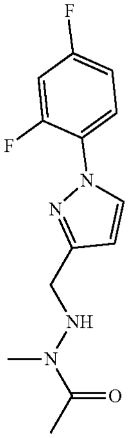

N'-((1-(2,4-difluorophenyl)-1H-pyrazol-3-yl)methyl)-N-methylacetohydrazide (Dc-5). Prepared following general procedure III-D starting with 3-(chloromethyl)-1-(2,4-difluorophenyl)-1H-pyrazole and N-methylacetohydrazide. ES/MS: m/z=281.1 $[M+H]^+$.

General Procedure IV-D for the Synthesis of Intermediates Dd

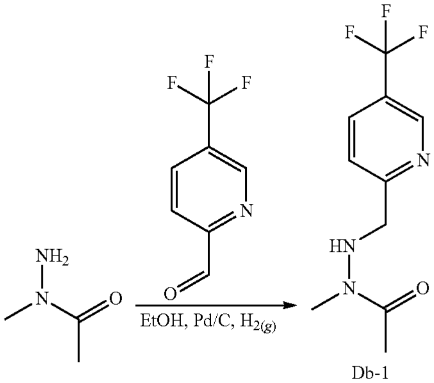

Db-1

N-methyl-N'-((5-(trifluoromethyl)pyridin-2-yl)methyl) acetohydrazide (Dd-1). To a solution of 5-(trifluoromethyl) picolinaldehyde (450 mg, 2.57 mmol) and N-methylaceto-hydrazide (0.250 g, 2.45 mmol) in EtOH (15 mL), was added Pd/C (10% w/w, 261 mg). The heterogenous mixture was then stirred vigorously at room temperature under an atmosphere of hydrogen (1 atm) until full conversion of the starting imine as determined by LCMS analysis. The crude mixture was then filtered over a pad of celite and evaporated to dryness to afford the desired product. ES/MS: m/z=248.0 $[M+H]^+$. $^1H$ NMR (400 MHz, MeOD) δ 8.90-8.84 (m, 1H), 8.15 (dd, J=8.2, 2.4 Hz, 1H), 7.73 (d, J=8.2 Hz, 1H), 4.23 (s, 2H), 3.16 (s, 3H), 2.02 (s, 3H).

General Procedure V-D for the Synthesis of Intermediates De.

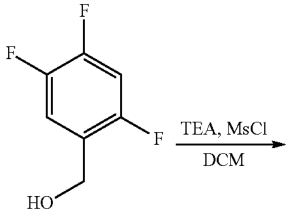

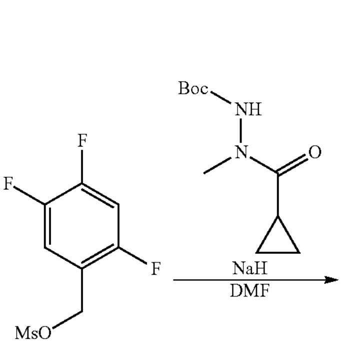

-continued

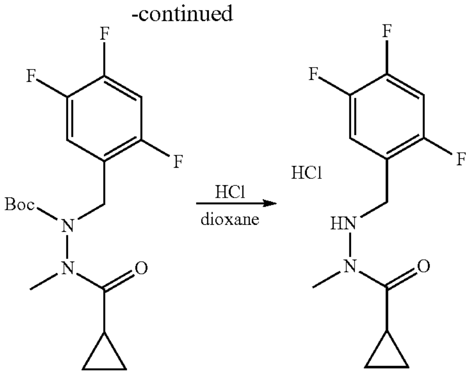

De-1

Step 1: 2,4,5-trifluorobenzyl methanesulfonate. A solution of (2,4,5-trifluorophenyl)methanol (1.0 equiv) in DCM (0.1 M) was cooled to 0 C and then triethylamine (1.2 equiv) was added followed by methanesulfonyl chloride (1.2 equiv). The reaction mixture was allowed to stir at 0 C for 10 min. At which point it was concentrated and used without further purification. ES/MS: m/z=241.0 $[M+H]^+$.

Step 2: tert-butyl 2-(cyclopropanecarbonyl)-2-methyl-1-(2,4,5-trifluorobenzyl)hydrazine-1-carboxylate. To a solution of tert-butyl 2-(cyclopropanecarbonyl)-2-methylhydrazine-1-carboxylate (1.0 equiv) in DMF (0.2 M) at 0 C, was added sodium hydride (1.2 equiv) followed by 2,4,5-trifluorobenzyl methanesulfonate (1.05 equiv). The reaction mixture was allowed to stir at 50 C overnight. at which point the reaction mixture was diluted with EtOAc and washed with 5% aqueous lithium chloride. The mixture was dried, filtered, concentrated and purified by column chromatography.

Step 4: N-methyl-N'-(2,4,5-trifluorobenzyl)cyclopropanecarbohydrazide hydrochloride (De-1): tert-butyl 2-(cyclopropanecarbonyl)-2-methyl-1-(2,4,5-trifluorobenzyl)hydrazine-1-carboxylate (1.0 equiv) as dissolved in DCM (0.5 M) and HCl in Dioxane (4.0 M, 5.0 equiv) and allowed to stir overnight at room temperature. The reaction mixture was concentrated and used without further purification. ES/MS: m/z=259.2 $[M+H]^+$.

General Procedure I-E for the Synthesis of Amine Ea:

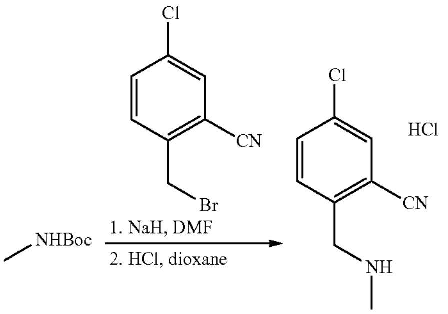

Ea-1

5-chloro-2-(methylaminomethyl)benzonitrile (Ea-1). NaH (60% dispersion in mineral oil, 18 mg, 0.46 mmol) was added to a solution of tert-butyl N-methylcarbamate (50 g, 0.38 mmol) in DMF (3 mL) at 0° C. After stirring for 30 minutes, 2-(bromomethyl)-5-chloro-benzonitrile (132 mg, 0.57 mmol) was added. The mixture was stirred for 3 hours, then quenched by addition of sat. aq. $NH_4Cl$. The reaction mixture was diluted with EtOAc and transferred to a separatory funnel. The organic layer was washed with brine, dried over $MgSO_4$, filtered, and concentrated. The resulting residue was purified by silica gel column chromatography to afford an intermediate protected amine. The intermediate was suspended in dioxane (1 mL) and HCl (4.0 M in dioxane, 1 mL, 4 mmol) was added. After stirring overnight, the reaction mixture was connected under reduced pressure to afford 5-chloro-2-(methylaminomethyl)benzonitrile Ea-1 as the HCl salt. ES/MS: m/z=181.0 $[M+H]^+$. $^1H$ NMR (400 MHz, DMSO-d6) δ 7.95-7.62 (m, 3H), 4.92 (s, 2H), 3.43 (s, 3H).

General Procedure II-E for the Synthesis of Amine Eb-1:

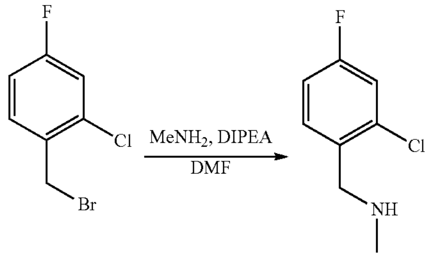

Eb-1

1-(2-chloro-4-fluoro-phenyl)-N-methyl-methanamine (Eb-1). Methylamine (2.0 M in MeOH, 0.34 mL, 0.67 mmol) and DIPEA (0.12 mL, 0.67 mmol) were added to a solution of 1-(bromomethyl)-2-chloro-4-fluoro-benzene (100 mg, 0.45 mmol) in DMF (2.0 mL). After stirring for 2 hours, the reaction mixture was diluted with EtOAc transferred to a separatory funnel, and washed with water, 10% aq. LiCl, and brine. The organic extract was dried over $MgSO_4$, filtered, and concentrated under reduced pressure to afford 1-(2-chloro-4-fluoro-phenyl)-N-methyl-methanamine Eb-1. ES/MS: m/z=174.0 $[M+H]^+$. $^1H$ NMR (400 MHz, DMSO-d6) δ 7.58 (td, J=9.3, 6.6 Hz, 1H), 7.42 (dt, J=9.0, 3.2 Hz, 1H), 7.24 (tt, J=8.6, 2.9 Hz, 1H), 3.72 (s, 2H), 3.66 (s, 3H).

Eb-2

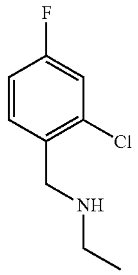

N-(2-chloro-4-fluorobenzyl)ethanamine (Eb-2). Prepared according to general procedure II-E starting with ethylamine. ES/MS: m/z=188.0 $[M+H]^+$.

Eb-3

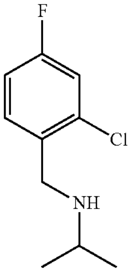

N-(2-chloro-4-fluorobenzyl)propan-2-amine (Eb-3). Prepared according to general procedure II-E starting with isopropylamine. ES/MS: m/z=202.0 $[M+H]^+$.

Eb-4

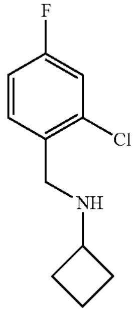

N-(2-chloro-4-fluorobenzyl)cyclobutanamine (Eb-4). Prepared according to general procedure II-E starting with cyclobutylamine. ES/MS: m/z=213.9 $[M+H]^+$.

General Procedure III-E for the Synthesis of Amines Ec:

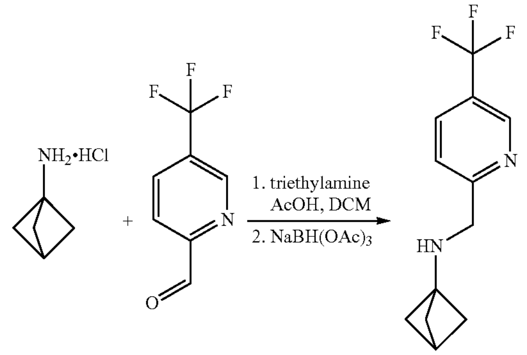

N-((5-(trifluoromethyl)pyridin-2-yl)methyl)bicyclo[1.1.1]pentan-1-amine (Ec-1). To a solution of 5-(trifluoromethyl)pyridine-2-carbaldehyde (1225 mg, 7.0 mmol) and bicyclo[1.1.1]pentan-1-amine; hydrochloride (1004 mg, 8.4 mmol) in DCM (20 mL) was added triethylamine (1.2 mL, 8.4 mmol), followed by acetic acid (0.52 mL, 9.1 mmol). Orange solution. After 15 minutes, added sodium triacetoxyborohydride (2343 mg, 11 mmol). The reaction was stirred at rt overnight, then diluted with DCM and ice water. Added saturated sodium carbonate solution. Extracted 3× with dichloromethane. Dried combined organic extracts with sodium sulfate and purified by flash chromatography to give title compound. ES/MS: m/z=243.0. $[M+H]^+$. $^1H$ NMR (400 MHz, Chloroform-d) δ 8.82 (s, 1H), 7.91-7.85 (m, 1H), 7.51 (d, J=8.2 Hz, 1H), 4.01 (s, 2H), 2.41 (s, 1H), 1.80 (s, 6H).

Ec-2

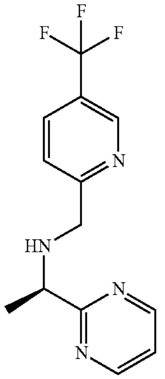

(R)-1-(pyrimidin-2-yl)-N-((5-(trifluoromethyl)pyridin-2-yl)methyl)ethan-1-amine (Ec-2). Prepared following general procedure III-E starting with 5-(trifluoromethyl)picolinaldehyde and (1R)-1-pyrimidin-2-ylethanamine hydrochloride. ES/MS: m/z=283.2 $[M+H]^+$. $^1H$ NMR (400 MHz, Chloroform-d) δ 8.78 (dt, J=2.3, 1.0 Hz, 1H), 8.70 (dd, J=4.9, 0.7 Hz, 2H), 7.84 (dd, J=8.3, 2.3 Hz, 1H), 7.51 (dd, J=8.3, 1.2 Hz, 1H), 7.16 (t, J=4.9 Hz, 1H), 4.06 (q, J=6.8 Hz, 1H), 3.97-3.78 (m, 2H), 2.80 (br s, 1H), 1.74-1.39 (m, 3H).

Ec-3

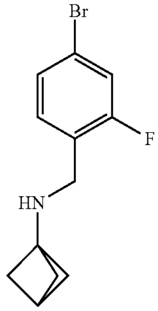

N-(4-bromo-2-fluorobenzyl)bicyclo[1.1.1]pentan-1-amine (Ec-3). Prepared following general procedure III-E starting with 4-bromo-2-fluorobenzaldehyde and bicyclo[1.1.1]pentan-1-amine hydrochloride. ES/MS: m/z=271.2 $[M+H]^+$.

Ec-4

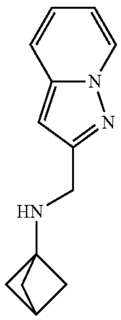

N-(pyrazolo[1,5-a]pyridin-2-ylmethyl)bicyclo[1.1.1]pentan-1-amine (Ec-4). Prepared following general procedure III-E starting with pyrazolo[1,5-a]pyridine-2-carbaldehyde and bicyclo[1.1.1]pentan-1-amine hydrochloride. ES/MS: m/z=214.2 $[M+H]^+$.

Ec-5

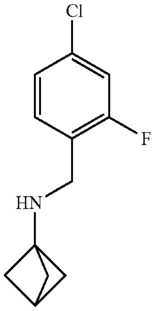

N-(4-chloro-2-fluorobenzyl)bicyclo[1.1.1]pentan-1-amine (Ec-5). Prepared following general procedure III-E starting with 4-chloro-2-fluorobenzaldehyde and bicyclo[1.1.1]pentan-1-amine hydrochloride. ES/MS: m/z=226.0 $[M+H]^+$.

Ec-6

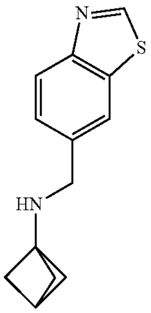

N-(benzo[d]thiazol-6-ylmethyl)bicyclo[1.1.1]pentan-1-amine (Ec-6). Prepared following procedure III-E starting with 1,3-benzothiazole-6-carbaldehyde and bicyclo[1.1.1]pentan-1-amine hydrochloride. ES/MS: m/z=231.2 $[M+H]^+$.

Ec-7

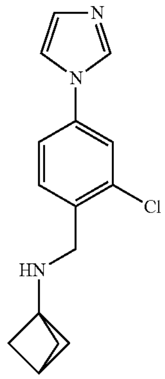

N-(2-chloro-4-(1H-imidazol-1-yl)benzyl)bicyclo[1.1.1]pentan-1-amine (Ec-7). Prepared following procedure III-E starting with 2-chloro-4-imidazol-1-yl-benzaldehyde and bicyclo[1.1.1]pentan-1-amine hydrochloride. ES/MS: m/z=274.2 $[M+H]^+$.

Ec-8

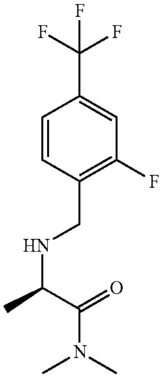

(2R)-2-[[2-fluoro-4-(trifluoromethyl)phenyl]methyl-amino]-N,N-dimethyl-propanamide (Ec-8). Prepared following procedure III-E starting with 4-trifluoromethyl-2-fluorobenzaldehyde and (2R)-2-amino-N,N-dimethyl-propanamide;hydrochloride. ES/MS: m/z =293.1 $[M+H]^+$.

Ec-9

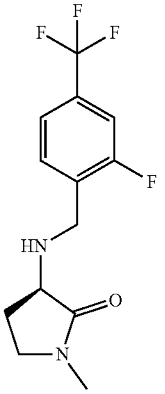

(3R)-3-[[2-fluoro-4-(trifluoromethyl)phenyl]methyl-amino]-1-methyl-pyrrolidin-2-one (Ec-9). Prepared following procedure III-E starting with 4-trifluoromethyl-2-fluorobenzaldehyde and (3R)-3-amino-1-methyl-pyrrolidin-2-one;4-methylbenzenesulfonic acid. ES/MS: m/z=291.2 $[M+H]^+$.

Ec-10

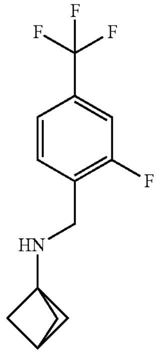

N-(2-fluoro-4-(trifluoromethyl)benzyl)bicyclo[1.1.1]pentan-1-amine (Ec-10). Prepared following general procedure III-E starting with 2-fluoro-4-(trifluoromethyl)benzaldehyde and bicyclo[1.1.1]pentan-1-amine hydrochloride. ES/MS: m/z 260.2 $[M+H]^+$.

Ec-11

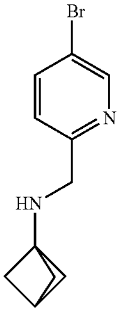

N-((5-bromopyridin-2-yl)methyl)bicyclo[1.1.1]pentan-1-amine (Ec-11): Prepared following general procedure III-E starting with 5-bromopicolinaldehyde and bicyclo[1.1.1]pentan-1-amine hydrochloride. ES/MS: m/z=254.2 $[M+H]^+$.

Ec-12

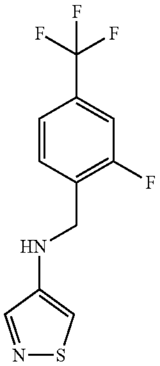

N-(2-fluoro-4-(trifluoromethyl)benzyl)isothiazol-4-amine (Ec-12): Prepared following general procedure III-E starting with 2-fluoro-4-(trifluoromethyl)benzaldehyde and isothiazol-4-amine hydrochloride. ES/MS: m/z=277.0 $[M+H]^+$.

Ec-13

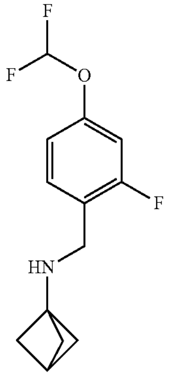

N-(4-(difluoromethoxy)-2-fluorobenzyl)bicyclo[1.1.1]pentan-1-amine (Ec-13). Prepared following procedure III-E starting with bicyclo[1.1.1]pentan-1-amine hydrochloride and 4-(difluoromethoxy)-2-fluoro-benzaldehyde. ES/MS: m/z=258.0 [M+H]$^+$.

Ec-14

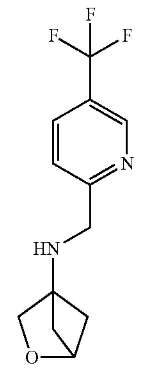

N-((5-(trifluoromethyl)pyridin-2-yl)methyl)-2-oxabicyclo[2.1.1]hexan-4-amine (Ec-14). Prepared following procedure III-E starting with 2-oxabicyclo[2.1.1]hexan-4-amine hydrochloride and 5-(trifluoromethyl) picolinaldehyde. ES/MS: m/z=259.0 [M+H]$^+$.

Ec-15

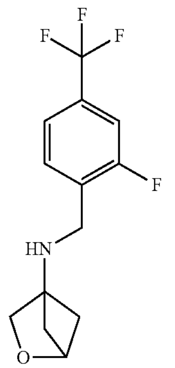

N-(2-fluoro-4-(trifluoromethyl)benzyl)-2-oxabicyclo [2.1.1]hexan-4-amine (Ec-15). Prepared following procedure III-E starting with 2-oxabicyclo[2.1.1]hexan-4-amine hydrochloride and 2-fluoro-4-(trifluoromethyl)benzaldehyde. ES/MS: m/z=276.0 [M+H]$^+$.

Ec-16

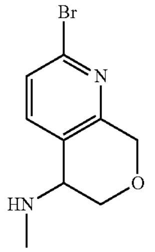

2-bromo-N-methyl-5,8-dihydro-6H-pyrano[3,4-b]pyridin-5-amine (Ec-16). Prepared following procedure III-E starting with methanamine hydrochloride and 2-bromo-8H-pyrano[3,4-b]pyridin-5-one. ES/MS: m/z=244.0 [M+H]$^+$.

Ec-17

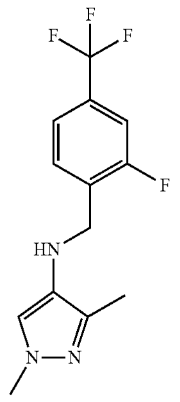

N-[[2-fluoro-4-(trifluoromethyl)phenyl]methyl]-1,3-dimethyl-pyrazol-4-amine (Ec-17). Prepared following general procedure III-E starting with 2-fluoro-4-(trifluoromethyl) benzaldehyde and 1,3-dimethylpyrazol-4-amine;hydrochloride. ES/MS: m/z=288.2 [M+H]$^+$.

Ec-18

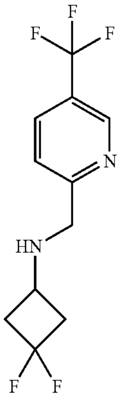

3,3-difluoro-N-[[5-(trifluoromethyl)-2-pyridyl]methyl] cyclobutanamine (Ec-18). Prepared following general procedure III-E starting with 5-(trifluoromethyl)pyridine-2-carbaldehyde and 3,3-difluorocyclobutanamine;hydrochloride. ES/MS: m/z=267.2 [M+H]$^+$.

Ec-19

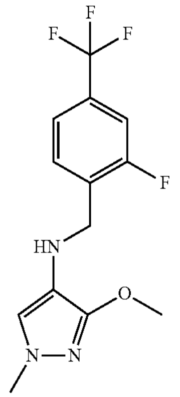

N-[[2-fluoro-4-(trifluoromethyl)phenyl]methyl]-3-methoxy-1-methyl-pyrazol-4-amine (Ec-19). Prepared following general procedure III-E starting with 2-fluoro-4-(trifluoromethyl)benzaldehyde and 3-methoxy-1-methyl-pyrazol-4-amine hydrochloride. ES/MS: m/z=304.3 $[M+H]^+$.

Ec-20

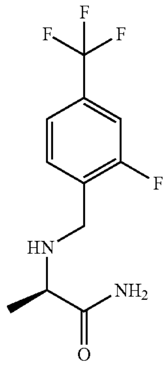

(2R)-2-[[2-fluoro-4-(trifluoromethyl)phenyl]methylamino]propanamide (Ec-20). Prepared following general procedure III-E starting with 2-fluoro-4-(trifluoromethyl) benzaldehyde and (2R)-2-aminopropanamide;hydrochloride. ES/MS: m/z=265.2 $[M+H]^+$.

Ec-21

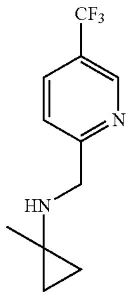

1-methyl-N-((5-(trifluoromethyl)pyridin-2-yl)methyl)cyclopropan-1-amine (Ec-21). Prepared following general procedure III-E starting with 5-(trifluoromethyl)pyridine-2-carbaldehyde and 1-methylcyclopropanamine;hydrochloride. ES/MS: m/z=231.1 $[M+H]^+$.

General Procedure IV-E for the Synthesis of Amines Ed:

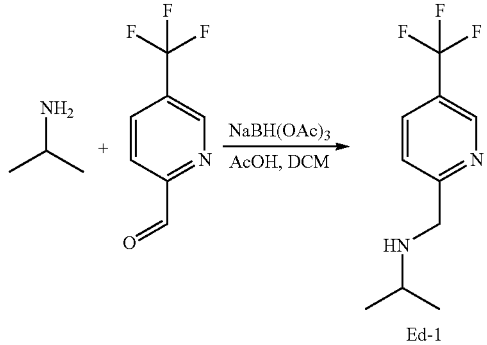

Ed-1

N-((5-(trifluoromethyl)pyridin-2-yl)methyl)propan-2-amine (Ed-1). To a solution of 5-(trifluoromethyl)pyridine-2-carbaldehyde (500 mg, 2.9 mmol), propan-2-amine (0.29 mL, 3.4 mmol), and acetic acid (0.21 mL, 3.7 mmol), in DCM (10 mL), was added sodium triacetoxyborohydride (956 mg, 4.5 mmol). The reaction was stirred at rt overnight, then diluted with DCM and ice water. Added saturated sodium carbonate solution. Extracted 3× with dichloromethane. Dried combined organic extracts with sodium sulfate and purified by flash chromatography to give title compound. ES/MS: m/z=219.2 $[M+H]^+$. $^1H$ NMR (400 MHz, Chloroform-d) δ 8.78 (dd, J=2.2, 1.1 Hz, 1H), 7.84 (dd, J=8.2, 2.4 Hz, 1H), 7.46 (d, J=8.1 Hz, 1H), 3.97 (s, 2H), 2.85 (p, J=6.3 Hz, 1H), 2.46 (s, 1H), 1.10 (d, J=6.3 Hz, 6H).

Ed-2

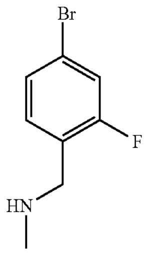

1-(4-bromo-2-fluorophenyl)-N-methylmethanamine (Ed-2). Prepared using general procedure IV-E starting with 4-bromo-2-fluorobenzaldehyde and methylamine. ES/MS: m/z=219.0 $[M+H]^+$.

Ed-3

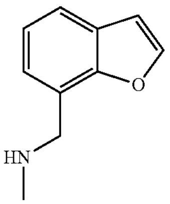

1-(benzofuran-7-yl)-N-methylmethanamine (Ed-3). Prepared using general procedure IV-E starting with benzofuran-7-carbaldehyde and methylamine. ES/MS: m/z=161.9 $[M+H]^+$.

Ed-4

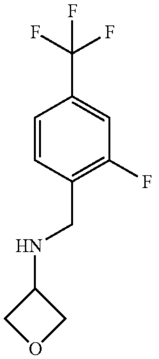

N-[[2-fluoro-4-(trifluoromethyl)phenyl]methyl]oxetan-3-amine (Ed-4). Prepared following general procedure IV-E starting with 4-trifluoromethyl-2-fluorobenzaldehyde and oxetan-3-amine. EZ/MS: m/z=250.1 [M+H]$^+$.

Ed-5

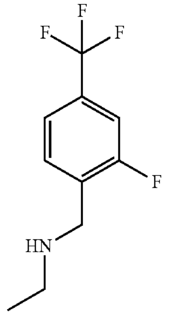

N-[[2-fluoro-4-(trifluoromethyl)phenyl]methyl] ethanamine (Ed-5). Prepared following general procedure IV-E starting with 4-trifluoromethyl-2-fluorobenzaldehyde and ethanamine. EZ/MS: m/z=222.1 [M+H]$^+$.

Ed-6

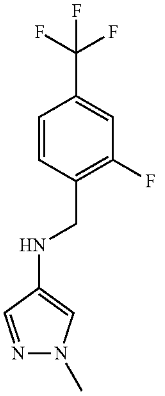

N-(2-fluoro-4-(trifluoromethyl)benzyl)-1-methyl-1H-pyrazol-4-amine (Ed-6). repared following general procedure IV-E starting with 4-trifluoromethyl-2-fluorobenzaldehyde and 1-methylpyrazol-4-amine. ES/MS: m/z=274.2 [M+H]$^+$.

Ed-7

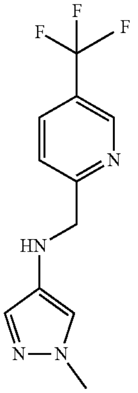

1-methyl-N-((5-(trifluoromethyl)pyridin-2-yl)methyl)-1H-pyrazol-4-amine (Ed-7). Prepared following general procedure IV-E starting with 5-(trifluoromethyl)pyridine-2-carbaldehyde and 1-methylpyrazol-4-amine. ES/MS: m/z=257.2 [M+H]$^+$.

Ed-8

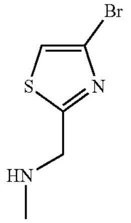

1-(4-bromothiazol-2-yl)-N-methylmethanamine (Ed-8). Prepared using general procedure IV-E starting with 4-bromothiazole-2-carbaldehyde and methylamine. ES/MS: m/z=209.0 [M+H]$^+$.

Ed-9

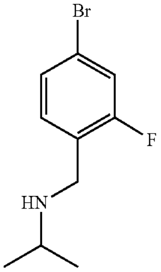

N-(4-bromo-2-fluorobenzyl)propan-2-amine (Ed-9). Prepared using general procedure to IV-E starting with 4-bromo-2-fluorobenzaldehyde and isopropylamine. ES/MS: m/z=247.2 [M+H]$^+$.

Ed-10

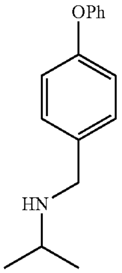

N-(4-phenoxybenzyl)propan-2-amine (Ed-10). Prepared using a similar procedure to IV-E starting with 4-phenoxybenzaldehyde and isopropylamine. ES/MS: m/z=242.9 [M+H]$^+$.

Ed-11

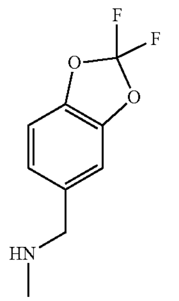

1-(2,2-difluorobenzo[d][1,3]dioxol-5-yl)-N-methylmethanamine (Ed-11). Prepared using general procedure IV-E starting with 2,2-difluoro-1,3-benzodioxole-5-carbaldehyde and methylamine. ES/MS: m/z=202.0 $[M+H]^+$.

Ed-12

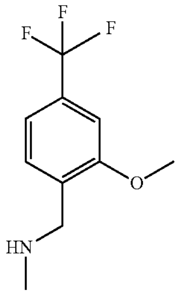

1-(2-methoxy-4-(trifluoromethyl)phenyl)-N-methylmethanamine (Ed-12). Prepared using general procedure IV-E starting with 2-methoxy-4-(trifluoromethyl)benzaldehyde and methylamine. ES/MS: m/z=220.2 $[M+H]^+$.

Ed-13

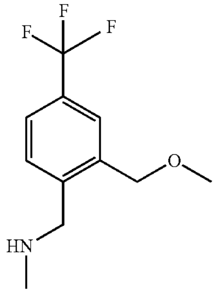

1-(2-(methoxymethyl)-4-(trifluoromethyl)phenyl)-N-methylmethanamine (Ed-13). Prepared using general procedure IV-E starting with 2-(methoxymethyl)-4-(trifluoromethyl)benzaldehyde and methylamine. ES/MS: m/z=234.2 $[M+H]^+$.

Ed-14

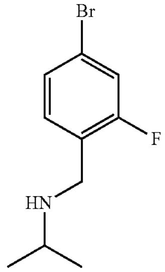

N-(4-bromo-2-fluorobenzyl)propan-2-amine (Ed-14): Prepared following general procedure IV-E starting with 4-bromo-2-fluorobenzaldehyde and propan-2-amine. ES/MS: m/z =247.2 $[M+H]^+$.

Ed-15

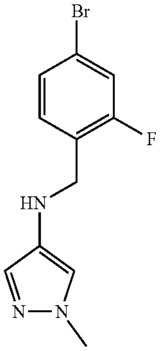

N-(4-bromo-2-fluorobenzyl)-1-methyl-1H-pyrazol-4-amine (Ed-15): Prepared following general procedure IV-E starting with 4-bromo-2-fluorobenzaldehyde and 1-methyl-1H-pyrazol-4-amine. ES/MS: m/z=285.0 $[M+H]^+$.

Ed-16

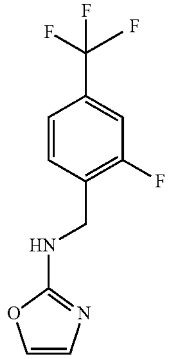

N-(2-fluoro-4-(trifluoromethyl)benzyl)oxazol-2-amine (Ed-16). Prepared following general procedure IV-E starting with 2-fluoro-4-(trifluoromethyl)benzaldehyde and oxazol-2-amine. ES/MS: m/z=261.0 $[M+H]^+$.

Ed-17

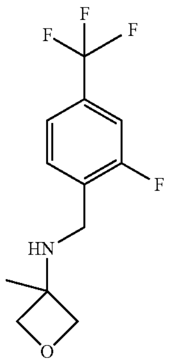

N-(2-fluoro-4-(trifluoromethyl)benzyl)-3-methyloxetan-3-amine (Ed-17). Prepared following procedure IV-E starting with 3-methyloxetan-3-amine and 2-fluoro-4-(trifluoromethyl)benzaldehyde. ES/MS: m/z=264.0 [M+H]+.

Ed-18

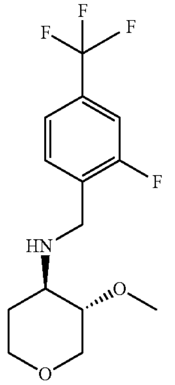

(3S,4R)—N-(2-fluoro-4-(trifluoromethyl)benzyl)-3-methoxytetrahydro-2H-pyran-4-amine (Ed-18). Prepared following procedure IV-E starting with (3S,4R)-3-methoxytetrahydropyran-4-amine and 2-fluoro-4-(trifluoromethyl)benzaldehyde. ES/MS: m/z=308.0 [M+H]+.

Ed-19

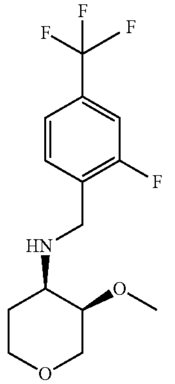

(3R,4R)—N-(2-fluoro-4-(trifluoromethyl)benzyl)-3-methoxytetrahydro-2H-pyran-4-amine (Ed-19). Prepared following procedure IV-E starting with (3R,4R)-3-methoxytetrahydropyran-4-amine and 2-fluoro-4-(trifluoromethyl)benzaldehyde. ES/MS: m/z=308.0 [M+H]+.

Ed-20

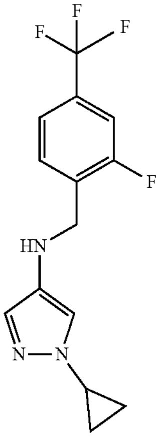

1-cyclopropyl-N-(2-fluoro-4-(trifluoromethyl)benzyl)-1H-pyrazol-4-amine (Ed-20). Prepared following procedure IV-E starting with 1-cyclopropylpyrazol-4-amine and 2-fluoro-4-(trifluoromethyl)benzaldehyde. ES/MS: m/z=300.0 [M+H]+.

Ed-21

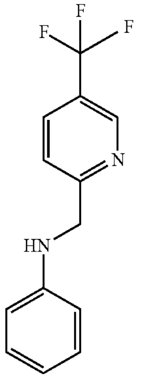

N-((5-(trifluoromethyl)pyridin-2-yl)methyl)aniline (Ed-21). Prepared following procedure IV-E starting with aniline and 5-(trifluoromethyl)pyridine-2-carbaldehyde. ES/MS: m/z=253.0 [M+H]+.

Ed-22

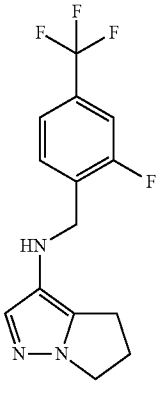

N-(2-fluoro-4-(trifluoromethyl)benzyl)-5,6-dihydro-4H-pyrrolo[1,2-b]pyrazol-3-amine (Ed-22). Prepared following procedure IV-E starting with 5,6-dihydro-4H-pyrrolo[1,2-b]pyrazol-3-amine and 2-fluoro-4-(trifluoromethyl)benzaldehyde. ES/MS: m/z=300.0 $[M+H]^+$.

Ed-23

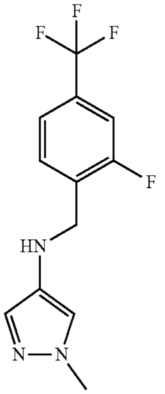

N-(2-fluoro-4-(trifluoromethyl)benzyl)-1-methyl-1H-pyrazol-3-amine (Ed-23). Prepared following procedure IV-E starting with 1-methylpyrazol-3-amine and 2-fluoro-4-(trifluoromethyl)benzaldehyde. ES/MS: m/z=274.0 $[M+H]^+$.

Ed-24

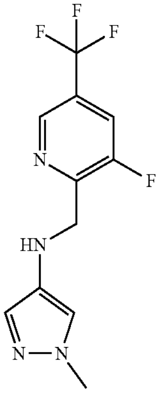

N-((3-fluoro-5-(trifluoromethyl)pyridin-2-yl)methyl)-1-methyl-1H-pyrazol-4-amine (Ed-24). Prepared following procedure IV-E starting with 1-methylpyrazol-4-amine and 3-fluoro-5-(trifluoromethyl)pyridine-2-carbaldehyde. ES/MS: m/z=275.2 $[M+H]^+$.

Ed-25

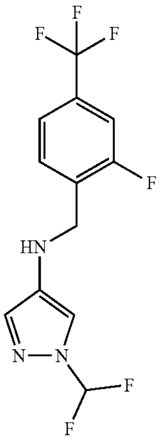

1-(difluoromethyl)-N-(2-fluoro-4-(trifluoromethyl)benzyl)-1H-pyrazol-4-amine (Ed-25). Prepared following procedure IV-E starting with 1-(difluoromethyl)pyrazol-4-amine and 2-fluoro-4-(trifluoromethyl)benzaldehyde. ES/MS: m/z=310.2 $[M+H]^+$.

Ed-26

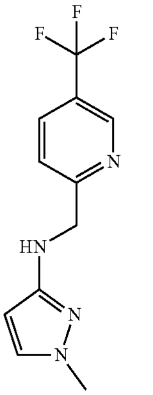

1-methyl-N-((5-(trifluoromethyl)pyridin-2-yl)methyl)-1H-pyrazol-3-amine (Ed-26). Prepared following procedure IV-E starting with 1-methylpyrazol-3-amine and 5-(trifluoromethyl)pyridine-2-carbaldehyde. ES/MS: m/z=257.0 $[M+H]^+$.

Ed-27

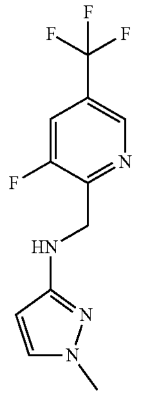

N-((3-fluoro-5-(trifluoromethyl)pyridin-2-yl)methyl)-1-methyl-1H-pyrazol-3-amine (Ed-27). Prepared following procedure IV-E starting with 1-methylpyrazol-3-amine and 3-fluoro-5-(trifluoromethyl)pyridine-2-carbaldehyde. ES/MS: m/z=275.0 $[M+H]^+$.

Ed-28

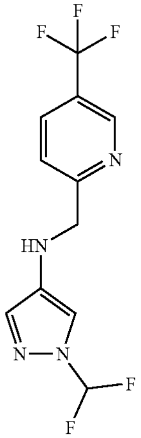

1-(difluoromethyl)-N-((5-(trifluoromethyl)pyridin-2-yl)methyl)-1H-pyrazol-4-amine (Ed-28). Prepared following procedure IV-E starting with 1-(difluoromethyl)pyrazol-4-amine and 5-(trifluoromethyl)pyridine-2-carbaldehyde. ES/MS: m/z=293.0 $[M+H]^+$.

Ed-29

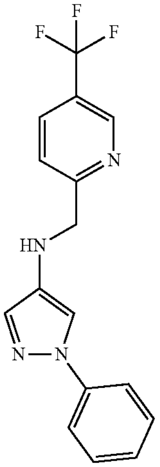

1-phenyl-N-((5-(trifluoromethyl)pyridin-2-yl)methyl)-1H-pyrazol-4-amine (Ed-29). Prepared following procedure IV-E starting with 1-phenylpyrazol-4-amine and 5-(trifluoromethyl)pyridine-2-carbaldehyde. ES/MS: m/z=319.0 $[M+H]^+$.

Ed-30

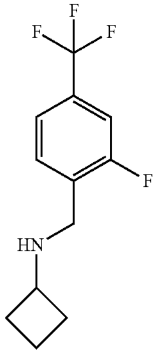

N-[[2-fluoro-4-(trifluoromethyl)phenyl]methyl]cyclobutanamine (Ed-30). Prepared following general procedure IV-E starting with 2-fluoro-4-(trifluoromethyl)benzaldehyde and cyclobutanamine. ES/MS: m/z=248.1 $[M+H]^+$.

Ed-31

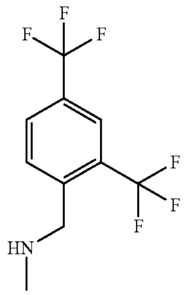

1-[2,4-bis(trifluoromethyl)phenyl]-N-methyl-methanamine (Ed-31). Prepared following general procedure IV-E starting with 2,4-bis(trifluoromethyl)benzaldehyde and methanamine. ES/MS: m/z=258.1 $[M+H]^+$.

Ed-32

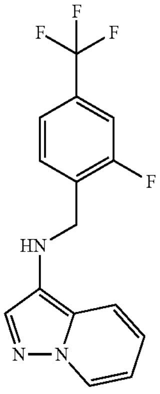

N-[[2-fluoro-4-(trifluoromethyl)phenyl]methyl]pyrazolo[1,5-a]pyridin-3-amine (Ed-32). Prepared following general procedure IV-E starting with 2-fluoro-4-(trifluoromethyl)benzaldehyde and pyrazolo[1,5-a]pyridin-3-amine. ES/MS: m/z=310.3 $[M+H]^+$.

Ed-33

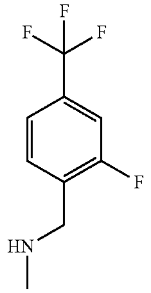

1-[2-fluoro-4-(trifluoromethyl)phenyl]-N-methyl-methanamine (Ed-33). Prepared following general procedure IV-E starting with 2-fluoro-4-(trifluoromethyl)benzaldehyde and methanamine. ES/MS: m/z=207.2 $[M+H]^+$.

Ed-34

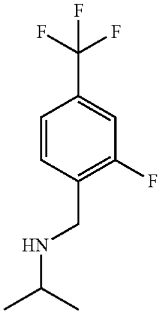

N-[[2-fluoro-4-(trifluoromethyl)phenyl]methyl]propan-2-amine (Ed-34). Prepared following general procedure IV-E starting with 2-fluoro-4-(trifluoromethyl)benzaldehyde and propan-2-amine. ES/MS: m/z=236.2 $[M+H]^+$.

Ed-35

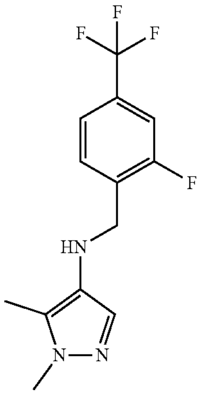

N-[[2-fluoro-4-(trifluoromethyl)phenyl]methyl]-1,5-dimethyl-pyrazol-4-amine (Ed-35). Prepared following general procedure IV-E starting with 2-fluoro-4-(trifluoromethyl)benzaldehyde and 1,5-dimethylpyrazol-4-amine. ES/MS: m/z=288.2 $[M+H]^+$.

Ed-36

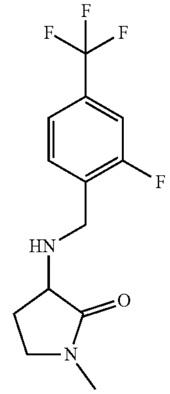

3-((2-fluoro-4-(trifluoromethyl)benzyl)amino)-1-methylpyrrolidin-2-one (Ed-36). Prepared following general procedure IV-E starting with 2-fluoro-4-(trifluoromethyl)benzaldehyde and 3-amino-1-methyl-pyrrolidin-2-one. ES/MS: m/z=291.2 $[M+H]^+$.

Ed-37

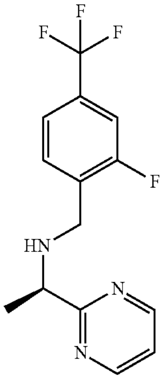

(1R)—N-[[2-fluoro-4-(trifluoromethyl)phenyl]methyl]-1-pyrimidin-2-yl-ethanamine (Ed-37). Prepared following general procedure IV-E starting with 2-fluoro-4-(trifluoromethyl)benzaldehyde and (1R)-1-pyrimidin-2-ylethanamine. ES/MS: m/z=300.2

Ed-38

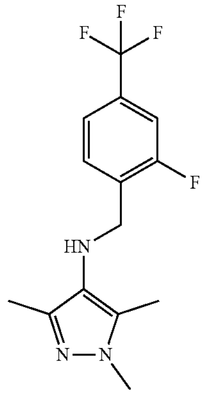

N-[[2-fluoro-4-(trifluoromethyl)phenyl]methyl]-1,3,5-trimethyl-pyrazol-4-amine (Ed-38). Prepared following general procedure IV-E starting with 2-fluoro-4-(trifluoromethyl)benzaldehyde and 1,3,5-trimethylpyrazol-4-amine. ES/MS: m/z=301.3 $[M+H]^+$.

Ed-39

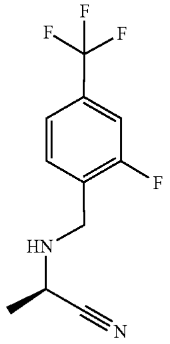

(R)-2-((2-fluoro-4-(trifluoromethyl)benzyl)amino)propanenitrile (Ed-39). Prepared following general procedure IV-E starting with 2-fluoro-4-(trifluoromethyl)benzaldehyde and (R)-2-aminopropanenitrile. ES/MS: m/z=247.2 $[M+H]^+$.

Ed-40

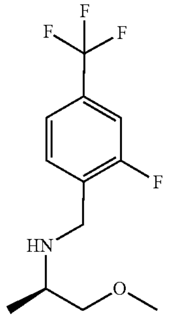

(2R)—N-[[2-fluoro-4-(trifluoromethyl)phenyl]methyl]-1-methoxy-propan-2-amine (Ed-40). Prepared following general procedure IV-E starting with 2-fluoro-4-(trifluoromethyl)benzaldehyde and (2R)-1-methoxypropan-2-amine. ES/MS: m/z=266.2 $[M+H]^+$.

Ed-41

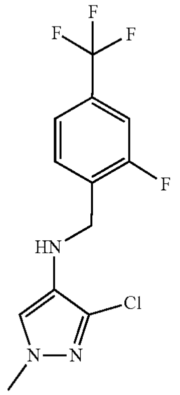

3-chloro-N-[[2-fluoro-4-(trifluoromethyl)phenyl]methyl]-1-methyl-pyrazol-4-amine (Ed-41). Prepared following general procedure IV-E starting with 2-fluoro-4-(trifluoromethyl)benzaldehyde and 3-chloro-1-methyl-pyrazol-4-amine. ES/MS: m/z=308.6 $[M+H]^+$.

Ed-42

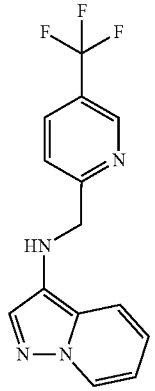

N-[[5-(trifluoromethyl)-2-pyridyl]methyl]pyrazolo[1,5-a]pyridin-3-amine (Ed-42). Prepared following general procedure IV-E starting with 5-(trifluoromethyl)pyridine-2-carbaldehyde and pyrazolo[1,5-a]pyridin-3-amine. ES/MS: m/z=293.2 $[M+H]^+$.

Ed-44

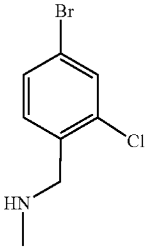

1-(4-bromo-2-chlorophenyl)-N-methylmethanamine (Ed-44). Prepared using general procedure IV-E starting with 4-bromo2-chloro-benzaldehyde and methylamine. ES/MS: m/z=234.1 $[M+H]^+$.

Ed-45

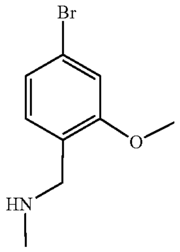

1-(4-bromo-2-methoxyphenyl)-N-methylmethanamine (Ed-45). Prepared using general procedure IV-E starting with 4-bromo-2-methoxy-benzaldehyde and methylamine. ES/MS: m/z=230.1 $[M+H]^+$.

Ed-46

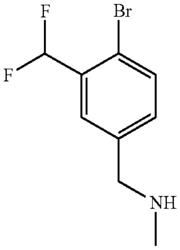

1-(4-bromo-3-(difluoromethyl)phenyl)-N-methylmethanamine (Ed-46). Prepared following procedure IV-E starting with 4-bromo-3-(difluoromethyl)benzaldehyde and methylamine. ES/MS: m/z=250.0, 252.0 $[M+H]^+$.

General Procedure V-E for the Synthesis of Amine Ee:

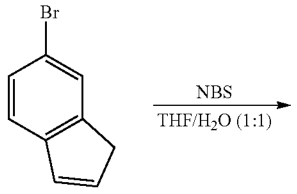

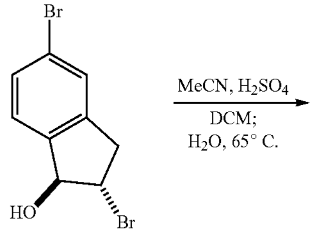

(rac)

-continued

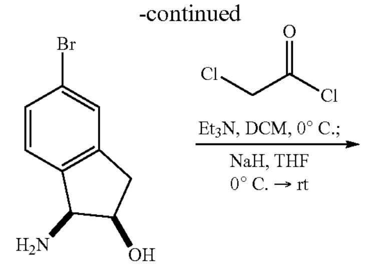

(rac)

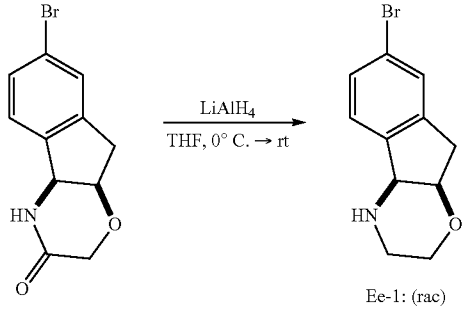

Ee-1: (rac)

(rac)

Step 1. Racemic (1S,2S)-2,5-dibromo-2,3-dihydro-1H-inden-1-ol. NBS (2.36 g, 13.3 mmol) was added to a solution of 6-bromo-1H-indene (2.35 g, 12 mmol) in THF/$H_2O$ (1:1, 10 mL). The suspension was stirred overnight, then quenched via addition of 10% aq. $Na_2S_2O_4$. The resulting mixture was transferred to a separatory funnel and extracted with EtOAc. The organic extract was then washed with brine, dried over $MgSO_4$, filtered, and concentrated under reduced pressure. Purification by silica gel column chromatography afforded racemic (1S,2S)-2,5-dibromoindan-1-ol. ES/MS: m/z=274.8 $[M+H]^+$. $^1H$ NMR (400 MHz, Chloroform-d) δ 7.45-7.41 (m, 1H), 7.39 (s, 1H), 7.29 (d, J=8.1 Hz, 1H), 5.26 (t, J=5.4 Hz, 1H), 4.27 (td, J=7.3, 5.8 Hz, 1H), 3.57 (dd, J=16.4, 7.2 Hz, 1H), 3.21 (dd, J=16.4, 7.4 Hz, 1H), 2.35 (d, J=5.8 Hz, 1H).

Step 2. Racemic (1S,2R)-1-amino-5-bromo-2,3-dihydro-1H-inden-2-ol. To a suspension of (1S,2S)-2,5-dibromoindan-1-ol (350 mg, 1.2 mmol) in DCM (1.5 mL) at 0° C. was added acetonitrile (0.13 mL, 2.5 mmol) followed by dropwise addition of conc. $H_2SO_4$ (0.1 mL, 1.8 mmol). The mixture was warmed to room temperature and stirred for 3 h. $H_2O$ (2.5 mL) was then added and the reaction mixture was brought, open, to 65° C. to drive off DCM. The reaction vessel was then sealed and allowed to stir at this temperature overnight. After cooling to room temperature, 6M NaOH was added until pH 12. The resulting slurry was extracted with DCM until no solids remained. The combined organic extracts were dried over $MgSO_4$, filtered, and concentrated to afford crude cis-(1S,2R)-1-amino-5-bromo-indan-2-ol (175 mg, ca. 64%) which was used directly in the subsequent step. ES/MS: m/z=229.9 $[M+H]^+$.

Step 3. Racemic (4aS,9aR)-7-bromo-4,4a,9,9a-tetrahydroindeno[2,1-b][1,4]oxazin-3(2H)-one. To a stirred suspension of the crude residue from the previous step (175 mg, ca. 0.77 mmol) and triethylamine (0.14 mL, 1.0 mmol) in DCM (6 mL) at 0° C. was added chloroacetyl chloride (0.07 mL, 0.92 mmol) dropwise. After stirring for 1 hour, the reaction was quenched with water. The mixture was transferred to a separatory funnel and extracted with EtOAc. The organic extract was washed with brine, dried over $MgSO_4$, filtered, and concentrated under reduced pressure. The resulting solid was suspended in dry THF (3 mL) and added dropwise to a suspension of NaH (60% dispersion in mineral oil, 59 mg, 1.53 mmol) in THF (3 mL) at 0° C. The mixture was warmed to room temperature and allowed to stir for 3 hours. After careful quenching with water, the reaction mixture was transferred to a separatory funnel and extracted with EtOAc. The organic extract was washed with brine, dried over $MgSO_4$, filtered, and concentrated under reduced pressure. Purification of the crude residue by silica gel column chromatography afforded racemic (4aS,9aR)-7-bromo-4,4a,9,9a-tetrahydroindeno [2,1-b][1,4]oxazin-3-one. ES/MS: m/z=267.9 $[M+H]^+$. $^1H$ NMR (400 MHz, Chloroform-d) δ 7.42 (d, J=10.7 Hz, 2H), 7.17 (d, J=7.9 Hz, 1H), 4.72 (t, J=4.1 Hz, 1H), 4.53 (t, J=4.5 Hz, 1H), 4.16 (s, 2H), 3.21 (dd, J=17.0, 4.9 Hz, 1H), 3.07 (d, J=17.0 Hz, 1H).

Step 4. Cis-(4aS,9aR)-7-bromo-2,3,4,4a,9,9a-hexahydroindeno[2,1-b][1,4]oxazine Ee-1. $LiAlH_4$ (2.0M in THF, 0.71 mL, 1.43 mmol) was added to a solution of racemic (4aS,9aR)-7-bromo-4,4a,9,9a-tetrahydroindeno[2,1-b][1,4] oxazin-3-one (120 mg, 0.36 mmol) in THF (3 mL) at 0° C. The mixture was warmed to room temperature and allowed to stir overnight. The reaction was then cooled to 0° C. and quenched by slow addition of 2M NaOH until the evolution of gas was no longer detected. $MgSO_4$ was added and the mixture was filtered over celite, washing with EtOAc. The resulting filtrate was concentrated under reduced pressure and purified by silica gel column chromatography to afford racemic (4aS,9aR)-7-bromo-2,3,4,4a,9,9a-hexahydroindeno [2,1-b][1,4]oxazine Ee-1. ES/MS: m/z=253.9 $[M+H]^+$. $^1H$ NMR (400 MHz, Chloroform-d) δ 7.47-7.37 (m, 2H), 7.36-7.24 (m, 1H), 4.42-4.19 (m, 2H), 3.77-3.54 (m, 2H), 3.07-2.64 (m, 4H).

Ee-2: (rac)

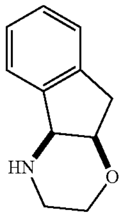

Cis-(4aS,9aR)-2,3,4,4a,9,9a-hexahydroindeno[2,1-b][1,4]oxazine (Ee-2). Prepared following general procedure V-E starting with indene. EZ/MS: m/z=176.0 $[M+H]^+$.

Ee-3: (rac)

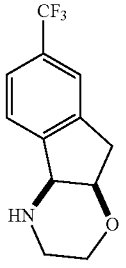

Cis-(4aS,9aR)-7-(trifluoromethyl)-2,3,4,4a,9,9a-hexahydroindeno[2,1-b][1,4]oxazine (Ee-3). Prepared following general procedure V-E starting with 6-(trifluoromethyl)-1H-indene. EZ/MS: m/z=244.0 $[M+H]^+$.

Ee-4: (rac)

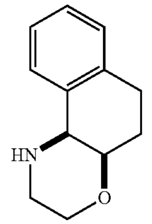

cis-2,3,4a,5,6,10b-hexahydro-1H-benzo[f][1,4]benzoxazine (Ee-4). Prepared following steps 3 and 4 from general procedure V-E using rac-(1S,2R)-1-aminotetralin-2-ol. ES/MS: m/z=204.2 $[M+H]^+$.

General Procedure VI-E for the Synthesis of Amine Ef:

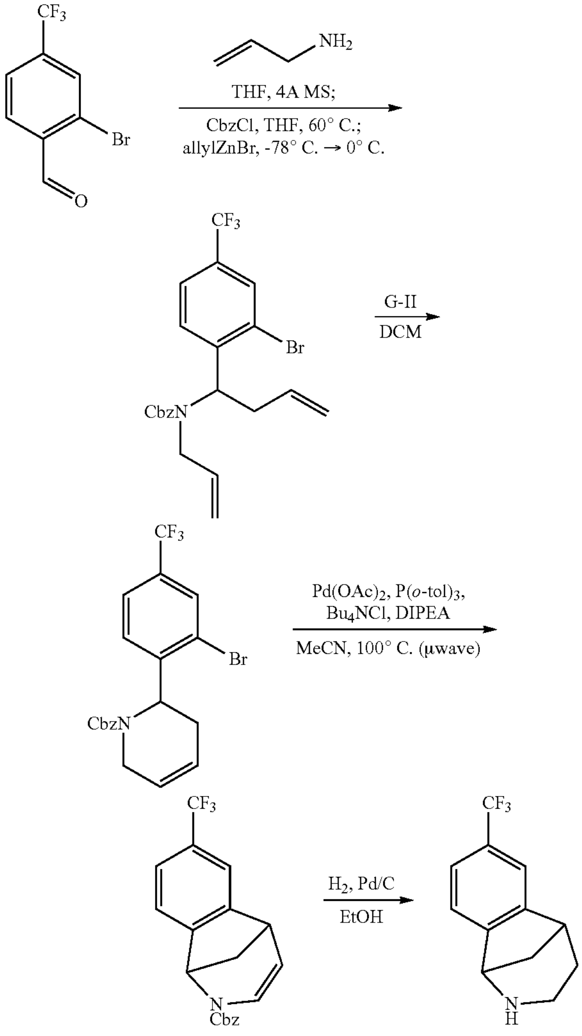

Ef-1

Step 1. Benzyl N-allyl-N-[1-[2-bromo-4-(trifluoromethyl)phenyl]but-3-enyl]carbamate. A mixture of 2-bromo-4-(trifluoromethyl)benzaldehyde (746 mg, 2.95 mmol), allylamine (0.44 mL, 5.89 mmol) and 4A MS in THF (8 mL) was stirred overnight at room temperature. The mixture was filtered and concentrated under reduced pressure. The resulting residue was resuspended in dry THF (10 mL) and benzyl chloroformate (0.44 mL, 3.13 mL) was added. The mixture was heated to 60° C. for 1 hour, then cooled to −78 C. A freshly prepared solution of allylzinc bromide (ca. 1.7M in THF, 2.5 mL, 4.26 mmol) was then added dropwise. The reaction was allowed to stir for 2 hours, then warmed to 0° C. and quenched by slow addition of sat. aq. NH4Cl. The mixture was transferred to a separatory funnel, diluted with EtOAc, and washed with water followed by brine. The organic extract was dried over $MgSO_4$, filtered, and concentrated. Purification by silica gel column chromatography afforded benzyl N-allyl-N-[1-[2-bromo-4-(trifluoromethyl)phenyl]but-3-enyl]carbamate. ES/MS: m/z=467.7 $[M+H]^+$. $^1$H NMR (400 MHz, Chloroform-d) δ 7.57 (s, 1H), 7.45-7.30 (m, 7H), 5.83-5.54 (m, 2H), 5.45 (t, J=7.8 Hz, 1H), 5.19 (s, 2H), 5.15-4.76 (m, 4H), 3.85-3.54 (m, 2H), 2.95-2.61 (m, 2H).

Step 2. Benzyl 2-(2-bromo-4-(trifluoromethyl)phenyl)-3,6-dihydropyridine-1(2H)-carboxylate. A solution of benzyl N-allyl-N-[1-[2-bromo-4-(trifluoromethyl)phenyl]but-3-enyl]carbamate (850 mg, 1.82 mmol) in DCM (50 mL) was sparged with argon for 10 minutes. Grubbs second generation catalyst (77 mg, 0.09 mmol) was then added, and the mixture was allowed to stir overnight at room temperature. The reaction mixture was concentrated under reduced pressure and the resulting residue was purified by silica gel column chromatography to afford benzyl 2-[2-bromo-4-(trifluoromethyl)phenyl]-3,6-dihydro-2H-pyridine-1-carboxylate. ES/MS: m/z=439.8 $[M+H]^+$. $^1$H NMR (400 MHz, Chloroform-d) δ 7.85-7.72 (m, 1H), 7.45 (d, J=7.7 Hz, 1H), 7.37-7.12 (m, 6H), 5.91 (s, 1H), 5.85-5.64 (m, 2H), 5.12 (q, J=12.8 Hz, 2H), 4.29 (dd, J=18.5, 3.3 Hz, 1H), 3.98 (d, J=18.6 Hz, 1H), 2.76 (ddt, J=17.1, 6.7, 3.2 Hz, 1H), 2.42 (dd, J=17.6, 6.2 Hz, 1H).

Step 3. Benzyl 7-(trifluoromethyl)-1,5-dihydro-2H-1,5-methanobenzo[c]azepine-2-carboxylate. A degassed solution of benzyl 2-[2-bromo-4-(trifluoromethyl)phenyl]-3,6-dihydro-2H-pyridine-1-carboxylate (300 mg, 0.68 mmol) in MeCN (3.5 mL) was added to a mixture of palladium acetate (15 mg, 0.07 mmol), tri-o-tolylphosphine (42 mg, 0.14 mmol), and tetrabutylammonium chloride (189 mg, 0.68 mmol) in an argon flushed microwave vial. DIPEA (0.24 mL, 1.36 mmol) was then added and the mixture was allowed to stir for 5 minutes before being heated to 100° C. for 1 hour in a microwave reactor. The mixture was then diluted with EtOAc, filtered over Celite, and concentrated. Purification by silica gel column chromatography afforded benzyl 4-(trifluoromethyl)-9-azatricyclo[6.3.1.02,7]dodeca-2,4,6,10-tetraene-9-carboxylate. ES/MS: m/z=359.9 $[M+H]^+$. $^1$H NMR (400 MHz, Chloroform-d) δ 7.61-7.31 (m, 8H), 6.46 (dd, J=38.2, 7.6 Hz, 1H), 5.58 (dd, J=51.0, 4.1 Hz, 1H), 5.37-5.05 (m, 3H), 3.42 (d, J=5.8 Hz, 1H), 2.46-2.22 (m, 1H), 2.13 (dd, J=11.1, 3.8 Hz, 1H).

Step 4. 4-(trifluoromethyl)-9-azatricyclo[6.3.1.02,7]dodeca-2,4,6-triene (Ef-1). A flask containing benzyl 4-(trifluoromethyl)-9-azatricyclo[6.3.1.02,7]dodeca-2,4,6,10-tetraene-9-carboxylate (30 mg, 0.08 mmol) and Pd/C (10% w/w, 44 mg, 0.04 mmol) in EtOH (1 mL) was flushed with hydrogen gas. After stirring overnight, the reaction vessel was flushed with argon and the mixture was filtered, rinsing with EtOAc. Concentration of the resulting filtrate under reduced pressure afforded 4-(trifluoromethyl)-9-azatricyclo[6.3.1.02,7]dodeca-2,4,6-triene Ef-1. ES/MS: m/z=228.0 $[M+H]^+$. $^1$H NMR (400 MHz, Chloroform-d) δ 7.57-7.38 (m, 3H), 4.35 (d, J=4.2 Hz, 1H), 3.29 (d, J=5.3 Hz, 1H), 2.96 (s, 1H), 2.82 (dd, J=12.4, 5.9 Hz, 1H), 2.42-2.18 (m, 2H), 2.15-1.96 (m, 2H).

Ef-2

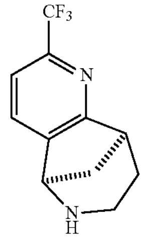

(Rac)-2-(trifluoromethyl)-6,7,8,9-tetrahydro-5H-5,9-methanopyrido[3,2-c]azepine (Ef-2). Prepared according to general procedure VI-E (allylMgBr was used in place of allylZnBr) starting with 2-bromo-6-(trifluoromethyl)pyridine-3-carbaldehyde. ES/MS: m/z=229.0 $[M+H]^+$.

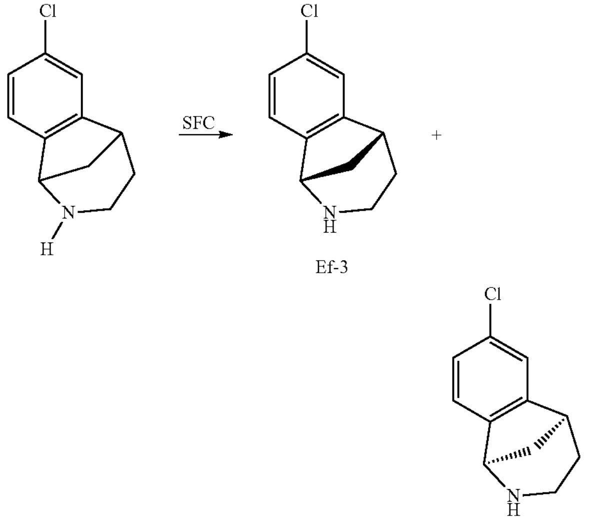

Ef-3

Ef-4

Prepared following general procedure VI-E starting with -bromo-4-chlorobenzaldehyde and allylamine. The racemic amine was purified by SFC [with the following conditions: Column: CHIRALPAK IE, 3*25 cm, 5 m; Mobile Phase A: $CO_2$, Mobile Phase B: MeOH (20 mmol/L $NH_3$); Flow rate: 100 mL/min; Gradient: isocratic 20% B; Column Temperature (° C.): 35; Back Pressure (bar): 100; Wave Length: 204/220 nm; RT1 (min): 7.17].

Ef-3

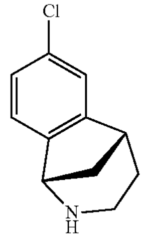

(1S,5R)-7-chloro-2,3,4,5-tetrahydro-1H-1,5-methanobenzo[c]azepine (Ef-3). Peak 1. ES/MS: m/z=194.2 $[M+H]^+$.

Ef-4

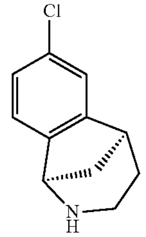

(1R,5S)-7-chloro-2,3,4,5-tetrahydro-1H-1,5-methanobenzo[c]azepine (Ef-4). Peak 2. ES/MS: m/z=194.2 $[M+H]^+$.

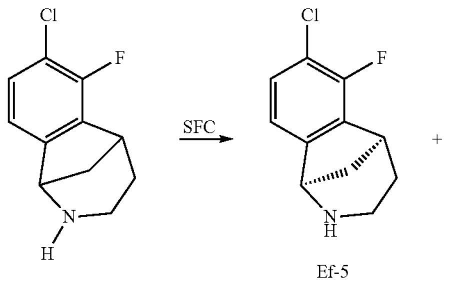

Ef-5

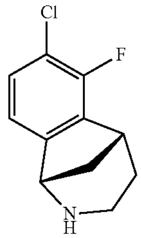

Ef-6

Prepared following general procedure VI-E starting with 2-bromo-4-chloro-3-fluorobenzaldehyde and prop-2-en-1-amine hydrochloride. The racemic amine was purified by SFC [with the following conditions: Column: CHIRALPAK IG, 3*25 cm, 5 m; Mobile Phase A: $CO_2$, Mobile Phase B: MeOH (20 mM $NH_3$); Flow rate: 100 mL/min; Gradient: isocratic 25% B; Column Temperature (° C.): 35; Back Pressure (bar): 100; Wave Length: 204/220 nm; RT1 (min): 3.60, RT2 (min): 4.72].

Ef-5

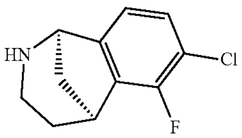

(1R,5S)-7-chloro-6-fluoro-2,3,4,5-tetrahydro-1H-1,5-methanobenzo[c]azepine (Ef-5). Peak 1. ES/MS: m/z=212.0 $[M+H]^+$.

Ef-6

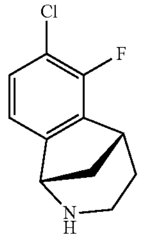

(1S,5R)-7-chloro-6-fluoro-2,3,4,5-tetrahydro-1H-1,5-methanobenzo[c]azepine (Ef-6). Peak 2. ES/MS: m/z=212.0 $[M+H]^+$.

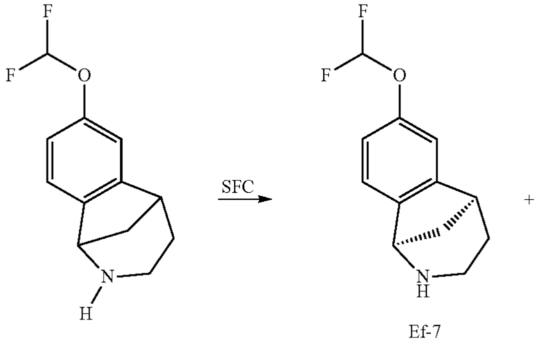

Ef-7

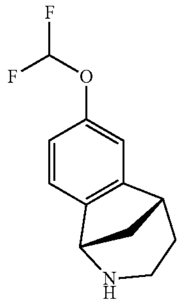

Ef-8

Prepared following general procedure VI-E starting with 2-bromo-4-(difluoromethoxy)benzaldehyde and prop-2-en-1-amine hydrochloride. The racemic amine was purified by SFC [with the following conditions: Column: CHIRALPAK IE, 3*25 cm, 5 m; Mobile Phase A: $CO_2$, Mobile Phase B: MeOH (20 mN $NH_3$); Flow rate: 100 mL/min; Gradient: isocratic 20% B; Column Temperature (° C.): 35; Back Pressure (bar): 100; Wave Length: 204/220 nm; RT1 (min): 7.17, RT2 (min): 8.73].

Ef-7

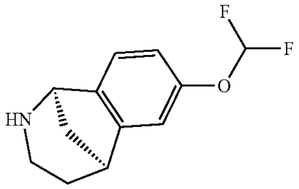

(1R,5S)-7-(difluoromethoxy)-2,3,4,5-tetrahydro-1H-1,5-methanobenzo[c]azepine (Ef-7). Peak 1. ES/MS: m/z=226.1 $[M+H]^+$.

Ef-8

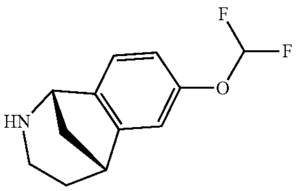

(1S,5R)-7-(difluoromethoxy)-2,3,4,5-tetrahydro-1H-1,5-methanobenzo[c]azepine (Ef-8). Peak 2. ES/MS: m/z=226.2 [M+H]+.

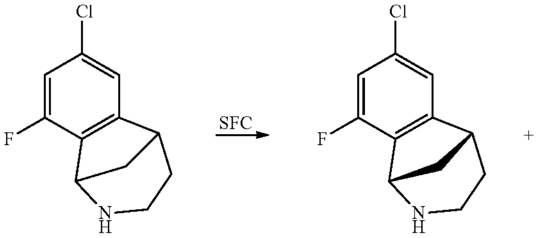

Ef-9

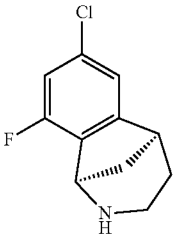

Ef-10

Prepared following general procedure VI-E starting with 2-bromo-4-chloro-6-fluorobenzaldehyde and prop-2-en-1-amine hydrochloride. The racemic amine was purified by SFC [with the following conditions: Column: CHIRALPAK IG, 3*25 cm, 5 m; Mobile Phase A: $CO_2$, Mobile Phase B: MeOH; Flow rate: 100 mL/min; Gradient: isocratic 20% B; Column Temperature (° C.): 35; Back Pressure (bar): 100; Wave Length: 206/230 nm; RT1 (min): 5.02, RT2 (min): 6.28].

Ef-9

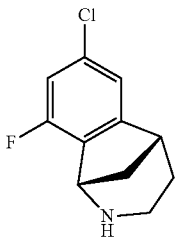

(1S,5R)-7-chloro-9-fluoro-2,3,4,5-tetrahydro-1H-1,5-methanobenzo[c]azepine (Ef-9). Peak 1. ES/MS: m/z=212.2 [M+H]+.

Ef-10

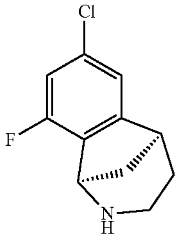

(1R,5S)-7-chloro-9-fluoro-2,3,4,5-tetrahydro-1H-1,5-methanobenzo[c]azepine (Ef-10). Peak 2. ES/MS: m/z=212.2 [M+H]+.

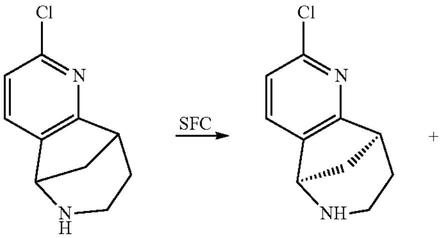

Ef-11

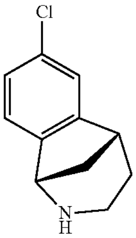

Ef-12

The mixture of Ef-11 and Ef-12 was prepared following general procedure VI-E starting with 2-bromo-6-chloropyridine-3-carbaldehyde and prop-2-en-1-amine hydrochloride. The racemic amine was purified by SFC.

Ef-11

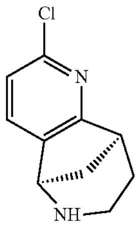

(5R,9S)-2-chloro-6,7,8,9-tetrahydro-5H-5,9-methanopyrido[3,2-c]azepine (Ef-11). Peak 1. ES/MS: m/z=195.2 [M+H]+.

Ef-12

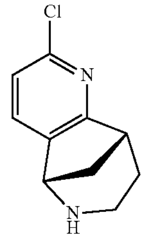

(5S,9R)-2-chloro-6,7,8,9-tetrahydro-5H-5,9-methano-pyrido[3,2-c]azepine (Ef-12). Peak 2. ES/MS: m/z=195.2 $[M+H]^+$.

General Procedure VII-E for the Synthesis of Intermediates E-g

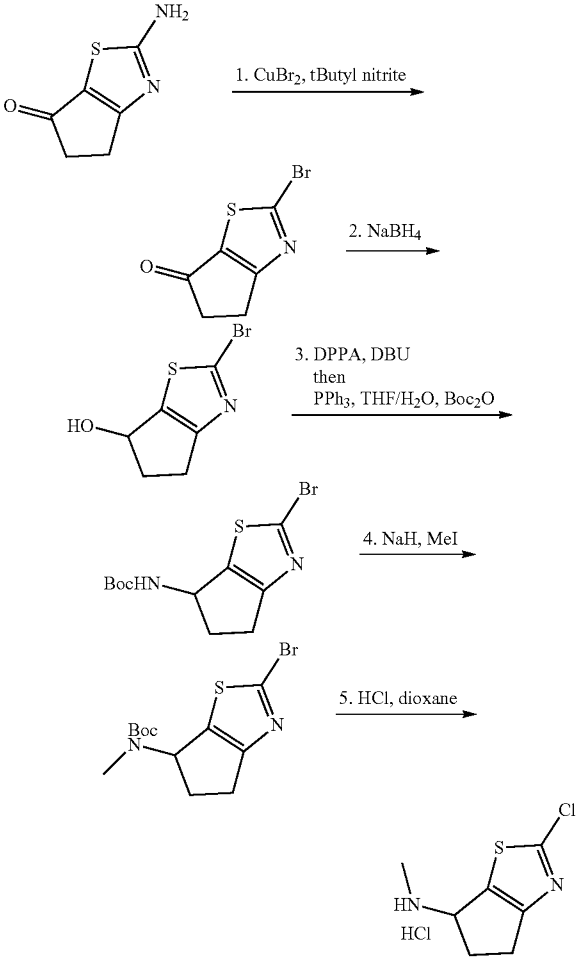

Eg-1

Step 1. 2-bromo-4,5-dihydro-6H-cyclopenta[d]thiazol-6-one. 2-amino-4,5-dihydrocyclopenta[d]thiazol-6-one (300 mg, 1.9 mmol) in MeCN (10 mL) was added $CuBr_2$ (565 mg, 2.5 mmol) and tert-butyl nitrite (0.33 mL, 2.5 mmol), respectively. The mixture was stirred at 60° C. for 5 hours before filtering and diluting with EtOAc (50 mL). The solution was washed with brine (100 mL) and dried over sodium sulfate. The crude residue was purified by flash chromatography to give desired product. ES/MS: m/z=219.0 $[M+H]^+$.

Step 2. 2-bromo-5,6-dihydro-4H-cyclopenta[d]thiazol-6-ol. Bromo-4,5-dihydrocyclopenta[d]thiazol-6-one (325 mg, 1.5 mmol) in DCM (10 mL) and MeOH (10 mL) was added $NaBH_4$ (60 mg, 1.6 mmol). The mixture was stirred at 25° C. for 30 mins before addition of methyl iodide (0.13 mL, 2.1 mmol). The reaction was stirred for additional 10 hours at 25° C. before quenching with saturated aq. $NH_4Cl$ (50 mL). The mixture was extracted with DCM (50 mL×3), washed with brine (100 mL), and dried over sodium sulfate. The crude residue was purified by flash chromatography to give desired product. ES/MS: m/z=221.0 $[M+H]^+$.

Step 3. tert-butyl (2-bromo-5,6-dihydro-4H-cyclopenta[d]thiazol-6-yl)carbamate. 2-bromo-5,6-dihydro-4H-cyclopenta[d]thiazol-6-ol (160 mg, 0.73 mmol) in toluene (4 mL) was added DBU (0.16 mL, 1.1 mmol) and DPPA (260 mg, 0.95 mmol) respectively at 0° C. The mixture was warmed to 25° C. and stirred for 5 hrs before addition of water (20 mL). The mixture was extracted with EtOAc (50 mL×3), washed with brine (100 mL), dried over sodium sulfate, and concentrated. The crude residue was redissolved in THF (3 mL) and water (1 mL). Triphenylphosphine (330 mg, 1.3 mmol) was added, and the mixture was stirred at 50° C. and for 12 hrs. Triethylamine (0.26 mL 1.9 mmol) and $Boc_2O$ (206 mg, 0.94 mmol) were added at 25° C. and stirred for 3 hours before addition of water (20 mL). The mixture was extracted with EtOAc (50 mL×3), washed with brine (100 mL), dried over sodium sulfate, and concentrated. The crude residue was purified by flash chromatography to give desired product. ES/MS: m/z=318.0 $[M+H]^+$.

Step 4. tert-butyl (2-bromo-5,6-dihydro-4H-cyclopenta[d]thiazol-6-yl)(methyl)carbamate. tert-butyl N-(2-bromo-5,6-dihydro-4H-cyclopenta[d]thiazol-6-yl)carbamate (180 mg, 0.56 mmol) in DMF (3 mL) was added NaH (60%, 40 mg, 1.0 mmol) at 0° C. The mixture was stirred at 0° C. for 30 mins before addition of methyl iodide (0.040 mL, 0.62 mmol). The reaction was stirred for additional 10 hours at 25° C. before quenching with saturated aq. $NH_4Cl$ (20 mL). The mixture was extracted with EtOAc (20 mL×3), washed with brine (30 mL), and dried over sodium sulfate. The crude residue was purified by flash chromatography to give desired product. ES/MS: m/z=334.0 $[M+H]^+$.

Step 5. 2-chloro-N-methyl-5,6-dihydro-4H-cyclopenta[d]thiazol-6-amine hydrogen chloride (Eg-1). Tert-butyl N-(2-bromo-5,6-dihydro-4H-cyclopenta[d]thiazol-6-yl)carbamate (185 mg, 0.56 mmol) in dioxane (3 mL) was added HCl (4M in dioxane, 2.8 mL, 11 mmol) at 25° C. The mixture was stirred at 25° C. for 12 hours before concentrating in vacuo to give the desired product. ES/MS: m/z=189.0 $[M+H]^+$. $^1H$ NMR (400 MHz, Chloroform-d) δ 7.47-7.37 (m, 2H), 7.36-7.24 (m, 1H), 4.42-4.19 (m, 2H), 3.77-3.54 (m, 2H), 3.07-2.64 (m, 4H).

General Procedure VIII-E for Intermediate Eh:

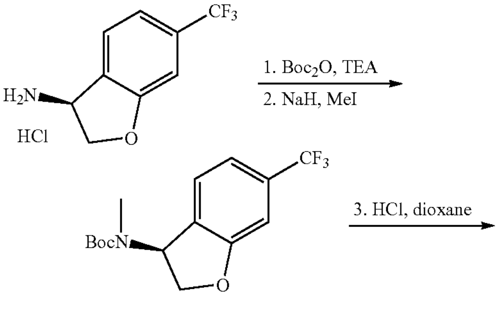

-continued

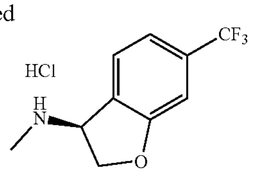

Eh-1

Step 1. tert-butyl (S)-(6-(trifluoromethyl)-2,3-dihydrobenzofuran-3-yl)carbamate. (3S)-6-(trifluoromethyl)-2,3-dihydrobenzofuran-3-amine hydrochloride (500 mg, 2.1 mmol) in DCM (7 mL) was added triethylamine (0.87 mL, 6.3 mmol) and $Boc_2O$ (500 mg, 2.3 mmol), respectively. The mixture was stirred at 25° C. for 5 hrs before concentrating under reduced pressure. The crude residue was purified by flash chromatography to give tert-butyl (S)-(6-(trifluoromethyl)-2,3-dihydrobenzofuran-3-yl)carbamate. ES/MS: m/z=304.0 $[M+H]^+$.

Step 2. Tert-butyl (S)-methyl(6-(trifluoromethyl)-2,3-dihydrobenzofuran-3-yl)carbamate. Tert-butyl (S)-(6-(trifluoromethyl)-2,3-dihydrobenzofuran-3-yl)carbamate (550 mg, 1.8 mmol) in DMF (7 mL) was added NaH (60%, 105 mg, 2.7 mmol) at 0° C. The mixture was stirred at 0° C. for 30 mins before addition of methyl iodide (0.13 mL, 2.1 mmol). The reaction was stirred for additional 10 hrs at 25° C. before quenching with saturated aq. $NH_4Cl$ (50 mL). The mixture was extracted with EtOAc (50 mL×3), washed with brine (100 mL), and dried over sodium sulfate. The crude residue was purified by flash chromatography to give tert-butyl (S)-methyl(6-(trifluoromethyl)-2,3-dihydrobenzofuran-3-yl)carbamate. ES/MS: m/z=318.0 $[M+H]^+$.

Step 3. (S)—N-methyl-6-(trifluoromethyl)-2,3-dihydrobenzofuran-3-amine hydrogen chloride. Tert-butyl (S)-methyl(6-(trifluoromethyl)-2,3-dihydrobenzofuran-3-yl) carbamate (530 mg, 1.7 mmol) in dioxane (3 mL) was added HCl (4M in dioxane, 4.2 mL, 17 mmol) at 25° C. The mixture was stirred at 25° C. for 5 hours before concentrating in vacuo to give (S)—N-methyl-6-(trifluoromethyl)-2,3-dihydrobenzofuran-3-amine hydrochloride Eh-1. ES/MS: m/z=218.0 $[M+H]^+$.

Eh-2

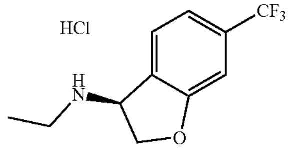

(S)—N-ethyl-6-(trifluoromethyl)-2,3-dihydrobenzofuran-3-amine hydrochloride (Eh-2). Prepared following procedure VIII-E using ethyl iodide. ES/MS: m/z=232.0 $[M+H]^+$.

Eh-3

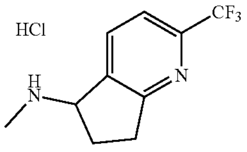

N-methyl-2-(trifluoromethyl)-6,7-dihydro-5H-cyclopenta[b]pyridin-5-amine hydrochloride (Eh-3). Prepared following procedure VIII-1 starting with 2-(trifluoromethyl)-6,7-dihydro-5H-cyclopenta[b]pyridin-5-amine hydrochloride. ES/MS: m/z=217.0 $[M+H]^+$.

Eh-4

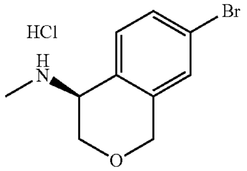

(S)-7-bromo-N-methylisochroman-4-amine hydrochloride (Eh-4). Prepared following procedure VIII-E starting with (S)-7-bromoisochroman-4-amine hydrochloride ES/MS: m/z=242.0 $[M+H]^+$.

Eh-5

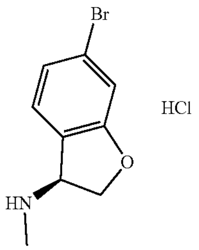

(S)-6-bromo-N-methyl-2,3-dihydrobenzofuran-3-amine (Eh-5). Prepared following procedure VIII-E starting with (S)-6-bromo-2,3-dihydrobenzofuran-3-amine hydrochloride. EZ/MS: m/s=229.7 $[M+H]^+$. $^1H$ NMR (400 MHz, MeOD) δ 7.55-7.45 (m, 1H), 7.29-7.16 (m, 2H), 5.01 (s, 1H), 4.85-4.78 (m, 1H), 4.74 (dd, J=11.9, 7.4 Hz, 1H), 3.68 (s, 2H), 2.73 (s, 3H).

Eh-6

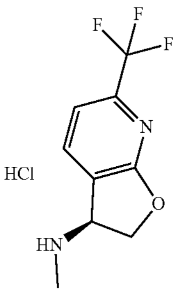

(S)—N-methyl-6-(trifluoromethyl)-2,3-dihydrofuro[2,3-b]pyridin-3-amine (Eh-6). Prepared following procedure VIII-E starting with (S)-6-(trifluoromethyl)-2,3-dihydrofuro[2,3-b]pyridin-3-amine hydrochloride. EZ/MS: m/z=219.1 $[M+H]^+$.

Eh-7

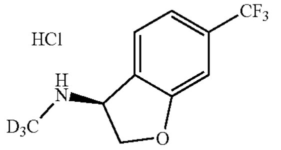

(S)—N-(methyl-d3)-6-(trifluoromethyl)-2,3-dihydrobenzofuran-3-amine hydrochloride (Eh-7). Prepared following procedure VIII-E using iodomethane-d3. EZ/MS: m/z=221.0 $[M+H]^+$.

Eh-8

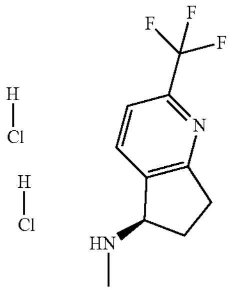

(R)—N-methyl-2-(trifluoromethyl)-6,7-dihydro-5H-cyclopenta[b]pyridin-5-amine dihydrochloride (Eh-8). Prepared following procedure VIII-E starting with (R)-2-(trifluoromethyl)-6,7-dihydro-5H-cyclopenta[b]pyridin-5-amine dihydrochloride. ES/MS: m/z=217.0 $[M+H]^+$.

Eh-9

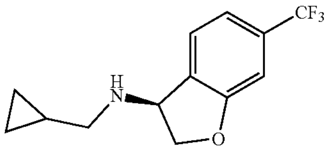

(3S)—N-(cyclopropylmethyl)-6-(trifluoromethyl)-2,3-dihydrobenzofuran-3-amine (Eh-9). Prepared following procedure VIII-E using bromomethylcyclopropane. ES/MS: m/z=258.0 $[M+H]^+$.

Eh-10

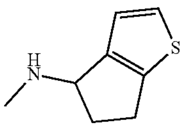

N-methyl-5,6-dihydro-4H-cyclopenta[b]thiophen-4-amine (Eh-10). Prepared following procedure VIII-E using 5,6-dihydro-4H-cyclopenta[b]thiophen-4-amine. ES/MS: m/z =154.1 $[M+H]^+$.

Eh-11

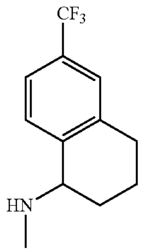

N-methyl-6-(trifluoromethyl)tetralin-1-amine (Eh-11). Prepared following procedure VIII-E using 6-(trifluoromethyl)-1,2,3,4-tetrahydronaphthalen-1-amine. ES/MS: m/z =230.2

Eh-12

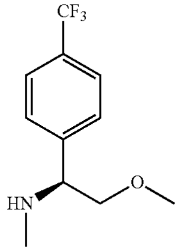

(S)-2-methoxy-N-methyl-1-(4-(trifluoromethyl)phenyl)ethan-1-amine (Eh-12). Prepared following procedure VIII-E using (1S)-2-methoxy-1-[4-(trifluoromethyl)phenyl]ethanamine hydrochloride. ES/MS: m/z=234.2 $[M+H]^+$.

Eh-13

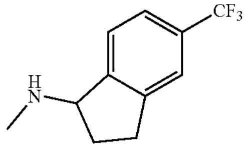

N-methyl-5-(trifluoromethyl)indan-1-amine (Eh-13). Prepared following procedure VIII-E using 2,3-dihydro-5-(trifluoromethyl)-1H-inden-1-amine. ES/MS: m/z=258.0 $[M+H]^+$.

Eh-14

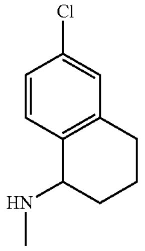

6-chloro-N-methyl-1,2,3,4-tetrahydronaphthalen-1-amine (Eh-14). Prepared following procedure VIII-E using 6-chloro-N-methyl-1,2,3,4-tetrahydronaphthalen-1-amine. ES/MS: m/z=196.0.

Eh-15

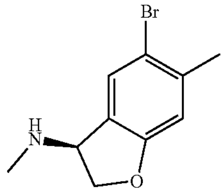

(S)-5-bromo-N,6-dimethyl-2,3-dihydrobenzofuran-3-amine (Eh-15). Prepared following procedure VIII-E starting with (S)-5-bromo-6-methyl-2,3-dihydrobenzofuran-3-amine. ES/MS: m/z 243.8 $[M+H]^+$.

Eh-16

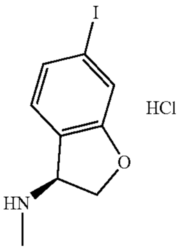

(S)-6-iodo-N-methyl-2,3-dihydrobenzofuran-3-amine hydrochloride (Eh-16). Prepared following procedure VIII-E starting with (S)-6-iodo-2,3-dihydrobenzofuran-3-amine. ES/MS: m/s=276.2 $[M+H]^+$.

Eh-17

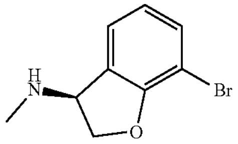

(S)-7-bromo-N-methyl-2,3-dihydrobenzofuran-3-amine (Eh-17). Prepared following procedure VIII-E starting with (S)-7-bromo-2,3-dihydrobenzofuran-3-amine. ES/MS: m/z 229.8 $[M+H]^+$.

Eh-18

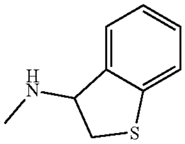

N-methyl-2,3-dihydrobenzo[b]thiophen-3-amine (Eh-18). Prepared following procedure VIII-E starting with 2,3-dihydrobenzo[b]thiophen-3-amine. ES/MS: m/z 166.1 $[M+H]^+$.

Eh-19

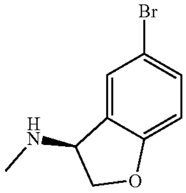

(S)-5-bromo-N-methyl-2,3-dihydrobenzofuran-3-amine (Eh-19). Prepared following procedure VIII-E starting with (3S)-5-bromo-2,3-dihydrobenzofuran-3-amine. ES/MS: m/z 229.5 $[M+H]^+$.

Eh-20

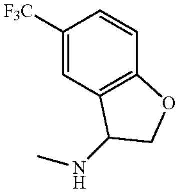

N-methyl-5-(trifluoromethyl)-2,3-dihydrobenzofuran-3-amine (Eh-20). Prepared following procedure VIII-E starting with 2-hydroxy-5-(trifluoromethyl)benzaldehyde and 2-methylpropane-2-sulfinamide. ES/MS: m/z 217.9 $[M+H]^+$.

Eh-21

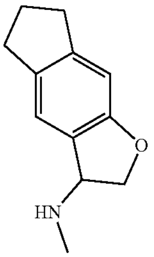

N-methyl-3,5,6,7-tetrahydro-2H-indeno[5,6-b]furan-3-amine (Eh-21). Prepared following procedure VIII-E starting with 2-hydroxy-5-(trifluoromethyl)benzaldehyde and 2-methylpropane-2-sulfinamide. ES/MS: m/z 190.9 $[M+H]^+$.

Eh-22

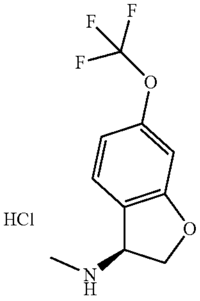

(S)—N-methyl-6-(trifluoromethoxy)-2,3-dihydrobenzofuran-3-amine hydrogen chloride (Eh-22). Prepared following procedure VIII-E using commercial (S)-6-(trifluoromethoxy)-2,3-dihydrobenzofuran-3-amine hydrogen chloride. ES/MS: m/z=233.8 [M+H]$^+$.

Eh-23

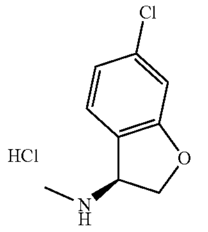

(S)—N-methyl-6-chloro-2,3-dihydrobenzofuran-3-amine hydrogen chloride (Eh-23). Prepared following procedure VIII-E using commercial (S)-6-chloro-2,3-dihydrobenzofuran-3-amine hydrogen chloride. ES/MS: m/z=184.2 [M+H]$^+$.

Eh-24

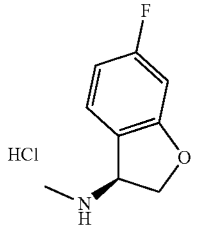

(S)—N-methyl-6-fluoro-2,3-dihydrobenzofuran-3-amine hydrogen chloride (Eh-24). Prepared following procedure VIII-E using commercial (S)-6-fluoro-2,3-dihydrobenzofuran-3-amine hydrogen chloride. ES/MS: m/z=167.8 [M+H]$^+$.

Eh-25

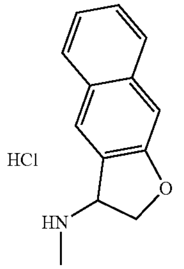

N-methyl-2,3-dihydronaphtho[2,3-b]furan-3-amine (Eh-25). Prepared following procedure VIII-E starting with 3-hydroxynapththalene-2-carbaldehyde and methylamine. ES/MS: m/z=169.2 (—$NHCH_3$) [M+H]$^+$.

General Procedure IX-E for Intermediates Ei:

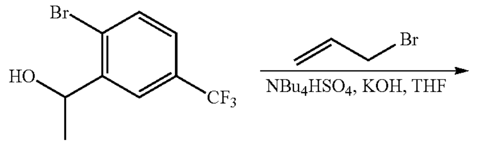

-continued

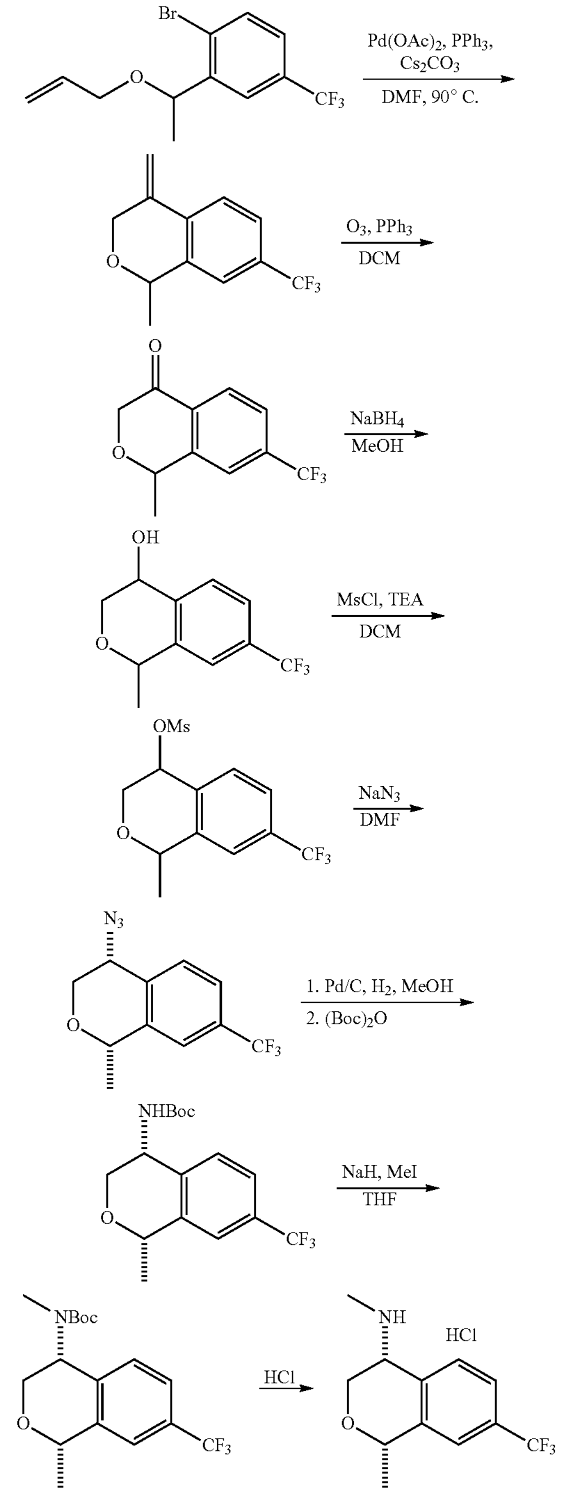

(+/-) Ei-2

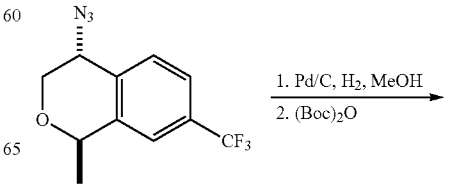

-continued

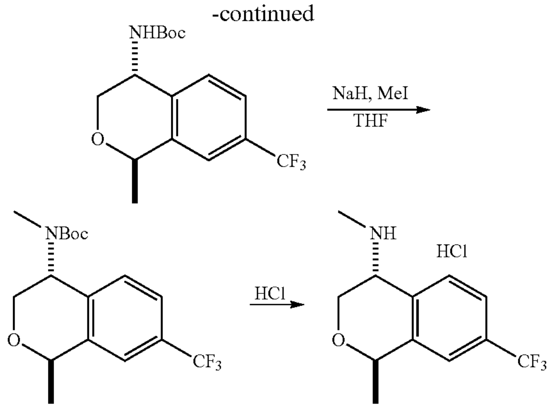

(+/-) Ei-1

Step 1. 2-(1-(allyloxy)ethyl)-1-bromo-4-(trifluoromethyl) benzene. To a solution of 1-(2-bromo-5-(trifluoromethyl) phenyl)ethan-1-ol (48.5 g, 0.18 mol, 1.0 eq) and compound 3 (21.8 g, 0.18 mol, 1.0 eq) at 0° C. in THF (100 mL) was added KOH (19.2 g, 0.34 mol, 1.9 eq) and $NBu_4HSO_4$ (9.2 g, 27 mmol, 0.15 eq). The reaction was stirred at rt for 16 h. The mixture was diluted with water (200 mL) and extracted with EtOAc (100 mL×3). The organic layers were washed with brine, dried over anhydrous $Na_2SO_4$, filtered and concentrated. The residue was purified by silica gel chromatography to afford the desired compound. ES/MS: m/z=308.0 $[M+H]^+$.

Step 2. 1-methyl-4-methylene-7-(trifluoromethyl)isochromane. To a solution of 2-(1-(allyloxy)ethyl)-1-bromo-4-(trifluoromethyl)benzene (41.1 g, 0.13 mol, 1.0 eq) and $PPh_3$ (15.7 g, 60 mmol, 0.45 eq) in DMF (100 mL) was added $Cs_2CO_3$ (52 g, 0.16 mol, 1.2 eq) and $Pd(OAc)_2$ (4.5 g, 20 mmol, 0.15 eq). The reaction was stirred at 90° C. for 16 h under $N_2$ atmosphere. After concentration, the residue was diluted with EtOAc (400 mL) and washed with water (100 mL×3). The organic layers were washed with brine, dried over anhydrous $Na_2SO_4$, filtered and concentrated. The residue was purified by silica gel chromatography to afford the desired compound. ES/MS: m/z=228.08 $[M+H]^+$.

Step 3. 1-methyl-7-(trifluoromethyl)isochroman-4-one. Ozone was bubbled into a solution of 1-methyl-4-methylene-7-(trifluoromethyl)isochromane (18.4 g, 80.7 mmol) in DCM (100 mL) at −78° C. for 1 h. Then ozone was removed with nitrogen, and $PPh_3$ (21.2 g, 80.7 mmol, 1.0 eq) was added. The reaction was stirred at rt for 16 h. The reaction was washed with water (100 mL×3), brine, dried over $Na_2SO_4$, filtered and concentrated. The residue was purified by silica gel chromatography to afford the desired compound. ES/MS: m/z=230.06 $[M+H]^+$.

Step 4. 1-methyl-7-(trifluoromethyl)isochroman-4-ol. To a solution of 1-methyl-7-(trifluoromethyl)isochroman-4-one (11.8 g, 51.3 mmol) in methanol (100 mL) at 0° C. was added $NaBH_4$ (2.5 g, 66.7 mmol, 1.3 eq). The reaction was stirred at RT for 30 min. The reaction was quenched with saturated solution of $NH_4Cl$ and extracted with DCM (100 mL×3). The combined organic layers were washed with brine, dried over anhydrous $Na_2SO_4$, filtered and concentrated. The residue was purified by silica gel chromatography to afford the desired compound. ES/MS: m/z=232.07 $[M+H]^+$.

Step 5. 1-methyl-7-(trifluoromethyl)isochroman-4-yl methanesulfonate. To a solution of 1-methyl-7-(trifluoromethyl)isochroman-4-ol (10.9 g, 47.0 mmol, 1.0 eq) in DCM (100 mL) at 0° C. was added MsCl (7.0 g, 61.1 mmol, 1.3 eq) and triethylamine (6.6 g, 65.8 mmol, 1.4 eq). The reaction was stirred at rt for 2 h. The mixture was diluted with water (200 mL) and extracted with DCM (100 mL×3). The organic layers were washed with brine, dried over $Na_2SO_4$, filtered and concentrated. The residue was purified by silica gel chromatography to afford the desired compound. ES/MS: m/z=310.05 $[M+H]^+$.

Step 6. Rac-(1R,4R)-4-azido-1-methyl-7-(trifluoromethyl)isochromane and rac-(1S,4R)-4-azido-1-methyl-7-(trifluoromethyl)isochromane. To a solution of 1-methyl-7-(trifluoromethyl)isochroman-4-yl methanesulfonate (13.8 g, 53.7 mmol) in DMF (100 mL) was added $NaN_3$ (7.0 g, 107.4 mmol, 2.0 eq). The reaction was stirred at rt for 16 h. The mixture was diluted with EA (200 mL) and washed with water (100 mL), brine, dried over $Na_2SO_4$, filtered and concentrated. The reside was purified by column chromatography to get rac-(1R,4R)-4-azido-1-methyl-7-(trifluoromethyl)isochromane and rac-(1S,4R)-4-azido-1-methyl-7-(trifluoromethyl)isochromane.

rac-(1R,4R)-4-azido-1-methyl-7-(trifluoromethyl)isochromane: $^1H$ NMR (400 MHz, $CDCl_3$) δ 7.58 (d, J=8.0 Hz, 1H), 7.48-7.44 (m, 2H), 4.85-4.80 (m, 1H), 4.34-4.31 (m, 1H), 4.10 (s, 1H), 3.95-3.92 (m, 1H), 1.63 (d, J=8.0 Hz, 3H).

rac-(1S,4R)-4-azido-1-methyl-7-(trifluoromethyl)isochromane: $^1H$ NMR (400 MHz, $CDCl_3$) δ 7.58-7.53 (m, 2H), 7.36 (s, 1H), 4.99-4.96 (m, 1H), 4.44-4.41 (m, 1H), 4.30-4.26 (m, 1H), 3.86-3.82 (m, 1H), 1.55 (d, J=8.0 Hz, 3H).

Note: the following synthetic sequence will be described starting with rac-(1R,4R)-4-azido-1-methyl-7-(trifluoromethyl)isochromane.

Step 7. Rac-tert-butyl ((1R,4R)-1-methyl-7-(trifluoromethyl)isochroman-4-yl)carbamate. To a solution of rac-(1R,4R)-4-azido-1-methyl-7-(trifluoromethyl)isochromane (3.0 g, 11.7 mmol) in methanol (30 mL) was added Pd/C (300 mg, 10% wt.). The reaction was stirred at rt for 1 h under hydrogen atmosphere. Then $(Boc)_2O$ (3.1 g, 14.0 mmol, 1.2 eq) was added. The reaction was stirred at rt for 1 h. The solid was filtered through a pad of Celite, and the filtrate was concentrated. The reside was purified by column chromatography to afford the desired product. ES/MS: m/z=332.05 $[M+H]^+$.

Step 8. Rac-tert-butyl methyl((1R,4R)-1-methyl-7-(trifluoromethyl)isochroman-4-yl)carbamate. To a solution of rac-tert-butyl ((1R,4R)-1-methyl-7-(trifluoromethyl)isochroman-4-yl)carbamate (1.5 g, 4.5 mmol) in THF (20 mL) at 0° C. was added NaH (720 mg, 18.0 mmol, 4.0 eq, 60% in mineral oil) under $N_2$ atmosphere. The reaction was stirred at rt for 1 h. Then iodomethane (3.2 g, 22.5 mmol, 5.0 eq) was added. The reaction was stirred at rt for 16 h. The reaction was quenched with saturated solution of $NH_4Cl$ (50 mL) and extracted with DCM (50 mL×3). The organic layers were washed with brine, dried over $Na_2SO_4$, filtered and concentrated. The reside was purified by column chromatography to afford the desired product. ES/MS: m/z=346.05 $[M+H]^+$.

Step 9. Rac-(1R,4R)—N,1-dimethyl-7-(trifluoromethyl) isochroman-4-amine hydrochloride salt ((±)-Ei-1). To a solution of rac-tert-butyl methyl((1R,4R)-1-methyl-7-(trifluoromethyl)isochroman-4-yl)carbamate (1.3 g, 3.8 mmol) in EA (5 mL) at 0° C. was added HCl/EtOAc (4 M, 15 mL). The reaction was stirred at rt for 1 h. After concentration, the residue was triturated with diethyl ether and filtered to get the desired product. ES/MS: m/z=246.1 $[M+H]^+$. $^1H$NMR (400 MHz, $CDCl_3$) δ 10.19 (s, 1H), 10.09 (s, 1H), 7.99 (d, J=8.0 Hz, 1H), 7.61 (d, J=8.0 Hz, 1H), 7.46 (s, 1H), 4.83-4.79 (m, 2H), 4.40 (s, 1H), 3.92 (d, J=12.0 Hz, 1H), 2.67-2.59 (m, 3H), 1.67 (d, J=8.0 Hz, 3H).

Rac-(1S,4R)—N,1-dimethyl-7-(trifluoromethyl)isochroman-4-amine hydrochloride salt ((±)-Ei-2) was prepared in a similar fashion as (±)-Ei-1 starting with rac-(1S,4R)-4-azido-1-methyl-7-(trifluoromethyl)isochromane. ES/MS: m/z=246.1 [M+H]$^+$. $^1$HNMR (400 MHz, $CDCl_3$) δ 10.14 (s, 1H), 10.07 (s, 1H), 7.91 (d, J=8.0 Hz, 1H), 7.58 (d, J=8.0 Hz, 1H), 7.38 (s, 1H), 5.23-5.18 (m, 1H), 4.49 (d, J=16.0 Hz, 1H), 3.31 (s, 1H), 4.15 (d, J=12.0 Hz, 1H), 2.62-2.54 (m, 3H), 1.53 (d, J=8.0 Hz, 3H).

(S)—N-methyl-2-(trifluoromethyl)-5,8-dihydro-6H-pyrano[3,4-b]pyridin-5-amine hydrochloride (Ei-3) and (R)—N-methyl-2-(trifluoromethyl)-5,8-dihydro-6H-pyrano[3,4-b]pyridin-5-amine hydrochloride (Ei-4) were prepared following procedure IX-E starting with (3-bromo-6-(trifluoromethyl)pyridin-2-yl)methanol and separated using chiral SFC.

Ei-3

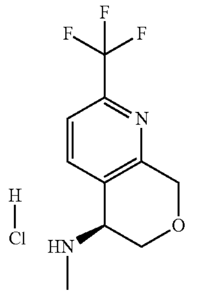

(S)—N-methyl-2-(trifluoromethyl)-5,8-dihydro-6H-pyrano[3,4-b]pyridin-5-amine hydrochloride (Ei-3). Peak 1 Chiralcel OZ-H (Hex/EtOH/DEA 90:10:0.1, 1.0 mL/min) RT=5.45 min. ES/MS: m/z=233.0 [M+H]$^+$.

Ei-4

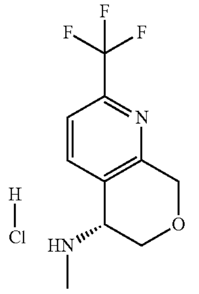

(R)—N-methyl-2-(trifluoromethyl)-5,8-dihydro-6H-pyrano[3,4-b]pyridin-5-amine hydrochloride (Ei-4). Prepared following procedure IX-E starting with (3-bromo-6-(trifluoromethyl)pyridin-2-yl)methanol. Peak 2 Chiralcel OZ-H (Hex/EtOH/DEA 90:10:0.1, 1.0 mL/min) RT=6.09 min. ES/MS: m/z=233.0 [M+H]$^+$.

General Procedure X-E for Intermediates Ej

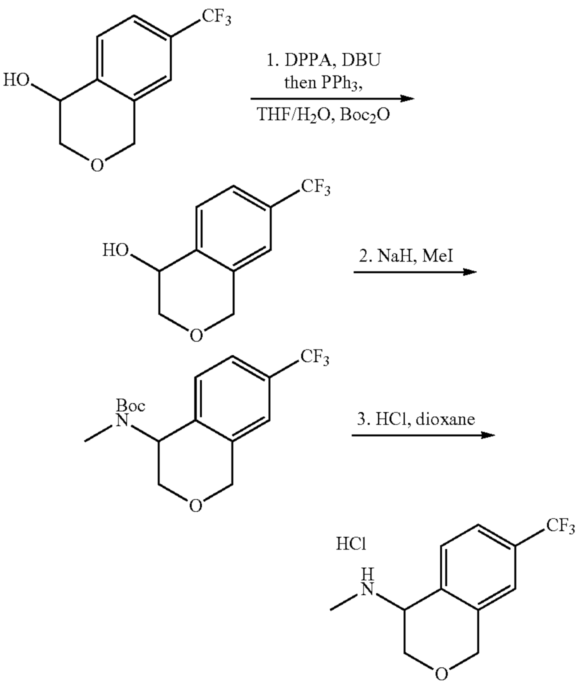

Ej-1

Step 1. tert-butyl N-[7-(trifluoromethyl)isochroman-4-yl]carbamate. 7-(trifluoromethyl)isochroman-4-ol (385 mg, 1.8 mmol) in toluene (9 mL) was added DBU (0.40 mL, 2.6 mmol) and DPPA (630 mg, 2.3 mmol) respectively at 0° C. The mixture was warmed to 25° C. and stirred for 5 hrs before addition of water (50 mL). The mixture was extracted with EtOAc (80 mL×3), washed with brine (100 mL), dried over sodium sulfate, and concentrated. The crude residue was purified by flash chromatography to give desired product. The product was then dissolved in THF (6 mL) and water (2 mL). Triphenylphosphine (108 mg, 0.41 mmol) was added, and the mixture was stirred at 50° C. and for 12 hrs. Triethylamine (0.09 mL 0.62 mmol) and $Boc_2O$ (67 mg, 0.31 mmol) were added at 25° C. and stirred for 3 hrs before addition of water (20 mL). The mixture was extracted with EtOAc (50 mL×3), washed with brine (100 mL), dried over sodium sulfate, and concentrated. The crude residue was purified by flash chromatography to give desired product. ES/MS: m/z=318.0 [M+H]$^+$.

Step 2. tert-butyl N-methyl-N-[7-(trifluoromethyl)isochroman-4-yl]carbamate. tert-butyl N-[7-(trifluoromethyl)isochroman-4-yl]carbamate (48 mg, 0.15 mmol) in DMF (1 mL) was added NaH (60%, 10 mg, 0.27 mmol) at 0° C. The mixture was stirred at 0° C. for 30 mins before addition of methyl iodide (0.01 mL, 0.17 mmol). The reaction was stirred for additional 10 hrs at 25° C. before quenching with saturated aq. $NH_4Cl$ (20 mL). The mixture was extracted with EtOAc (20 mL×3), washed with brine (30 mL), and dried over sodium sulfate. The crude residue was purified by flash chromatography to give desired product. ES/MS: m/z=332.0 [M+H]$^+$.

Step 3. N-methyl-7-(trifluoromethyl)isochroman-4-amine hydrochloride (Ej-1). tert-butyl N-methyl-N-[7-(trifluoromethyl)isochroman-4-yl]carbamate (40 mg, 0.12 mmol) in dioxane (3 mL) was added HCl (4M in dioxane, 0.6 mL, 2.4 mmol) at 25° C. The mixture was stirred at 25° C. for 6 hrs before concentrating in vacuo to give the desired product. ES/MS: m/z=268.0 [M+H]$^+$.

Ej-2

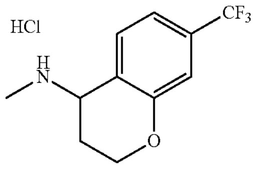

N-methyl-7-(trifluoromethyl)chroman-4-amine hydrochloride (Ej-2). Prepared following general procedure X-E starting with 7-(trifluoromethyl)chroman-4-ol. ES/MS: m/z=268.0 [M+H]$^+$.

Ej-3

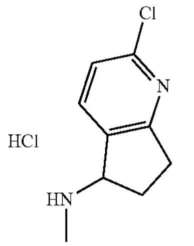

2-chloro-N-methyl-6,7-dihydro-5H-cyclopenta[b]pyridin-5-amine hydrochloride (Ej-2): Prepared following general procedure X-E starting with 2-chloro-6,7-dihydro-5H-cyclopenta[b]pyridin-5-ol. ES/MS: m/z=183.0

Ej-4

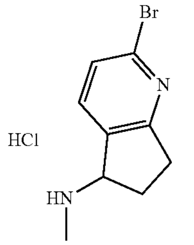

2-bromo-N-methyl-6,7-dihydro-5H-cyclopenta[b]pyridin-5-amine hydrogen chloride (Ej-4): Prepared following general procedure X-E starting with 2-bromo-6,7-dihydro-5H-cyclopenta[b]pyridin-5-ol. ES/MS: m/z=228.2 [M+H]$^+$.

Ej-5

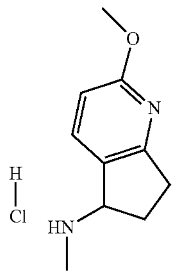

2-methoxy-N-methyl-6,7-dihydro-5H-cyclopenta[b]pyridin-5-amine hydrochloride (Ej-5). Prepared following procedure X-E starting with 2-methoxy-6,7-dihydro-5H-cyclopenta[b]pyridin-5-ol. ES/MS: m/z=179.0 [M+H]$^+$.

Ej-6

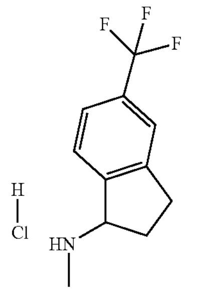

N-methyl-5-(trifluoromethyl)-2,3-dihydro-1H-inden-1-amine hydrochloride (Ej-6). Prepared following procedure X-E starting with 2-methoxy-6,7-dihydro-5H-cyclopenta[b]pyridin-5-ol. ES/MS: m/z=216.0 [M+H]$^+$.

General Procedure XI-E for Intermediates Ek

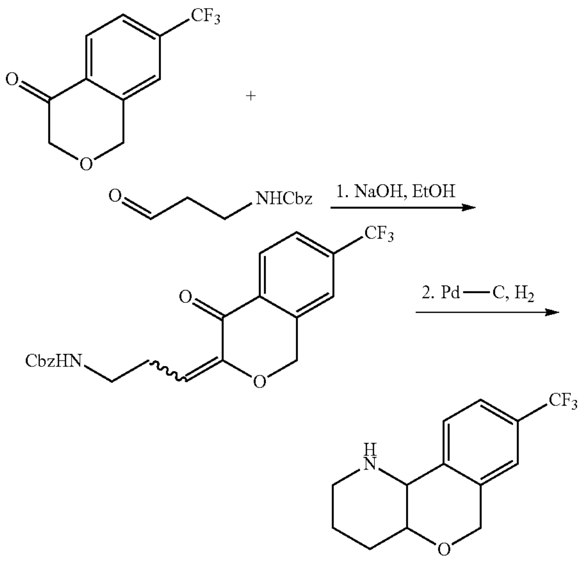

Ek-1

Step 1. benzyl (3-(4-oxo-7-(trifluoromethyl)isochroman-3-ylidene)propyl)carbamate. 7-(trifluoromethyl)isochroman-4-one (110 mg, 0.51 mmol) and benzyl N-(3-oxopropyl)carbamate (130 mg, 0.61 mmol) in EtOH (3 mL) was added NaOH (1M aq., 0.5 mL, 0.50 mmol) at 0° C. The mixture was stirred at 0° C. for 1 hrs before diluting with DCM (20 mL). The solution was washed with water (10 mL×2) and dried over sodium sulfate. The crude residue was purified by flash chromatography to give desired product. ES/MS: m/z=406.0 [M+H]$^+$.

Step 2. 8-(trifluoromethyl)-2,3,4,4a,6,10b-hexahydro-1H-isochromeno[4,3-b]pyridine (Ek-1). Benzyl (3-(4-oxo-7-(trifluoromethyl)isochroman-3-ylidene)propyl)carbamate (40 mg, 0.10 mmol) in EtOH (5 mL) was added 10% palladium on carbon (16 mg, 0.015 mmol). The mixture was stirred at 25° C. under 1 atm of hydrogen balloon for 30 mins before filtering. The mixture was concentrated and was purified by flash chromatography to give desired product. ES/MS: m/z=258.0 $[M+H]^+$.

General Procedure XII-E for the Synthesis of Intermediates El

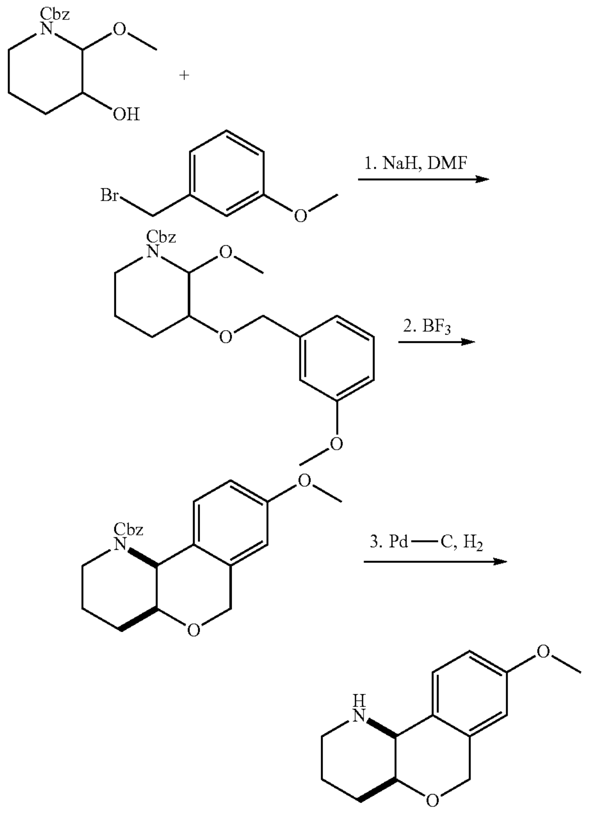

El-1
(±)

Step 1. benzyl 2-methoxy-3-[(3-methoxyphenyl)methoxy]piperidine-1-carboxylate. Benzyl 3-hydroxy-2-methoxy-piperidine-1-carboxylate (200 mg, 0.75 mmol) in DMF (5 mL) was added NaH (60%, 43 mg, 1.1 mmol) at 0° C. The mixture was stirred at 0° C. for 30 mins before addition of 1-(bromomethyl)-3-methoxy-benzene (180 mg, 0.90 mmol). The reaction was stirred for additional 10 hrs at 25° C. before quenching with saturated aq. $NH_4Cl$ (20 mL). The mixture was extracted with EtOAc (20 mL×3), washed with brine (30 mL), and dried over sodium sulfate. The crude residue was purified by flash chromatography to give desired product. ES/MS: m/z=386.2 $[M+H]^+$.

Step 2. benzyl (cis)-8-methoxy-2,3,4,4a,6,10b-hexahydro-1H-isochromeno[4,3-b]pyridine-1-carboxylate. Benzyl 2-methoxy-3-[(3-methoxyphenyl)methoxy]piperidine-1-carboxylate (80 mg, 0.21 mmol) in DCM (2 mL) at 0° C. was added $BF_3$-$Et_2O$ (0.05 mL, 0.42 mmol). The mixture was stirred at 0° C. for 30 mins before quenching with saturated aq. $NaHCO_3$ (5 mL). The mixture was extracted with EtOAc (20 mL×3), washed with brine (30 mL), and dried over sodium sulfate. The crude residue was purified by flash chromatography to give desired product. ES/MS: m/z=354.0 $[M+H]^+$.

Step 3. Cis-(4aS,10bS)-8-methoxy-2,3,4,4a,6,10b-hexahydro-1H-isochromeno[4,3-b]pyridine (El-1). Benzyl (cis)-8-methoxy-2,3,4,4a,6,10b-hexahydro-1H-isochromeno[4,3-b]pyridine-1-carboxylate (65 mg, 0.18 mmol) in EtOH (5 mL) was added 10% palladium on carbon (30 mg, 0.028 mmol). The mixture was stirred at 25° C. under 1 atm of hydrogen balloon for 30 mins before filtering. The mixture was concentrated and was purified by flash chromatography to give desired product. ES/MS: m/z=220.0 $[M+H]^+$.

El-2

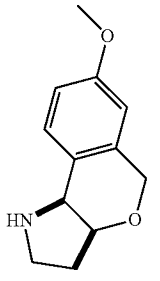

(±)

Cis-(3aS,9bS)-7-methoxy-1,2,3,3a,5,9b-hexahydroisochromeno[4,3-b]pyrrole (El-2). Prepared following procedure XII-E starting with benzyl 3-hydroxy-2-methoxy-pyrrolidine-1-carboxylate. ES/MS: m/z=206.2 $[M+H]^+$.

El-3

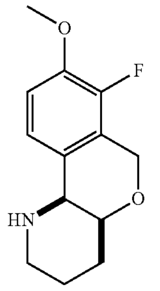

(±)

Cis-(4aS,10bS)-7-fluoro-8-methoxy-2,3,4,4a,6,10b-hexahydro-1H-isochromeno[4,3-b]pyridine (El-3). Prepared following procedure XII-E starting with 1-(bromomethyl)-2-fluoro-3-methoxy-benzene. ES/MS: m/z=238.0 $[M+H]^+$.

El-4

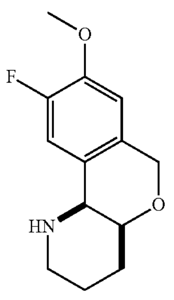

(±)

Cis-(4aS,10bS)-9-fluoro-8-methoxy-2,3,4,4a,6,10b-hexahydro-1H-isochromeno[4,3-b]pyridine (El-4). Prepared following procedure XII-E starting with 4-(bromomethyl)-1-fluoro-2-methoxy-benzene. ES/MS: m/z=238.0 $[M+H]^+$.

El-5

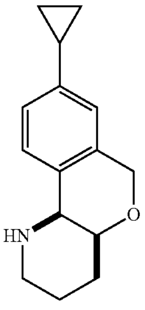

(±)

Cis-(4aS,10bS)-8-cyclopropyl-2,3,4,4a,6,10b-hexahydro-1H-isochromeno[4,3-b]pyridine (E1-5). Prepared following procedure XII-E starting with 4-(bromomethyl)-1-fluoro-2-methoxy-benzene. ES/MS: m/z=230.0 [M+H]$^+$.

General Procedure XIII-E for the Synthesis of Intermediates Em

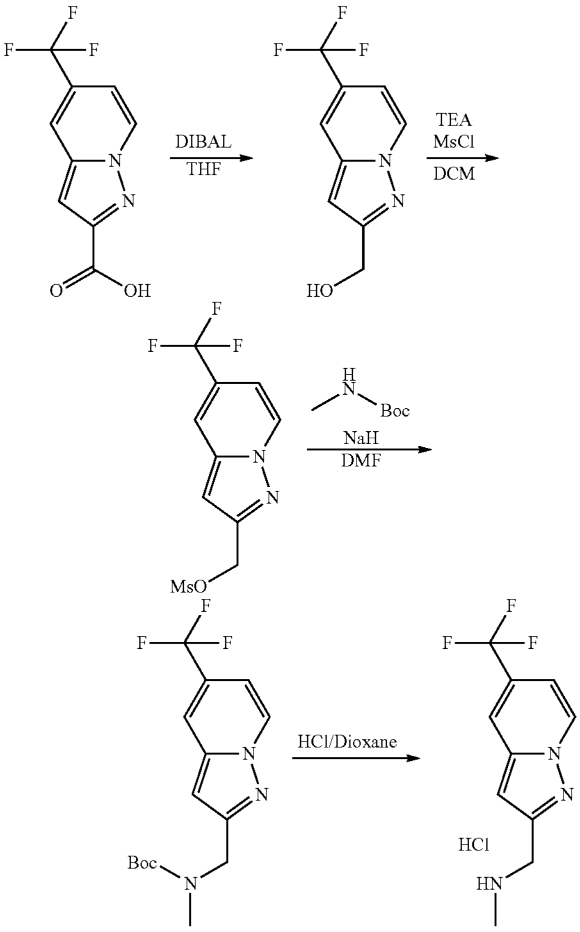

Em-1

Step 1. [5-(trifluoromethyl)pyrazolo[1,5-a]pyridin-2-yl] methanol. To a solution of 5-(trifluoromethyl)pyrazolo[1,5-a]pyridine-2-carboxylic acid (1.3 mmol) in THF (0.4 M) under and atmosphere of nitrogen cooled to 0° C. DIBAL (1.0 M in THF, 4.0 equiv) was added dropwise. The Reaction mixture was allowed to warm to room temperature and stirred for 5 h. At which point the reaction mixture was cooled in an ice bath, and diluted with Ether, and water (1.0 equiv) was added followed by Sodium hydroxide (1.0 equiv, 15% soln in water) dried, filtered and concentrated. Purification by column chromatography. ES/MS: m/z=217.0 [M+H]$^+$.

Step 2. (5-(trifluoromethyl)pyrazolo[1,5-a]pyridin-2-yl) methyl methanesulfonate. A solution of [5-(trifluoromethyl) pyrazolo[1,5-a]pyridin-2-yl]methanol (1.0 equiv) in DCM (0.1 M) was cooled to 0° C. and then triethylamine (1.2 equiv) was added followed by methanesulfonyl chloride (1.2 equiv). The reaction mixture was allowed to stir at 0 C for 10 min. At which point it was concentrated and used without further purification. ES/MS: m/z=295.0 [M+H]$^+$.

Step 3. tert-butyl methyl((5-(trifluoromethyl)pyrazolo[1,5-a]pyridin-2-yl)methyl)carbamate. To a solution of tert-butyl N-methylcarbamate (1.0 equiv) in DMF (0.2 M) at 0 C, was added sodium hydride (1.2 equiv) followed by (5-(trifluoromethyl)pyrazolo[1,5-a]pyridin-2-yl)methyl methanesulfonate (1.05 equiv). The reaction mixture was allowed to stir at 50 C overnight. at which point the reaction mixture was diluted with EtOAc and washed with 5% aqueous lithium chloride. The mixture was dried, filtered, concentrated and purified by column chromatography. ES/MS: m/z=329.9 [M+H]$^+$.

Step 4. N-methyl-1-(5-(trifluoromethyl)pyrazolo[1,5-a] pyridin-2-yl)methanamine hydrochloride (Em-1). tert-butyl methyl((5-(trifluoromethyl)pyrazolo[1,5-a]pyridin-2-yl) methyl)carbamate (1.0 equiv) as dissolved in DCM (0.5 M) and HCl in Dioxane (4.0 M, 5.0 equiv) and allowed to stir overnight at room temperature. The reaction mixture was concentrated and used without further purification. ES/MS: m/z=230.1 [M+H]$^+$.

General Procedure XIV-E for the Synthesis of Intermediates En

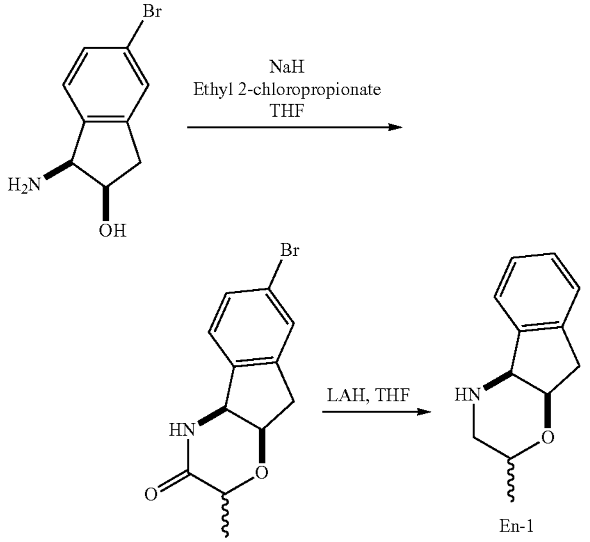

En-1

Step 1. Rac-(4aS,9aR)-7-bromo-2-methyl-4,4a,9,9a-tetrahydroindeno[2,1-b][1,4]oxazin-3(2H)-one. To a solution of cis-(1S,2R)-1-amino-5-bromo-indan-2-ol (92.0 mg, 0.403 mmol) reported in general procedure V-E in THF (5 mL) at 0° C., was added sodium hydride (60.0%, 24.3 mg, 0.634 mmol). The reaction was stirred for 15 min, then added Ethyl 2-chloropropionate (0.0565 mL, 0.444 mmol), Stirred at rt for 5 min, then heated at 65 deg for 9 hr. The reaction was diluted with EtOAc and washed with saturated NH4Cl. Dried organic extract with sodium sulfate and purified by flash chromatography to give title compound. ES/MS: m/z=282.0, 284.0 $[M+H]^+$. $^1H$ NMR (400 MHz, Chloroform-d) δ 7.45 (s, 1H), 7.43 (d, J=8.1 Hz, 1H), 7.22-7.11 (m, 1H), 6.88 (s, 1H), 4.82 (td, J=5.1, 1.8 Hz, 0.5H, diastereomer), 4.75 (t, J=4.3 Hz, 0.5H, diastereomer), 4.71 (t, J=4.1 Hz, 0.5H, diastereomer), 4.60 (t, J=4.6 Hz, 0.5H, diastereomer), 4.26-4.07 (m, 1H), 3.25 (t, J=4.6 Hz, 0.3H, minor diastereomer), 3.22-3.17 (m, 0.7H, major diastereomer), 3.11 (s, 0.7H, major diastereomer), 3.07 (s, 0.3H, minor diastereomer), 1.55 (d, J=7.1 Hz, 1.5H, diastereomer), 1.40 (d, J=6.8 Hz, 1.5H, diastereomer).

Step 2. Rac-(4aS,9aR)-2-methyl-2,3,4,4a,9,9a-hexahydroindeno[2,1-b][1,4]oxazine (En-1). To a solution of rac-(4aS,9aR)-7-bromo-2-methyl-4,4a,9,9a-tetrahydroindeno[2,1-b][1,4]oxazin-3(2H)-one. (41.0 mg, 0.116 mmol) THF (3 mL) at 0° C., was added lithium aluminum hydride (2000 mmol/L, 0.233 mL, 0.465 mmol). After 1 hr, the reaction was cooled to 0 deg, diluted with $Et_2O$, added 18 uL water, 18 uL 15% NaOH, 60 uL water, then warmed to rt and stirred for 15 min. added $MgSO_4$, stirred for 30 min, filtered, rinsed with $Et_2O$, and concentrated to give title compound, which was carried onto the next step without purification. $^1H$ NMR (400 MHz, Chloroform-d) δ 7.33-7.29 (m, 4H), 7.19 (s, 1H), 4.95-4.78 (m, 1H), 4.76 (t, J=4.0 Hz, 0.5H, diastereomer), 4.61 (t, J=4.7 Hz, 0.5H, diastereomer), 4.23 (dt, J=11.2, 6.9 Hz, 1H), 4.02-3.82 (m, 1H), 3.32-3.16 (m, 1H), 3.16-3.06 (m, 1H), 1.56 (d, J=7.1 Hz, 2H), 1.40 (d, J=6.9 Hz, 2H).

General Procedure XV-E for the Synthesis of Intermediates Eo

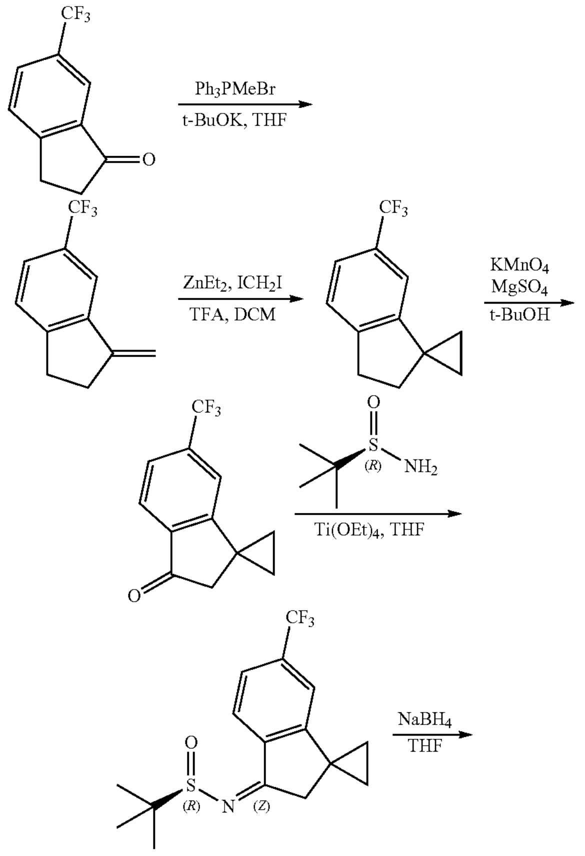

-continued

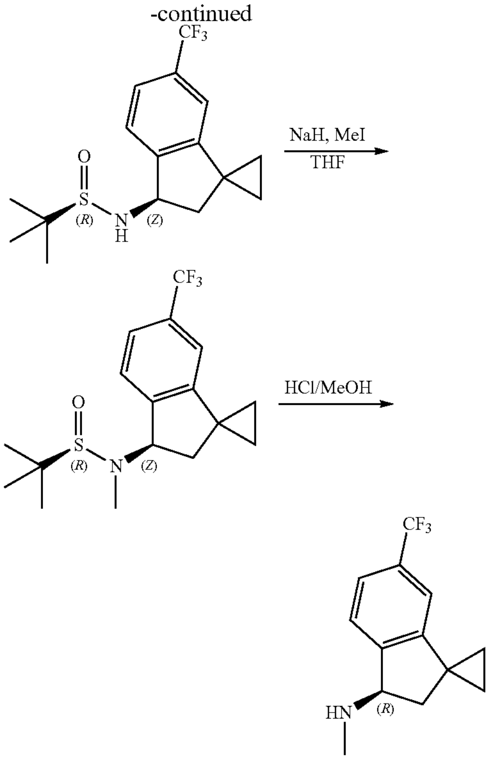

Eo-1

Step 1. 1-methylene-6-(trifluoromethyl)-2,3-dihydro-1H-indene. To a solution of 6-(trifluoromethyl)indan-1-one (5 g, 24.9 mmol, 1 eq.) in THF (100 mL) was added $Ph_3PMeBr$ (17.8 g, 49.9 mmol, 2 eq) and t-BuOK (1 M, 49.9 mL, 2 eq). The mixture was stirred at 25° C. for 12 hr. TLC indicated Reactant 1 was consumed completely and one new spot formed. The reaction was clean according to TLC. The reaction mixture was partitioned between $H_2O$ 50 mL and DCM 50 mL. The water phase was separated, extracted with DCM (50 mL×3). The combined organic phase was washed with brine (50 mL×3), dried over $Na_2SO_4$, filtered and concentrated under reduced pressure to give a residue. The residue was purified by flash silica gel chromatography to give 1-methylene-6-(trifluoromethyl)-2,3-dihydro-1H-indene. $^1H$ NMR (400 MHz, DMSO-$d_6$) δ 7.90 (s, 1H), 7.58-7.46 (m, 2H), 5.72 (t, J=2.6 Hz, 1H), 5.15 (t, J=2.2 Hz, 1H), 3.03-2.97 (m, 2H), 2.79 (tdd, J=2.3, 4.7, 9.3 Hz, 2H).

Step 2. 6'-(trifluoromethyl)-2',3'-dihydrospiro[cyclopropane-1,1'-indene]. To a solution of $ZnEt_2$ (1 M, 30.2 mL, 3 eq) in DCM (80 mL) was added $CH_2I_2$ (8.1 g, 30.2 mmol, 2.4 mL, 3 eq) at −78° C. The mixture was stirred at 0° C. for 30 min. TFA (3.4 g, 30.2 mmol, 2.2 mL, 3 eq) was added to the mixture at 0° C. The mixture was stirred at 0° C. for 30 min. 1-methylene-6-(trifluoromethyl)-2,3-dihydro-1H-indene (2 g, 10.0 mmol, 1 eq) in DCM (20 mL) was added to the mixture at 0° C. The mixture was stirred at 25° C. for 12 hr. TLC indicated Reactant 2 was consumed completely and many new spots formed. The reaction was messy according to TLC. The reaction mixture was partitioned between $NH_4Cl$ 50 mL and DCM 50 mL. The water phase was separated, extracted with DCM (50 mL×3). The combined organic phase was dried over $Na_2SO_4$, filtered and concentrated under reduced pressure to give a residue. The residue was purified by flash silica gel chromatography to give 6'-(trifluoromethyl)-2',3'-dihydrospiro[cyclopropane-1,1'- indene]. $^1$H NMR (400 MHz, DMSO-$d_6$) δ 7.43-7.36 (m, 2H), 7.05 (s, 1H), 3.04 (br t, J=7.6 Hz, 2H), 2.12 (t, J=7.7 Hz, 2H), 0.98 (s, 4H).

Step 3. 6'-(trifluoromethyl)spiro[cyclopropane-1,1'-inden]-3'(2'H)-one. To a solution of 6'-(trifluoromethyl)-2',3'-dihydrospiro[cyclopropane-1,1'-indene] (1.1 g, 5.1 mmol, 1 eq) in t-BuOH (36 mL) and 15% $MgSO_4$ (4 mL) ($H_2O$ solution) was added $KMnO_4$ (983.0 mg, 6.2 mmol, 1.2 eq) at 25° C. The mixture was stirred at 40° C. for 12 hr. TLC indicated one new spot formed. The reaction was clean according to TLC. The reaction was quenched the reaction with $Na_2SO_3$ aqueous. The mixture was filtered through celite and the filtrate was concentrate under reduced pressure. The reaction mixture was partitioned between $H_2O$ 40 mL and DCM 40 mL. The water phase was separated, extracted with DCM (40 mL×3). The combined organic phase was dried over $Na_2SO_4$, filtered and concentrated under reduced pressure to give a residue. The residue was purified by flash silica gel chromatography to give 6'-(trifluoromethyl)spiro[cyclopropane-1,1'-inden]-3'(2'H)-one. ES/MS: m/z=227.1 [M+H]$^+$. $^1$H NMR (400 MHz, DMSO-$d_6$) δ 7.78 (d, J=8.0 Hz, 1H), 7.67 (d, J=8.0 Hz, 1H), 7.59 (s, 1H), 2.83 (s, 2H), 1.31 (br d, J=5.9 Hz, 4H).

Step 4. (R,Z)-2-methyl-N-(6'-(trifluoromethyl)spiro[cyclopropane-1,1'-inden]-3'(2'H)-ylidene)propane-2-sulfinamide. To a solution of 6'-(trifluoromethyl)spiro[cyclopropane-1,1'-inden]-3'(2'H)-one (630 mg, 2.7 mmol, 1 eq) in THF (6 mL) was added (R)-2-methylpropane-2-sulfinamide (506.3 mg, 4.1 mmol, 1.5 eq) and $Ti(OEt)_4$ (1.2 g, 5.5 mmol, 1.1 mL, 2 eq). The mixture was stirred at 70° C. for 12 hr. LC-MS showed the desired compound was detected. TLC indicated Reactant 4 was consumed completely and one new spot formed. The reaction was clean according to TLC. The crude product (R,Z)-2-methyl-N-(6'-(trifluoromethyl)spiro[cyclopropane-1,1'-inden]-3'(2'H)-ylidene)propane-2-sulfinamide was used into the next step without further purification. ES/MS: m/z=330.1 [M+H]$^+$.

Step 5. (R)-2-methyl-N—((R)-6'-(trifluoromethyl)-2',3'-dihydrospiro[cyclopropane-1,1'-inden]-3'-yl)propane-2-sulfinamide. To a solution of (R,Z)-2-methyl-N-(6'-(trifluoromethyl)spiro[cyclopropane-1,1'-inden]-3'(2'H)-ylidene)propane-2-sulfinamide (900 mg, 2.7 mmol, 1 eq) in THF (4 mL) was added $NaBH_4$ (620.2 mg, 16.3 mmol, 6 eq) at 0° C. The mixture was stirred at 0° C. for 2 hr under $N_2$. LC-MS showed the desired compound was detected. TLC indicated Reactant 5 was consumed completely and one new spot formed. The reaction was clean according to TLC. The reaction mixture was partitioned between $NH_4Cl$ solution 20 mL and EtOAc 20 mL. The water phase was separated, extracted with EtOAc (20 mL×3). The combined organic phase was washed with brine (20 mL×3), dried over $Na_2SO_4$, filtered and concentrated under reduced pressure to give a residue. The residue was purified by flash silica gel chromatography to give (R)-2-methyl-N—((R)-6'-(trifluoromethyl)-2',3'-dihydrospiro[cyclopropane-1,1'-inden]-3'-yl)propane-2-sulfinamide. ES/MS: m/z=332.1 [M+H]$^+$. $^1$H NMR (400 MHz, DMSO-$d_6$) δ 7.72 (d, J=7.9 Hz, 1H), 7.53 (d, J=7.8 Hz, 1H), 7.12 (s, 1H), 5.98 (d, J=8.5 Hz, 1H), 2.35-2.23 (m, 2H), 1.26-1.22 (m, 1H), 1.15 (s, 9H), 1.12-1.08 (m, 1H), 0.93-0.87 (m, 1H), 0.76 (ddd, J=3.9, 6.3, 9.8 Hz, 1H).

Step 6. (R)—N,2-dimethyl-N—((R)-6'-(trifluoromethyl)-2',3'-dihydrospiro[cyclopropane-1,1'-inden]-3'-yl)propane-2-sulfinamide. To a solution of (R)-2-methyl-N—((R)-6'-(trifluoromethyl)-2',3'-dihydrospiro[cyclopropane-1,1'-inden]-3'-yl)propane-2-sulfinamide (380 mg, 1.1 mmol, 1 eq) in THF (2 mL) was added NaH (91.7 mg, 2.2 mmol, 60% purity, 2 eq.) at 0° C. The mixture was stirred at 0° C. for 30 min. MeI (162.7 mg, 1.1 mmol, 71.3 μL, 1 eq) was added to the mixture. The mixture was stirred at 25° C. for 12 hr. LC-MS showed the desired compound was detected. The reaction mixture was partitioned between $NH_4Cl$ 10 mL and EtOAc 10 mL. The water phase was separated, extracted with EtOAc (10 mL×3). The combined organic phase was washed with brine (10 mL×3), dried over $Na_2SO_4$, filtered and concentrated under reduced pressure to give (R)—N,2-dimethyl-N—((R)-6'-(trifluoromethyl)-2',3'-dihydrospiro[cyclopropane-1,1'-inden]-3'-yl)propane-2-sulfinamide. ES/MS: m/z=346.2 [M+H]$^+$.

Step 7. (R)—N-methyl-6'-(trifluoromethyl)-2',3'-dihydrospiro[cyclopropane-1,1'-inden]-3'-amine Eo-1. The solution of (R)—N,2-dimethyl-N—((R)-6'-(trifluoromethyl)-2',3'-dihydrospiro[cyclopropane-1,1'-inden]-3'-yl)propane-2-sulfinamide (480 mg, 1.3 mmol, 1 eq) in HCl/MeOH (3 mL) (4M) was stirred at 25° C. for 1 hr. LC-MS showed the desired compound was detected. The reaction mixture was concentrated under reduced pressure to remove solvent. The residue was purified by prep-HPLC to give (R)—N-methyl-6'-(trifluoromethyl)-2',3'-dihydrospiro[cyclopropane-1,1'-inden]-3'-amine. ES/MS: m/z=242.2 [M+H]$^+$. $^1$H NMR (400 MHz, DMSO-$d_6$) δ 9.60 (br s, 2H), 7.92 (d, J=7.9 Hz, 1H), 7.63 (d, J=7.3 Hz, 1H), 7.26 (s, 1H), 4.98 (dd, J=5.4, 8.1 Hz, 1H), 2.56-2.51 (m, 4H), 2.30 (dd, J=5.3, 14.0 Hz, 1H), 1.23-1.16 (m, 1H), 1.15-1.09 (m, 2H), 1.08-1.03 (m, 1H).

General Procedure XVI-E for the Synthesis of Intermediates Ep

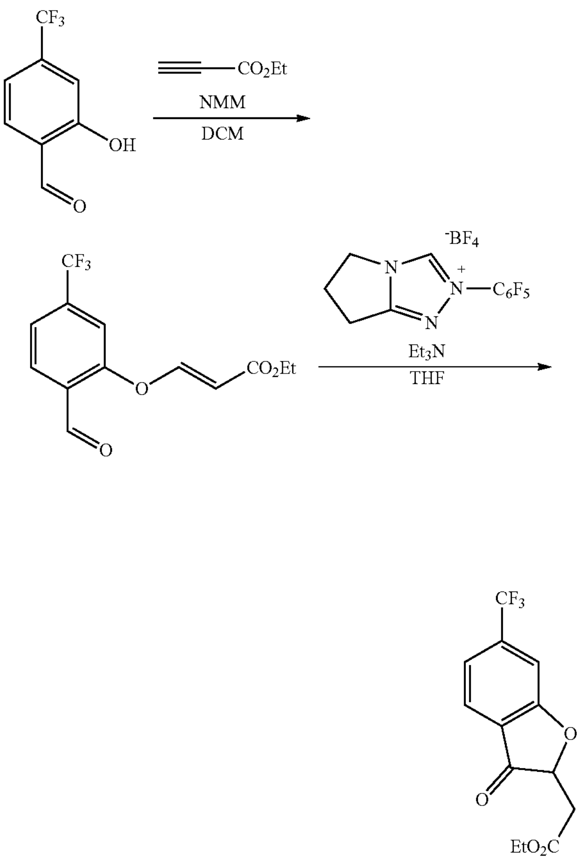

-continued

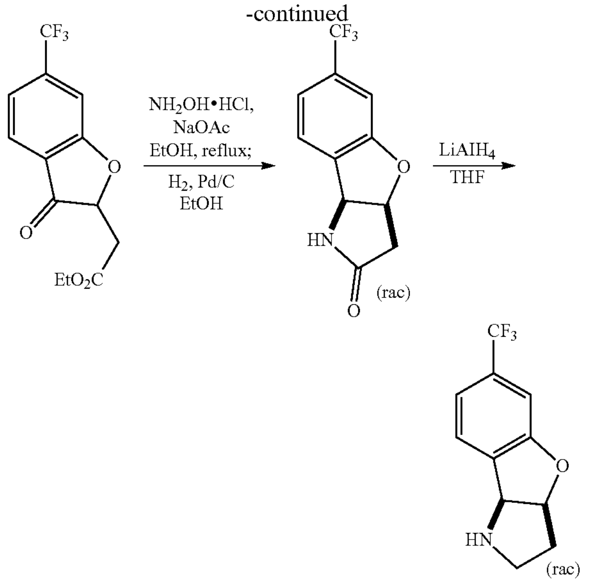

Ep-1

Step 1. ethyl (E)-3-(2-formyl-5-(trifluoromethyl)phenoxy)acrylate. To a solution of 2-hydroxy-4-(trifluoromethyl)benzaldehyde (2.5 g, 13.1 mmol) and ethyl propiolate (1.47 mL, 14.5 mmol) in DCM (50 mL) at 0° C. was added N-methylmorpholine (0.15 mL, 1.31 mmol). The reaction mixture was warmed to room temperature and stirred for 2 hours, then concentrated. Purification by silica gel flash column chromatography afforded ethyl (E)-3-(2-formyl-5-(trifluoromethyl)phenoxy)acrylate. ES/MS: m/z=288.9 $[M+H]^+$. $^1H$ NMR (400 MHz, Chloroform-d) δ 10.42 (d, J=0.8 Hz, 1H), 8.05 (dd, J=8.1, 1.0 Hz, 1H), 7.83 (d, J=12.2 Hz, 1H), 7.68-7.52 (m, 1H), 7.50-7.32 (m, 1H), 5.73 (d, J=12.2 Hz, 1H), 4.24 (q, J=7.1 Hz, 2H), 1.31 (t, J=7.1 Hz, 3H).

Step 2. ethyl 2-(3-oxo-6-(trifluoromethyl)-2,3-dihydrobenzofuran-2-yl)acetate. To a degassed solution of 2-(2,3,4,5,6-pentafluorophenyl)-6,7-dihydro-5H-pyrrolo[2,1-c][1,2,4]triazol-2-ium tetrafluoroborate (128 mg, 0.35 mmol) in THF (20 mL) was added triethylamine (0.05 mL, 0.35 mmol). After stirring for 5 minutes, a solution of ethyl (E)-3-(2-formyl-5-(trifluoromethyl)phenoxy)acrylate (1.7 g, 5.9 mmol) in degassed THF (40 mL) was added slowly. After stirring for 30 minutes, the reaction was quenched with sat. aq. $NH_4Cl$, diluted with EtOAc, and transferred to a separatory funnel. The organic layer was separated, washed with brine, dried over $MgSO_4$, filtered, and concentrated. Purification by silica gel flash column chromatography afforded ethyl 2-(3-oxo-6-(trifluoromethyl)-2,3-dihydrobenzofuran-2-yl)acetate. ES/MS: m/z=288.9 $[M+H]^+$. $^1H$ NMR (400 MHz, Chloroform-d) δ 7.81 (d, J=8.0 Hz, 1H), 7.40 (s, 1H), 7.36 (d, J=8.1 Hz, 1H), 4.91 (dd, J=6.5, 4.0 Hz, 1H), 4.21-4.09 (m, 2H), 3.13 (dd, J=17.3, 4.1 Hz, 1H), 2.95 (dd, J=17.3, 6.5 Hz, 1H), 1.18 (t, J=7.1 Hz, 3H).

Step 3. (3aS,8bS)-6-(trifluoromethyl)-1,3,3a,8b-tetrahydro-2H-benzofuro[3,2-b]pyrrol-2-one. To a solution of ethyl 2-(3-oxo-6-(trifluoromethyl)-2,3-dihydrobenzofuran-2-yl)acetate (1.6 g, 5.55 mmol) in EtOH (11 mL) was added hydroxylamine hydrochloride (770 mg, 11.1 mmol) and sodium acetate (911 mg, 11.1 mmol). The mixture was heated to reflux for 1 hour, then cooled to room temperature and filtered, washing with additional EtOH. The filtrate as concentrated then resuspended in EtOH (11 mL) and Pd/C (10% w/w, was added (1.47 g, 1.39 mmol). The atmosphere was flushed with $H_2$ (1 atm) and the reaction was allowed to stir overnight. After purging with argon, the reaction mixture was filtered over celite and concentrated. Purification by silica gel flash column chromatography afforded racemic (3aS,8bS)-6-(trifluoromethyl)-1,3,3a,8b-tetrahydro-2H-benzofuro[3,2-b]pyrrol-2-one. ES/MS: m/z=243.9 $[M+H]^+$. $^1H$ NMR (400 MHz, Chloroform-d) δ 7.40 (d, J=7.7 Hz, 1H), 7.21 (ddd, J=7.7, 1.6, 0.8 Hz, 1H), 7.09 (t, J=1.0 Hz, 1H), 5.46 (td, J=7.0, 1.6 Hz, 1H), 5.24 (d, J=6.9 Hz, 1H), 2.87 (d, J=6.9 Hz, 1H), 2.78 (dd, J=18.5, 1.7 Hz, 1H).

Step 4. Cis-(3aS,8bS)-6-(trifluoromethyl)-2,3,3a,8b-tetrahydro-1H-benzofuro[3,2-b]pyrrole (Ep-1). To a solution of (3aS,8bS)-6-(trifluoromethyl)-1,3,3a,8b-tetrahydro-2H-benzofuro[3,2-b]pyrrol-2-one (300 mg, 1.23 mmol) in THF (10 mL) at 0° C. was added $LiAlH_4$ (2.0 M in THF, 1.85 mL, 3.7 mmol). The reaction mixture was allowed to warm to room temperature and stir overnight. The reaction mixture was quenched by addition of a small portion of $H_2O$, 2.0 M NaOH, followed by dilution with EtOAc and drying with $MgSO_4$. Filtration of the resulting slurry followed by concentration under reduced pressure and by purification by silica gel flash column chromatography afforded cis-(3aS,8bS)-6-(trifluoromethyl)-2,3,3a,8b-tetrahydro-1H-benzofuro[3,2-b]pyrrole. ES/MS: m/z=230.0 $[M+H]^+$. $^1H$ NMR (400 MHz, Chloroform-d) δ 7.74 (d, J=7.8 Hz, 1H), 7.19 (d, J=8.0 Hz, 1H), 7.05 (s, 1H), 5.57 (d, J=6.5 Hz, 1H), 5.45 (t, J=5.8 Hz, 1H), 4.06 (ddd, J=11.3, 8.3, 1.5 Hz, 1H), 3.55 (td, J=11.5, 6.2 Hz, 1H), 2.56-2.40 (m, 2H).

General Procedure XVII-E for the Synthesis of Intermediates Eq

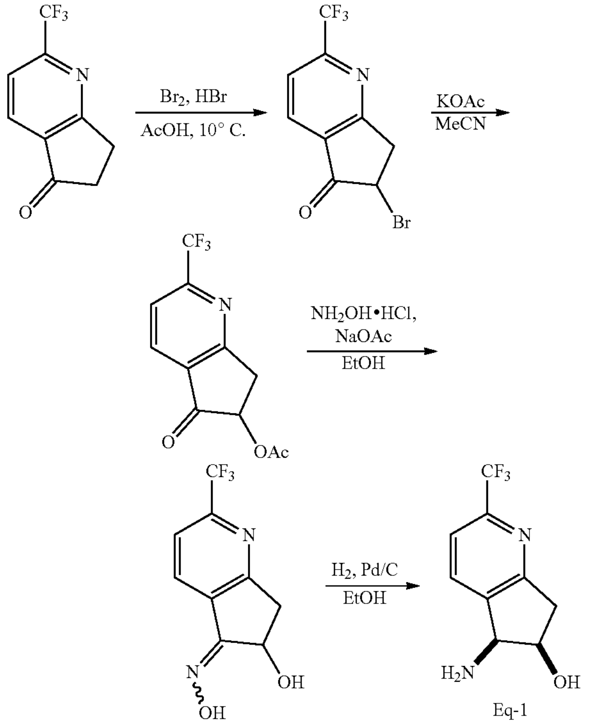

Eq-1
(±)

Step 1: 6-bromo-2-(trifluoromethyl)-6,7-dihydro-5H-cyclopenta[b]pyridin-5-one. To a solution of 2-(trifluoromethyl)-6,7-dihydro-5H-cyclopenta[b]pyridin-5-one (500 mg, 2.5 mmol) in HBr (30% in AcOH, 3.3 mL) was added bromine (0.12 mL, 2.2 mmol) at 10° C. After stirring for 1.5 hours, the mixture was diluted with DCM and EtOAc and carefully neutralized with sat. aq. $NaHCO_3$. The organic layer was separated, washed with brine, dried over $MgSO_4$, filtered, and concentrated to afford 6-bromo-2-(trifluoromethyl)-6,7-dihydro-5H-cyclopenta[b]pyridin-5-one which was used without further purification. ES/MS: m/z=279.8 $[M+H]^+$. $^1H$ NMR (400 MHz, Chloroform-d) δ 8.31 (d, J=8.0 Hz, 1H), 7.79 (d, J=8.0 Hz, 1H), 4.78 (dd, J=7.7, 3.0 Hz, 1H), 4.04 (dd, J=19.2, 7.7 Hz, 1H), 3.64 (dd, J=19.2, 3.0 Hz, 1H).

Step 2: 5-oxo-2-(trifluoromethyl)-6,7-dihydro-5H-cyclopenta[b]pyridin-6-yl acetate. To a solution of 6-bromo-2-(trifluoromethyl)-6,7-dihydro-5H-cyclopenta[b]pyridin-5-one (600 mg, 2.1 mmol) in acetonitrile (15 mL) was added KOAc (420 mg, 4.3 mmol). After stirring overnight, the mixture was concentrated, resuspended in DCM, and washed with H2O. The mixture was dried over $MgSO_4$, filtered, and concentrated. Purification by silica gel flash column chromatography afforded 5-oxo-2-(trifluoromethyl)-6,7-dihydro-5H-cyclopenta[b]pyridin-6-yl acetate. ES/MS: m/z=259.9 $[M+H]^+$. $^1H$ NMR (400 MHz, Chloroform-d) δ 8.25 (d, J=7.9 Hz, 1H), 7.77 (d, J=7.9 Hz, 1H), 5.47 (dd, J=8.4, 5.0 Hz, 1H), 3.93-3.79 (m, 1H), 3.32 (dd, J=18.0, 5.0 Hz, 1H), 2.20 (s, 3H).

Step 3: 6-hydroxy-2-(trifluoromethyl)-6,7-dihydro-5H-cyclopenta[b]pyridin-5-one oxime. To a solution of 5-oxo-2-(trifluoromethyl)-6,7-dihydro-5H-cyclopenta[b]pyridin-6-yl acetate (320 mg, 1.23 mmol) in EtOH (3 mL) was added hydroxylamine hydrochloride (515 mg, 7.4 mmol) and sodium acetate (610 mg, 7.4 mmol). The mixture was heated to reflux overnight, then cooled to room temperature, filtered, and concentrated. Purification by silica gel flash column chromatography afforded 6-hydroxy-2-(trifluoromethyl)-6,7-dihydro-5H-cyclopenta[b]pyridin-5-one oxime. ES/MS: m/z=233.0 $[M+H]^+$.

Step 4: cis-5-amino-2-(trifluoromethyl)-6,7-dihydro-5H-cyclopenta[b]pyridin-6-ol (Eq-1). A suspension of 6-hydroxy-2-(trifluoromethyl)-6,7-dihydro-5H-cyclopenta[b]pyridin-5-one oxime (220 mg, 0.95 mmol) and palladium on carbon (10% w/w, 250 mg, 0.24 mmol) in EtOH (5 mL) was stirred under an atmosphere of hydrogen overnight. The mixture was filtered to afford 5-amino-2-(trifluoromethyl)-6,7-dihydro-5H-cyclopenta[b]pyridin-6-ol. ES/MS: m/z=219.0 $[M+H]^+$.

General Procedure XVIII-E for the Synthesis of Intermediates Er.

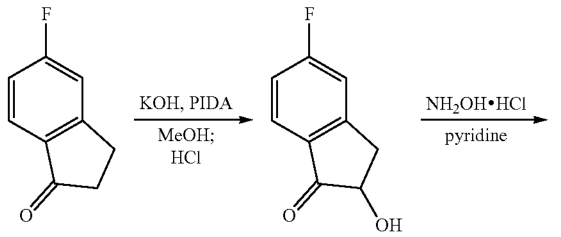

-continued

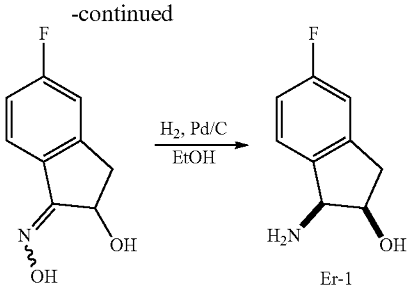

Er-1
(±)

Step 1: 5-fluoro-2-hydroxy-indan-1-one. A solution of 5-fluoroindan-1-one (2.15 g, 14.3 mmol) in MeOH (50 mL) was added KOH (8.8 g, 158 mmol) at 0° C. After stirring for 30 minutes, iodobenzene diacetate (5.53 g, 17.2 mmol) was added. The mixture was stirred for one hour, then warmed to room temperature and stirred for an additional 30 minutes, then concentrated. The residue was suspended in $Et_2O$ and washed with 3% aq. $NaHCO_3$ and water. The ethereal solution was concentrated, then suspended in THF (25 mL) and 6N HCl (3 mL) was added. After stirring for 30 minutes, the mixture was extracted with $Et_2O$ and the organic extract was washed with sat. aq. $NaHCO_3$ and brine. The organic extract was dried over $MgSO_4$, filtered, and concentrated to afford 5-fluoro-2-hydroxy-indan-1-one. ES/MS: m/z=167.0 $[M+H]^+$.

Step 2: 5-fluoro-2-hydroxy-indan-1-one oxime. Hydroxylamine hydrochloride (276 mg, 3.97 mmol) was added to a solution of 5-fluoro-2-hydroxy-indan-1-one (600 mg, 3.61 mmol) in pyridine (15 mL). after stirring for 1 hour, the mixture was concentrated and purified by silica gel flash column chromatography to afford 5-fluoro-2-hydroxy-indan-1-one oxime as a mixture of (E) and (Z) isomers. ES/MS: m/z=182.0 $[M+H]^+$.

Step 3: cis-1-amino-5-fluoro-indan-2-ol (Er-1). A suspension of 5-fluoro-2-hydroxy-indan-1-one oxime (600 mg, 3.31 mmol) and palladium on carbon (10% w/w, 350 mg, 0.33 mmol) in EtOH (12 mL) was stirred under and atmosphere of hydrogen overnight. The mixture was filtered over Celite and concentrated to afford cis-1-amino-5-fluoro-indan-2-ol. ES/MS: m/z =168.0 $[M+H]^+$.

General Procedure XIX-E for the Synthesis of Intermediates Es.

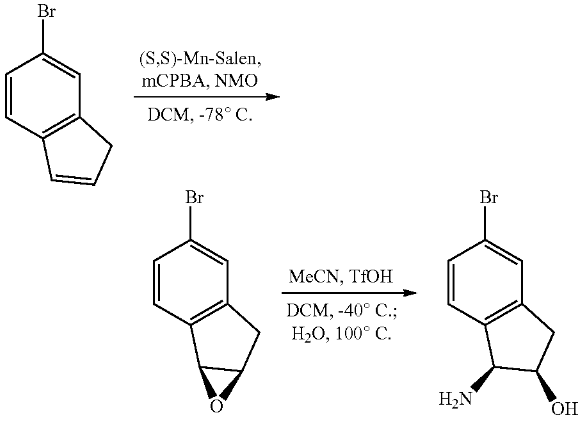

Es-1

Step 1: (1aS,6aR)-4-bromo-1a,6a-dihydro-6H-indeno[1,2-b]oxirene. To a solution of 6-bromo-1H-indene (5.0 g, 25.6 mmol) in DCM (20 mL) at −78° C. was added N-methylmorpholine N-oxide monohydrate (15 g, 128 mmol) and (S,S)-(+)—N,N'-Bis(3,5-di-tert-butylsalicylidene)-1,2-cyclohexanediaminomanganese(III) chloride (1.1 g, 1.8 mmol). 3-chloroperbenzoic acid (8.8 g, 51 mmol) portionwise. After stirring for 2 hours, the mixture was warmed to 0° C. and quenched via addition of 2M Aq. NaOH. The organic layer was separated, washed with brine, and filtered over celite to afford crude (1aS,6aR)-4-bromo-1a,6a-dihydro-6H-indeno[1,2-b]oxirene, which was used without further purification.

Step 2: (1S,2R)-1-amino-5-bromo-2,3-dihydro-1H-inden-2-ol (Es-1). To a solution of crude (1aS,6aR)-4-bromo-1a,6a-dihydro-6H-indeno[1,2-b]oxirene (4.9 g, 23 mmol) in acetonitrile (70 mL) at −40° C. was added trifluoromethanesulfonic acid (4.1 mL, 46 mmol) dropwise. The mixture was warmed to room temperature and stirred for 1 hour. Water (60 mL) was added and the mixture was stirred for 15 minutes before removal of the acetonitrile under reduced pressure. The aqueous suspension was then heated to 100° C. overnight. After cooling to room temperature, the mixture was diluted with DCM and the aqueous layer was separated. Following basification to pH 12 with 6M aq. NaOH, the aqueous layer was extracted with ethyl acetate. The organic extract was dried over $MgSO_4$, filtered, and concentrated. Recrystallization of the crude residue from toluene afforded (1S,2R)-1-amino-5-bromo-2,3-dihydro-1H-inden-2-ol. ES/MS: m/z=228.0 $[M+H]^+$. $^1H$ NMR (400 MHz, Methanol-$d_4$) δ 7.42-7.35 (m, 2H), 7.32 (d, J=8.0 Hz, 1H), 4.44-4.38 (m, 1H), 4.15-4.09 (m, 1H), 3.10-3.06 (m, 1H), 2.92-2.87 (m, 1H).

Es-2

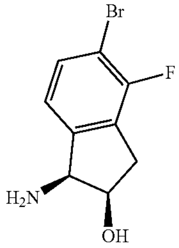

(1S,2R)-1-amino-5-bromo-4-fluoro-2,3-dihydro-1H-inden-2-ol (Es-2). Prepared following procedure XIX-E starting with 6-bromo-7-fluoro-1H-indene (prepared via reduction of 5-bromo-4-fluoro-2,3-dihydro-1H-inden-1-one with NaBH4 followed by elimination with p-TsOH). $^1H$ NMR (400 MHz, Chloroform-d) δ 7.48-7.41 (m, 1H), 7.01 (d, J=7.9 Hz, 1H), 4.44 (td, J=5.4, 2.8 Hz, 1H), 4.34 (dd, J=5.4, 1.1 Hz, 1H), 3.09 (qd, J=16.9, 4.1 Hz, 2H).

Es-3

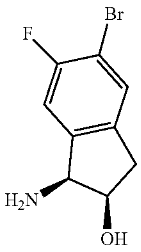

(1S,2R)-1-amino-5-bromo-6-fluoro-2,3-dihydro-1H-inden-2-ol (Es-3). Prepared following procedure XIX-E starting with 6-bromo-5-fluoro-1H-indene (prepared via reduction of 5-bromo-6-fluoro-2,3-dihydro-1H-inden-1-one with NaBH4 followed by elimination with p-TsOH). $^1H$ NMR (400 MHz, Chloroform-d) δ 7.45-7.40 (m, 1H), 7.09 (d, J=8.2 Hz, 1H), 4.42 (td, J=5.3, 2.6 Hz, 1H), 4.30 (d, J=5.3 Hz, 1H), 3.28-3.02 (m, 1H), 2.99-2.74 (m, 1H).

Es-4

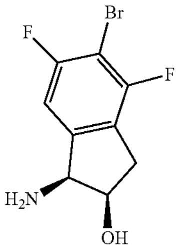

(1S,2R)-1-amino-5-bromo-4,6-difluoro-2,3-dihydro-1H-inden-2-ol (Es-4). Prepared following procedure XIX-E starting with 6-bromo-5,7-difluoro-1H-indene (prepared via reduction of 5-bromo-6-fluoro-2,3-dihydro-1H-inden-1-one with NaBH4 followed by elimination with p-TsOH). $^1H$ NMR (400 MHz, Chloroform-d) δ 6.97 (s, 1H), 4.76 (t, J=4.1 Hz, 1H), 4.60 (td, J=4.1, 1.3 Hz, 1H), 4.20 (s, 2H), 3.26-3.19 (m, 2H).

Es-5

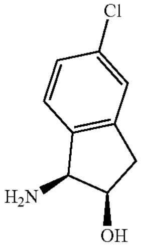

(1S,2R)-1-amino-5-chloro-2,3-dihydro-1H-inden-2-ol (Es-5). Prepared following procedure XIX-E starting with 6-chloro-1H-indene. ES/MS: m/z=184.5.

Es-6

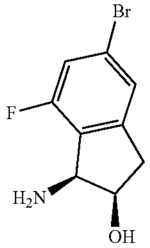

(1S,2R)-1-amino-7-fluoro-5-bromo-2,3-dihydro-1H-inden-2-ol (Es-6). Prepared following general procedure XIX-E starting with 4-fluoro-6-bromo-1H-indene. ES/MS: m/z=248.0.

Es-7

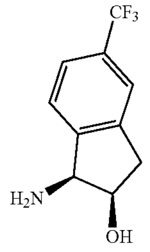

(1S,2R)-1-amino-5-(trifluoromethyl)-2,3-dihydro-1H-inden-2-ol (Es-7). Prepared following general procedure XIX-E starting with 6-(trifluoromethyl)-1H-indene. The desired product was obtained after SFC purification (column: DAICEL CHIRALPAK AD (250 mm*30 mm, 10 um); mobile phase: [A: $CO_2$; B: MeOH (0.1% $NH_3H_2O$)]; B %: 20%, 3.50 min). ES/MS: m/z=218.1.

General Procedure XX-E for the Synthesis of Intermediates Et.

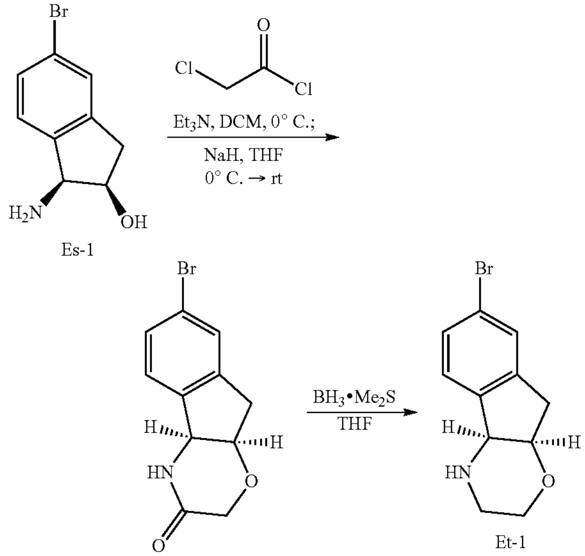

Es-1

Et-1

(4aS,9aR)-7-bromo-4,4a,9,9a-tetrahydroindeno[2,1-b][1,4]oxazin-3-one. To a stirred suspension of (1S,2R)-1-amino-5-bromo-2,3-dihydro-1H-inden-2-ol Es-1 (500 mg, 2.2 mmol) and triethylamine (0.43 mL, 3.1 mmol) in DCM (7 mL) at 0° C. was added chloroacetyl chloride (0.21 mL, 2.6 mmol) dropwise. After stirring for 1 hour, the reaction was quenched with water. The mixture was transferred to a separatory funnel and extracted with EtOAc. The organic extract was washed with brine, dried over $MgSO_4$, filtered, and concentrated under reduced pressure. The resulting solid was suspended in dry THF (7 mL) and NaH (60% dispersion in mineral oil, 170 mg, 4.4 mmol) was added at 0° C. The mixture was warmed to room temperature and allowed to stir for 3 hours. After careful quenching with water, the mixture was transferred to a separatory funnel and extracted with EtOAc. The organic extract was washed with brine, dried over $MgSO_4$, filtered, and concentrated under reduced pressure. Purification of the crude residue by silica gel column chromatography afforded (4aS,9aR)-7-bromo-4,4a,9,9a-tetrahydroindeno[2,1-b][1,4]oxazin-3-one. ES/MS: m/z=267.9 $[M+H]^+$. $^1H$ NMR (400 MHz, Chloroform-d) δ 7.42 (d, J=10.7 Hz, 2H), 7.17 (d, J=7.9 Hz, 1H), 4.72 (t, J=4.1 Hz, 1H), 4.53 (t, J=4.5 Hz, 1H), 4.16 (s, 2H), 3.21 (dd, J=17.0, 4.9 Hz, 1H), 3.07 (d, J=17.0 Hz, 1H).

(4aS,9aR)-7-bromo-2,3,4,4a,9,9a-hexahydroindeno[2,1-b][1,4]oxazine (Et-1). Borane dimethyl sulfide complex (0.98 mL, 10 mmol) was added to a solution of (4aS,9aR)-7-bromo-4,4a,9,9a-tetrahydroindeno[2,1-b][1,4]oxazin-3-one (457 mg, 1.7 mmol) in THF (6 mL) at 0° C. The mixture was warmed to room temperature and allowed to stir overnight. The reaction was then cooled to 0° C. and quenched by slow addition of MeOH until the evolution of gas was no longer detected. HCl (4.0M in dioxane, 1.7 mL, 6.8 mmol) was then added and the mixture was allowed to stir for a further 30 minutes. The mixture was concentrated to afford (4aS,9aR)-7-bromo-2,3,4,4a,9,9a-hexahydroindeno[2,1-b][1,4]oxazine as the hydrochloride salt. ES/MS: m/z =253.9 $[M+H]^+$. $^1H$ NMR (400 MHz, Chloroform-d) δ 7.47-7.37 (m, 2H), 7.36-7.24 (m, 1H), 4.42-4.19 (m, 2H), 3.77-3.54 (m, 2H), 3.07-2.64 (m, 4H).

Et-2

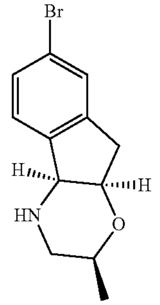

(2S,4aS,9aR)-7-bromo-2-methyl-2,3,4,4a,9,9a-hexahydroindeno[2,1-b][1,4]oxazine (Et-2). Prepared according to general procedure XX-E (KOtBu was used in place of NaH) starting with (R)-2-chloropropanoyl chloride and (1S,2R)-1-amino-5-bromo-2,3-dihydro-1H-inden-2-ol (Es-1). ES/MS: m/z=267.9 $[M+H]^+$.

Et-3

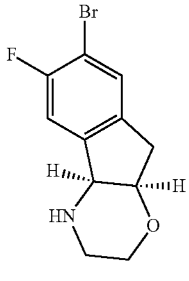

(4aS,9aR)-7-bromo-8-fluoro-2,3,4,4a,9,9a-hexahydroindeno[2,1-b][1,4]oxazine (Et-3). Prepared following procedure XX-E starting with (1S,2R)-1-amino-5-bromo-6-fluoro-2,3-dihydro-1H-inden-2-ol Es-3. ES/MS: m/z=272.0, 274.8 $[M+H]^+$.

Et-4

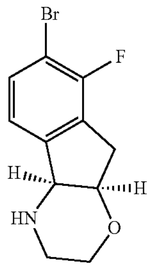

(4aS,9aR)-7-bromo-8-fluoro-2,3,4,4a,9,9a-hexahydroindeno[2,1-b][1,4]oxazine (Et-4). Prepared following procedure XX-E starting with (1S,2R)-1-amino-5-bromo-4-fluoro-2,3-dihydro-1H-inden-2-ol Es-2. ES/MS: m/z=271.971, 273.909 [M+H]$^+$.

Et-5

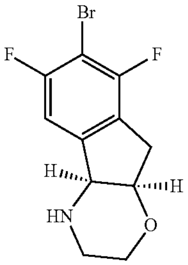

(4aS,9aR)-7-bromo-6,8-difluoro-2,3,4,4a,9,9a-hexahydroindeno[2,1-b][1,4]oxazine (Et-5). Prepared following procedure XX-E starting with (1S,2R)-1-amino-5-bromo-4,6-difluoro-2,3-dihydro-1H-inden-2-ol Es-4. ES/MS: m/z=290.0, 291.8 [M+H]$^+$.

Et-6

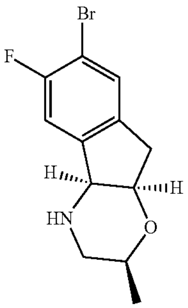

(2S,4aS,9aR)-7-bromo-6-fluoro-2-methyl-2,3,4,4a,9,9a-hexahydroindeno[2,1-b][1,4]oxazine (Et-6). Prepared according to general procedure XX-E (KOtBu was used in place of NaH) starting with (R)-2-chloropropanoyl chloride and (1S,2R)-1-amino-5-bromo-6-fluoro-2,3-dihydro-1H-inden-2-ol Es-3. ES/MS: m/z=286.0, 288.0 [M+H]$^+$.

Et-7

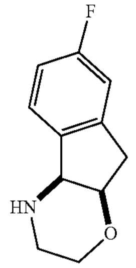

(±)

Cis-(4aS,9aR)-7-fluoro-2,3,4,4a,9,9a-hexahydroindeno[2,1-b][1,4]oxazine (Et-7). Prepared according to general procedure XX-E starting with cis-1-amino-5-fluoro-indan-2-ol Er-1. ES/MS: m/z=194.0 [M+H]$^+$.

Et-8

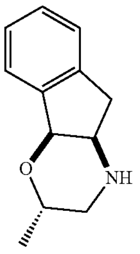

(2S)-2-methyl-2,3,4,4a,5,9b-hexahydroindeno[1,2-b][1,4]oxazine (Et-8). Prepared according to general procedure XX-E (KOtBu was used in place of NaH) starting with commercial cis-2-amino-2,3-dihydro-1H-inden-1-ol and (R)-2-chloropropanoyl chloride (prepared by mixing (2R)-2-chloropropanoic acid, oxalyl chloride and $DMF_{cat.}$ in DCM at 0° C., followed by concentrating at 0° C.). ES/MS: m/z=190.1 [M+H]$^+$.

General Procedure XXI-E for the Synthesis of Intermediates Eu:

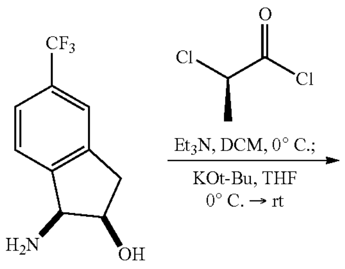

-continued

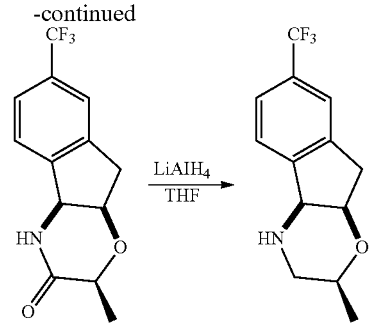

Eu-1

Step 1: (2S)-2-methyl-7-(trifluoromethyl)-4,4a,9,9a-tetrahydroindeno[2,1-b][1,4]oxazin-3(2H)-one. To a solution of 1-amino-5-(trifluoromethyl)indan-2-ol (prepared according to general procedure V-E) (120 mg, 0.55 mmol) and triethylamine (0.1 mL, 0.72 mmol) in DCM (4 mL) was added (R)-2-chloropropanoyl chloride (prepared by mixing (R)-2-chloropropionic acid (66 mg, 1.5 mmol), oxalyl chloride (2.0 M in DCM, 0.35 mL, 0.72 mmol) and DMF (5 μL) in DCM (4 mL) at 0° C., followed by concentrating at 0° C.) dropwise. After stirring for 15 minutes, water and EtOAc were added, and the mixture was transferred to a separatory funnel. The organic layer was separated, washed with brine, dried over $MgSO_4$, filtered, and concentrated. The resulting residue was suspended in THF (4 mL) and potassium tert-butoxide (1.0 M in THF, 1.2 mL, 1.2 mmol) was added dropwise at 0° C. Following warming to room temperature and stirring for 1 hour, the mixture was quenched with sat. aq. $NH_4Cl$ and diluted with EtOAc. The organic layer was separated, washed with brine, and dried over $MgSO_4$. Purification by silica gel flash column chromatography afforded (2S)-2-methyl-7-(trifluoromethyl)-4,4a,9,9a-tetrahydroindeno[2,1-b][1,4]oxazin-3(2H)-one. ES/MS: m/z=272.0 $[M+H]^+$.

Step 2: (2S)-2-methyl-7-(trifluoromethyl)-2,3,4,4a,9,9a-hexahydroindeno[2,1-b][1,4]oxazine (Eu-1). To a solution of (2S)-2-methyl-7-(trifluoromethyl)-4,4a,9,9a-tetrahydroindeno[2,1-b][1,4]oxazin-3(2H)-one (100 mg, 0.37 mmol) in THF (4 mL) was added LiAlH4 (2.0 M in THF, 0.55 mL, 1.1 mmol). The mixture was stirred overnight at room temperature before being cooled to 0° C. and quenched by slow addition of 2M NaOH until the evolution of gas was no longer detected. $MgSO_4$ was added and the mixture was filtered over celite, washing with EtOAc. The resulting filtrate was concentrated under reduced pressure to afford (2S)-2-methyl-7-(trifluoromethyl)-2,3,4,4a,9,9a-hexahydroindeno[2,1-b][1,4]oxazine. ES/MS: m/z=258.0 $[M+H]^+$.

Eu-2

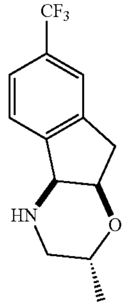

(2R)-2-methyl-7-(trifluoromethyl)-2,3,4,4a,9,9a-hexahydroindeno[2,1-b][1,4]oxazine (Eu-2). Prepared according to general procedure XXI-E starting with (S)-2-chloropropionic acid and 1-amino-5-(trifluoromethyl)indan-2-ol (prepared according to general procedure V-E). ES/MS: m/z=258.0 $[M+H]^+$.

Eu-3

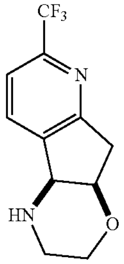

(Rac)-(2S,7R)-11-(trifluoromethyl)-6-oxa-3,10-diazatricyclo[7.4.0.02,7]trideca-1(13), 9,11-triene (Eu-3). Prepared according to general procedure XXI-E starting with 5-amino-2-(trifluoromethyl)-6,7-dihydro-5H-cyclopenta[b]pyridin-6-ol Eq-1 and chloroacetyl chloride. ES/MS: m/z=245.0 $[M+H]^+$.

General Procedure XXII-E for the Synthesis of Intermediates Ev:

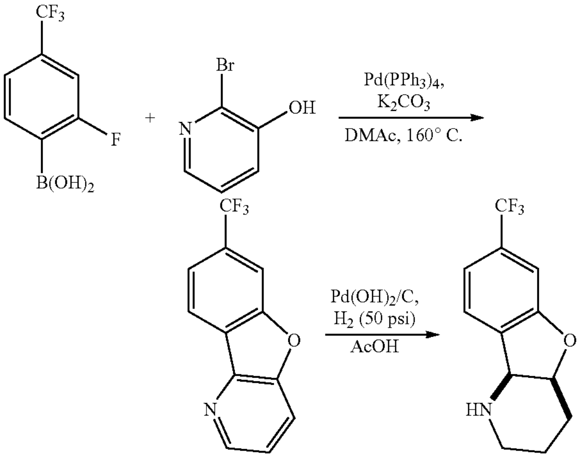

Ev-1
(±)

Step 1: 7-(trifluoromethyl)benzofuro[3,2-b]pyridine. 2-bromopyridin-3-ol (480 mg, 2.8 mmol), [2-fluoro-4-(trifluoromethyl)phenyl]boronic acid (630 mg, 3.0 mmol), $Pd(PPh_3)_4$ (160 mg, 0.14 mmol), and $K_2CO_3$ (1.5 g, 11 mmol) were stirred in DMAc (5.5 mmol) at 160° C. overnight. After cooling to room temperature, the mixture was diluted with EtOAc, water. The organic layer was separated, and washed with 10% Aq. LiCl, dried over $MgSO_4$, filtered, and concentrated. The crude residue was purified by flash column chromatography to afford 7-(trifluoromethyl)benzofuro[3,2-b]pyridine. ES/MS: m/z=237.9 $[M+H]^+$. $^1H$ NMR (400 MHz, Methanol-d4) δ 8.70 (dd, J=4.9, 1.3 Hz, 1H), 8.44-8.37 (m, 1H), 8.17 (dd, J=8.5, 1.3 Hz, 1H), 8.11-8.03 (m, 1H), 7.81 (dt, J=8.1, 1.0 Hz, 1H), 7.65 (dd, J=8.5, 4.8 Hz, 1H).

Step 2: cis-7-(trifluoromethyl)-1,2,3,4,4a,9b-hexahydrobenzofuro[3,2-b]pyridine (Ev-1). 7-(trifluoromethyl)benzofuro[3,2-b]pyridine (110 mg, 0.46 mmol) was suspended in AcOH (2 mL) and $Pd(OH)_2/C$ (20% w/w, 326 mg, 0.46 mmol) was added. The mixture was shaken in a Parr reactor under $H_2$ (50 psi) overnight. Following filtration over celite and concentration, the crude residue was suspended in EtOAc and washed with sat. aq. $NaHCO_3$. The organic extract was dried over $MgSO_4$, filtered, and concentrated to afford cis-7-(trifluoromethyl)-1,2,3,4,4a,9b-hexahydrobenzofuro[3,2-b]pyridine. ES/MS: m/z=244.0 $[M+H]^+$. 1H NMR (400 MHz, Methanol-d4) δ 7.53 (d, J=7.7 Hz, 1H), 7.22 (d, J=7.8 Hz, 1H), 7.11 (s, 1H), 4.54 (q, J=4.5 Hz, 1H), 4.26 (d, J=5.4 Hz, 1H), 2.93-2.80 (m, 1H), 2.74-2.60 (m, 1H), 2.32-2.19 (m, 1H), 2.11-1.97 (m, 1H), 1.74-1.48 (m, 2H).

Ev-2

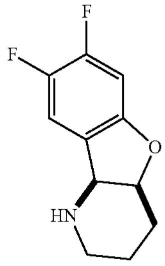

(±)

cis-7,8-difluoro-1,2,3,4,4a,9b-hexahydrobenzofuro[3,2-b]pyridine (Ev-2). Prepared according to general procedure XXII-E starting with (2,4,5-trifluorophenyl)boronic acid and 2-bromopyridin-3-ol. ES/MS: m/z=212.0 $[M+H]^+$.

Ev-3

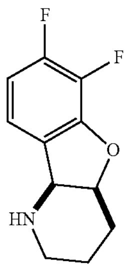

(±)

cis-6,7-difluoro-1,2,3,4,4a,9b-hexahydrobenzofuro[3,2-b]pyridine (Ev-3). Prepared according to general procedure XXII-E starting with (2,3,4-trifluorophenyl)boronic acid and 2-bromopyridin-3-ol. ES/MS: m/z=212.0 $[M+H]^+$.

Ev-4

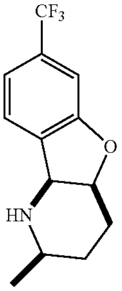

(±)

cis-2-methyl-7-(trifluoromethyl)-1,2,3,4,4a,9b-hexahydrobenzofuro[3,2-b]pyridine (Ev-4). Prepared according to general procedure XXII-E starting with [2-fluoro-4-(trifluoromethyl)phenyl]boronic acid and 2-bromo-6-methyl-pyridin-3-ol. ES/MS: m/z=258.0 $[M+H]^+$.

Ev-5

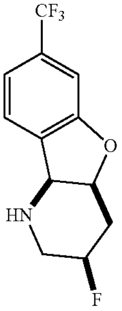

(±)

cis-3-fluoro-7-(trifluoromethyl)-1,2,3,4,4a,9b-hexahydrobenzofuro[3,2-b]pyridine (Ev-5). Prepared according to general procedure XXII-E (Performed in MeOH with 2.4 equivalents of conc. HCl under 50 bar H2 pressure) starting with [2-fluoro-4-(trifluoromethyl)phenyl]boronic acid and 2-bromo-5-fluoro-pyridin-3-ol. ES/MS: m/z=261.9 $[M+H]^+$.

Ev-6

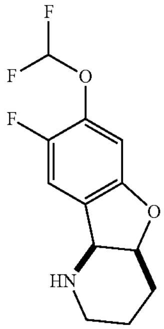

(±)

cis-7-(difluoromethoxy)-8-fluoro-1,2,3,4,4a,9b-hexahydrobenzofuro[3,2-b]pyridine (Ev-6). Prepared according to general procedure XXII-E (The product was obtained following purification of the Boc protected amine with $Boc_2O$, and deprotection using HCl in 1,4-dioxane.) starting with [4-(difluoromethoxy)-2,5-difluoro-phenyl]boronic acid. ES/MS: m/z=260.2 [M+H]$^+$.

Ev-7

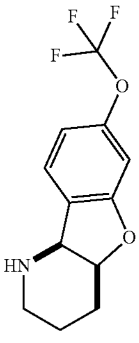

(±)

cis-7-(trifluoromethoxy)-1,2,3,4,4a,9b-hexahydrobenzofuro[3,2-b]pyridine (Ev-7). Prepared following procedure XXII-E starting with [2-fluoro-4-(trifluoromethoxy)phenyl] boronic acid and 2-bromopyridin-3-ol. ES/MS: m/z=260.0 [M+H]$^+$.

Ev-8

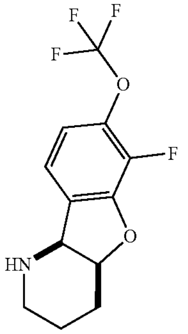

(±)

cis-6-fluoro-7-(trifluoromethoxy)-1,2,3,4,4a,9b-hexahydrobenzofuro[3,2-b]pyridine (Ev-8). Prepared following procedure XXII-E starting with [2,3-difluoro-4-(trifluoromethoxy)phenyl]boronic acid and 2-bromopyridin-3-ol. ES/MS: m/z=278.0 [M+H]$^+$.

Ev-9

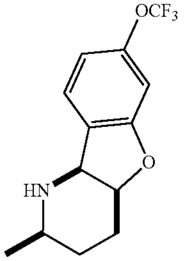

(±)

cis-(2R,4aS,9bS)$_2$-methyl-7-(trifluoromethoxy)-1,2,3,4,4a,9b-hexahydrobenzofuro[3,2-b]pyridine (Ev-9). Prepared according to general procedure XXII-E staring with [2-fluoro-4-(trifluoromethoxy)phenyl]boronic acid and 2-bromo-6-methyl-pyridin-3-ol. ES/MS: m/z=274.0 [M+H]$^+$.

Ev-10

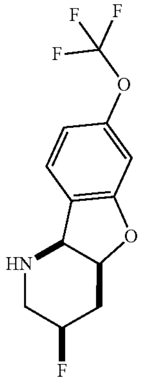

(±)

cis-(3R,4aS,9bS)-3-fluoro-7-(trifluoromethoxy)-1,2,3,4,4a,9b-hexahydrobenzofuro[3,2-b]pyridine (Ev-10). Prepared following procedure XXII-E starting with [2-fluoro-4-(trifluoromethoxy)phenyl]boronic acid and 2-bromo-5-fluoro-pyridin-3-ol. (conc. HCl was used instead of AcOH in step 2) ES/MS: m/z=278.0 [M+H]$^+$.

General Procedure XXIII-E for the Synthesis of Intermediates Ew.

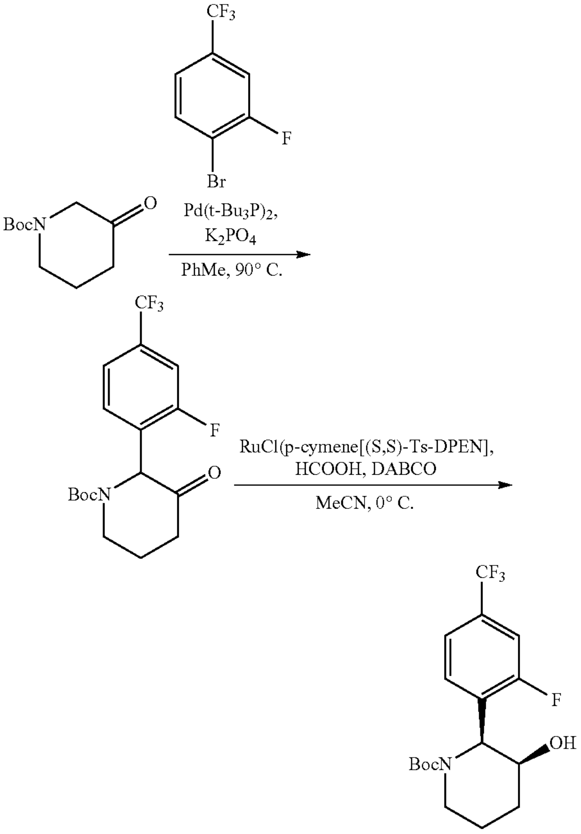

-continued

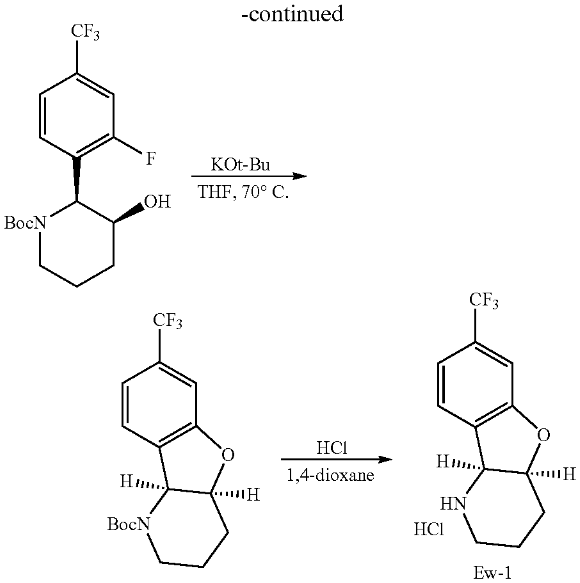

Ew-1

Step 1: tert-butyl 2-[2-fluoro-4-(trifluoromethyl)phenyl]-3-oxo-piperidine-1-carboxylate. To a stirred solution of tert-butyl 3-oxopiperidine-1-carboxylate (1.97 g, 9.9 mmol) and 1-bromo-2-fluoro-4-(trifluoromethyl)benzene (1.2 g, 4.9 mmol) in toluene (16 mL) was added $K_3PO_4$ (2.6 g, 12 mmol) and $Pd(t\text{-}Bu3P)_2$ (177 mg, 0.35 mmol). The mixture was heated to 90° C. for 3 hours, then cooled to room temperature, filtered over celite, and concentrated. Purification by silica gel flash column chromatography afforded tert-butyl 2-[2-fluoro-4-(trifluoromethyl)phenyl]-3-oxo-piperidine-1-carboxylate. ES/MS: m/z=305.8 $[M\text{-}tBu+H]^+$. $^1H$ NMR (400 MHz, Chloroform-d) δ 7.44-7.37 (m, 2H), 7.34 (d, J=10.2 Hz, 1H), 5.69 (s, 1H), 4.21-4.08 (m, 1H), 3.43-3.30 (m, 1H), 2.73-2.54 (m, 2H), 2.25-2.00 (m, 2H), 1.38 (s, 9H).

Step 2: tert-butyl (2S,3S)-2-[2-fluoro-4-(trifluoromethyl)phenyl]-3-hydroxy-piperidine-1-carboxylate. To a solution of tert-butyl 2-[2-fluoro-4-(trifluoromethyl)phenyl]-3-oxo-piperidine-1-carboxylate (850 mg, 2.4 mmol) in acetonitrile (24 mL) at 0° C. was added DABCO (1.45 g, 13 mmol), formic acid (0.27 mL, 7.1 mmol), and RuCl(p-cymene)[(S,S)-Ts-DPEN] (45 mg, 0.07 mmol). After stirring for 3 hours, sat. aq. $NaHCO_3$ was added and the mixture was diluted with EtOAc. The mixture was transferred to a separatory funnel and the organic layer was washed with brine, dried over $MgSO_4$, filtered, and concentrated. Purification by silica gel flash column chromatography afforded tert-butyl (2S,3S)-2-[2-fluoro-4-(trifluoromethyl)phenyl]-3-hydroxy-piperidine-1-carboxylate. ES/MS: m/z=307.9 $[M\text{-}tBu+H]^+$. $^1H$ NMR (400 MHz, Chloroform-d) δ 7.55 (t, J=7.6 Hz, 1H), 7.41 (d, J=8.2 Hz, 1H), 7.35 (d, J=10.3 Hz, 1H), 5.54 (d, J=5.9 Hz, 1H), 4.29-4.20 (m, 1H), 4.19-4.05 (m, 1H), 3.36-3.25 (m, 1H), 1.94-1.74 (m, 4H), 1.33 (s, 9H).

Step 3: tert-butyl (4aS,9bS)-7-(trifluoromethyl)-3,4,4a,9b-tetrahydro-2H-benzofuro[3,2-b]pyridine-1-carboxylate. Potassium tert-butoxide (255 mg, 2.3 mmol) was added to a solution of tert-butyl (2S,3S)-2-[2-fluoro-4-(trifluoromethyl)phenyl]-3-hydroxy-piperidine-1-carboxylate (550 mg, 1.5 mmol) in THF (10 mL). The mixture was heated to 70° C. for 10 minutes, then cooled to room temperature and sat. aq. $NH_4Cl$ was added. The mixture was diluted with EtOAc and transferred to a separatory funnel. The organic layer was washed with brine, dried over $MgSO_4$, filtered, and concentrated. Purification by silica gel flash column chromatography afforded tert-butyl (4aS,9bS)-7-(trifluoromethyl)-3,4,4a,9b-tetrahydro-2H-benzofuro[3,2-b]pyridine-1-carboxylate. ES/MS: m/z=288.0 $[M\text{-}tBu+H]^+$. $^1H$ NMR (400 MHz, Chloroform-d) δ 7.33 (s, 1H), 7.18 (d, J=7.7 Hz, 1H), 7.05 (s, 1H), 6.11-5.76 (m, 1H), 4.99 (s, 1H), 4.08-3.66 (m, 1H), 2.75 (s, 1H), 2.01-1.84 (m, 2H), 1.68 (dh, J=15.1, 7.3 Hz, 2H), 1.55 (s, 9H).

Step 4: (4aS,9bS)-7-(trifluoromethyl)-1,2,3,4,4a,9b-hexahydrobenzofuro[3,2-b]pyridine hydrochloride (Ew-1). A solution of (4aS,9bS)-7-(trifluoromethyl)-3,4,4a,9b-tetrahydro-2H-benzofuro[3,2-b]pyridine-1-carboxylate (410 mg, 1.2 mmol) in 1,4-dioxane (12 mL) was treated with HCl (4.0 M in dioxane, ×2 mL, 12 mmol). After stirring overnight, the mixture was concentrated to afford (4aS,9bS)-7-(trifluoromethyl)-1,2,3,4,4a,9b-hexahydrobenzofuro[3,2-b]pyridine as the hydrochloride salt. ES/MS: m/z=244.0 $[M+H]^+$. $^1H$ NMR (400 MHz, Methanol-d4) δ 7.69 (d, J=7.9 Hz, 1H), 7.40 (d, J=8.5 Hz, 1H), 7.33 (s, 1H), 4.97-4.74 (m, 2H), 3.40-3.23 (m, 1H), 3.17-3.02 (m, 1H), 2.46 (d, J=15.7 Hz, 1H), 2.25-2.04 (m, 1H), 2.00-1.75 (m, 2H).

Ew-2

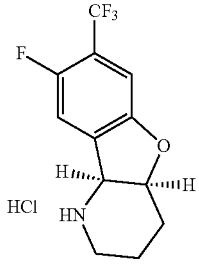

(4aS,9bS)-8-fluoro-7-(trifluoromethyl)-1,2,3,4,4a,9b-hexahydrobenzofuro[3,2-b]pyridine hydrochloride (Ew-2). Prepared according to general procedure XXIII-E starting with tert-butyl 3-oxopiperidine-1-carboxylate and 1-bromo-2,5-difluoro-4-(trifluoromethyl)benzene. ES/MS: m/z=261.9 $[M+H]^+$.

Ew-3

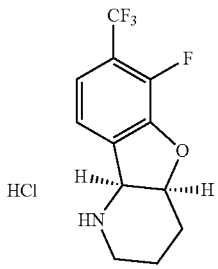

(4aS,9bS)-6-fluoro-7-(trifluoromethyl)-1,2,3,4,4a,9b-hexahydrobenzofuro[3,2-b]pyridine hydrochloride (Ew-3). Prepared according to general procedure XXIII-E starting with tert-butyl 3-oxopiperidine-1-carboxylate and 1-bromo-2,3-difluoro-4-(trifluoromethyl)benzene. ES/MS: m/z=261.9 $[M+H]^+$.

Ew-4

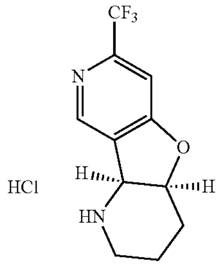

(4aS,9bS)-7-(trifluoromethyl)-1,2,3,4,4a,9b-hexahydro-furo[3,2-b:4,5-c']dipyridine hydrochloride (Ew-4). Prepared according to general procedure XXIII-E starting with tert-butyl 3-oxopiperidine-1-carboxylate and 4-chloro-5-iodo-2-(trifluoromethyl)pyridine. ES/MS: m/z=244.9 $[M+H]^+$.

Ew-5

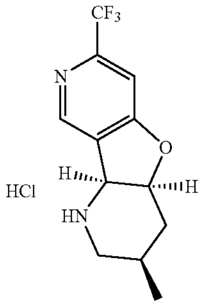

(3R,4aS,9bS)-3-methyl-7-(trifluoromethyl)-1,2,3,4,4a,9b-hexahydrofuro[3,2-b:4,5-c']dipyridine hydrochloride (Ew-5). Prepared according to general procedure XXIII-E starting with tert-butyl 3-oxopiperidine-1-carboxylate and tert-butyl (3R)-3-methyl-5-oxo-piperidine-1-carboxylate and 4-chloro-5-iodo-2-(trifluoromethyl)pyridine. ES/MS: m/z=258.9 $[M+H]^+$.

Ew-6

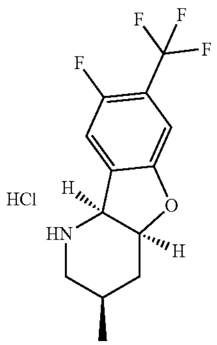

(3R,4aS,9bS)-8-fluoro-3-methyl-7-(trifluoromethyl)-1,2,3,4,4a,9b-hexahydrobenzofuro[3,2-b]pyridine hydrochloride (Ew-6): Prepared using general procedure XXIII-E starting with tert-butyl (3R)-3-methyl-5-oxo-piperidine-1-carboxylate and 1-bromo-2,5-difluoro-4-(trifluoromethyl) benzene. ES/MS: m/z=276.2 $[M+H]^+$.

Ew-7

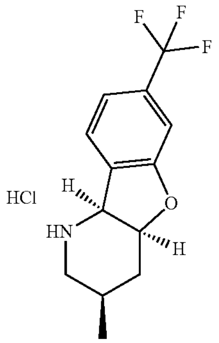

(3R,4aS,9bS)-3-methyl-7-(trifluoromethyl)-1,2,3,4,4a,9b-hexahydrobenzofuro[3,2-b]pyridine hydrochloride (Ew-7): Prepared using general procedure XXIII-E starting with tert-butyl (3R)-3-methyl-5-oxo-piperidine-1-carboxylate and 1-bromo-2-fluoro-4-(trifluoromethyl)benzene. ES/MS: m/z=258.2 $[M+H]^+$.

Ew-8

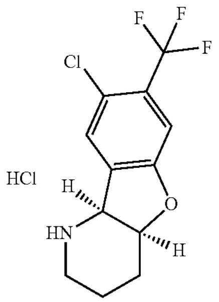

(4aS,9bS)-8-chloro-7-(trifluoromethyl)-1,2,3,4,4a,9b-hexahydrobenzofuro[3,2-b]pyridine hydrochloride (Ew-8): Prepared using general procedure XXIII-E starting with tert-butyl 3-oxopiperidine-1-carboxylate and 1-chloro-4-fluoro-5-iodo-2-(trifluoromethyl)benzene. ES/MS: m/z=278.0 $[M+H]^+$.

Ew-9

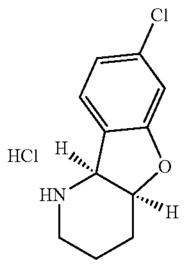

(4aS,9bS)-7-chloro-1,2,3,4,4a,9b-hexahydrobenzofuro[3,2-b]pyridine hydrochloride (Ew-9): Prepared using general procedure XXIII-E starting with tert-butyl 3-oxopiperidine-1-carboxylate and 1-bromo-4-chloro-2-fluoro-benzene. ES/MS: m/z=210.2 $[M+H]^+$.

Ew-10

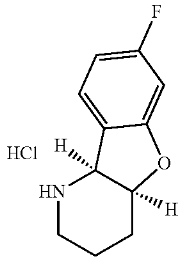

(4aS,9bS)-7-fluoro-1,2,3,4,4a,9b-hexahydrobenzofuro[3,2-b]pyridine hydrochloride (Ew-10): Prepared using general procedure XXIII-E starting with tert-butyl 3-oxopiperidine-1-carboxylate and 1-bromo-2,4-difluoro-benzene. ES/MS: m/z=194.2 [M+H]$^+$.

Ew-11

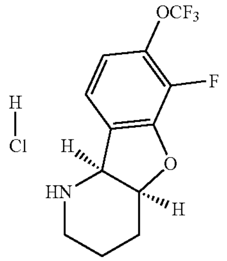

(4aS,9bS)-6-fluoro-7-(trifluoromethoxy)-1,2,3,4,4a,9b-hexahydrobenzofuro[3,2-b]pyridine hydrochloride (Ew-11). Prepared following procedure XXIII-E starting with tert-butyl 3-oxopiperidine-1-carboxylate and 1-bromo-2,3-difluoro-4-(trifluoromethoxy)benzene. ES/MS: m/z=278.0 [M+H]$^+$.

Ew-12

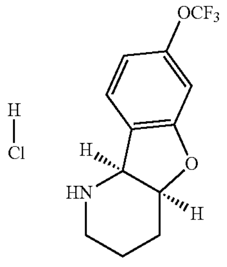

(4aS,9bS)-7-(trifluoromethoxy)-1,2,3,4,4a,9b-hexahydrobenzofuro[3,2-b]pyridine hydrochloride (Ew-12). Prepared following procedure XXIII-E starting with tert-butyl 3-oxopiperidine-1-carboxylate and 1-bromo-2-fluoro-4-(trifluoromethoxy)benzene. ES/MS: m/z=260.0 [M+H]$^+$.

Ew-14

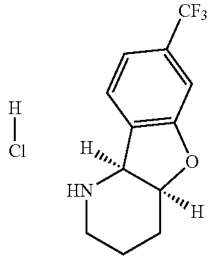

(4aS,9bS)-7-(trifluoromethyl)-1,2,3,4,4a,9b-hexahydrofuro[2,3-b:4,5-b']dipyridine hydrochloride (Ew-14). Prepared following procedure XXIII-E starting with tert-butyl 3-oxopiperidine-1-carboxylate and 2-chloro-3-iodo-6-(trifluoromethyl)pyridine. ES/MS: m/z=245.2 [M+H]$^+$.

Ew-15

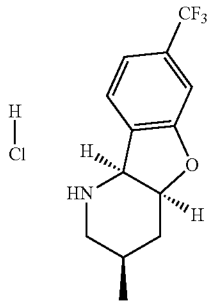

(3R,4aS,9bS)-3-methyl-7-(trifluoromethyl)-1,2,3,4,4a,9b-hexahydrofuro[2,3-b:4,5-b']dipyridine hydrochloride (Ew-15). Prepared following procedure XXIII-E starting with tert-butyl (3R)-3-methyl-5-oxo-piperidine-1-carboxylate and 2-chloro-3-iodo-6-(trifluoromethyl)pyridine. ES/MS: m/z=259.2 [M+H]$^+$.

Ew-16

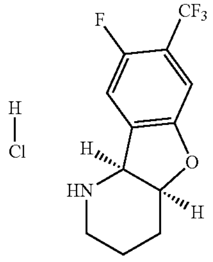

(4aS,9bS)-8-fluoro-7-(trifluoromethoxy)-1,2,3,4,4a,9b-hexahydrobenzofuro[3,2-b]pyridine hydrochloride (Ew-16). Prepared following procedure XXIII-E starting tert-butyl 3-oxopiperidine-1-carboxylate and 1-bromo-2,5-difluoro-4-(trifluoromethoxy)benzene. ES/MS: m/z=278.2 [M+H]$^+$.

Ew-17

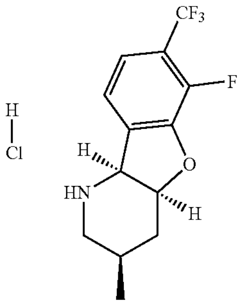

(3R,4aS,9bS)-6-fluoro-3-methyl-7-(trifluoromethyl)-1,2,3,4,4a,9b-hexahydrobenzofuro[3,2-b]pyridine hydrochloride (Ew-17). Prepared following procedure XXIII-E starting with tert-butyl (3R)-3-methyl-5-oxo-piperidine-1-carboxylate and 1-bromo-2,3-difluoro-4-(trifluoromethyl)benzene. ES/MS: m/z=276.2 $[M+H]^+$.

Ew-18

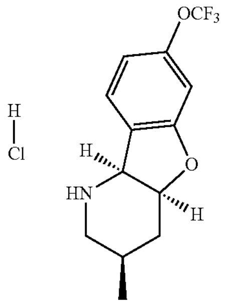

(3R,4aS,9bS)-3-methyl-7-(trifluoromethoxy)-1,2,3,4,4a,9b-hexahydrobenzofuro[3,2-b]pyridine (Ew-18). Prepared following general procedure XXIII-E starting with tert-butyl (3R)-3-methyl-5-oxo-piperidine-1-carboxylate and 1-bromo-2-fluoro-4-(trifluoromethoxy)benzene. ES/MS: m/z=274.0 $[M+H]^+$.

Ew-19

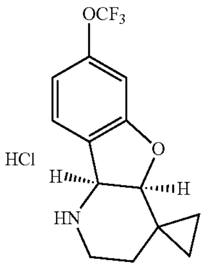

(4aS,9bS)-7-(trifluoromethoxy)-2,3,4a,9b-tetrahydro-1H-spiro[benzofuro[3,2-b]pyridine-4,1'-cyclopropane]hydrochloride (Ew-19). Prepared according to general procedure XXIII-E starting with tert-butyl 4-oxo-6-azaspiro[2.5]octane-6-carboxylate and 1-bromo-2-fluoro-4-(trifluoromethoxy)benzene. ES/MS: m/z=286.0 $[M+H]^+$.

Ew-20

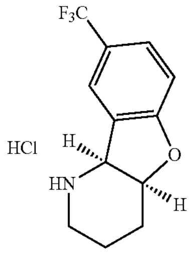

(4aS,9bS)-8-(trifluoromethyl)-1,2,3,4,4a,9b-hexahydrobenzofuro[3,2-b]pyridine hydrochloride (Ew-20). Prepared according to general procedure XXIII-E starting with 2-bromo-1-fluoro-4-(trifluoromethyl)benzene. ES/MS: m/z=244.1 $[M+H]^+$.

Ew-21

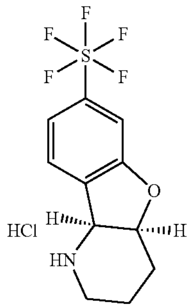

(4aS,9bS)-7-(pentafluoro-16-sulfaneyl)-1,2,3,4,4a,9b-hexahydrobenzofuro[3,2-b]pyridine hydrochloride (Ew-21). Prepared according to general procedure XXIII-E starting with tert-butyl 3-oxopiperidine-1-carboxylate and (4aS,9bS)-7-(pentafluoro-16-sulfaneyl)-1,2,3,4,4a,9b-hexahydrobenzofuro[3,2-b]pyridine. ES/MS: m/z=302.0 $[M+H]^+$.

Ew-22

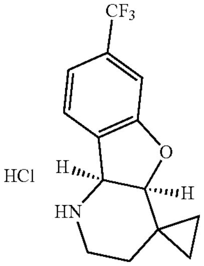

(4aS,9bS)-7-(trifluoromethyl)-2,3,4a,9b-tetrahydro-1H-spiro[benzofuro[3,2-b]pyridine-4,1'-cyclopropane]hydrochloride (Ew-22). Prepared following procedure XXIII-E starting with tert-butyl 4-oxo-6-azaspiro[2.5]octane-6-carboxylate and 1-bromo-2-fluoro-4-(trifluoromethyl)benzene. ES/MS: m/z=270.2 $[M+H]^+$.

General Procedure XXIV-E for the Synthesis of Intermediates Ex

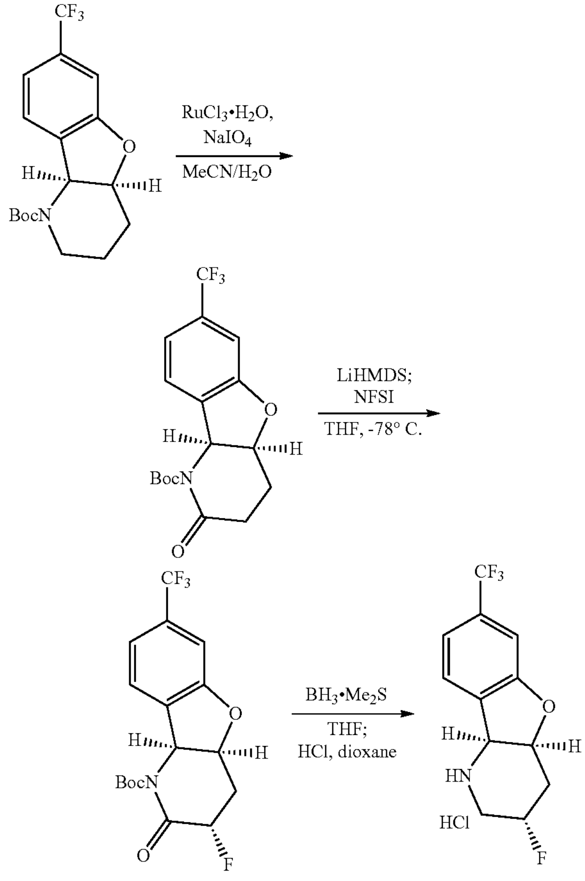

Ex-1

Step 1: tert-butyl (4aS,9bS)-2-oxo-7-(trifluoromethyl)-3,4,4a,9b-tetrahydrobenzofuro[3,2-b]pyridine-1-carboxylate. Ruthenium (III) chloride hydrate (13 mg, 0.06 mmol) was added to a solution of Sodium periodate (934 mg, 4.4 mol) in $H_2O$ (18 mL). The resulting mixture was added to a solution of tert-butyl (4aS,9bS)-7-(trifluoromethyl)-3,4,4a,9b-tetrahydro-2H-benzofuro[3,2-b]pyridine-1-carboxylate (prepared according to general procedure XXIII-E, 500 mg, 1.5 mmol) in acetonitrile (6 mL). The mixture was stirred overnight before being diluted with EtOAc. The organic layer was separated, washed with brine, dried over $MgSO_4$, filtered, and concentrated. Purification by silica gel flash column chromatography afforded tert-butyl (4aS,9bS)-2-oxo-7-(trifluoromethyl)-3,4,4a,9b-tetrahydrobenzofuro[3,2-b]pyridine-1-carboxylate. ES/MS: m/z=257.9 $[M-Boc+H]^+$. $^1H$ NMR (400 MHz, Chloroform-d) δ 7.55 (d, J=7.9 Hz, 1H), 7.16 (d, J=7.8 Hz, 1H), 7.04 (s, 1H), 6.04 (d, J=9.8 Hz, 1H), 5.32-5.20 (m, 1H), 2.57-2.46 (m, 1H), 2.43-2.27 (m, 2H), 2.15-1.98 (m, 1H), 1.59 (s, 9H).

Step 2: tert-butyl (3S,4aS,9bS)-3-fluoro-2-oxo-7-(trifluoromethyl)-3,4,4a,9b-tetrahydrobenzofuro[3,2-b]pyridine-1-carboxylate. LiHMDS (1.0 M in THF, 0.62 mL, 0.62 mmol) was slowly added to a solution of tert-butyl (4aS,9bS)-2-oxo-7-(trifluoromethyl)-3,4,4a,9b-tetrahydrobenzofuro[3,2-b]pyridine-1-carboxylate (200 mg, 0.56 mmol) in THF (3 mL) at −78° C. After 30 minutes, NFSI (194 mg, 0.62 mmol) was added and the mixture was allowed to slowly warm to −40° C. Sat. aq. $NaHCO_3$ was added and the mixture was diluted with EtOAc. The organic layer was separated, washed with brine, dried over $MgSO_4$, filtered, and concentrated. Purification by silica gel flash column chromatography afforded tert-butyl (3S,4aS,9bS)-3-fluoro-2-oxo-7-(trifluoromethyl)-3,4,4a,9b-tetrahydrobenzofuro[3,2-b]pyridine-1-carboxylate. ES/MS: m/z=275.8 $[M-Boc+H]^+$. $^1H$ NMR (400 MHz, Chloroform-d) δ 7.49 (d, J=8.0 Hz, 1H), 7.20 (d, J=8.7 Hz, OH), 7.09 (s, 1H), 6.10 (d, J=9.8 Hz, 1H), 5.37-5.23 (m, 1H), 4.80 (ddd, J=46.9, 13.4, 4.8 Hz, 1H), 2.83 (dtd, J=13.8, 5.0, 2.3 Hz, 1H), 2.37 (tdd, J=13.6, 5.6, 3.9 Hz, 1H), 1.60 (s, 9H).

Step 3: (3S,4aS,9bS)-3-fluoro-7-(trifluoromethyl)-1,2,3,4,4a,9b-hexahydrobenzofuro[3,2-b]pyridine hydrochloride (Ex-1). Borane dimethyl sulfide complex (0.46 mL, 0.48 mmol) was added to a solution of tert-butyl (3S,4aS,9bS)-3-fluoro-2-oxo-7-(trifluoromethyl)-3,4,4a,9b-tetrahydrobenzofuro[3,2-b]pyridine-1-carboxylate (30 mg, 0.08 mmol) in THF (1 mL). After stirring overnight, MeOH (1 mL) was carefully added and the mixture was concentrated. The crude residue was suspended in 1,4-dioxane (1 mL) and HCl (4.0 M in dioxane, 0.2 mL, 0.8 mmol) was added. The mixture was stirred overnight, then concentrated to afford (3S,4aS,9bS)-3-fluoro-7-(trifluoromethyl)-1,2,3,4,4a,9b-hexahydrobenzofuro[3,2-b]pyridine as the hydrochloride salt. ES/MS: m/z=261.9 $[M+H]^+$.

Ex-2

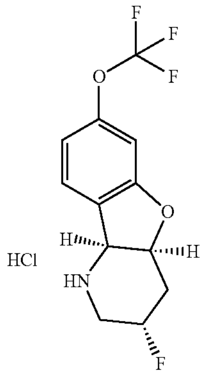

(3S,4aS,9bS)-3-fluoro-7-(trifluoromethoxy)-1,2,3,4,4a,9b-hexahydrobenzofuro[3,2-b]pyridine hydrochloride (Ex-2). Prepared according to general procedure XXIV-E starting with tert-butyl (4aS,9bS)-7-(trifluoromethoxy)-3,4,4a,9b-tetrahydro-2H-benzofuro[3,2-b]pyridine-1-carboxylate (prepared according to general procedure XXIII-E). ES/MS: m/z=278.1 $[M+H]^+$.

General Procedure XXV-E for the Synthesis of Intermediates Ey

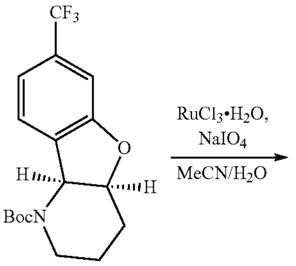

-continued

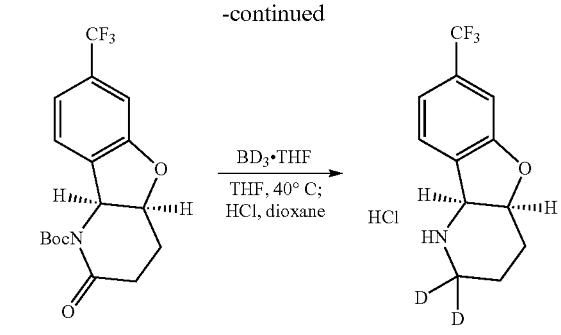

Ey-1

Step 1: tert-butyl (4aS,9bS)-2-oxo-7-(trifluoromethyl)-3,4,4a,9b-tetrahydrobenzofuro[3,2-b]pyridine-1-carboxylate. Ruthenium (III) chloride hydrate (13 mg, 0.06 mmol) was added to a solution of Sodium periodate (934 mg, 4.4 mol) in $H_2O$ (18 mL). The resulting mixture was added to a solution of tert-butyl (4aS,9bS)-7-(trifluoromethyl)-3,4,4a,9b-tetrahydro-2H-benzofuro[3,2-b]pyridine-1-carboxylate (Prepared according to general procedure XXIII-E) (500 mg, 1.5 mmol) in acetonitrile (6 mL). The mixture was stirred overnight before being diluted with EtOAc. The organic layer was separated, washed with brine, dried over $MgSO_4$, filtered, and concentrated. Purification by silica gel flash column chromatography afforded tert-butyl (4aS,9bS)-2-oxo-7-(trifluoromethyl)-3,4,4a,9b-tetrahydrobenzofuro[3,2-b]pyridine-1-carboxylate. ES/MS: m/z=257.9 $[M-Boc+H]^+$. $^1H$ NMR (400 MHz, Chloroform-d) δ 7.55 (d, J=7.9 Hz, 1H), 7.16 (d, J=7.8 Hz, 1H), 7.04 (s, 1H), 6.04 (d, J=9.8 Hz, 1H), 5.32-5.20 (m, 1H), 2.57-2.46 (m, 1H), 2.43-2.27 (m, 2H), 2.15-1.98 (m, 1H), 1.59 (s, 9H).

Step 2: (4aS,9bS)-7-(trifluoromethyl)-1,2,3,4,4a,9b-hexahydrobenzofuro[3,2-b]pyridine-2,2-d2 hydrochloride (Ey-1). Borane-d3 (1.0 M in THF, 1.0 mL, 1.0 mmol) was added to a solution of tert-butyl (3S,4aS,9bS)-3-fluoro-2-oxo-7-(trifluoromethyl)-3,4,4a,9b-tetrahydrobenzofuro[3,2-b]pyridine-1-carboxylate (30 mg, 0.08 mmol) in THF (1 mL). After stirring overnight at 40° C., MeOH (1 mL) was carefully added and the mixture was concentrated. The crude residue was suspended in 1,4-dioxane (1 mL) and HCl (4.0 M in dioxane, 0.2 mL, 0.8 mmol) was added. The mixture was stirred overnight, then concentrated to afford (4aS,9bS)-2,2-dideuterio-7-(trifluoromethyl)-3,4,4a,9b-tetrahydro-1H-benzofuro[3,2-b]pyridine as the hydrochloride salt. ES/MS: m/z=246.0 $[M+H]^+$.

Ey-2

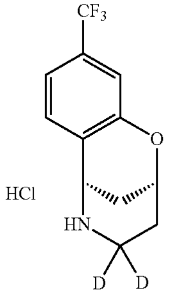

(2S,6R)-9-(trifluoromethyl)-3,4,5,6-tetrahydro-2H-2,6-methanobenzo[b][1,5]oxazocine-4,4-d2 hydrochloride (Ey-2). Prepared following general procedure XXV-E starting with tert-butyl (2S,6R)-9-(trifluoromethyl)-3,4-dihydro-2H-2,6-methanobenzo[b][1,5]oxazocine-5(6H)-carboxylate (prepared from Ebi-1). ES/MS: m/z=246.2 $[M+H]^+$.

Ey-3

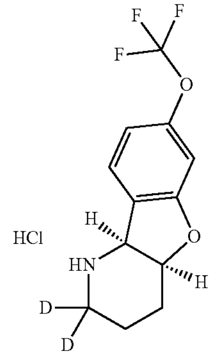

(4aS,9bS)-7-(trifluoromethoxy)-1,2,3,4,4a,9b-hexahydrobenzofuro[3,2-b]pyridine-2,2-d2 hydrochloride (Ey-3). Prepared following general procedure XXV-E starting with tert-butyl (4aS,9bS)-7-(trifluoromethoxy)-3,4,4a,9b-tetrahydrobenzofuro[3,2-b]pyridine-1(2H)-carboxylate (prepared according to general procedure XXIII-E). ES/MS: m/z=262.2 $[M+H]^+$.

General Procedure XXVI-E for the Synthesis of Intermediates Ez:

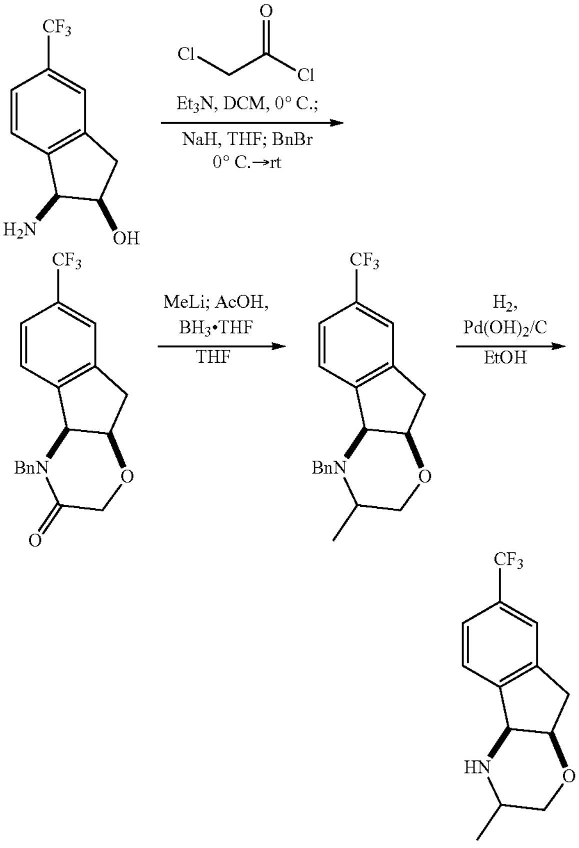

Ez-1
(±)

Step 1: 4-benzyl-7-(trifluoromethyl)-9,9a-dihydro-4aH-indeno[2,1-b][1,4]oxazin-3-one. To a solution of 1-amino-5-(trifluoromethyl)indan-2-ol (prepared according to general procedure V-E) (120 mg, 0.55 mmol) and triethylamine (0.1 mL, 0.72 mmol) in DCM (4 mL) was added chloroacetyl chloride (0.05 mL, 0.66 mmol) dropwise. After stirring for 15 minutes, water and EtOAc were added, and the mixture was transferred to a separatory funnel. The organic layer was separated, washed with brine, dried over $MgSO_4$, filtered, and concentrated. The resulting residue was suspended in THF (4 mL) and sodium hydride (60% dispersion in mineral oil, 42 mg, 1.1 mmol) was added at 0° C. Following warming to room temperature and stirring for 1 hour, benzyl bromide (0.08 mL, 0.66 mmol) was added and the mixture was allowed to stir at room temperature overnight., The mixture was quenched with sat. aq. $NH_4Cl$ and diluted with EtOAc. The organic layer was separated, washed with brine, and dried over $MgSO_4$. Purification by silica gel flash column chromatography afforded 4-benzyl-7-(trifluoromethyl)-9,9a-dihydro-4aH-indeno[2,1-b][1,4]oxazin-3-one. ES/MS: m/z=347.9 $[M+H]^+$.

Step 2: 4-benzyl-3-methyl-7-(trifluoromethyl)-3,4a,9,9a-tetrahydro-2H-indeno[2,1-b][1,4]oxazine. To a solution of 4-benzyl-7-(trifluoromethyl)-9,9a-dihydro-4aH-indeno[2,1-b][1,4]oxazin-3-one (75 mg, 0.2 mmol) in THF (2 mL) at −78° C. was added MeLi (3.0 M in DME, 0.11 mL, 0.32 mmol) dropwise. The mixture was slowly warmed to 0° C. and stirred for 2 hours. AcOH (0.02 mL, 0.32 mmol) was added followed by borane (1.0 M in THF, 0.65 mL, 0.65 mmol). After 1 hour, MeOH was added followed by sat. aq. $NH_4Cl$. The mixture was diluted with EtOAc and the organic layer was washed with water, brine, then dried over $MgSO_4$, filtered, and concentrated. Purification by silica gel flash column chromatography afforded 4-benzyl-3-methyl-7-(trifluoromethyl)-3,4a,9,9a-tetrahydro-2H-indeno[2,1-b][1,4]oxazine as a mixture of diastereomers. ES/MS: m/z=348.0 $[M+H]^+$.

Step 3: cis-3-methyl-7-(trifluoromethyl)-2,3,4,4a,9,9a-hexahydroindeno[2,1-b][1,4]oxazine (Ez-1). A mixture of 4-benzyl-3-methyl-7-(trifluoromethyl)-3,4a,9,9a-tetrahydro-2H-indeno[2,1-b][1,4]oxazine (45 mg, 0.13 mmol) and $Pd(OH)_2/C$ (20% w/w, 23 mg, 0.03 mmol) was stirred under an atmosphere of hydrogen overnight. The mixture was then filtered over celite and concentrated to afford 3-methyl-7-(trifluoromethyl)-2,3,4,4a,9,9a-hexahydroindeno[2,1-b][1,4]oxazine. ES/MS: m/z=258.0 $[M+H]^+$.

General Procedure XXVII-E for the Synthesis of Intermediates Eaa:

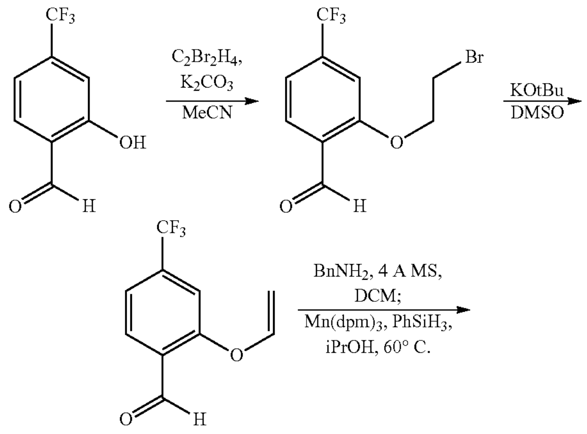

-continued

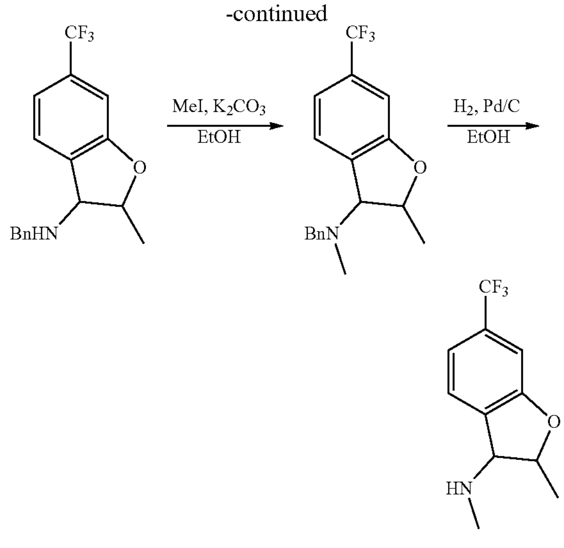

Eaa-1

Step 1: 2-(2-bromoethoxy)-4-(trifluoromethyl)benzaldehyde. To a solution of 2-hydroxy-4-(trifluoromethyl)benzaldehyde (2.5 g, 13.1 mmol) in acetonitrile (3 mL) was added potassium carbonate (1.8 g, 13.1 mmol). The mixture was refluxed for 1 hour, then 1,2-dibromoethane (11.3 mL, 131 mmol) was added. The mixture was refluxed overnight, the concentrated. Purification by silica gel flash column chromatography afforded 2-(2-bromoethoxy)-4-(trifluoromethyl)benzaldehyde. ES/MS: m/z=298.8 $[M+H]^+$.

Step 2: 4-(trifluoromethyl)-2-vinyloxy-benzaldehyde. To a solution of 2-(2-bromoethoxy)-4-(trifluoromethyl)benzaldehyde (2.38 g, 8.0 mmol) in DMSO (8 mL) was added KOtBu (1.08 g, 9.6 mmol). After stirring overnight, the mixture was diluted with Et2O and washed with water, brine, and dried over $MgSO_4$, filtered, and concentrated. Purification by silica gel flash column chromatography afforded 4-(trifluoromethyl)-2-vinyloxy-benzaldehyde. $^1H$ NMR (400 MHz, Chloroform-d) δ 10.49 (d, J=0.8 Hz, 1H), 8.00 (dd, J=8.1, 1.0 Hz, 1H), 7.50-7.40 (m, 1H), 7.37-7.31 (m, 1H), 6.72 (dd, J=13.6, 6.0 Hz, 1H), 4.98 (dd, J=13.6, 2.3 Hz, 1H), 4.75 (dd, J=6.0, 2.3 Hz, 1H).

Step 3: N-benzyl-2-methyl-6-(trifluoromethyl)-2,3-dihydrobenzofuran-3-amine. Benzylamine (0.15 mL, 1.4 mmol) was added to a mixture of 4-(trifluoromethyl)-2-vinyloxy-benzaldehyde (300 mg, 1.4 mmol) and molecular sieves. After stirring overnight, the mixture was filtered and concentrated, then resuspended in isopropanol (14 mL). $Mn(dpm)_3$ (42 mg, 0.07 mmol) was then added followed by phenylsilane (0.34 mL, 2.75 mmol) under air. The mixture was heated to 55° C., and an additional portion of phenylsilane (0.34 mL, 2.75 mmol) was added after 4 hours. After stirring overnight, the mixture was concentrated, then purified by silica gel flash column chromatography to afford N-benzyl-2-methyl-6-(trifluoromethyl)-2,3-dihydrobenzofuran-3-amine as a mixture of diastereomers. ES/MS: m/z=307.9 $[M+H]^+$.

Step 4: N-benzyl-2-methyl-6-(trifluoromethyl)-2,3-dihydrobenzofuran-3-amine. Iodomethane (0.02 mL, 0.29 mmol) was added to a mixture of N-benzyl-2-methyl-6-(trifluoromethyl)-2,3-dihydrobenzofuran-3-amine (80 mg, 0.26 mmol) and potassium carbonate (54 mg, 0.39 mmol) in EtOH (2.5 mL) at 0° C. After stirring overnight, the mixture was diluted with EtOAc and washed with water, brine. The organic extract was dried over $MgSO_4$, filtered, and concentrated. Purification by silica gel flash column chromatography afforded N-benzyl-N,2-dimethyl-6-(trifluoromethyl)-2,3-dihydrobenzofuran-3-amine. ES/MS: m/z=322.0 $[M+H]^+$.

Step 5: N,2-dimethyl-6-(trifluoromethyl)-2,3-dihydrobenzofuran-3-amine (Eaa-1). A mixture of N-benzyl-N,2-dimethyl-6-(trifluoromethyl)-2,3-dihydrobenzofuran-3-amine (80 mg) and palladium on carbon (10% w/w, 66 mg, 0.06 mmol) in EtOH (2.5 mL) was stirred under an atmosphere of hydrogen overnight. The mixture was filtered over celite, then concentrated to afford N,2-dimethyl-6-(trifluoromethyl)-2,3-dihydrobenzofuran-3-amine. ES/MS: m/z=200.9 $[M-MeNH]^+$.

General Procedure XXVIII-E for the Synthesis of Intermediates Eab:

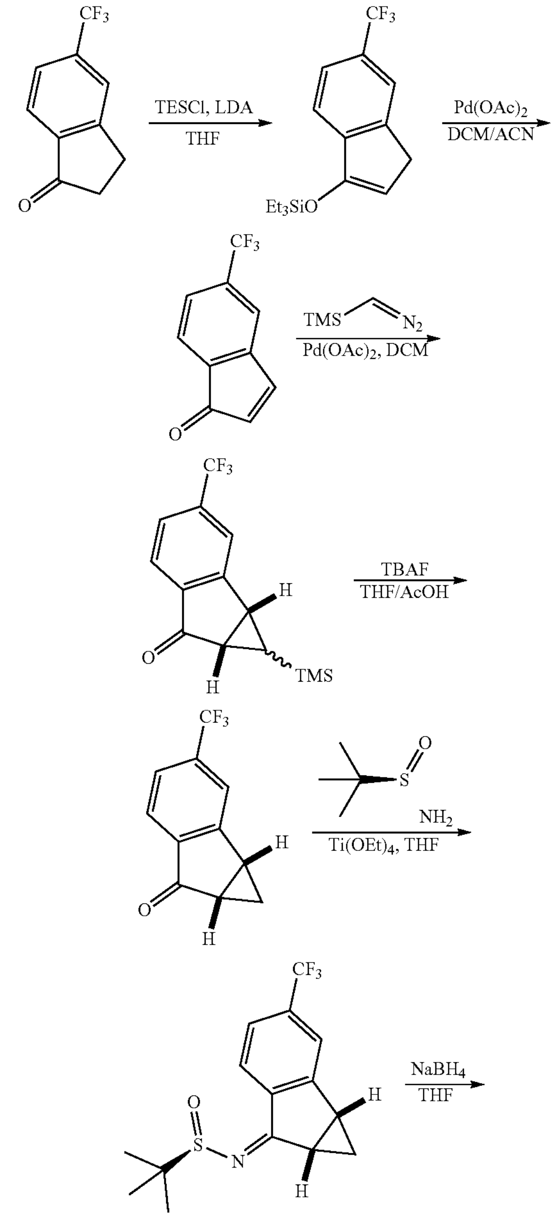

-continued

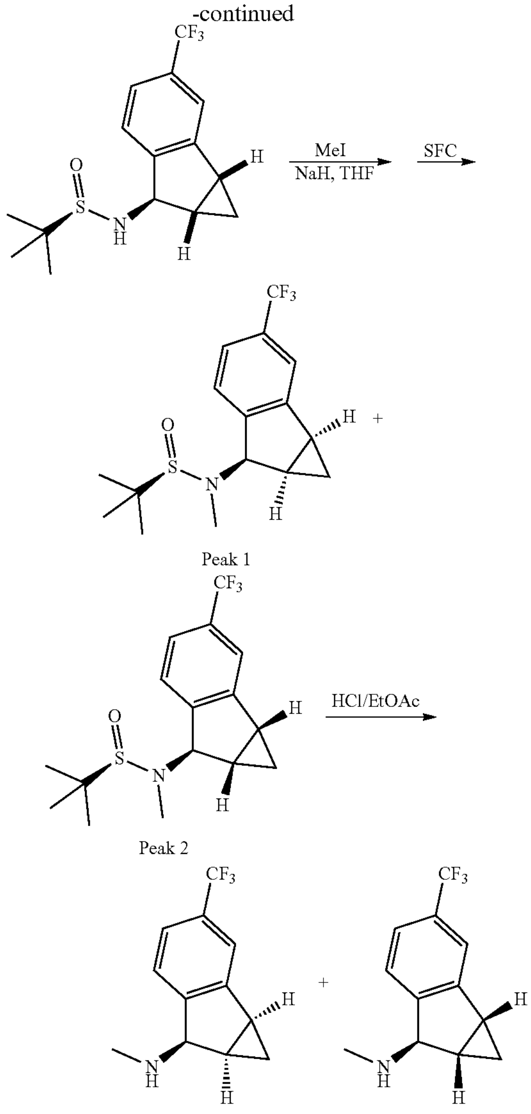

Eab-1 Eab-2

Step 1: triethyl((6-(trifluoromethyl)-1H-inden-3-yl)oxy)silane. A solution of 5-(trifluoromethyl)-2,3-dihydro-1H-inden-1-one (12.5 g, 62.4 mmol, 1 eq) in THF (150 mL) was cooled to −78° C. Then LDA (2 M, 40.5 mL, 1.3 eq) was dropwise added to the solution at −78° C. After 60 min, chloro(triethyl)silane (11.3 g, 74.9 mmol, 12.7 mL, 1.2 eq) was added to the solution at −78° C. The mixture was stirred at 20° C. for 12 hr. TLC showed consumption of starting material. The reaction mixture was quenched by addition sat $NH_4Cl$ 500 mL at 0° C. under $N_2$ protection and extracted with ethyl acetate (400 mL×3). The combined organic layers were washed with brine (200 mL×3), dried over $Na_2SO_4$, filtered, and concentrated under reduced pressure to give crude product which was used into the next step without further purification. $^1$H NMR (400 MHz, CHLOROFORM-d) δ 7.63 (s, 1H), 7.57 (d, J=7.9 Hz, 1H), 7.47 (d, J=7.9 Hz, 1H), 5.58 (t, J=2.4 Hz, 1H), 3.33 (d, J=2.3 Hz, 2H), 1.06-1.01 (m, 9H), 0.84-0.77 (m, 6H).

Step 2: 5-(trifluoromethyl)-1H-inden-1-one. To a solution of $Pd(OAc)_2$ (12.5 g, 55.9 mmol, 1 eq) in ACN (60 mL) was added a solution of triethyl((6-(trifluoromethyl)-1H-inden-3-yl)oxy)silane (18.5 g, 55.9 mmol, 1 eq) in DCM (24 mL)

under $N_2$. The mixture was stirred at 20° C. for 8 hr under $N_2$ and dark condition. TLC showed consumption of starting material. The reaction mixture was filtered washed with 200 mL DCM and concentrated under reduced pressure to give a residue. The residue was purified by flash chromatography to give title compound. $^1$H NMR (400 MHz, CHLOROFORM-d) δ 7.67 (d, J=6.0 Hz, 1H), 7.60-7.52 (m, 2H), 7.33 (s, 1H), 6.06 (d, J=6.0 Hz, 1H).

Step 3: (1rR,6rS)-3-(trifluoromethyl)-1-(trimethylsilyl)-1a,6a-dihydrocyclopropa[a]inden-6(1H)-one. A mixture of 5-(trifluoromethyl)-1H-inden-1-one, $Pd(OAc)_2$ (900.8 mg, 4.0 mmol, 0.15 eq) in Tol. (80 mL) was degassed and purged with $N_2$ for 3 times, and then the mixture was cooled to 0° C. $TMSCHN_2$ (2 M, 26.7 mL, 2 eq) was added to the solution at 0° C. The mixture was stirred at 30° C. for 12 hr under $N_2$ atmosphere. The reaction mixture was diluted with $H_2O$ 50 mL and extracted with ethyl acetate (80 mL×3). The combined organic layers were washed with NaCl (50 mL×3), dried over $Na_2SO_4$, filtered, and concentrated under reduced pressure to give a residue. The residue was purified by flash chromatography to give title compound. ES/MS: m/z=285.2 [M+H]$^+$. $^1$H NMR (400 MHz, DMSO-$d_6$) δ 7.89 (s, 1H), 7.72-7.64 (m, 2H), 3.13 (t, J=4.4 Hz, 1H), 2.68-2.63 (m, 1H), 1.06 (t, J=4.9 Hz, 1H), 0.05 (s, 9H).

Step 4: (1rR,6rS)-3-(trifluoromethyl)-1a,6a-dihydrocyclopropa[a]inden-6(1H)-one. To a solution of (1rR,6rS)-3-(trifluoromethyl)-1-(trimethylsilyl)-1a,6a-dihydrocyclopropa[a]inden-6(1H)-one (4.0 g, 14.1 mmol) in tetrahydrofuran (40.0 mL) was added Tetra-n-butyl ammonium fluoride (1.0 mol/L, 28.1 mL, 28.1 mmol) in tetrahydrofuran and acetic acid (0.0422 g, 0.7 mmol). The mixture was stirred at 60° C. for 48 hr. The reaction mixture was diluted with $H_2O$ 40 mL and extracted with Ethyl acetate 120 mL (40 mL×3). The combined organic layers were washed with brine 60 mL (20 mL×3), dried over $Na_2SO_4$, filtered, and concentrated under reduced pressure to give a residue. The residue was purified by flash chromatography to give title compound. $^1$H NMR (400 MHz, DMSO-$d_6$) δ 7.95 (s, 1H), 7.73-7.63 (m, 2H), 3.21 (td, J=3.9, 7.4 Hz, 1H), 2.65 (td, J=4.1, 9.0 Hz, 1H), 1.68 (ddd, J=4.1, 7.2, 9.0 Hz, 1H), 1.37 (q, J=3.7 Hz, 1H).

Step 5: (R)-2-methyl-N-((1rR,6rS,Z)-3-(trifluoromethyl)-1a,6a-dihydrocyclopropa[a]inden-6(1H)-ylidene)propane-2-sulfinamide. To a solution of (1rR,6rS)-3-(trifluoromethyl)-1a,6a-dihydrocyclopropa[a]inden-6(1H)-one in tetrahydrofuran (10.0 mL) was added (R)-2-methylpropane-2-sulfinamide (0.514 g, 4.2 mmol) and tetraethoxytitanium (1.29 g, 5.6 mmol). The mixture was stirred at 70° C. for 12 hr. The reaction mixture was partitioned between $H_2O$ 30 mL and Ethyl acetate 90 mL (30 mL×3). The organic phase was separated, washed with brine 60 mL (20 mL×3), dried over $Na_2SO_4$, filtered, and concentrated under reduced pressure to give crude product, which was used into the next step without further purification. ES/MS: m/z=316.0 [M+H]$^+$. $^1$H NMR (400 MHz, DMSO-$d_6$) δ 7.92 (s, 1H), 7.80 (d, J=8.0 Hz, 1H), 7.65 (br d, J=8.0 Hz, 1H), 3.55-3.35 (m, 1H), 3.21-3.12 (m, 1H), 1.73-1.61 (m, 1H), 1.24 (s, 9H), 1.17-1.15 (m, 1H).

Step 6: (R)-2-methyl-N-((1rR,6R,6rS)-3-(trifluoromethyl)-1,1a,6,6a-tetrahydrocyclopropa[a]inden-6-yl)propane-2-sulfinamide. To a solution of (R)-2-methyl-N-((1rR,6rS,Z)-3-(trifluoromethyl)-1a,6a-dihydrocyclopropa[a]inden-6(1H)-ylidene)propane-2-sulfinamide (0.97 g, 3.0 mmol) in tetrahydrofuran (10.0 mL) was added sodium borohydride (0.291 g, 7.6 mmol) at 0° C. The mixture was stirred at 0° C. for 2 hr. The reaction mixture was partitioned between $NH_4Cl$ 20 mL and ethyl acetate (20 mL×3). The organic phase was separated, washed with brine (10 mL×3), dried over $Na_2SO_4$, filtered, and concentrated under reduced pressure to give a residue. The residue was purified by flash chromatography to give title compound. ES/MS: m/z=318.0 [M+H]$^+$. $^1$H NMR (400 MHz, DMSO-d6) δ 7.64 (d, J=7.8 Hz, 1H), 7.60-7.57 (m, 1H), 7.51-7.48 (m, 1H), 5.69 (d, J=8.4 Hz, 1H), 2.11 (qd, J=4.5, 8.9 Hz, 1H), 2.06-2.00 (m, 1H), 1.19-1.17 (m, 9H), 0.96-0.92 (m, 1H), 0.66 (q, J=4.1 Hz, 1H).

Step 7: (R)—N,2-dimethyl-N-((1aS,6R,6aR)-3-(trifluoromethyl)-1,1a,6,6a-tetrahydrocyclopropa[a]inden-6-yl)propane-2-sulfinamide and (R)—N,2-dimethyl-N-((1aR,6R,6aS)-3-(trifluoromethyl)-1,1a,6,6a-tetrahydrocyclopropa[a]inden-6-yl)propane-2-sulfinamide. To a solution of (R)-2-methyl-N-((1rR,6R,6rS)-3-(trifluoromethyl)-1,1a,6,6a-tetrahydrocyclopropa[a]inden-6-yl)propane-2-sulfinamide (0.64 g, 2.0 mmol) in Tetrahydrofuran (10.0 mL) was added sodium hydride (60.0%, 0.155 g, 4.0 mmol) under $N_2$ at 0° C. Then after 30 min, iodomethane (0.572 g, 4.0 mol) was added to the solution at 0° C. The mixture was stirred at 20° C. for 2 hr. The reaction mixture was quenched by addition of $NH_4Cl$ 20 mL at 0° C., and then diluted with ethyl acetate 10 mL and extracted with ethyl acetate 10 mL×2. The combined organic layers were washed with brine (10 mL×3), dried over $Na_2SO_4$, filtered, and concentrated under reduced pressure to give a residue. The residue was purified by flash chromatography to give title compound.

The residue was further separated by prep-SFC (column: DAICEL CHIRALPAK AD (250 mm*30 mm, 10 um); mobile phase: [A: $CO_2$;B: EtOH (0.1% $NH_3H_2O$)];B %: 15.0%-15.0%, 9.0 min) to isolate Peak 1 (RT=1.167 min) and Peak 2 (RT=2.075 min).

Peak 1 was purified by prep-SFC (column: DAICEL CHIRALPAK AD (250 mm*30 mm, 10 um); mobile phase: [A: $CO_2$;B: IPA (0.1% $NH_3H_2O$)];B %: 15.0%-15.0%, 9.0 min) to give (R)—N-[(1rS,6R,6rR)-3-(trifluoromethyl)-1,1a,6,6a-tetrahydrocyclopropa[a]inden-6-yl]-N,2-dimethyl-propane-2-sulfinamide (arbitrary assignment). ES/MS: m/z=332.2 [M+H]$^+$. $^1$H NMR (400 MHz, DMSO-d6) δ 7.72 (s, 1H), 7.57-7.51 (m, 1H), 7.49-7.44 (m, 1H), 4.74 (s, 1H), 2.65 (br d, J=4.1 Hz, 1H), 2.22 (s, 3H), 2.16-2.07 (m, 1H), 1.32-1.21 (m, 1H), 1.14 (s, 9H), 0.16-0.07 (m, 1H).

Peak 2 was purified by prep-SFC (column: REGIS (s,s) WHELK-01 (250 mm*30 mm, 5 um); mobile phase: [A: $CO_2$;B: IPA (0.1% $NH_3H_2O$)];B %: 20.0%-20.0%, 10.0 min) to give (R)—N-[(1rR,6R,6rS)-3-(trifluoromethyl)-1,1a,6,6a-tetrahydrocyclopropa[a]inden-6-yl]-N,2-dimethyl-propane-2-sulfinamide (arbitrary assignment). ES/MS: m/z=332.2 [M+H]$^+$. $^1$H NMR (400 MHz, DMSO-d6) δ 7.64 (s, 1H), 7.56 (d, J=7.9 Hz, 1H), 7.27 (d, J=7.9 Hz, 1H), 5.40 (br d, J=6.4 Hz, 1H), 2.47 (br d, J=2.8 Hz, 1H), 2.44 (s, 3H), 1.95-1.86 (m, 1H), 1.19 (s, 9H), 1.12-1.02 (m, 1H), 0.61-0.53 (m, 1H).

Step 8: (1aS,6R,6aR)—N-methyl-3-(trifluoromethyl)-1,1a,6,6a-tetrahydrocyclopropa[a]inden-6-amine (Eab-1). A solution (R)—N-[(1rR,6R,6rS)-3-(trifluoromethyl)-1,1a,6,6a-tetrahydrocyclopropa[a]inden-6-yl]-N,2-dimethyl-propane-2-sulfinamide (0.2 g, 0.6 mmol) of HCl in Ethyl acetate (2.00 mL, 4M) was stirred at 20° C. for 2 hr. The reaction mixture was concentrated under reduced pressure to give a residue. The residue was passed through a syringe filter and the filtrate was purified by prep-HPLC (HCl condition, column: Phenomenex luna C18 100*40 mm*5 um; mobile phase:[A: $H_2O$ (0.04% HCl);B: ACN]; B %: 1.00%-40.00%, 7.00 min) to give title compound. ES/MS: m/z=228.2 [M+H]$^+$. $^1$H NMR (400 MHz, DMSO-d6) δ 10.32 (br s, 1H), 8.85 (br s, 1H), 7.93 (d, J=8.0 Hz, 1H), 7.73 (s, 1H), 7.63 (d, J=7.8 Hz, 1H), 5.14 (br s, 1H), 2.85-2.71 (m, 4H), 2.26-2.15 (m, 1H), 1.22-1.13 (m, 1H), 0.91-0.84 (m, 1H).

(1aR,6R,6aS)—N-methyl-3-(trifluoromethyl)-1,1a,6,6a-tetrahydrocyclopropa[a]inden-6-amine (Eab-2). A solution (R)—N—[(IrS,6R,6rR)-3-(trifluoromethyl)-1,1a,6,6a-tetrahydrocyclopropa[a]inden-6-yl]-N,2-dimethyl-propane-2-sulfinamide (0.14 g, 0.4 mol) and HCl in Ethyl acetate (2.00 mL, 4M) was stirred at 20° C. for 2 hr. The reaction mixture was concentrated under reduced pressure to give a residue. The residue was passed through a syringe filter and the filtrate was purified by prep-HPLC(HCl condition, column: Phenomenex luna C18 100*40 mm*5 um; mobile phase: [A: $H_2O$(0.04% HCl);B: ACN];B %: 5.00%-35.00%, 7.00 min) to give title compound. ES/MS: m/z=228 $[M+H]^+$. $^1H$ NMR (400 MHz, DMSO-d6) δ 9.49-9.25 (m, 2H), 7.91-7.80 (m, 2H), 7.63 (d, J=8.4 Hz, 1H), 4.73 (s, 1H), 2.80-2.70 (m, 1H), 2.53-2.50 (m, 3H), 2.34-2.25 (m, 1H), 1.40-1.31 (m, 1H), 0.21-0.13 (m, 1H).

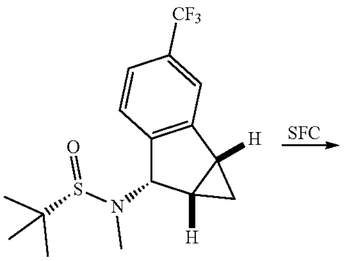

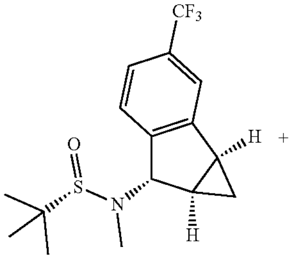

Peak 1

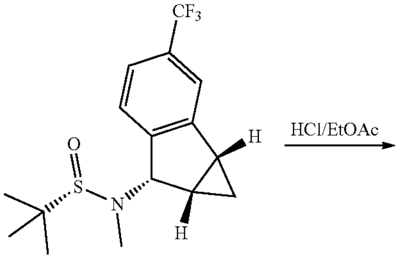

Peak 2

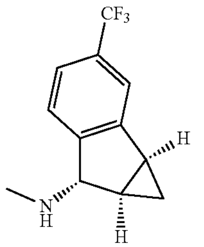

Eab-3

+

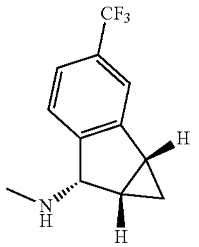

Eab-4

(1aS,6S,6aR)—N-methyl-3-(trifluoromethyl)-1,1a,6,6a-tetrahydrocyclopropa[a]inden-6-amine. (Eab-3) and (1aR,6S,6aS)—N-methyl-3-(trifluoromethyl)-1,1a,6,6a-tetrahydrocyclopropa[a]inden-6-amine (Eab-4)

Prepared following procedure XXVIII-E starting with (S)-2-methylpropane-2-sulfinamide in step 5. SFC separation of step 7 gave peak 1 and peak 2, which were deprotected with HCl to give Eab-3 and Eab-4, respectively.

(S)—N,2-dimethyl-N-((1aRS,6S,6aSR)-3-(trifluoromethyl)-1,1a,6,6a-tetrahydrocyclopropa[a]inden-6-yl)propane-2-sulfinamide was separated by prep-SFC (column: DAICEL CHIRALPAK AD (250 mm*30 mm, 10 um); mobile phase: [A: $CO_2$;B: EtOH (0.1% $NH_3H_2O$)];B %: 14.00%-14.00%, 4.00 min) to give peak 1 (S)—N,2-dimethyl-N-((1aS,6S,6aR)-3-(trifluoromethyl)-1,1a,6,6a-tetrahydrocyclopropa[a]inden-6-yl)propane-2-sulfinamide (RT: 1.603 min) and peak 2 (S)—N,2-dimethyl-N—((1aR,6S,6aS)-3-(trifluoromethyl)-1,1a,6,6a-tetrahydrocyclopropa[a]inden-6-yl)propane-2-sulfinamide (RT: 1.916 min), both arbitrarily assigned.

Peak 1: ES/MS: m/z=332.1 $[M+H]^+$. $^1H$ NMR (400 MHz, CHLOROFORM-d) δ 7.57 (s, 1H), 7.52 (d, J=7.9 Hz, 1H), 7.45-7.40 (m, 1H), 4.76 (s, 1H), 2.63-2.52 (m, 1H), 2.35 (s, 3H), 2.13-2.07 (m, 1H), 1.27 (br s, 1H), 1.25 (s, 9H), 0.17 (q, J=4.1 Hz, 1H).

Peak 2: ES/MS: m/z=332.1 $[M+H]^+$. $^1H$ NMR (400 MHz, CHLOROFORM-d) δ 7.48 (s, 1H), 7.45-7.41 (m, 1H), 7.39-7.34 (m, 1H), 5.43 (d, J=6.4 Hz, 1H), 2.57 (s, 3H), 2.43-2.37 (m, 1H), 1.88 (dtd, J=4.6, 6.1, 7.9 Hz, 1H), 1.29 (s, 9H), 1.08 (dt, J=5.0, 7.9 Hz, 1H), 0.64-0.59 (m, 1H)

(1aS,6S,6aR)—N-methyl-3-(trifluoromethyl)-1,1a,6,6a-tetrahydrocyclopropa[a]inden-6-amine. (Eab-3). A solution of (S)—N,2-dimethyl-N-((1aS,6S,6aR)-3-(trifluoromethyl)-1,1a,6,6a-tetrahydrocyclopropa[a]inden-6-yl)propane-2-sulfinamide (0.266 g, 0.8 mmol) in hydrochloric acid/ethyl acetate (3.0 mL, 4M). The mixture was stirred at 25° C. for 2 hr. The reaction mixture was filtered, concentrated, and purified by prep-HPLC (HCl condition; column: Phenomenex luna C18 100*40 mm*5 um; mobile phase: [A: $H_2O$ (0.04% HCl); B: ACN];B %: 5.00%-30.00%, 8.00 min) to give title compound. ES/MS: m/z =228.2 $[M+H]^+$. $^1H$ NMR (400 MHz, DMSO-$d_6$) δ 9.59-9.36 (m, 2H), 7.90-7.83 (m, 2H), 7.63 (br d, J=7.9 Hz, 1H), 4.74 (br s, 1H), 2.79-2.71 (m, 1H), 2.49 (br s, 3H), 2.31 (td, J=4.6, 8.8 Hz, 1H), 1.35 (dt, J=4.8, 8.2 Hz, 1H), 0.17 (q, J=4.3 Hz, 1H).

(1aR,6S,6aS)—N-methyl-3-(trifluoromethyl)-1,1a,6,6a-tetrahydrocyclopropa[a]inden-6-amine (Eab-4). A solution of (S)—N,2-dimethyl-N-((1aR,6S,6aS)-3-(trifluoromethyl)-1,1a,6,6a-tetrahydrocyclopropa[a]inden-6-yl)propane-2-sulfinamide (0.282 g, 0.851 mmol) in hydrochloric acid/ethyl acetate (3.00 mL, 4M) was stirred at 25° C. for 2 hr. The reaction mixture was filtered, concentrated, and purified by prep-HPLC (HCl condition; column: Phenomenex luna C18 100*40 mm*5 um; mobile phase: [A: H2O(0.04% HCl);B: ACN];B %: 5.00%-30.00%, 8.00 min) to give title compound. ES/MS: m/z=228.2 $[M+H]^+$. $^1H$ NMR (400 MHz, DMSO-$d_6$) δ 10.59 (br s, 1H), 9.08-8.89 (m, 1H), 7.99 (br d, J=7.9 Hz, 1H), 7.71 (s, 1H), 7.61 (br d, J=7.8 Hz, 1H), 5.12 (br s, 2H), 2.81-2.70 (m, 3H), 2.26-2.12 (m, 1H), 1.14 (br s, 1H), 0.92 (q, J=4.0 Hz, 1H).

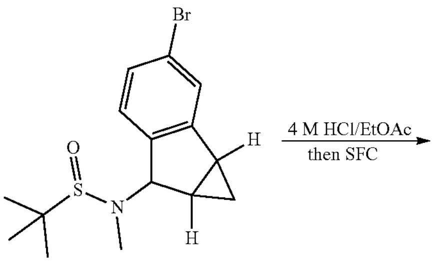

-continued

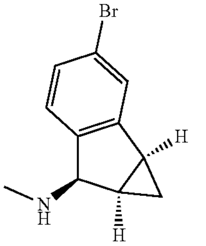 + 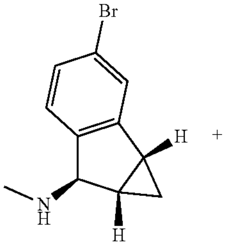 +

Eab-5 Eab-6

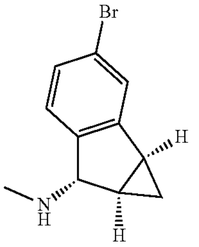 + 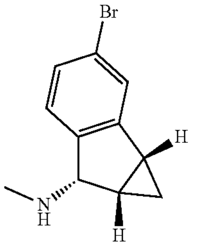

Eab-7 Eab-8

(1aS,6R,6aR)-3-bromo-N-methyl-1,1a,6,6a-tetrahydrocyclopropa[a]inden-6-amine (Eab-5), (1aR,6R,6aS)-3-bromo-N-methyl-1,1a,6,6a-tetrahydrocyclopropa[a]inden-6-amine (Eab-6), (1aS,6R,6aR)-3-bromo-N-methyl-1,1a,6,6a-tetrahydrocyclopropa[a]inden-6-amine (Eab-7), and (1aR,6R,6aS)-3-bromo-N-methyl-1,1a,6,6a-tetrahydrocyclopropa[a]inden-6-amine (Eab-8). Prepared following procedure XXVIII-E starting with 5-bromoindan-1-one in step 1 and racemic 2-methylpropane-2-sulfinamide in step 5. SFC separation of step 8 HCl de-protection gave peak 1 and peak 2, which were mixtures of diastereomer pairs Eab-5 and Eab-7 as peak 1, and Eab-6 and Eab-8 as peak 2, which were further separated by SFC to give individual compounds.

A solution of rac-N-((1rR,6rS)-3-bromo-1,1a,6,6a-tetrahydrocyclopropa[a]inden-6-yl)-N,2-dimethylpropane-2-sulfinamide (2.4 g, 7.01 mmol, 1 eq) in 4M HCl/EtOAc (4 M, 20 mL, 11.41 eq) was stirred at 20° C. for 2 hr. LC-MS showed the desired mass was detected. The reaction mixture was filtered, washed with ethyl acetate 10 mL to give a filter cake. The filter cake was diluted with ethyl acetate 10 mL and $NHCO_3$ 30 mL (adjust the pH to 8) and extracted with ethyl acetate (20 mL×2). The combined organic layers were dried over $Na_2SO_4$, filtered, and concentrated under reduced pressure. The residue was purified by prep-SFC (column: DAICEL CHIRALPAK IC (250 mm*30 mm, 10 um); mobile phase: [$CO_2$—MeOH (0.1% $NH_3H_2O$)];B %: 33%, isocratic elution mode) to give peak 1 (RT=1.8 min) and peak 2 (RT=1.95 min), each containing 2 enantiomers to be further separated.

Peak 1 was further purified by prep-SFC (ChiralPak IH, 250*30 mm, 10 um; mobile phase: [$CO_2$-MeOH (0.1% $NH_3H_2O$)];B %: 12%, isocratic elution mode) to give (1aS, 6R,6aR)-3-bromo-N-methyl-1,1a,6,6a-tetrahydrocyclopropa[b]inden-6-amine (Eab-5) (RT=1.920 min) and (1aR, 6S,6aS)-3-bromo-N-methyl-1,1a,6,6a-tetrahydrocyclopropa[a]inden-6-amine (Eab-8) (RT=2.055 min).

Eab-5: ES/MS: m/z=238.1/240.1 $[M+H]^+$. $^1H$ NMR (400 MHz, DMSO-$d_6$) δ 7.40 (d, J=1.8 Hz, 1H), 7.28-7.21 (m, 1H), 7.11 (d, J=8.0 Hz, 1H), 4.32 (d, J=6.0 Hz, 1H), 2.45 (s, 3H), 2.41-2.34 (m, 1H), 2.03-1.95 (m, 1H), 0.91-0.83 (m, 1H), 0.35-0.27 (m, 1H).

Eab-8: ES/MS: m/z=238.1/240.1 $[M+H]^+$. $^1H$ NMR (400 MHz, DMSO-$d_6$) δ 7.40 (d, J=1.8 Hz, 1H), 7.28-7.21 (m, 1H), 7.12 (d, J=8.0 Hz, 1H), 4.33 (d, J=6.0 Hz, 1H), 2.45 (s, 3H), 2.42-2.34 (m, 1H), 2.02-1.94 (m, 1H), 0.92-0.83 (m, 1H), 0.34-0.28 (m, 1H).

P2 was further purified by prep-SFC (DAICEL CHIRALCEL OZ 250*25 mm I.D. 10 um; mobile phase: [$CO_2$-MeOH (0.1% $NH_3H_2O$)];B %: 25%, isocratic elution mode) to give (1aR,6R,6aS)-3-bromo-N-methyl-1,1a,6,6a-tetrahydrocyclopropa[a]inden-6-amine (Eab-6) (RT=1.191 min) as and (1aS,6S,6aR)-3-bromo-N-methyl-1,1a,6,6a-tetrahydrocyclopropa[a]inden-6-amine (Eab-7) (RT=1.440 min).

Eab-6: ES/MS: m/z=238.1/240.1 $[M+H]^+$. $^1H$ NMR (400 MHz, DMSO-$d_6$) δ 7.50 (d, J=1.5 Hz, 1H), 7.30-7.22 (m, 2H), 3.88-3.84 (m, 1H), 2.46-2.36 (m, 1H), 2.23 (s, 3H), 2.14-2.01 (m, 1H), 2.01-1.90 (m, 1H), 1.18-1.12 (m, 1H), −0.04-−0.08 (m, 1H).

Eab-7: ES/MS: m/z=238.1/240.1 $[M+H]^+$. $^1H$ NMR (400 MHz, DMSO-$d_6$) δ 7.49 (d, J=1.5 Hz, 1H), 7.31-7.20 (m, 2H), 3.85 (d, J=1.4 Hz, 1H), 2.44-2.36 (m, 1H), 2.22 (s, 3H), 2.14-1.99 (m, 1H), 1.98-1.90 (m, 1H), 1.20-1.09 (m, 1H), −0.02111−0.11 (m, 1H).

General Procedure XXIX-E for the Synthesis of Intermediates Eac:

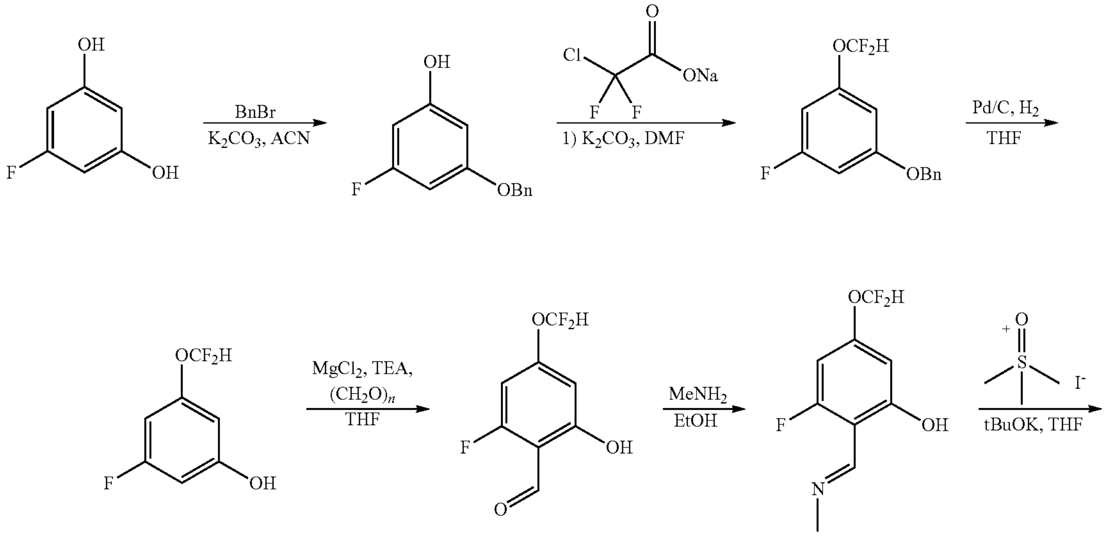

-continued

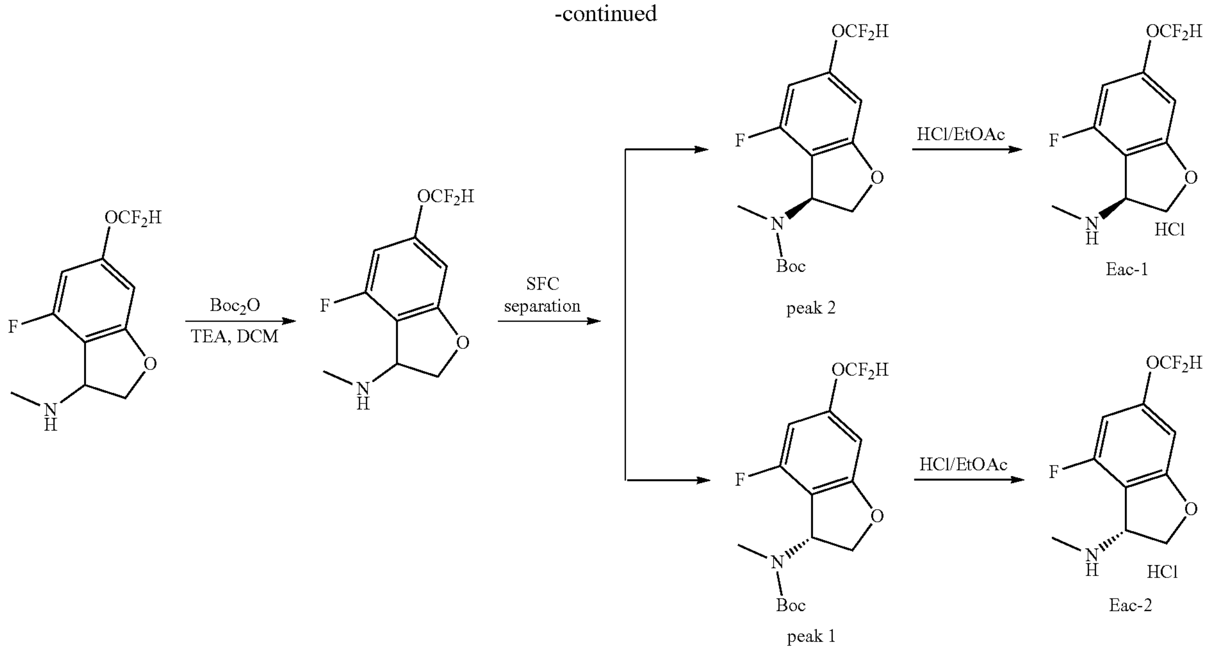

Step 1: 3-(benzyloxy)-5-fluorophenol. To a solution of 5-fluorobenzene-1,3-diol (10.0 g, 78.0 mmol) in Dimethylformamide (100 mL) was added potassium carbonate (16.2 g, 110.0 mmol) and bromomethylbenzene (13.4 g, 78.1 mmol). The mixture was stirred at 120° C. for 12 hr. LC-MS showed Reactant 1 was consumed completely and the desired mass was detected. The reaction mixture was partitioned between $H_2O$ 200 mL and Ethyl acetate 300 mL (100 mL×3). The organic phase was separated, washed with brine 300 mL (100 mL×3), dried over $Na_2SO_4$, filtered, and concentrated under reduced pressure to give a residue. The residue was purified by flash silica gel chromatography to give product. ES/MS: m/z=219.0 $[M+H]^+$. $^1H$ NMR (400 MHz, DMSO-$d_6$) δ 7.95 (s, 1H), 7.45-7.40 (m, 5H), 7.33-7.30 (m, 3H), 5.04 (s, 2H).

Step 2: 1-(benzyloxy)-3-(difluoromethoxy)-5-fluorobenzene. To a solution of 3-(benzyloxy)-5-fluorophenol (8.7 g, 39.9 mmol) in DMF (100.0 mL) was added potassium carbonate (11.0 g, 79.7 mmol). The mixture was stirred at 100° C. for 15 min. (2-chloro-2,2-difluoro-acetyl)oxysodium (12.2 g, 79.7 mmol) was added to the mixture. The mixture was stirred at 100° C. for 12 hr. The reaction mixture was partitioned between $H_2O$ 100 mL and Ethyl acetate 300 mL (100 mL×3). The organic phase was separated, washed with brine 300 mL (100 mL×3), dried over $Na_2SO_4$, filtered, and concentrated under reduced pressure to give a residue. The residue was purified by flash silica gel chromatography to give product. ES/MS: m/z=269.0 $[M+H]^+$. $^1H$ NMR (400 MHz, DMSO-$d_6$) δ 7.46-7.39 (m, 5H), 7.31-7.10 (m, 1H), 6.83 (td, J=2.2, 10.9 Hz, 1H), 6.71 (d, J=2.1 Hz, 1H), 6.54-6.47 (m, 1H), 5.13 (s, 2H)

Step 3: 3-(difluoromethoxy)-5-fluorophenol. To a solution of Pd/C (10.0%, 3.0 g, 2.8 mmol) in tetrahydrofuran (100.0 mL) was added 1-(benzyloxy)-3-(difluoromethoxy)-5-fluorobenzene (5.6 g, 20.9 mmol) under $N_2$ atmosphere. The suspension was degassed and purged with $H_2$ for 3 times. The mixture was stirred under $H_2$ (15 psi) at 25° C. for 2 hr. The suspension was filtered through a pad of Celite and the pad was washed with Ethyl acetate (300 mL×3). The filtrate was collected and concentrated under reduced pressure to give product used into the next step without further purification. $^1H$ NMR (400 MHz, DMSO-$d_6$) δ 9.70-9.59 (m, 1H), 7.24 (t, J=73.7 Hz, 1H), 6.53-6.43 (m, 2H), 6.41 (s, 1H).

Step 4: 4-(difluoromethoxy)-2-fluoro-6-hydroxybenzaldehyde. To a solution of paraformaldehyde (11.4 g, 126.0 mmol) in Tetrahydrofuran (100 mL) was added Triethylamine (7.6 g, 75.8 mmol) and dichloromagnesium (4.8 g, 50.5 mmol). The mixture was stirred at 25° C. for 15 min under $N_2$. 3-(difluoromethoxy)-5-fluorophenol (4.5 g, 25.3 mmol) was added to the mixture. The mixture was stirred at 75° C. for 12 hr under $N_2$. The reaction mixture was partitioned between $H_2O$ 100 mL and Ethyl acetate 300 mL (100 mL×3). The organic phase was separated, washed with brine 300 mL (100 mL×3), dried over $Na_2SO_4$, filtered, and concentrated under reduced pressure to give a residue. The residue was purified by flash silica gel chromatography to give product. ES/MS: m/z=205.0 $[M+H]^+$. $^1H$ NMR (400 MHz, DMSO-$d_6$) δ 11.75 (br s, 1H), 10.16 (s, 1H), 7.43-7.24 (m, 1H), 6.82-6.67 (m, 2H).

Step 5: (E)-5-(difluoromethoxy)-3-fluoro-2-((methylimino)methyl)phenol. To a solution of 4-(difluoromethoxy)-2-fluoro-6-hydroxybenzaldehyde (0.6 g, 2.9 mmol) in ethanol (20.0 mL) was added methanamine (33.0%, 0.2 g, 2.9 mmol). The mixture was stirred at 25° C. for 12 hr. The reaction mixture was concentrated under reduced pressure to remove solvent. The reaction mixture was partitioned between $NH_4Cl$ 30 mL and Ethyl acetate 90 mL (30 mL×3). The organic phase was separated, washed with brine 90 mL (30 mL×3), dried over $Na_2SO_4$, filtered, and concentrated under reduced pressure to give crude product, which was used into the next step without further purification. ES/MS: m/z=219.9 $[M+H]^+$. $^1H$ NMR (400 MHz, DMSO-$d_6$) δ 8.62-8.53 (m, 2H), 7.33 (d, J=5.8 Hz, 1H), 6.21 (dd, J=2.2, 4.1 Hz, 1H), 3.33 (br s, 3H).

Step 6: 6-(difluoromethoxy)-4-fluoro-N-methyl-2,3-dihydrobenzofuran-3-amine. To a solution of trimethylsulfoxonium iodide (1.4 g, 6.3 mmol) in THF (20 mL) was added Potassium tert-butoxide (0.7 g, 6.3 mmol). The mixture was stirred at 25° C. for 30 min. (E)-5-(difluoromethoxy)-3-fluoro-2-((methylimino)methyl)phenol (80.0%, 0.7 g, 2.5 mmol) in THF (5 mL) was added to the mixture at 25° C. under $N_2$. The mixture was stirred at 50° C. for 1 hr under $N_2$. The suspension was filtered through a pad of Celite and the pad was washed with Ethyl acetate (10 mL×3). The filtrate was collected and concentrated under reduced pressure to give crude product used into the next step without further purification. ES/MS: m/z=234.0 $[M+H]^+$.

Step 7: tert-butyl (S)-(6-(difluoromethoxy)-4-fluoro-2,3-dihydrobenzofuran-3-yl)(methyl)carbamate & tert-butyl (R)-(6-(difluoromethoxy)-4-fluoro-2,3-dihydrobenzofuran-3-yl)(methyl)carbamate. To a solution of 6-(difluoromethoxy)-4-fluoro-N-methyl-2,3-dihydrobenzofuran-3-amine (0.9 g, 3.8 mmol) in dichloromethane (10.0 mL) was added Triethylamine (0.7 g, 7.7 mmol) and tert-butoxycarbonyl tert-butyl carbonate (1.2 g, 5.7 mmol). The mixture was stirred at 25° C. for 12 hr. The reaction mixture was partitioned between $H_2O$ 30 mL and Ethyl acetate 60 mL (20 mL×3). The organic phase was separated, washed with brine 60 mL (20 mL×3), dried over $Na_2SO_4$, filtered, and concentrated under reduced pressure to give a residue. The residue was purified by flash silica gel chromatography. The residue was passed through a syringe filter and the filtrate was purified by prep-HPLC (basic condition; column: DAICEL CHIRALCEL OJ (250 mm*30 mm, 10 um); mobile phase: [A: Heptane;B: IPA];B %: 5.00%-5.00%, 10.00 min) to give peak 2 tert-butyl (S)-(6-(difluoromethoxy)-4-fluoro-2,3-dihydrobenzofuran-3-yl)(methyl)carbamate (RT 0.769 min) and peak 1 tert-butyl (R)-(6-(difluoromethoxy)-4-fluoro-2,3-dihydrobenzofuran-3-yl)(methyl)carbamate (RT 0.687 min). ES/MS: m/z=278.0 $[M+H]^+$.

Step 8: (S)-6-(difluoromethoxy)-4-fluoro-N-methyl-2,3-dihydrobenzofuran-3-amine hydrochloride (Eac-1). A mixture of tert-butyl (S)-(6-(difluoromethoxy)-4-fluoro-2,3-dihydrobenzofuran-3-yl)(methyl)carbamate (0.03 g, 9.00e-5 mol) in hydrogen chloride (4.0 mol/L in Ethyl acetate, 1.0 mL, 4.0 mmol) was stirred at 25° C. for 1 hr. The reaction mixture was concentrated under reduced pressure to remove solvent to give title product. ES/MS: m/z=234.1 $[M+H]^+$. $^1H$ NMR (400 MHz, DMSO-$d_6$) δ 9.44 (br s, 2H), 7.36 (t, J=73.2 Hz, 1H), 6.85-6.76 (m, 2H), 5.23-5.16 (m, 1H), 4.89 (dd, J=1.9, 11.4 Hz, 1H), 4.75 (dd, J=7.5, 11.5 Hz, 1H), 2.56 (s, 3H).

Step 8: (R)-6-(difluoromethoxy)-4-fluoro-N-methyl-2,3-dihydrobenzofuran-3-amine hydrochloride (Eac-2). A mixture of tert-butyl (R)-(6-(difluoromethoxy)-4-fluoro-2,3-dihydrobenzofuran-3-yl)(methyl)carbamate (0.02 g, 6.00e-5 mol) in hydrogen chloride (4.0 mol/L in Ethyl acetate, 1.0 mL, 4.0 mmol) was stirred at 25° C. for 1 hr. The reaction mixture was concentrated under reduced pressure to remove solvent to give title product. ES/MS: m/z=234.1 $[M+H]^+$. $^1H$ NMR (400 MHz, DMSO-$d_6$) δ 9.57 (br s, 2H), 7.36 (t, J=73.2 Hz, 1H), 6.83-6.74 (m, 2H), 5.19 (dd, J=1.6, 7.3 Hz, 1H), 4.91 (dd, J=1.9, 11.4 Hz, 1H), 4.75 (dd, J=7.5, 11.5 Hz, 1H), 2.55 (s, 3H).

General Procedure XXX-E for the Synthesis of Intermediates Ead:

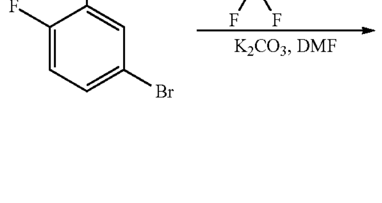

-continued

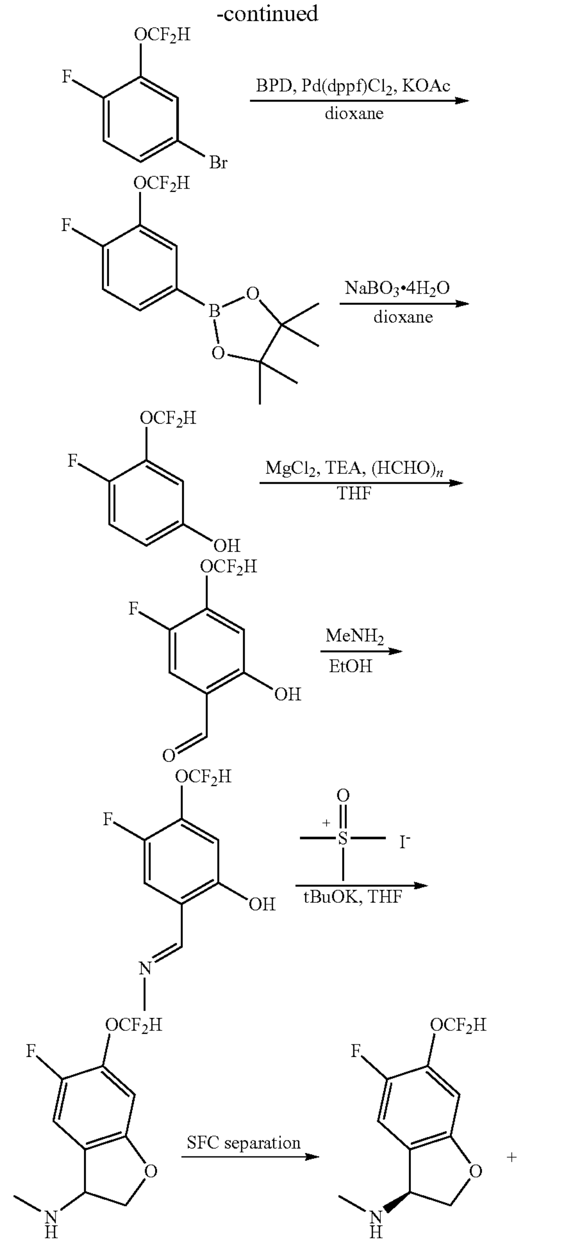

Ead-1
peak 1

Ead-2
peak 2

Step 1: 4-bromo-2-(difluoromethoxy)-1-fluorobenzene. To a solution of 5-bromo-2-fluoro-phenol (35.0 g, 183 mmol) in Dimethylformamide (400 mL) was added (2-chloro-2,2-difluoro-acetyl) oxysodium (55.9 g, 366 mmol) and potassium carbonate (50.7 g, 366 mmol). The mixture was stirred at 110° C. for 3 hrs. The reaction was clean according to TLC. The reaction mixture was concentrated under reduced pressure to remove solvent. The residue was diluted with water 100 mL and extracted with Ethyl acetate (200 mL×3). The combined organic layers were washed with brine (200 mL×3), dried over $Na_2SO_4$, filtered, and concentrated under reduced pressure to give a residue. The residue was purified by flash silica gel chromatography to give product. $^1$H NMR (400 MHz, CHLOROFORM-d) δ 7.45-7.39 (m, 1H), 7.38-7.30 (m, 1H), 7.07 (t, J=9.4 Hz, 1H), 6.56 (t, J=72.9 Hz, 1H).

Step 2: 2-(3-(difluoromethoxy)-4-fluorophenyl)-4,4,5,5-tetramethyl-1,3,2-dioxaborolane. A mixture of 4-bromo-2-(difluoromethoxy)-1-fluorobenzene (11.0 g, 456 mmol), Bis (pinacolato)diboron (13.9 g, 548 mmol), potassium acetate (21.4 g, 114 mmol) and (1,1'-bis(diphenylphosphino)ferrocene)-dichloropalladium(II) (6.2 g, 4.7 mmol) in 1,4-Dioxane (100 mL) was degassed and purged with $N_2$ for 3 times, the mixture was then stirred at 90° C. for 2 hrs under $N_2$ atmosphere. The reaction mixture was concentrated under reduced pressure to remove solvent. The residue was diluted with water 100 mL and extracted with Ethyl acetate (200 mL×3). The combined organic layers were washed with brine (200 mL×3), dried over $Na_2SO_4$, filtered, and concentrated under reduced pressure to give a residue. The residue was purified by flash silica gel chromatography to give product. $^1$H NMR (400 MHz, CHLOROFORM-d) δ 7.70-7.61 (m, 2H), 7.17 (dd, J=8.6, 10.4 Hz, 1H), 6.57 (t, J=73.6 Hz, 1H), 1.37-1.33 (m, 12H)

Step 3: 3-(difluoromethoxy)-4-fluorophenol. To a solution of 2-(3-(difluoromethoxy)-4-fluorophenyl)-4,4,5,5-tetramethyl-1,3,2-dioxaborolane (6.0 g, 41.7 mmol) in tetrahydrofuran (50.0 mL) and water (25.0 mL) was added 3-oxidodioxaborirane;tetrahydrate (9.5 g, 146 mmol). The mixture was stirred at 25° C. for 2 hr. The reaction mixture was quenched by addition of 50 ml HCl (2 M). The reaction mixture was partitioned between $H_2O$ 200 mL and Ethyl acetate 300 mL (100 mL×3). The organic phase was separated, washed with brine 300 mL (100 mL×3), dried over $Na_2SO_4$, filtered, and concentrated under reduced pressure to give a residue. The residue was purified by flash silica gel chromatography to give product. $^1$H NMR (400 MHz, CHLOROFORM-d) δ 7.03 (t, J=9.5 Hz, 1H), 6.79-6.71 (m, 1H), 6.65 (td, J=3.2, 8.9 Hz, 1H), 6.56-6.33 (m, 1H), 5.50 (br s, 1H).

Step 4: 4-(difluoromethoxy)-5-fluoro-2-hydroxybenzaldehyde. A solution of paraformaldehyde (18.5 g, 205 mmol) and dichloromagnesium (7.8 g, 82.0 mmol) in tetrahydrofuran (100 mL) was stirred at 25° C. for 0.5 hr under $N_2$. 3-(difluoromethoxy)-4-fluorophenol (7.3 g, 41.0 mmol) in tetrahydrofuran (50.0 mL) was added the mixture. The mixture was stirred at 70° C. for 12 hrs under $N_2$. The reaction mixture was quenched by addition of 50 mL HCl (1 M). The reaction mixture was partitioned between $H_2O$ 200 mL and Ethyl acetate 300 mL (100 mL×3). The organic phase was separated, washed with brine 300 mL (100 mL×3), dried over $Na_2SO_4$, filtered, and concentrated under reduced pressure to give a residue. The residue was purified by flash silica gel chromatography to give product. $^1$H NMR (400 MHz, CHLOROFORM-d) 6=11.09 (s, 1H), 9.80 (s, 1H), 7.37 (d, J=9.5 Hz, 1H), 6.88-6.81 (m, 1H), 6.69-6.46 (m, 1H).

Step 5: (E)-5-(difluoromethoxy)-4-fluoro-2-((methylimino)methyl)phenol. A mixture of 4-(difluoromethoxy)-5-fluoro-2-hydroxybenzaldehyde (4.8 g, 23.3 mmol) in ethanol (50.0 mL). Then the methanamine (33.0%, 4.4 g, 46.6 mmol) was added the above mixture was degassed and purged with $N_2$ for 3 times, the mixture was then stirred at 40° C. for 12 hrs under $N_2$ atmosphere. The reaction mixture was concentrated under reduced pressure to remove solvent to give crude product, which used into the next step without further purification. $^1$H NMR (400 MHz, CHLOROFORM-d) δ 13.81-13.49 (m, 1H), 8.24 (d, J=1.4 Hz, 1H), 7.04 (d, J=10.3 Hz, 1H), 6.80-6.40 (m, 2H), 3.49 (d, J=1.4 Hz, 3H).

Step 6: (S)-6-(difluoromethoxy)-5-fluoro-N-methyl-2,3-dihydrobenzofuran-3-amine (Ead-1) and (R)-6-(difluoromethoxy)-5-fluoro-N-methyl-2,3-dihydrobenzofuran-3-amine (Ead-2) To a solution of trimethylsulfoxonium iodide (10.0 g, 45.6 mmol) in tetrahydrofuran (100 mL) was added Potassium tert-butoxide (5.1 g, 45.6 mmol). The mixture was stirred at 20° C. for 0.5 hr. Then the (E)-5-(difluoromethoxy)-4-fluoro-2-((methylimino)methyl)phenol (4.0 g, 18.3 mmol) in tetrahydrofuran (50.0 mL) was added to above solution and then the mixture was stirred at 20° C. for 1 hr and 50° C. for 3 hrs under $N_2$ atmosphere. The suspension was filtered through a pad of Celite and the pad was washed with THF (200 mL×3). The filtrate was collected and concentrated under reduced pressure to give product as a yellow oil. The crude product 6-(difluoromethoxy)-5-fluoro-N-methyl-2,3-dihydrobenzofuran-3-amine (3.0 g, 12.9 mmol, yield: 70.5%) was purified by prep-HPLC ($NH_4HCO_3$ condition column: Phenomenex luna C18 100*40 mm*5 um; mobile phase: [A: $H_2O$(0.04% HCl);B: ACN];B %: 1.00%-25.00%, 8.00 mi) to give residue, which was further separated by SFC (Heptane-EtOH (0.1% IPAm) condition, column: Daicel ChiralPak IG (250*30 mm, 10 um); mobile phase: [A: Heptane;B: EtOH (0.1% IPAm)];B %: 30.00%-50.00%, 8.00 min) to isolate (3S)-6-(difluoromethoxy)-5-fluoro-N-methyl-2,3-dihydrobenzofuran-3-amine (peak 1, RT 2.204 min) and (3R)-6-(difluoromethoxy)-5-fluoro-N-methyl-2,3-dihydrobenzofuran-3-amine (peak 2, RT 2.762 min).

Peak 1. (3S)-6-(difluoromethoxy)-5-fluoro-N-methyl-2,3-dihydrobenzofuran-3-amine (Ead-1). ES/MS: m/z=234.1 $[M+H]^+$. $^1$H NMR (400 MHz, DMSO-d6) δ=9.83 (br s, 2H), 7.81 (d, J=9.9 Hz, 1H), 7.30 (t, J=73.0 Hz, 1H), 7.05 (d, J=6.4 Hz, 1H), 5.06 (dd, J=2.3, 7.9 Hz, 1H), 4.84 (dd, J=3.0, 11.5 Hz, 1H), 4.75-4.66 (m, 1H), 2.49 (s, 3H).

Peak 2. (3R)-6-(difluoromethoxy)-5-fluoro-N-methyl-2,3-dihydrobenzofuran-3-amine (Ead-2). ES/MS: m/z=234.1 $[M+H]^+$. $^1$H NMR (400 MHz, DMSO-d6) δ=9.79-9.56 (m, 2H), 7.82-7.72 (m, 1H), 7.29 (t, J=73.0 Hz, 1H), 7.05 (d, J=6.4 Hz, 1H), 5.05 (br d, J=7.5 Hz, 1H), 4.89-4.79 (m, 1H), 4.74-4.66 (m, 1H), 2.50 (d, J=1.9 Hz, 3H).

General Procedure XXXI-E for the Synthesis of Intermediates Eae:

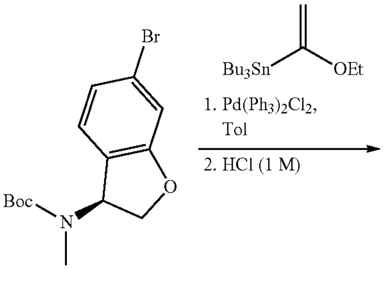

-continued

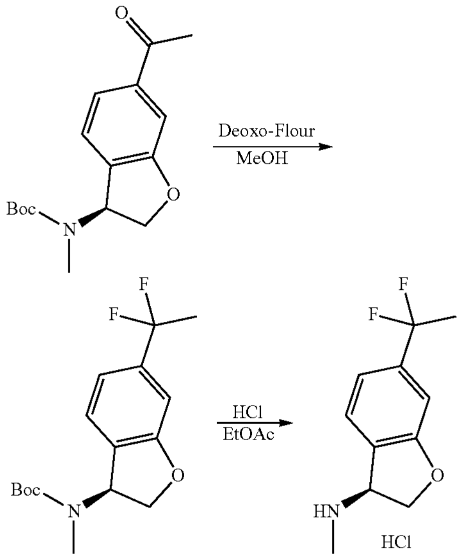

Eae-1

Step 1: tert-butyl (S)-(6-acetyl-2,3-dihydrobenzofuran-3-yl)(methyl)carbamate. To a solution of tert-butyl (S)-(6-bromo-2,3-dihydrobenzofuran-3-yl)(methyl)carbamate (prepared according to general procedure VIII-E starting with (S)-6-bromo-2,3-dihydrobenzofuran-3-amine hydrochloride, 1.0 g, 3.05 mmol) in toluene (10.0 mL) was added tributyl(1-ethoxyvinyl)stannane (1.32 g, 3.66 mmol). Then bis(triphenylphosphine)palladium chloride (0.0855 g, 0.122 mmol) was added to the solution at 25° C. under $N_2$ atmosphere. The mixture was stirred at 90° C. for 16 hr under $N_2$ atmosphere. The reaction mixture was stirred with 1N HCl (40 mL), then quenched by addition KF 50 mL, and then extracted with ethyl acetate (50 mL×3). The combined organic layers were washed with brine (30 mL×3), dried over $Na_2SO_4$, filtered, and concentrated under reduced pressure to give a residue. The residue was purified by flash silica gel chromatography to give product. ES/MS: m/z=236.1 $[M-55]^+$. $^1H$ NMR (400 MHz, CHLOROFORM-d) δ 7.56 (dd, J=1.4, 7.8 Hz, 1H), 7.41 (d, J=1.1 Hz, 1H), 7.32 (br d, J=7.5 Hz, 1H), 6.18-5.75 (m, 1H), 4.68 (br t, J=9.8 Hz, 1H), 4.44 (brs, 1H), 2.64-2.48 (m, 6H), 1.51 (s, 9H).

Step 2: (S)-tert-butyl (6-(difluoromethyl)-2,3-dihydrobenzofuran-3-yl)(methyl)carbamate. To a solution of tert-butyl (S)-(6-acetyl-2,3-dihydrobenzofuran-3-yl)(methyl) carbamate (0.6 g, 2.06 mmol) in bis(2-methoxyethyl) aminosulfur Trifluoride (10.0 mL) was added methanol (0.0100 mL, 0.021 mmol) under $N_2$ atmosphere. The mixture was stirred at 60° C. for 16 hr under $N_2$ atmosphere. The reaction mixture was quenched by addition ice water 200 mL at 0° C., neutralize with saturated sodium bicarbonate (300 mL) and then extracted with Ethyl acetate (500 mL×3). The combined organic layers were washed with brine (300 mL×3), dried over $Na_2SO_4$, filtered, and concentrated under reduced pressure to give a residue. The residue was purified by flash silica gel chromatography to give product. ES/MS: m/z=258.2 $[M-55]^+$. $^1H$ NMR (400 MHz, CHLOROFORM-d) δ 7.27 (s, 1H), 7.08 (d, J=7.8 Hz, 1H), 6.98 (s, 1H), 6.15-5.73 (m, 1H), 4.65 (br t, J=9.6 Hz, 1H), 4.41 (br d, J=6.8 Hz, 1H), 2.55 (br s, 3H), 1.91 (t, J=18.1 Hz, 3H), 1.50 (s, 9H).

Step 3: (S)-6-(1,1-difluoroethyl)-N-methyl-2,3-dihydrobenzofuran-3-amine hydrochloride (Eae-1). A solution of (S)-tert-butyl (6-(difluoromethyl)-2,3-dihydrobenzofuran-3-yl)(methyl)carbamate (0.4 g, 1.28 mmol) in HCl/Ethyl acetate (3.0 mL, 4M in EtOAc). The mixture was stirred at 25° C. for 2 hr. The reaction mixture was concentrated under reduced pressure to give a residue. The residue was triturated with Ethyl acetate (3 mL) at 25° C. for 1 hr. The residue was filtered, washed with Ethyl acetate (3 mL) and then the filter cake was dried under reduced pressure to give desired product. ES/MS: m/z=183.0 $[M-NHMe+H]^+$. $^1H$ NMR (400 MHz, DMSO-d6) δ 9.51 (br s, 2H), 7.77 (d, J=7.9 Hz, 1H), 7.21 (dd, J=0.6, 7.9 Hz, 1H), 7.14 (s, 1H), 5.08 (dd, J=2.4, 7.8 Hz, 1H), 4.85-4.79 (m, 1H), 4.74-4.66 (m, 1H), 2.53 (s, 3H), 1.95 (t, J=18.9 Hz, 3H).

General Procedure XXXII-E for the Synthesis of Intermediates Eaf:

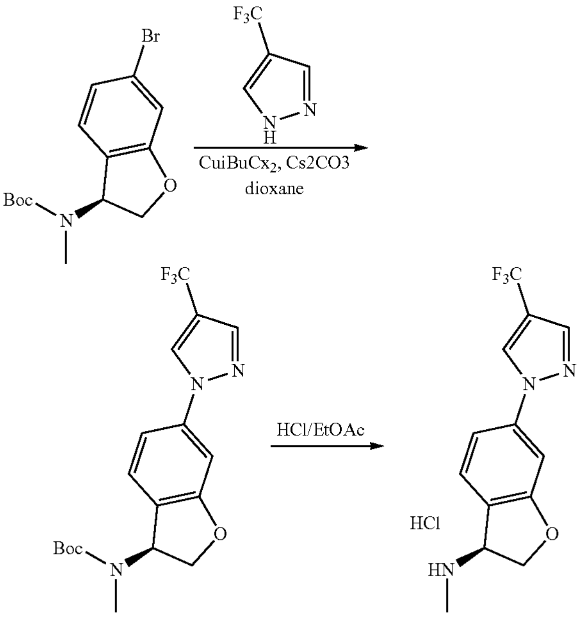

Eaf-1

Step 1: tert-butyl (S)-methyl(6-(4-(trifluoromethyl)-1H-pyrazol-1-yl)-2,3-dihydrobenzofuran-3-yl)carbamate. To a solution of tert-butyl N-[(3S)-6-bromo-2,3-dihydrobenzofuran-3-yl]-N-methyl-carbamate (prepared according to general procedure VIII-E starting with (S)-6-bromo-2,3-dihydrobenzofuran-3-amine hydrochloride, 250 mg, 761.7 μmol, 1 eq) in dioxane (10 mL) was added 4-(trifluoromethyl)-1H-pyrazole (155.4 mg, 1.1 mmol, 1.5 eq), cesium carbonate (496.3 mg, 1.5 mmol, 2 eq) and bis[(1Z)-2-methyl-1-(2-oxocyclohexylidene)propoxy]copper (30.3 mg, 76.1 μmol, 0.1 eq). The mixture was stirred at 120° C. for 12 hr under $N_2$. The reaction mixture was partitioned between $H_2O$ 30 mL and EtOAc 30 mL. The water phase was separated, extracted with EtOAc (30 mL×3). The combined organic phase was washed with brine (30 mL×3), dried over $Na_2SO_4$, filtered, and concentrated under reduced pressure to give a residue. The residue was purified by flash silica gel chromatography to give product. ES/MS: m/z=328.0 $[M-55]^+$. $^1H$ NMR (400 MHz, DMSO-$d_6$) δ 9.18 (s, 1H), 8.20 (s, 1H), 7.49 (dd, J=1.9, 8.1 Hz, 1H), 7.42 (d, J=1.6 Hz, 1H), 7.37 (br d, J=8.0 Hz, 1H), 6.03-5.66 (m, 1H), 4.77-4.64 (m, 1H), 4.59-4.45 (m, 1H), 2.54-2.52 (m, 3H), 1.43 (br s, 9H).

Step 2: (S)—N-methyl-6-(4-(trifluoromethyl)-1H-pyrazol-1-yl)-2,3-dihydrobenzofuran-3-amine hydrochloride (Eaf-1). The solution of tert-butyl N-methyl-N-[(3S)-6-[4-(trifluoromethyl)pyrazol-1-yl]-2,3-dihydrobenzofuran-3-yl] carbamate (250 mg, 652.1 mol, 1 eq) in 1M HCl/EtOAc (3 mL) was stirred at 25° C. for 12 hr. The reaction mixture was concentrated under reduced pressure to remove solvent. The residue was purified by prep-HPLC (HCl condition; column: Phenomenex luna C18 100*40 mm*5 um; mobile phase: [$H_2O$(0.04% HCl)-ACN]; gradient:10%-40% B over 8.0 min) to give title product. ES/MS: m/z =253.1 $[M-NHMe]^+$. $^1H$ NMR (400 MHz, DMSO-$d_6$) δ 9.42 (br s, 2H), 9.24 (s, 1H), 8.24 (s, 1H), 7.79 (d, J=8.3 Hz, 1H), 7.58 (dd, J=1.9, 8.3 Hz, 1H), 7.54 (d, J=1.8 Hz, 1H), 5.08 (dd, J=2.5, 7.8 Hz, 1H), 4.89-4.82 (m, 1H), 4.79-4.71 (m, 1H), 2.55 (s, 3H).

Eaf-2

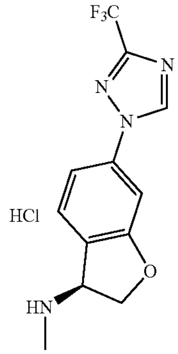

(S)—N-methyl-6-(3-(trifluoromethyl)-1H-1,2,4-triazol-1-yl)-2,3-dihydrobenzofuran-3-amine hydrochloride (Eaf-2). Prepared using general procedure XXXII-E starting with 3-(trifluoromethyl)-1H-1,2,4-triazole. ES/MS: m/z=285.2 $[M+H]^+$. 1H NMR (400 MHz, DMSO-$d_6$) δ 9.62 (s, 1H), 9.55 (br s, 2H), 7.93-7.80 (m, 1H), 7.62-7.44 (m, 2H), 5.18-5.08 (m, 1H), 4.93-4.85 (m, 1H), 4.83-4.71 (m, 1H), 2.56 (s, 3H).

General Procedure XXXIII-E for the Synthesis of Intermediates Eag:

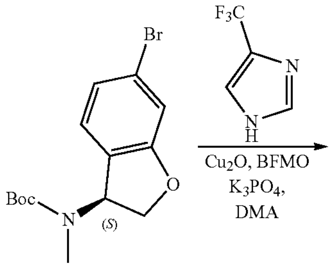

-continued

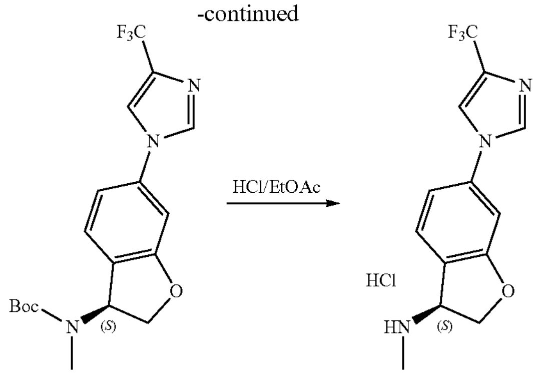

Eag-1

Step 1: tert-butyl N-methyl-N-[(3S)-6-[4-(trifluoromethyl)imidazol-1-yl]-2,3-dihydrobenzofuran-3-yl]carbamate. A mixture of tert-butyl N-[(3S)-6-bromo-2,3-dihydrobenzofuran-3-yl]-N-methyl-carbamate (prepared according to general procedure VIII-E starting with (S)-6-bromo-2,3-dihydrobenzofuran-3-amine hydrochloride, 0.5 g, 1.5 mmol, 1 eq), 4-(trifluoromethyl)-1H-imidazole (310.9 mg, 2.2 mmol, 1.5 eq), $K_3PO_4$ (646.7 mg, 3.0 mmol, 2 eq), $Cu_2O$ (21.8 mg, 152.3 μmol, 15.5 μL, 0.1 eq), N,N'-bis(2-furylmethyl)oxamide (37.8 mg, 152.3 mol, 0.1 eq) in DMSO (5 mL) was degassed and purged with $N_2$ for 3 times, and then the mixture was stirred at 120° C. for 12 hr under $N_2$ atmosphere. The reaction mixture was diluted with water 5 mL and extracted with EtOAc (5 mL×3). The combined organic layers were washed with brine (5 mL×3), dried over $Na_2SO_4$, filtered, and concentrated under reduced pressure to give a residue. The residue was purified by flash silica gel chromatography to give product. ES/MS: m/z=384.3 $[M+H]^+$. $^1H$ NMR (400 MHz, CHLOROFORM-d) δ 7.86 (s, 1H), 7.59 (s, 1H), 7.36 (br d, J=9.1 Hz, 1H), 6.96 (dd, J=1.9, 7.9 Hz, 1H), 6.87 (d, J=1.9 Hz, 1H), 6.22-5.74 (m, 1H), 4.73 (br t, J=9.7 Hz, 1H), 4.54-4.44 (m, 1H), 2.68-2.53 (m, 3H), 1.52 (s, 9H).

Step 2: (S)—N-methyl-6-(4-(trifluoromethyl)-1H-imidazol-1-yl)-2,3-dihydrobenzofuran-3-amine hydrochloride (Eag-1). To a bottle with tert-butyl N-methyl-N—[(3S)-6-[4-(trifluoromethyl)imidazol-1-yl]-2,3-dihydrobenzofuran-3-yl]carbamate (0.07 g, 182.5 mol, 1 eq) in HCl/EtOAc (2 mL) (4M). The mixture was stirred at 25° C. for 1 hr. The reaction mixture was concentrated under reduced pressure to remove solvent. The crude product was triturated with Ethyl acetate at 25° C. for 20 min. The reaction mixture was filtered and concentrated under reduced pressure to give title product. ES/MS: m/z=253.1 $[M-NMe]^+$. $^1H$ NMR (400 MHz, DMSO-$d_6$) δ 9.74 (br s, 2H), 8.52 (d, J=11.3 Hz, 2H), 7.86 (d, J=8.1 Hz, 1H), 7.46 (d, J=1.8 Hz, 1H), 7.41 (dd, J=1.9, 8.2 Hz, 1H), 5.10 (br d, J=4.5 Hz, 1H), 4.88 (dd, J=2.9, 11.4 Hz, 1H), 4.81-4.70 (m, 1H), 2.54 (s, 3H).

Eag-2

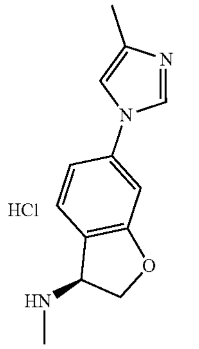

(S)—N-methyl-6-(4-methyl-1H-imidazol-1-yl)-2,3-dihydrobenzofuran-3-amine hydrochloride (Eag-2). Prepared using general procedure XXXIII-E starting with 4-methyl-1H-imidazole. ES/MS: m/z=230.1 $[M+H]^+$. $^1H$ NMR (400 MHz, DMSO-d6) δ=9.98 (brs, 2H), 9.64 (brs, 1H), 8.07-8.01 (m, 1H), 7.97 (d, J=8.1 Hz, 1H), 7.46 (d, J=1.6 Hz, 1H), 7.41 (dd, J=1.9, 8.1 Hz, 1H), 5.14 (brs, 1H), 4.92 (dd, J=3.1, 11.4 Hz, 1H), 4.82-4.74 (m, 1H), 2.54-2.51 (m, 3H), 2.35 (s, 3H)

Eag-3

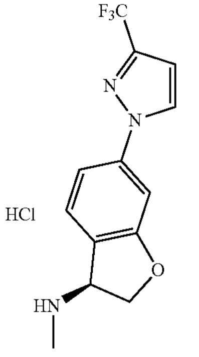

(S)—N-methyl-6-(3-(trifluoromethyl)-1H-pyrazol-1-yl)-2,3-dihydrobenzofuran-3-amine hydrochloride (Eag-3). Prepared using general procedure XXXIII-E starting with 3-(trifluoromethyl)-1H-pyrazole. ES/MS: m/z=253.1 $[M+H]^+$. $^1H$ NMR (400 MHz, $DMSO-d_6$) δ 9.78 (br s, 2H), 8.79 (d, J=1.6 Hz, 1H), 7.86 (d, J=8.3 Hz, 1H), 7.56 (dd, J=1.9, 8.2 Hz, 1H), 7.51 (d, J=1.9 Hz, 1H), 7.07 (d, J=2.5 Hz, 1H), 5.10 (br d, J=5.8 Hz, 1H), 4.89 (dd, J=2.9, 11.5 Hz, 1H), 4.79-4.72 (m, 1H), 2.52 (br s, 3H).

General Procedure XXXIV-E for the Synthesis of Intermediates Eah:

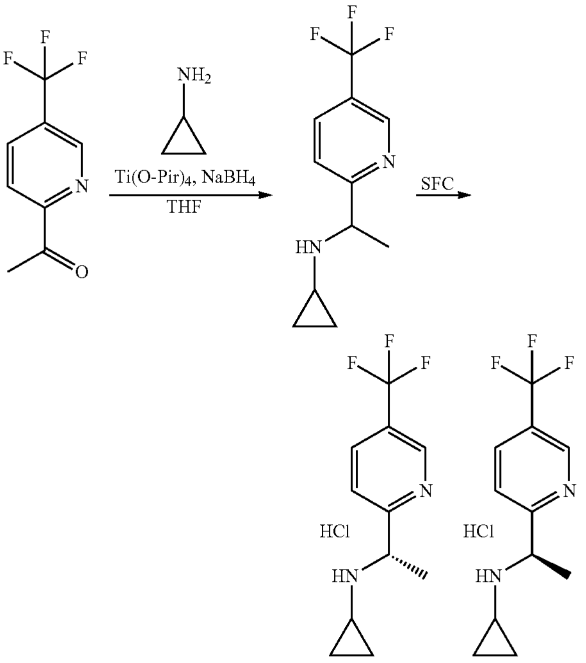

Eah-1 peak 1

Eah-2 peak 2

N-[(1S)-1-[5-(trifluoromethyl)-2-pyridyl]ethyl]cyclopropanamine (Eah-1) and N-[(1R)-1-[5-(trifluoromethyl)-2-pyridyl]ethyl]cyclopropanamine (Eah-2). To a solution of 1-[5-(trifluoromethyl)-2-pyridyl]ethanone (0.7 g, 3.7 mmol, 1 eq) in THF (30 mL) was added tetraisopropoxytitanium (2.1 g, 7.4 mmol, 2.1 mL, 2 eq) and cyclopropanamine (422.6 mg, 7.4 mmol, 512.8 uL, 2 eq). The mixture was stirred at 65° C. for 12 hr. Then the solution was cooled to 0° C. and $NaBH_4$ (840.0 mg, 22.2 mmol, 6 eq) was added to the solution. The mixture was stirred at 0° C. for 2 hr. The reaction mixture was quenched by addition of sat. $NH_4Cl$ (50 mL) at 0° C. and extracted with ethyl acetate (50 mL×3). The combined organic layers were washed with NaCl (50 mL×3), dried over $Na_2SO_4$, filtered, and concentrated under reduced pressure to give a residue. The residue was purified by flash silica gel chromatography to give product. The product-containing eluent was concentrated into a residue and was separated by prep-SFC (column: DAICEL CHIRALPAK IG (250 mm×30 mm, 10 um); mobile phase: [Heptane-MtBE];B %: 10%-10%, 8 min to give P1 (Rt=2.32 min) and P2 (Rt=3.73 min). Then the residue of P1 and P2 were dissolved in 4 mL MeOH and added aqueous HCl (1M, 0.3 mL), respectively. Then the P1 and P2 eluent were concentrated under reduced pressure respectively to give the desired products.

Peak 1: (S)—N-(1-(5-(trifluoromethyl)pyridin-2-yl)ethyl) cyclopropanamine hydrochloride (Eah-1). ES/MS: m/z=231.3 $[M+H]^+$. 1H NMR (400 MHz, $DMSO-d_6$) δ 9.95 (br s, 1H), 9.61 (br s, 1H), 9.06 (s, 1H), 8.44-8.33 (m, 1H), 7.89 (d, J=8.2 Hz, 1H), 4.82-4.67 (m, 1H), 1.59 (d, J=6.8 Hz, 3H), 1.00-0.92 (m, 1H), 0.87-0.78 (m, 1H), 0.71-0.57 (m, 2H).

Peak 2: (R)—N-(1-(5-(trifluoromethyl)pyridin-2-yl) ethyl)cyclopropanamine hydrochloride (Eah-2). ES/MS: m/z=231.3 $[M+H]^+$. 1H NMR (400 MHz, $DMSO-d_6$) δ 10.03-9.74 (m, 1H), 9.70-9.44 (m, 1H), 9.07 (s, 1H), 8.48-

8.32 (m, 1H), 7.89 (d, J=8.2 Hz, 1H), 4.83-4.67 (m, 1H), 1.59 (d, J=6.7 Hz, 3H), 1.00-0.90 (m, 1H), 0.87-0.77 (m, 1H), 0.72-0.57 (m, 2H).

General Procedure XXXV-E for the Synthesis of Intermediates Eai.

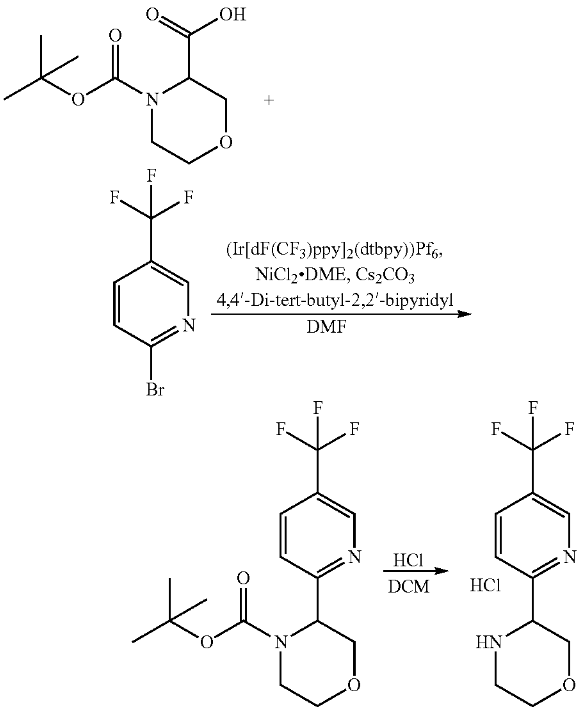

Eai-1

Step 1: tert-butyl 3-(5-(trifluoromethyl)pyridin-2-yl)morpholine-4-carboxylate. In a 40 mL reaction vial, a suspension of 2-bromo-5-(trifluoromethyl)pyridine (100 mg, 0.442 mmol), 4-tert-butoxycarbonylmorpholine-3-carboxylic acid (154 mg, 0.664 mmol), (Ir[dF(CF3)ppy]2(dtbpy))PF6 (4.96 mg, 0.00442 mmol), nickel chloride dimethoxyethane adduct (9.72 mg, 0.0442 mmol), 4,4'-Di-tert-butyl-2,2'-dipyridyl (17.8 mg, 0.0664 mmol), and cesium carbonate (433 mg, 1.33 mmol) in DMF (3 m mL) was degassed with Ar for 5 min. The reaction was then mixed at room temperature under irradiation from a blue LED (456 nm wavelength) Kessil lamp (100% LED) for 2 h. The reaction mixture was diluted with EtOAc and washed with LiCl 5% and brine. The organic extract was dried over sodium sulfate, filtered, and concentrated. Purification by flash chromatography gave desired product. ES/MS: m/z=332.2 $[M+H]^+$. 1H NMR (400 MHz, Chloroform-d) δ 8.90 (d, J=2.2 Hz, 1H), 7.93 (dd, J=8.3, 2.3 Hz, 1H), 7.33 (d, J=8.2 Hz, 1H), 5.16 (s, 1H), 4.77 (d, J=11.7 Hz, 1H), 4.05-3.89 (m, 1H), 3.89-3.75 (m, 2H), 3.61 (td, J=11.7, 3.1 Hz, 1H), 3.27 (td, J=12.9, 3.9 Hz, 1H), 1.47 (s, 9H).

Step 2: 3-(5-(trifluoromethyl)pyridin-2-yl)morpholine hydrochloride (Eai-1). A solution of tert-butyl 3-[5-(trifluoromethyl)-2-pyridyl]morpholine-4-carboxylate (70.2 mg, 0.211 mmol) and Hydrochloric acid in dioxane solution (4000 mmol/L, 0.528 mL, 2.11 mmol) in DCM (3 mL) was stirred at rt overnight. The reaction mixture was concentrated to dryness and used without further purification. ES/MS: m/z=233.2 $[M+H]^+$.

Eai-2

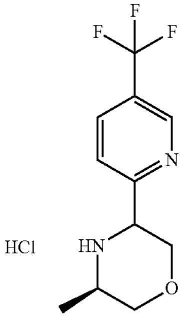

(3R)-3-methyl-5-(5-(trifluoromethyl)pyridin-2-yl)morpholine hydrochloride (Eai-2). Prepared using general procedure XXV-E starting with (3R,5R)-4-tert-butoxycarbonyl-5-methyl-morpholine-3-carboxylic acid. ES/MS: m/z=247.2 $[M+H]^+$.

Eai-3

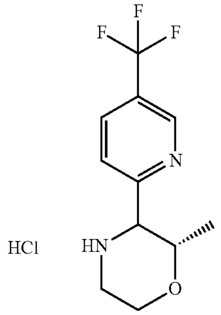

(2S)-2-methyl-3-(5-(trifluoromethyl)pyridin-2-yl)morpholine hydrochloride (Eai-3). Prepared using general procedure XXXV-E starting with (2S,3R)-4-tert-butoxycarbonyl-2-methyl-morpholine-3-carboxylic acid. ES/MS: m/z=247.2 $[M+H]^+$.

Eai-4

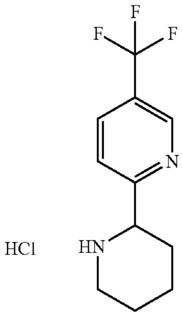

2-(piperidin-2-yl)-5-(trifluoromethyl)pyridine hydrochloride (Eai-4). Prepared using general procedure XXXV-E starting with 1-tert-butoxycarbonylpiperidine-2-carboxylic acid. ES/MS: m/z=231.2 $[M+H]^+$.

Eai-5

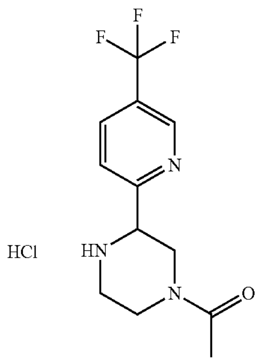

1-(3-(5-(trifluoromethyl)pyridin-2-yl)piperazin-1-yl) ethan-1-one hydrochloride (Eai-5). Prepared using general procedure XXXV-E starting with 4-acetyl-1-tert-butoxycarbonyl-piperazine-2-carboxylic acid. ES/MS: m/z=274.2 $[M+H]^+$.

Eai-6

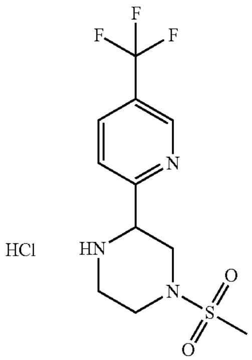

1-(methylsulfonyl)-3-(5-(trifluoromethyl)pyridin-2-yl) piperazine hydrochloride (Eai-6). Prepared using general procedure XXXV-E starting with 1-tert-butoxycarbonyl-4-methylsulfonyl-piperazine-2-carboxylic acid. ES/MS: m/z=310.0 $[M+H]^+$.

Eai-7

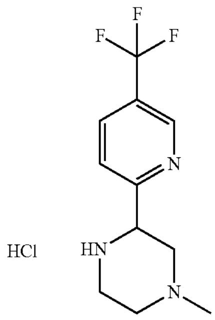

1-methyl-3-(5-(trifluoromethyl)pyridin-2-yl)piperazine hydrochloride (Eai-7). Prepared using general procedure XXXV-E starting with 1-tert-butoxycarbonyl-4-methyl-piperazine-2-carboxylic acid. ES/MS: m/z=246.2 $[M+H]^+$.

Eai-8

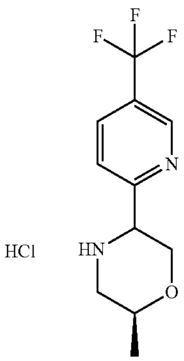

(2S)-2-methyl-5-(5-(trifluoromethyl)pyridin-2-yl)morpholine hydrochloride (Eai-8). Prepared using general procedure XXXV-E starting with (3S,6S)-4-tert-butoxycarbonyl-6-methyl-morpholine-3-carboxylic acid. ES/MS: m/z=247.2 $[M+H]^+$.

Eai-9

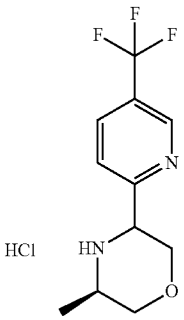

(3R)-3-methyl-5-(5-(trifluoromethyl)pyridin-2-yl)morpholine hydrochloride (Eai-9). Prepared using general procedure XXXV-E starting with (3R,5R)-4-tert-butoxycarbonyl-5-methyl-morpholine-3-carboxylic acid. ES/MS: m/z=247.2 $[M+H]^+$.

Eai-10

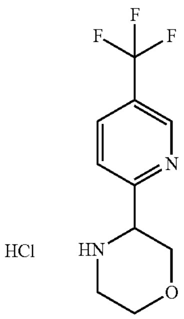

3-(5-(trifluoromethyl)pyridin-2-yl)morpholine hydrochloride (Eai-10). Prepared using general procedure XXXV-E starting with 4-tert-butoxycarbonylmorpholine-3-carboxylic acid. ES/MS: m/z=233.2 $[M+H]^+$.

Eai-11

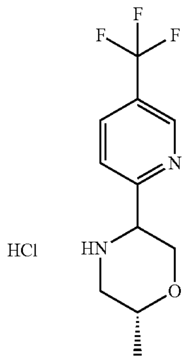

(2R)-2-methyl-5-(5-(trifluoromethyl)pyridin-2-yl)morpholine hydrochloride (Eai-11). Prepared using general procedure XXXV-E starting with (3R,6R)-4-tert-butoxycarbonyl-6-methyl-morpholine-3-carboxylic acid. ES/MS: m/z=247.2 $[M+H]^+$.

Eai-12

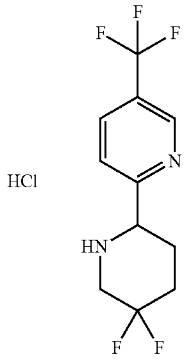

2-(5,5-difluoropiperidin-2-yl)-5-(trifluoromethyl)pyridine hydrochloride (Eai-12): Prepared using general procedure XXXV-E starting with 1-(tert-butoxycarbonyl)-5,5-difluoropiperidine-2-carboxylic acid. ES/MS: m/z=267.0 $[M+H]^+$.

Eai-13

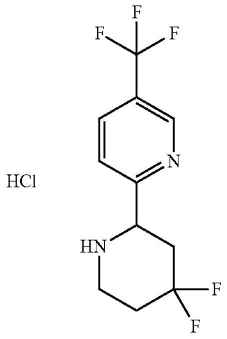

2-(4,4-difluoropiperidin-2-yl)-5-(trifluoromethyl)pyridine hydrochloride (Eai-13): Prepared using general procedure XXXV-E starting with 1-tert-butoxycarbonyl-4,4-difluoro-piperidine-2-carboxylic acid. ES/MS: m/z=267.0 $[M+H]^+$.

Eai-14

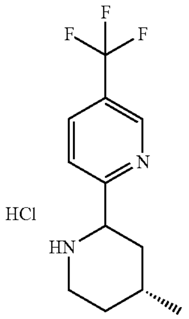

2-((4R)-4-methylpiperidin-2-yl)-5-(trifluoromethyl)pyridine hydrochloride (Eai-14): Prepared using general procedure XXXV-E starting with (4R)-1-tert-butoxycarbonyl-4-methyl-piperidine-2-carboxylic acid. ES/MS: m/z=245.2 $[M+H]^+$.

Eai-15

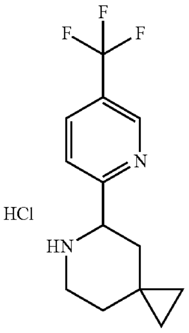

5-(5-(trifluoromethyl)pyridin-2-yl)-6-azaspiro[2.5]octane hydrochloride (Eai-15): Prepared using general procedure XXXV-E starting with (6-tert-butoxycarbonyl-6-azaspiro[2.5]octane-7-carboxylic acid. ES/MS: m/z=257.2 $[M+H]^+$.

Eai-16

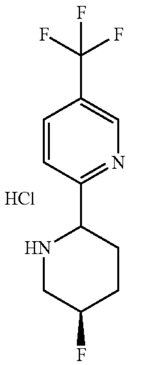

2-((5R)-5-fluoropiperidin-2-yl)-5-(trifluoromethyl)pyridine hydrochloride (Eai-16): Prepared using general procedure XXXV-E starting with (5R)-1-tert-butoxycarbonyl-5-fluoro-piperidine-2-carboxylic acid. ES/MS: m/z=249.2 $[M+H]^+$.

Eai-17

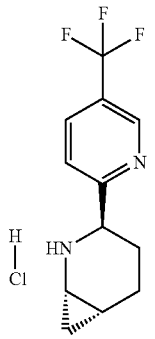

Rac-(1S,3R,6R)-3-(5-(trifluoromethyl)pyridin-2-yl)-2-azabicyclo[4.1.0]heptane hydrochloride (Eai-17). Prepared following procedure XXXV-E starting with 2-tert-butoxycarbonyl-2-azabicyclo[4.1.0]heptane-3-carboxylic acid. ES/MS: m/z=243.2 $[M+H]^+$.

Eai-18

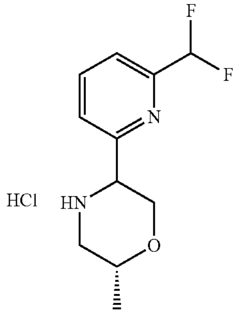

(2R)-5-(6-(difluoromethyl)pyridin-2-yl)-2-methylmorpholine hydrochloride (Eai-18). Prepared using general procedure XXXV-E starting with 2-bromo-6-(difluoromethyl) pyridine and (3R,6R)-4-tert-butoxycarbonyl-6-methylmorpholine-3-carboxylic acid. ES/MS: m/z=229.2 $[M+H]^+$.

Eai-19

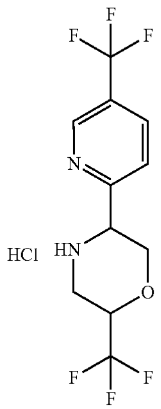

2-(trifluoromethyl)-5-(5-(trifluoromethyl)pyridin-2-yl) morpholine hydrochloride (Eai-19). Prepared following procedure XXXV-E starting with 4-(tert-butoxycarbonyl)-6-(trifluoromethyl)morpholine-3-carboxylic acid. ES/MS: m/z=301.2 [M+H]+

Eai-20

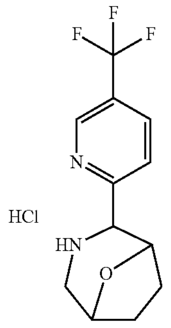

2-(5-(trifluoromethyl)pyridin-2-yl)-8-oxa-3-azabicyclo [3.2.1]octane hydrochloride (Eai-20). Prepared following procedure XXXV-E starting with 3-(tert-butoxycarbonyl)-8-oxa-3-azabicyclo[3.2.1]octane-2-carboxylic acid. ES/MS: m/z=259.3 [M+H]+

Eai-21

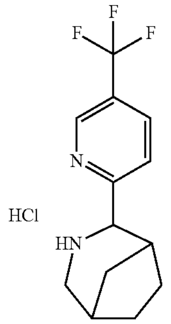

2-(5-(trifluoromethyl)pyridin-2-yl)-3-azabicyclo[3.2.1] octane hydrochloride (Eai-21). Prepared following procedure XXXV-E starting with 3-(tert-butoxycarbonyl)-3-azabicyclo[3.2.1]octane-2-carboxylic acid. ES/MS: m/z=257.3 [M+H]+

Eai-22

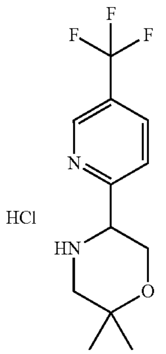

2,2-dimethyl-5-(5-(trifluoromethyl)pyridin-2-yl)morpholine hydrochloride (Eai-22). Prepared following procedure XXXV-E starting with 4-(tert-butoxycarbonyl)-6,6-dimethylmorpholine-3-carboxylic acid. ES/MS: m/z=261.2 $[M+H]^+$.

General Procedure XXXVI-E for the Synthesis of Intermediates Eaj:

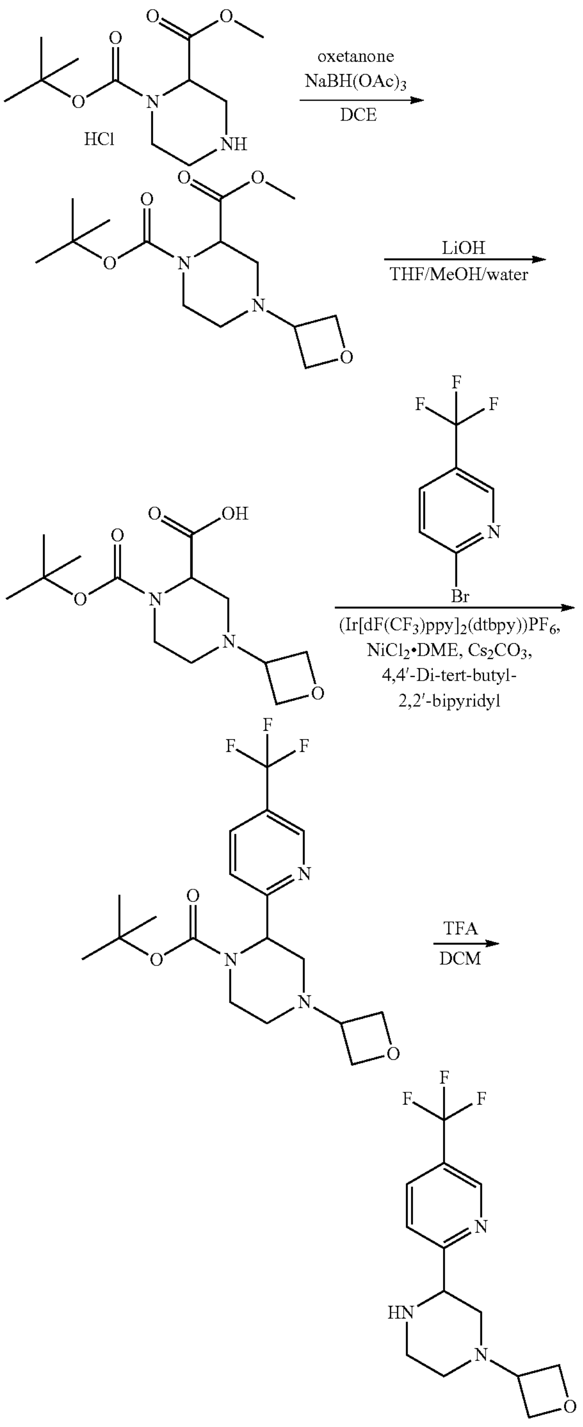

Eaj-1

Step 1: 1-(tert-butyl) 2-methyl 4-(oxetan-3-yl)piperazine-1,2-dicarboxylate. A solution of oxetanone (0.0813 mL, 1.39 mmol) and O1-tert-butyl O2-methyl piperazine-1,2-dicarboxylate;hydrochloride (468 mg, 1.67 mmol) in DCE was stirred at rt for 1 hr, then added sodium;triacetoxyboranuide (471 mg, 2.22 mmol). Stirred at rt overnight. The reaction was diluted with DCM and washed with saturated sodium bicarbonate solution and brine. Dried over sodium sulfate, filtered, and concentrated. Purification by flash chromatography gave desired product. ES/MS: m/z=301.2 $[M+H]^+$. $^1H$ NMR (400 MHz, Chloroform-d) δ 4.79 (s, 1H), 4.66 (q, J=6.6 Hz, 2H), 4.56 (dt, J=12.1, 6.2 Hz, 2H), 3.92 (d, J=13.2 Hz, 1H), 3.80 (d, J=3.3 Hz, 3H), 3.49 (p, J=6.4 Hz, 1H), 3.31-3.04 (m, 2H), 2.63 (dd, J=29.9, 11.1 Hz, 1H), 2.13 (dt, J=11.4, 3.8 Hz, 1H), 1.96 (t, J=11.5 Hz, 1H), 1.48 (d, J=16.1 Hz, 7H).

Step 2: 1-(tert-butoxycarbonyl)-4-(oxetan-3-yl)piperazine-2-carboxylic acid. A suspension of 1-(tert-butyl) 2-methyl 4-(oxetan-3-yl)piperazine-1,2-dicarboxylate (275 mg, 0.916 mmol) and Lithium hydroxide, monohydrate (115 mg, 2.75 mmol) in MeOH (2 mL), THF (2 mL), and water (2 mL) was stirred at rt overnight. The reaction was concentrated to dryness and added 2 mL water, 2 mL CH3CN, and −2.75 mL 1N HCl to pH 5. Diluted with EtOAc and separated organic layer. Extracted aqueous once more with EtOAc. Dried over sodium sulfate to give desired product, which was carried onto next step without purification. ES/MS: m/z=287.0 $[M+H]^+$. $^1H$ NMR (400 MHz, Methanol-d4) δ 4.69 (dt, J=9.0, 6.5 Hz, 2H), 4.62 (s, 1H), 4.56 (dt, J=9.7, 6.0 Hz, 2H), 3.82 (d, J=10.9 Hz, 1H), 3.50 (p, J=6.2 Hz, 1H), 3.30-3.21 (m, 1H), 3.16 (d, J=3.7 Hz, 1H), 2.73 (dd, J=24.2, 11.3 Hz, 1H), 2.13 (ddd, J=11.9, 7.8, 4.1 Hz, 1H), 1.94 (t, J=11.9 Hz, 1H), 1.47 (d, J=12.1 Hz, 9H).

Step 3: tert-butyl 4-(oxetan-3-yl)-2-(5-(trifluoromethyl)pyridin-2-yl)piperazine-1-carboxylate. In a 40 mL reaction vial, a suspension of 2-bromo-5-(trifluoromethyl)pyridine (100 mg, 0.442 mmol), 1-tert-butoxycarbonyl-4-(oxetan-3-yl)piperazine-2-carboxylic acid (190 mg, 0.664 mmol), nickel chloride dimethoxyethane adduct (9.72 mg, 0.0442 mmol), 4,4'-Di-tert-butyl-2,2'-dipyridyl (17.8 mg, 0.0664 mmol), and cesium carbonate (433 mg, 1.33 mmol) in DMF (3 m mL) was degassed with Ar for 5 min. The reaction was then mixed at room temperature under irradiation from a blue LED (456 nm wavelength) Kessil lamp (100% LED) for 2 h. The reaction mixture was diluted with EtOAc and washed with LiCl 5% and brine. The organic extract was dried over sodium sulfate, filtered, and concentrated. Purification by flash chromatography gave desired product. ES/MS: m/z=388.2 $[M+H]^+$. $^1H$ NMR (400 MHz, Chloroform-d) δ 8.89 (d, J=2.3 Hz, 1H), 7.93 (dd, J=8.4, 2.3 Hz, 1H), 7.28 (d, J=8.2 Hz, 1H), 5.32 (s, 1H), 4.67 (t, J=6.5 Hz, 1H), 4.62 (t, J=6.6 Hz, 1H), 4.49 (d, J=7.0 Hz, 2H), 4.12 (dd, J=11.1, 7.3 Hz, 1H), 3.74 (d, J=11.2 Hz, 1H), 3.49 (t, J=6.3 Hz, 1H), 3.24-2.99 (m, 1H), 2.63 (d, J=10.3 Hz, 1H), 2.34 (dd, J=11.3, 4.2 Hz, 1H), 2.16-2.03 (m, 1H), 1.48 (s, 9H).

Step 4: 1-(oxetan-3-yl)-3-(5-(trifluoromethyl)pyridin-2-yl)piperazine (Eaj-1). A solution of tert-butyl 4-(oxetan-3-yl)-2-[5-(trifluoromethyl)-2-pyridyl]piperazine-1-carboxylate (80.6 mg, 0.208 mmol) and 2,2,2-trifluoroacetic acid (0.474 mL, 6.24 mmol) in DCM (3 mL) was stirred at rt until starting material is consumed. The reaction was diluted with DCM and washed with saturated sodium bicarbonate solution and extracted with 7:3 $CHCl_3$/iPrOH. Dried over sodium sulfate to give product, which was used without further purification. ES/MS: m/z=288.2 $[M+H]^+$.

General Procedure XXXVII-E for the Synthesis of Intermediates Eak:

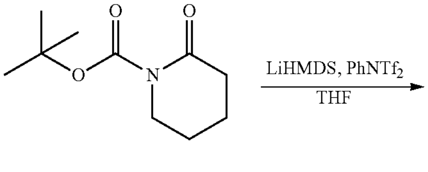

-continued

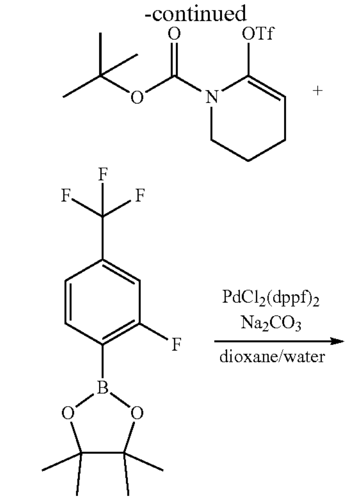

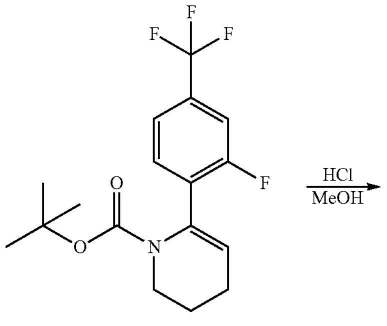

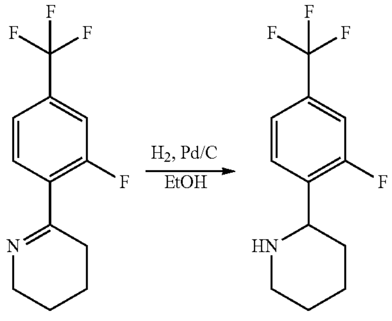

Eak-1

Step 1: tert-butyl 6-(((trifluoromethyl)sulfonyl)oxy)-3,4-dihydropyridine-1(2H)-carboxylate. To a solution of tert-butyl 2-oxopiperidine-1-carboxylate (500 mg, 2.5 mmol) in THF (10 mL) at −78 deg, was added Lithium bis(trimethylsilyl)amide (1.0 mmol/L, 3764 mL, 3.8 mmol). After 90 min at −78 deg, added a solution of N-Phenylbis(trifluoromethane)sulfonimide (2010 mg, 5.6 mmol) in THF (10 mL). Gradually warmed to rt o/n. Added water and extracted with EtOAc. Washed with brine and dried over sodium sulfate. Purification by flash chromatography gave title compound. 1H NMR (400 MHz, Chloroform-d) δ 5.31 (t, J=3.8 Hz, 1H), 3.88-3.30 (m, 2H), 2.29 (td, J=6.8, 3.9 Hz, 2H), 1.86-1.66 (m, 2H), 1.52 (d, J=0.7 Hz, 9H).

Step 2: tert-butyl 6-(2-fluoro-4-(trifluoromethyl)phenyl)-3,4-dihydropyridine-1(2H)-carboxylate. A suspension of tert-butyl 6-(trifluoromethylsulfonyloxy)-3,4-dihydro-2H-pyridine-1-carboxylate (150 mg, 0.45 mmol), 2-[2-fluoro-4-(trifluoromethyl)phenyl]-4,4,5,5-tetramethyl-1,3,2-dioxaborolane (144 mg, 0.50 mmol), 1,1'-Bis(diphenylphosphino)ferrocene palladium dichloride (27 mg, 0.045 mmol), and sodium carbonate (144 mg, 1.4 mmol) in 1,4-Dioxane (3 mL) and Water (1 mL) was degassed with argon for 5 min, then heated thermally at 80 deg overnight. Diluted with brine and EtOAc. Organic layer was dried over sodium sulfate. Purification by flash chromatography gave title compound. ES/MS: m/z=346.1 $[M+H]^+$. 1H NMR (400 MHz, Chloroform-d) δ 7.45-7.33 (m, 2H), 7.29 (dd, J=10.5, 1.6 Hz, 1H), 5.62-5.28 (m, 1H), 3.87-3.64 (m, 2H), 2.33 (td, J=6.8, 3.8 Hz, 2H), 2.02-1.82 (m, 2H), 1.13 (s, 9H).

Step 3: 6-(2-fluoro-4-(trifluoromethyl)phenyl)-2,3,4,5-tetrahydropyridine. To a suspension of tert-butyl 6-[2-fluoro-4-(trifluoromethyl)phenyl]-3,4-dihydro-2H-pyridine-1-carboxylate (86 mg, 0.25 mmol) in MeOH (2 mL) at rt, was added hydrochloric acid (4M in dioxane) (4000 mmol/L, 0.25 mL, 1.0 mmol). The reaction was stirred at rt overnight. The reaction was concentrated to dryness and carried onto the next step without purification. ES/MS: m/z=246.2 $[M+H]^+$.

Step 4: 2-(2-fluoro-4-(trifluoromethyl)phenyl)piperidine (Eak-1). A solution of 6-[2-fluoro-4-(trifluoromethyl)phenyl]-2,3,4,5-tetrahydropyridine (61 mg, 0.25 mmol) in EtOH (5 mL) was degassed with Ar/vacuum (3 times) and Pd/C (10%, 27 mg, 0.025 mmol) was added. The mixture was degassed with Ar/vacuum (2 times), then stirred at room temperature overnight with a balloon of hydrogen. The reaction was diluted with EtOAc and filtered through fritted funnel with Celite. The filtrate was concentrated to dryness to give desired product, which was used in subsequent steps without purification. ES/MS: m/z=248.2 $[M+H]^+$. $^1H$ NMR (400 MHz, Chloroform-d) δ 9.99-9.90 (m, 2H), 8.14 (s, 1H), 7.46 (d, J=6.0 Hz, 1H), 7.38 (d, J=9.4 Hz, 1H), 4.39 (s, 1H), 3.31 (d, J=15.1 Hz, 1H), 2.90 (s, 1H), 2.05 (dt, J=27.5, 7.3 Hz, 4H), 1.82 (d, J=12.9 Hz, 1H), 1.65 (d, J=11.8 Hz, 1H).

Eak-2

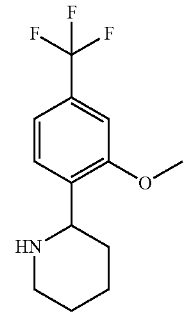

2-(2-methoxy-4-(trifluoromethyl)phenyl)piperidine (Eak-2). Prepared using general procedure XXXVII-E using [2-methoxy-4-(trifluoromethyl)phenyl]boronic acid in step 2. ES/MS: m/z=260.2 $[M+H]^+$. $^1H$ NMR (400 MHz, Chloroform-d) δ 9.47 (s, 1H), 7.81 (d, J=7.8 Hz, 1H), 7.25 (d, J=7.1 Hz, 1H), 7.11 (s, 1H), 4.38 (s, 1H), 3.93 (s, 3H), 3.15 (d, J=27.2 Hz, 1H), 2.83 (s, 1H), 2.17 (d, J=12.5 Hz, 1H), 2.11-1.87 (m, 3H), 1.77 (d, J=12.3 Hz, 1H), 1.61 (d, J=12.2 Hz, 1H).

Eak-3

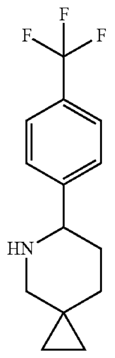

6-(4-(trifluoromethyl)phenyl)-5-azaspiro[2.5]octane (Eak-3). Prepared using general procedure XXXVII-E starting with tert-butyl 6-oxo-5-azaspiro[2.5]octane-5-carboxylate in step 1 and [4-(trifluoromethyl)phenyl]boronic acid in step 2. ES/MS: m/z=256.2 $[M+H]^+$.

Eak-4

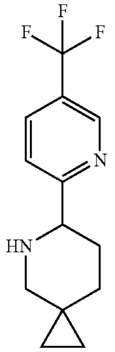

6-(5-(trifluoromethyl)pyridin-2-yl)-5-azaspiro[2.5]octane (Eak-4). Prepared using general procedure XXXVII-E starting with tert-butyl 6-oxo-5-azaspiro[2.5]octane-5-carboxylate in step 1 and [5-(trifluoromethyl)-2-pyridyl]boronic acid in step 2. ES/MS: m/z=257.2 $[M+H]^+$.

General Procedure XXXVIII for the Synthesis of Intermediates Eal:

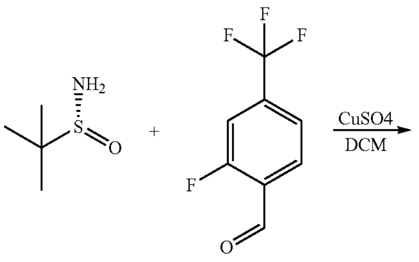

-continued

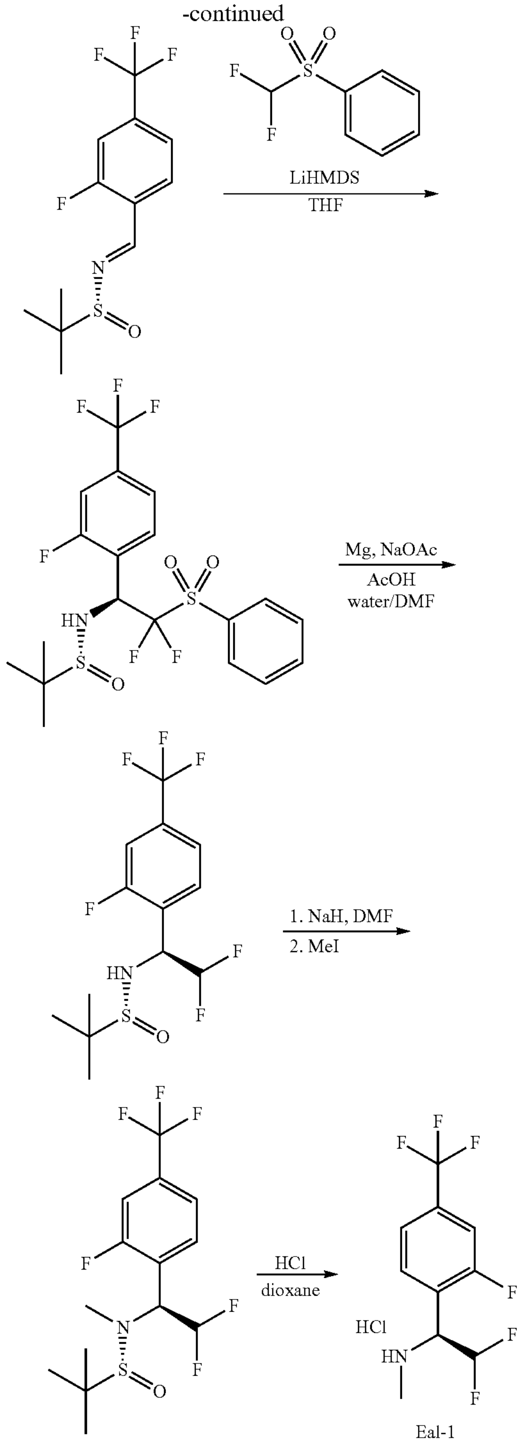

Eal-1

Step 1: (NE,S)—N-[[2-fluoro-4-(trifluoromethyl)phenyl]methylene]-2-methyl-propane-2-sulfinamide. To a solution of 2-fluoro-4-(trifluoromethyl)benzaldehyde (10 g, 52 mmol) and (R)-(+)-2-methyl-2-propanesulfinamide (6.4 g, 53 mmol) in DCM (175 ml), was added cupric sulfate (16.6 g, 104 mmol). Stirred at rt o/n. The reaction was filtered over celite, washed with DCM, concentrated. Purification by flash chromatography gave title compound. ES/MS: m/z=296 $[M+H]^+$. $^1H$ NMR (400 MHz, Chloroform-d) δ 8.94 (s, 1H), 8.16 (t, J=7.4 Hz, 1H), 7.53 (ddd, J=8.2, 1.8, 0.8 Hz, 1H), 7.47 (dd, J=9.9, 1.6 Hz, 1H), 1.31 (s, 9H).

Step 2: (R)—N-[(1S)-2-(benzenesulfonyl)-2,2-difluoro-1-[2-fluoro-4-(trifluoromethyl)phenyl]ethyl]-2-methyl-propane-2-sulfinamide. To a solution of (NE,S)—N-[[2-fluoro-4-(trifluoromethyl)phenyl]methylene]-2-methyl-propane-2-sulfinamide (1400 mg, 4.7 mmol) and difluoromethyl phenyl sulfone (1367 mg, 7.1 mmol) in THF (15 mL) at −78° C., was added Lithium bis(trimethylsilyl)amide (1000 mmol/L, 7.1 mL, 7.1 mmol). Stirred at −78° C. for 90 min, then gradually warmed to rt o/n. Diluted with EtOAc and saturated NH4Cl. Separated organic and washed once more with brine, then dried over sodium sulfate. Purification by flash chromatography gave title compound. ES/MS: m/z=488.0 $[M+H]^+$. $^1H$ NMR (400 MHz, Chloroform-d) δ 8.02-7.94 (m, 2H), 7.77 (d, J=7.5 Hz, 1H), 7.64 (ddd, J=8.5, 7.2, 1.8 Hz, 3H), 7.49 (dd, J=8.3, 1.7 Hz, 1H), 7.40 (dd, J=10.3, 1.7 Hz, 1H), 5.67 (ddd, J=18.4, 10.5, 7.4 Hz, 1H), 4.45-4.26 (m, 1H), 1.33 (s, 9H).

Step 3: (R)—N-[(1S)-2,2-difluoro-1-[2-fluoro-4-(trifluoromethyl)phenyl]ethyl]-2-methyl-propane-2-sulfinamide. To a solution of (R)—N-[(1S)-2-(benzenesulfonyl)-2,2-difluoro-1-[2-fluoro-4-(trifluoromethyl)phenyl]ethyl]-2-methyl-propane-2-sulfinamide (967 mg, 2.0 mmol) in DMF (15 mL) in a rt water bath, was added a solution of sodium acetate (1627 mg, 20 mmol) in acetic acid (1.1 mL, 20 mmol) and water (3.3 mL), followed by slow addition of magnesium (723 mg, 30 mmol) in small portions. The reaction was stirred for 4 hr. Diluted with EtOAc and washed with water and 5% LiCl. Separated organic and washed with brine and 5% LiCl. Dried over sodium sulfate. Purification by flash chromatography gave title compound.

ES/MS: m/z=348.0 $[M+H]^+$. $^1H$ NMR (400 MHz, Chloroform-d) δ 7.57 (t, J=7.4 Hz, 1H), 7.50 (dd, J=8.2, 1.7 Hz, 1H), 7.41 (dd, J=10.2, 1.7 Hz, 1H), 6.04 (tdd, J=55.5, 3.4, 0.9 Hz, 1H), 4.97 (tdd, J=12.7, 9.0, 3.4 Hz, 1H), 4.04 (d, J=8.9 Hz, 1H), 1.27 (s, 9H).

Step 4: (1S)-2,2-difluoro-1-[2-fluoro-4-(trifluoromethyl)phenyl]-N-methyl-ethanamine. To a solution of (R)—N-[(1S)-2,2-difluoro-1-[2-fluoro-4-(trifluoromethyl)phenyl]ethyl]-2-methyl-propane-2-sulfinamide (335 mg, 0.96 mmol) in DMF (5 mL) at 0 deg, was added sodium hydride (60%, 52 mg, 1.4 mmol). After 15 min, added iodomethane (0.30 mL, 4.8 mmol). Gradually warmed to rt o/n. Diluted with EtOAc and washed with 5% LiCl 2× and brine. Dried over sodium sulfate. Purification by flash chromatography gave title compound. ES/MS: m/z=362.0 $[M+H]^+$. $^1H$ NMR (400 MHz, Chloroform-d) δ 7.65 (t, J=7.5 Hz, 1H), 7.50 (dd, J=8.1, 1.7 Hz, 1H), 7.43 (dd, J=10.1, 1.7 Hz, 1H), 6.34 (tdd, J=54.9, 4.4, 1.2 Hz, 1H), 5.02 (td, J=13.4, 4.4 Hz, 1H), 2.77-2.49 (m, 3H), 1.23 (s, 9H).

Step 5. (S)-2,2-difluoro-1-(2-fluoro-4-(trifluoromethyl)phenyl)-N-methylethan-1-amine hydrochloride (Eal-1). A solution of (R)—N-[(1S)-2,2-difluoro-1-[2-fluoro-4-(trifluoromethyl)phenyl]ethyl]-N,2-dimethyl-propane-2-sulfinamide (162 mg, 0.447 mmol) and Hydrochloric acid in dioxane solution (4000 mmol/L, 2.23 mL, 8.94 mmol) in DCM (5 mL) was stirred at rt. The reaction mixture was concentrated to dryness and used without further purification. ES/MS: m/z=258.2 $[M+H]^+$.

Eal-2

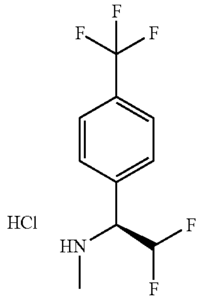

(S)-2,2-difluoro-N-methyl-1-(4-(trifluoromethyl)phenyl)ethan-1-amine hydrochloride (Eal-2). Prepared using general procedure XXXVIII-E starting with 4-(trifluoromethyl)benzaldehyde in step 1. ES/MS: m/z=240.2 $[M+H]^+$.

Eal-3

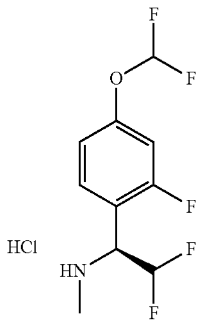

(S)-1-(4-(difluoromethoxy)-2-fluorophenyl)-2,2-difluoro-N-methylethan-1-amine hydrochloride (Eal-3). Prepared using general procedure XXXVIII-E starting with 4-(difluoromethoxy)-2-fluoro-benzaldehyde in step 1. ES/MS: m/z=256.1 $[M+H]^+$.

Eal-4

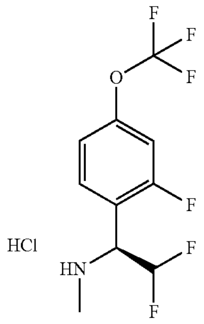

(S)-2,2-difluoro-1-(2-fluoro-4-(trifluoromethoxy)phenyl)-N-methylethan-1-amineamine hydrochloride (Eal-4). Prepared using general procedure XXXVIII-E starting with 2-fluoro-4-(trifluoromethyl)benzaldehyde in step 1. ES/MS: m/z=274.1 $[M+H]^+$.

Eal-5

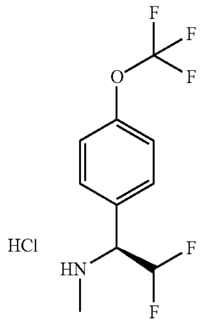

(S)-2,2-difluoro-N-methyl-1-(4-(trifluoromethoxy)phenyl)ethan-1-amine hydrochloride (Eal-5). Prepared using general procedure XXXVIII-E starting with 2-fluoro-4-(trifluoromethyl)benzaldehyde in step 1. ES/MS: m/z=256.1 $[M+H]^+$.

Eal-6

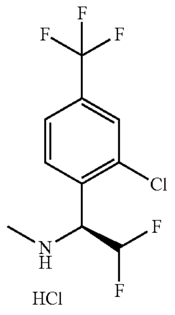

(S)-1-(2-chloro-4-(trifluoromethyl)phenyl)-2,2-difluoro-N-methylethan-1-amine hydrochloride (Eal-6). Prepared using general procedure XXXVIII-E starting with commercial 2-chloro-4-(trifluoromethyl)benzaldehyde. ES/MS: m/z=274.4 [M+H]+(S)-2,2-difluoro-1-(2-fluoro-4-(trifluoromethyl)phenyl)-N-(methyl-d3)ethan-1-amine (Eal-7)

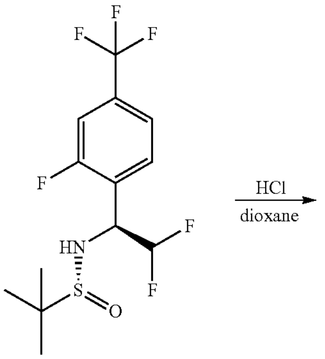

-continued

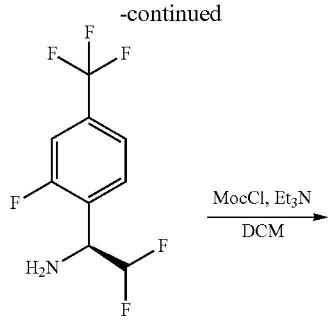

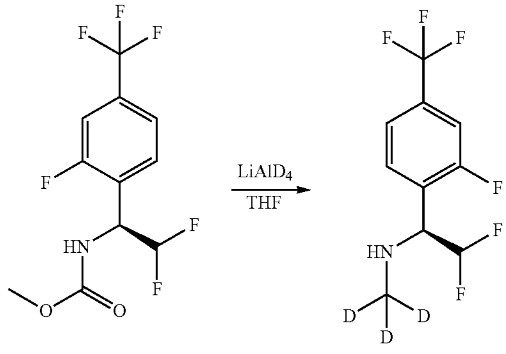

Eal-7

Step 1. (S)-2,2-difluoro-1-(2-fluoro-4-(trifluoromethyl)phenyl)ethan-1-amine. A solution of (R)—N—((S)-2,2-difluoro-1-(2-fluoro-4-(trifluoromethyl)phenyl)ethyl)-2-methylpropane-2-sulfinamide (prepared following steps 1-3 of general procedure XXXVIII, 200 mg, 0.576 mmol) and Hydrochloric acid in dioxane solution (4000 mmol/L, 1.44 mL, 5.76 mmol) in DCM (4 mL) was stirred at rt for 1 hr. The reaction was concentrated to dryness to give a colorless oil and used without further purification. ES/MS: m/z=244.0 $[M+H]^+$.

Step 2. methyl (S)-(2,2-difluoro-1-(2-fluoro-4-(trifluoromethyl)phenyl)ethyl)carbamate. To a solution of (S)-2,2-difluoro-1-(2-fluoro-4-(trifluoromethyl)phenyl)ethan-1-amine in DCM (5 mL) at 0 deg, was added triethylamine (0.401 mL, 2.88 mmol), followed by methyl chloroformate (0.100 mL, 1.29 mmol). Gradually warmed to rt o/n. Diluted with EtOAc and washed with brine. Dried over sodium sulfate. Purification by flash chromatography gave title compound. ES/MS: m/z=302.0 $[M+H]^+$. $^1H$ NMR (400 MHz, Chloroform-d) δ 7.56-7.47 (m, 2H), 7.42 (d, J=10.3 Hz, 1H), 6.06 (t, J=55.2 Hz, 1H), 5.69-5.37 (m, 2H), 3.75 (s, 3H).

Step 3. (S)-2,2-difluoro-1-(2-fluoro-4-(trifluoromethyl)phenyl)-N-(methyl-d3)ethan-1-amine (Eal-7). To a solution of methyl (S)-(2,2-difluoro-1-(2-fluoro-4-(trifluoromethyl)phenyl)ethyl)carbamate (54.1 mg, 0.180 mmol) in THF (4 mL) at rt, was added lithium aluminum deuteride (30.2 mg, 0.718 mmol). The reaction was heated at 40 deg overnight, then cooled to 0 deg and diluted with ether. Added 30 uL water, 30 uL 15% NaOH, and 90 uL water. The mixture was warmed to rt and stirred for 15 min, then added $MgSO_4$. Filtered and concentrated to give desired product and used without further purification. ES/MS: m/z=261.2 $[M+H]^+$.

General Procedure XXXIX-E for the Synthesis of Intermediates Eam:

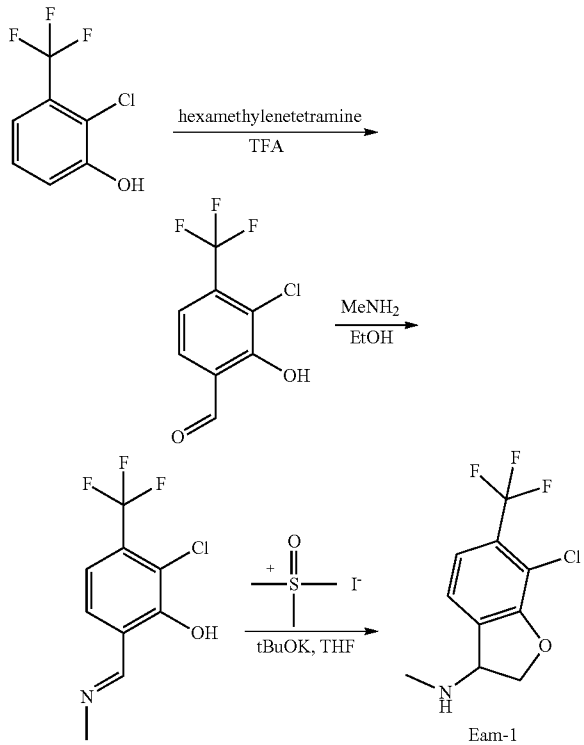

Eam-1

Step 1: 3-chloro-2-hydroxy-4-(trifluoromethyl)benzaldehyde. To a solution of 2-chloro-3-(trifluoromethyl)phenol (1000 mg, 5.09 mmol) in TFA (7 mL), was added Hexamethylenetetramine (1783 mg, 12.7 mmol)). Heated at 80 deg for 72 hr. Added ice and stirred for 10 min. Extract 3× with EtOAc. Washed with water and brine. Dried over sodium sulfate, concentrated, and purified by flash silica gel chromatography to give title compound. ES/MS: m/z=238.0 $[M+H]^+$.

Step 2: (E)-2-chloro-6-((methylimino)methyl)-3-(trifluoromethyl)phenol. To a solution of 3-chloro-2-hydroxy-4-(trifluoromethyl)benzaldehyde (470 mg, 2.09 mmol) in EtOH (5 mL) was added methanamine (40.0%, 487 mg, 6.28 mmol). Stirred at room temperature overnight. The reaction diluted with water and extracted with EtOAc. Dried over sodium sulfate to give crude product, which used into the next step without further purification. ES/MS: m/z=238.0 $[M+H]^+$.

Step 3: 7-chloro-N-methyl-6-(trifluoromethyl)-2,3-dihydrobenzofuran-3-amine (Eam-1). A suspension of trimethylsulfoxonium iodide (1381 mg, 6.28 mmol) and Potassium tert-butoxide (939 mg, 8.37 mmol) in THF (10 mL) was heated at 50 deg o/n. A solution of the (E)-2-chloro-6-((methylimino)methyl)-3-(trifluoromethyl)phenol (479 mg, 2.02 mmol) in THF (5 mL) was added to the KOtBu/TMSSOI suspension and heated at 50° C. o/n. The reaction was diluted with EtOAc and saturated $NH_4Cl$. Dried organic extract with sodium sulfate, concentrated, and purified by flash silica gel chromatography to give title compound. ES/MS: m/z=252.0 $[M+H]^+$. $^1H$ NMR (400 MHz, $CDCl_3$) δ 7.35-7.24 (m, 2H), 4.84-4.61 (m, 1H), 4.66-4.44 (m, 2H), 2.47 (s, 3H).

Eam-2

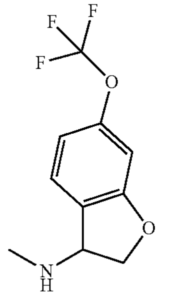

N-methyl-6-(trifluoromethoxy)-2,3-dihydrobenzofuran-3-amine (Eam-2). Prepared following steps 2 and 3 of general procedure XXXIX-E starting with commercial 2-hydroxy-4-(trifluoromethoxy)benzaldehyde. $^1H$ NMR (400 MHz, $CD_3CN$) δ 7.40 (dd, J=8.2, 0.7 Hz, 1H), 6.83 (ddq, J=8.2, 2.2, 1.1 Hz, 1H), 6.76 (dd, J=2.2, 1.1 Hz, 1H), 4.69-4.52 (m, 1H), 4.51-4.35 (m, 2H), 2.34 (s, 3H).

Eam-3

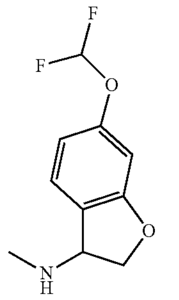

6-(difluoromethoxy)-N-methyl-2,3-dihydrobenzofuran-3-amine (Eam-3). Prepared following steps 2 and 3 of general procedure XXXIX-E starting with commercial 2-hydroxy-4-(difluoromethoxy)benzaldehyde. $^1H$ NMR (400 MHz, $CDCl_3$) δ 7.31 (d, J=8.1 Hz, 1H), 6.69-6.61 (m, 2H), 6.63-6.15 (m, 1H), 4.58 (dd, J=9.9, 7.6 Hz, 1H), 4.52-4.35 (m, 2H), 2.43 (s, 3H).

Eam-4

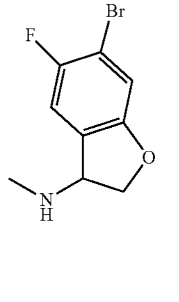

6-bromo-5-fluoro-N-methyl-2,3-dihydrobenzofuran-3-amine (Eam-4). Prepared following steps 2 and 3 of general procedure XXXIX-E starting with commercial 4-bromo-5-fluoro-2-hydroxybenzaldehyde. $^1H$ NMR (400 MHz, MeOD) δ 7.27 (dd, J=7.9, 0.7 Hz, 1H), 7.05 (d, J=5.4 Hz, 1H), 4.60 (dd, J=9.5, 7.3 Hz, 1H), 4.56-4.35 (m, 2H), 2.36 (s, 3H).

Eam-5

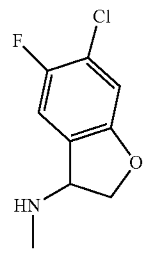

6-chloro-5-fluoro-N-methyl-2,3-dihydrobenzofuran-3-amine (Eam-5). Prepared following steps 2 and 3 of general procedure XXXIX-E starting with 4-chloro-5-fluoro-2-hydroxybenzaldehyde and methylamine. ES/MS: m/z=186.2 (—$CH_3$) [M-Me]$^+$.

Eam-6

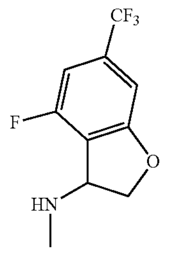

4-fluoro-N-methyl-6-(trifluoromethyl)-2,3-dihydrobenzofuran-3-amine (Eam-6). Prepared following steps 2 and 3 of general procedure XXXIX-E starting with 2-fluoro-6-hydroxy-4-(trifluoromethyl)benzaldehyde and methylamine. ES/MS: m/z=236.2 [M+H]$^+$.

Eam-7

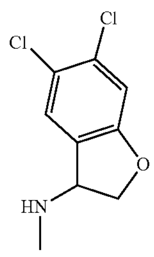

5,6-dichloro-N-methyl-2,3-dihydrobenzofuran-3-amine (Eam-7). Prepared following steps 2 and 3 of general procedure XXXIX-E starting with 4,5-dichloro-2-hydroxybenzaldehyde and methylamine. ES/MS: m/z=217.7, 219.7 [M+H]$^+$.

Eam-8

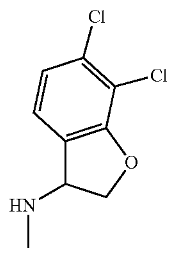

6,7-dichloro-N-methyl-2,3-dihydrobenzofuran-3-amine (Eam-8). Prepared following steps 2 and 3 of general procedure XXXIX-E starting with 3,4-dichloro-2-hydroxybenzaldehyde and methylamine. ES/MS: m/z=217.7, 219.7 [M+H]$^+$.

Eam-9

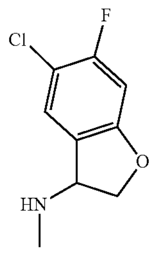

5-chloro-6-fluoro-N-methyl-2,3-dihydrobenzofuran-3-amine (Eam-9). Prepared following steps 2 and 3 of general procedure XXXIX-E starting with 5-chloro-4-fluoro-2-hydroxybenzaldehyde and methylamine. ES/MS: m/z=202.9 [M+H]$^+$.

Eam-10

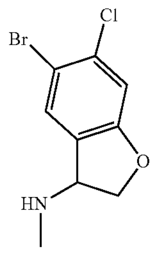

5-bromo-6-chloro-N-methyl-2,3-dihydrobenzofuran-3-amine (Eam-10). Prepared following steps 2 and 3 of general procedure XXXIX-E starting with 5-bromo-4-chloro-2-hydroxybenzaldehyde and methylamine (XX). ES/MS: m/z=263.6 [M+H]$^+$.

Eam-11

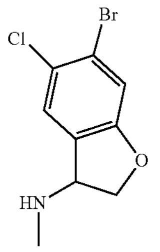

6-bromo-5-chloro-N-methyl-2,3-dihydrobenzofuran-3-amine (Eam-11). Prepared following steps 2 and 3 of general procedure XXXIX-E starting with 4-bromo-5-chloro-2-hydroxybenzaldehyde and methylamine. ES/MS: m/z=263.6 $[M+H]^+$.

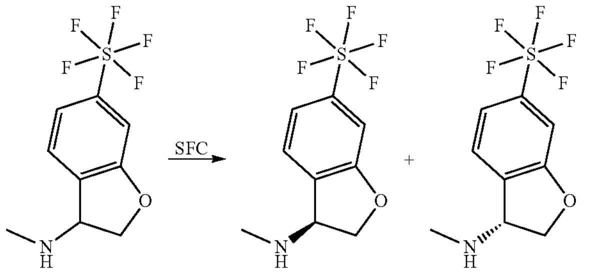

Eam-12
peak 1 peak 2

(S)—N-methyl-6-(pentafluoro-16-sulfaneyl)-2,3-dihydrobenzofuran-3-amine (Eam-12). Prepared following steps 2 and 3 of general procedure XXXIX-E starting with commercial 3-(pentafluoro-lambda6-sulfanyl)phenol. The racemic mixture was then purified by SFC (column: DAICEL CHIRALPAK AD (250 mm*30 mm, 10 um); mobile phase: [A: $CO_2$;B: EtOH (0.1% $NH_3H_2O$)];B %: 15.00%-15.00%, 4.00 min) to isolate (S)—N-methyl-6-(pentafluoro-16-sulfaneyl)-2,3-dihydrobenzofuran-3-amine as peak 1 (RT 1.792 min, 99.2% ee) and (R)—N-methyl-6-(pentafluoro-16-sulfaneyl)-2,3-dihydrobenzofuran-3-amine as peak 2 (RT 2.168 min, 98.3% ee).

(S)—N-methyl-6-(pentafluoro-16-sulfaneyl)-2,3-dihydrobenzofuran-3-amine Eam-12 (peak 1, RT 1.792 min, 99.2% ee) ES/MS: m/z=276.1 $[M+H]^+$. $^1$H NMR (400 MHz, METHANOL-$d_4$) δ 7.70 (d, J=8.4 Hz, 1H), 7.49 (dd, J=2.0, 8.4 Hz, 1H), 7.40 (d, J=1.9 Hz, 1H), 4.93 (dd, J=3.8, 6.6 Hz, 1H), 4.80-4.75 (m, 2H), 2.64 (s, 3H).

General Procedure XL-E for the Synthesis of Intermediates Ean:

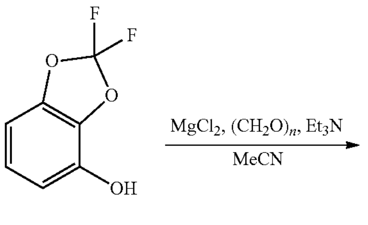

-continued

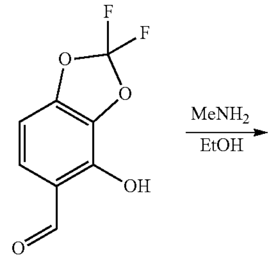

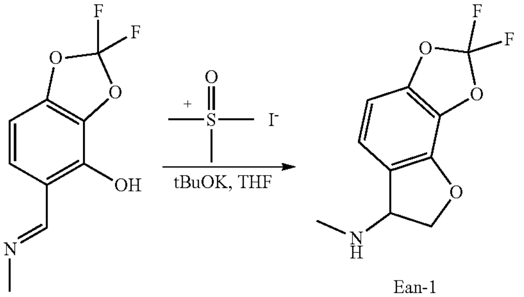

Ean-1

Step 1: 2,2-difluoro-4-hydroxybenzo[d][1,3]dioxole-5-carbaldehyde. To a solution of 2,2-difluoro-1,3-benzodioxol-4-ol (1000 mg, 5.74 mmol) in $CH_3CN$ (15 mL), was added magnesium chloride (1367 mg, 14.4 mmol) (exotherm), followed by triethylamine (5.00 mL, 35.9 mmol). Paraformaldehyde (3518 mg, 39.1 mmol) was added in portions. Heated at reflux overnight. The reaction was cooled to rt, then poured into a vigorously stirred solution of 50 mL Et2O and 50 mL 5% HCl. Separated organic and extracted aqueous with Et2O, then washed combined organic extracts with brine and dried over sodium sulfate. Purified by flash silica gel chromatography to give title compound. $^1$H NMR (400 MHz, $CDCl_3$) δ 11.25 (s, 1H), 9.87 (s, 1H), 7.42 (d, J=8.4 Hz, 1H), 6.83 (d, J=8.4 Hz, 1H).

Step 2: (E)-2,2-difluoro-5-((methylimino)methyl)benzo[d][1,3]dioxol-4-ol. To a solution of 2,2-difluoro-4-hydroxy-1,3-benzodioxole-5-carbaldehyde (406 mg, 2.01 mmol) in EtOH (5 mL) was added methanamine (40.0%, 191 mg, 2.46 mmol). Stirred art room temperature overnight. The reaction diluted with water and extracted with EtOAc. Dried over sodium sulfate and purified by flash silica gel chromatography to give title compound. ES/MS: m/z=216.2 $[M+H]^+$. $^1$H NMR (400 MHz, CDCl3) δ 14.53 (s, 1H), 8.16 (q, J=1.3 Hz, 1H), 6.96 (d, J=8.5 Hz, 1H), 6.50 (d, J=8.5 Hz, 1H), 3.47 (d, J=1.2 Hz, 3H).

Step 3: 2,2-difluoro-N-methyl-6,7-dihydro-[1,3]dioxolo[4,5-g]benzofuran-6-amine (Ean-1). Separately, a suspension of trimethylsulfoxonium iodide (1327 mg, 6.03 mmol) and potassium tert-butoxide (902 mg, 8.04 mmol) in THF (10 mL) was heated at 50° C. o/n After o/n, a solution of the 2,2-difluoro-5-[(E)-methyliminomethyl]-1,3-benzodioxol-4-ol (203 mg, 0.941 mmol, yield) in THF (5 mL) was added to the KOtBu/TMSSOI suspension and heated at 50° C. o/n. The reaction was diluted with EtOAc and saturated $NH_4Cl$. Dried organic extract with sodium sulfate, concentrated, and purified by flash silica gel chromatography to give title compound. $^1$H NMR (400 MHz, $CDCl_3$) δ 7.10 (dd, J=8.1, 0.9 Hz, 1H), 6.66 (d, J=8.0 Hz, 1H), 4.75-4.58 (m, 2H), 4.51 (ddd, J=7.4, 3.4, 0.8 Hz, 1H), 2.45 (s, 3H).

(S)-6-(difluoromethoxy)-7-fluoro-N-methyl-2,3-dihydrobenzofuran-3-amine (Ean-2)

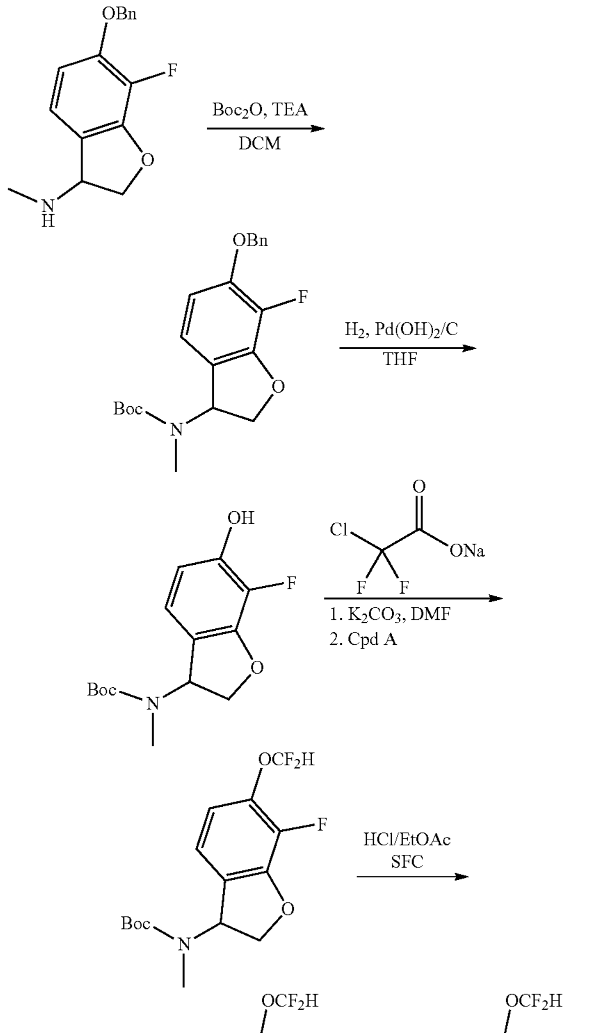

peak 1

Ean-2
Peak 2

Step 1. tert-butyl (6-(benzyloxy)-7-fluoro-2,3-dihydrobenzofuran-3-yl)(methyl)carbamate. To a solution of 6-(benzyloxy)-7-fluoro-N-methyl-2,3-dihydrobenzofuran-3-amine (prepared according to general procedure XL-E starting with 3-(benzyloxy)-2-fluorophenol, 19.2 g, 70.3 mmol) in dichloromethane (200 mL) was added Triethylamine (14.2 g, 141 mmol) and Di-tert-butyl dicarbonate (98.0%, 15.6 g, 70.3 mmol). The mixture was stirred at 25° C. for 12 hr. LC-MS showed Reactant 5 was consumed completely and the desired mass was not detected. TLC indicated the reactant 5 was consumed completely and one new spot formed. The reaction mixture was concentrated under reduced pressure to give a residue. The residue was purified by flash silica gel chromatography to give desired product. $^1H$ NMR (400 MHz, $CDCl_3$) δ 7.47-7.34 (m, 5H), 6.88 (br d, J=7.3 Hz, 1H), 6.58 (dd, J=6.8, 8.3 Hz, 1H), 6.15-5.70 (m, 1H), 5.14 (s, 2H), 4.71 (br t, J=9.2 Hz, 1H), 4.53-4.42 (m, 1H), 2.55 (br s, 3H), 1.49 (s, 9H).

Step 2. tert-butyl (7-fluoro-6-hydroxy-2,3-dihydrobenzofuran-3-yl)(methyl)carbamate. To a solution of palladium hydroxide on carbon (20.0%, 3.0 g) in Tetrahydrofuran (50.0 mL) was added tert-butyl (6-(benzyloxy)-7-fluoro-2,3-dihydrobenzofuran-3-yl)(methyl)carbamate (5.8 g, 15.5 mmol) in Tetrahydrofuran (100 mL) under $N_2$ atmosphere. The suspension was degassed and purged with $H_2$ for 3 times. The mixture was stirred under $H_2$ (15 psi.) at 25° C. for 5 hr. LC-MS showed Reactant 6 was consumed completely and the desired mass was not detected, and TLC indicated the reactant 6 was consumed completely and one new spot formed. The reaction mixture was filtered and concentrated under reduced pressure to give a residue. The residue was purified by flash silica gel chromatography to give desired product. $^1H$ NMR (400 MHz, $CDCl_3$) δ 6.85 (br d, J=7.9 Hz, 1H), 6.61-6.53 (m, 1H), 6.06-5.74 (m, 1H), 4.70 (br t, J=9.5 Hz, 1H), 4.51-4.42 (m, 1H), 2.55 (br s, 3H), 1.49 (s, 9H).

Step 3. tert-butyl (6-(difluoromethoxy)-7-fluoro-2,3-dihydrobenzofuran-3-yl)(methyl)carbamate. Potassium carbonate (2.9 g, 21.2 mmol) in dimethylformamide (20.0 mL) was stirred at 110° C. Then tert-butyl (7-fluoro-6-hydroxy-2,3-dihydrobenzofuran-3-yl)(methyl)carbamate and (2-chloro-2,2-difluoro-acetyl)oxy sodium (3.2 g, 21.2 mmol) in dimethylformamide (30.0 mL) was added to the solution at 110° C. The mixture was stirred at 110° C. for 3 hr. LC-MS showed starting material were consumed completely and the desired mass was detected. The reaction mixture was diluted with $H_2O$ 40 mL and extracted with ethyl acetate 120 mL (40 mL×3). The combined organic layers were washed with brine 60 mL (20 mL×3), dried over $Na_2SO_4$, filtered and concentrated under reduced pressure to give a residue. The residue was purified by flash silica gel chromatography to give desired product. ES/MS: m/z=278.1 $[M+H]^+$. $^1H$ NMR (400 MHz, $CDCl_3$) δ 6.98 (br d, J=7.9 Hz, 1H), 6.79 (dd, J=6.8, 7.7 Hz, 1H), 6.74-6.33 (m, 1H), 6.18-5.75 (m, 1H), 4.75 (br t, J=9.7 Hz, 1H), 4.52 (br d, J=7.8 Hz, 1H), 2.58 (br s, 3H), 1.49 (s, 9H).

Step 4. (R)-6-(difluoromethoxy)-7-fluoro-N-methyl-2,3-dihydrobenzofuran-3-amine & (S)-6-(difluoromethoxy)-7-fluoro-N-methyl-2,3-dihydrobenzofuran-3-amine (Ean-2). Tert-butyl (6-(difluoromethoxy)-7-fluoro-2,3-dihydrobenzofuran-3-yl)(methyl)carbamate (0.22 g, 0.66 mmol, 1 eq) in HCl/EtOAc (4 mL) (4M) was stirred at 25° C. for 3 hr. The reaction mixture concentrated under reduced pressure to give a residue. The residue was triturated with Ethyl acetate (5 mL) at 25° C. for 1 hr. The residue was filtered, washed with Ethyl acetate (5 mL) and then the filter cake was dried under reduced pressure. The residue further separated by SFC (column: DAICEL CHIRALPAK AD (250 mm*30 mm, 10 um); mobile phase: [$CO_2$ MeOH (0.1% $NH_3H_2O$)];B %: 14%, isocratic elution mode, P1RT: 1.736 min, 99.3% purity, P2RT: 1.916 min, 96.5% purity). The residue Peak 1 was purified by prep-HPLC (HCl condition; column: Phenomenex luna C18 100*40 mm*5 um; mobile phase: [$H_2O$(0.04% HCl)-ACN];gradient: 1%-35% B over 8.0 min) to give (R)-6-(difluoromethoxy)-7-fluoro-N-methyl-2,3-dihydrobenzofuran-3-amine. (Peak 1 RT 1.736 min) ES/MS: m/z=234.1 $[M+H]^+$. $^1H$ NMR (400 MHz, $CD_3OD$) δ 7.42 (br d, J=8.4 Hz, 1H), 7.11-6.70 (m, 2H), 5.10 (br d, J=7.0 Hz, 1H), 4.95 (br d, J=2.0 Hz, 2H), 2.73 (s, 3H)

The residue P2 was purified by prep-HPLC (HCl condition; column: Phenomenex luna C18 100*40 mm*5 um; mobile phase: [$H_2O$(0.04% HCl)-ACN];gradient: 1%-30% B over 8.0 min) to give (S)-6-(difluoromethoxy)-7-fluoro-N-methyl-2,3-dihydrobenzofuran-3-amine (Ean-2) (peak 2, RT 1.916 min) ES/MS: m/z=234.1 $[M+H]^+$. $^1H$ NMR (400 MHz, $CD_3OD$) δ 7.42 (dd, J=1.3, 8.4 Hz, 1H), 7.10-6.72 (m, 2H), 5.12-5.08 (m, 1H), 4.98-4.94 (m, 2H), 2.73 (s, 3H)

General Procedure XLI-E for the Synthesis of Intermediates Eao:

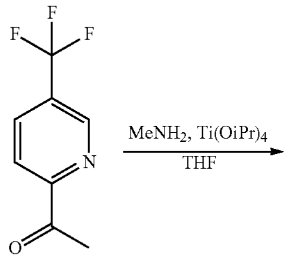

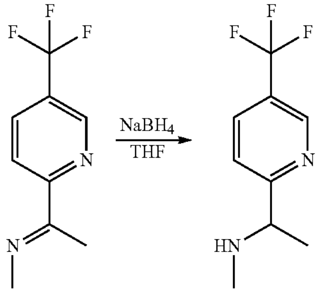

Eao-1

Step 1: (E)-N-methyl-1-(5-(trifluoromethyl)pyridin-2-yl)ethan-1-imine. To a solution of 1-[5-(trifluoromethyl)-2-pyridyl]ethanone (2 g, 10.6 mmol, 1 eq) in THF (30 mL) was added methanamine (5.5 g, 52.9 mmol, 13.2 mL, 30% purity, 5 eq) (EtOH solution) and tetraisopropoxytitanium (6.0 g, 21.2 mmol, 6.2 mL, 2 eq). The mixture was stirred at 70° C. for 12 hours. The crude product was carried onto the next step without further purification.

Step 2: N-methyl-1-(5-(trifluoromethyl)pyridin-2-yl)ethan-1-amine (Eao-1). To a solution of (E)-N-methyl-1-(5-(trifluoromethyl)pyridin-2-yl)ethan-1-imine (2 g, 9.9 mmol, 1 eq) in THF (25 mL) was added $NaBH_4$ (2.3 g, 59.4 mmol, 6 eq) at 0° C. The mixture was stirred at 0° C. for 2 hr. LC-MS showed desired compound was detected. The reaction mixture was quenched by addition sat $NH_4Cl$ 25 mL at 0° C. and extracted with ethyl acetate (30 mL×3). The combined organic layers were washed with NaCl (30 mL×3), dried over $Na_2SO_4$, filtered, and concentrated under reduced pressure to give a residue. The residue was purified by flash silica gel chromatography, then dissolved in 4 mL MeOH and 1.5 mL 1M HCl was added to the solution. Then the solution was concentrated under reduced pressure to give title compound as an HCl salt. ES/MS: m/z=205.3 $[M+H]^+$. $^1H$ NMR (400 MHz, DMSO-$d_6$) δ 9.85 (br s, 1H), 9.38 (br s, 1H), 9.12-8.94 (m, 1H), 8.37 (dd, J=1.9, 8.2 Hz, 1H), 7.85 (d, J=8.3 Hz, 1H), 4.60 (sxt, J=6.5 Hz, 1H), 2.47 (t, J=5.4 Hz, 3H), 1.55 (d, J=6.9 Hz, 3H).

General Procedure XLII-E for the Synthesis of Intermediates Eap:

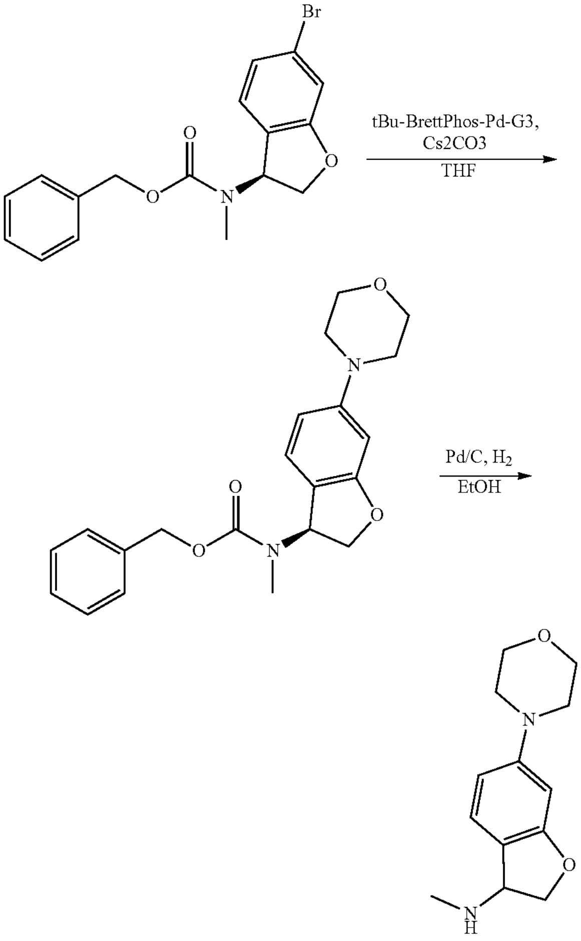

Eap-1

Step 1: benzyl (S)-methyl(6-morpholino-2,3-dihydrobenzofuran-3-yl)carbamate. A suspension of benzyl N-[(3S)-6-bromo-2,3-dihydrobenzofuran-3-yl]-N-methyl-carbamate (Prepared according to general procedure VIII-E starting with (S)-6-bromo-2,3-dihydrobenzofuran-3-amine hydrochloride and Cbz-ONSu) (150 mg, 0.414 mmol), morpholine (0.0357 mL, 0.471 mmol), tBu-BrettPhos-Pd-G3 (35.4 mg, 0.0414 mmol)), and Cesium carbonate (270 mg, 0.828 mmol) in THF (4 mL) was degassed for 5 min with Ar, then heated at 70 deg o/n. The reaction was diluted with EtOAc, washed with brine and dried over sodium sulfate. Purified by flash silica gel chromatography to give title compound. ES/MS: m/z=369.1 $[M+H]^+$.

Step 2: (S)—N-methyl-6-morpholino-2,3-dihydrobenzofuran-3-amine (Eap-1). A suspension of benzyl (S)-methyl (6-morpholino-2,3-dihydrobenzofuran-3-yl)carbamate (51.5 mg, 0.140 mmol) in EtOH (5 mL) was degassed with Ar/vacuum (3 times). Added Pd/C (10.0%, 14.9 mg, 0.0140 mmol), degassed with Ar/vacuum (2 times), and stirred at rt with a balloon of hydrogen. The reaction was filtered over a Celite pad, and concentrate to give title product, which was used without further purification. ES/MS: m/z=204.2 $[M-NHMe]^+$.

General Procedure XLIII-E for the Synthesis of Intermediates Eaq:

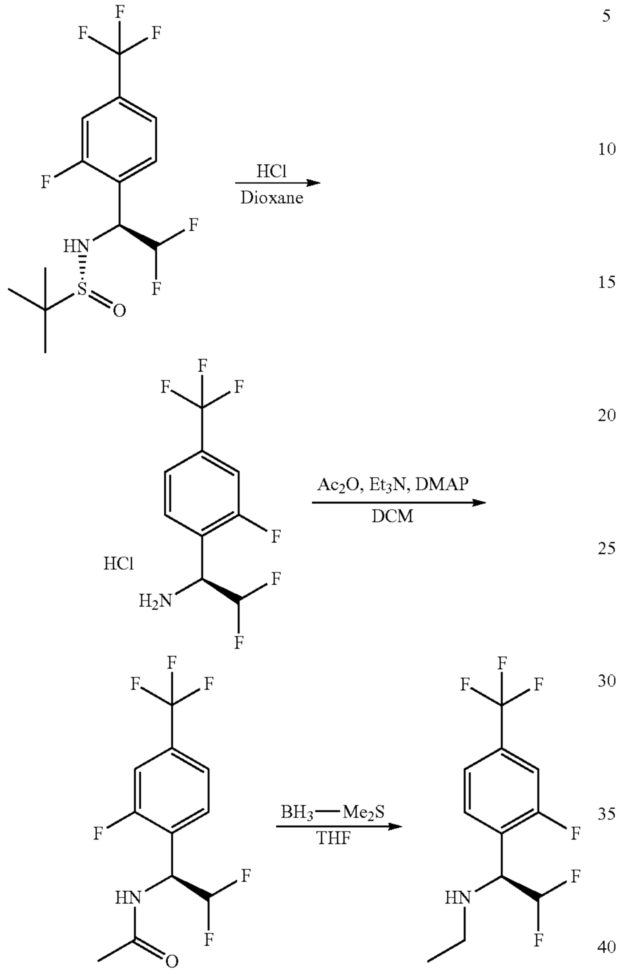

Eaq-1

Step 1: (S)-2,2-difluoro-1-(2-fluoro-4-(trifluoromethyl)phenyl)ethan-1-amine hydrochloride. A solution of N-[(1S)-2,2-difluoro-1-[2-fluoro-4-(trifluoromethyl)phenyl]ethyl]-2-methyl-propane-2-sulfinamide (prepared according to general procedure XXXVIII-E, 100 mg, 0.288 mmol) and hydrochloric acid in dioxane solution (4000 mmol/L, 0.720 mL, 2.88 mmol) in DCM (3 mL) was stirred at rt. After 1 hr, the reaction was concentrated to dryness to give title compound, which was carried onto the next step without further purification. ES/MS: m/z=244.0 $[M+H]^+$.

Step 2: (S)—N-(2,2-difluoro-1-(2-fluoro-4-(trifluoromethyl)phenyl)ethyl)acetamide. To a solution of (1S)-2,2-difluoro-1-[2-fluoro-4-(trifluoromethyl)phenyl]ethanamine hydrochloride (70.0 mg, 0.252 mmol) and 4-Dimethylaminopyridine (8.00 mg, 0.0655 mmol) in DCM (4 mL), was added Triethylamine (0.161 mL, 1.15 mmol) and acetic anhydride (0.0400 mL, 0.423 mmol). Stirred at rt o/n. Diluted with EtOAc and washed with brine. Dried with sodium sulfate and purified by flash silica gel chromatography to give title compound. ES/MS: m/z=286.0 $[M+H]^+$. $^1$H NMR (400 MHz, Chloroform-d) δ 7.56-7.45 (m, 3H), 7.45-7.38 (m, 1H), 6.24 (d, J=8.9 Hz, 1H), 6.21-5.86 (m, 1H), 5.81-5.63 (m, 1H), 2.13 (s, 3H).

Step 3: (S)—N-ethyl-2,2-difluoro-1-(2-fluoro-4-(trifluoromethyl)phenyl)ethan-1-amine (Eaq-1). To a solution of (S)—N-(2,2-difluoro-1-(2-fluoro-4-(trifluoromethyl)phenyl)ethyl)acetamide (63.5 mg, 0.223 mmol) in THF at 0° C., was added borane dimethyl sulfide complex (0.106 mL, 1.11 mmol). Stirred o/n at rt. Additional borane dimethyl sulfide complex (0.106 mL, 1.11 mmol) was added and the reaction was heated to 50° C. for 2 hr. The reaction was cooled to rt, added MeOH (5 mL) until no more bubbling, then added Hydrochloric acid in dioxane solution (4000 mmol/L, 0.557 mL, 2.23 mmol). Stirred for 5 min. Concentrated to dryness to give title compound, which was used without further purification. ES/MS: m/z=272.0 $[M+H]^+$. $^1$H NMR (400 MHz, Chloroform-d) δ 10.99 (s, 1H), 10.72 (s, 1H), 8.34 (t, J=7.6 Hz, 1H), 7.80-7.55 (m, 1H), 7.51 (dd, J=9.6, 1.7 Hz, 1H), 6.83 (td, J=54.3, 3.8 Hz, 1H), 4.96 (d, J=16.9 Hz, 1H), 3.74 (d, J=5.7 Hz, 4H), 3.28-3.10 (m, 1H), 2.96 (s, 1H), 1.87-1.62 (m, 4H), 1.52 (t, J=7.3 Hz, 3H).

General Procedure XLIV-E for the Synthesis of Intermediates Ear:

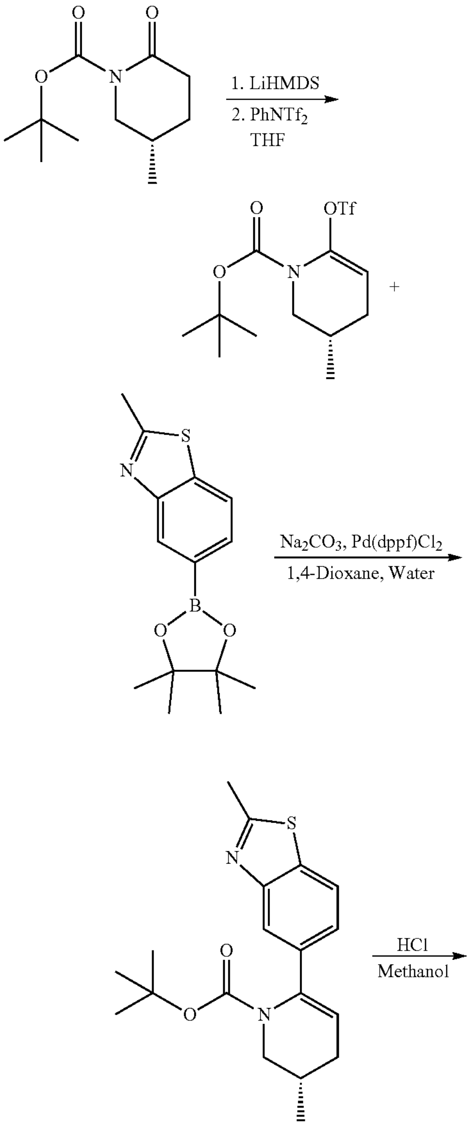

-continued

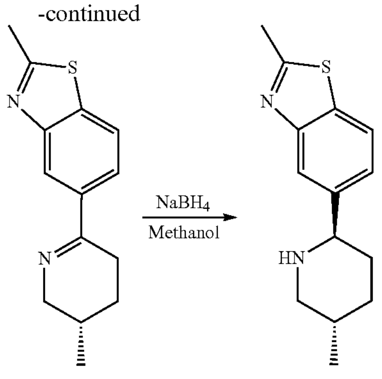

Ear-1

Step 1: tert-butyl (S)-3-methyl-6-(((trifluoromethyl)sulfonyl)oxy)-3,4-dihydropyridine-1(2H)-carboxylate. To a solution of tert-butyl (S)-5-methyl-2-oxopiperidine-1-carboxylate (1000 mg, 4.7 mmol) in THF (10 mL0 at −78 deg, was added Lithium bis(trimethylsilyl)amide (1.0 mmol/L, 7033 mL, 7.0 mmol). The reaction was stirred at −78 deg for 90 min. Added a solution of N-Phenylbis(trifluoromethane) sulfonimide (2010 mg, 5.6 mmol) in THF (10 mL). Gradually warmed to rt o/n. The reaction was diluted with water and extracted with EtOAc. The organic extract was washed with brine, dried over sodium sulfate, and purified by flash silica gel chromatography to give title product. ES/MS: m/z=346.0 $[M+H]^+$. $^1H$ NMR (400 MHz, DMSO-d6) δ 5.51 (t, J=3.6 Hz, 1H), 3.67 (dd, J=12.7, 2.9 Hz, 1H), 3.06 (dd, J=12.7, 8.3 Hz, 1H), 2.46-2.30 (m, 1H), 2.04-1.69 (m, 2H), 1.43 (s, 9H), 0.92 (d, J=6.5 Hz, 3H).

Step 2: tert-butyl (S)-3-methyl-6-(2-methylbenzo[d]thiazol-5-yl)-3,4-dihydropyridine-1(2H)-carboxylate A stirred solution of 2-methyl-5-(4,4,5,5-tetramethyl-1,3,2-dioxaborolan-2-yl)benzo[d]thiazole (1.6 g, 5.818 mmol), tert-butyl (S)-3-methyl-6-(((trifluoromethyl)sulfonyl)oxy)-3,4-dihydropyridine-1(2H)-carboxylate (2.0 g, 5.797 mmol), and sodium carbonate (1.22 g, 11.509 mmol) in 1,4 dioxane (30 mL) and water (6 mL) was degassed for 10 min using argon, then added $Pd(dppf)Cl_2$ (250 mg, 0.412 mmol) and degassed for another 10 min. The reaction mixture was heated to 80° C. for 16 h. The reaction mixture was filtered through celite pad and washed with ethyl acetate twice. The filtrate was evaporated to dryness and purified by flash silica gel chromatography to give title product. ES/MS: m/z=345.2 $[M+H]^+$.

Step 3: (S)-2-methyl-5-(5-methyl-3,4,5,6-tetrahydropyridin-2-yl)benzo[d]thiazole. To a solution of tert-butyl (S)-3-methyl-6-(2-methylbenzo[d]thiazol-5-yl)-3,4-dihydropyridine-1(2H)-carboxylate (2.6 g, 7.558 mmol) in methanol (15.6 mL) at 0° C. was added 4M HCL in 1,4-Dioxane (7.8 mL, 31.2 mmol) dropwise and the reaction mixture was stirred at rt for 3 h. The reaction was concentrated to dryness, then triturated with MTBE. The resulting solid was filtered and dried to give desired product. ES/MS: m/z=245.2 $[M+H]^+$.

Step 4: 2-methyl-5-((2R,5S)-5-methylpiperidin-2-yl) benzo[d]thiazole (Ear-1). To a solution of (S)-2-methyl-5-(5-methyl-3,4,5,6-tetrahydropyridin-2-yl)benzo[d]thiazole (1.3 g, 3.63 mmol) in methanol (13 mL) at 0° C. was added $NaBH_4$ (0.19 g, 5.3 mmol) portion wise and the reaction mixture was stirred at rt for 3 h. The reaction was concentrated to dryness, then added ice, then stirred for 30 min to give precipitate, which was filtered and dried. Purification by prep HPLC gave desired product. ES/MS: m/z=247.2 $[M+H]^+$.

General Procedure XLV-E for the Synthesis of Intermediates Eas:

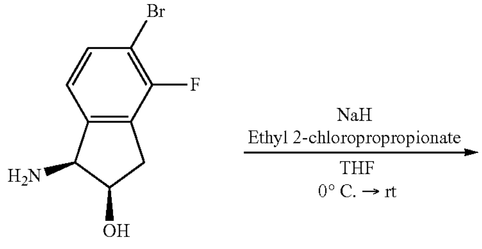

Es-1

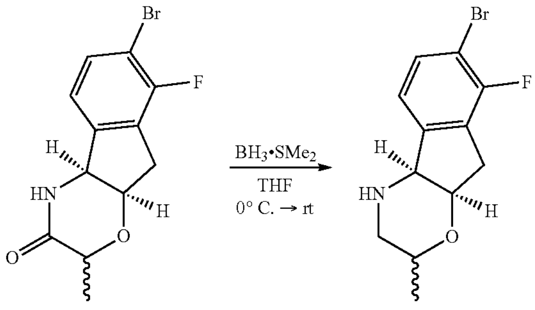

Eas-1

Step 1: (4aS,9aR)-7-bromo-8-fluoro-2-methyl-4,4a,9,9a-tetrahydroindeno[2,1-b][1,4]oxazin-3(2H)-one. To a solution of (1S,2R)-1-amino-5-bromo-4-fluoro-2,3-dihydro-1H-inden-2-ol (514 mg, 2.1 mmol) in THF (10 mL) and toluene (20 mL) at 0 deg, was added sodium hydride (60.0%, 135 mg, 3.53 mmol). The reaction was stirred for 30 min, then added Ethyl 2-chloropropionate (0.293 mL, 2.3 mmol), Stirred at rt for 5 min, then heated at 65° C. overnight. The reaction was diluted with EtOAc and washed with saturated NH4Cl. Dried organic extract with sodium sulfate and purified by flash chromatography to give title compound. ES/MS: m/z=300.0, 301.9 $[M+H]^+$.

Step 2: (4aS,9aR)-7-bromo-8-fluoro-2-methyl-2,3,4,4a,9,9a-hexahydroindeno[2,1-b][1,4]oxazine (Eas-1). To a solution of (4aS,9aR)-7-bromo-8-fluoro-2-methyl-4,4a,9,9a-tetrahydroindeno[2,1-b][1,4]oxazin-3(2H)-one. (60.0 mg, 0.2 mmol) THF (2 mL) at 0° C., was added borane-dimethyl sulfide complex (122 mg, 1.6 mmol). The reaction was stirred overnight and quenched by MeOH followed by 4N HCl dioxane solution. The solution was heated to 40° C. for two hours and then concentrated to afford the title compound, which was carried onto the next step without purification. ES/MS: m/z=286.0, 288.0 $[M+H]^+$.

Eas-2

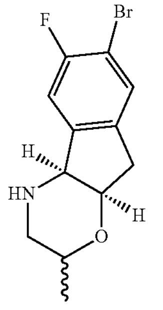

(4aS,9aR)-7-bromo-6-fluoro-2-methyl-2,3,4,4a,9,9a-hexahydroindeno[2,1-b][1,4]oxazine (Eas-2). Prepared following procedure XLV-E starting with (1S,2R)-1-amino-5-bromo-6-fluoro-2,3-dihydro-1H-inden-2-ol Es-3. ES/MS: m/z=286.0, 288.0 $[M+H]^+$.

Eas-3

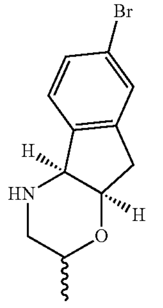

(4aS,9aR)-7-bromo-2-methyl-2,3,4,4a,9,9a-hexahydroindeno[2,1-b][1,4]oxazine (Eas-3). Prepared following procedure XLV-E starting with (1S,2R)-1-amino-5-bromo-2,3-dihydro-1H-inden-2-ol Es-1. ES/MS: m/z=267.9 $[M+H]^+$.

Eas-4

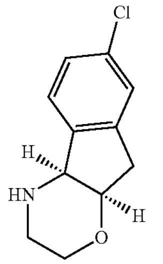

(4aS,9aR)-7-chloro-2,3,4,4a,9,9a-hexahydroindeno[2,1-b][1,4]oxazine (Eas-4). Prepared following general procedure XLV-E starting with (1S,2R)-1-amino-5-chloro-2,3-dihydro-1H-inden-2-ol (Es-5) and chloroacetyl chloride. ES/MS: m/z=211.0 $[M+H]^+$.

Eas-5

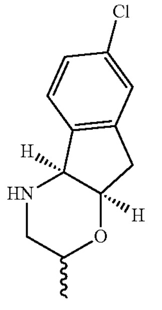

(4aS,9aR)-7-chloro-2-methyl-2,3,4,4a,9,9a-hexahydroindeno[2,1-b][1,4]oxazine (Eas-5). Prepared following general procedure XLV-E starting with (1S,2R)-1-amino-5-chloro-2,3-dihydro-1H-inden-2-ol (Es-5) and 2-chloropropanoyl chloride. ES/MS: m/z=224.2 $[M+H]^+$.

General Procedure XLVI-E for the Synthesis of Intermediates Eat:

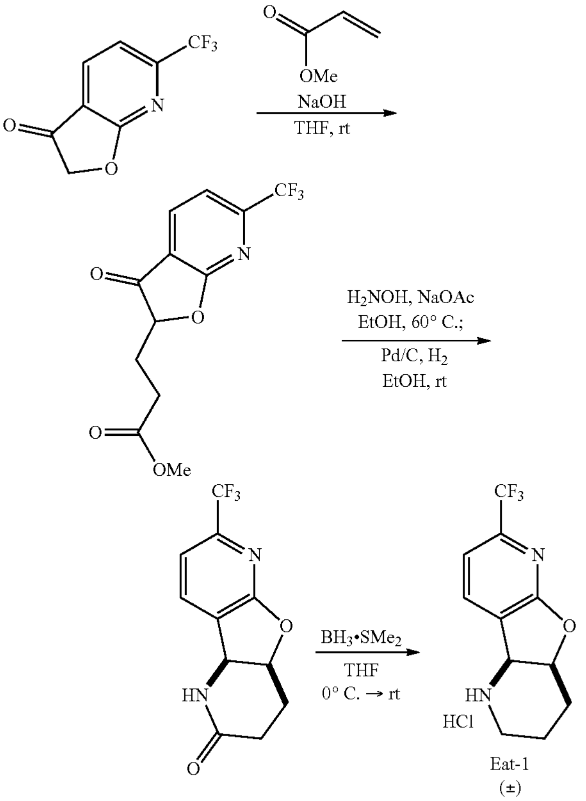

Eat-1
(±)

Step 1: Methyl 3-(3-oxo-6-(trifluoromethyl)-2,3-dihydrofuro[2,3-b]pyridin-2-yl)propanoate. 6-(trifluoromethyl)furo[2,3-b]pyridin-3(2H)-one (1.2 g, 5.8 mmol) and methyl acrylate (496 mg, 5.8 mmol) in THF (18 mL) was added NaH (60% dispersion in mineral oil, 230 mg, 5.8 mmol). The mixture was stirred at rt for 10 min before quenched by HOAc. The solution was diluted with EtOAc and washed with brine and dried over sodium sulfate. The crude residue was purified by flash chromatography to give desired product. ES/MS: m/z=290.0 $[M+H]^+$.

Step 2: cis-7-(trifluoromethyl)-3,4,4a,9b-tetrahydrofuro[2,3-b:4,5-b']dipyridin-2(1H)-one. To the solution of cis-methyl 3-(3-oxo-6-(trifluoromethyl)-2,3-dihydrofuro[2,3-b]pyridin-2-yl)propanoate (215 mg, 0.74 mmol) in EtOH (6 mL) was added hydroxyamine hydrochloride (103 mg, 1.5 mmol) and sodium acetate (122 mg, 1.5 mmol). The mixture was stirred at 60° C. for 4 hours. The mixture was cool to rt and filtered. The solution was concentrated and resuspended in EtOH (20 mL) followed by the addition of 10% palladium on carbon (197 mg, 0.19 mmol). The mixture was stirred under 1 atm of hydrogen balloon for 30 mins before filtering. The mixture was concentrated and was purified by flash chromatography to give desired product. ES/MS: m/z=259.0 $[M+H]^+$.

Step 3. cis-(4aS,9bS)-7-(trifluoromethyl)-1,2,3,4,4a,9b-hexahydrofuro[2,3-b:4,5-b']dipyridine hydrochloride (Eat-1). To a solution of cis-7-(trifluoromethyl)-3,4,4a,9b-tetrahydrofuro[2,3-b:4,5-b']dipyridin-2(1H)-one (32 mg, 0.12 mmol) THF (1 mL) at 0° C., was added borane-dimethyl sulfide complex (38 mg, 0.5 mmol). The reaction was stirred overnight and quenched by MeOH followed by 4N HCl dioxane solution. The solution was heated to 40° C. for two hours and then concentrated to afford the title compound, which was carried onto the next step without purification. ES/MS: m/z=245.2 $[M+H]^+$.

General Procedure XLVII-E for the Synthesis of Intermediates Eau.

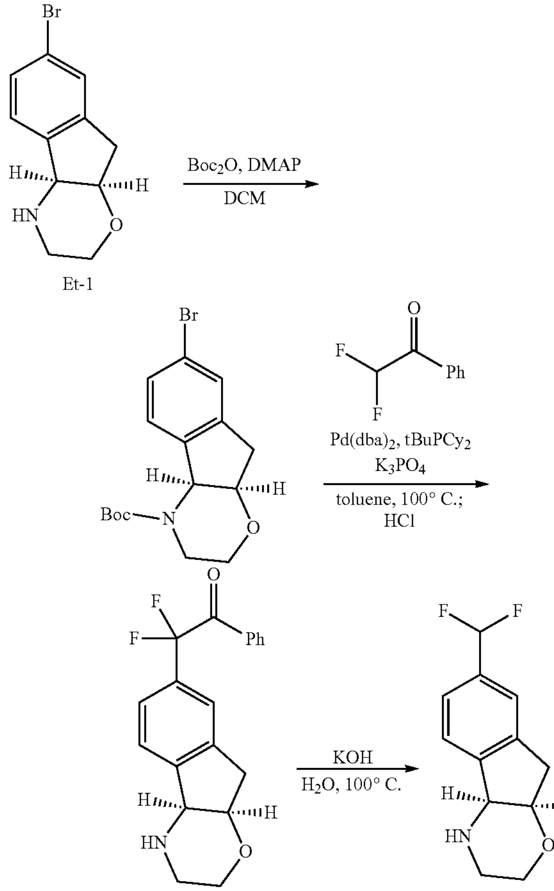

Step 1: tert-butyl (4aS,9aR)-7-bromo-2,3,9,9a-tetrahydroindeno[2,1-b][1,4]oxazine-4(4aH)-carboxylate. To a solution of (4aS,9aR)-7-bromo-2,3,4,4a,9,9a-hexahydroindeno[2,1-b][1,4]oxazine Et-1 (218 mg, 0.86 mmol) in DCM (1 mL) was added Boc anhydride (209 mg, 0.96 mmol) and DMAP (4.2 mg, 0.03 mmol). The solution was stirred at rt for 1 hr and then was diluted by DCM and washed by water. The organic layer was separated, concentrated, and purified by flash chromatography to give title product. ES/MS: m/z=339.2 $[M-Me]^+$.

Step 2: 2,2-difluoro-2-((4aS,9aR)-2,3,4,4a,9,9a-hexahydroindeno[2,1-b][1,4]oxazin-7-yl)-1-phenylethan-1-one. A screw-capped vial was charged with tert-butyl (4aS,9aR)-7-bromo-2,3,9,9a-tetrahydroindeno[2,1-b][1,4]oxazine-4(4aH)-carboxylate (196 mg, 0.553 mmol), bis(dibenzylideneacetone)palladium (31.8 mg, 0.055 mmol), α,α-difluoroacetophenone (173 mg, 1.11 mmol), $K_3PO_4$ (470 mg, 2.21 mmol), toluene (2.5 mL), and a magnetic stirring bar. The mixture was stirred at 100° C. for 30 h and then cooled to room temperature and concentrated. To the mixture, was added 4N HCl in dioxane (1 mL), and the resulting suspension was stirred at rt for 2 h. The solvent was then evaporated under reduced pressure. The crude product was directly used in next step. ES/MS: m/z=330.0 $[M+H]^+$.

Step 3: (4aS,9aR)-7-(difluoromethyl)-2,3,4,4a,9,9a-hexahydroindeno[2,1-b][1,4]oxazine (Eau-1). To the crude product from the previous step was added KOH (1 g) and $H_2O$ (2 mL), and the resulting suspension was stirred at 100° C. for 2 h. After the mixture was cooled to room temperature, the mixture was diluted with $H_2O$ and extracted with EtOAc. The organic layer was collected, concentrated, and purified by flash chromatography to give title product. ES/MS: m/z=226.02 $[M+H]^+$.

Eau-2

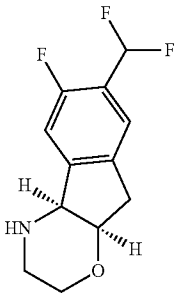

(4aS,9aR)-7-(difluoromethyl)-6-fluoro-2,3,4,4a,9,9a-hexahydroindeno[2,1-b][1,4]oxazine (Eau-2). Prepared following procedure XLVII-E starting with (4aS,9aR)-7-bromo-6-fluoro-2,3,4,4a,9,9a-hexahydroindeno[2,1-b][1,4]oxazine Et-3. ES/MS: m/z=244.0 $[M+H]^+$.

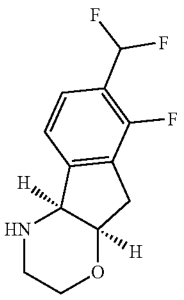

Eau-3

(4aS,9aR)-7-(difluoromethyl)-8-fluoro-2,3,4,4a,9,9a-hexahydroindeno[2,1-b][1,4]oxazine (Eau-3). Prepared following procedure XLVII-E starting with (4aS,9aR)-7-bromo-8-fluoro-2,3,4,4a,9,9a-hexahydroindeno[2,1-b][1,4]oxazine Et-4. ES/MS: m/z=244.0 [M+H]$^+$.

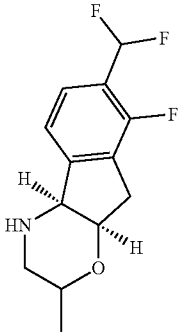

Eau-4

(4aS,9aR)-7-(difluoromethyl)-8-fluoro-2-methyl-2,3,4,4a,9,9a-hexahydroindeno[2,1-b][1,4]oxazine (Eau-4). Prepared following procedure XLVII-E starting with (4aS,9aR)-7-bromo-8-fluoro-2-methyl-2,3,4,4a,9,9a-hexahydroindeno[2,1-b][1,4]oxazine Eas-1. ES/MS: m/z =258.0 [M+H]$^+$.

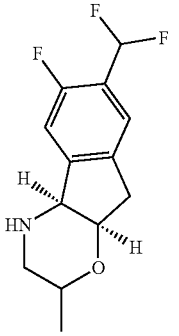

Eau-5

(4aS,9aR)-7-(difluoromethyl)-6-fluoro-2-methyl-2,3,4,4a,9,9a-hexahydroindeno[2,1-b][1,4]oxazine (Eau-5). Prepared following procedure XLVII-E starting with (4aS,9aR)-7-bromo-6-fluoro-2-methyl-2,3,4,4a,9,9a-hexahydroindeno[2,1-b][1,4]oxazine Eas-2. ES/MS: m/z =258.0 [M+H]$^+$.

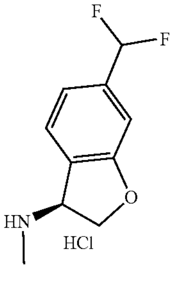

Eau-6

(S)-6-(difluoromethyl)-N-methyl-2,3-dihydrobenzofuran-3-amine hydrogen chloride (Eau-6). Prepared following procedure XLVII-E starting with (S)-6-bromo-N-methyl-2,3-dihydrobenzofuran-3-amine Eh-5. ES/MS: m/z=168.9 [M-NHMe]$^+$.

General Procedure XLVIII-E for the Synthesis of Intermediates Eav.

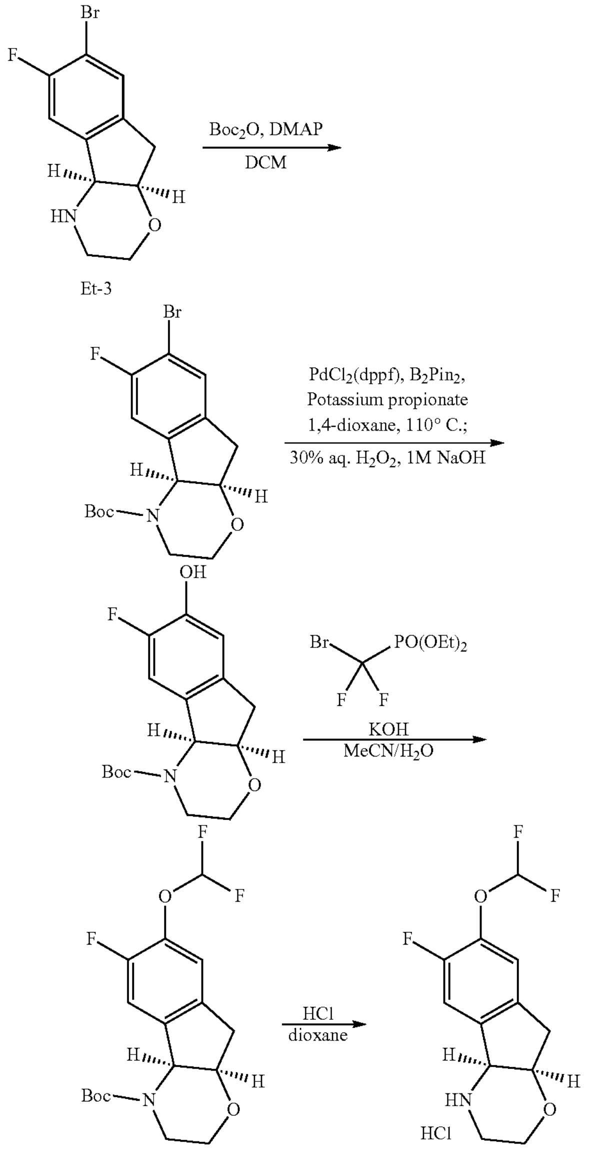

Step 1: tert-butyl (4aS,9aR)-7-bromo-6-fluoro-2,3,9,9a-tetrahydroindeno[2,1-b][1,4]oxazine-4(4aH)-carboxylate. To a solution of (4aS,9aR)-7-bromo-6-fluoro-2,3,4,4a,9,9a-hexahydroindeno[2,1-b][1,4]oxazine Et-3 (467 mg, 1.72 mmol) in DCM (6 mL) was added Boc anhydride (412 mg, 1.89 mmol), triethylamine (0.72 mL, 5.15 mmol) and DMAP (8.4 mg, 0.07 mmol). The solution was stirred at rt for 1 hr and then was diluted by DCM and washed by water. The organic layer was separated, concentrated and purified by flash chromatography to give title product. ES/MS: m/z=357.2 [M-Me]$^+$.

Step 2: tert-butyl (4aS,9aR)-6-fluoro-7-hydroxy-2,3,9,9a-tetrahydroindeno[2,1-b][1,4]oxazine-4(4aH)-carboxylate A screw-capped vial was charged with tert-butyl (4aS,9aR)-7-bromo-6-fluoro-2,3,9,9a-tetrahydroindeno[2,1-b][1,4]oxazine-4(4aH)-carboxylate (244 mg, 0.66 mmol), $PdCl_2$(dppf) (72.9 mg, 0.009 mmol), 1,4-dioxane (2.0 mL), and a magnetic stirring bar. The mixture was stirred at 110° C. for 1 h and then cooled to room temperature, dissolved in EtOAc and filtered through a pad of celite. The solution was concentrated and redissolved in dioxane again. 30% aqueous $H_2O_2$ (0.2 mL) and 1M NaOH (1.64 mL) was added at rt. The mixture was stirred for 1 hour and then slowly quenched with water. The aqueous phase was extracted by EtOAc for three times and the organic layer was combined, dried with $MgSO_4$ and reduced in vacuo. The residue was purified by chromatography. ES/MS: m/z=294.5 $[M-Me]^+$.

Step 3: tert-butyl (4aS,9aR)-7-(difluoromethoxy)-6-fluoro-2,3,9,9a-tetrahydroindeno[2,1-b][1,4]oxazine-4(4aH)-carboxylate. To the product from the previous step (80 mg, 0.26 mmol) was added a 1:1 mixture of acetonitrile/water (3 mL) and KOH (290 mg, 6 mmol), which was cooled using an ice bath. The mixture was vigorously mixed for 15 min and then bromodifluoromethyl diethylphosphonate (138 mg, 0.52 mmol) was added to the mixture in one portion, and mixing and cooling was maintained for an additional 15 -60 min, followed by 2.5 h at r.t. The reaction mixture was then diluted with diethyl ether and the organic phase separated. The water phase was further washed with diethyl ether. The combined organic phase was dried over anhydrous $Na_2SO_4$ and the solvent evaporated to provide a crude product which was purified using column chromatography on silica gel ES/MS: m/z=344.6 $[M-Me]^+$.

Step 4: (4aS,9aR)-7-(difluoromethoxy)-6-fluoro-2,3,4,4a,9,9a-hexahydroindeno[2,1-b][1,4]oxazine hydrochloride (Eav-1). To tert-butyl (4aS,9aR)-7-(difluoromethoxy)-6-fluoro-2,3,9,9a-tetrahydroindeno[2,1-b][1,4]oxazine-4(4aH)-carboxylate (80 mg, 0.23 mmol) was added 1 mL 4N HCl in 1,4-dioxane. The solution was stirred at rt for 1 hour and then concentrated to afford the title compound without any purification. ES/MS: m/z=260.0 $[M+H]^+$.

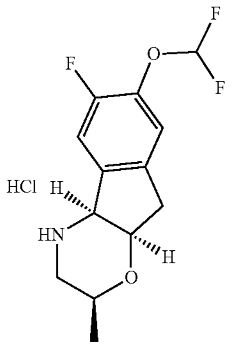

Eav-2

(2S,4aS,9aR)-7-(difluoromethoxy)-6-fluoro-2-methyl-2,3,4,4a,9,9a-hexahydroindeno[2,1-b][1,4]oxazine hydrochloride (Eav-2). Prepared following procedure XLVIII-E starting with (2S,4aS,9aR)-7-bromo-6-fluoro-2-methyl-2,3,4,4a,9,9a-hexahydroindeno[2,1-b][1,4]oxazine Et-6. ES/MS: m/z=274.0 $[M+H]^+$.

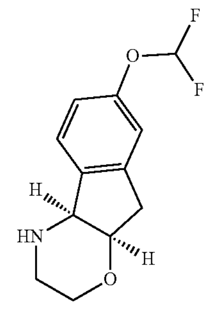

Eav-3

(4aS,9aR)-7-(difluoromethoxy)-2,3,4,4a,9,9a-hexahydroindeno[2,1-b][1,4]oxazine hydrochloride (Eav-3): Prepared using general procedure XLVIII-E starting with (4aS,9aR)-7-bromo-2,3,4,4a,9,9a-hexahydroindeno[2,1-b][1,4]oxazine Et-1. ES/MS: m/z=242.0 $[M+H]^+$.

General Procedure XLIX-E for the Synthesis of Intermediates Eaw:

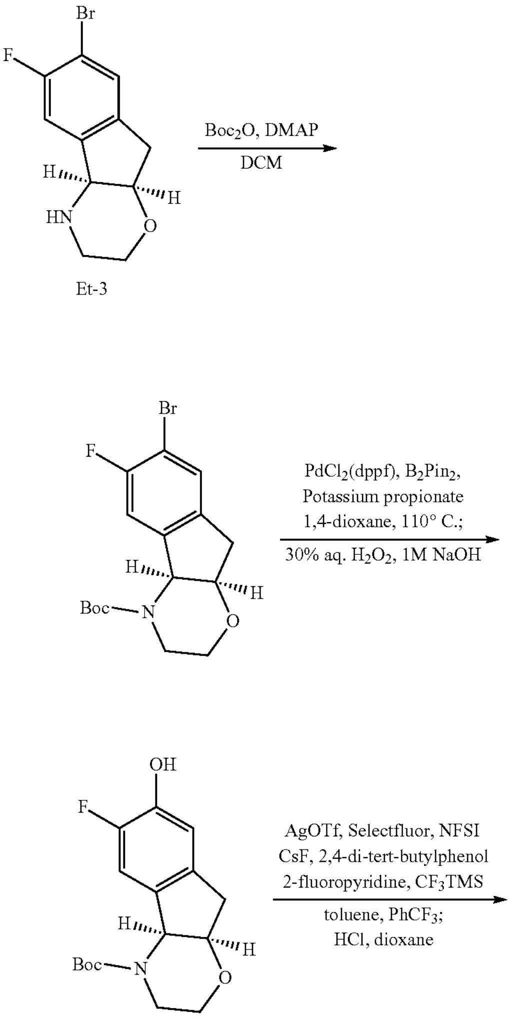

-continued

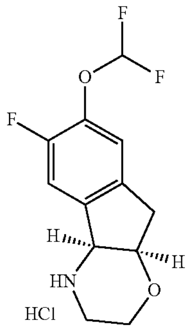

Eaw-1

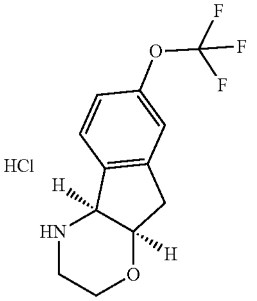

Eaw-2

Step 1: tert-butyl (4aS,9aR)-7-bromo-6-fluoro-2,3,9,9a-tetrahydroindeno[2,1-b][1,4]oxazine-4(4aH)-carboxylate. To a solution of (4aS,9aR)-7-bromo-6-fluoro-2,3,4,4a,9,9a-hexahydroindeno[2,1-b][1,4]oxazine Et-3 (467 mg, 1.72 mmol) in DCM (6 mL) was added Boc anhydride (412 mg, 1.89 mmol), triethylamine (0.72 mL, 5.15 mmol) and DMAP (8.4 mg, 0.07 mmol). The solution was stirred at rt for 1 hr and then was diluted by DCM and washed by water. The organic layer was separated, concentrated and purified by flash chromatography to give title product. ES/MS: m/z=357.2 [M-Me]$^+$.

Step 2: tert-butyl (4aS,9aR)-6-fluoro-7-hydroxy-2,3,9,9a-tetrahydroindeno[2,1-b][1,4]oxazine-4(4aH)-carboxylate. In a screw-capped vial was charged with tert-butyl (4aS,9aR)-7-bromo-6-fluoro-2,3,9,9a-tetrahydroindeno[2,1-b][1,4]oxazine-4(4aH)-carboxylate (244 mg, 0.66 mmol), $PdCl_2$(dppf) (72.9 mg, 0.009 mmol), 1,4-dioxane (2.0 mL), and a magnetic stirring bar. The mixture was stirred at 110° C. for 1 h and then cooled to room temperature, dissolved in EtOAc and filtered through a pad of celite. The solution was concentrated and redissolved in dioxane again. 30% aqueous $H_2O_2$ (0.2 mL) and 1M NaOH (1.64 mL) was added at rt. The mixture was stirred for 1 hour and then slowly quenched with water. The aqueous phase was extracted by EtOAc for three times and the organic layer was combined, dried with $MgSO_4$ and reduced in vacuo. The residue was purified by chromatography. ES/MS: m/z=294.5 [M-Me]$^+$.

Step 3: (4aS,9aR)-6-fluoro-7-(trifluoromethoxy)-2,3,4,4a,9,9a-hexahydroindeno[2,1-b][1,4]oxazine hydrochloride (Eaw-1). To a reaction tube that was equipped with a stirring bar, tert-butyl (4aS,9aR)-6-fluoro-7-hydroxy-2,3,9,9a-tetrahydroindeno[2,1-b][1,4]oxazine-4(4aH)-carboxylate (40 mg, 0.13 mmol), AgOTf (166 mg, 0.65 mmol), Selectfluor (91.6 mg, 0.26 mmol), NFSI (81.6 mg, 0.26 mmol), CsF (118 mg, 0.77 mmol), 2,4-di-tert-butylphenol (40.1 mg, 0.19 mmol) were added successively in a nitrogen-filled glovebox. Then toluene (0.65 mL), $PhCF_3$ (1.3 mL), 2-fluoropyridine (0.056 mL, 0.65 mmol) and $CF_3TMS$ (0.1 mL, 0.65 mmol) were added successively under Ar atmosphere. The reaction mixture was stirred at room temperature. After 16 h, the reaction mixture was filtered through a plug of silica (eluted with ethyl acetate). The filtrate was concentrated, and treated by 1 mL 4N HCl in 1,4-dioxane at rt for 1 hr. The solution was concentrated and then purified by column chromatography. ES/MS: m/z=278.0 [M+H]$^+$.

(4aS,9aR)-7-(trifluoromethoxy)-2,3,4,4a,9,9a-hexahydroindeno[2,1-b][1,4]oxazine hydrochloride (Eaw-2). Prepared following procedure XLIX-E starting with (4aS,9aR)-7-bromo-2,3,4,4a,9,9a-hexahydroindeno[2,1-b][1,4]oxazine Et-1. ES/MS: m/z=260.0 [M+H]$^+$.

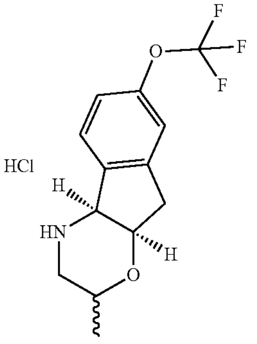

Eaw-3

(4aS,9aR)-2-methyl-7-(trifluoromethoxy)-2,3,4,4a,9,9a-hexahydroindeno[2,1-b][1,4]oxazine hydrochloride (Eaw-3). Prepared following procedure XLIX-E starting with (4aS,9aR)-7-bromo-2-methyl-2,3,4,4a,9,9a-hexahydroindeno[2,1-b][1,4]oxazine Eas-3. ES/MS: m/z=274.0 [M+H]$^+$.

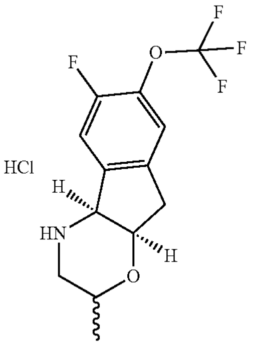

Eaw-4

(4aS,9aR)-6-fluoro-2-methyl-7-(trifluoromethoxy)-2,3,4,4a,9,9a-hexahydroindeno[2,1-b][1,4]oxazine hydrochloride (Eaw-4). Prepared following procedure XLIX-E starting with (4aS,9aR)-7-bromo-6-fluoro-2-methyl-2,3,4,4a,9,9a-hexahydroindeno[2,1-b][1,4]oxazine Eas-2. ES/MS: m/z=292.0 $[M+H]^+$.

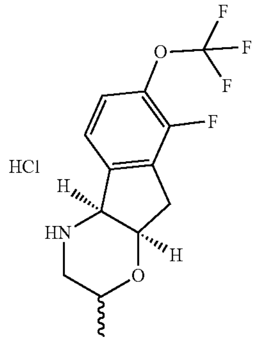

Eaw-5

(4aS,9aR)-8-fluoro-2-methyl-7-(trifluoromethoxy)-2,3,4,4a,9,9a-hexahydroindeno[2,1-b][1,4]oxazine (Eaw-5). Prepared following procedure XLIX-E starting with (4aS,9aR)-7-bromo-8-fluoro-2-methyl-2,3,4,4a,9,9a-hexahydroindeno[2,1-b][1,4]oxazine Eas-1. ES/MS: m/z=292.0 $[M+H]^+$.

General Procedure L-E for the Synthesis of Intermediates Eax.

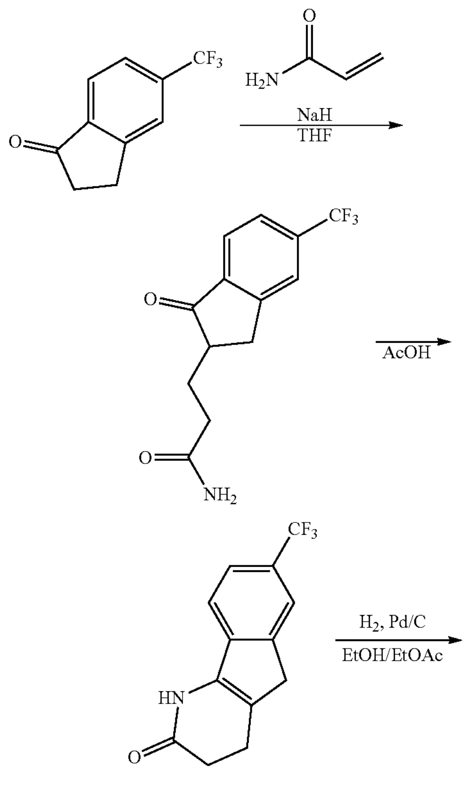

-continued

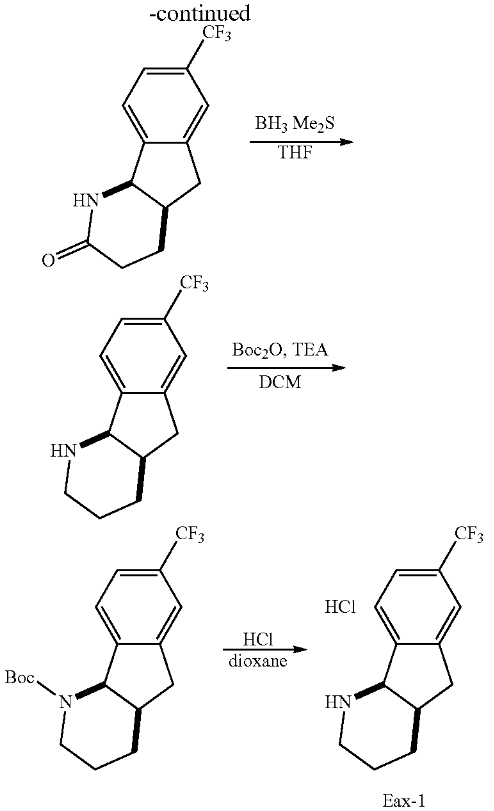

Eax-1
(±)

Step 1: 3-(1-oxo-5-(trifluoromethyl)-2,3-dihydro-1H-inden-2-yl)propenamide. A 100 mL round bottom flask was charged with 5-(trifluoromethyl)indan-1-one (1.00 g, 5.00 mmol) and prop-2-enamide (373 mg, 5.25 mmol) which was suspended with THF (25.0 mL). The solution was placed in a 0° C. bath. NaH (249 mg, 6.49 mmol, 60% purity) was slowly added to the flask. The flask was warmed to room temperature and left to stir for 24 hours. The solution was carefully quenched with NH4Cl and extracted with ethyl acetate (x2). The organic layer was then extracted with brine (x1), dried over magnesium sulfate, filtered, and concentrated under reduced pressure. The crude product was purified with silica gel chromatography to afford the desired product. ES/MS: m/z=272.0 $[M+H]^+$.

Step 2: 7-(trifluoromethyl)-1,3,4,5-tetrahydro-2H-indeno[1,2-b]pyridin-2-one. A 25 ml round bottom flask was charged with 3-(1-oxo-5-(trifluoromethyl)-2,3-dihydro-1H-inden-2-yl)propanamide (155 mg, 0.571 mmol) which was suspended in AcOH (3.00 mL). The solution was left to stir at 90° C. for 5 hours, which was then cooled to room temperature and dry loaded with silica gel chromatography: 0-100% ethyl acetate in hexanes to afford the desired product. ES/MS: m/z=254.2 $[M+H]^+$.

Step 3: cis-7-(trifluoromethyl)-1,3,4,4a,5,9b-hexahydro-2H-indeno[1,2-b]pyridin-2-one. To a solution of 7-(trifluoromethyl)-1,3,4,5-tetrahydro-2H-indeno[1,2-b]pyridin-2-one (130 mg, 0.513 mmol) in ethanol (10 mL) and ethyl acetate (1 mL) was added Pd/C (10% w/w, 82 mg). The heterogeneous mixture was stirred vigorously at room temperature under hydrogen gas (1 atm) for 1 hour. The mixture was filtered through a pad of celite and the organic solution was reduced under pressure and continued forward without further purification. ES/MS: m/z=256.0 $[M+H]^+$.

Step 4: cis-7-(trifluoromethyl)-2,3,4,4a,5,9b-hexahydro-1H-indeno[1,2-b]pyridine. To a solution of cis-7-(trifluoromethyl)-1,3,4,4a,5,9b-hexahydro-2H-indeno[1,2-b]pyridin-2-one (128 mg, 0.501 mmol) in THF (2.0 mL) was added borane dimethyl sulfide complex (0.285 mL, 3.01 mmol) at room temperature. The reaction was allowed to stir for 16 hours before being cooled to 0° C. MeOH (5 mL) was then added slowly and the mixture was allowed to stir for 15 min. After this time, 5 mL of HCl in dioxane added and the reaction was allowed to warm from 0° C. to 23° C. over 5 minutes while stirring. After this time, the mixture was concentrated. The resulting crude product was carried forward to the next step. ES/MS: m/z=242.2 $[M+H]^+$.

Step 5: cis-tert-butyl 7-(trifluoromethyl)-2,3,4,4a,5,9b-hexahydro-1H-indeno[1,2-b]pyridine-1-carboxylate. A 25 mL round bottom flask was charged with cis-7-(trifluoromethyl)-2,3,4,4a,5,9b-hexahydro-1H-indeno[1,2-b]pyridine (121 mg, 0.502 mmol), which was suspended in DCM (2.00 mL) and Triethylamine (0.210 mL, 1.50 mmol). Di-tert-butyl dicarbonate (164 mg, 0.752 mmol) was then added in a single portion and the resulting mixture was allowed to stir at 23° C. for 2 hours. After the allotted time, the reaction was concentrated, and the resulting mixture was purified by silica gel column chromatography. ES/MS: m/z=286.0 $[M-tBu+H]^+$.

Step 6: cis-(4aR,9bR)-7-(trifluoromethyl)-2,3,4,4a,5,9b-hexahydro-1H-indeno[1,2-b]pyridine (Eax-1). A 25 mL round bottom flask with tert-butyl cis-7-(trifluoromethyl)-2,3,4,4a,5,9b-hexahydro-1H-indeno[1,2-b]pyridine-1-carboxylate (150 mg, 0.439 mmol) was suspended in 2 mL of HCl in dioxane (4.0 M). The mixture was left to stir for 1 hour. After this time, the mixture was concentrated and the resulting crude product was carried forward. ES/MS: m/z=242.2 $[M+H]^+$.

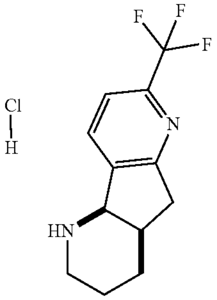

Eax-2
(±)

Cis-(4bR,8aR)-2-(trifluoromethyl)-4b,6,7,8,8a,9-hexahydro-5H-cyclopenta[1,2-b:3,4-b']dipyridine hydrochloride (Eax-2). Prepared following procedure L-E starting with 2-(trifluoromethyl)-6,7-dihydrocyclopenta[b]pyridin-5-one. ES/MS: m/z=243.0 $[M+H]^+$.

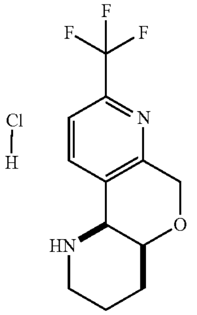

Eax-3
(±)

Cis-(4aS,10bS)-8-(trifluoromethyl)-2,3,4,4a,6,10b-hexahydro-1H-pyrano[3,2-b:5,4-b']dipyridine hydrochloride (Eax-3). Prepared following procedure L-E starting with 2-(trifluoromethyl)-8H-pyrano[3,4-b]pyridin-5-one. ES/MS: m/z=259.0 $[M+H]^+$.

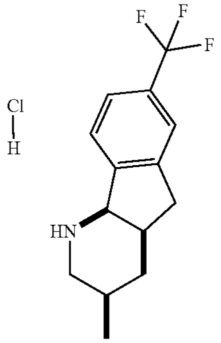

Eax-4
(±)

Cis-(3R,4aR,9bR)-3-methyl-7-(trifluoromethyl)-2,3,4,4a,5,9b-hexahydro-1H-indeno[1,2-b]pyridine hydrochloride (Eax-4). Prepared following procedure L-E starting with 5-(trifluoromethyl)indan-1-one and 2-methylprop-2-enamide. ES/MS: m/z=256.0 $[M+H]^+$.

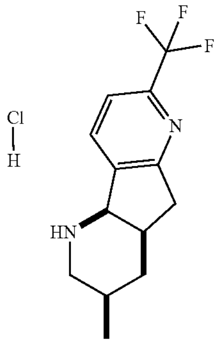

Eax-5
(±)

Cis-(4bR,7R,8aR)-7-methyl-2-(trifluoromethyl)-4b,6,7,8,8a,9-hexahydro-5H-cyclopenta[1,2-b:3,4-b']dipyridine hydrochloride (Eax-5). Prepared following procedure L-E starting with 2-(trifluoromethyl)-6,7-dihydrocyclopenta[b]pyridin-5-one and 2-methylprop-2-enamide. ES/MS: m/z=257.0 $[M+H]^+$.

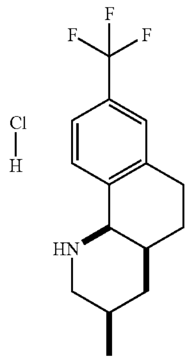

Eax-6
(±)

Cis-(3R,4aS,10bR)-3-methyl-8-(trifluoromethyl)-1,2,3,4,4a,5,6,10b-octahydrobenzo[h]quinoline hydrochloride (Eax-6). Prepared following procedure L-E starting with 6-(trifluoromethyl)tetralin-1-one and 2-methylprop-2-enamide. ES/MS: m/z=270.0 $[M+H]^+$.

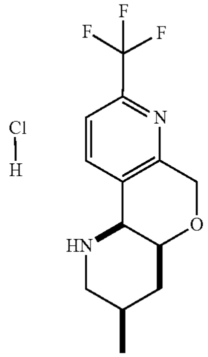

Eax-7
(±)

Cis-(3R,4aS,10bS)-3-methyl-8-(trifluoromethyl)-2,3,4,4a,6,10b-hexahydro-1H-pyrano[3,2-b:5,4-b']dipyridine hydrochloride (Eax-7). Prepared following procedure L-E starting with 2-(trifluoromethyl)-8H-pyrano[3,4-b]pyridin-5-one and 2-methylprop-2-enamide. ES/MS: m/z=273.0 $[M+H]^+$.

General Procedure LI-E for the Synthesis of Intermediates Eay:

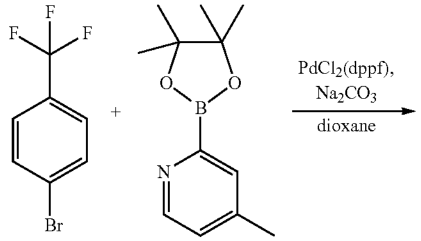

-continued

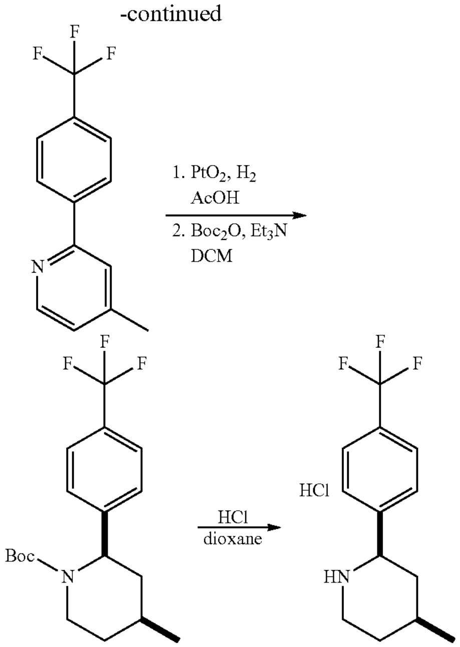

Eay-1
(±)

Step 1: 4-methyl-2-(4-(trifluoromethyl)phenyl)pyridine. To a solution of 1-bromo-4-(trifluoromethyl)benzene (1.13 g, 5.02 mmol), 4-methyl-2-(4,4,5,5-tetramethyl-1,3,2-dioxaborolan-2-yl)pyridine (1.00 g, 4.56 mmol), and PdCl2(dppf) (508 mg, 0.685 mmol) in dioxane (20 mL), was added 2M $Na_2CO_3$ (11.4 mL, 22.8 mmol). The mixture was bubbled through argon for 1 minute and left to stir at 90 C for 6 hours. The mixture was filtered through a pad of celite and anhydrous $MgSO_4$. The solution was reduced under pressure and the crude was purified by flash chromatography. ES/MS: m/z=238.2

Step 2: Cis-tert-butyl 4-methyl-2-(4-(trifluoromethyl)phenyl)piperidine-1-carboxylate. To a solution of 4-methyl-2-(4-(trifluoromethyl)phenyl)pyridine (50 mg, 0.211 mmol) in AcOH (10 mL) was added $PtO_2H_2O$ (26 mg, 105 mmol). The heterogenous mixture was then stirred vigorously at room temperature under an atmosphere of hydrogen (1 atm) until full conversion of the starting pyridine by LCMS. The solution was filtered through a pad of celite and reduced in vacuo. The crude residue was dissolved in 2 mL of DCM, followed by the addition of triethylamine (208 mg, 2.06 mmol) and $Boc_2O$ (54 mg, 0.247 mmol). When the reaction was complete as judged by LCMS analysis, the reaction was evaporated to dryness and purified by column chromatography over silica gel to afford the desired product. ES/MS: m/z=288.0 $[M-tBu+H]^+$ Step 3: Cis-(2R,4S)-4-methyl-2-(4-(trifluoromethyl)phenyl)piperidine hydrochloride (Eay-1). tert-butyl (2R,4S)-4-methyl-2-(4-(trifluoromethyl)phenyl)piperidine-1-carboxylate (64 mg, 0.186 mmol) was dissolved in 3 mL of 4M HCl in Dioxane. When the reaction was complete as judged by LCMS analysis, the reaction was evaporated to dryness and used without further purification. ES/MS: m/z=244.0 $[M+H]^+$ General Procedure LII-E for the Synthesis of Intermediates Eaz:

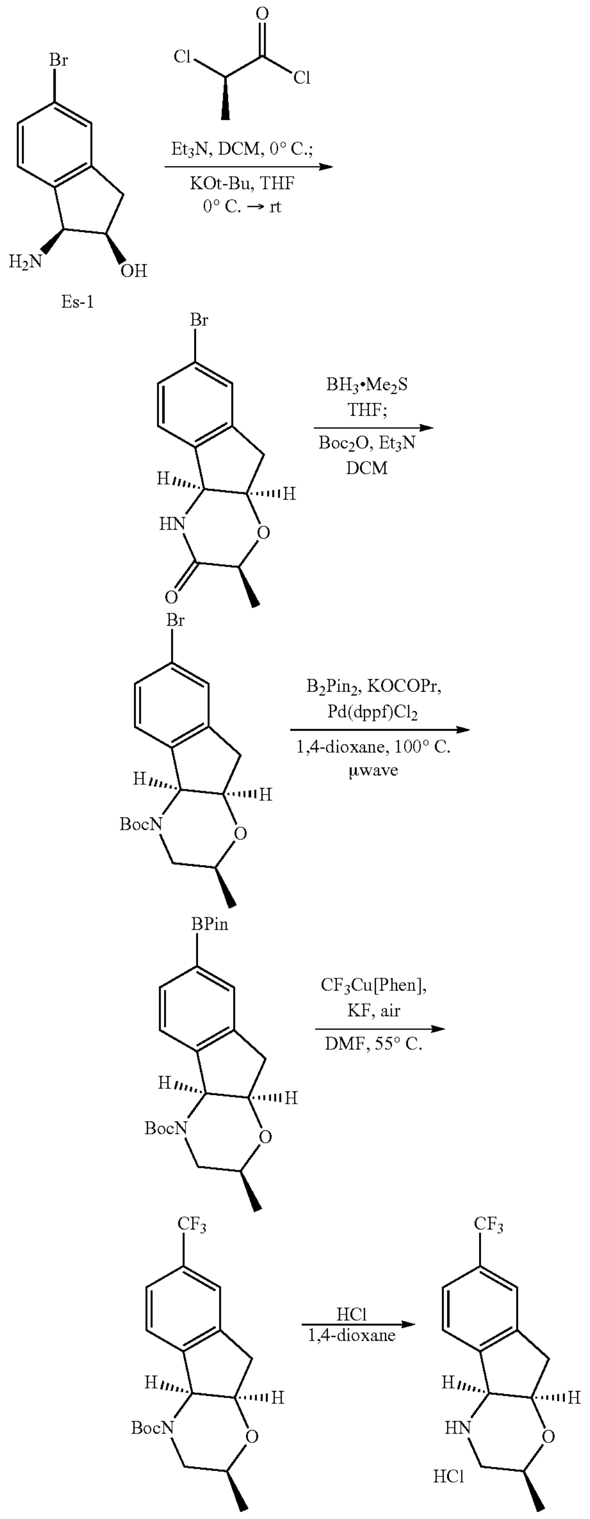

Es-1

Eaz-1

Step 1: (2S,4aS,9aR)-7-bromo-2-methyl-4,4a,9,9a-tetrahydroindeno[2,1-b][1,4]oxazin-3(2H)-one. To a solution of (1S,2R)-1-amino-5-bromo-2,3-dihydro-1H-inden-2-ol Es-1 (300 mg, 1.3 mmol) and triethylamine (0.24 mL, 1.7 mmol) in DCM (4 mL) was added (R)-2-chloropropanoyl chloride (prepared by mixing (R)-2-chloropropionic acid (164 mg, 1.5 mmol), oxalyl chloride (0.15 mL, 1.7 mmol) and DMF (15 μL) in DCM (4 mL) at 0° C., followed by concentrating at 0° C.) dropwise. After stirring for 15 minutes, water and EtOAc were added, and the mixture was transferred to a separatory funnel. The organic layer was separated, washed with brine, dried over $MgSO_4$, filtered, and concentrated. The resulting residue was suspended in THF (1 mL) and potassium tert-butoxide (1.0 M in THF, 1.3 mL, 1.3 mmol) was added dropwise at 0° C. Following warming to room temperature and stirring for 1 hour, the mixture was quenched with sat. aq. $NH_4Cl$ and diluted with EtOAc. The organic layer was separated, washed with brine, and dried over $MgSO_4$. Purification by silica gel flash column chromatography afforded (2S,4aS,9aR)-7-bromo-2-methyl-4,4a,9,9a-tetrahydroindeno[2,1-b][1,4]oxazin-3(2H)—. ES/MS: m/z=282.0 $[M+H]^+$.

Step 2: tert-butyl (2S,4aS,9aR)-7-bromo-2-methyl-2,3,9,9a-tetrahydroindeno[2,1-b][1,4]oxazine-4(4aH)-carboxylate. To a solution of (2S,4aS,9aR)-7-bromo-2-methyl-4,4a,9,9a-tetrahydroindeno[2,1-b][1,4]oxazin-3(2H)-one (180 mg, 0.64 mmol) in THF (2 mL) was added borane dimethyl sulfide complex (0.36 mL, 3.8 mmol). After stirring overnight, the mixture was cooled to 0° C. and MeOH (5 mL) was added slowly. After stirring for an additional 15 minutes, HCl (4.0 M in dioxane, 5 mL, 20 mmol) was added and the mixture was allowed to warm to room temperature and concentrated. The resulting residue was suspended in DCM (2 mL) and triethylamine (0.27 mL, 1.9 mmol) was added followed by Di-tert-butyl dicarbonate (167 mg, 0.77 mmol). After stirring for 2 hours, the mixture was concentrated and purified by silica gel flash column chromatography to afford tert-butyl (2S,4aS,9aR)-7-bromo-2-methyl-2,3,9,9a-tetrahydroindeno[2,1-b][1,4]oxazine-4(4aH)-carboxylate. ES/MS: m/z=311.8 $[M-tBu+H]^+$.

Step 3: tert-butyl (2S,4aS,9aR)-2-methyl-7-(4,4,5,5-tetramethyl-1,3,2-dioxaborolan-2-yl)-2,3,9,9a-tetrahydroindeno[2,1-b][1,4]oxazine-4(4aH)-carboxylate. A mixture of tert-butyl (2S,4aS,9aR)-7-bromo-2-methyl-2,3,9,9a-tetrahydroindeno[2,1-b][1,4]oxazine-4(4aH)-carboxylate (250 mg, 0.68 mmol), $Pd(dppf)Cl_2$ (75 mg, 0.10 mmol), potassium propionate (228 mg, 2.0 mmol), and bis(pinacolato)diboron (207 mg, 0.82 mmol) in 1,4-dioxane (2.5 mL) were sealed in a microwave vial and heated to 100° C. in a microwave reactor for 1 hour. The resulting mixture was concentrated and purified by silica gel flash column chromatography to afford tert-butyl (2S,4aS,9aR)-2-methyl-7-(4,4,5,5-tetramethyl-1,3,2-dioxaborolan-2-yl)-2,3,9,9a-tetrahydroindeno[2,1-b][1,4]oxazine-4(4aH)-carboxylate. ES/MS: m/z=360.0 $[M-tBu+H]^+$.

Step 4: tert-butyl (2S,4aS,9aR)-2-methyl-7-(trifluoromethyl)-2,3,9,9a-tetrahydroindeno[2,1-b][1,4]oxazine-4(4aH)-carboxylate. Trifluoromethyl(1,10-phenanthroline) copper (565 mg, 1.8 mmol) was added to a mixture of tert-butyl (2S,4aS,9aR)-2-methyl-7-(4,4,5,5-tetramethyl-1,3,2-dioxaborolan-2-yl)-2,3,9,9a-tetrahydroindeno[2,1-b][1,4]oxazine-4(4aH)-carboxylate (300 mg, 0.72 mmol) and potassium fluoride (84 mg, 1.4 mmol) in DMF (15 mL). Air was bubbled through the solution for 10 minutes, then the reaction vessel was sealed and heated to 60° C. overnight. After cooling to room temperature, the mixture was diluted with EtOAc, transferred to a separatory funnel, and successively washed with water and brine. The organic extract was dried over $MgSO_4$, filtered, and concentrated. Purification by silica gel flash column chromatography afforded tert-butyl (2S,4aS,9aR)-2-methyl-7-(trifluoromethyl)-2,3,9,9a-tetrahydroindeno[2,1-b][1,4]oxazine-4(4aH)-carboxylate. ES/MS: m/z =301.9 $[M-tBu+H]^+$.

Step 5: (2S,4aS,9aR)-2-methyl-7-(trifluoromethyl)-2,3,4,4a,9,9a-hexahydroindeno[2,1-b][1,4]oxazine hydrochloride (Eaz-1). To a solution of tert-butyl (2S,4aS,9aR)-2-methyl-7-(trifluoromethyl)-2,3,9,9a-tetrahydroindeno[2,1-b][1,4]oxazine-4(4aH)-carboxylate (120 mg, 0.34 mmol) in 1,4-dioxane (2 mL) was added HCl (4.0 M in dioxane, 0.5 mL, 2.0 mmol). After stirring overnight, the mixture was concentrated and used in the next step without further purification. ES/MS: m/z=258.0 $[M+H]^+$. $^1H$ NMR (400 MHz, Methanol-d4) δ 7.77-7.49 (m, 3H), 4.57-4.49 (m, 2H), 3.79-3.66 (m, 2H), 3.13 (d, J=4.3 Hz, 1H), 2.96 (d, J=16.6 Hz, 1H), 2.86 (dd, J=12.8, 2.2 Hz, 1H), 2.45 (dd, J=12.8, 10.3 Hz, 1H), 1.03 (d, J=6.3 Hz, 3H).

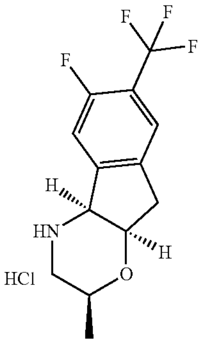

Eaz-2

(2S,4aS,9aR)-6-fluoro-2-methyl-7-(trifluoromethyl)-2,3,4,4a,9,9a-hexahydroindeno[2,1-b][1,4]oxazine hydrochloride (Eaz-2): Prepared using general procedure LII-E starting with (1S,2R)-1-amino-5-bromo-6-fluoro-2,3-dihydro-1H-inden-2-ol Es-3 and (R)-2-chloropropanoyl chloride. ES/MS: m/z=276.0 $[M+H]^+$.

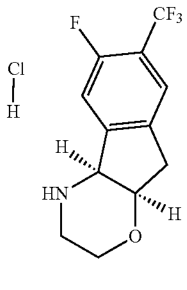

Eaz-3

(4aS,9aR)-6-fluoro-7-(trifluoromethyl)-2,3,4,4a,9,9a-hexahydroindeno[2,1-b][1,4]oxazine hydrochloride (Eaz-3). Prepared following general procedure LII-E starting with (1S,2R)-1-amino-5-bromo-6-fluoro-2,3-dihydro-1H-inden-2-ol Es-3 and 2-chloroacetyl chloride. ES/MS: m/z=262.0 $[M+H]^+$.

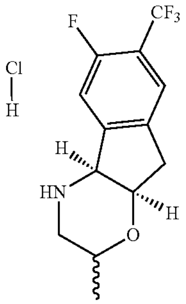

Eaz-4

(4aS,9aR)-6-fluoro-2-methyl-7-(trifluoromethyl)-2,3,4,4a,9,9a-hexahydroindeno[2,1-b][1,4]oxazine hydrochloride (Eaz-4). Prepared following procedure LII-E starting with (1S,2R)-1-amino-5-bromo-6-fluoro-2,3-dihydro-1H-inden-2-ol Es-3 and 2-chloropropanoyl chloride. ES/MS: m/z=276.0 $[M+H]^+$. (Eaz-4 was contaminated by Eaz-5, see below).

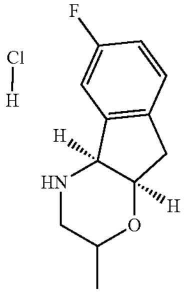

Eaz-5

(4aS,9aR)-6-fluoro-2-methyl-2,3,4,4a,9,9a-hexahydroindeno[2,1-b][1,4]oxazine hydrochloride (Eaz-5). Prepared as debrominated byproduct in the synthesis of Eaz-4. ES/MS: m/z=208.0 $[M+H]^+$.

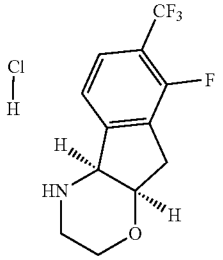

Eaz-6

(4aS,9aR)-8-fluoro-7-(trifluoromethyl)-2,3,4,4a,9,9a-hexahydroindeno[2,1-b][1,4]oxazine hydrochloride (Eaz-6). Prepared following procedure LII-E starting with (1S,2R)-1-amino-5-bromo-4-fluoro-2,3-dihydro-1H-inden-2-ol Es-2 and 2-chloroacetyl chloride. ES/MS: m/z=262.0 $[M+H]^+$.

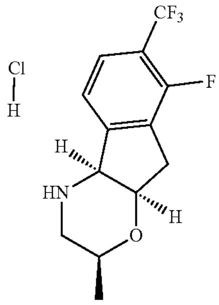

Eaz-7

(2S,4aS,9aR)-8-fluoro-2-methyl-7-(trifluoromethyl)-2,3,4,4a,9,9a-hexahydroindeno[2,1-b][1,4]oxazine hydrochloride (Eaz-7). Prepared following procedure LII-E starting with (1S,2R)-1-amino-5-bromo-4-fluoro-2,3-dihydro-1H-inden-2-ol Es-2 and (2R)-2-chloropropanoyl chloride. ES/MS: m/z=276.2 [M+H]+.

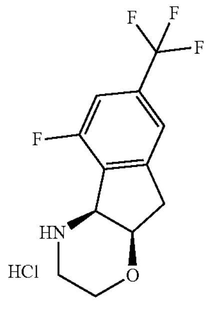

Eaz-8

(4aS,9aR)-5-fluoro-7-(trifluoromethyl)-2,3,4,4a,9,9a-hexahydroindeno[2,1-b][1,4]oxazine hydrogen chloride (Eaz-8). Prepared following procedure LII-E starting with (1S,2R)-1-amino-7-fluoro-5-bromo-2,3-dihydro-1H-inden-2-ol Es-6. ES/MS: m/z=262.2 [M+H]+.

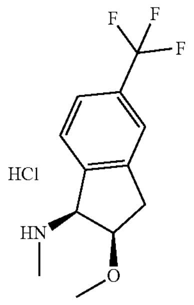

Eaz-9

(1S,2R)-2-methoxy-N-methyl-5-(trifluoromethyl)-2,3-dihydro-1H-inden-1-amine hydrochloride (Eaz-9). Prepared following steps 3-5 of procedure LII-E starting with tert-butyl ((1S,2R)-2-methoxy-5-(4,4,5,5-tetramethyl-1,3,2-dioxaborolan-2-yl)-2,3-dihydro-1H-inden-1-yl)(methyl)carbamate (intermediate reported in general procedure LXVI-E) ES/MS: m/z=246.1 [M+H]+.

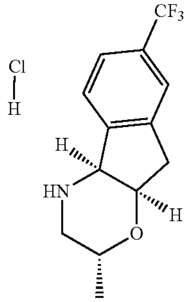

Eaz-10

(2R,4aS,9aR)-2-methyl-7-(trifluoromethyl)-2,3,4,4a,9,9a-hexahydroindeno[2,1-b][1,4]oxazine hydrochloride (Eaz-10). Prepared following steps 3-5 of procedure LII-E starting with (1S,2R)-1-amino-5-(trifluoromethyl)-2,3-dihydro-1H-inden-2-ol Es-7 and (S)-2-chloropropanoyl chloride. ES/MS: m/z=258.0 [M+H]+.

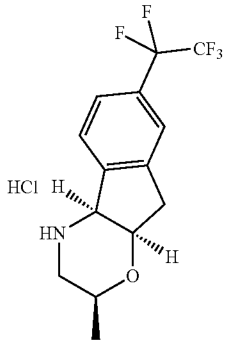

Eaz-11

(2S,4aS,9aR)-2-methyl-7-(perfluoroethyl)-2,3,4,4a,9,9a-hexahydroindeno[2,1-b][1,4]oxazine (Eaz-11). Prepared following general procedure LII-E starting with (1S,2R)-1-amino-5-bromo-2,3-dihydro-1H-inden-2-ol Es-1, (R)-2-chloropropionic acid, and perfluoroethyl(1,10-phenanthroline)copper. ES/MS: m/z=307.9 [M+H]+.

General Procedure LIII-E for the Synthesis of Intermediates Eba:

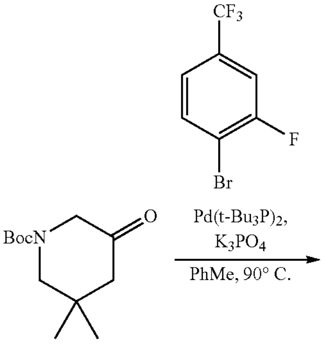

-continued

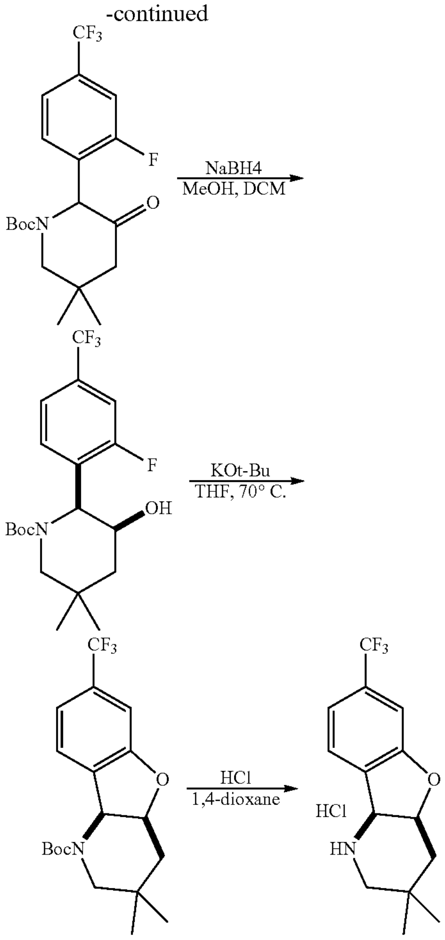

Eba-1
(±)

Step 1: tert-butyl 2-(2-fluoro-4-(trifluoromethyl)phenyl)-5,5-dimethyl-3-oxopiperidine-1-carboxylate. To a stirred solution of tert-butyl 3,3-dimethyl-5-oxo-piperidine-1-carboxylate (606 mg, 2.7 mmol) and 1-bromo-2-fluoro-4-(trifluoromethyl)benzene (360 mg, 1.5 mmol) in toluene (9 mL) was added $K_3PO_4$ (786 mg, 3.7 mmol) and Pd(t-Bu3P)$_2$ (53 mg, 0.10 mmol). The mixture was heated to 90° C. for 3 hours, then cooled to room temperature, filtered over celite, and concentrated. Purification by silica gel flash column chromatography afforded the desired product. ES/MS: m/z=334.8 [M-tBu+H]$^+$.

Step 2: tert-butyl 2-(2-fluoro-4-(trifluoromethyl)phenyl)-3-hydroxy-5,5-dimethylpiperidine-1-carboxylate. To a solution of tert-butyl 2-(2-fluoro-4-(trifluoromethyl)phenyl)-5,5-dimethyl-3-oxopiperidine-1-carboxylate (200 mg, 0.51 mmol) in MeOH (3 mL) and DCM (3 mL) at 0° C. was added $NaBH_4$ (1.45 g, 13 mmol). The solution was warmed to room temperature and left to stir for 30 minutes. The mixture was carefully quenched by the addition of water. The solution was extracted three times with EtOAc. The organic layers were then washed with brine, dried over $MgSO_4$, filtered and concentrated. Purification by silica gel flash column chromatography afforded the desired product. ES/MS: m/z=336.0 [M-tBu+H]$^+$.

Step 3: tert-butyl (4aS,9bS)-3,3-dimethyl-7-(trifluoromethyl)-3,4,4a,9b-tetrahydrobenzofuro[3,2-b]pyridine-1(2H)-carboxylate. Potassium tert-butoxide (84 mg, 0.75 mmol) was added to a solution of tert-butyl 2-(2-fluoro-4-(trifluoromethyl)phenyl)-3-hydroxy-5,5-dimethylpiperidine-1-carboxylate (195 mg, 0.50 mmol) in THF (2 mL). The mixture was heated to 70° C. for 10 minutes, then cooled to room temperature and sat. aq. $NH_4Cl$ was added. The mixture was diluted with EtOAc and transferred to a separatory funnel. The organic layer was washed with brine, dried over $MgSO_4$, filtered, and concentrated. Purification by silica gel flash column chromatography afforded the desired product. ES/MS: m/z=316.2 [M-tBu+H]$^+$.

Step 4: Cis-(4aS,9bS)-3,3-dimethyl-7-(trifluoromethyl)-1,2,3,4,4a,9b-hexahydrobenzofuro[3,2-b]pyridine hydrogen chloride (Eba-1). A solution of tert-butyl (4aS,9bS)-3,3-dimethyl-7-(trifluoromethyl)-3,4,4a,9b-tetrahydrobenzofuro[3,2-b]pyridine-1(2H)-carboxylate (28 mg, 0.075 mmol) in 1,4-dioxane (2 mL) was treated with HCl (4.0 M in dioxane, 2 mL, 12 mmol). After stirring overnight, the mixture was concentrated to afford the desired product as the hydrochloride salt. ES/MS: m/z=272.2 [M+H]$^+$.

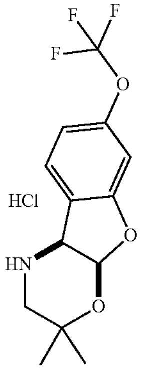

Eba-2
(±)

Cis-(4aS,9bS)-3,3-dimethyl-7-(trifluoromethoxy)-1,2,3,4,4a,9b-hexahydrobenzofuro[3,2-b]pyridine hydrochloride (Eba-2): Prepared using general procedure LIII-E starting with tert-butyl 3,3-dimethyl-5-oxo-piperidine-1-carboxylate and 1-bromo-2-fluoro-4-(trifluoromethoxy)benzene. ES/MS: m/z=288.2 [M+H]$^+$.

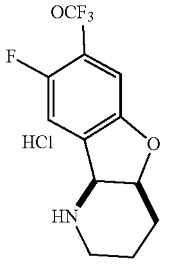

Eba-3
(±)

Cis-(4aS,9bS)-8-fluoro-7-(trifluoromethoxy)-1,2,3,4,4a,9b-hexahydrobenzofuro[3,2-b]pyridine hydrochloride (Eba-3). Prepared following general procedure LIII-E starting with tert-butyl 3-oxopiperidine-1-carboxylate and 1-bromo-2,5-difluoro-4-(trifluoromethoxy)benzene ES/MS: m/z=278.2 [M+H]$^+$.

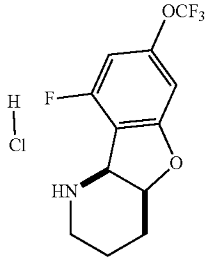

Eba-4
(±)

Cis-(4aS,9bS)-9-fluoro-7-(trifluoromethoxy)-1,2,3,4,4a,9b-hexahydrobenzofuro[3,2-b]pyridine hydrochloride (Eba-4). Prepared following procedure LIII-E starting with tert-butyl 3-oxopiperidine-1-carboxylate and 2-bromo-1,3-difluoro-5-(trifluoromethoxy)benzene. ES/MS: m/z=278.0 $[M+H]^+$.

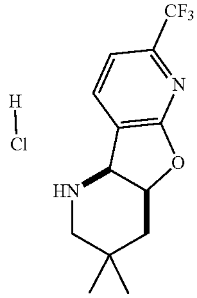

Eba-5
(±)

Cis-(4aS,9bS)-3,3-dimethyl-7-(trifluoromethyl)-1,2,3,4,4a,9b-hexahydrofuro[2,3-b:4,5-b']dipyridine hydrochloride (Eba-5). Prepared following procedure LIII-E starting with tert-butyl 3,3-dimethyl-5-oxo-piperidine-1-carboxylate and 2-chloro-3-iodo-6-(trifluoromethyl)pyridine. ES/MS: m/z=273.2 $[M+H]^+$.

Eba-6

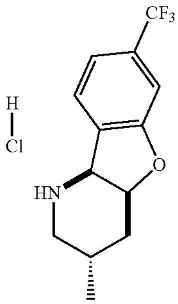

Cis-(3S)-3-methyl-7-(trifluoromethyl)-1,2,3,4,4a,9b-hexahydrobenzofuro[3,2-b]pyridine hydrochloride (Eba-6). Prepared following procedure LIII-E starting with tert-butyl (3S)-3-methyl-5-oxo-piperidine-1-carboxylate and 1-bromo-2,3-difluoro-4-(trifluoromethyl)benzene. ES/MS: m/z=258.2 $[M+H]^+$.

Eba-7

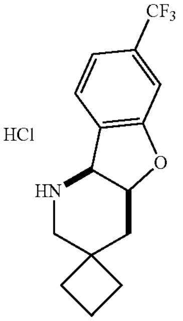

(±)

Cis-7-(trifluoromethyl)-1,4,4a,9b-tetrahydro-2H-spiro[benzofuro[3,2-b]pyridine-3,1'-cyclobutane]hydrochloride (Eba-7). Prepared following procedure LIII-E starting with tert-butyl 8-oxo-6-azaspiro[3.5]nonane-6-carboxylate and 1-bromo-2-fluoro-4-(trifluoromethyl)benzene. ES/MS: m/z=284.0 $[M+H]^+$.

General Procedure LIV-E for the Synthesis of Intermediates Ebb:

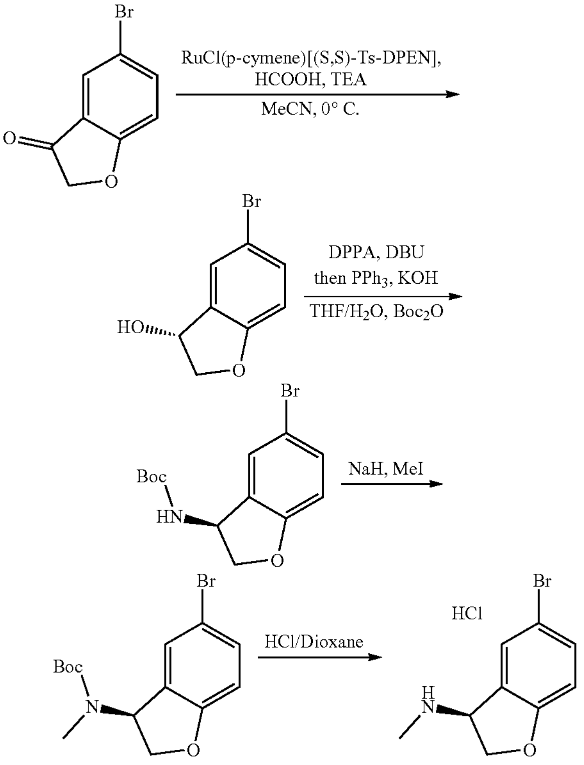

Ebb-1

Step 1: (R)-5-bromo-2,3-dihydrobenzofuran-3-ol. To a solution of 5-bromobenzofuran-3(2H)-one (1.00 g, 4.69 mmol) in acetonitrile (18 mL) at 0° C. was added TEA (1.96 mL, 14.1 mmol), formic acid (0.62 mL, 16.4 mmol), and RuCl(p-cymene)[(S,S)-Ts-DPEN](90 mg, 0.14 mmol). After stirring for 3 hours, sat. aq. $NaHCO_3$ was added and the mixture was diluted with EtOAc. The mixture was transferred to a separatory funnel and the organic layer was washed with brine, dried over $MgSO_4$, filtered, and concentrated. Purification by silica gel flash column chromatography afforded the desired product. ES/MS: m/z=197.0 $[M-OH+H]^+$.

Step 2: tert-butyl (S)-(5-bromo-2,3-dihydrobenzofuran-3-yl)carbamate. (R)-5-bromo-2,3-dihydrobenzofuran-3-ol (720 mg, 3.4 mmol) in toluene (12 mL) was added DBU (0.75 mL, 5.02 mmol) and DPPA (1.11 g, 4.02 mmol) respectively at 0° C. The mixture was warmed to 25° C. and stirred for 5 hrs before addition of water (50 mL). The mixture was extracted with EtOAc (80 mL×3), washed with brine (100 mL), dried over sodium sulfate, and concentrated. The crude residue was purified by flash chromatography to give desired product. The product was then dissolved in THF (6 mL) and water (2 mL). Triphenylphosphine (1.75 g, 6.7 mmol) and potassium hydroxide (467 mg, 8.3 mmol) was added, and the mixture was stirred at 50° C. and for 12 hrs. Triethylamine (0.09 mL 0.62 mmol) and $Boc_2O$ (67 mg, 0.31 mmol) were added at 25° C. and stirred for 3 hrs before addition of water (20 mL). The mixture was extracted with EtOAc (50 mL×3), washed with brine (100 mL), dried over sodium sulfate, and concentrated. The crude residue was purified by flash chromatography to give desired product. ES/MS: m/z=258.0 $[M-tBu+H]^+$.

Step 3: tert-butyl (S)-(5-bromo-2,3-dihydrobenzofuran-3-yl)(methyl)carbamate. tert-butyl (S)-(5-bromo-2,3-dihydrobenzofuran-3-yl)carbamate (510 mg, 1.62 mmol) in DMF (5 mL) was added NaH (60%, 124 mg, 3.3 mmol) at 0° C. The mixture was stirred at 0° C. for 30 mins before addition of methyl iodide (0.152 mL, 2.4 mmol). The reaction was stirred for additional 10 hrs at 25° C. before quenching with saturated aq. $NH_4Cl$ (20 mL). The mixture was extracted with EtOAc (20 mL×3), washed with brine (30 mL), and dried over sodium sulfate. The crude residue was purified by flash chromatography to give desired product. ES/MS: m/z=268.0 $[M-tBu+H]^+$.

Step 4: (S)-5-bromo-N-methyl-2,3-dihydrobenzofuran-3-amine hydrochloride (Ebb-1). tert-butyl (S)-(5-bromo-2,3-dihydrobenzofuran-3-yl)(methyl)carbamate (510 mg, 1.62 mmol) in dioxane (10 mL) was added HCl (4M in dioxane, 2 mL, 8.1 mmol) at 25° C. The mixture was stirred at 25° C. for 6 hrs before concentrating in vacuo to give the desired product. ES/MS: m/z=227.0 $[M+H]^+$.

Ebb-2

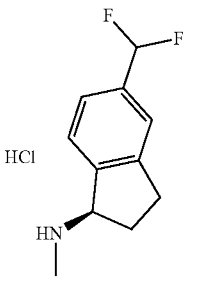

(1R)-5-(difluoromethyl)-N-methyl-indan-1-amine hydrochloride (Ebb-2). Prepared following procedure LIV-E starting with 5-(difluoromethyl)-2,3-dihydro-1H-inden-1-one. ES/MS: m/z=197.9 $[M+H]^+$.

General Procedure LV-E for the Synthesis of Intermediates Ebc:

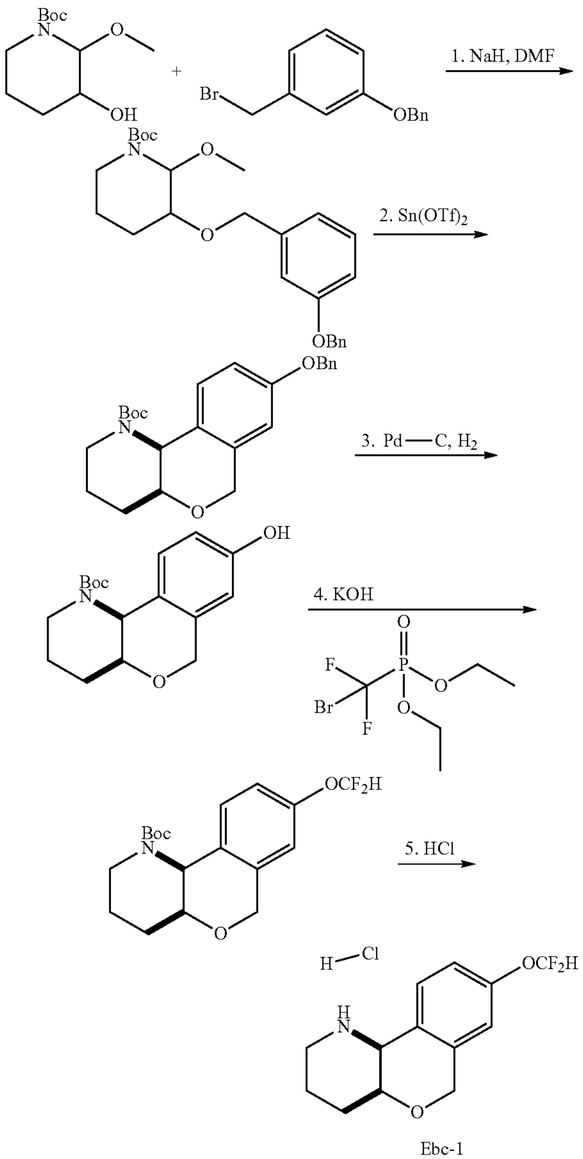

Ebc-1
(±)

Step 1. tert-butyl 3-[(3-benzyloxyphenyl)methoxy]-2-methoxy-piperidine-1-carboxylate. tert-butyl 3-hydroxy-2-methoxy-piperidine-1-carboxylate (350 mg, 1.5 mmol) in DMF (5 mL) was added NaH (60%, 87 mg, 2.3 mmol) at 0° C. The mixture was stirred at 0° C. for 30 mins before addition of 1-benzyloxy-3-(bromomethyl)benzene (500 mg, 1.8 mmol). The reaction was stirred for additional 10 hrs at 25° C. before quenching with saturated aq. $NH_4Cl$ (20 mL). The mixture was extracted with EtOAc (20 mL×3), washed with brine (30 mL), and dried over sodium sulfate. The crude residue was purified by flash chromatography to give desired product. ES/MS: m/z=429.2 $[M+H]^+$.

Step 2. Cis-tert-butyl (4aS,10bS)-8-(benzyloxy)-2,3,4,4a,6,10b-hexahydro-1H-isochromeno[4,3-b]pyridine-1-carboxylate. tert-butyl 3-[(3-benzyloxyphenyl)methoxy]-2-methoxy-piperidine-1-carboxylate (495 mg, 1.2 mmol) in DCM (12 mL) at 0° C. was added tin(II) trifluoromethanesulfonate (120 mg, 0.29 mmol). The mixture was stirred at 0° C. for 30 mins before quenching with saturated aq. $NaHCO_3$ (5 mL). The mixture was extracted with EtOAc (20 mL×3), washed with brine (30 mL), and dried over sodium sulfate. The crude residue was purified by flash chromatography to give desired product. ES/MS: m/z=396.0 $[M+H]^+$.

Step 3. Cis-tert-butyl (4aS,10bS)-8-hydroxy-2,3,4,4a,6,10b-hexahydroisochromeno[4,3-b]pyridine-1-carboxylate. Cis-tert-butyl (4aS,10bS)-8-(benzyloxy)-2,3,4,4a,6,10b-hexahydro-1H-isochromeno[4,3-b]pyridine-1-carboxylate (223 mg, 0.56 mmol) in EtOH (11 mL) was added 10% palladium on carbon (90 mg, 0.085 mmol). The mixture was stirred at 25° C. under 1 atm of hydrogen balloon for 30 mins before filtering. The mixture was concentrated and was purified by flash chromatography to give desired product. ES/MS: m/z=306.0 $[M+H]^+$.

Step 4. Cis-tert-butyl (4aS,10bS)-8-(difluoromethoxy)-2,3,4,4a,6,10b-hexahydro-1H-isochromeno[4,3-b]pyridine-1-carboxylate. Cis-tert-butyl (4aS,10bS)-8-hydroxy-2,3,4,4a,6,10b-hexahydroisochromeno[4,3-b]pyridine-1-carboxylate (170 mg, 0.56 mmol) in MeCN/water (1:1, 10 mL total) was added KOH (780 mg, 14 mmol) and 1-[[bromo(difluoro)methyl]-ethoxy-phosphoryl]oxyethane (0.40 mL, 2.2 mmol). The mixture was stirred at 25° C. for 20 h. The mixture was extracted with EtOAc (20 mL×3), washed with brine (30 mL), and dried over sodium sulfate. The crude residue was purified by flash chromatography to give desired product. ES/MS: m/z=356.0 $[M+H]^+$.

Step 5. Cis-(4aS,10bS)-8-(difluoromethoxy)-2,3,4,4a,6,10b-hexahydro-1H-isochromeno[4,3-b]pyridine hydrochloride (Ebc-1). Cis-tert-butyl (4aS,10bS)-8-(difluoromethoxy)-2,3,4,4a,6,10b-hexahydro-1H-isochromeno[4,3-b]pyridine-1-carboxylate (140 mg, 0.40 mmol) in dioxane (2 mL) was added HCl (4 M in dioxane, 1 mL, 4.0 mmol). The mixture was stirred at 25° C. for 20 h, concentrated, and used without further purification. ES/MS: m/z=256.0 $[M+H]^+$.

General Procedure LVI-E for the Synthesis of Intermediates Ebd:

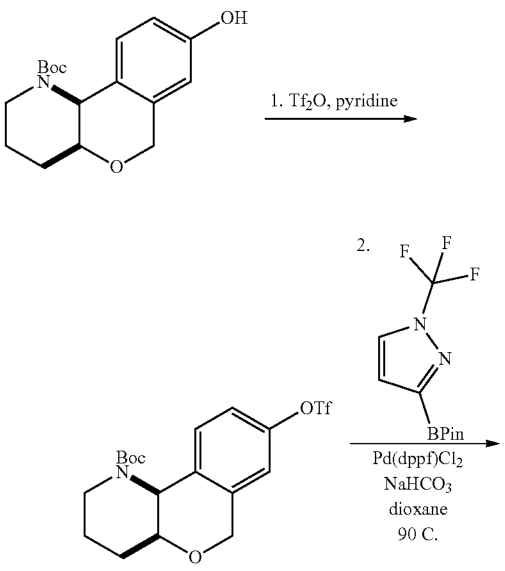

-continued

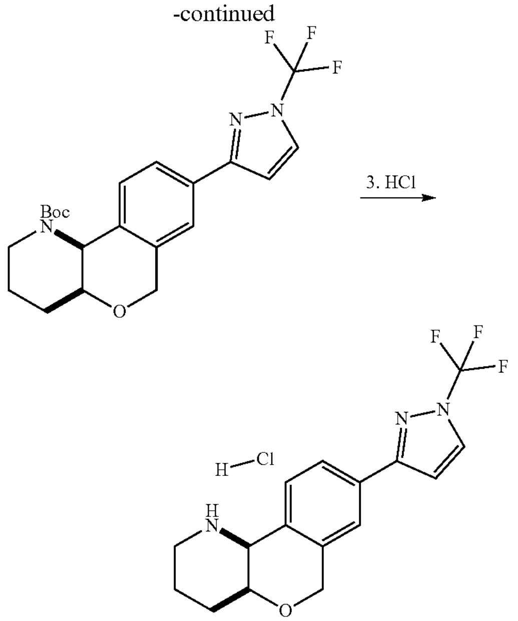

Ebd-1
(±)

Step 1. Cis-tert-butyl (4aS,10bS)-8-(((trifluoromethyl)sulfonyl)oxy)-2,3,4,4a,6,10b-hexahydro-1H-isochromeno[4,3-b]pyridine-1-carboxylate. Cis-tert-butyl (4aS,10bS)-8-hydroxy-2,3,4,4a,6,10b-hexahydroisochromeno[4,3-b]pyridine-1-carboxylate from procedure LV-E (360 mg, 1.2 mmol) and pyridine (0.19 mL, 2.4 mmol)) in THF (4 mL) was added trifluoromethanesulfonic anhydride (1 M in DCM, 1.5 mL, 1.5 mmol) at 0° C. The mixture was warmed to rt and stirred for 12 h before quenching with saturated aq. $NaHCO_3$ (20 mL). The mixture was extracted with EtOAc (20 mL×3), washed with brine (30 mL), and dried over sodium sulfate. The crude residue was purified by flash chromatography to give desired product. ES/MS: m/z=460.0 $[M+Na]^+$.

Step 2. Cis-tert-butyl (4aS,10bS)-8-(1-(trifluoromethyl)-1H-pyrazol-3-yl)-2,3,4,4a,6,10b-hexahydro-1H-isochromeno[4,3-b]pyridine-1-carboxylate. To a solution of cis-tert-butyl (4aS,10bS)-8-(((trifluoromethyl)sulfonyl)oxy)-2,3,4,4a,6,10b-hexahydro-1H-isochromeno[4,3-b]pyridine-1-carboxylate (50 mg, 0.14 mmol) in dioxane (1.0 mL) was added $PdCl_2$(dppf) (13 mg, 0.017 mmol), 3-(4,4,5,5-tetramethyl-1,3,2-dioxaborolan-2-yl)-1-(trifluoromethyl)pyrazole (90 mg, 0.34 mmol), and aqueous $NaHCO_3$ (2 M, 0.46 mL, 0.91 mmol). The reaction mixture was then degassed with argon for 5 min. The reaction mixture was then heated at 90° C. for 5 h. LCMS analysis confirms full conversion to product. Reaction mixture was diluted with EtOAc, washed with water and 5% aq LiCl, dried over $MgSO_4$, filtered and concentrated under reduced pressure to give a residue. The crude residue was purified by flash chromatography to give desired product. ES/MS: m/z=446.0 $[M+Na]^+$.

Step 3. Cis-(4aS,10bS)-8-(1-(trifluoromethyl)-1H-pyrazol-3-yl)-2,3,4,4a,6,10b-hexahydro-1H-isochromeno[4,3-b]pyridine hydrochloride (Ebd-1). Cis-tert-butyl (4aS,10bS)-8-(1-(trifluoromethyl)-1H-pyrazol-3-yl)-2,3,4,4a,6,10b-hexahydro-1H-isochromeno[4,3-b]pyridine-1-carboxylate (25 mg, 0.060 mmol) in dioxane (2 mL) was added HCl (4 M in dioxane, 0.15 mL, 0.6 mmol). The mixture was stirred at 25° C. for 20 h, concentrated, and used without further purification. ES/MS: m/z=324.0 $[M+H]^+$.

Ebd-2

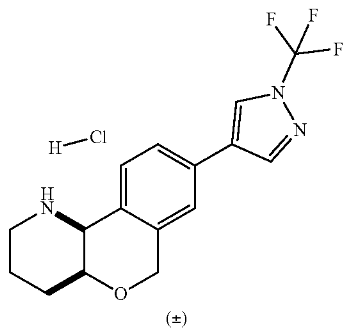

Cis-(4aS,10bS)-8-(1-(trifluoromethyl)-1H-pyrazol-4-yl)-2,3,4,4a,6,10b-hexahydro-1H-isochromeno[4,3-b]pyridine hydrochloride (Ebd-2). Prepared following procedure LVI-E starting with 4-(4,4,5,5-tetramethyl-1,3,2-dioxaborolan-2-yl)-1-(trifluoromethyl)pyrazole. ES/MS: m/z=324.0 $[M+H]^+$.

Ebd-3

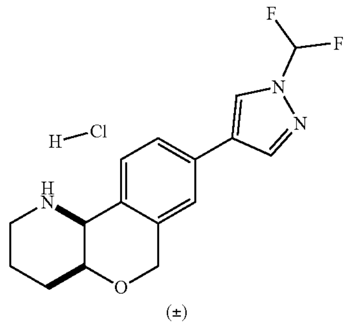

Cis-(4aS,10bS)-8-(1-(difluoromethyl)-1H-pyrazol-4-yl)-2,3,4,4a,6,10b-hexahydro-1H-isochromeno[4,3-b]pyridine hydrochloride (Ebd-3). Prepared following procedure LVI-E starting with 4-(4,4,5,5-tetramethyl-1,3,2-dioxaborolan-2-yl)-1-(difluoromethyl)pyrazole. ES/MS: m/z=306.0 $[M+H]^+$.

Ebd-4

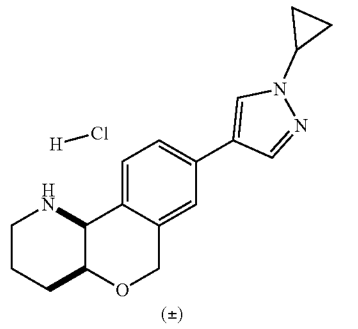

Cis-(4aS,10bS)-8-(1-cyclopropyl-1H-pyrazol-4-yl)-2,3,4,4a,6,10b-hexahydro-1H-isochromeno[4,3-b]pyridine hydrochloride (Ebd-4). Prepared following procedure LVI-E starting with 1-cyclopropyl-4-(4,4,5,5-tetramethyl-1,3,2-dioxaborolan-2-yl)pyrazole. ES/MS: m/z=296.0 $[M+H]^+$.

Ebd-5

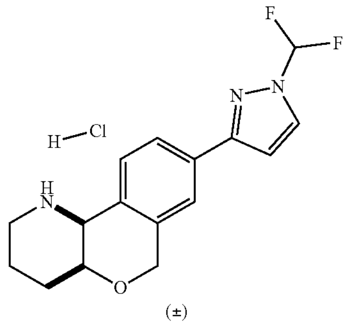

Cis-(4aS,10bS)-8-(1-(difluoromethyl)-1H-pyrazol-3-yl)-2,3,4,4a,6,10b-hexahydro-1H-isochromeno[4,3-b]pyridine hydrochloride (Ebd-5). Prepared following procedure LVI-E starting with 1-(difluoromethyl)-3-(4,4,5,5-tetramethyl-1,3,2-dioxaborolan-2-yl)pyrazole. ES/MS: m/z=306.0 $[M+H]^+$.

Ebd-6

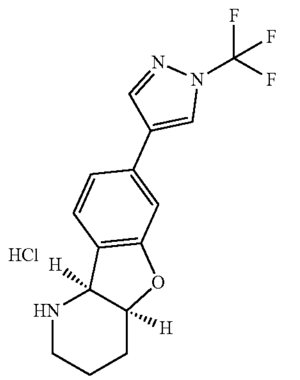

(4aS,9bS)-7-(1-(trifluoromethyl)-1H-pyrazol-4-yl)-1,2,3,4,4a,9b-hexahydrobenzofuro[3,2-b]pyridine hydrochloride (Ebd-6). Prepared following general procedure LVI-E starting from (4aS,9bS)-1,2,3,4,4a,9b-hexahydrobenzofuro[3,2-b]pyridin-7-ol and 4-(4,4,5,5-tetramethyl-1,3,2-dioxaborolan-2-yl)-1-(trifluoromethyl)-1H-pyrazole using N-phenyl bis(trifluoromethanesulfonimide) instead of triflic anhydride and TEA and DMAP instead of pyridine in step 1. (4aS,9bS)-1,2,3,4,4a,9b-hexahydrobenzofuro[3,2-b]pyridin-7-ol was prepared following general procedure XXIII-E starting with 4-(benzyloxy)-1-bromo-2-fluorobenzene instead of 1-bromo-2-fluoro-4-(trifluoromethyl)benzene, followed by step 3 of general procedure LV-E. ES/MS: m/z=310.0 $[M+H^+]$.

Ebd-7

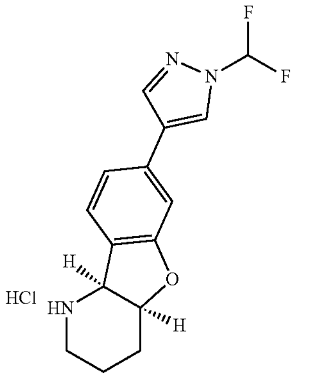

(4aS,9bS)-7-(1-(difluoromethyl)-1H-pyrazol-4-yl)-1,2,3,4,4a,9b-hexahydrobenzofuro[3,2-b]pyridine hydrochloride (Ebd-7). Prepared following general procedure LVI-E starting from (4aS,9bS)-1,2,3,4,4a,9b-hexahydrobenzofuro[3,2-b]pyridin-7-ol and 1-(difluoromethyl)-4-(4,4,5,5-tetramethyl-1,3,2-dioxaborolan-2-yl)-1H-pyrazole using N-phenyl bis(trifluoromethanesulfonimide) instead of triflic anhydride and TEA and DMAP instead of pyridine in step 1. (4aS,9bS)-1,2,3,4,4a,9b-hexahydrobenzofuro[3,2-b]pyridin-7-ol was prepared following general procedure XXIII-E starting with 4-(benzyloxy)-1-bromo-2-fluorobenzene instead of 1-bromo-2-fluoro-4-(trifluoromethyl)benzene, followed by step 3 of general procedure LV-E. ES/MS: m/z=292.0 [M-tBu+H$^+$].

General Procedure LVII-E for the Synthesis of Intermediates Ebe:

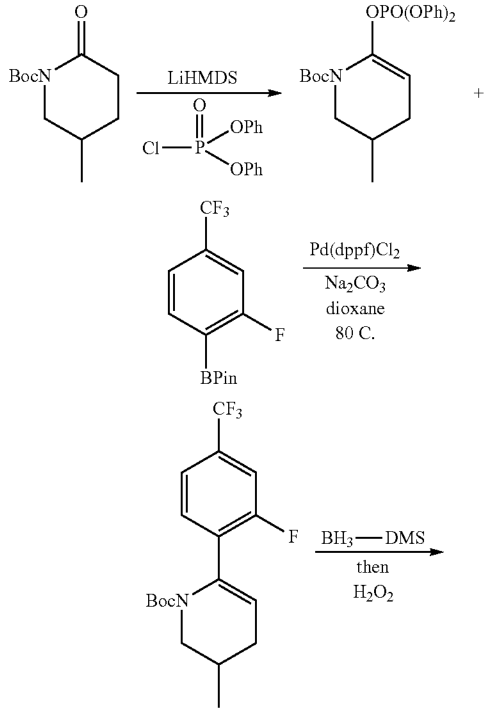

-continued

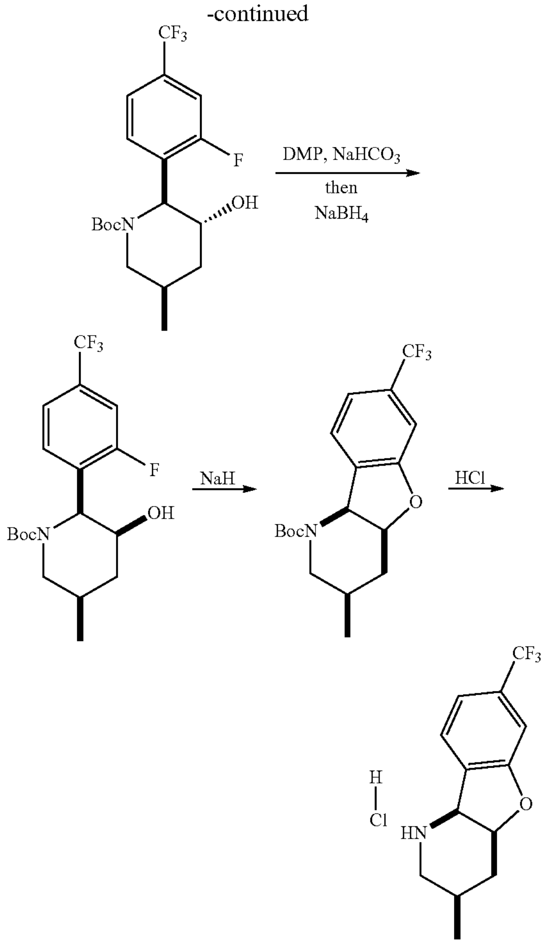

Ebe-1
(±)

Step 1. tert-butyl 6-((diphenoxyphosphoryl)oxy)-3-methyl-3,4-dihydropyridine-1(2H)-carboxylate. tert-butyl 5-methyl-2-oxo-piperidine-1-carboxylate (500 mg, 2.3 mmol) in THF (5 mL) was added LHMDS (1 M in THF, 2.7 mL, 2.7 mmol) at −78° C. The mixture was stirred at −78° C. for 20 mins before addition of diphenyl chlorophosphate (700 mg, 2.6 mmol). The reaction was warmed to 0° C. and stirred for 30 min before quenching with saturated aq. $NH_4Cl$ (20 mL). The mixture was extracted with EtOAc (20 mL×3), washed with brine (30 mL), and dried over sodium sulfate. The crude residue was purified by flash chromatography to give desired product. ES/MS: m/z=446.2 [M+H]$^+$.

Step 2. tert-butyl 6-(2-fluoro-4-(trifluoromethyl)phenyl)-3-methyl-3,4-dihydropyridine-1(2H)-carboxylate. To a solution of tert-butyl 6-((diphenoxyphosphoryl)oxy)-3-methyl-3,4-dihydropyridine-1(2H)-carboxylate (600 mg, 1.40 mmol) in dioxane (6.0 mL) was added PdCl2(dppf) (155 mg, 0.21 mmol), 2-[2-fluoro-4-(trifluoromethyl)phenyl]-4,4,5,5-tetramethyl-1,3,2-dioxaborolane (486 mg, 1.68 mmol), and aqueous $NaHCO_3$ (2 M, 2.1 mL, 4.2 mmol). The reaction mixture was then degassed with argon for 5 min. The reaction mixture was then heated at 80° C. for 5 h. LCMS analysis confirms full conversion to product. Reaction mixture was diluted with EtOAc, washed with water and 5% aq LiCl, dried over $MgSO_4$, filtered and concentrated under reduced pressure to give a residue. The crude residue was purified by flash chromatography to give desired product. ES/MS: compound did not ionize.

Step 3. Cis-tert-butyl (2S,3R,5R)-2-(2-fluoro-4-(trifluoromethyl)phenyl)-3-hydroxy-5-methylpiperidine-1-carboxylate. tert-butyl 6-(2-fluoro-4-(trifluoromethyl)phenyl)-3-methyl-3,4-dihydropyridine-1(2H)-carboxylate (200 mg, 0.56 mmol) in THF (3 mL) at 0° C. was added borane dimethyl sulfide complex (0.11 mL, 1.1 mmol). The mixture was warmed to rt and stirred for 24 h. The mixture was cooled to 0° C., followed by addition of NaOH (2M in water, 0.5 mL, 1.0 mmol) and hydrogen peroxide (30%, 0.5 mL). The mixture was warmed to rt and stirred for 1 h before quenching with saturated aq. $NaHCO_3$ (10 mL). The mixture was extracted with EtOAc (20 mL×3), washed with brine (30 mL), and dried over sodium sulfate. The crude residue was purified by flash chromatography to give desired product. ES/MS: m/z=322.0 $[M-56]^+$.

Step 4. Cis-tert-butyl (2S,3S,5R)-2-(2-fluoro-4-(trifluoromethyl)phenyl)-3-hydroxy-5-methylpiperidine-1-carboxylate. Cis-tert-butyl (2S,3R,5R)-2-(2-fluoro-4-(trifluoromethyl)phenyl)-3-hydroxy-5-methylpiperidine-1-carboxylate (100 mg, 0.26 mmol) and $NaHCO_3$ (162 mg, 2.6 mmol) in DCM (3 mL) was added Dess-Martin Periodinane (200 mg, 0.48 mmol) at rt. The mixture was stirred at 25° C. for 30 min before quenching with saturated aq. $NaHCO_3$ (10 mL). The mixture was extracted with ether (20 mL×3), washed with brine (30 mL), dried over sodium sulfate, and concentrated. The mixture was re-dissolved in DCM/MeOH (1:1, 4.0 mL), and $NaBH_4$ (10 mg, 0.26 mmol) was added at 0° C. The mixture was warmed to rt and stirred for 30 min before quenching with saturated aq. $NaHCO_3$ (10 mL). The mixture was extracted with EtOAc (20 mL×3), washed with brine (30 mL), dried over sodium sulfate. The mixture was concentrated and was purified by flash chromatography to give desired product. ES/MS: m/z=322.0 $[M-56]^+$.

Step 5. Cis-tert-butyl (3R,4aS,9bS)-3-methyl-7-(trifluoromethyl)-3,4,4a,9b-tetrahydrobenzofuro[3,2-b]pyridine-1(2H)-carboxylate. Cis-tert-butyl (2S,3S,5R)-2-(2-fluoro-4-(trifluoromethyl)phenyl)-3-hydroxy-5-methylpiperidine-1-carboxylate (90 mg, 0.24 mmol) in DMF (3.0 mL) was added sodium hydride (60%, 14 mg, 0.36 mmol) at rt. The mixture was stirred at 25° C. for 45 min before quenching with saturated aq. $NH_4Cl$ (10 mL). The mixture was extracted with ether (20 mL×3), washed with brine (30 mL), and dried over sodium sulfate. The crude residue was purified by flash chromatography to give desired product. ES/MS: m/z=302.0 $[M-56]^+$.

Step 6. Cis-(3R,4aS,9bS)-3-methyl-7-(trifluoromethyl)-1,2,3,4,4a,9b-hexahydro benzofuro[3,2-b]pyridine hydrochloride (Ebe-1). Cis-tert-butyl (3R,4aS,9bS)-3-methyl-7-(trifluoromethyl)-3,4,4a,9b-tetrahydrobenzofuro[3,2-b]pyridine-1(2H)-carboxylate (40 mg, 0.11 mmol) in dioxane (1 mL) was added HCl (4 M in dioxane, 0.30 mL, 1.2 mmol). The mixture was stirred at 25° C. for 20 h, concentrated, and used without further purification. ES/MS: m/z=258.2 $[M+H]^+$.

Ebe-2

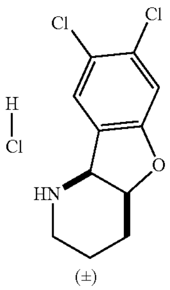

Cis-(4aS,9bS)-7,8-dichloro-1,2,3,4,4a,9b-hexahydrobenzofuro[3,2-b]pyridine hydrochloride (Ebe-2). Prepared following procedure LVII-E starting with tert-butyl 2-oxo-piperidine-1-carboxylate and 2-(4,5-dichloro-2-fluoro-phenyl)-4,4,5,5-tetramethyl-1,3,2-dioxaborolane. ES/MS: m/z=243.0 $[M+H]^+$.

Ebe-3

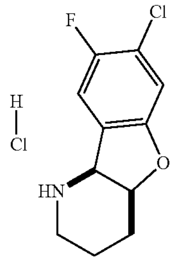

Cis-(4aS,9bS)-7-chloro-8-fluoro-1,2,3,4,4a,9b-hexahydrobenzofuro[3,2-b]pyridine hydrochloride (Ebe-3). Prepared following procedure LVII-E starting with tert-butyl 2-oxo-piperidine-1-carboxylate and 2-(4-chloro-2,5-difluoro-phenyl)-4,4,5,5-tetramethyl-1,3,2-dioxaborolane. ES/MS: m/z=228.0 $[M+H]^+$.

Ebe-4

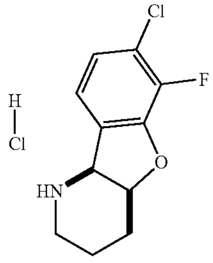

Cis-(4aS,9bS)-7-chloro-6-fluoro-1,2,3,4,4a,9b-hexahydrobenzofuro[3,2-b]pyridine hydrochloride (Ebe-4). Prepared following procedure LVII-E starting with tert-butyl 2-oxo-piperidine-1-carboxylate and 2-(4-chloro-2,3-difluoro-phenyl)-4,4,5,5-tetramethyl-1,3,2-dioxaborolane. ES/MS: m/z=228.0 $[M+H]^+$.

Ebe-5

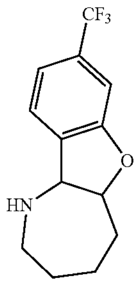

8-(trifluoromethyl)-2,3,4,5,5a,10b-hexahydro-1H-benzofuro[3,2-b]azepine (Ebe-5). Prepared following procedure LVII-E using tert-butyl 2-oxoazepane-1-carboxylate. ES/MS: m/z =258.2 $[M+H]^+$.

General Procedure LVIII-E for the Synthesis of Intermediates Ebf:

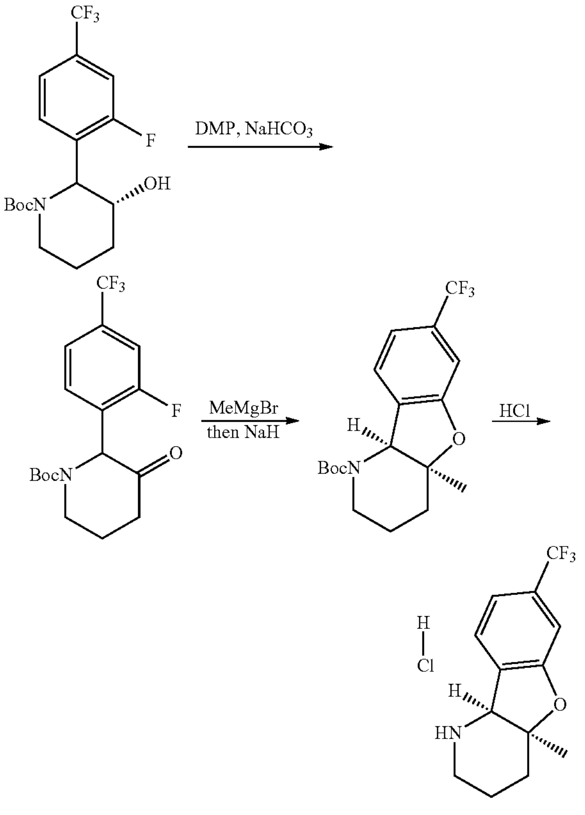

Ebf-1

Step 1. tert-butyl 2-(2-fluoro-4-(trifluoromethyl)phenyl)-3-oxopiperidine-1-carboxylate. Rac-tert-butyl (3R)-2-(2-fluoro-4-(trifluoromethyl)phenyl)-3-hydroxypiperidine-1-carboxylate prepared from general procedure LVII-E starting with tert-butyl 2-oxo-piperidine-1-carboxylate (200 mg, 0.55 mmol) and $NaHCO_3$ (162 mg, 2.6 mmol) in DCM (3 mL) was added Dess-Martin Periodinane (400 mg, 0.96 mmol) at rt. The mixture was stirred at 25° C. for 30 min before quenching with saturated aq. $NaHCO_3$ (10 mL). The mixture was extracted with ether (20 mL×3), washed with brine (30 mL), dried over sodium sulfate, and concentrated. The mixture was concentrated and was purified by flash chromatography to give desired product. ES/MS: m/z=306.0 $[M-56]^+$.

Step 2. Rac-tert-butyl (4aS,9bS)-4a-methyl-7-(trifluoromethyl)-3,4,4a,9b-tetrahydrobenzofuro[3,2-b]pyridine-1(2H)-carboxylate. To a solution of tert-butyl 2-(2-fluoro-4-(trifluoromethyl)phenyl)-3-oxopiperidine-1-carboxylate (28 mg, 0.077 mmol) in THF (1.0 mL) was added MeMgBr (3 M in THF, 0.07 mL, 0.21 mmol) at 0° C. The reaction mixture was then warmed to rt and stirred for 2 h before quenching with aq. $NH_4Cl$ (5 mL). The mixture was extracted with ether (20 mL×3), washed with brine (30 mL), dried over sodium sulfate, and concentrated. The crude residue was redissolved in DMF (2 mL), and NaH (60%, 4.5 mg, 0.12 mmol) was added at rt. The mixture was stirred for 30 min before quenching with aq. $NH_4Cl$ (5 mL). The mixture was extracted with ether (20 mL×3), washed with brine (30 mL), dried over sodium sulfate, and concentrated. The crude residue was purified by flash chromatography to give desired product. ES/MS: m/z=302.0 $[M-56]^+$.

Step 3. Rac-(4aS,9bS)-4a-methyl-7-(trifluoromethyl)-1,2,3,4,4a,9b-hexahydrobenzofuro[3,2-b]pyridine hydrochloride (Ebf-1). Rac-tert-butyl (4aS,9bS)-4a-methyl-7-(trifluoromethyl)-3,4,4a,9b-tetrahydrobenzofuro[3,2-b]pyridine-1(2H)-carboxylate (4.0 mg, 0.11 mmol) in dioxane (1 mL) was added HCl (4 M in dioxane, 0.03 mL, 0.12 mmol). The mixture was stirred at 25° C. for 20 h, concentrated, and used without further purification. ES/MS: m/z=258.0 $[M+H]^+$.

General Procedure LIX-E for the Synthesis of Intermediates Ebg

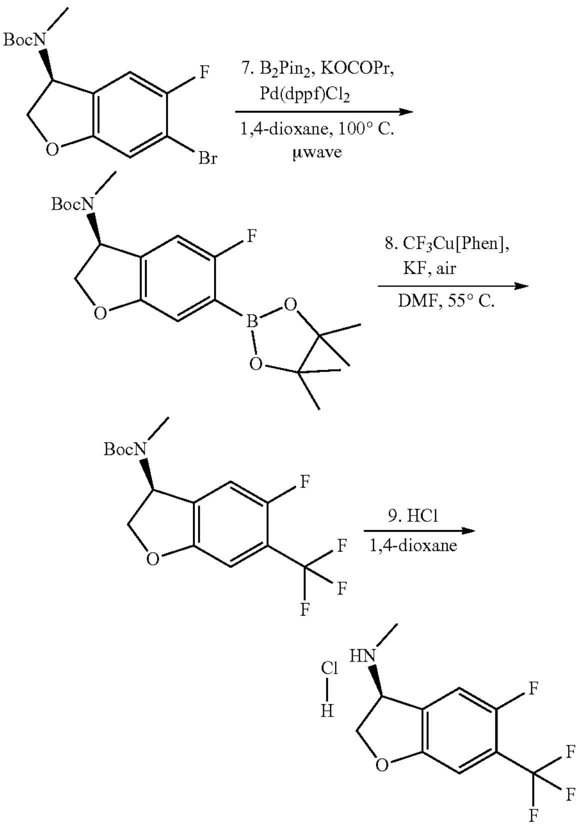

Ebg-1

Step 1. tert-butyl (S)-(5-fluoro-6-(4,4,5,5-tetramethyl-1,3,2-dioxaborolan-2-yl)-2,3-dihydrobenzofuran-3-yl)(methyl)carbamate. A mixture of (S)-tert-butyl (6-bromo-5-fluoro-2,3-dihydrobenzofuran-3-yl)(methyl)carbamate (prepared following general procedure LIV-E starting with 6-bromo-5-fluorobenzofuran-3(2H)-one (540 mg, 1.36 mmol), $Pd(dppf)Cl_2$ (150 mg, 0.20 mmol), potassium propionate (460 mg, 4.0 mmol), and bis(pinacolato)diboron (414 mg, 1.64 mmol) in 1,4-dioxane (5.0 mL) were sealed in a microwave vial and heated to 100° C. in a microwave reactor for 1 hour. The resulting mixture was concentrated and purified by silica gel flash column chromatography to afford tert-butyl (S)-(5-fluoro-6-(4,4,5,5-tetramethyl-1,3,2-dioxaborolan-2-yl)-2,3-dihydrobenzofuran-3-yl)(methyl) carbamate. ES/MS: m/z=338.0 $[M-56]^+$.

Step 2. tert-butyl (S)-(5-fluoro-6-(trifluoromethyl)-2,3-dihydrobenzofuran-3-yl)(methyl)carbamate. Trifluoromethyl(1,10-phenanthroline)copper (600 mg, 1.93 mmol) was added to a mixture of tert-butyl (S)-(5-fluoro-6-(4,4,5,5-tetramethyl-1,3,2-dioxaborolan-2-yl)-2,3-dihydrobenzofuran-3-yl)(methyl)carbamate (330 mg, 0.840 mmol) and potassium fluoride (83 mg, 1.43 mmol) in DMF (15 mL). Air was bubbled through the solution for 10 minutes, then the reaction vessel was sealed and heated to 60° C. overnight. After cooling to room temperature, the mixture was diluted with EtOAc, transferred to a separatory funnel, and successively washed with water and brine. The organic extract was dried over $MgSO_4$, filtered, and concentrated. Purification by silica gel flash column chromatography afforded tert-butyl (S)-(5-fluoro-6-(trifluoromethyl)-2,3-dihydrobenzofuran-3-yl)(methyl)carbamate. ES/MS: m/z=280.0 $[M-56]^+$.

Step 3. (S)-5-fluoro-N-methyl-6-(trifluoromethyl)-2,3-dihydrobenzofuran-3-amine hydrochloride (Ebg-1). To a solution of tert-butyl (S)-(5-fluoro-6-(trifluoromethyl)-2,3-dihydrobenzofuran-3-yl)(methyl)carbamate (173 mg, 0.51 mmol) in 1,4-dioxane (3 mL) was added HCl (4.0 M in dioxane, 2.1 mL, 8.4 mmol). After stirring overnight, the mixture was concentrated to afford (S)-5-fluoro-N-methyl-6-(trifluoromethyl)-2,3-dihydrobenzofuran-3-amine hydrochloride. ES/MS: m/z=236.2 $[M+H]^+$.

Ebg-2

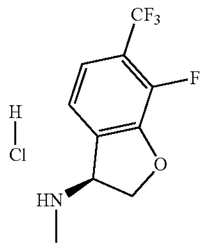

(S)-7-fluoro-N-methyl-6-(trifluoromethyl)-2,3-dihydrobenzofuran-3-amine hydrochloride (Ebg-2). Prepared following procedure LIX-E starting with tert-butyl (S)-(6-bromo-7-fluoro-2,3-dihydrobenzofuran-3-yl)(methyl) carbamate (prepared following general procedure LIV-E starting with 1-(4-bromo-3-fluoro-2-hydroxyphenyl)ethan-1-one.) ES/MS: m/z =236.2 $[M+H]^+$.

General Procedure LX-E for the Synthesis of Intermediates Ebh:

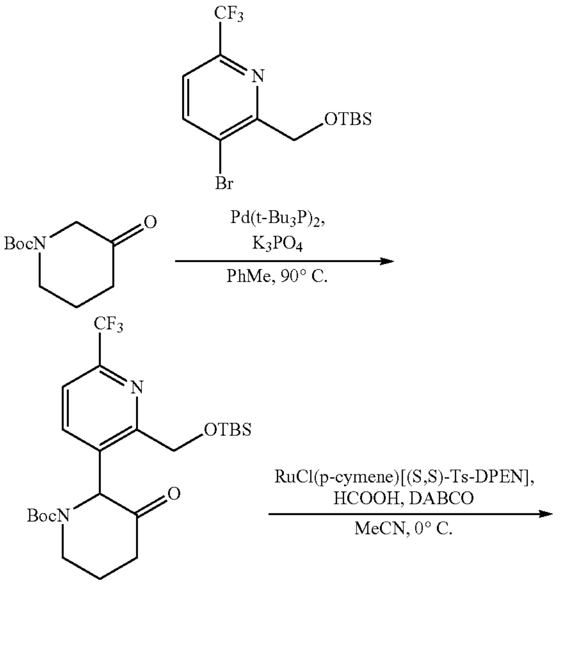

-continued

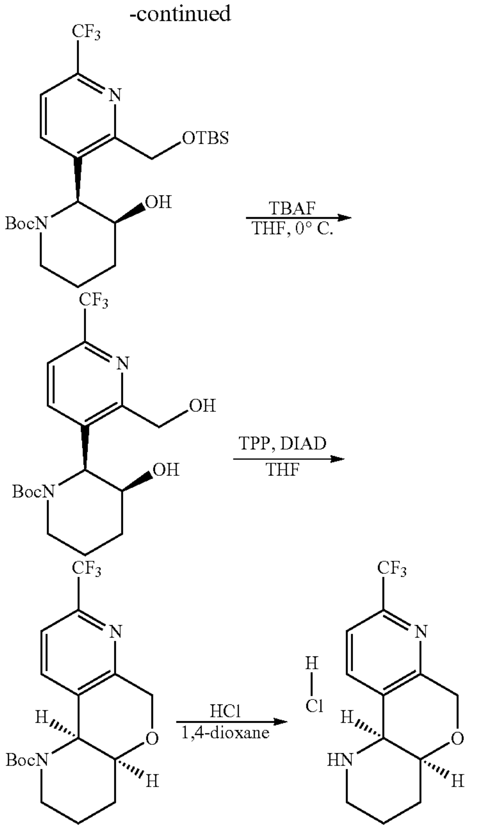

Ebh-1

Step 1. tert-butyl 2-(2-(((tert-butyldimethylsilyl)oxy)methyl)-6-(trifluoromethyl)pyridin-3-yl)-3-oxopiperidine-1-carboxylate. To a stirred solution of tert-butyl 3-oxopiperidine-1-carboxylate (710 mg, 3.6 mmol) and [3-bromo-6-(trifluoromethyl)-2-pyridyl]methoxy-tert-butyl-dimethyl-silane (600 mg, 1.8 mmol) in toluene (12 mL) was added $K_3PO_4$ (950 mg, 4.6 mmol) and $Pd(t\text{-}Bu_3P)_2$ (90 mg, 0.18 mmol). The mixture was heated to 90° C. for 3 hours, then cooled to room temperature, filtered over celite, and concentrated. Purification by silica gel flash column chromatography afforded tert-butyl 2-(2-(((tert-butyldimethylsilyl)oxy)methyl)-6-(trifluoromethyl)pyridin-3-yl)-3-oxopiperidine-1-carboxylate. ES/MS: m/z=489.0 $[M+H]^+$.

Step 2. tert-butyl (2S,3S)-2-(2-(((tert-butyldimethylsilyl)oxy)methyl)-6-(trifluoromethyl)pyridin-3-yl)-3-hydroxypiperidine-1-carboxylate. To a solution of tert-butyl 2-(2-(((tert-butyldimethylsilyl)oxy)methyl)-6-(trifluoromethyl)pyridin-3-yl)-3-oxopiperidine-1-carboxylate (470 mg, 0.96 mmol) in acetonitrile (10 mL) at 0° C. was added DABCO (600 mg, 5.3 mmol), formic acid (0.11 mL, 2.9 mmol), and RuCl(p-cymene)[(S,S)-Ts-DPEN] (15 mg, 0.024 mmol). After stirring for 3 hours, sat. aq. $NaHCO_3$ was added and the mixture was diluted with EtOAc. The mixture was transferred to a separatory funnel and the organic layer was washed with brine, dried over $MgSO_4$, filtered, and concentrated. Purification by silica gel flash column chromatography afforded tert-butyl (2S,3S)-2-(2-(((tert-butyldimethylsilyl)oxy)methyl)-6-(trifluoromethyl)pyridin-3-yl)-3-hydroxypiperidine-1-carboxylate. ES/MS: m/z=491.0 $[M+H]^+$.

Step 3. tert-butyl (2S,3S)-3-hydroxy-2-(2-(hydroxymethyl)-6-(trifluoromethyl)pyridin-3-yl)piperidine-1-carboxylate. To a solution of tert-butyl (2S,3S)-2-(2-(((tert-butyldimethylsilyl)oxy)methyl)-6-(trifluoromethyl)pyridin-3-yl)-3-hydroxypiperidine-1-carboxylate (350 mg, 0.71 mmol) in THF (4.0 mL) at 0° C. was added TBAF (1.0 M in THF, 0.80 mL, 0.80 mmol). After stirring for 2 hours, sat. aq. $NaHCO_3$ was added and the mixture was diluted with EtOAc. The mixture was transferred to a separatory funnel and the organic layer was washed with brine, dried over $MgSO_4$, filtered, and concentrated. Purification by silica gel flash column chromatography afforded tert-butyl (2S,3S)-3-hydroxy-2-(2-(hydroxymethyl)-6-(trifluoromethyl)pyridin-3-yl)piperidine-1-carboxylate. ES/MS: m/z=377.0 $[M+H]^+$.

Step 4. tert-butyl (4aS,10bS)-8-(trifluoromethyl)-2,3,4,4a,6,10b-hexahydro-1H-pyrano[3,2-b:5,4-b']dipyridine-1-carboxylate. To a solution of tert-butyl (2S,3S)-3-hydroxy-2-(2-(hydroxymethyl)-6-(trifluoromethyl)pyridin-3-yl) piperidine-1-carboxylate (260 mg, 0.15 mmol) and triphenylphosphine (217 mg, 0.83 mmol) in THF (4.0 mL) at 0° C. was added DIAD (0.16 mL, 0.83 mmol). After stirring for 2 hours at rt, the mixture was concentrated. Purification by silica gel flash column chromatography afforded tert-butyl (4aS,10bS)-8-(trifluoromethyl)-2,3,4,4a,6,10b-hexahydro-1H-pyrano[3,2-b:5,4-b']dipyridine-1-carboxylate. ES/MS: m/z=359.0 $[M+H]^+$.

Step 5. (4aS,10bS)-8-(trifluoromethyl)-2,3,4,4a,6,10b-hexahydro-1H-pyrano[3,2-b:5,4-b']dipyridine hydrochloride (Ebh-1). A solution of tert-butyl (4aS,10bS)-8-(trifluoromethyl)-2,3,4,4a,6,10b-hexahydro-1H-pyrano[3,2-b:5,4-b']dipyridine-1-carboxylate (165 mg, 0.46 mmol) in 1,4-dioxane (5.0 mL) was treated with HCl (4.0 M in dioxane, 1.2 mL, 4.6 mmol). After stirring overnight, the mixture was concentrated to afford (4aS,10bS)-8-(trifluoromethyl)-2,3,4,4a,6,10b-hexahydro-1H-pyrano[3,2-b:5,4-b']dipyridine hydrochloride. ES/MS: m/z=259.2 $[M+H]^+$.

General Procedure LXI-E for the Synthesis of Intermediates Ebi:

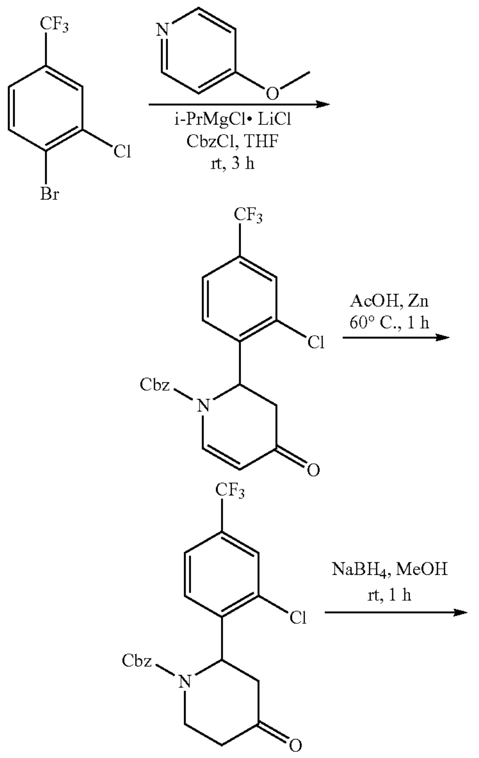

-continued

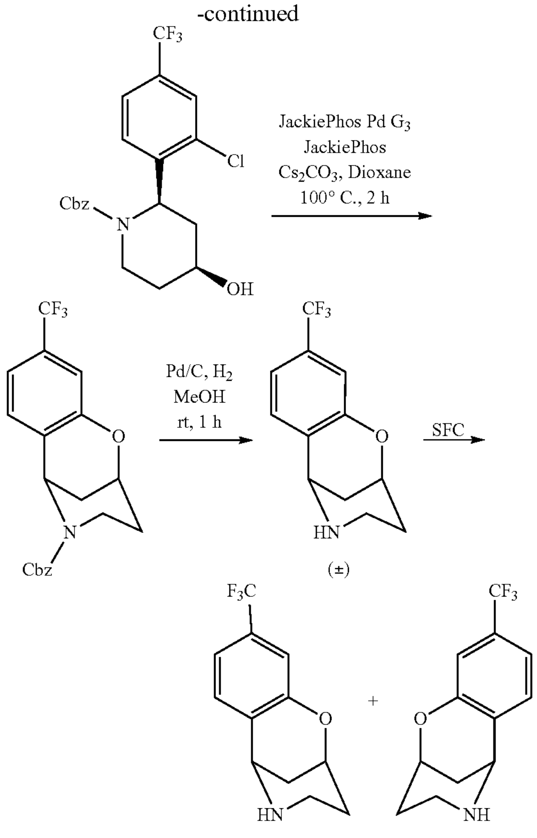

Ebi-1 Ebi-2

Step 1. benzyl 2-(2-chloro-4-(trifluoromethyl)phenyl)-4-oxo-3,4-dihydropyridine-1(2H)-carboxylate. To a solution of 1-bromo-2-chloro-4-(trifluoromethyl)benzene (10.0 g, 38.5 mmol, 1.00 equiv) in THF (60.0 mL) at room temperature was added i-PrMgCl·LiCl (28.5 mL, 37.0 mmol, 0.960 equiv) dropwise under nitrogen atmosphere. The resulting mixture was stirred under nitrogen atmosphere at room temperature for 1.5 h. The resulting mixture was diluted with THF (140 mL). The mixture was allowed to cool down to −5° C. To the above mixture was added 4-methoxypyridine (3.66 g, 33.5 mmol, 0.870 equiv) and CbzCl (5.85 g, 34.3 mmol, 0.890 equiv) dropwise over 10 min at −5° C. The resulting mixture was stirred at room temperature for additional 1.5 h. The reaction was monitored by LCMS. The reaction was quenched by the addition of aq. HCl (100 mL, 6 mol/L) at 0° C. The resulting mixture was extracted with EtOAc (3×200 mL). The combined organic layers were washed with brine (2×100 mL), dried over anhydrous $Na_2SO_4$. After filtration, the filtrate was concentrated under reduced pressure. The residue was purified by silica gel column chromatography, eluted with PE/EA (10:1) to afford benzyl 2-(2-chloro-4-(trifluoromethyl)phenyl)-4-oxo-3,4-dihydropyridine-1(2H)-carboxylate. ES/MS: m/z=410.1 $[M+H]^+$.

Step 2. benzyl 2-(2-chloro-4-(trifluoromethyl)phenyl)-4-oxopiperidine-1-carboxylate. A solution of benzyl 2-(2-chloro-4-(trifluoromethyl)phenyl)-4-oxo-3,4-dihydropyridine-1(2H)-carboxylate (12.0 g, 29.3 mmol, 1.00 equiv) in AcOH (120 mL) was added Zn (5.74 g, 87.9 mmol, 3.00 equiv). The mixture was stirred under nitrogen atmosphere at 60° C. for 1 h. The mixture was allowed to cool down to room temperature. The resulting mixture was diluted with water (200 mL). The resulting mixture was extracted with EtOAc (3×300 mL). The combined organic layers were washed with brine (2×200 mL), dried over anhydrous $Na_2SO_4$. After filtration, the filtrate was concentrated under reduced pressure. The residue was purified by silica gel column chromatography, eluted with PE/EA (5:1) to afford benzyl 2-(2-chloro-4-(trifluoromethyl)phenyl)-4-oxopiperidine-1-carboxylate. ES/MS: m/z=412.1 $[M+H]^+$.

Step 3. Rac-benzyl (2R,4S)-2-(2-chloro-4-(trifluoromethyl)phenyl)-4-hydroxypiperidine-1-carboxylate. To a solution of benzyl 2-(2-chloro-4-(trifluoromethyl)phenyl)-4-oxopiperidine-1-carboxylate (8.30 g, 20.2 mmol, 1.00 equiv) in MeOH (83.0 mL) was added $NaBH_4$ (1.14 g, 30.2 mmol, 1.50 equiv) in portions at 0° C. The resulting mixture was stirred at room temperature for 1 h. The reaction was quenched with sat. $NH_4Cl$ at 0° C. The resulting mixture was diluted with water (100 mL). The resulting mixture was extracted with EtOAc (3×300 mL). The combined organic layers were washed with brine (2×100 mL), dried over anhydrous $Na_2SO_4$. After filtration, the filtrate was concentrated under reduced pressure. The residue was purified by silica gel column chromatography, eluted with PE/EA (5:1) to afford benzyl 2-(2-chloro-4-(trifluoromethyl)phenyl)-4-hydroxypiperidine-1-carboxylate. ES/MS: m/z=414.1 $[M+H]^+$.

Step 4. Rac-benzyl (2S,6R)-9-(trifluoromethyl)-3,4-dihydro-2H-2,6-methanobenzo[b][1,5]oxazocine-5(6H)-carboxylate. To a solution of rac-benzyl 2-(2-chloro-4-(trifluoromethyl)phenyl)-4-hydroxypiperidine-1-carboxylate (5.00 g, 12.1 mmol, 1.00 equiv) and $Cs_2CO_3$ (7.87 g, 24.2 mmol, 2.00 equiv) in dioxane (100 mL) was added JackiePhos (962 mg, 1.21 mmol, 0.10 equiv) and JackiePhos Pd G3 (1.41 g, 1.21 mmol, 0.10 equiv). The mixture was stirred at 100° C. for 2 h under $N_2$ atmosphere. The mixture was allowed to cool down to room temperature. The resulting mixture was filtered, the filter cake was washed with acetonitrile (3×20 mL). The resulting mixture was diluted with water (100 mL). The resulting mixture was extracted with EtOAc (3×300 mL). The combined organic layers were washed with brine (2×100 mL), dried over anhydrous $Na_2SO_4$. After filtration, the filtrate was concentrated under reduced pressure. The residue was purified by reversed-phase flash chromatography [with the following conditions: column: C18; mobile phase A: Water (0.1% TFA), mobile phase B: MeCN; gradient: 0% B to 100% B in 20 min; detector, UV 254 nm] to afford benzyl 9-(trifluoromethyl)-3,4-dihydro-2H-2,6-methanobenzo[b][1,5]oxazocine-5(6H)-carboxylate. ES/MS: m/z=378.1 $[M+H]^+$.

Step 5. Rac-(2S,6R)-9-(trifluoromethyl)-3,4,5,6-tetrahydro-2H-2,6-methanobenzo[b][1,5]oxazocine. To a solution of rac-benzyl (2S,6R)-9-(trifluoromethyl)-3,4-dihydro-2H-2,6-methanobenzo[b][1,5]oxazocine-5(6H)-carboxylate (2.20 g, 5.83 mmol, 1.00 equiv) in MeOH (22.0 mL) was added Pd/C (2.20 g, 5% wt) in portions. The mixture was stirred under hydrogen atmosphere at room temperature for 1 h. The resulting mixture was filtered through a short pad of Celite. The pad was washed with acetonitrile (3×10 mL). The combined filtrate was concentrated under reduced pressure to afford 9-(trifluoromethyl)-3,4,5,6-tetrahydro-2H-2,6-methanobenzo[b][1,5]oxazocine. ES/MS: m/z=244.1 $[M+H]^+$.

Step 6. (2S,6R)-9-(trifluoromethyl)-3,4,5,6-tetrahydro-2H-2,6-methanobenzo[b][1,5]oxazocine (Ebi-1) and (2R,6S)-9-(trifluoromethyl)-3,4,5,6-tetrahydro-2H-2,6-methanobenzo[b][1,5]oxazocine (Ebi-2). Rac-9-(trifluoromethyl)-3,4,5,6-tetrahydro-2H-2,6-methanobenzo[b][1,5] oxazocineas (1.10 g, 4.52 mmol, 1.00 equiv) was purified by prep-Chiral HPLC [with the following conditions: Column: NB_CHIRALPAK AD-H, 3*25 cm, 5 m; Mobile Phase A: $CO_2$, Mobile Phase B: IPA:HEX=1:2 (0.2% DEA); Flow rate: 100 mL/min; Gradient: isocratic 15% B; Column Temperature (° C.): 35; Back Pressure (bar): 100; Wave Length: 212/286 nm; RT1 (min): 10.42; RT2 (min): 11.73] to afford 5-(trifluoromethyl)-8-oxa-12-azatricyclo[7.3.1.0(2,7]trideca-2(7),3,5-triene Ebi-1 and 5-(trifluoromethyl)-8-oxa-12-azatricyclo[7.3.1.0(2,7]trideca-2(7),3,5-triene Ebi-2.

(2S,6R)-9-(trifluoromethyl)-3,4,5,6-tetrahydro-2H-2,6-methanobenzo[b][1,5]oxazocine (Ebi-1). ES/MS: m/z=244.1 $[M+H]^+$. $^1H$ NMR (400 MHz, DMSO-$d_6$) δ 7.34 (d, J=7.8 Hz, 1H), 7.16 (dd, J=7.9, 1.9 Hz, 1H), 7.06 (s, 1H), 4.74-4.65 (m, 1H), 4.03-3.95 (m, 1H), 2.74-2.56 (m, 2H), 2.40-2.26 (m, 1H), 2.13-1.99 (m, 1H), 1.87-1.67 (m, 3H).

(2R,6S)-9-(trifluoromethyl)-3,4,5,6-tetrahydro-2H-2,6-methanobenzo[b][1,5]oxazocine (Ebi-2). ES/MS: m/z=244.1 $[M+H]^+$. $^1H$ NMR (400 MHz, DMSO-$d_6$) δ 7.34 (d, J=7.8 Hz, 1H), 7.16 (dd, J=7.9, 1.9 Hz, 1H), 7.06 (s, 1H), 4.74-4.65 (m, 1H), 4.03-3.95 (m, 1H), 2.74-2.56 (m, 2H), 2.40-2.26 (m, 1H), 2.13-1.99 (m, 1H), 1.87-1.67 (m, 3H).

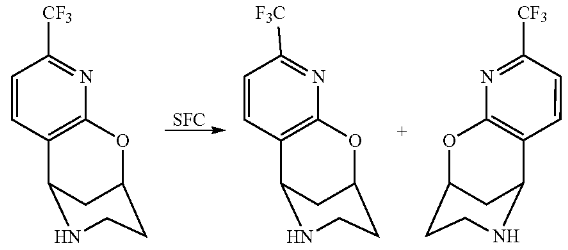

(±) Ebi-3 Ebi-4

(2S,6R)-9-(trifluoromethyl)-3,4,5,6-tetrahydro-2H-2,6-methanopyrido[2,3-b][1,5]oxazocine (Ebi-3) and (2R,6S)-9-(trifluoromethyl)-3,4,5,6-tetrahydro-2H-2,6-methanopyrido[2,3-b][1,5]oxazocine (Ebi-4). Rac-(2S,6R)-9-(trifluoromethyl)-3,4,5,6-tetrahydro-2H-2,6-methanopyrido [2,3-b][1,5]oxazocine prepared from procedure LXI-E starting with 3-bromo-2-chloro-6-(trifluoromethyl)pyridine was purified by prep-Chiral HPLC [with the following conditions: Column: CHIRALPAK IG, 3*25 cm, 5 m; Mobile Phase A: $CO_2$, Mobile Phase B: MeOH (20 mmol/L $NH_3$); Flow rate: 100 mL/min; Gradient: isocratic 35% B; Column Temperature (° C.): 35; Back Pressure (bar): 100; Wave Length: 280/260 nm; RT1 (min): 2.12; RT2 (min): 3.37] to afford (2S,6R)-9-(trifluoromethyl)-3,4,5,6-tetrahydro-2H-2,6-methanopyrido[2,3-b][1,5]oxazocine Ebi-3 and (2R,6S)-9-(trifluoromethyl)-3,4,5,6-tetrahydro-2H-2,6-methanopyrido[2,3-b][1,5]oxazocine as Ebi-4.

(2S,6R)-9-(trifluoromethyl)-3,4,5,6-tetrahydro-2H-2,6-methanopyrido[2,3-b][1,5]oxazocine (Ebi-3). ES/MS: m/z=245.2 $[M+H]^+$. $^1H$ NMR (400 MHz, Chloroform-d) δ 7.70-7.59 (m, 1H), 7.28 (d, J=5.2 Hz, 1H), 5.01-4.90 (m, 1H), 4.23-4.14 (m, 1H), 2.95-2.82 (m, 1H), 2.74-2.59 (m, 1H), 2.24 (d, J=13.5 Hz, 1H), 2.17-2.10 (m, 2H), 2.01 (d, J=13.7 Hz, 1H), 1.97-1.85 (m, 1H).

(2R,6S)-9-(trifluoromethyl)-3,4,5,6-tetrahydro-2H-2,6-methanopyrido[2,3-b][1,5]oxazocine (Ebi-4). ES/MS: m/z=245.2 $[M+H]^+$. $^1H$ NMR (400 MHz, Chloroform-d) δ 7.70-7.59 (m, 1H), 7.28 (d, J=5.2 Hz, 1H), 5.01-4.90 (m, 1H), 4.23-4.14 (m, 1H), 2.95-2.82 (m, 1H), 2.74-2.59 (m, 1H), 2.24 (d, J=13.5 Hz, 1H), 2.17-2.10 (m, 2H), 2.01 (d, J=13.7 Hz, 1H), 1.97-1.85 (m, 1H).

Ebi-5

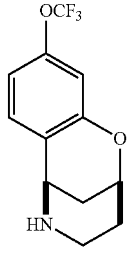

(±)

Rac-(2S,6R)-9-(trifluoromethoxy)-3,4,5,6-tetrahydro-2H-2,6-methanobenzo[b][1,5]oxazocine (Ebi-5). Prepared following procedure LXI-E starting with 1-bromo-2-chloro-4-(trifluoromethoxy)benzene. ES/MS: m/z=260.0 $[M+H]^+$.

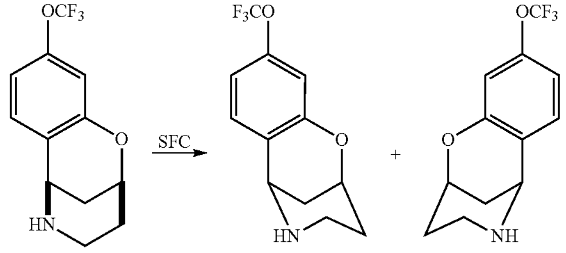

Ebi-5 ± Ebi-6 Ebi-7

(2S,6R)-9-(trifluoromethoxy)-3,4,5,6-tetrahydro-2H-2,6-methanobenzo[b][1,5]oxazocine (Ebi-6) and (2R,6S)-9-(trifluoromethoxy)-3,4,5,6-tetrahydro-2H-2,6-methanobenzo[b][1,5]oxazocine (Ebi-7). Rac-9-(trifluoromethoxy)-3,4,5,6-tetrahydro-2H-2,6-methanobenzo[b][1,5]oxazocine prepared Ebi-5 was purified by prep-Chiral HPLC [with the following conditions: Column: CHIRALPAK IG, 3*25 cm, 5 m; Mobile Phase A: $CO_2$, Mobile Phase B: MeOH (20 mmol/L NH3); Flow rate: 100 mL/min; Gradient: isocratic 35% B; Column Temperature (° C.): 35; Back Pressure (bar): 100; Wave Length: 280/260 nm; RT1 (min): 2.12; RT2 (min): 3.37] to afford the title compounds.

(2S,6R)-9-(trifluoromethoxy)-3,4,5,6-tetrahydro-2H-2,6-methanobenzo[b][1,5]oxazocine (Ebi-6) ES/MS: m/z=260.1 $[M+H]^+$.

(2R,6S)-9-(trifluoromethoxy)-3,4,5,6-tetrahydro-2H-2,6-methanobenzo[b][1,5]oxazocine (Ebi-7). ES/MS: m/z=260.0 $[M+H]^+$.

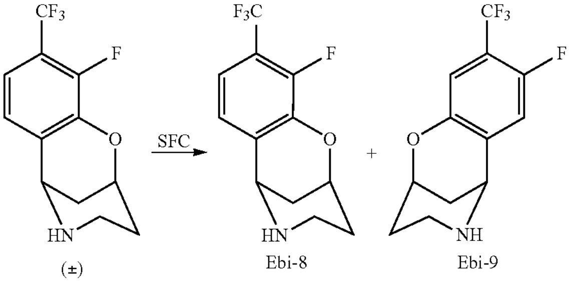

(±) Ebi-8 Ebi-9

(2S,6R)-10-fluoro-9-(trifluoromethyl)-3,4,5,6-tetrahydro-2H-2,6-methanobenzo[b][1,5]oxazocine (Ebi-8) and (2R,6S)-10-fluoro-9-(trifluoromethyl)-3,4,5,6-tetrahydro-2H-2,6-methanobenzo[b][1,5]oxazocine (Ebi-9). Rac-10-fluoro-9-(trifluoromethyl)-3,4,5,6-tetrahydro-2H-2,6-methanobenzo[b][1,5]oxazocine prepared from procedure LXI-E starting with 1-bromo-2-chloro-3-fluoro-4-(trifluoromethyl)benzene was purified by prep-Chiral HPLC [with the following conditions: Column: CHIRALPAK IG, 3*25 cm, 5 m; Mobile Phase A: $CO_2$, Mobile Phase B: MeOH (20 mmol/L NH3); Flow rate: 100 mL/min; Gradient: isocratic 35% B; Column Temperature (° C.): 35; Back Pressure (bar): 100; Wave Length: 280/260 nm; RT1 (min): 2.12; RT2 (min): 3.37] to afford the title compound (2S,6R)-10-fluoro-9-(trifluoromethyl)-3,4,5,6-tetrahydro-2H-2,6-methanobenzo[b][1,5]oxazocine (Ebi-8) ES/MS: m/z=261.9 $[M+H]^+$.

(2R,6S)-10-fluoro-9-(trifluoromethyl)-3,4,5,6-tetrahydro-2H-2,6-methanobenzo[b][1,5]oxazocine (Ebi-9). ES/MS: m/z=261.9 $[M+H]^+$.

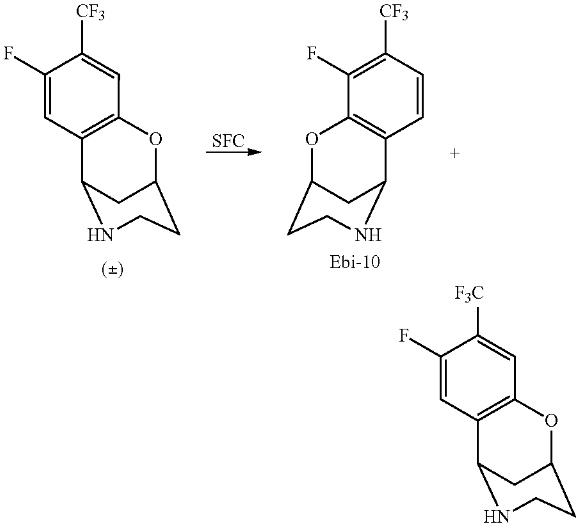

(±) Ebi-10

Ebi-11

(2S,6R)-8-fluoro-9-(trifluoromethyl)-3,4,5,6-tetrahydro-2H-2,6-methanobenzo[b][1,5]oxazocine (Ebi-10) and (2R,6S)-8-fluoro-9-(trifluoromethyl)-3,4,5,6-tetrahydro-2H-2,6-methanobenzo[b][1,5]oxazocine (Ebi-11). Rac-8-fluoro-9-(trifluoromethyl)-3,4,5,6-tetrahydro-2H-2,6-methanobenzo[b][1,5]oxazocine prepared from procedure LXI-E starting with 1-bromo-2-chloro-5-fluoro-4-(trifluoromethyl)benzene was purified by prep-Chiral HPLC [with the following conditions: Column: CHIRALPAK IG, 3*25 cm, 5 m; Mobile Phase A: $CO_2$, Mobile Phase B: MeOH (20 mmol/L NH3); Flow rate: 100 mL/min; Gradient: isocratic 35% B; Column Temperature (° C.): 35; Back Pressure (bar): 100; Wave Length: 280/260 nm; RT1 (min): 2.12; RT2 (min): 3.37] to afford the title compound (2R,6S)-8-fluoro-9-(trifluoromethyl)-3,4,5,6-tetrahydro-2H-2,6-methanobenzo[b][1,5]oxazocine (Ebi-10) ES/MS: m/z=262.0 $[M+H]^+$.

(2S,6R)-8-fluoro-9-(trifluoromethyl)-3,4,5,6-tetrahydro-2H-2,6-methanobenzo[b][1,5]oxazocine (Ebi-11). ES/MS: m/z=261.9 $[M+H]^+$.

General Procedure LXII-E for the Synthesis of Intermediates Ebj:

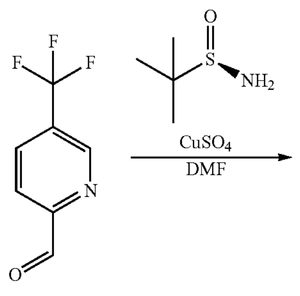

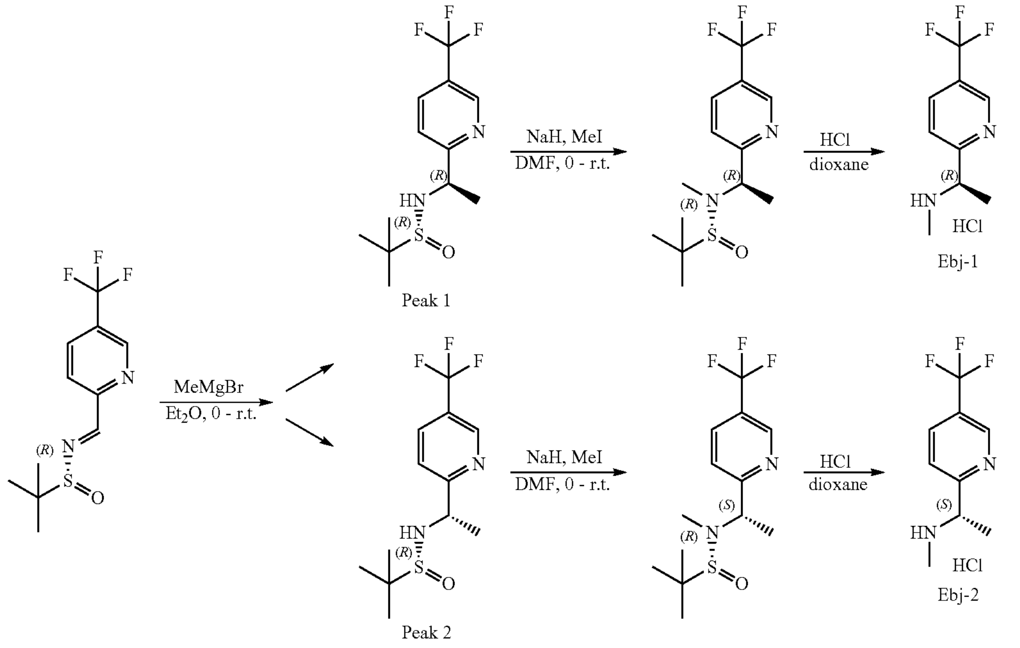

Peak 1
Ebj-1
Peak 2
Ebj-2

Step 1. (R,E)-2-methyl-N-((5-(trifluoromethyl)pyridin-2-yl)methylene)propane-2-sulfinamide. A solution of 5-(trifluoromethyl)picolinaldehyde (2.9 mmol, 1.0 equiv), and copper (II) sulfate (5.7 mmol, 2,0 equiv) and (R)-2-methylpropane-2-sulfinamide (2.9 mmol, 1.0 equiv) in DCM was stirred at room temperature for 16 h. The reaction mixture was then filtered through celite and rinsed with DCM, concentrated, and purified by silica gel chromatography to afford the desired compound. ES/MS: m/z=279.2 $[M+H]^+$.

Step 2. (R)-2-methyl-N—((R)-1-(5-(trifluoromethyl)pyridin-2-yl)ethyl)propane-2-sulfinamide. To a solution of (R,E)-2-methyl-N-((5-(trifluoromethyl)pyridin-2-yl)methylene)propane-2-sulfinamide (0.72 mmol, 1.0 equiv) in diethyl ether (5.0 mL) at 0 C. To this was added methyl magnesium bromide (3.0 M in diethyl ether, 1.2 mmol, 1.7 equiv) dropwise. The reaction mixture was then stirred at 0 C for 30 minutes then warmed to room temperature and stirred for 4 h. The reaction was mixture was then quenched with saturated ammonium chloride, extracted with EtOAc, dried over magnesium sulfate, concentrated and purified by silica gel chromatography to provide the desired products. ES/MS: m/z=295.1 $[M+H]^+$.

Step 3. (R)—N,2-dimethyl-N—((R)-1-(5-(trifluoromethyl)pyridin-2-yl)ethyl)propane-2-sulfinamide. To a solution of (R)-2-methyl-N—((R)-1-(5-(trifluoromethyl)pyridin-2-yl)ethyl)propane-2-sulfinamide (peak 1, 0.52 mmol, 1 equiv), at 0 C was added sodium hydride (0.63 mmol, 1.2 equiv). The reaction mixture was stirred at 0 C for 15 min. Then iodomethane (0.58 mmol, 1.1 equiv) was added dropwise and the reaction mixture was allowed to warm to room temperature. After 3 h the reaction mixture was quenched with ammonium chloride, diluted with EtOAc, dried over magnesium sulfate, concentrated and purified by silica gel chromatography. ES/MS: m/z=309.0 [M+H]+

Step 4. (R)—N-methyl-1-(5-(trifluoromethyl)pyridin-2-yl)ethan-1-amine hydrochloride (Ebj-1). To a solution of (R)-2-methyl-N—((R)-1-(5-(trifluoromethyl)pyridin-2-yl)ethyl)propane-2-sulfinamide (0.50 mmol, 1.0 equiv) in DCM was added hydrochloric acid (4.0 M in DCM, 0.5 mmol, 1.0 equiv) and the reaction mixture was stirred for 1 h at room temperature. The reaction mixture was then concentrated to afford the desired compound. ES/MS: m/z=205.1 [M+H]+

(S)—N-methyl-1-(5-(trifluoromethyl)pyridin-2-yl)ethan-1-amine hydrochloride (Ebj-2). Prepared following step 3 and 4 starting with peak 2 isolated after step 2. ES/MS: m/z=205.1 [M+H]+

Ebj-3

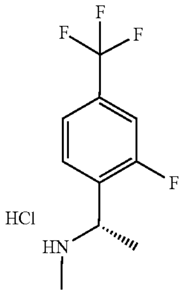

(S)-1-(2-fluoro-4-(trifluoromethyl)phenyl)-N-methylethan-1-amine hydrogen chloride (Ebj-3). Prepared using general procedure LXII-E starting with commercial 2-fluoro-4-(trifluoromethyl)benaldehyde. Isolating Peak 1. ES/MS: m/z=222.1[M+H]$^+$.

Ebj-4

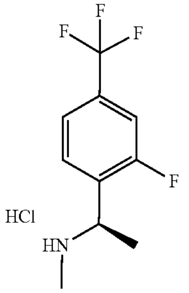

(R)-1-(2-fluoro-4-(trifluoromethyl)phenyl)-N-methylethan-1-amine hydrogen chloride (Ebj-4) was prepared using general procedure LXII-E starting with commercial 2-fluoro-4-(trifluoromethyl)benzaldehyde. Isolating Peak 2. ES/MS: m/z=222.1 [M+H]$^+$.

Ebj-5

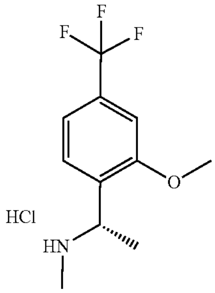

(S)-1-(2-methoxy-4-(trifluoromethyl)phenyl)-N-methylethan-1-amine hydrogen chloride (Ebj-5) was prepared using general procedure LXII-E starting with commercial 2-methoxy-4-(trifluoromethyl)benzaldehyde. Isolating Peak 1. ES/MS: m/z=234.0 [M+H]$^+$.

Ebj-6

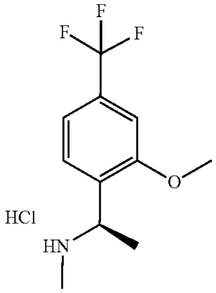

(R)-1-(2-methoxy-4-(trifluoromethyl)phenyl)-N-methylethan-1-amine hydrogen chloride (Ebj-6) was prepared using general procedure LXII-E starting with commercial 2-methoxy-4-(trifluoromethyl)benzaldehyde. Isolating Peak 2. ES/MS: m/z=234.1 [M+H]$^+$.

Ebj-7

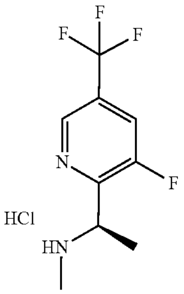

(R)-1-(3-fluoro-5-(trifluoromethyl)pyridin-2-yl)-N-methylethan-1-amine hydrogen chloride (Ebj-7) was prepared using general procedure LXII-E starting with 3-fluoro-5-(trifluoromethyl)picolinaldehyde. Isolating Peak 1. ES/MS: m/z=223.2 [M+H]$^+$.

Ebj-8

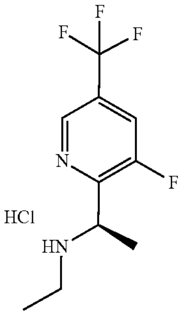

(R)-1-(3-fluoro-5-(trifluoromethyl)pyridin-2-yl)-N-methylethan-1-amine hydrogen chloride (Ebj-8) was prepared using general procedure LXII-E starting with 3-fluoro-5-(trifluoromethyl)picolinaldehyde and ethyl iodide. Isolating Peak 1. ES/MS: m/z=237.2 [M+H]$^+$.

Ebj-9

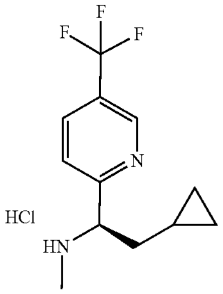

(R)-2-cyclopropyl-N-methyl-1-(5-(trifluoromethyl)pyridin-2-yl)ethan-1-amine hydrogen chloride (Ebj-9) was prepared using general procedure LXII-E starting with 5-(trifluoromethyl)picolinaldehyde and bromo(cyclopropyl methyl)magnesium. Isolating Peak 1. ES/MS: m/z=245.1 $[M+H]^+$.

Ebj-10

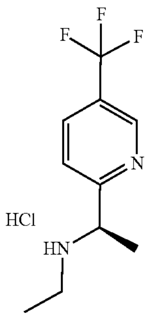

(R)—N-ethyl-1-(5-(trifluoromethyl)pyridin-2-yl)ethan-1-amine hydrogen chloride (Ebj-10) was prepared using general procedure LXII-E starting with 5-(trifluoromethyl)picolinaldehyde. Isolating Peak 1. ES/MS: m/z=219.2 $[M+H]^+$.

Ebj-11

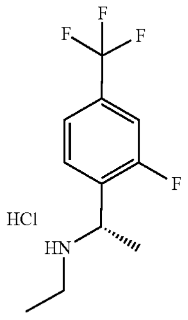

(S)—N-ethyl-1-(5-(trifluoromethyl)pyridin-2-yl)ethan-1-amine hydrogen chloride (Ebj-11) was prepared using general procedure LXII-E starting with 5-(trifluoromethyl)picolinaldehyde. Isolating Peak 2. ES/MS: m/z=219.2 $[M+H]^+$.

General Procedure LXIII-E for the Synthesis of Intermediates Ebk:

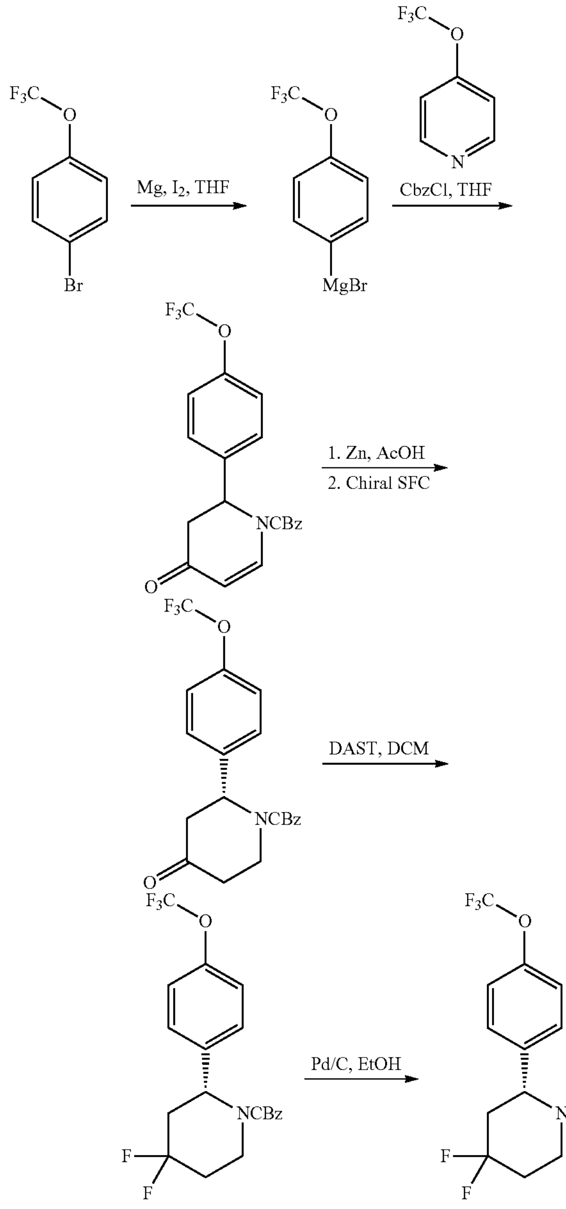

Ebk-1

Step 1. (4-(trifluoromethoxy)phenyl)magnesium bromide. A flask was charged with Magnesium Chips (22.2 g, 912.8 mmol, 2.2 eq), then suspended in anhydrous THF (1 L). 12 (2.6 g, 20.7 mmol, 0.05 eq) was then added at room temperature under nitrogen. The solution was then heated to 60° C. and 1-bromo-4-(trifluoromethoxy)benzene (100.0 g, 414.9 mmol, 1.0 eq) in anhydrous THF (100 mL) was added dropwise. After that the reaction mixture was allowed to cool to room temperature and stirred for 4 h. The resultant product was then used as in the subsequent step.

Step 2. Benzyl 4-oxo-2-(4-(trifluoromethoxy)phenyl)-3,4-dihydropyridine-1(2H)-carboxylate. A solution of 4-methoxypyridine (50.0 g, 458.2 mmol, 1.0 eq) in THF (2.5 L) was cooled to −30° C. CbzCl (78.2 g, 458.2 mmol, 1.0 eq) was then added drop-wise and the reaction mixture was stirred for 30 min. A solution of (4-(trifluoromethoxy) phenyl)magnesium bromide (2.4 L, 829.6 mmol, 1.8 eq) in THF was added drop-wise to the mixture at −30° C. The mixture was allowed to stir for 30 minutes before being warmed up to room temperature. It was allowed to stir for an additional 30 minutes before being quenched with 2 M HCl (2 L). The organic solvent was removed under pressure and the crude material was purified by silica gel column chromatography to afford benzyl 4-oxo-2-(4-(trifluoromethoxy)phenyl)-3,4-dihydropyridine-1(2H)-carboxylate. ES/MS: m/z=392.0 $[M+H]^+$. $^1$HNMR (400 MHz, $CDCl_3$): δ 7.98-7.96 (m, 1H), 7.35-7.34 (m, 3H), 7.26-7.22 (m, 4H), 7.14-7.12 (m, 2H), 5.73 (d, J=7.2 Hz, 1H), 5.41 (d, J=8.4 Hz, 1H), 5.24 (q, J=12.0 Hz, 2H), 3.19-3.13 (m, 1H), 2.79-2.74 (m, 1H).

Step 3. Benzyl-4-oxo-2-(4-(trifluoromethoxy)phenyl)piperidine-1-carboxylate. A flask was charged with benzyl 4-oxo-2-(4-(trifluoromethoxy)phenyl)-3,4-dihydropyridine-1(2H)-carboxylate (50.0 g, 127.8 mmol, 1.0 eq) which was suspended in AcOH (500 mL). Zn powder (83.5 g, 1.28 mol, 10.0 eq) was added portion-wise at room temperature. The resulting solution was then heated to 90° C. and stirred for 1 h. The reaction mixture was cooled to room temperature and filtered. The filtrate was concentrated in vacuo, and the resulting residue was purified via flash silica gel column chromatography to afford benzyl 4-oxo-2-(4-(trifluoromethoxy)phenyl)piperidine-1-carboxylate. ES/MS: m/z=416.0 $[M+Na]^+$. The resulting mixture of enantiomers was then separated by SFC to afford the (R)-enantiomer.

Step 4. Benzyl (R)-4,4-difluoro-2-(4-(trifluoromethoxy) phenyl)piperidine-1-carboxylate. A solution of Benzyl-(R)-4-oxo-2-(4-(trifluoromethoxy)phenyl)piperidine-1-carboxylate (10.0 g, 25.4 mmol, 1.0 eq) was suspended in DCM (100 mL) under argon. The solution was cooled to 0° C., and DAST (20.5 g, 127.1 mmol, 5.0 eq) was added dropwise. The reaction mixture was then stirred at room temperature for 18 h. After the allotted time, the mixture was quenched with sat. aq. $NaHCO_3$ (1.0 L) at 0° C. and extracted with DCM (300 mL×2). The combined organic phase was dried over $Na_2SO_4$, filtered and concentrated. The residue was purified by prep-HPLC to afford benzyl (R)-4,4-difluoro-2-(4-(trifluoromethoxy)phenyl)piperidine-1-carboxylate. $^1$HNMR (400 MHz, DMSO-$d_6$): δ 7.36-7.32 (m, 9H), 5.61-5.60 (m, 1H), 5.18-5.11 (m, 2H), 4.26-4.23 (m, 1H), 3.13-3.06 (m, 1H), 2.83-2.77 (m, 1H), 2.53-2.41 (m, 1H), 2.11-2.00 (m, 2H).

Step 5. (R)-4,4-difluoro-2-(4-(trifluoromethoxy)phenyl) piperidine (Ebk-1). Benzyl (R)-4,4-difluoro-2-(4-(trifluoromethoxy)phenyl)piperidine-1-carboxylate (2.68 g, 6.46 mmol, 1.0 equiv) was dissolved in EtOH (45 mL). Pd/C (20% by weight, 537 mg) was then added to the reaction vessel which was flushed with hydrogen (3×) before being brought to 45 psi and shaken for 2 hours. After the allotted time, the mixture was filtered over celite using ethyl acetate and concentrated to afford the crude product which was used as is in subsequent reactions. ES/MS: m/z=282.2 $[M+H]^+$.

General Procedure LXIV-E for the Synthesis of Intermediates Ebl:

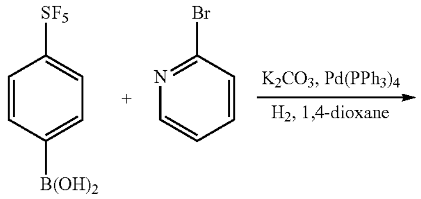

-continued

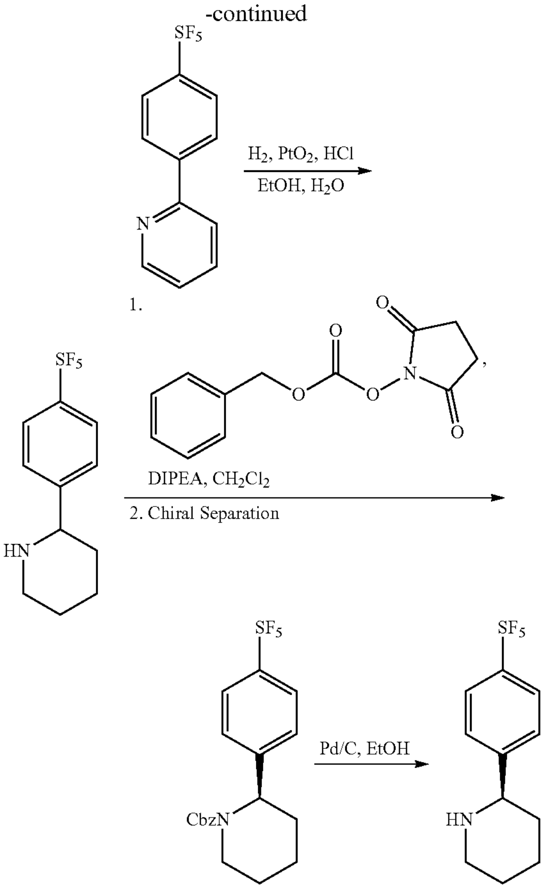

Ebi-1

Step 1. 2-(4-(pentafluoro-λ6-sulfaneyl)phenyl)pyridine. A pressure tube was charged with 2-bromopyridine (687 mg, 4.3 mmol, 1.1 equiv), $Pd(PPh_3)_4$ (100 mg, 22 mol %, 0.087 mmol), (4-(pentafluoro-λ6-sulfaneyl)phenyl)boronic acid (980 mg, 4.0 mmol, 1.0 equiv) and potassium carbonate (1.00 g, 7.2 mmol, 1.8 equiv). The contents of the tube were then suspended in water (5.0 mL) and 1,4-dioxane (50 mL). The tube was flushed with argon, sealed and heated to 110° C. overnight. The resulting mixture was then cooled to room temperature, concentrated and purified via silica gel flash column chromatography to afford 2-(4-(pentafluoro-λ6-sulfaneyl)phenyl)pyridine. ES/MS: m/z=282.0 $[M+H]^+$.

Step 2. 2-(4-(pentafluoro-λ6-sulfaneyl)phenyl)piperidine. A flask was charged with 2-(4-(pentafluoro-λ6-sulfaneyl) phenyl)pyridine (984 mg, 3.5 mmol, 1.0 equiv) and platinum (IV) oxide (200 mg, 0.88 mmol, 25 mol %). The contents of the flask were then suspended in ethanol (50 mL), water (3.5 mL) and 1.0 M hydrochloric acid (3.5 mL). The flask was then purged with hydrogen gas, and allowed to stir overnight at 23° C. The contents of the flask were then filtered over a plug of celite and concentrated under reduced pressure to provide crude product, which was carried forward to the next step. ES/MS: m/z=288.1 $[M+H]^+$.

Step 3. Benzyl (R)-2-(4-(pentafluoro-λ6-sulfaneyl)phenyl)piperidine-1-carboxylate. A flask was charged with 2-(4-(pentafluoro-λ6-sulfaneyl)phenyl)piperidine (1.1 g, 3.3 mmol, 1.0 equiv) and benzyl (2,5-dioxopyrrolidin-1-yl) carbonate (1.0 g, 4.0 mmol, 1.2 equiv). The contents of the vial were then suspended in methylene chloride (30 mL) and N,N-diisopropylethylamine (1.14 mL, 6.5 mmol, 2.0 equiv).

The flask was allowed to stir at room temperature overnight. The product was then concentrated and purified via silica gel column chromatography. The mixture of enantiomers could then be separated using chiral SFC.

Step 4. (R)-2-(4-(pentafluoro-λ6-sulfaneyl)phenyl)piperidine (Ebl-1). (R)-4,4-difluoro-2-(4-(trifluoromethoxy)phenyl)piperidine (90 mg, 0.214 mmol, 1.0 equiv) and Pd/C (2.27 mg, 10 mol %, 0.0214 mmol) were dissolved in ethanol (10 mL). The flask was then flushed with hydrogen gas, before the mixture was allowed to stir at room temperature for three days under positive pressure of hydrogen. After the allotted time, the mixture was filtered over celite using ethyl acetate and concentrated to afford the crude product which was used as is in subsequent reactions. ES/MS: m/z=288.1 $[M+H]^+$.

General Procedure LXV-E for the Synthesis of Intermediates Ebm:

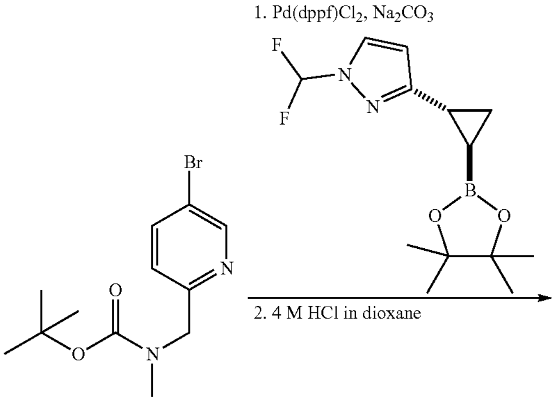

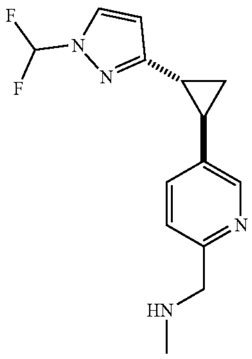

Ebm-1

Trans-1-[5-[(1R,2R)-2-[1-(difluoromethyl)pyrazol-3-yl]cyclopropyl]-2-pyridyl]-N-methyl-methanamine (Ebm-1). To a dried, rounded microwave vial was added tert-butyl N-[(5-bromo-2-pyridyl)methyl]-N-methyl-carbamate (110 mg, 0.37 mmol), 1-(difluoromethyl)-4-[(1R,2R)-2-(4,4,5,5-tetramethyl-1,3,2-dioxaborolan-2-yl)cyclopropyl]pyrazole (104 mg, 0.37 mmol), [1,1'-Bis(diphenylphosphino)ferrocene]dichloropalladium(II) (40.6 mg, 0.055 mmol), sodium carbonate (116 mg, 1.1 mmol), in 1 mL of dioxane/water (3/1). The mixture was sparged with argon for 5 minutes before vial sealed with cape. It was heated to 140° C. for 1 hour. The mixture was filtered and purified by HPLC prep to get desired product. After lyophilization, the power was dissolved in 1 mL of 4 M HCl in dioxane. It was stirred for 2 hours. Diluted with 10 mL of EtOAc and washed with saturated sodium bicarbonate twice. The organic layer was dried and concentrated to afford Ebm-1. ES/MS: m/z=279.2 $[M+H]^+$.

Ebm-2

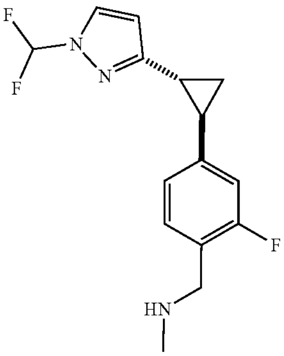

Trans-1-[4-[(1R,2R)-2-[1-(difluoromethyl)pyrazol-3-yl]cyclopropyl]-2-fluoro-phenyl]-N-methyl-methanamine (Ebm-2). Prepared following general procedure LXV-E using tert-butyl N-[(4-bromo-2-fluoro-phenyl)methyl]-N-methyl-carbamate. ES/MS: m/z=285.2 $[M+H]^+$.

Ebm-3

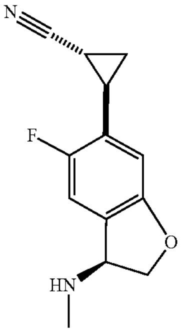

Trans-2-[(3S)-5-fluoro-3-(methylamino)-2,3-dihydrobenzofuran-6-yl]cyclopropanecarbonitrile (Ebm-3). Prepared following general procedure LXV-E using tert-butyl N-[(3S)-6-bromo-5-fluoro-2,3-dihydrobenzofuran-3-yl]-N-methyl-carbamate and trans-potassium (2-cyanocyclopropyl)trifluoroborate. ES/MS: m/z=233.2 $[M+H]^+$.

General Procedure LXVI-E for the Synthesis of Intermediates Ebn:

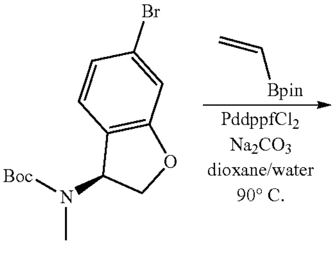

-continued

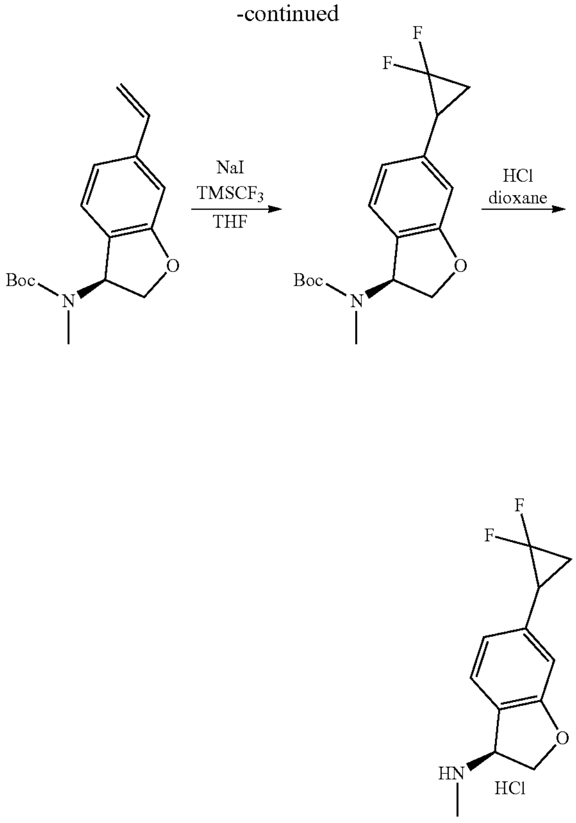

Ebn-1

Step 1: tert-butyl (S)-methyl(6-vinyl-2,3-dihydrobenzofuran-3-yl)carbamate. To a solution of tert-butyl (S)-(6-bromo-2,3-dihydrobenzofuran-3-yl)(methyl)carbamate (0.69 mmol, 1.0 equiv) and 4,4,5,5-tetramethyl-2-vinyl-1,3,2-dioxaborolane (1.4 mmol, 2.0 equiv), and $PdCl_2$(dppf) 0.10 mmol, 0.15 equiv) in dioxane (5 mL), was added 2M $Na_2CO_3$ (3.4 mmol, 5.0 equiv). The mixture was bubbled through argon for 1 minute and left to stir at 90° C. for 1 hours. The mixture was filtered through a pad of celite and anhydrous $MgSO_4$. The solution was reduced under pressure and the crude was purified by flash chromatography. ES/MS: m/z=276.2 [M+H]+

Step 2: tert-butyl ((3S)-6-(2,2-difluorocyclopropyl)-2,3-dihydrobenzofuran-3-yl)(methyl)carbamate. To a solution of tert-butyl (S)-methyl(6-vinyl-2,3-dihydrobenzofuran-3-yl)carbamate (0.064 mmol, 1.0 equiv) in THF (3 mL) was added sodium iodide (0.13 mmol, 0.2. equiv) and trifluoromethyltrimethyl silane (1.6 mmol, 2.5 equiv). The reaction mixture was stirred for 2 h at 80 C. The mixture was filtered through a pad of celite and anhydrous $MgSO_4$. The solution was reduced under pressure and the crude was purified by flash chromatography. ES/MS: m/z=325.7 $[M+H]^+$.

Step 3: (3S)-6-(2,2-difluorocyclopropyl)-N-methyl-2,3-dihydrobenzofuran-3-amine hydrogen chloride (Ebn-1). To a solution of tert-butyl ((3S)-6-(2,2-difluorocyclopropyl)-2,3-dihydrobenzofuran-3-yl)(methyl)carbamate (0.26 mmol, 1.0 equiv) in DCM (2 mL) was added hydrochloric acid (4.0 M in dioxane, 2.6 mmol, 10 equiv). The reaction mixture was stirred at room temperature for 1 h. Then concentrated to provide the desired product. ES/MS: m/z=195.1 $[M-NHMe]^+$.

Ebn-2

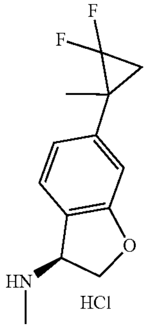

(3S)-6-(2,2-difluoro-1-methylcyclopropyl)-N-methyl-2,3-dihydrobenzofuran-3-amine hydrogen chloride (Ebn-2). Prepared following procedure LXVI-E using commercial 4,4,5,5-tetramethyl-2-(prop-1-en-2-yl)-1,3,2-dioxaborolane. ES/MS: m/z=209.2 $[M-NHMe]^+$.

General Procedure LXVI-E for the Synthesis of Intermediates Ebo:

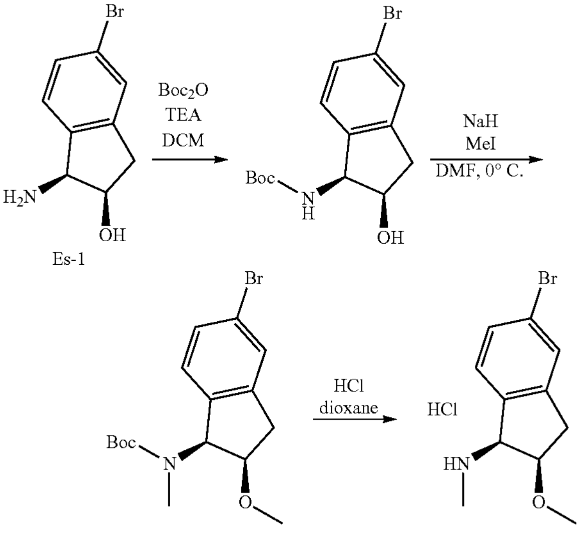

Es-1

Ebo-1

Step 1. tert-butyl ((1S,2R)-5-bromo-2-hydroxy-2,3-dihydro-1H-inden-1-yl)carbamate. To a solution of (1S,2R)-1-amino-5-bromo-2,3-dihydro-1H-inden-2-ol Es-1 (0.88 mmol, 1.0 equiv) in DCM (0.1 M) was added triethylamine (2.6 mmol, 3.0 equiv) and tert-butoxycarbonyl tert-butyl carbonate (0.96 mmol, 1.1 equiv). The reaction mixture was stirred for 5 h at r.t. Then concentrated and purified by silica gel chromatography. To yield the desired product. ES/MS: m/z=328.2 $[M+H]^+$.

Step 2. tert-butyl ((1S,2R)-5-bromo-2-methoxy-2,3-dihydro-1H-inden-1-yl)(methyl)carbamate. To a solution of tert-butyl ((1S,2R)-5-bromo-2-hydroxy-2,3-dihydro-1H-inden-1-yl)carbamate (0.30 mmol, 1.0 equiv) in DMF (0.2M) at 0 C was added sodium hydride (0.76 mmol, 2.5 equiv) and the reaction mixture was stirred for 15 min at 0 C. Then methyl iodide was added (0.76 mmol, 2.5 equiv) and the reaction was slowly warmed to room temperature and stirred for 3 h. Then quenched with saturated ammonium chloride and diluted with EtOAc, dried over magnesium sulfate and purified by silica gel chromatography. ES/MS: m/z=355.7 $[M+H]^+$.

Step 3. (1S,2R)-5-bromo-2-methoxy-N-methyl-2,3-dihydro-1H-inden-1-amine hydrochloride (Ebo-1). To a solution of tert-butyl ((1S,2R)-5-bromo-2-methoxy-2,3-dihydro-1H-inden-1-yl)(methyl)carbamate (2.0 mmol, 1.0 equiv) in DCM (0.1 M) was added hydrochloric acid (4.0 M in dioxane, 30 mmol, 15.0 equiv). The reaction mixture was stirred for 1 h at room temperature, then concentrated to provide the desired product. ES/MS: m/z=256.1 [M+H]$^+$.

General Procedure LXVII-E for Intermediates Ebp:

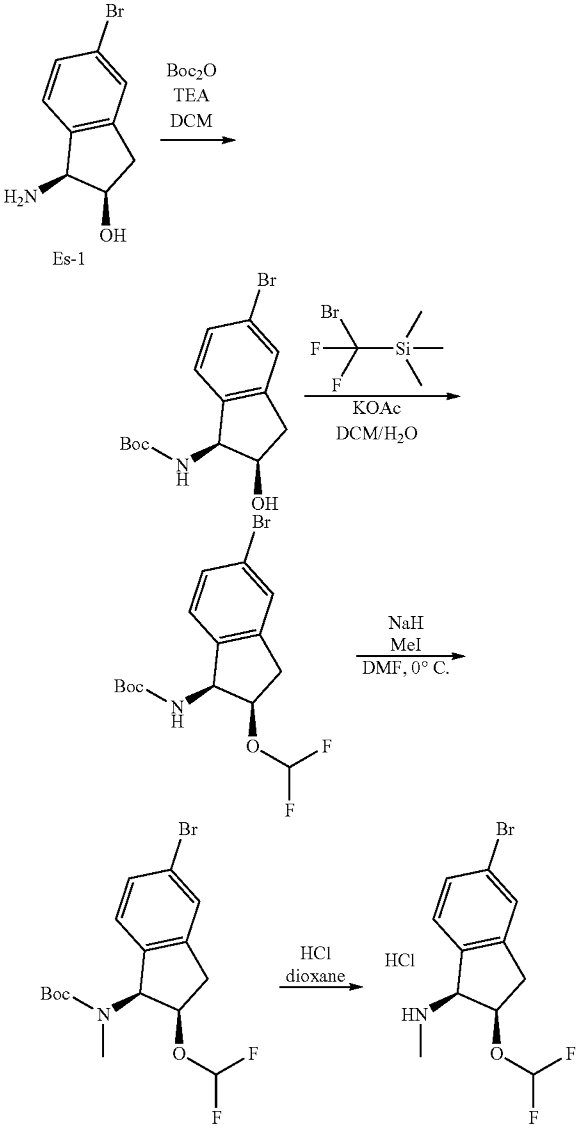

Es-1

Ebp-1

Step 1. tert-butyl ((1S,2R)-5-bromo-2-hydroxy-2,3-dihydro-1H-inden-1-yl)carbamate. To a solution of (1S,2R)-1-amino-5-bromo-2,3-dihydro-1H-inden-2-ol, JDF-Es-1 (0.88 mmol, 1.0 equiv) in DCM (0.1 M) was added triethylamine (2.6 mmol, 3.0 equiv) and tert-butoxycarbonyl tert-butyl carbonate (0.96 mmol, 1.1 equiv). The reaction mixture was stirred for 5 h at r.t. Then concentrated and purified by silica gel chromatography. To yield the desired product. ES/MS: m/z=328.2 [M+H]$^+$.

Step 2. tert-butyl ((1S,2R)-5-bromo-2-(difluoromethoxy)-2,3-dihydro-1H-inden-1-yl)carbamate. To a solution of tert-butyl ((1S,2R)-5-bromo-2-hydroxy-2,3-dihydro-1H-inden-1-yl)carbamate (0.77 mmol, 1.0 equiv) in DCM/water (1:1, 0.1 M) was added potassium acetate (4.62 mmol, 6.0 equiv) and (bromodifluoromethyl)trimethylsilane (2.3 mmol, 3.0 equiv). THE reaction mixture was stirred at room temperature overnight. The reaction mixture was then diluted with DCM, dried, concentrated and purified by silica gel chromatography. ES/MS: m/z=329.7 [M-tBu+H]$^+$.

Step 3. tert-butyl ((1S,2R)-5-bromo-2-(difluoromethoxy)-2,3-dihydro-1H-inden-1-yl)(methyl)carbamate. To a solution of tert-butyl ((1S,2R)-5-bromo-2-(difluoromethoxy)-2,3-dihydro-1H-inden-1-yl)carbamate (0.13, 1.0 equiv) in DMF (0.2M) at 0 C was added sodium hydride (0.20 mmol, 1.5 equiv) and the reaction mixture was stirred for 15 min at 0 C. Then methyl iodide was added (0.15 mmol, 1.1 equiv) and the reaction was slowly warmed to room temperature and stirred for 3 h. Then quenched with saturated ammonium chloride and diluted with EtOAc, dried over magnesium sulfate and purified by silica gel chromatography. ES/MS: m/z=392.1 [M+H]$^+$.

Step 4. (1S,2R)-5-bromo-2-(difluoromethoxy)-N-methyl-2,3-dihydro-1H-inden-1-amine hydrochloride (Ebp-1). To a solution of tert-butyl ((1S,2R)-5-bromo-2-(difluoromethoxy)-2,3-dihydro-1H-inden-1-yl)(methyl)carbamate (0.174 mmol, 1.0 equiv) in 1,4-dioxane (2 mL) was added HCl (4.0 M in dioxane, 1.7 mmol, 10 equiv). The reaction mixture was stirred for 1 h at room temperature then concentrated to afford the desired product. ES/MS: m/z=292.0 [M+H]$^+$.

General Procedure LXVIII-E for Intermediates Ebq:

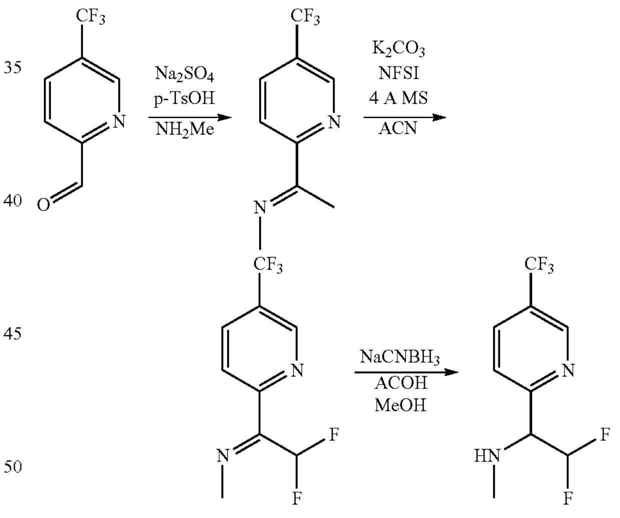

Ebq-1

Step 1: (E)-N-methyl-1-(5-(trifluoromethyl)pyridin-2-yl)ethan-1-imine. To a solution of 5-(trifluoromethyl)picolinaldehyde (1.6 mmol, 1.0 equiv.) in methylamine (13 mmol, 8.3 equiv.) was added sodium sulfate (9.5 mmol, 6.0 equiv.) and p-toluenesulfonic acid monohydrate (0.48 mmol, 0.30 equiv). The reaction mixture was tired overnight at room temperature. The reaction mixture was then concentrated and used in the next step without purification. ES/MS: m/z=203.2 [M+H]$^+$.

Step 2: (Z)-2,2-difluoro-N-methyl-1-(5-(trifluoromethyl)pyridin-2-yl)ethan-1-imine. To a mixture of N-fluorobenzenesulfonamide (4.0 mmol, 3.0 equiv.), potassium carbonate (2.7 mmol, 2.0 equiv.) and 4A molecular sieves (2.3 g) in ACN (8.0 mL) was added (E)-N-methyl-1-(5-(trifluoromethyl)pyridin-2-yl)ethan-1-imine (1.3 mmol, 1.0 equiv.) in ACN (3.0 mL). The reaction mixture was stirred at room temperature overnight. Then triethylamine (1.3 ml was added and the mixture was diluted with diethyl ether, filtered over celite and concentrated. Material was then redissolved in diethyl ether, washed with water and sodium hydroxide (0.5 M), dried over magnesium sulfate, concentrated and used in the next step without further purification. $^1$H NMR (400 MHz, MeOD) δ 8.27-8.17 (m, 2H), 7.35 (d, J=7.5 Hz, 1H), 6.44 (t, J=54.7 Hz, 1H), 2.04 (d, J=8.7 Hz, 3H).

Step 3: 2,2-difluoro-N-methyl-1-(5-(trifluoromethyl)pyridin-2-yl)ethan-1-amine. To a solution of (Z)-2,2-difluoro-N-methyl-1-(5-(trifluoromethyl)pyridin-2-yl)ethan-1-imine (1.3 mmol, 1.0 equiv.) in MeOH (5.0 mL) was added acetic acid (1.4 mmol, 1.1 equiv.) at 0° C., followed by the slow addition of sodium cyanoborohydride (1.4 mmol, 1.1 equiv.). The reaction mixture was then allowed to warm to room temperature and stirred overnight. The reaction mixture was then concentrated and used without further purification. ES/MS: m/z=241.5 [M+H]$^+$.

General Procedure LXIX-E for Intermediates Ebr:

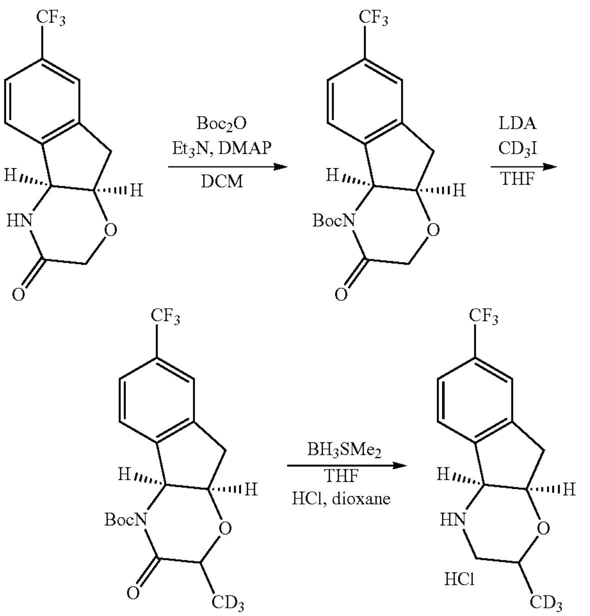

Ebr-1

Step 1: tert-butyl (4aS,9aR)-3-oxo-7-(trifluoromethyl)-2,3,9,9a-tetrahydroindeno[2,1-b][1,4]oxazine-4(4aH)-carboxylate. To a solution of (4aS,9aR)-7-(trifluoromethyl)-4,4a,9,9a-tetrahydroindeno[2,1-b][1,4]oxazin-3(2H)-one (prepared following general procedure XX-E, 80 mg, 0.3 mmol) in DCM (2 mL) was added tert-butoxycarbonyl tert-butyl carbonate (75 mg, 0.34 mmol), triethylamine (0.04 mL, 0.31 mmol) and DMAP (19 mg, 0.16 mmol). The mixture was stirred at rt overnight and then concentrated and purified by flash column to give the title compound. ES/MS: m/z=302.0 [M-tBu+H]$^+$.

Step 2: tert-butyl (4aS,9aR)-2-(methyl-d3)-3-oxo-7-(trifluoromethyl)-2,3,9,9a-tetrahydroindeno[2,1-b][1,4]oxazine-4(4aH)-carboxylate. To a solution of tert-butyl (4aS,9aR)-3-oxo-7-(trifluoromethyl)-2,3,9,9a-tetrahydroindeno[2,1-b][1,4]oxazine-4(4aH)-carboxylate (90 mg, 0.25 mmol) in THF (1 mL) was added lithium diisopropylamide (1 M in THF, 0.28 mL, 0.28 mmol) dropwise at −78° C. The mixture was stirred for 30 min and then added trideuterio(iodo)methane (44 mg, 0.3 mmol) at −78° C. The resulting mixture was warmed up to rt slowly and stirred overnight before being quenched by water and diluted with EtOAc. The organic layer was separated, washed with brine, dried over $MgSO_4$, filtered, and concentrated. Purification by silica gel flash column chromatography afforded the title compound as a pair of distereomers. ES/MS: m/z=319.0 [M-tBu+H]$^+$.

Step 3: (4aS,9aR)-2-(methyl-d3)-7-(trifluoromethyl)-2,3,4,4a,9,9a-hexahydroindeno[2,1-b][1,4]oxazine hydrochloride (Ebr-1). Borane dimethyl sulfide (0.16 mL, 1.7 mmol) was added to a solution of tert-butyl (4aS,9aR)-2-(methyl-d3)-3-oxo-7-(trifluoromethyl)-2,3,9,9a-tetrahydroindeno[2,1-b][1,4]oxazine-4(4aH)-carboxylate (78 mg, 0.21 mmol) in THF (1 mL). After stirring overnight at rt, MeOH (1 mL) was carefully added and the mixture was concentrated. The crude residue was suspended in 1,4-dioxane (1 mL) and HCl (4.0M in dioxane, 0.63 mL, 2.5 mmol) was added. The mixture was stirred overnight, then concentrated to afford the title compound as the hydrochloride salt. ES/MS: m/z=261.1 [M+H]$^+$.

General Procedure LXX-E for the Synthesis of Intermediates Ebs:

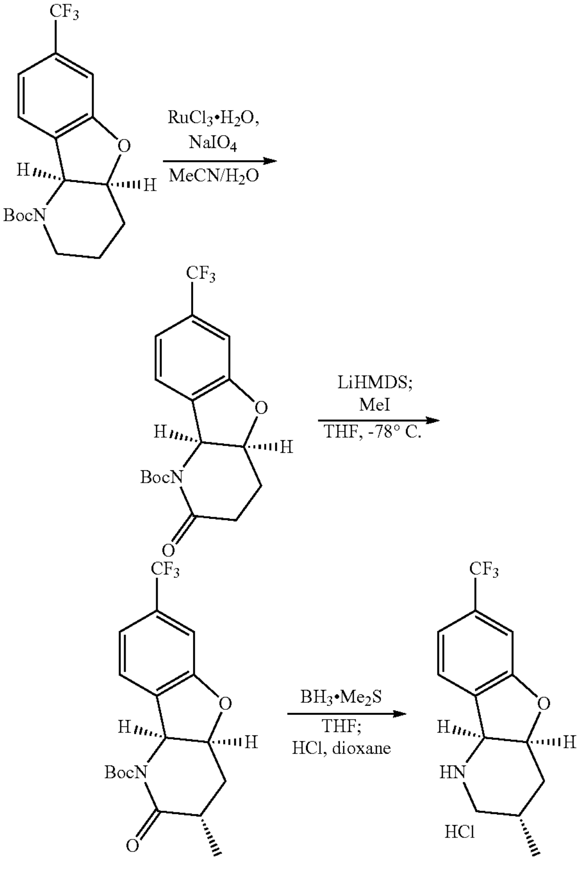

Ebs-1

Step 1. tert-butyl (4aS,9bS)-2-oxo-7-(trifluoromethyl)-3,4,4a,9b-tetrahydrobenzofuro[3,2-b]pyridine-1-carboxylate. Ruthenium (III) chloride hydrate (13 mg, 0.06 mmol) was added to a solution of Sodium periodate (934 mg, 4.4 mol)

in $H_2O$ (18 mL). The resulting mixture was added to a solution of tert-butyl (4aS,9bS)-7-(trifluoromethyl)-3,4,4a,9b-tetrahydro-2H-benzofuro[3,2-b]pyridine-1-carboxylate (Prepared according to general procedure XXIII-E) (500 mg, 1.5 mmol) in acetonitrile (6 mL). The mixture was stirred overnight before being diluted with EtOAc. The organic layer was separated, washed with brine, dried over $MgSO_4$, filtered, and concentrated. Purification by silica gel flash column chromatography afforded tert-butyl (4aS,9bS)-2-oxo-7-(trifluoromethyl)-3,4,4a,9b-tetrahydrobenzofuro[3,2-b]pyridine-1-carboxylate. ES/MS: m/z=257.9 $[M-Boc+H]^+$. $^1H$ NMR (400 MHz, Chloroform-d) δ 7.55 (d, J=7.9 Hz, 1H), 7.16 (d, J=7.8 Hz, 1H), 7.04 (s, 1H), 6.04 (d, J=9.8 Hz, 1H), 5.32-5.20 (m, 1H), 2.57-2.46 (m, 1H), 2.43-2.27 (m, 2H), 2.15-1.98 (m, 1H), 1.59 (s, 9H).

Step 2. tert-butyl (3S,4aS,9bS)-3-methyl-2-oxo-7-(trifluoromethyl)-3,4,4a,9b-tetrahydrobenzofuro[3,2-b]pyridine-1(2H)-carboxylate. LiHMDS (1.0 M in THF, 0.24 mL, 0.24 mmol) was slowly added to a solution of tert-butyl (4aS,9bS)-2-oxo-7-(trifluoromethyl)-3,4,4a,9b-tetrahydrobenzofuro[3,2-b]pyridine-1-carboxylate (70 mg, 0.20 mmol) in THF (2 mL) at −78° C. After 30 minutes, MeI (0.012 mL, 0.20 mmol) was added and the mixture was allowed to slowly warm to room temperature and stir overnight. Sat. aq. $NaHCO_3$ was added and the mixture was diluted with EtOAc. The organic layer was separated, washed with brine, dried over $MgSO_4$, filtered, and concentrated. Purification by silica gel flash column chromatography afforded tert-butyl (3S,4aS,9bS)-3-methyl-2-oxo-7-(trifluoromethyl)-3,4,4a,9b-tetrahydrobenzofuro[3,2-b]pyridine-1(2H)-carboxylate. ES/MS: m/z=271.9 $[M-Boc+H]^+$.

Step 3. (3S,4aS,9bS)-3-methyl-7-(trifluoromethyl)-1,2,3,4,4a,9b-hexahydrobenzofuro[3,2-b]pyridine hydrochloride (Ebs-1). Borane dimethyl sulfide complex (0.08 mL, 0.86 mmol) was added to a solution of tert-butyl (3S,4aS,9bS)-3-methyl-2-oxo-7-(trifluoromethyl)-3,4,4a,9b-tetrahydrobenzofuro[3,2-b]pyridine-1(2H)-carboxylate (40 mg, 0.11 mmol) in THF (2 mL). After stirring overnight at 40° C., MeOH (1 mL) was carefully added and the mixture was concentrated. The crude residue was suspended in 1,4-dioxane (1 mL) and HCl (4.0 M in dioxane, 0.2 mL, 0.8 mmol) was added. The mixture was stirred overnight, then concentrated to afford (3S,4aS,9bS)-3-methyl-7-(trifluoromethyl)-1,2,3,4,4a,9b-hexahydrobenzofuro[3,2-b]pyridine as the hydrochloride salt. ES/MS: m/z=257.9 $[M+H]^+$.

Ebs-2

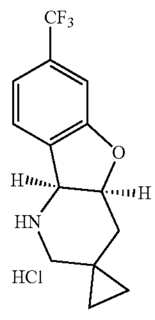

(4aS,9bS)-7-(trifluoromethyl)-1,4,4a,9b-tetrahydro-2H-spiro[benzofuro[3,2-b]pyridine-3,1'-cyclopropane]hydrochloride (Ebs-2). Prepared following general procedure LXX-E using (2-Bromoethyl)diphenylsulfonium trifluoromethanesulfonate instead of iodomethane as the electrophile. ES/MS: m/z=269.9 $[M+H]^+$.

Ebs-3

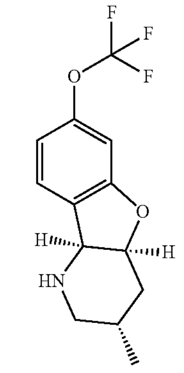

(3S,4aS,9bS)-3-methyl-7-(trifluoromethoxy)-1,2,3,4,4a,9b-hexahydrobenzofuro[3,2-b]pyridine (Ebs-3). Prepared according to general procedure LXX-E starting with tert-butyl (3S,4aS,9bS)-3-methyl-7-(trifluoromethoxy)-3,4,4a,9b-tetrahydrobenzofuro[3,2-b]pyridine-1(2H)-carboxylate (Prepared according to general procedure XXIII-E) and methyl iodide. ES/MS: m/z=274.1 $[M+H]^+$.

Ebs-4

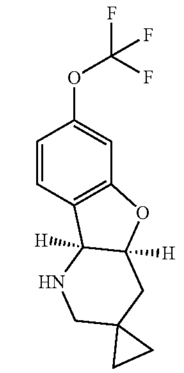

(4aS,9bS)-7-(trifluoromethoxy)-1,4,4a,9b-tetrahydro-2H-spiro[benzofuro[3,2-b]pyridine-3,1'-cyclopropane] (Ebs-4). Prepared according to general procedure LXX-E starting with tert-butyl (3S,4aS,9bS)-3-methyl-7-(trifluoromethoxy)-3,4,4a,9b-tetrahydrobenzofuro[3,2-b]pyridine-1(2H)-carboxylate (prepared according to general procedure XXIII-E) and (2-Bromoethyl)diphenylsulfonium trifluoromethanesulfonate instead of iodomethane. ES/MS: m/z=285.9 $[M+H]^+$.

General Procedure LXXI-E for the Synthesis of Intermediates Ebt:

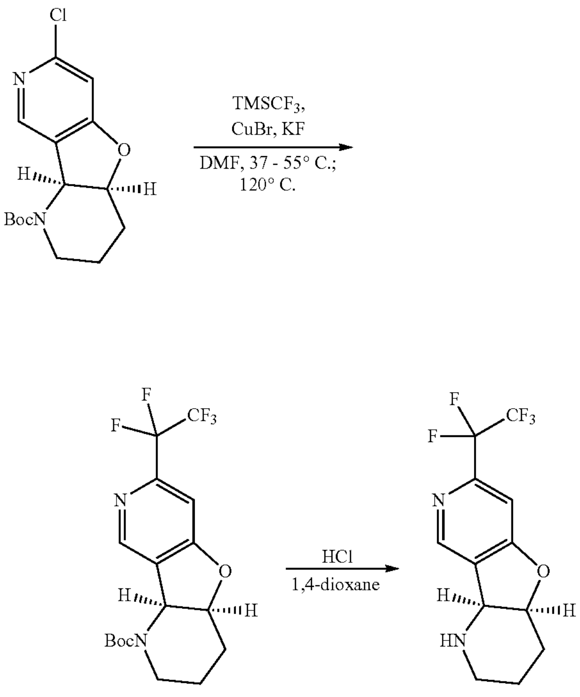

Ebt-1

Step 1. tert-butyl (4aS,9bS)-7-(perfluoroethyl)-3,4,4a,9b-tetrahydrofuro[3,2-b:4,5-c']dipyridine-1(2H)-carboxylate. A mixture of KF (100 mg, 1.72 mmol) and CuBr (309 mg, 2.15 mmol) were dried under vacuum at 80° C. for 3 hours. After cooling to room temperature and purging with argon, DMF (4.3 mL) was added and the mixture was stirred for 10 minutes before $TMSCF_3$ (0.25 mL, 1.72 mmol) was added dropwise. The mixture was warmed to 37° C. for 15 hours, then warmed to 55° C. for an additional 6 hours. Stirring was stopped and the solids were allowed to settle at room temperature. The supernatant (~0.4M, 3 mL, 1.2 mmol) was transferred via syringe to an argon flushed vessel containing tert-butyl (4aS,9bS)-7-chloro-3,4,4a,9b-tetrahydrofuro[3,2-b:4,5-c']dipyridine-1(2H)-carboxylate (prepared according to general procedure XXIII-E starting with 5-bromo-2,4-dichloro-pyridine) (90 mg, 0.29 mmol). The mixture was heated, with stirring, to 120° C. overnight. After cooling to room temperature, the mixture was diluted with EtOAc and washed with 10% aq. LiCl followed by brine. The organic layer was dried over $MgSO_4$, filtered and concentrated. Purification by silica gel flash column chromatography afforded tert-butyl (4aS,9bS)-7-(perfluoroethyl)-3,4,4a,9b-tetrahydrofuro[3,2-b:4,5-c']dipyridine-1(2H)-carboxylate. ES/MS: m/z=394.9 $[M+H]^+$.

Step 2. (4aS,9bS)-7-(perfluoroethyl)-1,2,3,4,4a,9b-hexahydrofuro[3,2-b:4,5-c']dipyridine hydrochloride (Ebt-1). Tert-butyl (4aS,9bS)-7-(perfluoroethyl)-3,4,4a,9b-tetrahydrofuro[3,2-b:4,5-c']dipyridine-1(2H)-carboxylate (40 mg, 0.1 mmol) was suspended in 1,4-dioxane (1 mL) and HCl (4.0 M in dioxane, 1.0 mL, 4.0 mmol) was added. The mixture was stirred for three hours, then concentrated to afford (4aS,9bS)-7-(perfluoroethyl)-1,2,3,4,4a,9b-hexahydrofuro[3,2-b:4,5-c']dipyridine as the hydrochloride salt. ES/MS: m/z=294.9 $[M+H]^+$.

General Procedure LXXII-E for the Synthesis of Intermediates Ebu:

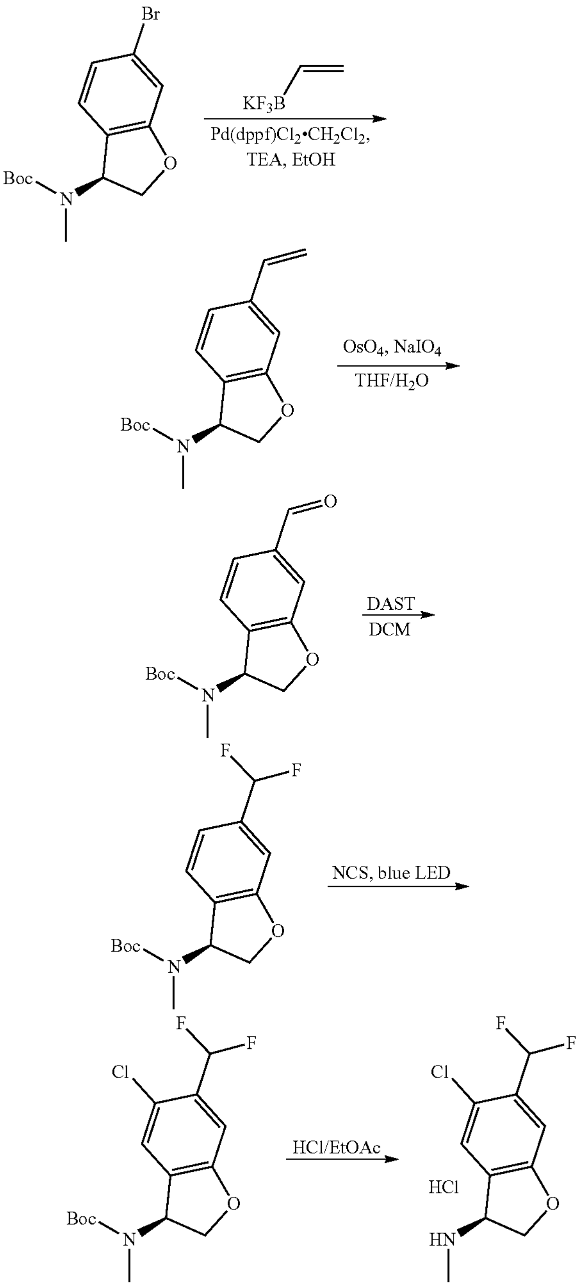

Ebu-1

Step 1. tert-butyl (S)-methyl(6-vinyl-2,3-dihydrobenzofuran-3-yl)carbamate. A mixture of tert-butyl N-[(3S)-6-bromo-2,3-dihydrobenzofuran-3-yl]-N-methyl-carbamate (5.0 g, 15.2 mmol), Potassium Vinyltrifluoroborate (2.5 g, 18.3 mmol), Triethylamine (4.6 g, 45.7 mmol), 1,1'-Bis (diphenylphosphino)ferrocene-palladium(II)dichloride dichloromethane complex (0.13 g, 0.152 mmol) in ethanol (50.0 mL) was degassed and purged with $N_2$ for 3 times, the mixture was then stirred at 85° C. for 12 hrs under $N_2$ atmosphere. The reaction mixture was concentrated under reduced pressure to remove solvent. The residue was diluted with water 100 mL and extracted with Ethyl acetate 150 mL (50 mL×3). The combined organic layers were washed with brine 150 mL (50 mL×3), dried over $Na_2SO_4$, filtered and concentrated under reduced pressure to give a residue. The residue was purified by flash silica gel chromatography to give desired product. ES/MS: m/z=220.2 $[M-tBu+H]^+$. $^1H$ NMR (400 MHz, $CDCl_3$) δ 7.19 (br d, J=7.5 Hz, 1H), 6.97 (dd, J=1.1, 7.7 Hz, 1H), 6.91 (s, 1H), 6.69 (dd, J=10.8, 17.6 Hz, 1H), 6.14-5.80 (m, 1H), 5.74 (d, J=17.5 Hz, 1H), 5.26 (d, J=10.9 Hz, 1H), 4.62 (br t, J=9.3 Hz, 1H), 4.38 (br dd, J=3.2, 9.9 Hz, 1H), 2.55 (br s, 3H), 1.51 (s, 9H).

Step 2. tert-butyl (S)-(6-formyl-2,3-dihydrobenzofuran-3-yl)(methyl)carbamate. To a solution of tert-butyl (S)-methyl (6-vinyl-2,3-dihydrobenzofuran-3-yl)carbamate (3.8 g, 13.8 mmol) in tetrahydrofuran (70.0 mL) and water (21.0 mL) was added periodyloxysodium (8.9 g, 41.4 mmol) and tetraoxoosmium (0.1 g, 0.276 mmol). The mixture was stirred at 25° C. for 2 hrs. The reaction mixture was partitioned between water 100 mL and Ethyl acetate 300 mL (100 mL×3). The organic phase was separated, washed with brine 300 mL (100 mL×3), dried over $Na_2SO_4$, filtered and concentrated under reduced pressure to give a residue. The residue was purified by flash silica gel chromatography to give desired product. ES/MS: m/z=222.1 $[M-tBu+H]^+$. $^1H$ NMR (400 MHz, $CDCl_3$) δ 9.97 (s, 1H), 7.51-7.45 (m, 1H), 7.40 (br d, J=7.5 Hz, 1H), 7.33 (s, 1H), 6.23-5.77 (m, 1H), 4.76-4.62 (m, 1H), 4.45 (br d, J=5.8 Hz, 1H), 2.56 (br s, 3H), 1.50 (s, 9H).

Step 3. tert-butyl (S)-(6-(difluoromethyl)-2,3-dihydrobenzofuran-3-yl)(methyl)carbamate. To a solution of tert-butyl (S)-(6-formyl-2,3-dihydrobenzofuran-3-yl)(methyl) carbamate (1.0 g, 3.61 mmol) in dichloromethane (10.0 mL) was added diethylaminosulfur trifluoride (2.9 g, 18.0 mmol) at 0° C. The mixture was stirred at 25° C. for 3 hrs. The reaction mixture was partitioned between water 5 mL and Ethyl acetate 15 mL (5 mL×3). The organic phase was separated, washed with brine 15 mL (5 mL×3), dried over $Na_2SO_4$, filtered and concentrated under reduced pressure to give a residue. The residue was purified by flash silica gel chromatography to give desired product. ES/MS: m/z=244.2 $[M-tBu+H]^+$. $^1H$ NMR (400 MHz, $CDCl_3$) δ 7.31 (br d, J=7.3 Hz, 1H), 7.07 (d, J=7.6 Hz, 1H), 6.99 (s, 1H), 6.61 (t, J=56.4 Hz, 1H), 6.17-5.73 (m, 1H), 4.66 (br t, J=9.6 Hz, 1H), 4.42 (br d, J=6.9 Hz, 1H), 2.55 (br s, 3H), 1.50 (s, 9H).

Step 4. tert-butyl (S)-(5-chloro-6-(difluoromethyl)-2,3-dihydrobenzofuran-3-yl)(methyl)carbamate. To a solution of tert-butyl N-[(3S)-6-(difluoromethyl)-2,3-dihydrobenzofuran-3-yl]-N-methyl-carbamate (0.800 g, 0.00267 mol) in Acetonitrile (10.0 mL) was added N-Chlorosuccinimide (0.464 g, 3.47 mmol). The mixture was stirred at 45° C. for 30 min under blue light (hv=450 nm/24 W). The reaction mixture was concentrated under reduced pressure to remove solvent. The residue was diluted with water 5 mL and extracted with Ethyl acetate 30 mL (10 mL×3). The combined organic layers were washed with brine 30 mL (10 mL×3), dried over $Na_2SO_4$, filtered and concentrated under reduced pressure to give a residue. The residue was purified by flash silica gel chromatography to give desired product. ES/MS: m/z=278.1 $[M-tBu+H]^+$. $^1H$ NMR (400 MHz, $CD_3OD$) δ 7.34 (s, 1H), 7.14-6.81 (m, 2H), 6.12-5.65 (m, 1H), 4.75-4.64 (m, 1H), 4.52 (br dd, J=4.3, 10.4 Hz, 1H), 2.63 (br s, 3H), 1.47 (br s, 9H).

Step 5. (S)-5-chloro-6-(difluoromethyl)-N-methyl-2,3-dihydrobenzofuran-3-amine hydrochloride (Ebu-1) To a solution of tert-butyl (S)-(5-chloro-6-(difluoromethyl)-2,3-dihydrobenzofuran-3-yl)(methyl)carbamate (0.4 g, 1.17 mmol) in HCl/Ethyl acetate (3.0 mL) (4M). The mixture was stirred at 25° C. for 0.5 hr. The reaction mixture was concentrated under reduced pressure to remove solvent. The residue was passed through a syringe filter and the filtrate was purified by prep-HPLC (HCl condition column: Phenomenex luna C18 100*40 mm*5 um; mobile phase: [A: $H_2O$ (0.04% HCl);B: ACN];B %: 1.00%-25.00%, 8.00 min) to give desired product as HCl salt. ES/MS: m/z=234.1 $[M+H]^+$. $^1H$ NMR (400 MHz, DMSO-d6) δ 9.64 (br s, 2H), 7.93 (br s, 1H), 7.34-7.03 (m, 2H), 5.12 (br d, J=6.0 Hz, 1H), 4.92-4.82 (m, 1H), 4.80-4.69 (m, 1H), 2.54 (s, 3H).

General Procedure LXXIII-E for the Synthesis of Intermediates Ebv:

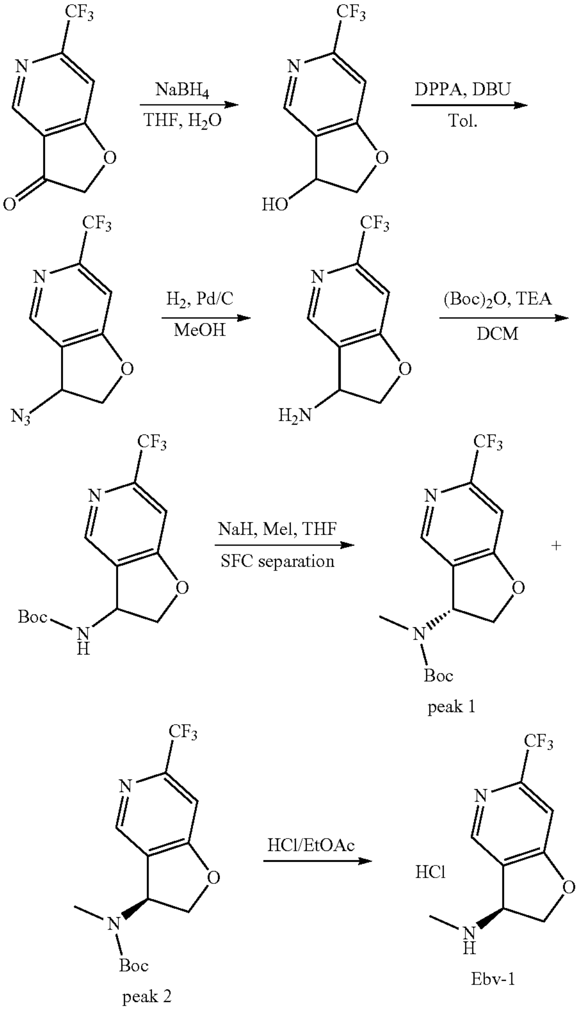

Step 1. 6-(trifluoromethyl)-2,3-dihydrofuro[3,2-c]pyridin-3-ol. Sodium borohydride (2.8 g, 75.8 mmol) was added to a solution of 6-(trifluoromethyl)furo[3,2-c]pyridin-3(2H)-one (3.8 g, 19.0 mol) in 82 mL THF and 40 mL $H_2O$ at 0° C. under $N_2$. The mixture was stirred at 25° C. for 12 hr under $N_2$. The reaction mixture was quenched by addition $NH_4Cl$ 120 mL, and extracted with Ethyl acetate 600 mL (200 mL×3). The combined organic layers were washed with brine 600 mL (200 mL×3), dried over $Na_2SO_4$, filtered and concentrated under reduced pressure to give a residue. The residue was purified by flash silica gel chromatography to give desired product. ES/MS: m/z=206.1 $[M+H]^+$. $^1H$ NMR (400 MHz, $CDCl_3$) δ 8.55 (s, 1H), 7.20 (s, 1H), 5.55 (dd, J=2.6, 6.7 Hz, 1H), 4.76-4.70 (m, 1H), 4.65-4.60 (m, 1H), 3.12 (br s, 1H)

Step 2. 3-azido-6-(trifluoromethyl)-2,3-dihydrofuro[3,2-c]pyridine. To a solution of 6-(trifluoromethyl)-2,3-dihydrofuro[3,2-c]pyridin-3-ol (2.2 g, 10.8 mmol) in toluene (20.0 mL) cooled to 0° C. was added Diphenylphosphoryl azide, 98% (3.5 g, 13.0 mmol) under $N_2$ atmosphere. Then 1,8-Diazabicyclo[5.4.0]undec-7-ene (2.4 g, 16.2 mmol) in toluene (6.00 mL) was added to the solution at 0° C. under $N_2$ atmosphere. The mixture was stirred at 25° C. for 12 hr under $N_2$ atmosphere. The reaction mixture was diluted with $H_2O$ 400 mL and extracted with Ethyl acetate 1200 mL (400 mL×3). The combined organic layers were washed with brine 600 mL (200 mL×3), dried over $Na_2SO_4$, filtered and concentrated under reduced pressure to give desired product, which was used into the next step without further purification. ES/MS: m/z=230.9 $[M+H]^+$.

Step 3. 6-(trifluoromethyl)-2,3-dihydrofuro[3,2-c]pyridin-3-amine. To a solution of Pd/C (10.0%, 1.0 g, 0.94 mmol) in methanol (10.0 mL) was added 3-azido-6-(trifluoromethyl)-2,3-dihydrofuro[3,2-c]pyridine (60.0%, 3.5 g, 9.1 mmol) in methanol (20.0 mL) under $N_2$ atmosphere. The suspension was degassed and purged with $H_2$ for 3 times. The mixture was stirred under $H_2$ (15 psi.) at 25° C. for 6 hr. The reaction mixture was filtered and concentrated under reduced pressure to give desired product, which was used into the next step without further purification. ES/MS: m/z=205.1 $[M+H]^+$. $^1H$ NMR (400 MHz, DMSO-$d_6$) δ 8.58 (br s, 1H), 7.37 (br d, J=2.6 Hz, 1H), 4.85-4.69 (m, 2H), 4.28 (br dd, J=4.8, 8.8 Hz, 1H)

Step 4. tert-butyl (6-(trifluoromethyl)-2,3-dihydrofuro[3,2-c]pyridin-3-yl)carbamate. To a solution of 6-(trifluoromethyl)-2,3-dihydrofuro[3,2-c]pyridin-3-amine (53.8%, 2.7 g, 7.3 mmol) in dichloromethane (27.0 mL) was added Triethylamine (1.4 g, 14.7 mmol) and Di-tert-butyl dicarbonate (98.0%, 1.4 g, 6.5 mmol). The mixture was stirred at 25° C. for 12 hr. The reaction mixture was concentrated under reduced pressure to give a residue. The residue was purified by flash silica gel chromatography to give desired product. ES/MS: m/z=305.3 $[M+H]^+$. $^1H$ NMR (400 MHz, $CDCl_3$) δ 8.61 (s, 1H), 7.17 (s, 1H), 5.51 (br s, 1H), 4.97 (br s, 1H), 4.89-4.80 (m, 1H), 4.53 (dd, J=4.4, 10.4 Hz, 1H), 1.47 (s, 9H)

Step 5. tert-butyl (R)-methyl(6-(trifluoromethyl)-2,3-dihydrofuro[3,2-c]pyridin-3-yl)carbamate & tert-butyl (S)-methyl(6-(trifluoromethyl)-2,3-dihydrofuro[3,2-c]pyridin-3-yl)carbamate. To a solution of tert-butyl (6-(trifluoromethyl)-2,3-dihydrofuro[3,2-c]pyridin-3-yl) carbamate (1.4 g, 4.6 mmol) in Tetrahydrofuran (28.0 mL) was added Sodium hydride (60.0%, 0.3 g, 9.2 mmol) at 0° C. under $N_2$ atmosphere. The mixture was stirred at 0° C. for 30 min. Then iodomethane (0.7 g, 5.1 mmol) was added to the solution at 0° C. The mixture was stirred at 25° C. for 12 hr. LC-MS showed the desired mass was detected and TLC indicated the reactant 8 was consumed completely and one new spot formed. The reaction mixture was quenched by addition $NH_4Cl$ 30 mL at 0° C., and then the reaction mixture was extracted with Ethyl acetate 90 mL (30 mL×3). The combined organic layers were washed with brine 60 mL (20 mL×3), dried over $Na_2SO_4$, filtered and concentrated under reduced pressure to give a residue. The residue was purified by flash silica gel chromatography (20 g Silica Flash Column, Eluent of 0~15% Ethyl acetate/Petroleum ether gradient @ 80 mL/min), which was further separated by prep-SFC (column: REGIS(S,S)WHELK-O1 (250 mm*25 mm, 10 um); mobile phase: [A: $CO_2$;B: IPA (0.1% $NH_3H_2O$)];B %: 23.00%-23.00%, 4.00 min) to give tert-butyl (R)-methyl(6-(trifluoromethyl)-2,3-dihydrofuro[3,2-c]pyridin-3-yl)carbamate as peak 1 (RT=0.756 min, ee %: 98.18%) and tert-butyl (S)-methyl(6-(trifluoromethyl)-2,3-dihydrofuro[3,2-c]pyridin-3-yl)carbamate as peak 2 (RT=0.896 min, ee %: 95.32)

tert-butyl (R)-methyl(6-(trifluoromethyl)-2,3-dihydrofuro[3,2-c]pyridin-3-yl)carbamate (peak 1, RT=0.756 min, ee %: 98.18%) ES/MS: m/z=318.9 $[M+H]^+$. $^1H$ NMR (400 MHz, $CDCl_3$) δ 8.50 (s, 1H), 7.18 (s, 1H), 6.29-5.77 (m, 1H), 4.78 (t, J=9.9 Hz, 1H), 4.61-4.51 (m, 1H), 2.60 (br s, 3H), 1.50 (s, 9H)

tert-butyl (S)-methyl(6-(trifluoromethyl)-2,3-dihydrofuro[3,2-c]pyridin-3-yl)carbamate as (peak 2, RT=0.896 min, ee %: 95.32) ES/MS: m/z=318.9 $[M+H]^+$. $^1H$ NMR (400 MHz, $CDCl_3$) δ 8.50 (s, 1H), 7.18 (s, 1H), 6.29-5.79 (m, 1H), 4.78 (t, J=9.9 Hz, 1H), 4.62-4.49 (m, 1H), 2.60 (br s, 3H), 1.50 (s, 9H)

Step 6. (S)—N-methyl-6-(trifluoromethyl)-2,3-dihydrofuro[3,2-c]pyridin-3-amine hydrochloride (Ebv-1). Tert-butyl (S)-methyl(6-(trifluoromethyl)-2,3-dihydrofuro[3,2-c]pyridin-3-yl)carbamate (380 mg, 1.08 mmol) in hydrochloric acid/Ethyl acetate (4.0 mol/L, 4.4 mL). The mixture was stirred at 25° C. for 2 hr. The mixture was concentrated and purified by prep-HPLC (neutral condition; column: Waters Xbridge Prep OBD C18 150*40 mm*10 um; mobile phase: [A: $H_2O$(10 mM $NH_4HCO_3$);B: ACN];B %: 10.00%-40.00%, 8.00 min to give a residue. Then the residue was passed through a syringe filter and the filtrate was purified by prep-HPLC (HCl condition; column: Phenomenex luna C18 100*40 mm*5 um; mobile phase: [A: $H_2O$(0.04% HCl);B: ACN];B %: 1.00%-15.00%, 8.00 min) to give desired product. ES/MS: m/z=219.1 $[M+H]^+$. $^1H$ NMR (400 MHz, DMSO-$d_6$) δ 10.19 (br s, 2H), 8.99 (s, 1H), 7.60 (s, 1H), 5.25 (br d, J=2.8 Hz, 1H), 5.11-4.99 (m, 1H), 4.95-4.82 (m, 1H), 2.56 (br s, 3H).

General Procedure LXXIV-E for the Synthesis of Intermediates Ebw

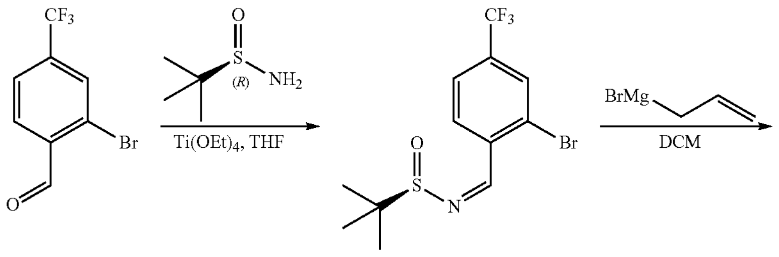

-continued

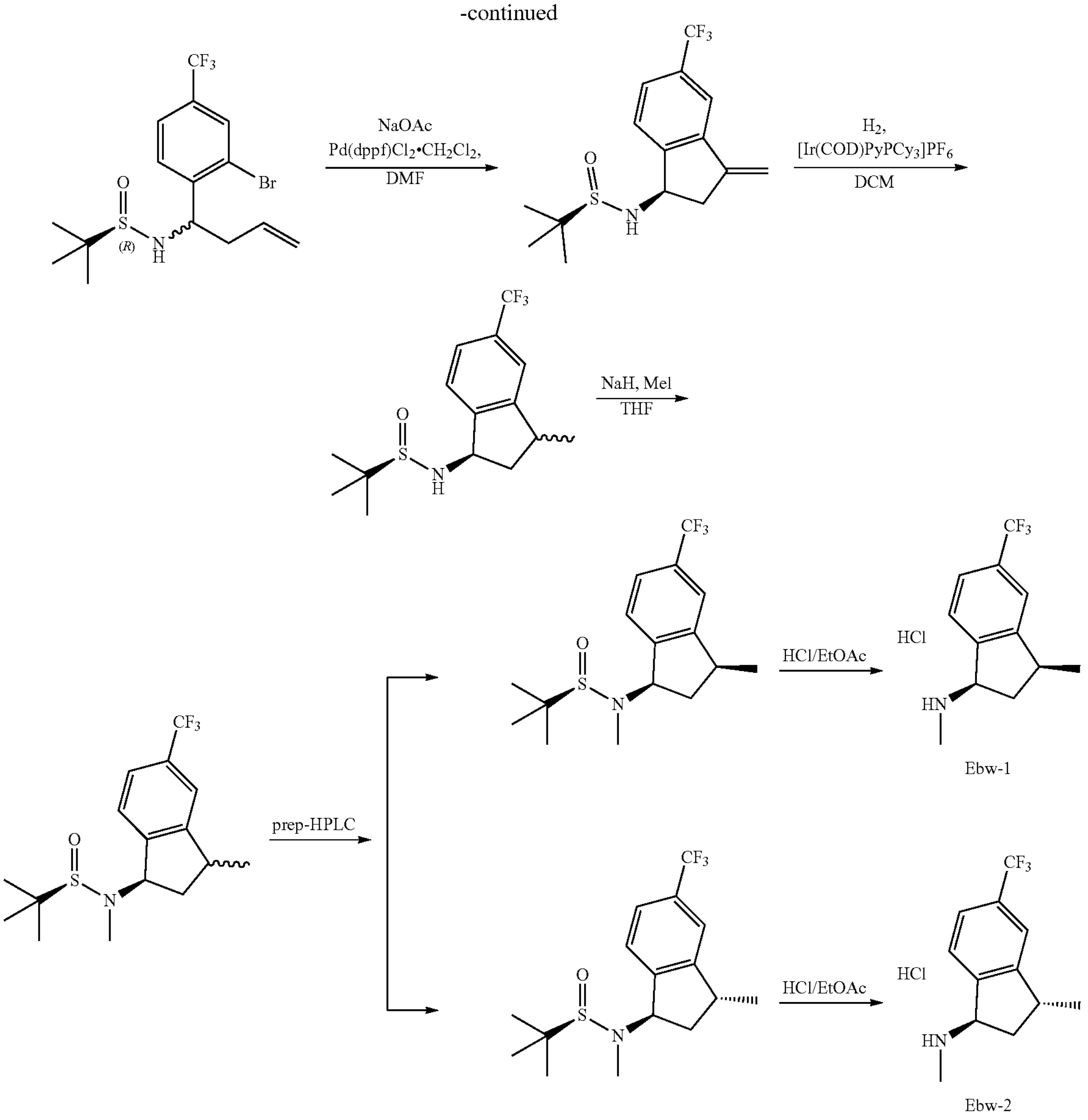

Step 1. (R,Z)—N-(2-bromo-4-(trifluoromethyl)benzylidene)-2-methylpropane-2-sulfinamide.

To a solution of 2-bromo-4-(trifluoromethyl)benzaldehyde (10.0 g, 39.5 mmol) in tetrahydrofuran (100 mL) was added (R)-2-methylpropane-2-sulfinamide (7.1 g, 59.3 mmol) and Titanium(IV) ethoxide (18.0 g, 79.0 mmol). The mixture was stirred at 70° C. for 12 hr. The reaction mixture was quenched by $H_2O$ 200 mL and EtOAc 200 mL. The suspension was filtered through a pad of Celite and the pad was washed with $H_2O$ (100 mL×3). The filtrate was collected and was partitioned between $H_2O$ 100 mL and EtOAc 600 mL. The organic phase was separated, washed with brine (100 mL×3), dried over $Na_2SO_4$, filtered and concentrated under reduced pressure to give desired product, which was used into the next step without further purification. ES/MS: m/z=355.8 $[M+H]^+$. $^1$H NMR (400 MHz, $CDCl_3$) δ 8.99 (s, 1H), 8.15 (d, J=8.3 Hz, 1H), 7.92 (s, 1H), 7.65 (d, J=8.1 Hz, 1H), 1.29 (s, 9H).

Step 2. (R)—N—((R)-1-(2-bromo-4-(trifluoromethyl)phenyl)but-3-en-1-yl)-2-methylpropane-2-sulfinamide. To a solution of (R,Z)—N-(2-bromo-4-(trifluoromethyl)benzylidene)-2-methylpropane-2-sulfinamide (16.0 g, 44.9 mmol) in dichloromethane (150 mL) was added allyl(bromo)magnesium (1.00 mol/L, 89.8 mL, 89.8 mmol) at −78° C. under $N_2$. The mixture was stirred at 25° C. for 12 hr under $N_2$. The reaction mixture was partitioned between $NH_4Cl$ 300 mL and Ethyl acetate 900 mL (300 mL×3). The organic phase was separated, washed with brine 900 mL (300 mL×3), dried over $Na_2SO_4$, filtered and concentrated under reduced pressure to give a residue. The residue was purified by flash silica gel chromatography to give desired product. ES/MS: m/z=397.9 $[M+H]^+$. $^1$H NMR (400 MHz, $CDCl_3$) δ 7.83 (s, 1H), 7.59-7.52 (m, 2H), 5.82-5.68 (m, 1H), 5.25 (s, 1H), 5.23-5.19 (m, 1H), 5.06-4.99 (m, 1H), 2.77-2.66 (m, 1H), 2.51-2.36 (m, 1H), 1.23-1.21 (m, 9H)

Step 3. (R)-2-methyl-N—((R)-3-methylene-5-(trifluoromethyl)-2,3-dihydro-1H-inden-1-yl)propane-2-sulfinamide. To a solution of (R)—N—((R)-1-(2-bromo-4-(trifluoromethyl)phenyl)but-3-en-1-yl)-2-methylpropane-2-sulfinamide (5.0 g, 12.6 mmol) in N,N-dimethylformamide (100 mL) was added sodium acetate (3.0 g, 37.7 mmol) and 1,1'-Bis(diphenylphosphino)ferrocene-palladium(II)dichloride dichloromethane complex (1.0 g, 1.2 mmol). The mixture was stirred at 100° C. for 5 hr under $N_2$. The reaction mixture was quenched by $H_2O$ 200 mL and EtOAc 200 mL. The suspension was filtered through a pad of Celite and the pad was washed with $H_2O$ (100 mL×3). The filtrate was collected and was partitioned between $H_2O$ 100 mL and EtOAc 600 mL. The organic phase was separated, washed with brine (100 mL×3), dried over $Na_2SO_4$, filtered and concentrated under reduced pressure to give a residue. The residue was purified by flash silica gel chromatography to give desired product. ES/MS: m/z=318.2 $[M+H]^+$. $^1H$ NMR (400 MHz, DMSO-$d_6$) δ 7.96 (s, 1H), 7.84 (d, J=8.0 Hz, 1H), 7.68 (d, J=8.0 Hz, 1H), 6.04 (d, J=8.6 Hz, 1H), 5.77 (t, J=2.1 Hz, 1H), 5.17 (s, 1H), 4.89 (q, J=8.0 Hz, 1H), 3.18 (dd, J=8.3, 16.6 Hz, 1H), 2.74 (tdd, J=2.9, 6.2, 16.7 Hz, 1H), 1.17-1.14 (m, 9H)

Step 4. (R)-2-methyl-N-((1R)-3-methyl-5-(trifluoromethyl)-2,3-dihydro-1H-inden-1-yl)propane-2-sulfinamide. To a solution of (R)-2-methyl-N-[(1R)-3-methylene-5-(trifluoromethyl)indan-1-yl]propane-2-sulfinamide (1.2 g, 3.8 mmol) in dichloromethane (10.0 mL) was added (Tricyclohexylphosphine)(1,5-cyclooctadiene)(pyridine)iridium (I) hexafluorophosphate, CRABTREE'S CATALYST (268 mg, 0.3 mmol). The mixture was stirred at 25° C. for 12 hr under $H_2$ (15 PSI). The reaction mixture was concentrated under reduced pressure to remove solvent. The residue was purified by flash silica gel chromatography to give desired product. ES/MS: m/z=319.9 $[M+H]^+$. $^1H$ NMR (400 MHz, CHLOROFORM-d) δ 7.63 (d, J=7.9 Hz, 1H), 7.51 (s, 1H), 7.45 (s, 1H), 4.97 (q, J=5.8 Hz, 1H), 4.85 (q, J=8.3 Hz, 1H), 3.60 (br d, J=8.1 Hz, 1H), 2.79 (td, J=7.2, 12.7 Hz, 1H), 2.35 (ddd, J=4.6, 7.6, 13.3 Hz, 1H), 1.26 (s, 3H), 1.21 (s, 9H)

Step 5. (R)—N,2-dimethyl-N-((1R,3R)-3-methyl-5-(trifluoromethyl)-2,3-dihydro-1H-inden-1-yl)propane-2-sulfinamide & (R)—N,2-dimethyl-N-((1R,3S)-3-methyl-5-(trifluoromethyl)-2,3-dihydro-1H-inden-1-yl)propane-2-sulfinamide. To a solution of (R)-2-methyl-N-((1R)-3-methyl-5-(trifluoromethyl)-2,3-dihydro-1H-inden-1-yl) propane-2-sulfinamide (1.0 g, 3.1 mmol) in tetrahydrofuran (20.0 mL) was added sodium hydride (60.0%, 250 mg, 6.2 mmol) at 0° C. The mixture was stirred at 0° C. for 30 min. iodomethane (533 mg, 3.7 mmol) was added to the mixture. The mixture was stirred at 25° C. for 12 hr. The reaction mixture was partitioned between $NH_4Cl$ 20 mL and EtOAc 20 mL. The organic phase was separated, washed with EtOAc (20 mL×3), dried over $Na_2SO_4$, filtered and concentrated under reduced pressure to give a residue. The residue was passed through a syringe filter and the filtrate was purified by prep-HPLC (basic condition; column: Waters Xbridge Prep OBD C18 150*40 mm*10 um; mobile phase: [A: $H_2O$(10 mM $NH_4HCO_3$);B: ACN];B %: 40.00%-70.00%, 8.00 min) to afford 2 diastereomers:

(R)—N,2-dimethyl-N-((1R,3S)-3-methyl-5-(trifluoromethyl)-2,3-dihydro-1H-inden-1-yl)propane-2-sulfinamide. ES/MS: m/z=334.1 $[M+H]^+$. $^1H$ NMR (400 MHz, DMSO-$d_6$) δ 7.64-7.59 (m, 2H), 7.38 (d, J=7.8 Hz, 1H), 5.02 (br t, J=8.9 Hz, 1H), 3.15-3.03 (m, 1H), 2.50-2.46 (m, 1H), 2.32 (s, 3H), 1.69 (td, J=10.4, 12.3 Hz, 1H), 1.34 (d, J=6.8 Hz, 3H), 1.16 (s, 9H)

(R)—N,2-dimethyl-N-((1R,3R)-3-methyl-5-(trifluoromethyl)-2,3-dihydro-1H-inden-1-yl)propane-2-sulfinamide. ES/MS: m/z=334.1 $[M+H]^+$. $^1H$ NMR (400 MHz, DMSO-$d_6$) δ 7.65-7.59 (m, 2H), 7.44 (d, J=7.8 Hz, 1H), 5.14 (t, J=7.5 Hz, 1H), 3.37 (dt, J=4.3, 7.4 Hz, 1H), 2.38 (ddd, J=6.9, 8.3, 13.4 Hz, 1H), 2.28 (s, 3H), 1.95 (ddd, J=4.2, 8.6, 13.2 Hz, 1H), 1.23 (d, J=7.1 Hz, 3H), 1.13 (s, 9H)

Step 6a. (1R,3S)—N,3-dimethyl-5-(trifluoromethyl)-2,3-dihydro-1H-inden-1-amine hydrochloride (Ebw-1). A mixture of (R)—N,2-dimethyl-N-((1R,3S)-3-methyl-5-(trifluoromethyl)-2,3-dihydro-1H-inden-1-yl)propane-2-sulfinamide (0.2 g, 0.6 mmol) in hydrogen chloride (4.00 mol/L in EtOAc, 2.0 mL, 4.0 mmol) was stirred at 25° C. for 1 hr. LC-MS showed Reactant 6A was consumed completely and the desired mass was detected. The reaction mixture was concentrated under reduced pressure to remove solvent. The residue was passed through a syringe filter and the filtrate was purified by prep-HPLC (HCl condition; column: Phenomenex Luna C18 100*30 mm*5 um; mobile phase: [A: $H_2O$(0.04% HCl);B: ACN];B %: 5.00%-30.00%, 8.00 min) to afford desired product. ES/MS: m/z=230.1 $[M+H]^+$. $^1H$ NMR (400 MHz, DMSO-$d_6$) δ 9.88 (br s, 1H), 9.27 (br s, 1H), 7.96 (d, J=8.0 Hz, 1H), 7.75-7.67 (m, 2H), 4.79 (q, J=7.6 Hz, 1H), 3.28-3.16 (m, 1H), 2.77 (td, J=7.6, 12.6 Hz, 1H), 2.63 (t, J=5.3 Hz, 3H), 1.67 (td, J=9.6, 12.5 Hz, 1H), 1.38 (d, J=6.8 Hz, 3H)

Step 6b. (1R,3R)—N,3-dimethyl-5-(trifluoromethyl)-2,3-dihydro-1H-inden-1-amine hydrochloride (Ebw-2). A mixture of (R)—N,2-dimethyl-N-((1R,3R)-3-methyl-5-(trifluoromethyl)-2,3-dihydro-1H-inden-1-yl)propane-2-sulfinamide (0.3 g, 0.9 mmol) in hydrogen chloride (4.00 mol/L in EtOAc, 2.0 mL, 4.0 mmol) was stirred at 25° C. for 1 hr. The reaction mixture was concentrated under reduced pressure to remove solvent. The residue was passed through a syringe filter and the filtrate was purified by prep-HPLC (HCl condition; column: Phenomenex Luna C18 100*30 mm*5 um; mobile phase: [A: $H_2O$(0.04% HCl);B: ACN];B %: 5.00%-30.00%, 8.00 min) to afford desired product. ES/MS: m/z=230.1 $[M+H]^+$. $^1H$ NMR (400 MHz, DMSO-$d_6$) δ 9.40 (br s, 2H), 7.88 (d, J=8.0 Hz, 1H), 7.77-7.65 (m, 2H), 4.77 (br d, J=3.4 Hz, 1H), 3.59-3.57 (m, 1H), 2.56 (t, J=5.4 Hz, 3H), 2.50-2.47 (m, 1H), 2.06-1.97 (m, 1H), 1.28 (d, J=7.0 Hz, 3H).

General Procedure LXXV-E for the Synthesis of Intermediates Ebx:

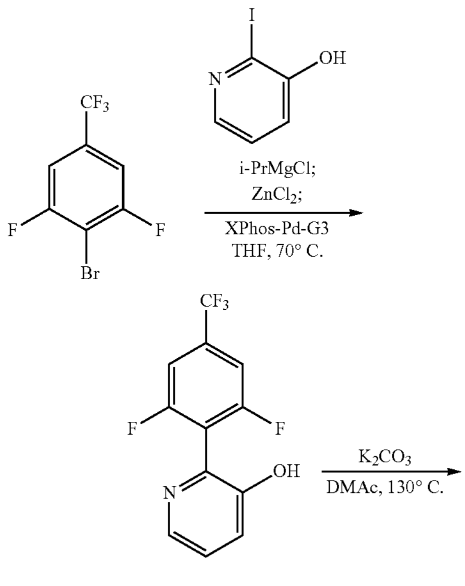

-continued

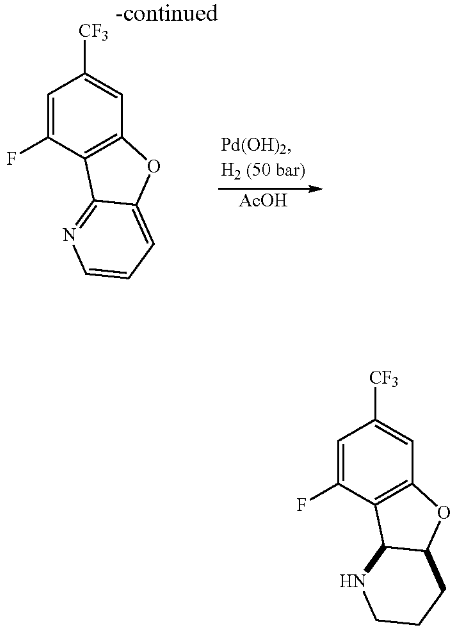

Ebx-1

Step 1. 2-[2,6-difluoro-4-(trifluoromethyl)phenyl]pyridin-3-ol. Isopropylmagnesium chloride (2.0 M in THF, 5.3 mL, 10.5 mmol) was added to a solution of 2-bromo-1,3-difluoro-5-(trifluoromethyl)benzene (2.5 g, 9.6 mmol) in THF (10 mL) at 0° C. After stirring at this temperature for one hour, zinc chloride (1.9M in 2-Me-THF, 6.1 mL, 11.5 mmol) was added and the mixture was allowed to warm to room temperature and stir for a further hour. 2-iodopyridin-3-ol (1.05 g, 4.8 mmol) and XPhos Pd-G3 (216 mg, 0.29 mmol) were then added in a single portion. The mixture was heated to 70° C. overnight, then cooled to room temperature, filtered, and concentrated. Purification of the crude residue by silica gel flash column chromatography afforded 2-[2,6-difluoro-4-(trifluoromethyl)phenyl]pyridin-3-ol. ES/MS: m/z=275.8 $[M+H]^+$.

Step 2. 9-fluoro-7-(trifluoromethyl)benzofuro[3,2-b]pyridine. Potassium carbonate (181 mg, 1.3 mmol) was added to a solution of 2-[2,6-difluoro-4-(trifluoromethyl)phenyl]pyridin-3-ol (180 mg, 0.65 mmol) in DMAc (3 mL). The mixture was heated to 130° C. for 10 minutes, then cooled to room temperature and diluted with EtOAc. The mixture was washed with 10% aq. LiCl and brine, then dried over $MgSO_4$, filtered, and concentrated. Purification of the residue by silica gel flash column chromatography afforded 9-fluoro-7-(trifluoromethyl)benzofuro[3,2-b]pyridine. ES/MS: m/z=255.8 $[M+H]^+$.

Step 3. Cis-9-fluoro-7-(trifluoromethyl)-1,2,3,4,4a,9b-hexahydrobenzofuro[3,2-b]pyridine (Ebx-1). $Pd(OH)_2/C$ (20% w/w, 220 mg, 0.31 mmol) was added to a solution of 9-fluoro-7-(trifluoromethyl)benzofuro[3,2-b]pyridine (80 mg, 0.31 mmol) in AcOH (4 mL). The mixture was shaken under 50 psi of hydrogen for 48 hours. The mixture was then filtered over celite and concentrated. The resulting residue was suspended in EtOAc and washed with sat. aq. $NaHCO_3$, dried over $MgSO_4$, filtered, and concentrated to afford crude cis-9-fluoro-7-(trifluoromethyl)-1,2,3,4,4a,9b-hexahydrobenzofuro[3,2-b]pyridine which was of suitable purity for use. ES/MS: m/z=261.9 $[M+H]^+$.

General Procedure LXXVI-E for the Synthesis of Intermediates Eby:

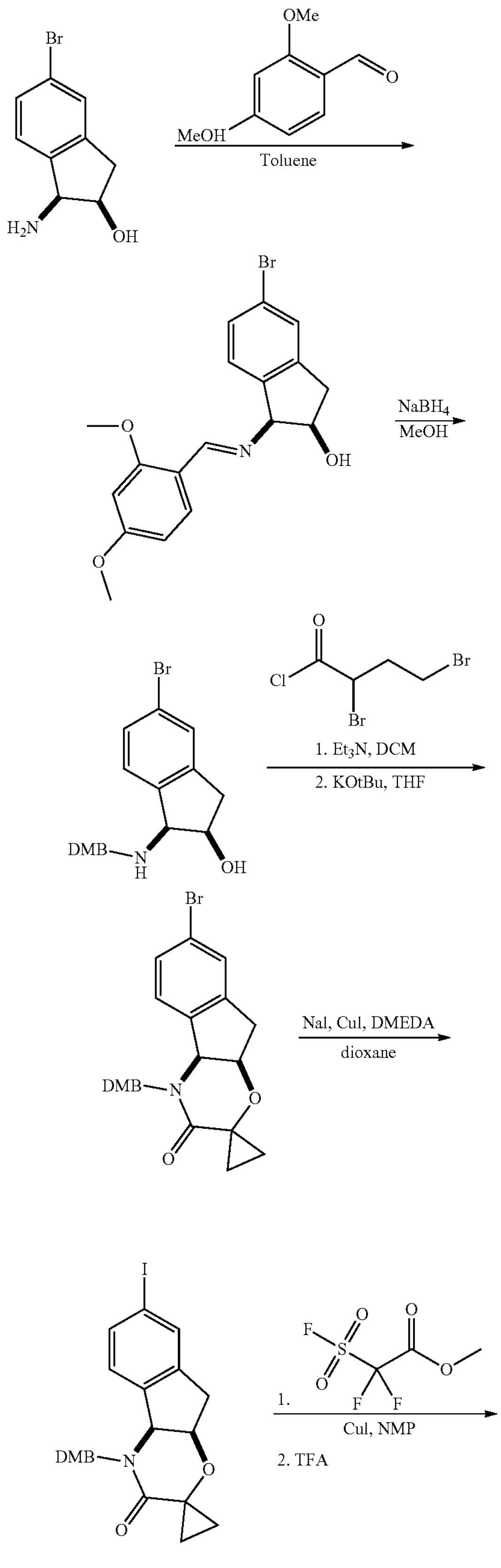

-continued

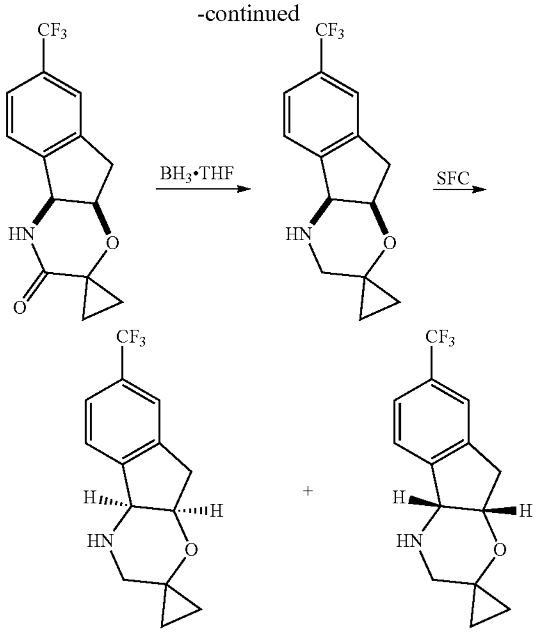

Eby-1
Peak 1

Eby-2
Peak 2

Step 1. Cis-5-bromo-1-(((E)-2,4-dimethoxybenzylidene)amino)-2,3-dihydro-1H-inden-2-ol. To a solution of cis-1-amino-5-bromo-indan-2-ol (19.0 g, 81.6 mmol) in toluene (218 mL) was added 2,4-dimethoxybenzaldehyde (13.6 g, 81.6 mmol). The reaction was stirred at 100° C. for 6 hours. The mixture was concentrated under reduced pressure to give the crude product which was used into the next step without further purification. ES/MS: m/z=375.8, 377.8 $[M+H]^+$.

Step 2. Cis-5-bromo-1-((3,4-dimethylbenzyl)amino)-2,3-dihydro-1H-inden-2-ol. To a solution of cis-5-bromo-1-(((E)-2,4-dimethoxybenzylidene)amino)-2,3-dihydro-1H-inden-2-ol (30.7 g, 81.6 mmol) in MeOH (318 mL) was added $NaBH_4$ (6.7 g, 180 mmol) at 0° C. under $N_2$ atmosphere. The reaction was stirred at 25° C. for 2 hours under $N_2$ atmosphere. The mixture was quenched by addition $NH_4Cl$ (500 mL), and then extracted with Ethyl acetate (500 mL×3). The combined organic layers were washed with brine (300 mL×3), dried over $Na_2SO_4$, filtered and concentrated under reduced pressure to give a residue. The residue was triturated with MTBE (60 mL) at 25° C. for 1 hour. The residue was filtered, washed with MTBE (20 mL) and then the filter cake was dried under reduced pressure to give the desired product. ES/MS: m/z=377.9, 379.8 $[M+H]^+$. $^1H$ NMR (400 MHz, $CDCl_3$) δ 7.36 (s, 1H), 7.29 (d, J=8.0 Hz, 1H), 7.17 (d, J=8.1 Hz, 1H), 6.91 (d, J=8.0 Hz, 1H), 6.51 (d, J=2.3 Hz, 1H), 6.46 (dd, J=2.3, 8.1 Hz, 1H), 4.43 (dt, J=2.6, 4.9 Hz, 1H), 4.05 (d, J=5.0 Hz, 1H), 3.99 (d, J=13.0 Hz, 1H), 3.86 (s, 3H), 3.82 (s, 3H), 3.77 (d, J=13.0 Hz, 1H), 3.02-2.97 (m, 2H).

Step 3. Cis-7'-bromo-4'-(3,4-dimethylbenzyl)-4',4a',9',9a'-tetrahydro-3'H-spiro[cyclopropane-1,2'-indeno[2,1-b][1,4]oxazin]-3'-one. To a solution of cis-5-bromo-1-((2,4-dimethoxybenzyl)amino)-2,3-dihydro-1H-inden-2-ol (96.7%, 10.0 g, 25.6 mmol) in DCM (153 mL) was added triethylamine (10.7 mL, 76.7 mmol) and 2,4-dibromobutanoyl chloride (13.5 g, 51.1 mmol). The reaction was stirred at 0° C. for 30 min. The solution was concentrated by $N_2$ flow, dissovled in Tetrahydrofuran (153 mL) and t-BuOK (1M in tetrahydrofuran12-14 wgt %) (1.0 mol/L, 145 mL, 145 mmol) was added to the solution at 0° C. The reaction was stirred at 0° C. for 1 hour. The mixture was quenched by addition $NH_4Cl$ (200 mL), diluted with $H_2O$ (30 mL) and extracted with ethyl acetate (200 mL×3). The combined organic layers were washed with brine (150 mL×3), dried over $Na_2SO_4$, filtered, and concentrated under reduced pressure to give a residue. The residue was purified by flash silica gel chromatography (40 g Flash Silica Column, Eluent of 0-30% Ethyl acetate/Petroleum ether gradient @ 80 mL/min) to give the desired product. ES/MS: m/z=444.0, 445.9 $[M+H]^+$. $^1H$ NMR (400 MHz, $CDCl_3$) δ 7.39 (s, 3H), 7.27 (s, 2H), 6.53-6.45 (m, 2H), 5.45 (d, J=14.9 Hz, 1H), 4.72 (d, J=3.6 Hz, 1H), 4.58 (d, J=14.8 Hz, 1H), 4.51 (t, J=3.9 Hz, 1H), 3.82 (s, 3H), 3.78 (s, 3H), 3.09-3.01 (m, 1H), 2.96-2.88 (m, 1H), 1.52 (ddd, J=4.8, 7.6, 10.5 Hz, 1H), 1.21 (ddd, J=3.7, 7.3, 10.7 Hz, 1H), 1.07-0.99 (m, 1H), 0.97-0.90 (m, 1H).

Step 4. cis-4'-(2,4-dimethoxybenzyl)-7'-iodo-4',4a',9',9a'-tetrahydro-3'H-spiro[cyclopropane-1,2'-indeno[2,1-b][1,4]oxazin]-3'-one. To a solution of cis-7'-bromo-4'-(2,4-dimethoxybenzyl)-4',4a',9',9a'-tetrahydro-3'H-spiro[cyclopropane-1,2'-indeno[2,1-b][1,4]oxazin]-3'-one (2.6 g, 5.8 mmol) in 1,4-Dioxane (30.0 mL) was added NaI (1.7 g, 11.7 mmol), CuI (3.3 g, 17.6 mmol) and N,N-Dimethylethylenediamine (1.0 g, 11.7 mmol) under Ar atmosphere at 25° C. The reaction was stirred at 110° C. for 12 hours under Ar atmosphere (15 psi). The mixture was quenched by addition of sat. $NH_4Cl$ (30 mL) at 0° C. Then extracted with ethyl acetate (20 mL×3). The combined organic layers were washed with brine (10 mL×3), dried over $Na_2SO_4$, filtered, and concentrated under reduced pressure to give a residue. The residue was purified by flash silica gel chromatography (12 g Silica Flash Column, Eluent of 0-25% Ethyl acetate/Petroleum ether gradient @ 60 mL/min) to give the desired product. ES/MS: m/z=492.0 $[M+H]^+$. $^1H$ NMR (400 MHz, $CDCl_3$) δ 7.63-7.56 (m, 2H), 7.27 (s, 2H), 6.51-6.45 (m, 2H), 5.45 (d, J=14.9 Hz, 1H), 4.72 (d, J=3.6 Hz, 1H), 4.57 (d, J=14.9 Hz, 1H), 4.48 (t, J=3.9 Hz, 1H), 3.82 (s, 3H), 3.77 (s, 3H), 3.09-3.01 (m, 1H), 2.95-2.87 (m, 1H), 1.52 (ddd, J=4.8, 7.6, 10.5 Hz, 1H), 1.21 (ddd, J=3.8, 7.3, 10.7 Hz, 1H), 1.07-0.99 (m, 1H), 0.96-0.88 (m, 1H).

Step 5. cis-7'-(trifluoromethyl)-4',4a',9',9a'-tetrahydro-3'H-spiro[cyclopropane-1,2'-indeno[2,1-b][1,4]oxazin]-3'-one. To a solution of cis-4'-(2,4-dimethoxybenzyl)-7'-iodo-4',4a',9',9a'-tetrahydro-3'H-spiro[cyclopropane-1,2'-indeno[2,1-b][1,4]oxazin]-3'-one (1.8 g, 3.6 mmol) in NMP (20.0 mL) was added methyl 2,2-difluoro-2-fluorosulfonyl-acetate (3.5 g, 18.3 mmol) and Copper(I)Iodide (1.4 g, 7.3 mmol). The mixture was stirred at 110° C. for 12 hr under Ar (15 psi). The reaction mixture was filtered, then filtrate extracted with ethyl acetate 60 mL (20 mL×3). The combined organic layers were washed with brine 30 mL (10 mL×3), dried over $Na_2SO_4$, filtered, and concentrated under reduced pressure to give a residue. The residue was purified by flash silica gel chromatography (12 g Silica Flash Column, Eluent of 0-25% Ethyl acetate/Petroleum ether gradient @ 60 mL/min) to give cis-4'-(2,4-dimethoxybenzyl)-7'-(trifluoromethyl)-4',4a',9',9a'-tetrahydro-3'H-spiro[cyclopropane-1,2'-indeno[2,1-b][1,4]oxazin]-3'-one. A solution of cis-4'-(2,4-dimethoxybenzyl)-7'-(trifluoromethyl)-4',4a',9',9a'-tetrahydro-3'H-spiro[cyclopropane-1,2'-indeno[2,1-b][1,4]oxazin]-3'-one (2.2 g, 5.0 mmol) in Trifluoroacetic acid (20.0 mL, 0.2 mmol) was stirred at 80° C. for 3 hr. The mixture was concentrated under reduced pressure to give the crude product cis-7'-(trifluoromethyl)-4',4a',9',9a'-tetrahydro-3'H-spiro[cyclopropane-1,2'-indeno[2,1-b][1,4]

oxazin]-3'-one which was used into the next step without further purification. ES/MS: m/z=283.9 $[M+H]^+$. $^1H$ NMR (400 MHz, $CDCl_3$) δ 7.60 (d, J=8.3 Hz, 1H), 7.57 (s, 1H), 7.49 (d, J=7.9 Hz, 1H), 4.96-4.92 (m, 1H), 4.72 (t, J=4.4 Hz, 1H), 3.33-3.24 (m, 1H), 3.09 (d, J=17.1 Hz, 1H), 2.11-2.07 (m, 1H), 1.63-1.57 (m, 1H), 1.28-1.24 (m, 1H), 1.19 (s, 1H).

Step 6. (4a'R,9a'S)-7'-(trifluoromethyl)-4',4a',9',9a'-tetrahydro-3'H-spiro[cyclopropane-1,2'-indeno[2,1-b][1,4]oxazine] (Eby-1) and (4a'S,9a'R)-7'-(trifluoromethyl)-4',4a',9',9a'-tetrahydro-3'H-spiro[cyclopropane-1,2'-indeno[2,1-b][1,4]oxazine] (Eby-2). To a solution of cis-7'-(trifluoromethyl)-4',4a',9',9a'-tetrahydro-3'H-spiro[cyclopropane-1,2'-indeno[2,1-b][1,4]oxazin]-3'-one (1.4 g, 4.9 mmol) in tetrahydrofuran (14.0 mL) was added $BH_3$·THF (1.0 mol/L, 24.7 mL, 24.7 mmol in tetrahydrofuran) at 0° C. under $N_2$. The mixture was stirred at 60° C. for 12 hr under $N_2$. The mixture was quenched by addition MeOH 25 mL and HCl (1M) 17.5 mL, concentrated under reduced pressure to give a residue. The pH was adjusted to pH to 6-7 with $NaHCO_3$, and the mixture was extracted with ethyl acetate (20 mLx3). The combined organic layers were washed with brine (20 mLx3), dried over $Na_2SO_4$, filtered and concentrated under reduced pressure to give a residue. The residue filtrate was purified by prep-HPLC (HCl condition; column: Phenomenex luna C18 100*40 mm*5 um; mobile phase: [A: $H_2O$(0.04% HCl);B: ACN];B %: 10.00%-40.00%, 8.00 min) to give the desired racemic product, which was further separated by SFC (column: DAICEL CHIRALPAK AD (250 mm*30 mm, 10 um); mobile phase: [A: $CO_2$;B: EtOH (0.1% $NH_3H_2O$)];B %: 18.00%-18.00%, 2.60 min) to isolate (4a'R,9a'S)-7'-(trifluoromethyl)-4',4a',9',9a'-tetrahydro-3'H-spiro[cyclopropane-1,2'-indeno[2,1-b][1,4]oxazine] (Eby-1 ee %: 99.06%, RT=1.476 min, $[\alpha]_D^{20}$ 4.90°) and (4a'S,9a'R)-7'-(trifluoromethyl)-4',4a',9',9a'-tetrahydro-3'H-spiro[cyclopropane-1,2'-indeno[2,1-b][1,4]oxazine] Eby-2 which was further purified by prep-HPLC (HCl condition; column: Phenomenex luna C18 100*40 mm*5 um; mobile phase: [A: $H_2O$(0.04% HCl);B: ACN];B %: 5.00%-40.00%, 8.00 min) (ee %: 94.2%, HCl, RT=1.882 min, $[\alpha]_D^{20}$=−11.98°).

Eby1: ES/MS: m/z=270.2 $[M+H]^+$. $^1H$ NMR (400 MHz, DMSO-$d_6$) δ 10.50 (br s, 2H), 8.13 (d, J=8.3 Hz, 1H), 7.76-7.70 (m, 2H), 4.98 (br s, 1H), 4.62 (t, J=3.6 Hz, 1H), 3.24-3.13 (m, 2H), 2.93-2.82 (m, 2H), 0.94-0.84 (m, 1H), 0.82-0.73 (m, 2H), 0.72-0.65 (m, 1H).

EBy-2: ES/MS: m/z=270.2 $[M+H]^+$. $^1H$ NMR (400 MHz, DMSO-$d_6$) δ 10.70 (br s, 2H), 8.20 (d, J=8.3 Hz, 1H), 7.75-7.68 (m, 2H), 4.98 (br s, 1H), 4.61 (t, J=3.6 Hz, 1H), 3.17 (br dd, J=4.0, 16.5 Hz, 2H), 2.94-2.78 (m, 2H), 0.93-0.85 (m, 1H), 0.84-0.77 (m, 1H), 0.77-0.64 (m, 2H).

(4aS,9aR)-2,2-dimethyl-7-(trifluoromethyl)-2,3,4,4a,9,9a-hexahydroindeno[2,1-b][1,4]oxazine hydrochloride (Eby-3) and (4aR,9aS)-2,2-dimethyl-7-(trifluoromethyl)-2,3,4,4a,9,9a-hexahydroindeno[2,1-b][1,4]oxazine hydrochloride (Eby-4). Prepared following general procedure LXXVI-E using cis-1-amino-5-bromo-indan-2-ol as and 2-chloroacetyl chloride. Intermediate cis-(4aR,9aS)-7-bromo-4-(3,4-dimethylbenzyl)-4,4a,9,9a-tetrahydroindeno[2,1-b][1,4]oxazin-3(2H)-one was dialkylated using LDA (2 equiv.) and MeI (2 equiv.) (twice) to deliver cis-(4aR,9aS)-7-bromo-4-(3,4-dimethylbenzyl)-2,2-dimethyl-4,4a,9,9a-tetrahydroindeno[2,1-b][1,4]oxazin-3(2H)-one prior continuing the sequence to step 4. Prep-SFC (column: REGIS (s,s) WHELK-O1 (250 mm*50 mm, 10 um); mobile phase: [A: $CO_2$;B: IPA (0.1% $NH_3H_2O$)];B %: 11.00%-11.00%, 3.30 min) to isolate Eby-3 (RT=0.426 min, chiral purity 99.85%) and Eby-4 (RT=0.572 min, chiral purity 99.23%).

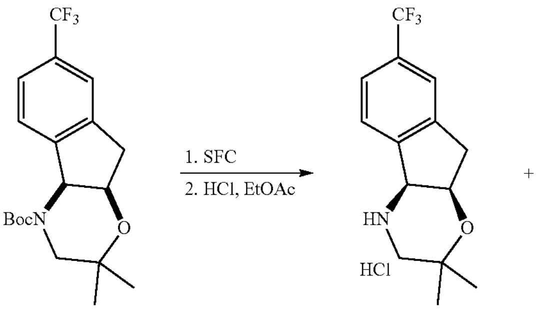

Eby-3
Peak 1

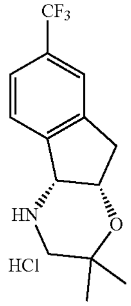

Eby-4
Peak 2

Eby-3: ES/MS: m/z=272.2 $[M+H]^+$. $^1H$ NMR (400 MHz, DMSO-$d_6$) δ 10.73-10.19 (m, 2H), 8.12 (br d, J=7.6 Hz, 1H), 7.76-7.67 (m, 2H), 4.85 (br d, J=2.5 Hz, 1H), 4.71-4.63 (m, 1H), 3.28-3.18 (m, 1H), 3.09 (d, J=12.9 Hz, 1H), 2.90 (d, J=17.0 Hz, 1H), 2.65 (br d, J=12.9 Hz, 1H), 1.40 (s, 3H), 1.06 (s, 3H).

Eby-4: ES/MS: m/z=272.2 $[M+H]^+$. $^1H$ NMR (400 MHz, DMSO-$d_6$) δ 10.74-10.26 (m, 2H), 8.13 (br d, J=7.9 Hz, 1H), 7.74-7.67 (m, 2H), 4.84 (br s, 1H), 4.66 (t, J=4.3 Hz, 1H), 3.30-3.19 (m, 1H), 3.09 (d, J=12.9 Hz, 1H), 2.90 (d, J=17.0 Hz, 1H), 2.65 (br d, J=12.9 Hz, 1H), 1.41 (s, 3H), 1.06 (s, 3H).

General Procedure LXXVII-E for the Synthesis of Intermediates Ebz:

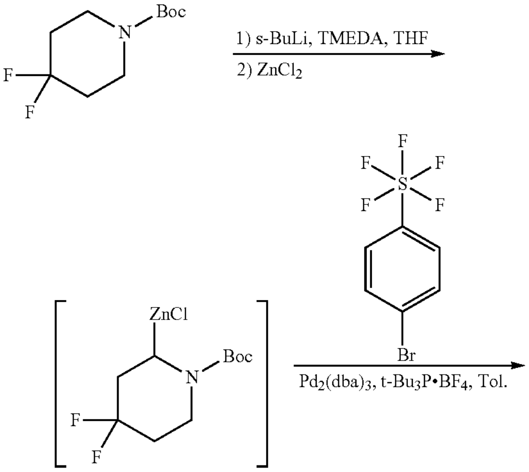

-continued

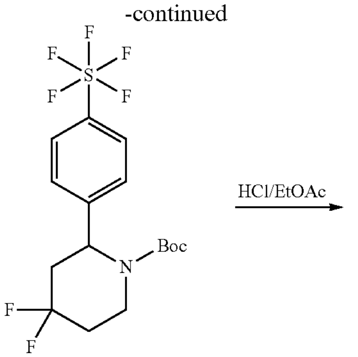

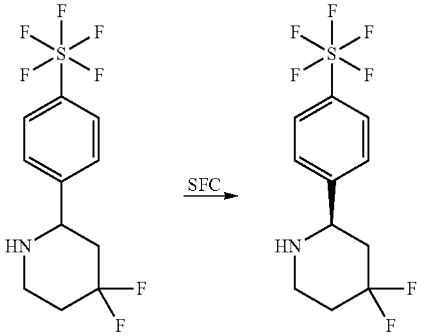

Ebz-1

Step 1. (1-(tert-butoxycarbonyl)-4,4-difluoropiperidin-2-yl)zinc(II) chloride. To a solution of tert-butyl 4,4-difluoropiperidine-1-carboxylate (4.7 g, 21.2 mmol) in Tetrahydrofuran (50.0 mL) was added N,N,N,N-Tetramethylethylenediamine (2.9 g, 25.5 mmol) and sec-butyllithium (1.3 mol/L, 19.6 mL, 25.5 mmol) at −70° C. under $N_2$ atmosphere. The mixture was stirred at −70° C. for 1 hr under $N_2$ atmosphere. Then Zincchloride (1.0 mol/L, 25.5 mL, 25.5 mmol) was added at −70° C. for 0.5 hr under $N_2$ atmosphere. The mixture was stirred at 25° C. for 1 hr under $N_2$ atmosphere. (1-(tert-butoxycarbonyl)-4,4-difluoropiperidin-2-yl)zinc(II) chloride in tetrahydrofuran was obtained and used for the next step under $N_2$ atmosphere.

Step 2. tert-butyl 4,4-difluoro-2-(4-(pentafluoro-%$^6$-sulfaneyl)phenyl)piperidine-1-carboxylate. A mixture of Tri-tert-butylphosphine tetrafluoroborate (304 mg, 1.4 mmol) and $Pd_2(dba)_3$ (1.3 g, 1.4 mmol) in toluene (15.0 mL) was degassed and purged with $N_2$ for 3 times, the mixture was stirred at 25° C. for 10 min under $N_2$ atmosphere. Then the mixture was added (4-bromophenyl)pentafluoro-λ$^6$-sulfane (4.2 g, 14.9 mmol), (1-(tert-butoxycarbonyl)-4,4-difluoropiperidin-2-yl)zinc(II) chloride (4.8 g, 14.9 mmol) in tetrahydrofuran and stirred at 60° C. for 12 hr under $N_2$ atmosphere. LC-MS showed desired mass was detected. The residue was diluted with $H_2O$ 10 mL, ethyl acetate 10 mL and filtered to obtain filtrate. The filtrate were extracted with ethyl acetate (10 mL×3), dried over $Na_2SO_4$, filtered and concentrated under reduced pressure to give a residue. The residue was purified by flash silica gel chromatography to give the desired product. $^1$H NMR (400 MHz, DMSO-$d_6$) δ 7.89 (d, J=8.9 Hz, 2H), 7.44 (br s, 2H), 5.55 (br d, J=5.5 Hz, 1H), 4.17 (br d, J=13.8 Hz, 1H), 3.07-2.97 (m, 1H), 2.86-2.75 (m, 1H), 2.47-2.36 (m, 1H), 2.11-2.01 (m, 1H), 1.44-1.40 (m, 1H), 1.39 (s, 9H).

Step 3. 4,4-difluoro-2-(4-(pentafluoro-%$^6$-sulfaneyl)phenyl)piperidine. A solution of tert-butyl 4,4-difluoro-2-[4-(pentafluoro-λ$^6$-sulfanyl)phenyl]piperidine-1-carboxylate (purity 32.1%, 3.0 g, 2.2 mmol,) in hydrochloric acid (4.0 mol/L, 6.0 mL, 24.0 mmol) in ethyl acetate was stirred at 25° C. for 1.5 hr. LC-MS showed desired mass was detected. The residue was diluted with $H_2O$ 30 mL and extracted with ethyl acetate (10 mL×3). The aqueous layers were basified with TEA until pH=7-8 and extracted with ethyl acetate (40 mL×3). The combined organic layers were dried over $Na_2SO_4$, filtered and concentrated under reduced pressure to give the desired product. $^1$H NMR (400 MHz, DMSO-$d_6$) δ 7.88 (d, J=8.6 Hz, 2H), 7.66 (br d, J=8.4 Hz, 2H), 3.86 (br d, J=11.4 Hz, 1H), 3.22-3.04 (m, 1H), 2.83-2.70 (m, 1H), 2.28-2.18 (m, 1H), 2.13-2.00 (m, 1H), 1.97-1.74 (m, 2H).

Step 4. (R)-4,4-difluoro-2-(4-(pentafluoro-%$^6$-sulfaneyl)phenyl)piperidine. [4-(4,4-difluoro-2-piperidyl)phenyl]-pentafluoro-)$^6$-sulfane (purity 91.5%, 522.0 mg, 1.4 mmol) was further separated by SFC (column: DAICEL CHIRALPAK AD (250 mm×30 mm, 10 um); mobile phase: [A: $CO_2$;B: MeOH (0.1% NH3H2O)];B %: 10.00%-10.00%, 4.00 min) to give (R)-4,4-difluoro-2-(4-(pentafluoro-λ$^6$-sulfaneyl)phenyl)piperidine Ebz-1 (ee %=98.9%, Rt=1.29 min). ES/MS: m/z=324.1 [M+H]$^+$. $^1$H NMR (400 MHz, DMSO-$d_6$) δ 7.96-7.79 (m, 2H), 7.65 (br d, J=7.5 Hz, 2H), 3.94-3.78 (m, 1H), 3.15 (br d, J=1.4 Hz, 1H), 2.84-2.70 (m, 1H), 2.30-2.16 (m, 1H), 2.12-1.73 (m, 3H).

General Procedure I-F for the Synthesis of Compounds Fa

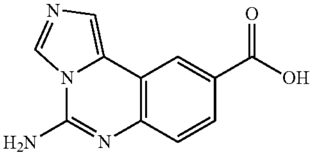

Ba-1

+

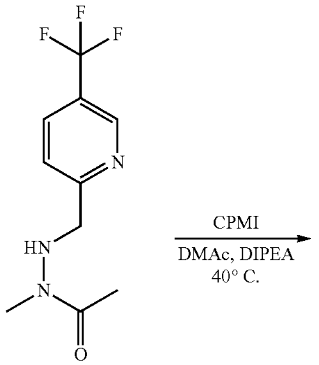

Dd-1

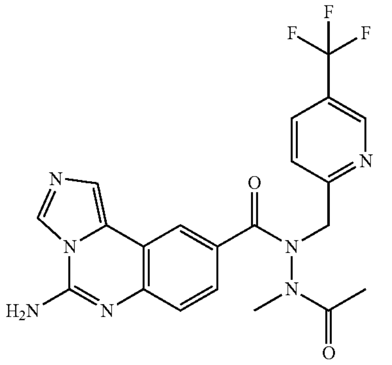

Example Fa-1

Example Fa-1: N'-acetyl-5-amino-N'-methyl-N-((5-(trifluoromethyl)pyridin-2-yl)methyl)imidazo[1,5-c]quinazoline-9-carbohydrazide. 5-aminoimidazo[1,5-c]quinazoline- 9-carboxylic acid Ba-1 (27.5 mg, 0.12 mmol), N-methyl-N'-((5-(trifluoromethyl)pyridin-2-yl)methyl)acetohydrazide Dd-1 (34.6 mg, 0.14 mmol) and 2-chloro-1-methyl-pyridin-1-ium iodide (44 mg, 0.17 mmol) were dissolved in DMAc (1.5 mL) and DIPEA (44 μL, 0.25 mmol) was added. The resulting mixture was stirred at 40° C. overnight and then diluted with EtOAc and 10% aq. LiCl solution and transferred to a separatory funnel. The organic layer was separated, and the aqueous layer was washed with a further portion of EtOAc. The combined organic layers were dried over anhydrous $MgSO_4$ and concentrated under reduced pressure. The crude residue was purified by preparative HPLC. EZ/MS: m/z=458.2 $[M+H]^+$. $^1H$ NMR (400 MHz, DMSO) δ 8.68 (s, 1H), 8.24 (d, J=8.2 Hz, 2H), 7.96 (d, J=4.9 Hz, 3H), 7.41 (dd, J=14.7, 9.3 Hz, 2H), 5.25 (d, J=33.2 Hz, 1H), 4.99 (d, J=15.0 Hz, 1H), 4.64 (brs, 1H), 3.05 (s, 3H), 1.90 (s, 3H).

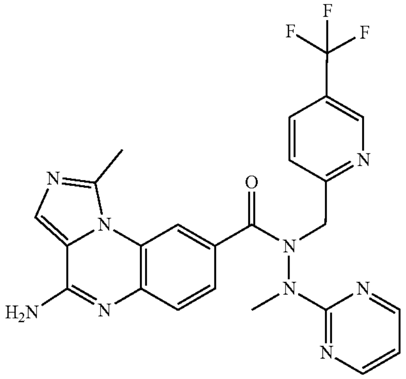 [SMILES: Cc1ncc2c(N)nc3ccc(C(=O)N(Cc4ccc(C(F)(F)F)cn4)N(C)c4ncccn4)cc3n12]

Example Fa-2: 4-amino-N',1-dimethyl-N'-pyrimidin-2-yl-N-[[5-(trifluoromethyl)-2-pyridyl]methyl]imidazo[1,5-a]quinoxaline-8-carbohydrazide. Prepared using general procedure I-F starting with 4-amino-1-methyl-imidazo[1,5-a]quinoxaline-8-carboxylic acid Ac-2 and 2-(1-methyl-2-((5-(trifluoromethyl)pyridin-2-yl)methyl)hydrazineyl)pyrimidine Da-4. ES/MS: m/z=507.9 $[M+H]^+$. $^1H$ NMR (400 MHz, DMSO-d6) δ 8.90 (s, 1H), 8.47 (d, J=4.8 Hz, 2H), 8.29-8.10 (m, 3H), 7.88 (d, J=8.3 Hz, 1H), 7.67 (d, J=8.4 Hz, 1H), 7.55 (d, J=8.5 Hz, 1H), 6.88 (t, J=4.8 Hz, 1H), 5.37 (d, J=15.6 Hz, 1H), 4.70 (d, J=15.6 Hz, 1H), 3.29 (s, 3H), 2.79 (s, 3H).

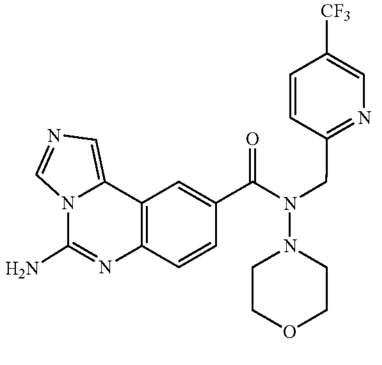 [SMILES: Nc1nc2ccc(C(=O)N(Cc3ccc(C(F)(F)F)cn3)N3CCOCC3)cc2c2cncn12]

Example Fa-3: 5-amino-N-morpholino-N-((5-(trifluoromethyl)pyridin-2-yl)methyl)imidazo[1,5-c]quinazoline-9-carboxamide. Prepared following general procedure I-F starting with 5-aminoimidazo[1,5-c]quinazoline-9-carboxylic acid Ba-1 and N-((5-(trifluoromethyl)pyridin-2-yl)methyl)morpholin-4-amine Da-3. ES/MS: m/z=472.0 $[M+H]^+$. $^1H$ NMR (400 MHz, MeOD) δ 9.11-8.83 (m, 2H), 8.38-8.23 (m, 1H), 8.17-8.06 (m, 2H), 7.89-7.69 (m, 2H), 7.64-7.38 (m, 1H), 5.05 (s, 2H), 3.76 (d, J=11.2 Hz, 2H), 3.37-3.15 (m, 2H), 3.06 (d, J=14.2 Hz, 2H), 2.93 (d, J=10.7 Hz, 2H).

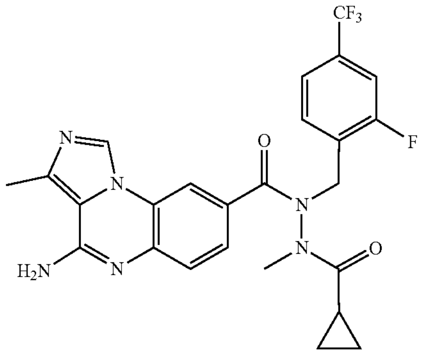 [SMILES: Cc1ncn2c1c(N)nc1ccc(C(=O)N(Cc3ccc(C(F)(F)F)cc3F)N(C)C(=O)C3CC3)cc12]

Example Fa-4: 4-amino-N'-(cyclopropanecarbonyl)-N-(2-fluoro-4-(trifluoromethyl)benzyl)-N',3-dimethylimidazo[1,5-a]quinoxaline-8-carbohydrazide. Prepared following general procedure I-F starting with 4-amino-3-methylimidazo[1,5-a]quinoxaline-8-carboxylic acid Aa-1 and N'-(2-fluoro-4-(trifluoromethyl)benzyl)-N-methylcyclopropanecarbohydrazide Db-1. ES/MS: m/z=515.0 $[M+H]^+$. $^1H$ NMR (400 MHz, MeOD) δ 9.21-9.14 (m, 1H), 8.54-8.20 (m, 1H), 7.99-7.38 (m, 5H), 5.56-5.11 (m, 1H), 4.99 (d, J=14.7 Hz, 1H), 3.36 (s, 1H, minor rotamer), 3.12 (s, 2H, major rotamer), 2.80 (s, 3H), 1.72-1.50 (m, 1H), 0.90-0.30 (m, 4H).

Example Fa-5: N'-acetyl-4-amino-N-(2-fluoro-4-(1-(trifluoromethyl)-1H-pyrazol-4-yl)benzyl)-N',3-dimethylimidazo[1,5-a]quinoxaline-8-carbohydrazide

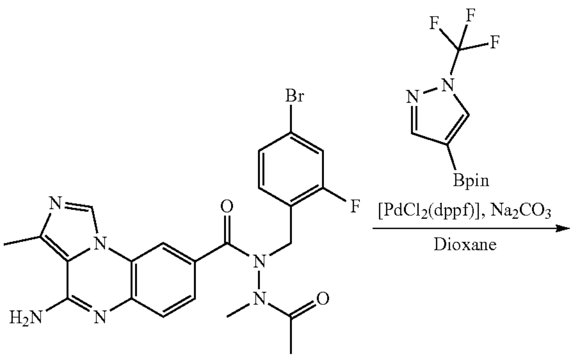

-continued

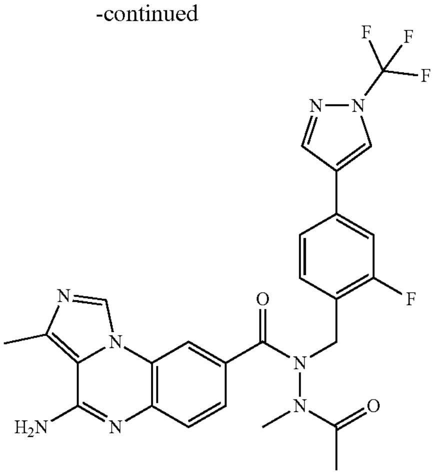

Example Fa-5

Intermediate N'-acetyl-4-amino-N-(4-bromo-2-fluorobenzyl)-N',3-dimethylimidazo[1,5-a]quinoxaline-8-carbohydrazide was prepared following general procedure I-F starting with 4-amino-3-methylimidazo[1,5-a]quinoxaline-8-carboxylic acid Aa-1 and N'-(4-bromo-2-fluorobenzyl)-N-methylacetohydrazide Dc-1. ES/MS: m/z=501.0 $[M+H]^+$.

N'-acetyl-4-amino-N-(2-fluoro-4-(1-(trifluoromethyl)-1H-pyrazol-4-yl)benzyl)-N',3-dimethylimidazo[1,5-a]quinoxaline-8-carbohydrazide: To a solution of 1N'-acetyl-4-amino-N-(4-bromo-2-fluorobenzyl)-N',3-dimethylimidazo[1,5-a]quinoxaline-8-carbohydrazide (14.5 mg, 0.029 mmol) and 4-(4,4,5,5-tetramethyl-1,3,2-dioxaborolan-2-yl)-1-(trifluoromethyl)-1H-pyrazole (10.0 mg, 0.030 mmol), and $PdCl_2$(dppf) (3.3 mg, 0.0045 mmol) in dioxane (2 mL), was added 2M $Na_2CO_3$ (0.0159 mg, 0.184 mmol). The mixture was bubbled through argon for 1 minute and left to stir at 90 C for 6 hours. The mixture was filtered through a pad of celite and anhydrous $MgSO_4$. The solution was reduced under pressure and the crude was purified by flash chromatography. (2.8 mg, 17%). ES/MS: m/z=555.0 $[M+H]^+$. $^1$H NMR (400 MHz, Methanol-d4) δ 9.19 (d, J=14.5 Hz, 1H), 8.70 (d, J=5.7 Hz, 1H), 8.36 (d, J=65.6 Hz, 2H), 7.52 (d, J=13.4 Hz, 5H), 5.28-4.94 (m, 0.4Hm minor rotamer), 4.73 (d, J=14.5 Hz, 1H), 3.18-3.07 (m, 3H), 2.80 (d, J=3.3 Hz, 3H), 2.68 (s, 1H), 1.81 (s, 3H).

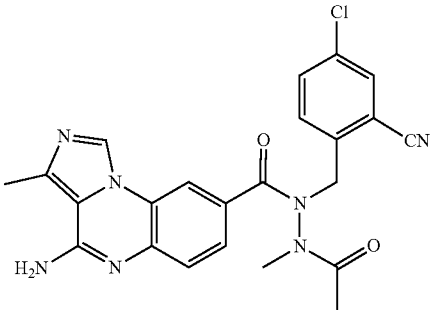 [SMILES: CC(=O)N(C)N(Cc1ccc(Cl)cc1C#N)C(=O)c1ccc2nc(N)c3c(C)ncn3c2c1]

Example Fa-6: N'-acetyl-4-amino-N-(4-chloro-2-cyanobenzyl)-N',3-dimethylimidazo[1,5-a]quinoxaline-8-carbohydrazide. Prepared following general procedure I-F starting with 4-amino-3-methylimidazo[1,5-a]quinoxaline-8-carboxylic acid Aa-1 and N'-(4-chloro-2-cyanobenzyl)-N-methylacetohydrazide Dc-4. ES/MS: m/z=461.9 $[M+H]^+$. $^1$H NMR (400 MHz, DMSO-d6) δ 9.35 (d, J=12.8 Hz, 1H), 8.48 (s, 0.33H, minor rotamer), 8.36 (s, 0.67H, major rotamer), 8.17 (s, 0.33H, minor rotamer), 8.11 (s, 0.67H, major rotamer), 7.95-7.74 (m, 2H), 7.68-7.49 (m, 2H), 5.21-5.01 (m, 1H), 4.74 (d, J=15.4 Hz, 1H), 3.26 (s, 2H, major rotamer), 3.00 (s, 1H, minor rotamer), 2.73 (s, 3H), 1.79 (s, 2H, major rotamer), 1.76 (s, 1H, minor rotamer).

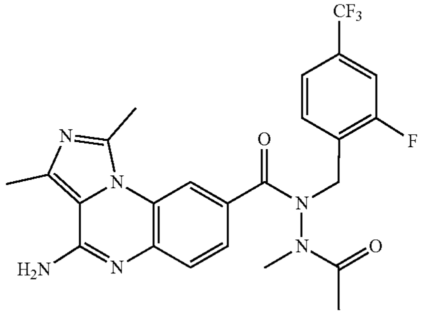 [SMILES: CC(=O)N(C)N(Cc1ccc(C(F)(F)F)cc1F)C(=O)c1ccc2nc(N)c3c(C)nc(C)n3c2c1]

Example Fa-7: N'-acetyl-4-amino-N-(2-fluoro-4-(trifluoromethyl)benzyl)-N',1,3-trimethylimidazo[1,5-a]quinoxaline-8-carbohydrazide. Prepared following general procedure I-F starting with 4-amino-1,3-dimethylimidazo[1,5-a]quinoxaline-8-carboxylic acid Ab-1 and N'-(2-fluoro-4-(trifluoromethyl)benzyl)-N-methylacetohydrazide Da-7. ES/MS: m/z=502.9 $[M+H]^+$. $^1$H NMR (400 MHz, DMSO-d6) δ 8.21 (s, 0.33H, minor rotamer), 8.11 (s, 0.67H, major rotamer), 7.91 (t, J=7.7 Hz, 1H), 7.81 (d, J=10.0 Hz, 0.33H, minor rotamer), 7.74 (dd, J=10.1, 1.7 Hz, 0.67H, major rotamer), 7.72-7.62 (m, 2H), 7.60 (s, 1H), 5.08 (d, J=14.4 Hz, 1H), 4.76 (d, J=15.2 Hz, 1H), 3.16 (s, 2H, major rotamer), 3.03 (s, 1H, minor rotamer), 3.01 (s, 1H, minor rotamer), 2.97 (s, 2H, major rotamer), 2.70 (s, 3H), 1.84 (s, 2H, major rotamer), 1.77 (s, 1H, minor rotamer).

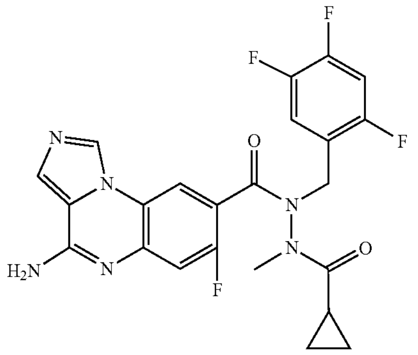 [SMILES: CN(C(=O)C1CC1)N(Cc1cc(F)c(F)cc1F)C(=O)c1cc2c(cc1F)nc(N)c1cncn12]

Example Fa-8: 4-amino-N'-(cyclopropanecarbonyl)-7-fluoro-N'-methyl-N-(2,4,5-trifluorobenzyl)imidazo[1,5-a]quinoxaline-8-carbohydrazide. Prepared following the general procedure I-F starting with intermediates 4-((tert-butoxycarbonyl)amino)-7-fluoroimidazo[1,5-a]quinoxaline-8-carboxylic acid Af-1 and N-methyl-N'-(2,4,5-trifluorobenzyl)cyclopropanecarbohydrazide hydrogen chloride De-1. ES/MS: m/z=487.0. 1H NMR (400 MHz, Methanol-d4) δ 9.40-9.09 (m, 1H), 8.68-8.40 (m, 1H), 8.28 (d, J=47.3 Hz, 1H), 7.76-6.98 (m, 3H), 5.44-4.93 (m, 1H), 4.76 (d, J=49.6 Hz, 1H), 3.58-3.37 (m, 1H), 3.21-2.67 (m, 2H), 2.10-1.50 (m, 1H), 1.22-0.23 (m, 4H).

General Procedure II-F for the Synthesis of Compounds Fb:

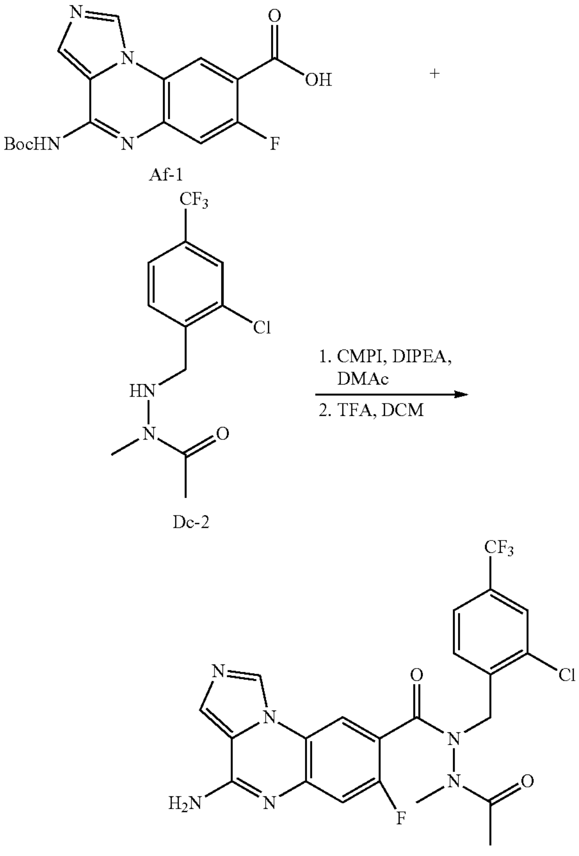

Af-1

Dc-2

Example Fb-1

Step 1. Tert-butyl (8-(2-acetyl-1-(2-chloro-4-(trifluoromethyl)benzyl)-2-methylhydrazine-1-carbonyl)-7-fluoroimidazo[1,5-a]quinoxalin-4-yl)carbamate. 4-((tert-butoxycarbonyl)amino)-7-fluoroimidazo[1,5-a]quinoxaline-8-carboxylic acid Af-1 (41.5 mg, 0.12 mmol), N'-(2-chloro-4-(trifluoromethyl)benzyl)-N-methylacetohydrazide Dc-2 (39 mg, 0.14 mmol) and 2-chloro-1-methyl-pyridin-1-ium iodide (44 mg, 0.17 mmol) were dissolved in DMAc (1.5 mL) and DIPEA (44 μL, 0.25 mmol) was added. The resulting mixture was stirred at 40° C. overnight and then diluted with EtOAc and 10% aq. LiCl solution and transferred to a separatory funnel. The organic layer was separated, and the aqueous layer was washed with a further portion of EtOAc. The combined organic layers were dried over anhydrous $MgSO_4$ and concentrated under reduced pressure. The crude residue was purified by column chromatography over silica gel. EZ/MS: m/z=609.9 $[M+H]^+$.

Step 2. N'-acetyl-4-amino-N-(2-chloro-4-(trifluoromethyl)benzyl)-7-fluoro-N'-methylimidazo[1,5-a]quinoxaline-8-carbohydrazide. Tert-butyl (8-(2-acetyl-1-(2-chloro-4-(trifluoromethyl)benzyl)-2-methylhydrazine-1-carbonyl)-7-fluoroimidazo[1,5-a]quinoxalin-4-yl)carbamate was dissolved in DCM (2 mL) and TFA (1 mL) was added. The resulting mixture was stirred for 2 hours at room temperature then evaporated to dryness and purified by preparative HPLC. EZ/MS: m/z=509.9 $[M+H]^+$. $^1H$ NMR (400 MHz, DMSO-$d_6$) δ 9.39-9.35 (m, 0.7H major rotamer), 9.31 (s, 0.3H minor rotamer), 8.71 (brs, 2H), 8.61 (d, J=6.2 Hz, 0.7H major rotamer), 8.45 (d, J=6.3 Hz, 0.3H minor rotamer), 8.30 (d, J=6.2 Hz, 0.5H minor rotamer), 8.26-8.15 (m, 1.5H major rotamer), 8.06-7.91 (m, 1H), 7.86-7.70 (m, 2H), 7.48-7.31 (m, 1H), 5.31 (d, J=15.8 Hz, 0.7H major rotamer), 5.30-5.22 (m, 0.3H minor rotamer), 5.12 (d, J=15.1 Hz, 0.3H minor rotamer), 4.62 (d, J=15.8 Hz, 0.7H major rotamer), 3.10 (s, 0.9H minor rotamer), 2.85 (s, 2.1H major rotamer), 1.79 (s, 0.9H minor rotamer), 1.76 (s, 2.1H major rotamer).

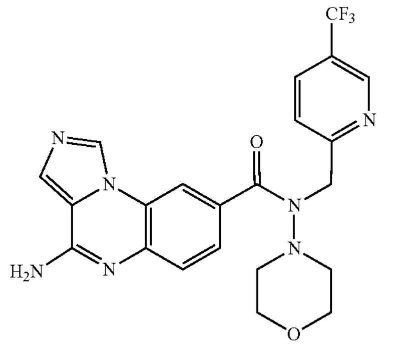 [SMILES: Nc1nc2ccc(C(=O)N(Cc3ccc(C(F)(F)F)cn3)N3CCOCC3)cc2n2cncc12]

Example Fb-2: 4-amino-N-morpholino-N-((5-(trifluoromethyl)pyridin-2-yl)methyl)imidazo[1,5-a]quinoxaline-8-carboxamide. Prepared using general procedure II-F starting with 4-((tert-butoxycarbonyl)amino)imidazo[1,5-a]quinoxaline-8-carboxylic acid Ae-1 and N-((5-(trifluoromethyl)pyridin-2-yl)methyl)morpholin-4-amine Da-3. ES/MS: m/z=472.0 $[M+H]^+$. $^1H$ NMR (400 MHz, MeOD) δ 9.34 (s, 1H), 8.92-8.87 (m, 1H), 8.47 (s, 1H), 8.43 (s, 1H), 8.14 (dd, J=8.3, 2.4 Hz, 1H), 7.84 (dd, J=8.4, 1.6 Hz, 1H), 7.76 (d, J=8.3 Hz, 1H), 7.68 (d, J=8.5 Hz, 1H), 5.06 (s, 2H), 3.76 (d, J=11.3 Hz, 2H), 3.29 (d, J=13.5 Hz, 2H), 3.05 (t, J=10.9 Hz, 2H), 2.94 (d, J=10.7 Hz, 2H).

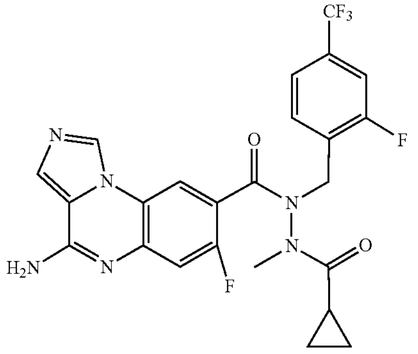 [SMILES: CN(C(=O)C1CC1)N(Cc1ccc(C(F)(F)F)cc1F)C(=O)c1cc2c(cc1F)nc(N)c1cncn12]

Example Fb-3: 4-amino-N'-(cyclopropanecarbonyl)-7-fluoro-N-(2-fluoro-4-(trifluoromethyl)benzyl)-N'-methyl-imidazo[1,5-a]quinoxaline-8-carbohydrazide. Prepared following general procedure II-F starting with 4-((tert-butoxycarbonyl)amino)-7-fluoroimidazo[1,5-a]quinoxaline-8-carboxylic acid Af-1 and N'-(2-fluoro-4-(trifluoromethyl)benzyl)-N-methylcyclopropanecarbohydrazide Db-1. ES/MS: m/z=519.0 $[M+H]^+$. $^1H$ NMR (400 MHz, MeOD) δ 9.33-9.04 (m, 1H), 8.70-8.10 (m, 2H), 7.94-7.76 (m, 1H), 7.63-7.49 (m, 2H), 7.47-7.38 (m, 1H), 5.47 (d, J=14.6 Hz, 0.7H, major rotamer), 5.19 (d, J=14.7 Hz, 0.3H, minor rotamer), 5.05 (d, J=15.0 Hz, 1H), 3.21-3.01 (m, 3H), 1.88-1.50 (m, 1H), 1.16-0.19 (m, 4H).

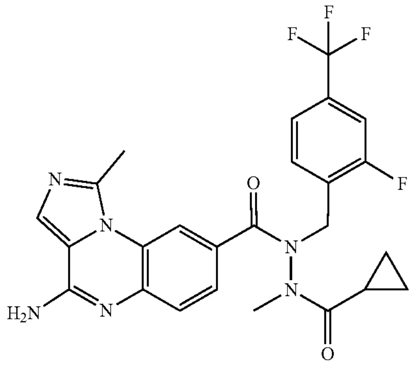 [SMILES: Cc1ncc2c(N)nc3ccc(C(=O)N(Cc4ccc(C(F)(F)F)cc4F)N(C)C(=O)C4CC4)cc3n12]

Example Fb-4: 4-amino-N'-(cyclopropanecarbonyl)-N-(2-fluoro-4-(trifluoromethyl)benzyl)-N',1-dimethylimidazo[1,5-a]quinoxaline-8-carbohydrazide. Prepared following general procedure II-F starting with 4-((tert-butoxycarbonyl)amino)-1-methylimidazo[1,5-a]quinoxaline-8-carboxylic acid Af-3 and N'-(2-fluoro-4-(trifluoromethyl)benzyl)-N-methylcyclopropanecarbohydrazide Db-1. EZ/MS: m/z=515.2 $[M+H]^+$. $^1$H NMR (400 MHz, MeOD) δ 8.44 (d, J=1.6 Hz, 1H), 8.33 (d, J=3.8 Hz, 1H), 7.92-7.72 (m, 2H), 7.67 (d, J=9.1 Hz, 1H), 7.56 (dt, J=25.9, 8.8 Hz, 2H), 5.49-5.33 (m, 0.5H major rotamer), 5.14 (d, J=14.9 Hz, 0.4H minor rotamer), 5.03 (d, J=14.5 Hz, 0.5H major rotamer), 4.91 (d, J=2.1 Hz, 0.3H minor rotamer), 3.36 (s, 1.6H minor rotamer), 3.19-3.07 (m, 4.7H major rotamer), 1.73 (dd, J=8.3, 4.0 Hz, 1H), 0.95-0.32 (m, 4H).

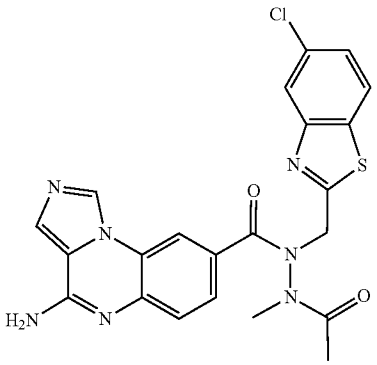 [SMILES: CC(=O)N(C)N(Cc1nc2cc(Cl)ccc2s1)C(=O)c1ccc2nc(N)c3cncn3c2c1]

Example Fb-5: N'-acetyl-4-amino-N-((5-chlorobenzo[d]thiazol-2-yl)methyl)-N'-methylimidazo[1,5-a]quinoxaline-8-carbohydrazide. Prepared using general procedure II-F starting with 4-((tert-butoxycarbonyl)amino)imidazo[1,5-a]quinoxaline-8-carboxylic acid Ae-1 and N'-[(5-chloro-1,3-benzothiazol-2-yl)methyl]-N-methyl-acetohydrazide Dc-3. ES/MS: m/z=480.3 $[M+H]^+$. $^1$H NMR (400 MHz, Methanol-d4) δ 9.29 (d, J=9.9 Hz, 1H), 8.54-8.26 (m, 2H), 8.02 (d, J=7.9 Hz, 1H), 7.79-7.60 (m, 2H), 7.50 (td, J=8.3, 2.0 Hz, 1H), 5.37 (dd, J=45.4, 15.8 Hz, 1H), 5.11 (d, J=15.8 Hz, 1H), 3.43 (s, 2H), 3.28-3.13 (m, 2H), 1.98 (d, J=21.0 Hz, 2H), 1.86 (s, 3H).

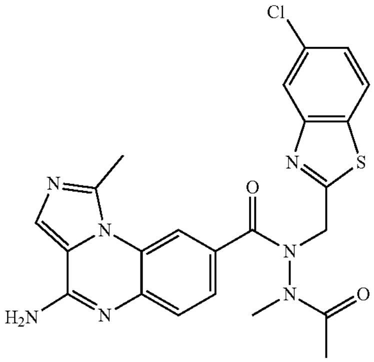 [SMILES: CC(=O)N(C)N(Cc1nc2cc(Cl)ccc2s1)C(=O)c1ccc2nc(N)c3cnc(C)n3c2c1]

Example Fb-6: N'-acetyl-4-amino-N-((5-chlorobenzo[d]thiazol-2-yl)methyl)-N',1-dimethylimidazo[1,5-a]quinoxaline-8-carbohydrazide. Prepared following general procedure II-F starting with 4-((tert-butoxycarbonyl)amino)-1-methylimidazo[1,5-a]quinoxaline-8-carboxylic acid Af-3 and N'-[(5-chloro-1,3-benzothiazol-2-yl)methyl]-N-methyl-acetohydrazide Dc-3. ES/MS: m/z=494.2 $[M+H]^+$. $^1$H NMR (400 MHz, Methanol-d4) 8.34 (d, J=15.2 Hz, 2H), 8.03 (dd, J=8.6, 2.5 Hz, 2H), 7.81-7.61 (m, 2H), 7.50 (td, J=8.3, 2.0 Hz, 1H), 5.57-5.26 (m, 1H), 5.13 (d, J=15.9 Hz, 1H), 3.40 (s, 3H), 3.24 (s, 1H), 3.11 (s, 3H), 1.93 (d, J=23.1 Hz, 3H).

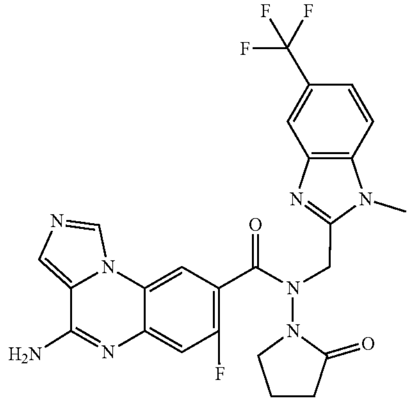 [SMILES: Cn1c(CN(C(=O)c2cc3c(cc2F)nc(N)c2cncn23)N2CCCC2=O)nc2cc(C(F)(F)F)ccc21]

Example Fb-7: 4-amino-7-fluoro-N-((1-methyl-5-(trifluoromethyl)-1H-benzo[d]imidazol-2-yl)methyl)-N-(2-oxopyrrolidin-1-yl)imidazo[1,5-a]quinoxaline-8-carboxamide. Prepared following general procedure II-F starting with 4-((tert-butoxycarbonyl)amino)-7-fluoroimidazo[1,5-a]quinoxaline-8-carboxylic acid Af-1 and 1-(((1-methyl-5-(trifluoromethyl)-1H-benzo[d]imidazol-2-yl)methyl)amino)pyrrolidin-2-one Da-6. ES/MS: m/z 541.3 $[M+H]^+$. $^1$H NMR (400 MHz, Methanol-d4) δ 9.24 (s, 1H), 8.36 (d, J=13.0 Hz, 2H), 7.97 (s, 1H), 7.80 (d, J=8.6 Hz, 1H), 7.67 (d, J=8.6 Hz, 1H), 7.44 (d, J=9.8 Hz, 1H), 5.72 (d, J=15.4 Hz, 1H), 5.10 (d, J=15.4 Hz, 1H), 4.13 (s, 3H), 3.85 (d, J=8.2 Hz, 1H), 3.68-3.44 (m, 1H), 2.16-1.53 (m, 4H).

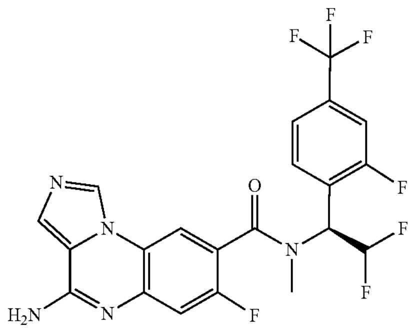 [SMILES: CN(C(=O)c1cc2c(cc1F)nc(N)c1cncn12)[C@@H](c1ccc(C(F)(F)F)cc1F)C(F)F]

Example Fb-8: (S)-4-amino-N-(2,2-difluoro-1-(2-fluoro-4-(trifluoromethyl)phenyl)ethyl)-7-fluoro-N-methylimidazo[1,5-a]quinoxaline-8-carboxamide. Prepared following general procedure II-F starting with 4-((tert-butoxycarbonyl)amino)-7-fluoroimidazo[1,5-a]quinoxaline-8-carboxylic acid Af-1 and (S)-2,2-difluoro-1-(2-fluoro-4-(trifluoromethyl)phenyl)-N-methylethan-1-amine hydrochloride Eal-1. ES/MS: m/z=486.0 $[M+H]^+$. $^1H$ NMR (400 MHz, Methanol-d4) δ 9.28 (s, 1H), 8.39 (d, J=5.9 Hz, 1H), 8.35 (s, 1H), 7.96 (t, J=7.6 Hz, 1H), 7.67 (s, 1H), 7.65 (s, 1H), 7.46 (d, J=9.7 Hz, 1H), 6.86 (td, J=54.9, 5.1 Hz, 1H), 6.21 (td, J=12.8, 5.1 Hz, 1H), 3.01 (s, 3H).

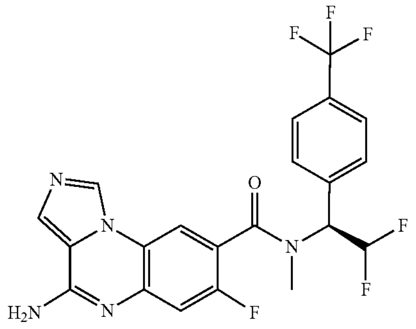 [SMILES: CN(C(=O)c1cc2c(cc1F)nc(N)c1cncn12)[C@@H](c1ccc(C(F)(F)F)cc1)C(F)F]

Example Fb-9: (S)-4-amino-N-(2,2-difluoro-1-(4-(trifluoromethyl)phenyl)ethyl)-7-fluoro-N-methylimidazo[1,5-a]quinoxaline-8-carboxamide. Prepared following general procedure II-F starting with 4-((tert-butoxycarbonyl)amino)-7-fluoroimidazo[1,5-a]quinoxaline-8-carboxylic acid Af-1 and (S)-2,2-difluoro-N-methyl-1-(4-(trifluoromethyl)phenyl)ethan-1-amine hydrochloride Eal-2. ES/MS: m/z=468.0 $[M+H]^+$. $^1H$ NMR (400 MHz, Methanol-d4) δ 9.30 (s, 1H), 8.46 (d, J=5.8 Hz, 1H), 8.37 (s, 1H), 7.80 (q, J=8.5 Hz, 3.8H, major rotamer), 7.68 (s, 0.2H, minor rotamer), 7.48 (d, J=9.8 Hz, 1H), 6.82 (td, J=54.8, 5.0 Hz, 1H), 6.10 (td, J=13.2, 4.9 Hz, 0.9H, major rotamer), 5.30 (s, 0.1H, minor rotamer), 3.07 (s, 1H, minor rotamer), 2.98 (d, J=1.1 Hz, 2H, major rotamer).

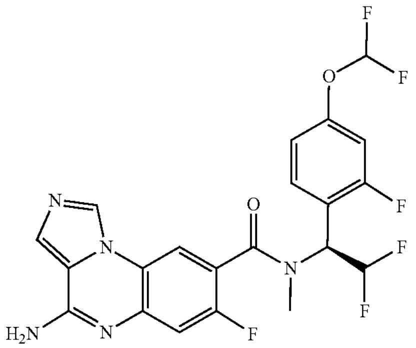 [SMILES: CN(C(=O)c1cc2c(cc1F)nc(N)c1cncn12)[C@@H](c1ccc(OC(F)F)cc1F)C(F)F]

Example Fb-10: (S)-4-amino-N-(1-(4-(difluoromethoxy)-2-fluorophenyl)-2,2-difluoroethyl)-7-fluoro-N-methylimidazo[1,5-a]quinoxaline-8-carboxamide. Prepared following general procedure II-F starting with 4-((tert-butoxycarbonyl)amino)-7-fluoroimidazo[1,5-a]quinoxaline-8-carboxylic acid Af-1 and (S)-1-(4-(difluoromethoxy)-2-fluorophenyl)-2,2-difluoro-N-methylethan-1-amine hydrochloride Eal-3. ES/MS: m/z=484.0 $[M+H]^+$. $^1H$ NMR (400 MHz, Methanol-d4) δ 9.31 (s, 1H), 8.40 (d, J=5.8 Hz, 1H), 8.37 (s, 1H), 7.78 (t, J=8.6 Hz, 1H), 7.45 (d, J=9.6 Hz, 1H), 7.23-7.08 (m, 2H), 6.98 (t, J=73.2 Hz, 1H), 6.78 (td, J=55.0, 5.1 Hz, 1H), 6.18 (td, J=13.0, 5.1 Hz, 1H), 2.97 (s, 3H).

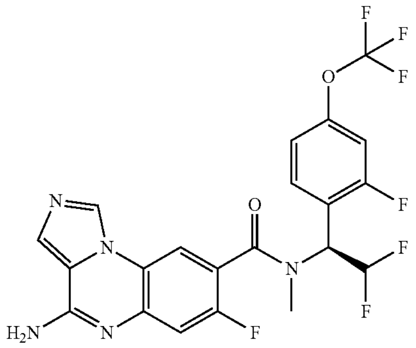 [SMILES: CN(C(=O)c1cc2c(cc1F)nc(N)c1cncn12)[C@@H](c1ccc(OC(F)(F)F)cc1F)C(F)F]

Example Fb-11: (S)-4-amino-N-(2,2-difluoro-1-(2-fluoro-4-(trifluoromethoxy)phenyl)ethyl)-7-fluoro-N-methylimidazo[1,5-a]quinoxaline-8-carboxamide. Prepared following general procedure II-F starting with 4-((tert-butoxycarbonyl)amino)-7-fluoroimidazo[1,5-a]quinoxaline-8-carboxylic acid Af-1 and (S)-2,2-difluoro-1-(2-fluoro-4-(trifluoromethoxy)phenyl)-N-methylethan-1-amine hydrochloride Eal-4. ES/MS: m/z=502.0 $[M+H]^+$. $^1H$ NMR (400 MHz, Methanol-d4) δ 9.31 (s, 1H), 8.40 (d, J=5.8 Hz, 1H), 8.37 (s, 1H), 7.78 (t, J=8.6 Hz, 1H), 7.45 (d, J=9.6 Hz, 1H), 7.23-7.08 (m, 2H), 6.98 (t, J=73.2 Hz, 1H), 6.78 (td, J=55.0, 5.1 Hz, 1H), 6.18 (td, J=13.0, 5.1 Hz, 1H), 2.97 (s, 3H).

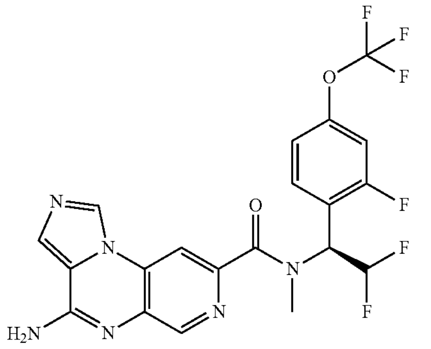 [SMILES: CN(C(=O)c1cc2c(cn1)nc(N)c1cncn12)[C@@H](c1ccc(OC(F)(F)F)cc1F)C(F)F]

Example Fb-12: (S)-4-amino-N-(2,2-difluoro-1-(2-fluoro-4-(trifluoromethoxy)phenyl)ethyl)-N-methylimidazo[1,5-a]pyrido[3,4-e]pyrazine-8-carboxamide. Prepared following general procedure II-F starting with 4-((tert-butoxycarbonyl)amino)imidazo[1,5-a]pyrido[3,4-e]pyrazine-8-carboxylic acid Af-6 and (S)-2,2-difluoro-1-(2-fluoro-4-(trifluoromethoxy)phenyl)-N-methylethan-1-amine hydrochloride Eal-4. ES/MS: m/z=485.0 $[M+H]^+$. $^1H$ NMR (400 MHz, Methanol-d4) δ 9.34 (d, J=11.1 Hz, 1H), 8.82 (d, J=14.7 Hz, 1H), 8.61 (s, 0.3H, minor rotamer), 8.49 (s, 0.7H, major rotamer), 8.26 (s, 1H), 7.89 (t, J=8.6 Hz, 1H), 7.29 (t, J=10.1 Hz, 2H), 6.83 (td, J=55.0, 4.9 Hz, 1H), 6.28 (s, 0.3H, minor rotamer), 6.16 (dd, J=14.0, 8.9 Hz, 0.7H, major rotamer), 3.12 (s, 2H, major rotamer), 3.04 (s, 1H, minor rotamer).

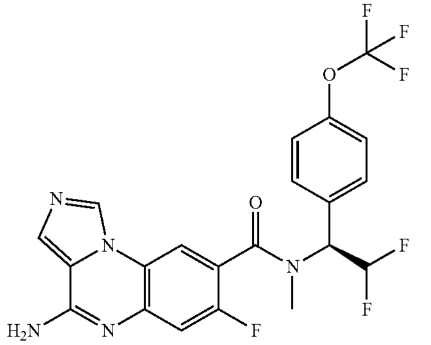 [SMILES: CN(C(=O)c1cc2c(cc1F)nc(N)c1cncn12)[C@@H](c1ccc(OC(F)(F)F)cc1)C(F)F]

Example Fb-13: (S)-4-amino-N-(2,2-difluoro-1-(4-(trifluoromethoxy)phenyl)ethyl)-7-fluoro-N-methylimidazo[1,5-a]quinoxaline-8-carboxamide. Prepared following general procedure II-F starting with 4-((tert-butoxycarbonyl)amino)-7-fluoroimidazo[1,5-a]quinoxaline-8-carboxylic acid Af-1 and (S)-2,2-difluoro-N-methyl-1-(4-(trifluoromethoxy)phenyl)ethan-1-amine hydrochloride Eal-5. ES/MS: m/z=484.0 $[M+H]^+$. $^1H$ NMR (400 MHz, Methanol-d4) δ 9.31 (s, 1H), 8.46 (d, J=5.8 Hz, 1H), 8.39 (d, J=0.6 Hz, 1H), 7.73-7.63 (m, 1.6H, major rotamer), 7.57 (d, J=8.4 Hz, 0.4H, minor rotamer), 7.48 (d, J=9.6 Hz, 1H), 7.43-7.37 (m, 2H), 6.77 (td, J=54.8, 5.0 Hz, 1H), 6.05 (td, J=13.3, 5.0 Hz, 0.9H, major rotamer), 5.22 (s, 0.1H, minor rotamer), 3.07 (s, 0.6H, minor rotamer), 2.96 (d, J=1.2 Hz, 2.4H, major rotamer).

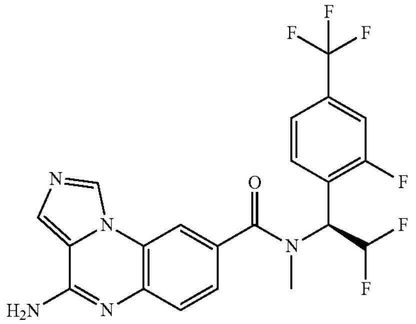 [SMILES: CN(C(=O)c1ccc2nc(N)c3cncn3c2c1)[C@@H](c1ccc(C(F)(F)F)cc1F)C(F)F]

Example Fb-14: (S)-4-amino-N-(2,2-difluoro-1-(2-fluoro-4-(trifluoromethyl)phenyl)ethyl)-N-methylimidazo[1,5-a]quinoxaline-8-carboxamide. Prepared following general procedure II-F starting with 4-((tert-butoxycarbonyl)amino)imidazo[1,5-a]quinoxaline-8-carboxylic acid Ae-1 and (S)-2,2-difluoro-1-(2-fluoro-4-(trifluoromethyl)phenyl)-N-methylethan-1-amine hydrochloride Eal-1. ES/MS: m/z=468.0 $[M+H]^+$. $^1H$ NMR (400 MHz, Methanol-d4) δ 9.35 (s, 1H), 8.42 (d, J=1.3 Hz, 2H), 7.96 (s, 1H), 7.77-7.61 (m, 4H), 6.85 (t, J=54.7 Hz, 1H), 6.20 (s, 1H), 3.06 (s, 3H).

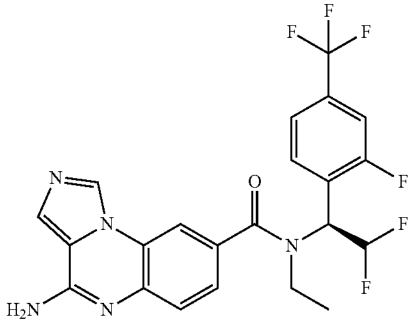 [SMILES: CCN(C(=O)c1ccc2nc(N)c3cncn3c2c1)[C@@H](c1ccc(C(F)(F)F)cc1F)C(F)F]

Example Fb-15: (S)-4-amino-N-(2,2-difluoro-1-(2-fluoro-4-(trifluoromethyl)phenyl)ethyl)-N-ethylimidazo[1,5-a]quinoxaline-8-carboxamide. Prepared following general procedure II-F starting with 4-((tert-butoxycarbonyl)amino)imidazo[1,5-a]quinoxaline-8-carboxylic acid Ae-1 and (S)—N-ethyl-2,2-difluoro-1-(2-fluoro-4-(trifluoromethyl)phenyl)ethan-1-amine Eaq-1. ES/MS: m/z=482.0 $[M+H]^+$. $^1H$ NMR (400 MHz, Methanol-d4) δ 9.35 (s, 1H), 8.41 (s, 2H), 8.11 (d, J=16.6 Hz, 1H), 7.75-7.59 (m, 4H), 6.95 (d, J=55.7 Hz, 1H), 5.61 (s, 1H), 3.64-3.42 (m, 2H), 1.06 (t, J=7.1 Hz, 3H).

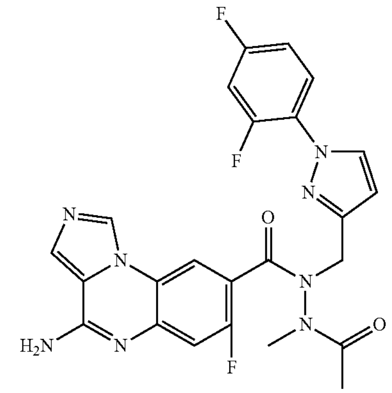 [SMILES: CC(=O)N(C)N(Cc1ccn(-c2ccc(F)cc2F)n1)C(=O)c1cc2c(cc1F)nc(N)c1cncn12]

Example Fb-16: N'-acetyl-4-amino-N-((1-(2,4-difluorophenyl)-1H-pyrazol-3-yl)methyl)-7-fluoro-N'-methylimidazo[1,5-a]quinoxaline-8-carbohydrazide. Prepared following general procedure II-F starting with 4-((tert-butoxycarbonyl)amino)-7-fluoroimidazo[1,5-a]quinoxaline-8-carboxylic acid Af-1 and N'-((1-(2,4-difluorophenyl)-1H-pyrazol-3-yl)methyl)-N-methylacetohydrazide Dc-5. ES/MS: m/z 509.3 $[M+H]^+$. $^1H$ NMR (400 MHz, Methanol-d4) δ 9.19 (d, J=42.0 Hz, 1H), 8.73-8.45 (m, 1H), 8.44-8.24 (m, 2H), 8.05 (t, J=18.2 Hz, 2H), 7.45 (dd, J=34.4, 10.8 Hz, 1H), 7.35-6.88 (m, 3H), 6.83-6.23 (m, 1H), 5.19 (dd, J=47.7, 13.5 Hz, 1H), 3.30-3.12 (m, 3H), 2.01 (s, 2H), 1.86 (d, J=25.9 Hz, 2H).

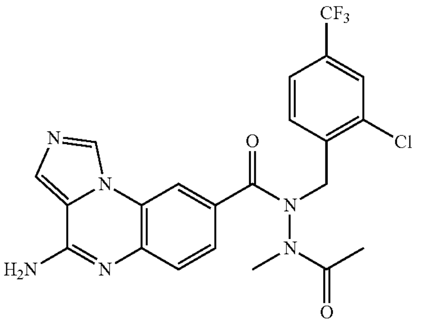 [SMILES: CC(=O)N(C)N(Cc1ccc(C(F)(F)F)cc1Cl)C(=O)c1ccc2nc(N)c3cncn3c2c1]

Example Fb-17: N'-acetyl-4-amino-N-(2-chloro-4-(trifluoromethyl)benzyl)-N'-methylimidazo[1,5-a]quinoxaline-8-carbohydrazide. Prepared following general procedure II-F starting with 4-((tert-butoxycarbonyl)amino)imidazo[1,5-a]quinoxaline-8-carboxylic acid Ae-1 and N'-(2-chloro-4-(trifluoromethyl)benzyl)-N-methylacetohydrazide Dc-2. ES/MS: m/z=491.1 $[M+H]^+$. $^1H$ NMR (400 MHz, DMSO-$d_6$) δ 9.43 (s, 0.58H major rotamer), 9.39 (s, 0.42H minor rotamer), 8.89 (brs, 2H), 8.55-8.23 (m, 2H), 8.02-7.74 (m, 3H), 7.69-7.48 (m, 2H), 5.33-5.02 (m, 1H+0.42H minor rotamer), 4.60 (d, J=15.7 Hz, 0.58H major rotamer), 3.16 (s, 1.74H major rotamer), 2.91 (s, 1.26H minor rotamer), 1.75 (s, 3H).

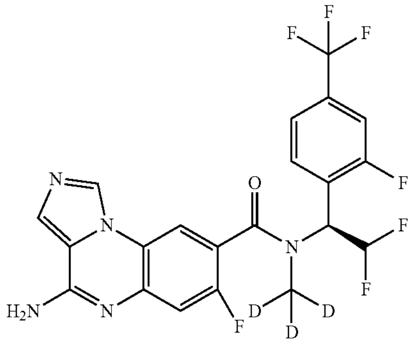 [SMILES: [2H]C([2H])([2H])N(C(=O)c1cc2c(cc1F)nc(N)c1cncn12)[C@@H](c1ccc(C(F)(F)F)cc1F)C(F)F]

Example Fb-18: (S)-4-amino-N-(2,2-difluoro-1-(2-fluoro-4-(trifluoromethyl)phenyl)ethyl)-7-fluoro-N-(methyl-d3)imidazo[1,5-a]quinoxaline-8-carboxamide. Prepared following general procedure II-F starting with 4-((tert-butoxycarbonyl)amino)-7-fluoroimidazo[1,5-a]quinoxaline-8-carboxylic acid Af-1 and (S)-2,2-difluoro-1-(2-fluoro-4-(trifluoromethyl)phenyl)-N-(methyl-d3)ethan-1-amine Eal-7. ES/MS: m/z=489.0 $[M+H]^+$. $^1H$ NMR (400 MHz, Methanol-d4) δ 9.28 (s, 1H), 8.39 (d, J=5.9 Hz, 1H), 8.33 (s, 1H), 7.96 (t, J=7.5 Hz, 1H), 7.66 (d, J=8.9 Hz, 2H), 7.43 (d, J=9.8 Hz, 1H), 6.86 (td, J=54.9, 5.2 Hz, 1H), 6.21 (td, J=12.8, 5.2 Hz, 1H).

General Procedure III-F for the Synthesis of Compounds Fc:

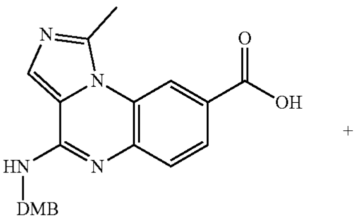

Ac-1

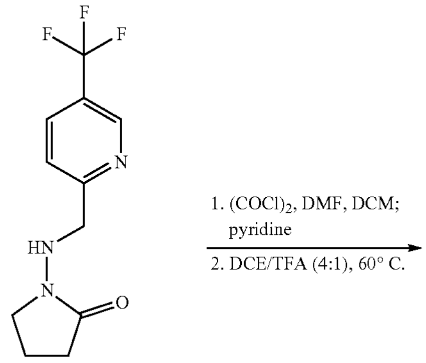

Da-5

-continued

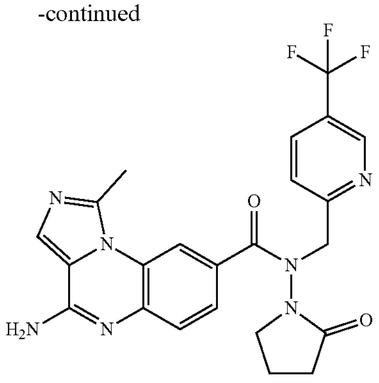

Example Fc-1

Example Fc-1: 4-amino-1-methyl-N-(2-oxopyrrolidin-1-yl)-N-[[5-(trifluoromethyl)-2-pyridyl]methyl]imid-azo[1,5-a]quinoxaline-8-carboxamide. To a stirred suspension of 4-[(2,4-dimethoxyphenyl)methylamino]-1-methyl-imidazo[1,5-a]quinoxaline-8-carboxylic acid Ac-1 (50 mg, 0.13 mmol) in DCM (2 mL) under argon was added oxalyl chloride (2.0 M in DCM, 0.1 mL, 0.19 mmol) followed by DMF (2 drops). The reaction was monitored by LCMS (MeOH quench) and after 30 minutes, additional oxalyl chloride (typically 0.5-0.75 equiv.) and DMF (1-2 drops) were added. After complete conversion to the acid chloride as indicated by LCMS (15 additional minutes), pyridine (0.08 mL, 1 mmol) was added followed 1-(((5-(trifluoromethyl)pyridin-2-yl)methyl)amino)pyrrolidin-2-one Da-5 (50 mg, 0.19 mmol). After stirring for 1 hour, the reaction was diluted with ethyl acetate (10 mL), washed with brine (3 mL), dried over magnesium sulfate, and concentrated. The residue was purified by flash column chromatography (silica gel, 0-20% methanol/DCM) to remove excess hydrazide and the coupled product was collected and concentrated. The residue was then resuspended in 1,2-dichloroethane (1.6 mL) and treated with trifluoroacetic acid (0.4 mL). The reaction was heated to 60° C. for two hours, then cooled to room temperature and concentrated under reduced pressure. The crude residue was purified by preparative HPLC to afford the desired product Fc-1. ES/MS: m/z=483.9 $[M+H]^+$. $^1H$ NMR (400 MHz, DMSO-d6) δ 9.00 (s, 1H), 8.40 (s, 1H), 8.30 (dd, J=8.3, 2.4 Hz, 1H), 8.25 (s, 1H), 7.94 (d, J=8.2 Hz, 1H), 7.68 (s, 2H), 5.20 (d, J=16.1 Hz, 1H), 4.94 (d, J=16.0 Hz, 1H), 3.67-3.54 (m, 1H), 3.38-3.25 (m, 1H), 3.02 (s, 3H), 2.29-2.17 (m, 1H), 2.10-1.95 (m, 1H), 1.94-1.83 (m, 1H), 1.71-1.55 (m, 1H).

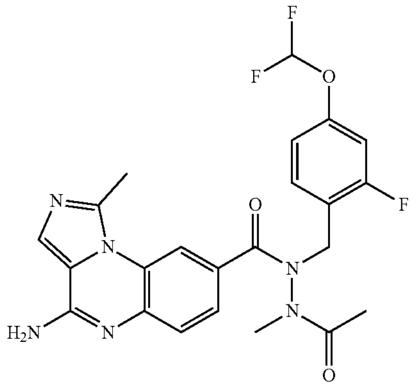 [SMILES: CC(=O)N(C)N(Cc1ccc(OC(F)F)cc1F)C(=O)c1ccc2nc(N)c3cnc(C)n3c2c1]

Example Fc-2: N'-acetyl-4-amino-N-(4-(difluoromethoxy)-2-fluorobenzyl)-N',1-dimethylimidazo[1,5-a]quinoxaline-8-carbohydrazide. Prepared using general procedure III-F starting with 4-[(2,4-dimethoxyphenyl)methylamino]-1-methyl-imidazo[1,5-a]quinoxaline-8-carboxylic acid Ac-1 and N'-(4-(difluoromethoxy)-2-fluorobenzyl)-N-methylacetohydrazide Da-2. ES/MS: m/z=487.2 $[M+H]^+$. $^1H$ NMR (400 MHz, DMSO-$d_6$) δ 9.15 (brs, 2H), 8.33 (d, J=4.3 Hz, 1H), 8.18 (d, J=43.8 Hz, 1H), 7.79-7.48 (m, 3H), 7.41-7.02 (m, 3H), 5.00 (d, J=14.7 Hz, 1H), 4.86 (d, J=14.5 Hz, 0.5H $1^{st}$ rotamer), 4.60 (d, J=14.8 Hz, 0.5H $2^{nd}$ rotamer), 3.05 (s, 1.5H $1^{st}$ rotamer), 3.04 (s, 1.5H $2^{nd}$ rotamer), 3.00 (s, 1.5H $1^{st}$ rotamer), 2.98 (s, 1.5H $2^{nd}$ rotamer), 1.79 (s, 1.5H $1^{st}$ rotamer), 1.69 (s, 1.5H $2^{nd}$ rotamer).

General Procedure IV-F for the Synthesis of Compounds Fd:

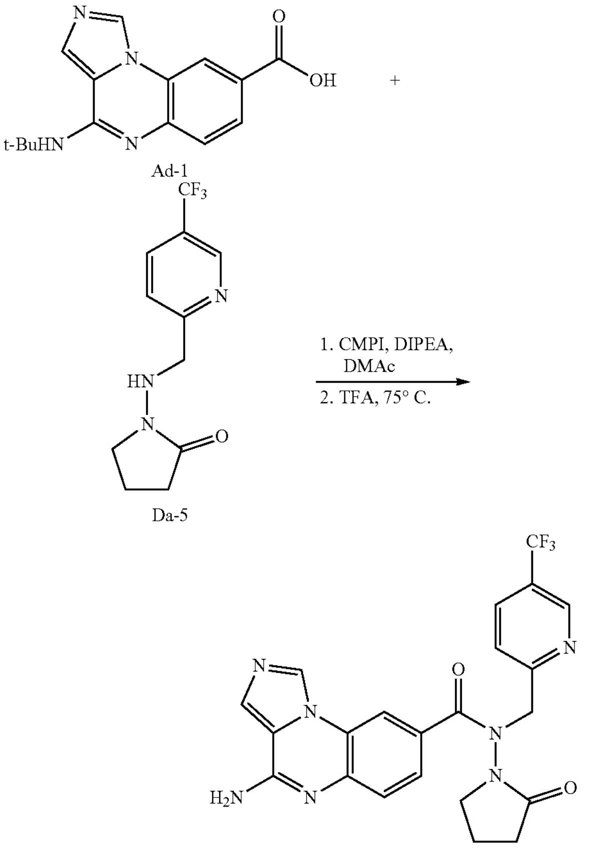

Ad-1

Da-5

Example Fd-1

Example Fd-1: 4-amino-N-(2-oxopyrrolidin-1-yl)-N-((5-(trifluoromethyl)pyridin-2-yl)methyl)imidazo[1,5-a]quinoxaline-8-carboxamide. 4-(tert-butylamino)imidazo[1,5-a]quinoxaline-8-carboxylic acid Ad-1 (40 mg, 0.14 mmol), 1-(((5-(trifluoromethyl)pyridin-2-yl)methyl)amino)pyrrolidin-2-one Da-5 (40 mg, 0.15 mmol) and 2-chloro-1-methyl-pyridin-1-ium iodide (47 mg, 0.18 mmol) were dissolved in DMAc (2.5 mL) and DIPEA (50 PL, 0.28 mmol) was added. The resulting mixture was stirred at 30° C. overnight and then the reaction mixture was diluted with water and EtOAc. The organic layer was separated and washed with 10% aq. LiCl, brine. The Organic layer was dried over $MgSO_4$, filtered, concentrated, and purified by silica gel column chromatography. The resulting product was suspended in TFA (1.0 mL) and heated to 75° C. overnight. The TFA was then removed under reduced pressure and the residue was purified by preparative HPLC to afford 4-amino-N-(2-oxopyrrolidin-1-yl)-N-((5-(trifluoromethyl)pyridin-2-yl)methyl)imidazo[1,5-a]quinoxaline-8-carboxamide Fd-1. ES/MS: m/z=469.9 $[M+H]^+$. $^1H$ NMR (400 MHz, DMSO-d6) δ 9.44 (s, 1H), 9.10-8.78 (m, 2H), 8.48 (s, 1H), 8.35-8.00 (m, 2H), 7.87 (dd, J=27.4, 8.2 Hz, 1H), 7.66-7.53 (m, 1H), 5.22 (d, J=16.0 Hz, 1H), 4.90 (d, J=15.9 Hz, 1H), 3.69-3.61 (m, 1H), 3.39-3.32 (m, 1H), 2.28-2.10 (m, 2H), 2.01-1.79 (m, 2H).

General Procedure V-F for the Synthesis of Compounds Fe:

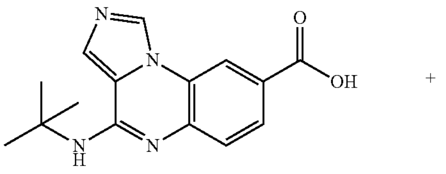

Ad-1

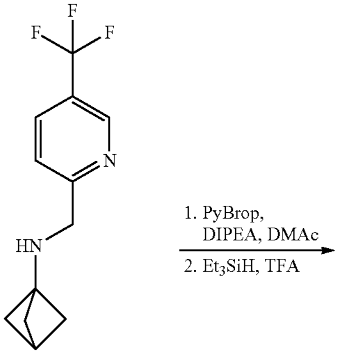

Ec-1

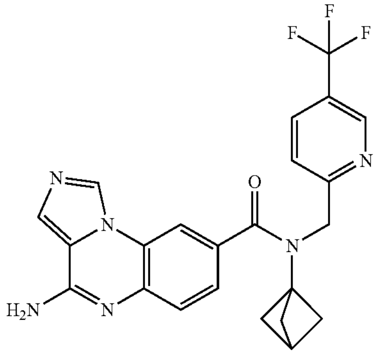

Example Fe-1

Example Fe-1: 4-amino-N-(bicyclo[1.1.1]pentan-1-yl)-N-((5-(trifluoromethyl)pyridin-2-yl)methyl)imidazo[1,5-a]quinoxaline-8-carboxamide. To a solution of 4-(tert-butylamino)imidazo[1,5-a]quinoxaline-8-carboxylic acid (44.4 mg, 0.156 mmol) and N-[[5-(trifluoromethyl)-2-pyridyl]methyl]bicyclo[1.1.1]pentan-1-amine Ec-1 (41.6 mg, 0.172 mmol) in DMAc (3 mL), was added DIPEA (0.0981 mL, 0.547 mmol) followed by PyBroP (94.6 mg, 0.203 mmol).

The reaction was stirred at room temperature overnight, then diluted with EtOAc and washed with 5% LiCl solution twice, saturated sodium bicarbonate twice, and brine. The organic extract was dried sodium sulfate and concentrated under reduced pressure. The crude residue was purified by flash chromatography. A solution of N-(1-bicyclo[1.1.1]pentanyl)-4-(tert-butylamino)-N-[[5-(trifluoromethyl)-2-pyridyl]methyl]imidazo[1,5-a]quinoxaline-8-carboxamide (25 mg, 0.049 mmol) and triethylsilane (0.020 mL, 0.13 mmol) in TFA (3 mL) was heated at 75° C. until disappearance of starting material. The reaction mixture was concentrated to dryness. The crude residue was purified by preparative HPLC. ES/MS: m/z=453.0 $[M+H]^+$. $^1H$ NMR (400 MHz, Methanol-d4) δ 9.32 (s, 1H), 9.01-8.63 (m, 1H), 8.59-8.26 (m, 2H), 8.15 (d, J=8.3 Hz, 1H), 7.71 (d, J=7.7 Hz, 2H), 4.96 (s, 2H), 2.33 (s, 1H), 2.12-1.58 (m, 6H).

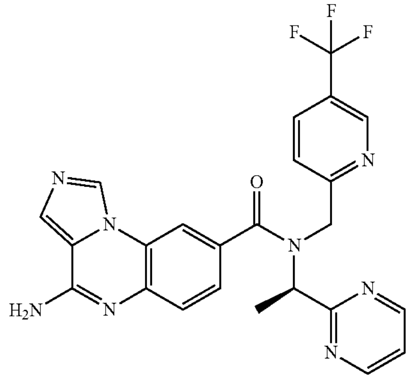 [SMILES: C[C@H](c1ncccn1)N(Cc1ccc(C(F)(F)F)cn1)C(=O)c1ccc2nc(N)c3cncn3c2c1]

Example Fe-2: (R)-4-amino-N-(1-(pyrimidin-2-yl)ethyl)-N-((5-(trifluoromethyl)pyridin-2-yl)methyl)imidazo[1,5-a]quinoxaline-8-carboxamide. Prepared using general procedure V-F starting with 4-((tert-butoxycarbonyl)amino)imidazo[1,5-a]quinoxaline-8-carboxylic acid Ae-1 and (R)-1-(pyrimidin-2-yl)-N-((5-(trifluoromethyl)pyridin-2-yl)methyl)ethan-1-amine Ec-2. ES/MS: m/z=493.2 $[M+H]^+$. $^1H$ NMR (400 MHz, DMSO-$d_6$) δ 9.45 (s, 0.75H major rotamer), 9.31 (s, 0.25H minor rotamer), 9.25 (brs, 2H), 8.87 (s, 0.25H minor rotamer), 8.85 (s, 0.75H major rotamer), 8.80 (s, 1H), 8.78 (s, 1H), 8.55 (s, 0.75H major rotamer), 8.39 (s, 0.75H major rotamer), 8.38-8.30 (m, 0.5H minor rotamer), 8.14-8.10 (m, 0.75H major rotamer), 8.03 (s, 0.25H minor rotamer), 7.76-7.47 (m, 3H), 7.41 (t, J=4.9 Hz, 1H), 5.79 (brs, 0.25H minor rotamer), 5.38-5.24 (m, 0.75H major rotamer), 4.95 (d, J=16.7 Hz, 0.75H major rotamer), 4.84 (brs, 0.5H minor rotamer), 4.57 (d, J=16.7 Hz, 0.75H major rotamer), 1.65 (d, J=6.9 Hz, 2.25H major rotamer), 1.62-1.57 (m, 0.75H minor rotamer).

General Procedure VI-F for Synthesis of Compound Ff

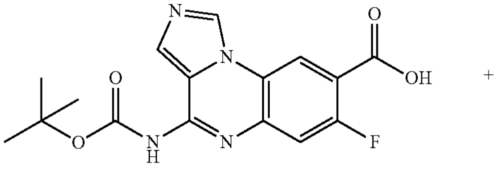

Af-1

-continued

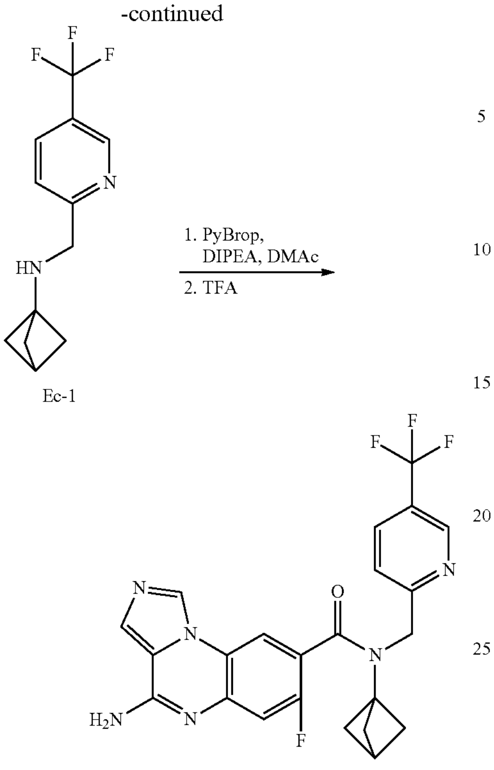

Ec-1

Example Ff-1

Example Ff-1: 4-amino-N-(bicyclo[1.1.1]pentan-1-yl)-7-fluoro-N-((5-(trifluoromethyl)pyridin-2-yl)methyl)imidazo[1,5-a]quinoxaline-8-carboxamide. To a solution of 4-(tert-butoxycarbonylamino)-7-fluoro-imidazo[1,5-a]quinoxaline-8-carboxylic acid Af-1 (50.0 mg, 0.144 mmol) and N-[[5-(trifluoromethyl)-2-pyridyl]methyl]bicyclo[1.1.1]pentan-1-amine Ec-1 (35.0 mg, 0.144 mmol) in DMAc (2 mL), was added DIPEA (0.0907 mL, 0.505 mmol) followed by PyBroP (87.5 mg, 0.188 mmol). The reaction was stirred at room temperature overnight, then diluted with EtOAc and washed with 5% LiCl solution twice, saturated sodium bicarbonate twice, and brine. The organic extract was dried sodium sulfate and concentrated under reduced pressure. The crude residue was purified by flash chromatography to provide tert-butyl tert-butyl (8-(bicyclo[1.1.1]pentan-1-yl((5-(trifluoromethyl)pyridin-2-yl)methyl)carbamoyl)-7-fluoroimidazo[1,5-a]quinoxalin-4-yl)carbamate.

A solution of tert-butyl tert-butyl (8-(bicyclo[1.1.1]pentan-1-yl((5-(trifluoromethyl)pyridin-2-yl)methyl)carbamoyl)-7-fluoroimidazo[1,5-a]quinoxalin-4-yl)carbamate (35.0 mg, 0.0613 mmol) and 2,2,2-trifluoroacetic acid (0.110 mL, 1.44 mmol) in DCM (3 mL) was stirred at room temperature overnight. The reaction mixture was concentrated to dryness. The crude residue was purified by preparative HPLC. ES/MS: m/z=471.0 $[M+H]^+$. $^1$H NMR (400 MHz, Methanol-d4) δ 9.31 (s, 1H), 9.17 (s, 0.3H, minor rotamer), 8.91 (d, J=10.4 Hz, 1H), 8.47 (d, J=5.8 Hz, 1H), 8.39 (s, 1H), 8.34 (s, 0.2H, minor rotamer), 8.19 (d, J=8.1 Hz, 1H), 8.08 (d, J=8.4 Hz, 0.3H, minor rotamer), 7.70 (d, J=8.3 Hz, 1H), 7.49 (d, J=9.4 Hz, 1H), 7.37 (d, J=9.6 Hz, 0.3H, minor rotamer), 5.12-4.97 (m, 2H), 2.28 (s, 1H), 1.84 (s, 6H).

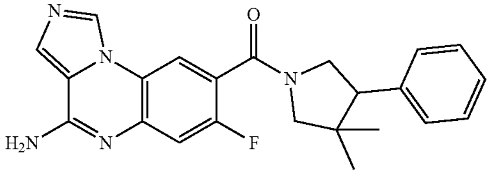 [SMILES: CC1(C)CN(C(=O)c2cc3c(cc2F)nc(N)c2cncn23)CC1c1ccccc1]

Example Ff-2: (4-amino-7-fluoroimidazo[1,5-a]quinoxalin-8-yl)(3,3-dimethyl-4-phenylpyrrolidin-1-yl)methanone. Prepared using general procedure VI-F starting with 4-(tert-butoxycarbonylamino)-7-fluoro-imidazo[1,5-a]quinoxaline-8-carboxylic acid Af-1 and commercial 3,3-dimethyl-4-phenylpyrrolidine. ES/MS: m/z=404.2 $[M+H]^+$. $^1$H NMR (400 MHz, DMSO-$d_6$) δ 9.38 (d, J=3.3 Hz, 1H), 9.04 (brs, 2H), 8.52 (dd, J=6.2, 1.8 Hz, 1H), 8.29 (s, 1H), 7.45-7.21 (m, 4H), 7.21-7.16 (m, 1H), 4.00-3.90 (m, 1H), 3.86-3.57 (m, 1H), 3.47-3.14 (m, 3H), 1.11 (s, 1.5H $1^{st}$ rotamer), 0.99 (s, 1.5H $2^{nd}$ rotamer), 0.80 (s, 1.5H $1^{st}$ rotamer), 0.68 (s, 1.5H 2md rotamer).

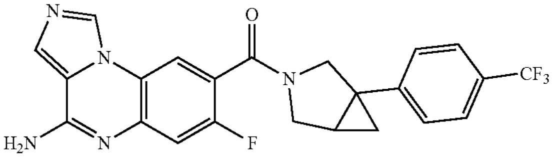 [SMILES: Nc1nc2cc(F)c(C(=O)N3CC4CC4(c4ccc(C(F)(F)F)cc4)C3)cc2n2cncc12]

Example Ff-3: (4-amino-7-fluoroimidazo[1,5-a]quinoxalin-8-yl)(1-(4-(trifluoromethyl)phenyl)-3-azabicyclo[3.1.0]hexan-3-yl)methanone. Prepared using general procedure VI-F starting with 4-(tert-butoxycarbonylamino)-7-fluoro-imidazo[1,5-a]quinoxaline-8-carboxylic acid Af-1 and commercial 1-(4-(trifluoromethyl)phenyl)-3-azabicyclo[3.1.0]hexane. ES/MS: m/z=456.0 $[M+H]^+$. $^1$H NMR (400 MHz, DMSO-$d_6$) δ 9.30 (d, J=2.7 Hz, 1H), 8.87 (brs, 2H), 8.46 (d, J=6.2 Hz, 1H), 8.25 (s, 1H), 7.69 (d, J=8.2 Hz, 1H), 7.62 (d, J=8.2 Hz, 1H), 7.50 (d, J=8.1 Hz, 1H), 7.43-7.36 (m, 2H), 4.44 (d, J=11.7 Hz, 0.5H $1^{st}$ rotamer), 4.11 (d, J=11.9 Hz, 0.5H $2^{nd}$ rotamer), 3.94-3.70 (m, 2H), 3.68-3.62 (m, 0.5H $1^{st}$ rotamer), 3.42 (d, J=10.7 Hz, 0.5H $2^{nd}$ rotamer), 2.29-2.08 (m, 1H), 1.29-1.16 (m, 1H), 0.99-0.96 (m, 1H).

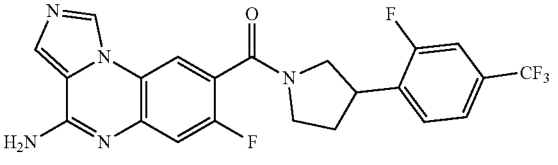 [SMILES: Nc1nc2cc(F)c(C(=O)N3CCC(c4ccc(C(F)(F)F)cc4F)C3)cc2n2cncc12]

Example Ff-4: (4-amino-7-fluoroimidazo[1,5-a]quinoxalin-8-yl)(3-(2-fluoro-4-(trifluoromethyl)phenyl)pyrrolidin-1-yl)methanone. Prepared using general procedure VI-F starting with 4-(tert-butoxycarbonylamino)-7-fluoro-imidazo[1,5-a]quinoxaline-8-carboxylic acid Af-1 and commercial 3-(2-fluoro-4-(trifluoromethyl)phenyl)pyrrolidine. ES/MS: m/z=462.2 $[M+H]^+$. $^1$H NMR (400 MHz, DMSO-$d_6$) δ 9.32 (d, J=5.3 Hz, 1H), 8.90 (brs, 2H), 8.53-8.44 (m, 1H), 8.26 (s, 1H), 7.80-7.54 (m, 3H), 7.45-7.32 (m, 1H), 4.05 (dd, J=11.9, 7.7 Hz, 1H), 3.84-3.37 (m, 4H), 2.43-2.03 (m, 3H).

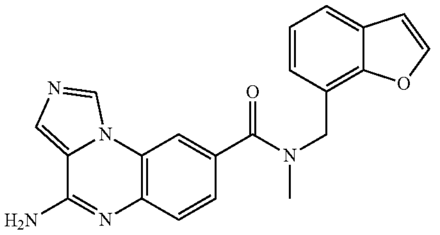 [SMILES: CN(Cc1cccc2ccoc12)C(=O)c1ccc2nc(N)c3cncn3c2c1]

Example Ff-5: 4-amino-N-(benzofuran-7-ylmethyl)-N-methylimidazo[1,5-a]quinoxaline-8-carboxamide. Prepared using general procedure VI-F starting with 4-((tert-butoxycarbonyl)amino)imidazo[1,5-a]quinoxaline-8-carboxylic acid Ae-1 and 1-(benzofuran-7-yl)-N-methylmethanamine Ed-3. ES/MS: m/z=372.2 $[M+H]^+$. $^1H$ NMR (400 MHz, DMSO-$d_6$) δ 9.49 (s, 0.5H $1^{st}$ rotamer), 9.41 (s, 0.5H $2^{nd}$ rotamer), 9.24 (brs, 2H), 8.53 (s, 1H), 8.39 (s, 1H), 8.08 (s, 0.5H 1 rotamer), 7.98 (s, 0.5H $2^{nd}$ rotamer), 7.68-7.56 (m, 3H), 7.39-7.12 (m, 2H), 7.05 (s, 0.5H 1 rotamer), 6.95 (s, 0.5H $2^{nd}$ rotamer), 5.04 (s, 1H), 4.84 (s, 1H), 2.99 (s, 3H).

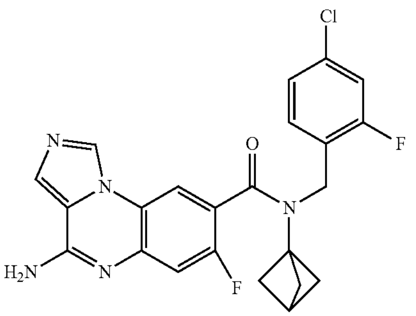 [SMILES: Nc1nc2cc(F)c(C(=O)N(Cc3ccc(Cl)cc3F)C34CC(C3)C4)cc2n2cncc12]

Example Ff-6: 4-amino-N-(bicyclo[1.1.1]pentan-1-yl)-N-(4-chloro-2-fluorobenzyl)-7-fluoroimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and N-(4-chloro-2-fluorobenzyl)bicyclo[1.1.1]pentan-1-amine Ec-5. ES/MS: m/z=454.1 $[M+H]^+$. $^1H$ NMR (400 MHz, DMSO-$d_6$) δ 9.37 (s, 1H), 8.91 (brs, 2H), 8.50 (d, J=6.2 Hz, 1H), 8.28 (s, 1H), 7.54 (d, J=8.7 Hz, 1H), 7.46 (d, J=10.1 Hz, 1H), 7.44-7.25 (m, 2H), 4.88 (d, J=16.5 Hz, 1H), 4.67 (d, J=16.5 Hz, 1H), 2.13 (brs, 1H), 1.71 (s, 6H).

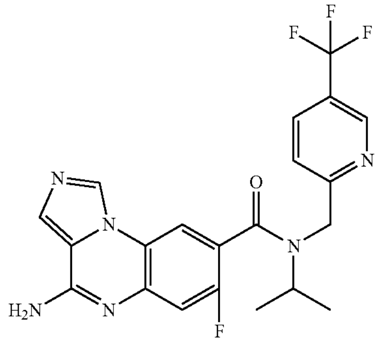 [SMILES: CC(C)N(Cc1ccc(C(F)(F)F)cn1)C(=O)c1cc2c(cc1F)nc(N)c1cncn12]

Example Ff-7: 4-amino-7-fluoro-N-isopropyl-N-((5-(trifluoromethyl)pyridin-2-yl)methyl)imidazo[1,5-a]quinoxaline-8-carboxamide. Prepared following general procedure VI-F starting with 4-(tert-butoxycarbonylamino)-7-fluoro-imidazo[1,5-a]quinoxaline-8-carboxylic acid Af-1 and N-((5-(trifluoromethyl)pyridin-2-yl)methyl)propan-2-amine Ed-1. ES/MS: m/z=447.0 $[M+H]^+$. $^1H$ NMR (400 MHz, Methanol-d4) δ 9.32 (d, J=0.7 Hz, 0.8H, major rotamer), 9.18 (s, 0.2H, minor rotamer), 8.97-8.88 (m, 0.8H, major rotamer), 8.86 (d, J=2.2 Hz, 0.2H, minor rotamer), 8.48 (d, J=5.8 Hz, 0.8H, major rotamer), 8.40 (d, J=0.6 Hz, 0.8H, major rotamer), 8.34 (t, J=2.9 Hz, 0.4H, minor rotamer), 8.16 (dd, J=8.4, 2.3 Hz, 0.8H, major rotamer), 8.01-7.88 (m, 0.2H, minor rotamer), 7.71 (d, J=8.3 Hz, 0.8H, major rotamer), 7.53 (d, J=9.5 Hz, 0.8H, major rotamer), 7.45 (d, J=8.2 Hz, 0.2H, minor rotamer), 7.35 (d, J=9.5 Hz, 0.2H, minor rotamer), 4.91 (d, J=18.6 Hz, 1.6H, major rotamer), 4.75 (s, 0.4H, minor rotamer), 4.23-3.90 (m, 1H), 1.30 (d, J=6.7 Hz, 1.5H), 1.25 (d, J=6.6 Hz, 4.5H, major

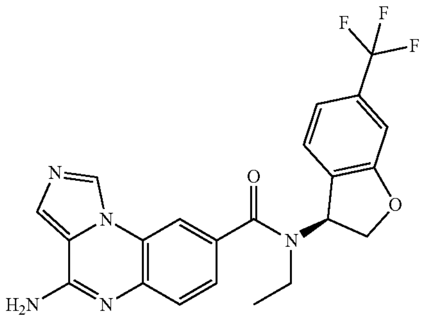 [SMILES: CCN(C(=O)c1ccc2nc(N)c3cncn3c2c1)[C@@H]1COc2cc(C(F)(F)F)ccc21]

Example Ff-8: (S)-4-amino-N-ethyl-N-(6-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and (S)—N-ethyl-6-(trifluoromethyl)-2,3-dihydrobenzofuran-3-amine hydrochloride Eh-2. ES/MS: m/z=442.0 $[M+H]^+$. $^1H$ NMR (400 MHz, MeOD) δ 9.35 (s, 1H), 8.43 (d, J=6.7 Hz, 2H), 7.77-7.67 (m, 2H), 7.67-7.58 (m, 1H), 7.30 (d, J=7.8 Hz, 1H), 7.14 (s, 1H), 6.36-5.50 (m, 1H), 4.79 (dd, J=10.1, 4.1 Hz, 2H), 3.38 (s, 2H), 1.03 (s, 3H).

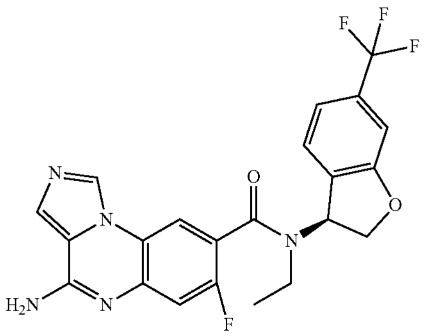 [SMILES: CCN(C(=O)c1cc2c(cc1F)nc(N)c1cncn12)[C@@H]1COc2cc(C(F)(F)F)ccc21]

Example Ff-9: (S)-4-amino-N-ethyl-7-fluoro-N-(6-(trifluoromethyl)-2,3-dihydrobenzofuran-3-yl)imidazo[1,5-a]quinoxaline-8-carboxamide. Prepared following general procedure VI-F starting with 4-(tert-butoxycarbonylamino)-7-fluoro-imidazo[1,5-a]quinoxaline-8-carboxylic acid Af-1 and (S)—N-ethyl-6-(trifluoromethyl)-2,3-dihydrobenzofuran-3-amine hydrochloride Eh-2. ES/MS: m/z=460.0 $[M+H]^+$. $^1H$ NMR (400 MHz, MeOD) δ 9.27 (s, 1H), 8.66-8.23 (m, 2H), 7.64-7.54 (m, 1H), 7.52-7.45 (m, 1H), 7.34-7.28 (m, 1H), 7.19-7.10 (m, 1H), 6.19-6.12 (m, 0.4H, minor rotamer), 5.64 (t, J=6.5 Hz, 0.6H, major rotamer), 4.98-4.91 (m, 0.4H, minor rotamer), 4.82-4.57 (m, 1.6H), 3.65-3.35 (m, 2H), 1.13 (t, J=7.0 Hz, 1.8H, major rotamer), 0.97 (t, J=7.1 Hz, 1.2H, minor

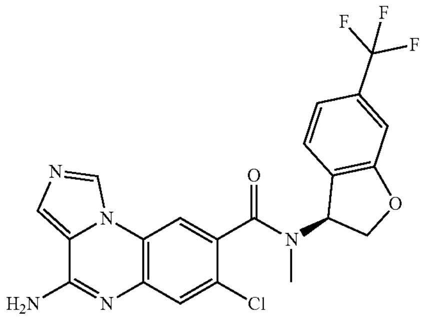

Example Ff-10: (S)-4-amino-7-chloro-N-methyl-N-(6-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)-7-chloroimidazo[1,5-a]quinoxaline-8-carboxylic acid Af-2 and (S)—N-methyl-6-(trifluoromethyl)-2,3-dihydrobenzofuran-3-amine hydrochloride Eh-1. ES/MS: m/z=462.0 $[M+H]^+$. $^1H$ NMR (400 MHz, MeOD) δ 9.42-9.16 (m, 1H), 8.61 (s, 0.2H, minor rotamer), 8.45-8.36 (m, 1.8H), 7.81 (s, 0.2H, minor rotamer), 7.77 (s, 0.2H, minor rotamer), 7.74 (s, 0.6H, major rotamer), 7.60 (t, J=7.0 Hz, 1H), 7.37-7.28 (m, 1H), 7.22-7.17 (m, 0.6H, major rotamer), 7.15 (s, 0.4H, minor rotamer), 6.73-6.51 (m, 0.6H, major rotamer), 5.57 (dt, J=8.8, 4.2 Hz, 0.4H, minor rotamer), 4.84-4.58 (m, 2H), 2.87 (d, J=2.8 Hz, 1.2H, minor rotamer), 2.67 (d, J=5.2 Hz, 1.8H, major rotamer).

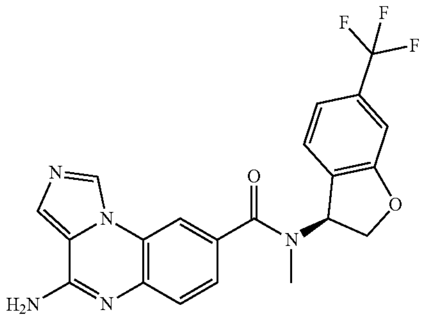

Example Ff-11: (S)-4-amino-N-methyl-N-(6-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and (S)—N-methyl-6-(trifluoromethyl)-2,3-dihydrobenzofuran-3-amine hydrochloride Eh-1. ES/MS: m/z=428.0 $[M+H]^+$. $^1H$ NMR (400 MHz, MeOD) δ 9.35 (s, 1H), 8.48 (s, 1H), 8.42 (s, 1H), 7.90-7.50 (m, 3H), 7.33 (d, J=7.8 Hz, 1H), 7.18 (s, 1H), 6.52 (s, 0.6H major), 5.77 (s, 0.4H, minor rotamer), 4.82-4.63 (m, 2H), 2.80 (s, 3H).

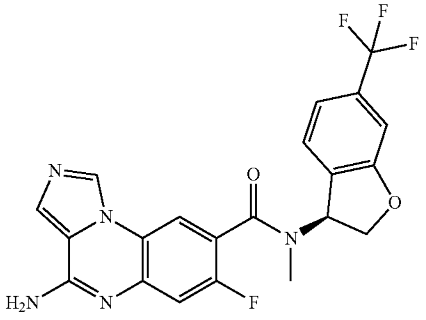

Example Ff-12: (S)-4-amino-7-fluoro-N-methyl-N-(6-(trifluoromethyl)-2,3-dihydrobenzofuran-3-yl)imidazo[1,5-a]quinoxaline-8-carboxamide. Prepared following general procedure VI-F starting with starting with 4-(tert-butoxycarbonylamino)-7-fluoro-imidazo[1,5-a]quinoxaline-8-carboxylic acid Af-1 and (S)—N-methyl-6-(trifluoromethyl)-2,3-dihydrobenzofuran-3-amine hydrochloride Eh-1. ES/MS: m/z=446.2 $[M+H]^+$. $^1H$ NMR (400 MHz, MeOD) δ 9.25 (s, 1H), 8.64-8.41 (m, 1H), 8.35 (d, J=2.0 Hz, 1H), 7.61 (d, J=7.8 Hz, 1H), 7.53-7.40 (m, 1H), 7.37-7.27 (m, 1H), 7.18 (d, J=16.7 Hz, 1H), 6.58 (dd, J=8.9, 3.7 Hz, 0.6H, major rotamer), 5.70 (t, J=6.7 Hz, 0.4H, minor rotamer), 4.78-4.70 (m, 2H), 2.86 (s, 1.2H, minor rotamer), 2.74 (s, 1.8H, major rotamer).

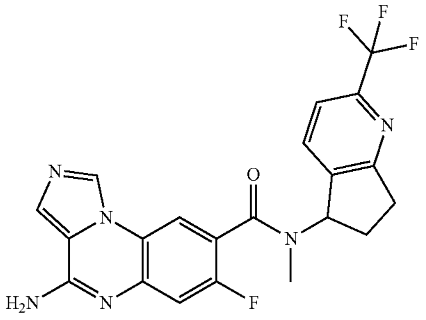

Example Ff-13: 4-amino-7-fluoro-N-methyl-N-(2-(trifluoromethyl)-6,7-dihydro-5H-cyclopenta[b]pyridin-5-yl)imidazo[1,5-a]quinoxaline-8-carboxamide. Prepared following general procedure VI-F starting with starting with 4-(tert-butoxycarbonylamino)-7-fluoro-imidazo[1,5-a]quinoxaline-8-carboxylic acid Af-1 and N-methyl-2-(trifluoromethyl)-6,7-dihydro-5H-cyclopenta[b]pyridin-5-amine hydrochloride Eh-3. ES/MS: m/z=445.0 $[M+H]^+$. $^1H$ NMR (400 MHz, MeOD) δ 9.26 (d, J=0.7 Hz, 1H), 8.46 (d, J=5.9 Hz, 0.6H, major rotamer), 8.41-8.35 (m, 1H), 7.61 (d, J=7.8 Hz, 0.4H, minor rotamer), 7.55-7.42 (m, 1H), 7.38-7.27 (m, 1H), 7.20 (s, 0.6H, major rotamer), 7.16 (s, 0.4H, minor rotamer), 6.58 (dd, J=9.0, 3.7 Hz, 0.6H, major rotamer), 5.69 (t, J=6.6 Hz, 0.4H, minor rotamer), 4.96-4.89 (m, 0.4H, minor rotamer), 4.74 (dd, J=10.7, 3.9 Hz, 1.6H), 3.32 (s, 1H, minor rotamer), 2.86 (s, 2H, major rotamer), 2.76-2.71 (m, 2H).

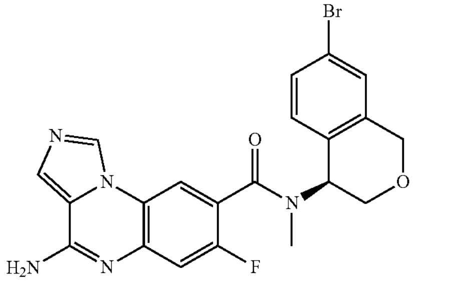 [SMILES: CN(C(=O)c1cc2c(cc1F)nc(N)c1cncn12)[C@@H]1COCc2cc(Br)ccc21]

Example Ff-14: (S)-4-amino-N-(7-bromoisochroman-4-yl)-7-fluoro-N-methylimidazo[1,5-a]quinoxaline-8-carboxamide. Prepared following general procedure VI-F starting with starting with 4-(tert-butoxycarbonylamino)-7-fluoro-imidazo[1,5-a]quinoxaline-8-carboxylic acid Af-1 and (S)-7-bromo-N-methylisochroman-4-amine hydrochloride Eh-4. ES/MS: m/z=470.0 $[M+H]^+$. $^1H$ NMR (400 MHz, MeOD) δ 9.29 (d, J=0.7 Hz, 1H), 8.48 (d, J=5.9 Hz, 1H), 8.37 (dd, J=2.0, 0.7 Hz, 1H), 7.56-7.45 (m, 2H), 7.43-7.35 (m, 1H), 7.35-7.24 (m, 1H), 5.84 (s, 1H), 4.86-4.84 (m, 0.3H, minor rotamer), 4.80 (d, J=9.4 Hz, 0.7H, major rotamer), 4.73 (d, J=15.3 Hz, 0.7H, major rotamer), 4.62 (d, J=15.4 Hz, 0.3H, minor rotamer), 4.28 (dd, J=12.4, 2.9 Hz, 0.7H, major rotamer), 4.19 (s, 0.3H, minor rotamer), 4.14 (dd, J=12.4, 4.5 Hz, 0.7H, major rotamer), 4.04 (s, 0.3H, minor rotamer), 2.95 (s, 1H, minor rotamer), 2.82 (d, J=1.1 Hz, 2H, major rotamer).

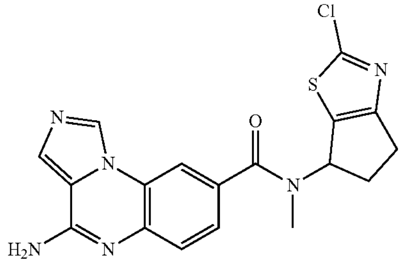 [SMILES: CN(C(=O)c1ccc2nc(N)c3cncn3c2c1)C1CCc2nc(Cl)sc21]

Example Ff-15: 4-amino-N-(2-chloro-5,6-dihydro-4H-cyclopenta[d]thiazol-6-yl)-N-methylimidazo[1,5-a]quinoxaline-8-carboxamide. Prepared following general procedure VI-F starting with starting with 4-((tert-butoxycarbonyl)amino)imidazo[1,5-a]quinoxaline-8-carboxylic acid Ae-1 and 2-chloro-N-methyl-5,6-dihydro-4H-cyclopenta[d]thiazol-6-amine hydrochloride Eg-1. ES/MS: m/z=399.0 $[M+H]^+$. $^1H$ NMR (400 MHz, MeOD) δ 9.34 (s, 1H), 8.54-8.30 (m, 2H), 7.81-7.58 (m, 2H), 6.18 (s, 0.6H, major rotamer), 5.52 (s, 0.4H, minor rotamer), 3.13-2.74 (m, 6H), 2.58 (ddt, J=12.3, 8.1, 3.6 Hz, 1H).

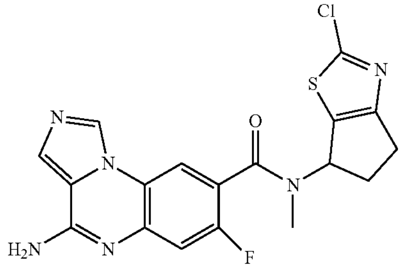 [SMILES: CN(C(=O)c1cc2c(cc1F)nc(N)c1cncn12)C1CCc2nc(Cl)sc21]

Example Ff-16: 4-amino-N-(2-chloro-5,6-dihydro-4H-cyclopenta[d]thiazol-6-yl)-7-fluoro-N-methylimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and 2-chloro-N-methyl-5,6-dihydro-4H-cyclopenta[d]thiazol-6-amine hydrochloride Eg-1. ES/MS: m/z=417.0 $[M+H]^+$. $^1H$ NMR (400 MHz, MeOD) δ 9.26 (d, J=3.7 Hz, 1H), 8.45 (dd, J=12.7, 5.9 Hz, 1H), 8.38 (s, 1H), 7.49 (dd, J=11.3, 9.7 Hz, 1H), 6.28 (d, J=7.9 Hz, 0.5H, rotamer 1), 5.48 (d, J=7.3 Hz, 0.5H, rotamer 2), 3.13-2.71 (m, 6H), 2.54 (tt, J=11.9, 4.3 Hz, 1H).

Example Ff-17: 4-amino-N,1-dimethyl-N-((3S)-6-((tetrahydrofuran-2-yl)ethynyl)-2,3-dihydrobenzofuran-3-yl)imidazo[1,5-a]quinoxaline-8-carboxamide

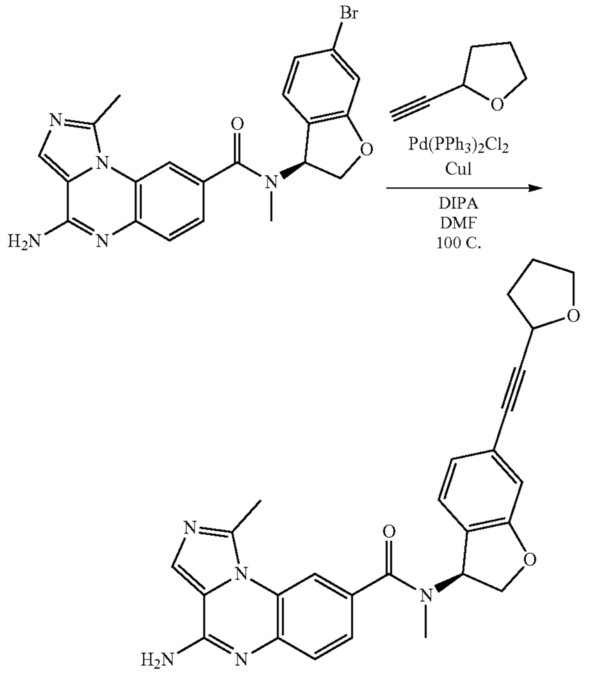

Example Ff-17

Intermediate (S)-4-amino-N-(6-bromo-2,3-dihydrobenzofuran-3-yl)-N,1-dimethylimidazo[1,5-a]quinoxaline-8-carboxamide was prepared following general procedure VI-F starting with starting with starting with 4-((tert-butoxycarbonyl)amino)-1-methylimidazo[1,5-a]quinoxaline-8-carboxylic acid Af-3 and (S)-6-bromo-N-methyl-2,3-dihydrobenzofuran-3-amine Eh-5.

To a solution of (S)-4-amino-N-(6-bromo-2,3-dihydrobenzofuran-3-yl)-N,1-dimethylimidazo[1,5-a]quinoxaline-8-carboxamide (35.0 mg, 0.07 mmol, 1 equiv) in DMF (0.5 M) was added $Pd(PPh_3)_2Cl_2$ (25.0 mg, 0.035 mmol, 0.5 equiv), CuI (6.7 mg, 0.035 mmol, 0.5 equiv), 2-ethynyltetrahydrofuran (51.2 mg, 0.35 mmol, 5 equiv) and diisopropylamine (0.20 mL, 1.4 mmol, 2.0 equiv). The reaction mixture was then degassed with argon for 5 min. The reaction mixture was then heated at 100 C for 1 h. LCMS analysis confirms full conversion to product. Reaction mixture was diluted with EtOAc, washed with water and 5% aq LiCl, dried over $MgSO_4$, filtered and concentrated under reduced pressure to give a residue. The residue was purified by column chromatography (4 g Silica Flash Column, Eluent 0-10% MeOH/EtOAc @ 13 mL/min). Final purification by reverse phase HPLC. ES/MS: m/z=468.3 $[M+H]^+$. $^1$H NMR (400 MHz, DMSO) δ 8.20 (s, 1H), 7.61 (s, 2H), 7.43 (d, J=8.0 Hz, 1H), 7.04 (d, J=7.6 Hz, 1H), 6.94 (s, 1H), 6.75-6.09 (m, 0.5H), 4.47 (brs, 0.3H), 4.86-4.44 (m, 3H), 3.84 (q, J=7.5 Hz, 1H), 3.79-3.69 (m, 1H), 3.03 (s, 3H), 2.73-2.60 (m, 3H), 2.27-2.13 (m, 1H), 2.07-1.78 (m, 3H).

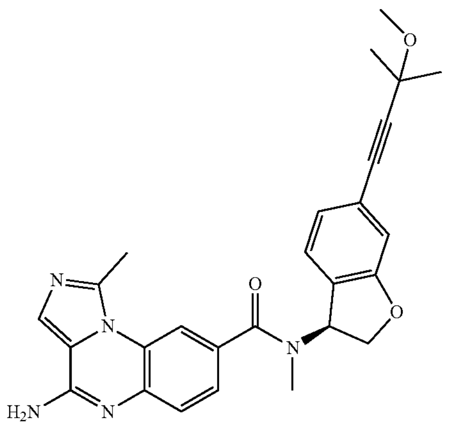 [SMILES: COC(C)(C)C#Cc1ccc2c(c1)OC[C@H]2N(C)C(=O)c1ccc2nc(N)c3cnc(C)n3c2c1]

Example Ff-18: (S)-4-amino-N-(6-(3-methoxy-3-methylbut-1-yn-1-yl)-2,3-dihydrobenzofuran-3-yl)-N,1-dimethylimidazo[1,5-a]quinoxaline-8-carboxamide. Prepared following the procedure reported for example Ff-17 starting with (S)-4-amino-N-(6-bromo-2,3-dihydrobenzofuran-3-yl)-N,1-dimethylimidazo[1,5-a]quinoxaline-8-carboxamide and 3-methoxy-3-methylbut-1-yne. EZ/MS: m/z=470.2 $[M+H]^+$. $^1$H NMR (400 MHz, MeOD) δ 8.32 (d, J=23.7 Hz, 2H), 7.71 (s, 2H), 7.41 (s, 1H), 7.22-6.75 (m, 2H), 4.72 (s, 1H), 3.42 (s, 3H), 3.15 (s, 3H), 2.79 (s, 3H), 2.68 (s, 5H), 1.53 (s, 6H).

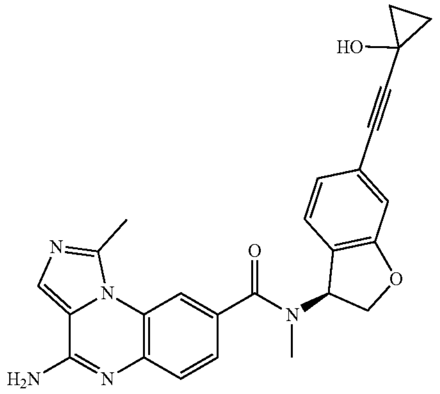 [SMILES: Cc1ncc2c(N)nc3ccc(C(=O)N(C)[C@@H]4COc5cc(C#CC6(O)CC6)ccc54)cc3n12]

Example Ff-19: (S)-4-amino-N-(6-((1-hydroxycyclopropyl)ethynyl)-2,3-dihydrobenzofuran-3-yl)-N,1-dimethylimidazo[1,5-a]quinoxaline-8-carboxamide. Prepared following the procedure reported for example Ff-17 starting with (S)-4-amino-N-(6-bromo-2,3-dihydrobenzofuran-3-yl)-N,1-dimethylimidazo[1,5-a]quinoxaline-8-carboxamide and 1-ethynylcyclopropan-1-ol. EZ/MS: m/z=454.3 $[M+H]^+$. $^1$H NMR (400 MHz, MeOD) δ 8.33 (d, J=17.7 Hz, 2H), 7.71 (s, 3H), 7.38 (s, 1H), 7.05 (d, J=7.7 Hz, 1H), 6.89 (s, 1H), 3.15 (s, 4H), 2.79 (s, 5H), 2.68 (s, 3H), 1.96 (s, 1H), 1.31 (s, 2H), 1.12-1.01 (m, 4H).

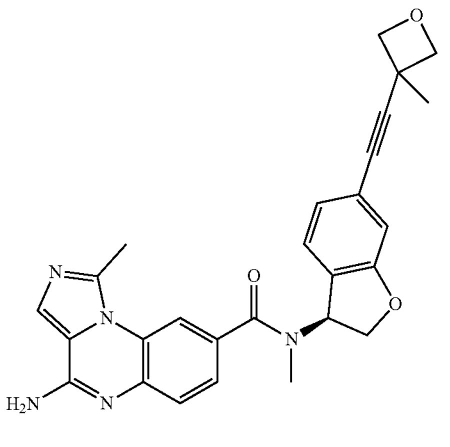

Example Ff-20: (S)-4-amino-N,1-dimethyl-N-(6-((3-methyloxetan-3-yl)ethynyl)-2,3-dihydrobenzofuran-3-yl)imidazo[1,5-a]quinoxaline-8-carboxamide. Prepared following the procedure reported for example Ff-17 starting with (S)-4-amino-N-(6-bromo-2,3-dihydrobenzofuran-3-yl)-N,1-dimethylimidazo[1,5-a]quinoxaline-8-carboxamide and 3-ethynyl-3-methyloxetane. EZ/MS: m/z=468.2 $[M+H]^+$. $^1$H NMR (400 MHz, MeOD) δ 8.31 (s, 1H), 8.02 (s, 1H), 7.63 (s, 2H), 7.39 (s, 1H), 7.07 (d, J=7.7 Hz, 1H), 6.91 (s, 1H), 4.70 (t, J=5.2 Hz, 1H), 4.51 (d, J=5.4 Hz, 2H), 3.11 (s, 3H), 2.80 (s, 3H), 1.70 (s, 3H), (4H missing under MeOH).

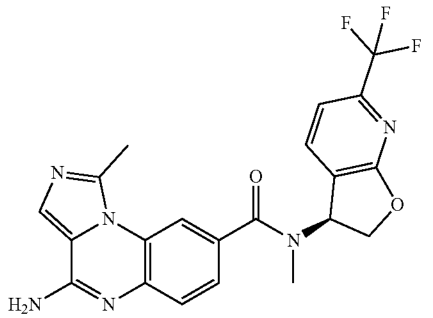

Example Ff-21: (S)-4-amino-N,1-dimethyl-N-(6-(trifluoromethyl)-2,3-dihydrofuro[2,3-b]pyridin-3-yl)imidazo[1,5-a]quinoxaline-8-carboxamide. Prepared following general procedure VI-F starting with starting with starting with 4-((tert-butoxycarbonyl)amino)-1-methylimidazo[1,5-a]quinoxaline-8-carboxylic acid Af-3 and (S)—N-methyl-6-(trifluoromethyl)-2,3-dihydrofuro[2,3-b]pyridin-3-amine Eh-6. EZ/MS: m/z=443.2 $[M+H]^+$. $^1$H NMR (400 MHz, MeOD) δ 8.36 (d, J=19.3 Hz, 2H), 8.11 (d, J=7.5 Hz, 1H), 7.74 (q, J=8.4 Hz, 2H), 7.47 (d, J=7.5 Hz, 1H), 6.40 (s, 1H), 5.04-4.92 (m, 0.3H minor rotamer), 4.84 (s, 1H), 3.15 (s, 3H), 2.91 (s, 3H).

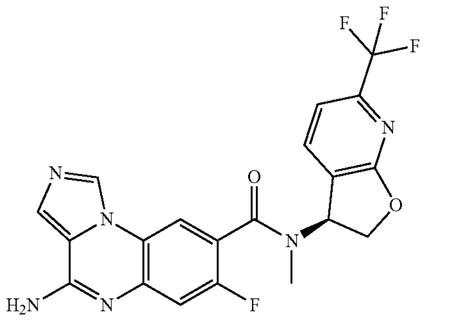

Example Ff-22: (S)-4-amino-7-fluoro-N-methyl-N-(6-(trifluoromethyl)-2,3-dihydrofuro[2,3-b]pyridin-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)—N-methyl-6-(trifluoromethyl)-2,3-dihydrofuro[2,3-b]pyridin-3-amine Eh-6. EZ/MS: m/z=447.2 $[M+H]^+$. $^1H$ NMR (400 MHz, MeOD) δ 9.24 (s, 1H), 8.64-8.29 (m, 2H), 8.02 (dd, J=21.1, 7.5 Hz, 1H), 7.64-7.28 (m, 2H), 6.47 (dd, J=9.4, 4.3 Hz, 1H), 5.78 (t, J=6.9 Hz, 0.3H), 5.15-4.93 (m, 3H), 4.81 (dd, J=10.5, 4.4 Hz, 1H), 2.89 (d, J=18.5 Hz, 3H).

Example Ff-23: 4-amino-N-(bicyclo[1.1.1]pentan-1-yl)-7-fluoro-N-(2-fluoro-4-(1-(trifluoromethyl)-1H-pyrazol-4-yl)benzyl)imidazo[1,5-a]quinoxaline-8-carboxamide

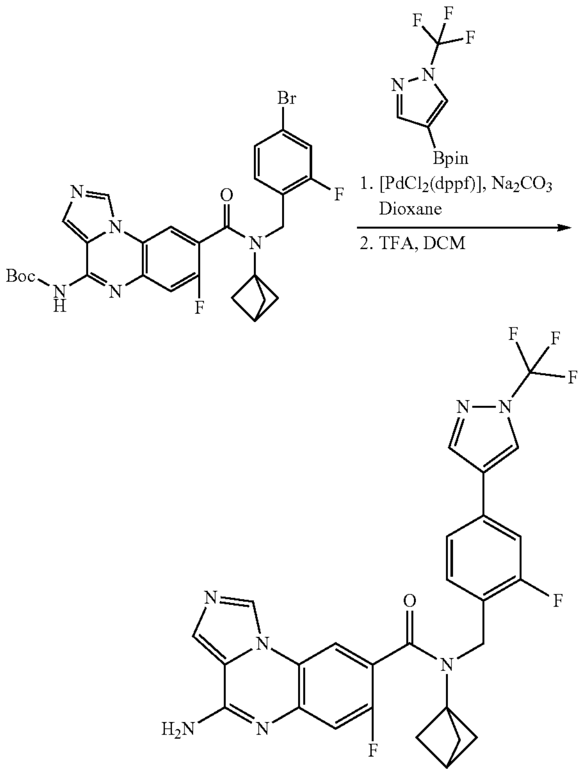

Example Ff-23

Intermediate tert-butyl (8-(bicyclo[1.1.1]pentan-1-yl(4-bromo-2-fluorobenzyl)carbamoyl)-7-fluoroimidazo[1,5-a]quinoxalin-4-yl)carbamate was prepared following step 1 of general procedure VI-F starting with starting with 4-((tert-butoxycarbonyl)amino)-7-fluoroimidazo[1,5-a]quinoxaline-8-carboxylic acid Af-1 and N-(4-bromo-2-fluorobenzyl)bicyclo[1.1.1]pentan-1-amine Ec-3. ES/MS: m/z=599.0 $[M+H]^+$.

Step 1. Tert-butyl (8-(bicyclo[1.1.1]pentan-1-yl(2-fluoro-4-(1-(trifluoromethyl)-1H-pyrazol-4-yl)benzyl)carbamoyl)-7-fluoroimidazo[1,5-a]quinoxalin-4-yl)carbamate. To a solution of tert-butyl (8-(bicyclo[1.1.1]pentan-1-yl(4-bromo-2-fluorobenzyl)carbamoyl)-7-fluoroimidazo[1,5-a]quinoxalin-4-yl)carbamate (22 mg, 0.037 mmol) and 4-(4,4,5,5-tetramethyl-1,3,2-dioxaborolan-2-yl)-1-(trifluoromethyl)-1H-pyrazole (24.5.0 mg, 0.074 mmol), and $PdCl_2$(dppf) (4.1 mg, 0.0055 mmol) in dioxane (2 mL), was added 2M $Na_2CO_3$ (0.0195 mg, 0.184 mmol). The mixture was bubbled through argon for 1 minute and left to stir at 90 C for 6 hours. The mixture was filtered through a pad of celite and anhydrous $MgSO_4$. The solution was reduced under pressure and the crude was purified by flash chromatography. ES/MS: m/z=654.0 $[M+H]^+$.

Step 2. 4-amino-N-(bicyclo[1.1.1]pentan-1-yl)-7-fluoro-N-(2-fluoro-4-(1-(trifluoromethyl)-1H-pyrazol-4-yl)benzyl)imidazo[1,5-a]quinoxaline-8-carboxamide. Tert-butyl (8-(bicyclo[1.1.1]pentan-1-yl(2-fluoro-4-(1-(trifluoromethyl)-1H-pyrazol-4-yl)benzyl)carbamoyl)-7-fluoroimidazo[1,5-a]quinoxalin-4-yl)carbamate (11 mg) was dissolved in DCM (1 mL) and TFA (0.5 mL) was added at room temperature. When the reaction was complete as judged by LCMS analysis the reaction was evaporated to dryness. The residue was then dissolved in MeOH and purified by preparative HPLC to afford the titled compound. (7 mg, 75%). ES/MS: m/z=554.0 $[M+H]^+$. $^1H$ NMR (400 MHz, Methanol-$d_4$) δ 9.31 (s, 1H), 8.68 (s, 1H), 8.33 (d, J=35.5 Hz, 2H), 7.60-7.36 (m, 5H), 5.07 (d, J=16.0 Hz, 1H), 4.64 (s, 1H), 2.68 (s, 1H), 2.28 (d, J=9.0 Hz, 2H), 1.83 (s, 6H).

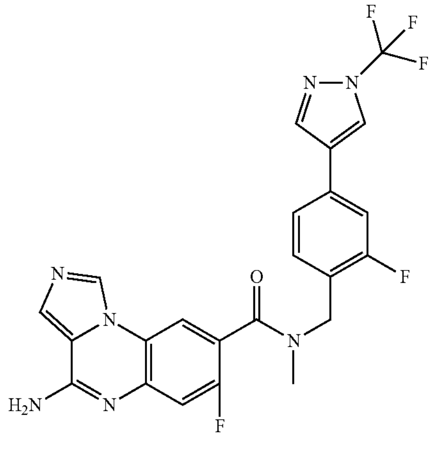 [SMILES: CN(Cc1ccc(-c2cnn(C(F)(F)F)c2)cc1F)C(=O)c1cc2c(cc1F)nc(N)c1cncn12]

Example Ff-24: 4-amino-7-fluoro-N-(2-fluoro-4-(1-(trifluoromethyl)-1H-pyrazol-4-yl)benzyl)-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, 1-(4-bromo-2-fluorophenyl)-N-methylmethanamine Ed-2 and 4-(4,4,5,5-tetramethyl-1,3,2-dioxaborolan-2-yl)-1-(trifluoromethyl)-1H-pyrazole. ES/MS: m/z=502.0 $[M+H]^+$. $^1H$ NMR (400 MHz, Methanol-$d_4$) δ 9.24 (d, J=36.6 Hz, 1H), 8.66 (d, J=25.4 Hz, 1H), 8.49-8.10 (m, 3H), 7.59-7.41 (m, 4H), 4.92 (s, 2H), 3.14 (s, 1H), 3.04 (d, J=1.2 Hz, 2H).

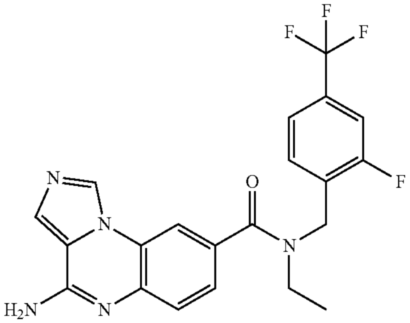 [SMILES: CCN(Cc1ccc(C(F)(F)F)cc1F)C(=O)c1ccc2nc(N)c3cncn3c2c1]

Example Ff-25: 4-amino-N-ethyl-N-[[2-fluoro-4-(trifluoromethyl)phenyl]methyl]imidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and N-[[2-fluoro-4-(trifluoromethyl)phenyl]methyl]ethanamine Ed-5. ES/MS: m/z=432.3 $[M+H]^+$. $^1$H NMR (400 MHz, Methanol-d4) δ 9.31 (d, J=39.3 Hz, 1H), 8.42 (d, J=8.9 Hz, 2H), 7.84-7.32 (m, 5H), 4.94 (s, 1H), 4.79 (s, 1H), 3.68-3.39 (m, 2H), 1.22 (s, 3H).

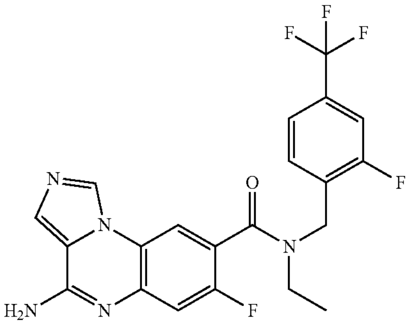 [SMILES: CCN(Cc1ccc(C(F)(F)F)cc1F)C(=O)c1cc2c(cc1F)nc(N)c1cncn12]

Example Ff-26: 4-amino-N-ethyl-7-fluoro-N-[[2-fluoro-4-(trifluoromethyl)phenyl]methyl]imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and N-[[2-fluoro-4-(trifluoromethyl)phenyl]methyl]ethanamine Ed-5. ES/MS: m/z=450.3 $[M+H]^+$. $^1$H NMR (400 MHz, Methanol-d4) δ 9.25 (d, J=35.4 Hz, 1H), 8.52-8.26 (m, 2H), 7.80-7.36 (m, 4H), 4.97 (s, 1H), 4.73 (s, 1H), 3.72-3.38 (m, 2H), 1.23 (dt, J=38.3, 7.1 Hz, 3H).

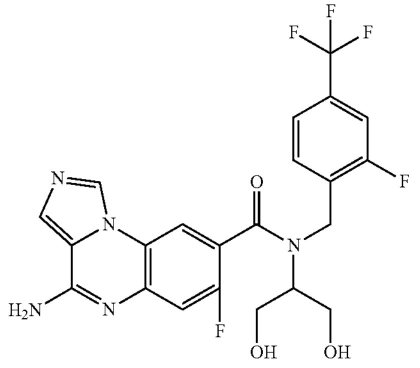 [SMILES: Nc1nc2cc(F)c(C(=O)N(Cc3ccc(C(F)(F)F)cc3F)C(CO)CO)cc2n2cncc12]

Example Ff-27: 4-amino-7-fluoro-N-[[2-fluoro-4-(trifluoromethyl)phenyl]methyl]-N-[2-hydroxy-1-(hydroxymethyl)ethyl]imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and N-[[2-fluoro-4-(trifluoromethyl)phenyl]methyl]oxetan-3-amine Ed-4. ES/MS: m/z=496.1 $[M+H]^+$. $^1$H NMR (400 MHz, Methanol-d4) δ 9.26 (s, 1H), 8.81 (d, J=6.4 Hz, 1H), 8.30 (s, 1H), 7.85 (t, J=7.7 Hz, 1H), 7.64 (dd, J=8.9, 4.8 Hz, 2H), 7.44 (d, J=11.3 Hz, 1H), 4.84-4.72 (m, 2H), 4.64 (d, J=3.0 Hz, 2H), 4.11 (dd, J=12.1, 4.2 Hz, 1H), 4.02 (dd, J=12.1, 5.1 Hz, 1H), 3.89 (q, J=5.1 Hz, 1H).

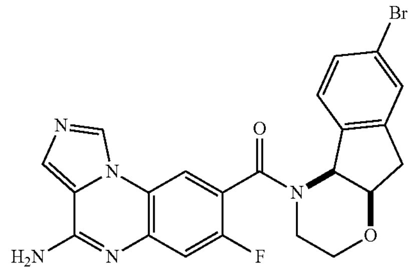

Example Ff-28: Racemic(4-amino-7-fluoroimidazo[1,5-a]quinoxalin-8-yl)((4aS,9aR)-7-bromo-2,3,9,9a-tetrahydroindeno[2,1-b][1,4]oxazin-4(4aH)-yl)methanone. Prepared following general procedure VI-F starting with starting with starting with 4-(tert-butoxycarbonylamino)-7-fluoro-imidazo[1,5-a]quinoxaline-8-carboxylic acid Af-1 and racemic (4aS,9aR)-7-bromo-2,3,4,4a,9,9a-hexahydroindeno[2,1-b][1,4]oxazine Ee-1. ES/MS: m/z=481.8 $[M+H]^+$. $^1$H NMR (400 MHz, DMSO-d6) δ 9.35 (d, J=27.3 Hz, 1H), 8.73 (s, 2H), 8.58 (d, J=6.3 Hz, 1H), 8.24 (d, J=13.4 Hz, 1H), 7.63-7.38 (m, 3H), 7.19 (s, 1H), 5.86 (s, 1H), 4.44-4.31 (m, 2H), 3.85 (d, 0.5H, rotamer 1), 3.66 (d, J=11.4 Hz, 0.5H, rotamer 2), 3.60-3.47 (m, 1H), 3.39-3.22 (m, 1H), 3.13-2.99 (m, 1H), 2.86-2.69 (m, 1H).

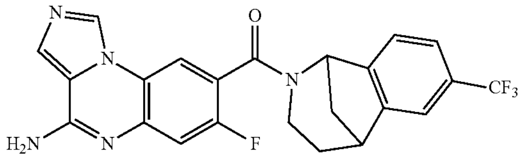 [SMILES: Nc1nc2cc(F)c(C(=O)N3CCC4CC3c3ccc(C(F)(F)F)cc34)cc2n2cncc12]

Example Ff-29: (4-amino-7-fluoroimidazo[1,5-a]quinoxalin-8-yl)(7-(trifluoromethyl)-1,3,4,5-tetrahydro-2H-1,5-methanobenzo[c]azepin-2-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 4-(trifluoromethyl)-9-azatricyclo[6.3.1.02,7]dodeca-2,4,6-triene Ef-1. ES/MS: m/z=455.9 [M+H]$^+$. $^1$H NMR (400 MHz, DMSO-d6) δ 9.37 (d, J=20.5 Hz, 1H), 8.57 (d, J=6.2 Hz, 1H), 8.25 (d, J=14.0 Hz, 1H), 7.83-7.57 (m, 2H), 7.57-7.22 (m, 2H), 6.00 (d, J=4.0 Hz, 0.5H, rotamer one), 4.92 (s, 0.5H, rotamer 2), 4.31 (s, 1H), 3.54 (s, 1H), 3.40-3.20 (m, 1H), 2.44-1.54 (m, 4H).

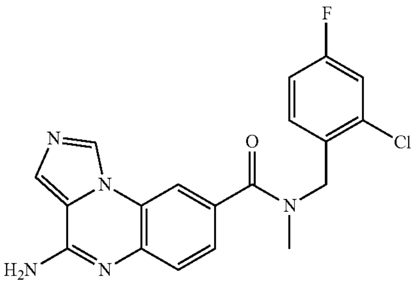 [SMILES: CN(Cc1ccc(F)cc1Cl)C(=O)c1ccc2nc(N)c3cncn3c2c1]

Example Ff-30: 4-amino-N-(2-chloro-4-fluorobenzyl)-N-methylimidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and 1-(2-chloro-4-fluoro-phenyl)-N-methyl-methanamine Eb-1. ES/MS: m/z=383.9 [M+H]$^+$. $^1$H NMR (400 MHz, DMSO-d6) δ 9.48 (d, J=41.7 Hz, 3H), 8.55 (d, J=1.1 Hz, 1H), 8.44 (s, 1H), 7.61 (d, J=61.7 Hz, 4H), 7.33 (td, J=8.5, 2.6 Hz, 1H), 4.81 (s, 1.4H, major rotamer), 4.64 (s, 0.6H, minor rotamer), 2.99 (s, 3H).

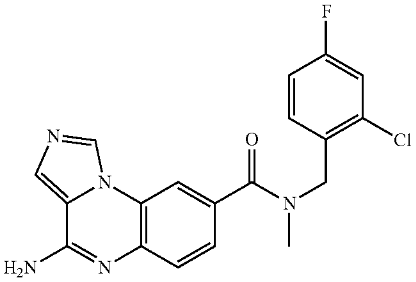 [SMILES: CN(Cc1ccc(F)cc1Cl)C(=O)c1ccc2nc(N)c3cncn3c2c1]

Example Ff-31: 4-amino-N-(2-chloro-4-fluorobenzyl)-7-fluoro-N-methylimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and 1-(2-chloro-4-fluoro-phenyl)-N-methyl-methanamine Eb-1. ES/MS: m/z=401.8 [M+H]$^+$. $^1$H NMR (400 MHz, DMSO-d6) δ 9.40 (s, 0.67H, major rotamer), 9.32 (s, 0.33H, minor rotamer), 9.21-8.69 (m, 2H), 8.53 (t, J=6.4 Hz, 1H), 8.29 (d, J=4.8 Hz, 1H), 7.64-7.22 (m, 4H), 4.84 (s, 1.33H, major rotamer), 4.60 (s, 0.67H, minor rotamer), 2.99 (s, 1H), 2.94 (d, J=1.2 Hz, 2H).

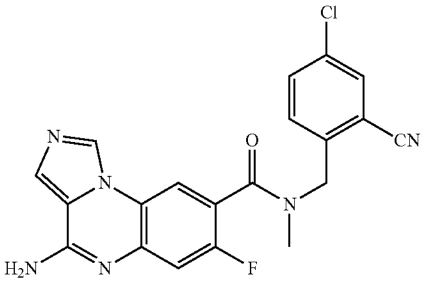 [SMILES: CN(Cc1ccc(Cl)cc1C#N)C(=O)c1cc2c(cc1F)nc(N)c1cncn12]

Example Ff-32: 4-amino-N-(4-chloro-2-cyanobenzyl)-7-fluoro-N-methylimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and 5-chloro-2-(methylaminomethyl)benzonitrile Ea-1. ES/MS: m/z=408.8 [M+H]$^+$. $^1$H NMR (400 MHz, DMSO-d6) δ 9.34 (s, 0.7H, major rotamer), 9.21 (s, 0.3H, minor rotamer), 8.48 (dd, J=14.4, 6.2 Hz, 1H), 8.24 (s, 1H), 8.16 (d, J=2.3 Hz, 0.7H, major rotamer), 8.02 (s, 0.3H, minor rotamer), 7.91 (dd, J=8.5, 2.3 Hz, 0.7H, major rotamer), 7.83 (d, J=9.0 Hz, 0.3H, minor rotamer), 7.59 (d, J=8.5 Hz, 0.7H, major rotamer), 7.45 (t, J=8.8 Hz, 1H), 7.34 (d, J=10.3 Hz, 0.3H, minor rotamer), 4.94 (s, 1.4H, major rotamer), 4.75 (s, 0.6H, minor rotamer), 3.09 (s, 1H, minor rotamer), 3.02 (d, J=1.3 Hz, 2H, major rotamer).

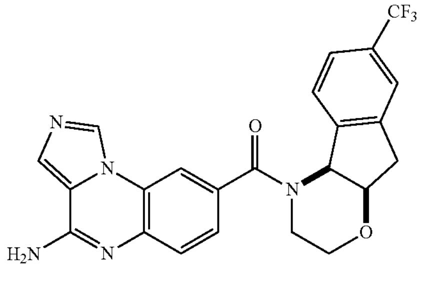 [SMILES: Nc1nc2ccc(C(=O)N3CCO[C@@H]4Cc5cc(C(F)(F)F)ccc5[C@@H]43)cc2n2cncc12]

Example Ff-33: Racemic (4-aminoimidazo[1,5-a]quinoxalin-8-yl)((4aS,9aR)-7-(trifluoromethyl)-2,3,9,9a-tetrahydroindeno[2,1-b][1,4]oxazin-4(4aH)-yl)methanone. Prepared following general procedure VI-F starting with starting with 4-((tert-butoxycarbonyl)amino)imidazo[1,5-a]quinoxaline-8-carboxylic acid Ae-1 and Cis-(4aS,9aR)-7-(trifluoromethyl)-2,3,4,4a,9,9a-hexahydroindeno[2,1-b][1,4]oxazine Ee-3. ES/MS: m/z=453.9 [M+H]$^+$. $^1$H NMR (400 MHz, DMSO-d6) δ 9.49 (s, 0.6H major rotamer), 9.38 (s, 0.4H minor rotamer), 8.65 (brs, 2H), 8.62 (s, 0.4H minor rotamer), 8.55 (s, 0.6H major rotamer), 8.34 (s, 1H), 7.80-7.48 (m, 5H), 5.96 (s, 0.6H major rotamer), 5.18 (s, 0.4H minor rotamer), 4.52-4.27 (m, 2H), 3.82 (s, 1H), 3.50 (d, J=14.1 Hz, 1H), 3.33 (d, J=16.5 Hz, 1H), 3.24-2.74 (m, 2H).

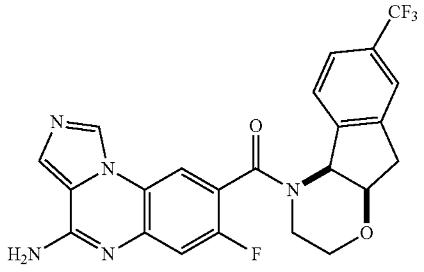 [SMILES: Nc1nc2cc(F)c(C(=O)N3CCO[C@@H]4Cc5cc(C(F)(F)F)ccc5[C@@H]43)cc2n2cncc12]

Example Ff-34: Racemic (4-amino-7-fluoroimidazo[1,5-a]quinoxalin-8-yl)((4aS,9aR)-7-(trifluoromethyl)-2,3,9,9a-tetrahydroindeno[2,1-b][1,4]oxazin-4(4aH)-yl)methanone. Prepared following general procedure VI-F starting with starting with starting with 4-(tert-butoxycarbonylamino)-7-fluoro-imidazo[1,5-a]quinoxaline-8-carboxylic acid Af-1 and cis-(4aS,9aR)-7-(trifluoromethyl)-2,3,4,4a,9,9a-hexahydroindeno[2,1-b][1,4]oxazine Ee-3. ES/MS: m/z=471.9 $[M+H]^+$. $^1H$ NMR (400 MHz, DMSO-d6) δ 9.33 (d, J=28.5 Hz, 1H), 8.65 (brs, 2H), 8.57 (d, J=6.3 Hz, 1H), 8.20 (d, J=16.0 Hz, 1H), 7.79-7.59 (m, 2H), 7.48-7.40 (m, 2H), 5.99 (s, 1H), 4.56-4.34 (m, 1H), 3.92-3.45 (m, 2H), 3.60-3.45 (m, 2H), 3.24-2.74 (m, 2H).

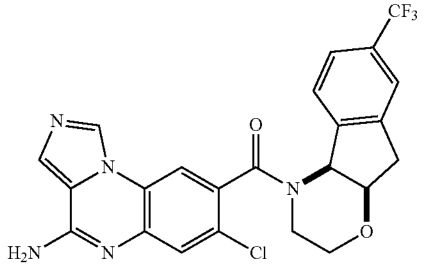

Example Ff-35: Racemic (4-amino-7-chloroimidazo[1,5-a]quinoxalin-8-yl)((4aS,9aR)-7-(trifluoromethyl)-2,3,9,9a-tetrahydroindeno[2,1-b][1,4]oxazin-4(4aH)-yl)methanone. Prepared following general procedure VI-F starting with starting with starting with 4-((tert-butoxycarbonyl)amino)-7-chloroimidazo[1,5-a]quinoxaline-8-carboxylic acid Af-2 and cis-(4aS,9aR)-7-(trifluoromethyl)-2,3,4,4a,9,9a-hexahydroindeno[2,1-b][1,4]oxazine Ee-3. ES/MS: m/z=487.8 $[M+H]^+$. $^1H$ NMR (400 MHz, DMSO-d6) δ 9.48-9.27 (m, 1H), 8.81-8.47 (m, 1H), 8.65 (brs, 2H), 8.20 (d, J=21.7 Hz, 1H), 7.92-7.51 (m, 4H), 5.98 (d, J=13.1 Hz, 1H), 5.14 (s, 0.4H, minor rotamer), 4.85 (s, 0.6H, major rotamer), 4.47 (tt, J=11.5, 4.1 Hz, 2H), 3.84 (d, J=11.2 Hz, 1H), 3.39-2.66 (m, 3H).

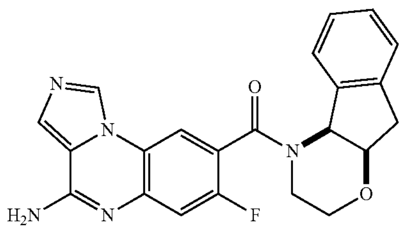 [SMILES: Nc1nc2cc(F)c(C(=O)N3CCO[C@@H]4Cc5ccccc5[C@@H]43)cc2n2cncc12]

Example Ff-36: Racemic(4-amino-7-fluoroimidazo[1,5-a]quinoxalin-8-yl)((4aS,9aR)-2,3,9,9a-tetrahydroindeno[2,1-b][1,4]oxazin-4(4aH)-yl)methanone. Prepared following general procedure VI-F starting with starting with starting with 4-(tert-butoxycarbonylamino)-7-fluoro-imidazo[1,5-a]quinoxaline-8-carboxylic acid Af-1 and cis-(4aS,9aR)-2,3,4,4a,9,9a-hexahydroindeno[2,1-b][1,4]oxazine Ee-2. ES/MS: m/z=404.0 $[M+H]^+$. $^1H$ NMR (400 MHz, DMSO-d6) δ 9.37 (d, J=23.3 Hz, 1H), 8.71 (d, J=36.5 Hz, 1H), 8.65 (brs, 2H), 8.58 (d, J=6.3 Hz, 1H), 8.24 (d, J=14.0 Hz, 1H), 7.60-7.11 (m, 4H), 5.90 (s, 1H), 4.55-4.26 (m, 2H), 3.75 (dd, J=70.8, 11.4 Hz, 1H), 3.60-3.22 (m, 2H), 3.15-2.69 (m, 2H).

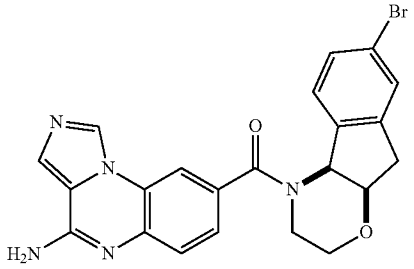 [SMILES: Nc1nc2ccc(C(=O)N3CCO[C@@H]4Cc5cc(Br)ccc5[C@@H]43)cc2n2cncc12]

Example Ff-37: Racemic (4-aminoimidazo[1,5-a]quinoxalin-8-yl)((4aS,9aR)-7-bromo-2,3,9,9a-tetrahydroindeno[2,1-b][1,4]oxazin-4(4aH)-yl)methanone. Prepared following general procedure VI-F starting with starting with starting with 4-((tert-butoxycarbonyl)amino)imidazo[1,5-a]quinoxaline-8-carboxylic acid Ae-1 and Cis-(4aS,9aR)-7-bromo-2,3,4,4a,9,9a-hexahydroindeno[2,1-b][1,4]oxazine Ee-1. ES/MS: m/z=465.9 $[M+H]^+$. $^1H$ NMR (400 MHz, DMSO-d6) δ 9.40-9.35 (m, 1H), 8.50 (brs, 2H), 8.20 (s, 1H), 7.83-7.10 (m, 5H), 5.83 (s, 0.6H, major rotamer), 5.08 (s, 0.4H, minor rotamer), 4.42 (s, 2H), 3.91-3.55 (m, 3H), 3.22-3.17 (m, 1H), 3.05-2.76 (m, 1H).

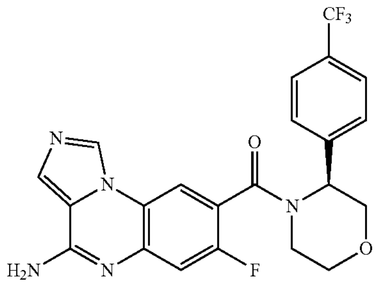

Example Ff-38: (S)-(4-amino-7-fluoroimidazo[1,5-a]quinoxalin-8-yl)(3-(4-(trifluoromethyl)phenyl)morpholino)methanone. Prepared following general procedure VI-F starting with starting with starting with 4-(tert-butoxycarbonylamino)-7-fluoro-imidazo[1,5-a]quinoxaline-8-carboxylic acid Af-1 and commercial (S)-3-(4-(trifluoromethyl)phenyl)morpholine. ES/MS: m/z=459.9 $[M+H]^+$. $^1H$ NMR (400 MHz, DMSO-d6) δ 9.40 (s, 1H), 8.96 (s, 2H), 8.61-8.46 (m, 1H), 8.30 (s, 1H), 7.93-7.70 (m, 3H), 7.63-7.36 (m, 1H), 5.82 (s, 1H), 4.51 (dd, J=78.0, 13.1 Hz, 1H), 4.10-3.73 (m, 2H), 3.73-3.49 (m, 1H), 3.45-3.24 (m, 1H).

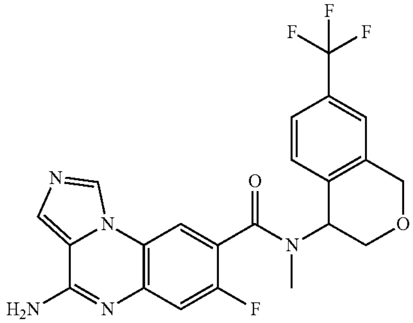

Example Ff-39: 4-amino-7-fluoro-N-methyl-N-(7-(trifluoromethyl)isochroman-4-yl)imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and N-methyl-7-(trifluoromethyl)isochroman-4-amine hydrochloride Ej-1. ES/MS: m/z=460.0 $[M+H]^+$. $^1H$ NMR (400 MHz, MeOD) δ 9.29 (d, J=0.7 Hz, 1H), 8.50 (d, J=5.8 Hz, 1H), 8.42-8.35 (m, 1H), 7.70-7.59 (m, 2H), 7.56 (s, 1H), 7.52-7.47 (m, 1H), 5.95 (s, 1H), 5.01-4.91 (m, 1H), 4.81 (d, J=15.5 Hz, 1H), 4.38-4.04 (m, 2H), 2.96 (s, 1H, minor rotamer), 2.86-2.81 (m, 2H, major rotamer).

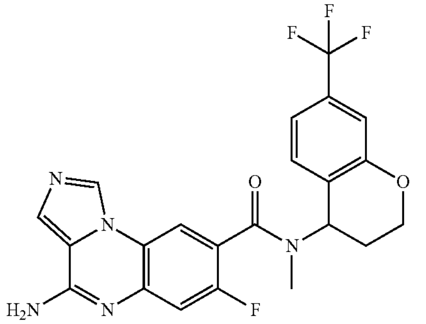 [SMILES: CN(C(=O)c1cc2c(cc1F)nc(N)c1cncn12)C1CCOc2cc(C(F)(F)F)ccc21]

Example Ff-40: 4-amino-7-fluoro-N-methyl-N-(7-(trifluoromethyl)chroman-4-yl)imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and N-methyl-7-(trifluoromethyl)chroman-4-amine hydrochloride Ej-2. ES/MS: m/z=460.0 $[M+H]^+$. $^1H$ NMR (400 MHz, MeOD) δ 9.31 (s, 0.6H, major rotamer), 9.26 (s, 0.4H, minor rotamer), 8.54 (d, J=5.9 Hz, 1H), 8.41-8.35 (m, 1H), 7.50 (dd, J=9.7, 6.5 Hz, 1H), 7.45-7.37 (m, 1H), 7.30-7.24 (m, 1H), 7.17-7.12 (m, 0.6H, major rotamer), 7.09 (d, J=1.4 Hz, 0.4H, minor rotamer), 6.16 (dd, J=10.6, 6.5 Hz, 0.6H, major rotamer), 5.14-5.06 (m, 0.4H, minor rotamer), 4.61-4.30 (m, 1.6H), 4.09 (s, 0.4H, minor rotamer), 2.90 (s, 1.2H, minor rotamer), 2.79 (d, J=1.1 Hz, 1.8H, major rotamer), 2.50-2.36 (m, 1H), 2.32-2.22 (m, 1H).

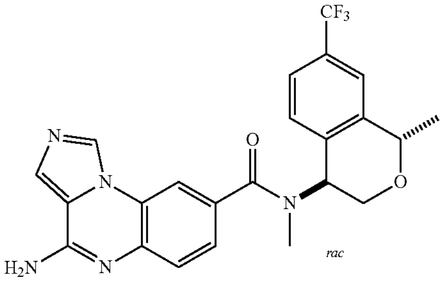 [SMILES: C[C@@H]1OC[C@@H](N(C)C(=O)c2ccc3nc(N)c4cncn4c3c2)c2ccc(C(F)(F)F)cc21]

Example Ff-41: Trans-4-amino-N-methyl-N-(trans-1-methyl-7-(trifluoromethyl)isochroman-4-yl)imidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and rac-(1R,4R)—N,1-dimethyl-7-(trifluoromethyl)isochroman-4-amine hydrochloride salt (±)-Ei-1. ES/MS: m/z=456.0 $[M+H]^+$. $^1H$ NMR (400 MHz, MeOD) δ 9.43-9.28 (m, 1H), 8.52 (d, J=1.8 Hz, 1H), 8.42 (d, J=4.1 Hz, 1H), 7.82-7.70 (m, 2H), 7.70-7.48 (m, 3H), 5.97 (t, J=6.5 Hz, 0.6H, major rotamer), 5.06 (d, J=6.5 Hz, 1H), 4.96 (d, J=6.5 Hz, 0.4H, minor rotamer), 4.50-4.22 (m, 1H), 4.08 (dd, J=11.5, 6.9 Hz, 1H), 2.93-2.78 (m, 3H), 1.61 (d, J=6.6 Hz, 1.8H, major rotamer), 1.46 (d, J=6.5 Hz, 1.2H, minor rotamer).

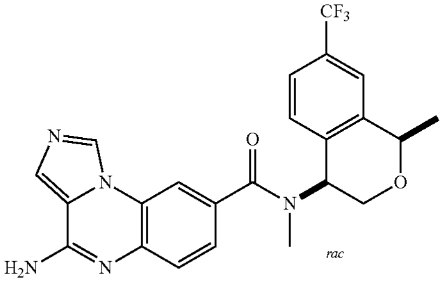 [SMILES: C[C@H]1OC[C@@H](N(C)C(=O)c2ccc3nc(N)c4cncn4c3c2)c2ccc(C(F)(F)F)cc21]

Example Ff-42: Cis-4-amino-N-methyl-N-(1-methyl-7-(trifluoromethyl)isochroman-4-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and rac-(1S,4R)—N,1-dimethyl-7-(trifluoromethyl)isochroman-4-amine hydrochloride salt (±)-Ei-2. ES/MS: m/z=456.2 $[M+H]^+$. $^1H$ NMR (400 MHz, DMSO-$d_6$) δ 9.47 (s, 0.7H major rotamer), 9.43 (s, 0.3H minor rotamer), 9.26 (brs, 2H), 8.60 (s, 0.3H minor rotamer), 8.51 (s, 0.7H major rotamer), 8.39 (s, 1H), 7.75-7.50 (m, 6H), 5.73 (brs, 0.6H minor rotamer), 4.92 4.86 (m, 1.4H major rotamer), 4.45-4.24 (m, 1H), 4.18-4.00 (m, 1H), 2.81 (s, 0.9H minor rotamer), 2.75 (s, 2.1H major rotamer), 1.57 (d, J=6.4 Hz, 3H).

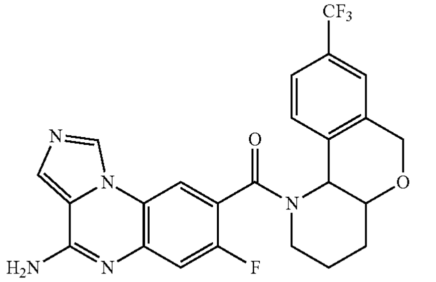 [SMILES: Nc1nc2cc(F)c(C(=O)N3CCCC4OCc5cc(C(F)(F)F)ccc5C43)cc2n2cncc12]

Example 5: (4-amino-7-fluoroimidazo[1,5-a]quinoxalin-8-yl)(8-(trifluoromethyl)-2,3,4,4a,6,10b-hexahydro-1H-isochromeno[4,3-b]pyridin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 8-(trifluoromethyl)-2,3,4,4a,6,10b-hexahydro-1H-isochromeno[4,3-b]pyridine Ek-1. ES/MS: m/z=486.0 $[M+H]^+$. $^1H$ NMR (400 MHz, MeOD) δ 9.30 (s, 1H), 8.54 (s, 1H), 8.35 (d, J=6.3 Hz, 1H), 7.82-7.32 (m, 4H), 6.15 (s, 1H), 5.10-4.90 (m, 2H), 4.40-3.93 (m, 1H), 3.85-3.38 (m, 1H), 2.98-2.79 (m, 1H), 2.05-1.58 (m, 4H).

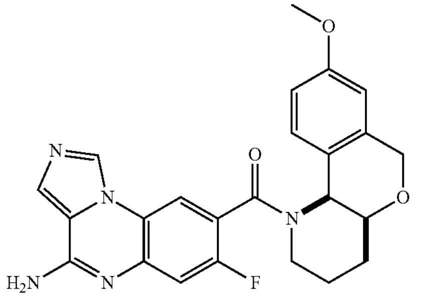 [SMILES: COc1ccc2c(c1)CO[C@H]1CCCN(C(=O)c3cc4c(cc3F)nc(N)c3cncn34)[C@@H]21]

Example Ff-44: Rac-(4-amino-7-fluoroimidazo[1,5-a]quinoxalin-8-yl)((cis)-8-methoxy-2,3,4,4a,6,10b-hexahydro-1H-isochromeno[4,3-b]pyridin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and cis-(4aS,10bS)-8-methoxy-2,3,4,4a,6,10b-hexahydro-1H-isochromeno[4,3-b]pyridine El-1. ES/MS: m/z=448.0 $[M+H]^+$. $^1H$ NMR (400 MHz, MeOD) δ 9.30 (s, 1H), 8.52 (s, 1H), 8.37 (s, 1H), 7.48 (d, J=9.7 Hz, 1H), 7.29 (s, 1H), 6.92 (d, J=8.5 Hz, 1H), 6.80-6.55 (m, 1H), 6.03 (s, 1H), 4.81-4.46 (m, 1H), 4.20 (s, 1H), 3.90-3.70 (m, 3H), 3.43-3.35 (m, 1H), 3.10-2.86 (m, 1H), 2.73-2.48 (m, 1H), 2.02-1.55 (m, 4H).

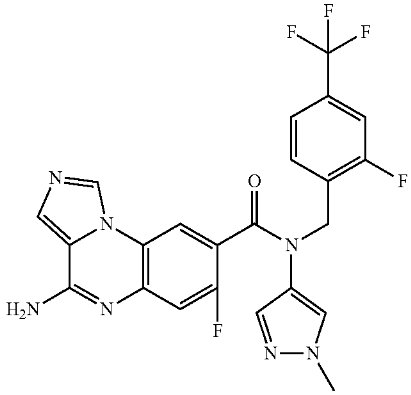 [SMILES: Cn1cc(N(Cc2ccc(C(F)(F)F)cc2F)C(=O)c2cc3c(cc2F)nc(N)c2cncn23)cn1]

Example Ff-45: 4-amino-7-fluoro-N-(2-fluoro-4-(trifluoromethyl)benzyl)-N-(1-methyl-1H-pyrazol-4-yl)imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and N-(2-fluoro-4-(trifluoromethyl)benzyl)-1-methyl-1H-pyrazol-4-amine Ed-6. ES/MS: m/z=502.0 $[M+H]^+$. $^1H$ NMR (400 MHz, MeOD) δ 9.23 (d, J=0.7 Hz, 1H), 8.40 (d, J=5.7 Hz, 1H), 8.37 (d, J=0.6 Hz, 1H), 7.74 (t, J=7.6 Hz, 1H), 7.61-7.47 (m, 3H), 7.26 (d, J=9.5 Hz, 1H), 7.22 (d, J=0.9 Hz, 1H), 5.20 (s, 2H), 3.66 (s, 3H).

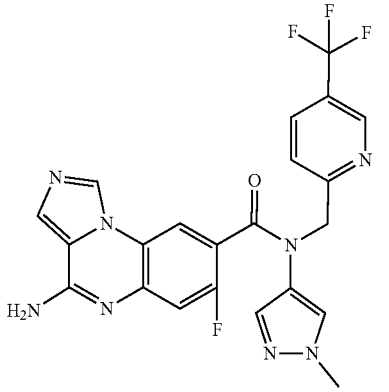 [SMILES: Cn1cc(N(Cc2ccc(C(F)(F)F)cn2)C(=O)c2cc3c(cc2F)nc(N)c2cncn23)cn1]

Example Ff-46: 4-amino-7-fluoro-N-(1-methyl-1H-pyrazol-4-yl)-N-((5-(trifluoromethyl)pyridin-2-yl)methyl)imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and 1-methyl-N-((5-(trifluoromethyl)pyridin-2-yl)methyl)-1H-pyrazol-4-amine Ed-7. ES/MS: m/z=485.0 $[M+H]^+$. $^1H$ NMR (400 MHz, MeOD) δ 9.25 (d, J=0.7 Hz, 1H), 8.92 (t, J=1.6 Hz, 1H), 8.43 (d, J=5.7 Hz, 1H), 8.38 (d, J=0.7 Hz, 1H), 8.18 (dd, J=8.1, 2.3 Hz, 1H), 7.73 (d, J=8.2 Hz, 1H), 7.64 (s, 1H), 7.34-7.25 (m, 2H), 5.25 (s, 2H), 3.67 (s, 3H).

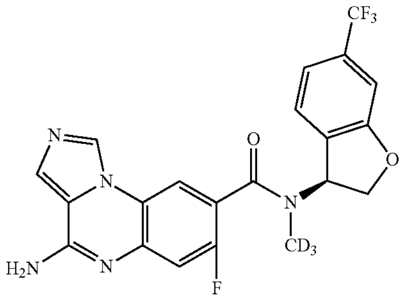 [SMILES: [2H]C([2H])([2H])N(C(=O)c1cc2c(cc1F)nc(N)c1cncn12)[C@@H]1COc2cc(C(F)(F)F)ccc21]

Example Ff-47: 4-amino-7-fluoro-N-(methyl-d3)-N-(6-(trifluoromethyl)-2,3-dihydrobenzofuran-3-yl)imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and (S)—N-(methyl-d3)-6-(trifluoromethyl)-2,3-dihydrobenzofuran-3-amine hydrochloride Eh-7. ES/MS: m/z=449.1 $[M+H]^+$. $^1H$ NMR (400 MHz, DMSO-$d_6$) δ 9.30 (d, J=5.5 Hz, 1H), 9.07-8.40 (m, 3H) 8.23 (d, J=5.5 Hz, 1H), 7.66-7.18 (m, 4H), 6.47 (brs, 1H), 5.66-5.54 (m, 1H), 4.95-4.82 (m, 1H), 4.78-4.61 (m, 1H).

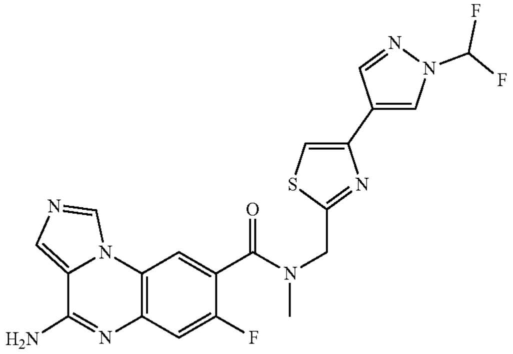 [SMILES: CN(Cc1nc(-c2cnn(C(F)F)c2)cs1)C(=O)c1cc2c(cc1F)nc(N)c1cncn12]

Example Ff-48: 4-amino-N-((4-(1-(difluoromethyl)-1H-pyrazol-4-yl)thiazol-2-yl)methyl)-7-fluoro-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, 1-(4-bromothiazol-2-yl)-N-methylmethanamine Ed-8 and 4-(4,4,5,5-tetramethyl-1,3,2-dioxaborolan-2-yl)-1-(difluoromethyl)-1H-pyrazole. ES/MS: m/z=473.2 $[M+H]^+$. $^1H$ NMR (400 MHz, MeOD) δ 9.16 (d, J=80.8 Hz, 1H), 8.55-8.25 (m, 3H), 8.11 (d, J=53.4 Hz, 1H), 7.73 (d, J=27.0 Hz, 1H), 7.62-7.25 (m, 2H), 5.02 (d, J=87.7 Hz, 2H), 3.24 (d, J=46.4 Hz, 3H).

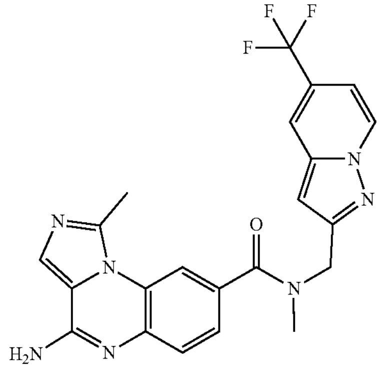 [SMILES: Cc1ncc2c(N)nc3ccc(C(=O)N(C)Cc4cc5cc(C(F)(F)F)ccn5n4)cc3n12]

Example Ff-49: 4-amino-N,1-dimethyl-N-((5-(trifluoromethyl)pyrazolo[1,5-a]pyridin-2-yl)methyl)imidazo[1,5-a]quinoxaline-8-carboxamide. Prepared following general procedure VI-F starting with 4-((tert-butoxycarbonyl)amino)-1-methylimidazo[1,5-a]quinoxaline-8-carboxylic acid Af-3 and N-methyl-1-(5-(trifluoromethyl)pyrazolo[1,5-a]pyridin-2-yl)methanamine Em-1. EZ/MS: m/z=454.2 $[M+H]^+$. $^1H$ NMR (400 MHz, MeOD)) δ 8.75 (s, 1H), 8.34 (d, J=48.1 Hz, 2H), 8.10 (s, 1H), 7.90-7.57 (m, 2H), 7.30-6.68 (m, 2H), 5.04 (s, 1H second H under solvent), Me group under solvent, 3.22-3.07 (m, 3H).

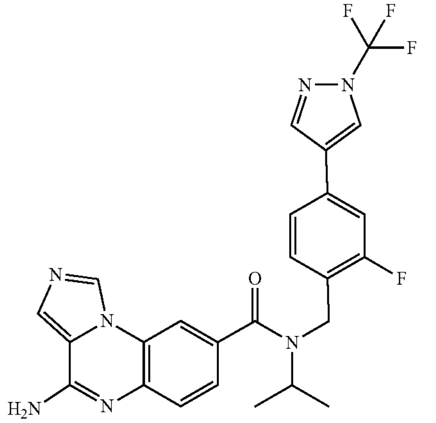 [SMILES: CC(C)N(Cc1ccc(-c2cnn(C(F)(F)F)c2)cc1F)C(=O)c1ccc2nc(N)c3cncn3c2c1]

Example Ff-50: 4-amino-N-(2-fluoro-4-(1-(trifluoromethyl)-1H-pyrazol-4-yl)benzyl)-N-isopropylimidazo[1,5-a]quinoxaline-8-carboxamide. Prepared following the procedure reported for example Ff-23 starting with 4-((tert-butoxycarbonyl)amino)imidazo[1,5-a]quinoxaline-8-carboxylic acid Ae-1, N-(4-bromo-2-fluorobenzyl)propan-2-amine Ed-9 and 4-(4,4,5,5-tetramethyl-1,3,2-dioxaborolan-2-yl)-1-(trifluoromethyl)-1H-pyrazole. ES/MS: m/z=512.0 $[M+H]^+$. $^1H$ NMR (400 MHz, Methanol-$d_4$) δ 9.13 (s, 1H), 8.63 (s, 1H), 8.24 (s, 2H), 7.95 (s, 1H), 7.53 (s, 5H), 4.78 (s, 2H), 1.27 (s, 7H).

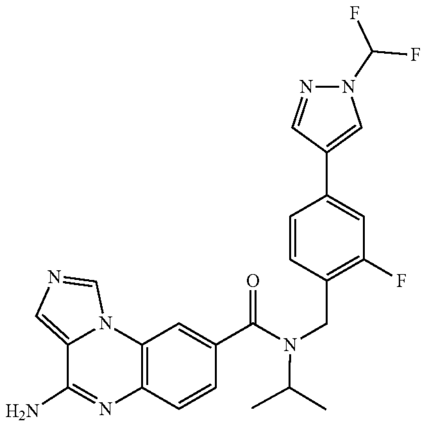 [SMILES: CC(C)N(Cc1ccc(-c2cnn(C(F)F)c2)cc1F)C(=O)c1ccc2nc(N)c3cncn3c2c1]

Example Ff-51: 4-amino-N-(4-(1-(difluoromethyl)-1H-pyrazol-4-yl)-2-fluorobenzyl)-N-isopropylimidazo[1,5-a]quinoxaline-8-carboxamide. Prepared following the procedure reported for example Ff-23 starting with 4-((tert-butoxycarbonyl)amino)imidazo[1,5-a]quinoxaline-8-carboxylic acid Ae-1, N-(4-bromo-2-fluorobenzyl)propan-2-amine Ed-9 and 1-(difluoromethyl)-4-(4,4,5,5-tetramethyl-1,3,2-dioxaborolan-2-yl)-1H-pyrazole. ES/MS: m/z=494.0 $[M+H]^+$. $^1$H NMR (400 MHz, Methanol-$d_4$) δ 9.14 (s, 1H), 8.55 (d, J=63.2 Hz, 1H), 8.33-7.83 (m, 3H), 7.72-7.35 (m, 5H), 4.78 (s, 2H), 1.29 (d, J=15.6 Hz, 8H).

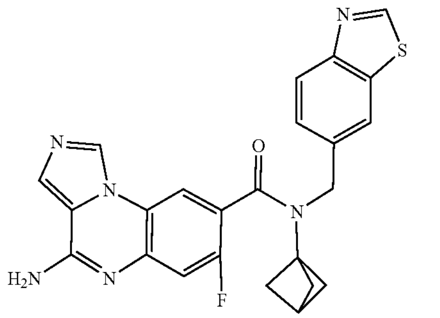 [SMILES: Nc1nc2cc(F)c(C(=O)N(Cc3ccc4ncsc4c3)C34CC(C3)C4)cc2n2cncc12]

Example Ff-52: 4-amino-N-(benzo[d]thiazol-6-ylmethyl)-N-(bicyclo[1.1.1]pentan-1-yl)-7-fluoroimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and N-(benzo[d]thiazol-6-ylmethyl)bicyclo[1.1.1]pentan-1-amine Ec-6. ES/MS: m/z=459.0 $[M+H]^+$. $^1$H NMR (400 MHz, MeOD) δ 9.32 (s, 1H), 9.28 (s, 1H), 8.50 (d, J=5.8 Hz, 1H), 8.39 (s, 1H), 8.16-8.08 (m, 2H), 7.66 (d, J=8.5 Hz, 1H), 7.50 (d, J=9.4 Hz, 1H), 5.15 (d, J=15.5 Hz, 1H), 4.98 (d, J=15.5 Hz, 1H), 2.29 (s, 1H), 1.81 (s, 6H).

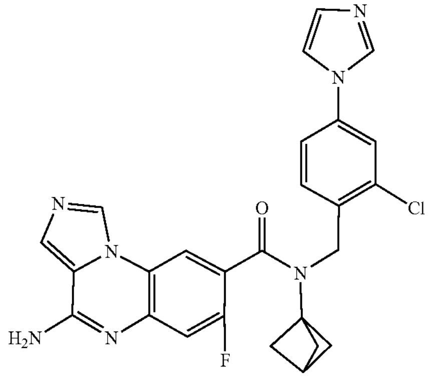 [SMILES: Nc1nc2cc(F)c(C(=O)N(Cc3ccc(-n4ccnc4)cc3Cl)C34CC(C3)C4)cc2n2cncc12]

Example Ff-53: 4-amino-N-(bicyclo[1.1.1]pentan-1-yl)-N-(2-chloro-4-(1H-imidazol-1-yl)benzyl)-7-fluoroimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and N-(2-chloro-4-(1H-imidazol-1-yl)benzyl)bicyclo[1.1.1]pentan-1-amine Ec-7. ES/MS: m/z=502.0 $[M+H]^+$. $^1$H NMR (400 MHz, MeOD) δ 9.50 (s, 1H), 9.28 (s, 1H), 8.49 (d, J=5.8 Hz, 1H), 8.38 (s, 1H), 8.14 (t, J=1.9 Hz, 1H), 8.00 (d, J=2.3 Hz, 1H), 7.85-7.76 (m, 2H), 7.69 (d, J=8.5 Hz, 1H), 7.55 (d, J=9.6 Hz, 1H), 5.19 (d, J=16.9 Hz, 1H), 4.89-4.64 (m, 1H), 2.41-2.18 (m, 2H), 1.86 (s, 5H).

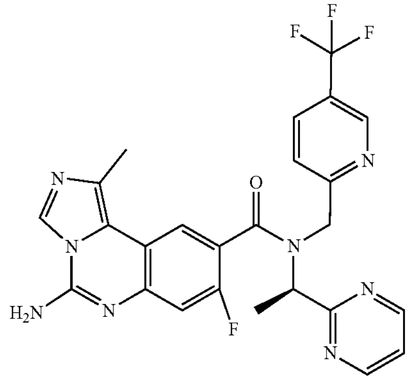 [SMILES: Cc1ncn2c(N)nc3cc(F)c(C(=O)N(Cc4ccc(C(F)(F)F)cn4)[C@H](C)c4ncccn4)cc3c12]

Example Ff-54: (R)-5-amino-8-fluoro-1-methyl-N-(1-(pyrimidin-2-yl)ethyl)-N-((5-(trifluoromethyl)pyridin-2-yl)methyl)imidazo[1,5-c]quinazoline-9-carboxamide. Prepared following general procedure VI-F starting with 5-((tert-butoxycarbonyl)amino)-8-fluoro-1-methylimidazo[1,5-c]quinazoline-9-carboxylic acid Bb-2 and (R)-1-(pyrimidin-2-yl)-N-((5-(trifluoromethyl)pyridin-2-yl)methyl)ethan-1-amine Ec-2. ES/MS: m/z=525.0 $[M+H]^+$. $^1$H NMR (400 MHz, Methanol-d4) δ 8.86 (s, 1H), 8.83-8.64 (m, 3H), 8.23 (d, J=6.9 Hz, 1H), 8.11 (d, J=8.4 Hz, 1H), 7.91 (t, J=9.1 Hz, 1H), 7.64 (d, J=8.3 Hz, 0.8H, major rotamer), 7.46 (d, J=8.1 Hz, 0.2H, minor rotamer), 7.43-7.30 (m, 1.7H, major rotamer), 7.21 (d, J=10.7 Hz, 0.3H, minor rotamer), 5.37 (q, J=7.0 Hz, 1H), 5.17 (d, J=16.7 Hz, 1H), 2.73 (s, 2.2H, major rotamer), 2.63 (s, 0.8H, minor rotamer), 1.77 (d, J=7.1 Hz, 0.8H, minor rotamer), 1.71 (d, J=7.0 Hz, 2.2H, major rotamer).

Examples Ff-55 and Ff-56: Prepared following general procedure VI-F starting with 4-(tert-butoxycarbonylamino)-

7-fluoro-imidazo[1,5-a]quinoxaline-8-carboxylic acid Af-1 and rac-(4aS,9aR)-2-methyl-2,3,4,4a,9,9a-hexahydroindeno[2,1-b][1,4]oxazine En-1. The relative stereochemistry was assigned arbitrarily.

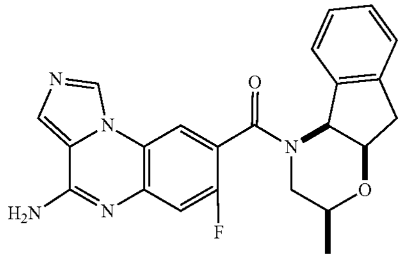 [SMILES: C[C@H]1CN(C(=O)c2cc3c(cc2F)nc(N)c2cncn23)[C@H]2c3ccccc3C[C@H]2O1]

Example Ff-55: Rac-(4-amino-7-fluoroimidazo[1,5-a]quinoxalin-8-yl)((2S,4aS,9aR)-2-methyl-2,3,9,9a-tetrahydroindeno[2,1-b][1,4]oxazin-4(4aH)-yl)methanone. First peak. ES/MS: m/z=418.0 $[M+H]^+$. $^1H$ NMR (400 MHz, Methanol-d4) δ 9.27 (s, 1H), 8.52 (s, 0.5H, diastereomer), 8.45 (s, 0.5H, diastereomer), 8.23 (s, 0.5H, diastereomer), 8.13 (s, 0.5H, diastereomer), 7.42 (t, J=9.4 Hz, 1H), 7.33 (s, 2H), 7.26 (s, 1H), 6.03 (s, 0.5H, diastereomer), 5.00 (s, 0.5H, diastereomer), 4.76 (d, J=21.6 Hz, 0.5H, diastereomer), 4.31 (d, J=13.3 Hz, 0.5H, diastereomer), 4.02 (s, 0.5H, diastereomer), 3.83 (s, 0.5H, diastereomer), 3.40 (s, 0.5H, diastereomer), 3.22 (s, 0.5H, diastereomer), 2.92 (d, J=16.3 Hz, 0.5H, diastereomer), 2.81 (d, J=16.3 Hz, 0.5H, diastereomer), 1.45 (d, J=6.7 Hz, 1H, minor diastereomer), 1.38-1.19 (m, 2H, major diastereomer).

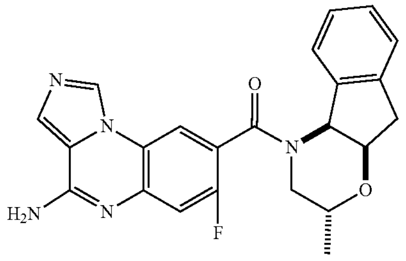 [SMILES: C[C@@H]1CN(C(=O)c2cc3c(cc2F)nc(N)c2cncn23)[C@H]2c3ccccc3C[C@H]2O1]

Example Ff-56: Rac-(4-amino-7-fluoroimidazo[1,5-a]quinoxalin-8-yl)((2R,4aS,9aR)-2-methyl-2,3,9,9a-tetrahydroindeno[2,1-b][1,4]oxazin-4(4aH)-yl)methanone. Second peak. ES/MS: m/z=418.0 $[M+H]^+$. $^1H$ NMR (400 MHz, Methanol-d4) δ 9.25 (s, 1.5H, major diastereomer), 9.22 (s, 0.5H, minor diastereomer), 8.53 (d, J=6.0 Hz, OH, minor diastereomer), 8.48 (s, 1H, major diastereomer), 8.27 (s, 1H, major diastereomer), 8.24 (s, OH, minor diastereomer), 7.45 (d, J=10.1 Hz, 1H, major diastereomer), 7.40 (d, J=9.9 Hz, OH, minor diastereomer), 7.37-7.12 (m, 3H), 5.95 (s, 0.5H, diastereomer), 4.97 (m, 0.5H, diastereomer), 4.64-4.43 (m, 1H), 3.69 (s, 1H), 3.24 (dd, J=16.3, 4.3 Hz, 0.5H, diastereomer), 2.99 (d, J=16.4 Hz, 1H), 2.87 (d, J=16.0 Hz, 1H), 2.58 (dd, J=13.2, 10.5 Hz, 0.5H, diastereomer), 1.14 (d, J=6.2 Hz, 1H, minor diastereomer), 0.97 (d, J=6.2 Hz, 2H, major diastereomer).

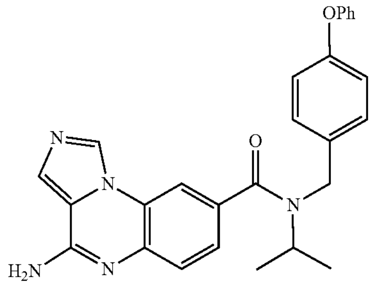 [SMILES: CC(C)N(Cc1ccc(Oc2ccccc2)cc1)C(=O)c1ccc2nc(N)c3cncn3c2c1]

Example Ff-57: 4-amino-N-isopropyl-N-(4-phenoxybenzyl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-(4-phenoxybenzyl)propan-2-amine Ed-10. ES/MS: m/z=452.2 $[M+H]^+$. $^1H$ NMR (400 MHz, DMSO-$d_6$) δ 9.46 (s, 1H), 9.02 (brs, 2H), 8.41 (s, 1H), 7.63 (s, 1H), 7.63 (s, 1H), 7.56 (s, 1H), 7.44 (brs, 2H), 7.39 (t, J=7.6 Hz, 1H), 7.13 (t, J=7.6 Hz, 1H), 6.99 (s, 4H), 4.63 (brs, 2H), 3.98 (brs, 1H), 1.12 (brs, 6H).

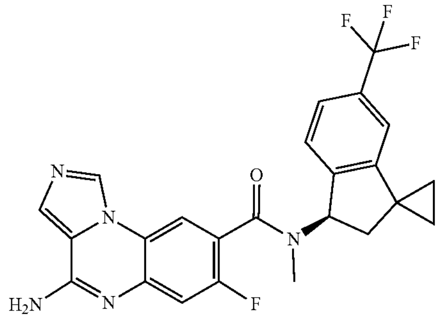 [SMILES: CN(C(=O)c1cc2c(cc1F)nc(N)c1cncn12)[C@@H]1CC2(CC2)c2cc(C(F)(F)F)ccc21]

Example Ff-58: (R)-4-amino-7-fluoro-N-methyl-N-(6'-(trifluoromethyl)-2',3'-dihydrospiro[cyclopropane-1,1'-inden]-3'-yl)imidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (R)—N-methyl-6'-(trifluoromethyl)-2',3'-dihydrospiro[cyclopropane-1,1'-inden]-3'-amine Eo-1. ES/MS: m/z=470.2 $[M+H]^+$. $^1H$ NMR (400 MHz, DMSO-$d_6$) δ 9.16 (s, 0.45H minor rotamer), 9.13 (s, 0.55H major rotamer), 8.46 (brs, 1H), 8.36 (d, J=6.6 Hz, 0.55H major rotamer), 7.93 (s, 0.45H minor rotamer), 7.92 (s, 0.55H major rotamer), 7.69-7.53 (m, 3H), 7.42 (d, J=7.9 Hz, 0.45H minor rotamer), 7.29-7.16 (m, 2H), 6.48-6.31 (m, 0.45H minor rotamer), 5.41 (t, J=7.6 Hz, 0.55H major rotamer), 2.75 (s, 1.65H major rotamer), 2.64 (s, 1.35H minor rotamer), 2.39-2.19 (m, 1H), 1.26-1.15 (m, 2H), 1.11-0.91 (m, 2H).

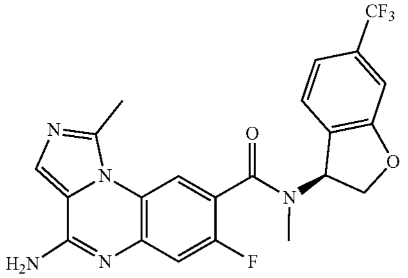

Example Ff-59: (S)-4-amino-7-fluoro-N,1-dimethyl-N-(6-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)-7-fluoro-1-methylimidazo[1,5-a]quinoxaline-8-carboxylic acid Af-5 and (S)—N-methyl-6-(trifluoromethyl)-2,3-dihydrobenzofuran-3-amine hydrochloride Eh-1. ES/MS: m/z=459.9 $[M+H]^+$. $^1$H NMR (400 MHz, DMSO-d6) δ 8.73 (s, 2H), 8.20 (d, J=28.0 Hz, 1H), 7.63 (d, J=7.8 Hz, 1H), 7.54-7.24 (m, 3H), 6.50 (d, J=8.7 Hz, 0.5H, rotamer one), 5.65 (s, 0.5H, rotamer two), 4.91 (t, J=9.9 Hz, 1H), 4.76 (dd, J=10.3, 4.3 Hz, 1H), 3.07 (d, J=10.1 Hz, 3H), 2.74 (s, 1.5H, rotamer one), 2.62 (s, 1.5H, rotamer two).

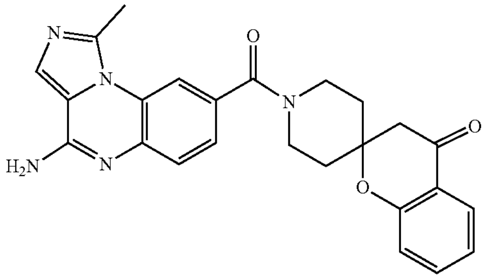 [SMILES: Cc1ncc2c(N)nc3ccc(C(=O)N4CCC5(CC4)CC(=O)c4ccccc4O5)cc3n12]

Example Ff-60: 1'-(4-amino-1-methylimidazo[1,5-a]quinoxaline-8-carbonyl)spiro[chromane-2,4'-piperidin]-4-one. Prepared using general procedure VI-F starting with 4-((tert-butoxycarbonyl)amino)-1-methylimidazo[1,5-a]quinoxaline-8-carboxylic acid Af-3 and commercial spiro[chromane-2,4'-piperidin]-4-one. ES/MS: m/z=442.2 $[M+H]^+$. $^1$H NMR (400 MHz, DMSO-d6) δ 8.34 (s, 1H), 8.14 (d, J=1.6 Hz, 1H), 7.75 (dd, J=7.8, 1.8 Hz, 1H), 7.66-7.53 (m, 3H), 7.18-6.97 (m, 2H), 3.45 (d, J=103.3 Hz, 8H), 3.04 (s, 3H), 2.90 (s, 2H).

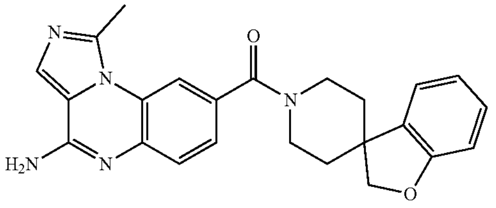 [SMILES: Cc1ncc2c(N)nc3ccc(C(=O)N4CCC5(CC4)COc4ccccc45)cc3n12]

Example Ff-61: (4-amino-1-methylimidazo[1,5-a]quinoxalin-8-yl)(2H-spiro[benzofuran-3,4'-piperidin]-1'-yl)methanone. Prepared using general procedure VI-F starting with 4-((tert-butoxycarbonyl)amino)-1-methylimidazo[1,5-a]quinoxaline-8-carboxylic acid Af-3 and commercial 2H-spiro[benzofuran-3,4'-piperidine]. ES/MS: m/z=414.2 $[M+H]^+$. Multiplet Report $^1$H NMR (400 MHz, DMSO-d6) δ 9.34 (s, 2H), 8.36 (s, 1H), 8.18 (d, J=1.4 Hz, 1H), 7.69-7.62 (m, 2H), 7.33 (dd, J=7.4, 1.3 Hz, 1H), 7.14 (td, J=7.7, 1.4 Hz, 1H), 6.89 (td, J=7.4, 1.0 Hz, 1H), 6.80 (d, J=7.9 Hz, 1H), 4.50 (s, 2H), 3.71 (s, 1H), 3.22 (s, 1H), 3.06 (s, 3H), 1.93 (s, 2H), 1.76 (s, 2H). Calcd: 23+1H, found: 21H.

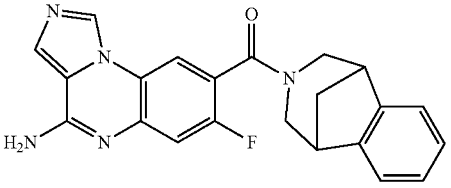 [SMILES: Nc1nc2cc(F)c(C(=O)N3CC4CC(C3)c3ccccc34)cc2n2cncc12]

Example Ff-62: (4-amino-7-fluoroimidazo[1,5-a]quinoxalin-8-yl)(1,2,4,5-tetrahydro-3H-1,5-methanobenzo[d]azepin-3-yl)methanone. Prepared following general procedure VI-F starting with 4-(tert-butoxycarbonylamino)-7-fluoro-imidazo[1,5-a]quinoxaline-8-carboxylic acid Af-1 and commercial 2,3,4,5-Tetrahydro-lh-1,5-methanobenzo[d]azepine hydrochloride. ES/MS: m/z=388.0 $[M+H]^+$. $^1$H NMR (400 MHz, MeOD) δ 9.29-8.82 (m, 1H), 8.37 (d, J=0.7 Hz, 1H), 7.49-7.00 (m, 6H), 4.58 (d, J=12.8 Hz, 1H), 3.65 (d, J=12.4 Hz, 1H), 3.46 (s, 1H), 3.40-3.25 (m, 2H), 3.15 (d, J=4.3 Hz, 1H), 2.37 (dt, J=10.5, 5.1 Hz, 1H), 2.09 (d, J=10.9 Hz, 1H).

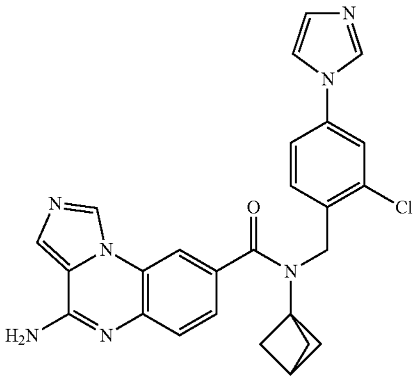 [SMILES: Nc1nc2ccc(C(=O)N(Cc3ccc(-n4ccnc4)cc3Cl)C34CC(C3)C4)cc2n2cncc12]

Example Ff-63: 4-amino-N-(bicyclo[1.1.1]pentan-1-yl)-N-(2-chloro-4-(1H-imidazol-1-yl)benzyl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-(2-chloro-4-(1H-imidazol-1-yl)benzyl)bicyclo[1.1.1]pentan-1-amine Ec-7. ES/MS: m/z=484.2 $[M+H]^+$. $^1$H NMR (400 MHz, MeOD) δ 9.41 (s, 1H), 9.31 (s, 1H), 8.46 (s, 1H), 8.40 (s, 1H), 8.10 (t, J=1.8 Hz, 1H), 7.96 (s, 1H), 7.87-7.58 (m, 5H), 4.95 (s, 2H), 2.35 (s, 1H), 1.93 (s, 6H).

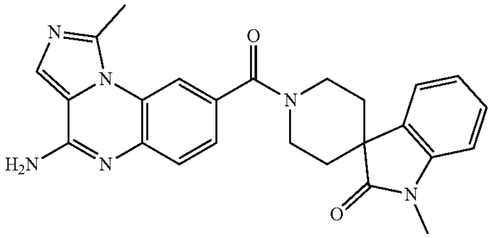 [SMILES: Cc1ncc2c(N)nc3ccc(C(=O)N4CCC5(CC4)C(=O)N(C)c4ccccc45)cc3n12]

Example Ff-64: 1'-(4-amino-1-methylimidazo[1,5-a]quinoxaline-8-carbonyl)-1-methylspiro[indoline-3,4'-piperidin]-2-one. Prepared using general procedure VI-F starting with 4-((tert-butoxycarbonyl)amino)-1-methylimidazo[1,5-a]quinoxaline-8-carboxylic acid Af-3 and commercial 1-methylspiro[indoline-3,4'-piperidin]-2-one. ES/MS: m/z=441.0 $[M+H]^+$. $^1H$ NMR (400 MHz, DMSO-$d_6$) δ 9.31 (s, 2H), 8.36 (s, 1H), 8.22 (d, J=1.2 Hz, 1H), 7.68 (d, J=1.5 Hz, 2H), 7.58 (dd, J=7.5, 1.1 Hz, 1H), 7.32 (td, J=7.8, 1.2 Hz, 1H), 7.12-7.01 (m, 2H), 4.14 (s, 7H), 3.69 (s, 1H), 3.15 (s, 3H), 3.07 (s, 3H), 3.02 (dtd, J=6.6, 4.0, 2.4 Hz, 1H).

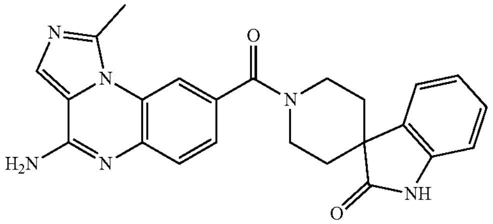 [SMILES: Cc1ncc2c(N)nc3ccc(C(=O)N4CCC5(CC4)C(=O)Nc4ccccc45)cc3n12]

Example Ff-65: 1'-(4-amino-1-methylimidazo[1,5-a]quinoxaline-8-carbonyl)spiro[indoline-3,4'-piperidin]-2-one. Prepared using general procedure VI-F starting with 4-((tert-butoxycarbonyl)amino)-1-methylimidazo[1,5-a]quinoxaline-8-carboxylic acid Af-3 and commercial spiro[indoline-3,4'-piperidin]-2-one. ES/MS: m/z=427.2 $[M+H]^+$. $^1H$ NMR (400 MHz, DMSO-$d_6$) δ 10.47 (s, 1H), 9.32 (s, 2H), 8.36 (s, 1H), 8.22 (s, 1H), 7.68 (s, 2H), 7.52 (d, J=7.4 Hz, 1H), 7.21 (td, J=7.7, 1.1 Hz, 1H), 7.00 (td, J=7.6, 1.0 Hz, 1H), 6.88 (d, J=7.7 Hz, 1H), 3.79 (d, J=100.2 Hz, 8H), 3.07 (s, 4H).

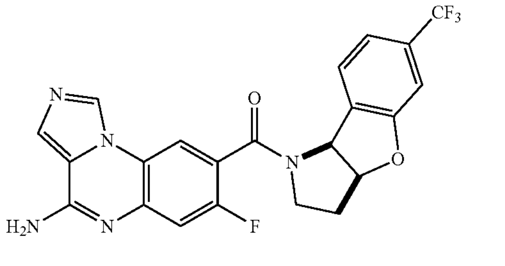 [SMILES: Nc1nc2cc(F)c(C(=O)N3CC[C@@H]4Oc5cc(C(F)(F)F)ccc5[C@@H]43)cc2n2cncc12]

Example Ff-66: (4-amino-7-fluoroimidazo[1,5-a]quinoxalin-8-yl)((3aS,8bS)-6-(trifluoromethyl)-2,3,3a,8b-tetrahydro-1H-benzofuro[3,2-b]pyrrol-1-yl)methanone. Prepared following general procedure VI-F starting with 4-(tert-butoxycarbonylamino)-7-fluoro-imidazo[1,5-a]quinoxaline-8-carboxylic acid Af-1 and cis-(3aS,8bS)-6-(trifluoromethyl)-2,3,3a,8b-tetrahydro-1H-benzofuro[3,2-b]pyrrole Ep-1. ES/MS: m/z=457.9 $[M+H]^+$. $^1H$ NMR (400 MHz, Acetonitrile-d3) δ 8.84 (s, 1H), 8.27 (s, 1H), 8.10 (d, J=5.9 Hz, 1H), 7.84 (d, J=7.8 Hz, 1H), 7.42-7.25 (m, 2H), 7.18 (d, J=1.1 Hz, 1H), 5.96 (d, J=6.6 Hz, 1H), 5.63-5.42 (m, 1H), 3.62-3.33 (m, 2H), 2.38-2.24 (m, 2H).

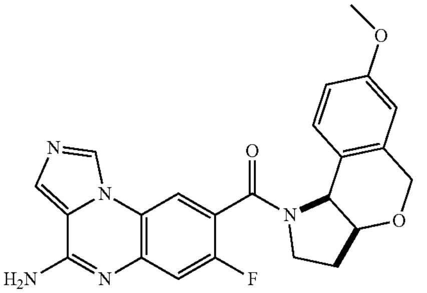 [SMILES: COc1ccc2c(c1)CO[C@H]1CCN(C(=O)c3cc4c(cc3F)nc(N)c3cncn34)[C@@H]21]

Example Ff-67: Rac-(4-amino-7-fluoroimidazo[1,5-a]quinoxalin-8-yl)((3aS,9bS)-7-methoxy-3,3a,5,9b-tetrahydroisochromeno[4,3-b]pyrrol-1(2H)-yl)methanone. Prepared following general procedure VI-F starting with 4-(tert-butoxycarbonylamino)-7-fluoro-imidazo[1,5-a]quinoxaline-8-carboxylic acid Af-1 and Cis-(3aS,9bS)-7-methoxy-1,2,3,3a,5,9b-hexahydroisochromeno[4,3-b]pyrrole El-2. ES/MS: m/z=434.0 $[M+H]^+$. $^1H$ NMR (400 MHz, MeOD) δ 9.26 (s, 1H), 8.41 (d, J=5.9 Hz, 1H), 8.33 (s, 1H), 8.06 (d, J=8.8 Hz, 1H), 7.42 (d, J=10.0 Hz, 1H), 6.85 (dd, J=8.8, 2.7 Hz, 1H), 6.70 (s, 1H), 5.27 (d, J=4.7 Hz, 1H), 4.77 (d, J=14.8 Hz, 1H), 4.66 (d, J=14.7 Hz, 1H), 4.55 (s, 1H), 3.81 (s, 4H), 3.57 (d, J=8.8 Hz, 1H), 2.08 (d, J=7.0 Hz, 2H).

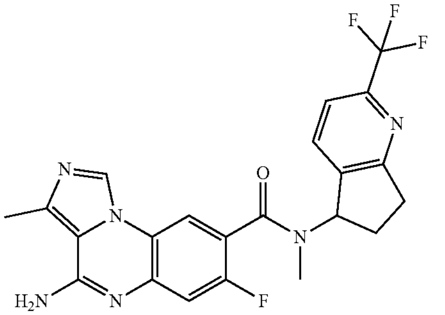 [SMILES: Cc1ncn2c1c(N)nc1cc(F)c(C(=O)N(C)C3CCc4nc(C(F)(F)F)ccc43)cc12]

Example Ff-68: 4-amino-7-fluoro-N,3-dimethyl-N-(2-(trifluoromethyl)-6,7-dihydro-5H-cyclopenta[b]pyridin-5-yl)imidazo[1,5-a]quinoxaline-8-carboxamide. Prepared following general procedure VI-F starting with 4-((tert-butoxycarbonyl)amino)-7-fluoro-3-methylimidazo[1,5-a]quinoxaline-8-carboxylic acid Af-4 and N-methyl-2-(trifluoromethyl)-6,7-dihydro-5H-cyclopenta[b]pyridin-5-amine hydrochloride Eh-3. ES/MS: m/z=459.0 $[M+H]^+$. $^1H$ NMR (400 MHz, MeOD) δ 9.18 (s, 1H), 8.42 (d, J=5.9 Hz, 1H), 7.94 (d, J=7.8 Hz, 1H), 7.74 (d, J=7.9 Hz, 1H), 7.47 (d, J=9.7 Hz, 1H), 6.37 (t, J=8.2 Hz, 0.6H, major rotamer), 5.47 (t, J=8.4 Hz, 0.4H, minor rotamer), 3.27-3.17 (m, 1H), 3.06-2.86 (m, 2H), 2.86-2.65 (m, 5H), 2.61-2.27 (m, 2H).

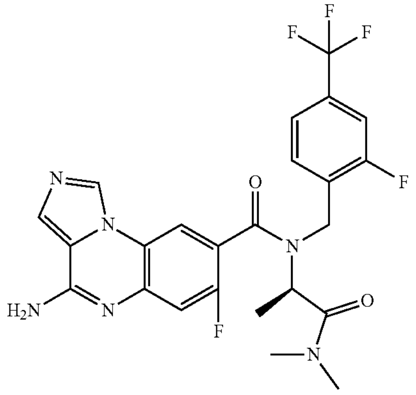 [SMILES: C[C@H](C(=O)N(C)C)N(Cc1ccc(C(F)(F)F)cc1F)C(=O)c1cc2c(cc1F)nc(N)c1cncn12]

Example Ff-69: 4-amino-N-[(1R)-2-(dimethylamino)-1-methyl-2-oxo-ethyl]-7-fluoro-N-[[2-fluoro-4-(trifluoromethyl)phenyl]methyl]imidazo[1,5-a]quinoxaline-8-carboxamide. Prepared following general procedure VI-F starting with 4-(tert-butoxycarbonylamino)-7-fluoro-imidazo[1,5-a]quinoxaline-8-carboxylic acid Af-1 and (2R)-2-[[2-fluoro-4-(trifluoromethyl)phenyl]methylamino]-N,N-dimethyl-propanamide Ec-8. ES/MS: m/z=521.4 $[M+H]^+$. $^1H$ NMR (400 MHz, Methanol-d4) δ 9.15 (s, 1H), 8.36 (d, J=8.6 Hz, 1H), 8.28 (d, J=5.8 Hz, 1H), 7.73-7.42 (m, 2H), 7.35-7.23 (m, 2H), 5.82 (q, J=7.0 Hz, 1H), 4.85 (s, 2H), 3.26 (s, 3H), 2.90 (s, 3H), 1.51-1.41 (m, 3H).

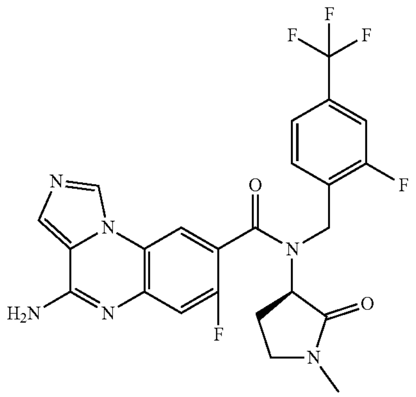 [SMILES: CN1CC[C@@H](N(Cc2ccc(C(F)(F)F)cc2F)C(=O)c2cc3c(cc2F)nc(N)c2cncn23)C1=O]

Example Ff-70: 4-amino-7-fluoro-N-[[2-fluoro-4-(trifluoromethyl)phenyl]methyl]-N-[(3R)-1-methyl-2-oxo-pyrrolidin-3-yl]imidazo[1,5-a]quinoxaline-8-carboxamide. Prepared following general procedure VI-F starting with 4-(tert-butoxycarbonylamino)-7-fluoro-imidazo[1,5-a]quinoxaline-8-carboxylic acid Af-1 and (3R)-3-[[2-fluoro-4-(trifluoromethyl)phenyl]methylamino]-1-methyl-pyrrolidin-2-one Ec-9. ES/MS: m/z=519.4 $[M+H]^+$. $^1H$ NMR (400 MHz, Methanol-d4) δ 9.33-9.15 (m, 1H), 8.61-8.32 (m, 2H), 7.91-7.62 (m, 1H), 7.60-7.35 (m, 3H), 5.18-5.04 (m, 1H), 4.85-4.72 (m, 1H), 4.59-4.31 (m, 1H), 3.59-3.37 (m, 2H), 2.95-2.78 (m, 3H), 2.53-2.07 (m, 2H).

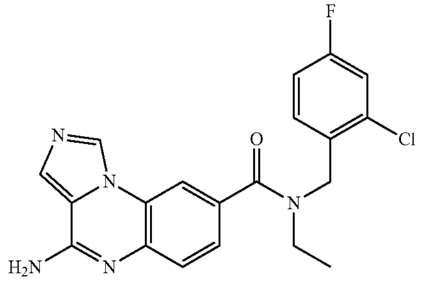 [SMILES: CCN(Cc1ccc(F)cc1Cl)C(=O)c1ccc2nc(N)c3cncn3c2c1]

Example Ff-71: 4-amino-N-(2-chloro-4-fluorobenzyl)-N-ethylimidazo[1,5-a]quinoxaline-8-carboxamide. Prepared following general procedure VI-F starting with 4-(tert-butoxycarbonylamino)imidazo[1,5-a]quinoxaline-8-carboxylic acid Ae-1 and N-[(2-chloro-4-fluoro-phenyl)methyl]ethanamine Eb-2. ES/MS: m/z=397.9 $[M+H]^+$. $^1H$ NMR (400 MHz, DMSO-d6) δ 9.52 (s, 3H), 8.64-8.36 (m, 2H), 7.63 (m, 4H), 7.32 (td, J=8.5, 2.7 Hz, 1H), 4.71 (m, 2H), 3.38 (m, 2H), 1.11 (s, 3H).

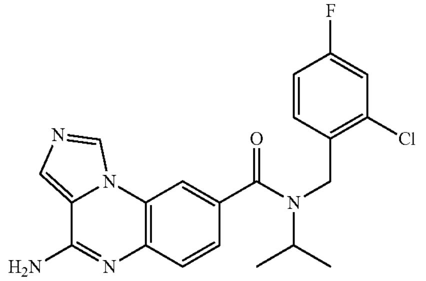 [SMILES: CC(C)N(Cc1ccc(F)cc1Cl)C(=O)c1ccc2nc(N)c3cncn3c2c1]

Example Ff-72: 4-amino-N-(2-chloro-4-fluorobenzyl)-N-isopropylimidazo[1,5-a]quinoxaline-8-carboxamide. Prepared following general procedure VI-F starting with 4-(tert-butoxycarbonylamino)imidazo[1,5-a]quinoxaline-8-carboxylic acid Ae-1 and N-[(2-chloro-4-fluoro-phenyl)methyl]propan-2-amine Eb-3. ES/MS: m/z=411.9 $[M+H]^+$. $^1H$ NMR (400 MHz, DMSO-d6) δ 9.46 (s, 1H), 8.47 (s, 1H), 8.33 (s, 1H), 7.66 (s, 2H), 7.59-7.43 (m, 1H), 7.28 (td, J=8.5, 2.7 Hz, 1H), 4.63 (s, 2H), 4.13 (s, 1H), 1.17 (s, 6H).

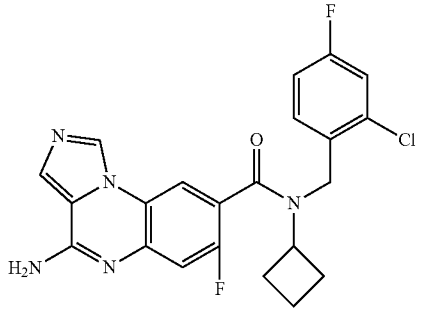 [SMILES: Nc1nc2cc(F)c(C(=O)N(Cc3ccc(F)cc3Cl)C3CCC3)cc2n2cncc12]

Example Ff-73: 4-amino-N-(2-chloro-4-fluorobenzyl)-N-cyclobutyl-7-fluoroimidazo[1,5-a]quinoxaline-8-carboxamide. Prepared following general procedure VI-F starting with 4-(tert-butoxycarbonylamino)-7-fluoro-imidazo[1,5-a]quinoxaline-8-carboxylic acid Af-1 and N-[(2-chloro-4-fluoro-phenyl)methyl]cyclobutanamine Eb-4. ES/MS: m/z=441.9 $[M+H]^+$. $^1H$ NMR (400 MHz, DMSO-d6) δ 9.38 (s, 1H), 8.48 (d, J=6.2 Hz, 1H), 8.28 (s, 1H), 7.63-7.44 (m, 2H), 7.39-7.24 (m, 2H), 4.85 (s, 2H), 4.30 (t, J=8.6 Hz, 1H), 2.12 (q, J=10.2 Hz, 2H), 1.94 (s, 2H), 1.47 (m, 2H).

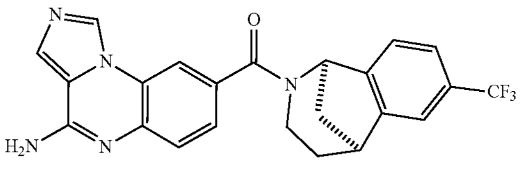

(±)

Example Ff-74: (Rac)-(4-aminoimidazo[1,5-a]quinoxalin-8-yl)(7-(trifluoromethyl)-1,3,4,5-tetrahydro-2H-1,5-methanobenzo[c]azepin-2-yl)methanone. Prepared following general procedure VI-F starting with 4-(tert-butoxycarbonylamino)imidazo[1,5-a]quinoxaline-8-carboxylic acid Ae-1 and 4-(trifluoromethyl)-9-azatricyclo[6.3.1.02,7]dodeca-2(7),3,5-triene Ef-1. ES/MS: m/z=438.0 $[M+H]^+$. $^1H$ NMR (400 MHz, DMSO-d6) δ 9.49 (s, 1H), 8.48 (m, 2H), 7.85-7.39 (m, 4H), 5.03 (s, 1H), 4.19 (s, 1H), 3.49 (m, 2H), 2.43-1.95 (m, 2H), 1.90-1.51 (m, 2H).

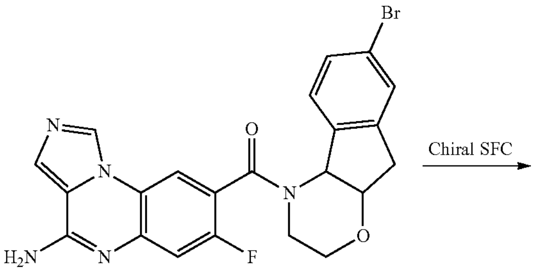

Example Ff-28

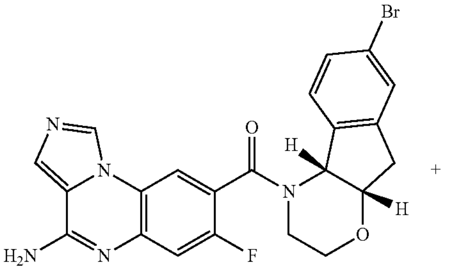

Example Ff-75

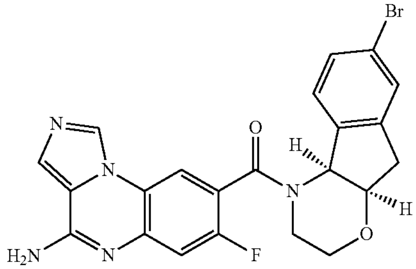

Example Ff-76

Examples Ff-75 and Ff-76. Example Ff-28 was separated by chiral SFC (SFC IC column, 50% EtOH, 60 mL/min) to give Ff-75 (peak 1, RT=8.0 min) and Ff-76 (peak 2, RT=14.1 min).

Example Ff-75: (4-amino-7-fluoroimidazo[1,5-a]quinoxalin-8-yl)((4aR,9aS)-7-bromo-2,3,9,9a-tetrahydroindeno[2,1-b][1,4]oxazin-4(4aH)-yl)methanone. Peak 1. ES/MS: m/z=481.8 $[M+H]^+$. $^1H$ NMR (400 MHz, DMSO-d6) δ 9.35 (d, J=27.3 Hz, 1H), 8.73 (s, 2H), 8.58 (d, J=6.3 Hz, 1H), 8.24 (d, J=13.4 Hz, 1H), 7.63-7.38 (m, 3H), 7.19 (s, 1H), 5.86 (s, 1H), 4.44-4.31 (m, 2H), 3.85 (d, 0.5H, rotamer 1), 3.66 (d, J=11.4 Hz, 0.5H, rotamer 2), 3.60-3.47 (m, 1H), 3.39-3.22 (m, 1H), 3.13-2.99 (m, 1H), 2.86-2.69 (m, 1H).

Example Ff-76: (4-amino-7-fluoroimidazo[1,5-a]quinoxalin-8-yl)((4aS,9aR)-7-bromo-2,3,9,9a-tetrahydroindeno[2,1-b][1,4]oxazin-4(4aH)-yl)methanone. Peak 2. ES/MS: m/z=481.8 $[M+H]^+$. $^1H$ NMR (400 MHz, DMSO-d6) δ 9.35 (d, J=27.3 Hz, 1H), 8.73 (s, 2H), 8.58 (d, J=6.3 Hz, 1H), 8.24 (d, J=13.4 Hz, 1H), 7.63-7.38 (m, 3H), 7.19 (s, 1H), 5.86 (s, 1H), 4.44-4.31 (m, 2H), 3.85 (d, 0.5H, rotamer 1), 3.66 (d, J=11.4 Hz, 0.5H, rotamer 2), 3.60-3.47 (m, 1H), 3.39-3.22 (m, 1H), 3.13-2.99 (m, 1H), 2.86-2.69 (m, 1H).

Examples Ff-77 (Peak 1) and Ff-78 (Peak 2) were Separated by Reverse Phase HPLC

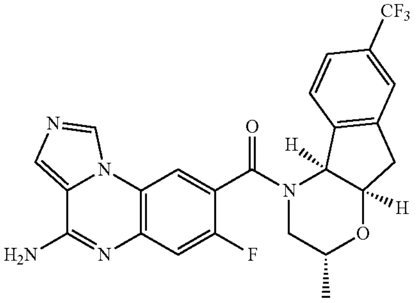 [SMILES: C[C@@H]1CN(C(=O)c2cc3c(cc2F)nc(N)c2cncn23)[C@H]2c3ccc(C(F)(F)F)cc3C[C@H]2O1]

Example Ff-77: (4-amino-7-fluoroimidazo[1,5-a]quinoxalin-8-yl)((2R,4aS,9aR)-2-methyl-7-(trifluoromethyl)-2,3,9,9a-tetrahydroindeno[2,1-b][1,4]oxazin-4(4aH)-yl) methanone. Prepared following general procedure VI-F starting with 4-(tert-butoxycarbonylamino)-7-fluoro-imidazo[1,5-a]quinoxaline-8-carboxylic acid Af-1 and (2R)-2-methyl-7-(trifluoromethyl)-2,3,4,4a,9,9a-hexahydroindeno[2,1-b][1,4]oxazine Eu-2 and isolated as the first isomer. ES/MS: m/z=485.9 $[M+H]^+$. $^1H$ NMR (400 MHz, DMSO-d6) δ 9.37 (s, 1H), 8.54 (s, 1H), 8.17 (d, J=14.6 Hz, 1H), 7.80-7.61 (m, 3H), 7.53-7.33 (m, 1H), 6.04 (s, 1H), 4.70 (t, J=4.2 Hz, 1H), 4.61 (t, J=4.1 Hz, 1H) 4.23 (d, J=13.3 Hz, 1H), 4.01 (s, 1H), 3.80 (s, 1H), 3.37-3.02 (m, 1H), 3.02-2.68 (m, 1H), 1.40 (d, J=16.5 Hz, 1.5H, rotamer one), 1.25 (d, J=6.7 Hz, 1.5H, rotamer two).

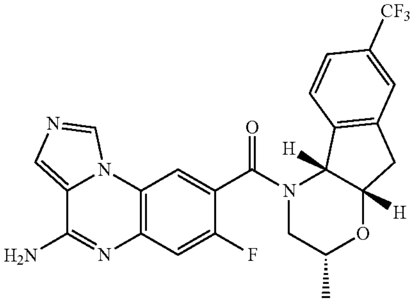 [SMILES: C[C@@H]1CN(C(=O)c2cc3c(cc2F)nc(N)c2cncn23)[C@@H]2c3ccc(C(F)(F)F)cc3C[C@@H]2O1]

Example Ff-78: (4-amino-7-fluoroimidazo[1,5-a]quinoxalin-8-yl)((2R,4aR,9aS)-2-methyl-7-(trifluoromethyl)-2,3,9,9a-tetrahydroindeno[2,1-b][1,4]oxazin-4(4aH)-yl) methanone. Prepared following general procedure VI-F starting with 4-(tert-butoxycarbonylamino)-7-fluoro-imidazo[1,5-a]quinoxaline-8-carboxylic acid Af-1 and (2R)-2-methyl-7-(trifluoromethyl)-2,3,4,4a,9,9a-hexahydroindeno [2,1-b][1,4]oxazine Eu-2 and isolated as the second isomer. ES/MS: m/z=485.9 $[M+H]^+$. $^1H$ NMR (400 MHz, DMSO-d6) δ 9.34 (s, 0.67H major rotamer), 9.26 (s, 0.33H minor rotamer), 8.57 (d, J=6.2 Hz, 1H), 8.22 (d, J=18.1 Hz, 1H), 7.79-7.58 (m, 2H), 7.43 (d, J=10.5 Hz, 1H), 7.36 (d, J=10.3 Hz, 1H), 5.97 (s, 1H), 4.64-4.32 (m, 2H), 3.44-3.24 (m, 2H), 3.17-2.64 (m, 2H), 1.09 (d, J=6.2 Hz, 1H, minor rotamer), 0.93 (d, J=6.2 Hz, 2H, major rotamer).

Examples Ff-80 (Peak 1) and Ff-81 (Peak 2) were Separated by Reverse Phase HPLC

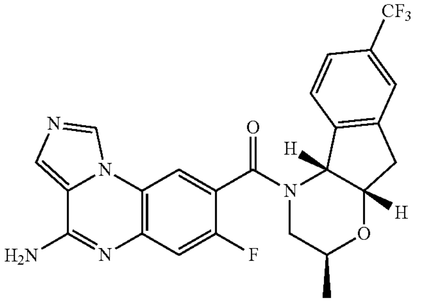 [SMILES: C[C@H]1CN(C(=O)c2cc3c(cc2F)nc(N)c2cncn23)[C@@H]2c3ccc(C(F)(F)F)cc3C[C@@H]2O1]

Example Ff-80: (4-amino-7-fluoroimidazo[1,5-a]quinoxalin-8-yl)((2S,4aR,9aS)-2-methyl-7-(trifluoromethyl)-2,3,9,9a-tetrahydroindeno[2,1-b][1,4]oxazin-4(4aH)-yl) methanone. Prepared following general procedure VI-F starting with 4-(tert-butoxycarbonylamino)-7-fluoro-imidazo[1,5-a]quinoxaline-8-carboxylic acid Af-1 and (2S)-2-methyl-7-(trifluoromethyl)-2,3,4,4a,9,9a-hexahydroindeno [2,1-b][1,4]oxazine Eu-1 and isolated as the first isomer (peak 1). ES/MS: m/z=485.9 $[M+H]^+$. $^1H$ NMR (400 MHz, DMSO-d6) δ 9.37 (s, 1H), 8.54 (s, 1H), 8.17 (d, J=14.6 Hz, 1H), 7.80-7.61 (m, 3H), 7.53-7.33 (m, 1H), 6.04 (s, 1H), 4.69 (dt, J=37.1, 4.2 Hz, 1H), 4.23 (d, J=13.3 Hz, 1H), 4.01 (s, 1H), 3.80 (s, 1H), 3.37-3.02 (m, 1H), 3.02-2.68 (m, 1H), 1.40 (d, J=16.5 Hz, 1.5H, rotamer one), 1.25 (d, J=6.7 Hz, 1.5H, rotamer two).

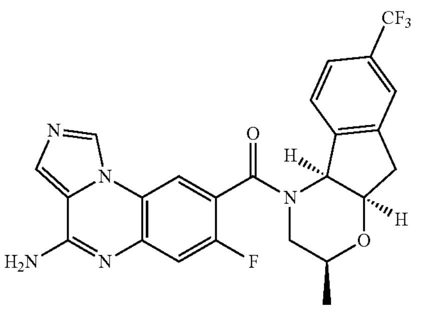 [SMILES: C[C@H]1CN(C(=O)c2cc3c(cc2F)nc(N)c2cncn23)[C@H]2c3ccc(C(F)(F)F)cc3C[C@H]2O1]

Example Ff-81: (4-amino-7-fluoroimidazo[1,5-a]quinoxalin-8-yl)((2S,4aS,9aR)-2-methyl-7-(trifluoromethyl)-2,3,9,9a-tetrahydroindeno[2,1-b][1,4]oxazin-4(4aH)-yl) methanone. Prepared following general procedure VI-F starting with 4-(tert-butoxycarbonylamino)-7-fluoro-imidazo[1,5-a]quinoxaline-8-carboxylic acid Af-1 and (2S)-2-methyl-7-(trifluoromethyl)-2,3,4,4a,9,9a-hexahydroindeno [2,1-b][1,4]oxazine Eu-1 and isolated as the second isomer (peak 2). ES/MS: m/z=485.9 $[M+H]^+$. $^1H$ NMR (400 MHz, DMSO-d6) δ 9.37 (s, 0.67H major rotamer), 9.29 (s, 0.33H minor rotamer), 8.87 (brs, 2H), 8.65 (brs, 0.33H minor rotamer), 8.57 (d, J=6.2 Hz, 0.67H major rotamer), 8.26 (s, 0.67H major rotamer), 8.22 (s, 0.33H minor rotamer), 7.79-7.58 (m, 2H), 7.46 (d, J=10.3 Hz, 0.67H major rotamer), 7.39 (d, J=10.3 Hz, 0.33H major rotamer), 7.34 (brs, 1H), 5.94 (s, 0.67H, major rotamer), 5.02 (s, 0.33H, minor rotamer), 4.64-4.32 (m, 1H), 3.70-3.54 (m, 1H), 3.41-3.24 (m, 1H), 3.17-2.64 (m, 2H), 1.09 (d, J=6.2 Hz, 0.99H, minor rotamer), 0.93 (d, J=6.2 Hz, 2.01H, major rotamer).

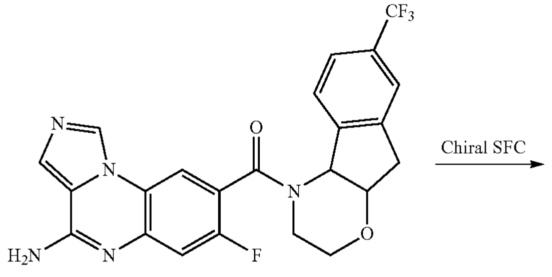

Example Ff-34

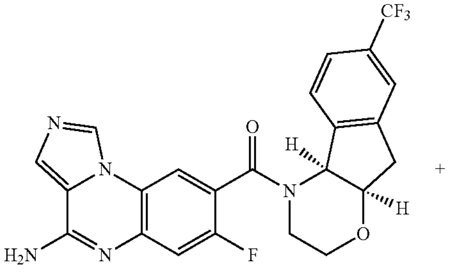

+

Example Ff-82

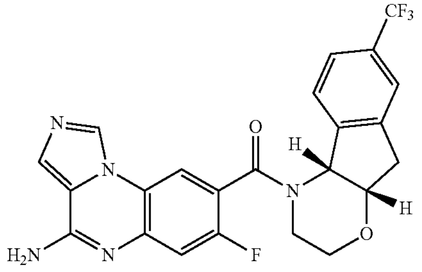

Example Ff-83

Examples Ff-82 and Ff-83. Example Ff-34 was separated by chiral SFC (SFC IG column, 40% MeOH, 60 mL/min) to give Ff-82 (peak 1, RT=11.7 min) and Ff-83 (peak 2, RT=15.65 min).

Example Ff-82: (4-amino-7-fluoroimidazo[1,5-a]quinoxalin-8-yl)((4aS,9aR)-7-(trifluoromethyl)-2,3,9,9a-tetrahydroindeno[2,1-b][1,4]oxazin-4(4aH)-yl)methanone. ES/MS: m/z=471.9 $[M+H]^+$. $^1H$ NMR (400 MHz, DMSO-d6) δ 9.33 (m, 1H), 8.57 (d, J=6.3 Hz, 1H), 8.20 (d, J=16.0 Hz, 1H), 7.79-7.59 (m, 2H), 7.42 (dd, J=25.4, 10.4 Hz, 2H), 5.99 (s, 1H), 4.56-4.34 (m, 1H), 3.92-3.45 (m, 2H), 3.35 (t, J=14.3 Hz, 2H), 3.05 (dd, J=43.0, 15.2 Hz, 2H).

Example Ff-83: (4-amino-7-fluoroimidazo[1,5-a]quinoxalin-8-yl)((4aR,9aS)-7-(trifluoromethyl)-2,3,9,9a-tetrahydroindeno[2,1-b][1,4]oxazin-4(4aH)-yl)methanone. ES/MS: m/z=471.9 $[M+H]^+$. $^1H$ NMR (400 MHz, DMSO-d6) δ 9.33 (m, 1H), 8.57 (d, J=6.3 Hz, 1H), 8.20 (d, J=16.0 Hz, 1H), 7.79-7.59 (m, 2H), 7.42 (dd, J=25.4, 10.4 Hz, 2H), 5.99 (s, 1H), 4.56-4.34 (m, 1H), 3.92-3.45 (m, 2H), 3.35 (t, J=14.3 Hz, 2H), 3.05 (dd, J=43.0, 15.2 Hz, 2H).

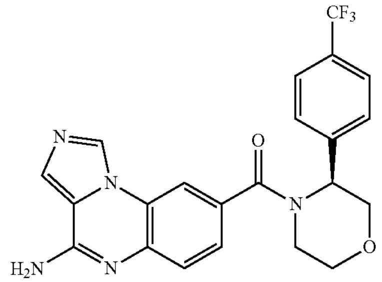 [SMILES: Nc1nc2ccc(C(=O)N3CCOC[C@@H]3c3ccc(C(F)(F)F)cc3)cc2n2cncc12]

Example Ff-84: (S)-(4-aminoimidazo[1,5-a]quinoxalin-8-yl)(3-(4-(trifluoromethyl)phenyl)morpholino)methanone. Prepared following general procedure VI-F starting with 4-(tert-butoxycarbonylamino)imidazo[1,5-a]quinoxaline-8-carboxylic acid Ae-1 and commercial (3S)-3-[4-(trifluoromethyl)phenyl]morpholine. ES/MS: m/z=441.9 $[M+H]^+$. $^1H$ NMR (400 MHz, DMSO-d6) δ 9.49 (s, 1H), 8.52 (d, J=1.5 Hz, 1H), 8.43 (s, 1H), 7.97-7.51 (m, 5H), 5.74 (s, 1H), 4.55 (d, J=12.3 Hz, 2H), 4.13-3.78 (m, 2H), 3.67 (td, J=11.5, 2.9 Hz, 1H), 3.29 (s, 1H).

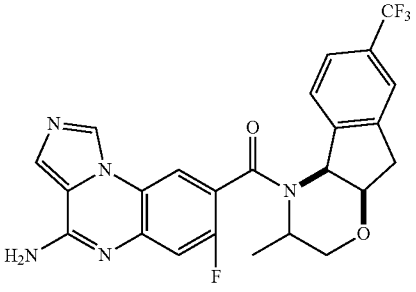

Example Ff-85: (4-amino-7-fluoroimidazo[1,5-a]quinoxalin-8-yl)(3-methyl-7-(trifluoromethyl)-2,3,9,9a-tetrahydroindeno[2,1-b][1,4]oxazin-4(4aH)-yl)methanone. Prepared following general procedure VI-F starting with 4-(tert-butoxycarbonylamino)-7-fluoro-imidazo[1,5-a]quinoxaline-8-carboxylic acid Af-1 and 3-methyl-7-(trifluoromethyl)-2,3,4,4a,9,9a-hexahydroindeno[2,1-b][1,4]oxazine Ez-1. ES/MS: m/z=485.9 $[M+H]^+$. $^1H$ NMR (400 MHz, DMSO-d6) δ 9.32 (s, 1H), 8.59 (s, 1H), 8.13 (s, 1H), 7.81-7.28 (m, 4H), 5.81 (s, 1H), 4.84-4.71 (m, 1H), 4.53-4.42 (m, 1H), 3.73 (d, J=16.2 Hz, 2H), 3.31-2.94 (m, 2H), 1.05-0.92 (m, 1.5H, diastereomer), 0.77 (d, J=6.9 Hz, 1.5H, diastereomer).

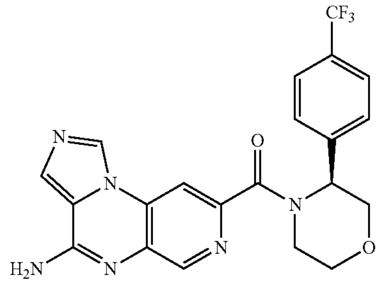 [SMILES: Nc1nc2cnc(C(=O)N3CCOC[C@@H]3c3ccc(C(F)(F)F)cc3)cc2n2cncc12]

Example Ff-86: (S)-(4-aminoimidazo[1,5-a]pyrido[3,4-e]pyrazin-8-yl)(3-(4-(trifluoromethyl)phenyl)morpholino)methanone. Prepared following general procedure VI-F starting with 4-((3,4-dimethoxybenzyl)amino)imidazo[1,5-a]pyrido[3,4-e]pyrazine-8-carboxylic acid Af-7 and commercial (3S)-3-[4-(trifluoromethyl)phenyl]morpholine (the DMB deprotection was performed in TFA/DCE (5:1) at 50° C. overnight). ES/MS: m/z=442.9 $[M+H]^+$. $^1H$ NMR (400 MHz, DMSO-d6) δ 9.41 (s, 1H), 8.75 (s, 0.67H, minor rotamer), 8.62 (s, 1.33H, major rotamer), 8.12 (s, 2H), 7.82 (m, 4H), 5.80 (s, 0.67H, major rotamer), 5.63 (s, 0.33H, minor rotamer), 4.60 (d, J=12.5 Hz, 2H), 3.94 (dd, J=12.4, 3.6 Hz, 1H), 3.83 (d, J=13.9 Hz, 1H), 3.37 (d, J=12.2 Hz, 2H).

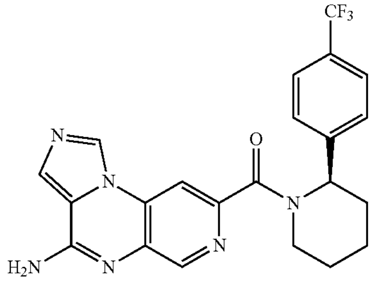 [SMILES: Nc1nc2cnc(C(=O)N3CCCC[C@@H]3c3ccc(C(F)(F)F)cc3)cc2n2cncc12]

Example Ff-87: (R)-(4-aminoimidazo[1,5-a]pyrido[3,4-e]pyrazin-8-yl)(2-(4-(trifluoromethyl)phenyl)piperidin-1-yl)methanone. Prepared following general procedure VI-F starting with 4-((3,4-dimethoxybenzyl)amino)imidazo[1,5-a]pyrido[3,4-e]pyrazine-8-carboxylic acid Af-7 and commercial (2R)-2-[4-(trifluoromethyl)phenyl]piperidine hydrochloride (the DMB deprotection was performed in TFA/DCE (5:1) at 50° C. overnight). ES/MS: m/z=441.0 $[M+H]^+$. $^1H$ NMR (400 MHz, DMSO-d6) δ 9.49-9.36 (m, 1H), 8.79 (s, 0.67H, minor rotamer), 8.61 (s, 1.33H, major rotamer), 8.16 (s, 1H), 7.90-7.76 (m, 2H), 7.67 (d, J=8.3 Hz, 2H), 6.00 (s, 0.67H, major rotamer), 5.47 (s, 0.33H, minor rotamer), 3.86-3.77 (m, 1H), 3.13-2.94 (m, 1H), 2.06-1.89 (m, 1H), 1.76-1.52 (m, 4H), 1.51-1.34 (m, 1H).

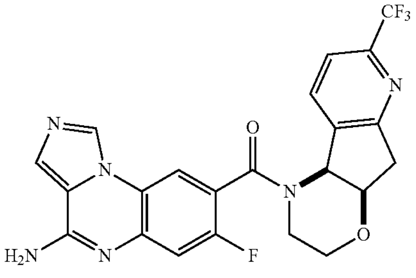

(±)

Example Ff-88: Rac-(4-amino-7-fluoroimidazo[1,5-a]quinoxalin-8-yl)((4aR,9bS)-7-(trifluoromethyl)-2,3,5,9b-tetrahydropyrido[3',2':3,4]cyclopenta[1,2-b][1,4]oxazin-1(4aH)-yl)methanone. Prepared following general procedure VI-F starting with 4-(tert-butoxycarbonylamino)-7-fluoro-imidazo[1,5-a]quinoxaline-8-carboxylic acid Af-1 and 11-(trifluoromethyl)-6-oxa-3,10-diazatricyclo[7.4.0.02,7]trideca-1(9), 10,12-triene Eu-3. ES/MS: m/z=472.9 $[M+H]^+$. $^1H$ NMR 1H NMR (400 MHz, DMSO-d6) δ 9.36 (s, 1H), 8.70-8.47 (m, 1H), 8.23 (d, J=17.8 Hz, 1H), 7.87 (t, J=12.6 Hz, 2H), 7.44 (dd, J=26.5, 10.3 Hz, 1H), 6.07 (s, 1H), 4.59-4.36 (m, 1H), 3.61-3.47 (m, 4H), 3.13 (d, J=11.5 Hz, 1H), 2.84 (d, J=17.2 Hz, 1H).

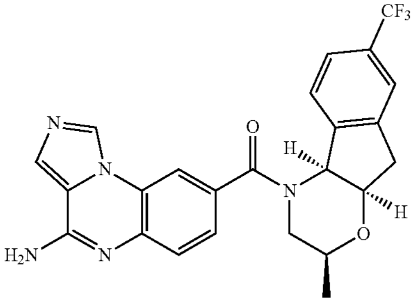 [SMILES: C[C@H]1CN(C(=O)c2ccc3nc(N)c4cncn4c3c2)[C@H]2c3ccc(C(F)(F)F)cc3C[C@H]2O1]

Example Ff-89: (4-aminoimidazo[1,5-a]quinoxalin-8-yl)((2S,4aS,9aR)-2-methyl-7-(trifluoromethyl)-2,3,9,9a-tetrahydroindeno[2,1-b][1,4]oxazin-4(4aH)-yl)methanone. Prepared following general procedure VI-F starting with 4-(tert-butoxycarbonylamino)imidazo[1,5-a]quinoxaline-8-carboxylic acid Ae-1 and (2S)-2-methyl-7-(trifluoromethyl)-2,3,4,4a,9,9a-hexahydroindeno[2,1-b][1,4]oxazine Eu-1 and isolated as the second isomer. ES/MS: m/z=467.9 $[M+H]^+$. $^1H$ NMR (400 MHz, DMSO-d6) δ 9.54 (s, 0.67H, major rotamer), 9.43 (s, 0.33H, minor rotamer), 8.65 (s, 0.33H, minor rotamer), 8.57 (s, 0.67H, major rotamer), 8.41 (d, J=17.2 Hz, 1H), 7.83-7.41 (m, 5H), 5.94 (s, 0.67H, major rotamer), 5.12 (s, 0.33H, minor rotamer), 4.65-4.32 (m, 2H), 3.70 (t, J=8.5 Hz, 1H), 3.54-3.32 (m, 1H), 3.10-2.72 (m, 2H), 1.09 (d, J=6.2 Hz, 1H, minor rotamer), 0.91 (d, J=6.2 Hz, 2H, major rotamer).

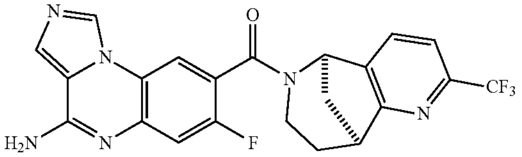

(±)

Example Ff-90: Rac-(4-amino-7-fluoroimidazo[1,5-a]quinoxalin-8-yl)((5R,9S)-2-(trifluoromethyl)-5,7,8,9-tetrahydro-6H-5,9-methanopyrido[3,2-c]azepin-6-yl)methanone. Prepared following general procedure VI-F starting with 4-(tert-butoxycarbonylamino)-7-fluoro-imidazo[1,5-a]quinoxaline-8-carboxylic acid Af-1 and 4-(trifluoromethyl)-3,9-diazatricyclo[6.3.1.02,7]dodeca-2(7),3,5-triene Ef-2. ES/MS: m/z=456.9 $[M+H]^+$. $^1H$ NMR (400 MHz, DMSO-d6) δ 9.34 (d, J=14.4 Hz, 1H), 8.57 (d, J=6.2 Hz, 0.5H, rotamer), 8.24 (d, J=10.1 Hz, 1H), 8.13 (d, J=7.7 Hz, 0.5H, rotamer), 7.98-7.77 (m, 2H), 7.46 (d, J=10.3 Hz, 0.5H rotamer), 7.33 (s, 0.5H rotamer), 6.08 (s, 0.5H, rotamer), 5.06 (s, 0.5H, rotamer), 4.45-4.24 (m, 1H), 3.54-3.33 (m, 2H), 2.42-2.00 (m, 3H), 1.98-1.67 (m, 1H).

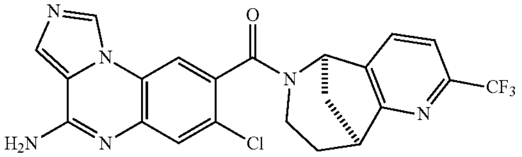

(±)

Example Ff-91: Rac-(4-amino-7-chloroimidazo[1,5-a]quinoxalin-8-yl)((5R,9S)-2-(trifluoromethyl)-5,7,8,9-tetrahydro-6H-5,9-methanopyrido[3,2-c]azepin-6-yl)methanone. Prepared following general procedure VI-F starting with 4-(tert-butoxycarbonylamino)-7-chloro-imidazo[1,5-a]quinoxaline-8-carboxylic acid Af-2 and 4-(trifluoromethyl)-3,9-diazatricyclo[6.3.1.02,7]dodeca-2(7),3,5-triene Ef-2. ES/MS: m/z=472.8 $[M+H]^+$. $^1H$ NMR (400 MHz, DMSO-d6) δ 9.47-9.21 (m, 1H), 8.67-8.44 (m, 1H), 8.37-8.07 (m, 2H), 7.99-7.50 (m, 2H), 6.11 (d, J=3.9 Hz, 0.5H, rotamer), 4.89 (dd, J=30.6, 4.0 Hz, 0.5H, rotamer), 4.39 (dt, J=13.8, 6.7 Hz, 1H), 3.45 (d, J=16.4 Hz, 1H), 3.30-3.15 (m, 1H), 2.37-1.63 (m, 4H).

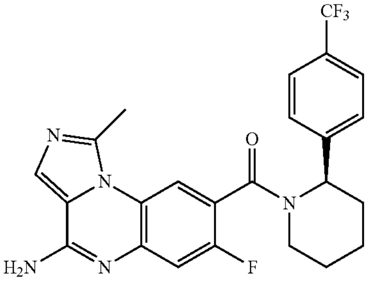 [SMILES: Cc1ncc2c(N)nc3cc(F)c(C(=O)N4CCCC[C@@H]4c4ccc(C(F)(F)F)cc4)cc3n12]

Example Ff-92: (S)-(4-amino-7-fluoro-1-methylimidazo[1,5-a]quinoxalin-8-yl)(3-(4-(trifluoromethyl)phenyl)morpholino)methanone. Prepared following general procedure VI-F starting with 4-(tert-butoxycarbonylamino)-7-fluoro- 1-methyl-imidazo[1,5-a]quinoxaline-8-carboxylic acid Af-5 and commercial (3S)-3-[4-(trifluoromethyl)phenyl]morpholine. ES/MS: m/z=473.9 $[M+H]^+$. $^1H$ NMR (400 MHz, DMSO-d6) δ 8.17 (s, 2H), 7.95-7.33 (m, 5H), 5.80 (s, 1H), 4.59 (d, J=12.3 Hz, 2H), 3.96 (s, 2H), 3.49-3.21 (m, 2H), 3.06 (s, 3H).

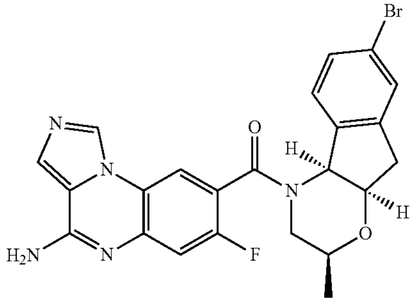 [SMILES: C[C@H]1CN(C(=O)c2cc3c(cc2F)nc(N)c2cncn23)[C@H]2c3ccc(Br)cc3C[C@H]2O1]

Example Ff-93: (4-amino-7-fluoroimidazo[1,5-a]quinoxalin-8-yl)((2S,4aS,9aR)-7-bromo-2-methyl-2,3,9,9a-tetrahydroindeno[2,1-b][1,4]oxazin-4(4aH)-yl)methanone. Prepared following general procedure VI-F starting with 4-(tert-butoxycarbonylamino)-7-fluoro-imidazo[1,5-a]quinoxaline-8-carboxylic acid Af-1 and (2S,4aS,9aR)-7-bromo-2-methyl-2,3,4,4a,9,9a-hexahydroindeno[2,1-b][1,4]oxazine Et-2. ES/MS: m/z=495.8 $[M+H]^+$. $^1H$ NMR (400 MHz, DMSO-d6) δ 9.40-9.23 (m, 1H), 8.54 (s, 1H), 8.15 (s, 1H), 7.64-7.07 (m, 4H), 5.90 (s, 1H), 4.61-4.34 (m, 1H), 3.43-3.10 (m, 3H), 3.02-2.62 (m, 2H), 1.10 (d, J=6.2 Hz, 1H, minor rotamer), 0.93 (d, J=6.2 Hz, 2H, major rotamer).

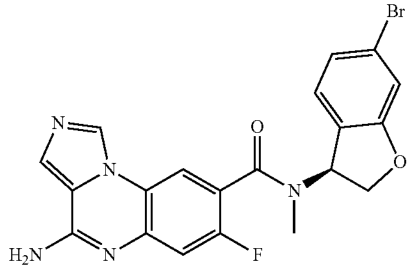 [SMILES: CN(C(=O)c1cc2c(cc1F)nc(N)c1cncn12)[C@@H]1COc2cc(Br)ccc21]

Example Ff-94: (S)-4-amino-N-(6-bromo-2,3-dihydrobenzofuran-3-yl)-7-fluoro-N-methylimidazo[1,5-a]quinoxaline-8-carboxamide. Prepared following general procedure VI-F starting with 4-(tert-butoxycarbonylamino)-7-fluoro-imidazo[1,5-a]quinoxaline-8-carboxylic acid Af-1 and (S)-6-bromo-N-methyl-2,3-dihydrobenzofuran-3-amine Eh-5. ES/MS: m/z=458.0 $[M+H]^+$. $^1H$ NMR (400 MHz, DMSO-$d_6$) δ 9.33 (s, 1H), 9.06 (brs, 2H), 8.59 (brs, 1H), 8.47 (d, J=6.2 Hz, 0.55H major rotamer), 8.29 (s, 1H), 7.54-7.11 (m, 3H+0.45H minor rotamer), 6.38 (dd, J=9.0, 3.9 Hz, 0.55H major rotamer), 5.47 (d, J=6.7 Hz, 0.45H minor rotamer), 4.82 (dd, J=10.5, 9.0 Hz, 0.55H major rotamer), 4.61 (dd, J=10.6, 3.8 Hz, 1H+0.45H minor rotamer), 2.69 (s, 1.65H major rotamer), 2.58 (s, 1.35H minor rotamer).

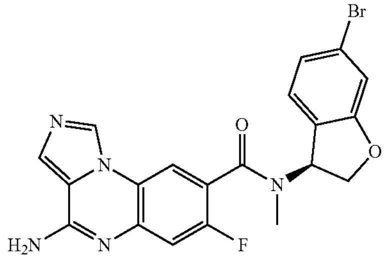

Example Ff-94

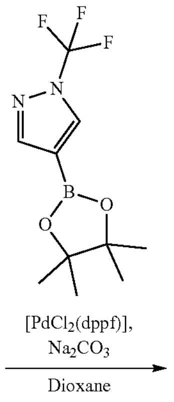

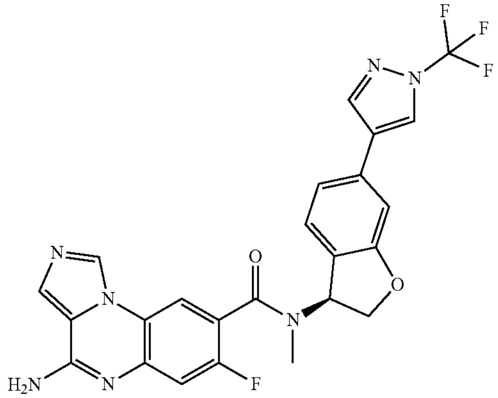

Example Ff-95

Example Ff-95: (S)-4-amino-7-fluoro-N-methyl-N-(6-(1-(trifluoromethyl)-1H-pyrazol-4-yl)-2,3-dihydrobenzofuran-3-yl)imidazo[1,5-a]quinoxaline-8-carboxamide. To a solution of (S)-4-amino-N-(6-bromo-2,3-dihydrobenzofuran-3-yl)-7-fluoro-N-methylimidazo[1,5-a]quinoxaline-8-carboxamide (Example Ff-94 20 mg, 0.035 mmol) and 4-(4,4,5,5-tetramethyl-1,3,2-dioxaborolan-2-yl)-1-(trifluoromethyl)-1H-pyrazole (24.5.0 mg, 0.070 mmol), and $PdCl_2$(dppf) (3.9 mg, 0.0053 mmol) in dioxane (2 mL), was added 2M $Na_2CO_3$ (0.0186 mg, 0.175 mmol). The mixture was bubbled through argon for 1 minute and left to stir at 90 C for 6 hours. The mixture was filtered through a pad of celite and anhydrous $MgSO_4$. The solution was reduced under pressure and the crude was purified by flash chromatography followed by preparative HPLC. ES/MS: m/z=512.0 $[M+H]^+$. $^1H$ NMR (400 MHz, Methanol-d4) δ 9.27 (s, 1H), 8.61 (d, J=12.7 Hz, 1H), 8.50-8.17 (m, 2H), 7.61-7.10 (m, 4H), 6.53 (dd, J=8.7, 3.4 Hz, 1H), 5.60 (t, J=6.2 Hz, 1H), 4.86-4.79 (m, 1H), 4.67 (dd, J=10.6, 3.6 Hz, 1H), 2.97-2.55 (m, 3H).

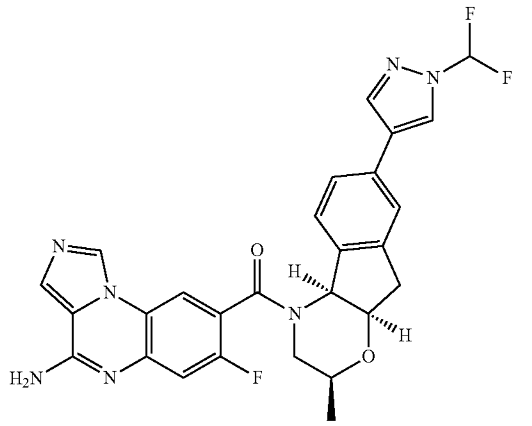 [SMILES: C[C@H]1CN(C(=O)c2cc3c(cc2F)nc(N)c2cncn23)[C@H]2c3ccc(-c4cnn(C(F)F)c4)cc3C[C@H]2O1]

Example Ff-96: (4-amino-7-fluoroimidazo[1,5-a]quinoxalin-8-yl)((2S,4aS,9aR)-7-(1-(difluoromethyl)-1H-pyrazol-4-yl)-2-methyl-2,3,9,9a-tetrahydroindeno[2,1-b][1,4]oxazin-4(4aH)-yl)methanone. Prepared following example Ff-95 starting with [(2S,4aS,9aR)-7-bromo-2-methyl-3,4a,9,9a-tetrahydro-2H-indeno[2,1-b][1,4]oxazin-4-yl]-(4-amino-7-fluoro-imidazo[1,5-a]quinoxalin-8-yl)methanone example Ff-93 and 1-(difluoromethyl)-4-(4,4,5,5-tetramethyl-1,3,2-dioxaborolan-2-yl)pyrazole. ES/MS: m/z=533.9 $[M+H]^+$. $^1H$ NMR (400 MHz, DMSO-d6) δ 9.30 (s, 1H), 8.70-8.47 (m, 1H), 8.13 (m, 2H), 7.86 (d, J=1.4 Hz, 1H), 7.75-7.54 (m, 2H), 7.49-7.16 (m, 3H), 5.90 (s, 1H), 4.56-4.33 (m, 2H), 3.38-3.16 (m, 2H), 3.01-2.64 (m, 2H), 1.07 (d, J=6.2 Hz, 1H, minor rotamer), 0.90 (d, J=6.1 Hz, 2H, major rotamer).

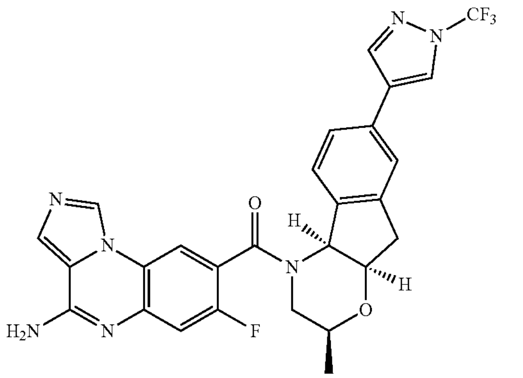 [SMILES: C[C@H]1CN(C(=O)c2cc3c(cc2F)nc(N)c2cncn23)[C@H]2c3ccc(-c4cnn(C(F)(F)F)c4)cc3C[C@H]2O1]

Example Ff-97: (4-amino-7-fluoroimidazo[1,5-a]quinoxalin-8-yl)((2S,4aS,9aR)-2-methyl-7-(1-(trifluoromethyl)-1H-pyrazol-4-yl)-2,3,9,9a-tetrahydroindeno[2,1-b][1,4]oxazin-4(4aH)-yl)methanone. Prepared following example Ff-95 starting with [(2S,4aS,9aR)-7-bromo-2-methyl-3,4a,9,9a-tetrahydro-2H-indeno[2,1-b][1,4]oxazin-4-yl]-(4-amino-7-fluoro-imidazo[1,5-a]quinoxalin-8-yl)methanone example Ff-93 and 4-(4,4,5,5-tetramethyl-1,3,2-dioxaborolan-2-yl)-1-(trifluoromethyl)pyrazole. ES/MS: m/z=551.9 $[M+H]^+$. $^1H$ NMR (400 MHz, DMSO-d6) δ 9.34 (s, 1H), 8.99 (d, J=12.3 Hz, 1H), 8.63-8.46 (m, 2H), 8.18 (m, 1H), 7.80-7.60 (m, 2H), 7.54-7.25 (m, 2H), 5.95 (s, 1H), 4.58-4.39 (m, 2H), 3.32 (dd, J=42.1, 14.3 Hz, 2H), 3.08-2.75 (m, 2H), 1.10 (d, J=6.2 Hz, 1.5H, rotamer), 0.93 (d, J=6.2 Hz, 1.5H, rotamer).

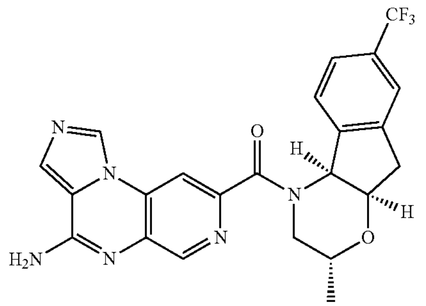 [SMILES: C[C@@H]1CN(C(=O)c2cc3c(cn2)nc(N)c2cncn23)[C@H]2c3ccc(C(F)(F)F)cc3C[C@H]2O1]

Example Ff-98: (4-aminoimidazo[1,5-a]pyrido[3,4-e]pyrazin-8-yl)((2R,4aS,9aR)-2-methyl-7-(trifluoromethyl)-2,3,9,9a-tetrahydroindeno[2,1-b][1,4]oxazin-4(4aH)-yl)methanone. Prepared following general procedure VI-F (the DMB deprotection was performed in TFA/DCE (5:1) at 50° C. overnight) starting with 4-((3,4-dimethoxybenzyl)amino)imidazo[1,5-a]pyrido[3,4-e]pyrazine-8-carboxylic acid Af-7 and (2R)-2-methyl-7-(trifluoromethyl)-2,3,4,4a,9,9a-hexahydroindeno[2,1-b][1,4]oxazine Eu-2 and isolated as the first isomer (first peak by HPLC purification). ES/MS: m/z=468.9 $[M+H]^+$. $^1H$ NMR (400 MHz, DMSO-d6) δ 9.44 (d, J=1.9 Hz, 1H), 8.77 (s, 0.5H, rotamer), 8.71 (s, 0.5H, rotamer), 8.68 (s, 0.5H, rotamer), 8.61 (s, 0.5H, rotamer), 8.11 (d, J=12.6 Hz, 1H), 7.79-7.60 (m, 3H), 6.00 (s, 0.5H, rotamer), 5.52 (s, 0.5H, rotamer), 4.76 (t, J=4.2 Hz, 0.5H, rotamer), 4.62 (t, J=4.2 Hz, 0.5H, rotamer), 4.25 (d, J=13.0 Hz, 1H), 3.33 (d, J=16.8 Hz, 1H), 3.21 (d, J=10.4 Hz, 1H), 1.33 (dd, J=17.7, 6.7 Hz, 3H).

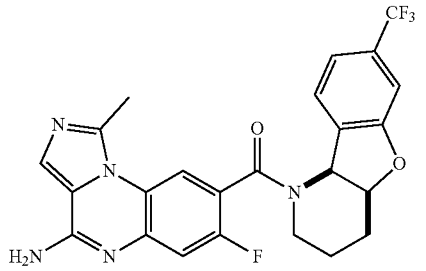

(±)

Example Ff-99: Rac-(4-amino-7-fluoro-1-methylimidazo[1,5-a]quinoxalin-8-yl)(7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-1-methyl-imidazo[1,5-a]quinoxaline-8-carboxylic acid Af-5 and cis-7-(trifluoromethyl)-1,2,3,4,4a,9b-hexahydrobenzofuro[3,2-b]pyridine Ev-1. ES/MS: m/z=485.9 $[M+H]^+$. $^1H$ NMR (400 MHz, DMSO-d6) δ 8.15 (d, J=13.6 Hz, 2H), 7.66-7.47 (m, 1H), 7.45-7.20 (m, 3H), 6.50-6.31 (m, 1H), 5.32-5.16 (m, 1H), 3.05 (s, 3H), 2.98-2.83 (m, 2H), 1.99-1.83 (m, 1H), 1.80-1.68 (m, 1H), 1.64-1.45 (m, 2H).

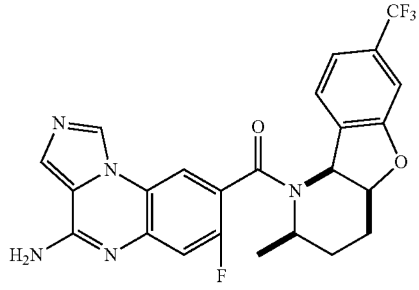

(±)

Example Ff-100: Rac-(4-amino-7-fluoroimidazo[1,5-a]quinoxalin-8-yl)((2R,4aS,9bS)-2-methyl-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-imidazo[1,5-a]quinoxaline-8-carboxylic acid Af-1 and cis-2-methyl-7-(trifluoromethyl)-1,2,3,4,4a,9b-hexahydrobenzofuro[3,2-b]pyridine Ev-4. ES/MS: m/z=485.9 $[M+H]^+$. $^1$H NMR (400 MHz, Methanol-d4) δ 9.28 (d, J=26.6 Hz, 1H), 8.77-8.41 (m, 1H), 8.37 (s, 1H), 7.65-7.41 (m, 2H), 7.38-6.94 (m, 2H), 6.65 (d, J=10.1 Hz, 0.33H, minor rotamer), 5.78 (s, 0.67H, major rotamer), 5.28 (d, J=11.7 Hz, 1H), 4.56 (s, 0.67H, major rotamer), 3.95 (s, 0.33H, minor rotamer), 2.24-1.75 (m, 3H), 1.39 (q, J=13.4, 12.9 Hz, 1H), 1.08 (d, J=6.5 Hz, 2H, major rotamer), 0.77 (d, J=6.6 Hz, 1H, minor rotamer).

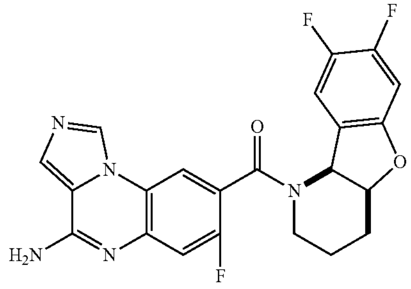

(±)

Example Ff-101: Rac-(4-amino-7-fluoroimidazo[1,5-a]quinoxalin-8-yl)((4aS,9bS)-7,8-difluoro-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-imidazo[1,5-a]quinoxaline-8-carboxylic acid Af-1 and cis-7,8-difluoro-1,2,3,4,4a,9b-hexahydrobenzofuro[3,2-b]pyridine Ev-2. ES/MS: m/z=439.9 $[M+H]^+$. $^1$H NMR (400 MHz, Methanol-d4) δ 9.27 (s, 1H), 8.43 (d, J=5.9 Hz, 1H), 8.36 (s, 1H), 7.45 (d, J=9.7 Hz, 1H), 7.24 (d, J=47.3 Hz, 1H), 6.82 (dd, J=10.7, 6.3 Hz, 1H), 6.29 (d, J=8.5 Hz, 0.8H, major rotamer), 5.53 (d, J=9.0 Hz, 0.2H, minor rotamer), 5.14 (dt, J=8.5, 4.1 Hz, 0.8H, major rotamer), 4.50-4.35 (m, 0.2H, minor rotamer), 3.50-3.37 (m, 1H), 3.10-2.92 (m, 1H), 2.16-1.95 (m, 2H), 1.91-1.62 (m, 2H).

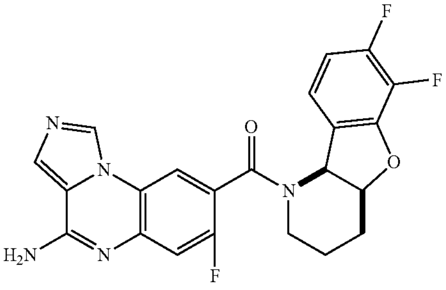

(±)

Example Ff-102: Rac-(4-amino-7-fluoroimidazo[1,5-a]quinoxalin-8-yl)((4aS,9bS)-6,7-difluoro-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-imidazo[1,5-a]quinoxaline-8-carboxylic acid Af-1 and cis-6,7-difluoro-1,2,3,4,4a,9b-hexahydrobenzofuro[3,2-b]pyridine Ev-3. ES/MS: m/z=439.9 $[M+H]^+$. $^1$H NMR (400 MHz, Methanol-d4) δ 9.27 (s, 1H), 8.42 (d, J=5.9 Hz, 1H), 8.36 (s, 1H), 7.46 (d, J=9.6 Hz, 1H), 7.18 (s, 0.67H, major rotamer), 7.04 (s, 0.33H, minor rotamer), 6.86 (dt, J=10.9, 7.6 Hz, 1H), 6.37 (d, J=8.6 Hz, 0.67H, major rotamer), 5.58 (d, J=9.2 Hz, 0.33H, minor rotamer), 5.27 (dt, J=8.5, 4.2 Hz, 0.67H, major rotamer), 4.49-4.38 (m, 0.33H, minor rotamer), 3.51-3.39 (m, 1H), 3.03 (dt, J=14.6, 7.7 Hz, 0.67H, major rotamer), 2.90-2.77 (m, 0.33H, minor rotamer), 2.24-1.98 (m, 2H), 1.91-1.67 (m, 2H).

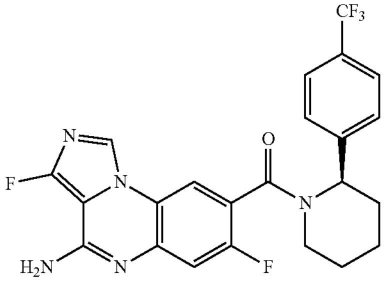 [SMILES: Nc1nc2cc(F)c(C(=O)N3CCCC[C@@H]3c3ccc(C(F)(F)F)cc3)cc2n2cnc(F)c12]

Example Ff-103: (S)-(4-amino-3-fluoroimidazo[1,5-a]quinoxalin-8-yl)(3-(4-(trifluoromethyl)phenyl)morpholino)methanone. Prepared following general procedure VI-F starting with 4-(tert-butoxycarbonylamino)-3-fluoro-imidazo[1,5-a]quinoxaline-8-carboxylic acid Ah-1 and commercial (3S)-3-[4-(trifluoromethyl)phenyl]morpholine. ES/MS: m/z=459.9 $[M+H]^+$. $^1$H NMR (400 MHz, Methanol-d4) δ 8.95 (s, 1H), 8.33 (d, J=1.5 Hz, 1H), 7.87-7.51 (m, 6H), 4.55 (d, J=12.5 Hz, 1H), 4.04 (dd, J=12.4, 3.6 Hz, 1H), 3.89 (d, J=11.4 Hz, 1H), 3.72 (td, J=11.6, 2.8 Hz, 1H), 3.38 (d, J=12.3 Hz, 1H).

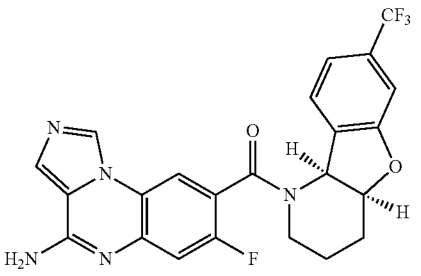 [SMILES: Nc1nc2cc(F)c(C(=O)N3CCC[C@@H]4Oc5cc(C(F)(F)F)ccc5[C@@H]43)cc2n2cncc12]

Example Ff-104: (4-amino-7-fluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-imidazo[1,5-a] quinoxaline-8-carboxylic acid Af-1 and (4aS,9bS)-7-(trifluoromethyl)-1,2,3,4,4a,9b-hexahydrobenzofuro[3,2-b] pyridine Ew-1. ES/MS: m/z=471.9 $[M+H]^+$. $^1$H NMR (400 MHz, DMSO-d6) δ 9.35 (s, 1H), 8.97 (brs, 2H), 8.48 (d, J=6.2 Hz, 1H), 8.27 (s, 1H), 7.57-7.17 (m, 4H), 6.38 (d, J=9.0 Hz, 0.67H, major rotamer), 5.57 (d, J=9.2 Hz, 0.33H, minor rotamer), 5.23 (dt, J=9.3, 4.8 Hz, 0.67H, major rotamer), 5.12 (s, 0.33H, minor rotamer), 4.39-4.26 (m, 0.33H, minor rotamer), 3.41-3.29 (m, 0.67H, major rotamer), 2.95-2.83 (m, 0.67H, major rotamer), 2.74-2.62 (m, 0.33H, minor rotamer), 2.02-1.85 (m, 2H), 1.79-1.52 (m, 2H).

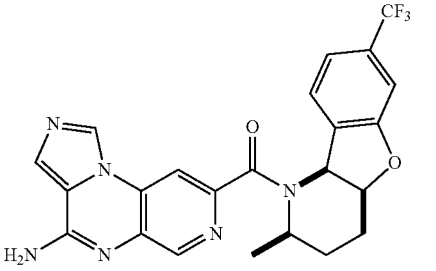

(±)

Example Ff-106: Rac-(4-aminoimidazo[1,5-a]pyrido[3,4-e]pyrazin-8-yl)((2R,4aS,9bS)-2-methyl-7-(trifluoromethyl)-3,4,4a,9b-tetrahydrobenzofuro[3,2-b]pyridin-1(2H)-yl) methanone. Prepared following general procedure VI-F starting with 7-(tert-butoxycarbonylamino)-2,4,8,11-tetrazatricyclo[7.4.0.02,6]trideca-1(13), 3,5,7,9,11-hexaene-12-carboxylic acid Af-6 and 2-methyl-7-(trifluoromethyl)-1,2,3,4,4a,9b-hexahydrobenzofuro[3,2-b]pyridine Ev-4. ES/MS: m/z=468.9 $[M+H]^+$. $^1$H NMR (400 MHz, Methanol-d4) δ 9.34 (s, 1H), 8.82 (s, 1H), 8.56 (s, 1H), 8.30 (s, 1H), 7.92 (d, J=7.8 Hz, 1H), 7.24 (d, J=7.8 Hz, 1H), 7.03 (s, 1H), 6.05 (d, J=10.1 Hz, 1H), 5.13 (d, J=10.3 Hz, 1H), 4.66-4.53 (m, 1H), 2.10-1.95 (m, 2H), 1.79 (t, J=14.6 Hz, 1H), 1.50-1.33 (m, 1H), 1.05 (d, J=6.4 Hz, 2H, major rotamer), 0.80 (s, 1H, minor rotamer).

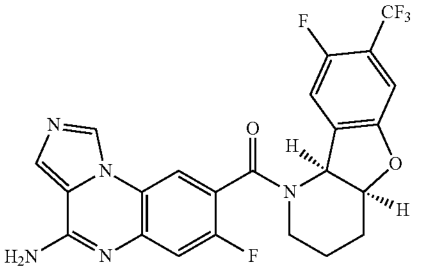 [SMILES: Nc1nc2cc(F)c(C(=O)N3CCC[C@@H]4Oc5cc(C(F)(F)F)c(F)cc5[C@@H]43)cc2n2cncc12]

Example Ff-105: (4-amino-7-fluoroimidazo[1,5-a]quinoxalin-8-yl)((4aS,9bS)-8-fluoro-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-imidazo[1,5-a] quinoxaline-8-carboxylic acid Af-1 and (4aS,9bS)-8-fluoro-7-(trifluoromethyl)-1,2,3,4,4a,9b-hexahydrobenzofuro[3,2-b]pyridine Ew-2. ES/MS: m/z=489.9 $[M+H]^+$. $^1$H NMR (400 MHz, Methanol-d4) δ 9.28 (s, 1H), 8.46 (d, J=5.9 Hz, 1H), 8.37 (s, 1H), 7.46 (d, J=9.6 Hz, 1H), 7.36 (s, 1H), 7.15 (d, J=5.3 Hz, 1H), 6.42 (d, J=8.9 Hz, 0.8H, major rotamer), 5.66 (d, J=8.9 Hz, 0.2H, minor rotamer), 5.19 (dt, J=9.0, 4.6 Hz, 1H), 3.48 (dt, J=3.3, 1.6 Hz, 1H), 3.04 (d, J=10.5 Hz, 0.8H, major rotamer), 2.95-2.75 (m, 0.2H, minor rotamer), 2.12-1.60 (m, 4H).

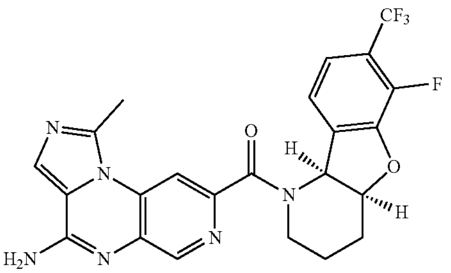 [SMILES: Cc1ncc2c(N)nc3cnc(C(=O)N4CCC[C@@H]5Oc6c(ccc(C(F)(F)F)c6F)[C@@H]54)cc3n12]

Example Ff-107: (4-amino-1-methylimidazo[1,5-a] pyrido[3,4-e]pyrazin-8-yl)((4aS,9bS)-6-fluoro-7-(trifluoromethyl)-3,4,4a,9b-tetrahydrobenzofuro[3,2-b]pyridin-1 (2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (4aS,9bS)-6-fluoro-7-(trifluoromethyl)-1,2,3,4,4a,9b-hexahydrobenzofuro[3,2-b] pyridine Ew-3. ES/MS: m/z=486.9 $[M+H]^+$. $^1$H NMR (400 MHz, Methanol-d4) δ 8.83 (s, 1H), 8.49 (d, J=38.6 Hz, 1H), 8.24 (s, 1H), 7.70 (s, 0.5H, rotamer), 7.41 (s, 0.5H, rotamer), 7.27 (t, J=6.7 Hz, 1H), 6.39 (s, 0.5H, rotamer), 6.20 (s, 0.5H, rotamer), 5.29 (s, 0.5H, rotamer), 5.13 (s, 0.5H, rotamer), 4.53-4.35 (m, 0.5H, rotamer), 4.01-3.76 (m, 0.5H, rotamer), 3.15 (s, 3H), 3.04-2.95 (m, 0.5H, rotamer), 2.87-2.69 (m, 0.5H, rotamer), 2.27-1.64 (m, 4H).

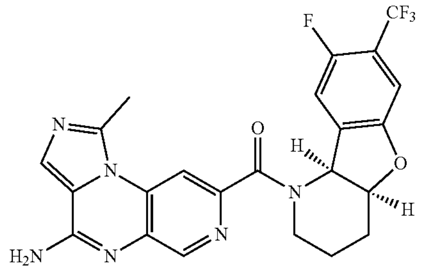 [SMILES: Cc1ncc2c(N)nc3cnc(C(=O)N4CCC[C@@H]5Oc6cc(C(F)(F)F)c(F)cc6[C@@H]54)cc3n12]

Example Ff-108: (4-amino-1-methylimidazo[1,5-a]pyrido[3,4-e]pyrazin-8-yl)((4aS,9bS)-8-fluoro-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (4aS,9bS)-8-fluoro-7-(trifluoromethyl)-1,2,3,4,4a,9b-hexahydrobenzofuro[3,2-b]pyridine Ew-2. ES/MS: m/z=486.9 $[M+H]^+$. $^1H$ NMR (400 MHz, Methanol-d4) δ 8.83 (d, J=13.0 Hz, 1H), 8.49 (d, J=35.3 Hz, 1H), 8.24 (s, 1H), 7.75 (d, J=9.6 Hz, 0.5H, rotamer), 7.43 (d, J=9.5 Hz, 0.5H, rotamer), 7.12 (d, J=11.6 Hz, 1H), 6.32 (d, J=8.9 Hz, 0.5H, rotamer), 6.09 (d, J=8.9 Hz, 0.5H, rotamer), 5.18 (s, 0.5H, rotamer), 5.01 (s, 0.5H, rotamer), 4.54-4.31 (m, 0.5H, rotamer), 4.01-3.75 (m, 0.5H, rotamer), 3.15 (s, 3H), 3.02-2.95 (m, 0.5H, rotamer), 2.87-2.73 (m, 0.5H, rotamer), 2.20-1.62 (m, 4H).

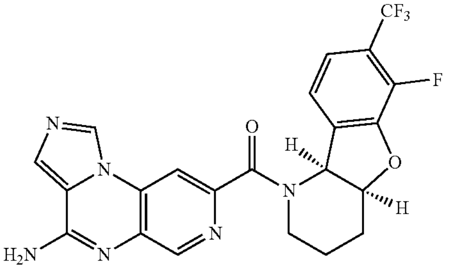

Example Ff-109: (4-aminoimidazo[1,5-a]pyrido[3,4-e]pyrazin-8-yl)((4aS,9bS)-6-fluoro-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (4aS,9bS)-6-fluoro-7-(trifluoromethyl)-1,2,3,4,4a,9b-hexahydrobenzofuro[3,2-b]pyridine Ew-3. ES/MS: m/z=472.9 $[M+H]^+$. $^1H$ NMR (400 MHz, Methanol-d4) δ 9.33 (s, 1H), 8.82 (d, J=9.6 Hz, 1H), 8.57 (d, J=36.8 Hz, 1H), 8.28 (s, 1H), 7.66 (d, J=7.9 Hz, 0.5H, rotamer), 7.40 (d, J=7.8 Hz, 0.5H, rotamer), 7.27 (dd, J=7.9, 5.6 Hz, 1H), 6.40 (d, J=8.7 Hz, 0.5H, rotamer), 6.12 (d, J=8.9 Hz, 0.5H, rotamer), 5.30 (s, 0.5H, rotamer), 5.14 (s, 0.5H, rotamer), 4.51-4.36 (m, 0.5H, rotamer), 3.92-3.70 (m, 0.5H, rotamer), 3.06-2.87 (m, 0.5H, rotamer), 2.86-2.72 (m, 0.5H, rotamer), 2.26-1.67 (m, 4H).

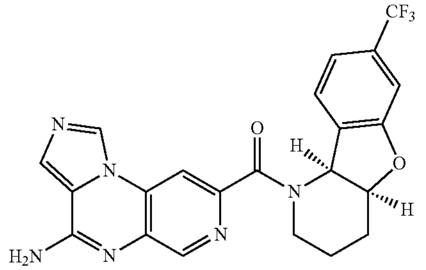

Example Ff-110: (4-aminoimidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (4aS,9bS)-7-(trifluoromethyl)-1,2,3,4,4a,9b-hexahydrobenzofuro[3,2-b]pyridine Ew-1. ES/MS: m/z=454.9 $[M+H]^+$. $^1H$ NMR (400 MHz, Methanol-d4) δ 9.35 (s, 1H), 8.86-8.80 (m, 1H), 8.64 (s, 0.5H rotamer), 8.55 (s, 0.5H rotamer) 8.31 (s, 1H), 7.84 (d, J=8.0 Hz, 0.5H, rotamer), 7.61 (d, J=8.0 Hz, 0.5H, rotamer), 7.28 (d, J=7.8 Hz, 1H), 7.15-7.07 (m, 1H), 6.35 (d, J=9.0 Hz, 0.5H, rotamer), 6.01 (d, J=9.2 Hz, 0.5H, rotamer), 5.18 (s, 0.5H, rotamer), 5.02 (s, 0.5H, rotamer), 4.55-4.28 (m, 0.5H, rotamer), 3.85-3.66 (m, 0.5H, rotamer), 3.03-2.92 (m, 0.5H, rotamer), 2.88-2.71 (m, 0.5H, rotamer), 2.21-1.61 (m, 4H).

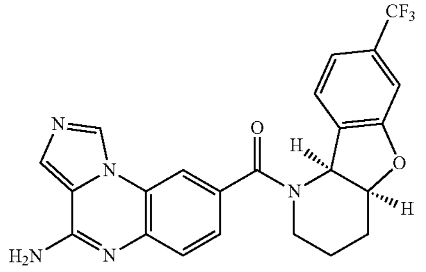 [SMILES: Nc1nc2ccc(C(=O)N3CCC[C@@H]4Oc5cc(C(F)(F)F)ccc5[C@@H]43)cc2n2cncc12]

Example Ff-111: (4-aminoimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)imidazo[1,5-a]quinoxaline-8-carboxylic acid Ae-1 and (4aS,9bS)-7-(trifluoromethyl)-1,2,3,4,4a,9b-hexahydrobenzofuro[3,2-b]pyridine Ew-1. ES/MS: m/z=453.9 $[M+H]^+$. $^1H$ NMR (400 MHz, Methanol-d4) δ 9.34 (d, J=0.6 Hz, 1H), 8.44 (s, 1H), 8.39 (d, J=0.6 Hz, 1H), 7.69 (s, 2H), 7.61 (d, J=7.8 Hz, 1H), 7.29 (d, J=7.8 Hz, 1H), 7.12 (s, 1H), 6.33 (s, 1H), 5.16 (s, 1H), 3.67-3.49 (m, 1H), 3.07-2.81 (m, 1H), 2.08 (brs, 2H), 1.93-1.81 (m, 1H), 1.79-1.65 (m, 1H).

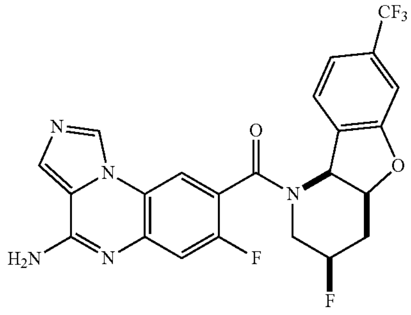

(±)

Example Ff-112: Rac-(4-amino-7-fluoroimidazo[1,5-a]quinoxalin-8-yl)((3R,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-imidazo[1,5-a]quinoxaline-8-carboxylic acid Af-1 and (3R,4aS,9bS)-3-fluoro-7-(trifluoromethyl)-1,2,3,4,4a,9b-hexahydrobenzofuro[3,2-b]pyridine Ev-5. ES/MS: m/z=489.9 $[M+H]^+$. $^1H$ NMR (400 MHz, Methanol-d4) δ 9.25 (s, 1H), 8.41 (d, J=5.9 Hz, 1H), 8.35 (s, 1H), 7.67 (s, 1H), 7.45 (d, J=9.8 Hz, 1H), 7.32 (d, J=7.9 Hz, 1H), 7.17 (s, 1H), 6.34 (d, J=8.7 Hz, 0.8H, major rotamer), 5.65 (s, 0.2H, minor rotamer), 5.30-4.99 (m, 2H), 3.97-3.81 (m, 1H), 2.91 (td, J=16.1, 7.7 Hz, 1H), 2.64-2.27 (m, 2H).

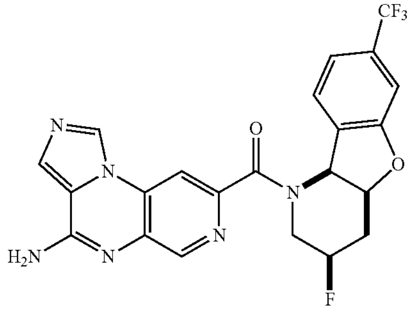

(±)

Example Ff-113: Rac-(4-aminoimidazo[1,5-a]pyrido[3,4-e]pyrazin-8-yl)((3R,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (3R,4aS,9bS)-3-fluoro-7-(trifluoromethyl)-1,2,3,4,4a,9b-hexahydrobenzofuro[3,2-b]pyridine Ev-5. ES/MS: m/z=472.9 $[M+H]^+$. $^1H$ NMR (400 MHz, Methanol-d4) δ 9.30 (s, 1H), 8.84 (d, J=28.8 Hz, 1H), 8.60 (d, J=23.4 Hz, 1H), 8.23 (s, 1H), 8.01 (s, 0.4H, minor rotamer), 7.70 (d, J=7.7 Hz, 0.6H, major rotamer), 7.31 (d, J=7.9 Hz, 1H), 7.14 (d, J=18.2 Hz, 1H), 6.20 (d, J=8.3 Hz, 0.6H, major rotamer), 6.11 (s, 0.4H, minor rotamer), 5.37 (d, J=51.4 Hz, 1H), 5.23 (s, 1H), 4.29 (s, 1H), 2.87-2.37 (m, 3H).

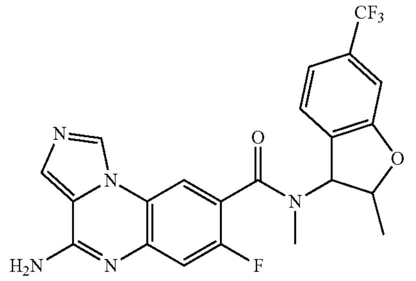 [SMILES: CC1Oc2cc(C(F)(F)F)ccc2C1N(C)C(=O)c1cc2c(cc1F)nc(N)c1cncn12]

Example Ff-114: 4-amino-7-fluoro-N-methyl-N-(2-methyl-6-(trifluoromethyl)-2,3-dihydrobenzofuran-3-yl)imidazo[1,5-a]quinoxaline-8-carboxamide. Prepared following general procedure VI-F starting with 4-(tert-butoxycarbonylamino)-7-fluoro-imidazo[1,5-a]quinoxaline-8-carboxylic acid Af-1 and N,2-dimethyl-6-(trifluoromethyl)-2,3-dihydrobenzofuran-3-amine Eaa-1. ES/MS: m/z=459.9 $[M+H]^+$. $^1H$ NMR (400 MHz, Methanol-d4) δ 9.35-9.15 (m, 1H), 8.44 (dd, J=7.8, 5.9 Hz, 1H), 8.33 (t, J=1.2 Hz, 1H), 7.67-7.40 (m, 2H), 7.32 (t, J=8.5 Hz, 1H), 7.21-7.04 (m, 1H), 6.26 (s, 0.5H, diastereomer), 6.15 (d, J=4.4 Hz, 0.5H, diastereomer), 5.11-4.92 (m, 1H), 2.78-2.64 (m, 1.5H, diastereomer), 2.58 (s, 1.5H, diastereomer), 1.58 (d, J=6.7 Hz, 3H).

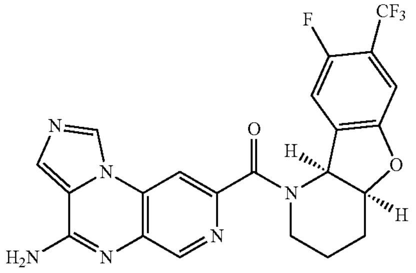 [SMILES: Nc1nc2cnc(C(=O)N3CCC[C@@H]4Oc5cc(C(F)(F)F)c(F)cc5[C@@H]43)cc2n2cncc12]

Example Ff-115: (4-aminoimidazo[1,5-a]pyrido[3,4-e]pyrazin-8-yl)((4aS,9bS)-8-fluoro-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (4aS,9bS)-8-fluoro-7-(trifluoromethyl)-1,2,3,4,4a,9b-hexahydrobenzofuro[3,2-b]pyridine Ew-2. ES/MS: m/z=472.7 $[M+H]^+$. $^1H$ NMR (400 MHz, Methanol-d4) δ 9.38 (d, J=5.6 Hz, 1H), 8.85 (d, J=15.4 Hz, 1H), 8.67 (s, 0.5H rotamer), 8.59 (s, 0.5H rotamer), 8.37 (s, 1H), 7.70 (d, J=9.3 Hz, 0.5H, rotamer), 7.40 (d, J=9.5 Hz, 0.5H, rotamer), 7.12 (dd, J=18.5, 5.4 Hz, 1H), 6.33 (d, J=8.5 Hz, 0.5H, rotamer), 6.00 (d, J=9.3 Hz, 0.5H, rotamer), 5.27-5.13 (m, 0.5H, rotamer), 5.08-4.99 (m, 0.5H, rotamer), 4.57-4.30 (m, 0.5H, rotamer), 3.89-3.66 (m, 0.5H, rotamer), 3.06-2.91 (m, 0.5H, rotamer), 2.80 (d, J=9.0 Hz, 0.5H, rotamer), 2.17-1.62 (m, 4H).

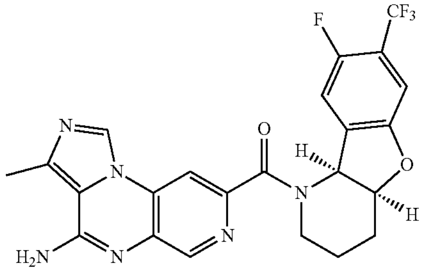 [SMILES: Cc1ncn2c1c(N)nc1cnc(C(=O)N3CCC[C@@H]4Oc5cc(C(F)(F)F)c(F)cc5[C@@H]43)cc12]

Example Ff-116: (4-amino-3-methylimidazo[1,5-a]pyrido[3,4-e]pyrazin-8-yl)((4aS,9bS)-8-fluoro-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and (4aS,9bS)-8-fluoro-7-(trifluoromethyl)-1,2,3,4,4a,9b-hexahydrobenzofuro[3,2-b]pyridine Ew-2. ES/MS: m/z=486.8 $[M+H]^+$. $^1H$ NMR (400 MHz, Methanol-d4) δ 9.26 (d, J=5.6 Hz, 1H), 8.81 (d, J=16.9 Hz, 1H), 8.52 (d, J=31.5 Hz, 1H), 7.69 (d, J=9.6 Hz, 0.5H, rotamer), 7.40 (d, J=9.5 Hz, 0.5H, rotamer), 7.11 (dd, J=18.2, 5.3 Hz, 1H), 6.32 (d, J=8.6 Hz, 0.5H, rotamer), 5.99 (d, J=9.1 Hz, 0.5H, rotamer), 5.23-5.11 (m, 0.5H, rotamer), 5.08-4.93 (m, 0.5H, rotamer), 4.42 (s, 0.5H, rotamer), 3.76 (d, J=11.7 Hz, 0.5H, rotamer), 2.98 (dt, J=14.7, 7.3 Hz, 1H), 2.79 (s, 3H), 2.17-1.65 (m, 4H).

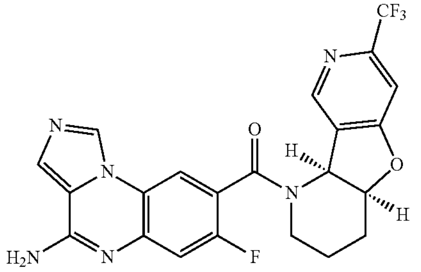 [SMILES: Nc1nc2cc(F)c(C(=O)N3CCC[C@@H]4Oc5cc(C(F)(F)F)ncc5[C@@H]43)cc2n2cncc12]

Example Ff-117: (4-amino-7-fluoroimidazo[1,5-a]quinoxalin-8-yl)((4aS,9bS)-7-(trifluoromethyl)-3,4,4a,9b-tetrahydrofuro[3,2-b:4,5-c']dipyridin-1(2H)-yl)methanone. Prepared following general procedure VI-F starting with 4-amino-7-fluoro-imidazo[1,5-a]quinoxaline-8-carboxylic acid Af-1 and (2S,7S)-11-(trifluoromethyl)-8-oxa-3,12-diazatricyclo[7.4.0.02,7]trideca-1(9),10,12-triene Ew-4. ES/MS: m/z=472.9 $[M+H]^+$. $^1H$ NMR (400 MHz, Methanol-d4) δ 9.25 (s, 1H), 8.63 (s, 1H), 8.43 (d, J=5.9 Hz, 1H), 8.31 (s, 1H), 7.53-7.25 (m, 2H), 6.49 (d, J=8.9 Hz, 0.8H, major rotamer), 5.78 (d, J=9.1 Hz, 0.2H, minor rotamer), 5.42-5.31 (m, 1H), 3.53-3.42 (m, 1H), 3.09-2.98 (m, 1H), 2.26-1.99 (m, 2H), 1.97-1.77 (m, 1H), 1.79-1.61 (m, 1H).

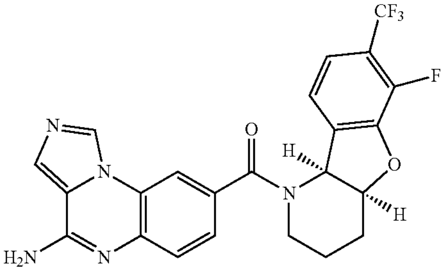

Example Ff-118: (4-aminoimidazo[1,5-a]quinoxalin-8-yl)((4aS,9bS)-6-fluoro-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)imidazo[1,5-a]quinoxaline-8-carboxylic acid Ae-1 and (4aS,9bS)-6-fluoro-7-(trifluoromethyl)-1,2,3,4,4a,9b-hexahydrobenzofuro[3,2-b]pyridine Ew-3. ES/MS: m/z=471.8 $[M+H]^+$. $^1H$ NMR (400 MHz, Methanol-d4) δ 9.34 (s, 1H), 8.43 (s, 1H), 8.39 (s, 1H), 7.69 (s, 2H), 7.41 (d, J=8.0 Hz, 1H), 7.31-7.23 (m, 1H), 6.38 (s, 1H), 5.28 (s, 1H), 2.98 (s, 1H), 2.13 (s, 2H), 1.98-1.84 (m, 1H), 1.83-1.68 (m, 1H), 1.49-1.18 (m, 1H).

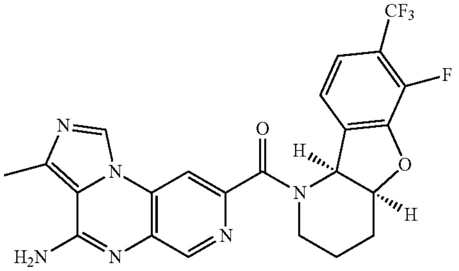 [SMILES: Cc1ncn2c1c(N)nc1cnc(C(=O)N3CCC[C@@H]4Oc5c(ccc(C(F)(F)F)c5F)[C@@H]43)cc12]

Example Ff-119: (4-amino-3-methylimidazo[1,5-a]pyrido[3,4-e]pyrazin-8-yl)((4aS,9bS)-6-fluoro-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and (4aS,9bS)-6-fluoro-7-(trifluoromethyl)-1,2,3,4,4a,9b-hexahydrobenzofuro[3,2-b]pyridine Ew-3. ES/MS: m/z=486.8 $[M+H]^+$. $^1H$ NMR (400 MHz, Methanol-d4) δ 9.22 (s, 1H), 8.78 (d, J=9.5 Hz, 1H), 8.54 (s, 0.5H, rotamer), 8.45 (s, 0.5H, rotamer), 7.64 (s, 0.5H, rotamer), 7.40 (d, J=7.8 Hz, 0.5H, rotamer), 7.26 (dd, J=7.9, 5.6 Hz, 1H), 6.40 (d, J=8.8 Hz, 0.5H, rotamer), 6.17-6.03 (m, 0.5H, rotamer), 5.35-5.23 (m, 0.5H, rotamer), 5.21-5.07 (m, 0.5H, rotamer), 4.51-4.32 (m, 0.5H, rotamer), 3.89-3.65 (m, 0.5H, rotamer), 3.06-2.90 (m, 1H), 2.79 (s, 3H), 2.21-1.67 (m, 4H).

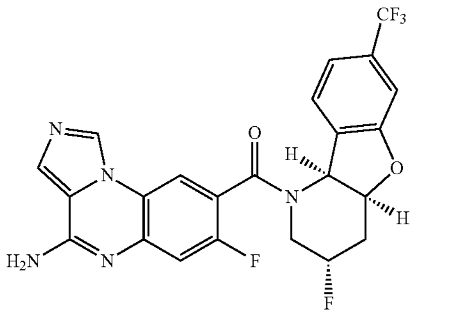 [SMILES: Nc1nc2cc(F)c(C(=O)N3C[C@@H](F)C[C@@H]4Oc5cc(C(F)(F)F)ccc5[C@@H]43)cc2n2cncc12]

Example Ff-120: (4-amino-7-fluoroimidazo[1,5-a]quinoxalin-8-yl)((3S,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)-7-fluoro-imidazo[1,5-a]quinoxaline-8-carboxylic acid Af-1 and (3S,4aS,9bS)-3-fluoro-7-(trifluoromethyl)-1,2,3,4,4a,9b-hexahydrobenzofuro[3,2-b]pyridine Ex-1. ES/MS: m/z=489.8 $[M+H]^+$. $^1$H NMR (400 MHz, Methanol-d4) δ 9.32 (s, 0.2H, minor rotamer), 9.20 (s, 1H), 8.39 (d, J=5.8 Hz, 1H), 8.33 (s, 1H), 7.66 (d, J=7.7 Hz, 1H), 7.54-7.24 (m, 2H), 7.16 (s, 1H), 6.39 (d, J=8.3 Hz, 1H), 5.31-5.19 (m, 1H), 5.05-4.93 (m, 1H), 3.79-3.60 (m, 1H), 3.25-3.07 (m, 1H), 2.90-2.76 (m, 1H), 2.37-2.14 (m, 1H).

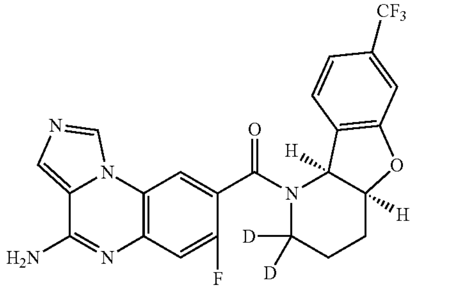 [SMILES: [2H]C1([2H])CC[C@@H]2Oc3cc(C(F)(F)F)ccc3[C@@H]2N1C(=O)c1cc2c(cc1F)nc(N)c1cncn12]

Example Ff-121: (4-amino-7-fluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl-2,2-d2)methanone. Prepared following general procedure VI-F starting with 4-(tert-butoxycarbonylamino)-7-fluoro-imidazo[1,5-a]quinoxaline-8-carboxylic acid Af-1 and (4aS,9bS)-2,2-dideuterio-7-(trifluoromethyl)-3,4,4a,9b-tetrahydro-1H-benzofuro[3,2-b]pyridine Ey-1. ES/MS: m/z=473.8 $[M+H]^+$. $^1$H NMR (400 MHz, Methanol-d4) δ 9.25 (s, 1H), 8.41 (d, J=5.9 Hz, 1H), 8.31 (s, 1H), 7.58 (s, 1H), 7.52-7.39 (m, 1H), 7.33-7.18 (m, 1H), 7.14 (s, 0.7H, major rotamer), 7.07 (s, 0.3H, minor rotamer), 6.44 (d, J=8.9 Hz, 0.7H, major rotamer), 5.63 (d, J=8.9 Hz, 0.3H, minor rotamer), 5.19 (dt, J=8.8, 4.4 Hz, 1H), 2.13-1.98 (m, 1H), 1.89-1.63 (m, 1H), 1.47-1.25 (m, 2H).

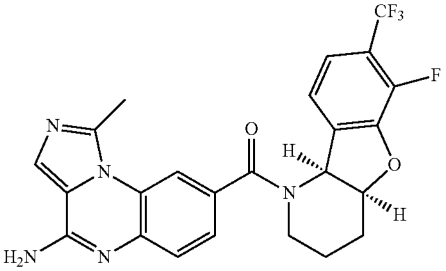 [SMILES: Cc1ncc2c(N)nc3ccc(C(=O)N4CCC[C@@H]5Oc6c(ccc(C(F)(F)F)c6F)[C@@H]54)cc3n12]

Example Ff-122: (4-amino-1-methylimidazo[1,5-a]quinoxalin-8-yl)((4aS,9bS)-6-fluoro-7-(trifluoromethyl)-3,4,4a,9b-tetrahydrobenzofuro[3,2-b]pyridin-1(2H)-yl)methanone. Prepared following general procedure VI-F starting with 4-(tert-butoxycarbonylamino)-1-methyl-imidazo[1,5-a]quinoxaline-8-carboxylic acid Af-3 and (4aS,9bS)-6-fluoro-7-(trifluoromethyl)-1,2,3,4,4a,9b-hexahydrobenzofuro[3,2-b]pyridine Ew-3. ES/MS: m/z=485.8 $[M+H]^+$. $^1$H NMR (400 MHz, Methanol-d4) δ 8.33 (d, J=8.8 Hz, 2H), 7.70 (d, J=2.5 Hz, 2H), 7.42 (d, J=7.9 Hz, 1H), 7.28 (dd, J=7.9, 5.5 Hz, 1H), 6.30 (s, 1H), 5.37-5.14 (m, 1H), 3.13 (s, 3H), 3.07-2.83 (m, 1H), 2.14 (d, J=6.7 Hz, 1H), 1.97-1.65 (m, 2H), 1.50-1.17 (m, 2H).

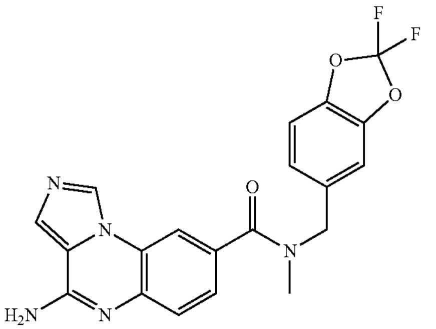 [SMILES: CN(Cc1ccc2c(c1)OC(F)(F)O2)C(=O)c1ccc2nc(N)c3cncn3c2c1]

Example Ff-123: 4-amino-N-((2,2-difluorobenzo[d][1,3]dioxol-5-yl)methyl)-N-methylimidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and 1-(2,2-difluorobenzo[d][1,3]dioxol-5-yl)-N-methylmethanamine Ed-11. ES/MS: m/z=412.0 $[M+H]^+$. $^1$H NMR (400 MHz, Methanol-$d_4$) δ 9.36 (s, 0.7H, major rotamer), 9.24 (s, 0.3H, minor rotamer), 8.46 (s, 1H), 8.41 (s, 1H), 7.70 (s, 1H), 7.36 (s, 0.7H, major rotamer), 7.25 (t, J=7.9 Hz, 2H), 7.11-7.00 (m, 0.3H, minor rotamer), 4.82 (s, 1H), 4.64 (s, 1H), 3.08 (s, 0.9H, minor rotamer), 3.07 (s, 2.1H, major rotamer).

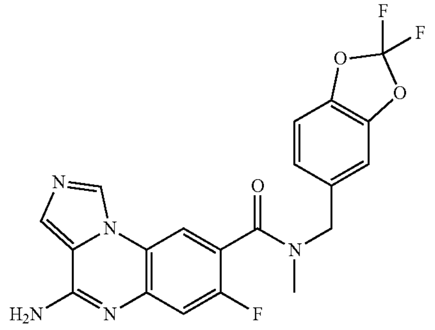 [SMILES: CN(Cc1ccc2c(c1)OC(F)(F)O2)C(=O)c1cc2c(cc1F)nc(N)c1cncn12]

Example Ff-124: 4-amino-N-((2,2-difluorobenzo[d][1,3]dioxol-5-yl)methyl)-7-fluoro-N-methylimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and 1-(2,2-difluorobenzo[d][1,3]dioxol-5-yl)-N-methylmethanamine Ed-11. ES/MS: m/z=430.2 $[M+H]^+$. 1H NMR (400 MHz, MeOD) δ 9.32-9.24 (m, 0.7H, major rotamer), 9.20 (s, 0.3H, minor rotamer), 8.45 (d, J=5.9 Hz, 1H), 8.40-8.30 (m, 1H), 7.47 (dd, J=9.7, 7.2 Hz, 1H), 7.32 (dd, J=1.5, 0.7 Hz, 0.7H, major rotamer), 7.26 (t, J=1.3 Hz, 1H), 7.19 (d, J=8.3 Hz, 0.3H, minor rotamer), 7.10 (d, J=1.7 Hz, 0.5H, rotamer), 7.04 (dd, J=8.3, 1.8 Hz, 0.5H, rotamer), 4.84 (s, 1H), 4.59 (s, 1H), 3.10 (s, 1H, minor rotamer), 2.98 (d, J=1.2 Hz, 2H, major rotamer).

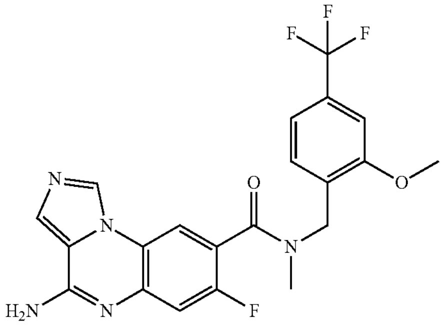 [SMILES: COc1cc(C(F)(F)F)ccc1CN(C)C(=O)c1cc2c(cc1F)nc(N)c1cncn12]

Example Ff-125: 4-amino-N-(2-methoxy-4-(trifluoromethyl)benzyl)-N-methylimidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and 1-(2-methoxy-4-(trifluoromethyl)phenyl)-N-methylmethanamine Ed-12. ES/MS: m/z=430.2 $[M+H]^+$. 1H NMR (400 MHz, MeOD) δ 9.36 (s, 0.5H, rotamer), 9.23 (s, 0.5H, rotamer), 8.58-8.35 (m, 2H), 7.73 (s, 1H), 7.65 (s, 1H), 7.54 (d, J=7.8 Hz, 0.5H, rotamer), 7.44 (d, J=7.9 Hz, 0.5H, rotamer), 7.38-7.31 (m, 1H), 7.30 (s, 0.5H, rotamer), 7.20 (s, 0.5H, rotamer), 4.68 (s, 1H), 3.99 (s, 1.5H, rotamer), 3.82 (s, 1.5H, major rotamer), 3.08 (s, 3H).

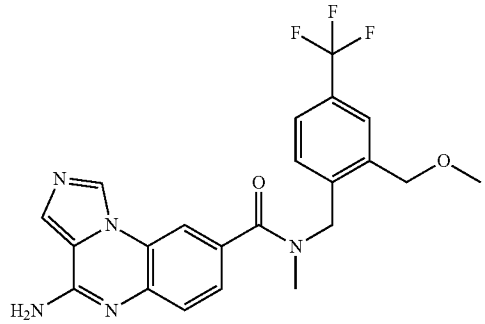 [SMILES: COCc1cc(C(F)(F)F)ccc1CN(C)C(=O)c1ccc2nc(N)c3cncn3c2c1]

Example Ff-126: 4-amino-N-(2-(methoxymethyl)-4-(trifluoromethyl)benzyl)-N-methylimidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and 1-(2-(methoxymethyl)-4-(trifluoromethyl)phenyl)-N-methylmethanamine Ed-13. ES/MS: m/z=444.1 $[M+H]^+$. 1H NMR (400 MHz, MeOD) δ 9.37 (s, 0.7H, major rotamer), 9.12 (s, 0.3H, minor rotamer), 8.48 (s, 0.6H, minor rotamer), 8.39 (d, J=12.0 Hz, 1.4H, major rotamer), 7.75 (d, J=16.7 Hz, 3H), 7.61 (d, J=7.4 Hz, 2H), 4.98 (s, 1.4H, major rotamer), 4.80 (s, 0.6H, minor rotamer), 4.68 (s, 1.4H, major rotamer), 4.38 (s, 0.6H, minor rotamer), 3.47 (s, 2H, major rotamer), 3.25 (s, 1H, minor rotamer), 3.20-3.07 (m, 1H, minor rotamer), 3.05 (s, 2H, major rotamer).

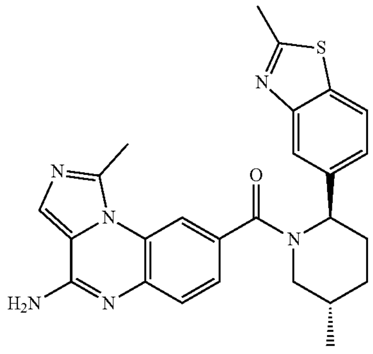 [SMILES: Cc1nc2cc([C@H]3CC[C@H](C)CN3C(=O)c3ccc4nc(N)c5cnc(C)n5c4c3)ccc2s1]

Example Ff-127: (4-aminoimidazo[1,5-a]quinoxalin-8-yl)((2R,5S)-5-methyl-2-(2-methylbenzo[d]thiazol-5-yl)piperidin-1-yl)methanone. Prepared following general procedure II-F starting with 4-((tert-butoxycarbonyl)amino)imidazo[1,5-a]quinoxaline-8-carboxylic acid Ae-1 and 2-methyl-5-((2R,5S)-5-methylpiperidin-2-yl)benzo[d]thiazole Ear-1. ES/MS: m/z=471.0 $[M+H]^+$. 1H NMR (400 MHz, Methanol-d4) δ 8.30 (s, 1H), 8.13 (s, 1H), 8.01 (d, J=8.4 Hz, 1H), 7.88 (s, 1H), 7.71 (d, J=1.2 Hz, 2H), 7.53-7.43 (m, 1H), 5.59 (s, 1H), 4.03 (s, 1H), 3.43 (dd, J=13.6, 3.8 Hz, 1H), 2.87 (s, 3H), 2.81 (s, 3H), 2.34 (dt, J=9.8, 4.7 Hz, 2H), 1.99 (brs, 1H), 1.90 (td, J=9.9, 5.1 Hz, 1H), 1.65-1.37 (m, 1H), 1.15 (d, J=7.0 Hz, 3H).

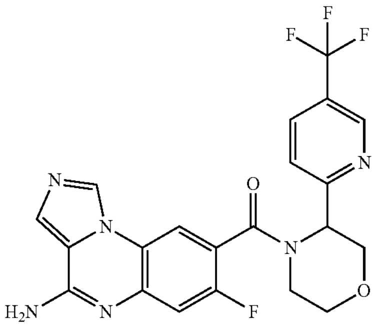

Example Ff-128: (4-amino-7-fluoroimidazo[1,5-a]quinoxalin-8-yl)(3-(5-(trifluoromethyl)pyridin-2-yl)morpholino)methanone. Prepared following general procedure VI-F starting with starting with starting with 4-(tert-butoxycarbonylamino)-7-fluoro-imidazo[1,5-a]quinoxaline-8-carboxylic acid Af-1 and 3-(5-(trifluoromethyl)pyridin-2-yl) morpholine hydrochloride Eai-10. ES/MS: m/z=461.0 $[M+H]^+$. $^1$H NMR (400 MHz, Methanol-d4) δ 9.30 (s, 0.7H, major rotamer), 9.20 (s, 0.3H, minor rotamer), 8.99 (s, 0.7H, major rotamer), 8.96 (s, 0.3H, minor rotamer), 8.49 (d, J=5.8 Hz, 0.7H, major rotamer), 8.43 (s, 0.3H, minor rotamer), 8.35 (s, 0.7H, major rotamer), 8.31 (s, 0.3H, minor rotamer), 8.21 (d, J=8.1 Hz, 0.7H, major rotamer), 8.13 (d, J=8.2 Hz, 0.3H, minor rotamer), 7.77 (d, J=8.4 Hz, 0.7H, major rotamer), 7.70 (d, J=8.3 Hz, 0.3H, minor rotamer), 7.48 (d, J=9.8 Hz, 0.7H, major rotamer), 7.39 (s, 0.3H, minor rotamer), 5.85 (s, 1H), 4.71 (d, J=12.2 Hz, 0.5H, minor rotamer), 4.46 (d, J=13.8 Hz, 0.5H, minor rotamer), 4.04 (t, J=15.4 Hz, 2H), 3.87-3.60 (m, 2.4H, major rotamer), 3.54 (d, J=9.7 Hz, 0.6H, minor rotamer).

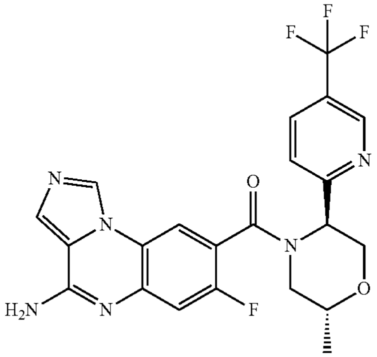 [SMILES: C[C@@H]1CN(C(=O)c2cc3c(cc2F)nc(N)c2cncn23)[C@@H](c2ccc(C(F)(F)F)cn2)CO1]

Example Ff-129: (4-amino-7-fluoroimidazo[1,5-a]quinoxalin-8-yl)((2R,5S)-2-methyl-5-(5-(trifluoromethyl)pyridin-2-yl)morpholino)methanone. Prepared following general procedure VI-F starting with starting with starting with 4-(tert-butoxycarbonylamino)-7-fluoro-imidazo[1,5-a]quinoxaline-8-carboxylic acid Af-1 and (2R)-2-methyl-5-(5-(trifluoromethyl)pyridin-2-yl)morpholine hydrochloride Eai-11 ES/MS: m/z=475.0 $[M+H]^+$. $^1$H NMR (400 MHz, Methanol-d4) δ 9.24 (s, 1H), 8.95 (s, 1H), 8.40 (s, 1H), 8.28 (s, 1H), 8.14 (d, J=11.7 Hz, 1H), 7.74 (s, 1H), 7.42 (s, 1H), 5.60 (s, 1H), 4.35 (d, J=4.3 Hz, 2H), 4.08 (s, 1H), 3.84 (s, 1H), 3.36-3.34 (m, 1H), 1.31 (s, 3H).

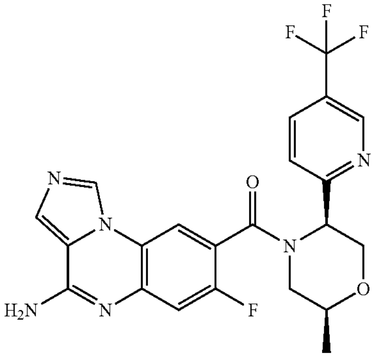 [SMILES: C[C@H]1CN(C(=O)c2cc3c(cc2F)nc(N)c2cncn23)[C@@H](c2ccc(C(F)(F)F)cn2)CO1]

Example Ff-130: (4-amino-7-fluoroimidazo[1,5-a]quinoxalin-8-yl)((2S,5S)-2-methyl-5-(5-(trifluoromethyl)pyridin-2-yl)morpholino)methanone. Prepared following general procedure VI-F starting with starting with starting with 4-(tert-butoxycarbonylamino)-7-fluoro-imidazo[1,5-a]quinoxaline-8-carboxylic acid Af-1 and (2S)-2-methyl-5-(5-(trifluoromethyl)pyridin-2-yl)morpholine hydrochloride Eai-8. ES/MS: m/z=475.0 $[M+H]^+$. $^1$H NMR (400 MHz, Methanol-d4) δ 9.33 (s, 0.6H, major rotamer), 9.22 (s, 0.4H, minor rotamer), 8.99 (s, 0.6H, major rotamer), 8.96 (s, 0.4H, minor rotamer), 8.51 (d, J=5.7 Hz, 0.6H, major rotamer), 8.45 (s, 0.4H, minor rotamer), 8.42 (s, 0.6H, major rotamer), 8.37 (s, 0.4H, minor rotamer), 8.26-8.17 (m, 0.6H, major rotamer), 8.13 (dd, J=8.5, 2.2 Hz, 0.4H, minor rotamer), 7.75 (d, J=8.3 Hz, 0.6H, major rotamer), 7.69 (d, J=8.4 Hz, 0.4H, minor rotamer), 7.53 (d, J=9.6 Hz, 0.6H, major rotamer), 7.42 (d, J=9.4 Hz, 0.4H, minor rotamer), 5.84 (s, 1H), 4.74 (d, J=12.2 Hz, 0.5H, rotamer), 4.50 (d, J=13.7 Hz, 0.5H, rotamer), 4.14 (dd, J=12.2, 3.3 Hz, 0.4H, minor rotamer), 4.09 (dd, J=12.2, 3.7 Hz, 0.6H, major rotamer), 3.89-3.78 (m, 0.6H, major rotamer), 3.75 (s, 1H), 3.55 (s, 0.4H, minor rotamer), 3.52-3.46 (m, 0.4H, minor rotamer), 3.31-3.23 (m, 0.6H, major rotamer), 1.21 (d, J=6.2 Hz, 1.2H, minor rotamer), 1.03 (d, J=6.1 Hz, 1.8H, major rotamer).

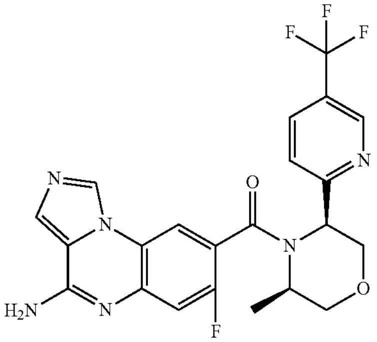 [SMILES: C[C@@H]1COC[C@H](c2ccc(C(F)(F)F)cn2)N1C(=O)c1cc2c(cc1F)nc(N)c1cncn12]

Example Ff-131: (4-amino-7-fluoroimidazo[1,5-a]quinoxalin-8-yl)((3R,5S)-3-methyl-5-(5-(trifluoromethyl)pyridin-2-yl)morpholino)methanone. Prepared following general procedure VI-F starting with starting with starting with 4-(tert-butoxycarbonylamino)-7-fluoro-imidazo[1,5-a]quinoxaline-8-carboxylic acid Af-1 and (3R)-3-methyl-5-(5-(trifluoromethyl)pyridin-2-yl)morpholine hydrochloride Eai-2. ES/MS: m/z=475.0 $[M+H]^+$. $^1$H NMR (400 MHz, Methanol-d4) δ 9.33 (s, 1H), 8.98 (s, 1H), 8.57 (s, 1H), 8.15 (s, 1H), 7.85 (s, 1H), 7.45 (s, 1H), 5.89 (s, 1H), 5.27 (s, 1H), 3.87 (s, 4H), 0.89 (d, J=7.0 Hz, 3H).

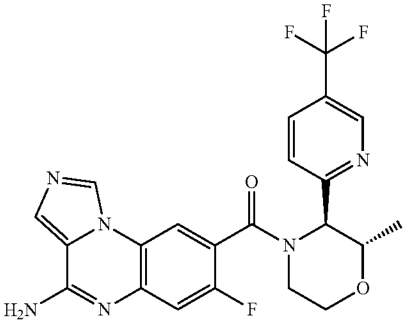 [SMILES: C[C@@H]1OCCN(C(=O)c2cc3c(cc2F)nc(N)c2cncn23)[C@H]1c1ccc(C(F)(F)F)cn1]

Example Ff-132: (4-amino-7-fluoroimidazo[1,5-a]quinoxalin-8-yl)((2S,3S)-2-methyl-3-(5-(trifluoromethyl)pyridin-2-yl)morpholino)methanone. Prepared following general procedure VI-F starting with starting with starting with 4-(tert-butoxycarbonylamino)-7-fluoro-imidazo[1,5-a]quinoxaline-8-carboxylic acid Af-1 and (2S)-2-methyl-3-(5-(trifluoromethyl)pyridin-2-yl)morpholine hydrochloride Eai-3. ES/MS: m/z=475.0 $[M+H]^+$. $^1H$ NMR (400 MHz, Methanol-d4) δ 9.30 (s, 1H), 8.97 (s, 1H), 8.45 (s, 1H), 8.36 (s, 1H), 8.18 (s, 1H), 7.77 (s, 1H), 7.47 (s, 1H), 5.50 (s, 1H), 4.10 (d, J=12.4 Hz, 1.3H, minor rotamer), 3.70 (s, 1.7H, major rotamer), 3.54 (s, 1H), 1.50 (d, J=6.6 Hz, 3H).

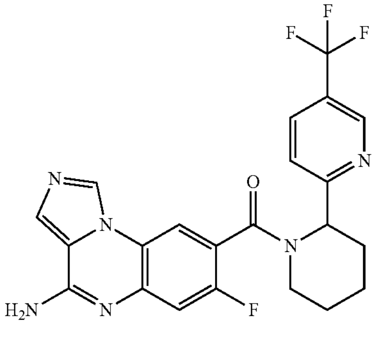 [SMILES: Nc1nc2cc(F)c(C(=O)N3CCCCC3c3ccc(C(F)(F)F)cn3)cc2n2cncc12]

Example Ff-133: (4-amino-7-fluoroimidazo[1,5-a]quinoxalin-8-yl)(2-(5-(trifluoromethyl)pyridin-2-yl)piperidin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 2-(piperidin-2-yl)-5-(trifluoromethyl)pyridine hydrochloride Eai-4 ES/MS: m/z=459.0 $[M+H]^+$. $^1H$ NMR (400 MHz, Methanol-d4) δ 9.32 (s, 0.7H, major rotamer), 9.14 (s, 0.3H, minor rotamer), 8.96 (s, 1H), 8.49 (s, 0.7H, major rotamer), 8.41 (s, 1H), 8.39-8.29 (m, 0.3H, minor rotamer), 8.18 (dd, J=8.4, 2.4 Hz, 0.7H, major rotamer), 8.11 (d, J=8.4 Hz, 0.3H, minor rotamer), 7.70 (s, 0.7H, major rotamer), 7.60 (d, J=8.3 Hz, 0.3H, minor rotamer), 7.53 (d, J=9.5 Hz, 0.7H, major rotamer), 7.45 (s, 0.3H, minor rotamer), 6.09 (s, 1H), 5.05 (s, 0.5H, rotamer), 4.69 (d, J=13.6 Hz, 0.5H, rotamer), 3.62 (d, J=13.8 Hz, 0.5H, rotamer), 3.46-3.35 (m, 0.5H, rotamer), 2.74 (brs, 1H), 2.20-1.98 (m, 1H), 1.88-1.31 (m, 4H).

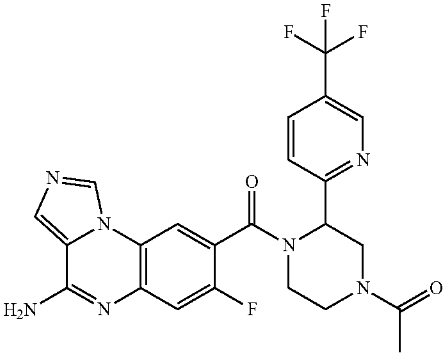 [SMILES: CC(=O)N1CCN(C(=O)c2cc3c(cc2F)nc(N)c2cncn23)C(c2ccc(C(F)(F)F)cn2)C1]

Example Ff-134: 1-(4-(4-amino-7-fluoroimidazo[1,5-a]quinoxaline-8-carbonyl)-3-(5-(trifluoromethyl)pyridin-2-yl)piperazin-1-yl)ethan-1-one. Prepared following general procedure VI-F starting with starting with starting with 4-(tert-butoxycarbonylamino)-7-fluoro-imidazo[1,5-a]quinoxaline-8-carboxylic acid Af-1 and 1-(3-(5-(trifluoromethyl)pyridin-2-yl)piperazin-1-yl)ethan-1-one hydrochloride Eai-5. ES/MS: m/z=502.0 $[M+H]^+$. $^1H$ NMR (400 MHz, Methanol-d4) δ 9.30 (s, 0.8H, major rotamer), 9.20 (s, 0.2H, minor rotamer), 9.07-8.97 (m, 0.5H, rotamer), 8.97-8.85 (m, 0.5H, rotamer), 8.52 (d, J=5.8 Hz, 0.7H, major rotamer), 8.46 (d, J=5.8 Hz, 0.3H, minor rotamer), 8.40 (d, J=1.9 Hz, 0.8H, major rotamer), 8.36 (s, 0.2H, minor rotamer), 8.23 (dd, J=8.4, 2.3 Hz, 1H), 8.18-8.10 (m, 0.6H, major rotamer), 8.04 (d, J=8.4 Hz, 0.3H, minor rotamer), 7.75 (t, J=10.7 Hz, 0.7H, major rotamer), 7.60 (dd, J=18.6, 8.5 Hz, 0.3H, minor rotamer), 7.53 (dd, J=9.7, 2.4 Hz, 0.7H, major rotamer), 7.43 (s, 0.3H, minor rotamer), 6.06 (s, 0.6H, major rotamer), 5.93 (s, 0.4H, minor rotamer), 5.16 (s, 1H), 5.11-5.00 (m, 0.3H, minor rotamer), 4.95 (d, J=14.3 Hz, 0.7H, major rotamer), 4.70 (d, J=13.8 Hz, 0.3H, minor rotamer), 4.55 (t, J=16.6 Hz, 0.7H, major rotamer), 4.29 (d, J=13.3 Hz, 0.7H, major rotamer), 4.06 (d, J=13.3 Hz, 0.3H, minor rotamer), 3.89 (d, J=13.6 Hz, 0.3H, minor rotamer), 3.82 (dd, J=14.1, 4.4 Hz, 0.7H, major rotamer), 3.73 (d, J=14.3 Hz, 0.7H, major rotamer, 3.61 (d, J=4.7 Hz, 0.2H, minor rotamer), 3.58-3.39 (m, 1H), 3.21 (t, J=12.4 Hz, 0.2H, minor rotamer), 3.06 (t, J=12.1 Hz, 0.8H, major rotamer), 2.19 (s, 2H, major rotamer), 2.10 (d, J=6.7 Hz, 1H, minor rotamer).

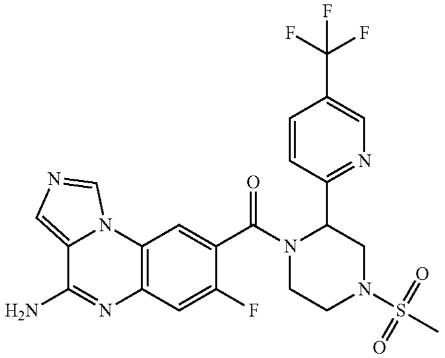 [SMILES: CS(=O)(=O)N1CCN(C(=O)c2cc3c(cc2F)nc(N)c2cncn23)C(c2ccc(C(F)(F)F)cn2)C1]

Example Ff-135: (4-amino-7-fluoroimidazo[1,5-a]quinoxalin-8-yl)(4-(methylsulfonyl)-2-(5-(trifluoromethyl)pyridin-2-yl)piperazin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 1-(methylsulfonyl)-3-(5-(trifluoromethyl)pyridin-2-yl)piperazine hydrochloride Eai-6. ES/MS: m/z=538.0 [M+H]$^+$. $^1$H NMR (400 MHz, Methanol-d4) δ 9.29 (s, 0.7H, major rotamer), 9.21 (s, 0.3H, minor rotamer), 9.01 (s, 1H), 8.49 (d, J=5.9 Hz, 1H), 8.35 (s, 0.6H, major rotamer), 8.31 (s, 0.4H, minor rotamer), 8.21 (d, J=8.3 Hz, 0.6H, major rotamer), 8.14 (d, J=8.4 Hz, 0.4H, minor rotamer), 7.75 (dd, J=18.8, 8.1 Hz, 1H), 7.49 (d, J=9.8 Hz, 0.6H, major rotamer), 7.41 (d, J=9.9 Hz, 0.4H, minor rotamer), 6.16 (s, 1H), 5.18 (s, 0.7H, major rotamer), 4.77 (d, J=12.2 Hz, 0.3H, minor rotamer), 4.69 (d, J=11.2 Hz, 0.7H, major rotamer), 4.60 (d, J=12.5 Hz, 0.3H, minor rotamer), 3.78 (d, J=13.2 Hz, 1H), 3.62 (d, J=12.3 Hz, 1H), 3.48-3.37 (m, 1H), 3.07 (d, J=11.9 Hz, 1H), 2.93 (s, 1H), 2.90 (s, 2H, major rotamer).

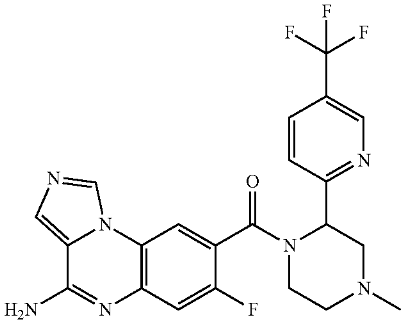 [SMILES: CN1CCN(C(=O)c2cc3c(cc2F)nc(N)c2cncn23)C(c2ccc(C(F)(F)F)cn2)C1]

Example Ff-136: (4-amino-7-fluoroimidazo[1,5-a]quinoxalin-8-yl)(4-methyl-2-(5-(trifluoromethyl)pyridin-2-yl)piperazin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 1-methyl-3-(5-(trifluoromethyl)pyridin-2-yl)piperazine hydrochloride Eai-7. ES/MS: m/z=474.0 [M+H]$^+$. $^1$H NMR (400 MHz, Methanol-d4) δ 9.10 (s, 1H), 9.01 (s, 1H), 8.35 (d, J=6.9 Hz, 2H), 8.17 (s, 1H), 7.90 (d, J=8.3 Hz, 1H), 7.39 (d, J=10.7 Hz, 1H), 6.49 (s, 1H), 4.42 (d, J=13.0 Hz, 1H), 3.90 (d, J=14.8 Hz, 1H), 3.64 (d, J=13.0 Hz, 1H), 3.58-3.46 (m, 2H), 3.42-3.35 (m, 1H), 3.10 (s, 3H).

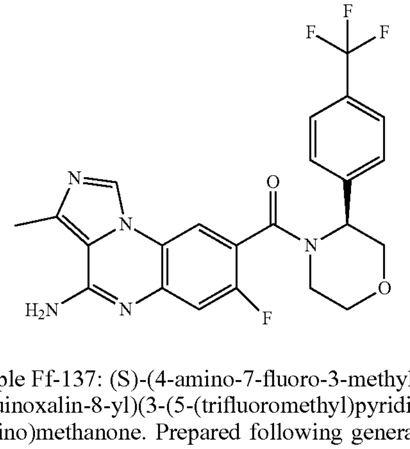

Example Ff-137: (S)-(4-amino-7-fluoro-3-methylimidazo[1,5-a]quinoxalin-8-yl)(3-(5-(trifluoromethyl)pyridin-2-yl)morpholino)methanone. Prepared following general procedure VI-F starting with starting with starting with 4-((tert-butoxycarbonyl)amino)-7-fluoro-3-methylimidazo[1,5-a]quinoxaline-8-carboxylic acid Af-4 and commercial (S)-3-(4-(trifluoromethyl)phenyl)morpholine. ES/MS: m/z=474.0 [M+H]$^+$. $^1$H NMR (400 MHz, Methanol-d4) δ 9.18 (s, 1H), 8.38 (s, 1H), 7.84 (s, 2H), 7.75 (d, J=8.1 Hz, 2H), 7.57 (s, 0.3H, minor rotamer), 7.44 (d, J=9.7 Hz, 0.7H, major rotamer), 5.89 (s, 1H), 4.65 (d, J=12.5 Hz, 0.7H, major rotamer), 4.49 (s, 0.3H, minor rotamer), 4.02 (d, J=13.4 Hz, 1H), 3.87 (s, 1H), 3.77-3.59 (m, 1H), 3.40 (s, 2H), 2.80 (s, 3H).

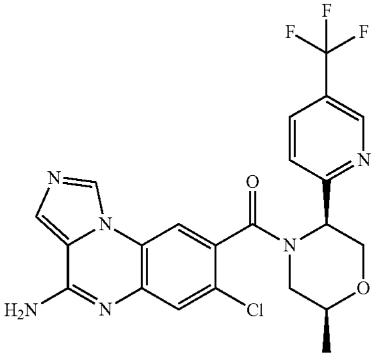 [SMILES: C[C@H]1CN(C(=O)c2cc3c(cc2Cl)nc(N)c2cncn23)[C@@H](c2ccc(C(F)(F)F)cn2)CO1]

Example Ff-138: (4-amino-7-chloroimidazo[1,5-a]quinoxalin-8-yl)((2S,5S)-2-methyl-5-(5-(trifluoromethyl)pyridin-2-yl)morpholino)methanone. Prepared following general procedure VI-F starting with starting with starting with 4-((tert-butoxycarbonyl)amino)-7-chloroimidazo[1,5-a]quinoxaline-8-carboxylic acid Af-2 and (2S)-2-methyl-5-(5-(trifluoromethyl)pyridin-2-yl)morpholine hydrochloride Eai-8. ES/MS: m/z=491.0 [M+H]$^+$. $^1$H NMR (400 MHz, Methanol-d4) δ 9.40-9.20 (m, 1H), 9.16-8.83 (m, 1H), 8.51 (s, 0.5H, rotamer), 8.42 (s, 0.5H, rotamer), 8.40 (d, J=1.5 Hz, 0.5H, rotamer), 8.32 (d, J=6.3 Hz, 0.5H, rotamer), 8.22 (dt, J=7.4, 3.3 Hz, 0.5H, rotamer), 8.12 (dd, J=8.4, 2.4 Hz, 0.5H, rotamer), 7.83 (d, J=8.3 Hz, 0.5H, rotamer), 7.77 (d, J=8.8 Hz, 0.5H, rotamer), 7.72 (m, 1H), 5.84 (s, 0.5H, rotamer), 4.93 (d, J=12.2 Hz, 0.5H, rotamer), 4.73 (d, J=12.6 Hz, 0.4H), 4.68-4.50 (m, 0.6H, major rotamer), 4.27-4.03 (m, 1H), 3.88-3.76 (m, 1H), 3.41 (td, J=14.1, 2.8 Hz, 0.5H, rotamer), 3.28-3.14 (m, 0.5H, rotamer), 3.13-3.04 (m, 0.5H, rotamer), 2.77 (dd, J=13.6, 11.0 Hz, 0.5H, rotamer), 1.23 (dd, J=16.0, 6.2 Hz, 1H, minor rotamer), 1.01 (dd, J=7.6, 6.2 Hz, 2H, major rotamer).

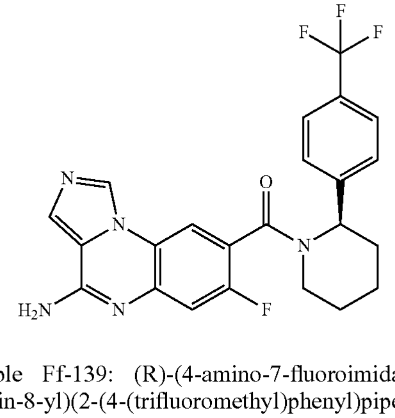

Example Ff-139: (R)-(4-amino-7-fluoroimidazo[1,5-a]quinoxalin-8-yl)(2-(4-(trifluoromethyl)phenyl)piperidin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and commercial (R)-2-(4-(trifluoromethyl) phenyl)piperidine hydrochloride. ES/MS: m/z=458.0 $[M+H]^+$. $^1$H NMR (400 MHz, Methanol-d4) δ 9.33 (s, 1H), 8.53 (d, J=5.8 Hz, 1H), 8.39 (s, 0.7H, major rotamer), 8.35 (s, 0.3H, minor rotamer), 7.77 (d, J=8.1 Hz, 1.7H, major rotamer), 7.71 (d, J=7.7 Hz, 0.3H, minor rotamer), 7.65 (d, J=8.1 Hz, 2H), 7.51 (d, J=9.7 Hz, 1H), 6.14 (s, 1H), 5.04 (s, 0.7H, major rotamer), 4.71 (d, J=13.6 Hz, 0.3H, minor rotamer), 3.56 (d, J=13.9 Hz, 1H), 3.15 (p, J=1.6 Hz, 0.7H, major rotamer), 2.93 (s, 0.3H, minor rotamer), 2.65 (d, J=16.7 Hz, 0.6H, major rotamer), 2.52 (s, 0.4H, minor rotamer), 2.28-2.02 (m, 1H), 1.79 (d, J=11.2 Hz, 1H), 1.62 (s, 2H).

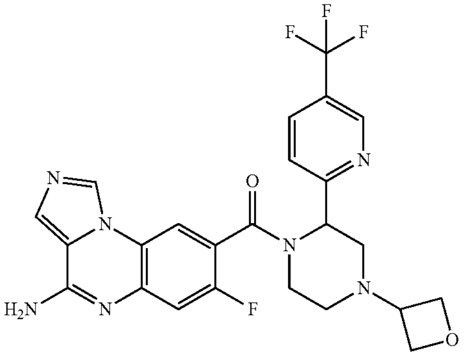 [SMILES: Nc1nc2cc(F)c(C(=O)N3CCN(C4COC4)CC3c3ccc(C(F)(F)F)cn3)cc2n2cncc12]

Example Ff-140: (4-amino-7-fluoroimidazo[1,5-a]quinoxalin-8-yl)(4-(oxetan-3-yl)-2-(5-(trifluoromethyl)pyridin-2-yl)piperazin-1-yl)methanone. Prepared following general procedure VI-F starting with starting with starting with 4-(tert-butoxycarbonylamino)-7-fluoro-imidazo[1,5-a] quinoxaline-8-carboxylic acid Af-1 and 1-(oxetan-3-yl)-3-(5-(trifluoromethyl)pyridin-2-yl)piperazine Eaj-1. ES/MS: m/z=516.0 $[M+H]^+$. $^1$H NMR (400 MHz, Methanol-d4) δ 9.09 (s, 1H), 9.01 (s, 0.7H, major rotamer), 8.94 (s, 0.3H, minor rotamer), 8.33 (d, J=6.2 Hz, 1H), 8.21 (d, J=8.4 Hz, 0.8H, major rotamer), 8.14 (d, J=8.3 Hz, 0.2H, minor rotamer), 7.98 (s, 0.8H, major rotamer), 7.92 (s, 0.2H, minor rotamer), 7.71 (t, J=8.7 Hz, 2H), 7.33 (d, J=11.0 Hz, 0.8H, major rotamer), 7.22 (s, 0.2H, minor rotamer), 6.02 (s, 0.8H, major rotamer), 5.05 (s, 0.2H, minor rotamer), 4.74 (t, J=6.5 Hz, 1H), 4.63 (t, J=6.6 Hz, 0.7H, minor rotamer), 4.58-4.49 (m, 1.3H, major rotamer), 4.47 (t, J=6.1 Hz, 1H), 3.95 (s, 0.7H, minor rotamer), 3.72 (d, J=13.4 Hz, 1.3H, major rotamer), 3.55 (d, J=7.3 Hz, 2H), 2.87 (s, 0.2H, minor rotamer), 2.69 (d, J=11.4 Hz, 0.8H, major rotamer), 2.54 (d, J=11.2 Hz, 0.2H, minor rotamer), 2.46 (d, J=12.3 Hz, 0.8H, major rotamer), 2.17 (s, 1H).

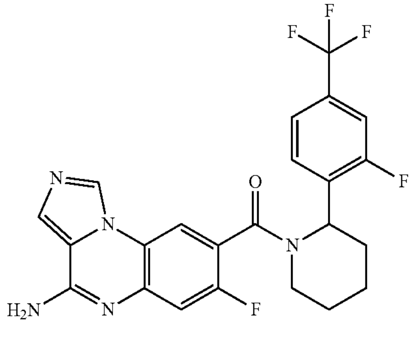 [SMILES: Nc1nc2cc(F)c(C(=O)N3CCCCC3c3ccc(C(F)(F)F)cc3F)cc2n2cncc12]

Example Ff-141: (4-amino-7-fluoroimidazo[1,5-a]quinoxalin-8-yl)(2-(2-fluoro-4-(trifluoromethyl)phenyl)piperidin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 2-(2-fluoro-4-(trifluoromethyl)phenyl)piperidine Eak-1. ES/MS: m/z=476.0 $[M+H]^+$. $^1$H NMR (400 MHz, Methanol-d4) δ 9.30 (s, 1H), 8.39 (s, 1H), 7.69 (t, J=7.9 Hz, 1H), 7.65-7.56 (m, 1H), 7.52 (t, J=10.9 Hz, 2H), 7.38 (s, 1H), 6.06 (s, 1H), 5.22 (s, 0.5H, rotamer), 4.76 (s, 0.5H, rotamer), 3.70 (d, J=13.7 Hz, 1H), 3.59-3.43 (m, 1H), 2.36 (d, J=14.4 Hz, 1.5H, major rotamer), 2.22-2.07 (m, 0.5H, minor rotamer), 1.73 (brs, 5H).

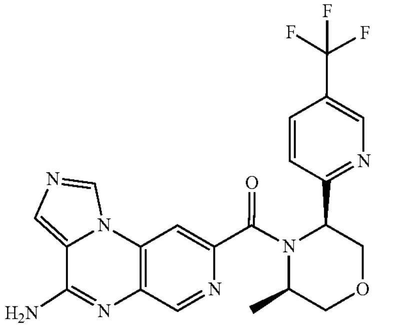 [SMILES: C[C@@H]1COC[C@H](c2ccc(C(F)(F)F)cn2)N1C(=O)c1cc2c(cn1)nc(N)c1cncn12]

Example Ff-142: (4-aminoimidazo[1,5-a]pyrido[3,4-e] pyrazin-8-yl)((3R,5S)-3-methyl-5-(5-(trifluoromethyl)pyridin-2-yl)morpholino)methanone. Prepared following general procedure VI-F starting with starting with starting with 4-((tert-butoxycarbonyl)amino)imidazo[1,5-a]pyrido[3,4-e] pyrazine-8-carboxylic acid Af-6 and (3R)-3-methyl-5-(5-(trifluoromethyl)pyridin-2-yl)morpholine hydrochloride Eai-2. ES/MS: m/z=458.0 $[M+H]^+$. $^1$H NMR (400 MHz, Methanol-d4) δ 9.33 (s, 1H), 8.98 (s, 1H), 8.57 (s, 1H), 8.15 (s, 1H), 7.85 (s, 1H), 7.45 (s, 1H), 5.89 (s, 1H), 5.27 (s, 1H), 3.87 (s, 4H), 0.89 (d, J=7.0 Hz, 3H).

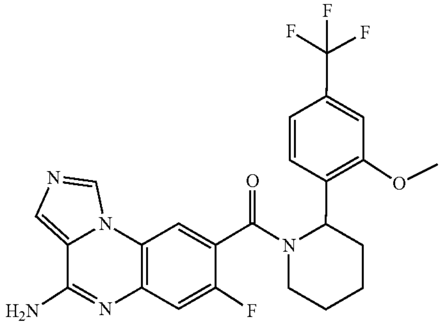 [SMILES: COc1cc(C(F)(F)F)ccc1C1CCCCN1C(=O)c1cc2c(cc1F)nc(N)c1cncn12]

Example Ff-143: (4-amino-7-fluoroimidazo[1,5-a]quinoxalin-8-yl)(2-(2-methoxy-4-(trifluoromethyl)phenyl)piperidin-1-yl)methanone. Prepared following general procedure VI-F starting with starting with starting with 4-(tert-butoxycarbonylamino)-7-fluoro-imidazo[1,5-a] quinoxaline-8-carboxylic acid Af-1 and 2-(2-methoxy-4-(trifluoromethyl)phenyl)piperidine Eak-2. ES/MS: m/z=488.0 $[M+H]^+$. $^1$H NMR (400 MHz, Methanol-d4) δ 9.30 (s, 1H), 8.37 (d, J=17.6 Hz, 2H), 7.52 (dd, J=18.0, 8.8 Hz, 1.7H, major rotamer), 7.37-7.24 (m, 2.0H), 6.99 (s, 0.3H, minor rotamer), 5.97 (s, 1H), 5.16 (s, 0.5H, rotamer), 4.71 (d, J=13.8 Hz, 0.5H, rotamer), 3.98 (s, 2.3H, major rotamer), 3.78-3.47 (m, 2H), 3.60 (s, 0.7H, minor rotamer), 2.26 (s, 0.5H, rotamer), 2.07 (d, J=17.6 Hz, 0.5H, rotamer), 1.80-1.50 (m, 4H).

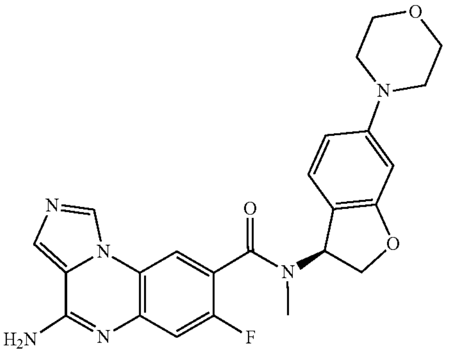 [SMILES: CN(C(=O)c1cc2c(cc1F)nc(N)c1cncn12)[C@@H]1COc2cc(N3CCOCC3)ccc21]

Example Ff-144: (S)-4-amino-7-fluoro-N-methyl-N-(6-morpholino-2,3-dihydrobenzofuran-3-yl)imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and (S)—N-methyl-6-morpholino-2,3-dihydrobenzofuran-3-amine Eap-1. ES/MS: m/z=463.0 $[M+H]^+$. $^1$H NMR (400 MHz, MeOD) δ 9.31 (s, 0.1H, minor rotamer), 9.27 (s, 0.9H, major rotamer), 8.65 (d, J=6.3 Hz, 0.1H, minor rotamer), 8.44 (d, J=5.9 Hz, 0.9H, major rotamer), 8.39 (d, J=4.5 Hz, 1H), 7.57 (d, J=8.7 Hz, 0.1H, minor rotamer), 7.53-7.40 (m, 0.9H, major rotamer), 7.26 (d, J=8.4 Hz, 0.4H, minor rotamer), 7.21-7.12 (m, 0.6H, major rotamer), 6.66 (dd, J=8.4, 2.2 Hz, 0.6H, major rotamer), 6.61 (d, J=8.3 Hz, 0.4H, minor rotamer), 6.53 (d, J=2.2 Hz, 0.5H, rotamer), 6.45 (s, 0.4H, minor rotamer), 6.40 (dd, J=8.5, 2.9 Hz, 0.6H, major rotamer), 5.45 (s, 1H), 4.96 (m, 0.6H, major rotamer), 4.76 (dd, J=10.7, 8.4 Hz, 0.4H, minor rotamer), 4.59 (dd, J=10.6, 3.1 Hz, 1H), 4.05-3.91 (m, 0.4H, minor rotamer), 3.83 (dt, J=10.2, 4.8 Hz, 3.6H, major rotamer), 3.23-3.08 (m, 4H), 2.84 (s, 1.5H, rotamer), 2.67 (t, J=0.8 Hz, 1.5H, rotamer).

-continued

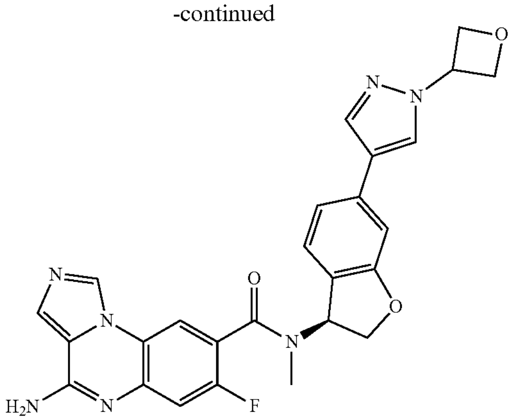

Example Ff-145

Example Ff-145: (S)-4-amino-7-fluoro-N-methyl-N-(6-(1-(oxetan-3-yl)-1H-pyrazol-4-yl)-2,3-dihydrobenzofuran-3-yl)imidazo[1,5-a]quinoxaline-8-carboxamide. Intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate was prepared following step 1 of general procedure VI-F starting with starting with 4-((tert-butoxycarbonyl)amino)-7-fluoroimidazo[1,5-a]quinoxaline-8-carboxylic acid Af-1 and (S)-(6-bromo-2,3-dihydrobenzofuran-3-yl)(methyl)-12-azane Eh-5.

A suspension of tert-butyl (S)-(8-((6-bromo-2,3-dihydrobenzofuran-3-yl)(methyl)carbamoyl)-7-fluoroimidazo[1,5-a]quinoxalin-4-yl)carbamate (50.0 mg, 0.0899 mmol), 1-(oxetan-3-yl)-4-(4,4,5,5-tetramethyl-1,3,2-dioxaborolan-2-yl)pyrazole (27.9 mg, 0.111 mmol), XPhos Pd G3 (7.86 mg, 0.00929 mmol) and sodium carbonate (2000 mmol/L, 0.152 mL, 0.303 mmol) in dioxane (1.5 mL) was degassed with Ar for 5 min, then heated at 80 deg o/n. The reaction was diluted with EtOAc and washed with brine. Dried over sodium sulfate and purified by flash chromatography. Further purification by preparative HPLC, followed by conversion to free base (dissolved product fractions in EtOAc and washed with saturated sodium bicarbonate solution 3× and brine) gave title compound. ES/MS: m/z=500.0 $[M+H]^+$. $^1$H NMR (400 MHz, Methanol-d4) δ 9.06 (s, 1H), 8.26 (d, J=6.3 Hz, 1H), 8.21-8.10 (m, 1H), 7.99 (s, 1H), 7.96 (d, J=15.1 Hz, 1H), 7.46-7.01 (m, 4H), 6.49 (dd, J=8.6, 3.4 Hz, 1H), 5.60 (q, J=6.8 Hz, 1.5H, major rotamer), 5.08 (dd, J=6.9, 4.3 Hz, 4H), 4.80 (dd, J=10.6, 8.7 Hz, 0.5H, minor rotamer), 4.64 (dd, J=10.5, 3.5 Hz, 1H), 2.85 (s, 1.5H, rotamer), 2.72 (d, J=1.3 Hz, 1.5H, rotamer).

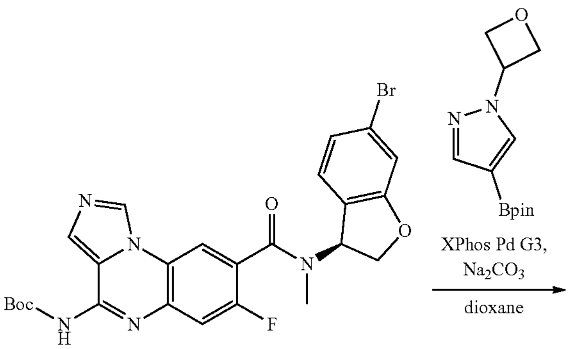

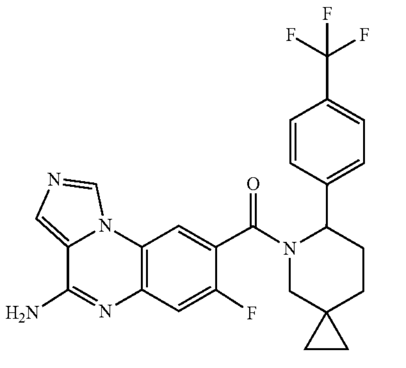 [SMILES: Nc1nc2cc(F)c(C(=O)N3CC4(CCC3c3ccc(C(F)(F)F)cc3)CC4)cc2n2cncc12]

Example Ff-146: (4-amino-7-fluoroimidazo[1,5-a]quinoxalin-8-yl)(6-(2-fluoro-4-(trifluoromethyl)phenyl)-5-azaspiro[2.5]octan-5-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 6-(4-(trifluoromethyl)phenyl)-5-azaspiro[2.5]octane Eak-3. ES/MS: m/z=484.0 $[M+H]^+$. $^1H$ NMR (400 MHz, Methanol-d4) δ 9.34 (s, 0.6H, major rotamer), 9.09 (s, 0.4H, minor rotamer), 8.53 (s, 0.6H, minor rotamer), 8.36 (s, 1.3H, major rotamer), 7.79 (d, J=7.9 Hz, 2H), 7.72 (d, J=10.5 Hz, 2H), 7.56 (d, J=8.1 Hz, 0.5H, rotamer), 7.49 (d, J=9.7 Hz, 0.5H, rotamer), 6.23 (s, 0.6H, major rotamer), 5.11 (s, 0.4H, minor rotamer), 3.93 (d, J=13.6 Hz, 0.4H, minor rotamer), 3.61 (d, J=13.8 Hz, 0.6H, major rotamer), 2.86-2.64 (m, 1.6H, major rotamer), 2.56 (s, 0.4H, minor rotamer), 2.47-2.22 (m, 1H), 2.14-1.91 (m, 1H), 1.04 (d, J=13.0 Hz, 1H), 0.81-0.02 (m, 4H).

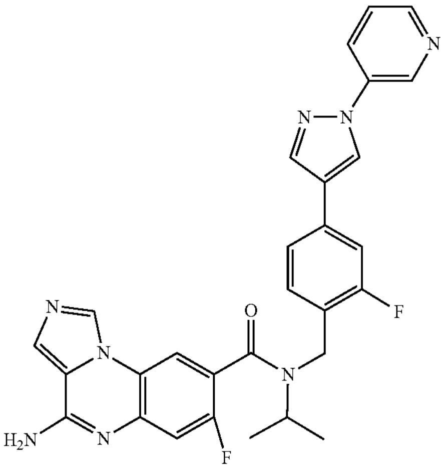

Example Ff-147: 4-amino-7-fluoro-N-(2-fluoro-4-(1-(pyridin-2-yl)-1H-pyrazol-4-yl)benzyl)-N-isopropylimidazo[1,5-a]quinoxaline-8-carboxamide. Prepared following the procedure reported for example Ff-23 starting with 4-(tert-butoxycarbonylamino)-7-fluoro-imidazo[1,5-a]quinoxaline-8-carboxylic acid Af-1, N-(4-bromo-2-fluorobenzyl)propan-2-amine Ed-9 and 2-[4-(4,4,5,5-tetramethyl-1,3,2-dioxaborolan-2-yl)pyrazol-1-yl]pyridine. ES/MS: m/z=539.0 $[M+H]^+$. $^1H$ NMR (400 MHz, Methanol-$d_4$) δ 9.33 (s, 0.7H, major rotamer), 9.10 (s, 0.3H, minor rotamer), 9.00 (d, J=0.8 Hz, 0.7H, major rotamer), 8.84 (s, 0.3H, minor rotamer), 8.48 (d, J=6.6 Hz, 1.3H, major rotamer), 8.35 (s, 0.6H, minor rotamer), 8.20 (d, J=5.8 Hz, 1H), 8.15 (d, J=5.9 Hz, 0.4H, minor rotamer), 8.04-7.87 (m, 2.6H, major rotamer), 7.68-7.42 (m, 3H), 7.42-7.28 (m, 1.7H, major rotamer), 7.22 (d, J=11.6 Hz, 0.3H, minor rotamer), 4.79 (s, 1H), 4.61 (s, 1H), 4.10 (q, J=6.5 Hz, 1H), 1.41 (d, J=6.8 Hz, 2H, minor rotamer), 1.24 (d, J=6.6 Hz, 4H, major rotamer).

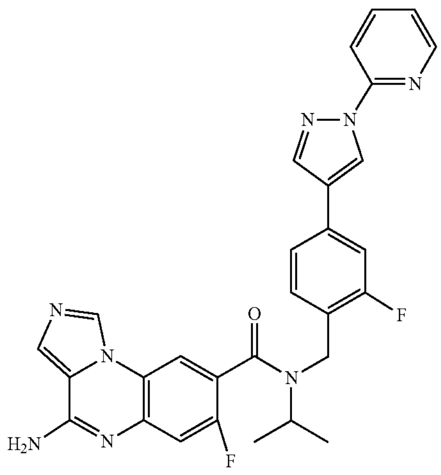 [SMILES: CC(C)N(Cc1ccc(-c2cnn(-c3ccccn3)c2)cc1F)C(=O)c1cc2c(cc1F)nc(N)c1cncn12]

Example Ff-148: 4-amino-7-fluoro-N-(2-fluoro-4-(1-(pyridin-3-yl)-1H-pyrazol-4-yl)benzyl)-N-isopropylimidazo[1,5-a]quinoxaline-8-carboxamide. Prepared following the procedure reported for example Ff-23 starting with 4-(tert-butoxycarbonylamino)-7-fluoro-imidazo[1,5-a]quinoxaline-8-carboxylic acid Af-1, N-(4-bromo-2-fluorobenzyl)propan-2-amine Ed-9 and 3-[4-(4,4,5,5-tetramethyl-1,3,2-dioxaborolan-2-yl)pyrazol-1-yl]pyridine. ES/MS: m/z=539.0 $[M+H]^+$. $^1H$ NMR (400 MHz, Methanol-$d_4$) δ 9.34 (s, 1H), 9.17 (d, J=2.6 Hz, 1H), 9.11 (d, J=4.2 Hz, 1H), 8.86 (s, 0.7H, major rotamer), 8.70 (s, 0.3H, minor rotamer), 8.57 (dd, J=4.8, 1.5 Hz, 1H), 8.49 (d, J=5.9 Hz, 0.3H, minor rotamer), 8.43-8.36 (m, 0.7H, major rotamer), 8.35 (d, J=8.5 Hz, 0.3H, minor rotamer), 8.23 (s, 0.7H, major rotamer), 8.15 (d, J=5.8 Hz, 0.5H, rotamer), 8.07 (s, 0.5H, rotamer), 7.68 (td, J=9.8, 9.2, 4.8 Hz, 1H), 7.59-7.42 (m, 3H), 7.41-7.30 (m, 0.5H, rotamer), 7.23 (d, J=11.6 Hz, 0.5H, rotamer), 4.83 (s, 1H), 4.62 (s, 1H), 4.18-4.01 (m, 1H), 1.41 (d, J=6.8 Hz, 2H, minor rotamer), 1.24 (d, J=6.6 Hz, 4H, major rotamer).

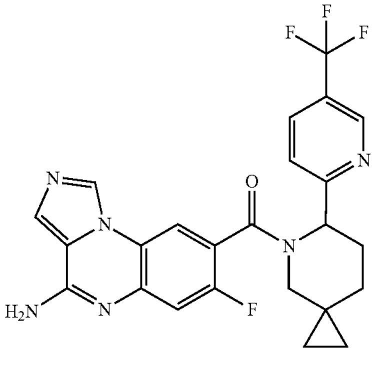 [SMILES: Nc1nc2cc(F)c(C(=O)N3CC4(CCC3c3ccc(C(F)(F)F)cn3)CC4)cc2n2cncc12]

Example Ff-149: (4-amino-7-fluoroimidazo[1,5-a]quinoxalin-8-yl)(6-(5-(trifluoromethyl)pyridin-2-yl)-5-azaspiro[2.5]octan-5-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 6-(5-(trifluoromethyl)pyridin-2-yl)-5-azaspiro[2.5]octane Eak-4. ES/MS: m/z=485.0 $[M+H]^+$. $^1H$ NMR (400 MHz, Methanol-d4) δ 9.32 (s, 1H), 8.99 (s, 1H), 8.36 (s, 0.5H, rotamer), 8.32 (s, 0.5H, rotamer), 8.27-8.15 (m, 0.5H, rotamer), 8.12 (d, J=8.7

Hz, 0.5H, rotamer), 7.74 (s, 1H), 7.63 (d, J=8.4 Hz, 1H), 7.46 (d, J=9.6 Hz, 1H), 6.20 (s, 1H), 5.12 (s, 1H), 3.83 (d, J=14.5 Hz, 1H), 2.73 (t, J=11.8 Hz, 1H), 2.28 (brs, 1H), 2.15-1.81 (m, 1H), 1.01 (d, J=13.9 Hz, 1H), 0.60-0.17 (m, 4H).

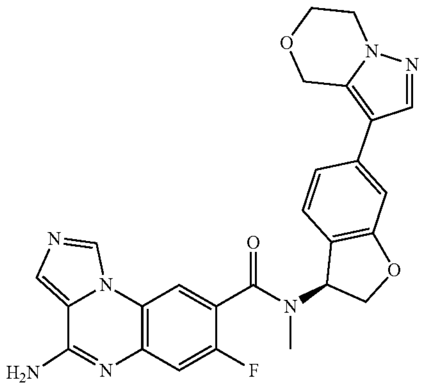 [SMILES: CN(C(=O)c1cc2c(cc1F)nc(N)c1cncn12)[C@@H]1COc2cc(-c3cnn4c3COCC4)ccc21]

Example Ff-150: (S)-4-amino-N-(6-(6,7-dihydro-4H-pyrazolo[5,1-c][1,4]oxazin-3-yl)-2,3-dihydrobenzofuran-3-yl)-7-fluoro-N-methylimidazo[1,5-a]quinoxaline-8-carboxamide. Prepared following the procedure reported for example Ff-145 starting with 4-((tert-butoxycarbonyl)amino)-7-fluoroimidazo[1,5-a]quinoxaline-8-carboxylic acid Af-1, (S)-(6-bromo-2,3-dihydrobenzofuran-3-yl)(methyl)-12-azane Eh-5 and 3-(4,4,5,5-tetramethyl-1,3,2-dioxaborolan-2-yl)-6,7-dihydro-4H-pyrazolo[5,1-c][1,4]oxazine. ES/MS: m/z=500.0 $[M+H]^+$. $^1$H NMR (400 MHz, Methanol-d4) δ 9.27 (s, 0.5H), 8.45 (d, J=5.9 Hz, 0.5H, rotamer), 8.37 (s, 1H), 7.81 (s, 0.5H, rotamer), 7.77 (s, 0.5H, rotamer), 7.56-7.38 (m, 1.5H, major rotamer), 7.35 (d, J=7.8 Hz, 0.5H, minor rotamer), 7.06-6.99 (m, 0.5H, rotamer), 6.98 (d, J=7.9 Hz, 0.5H, rotamer), 6.91 (s, 0.5H, rotamer), 6.84 (s, 0.5H, rotamer), 6.51 (d, J=5.5 Hz, 1H), 5.58 (s, 1H), 5.04 (d, J=14.2 Hz, 2H), 4.79 (0.5H, rotamer), 4.65 (dd, J=10.6, 3.3 Hz, 0.5H, rotamer), 4.19 (dd, J=11.6, 6.6 Hz, 4H), 2.88 (s, 1.5H, rotamer), 2.72 (s, 1.5H, rotamer).

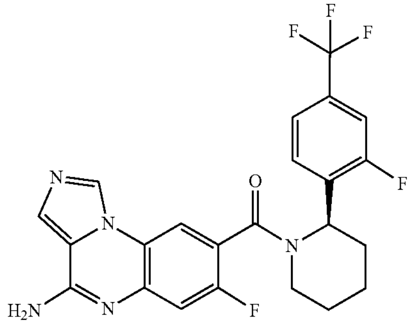 [SMILES: Nc1nc2cc(F)c(C(=O)N3CCCC[C@@H]3c3ccc(C(F)(F)F)cc3F)cc2n2cncc12]

Example Ff-151: (R)-(4-amino-7-fluoroimidazo[1,5-a]quinoxalin-8-yl)(2-(2-fluoro-4-(trifluoromethyl)phenyl)piperidin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 2-(2-fluoro-4-(trifluoromethyl)phenyl)piperidine Eak-1. Chiral separation by SFC (AD-H, EtOH, 60 mL/min) gave the title compound as peak 1. ES/MS: m/z=476.0 $[M+H]^+$. $^1$H NMR (400 MHz, Methanol-d4) δ 9.29 (s, 1H), 8.42 (brs, 0.2H, minor rotamer), 8.38 (s, 0.8H, major rotamer), 7.69 (t, J=7.9 Hz, 1H), 7.59 (d, J=8.1 Hz, 1H), 7.54 (d, J=10.7 Hz, 0.2H, minor rotamer), 7.46 (d, J=9.7 Hz, 0.8H, major rotamer), 7.37 (br s, 1H), 6.06 (s, 1H), 5.23 (s, 0.2H, minor rotamer), 4.79 (br s, 0.8H, major rotamer), 3.70 (d, J=13.3 Hz, 1H), 3.51 (td, J=8.1, 6.5, 3.3 Hz, 1H), 2.34 (s, 1H), 2.20-1.98 (m, 1H), 1.76 (s, 3H).

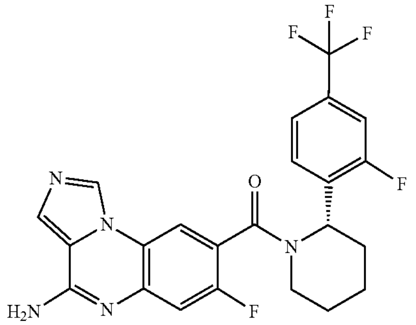 [SMILES: Nc1nc2cc(F)c(C(=O)N3CCCC[C@H]3c3ccc(C(F)(F)F)cc3F)cc2n2cncc12]

Example Ff-152: (S)-(4-amino-7-fluoroimidazo[1,5-a]quinoxalin-8-yl)(2-(2-fluoro-4-(trifluoromethyl)phenyl)piperidin-1-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 2-(2-fluoro-4-(trifluoromethyl)phenyl)piperidine Eak-1. Chiral separation by SFC (AD-H, EtOH, 60 mL/min) gave title compound as peak 2. ES/MS: m/z=476.0 $[M+H]^+$. $^1$H NMR (400 MHz, Methanol-d4) δ 9.31 (s, 1H), 8.44 (brs, 0.2H, minor rotamer), 8.40 (s, 0.8H, major rotamer), 7.69 (t, J=7.9 Hz, 1H), 7.54 (dd, J=35.8, 9.8 Hz, 2.5H, major rotamer), 7.38 (s, 0.5H, minor rotamer), 6.06 (s, 1H), 5.22 (s, 0.2H, minor rotamer), 4.79 (s, 0.8H, major rotamer), 3.69 (d, J=13.8 Hz, 1H), 3.61-3.46 (m, 1H), 2.36 (d, J=14.6 Hz, 1H), 2.21-2.01 (m, 1H), 1.98-1.58 (m, 3H).

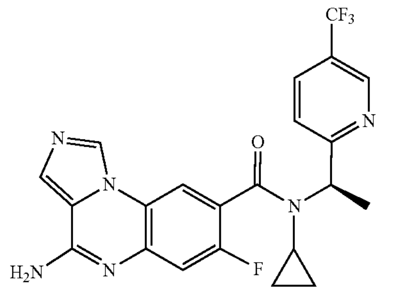 [SMILES: C[C@H](c1ccc(C(F)(F)F)cn1)N(C(=O)c1cc2c(cc1F)nc(N)c1cncn12)C1CC1]

Example Ff-153: (R)-4-amino-N-cyclopropyl-7-fluoro-N-(1-(5-(trifluoromethyl)pyridin-2-yl)ethyl)imidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and (R)—N-(1-(5-(trifluoromethyl)pyridin-2-yl)ethyl)cyclopropanamine Eah-2. ES/MS: m/z=459.0 $[M+H]^+$. $^1$H NMR (400 MHz, Methanol-d4) δ 9.28 (s, 1H), 8.89 (d, J=2.2 Hz, 1H), 8.43 (d, J=5.9 Hz, 1H), 8.38 (d, J=0.6 Hz, 1H), 8.18-7.98 (m, 1H), 7.70 (d, J=8.4 Hz, 1H), 7.46 (d, J=9.8 Hz, 1H), 5.58 (d, J=7.4 Hz, 1H), 3.01 (s, 1H), 1.96 (d, J=7.1 Hz, 3H), 0.70-0.49 (m, 4H).

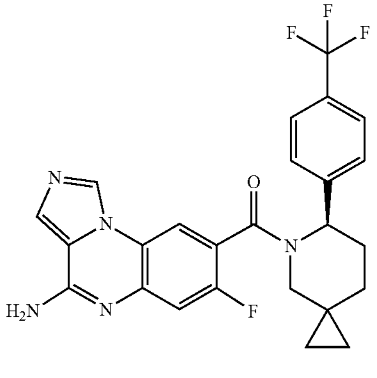 [SMILES: Nc1nc2cc(F)c(C(=O)N3CC4(CC[C@@H]3c3ccc(C(F)(F)F)cc3)CC4)cc2n2cncc12]

Example Ff-154: (R)-(4-amino-7-fluoroimidazo[1,5-a]quinoxalin-8-yl)(6-(4-(trifluoromethyl)phenyl)-5-azaspiro[2.5]octan-5-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 6-(4-(trifluoromethyl)phenyl)-5-azaspiro[2.5]octane Eak-3. Chiral separation by SFC (AD-H, MeOH, 60 mL/min) gave title compound as peak 1. ES/MS: m/z=484.0 $[M+H]^+$. $^1$H NMR (400 MHz, Methanol-d4) δ 9.33 (s, 0.6H, major rotamer), 9.09 (br s, 0.4H, minor rotamer), 8.51 (s, 0.5H, rotamer), 8.33 (s, 0.5H, rotamer), 7.79 (d, J=7.5 Hz, 2H), 7.72 (d, J=9.9 Hz, 3H), 7.56 (d, J=8.2 Hz, 0.5H, rotamer), 7.46 (d, J=9.8 Hz, 0.5H, rotamer), 6.24 (s, 0.6H, major rotamer), 5.11 (s, 0.5H, major rotamer), 3.94 (d, J=13.6 Hz, 0.4H, minor rotamer), 3.61 (d, J=13.9 Hz, 0.6H, major rotamer), 2.86-2.59 (m, 1.5H, major rotamer), 2.56 (s, 0.5H, minor rotamer), 2.31 (q, J=14.9, 13.7 Hz, 1H), 2.15-1.87 (m, 1H), 1.05 (d, J=13.1 Hz, 1H), 0.78-0.03 (m, 4H).

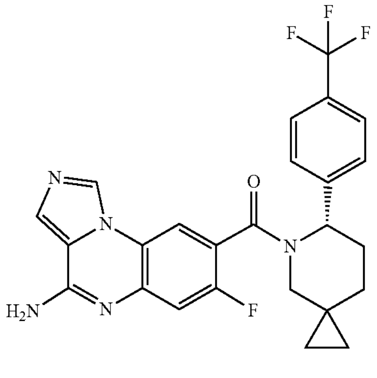

Example Ff-155: (S)-(4-amino-7-fluoroimidazo[1,5-a]quinoxalin-8-yl)(6-(4-(trifluoromethyl)phenyl)-5-azaspiro[2.5]octan-5-yl)methanone. Prepared following general procedure VI-F starting with starting with starting with 4-(tert-butoxycarbonylamino)-7-fluoro-imidazo[1,5-a]quinoxaline-8-carboxylic acid Af-1 and 6-(4-(trifluoromethyl)phenyl)-5-azaspiro[2.5]octane Eak-3. Chiral separation by SFC (AD-H, MeOH, 60 mL/min) gave title compound as peak 2. ES/MS: m/z=484.0 $[M+H]^+$. $^1$H NMR (400 MHz, Methanol-d4) δ 9.32 (s, 0.6H, major rotamer), 9.06 (br s, 0.4H, minor rotamer), 8.52 (d, J=9.8 Hz, 0.5H, rotamer), 8.32 (s, 0.5H, rotamer), 7.78 (s, 2H), 7.72 (d, J=9.4 Hz, 3H), 7.56 (d, J=8.1 Hz, 0.5H, rotamer), 7.45 (d, J=9.9 Hz, 0.5H, rotamer), 6.24 (s, 0.5H, rotamer), 5.11 (s, 0.5H, rotamer), 3.94 (d, J=13.4 Hz, 0.3H, minor rotamer), 3.61 (d, J=13.9 Hz, 0.7H, major rotamer), 2.85-2.62 (m, 1.5H, major rotamer), 2.55 (s, 0.5H, minor rotamer), 2.31 (q, J=15.6, 14.0 Hz, 1H), 2.05-1.98 (m, 1H), 1.05 (d, J=13.6 Hz, 1H), 0.89-0.05 (m, 4H).

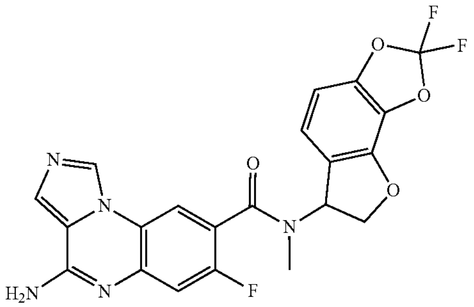 [SMILES: CN(C(=O)c1cc2c(cc1F)nc(N)c1cncn12)C1COc2c1ccc1c2OC(F)(F)O1]

Example Ff-156: 4-amino-N-(2,2-difluoro-6,7-dihydro-[1,3]dioxolo[4,5-g]benzofuran-6-yl)-7-fluoro-N-methylimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and 2,2-difluoro-N-methyl-6,7-dihydro-[1,3]dioxolo[4,5-g]benzofuran-6-amine Ean-1. ES/MS: m/z=458.0 $[M+H]^+$. 1H NMR (400 MHz, Methanol-d4) δ 9.35-9.13 (m, 1H), 8.44 (d, J=5.9 Hz, 0.5H, minor rotamer), 8.36 (dd, J=1.8, 0.7 Hz, 1.5H, major rotamer), 7.49 (d, J=11.0 Hz, 0.5H, rotamer), 7.46 (d, J=9.8 Hz, 0.5H, rotamer), 7.23 (dd, J=8.1, 0.9 Hz, 0.5H, rotamer), 7.14 (dd, J=8.2, 0.9 Hz, 0.5H, rotamer), 6.90 (d, J=8.1 Hz, 0.5H, rotamer), 6.86 (d, J=8.2 Hz, 0.5H, rotamer), 6.54 (dd, J=8.7, 3.4 Hz, 1H), 5.65 (t, J=6.3 Hz, 0.4H, minor rotamer), 4.98 (dd, J=10.7, 8.7 Hz, 0.6H, major rotamer), 4.85-4.77 (m, 1H), 2.88 (s, 1.4H, minor rotamer), 2.74 (d, J=1.2 Hz, 1.6H, major rotamer).

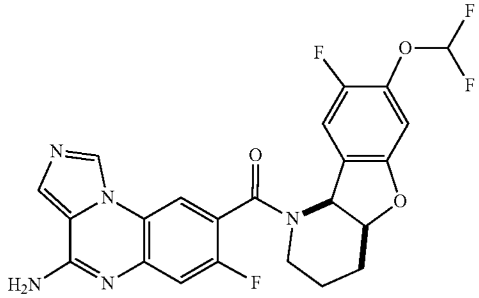

(±)

Example Ff-157: rac-(4-amino-7-fluoroimidazo[1,5-a]quinoxalin-8-yl)((4aS,9bS)-7-(difluoromethoxy)-8-fluoro-3,4,4a,9b-tetrahydrobenzofuro[3,2-b]pyridin-1(2H)-yl)methanone. Prepared following general procedure VI-F starting with starting with starting with 4-(tert-butoxycarbonylamino)-7-fluoro-imidazo[1,5-a]quinoxaline-8-carboxylic acid Af-1 and cis-7-(difluoromethoxy)-8-fluoro-1,2,3,4,4a,9b-hexahydrobenzofuro[3,2-b]pyridine Ev-6. ES/MS: m/z=488.0 $[M+H]^+$. $^1$H NMR (400 MHz, Methanol-d4) δ 9.28 (s, 1H), 8.54 (s, 0.3H, minor rotamer), 8.44 (d, J=5.9 Hz, 0.7H, major rotamer), 8.35 (s, 1H), 7.48 (dd, J=15.6, 9.7 Hz, 1H), 7.32 (s, 0.7H, major rotamer), 7.20 (s, 0.3H, minor rotamer), 6.87 (s, 1H), 6.84 (d, J=5.9 Hz, 0.7H, major rotamer), 6.77 (d, J=6.1 Hz, 0.3H, minor rotamer), 6.34 (d, J=8.7 Hz, 0.7H, major rotamer), 5.58 (s, 0.3H, minor rotamer), 5.16 (dt, J=8.5, 4.2 Hz, 1H), 5.08 (s, 0.5H, minor rotamer), 4.46 (s, 0.5H, minor rotamer), 3.58-3.38 (m, 1H), 3.04 (dd, J=14.5, 7.8 Hz, 0.7H, major rotamer), 2.90-2.78 (m, 0.3H, minor rotamer), 2.15-1.93 (m, 1H), 1.96-1.69 (m, 2H).

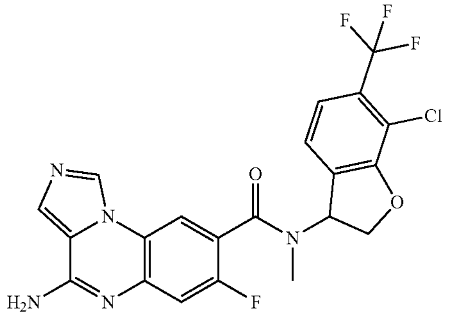 [SMILES: CN(C(=O)c1cc2c(cc1F)nc(N)c1cncn12)C1COc2c1ccc(C(F)(F)F)c2Cl]

Example Ff-158: 4-amino-N-(7-chloro-6-(trifluoromethyl)-2,3-dihydrobenzofuran-3-yl)-7-fluoro-N-methylimidazo[1,5-a]quinoxaline-8-carboxamide. Prepared following general procedure VI-F starting with starting with starting with 4-(tert-butoxycarbonylamino)-7-fluoro-imidazo[1,5-a]quinoxaline-8-carboxylic acid Af-1 and 7-chloro-N-methyl-6-(trifluoromethyl)-2,3-dihydrobenzofuran-3-amine Eam-1. ES/MS: m/z=480.0 [M+H]$^+$. 1H NMR (400 MHz, Methanol-d4) δ 9.24 (s, 1H), 8.44 (d, J=5.9 Hz, 1H), 8.36 (s, 1H), 7.56-7.37 (m, 3H), 6.75-6.50 (m, 0.5H, minor rotamer), 5.80 (t, J=6.9 Hz, 0.5H, minor rotamer), 5.00 (dd, J=10.7, 9.1 Hz, 1.5H, major rotamer), 4.84 (d, J=6.7 Hz, 0.5H, minor rotamer), 2.91 (s, 1H, minor rotamer), 2.79 (s, 2H, major rotamer).

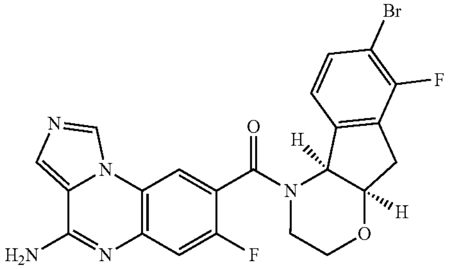

Example Ff-159: (4-amino-7-fluoroimidazo[1,5-a]quinoxalin-8-yl)((4aS,9aR)-7-bromo-8-fluoro-2,3,9,9a-tetrahydroindeno[2,1-b][1,4]oxazin-4(4aH)-yl)methanone Prepared using general procedure VI-F starting with 4-((tert-butoxycarbonyl)amino)-7-fluoroimidazo[1,5-a]quinoxaline-8-carboxylic acid Af-1 and (4aS,9aR)-7-bromo-8-fluoro-2,3,4,4a,9,9a-hexahydroindeno[2,1-b][1,4]oxazine Et-4. ES/MS: m/z=500.2 [M+H]$^+$. $^1$H NMR (400 MHz, DMSO-d6) δ 9.38 (s, 0.66H, major rotamer), 9.30 (s, 0.34H, minor rotamer), 9.20 (br, 2H), 8.64 (br, 0.34H, minor rotamer), 8.57 (d, J=6.2 Hz, 0.66H, major rotamer), 8.29 (s, 0.66H, major rotamer), 8.25 (s, 0.34H, minor rotamer), 7.66 (t, J=7.1 Hz, 0.66H, major rotamer), 7.61 (t, J=7.1 Hz, 0.34H, minor rotamer), 7.46 (d, J=10.2 Hz, 0.66H, major rotamer), 7.41 (d, J=10.2 Hz, 0.34H, minor rotamer), 7.28 (br, 0.34H, minor rotamer), 7.01 (br, 0.66H, major rotamer), 5.91 (s, 0.66H, major rotamer), 5.00 (s, 0.34H, minor rotamer), 4.44 (t, J=4.1 Hz, 0.66H, major rotamer), 4.36 (m, 0.34H, minor rotamer), 4.34-4.29 (m, 0.34H, minor rotamer), 3.86-3.78 (m, 0.34H, minor rotamer), 3.69-3.61 (m, 0.66H, major rotamer), 3.58-3.45 (m, 1H), 3.37-3.31 (m, 0.66H, major rotamer), 3.30-3.24 (m, 0.66H, major rotamer), 3.12-2.99 (m, 1H), 2.99-2.91 (m, 0.66H, major rotamer), 2.86-2.78 (m, 0.34H, minor rotamer), 2.84-2.75 (m, 0.34H, minor rotamer).

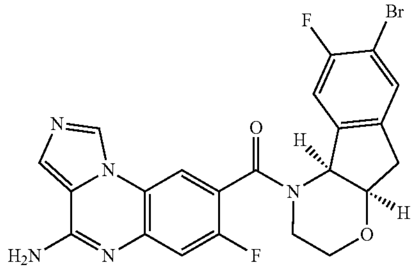

Example Ff-160: (4-amino-7-fluoroimidazo[1,5-a]quinoxalin-8-yl)((4aS,9aR)-7-bromo-6-fluoro-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-7-bromo-6-fluoro-2,3,4,4a,9,9a-hexahydroindeno[2,1-b][1,4]oxazine Et-3. ES/MS: m/z=500.2 [M+H]$^+$. $^1$H NMR (400 MHz, DMSO-d6) δ 9.36 (s, 0.66H, major rotamer), 9.28 (s, 0.34H, minor rotamer), 8.99 (br, 2H), 8.81-8.75 (m, 0.34H, minor rotamer), 8.58 (d, J=6.2 Hz, 0.66H, major rotamer), 8.28 (s, 0.66H, major rotamer), 8.25 (s, 0.34H, minor rotamer), 7.74-7.67 (m, 0.66H, major rotamer), 7.63-7.57 (m, 0.34H, major rotamer), 7.49-7.43 (m, 0.66H, major rotamer), 7.42-7.38 (m, 0.34H, minor rotamer), 7.33-7.28 (m, 0.34H, minor rotamer), 7.12 (br, 0.66H, major rotamer), 5.85 (s, 0.66H, major rotamer), 4.93 (s, 0.34H, minor rotamer), 4.44-4.40 (m, 0.66H, major rotamer), 4.37 (m, 0.34H, minor rotamer), 4.34-4.29 (m, 0.34H, minor rotamer), 3.84-3.78 (m, 0.34H, minor rotamer), 3.69-3.61 (m, 0.66H, major rotamer), 3.58-3.45 (m, 1H), 3.35-3.28 (m, 0.66H, major rotamer), 3.25-3.17 (m, 0.66H, major rotamer), 3.12-3.02 (m, 1H), 3.00-2.91 (m, 0.33H, minor rotamer), 2.86-2.75 (m, 1H).

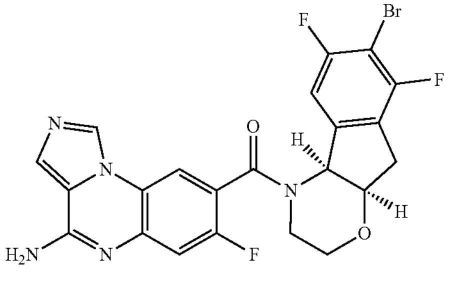 [SMILES: Nc1nc2cc(F)c(C(=O)N3CCO[C@@H]4Cc5c(cc(F)c(Br)c5F)[C@@H]43)cc2n2cncc12]

Example Ff-161: (4-amino-7-fluoroimidazo[1,5-a]quinoxalin-8-yl)((4aS,9aR)-7-bromo-6,8-difluoro-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-7-bromo-6,8-difluoro-2,3,4,4a,9,9a-hexahydroindeno[2,1-b][1,4]oxazine Et-5. ES/MS: m/z=518.2 [M+H]$^+$. $^1$H NMR (400 MHz, MeOD-$d_4$) δ 9.30 (s, 0.7H, major rotamer), 9.24 (s, 0.3H, minor rotamer), 8.63-8.47 (m, 1H), 8.37 (s, 0.7H, major rotamer), 8.34 (m, 0.3H, minor rotamer) 7.51 (d, J=9.8 Hz, 0.7H, major rotamer), 7.47 (d, J=9.8 Hz, 0.3H, minor rotamer), 7.18-6.94 (m, 1H), 5.99 (s, 0.7H, major rotamer), 5.08 (s, 0.3H, minor rotamer), 4.55 (t, J=4.1 Hz, 0.7H, major rotamer), 4.51-4.46 (m, 0.3H, minor rotamer), 3.93-3.87 (m, 0.3H, minor rotamer), 3.78-3.67 (m, 1H), 3.67-3.57 (m, 0.7H, major rotamer), 3.46 (d, J=13.4 Hz, 0.7H, major rotamer), 3.36-3.34 (m, 0.3H, minor rotamer), 3.32-3.23 (m, 1H), 3.22-3.18 (m, 0.7H, major rotamer), 3.07 (d, J=16.6 Hz, 0.7H, major rotamer), 3.03-2.98 (m, 0.3H, minor rotamer), 2.97-2.95 (m, 0.3H, minor rotamer).

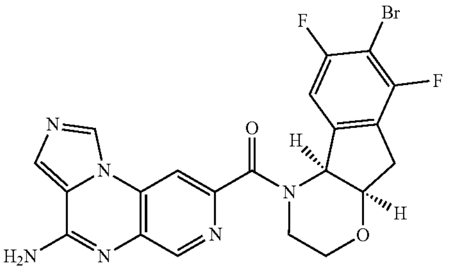 [SMILES: Nc1nc2cnc(C(=O)N3CCO[C@@H]4Cc5c(cc(F)c(Br)c5F)[C@@H]43)cc2n2cncc12]

Example Ff-162: (4-aminoimidazo[1,5-a]pyrido[3,4-e]pyrazin-8-yl)((4aS,9aR)-7-bromo-6,8-difluoro-2,3,9,9a-tetrahydroindeno[2,1-b][1,4]oxazin-4(4aH)-yl)methanone. Prepared using general procedure VI-F starting with 4-((tert-butoxycarbonyl)amino)imidazo[1,5-a]pyrido[3,4-e]pyrazine-8-carboxylic acid Af-6 and (4aS,9aR)-7-bromo-6,8-difluoro-2,3,4,4a,9,9a-hexahydroindeno[2,1-b][1,4]oxazine Et-5. ES/MS: m/z=501.2 $[M+H]^+$. $^1H$ NMR (400 MHz, MeOD-$d_4$) δ 9.36 (s, 0.5H, rotamer), 9.35 (s, 0.5H, rotamer), 8.86 (s, 0.5H, rotamer), 8.72 (s, 0.5H, rotamer), 8.66 (s, 0.5H, rotamer), 8.63 (s, 0.5H, rotamer), 8.33-8.26 (m, 1H), 7.31 (d, J=7.6 Hz, 0.5H, rotamer), 7.07 (d, J=7.4 Hz, 0.5H, rotamer), 5.96 (d, J=3.9 Hz, 0.5H, rotamer), 5.56 (d, J=3.9 Hz, 0.5H, rotamer), 4.60-4.50 (m, 1H), 4.45-4.41 (m, 0.5H, rotamer), 3.93-3.84 (m, 1H), 3.76-3.69 (m, 1H), 3.69-3.64 (m, 0.5H, rotamer), 3.29-3.20 (m, 1H), 3.07 (d, J=16.6 Hz, 0.5H, rotamer), 3.03-2.96 (m, 1H), 2.97-2.87 (m, 0.5H, rotamer).

Examples Ff-163 and Ff-164: Prepared following general procedure VI-F starting with 4-((tert-butoxycarbonyl)amino)-7-fluoroimidazo[1,5-a]quinoxaline-8-carboxylic acid Af-1 and (4aS,9aR)-7-bromo-8-fluoro-2-methyl-2,3,4,4a,9,9a-hexahydroindeno[2,1-b][1,4]oxazine Eas-1.

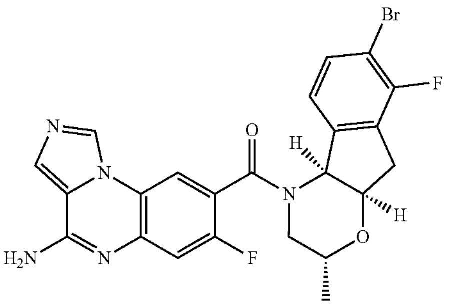 [SMILES: C[C@@H]1CN(C(=O)c2cc3c(cc2F)nc(N)c2cncn23)[C@H]2c3ccc(Br)c(F)c3C[C@H]2O1]

Example Ff-163: (4-amino-7-fluoroimidazo[1,5-a]quinoxalin-8-yl)((2R,4aS,9aR)-7-bromo-8-fluoro-2-methyl-2,3,9,9a-tetrahydroindeno[2,1-b][1,4]oxazin-4(4aH)-yl)methanone. Peak 1: ES/MS: m/z=514.2 $[M+H]^+$. $^1H$ NMR (400 MHz, DMSO-d6) δ 9.40 (s, 0.6H, major rotamer), 9.31 (s, 0.4H, minor rotamer), 8.99 (br, 2H), 8.65 (br, 0.4H, minor rotamer), 8.55 (d, J=6.1 Hz, 0.6H, major rotamer), 8.29 (s, 0.6H, major rotamer), 8.26 (s, 0.4H, minor rotamer), 7.71-7.59 (m, 1H), 7.47-4.41 (m, 1H), 7.29 (br, 0.4H, minor rotamer), 7.05 (br, 0.6H, major rotamer), 5.95 (s, 0.6H, major rotamer), 4.71 (s, 0.4H, minor rotamer), 4.70 (t, J=4.3 Hz, 0.6H, major rotamer), 4.61 (t, J=4.3 Hz, 0.4H, minor rotamer), 4.19 (d, J=13.3 Hz, 0.6H, major rotamer), 3.99 (br, 0.4H, minor rotamer), 3.80 (d, J=7.1 Hz, 0.6H, major rotamer), 3.33-3.19 (m, 1H), 3.11 (d, J=13.4 Hz, 0.6H, major rotamer), 3.07-2.99 (m, 0.4H, minor rotamer), 2.94-2.87 (m, 1H), 2.79-2.74 (m, 0.4H, minor rotamer) 1.33 (d, J=6.4 Hz, 1.2H, minor rotamer), 1.20 (d, J=6.7 Hz, 1.8H, major rotamer).

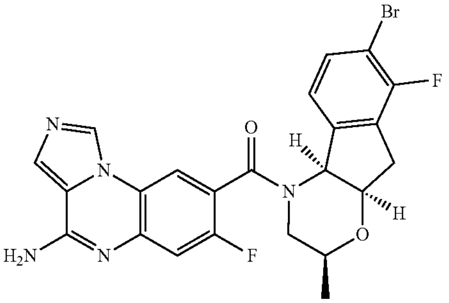 [SMILES: C[C@H]1CN(C(=O)c2cc3c(cc2F)nc(N)c2cncn23)[C@H]2c3ccc(Br)c(F)c3C[C@H]2O1]

Example Ff-164: (4-amino-7-fluoroimidazo[1,5-a]quinoxalin-8-yl)((2S,4aS,9aR)-7-bromo-8-fluoro-2-methyl-2,3,9,9a-tetrahydroindeno[2,1-b][1,4]oxazin-4(4aH)-yl)methanone. Peak 2: ES/MS: m/z=514.2 $[M+H]^+$. $^1H$ NMR (400 MHz, DMSO-d6) δ 9.39 (s, 0.66H, major rotamer), 9.30 (s, 0.34H, minor rotamer), 9.10 (br, 2H), 8.65 (br, 0.34H, minor rotamer), 8.57 (d, J=6.1 Hz, 0.66H, major rotamer), 8.31 (s, 0.66H, major rotamer), 8.27 (s, 0.34H, minor rotamer), 7.65 (t, J=7.1 Hz, 0.66H, major rotamer), 7.60 (t, J=7.1 Hz, 0.34H, minor rotamer), 7.47 (d, J=10.2 Hz, 0.66H, major rotamer), 7.41 (d, J=10.2 Hz, 0.34H, minor rotamer), 7.26 (br, 0.34H, minor rotamer), 6.96 (br, 0.66H, major rotamer), 5.89 (s, 0.66H, major rotamer), 4.97 (s, 0.34H, minor rotamer), 4.51 (t, J=4.1 Hz, 0.66H, major rotamer), 4.44 (t, J=4.1 Hz, 0.34H, minor rotamer), 4.37 (d, J=13.3 Hz, 0.34H, minor rotamer), 3.71-3.53 (m, 1H), 3.34 (d, J=14.8 Hz, 0.66H, major rotamer), 3.32-3.24 (m, 0.66H major rotamer), 3.10-3.00 (m, 0.34H, minor rotamer), 2.95 (d, J=16.5 Hz, 0.66H, major rotamer), 2.83-2.81 (m, 0.34H, minor rotamer), 2.76-2.65 (m, 0.66H, major rotamer), 2.46-2.37 (m, 0.34H, minor rotamer) 1.08 (d, J=6.2 Hz, 1.02H, minor rotamer), 0.91 (d, J=6.2 Hz, 1.98H, major rotamer).

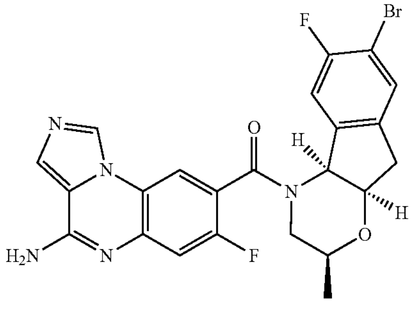 [SMILES: C[C@H]1CN(C(=O)c2cc3c(cc2F)nc(N)c2cncn23)[C@H]2c3cc(F)c(Br)cc3C[C@H]2O1]

Example Ff-165: (4-amino-7-fluoroimidazo[1,5-a]quinoxalin-8-yl)((2S,4aS,9aR)-7-bromo-6-fluoro-2-methyl-2,3,9,9a-tetrahydroindeno[2,1-b][1,4]oxazin-4(4aH)-yl) methanone Prepared using general procedure VI-F starting with 4-((tert-butoxycarbonyl)amino)-7-fluoroimidazo[1,5-a]quinoxaline-8-carboxylic acid Af-1 and (2S,4aS,9aR)-7-bromo-6-fluoro-2-methyl-2,3,4,4a,9,9a-hexahydroindeno[2,1-b][1,4]oxazine Et-6. ES/MS: m/z=514.2 $[M+H]^+$. $^1H$ NMR (400 MHz, DMSO-d6) δ 9.37 (s, 0.6H, major rotamer), 9.28 (s, 0.4H, minor rotamer), 8.94 (br, 2H), 8.73 (br, 0.4H, minor rotamer), 8.57 (d, J=6.1 Hz, 0.6H, major rotamer), 8.28 (s, 0.6H, major rotamer), 8.24 (s, 0.4H, minor rotamer), 7.69 (d, J=6.4 Hz, 0.6H, major rotamer), 7.58 (d, J=6.3 Hz, 0.4H, minor rotamer), 7.46 (d, J=10.3 Hz, 0.6H, major rotamer), 7.40 (d, J=10.1 Hz, 0.4H, minor rotamer), 7.24 (br, 0.4H, minor rotamer), 6.97 (br, 0.6H, major rotamer), 5.84 (s, 0.6H, major rotamer), 4.90 (s, 0.4H, minor rotamer), 4.49 (t, J=4.3 Hz, 0.6H, major rotamer), 4.43-4.34 (m, 0.8H), 3.65-3.53 (m, 1H), 3.34 (d, J=14.8 Hz, 0.6H, major rotamer), 3.32-3.24 (m, 0.6H major rotamer), 3.01-2.92 (m, 0.4H, minor rotamer), 2.85 (d, J=16.5 Hz, 0.6H, major rotamer), 2.78-2.65 (m, 1H, major rotamer), 2.46-2.37 (m, 0.4H, minor rotamer) 1.07 (d, J=6.2 Hz, 1.02H, minor rotamer), 0.89 (d, J=6.2 Hz, 1.98H, major rotamer).

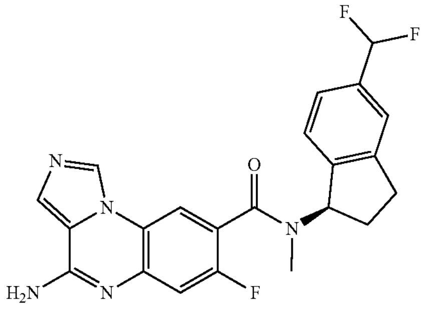

Example Ff-166: (R)-4-amino-N-(5-(difluoromethyl)-2,3-dihydro-1H-inden-1-yl)-7-fluoro-N-methylimidazo[1,5-a]quinoxaline-8-carboxamide. Prepared using general procedure VI-F starting with 4-((tert-butoxycarbonyl)amino)-7-fluoroimidazo[1,5-a]quinoxaline-8-carboxylic acid Af-1 and (R)-5-(difluoromethyl)-2,3-dihydro-1H-inden-1-amine Ebb-2 ES/MS: m/z=426.1 $[M+H]^+$. $^1H$ NMR (400 MHz, DMSO-d6) δ 9.40 (s, 0.4H, minor rotamer), 9.37 (s, 0.6, major rotamer), 9.18 (br, 2H), 8.70-8.48 (m, 1H), 8.37-8.24 (m, 1H), 7.57-7.23 (m, 4H), 7.06 (t, J=55.9 Hz, 0.4H, minor rotamer), 7.01 (t, J=55.9 Hz, 0.6H, major rotamer), 6.29 (t, J=8.3 Hz, 0.4H, minor rotamer), 5.23 (t, J=8.0 Hz, 0.6H, major rotamer), 3.16-2.80 (m, 2H), 2.76 (s, 1.8H, major rotamer), 2.60 (s, 1.2H, minor rotamer), 2.45-2.05 (m, 2H).

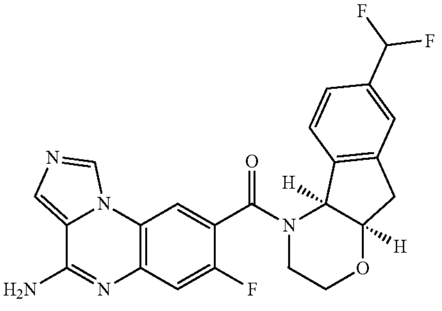 [SMILES: Nc1nc2cc(F)c(C(=O)N3CCO[C@@H]4Cc5cc(C(F)F)ccc5[C@@H]43)cc2n2cncc12]

Example Ff-167: (4-amino-7-fluoroimidazo[1,5-a]quinoxalin-8-yl)((4aS,9aR)-7-(difluoromethyl)-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-7-(difluoromethyl)-2,3,4,4a,9,9a-hexahydroindeno[2,1-b][1,4]oxazine Eau-1. ES/MS: m/z=454.2 $[M+H]^+$. $^1H$ NMR (400 MHz, DMSO-d6) δ 9.37 (s, 0.7H, major rotamer), 9.30 (s, 0.3H, minor rotamer), 8.77 (br, 2H), 8.65 (br, 0.3H, minor rotamer), 8.56 (d, J=6.3 Hz, 0.7H, major rotamer), 8.24 (s, 0.7H, major rotamer), 8.20 (s, 0.3H, minor rotamer), 7.70-7.21 (m, 4H), 7.05 (t, J=56.0 Hz, 0.7H, minor rotamer), 6.99 (t, J=55.9 Hz, 0.3H, major rotamer), 5.92 (s, 0.7H, major rotamer), 4.99 (s, 0.3H, minor rotamer), 4.43 (t, J=4.0 Hz, 0.7H, major rotamer), 4.38 (m, 0.3H, minor rotamer), 4.34-4.29 (m, 0.3H, minor rotamer), 3.83-3.76 (m, 0.3H, minor rotamer), 3.66-3.60 (m, 0.7H, major rotamer), 3.58-3.45 (m, 1H), 3.35-3.28 (m, 0.7H, major rotamer), 3.27-3.23 (m, 0.3H, major rotamer), 3.12-3.02 (m, 1H), 3.00-2.91 (m, 0.7H, minor rotamer), 2.86-2.75 (m, 1H).

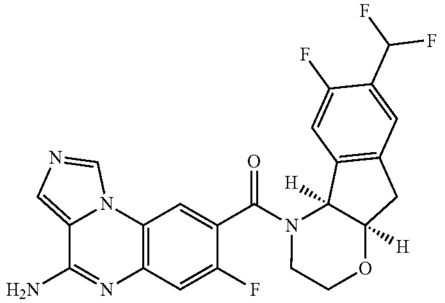 [SMILES: Nc1nc2cc(F)c(C(=O)N3CCO[C@@H]4Cc5cc(C(F)F)c(F)cc5[C@@H]43)cc2n2cncc12]

Example Ff-168: (4-amino-7-fluoroimidazo[1,5-a]quinoxalin-8-yl)((4aS,9aR)-7-(difluoromethyl)-6-fluoro-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-7-(difluoromethyl)-6-fluoro-2,3,4,4a,9,9a-hexahydroindeno[2,1-b][1,4]oxazine Eau-2. ES/MS: m/z=472.2 $[M+H]^+$. $^1H$ NMR (400 MHz, DMSO-d6) δ 9.34 (s, 0.7H, major rotamer), 9.26 (s, 0.3H, minor rotamer), 8.69 (br, 2H), 8.60-8.51 (m, 1H), 8.22 (s, 0.7H, major rotamer), 8.18 (s, 0.3H, minor rotamer), 7.64-6.94 (m, 4H), 5.93 (s, 0.7H, major rotamer), 5.02 (s, 0.3H, minor rotamer), 4.44 (t, J=4.0 Hz, 0.7H, major rotamer), 4.38 (m, 0.3H, minor rotamer), 4.34-4.29 (m, 0.3H, minor rotamer), 3.83-3.76 (m, 0.3H, minor rotamer), 3.66-3.60 (m, 0.7H, major rotamer), 3.58-3.45 (m, 1H), 3.35-3.28 (m, 0.7H, major rotamer), 3.27-3.23 (m, 0.7H, major rotamer), 3.12-2.99 (m, 1H), 2.93-2.87 (m, 0.3H, minor rotamer), 2.83-2.75 (m, 1H).

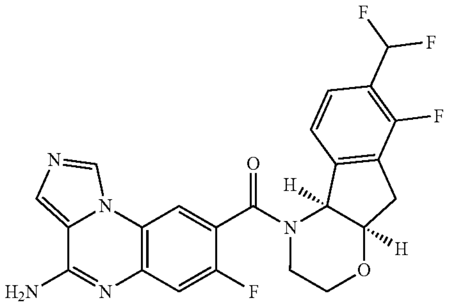 [SMILES: Nc1nc2cc(F)c(C(=O)N3CCO[C@@H]4Cc5c(ccc(C(F)F)c5F)[C@@H]43)cc2n2cncc12]

Example Ff-169: (4-amino-7-fluoroimidazo[1,5-a]quinoxalin-8-yl)((4aS,9aR)-7-(difluoromethyl)-8-fluoro-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-7-(difluoromethyl)-8-fluoro-2,3,4,4a,9,9a-hexahydroindeno[2,1-b][1,4]oxazine Eau-3. ES/MS: m/z=472.2 $[M+H]^+$. $^1H$ NMR (400 MHz, DMSO-d6) δ 9.38 (s, 0.7H, major rotamer), 9.31 (s, 0.3H, minor rotamer), 9.02 (br, 2H), 8.72-8.62 (m, 0.3H, minor rotamer), 8.58 (d, J=6.2 Hz, 0.7H, major rotamer), 8.29 (s, 0.7H, major rotamer), 8.25 (s, 0.3H, minor rotamer), 7.61 (t, J=7.0 Hz, 0.7H, major rotamer), 7.55 (t, J=7.0 Hz, 0.3H, minor rotamer), 7.46 (d, J=10.3 Hz, 0.7H, major rotamer), 7.40 (d, J=10.1 Hz, 0.3H, minor rotamer), 7.37-7.01 (m, 2H), 5.98 (s, 0.7H, major rotamer), 5.06 (s, 0.3H, minor rotamer), 4.48 (t, J=4.0 Hz, 0.7H, major rotamer), 4.40 (m, 0.3H, minor rotamer), 4.38-4.33 (m, 0.3H, minor rotamer), 3.85-3.80 (m, 0.3H, minor rotamer), 3.69-3.62 (m, 0.7H, major rotamer), 3.58-3.45 (m, 1H), 3.35-3.28 (m, 0.7H, major rotamer), 3.27-3.23 (m, 0.7H, major rotamer), 3.11-2.99 (m, 1H), 2.96 (d, J=16.5 Hz, 0.7H, minor rotamer), 2.83-2.80 (m, 0.3H, minor rotamer), 2.80-2.74 (m, 0.3H, minor rotamer).

Examples Ff-170 and Ff-171: Prepared following general procedure VI-F starting with 4-((tert-butoxycarbonyl)amino)-7-fluoroimidazo[1,5-a]quinoxaline-8-carboxylic acid Af-1 and (4aS,9aR)-7-(difluoromethyl)-8-fluoro-2-methyl-2,3,4,4a,9,9a-hexahydroindeno[2,1-b][1,4]oxazine Eau-4.

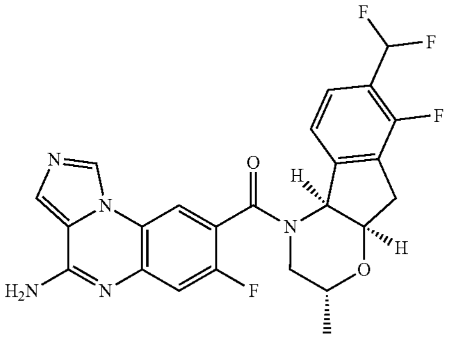 [SMILES: C[C@@H]1CN(C(=O)c2cc3c(cc2F)nc(N)c2cncn23)[C@H]2c3ccc(C(F)F)c(F)c3C[C@H]2O1]

Example Ff-170: (4-amino-7-fluoroimidazo[1,5-a]quinoxalin-8-yl)((2R,4aS,9aR)-7-(difluoromethyl)-8-fluoro-2-methyl-2,3,9,9a-tetrahydroindeno[2,1-b][1,4]oxazin-4(4aH)-yl)methanone. Peak one: ES/MS: m/z=486.2 $[M+H]^+$. $^1H$ NMR (400 MHz, MeOD-$d_4$) δ 9.36 (s, 0.6H, major rotamer), 9.27 (br, 0.4H, minor rotamer), 8.58 (d, J=6.1 Hz, 0.4H, minor rotamer), 8.53 (d, J=6.1 Hz, 0.6H, major rotamer), 8.39 (s, 0.6H, major rotamer), 8.35 (s, 0.4H, minor rotamer), 7.65-7.45 (m, 2H), 7.40-7.22 (m, 1H), 7.02 (t, J=56.0 Hz, 0.6H, major rotamer), 6.96 (t, J=55.9 Hz, 0.4H, minor rotamer), 6.15 (s, 0.6H, major rotamer), 5.10 (s, 0.4H, minor rotamer), 4.79 (t, J=4.3 Hz, 0.6H, major rotamer), 4.63 (t, J=4.3 Hz, 0.4H, minor rotamer), 4.35 (d, J=13.3 Hz, 0.4H, major rotamer), 4.06 (br, 0.4H, minor rotamer), 3.88 (br, 0.6H, major rotamer), 3.44-3.35 (m, 0.6H, minor rotamer), 3.31-3.20 (m. 1H), 3.16-3.12 (m, 0.4H, minor rotamer), 3.06-3.00 (m, 0.6H, major rotamer), 2.99-2.80 (m, 1H), 1.46 (d, J=6.4 Hz, 1.2H, minor rotamer), 1.34 (d, J=6.7 Hz, 1.8H, major rotamer).

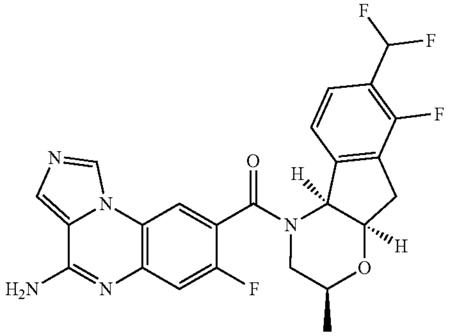 [SMILES: C[C@H]1CN(C(=O)c2cc3c(cc2F)nc(N)c2cncn23)[C@H]2c3ccc(C(F)F)c(F)c3C[C@H]2O1]

Example Ff-171: (4-amino-7-fluoroimidazo[1,5-a]quinoxalin-8-yl)((2S,4aS,9aR)-7-(difluoromethyl)-8-fluoro-2-methyl-2,3,9,9a-tetrahydroindeno[2,1-b][1,4]oxazin-4(4aH)-yl)methanone. Peak 2: ES/MS: m/z=486.2 $[M+H]^+$. $^1H$ NMR (400 MHz, MeOD-$d_4$) δ 9.31 (s, 0.7H, major rotamer), 9.26 (s, 0.3H, minor rotamer), 8.61-8.50 (m, 1H), 8.38 (s, 0.7H, major rotamer), 8.34 (s, 0.3H, minor rotamer), 7.63-7.54 (m, 1H), 7.52 (d, J=10.2 Hz, 0.7H, major rotamer), 7.46 (d, J=10.2 Hz, 0.3H, minor rotamer), 7.36-7.20 (m, 1H), 7.02 (t, J=56.0 Hz, 0.7H, major rotamer), 6.95 (t, J=55.9 Hz, 0.3H, minor rotamer), 6.04 (s, 0.7H, major rotamer), 5.09 (s, 0.3H, minor rotamer), 4.63 (t, J=4.1 Hz, 0.7H, major rotamer), 4.57 (t, J=4.1 Hz, 0.3H, minor rotamer), 4.50 (d, J=13.3 Hz, 0.3H, minor rotamer), 3.81-3.67 (m, 1H), 3.42 (d, J=14.8 Hz, 0.7H, major rotamer), 3.32-3.24 (m, 0.7H major rotamer), 3.12 (d, J=16.5 Hz, 0.7H, major rotamer), 3.10-3.00 (m, 0.3H, minor rotamer), 2.92-2.79 (m, 1H), 2.61-2.52 (m, 0.3H, minor rotamer) 1.16 (d, J=6.2 Hz, 0.9H, minor rotamer), 0.99 (d, J=6.2 Hz, 2.1H, major rotamer).

Examples Ff-172 and Ff-173: Prepared following general procedure VI-F starting with 4-((tert-butoxycarbonyl)amino)-7-fluoroimidazo[1,5-a]quinoxaline-8-carboxylic acid Af-1 and (4aS,9aR)-7-(difluoromethyl)-6-fluoro-2-methyl-2,3,4,4a,9,9a-hexahydroindeno[2,1-b][1,4]oxazine Eau-5.

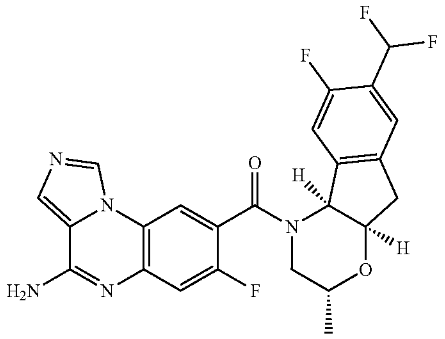 [SMILES: C[C@@H]1CN(C(=O)c2cc3c(cc2F)nc(N)c2cncn23)[C@H]2c3cc(F)c(C(F)F)cc3C[C@H]2O1]

Example Ff-172: (4-amino-7-fluoroimidazo[1,5-a]quinoxalin-8-yl)((2R,4aS,9aR)-7-(difluoromethyl)-6-fluoro-2-methyl-2,3,9,9a-tetrahydroindeno[2,1-b][1,4]oxazin-4(4aH)-yl)methanone. Peak 1: ES/MS: m/z=486.2 $[M+H]^+$. $^1H$ NMR (400 MHz, MeOD-$d_4$) δ 9.43-9.20 (m, 1H), 8.64-8.50 (m, 1H), 8.39 (s, 0.6H, major rotamer), 8.36 (s, 0.4H, minor rotamer), 7.61-7.42 (m, 2H), 7.39-7.17 (m, 1H), 7.02 (t, J=56.0 Hz, 0.6H, major rotamer), 6.96 (t, J=55.9 Hz, 0.4H, minor rotamer), 6.08 (s, 0.6H, major rotamer), 5.06 (s, 0.4H, minor rotamer), 4.83 (t, J=4.3 Hz, 0.6H, major rotamer), 4.76 (t, J=4.3 Hz, 0.4H, minor rotamer), 4.36 (d, J=13.3 Hz, 0.4H, minor rotamer), 4.05 (br, 0.4H, minor rotamer), 3.87 (br, 0.6H, major rotamer), 3.44-3.35 (m, 0.6H, minor rotamer), 3.31-3.20 (m. 1H), 3.17-3.10 (m, 0.4H, minor rotamer), 3.06-3.00 (m, 0.6H, major rotamer), 2.99-2.80 (m, 1H), 1.45 (d, J=6.4 Hz, 1.2H, minor rotamer), 1.33 (d, J=6.7 Hz, 1.8H, major rotamer).

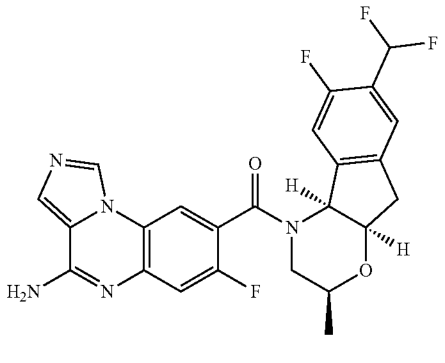 [SMILES: C[C@H]1CN(C(=O)c2cc3c(cc2F)nc(N)c2cncn23)[C@H]2c3cc(F)c(C(F)F)cc3C[C@H]2O1]

Example Ff-173: (4-amino-7-fluoroimidazo[1,5-a]quinoxalin-8-yl)((2S,4aS,9aR)-7-(difluoromethyl)-6-fluoro-2-methyl-2,3,9,9a-tetrahydroindeno[2,1-b][1,4]oxazin-4(4aH)-yl)methanone. Peak 2: ES/MS: m/z=486.2 $[M+H]^+$. $^1H$ NMR (400 MHz, MeOD-$d_4$) δ 9.31 (s, 0.7H, major rotamer), 9.26 (s, 0.3H, minor rotamer), 8.65-8.50 (m, 1H), 8.39 (s, 0.7H, major rotamer), 8.36 (s, 0.3H, minor rotamer), 7.63-7.43 (m, 2H), 7.23 (br, 1H), 7.00 (t, J=56.0 Hz, 0.7H, major rotamer), 6.95 (t, J=55.9 Hz, 0.3H, minor rotamer), 6.00 (s, 0.7H, major rotamer), 5.05 (s, 0.3H, minor rotamer), 4.60 (t, J=4.1 Hz, 0.7H, major rotamer), 4.54 (t, J=4.1 Hz, 0.3H, minor rotamer), 4.51 (d, J=13.3 Hz, 0.3H, minor rotamer), 3.80-3.66 (m, 1H), 3.42 (d, J=14.8 Hz, 0.7H, major rotamer), 3.32-3.22 (m, 0.7H major rotamer), 3.03 (d, J=16.5 Hz, 0.7H, major rotamer), 3.02-2.95 (m, 0.3H, minor rotamer), 2.92-2.79 (m, 1H), 2.61-2.52 (m, 0.3H, minor rotamer), 1.16 (d, J=6.2 Hz, 0.9H, minor rotamer), 0.99 (d, J=6.2 Hz, 2.1H, major rotamer).

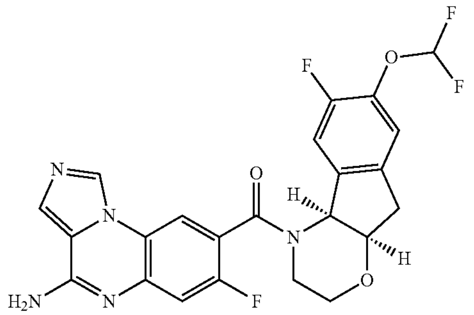 [SMILES: Nc1nc2cc(F)c(C(=O)N3CCO[C@@H]4Cc5cc(OC(F)F)c(F)cc5[C@@H]43)cc2n2cncc12]

Example Ff-174: (4-amino-7-fluoroimidazo[1,5-a]quinoxalin-8-yl)((4aS,9aR)-7-(difluoromethoxy)-6-fluoro-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-7-(difluoromethoxy)-6-fluoro-2,3,4,4a,9,9a-hexahydroindeno[2,1-b][1,4]oxazine Eav-1. ES/MS: m/z=488.2 $[M+H]^+$. $^1H$ NMR (400 MHz, DMSO-$d_6$) δ 9.35 (s, 0.7H, major rotamer), 9.28 (s, 0.3H, minor rotamer), 8.82 (br, 2H), 8.64-8.51 (m, 1H), 8.25 (s, 0.7H, major rotamer), 8.22 (s, 0.3H, minor rotamer), 7.53-6.88 (m, 4H), 5.87 (s, 0.7H, major rotamer), 4.96 (s, 0.3H, minor rotamer), 4.42 (t, J=4.0 Hz, 0.7H, major rotamer), 4.39-4.35 (m, 0.3H, minor rotamer), 4.34-4.29 (m, 0.3H, minor rotamer), 3.83-3.76 (m, 0.3H, minor rotamer), 3.66-3.60 (m, 0.7H, major rotamer), 3.58-3.45 (m, 1H), 3.35-3.28 (m, 0.7H, major rotamer), 3.26-3.18 (m, 0.7H, major rotamer), 3.12-2.99 (m, 1H), 2.93-2.91 (m, 0.3H, minor rotamer), 2.83-2.75 (m, 1H).

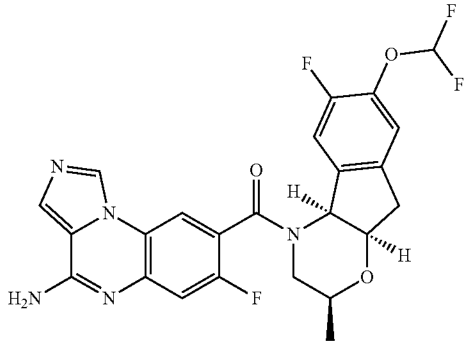 [SMILES: C[C@H]1CN(C(=O)c2cc3c(cc2F)nc(N)c2cncn23)[C@H]2c3cc(F)c(OC(F)F)cc3C[C@H]2O1]

Example Ff-175: (4-amino-7-fluoroimidazo[1,5-a]quinoxalin-8-yl)((2S,4aS,9aR)-7-(difluoromethoxy)-6-fluoro-2-methyl-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and ((2S,4aS,9aR)-7-(difluoromethoxy)-6-fluoro-2-methyl-2,3,4,4a,9,9a-hexahydroindeno[2,1-b][1,4]oxazine Eav-2. ES/MS: m/z=502.2 $[M+H]^+$. $^1H$ NMR (400 MHz, DMSO-$d_6$) δ 9.35 (s, 0.65H, major rotamer), 9.27 (s, 0.35H, minor rotamer), 8.81 (br, 2H), 8.65-8.50 (m, 1H), 8.25 (s, 0.65H, major rotamer), 8.21 (s, 0.35H, minor rotamer), 7.48-6.89 (m, 4H), 5.85 (s, 0.65H, major rotamer), 4.92 (s, 0.35H, minor rotamer), 4.49 (t, J=4.1 Hz, 0.65H, major rotamer), 4.43-4.39 (m, 0.35H, minor rotamer), 4.39-4.35 (m, 0.35H, minor rotamer), 3.62-3.57 (m, 1H), 3.34 (d, J=13.2 Hz, 0.65H, major rotamer), 3.22 (d, J=16.1 Hz, 0.65H, major rotamer), 2.97 (d, J=16.5 Hz, 0.35H, minor rotamer), 2.90-2.82 (m, 0.65H, major rotamer), 2.77-2.67 (m, 1H), 2.48-2.41 (m, 0.35H, minor rotamer), 1.16 (d, J=6.2 Hz, 1.05H, minor rotamer), 0.99 (d, J=6.2 Hz, 1.95H, major rotamer).

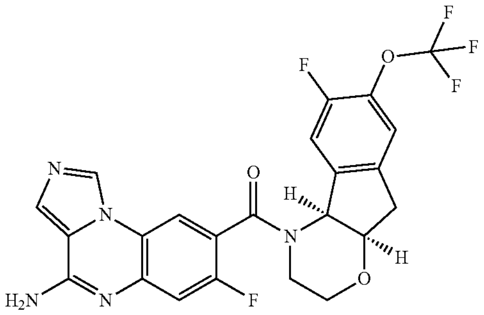 [SMILES: Nc1nc2cc(F)c(C(=O)N3CCO[C@@H]4Cc5cc(OC(F)(F)F)c(F)cc5[C@@H]43)cc2n2cncc12]

Example Ff-176: (4-amino-7-fluoroimidazo[1,5-a]quinoxalin-8-yl)((4aS,9aR)-6-fluoro-7-(trifluoromethoxy)-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-6-fluoro-7-(trifluoromethoxy)-2,3,4,4a,9,9a-hexahydroindeno[2,1-b][1,4]oxazine Eaw-1. ES/MS: m/z=506.2 $[M+H]^+$. $^1H$ NMR (400 MHz, DMSO-$d_6$) δ 9.32 (s, 0.7H, major rotamer), 9.24 (s, 0.3H, minor rotamer), 8.68 (brs, 2H), 8.64-8.51 (m, 1H), 8.21 (s, 0.7H, major rotamer), 8.17 (s, 0.3H, minor rotamer), 7.59 (d, J=7.0 Hz, 0.7H, major rotamer), 7.48 (d, J=7.0 Hz, 0.3H, minor rotamer), 7.43 (d, J=10.4 Hz, 0.7H, major rotamer), 7.38 (d, J=10.3 Hz, 0.3H, minor rotamer), 7.21 (brs, 1H), 5.91 (s, 0.7H, major rotamer), 5.03 (s, 0.3H, minor rotamer), 4.43 (t, J=4.0 Hz, 0.7H, major rotamer), 4.38 (m, 0.3H, minor rotamer), 4.34-4.29 (m, 0.3H, minor rotamer), 3.83-3.76 (m, 0.3H, minor rotamer), 3.66-3.60 (m, 0.7H, major rotamer), 3.58-3.45 (m, 1H), 3.35-3.28 (m, 0.7H, major rotamer), 3.26-3.18 (m, 0.7H, major rotamer), 3.14-3.04 (m, 1H), 3.03-2.95 (m, 0.3H, minor rotamer), 2.83-2.75 (m, 1H).

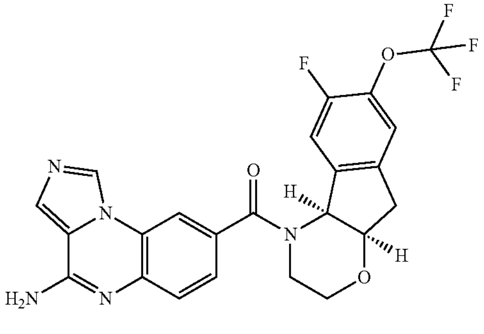 [SMILES: Nc1nc2ccc(C(=O)N3CCO[C@@H]4Cc5cc(OC(F)(F)F)c(F)cc5[C@@H]43)cc2n2cncc12]

Example Ff-177: (4-aminoimidazo[1,5-a]quinoxalin-8-yl)((4aS,9aR)-6-fluoro-7-(trifluoromethoxy)-2,3,9,9a-tetrahydroindeno[2,1-b][1,4]oxazin-4(4aH)-yl)methanone. Prepared using general procedure VI-F starting with 4-(tert-butoxycarbonylamino)imidazo[1,5-a]quinoxaline-8-carboxylic acid Ae-1 and (4aS,9aR)-6-fluoro-7-(trifluoromethoxy)-2,3,4,4a,9,9a-hexahydroindeno[2,1-b][1,4]oxazine Eaw-1. ES/MS: m/z=488.2 $[M+H]^+$. $^1H$ NMR (400 MHz, DMSO-$d_6$) δ 9.45 (s, 0.7H, major rotamer), 9.36 (s, 0.3H, minor rotamer), 8.99 (br, 2H), 8.60 (s, 0.7H, major rotamer), 8.53 (s, 0.3H, minor rotamer), 8.35 (m, 1H), 7.82-7.23 (m, 4H), 5.88 (s, 0.7H, major rotamer), 5.08 (s, 0.3H, minor rotamer), 4.43 (m, 0.7H, major rotamer), 4.37 (m, 0.3H, minor rotamer), 4.34-4.29 (m, 0.3H, minor rotamer), 3.83-3.76 (m, 0.3H, minor rotamer), 3.66-3.60 (m, 0.7H, major rotamer), 3.58-3.45 (m, 1H), 3.35-3.28 (m, 0.7H, major rotamer), 3.26-3.18 (m, 0.7H, major rotamer), 3.14-3.04 (m, 1H), 3.03-2.95 (m, 0.3H, minor rotamer), 2.83-2.75 (m, 1H).

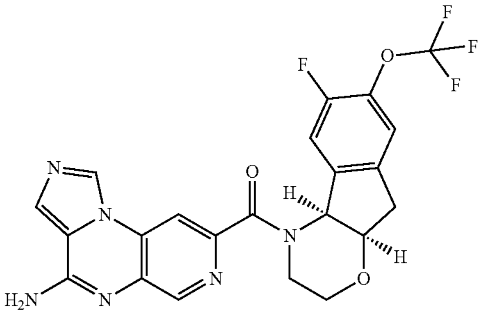 [SMILES: Nc1nc2cnc(C(=O)N3CCO[C@@H]4Cc5cc(OC(F)(F)F)c(F)cc5[C@@H]43)cc2n2cncc12]

Example Ff-178: (4-aminoimidazo[1,5-a]pyrido[3,4-e]pyrazin-8-yl)((4aS,9aR)-6-fluoro-7-(trifluoromethoxy)-2,3,9,9a-tetrahydroindeno[2,1-b][1,4]oxazin-4(4aH)-yl)methanone. Prepared using general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid AF-6 and (4aS,9aR)-6-fluoro-7-(trifluoromethoxy)-2,3,4,4a,9,9a-hexahydroindeno[2,1-b][1,4]oxazine Eaw-1. ES/MS: m/z=489.2 $[M+H]^+$. $^1H$ NMR (400 MHz, MeOD-$d_4$) δ 9.42 (s, 0.5H, rotamer), 9.41 (s, 0.5H, rotamer), 8.89 (s, 0.5H, rotamer), 8.75 (s, 0.5H, rotamer), 8.70 (s, 0.5H, rotamer), 8.67 (s, 0.5H, rotamer), 8.39 (s, 0.5H, rotamer), 8.38 (s, 0.5H, rotamer), 7.52 (d, J=9.7 Hz, 0.5H, rotamer), 7.42 (d, J=7.0 Hz, 0.5H, rotamer), 7.34 (d, J=7.0 Hz, 0.5H, rotamer), 7.26 (d, J=9.5 Hz, 0.5H, rotamer), 5.96 (s, 0.5H, rotamer), 5.50 (s, 0.5H, rotamer), 4.58-4.50 (m, 1H), 4.40 (m, 0.5H, rotamer), 3.93-3.85 (m, 1H), 3.83 (m, 0.5H, rotamer), 3.74-3.68 (m, 1H), 3.67-3.62 (m, 0.5H, rotamer), 3.04-2.85 (m, 2H), 1.30 (brs, 1H).

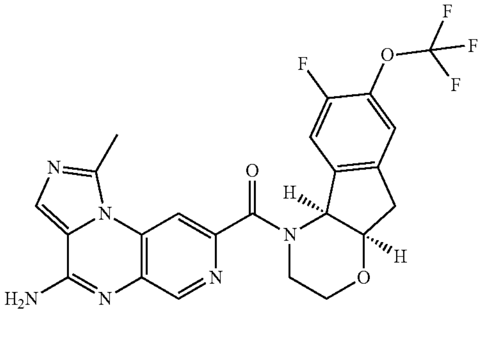 [SMILES: Cc1ncc2c(N)nc3cnc(C(=O)N4CCO[C@@H]5Cc6cc(OC(F)(F)F)c(F)cc6[C@@H]54)cc3n12]

Example Ff-179: (4-amino-1-methylimidazo[1,5-a]pyrido[3,4-e]pyrazin-8-yl)((4aS,9aR)-6-fluoro-7-(trifluoromethoxy)-2,3,9,9a-tetrahydroindeno[2,1-b][1,4]oxazin-4(4aH)-yl)methanone. Prepared using general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (4aS,9aR)-6-fluoro-7-(trifluoromethoxy)-2,3,4,4a,9,9a-hexahydroindeno[2,1-b]

[1,4]oxazine Eaw-1. ES/MS: m/z=503.2 [M+H]$^+$. $^1$H NMR (400 MHz, DMSO-$d_6$) δ 8.76 (s, 0.5H, rotamer), 8.62 (s, 0.5H, rotamer), 8.41 (s, 0.5H, rotamer), 8.36 (s, 0.5H, rotamer), 8.21 (br, 2H), 8.08 (s, 0.5H, rotamer), 8.05 (s, 0.5H, rotamer), 7.62-7.55 (m, 1H), 7.48 (d, J=7.0 Hz, 0.5H, rotamer), 7.27 (d, J=7.0 Hz, 0.5H, rotamer), 5.86 (d, J=3.8 Hz, 0.5H, rotamer), 5.55 (d, J=3.6 Hz, 0.5H, rotamer), 4.47 (t, J=4.0 Hz, 0.5H), 4.39 (d, J=13.5 Hz, 0.5H), 4.33 (t, J=3.9 Hz, 0.5H), 3.90-3.76 (m, 1H), 3.58-3.45 (m, 1H), 3.35-3.28 (m, 0.5H, rotamer), 3.26-3.18 (m, 0.5H, rotamer), 3.14-3.04 (m, 1H), 3.06 (s, 1.5H, rotamer), 3.03 (s, 1.5H, rotamer), 3.03-2.95 (m, 0.5H, rotamer), 2.83-2.75 (m, 1H).

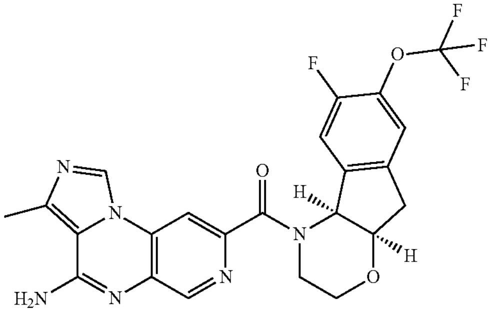 [SMILES: Cc1ncn2c1c(N)nc1cnc(C(=O)N3CCO[C@@H]4Cc5cc(OC(F)(F)F)c(F)cc5[C@@H]43)cc12]

Example Ff-180: (4-amino-3-methylimidazo[1,5-a]pyrido[3,4-e]pyrazin-8-yl)((4aS,9aR)-6-fluoro-7-(trifluoromethoxy)-2,3,9,9a-tetrahydroindeno[2,1-b][1,4]oxazin-4(4aH)-yl)methanone. Prepared using general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and (4aS,9aR)-6-fluoro-7-(trifluoromethoxy)-2,3,4,4a,9,9a-hexahydroindeno[2,1-b][1,4]oxazine Eaw-1. ES/MS: m/z=503.3 [M+H]$^+$. $^1$H NMR (400 MHz, DMSO-$d_6$) δ 9.28 (s, 0.5H, rotamer), 9.25 (s, 0.5H, rotamer), 8.70 (s, 0.5H, rotamer), 8.60 (s, 0.5H, rotamer), 8.57 (s, 0.5H, rotamer), 8.54 (s, 0.5H, rotamer), 7.62 (br, 2H), 7.57 (d, J=7.0 Hz, 0.5H, rotamer), 7.50 (s, 0.5H, rotamer), 7.48 (s, 0.5H, rotamer), 7.18 (d, J=9.6 Hz, 0.5H, rotamer), 5.86 (d, J=3.8 Hz, 0.5H, rotamer), 5.47 (d, J=3.6 Hz, 0.5H, rotamer), 4.46 (t, J=4.0 Hz, 0.5H rotamer), 4.38 (d, J=13.5 Hz, 0.5H, rotamer), 4.31 (t, J=3.9 Hz, 0.5H, rotamer), 3.88-3.79 (m, 1H), 3.67-3.53 (m, 1H), 3.35-3.20 (m, 1H), 3.14-3.04 (m, 1H), 3.01-2.95 (m, 0.5H, rotamer), 2.83-2.75 (m, 1H), 2.68 (s, 1.5H, rotamer), 2.66 (s, 1.5H, rotamer).

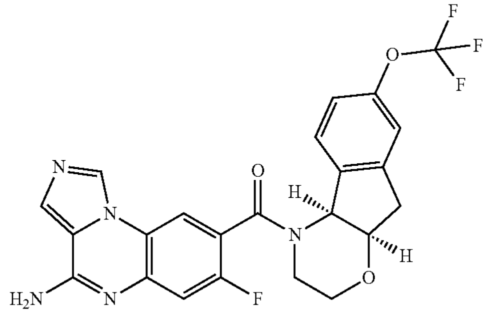 [SMILES: Nc1nc2cc(F)c(C(=O)N3CCO[C@@H]4Cc5cc(OC(F)(F)F)ccc5[C@@H]43)cc2n2cncc12]

Example Ff-181: (4-amino-7-fluoroimidazo[1,5-a]quinoxalin-8-yl)((4aS,9aR)-7-(trifluoromethoxy)-2,3,9,9a-tetrahydroindeno[2,1-b][1,4]oxazin-4(4aH)-yl)methanone. Prepared using general procedure VI-F starting with 4-((tert-butoxycarbonyl)amino)-7-fluoroimidazo[1,5-a]quinoxaline-8-carboxylic acid Af-1 and (4aS,9aR)-7-(trifluoromethoxy)-2,3,4,4a,9,9a-hexahydroindeno[2,1-b][1,4]oxazine Eaw-2. ES/MS: m/z=488.2 [M+H]$^+$. $^1$H NMR (400 MHz, MeOD-$d_4$) δ 9.32 (s, 0.7H, major rotamer), 9.27 (s, 0.3H, minor rotamer), 8.59 (d, J=5.9 Hz, 0.3H, minor rotamer), 8.55 (d, J=5.8 Hz, 0.7H, major rotamer). 8.37 (s, 0.7H, major rotamer), 8.34 (s, 0.3H, minor rotamer), 7.50 (d, J=9.7 Hz, 0.7H, major rotamer), 7.45 (d, J=9.7 Hz, 0.3H, minor rotamer), 7.38 (br, 1H), 7.30-7.17 (m, 2H), 5.99 (s, 0.7H, major rotamer), 5.05 (s, 0.3H, minor rotamer), 4.53 (t, J=4.0 Hz, 0.7H, major rotamer), 3.92-3.86 (m, 0.3H, minor rotamer), 3.78-3.58 (m, 2H), 3.43 (d, J=13.3 Hz, 0.7H, major rotamer), 3.35-3.28 (m, 0.3H, minor rotamer), 3.27-3.20 (m, 1H), 3.07-2.87 (m, 2H).

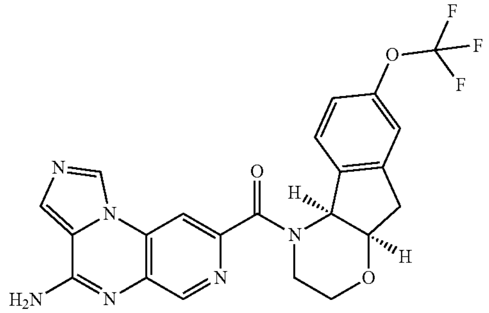 [SMILES: Nc1nc2cnc(C(=O)N3CCO[C@@H]4Cc5cc(OC(F)(F)F)ccc5[C@@H]43)cc2n2cncc12]

Example Ff-182: (4-aminoimidazo[1,5-a]pyrido[3,4-e]pyrazin-8-yl)((4aS,9aR)-7-(trifluoromethoxy)-2,3,9,9a-tetrahydroindeno[2,1-b][1,4]oxazin-4(4aH)-yl)methanone. Prepared using general procedure VI-F starting with 4-((tert-butoxycarbonyl)amino)imidazo[1,5-a]pyrido[3,4-e]pyrazine-8-carboxylic acid Af-6 and (4aS,9aR)-7-(trifluoromethoxy)-2,3,4,4a,9,9a-hexahydroindeno[2,1-b][1,4]oxazine Eaw-2. ES/MS: m/z=471.2 [M+H]$^+$. $^1$H NMR (400 MHz, MeOD-$d_4$) δ 9.41 (s, 0.5H, rotamer), 9.39 (s, 0.5H, rotamer), 8.88 (s, 0.5H, rotamer), 8.75 (s, 0.5H, rotamer), 8.68 (s, 0.5H, rotamer), 8.64 (s, 0.5H, rotamer), 8.36 (s, 0.5H, rotamer), 8.35 (s, 0.5H, rotamer), 7.60 (d, J=8.7 Hz, 0.5H, rotamer), 7.39 (d, J=8.4 Hz, 0.5H, rotamer), 7.28 (s, 0.5H, rotamer), 7.21 (s, 0.5H, rotamer), 7.19 (s, 1H), 5.96 (d, J=3.9 Hz, 0.5H, rotamer), 5.50 (d, J=3.8 Hz, 0.5H, rotamer), 4.55 (t, J=4.1 Hz, 0.5H, rotamer), 4.50 (d, J=13.4 Hz, 0.5H, rotamer), 4.42 (t, J=3.8 Hz, 0.5H, rotamer), 3.89 (dd, J=11.8, 3.1 Hz, 0.5H, rotamer), 3.82 (d, J=13.7 Hz, 0.5H, rotamer), 3.75-3.69 (m, 1H), 3.69-3.65 (m, 0.5H, rotamer), 3.30-3.22 (m, 1H), 3.06-2.87 (m, 2H).

Examples Ff-183 and Ff-184: Prepared following general procedure VI-F starting with 4-((tert-butoxycarbonyl)amino)-7-fluoroimidazo[1,5-a]quinoxaline-8-carboxylic acid Af-1 and (4aS,9aR)-2-methyl-7-(trifluoromethoxy)-2,3,4,4a,9,9a-hexahydroindeno[2,1-b][1,4]oxazine Eaw-3.

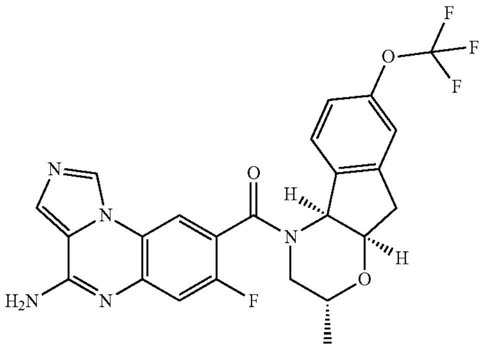 [SMILES: C[C@@H]1CN(C(=O)c2cc3c(cc2F)nc(N)c2cncn23)[C@H]2c3ccc(OC(F)(F)F)cc3C[C@H]2O1]

Example Ff-183: (4-amino-7-fluoroimidazo[1,5-a]quinoxalin-8-yl)((2R,4aS,9aR)-2-methyl-7-(trifluoromethoxy)-2,3,9,9a-tetrahydroindeno[2,1-b][1,4]oxazin-4(4aH)-yl) methanone. Peak 1: ES/MS: m/z=502.2 $[M+H]^+$. $^1H$ NMR (400 MHz, MeOD-$d_4$) δ 9.42-9.20 (m, 1H), 8.56 (d, J=5.8 Hz, 0.6H, major rotamer), 8.51 (d, J=5.9 Hz, 0.4H, minor rotamer), 8.34 (s, 0.6H, major rotamer), 8.31 (s, 0.4H, minor rotamer), 7.55-7.33 (m, 2H), 7.30-7.16 (m, 2H), 6.04 (s, 0.6H, major rotamer), 5.02 (s, 0.4H, minor rotamer), 4.81 (t, J=4.3 Hz, 0.6H, major rotamer), 4.75 (t, J=4.3 Hz, 0.4H, minor rotamer), 4.33 (d, J=13.3 Hz, 0.4H, minor rotamer), 4.05 (br, 0.4H, minor rotamer), 3.87 (br, 0.6H, major rotamer), 3.44-3.35 (m, 0.6H, major rotamer), 3.31-3.20 (m. 1H), 3.19-2.99 (m, 1H), 2.99-2.91 (m, 0.6H, major rotamer), 2.88-2.80 (m, 0.4H, minor rotamer), 1.46 (d, J=6.4 Hz, 1.2H, minor rotamer), 1.34 (d, J=6.7 Hz, 1.8H, major rotamer).

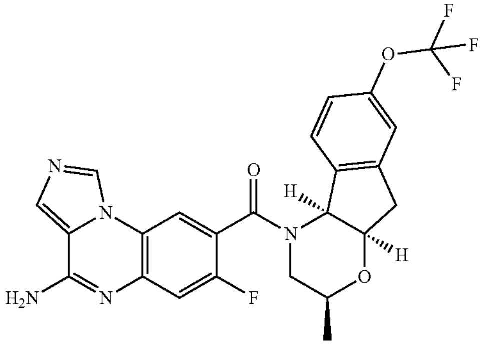 [SMILES: C[C@H]1CN(C(=O)c2cc3c(cc2F)nc(N)c2cncn23)[C@H]2c3ccc(OC(F)(F)F)cc3C[C@H]2O1]

Example Ff-184: (4-amino-7-fluoroimidazo[1,5-a]quinoxalin-8-yl)((2S,4aS,9aR)-2-methyl-7-(trifluoromethoxy)-2,3,9,9a-tetrahydroindeno[2,1-b][1,4]oxazin-4(4aH)-yl) methanone. Peak 2: ES/MS: m/z=502.2 $[M+H]^+$. $^1H$ NMR (400 MHz, MeOD-$d_4$) δ 9.30 (s, 0.7H, major rotamer), 9.25 (s, 0.3H, minor rotamer), 8.56 (d, J=5.9 Hz, 0.3H, minor rotamer), 8.54-8.46 (m, 0.7H, major rotamer), 8.35 (s, 0.7H, major rotamer), 8.32 (s, 0.3H, minor rotamer), 7.50 (d, J=9.8 Hz, 0.7H, major rotamer), 7.44 (d, J=9.7 Hz, 0.3H, minor rotamer), 7.37 (br, 1H), 7.28 (s, 0.7H, major rotamer), 7.23 (s, 0.3H, minor rotamer), 7.22-7.16 (m, 1H), 5.96 (s, 0.7H, major rotamer), 5.01 (s, 0.3H, minor rotamer), 4.59 (t, J=4.1 Hz, 0.7H, major rotamer), 4.53 (t, J=4.1 Hz, 0.3H, minor rotamer), 4.50 (d, J=13.3 Hz, 0.3H, minor rotamer), 3.80-3.66 (m, 1H), 3.40 (d, J=14.8 Hz, 0.7H, major rotamer), 3.32-3.22 (m, 0.7H major rotamer), 3.03 (d, J=16.5 Hz, 1H,), 2.94-2.79 (m, 1H), 2.59 (dd, J=13.3, 10.6 Hz, 0.3H, minor rotamer), 1.16 (d, J=6.2 Hz, 0.9H, minor rotamer), 0.99 (d, J=6.2 Hz, 2.1H, major rotamer).

Examples Ff-185 and Ff-186: Prepared following general procedure VI-F starting with 4-((tert-butoxycarbonyl) amino)imidazo[1,5-a]pyrido[3,4-e]pyrazine-8-carboxylic acid Af-6 and (4aS,9aR)-2-methyl-7-(trifluoromethoxy)-2,3,4,4a,9,9a-hexahydroindeno[2,1-b][1,4]oxazine Eaw-3.

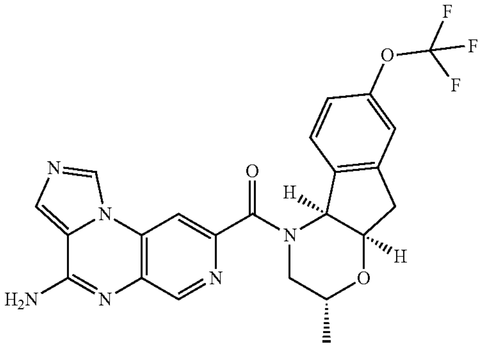 [SMILES: C[C@@H]1CN(C(=O)c2cc3c(cn2)nc(N)c2cncn23)[C@H]2c3ccc(OC(F)(F)F)cc3C[C@H]2O1]

Example Ff-185: (4-aminoimidazo[1,5-a]pyrido[3,4-e]pyrazin-8-yl)((2R,4aS,9aR)-2-methyl-7-(trifluoromethoxy)-2,3,9,9a-tetrahydroindeno[2,1-b][1,4]oxazin-4(4aH)-yl) methanone. Peak 1: ES/MS: m/z=485.2 $[M+H]^+$. $^1H$ NMR (400 MHz, DMSO-$d_6$) δ 9.41-9.36 (m, 1H), 8.72 (s, 0.5H, rotamer), 8.65 (s, 0.5H, rotamer), 8.61 (s, 0.5H, rotamer), 8.58 (s, 0.5H, rotamer), 8.09-7.87 (m, 3H), 7.57 (d, J=8.7 Hz, 0.5H, rotamer), 7.36 (s, 0.5H, rotamer), 7.32-7.22 (m, 2H), 5.90 (d, J=3.9 Hz, 0.5H, rotamer), 5.42 (d, J=3.8 Hz, 0.5H, rotamer), 4.70 (t, J=4.3 Hz, 0.5H, rotamer), 4.57 (t, J=4.3 Hz, 0.5H, rotamer), 4.20 (d, J=13.3 Hz, 0.5H, rotamer), 3.97 (br, 0.5H, rotamer), 3.80 (br, 0.5H, rotamer), 3.66 (d, J=13.3 Hz, 0.5H, rotamer), 3.31-3.16 (m. 1H), 3.03-2.98 (m, 0.5H, rotamer), 2.94-2.83 (m, 1H), 2.76-2.67 (m, 0.5H, rotamer), 1.31 (d, J=6.4 Hz, 1.5H, rotamer), 1.26 (d, J=6.7 Hz, 1.5H, rotamer).

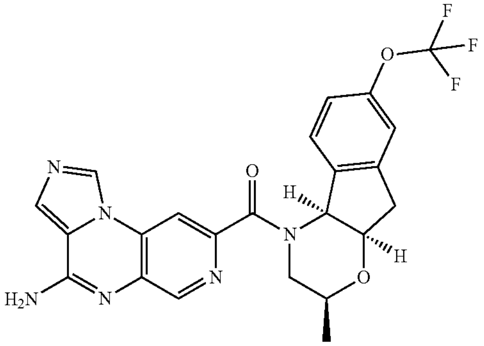 [SMILES: C[C@H]1CN(C(=O)c2cc3c(cn2)nc(N)c2cncn23)[C@H]2c3ccc(OC(F)(F)F)cc3C[C@H]2O1]

Example Ff-186: (4-aminoimidazo[1,5-a]pyrido[3,4-e]pyrazin-8-yl)((2S,4aS,9aR)-2-methyl-7-(trifluoromethoxy)-2,3,9,9a-tetrahydroindeno[2,1-b][1,4]oxazin-4(4aH)-yl) methanone. Peak 2: ES/MS: m/z=485.2 $[M+H]^+$. $^1H$ NMR (400 MHz, DMSO-$d_6$) δ 9.42 (s, 0.5H, rotamer), 9.39 (s, 0.5H, rotamer), 8.77 (s, 0.5H, rotamer), 8.68 (s, 0.5H, rotamer), 8.63 (s, 0.5H, rotamer), 8.60 (s, 0.5H, rotamer), 8.30 (br, 2H), 8.17-8.09 (m, 1H), 7.50 (d, J=8.0 Hz, 0.5H, rotamer), 7.36 (s, 0.5H, rotamer), 7.31-7.22 (m, 2H), 5.84 (d, J=3.9 Hz, 0.5H, rotamer), 5.44 (d, J=3.8 Hz, 0.5H, rotamer), 4.52 (t, J=4.1 Hz, 0.5H, rotamer), 4.43-4.35 (m, 1H), 3.78-3.73 (m, 1H), 3.27 (dd, J=16.4, 4.2 Hz, 0.5H, rotamer), 3.01 (dd, J=16.9, 4.0 Hz, 0.5H, rotamer), 2.96-2.84 (m, 1H), 2.80

(d, J=16.7 Hz, 0.5H, rotamer), 2.75-2.66 (m, 0.5H, rotamer), 2.39 (dd, J=13.4, 10.6 Hz, 0.5H, rotamer), 1.07 (d, J=6.2 Hz, 1.5H, rotamer), 0.91 (d, J=6.2 Hz, 1.5H, major rotamer).

Examples Ff-187 and Ff-188: Prepared following general procedure VI-F starting with 4-((tert-butoxycarbonyl) amino)imidazo[1,5-a]quinoxaline-8-carboxylic acid Ae-1 and and (4aS,9aR)-2-methyl-7-(trifluoromethoxy)-2,3,4,4a,9,9a-hexahydroindeno[2,1-b][1,4]oxazine Eaw-3.

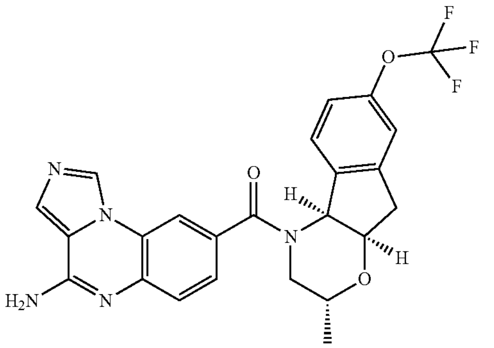 [SMILES: C[C@@H]1CN(C(=O)c2ccc3nc(N)c4cncn4c3c2)[C@H]2c3ccc(OC(F)(F)F)cc3C[C@H]2O1]

Example Ff-187: (4-aminoimidazo[1,5-a]quinoxalin-8-yl)((2R,4aS,9aR)-2-methyl-7-(trifluoromethoxy)-2,3,9,9a-tetrahydroindeno[2,1-b][1,4]oxazin-4(4aH)-yl)methanone. Peak 1: ES/MS: m/z=484.2 $[M+H]^+$. $^1H$ NMR (400 MHz, DMSO-$d_6$) δ 9.44 (s, 1H), 8.95 (br, 2H), 8.52 (s, 1H), 8.32 (s, 1H), 7.75-7.21 (m, 4H), 5.89 (s, 0.6H, major rotamer), 5.05 (s, 0.4H, minor rotamer), 4.65 (m, 0.6H, major rotamer), 4.19-4.10 (m, 0.4H, minor rotamer), 3.97 (br, 0.4H, minor rotamer), 3.78 (br, 0.6H, major rotamer), 3.34-3.15 (m, 3H), 3.06-2.89 (m, 1H), 2.85-2.71 (m, 1H), 1.42-1.09 (m, 3H).

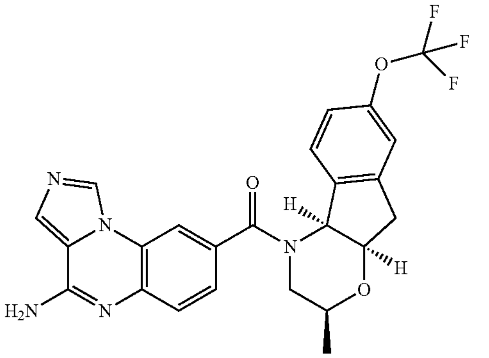 [SMILES: C[C@H]1CN(C(=O)c2ccc3nc(N)c4cncn4c3c2)[C@H]2c3ccc(OC(F)(F)F)cc3C[C@H]2O1]

Example Ff-188: (4-aminoimidazo[1,5-a]quinoxalin-8-yl)((2S,4aS,9aR)-2-methyl-7-(trifluoromethoxy)-2,3,9,9a-tetrahydroindeno[2,1-b][1,4]oxazin-4(4aH)-yl)methanone. Peak 2: ES/MS: m/z=484.2 $[M+H]^+$. $^1H$ NMR (400 MHz, DMSO-$d_6$) δ 9.48 (s, 0.6H, major rotamer), 9.37 (s, 0.4H, minor rotamer), 9.11 (br, 2H), 8.59 (s, 0.4H, minor rotamer), 8.51 (s, 0.6H, major rotamer), 8.37 (s, 0.6H, major rotamer), 8.33 (s, 0.4H, minor rotamer), 7.74-7.18 (m, 5H), 5.84 (d, J=3.9 Hz, 0.6H, major rotamer), 5.04 (d, J=3.8 Hz, 0.4H, minor rotamer), 4.53-4.46 (m, 1H), 4.33 (d, J=13.3 Hz, 0.4H, minor rotamer), 3.70-3.64 (m, 1H), 3.30-3.23 (m, 0.6H, major rotamer), 3.03-2.94 (m, 0.4H, minor rotamer), 2.91 (d, J=13.3 Hz, 0.6H, major rotamer), 2.84-2.73 (m, 1H), 2.45-2.30 (m, 1H), 1.07 (d, J=6.2 Hz, 1.2H, rotamer), 0.89 (d, J=6.2 Hz, 1.8H, major rotamer).

Examples Ff-189 and Ff-190: Prepared following general procedure VI-F starting with 4-(tert-butoxycarbonylamino)-1-methyl-imidazo[1,5-a]quinoxaline-8-carboxylic acid Af-3 and (4aS,9aR)-2-methyl-7-(trifluoromethoxy)-2,3,4,4a,9,9a-hexahydroindeno[2,1-b][1,4]oxazine Eaw-3.

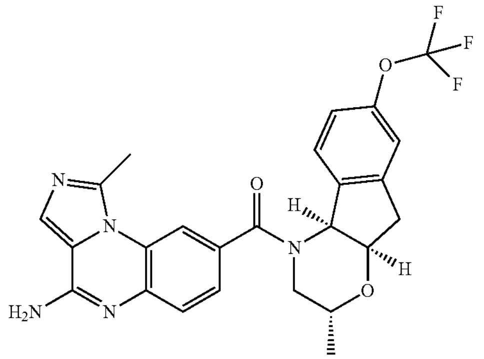 [SMILES: Cc1ncc2c(N)nc3ccc(C(=O)N4C[C@@H](C)O[C@@H]5Cc6cc(OC(F)(F)F)ccc6[C@@H]54)cc3n12]

Example Ff-189: (4-amino-1-methylimidazo[1,5-a]quinoxalin-8-yl)((2R,4aS,9aR)-2-methyl-7-(trifluoromethoxy)-2,3,9,9a-tetrahydroindeno[2,1-b][1,4]oxazin-4(4aH)-yl) methanone Peak 1: ES/MS: m/z=498.3 $[M+H]^+$. $^1H$ NMR (400 MHz, DMSO-$d_6$) δ 9.28 (br, 2H), 8.34 (s, 1H), 8.22 (s, 1H), 7.80-7.18 (m, 5H), 5.86 (m, 0.5H, rotamer), 5.16 (m, 0.5H, rotamer), 4.71-4.55 (m, 1H), 4.34-4.12 (m, 1H), 3.34-3.15 (m, 2H), 3.02 (s, 3H), 2.92-2.70 (m, 2H), 1.35-1.19 (m, 3H).

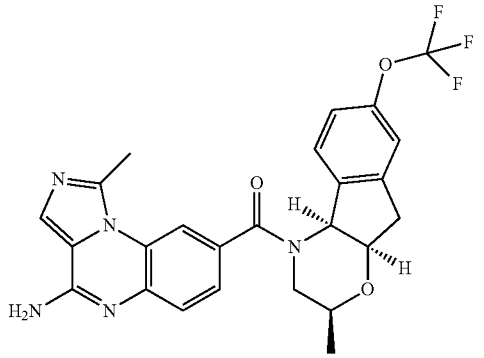 [SMILES: Cc1ncc2c(N)nc3ccc(C(=O)N4C[C@H](C)O[C@@H]5Cc6cc(OC(F)(F)F)ccc6[C@@H]54)cc3n12]

Example Ff-190: (4-amino-1-methylimidazo[1,5-a]quinoxalin-8-yl)((2S,4aS,9aR)-2-methyl-7-(trifluoromethoxy)-2,3,9,9a-tetrahydroindeno[2,1-b][1,4]oxazin-4(4aH)-yl) methanone. Peak 2: ES/MS: m/z=498.2 $[M+H]^+$. $^1H$ NMR (400 MHz, DMSO-$d_6$) δ 9.25 (br, 2H), 8.36 (s, 0.5H, rotamer), 8.31 (s, 0.5H, rotamer), 8.27 (s, 0.5H, rotamer), 8.23 (s, 0.5H, rotamer), 7.77-7.62 (m, 2H), 7.59 (d, J=8.1 Hz, 0.5H), 7.39 (d, J=8.1 Hz, 0.5H), 7.37-7.20 (m, 2H), 5.83 (d, J=3.9 Hz, 0.5H, rotamer), 5.14 (d, J=3.8 Hz, 0.5H, rotamer), 4.53 (t, J=4.1 Hz, 0.5H, rotamer), 4.42 (t, J=4.1 Hz, 0.5H, rotamer), 4.34 (d, J=13.3 Hz, 0.5H, rotamer), 3.46-3.39 (m, 1H), 3.30-3.23 (m, 0.5H, rotamer), 3.28 (s, 1.5H, rotamer), 2.98 (s, 1.5H, rotamer), 3.03-2.94 (m, 1H, rotamer), 2.84-2.73 (m, 1H), 2.45-2.30 (m, 1H), 1.04 (d, J=6.2 Hz, 1.5H, rotamer), 0.90 (d, J=6.2 Hz, 1.5H, rotamer).

Examples Ff-191 and Ff-192: Prepared following general procedure VI-F starting with 4-((tert-butoxycarbonyl) amino)-7-fluoroimidazo[1,5-a]quinoxaline-8-carboxylic acid Af-1 and and (4aS,9aR)-8-fluoro-2-methyl-7-(trifluoromethoxy)-2,3,4,4a,9,9a-hexahydroindeno[2,1-b][1,4] oxazine Eaw-5.

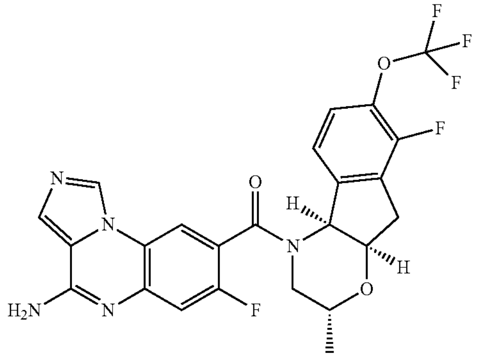 [SMILES: C[C@@H]1CN(C(=O)c2cc3c(cc2F)nc(N)c2cncn23)[C@H]2c3ccc(OC(F)(F)F)c(F)c3C[C@H]2O1]

Example Ff-191: (4-amino-7-fluoroimidazo[1,5-a]quinoxalin-8-yl)((2R,4aS,9aR)-8-fluoro-2-methyl-7-(trifluoromethoxy)-2,3,9,9a-tetrahydroindeno[2,1-b][1,4]oxazin-4(4aH)-yl)methanone. Peak 1: ES/MS: m/z=520.3 $[M+H]^+$. $^1$H NMR (400 MHz, MeOD-$d_4$) δ 9.42-9.20 (m, 1H), 8.57 (d, J=5.8 Hz, 0.4H, minor rotamer), 8.54 (d, J=5.9 Hz, 0.6H, major rotamer), 8.40 (s, 0.6H, major rotamer), 8.37 (s, 0.4H, minor rotamer), 7.90-7.77 (m, 0.6H, major rotamer), 7.66-7.59 (m, 0.4H, minor rotamer), 7.56-7.50 (m, 0.6H, major rotamer), 7.42-7.38 (m, 0.4H, minor rotamer), 7.33-7.16 (m, 1H), 6.09 (s, 0.6H, major rotamer), 5.08 (s, 0.4H, minor rotamer), 4.85 (t, J=4.3 Hz, 0.6H, major rotamer), 4.78 (t, J=4.3 Hz, 0.4H, minor rotamer), 4.35 (d, J=13.3 Hz, 0.4H, minor rotamer), 4.07 (br, 0.4H, minor rotamer), 3.88 (br, 0.6H, major rotamer), 3.45-3.38 (m, 0.6H, major rotamer), 3.29-3.22 (m. 1H), 3.16-3.09 (m, 0.6H, major rotamer), 3.06 (d, J=16.7 Hz, 0.6H, major rotamer), 3.01-2.95 (m, 0.4H, minor rotamer), 2.93-2.88 (m, 0.4H, minor rotamer), 1.46 (d, J=6.4 Hz, 1.2H, minor rotamer), 1.34 (d, J=6.7 Hz, 1.8H, major rotamer).

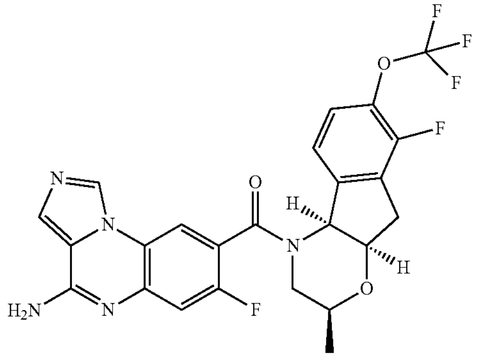 [SMILES: C[C@H]1CN(C(=O)c2cc3c(cc2F)nc(N)c2cncn23)[C@H]2c3ccc(OC(F)(F)F)c(F)c3C[C@H]2O1]

Example Ff-192: (4-amino-7-fluoroimidazo[1,5-a]quinoxalin-8-yl)((2S,4aS,9aR)-8-fluoro-2-methyl-7-(trifluoromethoxy)-2,3,9,9a-tetrahydroindeno[2,1-b][1,4]oxazin-4(4aH)-yl)methanone. Peak 2: ES/MS: m/z=520.3 $[M+H]^+$. $^1$H NMR (400 MHz, MeOD-$d_4$) δ 9.32 (s, 0.7H, major rotamer), 9.27 (s, 0.3H, minor rotamer), 8.57 (d, J=5.8 Hz, 0.3H, minor rotamer), 8.54 (d, J=5.9 Hz, 0.7H, major rotamer), 8.40 (s, 0.7H, major rotamer), 8.37 (s, 0.3H, minor rotamer), 7.53 (d, J=9.7 Hz, 0.7H, major rotamer), 7.47 (d, J=9.6 Hz, 0.3H, minor rotamer), 7.42-7.31 (m, 1H), 7.30-7.12 (m, 1H), 6.01 (s, 0.7H, major rotamer), 5.07 (s, 0.3H, minor rotamer), 4.63 (t, J=4.3 Hz, 0.7H, major rotamer), 4.58-4.55 (m, 0.3H, minor rotamer), 4.51 (d, J=13.3 Hz, 0.3H, minor rotamer), 3.82-3.65 (m, 1H), 3.41 (d, J=13.3 Hz, 0.7H, major rotamer), 3.30-3.23 (m. 0.7H, major rotamer), 3.13 (d, J=16.7 Hz, 0.7H, major rotamer), 3.03-2.99 (m, 0.3H, minor rotamer), 2.91-2.82 (m, 1H), 2.63-2.55 (m, 0.3H, minor rotamer), 1.17 (d, J=6.2 Hz, 0.9H, minor rotamer), 1.00 (d, J=6.2 Hz, 2.1H, major rotamer).

Examples Ff-193 and Ff-194: Prepared following general procedure VI-F starting with 4-((tert-butoxycarbonyl)amino)imidazo[1,5-a]pyrido[3,4-e]pyrazine-8-carboxylic acid Af-6 and (4aS,9aR)-8-fluoro-2-methyl-7-(trifluoromethoxy)-2,3,4,4a,9,9a-hexahydroindeno[2,1-b][1,4]oxazine Eaw-5.

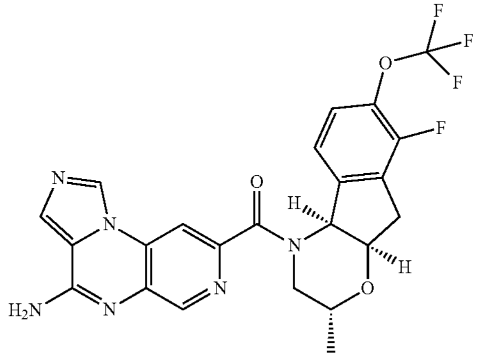 [SMILES: C[C@@H]1CN(C(=O)c2cc3c(cn2)nc(N)c2cncn23)[C@H]2c3ccc(OC(F)(F)F)c(F)c3C[C@H]2O1]

Example Ff-193: (4-aminoimidazo[1,5-a]pyrido[3,4-e]pyrazin-8-yl)((2R,4aS,9aR)-8-fluoro-2-methyl-7-(trifluoromethoxy)-2,3,9,9a-tetrahydroindeno[2,1-b][1,4]oxazin-4(4aH)-yl)methanone. Peak 1: ES/MS: m/z=503.2 $[M+H]^+$. $^1$H NMR (400 MHz, MeOD-d4) δ 9.40 (s, 1H), 8.86 (s, 0.5H, rotamer), 8.74 (s, 0.5H, rotamer), 8.69 (s, 0.5H, rotamer), 8.64 (s, 0.5H, rotamer), 8.34 (s, 1H), 7.48 (d, J=8.2 Hz, 0.5H, rotamer), 7.38 (t, J=7.5 Hz, 1H), 7.24 (d, J=8.2 Hz, 0.5H, rotamer), 6.04 (d, J=3.9 Hz, 0.5H, rotamer), 5.55 (d, J=3.8 Hz, 0.5H, rotamer), 4.73 (t, J=4.3 Hz, 0.5H, rotamer), 4.35 (d, J=13.3 Hz, 0.5H, rotamer), 4.08 (br, 0.5H, rotamer), 3.89 (br, 0.5H, rotamer), 3.74 (d, J=13.3 Hz, 0.5H, rotamer), 3.43-3.36 (m, 0.5H, rotamer), 3.29-3.19 (m. 1H), 3.16-3.09 (m, 0.5H, rotamer), 3.06 (d, J=16.7 Hz, 0.5H, rotamer), 3.01-2.95 (m, 1H), 1.47-1.34 (m, 3H).

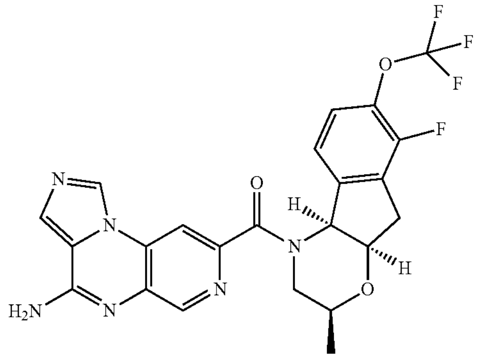 [SMILES: C[C@H]1CN(C(=O)c2cc3c(cn2)nc(N)c2cncn23)[C@H]2c3ccc(OC(F)(F)F)c(F)c3C[C@H]2O1]

Example Ff-194: (4-aminoimidazo[1,5-a]pyrido[3,4-e]pyrazin-8-yl)((2S,4aS,9aR)-8-fluoro-2-methyl-7-(trifluoromethoxy)-2,3,9,9a-tetrahydroindeno[2,1-b][1,4]oxazin-4(4aH)-yl)methanone. Peak 2: ES/MS: m/z=503.2 $[M+H]^+$. $^1$H NMR (400 MHz, MeOD-d4) δ 9.38 (s, 0.5H, rotamer), 9.36 (s, 0.5H, rotamer), 8.87 (s, 0.5H, rotamer), 8.72 (s, 0.5H, rotamer), 8.66 (s, 0.5H, rotamer), 8.61 (s, 0.5H, rotamer), 8.32 (s, 0.5H, rotamer), 8.31 (s, 0.5H, rotamer), 7.42 (d, J=8.1 Hz, 0.5H, rotamer), 7.38-7.32 (m, 1H), 7.19 (d, J=8.3 Hz, 0.5H, rotamer), 5.99 (d, J=3.9 Hz, 0.5H, rotamer), 5.55 (d, J=3.8 Hz, 0.5H, rotamer), 4.65 (t, J=4.3 Hz, 0.5H, rotamer), 4.55-4.50 (m, 1H), 3.85-3.80 (m, 0.5H, rotamer), 3.79-3.71 (m, 1H), 3.26-3.23 (m. 0.5H, rotamer), 3.15-3.09 (m, 0.5H, rotamer), 3.03-2.99 (m, 0.5H, rotamer), 2.92-2.82 (m, 1H), 2.61-2.53 (m, 0.5H, rotamer), 1.17 (d, J=6.2 Hz, 1.5H, rotamer), 1.01 (d, J=6.2 Hz, 1.5H, rotamer).

Examples Ff-195 and Ff-196: Prepared following general procedure VI-F starting with 4-((tert-butoxycarbonyl)amino)imidazo[1,5-a]pyrido[3,4-e]pyrazine-8-carboxylic acid Af-6 and (4aS,9aR)-6-fluoro-2-methyl-7-(trifluoromethoxy)-2,3,4,4a,9,9a-hexahydroindeno[2,1-b][1,4]oxazine Eaw-4.

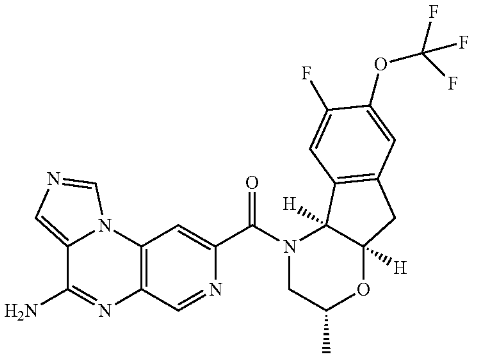 [SMILES: C[C@@H]1CN(C(=O)c2cc3c(cn2)nc(N)c2cncn23)[C@H]2c3cc(F)c(OC(F)(F)F)cc3C[C@H]2O1]

Example Ff-195: (4-aminoimidazo[1,5-a]pyrido[3,4-e]pyrazin-8-yl)((2R,4aS,9aR)-6-fluoro-2-methyl-7-(trifluoromethoxy)-2,3,9,9a-tetrahydroindeno[2,1-b][1,4]oxazin-4(4aH)-yl)methanone. Peak 1: ES/MS: m/z=503.2 $[M+H]^+$. $^1H$ NMR (400 MHz, DMSO-$d_6$) δ 9.41 (s, 0.6H, major rotamer), 9.39 (s, 0.4H, minor rotamer), 8.74 (s, 0.6H, major rotamer), 8.68 (s, 0.4H, minor rotamer), 8.65 (s, 0.6H, major rotamer), 8.61 (s, 0.4H, minor rotamer), 8.30-8.02 (br, 3H), 7.60-7.53 (m, 1H), 7.48 (d, J=7.0 Hz, 0.6H, major rotamer), 7.22 (d, J=9.5 Hz, 0.4H, minor rotamer), 5.91 (d, J=3.9 Hz, 0.4H, minor rotamer), 5.40 (d, J=3.8 Hz, 0.6H, major rotamer), 4.71 (t, J=4.3 Hz, 0.4H, minor rotamer), 4.55 (t, J=4.3 Hz, 0.6H, major rotamer), 4.21 (d, J=13.3 Hz, 0.6H, major rotamer), 3.98 (br, 0.6H, major rotamer), 3.82 (br, 0.4H, minor rotamer), 3.29-3.19 (m. 1H), 3.03-2.86 (m, 2H), 2.82 (d, J=13.3 Hz, 0.4H, minor rotamer), 1.32-1.21 (m, 3H).

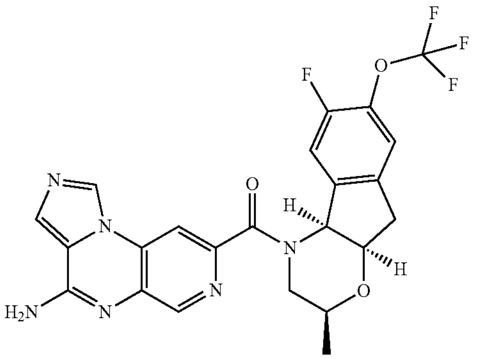 [SMILES: C[C@H]1CN(C(=O)c2cc3c(cn2)nc(N)c2cncn23)[C@H]2c3cc(F)c(OC(F)(F)F)cc3C[C@H]2O1]

Example Ff-196: (4-aminoimidazo[1,5-a]pyrido[3,4-e]pyrazin-8-yl)((2S,4aS,9aR)-6-fluoro-2-methyl-7-(trifluoromethoxy)-2,3,9,9a-tetrahydroindeno[2,1-b][1,4]oxazin-4(4aH)-yl)methanone. Peak 2: ES/MS: m/z=503.3 $[M+H]^+$. $^1H$ NMR (400 MHz, DMSO-$d_6$) δ 9.37 (s, 0.5H, rotamer), 9.34 (s, 0.5H, rotamer), 8.75 (s, 0.5H, rotamer), 8.66 (s, 0.5H, rotamer), 8.62 (s, 0.5H, rotamer), 8.58 (s, 0.5H, rotamer), 8.16-7.91 (br, 3H), 7.57 (d, J=7.0 Hz, 0.5H, rotamer), 7.51-7.45 (m, 1H), 7.17 (d, J=9.5 Hz, 0.5H, rotamer), 5.84 (d, J=3.9 Hz, 0.5H, rotamer), 5.45 (d, J=3.8 Hz, 0.5H, rotamer), 4.53 (t, J=4.3 Hz, 0.5H, rotamer), 4.45-4.36 (m, 1H), 3.85-3.80 (m, 0.5H, rotamer), 3.26-3.23 (m. 0.5H, rotamer), 3.03-2.99 (m, 0.5H, rotamer), 2.92-2.82 (m, 1H), 2.77-2.65 (m, 1H), 2.46-2.41 (m, 1H), 1.08 (d, J=6.2 Hz, 1.5H, rotamer), 0.92 (d, J=6.2 Hz, 1.5H, rotamer).

Examples Ff-197 and Ff-198: Prepared following general procedure VI-F starting with 4-((tert-butoxycarbonyl)amino)-7-fluoroimidazo[1,5-a]quinoxaline-8-carboxylic acid Af-1 and (4aS,9aR)-6-fluoro-2-methyl-7-(trifluoromethoxy)-2,3,4,4a,9,9a-hexahydroindeno[2,1-b][1,4]oxazine Eaw-4.

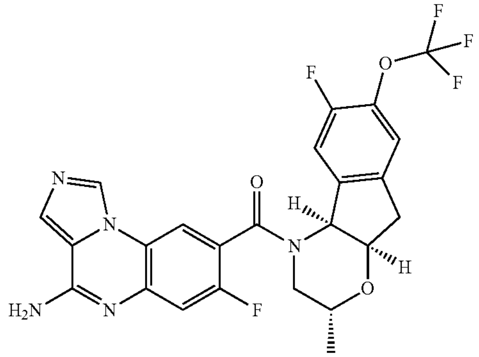 [SMILES: C[C@@H]1CN(C(=O)c2cc3c(cc2F)nc(N)c2cncn23)[C@H]2c3cc(F)c(OC(F)(F)F)cc3C[C@H]2O1]

Example Ff-197: (4-amino-7-fluoroimidazo[1,5-a]quinoxalin-8-yl)((2R,4aS,9aR)-6-fluoro-2-methyl-7-(trifluoromethoxy)-2,3,9,9a-tetrahydroindeno[2,1-b][1,4]oxazin-4(4aH)-yl)methanone. Peak 1: ES/MS: m/z=520.3 $[M+H]^+$. $^1H$ NMR (400 MHz, DMSO-$d_6$) δ 9.34 (s, 0.6H, major rotamer), 9.23 (br, 0.4H, minor rotamer), 8.97-8.40 (m, 3H), 8.22 (s, 0.6H, major rotamer), 8.18 (s, 0.4H, minor rotamer), 7.72-7.52 (m, 1H), 7.51-7.20 (m, 2H), 5.96 (m, 0.6H, major rotamer), 4.98 (m, 0.4H, minor rotamer), 4.69 (t, J=4.3 Hz, 0.6H, major rotamer), 4.57 (t, J=4.3 Hz, 0.4H, minor rotamer), 4.20 (d, J=13.3 Hz, 0.4H, minor rotamer), 3.99 (m, 0.4H, minor rotamer), 3.80 (m, 0.6H, major rotamer), 3.29-3.19 (m, 1H), 3.16-3.11 (m, 1H), 3.02-2.93 (m, 1H), 2.83 (d, J=13.3 Hz, 0.6H, major rotamer), 1.32-1.17 (m, 3H).

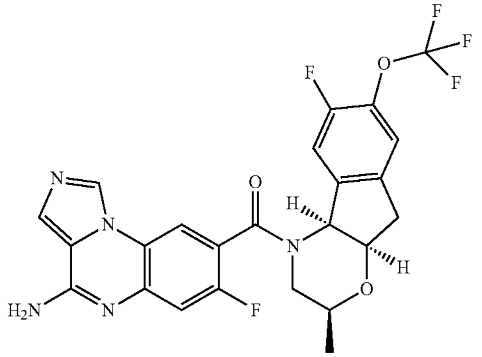 [SMILES: C[C@H]1CN(C(=O)c2cc3c(cc2F)nc(N)c2cncn23)[C@H]2c3cc(F)c(OC(F)(F)F)cc3C[C@H]2O1]

Example Ff-198: (4-amino-7-fluoroimidazo[1,5-a]quinoxalin-8-yl)((2S,4aS,9aR)-6-fluoro-2-methyl-7-(trifluoromethoxy)-2,3,9,9a-tetrahydroindeno[2,1-b][1,4]oxazin-4(4aH)-yl)methanone. Peak 2: ES/MS: m/z=520.2 $[M+H]^+$. $^1$H NMR (400 MHz, DMSO-$d_6$) δ 9.35 (s, 0.6H, major rotamer), 9.26 (s, 0.4H, minor rotamer), 8.87 (br, 2H), 8.56 (d, J=6.2 Hz, 1H), 8.27 (s, 0.6H, major rotamer), 8.22 (s, 0.4H, minor rotamer), 7.58 (d, J=7.0 Hz, 0.6H, major rotamer), 7.51-7.42 (m, 1H), 7.40 (d, J=10.1 Hz, 0.4H, minor rotamer), 7.33-6.96 (m, 1H), 5.88 (m, 0.6H, major rotamer), 4.97 (m, 0.4H, minor rotamer), 4.50 (t, J=4.3 Hz, 0.6H, major rotamer), 4.45-4.40 (m, 0.4H, minor rotamer), 4.40-4.36 (m, 0.4H, minor rotamer), 3.63-3.57 (m, 1H), 3.39-3.23 (m, 1H), 3.03-2.88 (m, 1H), 2.81-2.75 (m, 0.6H, major rotamer), 2.75-2.65 (m, 0.6H, major rotamer), 2.50-2.41 (m, 0.4H, minor rotamer), 1.08 (d, J=6.2 Hz, 1.2H, rotamer), 0.92 (d, J=6.2 Hz, 1.8H, rotamer).

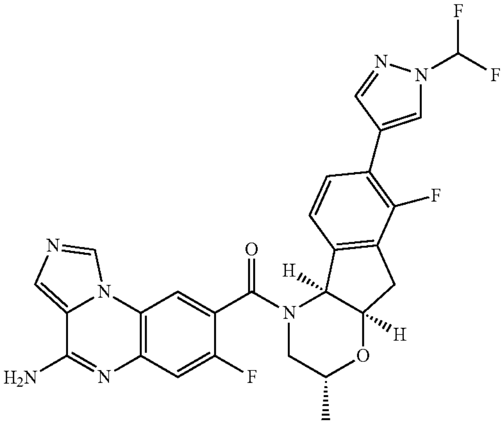 [SMILES: C[C@@H]1CN(C(=O)c2cc3c(cc2F)nc(N)c2cncn23)[C@H]2c3ccc(-c4cnn(C(F)F)c4)c(F)c3C[C@H]2O1]

Example Ff-199: (4-amino-7-fluoroimidazo[1,5-a]quinoxalin-8-yl)((2R,4aS,9aR)-7-(1-(difluoromethyl)-1H-pyrazol-4-yl)-8-fluoro-2-methyl-2,3,9,9a-tetrahydroindeno[2,1-b][1,4]oxazin-4(4aH)-yl)methanone. Prepared following example Ff-95 starting with (4-amino-7-fluoroimidazo[1,5-a]quinoxalin-8-yl)((2R,4aS,9aR)-7-bromo-8-fluoro-2-methyl-2,3,9,9a-tetrahydroindeno[2,1-b][1,4]oxazin-4(4aH)-yl)methanone Ff-163 and 1-(difluoromethyl)-4-(4,4,5,5-tetramethyl-1,3,2-dioxaborolan-2-yl)pyrazole. ES/MS: m/z=552.2 $[M+H]^+$. $^1$H NMR (400 MHz, DMSO-d6) δ 9.36 (s, 0.66H, major rotamer), 9.29 (s, 0.34H, minor rotamer), 8.81-8.35 (m, 3H), 8.27 (d, J=16.5 Hz, 0.66H, major rotamer), 8.18 (d, J=14.4 Hz, 0.66H, major rotamer), 8.02 (d, J=15.7 Hz, 0.34H, minor rotamer), 7.88 (d, J=15.8 Hz, 0.34H, minor rotamer), 7.79-7.71 (m, 1H), 7.46-7.35 (m, 1H), 7.16 (br, 1H), 6.00 (s, 0.66H, major rotamer), 5.00 (s, 0.34H, minor rotamer), 4.72 (t, J=4.1 Hz, 0.66H, major rotamer), 4.64 (t, J=4.1 Hz, 0.34H, minor rotamer), 4.18 (d, J=13.3 Hz, 0.66H, major isomer), 4.00 (br, 3H), 3.32-3.19 (m, 1H), 3.13 (d, J=13.4 Hz, 0.34H, minor rotamer), 3.08-2.94 (m, 1H), 2.99-2.77 (m, 1H), 1.35 (m, 1.02H, minor rotamer), 1.22 (d, J=6.7 Hz, 1.98H, major rotamer).

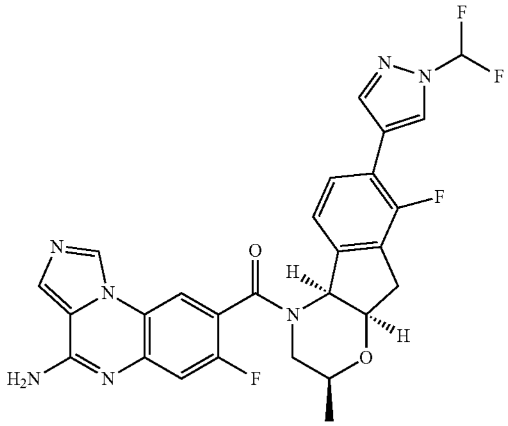 [SMILES: C[C@H]1CN(C(=O)c2cc3c(cc2F)nc(N)c2cncn23)[C@H]2c3ccc(-c4cnn(C(F)F)c4)c(F)c3C[C@H]2O1]

Example Ff-200: (4-amino-7-fluoroimidazo[1,5-a]quinoxalin-8-yl)((2S,4aS,9aR)-7-(1-(difluoromethyl)-1H-pyrazol-4-yl)-8-fluoro-2-methyl-2,3,9,9a-tetrahydroindeno[2,1-b][1,4]oxazin-4(4aH)-yl)methanone. Prepared following example Ff-95 starting with (4-amino-7-fluoroimidazo[1,5-a]quinoxalin-8-yl)((2R,4aS,9aR)-7-bromo-8-fluoro-2-methyl-2,3,9,9a-tetrahydroindeno[2,1-b][1,4]oxazin-4(4aH)-yl)methanone Ff-164 and 1-(difluoromethyl)-4-(4,4,5,5-tetramethyl-1,3,2-dioxaborolan-2-yl)pyrazole ES/MS: m/z=552.2 $[M+H]^+$. $^1$H NMR (400 MHz, DMSO-d6) δ 9.33 (s, 0.66H, major rotamer), 9.25 (s, 0.34H, minor rotamer), 8.81-8.43 (m, 3H), 8.27 (d, J=16.5 Hz, 0.66H, major rotamer), 8.21-8.00 (m, 1H), 7.88 (d, J=16.3 Hz, 0.34H, minor rotamer), 7.80-7.66 (m, 1H), 7.42 (d, J=10.2 Hz, 0.66H, major rotamer), 7.36 (d, J=10.2 Hz, 0.34H, minor rotamer), 7.06 (br, 1H), 5.94 (s, 0.66H, major rotamer), 5.00 (s, 0.34H, minor rotamer), 4.52 (t, J=4.1 Hz, 0.66H, major rotamer), 4.46 (t, J=4.1 Hz, 0.34H, minor rotamer), 4.41 (d, J=13.3 Hz, 0.34H, minor rotamer), 3.64-3.53 (m, 3H), 3.39-3.32 (m, 0.66H, major rotamer), 3.32-3.24 (m, 0.66H major rotamer), 3.09-3.01 (m, 0.34H, minor rotamer), 2.98 (d, J=16.5 Hz, 0.66H, major rotamer), 2.89-2.81 (m, 0.34H, minor rotamer), 2.79-2.63 (m, 0.66H, major rotamer), 2.46-2.37 (m, 0.34H, minor rotamer) 1.08 (d, J=6.2 Hz, 1.02H, minor rotamer), 0.91 (d, J=6.2 Hz, 1.98H, major rotamer).

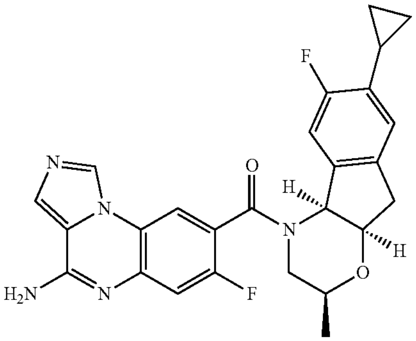 [SMILES: C[C@H]1CN(C(=O)c2cc3c(cc2F)nc(N)c2cncn23)[C@H]2c3cc(F)c(C4CC4)cc3C[C@H]2O1]

Example Ff-201: (4-amino-7-fluoroimidazo[1,5-a]quinoxalin-8-yl)((2S,4aS,9aR)-7-cyclopropyl-6-fluoro-2-methyl-2,3,9,9a-tetrahydroindeno[2,1-b][1,4]oxazin-4(4aH)-yl)methanone. Prepared following example Ff-95 (with 2 equivalents of potassium propionate as an additive) starting with (4-amino-7-fluoroimidazo[1,5-a]quinoxalin-8-yl)((2S,4aS,9aR)-7-bromo-6-fluoro-2-methyl-2,3,9,9a-tetrahydroindeno[2,1-b][1,4]oxazin-4(4aH)-yl)methanone Ff-165 and cyclopropylboronic acid. ES/MS: m/z=476.3 $[M+H]^+$. $^1H$ NMR (400 MHz, DMSO-d6) δ 9.31 (s, 0.66H, major rotamer), 9.23 (s, 0.34H, minor rotamer), 8.54 (br, 1H), 8.19-8.08 (m, 1H), 7.40 (d, J=10.6 Hz, 0.66H, major rotamer), 7.34 (d, J=10.5 Hz, 0.34H, minor rotamer), 6.94 (d, J=6.8 Hz, 0.66H, major rotamer), 6.84 (d, J=7.1 Hz, 0.34H, minor rotamer), 5.80 (s, 0.66H, major rotamer), 4.87 (s, 0.34H, minor rotamer), 4.44 (t, J=4.1 Hz, 0.66H, major rotamer), 4.39 (m, 0.34H, minor rotamer), 4.36 (m, 0.34H, minor rotamer), 3.67-3.52 (m, 1H), 3.32-3.29 (m, 1H), 3.17-3.08 (m, 0.66H, major isomer), 2.90-2.84 (m, 0.66H, major rotamer), 2.82-2.61 (m, 2H), 2.47-2.38 (m, 0.34H, minor isomer), 2.35-2.30 (m, 0.34H, minor rotamer), 2.10-2.03 (m, 0.66H, major rotamer), 2.01-1.94 (m, 0.66, major rotamer), 1.38-1.20 (m, 1.68H), 1.06 (d, J=6.2 Hz, 1.02H, minor rotamer), 1.01-0.95 (m, 0.66H), 0.89 (d, J=6.2 Hz, 1.98H, major rotamer), 0.77-0.67 (m, 1H).

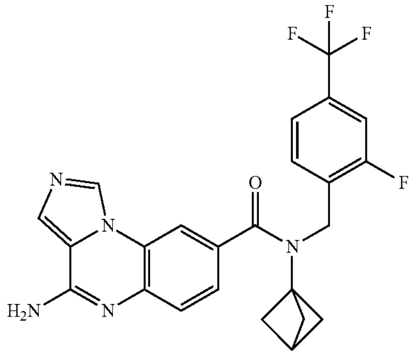 [SMILES: Nc1nc2ccc(C(=O)N(Cc3ccc(C(F)(F)F)cc3F)C34CC(C3)C4)cc2n2cncc12]

Example Ff-202: 4-amino-N-(bicyclo[1.1.1]pentan-1-yl)-N-(2-fluoro-4-(trifluoromethyl)benzyl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-(2-fluoro-4-(trifluoromethyl)benzyl)bicyclo[1.1.1]pentan-1-amine Ec-10. ES/MS: m/z=470.0 $[M+H]^+$. 1H NMR (400 MHz, Methanol-d4) δ 9.33 (s, 1H), 8.52-8.28 (m, 2H), 7.85-7.30 (m, 5H), 4.91 (s, 2H), 2.33 (brs, 1H), 1.93 (brs, 6H).

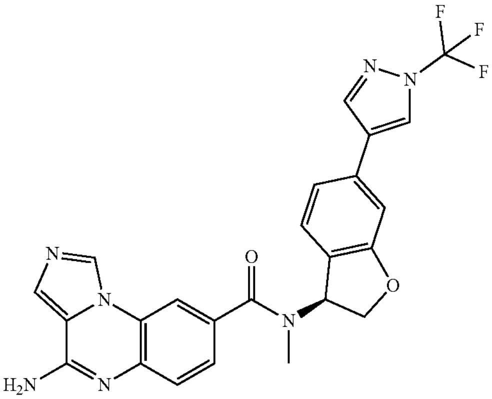 [SMILES: CN(C(=O)c1ccc2nc(N)c3cncn3c2c1)[C@@H]1COc2cc(-c3cnn(C(F)(F)F)c3)ccc21]

Example Ff-203: (S)-4-amino-N-methyl-N-(6-(1-(trifluoromethyl)-1H-pyrazol-4-yl)-2,3-dihydrobenzofuran-3-yl)imidazo[1,5-a]quinoxaline-8-carboxamide. Prepared following the procedure reported for example Ff-95 starting with intermediates 4-((tert-butoxycarbonyl)amino)imidazo[1,5-a]quinoxaline-8-carboxylic acid Ae-1, (S)-6-bromo-N-methyl-2,3-dihydrobenzofuran-3-amine hydrogen chloride Eh-5, and 4-(4,4,5,5-tetramethyl-1,3,2-dioxaborolan-2-yl)-1-(trifluoromethyl)-1H-pyrazole. ES/MS: m/z=494.0 $[M+H]^+$. 1H NMR (400 MHz, Methanol-d4) δ 9.35 (s, 1H), 8.61 (s, 1H), 8.47 (s, 1H), 8.41 (s, 1H), 8.23 (s, 1H), 7.72 (s, 2H), 7.60-7.44 (m, 1H), 7.33 (s, 1H), 7.22 (s, 1H), 6.46 (brs, 0.6H major rotamer), 5.68 (s, 0.4H minor rotamer), 4.79-4.62 (m, 2H), 2.89-2.76 (m, 2H).

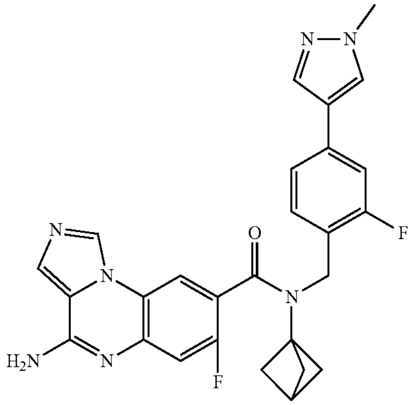 [SMILES: Cn1cc(-c2ccc(CN(C(=O)c3cc4c(cc3F)nc(N)c3cncn34)C34CC(C3)C4)c(F)c2)cn1]

Example Ff-204: 4-amino-N-(bicyclo[1.1.1]pentan-1-yl)-7-fluoro-N-(2-fluoro-4-(1-methyl-1H-pyrazol-4-yl)benzyl)imidazo[1,5-a]quinoxaline-8-carboxamide Prepared following the procedure reported for example Ff-95 starting with intermediates 4-((tert-butoxycarbonyl)amino)-7-fluoroimidazo[1,5-a]quinoxaline-8-carboxylic acid Af-1, N-(4-bromo-2-fluorobenzyl)bicyclo[1.1.1]pentan-1-amine Ec-3, and 1-methyl-4-(4,4,5,5-tetramethyl-1,3,2-dioxaborolan-2-yl)pyrazole. ES/MS: m/z=500.0 $[M+H]^+$. 1H NMR (400 MHz, Methanol-d4) δ 9.41-9.04 (m, 1H), 8.61-8.20 (m, 2H), 8.16-7.71 (m, 2H), 7.69-7.09 (m, 3H), 5.04 (d, J=15.8 Hz, 1H), 4.85-4.48 (m, 2H), 3.94 (d, J=12.6 Hz, 3H), 2.60-2.23 (m, 2H), 1.82 (s, 4H).

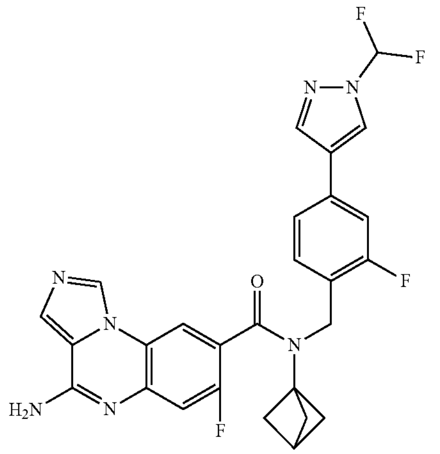 [SMILES: Nc1nc2cc(F)c(C(=O)N(Cc3ccc(-c4cnn(C(F)F)c4)cc3F)C34CC(C3)C4)cc2n2cncc12]

Example Ff-205: 4-amino-N-(bicyclo[1.1.1]pentan-1-yl)-N-(4-(1-(difluoromethyl)-1H-pyrazol-4-yl)-2-fluorobenzyl)-7-fluoroimidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, N-(4-bromo-2-fluorobenzyl)bicyclo[1.1.1]pentan-1-amine Ec-3, and 1-(difluoromethyl)-4-(3,3,4,4-tetramethyl-1lambda3,2,5-bromadioxolan-1-yl)pyrazole. ES/MS: m/z=536.0 $[M+H]^+$. $^1H$ NMR (400 MHz, Methanol-d4) δ 9.35-9.08 (m, 1H), 8.59-8.41 (m, 1H), 8.40-8.26 (m, 1H), 8.15 (s, 1H), 7.72-7.18 (m, 5H), 5.06 (d, J=15.9 Hz, 1H), 4.85-4.61 (m, 1H), 2.38-2.24 (m, 2H), 1.89 (s, 4H).

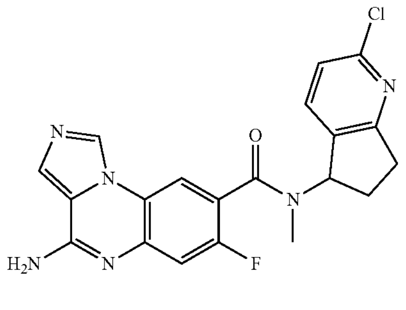 [SMILES: CN(C(=O)c1cc2c(cc1F)nc(N)c1cncn12)C1CCc2nc(Cl)ccc21]

Example Ff-208: 4-amino-N-(2-chloro-6,7-dihydro-5H-cyclopenta[b]pyridin-5-yl)-7-fluoro-N-methylimidazo[1,5-a]quinoxaline-8-carboxamide. Prepared following general procedure VI-F using 4-((tert-butoxycarbonyl)amino)-7-fluoroimidazo[1,5-a]quinoxaline-8-carboxylic acid Af-1 and 2-chloro-N-methyl-6,7-dihydro-5H-cyclopenta[b]pyridin-5-amine hydrochloride Ej-3. ES/MS: m/z=411.0 $[M+H]^+$. 1H NMR (400 MHz, Methanol-d4) δ 9.28 (d, J=5.6 Hz, 1H), 8.59-8.30 (m, 2H), 7.75 (d, J=8.0 Hz, 1H), 7.51 (d, J=9.6 Hz, 1H), 7.38 (dd, J=8.3, 5.3 Hz, 1H), 6.33 (t, J=8.0 Hz, 0.5H rotamer), 5.39 (t, J=8.0 Hz, 0.5H rotamer), 3.26-3.02 (m, 2H), 2.90 (s, 2H), 2.79 (d, J=1.0 Hz, 1H), 2.75-2.61 (m, 1H), 2.39-2.23 (m, 2H).

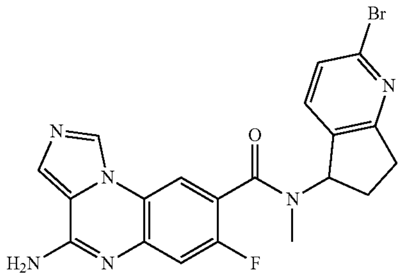

Example Ff-209: 4-amino-N-(2-bromo-6,7-dihydro-5H-cyclopenta[b]pyridin-5-yl)-7-fluoro-N-methylimidazo[1,5-a]quinoxaline-8-carboxamide. Prepared following general procedure VI-F using 4-((tert-butoxycarbonyl)amino)-7-fluoroimidazo[1,5-a]quinoxaline-8-carboxylic acid Af-1 and 2-bromo-N-methyl-6,7-dihydro-5H-cyclopenta[b]pyridin-5-amine hydrogen chloride Ej-4. ES/MS: m/z=455.0 $[M+H]^+$. 1H NMR (400 MHz, Methanol-d4) δ 9.28 (d, J=5.9 Hz, 1H), 8.62-8.26 (m, 2H), 7.86-7.22 (m, 3H), 6.31 (t, J=8.0 Hz, 0.5H, rotamer), 5.36 (t, J=8.0 Hz, 0.5H, rotamer), 3.28-3.01 (m, 2H), 2.90 (s, 1.5H rotamer), 2.79 (m, 1.5H rotamer), 2.73-2.12 (m, 3H).

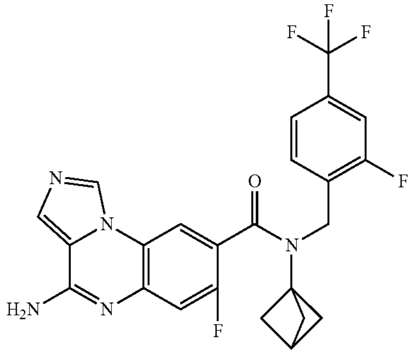 [SMILES: Nc1nc2cc(F)c(C(=O)N(Cc3ccc(C(F)(F)F)cc3F)C34CC(C3)C4)cc2n2cncc12]

Example Ff-210: 4-amino-N-(bicyclo[1.1.1]pentan-1-yl)-7-fluoro-N-(2-fluoro-4-(trifluoromethyl)benzyl)imidazo[1,5-a]quinoxaline-8-carboxamide. Prepared following general procedure VI-F using 4-((tert-butoxycarbonyl)amino)-7-fluoroimidazo[1,5-a]quinoxaline-8-carboxylic acid Af-1 and N-(2-fluoro-4-(trifluoromethyl)benzyl)bicyclo[1.1.1]pentan-1-amine Ec-10. ES/MS: m/z=488.2 $[M+H]^+$. 1H NMR (400 MHz, Methanol-d4) δ 9.31 (s, 1H), 8.60-8.17 (m, 2H), 7.82-7.27 (m, 4H), 5.27-4.91 (m, 2H), 2.48 (d, J=156.4 Hz, 2H), 1.84 (s, 5H).

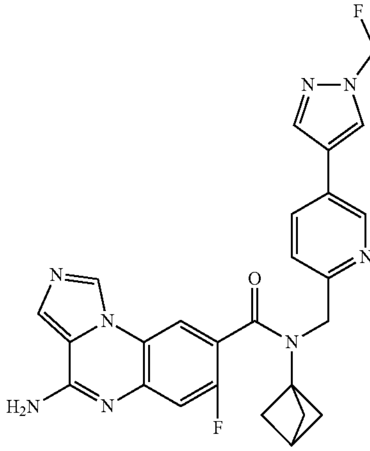

Example Ff-211: 4-amino-N-(bicyclo[1.1.1]pentan-1-yl)-7-fluoro-N-((5-(1-(trifluoromethyl)-1H-pyrazol-4-yl)pyridin-2-yl)methyl)imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, N-((5-bromopyridin-2-yl)methyl)bicyclo[1.1.1]pentan-1-amine Ec-11, and 4-(4,4,5,5-tetramethyl-1,3,2-dioxaborolan-2-yl)-1-(trifluoromethyl)pyrazole. ES/MS: m/z=537.0 $[M+H]^+$. 1H NMR (400 MHz, Methanol-d4) δ 9.36-9.08 (m, 1H), 8.99-8.67 (m, 2H), 8.59-7.92 (m, 4H), 7.75-7.20 (m, 2H), 5.30-4.93 (m, 1H), 4.67 (s, 1H), 2.85-2.12 (m, 3H), 1.84 (s, 4H).

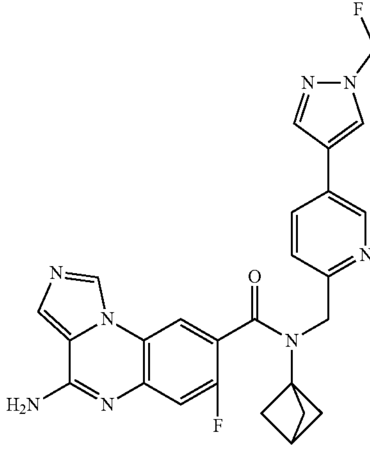

Example Ff-212: 4-amino-N-(bicyclo[1.1.1]pentan-1-yl)-N-((5-(1-(difluoromethyl)-1H-pyrazol-4-yl)pyridin-2-yl)methyl)-7-fluoroimidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, N-((5-bromopyridin-2-yl)methyl)bicyclo[1.1.1]pentan-1-amine Ec-11, and 1-(difluoromethyl)-4-(4,4,5,5-tetramethyl-1,3,2-dioxaborolan-2-yl)pyrazole. ES/MS: m/z=519.0 $[M+H]^+$. $^1$H NMR (400 MHz, Methanol-d4) δ 9.30 (s, 0.7H, major rotamer), 9.12 (s, 0.3H, minor rotamer), 8.91 (s, 0.7H, major rotamer), 8.80 (s, 0.3H, minor rotamer), 88.75-8.31 (m, 3H), 8.30-7.94 (m, 2H), 7.78-7.11 (m, 3H), 5.23-4.91 (m, 1H), 4.66 (s, 1H), 2.67 (s, 1H), 2.26 (d, J=13.3 Hz, 2H), 1.84 (s, 5H).

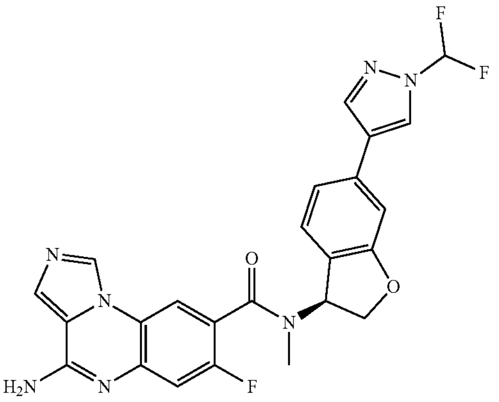 [SMILES: CN(C(=O)c1cc2c(cc1F)nc(N)c1cncn12)[C@@H]1COc2cc(-c3cnn(C(F)F)c3)ccc21]

Example Ff-213: (S)-4-amino-N-(6-(1-(difluoromethyl)-1H-pyrazol-4-yl)-2,3-dihydrobenzofuran-3-yl)-7-fluoro-N-methylimidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine hydrochloride Eh-5, and 1-(difluoromethyl)-4-(4,4,5,5-tetramethyl-1,3,2-dioxaborolan-2-yl)pyrazole. ES/MS: m/z=494.0 $[M+H]^+$. $^1$H NMR (400 MHz, Methanol-d4) δ 9.27 (s, 1H), 8.68-8.28 (m, 3H), 8.10 (d, J=15.1 Hz, 1H), 7.69-6.37 (m, 5H), 5.59 (t, J=6.2 Hz, 1H), 4.83 (dd, J=10.6, 8.7 Hz, 1H), 4.66 (dd, J=10.6, 3.4 Hz, 1H), 2.97-2.62 (m, 3H).

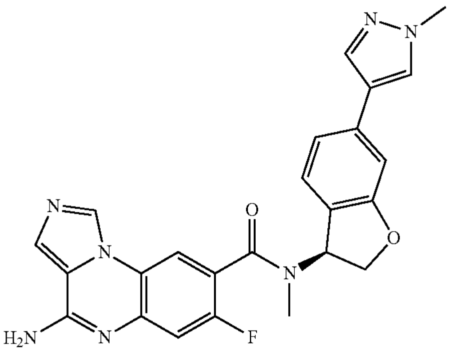 [SMILES: CN(C(=O)c1cc2c(cc1F)nc(N)c1cncn12)[C@@H]1COc2cc(-c3cnn(C)c3)ccc21]

Example Ff-214: (S)-4-amino-7-fluoro-N-methyl-N-(6-(1-methyl-1H-pyrazol-4-yl)-2,3-dihydrobenzofuran-3-yl)imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine hydrochloride Eh-5, and 1-methyl-4-(4,4,5,5-tetramethyl-1,3,2-dioxaborolan-2-yl)pyrazole. ES/MS: m/z=458.0 $[M+H]^+$. $^1$H NMR (400 MHz, Methanol-d4) δ 9.27 (s, 1H), 8.70-8.27 (m, 2H), 8.17-7.66 (m, 2H), 7.59-6.34 (m, 4H), 5.55 (d, J=6.8 Hz, 1H), 4.80 (dd, J=10.6, 8.6 Hz, 1H), 4.64 (dd, J=10.6, 3.3 Hz, 1H), 3.93 (d, J=5.7 Hz, 3H), 2.98-2.61 (m, 3H).

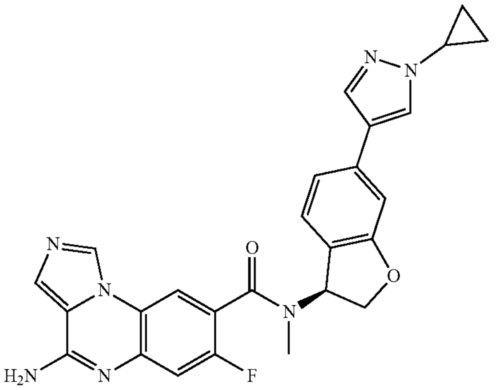 [SMILES: CN(C(=O)c1cc2c(cc1F)nc(N)c1cncn12)[C@@H]1COc2cc(-c3cnn(C4CC4)c3)ccc21]

Example Ff-215: (S)-4-amino-N-(6-(1-cyclopropyl-1H-pyrazol-4-yl)-2,3-dihydrobenzofuran-3-yl)-7-fluoro-N-methylimidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine hydrogen chloride Eh-5, and 1-cyclopropyl-4-(4,4,5,5-tetramethyl-1,3,2-dioxaborolan-2-yl)pyrazole. ES/MS: m/z=484.0 $[M+H]^+$. $^1H$ NMR (400 MHz, Methanol-d4) δ 9.27 (s, 1H), 8.62-8.24 (m, 2H), 8.19-7.70 (m, 2H), 7.63-6.94 (m, 4H), 6.49 (dd, J=8.6, 3.3 Hz, 0.5H, rotamer), 5.55 (s, 0.5H, rotamer), 4.85-4.52 (m, 2H), 3.69 (dtd, J=9.4, 7.2, 3.9 Hz, 1H), 3.02-2.56 (m, 3H), 1.24-0.94 (m, 4H).

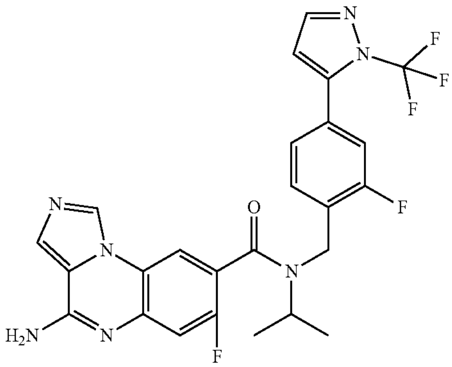 [SMILES: CC(C)N(Cc1ccc(-c2ccnn2C(F)(F)F)cc1F)C(=O)c1cc2c(cc1F)nc(N)c1cncn12]

Example Ff-216: Prepared following the procedure reported for example Ff-95 starting with intermediates 4-((tert-butoxycarbonyl)amino)-7-fluoroimidazo[1,5-a]quinoxaline-8-carboxylic acid Af-1, N-(4-bromo-2-fluorobenzyl)propan-2-amine Ed-9, and 5-(4,4,5,5-tetramethyl-1,3,2-dioxaborolan-2-yl)-1-(trifluoromethyl)pyrazole. ES/MS: m/z=530.0 $[M+H]^+$. 1H NMR (400 MHz, Methanol-d4) δ 9.32 (s, 0.8H, major rotamer), 9.17 (s, 0.2H, minor rotamer), 8.60-8.19 (m, 2H), 8.01-7.76 (m, 1H), 7.67-7.26 (m, 5H), 6.72-6.33 (m, 1H), 4.82-4.54 (m, 1H), 4.13 (p, J=6.6 Hz, 1H), 1.39 (d, J=6.8 Hz, 1H, minor rotamer),), 1.25 (d, J=6.7 Hz, 5H, major rotamer).

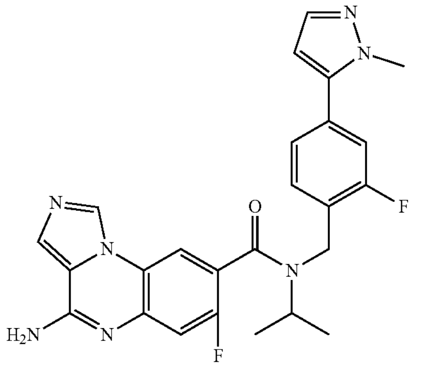 [SMILES: CC(C)N(Cc1ccc(-c2ccnn2C)cc1F)C(=O)c1cc2c(cc1F)nc(N)c1cncn12]

Example Ff-217: 4-amino-7-fluoro-N-(2-fluoro-4-(1-methyl-1H-pyrazol-5-yl)benzyl)-N-isopropylimidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, N-(4-bromo-2-fluorobenzyl)propan-2-amine Ed-9, and (2-methylpyrazol-3-yl)boronic acid. ES/MS: m/z=476.0 $[M+H]^+$. 1H NMR (400 MHz, Methanol-d4) δ 9.35 (d, J=0.7 Hz, 0.8H, major rotamer), 9.18 (s, 0.2H, minor rotamer), 8.71-8.05 (m, 2H), 7.78-7.02 (m, 5H), 6.45 (d, J=2.0 Hz, 0.8H, major rotamer), 6.29 (d, J=2.0 Hz, 0.2H, minor rotamer), 4.95 (s, 1H), 4.85-4.62 (m, 1H), 3.93 (s, 2H, major rotamer), 3.80 (s, 1H, minor rotamer), 1.40 (d, J=6.8 Hz, 1H, minor rotamer), 1.25 (d, J=6.6 Hz, 5H, major rotamer).

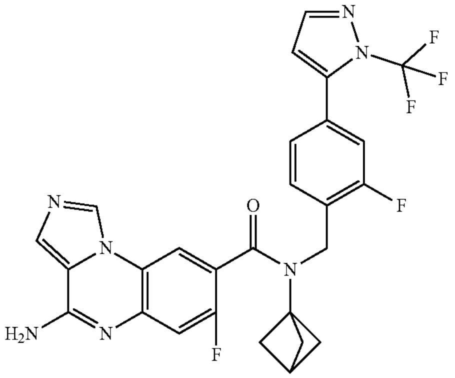 [SMILES: Nc1nc2cc(F)c(C(=O)N(Cc3ccc(-c4ccnn4C(F)(F)F)cc3F)C34CC(C3)C4)cc2n2cncc12]

Example Ff-218: 4-amino-N-(bicyclo[1.1.1]pentan-1-yl)-7-fluoro-N-(2-fluoro-4-(1-(trifluoromethyl)-1H-pyrazol-5-yl)benzyl)imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, N-(4-bromo-2-fluorobenzyl)bicyclo[1.1.1]pentan-1-amine Ec-3, and 5-(4,4,5,5-tetramethyl-1,3,2-dioxaborolan-2-yl)-1-(trifluoromethyl)pyrazole. ES/MS: m/z=554.0 $[M+H]^+$. 1H NMR (400 MHz, Methanol-d4) δ 9.31 (s, 1H), 8.62-8.21 (m, 2H), 7.86 (s, 1H), 7.73-7.10 (m, 4H), 6.65 (s, 1H), 5.20-4.92 (m, 2H), 2.29 (s, 2H), 1.90 (s, 5H).

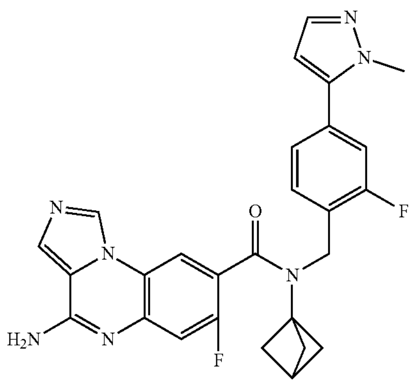 [SMILES: Cn1nccc1-c1ccc(CN(C(=O)c2cc3c(cc2F)nc(N)c2cncn23)C23CC(C2)C3)c(F)c1]

Example Ff-219: 4-amino-N-(bicyclo[1.1.1]pentan-1-yl)-7-fluoro-N-(2-fluoro-4-(1-methyl-1H-pyrazol-5-yl)benzyl) imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, N-(4-bromo-2-fluorobenzyl)bicyclo[1.1.1]pentan-1-amine Ec-3, and (2-methylpyrazol-3-yl)boronic acid. ES/MS: m/z=500.0 $[M+H]^+$. 1H NMR (400 MHz, Methanol-d4) δ 9.33 (s, 1H), 8.66-8.20 (m, 2H), 7.73-7.48 (m, 3H), 7.47-7.31 (m, 2H), 6.64-6.20 (m, 1H), 5.09 (d, J=16.0 Hz, 1H), 4.69 (s, 1H), 3.94 (s, 3H), 2.29 (s, 1H), 1.91 (s, 6H).

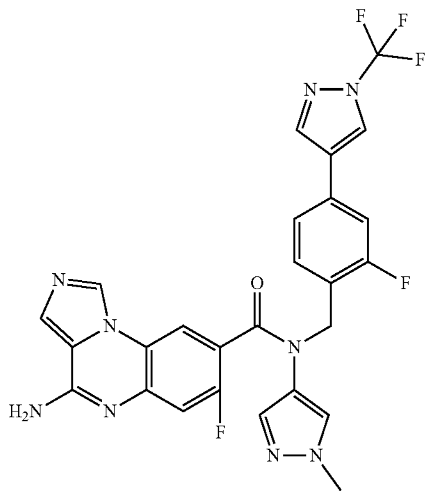 [SMILES: Cn1cc(N(Cc2ccc(-c3cnn(C(F)(F)F)c3)cc2F)C(=O)c2cc3c(cc2F)nc(N)c2cncn23)cn1]

Example Ff-220: 4-amino-7-fluoro-N-(2-fluoro-4-(1-(trifluoromethyl)-1H-pyrazol-4-yl)benzyl)-N-(1-methyl-1H-pyrazol-4-yl)imidazo[1,5-a]quinoxaline-8-carboxamide: Prepared following the procedure reported for example Ff-95 starting with intermediates 4-((tert-butoxycarbonyl) amino)-7-fluoroimidazo[1,5-a]quinoxaline-8-carboxylic acid Af-1, N-(4-bromo-2-fluorobenzyl)-1-methyl-1H-pyrazol-4-amine Ed-15, and 4-(4,4,5,5-tetramethyl-1,3,2-dioxaborolan-2-yl)-1-(trifluoromethyl)pyrazole. ES/MS: m/z=568.0 $[M+H]^+$. $^1H$ NMR (400 MHz, Methanol-d4) δ 9.23 (s, 1H), 8.68 (s, 1H), 8.38 (d, J=5.7 Hz, 1H), 8.34 (d, J=0.6 Hz, 1H), 8.30-8.23 (m, 1H), 7.59-7.43 (m, 4H), 7.26-7.13 (m, 2H), 5.15 (s, 2H), 3.65 (s, 3H).

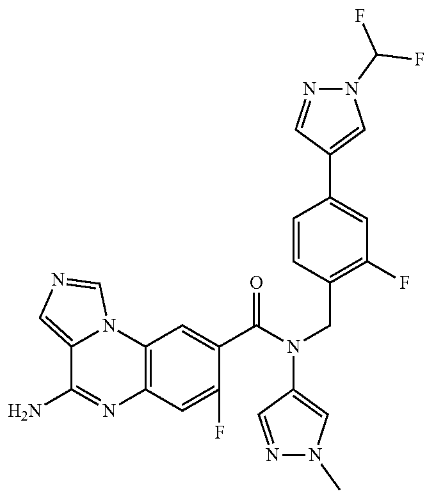 [SMILES: Cn1cc(N(Cc2ccc(-c3cnn(C(F)F)c3)cc2F)C(=O)c2cc3c(cc2F)nc(N)c2cncn23)cn1]

Example Ff-221: 4-amino-N-(4-(1-(difluoromethyl)-1H-pyrazol-4-yl)-2-fluorobenzyl)-7-fluoro-N-(1-methyl-1H-pyrazol-4-yl)imidazo[1,5-a]quinoxaline-8-carboxamide. Prepared following the procedure reported for example Ff-95 starting with intermediates 4-((tert-butoxycarbonyl) amino)-7-fluoroimidazo[1,5-a]quinoxaline-8-carboxylic acid Af-1, N-(4-bromo-2-fluorobenzyl)-1-methyl-1H-pyrazol-4-amine Ed-15, and 1-(difluoromethyl)-4-(4,4,5,5-tetramethyl-1,3,2-dioxaborolan-2-yl)pyrazole. ES/MS: m/z=550.0 $[M+H]^+$. $^1H$ NMR (400 MHz, Methanol-d4) δ 9.29-9.15 (m, 1H), 8.52 (d, J=0.7 Hz, 1H), 8.43-8.25 (m, 2H), 8.14 (s, 1H), 7.57-7.35 (m, 5H), 7.29-7.15 (m, 2H), 5.14 (s, 2H), 3.65 (s, 3H).

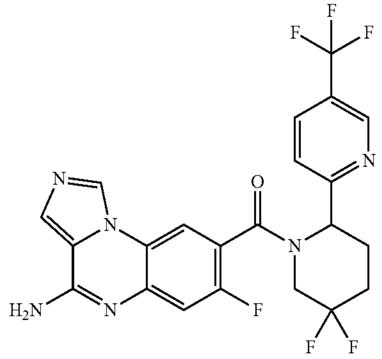 [SMILES: Nc1nc2cc(F)c(C(=O)N3CC(F)(F)CCC3c3ccc(C(F)(F)F)cn3)cc2n2cncc12]

Example Ff-222: (4-amino-7-fluoroimidazo[1,5-a]quinoxalin-8-yl)(5,5-difluoro-2-(5-(trifluoromethyl)pyridin-2-yl)piperidin-1-yl)methanone. Prepared following general procedure VI-F using 4-((tert-butoxycarbonyl)amino)-7-fluoroimidazo[1,5-a]quinoxaline-8-carboxylic acid Af-1 and 2-(5,5-difluoropiperidin-2-yl)-5-(trifluoromethyl)pyridine hydrochloride Eai-12. ES/MS: m/z=495.0 $[M+H]^+$. $^1H$ NMR (400 MHz, Methanol-d4) δ 9.31 (s, 1H), 8.60-8.17 (m, 2H), 7.82-7.27 (m, 4H), 5.27-4.91 (m, 2H), 2.48 (m, 2H), 1.84 (s, 3H).

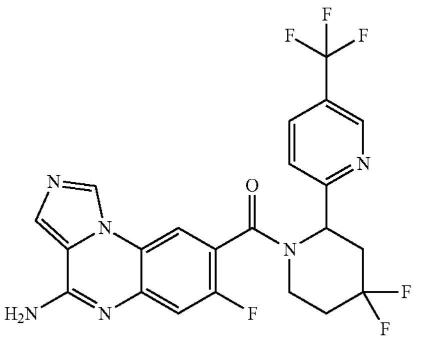 [SMILES: Nc1nc2cc(F)c(C(=O)N3CCC(F)(F)CC3c3ccc(C(F)(F)F)cn3)cc2n2cncc12]

Example Ff-223: (4-amino-7-fluoroimidazo[1,5-a]quinoxalin-8-yl)(4,4-difluoro-2-(5-(trifluoromethyl)pyridin-2-yl)piperidin-1-yl)methanone. Prepared following general procedure VI-F using 4-((tert-butoxycarbonyl)amino)-7-fluoroimidazo[1,5-a]quinoxaline-8-carboxylic acid Af-1 and 2-(4,4-difluoropiperidin-2-yl)-5-(trifluoromethyl)pyridine hydrogen chloride Eai-13. ES/MS: m/z=495.0 $[M+H]^+$. $^1H$ NMR (400 MHz, Methanol-d4) δ 9.31 (s, 1H), 8.96 (s, 1H), 8.61-8.01 (m, 3H), 7.81-7.21 (m, 2H), 5.82 (d, J=374.6 Hz, 1H), 3.94-3.63 (m, 2H), 2.90-2.43 (m, 2H), 2.34-1.74 (m, 2H).

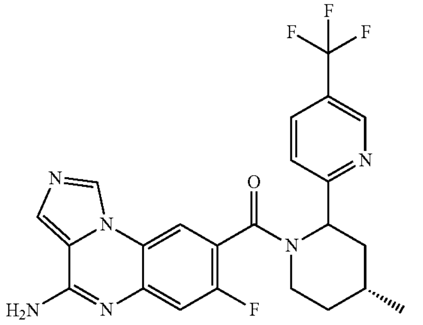 [SMILES: C[C@@H]1CCN(C(=O)c2cc3c(cc2F)nc(N)c2cncn23)C(c2ccc(C(F)(F)F)cn2)C1]

Example Ff-224: (4-amino-7-fluoroimidazo[1,5-a]quinoxalin-8-yl)((4R)-4-methyl-2-(5-(trifluoromethyl)pyridin-2-yl)piperidin-1-yl)methanone. Prepared following general procedure VI-F using 4-((tert-butoxycarbonyl)amino)-7-fluoroimidazo[1,5-a]quinoxaline-8-carboxylic acid Af-1 and 2-((4R)-4-methylpiperidin-2-yl)-5-(trifluoromethyl)pyridine hydrochloride Eai-14. ES/MS: m/z=473.0 $[M+H]^+$. $^1H$ NMR (400 MHz, Methanol-d4) δ 9.22 (s, 1H), 8.89 (s, 1H), 8.43-7.92 (m, 3H), 7.68 (s, 1H), 7.41 (s, 1H), 5.49 (s, 1H), 4.02-3.44 (m, 3H), 2.37-1.82 (m, 1H), 1.41-1.24 (m, 2H), 0.96 (s, 4H).

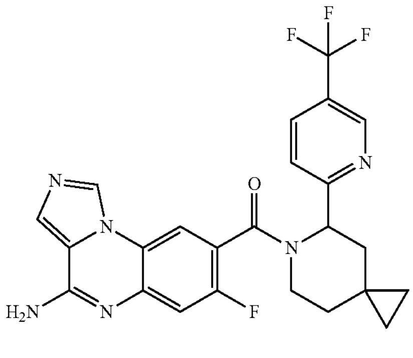 [SMILES: Nc1nc2cc(F)c(C(=O)N3CCC4(CC4)CC3c3ccc(C(F)(F)F)cn3)cc2n2cncc12]

Example Ff-225: (4-amino-7-fluoroimidazo[1,5-a]quinoxalin-8-yl)(5-(5-(trifluoromethyl)pyridin-2-yl)-6-azaspiro[2.5]octan-6-yl)methanone. Prepared following general procedure VI-F using 4-((tert-butoxycarbonyl)amino)-7-fluoroimidazo[1,5-a]quinoxaline-8-carboxylic acid Af-1 and 5-(5-(trifluoromethyl)pyridin-2-yl)-6-azaspiro[2.5]octane hydrochloride Eai-15. ES/MS: m/z=485.0 $[M+H]^+$. $^1H$ NMR (400 MHz, Methanol-d4) δ 9.34 (s, 1H), 8.94 (s, 0.7H, major rotamer), 8.88 (s, 0.3H, minor rotamer), 8.52 (d, J=5.7 Hz, 1H), 8.41 (s, 0.7H, major rotamer), 8.35 (s, 0.3H, minor rotamer), 8.26-7.99 (m, 1H), 7.82-7.40 (m, 2H), 6.12 (s, 1H), 3.70 (d, J=13.6 Hz, 2H), 2.74-1.85 (m, 3H), 1.22-0.76 (m, 1H), 0.48-0.22 (m, 4H).

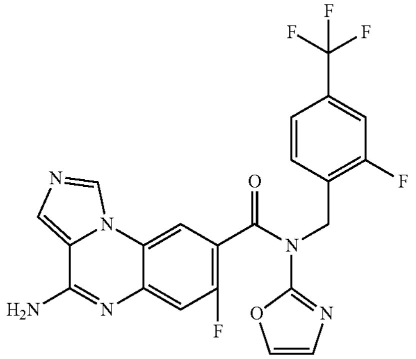 [SMILES: Nc1nc2cc(F)c(C(=O)N(Cc3ccc(C(F)(F)F)cc3F)c3ncco3)cc2n2cncc12]

Example Ff-226: 4-amino-7-fluoro-N-(2-fluoro-4-(trifluoromethyl)benzyl)-N-(oxazol-2-yl)imidazo[1,5-a]quinoxaline-8-carboxamide: Prepared following general procedure VI-F using 4-((tert-butoxycarbonyl)amino)-7-fluoroimidazo[1,5-a]quinoxaline-8-carboxylic acid Af-1 and N-(2-fluoro-4-(trifluoromethyl)benzyl)oxazol-2-amine Ed-16. ES/MS: m/z=489.0 $[M+H]^+$. $^1H$ NMR (400 MHz, Methanol-d4) δ 9.19 (s, 1H), 8.47 (d, J=6.2 Hz, 1H), 8.15 (m, 1H), 7.77 (d, J=7.7 Hz, 1H), 7.74-7.65 (m, 1H), 7.55-7.48 (m, 2H), 7.20 (d, J=10.8 Hz, 1H), 6.95 (d, J=1.0 Hz, 1H), 5.39 (s, 2H).

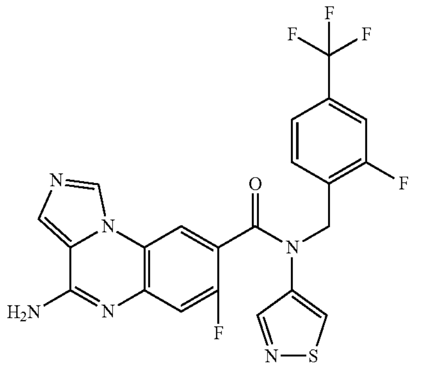 [SMILES: Nc1nc2cc(F)c(C(=O)N(Cc3ccc(C(F)(F)F)cc3F)c3cnsc3)cc2n2cncc12]

Example Ff-227: 4-amino-7-fluoro-N-(2-fluoro-4-(trifluoromethyl)benzyl)-N-(isothiazol-4-yl)imidazo[1,5-a]quinoxaline-8-carboxamide. Prepared following general procedure VI-F using 4-((tert-butoxycarbonyl)amino)-7-fluoroimidazo[1,5-a]quinoxaline-8-carboxylic acid Af-1 and N-(2-fluoro-4-(trifluoromethyl)benzyl)isothiazol-4-amine Ec-12. ES/MS: m/z=505.0 $[M+H]^+$. $^1H$ NMR (400 MHz, Methanol-d4) δ 9.18 (d, J=0.7 Hz, 1H), 8.71 (s, 1H), 8.42 (d, J=5.8 Hz, 1H), 8.30 (d, J=4.0 Hz, 2H), 7.76 (d, J=7.7 Hz, 1H), 7.56-7.47 (m, 2H), 7.18 (d, J=10.0 Hz, 1H), 5.32 (s, 2H).

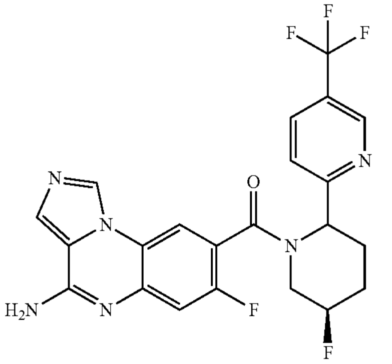 [SMILES: Nc1nc2cc(F)c(C(=O)N3C[C@H](F)CCC3c3ccc(C(F)(F)F)cn3)cc2n2cncc12]

Example Ff-228: (4-amino-7-fluoroimidazo[1,5-a]quinoxalin-8-yl)((5R)-5-fluoro-2-(5-(trifluoromethyl)pyridin-2-yl)piperidin-1-yl)methanone. Prepared following general procedure VI-F using 4-((tert-butoxycarbonyl)amino)-7-fluoroimidazo[1,5-a]quinoxaline-8-carboxylic acid Af-1 and 2-((5R)-5-fluoropiperidin-2-yl)-5-(trifluoromethyl)pyridine hydrochloride Eai-16. ES/MS: m/z=477.0 $[M+H]^+$. $^1H$ NMR (400 MHz, Methanol-d4) δ 9.30 (s, 1H), 8.97 (s, 1H), 8.57-8.13 (m, 3H), 7.83-7.46 (m, 2H), 6.32-5.90 (m, 1H), 5.21-4.45 (m, 1H), 4.01-3.46 (m, 2H), 2.82-1.39 (m, 4H).

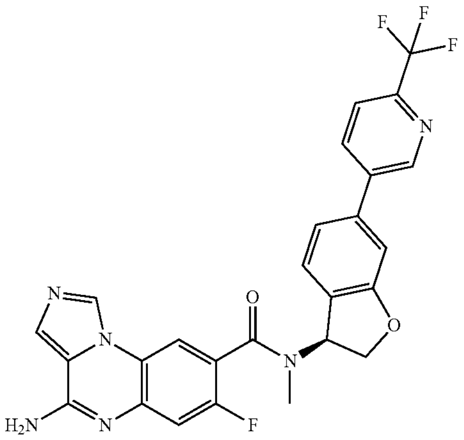 [SMILES: CN(C(=O)c1cc2c(cc1F)nc(N)c1cncn12)[C@@H]1COc2cc(-c3ccc(C(F)(F)F)nc3)ccc21]

Example Ff-229: (S)-4-amino-7-fluoro-N-methyl-N-(6-(6-(trifluoromethyl)pyridin-3-yl)-2,3-dihydrobenzofuran-3-yl)imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine hydrogen chloride Eh-5, and 5-(4,4,5,5-tetramethyl-1,3,2-dioxaborolan-2-yl)-2-(trifluoromethyl)pyridine. ES/MS: m/z=523.0 $[M+H]^+$. $^1H$ NMR (400 MHz, Methanol-d4) δ 9.28 (s, 1H), 9.08-8.86 (m, 1H), 8.73-8.36 (m, 2H), 8.36-8.17 (m, 1H), 8.01-7.83 (m, 1H), 7.64-7.11 (m, 4H), 6.59 (dd, J=8.8, 3.5 Hz, 0.6H, major rotamer), 5.68 (t, J=6.3 Hz, 0.4H, minor rotamer), 4.91 (s, 1H), 4.72 (dd, J=10.6, 3.6 Hz, 1H), 2.96-2.61 (m, 3H).

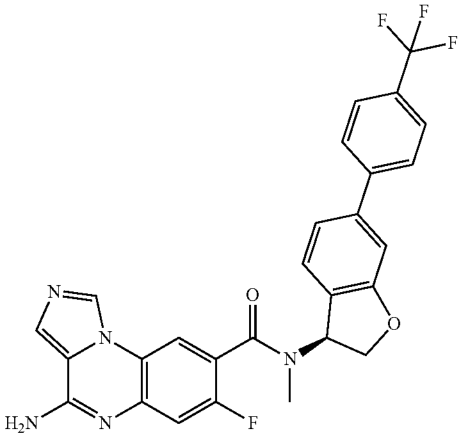

Example Ff-230: (S)-4-amino-7-fluoro-N-methyl-N-(6-(4-(trifluoromethyl)phenyl)-2,3-dihydrobenzofuran-3-yl) imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine hydrogen chloride Eh-5, and [4-(trifluoromethyl)phenyl]boronic acid. ES/MS: m/z=522.0 $[M+H]^+$. $^1H$ NMR (400 MHz, Methanol-d4) δ 9.45-9.18 (m, 1H), 8.69-8.31 (m, 1H), 8.01-7.72 (m, 4H), 7.65 (d, J=7.9 Hz, 1H), 7.59-7.10 (m, 4H), 6.57 (dd, J=8.7, 3.4 Hz, 0.6H, major rotamer), 5.65 (t, J=6.3 Hz, 0.4H, minor rotamer), 4.85 (d, J=5.3 Hz, 1H), 4.70 (dd, J=10.6, 3.5 Hz, 1H), 2.98-2.59 (m, 3H).

Example Ff-231: (S)-4-amino-7-fluoro-N-methyl-N-(6-(2-(trifluoromethyl)thiazol-4-yl)-2,3-dihydrobenzofuran-3-yl)imidazo[1,5-a]quinoxaline-8-carboxamide

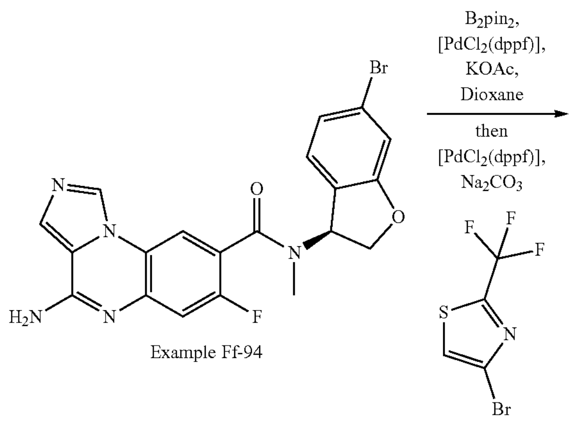

Example Ff-94

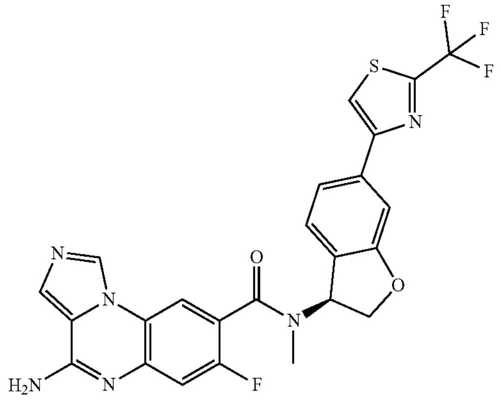

Example Ff-231

To a solution of (S)-4-amino-N-(6-bromo-2,3-dihydrobenzofuran-3-yl)-7-fluoro-N-methylimidazo[1,5-a]quinoxaline-8-carboxamide Ff-94 (20.0 mg, 0.0441 mmol), $PdCl_2$(dppf) (4.9 mg, 0.00661 mmol), bis(pinacolato)diboron (13.4 mg, 0.0529 mmol) in dioxane (2 mL), was added potassium propionate (14.8 mg, 0.132 mmol). The mixture was bubbled through argon for 1 minute and left to stir at 110 C for 1 hour. After, 4-bromo-2-(trifluoromethyl)thiazole (12.3 mg, 0.0529 mmol), 2M $Na_2CO_3$ (11.7 mg, 0.110 mmol), and $PdCl_2$(dppf) (1.6 mg, 0.00220 mmol) was added to the mixture and bubbled through argon for 1 minute. The reaction was left to stir at 90 C for 6 hours. The mixture was filtered through a pad of celite and anhydrous $MgSO_4$ and the solution was reduced under pressure and the crude was purified by preparative HPLC. ES/MS: m/z=529.0 $[M+H]^+$. $^1H$ NMR (400 MHz, Methanol-d4) δ 9.28 (s, 1H), 8.47 (d, J=5.9 Hz, 1H), 8.38 (s, 1H), 8.25 (d, J=13.5 Hz, 1H), 7.67 (ddd, J=19.4, 7.8, 1.5 Hz, 1H), 7.58-7.35 (m, 3H), 6.55 (dd, J=8.8, 3.5 Hz, 0.6H, major rotamer), 5.63 (t, J=6.2 Hz, 0.4H, minor rotamer), 4.70 (dd, J=10.6, 3.5 Hz, 2H), 3.01-2.69 (m, 3H).

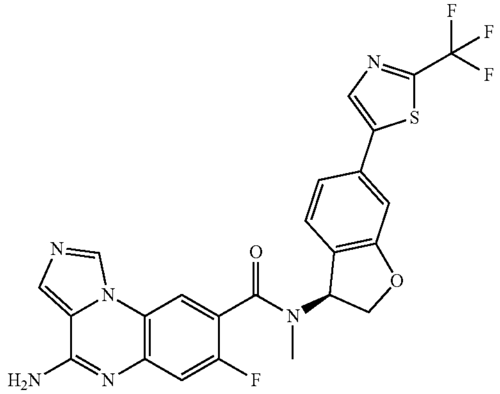 [SMILES: CN(C(=O)c1cc2c(cc1F)nc(N)c1cncn12)[C@@H]1COc2cc(-c3cnc(C(F)(F)F)s3)ccc21]

Example Ff-232: (S)-4-amino-7-fluoro-N-methyl-N-(6-(2-(trifluoromethyl)thiazol-5-yl)-2,3-dihydrobenzofuran-3-yl)imidazo[1,5-a]quinoxaline-8-carboxamide. Prepared following the procedure reported for example Ff-231 starting with intermediates (S)-4-amino-N-(6-bromo-2,3-dihydrobenzofuran-3-yl)-7-fluoro-N-methylimidazo[1,5-a]quinoxaline-8-carboxamide Ff-94 and 5-bromo-2-(trifluoromethyl)thiazole. ES/MS: m/z=529.0 $[M+H]^+$. 1H NMR (400 MHz, Methanol-d4) δ 9.27 (s, 1H), 8.67-8.21 (m, 3H), 7.77-7.05 (m, 4H), 6.56 (dd, J=8.8, 3.6 Hz, 1H), 5.65 (t, J=6.4 Hz, 1H), 4.72 (dd, J=10.7, 3.6 Hz, 1H), 2.97-2.47 (m, 3H).

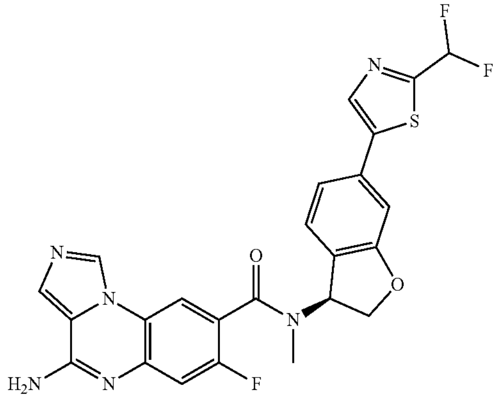 [SMILES: CN(C(=O)c1cc2c(cc1F)nc(N)c1cncn12)[C@@H]1COc2cc(-c3cnc(C(F)F)s3)ccc21]

Example Ff-233: (S)-4-amino-N-(6-(2-(difluoromethyl)thiazol-5-yl)-2,3-dihydrobenzofuran-3-yl)-7-fluoro-N-methylimidazo[1,5-a]quinoxaline-8-carboxamide. Prepared following the procedure reported for example Ff-231 starting with intermediates (S)-4-amino-N-(6-bromo-2,3-dihydrobenzofuran-3-yl)-7-fluoro-N-methylimidazo[1,5-a]quinoxaline-8-carboxamide Ff-94 and 5-bromo-2-(difluoromethyl)thiazole. ES/MS: m/z=511.0 $[M+H]^+$. $^1H$ NMR (400 MHz, Methanol-d4) δ 9.27 (s, 1H), 8.51-8.33 (m, 2H), 8.32-8.14 (m, 1H), 7.64-7.23 (m, 4H), 7.03 (td, J=54.5, 4.2 Hz, 1H), 6.55 (dd, J=8.8, 3.5 Hz, 0.5H, rotamer), 5.64 (t, J=6.3 Hz, 0.5H, rotamer), 4.86-4.53 (m, 2H), 2.98-2.73 (m, 3H).

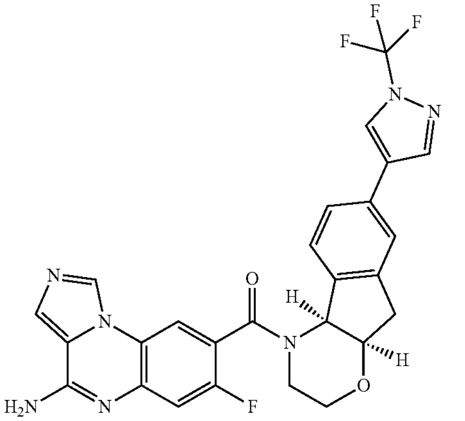 [SMILES: Nc1nc2cc(F)c(C(=O)N3CCO[C@@H]4Cc5cc(-c6cnn(C(F)(F)F)c6)ccc5[C@@H]43)cc2n2cncc12]

Example Ff-234: (4-amino-7-fluoroimidazo[1,5-a]quinoxalin-8-yl)((4aS,9aR)-7-(1-(trifluoromethyl)-1H-pyrazol-4-yl)-2,3,9,9a-tetrahydroindeno[2,1-b][1,4]oxazin-4(4aH)-yl)methanone: Prepared following the procedure reported for example Ff-95 starting with intermediates 4-((tert-butoxycarbonyl)amino)-7-fluoroimidazo[1,5-a]quinoxaline-8-carboxylic acid Af-1, (4aS,9aR)-7-bromo-2,3,4,4a,9,9a-hexahydroindeno[2,1-b][1,4]oxazine Et-1, and 4-(4,4,5,5-tetramethyl-1,3,2-dioxaborolan-2-yl)-1-(trifluoromethyl) pyrazole. ES/MS: m/z=538.0 $[M+H]^+$. $^1$H NMR (400 MHz, Methanol-d4) δ 9.28 (s, 1H), 8.68-8.45 (m, 2H), 8.40-8.05 (m, 2H), 7.66-7.26 (m, 4H), 6.01 (s, 0.8H, major rotamer), 5.07 (s, 0.2H, minor rotamer), 4.50 (dt, J=19.0, 3.8 Hz, 1H), 4.02-3.59 (m, 3H), 3.53-3.38 (m, 1H), 3.11-2.79 (m, 2H).

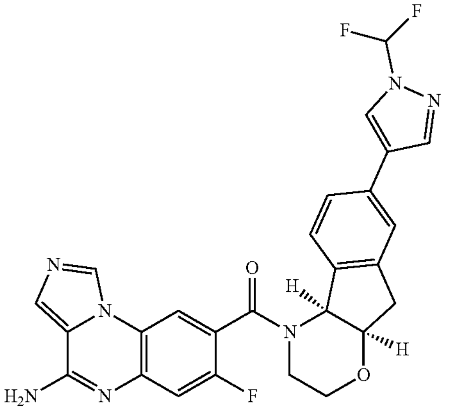 [SMILES: Nc1nc2cc(F)c(C(=O)N3CCO[C@@H]4Cc5cc(-c6cnn(C(F)F)c6)ccc5[C@@H]43)cc2n2cncc12]

Example Ff-235: (4-amino-7-fluoroimidazo[1,5-a]quinoxalin-8-yl)((4aS,9aR)-7-(1-(difluoromethyl)-1H-pyrazol-4-yl)-2,3,9,9a-tetrahydroindeno[2,1-b][1,4]oxazin-4(4aH)-yl)methanone. Prepared following the procedure reported for Ff-95 starting with intermediates 4-((tert-butoxycarbonyl)amino)-7-fluoroimidazo[1,5-a]quinoxaline-8-carboxylic acid Af-1, (4aS,9aR)-7-bromo-2,3,4,4a,9,9a-hexahydroindeno[2,1-b][1,4]oxazine Et-1, and 1-(difluoromethyl)-4-(4,4,5,5-tetramethyl-1,3,2-dioxaborolan-2-yl)pyrazole. ES/MS: m/z=520.0 $[M+H]^+$. $^1$H NMR (400 MHz, Methanol-d4) δ 9.30 (s, 1H), 8.71-8.51 (m, 1H), 8.48-8.29 (m, 1H), 8.10 (m, 1H), 7.75-7.17 (m, 5H), 6.01 (s, 0.7H, major rotamer), 5.07 (s, 0.3H, minor rotamer), 4.50 (dt, J=18.4, 3.9 Hz, 2H), 3.99-3.37 (m, 3H), 3.21-2.82 (m, 3H).

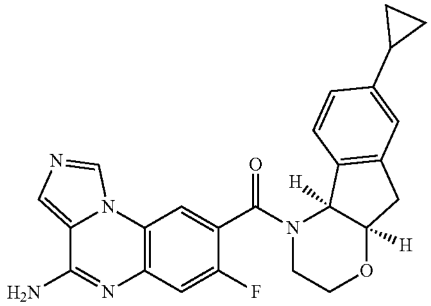 [SMILES: Nc1nc2cc(F)c(C(=O)N3CCO[C@@H]4Cc5cc(C6CC6)ccc5[C@@H]43)cc2n2cncc12]

Example Ff-236: (4-amino-7-fluoroimidazo[1,5-a]quinoxalin-8-yl)((4aS,9aR)-7-cyclopropyl-2,3,9,9a-tetrahydroindeno[2,1-b][1,4]oxazin-4(4aH)-yl)methanone Prepared following the procedure reported for Ff-95 starting with intermediates 4-((tert-butoxycarbonyl)amino)-7-fluoroimidazo[1,5-a]quinoxaline-8-carboxylic acid Af-1, (4aS,9aR)-7-bromo-2,3,4,4a,9,9a-hexahydroindeno[2,1-b][1,4]oxazine Et-1, and cyclopropylboronic acid (using cataCXium Pd G3 and KOAc as an additive). ES/MS: m/z=444.0 $[M+H]^+$. $^1$H NMR (400 MHz, Methanol-d4) δ 9.40-9.15 (m, 1H), 8.65-8.43 (m, 1H), 8.41-8.26 (m, 1H), 7.59-7.35 (m, 1H), 7.30-6.78 (m, 3H), 5.91 (s, 1H), 4.43 (dt, J=14.8, 3.8 Hz, 1H), 3.92-3.35 (m, 3H), 3.27-2.64 (m, 3H), 1.94 (s, 1H), 1.03-0.82 (m, 2H), 0.77-0.55 (m, 2H).

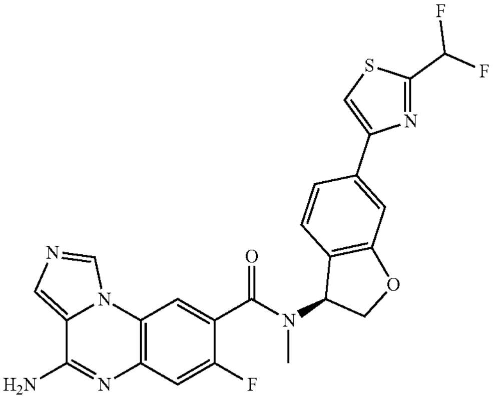 [SMILES: CN(C(=O)c1cc2c(cc1F)nc(N)c1cncn12)[C@@H]1COc2cc(-c3csc(C(F)F)n3)ccc21]

Example Ff-237: (S)-4-amino-N-(6-(2-(difluoromethyl)thiazol-4-yl)-2,3-dihydrobenzofuran-3-yl)-7-fluoro-N-methylimidazo[1,5-a]quinoxaline-8-carboxamide. Prepared following the procedure reported for Ff-231 starting with intermediates (S)-4-amino-N-(6-bromo-2,3-dihydrobenzofuran-3-yl)-7-fluoro-N-methylimidazo[1,5-a]quinoxaline-8-carboxamide Ff-94 and 4-bromo-2-(difluoromethyl)thiazole. ES/MS: m/z=511.0 $[M+H]^+$. $^1$H NMR (400 MHz, Methanol-d4) δ 9.23 (s, 1H), 8.42 (d, J=5.9 Hz, 1H), 8.29 (s, 0.5H, rotamer), 8.28 (s, 0.5H, rotamer), 8.16 (s, 0.5H, rotamer), 8.14 (s, 0.5H, rotamer), 7.78-7.58 (m, 1H), 7.57-7.33 (m, 3H), 7.11 (t, J=54.6, 0.5H, rotamer), 7.09 (t, J=54.6, 0.5H, rotamer), 6.55 (dd, J=8.7, 3.5 Hz, 0.5H, rotamer), 5.62 (s, 0.5H, rotamer), 4.75-4.63 (m, 2H), 2.90 (s, 1.5H, rotamer), 2.75 (d, J=1.2 Hz, 1.5H, rotamer).

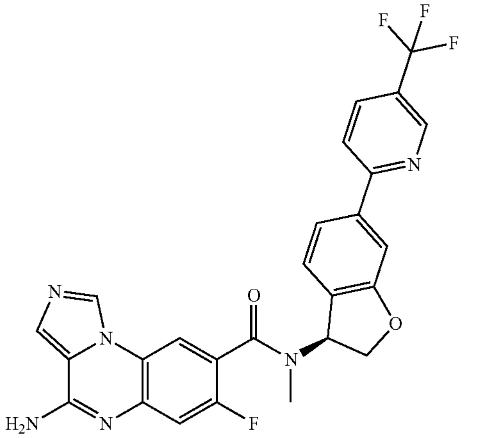 [SMILES: CN(C(=O)c1cc2c(cc1F)nc(N)c1cncn12)[C@@H]1COc2cc(-c3ccc(C(F)(F)F)cn3)ccc21]

Example Ff-238: (S)-4-amino-7-fluoro-N-methyl-N-(6-(5-(trifluoromethyl)pyridin-2-yl)-2,3-dihydrobenzofuran-3-yl)imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine hydrogen chloride Eh-5, and [5-(trifluoromethyl)-2-pyridyl] boronic acid. ES/MS: m/z=523.0 $[M+H]^+$. $^1H$ NMR (400 MHz, Methanol-d4) δ 9.25 (s, 1H), 8.94 (d, J=8.1 Hz, 1H), 8.45 (d, J=5.9 Hz, 1H), 8.33 (s, 1H), 8.28-8.14 (m, 1H), 8.08 (dd, J=15.8, 8.4 Hz, 1H), 7.84-7.70 (m, 1H), 7.67 (d, J=1.5 Hz, 1H), 7.62-7.54 (m, 1H), 7.47 (dd, J=14.6, 8.8 Hz, 2H), 6.59 (dd, J=8.8, 3.5 Hz, 0.5H, rotamer), 5.67 (s, 0.5H, rotamer), 4.76-4.66 (m, 2H), 2.91 (s, 1.5H, rotamer), 2.80-2.64 (m, 1.5H,

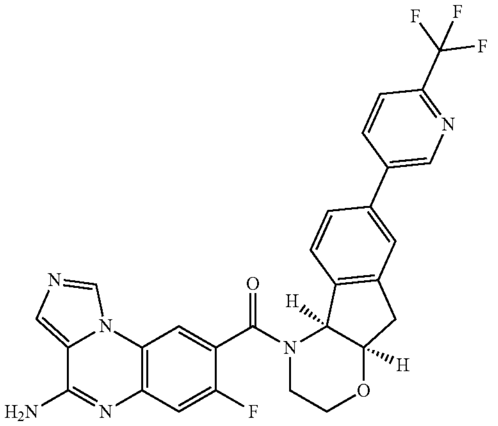 [SMILES: Nc1nc2cc(F)c(C(=O)N3CCO[C@@H]4Cc5cc(-c6ccc(C(F)(F)F)nc6)ccc5[C@@H]43)cc2n2cncc12]

Example Ff-239: (4-amino-7-fluoroimidazo[1,5-a]quinoxalin-8-yl)((4aS,9aR)-7-(6-(trifluoromethyl)pyridin-3-yl)-2,3,9,9a-tetrahydroindeno[2,1-b][1,4]oxazin-4(4aH)-yl) methanone. Prepared following the procedure reported for example Ff-23 starting with intermediates 4-((tert-butoxycarbonyl)amino)-7-fluoroimidazo[1,5-a]quinoxaline-8-carboxylic acid Af-1, (4aS,9aR)-7-bromo-2,3,4,4a,9,9a-hexahydroindeno[2,1-b][1,4]oxazine Et-1, and 5-(4,4,5,5-tetramethyl-1,3,2-dioxaborolan-2-yl)-2-(trifluoromethyl) pyridine. ES/MS: m/z=549.0 $[M+H]^+$. $^1H$ NMR (400 MHz, Methanol-d4) δ 9.42-9.25 (m, 1H), 9.10-8.85 (m, 1H), 8.70-8.45 (m, 1H), 8.44-8.20 (m, 2H), 7.97-7.80 (m, 1H), 7.80-7.37 (m, 4H), 6.06 (s, 0.5H, rotamer), 5.09 (s, 0.5H, rotamer), 4.61-4.48 (m, 2H), 3.93-3.58 (m, 2H), 3.53-3.41 (m, 1H), 3.18-2.93 (m, 2H).

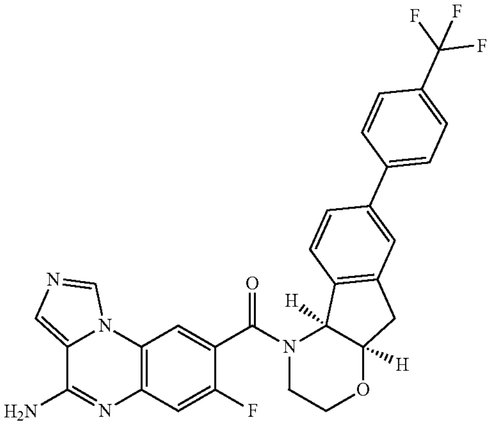 [SMILES: Nc1nc2cc(F)c(C(=O)N3CCO[C@@H]4Cc5cc(-c6ccc(C(F)(F)F)cc6)ccc5[C@@H]43)cc2n2cncc12]

Example Ff-240: (4-amino-7-fluoroimidazo[1,5-a]quinoxalin-8-yl)((4aS,9aR)-7-(4-(trifluoromethyl)phenyl)-2,3,9,9a-tetrahydroindeno[2,1-b][1,4]oxazin-4(4aH)-yl)methanone. Prepared following the procedure reported for example Ff-23 starting with intermediates 4-((tert-butoxycarbonyl)amino)-7-fluoroimidazo[1,5-a]quinoxaline-8-carboxylic acid Af-1, (4aS,9aR)-7-bromo-2,3,4,4a,9,9a-hexahydroindeno[2,1-b][1,4]oxazine Et-1, and [4-(trifluoromethyl)phenyl]boronic acid. ES/MS: m/z=548.0 $[M+H]^+$. $^1H$ NMR (400 MHz, Methanol-d4) δ 9.37-9.23 (m, 1H), 8.63-8.46 (m, 1H), 8.42-8.29 (m, 1H), 7.91-7.36 (m, 8H), 6.04 (s, 0.5H, rotamer), 5.09 (s, 0.5H, rotamer), 4.60-4.44 (m, 2H), 4.01-3.40 (m, 3H), 3.16-2.90 (m, 2H).

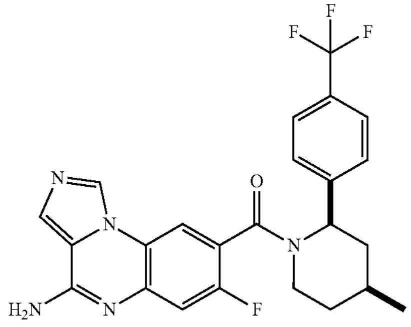

(±)

Example Ff-241: Rac-(4-amino-7-fluoroimidazo[1,5-a] quinoxalin-8-yl)((2R,4S)-4-methyl-2-(4-(trifluoromethyl) phenyl)piperidin-1-yl)methanone. Prepared following general procedure VI-F using 4-((tert-butoxycarbonyl)amino)-7-fluoroimidazo[1,5-a]quinoxaline-8-carboxylic acid Af-1 and rac-(2R,4S)-4-methyl-2-(4-(trifluoromethyl)phenyl)piperidine hydrochloride Eay-1. ES/MS: m/z=472.0 $[M+H]^+$. $^1H$ NMR (400 MHz, Methanol-d4) δ 9.26 (s, 1H), 8.33 (s, 1H), 7.88-7.17 (m, 6H), 5.48 (s, 1H), 3.66 (s, 1H), 3.36-3.34 (m, 1H), 2.33-1.97 (m, 3H), 1.94-1.77 (m, 1H), 1.35 (s, 1H), 1.01 (d, J=6.6 Hz, 3H).

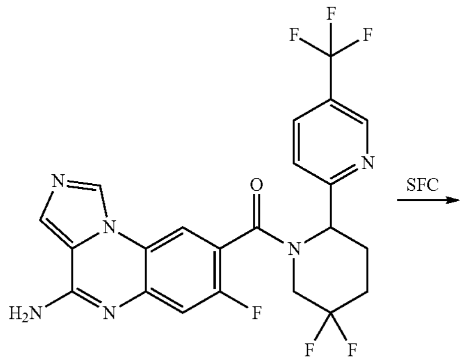

Example Ff-222

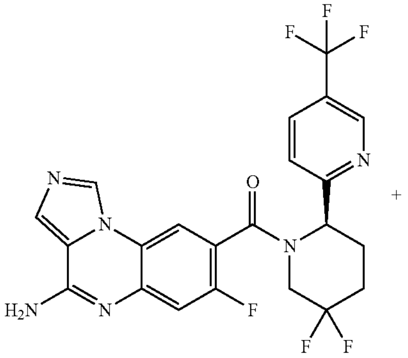

Peak 1
Example Ff-242

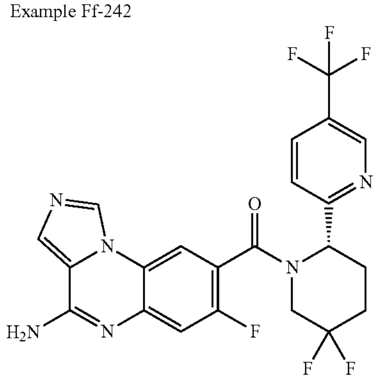

Peak 2
Example Ff-243

Example Ff-222 was subjected to supercritical fluid chromatography (ID—5 um-4.6×100 mm column, 30% EtOH, 3 mL/min, 100 bar, 40° C.)

Example Ff-242: (R)-(4-amino-7-fluoroimidazo[1,5-a]quinoxalin-8-yl)(5,5-difluoro-2-(5-(trifluoromethyl)pyridin-2-yl)piperidin-1-yl)methanone. Peak 1 (RT=4.35 min): ES/MS: m/z=495.0 $[M+H]^+$. $^1H$ NMR (400 MHz, Methanol-d4) δ 9.31 (s, 1H), 9.06-8.84 (m, 1H), 8.52-8.30 (m, 2H), 8.25-8.17 (m, 0.6H, major rotamer), 8.12 (d, J=8.4 Hz, 0.4H, minor rotamer), 7.77 (d, J=8.3 Hz, 0.6H, major rotamer), 7.58 (d, J=8.3 Hz, 0.4H, minor rotamer), 7.51 (d, J=9.6 Hz, 0.6H, major rotamer), 7.43 (s, 0.4H, minor rotamer), 6.17 (s, 0.5H, rotamer), 5.16 (s, 0.5H, rotamer), 3.79 (dq, J=29.7, 13.9 Hz, 1H), 2.68 (m, 1H), 2.46-1.99 (m, 4H).

Example Ff-243: (S)-(4-amino-7-fluoroimidazo[1,5-a]quinoxalin-8-yl)(5,5-difluoro-2-(5-(trifluoromethyl)pyridin-2-yl)piperidin-1-yl)methanone. Peak 2 (RT=5.39 min): ES/MS: m/z=495.0 $[M+H]^+$. $^1H$ NMR (400 MHz, Methanol-d4) δ 9.31 (s, 1H), 8.99 (s, 1H), 8.58-8.30 (m, 2H), 8.28-8.07 (m, 1H), 7.78 (s, 0.6H, major rotamer), 7.58 (d, J=8.4 Hz, 0.4H, minor rotamer), 7.52 (d, J=9.5 Hz, 0.6H, major rotamer), 7.45 (s, 0.4H, minor rotamer), 6.17 (s, 0.5H, rotamer), 5.16 (s, 0.5H, rotamer), 3.79 (m, 1H), 2.68 (m, 1H), 2.44-1.74 (m, 4H).

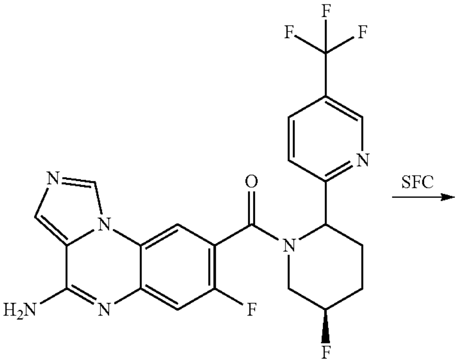

Example Ff-228

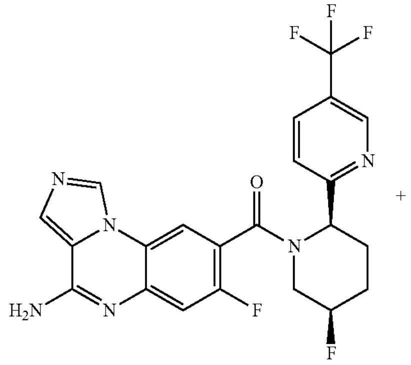

Peak 1
Example Ff-244

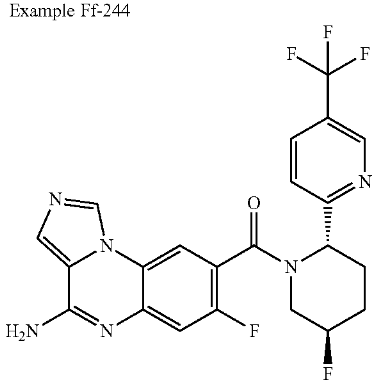

Peak 2
Example Ff-245

Example Ff-228 was subjected to supercritical fluid chromatography (AD-H4 6×100 mm column, 30% EtOH, 3 mL/min, 100 bar, 40° C.).

Example Ff-244: (4-amino-7-fluoroimidazo[1,5-a]quinoxalin-8-yl)((2R,5R)-5-fluoro-2-(5-(trifluoromethyl)pyridin-2-yl)piperidin-1-yl)methanone. Peak 1 (RT=3.06 min): ES/MS: m/z=477.0 $[M+H]^+$. $^1H$ NMR (400 MHz, Methanol-d4) δ 9.31 (s, 1H), 8.97 (s, 1H), 8.64-8.31 (m, 2H), 8.24-8.05 (m, 1H), 7.89-7.38 (m, 2H), 6.18 (s, 1H), 5.04 (m, 1H), 3.93-3.49 (m, 2H), 2.68 (s, 2H), 2.11-1.61 (m, 2H).

Example Ff-245: (4-amino-7-fluoroimidazo[1,5-a]quinoxalin-8-yl)((2S,5R)-5-fluoro-2-(5-(trifluoromethyl)pyrididin-2-yl)piperidin-1-yl)methanone. Peak 2 (RT=4.55 min): ES/MS: m/z=477.0 $[M+H]^+$. $^1H$ NMR (400 MHz, Methanol-d4) δ 9.23 (s, 1H), 8.98 (s, 1H), 8.44 (s, 1H), 8.35-8.04 (m, 2H), 7.83-7.32 (m, 2H), 5.98 (s, 1H), 4.89 (d, J=1.7 Hz, 1H), 4.01-3.45 (m, 2H), 2.68 (s, 2H), 2.06 (m, 2H).

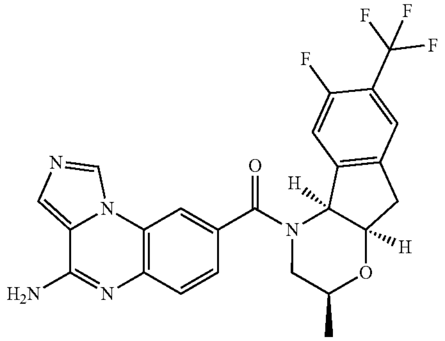 [SMILES: C[C@H]1CN(C(=O)c2ccc3nc(N)c4cncn4c3c2)[C@H]2c3cc(F)c(C(F)(F)F)cc3C[C@H]2O1]

Example Ff-246: (4-aminoimidazo[1,5-a]quinoxalin-8-yl)((2S,4aS,9aR)-6-fluoro-2-methyl-7-(trifluoromethyl)-2,3,9,9a-tetrahydroindeno[2,1-b][1,4]oxazin-4(4aH)-yl)methanone. Prepared following general procedure VI-F using 4-((tert-butoxycarbonyl)amino)imidazo[1,5-a]quinoxaline-8-carboxylic acid Ae-1 and (2S,4aS,9aR)-6-fluoro-2-methyl-7-(trifluoromethyl)-2,3,4,4a,9,9a-hexahydroindeno[2,1-b][1,4]oxazine hydrogen chloride Eaz-2. ES/MS: m/z=486.0 $[M+H]^+$. $^1H$ NMR (400 MHz, Methanol-d4) δ 9.34 (d, J=45.1 Hz, 1H), 8.54 (s, 1H), 8.39 (d, J=13.7 Hz, 1H), 7.90-7.62 (m, 3H), 7.62-7.23 (m, 1H), 6.01 (s, 0.8H, major rotamer), 5.19 (s, 0.2H, minor rotamer), 4.72-4.41 (m, 1H), 4.00-3.45 (m, 2H), 3.26-2.75 (m, 3H), 1.16 (d, J=6.2 Hz, 1H), 0.98 (d, J=6.2 Hz, 2H).

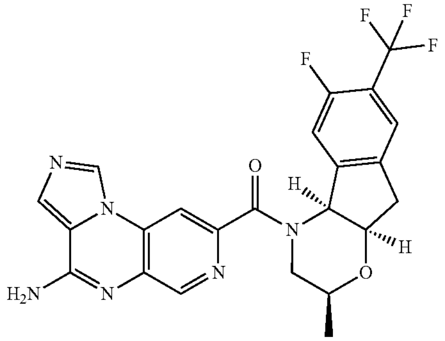 [SMILES: C[C@H]1CN(C(=O)c2cc3c(cn2)nc(N)c2cncn23)[C@H]2c3cc(F)c(C(F)(F)F)cc3C[C@H]2O1]

Example Ff-247: (4-aminoimidazo[1,5-a]pyrido[3,4-e]pyrazin-8-yl)((2S,4aS,9aR)-6-fluoro-2-methyl-7-(trifluoromethyl)-2,3,9,9a-tetrahydroindeno[2,1-b][1,4]oxazin-4(4aH)-yl)methanone. Prepared following general procedure VI-F using 4-((tert-butoxycarbonyl)amino)imidazo[1,5-a]pyrido[3,4-e]pyrazine-8-carboxylic acid Af-6 and (2S,4aS,9aR)-6-fluoro-2-methyl-7-(trifluoromethyl)-2,3,4,4a,9,9a-hexahydroindeno[2,1-b][1,4]oxazine hydrochloride Eaz-2. ES/MS: m/z=487.0 $[M+H]^+$. $^1H$ NMR (400 MHz, Methanol-d4) δ 9.32 (d, J=6.4 Hz, 1H), 8.91-8.50 (m, 2H), 8.22 (d, J=2.6 Hz, 1H), 7.74-7.16 (m, 2H), 5.99 (s, 0.5H, rotamer), 5.58 (s, 0.5H, rotamer), 4.69-4.42 (m, 1H), 3.93-3.46 (m, 2H), 3.17-2.46 (m, 3H), 1.16 (d, J=6.2 Hz, 1H), 1.00 (d, J=6.2 Hz, 2H).

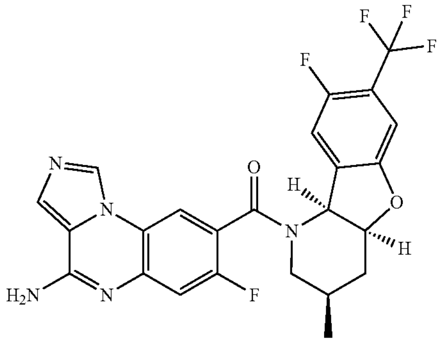 [SMILES: C[C@@H]1C[C@@H]2Oc3cc(C(F)(F)F)c(F)cc3[C@@H]2N(C(=O)c2cc3c(cc2F)nc(N)c2cncn23)C1]

Example Ff-248: (4-amino-7-fluoroimidazo[1,5-a]quinoxalin-8-yl)((3R,4aS,9bS)-8-fluoro-3-methyl-7-(trifluoromethyl)-3,4,4a,9b-tetrahydrobenzofuro[3,2-b]pyridin-1(2H)-yl)methanone: Prepared following general procedure VI-F using 4-((tert-butoxycarbonyl)amino)-7-fluoroimidazo[1,5-a]quinoxaline-8-carboxylic acid Af-1 and (3R,4aS,9bS)-8-fluoro-3-methyl-7-(trifluoromethyl)-1,2,3,4,4a,9b-hexahydrobenzofuro[3,2-b]pyridine hydrochloride Ew-6. ES/MS: m/z=504.0 $[M+H]^+$. $^1H$ NMR (400 MHz, Methanol-d4) δ 9.24 (d, J=12.8 Hz, 1H), 8.67-8.27 (m, 2H), 7.47 (dd, J=9.8, 3.9 Hz, 1H), 7.33 (s, 1H), 7.11 (dd, J=31.4, 5.3 Hz, 1H), 6.41 (s, 0.8H, major rotamer), 5.59 (s, 0.2H, minor rotamer), 5.14 (m, 1H), 3.52-3.39 (m, 1H), 2.66 (s, 1H), 2.39-2.14 (m, 1H), 1.94 (s, 1H), 1.54 (m, 1H), 1.02 (d, J=6.7 Hz, 0.6H, minor rotamer), 0.87 (d, J=6.7 Hz, 2.4H, major rotamer).

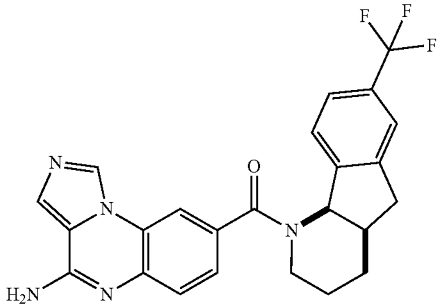

(±)

Example Ff-249: Rac-(4-aminoimidazo[1,5-a]quinoxalin-8-yl)((4aR,9bR)-7-(trifluoromethyl)-2,3,4,4a,5,9b-hexahydro-1H-indeno[1,2-b]pyridin-1-yl)methanone. Prepared following general procedure VI-F using 4-((tert-butoxycarbonyl)amino)imidazo[1,5-a]quinoxaline-8-carboxylic acid Ae-1 and cis-(4aR,9bR)-7-(trifluoromethyl)-2,3,4,4a,5,9b-hexahydro-1H-indeno[1,2-b]pyridine Eax-1. ES/MS: m/z=452.0 $[M+H]^+$. $^1H$ NMR (400 MHz, Methanol-d4) δ 9.40 (s, 0.6H, major rotamer), 9.29 (s, 0.4H, minor rotamer), 8.51 (t, J=1.1 Hz, 1H), 8.42 (s, 1H), 7.81-7.42 (m, 5H), 6.23 (s, 0.6H, major rotamer), 5.29 (s, 0.4H, minor rotamer), 4.66 (s, 0.4H, minor rotamer), 3.73 (d, J=13.5 Hz, 0.6H, major rotamer), 3.26-2.41 (m, 4H), 2.06-1.40 (m, 3H), 1.36-1.03 (m, 1H).

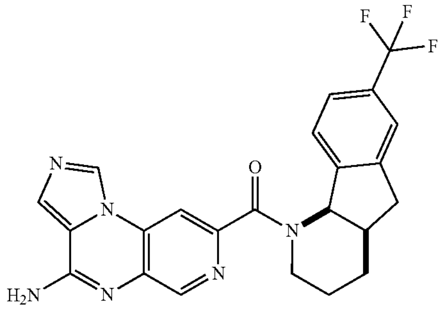

(±)

Example Ff-250: Rac-(4-aminoimidazo[1,5-a]pyrido[3,4-e]pyrazin-8-yl)((4aR,9bR)-7-(trifluoromethyl)-2,3,4,4a,5,9b-hexahydro-1H-indeno[1,2-b]pyridin-1-yl)methanone. Prepared following general procedure VI-F using 4-((tert-butoxycarbonyl)amino)imidazo[1,5-a]pyrido[3,4-e]pyrazine-8-carboxylic acid Af-6 and cis-(4aR,9bR)-7-(trifluoromethyl)-2,3,4,4a,5,9b-hexahydro-1H-indeno[1,2-b]pyridine Eax-1. ES/MS: m/z=453.0 $[M+H]^+$. $^1H$ NMR (400 MHz, Methanol-d4) δ 9.38 (s, 0.6H, major rotamer), 9.35 (s, 0.4H, minor rotamer), 8.88 (s, 0.6H, major rotamer), 8.73 (s, 0.4H, minor rotamer), 8.58 (d, J=5.3 Hz, 1H), 8.32 (d, J=5.7 Hz, 1H), 7.74-7.44 (m, 3H), 6.23 (d, J=6.7 Hz, 0.6H, major rotamer), 5.50 (d, J=6.4 Hz, 0.4H, minor rotamer), 4.69 (d, J=13.2 Hz, 0.4H, minor rotamer), 3.83 (d, J=13.6 Hz, 0.6H, major rotamer), 3.23-2.47 (m, 4H), 2.06-1.45 (m, 3H), 1.39-1.05 (m, 1H),

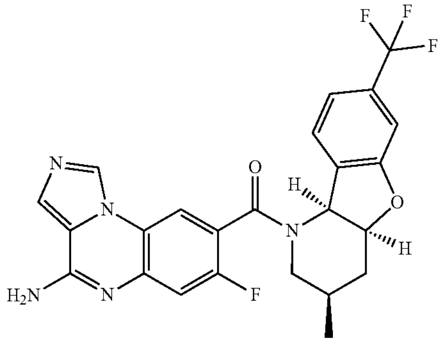 [SMILES: C[C@@H]1C[C@@H]2Oc3cc(C(F)(F)F)ccc3[C@@H]2N(C(=O)c2cc3c(cc2F)nc(N)c2cncn23)C1]

Example Ff-251: (4-amino-7-fluoroimidazo[1,5-a]quinoxalin-8-yl)((3R,4aS,9bS)-3-methyl-7-(trifluoromethyl)-3,4,4a,9b-tetrahydrobenzofuro[3,2-b]pyridin-1(2H)-yl)methanone. Prepared following general procedure VI-F using 4-((tert-butoxycarbonyl)amino)-7-fluoroimidazo[1,5-a]quinoxaline-8-carboxylic acid Af-1 and (3R,4aS,9bS)-3-methyl-7-(trifluoromethyl)-1,2,3,4,4a,9b-hexahydrobenzofuro[3,2-b]pyridine hydrochloride Ew-7. ES/MS: m/z=486.0 $[M+H]^+$. $^1H$ NMR (400 MHz, Methanol-d4) δ 9.27 (d, J=8.4 Hz, 1H), 8.47 (d, J=5.9 Hz, 1H), 8.35 (d, J=5.1 Hz, 1H), 7.48 (dd, J=9.8, 4.5 Hz, 2H), 7.33 (d, J=8.1 Hz, 1H), 7.12 (d, J=31.1 Hz, 1H), 6.43 (s, 0.7H, major rotamer), 5.58 (s, 0.3H, minor rotamer), 5.15 (td, J=7.9, 5.4 Hz, 1H), 3.58-3.42 (m, 1H), 2.68 (m, 1H), 2.37-2.17 (m, 1H), 1.96 (s, 1H), 1.66-1.43 (m, 1H), 1.03 (d, J=6.6 Hz, 0.7H, minor rotamer), 0.88 (d, J=6.7 Hz, 2.3H, major rotamer).

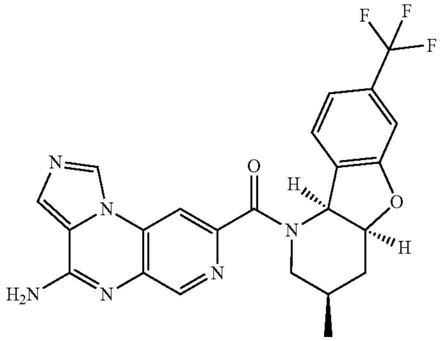 [SMILES: C[C@@H]1C[C@@H]2Oc3cc(C(F)(F)F)ccc3[C@@H]2N(C(=O)c2cc3c(cn2)nc(N)c2cncn23)C1]

Example Ff-252: (4-aminoimidazo[1,5-a]pyrido[3,4-e]pyrazin-8-yl)((3R,4aS,9bS)-3-methyl-7-(trifluoromethyl)-3,4,4a,9b-tetrahydrobenzofuro[3,2-b]pyridin-1(2H)-yl)methanone. Prepared following general procedure VI-F using 4-((tert-butoxycarbonyl)amino)imidazo[1,5-a]pyrido[3,4-e]pyrazine-8-carboxylic acid Af-6 and (3R,4aS,9bS)-3-methyl-7-(trifluoromethyl)-1,2,3,4,4a,9b-hexahydrobenzofuro[3,2-b]pyridine hydrochloride Ew-7. ES/MS: m/z=469.0 $[M+H]^+$. $^1H$ NMR (400 MHz, Methanol-d4) δ 9.34 (s, 1H), 8.82 (d, J=12.1 Hz, 1H), 8.62 (s, 0.4H, minor rotamer), 8.54 (s, 0.6H, major rotamer), 8.28 (s, 1H), 7.87 (d, J=7.7 Hz, 0.4H, minor rotamer), 7.60 (d, J=7.7 Hz, 0.6H, major rotamer), 7.32 (t, J=7.8 Hz, 1H), 7.12 (d, J=24.8 Hz, 1H), 6.34 (d, J=8.4 Hz, 0.6H, major rotamer), 5.97 (d, J=8.3 Hz, 0.4H, minor rotamer), 5.29-4.93 (m, 1H), 4.54 (dd, J=13.5, 4.9 Hz, 0.4H, minor rotamer), 3.81 (dd, J=13.5, 5.3 Hz, 0.6H, major rotamer), 2.42-2.09 (m, 1H), 1.96 (s, 1H), 1.67 (dt, J=13.6, 6.9 Hz, 0.6H, major rotamer), 1.59-1.45 (m, 0.4H, minor rotamer), 1.05 (d, J=6.7 Hz, 1.3H, minor rotamer), 0.91 (d, J=6.6 Hz, 1.7H, major rotamer).

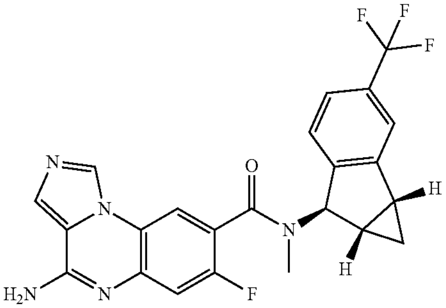 [SMILES: CN(C(=O)c1cc2c(cc1F)nc(N)c1cncn12)[C@H]1c2ccc(C(F)(F)F)cc2[C@@H]2C[C@@H]21]

Example Ff-253: 4-amino-7-fluoro-N-methyl-N-((1aR,6R,6aS)-3-(trifluoromethyl)-1,1a,6,6a-tetrahydrocyclopropa[a]inden-6-yl)imidazo[1,5-a]quinoxaline-8-carboxamide. Prepared following general procedure VI-F using 4-((tert-butoxycarbonyl)amino)-7-fluoroimidazo[1,5-a]quinoxaline-8-carboxylic acid Af-1 and (1aR,6R,6aS)—N-methyl-3-(trifluoromethyl)-1,1a,6,6a-tetrahydrocyclopropa[a]inden-6-amine Eab-2. ES/MS: m/z=456.0 $[M+H]^+$. $^1H$ NMR (400 MHz, Methanol-d4) δ 9.38-9.19 (m, 1H), 8.69-8.45 (m, 1H), 8.40 (dd, J=4.5, 0.7 Hz, 1H), 7.72 (d, J=14.2 Hz, 1H), 7.62-7.43 (m, 3H), 6.22 (s, 0.6H, major rotamer), 5.07 (s, 0.4H, minor rotamer), 2.90-2.53 (m, 4H), 2.21 (ddt, J=27.2, 9.3, 4.9 Hz, 1H), 1.53-1.18 (m, 1H), 0.41–-0.16 (m, 1H).

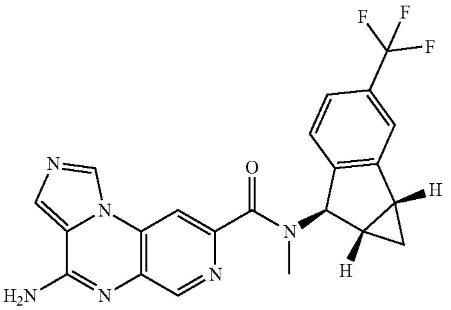 [SMILES: CN(C(=O)c1cc2c(cn1)nc(N)c1cncn12)[C@H]1c2ccc(C(F)(F)F)cc2[C@@H]2C[C@@H]21]

Example Ff-254: 4-amino-N-methyl-N-((1aR,6R,6aS)-3-(trifluoromethyl)-1,1a,6,6a-tetrahydrocyclopropa[a]inden-6-yl)imidazo[1,5-a]pyrido[3,4-e]pyrazine-8-carboxamide. Prepared following general procedure VI-F using 4-((tert-butoxycarbonyl)amino)imidazo[1,5-a]pyrido[3,4-e]pyrazine-8-carboxylic acid Af-6 and (1aR,6R,6aS)—N-methyl-3-(trifluoromethyl)-1,1a,6,6a-tetrahydrocyclopropa[a]inden-6-amine Eab-2. ES/MS: m/z=439.0 $[M+H]^+$. $^1H$ NMR (400 MHz, Methanol-d4) δ 9.36 (d, J=9.9 Hz, 1H), 8.91 (s, 0.6H, major rotamer), 8.83 (s, 0.4H, minor rotamer), 8.61 (s, 0.6H, major rotamer), 8.55 (s, 0.4H, minor rotamer), 8.45-8.14 (m, 1H), 7.90-7.29 (m, 3H), 6.19 (s, 0.4H, minor rotamer), 5.47 (s, 0.6H, major rotamer), 2.87-2.60 (m, 4H), 2.23 (td, J=8.2, 4.3 Hz, 1H), 1.43 (td, J=8.2, 4.8 Hz, 0.4H, minor rotamer), 1.30 (td, J=8.2, 4.9 Hz, 0.6H, major rotamer), 0.32 (t, J=4.1 Hz, 0.4H, minor rotamer), 0.06 (q, J=4.2 Hz, 0.6H, major rotamer).

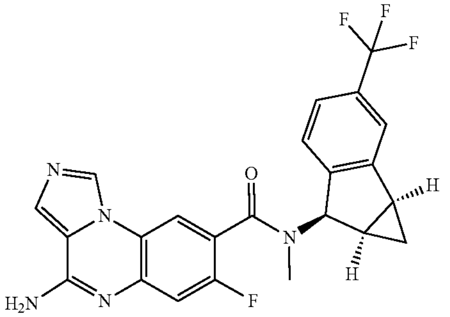 [SMILES: CN(C(=O)c1cc2c(cc1F)nc(N)c1cncn12)[C@H]1c2ccc(C(F)(F)F)cc2[C@H]2C[C@H]21]

Example Ff-255: 4-amino-7-fluoro-N-methyl-N-((1aS,6R,6aR)-3-(trifluoromethyl)-1,1a,6,6a-tetrahydrocyclopropa[a]inden-6-yl)imidazo[1,5-a]quinoxaline-8-carboxamide. Prepared following general procedure VI-F using 4-((tert-butoxycarbonyl)amino)-7-fluoroimidazo[1,5-a]quinoxaline-8-carboxylic acid Af-1 and (1aS,6R,6aR)—N-methyl-3-(trifluoromethyl)-1,1a,6,6a-tetrahydrocyclopropa[a]inden-6-amine Eab-1. ES/MS: m/z=456.0 $[M+H]^+$. $^1H$ NMR (400 MHz, Methanol-d4) δ 9.61-9.14 (m, 1H), 8.65-8.19 (m, 2H), 7.83-7.08 (m, 4H), 6.66 (d, J=6.6 Hz, 0.6H, major rotamer), 5.90-5.58 (m, 0.4H, minor rotamer), 3.05-2.39 (m, 4H), 2.17-1.83 (m, 1H), 1.22 (td, J=7.9, 5.1 Hz, 1H), 0.99-0.56 (m, 1H).

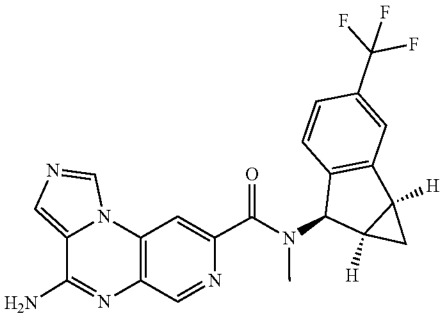 [SMILES: CN(C(=O)c1cc2c(cn1)nc(N)c1cncn12)[C@H]1c2ccc(C(F)(F)F)cc2[C@H]2C[C@H]21]

Example Ff-256: 4-amino-N-methyl-N-((1aS,6R,6aR)-3-(trifluoromethyl)-1,1a,6,6a-tetrahydrocyclopropa[a]inden-6-yl)imidazo[1,5-a]pyrido[3,4-e]pyrazine-8-carboxamide. Prepared following general procedure VI-F using 4-((tert-butoxycarbonyl)amino)imidazo[1,5-a]pyrido[3,4-e]pyrazine-8-carboxylic acid Af-6 and (1aS,6R,6aR)—N-methyl-3-(trifluoromethyl)-1,1a,6,6a-tetrahydrocyclopropa[a]inden-6-amine Eab-1. ES/MS: m/z=439.0 $[M+H]^+$. $^1H$ NMR (400 MHz, Methanol-d4) δ 9.37 (d, J=4.5 Hz, 1H), 8.86 (d, J=19.3 Hz, 1H), 8.59 (d, J=4.1 Hz, 1H), 8.34 (s, 1H), 7.85-7.25 (m, 3H), 6.63 (d, J=6.6 Hz, 0.4H, minor rotamer), 6.02 (d, J=6.4 Hz, 0.6H, major rotamer), 3.24-2.82 (m, 3H), 2.68 (s, 0.6H, major rotamer), 2.62-2.45 (m, 0.4H, minor rotamer), 2.30-1.91 (m, 1H), 1.20 (td, J=7.9, 5.1 Hz, 1H), 0.77 (dq, J=24.8, 4.4 Hz, 1H).

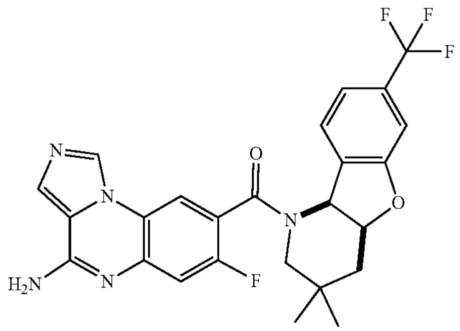

(±)

Example Ff-257: Rac-(4-amino-7-fluoroimidazo[1,5-a]quinoxalin-8-yl)((4aR,9bR)-3,3-dimethyl-7-(trifluoromethyl)-3,4,4a,9b-tetrahydrobenzofuro[3,2-b]pyridin-1(2H)-yl)methanone. Prepared following general procedure VI-F using 4-((tert-butoxycarbonyl)amino)-7-fluoroimidazo[1,5-a]quinoxaline-8-carboxylic acid Af-1 and cis-(4aS,9bS)-3,3-dimethyl-7-(trifluoromethyl)-1,2,3,4,4a,9b-hexahydrobenzofuro[3,2-b]pyridine hydrochloride Eba-1 ES/MS: m/z=500.0 $[M+H]^+$. $^1H$ NMR (400 MHz, Methanol-d4) δ 9.30 (s, 1H), 8.44 (s, 1H), 8.36 (s, 1H), 7.74-7.04 (m, 4H), 6.48 (d, J=8.5 Hz, 0.7H, major rotamer), 5.55 (s, 0.3H, minor rotamer), 5.31-5.03 (m, 1H), 4.36 (d, J=13.3 Hz, 0.3H, minor rotamer), 3.23-3.09 (m, 0.7H, major rotamer), 2.92 (d, J=13.7 Hz, 0.7H, major rotamer), 2.51 (d, J=13.2 Hz, 0.3H, minor rotamer), 2.11-1.62 (m, 2H), 1.16 (s, 1H, minor rotamer), 1.07 (s, 1H, minor rotamer), 0.97 (s, 2H, major rotamer), 0.89 (s, 2H, major rotamer).

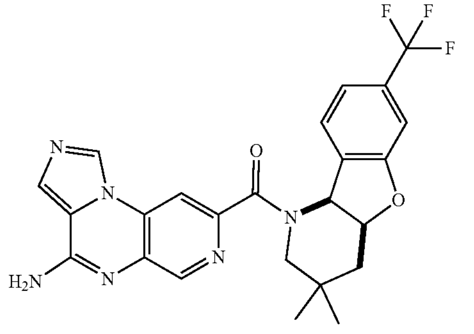

(±)

Example Ff-258: Rac-(4-aminoimidazo[1,5-a]pyrido[3,4-e]pyrazin-8-yl)((4aR,9bR)-3,3-dimethyl-7-(trifluoromethyl)-3,4,4a,9b-tetrahydrobenzofuro[3,2-b]pyridin-1(2H)-yl)methanone. Prepared following general procedure VI-F using 4-((tert-butoxycarbonyl)amino)imidazo[1,5-a]pyrido[3,4-e]pyrazine-8-carboxylic acid Af-6 and cis-(4aS,9bS)-3,3-dimethyl-7-(trifluoromethyl)-1,2,3,4,4a,9b-hexahydrobenzofuro[3,2-b]pyridine hydrochloride Eba-1. ES/MS: m/z=483.0 $[M+H]^+$. $^1H$ NMR (400 MHz, Methanol-d4) δ 9.36 (d, J=11.6 Hz, 1H), 8.83 (s, 1H), 8.63 (s, 0.6H, major rotamer), 8.53 (s, 0.4H, minor rotamer), 8.29 (s, 1H), 7.89 (d, J=7.8 Hz, s, 0.6H, major rotamer), 7.62 (d, J=7.8 Hz, 0.4H, minor rotamer), 7.32 (d, J=7.8 Hz, 1H), 7.12 (d, J=24.9 Hz, 1H), 6.43 (d, J=8.4 Hz, 0.4H, minor rotamer), 5.99 (d, J=8.4 Hz, 0.6H, major rotamer), [1469]5.22 (d, J=7.1 Hz, 0.4H, minor rotamer), 5.05 (d, J=7.1 Hz, 0.6H, major rotamer), 4.32 (d, J=13.3 Hz, 0.4H, minor rotamer), 3.67-3.45 (m, 0.6H, major rotamer), 2.85 (d, J=13.7 Hz, 0.4H, minor rotamer), 2.49 (d, J=13.3 Hz, 0.6H, major rotamer), 2.06-1.64 (m, 2H), 1.16 (s, 1.6H, major rotamer), 1.08 (s, 1.6H, major rotamer), 1.04 (s, 1.4H, minor rotamer), 0.92 (s, 1.4H, minor rotamer).

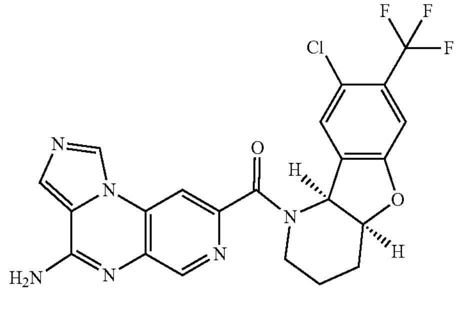 [SMILES: Nc1nc2cnc(C(=O)N3CCC[C@@H]4Oc5cc(C(F)(F)F)c(Cl)cc5[C@@H]43)cc2n2cncc12]

Example Ff-259: (4-aminoimidazo[1,5-a]pyrido[3,4-e]pyrazin-8-yl)((4aS,9bS)-8-chloro-7-(trifluoromethyl)-3,4,4a,9b-tetrahydrobenzofuro[3,2-b]pyridin-1(2H)-yl)methanone. Prepared following general procedure VI-F using 4-((tert-butoxycarbonyl)amino)imidazo[1,5-a]pyrido[3,4-e]pyrazine-8-carboxylic acid Af-6 and (4aS,9bS)-8-chloro-7-(trifluoromethyl)-1,2,3,4,4a,9b-hexahydrobenzofuro[3,2-b]pyridine hydrogen chloride Ew-8. ES/MS: m/z=489.0 $[M+H]^+$. 1H NMR (400 MHz, Methanol-d4) δ 9.37 (s, 1H), 8.86 (d, J=13.8 Hz, 1H), 8.66 (s, 0.5H, rotamer), 8.58 (s, 0.5H, rotamer), 8.33 (s, 1H), 7.93 (s, 0.5H, rotamer), 7.66 (s, 0.5H, rotamer), 7.26 (d, J=17.9 Hz, 1H), 6.34 (d, J=8.8 Hz, 0.6H, major rotamer), 6.05 (d, J=9.0 Hz, 0.4H, minor rotamer), 5.31-5.02 (m, 1H), 4.45 (s, 0.5H, rotamer), 3.81 (s, 0.5H, rotamer), 2.91 (m, 2H), 1.96 (m, 2H).

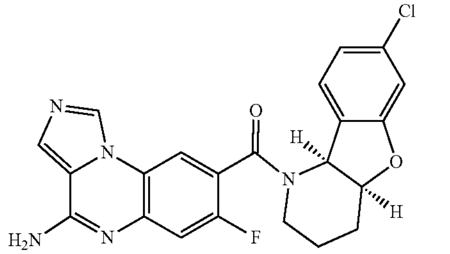 [SMILES: Nc1nc2cc(F)c(C(=O)N3CCC[C@@H]4Oc5cc(Cl)ccc5[C@@H]43)cc2n2cncc12]

Example Ff-260: (4-amino-7-fluoroimidazo[1,5-a]quinoxalin-8-yl)((4aS,9bS)-7-chloro-3,4,4a,9b-tetrahydrobenzofuro[3,2-b]pyridin-1(2H)-yl)methanone. Prepared following general procedure VI-F using 4-((tert-butoxycarbonyl)amino)-7-fluoroimidazo[1,5-a]quinoxaline-8-carboxylic acid Af-1 and (4aS,9bS)-7-chloro-1,2,3,4,4a,9b-hexahydrobenzofuro[3,2-b]pyridine hydrogen chloride Ew-9. ES/MS: m/z=438.0 $[M+H]^+$. $^1H$ NMR (400 MHz, Methanol-d4) δ 9.30 (d, J=5.9 Hz, 1H), 8.75-8.33 (m, 2H), 7.57-7.16 (m, 2H), 7.09-6.74 (m, 2H), 6.35 (d, J=8.8 Hz, 0.7H, major rotamer), 5.54 (d, J=9.1 Hz, 0.3H, minor rotamer), 5.15 (dt, J=8.5, 4.2 Hz, 1H), 3.57-3.40 (m, 0.4H, minor rotamer), 3.09-2.61 (m, 1.6H, major rotamer), 2.22-1.50 (m, 4H).

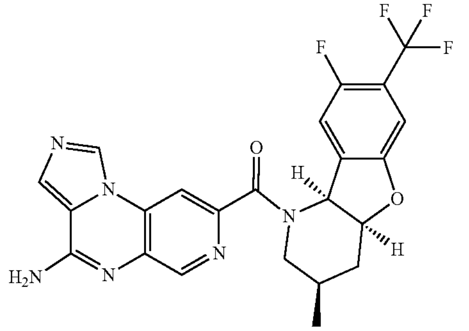 [SMILES: C[C@@H]1C[C@@H]2Oc3cc(C(F)(F)F)c(F)cc3[C@@H]2N(C(=O)c2cc3c(cn2)nc(N)c2cncn23)C1]

Example Ff-261: (4-aminoimidazo[1,5-a]pyrido[3,4-e]pyrazin-8-yl)((3R,4aS,9bS)-8-fluoro-3-methyl-7-(trifluoromethyl)-3,4,4a,9b-tetrahydrobenzofuro[3,2-b]pyridin-1(2H)-yl)methanone. Prepared following general procedure VI-F using 4-((tert-butoxycarbonyl)amino)imidazo[1,5-a]pyrido[3,4-e]pyrazine-8-carboxylic acid Af-6 and (3R,4aS,9bS)-8-fluoro-3-methyl-7-(trifluoromethyl)-1,2,3,4,4a,9b-hexahydrobenzofuro[3,2-b]pyridine hydrogen chloride Ew-6. ES/MS: m/z=487.0 $[M+H]^+$. $^1H$ NMR (400 MHz, Methanol-d4) δ 9.32 (d, J=2.1 Hz, 1H), 8.81 (d, J=9.2 Hz, 1H), 8.61 (s, 0.4H, minor rotamer), 8.55 (s, 0.6H, major rotamer), 8.25 (d, J=3.5 Hz, 1H), 7.72 (d, J=9.6 Hz, 0.4H, minor rotamer), 7.40 (d, J=9.4 Hz, 0.6H, major rotamer), 7.15 (d, J=5.3 Hz, 0.6H, major rotamer), 7.10 (d, J=5.3 Hz, 0.4H, minor rotamer), 6.33 (d, J=8.3 Hz, 0.6H, major rotamer), 5.99 (d, J=8.4 Hz, 0.4H, minor rotamer), 5.25-5.11 (m, 0.6H, major rotamer), 5.02-4.93 (m, 0.4H, minor rotamer), 4.55 (d, J=14.1 Hz, 0.4H, minor rotamer), 3.84 (dd, J=13.5, 5.2 Hz, 0.6H, major rotamer), 2.64-2.50 (m, 0.6H, major rotamer), 2.39-2.30 (m, 0.4H, minor rotamer), 2.29-1.85 (m, 2H), 1.65 (dt, J=13.8, 7.1 Hz, 0.6H, major rotamer), 1.58-1.41 (m, 0.4H, minor rotamer), 1.05 (d, J=6.7 Hz, 1.4H, minor rotamer), 0.92 (d, J=6.7 Hz, 1.6H, major rotamer).

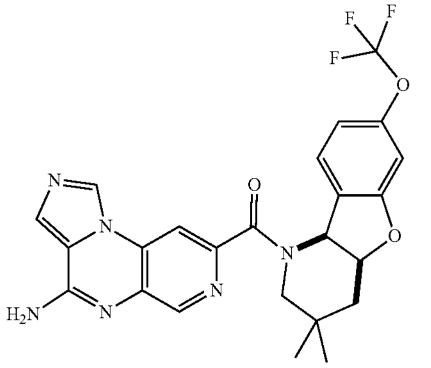 [SMILES: CC1(C)C[C@@H]2Oc3cc(OC(F)(F)F)ccc3[C@@H]2N(C(=O)c2cc3c(cn2)nc(N)c2cncn23)C1]

Example Ff-262: Rac-(4-aminoimidazo[1,5-a]pyrido[3,4-e]pyrazin-8-yl)((4aS,9bS)-3,3-dimethyl-7-(trifluoromethoxy)-3,4,4a,9b-tetrahydrobenzofuro[3,2-b]pyridin-1(2H)-yl)methanone. Prepared following general procedure VI-F using 4-((tert-butoxycarbonyl)amino)imidazo[1,5-a]pyrido[3,4-e]pyrazine-8-carboxylic acid Af-6 and cis-(4aS,9bS)-3,3-dimethyl-7-(trifluoromethoxy)-1,2,3,4,4a,9b-hexahydrobenzofuro[3,2-b]pyridine hydrochloride Eba-2. ES/MS: m/z=499.0 $[M+H]^+$. $^1H$ NMR (400 MHz, Methanol-d4) δ 9.33 (d, J=11.6 Hz, 1H), 8.81 (d, J=12.2 Hz, 1H), 8.59 (s, 0.6H, major rotamer), 8.49 (s, 0.4H, minor rotamer), 8.23 (s, 1H), 7.78 (d, J=8.2 Hz, 0.6H, major rotamer), 7.52 (d, J=8.2 Hz, 0.4H, minor rotamer), 6.91 (d, J=8.3 Hz, 1H), 6.78 (m, 1H), 6.34 (d, J=8.4 Hz, 0.5H, rotamer), 5.91 (d, J=8.3 Hz, 0.5H, rotamer), 5.28-4.97 (m, 1H), 4.29 (d, J=13.3 Hz, 0.5H, rotamer), 3.62 (d, J=14.0 Hz, 0.5H, rotamer), 2.85 (d, J=13.8 Hz, 0.6H, major rotamer), 2.51 (d, 0.4H, minor rotamer), 1.84 (d, J=12.9 Hz, 2H), 1.27-0.80 (m, 6H).

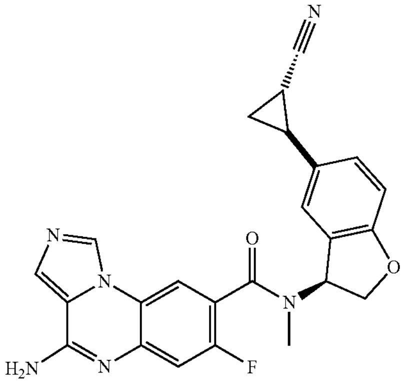

Example Ff-263: Trans-4-amino-N-((3S)-5-(2-cyanocyclopropyl)-2,3-dihydrobenzofuran-3-yl)-7-fluoro-N-methylimidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-5-bromo-N-methyl-2,3-dihydrobenzofuran-3-amine hydrochloride Ebb-1, and trans-2-(trifluoro-14-boraneyl)cyclopropane-1-carbonitrile, potassium salt. ES/MS: m/z=443. 1 $[M+H]^+$. $^1H$ NMR (400 MHz, Methanol-d4) δ 9.23 (s, 1H), 8.42 (dd, J=6.1, 2.5 Hz, 1H), 8.33 (s, 1H), 7.52-7.06 (m, 3H), 6.84 (dd, J=18.7, 8.3 Hz, 1H), 6.48 (dd, J=8.8, 3.4 Hz, 0.6H, major rotamer), 5.56 (s, 0.4H, minor rotamer), 4.84-4.52 (m, 2H), 2.83 (s, 1.5H, rotamer), 2.69 (s, 1.5H, rotamer), 2.68-2.62 (m, 1H), 1.85-1.35 (m, 3H).

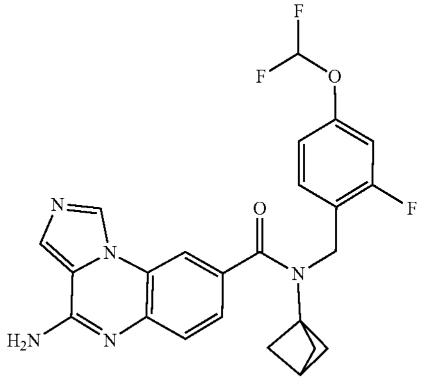 [SMILES: Nc1nc2ccc(C(=O)N(Cc3ccc(OC(F)F)cc3F)C34CC(C3)C4)cc2n2cncc12]

Example Ff-264: 4-amino-N-(bicyclo[1.1.1]pentan-1-yl)-N-(4-(difluoromethoxy)-2-fluorobenzyl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-(4-(difluoromethoxy)-2-fluorobenzyl)bicyclo[1.1.1]pentan-1-amine Ec-13. ES/MS: m/z=468.0 $[M+H]^+$. $^1H$ NMR (400 MHz, MeOD) δ 9.33 (s, 1H), 8.44-8.38 (m, 2H), 7.69 (d, J=8.4 Hz, 1H), 7.62 (dd, J=8.3, 1.6 Hz, 1H), 7.51 (t, J=8.5 Hz, 1H), 7.15-6.94 (m, 2H), 6.90 (t, J=73.4 Hz, 1H), 4.82 (s, 2H), 2.33 (s, 1H), 2.22-1.60 (m, 6H).

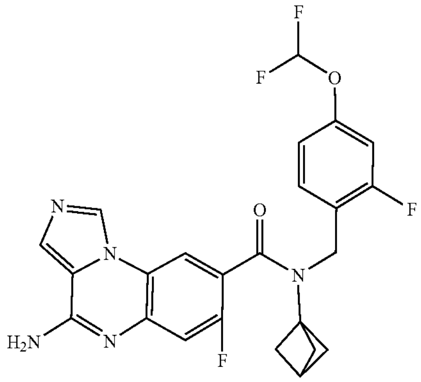 [SMILES: Nc1nc2cc(F)c(C(=O)N(Cc3ccc(OC(F)F)cc3F)C34CC(C3)C4)cc2n2cncc12]

Example Ff-265: 4-amino-N-(bicyclo[1.1.1]pentan-1-yl)-N-(4-(difluoromethoxy)-2-fluorobenzyl)-7-fluoroimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-(4-(difluoromethoxy)-2-fluorobenzyl)bicyclo[1.1.1]pentan-1-amine Ec-13. ES/MS: m/z=486.0 $[M+H]^+$. $^1H$ NMR (400 MHz, MeOD) δ 9.30 (s, 1H), 8.50-8.22 (m, 2H), 7.62-7.26 (m, 2H), 7.05 (t, J=10.7 Hz, 2H), 6.91 (t, J=73.6 Hz, 1H), 5.00 (d, J=15.8 Hz, 1H), 4.80 (d, J=15.8 Hz, 1H), 2.43-2.13 (m, 2H), 1.94-1.62 (m, 5H).

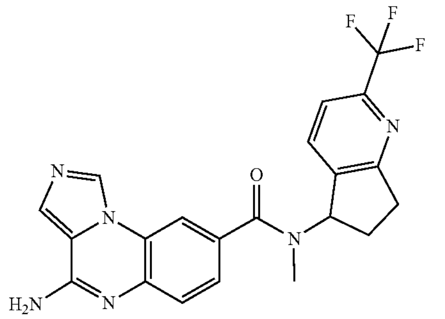 [SMILES: CN(C(=O)c1ccc2nc(N)c3cncn3c2c1)C1CCc2nc(C(F)(F)F)ccc21]

Example 266: 4-amino-N-methyl-N-(2-(trifluoromethyl)-6,7-dihydro-5H-cyclopenta[b]pyridin-5-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-methyl-2-(trifluoromethyl)-6,7-dihydro-5H-cyclopenta[b]pyridin-5-amine hydrochloride Eh-3. ES/MS: m/z=427.0 $[M+H]^+$. $^1H$ NMR (400 MHz, MeOD) δ 9.35 (d, J=15.6 Hz, 1H), 8.50 (s, 1H), 8.42 (s, 1H), 8.03 (d, J=7.7 Hz, 1H), 7.87-7.68 (m, 3H), 6.33 (s, 0.6H, major rotamer), 5.53 (s, 0.4H, minor rotamer), 3.27-2.82 (m, 5H), 2.78-2.28 (m, 2H).

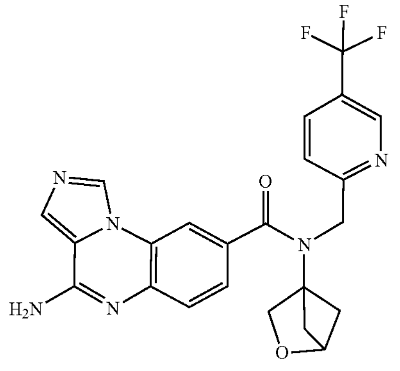 [SMILES: Nc1nc2ccc(C(=O)N(Cc3ccc(C(F)(F)F)cn3)C34COC(C3)C4)cc2n2cncc12]

Example Ff-267: 4-amino-N-(2-oxabicyclo[2.1.1]hexan-4-yl)-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-((5-(trifluoromethyl)pyridin-2-yl)methyl)-2-oxabicyclo[2.1.1]hexan-4-amine Ec-14. ES/MS: m/z=469.0 $[M+H]^+$. $^1H$ NMR (400 MHz, MeOD) δ 9.09-8.83 (m, 2H), 8.31 (d, J=1.7 Hz, 1H), 8.17-7.93 (m, 2H), 7.72-7.40 (m, 3H), 4.93 (s, 2H), 4.41 (s, 1H), 3.74 (s, 2H), 2.19-1.67 (m, 4H).

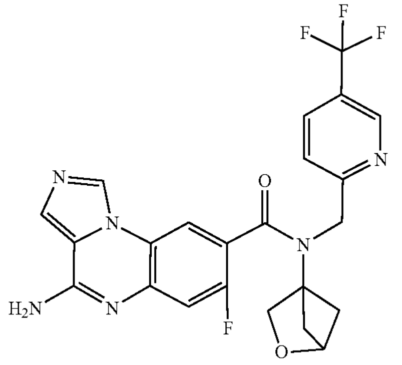 [SMILES: Nc1nc2cc(F)c(C(=O)N(Cc3ccc(C(F)(F)F)cn3)C34COC(C3)C4)cc2n2cncc12]

Example Ff-268: 4-amino-N-(2-oxabicyclo[2.1.1]hexan-4-yl)-7-fluoro-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-((5-(trifluoromethyl)pyridin-2-yl)methyl)-2-oxabicyclo[2.1.1]hexan-4-amine Ec-14. ES/MS: m/z=487.0 $[M+H]^+$. $^1H$ NMR (400 MHz, MeOD) δ 9.17-8.79 (m, 2H), 8.32-7.85 (m, 3H), 7.80-7.04 (m, 2H), 5.02 (s, 1H), 4.83 (s, 1H), 4.63-4.17 (m, 1H), 3.93-3.53 (m, 2H), 2.40-1.84 (m, 3H), 1.74-1.19 (m, 1H).

Example Ff-269: (S)-4-amino-N-(6-cyano-2,3-dihydrobenzofuran-3-yl)-7-fluoro-N-methylimidazo[1,5-a]quinoxaline-8-carboxamide

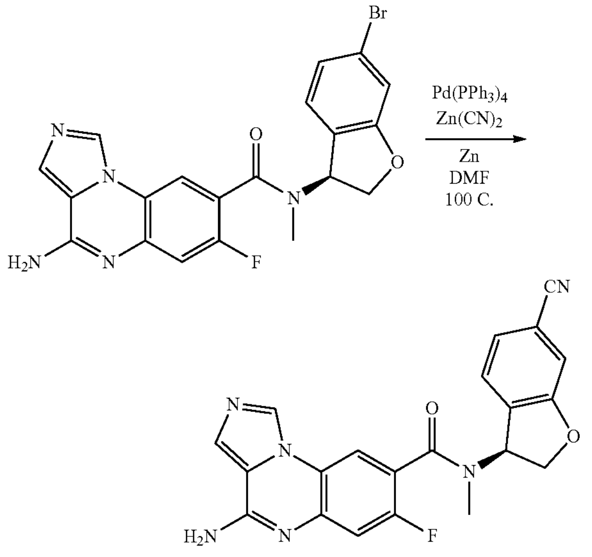

Example Ff-269

Intermediate (S)-4-amino-N-(6-bromo-2,3-dihydrobenzofuran-3-yl)-7-fluoro-N-methylimidazo[1,5-a]quinoxaline-8-carboxamide was prepared following general procedure VI-F starting with starting with starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine Eh-5. ES/MS: m/z=467.2. $[M+H]^+$.

To a solution of (S)-4-amino-N-(6-bromo-2,3-dihydrobenzofuran-3-yl)-7-fluoro-N-methylimidazo[1,5-a]quinoxaline-8-carboxamide (14.0 mg, 0.032 mmol, 1 equiv) in DMF (2.0 mL) was added $Pd(PPh_3)_4$ (18.0 mg, 0.016 mmol, 0.5 equiv), zinc cyanide (11.0 mg, 0.095 mmol, 3.0 equiv), and zinc powder (0.10 mg, 0.002 mmol, 0.05 equiv). The reaction mixture was then degassed with argon for 5 min. The reaction mixture was then heated at 100° C. for 20 h. LCMS analysis confirms full conversion to product. Reaction mixture was diluted with EtOAc, washed with water and 5% aq LiCl, dried over $MgSO_4$, filtered and concentrated under reduced pressure to give a residue. The residue was purified by column chromatography and further purified by reverse phase HPLC. ES/MS: m/z=403.2 $[M+H]^+$. $^1H$ NMR (400 MHz, MeOD) δ 9.26 (s, 1H), 8.45 (d, J=5.9 Hz, 1H), 8.38 (d, J=2.4 Hz, 1H), 7.60-7.45 (m, 2H), 7.44-7.33 (m, 1H), 7.30-7.22 (m, 1H), 6.57 (dd, J=9.0, 3.9 Hz, 0.6H, major rotamer), 5.71 (t, J=6.7 Hz, 0.4H, minor rotamer), 4.96-4.89 (m, 0.8H, minor rotamer), 4.74 (dd, J=10.7, 4.0 Hz, 1.2H, major rotamer), 2.85 (s, 1.2H, minor rotamer), 2.74 (s, 1.8H, major rotamer).

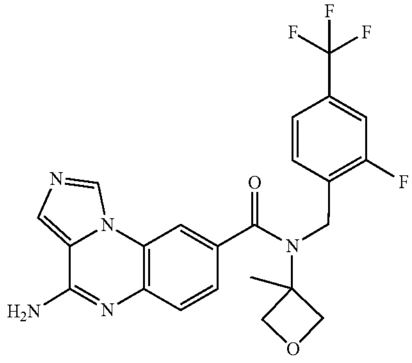 [SMILES: CC1(N(Cc2ccc(C(F)(F)F)cc2F)C(=O)c2ccc3nc(N)c4cncn4c3c2)COC1]

Example Ff-270: 4-amino-N-(2-fluoro-4-(trifluoromethyl)benzyl)-N-(3-methyloxetan-3-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-(2-fluoro-4-(trifluoromethyl)benzyl)-3-methyloxetan-3-amine Ed-17. ES/MS: m/z=474.0 $[M+H]^+$. $^1H$ NMR (400 MHz, MeOD) δ 8.98 (s, 1H), 8.21-8.16 (m, 1H), 7.93 (s, 1H), 7.66 (t, J=7.7 Hz, 1H), 7.56-7.42 (m, 3H), 7.31 (dd, J=10.3, 1.8 Hz, 1H), 5.02 (d, J=6.5 Hz, 2H), 4.75 (s, 2H), 4.39 (d, J=6.5 Hz, 2H), 1.71 (s, 3H).

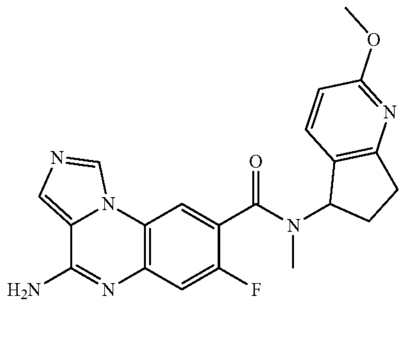 [SMILES: COc1ccc2c(n1)CCC2N(C)C(=O)c1cc2c(cc1F)nc(N)c1cncn12]

Example Ff-271: 4-amino-7-fluoro-N-(2-methoxy-6,7-dihydro-5H-cyclopenta[b]pyridin-5-yl)-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 2-methoxy-N-methyl-6,7-dihydro-5H-cyclopenta[b]pyridin-5-amine hydrochloride Ej-5. ES/MS: m/z=407.0 $[M+H]^+$. $^1H$ NMR (400 MHz, MeOD) δ 9.09 (s, 1H), 8.39-8.22 (m, 1H), 8.03 (s, 1H), 7.61 (t, J=9.0 Hz, 1H), 7.32 (dd, J=10.7, 5.7 Hz, 1H), 6.71 (t, J=9.7 Hz, 1H), 6.31 (dd, J=8.8, 5.8 Hz, 0.4H, minor rotamer), 5.33 (t, J=7.5 Hz, 0.6H, major rotamer), 4.03-3.83 (m, 3H), 3.21-2.93 (m, 2H), 2.91-2.69 (m, 3H), 2.69-2.34 (m, 1H), 2.27-2.14 (m, 1H).

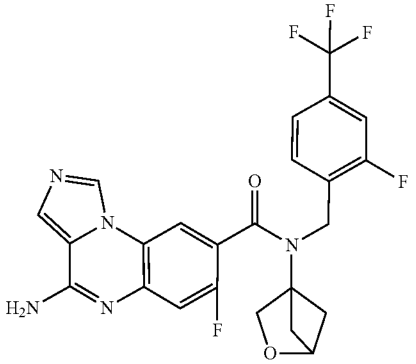 [SMILES: Nc1nc2cc(F)c(C(=O)N(Cc3ccc(C(F)(F)F)cc3F)C34COC(C3)C4)cc2n2cncc12]

Example Ff-272: 4-amino-N-(2-oxabicyclo[2.1.1]hexan-4-yl)-7-fluoro-N-(2-fluoro-4-(trifluoromethyl)benzyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-(2-fluoro-4-(trifluoromethyl)benzyl)-2-oxabicyclo[2.1.1]hexan-4-amine Ec-15. ES/MS: m/z=504.0 $[M+H]^+$. $^1H$ NMR (400 MHz, MeOD) δ 9.22-8.85 (m, 1H), 8.22 (s, 1H), 8.00 (s, 1H), 7.85-7.13 (m, 4H), 5.18-4.91 (m, 2H), 4.59-4.15 (m, 1H), 3.87-3.48 (m, 2H), 2.33-1.71 (m, 4H).

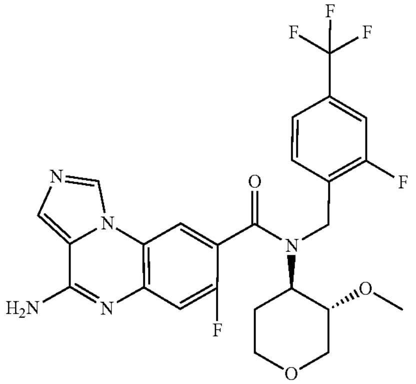 [SMILES: CO[C@@H]1COCC[C@H]1N(Cc1ccc(C(F)(F)F)cc1F)C(=O)c1cc2c(cc1F)nc(N)c1cncn12]

Example Ff-273: 4-amino-7-fluoro-N-(2-fluoro-4-(trifluoromethyl)benzyl)-N-((3S,4R)-3-methoxytetrahydro-2H-pyran-4-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (3S,4R)—N-(2-fluoro-4-(trifluoromethyl)benzyl)-3-methoxytetrahydro-2H-pyran-4-amine Ed-18. ES/MS: m/z=536.0 $[M+H]^+$. $^1H$ NMR (400 MHz, MeOD) δ 9.42-9.12 (m, 1H), 8.47-8.18 (m, 2H), 7.87-7.68 (m, 1H), 7.65-7.22 (m, 3H), 5.08 (d, J=16.8 Hz, 1H), 4.84-4.73 (m, 1H), 4.37-4.07 (m, 1H), 4.02-3.64 (m, 2H), 3.42 (s, 3H), 3.24 (d, J=12.3 Hz, 2H), 2.77 (t, J=10.5 Hz, 1H), 2.15-1.71 (m, 2H).

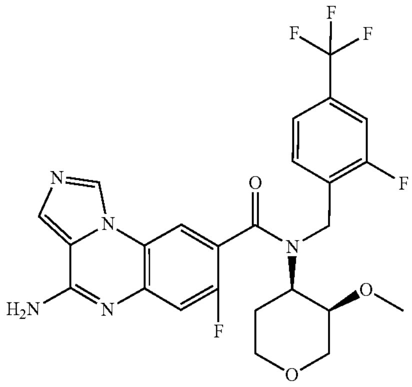 [SMILES: CO[C@H]1COCC[C@H]1N(Cc1ccc(C(F)(F)F)cc1F)C(=O)c1cc2c(cc1F)nc(N)c1cncn12]

Example Ff-274: 4-amino-7-fluoro-N-(2-fluoro-4-(trifluoromethyl)benzyl)-N-((3R,4R)-3-methoxytetrahydro-2H-pyran-4-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (3R,4R)—N-(2-fluoro-4-(trifluoromethyl)benzyl)-3-methoxytetrahydro-2H-pyran-4-amine Ed-19. ES/MS: m/z=536.0 $[M+H]^+$. $^1H$ NMR (400 MHz, MeOD) δ 9.30 (s, 0.6H, major rotamer), 9.05 (s, 0.4H, minor rotamer), 8.49 (s, 0.6H, major rotamer), 8.41-8.28 (m, 1H), 8.15 (d, J=5.8 Hz, 0.4H, minor rotamer), 7.74-7.14 (m, 4H), 5.25-4.94 (m, 2H), 4.33-3.84 (m, 3H), 3.79-3.39 (m, 3H), 3.26-2.94 (m, 3H), 2.39 (s, 1H), 1.57 (d, J=13.3 Hz, 1H).

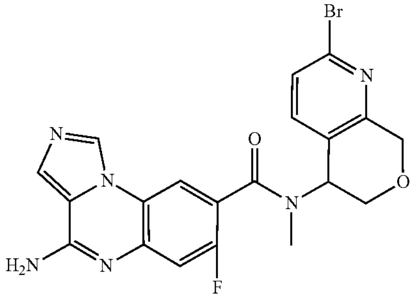 [SMILES: CN(C(=O)c1cc2c(cc1F)nc(N)c1cncn12)C1COCc2nc(Br)ccc21]

Example Ff-275: 4-amino-N-(2-bromo-5,8-dihydro-6H-pyrano[3,4-b]pyridin-5-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 2-bromo-N-methyl-5,8-dihydro-6H-pyrano[3,4-b]pyridin-5-amine Ec-16. ES/MS: m/z=472.0 $[M+H]^+$. $^1H$ NMR (400 MHz, MeOD) δ 9.27 (d, J=0.7 Hz, 0.7H, major rotamer), 9.26 (d, J=0.7 Hz, 0.3H, minor rotamer), 8.65-8.46 (m, 1H), 8.38 (dd, J=2.3, 0.7 Hz, 1H), 7.73 (d, J=8.2 Hz, 1H), 7.69-7.56 (m, 1H), 7.53-7.45 (m, 1H), 5.98-5.85 (m, 1H), 4.84-4.55 (m, 2H), 4.36-3.99 (m, 2H), 2.97 (s, 1H, minor rotamer), 2.87 (d, J=1.1 Hz, 2H, major rotamer).

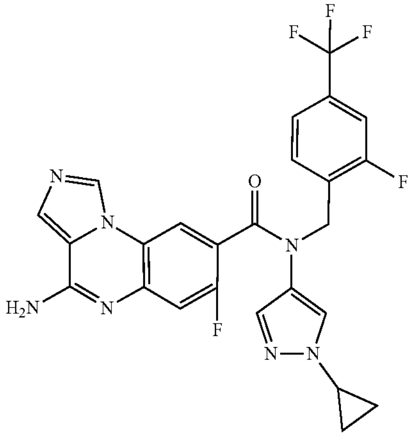 [SMILES: Nc1nc2cc(F)c(C(=O)N(Cc3ccc(C(F)(F)F)cc3F)c3cnn(C4CC4)c3)cc2n2cncc12]

Example Ff-276: 4-amino-N-(1-cyclopropyl-1H-pyrazol-4-yl)-7-fluoro-N-(2-fluoro-4-(trifluoromethyl)benzyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 1-cyclopropyl-N-(2-fluoro-4-(trifluoromethyl)benzyl)-1H-pyrazol-4-amine Ed-20. ES/MS: m/z=528.0 $[M+H]^+$. $^1H$ NMR (400 MHz, MeOD) δ 9.24-9.20 (m, 1H), 8.38 (d, J=5.7 Hz, 1H), 8.36 (d, J=0.6 Hz, 1H), 7.72 (t, J=7.6 Hz, 1H), 7.64 (s, 1H), 7.57 (d, J=8.0 Hz, 1H), 7.54-7.46 (m, 1H), 7.26 (d, J=9.5 Hz, 1H), 7.19 (d, J=1.0 Hz, 1H), 5.19 (s, 2H), 3.51-3.41 (m, 1H), 0.98-0.76 (m, 4H).

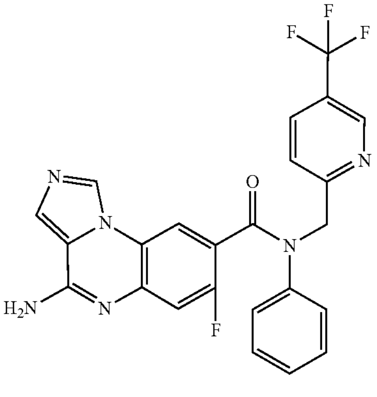 [SMILES: Nc1nc2cc(F)c(C(=O)N(Cc3ccc(C(F)(F)F)cn3)c3ccccc3)cc2n2cncc12]

Example Ff-277: 4-amino-7-fluoro-N-phenyl-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-((5-(trifluoromethyl)pyridin-2-yl)methyl)aniline Ed-21. ES/MS: m/z=481.0 $[M+H]^+$. $^1H$ NMR (400 MHz, MeOD) δ 9.19 (s, 1H), 8.89 (s, 1H), 8.40 (d, J=5.7 Hz, 1H), 8.30 (s, 1H), 8.16 (d, J=8.3 Hz, 1H), 7.78 (d, J=8.2 Hz, 1H), 7.32 (d, J=7.7 Hz, 2H), 7.27-7.09 (m, 4H), 5.38 (s, 2H).

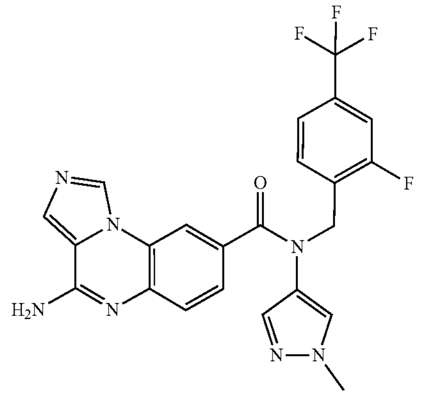 [SMILES: Cn1cc(N(Cc2ccc(C(F)(F)F)cc2F)C(=O)c2ccc3nc(N)c4cncn4c3c2)cn1]

Example Ff-278: 4-amino-N-(2-fluoro-4-(trifluoromethyl)benzyl)-N-(1-methyl-1H-pyrazol-4-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-(2-fluoro-4-(trifluoromethyl)benzyl)-1-methyl-1H-pyrazol-4-amine Ed-6. ES/MS: m/z=484.0 [M+H]$^+$. $^1$H NMR (400 MHz, MeOD) δ 9.24 (d, J=0.7 Hz, 1H), 8.41-8.35 (m, 2H), 7.75 (s, 1H), 7.65-7.39 (m, 5H), 7.24 (s, 1H), 5.20 (s, 2H), 3.68 (s, 3H).

Example Ff-279: (S)-4-amino-7-fluoro-N-methyl-N-(7-(1-(trifluoromethyl)-1H-pyrazol-4-yl)isochroman-4-yl)imidazo[1,5-a]quinoxaline-8-carboxamide

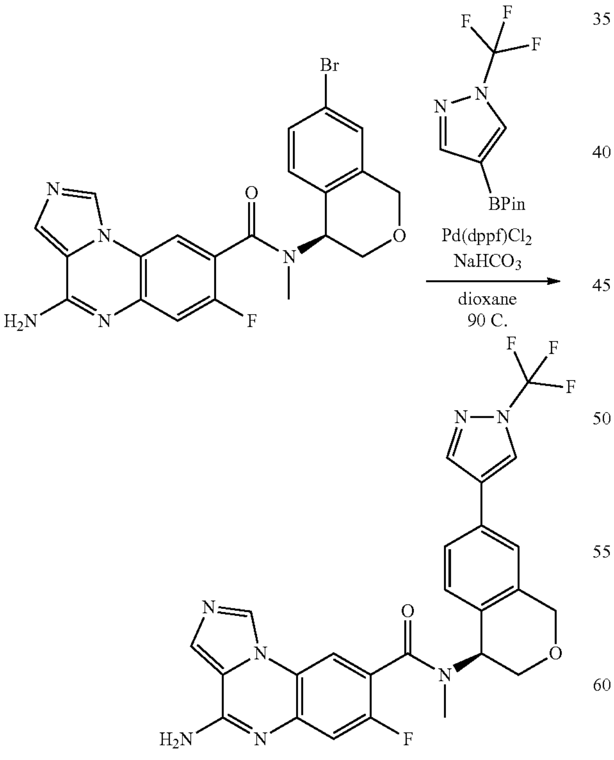

Example Ff-279

Intermediate (S)-4-amino-N-(7-bromoisochroman-4-yl)-7-fluoro-N-methylimidazo[1,5-a]quinoxaline-8-carboxamide was prepared following general procedure VI-F starting with starting with starting with 4-((tert-butoxycarbonyl)amino)-7-fluoroimidazo[1,5-a]quinoxaline-8-carboxylic acid Af-1 and (S)-7-bromo-N-methylisochroman-4-amine hydrochloride Eh-4. ES/MS: m/z=471.2. [M+H]$^+$.

To a solution of (S)-4-amino-N-(7-bromoisochroman-4-yl)-7-fluoro-N-methylimidazo[1,5-a]quinoxaline-8-carboxamide (30.0 mg, 0.064 mmol, 1 equiv) in dioxane (1.0 mL) was added $PdCl_2$(dppf) (7.0 mg, 0.010 mmol, 0.15 equiv), 4-(4,4,5,5-tetramethyl-1,3,2-dioxaborolan-2-yl)-1-(trifluoromethyl)pyrazole (50.0 mg, 0.19 mmol, 3.0 equiv), and aqueous $NaHCO_3$ (2M, 0.25 mL, 0.50 mmol, 8.0 equiv). The reaction mixture was then degassed with argon for 5 min. The reaction mixture was then heated at 90° C. for 5 h. LCMS analysis confirms full conversion to product. Reaction mixture was diluted with EtOAc, washed with water and 5% aq LiCl, dried over $MgSO_4$, filtered and concentrated under reduced pressure to give a residue. The residue was purified by column chromatography. Final purification by reverse phase HPLC. ES/MS: m/z=526.0 [M+H]$^+$. $^1$H NMR (400 MHz, MeOD) δ 9.33-9.28 (m, 1H), 8.69-8.56 (m, 1H), 8.50 (d, J=5.9 Hz, 1H), 8.42-8.36 (m, 1H), 8.29-8.21 (m, 1H), 7.66 (dt, J=11.5, 5.8 Hz, 1H), 7.56-7.36 (m, 3H), 5.88 (s, 0.6H, major rotamer), 4.94 (d, J=15.1 Hz, 1H), 4.80 (d, J=15.2 Hz, 1H), 4.68 (d, J=15.2 Hz, 0.4H, minor rotamer), 4.42-3.93 (m, 2H), 2.98 (s, 1.2H, minor rotamer), 2.84 (d, J=1.1 Hz, 1.8H, major rotamer).

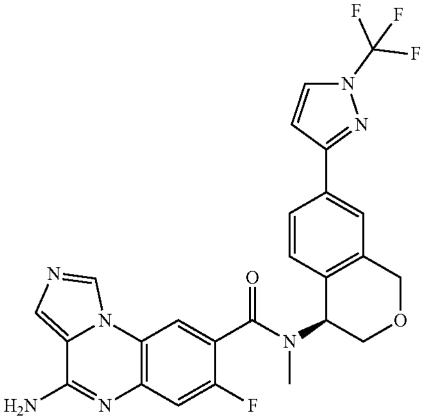 [SMILES: CN(C(=O)c1cc2c(cc1F)nc(N)c1cncn12)[C@@H]1COCc2cc(-c3ccn(C(F)(F)F)n3)ccc21]

Example Ff-280: (S)-4-amino-7-fluoro-N-methyl-N-(7-(1-(trifluoromethyl)-1H-pyrazol-3-yl)isochroman-4-yl)imidazo[1,5-a]quinoxaline-8-carboxamide Prepared following procedure reported for example Ff-279 starting with 4-((tert-butoxycarbonyl)amino)-7-fluoroimidazo[1,5-a]quinoxaline-8-carboxylic acid Af-1, (S)-7-bromo-N-methylisochroman-4-amine hydrochloride Eh-4 and 3-(4,4,5,5-tetramethyl-1,3,2-dioxaborolan-2-yl)-1-(trifluoromethyl)pyrazole. ES/MS: m/z=526.0 [M+H]$^+$. $^1$H NMR (400 MHz, MeOD) δ 9.30 (s, 1H), 8.50 (d, J=5.9 Hz, 1H), 8.37 (d, J=3.3 Hz, 1H), 8.27-8.20 (m, 1H), 7.94-7.83 (m, 1H), 7.81-7.65 (m, 1H), 7.53-7.41 (m, 2H), 7.04-6.96 (m, 1H), 5.95-5.90 (m, 1H), 5.02-4.92 (m, 1H), 4.82 (d, J=15.2 Hz, 1H), 4.38-4.00 (m, 2H), 2.99 (s, 1H, minor rotamer), 2.85 (d, J=1.1 Hz, 2H, major rotamer).

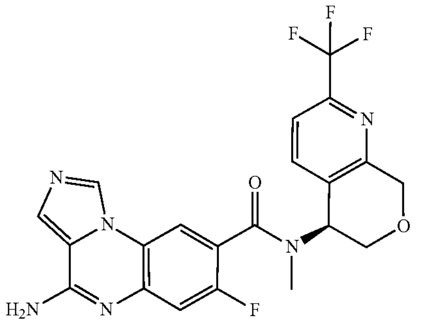

Example Ff-281: (S)-4-amino-7-fluoro-N-methyl-N-(2-(trifluoromethyl)-5,8-dihydro-6H-pyrano[3,4-b]pyridin-5-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)—N-methyl-2-(trifluoromethyl)-5,8-dihydro-6H-pyrano[3,4-b]pyridin-5-amine hydrochloride Ei-3. ES/MS: m/z=461.0 $[M+H]^+$. $^1$H NMR (400 MHz, MeOD) δ 9.30-9.24 (m, 1H), 8.51 (d, J=5.8 Hz, 1H), 8.42-8.37 (m, 1H), 8.07 (d, J=8.1 Hz, 0.7H, major rotamer), 8.02 (d, J=8.1 Hz, 0.3H, minor rotamer), 7.82 (d, J=8.1 Hz, 1H), 7.56-7.47 (m, 1H), 6.01 (t, J=4.2 Hz, 0.7H, major rotamer), 5.04-4.91 (m, 1H), 4.82 (d, J=16.2 Hz, 1H), 4.71 (d, J=16.3 Hz, 0.3H, minor rotamer), 4.47-4.01 (m, 2H), 2.97 (s, 0.9H, minor rotamer), 2.89 (d, J=1.1 Hz, 2.1H, major rotamer).

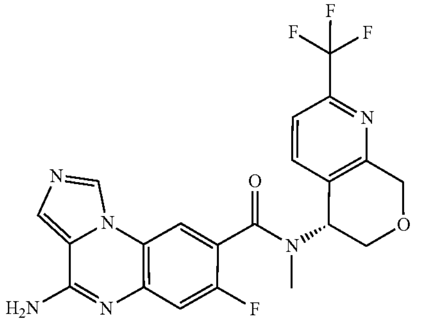 [SMILES: CN(C(=O)c1cc2c(cc1F)nc(N)c1cncn12)[C@H]1COCc2nc(C(F)(F)F)ccc21]

Example Ff-282: (R)-4-amino-7-fluoro-N-methyl-N-(2-(trifluoromethyl)-5,8-dihydro-6H-pyrano[3,4-b]pyridin-5-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (R)—N-methyl-2-(trifluoromethyl)-5,8-dihydro-6H-pyrano[3,4-b]pyridin-5-amine hydrochloride Ei-4. ES/MS: m/z=461.0 $[M+H]^+$. $^1$H NMR (400 MHz, MeOD) δ 9.29-9.23 (m, 1H), 8.50 (d, J=5.9 Hz, 1H), 8.39-8.34 (m, 1H), 8.07 (d, J=8.0 Hz, 0.7H, major rotamer), 8.02 (d, J=8.1 Hz, 0.3H, minor rotamer), 7.85-7.75 (m, 1H), 7.53-7.44 (m, 1H), 6.01 (s, 0.7H, major rotamer), 5.05-4.92 (m, 1H), 4.82 (d, J=16.3 Hz, 1H), 4.72 (d, J=16.3 Hz, 0.3H, minor rotamer), 4.43-3.99 (m, 2H), 2.97 (s, 0.9H, minor rotamer), 2.89 (d, J=1.1 Hz, 2.1H, major rotamer).

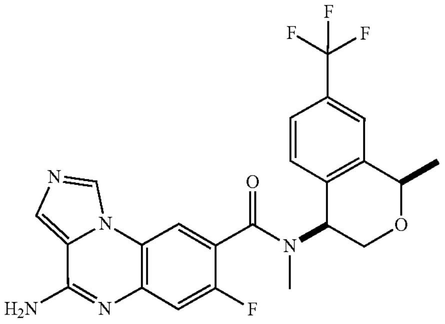

(±)

Example Ff-283: Rac-4-amino-7-fluoro-N-methyl-N-((1R,4S)-1-methyl-7-(trifluoromethyl)isochroman-4-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and rac-(1S,4R)—N,1-dimethyl-7-(trifluoromethyl)isochroman-4-amine hydrochloride (±)-Ei-2. ES/MS: m/z=474.0 $[M+H]^+$. $^1$H NMR (400 MHz, MeOD) δ 9.29 (d, J=0.7 Hz, 1H), 8.50 (d, J=5.9 Hz, 1H), 8.38 (dd, J=1.8, 0.6 Hz, 1H), 7.71-7.57 (m, 3H), 7.55-7.45 (m, 1H), 5.88 (d, J=3.7 Hz, 1H), 4.85-4.72 (m, 1H), 4.38 (dd, J=12.8, 1.6 Hz, 1H), 4.19 (dd, J=12.8, 4.0 Hz, 1H), 3.00 (s, 1H, minor rotamer), 2.86 (d, J=1.1 Hz, 2H, major rotamer), 1.68-1.61 (m, 3H).

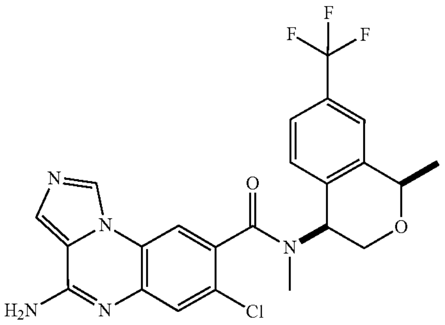

(±)

Example Ff-284: Rac-4-amino-7-chloro-N-methyl-N-((1R,4S)-1-methyl-7-(trifluoromethyl)isochroman-4-yl)imidazo[1,5-a]quinoxaline-8-carboxamide. Prepared following general procedure VI-F starting with 4-((tert-butoxycarbonyl)amino)-7-chloroimidazo[1,5-a]quinoxaline-8-carboxylic acid Af-2 and rac-(1S,4R)—N,1-dimethyl-7-(trifluoromethyl)isochroman-4-amine hydrochloride (±)-Ei-2. ES/MS: m/z=491.0 $[M+H]^+$. $^1$H NMR (400 MHz, MeOD) δ 9.39-9.23 (m, 1H), 8.70-8.43 (m, 1H), 8.38 (d, J=1.7 Hz, 1H), 7.83-7.52 (m, 4H), 5.90 (s, 1H), 4.89-4.65 (m, 1H), 4.53-4.10 (m, 1.8H, major rotamer), 4.07-3.84 (m, 0.2H, minor rotamer), 3.01 (d, J=16.3 Hz, 0.6H, minor rotamer), 2.79 (s, 2.4H, major rotamer), 1.64 (d, J=6.5 Hz, 3H).

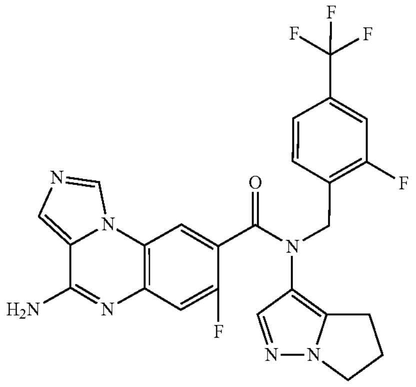 [SMILES: Nc1nc2cc(F)c(C(=O)N(Cc3ccc(C(F)(F)F)cc3F)c3cnn4c3CCC4)cc2n2cncc12]

Example Ff-285: 4-amino-N-(5,6-dihydro-4H-pyrrolo[1,2-b]pyrazol-3-yl)-7-fluoro-N-(2-fluoro-4-(trifluoromethyl)benzyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-(2-fluoro-4-(trifluoromethyl)benzyl)-5,6-dihydro-4H-pyrrolo[1,2-b]pyrazol-3-amine Ed-22. ES/MS: m/z=528.0 $[M+H]^+$. $^1H$ NMR (400 MHz, MeOD) δ 9.23 (d, J=0.7 Hz, 1H), 8.40 (d, J=5.8 Hz, 1H), 8.31 (d, J=0.7 Hz, 1H), 7.73 (t, J=7.6 Hz, 1H), 7.61-7.54 (m, 1H), 7.51 (d, J=9.9 Hz, 1H), 7.28-7.20 (m, 2H), 5.18 (s, 2H), 3.90 (t, J=7.2 Hz, 2H), 2.52 (t, J=7.2 Hz, 2H), 2.42 (p, J=7.0 Hz, 2H).

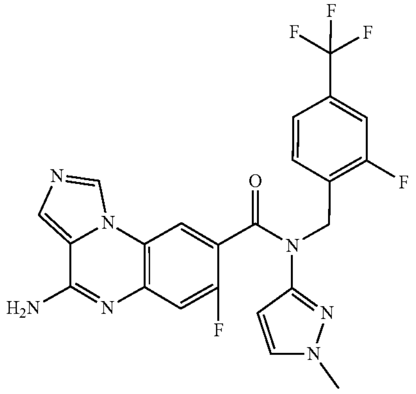 [SMILES: Cn1ccc(N(Cc2ccc(C(F)(F)F)cc2F)C(=O)c2cc3c(cc2F)nc(N)c2cncn23)n1]

Example Ff-286: 4-amino-7-fluoro-N-(2-fluoro-4-(trifluoromethyl)benzyl)-N-(1-methyl-1H-pyrazol-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-(2-fluoro-4-(trifluoromethyl)benzyl)-1-methyl-1H-pyrazol-3-amine Ed-23. ES/MS: m/z=502.0 $[M+H]^+$. $^1H$ NMR (400 MHz, MeOD) δ 9.21 (s, 1H), 8.36 (d, J=5.9 Hz, 1H), 8.29 (s, 1H), 7.79 (t, J=7.8 Hz, 1H), 7.53 (d, J=8.0 Hz, 1H), 7.46 (d, J=10.0 Hz, 1H), 7.33 (s, 1H), 7.22 (d, J=9.7 Hz, 1H), 5.95 (s, 1H), 5.28 (s, 2H), 3.65 (s, 3H).

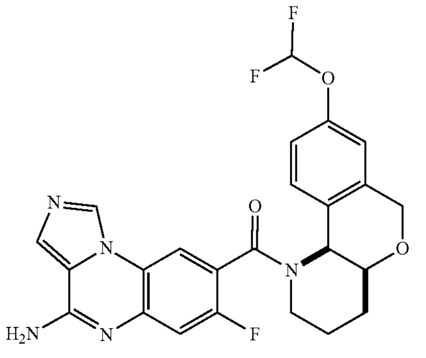

(±)

Example Ff-287: Rac-(4-amino-7-fluoroimidazo[1,5-a]quinoxalin-8-yl)((4aS,10bS)-8-(difluoromethoxy)-2,3,4,4a,6,10b-hexahydro-1H-isochromeno[4,3-b]pyridin-1-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,10bS)-8-(difluoromethoxy)-2,3,4,4a,6,10b-hexahydro-1H-isochromeno[4,3-b]pyridine hydrochloride Ebc-1. ES/MS: m/z=484.0 $[M+H]^+$. $^1H$ NMR (400 MHz, MeOD) δ 9.31 (s, 1H), 8.53 (s, 1H), 8.39 (d, J=11.0 Hz, 1H), 7.60-7.30 (m, 2H), 7.13 (dd, J=8.5, 2.5 Hz, 1H), 7.07-6.59 (m, 2H), 6.05 (s, 1H), 4.94 (d, J=16.0 Hz, 1H), 4.84-4.48 (m, 1H), 4.22 (dt, J=11.3, 6.2 Hz, 1H), 3.41 (d, J=13.9 Hz, 1H), 2.99-2.49 (m, 1H), 2.01-1.57 (m, 4H).

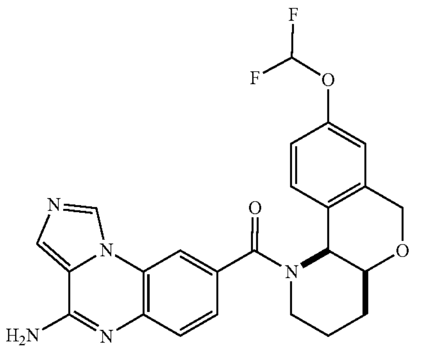

(±)

Example Ff-288: Rac-(4-aminoimidazo[1,5-a]quinoxalin-8-yl)((4aS,10bS)-8-(difluoromethoxy)-2,3,4,4a,6,10b-hexahydro-1H-isochromeno[4,3-b]pyridin-1-yl)methanone. Prepared following general procedure VI-F starting with 4-((tert-butoxycarbonyl)amino)imidazo[1,5-a]quinoxaline-8-carboxylic acid Ae-1 and rac-(4aS,10bS)-8-(difluoromethoxy)-2,3,4,4a,6,10b-hexahydro-1H-isochromeno[4,3-b]pyridine hydrochloride Ebc-1. ES/MS: m/z=466.0 $[M+H]^+$. $^1H$ NMR (400 MHz, MeOD) δ 9.36 (s, 1H), 8.51 (t, J=1.1 Hz, 1H), 8.42 (s, 1H), 7.78-7.68 (m, 2H), 7.46 (d, J=8.6 Hz, 1H), 7.16 (dd, J=8.5, 2.5 Hz, 1H), 6.95 (s, 1H), 6.85 (t, J=74.0 Hz, 1H), 5.99 (s, 1H), 4.97-4.62 (m, 3H), 4.26 (dt, J=10.9, 5.6 Hz, 1H), 2.82 (s, 1H), 2.03-1.63 (m, 4H).

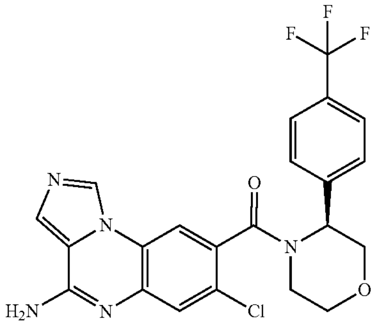 [SMILES: Nc1nc2cc(Cl)c(C(=O)N3CCOC[C@@H]3c3ccc(C(F)(F)F)cc3)cc2n2cncc12]

Example Ff-289: (S)-(4-amino-7-chloroimidazo[1,5-a]quinoxalin-8-yl)(3-(4-(trifluoromethyl)phenyl)morpholino)methanone. Prepared following general procedure VI-F starting with 4-((tert-butoxycarbonyl)amino)-7-chloroimidazo[1,5-a]quinoxaline-8-carboxylic acid Af-2 and commercial (3S)-3-[4-(trifluoromethyl)phenyl]morpholine. ES/MS: m/z=477.0 $[M+H]^+$. $^1H$ NMR (400 MHz, MeOD) δ 9.38-9.27 (m, 1H), 8.57-8.29 (m, 2H), 7.95-7.88 (m, 2H), 7.77-7.56 (m, 3H), 5.94-5.86 (m, 1H), 4.69-4.58 (m, 1H), 4.10-4.02 (m, 1H), 3.94-3.63 (m, 2H), 3.43-3.21 (m, 2H).

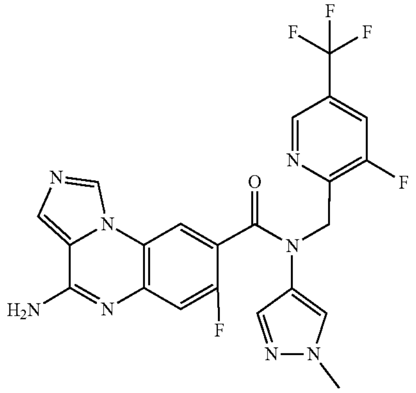 [SMILES: Cn1cc(N(Cc2ncc(C(F)(F)F)cc2F)C(=O)c2cc3c(cc2F)nc(N)c2cncn23)cn1]

Example Ff-290: 4-amino-7-fluoro-N-((3-fluoro-5-(trifluoromethyl)pyridin-2-yl)methyl)-N-(1-methyl-1H-pyrazol-4-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-((3-fluoro-5-(trifluoromethyl)pyridin-2-yl)methyl)-1-methyl-1H-pyrazol-4-amine Ed-24. ES/MS: m/z=503.0 $[M+H]^+$. $^1H$ NMR (400 MHz, MeOD) δ 9.28 (d, J=0.7 Hz, 1H), 8.87-8.82 (m, 1H), 8.41-8.35 (m, 2H), 8.04 (dd, J=9.5, 1.9 Hz, 1H), 7.69 (s, 1H), 7.38 (s, 1H), 7.27 (d, J=9.4 Hz, 1H), 5.31 (s, 2H), 3.67 (s, 3H).

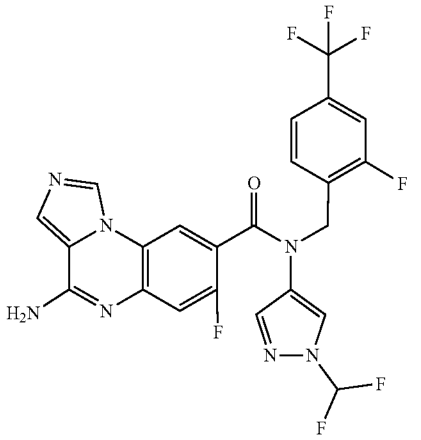 [SMILES: Nc1nc2cc(F)c(C(=O)N(Cc3ccc(C(F)(F)F)cc3F)c3cnn(C(F)F)c3)cc2n2cncc12]

Example Ff-291: 4-amino-N-(1-(difluoromethyl)-1H-pyrazol-4-yl)-7-fluoro-N-(2-fluoro-4-(trifluoromethyl)benzyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 1-(difluoromethyl)-N-(2-fluoro-4-(trifluoromethyl)benzyl)-1H-pyrazol-4-amine Ed-25. ES/MS: m/z=538.0 $[M+H]^+$. $^1H$ NMR (400 MHz, MeOD) δ 9.22 (s, 1H), 8.42 (d, J=5.8 Hz, 1H), 8.35 (s, 1H), 8.06 (s, 1H), 7.75 (t, J=7.6 Hz, 1H), 7.57 (d, J=8.0 Hz, 1H), 7.51 (d, J=8.8 Hz, 2H), 7.45-7.00 (m, 2H), 5.24 (s, 2H).

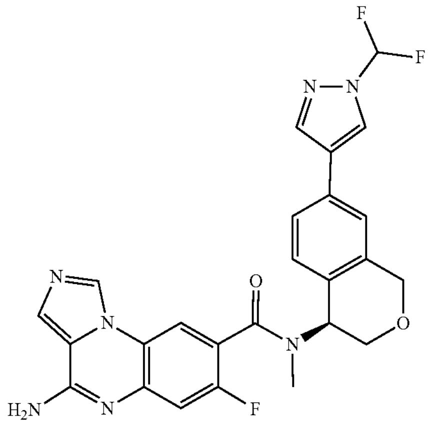 [SMILES: CN(C(=O)c1cc2c(cc1F)nc(N)c1cncn12)[C@@H]1COCc2cc(-c3cnn(C(F)F)c3)ccc21]

Example Ff-292: (S)-4-amino-7-fluoro-N-methyl-N-(7-(1-(difluoromethyl)-1H-pyrazol-4-yl)isochroman-4-yl)imidazo[1,5-a]quinoxaline-8-carboxamide. Prepared following procedure reported for example Ff-279 starting with 4-((tert-butoxycarbonyl)amino)-7-fluoroimidazo[1,5-a]quinoxaline-8-carboxylic acid Af-1, (S)-7-bromo-N-methylisochroman-4-amine hydrochloride Eh-4, and 1-(difluoromethyl)-4-(4,4,5,5-tetramethyl-1,3,2-dioxaborolan-2-yl)pyrazole. ES/MS: m/z=508.0 $[M+H]^+$. $^1H$ NMR (400 MHz, MeOD) δ 9.36-9.25 (m, 1H), 8.53-8.43 (m, 2H), 8.41-8.36 (m, 1H), 8.14 (s, 0.7H, major rotamer), 8.10 (s, 0.3H, minor rotamer), 7.72-7.34 (m, 5H), 5.88 (s, 1H), 4.98-4.90 (m, 1H), 4.83-4.60 (m, 1H), 4.35-3.98 (m, 2H), 2.98 (s, 0.9H, minor rotamer), 2.84 (d, J=1.1 Hz, 2.1H, major rotamer).

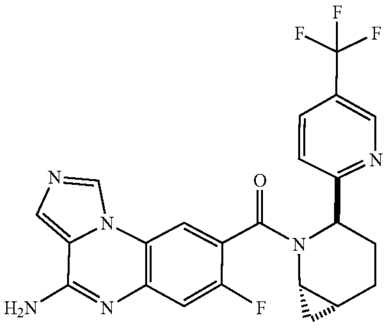

(±)

Example Ff-293: Rac-(4-amino-7-fluoroimidazo[1,5-a]quinoxalin-8-yl)((1S,3R,6R)-3-(5-(trifluoromethyl)pyridin-2-yl)-2-azabicyclo[4.1.0]heptan-2-yl)methanone. Prepared following general procedure VI-F starting with 4-((tert-butoxycarbonyl)amino)-7-chloroimidazo[1,5-a]quinoxaline-8-carboxylic acid Af-1 and rac-(1S,3R,6R)-3-(5-(trifluoromethyl)pyridin-2-yl)-2-azabicyclo[4.1.0]heptane hydrochloride Eai-17. ES/MS: m/z=471.0 $[M+H]^+$. $^1$H NMR (400 MHz, MeOD) δ 9.31 (d, J=0.7 Hz, 1H), 8.94 (dt, J=1.9, 1.0 Hz, 0.8H, major rotamer), 8.83 (d, J=2.3 Hz, 0.2H, minor rotamer), 8.52 (d, J=5.7 Hz, 1H), 8.41 (d, J=0.6 Hz, 0.8H, major rotamer), 8.35 (s, 0.2H, minor rotamer), 8.22-8.12 (m, 1H), 7.78-7.67 (m, 1H), 7.54 (d, J=9.5 Hz, 0.8H, major rotamer), 7.36 (s, 0.2H, minor rotamer), 5.61 (t, J=5.0 Hz, 1H), 2.98 (dt, J=8.3, 4.9 Hz, 1H), 2.36 (dq, J=14.3, 4.8 Hz, 1H), 2.13-1.93 (m, 1H), 1.85-1.10 (m, 3H), 0.69 (dd, J=8.2, 5.0 Hz, 2H).

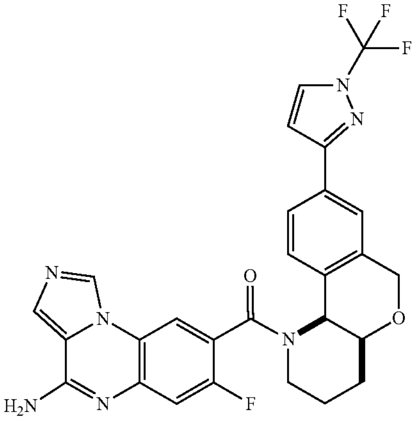

(±)

Example Ff-294: Rac-(4-amino-7-fluoroimidazo[1,5-a]quinoxalin-8-yl)((4aS,10bS)-8-(1-(trifluoromethyl)-1H-pyrazol-3-yl)-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-8-(1-(trifluoromethyl)-1H-pyrazol-3-yl)-2,3,4,4a,6,10b-hexahydro-1H-isochromeno[4,3-b]pyridine hydrochloride Ebd-1. ES/MS: m/z=552.0 $[M+H]^+$. $^1$H NMR (400 MHz, MeOD) δ 9.31 (s, 1H), 8.73-8.47 (m, 2H), 8.46-8.30 (m, 1H), 8.29-8.14 (m, 1H), 7.66 (d, J=8.0 Hz, 1H), 7.57-7.32 (m, 3H), 6.12 (s, 1H), 5.08-4.92 (m, 1H), 4.80-4.46 (m, 1H), 4.25 (d, J=8.9 Hz, 1H), 3.44 (d, J=13.9 Hz, 1H), 2.97 (s, 1H), 2.07-1.51 (m, 4H).

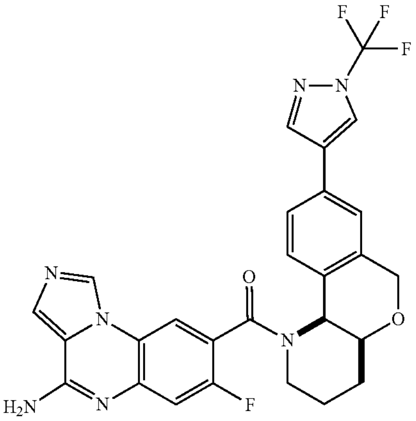

(±)

Example Ff-295: Rac-(4-amino-7-fluoroimidazo[1,5-a]quinoxalin-8-yl)((4aS,10bS)-8-(1-(trifluoromethyl)-1H-pyrazol-4-yl)-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-8-(1-(trifluoromethyl)-1H-pyrazol-4-yl)-2,3,4,4a,6,10b-hexahydro-1H-isochromeno[4,3-b]pyridine hydrochloride Ebd-2. ES/MS: m/z=552.0 $[M+H]^+$. $^1$H NMR (400 MHz, MeOD) δ 9.28 (s, 1H), 8.54 (s, 1H), 8.37-8.30 (m, 1H), 8.27-8.20 (m, 1H), 7.89 (s, 1H), 7.77-7.59 (m, 1H), 7.59-7.37 (m, 2H), 7.03-6.94 (m, 1H), 6.14 (s, 1H), 5.07-4.94 (m, 1H), 4.79-4.47 (m, 1H), 4.26 (q, J=7.1 Hz, 1H), 3.45 (d, J=13.9 Hz, 1H), 3.07-2.89 (m, 1H), 2.09-1.59 (m, 4H).

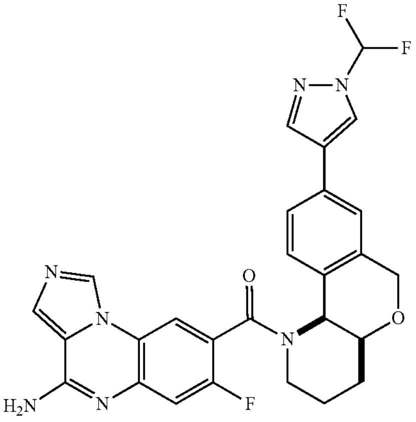

(±)

Example Ff-296: Rac-(4-amino-7-fluoroimidazo[1,5-a]quinoxalin-8-yl)((4aS,10bS)-8-(1-(difluoromethyl)-1H-pyrazol-4-yl)-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-8-(1-(difluoromethyl)-1H-pyrazol-4-yl)-2,3,4,4a,6,10b-hexahydro-1H-isochromeno[4, 3-b]pyridine hydrochloride Ebd-3. ES/MS: m/z=534.0 $[M+H]^+$. $^1H$ NMR (400 MHz, MeOD) δ 9.30 (s, 1H), 8.54 (s, 1H), 8.48-8.40 (m, 1H), 8.40-8.30 (m, 1H), 8.17-8.04 (m, 1H), 7.70-7.60 (m, 1H), 7.56-7.23 (m, 4H), 6.11 (s, 1H), 5.00 (d, J=15.8 Hz, 1H), 4.77-4.43 (m, 1H), 4.25 (q, J=7.0 Hz, 1H), 3.44 (d, J=13.9 Hz, 1H), 2.98 (s, 1H), 2.07-1.52 (m, 4H).

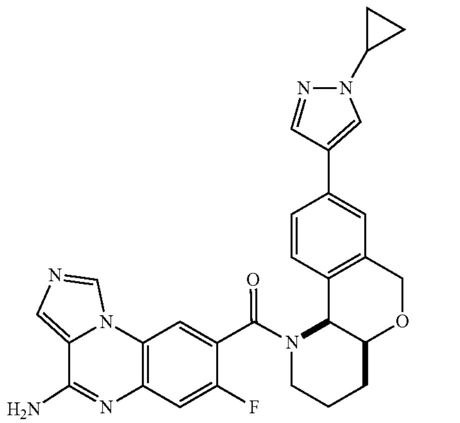

(±)

Example Ff-297: Rac-(4-amino-7-fluoroimidazo[1,5-a]quinoxalin-8-yl)((4aS,10bS)-8-(1-cyclopropyl-1H-pyrazol-4-yl)-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-8-(1-cyclopropyl-1H-pyrazol-4-yl)-2,3,4,4a,6,10b-hexahydro-1H-isochromeno[4,3-b]pyridine hydrochloride Ebd-4. ES/MS: m/z=524.0 $[M+H]^+$. $^1H$ NMR (400 MHz, MeOD) δ 9.30 (s, 1H), 8.54 (s, 1H), 8.40-8.32 (m, 1H), 8.15-7.98 (m, 1H), 7.90-7.74 (m, 1H), 7.61-7.20 (m, 4H), 6.10 (s, 1H), 4.98 (d, J=15.7 Hz, 1H), 4.71-4.42 (m, 1H), 4.23 (d, J=7.5 Hz, 1H), 3.79-3.59 (m, 1H), 3.42 (d, J=13.5 Hz, 1H), 2.98 (s, 1H), 2.04-1.58 (m, 4H), 1.26-0.96 (m, 4H).

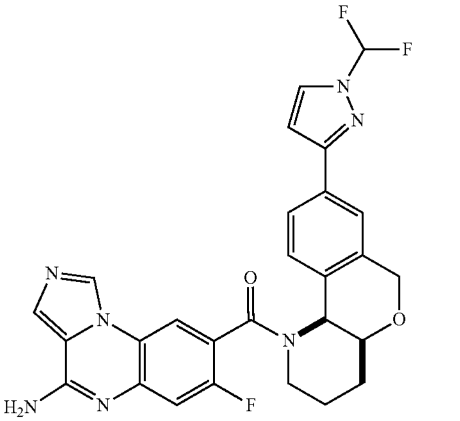

(±)

Example Ff-298: Rac-(4-amino-7-fluoroimidazo[1,5-a]quinoxalin-8-yl)((4aS,10bS)-8-(1-(difluoromethyl)-1H-pyrazol-3-yl)-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-8-(1-(difluoromethyl)-1H-pyrazol-3-yl)-2,3,4,4a,6,10b-hexahydro-1H-isochromeno[4,3-b]pyridine hydrochloride Ebd-5. ES/: m/z=534.0 $[M+H]^+$. $^1H$ NMR (400 MHz, MeOD) δ 9.29 (s, 1H), 8.55 (s, 1H), 8.41-8.29 (m, 1H), 8.13-8.06 (m, 1H), 7.87 (s, 1H), 7.78-7.27 (m, 4H), 7.04-6.79 (m, 1H), 6.13 (s, 1H), 5.06-4.94 (m, 1H), 4.78-4.46 (m, 1H), 4.26 (d, J=7.7 Hz, 1H), 3.45 (d, J=13.7 Hz, 1H), 2.98 (s, 1H), 2.06-1.59 (m, 4H).

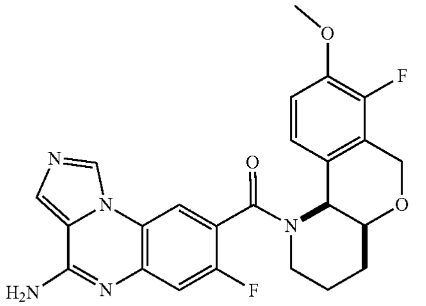

(±)

Example Ff-299: Rac-(4-amino-7-fluoroimidazo[1,5-a]quinoxalin-8-yl)((4aS,10bS)-7-fluoro-8-methoxy-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-7-fluoro-8-methoxy-2,3,4,4a,6,10b-hexahydro-1H-isochromeno[4,3-b]pyridine El-3. ES/MS: m/z=466.0 $[M+H]^+$. $^1H$ NMR (400 MHz, MeOD) δ 9.29 (s, 1H), 8.52 (s, 1H), 8.37 (s, 1H), 7.50 (d, J=9.7 Hz, 1H), 7.14 (d, J=7.1 Hz, 2H), 6.03 (s, 1H), 4.99-4.78 (m, 1H), 4.77-4.44 (m, 1H), 4.19 (q, J=7.0 Hz, 1H), 4.00-3.82 (m, 3H), 3.40 (d, J=13.9 Hz, 1H), 2.94 (s, 1H), 1.98-1.83 (m, 2H), 1.78-1.57 (m, 2H).

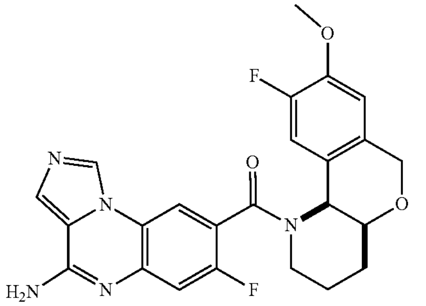

(±)

Example Ff-300: Rac-(4-amino-7-fluoroimidazo[1,5-a]quinoxalin-8-yl)((4aS,10bS)-9-fluoro-8-methoxy-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-9-fluoro-8-methoxy-2,3,4,4a,6,10b-hexahydro-1H-isochromeno[4,3-b]pyridine El-4. ES/MS: m/z=466.0 $[M+H]^+$. $^1H$ NMR (400 MHz, MeOD) δ 9.29 (s, 1H), 8.53 (s, 1H), 8.38 (s, 1H), 7.51 (d, J=9.8 Hz, 1H), 7.08 (s, 1H), 6.89 (d, J=8.3 Hz, 0.8H, major rotamer), 6.82 (d, J=8.2 Hz, 0.2H, minor rotamer), 5.98 (s, 1H), 4.83-4.44 (m, 2H), 4.19

(q, J=7.0 Hz, 1H), 3.99-3.71 (m, 3H), 3.41 (d, J=14.0 Hz, 1H), 2.96 (dt, J=14.4, 8.1 Hz, 0.8H, major rotamer), 2.62 (t, J=12.6 Hz, 0.2H, minor rotamer), 1.99-1.81 (m, 2H), 1.71-1.64 (m, 2H).

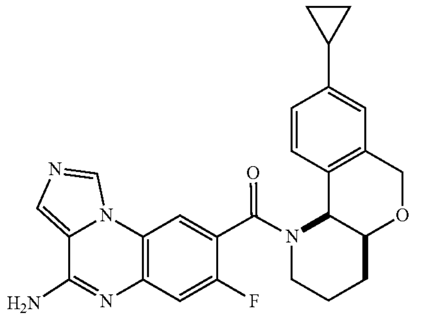

(±)

Example Ff-301: Rac-(4-amino-7-fluoroimidazo[1,5-a]quinoxalin-8-yl)((4aS,10bS)-8-cyclopropyl-2,3,4,4a,6,10b-hexahydro-1H-isochromeno[4,3-b]pyridin-1-yl)methanone. Prepared following general procedure VI-F starting with 4-((tert-butoxycarbonyl)amino)-7-chloroimidazo[1,5-a]quinoxaline-8-carboxylic acid Af-1 and rac-(4aS,10bS)-8-cyclopropyl-2,3,4,4a,6,10b-hexahydro-1H-isochromeno[4,3-b]pyridine El-5. ES/MS: m/z=458.0 $[M+H]^+$. $^1H$ NMR (400 MHz, MeOD) δ 9.29 (s, 1H), 8.51 (s, 1H), 8.35 (d, J=8.0 Hz, 1H), 7.49 (d, J=9.7 Hz, 1H), 7.25 (s, 1H), 7.06 (s, 1H), 6.87 (s, 0.7H, major rotamer), 6.78 (s, 0.3H, minor rotamer), 6.05 (s, 1H), 4.82-4.40 (m, 2H), 4.29-4.09 (m, 1H), 3.39 (d, J=14.0 Hz, 1H), 2.94 (s, 0.7H, major rotamer), 2.63 (s, 0.3H, minor rotamer), 2.03-1.54 (m, 5H), 0.97 (dd, J=13.3, 8.2 Hz, 2H), 0.78-0.58 (m, 2H).

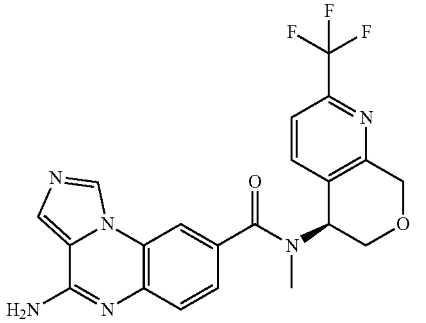

Example Ff-302: (S)-4-amino-N-methyl-N-(2-(trifluoromethyl)-5,8-dihydro-6H-pyrano[3,4-b]pyridin-5-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and (S)—N-methyl-2-(trifluoromethyl)-5,8-dihydro-6H-pyrano[3,4-b]pyridin-5-amine hydrochloride Ei-3. ES/MS: m/z=443.0 $[M+H]^+$. $^1H$ NMR (400 MHz, MeOD) δ 9.36 (s, 1H), 8.54-8.49 (m, 1H), 8.42 (d, J=0.6 Hz, 1H), 8.16-7.98 (m, 1H), 7.84-7.70 (m, 3H), 5.97 (s, 1H), 4.99-4.73 (m, 2H), 4.46-4.06 (m, 2H), 2.93 (s, 3H).

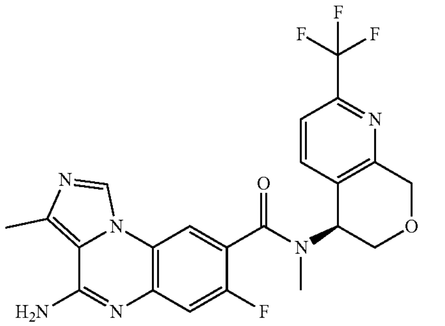 [SMILES: Cc1ncn2c1c(N)nc1cc(F)c(C(=O)N(C)[C@@H]3COCc4nc(C(F)(F)F)ccc43)cc12]

Example Ff-303: (S)-4-amino-7-fluoro-N,3-dimethyl-N-(2-(trifluoromethyl)-5,8-dihydro-6H-pyrano[3,4-b]pyridin-5-yl)imidazo[1,5-a]quinoxaline-8-carboxamide. Prepared following general procedure VI-F starting with 4-((tert-butoxycarbonyl)amino)-7-fluoro-3-methylimidazo[1,5-a]quinoxaline-8-carboxylic acid Af-4 and (S)—N-methyl-2-(trifluoromethyl)-5,8-dihydro-6H-pyrano[3,4-b]pyridin-5-amine hydrochloride Ei-3. ES/MS: m/z=475.0 $[M+H]^+$. $^1H$ NMR (400 MHz, MeOD) δ 9.19-9.13 (m, 1H), 8.43 (d, J=5.8 Hz, 1H), 8.11-7.98 (m, 1H), 7.82 (d, J=8.1 Hz, 1H), 7.53-7.44 (m, 1H), 6.00 (t, J=4.3 Hz, 1H), 5.04-4.91 (m, 1H), 4.86-4.65 (m, 1H), 4.39-4.01 (m, 2H), 2.96 (s, 1H, minor rotamer), 2.88 (d, J=1.1 Hz, 2H, major rotamer), 2.80 (d, J=1.4 Hz, 3H).

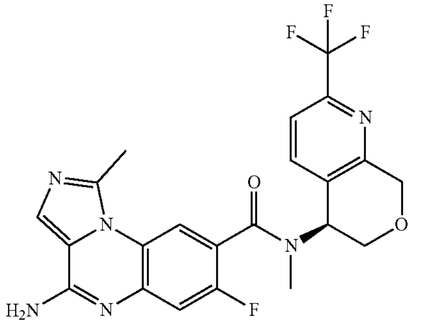 [SMILES: Cc1ncc2c(N)nc3cc(F)c(C(=O)N(C)[C@@H]4COCc5nc(C(F)(F)F)ccc54)cc3n12]

Example Ff-304: (S)-4-amino-7-fluoro-N,1-dimethyl-N-(2-(trifluoromethyl)-5,8-dihydro-6H-pyrano[3,4-b]pyridin-5-yl)imidazo[1,5-a]quinoxaline-8-carboxamide. Prepared following general procedure VI-F starting with 4-((tert-butoxycarbonyl)amino)-7-fluoro-1-methylimidazo[1,5-a]quinoxaline-8-carboxylic acid Af-5 and (S)—N-methyl-2-(trifluoromethyl)-5,8-dihydro-6H-pyrano[3,4-b]pyridin-5-amine hydrochloride Ei-3. ES/MS: m/z=475.0 $[M+H]^+$. $^1H$ NMR (400 MHz, MeOD) δ 8.42-8.30 (m, 2H), 8.12-8.02 (m, 1H), 7.85-7.77 (m, 1H), 7.55-7.46 (m, 1H), 6.00 (s, 1H), 5.11-4.92 (m, 1H), 4.84-4.65 (m, 1H), 4.46-4.03 (m, 2H), 3.17-3.11 (m, 3H), 2.97 (s, 1H, minor rotamer), 2.89 (s, 2H, major rotamer).

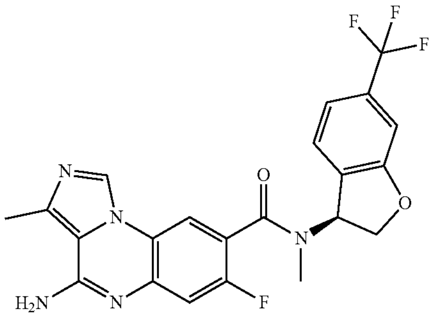

Example Ff-305: (S)-4-amino-7-fluoro-N,3-dimethyl-N-(6-(trifluoromethyl)-2,3-dihydrobenzofuran-3-yl)imidazo[1,5-a]quinoxaline-8-carboxamide Prepared following general procedure VI-F starting with 4-((tert-butoxycarbonyl)amino)-7-fluoro-3-methylimidazo[1,5-a]quinoxaline-8-carboxylic acid Af-4 and (S)—N-methyl-6-(trifluoromethyl)-2,3-dihydrobenzofuran-3-amine hydrochloride Eh-1. ES/MS: m/z=460.0 $[M+H]^+$. $^1H$ NMR (400 MHz, MeOD) δ 9.15 (s, 1H), 8.38 (d, J=5.8 Hz, 1H), 7.65-7.42 (m, 2H), 7.37-7.26 (m, 1H), 7.22-7.13 (m, 1H), 6.57 (dd, J=9.0, 3.7 Hz, 0.6H, major rotamer), 5.69 (t, J=6.6 Hz, 0.4H, minor rotamer), 4.77-4.69 (m, 2H), 2.89-2.70 (m, 6H).

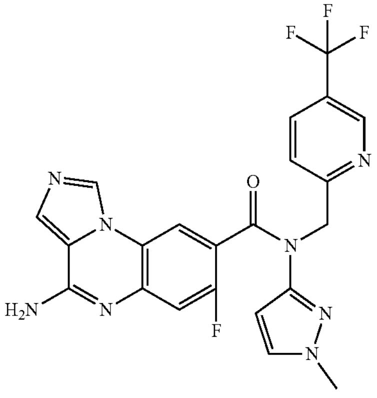 [SMILES: Cn1ccc(N(Cc2ccc(C(F)(F)F)cn2)C(=O)c2cc3c(cc2F)nc(N)c2cncn23)n1]

Example Ff-306: 4-amino-7-fluoro-N-(1-methyl-1H-pyrazol-3-yl)-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 1-methyl-N-((5-(trifluoromethyl)pyridin-2-yl)methyl)-1H-pyrazol-3-amine Ed-26. ES/MS: m/z=485.0 $[M+H]^+$. $^1H$ NMR (400 MHz, MeOD) δ 9.25 (s, 1H), 8.87 (s, 1H), 8.44 (d, J=5.8 Hz, 1H), 8.37 (d, J=0.7 Hz, 1H), 8.16 (d, J=8.3 Hz, 1H), 7.82 (d, J=8.3 Hz, 1H), 7.36-7.25 (m, 2H), 6.00 (s, 1H), 5.34 (s, 2H), 3.66 (s, 3H).

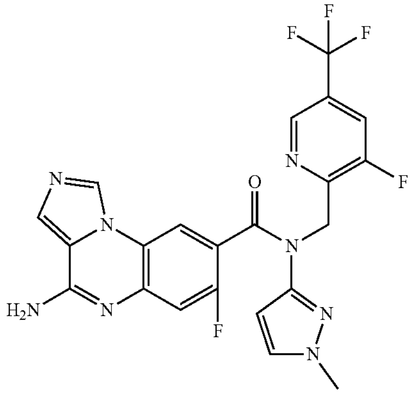 [SMILES: Cn1ccc(N(Cc2ncc(C(F)(F)F)cc2F)C(=O)c2cc3c(cc2F)nc(N)c2cncn23)n1]

Example Ff-307: 4-amino-7-fluoro-N-((3-fluoro-5-(trifluoromethyl)pyridin-2-yl)methyl)-N-(1-methyl-1H-pyrazol-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-((3-fluoro-5-(trifluoromethyl)pyridin-2-yl)methyl)-1-methyl-1H-pyrazol-3-amine Ed-24. ES/MS: m/z=503.0 $[M+H]^+$. $^1H$ NMR (400 MHz, MeOD) δ 9.24 (s, 1H), 8.76 (s, 1H), 8.38-8.31 (m, 2H), 8.02 (d, J=9.4 Hz, 1H), 7.31 (s, 1H), 7.25 (d, J=9.6 Hz, 1H), 5.98 (s, 1H), 5.41 (s, 2H), 3.66 (s, 3H).

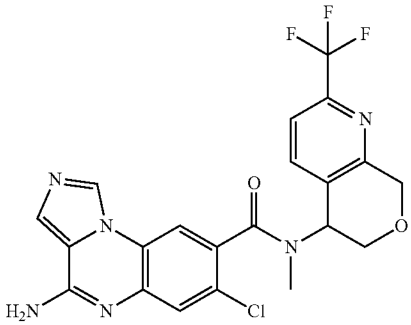 [SMILES: CN(C(=O)c1cc2c(cc1Cl)nc(N)c1cncn12)C1COCc2nc(C(F)(F)F)ccc21]

Example Ff-308: (S)-4-amino-7-chloro-N-methyl-N-(2-(trifluoromethyl)-5,8-dihydro-6H-pyrano[3,4-b]pyridin-5-yl)imidazo[1,5-a]quinoxaline-8-carboxamide. Prepared following general procedure VI-F starting with 4-((tert-butoxycarbonyl)amino)-7-chloroimidazo[1,5-a]quinoxaline-8-carboxylic acid Af-2 and (S)—N-methyl-2-(trifluoromethyl)-5,8-dihydro-6H-pyrano[3,4-b]pyridin-5-amine hydrochloride Ei-3. ES/MS: m/z=477.0 $[M+H]^+$. $^1H$ NMR (400 MHz, MeOD) δ 9.30-9.24 (m, 1H), 8.52-8.46 (m, 1H), 8.39-8.33 (m, 1H), 8.22-8.06 (m, 1H), 7.87-7.77 (m, 1H), 7.77-7.70 (m, 1H), 6.05 (s, 1H), 5.01-4.90 (m, 1H), 4.85-4.61 (m, 1H), 4.45-4.05 (m, 2H), 2.98 (d, J=15.4 Hz, 1H, minor rotamer), 2.82 (s, 2H, major rotamer).

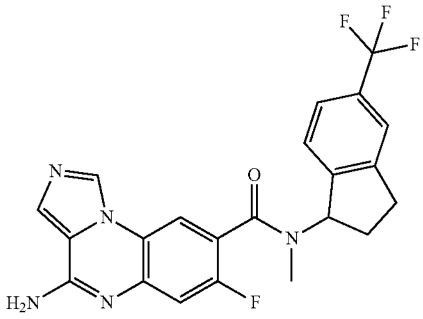 [SMILES: CN(C(=O)c1cc2c(cc1F)nc(N)c1cncn12)C1CCc2cc(C(F)(F)F)ccc21]

Example Ff-309: 4-amino-7-fluoro-N-methyl-N-(5-(trifluoromethyl)-2,3-dihydro-1H-inden-1-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-methyl-5-(trifluoromethyl)-2,3-dihydro-1H-inden-1-amine hydrochloride Ej-6. ES/MS: m/z=444.0 $[M+H]^+$. $^1H$ NMR (400 MHz, MeOD) δ 9.32-9.25 (m, 1H), 8.63-8.44 (m, 1H), 8.40-8.34 (m, 1H), 7.77-7.39 (m, 3H), 7.42-7.17 (m, 1H), 6.43 (t, J=8.1 Hz, 0.6H, major rotamer), 5.40 (t, J=8.2 Hz, 0.4H, minor rotamer), 3.27-3.00 (m, 2H), 2.89 (s, 2H), 2.76 (d, J=1.1 Hz, 1H), 2.67-2.19 (m, 2H).

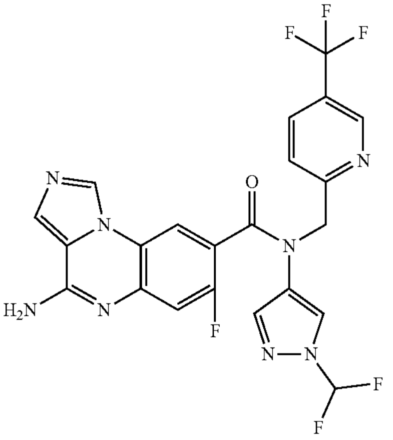 [SMILES: Nc1nc2cc(F)c(C(=O)N(Cc3ccc(C(F)(F)F)cn3)c3cnn(C(F)F)c3)cc2n2cncc12]

Example Ff-311: 4-amino-N-(1-(difluoromethyl)-1H-pyrazol-4-yl)-7-fluoro-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 1-(difluoromethyl)-N-((5-(trifluoromethyl)pyridin-2-yl)methyl)-1H-pyrazol-4-amine Ed-28. ES/MS: m/z=521.0 $[M+H]^+$. $^1H$ NMR (400 MHz, MeOD) δ 9.25 (s, 1H), 8.96-8.89 (m, 1H), 8.58-8.42 (m, 1H), 8.37 (s, 1H), 8.22-7.93 (m, 2H), 7.73 (d, J=8.3 Hz, 1H), 7.61 (s, 1H), 7.53-7.04 (m, 2H), 5.29 (s, 2H).

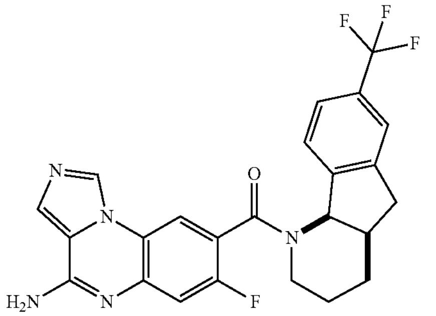

(±)

Example Ff-310: Rac-(4-amino-7-fluoroimidazo[1,5-a]quinoxalin-8-yl)((4aR,9bR)-7-(trifluoromethyl)-2,3,4,4a,5,9b-hexahydro-1H-indeno[1,2-b]pyridin-1-yl)methanone. Prepared following general procedure VI-F starting with 4-((tert-butoxycarbonyl)amino)-7-fluoroimidazo[1,5-a]quinoxaline-8-carboxylic acid Af-1 and cis-7-(trifluoromethyl)-2,3,4,4a,5,9b-hexahydro-1H-indeno[1,2-b]pyridine Eax-1. ES/MS: m/z=470.0 $[M+H]^+$. $^1H$ NMR (400 MHz, MeOD) δ 9.31 (s, 1H), 8.82-8.14 (m, 2H), 7.88-7.15 (m, 4H), 6.27 (s, 0.7H, major rotamer), 5.19 (s, 0.3H, minor rotamer), 3.59 (d, J=13.5 Hz, 1H), 3.25 (dd, J=15.8, 6.3 Hz, 1H), 2.96 (s, 1H), 2.87-2.58 (m, 2H), 1.88 (s, 1H), 1.79-1.48 (m, 2H), 1.28-1.07 (m,

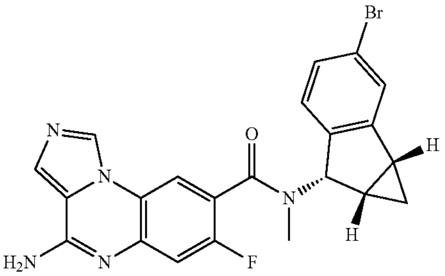 [SMILES: CN(C(=O)c1cc2c(cc1F)nc(N)c1cncn12)[C@@H]1c2ccc(Br)cc2[C@@H]2C[C@H]12]

Example Ff-312: 4-amino-N-((1aR,6S,6aS)-3-bromo-1,1a,6,6a-tetrahydrocyclopropa[a]inden-6-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (1aR,6S,6aS)-3-bromo-N-methyl-1,1a,6,6a-tetrahydrocyclopropa[a]inden-6-amine Eab-8. ES/MS: m/z=466.0 $[M+H]^+$. $^1H$ NMR (400 MHz, MeOD) δ 9.33-9.27 (m, J=14.8 Hz, 1H), 8.55-8.50 (m, 1H), 8.41-8.35 (m, 1H), 7.64-7.33 (m, 3H), 7.21-7.02 (m, 1H), 6.55 (d, J=6.5 Hz, 0.6H, major rotamer), 5.59 (d, J=6.3 Hz, 0.4H, minor rotamer), 3.03 (s, 1.2H, minor rotamer), 2.91 (d, J=1.1 Hz, 1.8H, major rotamer), 2.63-2.54 (m, 0.4H, minor rotamer), 2.41 (s, 0.6H, major rotamer), 2.08 (dt, J=12.3, 6.3 Hz, 0.6H, major rotamer), 1.87 (s, 0.4H, minor rotamer), 1.17 (td, J=7.9, z5.1 Hz, 1H), 0.89-0.51 (m, 1H).

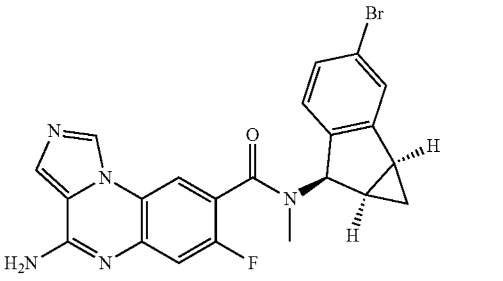 [SMILES: CN(C(=O)c1cc2c(cc1F)nc(N)c1cncn12)[C@H]1c2ccc(Br)cc2[C@H]2C[C@H]21]

Example Ff-313: 4-amino-N-((1aS,6R,6aR)-3-bromo-1,1a,6,6a-tetrahydrocyclopropa[a]inden-6-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (1aS,6R,6aR)-3-bromo-N-methyl-1,1a,6,6a-tetrahydrocyclopropa[a]inden-6-amine Eab-5. ES/MS: m/z=466.0 $[M+H]^+$. $^1H$ NMR (400 MHz, MeOD) δ 9.33-9.27 (m, J=14.8 Hz, 1H), 8.53-8.52 (m, 1H), 8.41-8.35 (m, 1H), 7.61-7.31 (m, 3H), 7.21-7.02 (m, 1H), 6.55 (d, J=6.5 Hz, 0.6H, major rotamer), 5.59 (d, J=6.3 Hz, 0.4H, minor rotamer), 3.02 (s, 1.2H, minor rotamer), 2.91 (d, J=1.1 Hz, 1.8H, major rotamer), 2.63-2.54 (m, 0.4H, minor rotamer), 2.41 (s, 0.6H, major rotamer), 2.08 (dt, J=12.3, 6.3 Hz, 0.6H, major rotamer), 1.87 (s, 0.4H, minor rotamer), 1.17 (td, J=7.9, z5.1 Hz, 1H), 0.89-0.59 (m, 1H).

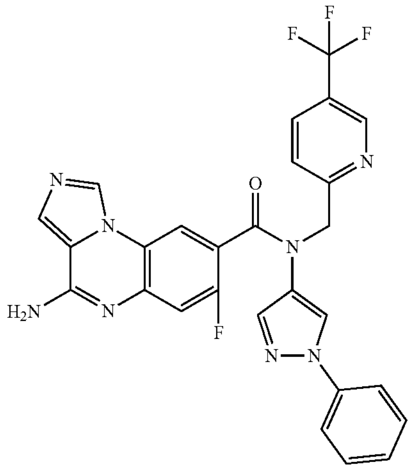

Example Ff-315: 4-amino-7-fluoro-N-(1-phenyl-1H-pyrazol-4-yl)-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 1-phenyl-N-((5-(trifluoromethyl)pyridin-2-yl)methyl)-1H-pyrazol-4-amine Ed-29. ES/MS: m/z=547.0 $[M+H]^+$. $^1H$ NMR (400 MHz, MeOD) δ 9.25 (d, J=0.7 Hz, 1H), 8.95 (d, J=2.2 Hz, 1H), 8.48 (d, J=5.7 Hz, 1H), 8.40-8.31 (m, 2H), 8.19 (dd, J=8.3, 2.4 Hz, 1H), 7.81-7.70 (m, 1H), 7.62-7.53 (m, 3H), 7.41 (dd, J=8.7, 7.2 Hz, 2H), 7.35-7.18 (m, 2H), 5.33 (s, 2H).

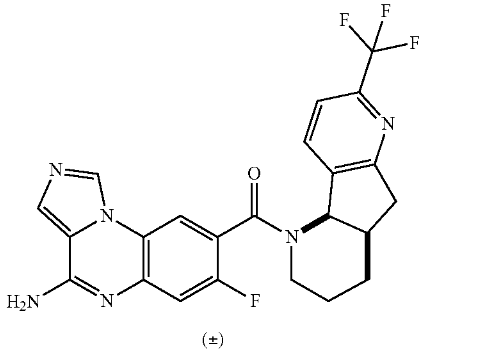

(±)

Example Ff-314: Rac-(4-amino-7-fluoroimidazo[1,5-a]quinoxalin-8-yl)((4bR,8aR)-2-(trifluoromethyl)-4b,6,7,8,8a,9-hexahydro-5H-cyclopenta[1,2-b:3,4-b']dipyridin-5-yl)methanone. Prepared following general procedure VI-F starting with 4-((tert-butoxycarbonyl)amino)-7-fluoroimidazo[1,5-a]quinoxaline-8-carboxylic acid Af-1 and rac-(4bR,8aR)-2-(trifluoromethyl)-4b,6,7,8,8a,9-hexahydro-5H-cyclopenta[1,2-b:3,4-b']dipyridine hydrochloride Eax-2. ES/MS: m/z=471.0 $[M+H]^+$. $^1H$ NMR (400 MHz, MeOD) δ 9.30 (s, 1H), 8.54 (s, 1H), 8.47-8.29 (m, 1H), 8.05-7.65 (m, 2H), 7.60-7.33 (m, 1H), 6.33 (s, 0.7H, major rotamer), 5.30 (s, 0.3H, minor rotamer), 3.63 (d, J=13.5 Hz, 1H), 3.44-3.33 (m, 1H), 3.18-2.59 (m, 3H), 1.97 (d, J=9.1 Hz, 1H), 1.80-1.47 (m, 2H), 1.26-1.12 (m, 1H).

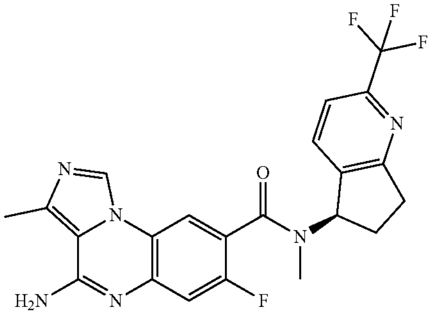

Example Ff-316: (R)-4-amino-7-fluoro-N,3-dimethyl-N-(2-(trifluoromethyl)-6,7-dihydro-5H-cyclopenta[b]pyridin-5-yl)imidazo[1,5-a]quinoxaline-8-carboxamide. Prepared following general procedure VI-F starting with 4-((tert-butoxycarbonyl)amino)-7-fluoro-3-methylimidazo[1,5-a]quinoxaline-8-carboxylic acid Af-4 and (R)—N-methyl-2-(trifluoromethyl)-6,7-dihydro-5H-cyclopenta[b]pyridin-5-amine dihydrochloride Eh-8. ES/MS: m/z=459.0 $[M+H]^+$. $^1H$ NMR (400 MHz, MeOD) δ 9.17 (d, J=6.3 Hz, 1H), 8.44 (t, J=6.8 Hz, 1H), 7.94 (d, J=7.8 Hz, 1H), 7.74 (d, J=7.9 Hz, 1H), 7.52-7.45 (m, 1H), 6.37 (t, J=8.2 Hz, 0.5H, rotamer A), 5.47 (t, J=8.4 Hz, 0.5H, rotamer B), 3.30-3.10 (m, 1H), 3.06-2.89 (m, 2H), 2.85-2.78 (m, 4H), 2.77-2.64 (m, 1H), 2.61-2.27 (m, 2H).

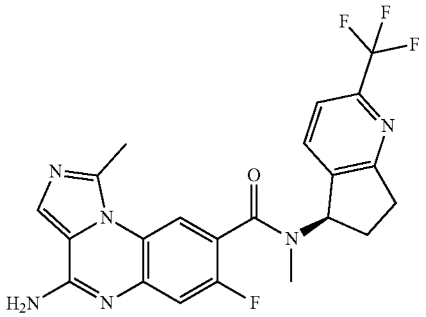 [SMILES: Cc1ncc2c(N)nc3cc(F)c(C(=O)N(C)[C@@H]4CCc5nc(C(F)(F)F)ccc54)cc3n12]

Example Ff-317: (R)-4-amino-7-fluoro-N,1-dimethyl-N-(2-(trifluoromethyl)-6,7-dihydro-5H-cyclopenta[b]pyridin-5-yl)imidazo[1,5-a]quinoxaline-8-carboxamide. Prepared following general procedure VI-F starting with 4-((tert-butoxycarbonyl)amino)-7-fluoro-1-methylimidazo[1,5-a]quinoxaline-8-carboxylic acid Af-5 and (R)—N-methyl-2-(trifluoromethyl)-6,7-dihydro-5H-cyclopenta[b]pyridin-5-amine dihydrochloride Eh-8. ES/MS: m/z=459.0 $[M+H]^+$. $^1$H NMR (400 MHz, MeOD) δ 8.39-8.30 (m, 2H), 8.07-7.89 (m, 1H), 7.74 (dd, J=7.9, 2.9 Hz, 1H), 7.51 (dd, J=9.8, 1.4 Hz, 1H), 6.38 (t, J=8.2 Hz, 0.5H, rotamer A), 5.49 (t, J=8.4 Hz, 0.5H, rotamer B), 3.30-3.09 (m, 5H), 3.05-2.88 (m, 2H), 2.86-2.64 (m, 2H), 2.61-2.22 (m, 1H).

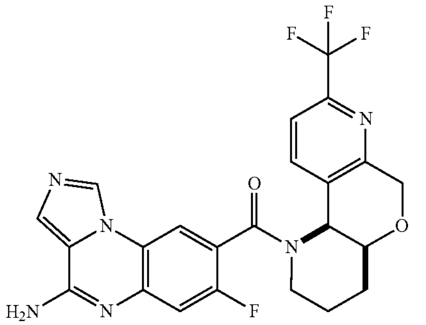

(±)

Example Ff-319: Rac-(4-amino-7-fluoroimidazo[1,5-a]quinoxalin-8-yl)((4aS,10bS)-8-(trifluoromethyl)-2,3,4,4a,6,10b-hexahydro-1H-pyrano[3,2-b:5,4-b']dipyridin-1-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,10bS)-8-(trifluoromethyl)-2,3,4,4a,6,10b-hexahydro-1H-pyrano[3,2-b:5,4-b']dipyridine hydrochloride Eax-3. ES/MS: m/z=487.0 $[M+H]^+$. $^1$H NMR (400 MHz, MeOD) δ 9.30 (s, 1H), 8.57 (s, 1H), 8.40 (s, 1H), 8.16-7.89 (m, 1H), 7.82 (d, J=8.1 Hz, 1H), 7.52 (d, J=9.6 Hz, 1H), 6.21 (s, 0.8H, major rotamer), 5.12 (s, 0.2H, minor rotamer), 5.04-4.89 (m, 1H), 4.79-4.51 (m, 1H), 4.33 (dt, J=10.8, 5.1 Hz, 1H), 3.54-3.39 (m, 1H), 2.90 (s, 1H), 2.12-1.56 (m, 4H).

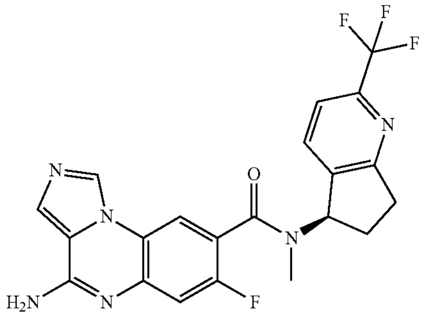

Example Ff-318: (R)-4-amino-7-fluoro-N-methyl-N-(2-(trifluoromethyl)-6,7-dihydro-5H-cyclopenta[b]pyridin-5-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (R)—N-methyl-2-(trifluoromethyl)-6,7-dihydro-5H-cyclopenta[b]pyridin-5-amine dihydrochloride Eh-8. ES/MS: m/z=445.0 $[M+H]^+$. $^1$H NMR (400 MHz, MeOD) δ 9.38-9.22 (m, 1H), 8.50 (d, J=5.9 Hz, 1H), 8.43-8.36 (m, 1H), 7.95 (d, J=7.9 Hz, 1H), 7.74 (d, J=7.8 Hz, 1H), 7.55-7.41 (m, 1H), 6.38 (t, J=8.3 Hz, 0.5H, rotamer A), 5.47 (t, J=8.3 Hz, 0.5H, rotamer B), 3.29-3.13 (m, 1H), 2.92 (s, 1.5H, rotamer A), 2.84 (d, J=1.1 Hz, 1.5H rotamer B), 2.78-2.67 (m, 1H), 2.62-2.27 (m, 2H).

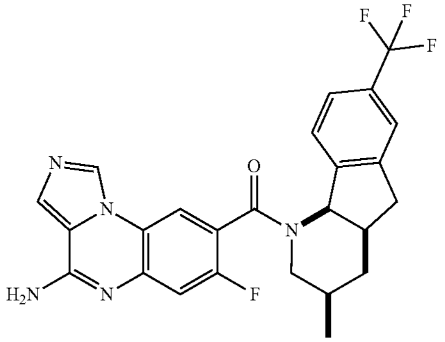

(±)

Example Ff-320: Rac-(4-amino-7-fluoroimidazo[1,5-a]quinoxalin-8-yl)((3R,4aR,9bR)-3-methyl-7-(trifluoromethyl)-2,3,4,4a,5,9b-hexahydro-1H-indeno[1,2-b]pyridin-1-yl)methanone. Prepared following general procedure VI-F starting with 4-((tert-butoxycarbonyl)amino)-7-fluoroimidazo[1,5-a]quinoxaline-8-carboxylic acid Af-1 and rac-cis-(3R,4aR,9bR)-3-methyl-7-(trifluoromethyl)-2,3,4,4a,5,9b-hexahydro-1H-indeno[1,2-b]pyridine hydrochloride Eax-4. ES/MS: m/z=484.0 $[M+H]^+$. $^1$H NMR (400 MHz, MeOD) δ 9.29 (s, 1H), 8.54 (d, J=6.1 Hz, 1H), 8.45-8.28 (m, 1H), 7.80-7.23 (m, 4H), 6.27 (s, 0.8H, major rotamer), 5.17 (s, 0.2H, minor rotamer), 4.61 (d, J=12.8 Hz, 0.2H, minor rotamer), 3.45 (d, J=13.1 Hz, 0.8H, major rotamer), 3.26 (dd, J=15.7, 6.3 Hz, 1H), 3.05-2.71 (m, 2H), 2.71-2.45 (m, 1H), 1.93-1.62 (m, 2H), 0.99-0.58 (m, 4H).

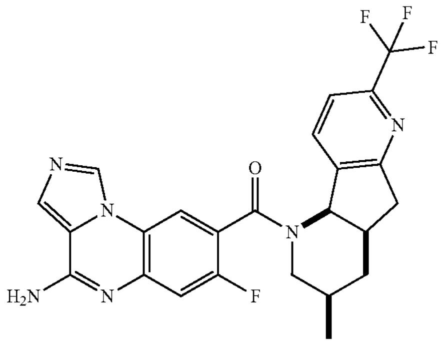

(±)

Example Ff-321: Rac-(4-amino-7-fluoroimidazo[1,5-a]quinoxalin-8-yl)((4bR,7R,8aR)-7-methyl-2-(trifluoromethyl)-4b,6,7,8,8a,9-hexahydro-5H-cyclopenta[1,2-b:3,4-b']dipyridin-5-yl)methanone. Prepared following general procedure VI-F starting with 4-((tert-butoxycarbonyl)amino)-7-fluoroimidazo[1,5-a]quinoxaline-8-carboxylic acid Af-1 and rac-cis-(4bR,7R,8aR)-7-methyl-2-(trifluoromethyl)-4b,6,7,8,8a,9-hexahydro-5H-cyclopenta[1,2-b:3,4-b']dipyridine hydrochloride Eax-5. ES/MS: m/z=485.0 $[M+H]^+$. $^1H$ NMR (400 MHz, MeOD) δ 9.30 (s, 1H), 8.52 (d, J=5.9 Hz, 1H), 8.42-8.32 (m, 1H), 8.20-7.62 (m, 2H), 7.58-7.27 (m, 1H), 6.33 (s, 0.8H, major rotamer), 5.29 (s, 0.2H, minor rotamer), 4.64 (d, J=13.1 Hz, 0.2H, minor rotamer), 3.56-3.36 (m, 0.8H, major rotamer), 3.20-2.44 (m, 3.8H), 2.29 (t, J=12.4 Hz, 0.2H, minor rotamer), 1.94 (d, J=8.5 Hz, 1H), 1.77 (s, 1H), 0.93 (d, J=6.6 Hz, 1H), 0.90-0.59 (m, 3H).

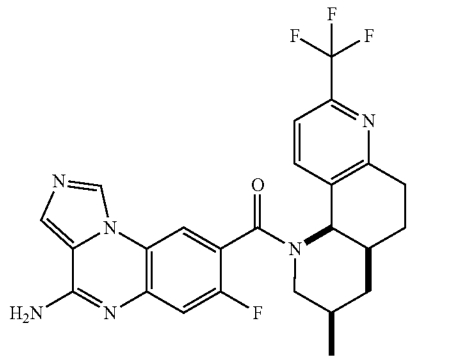

(±)

Example Ff-322: Rac-(4-amino-7-fluoroimidazo[1,5-a]quinoxalin-8-yl)((3R,4aS,10bR)-3-methyl-8-(trifluoromethyl)-3,4,4a,5,6,10b-hexahydrobenzo[h]quinolin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and rac-(3R,4aS,10bR)-3-methyl-8-(trifluoromethyl)-1,2,3,4,4a,5,6,10b-octahydrobenzo[h]quinoline hydrochloride Eax-6. ES/MS: m/z=498.0 $[M+H]^+$. $^1H$ NMR (400 MHz, MeOD) δ 9.51-9.15 (m, 1H), 8.71-8.47 (m, 1H), 8.45-8.28 (m, 1H), 7.66-7.36 (m, 4H), 6.07 (s, 1H), 4.57 (d, J=12.8 Hz, 0.2H, minor rotamer), 3.39 (d, J=13.7 Hz, 0.8H, major rotamer), 3.12-2.69 (m, 2H), 2.61-2.31 (m, 2H), 2.26-2.12 (m, 1H), 2.09-1.65 (m, 3H), 1.28-1.14 (m, 1H), 0.95 (d, J=6.6 Hz, 1H), 0.73 (s, 2H).

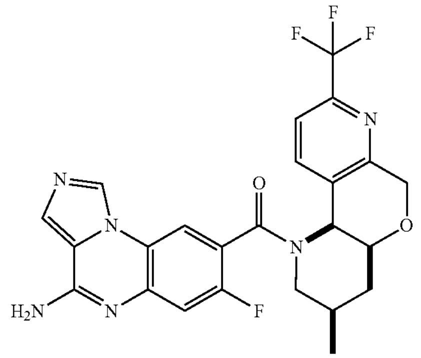

Example Ff-323: Rac-(4-amino-7-fluoroimidazo[1,5-a]quinoxalin-8-yl)((3R,4aS,10bS)-3-methyl-8-(trifluoromethyl)-2,3,4,4a,6,10b-hexahydro-1H-pyrano[3,2-b:5,4-b']dipyridin-1-yl)methanone. Prepared following general procedure VI-F starting with 4-((tert-butoxycarbonyl)amino)-7-fluoroimidazo[1,5-a]quinoxaline-8-carboxylic acid Af-1 and rac-(3R,4aS,10bS)-3-methyl-8-(trifluoromethyl)-2,3,4,4a,6,10b-hexahydro-1H-pyrano[3,2-b:5,4-b']dipyridine hydrochloride Eax-7. ES/MS: m/z=501.0 $[M+H]^+$. $^1H$ NMR (400 MHz, MeOD) δ 9.26 (s, 1H), 8.47 (s, 1H), 8.29 (s, 1H), 8.10 (s, 1H), 7.81 (s, 1H), 7.44 (d, J=10.4 Hz, 1H), 6.13 (s, 1H), 5.05-4.86 (m, 2H), 4.49 (s, 1H), 3.29-3.13 (m, 2H), 2.11 (s, 2H), 1.67 (s, 1H), 1.46-0.86 (m, 3H).

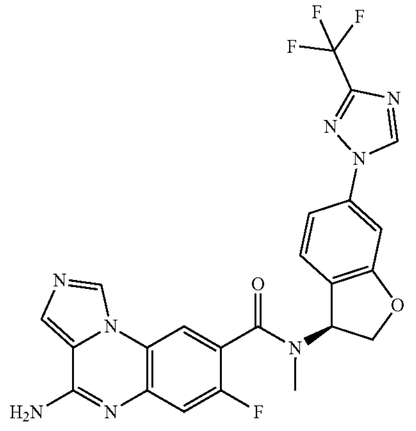 [SMILES: CN(C(=O)c1cc2c(cc1F)nc(N)c1cncn12)[C@@H]1COc2cc(-n3cnc(C(F)(F)F)n3)ccc21]

Example Ff-324: (S)-4-amino-7-fluoro-N-methyl-N-(6-(3-(trifluoromethyl)-1H-1,2,4-triazol-1-yl)-2,3-dihydrobenzofuran-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)—N-methyl-6-(3-(trifluoromethyl)-1H-1,2,4-triazol-1-yl)-2,3-dihydrobenzofuran-3-amine Eaf-2. ES/MS: m/z=513.0 $[M+H]^+$. $^1H$ NMR (400 MHz, MeOD) δ 9.29-9.21 (m, 2H), 8.47 (d, J=5.9 Hz, 1H), 8.38 (s, 1H), 7.68-7.36 (m, 4H), 6.58 (dd, J=8.8, 3.6 Hz, 0.6H, major rotamer), 5.69 (t, J=6.4 Hz, 0.4H, minor rotamer), 4.93 (dd, J=10.8, 8.9 Hz, 1H), 4.77 (dd, J=10.7, 3.6 Hz, 1H), 2.90 (s, 1.2H, minor rotamer), 2.80-2.75 (m, 1.8H, major rotamer).

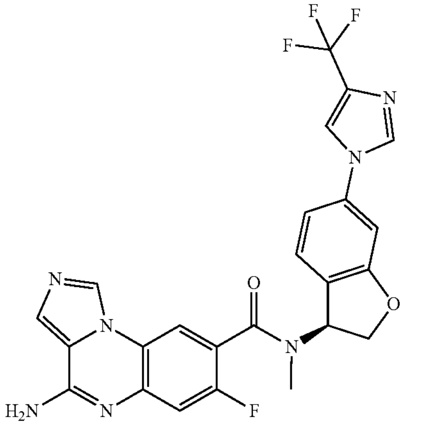 [SMILES: CN(C(=O)c1cc2c(cc1F)nc(N)c1cncn12)[C@@H]1COc2cc(-n3cnc(C(F)(F)F)c3)ccc21]

Example Ff-325: (S)-4-amino-7-fluoro-N-methyl-N-(6-(4-(trifluoromethyl)-1H-imidazol-1-yl)-2,3-dihydrobenzofuran-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)—N-methyl-6-(4-(trifluoromethyl)-1H-imidazol-1-yl)-2,3-dihydrobenzofuran-3-amine Eag-1. ES/MS: m/z=512.0 $[M+H]^+$. $^1H$ NMR (400 MHz, MeOD) δ 9.28 (s, 1H), 8.47 (d, J=5.9 Hz, 1H), 8.41 (d, J=3.4 Hz, 1H), 8.30 (d, J=10.0 Hz, 1H), 8.15 (dt, J=9.9, 1.3 Hz, 1H), 7.64-7.43 (m, 2H), 7.36-7.15 (m, 2H), 6.57 (dd, J=8.8, 3.5 Hz, 0.6H, major rotamer), 5.67 (t, J=6.3 Hz, 0.4H, minor rotamer), 4.96-4.89 (m, 0.8H, minor rotamer), 4.76 (dd, J=10.7, 3.6 Hz, 1.2H, major rotamer), 2.89 (s, 1.2H, minor rotamer), 2.79-2.74 (m, 1.8H, major rotamer).

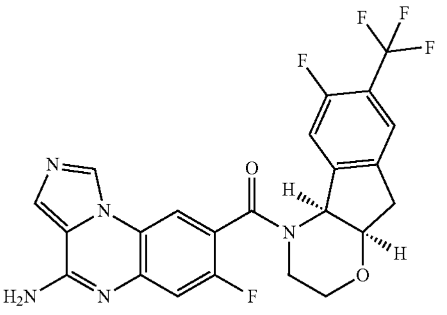 [SMILES: Nc1nc2cc(F)c(C(=O)N3CCO[C@@H]4Cc5cc(C(F)(F)F)c(F)cc5[C@@H]43)cc2n2cncc12]

Example Ff-326: (4-amino-7-fluoroimidazo[1,5-a]quinoxalin-8-yl)((4aS,9aR)-6-fluoro-7-(trifluoromethyl)-2,3,9,9a-tetrahydroindeno[2,1-b][1,4]oxazin-4(4aH)-yl)methanone. Prepared following general procedure VI-F starting with 4-((tert-butoxycarbonyl)amino)-7-fluoroimidazo[1,5-a]quinoxaline-8-carboxylic acid Af-1 and (4aS,9aR)-6-fluoro-7-(trifluoromethyl)-2,3,4,4a,9,9a-hexahydroindeno[2,1-b][1,4]oxazine hydrochloride Eaz-3. ES/MS: m/z=490.0 $[M+H]^+$. $^1H$ NMR (400 MHz, MeOD) δ 9.52-9.12 (m, 1H), 8.69-8.49 (m, 1H), 8.42-8.34 (m, 1H), 7.67 (d, J=6.3 Hz, 1H), 7.60-7.45 (m, 1H), 7.42-7.04 (m, 1H), 6.04 (s, 0.8H, major rotamer), 5.12 (s, 0.2H, minor rotamer), 4.58-4.45 (m, 1H), 3.98-3.59 (m, 2H), 3.56-3.42 (m, 1H), 3.27-2.82 (m, 3H).

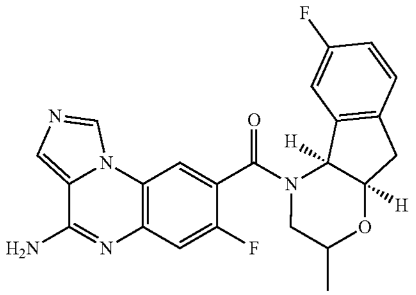 [SMILES: CC1CN(C(=O)c2cc3c(cc2F)nc(N)c2cncn23)[C@H]2c3cc(F)ccc3C[C@H]2O1]

Example Ff-327: (4-amino-7-fluoroimidazo[1,5-a]quinoxalin-8-yl)((4aS,9aR)-6-fluoro-2-methyl-2,3,9,9a-tetrahydroindeno[2,1-b][1,4]oxazin-4(4aH)-yl)methanone. Prepared following general procedure VI-F starting with 4-((tert-butoxycarbonyl)amino)-7-fluoroimidazo[1,5-a]quinoxaline-8-carboxylic acid Af-1 and (4aS,9aR)-6-fluoro-2-methyl-2,3,4,4a,9,9a-hexahydroindeno[2,1-b][1,4]oxazine hydrochloride Eaz-5. ES/MS: m/z=436.0 $[M+H]^+$. $^1H$ NMR (400 MHz, MeOD) δ 9.52-9.17 (m, 1H), 8.66-8.50 (m, 1H), 8.37 (d, J=12.3 Hz, 1H), 7.55-7.43 (m, 1H), 7.39-6.86 (m, 3H), 6.11-5.87 (m, 1H), 5.07-4.67 (m, 1H), 4.62-4.26 (m, 1H), 4.12-3.61 (m, 1H), 3.30-2.77 (m, 3H), 1.59-0.82 (m, 3H).

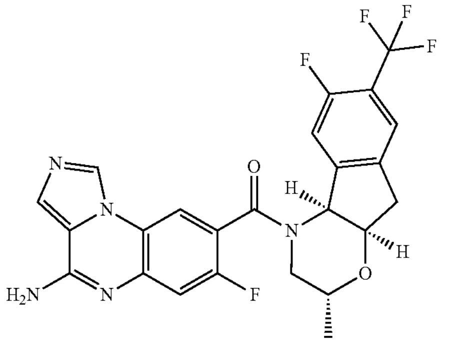 [SMILES: C[C@@H]1CN(C(=O)c2cc3c(cc2F)nc(N)c2cncn23)[C@H]2c3cc(F)c(C(F)(F)F)cc3C[C@H]2O1]

Example Ff-328: (4-amino-7-fluoroimidazo[1,5-a]quinoxalin-8-yl)((2R,4aS,9aR)-6-fluoro-2-methyl-7-(trifluoromethyl)-2,3,9,9a-tetrahydroindeno[2,1-b][1,4]oxazin-4(4aH)-yl)methanone. Prepared following general procedure VI-F starting with 4-((tert-butoxycarbonyl)amino)-7-fluoroimidazo[1,5-a]quinoxaline-8-carboxylic acid Af-1 and (2R,4aS,9aR)-6-fluoro-2-methyl-7-(trifluoromethyl)-2,3,4,4a,9,9a-hexahydroindeno[2,1-b][1,4]oxazine hydrochloride Eaz-4. Isolated as peak 1 after HPLC purification. ES/MS: m/z=504.0 $[M+H]^+$. $^1H$ NMR (400 MHz, MeOD) δ 9.33 (s, 1H), 8.55 (d, J=6.2 Hz, 1H), 8.33 (d, J=11.2 Hz, 1H), 7.73-7.09 (m, 3H), 6.11 (s, 1H), 4.87-4.70 (m, 1H), 4.11-3.71 (m, 2H), 3.44-3.35 (m, 1H), 3.20-2.76 (m, 2H), 1.45 (d, J=6.7 Hz, 1H, minor rotamer), 1.34 (d, J=6.7 Hz, 2H, major rotamer).

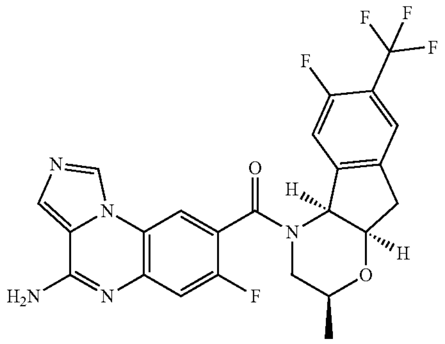 [SMILES: C[C@H]1CN(C(=O)c2cc3c(cc2F)nc(N)c2cncn23)[C@H]2c3cc(F)c(C(F)(F)F)cc3C[C@H]2O1]

Example Ff-329: (4-amino-7-fluoroimidazo[1,5-a]quinoxalin-8-yl)((2S,4aS,9aR)-6-fluoro-2-methyl-7-(trifluoromethyl)-2,3,9,9a-tetrahydroindeno[2,1-b][1,4]oxazin-4(4aH)-yl)methanone. Prepared following general procedure VI-F starting with 4-((tert-butoxycarbonyl)amino)-7-fluoroimidazo[11,5-a]quinoxaline-8-carboxylic acid Af-1 and (2R, 4aS,9aR)-6-fluoro-2-methyl-7-(trifluoromethyl)-2,3,4,4a,9,9a-hexahydroindeno[2,1-b][1,4]oxazine hydrochloride Eaz-4. Isolated as peak 2 after HPLC purification. ES/MS: m/z=504.0 $[M+H]^+$. $^1H$ NMR (400 MHz, MeOD) δ 9.37-9.17 (m, 1H), 8.57 (s, 1H), 8.39-8.27 (m, 1H), 7.71-7.54 (m, 1H), 7.53-7.41 (m, 1H), 7.33-7.19 (m, 1H), 6.03 (s, 1H), 4.68-4.47 (m, 1H), 3.72 (s, 1H), 3.43 (d, J=13.2 Hz, 1H), 3.27 (s, 1H), 3.10-2.77 (m, 2H), 1.16 (d, J=6.2 Hz, 1H, minor rotamer), 0.99 (d, J=6.2 Hz, 2H, major rotamer).

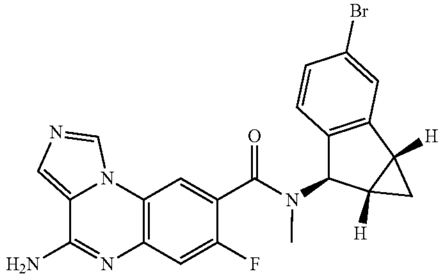 [SMILES: CN(C(=O)c1cc2c(cc1F)nc(N)c1cncn12)[C@H]1c2ccc(Br)cc2[C@@H]2C[C@@H]21]

Example Ff-330: 4-amino-N-((1aR,6R,6aS)-3-bromo-1,1a,6,6a-tetrahydrocyclopropa[a]inden-6-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (1aR,6R,6aS)-3-bromo-N-methyl-1,1a,6,6a-tetrahydrocyclopropa[a]inden-6-amine Eab-6. ES/MS: m/z=466.0 $[M+H]^+$. $^1H$ NMR (400 MHz, MeOD) δ 9.33-9.27 (m, 1H), 8.65-8.44 (m, 1H), 8.38 (dd, J=3.8, 0.7 Hz, 1H), 7.65-7.35 (m, 3H), 7.28 (d, J=8.1 Hz, 0.5H, rotamer 1), 7.22 (d, J=8.1 Hz, 0.5H, rotamer 2), 6.12 (s, 0.5H, rotamer 1), 4.96 (s, 0.5H, rotamer 2), 2.77 (s, 1.5H, rotamer 1), 2.68 (s, 1H), 2.62 (d, J=1.1 Hz, 1.5H, rotamer 2), 2.23-2.12 (m, 0.5H, rotamer 1), 2.09 (dt, J=9.1, 4.7 Hz, 0.5H, rotamer 2), 1.39 (td, J=8.2, 4.8 Hz, 0.5H, rotamer 1), 1.25 (s, 0.5H, rotamer 2), 0.30 (q, J=4.2 Hz, 0.5H, rotamer 1), 0.04 (s, 0.5H, rotamer 2).

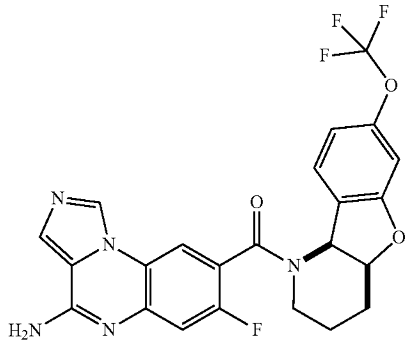

(±)

Example Ff-331: Rac-(4-amino-7-fluoroimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,9bS)-7-(trifluoromethoxy)-1,2,3,4,4a,9b-hexahydrobenzofuro[3,2-b]pyridine Ev-7. ES/MS: m/z=488.0 $[M+H]^+$. $^1H$ NMR (400 MHz, MeOD) δ 9.39-9.19 (m, 1H), 8.65-8.27 (m, 2H), 7.61-7.22 (m, 2H), 7.03-6.66 (m, 2H), 6.38 (d, J=8.8 Hz, 0.8H, major rotamer), 5.58 (d, J=9.1 Hz, 0.2H, minor rotamer), 5.19 (dt, J=8.6, 4.2 Hz, 1H), 3.45 (dd, J=12.3, 7.9 Hz, 1H), 3.04 (dt, J=15.1, 8.3 Hz, 0.8H, major rotamer), 2.85 (dt, J=13.7, 6.9 Hz, 0.2H, minor rotamer), 2.23-1.59 (m, 4H).

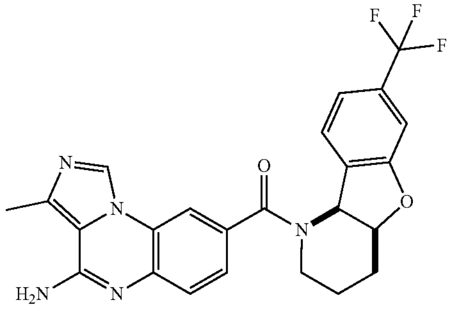

(±)

Example Ff-332: Rac-(4-amino-3-methylimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone. Prepared following general procedure VII-F starting with 4-amino-3-methylimidazo[1,5-a]quinoxaline-8-carboxylic acid Aa-1 and cis-7-(trifluoromethyl)-1,2,3,4,4a,9b-hexahydrobenzofuro[3,2-b]pyridine Ev-1. ES/MS: m/z=468.0 $[M+H]^+$. $^1H$ NMR (400 MHz, MeOD) δ 9.24 (s, 1H), 8.38 (s, 1H), 7.79-7.52 (m, 3H), 7.33-7.26 (m, 1H), 7.13 (s, 1H), 6.34 (s, 1H), 5.17 (s, 1H), 3.76-3.43 (m, 1H), 2.97 (s, 1H), 2.81 (s, 3H), 2.10 (s, 2H), 1.87 (qt, J=8.3, 4.1 Hz, 1H), 1.81-1.69 (m, 1H).

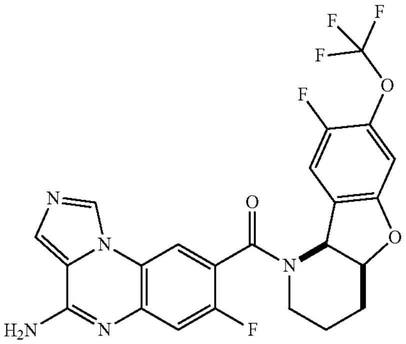

(±)

Example Ff-333: Rac-(4-amino-7-fluoroimidazo[1,5-a]quinoxalin-8-yl)((4aS,9bS)-8-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,9bS)-8-fluoro-7-(trifluoromethoxy)-1,2,3,4,4a,9b-hexahydrobenzofuro[3,2-b]pyridine hydrochloride Eba-3. ES/MS: m/z=506.0 $[M+H]^+$. $^1H$ NMR (400 MHz, MeOD) δ 9.06 (s, 1H), 8.45-8.15 (m, 1H), 7.97 (s, 1H), 7.60-7.18 (m, 2H), 7.03-6.75 (m, 1H), 6.37 (d, J=8.7 Hz, 0.7H, major rotamer), 5.64 (d, J=9.0 Hz, 0.3H, minor rotamer), 5.33-5.04 (m, 1H), 4.45 (s, 0.3H, minor rotamer), 3.61-3.42 (m, 0.7H, major rotamer), 3.14-2.71 (m, 1H), 2.23-1.57 (m, 4H).

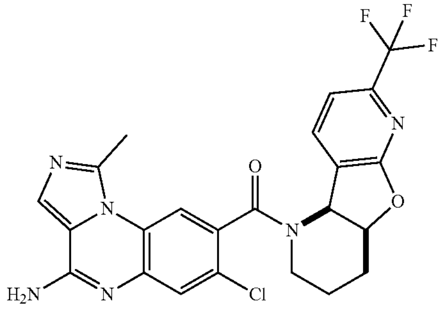

(±)

Example Ff-334: Rac-4-amino-7-chloro-1-methylimidazo[1,5-a]quinoxalin-8-yl)((4aS,9bS)-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-chloro-1-methylimidazo[1,5-a]quinoxaline-8-carboxylic acid Ai-1 and rac-(4aS,9bS)-7-(trifluoromethyl)-1,2,3,4,4a,9b-hexahydrofuro[2,3-b:4,5-b']dipyridine Eat-1. ES/MS: m/z=503.0 $[M+H]^+$. $^1H$ NMR (400 MHz, MeOD) δ 8.42-8.09 (m, 2H), 8.02 (t, J=9.4 Hz, 1H), 7.73 (d, J=14.8 Hz, 1H), 7.56-7.34 (m, 1H), 6.61-6.42 (m, 0.8H, major rotamer), 5.73-5.58 (m, 0.2H, minor rotamer), 5.42-5.24 (m, 1H), 3.47-3.39 (m, 1H), 3.20-2.89 (m, 4H), 2.23-2.00 (m, 2H), 1.98-1.59 (m, 2H).

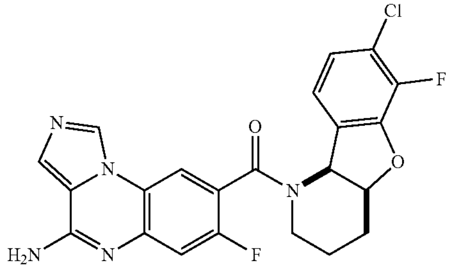

(±)

Example Ff-335: Rac-((4-amino-7-fluoroimidazo[1,5-a]quinoxalin-8-yl)((4aS,9bS)-7-chloro-6-fluoro-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,9bS)-7-chloro-6-fluoro-1,2,3,4,4a,9b-hexahydrobenzofuro[3,2-b]pyridine hydrochloride Ebe-4. ES/MS: m/z=456.0 $[M+H]^+$. $^1H$ NMR (400 MHz, MeOD) δ 9.30 (d, J=4.7 Hz, 1H), 8.54 (s, 0.3H, minor rotamer), 8.44 (d, J=5.8 Hz, 0.7H, major rotamer), 8.39 (s, 1H), 7.50 (dd, J=14.8, 9.6 Hz, 1H), 7.21 (s, 1H), 7.11-6.98 (m, 1H), 6.41 (d, J=8.8 Hz, 0.7H, major rotamer), 5.63 (d, J=9.1 Hz, 0.3H, minor rotamer), 5.35-5.07 (m, 1H), 4.45 (s, 0.3H, minor rotamer), 3.46 (d, J=7.3 Hz, 0.7H, major rotamer), 3.09-3.01 (m, 0.7H, major rotamer), 2.85 (dd, J=14.0, 7.0 Hz, 0.3H, minor rotamer), 2.17-2.01 (m, 2H), 1.98-1.62 (m, 2H).

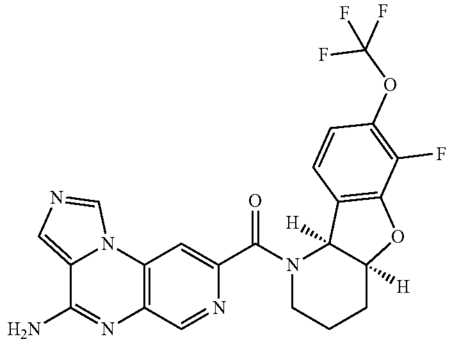

Example Ff-336: (4-aminoimidazo[1,5-a]pyrido[3,4-e]pyrazin-8-yl)((4aS,9bS)-6-fluoro-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (4aS,9bS)-6-fluoro-7-(trifluoromethoxy)-1,2,3,4,4a,9b-hexahydrobenzofuro[3,2-b]pyridine hydrochloride Ew-11. ES/MS: m/z=489.0 $[M+H]^+$. $^1H$ NMR (400 MHz, MeOD) δ 9.36 (s, 1H), 8.90-8.82 (m, 1H), 8.69-8.48 (m, 1H), 8.33 (s, 1H), 7.59 (d, J=8.3 Hz, 0.4H, minor rotamer), 7.33 (d, J=8.4 Hz, 0.6H, major rotamer), 7.01 (ddd, J=8.1, 6.4, 1.3 Hz, 1H), 6.35 (d, J=8.7 Hz, 0.6H, major rotamer), 6.04 (d, J=9.0 Hz, 0.4H, minor rotamer), 5.31 (s, 0.6H, major rotamer), 5.14 (s, 0.4H, minor rotamer), 4.44 (d, J=12.6 Hz, 0.4H, minor rotamer), 3.79 (s, 0.6H, major rotamer), 2.99 (dd, J=14.9, 7.3 Hz, 0.6H, major rotamer), 2.86-2.78 (m, 0.4H, minor rotamer), 2.37-1.63 (m, 4H).

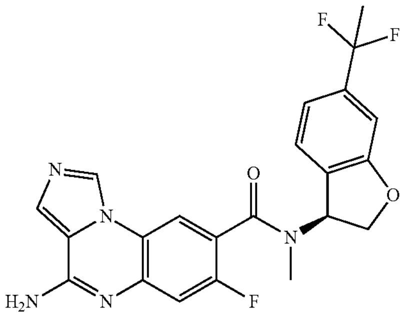 [SMILES: CN(C(=O)c1cc2c(cc1F)nc(N)c1cncn12)[C@@H]1COc2cc(C(C)(F)F)ccc21]

Example Ff-337: (S)-4-amino-N-(6-(1,1-difluoroethyl)-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)-6-(1,1-difluoroethyl)-N-methyl-2,3-dihydrobenzofuran-3-amine Eae-1. ES/MS: m/z=442.0 $[M+H]^+$. $^1$H NMR (400 MHz, MeOD) δ 9.29-9.25 (m, 1H), 8.45 (d, J=5.8 Hz, 1H), 8.39 (dd, J=3.7, 0.7 Hz, 1H), 7.62-7.33 (m, 2H), 7.24-7.13 (m, 1H), 7.09-6.96 (m, 1H), 6.54 (dd, J=8.9, 3.6 Hz, 0.6H, major rotamer), 5.63 (t, J=6.5 Hz, 0.4H, minor rotamer), 4.86-4.60 (m, 2H), 2.85 (s, 1.2H, minor rotamer), 2.71 (d, J=1.1 Hz, 1.8H, major rotamer), 2.00-1.83 (m, 3H).

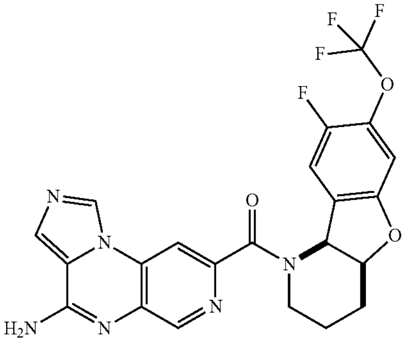

(±)

Example Ff-338: Rac-(4-aminoimidazo[1,5-a]pyrido[3,4-e]pyrazin-8-yl)((4aS,9bS)-8-fluoro-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and rac-(4aS,9bS)-8-fluoro-7-(trifluoromethoxy)-1,2,3,4,4a,9b-hexahydrobenzofuro[3,2-b]pyridine hydrochloride Eba-3. ES/MS: m/z=489.0 $[M+H]^+$. $^1$H NMR (400 MHz, MeOD) δ 9.35 (s, 1H), 8.90-8.76 (m, 1H), 8.68-8.47 (m, 1H), 8.30 (s, 1H), 7.73 (d, J=9.3 Hz, 0.4H, minor rotamer), 7.43 (d, J=8.9 Hz, 0.6, major rotamer), 7.06-6.80 (m, 1H), 6.28 (d, J=8.9 Hz, 0.6, major rotamer), 5.95 (d, J=8.8 Hz, 0.4H, minor rotamer), 5.21-5.17 (m, 0.6, major rotamer), 5.03-4.98 (m, 0.4H, minor rotamer), 4.53-4.35 (m, 0.4H, minor rotamer), 3.92-3.63 (m, 0.6, major rotamer), 3.09-2.71 (m, 1H), 2.29-1.55 (m, 4H).

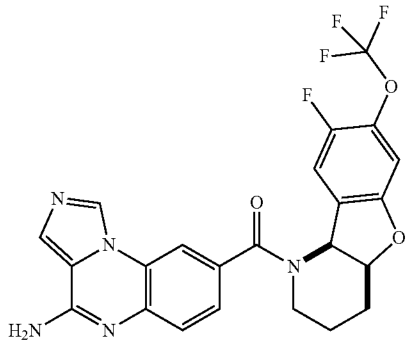

(±)

Example Ff-339: Rac-(4-aminoimidazo[1,5-a]quinoxalin-8-yl)((4aS,9bS)-8-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and rac-(4aS,9bS)-8-fluoro-7-(trifluoromethoxy)-1,2,3,4,4a,9b-hexahydrobenzofuro[3,2-b]pyridine hydrochloride Eba-3. ES/MS: m/z=488.0 $[M+H]^+$. $^1$H NMR (400 MHz, MeOD) δ 9.36 (d, J=0.7 Hz, 1H), 8.54-8.31 (m, 2H), 7.72 (s, 2H), 7.45 (d, J=9.0 Hz, 1H), 6.94 (d, J=5.9 Hz, 1H), 6.26 (s, 1H), 5.17 (s, 1H), 3.78-3.43 (m, 1H), 3.16-2.88 (m, 1H), 2.10 (s, 2H), 1.98-1.86 (m, 1H), 1.77 (d, J=11.3 Hz, 1H).

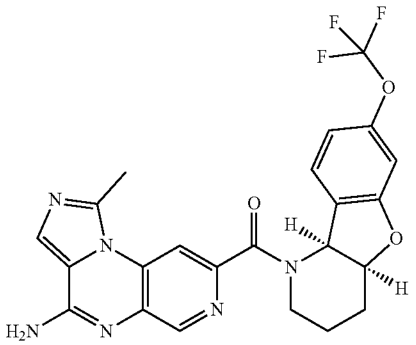 [SMILES: Cc1ncc2c(N)nc3cnc(C(=O)N4CCC[C@@H]5Oc6cc(OC(F)(F)F)ccc6[C@@H]54)cc3n12]

Example Ff-340: (4-amino-1-methylimidazo[1,5-a]pyrido[3,4-e]pyrazin-8-yl)((4aS,9bS)-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (4aS,9bS)-7-(trifluoromethoxy)-1,2,3,4,4a,9b-hexahydrobenzofuro[3,2-b]pyridine hydrochloride Ew-12. ES/MS: m/z=485.0 $[M+H]^+$. $^1$H NMR (400 MHz, MeOD) δ 8.79 (s, 1H), 8.66-8.34 (m, 1H), 8.03 (s, 1H), 7.93-7.37 (m, 1H), 6.89 (d, J=8.3 Hz, 1H), 6.78 (s, 1H), 6.41-5.97 (m, 1H), 5.28-5.00 (m, 1H), 4.61-4.22 (m, 0.2H, minor rotamer), 4.07-3.76 (m, 0.8H, major rotamer), 3.13 (s, 3H), 3.05-2.75 (m, 1H), 2.35-1.64 (m, 4H).

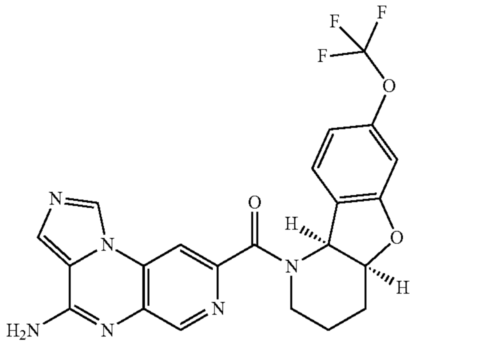 [SMILES: Nc1nc2cnc(C(=O)N3CCC[C@@H]4Oc5cc(OC(F)(F)F)ccc5[C@@H]43)cc2n2cncc12]

Example Ff-341: (4-aminoimidazo[1,5-a]pyrido[3,4-e]pyrazin-8-yl)((4aS,9bS)-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (4aS,9bS)-7-(trifluoromethoxy)-1,2,3,4,4a,9b-hexahydrobenzofuro[3,2-b]pyridine hydrochloride Ew-12. ES/MS: m/z=471.0 $[M+H]^+$. $^1H$ NMR (400 MHz, MeOD) δ 9.34 (s, 1H), 8.89-8.80 (m, 1H), 8.67-8.44 (m, 1H), 8.28 (s, 1H), 7.76 (d, J=8.3 Hz, 0.4H, minor rotamer), 7.53 (d, J=8.1 Hz, 0.6H, major rotamer), 6.92-6.86 (m, 1H), 6.84-6.68 (m, 1H), 6.29 (d, J=8.6 Hz, 0.6H, major rotamer), 5.95 (d, J=9.0 Hz, 0.4H, minor rotamer), 5.19 (s, 0.6H, major rotamer), 5.03 (s, 0.4H, minor rotamer), 4.40 (s, 0.4H, minor rotamer), 3.74 (s, 0.6H, major rotamer), 3.08-2.74 (m, 1H), 2.34-1.63 (m, 4H).

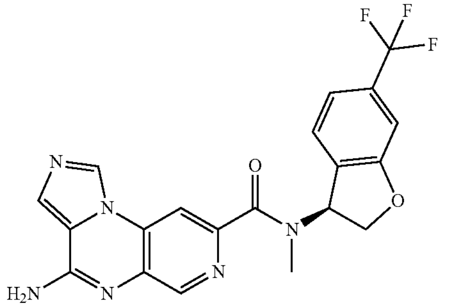 [SMILES: CN(C(=O)c1cc2c(cn1)nc(N)c1cncn12)[C@@H]1COc2cc(C(F)(F)F)ccc21]

Example Ff-342: (S)-4-amino-N-methyl-N-(6-(trifluoromethyl)-2,3-dihydrobenzofuran-3-yl)imidazo[1,5-a]pyrido[3,4-e]pyrazine-8-carboxamide. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (S)—N-methyl-6-(trifluoromethyl)-2,3-dihydrobenzofuran-3-amine hydrochloride Eh-1. ES/MS: m/z=429.0 $[M+H]^+$. $^1H$ NMR (400 MHz, MeOD) δ 9.40-9.33 (m, 1H), 8.90 (s, 0.6H, major rotamer), 8.84 (s, 0.4H, minor rotamer), 8.61 (s, 0.6H, major rotamer), 8.55 (s, 0.4H, minor rotamer), 8.37-8.31 (m, 1H), 7.69 (d, J=7.8 Hz, 0.6H, major rotamer), 7.63 (d, J=7.8 Hz, 0.4H, minor rotamer), 7.36-7.27 (m, 1H), 7.21-7.14 (m, 1H), 6.54 (d, J=8.9 Hz, 0.4H, minor rotamer), 6.07 (t, J=6.6 Hz, 0.6H, major rotamer), 4.78 (d, J=6.7 Hz, 2H), 2.88-2.82 (m, 3H).

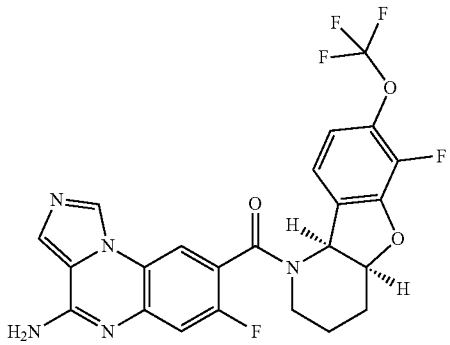 [SMILES: Nc1nc2cc(F)c(C(=O)N3CCC[C@@H]4Oc5c(ccc(OC(F)(F)F)c5F)[C@@H]43)cc2n2cncc12]

Example Ff-343: (4-amino-7-fluoroimidazo[1,5-a]quinoxalin-8-yl)((4aS,9bS)-6-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and (4aS,9bS)-6-fluoro-7-(trifluoromethoxy)-1,2,3,4,4a,9b-hexahydrobenzofuro[3,2-b]pyridine hydrochloride Ew-11. ES/MS: m/z=506.0 $[M+H]^+$. $^1H$ NMR (400 MHz, MeOD) δ 9.30 (d, J=4.8 Hz, 1H), 8.64-8.41 (m, 1H), 8.39 (s, 1H), 7.56-7.46 (m, 1H), 7.30 (s, 1H), 7.22-6.90 (m, 1H), 6.45 (d, J=8.8 Hz, 0.7H, major rotamer), 5.67 (d, J=9.1 Hz, 0.3H, minor rotamer), 5.46-5.15 (m, 1H), 4.48 (d, J=6.9 Hz, 0.3H, minor rotamer), 3.58-3.38 (m, 0.7H, major rotamer), 3.17-2.99 (m, 0.7H, major rotamer), 2.88 (dd, J=13.7, 7.0 Hz, 0.3H, minor rotamer), 2.18-2.04 (m, 2H), 2.01-1.65 (m, 2H).

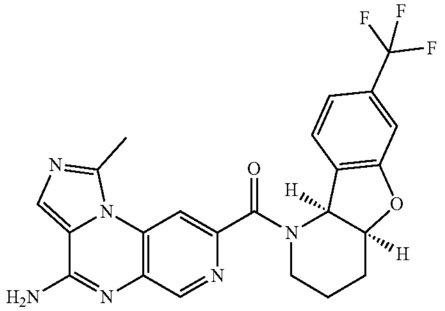 [SMILES: Cc1ncc2c(N)nc3cnc(C(=O)N4CCC[C@@H]5Oc6cc(C(F)(F)F)ccc6[C@@H]54)cc3n12]

Example Ff-344: (4-amino-1-methylimidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (4aS,9bS)-7-(trifluoromethyl)-1,2,3,4,4a,9b-hexahydrobenzofuro[3,2-b]pyridine; hydrochloride Ew-1. ES/MS: m/z=469.0 $[M+H]^+$. $^1H$ NMR (400 MHz, MeOD) δ 8.85 (s, 1H), 8.66-8.43 (m, 1H), 8.27 (s, 1H), 7.91 (s, 0.4H, minor rotamer), 7.64 (s, 0.6H, major rotamer), 7.30 (d, J=7.8 Hz, 1H), 7.13 (d, J=12.7 Hz, 1H), 6.36 (s, 0.6H, major rotamer), 6.13 (s, 0.4H, minor rotamer), 5.20 (s, 0.6H, major rotamer), 5.04 (s, 0.4H, minor rotamer), 4.44 (s, 0.4H, minor rotamer), 3.88 (s, 0.6H, major rotamer), 3.17 (s, 3H), 3.09-2.71 (m, 1H), 2.29-1.59 (m, 4H).

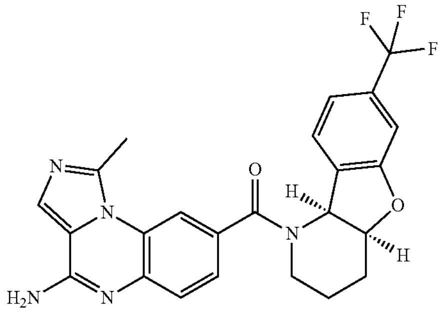 [SMILES: Cc1ncc2c(N)nc3ccc(C(=O)N4CCC[C@@H]5Oc6cc(C(F)(F)F)ccc6[C@@H]54)cc3n12]

Example Ff-345: (4-amino-1-methylimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)-1-methylimidazo[1,5-a]quinoxaline-8-carboxylic acid Af-3 and (4aS,9bS)-7-(trifluoromethyl)-1,2,3,4,4a,9b-hexahydrobenzofuro[3,2-b]pyridine;hydrochloride Ew-1. ES/MS: m/z=468.0 $[M+H]^+$. $^1H$ NMR (400 MHz, MeOD) δ 8.38-8.32 (m, 2H), 7.72 (s, 2H), 7.64 (d, J=7.8 Hz, 1H), 7.34-7.27 (m, 1H), 7.14 (s, 1H), 6.27 (s, 1H), 5.18 (s, 1H), 3.70 (s, 1H), 3.15 (s, 3H), 2.98 (s, 1H), 2.11 (s, 2H), 1.98-1.86 (m, 1H), 1.78 (t, J=9.4 Hz, 1H).

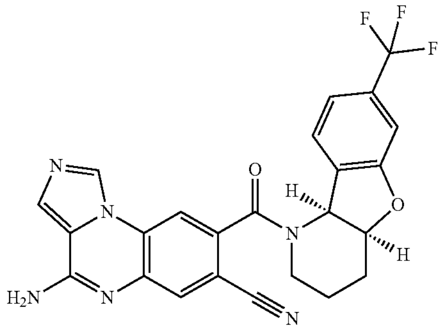 [SMILES: N#Cc1cc2nc(N)c3cncn3c2cc1C(=O)N1CCC[C@@H]2Oc3cc(C(F)(F)F)ccc3[C@@H]21]

Example Ff-346: 4-amino-8-((4aS,9bS)-7-(trifluoromethyl)-1,2,3,4,4a,9b-hexahydrobenzofuro[3,2-b]pyridine-1-carbonyl)imidazo[1,5-a]quinoxaline-7-carbonitrile. Prepared following general procedure VI-F starting with 4-(tert-butoxycarbonylamino)-7-cyano-imidazo[1,5-a]quinoxaline-8-carboxylic acid Al-1 and (4aS,9bS)-7-(trifluoromethyl)-1,2,3,4,4a,9b-hexahydrobenzofuro[3,2-b]pyridine; hydrochloride Ew-1. ES/MS: m/z=479.0 $[M+H]^+$. $^1H$ NMR (400 MHz, MeOD) δ 9.33 (s, 1H), 8.67-8.44 (m, 1H), 8.30 (s, 1H), 8.01 (s, 1H), 7.83-7.51 (m, 1H), 7.30 (d, J=7.9 Hz, 1H), 7.21-6.99 (m, 1H), 6.49 (d, J=8.9 Hz, 0.8H, major rotamer), 5.67 (s, 0.2H, minor rotamer), 5.23 (s, 1H), 4.45 (s, 0.2H, minor rotamer), 3.41 (s, 0.8H, major rotamer), 3.12-2.84 (m, 1H), 2.33-1.64 (m, 4H).

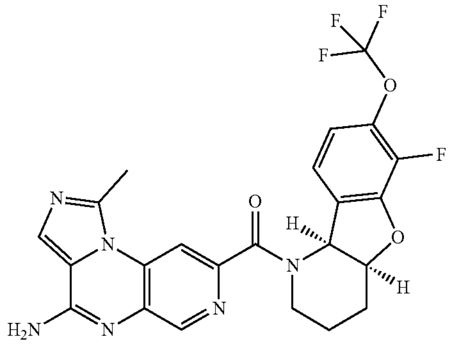 [SMILES: Cc1ncc2c(N)nc3cnc(C(=O)N4CCC[C@@H]5Oc6c(ccc(OC(F)(F)F)c6F)[C@@H]54)cc3n12]

Example Ff-347: (4-amino-1-methylimidazo[1,5-a]pyrido[3,4-e]pyrazin-8-yl)((4aS,9bS)-6-fluoro-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (4aS,9bS)-6-fluoro-7-(trifluoromethoxy)-1,2,3,4,4a,9b-hexahydrobenzofuro[3,2-b]pyridine hydrochloride Ew-11. ES/MS: m/z=503.0 $[M+H]^+$. $^1H$ NMR (400 MHz, MeOD) δ 8.84 (s, 1H), 8.62-8.37 (m, 1H), 8.25 (s, 1H), 7.63 (s, 0.4H, minor rotamer), 7.35 (s, 0.6H, major rotamer), 7.02 (t, J=7.2 Hz, 1H), 6.33 (s, 0.6H, major rotamer), 6.15 (s, 0.4H, minor rotamer), 5.30 (s, 0.6H, major rotamer), 5.15 (s, 0.4H, minor rotamer), 4.44 (s, 0.4H, minor rotamer), 3.91 (s, 0.6H, major rotamer), 3.17 (s, 3H), 3.06-2.77 (m, 1H), 2.35-1.65 (m, 4H).

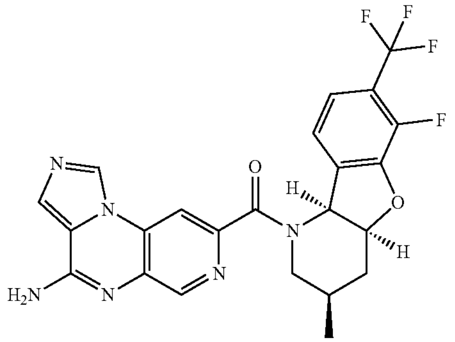 [SMILES: C[C@@H]1C[C@@H]2Oc3c(ccc(C(F)(F)F)c3F)[C@@H]2N(C(=O)c2cc3c(cn2)nc(N)c2cncn23)C1]

Example Ff-348: (4-aminoimidazo[1,5-a]pyrido[3,4-e]pyrazin-8-yl)((3R,4aS,9bS)-6-fluoro-3-methyl-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (3R,4aS,9bS)-6-fluoro-3-methyl-7-(trifluoromethyl)-1,2,3,4,4a,9b-hexahydrobenzofuro[3,2-b]pyridine hydrochloride Ew-17. ES/MS: m/z=487.0 $[M+H]^+$. $^1H$ NMR (400 MHz, MeOD) δ 9.46-9.25 (m, 1H), 8.86 (s, 0.6H, major rotamer), 8.82 (s, 0.4H, minor rotamer), 8.65 (s, 0.4H, minor rotamer), 8.58 (s, 0.6H, major rotamer), 8.39-8.35 (m, 1H), 7.68 (d, J=7.8 Hz, 0.4H, minor rotamer), 7.39 (d, J=7.8 Hz, 0.6H, major rotamer), 7.30 (dt, J=10.6, 7.7 Hz, 1H), 6.39 (d, J=8.4 Hz, 0.6H, major rotamer), 6.05 (d, J=8.3 Hz, 0.4H, minor rotamer), 5.33-5.23 (m, 0.6H, major rotamer), 5.07 (td, J=7.9, 5.5 Hz, 0.4H, minor rotamer), 4.55 (dd, J=13.3, 5.0

Hz, 0.4H, minor rotamer), 3.85 (dd, J=13.8, 5.4 Hz, 0.6H, major rotamer), 2.57 (dd, J=13.7, 11.2 Hz, 0.6H, major rotamer), 2.38-2.18 (m, 2H), 2.05-1.96 (m, 0.4H, minor rotamer), 1.71 (dt, J=14.1, 7.1 Hz, 0.6H, major rotamer), 1.57 (dt, J=14.1, 8.3 Hz, 0.4H, minor rotamer), 1.06 (d, J=6.7 Hz, 1.2H, minor rotamer), 0.93 (d, J=6.7 Hz, 1.8H, major rotamer).

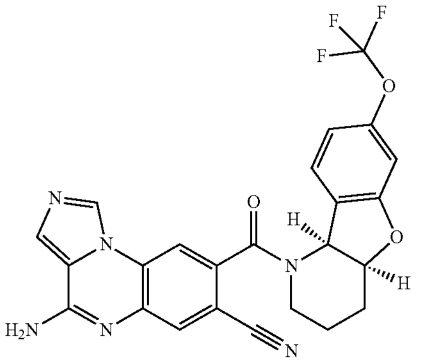 [SMILES: N#Cc1cc2nc(N)c3cncn3c2cc1C(=O)N1CCC[C@@H]2Oc3cc(OC(F)(F)F)ccc3[C@@H]21]

Example Ff-349: 4-amino-8-((4aS,9bS)-7-(trifluoromethoxy)-1,2,3,4,4a,9b-hexahydrobenzofuro[3,2-b]pyridine-1-carbonyl)imidazo[1,5-a]quinoxaline-7-carbonitrile. Prepared following general procedure VI-F starting with 4-(tert-butoxycarbonylamino)-7-cyano-imidazo[1,5-a]quinoxaline-8-carboxylic acid Al-1 and (4aS,9bS)-7-(trifluoromethoxy)-1,2,3,4,4a,9b-hexahydrobenzofuro[3,2-b]pyridine hydrochloride Ew-12. ES/MS: m/z=495.0 $[M+H]^+$. $^1H$ NMR (400 MHz, MeOD) δ 9.35 (s, 1H), 8.76-8.45 (m, 1H), 8.34 (d, J=0.6 Hz, 1H), 8.03 (s, 1H), 7.59 (d, J=8.2 Hz, 0.8H, major rotamer), 7.48 (s, 0.2H, minor rotamer), 6.90 (d, J=8.3 Hz, 1H), 6.86-6.64 (m, 1H), 6.41 (d, J=8.8 Hz, 0.8H, major rotamer), 5.58 (s, 0.2H, minor rotamer), 5.35-5.14 (m, 1H), 4.44 (s, 0.2H, minor rotamer), 3.47-3.36 (m, 0.8H, major rotamer), 3.12-2.83 (m, 1H), 2.14 (s, 2H), 1.91-1.85 (m, 1H), 1.76-1.72 (m, 1H).

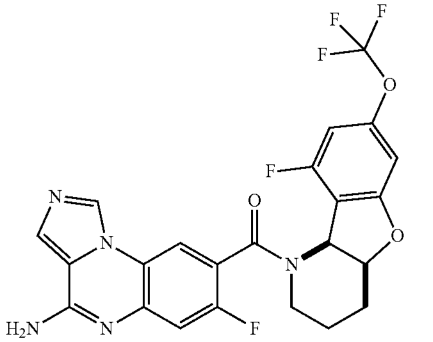

(±)

Example Ff-350: Rac-(4-amino-7-fluoroimidazo[1,5-a]quinoxalin-8-yl)((4aS,9bS)-9-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,9bS)-9-fluoro-7-(trifluoromethoxy)-1,2,3,4,4a,9b-hexahydrobenzofuro[3,2-b]pyridine hydrochloride Eba-4. ES/MS: m/z=506.0 $[M+H]^+$. $^1H$ NMR (400 MHz, MeOD) δ 9.36-9.28 (m, 1H), 8.55-8.26 (m, 2H), 7.58-7.36 (m, 1H), 6.76-6.63 (m, 2.7H), 5.77 (s, 0.3H, minor rotamer), 5.38-5.10 (m, 1H), 4.45 (s, 0.3H, minor rotamer), 3.56-3.42 (m, 0.7H, major rotamer), 3.16-2.79 (m, 1H), 2.16 (s, 1H), 2.08-1.92 (m, 1H), 1.89-1.68 (m, 2H).

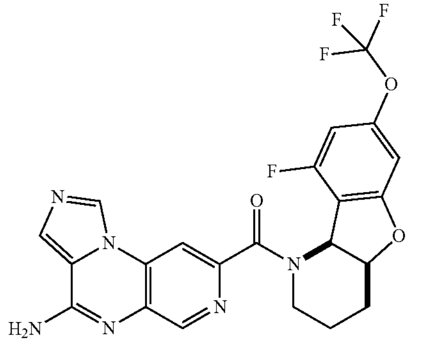

(±)

Example Ff-351: Rac-(4-aminoimidazo[1,5-a]pyrido[3,4-e]pyrazin-8-yl)((4aS,9bS)-9-fluoro-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and rac-(4aS,9bS)-9-fluoro-7-(trifluoromethoxy)-1,2,3,4,4a,9b-hexahydrobenzofuro[3,2-b]pyridine hydrochloride Eba-4. ES/MS: m/z=489.0 $[M+H]^+$. $^1H$ NMR (400 MHz, MeOD) δ 9.40 (s, 1H), 8.85 (s, 1H), 8.65-8.46 (m, 1H), 8.35 (d, J=0.6 Hz, 1H), 6.70 (s, 1H), 6.67-6.39 (m, 2H), 5.27 (dd, J=8.7, 4.0 Hz, 1H), 4.40 (s, 0.2H, minor rotamer), 3.82 (s, 0.8H, major rotamer), 3.09-2.83 (m, 1H), 2.28-1.91 (m, 3H), 1.76 (s, 1H).

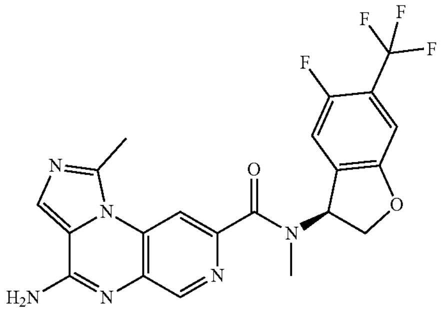 [SMILES: Cc1ncc2c(N)nc3cnc(C(=O)N(C)[C@@H]4COc5cc(C(F)(F)F)c(F)cc54)cc3n12]

Example Ff-352: (S)-4-amino-N-(5-fluoro-6-(trifluoromethyl)-2,3-dihydrobenzofuran-3-yl)-N,1-dimethylimidazo[1,5-a]quinoxaline-8-carboxamide. Prepared following general procedure VI-F starting with 4-((tert-butoxycarbonyl)amino)-1-methylimidazo[1,5-a]quinoxaline-8-carboxylic acid Af-3 and (S)-5-fluoro-N-methyl-6-(trifluoromethyl)-2,3-dihydrobenzofuran-3-amine hydrochloride Ebg-1. ES/MS: m/z=460.0 $[M+H]^+$. $^1H$ NMR (400 MHz, MeOD) δ 8.39 (d, J=1.4 Hz, 1H), 8.35 (s, 1H), 7.79-7.68 (m, 2H), 7.50 (d, J=9.5 Hz, 1H), 7.18 (d, J=5.3 Hz, 1H), 6.48 (s, 1H), 4.84-4.76 (m, 2H), 3.16 (s, 3H), 2.85 (s, 3H).

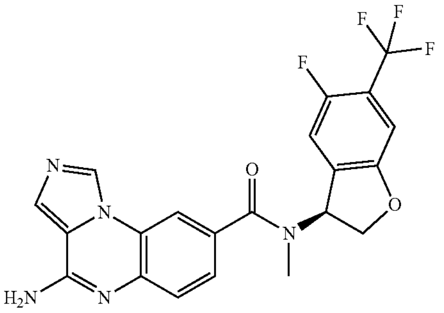 [SMILES: CN(C(=O)c1ccc2nc(N)c3cncn3c2c1)[C@@H]1COc2cc(C(F)(F)F)c(F)cc21]

Example Ff-353: (S)-4-amino-N-(5-fluoro-6-(trifluoromethyl)-2,3-dihydrobenzofuran-3-yl)-N-methylimidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and (S)-5-fluoro-N-methyl-6-(trifluoromethyl)-2,3-dihydrobenzofuran-3-amine hydrochloride Ebg-1. ES/MS: m/z=446.0 $[M+H]^+$. $^1H$ NMR (400 MHz, MeOD) δ 9.34 (s, 1H), 8.48 (s, 1H), 8.42 (d, J=0.6 Hz, 1H), 7.74 (s, 2H), 7.49 (d, J=9.5 Hz, 1H), 7.18 (d, J=5.3 Hz, 1H), 6.49 (s, 1H), 4.82-4.74 (m, 2H), 2.84 (s, 3H).

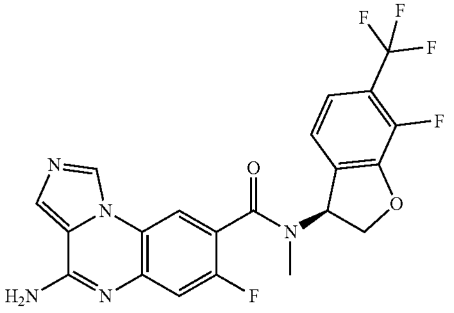 [SMILES: CN(C(=O)c1cc2c(cc1F)nc(N)c1cncn12)[C@@H]1COc2c1ccc(C(F)(F)F)c2F]

Example Ff-354: (S)-4-amino-7-fluoro-N-(7-fluoro-6-(trifluoromethyl)-2,3-dihydrobenzofuran-3-yl)-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)-7-fluoro-N-methyl-6-(trifluoromethyl)-2,3-dihydrobenzofuran-3-amine hydrochloride Ebg-2. ES/MS: m/z=464.0 $[M+H]^+$. $^1H$ NMR (400 MHz, MeOD) δ 9.34-9.20 (m, 1H), 8.46 (d, J=5.8 Hz, 1H), 8.42-8.37 (m, 1H), 7.56-7.46 (m, 1H), 7.43-7.22 (m, 2H), 6.61 (dd, J=9.0, 4.0 Hz, 0.6H, major rotamer), 5.78 (t, J=6.7 Hz, 0.4H, minor rotamer), 5.00 (dd, J=10.7, 9.0 Hz, 1H), 4.90-4.81 (m, 1H), 2.89 (s, 1.2H, minor rotamer), 2.79 (d, J=1.2 Hz, 1.8H, major rotamer).

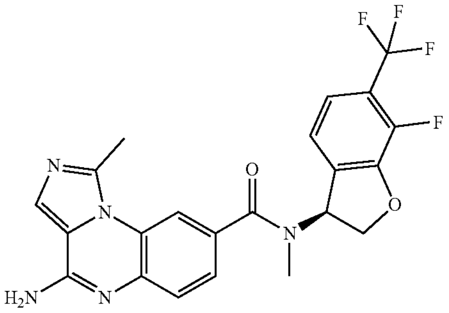 [SMILES: Cc1ncc2c(N)nc3ccc(C(=O)N(C)[C@@H]4COc5c4ccc(C(F)(F)F)c5F)cc3n12]

Example Ff-355: (S)-4-amino-N-(7-fluoro-6-(trifluoromethyl)-2,3-dihydrobenzofuran-3-yl)-N,1-dimethylimidazo[1,5-a]quinoxaline-8-carboxamide. Prepared following general procedure VI-F starting with 4-((tert-butoxycarbonyl)amino)-1-methylimidazo[1,5-a]quinoxaline-8-carboxylic acid Af-3 and (S)-7-fluoro-N-methyl-6-(trifluoromethyl)-2,3-dihydrobenzofuran-3-amine hydrochloride Ebg-2. ES/MS: m/z=460.0 $[M+H]^+$. $^1H$ NMR (400 MHz, MeOD) δ 8.37 (s, 1H), 8.35 (s, 1H), 7.79-7.69 (m, 2H), 7.43 (s, 1H), 7.30 (dd, J=7.9, 5.6 Hz, 1H), 6.53 (s, 1H), 5.05-4.91 (m, 2H), 3.15 (s, 3H), 2.85 (s, 3H).

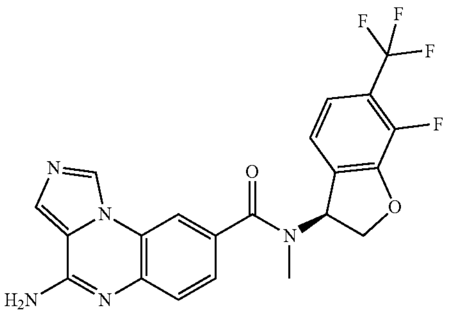 [SMILES: CN(C(=O)c1ccc2nc(N)c3cncn3c2c1)[C@@H]1COc2c1ccc(C(F)(F)F)c2F]

Example Ff-356: (S)-4-amino-N-(7-fluoro-6-(trifluoromethyl)-2,3-dihydrobenzofuran-3-yl)-N-methylimidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and (S)-7-fluoro-N-methyl-6-(trifluoromethyl)-2,3-dihydrobenzofuran-3-amine hydrochloride Ebg-2. ES/MS: m/z=446.0 $[M+H]^+$. $^1H$ NMR (400 MHz, MeOD) δ 9.34 (s, 1H), 8.47 (s, 1H), 8.43 (s, 1H), 7.73 (s, 2H), 7.43 (s, 1H), 7.31 (t, J=6.8 Hz, 1H), 6.55 (s, 1H), 5.06-4.93 (m, 2H), 2.84 (s, 3H).

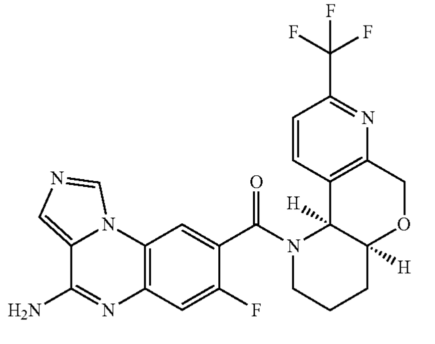 [SMILES: Nc1nc2cc(F)c(C(=O)N3CCC[C@@H]4OCc5nc(C(F)(F)F)ccc5[C@@H]43)cc2n2cncc12]

Example Ff-357: (4-amino-7-fluoroimidazo[1,5-a]quinoxalin-8-yl)((4aS,10bS)-8-(trifluoromethyl)-2,3,4,4a,6,10b-hexahydro-1H-pyrano[3,2-b:5,4-b']dipyridin-1-yl)methanone. Prepared following general procedure VI-F starting with 4-((tert-butoxycarbonyl)amino)-7-fluoroimidazo[1,5-a]quinoxaline-8-carboxylic acid Af-1 and (4aS,10bS)-8-(trifluoromethyl)-2,3,4,4a,6,10b-hexahydro-1H-pyrano[3,2-b:5,4-b']dipyridine hydrochloride Ebh-1. ES/MS: m/z=487.0 $[M+H]^+$. $^1H$ NMR (400 MHz, MeOD) δ 9.29 (s, 1H), 8.56 (s, 1H), 8.38 (s, 1H), 8.22-7.94 (m, 1H), 7.82 (d, J=8.1 Hz, 1H), 7.51 (d, J=9.7 Hz, 1H), 6.21 (s, 1H), 5.18-4.89 (m, 2H), 4.33 (dt, J=10.9, 5.2 Hz, 1H), 3.56-3.38 (m, 1H), 2.90 (s, 1H), 2.08-1.95 (m, 1H), 1.92-1.85 (m, 1H), 1.82-1.60 (m, 2H).

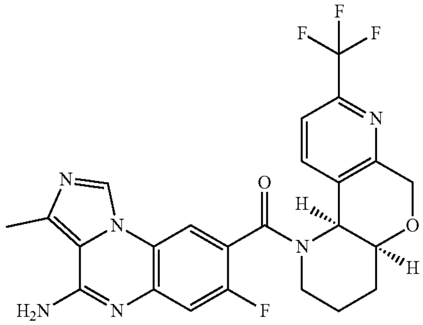 [SMILES: Cc1ncn2c1c(N)nc1cc(F)c(C(=O)N3CCC[C@@H]4OCc5nc(C(F)(F)F)ccc5[C@@H]43)cc12]

Example Ff-358: (4-amino-7-fluoro-3-methylimidazo[1,5-a]quinoxalin-8-yl)((4aS,10bS)-8-(trifluoromethyl)-2,3,4,4a,6,10b-hexahydro-1H-pyrano[3,2-b:5,4-b']dipyridin-1-yl)methanone. Prepared following general procedure VI-F starting with 4-((tert-butoxycarbonyl)amino)-7-fluoro-3-methylimidazo[1,5-a]quinoxaline-8-carboxylic acid Af-4 and (4aS,10bS)-8-(trifluoromethyl)-2,3,4,4a,6,10b-hexahydro-1H-pyrano[3,2-b:5,4-b']dipyridine hydrochloride Ebh-1. ES/MS: m/z=501.0 $[M+H]^+$. $^1H$ NMR (400 MHz, MeOD) δ 9.19 (s, 1H), 8.49 (s, 1H), 8.15-7.91 (m, 1H), 7.81 (d, J=8.0 Hz, 1H), 7.50 (d, J=9.6 Hz, 1H), 6.20 (s, 1H), 4.98 (d, J=17.1 Hz, 1H), 4.87-4.69 (m, 1H), 4.32 (dt, J=10.8, 5.1 Hz, 1H), 3.51-3.43 (m, 1H), 3.05-2.74 (m, 4H), 2.03-1.92 (m, 1H), 1.88 (d, J=8.8 Hz, 1H), 1.79-1.63 (m, 2H).

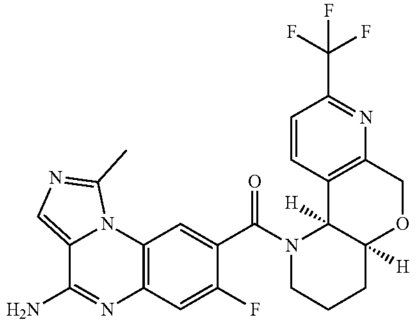 [SMILES: Cc1ncc2c(N)nc3cc(F)c(C(=O)N4CCC[C@@H]5OCc6nc(C(F)(F)F)ccc6[C@@H]54)cc3n12]

Example Ff-359: (4-amino-7-fluoro-1-methylimidazo[1,5-a]quinoxalin-8-yl)((4aS,10bS)-8-(trifluoromethyl)-2,3,4,4a,6,10b-hexahydro-1H-pyrano[3,2-b:5,4-b']dipyridin-1-yl)methanone. Prepared following general procedure VI-F starting with 4-((tert-butoxycarbonyl)amino)-7-fluoro-1-methylimidazo[1,5-a]quinoxaline-8-carboxylic acid Af-5 and (4aS,10bS)-8-(trifluoromethyl)-2,3,4,4a,6,10b-hexahydro-1H-pyrano[3,2-b:5,4-b']dipyridine hydrochloride Ebh-1. ES/MS: m/z=501.0 $[M+H]^+$. $^1H$ NMR (400 MHz, MeOD) δ 8.39 (d, J=5.8 Hz, 1H), 8.33 (s, 1H), 8.24-7.92 (m, 1H), 7.82 (d, J=8.1 Hz, 1H), 7.52 (d, J=9.7 Hz, 1H), 6.22 (s, 1H), 4.98 (d, J=17.4 Hz, 1H), 4.80-4.49 (m, 1H), 4.35 (s, 1H), 3.61-3.42 (m, 1H), 3.16 (s, 3H), 2.91 (s, 1H), 2.05-1.96 (m, 1H), 1.92-1.67 (m, 3H).

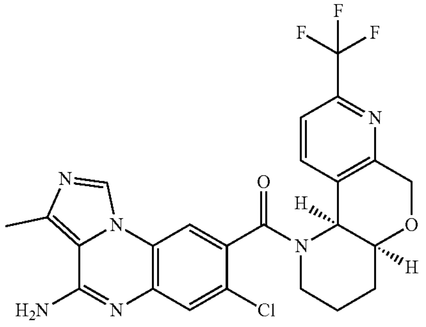 [SMILES: Cc1ncn2c1c(N)nc1cc(Cl)c(C(=O)N3CCC[C@@H]4OCc5nc(C(F)(F)F)ccc5[C@@H]43)cc12]

Example Ff-360: (4-amino-7-chloro-3-methylimidazo[1,5-a]quinoxalin-8-yl)((4aS,10bS)-8-(trifluoromethyl)-2,3,4,4a,6,10b-hexahydro-1H-pyrano[3,2-b:5,4-b']dipyridin-1-yl)methanone. Prepared following general procedure VI-F starting with 4-amino-7-chloro-3-methyl-imidazo[1,5-a]quinoxaline-8-carboxylic acid Aj-1 and (4aS,10bS)-8-(trifluoromethyl)-2,3,4,4a,6,10b-hexahydro-1H-pyrano[3,2-b:5,4-b']dipyridine hydrochloride Ebh-1. ES/MS: m/z=517.0 $[M+H]^+$. $^1H$ NMR (400 MHz, MeOD) δ 9.22 (s, 0.4H, minor rotamer), 9.17 (s, 0.6H, major rotamer), 8.48-8.40 (m, 1H), 8.22-8.11 (m, 1H), 7.87-7.77 (m, 1H), 7.75-7.65 (m, 1H), 6.20 (d, J=6.9 Hz, 1H), 4.98 (d, J=17.2 Hz, 1H), 4.80-4.56 (m, 1H), 4.50-4.25 (m, 1H), 3.57-3.35 (m, 1H), 3.06-2.71 (m, 4H), 2.14-1.53 (m, 4H).

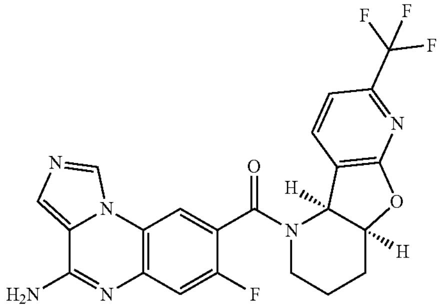

Example Ff-361: (4-amino-7-fluoroimidazo[1,5-a]quinoxalin-8-yl)((4aS,9bS)-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-chloroimidazo[1,5-a]quinoxaline-8-carboxylic acid Af-1 and (4aS,9bS)-7-(trifluoromethyl)-1,2,3,4,4a,9b-hexahydrofuro[2,3-b:4,5-b']dipyridine hydrochloride Ew-14. ES/MS: m/z=473.0 $[M+H]^+$. $^1H$ NMR (400 MHz, MeOD) δ 9.27 (s, 1H), 8.55 (s, 0.2H, minor rotamer), 8.47 (d, J=5.9 Hz, 0.8H, major rotamer), 8.38 (s, 1H), 8.02 (s, 0.8H, major rotamer), 7.94 (d, J=7.5 Hz, 0.2H, minor rotamer), 7.54-7.41 (m, 2H), 6.51 (d, J=8.9 Hz, 0.8H, major rotamer), 5.74 (d, J=9.2 Hz, 0.2H, minor rotamer), 5.32 (dt, J=9.1, 4.6 Hz, 1H), 4.48 (s, 0.2H, minor rotamer), 3.57-3.51 (m, 0.8H, major rotamer), 3.10 (dd, J=14.2, 7.1 Hz, 0.8H, major rotamer), 2.95-2.87 (m, 0.2H, minor rotamer), 2.23-2.02 (m, 2H), 1.97-1.63 (m, 2H).

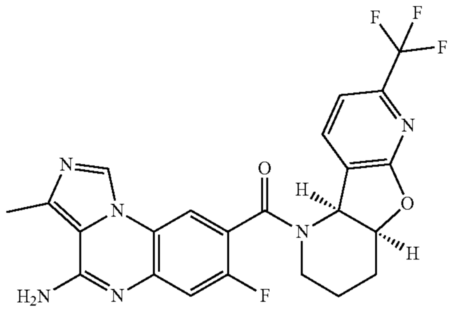

Example Ff-362: (4-amino-7-fluoro-3-methylimidazo[1,5-a]quinoxalin-8-yl)((4aS,9bS)-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-fluoro-3-methylimidazo[1,5-a]quinoxaline-8-carboxylic acid Af-4 and (4aS,9bS)-7-(trifluoromethyl)-1,2,3,4,4a,9b-hexahydrofuro[2,3-b:4,5-b']dipyridine hydrochloride Ew-14. ES/MS: m/z=487.0 $[M+H]^+$. $^1H$ NMR (400 MHz, MeOD) δ 9.16 (s, 1H), 8.47 (s, 0.2H, minor rotamer), 8.39 (d, J=5.8 Hz, 0.8H, major rotamer), 8.01 (s, 0.8H, major rotamer), 7.93 (d, J=7.3 Hz, 0.2H, minor rotamer), 7.52-7.42 (m, 2H), 6.50 (d, J=9.0 Hz, 0.8H, major rotamer), 5.73 (d, J=9.1 Hz, 0.2H, minor rotamer), 5.31 (dt, J=9.3, 4.7 Hz, 1H), 4.47 (s, 0.2H, minor rotamer), 3.63-3.43 (m, 0.8H, major rotamer), 3.12-3.04 (m, 0.8H, major rotamer), 2.91 (d, J=6.6 Hz, 0.2H, minor rotamer), 2.80 (s, 3H), 2.26-2.01 (m, 2H), 1.98-1.63 (m, 2H).

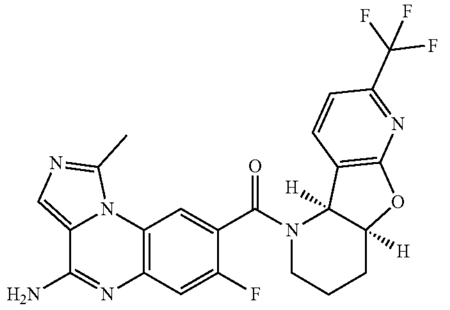

Example Ff-363: (4-amino-7-fluoro-1-methylimidazo[1,5-a]quinoxalin-8-yl)((4aS,9bS)-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-fluoro-1-methylimidazo[1,5-a]quinoxaline-8-carboxylic acid Af-5 and (4aS,9bS)-7-(trifluoromethyl)-1,2,3,4,4a,9b-hexahydrofuro[2,3-b:4,5-b']dipyridine hydrochloride Ew-14. ES/MS: m/z=487.0 $[M+H]^+$. $^1H$ NMR (400 MHz, MeOD) δ 8.45-8.22 (m, 2H), 8.12-7.88 (m, 1H), 7.66-7.34 (m, 2H), 6.50 (d, J=8.8 Hz, 0.8H, major rotamer), 5.76 (s, 0.2H, minor rotamer), 5.31 (s, 1H), 4.49 (s, 0.2H, minor rotamer), 3.64-3.45 (m, 0.8H, major rotamer), 3.22-2.84 (m, 4H), 2.25-2.00 (m, 2H), 1.96-1.65 (m, 2H).

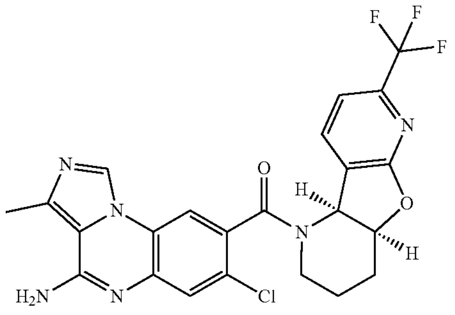 [SMILES: Cc1ncn2c1c(N)nc1cc(Cl)c(C(=O)N3CCC[C@@H]4Oc5nc(C(F)(F)F)ccc5[C@@H]43)cc12]

Example Ff-364: (4-amino-7-chloro-3-methylimidazo[1,5-a]quinoxalin-8-yl)((4aS,9bS)-7-(trifluoromethyl)-3,4,4a,9b-tetrahydrofuro[2,3-b:4,5-b']dipyridin-1(2H)-yl)methanone. Prepared following general procedure VI-F starting with 4-amino-7-chloro-3-methyl-imidazo[1,5-a]quinoxaline-8-carboxylic acid Aj-1 and (4aS,9bS)-7-(trifluoromethyl)-1,2,3,4,4a,9b-hexahydrofuro[2,3-b:4,5-b']dipyridine hydrochloride Ew-14. ES/MS: m/z=503.0 $[M+H]^+$. $^1H$ NMR (400 MHz, MeOD) δ 9.32-9.08 (m, 1H), 8.52 (s, 0.3H, minor rotamer), 8.43-8.31 (m, 0.7H, major rotamer), 8.12 (d, J=7.4 Hz, 0.3H, minor rotamer), 8.02 (t, J=8.3 Hz, 0.7H, major rotamer), 7.77-7.67 (m, 1H), 7.54-7.30 (m, 1H), 6.59-6.48 (m, 0.7H, major rotamer), 5.73-5.50 (m, 0.3H, minor rotamer), 5.43-5.10 (m, 1H), 4.53-4.45 (m, 0.3H, minor rotamer), 3.43-3.37 (m, 0.7H, major rotamer), 3.14-2.89 (m, 1H), 2.80 (d, J=3.8 Hz, 3H), 2.10 (d, J=14.7 Hz, 2H), 1.92-1.63 (m, 2H).

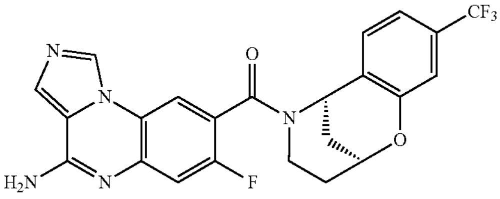 [SMILES: Nc1nc2cc(F)c(C(=O)N3CC[C@H]4C[C@@H]3c3ccc(C(F)(F)F)cc3O4)cc2n2cncc12]

Example Ff-365: (4-amino-7-fluoroimidazo[1,5-a]quinoxalin-8-yl)((2S,6R)-9-(trifluoromethyl)-3,4-dihydro-2H-2,6-methanobenzo[b][1,5]oxazocin-5(6H)-yl)methanone. Prepared following general procedure VI-F starting with 4-((tert-butoxycarbonyl)amino)-7-fluoroimidazo[1,5-a]quinoxaline-8-carboxylic acid Af-1 and (2S,6R)-9-(trifluoromethyl)-3,4,5,6-tetrahydro-2H-2,6-methanobenzo[b][1,5]oxazocine Ebi-1. ES/MS: m/z=472.0 $[M+H]^+$. $^1H$ NMR (400 MHz, MeOD) δ 9.33 (s, 0.3H, minor rotamer), 9.24 (s, 0.7H, major rotamer), 8.56 (d, J=5.8 Hz, 0.3H, minor rotamer), 8.50-8.25 (m, 1.7H), 7.65-6.98 (m, 4H), 6.11 (s, 1H), 4.95-4.86 (m, 1H), 4.56 (dd, J=14.0, 6.2 Hz, 0.3H, minor rotamer), 3.54-3.45 (m, 0.7H, major rotamer), 3.19-3.03 (m, 0.7H, major rotamer), 2.78 (t, J=14.0 Hz, 0.3H, minor rotamer), 2.47-1.88 (m, 4H).

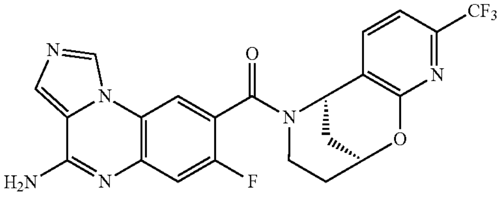 [SMILES: Nc1nc2cc(F)c(C(=O)N3CC[C@H]4C[C@@H]3c3ccc(C(F)(F)F)nc3O4)cc2n2cncc12]

Example Ff-366: (4-amino-7-fluoroimidazo[1,5-a]quinoxalin-8-yl)((2S,6R)-9-(trifluoromethyl)-3,4-dihydro-2H-2,6-methanopyrido[2,3-b][1,5]oxazocin-5(6H)-yl)methanone. Prepared following general procedure VI-F starting with 4-((tert-butoxycarbonyl)amino)-7-fluoroimidazo[1,5-a]quinoxaline-8-carboxylic acid Af-1 and (2S,6R)-9-(trifluoromethyl)-3,4,5,6-tetrahydro-2H-2,6-methanopyrido[2,3-b][1,5]oxazocine Ebi-3. ES/MS: m/z=473.0 [M+H]$^+$. $^1$H NMR (400 MHz, MeOD) δ 9.30 (s, 0.3H, minor rotamer), 9.22 (s, 0.7H, major rotamer), 8.55 (d, J=5.8 Hz, 0.3H, minor rotamer), 8.47-8.29 (m, 1.7H), 8.01 (d, J=7.5 Hz, 1H), 7.73-7.32 (m, 2H), 6.19 (s, 0.7H, major rotamer), 5.11 (s, 1H), 5.05 (s, 0.3H, minor rotamer), 4.61 (d, J=14.5 Hz, 0.3H, minor rotamer), 3.56 (dd, J=14.4, 5.7 Hz, 0.7H, major rotamer), 3.08 (t, J=13.5 Hz, 0.7H, major rotamer), 2.75 (t, J=13.4 Hz, 0.3H, minor rotamer), 2.53-2.22 (m, 2H), 2.12 (s, 2H).

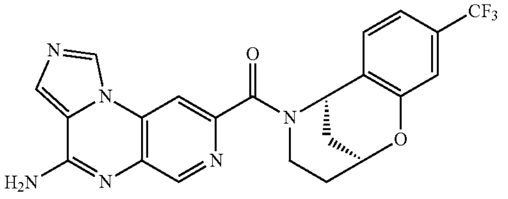 [SMILES: Nc1nc2cnc(C(=O)N3CC[C@H]4C[C@@H]3c3ccc(C(F)(F)F)cc3O4)cc2n2cncc12]

Example Ff-367: (4-aminoimidazo[1,5-a]pyrido[3,4-e]pyrazin-8-yl)((2S,6R)-9-(trifluoromethyl)-3,4-dihydro-2H-2,6-methanobenzo[b][1,5]oxazocin-5(6H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (2S,6R)-9-(trifluoromethyl)-3,4,5,6-tetrahydro-2H-2,6-methanobenzo[b][1,5]oxazocine Ebi-1. ES/MS: m/z=455.0 [M+H]$^+$. $^1$H NMR (400 MHz, MeOD) δ 9.39 (s, 0.4H, minor rotamer), 9.32 (s, 0.6H, major rotamer), 8.96 (s, 0.4H, minor rotamer), 8.79 (s, 0.6H, major rotamer), 8.60 (s, 0.4H, minor rotamer), 8.46 (s, 0.6H, major rotamer), 8.35 (s, 0.4H, minor rotamer), 8.31 (s, 0.6H, major rotamer), 7.50 (d, J=7.9 Hz, 1H), 7.37 (d, J=7.8 Hz, 0.4H, minor rotamer), 7.29-7.04 (m, 1.6H), 6.08 (s, 0.6H, major rotamer), 5.41 (s, 0.4H, minor rotamer), 4.53 (dd, J=14.2, 6.3 Hz, 0.4H, minor rotamer), 3.91-3.82 (m, 0.6H, major rotamer), 3.19-3.01 (m, 0.6H, major rotamer), 2.81 (td, J=13.8, 4.3 Hz, 0.4H, minor rotamer), 2.45 (d, J=13.5 Hz, 0.4H, minor rotamer), 2.35 (d, J=14.0 Hz, 0.6H, major rotamer), 2.24 (d, J=13.0 Hz, 1H), 2.06 (d, J=13.3 Hz, 2H), 1H overlapping with solvent.

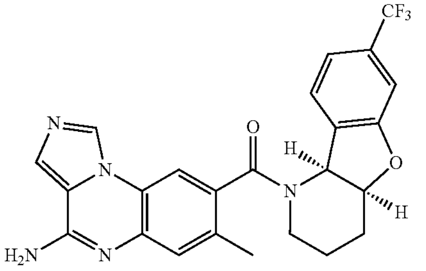

Example Ff-368: (4-amino-7-methylimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)-7-methylimidazo[1,5-a]quinoxaline-8-carboxylic acid Am-1 and (4aS,9bS)-7-(trifluoromethyl)-1,2,3,4,4a,9b-hexahydrobenzofuro[3,2-b]pyridine Ew-1. ES/MS: m/z=468.3 [M+H]$^+$. $^1$H NMR (400 MHz, DMSO-d$_6$) δ 9.44 (s, 0.3H, minor rotamer), 9.39 (s, 0.7H, major rotamer), 8.60 (s, 0.3H, minor rotamer), 8.42 (s, 0.7H, major rotamer), 8.33 (s, 0.7H, major rotamer), 8.24 (s, 0.3H, minor rotamer), 7.80 (d, J=7.8 Hz, 0.3H, minor rotamer), 7.55 (d, J=6.9 Hz, 0.7H, major rotamer), 7.49 (s, 0.7H, major rotamer), 7.46 (s, 0.7H, major rotamer), 7.37 (s, 0.3H, minor rotamer), 7.35 (s, 0.3H, minor rotamer), 7.27 (s, 0.7H, major rotamer), 7.18 (s, 0.3H, minor rotamer), 6.39 (d, J=9.4 Hz, 0.7H, major rotamer), 5.32 (d, J=9.3 Hz, 0.3H, minor rotamer), 5.24 (dt, J=9.1, 4.6 Hz, 0.7H, major rotamer), 5.14 (dt, J=9.3, 4.7 Hz, 0.3H, minor rotamer), 3.17 (s, 0.3H, minor rotamer), 2.81 (s, 0.7H, major rotamer), 2.40 (s, 2.1H, major rotamer), 2.30 (s, 0.9H, minor rotamer), 2.01 (s, 1H), 1.88 (m, 1H), 1.72-1.65 (m, 1H), 1.51 (m, 1H).

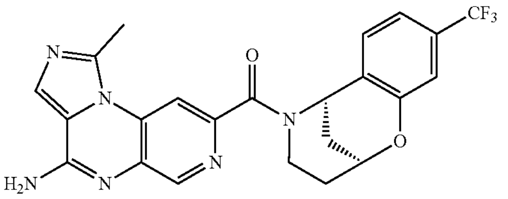 [SMILES: Cc1ncc2c(N)nc3cnc(C(=O)N4CC[C@H]5C[C@@H]4c4ccc(C(F)(F)F)cc4O5)cc3n12]

Example Ff-369: (4-amino-1-methylimidazo[1,5-a]pyrido[3,4-e]pyrazin-8-yl)((2S,6R)-9-(trifluoromethyl)-3,4-dihydro-2H-2,6-methanobenzo[b][1,5]oxazocin-5(6H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (2S,6R)-9-(trifluoromethyl)-3,4,5,6-tetrahydro-2H-2,6-methanobenzo[b][1,5]oxazocine Ebi-1. ES/MS: m/z=469.0 [M+H]$^+$. $^1$H NMR (400 MHz, MeOD) δ 8.97 (s, 0.4H, minor rotamer), 8.79 (s, 0.6H, major rotamer), 8.49 (s, 0.4H, minor rotamer), 8.38 (s, 0.6H, major rotamer), 8.31 (s, 0.4H, minor rotamer), 8.28 (s, 0.6H, major rotamer), 7.50 (d, J=7.9 Hz, 0.6H, major rotamer), 7.44 (d, J=7.8 Hz, 0.4H, minor rotamer), 7.28-7.10 (m, 2H), 6.07 (s, 0.6H, major rotamer), 5.54 (s, 0.4H, minor rotamer), 4.55 (dd, J=14.1, 6.3 Hz, 0.4H, minor rotamer), 4.00 (dd, J=14.1, 5.4 Hz, 0.6H, major rotamer), 3.20-3.04 (m, 3.6H), 2.81 (td, J=13.5, 4.1 Hz, 0.4H, minor rotamer), 2.45 (d, J=13.6 Hz, 0.4H, minor rotamer), 2.37 (d, J=13.8 Hz, 0.6H, major rotamer), 2.23 (d, J=13.0 Hz, 1H), 2.17-2.00 (m, 2H), 1H overlapping with solvent.

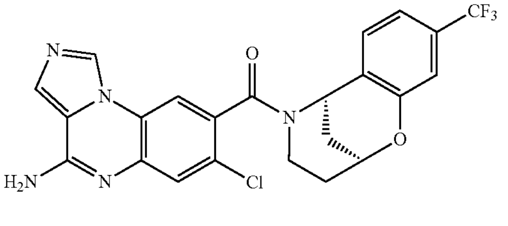 [SMILES: Nc1nc2cc(Cl)c(C(=O)N3CC[C@H]4C[C@@H]3c3ccc(C(F)(F)F)cc3O4)cc2n2cncc12]

Example Ff-370: (4-amino-7-chloroimidazo[1,5-a]quinoxalin-8-yl)((2S,6R)-9-(trifluoromethyl)-3,4-dihydro-2H-2,6-methanobenzo[b][1,5]oxazocin-5(6H)-yl)methanone. Prepared following general procedure VI-F starting with 4-((tert-butoxycarbonyl)amino)-7-chloroimidazo[1,5-a]quinoxaline-8-carboxylic acid Af-2 and (2S,6R)-9-(trifluoromethyl)-3,4,5,6-tetrahydro-2H-2,6-methanobenzo[b][1,5]oxazocine Ebi-1. ES/MS: m/z=488.0 [M+H]+. $^1$H NMR (400 MHz, MeOD) δ 9.49-9.16 (m, 1H), 8.61-8.36 (m, 1H), 8.35-8.20 (m, 1H), 7.90-7.62 (m, 1H), 7.52 (dd, J=13.2, 7.9 Hz, 1H), 7.31-7.08 (m, 2H), 6.13 (s, 1H), 4.85-4.52 (m, 1H), 3.42-3.34 (m, 1H), 3.22-2.97 (m, 0.7H, major rotamer), 2.90-2.72 (m, 0.3H, minor rotamer), 2.51 (d, J=13.5 Hz, 0.3H, minor rotamer), 2.40-2.20 (m, 1.7H), 2.19-1.88 (m, 2H).

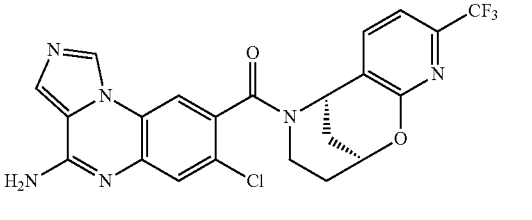 [SMILES: Nc1nc2cc(Cl)c(C(=O)N3CC[C@H]4C[C@@H]3c3ccc(C(F)(F)F)nc3O4)cc2n2cncc12]

Example Ff-371: (4-amino-7-chloroimidazo[1,5-a]quinoxalin-8-yl)((2S,6R)-9-(trifluoromethyl)-3,4-dihydro-2H-2,6-methanopyrido[2,3-b][1,5]oxazocin-5(6H)-yl)methanone. Prepared following general procedure VI-F starting with 4-((tert-butoxycarbonyl)amino)-7-chloroimidazo[1,5-a]quinoxaline-8-carboxylic acid Af-2 and (2S,6R)-9-(trifluoromethyl)-3,4,5,6-tetrahydro-2H-2,6-methanopyrido[2,3-b][1,5]oxazocine Ebi-3. ES/MS: m/z=489.0 [M+H]+. $^1$H NMR (400 MHz, MeOD) δ 9.39-9.12 (m, 1H), 8.60-8.17 (m, 2H), 8.07-7.99 (m, 1H), 7.89-7.59 (m, 1H), 7.57-7.31 (m, 1H), 6.22 (s, 1H), 5.10 (s, 1H), 4.67 (td, J=13.8, 6.2 Hz, 0.2H, minor rotamer), 3.46-3.38 (m, 0.8H, major rotamer), 3.13-2.82 (m, 1H), 2.43-1.97 (m, 4H).

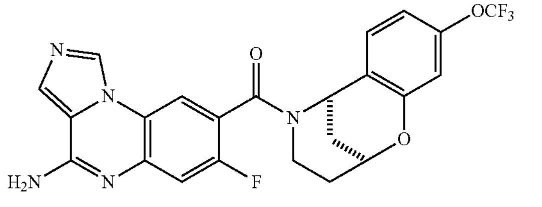

(±)

Example Ff-372: Rac-(4-amino-7-fluoroimidazo[1,5-a]quinoxalin-8-yl)((2S,6R)-9-(trifluoromethoxy)-3,4-dihydro-2H-2,6-methanobenzo[b][1,5]oxazocin-5(6H)-yl)methanone. Prepared following general procedure VI-F starting with 4-((tert-butoxycarbonyl)amino)-7-fluoroimidazo[1,5-a]quinoxaline-8-carboxylic acid Af-1 and rac-(2S,6R)-9-(trifluoromethoxy)-3,4,5,6-tetrahydro-2H-2,6-methanobenzo[b][1,5]oxazocine Ebi-5. ES/MS: m/z=488.0 [M+H]+. $^1$H NMR (400 MHz, MeOD) δ 9.37-9.17 (m, 1H), 8.54 (d, J=5.9 Hz, 0.4H, minor rotamer), 8.45-8.23 (m, 1.6H), 7.71-7.28 (m, 2H), 7.10-6.68 (m, 2H), 6.06 (s, 1H), 4.54 (dd, J=13.9, 6.3 Hz, 0.4H, minor rotamer), 3.56-3.42 (m, 0.6H, major rotamer), 3.21-3.04 (m, 0.6H, major rotamer), 2.80 (t, J=14.0 Hz, 0.4H, minor rotamer), 2.51-1.85 (m, 4H), 1H overlapping with solvent.

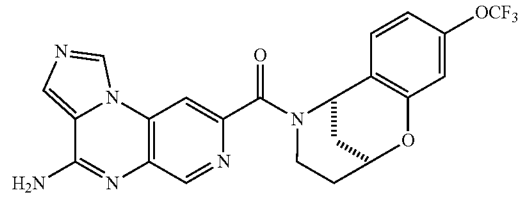

(±)

Example Ff-373: Rac-(4-aminoimidazo[1,5-a]pyrido[3,4-e]pyrazin-8-yl)((2S,6R)-9-(trifluoromethoxy)-3,4-dihydro-2H-2,6-methanobenzo[b][1,5]oxazocin-5(6H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and rac-(2S,6R)-9-(trifluoromethoxy)-3,4,5,6-tetrahydro-2H-2,6-methanobenzo[b][1,5]oxazocine Ebi-5. ES/MS: m/z=470.1 [M+H]+. $^1$H NMR (400 MHz, MeOD) δ 9.36 (s, 0.4H, minor rotamer), 9.29 (s, 0.6H, major rotamer), 8.94 (s, 0.4H, minor rotamer), 8.78 (s, 0.6H, major rotamer), 8.57 (s, 0.4H, minor rotamer), 8.44 (s, 0.6H, major rotamer), 8.30 (s, 0.4H, minor rotamer), 8.26 (s, 0.6H, major rotamer), 7.39 (d, J=8.4 Hz, 0.6H, major rotamer), 7.26 (d, J=8.2 Hz, 0.4H, minor rotamer), 6.92-6.72 (m, 2H), 6.03 (s, 0.6H, major rotamer), 5.35 (s, 0.4H, minor rotamer), 4.51 (dd, J=14.1, 6.3 Hz, 0.4H, minor rotamer), 3.89-3.80 (m, 0.6H, major rotamer), 3.16-3.06 (m, 0.6H, major rotamer), 2.83 (td, J=13.7, 4.1 Hz, 0.4H, minor rotamer), 2.50-2.30 (m, 1H), 2.30-2.17 (m, 1H), 2.04 (d, J=13.4 Hz, 2H), 1H overlapping with solvent.

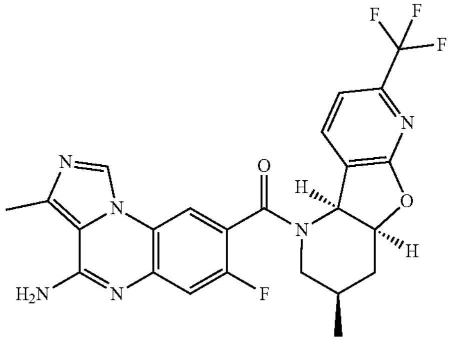 [SMILES: Cc1ncn2c1c(N)nc1cc(F)c(C(=O)N3C[C@H](C)C[C@@H]4Oc5nc(C(F)(F)F)ccc5[C@@H]43)cc12]

Example Ff-374: (4-amino-7-fluoro-3-methylimidazo[1,5-a]quinoxalin-8-yl)((3R,4aS,9bS)-3-methyl-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-fluoro-3-methylimidazo[1,5-a]quinoxaline-8-carboxylic acid Af-4 and (3R,4aS,9bS)-3-methyl-7-(trifluoromethyl)-1,2,3,4,4a,9b-hexahydrofuro[2,3-b:4,5-b']dipyridine hydrochloride Ew-15. ES/MS: m/z=501.0 [M+H]+. $^1$H NMR (400 MHz, MeOD) δ 9.28-9.03 (m, 1H), 8.48-8.39 (m, 1H), 7.96 (s, 1H), 7.51-7.42 (m, 2H), 6.47 (s, 0.8H, major rotamer), 5.66 (s, 0.2H, minor rotamer), 5.26 (td, J=8.4, 5.7 Hz, 0.8H, major rotamer), 5.10 (s, 0.2H, minor rotamer), 4.63 (d, J=13.3 Hz, 0.2H, minor rotamer), 3.57-3.45 (m, 0.8H, major rotamer), 2.80 (d, J=5.7 Hz, 3H), 2.75-2.60 (m, 1H), 2.34 (dt, J=14.5, 5.5 Hz, 1H), 2.10-1.81 (m, 1H), 1.54 (t, J=8.7 Hz, 1H), 1.04 (d, J=6.6 Hz, 0.6H, minor rotamer), 0.89 (d, J=6.7 Hz, 2.4H, major rotamer).

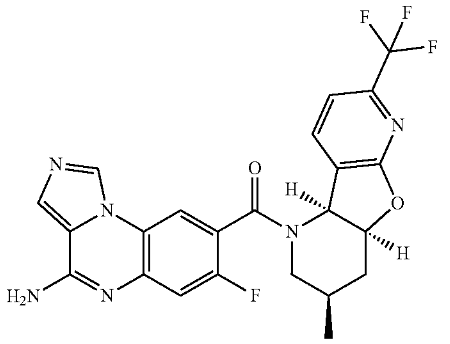 [SMILES: C[C@@H]1C[C@@H]2Oc3nc(C(F)(F)F)ccc3[C@@H]2N(C(=O)c2cc3c(cc2F)nc(N)c2cncn23)C1]

Example Ff-375: (4-amino-7-fluoroimidazo[1,5-a]quinoxalin-8-yl)((3R,4aS,9bS)-3-methyl-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and (3R,4aS,9bS)-3-methyl-7-(trifluoromethyl)-1,2,3,4,4a,9b-hexahydrofuro[2,3-b:4,5-b']dipyridine hydrochloride Ew-15. ES/MS: m/z=487.0 $[M+H]^+$. $^1H$ NMR (400 MHz, MeOD) δ 9.29-9.22 (m, 1H), 8.55-8.45 (m, 1H), 8.39-8.33 (m, 1H), 7.97 (s, 1H), 7.60-7.35 (m, 2H), 6.48 (s, 0.8H, major rotamer), 5.67 (d, J=8.1 Hz, 0.2H, minor rotamer), 5.27 (td, J=8.4, 5.8 Hz, 0.8H, major rotamer), 5.10 (s, 0.2H, minor rotamer), 4.64 (d, J=13.1 Hz, 0.2H, minor rotamer), 3.57-3.49 (m, 0.8H, major rotamer), 2.79-2.59 (m, 1H), 2.35 (dt, J=14.2, 5.5 Hz, 1H), 2.10-1.76 (m, 1H), 1.61-1.36 (m, 1H), 1.05 (d, J=6.7 Hz, 0.6H, minor rotamer), 0.89 (d, J=6.7 Hz, 2.4H, major rotamer).

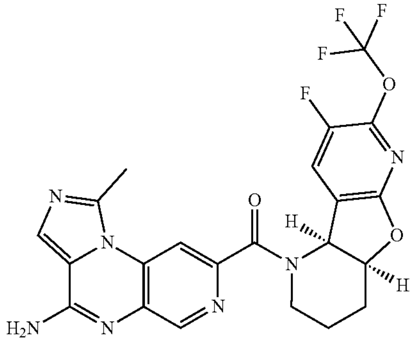 [SMILES: Cc1ncc2c(N)nc3cnc(C(=O)N4CCC[C@@H]5Oc6nc(OC(F)(F)F)c(F)cc6[C@@H]54)cc3n12]

Example Ff-376: (4-amino-1-methylimidazo[1,5-a]pyrido[3,4-e]pyrazin-8-yl)((4aS,9bS)-8-fluoro-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (4aS,9bS)-8-fluoro-7-(trifluoromethoxy)-1,2,3,4,4a,9b-hexahydrobenzofuro[3,2-b]pyridine hydrochloride Ew-16. ES/MS: m/z=503.0 $[M+H]^+$. $^1H$ NMR (400 MHz, MeOD) δ 8.84 (s, 1H), 8.63-8.40 (m, 1H), 8.22 (s, 1H), 7.78 (s, 0.4H, minor rotamer), 7.45 (s, 0.6H, major rotamer), 6.94 (s, 1H), 6.26 (s, 0.4H, minor rotamer), 6.05 (s, 0.6H, major rotamer), 5.18 (s, 0.6H, major rotamer), 5.01 (s, 0.4H, minor rotamer), 4.44 (s, 0.4H, minor rotamer), 3.89 (s, 0.6H, major rotamer), 3.17 (s, 3H), 3.10-2.73 (m, 1H), 2.31-1.65 (m, 4H).

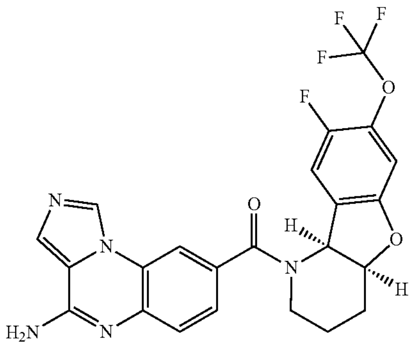 [SMILES: Nc1nc2ccc(C(=O)N3CCC[C@@H]4Oc5cc(OC(F)(F)F)c(F)cc5[C@@H]43)cc2n2cncc12]

Example Ff-377: (4-aminoimidazo[1,5-a]quinoxalin-8-yl)((4aS,9bS)-8-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (4aS,9bS)-8-fluoro-7-(trifluoromethoxy)-1,2,3,4,4a,9b-hexahydrobenzofuro[3,2-b]pyridine hydrochloride Ew-16. ES/MS: m/z=488.0 $[M+H]^+$. $^1H$ NMR (400 MHz, MeOD) δ 9.36 (d, J=0.7 Hz, 1H), 8.46 (s, 1H), 8.41 (d, J=0.7 Hz, 1H), 7.71 (s, 2H), 7.45 (d, J=9.0 Hz, 1H), 6.94 (d, J=5.9 Hz, 1H), 6.26 (s, 1H), 5.17 (s, 1H), 3.76-3.43 (m, 1H), 3.02 (s, 1H), 2.10 (s, 2H), 2.01-1.83 (m, 1H), 1.76 (s, 1H).

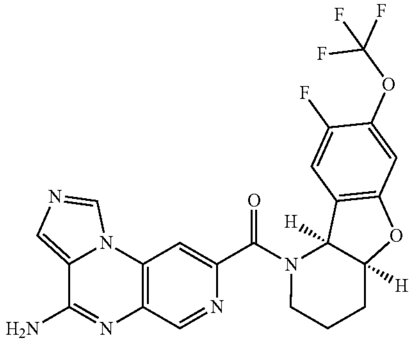 [SMILES: Nc1nc2cnc(C(=O)N3CCC[C@@H]4Oc5cc(OC(F)(F)F)c(F)cc5[C@@H]43)cc2n2cncc12]

Example Ff-378: (4-aminoimidazo[1,5-a]pyrido[3,4-e]pyrazin-8-yl)((4aS,9bS)-8-fluoro-7-(trifluoromethoxy)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (4aS,9bS)-8-fluoro-7-(trifluoromethoxy)-1,2,3,4,4a,9b-hexahydrobenzofuro[3,2-b]pyridine hydrochloride Ew-16. ES/MS: m/z=489.0 $[M+H]^+$. $^1H$ NMR (400 MHz, MeOD) δ 9.47-9.41 (m, 1H), 9.01-8.80 (m, 1H), 8.74-8.57 (m, 1H), 8.52-8.37 (m, 1H), 7.72 (d, J=9.2 Hz, 0.4H, minor rotamer), 7.43 (d, J=9.1 Hz, 0.6H, major rotamer), 6.98-6.90 (m, 1H), 6.28 (d, J=8.5 Hz, 0.6H, major rotamer), 5.92 (d, J=9.1 Hz, 0.4H, minor rotamer), 5.22-5.17 (m, 0.6H, major rotamer), 5.01-4.97 (m, 0.4H, minor rotamer), 4.50-4.14 (m, 1H), 3.06-2.74 (m, 1H), 2.31-1.66 (m, 4H).

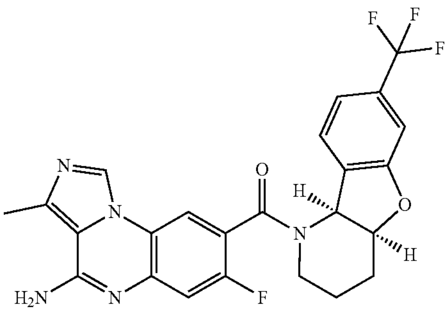

Example Ff-379: (4-amino-7-fluoro-3-methylimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoro-3-methylimidazo[1,5-a]quinoxaline-8-carboxylic acid Af-4 and (4aS,9bS)-7-(trifluoromethyl)-1,2,3,4,4a,9b-hexahydrobenzofuro[3,2-b]pyridine;hydrochloride Ew-1. ES/MS: m/z=486.0 $[M+H]^+$. $^1H$ NMR (400 MHz, MeOD) δ 9.19 (d, J=6.7 Hz, 1H), 8.66-8.29 (m, 1H), 7.67-7.41 (m, 2H), 7.36-7.21 (m, 1H), 7.20-7.04 (m, 1H), 6.45 (d, J=8.8 Hz, 0.8H, major rotamer), 5.65 (d, J=9.2 Hz, 0.2H, minor rotamer), 5.29-5.03 (m, 1H), 4.46 (d, J=9.7 Hz, 0.2H, minor rotamer), 3.62-3.39 (m, 0.8H, major rotamer), 3.13-2.94 (m, 1H), 2.80 (s, 3H), 2.20-1.98 (m, 2H), 1.93-1.63 (m, 2H).

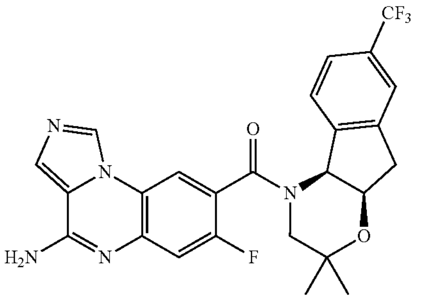 [SMILES: CC1(C)CN(C(=O)c2cc3c(cc2F)nc(N)c2cncn23)[C@H]2c3ccc(C(F)(F)F)cc3C[C@H]2O1]

Example Ff-380: (4-amino-7-fluoroimidazo[1,5-a]quinoxalin-8-yl)((4aS,9aR)-2,2-dimethyl-7-(trifluoromethyl)-2,3,9,9a-tetrahydroindeno[2,1-b][1,4]oxazin-4(4aH)-yl)methanone. Prepared according to general procedure VI-F starting with intermediate 4-(tert-butoxycarbonylamino)-7-fluoro-imidazo[1,5-a]quinoxaline-8-carboxylic acid Af-1 and (4aS,9aR)-2,2-dimethyl-7-(trifluoromethyl)-2,3,4,4a,9,9a-hexahydroindeno[2,1-b][1,4]oxazine hydrochloride Eby-3. EZ/MS: m/z=500.0 $[M+H]^+$. $^1H$ NMR (400 MHz, Methanol-d4) δ 9.37 (s, 1H), 8.60 (d, J=5.8 Hz, 0.4H rotamer), 8.55 (d, J=5.8 Hz, 0.6H rotamer), 8.44-8.32 (m, 1H), 7.70-7.43 (m, 4H), 6.09 (s, 0.6H rotamer), 5.03 (s, 0.4H rotamer), 4.81 (t, J=4.3 Hz, 0.6H rotamer), 4.74 (t, J=4.0 Hz, 0.4H rotamer), 4.38 (d, J=13.2 Hz, 0.4H, minor rotamer), 3.29-3.24 (m, 1H), 3.22 (d, J=13.3 Hz, 0.6H rotamer), 3.10-2.62 (m, 2H), 1.44 (s, 1.2H rotamer), 1.32 (s, 1.8H rotamer), 1.15 (s, 1.2H rotamer), 0.97 (s, 1.8H rotamer).

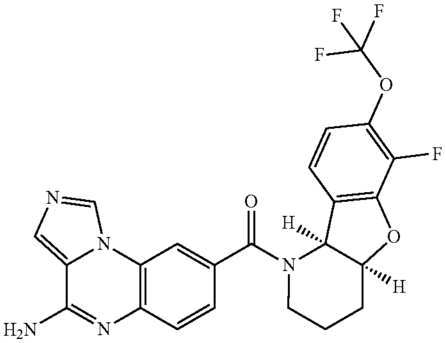 [SMILES: Nc1nc2ccc(C(=O)N3CCC[C@@H]4Oc5c(ccc(OC(F)(F)F)c5F)[C@@H]43)cc2n2cncc12]

Example Ff-381: (4-aminoimidazo[1,5-a]quinoxalin-8-yl)((4aS,9bS)-6-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (4aS,9bS)-6-fluoro-7-(trifluoromethoxy)-1,2,3,4,4a,9b-hexahydrobenzofuro[3,2-b]pyridine hydrochloride Ew-11. ES/MS: m/z=488.0 $[M+H]^+$. $^1H$ NMR (400 MHz, MeOD) δ 9.35 (d, J=0.7 Hz, 1H), 8.50-8.28 (m, 2H), 7.76-7.66 (m, 2H), 7.33 (d, J=8.4 Hz, 1H), 7.02 (ddd, J=8.2, 6.3, 1.3 Hz, 1H), 6.32 (s, 1H), 5.28 (s, 1H), 3.75-3.51 (m, 1H), 3.19-2.86 (m, 1H), 2.35-2.04 (m, 2H), 2.02-1.83 (m, 1H), 1.83-1.68 (m, 1H).

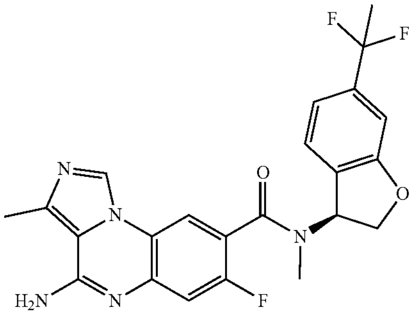 [SMILES: Cc1ncn2c1c(N)nc1cc(F)c(C(=O)N(C)[C@@H]3COc4cc(C(C)(F)F)ccc43)cc12]

Example Ff-382: (S)-4-amino-N-(6-(1,1-difluoroethyl)-2,3-dihydrobenzofuran-3-yl)-7-fluoro-N,3-dimethylimidazo[1,5-a]quinoxaline-8-carboxamide. Prepared following general procedure VI-F starting with 4-((tert-butoxycarbonyl)amino)-7-fluoro-3-methylimidazo[1,5-a]quinoxaline-8-carboxylic acid Af-4 and (S)-6-(1,1-difluoroethyl)-N-methyl-2,3-dihydrobenzofuran-3-amine Eae-1. ES/MS: m/z=456.0 $[M+H]^+$. $^1H$ NMR (400 MHz, MeOD) δ 9.15 (s, 1H), 8.37 (d, J=5.8 Hz, 1H), 7.59-7.36 (m, 2H), 7.31-7.14 (m, 1H), 7.07 (s, 0.6H, major rotamer), 7.01 (s, 0.4H, minor rotamer), 6.53 (d, J=5.8 Hz, 0.4H, minor rotamer), 5.62 (s, 0.6H, major rotamer), 4.86-4.79 (m, 1H), 4.68 (dd, J=10.7, 3.6 Hz, 1H), 2.91-2.80 (m, 3H), 2.71 (d, J=1.2 Hz, 1.8H, major rotamer), 2.68 (s, 1.2H, minor rotamer), 2.00-1.83 (m, 3H).

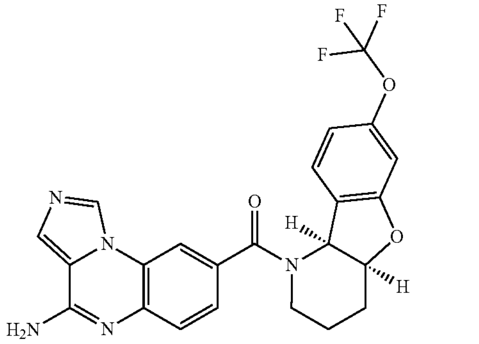 [SMILES: Nc1nc2ccc(C(=O)N3CCC[C@@H]4Oc5cc(OC(F)(F)F)ccc5[C@@H]43)cc2n2cncc12]

Example Ff-383: (4-aminoimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (4aS,9bS)-7-(trifluoromethoxy)-1,2,3,4,4a,9b-hexahydrobenzofuro[3,2-b]pyridine hydrochloride Ew-12. ES/MS: m/z=470.0 $[M+H]^+$. $^1H$ NMR (400 MHz, MeOD) δ 9.36 (d, J=0.7 Hz, 1H), 8.47-8.39 (m, 2H), 7.76-7.69 (m, 2H), 7.52 (d, J=8.4 Hz, 1H), 6.90 (d, J=8.2 Hz, 1H), 6.79 (s, 1H), 6.27 (s, 1H), 5.17 (s, 1H), 3.76-3.44 (m, 1H), 3.09-2.80 (m, 1H), 2.10 (s, 2H), 1.98-1.85 (m, 1H), 1.76 (s, 1H).

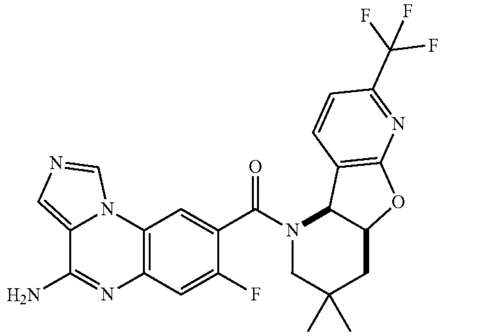

(±)

Example Ff-384: Rac-(4-amino-7-fluoroimidazo[1,5-a]quinoxalin-8-yl)((4aS,9bS)-3,3-dimethyl-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,9bS)-3,3-dimethyl-7-(trifluoromethyl)-1,2,3,4,4a,9b-hexahydrofuro[2,3-b:4,5-b']dipyridine hydrochloride Eba-5. ES/MS: m/z=501.0 $[M+H]^+$. $^1H$ NMR (400 MHz, MeOD) δ 9.29 (s, 1H), 8.62-8.41 (m, 1H), 8.38 (d, J=3.0 Hz, 1H), 7.99 (s, 1H), 7.66-7.33 (m, 2H), 6.54 (d, J=8.6 Hz, 0.7H, major rotamer), 5.65 (d, J=8.4 Hz, 0.3H, minor rotamer), 5.33 (td, J=8.2, 5.6 Hz, 0.7H, major rotamer), 5.21 (s, 0.3H, minor rotamer), 4.41 (d, J=13.4 Hz, 0.3H, minor rotamer), 3.21 (d, J=13.6 Hz, 0.7, major rotamer H), 2.96 (d, J=13.6 Hz, 1H), 2.04 (td, J=13.7, 5.6 Hz, 1H), 1.74 (dd, J=14.3, 7.9 Hz, 1H), 1.16 (s, 0.9H, minor rotamer), 1.08 (s, 0.9H, minor rotamer), 0.99 (s, 2.1H, major rotamer), 0.91 (s, 2.1H, major rotamer).

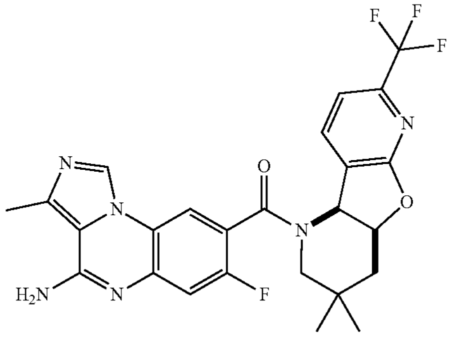

(±)

Example Ff-385: Rac-(4-amino-7-fluoro-3-methylimidazo[1,5-a]quinoxalin-8-yl)((4aS,9bS)-3,3-dimethyl-7-(trifluoromethyl)-3,4,4a,9b-tetrahydrofuro[2,3-b:4,5-b']dipyridin-1(2H)-yl)methanone. Prepared following general procedure VI-F starting with 4-((tert-butoxycarbonyl)amino)-7-fluoro-3-methylimidazo[1,5-a]quinoxaline-8-carboxylic acid Af-4 and rac-(4aS,9bS)-3,3-dimethyl-7-(trifluoromethyl)-1,2,3,4,4a,9b-hexahydrofuro[2,3-b:4,5-b']dipyridine hydrochloride Eba-5. ES/MS: m/z=515.0 $[M+H]^+$. $^1H$ NMR (400 MHz, MeOD) δ 9.18 (s, 1H), 8.60-8.32 (m, 1H), 7.98 (s, 1H), 7.61-7.35 (m, 2H), 6.54 (d, J=8.6 Hz, 0.7H, major rotamer), 5.64 (s, 0.3H, minor rotamer), 5.41-5.10 (m, 1H), 4.40 (d, J=13.3 Hz, 0.3H, minor rotamer), 3.18 (t, J=13.2 Hz, 0.7H, major rotamer), 2.95 (d, J=13.6 Hz, 0.7H, major rotamer), 2.80 (d, J=2.6 Hz, 3H), 2.55 (d, J=13.5 Hz, 0.3H, minor rotamer), 2.03 (dd, J=14.1, 5.7 Hz, 1H), 1.74 (dd, J=14.3, 7.9 Hz, 1H), 1.16 (s, 0.9H, minor rotamer), 1.08 (s, 0.9H, minor rotamer), 0.99 (s, 2.1H, major rotamer), 0.91 (s, 2.1H, major rotamer).

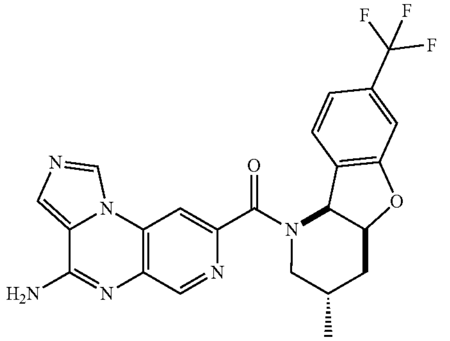

Example Ff-386: (4-aminoimidazo[1,5-a]pyrido[3,4-e]pyrazin-8-yl)((3S)-3-methyl-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and cis-(3S)-3-methyl-7-(trifluoromethyl)-1,2,3,4,4a,9b-hexahydrobenzofuro[3,2-b]pyridine hydrochloride Eba-6. ES/MS: m/z=469.0 $[M+H]^+$. $^1H$ NMR (400 MHz, MeOD) δ 9.36 (s, 1H), 8.83 (d, J=13.2 Hz, 1H), 8.68-8.50 (m, 1H), 8.33 (s, 1H), 7.86 (d, J=7.7 Hz, 0.5H, isomer A), 7.60 (d, J=7.8 Hz, 0.5H, isomer B), 7.30 (q, J=8.6 Hz, 1H), 7.17-7.06 (m, 1H), 6.51-6.27 (m, 0.5H, isomer A), 6.11-5.91 (m, 0.5H, isomer B), 5.37-4.91 (m, 1H), 4.09-3.70 (m, 1H), 2.62-1.92 (m, 3H), 1.76-1.46 (m, 1H), 1.28-0.78 (m, 3H).

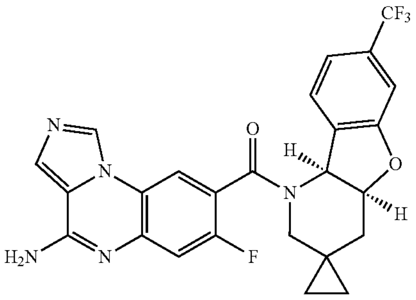 [SMILES: Nc1nc2cc(F)c(C(=O)N3CC4(CC4)C[C@@H]4Oc5cc(C(F)(F)F)ccc5[C@@H]43)cc2n2cncc12]

Example Ff-387: (4-amino-7-fluoroimidazo[1,5-a]quinoxalin-8-yl)((4a'S,9a'R)-7'-(trifluoromethyl)-9',9a'-dihydro-3'H-spiro[cyclopropane-1,2'-indeno[2,1-b][1,4]oxazin]-4'(4a'H)-yl)methanone. Prepared following general procedure VI-F starting with 4-(tert-butoxycarbonylamino)-7-fluoro-imidazo[1,5-a]quinoxaline-8-carboxylic acid Af-1 and (4a'S,9a'R)-7'-(trifluoromethyl)-4',4a',9',9a'-tetrahydro-3'H-spiro[cyclopropane-1,2'-indeno[2,1-b][1,4]oxazine] Eby-1. ES/MS: m/z=498.0 $[M+H]^+$. $^1H$ NMR (400 MHz, Methanol-$d_4$) δ 9.32 (s, 1H), 8.58 (d, J=5.9 Hz, 0.3H, minor rotamer), 8.53 (d, J=5.9 Hz, 0.7H, major rotamer), 8.35 (s, 0.7H, major rotamer), 8.32 (s, 0.3H, minor rotamer), 7.77-7.39 (m, 4H), 6.15 (s, 0.7H, major rotamer), 5.16 (s, 0.3H, minor rotamer), 4.66 (t, J=4.1 Hz, 0.7H, major rotamer), 4.60 (t, J=3.8 Hz, 0.3H, minor rotamer), 4.03 (d, J=13.5 Hz, 0.3H, minor rotamer), 3.75 (d, J=13.5 Hz, 0.7H, major rotamer), 3.50-3.34 (m, 0.7H, major rotamer), 3.11-3.01 (m, 0.3H, minor rotamer), 3.01-2.80 (m, 2H), 1.01-0.31 (m, 4H).

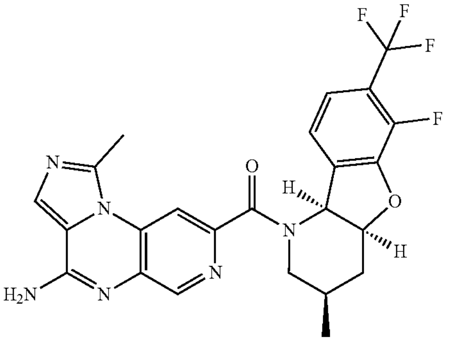 [SMILES: Cc1ncc2c(N)nc3cnc(C(=O)N4C[C@H](C)C[C@@H]5Oc6c(ccc(C(F)(F)F)c6F)[C@@H]54)cc3n12]

Example Ff-388: (4-amino-1-methylimidazo[1,5-a]pyrido[3,4-e]pyrazin-8-yl)((3R,4aS,9bS)-6-fluoro-3-methyl-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (3R,4aS,9bS)-6-fluoro-3-methyl-7-(trifluoromethyl)-1,2,3,4,4a,9b-hexahydrobenzofuro[3,2-b]pyridine hydrochloride Ew-17. ES/MS: m/z=501.0 $[M+H]^+$. $^1H$ NMR (400 MHz, MeOD) δ 8.88-8.74 (m, 1H), 8.60-8.42 (m, 1H), 8.25 (s, 1H), 7.72 (d, J=7.9 Hz, 0.4H, minor rotamer), 7.41 (d, J=7.9 Hz, 0.6H, minor rotamer), 7.31 (dt, J=13.4, 6.8 Hz, 1H), 6.38 (d, J=8.4 Hz, 0.6H, minor rotamer), 6.13 (d, J=8.3 Hz, 0.4H, major rotamer), 5.28 (d, J=6.6 Hz, 0.6H, major rotamer), 5.07 (d, J=7.1 Hz, 0.4H, minor rotamer), 4.56 (d, J=13.3 Hz, 0.4H, minor rotamer), 4.13-3.85 (m, 0.6H, major rotamer), 3.16 (s, 3H), 2.58 (t, J=12.3 Hz, 0.6H, major rotamer), 2.42-2.15 (m, 2H), 2.13-1.95 (m, 0.4H, minor rotamer), 1.83-1.49 (m, 1H), 1.17-0.89 (m, 3H).

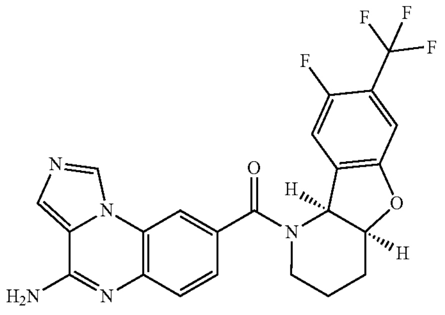 [SMILES: Nc1nc2ccc(C(=O)N3CCC[C@@H]4Oc5cc(C(F)(F)F)c(F)cc5[C@@H]43)cc2n2cncc12]

Example Ff-389: (4-aminoimidazo[1,5-a]quinoxalin-8-yl)((4aS,9bS)-8-fluoro-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (4aS,9bS)-8-fluoro-7-(trifluoromethyl)-1,2,3,4,4a,9b-hexahydrobenzofuro[3,2-b]pyridine hydrochloride Ew-2 ES/MS: m/z=472.0 $[M+H]^+$. $^1H$ NMR (400 MHz, MeOD) δ 9.36 (d, J=0.7 Hz, 1H), 8.46 (s, 1H), 8.42 (d, J=0.6 Hz, 1H), 7.79-7.65 (m, 2H), 7.45 (d, J=9.4 Hz, 1H), 7.14 (d, J=5.3 Hz, 1H), 6.33 (s, 1H), 5.18 (s, 1H), 3.77-3.47 (m, 1H), 3.02 (s, 1H), 2.10 (s, 2H), 1.94-1.82 (m, 1H), 1.82-1.64 (m, 1H).

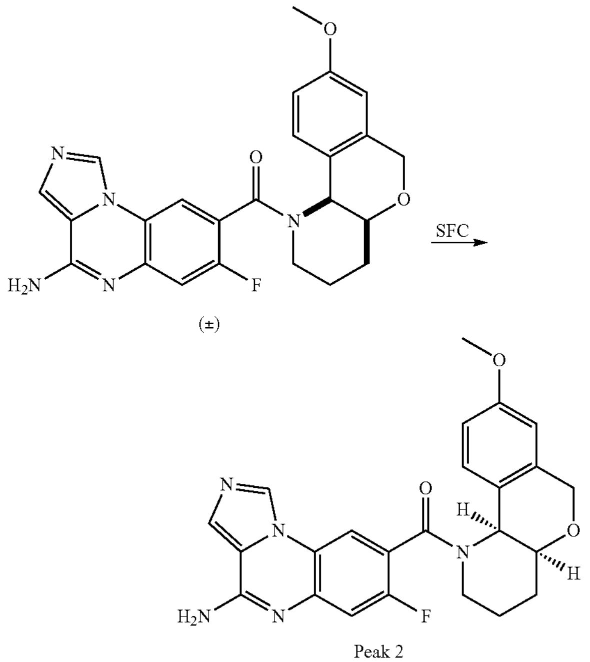

Peak 2
Example Ff-390

Rac-(4-amino-7-fluoroimidazo[1,5-a]quinoxalin-8-yl)((4aS,10bS)-8-methoxy-2,3,4,4a,6,10b-hexahydro-1H-isochromeno[4,3-b]pyridin-1-yl)methanone prepared following general procedure VI-F starting with 4-((tert-butoxycarbonyl)amino)-7-fluoroimidazo[1,5-a]quinoxaline-8-carboxylic acid Af-1 and Rac-(4aS,10bS)-8-methoxy-2,3,4,4a,6,10b-hexahydro-1H-isochromeno[4,3-b]

pyridine El-1 was subjected to supercritical fluid chromatography (AD-H 4.6×100 mm column, 45% EtOH, 3 mL/min, 100 bar, 40° C.).

Example Ff-390: (4-amino-7-fluoroimidazo[1,5-a]quinoxalin-8-yl)((4aS,10bS)-8-methoxy-2,3,4,4a,6,10b-hexahydro-1H-isochromeno[4,3-b]pyridin-1-yl)methanone. (Peak 2, RT=6.6 min). ES/MS: m/z=448.0 $[M+H]^+$. $^1H$ NMR (400 MHz, MeOD) δ 9.30 (s, 1H), 8.52 (s, 1H), 8.37 (s, 1H), 7.48 (d, J=9.7 Hz, 1H), 7.29 (s, 1H), 6.92 (d, J=8.5 Hz, 1H), 6.80-6.55 (m, 1H), 6.03 (s, 1H), 4.81-4.46 (m, 1H), 4.20 (s, 1H), 3.90-3.70 (m, 3H), 3.43-3.35 (m, 1H), 3.10-2.86 (m, 1H), 2.73-2.48 (m, 1H), 2.02-1.55 (m, 4H).

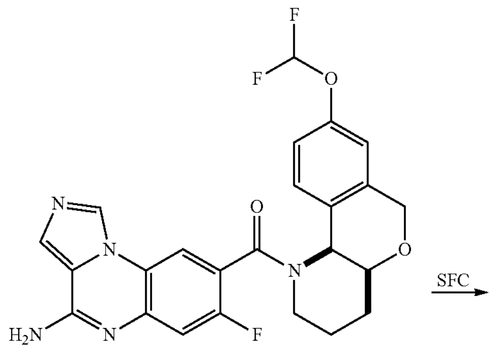

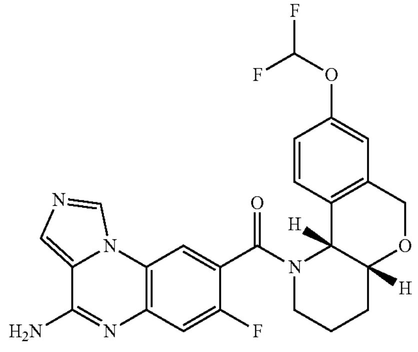

Peak 1
Example Ff-391

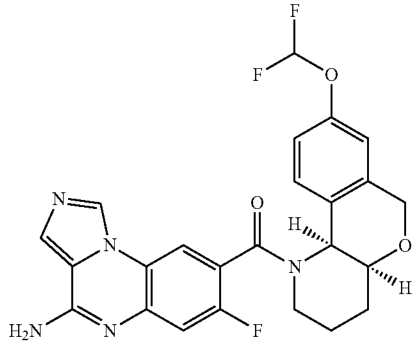

Peak 2
Example Ff-392

Rac-(4-amino-7-fluoroimidazo[1,5-a]quinoxalin-8-yl)((4aS,10bS)-8-(difluoromethoxy)-2,3,4,4a,6,10b-hexahydro-1H-isochromeno[4,3-b]pyridin-1-yl)methanone prepared following general procedure VI-F starting with 4-((tert-butoxycarbonyl)amino)-7-fluoroimidazo[1,5-a]quinoxaline-8-carboxylic acid Af-1 and rac-(4aS,10bS)-8-(difluoromethoxy)-2,3,4,4a,6,10b-hexahydro-1H-isochromeno[4,3-b]pyridine hydrochloride Ebc-1 was subjected to supercritical fluid chromatography (IG 4.6×100 mm column, 50% MeOH).

Example Ff-391: (4-amino-7-fluoroimidazo[1,5-a]quinoxalin-8-yl)((4aR,10bR)-8-(difluoromethoxy)-2,3,4,4a,6,10b-hexahydro-1H-isochromeno[4,3-b]pyridin-1-yl)methanone (Peak 1, RT=7.9 min). ES/MS: m/z=484.0 $[M+H]^+$. $^1H$ NMR (400 MHz, MeOD) δ 9.31 (s, 1H), 8.53 (s, 1H), 8.39 (d, J=11.0 Hz, 1H), 7.60-7.30 (m, 2H), 7.13 (dd, J=8.5, 2.5 Hz, 1H), 7.07-6.59 (m, 2H), 6.05 (s, 1H), 4.94 (d, J=16.0 Hz, 1H), 4.84-4.48 (m, 1H), 4.22 (dt, J=11.3, 6.2 Hz, 1H), 3.41 (d, J=13.9 Hz, 1H), 2.99-2.49 (m, 1H), 2.01-1.57 (m, 4H).

Example Ff-392: (4-amino-7-fluoroimidazo[1,5-a]quinoxalin-8-yl)((4aS,10bS)-8-(difluoromethoxy)-2,3,4,4a,6,10b-hexahydro-1H-isochromeno[4,3-b]pyridin-1-yl)methanone (Peak 2, RT=10.6 min) ES/MS: m/z=484.0 $[M+H]^+$. $^1H$ NMR (400 MHz, MeOD) δ 9.30 (s, 1H), 8.53 (s, 1H), 8.38 (d, J=11.0 Hz, 1H), 7.59-7.30 (m, 2H), 7.13 (dd, J=8.5, 2.5 Hz, 1H), 7.07-6.59 (m, 2H), 6.05 (s, 1H), 4.94 (d, J=16.0 Hz, 1H), 4.84-4.48 (m, 1H), 4.22 (dt, J=11.3, 6.2 Hz, 1H), 3.40 (d, J=13.9 Hz, 1H), 2.99-2.49 (m, 1H), 2.01-1.56 (m, 4H).

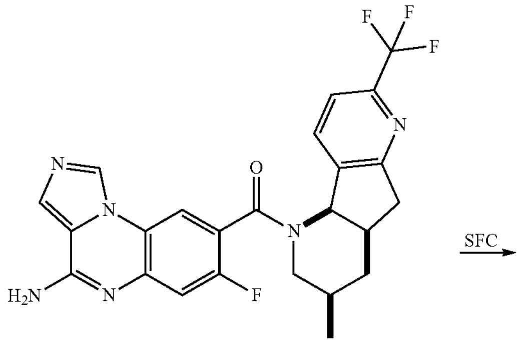

(±)
Example Ff-321

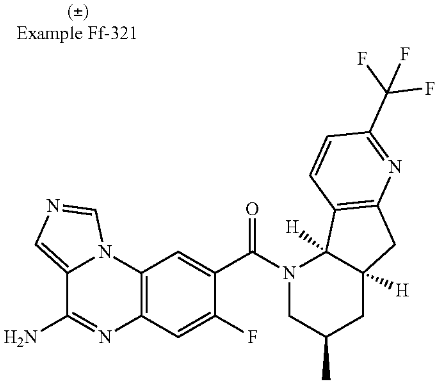

Peak 2
Example Ff-393

Rac-(4-amino-7-fluoroimidazo[1,5-a]quinoxalin-8-yl)((4bR,7R,8aR)-7-methyl-2-(trifluoromethyl)-4b,6,7,8,8a,9-hexahydro-5H-cyclopenta[1,2-b:3,4-b']dipyridin-5-yl)methanone (example Ff-321) was subjected to supercritical fluid chromatography (AD-H 4.6×100 mm column, 50% MeOH). Example Ff-393: (4-amino-7-fluoroimidazo[1,5-a]quinoxalin-8-yl)((4bR,7R,8aR)-7-methyl-2-(trifluoromethyl)-4b,6,7,8,8a,9-hexahydro-5H-cyclopenta[1,2-b:3,4-b']dipyridin-5-yl)methanone. (Peak 2, RT=3.35 min) ES/MS: m/z=485.0 $[M+H]^+$. $^1H$ NMR (400 MHz, MeOD) δ 9.31 (s, 1H), 8.52 (d, J=5.9 Hz, 1H), 8.43-8.32 (m, 1H), 8.20-7.62

(m, 2H), 7.58-7.27 (m, 1H), 6.33 (s, 0.8H, major rotamer), 5.29 (s, 0.2H, minor rotamer), 4.64 (d, J=13.1 Hz, 0.2H, minor rotamer), 3.56-3.36 (m, 0.8H, major rotamer), 3.21-2.45 (m, 3.8H), 2.29 (t, J=12.4 Hz, 0.2H, minor rotamer), 1.94 (d, J=8.5 Hz, 1H), 1.77 (s, 1H), 0.93 (d, J=6.6 Hz, 1H), 0.90-0.59 (m, 3H).

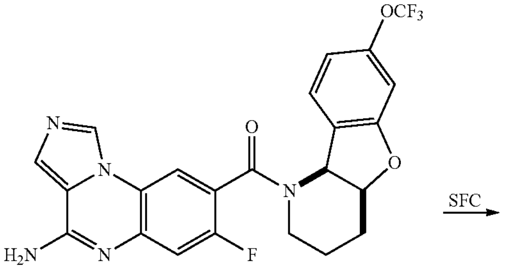

Example Ff-331

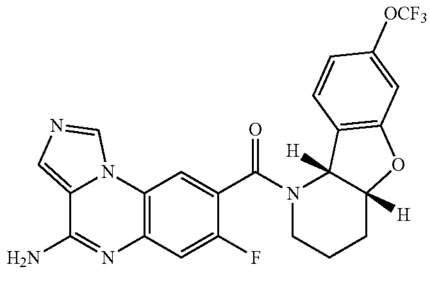

Peak 1
Example Ff-394

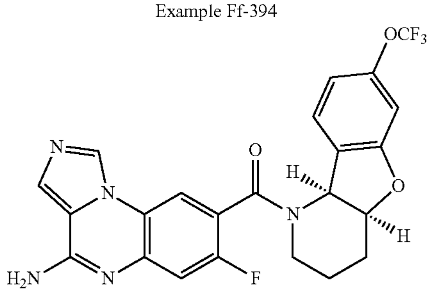

Peak 2
Example Ff-395

Rac-(4-amino-7-fluoroimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone (example Ff-331) was subjected to supercritical fluid chromatography (AD 4.6×100 mm column, 40% MeOH).

Example Ff-394: (4-amino-7-fluoroimidazo[1,5-a]quinoxalin-8-yl)((4aR,9bR)-7-(trifluoromethoxy)-3,4,4a,9b-tetrahydrobenzofuro[3,2-b]pyridin-1(2H)-yl)methanone (Peak 1, RT=2.31 min) ES/MS: m/z=488.0 $[M+H]^+$. $^1H$ NMR (400 MHz, MeOD) δ 9.39-9.19 (m, 1H), 8.65-8.27 (m, 2H), 7.61-7.22 (m, 2H), 7.03-6.66 (m, 2H), 6.38 (d, J=8.8 Hz, 0.8H, major rotamer), 5.58 (d, J=9.1 Hz, 0.2H, minor rotamer), 5.19 (dt, J=8.6, 4.2 Hz, 1H), 3.45 (dd, J=12.3, 7.9 Hz, 1H), 3.04 (dt, J=15.1, 8.3 Hz, 0.8H, major rotamer), 2.85 (dt, J=13.7, 6.9 Hz, 0.2H, minor rotamer), 2.23-1.59 (m, 4H).

Example Ff-395: (4-amino-7-fluoroimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone (Peak 2, RT=3.49 min) ES/MS: m/z=488.0 $[M+H]^+$. $^1H$ NMR (400 MHz, MeOD) δ 9.39-9.19 (m, 1H), 8.65-8.27 (m, 2H), 7.61-7.22 (m, 2H), 7.03-6.66 (m, 2H), 6.38 (d, J=8.8 Hz, 0.8H, major rotamer), 5.58 (d, J=9.1 Hz, 0.2H, minor rotamer), 5.19 (dt, J=8.6, 4.2 Hz, 1H), 3.45 (dd, J=12.3, 7.9 Hz, 1H), 3.04 (dt, J=15.1, 8.3 Hz, 0.8H, major rotamer), 2.85 (dt, J=13.7, 6.9 Hz, 0.2H, minor rotamer), 2.23-1.59 (m, 4H).

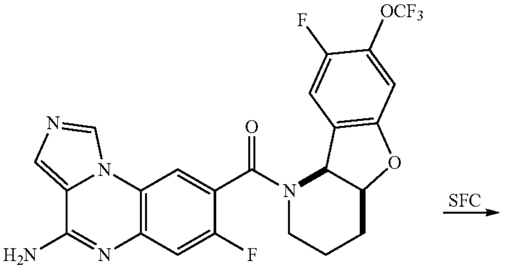

Example Ff-333

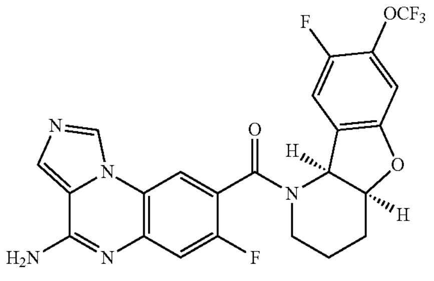

Peak 1
Example Ff-396

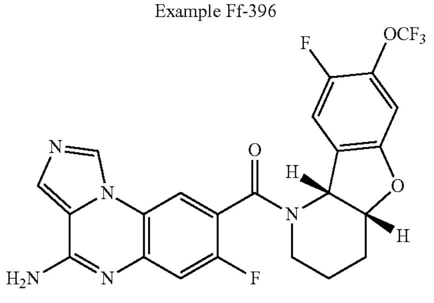

Peak 2
Example Ff-397

Rac-(4-amino-7-fluoroimidazo[1,5-a]quinoxalin-8-yl)((4aS,9bS)-8-fluoro-7-(trifluoromethoxy)-3,4,4a,9b-tetrahydrobenzofuro[3,2-b]pyridin-1(2H)-yl)methanone (example Ff-333) was subjected to supercritical fluid chromatography (AD 4.6×100 mm column, 50% MeOH).

Example Ff-396: (4-amino-7-fluoroimidazo[1,5-a]quinoxalin-8-yl)((4aS,9bS)-8-fluoro-7-(trifluoromethoxy)-3,4,4a,9b-tetrahydrobenzofuro[3,2-b]pyridin-1(2H)-yl)methanone (Peak 1, RT=1.32 min). ES/MS: m/z=506.0 $[M+H]^+$. $^1H$ NMR (400 MHz, MeOD) δ 9.06 (s, 1H), 8.45-8.15 (m, 1H), 7.97 (s, 1H), 7.60-7.18 (m, 2H), 7.04-6.73 (m, 1H), 6.37 (d, J=8.7 Hz, 0.7H, major rotamer), 5.64 (d, J=9.0 Hz, 0.3H, minor rotamer), 5.34-5.04 (m, 1H), 4.45 (s, 0.3H, minor rotamer), 3.61-3.42 (m, 0.7H, major rotamer), 3.14-2.70 (m, 1H), 2.23-1.57 (m, 4H).

Example Ff-397: (4-amino-7-fluoroimidazo[1,5-a]quinoxalin-8-yl)((4aR,9bR)-8-fluoro-7-(trifluoromethoxy)-3,4,4a,9b-tetrahydrobenzofuro[3,2-b]pyridin-1(2H)-yl)methanone (Peak 2, RT=1.98 min). ES/MS: m/z=506.0 $[M+H]^+$. $^1H$ NMR (400 MHz, MeOD) δ 9.06 (s, 1H), 8.45-8.15 (m, 1H), 7.97 (s, 1H), 7.60-7.18 (m, 2H), 7.03-6.75 (m, 1H), 6.37 (d, J=8.7 Hz, 0.7H, major rotamer), 5.64 (d, J=9.0 Hz, 0.3H, minor rotamer), 5.33-5.04 (m, 1H), 4.45 (s, 0.3H, minor rotamer), 3.61-3.42 (m, 0.7H, major rotamer), 3.14-2.71 (m, 1H), 2.23-1.57 (m, 4H).

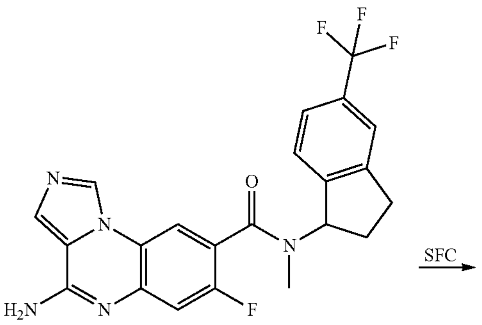

Example Ff-309

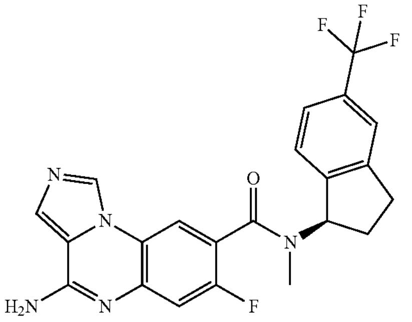

Peak 1
Example Ff-398

4-amino-7-fluoro-N-methyl-N-(5-(trifluoromethyl)-2,3-dihydro-1H-inden-1-yl)imidazo[1,5-a]quinoxaline-8-carboxamide (Example Ff-309) was subjected to supercritical fluid chromatography (AZ-H 4.6×100 mm column, 40% MeOH).

Example Ff-398: (R)-4-amino-7-fluoro-N-methyl-N-(5-(trifluoromethyl)-2,3-dihydro-1H-inden-1-yl)imidazo[1,5-a]quinoxaline-8-carboxamide (Peak 1, RT=4.91 min). ES/MS: m/z=444.0 $[M+H]^+$. $^1H$ NMR (400 MHz, MeOD) δ 9.11 (d, J=6.9 Hz, 1H), 8.34 (d, J=6.2 Hz, 1H), 8.06 (d, J=3.9 Hz, 1H), 7.66-7.55 (m, 2H), 7.49 (d, J=7.9 Hz, 1H), 7.35 (d, J=10.8 Hz, 1H), 6.43 (t, J=8.1 Hz, 0.4H, minor rotamer), 5.43 (t, J=8.3 Hz, 0.6H, major rotamer), 3.25-3.01 (m, 2H), 2.88 (s, 1.8H, major rotamer), 2.76 (d, J=1.2 Hz, 1.2H, minor rotamer), 2.71-2.15 (m, 2H).

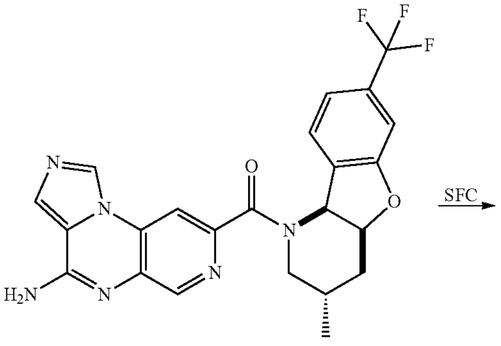

Example Ff-386

-continued

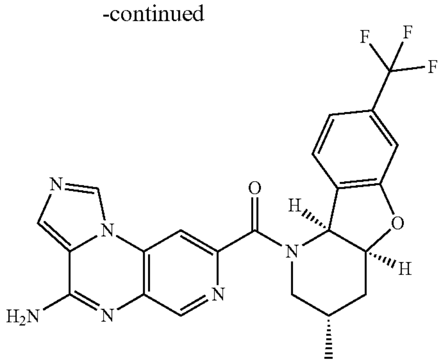

Peak 2
Example Ff-399

(4-aminoimidazo[1,5-a]pyrido[3,4-e]pyrazin-8-yl)((3S)-3-methyl-7-(trifluoromethyl)-3,4,4a,9b-tetrahydrobenzofuro[3,2-b]pyridin-1(2H)-yl)methanone (example Ff-386) was subjected to supercritical fluid chromatography (IK 4.6×100 mm column, 50% MeOH).

Example Ff-399: (4-aminoimidazo[1,5-a]pyrido[3,4-e]pyrazin-8-yl)((3S,4aS,9bS)-3-methyl-7-(trifluoromethyl)-3,4,4a,9b-tetrahydrobenzofuro[3,2-b]pyridin-1(2H)-yl)methanone (Peak 2, RT=4.22 min). ES/MS: m/z=469.0 $[M+H]^+$. $^1H$ NMR (400 MHz, MeOD) δ 9.36 (s, 1H), 8.93-8.79 (m, 1H), 8.68-8.45 (m, 1H), 8.30 (s, 1H), 7.85 (s, 0.6H, major rotamer), 7.65 (s, 0.4H, minor rotamer), 7.28 (d, J=7.8 Hz, 1H), 7.19-7.03 (m, 1H), 6.44 (s, 0.4H, minor rotamer), 6.05 (s, 0.6H, major rotamer), 5.38-5.06 (m, 1H), 4.12-3.90 (m, 1H), 3.42-3.38 (m, 0.4H, minor rotamer), 3.08-2.93 (m, 0.6H, major rotamer), 2.32-1.97 (m, 2H), 1.65 (s, 1H), 1.20-0.87 (m, 3H).

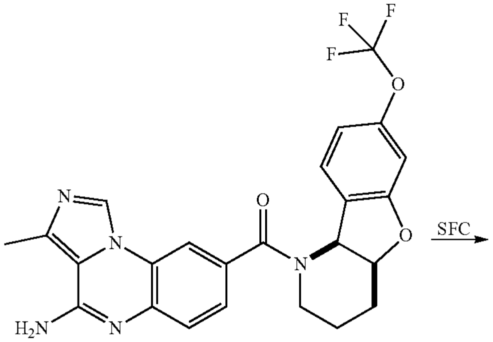

Example Ff-332

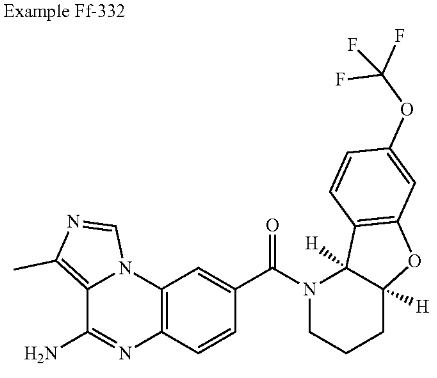

Peak 2
Example Ff-400

Rac-(4-amino-3-methylimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone (example Ff-332) was subjected to supercritical fluid chromatography (AD-H 4.6×100 mm column, 35% MeOH).

Example Ff-400: (4-amino-3-methylimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone (Peak 2, RT=6.71 min). ES/MS: m/z=484.0 $[M+H]^+$. $^1$H NMR (400 MHz, MeOD) δ 9.25 (s, 1H), 8.38 (s, 1H), 7.68 (s, 2H), 7.52 (d, J=8.2 Hz, 1H), 6.91 (d, J=8.2 Hz, 1H), 6.80 (s, 1H), 6.27 (s, 1H), 5.17 (s, 1H), 3.81-3.42 (m, 1H), 3.08-2.89 (m, 1H), 2.82 (s, 3H), 2.24-2.00 (m, 2H), 1.98-1.84 (m, 1H), 1.84-1.61 (m, 1H).

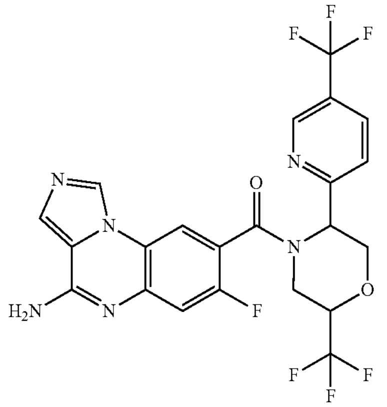 [SMILES: Nc1nc2cc(F)c(C(=O)N3CC(C(F)(F)F)OCC3c3ccc(C(F)(F)F)cn3)cc2n2cncc12]

Example Ff-401: (4-aminoimidazo[1,5-a]quinoxalin-8-yl)(2-(trifluoromethyl)-5-(5-(trifluoromethyl)pyridin-2-yl)morpholino)methanone. Prepared using general procedure VI-F starting with 4-(tert-butoxycarbonylamino)-7-fluoro-imidazo[1,5-a]quinoxaline-8-carboxylic acid Af-1 and 2-(trifluoromethyl)-5-(5-(trifluoromethyl)pyridin-2-yl)morpholine hydrochloride Eai-19. ES/MS: m/z=529.3 $[M+H]^+$. $^1$H NMR (400 MHz, MeOD) δ 9.27 (s, 0.5H major rotamer), 9.16 (s, 0.5H minor rotamer), 8.99 (d, J=7.4 Hz, 1H), 8.49 (d, J=5.9 Hz, 0.6H major rotamer), 8.42 (d, J=5.8 Hz, 0.4H minor rotamer), 8.34 (s, 0.5H major rotamer), 8.30 (s, 0.5H minor rotamer), 8.25-8.17 (m, 0.5H major rotamer), 8.13 (d, J=8.0 Hz, 0.5H minor rotamer), 7.79 (d, J=8.4 Hz, 0.5H major rotamer), 7.68 (d, J=8.4 Hz, 0.5H minor rotamer), 7.52 (d, J=10.0 Hz, 0.5H major rotamer), 7.40 (d, J=9.9 Hz, 0.5H minor rotamer), 5.92 (s, 1H), 5.12-4.93 (m, 1H), 4.83 (s, 0.5H), 4.71 (d, J=13.5 Hz, 1H), 4.36 (dd, J=12.8, 7.7 Hz, 1H), 4.23 (td, J=12.6, 3.8 Hz, 1H), 3.75 (d, J=8.1 Hz, 1H).

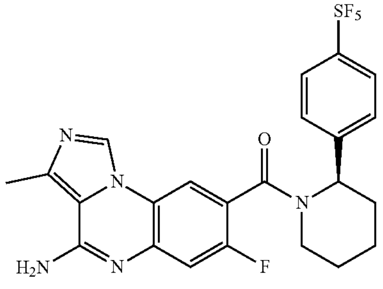

Example Ff-402: (R)-(4-amino-7-fluoro-3-methylimidazo[1,5-a]quinoxalin-8-yl)(2-(4-(pentafluoro-16-sulfaneyl)phenyl)piperidin-1-yl)methanone. Prepared using general procedure VI-F starting with 4-((tert-butoxycarbonyl)amino)-7-fluoro-3-methylimidazo[1,5-a]quinoxaline-8-carboxylic acid Af-4 and (R)-2-(4-(pentafluoro-6-sulfaneyl)phenyl)piperidine Ebl-1. ES/MS: m/z=530.0 $[M+H]^+$. $^1$H NMR (400 MHz, methanol-d4) δ 9.21 (s, 1H), 8.44 (d, J=5.8 Hz, 1H), 7.96-7.83 (m, 2H), 7.67-7.48 (m, 2H), 7.47 (d, J=X, 1H), 6.12 (s, 2H), 3.62-3.53 (m, 1H), 3.20-3.10 (m, 1H), 2.81 (s, 3H), 2.63 (d, J=14.5 Hz, 1H), 2.08 (d, J=19.8 Hz, 2H), 1.79 (d, J=11.2 Hz, 2H).

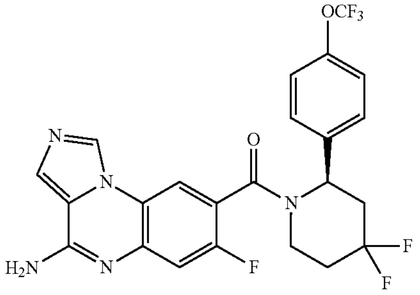

Example Ff-403: (R)-(4-amino-7-fluoroimidazo[1,5-a]quinoxalin-8-yl)(4,4-difluoro-2-(4-(trifluoromethoxy)phenyl)piperidin-1-yl)methanone. Prepared using general procedure VI-F starting with 4-((tert-butoxycarbonyl)amino)-7-fluoroimidazo[1,5-a]quinoxaline-8-carboxylic acid Af-1 and (R)-4,4-difluoro-2-(4-(trifluoromethoxy)phenyl)piperidine Ebk-1. ES/MS: m/z=510.0 $[M+H]^+$. $^1$H NMR (400 MHz, methanol-d4) δ 9.24 (s, 1H), 8.41 (m, 2H), 7.68-6.98 (m, 3H), 6.27 (s, 1H), 3.82 (s, 1H), 3.05 (s, 2H), 2.71-2.31 (m, 1H), 2.21-2.00 (m, 2H), 1.33 (m, 1H).

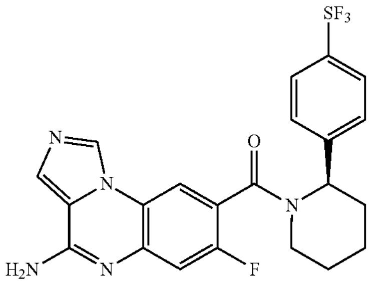

Example Ff-404: (R)-(4-amino-7-fluoroimidazo[1,5-a]quinoxalin-8-yl)(2-(4-(pentafluoro-$\lambda^6$-sulfaneyl)phenyl)piperidin-1-yl)methanone. Prepared using general procedure VI-F starting with 4-((tert-butoxycarbonyl)amino)-7-fluoroimidazo[1,5-a]quinoxaline-8-carboxylic acid Af-1 and (R)-2-(4-(pentafluoro-λ6-sulfaneyl)phenyl)piperidine Ebl-1. ES/MS: m/z=516.0 $[M+H]^+$. $^1$H NMR (400 MHz, methanol-d4) δ 9.32 (s, 1H), 8.52 (d, J=5.8 Hz, 1H), 8.40-8.27 (m, 1H), 7.96-7.82 (m, 2H), 7.67-7.48 (m, 3H), 6.13 (s, 1H), 3.57 (d, J=13.9 Hz, 1H), 3.24-2.80 (m, 2H), 2.71-2.48 (m, 1H), 2.20-2.05 (m, 1H), 1.95-1.42 (m, 4H).

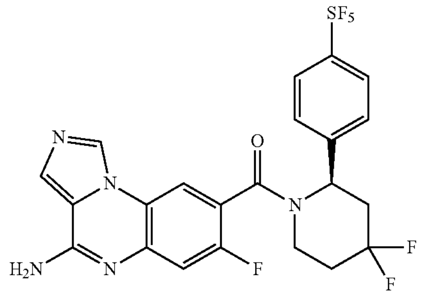

Example Ff-405: (R)-(4-amino-7-fluoroimidazo[1,5-a]quinoxalin-8-yl)(4,4-difluoro-2-(4-(pentafluoro-$\lambda^6$-sulfaneyl)phenyl)piperidin-1-yl)methanone. Prepared using general procedure VI-F starting with intermediates Af-1 and (R)-4,4-difluoro-2-(4-(pentafluoro-16-sulfaneyl)phenyl)piperidine Ebz-1. ES/MS: m/z=552.0 $[M+H]^+$. $^1$H NMR (400 MHz, methanol-d4) δ 9.04 (m, 1H), 8.32 (m, 1H), 7.92 (m, 2H), 7.62 (m, 2H), 7.33 (m, 2H), 6.30 (m, 2H), 3.12-3.00 (m, 1H), 2.72-2.42 (m, 2H), 2.34-1.96 (m, 2H), 1.41-1.22 (m, 2H).

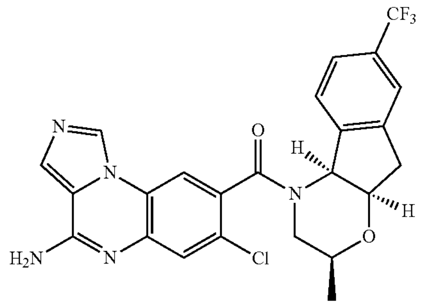 [SMILES: C[C@H]1CN(C(=O)c2cc3c(cc2Cl)nc(N)c2cncn23)[C@H]2c3ccc(C(F)(F)F)cc3C[C@H]2O1]

Example Ff-406: (4-amino-7-chloroimidazo[1,5-a]quinoxalin-8-yl)((2S,4aS,9aR)-2-methyl-7-(trifluoromethyl)-2,3,9,9a-tetrahydroindeno[2,1-b][1,4]oxazin-4(4aH)-yl)methanone. Prepared using general procedure VI-F starting with 4-((tert-butoxycarbonyl)amino)-7-chloroimidazo[1,5-a]quinoxaline-8-carboxylic acid Af-2 and (2S,4aS,9aR)-2-methyl-7-(trifluoromethyl)-2,3,4,4a,9,9a-hexahydroindeno[2,1-b][1,4]oxazine Eaz-1. ES/MS: m/z=502.0 $[M+H]^+$. $^1$H NMR (400 MHz, Methanol-d4) δ 9.46-9.21 (m, 1H), 8.66-8.44 (m, 1H), 8.43-8.19 (m, 1H), 7.86-7.43 (m, 3H), 6.02 (d, J=12.9 Hz, 1H), 4.72-4.42 (m, 1H), 4.02-3.60 (m, 2H), 3.28-2.47 (m, 3H), 1.96 (s, 1H), 1.62-1.22 (m, 1H), 1.27-0.71 (m, 3H).

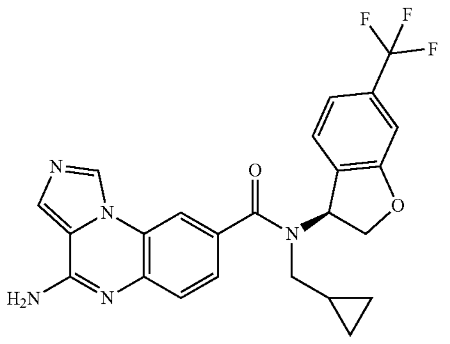 [SMILES: Nc1nc2ccc(C(=O)N(CC3CC3)[C@@H]3COc4cc(C(F)(F)F)ccc43)cc2n2cncc12]

Example Ff-407: (S)-4-amino-N-(cyclopropylmethyl)-N-[(3S)-6-(trifluoromethyl)-2,3-dihydrobenzofuran-3-yl]imidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and (3S)—N-(cyclopropylmethyl)-6-(trifluoromethyl)-2,3-dihydrobenzofuran-3-amine Eh-9. ES/MS: m/z=468.3 $[M+H]^+$. $^1$H NMR (400 MHz, Methanol-d4) δ 9.35 (s, 1H), 8.42 (d, J=3.0 Hz, 2H), 7.83-7.57 (m, 3H), 7.28 (dd, J=8.0, 1.5 Hz, 1H), 7.11 (s, 1H), 5.97 (s, 1H), 3.30 (d, J=6.8 Hz, 2H), 3.23 (dd, J=14.9, 6.5 Hz, 2H), 0.91 (s, 1H), 0.67-0.31 (m, 2H), 0.28--0.29 (m, 2H).

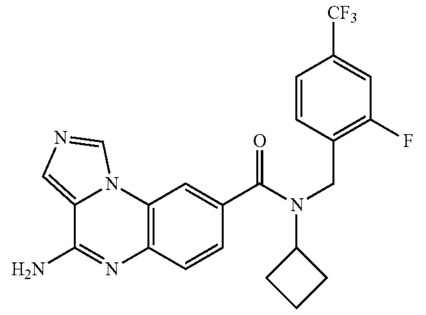 [SMILES: Nc1nc2ccc(C(=O)N(Cc3ccc(C(F)(F)F)cc3F)C3CCC3)cc2n2cncc12]

Example Ff-408: 4-amino-N-cyclobutyl-N-[[2-fluoro-4-(trifluoromethyl)phenyl]methyl]imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and N-[[2-fluoro-4-(trifluoromethyl)phenyl]methyl]cyclobutanamine Ed-30. ES/MS: m/z=458.3 $[M+H]^+$. $^1$H NMR (400 MHz, Methanol-d4) δ 9.34 (s, 1H), 8.42 (s, 2H), 7.81-7.62 (m, 2H), 7.61-7.39 (m, 3H), 4.98 (s, 2H), 4.47 (s, 1H), 2.35-2.10 (m, 2H), 2.08 (s, 2H), 1.80-1.25 (m, 2H).

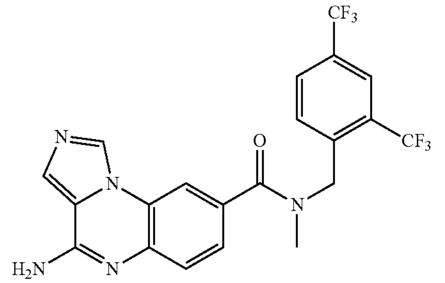 [SMILES: CN(Cc1ccc(C(F)(F)F)cc1C(F)(F)F)C(=O)c1ccc2nc(N)c3cncn3c2c1]

Example Ff-409: 4-amino-N-[[2,4-bis(trifluoromethyl)phenyl]methyl]-N-methyl-imidazo[1,5-a]quinoxaline-8-carboxamide. Prepared following general procedure VI-F starting with starting with starting with 4-((tert-butoxycarbonyl)amino)imidazo[1,5-a]quinoxaline-8-carboxylic acid Ae-1 and 1-[2,4-bis(trifluoromethyl)phenyl]-N-methyl-methanamine Ed-31. ES/MS: m/z=468.2 $[M+H]^+$. $^1$H NMR (400 MHz, Methanol-d4) δ 9.37 (s, 1H), 8.53 (s, 1H), 8.42 (s, 1H), 8.19-7.95 (m, 2H), 7.86-7.60 (m, 3H), 5.10 (s, 2H), 3.15 (d, J=13.5 Hz, 3H).

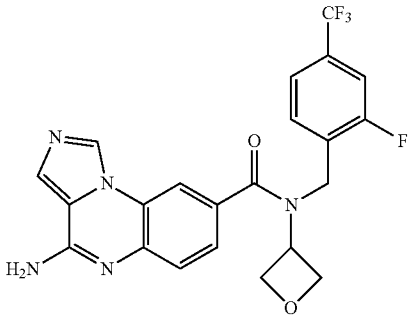 [SMILES: Nc1nc2ccc(C(=O)N(Cc3ccc(C(F)(F)F)cc3F)C3COC3)cc2n2cncc12]

Example Ff-410: 4-amino-N-[[2-fluoro-4-(trifluoromethyl)phenyl]methyl]-N-(oxetan-3-yl)imidazo[1,5-a]quinoxaline-8-carboxamide. Prepared following general procedure VI-F starting with 4-((tert-butoxycarbonyl)amino) imidazo[1,5-a]quinoxaline-8-carboxylic acid Ae-1 and N-[[2-fluoro-4-(trifluoromethyl)phenyl]methyl]oxetan-3-amine Ed-4 (the compound was free based using aqueous $NaHCO_3$ directly after reverse phase purification). ES/MS: m/z=460.3 $[M+H]^+$. $^1H$ NMR (400 MHz, Methanol-d4) δ 9.06 (s, 1H), 8.25 (d, J=1.6 Hz, 1H), 8.04-7.92 (m, 1H), 7.62-7.40 (m 5H), 5.07 (s, 2H), 4.9-4.7 (m, 3H), 4.72 (t, J=7.2 Hz, 2H).

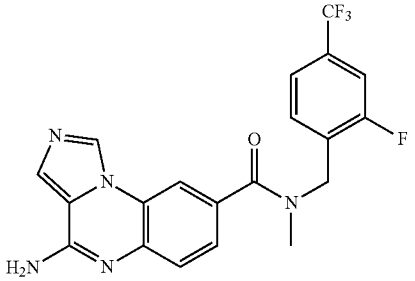 [SMILES: CN(Cc1ccc(C(F)(F)F)cc1F)C(=O)c1ccc2nc(N)c3cncn3c2c1]

Example Ff-411: 4-amino-N-[[2-fluoro-4-(trifluoromethyl)phenyl]methyl]-N-methyl-imidazo[1,5-a]quinoxaline-8-carboxamide. Prepared following general procedure VI-F starting with 4-((tert-butoxycarbonyl)amino)imidazo[1,5-a] quinoxaline-8-carboxylic acid Ae-1 and 1-[2-fluoro-4-(trifluoromethyl)phenyl]-N-methyl-methanamine Ed-33. ES/MS: m/z=418.2 $[M+H]^+$. $^1H$ NMR (400 MHz, Methanol-d4) δ 9.30 (d, J=43.5 Hz, 1H), 8.43 (d, J=16.0 Hz, 2H), 7.71 (s, 2H), 7.58 (t, J=10.8 Hz, 3H), 4.95 (s, 1H), 4.78 (s, 1H), 3.12 (s, 3H).

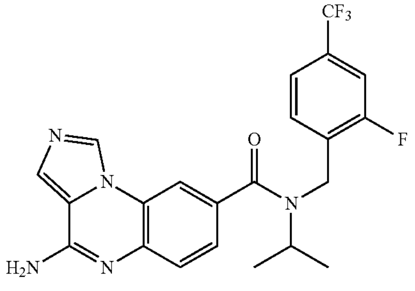 [SMILES: CC(C)N(Cc1ccc(C(F)(F)F)cc1F)C(=O)c1ccc2nc(N)c3cncn3c2c1]

Example Ff-412: 4-amino-N-[[2-fluoro-4-(trifluoromethyl)phenyl]methyl]-N-isopropyl-imidazo[1,5-a]quinoxaline-8-carboxamide. Prepared following general procedure VI-F starting with 4-((tert-butoxycarbonyl)amino)imidazo [1,5-a]quinoxaline-8-carboxylic acid Ae-1 and N-[[2-fluoro-4-(trifluoromethyl)phenyl]methyl]propan-2-amine Ed-34. ES/MS: m/z=446.2 $[M+H]^+$. $^1H$ NMR (400 MHz, Methanol-d4) δ 9.39 (s, 1H), 8.46-8.33 (m, 2H), 7.83-7.40 (m, 5H), 4.84 (s, 2H), 4.23 (s, 1H), 1.26 (brs, 6H).

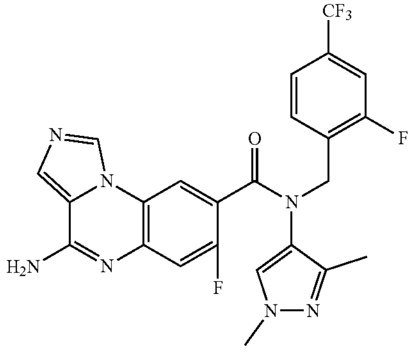 [SMILES: Cc1nn(C)cc1N(Cc1ccc(C(F)(F)F)cc1F)C(=O)c1cc2c(cc1F)nc(N)c1cncn12]

Example Ff-413: 4-amino-N-(1,3-dimethylpyrazol-4-yl)-7-fluoro-N-[[2-fluoro-4-(trifluoromethyl)phenyl]methyl] imidazo[1,5-a]quinoxaline-8-carboxamide. Prepared following general procedure VI-F starting with 4-((tert-butoxycarbonyl)amino)-7-fluoroimidazo[1,5-a] quinoxaline-8-carboxylic acid Af-1 and N-[[2-fluoro-4-(trifluoromethyl)phenyl]methyl]-1,3-dimethyl-pyrazol-4-amine Ec-17. ES/MS: m/z=516.2 $[M+H]^+$. $^1H$ NMR (400 MHz, Methanol-d4) δ 9.26 (s, 1H), 8.40 (d, J=5.7 Hz, 1H), 8.35 (s, 1H), 7.75 (t, J=7.6 Hz, 1H), 7.61-7.54 (m, 1H), 7.54-7.44 (m, 2H), 7.26 (d, J=9.6 Hz, 1H), 5.16 (s, 2H), 3.60 (s, 3H), 1.89 (s, 3H).

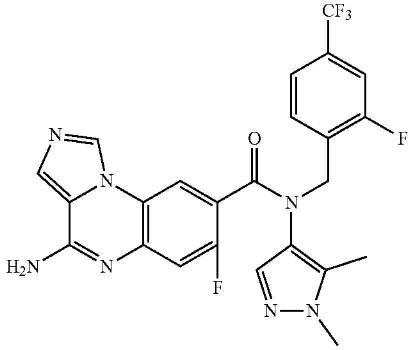 [SMILES: Cc1c(N(Cc2ccc(C(F)(F)F)cc2F)C(=O)c2cc3c(cc2F)nc(N)c2cncn23)cnn1C]

Example Ff-414: 4-amino-N-(1,5-dimethylpyrazol-4-yl)-7-fluoro-N-[[2-fluoro-4-(trifluoromethyl)phenyl]methyl] imidazo[1,5-a]quinoxaline-8-carboxamide. Prepared following general procedure VI-F starting with 4-((tert-butoxycarbonyl)amino)-7-fluoroimidazo[1,5-a] quinoxaline-8-carboxylic acid Af-1 and N-[[2-fluoro-4-(trifluoromethyl)phenyl]methyl]-1,5-dimethyl-pyrazol-4-amine Ed-35. ES/MS: m/z=516.2 $[M+H]^+$. $^1H$ NMR (400 MHz, Methanol-d4) δ 9.24 (d, J=0.7 Hz, 1H), 8.38 (d, J=5.7 Hz, 1H), 8.37-8.29 (m, 1H), 7.75 (t, J=7.6 Hz, 1H), 7.60-7.53 (m, 1H), 7.53-7.44 (m, 1H), 7.25 (d, J=9.6 Hz, 1H), 7.21 (d, J=1.4 Hz, 1H), 5.16 (s, 2H), 3.54 (s, 3H), 1.97 (s, 3H).

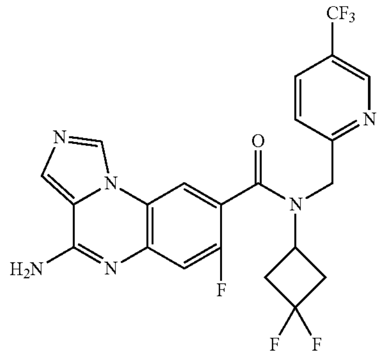 [SMILES: Nc1nc2cc(F)c(C(=O)N(Cc3ccc(C(F)(F)F)cn3)C3CC(F)(F)C3)cc2n2cncc12]

Example Ff-415: 4-amino-N-(3,3-difluorocyclobutyl)-7-fluoro-N-[[5-(trifluoromethyl)-2-pyridyl]methyl]imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 3,3-difluoro-N-[[5-(trifluoromethyl)-2-pyridyl]methyl]cyclobutanamine Ec-18. ES/MS: m/z=495.3 $[M+H]^+$. $^1H$ NMR (400 MHz, Methanol-d4) δ 9.27-9.15 (m, 1H), 8.92 (s, 1H), 8.45-8.28 (m, 2H), 8.21-7.97 (m, 1H), 7.75-7.49 (m, 1H), 7.46-7.32 (m, 1H), 5.05 (s, 1H), 4.85 (s, 1H), 4.51-4.31 (m, 1H), 3.12-2.73 (m, 4H).

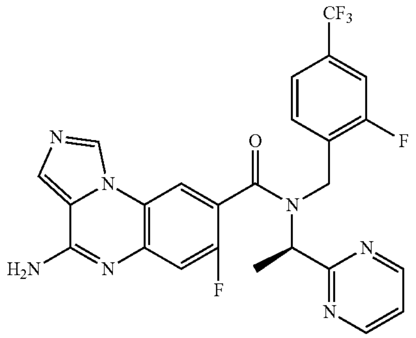 [SMILES: C[C@H](c1ncccn1)N(Cc1ccc(C(F)(F)F)cc1F)C(=O)c1cc2c(cc1F)nc(N)c1cncn12]

Example Ff-416: 4-amino-7-fluoro-N-[[2-fluoro-4-(trifluoromethyl)phenyl]methyl]-N-[(1R)-1-pyrimidin-2-yl-ethyl]imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (1R)—N-[[2-fluoro-4-(trifluoromethyl)phenyl]methyl]-1-pyrimidin-2-yl-ethanamine Ed-37. ES/MS: m/z=528.4 $[M+H]^+$. $^1H$ NMR (400 MHz, Methanol-d4) δ 9.35-9.14 (m, 1H), 8.82-8.66 (m, 2H), 8.62-8.25 (m, 2H), 7.71-7.20 (m, 5H), 5.30 (q, J=6.9 Hz, 1H), 5.14-5.00 (m, 1H), 1.85-1.67 (m, 3H).

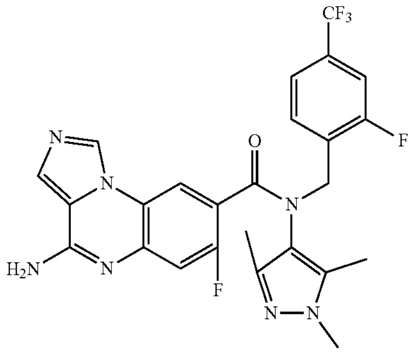 [SMILES: Cc1nn(C)c(C)c1N(Cc1ccc(C(F)(F)F)cc1F)C(=O)c1cc2c(cc1F)nc(N)c1cncn12]

Example Ff-417: 4-amino-7-fluoro-N-[[2-fluoro-4-(trifluoromethyl)phenyl]methyl]-N-(1,3,5-trimethylpyrazol-4-yl)imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and N-[[2-fluoro-4-(trifluoromethyl)phenyl]methyl]-1,3,5-trimethyl-pyrazol-4-amine Ed-38. ES/MS: m/z=530.3 $[M+H]^+$. $^1H$ NMR (400 MHz, Methanol-d4) δ 9.27 (d, J=0.6 Hz, 1H), 8.41 (d, J=5.8 Hz, 1H), 8.35 (s, 1H), 7.78 (t, J=7.6 Hz, 1H), 7.65-7.42 (m, 2H), 7.23 (d, J=9.8 Hz, 1H), 5.25-5.05 (m, 2H), 3.49 (s, 3H), 1.92 (d, J=1.0 Hz, 3H), 1.86 (s, 3H).

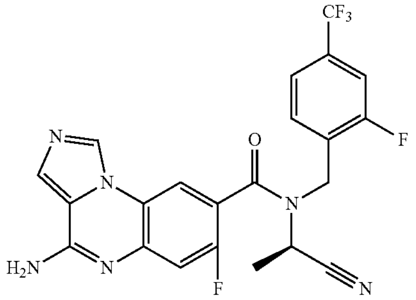 [SMILES: C[C@H](C#N)N(Cc1ccc(C(F)(F)F)cc1F)C(=O)c1cc2c(cc1F)nc(N)c1cncn12]

Example Ff-418: 4-amino-N-[(1R)-1-cyanoethyl]-7-fluoro-N-[[2-fluoro-4-(trifluoromethyl)phenyl]methyl]imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and (R)-2-((2-fluoro-4-(trifluoromethyl)benzyl)amino)propanenitrile Ed-39. ES/MS: m/z=475.2 $[M+H]^+$. $^1H$ NMR (400 MHz, Methanol-d4) δ 9.21 (s, 1H), 8.42 (s, 1H), 8.32 (s, 1H), 7.75-7.25 (m, 4H), 5.31 (s, 1H), 4.89 (s, 1H), 4.85 (s, 1H), 1.69 (s, 3H).

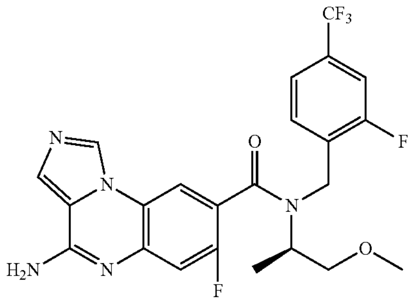 [SMILES: COC[C@@H](C)N(Cc1ccc(C(F)(F)F)cc1F)C(=O)c1cc2c(cc1F)nc(N)c1cncn12]

Example Ff-419: 4-amino-7-fluoro-N-[[2-fluoro-4-(trifluoromethyl)phenyl]methyl]-N-[(1R)-2-methoxy-1-methyl-ethyl]imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and (2R)—N-[[2-fluoro-4-(trifluoromethyl)phenyl]methyl]-1-methoxy-propan-2-amine Ed-40. ES/MS: m/z=494.3 [M+H]$^+$. $^1$H NMR (400 MHz, Methanol-d4) δ 9.23 (d, J=71.2 Hz, 1H), 8.49-8.13 (m, 2H), 7.83-7.65 (m, 1H), 7.61-7.21 (m, 3H), 4.91 (s, 2H), 4.25-4.09 (m, 1H), 3.44-3.35 (m, 1H), 3.28 (dd, J=10.4, 4.0 Hz, 1H), 3.21 (s, 3H), 1.42-1.13 (m, 3H).

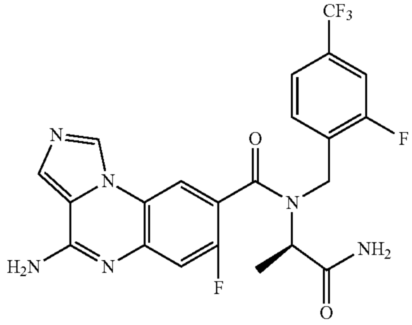 [SMILES: C[C@H](C(N)=O)N(Cc1ccc(C(F)(F)F)cc1F)C(=O)c1cc2c(cc1F)nc(N)c1cncn12]

Example Ff-420: 4-amino-N-[(1R)-2-amino-1-methyl-2-oxo-ethyl]-7-fluoro-N-[[2-fluoro-4-(trifluoromethyl)phenyl]methyl]imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and (2R)-2-[[2-fluoro-4-(trifluoromethyl)phenyl]methyl-amino]propanamide Ec-20. ES/MS: m/z=493.2 [M+H]$^+$. $^1$H NMR (400 MHz, Methanol-d4) δ 9.25-9.05 (m, 1H), 8.46-8.09 (m, 2H), 7.71 (d, J=9.6 Hz, 1H), 7.62-7.41 (m, 2H), 7.35-7.20 (m, 1H), 5.36-4.96 (m, 1H), 4.84 (s, 1H), 4.80-4.47 (m, 1H), 1.61-1.45 (m, 3H).

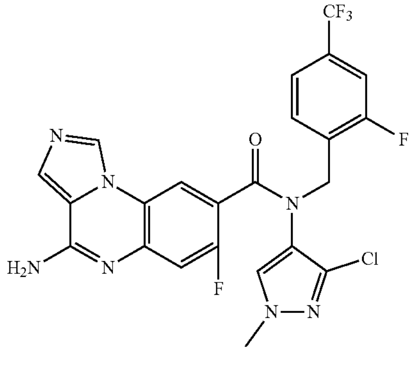 [SMILES: Cn1cc(N(Cc2ccc(C(F)(F)F)cc2F)C(=O)c2cc3c(cc2F)nc(N)c2cncn23)c(Cl)n1]

Example Ff-421: 4-amino-N-(3-chloro-1-methyl-pyrazol-4-yl)-7-fluoro-N-[[2-fluoro-4-(trifluoromethyl)phenyl]methyl]imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and 3-chloro-N-[[2-fluoro-4-(trifluoromethyl)phenyl]methyl]-1-methyl-pyrazol-4-amine Ed-41. ES/MS: m/z=536.2 [M+H]$^+$. $^1$H NMR (400 MHz, Methanol-d4) δ 9.24 (s, 1H), 8.40 (d, J=5.8 Hz, 1H), 8.29 (s, 1H), 7.76 (t, J=7.6 Hz, 1H), 7.70 (d, J=1.5 Hz, 1H), 7.56 (d, J=7.9 Hz, 1H), 7.49 (d, J=9.8 Hz, 1H), 7.21 (d, J=9.8 Hz, 1H), 5.15 (s, 2H), 3.66 (s, 3H).

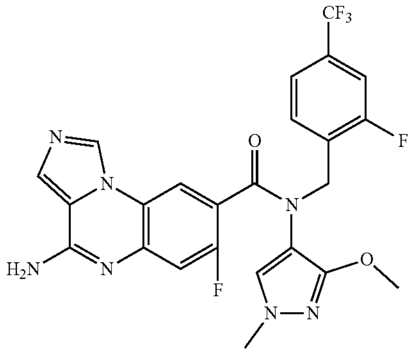 [SMILES: COc1nn(C)cc1N(Cc1ccc(C(F)(F)F)cc1F)C(=O)c1cc2c(cc1F)nc(N)c1cncn12]

Example Ff-422: 4-amino-7-fluoro-N-[[2-fluoro-4-(trifluoromethyl)phenyl]methyl]-N-(3-methoxy-1-methyl-pyrazol-4-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-[[2-fluoro-4-(trifluoromethyl)phenyl]methyl]-3-methoxy-1-methyl-pyrazol-4-amine Ec-19. ES/MS: m/z=532.3 [M+H]$^+$. $^1$H NMR (400 MHz, Methanol-d4) δ 9.27 (d, J=0.8 Hz, 1H), 8.43-8.29 (m, 2H), 7.73 (t, J=7.6 Hz, 1H), 7.58-7.51 (m, 1H), 7.47 (dd, J=10.0, 1.7 Hz, 1H), 7.39 (d, J=1.1 Hz, 1H), 7.27 (d, J=9.5 Hz, 1H), 5.10 (s, 2H), 3.64 (s, 3H), 3.51 (s, 3H).

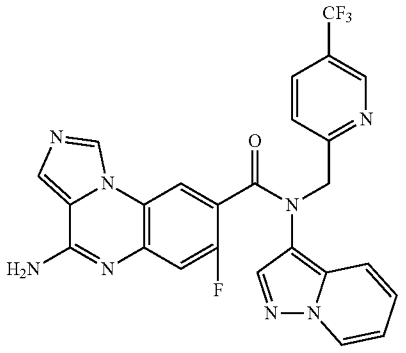 [SMILES: Nc1nc2cc(F)c(C(=O)N(Cc3ccc(C(F)(F)F)cn3)c3cnn4ccccc34)cc2n2cncc12]

Example Ff-423: 4-amino-7-fluoro-N-pyrazolo[1,5-a]pyridin-3-yl-N-[[5-(trifluoromethyl)-2-pyridyl]methyl]imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-[[5-(trifluoromethyl)-2-pyridyl]methyl]pyrazolo[1,5-a]pyridin-3-amine Ed-42. ES/MS: m/z=521.2 [M+H]$^+$. $^1$H NMR (400 MHz, Methanol-d4) δ 9.19 (d, J=0.7 Hz, 1H), 8.89 (dt, J=1.9, 1.0 Hz, 1H), 8.44 (d, J=5.8 Hz, 1H), 8.36-8.27 (m, 2H), 8.25-8.10 (m, 1H), 7.93 (d, J=1.1 Hz, 1H), 7.77 (d, J=8.2 Hz, 1H), 7.63 (dq, J=8.9, 1.0 Hz, 1H), 7.25 (ddd, J=9.0, 6.8, 1.0 Hz, 1H), 7.15 (d, J=9.5 Hz, 1H), 6.83 (td, J=6.9, 1.3 Hz, 1H), 5.34 (s, 2H).

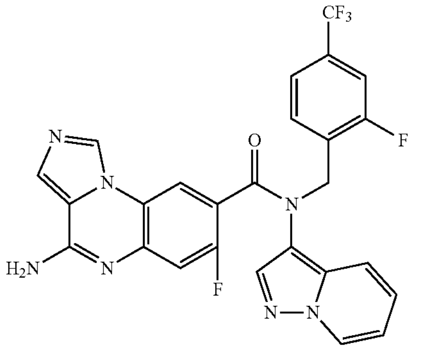 [SMILES: Nc1nc2cc(F)c(C(=O)N(Cc3ccc(C(F)(F)F)cc3F)c3cnn4ccccc34)cc2n2cncc12]

Example Ff-424: 4-amino-7-fluoro-N-[[2-fluoro-4-(trifluoromethyl)phenyl]methyl]-N-pyrazolo[1,5-a]pyridin-3-yl-imidazo[1,5-a]quinoxaline-8-carboxamide. Prepared following general procedure VI-F starting with 4-((tert-butoxycarbonyl)amino)-7-fluoroimidazo[1,5-a] quinoxaline-8-carboxylic acid Af-1 and N-[[2-fluoro-4-(trifluoromethyl)phenyl]methyl]pyrazolo[1,5-a]pyridin-3-amine Ed-32. ES/MS: m/z=538.2 $[M+H]^+$. 1H NMR (400 MHz, Methanol-d4) δ 9.22-9.10 (m, 1H), 8.40 (d, J=5.8 Hz, 1H), 8.35-8.24 (m, 2H), 7.82 (d, J=1.2 Hz, 1H), 7.76 (t, J=7.6 Hz, 1H), 7.53 (d, J=7.9 Hz, 1H), 7.46-7.33 (m, 2H), 7.20 (ddd, J=9.0, 6.8, 1.0 Hz, 1H), 7.13 (d, J=9.6 Hz, 1H), 6.81 (td, J=6.9, 1.4 Hz, 1H), 5.30 (s, 2H).

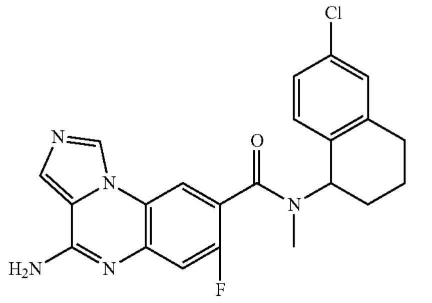 [SMILES: CN(C(=O)c1cc2c(cc1F)nc(N)c1cncn12)C1CCCc2cc(Cl)ccc21]

Example Ff-425: 4-amino-N-(6-chloro-1,2,3,4-tetrahydronaphthalen-1-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 6-chloro-N-methyl-1,2,3,4-tetrahydronaphthalen-1-amine Eh-14. ES/MS: m/z=424.4 $[M+H]^+$. $^1$H NMR (400 MHz, Methanol-d4) δ 9.44-9.19 (m, 1H), 8.52 (d, J=5.8 Hz, 1H), 8.47-8.28 (m, 1H), 7.51 (dd, J=9.6, 6.3 Hz, 1H), 7.39-7.08 (m, 3H), 5.97 (dd, J=10.4, 6.1 Hz, 1H), 2.87 (s, 2H), 2.73 (d, J=1.0 Hz, 2H), 2.31-1.83 (m, 4H), 1.60 (s,

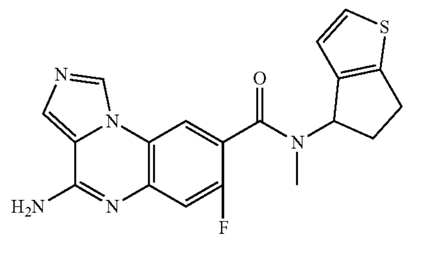 [SMILES: CN(C(=O)c1cc2c(cc1F)nc(N)c1cncn12)C1CCc2sccc21]

Example Ff-426: 4-amino-N-(5,6-dihydro-4H-cyclopenta[b]thiophen-4-yl)-7-fluoro-N-methyl-imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-methyl-5,6-dihydro-4H-cyclopenta[b]thiophen-4-amine Eh-10. ES/MS: m/z=382.2 $[M+H]^+$. $^1$H NMR (400 MHz, Methanol-d4) δ 9.28 (d, J=6.8 Hz, 1H), 8.65-8.38 (m, 1H), 8.35 (d, J=6.0 Hz, 1H), 7.48 (t, J=10.1 Hz, 1H), 7.40 (dt, J=10.9, 4.6 Hz, 1H), 7.04-6.85 (m, 1H), 5.58-5.14 (m, 1H), 3.21-2.91 (m, 3H), 2.86 (s, 2H), 2.70 (d, J=1.1 Hz, 1H), 2.65-2.40 (m, 1H).

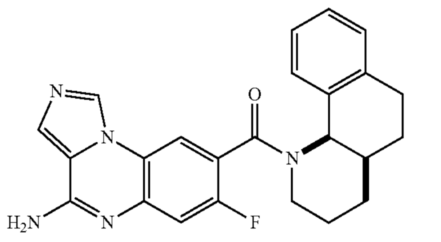

(±)

Example Ff-427: cis-2,3,4a,5,6,10b-hexahydrobenzo[f][1,4]benzoxazin-1-yl-(4-amino-7-fluoro-imidazo[1,5-a]quinoxalin-8-yl)methanone. Prepared following general procedure VI-F starting with starting with starting with 4-((tert-butoxycarbonyl)amino)-7-fluoroimidazo[1,5-a] quinoxaline-8-carboxylic acid Af-1 and cis-2,3,4a,5,6,10b-hexahydro-1H-benzo[f][1,4]benzoxazine Ee-4. ES/MS: m/z=418.4 $[M+H]^+$. 1H NMR (400 MHz, Methanol-d4) δ 9.17 (d, J=8.9 Hz, 1H), 8.58-8.25 (m, 2H), 7.52 (dd, J=11.4, 9.4 Hz, 1H), 7.33-7.07 (m, 4H), 5.82 (s, 1H), 4.61-4.35 (m, 1H), 4.25-4.09 (m, 1H), 4.04-3.62 (m, 2H), 3.24 (s, 1H), 3.18-2.85 (m, 1H), 2.71-2.62 (m, 1H), 2.37-2.13 (m, 1H), 2.13-1.93 (m, 1H).

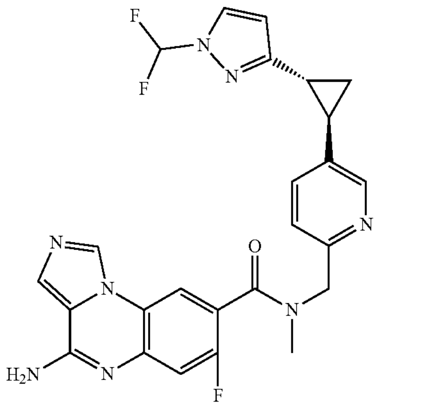 [SMILES: CN(Cc1ccc([C@@H]2C[C@H]2c2ccn(C(F)F)n2)cn1)C(=O)c1cc2c(cc1F)nc(N)c1cncn12]

Example Ff-428: 4-amino-N-[[5-[(1R,2R)-2-[1-(difluoromethyl)pyrazol-3-yl]cyclopropyl]-2-pyridyl]methyl]-7-fluoro-N-methyl-imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and 1-[5-[(1R,2R)-2-[1-(difluoromethyl)pyrazol-3-yl]cyclopropyl]-2-pyridyl]-N-methyl-methanamine Ebm-1. ES/MS: m/z=507.3 $[M+H]^+$. $^1$H NMR (400 MHz, Methanol-d4) δ 9.33-9.10 (m, 1H), 8.65-8.34 (m, 3H), 8.06-7.92 (m, 2H), 7.78-7.20 (m, 4H), 5.00 (s, 1H), 4.67 (s, 1H), 3.23-3.08 (m, 3H), 2.48-2.09 (m, 2H), 1.68-1.39 (m, 2H).

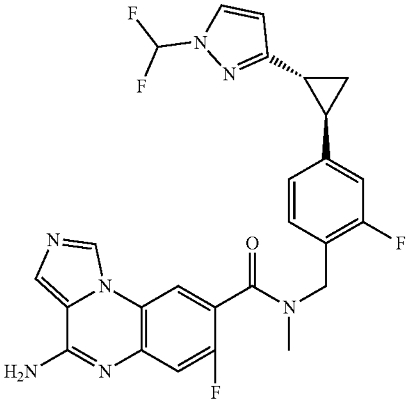 [SMILES: CN(Cc1ccc([C@@H]2C[C@H]2c2ccn(C(F)F)n2)cc1F)C(=O)c1cc2c(cc1F)nc(N)c1cncn12]

Example Ff-429: 4-amino-N-[[4-[(1R,2R)-2-[1-(difluoromethyl)pyrazol-3-yl]cyclopropyl]-2-fluoro-phenyl]methyl]-7-fluoro-N-methyl-imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and 1-[4-[(1R,2R)-2-[1-(difluoromethyl)pyrazol-3-yl]cyclopropyl]-2-fluoro-phenyl]-N-methyl-methanamine Ebm-2. ES/MS: m/z=524.4 $[M+H]^+$. $^1H$ NMR (400 MHz, Methanol-d4) δ 9.33-9.10 (m, 1H), 8.54-8.29 (m, 2H), 7.91 (d, J=10.1 Hz, 1H), 7.63 (d, J=12.2 Hz, 1H), 7.59-7.35 (m, 2H), 7.32-7.15 (m, 1H), 7.14-6.83 (m, 2H), 4.59 (s, 1H), 3.10 (s, 1H), 2.99 (d, J=1.2 Hz, 2H), 2.28-1.99 (m, 2H), 1.53-1.30 (m, 2H).

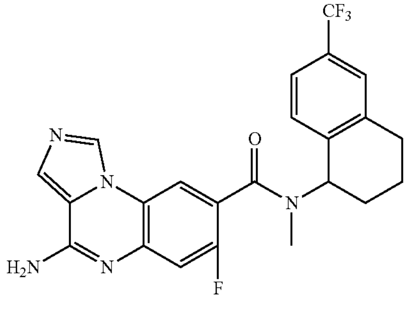 [SMILES: CN(C(=O)c1cc2c(cc1F)nc(N)c1cncn12)C1CCCc2cc(C(F)(F)F)ccc21]

Example Ff-430: 4-amino-7-fluoro-N-methyl-N-[6-(trifluoromethyl)tetralin-1-yl]imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and N-methyl-6-(trifluoromethyl)tetralin-1-amine Eh-11. ES/MS: m/z=458.4 $[M+H]^+$. $^1H$ NMR (400 MHz, Methanol-d4) δ 9.35-9.25 (m, 1H), 8.66-8.32 (m, 2H), 7.60-7.38 (m, 5H), 6.04 (t, J=8.4 Hz, 1H), 2.96 (t, J=8.0 Hz, 1H), 2.89 (s, 1H), 2.76 (d, J=1.0 Hz, 2H), 2.29-1.89 (m, 4H).

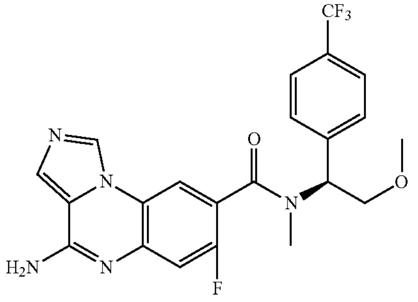 [SMILES: COC[C@H](c1ccc(C(F)(F)F)cc1)N(C)C(=O)c1cc2c(cc1F)nc(N)c1cncn12]

Example Ff-431: 4-amino-7-fluoro-N-[(1S)-2-methoxy-1-[4-(trifluoromethyl)phenyl]ethyl]-N-methyl-imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and (S)-2-methoxy-N-methyl-1-(4-(trifluoromethyl)phenyl)ethan-1-amine Eh-12. ES/MS: m/z=462.4 $[M+H]^+$. $^1H$ NMR (400 MHz, Methanol-d4) δ 8.98 (s, 1H), 8.67-8.01 (m, 3H), 7.78-7.18 (m, 4H), 4.98-4.72 (m, 1H), 4.42-4.11 (m, 3H), 4.03-3.54 (m, 6H).

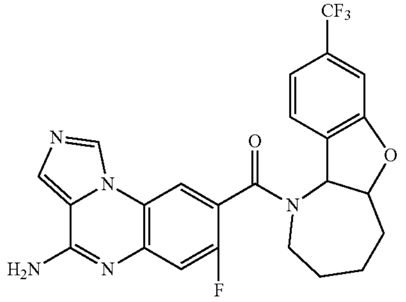 [SMILES: Nc1nc2cc(F)c(C(=O)N3CCCCC4Oc5cc(C(F)(F)F)ccc5C43)cc2n2cncc12]

Example Ff-432: (4-amino-7-fluoro-imidazo[1,5-a]quinoxalin-8-yl)-[8-(trifluoromethyl)-2,3,4,5,5a,10b-hexahydrobenzofuro[3,2-b]azepin-1-yl]methanone. Prepared following general procedure VI-F starting with starting with starting with 4-((tert-butoxycarbonyl)amino)-7-fluoroimidazo[1,5-a]quinoxaline-8-carboxylic acid Af-1 and 8-(trifluoromethyl)-2,3,4,5,5a,10b-hexahydro-1H-benzofuro[3,2-b]azepine Ebe-5. ES/MS: m/z=486.2 $[M+H]^+$. 1H NMR (400 MHz, Methanol-d4) δ 9.04-8.86 (m, 2H), 8.42-8.11 (m, 2H), 7.51 (dd, J=9.7, 5.7 Hz, 1H), 7.32-7.02 (m, 2H), 5.45-5.22 (m, 1H), 3.55-3.45 (m, 1H), 3.45-3.36 (m, 1H), 2.68-2.40 (m, 1H), 2.31-2.21 (m, 1H), 1.87-1.60 (m, 5H).

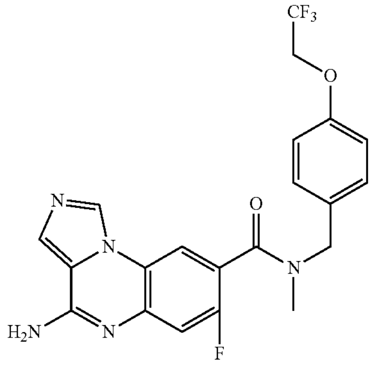 [SMILES: CN(Cc1ccc(OCC(F)(F)F)cc1)C(=O)c1cc2c(cc1F)nc(N)c1cncn12]

Example Ff-433: 4-amino-7-fluoro-N-methyl-N-[[4-(2,2,2-trifluoroethoxy)phenyl]methyl]imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and commercial N-methyl-1-(4-(2,2,2-trifluoroethoxy)phenyl)methanamine. ES/MS: m/z=448.3 $[M+H]^+$. $^1H$ NMR (400 MHz, Methanol-d4) δ 9.33-9.13 (m, 1H), 8.43 (dd, J=5.8, 2.1 Hz, 1H), 8.39 (d, J=4.1 Hz, 1H), 7.49 (dd, J=9.6, 4.0 Hz, 1H), 7.46-7.37 (m, 1H), 7.23-6.96 (m, 3H), 4.79 (s, 1H), 4.65-4.45 (m, 3H), 3.13-2.87 (m, 3H).

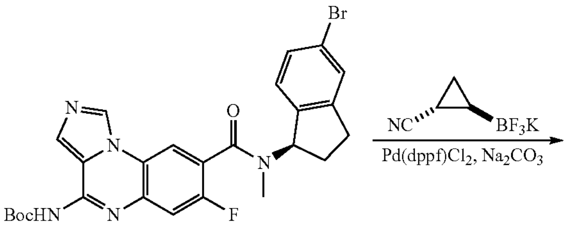

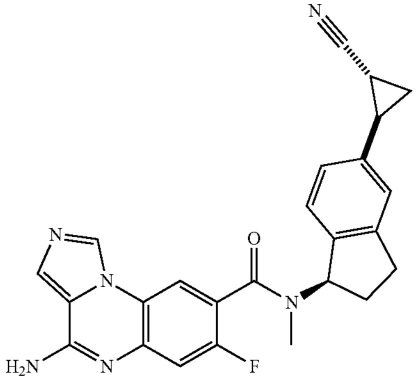

Example Ff-434

Example Ff-434: Trans-4-amino-N-[(1R)-5-(2-cyanocyclopropyl)indan-1-yl]-7-fluoro-N-methyl-imidazo[1,5-a]quinoxaline-8-carboxamide. Intermediate tert-butyl (R)-(8-((5-bromo-2,3-dihydro-1H-inden-1-yl)(methyl)carbamoyl)-7-fluoroimidazo[1,5-a]quinoxalin-4-yl)carbamate was prepared following step 1 of general procedure VI-F starting with 4-((tert-butoxycarbonyl)amino)-7-fluoroimidazo[1,5-a]quinoxaline-8-carboxylic acid Af-1 and commercial (R)-5-bromo-N-methyl-2,3-dihydro-1H-inden-1-amine. Example Ff-434 was prepared using the conditions reported in general procedure LXV-E starting with tert-butyl (R)-(8-((5-bromo-2,3-dihydro-1H-inden-1-yl)(methyl)carbamoyl)-7-fluoroimidazo[1,5-a]quinoxalin-4-yl)carbamate and trans-potassium (2-cyanocyclopropyl)trifluoroborate. ES/MS: m/z=441.4 $[M+H]^+$. $^1H$ NMR (400 MHz, Methanol-d4) δ 9.29 (d, J=5.3 Hz, 1H), 8.47 (d, J=5.8 Hz, 1H), 8.37 (d, J=3.1 Hz, 1H), 7.55-7.45 (m, 1H), 7.25 (d, J=7.8 Hz, 1H), 7.18-7.04 (m, 2H), 6.37 (t, J=8.1 Hz, 0.4H minor rotamer), 5.76 (t, J=8.2 Hz, 0.6H major rotamer), 3.19-2.93 (m, 1H), 2.88-2.79 (m, 3H), 2.75-2.46 (m, 2H), 2.39 (s, 1H), 2.32-2.10 (m, 1H), 1.87-1.76 (m, 1H), 1.62 (ddt, J=9.2, 8.1, 5.4 Hz, 1H), 1.58-1.43 (m, 1H).

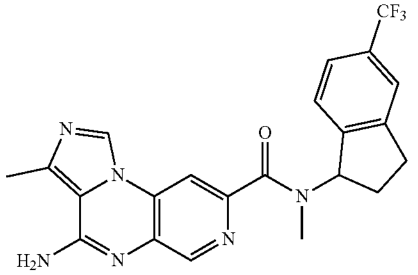 [SMILES: Cc1ncn2c1c(N)nc1cnc(C(=O)N(C)C3CCc4cc(C(F)(F)F)ccc43)cc12]

Example Ff-435: 7-amino-N,5-dimethyl-N-[5-(trifluoromethyl)indan-1-yl]-2,4,8,11-tetrazatricyclo[7.4.0.02,6]trideca-1(13),3,5,7,9,11-hexaene-12-carboxamide. Prepared following general procedure VI-F starting with starting with starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and N-methyl-5-(trifluoromethyl)indan-1-amine Eh-13. ES/MS: m/z=441.3 $[M+H]^+$. $^1H$ NMR (400 MHz, Methanol-d4) δ 9.11 (s, 1H), 8.81 (d, J=3.8 Hz, 1H), 8.39 (d, J=6.0 Hz, 1H), 7.66 (s, 1H), 7.56 (d, J=9.4 Hz, 1H), 7.52 (s, 1H), 6.38 (t, J=8.1 Hz, 0.4H minor rotamer), 5.75 (t, J=8.2 Hz, 0.6H major rotamer), 3.25-2.95 (m, 1H), 2.85 (d, J=12.4 Hz, 4H), 2.79 (d, J=3.0 Hz, 3H), 2.73-2.49 (m, 1H), 2.32-2.19 (m, 1H).

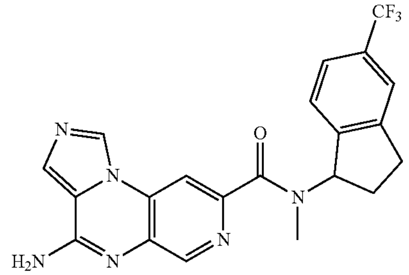 [SMILES: CN(C(=O)c1cc2c(cn1)nc(N)c1cncn12)C1CCc2cc(C(F)(F)F)ccc21]

Example Ff-436: 7-amino-N-methyl-N-[5-(trifluoromethyl)indan-1-yl]-2,4,8,11-tetrazatricyclo[7.4.0.02,6]trideca-1(13),3,5,7,9,11-hexaene-12-carboxamide. Prepared following general procedure VI-F starting with starting with starting with 4-((tert-butoxycarbonyl)amino)imidazo[1,5-a]pyrido[3,4-e]pyrazine-8-carboxylic acid Af-6 and N-methyl-5-(trifluoromethyl)indan-1-amine Eh-13. ES/MS: m/z=427.3 $[M+H]^+$. 1H NMR (400 MHz, Methanol-d4) δ 9.35 (s, 1H), 8.85 (d, J=4.4 Hz, 1H), 8.55 (d, J=4.2 Hz, 1H), 8.31 (d, J=1.5 Hz, 1H), 7.72-7.49 (m, 3H), 6.35-6.47 (m, 0.4H minor rotamer), 5.75-5.68 (m, 0.6H major rotamer), 3.28-3.00 (m, 1H), 2.95-2.76 (m, 4H), 2.72-2.45 (m, 1H), 2.44-2.21 (m, 1H).

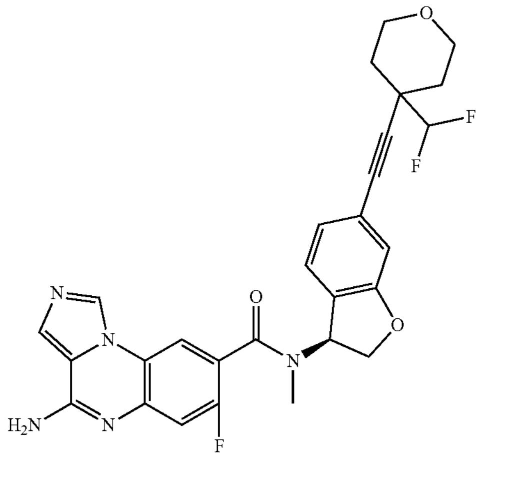 [SMILES: CN(C(=O)c1cc2c(cc1F)nc(N)c1cncn12)[C@@H]1COc2cc(C#CC3(C(F)F)CCOCC3)ccc21]

Example Ff-437: (S)-4-amino-N-(6-((4-(difluoromethyl) tetrahydro-2H-pyran-4-yl)ethynyl)-2,3-dihydrobenzofuran-3-yl)-7-fluoro-N-methylimidazo[1,5-a]quinoxaline-8-carboxamide. Prepared following general procedure example Ff-17 starting with 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 4-(difluoromethyl)-4-ethynyl-tetrahydropyran. ES/MS: m/z=536.3 $[M+H]^+$. $^1$H NMR (400 MHz, Methanol-d4) δ 9.26 (s, 1H), 8.44 (d, J=5.9 Hz, 1H), 8.36 (d, J=2.5 Hz, 1H), 7.59-7.25 (m, 2H), 7.21-7.05 (m, 1H), 7.05-6.85 (m, 1H), 6.52 (dd, J=8.8, 3.5 Hz, 0.55H major rotamer), 5.80 (td, J=56.3, 5.7 Hz, 1H), 5.60 (t, J=6.5 Hz, 0.45H minor rotamer), 4.83-4.61 (m, 1H), 4.01-3.90 (m, 2H), 3.75-3.90 (m, 2H), 2.93-2.64 (m, 3H), 1.94-1.80 (m, 2H), 1.65-1.76 (m, 2H).

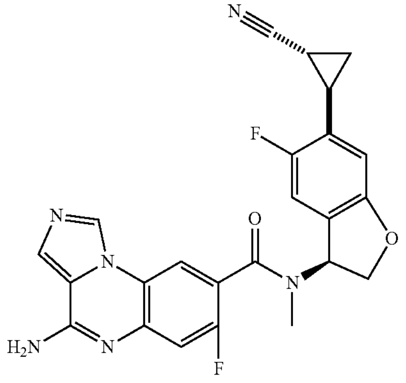

Example Ff-438: Trans-4-amino-N-[(3S)-6-(2-cyanocyclopropyl)-5-fluoro-2,3-dihydrobenzofuran-3-yl]-7-fluoro-N-methyl-imidazo[1,5-a]quinoxaline-8-carboxamide. Prepared following general procedure VI-F starting with starting with starting with 4-((tert-butoxycarbonyl)amino)-7-fluoroimidazo[1,5-a]quinoxaline-8-carboxylic acid Af-1 and rac-2-[(3S)-5-fluoro-3-(methylamino)-2,3-dihydrobenzofuran-6-yl]cyclopropanecarbonitrile Ebm-3. ES/MS: m/z=461.3 $[M+H]^+$. $^1$H NMR (400 MHz, Methanol-d4) δ 9.27 (s, 1H), 8.62-8.23 (m, 2H), 7.45-7.55 (m, 1H), 7.25-7.01 (m, 1H), 6.71-6.54 (m, 1H), 6.47 (dd, J=8.8, 3.5 Hz, 0.55H major rotamer), 5.56 (d, J=6.7 Hz, 0.45H minor rotamer), 4.73-4.80 (m, 1H), 4.64 (dd, J=10.7, 3.5 Hz, 1H), 2.94-2.62 (m, 4H), 1.95-1.78 (m, 1H), 1.74-1.63 (m, 1H), 1.64-1.47 (m, 1H).

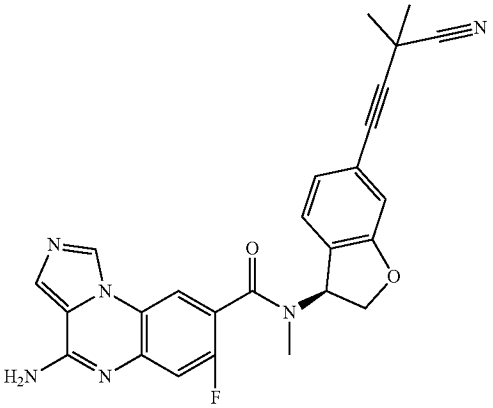 [SMILES: CN(C(=O)c1cc2c(cc1F)nc(N)c1cncn12)[C@@H]1COc2cc(C#CC(C)(C)C#N)ccc21]

Example Ff-439: 4-amino-N-[(3S)-6-(3-cyano-3-methyl-but-1-ynyl)-2,3-dihydrobenzofuran-3-yl]-7-fluoro-N-methyl-imidazo[1,5-a]quinoxaline-8-carboxamide. Prepared following general procedure example Ff-17 starting with intermediate 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 2,2-dimethylbut-3-ynenitrile. ES/MS: m/z=469.4 $[M+H]^+$. 1H NMR (400 MHz, Methanol-d4) δ 9.36 (s, 1H), 8.45 (d, J=5.8 Hz, 2H), 7.45-7.55 (m, 1H), 7.30-7.40 (m, 1H), 7.19-7.05 (m, 1H), 7.03-6.88 (m, 1H), 6.52 (dd, J=8.8, 3.5 Hz, 0.55H major rotamer), 5.60 (t, J=6.4 Hz, 0.45H minor rotamer), 4.82 (dd, J=10.8, 8.8 Hz, 1H), 4.66 (dd, J=10.7, 3.6 Hz, 1H), 2.95-2.64 (m, 3H), 1.75 (d, J=6.1 Hz, 6H).

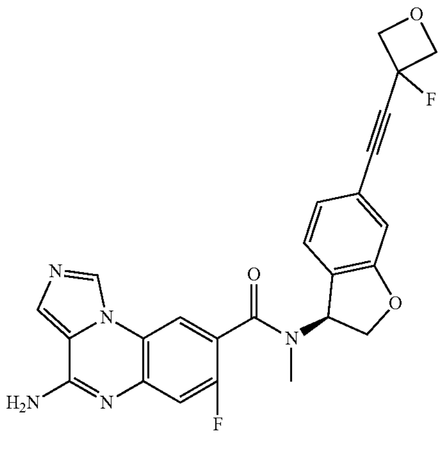 [SMILES: CN(C(=O)c1cc2c(cc1F)nc(N)c1cncn12)[C@@H]1COc2cc(C#CC3(F)COC3)ccc21]

Example Ff-440: 4-amino-7-fluoro-N-[(3S)-6-[2-(3-fluorooxetan-3-yl)ethynyl]-2,3-dihydrobenzofuran-3-yl]-N-methyl-imidazo[1,5-a]quinoxaline-8-carboxamide. Prepared following general procedure Ff-17 starting with intermediate 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 3-ethynyl-3-fluoro-oxetane. ES/MS: m/z=476.3 $[M+H]^+$. $^1H$ NMR (400 MHz, Methanol-d4) δ 9.29 (s, 1H), 8.50-8.33 (m, 2H), 7.62-7.32 (m, 2H), 7.25-7.11 (m, 1H), 7.05-6.99 (m, 1H), 6.53 (dd, J=8.8, 3.5 Hz, 0.55H major rotamer), 5.62 (t, J=6.4 Hz, 0.45H minor rotamer), 4.95 (ddd, J=13.6, 8.3, 6.2 Hz, 3H), 4.84-4.75 (m, 1H), 4.67 (dd, J=10.7, 3.7 Hz, 1H), 2.93-2.66 (m, 3H).

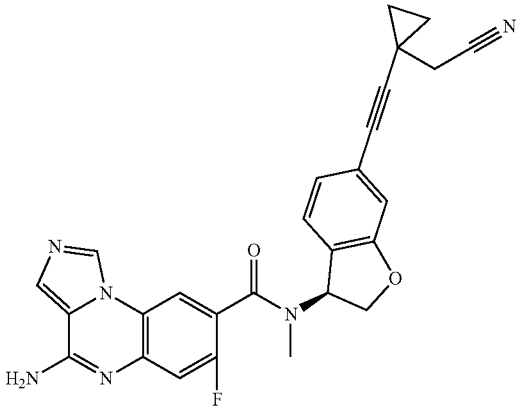 [SMILES: CN(C(=O)c1cc2c(cc1F)nc(N)c1cncn12)[C@@H]1COc2cc(C#CC3(CC#N)CC3)ccc21]

Example Ff-441: 4-amino-N-[(3S)-6-[2-[1-(cyanomethyl)cyclopropyl]ethynyl]-2,3-dihydrobenzofuran-3-yl]-7-fluoro-N-methyl-imidazo[1,5-a]quinoxaline-8-carboxamide. Prepared following general procedure example Ff-17 starting with intermediate 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 2-(1-ethynylcyclopropyl)acetonitrile. ES/MS: m/z=481.4 $[M+H]^+$. $^1H$ NMR (400 MHz, Methanol-d4) δ 9.35 (s, 1H), 8.74-8.21 (m, 2H), 7.46-7.53 (m, 1H), 7.25-7.35 (m, 1H), 7.15-6.99 (m, 1H), 6.82-6.92 (m, 1H), 6.50 (dd, J=8.8, 3.5 Hz, 0.52H major rotamer), 5.57 (t, J=6.4 Hz, 0.48H minor rotamer), 4.80 (dd, J=10.7, 8.8 Hz, 0.5H rotamer), 4.64 (dd, J=10.7, 3.6 Hz, 1.5H rotamer), 2.93-2.61 (m, 5H), 1.15 (td, J=6.9, 6.5, 4.6 Hz, 2H), 1.02 (brs, 2H).

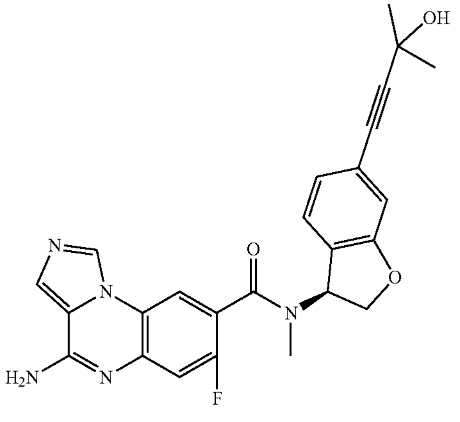 [SMILES: CN(C(=O)c1cc2c(cc1F)nc(N)c1cncn12)[C@@H]1COc2cc(C#CC(C)(C)O)ccc21]

Example Ff-442: 4-amino-7-fluoro-N-[(3S)-6-(3-hydroxy-3-methyl-but-1-ynyl)-2,3-dihydrobenzofuran-3-yl]-N-methyl-imidazo[1,5-a]quinoxaline-8-carboxamide. Prepared following general procedure example Ff-17 starting with intermediate 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 2-methylbut-3-yn-2-ol. ES/MS: m/z=460.1 $[M+H]^+$. $^1H$ NMR (400 MHz, Methanol-d4) δ 9.37 (s, 1H), 8.75-8.21 (m, 2H), 7.46-7.53 (m, 1H), 7.37 (d, J=7.7 Hz, 1H), 7.13-6.99 (m, 1H), 6.97-6.82 (m, 1H), 6.50 (dd, J=8.8, 3.5 Hz, 0.55H major rotamer), 5.58 (t, J=6.4 Hz, 0.45H minor rotamer), 4.80 (dd, J=10.7, 8.8 Hz, 1H), 4.64 (dd, J=10.7, 3.6 Hz, 1H), 2.83 (s, 1.35H minor rotamer), 2.69 (s, 1.65H major rotamer), 1.56 (d, J=5.8 Hz, 6H).

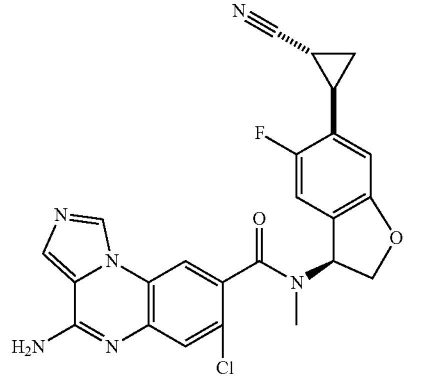

Example Ff-443: Trans-4-amino-7-chloro-N-[(3S)-6-(2-cyanocyclopropyl)-5-fluoro-2,3-dihydrobenzofuran-3-yl]-N-methyl-imidazo[1,5-a]quinoxaline-8-carboxamide. Prepared following general procedure VI-F starting with starting with starting with 4-(tert-butoxycarbonylamino)-7-chloro-imidazo[1,5-a]quinoxaline-8-carboxylic acid Af-2 and 2-[(3S)-5-fluoro-3-(methylamino)-2,3-dihydrobenzofuran-6-yl]cyclopropanecarbonitrile Ebm-3. ES/MS: m/z=477.2 $[M+H]^+$. $^1H$ NMR (400 MHz, Methanol-d4) δ 9.15-9.36 (m, 1H), 8.63-8.31 (m, 2H), 7.85-7.68 (m, 1H), 7.05-7.26 (m, 1H), 6.73-6.58 (m, 1H), 6.51 (dd, J=8.8, 3.5 Hz, 0.55H major rotamer), 5.49 (d, J=6.7 Hz, 0.45H minor rotamer), 4.80 (ddd, J=10.3, 8.7, 1.4 Hz, 1H), 4.72-4.58 (m, 1H), 2.86 (d, J=4.0 Hz, 1H), 2.77-2.60 (m, 1H), 2.64 (s, 2H), 1.99-1.80 (m, 1H), 1.63-1.70 (m, 1H), 1.61-1.46 (m, 1H).

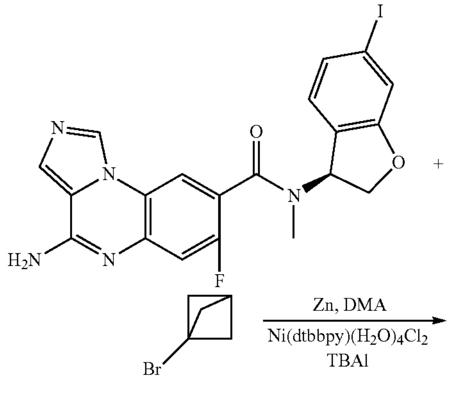

-continued

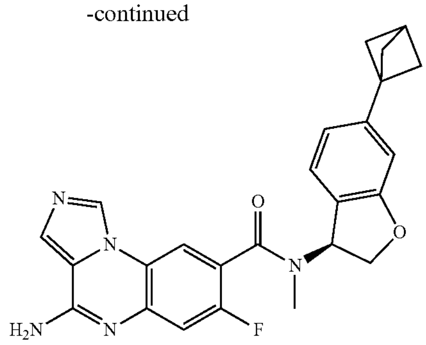

Example Ff-444

Example Ff-444: 4-amino-N-[(3S)-6-(1-bicyclo[1.1.1]pentanyl)-2,3-dihydrobenzofuran-3-yl]-7-fluoro-N-methyl-imidazo[1,5-a]quinoxaline-8-carboxamide. To a microwave vial was added (S)-4-amino-7-fluoro-N-(6-iodo-2,3-dihydrobenzofuran-3-yl)-N-methylimidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16; 50.5 mg, 0.1 mmol), 1-bromobicyclo[1.1.1]pentane (60 mg, 0.4 mmol), zinc (39.3 mg, 0.6 mmol), tetrabutylammonium iodide (44.4 mg, 0.12 mmol), and $Ni(dtbbpy)(H_2O)_4Cl_2$ (4.7 mg, 0.01 mmol) in 1 mL of DMA. The mixture was sparged with argon for 5 minute before vial sealed with cap. It was stirred vigorously overnight at 70 degrees. The mixture was filtered and purified by HPLC prep to get desired product. ES/MS: m/z=444.3 $[M+H]^+$. $^1H$ NMR (400 MHz, Methanol-d4) δ 9.25 (s, 1H), 8.62-8.27 (m, 2H), 7.44-7.53 (m, 1H), 7.19-7.42 (m, 1H), 7.03-6.88 (m, 1H), 6.88-6.75 (m, 1H), 6.47 (dd, J=8.6, 3.3 Hz, 0.52H major rotamer), 5.53 (t, J=6.2 Hz, 0.48H minor rotamer), 4.77 (dd, J=10.7, 8.6 Hz, 1H), 4.61 (dd, J=10.7, 3.4 Hz, 1H), 3.64-3.43 (m, 2H), 3.24 (d, J=6.7 Hz, 1H), 3.19-3.01 (m, 2H), 2.93-2.62 (m, 5H).

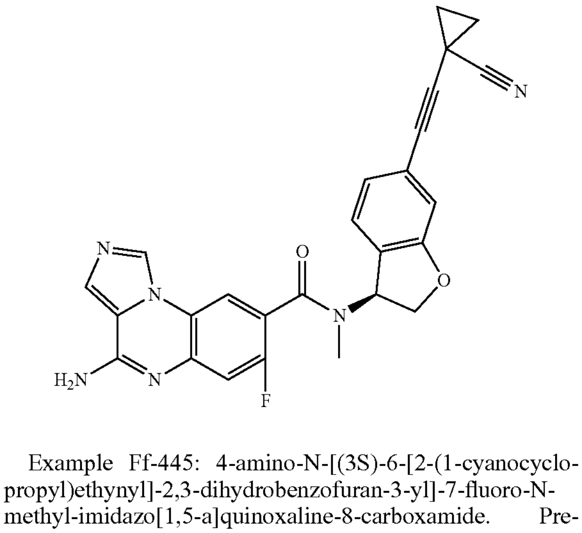

Example Ff-445: 4-amino-N-[(3S)-6-[2-(1-cyanocyclopropyl)ethynyl]-2,3-dihydrobenzofuran-3-yl]-7-fluoro-N-methyl-imidazo[1,5-a]quinoxaline-8-carboxamide. Prepared following general procedure example Ff-17 starting with intermediate 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 1-ethynylcyclopropanecarbonitrile. ES/MS: m/z=467.4 $[M+H]^+$. $^1H$ NMR (400 MHz, Methanol-d4) δ 9.37 (s, 1H), 8.76-8.24 (m, 2H), 77.44-7.53 (m, 1H), 7.19-7.42 (m, 1H), 7.19-7.01 (m, 1H), 7.01-6.85 (m, 1H), 6.50 (dd, J=8.8, 3.5 Hz, 0.55H major rotamer), 5.59 (t, J=6.4 Hz, 0.45H minor rotamer), 4.80 (dd, J=10.7, 8.8 Hz, 0.5H rotamer), 4.83-4.76 (m, 0.5H rotamer), 4.73-4.43 (m, 1.5H rotamer), 2.97-2.57 (m, 3H), 1.69-1.75 (m, 2H), 1.49-1.68 (m, 2H).

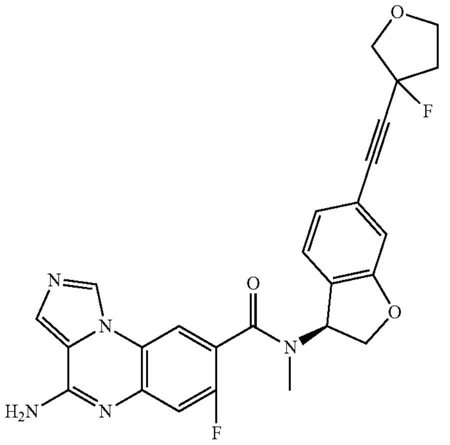 [SMILES: CN(C(=O)c1cc2c(cc1F)nc(N)c1cncn12)[C@@H]1COc2cc(C#CC3(F)CCOC3)ccc21]

Example Ff-446: 4-amino-7-fluoro-N-[(3S)-6-[2-(3-fluorotetrahydrofuran-3-yl)ethynyl]-2,3-dihydrobenzofuran-3-yl]-N-methyl-imidazo[1,5-a]quinoxaline-8-carboxamide. Prepared following general procedure example Ff-17 starting with intermediate 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 3-ethynyl-3-fluoro-tetrahydrofuran. ES/MS: m/z=490.1 $[M+H]^+$. $^1H$ NMR (400 MHz, Methanol-d4) δ 9.29 (s, 1H), 8.53-8.28 (m, 2H), 7.57-7.32 (m, 2H), 7.08-7.20 (m, 1H), 6.95-7.03 (m, 1H), 6.52 (dd, J=8.8, 3.5 Hz, 0.55H major rotamer), 5.61 (t, J=6.4 Hz, 0.45H minor rotamer), 4.85-4.57 (m, 2H), 4.30-4.10 (m, 1H), 4.03-4.10 (m, 2H), 3.85-4.02 (m, 1H), 2.93-2.67 (m, 3H), 2.67-2.26 (m, 2H).

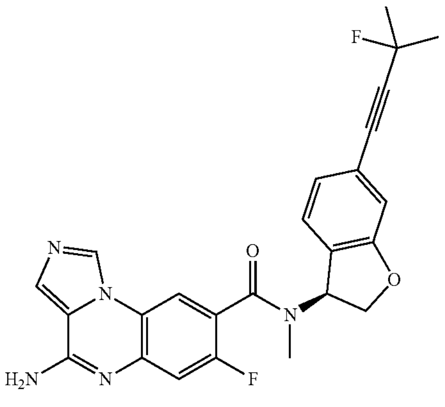 [SMILES: CN(C(=O)c1cc2c(cc1F)nc(N)c1cncn12)[C@@H]1COc2cc(C#CC(C)(C)F)ccc21]

Example Ff-447: 4-amino-7-fluoro-N-[(3S)-6-(3-fluoro-3-methyl-but-1-ynyl)-2,3-dihydrobenzofuran-3-yl]-N-methyl-imidazo[1,5-a]quinoxaline-8-carboxamide. Prepared following general procedure example Ff-17 starting with intermediate 4-amino-7-fluoro-N-[(3S)-6-iodo-2,3-dihydrobenzofuran-3-yl]-N-methyl-imidazo[1,5-a]quinoxaline-8-carboxamide (prepared following general procedure VI-F starting with 4-((tert-butoxycarbonyl)amino)-7-fluoro-imidazo[1,5-a]quinoxaline-8-carboxylic acid Af-1 and (S)-6-iodo-N-methyl-2,3-dihydrobenzofuran-3-amine Eh-16) and 3-fluoro-3-methyl-but-1-yne. ES/MS: m/z=462.0 $[M+H]^+$. $^1$H NMR (400 MHz, Methanol-d4) δ 9.26 (s, 1H), 8.63-8.30 (m, 2H), 7.61-7.26 (m, 2H), 7.02-7.15 (m, 1H), 7.01-6.85 (m, 1H), 6.51 (dd, J=8.8, 3.5 Hz, 0.55H major rotamer), 5.59 (t, J=6.4 Hz, 0.45H minor rotamer), 4.85-4.58 (m, 2H), 2.88 (d, J=0.7 Hz, 1H), 2.71 (d, J=1.1 Hz, 2H), 1.73 (d, J=6.1 Hz, 2.7H minor rotamer), 1.71 (d, J=6.1 Hz, 3.3H major

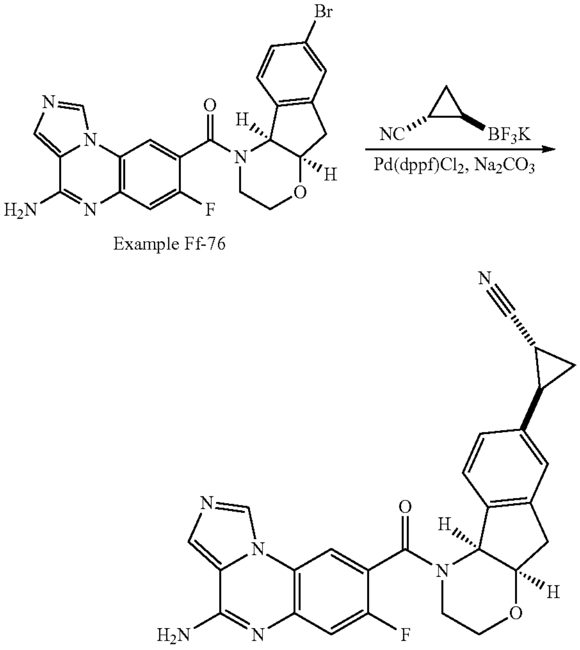

Example Ff-76

Example Ff-448

Example Ff-448: Trans-2-[(4aS,9aR)-4-(4-amino-7-fluoro-imidazo[1,5-a]quinoxaline-8-carbonyl)-3,4a,9,9a-tetrahydro-2H-indeno[2,1-b][1,4]oxazin-7-yl]cyclopropanecarbonitrile Example Ff-448 was prepared using the conditions reported in general procedure LXV-E starting with (4-amino-7-fluoroimidazo[1,5-a]quinoxalin-8-yl)((4aS,9aR)-7-bromo-2,3,9,9a-tetrahydroindeno[2,1-b][1,4]oxazin-4(4aH)-yl)methanone (example Ff-76) and trans-potassium (2-cyanocyclopropyl)trifluoroborate. ES/MS: m/z=469.3 $[M+H]^+$. $^1$H NMR (400 MHz, Methanol-d4) δ 9.48-9.15 (m, 1H), 8.48-8.56 (m, 1H), 8.43-8.23 (m, 1H), 8.02-7.53 (m, 1H), 7.51-7.40 (m, 1H), 7.35-7.21 (m, 1H), 7.20-7.02 (m, 1H), 5.98-5.82 (m, 0.6H), 5.03-4.88 (m, 0.4H), 4.68-4.36 (m, 2H), 3.83-3.49 (m, 2H), 3.40 (d, J=13.3 Hz, 1H), 3.28-3.11 (m, 1H), 2.95 (d, J=16.5 Hz, 1H), 2.77-2.58 (m, 1H), 1.92-1.72 (m, 1H), 1.72-1.42 (m, 2H).

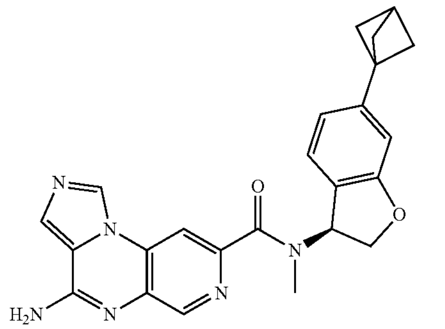 [SMILES: CN(C(=O)c1cc2c(cn1)nc(N)c1cncn12)[C@@H]1COc2cc(C34CC(C3)C4)ccc21]

Example Ff-449: 7-amino-N-[(3S)-6-(1-bicyclo[1.1.1]pentanyl)-2,3-dihydrobenzofuran-3-yl]-N-methyl-2,4,8,11-tetrazatricyclo[7.4.0.02,6]trideca-1(9),3,5,7,10,12-hexaene-12-carboxamide. Prepared using intermediate (S)-4-amino-N-(6-iodo-2,3-dihydrobenzofuran-3-yl)-N-methylimidazo[1,5-a]pyrido[3,4-e]pyrazine-8-carboxamide (prepared following general procedure VI-F starting with 4-((tert-butoxycarbonyl)amino)imidazo[1,5-a]pyrido[3,4-e]pyrazine-8-carboxylic acid Af-6 and (S)-6-iodo-N-methyl-2,3-dihydrobenzofuran-3-amine Eh-16) and 1-bromobicyclo[1.1.1]pentane following the reductive coupling procedure reported for example Ff-444. ES/MS: m/z=427.2 $[M+H]^+$. $^1$H NMR (400 MHz, Methanol-d4) δ 9.30-9.35 (m, 1H), 8.75-8.86 (m, 1H), 8.48-8.54 (m, 1H), 8.26 (d, J=7.2 Hz, 1H), 7.37 (d, J=7.8 Hz, 1H), 6.85-7.01 (m, 1H), 6.75-7.00 (m, 1H), 6.43 (dd, J=8.6, 3.3 Hz, 0.4H minor rotamer), 5.87 (t, J=6.2 Hz, 0.6H major rotamer), 4.86-4.79 (m, 1H), 4.73-4.58 (m, 1H), 3.47-3.55 (m, 2H), 3.18-3.02 (m, 3H), 2.92-2.71 (m, 5H).

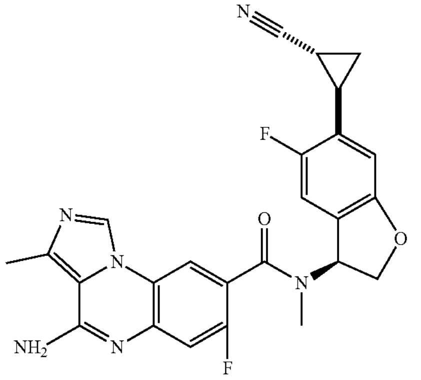

Example Ff-450: Trans-4-amino-N-[(3S)-6-(2-cyanocyclopropyl)-5-fluoro-2,3-dihydrobenzofuran-3-yl]-7-fluoro-N,3-dimethyl-imidazo[1,5-a]quinoxaline-8-carboxamide. Prepared following general procedure VI-F starting with starting with starting with 4-amino-7-fluoro-3-methyl-imidazo[1,5-a]quinoxaline-8-carboxylic acid Af-1 and 2-[(3S)-5-fluoro-3-(methylamino)-2,3-dihydrobenzofuran-6-yl]cyclopropanecarbonitrile Ebm-3. ES/MS: m/z=475.3 $[M+H]^+$. $^1$H NMR (400 MHz, Methanol-d4) δ 9.15 (s, 1H), 8.49-8.19 (m, 1H), 7.46 (t, J=11.3 Hz, 1H), 7.09-7.18 (m, 1H), 6.73-6.56 (m, 1H), 6.48 (t, J=8.1 Hz, 0.55H major rotamer), 5.57 (t, J=8.2 Hz, 0.45H minor rotamer), 4.78 (ddd, J=10.4, 8.7, 1.4 Hz, 1H), 4.74-4.59 (m, 1H), 2.83 (s, 1H), 2.80 (d, J=3.3 Hz, 3H), 2.71 (d, J=1.2 Hz, 3H), 1.97-1.81 (m, 1H), 1.79-1.60 (m, 1H), 1.60-1.45 (m, 1H).

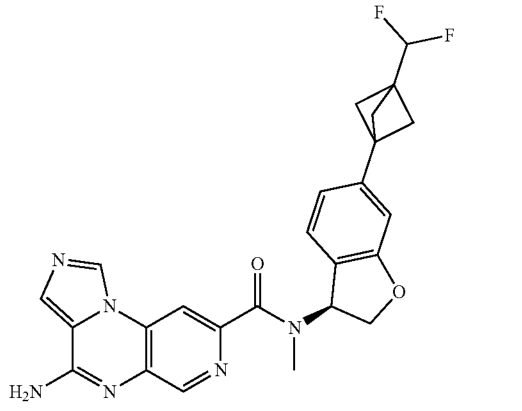 [SMILES: CN(C(=O)c1cc2c(cn1)nc(N)c1cncn12)[C@@H]1COc2cc(C34CC(C(F)F)(C3)C4)ccc21]

Example Ff-451: (S)-4-amino-N-(6-(3-(difluoromethyl)bicyclo[1.1.1]pentan-1-yl)-2,3-dihydrobenzofuran-3-yl)-N-methylimidazo[1,5-a]pyrido[3,4-e]pyrazine-8-carboxamide. Prepared using intermediate (S)-4-amino-N-(6-iodo-2,3-dihydrobenzofuran-3-yl)-N-methylimidazo[1,5-a]pyrido[3,4-e]pyrazine-8-carboxamide (prepared following general procedure VI-F starting with 4-((tert-butoxycarbonyl)amino)imidazo[1,5-a]pyrido[3,4-e]pyrazine-8-carboxylic acid Af-6 and (S)-6-iodo-N-methyl-2,3-dihydrobenzofuran-3-amine Eh-16) and 1-(difluoromethyl)-3-iodo-bicyclo[1.1.1]pentane following the reductive coupling procedure reported for example Ff-444. ES/MS: m/z=477.3 $[M+H]^+$. $^1H$ NMR (400 MHz, Methanol-d4) δ 9.30 (d, J=9.7 Hz, 1H), 8.77-8.85 (m, 1H), 8.46-8.52 (m, 1H), 8.22 (d, J=6.5 Hz, 1H), 7.39 (dd, J=7.6, 3.5 Hz, 1H), 6.96-6.82 (m, 1H), 6.73-6.80 (m, 1H), 6.44 (d, J=7.5 Hz, 0.45H minor rotamer), 6.08-5.66 (m, 1.55H major rotamer), 4.83-4.58 (m, 2H), 2.75-2.83 (m, 3H), 2.13 (d, J=7.3 Hz, 6H).

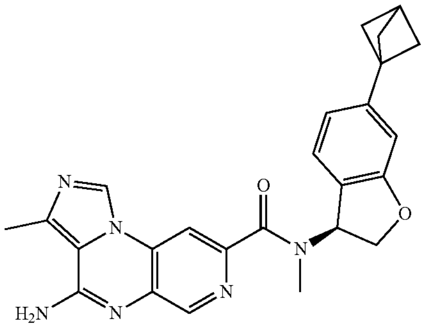 [SMILES: Cc1ncn2c1c(N)nc1cnc(C(=O)N(C)[C@@H]3COc4cc(C56CC(C5)C6)ccc43)cc12]

Example Ff-452: (S)-4-amino-N-(6-(bicyclo[1.1.1]pentan-1-yl)-2,3-dihydrobenzofuran-3-yl)-N,3-dimethylimidazo[1,5-a]pyrido[3,4-e]pyrazine-8-carboxamide. Prepared using intermediate (S)-4-amino-N-(6-iodo-2,3-dihydrobenzofuran-3-yl)-N,3-dimethylimidazo[1,5-a]pyrido[3,4-e]pyrazine-8-carboxamide (prepared following general procedure VI-F starting with 4-((tert-butoxycarbonyl)amino)-3-methylimidazo[1,5-a]pyrido[3,4-e]pyrazine-8-carboxylic acid Ag-2) and (S)-6-iodo-N-methyl-2,3-dihydrobenzofuran-3-amine Eh-16) and 1-bromobicyclo[1.1.1]pentane following the reductive coupling procedure reported for example Ff-444. ES/MS: m/z=441.3 $[M+H]^+$. 1H NMR (400 MHz, Methanol-d4) δ 9.24 (d, J=10.2 Hz, 1H), 8.75-8.83 (m, 1H), 8.42-8.50 (m, 1H), 7.36 (d, J=7.8 Hz, 1H), 6.90-6.95 (m, 1H), 6.78-6.84 (m, 1H), 6.44 (d, J=7.5 Hz, 0.45H minor rotamer), 5.85 (m, 0.55H major rotamer), 4.85-4.61 (m, 2H), 3.60-3.43 (m, 1H), 3.37 (s, 1H), 3.18-3.04 (m, 2H), 2.91-2.70 (m, 7H).

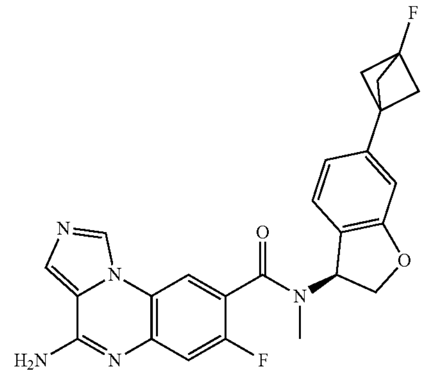 [SMILES: CN(C(=O)c1cc2c(cc1F)nc(N)c1cncn12)[C@@H]1COc2cc(C34CC(F)(C3)C4)ccc21]

Example Ff-453: 4-amino-7-fluoro-N-[(3S)-6-(3-fluoro-1-bicyclo[1.1.1]pentanyl)-2,3-dihydrobenzofuran-3-yl]-N-methyl-imidazo[1,5-a]quinoxaline-8-carboxamide. Prepared using intermediate (S)-4-amino-7-fluoro-N-(6-iodo-2,3-dihydrobenzofuran-3-yl)-N-methylimidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 1-fluoro-3-iodo-bicyclo[1.1.1]pentane following the reductive coupling procedure reported for example Ff-444. ES/MS: m/z=462.3 $[M+H]^+$. 1H NMR (400 MHz, Methanol-d4) δ 9.03 (s, 1H), 8.23 (d, J=6.3 Hz, 1H), 7.95 (d, J=3.8 Hz, 1H), 7.40-7.16 (m, 2H), 6.98-6.82 (m, 1H), 6.73-6.81 (m, 1H), 6.47 (d, J=7.5 Hz, 0.45H minor rotamer), 5.57 (m, 0.55H major rotamer), 4.82-4.56 (m, 2H), 2.91-2.61 (m, 3H), 2.29-2.36 (m, 6H).

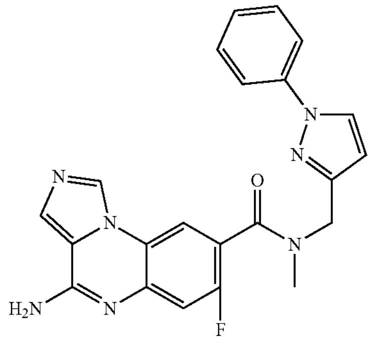 [SMILES: CN(Cc1ccn(-c2ccccc2)n1)C(=O)c1cc2c(cc1F)nc(N)c1cncn12]

Example Ff-454: 4-amino-7-fluoro-N-methyl-N-((1-phenyl-1H-pyrazol-3-yl)methyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and commercial N-methyl-1-(1-phenyl-1H-pyrazol-3-yl)methanamine. ES/MS: m/z=416.3 $[M+H]^+$. $^1H$ NMR (400 MHz, Chloroform-d) δ 8.89 (s, 1H), 8.62 (s, 1H), 8.38-8.43 (m, 1H), 8.14-8.18 (m, 1H), 7.88-7.94 (m, 1H), 7.58-7.65 (m, 2H), 7.46 (tt, J=7.9, 3.4 Hz, 3H), 7.34 (d, J=7.4 Hz, 1H), 6.39-6.48 (m, 1H), 4.68-4.74 (m, 2H), 3.34-2.87 (m, 3H).

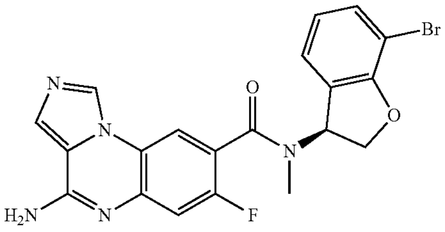 [SMILES: CN(C(=O)c1cc2c(cc1F)nc(N)c1cncn12)[C@@H]1COc2c(Br)cccc21]

Example Ff-455: (S)-4-amino-N-(7-bromo-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)-7-bromo-N-methyl-2,3-dihydrobenzofuran-3-amine Eh-17. ES/MS: m/z=456.3 $[M+H]^+$. $^1H$ NMR (400 MHz, Methanol-d4) δ 9.27 (s, 1H), 8.45 (d, J=5.8 Hz, 1H), 8.39 (d, J=3.4 Hz, 1H), 7.63-7.25 (m, 3H), 6.94 (dt, J=16.4, 7.8 Hz, 1H), 6.61 (dd, J=8.9, 3.6 Hz, 1H), 5.70 (s, 1H), 4.72 (dd, J=10.7, 3.7 Hz, 1H), 2.94-2.52 (m, 3H).

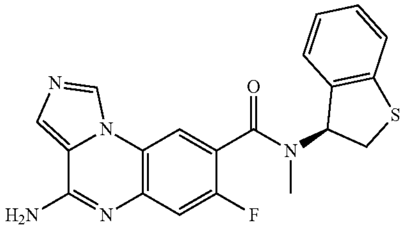 [SMILES: CN(C(=O)c1cc2c(cc1F)nc(N)c1cncn12)[C@@H]1CSc2ccccc21]

Example Ff-456: 4-amino-N-(2,3-dihydrobenzo[b]thiophen-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-methyl-2,3-dihydrobenzo[b]thiophen-3-amine Eh-18. ES/MS: m/z 394.3 $[M+H]^+$. $^1H$ NMR (400 MHz, Methanol-d4) δ 9.27 (d, J=2.9 Hz, 1H), 8.47 (d, J=5.9 Hz, 1H), 8.38 (s, 1H), 7.51 (t, J=9.5 Hz, 1H), 7.41-7.12 (m, 4H), 6.61 (dd, J=8.9, 5.5 Hz, 1H), 5.63 (s, 1H), 3.80 (dd, J=12.2, 8.9 Hz, 1H), 3.65-3.41 (m, 1H), 3.03-2.75 (m, 3H).

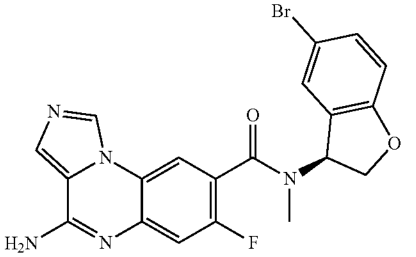 [SMILES: CN(C(=O)c1cc2c(cc1F)nc(N)c1cncn12)[C@@H]1COc2ccc(Br)cc21]

Example Ff-457: (S)-4-amino-N-(5-bromo-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)-5-bromo-N-methyl-2,3-dihydrobenzofuran-3-amine Eh-19. ES/MS: m/z=456.3 $[M+H]^+$. $^1H$ NMR (400 MHz, Methanol-d4) δ 9.27 (s, 1H), 8.46 (d, J=5.9 Hz, 1H), 8.40 (d, J=4.1 Hz, 1H), 7.59-7.35 (m, 3H), 6.84 (dd, J=17.1, 8.6 Hz, 1H), 6.50 (dd, J=8.9, 3.5 Hz, 1H), 5.71-5.49 (m, 1H), 4.81 (dd, J=10.7, 8.8 Hz, 1H), 4.66 (dd, J=10.7, 3.7 Hz, 1H), 2.90-2.64 (m, 3H).

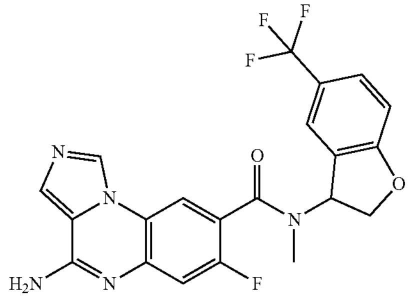 [SMILES: CN(C(=O)c1cc2c(cc1F)nc(N)c1cncn12)C1COc2ccc(C(F)(F)F)cc21]

Example Ff-458: 4-amino-7-fluoro-N-methyl-N-(5-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-methyl-5-(trifluoromethyl)-2,3-dihydrobenzofuran-3-amine Eh-20. ES/MS: m/z 446.3 $[M+H]^+$. $^1H$ NMR (400 MHz, Chloroform-d) δ 8.89-8.96 (m, 1H), 8.50 (d, J=8.9 Hz, 1H), 8.27 (s, 1H), 8.14 (d, J=5.5 Hz, 1H), 7.74-7.58 (m, 1H), 7.58-7.37 (m, 1H), 6.99 (dd, J=11.8, 8.5 Hz, 1H), 6.58 (dd, J=9.0, 3.5 Hz, 1H), 5.47 (dt, J=8.2, 3.6 Hz, 1H), 4.87 (dd, J=10.9, 8.8 Hz, 1H), 4.64 (dd, J=11.0, 3.6 Hz, 1H), 2.87 (s, 1H), 2.70 (d, J=2.0 Hz, 2H).

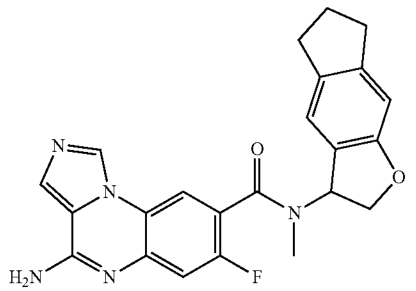 [SMILES: CN(C(=O)c1cc2c(cc1F)nc(N)c1cncn12)C1COc2cc3c(cc21)CCC3]

Example Ff-459: 4-amino-7-fluoro-N-methyl-N-(3,5,6,7-tetrahydro-2H-indeno[5,6-b]furan-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-methyl-3,5,6,7-tetrahydro-2H-indeno[5,6-b]furan-3-amine Eh-21. ES/MS: m/z 418.4 $[M+H]^+$. $^1H$ NMR (400 MHz, Methanol-d4) δ 9.23 (s, 1H), 8.33-8.38 (m, 2H), 7.43-7.49 (m, 1H), 7.13-7.19 (m, 1H), 6.70-6.74 (m 1H), 6.42 (dd, J=8.6, 3.1 Hz, 1H), 4.58 (dd, J=10.7, 3.3 Hz, 1H), 3.23 (d, J=7.3 Hz, 1H), 2.99-2.78 (m, 4H), 2.68 (d, J=1.2 Hz, 2H), 2.24-1.97 (m, 2H), 1.33 (t, J=7.3 Hz, 2H).

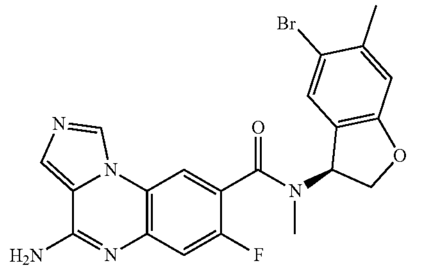 [SMILES: Cc1cc2c(cc1Br)[C@H](N(C)C(=O)c1cc3c(cc1F)nc(N)c1cncn13)CO2]

Example Ff-460: (S)-4-amino-N-(5-bromo-6-methyl-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)-5-bromo-N,6-dimethyl-2,3-dihydrobenzofuran-3-amine Eh-15. ES/MS: m/z=470.3 $[M+H]^+$. $^1$H NMR (400 MHz, Chloroform-d) δ 8.82 (d, J=12.9 Hz, 1H), 8.37 (d, J=5.5 Hz, 1H), 8.18-8.00 (m, 1H), 7.66-7.44 (m, 2H), 6.82 (d, J=12.4 Hz, 1H), 6.49 (dd, J=8.7, 3.2 Hz, 1H), 4.79 (dd, J=10.8, 8.7 Hz, 1H), 4.55 (dd, J=10.8, 3.3 Hz, 1H), 2.88 (s, 1H), 2.70 (d, J=2.0 Hz, 2H), 2.40 (d, J=10.2 Hz, 3H).

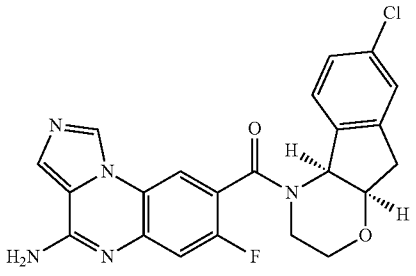 [SMILES: Nc1nc2cc(F)c(C(=O)N3CCO[C@@H]4Cc5cc(Cl)ccc5[C@@H]43)cc2n2cncc12]

Example Ff-461: (4-amino-7-fluoroimidazo[1,5-a]quinoxalin-8-yl)((4aS,9aR)-7-chloro-2,3,9,9a-tetrahydroindeno[2,1-b][1,4]oxazin-4(4aH)-yl)methanone. Prepared following general procedure VI-F starting with 4-((tert-butoxycarbonyl)amino)-7-fluoroimidazo[1,5-a]quinoxaline-8-carboxylic acid Af-1 and (4aS,9aR)-7-chloro-2,3,4,4a,9,9a-hexahydroindeno[2,1-b][1,4]oxazine Eas-4. ES/MS: m/z=438.3 $[M+H]^+$. $^1$H NMR (400 MHz, Methanol-d4) δ 9.38-9.24 (m, 1H), 8.49-8.59 (m, 1H), 8.34-8.40 (m, 1H), 7.44-7.54 (m, 1H), 7.41-7.14 (m, 3H), 5.94 (s, 1H), 4.45-455 (m, 2H), 3.68 (s, 2H), 3.54-3.36 (m, 1H), 3.33-3.16 (m, 2H), 3.10-2.80 (m, 2H).

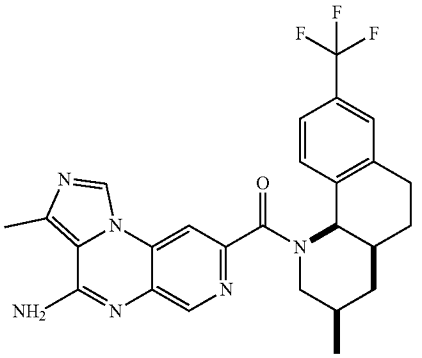

(±)

Example Ff-462: Rac-(4-amino-3-methylimidazo[1,5-a]pyrido[3,4-e]pyrazin-8-yl)((3R,4aS,10bR)-3-methyl-8-(trifluoromethyl)-3,4,4a,5,6,10b-hexahydrobenzo[h]quinolin-1(2H)-yl)methanone. Prepared following general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and cis-(3R,4aS,10bR)-3-methyl-8-(trifluoromethyl)-1,2,3,4,4a,5,6,10b octahydrobenzo[h]quinoline hydrochloride Eax-6. ES/MS: m/z=495.4 $[M+H]^+$. $^1$H NMR (400 MHz, Methanol-d4) δ 9.19-9.26 (m, 1H), 8.68-8.82 (m, 1H), 8.49 (d, J=3.3 Hz, 1H), 7.64-7.23 (m, 3H), 6.12-5.84 (m, 1H), 5.28 (s, 1H), 3.60-3.69 (m, 1H), 3.13-2.88 (m, 1H), 2.79 (d, J=10.4 Hz, 3H), 2.59-2.34 (m, 1H), 2.31-2.17 (m, 1H), 2.11-1.86 (m, 3H), 1.73 (d, J=13.3 Hz, 1H), 1.49-1.06 (m, 2H), 0.78-0.86 (m, 3H).

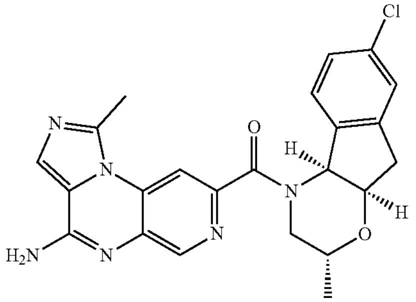 [SMILES: Cc1ncc2c(N)nc3cnc(C(=O)N4C[C@@H](C)O[C@@H]5Cc6cc(Cl)ccc6[C@@H]54)cc3n12]

Example Ff-463: (4-amino-1-methylimidazo[1,5-a]pyrido[3,4-e]pyrazin-8-yl)((2R,4aS,9aR)-7-chloro-2-methyl-2,3,9,9a-tetrahydroindeno[2,1-b][1,4]oxazin-4(4aH)-yl)methanone. Prepared following general procedure VI-F starting with 4-((tert-butoxycarbonyl)amino)-1-methylimidazo[1,5-a]pyrido[3,4-e]pyrazine-8-carboxylic acid Ag-1 and (4aS,9aR)-7-chloro-2-methyl-2,3,4,4a,9,9a-hexahydroindeno[2,1-b][1,4]oxazine Eas-5. Isolated as peak 1 after purification by HPLC. ES/MS: m/z=449.3 $[M+H]^+$. $^1$H NMR (400 MHz, Methanol-d4) δ 8.90 (d, J=8.2 Hz, 1H), 8.77 (s, 1H), 8.54 (dd, J=16.0, 7.2 Hz, 1H), 8.35 (dd, J=7.4, 3.2 Hz, 1H), 7.56 (d, J=6.2 Hz, 1H), 7.44-7.21 (m, 2H), 6.02-5.81 (m, 1H), 5.72-5.38 (m, 1H), 4.76-4.23 (m, 2H), 4.13-3.78 (m, 2H), 3.20 (d, J=6.3 Hz, 3H), 3.00-2.78 (m, 1H), 1.41 (d, J=6.7 Hz, 2H), 1.02-1.15 (m, 2H).

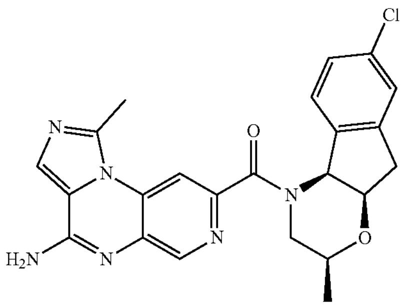 [SMILES: Cc1ncc2c(N)nc3cnc(C(=O)N4C[C@H](C)O[C@@H]5Cc6cc(Cl)ccc6[C@@H]54)cc3n12]

Example Ff-464: (4-amino-1-methylimidazo[1,5-a]pyrido[3,4-e]pyrazin-8-yl)((2S,4aS,9aR)-7-chloro-2-methyl-2,3,9,9a-tetrahydroindeno[2,1-b][1,4]oxazin-4(4aH)-yl)methanone. Prepared following general procedure VI-F starting with 4-((tert-butoxycarbonyl)amino)-1-methylimidazo[1,5-a]pyrido[3,4-e]pyrazine-8-carboxylic acid Ag-1 and (4aS,9aR)-7-chloro-2-methyl-2,3,4,4a,9,9a-hexahydroindeno[2,1-b][1,4]oxazine Eas-5. Isolated as peak 2 after purification by HPLC. ES/MS: m/z=449.3 $[M+H]^+$. $^1H$ NMR (400 MHz, Methanol-d4) δ 8.86 (s, 1H), 8.72 (s, 1H), 8.48-8.53 (m, 1H), 8.24 (d, J=5.9 Hz, 1H), 7.52 (d, J=7.9 Hz, 1H), 7.41-7.14 (m, 2H), 5.90 (d, J=3.9 Hz, 1H), 5.50 (d, J=3.7 Hz, 1H), 4.70-4.39 (m, 2H), 3.68 (s, 3H), 3.17 (d, J=7.9 Hz, 2H), 3.09-2.79 (m, 2H), 1.02-1.15 (m, 3H).

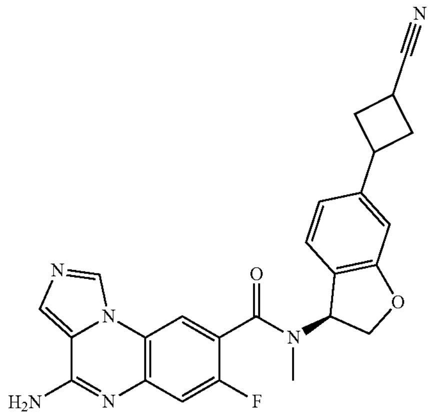 [SMILES: CN(C(=O)c1cc2c(cc1F)nc(N)c1cncn12)[C@@H]1COc2cc(C3CC(C#N)C3)ccc21]

Example Ff-465: (S)-4-amino-N-(6-(3-cyanocyclobutyl)-2,3-dihydrobenzofuran-3-yl)-7-fluoro-N-methylimidazo[1,5-a]quinoxaline-8-carboxamide. Prepared using intermediate (S)-4-amino-7-fluoro-N-(6-iodo-2,3-dihydrobenzofuran-3-yl)-N-methylimidazo[1,5-a]quinoxaline-8-carboxamide (prepared following general procedure VI-F starting with 4-((tert-butoxycarbonyl)amino)-7-fluoroimidazo[1,5-a]quinoxaline-8-carboxylic acid Af-1 and (S)-6-iodo-N-methyl-2,3-dihydrobenzofuran-3-amine Eh-16) and 3-bromocyclobutane-1-carbonitrile following the reductive coupling procedure reported for example Ff-444. ES/MS: m/z 457.3 $[M+H]^+$. $^1H$ NMR (400 MHz, Methanol-d4) δ 9.27 (s, 1H), 8.37-8.45 (m, 1H), 7.47-7.53 (m, 1H), 7.27-7.35 (m, 1H), 7.05-6.70 (m, 2H), 6.39-6.52 (m, 1H), 5.54 (t, J=6.6 Hz, 1H), 4.78 (dd, J=10.7, 8.7 Hz, 1H), 4.62 (dd, J=10.7, 3.5 Hz, 1H), 3.68 (s, 3H), 3.55-3.65 (m, 1H), 3.26 (td, J=8.3, 7.5, 2.4 Hz, 1H), 2.88-2.74 (m, 2H), 2.68 (s, 2H), 2.52-2.25 (m, 1H).

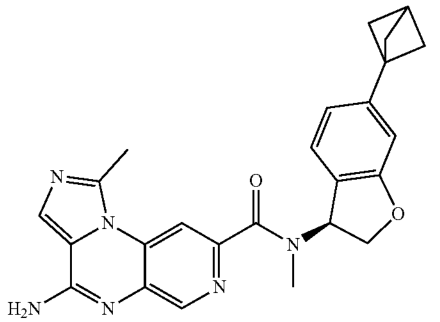 [SMILES: Cc1ncc2c(N)nc3cnc(C(=O)N(C)[C@@H]4COc5cc(C67CC(C6)C7)ccc54)cc3n12]

Example Ff-466: (S)-4-amino-N-(6-(bicyclo[1.1.1]pentan-1-yl)-2,3-dihydrobenzofuran-3-yl)-N,1-dimethylimidazo[1,5-a]pyrido[3,4-e]pyrazine-8-carboxamide. Prepared using intermediate (S)-4-amino-N-(6-iodo-2,3-dihydrobenzofuran-3-yl)-N,1-dimethylimidazo[1,5-a]pyrido[3,4-e]pyrazine-8-carboxamide (prepared following general procedure VI-F starting with 4-((tert-butoxycarbonyl)amino)-1-methylimidazo[1,5-a]pyrido[3,4-e]pyrazine-8-carboxylic acid Ag-1 and (S)-6-iodo-N-methyl-2,3-dihydrobenzofuran-3-amine Eh-16) and 1-bromobicyclo[1.1.1]pentane following the reductive coupling procedure reported for example Ff-444. ES/MS: m/z 441.3 $[M+H]^+$. $^1H$ NMR (400 MHz, Methanol-d4) δ 8.77-8.84 (m, 1H), 8.39-8.47 (m, 1H), 8.19 (t, J=3.1 Hz, 1H), 7.74-7.20 (m, 1H), 7.11-6.60 (m, 1H), 5.95 (t, J=6.4 Hz, 1H), 4.87 (m, 4H), 3.82-3.48 (m, 1H), 3.24-3.12 (m, 3H), 3.03 (s, 1H), 2.82 (d, J=8.4 Hz, 3H), 2.33-1.72 (m, 1H), 1.78-1.54 (m, 1H), 1.54-1.21 (m, 2H), 1.05 (t, J=7.3 Hz, 2H).

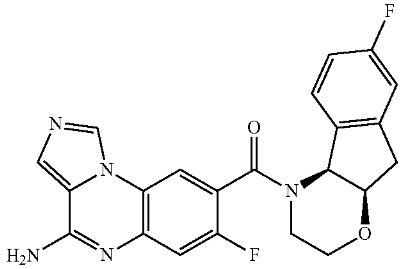 [SMILES: Nc1nc2cc(F)c(C(=O)N3CCO[C@@H]4Cc5cc(F)ccc5[C@@H]43)cc2n2cncc12]

Example Ff-467: (4-amino-7-fluoroimidazo[1,5-a]quinoxalin-8-yl)((4aS,9aR)-7-fluoro-2,3,9,9a-tetrahydroindeno[2,1-b][1,4]oxazin-4(4aH)-yl)methanone. Prepared following general procedure VI-F starting with 4-((tert-butoxycarbonyl)amino)-7-fluoroimidazo[1,5-a]quinoxaline-8-carboxylic acid Af-1 and rac-(4aS,9aR)-7-fluoro-2,3,4,4a,9,9a-hexahydroindeno[2,1-b][1,4]oxazine Et-7. Isolated as peak 2 after SFC (IC 5 uM 21×250 mm, MeOH 50%, 60 mL/min). ES/MS: m/z=422.2 $[M+H]^+$. $^1H$ NMR (400 MHz, DMSO-$d_6$) δ 9.31 (s, 0.65H major rotamer), 9.25 (s, 0.35H minor rotamer), 8.57 (brs, 2H), 8.51 (d, J=6.3 Hz, 1H), 8.17 (s, 0.65H major rotamer), 8.13 (s, 0.35H minor rotamer), 7.44-7.31 (m, 1H), 7.23-7.01 (m, 3H), 5.83 (s, 0.65H major rotamer), 4.94 (s, 0.35H minor rotamer), 4.46-4.21 (m, 1H), 3.33-2.62 (m, 4H), 2.16-1.97 (m, 0.65H major rotamer), 1.47 (brs, 0.35H minor rotamer), 1.32-1.22 (m, 1H).

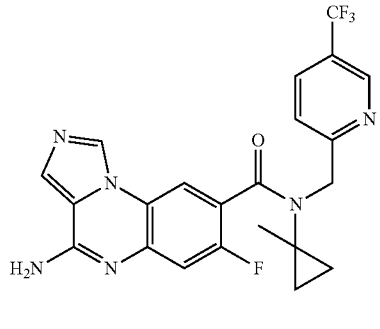 [SMILES: CC1(N(Cc2ccc(C(F)(F)F)cn2)C(=O)c2cc3c(cc2F)nc(N)c2cncn23)CC1]

Example Ff-468: 4-amino-7-fluoro-N-(1-methylcyclopropyl)-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 1-methyl-N-((5-(trifluoromethyl)pyridin-2-yl)methyl)cyclopropan-1-amine Ec-21. ES/MS: m/z=459.2 $[M+H]^+$. $^1H$ NMR (400 MHz, DMSO-$d_6$) δ 9.42 (s, 0.67H major rotamer), 9.27 (s, 0.33H minor rotamer), 9.11 (brs, 2H), 9.00-8.93 (m, 0.67H major rotamer), 8.94-8.88 (m, 0.33H minor rotamer), 8.52 (d, J=6.2 Hz, 0.67H major rotamer), 8.32 (s, 0.67H major rotamer), 8.28-8.19 (m, 1H+0.33H minor rotamer), 8.09-7.99 (m, 0.33H minor rotamer), 7.62-7.23 (m, 2H), 4.92 (s, 1.34H major rotamer), 4.68 (s, 0.66H minor rotamer), 1.31 (s, 2H major rotamer), 1.23 (s, 1H minor rotamer), 1.05-0.90 (m, 2H), 0.76 (brs, 0.66H minor rotamer), 0.48 (brs, 1.34H major rotamer).

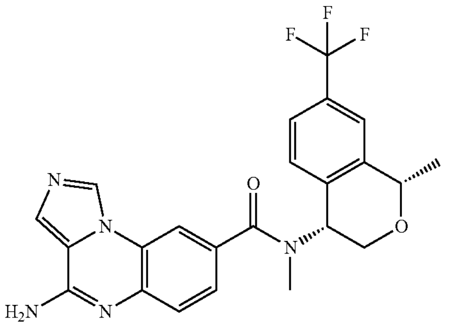 [SMILES: C[C@@H]1OC[C@H](N(C)C(=O)c2ccc3nc(N)c4cncn4c3c2)c2ccc(C(F)(F)F)cc21]

Example Ff-470: 4-amino-N-methyl-N-((1S,4R)-1-methyl-7-(trifluoromethyl)isochroman-4-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and rac-(1S,4R)—N,1-dimethyl-7-(trifluoromethyl)isochroman-4-amine hydrochloride salt (±)-Ei-2. Peak 1 of chiral SFC (IC Sum 21×250 mm, MeOH 45%, 60 mL/min). ES/MS: m/z=456.2 $[M+H]^+$. $^1H$ NMR (400 MHz, DMSO-$d_6$) δ 9.47 (s, 0.7H major rotamer), 9.43 (s, 0.3H minor rotamer), 9.21 (brs, 2H), 8.59 (s, 0.3H minor rotamer), 8.51 (s, 0.7H major rotamer), 8.39 (s, 1H), 7.78-7.51 (m, 5H), 5.72 (s, 1H), 4.92-4.68 (m, 2H), 4.38-4.05 (m, 2H), 2.80 (s, 0.9H minor rotamer), 2.75 (s, 2.1H major rotamer), 1.57 (d, J=6.4 Hz, 3H).

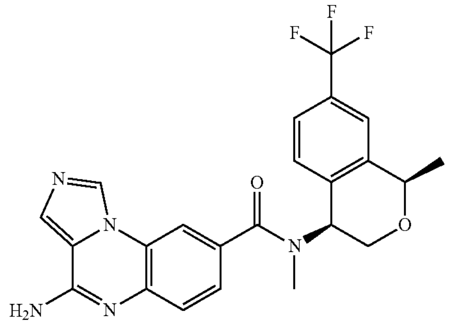 [SMILES: C[C@H]1OC[C@@H](N(C)C(=O)c2ccc3nc(N)c4cncn4c3c2)c2ccc(C(F)(F)F)cc21]

Example Ff-471: 4-amino-N-methyl-N-((1R,4S)-1-methyl-7-(trifluoromethyl)isochroman-4-yl)imidazo[1,5-a]quinoxaline-8-carboxamide. Prepared following general procedure VI-F starting with 4-((tert-butoxycarbonyl)amino)imidazo[1,5-a]quinoxaline-8-carboxylic acid Ae-1 and rac-(1S,4R)—N,1-dimethyl-7-(trifluoromethyl)isochroman-4-amine hydrochloride salt (±)-Ei-2. Peak 2 of chiral SFC (IC 5 μm 21×250 mm, MeOH 45%, 60 mL/min). ES/MS: m/z=456.2 $[M+H]^+$. $^1H$ NMR (400 MHz, DMSO-$d_6$) δ 9.47 (s, 0.7H major rotamer), 9.43 (s, 0.3H minor rotamer), 9.23 (brs, 2H), 8.59 (s, 0.3H minor rotamer), 8.51 (s, 0.7H major rotamer), 8.38 (s, 1H), 7.74-7.51 (m, 5H), 5.72 (s, 1H), 4.90-4.70 (m, 2H), 4.40-4.08 (m, 2H), 2.80 (s, 0.9H minor rotamer), 2.75 (s, 2.1H major rotamer), 1.57 (d, J=6.4 Hz, 3H).

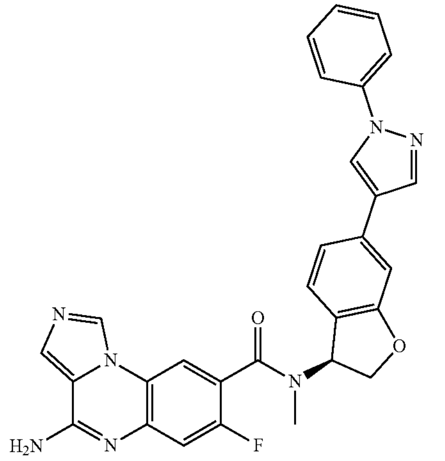 [SMILES: CN(C(=O)c1cc2c(cc1F)nc(N)c1cncn12)[C@@H]1COc2cc(-c3cnn(-c4ccccc4)c3)ccc21]

Example Ff-472: (S)-4-amino-7-fluoro-N-methyl-N-(6-(1-phenyl-1H-pyrazol-4-yl)-2,3-dihydrobenzofuran-3-yl)imidazo[1,5-a]quinoxaline-8-carboxamide. Prepared following the procedure reported for example Ff-95 starting with intermediates 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine hydrogen chloride Eh-5, and (1-phenylpyrazol-4-yl)boronic acid. ES/MS: m/z=520.2 $[M+H]^+$. $^1H$ NMR (400 MHz, DMSO-$d_6$) δ 9.33 (s, 1H), 9.03 (d, J=8.6 Hz, 2H), 8.90 (brs, 2H), 8.48 (d, J=6.2 Hz, 1H), 8.25 (s, 1H), 8.23 (s, 1H), 8.02-7.75 (m, 2H), 7.62-7.45 (m, 2H), 7.45-7.25 (m, 5H), 6.43 (dd, J=8.8, 3.7 Hz, 0.5H 1 rotamer), 5.49 (t, J=6.4 Hz, 0.5H $2^{nd}$ rotamer), 4.82 (dd, J=10.4, 8.9 Hz, 1H), 4.67-4.57 (m, 1H), 2.73 (s, 1.5H $1^{st}$ rotamer), 2.60 (s, 1.5H $2^{nd}$ rotamer).

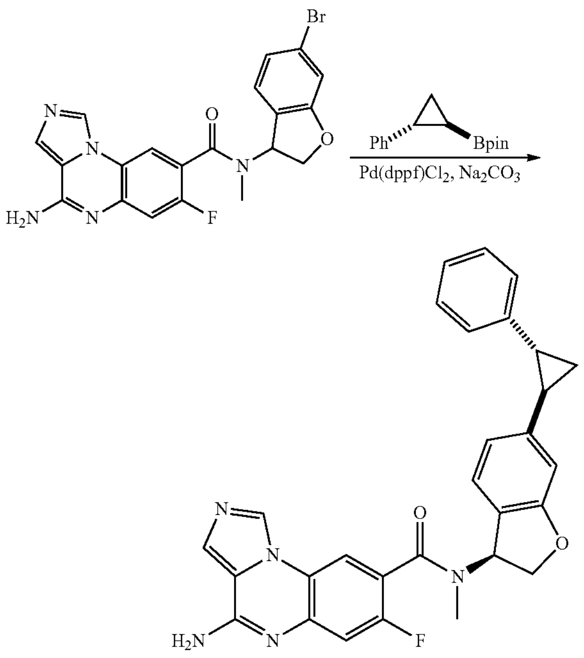

Example Ff-473

Example Ff-473: Trans-4-amino-7-fluoro-N-methyl-N-((3S)-6-(2-phenylcyclopropyl)-2,3-dihydrobenzofuran-3-yl)imidazo[1,5-a]quinoxaline-8-carboxamide. Example Ff-473 was prepared using the conditions reported in general procedure LXV-E starting with intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and trans-4,4,5,5-tetramethyl-2-(2-phenylcyclopropyl)-1,3,2-dioxaborolane. ES/MS: m/z=494.2 $[M+H]^+$. $^1H$ NMR (400 MHz, DMSO-$d_6$) δ 9.31 (s, 1H), 8.78 (brs, 2H), 8.45 (d, J=6.2 Hz, 1H), 8.23 (s, 1H), 7.51-7.34 (m, 1H), 7.34-6.96 (m, 6H), 6.85-6.63 (m, 2H), 6.37 (dd, J=8.9, 3.8 Hz, 0.4H minor rotamer), 5.47-5.38 (m, 0.4H minor rotamer), 4.75-4.70 (m, 0.6H major rotamer), 4.59-4.48 (m, 0.6H major rotamer), 2.68 (s, 2H major rotamer), 2.54 (s, 1H minor rotamer), 2.28-2.12 (m, 1H), 2.07-1.86 (m, 1H), 1.60-1.39 (m, 1H), 1.20 (brs, 1H), 1.11-0.82 (m, 1H), 0.08--0.06 (m, 1H).

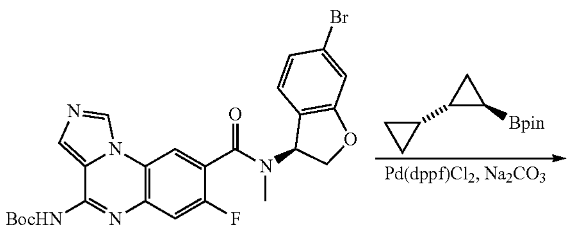

-continued

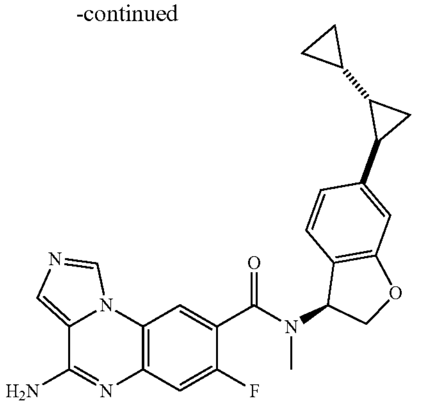

Example Ff-474

Example Ff-474: Trans-N-((3S)-6-([1,1'-bi(cyclopropan)]-2-yl)-2,3-dihydrobenzofuran-3-yl)-4-amino-7-fluoro-N-methylimidazo[1,5-a]quinoxaline-8-carboxamide. Example Ff-474 was prepared using the conditions reported in general procedure LXV-E starting with intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and trans-2-([1,1'-bi(cyclopropan)]-2-yl)-4,4,5,5-tetramethyl-1,3,2-dioxaborolane. ES/MS: m/z=458.2 $[M+H]^+$. $^1H$ NMR (400 MHz, DMSO-$d_6$) δ 9.29 (s, 0.6H major rotamer), 8.60 (brs, 2H), 8.43 (d, J=6.3 Hz, 0.4H minor rotamer), 8.20 (s, 1H), 7.46-7.33 (m, 1H), 7.17 (d, J=7.7 Hz, 0.6H major rotamer), 6.76-6.64 (m, 1H), 6.63-6.46 (m, 1H), 6.34 (dd, J=8.9, 3.6 Hz, 0.4H minor rotamer), 5.45-5.32 (d, J=6.6 Hz, 0.6H major rotamer), 4.72 (t, J=9.7 Hz, 0.4H minor rotamer), 4.58-4.44 (m, 1H), 2.66 (s, 1.8H major rotamer), 2.53 (s, 1.2H minor rotamer), 1.71-1.57 (m, 1H), 1.31-1.08 (m, 2H), 1.03-0.68 (m, 3H), 0.43-0.25 (m, 2H), 0.21-0.06 (m, 2H).

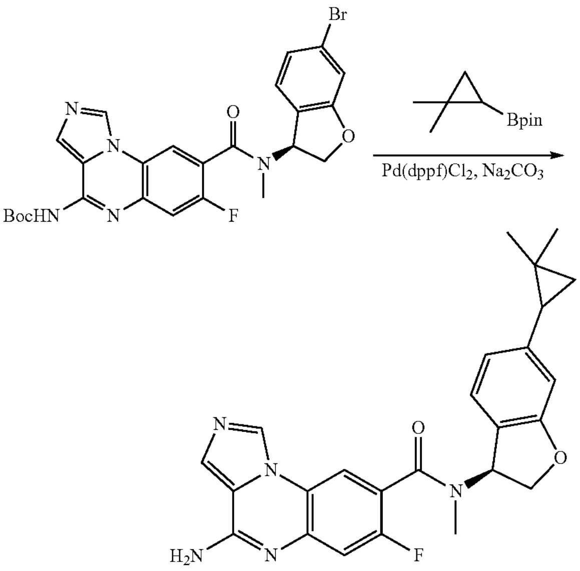

Example Ff-475

Example Ff-475: 4-amino-N-((3S)-6-(2,2-dimethylcyclopropyl)-2,3-dihydrobenzofuran-3-yl)-7-fluoro-N-methylimidazo[1,5-a]quinoxaline-8-carboxamide. Example Ff-475 was prepared using the conditions reported in general procedure LXV-E starting with intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and 2-(2,2-dimethylcyclopropyl)-4,4,5,5-tetramethyl-1,3,2-dioxaborolane. ES/MS: m/z=446.2 $[M+H]^+$. $^1H$ NMR (400 MHz, DMSO-$d_6$) δ 9.30 (s, 0.6H major rotamer), 8.61 (brs, 2H), 8.44 (d, J=6.2 Hz, 0.4H minor rotamer), 8.21 (s, 1H), 7.47-7.35 (m, 1H), 7.21 (d, J=7.7 Hz, 0.6H major rotamer), 6.90-6.58 (m, 3H), 6.49-6.28 (m, 0.4H minor rotamer), 5.50-5.40 (m, 0.6H major rotamer), 4.75 (t, J=9.6 Hz, 0.4H minor rotamer), 4.63-4.46 (m, 1H), 2.67 (s, 1.8H major rotamer), 2.53 (s, 1.2H major rotamer), 1.95-1.81 (m, 1H), 1.21-1.14 (m, 3H), 0.92-0.81 (m, 1H), 0.80-0.68 (m, 4H).

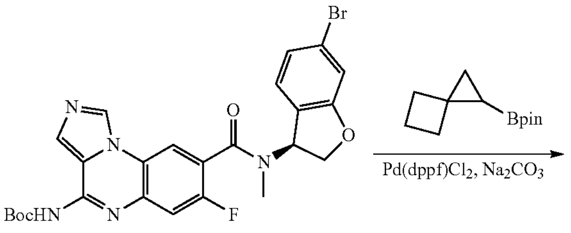

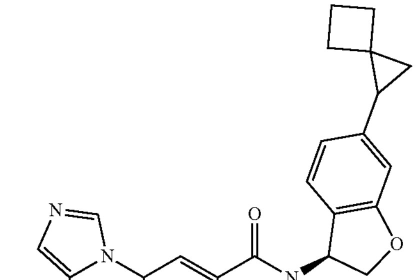

Example Ff-476

Example Ff-476: 4-amino-7-fluoro-N-methyl-N-((3S)-6-(spiro[2.3]hexan-1-yl)-2,3-dihydrobenzofuran-3-yl)imidazo[1,5-a]quinoxaline-8-carboxamide. Example Ff-476 was prepared using the conditions reported in general procedure LXV-E starting with intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and 4,4,5,5-tetramethyl-2-(spiro[2.3]hexan-1-yl)-1,3,2-dioxaborolane. ES/MS: m/z=458.2 $[M+H]^+$. $^1H$ NMR (400 MHz, DMSO-$d_6$) δ 9.32 (s, 0.5H rotamer), 8.91 (brs, 2H), 8.46 (d, J=6.2 Hz, 0.5H rotamer), 8.26 (d, J=2.8 Hz, 1H), 7.49-7.36 (m, 1H), 7.20 (d, J=7.7 Hz, 0.5H rotamer), 6.80-6.30 (m, 2H+0.5H rotamer), 5.41 (d, J=6.7 Hz, 0.5H rotamer), 4.74 (ddd, J=11.7, 8.9, 3.2 Hz, 0.5H rotamer), 4.64-4.50 (m, 2H), 2.67 (s, 1.5H rotamer), 2.53 (s, 1.5H rotamer), 2.33-1.67 (m, 8H), 1.11-0.82 (m, 2H+0.5H rotamer), 0.67-0.51 (m, 0.5H

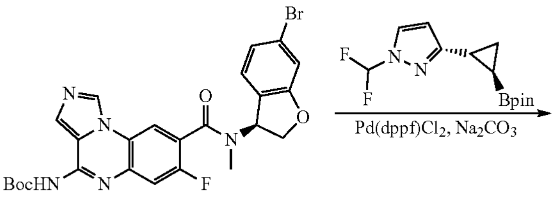

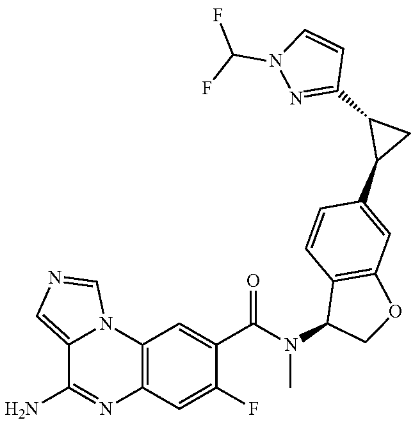

Example Ff-477

Example Ff-477: 4-amino-N—((S)-6-((1R,2R)-2-(1-(difluoromethyl)-1H-pyrazol-3-yl)cyclopropyl)-2,3-dihydrobenzofuran-3-yl)-7-fluoro-N-methylimidazo[1,5-a]quinoxaline-8-carboxamide. Example Ff-477 was prepared using the conditions reported in general procedure LXV-E starting with intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and 1-(difluoromethyl)-3-((1R,2R)-2-(4,4,5,5-tetramethyl-1,3,2-dioxaborolan-2-yl)cyclopropyl)-1H-pyrazole. ES/MS: m/z=534.2 $[M+H]^+$. $^1H$ NMR (400 MHz, DMSO-$d_6$) δ 9.32 (s, 0.6H major rotamer), 8.84 (brs, 2H), 8.46 (d, J=6.2 Hz, 0.4H minor rotamer), 8.26 (s, 1H), 8.14-8.05 (m, 1H), 7.88-7.34 (m, 1H), 7.75-7.64 (m, 2H), 7.56-7.37 (m, 1H), 7.20 (t, J=13.9 Hz, 1H), 6.90-6.61 (m, 2H), 6.37 (dd, J=8.8, 3.7 Hz, 0.4H minor rotamer), 5.42 (t, J=6.5 Hz, 0.6H major rotamer), 4.75 (dd, J=10.5, 8.9 Hz, 0.6H major rotamer), 4.54 (dd, J=10.4, 3.9 Hz, 1H+0.4H minor rotamer), 2.67 (s, 1.8H major rotamer), 2.55 (s, 1.2H minor rotamer), 2.20-1.97 (m, 2H), 1.45-1.19 (m, 2H).

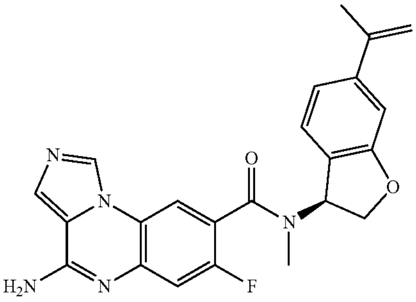 [SMILES: C=C(C)c1ccc2c(c1)OC[C@H]2N(C)C(=O)c1cc2c(cc1F)nc(N)c1cncn12]

Example Ff-478: (S)-4-amino-7-fluoro-N-methyl-N-(6-(prop-1-en-2-yl)-2,3-dihydrobenzofuran-3-yl)imidazo[1,5-a]quinoxaline-8-carboxamide. To a solution of intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5, 234 mg, 0.42 mmol) in triethylamine (0.18 mL, 3 equiv.) and ethanol (5 mL) was added potassium isopropenyltrifluoroborate (125 mg, 2 equiv.) and bis(diphenylphosphino)ferrocene]dichloropalladium(II) (25 mg, 0.1 equiv.) and the mixture was degassed with argon for 5 minutes. It was then heated to 90° C. for 2 hours, cooled back to room temperature and filtered over celite. Evaporation to dryness followed by column chromatography over silica gel gave example Ff-478 and intermediate tert-butyl (S)-(7-fluoro-8-(methyl(6-(prop-1-en-2-yl)-2,3-dihydrobenzofuran-3-yl)carbamoyl)imidazo[1,5-a]quinoxalin-4-yl)carbamate. ES/MS: m/z=418.1 $[M+H]^+$. $^1H$ NMR (400 MHz, DMSO-$d_6$) δ 9.28 (s, 1H), 8.59 (brs, 2H), 8.43 (d, J=6.3 Hz, 0.6H major rotamer), 8.17 (brs, 1H+0.4H minor rotamer), 7.53-7.10 (m, 1H), 7.08-6.92 (m, 1H), 6.45-6.39 (m, 1H), 5.55-5.39 (m, 2H), 5.12 (d, J=5.9 Hz, 1H), 4.79 (t, J=9.7 Hz, 1H), 4.68-4.53 (m, 2H), 2.70 (s, 1.8H major rotamer), 2.57 (s, 1.2H minor rotamer), 2.11 (s, 1.2H minor rotamer), 2.10 (s, 1.8H major rotamer).

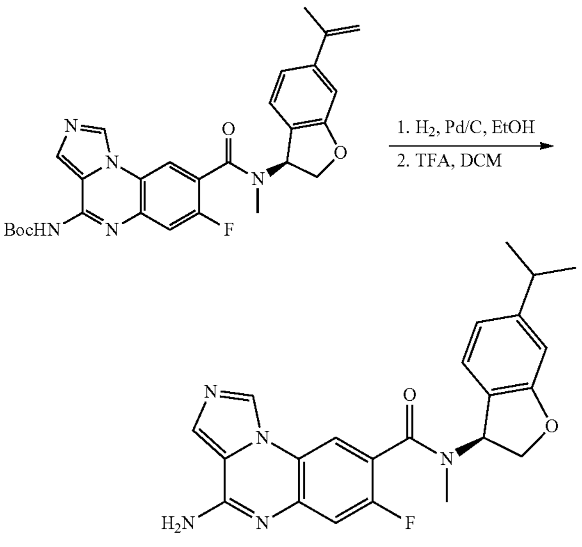

Example Ff-479

Example Ff-479: (S)-4-amino-7-fluoro-N-(6-isopropyl-2,3-dihydrobenzofuran-3-yl)-N-methylimidazo[1,5-a]quinoxaline-8-carboxamide. Pd/C (10% w/w, 50 mg) was added to a solution of intermediate tert-butyl (S)-(7-fluoro-8-(methyl(6-(prop-1-en-2-yl)-2,3-dihydrobenzofuran-3-yl)carbamoyl)imidazo[1,5-a]quinoxalin-4-yl)carbamate (42 mg, see example Ff-478) in EtOAc (2 mL). The mixture was degassed with argon and then placed under an atmosphere of hydrogen. It was stirred at room temperature until full conversion. The mixture was then filtered and evaporated to dryness. The residue was taken in DCM (1 mL) and TFA (1 mL) was added. Upon completion, the volatiles were evaporated and the residue purified by HPLC to deliver example Ff-479. ES/MS: m/z=420.2 $[M+H]^+$. $^1H$ NMR (400 MHz, DMSO-$d_6$) δ 9.33 (s, 0.5H rotamer), 8.94 (brs, 2H), 8.46 (d, J=6.2 Hz, 0.5H rotamer), 8.26 (d, J=2.3 Hz, 1H), 7.50-7.15 (m, 2H), 6.97-6.84 (m, 1H), 6.81 (s, 0.5H rotamer), 6.75 (s, 0.5H rotamer), 6.37 (dd, J=8.9, 3.7 Hz, 0.5H rotamer), 5.52-5.40 (m, 0.5H), 4.74 (dd, J=10.4, 8.9 Hz, 0.5H rotamer), 4.60-4.47 (m, 1+0.5H rotamer), 2.97-2.80 (m, 1H), 2.68 (s, 1.5H rotamer), 2.58-2.52 (m, 1.5H rotamer), 1.27-1.10 (m, 6H).

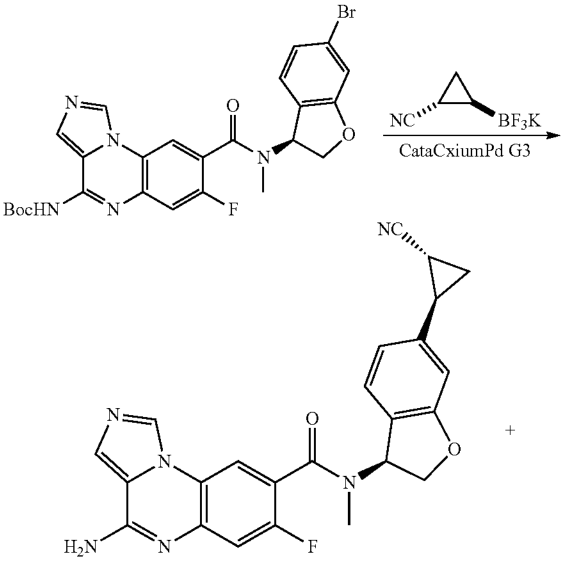

Example Ff-480

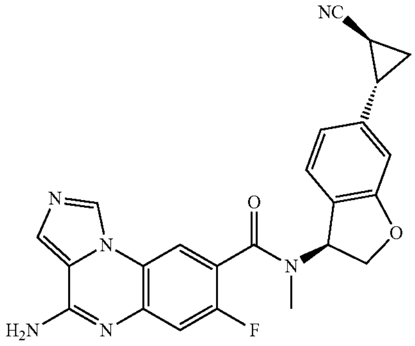

Example Ff-481

Example 480: 4-amino-N—((S)-6-((1R,2R)-2-cyanocyclopropyl)-2,3-dihydrobenzofuran-3-yl)-7-fluoro-N-methylimidazo[1,5-a]quinoxaline-8-carboxamide. Example Ff-480 was prepared using the conditions reported in general procedure LXV-E starting with intermediate tert-butyl (S)-

(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and trans-2-(trifluoro-14-boraneyl)cyclopropane-1-carbonitrile, potassium salt, cataCXium A PD G3 was used as a catalyst. Peak 1 of chiral SFC (AD-H Sum 21×250 mm, MeOH 35%, 60 mL/min). The stereochemistry was arbitrarily assigned. ES/MS: m/z=443.2 $[M+H]^+$. $^1H$ NMR (400 MHz, DMSO-$d_6$) δ 9.29 (s, 0.55H major rotamer), 8.63 (brs, 2H), 8.43 (d, J=6.3 Hz, 0.45H minor rotamer), 8.20 (s, 1H), 7.47-7.34 (m, 1H), 7.25 (d, J=7.7 Hz, 1H), 6.96-6.83 (m, 1H), 6.76 (d, J=1.4 Hz, 0.45H minor rotamer), 6.71 (d, J=1.5 Hz, 0.55H major rotamer), 6.38 (dd, J=9.0, 3.8 Hz, 0.45H minor rotamer), 5.44 (t, J=6.5 Hz, 0.55H major rotamer), 4.75 (dd, J=10.5, 8.9 Hz, 0.55H major rotamer), 4.62-4.45 (m, 1H+0.45H minor rotamer), 2.74-2.67 (m, 1H), 2.66 (s, 1.65H major rotamer), 2.54 (s, 1.35H minor rotamer), 2.10-1.90 (m, 1H), 1.67-1.57 (m, 1H), 1.55-1.44 (m, 1H).

Example Ff-481: 4-amino-N—((S)-6-((1S,2S)-2-cyanocyclopropyl)-2,3-dihydrobenzofuran-3-yl)-7-fluoro-N-methylimidazo[1,5-a]quinoxaline-8-carboxamide. Example Ff-482 was prepared using the conditions reported in general procedure LXV-E starting with intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and trans-2-(trifluoro-14-boraneyl)cyclopropane-1-carbonitrile, potassium salt, cataCXium A PD G3 was used as a catalyst. Peak 2 of chiral SFC (AD-H Sum 21×250 mm, MeOH 35%, 60 mL/min). The stereochemistry was arbitrarily assigned. ES/MS: m/z=443.2 $[M+H]^+$. $^1H$ NMR (400 MHz, DMSO-$d_6$) δ 9.29 (s, 0.55H major rotamer), 8.68 (brs, 2H), 8.44 (d, J=6.3 Hz, 0.45H minor rotamer), 8.21 (s, 1H), 7.46-7.34 (m, 1H), 7.25 (d, J=7.7 Hz, 1H), 6.93-6.83 (m, 1H), 6.75 (d, J=1.4 Hz, 0.45H minor rotamer), 6.69 (d, J=1.5 Hz, 0.55H major rotamer), 6.37 (dd, J=9.0, 3.8 Hz, 0.45H minor rotamer), 5.44 (t, J=6.5 Hz, 0.55H major rotamer), 4.76 (dd, J=10.5, 8.9 Hz, 0.55H major rotamer), 4.62-4.47 (m, 1H+0.45H minor rotamer), 2.74-2.67 (m, 1H), 2.66 (s, 1.65H major rotamer), 2.54 (s, 1.35H minor rotamer), 2.12-1.99 (m, 1H), 1.66-1.56 (m, 1H), 1.54-1.42 (m, 1H).

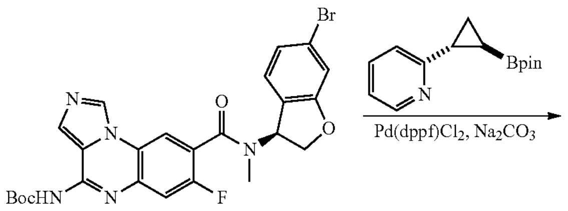

-continued

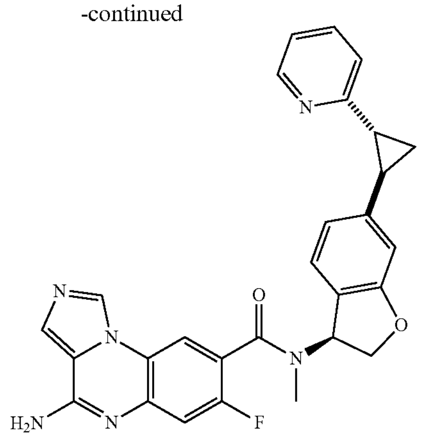

Example Ff-482

Example Ff-482: Trans-4-amino-7-fluoro-N-methyl-N-((3S)-6-(2-(pyridin-2-yl)cyclopropyl)-2,3-dihydrobenzofuran-3-yl)imidazo[1,5-a]quinoxaline-8-carboxamide. Example Ff-482 was prepared using the conditions reported in general procedure LXV-E starting with intermediate tert-butyl (S)-(8-((6-bromo-2,3-dihydrobenzofuran-3-yl)(methyl)carbamoyl)-7-fluoroimidazo[1,5-a]quinoxalin-4-yl)carbamate (ES/MS: m/z=556.1 $[M+H]^+$, prepared following step 1 of general procedure VI-F starting with 4-((tert-butoxycarbonyl)amino)-7-fluoroimidazo[1,5-a]quinoxaline-8-carboxylic acid Af-1 and (S)-6-bromo-N-methyl-2,3-dihydrobenzofuran-3-amine hydrogen chloride Eh-5) and trans-2-(2-(4,4,5,5-tetramethyl-1,3,2-dioxaborolan-2-yl)cyclopropyl)pyridine. ES/MS: m/z=495.1 $[M+H]^+$. $^1H$ NMR (400 MHz, DMSO-$d_6$) δ 9.26 (m, 0.6H major rotamer), 8.77-8.63 (m, 1H), 8.55 (brs, 2H), 8.41 (d, J=6.3 Hz, 0.4H minor rotamer), 8.16 (s, 1H), 7.81-7.69 (m, 2H), 7.44-7.14 (m, 2H), 6.96-6.66 (m, 1H+0.6H major rotamer), 6.39 (dd, J=8.9, 3.8 Hz, 0.4H minor rotamer), 5.46 (t, J=6.6 Hz, 0.6H major rotamer), 4.76 t, J=9.9 Hz, 0.4H minor rotamer), 4.65-4.51 (m, 2H), 2.67 (s, 1.8H major rotamer), 2.66-2.53 (m, 1H), 2.55 (s, 1.2H minor rotamer), 1.93-1.74 (m, 2H).

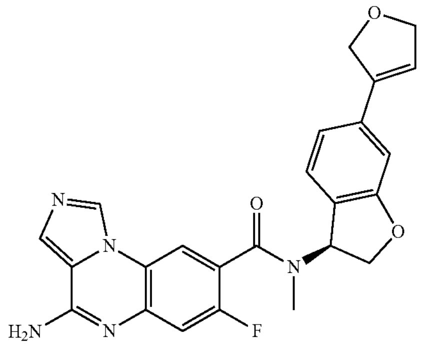 [SMILES: CN(C(=O)c1cc2c(cc1F)nc(N)c1cncn12)[C@@H]1COc2cc(C3=CCOC3)ccc21]

Example Ff-483: (S)-4-amino-N-(6-(2,5-dihydrofuran-3-yl)-2,3-dihydrobenzofuran-3-yl)-7-fluoro-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine Eh-5 and 2-(2,5-dihydrofuran-3-yl)-4,4,5,5-tetramethyl-1,3,2-dioxaborolane. ES/MS:

m/z=446.2 $[M+H]^+$. $^1H$ NMR (400 MHz, DMSO-$d_6$) δ 9.29 (s, 0.55H major rotamer), 8.62 (brs, 2H), 8.44 (d, J=6.3 Hz, 0.45H minor rotamer), 8.20 (s, 1H), 7.55-7.20 (m, 2H), 7.12-6.93 (m, 2H), 6.54 (d, J=8.1 Hz, 0.45H minor rotamer), 6.41 (dd, J=8.9, 3.8 Hz, 0.55H major rotamer), 5.49 (t, J=6.4 Hz, 0.55H major rotamer), 4.98-4.68 (m, 4H+0.45H minor rotamer), 4.66-4.50 (m, 1H), 2.70-2.65 (m, 1H), 2.69 (s, 1.65H major rotamer), 2.57 (s, 1.35H minor rotamer).

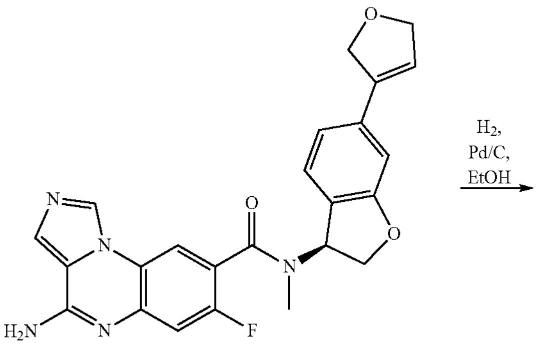

Example Ff-483

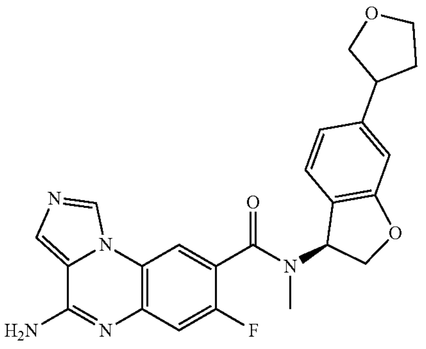

Example Ff-484

Example Ff-484: Rac-4-amino-7-fluoro-N-methyl-N-((3S)-6-(tetrahydrofuran-3-yl)-2,3-dihydrobenzofuran-3-yl) imidazo[1,5-a]quinoxaline-8-carboxamide. Prepared starting from example Ff-483 following step 1 of the procedure reported for example Ff-479. ES/MS: m/z=448.2 $[M+H]^+$. $^1H$ NMR (400 MHz, DMSO-$d_6$) δ 9.29 (s, 0.65H major rotamer), 8.61 (brs, 2H), 8.44 (d, J=6.3 Hz, 0.35H minor rotamer), 8.20 (s, 1H), 7.49-7.18 (m, 2H), 6.99-6.76 (m, 3H), 6.38 (dd, J=8.9, 3.8 Hz, 1H), 5.44 (t, J=6.6 Hz, 1H), 4.75 (dd, J=10.4, 8.9 Hz, 0.65H major rotamer), 4.64-4.49 (m, 1H+0.35H minor rotamer), 4.02-3.91 (m, 2H), 3.54-3.30 (m, 2H), 2.68 (s, 1.95H), 2.55 (s, 1.05H), 2.39-2.16 (m, 1H), 1.99-1.84 (m, 1H).

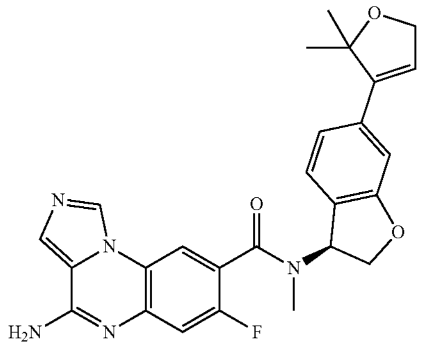 [SMILES: CN(C(=O)c1cc2c(cc1F)nc(N)c1cncn12)[C@@H]1COc2cc(C3=CCOC3(C)C)ccc21]

Example Ff-485: (S)-4-amino-N-(6-(2,2-dimethyl-2,5-dihydrofuran-3-yl)-2,3-dihydrobenzofuran-3-yl)-7-fluoro-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, (S)-6-bromo-N-methyl-2,3-dihydrobenzofuran-3-amine Eh-5 and 2-(2,2-dimethyl-2,5-dihydrofuran-3-yl)-4,4,5,5-tetramethyl-1,3,2-dioxaborolane. ES/MS: m/z=474.2 $[M+H]^+$. $^1H$ NMR (400 MHz, DMSO-$d_6$) δ 9.30 (s, 0.5H rotamer), 8.62 (brs, 2H), 8.45 (d, J=6.3 Hz, 0.5H rotamer), 8.20 (s, 1H), 7.44-7.24 (m, 2H), 7.20-7.03 (m, 1H), 6.99 (d, J=1.5 Hz, 0.5H rotamer), 6.94 (d, J=1.4 Hz, 0.5H rotamer), 6.41 (dd, J=9.0, 3.8 Hz, 0.5H rotamer), 6.27 (d, J=7.2 Hz, 0.5H rotamer), 5.49 (t, J=6.5 Hz, 0.5H rotamer), 4.79 (dd, J=10.4, 9.0 Hz, 0.5H rotamer), 4.68-4.47 (m, 4H), 2.71 (s, 1.5H rotamer), 2.58 (s, 1.5H rotamer), 1.41 (s, 3H), 1.39 (s, 1.5H rotamer), 1.38 (s, 1.5H rotamer).

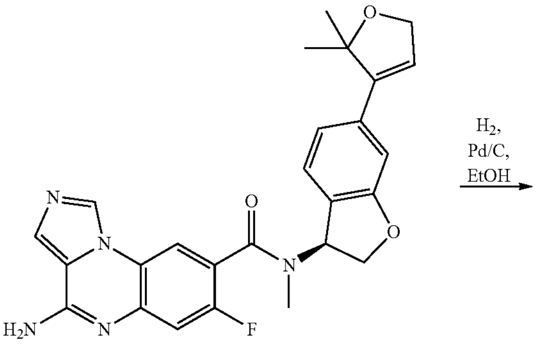

Example Ff-485

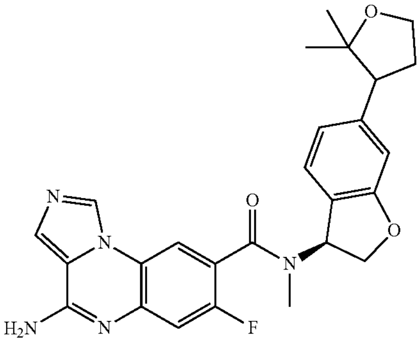

Example Ff-486

Example Ff-486: 4-amino-N-((3S)-6-(2,2-dimethyltetrahydrofuran-3-yl)-2,3-dihydrobenzofuran-3-yl)-7-fluoro-N-methylimidazo[1,5-a]quinoxaline-8-carboxamide. Prepared starting from example Ff-485 following step 1 of the procedure reported for example Ff-479. ES/MS: m/z=476.2 $[M+H]^+$. $^1$H NMR (400 MHz, DMSO-$d_6$) δ 9.27 (s, 0.5H rotamer), 8.52 (brs, 2H), 8.42 (d, J=6.3 Hz, 0.5H), 8.16 (s, 1H), 7.60-7.17 (m, 2H), 7.02-6.73 (m, 2H), 6.40 (dd, J=8.8, 3.7 Hz, 0.5H rotamer), 5.51-5.41 (s, 0.5H rotamer), 4.82-4.71 (m, 0.5H rotamer), 4.66-4.46 (m, 1H+0.5H rotamer), 4.12-3.75 (m, 2H), 3.11-2.95 (m, 1H), 2.67 (d, J=2.5 Hz, 1.5H rotamer), 2.54 (s, 1.5H rotamer), 2.39-2.16 (m, 2H), 1.22 (s, 1.5H rotamer), 1.19 (d, J=2.3 Hz, 1.5H rotamer), 0.75 (s, 1.5H rotamer), 0.69 (d, J=5.0 Hz, 1.5H rotamer).

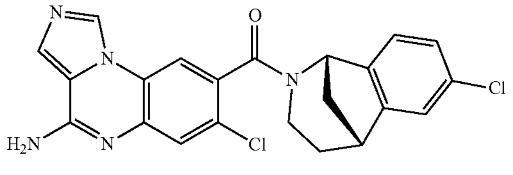 [SMILES: Nc1nc2cc(Cl)c(C(=O)N3CC[C@@H]4C[C@H]3c3ccc(Cl)cc34)cc2n2cncc12]

Example Ff-487: (4-amino-7-chloroimidazo[1,5-a]quinoxalin-8-yl)((1S,5R)-7-chloro-1,3,4,5-tetrahydro-2H-1,5-methanobenzo[c]azepin-2-yl)methanone. Prepared following general procedure VI-F starting with 4-((tert-butoxycarbonyl)amino)-7-chloroimidazo[1,5-a]quinoxaline-8-carboxylic acid Af-2 and (1S,5R)-7-chloro-2,3,4,5-tetrahydro-1H-1,5-methanobenzo[c]azepine Ef-3. ES/MS: m/z=438.2 $[M+H]^+$. $^1$H NMR (400 MHz, DMSO-$d_6$) δ 9.48-9.24 (m, 1H), 8.90 (brs, 2H), 8.54 (s, 0.65H major rotamer), 8.43 (s, 0.35H minor rotamer), 8.32-8.18 (m, 1H), 7.75-7.21 (m, 5H), 5.92-5.84 (m, 0.35H minor rotamer), 4.3-4.52 (m, 1H), 4.33-4.21 (m, 0.65H), 3.45-3.31 (m, 0.65H major rotamer), 3.22-3.01 (m, 1H), 2.36-1.71 (m, 4H), 1.61-1.44 (m, 0.35H minor rotamer).

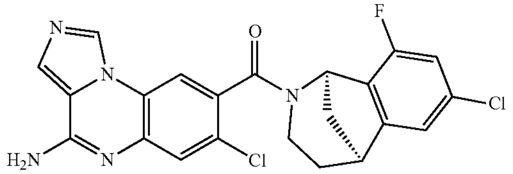 [SMILES: Nc1nc2cc(Cl)c(C(=O)N3CC[C@H]4C[C@@H]3c3c(F)cc(Cl)cc34)cc2n2cncc12]

Example Ff-488: (4-amino-7-chloroimidazo[1,5-a]quinoxalin-8-yl)((1R,5S)-7-chloro-9-fluoro-1,3,4,5-tetrahydro-2H-1,5-methanobenzo[c]azepin-2-yl)methanone. Prepared following general procedure VI-F starting with 4-((tert-butoxycarbonyl)amino)-7-chloroimidazo[1,5-a]quinoxaline-8-carboxylic acid Af-2 and (1R,5S)-7-chloro-9-fluoro-2,3,4,5-tetrahydro-1H-1,5-methanobenzo[c]azepine Ef-10. ES/MS: m/z=456.2 $[M+H]^+$. $^1$H NMR (400 MHz, Methanol-$d_4$) δ 9.36-9.13 (m, 1H), 8.51-8.18 (m, 2H), 7.82-7.58 (m, 1H), 7.49-7.04 (m, 2H), 6.07-6.01 (m, 0.6H major rotamer), 4.50-4.40 (m, 0.4H minor rotamer), 3.76-3.64 (m, 1H), 3.30-3.21 (m, 0.4H minor rotamer), 2.81-2.35 (m, 1H), 2.38-1.86 (m, 3H), 1.75-1.60 (m, 0.6H major rotamer).

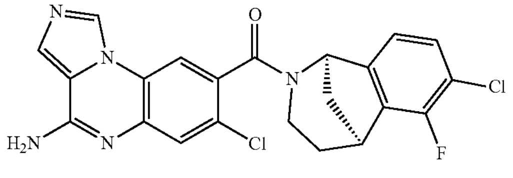 [SMILES: Nc1nc2cc(Cl)c(C(=O)N3CC[C@H]4C[C@@H]3c3ccc(Cl)c(F)c34)cc2n2cncc12]

Example Ff-489: (4-amino-7-chloroimidazo[1,5-a]quinoxalin-8-yl)((1R,5S)-7-chloro-6-fluoro-1,3,4,5-tetrahydro-2H-1,5-methanobenzo[c]azepin-2-yl)methanone. Prepared following general procedure VI-F starting with 4-((tert-butoxycarbonyl)amino)-7-chloroimidazo[1,5-a]quinoxaline-8-carboxylic acid Af-2 and (1R,5S)-7-chloro-6-fluoro-2,3,4,5-tetrahydro-1H-1,5-methanobenzo[c]azepine Ef-5. ES/MS: m/z=456.2 $[M+H]^+$. $^1$H NMR (400 MHz, DMSO-$d_6$) δ 9.39-9.25 (m, 1H), 8.84 (brs, 2H), 8.58-8.14 (m, 2H), 7.76-7.48 (m, 1H), 7.45-7.23 (m, 2H), 6.16-6.02 (m, 1H), 4.92-4.79 (m, 0.4H minor rotamer), 4.39-4.25 (m, 0.6H major rotamer), 3.53-3.40 (m, 1H), 3.21-3.05 (m, 1H), 2.40-1.87 (m, 4H), 1.86-1.40 (m, 1H).

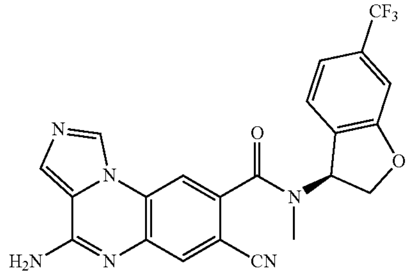

Example Ff-490: (S)-4-amino-7-cyano-N-methyl-N-(6-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)-7-cyanoimidazo[1,5-a]quinoxaline-8-carboxylic acid Al-1 and (S)—N-methyl-6-(trifluoromethyl)-2,3-dihydrobenzofuran-3-amine hydrogen chloride Eh-1. ES/MS: m/z=453.2 $[M+H]^+$. $^1$H NMR (400 MHz, DMSO-$d_6$) δ 9.28 (s, 1H), 8.60 (s, 0.4H minor rotamer), 8.49 (s, 0.6H major rotamer), 8.20 (brs, 2H), 8.09 (s, 1H), 7.97 (brs, 0.4H minor rotamer), 7.94 (s, 0.6H major rotamer), 7.61 (s, 0.4H minor rotamer), 7.59 (s, 0.6H major rotamer), 7.42-7.20 (m, 2H), 6.51 (dd, J=9.3, 4.0 Hz, 0.6H major rotamer), 5.63 (d, J=7.5 Hz, 0.4H minor rotamer), 4.92 (t, J=9.8 Hz, 1H), 4.69 (d, J=8.2 Hz, 1H), 2.74 (s, 1.2H minor rotamer), 2.62 (s, 1.8H major rotamer).

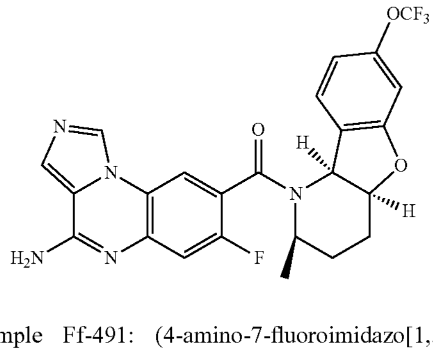

Example Ff-491: (4-amino-7-fluoroimidazo[1,5-a]quinoxalin-8-yl)((2R,4aS,9bS)-2-methyl-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and cis-(2R,4aS,9bS)-2-methyl-7-(trifluoromethoxy)-1,2,3,4,4a,9b-hexahydrobenzofuro[3,2-b]pyridine Ev-9. The desired product was isolated as peak 2 of SFC separation (AD-H 5um 21×250 mm, MeOH 45%, 60 mL/min). ES/MS:

m/z=502.3 [M+H]$^+$. $^1$H NMR (400 MHz, DMSO-$d_6$) δ 9.46-9.13 (m, 1H), 8.66 (brs, 2H), 8.59-8.33 (m, 1H), 8.20 (s, 1H), 7.60-7.17 (m, 2H), 7.05-6.81 (m, 2H), 6.48 (d, J=10.1 Hz, 0.4H minor rotamer), 5.80-5.54 (m, 0.6H major rotamer), 5.41-5.25 (m, 0.4H minor rotamer), 5.19 (brs, 0.6H major rotamer), 4.43 (brs, 1H), 2.10-1.61 (m, 3H), 1.40-1.11 (m, 1H), 0.98 (d, J=6.4 Hz, 1.8H major rotamer), 0.67 (d, J=6.5 Hz, 1.2H minor rotamer).

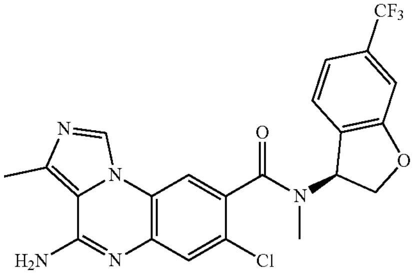 [SMILES: Cc1ncn2c1c(N)nc1cc(Cl)c(C(=O)N(C)[C@@H]3COc4cc(C(F)(F)F)ccc43)cc12]

Example Ff-492: (S)-4-amino-7-chloro-N,3-dimethyl-N-(6-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)-7-chloro-3-methylimidazo[1,5-a]quinoxaline-8-carboxylic acid Aj-1 and (S)—N-methyl-6-(trifluoromethyl)-2,3-dihydrobenzofuran-3-amine hydrogen chloride Eh-1. ES/MS: m/z=476.1 [M+H]$^+$. $^1$H NMR (400 MHz, DMSO-$d_6$) δ 9.30-9.07 (m, 1H), 9.14 (d, J=18.0 Hz, 1H), 8.61 (s, 0.33H minor rotamer), 8.35 (s, 0.67H major rotamer), 8.14 (brs, 2H), 7.73-7.47 (m, 1H), 7.45-7.22 (m, 2H), 6.53 (brs, 0.67H major rotamer), 5.47 (d, J=7.6 Hz, 0.33H minor rotamer), 4.89 (dd, J=10.4, 9.3 Hz, 0.67H major rotamer), 4.81-4.59 (m, 1H+0.33H minor rotamer), 2.71 (d, J=6.6 Hz, 1H minor rotamer), 2.67 (d, J=2.6 Hz, 2H major rotamer), 2.52 (s, 1H minor rotamer), 2.50 (s, 2H major rotamer).

-continued

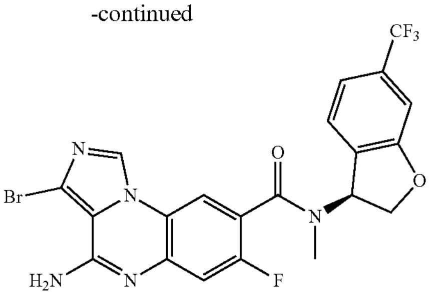

Example Ff-494

NBS (36 mg, 1.5 equiv.) was added to a solution of example Ff-12 (60 mg, 0.13 mmol) in $CHCl_3$ (4.0 mL) and the resulting mixture was stirred for 4 hours at room temperature. The mixture was evaporated to dryness and purified by preparative HPLC to afford examples Ff-493 and Ff-494.

Example Ff-493: (S)-4-amino-1-bromo-7-fluoro-N-methyl-N-(6-(trifluoromethyl)-2,3-dihydrobenzofuran-3-yl)imidazo[1,5-a]quinoxaline-8-carboxamide. Peak 1 by HPLC purification. ES/MS: m/z=524.1, 526.1 [M+H]$^+$. $^1$H NMR (400 MHz, DMSO-$d_6$) δ 8.99 (d, J=6.5 Hz, 1H), 8.16 (brs, 2H), 8.09 (s, 1H), 7.60-7.44 (m, 1H+0.4H minor rotamer), 7.42-7.19 (m, 4H), 6.52-6.40 (m, 0.6H major rotamer), 5.73-5.59 (m, 0.6H major rotamer), 4.86 (t, J=9.9 Hz, 0.4H minor rotamer), 4.77-4.65 (m, 1H), 2.69 (s, 1.2H minor rotamer), 2.62 (s, 1.8H major rotamer).

Example Ff-494: (S)-4-amino-3-bromo-7-fluoro-N-methyl-N-(6-(trifluoromethyl)-2,3-dihydrobenzofuran-3-yl)imidazo[1,5-a]quinoxaline-8-carboxamide. Peak 2 by HPLC purification. ES/MS: m/z=524.1, 526.1 [M+H]$^+$. $^1$H NMR (400 MHz, DMSO-$d_6$) δ 9.20 (s, 1H), 8.36 (d, J=6.4 Hz, 1H), 7.55 (d, J=6.4 Hz, 1H), 7.49 (brs, 2H), 7.37-7.19 (m, 3H), 6.48 (dd, J=9.1, 4.1 Hz, 0.5H rotamer), 5.64 (brs, 0.5H rotamer), 4.87 (t, J=9.8 Hz, 0.5H rotamer), 4.72-4.64 (m, 1H+0,5H rotamer), 2.69 (s, 1.5H rotamer), 2.65-2.56 (m, 1.5H rotamer).

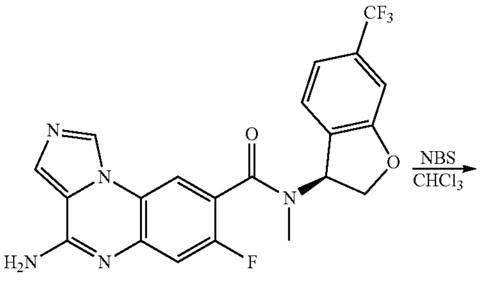

Example Ff-12

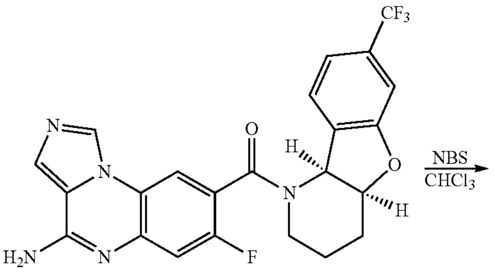

Example Ff-104

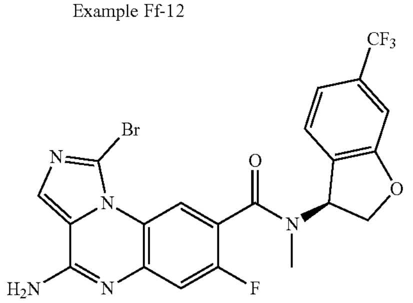

+

Example Ff-493

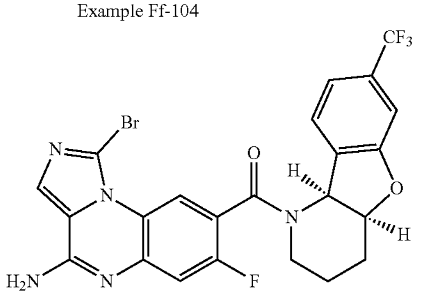

+

Example Ff-495

-continued

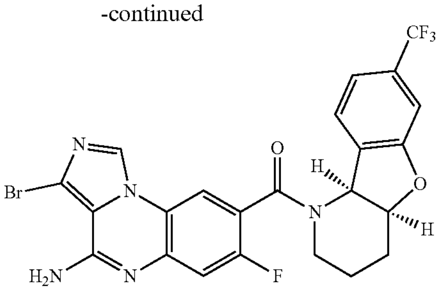

Examples Ff-495 was prepared following the procedure reported for examples Ff-493 and Ff-494 starting with example Ff-104.

Example Ff-495: (4-amino-1-bromo-7-fluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Peak 1 by HPLC purification. ES/MS: m/z=550.2, 552.2 $[M+H]^+$. $^1H$ NMR (400 MHz, DMSO-$d_6$) δ 8.99 (s, 1H), 8.07 (s, 1H), 8.04 (s, 1H), 7.54-7.16 (m, 4H), 6.35 (d, J=8.7 Hz, 0.65H major rotamer), 5.63 (brs, 0.35H minor rotamer), 5.19 (brs, 0.65H major rotamer), 5.12 (bs, 0.35H minor rotamer), 4.29 (s, 0.35H minor rotamer), 3.39 (s, 0.65H major rotamer), 2.87 (s, 1H), 2.08-1.80 (m, 2H), 1.79-1.48 (m, 2H).

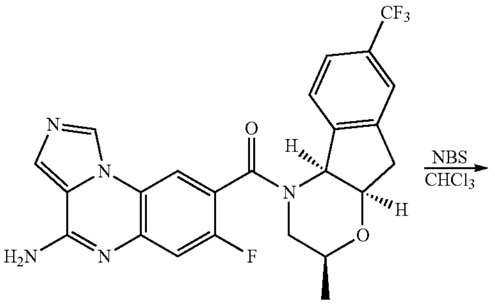

Example Ff-81

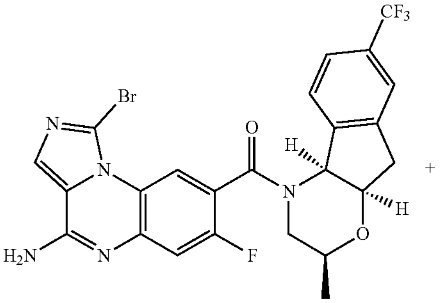

Example Ff-496

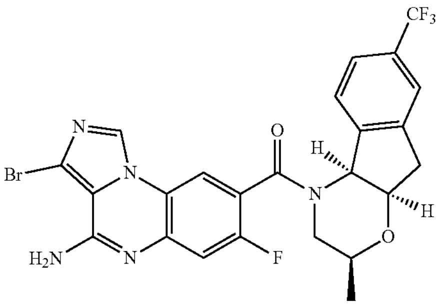

Examples Ff-496 was prepared following the procedure reported for examples Ff-493 and Ff-494 starting with example Ff-81.

Example Ff-496: (4-amino-1-bromo-7-fluoroimidazo[1,5-a]quinoxalin-8-yl)((2S,4aS,9aR)-2-methyl-7-(trifluoromethyl)-2,3,9,9a-tetrahydroindeno[2,1-b][1,4]oxazin-4(4aH)-yl)methanone. Peak 1 by HPLC purification. ES/MS: m/z=564.1, 566.2 $[M+H]^+$. $^1H$ NMR (400 MHz, DMSO-$d_6$) δ 9.05 (d, J=6.5 Hz, 1H), 8.09 (s, 0.6H major rotamer), 8.04 (s, 0.4H minor rotamer), 7.98 (brs, 2H), 7.74-7.60 (m, 2H), 7.49 (s, 0.4H minor rotamer), 7.44-7.30 (m, 1H+0.6H major rotamer), 5.92 (s, 0.6H major rotamer), 5.07 (s, 0.4H minor rotamer), 4.54 (t, J=4.1 Hz, 0.6H major rotamer), 4.49-4.31 (m, 0.4H minor rotamer), 3.50-3.23 (m, 1H+0.6H major rotamer), 3.10-2.61 (m, 2H), 2.44-2.31 (m, 0.4H minor rotamer), 1.04 (d, J=6.2 Hz, 1.2H minor rotamer), 0.89 (d, J=6.2 Hz, 1.8H major rotamer).

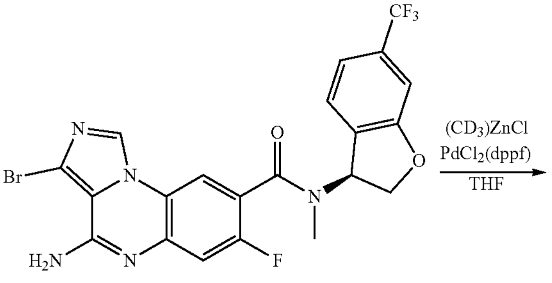

Example Ff-494

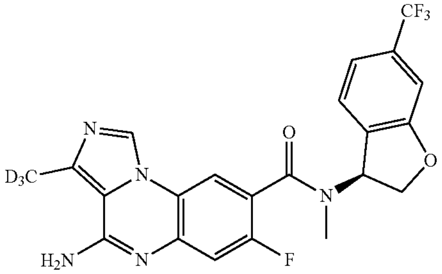

Example Ff-497

Example Ff-497: (S)-4-amino-7-fluoro-N-methyl-3-(methyl-d3)-N-(6-(trifluoromethyl)-2,3-dihydrobenzofuran-3-yl)imidazo[1,5-a]quinoxaline-8-carboxamide. A solution of $CD_3ZnCl$ (prepared from $CD_3MgCl$ and $ZnCl_2$, 0.3M in THF, 4 equiv.) was added to a solution of example Ff-494 (43 mg, 0.067 mmol) and $PdCl_2$(dppf) (5 mg, 0.1 equiv.) in THF (0.5 mL). The mixture was stirred at 40° C. for 2 hours. After usual work up the residue was purified by HPLC to afford the desired product. ES/MS: m/z=463.2 $[M+H]^+$. $^1H$ NMR (400 MHz, DMSO-$d_6$) δ 9.24 (s, 1H), 8.46 (brs, 2H), 8.40 (d, J=6.2 Hz, 1H), 7.55 (d, J=7.7 Hz, 1H), 7.46-7.32 (m, 3H), 7.29 (d, J=1.5 Hz, 0.5H rotamer), 7.26 (s, 0.5H rotamer), 6.47 (dd, J=9.3, 4.2 Hz, 0.5H rotamer), 5.61 (t, J=6.9 Hz, 0.5H rotamer), 4.88 (dd, J=10.5, 9.2 Hz, 0.5H), 4.68 (dd, J=10.4, 4.2 Hz, 1H+0.5H rotamer), 2.70 (s, 1.5H rotamer), 2.60 (s, 1.5H

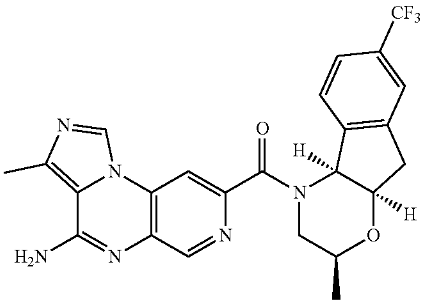 [SMILES: Cc1ncn2c1c(N)nc1cnc(C(=O)N3C[C@H](C)O[C@@H]4Cc5cc(C(F)(F)F)ccc5[C@@H]43)cc12]

Example Ff-498: (4-amino-3-methylimidazo[1,5-a]pyrido[3,4-e]pyrazin-8-yl)((2S,4aS,9aR)-2-methyl-7-(trifluoromethyl)-2,3,9,9a-tetrahydroindeno[2,1-b][1,4]oxazin-4(4aH)-yl)methanone. Prepared following general procedure VI-F starting with 4-((tert-butoxycarbonyl)amino)-3-methylimidazo[1,5-a]pyrido[3,4-e]pyrazine-8-carboxylic acid Ag-2 and (2S,4aS,9aR)-2-methyl-7-(trifluoromethyl)-2,3,4,4a,9,9a-hexahydroindeno[2,1-b][1,4]oxazine Eaz-1. ES/MS: m/z=483.2 $[M+H]^+$. $^1H$ NMR (400 MHz, DMSO-$d_6$) δ 9.28 (s, 0.55H major rotamer), 9.24 (s, 0.45H minor rotamer), 8.79-8.43 (m, 2H), 7.71-7.59 (m, 2H+0.45H minor rotamer), 7.54 (brs, 2H), 7.35 (d, J=7.9 Hz, 0.55H major rotamer), 5.89 (d, J=3.6 Hz, 0.55H major rotamer), 5.53 (s, 0.45H minor rotamer), 4.53 (t, J=4.1 Hz, 0.55H major rotamer), 4.45-4.33 (m, 1H), 3.79 (d, J=12.8 Hz, 0.45H minor rotamer), 3.35-3.25 (m, 0.45H minor rotamer), 3.12-2.77 (m, 1H+0.55H major rotamer), 2.67 (s, 1.65H major rotamer), 2.65 (s, 1.35H minor rotamer), 1.05 (d, J=6.2 Hz, 1.35H minor rotamer), 0.90 (d, J=6.2 Hz, 1.65H major rotamer).

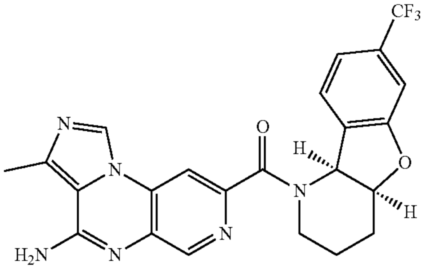 [SMILES: Cc1ncn2c1c(N)nc1cnc(C(=O)N3CCC[C@@H]4Oc5cc(C(F)(F)F)ccc5[C@@H]43)cc12]

Example Ff-499: (4-amino-3-methylimidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)-3-methylimidazo[1,5-a]pyrido[3,4-e]pyrazine-8-carboxylic acid Ag-2 and (4aS,9bS)-7-(trifluoromethyl)-1,2,3,4,4a,9b-hexahydrobenzofuro[3,2-b]pyridine Ew-1. ES/MS: m/z=469.2 $[M+H]^+$. $^1H$ NMR (400 MHz, DMSO-$d_6$) δ 9.28 (s, 1H), 8.76-8.42 (m, 2H), 7.85 (d, J=7.8 Hz, 0.5H rotamer), 7.66 (brs, 2H), 7.52 (d, J=7.7 Hz, 0.5H rotamer), 7.40-7.31 (m, 1H), 7.26 (s, 0.5H rotamer), 7.23 (s, 0.5H rotamer), 6.27 (d, J=8.8 Hz, 0.5H rotamer), 5.96 (d, J=9.1 Hz, 0.5H rotamer), 5.20 (dt, J=8.8, 4.5 Hz, 0.5H rotamer), 5.11-4.95 (m, 0.5H rotamer), 4.34-4.24 (m, 0.5H rotamer), 2.88-2.75 (m, 0.5H rotamer), 2.67 (s, 3H), 2.67-2.52 (m, 0.5H), 2.08-1.49 (m, 4H).

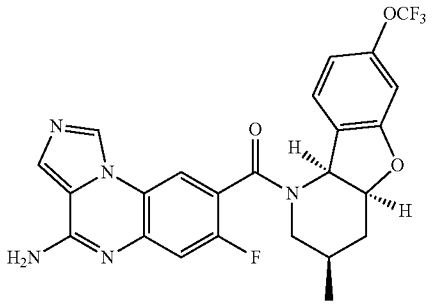 [SMILES: C[C@@H]1C[C@@H]2Oc3cc(OC(F)(F)F)ccc3[C@@H]2N(C(=O)c2cc3c(cc2F)nc(N)c2cncn23)C1]

Example Ff-500: (4-amino-7-fluoroimidazo[1,5-a]quinoxalin-8-yl)((3R,4aS,9bS)-3-methyl-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[11,5-a]quinoxaline-8-carboxylic acid Af-1 and (3R,4aS,9bS)-3-methyl-7-(trifluoromethoxy)-1,2,3,4,4a,9b-hexahydrobenzofuro[3,2-b]pyridine Ew-18. ES/MS: m/z=502.2 $[M+H]^+$. $^1H$ NMR (400 MHz, DMSO-$d_6$) δ 9.34 (s, 0.7H major rotamer), 9.29 (s, 0.3H minor rotamer), 8.92 (brs, 2H), 8.47 (d, J=6.2 Hz, 0.7H major rotamer), 8.26 (s, 1H), 8.25 (s, 0.3H minor rotamer), 7.51-7.25 (m, 2H), 7.04-6.83 (m, 2H), 6.27 (d, J=8.5 Hz, 0.7H major rotamer), 5.42 (brs, 0.3H minor rotamer), 5.21-5.09 (m, 0.7H major rotamer), 5.05-4.94 (m, 0.3H minor rotamer), 4.52-4.41 (m, 0.3H minor rotamer), 3.35 (dd, J=13.5, 4.9 Hz, 0.7H major rotamer), 2.60-2.46 (m, 1H), 2.24-2.06 (m, 1H), 1.78 (brs, 1H), 1.52-1.29 (m, 1H), 0.95 (d, J=6.7 Hz, 0.9H minor rotamer), 0.77 (d, J=6.6 Hz, 2.1H major rotamer).

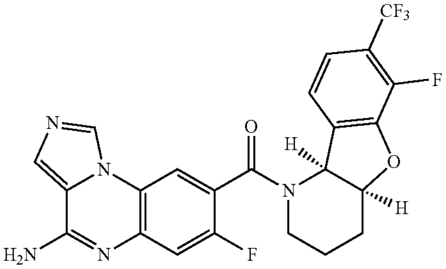

Example Ff-501: (4-amino-7-fluoroimidazo[1,5-a]quinoxalin-8-yl)((4aS,9bS)-6-fluoro-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and (4aS,9bS)-6-fluoro-7-(trifluoromethyl)-1,2,3,4,4a,9b-hexahydrobenzofuro[3,2-b]pyridine Ew-3. ES/MS: m/z=490.2 $[M+H]^+$. $^1H$ NMR (400 MHz, DMSO-$d_6$) δ 9.32 (s, 0.7H major rotamer), 9.31 (s, 0.3H minor rotamer), 8.83 (brs, 2H), 8.62 (brs, 0.3H minor rotamer), 8.45 (d, J=6.2 Hz, 0.7H major rotamer), 8.24 (s, 1H), 7.46-7.25 (m, 3H), 6.44 (d, J=8.9 Hz, 0.7H major rotamer), 5.65 (d, J=9.2 Hz, 0.3H minor rotamer), 5.35 (dt, J=9.3, 4.8 Hz, 0.7H major rotamer), 5.24 (brs, 0.3H minor rotamer), 4.38-4.29 (m, 0.3H minor rotamer), 3.42-3.32 (m, 0.7H major rotamer), 2.99-2.83 (m, 0.7H major rotamer), 2.79-2.62 (m, 0.3H minor rotamer), 2.07-1.85 (m, 2H), 1.84-1.51 (m, 2H).

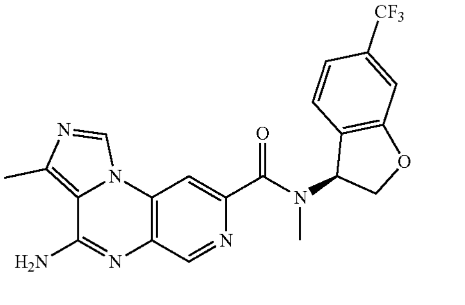 [SMILES: Cc1ncn2c1c(N)nc1cnc(C(=O)N(C)[C@@H]3COc4cc(C(F)(F)F)ccc43)cc12]

Example Ff-502: (S)-4-amino-N,3-dimethyl-N-(6-(trifluoromethyl)-2,3-dihydrobenzofuran-3-yl)imidazo[1,5-a]pyrido[3,4-e]pyrazine-8-carboxamide. Prepared following general procedure VI-F starting with 4-((tert-butoxycarbonyl)amino)-3-methylimidazo[1,5-a]pyrido[3,4-e]pyrazine-8-carboxylic acid Ag-2 and (S)—N-methyl-6-(trifluoromethyl)-2,3-dihydrobenzofuran-3-amine hydrogen chloride Eh-1. ES/MS: m/z=443.1 $[M+H]^+$. $^1H$ NMR (400 MHz, DMSO-$d_6$) δ 9.28 (s, 0.6H major rotamer), 9.27 (s, 0.4H minor rotamer), 8.69 (s, 0.6H major rotamer), 8.65 (s, 0.4H minor rotamer), 8.53 (s, 0.6H major rotamer), 8.48 (s, 0.4H minor rotamer), 7.73 (s, 0.6H major rotamer), 7.68 (brs, 2H), 7.56 (d, J=7.8 Hz, 0.4H minor rotamer), 7.42-7.23 (m, 2H), 6.50-6.41 (m, 0.4H minor rotamer), 6.01 (t, J=6.7 Hz, 0.6H major rotamer), 4.96-4.81 (m, 0.4H minor rotamer), 4.79-4.67 (m, 1H+0.6H major rotamer), 2.74 (s, 1.2H minor rotamer), 2.69 (s, 1.8H major rotamer), 2.67 (s, 3H).

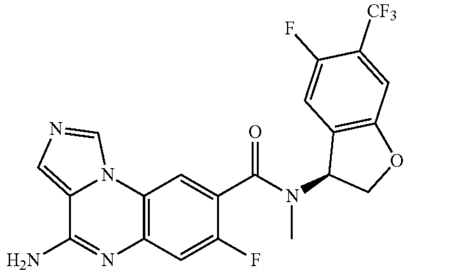

Example Ff-503: (S)-4-amino-7-fluoro-N-(5-fluoro-6-(trifluoromethyl)-2,3-dihydrobenzofuran-3-yl)-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)-5-fluoro-N-methyl-6-(trifluoromethyl)-2,3-dihydrobenzofuran-3-amine hydrochloride Ebg-1. ES/MS: m/z=464.1 $[M+H]^+$. $^1H$ NMR (400 MHz, DMSO-$d_6$) δ 9.29 (s, 0.6H major rotamer), 9.28 (s, 0.4H minor rotamer), 8.84 (brs, 2H), 8.56 (brs, 0.4H minor rotamer), 8.45 (d, J=6.2 Hz, 0.6H major rotamer), 8.24 (s, 1H), 7.50 (d, J=9.6 Hz, 0.6H major rotamer), 7.46-7.37 (m, 1H+0.4H minor rotamer), 7.34 (d, J=5.4 Hz, 0.6H major rotamer), 7.30 (d, J=5.4 Hz, 0.4H minor rotamer), 6.51-6.36 (m, 0.6H major rotamer), 5.70-5.56 (m, 0.4H), 4.89 (t, J=9.8 Hz, 0.6H major rotamer), 4.76-4.63 (m, 1H+0.4H minor rotamer), 2.74 (s, 1.2H minor rotamer), 2.66 (s, 1.8H major rotamer).

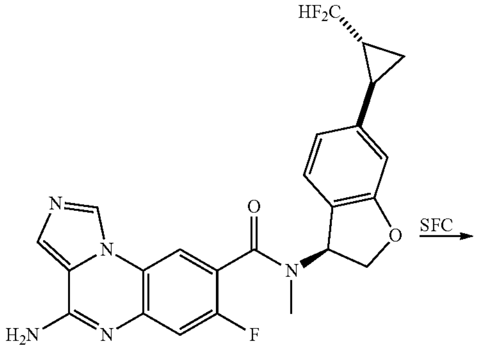

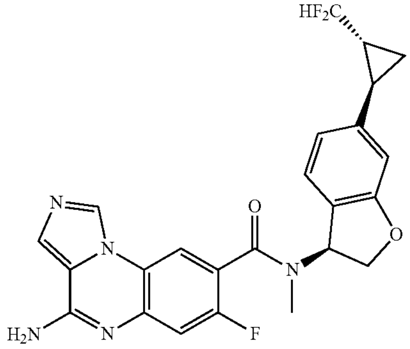
+

Example Ff-504

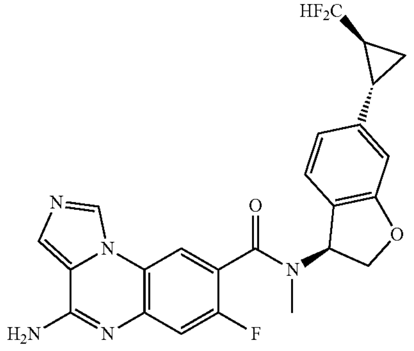

Example Ff-505

Examples Ff-504 and Ff-505 were prepared following the conditions reported in general procedure LXV-E staring with intermediates (S)-4-amino-N-(6-bromo-2,3-dihydrobenzofuran-3-yl)-7-fluoro-N-methylimidazo[1,5-a]quinoxaline-8-carboxamide (example Ff-94) and trans-2-(2-(difluoromethyl)cyclopropyl)-4,4,5,5-tetramethyl-1,3,2-dioxaborolane. The compounds were separated by chiral SFC (OJ-H 4.6×100 mm 5 mic, 40% $MeOH/CO_2$, 3 mL/min). The stereochemistry was arbitrarily assigned.

Example Ff-504: 4-amino-N—((S)-6-((1R,2R)-2-(difluoromethyl)cyclopropyl)-2,3-dihydrobenzofuran-3-yl)-7-fluoro-N-methylimidazo[1,5-a]quinoxaline-8-carboxamide. Peak 1. ES/MS: m/z=468.2 $[M+H]^+$. $^1H$ NMR (400 MHz, DMSO-$d_6$) δ 9.30 (s, 0.55H major rotamer), 8.76 (brs, 2H), 8.44 (d, J=6.2 Hz, 0.45H minor rotamer), 8.23 (s, 1H), 7.50-7.35 (m, 1H), 7.28-7.12 (m, 1H), 6.90-6.60 (m, 2H), 6.38-6.30 (m, 0.45H minor rotamer), 6.10-5.67 (m, 1H), 5.42 (t, J=6.4 Hz, 0.55H major rotamer), 4.78-4.71 (m, 0.55H major rotamer), 4.61-4.47 (m, 1H+0.45H minor rotamer), 2.67 (s, 1.6H major rotamer), 2.54 (s, 1.4H minor rotamer), 2.25-2.14 (m, 1H), 1.84-1.67 (m, 1H), 1.30-0.98 (m, 2H).

Example Ff-505: 4-amino-N—((S)-6-((1S,2S)-2-(difluoromethyl)cyclopropyl)-2,3-dihydrobenzofuran-3-yl)-7-fluoro-N-methylimidazo[1,5-a]quinoxaline-8-carboxamide. Peak 2. ES/MS: m/z=468.2 $[M+H]^+$. $^1H$ NMR (400 MHz, DMSO-$d_6$) δ 9.30 (s, 0.55H major rotamer), 8.76 (brs, 2H), 8.44 (d, J=6.2 Hz, 0.45H minor rotamer), 8.23 (s, 1H), 7.50-7.35 (m, 1H), 7.28-7.12 (m, 1H), 6.90-6.60 (m, 2H), 6.38-6.30 (m, 0.45H minor rotamer), 6.10-5.67 (m, 1H), 5.42 (t, J=6.4 Hz, 0.55H major rotamer), 4.78-4.71 (m, 0.55H major rotamer), 4.61-4.47 (m, 1H+0.45H minor rotamer), 2.67 (s, 1.6H major rotamer), 2.54 (s, 1.4H minor rotamer), 2.25-2.14 (m, 1H), 1.84-1.67 (m, 1H), 1.30-0.98 (m, 2H).

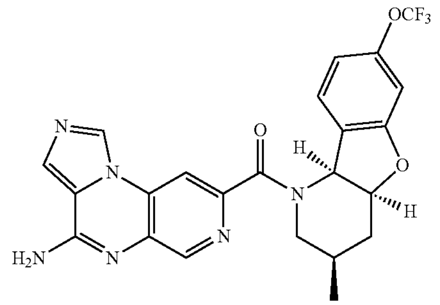 [SMILES: C[C@@H]1C[C@@H]2Oc3cc(OC(F)(F)F)ccc3[C@@H]2N(C(=O)c2cc3c(cn2)nc(N)c2cncn23)C1]

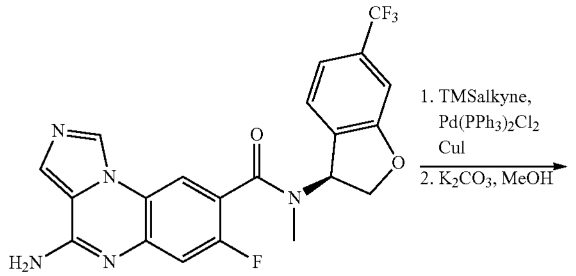

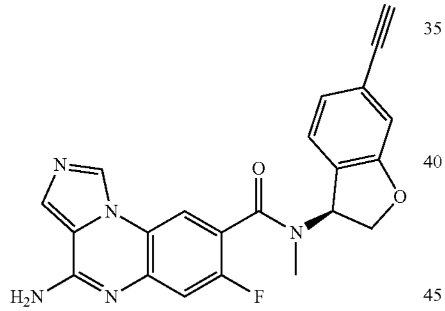

Example Ff-506

Example Ff-506: (S)-4-amino-N-(6-ethynyl-2,3-dihydrobenzofuran-3-yl)-7-fluoro-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide (example Ff-94) and trimethylsilylacetylene. The intermediate (S)-4-amino-7-fluoro-N-methyl-N-(6-((trimethylsilyl)ethynyl)-2,3-dihydrobenzofuran-3-yl)imidazo[1,5-a]quinoxaline-8-carboxamide was deprotected using $K_2CO_3$ (1.5 equiv.) in MeOH at room temperature. ES/MS: m/z=402.1 $[M+H]^+$. $^1H$ NMR (400 MHz, Methanol-$d_4$) δ 9.24 (s, 1H), 8.42 (d, J=6.0 Hz, 0.45H minor rotamer), 8.31 (s, 1H), 7.52-7.27 (m, 1H+0.55H major rotamer), 7.22-7.09 (m, 1H), 6.99 (s, 0.45H minor rotamer), 6.96-6.92 (m, 0.55H major rotamer), 6.51 (dd, J=8.8, 3.5 Hz, 1H), 5.60 (t, J=6.5 Hz, 1H), 4.84-4.78 (m, 1H), 4.65 (dd, J=10.6, 3.6 Hz, 1H), 3.55 (s, 0.55H major rotamer), 3.54 (s, 0.45H minor rotamer), 2.71 (s, 1.65H major rotamer), 2.68 (s, 1.35H minor rotamer).

Example Ff-507: (4-aminoimidazo[1,5-a]pyrido[3,4-e]pyrazin-8-yl)((3R,4aS,9bS)-3-methyl-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]pyrido[3,4-e]pyrazine-8-carboxylic acid Af-6 and (3R,4aS,9bS)-3-methyl-7-(trifluoromethoxy)-1,2,3,4,4a,9b-hexahydrobenzofuro[3,2-b]pyridine Ew-18. ES/MS: m/z=485.2 $[M+H]^+$. $^1H$ NMR (400 MHz, DMSO-$d_6$) δ 9.42 (s, 1H), 8.73 (s, 0.5H rotamer), 8.70 (s, 0.5H rotamer), 8.67 (s, 0.5H rotamer), 8.57 (s, 0.5H rotamer), 8.50 (brs, 2H), 8.18 (s, 0.5H rotamer), 8.16 (s, 0.5H rotamer), 7.73 (d, J=8.2 Hz, 0.5H rotamer), 7.38 (d, J=8.7 Hz, 0.5H rotamer), 7.01-6.88 (m, 2H), 6.17 (d, J=8.4 Hz, 0.5H rotamer), 5.80 (d, J=8.3 Hz, 0.5H rotamer), 5.24-5.11 (m, 0.5H rotamer), 5.01-4.90 (m, 0.5H rotamer), 4.44-4.32 (m, 0.5H rotamer), 3.78-3.64 (m, 0.5H rotamer), 2.50-2.36 (m, 0.5H rotamer), 2.22-1.83 (m, 2H+0.5H rotamer), 1.57-1.40 (m, 1H), 0.96 (d, J=6.8 Hz, 1.5H rotamer), 0.81 (d, J=6.7 Hz, 1.5H rotamer).

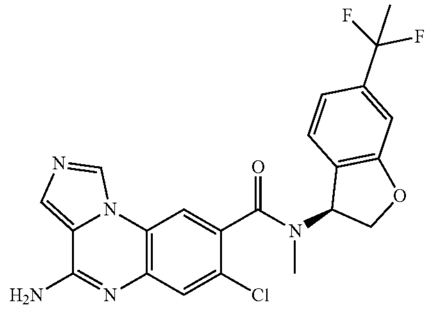 [SMILES: CN(C(=O)c1cc2c(cc1Cl)nc(N)c1cncn12)[C@@H]1COc2cc(C(C)(F)F)ccc21]

Example Ff-508: (S)-4-amino-7-chloro-N-(6-(1,1-difluoroethyl)-2,3-dihydrobenzofuran-3-yl)-N-methylimidazo[1,5-a]quinoxaline-8-carboxamide. Prepared following general procedure VI-F starting with 4-((tert-butoxycarbonyl)amino)-7-chloroimidazo[1,5-a]quinoxaline-8-carboxylic acid Af-2 and (S)-6-(1,1-difluoroethyl)-N-methyl-2,3-dihydrobenzofuran-3-amine Eae-1. ES/MS: m/z=458.1 $[M+H]^+$. $^1H$ NMR (400 MHz, DMSO-$d_6$) δ 9.39 (s, 0.5H rotamer), 9.29 (s, 0.5H rotamer), 9.25 (s, 0.5H rotamer), 8.92 (brs, 2H), 8.70 (s, 0.5H rotamer), 8.44 (s, 0.5H rotamer), 8.25 (s, 0.5H rotamer), 7.69-7.60 (m, 1H), 7.58-7.38 (m, 1H), 7.25-7.13 (m, 1H), 7.10 (s, 0.5H rotamer), 7.05 (s, 0.5H rotamer), 6.50 (s, 0.5H rotamer), 5.46-5.35 (m, 0.5H rotamer), 4.85 (dd, J=10.4, 9.1 Hz, 0.5H rotamer), 4.72-4.53 (m, 1H+0.5H rotamer), 2.72 (s, 1.5H rotamer), 2.71 (s, 1.5H rotamer), 1.95 (td, J=18.9, 12.8 Hz, 3H).

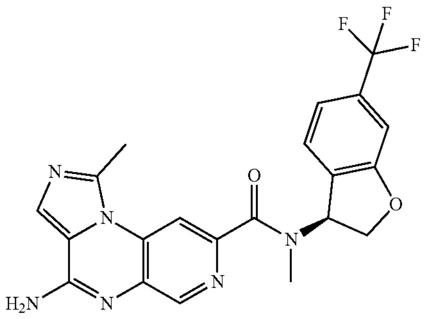 [SMILES: Cc1ncc2c(N)nc3cnc(C(=O)N(C)[C@@H]4COc5cc(C(F)(F)F)ccc54)cc3n12]

Example Ff-509: (S)-4-amino-N,1-dimethyl-N-(6-(trifluoromethyl)-2,3-dihydrobenzofuran-3-yl)imidazo[1,5-a]pyrido[3,4-e]pyrazine-8-carboxamide. Prepared following general procedure VI-F starting with 4-((tert-butoxycarbonyl)amino)-1-methylimidazo[1,5-a]pyrido[3,4-e]pyrazine-8-carboxylic acid Ag-1 and (S)—N-methyl-6-(trifluoromethyl)-2,3-dihydrobenzofuran-3-amine hydrochloride Eh-1. ES/MS: m/z=443.2 [M+H]$^+$. $^1$H NMR (400 MHz, DMSO-$d_6$) δ 8.76 (s, 0.65H major rotamer), 8.73 (s, 0.35H minor rotamer), 8.58 (brs, 2H), 8.34 (s, 0.65H major rotamer), 8.27 (s, 0.35H minor rotamer), 8.15 (s, 1H), 7.74 (d, J=7.8 Hz, 0.65H major rotamer), 7.61 (d, J=7.8 Hz, 0.35H minor rotamer), 7.33 (d, J=7.6 Hz, 1H), 7.28 (s, 0.35H minor rotamer), 7.25 (s, 0.65H major rotamer), 6.45 (dd, J=9.4, 4.2 Hz, 0.35H minor rotamer), 5.98 (t, J=6.8 Hz, 0.65H major rotamer), 4.87 (t, J=9.8 Hz, 0.35H minor rotamer), 4.78-4.68 (m, 1H+0.65H major rotamer), 3.04 (s, 1.95H major rotamer), 3.03 (s, 1.05 minor rotamer), 2.73 (s, 1.05H minor rotamer), 2.70 (s, 1.95H major rotamer).

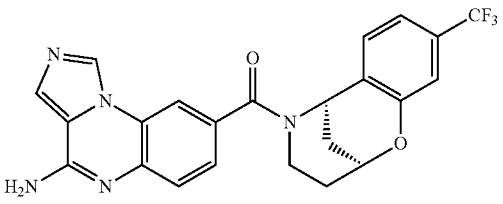 [SMILES: Nc1nc2ccc(C(=O)N3CC[C@H]4C[C@@H]3c3ccc(C(F)(F)F)cc3O4)cc2n2cncc12]

Example Ff-510: (4-aminoimidazo[1,5-a]quinoxalin-8-yl)((2S,6R)-9-(trifluoromethyl)-3,4-dihydro-2H-2,6-methanobenzo[b][1,5]oxazocin-5(6H)-yl)methanone. Prepared using general procedure VI-F starting with 4-((tert-butoxycarbonyl)amino)imidazo[1,5-a]quinoxaline-8-carboxylic acid Ae-1 and (2S,6R)-9-(trifluoromethyl)-3,4,5,6-tetrahydro-2H-2,6-methanobenzo[b][1,5]oxazocine Ebi-1. ES/MS: m/z=454.2 [M+H]$^+$. $^1$H NMR (400 MHz, DMSO-$d_6$) δ 9.46 (s, 1H), 9.32 (brs, 2H), 8.69-8.27 (m, 2H), 7.77-7.46 (m, 3H), 7.33-6.90 (m, 2H), 5.91 (s, 1H), 4.90 (s, 1H), 4.26 (brs, 1H), 3.62-3.41 (m, 1H), 3.03-2.86 (m, 1H), 2.34-1.80 (m, 4H).

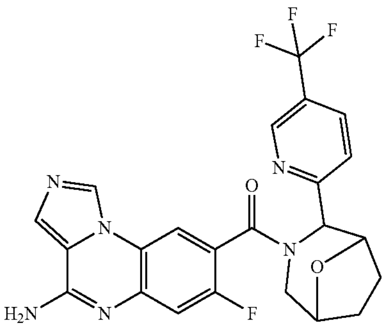 [SMILES: Nc1nc2cc(F)c(C(=O)N3CC4CCC(O4)C3c3ccc(C(F)(F)F)cn3)cc2n2cncc12]

Example Ff-511: (4-amino-7-fluoroimidazo[1,5-a]quinoxalin-8-yl)(2-(5-(trifluoromethyl)pyridin-2-yl)-8-oxa-3-azabicyclo[3.2.1]octan-3-yl)methanone. Prepared using general procedure VI-F starting with 4-(tert-butoxycarbonylamino)-7-fluoro-imidazo[1,5-a]quinoxaline-8-carboxylic acid Af-1 and 2-(5-(trifluoromethyl)pyridin-2-yl)-8-oxa-3-azabicyclo[3.2.1]octane hydrochloride Eai-20. ES/MS: m/z=487.2 [M+H]$^+$. $^1$H NMR (400 MHz, MeOD) δ 9.33 (d, J=8.9 Hz, 0.6H major rotamer), 8.99 (m, 0.6H major rotamer), 8.93 (m, 0.4H minor rotamer), 8.81 (d, J=6.7 Hz, 0.4H minor rotamer), 8.35 (s, 0.6H major rotamer), 8.28 (s, 0.4H minor rotamer), 8.20 (dd, J=8.4, 2.4 Hz, 0.6H major rotamer), 8.10 (d, J=8.0 Hz, 0.4H minor rotamer), 7.76-7.58 (m, 1H), 7.58-7.15 (m, 2H), 5.60 (s, 1H), 5.15 (s, 1H), 4.76-4.49 4 m, 1H), 4.32 (t, J=9.7 Hz, 1H), 3.91 (d, J=12.8 Hz, 1H), 3.69-3.36 (m, 2H), 2.38-1.83 (m, 4H).

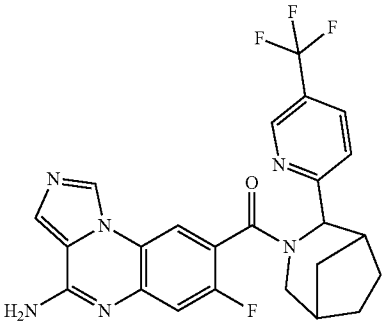 [SMILES: Nc1nc2cc(F)c(C(=O)N3CC4CCC(C4)C3c3ccc(C(F)(F)F)cn3)cc2n2cncc12]

Example Ff-512: (4-amino-7-fluoroimidazo[1,5-a]quinoxalin-8-yl)(2-(5-(trifluoromethyl)pyridin-2-yl)-3-azabicyclo[3.2.1]octan-3-yl)methanone. Prepared using general procedure VI-F starting with 4-(tert-butoxycarbonylamino)-7-fluoro-imidazo[1,5-a]quinoxaline-8-carboxylic acid Af-1 and 2-(5-(trifluoromethyl)pyridin-2-yl)-3-azabicyclo[3.2.1]octane hydrochloride Eai-21. ES/MS: m/z=485.2 [M+H]$^+$. $^1$H NMR (400 MHz, MeOD) δ 9.35 (s, 1H), 8.98 (s, 1H), 8.35 (s, 1H), 8.29-8.08 (m, 2H), 7.68 (s, 1H), 7.49-7.41 (m, 2H), 5.74 (s, 1H), 3.81 (d, J=12.6 Hz, 1H), 2.12-1.62 (m, 5H), 1.62-1.29 (m, 3H).

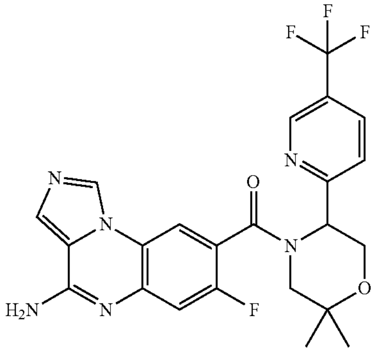 [SMILES: CC1(C)CN(C(=O)c2cc3c(cc2F)nc(N)c2cncn23)C(c2ccc(C(F)(F)F)cn2)CO1]

Example Ff-513: (4-amino-7-fluoroimidazo[1,5-a]quinoxalin-8-yl)(2,2-dimethyl-5-(5-(trifluoromethyl)pyridin-2-yl)morpholino)methanone. Prepared using general procedure VI-F starting with 4-(tert-butoxycarbonylamino)-7-fluoro-imidazo[1,5-a]quinoxaline-8-carboxylic acid Af-1 and 2,2-dimethyl-5-(5-(trifluoromethyl)pyridin-2-yl)morpholine Eai-22. ES/MS: m/z=489.3 $[M+H]^+$. $^1H$ NMR (400 MHz, MeOD) δ 9.33-9.24 (m, 1H), 9.00-8.96 (m, 1H), 8.59-8.27 (m, 2H), 8.22-8.20 (m, 1H), 7.85-7.66 (m, 1H), 7.52-7.35 (m, 1H), 5.81 (s, 1H), 4.71-4.20 (m, 3H), 3.62-3.37 (m, 1H), 1.47 (s, 1.5H rotamer), 1.30 (s, 1.5H rotamer), 1.23 (s, 1.5H rotamer), 1.06 (s, 1.5H rotamer).

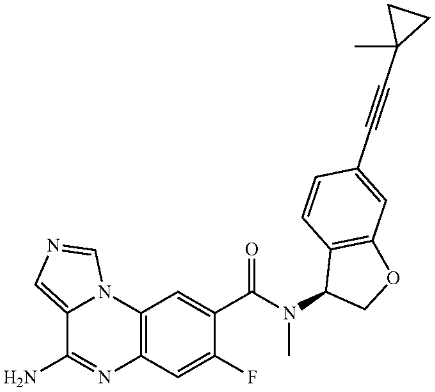 [SMILES: CN(C(=O)c1cc2c(cc1F)nc(N)c1cncn12)[C@@H]1COc2cc(C#CC3(C)CC3)ccc21]

Example Ff-514: (S)-4-amino-7-fluoro-N-methyl-N-(6-((1-methylcyclopropyl)ethynyl)-2,3-dihydrobenzofuran-3-yl)imidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 1-ethynyl-1-methylcyclopropane. EZ/MS: m/z=456.2 $[M+H]^+$. $^1H$ NMR (400 MHz, MeOD) δ 9.23 (s, 1H), 8.55-8.26 (m, 2H), 7.53-7.43 (m, 1H), 7.32 (d, J=7.7 Hz, 0.5H rotamer), 7.24 (d, J=7.7 Hz, 0.5H rotamer), 7.01 (dd, J=7.7, 1.3 Hz, 0.5H rotamer), 6.96 (d, J=7.7 Hz, 0.5H rotamer), 6.85 (s, 0.5H rotamer), 6.79 (s, 0.5H rotamer), 6.48 (dd, J=8.6, 3.4 Hz, 0.5H rotamer), 5.59-5.52 (m, 0.5H rotamer), 4.82-4.71 (m, 0.5H rotamer), 4.66-4.53 (m, 1H+0.5H, rotamer), 2.88-2.66 (m, 3H), 1.35 (s, 1.5H rotamer), 1.34 (s, 1.5H rotamer), 0.99-0.92 (m, 2H), 0.76-0.66 (m, 2H).

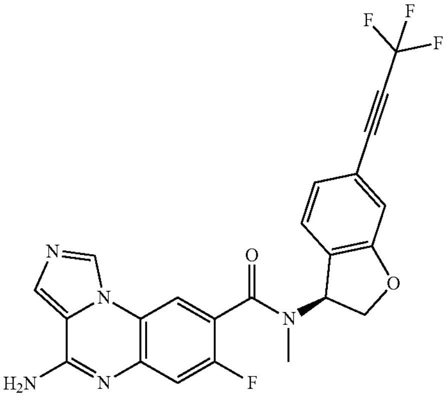 [SMILES: CN(C(=O)c1cc2c(cc1F)nc(N)c1cncn12)[C@@H]1COc2cc(C#CC(F)(F)F)ccc21]

Example Ff-515: (S)-4-amino-7-fluoro-N-methyl-N-(6-(3,3,3-trifluoroprop-1-yn-1-yl)-2,3-dihydrobenzofuran-3-yl)imidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 3,3,3-trifluoroprop-1-yne. EZ/MS: m/z=470.3 $[M+H]^+$. $^1H$ NMR (400 MHz, MeOD) δ 9.26 (s, 1H), 7.57-7.40 (m, 2H), 7.40-7.23 (m, 1H), 7.19-7.07 (m, 1H), 6.55 (dd, J=9.0, 3.7 Hz, 0.5H rotamer), 5.67 (t, J=6.4 Hz, 0.5H rotamer), 4.87-4.81 (m, 1H), 4.71 (dd, J=10.7, 3.9 Hz, 1H), 2.85 (s, 1.5H rotamer), 2.73 (s, 1.5H rotamer).

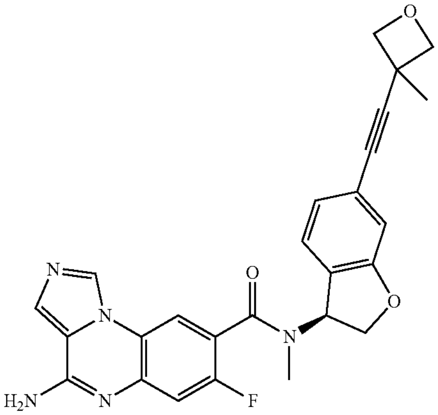 [SMILES: CN(C(=O)c1cc2c(cc1F)nc(N)c1cncn12)[C@@H]1COc2cc(C#CC3(C)COC3)ccc21]

Example Ff-516: (S)-4-amino-7-fluoro-N-methyl-N-(6-((3-methyloxetan-3-yl)ethynyl)-2,3-dihydrobenzofuran-3-yl)imidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 3-ethynyl-3-methyloxetane. EZ/MS: m/z=472.3 $[M+H]^+$. $^1H$ NMR (400 MHz, MeOD) δ 9.04 (s, 1H), 8.24 (d, J=6.3 Hz, 1H), 7.96 (d, J=3.2 Hz, 1H), 7.47-7.17 (m, 2H), 7.18-6.98 (m, 1H), 6.96-6.84 (m, 1H), 6.53-6.48 (m, 0.5H rotamer), 5.64-5.58 (m, 0.5H rotamer), 4.85-4.73 (m, 1H), 4.70-4.56 (m, 2H), 4.55-4.48 (m, 3H), 2.83 (s, 1.5H rotamer), 2.71 (s, 1.5H rotamer), 1.71 (s, 1.5H rotamer) 1.69 (s, 1.5H rotamer).

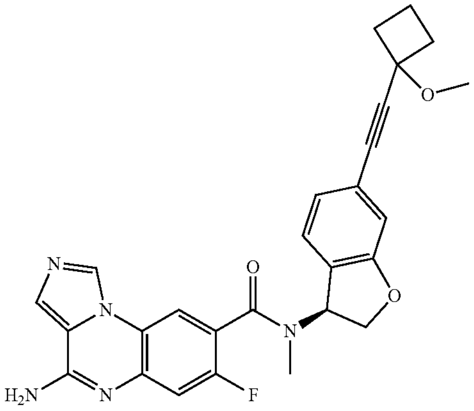 [SMILES: COC1(C#Cc2ccc3c(c2)OC[C@H]3N(C)C(=O)c2cc3c(cc2F)nc(N)c2cncn23)CCC1]

Example Ff-517: (S)-4-amino-7-fluoro-N-(6-((1-methoxycyclobutyl)ethynyl)-2,3-dihydrobenzofuran-3-yl)-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 1-ethynyl-1-methoxycyclobutane. EZ/MS: m/z=486.1 $[M+H]^+$. $^1H$ NMR (400 MHz, MeOD) δ 9.27 (s, 1H), 8.64-8.31 (m, 2H), 7.52 (d, J=9.7 Hz, 0.5H minor rotamer), 7.48 (d, J=9.7 Hz, 0.5H major rotamer), 7.40 (d, J=7.7 Hz, 0.5H major rotamer), 7.31 (d, J=7.7 Hz, 0.5H minor rotamer), 7.12 (dd, J=7.7, 1.3 Hz, 0.5H minor rotamer), 7.08 (d, J=8.0 Hz, 0.5H major rotamer), 6.97 (d, J=1.3 Hz, 0.5H major rotamer), 6.91 (s, 0.5H minor rotamer), 6.51 (dd, J=8.7, 3.5 Hz, 0.5H rotamer), 5.60 (t, J=6.2 Hz, 0.5H rotamer), 4.85-4.75 (m, 1H), 4.73-4.51 (m, 1H), 3.36-3.33 (m, 3H), 2.85 (s, 1.5H rotamer), 2.71 (s, 1.5H rotamer), 2.47-2.21 (m, 4H), 2.02-1.74 (m, 2H).

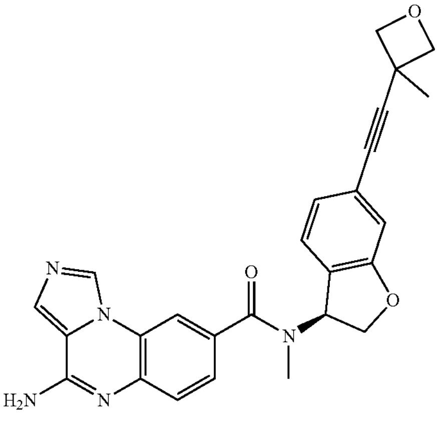 [SMILES: CN(C(=O)c1ccc2nc(N)c3cncn3c2c1)[C@@H]1COc2cc(C#CC3(C)COC3)ccc21]

Example Ff-518: (S)-4-amino-N-methyl-N-(6-((3-methyloxetan-3-yl)ethynyl)-2,3-dihydrobenzofuran-3-yl)imidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 3-ethynyl-3-methyloxetane. EZ/MS: m/z=454.2 $[M+H]^+$. $^1H$ NMR (400 MHz, MeOD) δ 9.11 (s, 1H), 8.29 (s, 1H), 7.96 (s, 1H), 7.66-7.52 (m, 2H), 7.41 (s, 1H), 7.07

(d, J=7.8 Hz, 1H), 6.91 (s, 1H), 6.42 (s, 0.8H major rotamer), 5.75 (s, 0.2H minor rotamer), 4.73-4.45 (m, 6H), 2.79 (s, 3H), 1.70 (s, 3H).

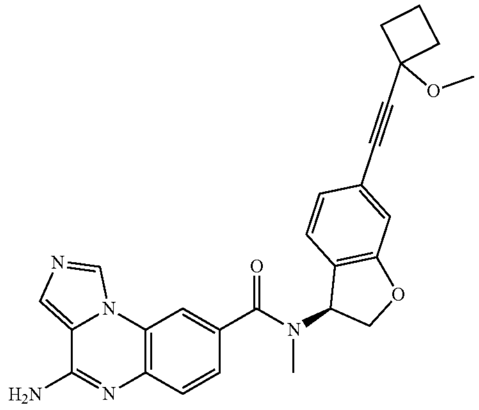 [SMILES: COC1(C#Cc2ccc3c(c2)OC[C@H]3N(C)C(=O)c2ccc3nc(N)c4cncn4c3c2)CCC1]

Example Ff-519: (S)-4-amino-N-(6-((1-methoxycyclobutyl)ethynyl)-2,3-dihydrobenzofuran-3-yl)-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 1-ethynyl-1-methoxycyclobutane. EZ/MS: m/z=468.1 $[M+H]^+$. $^1H$ NMR (400 MHz, MeOD) s 9.33 (s, 1H), 8.45 (s, 1H), 8.38 (s, 1H), 7.70 (s, 2H), 7.44 (s, 1H), 7.11 (s, 1H), 6.95 (s, 1H), 6.51-6.42 (m, 0.5H rotamer), 5.74-5.59 (m, 0.5H rotamer), 4.75-4.59 (m, 2H), 3.35-3.33 (m, 3H under solvent), 2.90-2.70 (m, 3H), 2.47-2.26 (m, 4H), 2.07-1.73 (m, 2H).

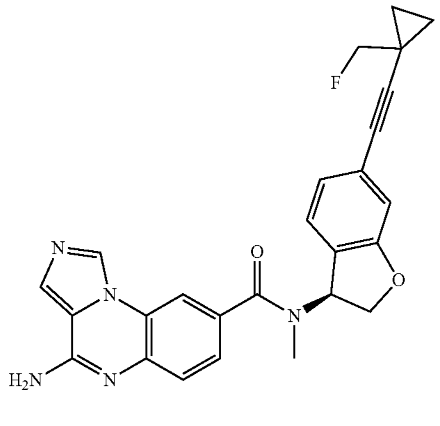 [SMILES: CN(C(=O)c1ccc2nc(N)c3cncn3c2c1)[C@@H]1COc2cc(C#CC3(CF)CC3)ccc21]

Example Ff-520: (S)-4-amino-N-(6-((1-(fluoromethyl)cyclopropyl)ethynyl)-2,3-dihydrobenzofuran-3-yl)-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 1-ethynyl-1-(fluoromethyl)cyclopropane. EZ/MS: m/z=456.3 $[M+H]^+$. $^1H$ NMR (400 MHz, MeOD) δ 9.33 (s, 1H), 8.44 (s, 1H), 8.38 (s, 1H), 7.70 (s, 2H), 7.39 (s, 1H), 7.04 (s, 1H), 6.88 (s, 1H), 6.43 (s, 0.6H major rotamer), 5.65 (s, 0.4H minor rotamer), 4.83-4.56 (m, 2H), 4.33 (d, J=48.5 Hz, 2H), 2.89-2.71 (m, 3H), 1.17-0.95 (m, 4H).

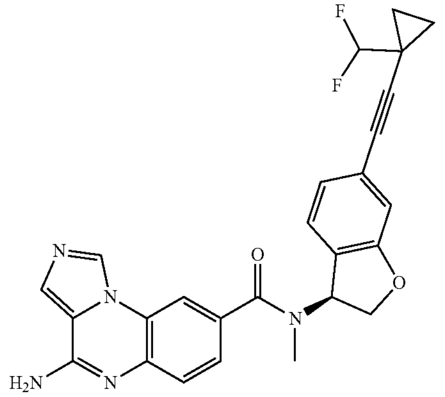 [SMILES: CN(C(=O)c1ccc2nc(N)c3cncn3c2c1)[C@@H]1COc2cc(C#CC3(C(F)F)CC3)ccc21]

Example Ff-521: (S)-4-amino-N-(6-((1-(difluoromethyl)cyclopropyl)ethynyl)-2,3-dihydrobenzofuran-3-yl)-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 1-(difluoromethyl)-1-ethynylcyclopropane. EZ/MS: m/z=474.4 $[M+H]^+$. $^1H$ NMR (400 MHz, MeOD) δ 9.38 (s, 1H), 8.46 (s, 2H), 7.71 (s, 2H), 7.41 (s, 1H), 7.07 (s, 1H), 6.91 (s, 1H), 6.44 (s, 1H), 5.69 (t, J=56.6 Hz, 1H), 4.82-4.55 (m, 3H), 2.76 (s, 2H), 1.27-1.00 (m, 4H).

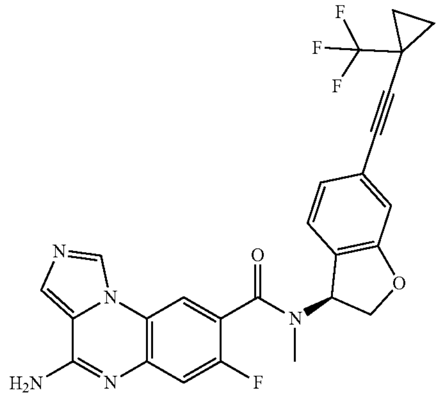 [SMILES: CN(C(=O)c1cc2c(cc1F)nc(N)c1cncn12)[C@@H]1COc2cc(C#CC3(C(F)(F)F)CC3)ccc21]

Example Ff-522: (S)-4-amino-7-fluoro-N-methyl-N-(6-((1-(trifluoromethyl)cyclopropyl)ethynyl)-2,3-dihydrobenzofuran-3-yl)imidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 1-ethynyl-1-(trifluoromethyl)cyclopropane. EZ/MS: m/z=510.2 $[M+H]^+$. $^1H$ NMR (400 MHz, MeOD) δ 9.26 (s, 1H), 8.60-8.30 (m, 2H), 7.55-7.29 (m, 2H), 7.13-7.03 (m, 1H), 6.94 (s, 0.5H rotamer), 6.89 (s, 0.5H rotamer), 6.54-6.47 (m, 0.5H rotamer), 5.62-5.55 (m, 0.5H rotamer), 4.85-4.75 (m, 1H), 4.72-4.56 (m, 1H), 2.84 (s, 1.5H rotamer), 2.70 (s, 1.5H rotamer), 1.46-1.39 (m, 2H), 1.34-1.25 (s, 2H).

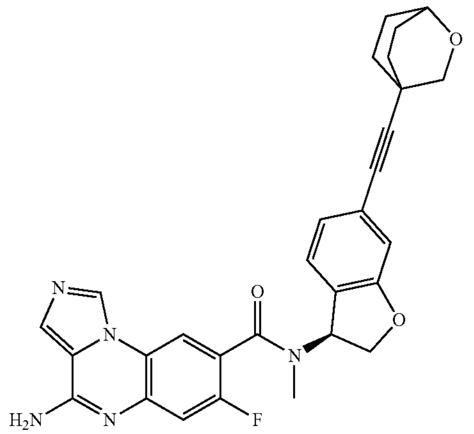 [SMILES: CN(C(=O)c1cc2c(cc1F)nc(N)c1cncn12)[C@@H]1COc2cc(C#CC34CCC(CC3)OC4)ccc21]

Example Ff-523: (S)—N-(6-((2-oxabicyclo[2.2.2]octan-4-yl)ethynyl)-2,3-dihydrobenzofuran-3-yl)-4-amino-7-fluoro-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 4-ethynyl-2-oxabicyclo[2.2.2]octane. EZ/MS: m/z=512.2 $[M+H]^+$. $^1H$ NMR (400 MHz, MeOD) δ 9.25 (s, 1H), 8.56-8.30 (m, 2H), 7.55-7.39 (m, 1H), 7.34 (d, J=7.7 Hz, 0.5H rotamer), 7.26 (d, J=7.8 Hz, 0.5H rotamer), 7.09-6.92 (m, 1H), 6.87 (s, 0.5H rotamer), 6.81 (s, 0.5H rotamer), 6.58-6.43 (m, 0.5H rotamer), 5.57 (s, 0.5H rotamer), 4.85-4.74 (m, 1H), 4.66-4.60 (m, 1H), 3.91 (d, J=7.2 Hz, 2H), 3.79 (s, 1H), 2.84 (s, 1.5H rotamer), 2.68 (s, 1.5H major rotamer), 2.20-1.62 (m, 8H).

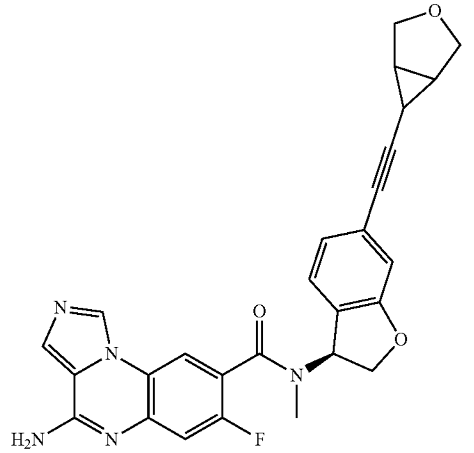 [SMILES: CN(C(=O)c1cc2c(cc1F)nc(N)c1cncn12)[C@@H]1COc2cc(C#CC3C4COCC34)ccc21]

Example Ff-524: N-((3S)-6-((3-oxabicyclo[3.1.0]hexan-6-yl)ethynyl)-2,3-dihydrobenzofuran-3-yl)-4-amino-7-fluoro-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 6-ethynyl-3-oxabicyclo[3.1.0]hexane. EZ/MS: m/z=484.2 $[M+H]^+$. $^1H$ NMR (400 MHz, MeOD) δ 9.25 (s, 1H), 8.58-8.08 (m, 2H), 7.55-7.16 (m, 2H), 7.11-6.72 (m, 2H), 6.48 (dd, J=8.8, 3.4 Hz, 0.5H rotamer), 5.56 (s, 0.5H rotamer), 4.83-4.46 (m, 2H), 3.92 (dd, J=8.7, 3.6 Hz, 2H), 3.71 (d, J=8.7 Hz, 2H), 2.91-2.54 (m, 3H), 2.05 (dd, J=6.7, 2.5 Hz, 2H), 1.46-1.30 (m, 1H).

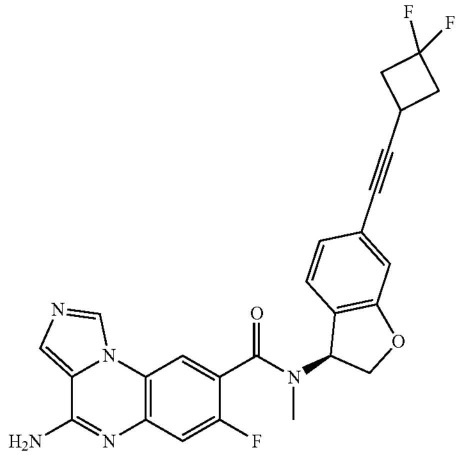 [SMILES: CN(C(=O)c1cc2c(cc1F)nc(N)c1cncn12)[C@@H]1COc2cc(C#CC3CC(F)(F)C3)ccc21]

Example Ff-525: (S)-4-amino-N-(6-((3,3-difluorocyclobutyl)ethynyl)-2,3-dihydrobenzofuran-3-yl)-7-fluoro-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-7-fluoro-N-methylimidazo[1,5-a]quinoxaline-8-carboxamide example Ff-94 and 3-ethynyl-1,1-difluorocyclobutane. EZ/MS: m/z=492.3 $[M+H]^+$. $^1H$ NMR (400 MHz, MeOD) δ 9.26 (s, 1H), 8.44 (d, J=5.9 Hz, 1H), 8.36 (s, 1H), 7.47 (m, 1H), 7.37 (d, J=7.7 Hz, 0.5H rotamer), 7.28 (d, J=7.8 Hz, 0.5H rotamer), 7.16-6.96 (m, 1H), 6.93 (d, J=1.2 Hz, 0.5 rotamer), 6.87 (s, 0.5H rotamer), 6.50 (dd, J=8.8, 3.5 Hz, 0.5H rotamer), 5.57 (d, J=6.8 Hz, 0.5H rotamer), 4.80 (m, 1H), 4.64 (m, 1H), 3.27-3.11 (m, 1H), 3.00 (m, 2H), 2.84 (s, 1.5H rotamer), 2.81-2.58 (m, 2+1.5H rotamer). Calculated 20H, found 18H

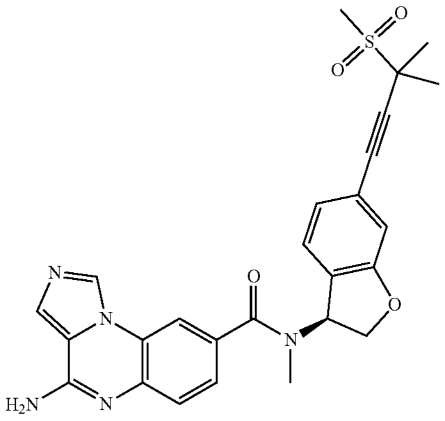 [SMILES: CN(C(=O)c1ccc2nc(N)c3cncn3c2c1)[C@@H]1COc2cc(C#CC(C)(C)S(C)(=O)=O)ccc21]

Example Ff-526: (S)-4-amino-N-methyl-N-(6-(3-methyl-3-(methylsulfonyl)but-1-yn-1-yl)-2,3-dihydrobenzofuran-3-yl)imidazo[1,5-a]quinoxaline-8-carboxamide Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 3-methyl-3-(methylsulfonyl)but-1-yne.

EZ/MS: m/z=504.1 $[M+H]^+$. $^1H$ NMR (400 MHz, MeOD δ 9.34 (s, 1H), 8.46 (s, 1H), 8.41 (s, 1H), 7.71 (s, 2H), 7.46 (s, 1H), 7.14 (d, J=7.6 Hz, 1H), 6.99 (s, 1H), 6.46 (s, 0.6H major rotamer), 5.69 (s, 0.4H minor rotamer), 4.83-4.60 (m, 2H), 3.14 (s, 3H), 2.73 (m, 3H), 1.73 (s, 6H)

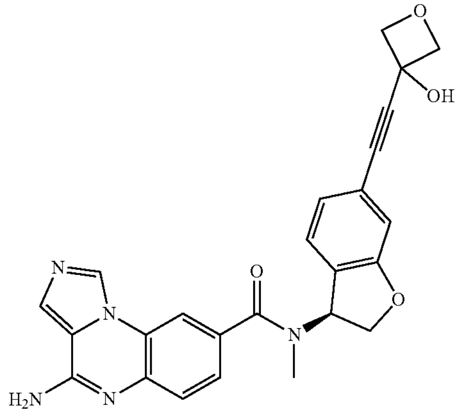 [SMILES: CN(C(=O)c1ccc2nc(N)c3cncn3c2c1)[C@@H]1COc2cc(C#CC3(O)COC3)ccc21]

Example Ff-527: (S)-4-amino-N-(6-((3-hydroxyoxetan-3-yl)ethynyl)-2,3-dihydrobenzofuran-3-yl)-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 3-ethynyloxetan-3-ol. EZ/MS: m/z=456.2 $[M+H]^+$. $^1H$ NMR (400 MHz, MeOD) δ 9.11 (s, 1H), 8.30 (s, 1H), 7.98 (s, 1H), 7.67-7.52 (m, 2H), 7.44 (s, 1H), 7.14 (d, J=7.6 Hz, 1H), 6.97 (s, 1H), 6.42 (s, 0.8H, major rotamer), 5.73 (s, 0.2H minor rotamer), 4.90-4.88 (m, 2H), 4.81-4.67 (m, 4H), 2.80 (s, 3H).

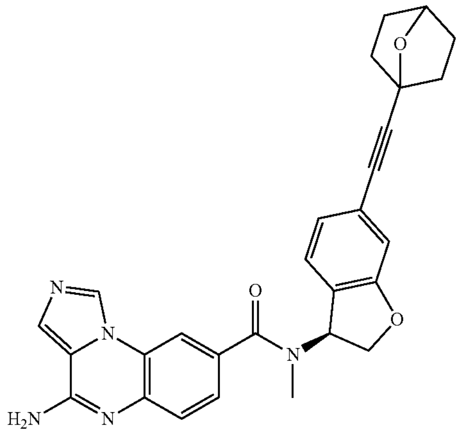 [SMILES: CN(C(=O)c1ccc2nc(N)c3cncn3c2c1)[C@@H]1COc2cc(C#CC34CCC(CC3)O4)ccc21]

Example Ff-528: (S)—N-(6-((7-oxabicyclo[2.2.1]heptan-1-yl)ethynyl)-2,3-dihydrobenzofuran-3-yl)-4-amino-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 1-ethynyl-7-oxabicyclo[2.2.1]heptane. EZ/MS: m/z=480.3 $[M+H]^+$. $^1H$ NMR (400 MHz, MeOD) δ 9.34 (s, 1H), 8.52-8.31 (m, 2H), 7.70 (s, 2H), 7.39 (s, 1H), 7.03 (s, 1H), 6.87 (s, 1H), 6.43 (s, 0.5H major rotamer), 5.65 (s, 0.5H minor rotamer), 4.74-4.50 (m, 3H), 2.89-2.66 (m, 5H), 2.13-1.47 (m, 6H).

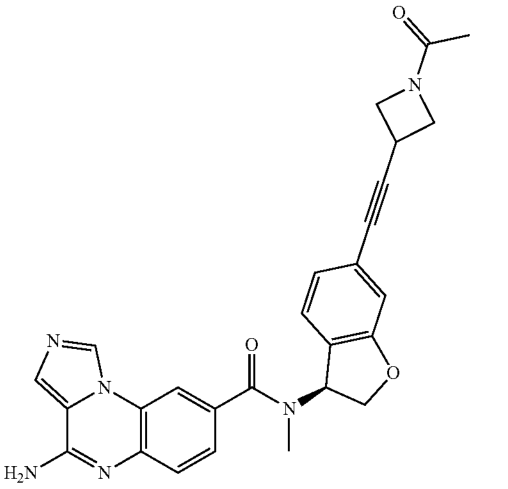 [SMILES: CC(=O)N1CC(C#Cc2ccc3c(c2)OC[C@H]3N(C)C(=O)c2ccc3nc(N)c4cncn4c3c2)C1]

Example Ff-529: ((S)—N-(6-((1-acetylazetidin-3-yl)ethynyl)-2,3-dihydrobenzofuran-3-yl)-4-amino-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 1-(3-ethynylazetidin-1-yl)ethan-1-one. EZ/MS: m/z=481.1 $[M+H]^+$. $^1$H NMR (400 MHz, MeOD δ 9.33 (s, 1H), 8.57-8.23 (m, 2H), 7.71 (s, 2H), 7.43 (s, 1H), 7.10 (s, 1H), 6.94 (s, 1H), 6.51-6.37 (m, 0.7H major rotamer), 5.77-5.62 (m, 0.3H, minor rotamer), 4.82-4.63 (m, 1H), 4.54 (t, J=8.6 Hz, 1H), 4.44-4.17 (m, 2H), 4.17-3.85 (m, 1H), 3.81-3.62 (m, 1H), 2.86-2.73 (m 3H), 2.68 (s, 1H), 1.90 (s, 3H).

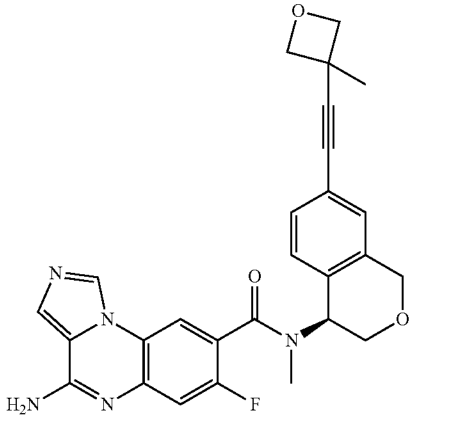 [SMILES: CN(C(=O)c1cc2c(cc1F)nc(N)c1cncn12)[C@@H]1COCc2cc(C#CC3(C)COC3)ccc21]

Example Ff-530: (S)-4-amino-7-fluoro-N-methyl-N-(7-((3-methyloxetan-3-yl)ethynyl)isochroman-4-yl)imidazo[1,5-a]quinoxaline-8-carboxamide. Prepared following the procedure reported for example Ff-17 starting with (R)-4-amino-N-(7-bromochroman-4-yl)-7-fluoro-N-methylimidazo[1,5-a]quinoxaline-8-carboxamide (made following general procedure VI-F starting with Af-1 and Eh-4) and 3-ethynyl-3-methyloxetane. EZ/MS: m/z=486.1 $[M+H]^+$. $^1$H NMR (400 MHz, MeOD δ 9.22 (s, 1H), 8.42 (d, J=5.9 Hz, 1H), 8.31 (s, 1H), 7.89-7.75 (m, 2H), 7.52-7.40 (m, 1H), 7.24-7.12 (m, 1H), 6.54-6.44 (m, 0.6H major rotamer), 5.70 (s, 0.4H minor rotamer), 4.97-4.91 (m, 2H), 4.78-4.67 (m, 1H), 4.52 (t, J=5.0 Hz, 1H), 3.82-3.70 (m, 1H), 3.54-3.46 (m, 1H), 2.91 (s, 1.2H minor rotamer), 2.81 (s, 1.8H major rotamer), 1.74-1.69 (m, 2H), 1.39-1.26 (m, 3H).

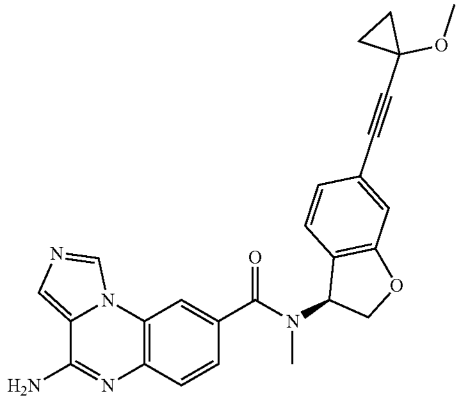 [SMILES: COC1(C#Cc2ccc3c(c2)OC[C@H]3N(C)C(=O)c2ccc3nc(N)c4cncn4c3c2)CC1]

Example Ff-531: (S)-4-amino-N-(6-((1-methoxycyclopropyl)ethynyl)-2,3-dihydrobenzofuran-3-yl)-N-methylimidazo[1,5-a]quinoxaline-8-carboxamide. Prepared following the procedure reported for example Ff-17 starting with (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 1-ethynyl-1-methoxycyclopropane. EZ/MS: m/z=454.3 $[M+H]^+$. $^1$H NMR (400 MHz, MeOD δ 9.34 (s, 1H), 8.55-8.24 (m, 2H), 7.71-7.25 (m, 2H), 7.58-7.28 (m, 1H), 7.08 (s, 1H), 6.92 (s, 1H), 6.44 (m, 0.6 major rotamer H), 5.67 (m, 0.4H minor rotamer), 4.82-4.42 (m, 2H), 3.44 (s, 3H), 3.23-2.67 (m, 3H), 1.91-1.84 (m, 2H), 1.19-0.96 (m, 2H).

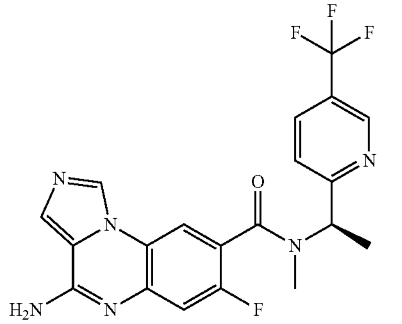 [SMILES: C[C@H](c1ccc(C(F)(F)F)cn1)N(C)C(=O)c1cc2c(cc1F)nc(N)c1cncn12]

Example Ff-532: (R)-4-amino-7-fluoro-N-methyl-N-(1-(5-(trifluoromethyl)pyridin-2-yl)ethyl)imidazo[1,5-a]quinoxaline-8-carboxamide. Prepared using general procedure VI-F starting with 4-(tert-butoxycarbonylamino)-7-fluoroimidazo[1,5-a]quinoxaline-8-carboxylic acid Af-1 and (R)—N-methyl-1-(5-(trifluoromethyl)pyridin-2-yl)ethan-1-amine hydrogen chloride Ebj-1. ES/MS: m/z=433.2 $[M+H]^+$. $^1$H NMR (400 MHz, MeOD) δ 9.26 (s, 1H), 8.93 (s, 1H), 8.67-8.28 (m, 2H), 8.18-8.12 (m, 1H), 7.92-7.22 (m, 2H), 6.12-5.93 (m, 1H), 3.03-2.90 (m, 3H), 1.78 (t, J=7.5 Hz, 3H).

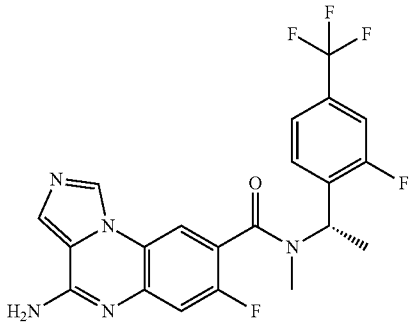 [SMILES: C[C@@H](c1ccc(C(F)(F)F)cc1F)N(C)C(=O)c1cc2c(cc1F)nc(N)c1cncn12]

Example Ff-533: (S)-4-amino-7-fluoro-N-(1-(2-fluoro-4-(trifluoromethyl)phenyl)ethyl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (S)-1-(2-fluoro-4-(trifluoromethyl)phenyl)-N-methylethan-1-amine hydrogen chloride Ebj-3. ES/MS: m/z=450.3 $[M+H]^+$. $^1H$ NMR (400 MHz, MeOD) δ 9.28 (d, J=5.1 Hz, 1H), 8.45-8.19 (m, 2H), 7.86-7.66 (m, 1H), 7.66-7.37 (m, 3H), 6.19 (q, J=7.1 Hz, 0.66H major rotamer), 5.30 (m, 0.34H minor rotamer), 2.94 (s, 1.02H minor rotamer), 2.82 (s, 1.98H major rotamer), 1.75 (d, J=6.9 Hz, 3H).

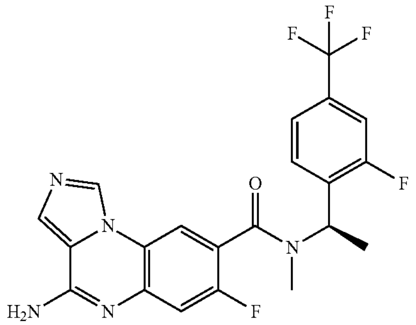 [SMILES: C[C@H](c1ccc(C(F)(F)F)cc1F)N(C)C(=O)c1cc2c(cc1F)nc(N)c1cncn12]

Example Ff-534: (R)-4-amino-7-fluoro-N-(1-(2-fluoro-4-(trifluoromethyl)phenyl)ethyl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (R)-1-(2-fluoro-4-(trifluoromethyl)phenyl)-N-methylethan-1-amine hydrogen chloride Ebj-4. ES/MS: m/z=450.3 $[M+H]^+$. $^1H$ NMR (400 MHz, MeOD) δ 9.28 (d, J=5.6 Hz, 1H), 8.45-8.19 (m, 2H), 7.87-7.66 (m, 1H), 7.68-7.31 (m, 3H), 6.19 (q, J=7.1 Hz, 0.66H major rotamer), 5.30 (m, 0.34H minor rotamer), 2.94 (s, 1.02H minor rotamer), 2.82 (s, 1.98H, major rotamer), 1.75 (d, J=7.0 Hz, 3H).

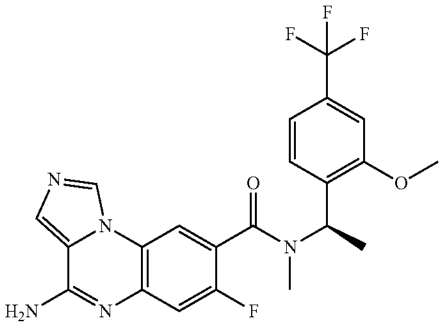 [SMILES: COc1cc(C(F)(F)F)ccc1[C@@H](C)N(C)C(=O)c1cc2c(cc1F)nc(N)c1cncn12]

Example Ff-535: (R)-4-amino-7-fluoro-N-(1-(2-methoxy-4-(trifluoromethyl)phenyl)ethyl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (R)-1-(2-methoxy-4-(trifluoromethyl)phenyl)-N-methylethan-1-amine hydrogen chloride Ebj-6. ES/MS: m/z=462.3 $[M+H]^+$. $^1H$ NMR (400 MHz, MeOD) δ 9.26 (m, 1H), 8.46-8.29 (m, 2H), 7.67-7.20 (m, 4H), 6.13 (m, 0.6H minor rotamer), 5.26 (s, 0.4H minor rotamer), 3.99 (s, 1.8H major rotamer), 3.76 (s, 1.2H minor rotamer), 2.91 (s, 1.2H minor rotamer), 2.78-2.65 (m, 1.8H major rotamer) 1.79-1.63 (m, 3H).

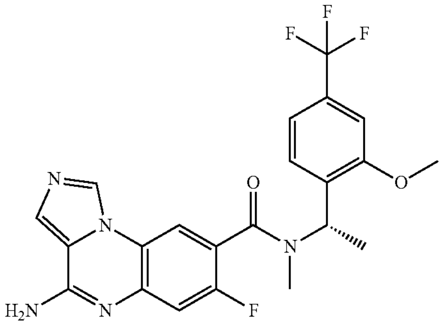 [SMILES: COc1cc(C(F)(F)F)ccc1[C@H](C)N(C)C(=O)c1cc2c(cc1F)nc(N)c1cncn12]

Example Ff-536: (S)-4-amino-7-fluoro-N-(1-(2-methoxy-4-(trifluoromethyl)phenyl)ethyl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (S)-1-(2-methoxy-4-(trifluoromethyl)phenyl)-N-methylethan-1-amine hydrogen chloride Ebj-5. ES/MS: m/z=462.2 $[M+H]^+$. $^1H$ NMR (400 MHz, MeOD) δ 9.21 (s, 1H), 8.34-8.18 (m, 2H), 7.63 (m, 1H), 7.50-7.25 (m, 3H), 6.12 (m, 0.6H major rotamer), 5.27 (s, 0.4H minor rotamer), 3.99 (s, 1.8H major rotamer), 3.75 (s, 1.2H minor rotamer), 2.91 (s, 1.2H minor rotamer), 2.68 (m, 1.8H major rotamer), 1.71 (m, 3H).

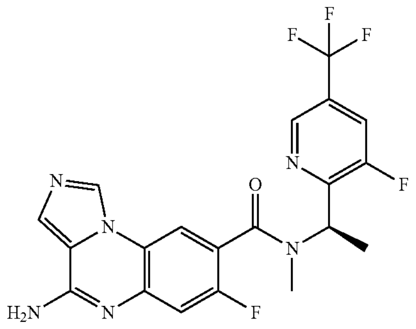 [SMILES: C[C@H](c1ncc(C(F)(F)F)cc1F)N(C)C(=O)c1cc2c(cc1F)nc(N)c1cncn12]

Example Ff-537: (R)-4-amino-7-fluoro-N-(1-(3-fluoro-5-(trifluoromethyl)pyridin-2-yl)ethyl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (R)-1-(3-fluoro-5-(trifluoromethyl)pyridin-2-yl)-N-methylethan-1-amine hydrogen chloride Ebj-7. ES/MS: m/z=451.3 $[M+H]^+$. $^1H$ NMR (400 MHz, MeOD) δ 9.29 (m, 1H), 8.88-8.76 (m, 1H), 8.64 (m, 0.5H rotamer), 8.38 (m, 1+0.5H rotamer), 8.12-7.88 (m, 1H), 7.60-7.37 (m, 1H), 6.27 (m, 0.5H rotamer), 5.69 (m, 0.5H rotamer), 3.08-3.01 (m, 3H), 1.78-1.6 (m, 3H).

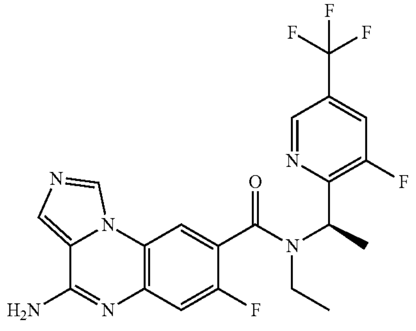 [SMILES: CCN(C(=O)c1cc2c(cc1F)nc(N)c1cncn12)[C@H](C)c1ncc(C(F)(F)F)cc1F]

Example Ff-538: (R)-4-amino-N-ethyl-7-fluoro-N-(1-(3-fluoro-5-(trifluoromethyl)pyridin-2-yl)ethyl)imidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (R)-1-(3-fluoro-5-(trifluoromethyl)pyridin-2-yl)-N-methylethan-1-amine hydrogen chloride Ebj-8. ES/MS: m/z=465.3 $[M+H]^+$. $^1H$ NMR (400 MHz, MeOD) δ 9.29 (s, 1H), 8.81 (s, 1H), 8.35 (m, 2H), 8.17-7.92 (m, 1H), 7.69-7.33 (m, 1H), 6.12 (m, 0.5H rotamer), 5.37 (s, 0.5H rotamer), 3.65-3.40 (m, 2H), 1.83-1.63 (m, 3H), 1.13-0.88 (m, 3H).

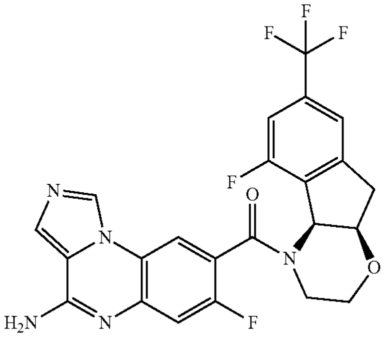 [SMILES: Nc1nc2cc(F)c(C(=O)N3CCO[C@@H]4Cc5cc(C(F)(F)F)cc(F)c5[C@@H]43)cc2n2cncc12]

Example Ff-539: (4-amino-7-fluoroimidazo[1,5-a]quinoxalin-8-yl)((4aS,9aR)-5-fluoro-7-(trifluoromethyl)-2,3,9,9a-tetrahydroindeno[2,1-b][1,4]oxazin-4(4aH)-yl)methanone. Prepared using general procedure VI-F starting with 4-(tert-butoxycarbonylamino)-7-fluoro-imidazo[1,5-a]quinoxaline-8-carboxylic acid Af-1 and (4aS,9aR)-5-fluoro-7-(trifluoromethyl)-2,3,4,4a,9,9a-hexahydroindeno[2,1-b][1,4]oxazine hydrogen chloride Eaz-8. ES/MS: m/z=490.2 $[M+H]^+$. $^1H$ NMR (400 MHz, MeOD) δ 9.30 (s, 1H), 8.55-8.15 (m, 2H), 7.60-7.27 (m, 3H), 6.26 (s, 0.8H major rotamer), 5.38 (s, 0.2H minor rotamer), 4.58-4.37 (m, 2H), 4.06-3.43 (m, 3H), 3.04 (m, 2H).

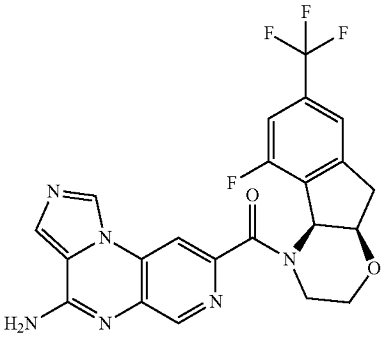 [SMILES: Nc1nc2cnc(C(=O)N3CCO[C@@H]4Cc5cc(C(F)(F)F)cc(F)c5[C@@H]43)cc2n2cncc12]

Example Ff-540: (4-aminoimidazo[1,5-a]pyrido[3,4-e]pyrazin-8-yl)((4aS,9aR)-5-fluoro-7-(trifluoromethyl)-2,3,9,9a-tetrahydroindeno[2,1-b][1,4]oxazin-4(4aH)-yl)methanone. Prepared using general procedure VI-F starting with 4-((tert-butoxycarbonyl)amino)imidazo[1,5-a]pyrido[3,4-e]pyrazine-8-carboxylic acid Af-6 and (4aS,9aR)-5-fluoro-7-(trifluoromethyl)-2,3,4,4a,9,9a-hexahydroindeno[2,1-b][1,4]oxazine hydrogen chloride Eaz-8. ES/MS: m/z=473.2 $[M+H]^+$. $^1H$ NMR (400 MHz, MeOD) δ 9.36 (s, 1H), 8.80 (m, 1H), 8.57 (m, 1H), 8.23 (m, 1H), 7.46 (m, 1H), 7.31 (m, 1H), 6.29 (m, 1H), 4.65-4.33 (m, 2H), 4.15-3.68 (m, 3H), 3.20-2.86 (m, 2H).

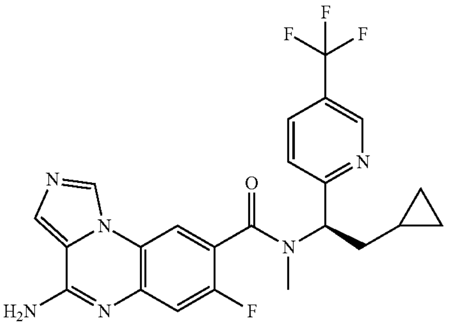 [SMILES: CN(C(=O)c1cc2c(cc1F)nc(N)c1cncn12)[C@H](CC1CC1)c1ccc(C(F)(F)F)cn1]

Example Ff-541: (R)-4-amino-N-(2-cyclopropyl-1-(5-(trifluoromethyl)pyridin-2-yl)ethyl)-7-fluoro-N-methylimidazo[1,5-a]quinoxaline-8-carboxamide. Prepared using general procedure VI-F starting with 4-((tert-butoxycarbonyl)amino)-7-fluoroimidazo[1,5-a]quinoxaline-8-carboxylic acid Af-1 and (R)-2-cyclopropyl-N-methyl-1-(5-(trifluoromethyl)pyridin-2-yl)ethan-1-amine Ebj-9. ES/MS: m/z=473.3 $[M+H]^+$. $^1H$ NMR (400 MHz, MeOD) δ 9.28 (s, 1H), 8.98-8.86 (m, 1H), 8.53-8.34 (m, 2H), 8.24-8.12 (m, 1H), 7.73 (d, J=8.2 Hz, 1H), 7.50 (m, 1H), 6.08-5.92 (m, 2H), 5.23-5.05 (m, 2H), 2.96 (d, J=1.3 Hz, 3H), 2.47-2.35 (m, 1H), 2.35-2.22 (m, 2H), 2.18-2.05 (m, 1H).

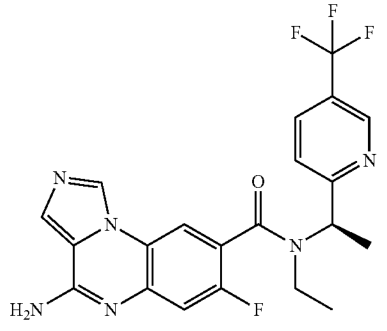 [SMILES: CCN(C(=O)c1cc2c(cc1F)nc(N)c1cncn12)[C@H](C)c1ccc(C(F)(F)F)cn1]

Example Ff-542: (R)-4-amino-N-ethyl-7-fluoro-N-(1-(5-(trifluoromethyl)pyridin-2-yl)ethyl)imidazo[1,5-a]quinoxaline-8-carboxamide. Prepared using general procedure VI-F starting with 4-((tert-butoxycarbonyl)amino)-7-fluoroimidazo[1,5-a]quinoxaline-8-carboxylic acid Af-1 and (R)—N-ethyl-1-(5-(trifluoromethyl)pyridin-2-yl)ethan-1-amine Ebj-10. ES/MS: m/z=447.3 $[M+H]^+$. $^1H$ NMR (400 MHz, MeOD) δ 9.30 (s, 1H), 8.92 (s, 1H), 8.59-8.32 (m, 2H), 8.24-8.05 (m, 1H), 7.78 (m, 0.5H rotamer), 7.65-7.41 (m, 1+0.5H, rotamer), 5.73-5.63 (m, 0.5H rotamer), 5.15-5.06 (m, 0.5H rotamer), 3.78-3.42 (m, 2H), 1.89 (d, J=7.1 Hz, 1.5H), 1.79 (d, J=7.0 Hz, 1.5H), 1.18 (t, J=7.0 Hz, 1.5H), 1.06 (t, J=7.1 Hz, 1.5H).

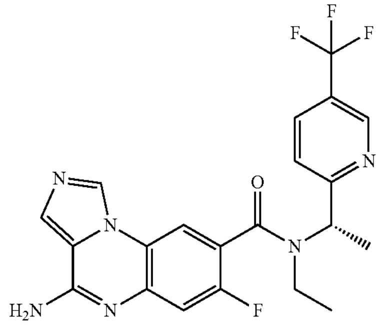 [SMILES: CCN(C(=O)c1cc2c(cc1F)nc(N)c1cncn12)[C@@H](C)c1ccc(C(F)(F)F)cn1]

Example Ff-543: (S)-4-amino-N-ethyl-7-fluoro-N-(1-(5-(trifluoromethyl)pyridin-2-yl)ethyl)imidazo[1,5-a]quinoxaline-8-carboxamide. Prepared using general procedure VI-F starting with 4-((tert-butoxycarbonyl)amino)-7-fluoroimidazo[1,5-a]quinoxaline-8-carboxylic acid Af-1 and (S)—N-ethyl-1-(5-(trifluoromethyl)pyridin-2-yl)ethan-1-amine Ebj-11. ES/MS: m/z=447.2 $[M+H]^+$. $^1H$ NMR (400 MHz, MeOD) δ 9.29 (s, 1H), 8.92 (s, 1H), 8.57-8.31 (m, 2H), 8.17-8.11 (m, 1H), 7.78 (d, J=8.3 Hz, 0.5H rotamer), 7.57 (d, J=8.3 Hz, 0.5H rotamer), 7.47 (d, J=9.6 Hz, 1H), 5.68 (q, J=7.0 Hz, 0.5H rotamer), 5.11 (d, J=7.1 Hz, 0.5H rotamer), 3.91-3.37 (m, 2H), 1.89 (d, J=7.1 Hz, 1.5H rotamer), 1.79 (d, J=7.0 Hz, 1.5H rotamer), 1.18 (t, J=7.0 Hz, 1.5H rotamer), 1.05 (t, J=7.1 Hz, 1.5H rotamer).

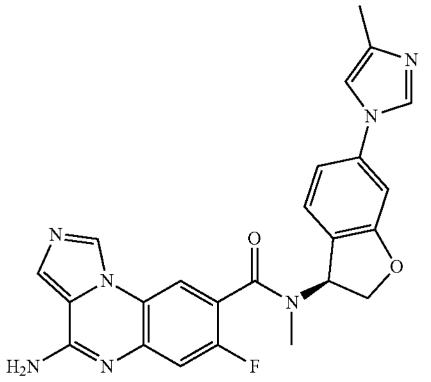 [SMILES: Cc1cn(-c2ccc3c(c2)OC[C@H]3N(C)C(=O)c2cc3c(cc2F)nc(N)c2cncn23)cn1]

Example Ff-544: (S)-4-amino-7-fluoro-N-methyl-N-(6-(4-methyl-1H-imidazol-1-yl)-2,3-dihydrobenzofuran-3-yl)imidazo[1,5-a]quinoxaline-8-carboxamide. Prepared using general procedure VI-F starting with 4-((tert-butoxycarbonyl)amino)-7-fluoroimidazo[1,5-a]quinoxaline-8-carboxylic acid Af-1 and (S)—N-methyl-6-(4-methyl-1H-imidazol-1-yl)-2,3-dihydrobenzofuran-3-amine Eag-2. ES/MS: m/z=458.2 $[M+H]^+$. $^1H$ NMR (400 MHz, MeOD) δ 9.41-9.27 (m, 1H), 9.22 (s, 1H), 8.60-8.39 (m, 1H), 8.33 (s, 1H), 7.80 (m, 1H), 7.71-7.41 (m, 2H), 7.41-7.13 (m, 2H), 6.66-6.43 (m, 0.6H major rotamer), 5.81-5.5.63 (m, 0.4H minor rotamer), 5.05-4.88 (m, 1H), 4.84-4.70 (m, 1H), 2.88 (s, 1.2H minor rotamer), 2.78 (s, 1.8H major rotamer), 2.56-2.37 (m, 3H).

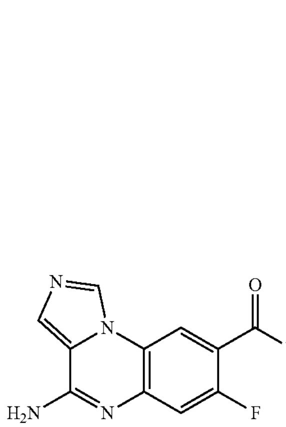

Example Ff-545: (S)-4-amino-7-fluoro-N-methyl-N-(6-(4-(trifluoromethyl)-1H-pyrazol-1-yl)-2,3-dihydrobenzofuran-3-yl)imidazo[1,5-a]quinoxaline-8-carboxamide. Prepared using general procedure VI-F starting with 4-((tert-butoxycarbonyl)amino)-7-fluoroimidazo[1,5-a]quinoxaline-8-carboxylic acid Af-1 and (S)—N-methyl-6-(4-(trifluoromethyl)-1H-pyrazol-1-yl)-2,3-dihydrobenzofuran-3-amine Eaf-1. ES/MS: m/z=512.2 $[M+H]^+$. $^1$H NMR (400 MHz, MeOD) δ 9.27 (s, 1H), 8.91-8.63 (m, 1H), 8.56-8.26 (m, 2H), 8.10-7.90 (m, 1H), 7.59-7.26 (m, 4H), 6.68-6.41 (m, 0.5H rotamer), 5.86-5.49 (m, 0.5H rotamer), 4.97-4.89 (m, 0.5H rotamer), 4.79-4.63 (m, 1+0.5H rotamer), 2.90 (s, 1.5H rotamer), 2.78-2.73 (m, 1.5H rotamer).

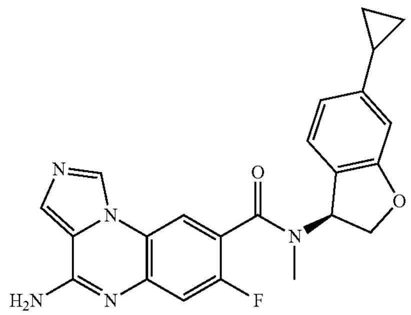 [SMILES: CN(C(=O)c1cc2c(cc1F)nc(N)c1cncn12)[C@@H]1COc2cc(C3CC3)ccc21]

Example Ff-546: (S)-4-amino-N-(6-cyclopropyl-2,3-dihydrobenzofuran-3-yl)-7-fluoro-N-methylimidazo[1,5-a]quinoxaline-8-carboxamide. Prepared following the procedure reported for example Ff-23 starting with (S)-4-amino-N-(6-bromo-2,3-dihydrobenzofuran-3-yl)-7-fluoro-N-methylimidazo[1,5-a]quinoxaline-8-carboxamide example Ff-94 and cyclopropylboronic acid monohydrate. ES/MS: m/z=418.2 $[M+H]^+$. $^1$H NMR (400 MHz, Methanol-d4) δ 9.24 (s, 1H), 8.54-8.19 (m, 2H), 7.65-7.37 (m, 1H), 7.35-7.12 (m, 1H), 6.87-6.52 (m, 2H), 6.52-6.33 (m, 0.4H minor rotamer), 5.61-5.34 (s, 0.6H major rotamer), 4.79-7.66 (m, 0.8H minor rotamer), 4.65-4.44 (m, 1.2H major rotamer), 2.82 (s, 1.2H minor rotamer), 2.67 (d, J=2.5 Hz, 1.8H major rotamer), 2.09-1.78 (m, 1H), 1.08-0.86 (m, 2H), 0.89-0.41 (m, 2H).

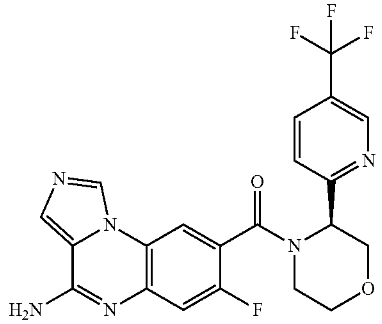 [SMILES: Nc1nc2cc(F)c(C(=O)N3CCOC[C@@H]3c3ccc(C(F)(F)F)cn3)cc2n2cncc12]

Example Ff-547: (S)-(4-amino-7-fluoroimidazo[1,5-a]quinoxalin-8-yl)(3-(5-(trifluoromethyl)pyridin-2-yl)morpholino)methanone. Example Ff-128 was separated using SFC (Column IC 5 uM 21×250 nm, MeOH 45%). The desired isomer was isolated as peak 2. ES/MS: m/z=461.4 $[M+H]^+$. $^1$H NMR (400 MHz, MeOD) δ 9.33 (s, 0.7H, major rotamer), 9.22 (s, 0.3H, minor rotamer), 8.99 (s, 0.7H, major rotamer), 8.96 (s, 0.3H, minor rotamer), 8.50 (s, 0.7H, major rotamer), 8.45 (s, 0.3H, minor rotamer), 8.40 (s, 0.7H, major rotamer), 8.36 (s, 0.3H, minor rotamer), 8.21 (d, J=8.2 Hz, 0.7H, major rotamer), 8.13 (d, J=8.3 Hz, 0.3H, minor rotamer), 7.77 (d, J=8.4 Hz, 0.7H, major rotamer), 7.70 (d, J=8.5 Hz, 0.3H, minor rotamer), 7.51 (d, J=9.6 Hz, 0.7H, major rotamer), 7.41 (d, J=9.5 Hz, 0.3H, minor rotamer), 5.85 (s, 1H), 4.72 (d, J=13.9 Hz, 0.7H, major rotamer), 4.45 (d, J=13.9 Hz, 0.3H minor rotamer), 4.05 (t, J=15.5 Hz, 2H), 3.88-3.50 (m, 3H).

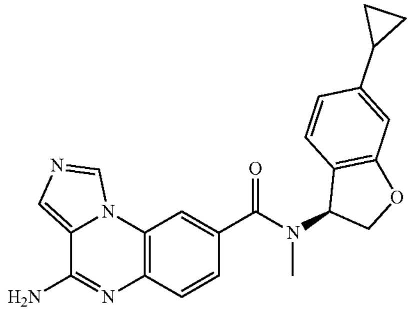 [SMILES: CN(C(=O)c1ccc2nc(N)c3cncn3c2c1)[C@@H]1COc2cc(C3CC3)ccc21]

Example Ff-548: (S)-4-amino-N-(6-cyclopropyl-2,3-dihydrobenzofuran-3-yl)-N-methylimidazo[1,5-a]quinoxaline-8-carboxamide. Prepared following the procedure reported for example Ff-23 starting with (S)-4-amino-N-(6-bromo-2,3-dihydrobenzofuran-3-yl)-N-methylimidazo[1,5-a]quinoxaline-8-carboxamide (prepared following genera procedure VI-F starting with Ae-1 and Eh-5) and cyclopropylboronic acid monohydrate. ES/MS: m/z=400.3 $[M+H]^+$. $^1$H NMR (400 MHz, Methanol-d4) δ 9.49-9.10 (s, 1H), 8.63-8.32 (m, 2H), 8.02-7.48 (m, 2H), 7.46-7.08 (m, 1H), 6.76-6.47 (m, 1H), 6.43-6.27 (m, 0.5H rotamer), 5.68-5.53 (m, 0.5H rotamer), 4.82-4.72 (m, 1H), 3.01-2.41 (m, 3H), 2.03-1.78 (m, 1H), 1.1-0.79 (m, 2H), 0.69-0.41 (m, 2H).

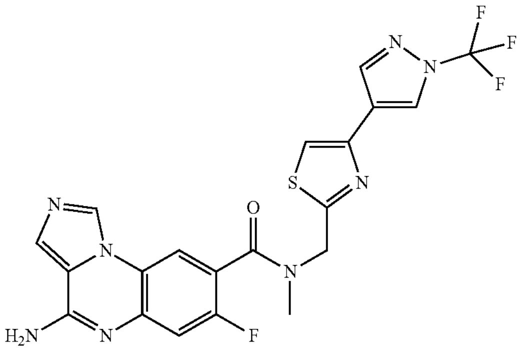 [SMILES: CN(Cc1nc(-c2cnn(C(F)(F)F)c2)cs1)C(=O)c1cc2c(cc1F)nc(N)c1cncn12]

Example Ff-550: 4-amino-7-fluoro-N-methyl-N-((4-(1-(trifluoromethyl)-1H-pyrazol-4-yl)thiazol-2-yl)methyl)imidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, 1-(4-bromothiazol-2-yl)-N-methylmethanamine Ed-8 and 4-(4,4,5,5-tetramethyl-1,3,2-dioxaborolan-2-yl)-1-(trifluoromethyl)-1H-pyrazole. ES/MS: m/z=491.1 $^1$H NMR (400 MHz, MeOD) δ 9.32-8.96 (m, 1H), 8.67-8.47 (m, 1H), 8.47-8.11 (m, 3H), 7.90-7.68 (m, 1H), 7.55-7.39 (m, 1H), 5.13 (s, 1.4H major rotamer), 4.91 (s, 0.6H minor rotamer), 3.30 (s, 0.9H minor rotamer), 3.20-3.17 (m, 2.1H major rotamer).

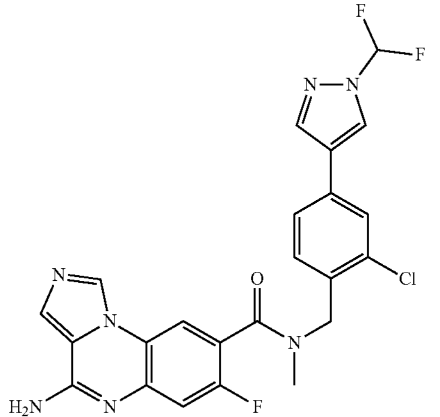 [SMILES: CN(Cc1ccc(-c2cnn(C(F)F)c2)cc1Cl)C(=O)c1cc2c(cc1F)nc(N)c1cncn12]

Example Ff-551: 4-amino-N-(2-chloro-4-(1-(difluoromethyl)-1H-pyrazol-4-yl)benzyl)-7-fluoro-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, 1-(4-bromo-2-chlorophenyl)-N-methylmethanamine Ed-44 and 4-(4,4,5,5-tetramethyl-1,3,2-dioxaborolan-2-yl)-1-(difluoromethyl)-1H-pyrazole. ES/MS: m/z=500.2 $[M+H]^+$. $^1$H NMR (400 MHz, MeOD) δ 9.36-9.11 (m, 1H), 8.65-8.30 (m, 3H), 8.21-8.07 (m, 1H), 7.91-7.59 (m, 2H), 7.59-7.28 (m, 3H), 4.99 (s, 1.2H major rotamer), 4.72 (s, 0.8H minor rotamer), 3.15 (s, 1.2H minor rotamer), 3.03 (s, 1.8H major rotamer).

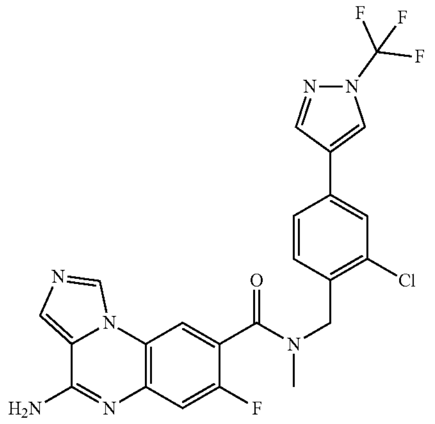 [SMILES: CN(Cc1ccc(-c2cnn(C(F)(F)F)c2)cc1Cl)C(=O)c1cc2c(cc1F)nc(N)c1cncn12]

Example Ff-552: 4-amino-N-(2-chloro-4-(1-(trifluoromethyl)-1H-pyrazol-4-yl)benzyl)-7-fluoro-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, 1-(4-bromo-2-chlorophenyl)-N-methylmethanamine Ed-44 and 4-(4,4,5,5-tetramethyl-1,3,2-dioxaborolan-2-yl)-1-(trifluoromethyl)-1H-pyrazole. ES/MS: m/z=518.2 $[M+H]^+$. $^1$H NMR (400 MHz, MeOD) δ 9.35-9.07 (m, 1H), 8.75-8.58 (m, 1H), 8.54-8.19 (m, 3H), 7.93-7.82 (m, 1H), 7.79-7.62 (m, 1H), 7.62-7.38 (m, 2H), 4.99 (s, 1.2H major rotamer), 4.73 (s, 0.8H minor rotamer), 3.15 (s, 1.2H minor rotamer), 3.09-2.98 (m, 1.8H major rotamer).

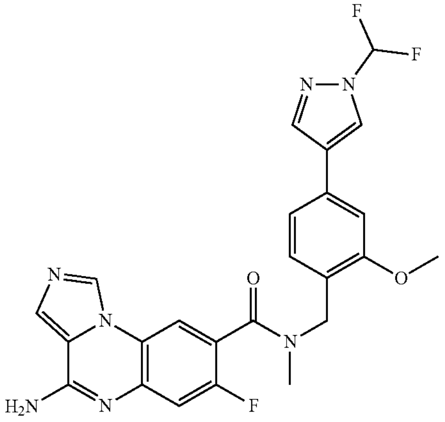 [SMILES: COc1cc(-c2cnn(C(F)F)c2)ccc1CN(C)C(=O)c1cc2c(cc1F)nc(N)c1cncn12]

Example Ff-553: 4-amino-N-(4-(1-(difluoromethyl)-1H-pyrazol-4-yl)-2-methoxybenzyl)-7-fluoro-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, 1-(4-bromo-2-chlorophenyl)-N-methylmethanamine Ed-45 and 4-(4,4,5,5-tetramethyl-1,3,2-dioxaborolan-2-yl)-1-(difluoromethyl)-1H-pyrazole. ES/MS: m/z=496.2 $[M+H]^+$. $^1$H NMR (400 MHz, MeOD) δ 9.36-9.13 (m, 1H), 8.57-8.31 (m, 3H), 8.21-8.01 (m, 1H), 7.73-7.13 (m, 5H), 4.68 (s, 1H rotamer), 4.57 (s, 1H rotamer), 3.99 (s, 1.5H rotamer), 3.82 (s, 1.5H rotamer), 3.10 (s, 1.5H rotamer), 2.99 (s, 1.5H rotamer).

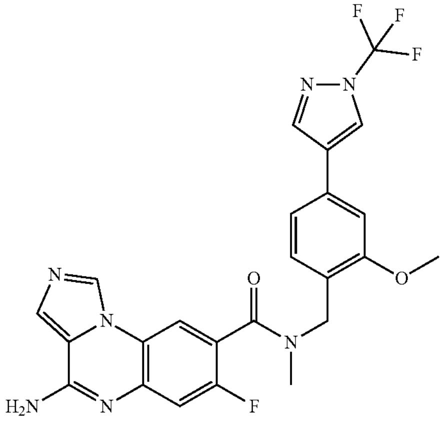 [SMILES: COc1cc(-c2cnn(C(F)(F)F)c2)ccc1CN(C)C(=O)c1cc2c(cc1F)nc(N)c1cncn12]

Example Ff-554: 4-amino-N-(4-(1-(trifluoromethyl)-1H-pyrazol-4-yl)-2-methoxybenzyl)-7-fluoro-N-methylimidazo[1,5-a]quinoxaline-8-carboxamide. Prepared following the procedure reported for example Ff-23 starting with 4-((tert-butoxycarbonyl)amino)-7-fluoroimidazo[1,5-a]quinoxaline-8-carboxylic acid Af-1, 1-(4-bromo-2-chlorophenyl)-N-methylmethanamine Ed-45 and 4-(4,4,5,5-tetramethyl-1,3,2-dioxaborolan-2-yl)-1-(trifluoromethyl)-1H-pyrazole. ES/MS: m/z=514.3 $[M+H]^+$. $^1H$ NMR (400 MHz, MeOD) δ 9.39-9.03 (m, 1H), 8.78-8.52 (m, 1H), 8.52-8.00 (m, 3H), 7.67-7.04 (m, 4H), 4.85 (s, 1H), 4.58 (s, 1H), 3.99 (s, 1.5H rotamer), 3.83 (s, 1.5H rotamer), 3.10 (s, 1.5H rotamer), 3.00 (s, 1.5H rotamer).

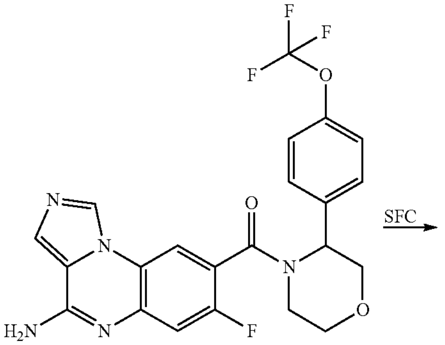

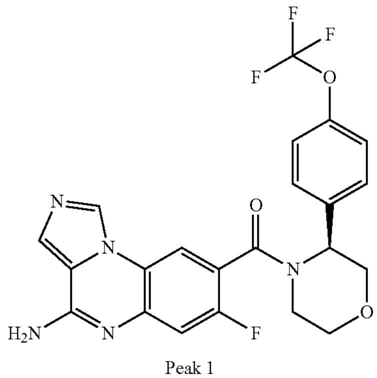

Peak 1
Example Ff-555

+

-continued

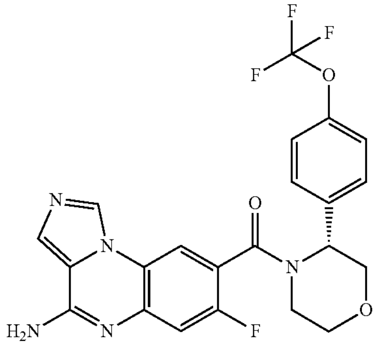

Peak 2
Example Ff-556

Examples Ff-555 and Ff-556 were prepared using general procedure VI-F starting with 4-(tert-butoxycarbonylamino)-7-fluoro-imidazo[1,5-a]quinoxaline-8-carboxylic acid Af-1 and commercial (5-(trifluoromethmethoxy)phenyl)morpholine. The isomers were separated using SFC (IG 4.6×100 mm column, EtOH 35%).

Example Ff-555: (S)-(4-amino-7-fluoroimidazo[1,5-a]quinoxalin-8-yl)(3-(4-(trifluoromethoxy)phenyl)morpholino)methanone. Peak 1. ES/MS: m/z=476.2 $[M+H]^+$. $^1H$ NMR (400 MHz, MeOD) δ 9.28 (s, 1H), 8.55-8.23 (m, 2H), 7.77 (s, 2H), 7.67-7.01 (m, 3H), 5.85 (s, 1H), 4.79-4.40 (m, 2H), 4.13-3.59 (m, 2H), 3.51-3.37 (m, 2H).

Example Ff-556: (R)-(4-amino-7-fluoroimidazo[1,5-a]quinoxalin-8-yl)(3-(4-(trifluoromethoxy)phenyl)morpholino)methanone. Peak 2. ES/MS: m/z=476.2 $[M+H]^+$. $^1H$ NMR (400 MHz, MeOD) δ 9.25 (s, 1H), 8.56-8.17 (m, 2H), 7.77 (s, 1H), 7.63-7.03 (m, 4H), 5.85 (s, 1H), 4.69-4.42 (m, 2H), 4.17-3.61 (m, 4H).

Examples Ff-557 and Ff-558 were prepared using general procedure IV-F starting with 4-(tert-butoxycarbonylamino)-7-fluoro-imidazo[1,5-a]quinoxaline-8-carboxylic acid Af-1 and N-methyl-6-(trifluoromethoxy)-2,3-dihydrobenzofuran-3-amine Eam-2. The isomers were separated using SFC (OJ-H 250×21 mm column, EtOH 25%).

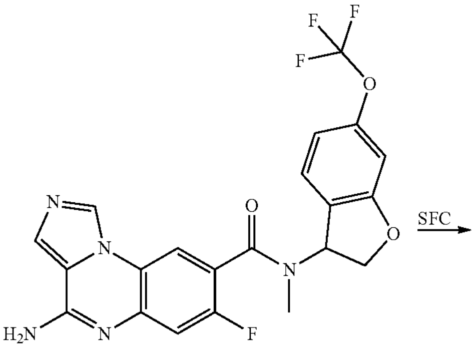

-continued

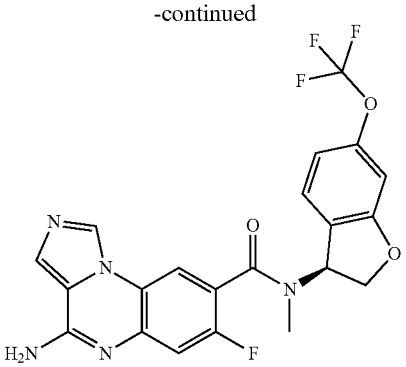

Example Ff-557
Peak 1

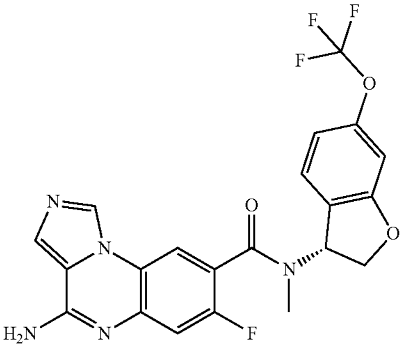

Example Ff-558
Peak 2

Example Ff-557: (S)-4-amino-7-fluoro-N-methyl-N-(6-(trifluoromethoxy)-2,3-dihydrobenzofuran-3-yl)imidazo[1,5-a]quinoxaline-8-carboxamide. Peak 1. ES/MS: m/z=462.2 $[M+H]^+$. $^1H$ NMR (400 MHz, MeOD) δ 9.25 (s, 1H), 8.76-8.24 (m, 2H), 7.75-7.23 (m, 2H), 7.23-6.61 (m, 2H), 6.61-6.24 (m, 0.5H rotamer), 5.86-5.44 (m, 0.5H rotamer), 4.98-4.86 (m, 1H), 4.78-4.67 (m, 1H), 2.85 (s, 1.5H rotamer), 2.78-2.70 (m, 1.5H rotamer).

Example Ff-558: (R)-4-amino-7-fluoro-N-methyl-N-(6-(trifluoromethoxy)-2,3-dihydrobenzofuran-3-yl)imidazo[1,5-a]quinoxaline-8-carboxamide. Peak 2. ES/MS: m/z=462.5 $[M+H]^+$. $^1H$ NMR (400 MHz, MeOD) δ 9.04 (s, 1H), 8.50-8.12 (m, 1H), 8.05-7.86 (m, 1H), 7.68-7.13 (m, 2H), 7.04-6.63 (m, 2H), 6.63-6.37 (m, 0.5H rotamer), 5.81-5.49 (m, 0.5H rotamer), 4.85 (s, 0.5H rotamer), 4.76-4.66 (m, 1+0.5H rotamer), 2.83 (s, 1.5H rotamer), 2.79-2.65 (m, 1.5H rotamer).

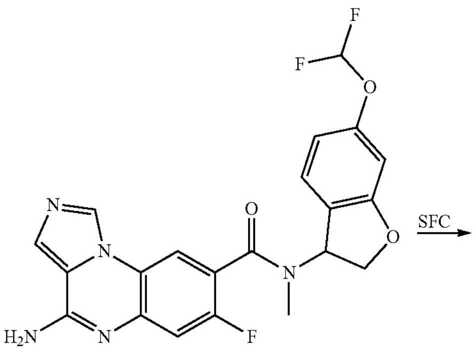

-continued

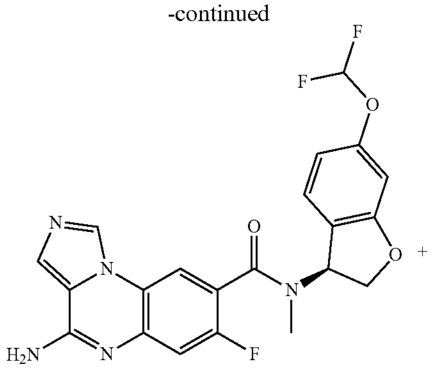

Peak 1
Example Ff-559

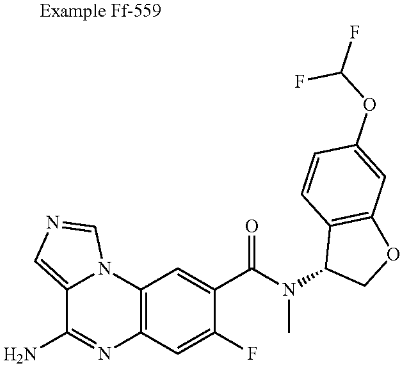

Peak 2

Example Ff-559: (S)-4-amino-N-(6-(difluoromethoxy)-2,3-dihydrobenzofuran-3-yl)-7-fluoro-N-methylimidazo[1,5-a]quinoxaline-8-carboxamide. Prepared using general procedure general procedure IV-F starting with 4-(tert-butoxycarbonylamino)-7-fluoro-imidazo[1,5-a]quinoxaline-8-carboxylic acid Af-1 and 6-(difluoromethoxy)-N-methyl-2,3-dihydrobenzofuran-3-amine Eam-3. The isomers were separated using SFC (OD-H 21×250 mm column, EtOH 25%). Peak 1. ES/MS: m/z=444.2 $[M+H]^+$. $^1H$ NMR (400 MHz, MeOD) δ 1H NMR (400 MHz, MeOD) δ 9.26 (s, 1H), 8.70-8.17 (m, 2H), 7.71-7.17 (m, 2H), 7.15-6.59 (m, 3H), 6.59-6.37 (m, 0.5H rotamer), 5.66-5.24 (m, 0.5H rotamer), 4.88-4.79 (m, 0.5H rotamer), 4.75-4.60 (m, 1+0.5H rotamer), 2.84 (s, 1.5H rotamer), 2.71 (s, 1.5H rotamer).

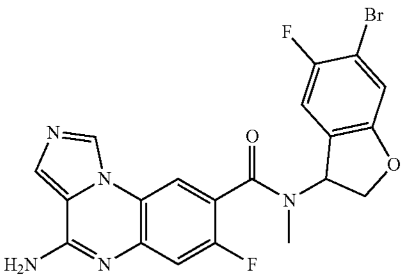 [SMILES: CN(C(=O)c1cc2c(cc1F)nc(N)c1cncn12)C1COc2cc(Br)c(F)cc21]

Example Ff-560: 4-amino-N-(6-bromo-5-fluoro-2,3-dihydrobenzofuran-3-yl)-7-fluoro-N-methylimidazo[1,5-a]quinoxaline-8-carboxamide. Prepared using general procedure IV-F starting with 4-(tert-butoxycarbonylamino)-7-fluoro-imidazo[1,5-a]quinoxaline-8-carboxylic acid Af-1 and 6-bromo-5-fluoro-N-methyl-2,3-dihydrobenzofuran-3-amine Eam-4. ES/MS: m/z=474.3 [M+H]$^+$. $^1$H NMR (400 MHz, MeOD) δ 9.26 (s, 1H), 8.53-8.21 (m, 2H), 7.58-7.41 (m, 1H), 7.30 (d, J=7.6 Hz, 1H), 7.19-7.13 (m, 1H), 6.47 (dd, J=8.8, 3.6 Hz, 0.6H major rotamer), 5.59 (t, J=6.5 Hz, 0.4H minor rotamer), 4.74-4.58 (m, 2H), 2.88 (s, 1.2H minor rotamer), 2.75 (s, 1.8H major rotamer).

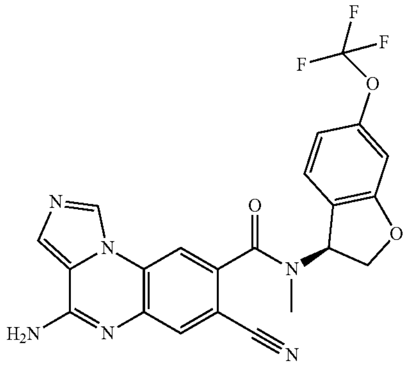 [SMILES: CN(C(=O)c1cc2c(cc1C#N)nc(N)c1cncn12)[C@@H]1COc2cc(OC(F)(F)F)ccc21]

Example Ff-561: (S)-4-amino-7-cyano-N-methyl-N-(6-(trifluoromethoxy)-2,3-dihydrobenzofuran-3-yl)imidazo[1,5-a]quinoxaline-8-carboxamide. Prepared using general procedure IV-F starting with 4-((tert-butoxycarbonyl)amino)-7-cyanoimidazo[1,5-a]quinoxaline-8-carboxylic acid Al-1 and (S)—N-methyl-6-(trifluoromethoxy)-2,3-dihydrobenzofuran-3-amine hydrogen chloride Eh-22. ES/MS: m/z=469.3 [M+H]$^+$. $^1$H NMR (400 MHz, MeOD) δ 9.40-9.19 (m, 1H), 8.59-8.47 (m, 1H), 8.31 (s, 1H), 8.13-7.91 (m, 1H), 7.66-7.42 (m, 1H), 7.01-6.78 (m, 2H), 6.65-6.49 (m, 0.6H major rotamer), 5.65-5.48 (m, 0.4H minor rotamer), 5.00-4.89 (m, 1H), 4.80-4.68 (m, 1H), 2.90 (s, 1.2H minor rotamer), 2.72 (s, 1.8H major rotamer).

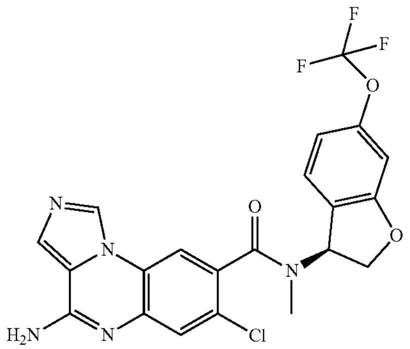 [SMILES: CN(C(=O)c1cc2c(cc1Cl)nc(N)c1cncn12)[C@@H]1COc2cc(OC(F)(F)F)ccc21]

Example Ff-562: (S)-4-amino-7-chloro-N-methyl-N-(6-(trifluoromethoxy)-2,3-dihydrobenzofuran-3-yl)imidazo[1,5-a]quinoxaline-8-carboxamide. Prepared using general procedure IV-F starting with 4-(tert-butoxycarbonylamino)-7-chloro-imidazo[1,5-a]quinoxaline-8-carboxylic acid Af-2 and (S)—N-methyl-6-(trifluoromethoxy)-2,3-dihydrobenzofuran-3-amine hydrogen chloride Eh-22. ES/MS: m/z=478.2 [M+H]$^+$. $^1$H NMR (400 MHz, MeOD) δ 9.42-9.04 (m, 1H), 8.65-8.22 (m, 2H), 7.86-7.60 (m, 1H), 7.60-7.30 (m, 1H), 7.06-6.70 (m, 2H), 6.57 (s, 0.7H major rotamer), 5.64-5.32 (m, 0.3H minor rotamer), 4.80-4.43 (m, 2H), 2.87 (s, 0.9H minor rotamer), 2.76-2.44 (m, 2.1H major rotamer).

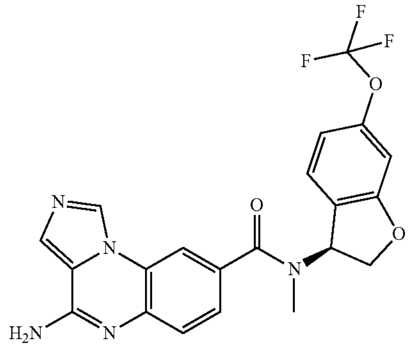

Example Ff-563: (S)-4-amino-N-methyl-N-(6-(trifluoromethoxy)-2,3-dihydrobenzofuran-3-yl)imidazo[1,5-a]quinoxaline-8-carboxamide. Prepared using general procedure IV-F starting with 4-(tert-butoxycarbonylamino)-imidazo[1,5-a]quinoxaline-8-carboxylic acid Ae-1 and (S)—N-methyl-6-(trifluoromethoxy)-2,3-dihydrobenzofuran-3-amine hydrogen chloride Eh-22. ES/MS: m/z=444.2 [M+H]$^+$. $^1$H NMR (400 MHz, MeOD) δ 9.44-9.13 (m, 1H), 8.91-8.24 (m, 2H), 8.16-7.45 (m, 3H), 7.10-6.80 (m, 2H), 6.46 (s, 0.5H rotamer), 6.00-5.81 (m, 0.5H rotamer), 4.88 (s, 0.5H rotamer), 4.82-4.46 (m, 1+0.5H rotamer), 2.91-2.72 (m, 3H).

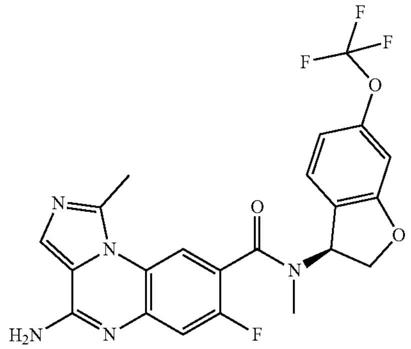 [SMILES: Cc1ncc2c(N)nc3cc(F)c(C(=O)N(C)[C@@H]4COc5cc(OC(F)(F)F)ccc54)cc3n12]

Example Ff-564: (S)-4-amino-7-fluoro-N,1-dimethyl-N-(6-(trifluoromethoxy)-2,3-dihydrobenzofuran-3-yl)imidazo[1,5-a]quinoxaline-8-carboxamide. Prepared using general procedure IV-F starting with 4-((tert-butoxycarbonyl)amino)-7-fluoro-1-methylimidazo[1,5-a]quinoxaline-8-carboxylic acid Af-5 and (S)—N-methyl-6-(trifluoromethoxy)-2,3-dihydrobenzofuran-3-amine hydrogen chloride Eh-22. ES/MS: m/z=476.3 [M+H]$^+$. $^1$H NMR (400 MHz, MeOD) δ 8.45-8.16 (m, 2H), 7.57-7.31 (m, 2H), 7.04-6.72 (m, 2H), 6.58-6.45 (m, 0.5H rotamer), 5.63 (s, 0.5H rotamer), 4.84 (1H), 4.77-4.68 (m, 1H), 3.20-3.06 (m, 3H), 2.86 (s, 1.5H rotamer), 2.78-2.64 (m, 1.5H rotamer). Example Ff-565

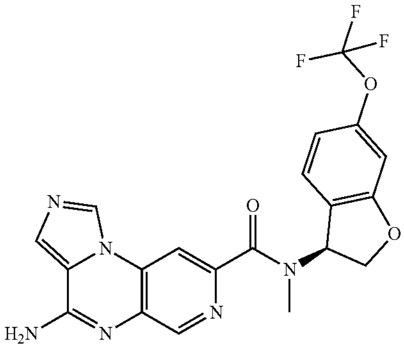 [SMILES: CN(C(=O)c1cc2c(cn1)nc(N)c1cncn12)[C@@H]1COc2cc(OC(F)(F)F)ccc21]

Example Ff-565: (S)-4-amino-N-methyl-N-(6-(trifluoromethoxy)-2,3-dihydrobenzofuran-3-yl)imidazo[1,5-a]pyrido[3,4-e]pyrazine-8-carboxamide. Prepared using general procedure IV-F starting with 4-((tert-butoxycarbonyl)amino)imidazo[1,5-a]pyrido[3,4-e]pyrazine-8-carboxylic acid Af-6 and (S)—N-methyl-6-(trifluoromethoxy)-2,3-dihydrobenzofuran-3-amine hydrogen chloride Eh-22. ES/MS: m/z=445.3 $[M+H]^+$. $^1H$ NMR (400 MHz, MeOD) δ 9.40-9.21 (m, 1H), 8.99-8.68 (m, 1H), 8.68-8.31 (m, 1H), 8.24-8.03 (m, 1H), 7.73-7.32 (m, 1H), 7.06-6.67 (m, 2H), 6.11-5.92 (m, 0.5H rotamer), 5.92-5.71 (m, 0.5H rotamer), 4.82-4.72 (m, 1H), 4.68-4.54 (m, 1H), 2.88-2.80 (m, 2.1H major rotamer), 2.68 (s, 0.9H minor rotamer).

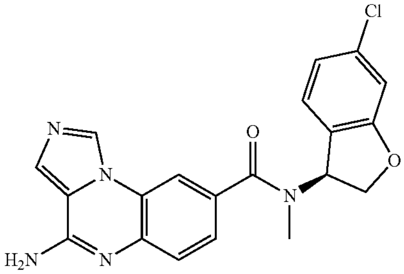 [SMILES: CN(C(=O)c1ccc2nc(N)c3cncn3c2c1)[C@@H]1COc2cc(Cl)ccc21]

Example Ff-566: (S)-4-amino-N-(6-chloro-2,3-dihydrobenzofuran-3-yl)-N-methylimidazo[1,5-a]quinoxaline-8-carboxamide. Prepared using general procedure IV-F starting with 4-(tert-butoxycarbonylamino)-imidazo[1,5-a]quinoxaline-8-carboxylic acid Ae-1 and (S)—N-methyl-6-chloro-2,3-dihydrobenzofuran-3-amine hydrogen chloride Eh-23. ES/MS: m/z=394.2 $[M+H]^+$. $^1H$ NMR (400 MHz, MeOD) δ 9.33 (s, 1H), 8.45-4.43 (m, 2H), 7.91-7.60 (m, 2H), 7.42 (s, 1H), 7.08-6.89 (m, 2H), 6.41 (m, 0.6H major rotamer), 5.66 (m, 0.4H minor rotamer), 4.85-4.59 (m, 2H), 2.88-2.77 (m, 3H).

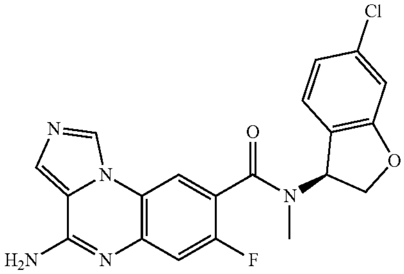 [SMILES: CN(C(=O)c1cc2c(cc1F)nc(N)c1cncn12)[C@@H]1COc2cc(F)ccc21]

Example Ff-567: (S)-4-amino-N-(6-chloro-2,3-dihydrobenzofuran-3-yl)-7-fluoro-N-methylimidazo[1,5-a]quinoxaline-8-carboxamide. Prepared using general procedure IV-F starting 4-(tert-butoxycarbonylamino)-7-fluoro-imidazo[1,5-a]quinoxaline-8-carboxylic acid Af-1 and (S)—N-methyl-6-chloro-2,3-dihydrobenzofuran-3-amine hydrogen chloride Eh-23. ES/MS: m/z=412.6 $[M+H]^+$. $^1H$ NMR (400 MHz, MeOD) δ 9.25 (s, 1H), 8.59-8.26 (m, 2H), 7.75-7.25 (m, 2H), 7.13-6.80 (m, 2H), 6.60-6.35 (m, 0.6H major rotamer), 5.61-5.43 (m, 0.4H minor rotamer), 4.85-4.56 (m, 2H), 2.85 (s, 1.4H minor rotamer), 2.78-2.58 (m, 1.6H major

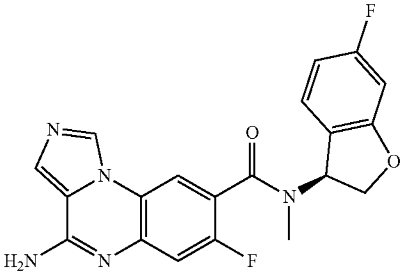

Example Ff-568: (S)-4-amino-N-(6-fluoro-2,3-dihydrobenzofuran-3-yl)-7-fluoro-N-methylimidazo[1,5-a]quinoxaline-8-carboxamide. Prepared using general procedure VI-F starting 4-(tert-butoxycarbonylamino)-7-fluoro-imidazo[1,5-a]quinoxaline-8-carboxylic acid Af-1 and (S)—N-methyl-6-fluoro-2,3-dihydrobenzofuran-3-amine hydrogen chloride Eh-24. ES/MS: m/z=396.2 $[M+H]^+$. $^1H$ NMR (400 MHz, MeOD) δ 9.21 (s, 1H), 8.47-8.22 (m, 2H), 7.52-7.26 (m, 2H), 6.89-6.60 (m, 2H), 6.54-6.43 (m, 0.7H major rotamer), 5.56 (s, 0.3H minor rotamer), 4.85-4.64 (m, 2H), 2.84 (s, 2.1H major rotamer), 2.71 (s, 0.9H minor rotamer).

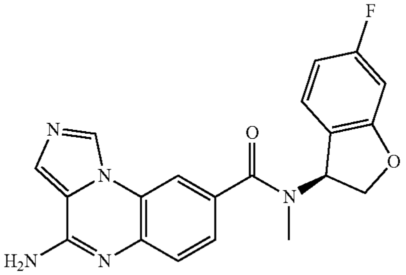

Example Ff-569: (S)-4-amino-N-(6-fluoro-2,3-dihydrobenzofuran-3-yl)-N-methylimidazo[1,5-a]quinoxaline-8-carboxamide. Prepared using general procedure VI-F starting with 4-(tert-butoxycarbonylamino)-imidazo[1,5-a]quinoxaline-8-carboxylic acid Ae-1 and (S)—N-methyl-6-fluoro-2,3-dihydrobenzofuran-3-amine hydrogen chloride Eh-24. ES/MS: m/z=378.2 $[M+H]^+$. $^1H$ NMR (400 MHz, MeOD) δ 9.34 (s, 1H), 8.57-8.17 (m, 2H), 7.71 (s, 2H), 7.44 (s, 1H), 7.01-6.55 (m, 2H), 6.41 (s, 0.6H major rotamer), 5.63 (s, 0.4H minor rotamer), 4.86-4.44 (m, 2H), 2.95-2.46 (m, 3H).

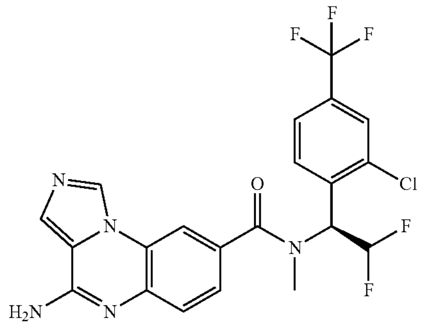 [SMILES: CN(C(=O)c1ccc2nc(N)c3cncn3c2c1)[C@@H](c1ccc(C(F)(F)F)cc1Cl)C(F)F]

Example Ff-570: (S)-4-amino-N-(1-(2-chloro-4-(trifluoromethyl)phenyl)-2,2-difluoroethyl)-N-methylimidazo[1,5-a]quinoxaline-8-carboxamide. Prepared using general procedure VI-F starting with 4-(tert-butoxycarbonylamino)-imidazo[1,5-a]quinoxaline-8-carboxylic acid Ae-1 and (S)-1-(2-chloro-4-(trifluoromethyl)phenyl)-2,2-difluoro-N-methylethan-1-amine hydrogen chloride Eal-6. ES/MS: m/z=484.3 $[M+H]^+$. $^1H$ NMR (400 MHz, MeOD) δ 9.37 (s, 1H), 8.42 (d, J=2.3 Hz, 2H), 8.06 (d, J=8.3 Hz, 1H), 7.96 (s, 1H), 7.87-7.76 (m, 1H), 7.76-7.57 (m, 2H), 6.82 (td, J=54.5, 4.5 Hz, 1H), 6.27 (s, 1H), 2.96 (s, 3H).

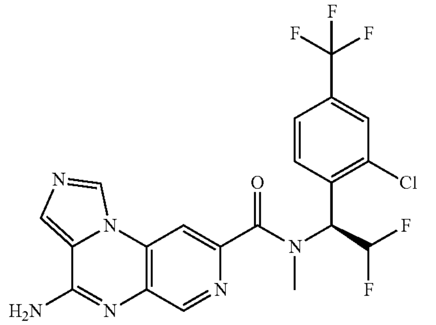 [SMILES: CN(C(=O)c1cc2c(cn1)nc(N)c1cncn12)[C@@H](c1ccc(C(F)(F)F)cc1Cl)C(F)F]

Example Ff-571: (S)-4-amino-N-(1-(2-chloro-4-(trifluoromethyl)phenyl)-2,2-difluoroethyl)-N-methylimidazo[1,5-a]pyrido[3,4-e]pyrazine-8-carboxamide. Prepared using general procedure VI-F starting with 4-((tert-butoxycarbonyl)amino)imidazo[1,5-a]pyrido[3,4-e]pyrazine-8-carboxylic acid Af-6 and (S)-1-(2-chloro-4-(trifluoromethyl)phenyl)-2,2-difluoro-N-methylethan-1-amine hydrogen chloride Eal-6. ES/MS: m/z=485.3 $[M+H]^+$. $^1H$ NMR (400 MHz, MeOD) δ 9.37 (s, 1H), 8.81 (s, 1H), 8.51 (s, 1H), 8.29 (s, 1H), 8.06 (d, J=8.5 Hz, 1H), 7.94 (s, 1H), 7.78 (d, J=8.8 Hz, 1H), 7.03-6.57 (m, 1H), 6.29 (t, J=12.7 Hz, 1H), 3.04 (s, 3H).

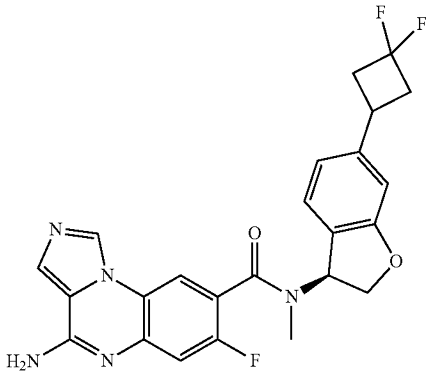 [SMILES: CN(C(=O)c1cc2c(cc1F)nc(N)c1cncn12)[C@@H]1COc2cc(C3CC(F)(F)C3)ccc21]

Example Ff-572: (S)-4-amino-N-(6-(3,3-difluorocyclobutyl)-2,3-dihydrobenzofuran-3-yl)-7-fluoro-N-methylimidazo[1,5-a]quinoxaline-8-carboxamide. Prepared using example Ff-94 and 3-bromo-1,1-difluoro-cyclobutane following the reductive coupling procedure reported for example Ff-444. ES/MS: m/z=468.3 $[M+H]^+$. $^1H$ NMR (400 MHz, MeOD) δ 9.21 (s, 1H), 8.49-8.20 (m, 2H), 7.53-7.24 (m, 2H), 7.08-6.76 (m, 2H), 6.62-6.35 (m, 0.5H rotamer), 5.62-5.43 (m, 0.5H rotamer), 4.84-4.60 (m, 2H), 3.22-2.26 (m, 8H).

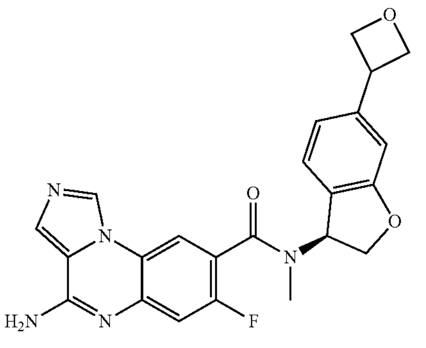 [SMILES: CN(C(=O)c1cc2c(cc1F)nc(N)c1cncn12)[C@@H]1COc2cc(C3COC3)ccc21]

Example Ff-573: (S)-4-amino-7-fluoro-N-methyl-N-(6-(oxetan-3-yl)-2,3-dihydrobenzofuran-3-yl)imidazo[1,5-a]quinoxaline-8-carboxamide. Prepared using example Ff-94 and 3-iodooxetane following the reductive coupling procedure reported for example Ff-444. ES/MS: m/z=418.2 $[M-Me]^+$. $^1H$ NMR (400 MHz, Methanol-d4) δ 9.19 (s, 1H), 8.52-8.00 (m, 2H), 7.60-7.12 (m, 2H), 7.03-6.61 (m, 2H), 6.56-6.47 (m, 0.5H rotamer), 5.59-5.41 (m, 0.5H rotamer), 5.15-4.98 (m, 1H), 4.86-4.52 (m, 1H), 3.46-3.37 (m, 1H), 3.30-3.11 (m, 4H), 2.86-2.62 (m, 3H).

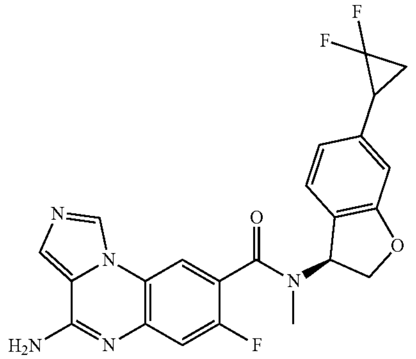 [SMILES: CN(C(=O)c1cc2c(cc1F)nc(N)c1cncn12)[C@@H]1COc2cc(C3CC3(F)F)ccc21]

Example Ff-574: 4-amino-N-((3S)-6-(2,2-difluorocyclopropyl)-2,3-dihydrobenzofuran-3-yl)-7-fluoro-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (3S)-6-(2,2-difluorocyclopropyl)-N-methyl-2,3-dihydrobenzofuran-3-amine hydrogen chloride Ebn-1. ES/MS: m/z=454.2 $[M+H]^+$. $^1H$ NMR (400 MHz, MeOD) δ 9.27 (s, 1H), 8.63-8.26 (m, 2H), 7.58-7.13 (m, 2H), 7.08-6.61 (m, 2H), 6.61-6.56-6.37 (m, 0.5H rotamer), 5.68-5.44 (m, 0.5H rotamer), 4.82-4.48 (s, 2H), 3.07-2.61 (m, 3H), 2.07-1.56 (m, 3H).

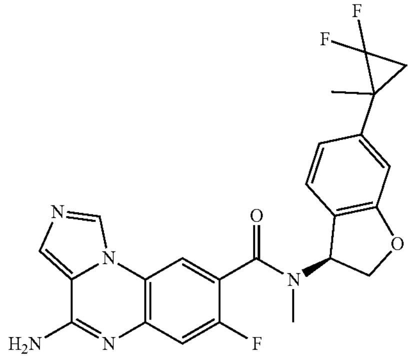 [SMILES: CN(C(=O)c1cc2c(cc1F)nc(N)c1cncn12)[C@@H]1COc2cc(C3(C)CC3(F)F)ccc21]

Example Ff-575: 4-amino-N-((3S)-6-(2,2-difluoro-1-methylcyclopropyl)-2,3-dihydrobenzofuran-3-yl)-7-fluoro-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (3S)-6-(2,2-difluoro-1-methylcyclopropyl)-N-methyl-2,3-dihydrobenzofuran-3-amine hydrogen chloride Ebn-2. ES/MS: m/z=468.2 $[M+H]^+$. $^1H$ NMR (400 MHz, MeOD) δ 9.26 (s, 1H), 8.76-8.32 (m, 2H), 7.67-7.21 (m, 2H), 7.23-6.81 (m, 2H), 6.59-6.35 (m, 0.5H rotamer), 5.66-5.41 (m, 0.5H rotamer), 4.86-4.37 (m, 2H), 2.97-2.76 (m, 1.5H rotamer), 2.76-2.57 (m, 1.5H rotamer), 1.88-1.60 (m, 2H), 1.60-1.38 (m, 3H).

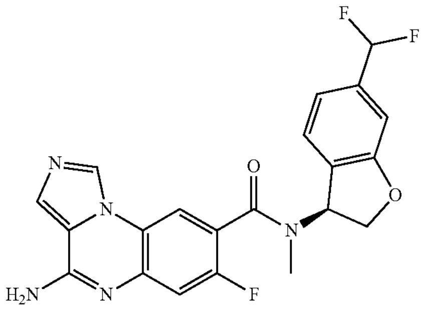 [SMILES: CN(C(=O)c1cc2c(cc1F)nc(N)c1cncn12)[C@@H]1COc2cc(C(F)F)ccc21]

Example Ff-576: (S)-4-amino-N-(6-(difluoromethyl)-2,3-dihydrobenzofuran-3-yl)-7-fluoro-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 (S)-6-(difluoromethyl)-N-methyl-2,3-dihydrobenzofuran-3-amine hydrogen chloride Eau-6. ES/MS: m/z=428.2 $[M+H]^+$. $^1H$ NMR (400 MHz, MeOD) δ 9.18 (s, 1H), 8.52-8.15 (m, 2H), 7.59-7.28 (m, 2H), 7.28-6.96 (m, 2H), 6.97-6.58 (m, 1H), 6.61-6.42 (s, 0.5H rotamer), 5.81-5.50 (s, 0.5H rotamer), 4.83-4.62 (m, 2H), 2.84 (s, 1.5H rotamer), 2.77-2.68 (m, 1.5H rotamer).

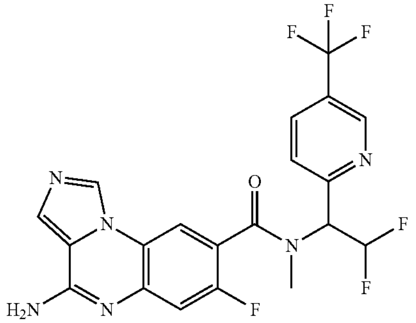 [SMILES: CN(C(=O)c1cc2c(cc1F)nc(N)c1cncn12)C(c1ccc(C(F)(F)F)cn1)C(F)F]

Example Ff-577: 4-amino-N-(2,2-difluoro-1-(5-(trifluoromethyl)pyridin-2-yl)ethyl)-7-fluoro-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and 2,2-difluoro-N-methyl-1-(5-(trifluoromethyl)pyridin-2-yl)ethan-1-amine Ebq-1. ES/MS: m/z=469.3 $[M+H]^+$. $^1H$ NMR (400 MHz, MeOD) δ 9.25 (s, 1H), 8.99 (s, 1H), 8.42-8.21 (m, 3H), 7.88-7.75 (m, 1H), 7.50-7.39 (m, 1H), 7.18-6.76 (m, 1H), 6.25-6.15 (m, 0.5H rotamer), 5.47-5.33 (m, 0.5H rotamer), 3.12 (s, 3H).

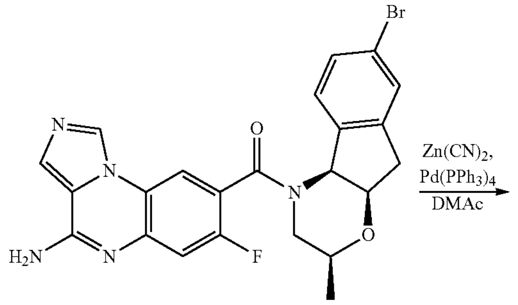

Example Ff-93

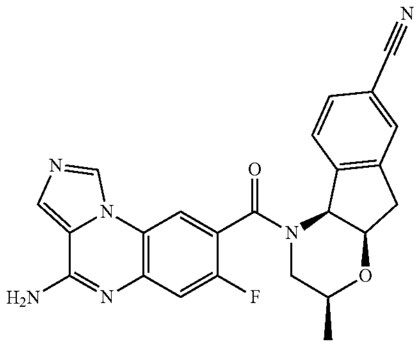

Example Ff-578

Example Ff-578: (2S,4aS,9aR)-4-(4-amino-7-fluoroimidazo[1,5-a]quinoxaline-8-carbonyl)-2-methyl-2,3,4,4a,9,9a-hexahydroindeno[2,1-b][1,4]oxazine-7-carbonitrile. To a solution of (4-amino-7-fluoroimidazo[1,5-a]quinoxalin-8-yl)((2S,4aS,9aR)-7-bromo-2-methyl-2,3,9,9a-tetrahydroindeno[2,1-b][1,4]oxazin-4(4aH)-yl)methanone (Example Ff-93) (0.082 mmol, 1.0 equiv) in DMAc (2.0 mL) was added tetrakis(triphenylphosphine)palladium(0) (0.041 mmol, 47 mg) and zinc cyanide (0.0041 mmol, 0.05 equiv) and the reaction mixture was stirred at 100 C for 20 h. The reaction was then diluted with EtOAc, washed with 5% aq LiCl, dried over magnesium sulfate, concentrated and purified by silica gel chromatography. The purified by reverse phase HPLC to afford the desired product. ES/MS: m/z=443.3 $[M+H]^+$. $^1$H NMR (400 MHz, MeOD) δ 9.43-9.01 (m, 1H), 8.66-8.13 (m, 2H), 7.84-7.25 (m, 4H), 6.16-5.88 (m, 1H), 4.65-4.48 (m, 1H), 3.89-3.35 (m, 3H), 3.22-2.72 (m, 2H), 1.06 (m, 3H). Calculated: 19H, found 17H

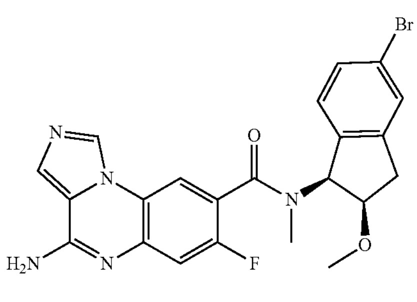 [SMILES: CO[C@@H]1Cc2cc(Br)ccc2[C@@H]1N(C)C(=O)c1cc2c(cc1F)nc(N)c1cncn12]

Example Ff-579: 4-amino-N-((1S,2R)-5-bromo-2-methoxy-2,3-dihydro-1H-inden-1-yl)-7-fluoro-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (1S,2R)-5-bromo-2-methoxy-N-methyl-2,3-dihydro-1H-inden-1-amine hydrochloride Ebo-1. ES/MS: m/z=484.5 $[M+H]^+$. $^1$H NMR (400 MHz, MeOD) δ 9.41-9.18 (m, 1H), 8.66-8.15 (m, 2H), 7.77-7.12 (m, 4H), 6.49-6.12 (m, 0.6H major rotamer), 5.42-5.08 (m, 0.4H minor rotamer), 4.60-4.23 (m, 0.6H major rotamer), 4.21-3.99 (m, 0.4H minor rotamer), 3.56-3.45 (m, 3H), 3.30-2.80 (m, 3H), 2.78-2.72 (m, 2H).

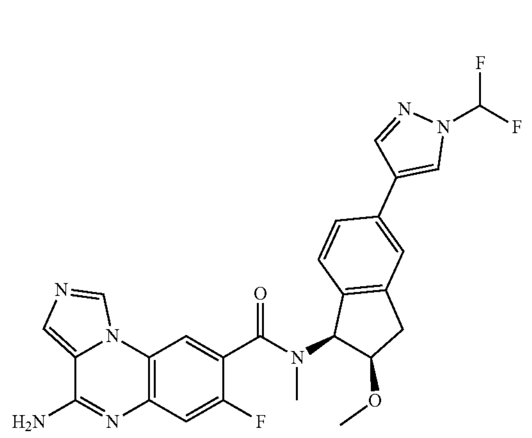 [SMILES: CO[C@@H]1Cc2cc(-c3cnn(C(F)F)c3)ccc2[C@@H]1N(C)C(=O)c1cc2c(cc1F)nc(N)c1cncn12]

Example Ff-580: 4-amino-N-((1S,2R)-5-(1-(difluoromethyl)-1H-pyrazol-4-yl)-2-methoxy-2,3-dihydro-1H-inden-1-yl)-7-fluoro-N-methylimidazo[1,5-a]quinoxaline-8-carboxamide. Prepared following the procedure reported for example Ff-23 starting with 4-amino-N-((1S,2R)-5-bromo-2-methoxy-2,3-dihydro-1H-inden-1-yl)-7-fluoro-N-methylimidazo[1,5-a]quinoxaline-8-carboxamide (Example Ff-579), and 1-(difluoromethyl)-4-(4,4,5,5-tetramethyl-1,3,2-dioxaborolan-2-yl)-1H-pyrazole. ES/MS: m/z=522.2 $[M+H]^+$. $^1$H NMR (400 MHz, MeOD) δ 9.37-9.07 (m, 1H), 8.68-8.28 (m, 3H), 8.28-7.92 (m, 1H), 7.75-7.21 (m, 5H), 6.47-6.20 (m, 0.6H major rotamer), 5.53-5.02 (m, 0.4H minor rotamer), 4.69-4.37 (m, 0.6H major rotamer), 4.35-4.06 (m, 0.4H minor rotamer), 3.61-3.45 (m, 3H), 3.23-2.84 (m, 3H), 2.81-2.73 (m, 2H).

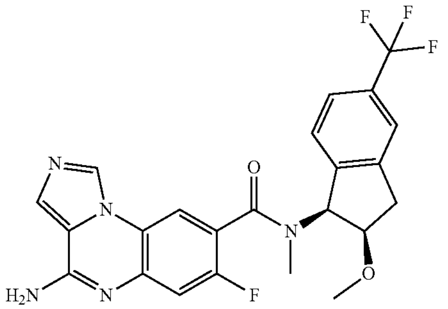 [SMILES: CO[C@@H]1Cc2cc(C(F)(F)F)ccc2[C@@H]1N(C)C(=O)c1cc2c(cc1F)nc(N)c1cncn12]

Example Ff-581: 4-amino-7-fluoro-N-((1S,2R)-2-methoxy-5-(trifluoromethyl)-2,3-dihydro-1H-inden-1-yl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (1S,2R)-2-methoxy-N-methyl-5-(trifluoromethyl)-2,3-dihydro-1H-inden-1-amine hydrochloride Eaz-9. ES/MS: m/z=484.5 $[M+H]^+$. $^1$H NMR (400 MHz, MeOD) δ 9.31 (s, 1H), 8.47 (d, J=5.8 Hz, 1H), 8.36 (d, J=3.5 Hz, 1H), 7.67 (d, J=9.0 Hz, 2H), 7.58-7.30 (m, 2H), 6.37 (d, J=7.1 Hz, 1H), 4.54 (q, J=7.0 Hz, 1H), 3.54 (s, 2H major rotamer), 3.49 (d, J=6.7 Hz, 1H minor rotamer), 3.40 (dd, J=17.3, 7.4 Hz, 1H), 3.16 (dd, J=17.3, 6.3 Hz, 1H), 2.92 (d, J=17.9 Hz, 1H minor rotamer), 2.77 (d, J=1.1 Hz, 2H major rotamer).

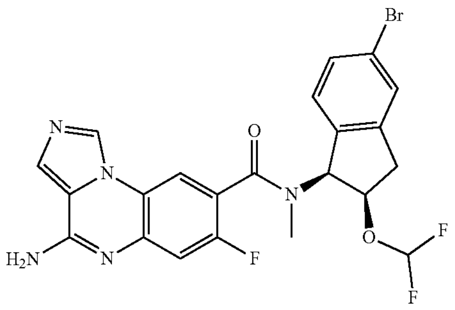 [SMILES: CN(C(=O)c1cc2c(cc1F)nc(N)c1cncn12)[C@H]1c2ccc(Br)cc2C[C@H]1OC(F)F]

Example Ff-582: 4-amino-N-((1S,2R)-5-bromo-2-(difluoromethoxy)-2,3-dihydro-1H-inden-1-yl)-7-fluoro-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (1S,2R)-5-bromo-2-(difluoromethoxy)-N-methyl-2,3-dihydro-1H-inden-1-amine Ebp-1. ES/MS: m/z=520.2 $[M+H]^+$. $^1$H NMR (400 MHz, MeOD) δ 9.22 (m, 1H), 8.63-8.22 (m, 2H), 7.77-7.42 (m, 2H), 7.42-7.11 (m, 2H), 6.85-6.35 (m, 1H), 6.35-6.20 (m, 0.5H rotamer), 5.40-5.21 (m, 0.5H rotamer), 3.46-3.38 (m, 1H), 3.24-3.06 (m, 2H), 2.84-2.65 (m, 3H).

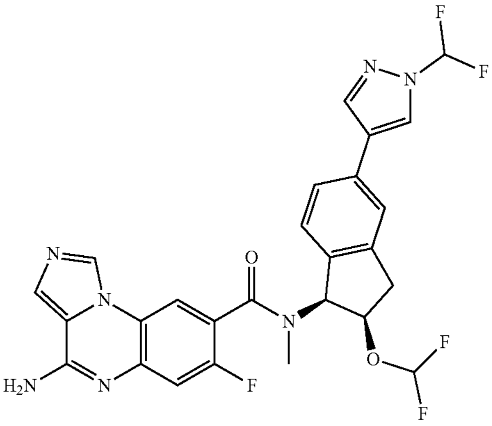 [SMILES: CN(C(=O)c1cc2c(cc1F)nc(N)c1cncn12)[C@H]1c2ccc(-c3cnn(C(F)F)c3)cc2C[C@H]1OC(F)F]

Example Ff-583: 4-amino-N-((1S,2R)-2-(difluoromethoxy)-5-(1-(difluoromethyl)-1H-pyrazol-4-yl)-2,3-dihydro-1H-inden-1-yl)-7-fluoro-N-methylimidazo[1,5-a]quinoxaline-8-carboxamide. Prepared following the procedure reported for example Ff-23 starting with 4-amino-N-((1S,2R)-5-bromo-2-(difluoromethoxy)-2,3-dihydro-1H-inden-1-yl)-7-fluoro-N-methylimidazo[1,5-a]quinoxaline-8-carboxamide (example Ff-582), and 1-(difluoromethyl)-4-(4,4,5,5-tetramethyl-1,3,2-dioxaborolan-2-yl)-1H-pyrazole. ES/MS: m/z=558.2 $[M+H]^+$. $^1$H NMR (400 MHz, MeOD) δ 9.35-9.06 (m, 1H), 8.65-8.28 (m, 3H), 8.12 (d, J=4.1 Hz, 1H), 7.82-7.29 (m, 5H), 6.98-6.11 (m, 2H), 5.53-5.19 (m, 1H), 3.55-3.19 (m, 2H), 3.00-2.79 (m, 3H).

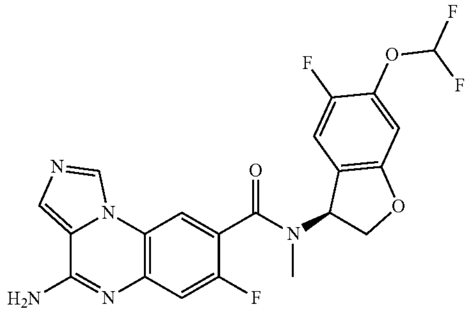 [SMILES: CN(C(=O)c1cc2c(cc1F)nc(N)c1cncn12)[C@@H]1COc2cc(OC(F)F)c(F)cc21]

Example Ff-584: (S)-4-amino-N-(6-(difluoromethoxy)-5-fluoro-2,3-dihydrobenzofuran-3-yl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (S)-6-(difluoromethoxy)-5-fluoro-N-methyl-2,3-dihydrobenzofuran-3-amine Ead-1 (HATU was used instead of Pybrop and MeCN was used as the solvent). ES/MS: m/z=462.0 $[M+H]^+$. $^1$H NMR (400 MHz, Methanol-d4) δ 9.26 (s, 1H), 8.45 (d, J=5.9 Hz, 1H), 8.39 (d, J=3.1 Hz, 1H), 7.48 (d, J=9.7 Hz, 1H), 7.33 (d, J=9.3 Hz, 1H), 7.09-6.66 (m, 1H), 6.83 (d, J=6.1 Hz, 0.5H rotamer), 6.49 (dd, J=8.8, 3.4 Hz, 0.5H rotamer), 5.60 (t, J=6.5 Hz, 0.5H rotamer), 4.86-4.78 (m, 0.5H rotamer), 4.74-4.59 (m, 2H), 2.87 (s, 1.5H rotamer), 2.75 (d, J=1.2 Hz, 1.5H rotamer).

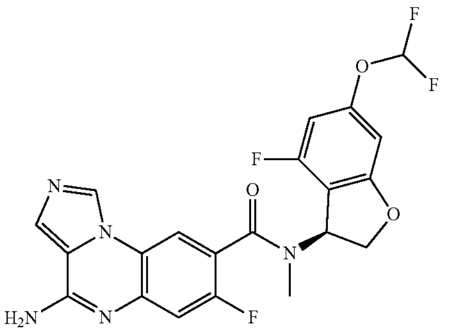 [SMILES: CN(C(=O)c1cc2c(cc1F)nc(N)c1cncn12)[C@@H]1COc2cc(OC(F)F)cc(F)c21]

Example Ff-585: (S)-4-amino-N-(6-(difluoromethoxy)-4-fluoro-2,3-dihydrobenzofuran-3-yl)-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (S)-6-(difluoromethoxy)-4-fluoro-N-methyl-2,3-dihydrobenzofuran-3-amine Eac-1 (HATU was used instead of Pybrop and MeCN was used as the solvent). ES/MS: m/z=462.0 $[M+H]^+$. $^1$H NMR (400 MHz, Methanol-d4) δ 9.35-9.25 (m, 1H), 8.63-8.30 (m, 2H), 7.60-7.40 (m, 1H), 6.90 (td, J=73.3, 11.3 Hz, 1H), 6.65-6.39 (m, 2H), 5.77 (d, J=6.7 Hz, 0.5H rotamer), 4.78 (m, 2H), 4.71 (dd, J=10.6, 3.4 Hz, 0.5H rotamer), 2.89 (s, 1.5H rotamer), 2.78 (d, J=1.2 Hz, 1.5H rotamer).

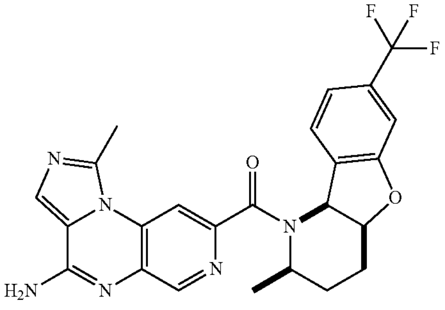

Example Ff-586: Rac-(4-amino-1-methylimidazo[1,5-a]pyrido[3,4-e]pyrazin-8-yl)(2-methyl-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)-1-methylimidazo[1,5-a]pyrido[3,4-e]pyrazine-8-carboxylic acid Ag-1 and cis-2-methyl-7-(trifluoromethyl)-1,2,3,4,4a,9b-hexahydrobenzofuro[3,2-b]pyridine Ev-4. ES/MS: m/z=483.0 $[M+H]^+$. $^1H$ NMR (400 MHz, Methanol-d4) δ 8.83 (s, 1H), 8.47 (s, 1H), 8.28 (s, 1H), 8.00 (d, J=7.8 Hz, 0.8H major rotamer), 7.67-7.58 (m, 0.2H minor rotamer), 7.30-7.22 (m, 1H), 7.14-6.98 (m, 1H), 6.70-6.59 (m, 0.2H minor rotamer), 6.14 (d, J=10.2 Hz, 0.8H rotamer), 5.32-5.26 (m, 0.2H, minor rotamer), 5.14 (d, J=10.2 Hz, 0.8H rotamer), 4.70-4.48 (m, 1H), 3.18 (s, 3H), 2.13-1.75 (m, 3H), 1.49-1.36 (m, 1H), 1.13-0.77 (m, 3H).

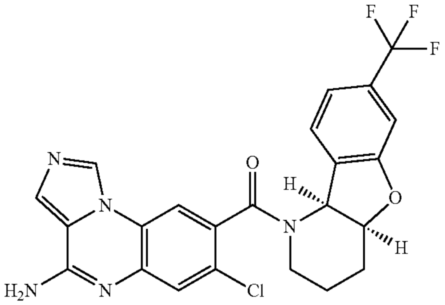 [SMILES: Nc1nc2cc(Cl)c(C(=O)N3CCC[C@@H]4Oc5cc(C(F)(F)F)ccc5[C@@H]43)cc2n2cncc12]

Example Ff-587: (4-amino-7-chloroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)-7-chloroimidazo[1,5-a]quinoxaline-8-carboxylic acid Af-2 and (4aS,9bS)-7-(trifluoromethyl)-1,2,3,4,4a,9b-hexahydrobenzofuro[3,2-b]pyridine Ew-1. ES/MS: m/z=488.0 $[M+H]^+$. $^1H$ NMR (400 MHz, Methanol-d4) δ 9.41-9.23 (m, 1H), 8.67-8.31 (m, 2H), 7.82-7.54 (m, 2H), 7.38-7.21 (m, 1H), 7.15 (s, 0.7H major rotamer), 7.07 (s, 0.3H minor rotamer), 6.49 (dd, J=12.4, 9.0 Hz, 0.7H major rotamer), 5.65-5.49 (m, 0.3H minor rotamer), 5.26-5.06 (m, 1H), 4.54-4.44 (m, 0.3H minor rotamer), 3.39-3.34 (m, 0.7H major rotamer), 3.11-2.83 (m, 1H), 2.21-1.98 (m, 2H), 1.97-1.63 (m, 2H).

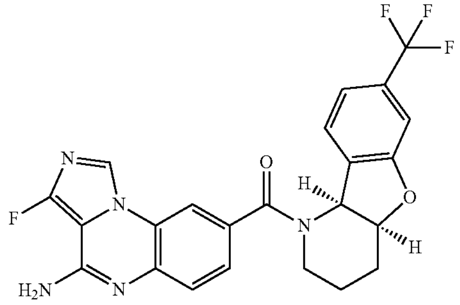 [SMILES: Nc1nc2ccc(C(=O)N3CCC[C@@H]4Oc5cc(C(F)(F)F)ccc5[C@@H]43)cc2n2cnc(F)c12]

Example Ff-588: (4-amino-3-fluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)-3-fluoroimidazo[1,5-a]quinoxaline-8-carboxylic acid Ah-1 and (4aS,9bS)-7-(trifluoromethyl)-1,2,3,4,4a,9b-hexahydrobenzofuro[3,2-b]pyridine Ew-1. ES/MS: m/z=472.0 $[M+H]^+$. $^1H$ NMR (400 MHz, Methanol-d4) δ 8.94 (d, J=1.2 Hz, 1H), 8.34 (s, 1H), 7.64 (s, 2H), 7.61-7.54 (m, 1H), 7.30-7.23 (m, 1H), 7.10 (s, 1H), 6.30 (s, 1H), 5.14 (s, 1H), 3.73-3.41 (m, 0.6H rotamer), 2.95 (s, 1H), 2.17-1.96 (m, 2H), 1.94-1.78 (m, 1H), 1.71 (ddt, J=14.1, 11.5, 7.4 Hz, 1H), 1.28 (d, J=3.8 Hz, 0.4H rotamer).

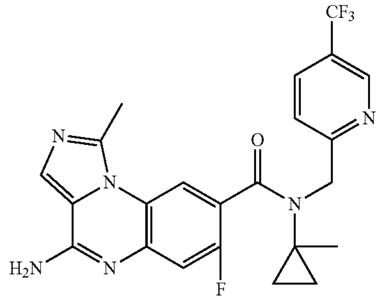 [SMILES: Cc1ncc2c(N)nc3cc(F)c(C(=O)N(Cc4ccc(C(F)(F)F)cn4)C4(C)CC4)cc3n12]

Example Ff-589: 4-amino-7-fluoro-1-methyl-N-(1-methylcyclopropyl)-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoro-1-methylimidazo[1,5-a]quinoxaline-8-carboxylic acid Af-5 and 1-methyl-N-((5-(trifluoromethyl)pyridin-2-yl)methyl)cyclopropan-1-amine Ec-21. ES/MS: m/z=473.0 $[M+H]^+$. $^1H$ NMR (400 MHz, DMSO-$d_6$) δ 9.12 (br, 2H), 8.94 (s, 1H), 8.37-7.88 (m, 3H), 7.62-7.29 (m, 2H), 4.93 (s, 1.4H, major rotamer), 4.69 (s, 0.6H, minor rotamer), 3.06 (s, 2.1H, major rotamer), 2.87 (s, 0.9H, minor rotamer), 1.32 (s, 2.1H, major rotamer), 1.19 (s, 0.9H, minor rotamer), 1.04-0.83 (m, 2H), 0.79-0.43 (m, 2H).

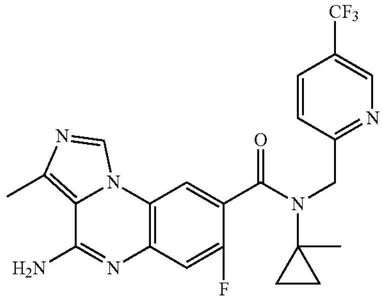 [SMILES: Cc1ncn2c1c(N)nc1cc(F)c(C(=O)N(Cc3ccc(C(F)(F)F)cn3)C3(C)CC3)cc12]

Example Ff-590: 4-amino-7-fluoro-3-methyl-N-(1-methylcyclopropyl)-N-((5-(trifluoromethyl)pyridin-2-yl)methyl)imidazo[1,5-a]quinoxaline-8-carboxamide. Prepared following general procedure VI-F starting with 4-((tert-butoxycarbonyl)amino)-7-fluoro-3-methylimidazo[1,5-a]quinoxaline-8-carboxylic acid Af-4 and 1-methyl-N-((5-(trifluoromethyl)pyridin-2-yl)methyl)cyclopropan-1-amine Ec-21. ES/MS: m/z=473.0 $[M+H]^+$. $^1H$ NMR (400 MHz, DMSO-$d_6$) δ 9.35 (s, 0.7H, major rotamer), 9.20 (s, 0.3H, minor rotamer), 8.97 (d, J=2.3 Hz, 0.7H, major rotamer), 8.96-8.89 (m, 0.3H, minor rotamer), 8.69 (br, 2H), 8.46 (d, J=6.1H, 0.7H, major rotamer), 8.26-8.17 (m, 1H), 8.03 (dd, J=8.3, 2.4 Hz, 0.3H, minor rotamer), 7.57 (d, J=8.3 Hz, 0.7H, major rotamer), 7.45 (d, J=10.1 Hz, 0.7H, major rotamer), 7.35 (d, J=8.2 Hz, 0.3H, minor rotamer), 7.24 (d, J=9.9 Hz, 0.3H, minor rotamer), 4.92 (s, 1.4H, major rotamer), 4.68 (s, 0.6H, minor rotamer), 2.71 (s, 2.1H, major rotamer), 2.67 (s, 0.9H, minor rotamer), 1.31 (s, 2.1H, major rotamer), 1.24 (s, 0.9H, minor rotamer), 1.02-0.90 (m, 2H), 0.76 (s, 0.6H, minor rotamer), 0.53-0.46 (m, 1.4H, major rotamer).

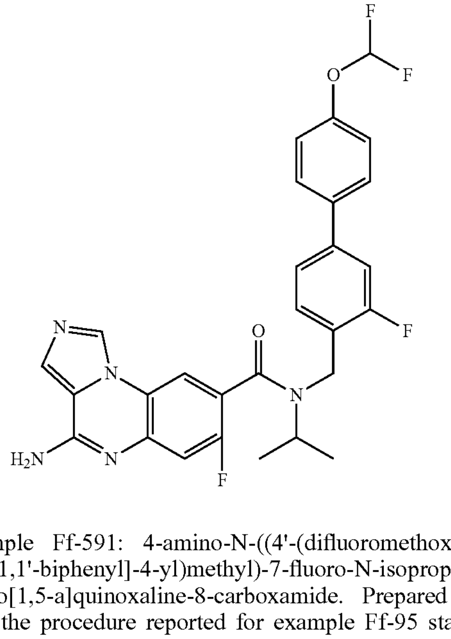

Example Ff-591: 4-amino-N-((4'-(difluoromethoxy)-3-fluoro-[1,1'-biphenyl]-4-yl)methyl)-7-fluoro-N-isopropylimidazo[1,5-a]quinoxaline-8-carboxamide. Prepared following the procedure reported for example Ff-95 starting with 4-((tert-butoxycarbonyl)amino)-7-fluoroimidazo[1,5-a]quinoxaline-8-carboxylic acid Af-1, N-(4-bromo-2-fluorobenzyl)propan-2-amine Ed-9 and commercial (4-(difluoromethoxy)phenyl)boronic acid. ES/MS: m/z=538.0 $[M+H]^+$. $^1H$ NMR (400 MHz, DMSO-$d_6$) δ 9.44-9.02 (m, 3H), 8.57-8.24 (m, 2H), 7.60-7.45 (m, 3H), 7.33-7.27 (m, 2H), 7.16-7.07 (m, 2H), 7.03-6.96 (m, 1H), 6.80-6.75 (m, 1H), 4.90-4.61 (m, 2H), 4.60-4.50 (m, 0.2H, minor rotamer), 3.98 (p, J=6.6 Hz, 0.8H, major rotamer), 1.27 (d, J=6.8 Hz, 1.2H, minor rotamer), 1.16 (d, J=6.6 Hz, 4.8H, major rotamer).

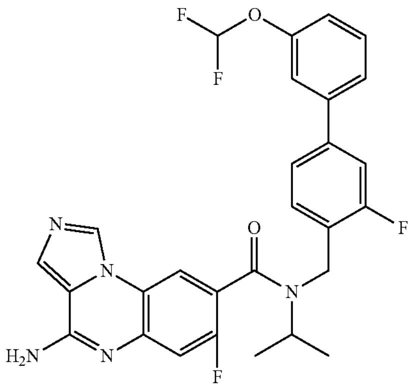 [SMILES: CC(C)N(Cc1ccc(-c2cccc(OC(F)F)c2)cc1F)C(=O)c1cc2c(cc1F)nc(N)c1cncn12]

Example Ff-592: 4-amino-N-((3'-(difluoromethoxy)-3-fluoro-[1,1'-biphenyl]-4-yl)methyl)-7-fluoro-N-isopropylimidazo[1,5-a]quinoxaline-8-carboxamide. Prepared following the procedure reported for example Ff-95 starting with 4-((tert-butoxycarbonyl)amino)-7-fluoroimidazo[1,5-a]quinoxaline-8-carboxylic acid Af-1, N-(4-bromo-2-fluorobenzyl)propan-2-amine Ed-9 and commercial (3-(difluoromethoxy)phenyl)boronic acid. ES/MS: m/z=538.0 $[M+H]^+$. $^1H$ NMR (400 MHz, DMSO-$d_6$) δ $^1H$ NMR (400 MHz, DMSO-$d_6$) δ 9.38 (s, 0.8H, major rotamer), 9.22 (s, 0.2H, minor rotamer), 8.84 (br, 2H), 8.51 (d, J=6.2 Hz, 0.8H, major rotamer), 8.34 (d, J=6.2 Hz, 0.2H, minor rotamer), 8.25 (s, 0.8H, major rotamer) 8.19 (s, 0.2H, minor rotamer), 7.69-7.61 (m, 1H), 7.59-7.49 (m, 3H), 7.52-7.35 (m, 3H), 7.25-7.16 (m, 2H), 4.82-4.56 (m, 2H), 3.98 (p, J=6.7 Hz, 1H), 1.27 (d, J=6.8 Hz, 1.2H, minor rotamer), 1.16 (d, J=6.6 Hz, 4.8H, major rotamer).

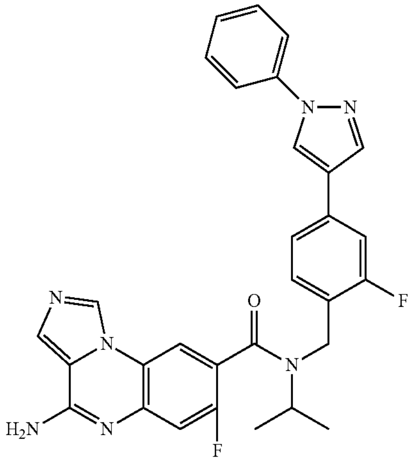 [SMILES: CC(C)N(Cc1ccc(-c2cnn(-c3ccccc3)c2)cc1F)C(=O)c1cc2c(cc1F)nc(N)c1cncn12]

Example Ff-593: 4-amino-7-fluoro-N-(2-fluoro-4-(1-phenyl-1H-pyrazol-4-yl)benzyl)-N-isopropylimidazo[1,5-a]quinoxaline-8-carboxamide. Prepared following the procedure reported for example Ff-95 starting with 4-((tert-butoxycarbonyl)amino)-7-fluoroimidazo[1,5-a]quinoxaline-8-carboxylic acid Af-1, N-(4-bromo-2-fluorobenzyl)propan-2-amine Ed-9 and commercial (1-phenyl-1H-pyrazol-4-yl)boronic acid. ES/MS: m/z=538.0 $[M+H]^+$. $^1H$ NMR (400 MHz, DMSO-$d_6$) δ 9.36 (s, 0.8H, major rotamer), 9.24 (s, 0.2H, minor rotamer), 9.08 (s, 0.8H, major rotamer), 8.97 (s, 0.2H, minor rotamer), 8.83-8.52 (m, 1H), 8.49 (d, J=6.3 Hz, 0.8H, major rotamer), 8.39 (d, J=6.2 Hz, 0.2H, minor rotamer), 8.30 (s, 0.8H, major rotamer), 8.20 (s, 0.8H, major rotamer), 8.19 (s, 0.2H, minor rotamer), 8.15 (s, 0.2H, minor rotamer), 7.96-7.86 (m, 2H), 7.68-7.47 (m, 3H), 7.48-7.25 (m, 3H), 4.88-4.60 (m, 2H), 4.60-4.50 (m, 0.2H, minor rotamer), 4.40-4.93 (m, 0.8H, major rotamer), 3.85 (br, 2H), 1.26 (d, J=6.7 Hz, 1.2H, minor rotamer), 1.14 (d, J=6.6 Hz, 4.8H, major rotamer).

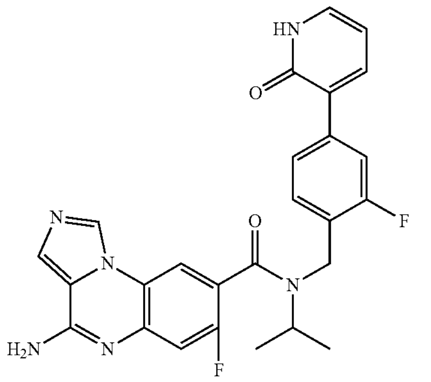 [SMILES: CC(C)N(Cc1ccc(-c2ccc[nH]c2=O)cc1F)C(=O)c1cc2c(cc1F)nc(N)c1cncn12]

Example Ff-594: 4-amino-7-fluoro-N-(2-fluoro-4-(2-oxo-1,2-dihydropyridin-3-yl)benzyl)-N-isopropylimidazo[1,5-a]quinoxaline-8-carboxamide. Prepared following the procedure reported for example Ff-95 starting with 4-((tert-butoxycarbonyl)amino)-7-fluoroimidazo[1,5-a]quinoxaline-8-carboxylic acid Af-1, N-(4-bromo-2-fluorobenzyl)propan-2-amine Ed-9 and commercial (2-oxo-1,2-dihydropyridin-3-yl)boronic acid. ES/MS: m/z=489.0 $[M+H]^+$. $^1H$ NMR (400 MHz, DMSO-$d_6$) δ 11.89 (s, 1H), 9.40 (s, 0.8H, major rotamer), 9.25 (s, 0.2H, minor rotamer), 9.00 (br, 2H), 8.52 (d, J=6.2 Hz, 0.8H, major rotamer), 8.36 (d, J=6.1 Hz, 0.2H, minor rotamer), 8.28 (s, 0.8H), 8.23 (s, 0.2H, major rotamer), 7.83-7.23 (m, 6H), 6.33 (d, J=6.7 Hz, 0.8H, major rotamer), 6.26 (t, J=6.7 Hz, 0.2H, minor rotamer), 4.88-4.60 (m, 2H), 4.57-4.45 (m, 0.20H, minor rotamer), 3.97 (p, J=6.6 Hz, 0.8H, major rotamer), 1.26 (d, J=6.8 Hz, 1.2H, minor rotamer), 1.15 (d, J=6.6 Hz, 4.8H, major rotamer).

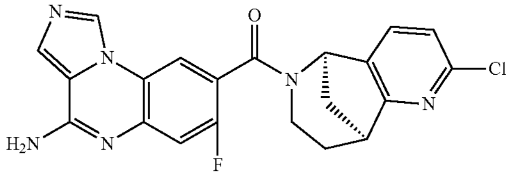 [SMILES: Nc1nc2cc(F)c(C(=O)N3CC[C@H]4C[C@@H]3c3ccc(Cl)nc34)cc2n2cncc12]

Example Ff-595: (4-amino-7-fluoroimidazo[1,5-a]quinoxalin-8-yl)((5R,9S)-2-chloro-5,7,8,9-tetrahydro-6H-5,9-methanopyrido[3,2-c]azepin-6-yl)methanone. Prepared following general procedure VI-F starting with 4-((tert-butoxycarbonyl)amino)-7-fluoroimidazo[1,5-a]quinoxaline-8-carboxylic acid Af-1 and (5R,9S)-2-chloro-6,7,8,9-tetrahydro-5H-5,9-methanopyrido[3,2-c]azepine Ef-11. ES/MS: m/z=423.0 $[M+H]^+$. $^1H$ NMR (400 MHz, DMSO-$d_6$) δ 9.35 (s, 1H), 8.87 (br, 2H), 8.60-8.19 (m, 2H), 7.89 (d, J=7.9 Hz, 0.5H, rotamer), 7.68 (d, J=7.9 Hz, 0.5H rotamer), 7.54-7.27 (m, 2H), 5.96 (d, J=3.9 Hz, 0.5H, rotamer), 4.92 (d, J=3.9 Hz, 0.5H, rotamer), 4.35-4.19 (m, 0.5H, rotamer), 3.37-3.33 (m, 0.5H rotamer), 2.70-2.58 (m, 0.5H, rotamer), 2.46-2.39 (m, 0.5H, rotamer), 2.35-2.05 (m, 2H), 2.05-1.83 (m, 2H), 1.71-1.42 (m, 1H).

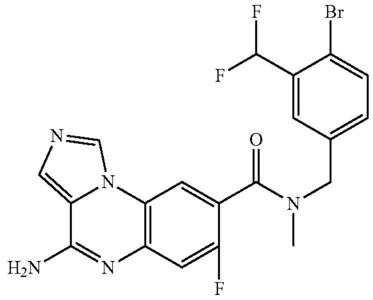 [SMILES: CN(Cc1ccc(Br)c(C(F)F)c1)C(=O)c1cc2c(cc1F)nc(N)c1cncn12]

Example Ff-596: 4-amino-N-(4-bromo-3-(difluoromethyl)benzyl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 1-(4-bromo-3-(difluoromethyl)phenyl)-N-methylmethanamine Ed-46. ES/MS: m/z=479.8 $[M+H]^+$. $^1H$ NMR (400 MHz, DMSO-$d_6$) δ 9.28 (s, 0.6H, major rotamer), 9.20 (s, 0.3H, minor rotamer), 8.44 (s, 0.7H, major rotamer), 8.16 (s, 0.7H, major rotamer), 7.83 (s, 0.3H, major rotamer), 7.74 (d, J=8.2 Hz, 0.3H, minor rotamer), 7.69 (d, J=2.1 Hz, 0.7H, major rotamer), 7.52-7.47 (m, 0.7H, major rotamer), 7.42 (s, 0.3H, minor rotamer), 7.39 (s, 0.3H, minor rotamer), 7.18 (m, 0.7H, major rotamer), 7.09 (m, 0.3H, minor rotamer), 4.80 (s, 1H, 1.4, major rotamer), 4.55 (s, 0.6H, minor rotamer), 2.99 (s, 0.9H, minor rotamer), 2.89 (d, J=1.2 Hz, 2.1H, major rotamer), 1.24 (d, J=2.9 Hz, 2H).

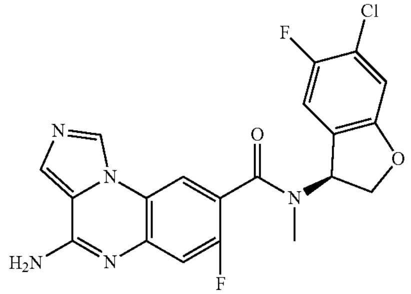 [SMILES: CN(C(=O)c1cc2c(cc1F)nc(N)c1cncn12)[C@@H]1COc2cc(Cl)c(F)cc21]

Example Ff-597: (S)-4-amino-N-(6-chloro-5-fluoro-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 6-chloro-5-fluoro-N-methyl-2,3-dihydrobenzofuran-3-amine Eam-5. The isomers were separated using SFC. Isolated as peak 1 of SFC separation (IA 4.6×100 mm 5 mic, MeOH 45%, 3.0 mL/min). ES/MS: m/z=430.0 $[M+H]^+$. $^1H$ NMR (400 MHz, DMSO-$d_6$) δ 9.32 (s, 0.6H, major rotamer), 9.31 (s, 0.4H, minor rotamer), 9.04 (s, 2H), 8.58 (s, 1H), 8.46 (d, J=6.2 Hz, 1H), 8.28 (s, 1H), 7.44 (s, 0.6H, major rotamer), 7.40 (s, 0.4H, minor rotamer), 7.38 (s, 0.4H, minor rotamer), 7.22 (dd, J=14.5, 5.8 Hz, 0.6H, major rotamer), 6.38 (dd, J=9.0, 4.0 Hz, 0.6H, major rotamer), 5.53 (t, J=6.8 Hz, 0.4H, minor rotamer), 4.85 (dd, J=10.4, 9.0 Hz, 0.6H, minor rotamer), 4.65 (dd, J=10.0, 4.0 Hz, 1.4H, major rotamer), 2.73 (s, 2.1H, major rotamer), 2.63 (s, 0.9H, minor rotamer).

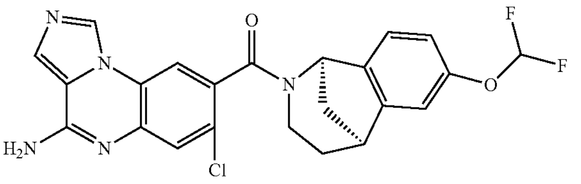 [SMILES: Nc1nc2cc(Cl)c(C(=O)N3CC[C@H]4C[C@@H]3c3ccc(OC(F)F)cc34)cc2n2cncc12]

Example Ff-598: (4-amino-7-chloroimidazo[1,5-a]quinoxalin-8-yl)((1R,5S)-7-(difluoromethoxy)-1,3,4,5-tetrahydro-2H-1,5-methanobenzo[c]azepin-2-yl)methanone. Prepared following general procedure VI-F starting with 4-((tert-butoxycarbonyl)amino)-7-chloroimidazo[1,5-a]quinoxaline-8-carboxylic acid Af-2 and (1R,5S)-7-(difluoromethoxy)-2,3,4,5-tetrahydro-1H-1,5-methanobenzo[c]azepine Ef-7. ES/MS: m/z=470.0 $[M+H]^+$. $^1H$ NMR (400 MHz, DMSO-$d_6$) δ 9.42 (s, 0.3H, minor rotamer), 9.28 (m, 0.7H, major rotamer), 9.42 (s, 0.3H, minor rotamer), 8.51 (s, 0.7H, major rotamer), 8.41 (s, 0.6H, minor rotamer), 8.20 (s, 1.4H, major rotamer), 7.66 (d, J=12.2 Hz, 0.7H, major rotamer), 7.60 (s, 0.3H, minor rotamer), 7.49 (s, 0.3H, minor rotamer), 7.45 (d, J=8.1 Hz, 0.3H, minor rotamer), 7.44-7.39 (m, 0.3H, minor rotamer), 7.29 (t, J=7.8 Hz, 0.7H, major rotamer), 7.24 (d, J=5.3 Hz, 0.6H, minor rotamer), 7.20-7.16 (m, 1.4H, major rotamer), 7.12-7.07 (m, 0.6H, minor rotamer), 7.05 (m, 1.4H, major rotamer), 5.89 (d, J=3.9 Hz, 0.7H, major rotamer), 4.66 (s, 0.3H, minor rotamer), 4.58 (s, 0.3H, minor rotamer), 4.28 (t, J=15.2 Hz, 0.7H, major rotamer), f3.11 (s, 0.3H, minor rotamer), 3.09 (d, J=6.7 Hz, 0.7H, major rotamer), 2.31-2.24 (m, 1.4H, major rotamer), 2.19 (m, 0.6H, minor rotamer), 2.03 (d, J=12.0 Hz, 1.4H, major rotamer), 1.93 (d, J=12.0 Hz, 0.6H, minor rotamer).

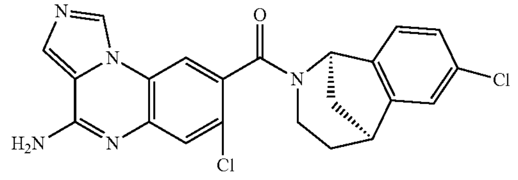 [SMILES: Nc1nc2cc(Cl)c(C(=O)N3CC[C@H]4C[C@@H]3c3ccc(Cl)cc34)cc2n2cncc12]

Example Ff-599: (4-amino-7-chloroimidazo[1,5-a]quinoxalin-8-yl)((1R,5S)-7-chloro-1,3,4,5-tetrahydro-2H-1,5-methanobenzo[c]azepin-2-yl)methanone. Prepared following general procedure VI-F starting with 4-((tert-butoxycarbonyl)amino)-7-chloroimidazo[1,5-a]quinoxaline-8-carboxylic acid Af-2 and (1R,5S)-7-chloro-2,3,4,5-tetrahydro-1H-1,5-methanobenzo[c]azepine Ef-4. ES/MS: m/z=438.0 $[M+H]^+$. $^1H$ NMR (400 MHz, DMSO-$d_6$) δ 9.44 (s, 0.3H, minor rotamer), 9.30 (s, 0.7H, major rotamer), 8.52 (d, J=9.4 Hz, 0.7H, major rotamer), 8.42 (s, 0.3H, minor rotamer), 8.21 (s, 1.4H, major rotamer), 7.64 (d, J=17.1 Hz, 0.6H, minor rotamer), 7.43 (d, J=7.5 Hz, 1.4H, major rotamer), 7.40 (d, J=7.8 Hz, 0.3H, minor rotamer), 7.37-7.31 (m, 0.7H, major rotamer), 7.27 (dd, J=7.9, 3.9 Hz, 0.6H, minor rotamer), 5.89 (s, 0.3H, minor rotamer), 4.63 (m, 0.7H, major rotamer), 4.28 (dt, J=13.7, 6.8 Hz, 0.6H, minor rotamer), 3.39 (d, J=15.4 Hz, 1.4H, major rotamer), 3.10 (s, 1H, major rotamer), 2.28 (d, J=8.2 Hz, 1.4H, major rotamer), 2.02 (d, J=10.7 Hz, 1.4H, major rotamer), 1.99-1.88 (m, 0.6H, minor rotamer), 1.77 (d, J=11.6 Hz, 0.6H, minor rotamer).

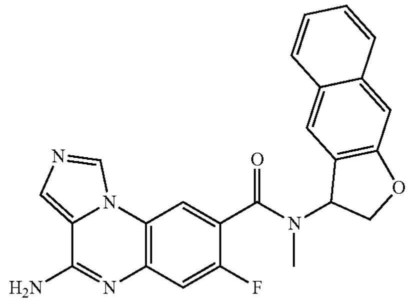 [SMILES: CN(C(=O)c1cc2c(cc1F)nc(N)c1cncn12)C1COc2cc3ccccc3cc21]

Example Ff-600: 4-amino-N-(2,3-dihydronaphtho[2,3-b]furan-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and N-methyl-2,3-dihydronaphtho[2,3-b]furan-3-amine Eh-25. ES/MS: m/z=428.0 $[M+H]^+$. $^1H$ NMR (400 MHz, DMSO-$d_6$) δ 9.34 (s, 0.7H, major rotamer), 8.95 (s, 2H), 8.51 (d, J=6.2 Hz, 0.3H, minor rotamer), 8.26 (d, J=4.0 Hz, 1H), 7.92 (t, J=4.3 Hz, 0.7H, major rotamer), 7.87 (s, 0.3H, minor rotamer), 7.83-7.74 (m, 1H,), 7.46 (m, J=8.0, 6.6, 1.3 Hz, 1.4H, major rotamer), 7.41 (d, J=10.3 Hz, 0.6H, minor rotamer), 7.39-7.33 (m, 1H), 7.28 (d, J=18.7 Hz, 1H,), 6.60 (dd, J=8.7, 4.0 Hz, 0.3H, minor rotamer), 5.69 (t, J=6.3 Hz, 0.7H, major rotamer), 4.88 (dd, J=10.2, 8.7 Hz, 0.3H, minor rotamer), 4.66 (dd, J=10.1, 4.0 Hz, 0.7H, major rotamer), 2.75 (s, 1.6H, major rotamer), 2.65-2.62 (m, 1.4H, major rotamer).

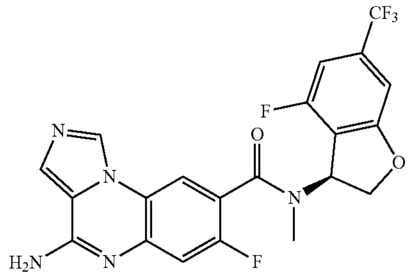 [SMILES: CN(C(=O)c1cc2c(cc1F)nc(N)c1cncn12)[C@@H]1COc2cc(C(F)(F)F)cc(F)c21]

Example Ff-601: (S)-4-amino-7-fluoro-N-(4-fluoro-6-(trifluoromethyl)-2,3-dihydrobenzofuran-3-yl)-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 4-fluoro-N-methyl-6-(trifluoromethyl)-2,3-dihydrobenzofuran-3-amine Eam-6. The isomers were separated using SFC. Isolated as peak 2 of SFC separation (IA 4.6×100 mm 5 mic, MeOH 45%, 3 mL/min). ES/MS: m/z=464.0 $[M+H]^+$. $^1H$ NMR (400 MHz, DMSO-$d_6$) δ 9.36 (s, 0.5H, rotamer), 9.11 (s, 2H), 8.46 (d, J=6.2 Hz, 0.5H, rotamer), 8.29 (s, 1H), 7.42 (t, J=10.4 Hz, 1H), 7.29 (d, J=8.5 Hz, 0.6H, minor rotamer), 7.26-7.16 (m, 1.4H, major rotamer), 6.61 (dd, J=9.3, 4.0 Hz, 0.6H, major rotamer), 5.83 (s, 0.4H, minor rotamer), 5.00-4.91 (m, 1H), 4.81 (d, J=6.3 Hz, 0.6H, major rotamer), 4.73 (dd, J=10.3, 4.1 Hz, 0.4H, major rotamer), 2.77 (s, 1.3H, minor rotamer), 2.70-2.66 (m, 1.7H, major rotamer).

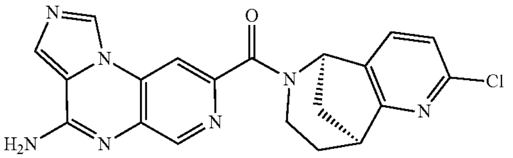 [SMILES: Nc1nc2cnc(C(=O)N3CC[C@H]4C[C@@H]3c3ccc(Cl)nc34)cc2n2cncc12]

Example Ff-602: (4-aminoimidazo[1,5-a]pyrido[3,4-e]pyrazin-8-yl)((5R,9S)-2-chloro-5,7,8,9-tetrahydro-6H-5,9-methanopyrido[3,2-c]azepin-6-yl)methanone. Prepared following general procedure VI-F starting with 4-((tert-butoxycarbonyl)amino)imidazo[1,5-a]pyrido[3,4-e]pyrazine-8-carboxylic acid Af-6 and (5R,9S)-2-chloro-6,7,8,9-tetrahydro-5H-5,9-methanopyrido[3,2-c]azepine Ef-11. ES/MS: m/z=406.0 $[M+H]^+$. $^1$H NMR (400 MHz, DMSO-$d_6$) δ 9.43 (s, 0.6H, major rotamer), 9.42 (s, 0.4H, minor rotamer), 8.75 (m, 1H), 8.56 (m, 1H), 8.21 (d, J=4.6 Hz, 1H), 7.89 (d, J=7.9 Hz, 0.4H, minor rotamer), 7.78 (d, J=7.9 Hz, 0.6H, major rotamer), 7.42 (d, J=7.8 Hz, 0.4H, minor rotamer), 7.37 (d, J=7.9 Hz, 0.6H, major rotamer), 5.93 (d, J=3.9 Hz, 0.4H, minor rotamer), 5.35 (d, J=4.1 Hz, 0.6H, major rotamer), 4.26 (dd, J=14.2, 6.7 Hz, 0.6H, major rotamer), 3.69 (dd, J=14.1, 6.3 Hz, 0.4H, minor rotamer), 2.63-2.71 (m, 0.4H, minor rotamer), 2.45-2.33 (m, 1H), 2.33-2.22 (m, 1H), 2.09-2.17 (m, 0.6H, major rotamer), 2.05 (d, J=11.2 Hz, 0.6H, major rotamer), 1.96 (d, J=11.2 Hz, 0.4H, minor rotamer), 1.88 (d, J=13.0 Hz, 0.6H, major rotamer), 1.65 (d, J=13.1 Hz, 0.4H, minor rotamer).

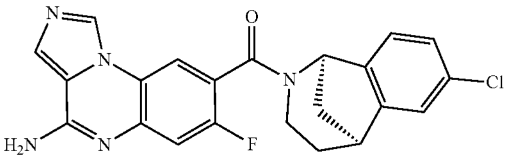 [SMILES: Nc1nc2cc(F)c(C(=O)N3CC[C@H]4C[C@@H]3c3ccc(Cl)cc34)cc2n2cncc12]

Example Ff-603: (4-amino-7-fluoroimidazo[1,5-a]quinoxalin-8-yl)((1R,5S)-7-chloro-1,3,4,5-tetrahydro-2H-1,5-methanobenzo[c]azepin-2-yl)methanone. Prepared following general procedure VI-F starting with 4-((tert-butoxycarbonyl)amino)-7-fluoroimidazo[1,5-a]quinoxaline-8-carboxylic acid Af-1 and (1R,5S)-7-chloro-2,3,4,5-tetrahydro-1H-1,5-methanobenzo[c]azepine Ef-4. ES/MS: m/z=422.0 $[M+H]^+$. $^1$H NMR (400 MHz, DMSO-$d_6$) δ 9.38 (s, 0.6H, major rotamer), 9.33 (s, 0.4H, minor rotamer), 8.84 (s, 2H), 8.54 (d, J=6.2 Hz, 1H), 8.25 (d, J=13.7 Hz, 1H), 7.48 (s, 0.4H, minor rotamer), 7.44 (s, 1H), 7.42 (d, J=7.9 Hz, 0.4H, minor rotamer), 7.36 (dd, J=7.9, 2.0 Hz, 0.6H, major rotamer), 7.22 (d, J=7.9 Hz, 0.6H, major rotamer), 5.87 (d, J=3.9 Hz, 0.4H, minor rotamer), 4.78 (d, J=3.6 Hz, 0.6H, major rotamer), 3.40 (s, 1H), 3.25 (dd, J=13.8, 6.1 Hz, 0.6H, major rotamer), 2.60 (dd, J=12.9, 4.8 Hz, 0.4H, minor rotamer), 2.35-2.21 (m, 0.4H, minor rotamer), 1.89 (m, J=11.1 Hz, 0.6H, major rotamer), 1.77 (d, J=9.5 Hz, 0.4H, minor rotamer), 1.55 (d, J=13.1 Hz, 0.6H, major

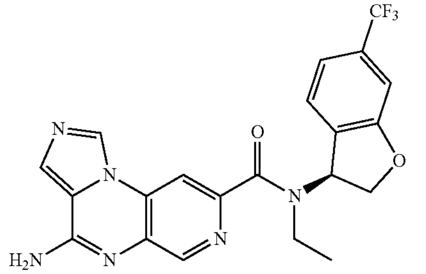

Example Ff-604: (S)-4-amino-N-ethyl-N-(6-(trifluoromethyl)-2,3-dihydrobenzofuran-3-yl)imidazo[1,5-a]pyrido[3,4-e]pyrazine-8-carboxamide. Prepared following general procedure VI-F starting with 4-((tert-butoxycarbonyl)amino)imidazo[1,5-a]pyrido[3,4-e]pyrazine-8-carboxylic acid Af-6 and (S)—N-ethyl-6-(trifluoromethyl)-2,3-dihydrobenzofuran-3-amine Eh-2. ES/MS: m/z=443.1 $[M+H]^+$. $^1$H NMR (400 MHz, DMSO-d6) δ 9.42 (s, 0.6H, major rotamer), 9.39 (s, 0.4H, minor rotamer), 8.75 (s, 0.6H, major rotamer), 8.71 (s, 0.4H, minor rotamer), 8.60 (s, 0.6H, major rotamer), 8.52 (s, 0.4H, minor rotamer), 8.38 (s, 2H), 8.16 (s, 1H), 7.76 (d, J=7.8 Hz, 0.6H, major rotamer), 7.57 (d, J=7.8 Hz, 0.4H, minor rotamer), 7.32 (t, J=8.8 Hz, 1H), 7.25 (d, J=5.4 Hz, 1H), 5.97 (s, 0.4H, minor rotamer), 5.93 (dd, J=8.6, 4.2 Hz, 0.6H, major rotamer), 4.89 (d, J=9.7 Hz, 0.4H, minor rotamer), 4.73 (t, J=9.7 Hz, 0.6H, major rotamer), 4.70 (d, J=4.3 Hz, 0.6H, major rotamer), 4.68-4.65 (m, 0.4H, minor rotamer), 0.97 (q, J=6.6 Hz, 3H).

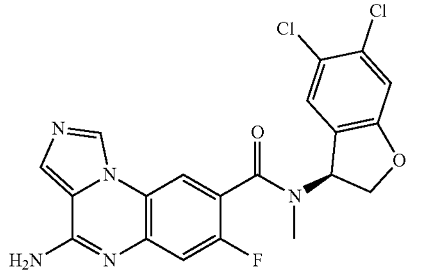 [SMILES: CN(C(=O)c1cc2c(cc1F)nc(N)c1cncn12)[C@@H]1COc2cc(Cl)c(Cl)cc21]

Example Ff-605: (S)-4-amino-N-(5,6-dichloro-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 5,6-dichloro-N-methyl-2,3-dihydrobenzofuran-3-amine Eam-7. The isomers were separated using SFC. Isolated as peak 1 of SFC separation using (AD-H 4.6×100 mm 5 mic, MeOH 40%, 3 mL/min). ES/MS: m/z=446.1, 448.1 $[M+H]^+$. $^1$H NMR (400 MHz, DMSO-$d_6$) δ 9.31 (d, J=10.1 Hz, 0.7H, major rotamer), 9.01 (s, 2H, major rotamer), 8.65 (s, 0.3H, minor rotamer), 8.48 (d, J=6.2 Hz, 0.3H, minor rotamer), 8.28 (s, 0.7H, major rotamer), 7.56 (s, 0.3H, minor rotamer), 7.42 (d, J=10.2 Hz, 0.7H, minor rotamer), 7.29 (d, J=14.4 Hz, 0.7H, major rotamer), 6.37 (dd, J=9.1, 4.1 Hz, 0.3H, minor rotamer), 5.54 (t, J=6.8 Hz, 0.7H, major rotamer), 4.87 (t, J=9.7 Hz, 0.6H, minor rotamer), 4.68 (dd, J=10.2, 4.3 Hz, 1.4H, major rotamer), 2.73 (s, 2.1H, major rotamer), 2.65 (s, 0.9H, minor rotamer).

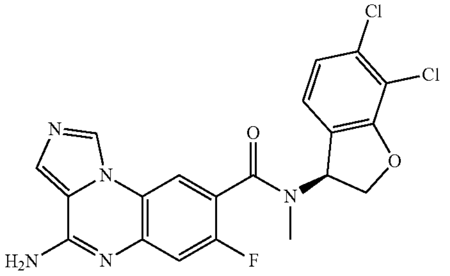 [SMILES: CN(C(=O)c1cc2c(cc1F)nc(N)c1cncn12)[C@@H]1COc2c1ccc(Cl)c2Cl]

Example Ff-606: (S)-4-amino-N-(6,7-dichloro-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 6,7-dichloro-N-methyl-2,3-dihydrobenzofuran-3-amine Eam-8. The isomers were separated using SFC. Isolated as peak 1 of SFC separation (IB 4.6×100 mm 5 mic, MeOH 25%, 3.0 mL/min). ES/MS: m/z=446.1, 448.1 $[M+H]^+$. $^1H$ NMR (400 MHz, DMSO-$d_6$) δ 9.41 (s, 0.3H, minor rotamer), 9.36 (s, 0.7H, major rotamer), 9.35 (s, 1.4H, major rotamer), 8.65 (s, 0.6H, minor rotamer), 8.58 (d, J=6.1 Hz, 0.3H, minor rotamer), 8.50 (d, J=6.1 Hz, 0.7H, major rotamer), 8.36 (d, J=4.4 Hz, 2H), 7.49-7.44 (m, 1H), 7.43 (d, J=10.0 Hz, 1H), 7.32 (d, J=8.1 Hz, 1H), 7.27 (d, J=8.0 Hz, 1H), 7.24 (d, J=8.4 Hz, 0.7H, major rotamer), 7.08 (d, J=8.5 Hz, 0.3H, minor rotamer), 6.47 (dd, J=9.1, 4.2 Hz, 0.7H, major rotamer), 6.00 (dd, J=10.6, 6.3 Hz, 0.3H), 5.61 (t, J=6.6 Hz, 1H), 4.97 (t, J=9.8 Hz, 1H), 4.78 (d, J=4.4 Hz, 1H), 4.75 (d, J=4.3 Hz, 1H), 2.74 (d, J=5.0 Hz, 0.9H, minor rotamer), 2.64 (d, J=4.8 Hz, 2.1H, major rotamer).

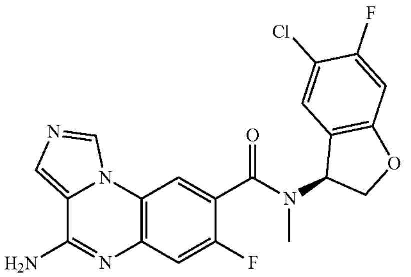

Example Ff-607: (S)-4-amino-N-(6-chloro-5-fluoro-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 5-chloro-6-fluoro-N-methyl-2,3-dihydrobenzofuran-3-amine Eam-9. The isomers were separated using SFC. Isolate as peak 1 of SFC separation (AD-H 4.6×100 mm 5 mic, EtOH 40%, 3.0 mL/min). ES/MS: m/z=430.2 $[M+H]^+$. $^1H$ NMR (400 MHz, DMSO-$d_6$) δ 9.32 (s, 0.4H, minor rotamer), 9.30 (s, 0.6H, major rotamer), 8.97 (s, 2H), 8.64 (s, 0.4H, minor rotamer), 8.47 (d, J=6.2 Hz, 0.6H, major rotamer), 8.27 (s, 1H), 7.50 (d, J=7.6 Hz, 0.4H, minor rotamer), 7.41 (d, J=10.3 Hz, 0.6H, major rotamer), 7.13 (d, J=9.9 Hz, 0.4H, minor rotamer), 7.10 (d, J=9.8 Hz, 0.6H, major rotamer), 6.37 (dd, J=9.1, 3.9 Hz, 0.6H, major rotamer), 5.56-5.48 (m, 0.6H, major rotamer), 4.88 (dd, J=10.5, 9.0 Hz, 0.8H, minor rotamer), 4.73-4.59 (m, 1.2H, major rotamer), 2.72 (s, 1.2H, minor rotamer), 2.63 (s, 1.8H, rotamer).

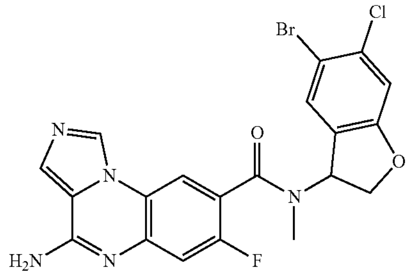 [SMILES: CN(C(=O)c1cc2c(cc1F)nc(N)c1cncn12)C1COc2cc(Cl)c(Br)cc21]

Example Ff-608: 4-amino-N-(5-bromo-6-chloro-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 5-bromo-6-chloro-N-methyl-2,3-dihydrobenzofuran-3-amine Eam-10. ES/MS: m/z=490.2, 492.1 $[M+H]^+$. $^1H$ NMR (400 MHz, DMSO-$d_6$) δ 9.17 (d, J=9.4 Hz, 0.7H, major rotamer), 8.37 (d, J=6.3 Hz, 0.3H, minor rotamer), 8.04 (s, 0.7H, major rotamer), 7.55 (s, 0.3H, minor rotamer), 7.40 (d, J=15.6 Hz, 0.7H, major rotamer), 7.30 (d, J=11.0 Hz, 0.3H, minor rotamer), 6.36 (s, 0.3H, minor rotamer), 5.56 (s, 0.7H, major rotamer), 4.86 (t, J=9.9 Hz, 0.3H, minor rotamer), 4.66 (t, J=5.2 Hz, 0.7H, major rotamer), 2.68 (m, 2.1H, major rotamer), 2.01 (d, J=14.4 Hz, 0.9H, minor rotamer).

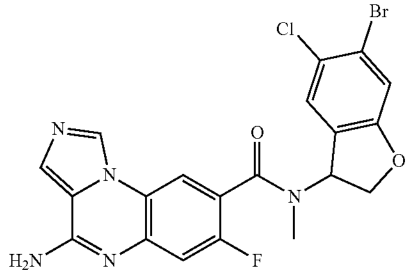

Example Ff-609: 4-amino-N-(6-bromo-5-chloro-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and 5-bromo-6-chloro-N-methyl-2,3-dihydrobenzofuran-3-amine Eam-11. ES/MS: m/z=490.1, 492.1 $[M+H]^+$. $^1H$ NMR (400 MHz, DMSO-$d_6$) δ 9.17 (s, 0.3H, minor rotamer), 9.14 (s, 0.7H, major rotamer), 8.37 (d, J=6.4 Hz, 0.3H, minor rotamer), 8.01 (s, 0.7H, major rotamer), 7.67 (s, 0.3H, minor rotamer), 7.29 (d, J=15.7 Hz, 0.7H, major rotamer), 6.42-6.24 (m, 0.3H, minor rotamer), 5.58 (s, 0.7H, major rotamer), 4.86 (t, J=9.9 Hz, 0.6H, minor rotamer), 4.67 (t, J=5.2 Hz, 1.4H, major rotamer), 2.68 (m, 2.1H, major rotamer), 2.01 (d, J=14.3 Hz, 0.9H, minor rotamer).

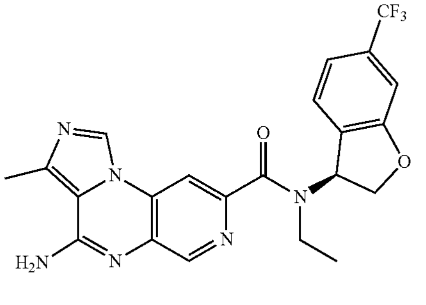 [SMILES: CCN(C(=O)c1cc2c(cn1)nc(N)c1c(C)ncn12)[C@@H]1COc2cc(C(F)(F)F)ccc21]

Example Ff-610: (S)-4-amino-N-ethyl-3-methyl-N-(6-(trifluoromethyl)-2,3-dihydrobenzofuran-3-yl)imidazo[1,5-a]pyrido[3,4-e]pyrazine-8-carboxamide. Prepared following general procedure VI-F starting with 4-((tert-butoxycarbonyl)amino)-3-methylimidazo[1,5-a]pyrido[3,4-e]pyrazine-8-carboxylic acid Ag-2 and (S)—N-ethyl-6-(trifluoromethyl)-2,3-dihydrobenzofuran-3-amine Eh-2. ES/MS: m/z=457.2 $[M+H]^+$. $^1$H NMR (400 MHz, DMSO-$d_6$) δ 9.22 (s, 0.7H, major rotamer), 9.18 (s, 0.3H, minor rotamer), 8.64 (s, 0.7H, major rotamer), 8.59 (s, 0.3H, minor rotamer), 8.47 (s, 0.7H, major rotamer), 8.38 (s, 0.3H, minor rotamer), 7.77 (d, J=7.9 Hz, 0.7H, major rotamer), 7.56 (d, J=7.8 Hz, 0.3H, minor rotamer), 7.34 (s, 0.3H, major rotamer), 7.25 (s, 0.7H, minor rotamer), 5.98 (dd, J=9.0, 4.4 Hz, 0.7H, minor rotamer), 5.03 (m, 0.3H, minor rotamer), 4.79-4.63 (m, 1.4H, major rotamer), 4.28-4.08 (m, 0.6H, minor rotamer), 2.65 (s, 2.1H, major rotamer), 2.02 (s, 0.9H, minor rotamer), 0.96 (t, J=6.9 Hz, 2.1H, major rotamer), 0.86 (t, J=6.6 Hz, 0.9H, minor rotamer).

Examples Ff-611 and Ff-612 were prepared following general procedure VI-F starting with 4-((tert-butoxycarbonyl)amino)-3-methylimidazo[1,5-a]pyrido[3,4-e]pyrazine-8-carboxylic acid Ag-2 and cis-2-methyl-7-(trifluoromethyl)-1,2,3,4,4a,9b-hexahydrobenzofuro[3,2-b]pyridine Ev-4. The isomers were separated using SFC separation (AD-H 4.6×100 mm 5 mic, EtOH 20%, 3.0 mL/min). The stereochemistry was arbitrarily assigned.

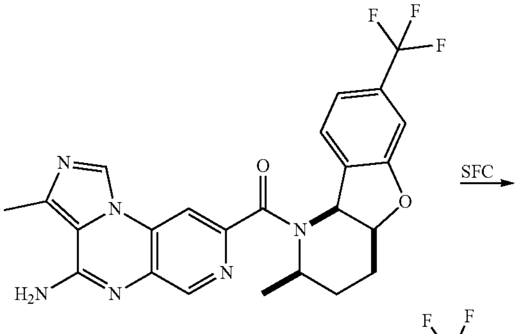

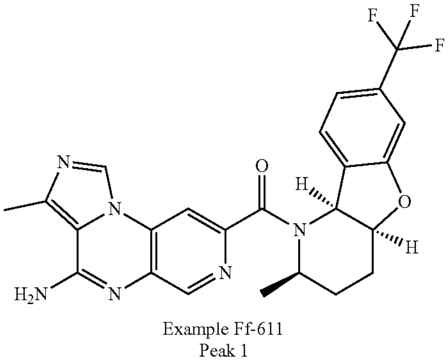

Example Ff-611
Peak 1

+

-continued

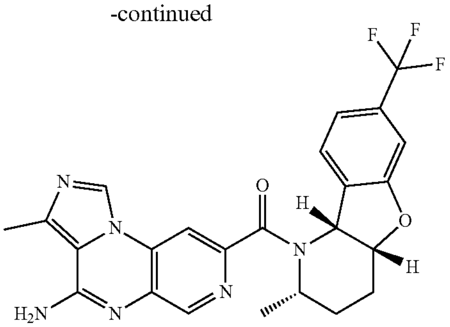

Example Ff-612
Peak 2

Example Ff-611: (4-amino-3-methylimidazo[1,5-a]pyrido[3,4-e]pyrazin-8-yl)((2R,4aS,9bS)-2-methyl-7-(trifluoromethyl)-3,4,4a,9b-tetrahydrobenzofuro[3,2-b]pyridin-1(2H)-yl)methanone. Peak 1. ES/MS: m/z=483.3 $[M+H]^+$. $^1$H NMR (400 MHz, Methanol-$d_4$) δ 8.83 (s, 1H), 8.47 (s, 1H), 8.28 (s, 1H), 8.00 (d, J=7.8 Hz, 1H), 7.28-7.22 (m, 1H), 7.05 (s, 1H), 6.16 (s, 1H), 5.14 (d, J=10.2 Hz, 1H), 2.65 (s, 3H), 2.10-2.04 (m, 1H), 1.83 (t, J=14.5 Hz, 1H), 1.43 (q, J=13.1 Hz, 1H), 1.09-1.04 (m, 3H).

Example Ff-612: (4-amino-3-methylimidazo[1,5-a]pyrido[3,4-e]pyrazin-8-yl)((2S,4aR,9bR)-2-methyl-7-(trifluoromethyl)-3,4,4a,9b-tetrahydrobenzofuro[3,2-b]pyridin-1(2H)-yl)methanone. Peak 2. ES/MS: m/z=483.3 $[M+H]^+$. $^1$H NMR (400 MHz, Methanol-$d_4$) δ 8.83 (s, 1H), 8.47 (s, 1H), 8.28 (s, 1H), 8.00 (d, J=7.8 Hz, 1H), 7.28-7.22 (m, 1H), 7.05 (s, 1H), 6.16 (s, 1H), 5.14 (d, J=10.2 Hz, 1H), 2.65 (s, 3H), 2.10-2.04 (m, 1H), 1.83 (t, J=14.5 Hz, 1H), 1.43 (q, J=13.1 Hz, 1H), 1.09-1.04 (m, 3H).

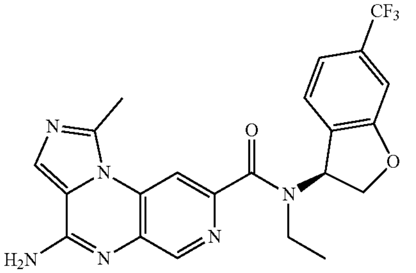 [SMILES: CCN(C(=O)c1cc2c(cn1)nc(N)c1cnc(C)n12)[C@@H]1COc2cc(C(F)(F)F)ccc21]

Example Ff-613: (S)-4-amino-N-ethyl-1-methyl-N-(6-(trifluoromethyl)-2,3-dihydrobenzofuran-3-yl)imidazo[1,5-a]pyrido[3,4-e]pyrazine-8-carboxamide. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (S)—N-ethyl-6-(trifluoromethyl)-2,3-dihydrobenzofuran-3-amine Eh-2. ES/MS: m/z=456.9 $[M+H]^+$. $^1$H NMR (400 MHz, DMSO-$d_6$) δ 9.33 (s, 2H), 8.36 (s, 1H), 8.17 (s, 1H), 7.70-7.62 (m, 2H), 7.31 (dd, J=7.9, 1.5 Hz, 1H), 7.24 (d, J=1.5 Hz, 1H), 5.77-5.83 (m, 1H), 4.75 (dd, J=9.9, 4.6 Hz, 1H), 3.33-3.17 (m, 2H), 3.06 (s, 3H), 0.94 (t, J=6.7 Hz, 2H).

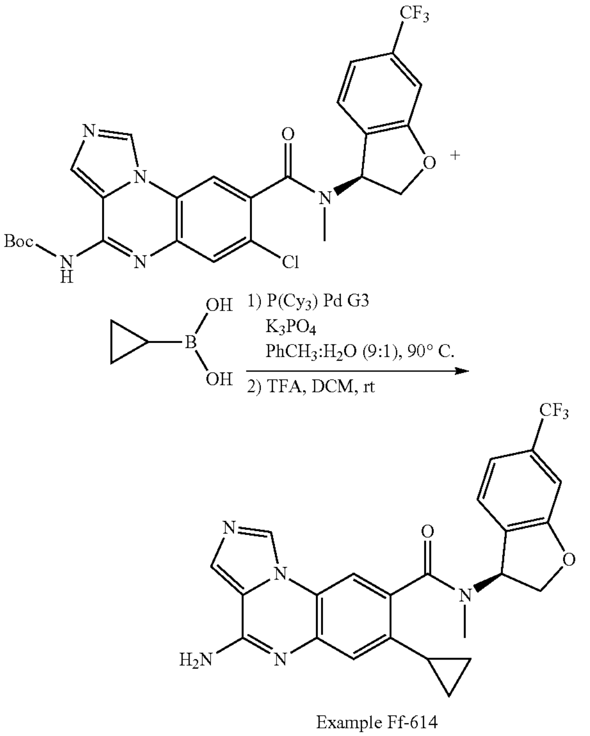

Example Ff-614

Example Ff-614: (S)-4-amino-7-cyclopropyl-N-methyl-N-(6-(trifluoromethyl)-2,3-dihydrobenzofuran-3-yl)imidazo[1,5-a]quinoxaline-8-carboxamide. A stirred solution of tert-butyl (S)-(7-chloro-8-(methyl(6-(trifluoromethyl)-2,3-dihydrobenzofuran-3-yl)carbamoyl)imidazo[1,5-a]quinoxalin-4-yl)carbamate (prepared following step 1 of general procedure VI-F starting with 4-((tert-butoxycarbonyl)amino)-7-chloroimidazo[1,5-a]quinoxaline-8-carboxylic acid Af-2 and (S)—N-methyl-6-(trifluoromethyl)-2,3-dihydrobenzofuran-3-amine hydrochloride Eh-1; 50 mg, 0.089 mmol), cyclopropylboronic acid (92 mg, 1.1 mmol), $P(Cy_3)$ Pd G3 (8.7 mg, 0.013 mmol), $K_3PO_4$ (57 mg, 0.27 mmol) in toluene/water (9:1, 1.1 mL) was degassed with argon for 1 min before stirring the mixture at 90° C. overnight. The reaction was quenched with saturated aqueous ammonium chloride and transferred to a separatory funnel and extracted with EtOAc. The organic extracts were washed with brine, dried over $MgSO_4$, filtered, and concentrated under reduced pressure. The crude was resuspended in dichloromethane (1 mL) and treated with TFA (1 mL) stirring at room temperature for 30 min. The mixture is neutralized with saturated aqueous sodium bicarbonate, transferred to a separatory funnel, and extracted with ethyl acetate. The organic extracts were washed with brine, dried over $MgSO_4$, filtered, and concentrated under reduced pressure. Purification of the crude residue by reverse-phase HPLC afforded the title compound. ES/MS: m/z=468.3 $[M+H]^+$. $^1H$ NMR (400 MHz, DMSO-$d_6$) δ 9.45 (s, 0.7H, major rotamer), 9.33 (s, 1H), 9.31 (s, 0.3H, minor rotamer), 8.57 (s, 0.6H, minor rotamer), 8.41 (s, 0.6H, minor rotamer), 8.40 (s, 1.4H, major rotamer), 8.29 (d, J=2.3 Hz, 1.4H, major rotamer), 7.73 (d, J=7.8 Hz, 0.7H, major rotamer), 7.49 (d, J=7.8 Hz, 0.3H, minor rotamer), 7.35 (s, 0.7H, major rotamer), 7.33 (s, 0.3H, minor rotamer), 7.30 (d, J=1.5 Hz, 1.4H, major rotamer), 7.26 (d, J=1.5 Hz, 0.6H, minor rotamer), 7.15 (s, 1H), 7.10 (s, 1H) 6.57 (s, 1H), 5.48 (dd, J=8.9, 5.5 Hz, 0.3H, minor rotamer), 5.43 (dd, J=9.3, 3.9 Hz, 0.7H, major rotamer), 4.90 (t, J=9.8 Hz, 1.4H, major rotamer), 4.79 (dd, J=10.6, 3.9 Hz, 0.7H, major rotamer), 4.73 (s, 0.6H, minor rotamer), 4.70-4.66 (m, 0.3H, minor rotamer), 4.66-4.59 (m, 1), 2.77 (s, 0.9H, minor rotamer), 2.73 (s, 2.1H, major rotamer), 2.10 (m, 0.3H, minor rotamer), 1.92-1.83 (m, 0.7H, major rotamer), 1.26 (dd, J=12.8, 6.4 Hz, 0.3H, minor rotamer), 1.15-1.06 (m, 2H), 0.90 (p, J=5.1, 4.4 Hz, 0.7H, major rotamer), 0.77-0.69 (m, 0.3H, minor rotamer), 0.69-0.61 (m, 0.7H, major rotamer).

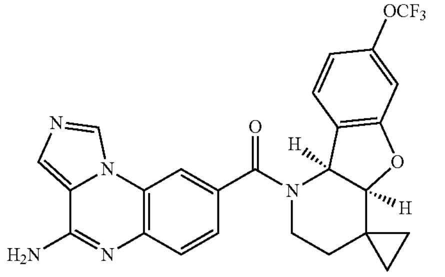 [SMILES: Nc1nc2ccc(C(=O)N3CCC4(CC4)[C@@H]4Oc5cc(OC(F)(F)F)ccc5[C@@H]43)cc2n2cncc12]

Example Ff-615: (4-aminoimidazo[1,5-a]quinoxalin-8-yl)((4aS,9bS)-7-(trifluoromethoxy)-2,3,4a,9b-tetrahydro-1H-spiro[benzofuro[3,2-b]pyridine-4,1'-cyclopropan]-1-yl)methanone. Prepared using general procedure VI-F starting with 4-((tert-butoxycarbonyl)amino)imidazo[1,5-a]quinoxaline-8-carboxylic acid Ae-1 and (4aS,9bS)-7-(trifluoromethoxy)-2,3,4a,9b-tetrahydro-1H-spiro[benzofuro[3,2-b]pyridine-4,1'-cyclopropane]Ew-19. ES/MS: m/z=496.0 $[M+H]^+$. $^1H$ NMR (400 MHz, DMSO-$d_6$) δ 9.48 (s, 1H), 9.32 (brs, 2H), 8.45 (brs, 1H), 8.37 (s, 1H), 7.72-7.47 (m, 1H), 6.95 (s, 2H), 6.24 (brs, 1H), 4.42 (brs, 1H), 2.92 (brs, 1H), 2.03-1.83 (m, 1H), 1.55-1.19 (m, 2H), 0.86-0.49 (m, 4H).

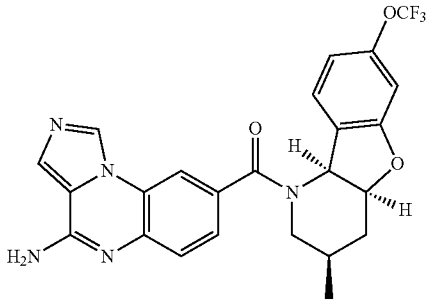 [SMILES: C[C@@H]1C[C@@H]2Oc3cc(OC(F)(F)F)ccc3[C@@H]2N(C(=O)c2ccc3nc(N)c4cncn4c3c2)C1]

Example Ff-616: (4-aminoimidazo[1,5-a]quinoxalin-8-yl)((3R,4aS,9bS)-3-methyl-7-(trifluoromethoxy)-3,4,4a,9b-tetrahydrobenzofuro[3,2-b]pyridin-1(2H)-yl)methanone. Prepared using general procedure VI-F starting with 4-((tert-butoxycarbonyl)amino)imidazo[1,5-a]quinoxaline-8-carboxylic acid Ae-1 and (3R,4aS,9bS)-3-methyl-7-(trifluoromethoxy)-1,2,3,4,4a,9b-hexahydrobenzofuro[3,2-b]pyridine Ew-18. ES/MS: m/z=484.2 $[M+H]^+$. $^1H$ NMR (400 MHz, DMSO-$d_6$) δ 9.44 (s, 1H), 9.23 (brs, 2H), 8.47 (s, 1H), 8.37 (s, 1H), 7.63 (s, 2H), 7.45 (s, 1H), 6.96 (s, 2H), 6.17 (s, 0.7H major rotamer), 5.49 (s, 0.3H minor rotamer), 5.15 (s, 0.7H major rotamer), 5.03 (s, 0.3H minor rotamer), 4.40 (s, 0.6H minor rotamer), 3.54-3.38 (m, 1.4H major rotamer), 2.25-1.69 (m, 3H), 1.59-1.18 (m, 1H), 1.06-0.72 (m, 3H).

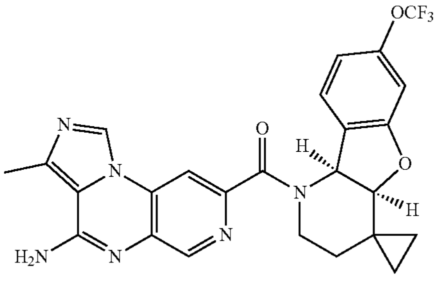 [SMILES: Cc1ncn2c1c(N)nc1cnc(C(=O)N3CCC4(CC4)[C@@H]4Oc5cc(OC(F)(F)F)ccc5[C@@H]43)cc12]

Example Ff-617: (4-amino-3-methylimidazo[1,5-a]pyrido[3,4-e]pyrazin-8-yl)((4aS,9bS)-7-(trifluoromethoxy)-2,3,4a,9b-tetrahydro-1H-spiro[benzofuro[3,2-b]pyridine-4,1'-cyclopropan]-1-yl)methanone. Prepared using general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and (4aS,9bS)-7-(trifluoromethoxy)-2,3,4a,9b-tetrahydro-1H-spiro[benzofuro[3,2-b]pyridine-4,1'-cyclopropane] Ew-19. ES/MS: m/z=511.3 $[M+H]^+$. $^1H$ NMR (400 MHz, DMSO-$d_6$) δ 9.37 (s, 0.5H rotamer), 9.33 (s, 0.5H rotamer), 8.72 (s, 0.5H rotamer), 8.65 (s, 0.5H rotamer), 8.59 (s, 0.5H rotamer), 8.48 (s, 0.5H rotamer), 7.86 (brs, 2H), 7.81 (d, J=8.1 Hz, 0.5H rotamer), 7.45 (d, J=8.0 Hz, 0.5H rotamer), 7.01-6.90 (m, 2H), 6.25 (d, J=8.7 Hz, 0.5H rotamer), 5.92 (d, J=9.0 Hz, 0.5H rotamer), 4.44 (d, J=8.7 Hz, 0.5H rotamer), 4.31-4.20 (m, 1H), 3.00-2.85 (m, 0.5H rotamer), 2.67 (s, 3H), 2.09-1.83 (m, 1H), 1.60-1.16 (m, 2H), 0.84-0.45 (m, 4H).

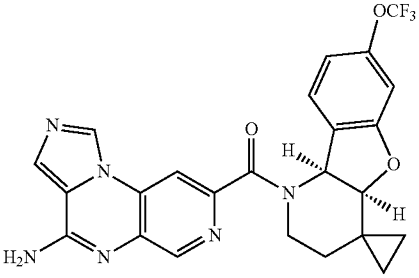 [SMILES: Nc1nc2cnc(C(=O)N3CCC4(CC4)[C@@H]4Oc5cc(OC(F)(F)F)ccc5[C@@H]43)cc2n2cncc12]

Example Ff-618: (4-aminoimidazo[1,5-a]pyrido[3,4-e]pyrazin-8-yl)((4aS,9bS)-7-(trifluoromethoxy)-2,3,4a,9b-tetrahydro-1H-spiro[benzofuro[3,2-b]pyridine-4,1'-cyclopropan]-1-yl)methanone. Prepared using general procedure VI-F starting with 4-((tert-butoxycarbonyl)amino)imidazo[1,5-a]pyrido[3,4-e]pyrazine-8-carboxylic acid Af-6 and (4aS,9bS)-7-(trifluoromethoxy)-2,3,4a,9b-tetrahydro-1H-spiro[benzofuro[3,2-b]pyridine-4,1'-cyclopropane] Ew-19. ES/MS: m/z=497.2 $[M+H]^+$. $^1H$ NMR (400 MHz, DMSO-$d_6$) δ 9.47 (s, 0.5H rotamer), 9.44 (s, 0.5H rotamer), 8.78 (s, 0.5H rotamer), 8.70 (s, 0.5H rotamer), 8.67 (s, 0.5H rotamer), 8.56 (s, 0.5H rotamer), 8.39 (brs, 2H), 8.15 (s, 1H), 7.82 (d, J=8.1 Hz, 0.5H rotamer), 7.45 (d, J=7.9 Hz, 0.5H rotamer), 7.02-6.90 (m, 2H), 6.26 (d, J=8.7 Hz, 0.5H rotamer), 5.92 (d, J=9.0 Hz, 0.5H rotamer), 4.45 (d, J=8.7 Hz, 0.5H rotamer), 4.35-4.20 (m, 1H), 3.79-3.70 (m, 0.5H rotamer), 2.99-2.85 (m, 0.5H rotamer), 2.77-2.67 (m, 0.5H rotamer), 2.03-1.85 (m, 1H), 1.57-1.29 (m, 1H), 0.87-0.44 (m, 4H).

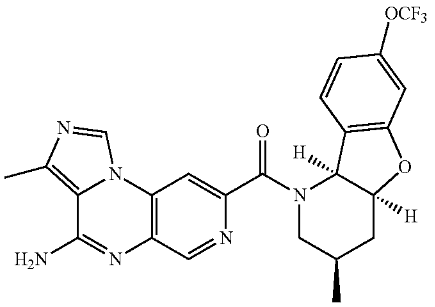 [SMILES: Cc1ncn2c1c(N)nc1cnc(C(=O)N3C[C@H](C)C[C@@H]4Oc5cc(OC(F)(F)F)ccc5[C@@H]43)cc12]

Example Ff-619: (4-amino-3-methylimidazo[1,5-a]pyrido[3,4-e]pyrazin-8-yl)((3R,4aS,9bS)-3-methyl-7-(trifluoromethoxy)-3,4,4a,9b-tetrahydrobenzofuro[3,2-b]pyridin-1(2H)-yl)methanone. Prepared using general procedure VI-F starting with 4-((tert-butoxycarbonyl)amino)-3-methylimidazo[1,5-a]pyrido[3,4-e]pyrazine-8-carboxylic acid Ag-2 and (3R,4aS,9bS)-3-methyl-7-(trifluoromethoxy)-1,2,3,4,4a,9b-hexahydrobenzofuro[3,2-b]pyridine Ew-18. ES/MS: m/z=499.3 $[M+H]^+$. $^1H$ NMR (400 MHz, DMSO-$d_6$) δ 9.31 (s, 1H), 8.69 (s, 0.5H rotamer), 8.65 (s, 0.5H rotamer), 8.59 (s, 0.5H rotamer), 8.50 (s, 0.5H rotamer), 7.94 (brs, 2H), 7.76-7.69 (m, 0.5H rotamer), 7.37 (dd, J=8.7 Hz, 0.5H rotamer), 7.00-6.93 (m, 1H+0.5H rotamer), 6.90 (s, 0.5H rotamer), 6.17 (d, J=8.4 Hz, 0.5H rotamer), 5.80 (d, J=8.3 Hz, 0.5H rotamer), 5.21-5.11 (m, 0.5H rotamer), 5.01-4.92 (m, 0.5H rotamer), 4.37 (dd, J=13.1, 5.3 Hz, 0.5H rotamer), 2.68 (s, 1.5H rotamer), 2.67 (s, 1.5H rotamer), 2.42 (dd, J=13.6, 11.2 Hz, 0.5H rotamer), 2.21-1.98 (m, 2H), 1.97-1.82 (m, 0.5H rotamer), 1.56-1.42 (m, 2H), 0.96 (d, J=6.7 Hz, 1.5H rotamer), 0.81 (d, J=6.7 Hz, 1.5H rotamer).

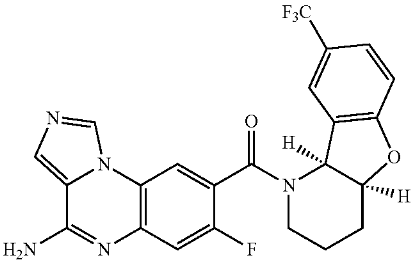 [SMILES: Nc1nc2cc(F)c(C(=O)N3CCC[C@@H]4Oc5ccc(C(F)(F)F)cc5[C@@H]43)cc2n2cncc12]

Example Ff-620: (4-amino-7-fluoroimidazo[1,5-a]quinoxalin-8-yl)((4aS,9bS)-8-(trifluoromethyl)-3,4,4a,9b-tetrahydrobenzofuro[3,2-b]pyridin-1(2H)-yl)methanone. Prepared using general procedure VI-F with intermediates with 4-((tert-butoxycarbonyl)amino)-7-fluoroimidazo[1,5-a]quinoxaline-8-carboxylic acid Af-1 and (4aS,9bS)-8-(trifluoromethyl)-1,2,3,4,4a,9b-hexahydrobenzofuro[3,2-b]pyridine hydrochloride Ew-20. ES/MS: m/z=472.1 $[M+H]^+$. $^1H$ NMR (400 MHz, Methanol-d4) δ 9.46-9.21 (m, 1H), 8.66-8.44 (m, 1H), 8.43-8.19 (m, 1H), 7.86-7.43 (m, 3H), 6.02 (d, J=12.9 Hz, 1H), 4.72-4.42 (m, 1H), 4.02-3.60 (m, 2H), 3.28-2.47 (m, 3H), 1.96 (s, 1H), 1.62-1.22 (m, 1H), 1.27-0.71 (m, 3H).

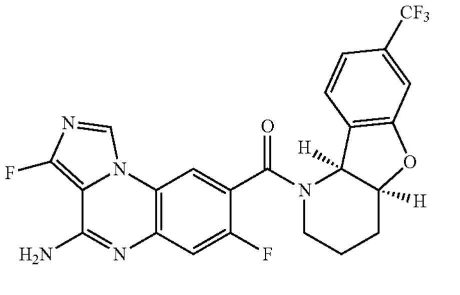 [SMILES: Nc1nc2cc(F)c(C(=O)N3CCC[C@@H]4Oc5cc(C(F)(F)F)ccc5[C@@H]43)cc2n2cnc(F)c12]

Example Ff-621: (4-amino-3,7-difluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)-3,7-difluoroimidazo[1,5-a]quinoxaline-8-carboxylic acid An-1 and (4aS,9bS)-7-(trifluoromethyl)-1,2,3,4,4a,9b-hexahydrobenzofuro[3,2-b]pyridine Ew-1. ES/MS: m/z=490.0 $[M+H]^+$. $^1H$ NMR (400 MHz, Methanol-d4) δ 8.14-8.08 (m, 1H), 7.86 (s, 1H), 7.61-7.44 (m, 1H), 7.37 (d, J=9.1 Hz, 1H), 7.30 (d, J=9.1 Hz, 1H), 7.15-7.06 (m, 1H), 6.48-6.37 (m, 1H), 5.24-5.01 (m, 1H), 3.57-3.39 (m, 1H), 3.08-2.95 (m, 1H), 2.13-1.97 (m, 2H), 1.90-1.65 (m, 2H).

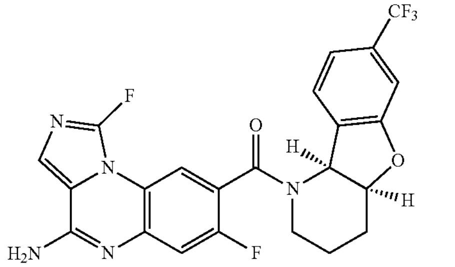 [SMILES: Nc1nc2cc(F)c(C(=O)N3CCC[C@@H]4Oc5cc(C(F)(F)F)ccc5[C@@H]43)cc2n2c(F)ncc12]

Example Ff-622: (4-amino-1,7-difluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)-1,7-difluoroimidazo[1,5-a]quinoxaline-8-carboxylic acid An-2 and (4aS,9bS)-7-(trifluoromethyl)-1,2,3,4,4a,9b-hexahydrobenzofuro[3,2-b]pyridine Ew-1. ES/MS: m/z=490.0 $[M+H]^+$. $^1H$ NMR (400 MHz, Methanol-d4) δ 8.81 (s, 1H), 8.31 (d, J=6.0 Hz, 1H), 7.65-7.23 (m, 3H), 7.16-7.06 (m, 1H), 6.45 (d, J=8.8 Hz, 1H), 5.27-5.15 (m, 1H), 4.50-4.41 (m, 1H), 3.58-3.44 (m, 1H), 3.07-2.96 (m, 1H), 2.12-2.00 (m, 2H), 1.90-1.66 (m, 2H).

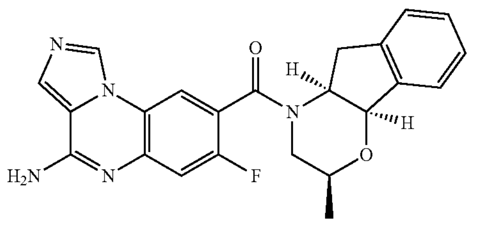 [SMILES: C[C@H]1CN(C(=O)c2cc3c(cc2F)nc(N)c2cncn23)[C@H]2Cc3ccccc3[C@H]2O1]

Example Ff-623: (4-amino-7-fluoroimidazo[1,5-a]quinoxalin-8-yl)((2S,4aS,9bR)-2-methyl-2,3,5,9b-tetrahydroindeno[1,2-b][1,4]oxazin-4(4aH)-yl)methanone. Prepared using general procedure VI-F with intermediates with 4-((tert-butoxycarbonyl)amino)-7-fluoroimidazo[1,5-a]quinoxaline-8-carboxylic acid Af-1 and (2S)-2-methyl-2,3,4,4a,5,9b-hexahydroindeno[1,2-b][1,4]oxazine Et-8. Isolated as peak 2 by HPLC purification. ES/MS: m/z=418.1 $[M+H]^+$. $^1H$ NMR (400 MHz, Methanol-d4) δ 9.27 (s, 1H), 8.45 (t, J=6.1 Hz, 1H), 8.40-8.30 (m, 1H), 7.53-7.14 (m, 5H), 5.07-4.98 (m, 1H), 4.56 (d, J=13.3 Hz, 1H), 4.09-3.99 (m, 1H), 3.88-3.70 (m, 1H), 3.53-3.10 (m, 2H), 3.02-2.75 (m, 1H), 1.29 (d, J=6.2 Hz, 1.60H, minor rotamer), 1.11 (d, J=6.2 Hz, 1.72H, major rotamer).

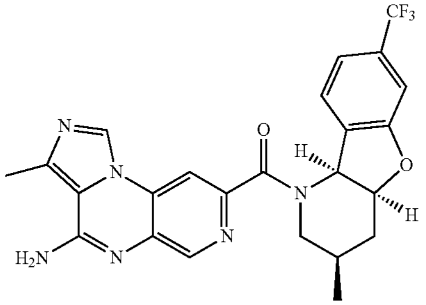 [SMILES: Cc1ncn2c1c(N)nc1cnc(C(=O)N3C[C@H](C)C[C@@H]4Oc5cc(C(F)(F)F)ccc5[C@@H]43)cc12]

Example Ff-624: (4-amino-3-methylimidazo[1,5-a]pyrido[3,4-e]pyrazin-8-yl)((3R,4aS,9bS)-3-methyl-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)-3-methylimidazo[1,5-a]pyrido[3,4-e]pyrazine-8-carboxylic acid Ag-2 and (3R,4aS,9bS)-3-methyl-7-(trifluoromethyl)-1,2,3,4,4a,9b-hexahydrobenzofuro[3,2-b]pyridine hydrogen chloride Ew-7. ES/MS: m/z=483.1 $[M+H]^+$. $^1H$ NMR (400 MHz, Methanol-d4) δ 9.19 (d, J=9.4 Hz, 1H), 8.76 (d, J=10.7 Hz, 1H), 8.54-8.42 (m, 1H), 7.86 (d, J=7.8, 0.4H, minor rotamer), 7.60 (d, J=7.8 Hz, 0.6H, major rotamer), 7.31 (t, J=7.3 Hz, 1H), 7.19-7.08 (m, 1H), 6.33 (d, J=8.4 Hz, 0.6H, major rotamer), 5.97 (d, J=8.4 Hz, 0.4H, minor rotamer) 3.98-3.91 (m, 1H), 3.87-3.64 (m, 2H), 3.21-3.11 (m, 1H), 2.84-2.66 (m, 3H), 2.61-2.50 (m, 1H), 2.37-2.17 (m, 2H), 1.04 (d, J=6.8 Hz, 1H, minor rotamer), 0.92 (d, J=6.8 Hz, 2H, major rotamer).

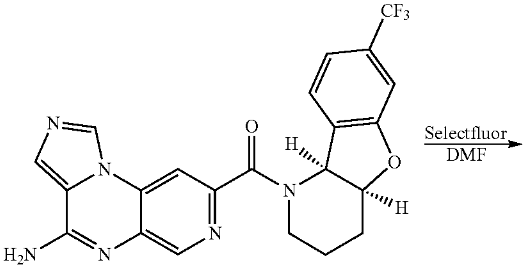

Example Ff-110

-continued

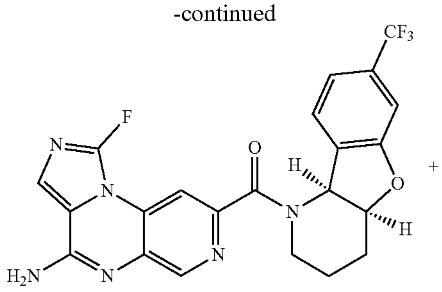

Example Ff-625

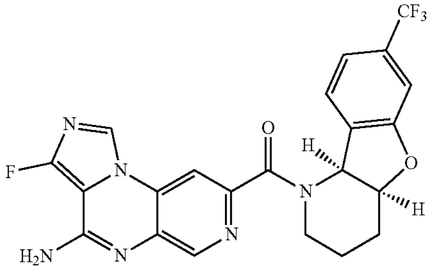

Example Ff-626

Examples Ff-625 and Ff-626. (4-aminoimidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl)methanone (example Ff-110, 70 mg, 0.154 mmol, 1.0 equiv) and Selectfluor (54.6 mg, 0.154 mmol, 1.0 equiv) were suspended in DMF (0.95 mL) and allowed to stir at room temperature overnight. After the allotted time, saturated ammonium chloride (10 mL) was carefully added to the mixture. The resulting mixture was transferred to a separatory funnel and extracted with ethyl acetate (2×10 mL). The combined organic layers were then dried over magnesium sulfate, filtered and concentrated under reduced pressure to afford crude product, which was purified via silica gel column chromatography to afford the desired products. Example Ff-625: [(4aS,9bS)-7-(trifluoromethyl)-3,4,4a,9b-tetrahydro-2H-benzofuro[3,2-b]pyridin-1-yl]-(7-amino-3-fluoro-2,4,8,11-tetrazatricyclo[7.4.0.02,6]trideca-1(9),3,5,7,10,12-hexaen-12-yl)methanone. Peak 1. ES/MS: m/z=473.1 $[M+H]^+$. $^1$H NMR (400 MHz, Methanol-d4) δ 8.59 (dd, J=6.7, 1.7 Hz, 1H), 7.86 (d, J=1.2 Hz, 1H), 7.65 (d, J=11.8 Hz, 1H), 4.46 (q, J=7.1 Hz, 2H), 1.63 (s, 9H), 1.44 (t, J=7.1 Hz, 3H).

Example Ff-626: [(4aS,9bS)-7-(trifluoromethyl)-3,4,4a,9b-tetrahydro-2H-benzofuro[3,2-b]pyridin-1-yl]-(7-amino-5-fluoro-2,4,8,11-tetrazatricyclo[7.4.0.02,6]trideca-1(9),3,5,7,10,12-hexaen-12-yl)methanone. Peak 2. ES/MS: m/z=473.1 $[M+H]^+$. $^1$H NMR (400 MHz, Methanol-d4) δ 8.86 (d, J=1.1 Hz, 1H), 8.71 (d, J=6.6 Hz, 1H), 7.61 (d, J=11.5 Hz, 1H), 4.47 (q, J=7.1 Hz, 2H), 1.60 (s, 9H), 1.45 (t, J=7.1 Hz, 3H).

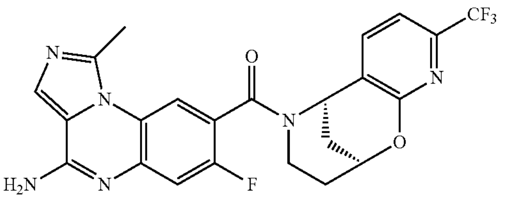 [SMILES: Cc1ncc2c(N)nc3cc(F)c(C(=O)N4CC[C@H]5C[C@@H]4c4ccc(C(F)(F)F)nc4O5)cc3n12]

Example Ff-627: (4-amino-7-fluoro-1-methylimidazo[1,5-a]quinoxalin-8-yl)((2S,6R)-9-(trifluoromethyl)-3,4-dihydro-2H-2,6-methanopyrido[2,3-b][1,5]oxazocin-5(6H)-yl)methanone. Prepared using general procedure VI-F starting with 4-(tert-butoxycarbonylamino)-7-fluoro-1-methyl-imidazo[1,5-a]quinoxaline-8-carboxylic acid Af-5 and (2S,6R)-9-(trifluoromethyl)-3,4,5,6-tetrahydro-2H-2,6-methanopyrido[2,3-b][1,5]oxazocine Ebi-3. ES/MS: m/z=487.2 $[M+H]^+$. $^1$H NMR (400 MHz, MeOD-$d_4$) δ 8.41-8.20 (m, 2H), 8.02 (d, J=7.6 Hz, 0.7H, major rotamer), 7.64 (br, 0.3H, minor rotamer), 7.61 (d, J=9.6 Hz, 0.3H, minor rotamer), 7.48 (d, J=7.5 Hz, 0.7H, major rotamer), 7.45 (d, J=9.5 Hz, 0.3H, minor rotamer), 7.39 (br, 0.7H, major rotamer), 6.18 (s, 0.7H, major rotamer), 5.11 (s, 1H), 5.05 (s, 0.3H, minor rotamer), 4.60 (dd, J=14.4, 6.3 Hz, 0.3H, minor rotamer), 3.56 (dd, J=14.4, 6.3 Hz, 0.7H, major rotamer), 3.15 (s, 0.9H, minor rotamer), 3.10 (s, 2.1H, major rotamer), 3.07-3.00 (m, 0.7H, major rotamer), 2.81-2.69 (m, 0.3H, minor rotamer), 2.49-2.43 (m, 0.3H, minor rotamer), 2.42-2.35 (m, 0.7H, major rotamer), 2.31-2.22 (m, 1H), 2.19-1.99 (m, 2H).

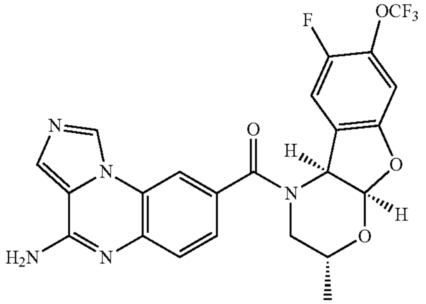 [SMILES: C[C@@H]1CN(C(=O)c2ccc3nc(N)c4cncn4c3c2)[C@H]2c3cc(F)c(OC(F)(F)F)cc3O[C@H]2O1]

Example Ff-628: (4-aminoimidazo[1,5-a]quinoxalin-8-yl)((2R,4aS,9aR)-6-fluoro-2-methyl-7-(trifluoromethoxy)-2,3,9,9a-tetrahydroindeno[2,1-b][1,4]oxazin-4(4aH)-yl)methanone. Prepared following general procedure VI-F starting with 4-(tert-butoxycarbonylamino)imidazo[1,5-a]quinoxaline-8-carboxylic acid Ae-1 and (4aS,9aR)-6-fluoro-2-methyl-7-(trifluoromethoxy)-2,3,4,4a,9,9a-hexahydroindeno[2,1-b][1,4]oxazine Eaw-4. Isolated as the first peak by HPLC purification. ES/MS: m/z=502.3 $[M+H]^+$. $^1$H NMR (400 MHz, MeOD-d4) δ 9.40 (s, 1H), 8.55 (s, 1H), 8.43 (s, 1H), 7.83-7.69 (m, 2H), 7.55-7.27 (m, 2H), 6.03 (s, 0.7H, major rotamer), 5.15 (s, 0.3H, minor rotamer), 4.80 (s, 0.7H, major rotamer), 4.33 (s, 0.3H, minor rotamer), 4.02 (s, 0.3H, minor rotamer), 3.87 (s, 0.7H, major rotamer), 3.49-3.39 (m, 1H), 3.29-3.19 (m, 1H), 2.98-2.81 (m, 2H), 1.52-1.26 (m, 3H).

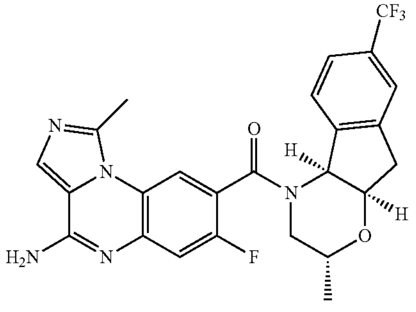 [SMILES: Cc1ncc2c(N)nc3cc(F)c(C(=O)N4C[C@@H](C)O[C@@H]5Cc6cc(C(F)(F)F)ccc6[C@@H]54)cc3n12]

Example Ff-629: (4-amino-7-fluoro-1-methylimidazo[1,5-a]quinoxalin-8-yl)((2R,4aS,9aR)-2-methyl-7-(trifluoromethyl)-2,3,9,9a-tetrahydroindeno[2,1-b][1,4]oxazin-4(4aH)-yl)methanone. Prepared following general procedure VI-F starting with 4-(tert-butoxycarbonylamino)-7-fluoro-1-methyl-imidazo[1,5-a]quinoxaline-8-carboxylic acid Af-5 and (2R,4aS,9aR)-2-methyl-7-(trifluoromethyl)-2,3,4,4a,9,9a-hexahydroindeno[2,1-b][1,4]oxazine hydrochloride Eaz-10. ES/MS: m/z=500.3 $[M+H]^+$. $^1H$ NMR (400 MHz, DMSO-d6) δ 8.70 (brs, 2H), 8.34-8.11 (m, 2H), 8.05-7.59 (m, 3H), 7.51-7.39 (m, 1H), 5.97 (s, 0.6H, major rotamer), 5.06 (s, 0.4H, minor rotamer), 4.71 (t, J=4.3 Hz, 0.6H, major rotamer), 4.60 (m. 0.4H, minor rotamer), 4.21 (d, J=13.3 Hz, 0.4H, minor rotamer), 4.01-3.94 (m, 1H), 3.31-3.24 (m. 1H), 3.19-3.14 (m, 1H), 3.03 (s, 1.8H, major rotamer), 3.01 (s, 1.2H, minor rotamer), 2.95-2.84 (m, 1H), 2.77 (d, J=16.7 Hz, 0.6H, major rotamer), 1.36-1.20 (m, 3H).

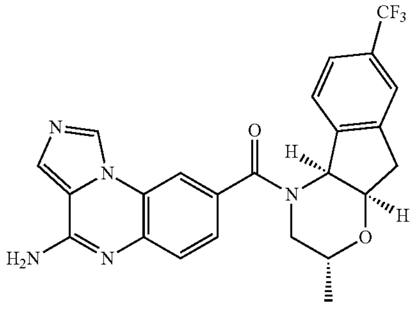 [SMILES: C[C@@H]1CN(C(=O)c2ccc3nc(N)c4cncn4c3c2)[C@H]2c3ccc(C(F)(F)F)cc3C[C@H]2O1]

Example Ff-630: (4-aminoimidazo[1,5-a]quinoxalin-8-yl)((2R,4aS,9aR)-2-methyl-7-(trifluoromethyl)-2,3,9,9a-tetrahydroindeno[2,1-b][1,4]oxazin-4(4aH)-yl)methanone. Prepared following general procedure VI-F starting with 4-(tert-butoxycarbonylamino)imidazo[1,5-a]quinoxaline-8-carboxylic acid Ae-1 and (2R,4aS,9aR)-2-methyl-7-(trifluoromethyl)-2,3,4,4a,9,9a-hexahydroindeno[2,1-b][1,4]oxazine Eaz-10. ES/MS: m/z=468.3 $[M+H]^+$. $^1H$ NMR (400 MHz, DMSO-$d_6$) δ 9.45 (s, 1H), 9.00 (br, 1H), 8.53 (s, 1H), 8.32 (s, 1H), 7.78-7.49 (m, 4H), 5.93 (s, 0.6H, major rotamer), 5.11 (s, 0.4H, minor rotamer), 4.74-4.61 (m, 1H), 4.25-4.09 (m, 0.6H, major rotamer), 4.02-3.89 (m, 0.4H, minor rotamer), 3.82-3.73 (m, 1H), 3.28-3.17 (m, 1H), 3.10-2.71 (m, 2H), 1.42-1.15 (m, 3H).

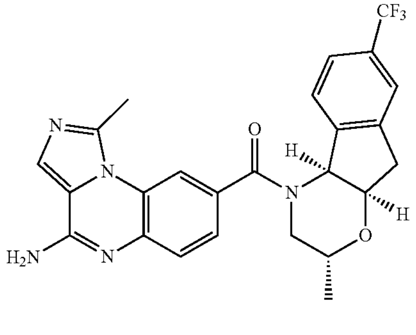 [SMILES: Cc1ncc2c(N)nc3ccc(C(=O)N4C[C@@H](C)O[C@@H]5Cc6cc(C(F)(F)F)ccc6[C@@H]54)cc3n12]

Example Ff-631: (4-amino-1-methylimidazo[1,5-a]quinoxalin-8-yl)((2R,4aS,9aR)-2-methyl-7-(trifluoromethyl)-2,3,9,9a-tetrahydroindeno[2,1-b][1,4]oxazin-4(4aH)-yl)methanone. Prepared following general procedure VI-F starting with 4-(tert-butoxycarbonylamino)-1-methyl-imidazo[1,5-a]quinoxaline-8-carboxylic acid Af-3 and (2R,4aS,9aR)-2-methyl-7-(trifluoromethyl)-2,3,4,4a,9,9a-hexahydroindeno[2,1-b][1,4]oxazine Eaz-10. ES/MS: m/z=482.3 $[M+H]^+$. $^1H$ NMR (400 MHz, DMSO-$d_6$) δ 9.09 (br, 1H), 8.31 (s, 1H), 8.23 (s, 1H), 7.91-7.52 (m, 4H), 5.94 (s, 0.6H, major rotamer), 5.22 (s, 0.4H, minor rotamer), 4.74-4.61 (m, 1H), 4.25-4.09 (m, 1H, major rotamer), 4.02-3.89 (m, 1H), 3.28-3.17 (m, 2H), 3.04 (m, 3H), 2.93-2.71 (m, 1H), 1.38-1.20 (m, 3H).

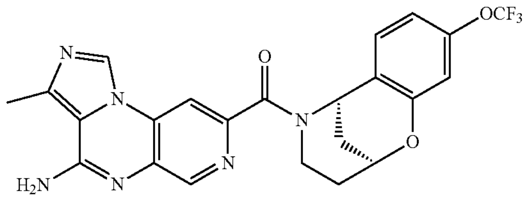 [SMILES: Cc1ncn2c1c(N)nc1cnc(C(=O)N3CC[C@H]4C[C@@H]3c3ccc(OC(F)(F)F)cc3O4)cc12]

Example Ff-632: (4-amino-3-methylimidazo[1,5-a]pyrido[3,4-e]pyrazin-8-yl)((2S,6R)-9-(trifluoromethoxy)-3,4-dihydro-2H-2,6-methanobenzo[b][1,5]oxazocin-5(6H)-yl)methanone. Prepared using general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and (2S,6R)-9-(trifluoromethoxy)-3,4,5,6-tetrahydro-2H-2,6-methanobenzo[b][1,5]oxazocine Ebi-6. ES/MS: m/z=485.2 $[M+H]^+$. $^1H$ NMR (400 MHz, MeOD-$d_4$) δ 9.28 (s, 0.4H, minor rotamer), 9.22 (s, 0.6H, major rotamer), 8.92 (s, 0.4H, minor rotamer), 8.75 (s, 0.6H, major rotamer), 8.51 (s, 0.4H, minor rotamer), 8.38 (s, 0.6H, major rotamer), 7.38 (d, J=8.4 Hz, 0.6H, major rotamer), 7.26 (d, J=8.2 Hz, 0.4H, minor rotamer), 6.89-6.75 (m, 2H), 6.02 (s, 0.6H, major rotamer), 5.33 (s, 0.4H, minor rotamer), 4.87-4.82 (m, 1H), 4.50 (dd, J=14.1, 6.3 Hz, 0.4H, minor rotamer), 3.98-3.67 (m, 0.6H, major rotamer), 3.17-3.05 (m, 0.6H, major rotamer), 2.86-2.83 (m, 0.4H, minor rotamer), 2.82 (s, 1.2H, minor rotamer), 2.79 (s, 1.8H, major rotamer), 2.45-2.38 (m, 0.4H, minor rotamer), 2.38-2.31 (m, 0.6H, major rotamer), 2.26-2.17 (m, 1H), 2.11-1.97 (m, 2H).

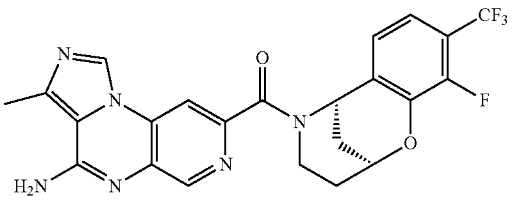 [SMILES: Cc1ncn2c1c(N)nc1cnc(C(=O)N3CC[C@H]4C[C@@H]3c3ccc(C(F)(F)F)c(F)c3O4)cc12]

Example Ff-633: (4-amino-3-methylimidazo[1,5-a]pyrido[3,4-e]pyrazin-8-yl)((2S,6R)-10-fluoro-9-(trifluoromethyl)-3,4-dihydro-2H-2,6-methanobenzo[b][1,5]oxazocin-5(6H)-yl)methanone. Prepared using general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and (2S,6R)-10-fluoro-9-(trifluoromethyl)-3,4,5,6-tetrahydro-2H-2,6-methanobenzo[b][1,5]oxazocine Ebi-8. ES/MS: m/z=487.2 $[M+H]^+$. $^1H$ NMR (400 MHz, MeOD-$d_4$) δ 9.28 (s, 0.4H, minor rotamer), 9.20 (s, 0.6H, major rotamer), 8.90 (s, 0.4H, minor rotamer), 8.74 (s, 0.6H, major rotamer), 8.52 (s, 0.4H, minor rotamer), 8.38 (s, 0.6H, major rotamer), 7.32-7.10 (m, 2H), 6.10 (s, 0.6H, major rotamer), 5.49 (s, 0.4H, minor rotamer), 5.01 (s, 1H), 4.55 (dd, J=14.1, 6.3 Hz, 0.4H, minor rotamer), 3.95-3.85 (m, 0.6H, major rotamer), 3.14-3.04 (m, 0.6H, major rotamer), 2.86-2.83 (m, 0.4H, minor rotamer), 2.82 (s, 1.2H, minor rotamer), 2.79 (s, 1.8H, major rotamer), 2.51-2.45 (m, 0.4H, minor rotamer), 2.43-2.35 (m, 0.6H, major rotamer), 2.31-2.21 (m, 1H), 2.16-2.02 (m, 2H).

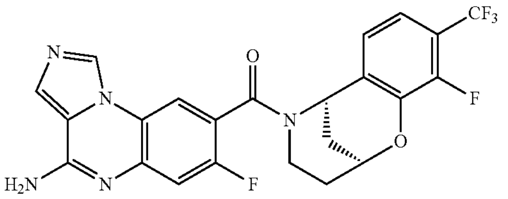 [SMILES: Nc1nc2cc(F)c(C(=O)N3CC[C@H]4C[C@@H]3c3ccc(C(F)(F)F)c(F)c3O4)cc2n2cncc12]

Example Ff-634: (4-amino-7-fluoroimidazo[1,5-a]quinoxalin-8-yl)((2S,6R)-10-fluoro-9-(trifluoromethyl)-3,4-dihydro-2H-2,6-methanobenzo[b][1,5]oxazocin-5(6H)-yl) methanone. Prepared using general procedure VI-F starting with 4-(tert-butoxycarbonylamino)-7-fluoro-imidazo[1,5-a] quinoxaline-8-carboxylic acid Af-1 and (2S,6R)-10-fluoro-9-(trifluoromethyl)-3,4,5,6-tetrahydro-2H-2,6-methanobenzo[b][1,5]oxazocine Ebi-8. ES/MS: m/z=490.3 $[M+H]^+$. $^1H$ NMR (400 MHz, MeOD-$d_4$) δ 9.32 (s, 0.4H, minor rotamer), 9.24 (s, 0.6H, major rotamer), 8.59-8.17 (m, 2H), 7.58 (d, J=9.6 Hz, 0.4H, minor rotamer), 7.44 (d, J=9.1 Hz, 0.6H, major rotamer), 7.33-7.20 (m, 1H), 7.12 (br, 0.4H, minor rotamer), 6.87 (br, 0.6H, major rotamer), 6.14 (s, 0.6H, major rotamer), 5.01 (s, 1H), 4.97 (s, 0.4H, minor rotamer), 4.57 (dd, J=14.1, 6.3 Hz, 0.4H, minor rotamer), 3.53 (dd, J=14.1, 6.3 Hz, 0.6H, minor rotamer), 3.20-3.07 (m, 0.6H, major rotamer), 2.86-2.71 (m, 0.4H, minor rotamer), 2.52-2.39 (m, 0.4H, minor rotamer), 2.39-2.32 (m, 0.6H, major rotamer), 2.31-2.21 (m, 1H), 2.16-2.02 (m, 2H).

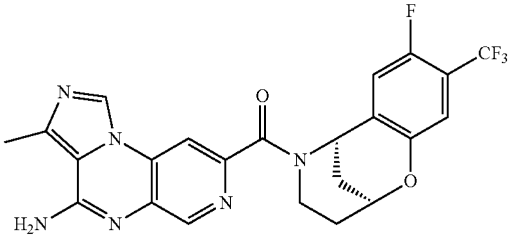 [SMILES: Cc1ncn2c1c(N)nc1cnc(C(=O)N3CC[C@H]4C[C@@H]3c3cc(F)c(C(F)(F)F)cc3O4)cc12]

Example Ff-635: (4-amino-3-methylimidazo[1,5-a]pyrido[3,4-e]pyrazin-8-yl)((2S,6R)-8-fluoro-9-(trifluoromethyl)-3,4-dihydro-2H-2,6-methanobenzo[b][1,5]oxazocin-5(6H)-yl)methanone. Prepared using general procedure VI-F starting with 7-(tert-butoxycarbonylamino)-5-methyl-2,4,8,11-tetrazatricyclo[7.4.0.02,6]trideca-1(13),3,5,7,9,11-hexaene-12-carboxylic acid Ag-2 and (2S,6R)-8-fluoro-9-(trifluoromethyl)-3,4,5,6-tetrahydro-2H-2,6-methanobenzo [b][1,5]oxazocine Ebi-11. ES/MS: m/z=487.2 $[M+H]^+$. $^1H$ NMR (400 MHz, MeOD-$d_4$) δ 9.27 (s, 0.4H, minor rotamer), 9.20 (s, 0.6H, major rotamer), 8.91 (s, 0.4H, minor rotamer), 8.74 (s, 0.6H, major rotamer), 8.52 (s, 0.4H, minor rotamer), 8.39 (s, 0.6H, major rotamer), 7.32-7.15 (m, 2H), 6.02 (s, 0.6H, major rotamer), 5.43 (s, 0.4H, minor rotamer), 4.85 (s, 1H), 4.55 (dd, J=14.1, 6.3 Hz, 0.4H, minor rotamer), 3.95-3.85 (m, 0.6H, major rotamer), 3.14-3.04 (m, 0.6H, major rotamer), 2.86-2.83 (m, 0.4H, minor rotamer), 2.82 (s, 1.2H, minor rotamer), 2.79 (s, 1.8H, major rotamer), 2.44-2.32 (m, 1H), 2.27-2.16 (m, 1H), 2.13-1.99 (m, 2H).

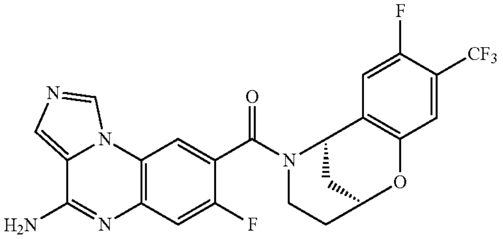

Example Ff-636: (4-amino-7-fluoroimidazo[1,5-a]quinoxalin-8-yl)((2S,6R)-8-fluoro-9-(trifluoromethyl)-3,4-dihydro-2H-2,6-methanobenzo[b][1,5]oxazocin-5(6H)-yl) methanone. Prepared using general procedure VI-F starting with 4-(tert-butoxycarbonylamino)-7-fluoro-imidazo[1,5-a] quinoxaline-8-carboxylic acid Af-1 and (2S,6R)-8-fluoro-9-(trifluoromethyl)-3,4,5,6-tetrahydro-2H-2,6-methanobenzo [b][1,5]oxazocine Ebi-11. ES/MS: m/z=490.2 $[M+H]^+$. $^1H$ NMR (400 MHz, MeOD-$d_4$) δ 9.33 (s, 0.4H, minor rotamer), 9.23 (s, 0.6H, major rotamer), 8.62-8.22 (m, 2H), 7.57 (m, 0.4H, minor rotamer), 7.44 (d, J=9.6 Hz, 0.6H, major rotamer), 7.29 (d, J=10.0 Hz, 0.4H, minor rotamer), 7.23-7.18 (m, 1H), 6.88 (br, 0.6H, major rotamer), 6.07 (s, 0.6H, major rotamer), 4.91 (s, 1H), 4.86 (s, 0.4H, minor rotamer), 4.57 (dd, J=14.1, 6.3 Hz, 0.4H, minor rotamer), 3.55-3.45 (m, 0.6H, major rotamer), 3.20-3.07 (m, 0.6H, major rotamer), 2.86-2.71 (m, 0.4H, minor rotamer), 2.44-2.39 (m, 0.4H, minor rotamer), 2.33-2.27 (m, 0.6H, major rotamer), 2.26-2.18 (m, 1H), 2.14-1.93 (m, 2H).

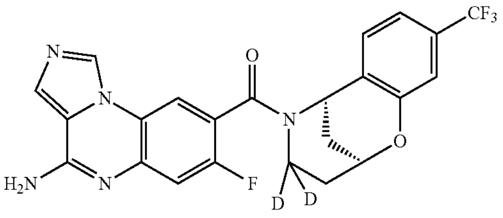 [SMILES: [2H]C1([2H])C[C@H]2C[C@H](c3ccc(C(F)(F)F)cc3O2)N1C(=O)c1cc2c(cc1F)nc(N)c1cncn12]

Example Ff-637: (4-amino-7-fluoroimidazo[1,5-a]quinoxalin-8-yl)((2S,6R)-9-(trifluoromethyl)-3,4-dihydro-2H-2,6-methanobenzo[b][1,5]oxazocin-5(6H)-yl-4,4-d2)methanone. Prepared using general procedure VI-F starting with 4-(tert-butoxycarbonylamino)-7-fluoro-imidazo[1,5-a]quinoxaline-8-carboxylic acid Af-1 and tert-butyl (2S,6R)-9-(trifluoromethyl)-3,4-dihydro-2H-2,6-methanobenzo[b][1,5]oxazocine-5(6H)-carboxylate-4,4-d2 Ey-2. ES/MS: m/z=474.2 $[M+H]^+$. $^1H$ NMR (400 MHz, DMSO-$d_6$) δ 9.35 (s, 0.4H, minor rotamer), 9.30 (s, 0.6H, major rotamer), 8.98-8.10 (m, 4H), 7.54-7.41 (m, 1H), 7.38-7.26 (m, 1H), 7.25-6.95 (m, 2H), 5.98 (s, 0.6H, major rotamer), 4.90 (s, 1H), 4.83 (s, 0.4H, minor rotamer), 2.15 (s, 1H), 2.12-2.06 (m, 0.4H, minor rotamer), 2.04-1.96 (m, 0.6H, major rotamer), 1.98-1.84 (m, 2H).

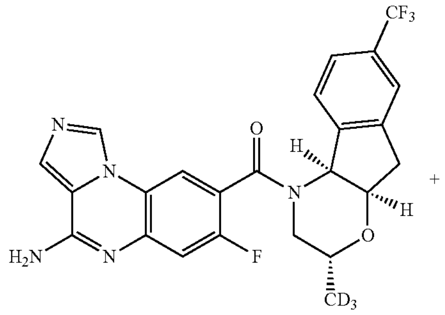

Example Ff-638
$1^{st}$ peak

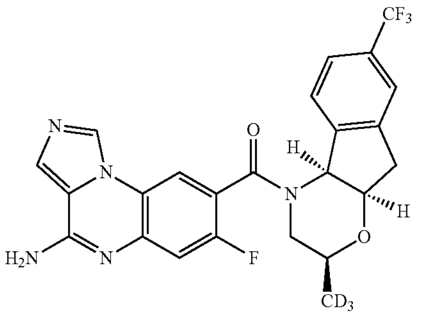

Example Ff-639
$2^{nd}$ peak

Examples Ff-638 and Ff-639. Prepared following general procedure VI-F starting with 4-(tert-butoxycarbonylamino)-7-fluoro-imidazo[1,5-a]quinoxaline-8-carboxylic acid Af-1 and (4aS,9aR)-2-(methyl-d3)-7-(trifluoromethyl)-2,3,4,4a,9,9a-hexahydroindeno[2,1-b][1,4]oxazine Ebr-1.

Example Ff-638: (4-amino-7-fluoroimidazo[1,5-a]quinoxalin-8-yl)((2R,4aS,9aR)-2-(methyl-d3)-7-(trifluoromethyl)-2,3,9,9a-tetrahydroindeno[2,1-b][1,4]oxazin-4(4aH)-yl)methanone. Isolated as the first peak of preparative HPLC. ES/MS: m/z=489.3 $[M+H]^+$. $^1H$ NMR (400 MHz, DMSO-d6) δ 9.34 (s, 1H), 8.76-8.19 (m, 3H), 8.21-8.05 (m, 1H), 7.79-7.56 (m, 2H), 7.555-7.15 (m, 2H), 6.00 (s, 0.6H, major rotamer), 5.02 (s, 0.4H, minor rotamer), 4.70 (t, J=4.3 Hz, 0.6H, major rotamer), 4.61 (t, J=4.3 Hz, 0.4H, minor rotamer), 4.27-4.10 (m, 0.6H, major rotamer), 3.96 (s, 0.4H, minor rotamer), 3.76 (s, 0.6H, major rotamer), 3.37-3.27 (m, 1H), 3.19-3.03 (m, 1H), 2.94-2.86 (m, 1H), 2.80-2.74 (m, 0.4H, minor rotamer).

Example Ff-639: (4-amino-7-fluoroimidazo[1,5-a]quinoxalin-8-yl)((2S,4aS,9aR)-2-(methyl-d3)-7-(trifluoromethyl)-2,3,9,9a-tetrahydroindeno[2,1-b][1,4]oxazin-4(4aH)-yl)methanone. Isolated as the second peak of preparative HPLC. ES/MS: m/z=489.3 $[M+H]^+$. $^1H$ NMR (400 MHz, DMSO-d6) δ 9.34 (s, 0.7H, major rotamer), 9.26 (s, 0.3H, minor rotamer), 8.87-8.27 (m, 3H), 8.23-8.10 (m, 1H), 7.77-7.56 (m, 2H), 7.55-7.15 (m, 2H), 5.93 (s, 0.7H, major rotamer), 5.02 (s, 0.3H, minor rotamer), 4.52 (t, J=4.3 Hz, 0.7H, major rotamer), 4.44 (t, J=4.3 Hz, 0.3H, minor rotamer), 4.42-4.35 (m, 0.3H, minor rotamer), 3.39-3.28 (m, 1H), 3.10-3.02 (m, 0.7H, major rotamer), 3.00-2.93 (m, 1H), 2.87-2.81 (m, 0.3H, minor rotamer), 2.74-2.64 (m, 1H), 2.45-2.36 (m, 0.7H, major rotamer).

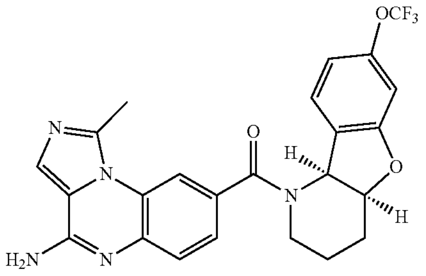 [SMILES: Cc1ncc2c(N)nc3ccc(C(=O)N4CCC[C@@H]5Oc6cc(OC(F)(F)F)ccc6[C@@H]54)cc3n12]

Example Ff-640: (4-amino-1-methylimidazo[1,5-a]quinoxalin-8-yl)((4aS,9bS)-7-(trifluoromethoxy)-3,4,4a,9b-tetrahydrobenzofuro[3,2-b]pyridin-1(2H)-yl)methanone. Prepared following general procedure VI-F starting with 4-(tert-butoxycarbonylamino)-1-methyl-imidazo[1,5-a]quinoxaline-8-carboxylic acid Af-3 and (4aS,9bS)-7-(trifluoromethoxy)-1,2,3,4,4a,9b-hexahydrobenzofuro[3,2-b]pyridine hydrochloride Ew-12. ES/MS: m/z=484.2 $[M+H]^+$. $^1H$ NMR (400 MHz, MeOD-$d_4$) δ 8.34 (s, 2H), 7.72 (s, 2H), 7.52 (d, J=8.2 Hz, 1H), 6.90 (ddd, J=8.2, 2.2, 1.0 Hz, 1H), 6.79 (s, 1H), 6.15 (s, 1H), 5.23-5.08 (m, 1H), 3.70 (brs, 1H), 3.12 (s, 3H), 3.07-2.92 (m, 1H), 2.21-2.03 (m, 2H), 1.97-1.86 (m, 1H), 1.84-1.69 (m, 1H).

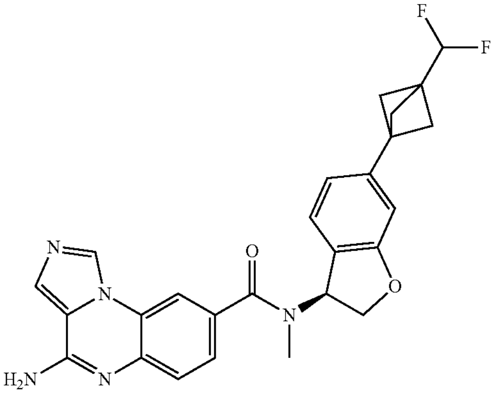 [SMILES: CN(C(=O)c1ccc2nc(N)c3cncn3c2c1)[C@@H]1COc2cc(C34CC(C(F)F)(C3)C4)ccc21]

Example Ff-641: (S)-4-amino-N-(6-(3-(difluoromethyl)bicyclo[1.1.1]pentan-1-yl)-2,3-dihydrobenzofuran-3-yl)-N-methylimidazo[1,5-a]quinoxaline-8-carboxamide. Prepared using (S)-4-amino-N-(6-bromo-2,3-dihydrobenzofuran-3-yl)-N-methylimidazo[1,5-a]quinoxaline-8-carboxamide (made following general procedure VI-F starting with Ae-1 and Eh-5) and 1-(difluoromethyl)-3-iodobicyclo[1.1.1]pentane following the reductive coupling procedure reported for example Ff-444. ES/MS: m/z=476.3 $[M+H]^+$. $^1H$ NMR (400 MHz, Methanol-d4) δ 9.35 (s, 1H), 8.44 (d, J=13.1 Hz, 2H), 7.87-7.58 (m, 2H), 7.35 (d, J=39.5 Hz, 1H), 7.03-6.66 (m, 2H), 6.41 (s, 1H), 5.88 (t, J=56.6 Hz, 1H), 4.66 (d, J=9.1 Hz, 2H), 2.76 (d, J=24.7 Hz, 3H), 2.12 (s, 6H).

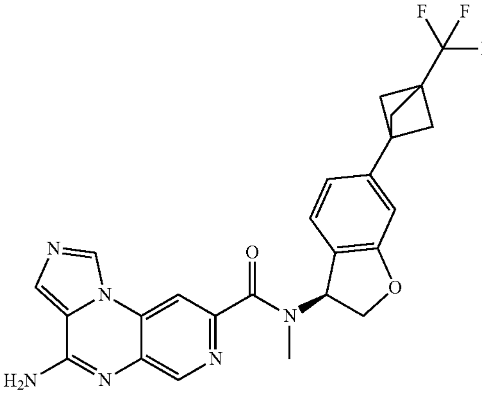

Example Ff-642: (S)-4-amino-N-methyl-N-(6-(3-(trifluoromethyl)bicyclo[1.1.1]pentan-1-yl)-2,3-dihydrobenzofuran-3-yl)imidazo[1,5-a]pyrido[3,4-e]pyrazine-8-carboxamide. Prepared using (S)-4-amino-N-(6-bromo-2,3-dihydrobenzofuran-3-yl)-N-methylimidazo[1,5-a]pyrido[3,4-e]pyrazine-8-carboxamide (made following general procedure VI-F starting with Af-6 and Eh-5) and 1-iodo-3-(trifluoromethyl)bicyclo[1.1.1]pentane following the reductive coupling procedure reported for example Ff-444. ES/MS: m/z=495.3 $[M+H]^+$. $^1H$ NMR (400 MHz, Methanol-d4) δ 9.23 (d, J=8.1 Hz, 1H), 8.79 (d, J=21.4 Hz, 1H), 8.46 (d, J=19.8 Hz, 1H), 8.10 (d, J=4.0 Hz, 1H), 7.41 (d, J=7.8 Hz, 1H), 7.03-6.66 (m, 2H), 4.68 (d, J=6.6 Hz, 1H), 3.50 (p, J=1.6 Hz, 1H), 3.15 (p, J=1.7 Hz, 1H), 2.79 (d, J=16.6 Hz, 3H), 2.27 (d, J=7.6 Hz, 6H), 1.96 (s, 1H).

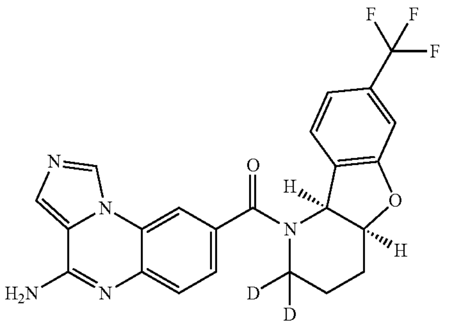 [SMILES: [2H]C1([2H])CC[C@@H]2Oc3cc(C(F)(F)F)ccc3[C@@H]2N1C(=O)c1ccc2nc(N)c3cncn3c2c1]

Example Ff-643: (4-aminoimidazo[1,5-a]quinoxalin-8-yl)((4aS,9bS)-7-(trifluoromethyl)-3,4,4a,9b-tetrahydrobenzofuro[3,2-b]pyridin-1(2H)-yl-2,2-d2)methanone. Prepared following general procedure VI-F starting with 4-(tert-butoxycarbonylamino)imidazo[1,5-a]quinoxaline-8-carboxylic acid Ae-1 and (4aS,9bS)-(4aS,9bS)-7-(trifluoromethyl)-1,2,3,4,4a,9b-hexahydrobenzofuro[3,2-b]pyridine-2,2-d2 Ey-1. ES/MS: m/z=456.3 $[M+H]^+$. $^1H$ NMR (400 MHz, Methanol-d4) δ 9.36 (d, J=0.7 Hz, 1H), 8.50-8.28 (m, 1H), 7.83-7.53 (m, 2H), 7.30 (dd, J=7.9, 1.4 Hz, 1H), 7.13 (s, 1H), 5.18 (s, 1H), 3.23-3.10 (m, 3H), 2.11 (s, 1H), 1.94-1.66 (m, 4H).

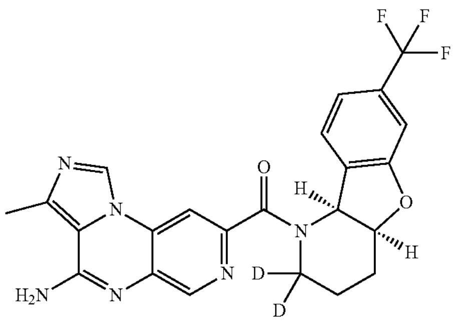 [SMILES: [2H]C1([2H])CC[C@@H]2Oc3cc(C(F)(F)F)ccc3[C@@H]2N1C(=O)c1cc2c(cn1)nc(N)c1c(C)ncn12]

Example Ff-644: (4-amino-3-methylimidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl-2,2-d2)methanone. Prepared following general procedure VI-F starting with 4-((tert-butoxycarbonyl)amino)-3-methylimidazo[1,5-a]pyrido[3,4-e]pyrazine-8-carboxylic acid Ag-2 and (4aS,9bS)-7-(trifluoromethyl)-1,2,3,4,4a,9b-hexahydrobenzofuro[3,2-b]pyridine-2,2-d2 Ey-1. ES/MS: m/z=471.3 $[M+H]^+$. 1H NMR (400 MHz, Methanol-d4) δ 9.22 (s, 1H), 8.85-8.75 (d, m, 1H), 8.54-8.45 (m, 1H), 7.86 (d, J=7.8 Hz, 1H), 7.62 (d, J=7.8 Hz, 1H), 7.34-7.23 (m, 1H), 7.13-7.09 (m, 1H), 6.36 (d, J=8.7 Hz, 1H), 6.03 (d, J=9.1 Hz, 1H), 5.19-5.04 (m, 1H), 3.18 (td, J=6.6, 3.7 Hz, 3H), 2.19-1.93 (m, 2H), 1.92-1.75 (m, 2H).

Examples Ff-646 and Ff-647. (4-amino-7-fluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone example Ff-104 (30 mg, 0.05 mmol) was suspended in $CHCl_3$ (2 mL) and NCS (7 mg, 0.05 mmol) was added. The mixture was heated to 50° C. for 1 hour then cooled to room temperature and purified by silica gel flash column chromatography, then purified by preparative HPLC to afford example Ff-646 (peak 1) and example Ff-647 (peak 2).

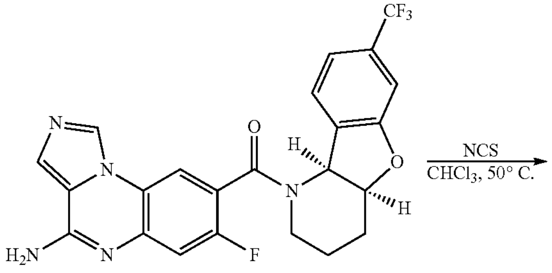

Example Ff-104

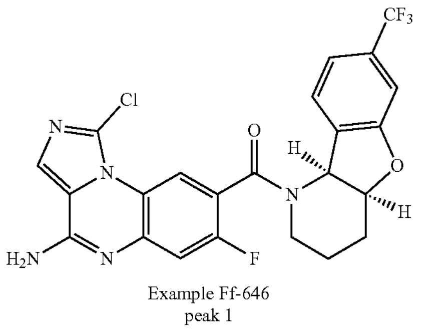

+

Example Ff-646
peak 1

-continued

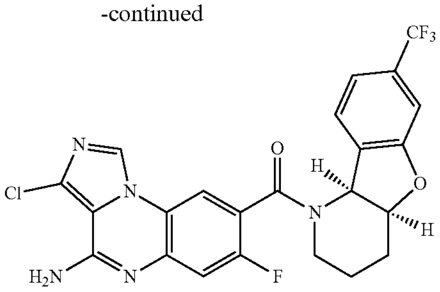

Example Ff-647
peak 2

Example Ff-646: (4-amino-1-chloro-7-fluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. ES/MS: m/z=505.7, 507.7 $[M+H]^+$. $^1$H NMR (400 MHz, Methanol-d4) δ 8.92 (s, 1H), 8.19 (s, 1H), 7.55 (s, 1H), 7.41 (d, J=10.1 Hz, 1H), 7.29 (d, J=7.7 Hz, 1H), 7.13 (s, 1H), 6.50-6.34 (m, 1H), 5.25-5.08 (m, 1H), 3.57-3.40 (m, 1H), 3.09-2.91 (m, 1H), 2.14-2.01 (m, 2H), 1.91-1.61 (m, 2H).

Example Ff-647: (4-amino-3-chloro-7-fluoroimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. ES/MS: m/z=505.7, 507.7 $[M+H]^+$. $^1$H NMR (400 MHz, Methanol-d4) δ 9.08 (s, 1H), 8.32 (d, J=6.0 Hz, 1H), 7.59 (s, 1H), 7.51-7.21 (m, 2H), 7.11 (d, J=26.3 Hz, 1H), 6.45 (s, 0.7H, major rotamer), 5.66 (d, J=9.2 Hz, 0.3H, minor rotamer), 5.19 (dt, J=8.8, 4.4 Hz, 1H), 3.55-3.42 (m, 1H), 3.09-2.93 (m, 1H), 2.14-1.99 (m, 2H), 1.92-1.58 (m, 2H).

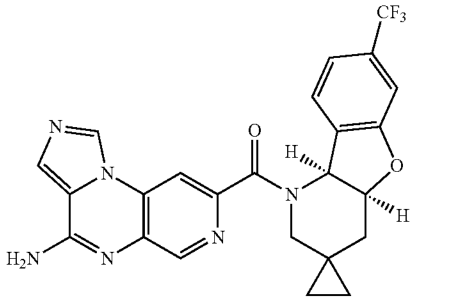 [SMILES: Nc1nc2cnc(C(=O)N3CC4(CC4)C[C@@H]4Oc5cc(C(F)(F)F)ccc5[C@@H]43)cc2n2cncc12]

Example Ff-648: (4-aminoimidazo[1,5-a]pyrido[3,4-e]pyrazin-8-yl)((4aS,9bS)-7-(trifluoromethyl)-4a,9b-dihydro-2H-spiro[benzofuro[3,2-b]pyridine-3,1'-cyclopropan]-1(4H)-yl)methanone. Prepared following general procedure VI-F starting with 4-((tertbutoxycarbonyl)amino)imidazo[1,5-a]pyrido[3,4-e]pyrazine-8-carboxylic acid Af-6 and (4aS,9bS)-7-(trifluoromethyl)-1,4,4a,9b-tetrahydro-2H-spiro[benzofuro[3,2-b]pyridine-3,1'-cyclopropane] Ebs-2. ES/MS: m/z=480.8 $[M+H]^+$. $^1$H NMR (400 MHz, Methanol-d4) δ 9.39-9.20 (m, 1H), 8.88-8.74 (m, 1H), 8.62 (s, 0.5H, rotamer), 8.52 (s, 0.5H, rotamer), 8.29-8.27 m, 1H), 7.77 (d, J=7.8 Hz, 0.5H, rotamer), 7.59 (d, J=7.6 Hz, 0.5H, rotamer), 7.40-7.20 (m, 1H), 7.13 (s, 0.5H, rotamer), 7.06 (s, 0.5H, rotamer), 6.54 (d, J=8.9 Hz, 0.5H, rotamer), 6.15 (d, J=9.1 Hz, 0.5H, rotamer), 5.40-5.21 (m, 0.5H, rotamer), 5.19-5.05 (m, 0.5H, rotamer), 4.23-3.92 (m, 1H), 2.91-2.73 (m, 1H), 2.28-2.03 (m, 1H), 1.78-1.61 (m, 1H), 0.64-0.06 (m, 4H).

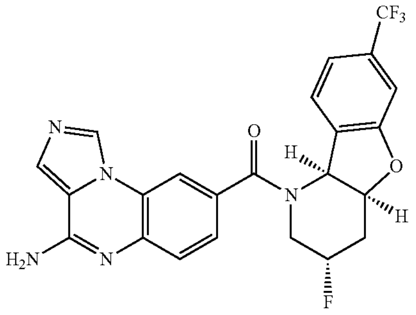 [SMILES: Nc1nc2ccc(C(=O)N3C[C@@H](F)C[C@@H]4Oc5cc(C(F)(F)F)ccc5[C@@H]43)cc2n2cncc12]

Example Ff-649: (4-aminoimidazo[1,5-a]quinoxalin-8-yl)((3S,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (3S,4aS,9bS)-3-fluoro-7-(trifluoromethyl)-1,2,3,4,4a,9b-hexahydrobenzofuro[3,2-b]pyridine Ex-1. ES/MS: m/z=471.8 $[M+H]^+$. $^1$H NMR (400 MHz, Methanol-d4) δ 9.32-9.04 (m, 1H), 8.45 (s, 1H), 8.33 (s, 1H), 7.86-7.55 (m, 3H), 7.35 (d, J=7.9 Hz, 1H), 7.16 (s, 1H), 6.39-6.12 (m, 1H), 5.39-5.19 (m, 1H), 5.19-5.03 (m, 1H), 4.13-3.81 (m, 1H), 3.21-2.79 (m, 2H), 2.46-2.17 (m, 1H).

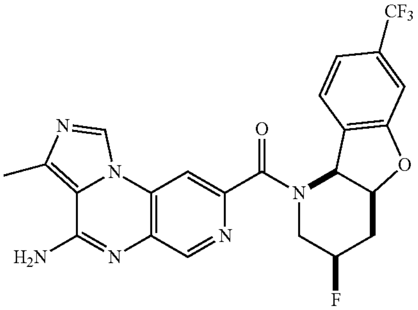

Example Ff-650: Rac-(4-amino-3-methylimidazo[1,5-a]pyrido[3,4-e]pyrazin-8-yl)((3R,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 4-((tertbutoxycarbonyl)amino)-3-methylimidazo[1,5-a]pyrido[3,4-e]pyrazine-8-carboxylic acid Ag-2 and cis-3-fluoro-7-(trifluoromethyl)-1,2,3,4,4a,9b-hexahydrobenzofuro[3,2-b]pyridine Ev-5. ES/MS: m/z=486.8 $[M+H]^+$. $^1$H NMR (400 MHz, Methanol-$d_4$) δ 9.20 (s, 1H), 8.83 (s, 0.33H, minor rotamer), 8.76 (s, 0.67H, major rotamer), 8.56 (s, 0.33H, minor rotamer), 8.50 (s, 0.67H, major rotamer), 7.99 (s, 0.33H, minor rotamer), 7.69 (d, J=7.8 Hz, 0.67H, major rotamer), 7.30 (d, J=7.9 Hz, 1H), 7.20-7.05 (m, 1H), 6.19 (d, J=8.5 Hz, 0.67H, major rotamer), 6.13-6.04 (m, 0.33H, minor rotamer), 5.48-5.26 (m, 1H), 5.26-4.98 (m, 2H), 4.34-4.18 (m, 1H), 2.78 (s, 3H), 1.45-1.22 (m, 2H).

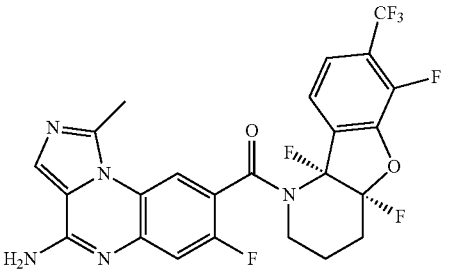 [SMILES: Cc1ncc2c(N)nc3cc(F)c(C(=O)N4CCC[C@]5(F)Oc6c(ccc(C(F)(F)F)c6F)[C@]45F)cc3n12]

Example Ff-651: (4-amino-7-fluoro-1-methylimidazo[1,5-a]quinoxalin-8-yl)((4aS,9bS)-6-fluoro-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoro-1-methylimidazo[1,5-a]quinoxaline-8-carboxylic acid Af-5 and (4aS,9bS)-6-fluoro-7-(trifluoromethyl)-1,2,3,4,4a,9b-hexahydrobenzofuro[3,2-b]pyridine Ew-3. ES/MS: m/z=503.8 $[M+H]^+$. $^1H$ NMR (400 MHz, Methanol-d4) δ 8.28 (s, 1H), 7.51-7.16 (m, 3H), 6.50 (s, 1H), 5.42-5.16 (m, 1H), 3.61-3.45 (m, 1H), 3.11 (s, 3H), 3.09-2.93 (m, 1H), 2.19-2.06 (m, 2H), 1.88-1.66 (m, 2H).

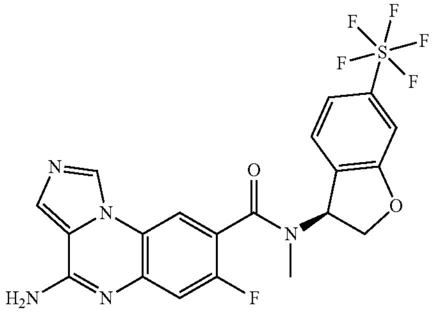 [SMILES: CN(C(=O)c1cc2c(cc1F)nc(N)c1cncn12)[C@@H]1COc2cc(S(F)(F)(F)(F)F)ccc21]

Example Ff-652: (S)-4-amino-7-fluoro-N-methyl-N-(6-(pentafluoro-16-sulfaneyl)-2,3-dihydrobenzofuran-3-yl)imidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (S)—N-methyl-6-(pentafluoro-16-sulfaneyl)-2,3-dihydrobenzofuran-3-amine Eam-12. EZ/MS: m/z=504.0 $[M+H]^+$. $^1H$ NMR (400 MHz, Methanol-d4) δ 9.25 (s, 1H), 8.45 (d, J=5.9 Hz, 1H), 8.37 (d, J=1.7 Hz, 1H), 7.71-7.25 (m, 4H), 6.57 (dd, J=9.1, 3.8 Hz, 0.5H rotamer), 5.70 (t, J=6.8 Hz, 0.5H rotamer), 4.77 (dd, J=10.7, 3.9 Hz, 1H), 2.95-2.72 (m, 3H).

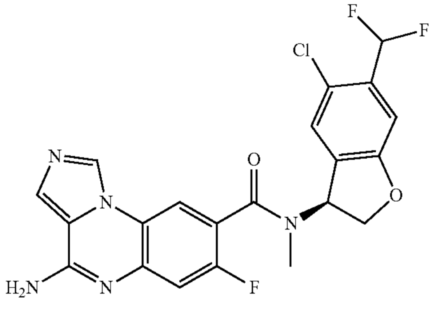 [SMILES: CN(C(=O)c1cc2c(cc1F)nc(N)c1cncn12)[C@@H]1COc2cc(C(F)F)c(Cl)cc21]

Example Ff-653: (S)-4-amino-N-(5-chloro-6-(difluoromethyl)-2,3-dihydrobenzofuran-3-yl)-7-fluoro-N-methylimidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (S)-5-chloro-6-(difluoromethyl)-N-methyl-2,3-dihydrobenzofuran-3-amine Ebu-1. EZ/MS: m/z=462.0 $[M+H]^+$. $^1H$ NMR (400 MHz, Methanol-d4) δ 9.25 (s, 1H), 8.51-8.29 (m, 1H), 7.65-7.33 (m, 2H), 7.25-6.80 (m, 2H), 6.51 (dd, J=9.2, 3.7 Hz, 0.5H rotamer), 5.68 (t, J=6.6 Hz, 0.5H rotamer), 4.90-4.82 (m, 1H rotamer), 4.73 (dd, J=10.7, 3.9 Hz, 1H rotamer), 3.25-3.35 (m, 1H), 2.86 (s, 1.5H rotamer), 2.76 (d, J=1.2 Hz, 1.5H rotamer).

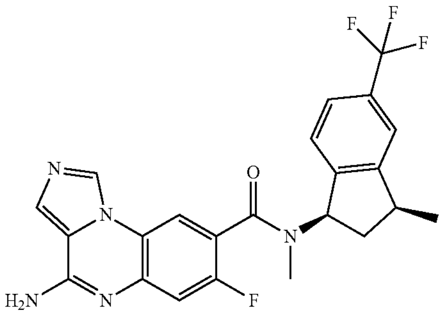 [SMILES: C[C@H]1C[C@@H](N(C)C(=O)c2cc3c(cc2F)nc(N)c2cncn23)c2ccc(C(F)(F)F)cc21]

Example Ff-654: 4-amino-7-fluoro-N-methyl-N-((1R,3S)-3-methyl-5-(trifluoromethyl)-2,3-dihydro-1H-inden-1-yl)imidazo[1,5-a]quinoxaline-8-carboxamide. Prepared using general procedure VI-F starting with 4-(tert-butoxycarbonylamino)-7-fluoro-imidazo[1,5-a]quinoxaline-8-carboxylic acid Af-1 and (1R,3S)—N,3-dimethyl-5-(trifluoromethyl)-2,3-dihydro-1H-inden-1-amine Ebw-1. EZ/MS: m/z=458.0 $[M+H]^+$. $^1H$ NMR (400 MHz, Methanol-d4) δ 9.29 (d, J=13.9 Hz, 1H), 8.52 (d, J=5.8 Hz, 1H), 8.43-8.35 (m, 1H), 7.61 (d, J=7.0 Hz, 2H), 7.55 (d, J=1.8 Hz, 1H), 7.53-7.39 (m, 1H), 6.35 (t, J=9.0 Hz, 0.5H rotamer), 5.30 (t, J=8.9 Hz, 0.5H rotamer), 3.21-3.00 (m, 0.5H rotamer), 2.91 (s, 1H+0.5H rotamer), 2.83-2.43 (m, 3H), 2.03-1.73 (m, 1H), 1.55-1.43 (m, 1.5H rotamer), 1.41 (s, 1.5H rotamer).

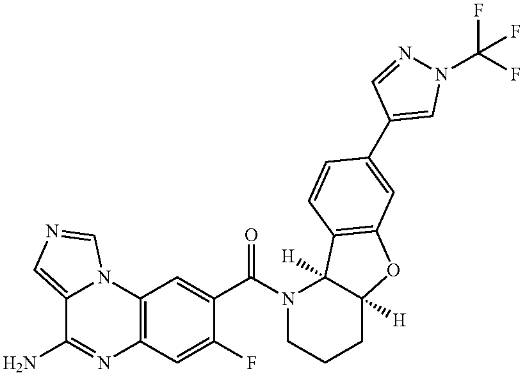 [SMILES: Nc1nc2cc(F)c(C(=O)N3CCC[C@@H]4Oc5cc(-c6cnn(C(F)(F)F)c6)ccc5[C@@H]43)cc2n2cncc12]

Example Ff-655: (4-amino-7-fluoroimidazo[1,5-a]quinoxalin-8-yl)((4aS,9bS)-7-(1-(trifluoromethyl)-1H-pyrazol-4-yl)-3,4,4a,9b-tetrahydrobenzofuro[3,2-b]pyridin-1(2H)-yl)methanone. Prepared using general procedure VI-F starting with 4-(tert-butoxycarbonylamino)-7-fluoro-imidazo[1,5-a]quinoxaline-8-carboxylic acid Af-1 and (4aS, 9bS)-7-(1-(trifluoromethyl)-1H-pyrazol-4-yl)-1,2,3,4,4a,9b-hexahydrobenzofuro[3,2-b]pyridine hydrochloride Ebd-6. EZ/MS: m/z=538.0 $[M+H]^+$. $^1H$ NMR (400 MHz, Methanol-d4 δ 9.30 (d, J=9.7 Hz, 1H), 8.71-7.99 (m, 4H), 7.61-7.06 (m, 4H), 6.38 (d, J=8.7 Hz, 1H), 5.56 (d, J=9.1 Hz, 1H), 3.21-2.71 (m, 1H), 2.24-1.97 (m, 2H), 1.62-2.00 (m, 2H), 1.30 (s,

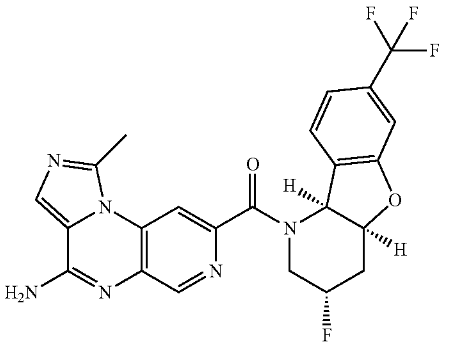 [SMILES: Cc1ncc2c(N)nc3cnc(C(=O)N4C[C@@H](F)C[C@@H]5Oc6cc(C(F)(F)F)ccc6[C@@H]54)cc3n12]

Example Ff-656: (4-amino-1-methylimidazo[1,5-a]pyrido[3,4-e]pyrazin-8-yl)((3S,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 7-(tert-butoxycarbonylamino)-3-methyl-2,4,8,11-tetrazatricyclo[7.4.0.02,6]trideca-1(13),3,5,7,9,11-hexaene-12-carboxylic acid Ag-1 and (3S,4aS,9bS)-3-fluoro-7-(trifluoromethyl)-1,2,3,4,4a,9b-hexahydrobenzofuro[3,2-b]pyridine Ex-1. EZ/MS: m/z=487.0 $[M+H]^+$. $^1H$ NMR (400 MHz, Methanol-d4) δ 8.91 (s, 0.5H rotamer), 8.81 (s, 0.5H rotamer), 8.60 (s, 0.5H rotamer), 8.43 (s, 0.5H rotamer), 8.29 (s, 1H), 8.04 (d, J=7.8 Hz, 0.5H rotamer), 7.69 (d, J=7.8 Hz, 0.5H rotamer), 7.34 (dd, J=7.8, 1.5 Hz, 1H), 7.15 (d, J=11.2 Hz, 1H), 6.40 (d, J=8.3 Hz, 0.5H rotamer), 6.24 (d, J=8.6 Hz, 0.5H rotamer), 5.26 (s, 0.5H rotamer), 5.20-5.00 (m, 1H), 4.42-4.21 (m, 0.5H rotamer), 3.18 (s, 1.5H rotamer), 3.16 (s, 1.5H rotamer), 3.01-2.59 (m, 2H), 2.40-2.03 (m, 2H).

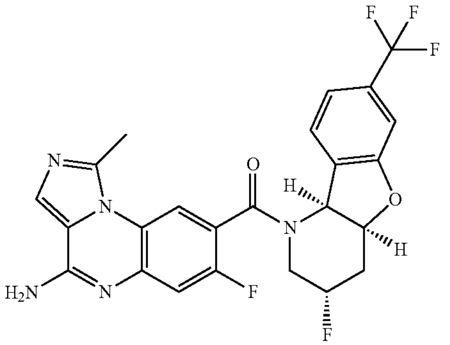 [SMILES: Cc1ncc2c(N)nc3cc(F)c(C(=O)N4C[C@@H](F)C[C@@H]5Oc6cc(C(F)(F)F)ccc6[C@@H]54)cc3n12]

Example Ff-657: (4-amino-7-fluoro-1-methylimidazo[1,5-a]quinoxalin-8-yl)((3S,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoro-1-methylimidazo[1,5-a]quinoxaline-8-carboxylic acid Af-5 and (3S,4aS,9bS)-3-fluoro-7-(trifluoromethyl)-1,2,3,4,4a,9b-hexahydrobenzofuro[3,2-b]pyridine Ex-1. EZ/MS: m/z=504.0 $[M+H]^+$. $^1H$ NMR (400 MHz, Methanol-d4) δ 8.29 (s, 1H), 8.25 (d, J=5.8 Hz, 1H), 7.68 (d, J=7.9 Hz, 1H), 7.44 (d, J=9.5 Hz, 1H), 7.36 (d, J=7.8 Hz, 1H), 7.18 (s, 1H), 6.39 (d, J=8.3 Hz, 1H), 5.26 (s, 1H), 5.04 (s, 1H), 3.80-3.63 (m, 1H), 3.20-3.02 (m, 3H), 2.87 (s, 1H), 2.30 (s, 1H), 1.40-1.17 (m, 1H).

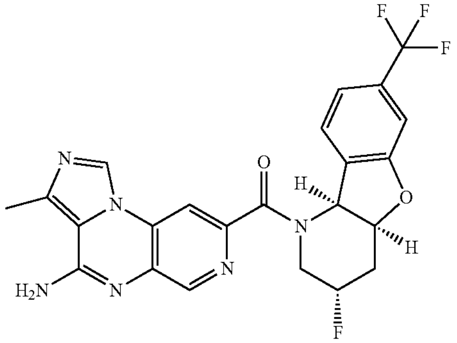 [SMILES: Cc1ncn2c1c(N)nc1cnc(C(=O)N3C[C@@H](F)C[C@@H]4Oc5cc(C(F)(F)F)ccc5[C@@H]43)cc12]

Example Ff-658: (4-amino-3-methylimidazo[1,5-a]pyrido[3,4-e]pyrazin-8-yl)((3S,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 4-((tertbutoxycarbonyl)amino)-3-methylimidazo[1,5-a]pyrido[3,4-e]pyrazine-8-carboxylic acid Ag-2 and (3S,4aS,9bS)-3-fluoro-7-(trifluoromethyl)-1,2,3,4,4a,9b-hexahydrobenzofuro[3,2-b]pyridine Ex-1. EZ/MS: m/z=487.0 $[M+H]^+$. $^1H$ NMR (400 MHz, Methanol-d4) δ 9.28 (s, 0.5H rotamer), 9.25 (s, 0.5H rotamer), 8.88 (s, 0.5H rotamer), 8.76 (s, 0.5H rotamer), 8.65 (s, 0.5H rotamer), 8.49 (s, 0.5H rotamer), 7.99 (d, J=7.9 Hz, 0.5H rotamer), 7.66 (d, J=7.8 Hz, 0.5H rotamer), 7.33 (dd, J=7.8, 1.5 Hz, 1H), 7.18 (s, 0.5H rotamer), 7.13 (s, 0.5H rotamer), 6.41 (d, J=8.3 Hz, 0.5H rotamer), 6.09 (d, J=8.6 Hz, 0.5H rotamer), 5.25 (d, J=7.8 Hz, 0.5H rotamer), 5.17-4.96 (m, 1H), 4.26 (dd, J=21.4, 16.0 Hz, 0.5H rotamer), 3.33 (s, 3H), 3.30-3.04 (m, 0.5H rotamer), 2.60-3.00 (m, 2H+0.5H rotamer), 2.37-2.03 (m, 1H).

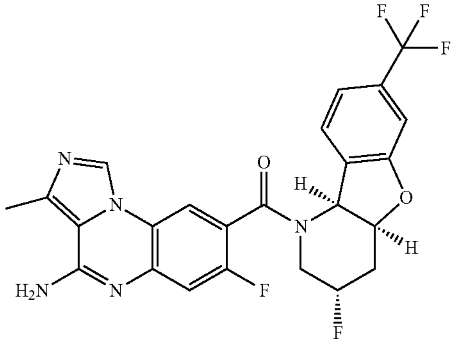 [SMILES: Cc1ncn2c1c(N)nc1cc(F)c(C(=O)N3C[C@@H](F)C[C@@H]4Oc5cc(C(F)(F)F)ccc5[C@@H]43)cc12]

Example Ff-659: (4-amino-7-fluoro-3-methylimidazo[1,5-a]quinoxalin-8-yl)((3S,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with starting with starting with 4-((tert-butoxycarbonyl)amino)-7-fluoro-3-methylimidazo[1,5-a]quinoxaline-8-carboxylic acid Af-4 and (3S,4aS,9bS)-3-fluoro-7-(trifluoromethyl)-1,2,3,4,4a,9b-hexahydrobenzofuro[3,2-b]pyridine Ex-1. EZ/MS: m/z=504.0 $[M+H]^+$. $^1H$ NMR (400 MHz, Methanol-d4) δ 9.24 (s, 0.3H minor rotamer), 9.13 (s, 0.7H major rotamer), 8.49 (brs, 1H), 8.31 (d, J=5.8 Hz, 1H), 7.63 (d, J=7.8 Hz, 1H), 7.54-7.36 (m, 1H), 7.37-7.21 (m, 1H), 7.20-7.03 (m, 1H), 6.37 (d, J=8.3 Hz, 1H), 5.50-5.65 (m, 0.3H minor rotamer) 5.29-5.17 (m, 1H), 4.95 (brs, 0.7H major rotamer), 3.50-3.75 (m, 1H), 3.25-3.07 (m, 1H), 3.00-2.75 (m, 3H), 2.34-2.08 (m, 1H).

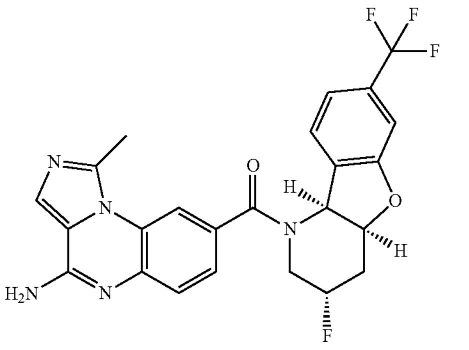 [SMILES: Cc1ncc2c(N)nc3ccc(C(=O)N4C[C@@H](F)C[C@@H]5Oc6cc(C(F)(F)F)ccc6[C@@H]54)cc3n12]

Example Ff-660: (4-amino-1-methylimidazo[1,5-a]quinoxalin-8-yl)((3S,4aS,9bS)-3-fluoro-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)-1-methylimidazo[1,5-a]quinoxaline-8-carboxylic acid Af-3 and (3S,4aS,9bS)-3-fluoro-7-(trifluoromethyl)-1,2,3,4,4a,9b-hexahydrobenzofuro[3,2-b]pyridine Ex-1. EZ/MS: m/z=486.0 $[M+H]^+$. $^1H$ NMR (400 MHz, Methanol-d4 δ 8.46-8.27 (m, 2H), 7.86-7.60 (m, 3H), 7.42-7.28 (m, 1H), 7.16 (s, 1H), 6.25 (s, 1H), 5.33-5.19 (m, 1H), 5.15-4.95 (m, 2H), 3.91 (brs, 1H), 3.12 (s, 3H), 2.88 (brs, 1H), 2.25-2.45 (m, 1H), 1.45-1.21 (m, 1H).

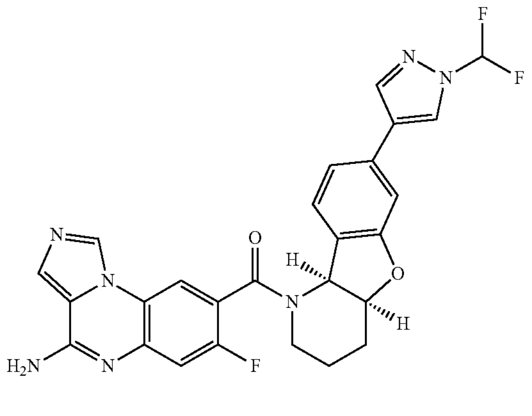 [SMILES: Nc1nc2cc(F)c(C(=O)N3CCC[C@@H]4Oc5cc(-c6cnn(C(F)F)c6)ccc5[C@@H]43)cc2n2cncc12]

Example Ff-661: (4-amino-7-fluoroimidazo[1,5-a]quinoxalin-8-yl)((4aS,9bS)-7-(1-(difluoromethyl)-1H-pyrazol-4-yl)-3,4,4a,9b-tetrahydrobenzofuro[3,2-b]pyridin-1(2H)-yl)methanone. Prepared using general procedure VI-F starting with 4-(tert-butoxycarbonylamino)-7-fluoro-imidazo[1,5-a]quinoxaline-8-carboxylic acid Af-1 and (4aS,9bS)-7-(1-(difluoromethyl)-1H-pyrazol-4-yl)-1,2,3,4,4a,9b-hexahydrobenzofuro[3,2-b]pyridine hydrochloride Ebd-7. EZ/MS: m/z=520.0 $[M+H]^+$. $^1H$ (400 MHz, Methanol-d4) δ 9.35-9.32 (m, 1H), 8.65-8.41 (m, 3H), 8.15-8.00 (m, 1H), 7.73-7.01 (m, 4H), 6.38 (d, J=8.7 Hz, 0.7H major rotamer), 5.56 (d, J=9.0 Hz, 0.3H minor rotamer), 5.16-5.13 (m, 0.7H major rotamer), 5.06 (brs, 0.3H minor rotamer), 4.50-4.35

(m, 0.3H minor rotamer), 3.35-3.50 (m, 0.7H major rotamer), 3.21-2.81 (m, 1H), 2.32-1.94 (m, 2H), 1.98-1.63 (m, 2H).

Example Ff-662: (4-amino-3-(methyl-d3)imidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl)methanone

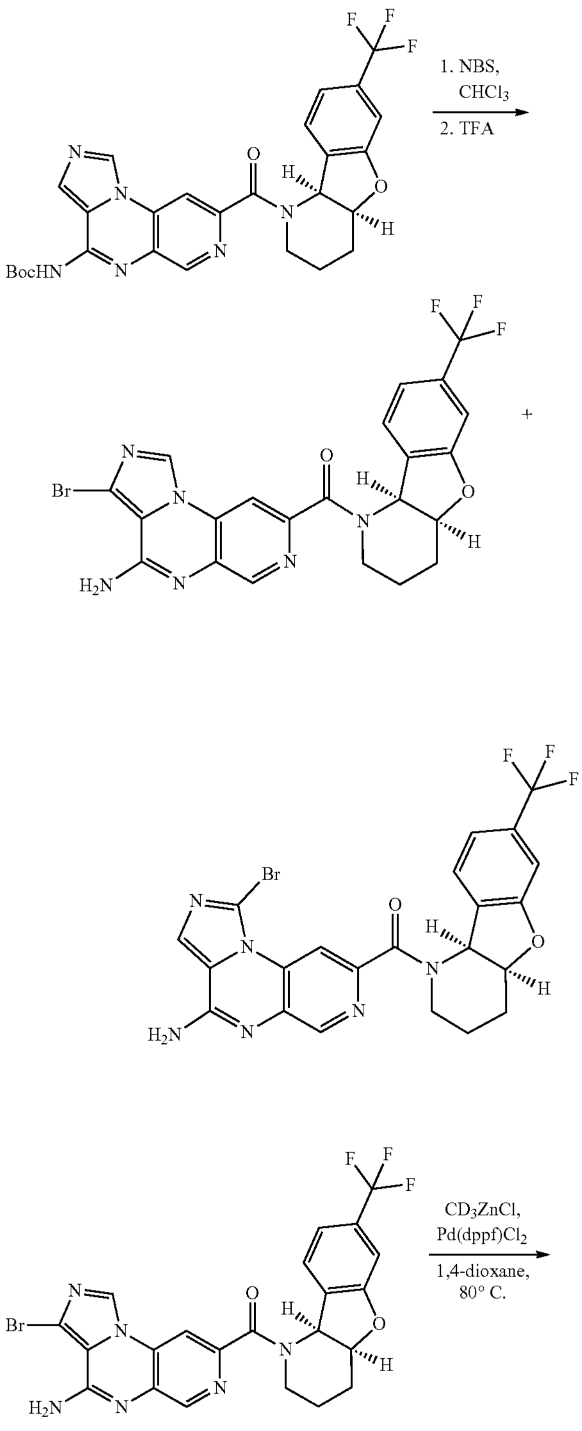

-continued

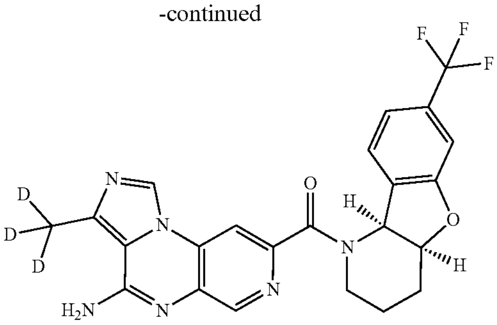

Example Ff-662

Step 1: tert-butyl (8-((4aS,9bS)-7-(trifluoromethyl)-1,2,3,4,4a,9b-hexahydrobenzofuro[3,2-b]pyridine-1-carbonyl) imidazo[1,5-a]pyrido[3,4-e]pyrazin-4-yl)-l2-azanecarboxylate. To a stirred solution of acid Af-1 (125 mg, 0.38 mmol), amine Ew-1 (106 mg, 0.380 mmol), and PyBrOP (230 mg, 0.493 mmol) in DMAc (3.0 mL) was added DIPEA (0.35 mL, 1.92 mmol). The mixture was stirred at room temperature overnight, then diluted with EtOAc and washed twice with 5% LiCl twice, saturated sodium bicarbonate twice, and brine once. The organic extract was dried over sodium sulfate and concentrated under reduced pressure. The crude residue was purified by flash chromatography (0-10% MeOH/EtOAc) to afford the desired product. ES/MS: m/z=555.0 [M+H+].

Step 1. (4-amino-3-bromoimidazo[1,5-a]pyrido[3,4-e] pyrazin-8-yl)((4aS,9bS)-7-(trifluoromethyl)-3,4,4a,9b-tetrahydrobenzofuro[3,2-b]pyridin-1(2H)-yl)methanone, (4-amino-1-bromoimidazo[1,5-a]pyrido[3,4-e]pyrazin-8-yl) ((4aS,9bS)-7-(trifluoromethyl)-3,4,4a,9b-tetrahydrobenzofuro[3,2-b]pyridin-1(2H)-yl)methanone. A stirred solution of tert-butyl (8-((4aS,9bS)-7-(trifluoromethyl)-1,2,3,4,4a,9b-hexahydrobenzofuro[3,2-b]pyridine-1-carbonyl)imidazo [1,5-a]pyrido[3,4-e]pyrazin-4-yl)-12-azanecarboxylate (prepared following step 1 of general procedure VI-F starting with Af-1 and Ew-1, 237 mg, 0.43 mmol) in $CHCl_3$ (4.0 mL) was cooled to 0° C. N-bromosuccinimide (76 mg, 0.43 mmol) was added, then the reaction mixture was warmed to room temperature and allowed to stir for 48 hours. The reaction mixture was diluted with a further 2.0 mL of $CHCl_3$ and TFA (0.65 mL, 8.6 mmol) was added. The reaction mixture was concentrated to dryness, and the crude residue was purified by preparative HPLC to afford the desired products. (4-amino-3-bromoimidazo[1,5-a]pyrido[3,4-e] pyrazin-8-yl)((4aS,9bS)-7-(trifluoromethyl)-3,4,4a,9b-tetrahydrobenzofuro[3,2-b]pyridin-1(2H)-yl)methanone. Peak 2 ES/MS: m/z=532.8 $[M+H]^+$. $^1$H NMR (400 MHz, Methanol-d4) δ 9.20 (d, J=10.4 Hz, 1H), 8.78 (d, J=15.0 Hz, 1H), 8.58-8.35 (m, 1H), 7.93-7.53 (m, 1H), 7.29 (d, J=7.9 Hz, 1H), 7.12 (d, J=19.2 Hz, 1H), 6.22 (dd, J=118.1, 9.1 Hz, 1H), 5.11 (d, J=61.2 Hz, 1H), 4.40 (s, 1H), 3.78 (s, 1H), 2.88 (d, J=73.0 Hz, 1H), 2.03 (d, J=60.1 Hz, 2H), 1.75 (s, 1H). (4-amino-1-bromoimidazo[1,5-a]pyrido[3,4-e]pyrazin-8-yl) ((4aS,9bS)-7-(trifluoromethyl)-3,4,4a,9b-tetrahydrobenzofuro[3,2-b]pyridin-1(2H)-yl)methanone. Peak 1. ES/MS: m/z=532.8 $[M+H]^+$. $^1$H NMR (400 MHz, Methanol-d4) δ 9.38 (d, J=33.1 Hz, 0.5H rotamer), 9.09 (d, J=37.8 Hz, 0.5H rotamer), 8.83 (s, 1H), 8.16 (d, J=15.3 Hz, 1H), 7.75 (d, J=103.0 Hz, 1H), 7.30 (d, J=7.8 Hz, 1H), 7.13 (s, 1H), 6.26 (d, J=71.0 Hz, 1H), 5.12 (d, J=54.3 Hz, 1H), 4.42 (s, 1H), 3.89 (s, 1H), 2.90 (d, J=68.7 Hz, 1H), 1.96 (s, 2H), 1.75 (d, J=25.2 Hz, 1H).

Step 2. (4-amino-3-(methyl-d3)imidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl)methanone. (4-amino-3-bromoimidazo[1,5-a]pyrido[3,4-e]pyrazin-8-yl) ((4aS,9bS)-7-(trifluoromethyl)-3,4,4a,9b-tetrahydrobenzofuro[3,2-b]pyridin-1(2H)-yl)methanone (18 mg, 0.028 mmol) and Pd(dppf)$Cl_2$ (2.1 mg, 0.0028 mmol) were dissolved in 1,4-dioxane (1.0 mL). The solution was degassed, and 0.5 M (methyl-d3)zinc chloride (0.14 mmol, 0.28 mL) was added. The reaction mixture was heated to 80° C. for 3 hours, then cooled to room temperature. Twice, an additional aliquot of 0.5 M (methyl-d3)zinc chloride (0.284 mmol, 0.58 mL) was added, and the reaction mixture was heated to 80° C. for 3 hours, then cooled to room temperature. The reaction mixture was diluted with MeOH and filtered. The crude residue was concentrated under reduced pressure and purified by preparative HPLC to afford the desired product. ES/MS: m/z=472.0 $[M+H]^+$. $^1$H NMR (400 MHz, Methanol-d) δ 9.26 (s, 1H), 8.81 (s, 0.5H rotamer), 8.79 (s, 0.5H rotamer) 8.55 (s, 0.5H rotamer), 8.46 (s, 0.5H rotamer), 7.83 (d, J=7.7 Hz, 0.5H rotamer), 7.60 (d, J=7.6 Hz, 0.5H rotamer), 7.28 (s, 0.5H rotamer), 7.26 (s, 0.5H rotamer) 7.15 (s, 0.5H rotamer), 7.11 (s, 0.5H rotamer), 6.35 (d, J=8.6 Hz, 0.5H rotamer), 5.99 (d, J=9.0 Hz, 0.5H rotamer), 5.18 (s, 0.5H rotamer), 5.02 (s, 0.5H rotamer), 4.40 (s, 0.5H rotamer), 3.74 (s, 0.5H rotamer), 2.96 (s, 0.5H rotamer), 2.79 (s, 0.5H rotamer), 2.27-1.60 (m, 4H).

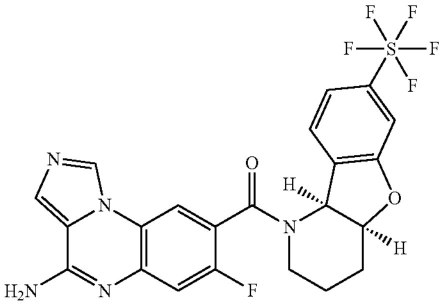 [SMILES: Nc1nc2cc(F)c(C(=O)N3CCC[C@@H]4Oc5cc(S(F)(F)(F)(F)F)ccc5[C@@H]43)cc2n2cncc12]

Example Ff-663: (4-amino-7-fluoroimidazo[1,5-a]quinoxalin-8-yl)((4aS,9bS)-7-(pentafluoro-16-sulfaneyl)-3,4,4a,9b-tetrahydrobenzofuro[3,2-b]pyridin-1(2H)-yl)methanone. Prepared following general procedure VI-F starting with 4-((tert-butoxycarbonyl)amino)-7-fluoroimidazo[1,5-a]quinoxaline-8-carboxylic acid Af-1 and (4aS,9bS)-7-(pentafluoro-16-sulfaneyl)-1,2,3,4,4a,9b-hexahydrobenzofuro [3,2-b]pyridine Ew-21. ES/MS: m/z=529.8 $[M+H]^+$. $^1$H NMR (400 MHz, MeOD) δ 9.31 (s, 0.3H, minor rotamer), 9.30 (s, 0.7H, major rotamer), 8.56 (s, 0.3H, minor rotamer), 8.46 (d, J=5.8 Hz, 0.7H, major rotamer), 8.42-8.35 (m, 1H), 7.59 (brs, 0.7H, major rotamer), 7.56-7.41 (m, 1H+0.3H minor rotamer), 7.34 (d, J=1.9 Hz, 0.7H, major rotamer), 7.27 (s, 0.3H, minor rotamer), 6.45 (d, J=8.8 Hz, 0.7H major rotamer), 5.66 (d, J=9.2 Hz, 0.3H, minor rotamer), 5.23 (dt, J=8.9, 4.5 Hz, 0.7H, major rotamer), 5.15 (s, 0.3H, minor rotamer), 4.58-4.40 (m, 0.3H, minor rotamer), 3.59-3.42 (m, 0.7H major rotamer), 3.14-2.97 (m, 0.7H, major rotamer), 2.93-2.78 (m, 0.3H, minor rotamer), 2.07 (brs, 2H), 1.91-1.60 (m, 2H).

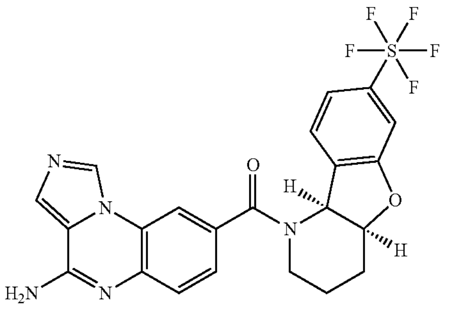 [SMILES: Nc1nc2ccc(C(=O)N3CCC[C@@H]4Oc5cc(S(F)(F)(F)(F)F)ccc5[C@@H]43)cc2n2cncc12]

Example Ff-664: (4-aminoimidazo[1,5-a]quinoxalin-8-yl)((4aS,9bS)-7-(pentafluoro-16-sulfaneyl)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (4aS,9bS)-7-(pentafluoro-16-sulfaneyl)-1,2,3,4,4a,9b-hexahydrobenzofuro[3,2-b]pyridine Ew-21. ES/MS: m/z=512.0 $[M+H]^+$. $^1H$ NMR (400 MHz, MeOD) δ 9.34 (s, 1H), 8.45 (s, 0.5H rotamer), 8.39 (s, 0.5H rotamer), 7.70 (s, 1H), 7.63 (d, J=8.4 Hz, 0.5H rotamer), 7.47 (dd, J=8.3, 2.0 Hz, 0.5H rotamer), 7.32 (s, 1H), 6.25 (brs, 1H), 5.20 (brs, 1H), 3.59 (brs, 1H), 3.00 (brs, 1H), 2.11 (brs, 2H), 1.92-1.81 (m, 1H), 1.81-1.61 (m, 1H), 0.99 (brs, 1H).

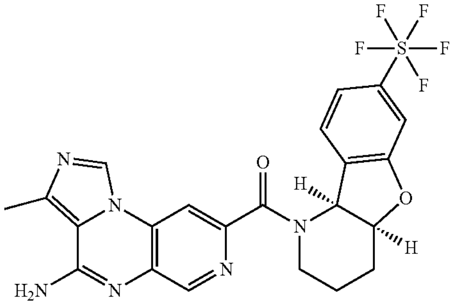 [SMILES: Cc1ncn2c1c(N)nc1cnc(C(=O)N3CCC[C@@H]4Oc5cc(S(F)(F)(F)(F)F)ccc5[C@@H]43)cc12]

Example Ff-665: (4-amino-3-methylimidazo[1,5-a]pyrido[3,4-e]pyrazin-8-yl)((4aS,9bS)-7-(pentafluoro-16-sulfaneyl)-3,4,4a,9b-tetrahydrobenzofuro[3,2-b]pyridin-1(2H)-yl)methanone. Prepared following general procedure VI-F starting with 4-((tert-butoxycarbonyl)amino)-3-methylimidazo[1,5-a]pyrido[3,4-e]pyrazine-8-carboxylic acid Ag-2 and (4aS,9bS)-7-(pentafluoro-16-sulfaneyl)-1,2,3,4,4a,9b-hexahydrobenzofuro[3,2-b]pyridine Ew-21. ES/MS: m/z=527.0 $[M+H]^+$. $^1H$ NMR (400 MHz, MeOD) δ 9.25 (s, 1H), 8.82 (s, 0.5H, rotamer), 8.79 (s, 0.5H, rotamer), 8.56 (s, 0.5H, rotamer), 8.47 (s, 0.5H, rotamer), 7.86 (d, J=8.2 Hz, 0.5H, rotamer), 7.61 (d, J=8.2 Hz, 0.5H, rotamer), 7.47 (d, J=2.0 Hz, 0.5H, rotamer), 7.45 (d, J=2.0 Hz, 0.5H, rotamer), 7.33 (s, 0.5H, rotamer), 7.28 (s, 0.5H, rotamer), 6.36 (d, J=8.7 Hz, 0.5H, rotamer), 6.03 (d, J=9.0 Hz, 0.5H, rotamer), 5.22 (s, 0.5H, rotamer), 5.06 (s, 0.5H, rotamer), 4.43 (s, 0.5H, rotamer), 3.77 (s, 0.5H, rotamer), 2.98 (d, J=9.9 Hz, 0.5H, rotamer), 2.81 (s, 0.5+1.5H, rotamer), 2.68 (s, 1.5H, rotamer), 2.25-1.70 (m, 3H).

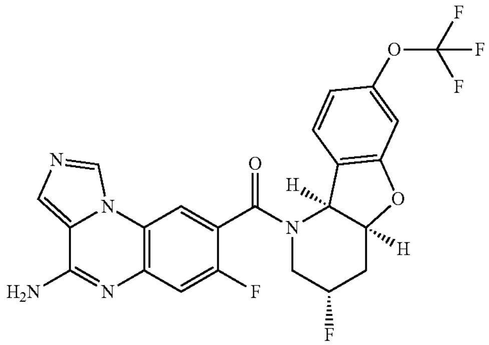 [SMILES: Nc1nc2cc(F)c(C(=O)N3C[C@@H](F)C[C@@H]4Oc5cc(OC(F)(F)F)ccc5[C@@H]43)cc2n2cncc12]

Example Ff-666: (4-amino-7-fluoroimidazo[1,5-a]quinoxalin-8-yl)((3S,4aS,9bS)-3-fluoro-7-(trifluoromethoxy)-3,4,4a,9b-tetrahydrobenzofuro[3,2-b]pyridin-1(2H)-yl) methanone. Prepared following general procedure VI-F starting with 4-((tert-butoxycarbonyl)amino)-7-fluoroimidazo[1,5-a]quinoxaline-8-carboxylic acid Af-1 and (3S,4aS,9bS)-3-fluoro-7-(trifluoromethoxy)-1,2,3,4,4a,9b-hexahydrobenzofuro[3,2-b]pyridine Ex-2. ES/MS: m/z=506.0 $[M+H]^+$. $^1H$ NMR (400 MHz, MeOD) δ 9.32 (s, 0.1H, minor rotamer), 9.21 (s, 0.9H, major rotamer), 8.55 (s, 0.1H, minor rotamer), 8.40 (d, J=5.8 Hz, 0.9H, major rotamer), 8.33 (s, 1H), 7.57 (d, J=8.2 Hz, 0.9H, major rotamer), 7.49 (s, 0.1H, minor rotamer), 7.42 (d, J=9.6 Hz, 0.9H, major rotamer), 7.36 (d, J=8.2 Hz, 0.1H, minor rotamer), 6.96 (d, J=8.2 Hz, 0.9H, major rotamer), 6.90 (s, 0.1H, minor rotamer), 6.83 (s, 0.9H, major rotamer), 6.78 (s, 0.1H, minor rotamer), 6.34 (d, J=8.2 Hz, 1H), 5.30-5.18 (m, 1H), 4.99 (s, 2H), 3.69 (dd, J=22.0, 15.8 Hz, 1H), 3.30-3.16 (m, 0.5H, rotamer), 3.05-2.75 (m, 0.5H, rotamer), 2.40-2.15 (m, 2H).

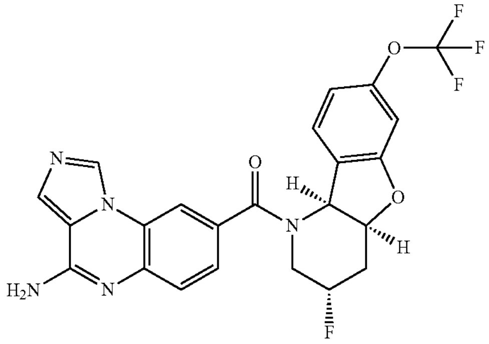 [SMILES: Nc1nc2ccc(C(=O)N3C[C@@H](F)C[C@@H]4Oc5cc(OC(F)(F)F)ccc5[C@@H]43)cc2n2cncc12]

Example Ff-667: (4-aminoimidazo[1,5-a]quinoxalin-8-yl)((3S,4aS,9bS)-3-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (3S,4aS,9bS)-3-fluoro-7-(trifluoromethoxy)-1,2,3,4,4a,9b-hexahydrobenzofuro[3,2-b]pyridine Ex-2. ES/MS: m/z=488.0 $[M+H]^+$. $^1H$ NMR (400 MHz, MeOD) δ 9.24 (s, 1H), 8.46 (s, 1H), 8.39 (s, 1H), 7.70 (q, J=8.6 Hz, 2H), 6.94 (d, J=8.3 Hz, 1H), 6.82 (s, 1H), 6.20 (s, 1H), 5.25 (d, J=7.4 Hz, 1H), 5.08 (s, 1H), 4.94 (s, 1H), 3.89 (brs, 2H), 2.94 (brs, 1H), 2.45-2.20 (m, 2H).

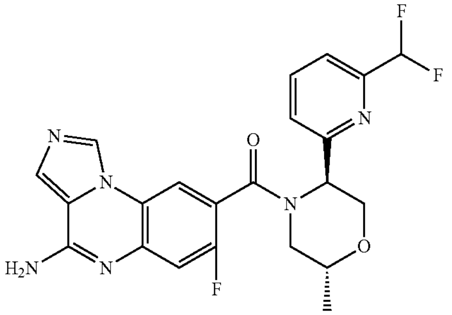 [SMILES: C[C@@H]1CN(C(=O)c2cc3c(cc2F)nc(N)c2cncn23)[C@@H](c2cccc(C(F)F)n2)CO1]

Example Ff-668: (4-amino-7-fluoroimidazo[1,5-a]quinoxalin-8-yl)((2R,5S)-5-(6-(difluoromethyl)pyridin-2-yl)-2-methylmorpholino)methanone. Prepared following general procedure VI-F starting with starting with starting with 4-(tert-butoxycarbonylamino)-7-fluoro-imidazo[1,5-a]quinoxaline-8-carboxylic acid Af-1 and (2R)-5-(6-(difluoromethyl)pyridin-2-yl)-2-methylmorpholine hydrochloride Eai-18. Isolated as the minor isomer and peak 1 by HPLC purification. ES/MS: m/z=457.0 $[M+H]^+$. $^1H$ NMR (400 MHz, Methanol-d4) δ 9.20 (s, 1H), 8.36 (s, 1H), 8.01 (s, 1H), 7.84-7.53 (m, 2H), 7.44 (d, J=10.9 Hz, 1H), 6.77 (t, J=55.2 Hz, 1H), 5.64 (s, 1H), 4.36 (d, J=4.4 Hz, 2H), 4.23-3.85 (m, 2H, major rotamer), 1.59-1.18 (m, 4H).

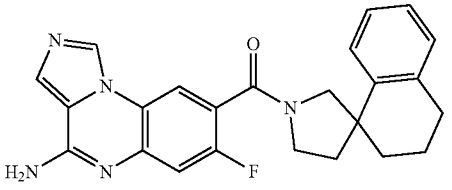 [SMILES: Nc1nc2cc(F)c(C(=O)N3CCC4(CCCc5ccccc54)C3)cc2n2cncc12]

Example Ff-669: (4-amino-7-fluoroimidazo[1,5-a]quinoxalin-8-yl)(3,4-dihydro-2H-spiro[naphthalene-1,3'-pyrrolidin]-1'-yl)methanone. Prepared following general procedure VI-F starting with 4-((tert-butoxycarbonyl)amino)-7-fluoroimidazo[1,5-a]quinoxaline-8-carboxylic acid Af-1 and commercial spiro[pyrrolidine-3,1'-tetralin] hydrochloride. ES/MS: m/z=416.0 $[M+H]^+$. $^1H$ NMR (400 MHz, $CD_3OD$) δ 9.05 (d, J=0.7 Hz, 0.5H, rotamer), 9.00 (d, J=0.8 Hz, 0.5H, rotamer), 8.27 (d, J=6.3 Hz, 0.5H, rotamer), 8.21 (d, J=6.3 Hz, 0.5H, rotamer), 7.96 (s, 0.5H, rotamer), 7.93 (s, 0.5H, rotamer), 7.50-7.30 (m, 1H), 7.28-7.03 (m, 4H), 4.08-3.58 (m, 4H), 3.56-3.38 (m, 1H), 2.87 (t, J=6.0 Hz, 1H), 2.84-2.68 (m, 1H), 2.28-2.50 (m, 1H), 2.22-1.58 (m, 4H).

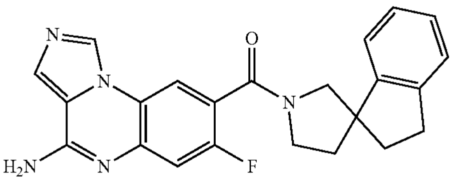 [SMILES: Nc1nc2cc(F)c(C(=O)N3CCC4(CCc5ccccc54)C3)cc2n2cncc12]

Example Ff-670: (4-amino-7-fluoroimidazo[1,5-a]quinoxalin-8-yl)(2,3-dihydrospiro[indene-1,3'-pyrrolidin]-1'-yl)methanone. Prepared following general procedure VI-F starting with 4-((tert-butoxycarbonyl)amino)-7-fluoroimidazo[1,5-a]quinoxaline-8-carboxylic acid Af-1 and commercial spiro[indane-1,3'-pyrrolidine] hydrochloride. ES/MS: m/z=402.0 $[M+H]^+$. $^1H$ NMR (400 MHz, $CD_3OD$) δ 9.06 (d, J=0.8 Hz, 0.5H, rotamer), 9.00 (d, J=0.8 Hz, 0.5H, rotamer), 8.27 (d, J=6.4 Hz, 0.5H, rotamer), 8.23 (d, J=6.3 Hz, 0.5H, rotamer), 7.96 (d, J=0.7 Hz, 0.5H, rotamer), 7.93 (d, J=0.7 Hz, 0.5H, rotamer), 7.40-7.11 (m, 5H), 4.00-3.91 (m, 1H), 3.87-3.76 (m, 1H), 3.69 (q, J=5.3, 4.0 Hz, 1H), 3.59 (d, J=10.8 Hz, 1H), 3.54-3.44 (m, 1H), 3.02 (t, J=7.2 Hz, 1H), 2.99-2.82 (m, 1H), 2.41-1.99 (m, 3H).

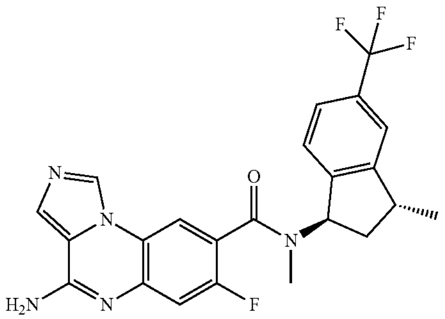 [SMILES: C[C@@H]1C[C@@H](N(C)C(=O)c2cc3c(cc2F)nc(N)c2cncn23)c2ccc(C(F)(F)F)cc21]

Example Ff-671: 4-amino-7-fluoro-N-methyl-N-((1R,3R)-3-methyl-5-(trifluoromethyl)-2,3-dihydro-1H-inden-1-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (1R,3R)—N,3-dimethyl-5-(trifluoromethyl)-2,3-dihydro-1H-inden-1-amine Ebw-2 (HATU was used instead of Pybrop). ES/MS: m/z=458.0 $[M+H]^+$. $^1H$ NMR (400 MHz, MeOD) δ 9.30 (s, 1H), 8.48 (d, J=5.9 Hz, 1H), 8.43-8.30 (m, 1H), 7.75-7.55 (m, 2H), 7.55-7.37 (m, 2H), 6.59-6.41 (m, 0.5H, rotamer), 5.44 (t, J=7.4 Hz, 0.5H, rotamer), 3.69-3.50 (m, 2H), 2.83 (s, 1.5H, rotamer), 2.71 (d, J=1.1 Hz, 1.5H, rotamer), 2.45-2.55 (m, 1H), 2.30-2.23 (m, 0.5H, rotamer), 2.07 (brs, 0.5H, rotamer), 1.40 (d, J=7.1 Hz, 1.5H, rotamer), 1.22 (d, J=7.1 Hz, 1.5H, rotamer).

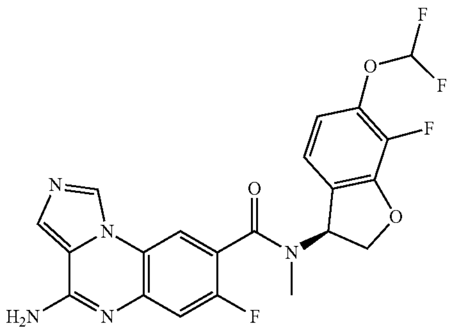 [SMILES: CN(C(=O)c1cc2c(cc1F)nc(N)c1cncn12)[C@@H]1COc2c1ccc(OC(F)F)c2F]

Example Ff-672: (S)-4-amino-N-(6-(difluoromethoxy)-7-fluoro-2,3-dihydrobenzofuran-3-yl)-7-fluoro-N-methylimidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)-6-(difluoromethoxy)-7-fluoro-N-methyl-2,3-dihydrobenzofuran-3-amine Ean-2 (HATU was used instead of Pybrop). ES/MS: m/z=462.0 $[M+H]^+$. $^1H$ NMR (400 MHz, MeOD) δ 9.25 (s, 1H), 8.44 (d, J=5.9 Hz, 1H), 8.36 (d, J=1.6 Hz, 1H), 7.49 (d, J=10.1 Hz, 0.5H, rotamer), 7.45 (d, J=9.8 Hz, 0.5H, rotamer), 7.22 (d, J=8.1 Hz, 0.5H, rotamer), 7.13 (d, J=8.3 Hz, 0.5H, rotamer), 6.97-6.89 (m, 1H), 6.87 (td, J=73.2, 7.5 Hz, 1H), 6.55 (dd, J=8.7, 3.5 Hz, 1H), 5.72-5.65 (m, 1H), 4.96 (dd, J=10.7, 8.8 Hz, 1H), 4.81 (dd, J=10.7, 3.6 Hz, 1H), 2.88 (s, 1.5H, rotamer), 2.75 (d, J=1.2 Hz, 1.5H, rotamer).

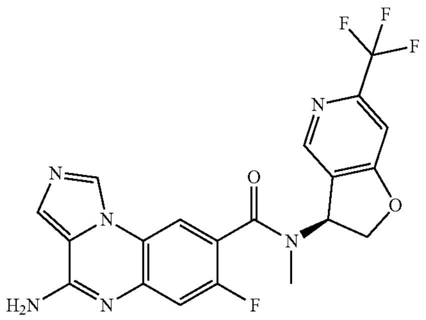 [SMILES: CN(C(=O)c1cc2c(cc1F)nc(N)c1cncn12)[C@@H]1COc2cc(C(F)(F)F)ncc21]

Example Ff-673: (S)-4-amino-7-fluoro-N-methyl-N-(6-(trifluoromethyl)-2,3-dihydrofuro[3,2-c]pyridin-3-yl)imidazo[1,5-a]quinoxaline-8-carboxamide. Prepared following general procedure VI-F starting with 4-((tert-butoxycarbonyl)amino)-7-fluoroimidazo[1,5-a]quinoxaline-8-carboxylic acid Af-1 and (S)—N-methyl-6-(trifluoromethyl)-2,3-dihydrofuro[3,2-c]pyridin-3-amine Ebv-1 (HATU was used instead of pybrop). ES/MS: m/z=447.0 $[M+H]^+$. $^1H$ NMR (400 MHz, MeOD) δ 9.27 (s, 1H), 8.64 (s, 0.7H, major rotamer), 8.56 (s, 0.3H, minor rotamer), 8.47 (d, J=5.8 Hz, 0.6H, minor rotamer), 8.41 (d, J=5.0 Hz, 1.4H, major rotamer), 7.55 (d, J=9.7 Hz, 0.3H, minor rotamer), 7.50 (d, J=9.7 Hz, 0.7H, major rotamer), 7.40 (d, J=9.2 Hz, 1H), 6.55 (dd, J=9.2, 4.0 Hz, 0.7H, major rotamer), 5.85 (t, J=6.7 Hz, 0.3H, minor rotamer), 5.04 (dd, J=10.8, 9.2 Hz, 0.7H, major rotamer), 4.95-4.90 (m, 0.3H, minor rotamer), 2.89 (s, 1H, minor rotamer), 2.84 (d, J=1.2 Hz, 2H, major rotamer).

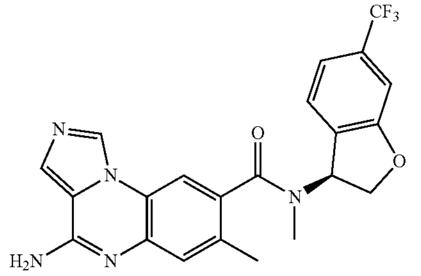 [SMILES: Cc1cc2nc(N)c3cncn3c2cc1C(=O)N(C)[C@@H]1COc2cc(C(F)(F)F)ccc21]

Example Ff-674: (S)-4-amino-N,7-dimethyl-N-(6-(trifluoromethyl)-2,3-dihydrobenzofuran-3-yl)imidazo[1,5-a]quinoxaline-8-carboxamide. Prepared following general procedure VI-F starting with 4-((tert-butoxycarbonyl)amino)-7-methylimidazo[1,5-a]quinoxaline-8-carboxylic acid Am-1 and (S)—N-methyl-6-(trifluoromethyl)-2,3-dihydrobenzofuran-3-amine; hydrochloride Eh-1. ES/MS: m/z=442.2 $[M+H]^+$. $^1H$ NMR (400 MHz, DMSO-$d_6$) δ 9.45 (s, 0.3H, minor rotamer), 9.33 (s, 0.7H, major rotamer), 8.57 (s, 0.3H, minor rotamer), 8.39 (s, 0.3H, minor rotamer), 8.38 (s, 0.7H, major rotamer), 8.29 (s, 0.7H, major rotamer), 7.78 (d, J=7.8 Hz, 0.3H, minor rotamer), 7.61 (s, 0.3H, minor rotamer), 7.50 (d, J=10.5 Hz, 0.7H, major rotamer), 7.46 (s, 0.7H, major rotamer), 7.42 (d, J=7.3 Hz, 0.3H, minor rotamer), 7.40-7.36 (m, 0.7H, major rotamer), 7.34 (d, J=8.8 Hz, 0.3H, minor rotamer), 7.31 (d, J=1.5 Hz, 0.7H, major rotamer), 7.25 (d, J=1.5 Hz, 0.3H, minor rotamer), 6.57-6.50 (m, 1H), 5.44 (s, 1H), 4.90 (dd, J=10.4, 9.2 Hz, 0.7H, major rotamer), 4.73 (dd, J=10.4, 4.2 Hz, 1H), 4.63 (t, J=10.1 Hz, 0.3H, minor rotamer), 2.73 (d, J=5.2 Hz, 2.1H, major rotamer), 2.35 (s, 2.1H, major rotamer), 2.33 (s, J=4.4 Hz, 0.9H, minor rotamer), 1.24 (d, J=3.0 Hz, 0.9H, minor rotamer).

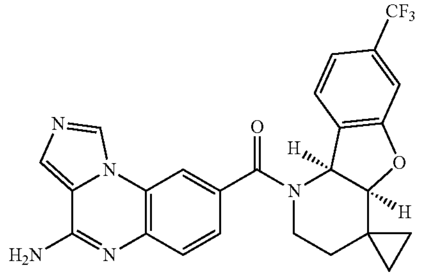 [SMILES: Nc1nc2ccc(C(=O)N3CCC4(CC4)[C@@H]4Oc5cc(C(F)(F)F)ccc5[C@@H]43)cc2n2cncc12]

Example Ff-675: (4-aminoimidazo[1,5-a]quinoxalin-8-yl)((4aS,9bS)-7-(trifluoromethyl)-2,3,4a,9b-tetrahydro-1H-spiro[benzofuro[3,2-b]pyridine-4,1'-cyclopropan]-1-yl)methanone. Prepared following general procedure VI-F starting with 4-((tert-butoxycarbonyl)amino)imidazo[1,5-a]quinoxaline-8-carboxylic acid Ae-1 and (4aS,9bS)-7-(trifluoromethyl)-2,3,4a,9b-tetrahydro-1H-spiro[benzofuro[3,2-b]pyridine-4,1'-cyclopropane]Ew-22. ES/MS: m/z=480.3 $[M+H]^+$. $^1H$ NMR (400 MHz, DMSO-$d_6$) δ 9.39 (s, 1H), 8.40 (s, 1H), 8.21 (s, 1H), 7.68 (d, J=7.1 Hz, 1H), 7.58 (d, J=15.9 Hz, 2H), 7.34 (d, J=7.7 Hz, 1H), 7.26 (s, 1H), 6.46-6.21 (m, 1H), 4.44 (s, 1H), 4.29-4.08 (m, 2H), 1.47 (s, 1H), 1.38 (d, J=12.3 Hz, 1H), 0.76 (s, 1H), 0.74-0.64 (m, 2H), 0.61-0.52 (m, 1H).

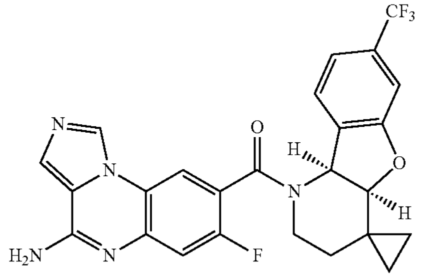 [SMILES: Nc1nc2cc(F)c(C(=O)N3CCC4(CC4)[C@@H]4Oc5cc(C(F)(F)F)ccc5[C@@H]43)cc2n2cncc12]

Example Ff-676: (4-amino-7-fluoroimidazo[1,5-a]quinoxalin-8-yl)((4aS,9bS)-7-(trifluoromethyl)-2,3,4a,9b-tetrahydro-1H-spiro[benzofuro[3,2-b]pyridine-4,1'-cyclopropan]-1-yl)methanone. Prepared following general procedure VI-F starting with 4-((tert-butoxycarbonyl)amino)-7-fluoroimidazo[1,5-a]quinoxaline-8-carboxylic acid Af-1 and (4aS,9bS)-7-(trifluoromethyl)-2,3,4a,9b-tetrahydro-1H-spiro[benzofuro[3,2-b]pyridine-4,1'-cyclopropane] Ew-22. ES/MS: m/z=498.3 $[M+H]^+$. $^1H$ NMR (400 MHz, DMSO-$d_6$) δ 9.36 (s, 0.5H rotamer), 9.34 (s, 0.5H rotamer) 8.62 (brs, 2H), 8.38 (d, J=6.2 Hz, 1H), 8.19 (s, 1H), 7.58 (brs, 1H), 7.44-7.20 (m, 3H), 6.43 (d, J=9.0 Hz, 0.5H rotamer), 5.55 (brs, 1H), 4.53 (d, J=9.0 Hz, 1H), 4.30 (brs, 1H), 3.25-3.50 (m, 1H), 2.97-3.03 (m, 1H), 1.75-2.00 (m, 1H), 1.22-1.35 (m, 1H), 0.83-0.70 (m, 2H), 0.69-0.53 (m, 2H).

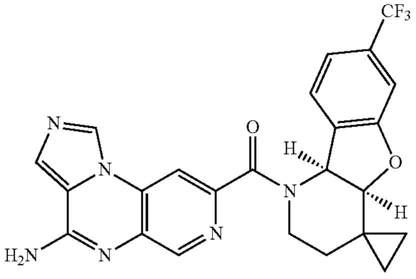 [SMILES: Nc1nc2cnc(C(=O)N3CCC4(CC4)[C@@H]4Oc5cc(C(F)(F)F)ccc5[C@@H]43)cc2n2cncc12]

Example Ff-677: (4-aminoimidazo[1,5-a]pyrido[3,4-e]pyrazin-8-yl)((4aS,9bS)-7-(trifluoromethyl)-2,3,4a,9b-tetrahydro-1H-spiro[benzofuro[3,2-b]pyridine-4,1'-cyclopropan]-1-yl)methanone. Prepared following general procedure VI-F starting with 4-((tert-butoxycarbonyl)amino)imidazo[1,5-a]pyrido[3,4-e]pyrazine-8-carboxylic acid Af-6 and (4aS,9bS)-7-(trifluoromethyl)-2,3,4a,9b-tetrahydro-1H-spiro[benzofuro[3,2-b]pyridine-4,1'-cyclopropane] Ew-22. ES/MS: m/z=481.3 $[M+H]^+$. $^1$H NMR (400 MHz, DMSO-$d_6$) δ 9.44 (s, 0.5H, rotamer), 9.41 (s, 0.5H, rotamer), 8.77 (s, 0.5H, rotamer), 8.69 (s, 0.5H, rotamer), 8.65 (s, 0.5H, rotamer), 8.54 (s, 0.5H, rotamer), 8.21 (s, 2H), 8.11 (s, 1H), 7.93 (d, J=7.8 Hz, 0.5H, rotamer), 7.57 (d, J=7.8 Hz, 0.5H, rotamer), 7.35 (d, J=1.5 Hz, 0.5H, rotamer), 7.36-7.30 (m, 0.5H, rotamer), 7.27 (s, 0.5H, rotamer), 7.23 (s, 0.5H, rotamer), 6.35 (d, J=8.8 Hz, 0.5H, rotamer), 6.02 (d, J=9.1 Hz, 0.5H, rotamer), 4.47 (d, J=8.9 Hz, 0.5H, rotamer), 4.27 (d, J=9.4 Hz, 0.5H, rotamer), 3.83-3.72 (m, 1H), 2.92 (m, J=14.3, 7.8 Hz, 0.5H, rotamer), 2.79-2.60 (m, 0.5H, rotamer), 1.90 (d, J=12.4 Hz, 1H), 1.50 (m, J=16.0, 8.6 Hz, 0.5H, rotamer), 1.38 (m, J=14.5, 7.6 Hz, 0.5H, rotamer), 0.79 (d, J=8.8 Hz, 1H), 0.71 (d, J=7.5 Hz, 1H), 0.59 (s, 1H), 0.56-0.48 (m, 1H).

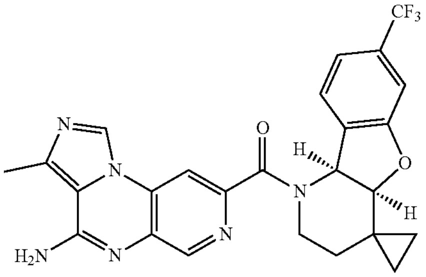 [SMILES: Cc1ncn2c1c(N)nc1cnc(C(=O)N3CCC4(CC4)[C@@H]4Oc5cc(C(F)(F)F)ccc5[C@@H]43)cc12]

Example Ff-678: (4-amino-3-methylimidazo[1,5-a]pyrido[3,4-e]pyrazin-8-yl)((4aS,9bS)-7-(trifluoromethyl)-2,3,4a,9b-tetrahydro-1H-spiro[benzofuro[3,2-b]pyridine-4,1'-cyclopropan]-1-yl)methanone. Prepared following general procedure VI-F starting with 4-((tert-butoxycarbonyl)amino)-3-methylimidazo[1,5-a]pyrido[3,4-e]pyrazine-8-carboxylic acid Ag-2 and (4aS,9bS)-7-(trifluoromethyl)-2,3,4a,9b-tetrahydro-1H-spiro[benzofuro[3,2-b]pyridine-4,1'-cyclopropane] Ew-22. ES/MS: m/z=495.3 $[M+H]^+$. $^1$H NMR (400 MHz, DMSO-$d_6$) δ 9.35 (s, 0.5H, rotamer), 9.32 (s, 0.5H, rotamer), 8.72 (s, 0.5H, rotamer), 8.65 (s, 0.5H, rotamer), 8.59 (s, 0.5H, rotamer), 8.48 (s, 0.5H, rotamer), 7.92 (d, J=7.8 Hz, 0.5H, rotamer), 7.67 (s, 2H), 7.57 (d, J=7.7 Hz, 0.5H, rotamer), 7.35 (d, J=1.5 Hz, 0.5H, rotamer), 7.33 (d, J=1.5 Hz, 0.5H, rotamer), 7.28 (s, 0.5H, rotamer), 7.23 (s, 0.5H, rotamer), 6.35 (d, J=8.9 Hz, 0.5H, rotamer), 6.03 (d, J=9.2 Hz, 0.5H, rotamer), 4.48 (d, J=8.8 Hz, 0.5H, rotamer), 4.28 (s, 0.5H, rotamer), 3.78 (s, 0.5H, rotamer), 2.91 (dt, J=14.3, 7.7 Hz, 0.5H, rotamer), 2.68 (s, 3H), 1.99 (t, J=5.3 Hz, 0.5H, rotamer), 1.90 (d, J=12.2 Hz, 0.5H, rotamer), 1.50 (q, J=9.3 Hz, 0.5H, rotamer), 1.37 (q, J=10.6, 9.8 Hz, 0.5H, rotamer), 0.84-0.76 (m, 1H), 0.71 (d, J=7.9 Hz, 1H), 0.59 (m, 1H), 0.58-0.47 (m, 1H).

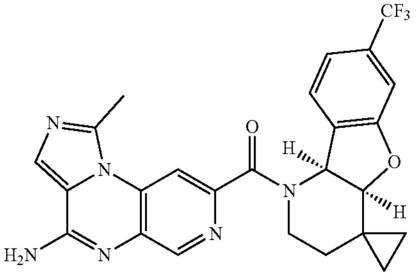 [SMILES: Cc1ncc2c(N)nc3cnc(C(=O)N4CCC5(CC5)[C@@H]5Oc6cc(C(F)(F)F)ccc6[C@@H]54)cc3n12]

Example Ff-679: (4-amino-1-methylimidazo[1,5-a]pyrido[3,4-e]pyrazin-8-yl)((4aS,9bS)-7-(trifluoromethyl)-2,3,4a,9b-tetrahydro-1H-spiro[benzofuro[3,2-b]pyridine-4,1'-cyclopropan]-1-yl)methanone. Prepared following general procedure VI-F starting with 4-((tert-butoxycarbonyl)amino)-1-methylimidazo[1,5-a]pyrido[3,4-e]pyrazine-8-carboxylic acid Ag-1 and (4aS,9bS)-7-(trifluoromethyl)-2,3,4a,9b-tetrahydro-1H-spiro[benzofuro[3,2-b]pyridine-4,1'-cyclopropane] Ew-22. ES/MS: m/z=495.3 $[M+H]^+$. $^1$H NMR (400 MHz, DMSO-$d_6$) δ 8.79 (s, 0.5H, rotamer), 8.73 (s, 0.5H, rotamer), 8.45 (s, 2H), 8.32 (s, 0.5H, rotamer), 8.26 (s, 0.5H, rotamer), 8.13 (s, 1H), 7.88-7.79 (m, 0.5H, rotamer), 7.62 (d, J=7.9 Hz, 0.5H, rotamer), 7.34 (d, J=1.5 Hz, 0.5H, rotamer), 7.32 (d, J=1.5 Hz, 0.5H, rotamer), 7.26 (s, 0.5H, rotamer), 7.24 (s, 0.5H, rotamer), 6.33 (d, J=8.7 Hz, 0.5H, rotamer), 6.08 (d, J=9.2 Hz, 0.5H, rotamer), 4.48 (d, J=8.9 Hz, 0.5H, rotamer), 4.28 (s, 0.5H, rotamer), 3.05 (s, 3H), 2.94 (m, J=16.4, 7.7 Hz, 0.5H, rotamer), 2.73-2.64 (m, 0.5H, rotamer), 2.01-1.85 (m, 1H), 1.53 (d, J=12.0 Hz, 0.5H, rotamer), 1.39 (s, 0.5H, rotamer), 0.75 (m, 2H), 0.58 (s, 2H).

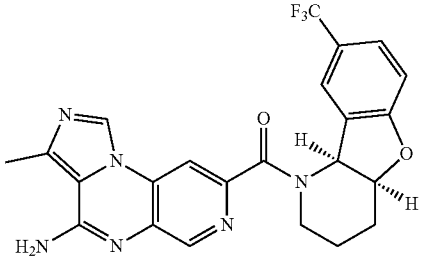 [SMILES: Cc1ncn2c1c(N)nc1cnc(C(=O)N3CCC[C@@H]4Oc5ccc(C(F)(F)F)cc5[C@@H]43)cc12]

Example Ff-680: (4-amino-3-methylimidazo[1,5-a]quinoxalin-8-yl)((4aS,9bS)-8-(trifluoromethyl)-3,4,4a,9b-tetrahydrobenzofuro[3,2-b]pyridin-1(2H)-yl)methanone. Prepared using general procedure VI-F with intermediates 4-((tert-butoxycarbonyl)amino)-3-methylimidazo[1,5-a]pyrido[3,4-e]pyrazine-8-carboxylic acid Ag-2 and (4aS,9bS)-8-(trifluoromethyl)-1,2,3,4,4a,9b-hexahydrobenzofuro[3,2-b]pyridine hydrochloride Ew-20. ES/MS: m/z=472.1 $[M+H]^+$. $^1$H NMR (400 MHz, Methanol-d4) δ 9.25 (s, 1H), 8.85-8.75 (m, 1H), 8.60-8.45 (m, 1H), 8.02 (s, 0.5H, rotamer), 7.74 (s, 0.5H, rotamer), 7.61 (d, J=8.8 Hz, 1H), 7.01 (dd, J=17.7, 8.7 Hz, 1H), 6.32 (d, J=8.7 Hz, 0.5H, rotamer), 6.00 (d, J=8.9 Hz, 0.5H, rotamer), 5.25-5.18 (m, 0.5H, rotamer), 5.09-5.01 (m, 0.5H, rotamer), 4.48-4.37 (m, 0.5H, rotamer), 3.85-3.74 (m, 0.5H, rotamer), 3.04-2.91 (m, 1H), 2.80 (s, 3H), 2.23-1.67 (m, 4H).

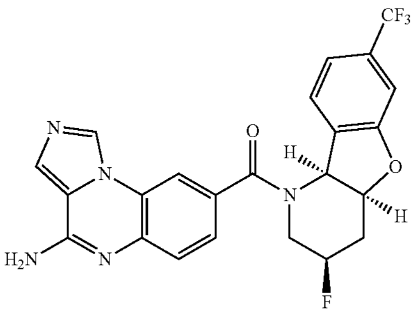 [SMILES: Nc1nc2ccc(C(=O)N3C[C@H](F)C[C@@H]4Oc5cc(C(F)(F)F)ccc5[C@@H]43)cc2n2cncc12]

Example Ff-681: (4-aminoimidazo[1,5-a]quinoxalin-8-yl)((3R,4aS,9bS)-3-fluoro-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and cis-3-fluoro-7-(trifluoromethyl)-1,2,3,4,4a,9b-hexahydrobenzofuro[3,2-b]pyridine Ev-5. Separation by chiral SFC (AD-H column, 45% EtOH, 60 mL/min) afforded the title compound (peak 2, RT=6.5 min). ES/MS: m/z=471.8 $[M+H]^+$. $^1H$ NMR (400 MHz, Methanol-d4) δ 9.42-9.22 (m, 1H), 8.54-8.30 (m, 2H), 7.81-7.60 (m, 3H), 7.42-7.26 (m, 1H), 7.14 (s, 1H), 6.17 (s, 1H), 5.31-4.99 (m, 2H), 4.01 (s, 1H), 2.86 (s, 1H), 2.68-2.30 (m, 2H).

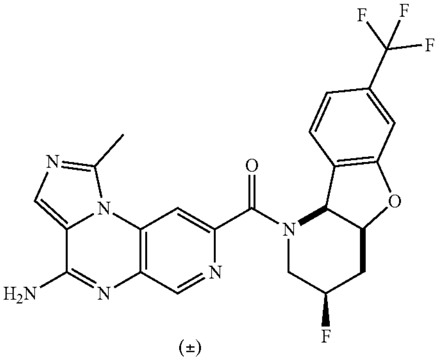

(±)

Example Ff-682: Rac-(4-amino-1-methylimidazo[1,5-a]pyrido[3,4-e]pyrazin-8-yl)((3R,4aS,9bS)-3-fluoro-7-(trifluoromethyl)-3,4,4a,9b-tetrahydrobenzofuro[3,2-b]pyridin-1(2H)-yl)methanone. Prepared according to general procedure VI-F starting with 4-((tert-butoxycarbonyl)amino)-1-methylimidazo[1,5-a]pyrido[3,4-e]pyrazine-8-carboxylic acid Ag-1 and cis-3-fluoro-7-(trifluoromethyl)-1,2,3,4,4a,9b-hexahydrobenzofuro[3,2-b]pyridine Ev-5 (TATU was used instead of PyBroP). EZ/MS: m/z=487.0 $[M+H]^+$. $^1H$ NMR (400 MHz, Methanol-d4) δ 8.86 (s, 1H), 8.55 (s, 1H), 8.31 (s, 1H), 7.74 (s, 1H), 7.33 (d, J=7.9 Hz, 1H), 7.18 (s, 1H), 6.19 (s, 1H), 5.50-5.40 (m, 1H), 5.24 (brs, 1H), 3.50 (brs, 1H), 3.21-3.11 (m, 3H), 2.68 (s, 1H), 1.96 (s, 1H), 1.31 (s, 1H).

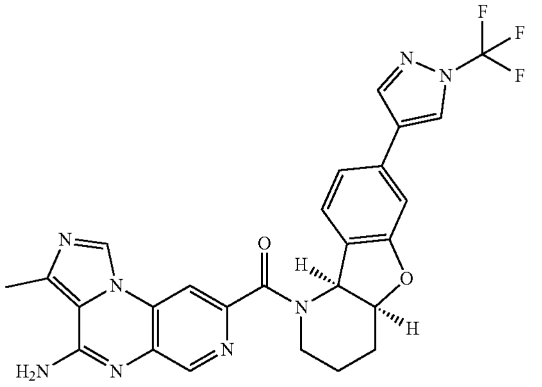 [SMILES: Cc1ncn2c1c(N)nc1cnc(C(=O)N3CCC[C@@H]4Oc5cc(-c6cnn(C(F)(F)F)c6)ccc5[C@@H]43)cc12]

Example Ff-683: (4-amino-3-methylimidazo[1,5-a]pyrido[3,4-e]pyrazin-8-yl)((4aS,9bS)-7-(1-(trifluoromethyl)-1H-pyrazol-4-yl)-3,4,4a,9b-tetrahydrobenzofuro[3,2-b]pyridin-1(2H)-yl)methanone. Prepared according to general procedure VI-F starting with 4-((tert-butoxycarbonyl)amino)-3-methylimidazo[1,5-a]pyrido[3,4-e]pyrazine-8-carboxylic acid Ag-2 and (4aS,9bS)-7-(1-(trifluoromethyl)-1H-pyrazol-4-yl)-1,2,3,4,4a,9b-hexahydrobenzofuro[3,2-b]pyridine hydrochloride Ebd-6 (TATU was used instead of PyBroP). EZ/MS: m/z=535.0 $[M+H]^+$. $^1H$ NMR (400 MHz, Methanol-$d_4$) δ 9.20 (s, 1H), 8.79 (s, 0.5H rotamer), 8.75 (0.5H, rotamer), 8.60 (s, 1H), 8.51 (s, 0.5H rotamer), 8.42 (s, 0.5H rotamer), 8.23 (s, 1H), 7.67 (s, 0.5H rotamer), 7.49 (s, 0.5H rotamer), 7.30 (s, 0.5H rotamer), 7.28 (s, 0.5H rotamer), 7.19 (s, 0.5H rotamer), 7.14 (s, 0.5H rotamer), 6.29 (s, 0.5H rotamer), 5.94 (s, 0.5H rotamer), 5.13 (brs, 1H), 4.96 (brs, 1H), 4.36 (brs, 1H), 3.70 (brs, 1H), 3.01 (brs, 1H), 2.79 (s, 3H), 2.27-1.60 (m, 2H).

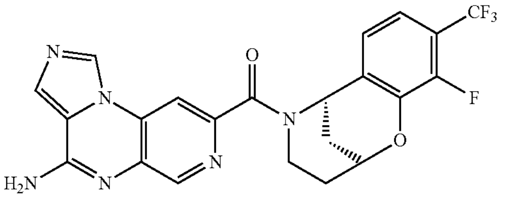

Example Ff-684: (4-aminoimidazo[1,5-a]pyrido[3,4-e]pyrazin-8-yl)((2S,6R)-10-fluoro-9-(trifluoromethyl)-3,4-dihydro-2H-2,6-methanobenzo[b][1,5]oxazocin-5(6H)-yl)methanone. Prepared using general procedure VI-F starting with 4-((tert-butoxycarbonyl)amino)imidazo[1,5-a]pyrido[3,4-e]pyrazine-8-carboxylic acid Af-6 and (2S,6R)-10-fluoro-9-(trifluoromethyl)-3,4,5,6-tetrahydro-2H-2,6-methanobenzo[b][1,5]oxazocine Ebi-8. ES/MS: m/z=473.2 $[M+H]^+$. $^1H$ NMR (400 MHz, DMSO-$d_6$) δ 9.40 (s, 0.5H rotamer), 9.38 (s, 0.5H rotamer), 8.82 (s, 0.5H rotamer), 8.66 (s, 0.5H rotamer), 8.61 (s, 0.5H rotamer), 8.51 (s, 0.5H rotamer), 8.33 (brs, 2H), 8.14 (s, 0.5H rotamer), 8.13 (s, 0.5H rotamer), 7.31-7.15 (m, 2H), 5.99 (s, 0.5H rotamer), 5.46 (s, 0.5H rotamer), 5.01 (s, 1H), 4.39 (dd, J=14.3, 6.4 Hz, 0.5H rotamer), 3.00-2.86 (m, 0.5H rotamer), 2.74-2.58 (m, 0.5H rotamer), 2.38-2.09 (m, 2H+0.5H rotamer), 2.09-1.90 (m, 2H).

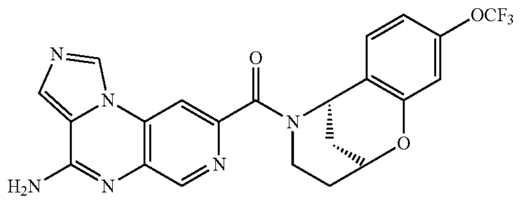

Example Ff-685: (4-aminoimidazo[1,5-a]pyrido[3,4-e]pyrazin-8-yl)((2S,6R)-9-(trifluoromethoxy)-3,4-dihydro-2H-2,6-methanobenzo[b][1,5]oxazocin-5(6H)-yl)methanone. Prepared using general procedure VI-F starting with 4-((tert-butoxycarbonyl)amino)imidazo[1,5-a]pyrido[3,4-e]pyrazine-8-carboxylic acid Af-6 and (2S,6R)-9-(trifluoromethoxy)-3,4,5,6-tetrahydro-2H-2,6-methanobenzo[b][1,5]oxazocine Ebi-6. ES/MS: m/z=471.2 $[M+H]^+$. $^1H$ NMR (400 MHz, DMSO-$d_6$) δ 9.41 (s, 0.5H rotamer), 9.39 (s, 0.5H rotamer), 8.83 (s, 0.5H rotamer), 8.66 (s, 0.5H rotamer), 8.61 (s, 0.5H rotamer), 8.51 (s, 0.5H rotamer), 8.44 (brs, 2H), 8.17 (s, 0.5H rotamer), 8.15 (s, 0.5H rotamer), 7.34 (d, J=8.3 Hz, 0.5H rotamer), 7.24 (d, J=8.3 Hz, 0.5H rotamer), 7.02-6.79 (m, 2H), 5.91 (s, 0.5H rotamer), 5.30 (s, 0.5H rotamer), 4.85 (s, 1H), 4.37 (dd, J=14.1, 6.3 Hz, 0.5H rotamer), 3.88-3.75 (m, 0.5H rotamer), 3.00-2.82 (m, 0.5H), 2.73-2.56 (m, 0.5H), 2.28-2.07 (m, 2H), 1.99-1.84 (m, 2H).

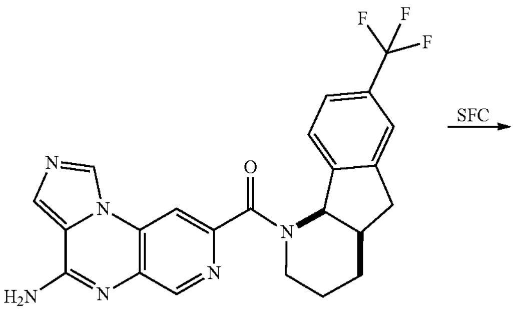

(±)
Example Ff-250

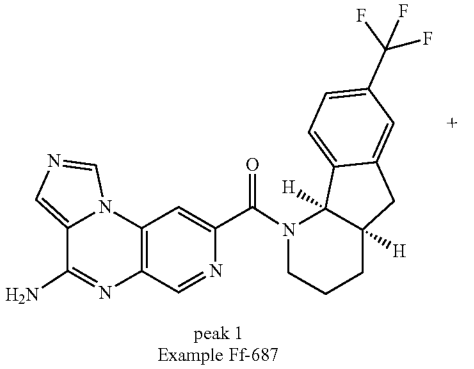

peak 1
Example Ff-687

+

-continued

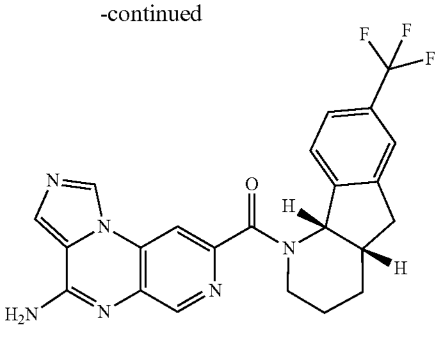

peak 2

Example Ff-687: (4-aminoimidazo[1,5-a]pyrido[3,4-e]pyrazin-8-yl)((4aR,9bR)-7-(trifluoromethyl)-2,3,4,4a,5,9b-hexahydro-1H-indeno[1,2-b]pyridin-1-yl)methanone. Prepared following general procedure VI-F using 4-((tert-butoxycarbonyl)amino)imidazo[1,5-a]pyrido[3,4-e]pyrazine-8-carboxylic acid Af-6 and (4aR,9bR)-7-(trifluoromethyl)-2,3,4,4a,5,9b-hexahydro-1H-indeno[1,2-b]pyridine Eax-1. The isomers were separated by SFC ( ). The desired product was isolated as peak 1 (Column AD-H, 5 μm 21×250 mm, 40° C., 100 bar, 35% EtOH, RT=7 min) ES/MS: m/z=453.2 $[M+H]^+$. $^1H$ NMR (400 MHz, DMSO-$d_6$) δ 9.40 (s, 0.5H rotamer), 9.37 (s, 0.5H rotamer), 8.76 (s, 0.5H rotamer), 8.61 (s, 0.5H rotamer), 8.60 (s, 0.5H rotamer), 8.58 (s, 0.5H rotamer), 8.27 (brs, 2H), 8.14 (s, 0.5H rotamer), 8.10 (s, 0.5H rotamer), 7.70 (s, 0.5H rotamer), 7.66-7.57 (m, 1H+0.5H rotamer), 7.34 (d, J=7.7 Hz, 0.5H rotamer), 6.10 (d, J=6.7 Hz, 0.5H rotamer), 5.45 (d, J=6.3 Hz, 0.5H rotamer), 4.55 (d, J=13.1 Hz, 0.5H rotamer), 3.79 (d, J=13.5 Hz, 0.5H rotamer), 3.25-3.14 (m, 0.5H rotamer), 2.90 (dd, J=15.8, 6.0 Hz, 0.5H rotamer), 2.85-2.32 (m, 2H), 1.87-1.35 (m, 3H), 1.17-0.93 (m, 1H).

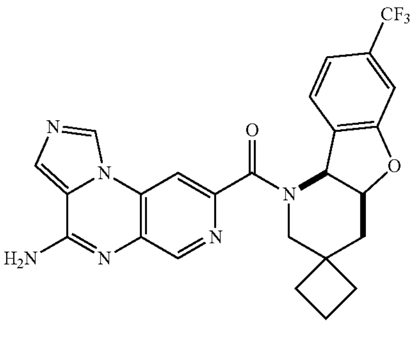 [SMILES: Nc1nc2cnc(C(=O)N3CC4(CCC4)C[C@@H]4Oc5cc(C(F)(F)F)ccc5[C@@H]43)cc2n2cncc12]

Example Ff-688: Rac-(4-aminoimidazo[1,5-a]pyrido[3,4-e]pyrazin-8-yl)((4aS,9bS)-7-(trifluoromethyl)-4a,9b-dihydro-2H-spiro[benzofuro[3,2-b]pyridine-3,1'-cyclobutan]-1(4H)-yl)methanone. Prepared following general procedure VI-F starting with 4-((tert-butoxycarbonyl)amino)imidazo[1,5-a]pyrido[3,4-e]pyrazine-8-carboxylic acid Af-6 and cis-7-(trifluoromethyl)-1,4,4a,9b-tetrahydro-2H-spiro[benzofuro[3,2-b]pyridine-3,1'-cyclobutane] Eba-7. ES/MS: m/z=495.0 $[M+H]^+$. $^1H$ NMR (400 MHz, Chloroform-d) δ 11.11 (s, 1H), 8.97 (s, 1H), 8.47 (s, 1H), 8.39 (s, 1H), 7.69 (d, J=6.9 Hz, 0.5H, rotamer), 7.45 (t, J=6.7 Hz, 0.50H, rotamer), 7.27-7.18 (m, 1H), 7.06 (d, J=5.5 Hz, 0.5H, rotamer), 7.01 (d, J=5.6 Hz, 0.5H, rotamer), 6.72 (s, 2H), 6.29 (d, J=7.1 Hz, 0.5H, rotamer), 6.01 (d, J=7.2 Hz, 0.5H, rotamer), 5.14-4.99 (m, 0.5H, rotamer), 4.86 (t, J=7.3 Hz, 0.5H, rotamer), 4.71-4.77 (m, 0.5H, rotamer), 4.25-4.32 (m, 0.5H, rotamer), 3.00-2.82 (m, 0.5H, rotamer), 2.68-2.62 (m, 0.5H, rotamer), 2.21-2.07 (m, 2H), 1.94 (m, 5H).

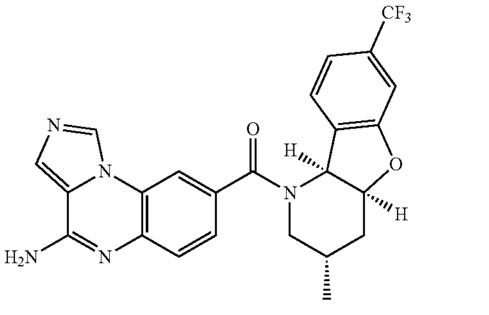 [SMILES: C[C@H]1C[C@@H]2Oc3cc(C(F)(F)F)ccc3[C@@H]2N(C(=O)c2ccc3nc(N)c4cncn4c3c2)C1]

Example Ff-689: (4-aminoimidazo[1,5-a]quinoxalin-8-yl)((3S,4aS,9bS)-3-methyl-7-(trifluoromethyl)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (3S)-3-methyl-7-(trifluoromethyl)-1,2,3,4,4a,9b-hexahydrobenzofuro[3,2-b]pyridine Eba-6. The isomers were separated using SFC (AD-H 4.6×100 mm 5 mic, 40° C., 45% MeOH co-solvent, 3 mL/min). The title product was isolated as peak 1, RT: 2.54 min. ES/MS: m/z=468.3 $[M+H]^+$. $^1$H NMR (400 MHz, DMSO-$d_6$) δ 9.45 (s, 1H), 8.49 (s, 1H), 8.38 (s, 1H), 7.66 (d, J=7.7 Hz, 1H), 7.60 (d, J=7.9 Hz, 2H), 7.31 (d, J=7.6 Hz, 1H), 7.22 (s, 1H), 6.37 (s, 1H), 5.27 (d, J=9.3 Hz, 1H), 2.05-1.99 (m, 1H), 2.01-1.95 (m, 1H), 1.83 (d, J=13.0 Hz, 1H), 1.72-1.58 (m, 2H), 0.87 (s, 3H).

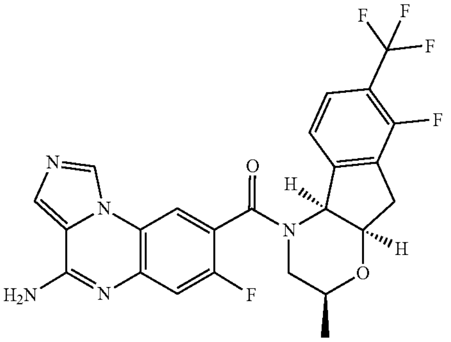 [SMILES: C[C@H]1CN(C(=O)c2cc3c(cc2F)nc(N)c2cncn23)[C@H]2c3ccc(C(F)(F)F)c(F)c3C[C@H]2O1]

Example Ff-690: (4-amino-7-fluoroimidazo[1,5-a]quinoxalin-8-yl)((2S,4aS,9aR)-8-fluoro-2-methyl-7-(trifluoromethyl)-2,3,9,9a-tetrahydroindeno[2,1-b][1,4]oxazin-4(4aH)-yl)methanone. Prepared following general procedure VI-F starting with 4-((tert-butoxycarbonyl)amino)-7-chloroimidazo[1,5-a]quinoxaline-8-carboxylic acid Af-1 and (2S,4aS,9aR)-8-fluoro-2-methyl-7-(trifluoromethyl)-2,3,4,4a,9,9a-hexahydroindeno[2,1-b][1,4]oxazine hydrochloride Eaz-7. ES/MS: m/z=504.0 $[M+H]^+$. $^1$H NMR (400 MHz, MeOD) δ 9.41-9.14 (m, 1H), 8.54 (dd, J=13.1, 5.9 Hz, 1H), 8.37-8.29 (m, 1H), 7.66 (q, J=8.4 Hz, 1H), 7.53-7.41 (m, 1H), 7.39-7.16 (m, 1H), 6.07 (s, 0.7H, major rotamer), 5.13 (s, 0.3H, minor rotamer), 4.67-4.46 (m, 1H), 3.73 (s, 1H), 3.43 (d, J=13.1 Hz, 1H), 3.29-2.96 (m, 2H), 2.84 (t, J=12.2 Hz, 0.7H, major rotamer), 2.57 (dd, J=13.4, 10.6 Hz, 0.3H, minor rotamer), 1.16 (d, J=6.3 Hz, 0.9H, minor rotamer), 1.00 (d, J=6.2 Hz, 2.1H, major rotamer).

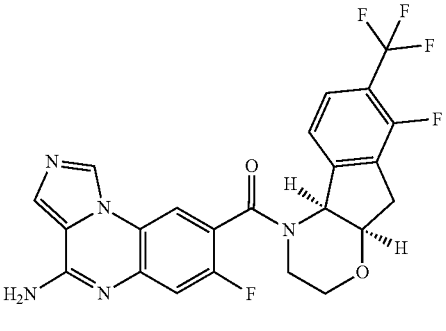 [SMILES: Nc1nc2cc(F)c(C(=O)N3CCO[C@@H]4Cc5c(ccc(C(F)(F)F)c5F)[C@@H]43)cc2n2cncc12]

Example Ff-691: (4-amino-7-fluoroimidazo[1,5-a]quinoxalin-8-yl)((4aS,9aR)-8-fluoro-7-(trifluoromethyl)-2,3,9,9a-tetrahydroindeno[2,1-b][1,4]oxazin-4(4aH)-yl)methanone. Prepared following general procedure VI-F starting with 4-((tert-butoxycarbonyl)amino)-7-chloroimidazo[1,5-a]quinoxaline-8-carboxylic acid Af-1 and 4aS,9aR)-8-fluoro-7-(trifluoromethyl)-2,3,4,4a,9,9a-hexahydroindeno[2,1-b][1,4]oxazine hydrochloride Eaz-6. ES/MS: m/z=490.0 $[M+H]^+$. $^1$H NMR (400 MHz, MeOD) δ 9.44-9.17 (m, 1H), 8.62-8.53 (m, 1H), 8.42-8.34 (m, 1H), 7.67 (q, J=8.4 Hz, 1H), 7.56-7.44 (m, 1H), 7.41-7.19 (m, 1H), 6.09 (s, 0.8H, major rotamer), 5.16 (s, 0.2H, minor rotamer), 4.65-4.41 (m, 1H), 3.90 (dd, J=11.8, 3.2 Hz, 0.2H, minor rotamer), 3.77-3.61 (m, 1.8H), 3.46 (d, J=13.4 Hz, 1H), 3.25 (d, J=4.3 Hz, 1H), 3.18-3.09 (m, 1H), 3.05-2.85 (m, 1H).

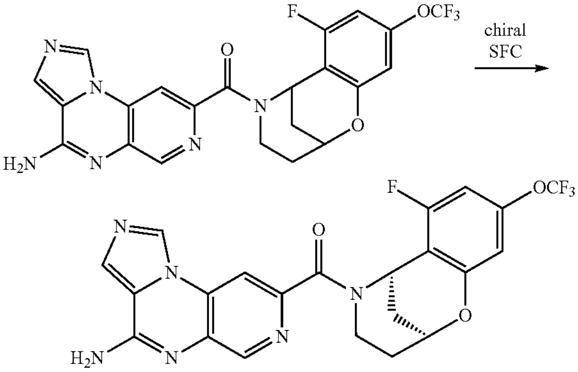

Example Ff-692

Example Ff-692: (4-aminoimidazo[1,5-a]pyrido[3,4-e]pyrazin-8-yl)((2S,6R)-7-fluoro-9-(trifluoromethoxy)-3,4-dihydro-2H-2,6-methanobenzo[b][1,5]oxazocin-5(6H)-yl)methanone. Prepared using general procedure VI-F starting with 4-((tert-butoxycarbonyl)amino)imidazo[1,5-a]pyrido[3,4-e]pyrazine-8-carboxylic acid Af-6 and rac-(2S,6R)-7-fluoro-9-(trifluoromethoxy)-3,4,5,6-tetrahydro-2H-2,6-methanobenzo[b][1,5]oxazocine Ebi-13. Isolated as peak 1 after chiral separation (ADH 5 μM 21×250 mm, 100 bar, EtOH 45%, peak 1 RT=3.7 min, peak 2 RT=5.0 min). ES/MS: m/z=489.2 $[M+H]^+$. $^1$H NMR (400 MHz, DMSO-$d_6$) δ 9.42 (s, 0.5H rotamer), 9.40 (s, 0.5H rotamer), 8.77 (s, 0.5H rotamer), 8.65 (s, 0.5H rotamer), 8.61 (s, 0.5H rotamer), 8.53 (s, 0.5H rotamer), 8.32 (brs, 2H), 8.14 (s, 0.5H rotamer), 8.13 (s, 0.5H rotamer), 6.94 (d, J=9.9 Hz, 1H), 6.80 (d, J=9.9 Hz, 1H), 6.15 (s, 0.5H rotamer), 5.64 (s, 0.5H rotamer), 4.91 (d, J=11.9 Hz, 1H), 4.32 (dd, J=14.0, 6.3 Hz, 0.5H rotamer), 3.09-2.90 (m, 0.5H rotamer), 2.70-2.58 (m, 0.5H rotamer), 2.48-2.39 (m, 0.5H rotamer), 2.29-1.88 (m, 4H).

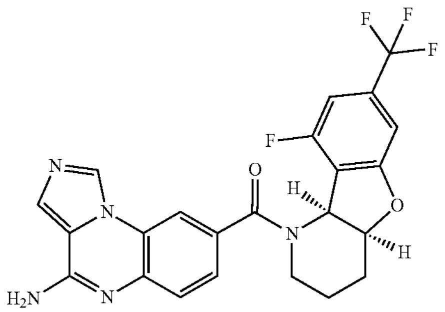 [SMILES: Nc1nc2ccc(C(=O)N3CCC[C@@H]4Oc5cc(C(F)(F)F)cc(F)c5[C@@H]43)cc2n2cncc12]

Example Ff-693: (4-aminoimidazo[1,5-a]quinoxalin-8-yl)((4aS,9bS)-9-fluoro-7-(trifluoromethyl)-3,4,4a,9b-tetrahydrobenzofuro[3,2-b]pyridin-1(2H)-yl)methanone. Prepared using general procedure VI-F starting with 4-((tert-butoxycarbonyl)amino)imidazo[1,5-a]quinoxaline-8-carboxylic acid Ae-1 and (4aS,9bS)-9-fluoro-7-(trifluoromethyl)-1,2,3,4,4a,9b-hexahydrobenzofuro[3,2-b]pyridine hydrochloride Ew-23 (4N HCl in dioxane was used for the removal of the Boc group). ES/MS: m/z=571.8 $[M+H]^+$. $^1H$ NMR (400 MHz, DMSO-$d_6$) δ 9.48 (s, 1H), 9.27 (brs, 1H), 8.43 (s, 1H), 8.40 (s, 1H), 7.67 (s, 0.4H minor rotamer), 7.65 (s, 0.6H major rotamer), 7.56 (brs, 1H), 7.24 (d, J=8.5 Hz, 1H), 7.17 (s, 1H), 6.62 (brs, 0.6H major rotamer), 5.96 (brs, 0.4H minor rotamer), 5.34-5.25 (m, 1H), 3.56-3.31 (m, 1H), 3.07-2.82 (m, 1H), 2.04-1.91 (m, 2H), 1.84-1.67 (m, 1H), 1.66-1.46 (m, 1H).

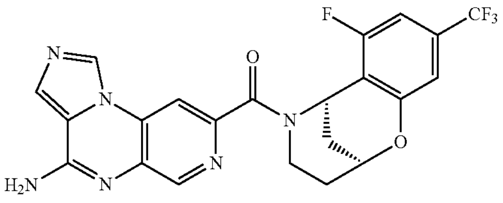 [SMILES: Nc1nc2cnc(C(=O)N3CC[C@H]4C[C@@H]3c3c(F)cc(C(F)(F)F)cc3O4)cc2n2cncc12]

Example Ff-694: (4-aminoimidazo[1,5-a]pyrido[3,4-e]pyrazin-8-yl)((2S,6R)-7-fluoro-9-(trifluoromethyl)-3,4-dihydro-2H-2,6-methanobenzo[b][1,5]oxazocin-5(6H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and Rac-(2S,6R)-7-fluoro-9-(trifluoromethyl)-3,4,5,6-tetrahydro-2H-2,6-methanobenzo[b][1,5]oxazocine Ebi-12. Peak 1 of chiral SFC (RT=1.94 min, AD-H 5 μm 21×250 mm, EtOH 45%, 60 mL/min). ES/MS: m/z=473.2 $[M+H]^+$. $^1H$ NMR (400 MHz, MeOD) δ 9.40 (s, 0.5H, rotamer), 9.33 (s, 0.5H), 8.90 (s, 0.5H, rotamer), 8.78 (s, 0.5H, rotamer), 8.60 (s, 0.5H, rotamer), 8.48 (s, 0.5H, rotamer), 8.32 (s, 0.5H, minor rotamer), 8.29 (s, 0.5H, rotamer), 7.10-7.01 (m, 1+0.5H, rotamer), 6.90 (d, J=8.9 Hz, 0.5H, rotamer), 6.36 (s, 0.5H, rotamer), 5.71 (s, 0.5H, rotamer), 5.00-4.90 (m, 1H), 4.48 (dd, J=14.2, 6.5 Hz, 0.5H, rotamer), 3.94-3.85 (m, 0.5H, rotamer), 3.25-3.16 (m, 0.5H, rotamer), 2.83 (td, J=13.6, 4.2 Hz, 0.5H, rotamer), 2.66 (d, J=14.1 Hz, 0.5H, rotamer), 2.37 (d, J=13.9 Hz, 0.5H, rotamer), 2.27 (d, J=14.5 Hz, 0.5H, rotamer), 2.22-2.00 (m, 2.5H, rotamer).

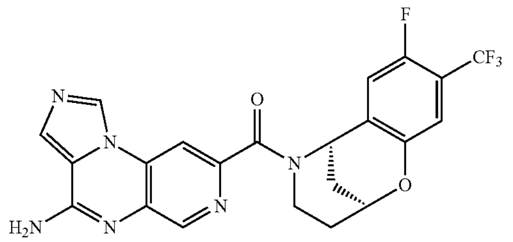 [SMILES: Nc1nc2cnc(C(=O)N3CC[C@H]4C[C@@H]3c3cc(F)c(C(F)(F)F)cc3O4)cc2n2cncc12]

Example Ff-695: (4-aminoimidazo[1,5-a]pyrido[3,4-e]pyrazin-8-yl)((2S,6R)-8-fluoro-9-(trifluoromethyl)-3,4-dihydro-2H-2,6-methanobenzo[b][1,5]oxazocin-5(6H)-yl)methanone. Prepared following general procedure VI-F starting with 7-(tert-butoxycarbonylamino)-2,4,8,11-tetrazatricyclo[7.4.0.02,6]trideca-1(13),3,5,7,9,11-hexaene-12-carboxylic acid Af-6 and (2S,6R)-8-fluoro-9-(trifluoromethyl)-3,4,5,6-tetrahydro-2H-2,6-methanobenzo[b][1,5]oxazocine Ebi-10. ES/MS: m/z=473.2 $[M+H]^+$. $^1H$ NMR (400 MHz, DMSO-$d_6$) δ 9.43 (s, 0.5H, rotamer), 9.41 (s, 0.5H, rotamer), 8.85 (s, 0.5H, rotamer), 8.69 (s, 0.5H, rotamer), 8.63 (s, 0.5H, rotamer), 8.54 (s, 0.5H, rotamer), 8.53 (br, 2H), 8.20 (s, 0.5H, minor rotamer), 8.18 (s, 0.5H, rotamer), 7.39-7.29 (m, 1H), 7.29-7.21 (m, 1H), 5.93 (s, 0.5H, rotamer), 5.36 (m, 0.5H, rotamer), 4.88 (s, 1H), 4.41 (dd, J=14.2, 6.3 Hz, 0.5H, rotamer), 3.86 (dd, J=12.9, 4.6 Hz, 0.5H, rotamer), 2.97-2.86 (m, 0.5H, rotamer), 2.69-2.57 (m, 0.5H, rotamer), 2.30-2.17 (m, 1H), 2.16-2.05 (m, 1H), 2.00-1.86 (m, 2H).

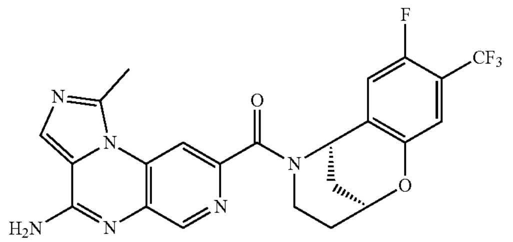 [SMILES: Cc1ncc2c(N)nc3cnc(C(=O)N4CC[C@H]5C[C@@H]4c4cc(F)c(C(F)(F)F)cc4O5)cc3n12]

Example Ff-696: (4-amino-1-methylimidazo[1,5-a]pyrido[3,4-e]pyrazin-8-yl)((2S,6R)-8-fluoro-9-(trifluoromethyl)-3,4-dihydro-2H-2,6-methanobenzo[b][1,5]oxazocin-5(6H)-yl)methanone. Prepared following general procedure VI-F starting with 4-((tert-butoxycarbonyl)amino)-1-methylimidazo[1,5-a]pyrido[3,4-e]pyrazine-8-carboxylic acid Ag-1 and (2S,6R)-8-fluoro-9-(trifluoromethyl)-3,4,5,6-tetrahydro-2H-2,6-methanobenzo[b][1,5]oxazocine Ebi-10. ES/MS: m/z=487.2 $[M+H]^+$. $^1H$ NMR (400 MHz, DMSO-$d_6$) δ 8.84 (s, 0.5H, rotamer), 8.66 (s, 0.5H, rotamer), 8.32 (m, 0.5H, rotamer), 8.28 (br, 2H), 8.24 (s, 0.5H, rotamer), 8.10 (s, 0.5H, rotamer), 8.08 (s, 0.5H, rotamer), 7.39-7.31 (m, 1H), 7.29-7.21 (m, 1H), 5.91 (s, 0.5H, rotamer), 5.40 (s, 0.5H, rotamer), 4.88 (s, 1H), 4.40 (dd, J=14.1, 6.1 Hz, 0.5H, rotamer), 4.00-3.94 (m, 0.5H, rotamer), 3.04 (s, 1.5H, rotamer), 3.01 (s, 1.5H, rotamer), 2.96-2.87 (m, 0.5H, rotamer), 2.69-2.58 (m, 0.5H, rotamer), 2.31-2.22 (m, 1H), 2.13-2.05 (m, 1H), 2.01-1.85 (m, 2H).

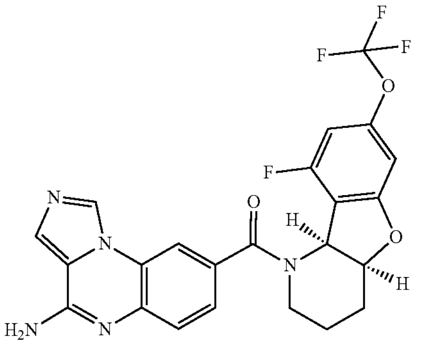 [SMILES: Nc1nc2ccc(C(=O)N3CCC[C@@H]4Oc5cc(OC(F)(F)F)cc(F)c5[C@@H]43)cc2n2cncc12]

Example Ff-697: (4-aminoimidazo[1,5-a]quinoxalin-8-yl)((4aS,9bS)-9-fluoro-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)imidazo[1,5-a]quinoxaline-8-carboxylic acid Ae-1 and (4aS,9bS)-9-fluoro-7-(trifluoromethoxy)-1,2,3,4,4a,9b-hexahydrobenzofuro[3,2-b]pyridine Ew-24 (4N HCl in dioxane was used for the removal of the Boc group). ES/MS: m/z=488.0 $[M+H]^+$. $^1$H NMR (400 MHz, Methanol-d4) δ 9.36 (s, 1H), 8.46-8.33 (m, 2H), 7.78-7.59 (m, 2H), 6.83-6.63 (m, 2H), 5.24 (d, J=8.9 Hz, 1H), 3.17 (s, 1H), 3.04 (s, 2H), 2.20-1.65 (m, 4H).

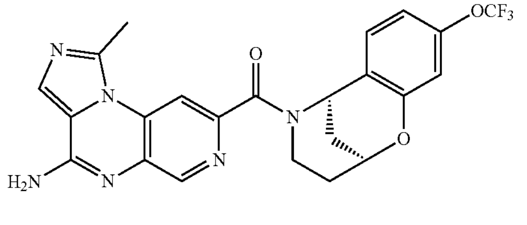 [SMILES: Cc1ncc2c(N)nc3cnc(C(=O)N4CC[C@H]5C[C@@H]4c4ccc(OC(F)(F)F)cc4O5)cc3n12]

Example Ff-698: (4-amino-1-methylimidazo[1,5-a]pyrido[3,4-e]pyrazin-8-yl)((2S,6R)-9-(trifluoromethoxy)-3,4-dihydro-2H-2,6-methanobenzo[b][1,5]oxazocin-5(6H)-yl)methanone. Prepared following general procedure VI-F starting with 4-((tert-butoxycarbonyl)amino)-1-methylimidazo[1,5-a]pyrido[3,4-e]pyrazine-8-carboxylic acid Ag-1 and (2S,6R)-9-(trifluoromethoxy)-3,4,5,6-tetrahydro-2H-2,6-methanobenzo[b][1,5]oxazocine Ebi-6. ES/MS: m/z=485.2 $[M+H]^+$. $^1$H NMR (400 MHz, DMSO-$d_6$) δ 8.82 (s, 0.5H rotamer), 8.65 (s, 0.5H rotamer), 8.28 (s, 0.5H rotamer), 8.25 (brs, 2H), 8.21 (s, 0.5H rotamer), 8.08 (s, 0.5H rotamer), 8.06 (s, 0.5H rotamer), 7.35 (d, J=8.2 Hz, 0.5H rotamer), 7.27 (d, J=8.3 Hz, 0.5H rotamer), 6.94-6.81 (m, 2H), 5.89 (s, 0.5H rotamer), 5.36 (s, 0.5H rotamer), 4.84 (s, 1H), 4.36 (dd, J=14.0, 6.2 Hz, 0.5H rotamer), 3.03 (s, 1.5H rotamer), 3.00 (s, 1.5H rotamer), 2.99-2.86 (m, 0.5H rotamer), 2.71-2.55 (m, 0.5H rotamer), 2.36-2.16 (m, 1H), 2.16-1.86 (m, 3+0.5H rotamer).

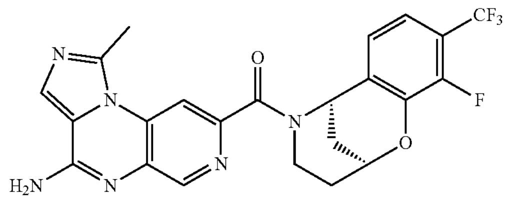 [SMILES: Cc1ncc2c(N)nc3cnc(C(=O)N4CC[C@H]5C[C@@H]4c4ccc(C(F)(F)F)c(F)c4O5)cc3n12]

Example Ff-699: (4-amino-1-methylimidazo[1,5-a]pyrido[3,4-e]pyrazin-8-yl)((2S,6R)-10-fluoro-9-(trifluoromethyl)-3,4-dihydro-2H-2,6-methanobenzo[b][1,5]oxazocin-5(6H)-yl)methanone. Prepared following general procedure VI-F starting with 4-((tert-butoxycarbonyl)amino)-1-methylimidazo[1,5-a]pyrido[3,4-e]pyrazine-8-carboxylic acid Ag-1 and (2S,6R)-10-fluoro-9-(trifluoromethyl)-3,4,5,6-tetrahydro-2H-2,6-methanobenzo[b][1,5]oxazocine Ebi-8. ES/MS: m/z=487.2 $[M+H]^+$. $^1$H NMR (400 MHz, DMSO-$d_6$) δ 8.80 (s, 0.5H rotamer), 8.68 (s, 0.5H rotamer), 8.63 (s, 0.5H rotamer), 8.59 (s, 0.5 rotamer), 8.29 (s, 0.5H rotamer), 8.21 (s, 0.5H rotamer), 8.08 (brs, 2H), 8.02 (s, 0.5H rotamer), 8.00 (s, 0.5H rotamer), 7.28 (s, 0.5H), 7.19 (s, 0.5H), 5.96 (s, 0.5H rotamer), 5.53 (s, 0.5H rotamer), 5.01 (s, 1H), 4.45-4.30 (m, 0.5H rotamer), 4.00 (d, J=15.1 Hz, 0.5H rotamer), 3.01 (s, 1.5H rotamer), 2.99 (s, 1.5H rotamer), 2.73-2.61 (m, 0.5H rotamer), 2.40-2.26 (m, 0.5H rotamer), 2.18-1.90 (m, 4H).

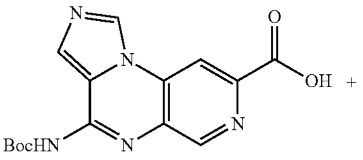

Af-6

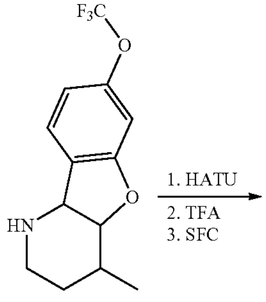

Eba-8

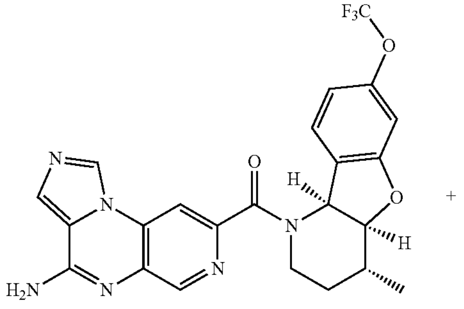

Example Ff-700

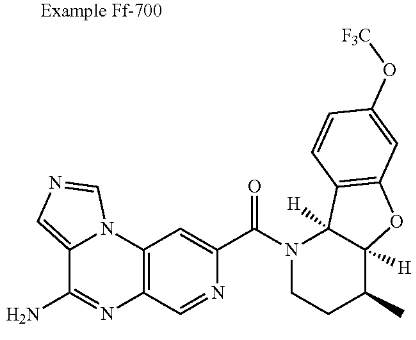

Example Ff-701

Example Ff-700: (4-aminoimidazo[1,5-a]pyrido[3,4-e]pyrazin-8-yl)((4R,4aS,9bS)-4-methyl-7-(trifluoromethoxy)-3,4,4a,9b-tetrahydrobenzofuro[3,2-b]pyridin-1(2H)-yl)methanone and example Ff-701: (4-aminoimidazo[1,5-a]pyrido[3,4-e]pyrazin-8-yl)((4S,4aS,9bS)-4-methyl-7-(trifluoromethoxy)-3,4,4a,9b-tetrahydrobenzofuro[3,2-b]pyridin-1(2H)-yl)methanone. Prepared following general procedure VI-F starting with 4-((tert-butoxycarbonyl)amino)-7-methylimidazo[1,5-a]quinoxaline-8-carboxylic acid Af-6 and (4aS,9bS)-7-(trifluoromethyl)-1,2,3,4,4a,9b-hexahydrobenzofuro[3,2-b]pyridine Eba-8. The isomers were separated using SFC (peak 1, Example Ff-700: 13 min, AD-H 4.6×100 mm 5 mic, 40° C., 40% MeOH-DEA co-solvent, 60 mL/min); (peak, 3, Example Ff-701: 50 min, AD-H 4.6×100 mm 5 mic, 40° C., 40% MeOH-DEA co-solvent, 60 mL/min).

Example Ff-700: ES/MS: m/z=485.2 $[M+H]^+$. $^1$H NMR (400 MHz, DMSO-$d_6$) δ 9.34 (s, 1H), 8.75 (s, 0.5H, rotamer), 8.66 (s, 0.5H, rotamer), 8.62 (s, 0.5H, rotamer), 8.50 (s, 0.5H, rotamer), 8.03 (s, 0.5H, rotamer), 7.89 (s, 2H), 7.83 (d, J=8.1 Hz, 0.5H, rotamer), 7.47 (d, J=8.1 Hz, 0.5H, rotamer), 6.98 (d, J=7.3 Hz, 0.5H, rotamer), 6.94 (s, 0.5H, rotamer), 6.18 (d, J=8.8 Hz, 0.5H, rotamer), 5.86 (d, J=9.0 Hz, 0.5H, rotamer), 5.04 (d, J=8.7 Hz, 0.5H, rotamer), 4.83 (d, J=9.1 Hz, 0.5H, rotamer), 4.24 (s, 0.5H, rotamer), 3.70 (d, J=11.5 Hz, 0.5H, rotamer), 2.73 (dd, J=14.7, 8.0 Hz, 0.5H, rotamer), 2.33-2.24 (m, 0.5H, rotamer), 2.09 (s, 2H, rotamer), 1.98-1.88 (m, 2H, rotamer), 1.18 (d, J=6.4 Hz, 1.5H), 1.11 (d, J=6.4 Hz, 1.5H).

Example Ff-701: ES/MS: m/z=485.2 $[M+H]^+$. $^1$H NMR (400 MHz, DMSO-$d_6$) δ 9.38 (s, 1H), 8.73 (s, 0.5H, rotamer), 8.63 (s, 0.5H, rotamer), 8.62 (s, 0.5H, rotamer), 8.56 (s, 0.5H, rotamer), 8.16 (s, 2H), 8.09 (d, J=6.6 Hz, 1H), 7.61 (d, J=8.1 Hz, 0.5H, rotamer), 7.31 (d, J=7.7 Hz, 0.5H, rotamer), 7.00-6.87 (m, 2H), 6.32 (d, J=8.6 Hz, 0.5H, rotamer), 5.93 (d, J=8.4 Hz, 0.5H, rotamer), 4.71 (t, J=8.3 Hz, 0.5H, rotamer), 4.54 (t, J=7.9 Hz, 0.5H, rotamer), 4.48 (d, J=13.5 Hz, 0.5H, rotamer), 3.86 (d, J=13.4 Hz, 0.5H, rotamer), 3.00-2.88 (m, 1H, rotamer), 2.64 (dd, J=16.0, 5.1 Hz, 1H, rotamer), 1.83-1.70 (m, 0.5H, rotamer), 1.67-1.56 (m, 1H, rotamer), 1.48-1.36 (m, 0.5H, rotamer), 1.32 (d, J=9.9 Hz, 1H, rotamer), 1.11 (d, J=6.7 Hz, 1.5H, rotamer), 1.08 (d, J=6.6 Hz, 1.5H, rotamer).

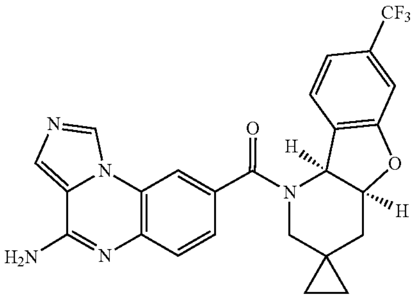 [SMILES: Nc1nc2ccc(C(=O)N3CC4(CC4)C[C@@H]4Oc5cc(C(F)(F)F)ccc5[C@@H]43)cc2n2cncc12]

Example Ff-702: (4-aminoimidazo[1,5-a]quinoxalin-8-yl)((4aS,9bS)-7-(trifluoromethyl)-4a,9b-dihydro-2H-spiro[benzofuro[3,2-b]pyridine-3,1'-cyclopropan]-1(4H)-yl)methanone. Prepared following general procedure VI-F starting with 4-((tert-butoxycarbonyl)amino)imidazo[1,5-a]quinoxaline-8-carboxylic acid Ae-1, and (4aS,9bS)-7-(trifluoromethyl)-1,4,4a,9b-tetrahydro-2H-spiro[benzofuro[3,2-b]pyridine-3,1'-cyclopropane] Ebs-2. ES/MS: m/z=480.0 $[M+H]^+$. $^1$H NMR (400 MHz, DMSO-$d_6$) δ 9.42 (s, 1H), 9.03 (br, 2H), 8.61-8.39 (m, 1H), 8.33 (s, 1H), 7.73-7.49 (m, 3H), 7.44-7.10 (m, 2H), 6.4 (s, 0.7H, major rotamer), 5.76 (s, 0.3H, minor rotamer), 5.26 (s, 1H), 4.04-3.93 (m, 0.3H, minor rotamer), 3.14-2.91 (m, 1+0.7H, major rotamer), 2.15-2.04 (m, 1H), 1.78-1.54 (m, 1H), 0.54-0.44 (m, 1H), 0.41-0.33 (m, 1H), 0.26-0.06 (m, 2H).

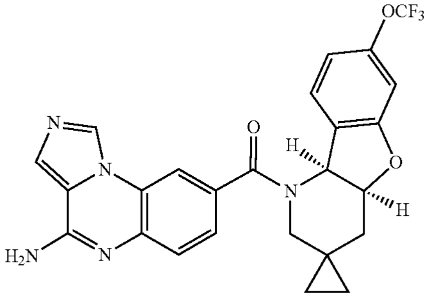 [SMILES: Nc1nc2ccc(C(=O)N3CC4(CC4)C[C@@H]4Oc5cc(OC(F)(F)F)ccc5[C@@H]43)cc2n2cncc12]

Example Ff-703: (4-aminoimidazo[1,5-a]quinoxalin-8-yl)((4aS,9bS)-7-(trifluoromethoxy)-4a,9b-dihydro-2H-spiro[benzofuro[3,2-b]pyridine-3,1'-cyclopropan]-1(4H)-yl)methanone. Prepared following general procedure VI-F starting with 4-((tert-butoxycarbonyl)amino)imidazo[1,5-a]quinoxaline-8-carboxylic acid Ae-1, and (4aS,9bS)-7-(trifluoromethoxy)-1,4,4a,9b-tetrahydro-2H-spiro[benzofuro[3,2-b]pyridine-3,1'-cyclopropane] Ebs-4. ES/MS: m/z=496.0 $[M+H]^+$. $^1$H NMR (400 MHz, DMSO-$d_6$) δ 9.42 (s, 1H), 9.00 (br, 2H), 8.58-8.39 (m, 1H), 8.37-8.24 (m, 1H), 7.76-7.44 (m, 3H), 7.06-6.82 (m, 2H), 6.33 (s, 0.7H, major rotamer), 5.69 (s, 0.3H, minor rotamer), 5.25 (s, 1H), 4.04-3.93 (m, 0.3H, minor rotamer), 3.14-2.88 (m, 1+0.7H, major rotamer), 2.15-2.04 (m, 1H), 1.78-1.54 (m, 1H), 0.54-0.43 (m, 1H), 0.41-0.32 (m, 1H), 0.25-0.05 (m, 2H).

General Procedure VII-F for Synthesis of Examples Fg

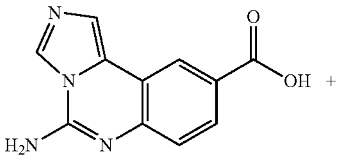

Ba-1

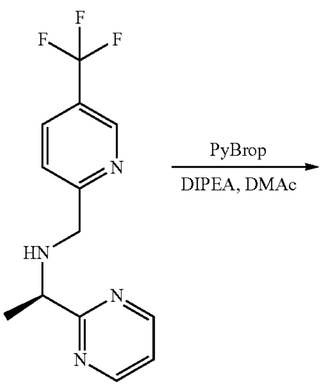

Ec-2

-continued

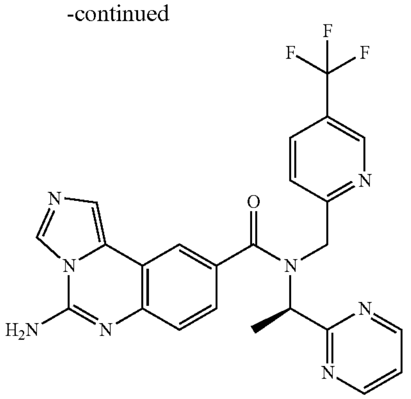

Example Fg-1

Example Fg-1: (R)-5-amino-N-(1-(pyrimidin-2-yl)ethyl)-N-((5-(trifluoromethyl)pyridin-2-yl)methyl)imidazo[1,5-c]quinazoline-9-carboxamide. To a solution of 5-aminoimidazo[1,5-c]quinazoline-9-carboxylic acid Ba-1 (33 mg, 0.144 mmol) and (R)-1-(pyrimidin-2-yl)-N-((5-(trifluoromethyl)pyridin-2-yl)methyl)ethan-1-amine Ec-2 (41 mg, 0.144 mmol) in DMAc (2 mL), was added DIPEA (0.0907 mL, 0.505 mmol) followed by PyBrop (87.5 mg, 0.188 mmol). The reaction was stirred at rt overnight, then diluted with EtOAc and washed with 5% LiCl solution twice, saturated sodium bicarbonate twice, and brine. The organic extract was dried sodium sulfate and concentrated under reduced pressure. The crude residue was purified by HPLC. ES/MS: m/z=493.2 $[M+H]^+$. $^1H$ NMR (400 MHz, DMSO-$d_6$) δ 8.98-8.69 (m, 2H), 8.50-8.19 (m, 3H), 8.20-8.00 (m, 2H), 7.70-7.32 (m, 4H), 5.71 (brs, 0.2H minor rotamer), 5.39 (brs, 0.8H major rotamer), 4.94 (d, J=17.6 Hz, 1H), 4.58 (d, J=17.1 Hz, 1H), 1.74-1.51 (m, 3H).

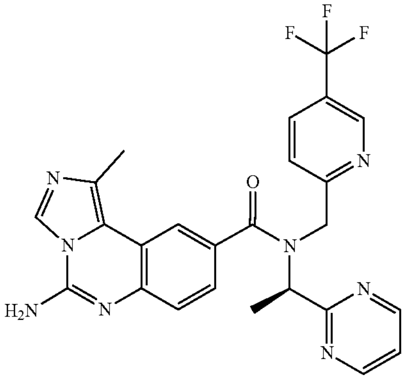 [SMILES: Cc1ncn2c(N)nc3ccc(C(=O)N(Cc4ccc(C(F)(F)F)cn4)[C@H](C)c4ncccn4)cc3c12]

Example Fg-2: (R)-5-amino-1-methyl-N-(1-(pyrimidin-2-yl)ethyl)-N-((5-(trifluoromethyl)pyridin-2-yl)methyl)imidazo[1,5-c]quinazoline-9-carboxamide. Prepared following general procedure VII-F starting with 5-amino-1-methylimidazo[1,5-c]quinazoline-9-carboxylic acid Bb-1 and (R)-1-(pyrimidin-2-yl)-N-((5-(trifluoromethyl)pyridin-2-yl)methyl)ethan-1-amine Ec-2. ES/MS: m/z=507.0 $[M+H]^+$. $^1H$ NMR (400 MHz, DMSO-d6) δ 8.84 (s, 2H), 8.81 (d, J=4.9 Hz, 2H), 8.56 (s, 1H), 8.21-8.07 (m, 1.8H, major rotamer), 8.05 (s, 0.2H, minor rotamer), 8.00-7.92 (m, 0.1H, minor rotamer), 7.80 (s, 1.9H, major rotamer), 7.67-7.51 (m, 1H), 7.50-7.36 (m, 1.6H), 7.36-7.21 (m, 0.4H, minor rotamer), 5.49 (s, 1H), 4.92 (d, J=16.6 Hz, 1H), 4.58 (d, J=16.6 Hz, 1H), 2.55 (s, 3H), 1.61 (d, J=7.0 Hz, 3H).

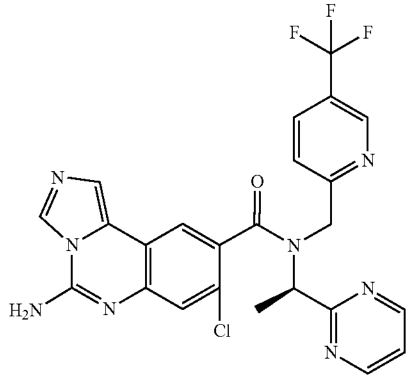 [SMILES: C[C@H](c1ncccn1)N(Cc1ccc(C(F)(F)F)cn1)C(=O)c1cc2c(cc1Cl)nc(N)n1cncc21]

Example Fg-3: (R)-5-amino-8-chloro-N-(1-(pyrimidin-2-yl)ethyl)-N-((5-(trifluoromethyl)pyridin-2-yl)methyl)imidazo[1,5-c]quinazoline-9-carboxamide. Prepared following general procedure VII-F starting with 5-amino-8-chloroimidazo[1,5-c]quinazoline-9-carboxylic acid Bc-2 and (R)-1-(pyrimidin-2-yl)-N-((5-(trifluoromethyl)pyridin-2-yl)methyl)ethan-1-amine Ec-2. ES/MS: m/z=527.0 $[M+H]^+$. $^1H$ NMR (400 MHz, DMSO-d6) δ 8.97-8.84 (m, 1H), 8.80 (d, J=4.9 Hz, 1H), 8.75-8.53 (m, 2H), 8.24 (dd, J=5.7, 3.3 Hz, 1H), 8.11 (s, 0.4H, minor rotamer), 8.03 (d, J=11.6 Hz, 1.6H, major rotamer), 7.96 (s, 1H), 7.85 (s, 0.5H, rotamer), 7.73 (d, J=8.3 Hz, 0.5H, rotamer), 7.57 (d, J=8.3 Hz, 0.3H, minor rotamer), 7.49 (s, 0.7H, major rotamer), 7.46-7.37 (m, 0.5H, rotamer), 7.34 (d, J=9.1 Hz, 0.5H, rotamer), 5.13 (d, J=16.8 Hz, 1H), 5.08-4.93 (m, 1H), 4.57 (d, J=16.8 Hz, 1H), 1.58 (dd, J=7.2, 5.0 Hz, 3H).

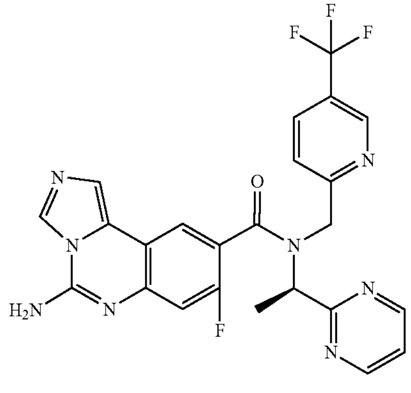 [SMILES: C[C@H](c1ncccn1)N(Cc1ccc(C(F)(F)F)cn1)C(=O)c1cc2c(cc1F)nc(N)n1cncc21]

Example Fg-4: (R)-5-amino-8-fluoro-N-(1-(pyrimidin-2-yl)ethyl)-N-((5-(trifluoromethyl)pyridin-2-yl)methyl)imidazo[1,5-c]quinazoline-9-carboxamide. Prepared following general procedure VII-F starting with 5-amino-8-fluoroimidazo[1,5-c]quinazoline-9-carboxylic acid Bc-1 and (R)-1-(pyrimidin-2-yl)-N-((5-(trifluoromethyl)pyridin-2-yl)methyl)ethan-1-amine Ec-2. ES/MS: m/z=511.0 $[M+H]^+$. $^1H$ NMR (400 MHz, DMSO-d6) δ 8.87 (d, J=2.2 Hz, 1H), 8.83-8.60 (m, 3H), 8.31-7.80 (m, 4H), 7.79 (s, 0.3H, minor rotamer), 7.55 (d, J=8.3 Hz, 0.8H, major rotamer), 7.48-7.30 (m, 1H), 7.24 (d, J=11.1 Hz, 0.7H, major rotamer), 7.06 (d, J=11.1 Hz, 0.3H, minor rotamer), 5.91 (d, J=7.2 Hz, 0.2H, minor rotamer), 5.20 (q, J=6.9 Hz, 0.8H, major rotamer), 5.05 (d, J=16.9 Hz, 0.7H, major rotamer), 4.80 (s, 0.3H, minor rotamer), 1.62 (dd, J=11.7, 7.1 Hz, 3H).

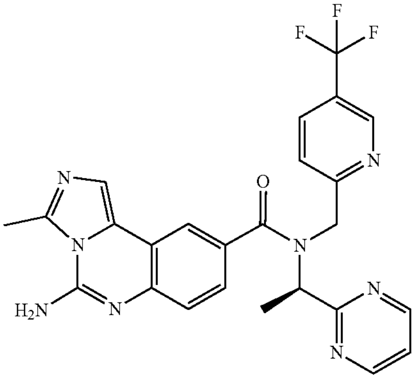 [SMILES: Cc1ncc2c3cc(C(=O)N(Cc4ccc(C(F)(F)F)cn4)[C@H](C)c4ncccn4)ccc3nc(N)n12]

Example Fg-5: (R)-5-amino-3-methyl-N-(1-(pyrimidin-2-yl)ethyl)-N-((5-(trifluoromethyl)pyridin-2-yl)methyl)imidazo[1,5-c]quinazoline-9-carboxamide. Prepared following general procedure VII-F starting with 5-amino-3-methylimidazo[1,5-c]quinazoline-9-carboxylic acid Ba-2 and (R)-1-(pyrimidin-2-yl)-N-((5-(trifluoromethyl)pyridin-2-yl)methyl)ethan-1-amine Ec-2. ES/MS: m/z=507.0 $[M+H]^+$. $^1H$ NMR (400 MHz, DMSO-d6) δ 8.93-8.83 (m, 1H), 8.80 (d, J=4.9 Hz, 2H), 8.17 (s, 1H), 8.14-8.03 (m, 2H), 7.63 (d, J=8.3 Hz, 1H), 7.58 (d, J=8.3 Hz, 1H), 7.42 (q, J=4.9, 4.4 Hz, 2H), 5.70 (s, 0.2H, minor rotamer), 5.36 (d, J=7.6 Hz, 0.8H, major rotamer), 4.93 (d, J=16.7 Hz, 1H), 4.56 (d, J=16.9 Hz, 1H), 3.02 (s, 3H), 1.63 (d, J=7.0 Hz, 3H).

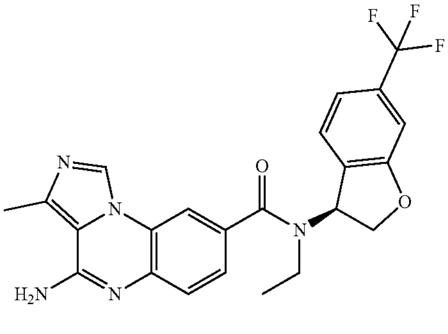 [SMILES: CCN(C(=O)c1ccc2nc(N)c3c(C)ncn3c2c1)[C@@H]1COc2cc(C(F)(F)F)ccc21]

Example Fg-6: (S)-4-amino-N-ethyl-3-methyl-N-(6-(trifluoromethyl)-2,3-dihydrobenzofuran-3-yl)imidazo[1,5-a]quinoxaline-8-carboxamide. Prepared following general procedure VII-F starting with 5-amino-3-methylimidazo[1,5-c]quinazoline-9-carboxylic acid Ba-2 and (S)—N-ethyl-6-(trifluoromethyl)-2,3-dihydrobenzofuran-3-amine hydrochloride Eh-2. ES/MS: m/z=456.0 $[M+H]^+$. $^1H$ NMR (400 MHz, MeOD) δ 9.23 (s, 1H), 8.36 (d, J=1.5 Hz, 1H), 7.76-7.54 (m, 3H), 7.29 (d, J=7.9 Hz, 1H), 7.14 (s, 1H), 6.39-5.49 (m, 1H), 4.82-4.74 (m, 2H), 3.40-3.35 (m, 2H), 2.81 (s, 3H), 1.28-0.59 (m, 3H).

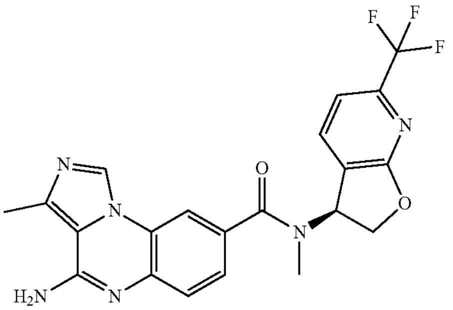

Example Fg-7: (S)-4-amino-N,3-dimethyl-N-(6-(trifluoromethyl)-2,3-dihydrofuro[2,3-b]pyridin-3-yl)imidazo[1,5-a]quinoxaline-8-carboxamide. Prepared following general procedure VII-F starting with 4-amino-3-methylimidazo[1,5-a]quinoxaline-8-carboxylic acid Aa-1 and (S)—N-methyl-6-(trifluoromethyl)-2,3-dihydrofuro[2,3-b]pyridin-3-amine Eh-6. ES/MS: m/z=443.0 $[M+H]^+$. $^1H$ NMR (400 MHz, MeOD) δ 9.21 (s, 1H), 8.39 (s, 1H), 8.09 (d, J=7.5 Hz, 1H), 7.75-7.68 (m, 2H), 7.47 (d, J=7.5 Hz, 1H), 6.41 (s, 0.7H, major rotamer), 5.86 (s, 0.3H, minor rotamer), 4.98 (s, 1H), 4.83 (dd, J=10.5, 4.5 Hz, 1H), 2.89 (s, 3H), 2.81 (s, 3H).

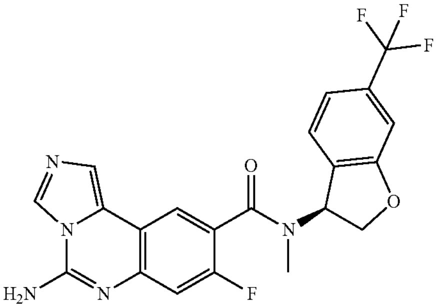 [SMILES: CN(C(=O)c1cc2c(cc1F)nc(N)n1cncc21)[C@@H]1COc2cc(C(F)(F)F)ccc21]

Example Fg-8: (S)-5-amino-8-fluoro-N-methyl-N-(6-(trifluoromethyl)-2,3-dihydrobenzofuran-3-yl)imidazo[1,2-c]quinazoline-9-carboxamide. Prepared following general procedure VII-F starting with 5-amino-8-fluoroimidazo[1,5-c]quinazoline-9-carboxylic acid Bc-1 and (S)—N-methyl-6-(trifluoromethyl)-2,3-dihydrobenzofuran-3-amine hydrochloride Eh-1. ES/MS: m/z=446.0 $[M+H]^+$. $^1H$ NMR (400 MHz, MeOD) δ 8.89 (s, 1H), 8.20 (d, 1H), 8.09-8.02 (m, 1H), 7.60 (d, J=7.8 Hz, 0.6H, major rotamer), 7.51 (d, J=8.1 Hz, 0.4H, minor rotamer), 7.32 (dd, J=14.9, 9.3 Hz, 2H), 7.16 (d, J=16.8 Hz, 1H), 6.59 (dd, J=9.1, 3.8 Hz, 0.6H, major rotamer), 5.68 (s, 0.4H, minor rotamer), 4.77-4.69 (m, 2H), 2.84 (s, 1.2H, minor rotamer), 2.74-2.65 (m, 1.8H, major rotamer).

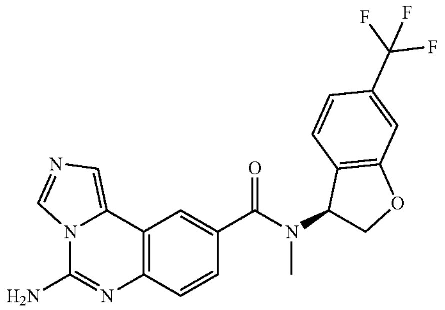

Example Fg-9: (S)-5-amino-N-methyl-N-(6-(trifluoromethyl)-2,3-dihydrobenzofuran-3-yl)imidazo[1,5-c]quinazoline-9-carboxamide. Prepared following general procedure VII-F starting with 5-aminoimidazo[1,5-c]quinazoline-9-carboxylic acid Ba-1 and (S)—N-methyl-6-(trifluoromethyl)-2,3-dihydrobenzofuran-3-amine hydrochloride Eh-1. ES/MS: m/z=428.0 $[M+H]^+$. $^1$H NMR (400 MHz, MeOD) δ 8.94 (s, 1H), 8.29 (d, J=1.7 Hz, 1H), 8.15 (s, 1H), 7.82-7.54 (m, 3H), 7.32 (d, J=7.8 Hz, 1H), 7.17 (s, 1H), 6.51 (s, 0.6H), 5.98-5.61 (m, 0.4H, minor rotamer), 4.81-4.73 (m, 2H), 2.79 (s, 3H).

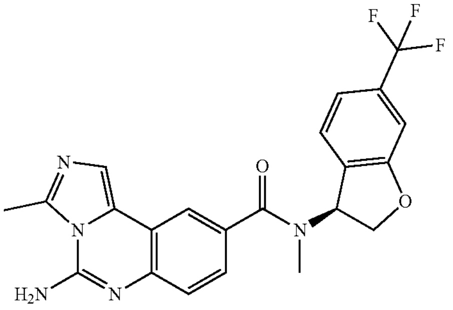 [SMILES: Cc1ncc2c3cc(C(=O)N(C)[C@@H]4COc5cc(C(F)(F)F)ccc54)ccc3nc(N)n12]

Example Fg-10: (S)-5-amino-N,3-dimethyl-N-(6-(trifluoromethyl)-2,3-dihydrobenzofuran-3-yl)imidazo[1,5-c]quinazoline-9-carboxamide. Prepared following general procedure VII-F starting with 5-amino-3-methylimidazo[1,5-c]quinazoline-9-carboxylic acid Ba-2 and (S)—N-methyl-6-(trifluoromethyl)-2,3-dihydrobenzofuran-3-amine hydrochloride Eh-1. ES/MS: m/z=442.0 $[M+H]^+$. $^1$H NMR (400 MHz, MeOD) δ 8.16 (d, J=1.8 Hz, 1H), 7.69-7.47 (m, 4H), 7.32 (d, J=7.5 Hz, 1H), 7.17 (s, 1H), 6.49 (s, 1H), 4.82-4.67 (m, 2H), 3.14 (s, 3H), 2.79 (s, 3H).

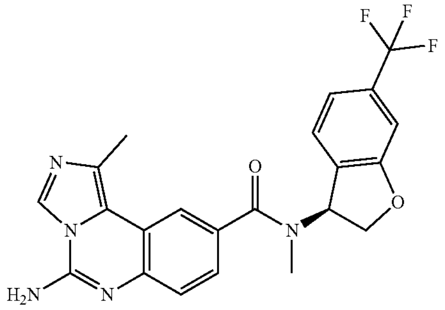 [SMILES: Cc1ncn2c(N)nc3ccc(C(=O)N(C)[C@@H]4COc5cc(C(F)(F)F)ccc54)cc3c12]

Example Fg-11: (S)-5-amino-N,1-dimethyl-N-(6-(trifluoromethyl)-2,3-dihydrobenzofuran-3-yl)imidazo[1,5-c]quinazoline-9-carboxamide. Prepared following general procedure VII-F starting with 5-amino-1-methylimidazo[1,5-c]quinazoline-9-carboxylic acid Bb-1 and (S)—N-methyl-6-(trifluoromethyl)-2,3-dihydrobenzofuran-3-amine hydrochloride Eh-1. ES/MS: m/z=442.0 $[M+H]^+$. $^1$H NMR (400 MHz, MeOD) δ 8.86 (s, 1H), 8.20 (d, J=1.7 Hz, 1H), 7.79-7.51 (m, 3H), 7.32 (d, J=7.9 Hz, 1H), 7.17 (s, 1H), 6.51 (s, 1H), 4.82-4.76 (m, 2H), 2.82 (s, 3H), 2.81 (s, 3H).

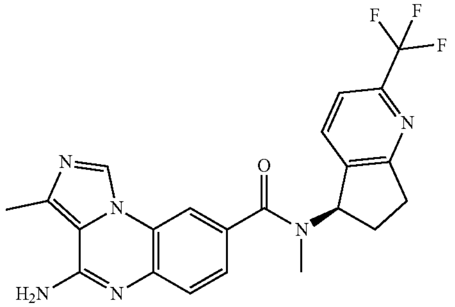 [SMILES: Cc1ncn2c1c(N)nc1ccc(C(=O)N(C)[C@@H]3CCc4nc(C(F)(F)F)ccc43)cc12]

Example Fg-12: 4-amino-N,3-dimethyl-N-(2-(trifluoromethyl)-6,7-dihydro-5H-cyclopenta[b]pyridin-5-yl)imidazo[1,5-a]quinoxaline-8-carboxamide. Prepared following general procedure VII-F starting with 4-amino-3-methylimidazo[1,5-a]quinoxaline-8-carboxylic acid Aa-1 and N-methyl-2-(trifluoromethyl)-6,7-dihydro-5H-cyclopenta[b]pyridin-5-amine hydrochloride Eh-3. ES/MS: m/z=441.2 $[M+H]^+$. $^1$H NMR (400 MHz, MeOD) δ 9.22 (s, 1H), 8.40 (d, J=1.1 Hz, 1H), 7.94-7.49 (m, 3H), 7.32 (d, J=7.8 Hz, 1H), 7.17 (s, 1H), 6.51 (s, 0.7H, major rotamer), 5.77 (s, 0.3H, minor rotamer), 4.77 (dd, J=10.5, 4.0 Hz, 2H), 2.84-2.76 (m, 6H). 1H overlaps with solvent.

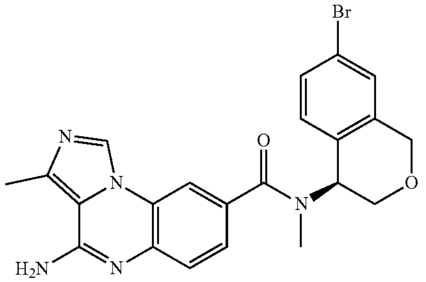 [SMILES: Cc1ncn2c1c(N)nc1ccc(C(=O)N(C)[C@@H]3COCc4cc(Br)ccc43)cc12]

Example Fg-13: (S)-4-amino-N-(7-bromoisochroman-4-yl)-N,3-dimethylimidazo[1,5-a]quinoxaline-8-carboxamide. Prepared following general procedure VII-F starting with 4-amino-3-methylimidazo[1,5-a]quinoxaline-8-carboxylic acid Aa-1 and (S)-7-bromo-N-methylisochroman-4-amine hydrochloride Eh-4. ES/MS: m/z=466.0 $[M+H]^+$. $^1$H NMR (400 MHz, MeOD) δ 9.28-9.19 (m, 1H), 8.41 (s, 1H), 7.72-7.66 (m, 2H), 7.51 (t, J=9.1 Hz, 1H), 7.42-7.21 (m, 2H), 5.79 (s, 1H), 4.85-4.52 (m, 2H), 4.35-4.18 (m, 1H), 4.18-4.03 (m, 1H), 2.92 (s, 1H, minor rotamer), 2.85 (s, 2H, major rotamer), 2.81 (s, 3H).

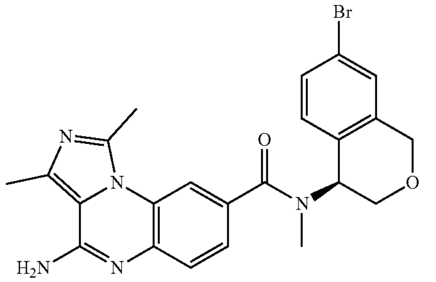 [SMILES: Cc1nc(C)n2c1c(N)nc1ccc(C(=O)N(C)[C@@H]3COCc4cc(Br)ccc43)cc12]

Example Fg-14: (S)-4-amino-N-(7-bromoisochroman-4-yl)-N,1,3-trimethylimidazo[1,5-a]quinoxaline-8-carboxamide. Prepared following general procedure VII-F starting with 4-amino-1,3-dimethylimidazo[1,5-a]quinoxaline-8-carboxylic acid Ab-1 and (S)-7-bromo-N-methylisochroman-4-amine hydrochloride Eh-4. ES/MS: m/z=480.0 $[M+H]^+$. $^1$H NMR (400 MHz, MeOD) δ 8.32-8.27 (m, 1H), 7.73-7.62 (m, 2H), 7.55-7.48 (m, 1H), 7.43-7.23 (m, 2H), 5.77 (s, 1H), 4.99 (s, 1H), 4.84-4.54 (m, 1H), 4.41-3.92 (m, 2H), 3.11-3.04 (m, 3H), 2.95-2.86 (m, 3H), 2.77 (s, 3H).

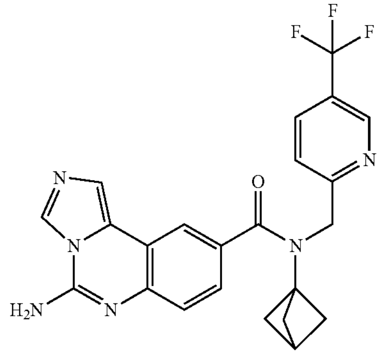 [SMILES: Nc1nc2ccc(C(=O)N(Cc3ccc(C(F)(F)F)cn3)C34CC(C3)C4)cc2c2cncn12]

Example Fg-15: 5-amino-N-(bicyclo[1.1.1]pentan-1-yl)-N-((5-(trifluoromethyl)pyridin-2-yl)methyl)imidazo[1,5-c]quinazoline-9-carboxamide. Prepared following general procedure VII-F starting with 5-aminoimidazo[1,5-c]quinazoline-9-carboxylic acid Ba-1 and N-((5-(trifluoromethyl)pyridin-2-yl)methyl)bicyclo[1.1.1]pentan-1-amine Ec-1. EZ/MS: m/z=453.2 $[M+H]^+$. $^1$H NMR (400 MHz, DMSO) δ 9.07-8.92 (m, 1H), 8.80 (s, 1H), 8.22 (dd, J=8.4, 2.4 Hz, 3H), 8.12 (d, J=1.8 Hz, 1H), 8.04 (s, 1H), 7.63 (d, J=8.3 Hz, 1H), 7.54-7.33 (m, 2H), 4.84 (s, 2H), 2.27 (s, 1H), 2.00-1.58 (m, 6H).

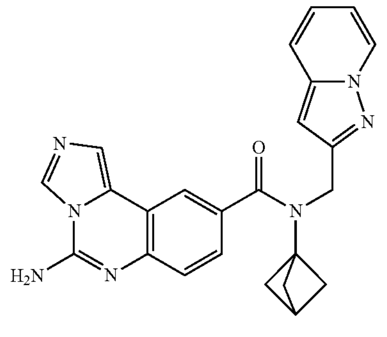 [SMILES: Nc1nc2ccc(C(=O)N(Cc3cc4ccccn4n3)C34CC(C3)C4)cc2c2cncn12]

Example Fg-16: 5-amino-N-(bicyclo[1.1.1]pentan-1-yl)-N-(pyrazolo[1,5-a]pyridin-2-ylmethyl)imidazo[1,5-c]quinazoline-9-carboxamide. Prepared following general procedure VII-F starting with 5-aminoimidazo[1,5-c]quinazoline-9-carboxylic acid Ba-1 and N-(pyrazolo[1,5-a]pyridin-2-ylmethyl)bicyclo[1.1.1]pentan-1-amine Ec-4. EZ/MS: m/z=424.3 $[M+H]^+$. $^1$H NMR (400 MHz, DMSO) δ 8.77 (s, 1H), 8.65 (dt, J=7.0, 1.1 Hz, 1H), 8.17 (d, J=27.7 Hz, 3H), 7.99 (s, 1H), 7.66 (dt, J=8.9, 1.3 Hz, 1H), 7.53-7.39 (m, 2H), 7.21 (ddd, J=8.9, 6.7, 1.1 Hz, 1H), 6.86 (td, J=6.8, 1.4 Hz, 1H), 6.57 (s, 1H), 4.78 (s, 2H), 2.28 (s, 1H), 1.85 (s, 7H).

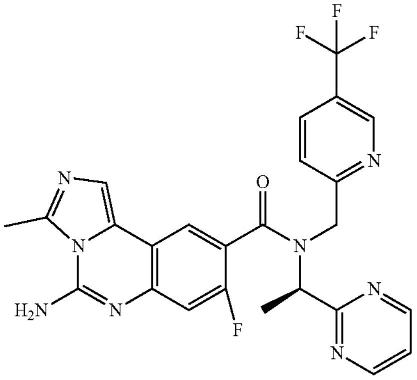 [SMILES: Cc1ncc2c3cc(C(=O)N(Cc4ccc(C(F)(F)F)cn4)[C@H](C)c4ncccn4)c(F)cc3nc(N)n12]

Example Fg-17: (R)-5-amino-8-fluoro-3-methyl-N-(1-(pyrimidin-2-yl)ethyl)-N-((5-(trifluoromethyl)pyridin-2-yl)methyl)imidazo[1,5-c]quinazoline-9-carboxamide. Prepared following general procedure VII-F starting with 5-amino-8-fluoro-3-methylimidazo[1,5-c]quinazoline-9-carboxylic acid Bc-3 and (R)-1-(pyrimidin-2-yl)-N-((5-(trifluoromethyl)pyridin-2-yl)methyl)ethan-1-amine Ec-2. ES/MS: m/z=525.0 $[M+H]^+$. $^1$H NMR (400 MHz, Methanol-d4) δ 8.78 (d, J=4.5 Hz, 1H), 8.72 (t, J=4.8 Hz, 2H), 8.17 (d, J=6.9 Hz, 0.7H, major rotamer), 8.09 (dd, J=8.6, 2.4 Hz, 1H), 7.96 (s, 0.3H, minor rotamer), 7.92 (d, J=6.3 Hz, 0.3, minor rotamer), 7.63 (d, J=8.3 Hz, 0.7H, major rotamer), 7.44 (d, J=8.3 Hz, 0.3H, minor rotamer), 7.33 (t, J=4.9 Hz, 0.7H, major rotamer), 7.27 (d, J=10.3 Hz, 0.7H, major rotamer), 7.11 (d, J=10.6 Hz, 0.3H, minor rotamer), 6.00 (q, J=7.0 Hz, 0.3H, minor rotamer), 5.30 (q, J=7.0 Hz, 1H), 5.18 (d, J=16.8 Hz, 1H), 4.92 (s, 0.7H, major rotamer), 3.16 (s, 2H, major rotamer), 3.12 (s, 1H), 1.76 (d, J=7.2 Hz, 1H, minor rotamer), 1.72 (d, J=7.0 Hz, 2H, major rotamer).

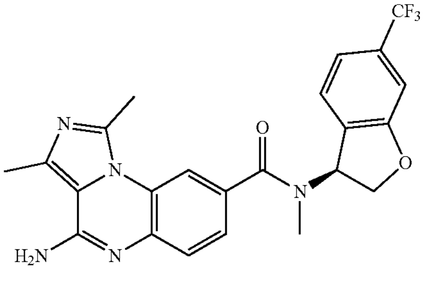 [SMILES: Cc1nc(C)n2c1c(N)nc1ccc(C(=O)N(C)[C@@H]3COc4cc(C(F)(F)F)ccc43)cc12]

Example Fg-18: (S)-4-amino-N,1,3-trimethyl-N-(6-(trifluoromethyl)-2,3-dihydrobenzofuran-3-yl)imidazo[1,5-a]quinoxaline-8-carboxamide. Prepared following general procedure VII-F starting with 4-amino-1,3-dimethylimidazo[1,5-a]quinoxaline-8-carboxylic acid Ab-1 and (S)—N-methyl-6-(trifluoromethyl)-2,3-dihydrobenzofuran-3-amine hydrochloride Eh-1. ES/MS: m/z=455.9 [M+H]+. $^{1}$H NMR (400 MHz, DMSO-d6) δ 8.20 (s, 1H), 7.77-7.63 (m, 3H), 7.37 (d, J=7.9 Hz, 1H), 7.30 (s, 1H), 6.42 (s, 1H), 4.80 (d, J=6.3 Hz, 2H), 3.04 (s, 3H), 2.71 (s, 3H), 2.69 (s, 3H).

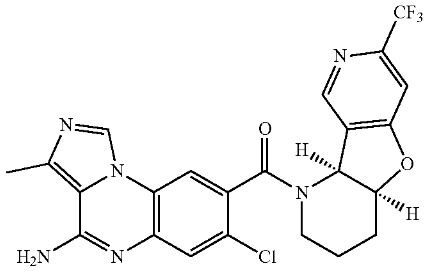 [SMILES: Cc1ncn2c1c(N)nc1cc(Cl)c(C(=O)N3CCC[C@@H]4Oc5cc(C(F)(F)F)ncc5[C@@H]43)cc12]

Example Fg-19: (4-amino-7-chloro-3-methylimidazo[1,5-a]quinoxalin-8-yl)((4aS,9bS)-7-(trifluoromethyl)-3,4,4a,9b-tetrahydrofuro[3,2-b:4,5-c']dipyridin-1(2H)-yl)methanone. Prepared following general procedure VII-F starting with 4-amino-7-chloro-3-methyl-imidazo[1,5-a]quinoxaline-8-carboxylic acid Aj-2 and (2S,7S)-11-(trifluoromethyl)-8-oxa-3,12-diazatricyclo[7.4.0.02,7]trideca-1(9),10,12-triene Ew-4. ES/MS: m/z=502.7 [M+H]+. $^{1}$H NMR (400 MHz, Methanol-d4) δ 9.26-9.06 (m, 1H), 8.75-8.50 (m, 1H), 8.34 (d, J=16.6 Hz, 1H), 7.71 (dd, J=21.3, 15.2 Hz, 1H), 7.34 (d, J=33.2 Hz, 1H), 6.52 (t, J=9.5 Hz, 0.75H, major rotamer), 5.69 (dd, J=32.9, 9.5 Hz, 0.25H, minor rotamer), 5.43-5.31 (m, 1H), 3.42-3.32 (m, 1H), 3.17-2.84 (m, 1H), 2.78 (s, 3H), 2.24-2.02 (m, 2H), 1.98-1.59 (m, 2H).

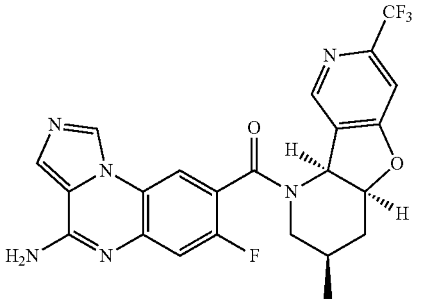 [SMILES: C[C@@H]1C[C@@H]2Oc3cc(C(F)(F)F)ncc3[C@@H]2N(C(=O)c2cc3c(cc2F)nc(N)c2cncn23)C1]

Example Fg-20: (4-amino-7-fluoroimidazo[1,5-a]quinoxalin-8-yl)((3R,4aS,9bS)-3-methyl-7-(trifluoromethyl)-3,4,4a,9b-tetrahydrofuro[3,2-b:4,5-c']dipyridin-1(2H)-yl) methanone. Prepared following general procedure VII-F starting with 4-amino-7-fluoro-imidazo[1,5-a]quinoxaline-8-carboxylic acid hydrochloride Ak-1 and (2S,5R,7S)-5-methyl-11-(trifluoromethyl)-8-oxa-3,12-diazatricyclo [7.4.0.02,7]trideca-1(9),10,12-triene Ew-5. ES/MS: m/z=486.8 [M+H]+. $^{1}$H NMR (400 MHz, Methanol-d4) δ 9.29 (s, 1H), 8.68-8.41 (m, 2H), 8.43-8.24 (m, 1H), 7.48 (d, J=9.8 Hz, 1H), 7.40 (s, 1H), 6.46 (d, J=8.6 Hz, 0.8H, major rotamer), 5.72 (d, J=8.4 Hz, 0.2H, minor rotamer), 5.34 (ddd, J=8.6, 7.1, 5.3 Hz, 1H), 3.60-3.45 (m, 1H), 2.65 (t, J=12.5 Hz, 1H), 2.33 (dt, J=14.2, 5.7 Hz, 1H), 1.98-2.05 (m, 1H), 1.68 (dt, J=14.7, 7.3 Hz, 1H), 1.06 (d, J=6.7 Hz, 0.6H, minor rotamer), 0.91 (d, J=6.7 Hz, 2.4H, major rotamer).

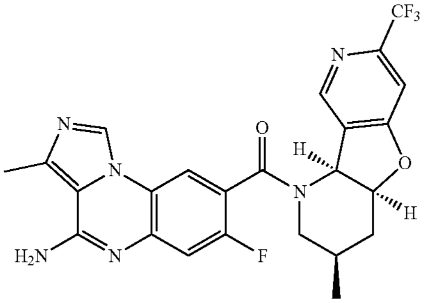 [SMILES: Cc1ncn2c1c(N)nc1cc(F)c(C(=O)N3C[C@H](C)C[C@@H]4Oc5cc(C(F)(F)F)ncc5[C@@H]43)cc12]

Example Fg-21: (4-amino-7-fluoro-3-methylimidazo[1,5-a]quinoxalin-8-yl)((3R,4aS,9bS)-3-methyl-7-(trifluoromethyl)-3,4,4a,9b-tetrahydrofuro[3,2-b:4,5-c']dipyridin-1 (2H)-yl)methanone. Prepared following general procedure VII-F starting with 4-amino-7-fluoro-3-methyl-imidazo[1,5-a]quinoxaline-8-carboxylic acid hydrochloride Ak-2 and (2S,5R,7S)-5-methyl-11-(trifluoromethyl)-8-oxa-3,12-diazatricyclo[7.4.0.02,7]trideca-1(9),10,12-triene Ew-5. ES/MS: m/z=500.8 [M+H]+. $^{1}$H NMR (400 MHz, Methanol-d4) δ 9.17 (s, 1H), 8.66-8.45 (m, 1H), 8.40 (d, J=5.9 Hz, 1H), 7.44 (d, J=9.7 Hz, 1H), 7.38 (s, 1H), 6.44 (d, J=8.5 Hz, 0.67H, major rotamer), 5.69 (d, J=8.5 Hz, 0.33H, minor rotamer), 5.32 (td, J=7.6, 5.3 Hz, 1H), 3.56-3.42 (m, 1H), 2.79 (s, 3H), 2.63 (t, J=12.5 Hz, 1H), 2.31 (dt, J=14.4, 5.6 Hz, 1H), 2.16-1.92 (m, 1H), 1.66 (dt, J=14.6, 7.4 Hz, 1H), 1.03 (d, J=6.7 Hz, 1H, minor rotamer), 0.89 (d, J=6.8 Hz, 2H, major rotamer).

Examples Fg-22 and Fg-23: Prepared following general procedure VII-F starting with 4-amino-3-methyl-imidazo[1,5-a]quinoxaline-8-carboxylic acid Aa-1 and (4aS,9aR)-2-methyl-7-(trifluoromethoxy)-2,3,4,4a,9,9a-hexahydroindeno[2,1-b][1,4]oxazine Eaw-3.

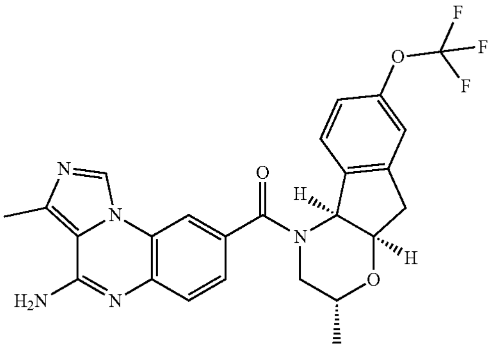 [SMILES: Cc1ncn2c1c(N)nc1ccc(C(=O)N3C[C@@H](C)O[C@@H]4Cc5cc(OC(F)(F)F)ccc5[C@@H]43)cc12]

Example Fg-22: (4-amino-3-methylimidazo[1,5-a]quinoxalin-8-yl)((2R,4aS,9aR)-2-methyl-7-(trifluoromethoxy)-2,3,9,9a-tetrahydroindeno[2,1-b][1,4]oxazin-4(4aH)-yl) methanone. Peak 1 by HPLC purification. ES/MS: m/z=498.3 [M+H]+. $^{1}$H NMR (400 MHz, DMSO-$d_6$) δ 9.44-9.32 (m, 1H), 8.82 (br, 2H), 8.55-8.39 (m, 1H), 7.75-7.18 (m, 5H), 5.89 (m, 0.5H, rotamer), 5.03 (m, 0.5H, rotamer), 4.71-4.48 (m, 1H), 4.34-4.12 (m, 1H), 3.97-3.78 (m, 1H), 3.34-3.15 (m, 2H), 3.06-2.78 (m, 1H), 2.77-2.66 (m, 3H), 1.42-1.19 (m, 3H).

4.45-4.52 (m, 1H), 3.96-3.38 (m, 2H), 3.29-3.10 (m, 2H, overlapped with solvent), 3.03-2.58 (m, 2H).

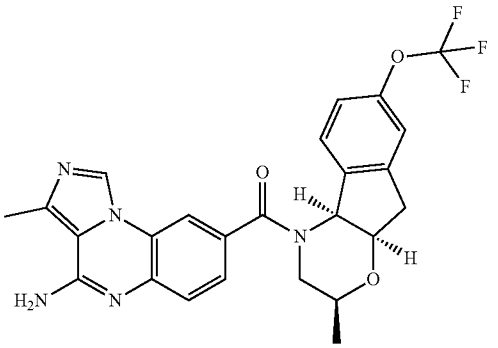 [SMILES: Cc1ncn2c1c(N)nc1ccc(C(=O)N3C[C@H](C)O[C@@H]4Cc5cc(OC(F)(F)F)ccc5[C@@H]43)cc12]

Example Fg-23: (4-amino-3-methylimidazo[1,5-a]quinoxalin-8-yl)((2S,4aS,9aR)-2-methyl-7-(trifluoromethoxy)-2,3,9,9a-tetrahydroindeno[2,1-b][1,4]oxazin-4(4aH)-yl)methanone. Peak 2 by HPLC purification. ES/MS: m/z=498.3 $[M+H]^+$. $^1$H NMR (400 MHz, DMSO-$d_6$) δ 9.40 (s, 0.6H, major rotamer), 9.29 (s, 0.4H, minor rotamer), 8.78 (br, 2H), 8.53 (s, 0.4H, minor rotamer), 8.44 (s, 0.6H, major rotamer), 7.70-7.66 (m, 0.6H, major rotamer), 7.66-7.61 (m, 1H), 7.60-7.52 (m, 1H), 7.39-7.32 (m, 1H), 7.30-7.24 (m, 1H), 7.24-7.18 (m, 0.4H, minor rotamer), 5.84 (d, J=3.9 Hz, 0.6H, major rotamer), 5.03 (d, J=3.8 Hz, 0.4H, minor rotamer), 4.53-4.45 (m, 1H), 4.33 (d, J=13.3 Hz, 0.4H, minor rotamer), 3.46-3.39 (m, 1H), 3.30-3.23 (m, 0.6H, major rotamer), 3.03-2.94 (m, 0.4H, minor rotamer), 2.91 (d, J=13.3 Hz, 0.6H, major rotamer), 2.84-2.73 (m, 1H), 2.73 (s, 1.8H, major rotamer), 2.69 (s, 1.2H, minor rotamer), 2.45-2.30 (m, 1H), 1.07 (d, J=6.2 Hz, 1.2H, rotamer), 0.89 (d, J=6.2 Hz, 1.8H, major rotamer).

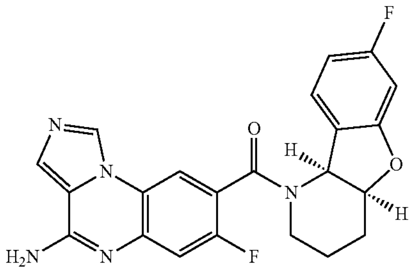

Example Fg-25: (4-amino-7-fluoroimidazo[1,5-a]quinoxalin-8-yl)((4aS,9bS)-7-fluoro-3,4,4a,9b-tetrahydrobenzofuro[3,2-b]pyridin-1(2H)-yl)methanone. Prepared following general procedure VII-F using 4-amino-7-fluoroimidazo[1,5-a]quinoxaline-8-carboxylic acid hydrochloride Ak-1 and (4aS,9bS)-7-fluoro-1,2,3,4,4a,9b-hexahydrobenzofuro[3,2-b]pyridine Ew-10. ES/MS: m/z=422.0 $[M+H]^+$. $^1$H NMR (400 MHz, Methanol-d4) δ 9.30 (d, J=6.8 Hz, 1H), 8.79-8.19 (m, 2H), 7.76-7.16 (m, 2H), 6.94-6.55 (m, 2H), 6.33 (d, J=8.8 Hz, 0.6H, major rotamer), 5.52 (d, J=9.1 Hz, 0.4H, minor rotamer), 5.17 (dt, J=8.5, 4.0 Hz, 1H), 3.54-3.42 (m, 1H), 2.89-2.97 (m, 1H), 2.22-1.58 (m, 4H).

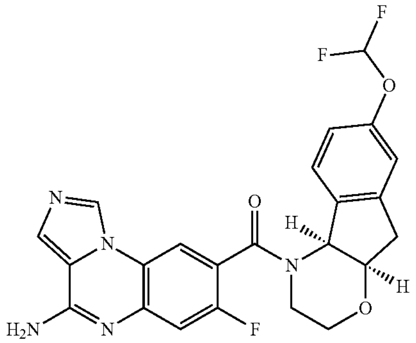 [SMILES: Nc1nc2cc(F)c(C(=O)N3CCO[C@@H]4Cc5cc(OC(F)F)ccc5[C@@H]43)cc2n2cncc12]

Example Fg-24: (4-amino-7-fluoroimidazo[1,5-a]quinoxalin-8-yl)((4aS,9aR)-7-(difluoromethoxy)-2,3,9,9a-tetrahydroindeno[2,1-b][1,4]oxazin-4(4aH)-yl)methanone. Prepared following general procedure VII-F using 4-amino-7-fluoroimidazo[1,5-a]quinoxaline-8-carboxylic acid hydrochloride Ak-1 and (4aS,9aR)-7-(difluoromethoxy)-2,3,4,4a,9,9a-hexahydroindeno[2,1-b][1,4]oxazine hydrochloride Eav-3. ES/MS: m/z=470.0 $[M+H]^+$. $^1$H NMR (400 MHz, Methanol-d4) δ 9.29 (d, J=18.4 Hz, 1H), 8.56 (dd, J=18.7, 5.8 Hz, 1H), 8.45-8.30 (m, 1H), 7.48 (dd, J=18.2, 9.7 Hz, 1H), 7.35 (d, J=24.5 Hz, 1H), 7.21-6.92 (m, 2H), 6.87-6.48 (m, 1H), 5.96 (s, 1H), 5.01 (s, 1H, overlapped with solvent),

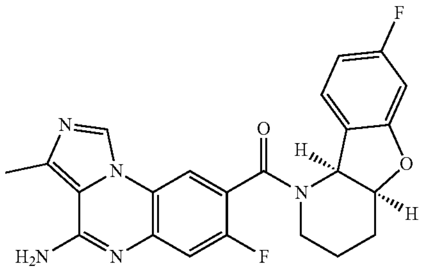 [SMILES: Cc1ncn2c1c(N)nc1cc(F)c(C(=O)N3CCC[C@@H]4Oc5cc(F)ccc5[C@@H]43)cc12]

Example Fg-26: (4-amino-7-fluoro-3-methylimidazo[1,5-a]quinoxalin-8-yl)((4aS,9bS)-7-fluoro-3,4,4a,9b-tetrahydrobenzofuro[3,2-b]pyridin-1(2H)-yl)methanone. Prepared following general procedure VII-F using 4-amino-7-fluoro-3-methylimidazo[1,5-a]quinoxaline-8-carboxylic acid hydrochloride Ak-2 and (4aS,9bS)-7-fluoro-1,2,3,4,4a,9b-hexahydrobenzofuro[3,2-b]pyridine hydrochloride Ew-10. ES/MS: m/z=436.0 $[M+H]^+$. $^1$H NMR (400 MHz, Methanol-d4) δ 9.19 (d, J=6.7 Hz, 1H), 8.54-8.29 (m, 1H), 7.55-7.19 (m, 2H), 6.80-6.47 (m, 2H), 6.32 (d, J=8.6 Hz, 0.6H, major rotamer), 5.51 (d, J=9.0 Hz, 0.4H, minor rotamer), 5.16 (dt, J=8.4, 4.1 Hz, 1H), 3.54-3.38 (m, 1H), 3.03 (dt, J=15.2, 8.0 Hz, 1H), 2.80 (s, 3H), 2.24-1.59 (m, 4H).

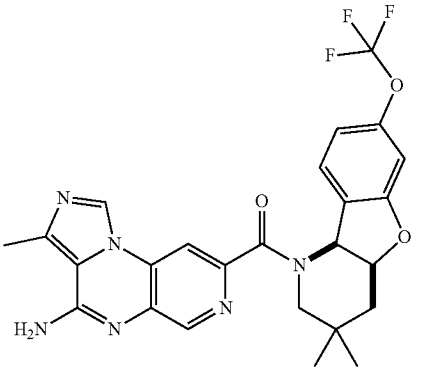

Example Fg-27: (4-amino-3-methylimidazo[1,5-a]pyrido[3,4-e]pyrazin-8-yl)(3,3-dimethyl-7-(trifluoromethoxy)-3,4,4a,9b-tetrahydrobenzofuro[3,2-b]pyridin-1(2H)-yl)methanone. Prepared following general procedure VII-F using 4-amino-3-methylimidazo[1,5-a]pyrido[3,4-e]pyrazine-8-carboxylic acid hydrochloride Ak-4 and 3,3-dimethyl-7-(trifluoromethoxy)-1,2,3,4,4a,9b-hexahydrobenzofuro[3,2-b]pyridine hydrochloride Eba-2. ES/MS: m/z=513.0 $[M+H]^+$. $^1H$ NMR (400 MHz, Methanol-d4) δ 9.27 (d, J=12.8 Hz, 1H), 8.79 (d, J=11.9 Hz, 1H), 8.50 (d, J=38.9 Hz, 1H), 7.64 (dd, J=105.7, 8.2 Hz, 1H), 6.90 (ddd, J=8.2, 2.2, 1.1 Hz, 1H), 6.78 (d, J=23.9 Hz, 1H), 6.10 (dd, J=180.6, 8.4 Hz, 1H), 5.32-4.98 (m, 1H), 4.29 (d, J=13.3 Hz, 1H), 3.59 (d, J=13.8 Hz, 1H), 2.80 (s, 3H), 2.50 (d, J=13.3 Hz, 1H), 1.96-1.71 (m, 2H), 1.19-0.82 (m, 6H).

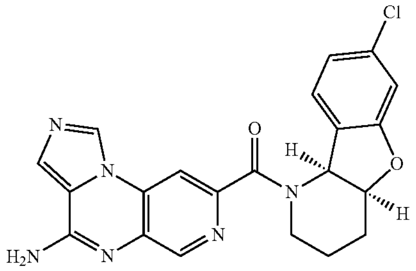 [SMILES: Nc1nc2cnc(C(=O)N3CCC[C@@H]4Oc5cc(Cl)ccc5[C@@H]43)cc2n2cncc12]

Example Fg-28: (4-aminoimidazo[1,5-a]pyrido[3,4-e]pyrazin-8-yl)((4aS,9bS)-7-chloro-3,4,4a,9b-tetrahydrobenzofuro[3,2-b]pyridin-1(2H)-yl)methanone. Prepared following general procedure VII-F using 4-aminoimidazo[1,5-a]pyrido[3,4-e]pyrazine-8-carboxylic acid hydrochloride Ak-5 and (4aS,9bS)-7-chloro-1,2,3,4,4a,9b-hexahydrobenzofuro[3,2-b]pyridine hydrochloride Ew-9. ES/MS: m/z=438.0 $[M+H]^+$. $^1H$ NMR (400 MHz, Methanol-d4) δ 9.30 (d, J=5.9 Hz, 1H), 8.75-8.33 (m, 2H), 7.57-7.16 (m, 2H), 7.09-6.74 (m, 2H), 6.35 (d, J=8.8 Hz, 0.7H, major rotamer), 5.54 (d, J=9.1 Hz, 0.3H, minor rotamer), 5.15 (dt, J=8.5, 4.2 Hz, 1H), 3.57-3.40 (m, 0.4H, minor rotamer), 3.09-2.61 (m, 1.6H, major rotamer), 2.22-1.50 (m, 4H).

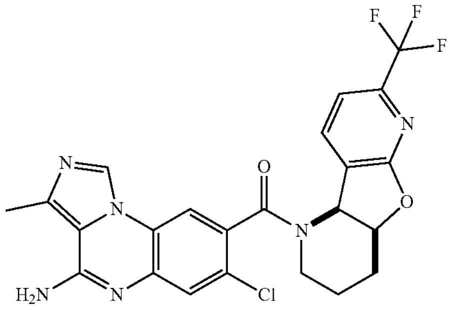

(±)

Example Fg-29: Rac-(4-amino-7-chloro-3-methylimidazo[1,5-a]quinoxalin-8-yl)((4aS,9bS)-7-(trifluoromethyl)-3,4,4a,9b-tetrahydrofuro[2,3-b:4,5-b']dipyridin-1(2H)-yl)methanone. Prepared following general procedure VII-F starting with 4-amino-7-chloro-3-methyl-imidazo[1,5-a]quinoxaline-8-carboxylic acid Aj-2 and cis-(4aS,9bS)-7-(trifluoromethyl)-1,2,3,4,4a,9b-hexahydrofuro[2,3-b:4,5-b']dipyridine hydrochloride Eat-1. ES/MS: m/z=503.0 $[M+H]^+$. $^1H$ NMR (400 MHz, MeOD) δ 9.32-9.08 (m, 1H), 8.52 (s, 0.3H, minor rotamer), 8.43-8.31 (m, 0.7H, major rotamer), 8.12 (d, J=7.4 Hz, 0.3H, minor rotamer), 8.02 (t, J=8.3 Hz, 0.7H, major rotamer), 7.77-7.67 (m, 1H), 7.54-7.30 (m, 1H), 6.59-6.48 (m, 0.7H, major rotamer), 5.73-5.50 (m, 0.3H, minor rotamer), 5.43-5.10 (m, 1H), 4.53-4.45 (m, 0.3H, minor rotamer), 3.43-3.37 (m, 0.7H, major rotamer), 3.14-2.89 (m, 1H), 2.80 (d, J=3.8 Hz, 3H), 2.10 (d, J=14.7 Hz, 2H), 1.92-1.63 (m, 2H).

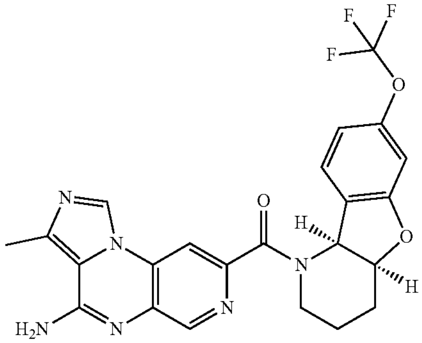 [SMILES: Cc1ncn2c1c(N)nc1cnc(C(=O)N3CCC[C@@H]4Oc5cc(OC(F)(F)F)ccc5[C@@H]43)cc12]

Example Fg-30: (4-amino-3-methylimidazo[1,5-a]pyrido[3,4-e]pyrazin-8-yl)((4aS,9bS)-7-(trifluoromethoxy)-3,4,4a,9b-tetrahydrobenzofuro[3,2-b]pyridin-1(2H)-yl)methanone. Prepared following general procedure VII-F starting with 4-amino-3-methylimidazo[1,5-a]pyrido[3,4-e]pyrazine-8-carboxylic acid hydrochloride Ak-4 and (4aS,9bS)-7-(trifluoromethoxy)-1,2,3,4,4a,9b-hexahydrobenzofuro[3,2-b]pyridine hydrochloride Ew-12. ES/MS: m/z=485.0 $[M+H]^+$. $^1H$ NMR (400 MHz, MeOD) δ 9.26 (s, 1H), 8.84 (s, 0.4H, minor rotamer), 8.79 (s, 0.6H, major rotamer), 8.55 (s, 0.4H, minor rotamer), 8.46 (s, 0.6H, major rotamer), 7.74 (d, J=8.2 Hz, 0.4H, minor rotamer), 7.52 (d, J=8.2 Hz, 0.6H, major rotamer), 6.92-6.85 (m, 1H), 6.82-6.73 (m, 1H), 6.28 (d, J=8.6 Hz, 0.6H, major rotamer), 5.92 (d, J=9.0 Hz, 0.4H, minor rotamer), 5.19 (s, 0.6H, major rotamer), 5.02 (s, 0.4H, minor rotamer), 4.39 (s, 0.4H, minor rotamer), 3.73 (s, 0.6H, major rotamer), 2.98 (d, J=9.4 Hz, 1H), 2.81 (s, 3H), 2.22-1.69 (m, 4H).

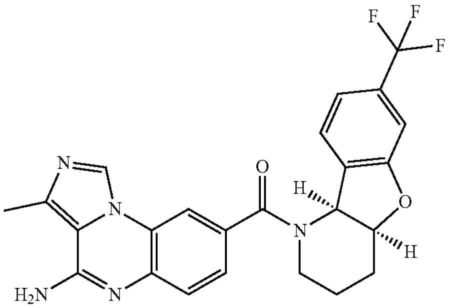 [SMILES: Cc1ncn2c1c(N)nc1ccc(C(=O)N3CCC[C@@H]4Oc5cc(C(F)(F)F)ccc5[C@@H]43)cc12]

Example Fg-31: (4-amino-3-methylimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared following general procedure VII-F starting with 4-amino-3-methylimidazo[1,5-a]quinoxaline-8-carboxylic acid Aa-1 and (4aS,9bS)-7-(trifluoromethyl)-1,2,3,4,4a,9b-hexahydrobenzofuro[3,2-b]pyridine;hydrochloride Ew-1. ES/MS: m/z=468.0 $[M+H]^+$. $^1$H NMR (400 MHz, MeOD) δ 9.24 (s, 1H), 8.38 (s, 1H), 7.76-7.57 (m, 3H), 7.30 (d, J=7.8 Hz, 1H), 7.13 (s, 1H), 6.34 (s, 1H), 5.17 (s, 1H), 3.74-3.43 (m, 1H), 3.06-2.90 (m, 1H), 2.81 (s, 3H), 2.10 (s, 2H), 1.98-1.82 (m, 1H), 1.79-1.69 (m, 1H).

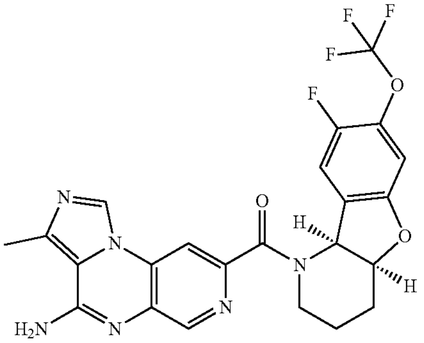 [SMILES: Cc1ncn2c1c(N)nc1cnc(C(=O)N3CCC[C@@H]4Oc5cc(OC(F)(F)F)c(F)cc5[C@@H]43)cc12]

Example Fg-32: (4-amino-3-methylimidazo[1,5-a]pyrido[3,4-e]pyrazin-8-yl)((4aS,9bS)-8-fluoro-7-(trifluoromethoxy)-3,4,4a,9b-tetrahydrobenzofuro[3,2-b]pyridin-1(2H)-yl)methanone. Prepared following general procedure VII-F starting with 7-amino-5-methyl-2,4,8,11-tetrazatricyclo[7.4.0.02,6]trideca-1(13),3,5,7,9,11-hexaene-12-carboxylic acid hydrochloride Ak-4 and (4aS,9bS)-8-fluoro-7-(trifluoromethoxy)-1,2,3,4,4a,9b-hexahydrobenzofuro[3,2-b]pyridine hydrochloride Ew-16. ES/MS: m/z=503.0 $[M+H]^+$. $^1$H NMR (400 MHz, MeOD) δ 9.25 (d, J=4.4 Hz, 1H), 8.88-8.74 (m, 1H), 8.59-8.37 (m, 1H), 7.72 (d, J=9.2 Hz, 0.4H, minor rotamer), 7.42 (d, J=9.1 Hz, 0.6H, major rotamer), 6.93 (dd, J=17.3, 6.0 Hz, 1H), 6.27 (d, J=8.6 Hz, 0.6H, major rotamer), 5.94 (d, J=9.0 Hz, 0.4H, minor rotamer), 5.18 (d, J=8.3 Hz, 0.6H, major rotamer), 5.00 (s, 0.4H, minor rotamer), 4.42 (s, 0.4H, minor rotamer), 3.76 (d, J=12.8 Hz, 0.6H, major rotamer), 3.00 (dd, J=15.1, 8.6 Hz, 1H), 2.80 (s, 3H), 2.23-1.67 (m, 4H).

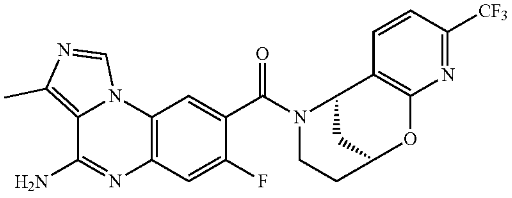

Example Fg-33: (4-amino-7-fluoro-3-methylimidazo[1,5-a]quinoxalin-8-yl)((2S,6R)-9-(trifluoromethyl)-3,4-dihydro-2H-2,6-methanopyrido[2,3-b][1,5]oxazocin-5(6H)-yl)methanone. Prepared using general procedure VII-F starting with 4-amino-7-fluoro-3-methylimidazo[1,5-a]quinoxaline-8-carboxylic acid hydrochloride Ak-2 and (2S,6R)-9-(trifluoromethyl)-3,4,5,6-tetrahydro-2H-2,6-methanopyrido[2,3-b][1,5]oxazocine Ebi-3. ES/MS: m/z=487.3 $[M+H]^+$. $^1$H NMR (400 MHz, MeOD-$d_4$) δ 9.19 (s, 0.3H, minor rotamer), 9.11 (s, 0.7H, major rotamer), 8.47 (d, J=5.8 Hz, 0.3H, minor rotamer), 8.30 (br, 0.7H, major rotamer), 8.00 (d, J=7.5 Hz, 0.7H, major rotamer), 7.66 (br, 0.3H, minor rotamer), 7.61-7.53 (m, 0.3H, minor rotamer), 7.48 (d, J=7.5 Hz, 1H), 7.46-7.30 (m, 0.7H, major rotamer), 6.18 (s, 0.7H, major rotamer), 5.10 (s, 1H), 5.04 (s, 0.3H, minor rotamer), 4.60 (dd, J=14.4, 6.3 Hz, 0.3H, minor rotamer), 3.55 (dd, J=14.4, 5.7 Hz, 0.7H, major rotamer), 3.13-3.01 (m, 0.7H, major rotamer), 2.82 (s, 0.9H, minor rotamer), 2.79 (s, 2.1H, major rotamer), 2.75-2.67 (m, 0.3H, minor rotamer), 2.43 (d, J=14.3 Hz, 0.3H, minor rotamer), 2.38-2.31 (m, 0.7H, major rotamer), 2.31-2.22 (m, 1H), 2.19-1.99 (m, 2H).

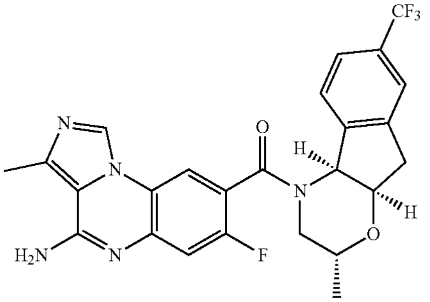 [SMILES: Cc1ncn2c1c(N)nc1cc(F)c(C(=O)N3C[C@@H](C)O[C@@H]4Cc5cc(C(F)(F)F)ccc5[C@@H]43)cc12]

Example Fg-34: (4-amino-7-fluoro-3-methylimidazo[1,5-a]quinoxalin-8-yl)((2R,4aS,9aR)-2-methyl-7-(trifluoromethyl)-2,3,9,9a-tetrahydroindeno[2,1-b][1,4]oxazin-4(4aH)-yl)methanone. Prepared following general procedure VII-F starting with 4-amino-7-fluoro-3-methylimidazo[1,5-a]quinoxaline-8-carboxylic acid hydrochloride Ak-2 and (2R,4aS,9aR)-2-methyl-7-(trifluoromethyl)-2,3,4,4a,9,9a-hexahydroindeno[2,1-b][1,4]oxazine hydrochloride Eaz-10. ES/MS: m/z=500.3 $[M+H]^+$. $^1$H NMR (400 MHz, DMSO-d6) δ 9.29 (s, 0.6H, major rotamer), 9.22 (s, 0.4H, minor rotamer), 8.58 (s, 0.4H, minor rotamer), 8.47 (d, J=6.1 Hz, 0.6H, major rotamer), 8.29 (br, 2H), 7.75-7.59 (m, 2H), 7.58-7.14 (m, 2H), 5.99 (s, 0.6H, major rotamer), 5.01 (s, 0.4H, minor rotamer), 4.71 (d, J=4.2 Hz, 0.6H, major rotamer), 4.61 (t, J=4.1 Hz, 0.4H, minor rotamer), 4.20 (d, J=13.3 Hz, 0.6H, major rotamer), 4.01-3.94 (m, 1H), 3.31-3.24 (m. 0.6H, major rotamer), 3.19-3.14 (m, 1H), 3.09-3.02 (m, 0.4H, minor rotamer), 2.95-2.84 (m, 1H), 2.78 (d, J=16.7 Hz, 0.4H, minor rotamer), 2.70 (s, 1.8H, major rotamer), 2.66 (s, 1.2H, minor rotamer), 1.34 (d, J=6.6 Hz, 1.2H, minor rotamer), 1.21 (d, J=6.7 Hz, 1.8H, major rotamer).

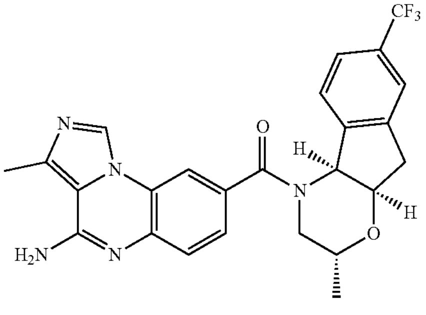 [SMILES: Cc1ncn2c1c(N)nc1ccc(C(=O)N3C[C@@H](C)O[C@@H]4Cc5cc(C(F)(F)F)ccc5[C@@H]43)cc12]

Example Fg-35: (4-amino-3-methylimidazo[1,5-a]quinoxalin-8-yl)((2R,4aS,9aR)-2-methyl-7-(trifluoromethyl)-2,3,9,9a-tetrahydroindeno[2,1-b][1,4]oxazin-4(4aH)-yl) methanone. Prepared following general procedure VII-F starting with 4-amino-3-methylimidazo[1,5-a]quinoxaline-8-carboxylic acid Aa-1 and (2R,4aS,9aR)-2-methyl-7-(trifluoromethyl)-2,3,4,4a,9,9a-hexahydroindeno[2,1-b][1,4] oxazine Eaz-10. ES/MS: m/z=482.3 $[M+H]^+$. $^1$H NMR (400 MHz, DMSO-d6) δ 9.40 (s, 1H), 8.89 (br, 1H), 8.58-8.43 (m, 1H), 7.78-7.49 (m, 4H), 5.93 (s, 0.6H, major rotamer), 5.08 (s, 0.4H, minor rotamer), 4.74-4.61 (m, 1H), 4.19-4.11 (m, 1H), 3.37-3.16 (m, 2H), 3.13-2.96 (m, 1H), 2.95-2.84 (m, 1H), 2.72 (s, 3H), 1.40-1.17 (m, 3H).

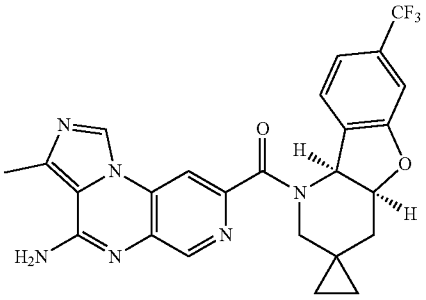 [SMILES: Cc1ncn2c1c(N)nc1cnc(C(=O)N3CC4(CC4)C[C@@H]4Oc5cc(C(F)(F)F)ccc5[C@@H]43)cc12]

Example Fg-36: (4-amino-3-methylimidazo[1,5-a]pyrido[3,4-e]pyrazin-8-yl)((4aS,9bS)-7-(trifluoromethyl)-4a,9b-dihydro-2H-spiro[benzofuro[3,2-b]pyridine-3,1'-cyclopropan]-1(4H)-yl)methanone. Prepared following general procedure VII-F starting with 4-amino-3-methylimidazo[1,5-a]pyrido[3,4-e]pyrazine-8-carboxylic acid hydrochloride Ak-4 and (4aS,9bS)-7-(trifluoromethyl)-1,4,4a,9b-tetrahydro-2H-spiro[benzofuro[3,2-b]pyridine-3,1'-cyclopropane] Ebs-2 (TATU was used instead of Pybrop). ES/MS: m/z=494.8 $[M+H]^+$. $^1$H NMR (400 MHz, Methanol-d4) δ 9.27 (d, J=7.6 Hz, 1H), 8.88-8.65 (m, 1H), 8.57 (s, 0.5H, rotamer), 8.47 (s, 0.5H, rotamer), 7.76 (d, J=7.7 Hz, 0.5H, rotamer), 7.58 (d, J=7.8 Hz, 0.5H, rotamer), 7.27 (d, J=7.8 Hz, 1H), 7.13 (s, 0.5H, rotamer), 7.06 (s, 0.5H, rotamer), 6.53 (d, J=8.8 Hz, 0.5H, rotamer), 6.12 (d, J=8.9 Hz, 0.5H, rotamer), 5.31-5.18 (m, 0.5H, rotamer), 5.18-5.03 (m, 0.5H, rotamer), 4.19-4.03 (m, 1H), 3.19-3.08 (m, 1H), 2.79 (s, 3H), 2.19-2.00 (m, 1H), 1.88-1.65 (m, 1H), 0.59-0.37 (m, 3H), 0.31-0.13 (m, 1H).

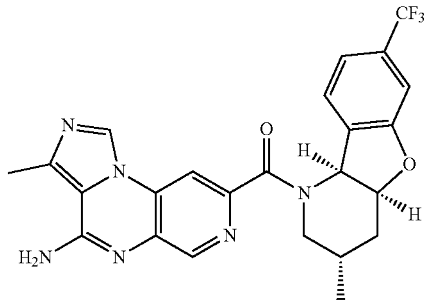 [SMILES: Cc1ncn2c1c(N)nc1cnc(C(=O)N3C[C@@H](C)C[C@@H]4Oc5cc(C(F)(F)F)ccc5[C@@H]43)cc12]

Example Fg-37: (4-amino-3-methylimidazo[1,5-a]pyrido[3,4-e]pyrazin-8-yl)((3S,4aS,9bS)-3-methyl-7-(trifluoromethyl)-3,4,4a,9b-tetrahydrobenzofuro[3,2-b]pyridin-1(2H)-yl)methanone. Prepared following general procedure VII-F starting with 4-amino-3-methylimidazo[1,5-a]pyrido[3,4-e]pyrazine-8-carboxylic acid hydrochloride Ak-4 and (3S,4aS,9bS)-3-methyl-7-(trifluoromethyl)-1,2,3,4,4a,9b-hexahydrobenzofuro[3,2-b]pyridine Ebs-1 (TATU was used instead of Pybrop). ES/MS: m/z=482.8 $[M+H]^+$. $^1$H NMR (400 MHz, Methanol-d4) δ 9.39-9.20 (m, 1H), 8.93-8.72 (m, 1H), 8.56 (s, 0.5H, rotamer), 8.46 (s, 0.5H, rotamer), 7.82 (d, J=7.8 Hz, 0.5H, rotamer), 7.61 (d, J=7.7 Hz, 0.5H, rotamer), 7.33-7.20 (m, 1H), 7.16-6.98 (m, 1H), 6.41 (d, J=9.2 Hz, 0.5H, rotamer), 6.00 (d, J=9.4 Hz, 0.5H, rotamer), 5.37-5.18 (m, 0.5H, rotamer), 5.18-5.02 (m, 0.5H, rotamer), 4.07-3.86 (m, 0.5H, rotamer), 3.41-3.33 (m, 0.5H, rotamer), 3.27-3.16 (m, 0.5H, rotamer), 3.07-2.91 (m, 0.5H, rotamer), 2.80 (s, 1H), 2.28-2.11 (m, 1H), 2.11-1.96 (m, 1H), 1.72-1.54 (m, 1H), 1.11 (d, J=6.7 Hz, 1.5H, rotamer), 0.97 (d, J=6.7 Hz, 1.5H, rotamer).

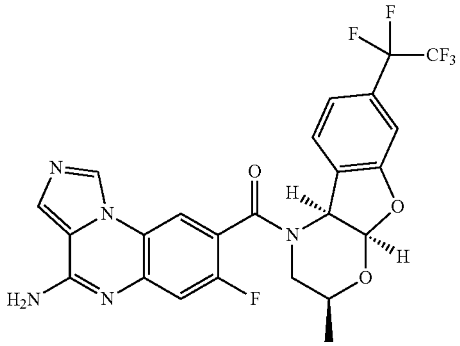 [SMILES: C[C@H]1CN(C(=O)c2cc3c(cc2F)nc(N)c2cncn23)[C@H]2c3ccc(C(F)(F)C(F)(F)F)cc3O[C@H]2O1]

Example Fg-38: (4-amino-7-fluoroimidazo[1,5-a]quinoxalin-8-yl)((2S,4aS,9aR)-2-methyl-7-(perfluoroethyl)-2,3,9,9a-tetrahydroindeno[2,1-b][1,4]oxazin-4(4aH)-yl) methanone. Prepared following general procedure VII-F starting with 4-amino-7-fluoroimidazo[1,5-a]quinoxaline-8-carboxylic acid hydrochloride Ak-1 and (2S,4aS,9aR)-2-methyl-7-(perfluoroethyl)-2,3,4,4a,9,9a-hexahydroindeno[2,1-b][1,4]oxazine Eaz-11 (TATU was used instead of Pybrop). ES/MS: m/z=535.8 $[M+H]^+$. $^1$H NMR (400 MHz, Methanol-d4) δ 9.29 (s, 0.67H, major rotamer), 9.25 (s, 0.33H, minor rotamer), 8.61-8.47 (m, 1H), 8.35 (s, 0.67H, major rotamer), 8.32 (s, 0.33H, minor rotamer), 7.65-7.40 (m, 4H), 6.02 (s, 0.67H, major rotamer), 5.06 (s, 0.33H, minor rotamer), 4.64-4.43 (m, 1H), 3.82-3.64 (m, 1H), 3.50-3.35 (m, 1H), 3.18-2.91 (m, 1H), 2.90-2.78 (m, 0.67H, major rotamer), 2.56 (dd, J=13.3, 10.5 Hz, 0.33H, minor rotamer), 1.14 (d, J=6.3 Hz, 1H, minor rotamer), 0.97 (d, J=6.3 Hz, 2H, major rotamer).

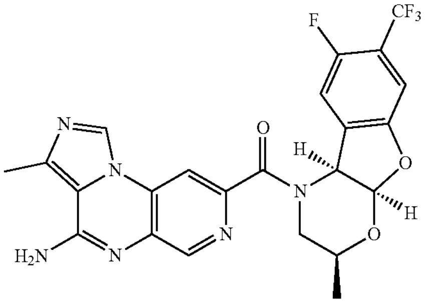 [SMILES: Cc1ncn2c1c(N)nc1cnc(C(=O)N3C[C@H](C)O[C@@H]4Oc5cc(C(F)(F)F)c(F)cc5[C@@H]43)cc12]

Example Fg-39: (4-amino-3-methylimidazo[1,5-a]pyrido[3,4-e]pyrazin-8-yl)((3R,4aS,9bS)-8-fluoro-3-methyl-7-(trifluoromethyl)-3,4,4a,9b-tetrahydrobenzofuro[3,2-b]pyridin-1(2H)-yl)methanone. Prepared following general procedure VII-F starting with 4-amino-3-methylimidazo[1,5-a]pyrido[3,4-e]pyrazine-8-carboxylic acid hydrochloride Ak-4 and (3R,4aS,9bS)-8-fluoro-3-methyl-7-(trifluoromethyl)-1,2,3,4,4a,9bhexahydrobenzofuro[3,2-b]pyridine Ew-6 (TATU was used instead of Pybrop). ES/MS: m/z=500.8 $[M+H]^+$. $^1$H NMR (400 MHz, Methanol-d4) δ 9.25-9.13 (m, 1H), 8.81-8.68 (m, 1H), 8.53 (s, 0.5H, rotamer), 8.47 (s, 0.5H, rotamer), 7.68 (d, J=9.5 Hz, 0.5H, rotamer), 7.37 (d, J=9.3 Hz, 0.5H, rotamer), 7.13 (d, J=5.3 Hz, 0.5H, rotamer), 7.08 (d, J=5.2 Hz, 0.5H, rotamer), 6.30 (d, J=8.4 Hz, 0.5H, rotamer), 5.95 (d, J=8.4 Hz, 0.5H, rotamer), 5.15 (q, J=7.1 Hz, 0.5H, rotamer), 4.99-4.90 (m, 0.5H, rotamer), 4.52 (d, J=13.6 Hz, 0.5H, rotamer), 3.81 (dd, J=13.6, 5.2 Hz, 0.5H, rotamer), 2.78 (s, 3H), 2.65-2.48 (m, 0.5H, rotamer), 2.39-2.09 (m, 2H), 1.99-1.87 (m, 0.5H, rotamer), 1.72-1.57 (m, 0.5H, rotamer), 1.57-1.42 (m, 0.5H, rotamer), 1.03 (d, J=6.7 Hz, 1.5H, rotamer), 0.90 (d, J=6.6 Hz, 1.5H, rotamer).

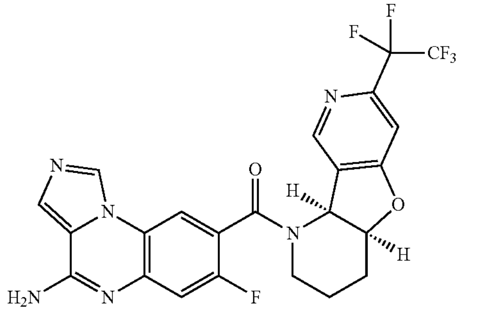 [SMILES: Nc1nc2cc(F)c(C(=O)N3CCC[C@@H]4Oc5cc(C(F)(F)C(F)(F)F)ncc5[C@@H]43)cc2n2cncc12]

Example Fg-40: (4-amino-7-fluoroimidazo[1,5-a]quinoxalin-8-yl)((4aS,9bS)-7-(perfluoroethyl)-3,4,4a,9b-tetrahydrofuro[3,2-b:4,5-c']dipyridin-1(2H)-yl)methanone. Prepared following general procedure VII-F starting with 4-amino-7-fluoroimidazo[1,5-a]quinoxaline-8-carboxylic acid hydrochloride Ak-1 and (4aS,9bS)-7-(perfluoroethyl)-1,2,3,4,4a,9b-hexahydrofuro[3,2-b:4,5-c']dipyridine Ebt-1 (TATU was used instead of Pybrop). ES/MS: m/z=522.8 $[M+H]^+$. $^1$H NMR (400 MHz, Methanol-d4) δ 9.25 (s, 1H), 8.66 (s, 1H), 8.44 (d, J=5.9 Hz, 1H), 8.32 (s, 1H), 7.55-7.29 (m, 2H), 6.49 (d, J=9.3 Hz, 0.7H, major rotamer), 5.83-5.73 (m, 0.3H, minor rotamer), 5.44-5.31 (m, 0.7H, major rotamer), 4.53-4.39 (m, 0.3H, minor rotamer), 3.58-3.42 (m, 1H), 3.10-2.99 (m, 1H), 2.23-2.00 (m, 2H), 1.94-1.80 (m, 1H), 1.79-1.66 (m, 1H).

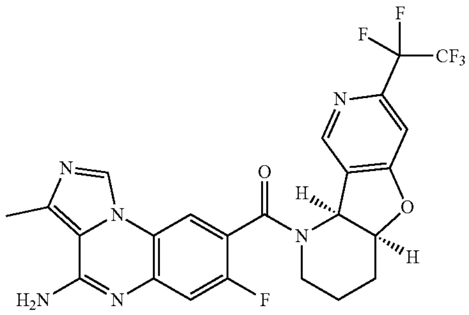 [SMILES: Cc1ncn2c1c(N)nc1cc(F)c(C(=O)N3CCC[C@@H]4Oc5cc(C(F)(F)C(F)(F)F)ncc5[C@@H]43)cc12]

Example Fg-41: (4-amino-7-fluoro-3-methylimidazo[1,5-a]quinoxalin-8-yl)((4aS,9bS)-7-(perfluoroethyl)-3,4,4a,9b-tetrahydrofuro[3,2-b:4,5-c']dipyridin-1(2H)-yl)methanone. Prepared following general procedure VII-F starting with 4-amino-7-fluoro-3-methylimidazo[1,5-a]quinoxaline-8-carboxylic acid hydrochloride Ak-2 and (4aS,9bS)-7-(perfluoroethyl)-1,2,3,4,4a,9b-hexahydrofuro[3,2-b:4,5-c']dipyridine Ebt-1 (TATU was used instead of Pybrop). ES/MS: m/z=536.8 $[M+H]^+$. $^1$H NMR (400 MHz, Methanol-d4) δ 9.14 (s, 1H), 8.74-8.55 (m, 1H), 8.41-8.24 (m, 1H), 7.50-7.27 (m, 2H), 6.55-6.36 (m, 1H), 5.46-5.25 (m, 1H), 3.57-3.41 (m, 1H), 3.20-3.10 (m, 1H), 2.77 (s, 3H), 2.23-1.97 (m, 2H), 1.96-1.79 (m, 1H), 1.78-1.65 (m, 1H).

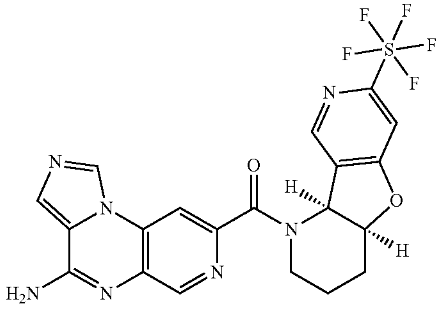 [SMILES: Nc1nc2cnc(C(=O)N3CCC[C@@H]4Oc5cc(S(F)(F)(F)(F)F)ncc5[C@@H]43)cc2n2cncc12]

Example Fg-42: (4-aminoimidazo[1,5-a]pyrido[3,4-e]pyrazin-8-yl)((4aS,9bS)-7-(pentafluoro-16-sulfaneyl)-3,4,4a,9b-tetrahydrobenzofuro[3,2-b]pyridin-1(2H)-yl)methanone. Prepared following general procedure VII-F starting with 4-aminoimidazo[1,5-a]pyrido[3,4-e]pyrazine-8-carboxylic acid hydrochloride Ak-5 and (4aS,9bS)-7-(pentafluoro-16-sulfaneyl)-1,2,3,4,4a,9b-hexahydrobenzofuro[3,2-b]pyridine Ew-21. ES/MS: m/z=513.0 $[M+H]^+$. $^1$H NMR (400 MHz, MeOD) δ 9.35 (s, 1H), 8.85 (d, J=12.2 Hz, 1H), 8.63 (s, 0.5H rotamer), 8.54 (s, 0.5H rotamer), 8.31 (s, 1H), 7.87 (d, J=8.3 Hz, 0.5H rotamer), 7.62 (d, J=8.3 Hz, 0.5H rotamer), 7.47 (dd, J=8.3, 2.0 Hz, 1H), 7.31 (d, J=20.0 Hz, 1H), 6.37 (d, J=8.8 Hz, 0.5H rotamer), 6.04 (d, J=9.1 Hz, 0.5H rotamer), 5.22 (d, J=8.3 Hz, 0.5H rotamer), 5.06 (s, 0.5H rotamer), 4.43 (s, 0.5H rotamer), 3.77 (d, J=11.0 Hz, 0.5H rotamer), 3.07-2.91 (m, 0.5H rotamer), 2.86-2.75 (m, 0.5H rotamer), 2.24-1.62 (m, 4H).

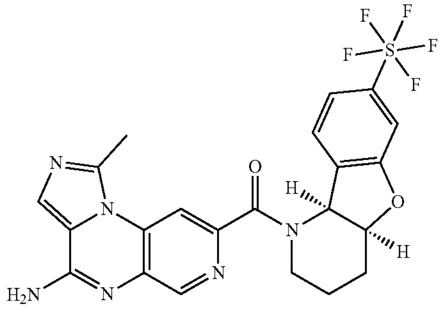 [SMILES: Cc1ncc2c(N)nc3cnc(C(=O)N4CCC[C@@H]5Oc6cc(S(F)(F)(F)(F)F)ccc6[C@@H]54)cc3n12]

Example Fg-43: (4-amino-1-methylimidazo[1,5-a]pyrido[3,4-e]pyrazin-8-yl)((4aS,9bS)-7-(pentafluoro-16-sulfaneyl)-3,4,4a,9b-tetrahydrobenzofuro[3,2-b]pyridin-1(2H)-yl)methanone. Prepared following general procedure VII-F starting with 4-amino-7-chloro-3-methylimidazo[1,5-a]quinoxaline-8-carboxylic acid hydrochloride Ak-3 and (4aS,9bS)-7-(pentafluoro-16-sulfaneyl)-1,2,3,4,4a,9b-hexahydrobenzofuro[3,2-b]pyridine Ew-21. ES/MS: m/z=527.0 $[M+H]^+$. $^1H$ NMR (400 MHz, MeOD) δ 8.82 (s, 1H), 8.49 (d, J=34.2 Hz, 1H), 8.19 (s, 1H), 7.91 (s, 0.5H, rotamer), 7.64 (s, 0.5H, rotamer), 7.47 (dd, J=8.3, 1.9 Hz, 1H), 7.31 (s, 1H), 6.35 (s, 0.5H, rotamer), 6.16 (s, 0.5H, rotamer), 5.22 (s, 0.5H, rotamer), 5.06 (s, 0.5H, rotamer), 4.44 (s, 0.5H, rotamer), 3.90 (s, 0.5H, rotamer), 3.16 (s, 3H), 3.01 (s, 0.5H, rotamer), 2.90-2.77 (m, 0.5H, rotamer), 1.97-2.04 (m, 3H), 1.79 (s, 1H).

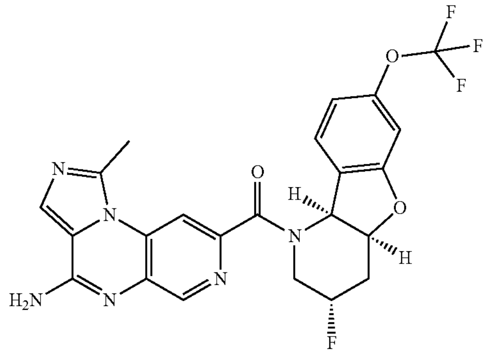

Example Fg-45: (4-amino-1-methylimidazo[1,5-a]pyrido[3,4-e]pyrazin-8-yl)((3S,4aS,9bS)-3-fluoro-7-(trifluoromethoxy)-3,4,4a,9b-tetrahydrobenzofuro[3,2-b]pyridin-1(2H)-yl)methanone. Prepared following general procedure VII-F starting with 4-amino-7-chloro-3-methylimidazo[1,5-a]quinoxaline-8-carboxylic acid hydrochloride Ak-3 and (3S,4aS,9bS)-3-fluoro-7-(trifluoromethoxy)-1,2,3,4,4a,9b-hexahydrobenzofuro[3,2-b]pyridine Ex-2. ES/MS: m/z=503.0 $[M+H]^+$. $^1H$ NMR (400 MHz, MeOD) δ 8.90 (s, 0.5H, rotamer), 8.81 (s, 0.5H, rotamer), 8.59 (s, 0.5H, rotamer), 8.42 (s, 0.5H, rotamer), 8.23 (s, 1H), 7.93 (s, 0.5H, rotamer), 7.59 (s, 0.5H, rotamer), 6.94 (ddd, J=8.3, 2.2, 1.1 Hz, 1H), 6.81 (s, 1H), 6.32 (s, 0.5H, rotamer), 6.18 (s, 0.5H, rotamer), 5.25 (s, 1H), 5.06 (d, J=25.5 Hz, 2H), 4.31 (s, 1H), 3.23-3.04 (m, 3H), 2.78-2.85 (m, 2H), 2.20 (s, 1H).

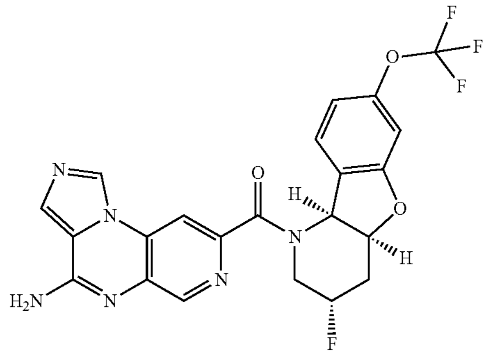 [SMILES: Nc1nc2cnc(C(=O)N3C[C@@H](F)C[C@@H]4Oc5cc(OC(F)(F)F)ccc5[C@@H]43)cc2n2cncc12]

Example Fg-44: (4-aminoimidazo[1,5-a]pyrido[3,4-e]pyrazin-8-yl)((3S,4aS,9bS)-3-fluoro-7-(trifluoromethoxy)-3,4,4a,9b-tetrahydrobenzofuro[3,2-b]pyridin-1(2H)-yl)methanone. Prepared following general procedure VII-F starting with 4-aminoimidazo[1,5-a]pyrido[3,4-e]pyrazine-8-carboxylic acid hydrochloride Ak-5 and (3S,4aS,9bS)-3-fluoro-7-(trifluoromethoxy)-1,2,3,4,4a,9b-hexahydrobenzofuro[3,2-b]pyridine Ex-2. ES/MS: m/z=489.0 $[M+H]^+$. $^1H$ NMR (400 MHz, MeOD) δ 9.36 (s, 0.5H, rotamer), 9.29 (s, 0.5H, rotamer), 8.90 (s, 0.5H, rotamer), 8.80 (s, 0.5H, rotamer), 8.65 (s, 0.5H, rotamer), 8.53 (s, 0.5H, rotamer), 8.27 (s, 1H), 7.89 (d, J=8.3 Hz, 0.5H, rotamer), 7.57 (d, J=8.3 Hz, 0.5H, rotamer), 6.94 (d, J=8.3 Hz, 1H), 6.81 (d, J=16.2 Hz, 1H), 6.35 (d, J=8.3 Hz, 0.5H, rotamer), 6.05 (d, J=8.5 Hz, 0.5H, rotamer), 5.32-4.99 (m, 3H), 4.74-4.80 (m, 0.5H, rotamer), 4.41-4.20 (m, 0.5H, rotamer), 2.96-2.70 (m, 1H), 2.07-2.14 (m, 1H).

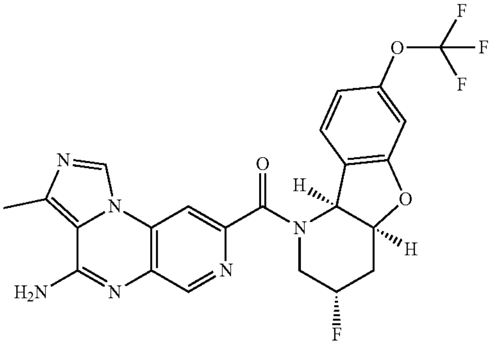 [SMILES: Cc1ncn2c1c(N)nc1cnc(C(=O)N3C[C@@H](F)C[C@@H]4Oc5cc(OC(F)(F)F)ccc5[C@@H]43)cc12]

Example Fg-46: (4-amino-3-methylimidazo[1,5-a]pyrido[3,4-e]pyrazin-8-yl)((3S,4aS,9bS)-3-fluoro-7-(trifluoromethoxy)-3,4,4a,9b-tetrahydrobenzofuro[3,2-b]pyridin-1(2H)-yl)methanone. Prepared following general procedure VII-F starting with 4-amino-3-methylimidazo[1,5-a]pyrido[3,4-e]pyrazine-8-carboxylic acid hydrochloride Ak-4 and (3S,4aS,9bS)-3-fluoro-7-(trifluoromethoxy)-1,2,3,4,4a,9b-hexahydrobenzofuro[3,2-b]pyridine Ex-2. ES/MS: m/z=503.0 $[M+H]^+$. $^1H$ NMR (400 MHz, MeOD) δ 9.25 (s, 0.5H, rotamer), 9.18 (s, 0.5H, rotamer), 8.85 (s, 0.5H, rotamer), 8.74 (s, 0.5H, rotamer), 8.58 (s, 0.5H, rotamer), 8.46 (s, 0.5H, rotamer), 7.88 (d, J=8.1 Hz, 0.5H, rotamer), 7.57 (d, J=8.1 Hz, 0.5H, rotamer), 6.93 (d, J=8.3 Hz, 1H), 6.80 (d, J=16.0 Hz, 1H), 6.34 (d, J=8.2 Hz, 0.5H, rotamer), 6.04 (d, J=8.6 Hz, 0.5H, rotamer), 5.25 (s, 0.5H, rotamer), 5.03 (d, J=35.2 Hz, 3H), 4.49-4.06 (m, 0.5H, rotamer), 2.80 (s, 4H), 2.11 (d, J=48.3 Hz, 1H).

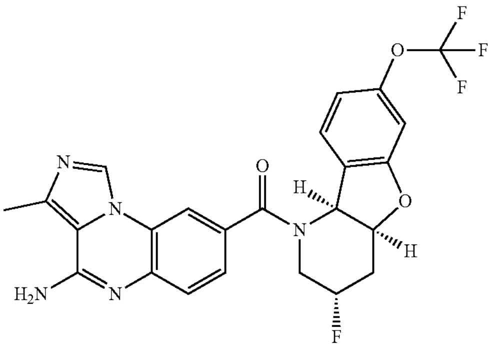 [SMILES: Cc1ncn2c1c(N)nc1ccc(C(=O)N3C[C@@H](F)C[C@@H]4Oc5cc(OC(F)(F)F)ccc5[C@@H]43)cc12]

Example Fg-47: (4-amino-3-methylimidazo[1,5-a]quinoxalin-8-yl)((3S,4aS,9bS)-3-fluoro-7-(trifluoromethoxy)-3,4,4a,9b-tetrahydrobenzofuro[3,2-b]pyridin-1(2H)-yl) methanone. Prepared following general procedure VII-F starting with 4-amino-3-methylimidazo[1,5-a]quinoxaline-8-carboxylic Aa-1 and (3S,4aS,9bS)-3-fluoro-7-(trifluoromethoxy)-1,2,3,4,4a,9b-hexahydrobenzofuro[3,2-b]pyridine Ex-2. ES/MS: m/z=502.0 $[M+H]^+$. $^1H$ NMR (400 MHz, MeOD) δ 9.13 (s, 1H), 8.40 (s, 1H), 7.96-7.47 (m, 3H), 6.94 (d, J=8.3 Hz, 1H), 6.81 (s, 1H), 6.20 (s, 1H), 5.24 (s, 1H), 5.08 (s, 0.5H, rotamer), 4.94 (s, 0.5H, rotamer), 3.87 (s, 1H), 3.22-3.00 (m, 1H), 2.95 (s, 1H), 2.81 (s, 3H), 2.44-2.17 (m, 1H).

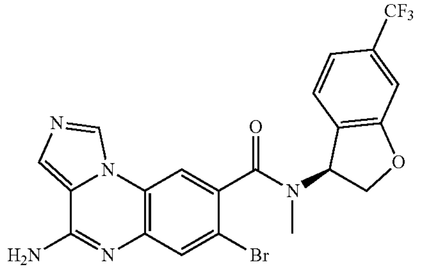 [SMILES: CN(C(=O)c1cc2c(cc1Br)nc(N)c1cncn12)[C@@H]1COc2cc(C(F)(F)F)ccc21]

Example Fg-48: (S)-4-amino-7-bromo-N-methyl-N-(6-(trifluoromethyl)-2,3-dihydrobenzofuran-3-yl)imidazo[1,5-a]quinoxaline-8-carboxamide. Prepared following general procedure VII-F starting with 4-amino-7-bromoimidazo[1,5-a]quinoxaline-8-carboxylic acid Ao-1 and (S)—N-methyl-6-(trifluoromethyl)-2,3-dihydrobenzofuran-3-amine; hydrochloride Eh-1. ES/MS: m/z=506.2, 508.1 $[M+H]^+$. $^1H$ NMR (400 MHz, DMSO-$d_6$) δ 9.35 (s, 0.2H, minor rotamer), 9.25 (s, 0.8H, major rotamer), 9.21 (s, 0.2H, minor rotamer), 8.67 (s, 0.2H, minor rotamer), 8.39 (s, 0.8H, major rotamer), 8.18 (s, 2H), 7.78 (d, J=10.7 Hz, 0.2H, minor rotamer), 7.75 (s, 0.8H, major rotamer), 7.71 (d, J=7.8 Hz, 0.2H, minor rotamer), 7.63 (s, 0.8H, minor rotamer), 7.60 (d, J=8.3 Hz, 0.4H, minor rotamer), 7.34 (d, J=8.0 Hz, 1.6H, major rotamer), 7.30 (d, J=1.4 Hz, 1.6H, major rotamer), 7.25 (d, J=1.5 Hz, 0.4H, minor rotamer), 6.57 (s, 0.8H, major rotamer), 5.48 (dd, J=8.8, 5.0 Hz, 0.2H, minor rotamer), 4.90 (dd, J=10.4, 9.2 Hz, 0.8H, major rotamer), 4.77-4.65 (m, 0.8H, major rotamer), 4.63 (s, 0.2H, minor rotamer), 4.61 (d, J=2.8 Hz, 0.2H, minor rotamer), 2.73 (s, 0.6H, minor rotamer), 2.72 (s, 2.4H, major rotamer).

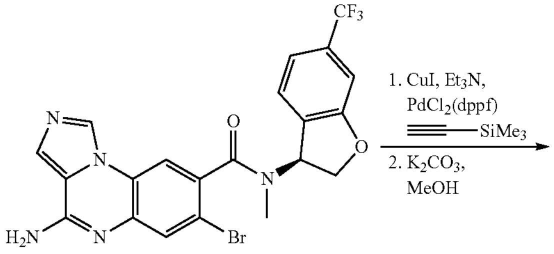

Example Fg-48

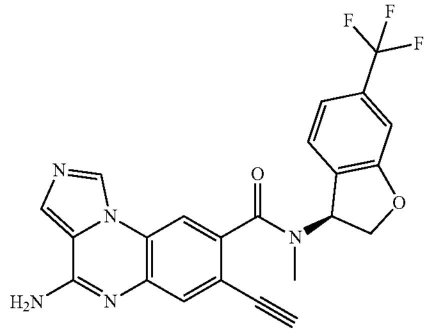

Example Fg-49

Example Fg-49: (S)-4-amino-7-ethynyl-N-methyl-N-(6-(trifluoromethyl)-2,3-dihydrobenzofuran-3-yl)imidazo[1,5-a]quinoxaline-8-carboxamide. To a degassed solution of (S)-4-amino-7-bromo-N-methyl-N-(6-(trifluoromethyl)-2,3-dihydrobenzofuran-3-yl)imidazo[1,5-a]quinoxaline-8-carboxamide (75.0 mg, 0.150 mmol) and triethylamine (75.0 mg, 0.10 mL, 0.74 mmol) in THF (5.0 mL) under an atmosphere of argon was added CuI (1.4 mg, 0.0074 mmol), 1,1'-bis(diphenylphosphino)ferrocene-palladium(II)dichloride dichloromethane complex (12.0 mg, 0.015 mmol), and trimethylsilylacetylene (73.0 mg, 0.10 mL) then heated at 90° C. overnight. The mixture was filtered through a pad of celite and the solvent removed under reduced pressure. The crude was redissolved in MeOH (3.0 mL), treated with potassium carbonate (41 mg, 0.30 mmol), and stirred at rt. The mixture was neutralized with saturated aqueous saturated ammonium chloride, transferred to a separatory funnel, and extracted with ethyl acetate. The organic extracts were washed with brine, dried over $MgSO_4$, filtered, and concentrated under reduced pressure. Purification of the crude residue by reverse-phase HPLC afforded the title compound. ES/MS: m/z=451.2 $[M+H]^+$. $^1H$ NMR (400 MHz, DMSO-$d_6$) δ 9.41 (s, 0.4H, minor rotamer), 9.35 (s, 0.6H, major rotamer), 9.29 (s, 0.4H, minor rotamer), 8.68 (s, 0.4H, minor rotamer), 8.43 (s, 0.6H, major rotamer), 8.32 (s, 0.6, major rotamer), 7.69 (s, 0.4H, minor rotamer), 7.66 (s, 0.6H, major rotamer), 7.62 (d, J=7.7 Hz, 0.4H, minor rotamer), 7.57 (d, J=7.8 Hz, 0.6H, major rotamer), 7.36 (dd, J=8.0, 1.5 Hz, 0.6H, major rotamer), 7.33 (d, J=7.6 Hz, 0.4H, minor rotamer), 7.30 (d, J=1.5 Hz, 0.6H, major rotamer), 7.26 (d, J=1.4 Hz, 0.4H, minor rotamer), 6.56 (dd, J=9.4, 4.1 Hz, 0.6H, major rotamer), 5.46 (t, J=6.9 Hz, 0.4H, minor rotamer), 4.90 (dd, J=10.4, 9.2 Hz, 1H), 4.66 (dd, J=10.3, 4.3 Hz, 1H), 4.62 (s, 0.6H, major rotamer), 4.56 (s, 0.4H, minor rotamer), 2.71 (s, 1H), 2.53 (s, 2H).

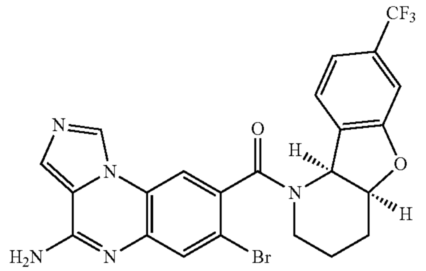 [SMILES: Nc1nc2cc(Br)c(C(=O)N3CCC[C@@H]4Oc5cc(C(F)(F)F)ccc5[C@@H]43)cc2n2cncc12]

Example Fg-50: (4-amino-7-bromoimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. Prepared following general procedure VII-F starting with 4-amino-7-bromoimidazo[1,5-a]quinoxaline-8-carboxylic acid Ao-1 and (4aS,9bS)-7-(trifluoromethyl)-1,2,3,4,4a,9b-hexahydrobenzofuro[3,2-b]pyridine Ew-1. ES/MS: m/z=532.4, 534.2 $[M+H]^+$.

$^1$H NMR (400 MHz, DMSO-$d_6$) δ 9.34 (s, 0.3H, minor rotamer), 9.26 (d, J=3.5 Hz, 0.7H, major rotamer), 8.70-8.65 (m, 0.7H, major rotamer), 8.41 (s, 0.3H, minor rotamer), 8.35 (s, 0.3H, minor rotamer), 8.29 (s, 0.3H, minor rotamer), 8.16-8.09 (m, 1H), 7.75 (d, J=6.7 Hz, 0.7H, major rotamer), 7.71 (d, J=7.0 Hz, 0.7H, major rotamer), 7.67 (d, J=7.7 Hz, 0.3H, minor rotamer), 7.61 (d, J=7.7 Hz, 0.7H, major rotamer), 7.37 (d, J=7.8 Hz, 0.3H, minor rotamer), 7.33 (d, J=7.7 Hz, 0.7H, major rotamer), 7.28 (m, 0.7H, major rotamer), 7.18 (d, J=1.5 Hz, 0.3H, minor rotamer), 6.44 (d, J=9.2 Hz, 0.7H, major rotamer), 6.40 (d, J=9.1 Hz, 0.3H, minor rotamer), 5.54 (d, J=9.2 Hz, 0.3H, minor rotamer), 5.45-5.40 (m, 0.7H, major rotamer), 5.23 (m, J=9.2, 4.6 Hz, 0.7H, major rotamer), 5.15 (m, J=9.0, 4.7 Hz, 0.3H, minor rotamer), 4.40-4.30 (m, 0.3H, minor rotamer), 4.30-4.07 (m, 0.7H, major rotamer), 2.91-2.84 (m, 0.7H, major rotamer), 2.76-2.64 (m, 0.3H, minor rotamer), 1.93-1.89 (m, 1H), 1.74 (d, J=5.6 Hz, 1H), 1.66-1.60 (m, 1H), 1.54-1.47 (m, 1H).

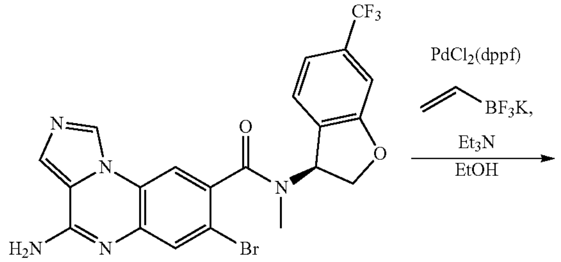

Example Fg-48

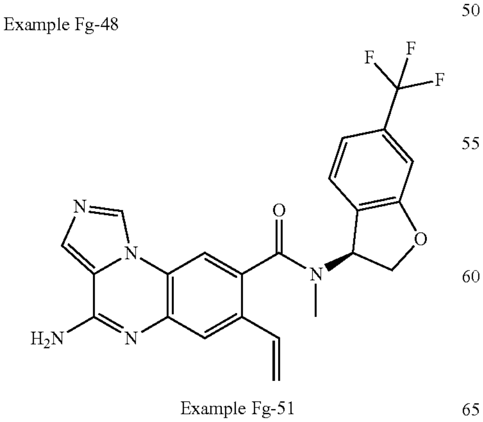

Example Fg-51

Example Fg-51: (S)-4-amino-N-methyl-N-(6-(trifluoromethyl)-2,3-dihydrobenzofuran-3-yl)-7-vinylimidazo[1,5-a]quinoxaline-8-carboxamide. A degassed solution of (S)-4-amino-7-bromo-N-methyl-N-(6-(trifluoromethyl)-2,3-dihydrobenzofuran-3-yl)imidazo[1,5-a]quinoxaline-8-carboxamide (Example Fg-48, 500.0 mg, 0.99 mmol), potassium vinyltrifluoroborate (265 mg, 2.0 mmol), 1,1'-Bis(diphenylphosphino)ferrocene-palladium(II)dichloride dichloromethane complex (82 mg, 0.099 mmol), and triethylamine (0.69 mL, 4.9 mmol) in EtOH (35 mL) was heated at 80° C. monitoring with LCMS. The reaction was filtered through celite, concentrated under reduced pressure, and purified by reverse-phase HPLC to afford the title compound. ES/MS: m/z=454.2 $[M+H]^+$. $^1$H NMR (400 MHz, DMSO-d6) δ 9.42 (s, 0.3H, minor rotamer), 9.32 (s, 0.7H, major rotamer), 8.59 (s, 0.3H, minor rotamer), 8.32 (s, 0.7H, major rotamer), 7.82 (s, 0.3H, minor rotamer), 7.80 (s, 0.7H, major rotamer), 7.70 (d, J=7.9 Hz, 0.3H, minor rotamer), 7.65 (d, J=7.8 Hz, 0.3H, major rotamer), 7.42-7.36 (m, 0.7H, major rotamer), 7.33 (d, J=8.3 Hz, 0.7H, major rotamer), 7.30 (d, J=1.5 Hz, 0.7H, major rotamer), 7.24 (d, J=1.4 Hz, 0.3H, minor rotamer), 6.90 (dd, J=17.4, 11.0 Hz, 0.3H, minor rotamer), 6.78 (dd, J=17.3, 11.0 Hz, 0.7H, major rotamer), 6.76-6.68 (m, 0.3H, minor rotamer), 6.54 (dd, J=9.3, 4.0 Hz, 0.7H, major rotamer), 5.98 (d, J=17.4 Hz, 0.3H, minor rotamer), 5.88 (d, J=17.4 Hz, 0.7H, major rotamer), 5.62 (d, J=11.1 Hz, 0.3H, minor rotamer), 5.56-5.48 (m, 0.7H, major rotamer), 4.90 (m, J=10.4, 9.2 Hz, 0.7H, major rotamer), 4.71 (dd, J=10.4, 4.2 Hz, 0.7H, major rotamer), 4.66-4.59 (m, 0.3H, minor rotamer), 4.48 (t, J=9.8 Hz, 0.3H, minor rotamer), 2.74 (s, J=11.1 Hz, 0.9H, minor rotamer), 2.46 (s, 2.1H, major

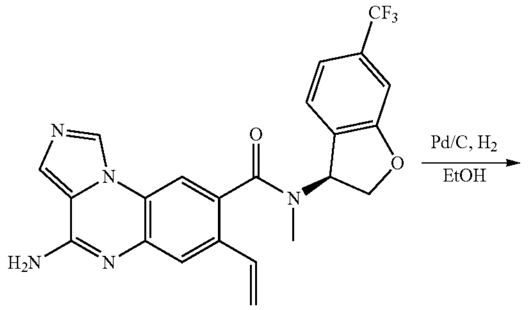

Example Fg-51

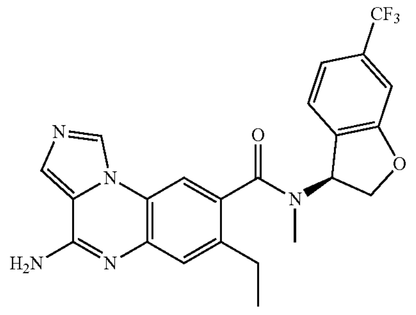

Example Fg-52

Example Fg-52: (S)-4-amino-7-ethyl-N-methyl-N-(6-(trifluoromethyl)-2,3-dihydrobenzofuran-3-yl)imidazo[1,5-a]quinoxaline-8-carboxamide. A suspension of (S)-4-amino-N-methyl-N-(6-(trifluoromethyl)-2,3-dihydrobenzofuran-3-yl)-7-vinylimidazo[1,5-a]quinoxaline-8-carboxamide (61 mg, 0.13 mmol) and 10% palladium on carbon (14 mg, 0.13 mmol) in EtOH (5 mL) was evacuated and backfilled with $H_2$ three times then stirred at rt. Upon completion, the reaction was passed through celite, concentrated under reduced pressure and purified by reverse-phase HPLC to afford the title compound. ES/MS: m/z=454.2 $[M+H]^+$.

$^1$H NMR (400 MHz, DMSO-$d_6$) δ 9.42 (s, 0.3H, minor rotamer), 9.32 (s, 0.7H, major rotamer), 8.59 (s, 0.3H, minor rotamer), 8.32 (s, 0.7H, major rotamer), 7.82 (s, 0.3H, minor rotamer), 7.80 (s, 0.7H, major rotamer), 7.70 (d, J=7.9 Hz, 0.3H, minor rotamer), 7.65 (d, J=7.8 Hz, 0.7H, major rotamer), 7.42-7.36 (m, 0.7H, major rotamer), 7.33 (d, J=8.3 Hz, 0.3H, minor rotamer), 7.30 (d, J=1.5 Hz, 0.7H, major rotamer), 7.24 (d, J=1.4 Hz, 0.3H, minor rotamer), 6.90 (dd, J=17.4, 11.0 Hz, 0.3H, minor rotamer), 6.78 (dd, J=17.3, 11.0 Hz, 0.7H, major rotamer), 6.76-6.68 (m, 0.3H, minor rotamer), 6.54 (dd, J=9.3, 4.0 Hz, 0.7H, major rotamer), 5.98 (d, J=17.4 Hz, 0.3H, minor rotamer), 5.88 (d, J=17.4 Hz, 0.7H, major rotamer), 5.62 (d, J=11.1 Hz, 0.3H, minor rotamer), 5.56-5.48 (m, 0.7H, major rotamer), 4.90 (m, J=10.4, 9.2 Hz, 0.7H, major rotamer), 4.71 (dd, J=10.4, 4.2 Hz, 0.7H, major rotamer), 4.66-4.59 (m, 0.3H, minor rotamer), 4.48 (t, J=9.8 Hz, 0.3H, minor rotamer), 2.74 (s, J=11.1 Hz, 0.9H, minor rotamer), 2.46 (s, 2.1H, major rotamer).

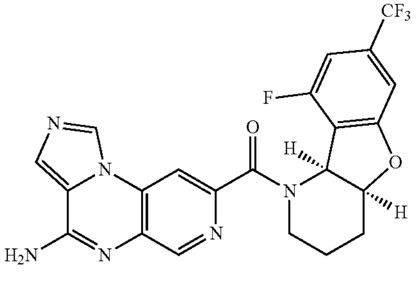 [SMILES: Nc1nc2cnc(C(=O)N3CCC[C@@H]4Oc5cc(C(F)(F)F)cc(F)c5[C@@H]43)cc2n2cncc12]

Example Fg-53: (4-aminoimidazo[1,5-a]pyrido[3,4-e]pyrazin-8-yl)((4aS,9bS)-9-fluoro-7-(trifluoromethyl)-3,4,4a,9b-tetrahydrobenzofuro[3,2-b]pyridin-1(2H)-yl)methanone. Prepared following general procedure VII-F starting with 4-aminoimidazo[1,5-a]pyrido[3,4-e]pyrazine-8-carboxylic acid Ak-5 and cis-9-fluoro-7-(trifluoromethyl)-1,2,3,4,4a,9b-hexahydrobenzofuro[3,2-b]pyridine Ebx-1 (TATU was used instead of Pybrop). Separation by chiral SFC (AD-H column, 45% MeOH, 60 mL/min) afforded the title compound (peak 1, RT=6.0 min). ES/MS: m/z=472.8 $[M+H]^+$. $^1$H NMR (400 MHz, Methanol-d4) δ 9.48-9.25 (m, 1H), 8.85-8.73 (m, 1H), 8.65-8.40 (m, 1H), 8.31 (s, 1H), 7.13-6.84 (m, 2H), 6.68-6.51 (m, 1H), 5.35-5.25 (m, 1H), 4.47-4.28 (m, 0.5H, rotamer), 3.95-3.77 (m, 0.5H, rotamer), 3.10-2.82 (m, 1H), 2.25-1.61 (m, 4H).

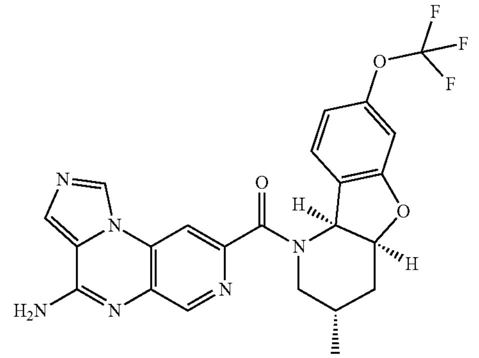 [SMILES: C[C@H]1C[C@@H]2Oc3cc(OC(F)(F)F)ccc3[C@@H]2N(C(=O)c2cc3c(cn2)nc(N)c2cncn23)C1]

Example Fg-54: (4-aminoimidazo[1,5-a]pyrido[3,4-e]pyrazin-8-yl)((3S,4aS,9bS)-3-methyl-7-(trifluoromethoxy)-3,4,4a,9b-tetrahydrobenzofuro[3,2-b]pyridin-1(2H)-yl)methanone. Prepared following general procedure VII-F starting with 4-aminoimidazo[1,5-a]pyrido[3,4-e]pyrazine-8-carboxylic acid hydrochloride Ak-5 and (3S,4aS,9bS)-3-methyl-7-(trifluoromethoxy)-1,2,3,4,4a,9b-hexahydrobenzofuro[3,2-b]pyridine Ebs-3. ES/MS: m/z=485.0 $[M+H]^+$. $^1$H NMR (400 MHz, MeOD) δ 9.33 (s, 1H), 8.85 (s, 1H), 8.54 (d, J=37.8 Hz, 1H), 8.25 (s, 1H), 7.74 (s, 1H), 7.55 (s, 1H), 6.88 (d, J=8.2 Hz, 1H), 6.76 (d, J=12.6 Hz, 1H), 6.36 (s, 0.5H, rotamer), 5.97 (s, 0.5H, rotamer), 5.24 (s, 1H), 5.10 (s, 1H), 3.98 (s, 0.5H, rotamer), 3.02 (s, 0.5H, rotamer), 2.36-1.96 (m, 1H), 1.62 (s, 1H), 1.13 (s, 1.3H, minor rotamer), 0.99 (s, 1.7H, major rotamer).

Example Fg-55: (4-aminoimidazo[1,5-a]pyrido[3,4-e]pyrazin-8-yl)((4aS,9bS)-9-fluoro-7-(trifluoromethoxy)-3,4,4a,9b-tetrahydrobenzofuro[3,2-b]pyridin-1(2H)-yl)methanone. Prepared following general procedure VII-F starting with 4-aminoimidazo[1,5-a]pyrido[3,4-e]pyrazine-8-carboxylic acid hydrochloride Ak-5 and cis-(4aS,9bS)-9-fluoro-7-(trifluoromethoxy)-1,2,3,4,4a,9b-hexahydrobenzofuro[3,2-b]pyridine hydrochloride Eba-4 (TATU was used instead of pybrop). The isomers were separated using SFC separation (AD-H 4.6×100 mm 5 mic, EtOH 40%, 3.0 mL/min). Example Fg-55 was isolated as peak 1 (RT=4.01 min).

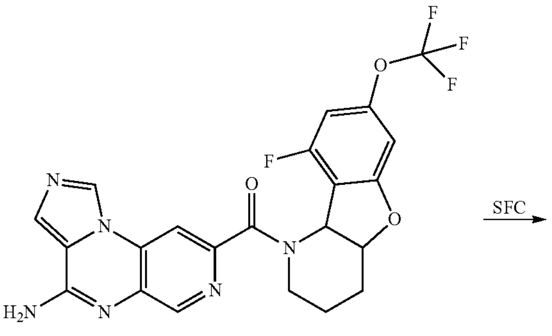

Example Ff-351

-continued

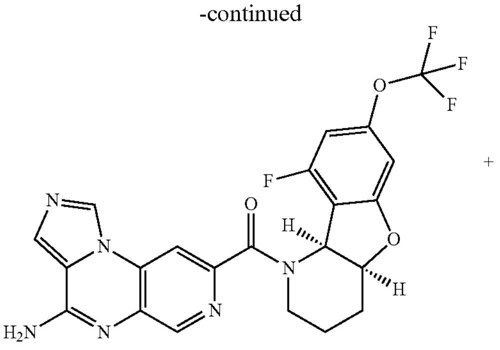

Example Fg-55
Peak 1

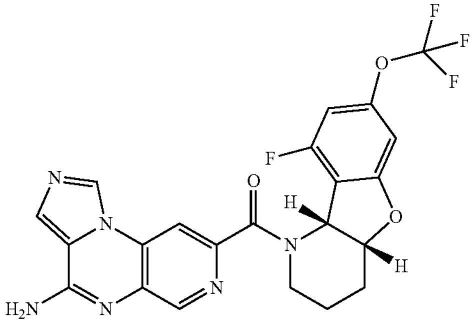

Peak 2

ES/MS: m/z=489.0 [M+H]$^+$. $^1$H NMR (400 MHz, Methanol-d4) δ 9.36 (s, 1H), 8.82 (s, 1H), 8.58 (s, 0.4H, rotamer), 8.49 (s, 0.6H, major rotamer), 8.28 (s, 1H), 6.75-6.50 (m, 3H), 5.32-5.23 (m, 1H), 4.40 (s, 0.4H, minor rotamer), 3.83 (s, 0.6H, major rotamer), 3.02 (s, 0.6H, major rotamer), 2.92 (s, 0.4H, minor rotamer), 2.44-1.88 (m, 3H), 1.89-1.63 (m, 1H).

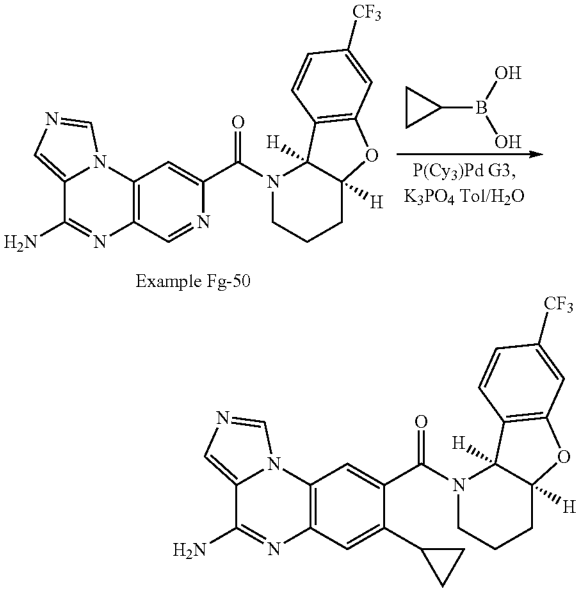

Example Fg-50

Example Fg-56

Example Fg-56: (4-amino-7-cyclopropylimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone. A degassed 9:1 toluene:$H_2O$ (3 mL) solution of example Fg-50 (4-amino-7-bromoimidazo[1,5-a]quinoxalin-8-yl)((4aS,9bS)-7-(trifluoromethyl)-3,4,4a,9b-tetrahydrobenzofuro[3,2-b]pyridin-1(2H)-yl)methanone (86.0 mg, 0.16 mmol), cyclopropylboronic acid (167 mg, 1.9 mmol), P($Cy_3$) Pd G3 (16 mg, 0.024 mmol), and potassium phosphate tribasic (103 mg, 0.48 mmol) was stirred at 90° C. monitoring with LCMS. The reaction was filtered through celite, concentrated under reduced pressure, and purified by reverse-phase HPLC to afford the title compound. ES/MS: m/z=494.3 [M+H]$^+$. $^1$H NMR (400 MHz, DMSO-$d_6$) δ 9.43 (s, 0.3H, minor rotamer), 9.37 (s, 1H), 8.59 (s, 0.7H, major rotamer), 8.37 (s, 0.7H, major rotamer), 8.36 (s, 0.3H, minor rotamer), 8.31 (s, 0.7H, major rotamer), 8.26 (s, 0.3H, minor rotamer), 8.20 (s, 0.3H, minor rotamer), 7.80-7.73 (m, 0.7H, major rotamer), 7.68 (d, J=7.8 Hz, 0.3H, minor rotamer), 7.58-7.51 (m, 0.7H, major rotamer), 7.43 (d, J=7.7 Hz, 0.3H, minor rotamer), 7.37 (d, J=7.9 Hz, 0.3H, minor rotamer), 7.32 (d, J=7.3 Hz, 0.7H, major rotamer), 7.27 (d, J=1.6 Hz, 0.7H, major rotamer), 7.18 (d, J=1.6 Hz, 0.3H, minor rotamer), 7.17 (s, 0.7H, major rotamer), 7.12-7.11 (m, 0.7H, major rotamer), 7.10 (s, 0.3H, minor rotamer), 6.44 (d, J=9.1 Hz, 0.3H, minor rotamer), 6.41 (d, J=8.9 Hz, 0.7H, major rotamer), 5.57-5.49 (m, 0.3H, minor rotamer), 5.45-5.35 (m, 0.7H, major rotamer), 5.25 (m, 1H), 5.10 (q, J=9.5, 4.8 Hz, 0.7H, major rotamer), 4.41 (q, J=13.6, 6.9 Hz, 0.7H, major rotamer), 3.28-3.07 (m, 1H), 2.80 (m, 1H), 2.07-1.98 (m, 1H), 1.93 (m, 1H), 1.74-1.57 (m, 1H), 1.52 (s, 1H), 1.16-1.07 (m, 1H), 1.07-1.00 (m, 0.3H, minor), 0.98-0.76 (m, 0.7H), 0.71 (q, J=4.6, 4.2 Hz, 0.7H, major rotamer), 0.59 (q, J=9.3, 6.8 Hz, 0.3H, minor rotamer).

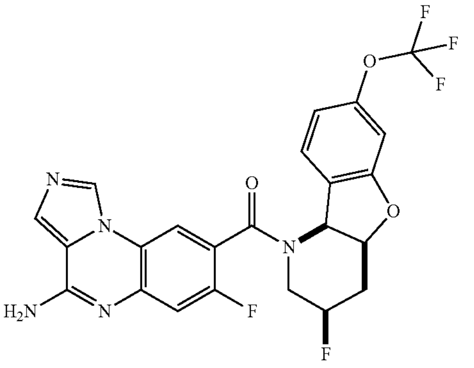

(±)

Example Fg-57: rac-(4-amino-7-fluoroimidazo[1,5-a]quinoxalin-8-yl)((3R,4aS,9bS)-3-fluoro-7-(trifluoromethoxy)-3,4,4a,9b-tetrahydrobenzofuro[3,2-b]pyridin-1(2H)-yl)methanone. Prepared following general procedure VII-F starting with 4-amino-7-fluoroimidazo[1,5-a]quinoxaline-8-carboxylic acid hydrochloride Ak-1 and cis-(3R,4aS,9bS)-3-fluoro-7-(trifluoromethoxy)-1,2,3,4,4a,9b-hexahydrobenzofuro[3,2-b]pyridine Ev-10. (TATU was used instead of pybrop in step 1). ES/MS: m/z=506.0 [M+H]$^+$. $^1$H NMR (400 MHz, Methanol-d4) δ 9.25 (s, 1H), 8.52 (s, 0.3H, minor rotamer), 8.40 (d, J=5.9 Hz, 0.7H, major rotamer), 8.32 (s, 1H), 7.59 (d, J=8.4 Hz, 1H), 7.44 (d, J=9.9 Hz, 0.7H, major rotamer), 7.38 (s, 0.3H, minor rotamer), 6.94 (d, J=8.3 Hz, 1H), 6.84 (s, 0.7H, major rotamer), 6.77 (s, 0.3H, minor rotamer), 6.28 (d, J=8.4 Hz, 1H), 5.59 (s, 0.3H, minor rotamer), 5.26 (d, J=8.5 Hz, 0.7H, major rotamer), 5.22-5.02

(m, 1H), 3.90 (brs, 1H), 3.04-2.88 (m, 0.7H, major rotamer), 2.84-2.68 (m, 0.3H, minor rotamer), 2.68-2.24 (m, 2H).

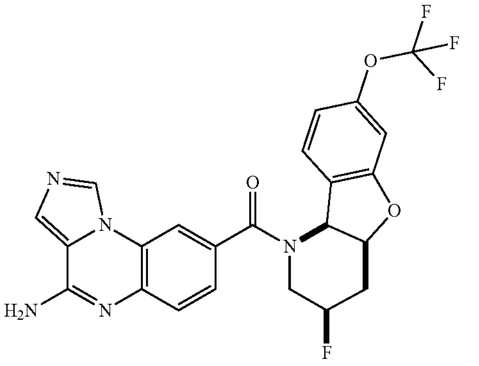

(±)

Example Fg-58: rac-(4-aminoimidazo[1,5-a]quinoxalin-8-yl)((3R,4aS,9bS)-3-fluoro-7-(trifluoromethoxy)-3,4,4a,9b-tetrahydrobenzofuro[3,2-b]pyridin-1(2H)-yl)methanone. Prepared following general procedure VII-F starting with 4-aminoimidazo[1,5-a]quinoxaline-8-carboxylic acid hydrochloride Ak-6 and cis-(3R,4aS,9bS)-3-fluoro-7-(trifluoromethoxy)-1,2,3,4,4a,9b-hexahydrobenzofuro[3,2-b]pyridine Ev-10. (TATU was used instead of pybrop in step 1). ES/MS: m/z=488.0 $[M+H]^+$. $^1H$ NMR (400 MHz, Methanol-d4) δ 9.32 (s, 1H), 8.41 (s, 1H), 8.36 (s, 1H), 7.71 (d, J=8.3 Hz, 1H), 7.60 (d, J=8.2 Hz, 1H), 6.93 (d, J=8.3 Hz, 1H), 6.82 (s, 1H), 6.09 (s, 1H), 5.23 (s, 1H), 5.11 (d, J=7.4 Hz, 1H), 4.08 (m, 2H), 2.88 (brs, 1H), 2.64-2.36 (m, 2H).

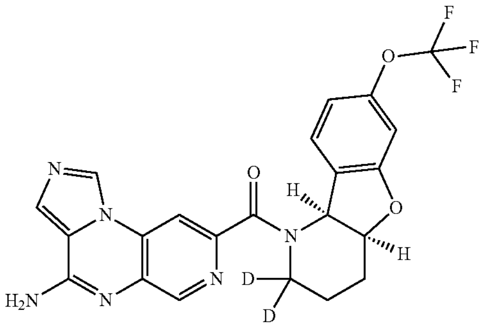 [SMILES: [2H]C1([2H])CC[C@@H]2Oc3cc(OC(F)(F)F)ccc3[C@@H]2N1C(=O)c1cc2c(cn1)nc(N)c1cncn12]

Example Fg-59: (4-aminoimidazo[1,5-a]pyrido[3,4-e]pyrazin-8-yl)((4aS,9bS)-7-(trifluoromethoxy)-3,4,4a,9b-tetrahydrobenzofuro[3,2-b]pyridin-1(2H)-yl-2,2-d2)methanone. Prepared following general procedure VII-F starting with 4-aminoimidazo[1,5-a]pyrido[3,4-e]pyrazine-8-carboxylic acid hydrochloride Ak-5 and (4aS,9bS)-7-(trifluoromethoxy)-1,2,3,4,4a,9b-hexahydrobenzofuro[3,2-b]pyridine-2,2-d2 Ey-3. ES/MS: m/z=473.2 $[M+H]^+$. $^1H$ NMR (400 MHz, DMSO-$d_6$) δ 9.34 (d, J=2.6 Hz, 1H), 8.71 (s, 0.5H rotamer), 8.67 (s, 0.5H rotamer), 8.62 (s, 0.5H rotamer), 8.52 (s, 0.5H rotamer), 8.04 (s, 1H), 7.95 (brs, 2H), 7.77 (d, J=8.2 Hz, 0.5H rotamer), 7.42 (d, J=8.8 Hz, 0.5H rotamer), 6.96 (s, 1H), 6.64 (s, 0.5H rotamer), 6.90 (s, 0.5H rotamer), 6.19 (d, J=8.7 Hz, 0.5H rotamer), 5.88 (d, J=8.9 Hz, 0.5H rotamer), 5.24-5.15 (m, 0.5H rotamer), 5.05-4.96 (m, 0.5H rotamer), 2.08-1.48 (m, 4H).

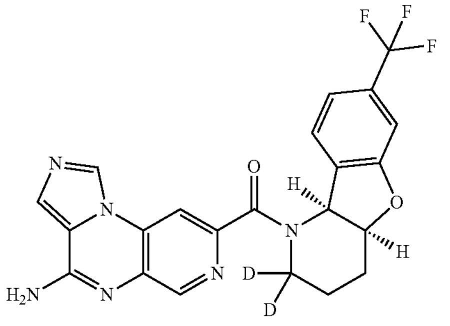 [SMILES: [2H]C1([2H])CC[C@@H]2Oc3cc(C(F)(F)F)ccc3[C@@H]2N1C(=O)c1cc2c(cn1)nc(N)c1cncn12]

Example Fg-60: (4-aminoimidazo[1,5-a]pyrido[3,4-e]pyrazin-8-yl)((4aS,9bS)-7-(trifluoromethyl)-3,4,4a,9b-tetrahydrobenzofuro[3,2-b]pyridin-1(2H)-yl-2,2-d2)methanone. Prepared following general procedure VII-F starting with 4-aminoimidazo[1,5-a]pyrido[3,4-e]pyrazine-8-carboxylic acid hydrochloride Ak-5 and (4aS,9bS)-7-(trifluoromethyl)-1,2,3,4,4a,9b-hexahydrobenzofuro[3,2-b]pyridine-2,2-d2 Ey-1. ES/MS: m/z=457.3 $[M+H]^+$. $^1H$ NMR (400 MHz, Methanol-$d_4$) δ 8.54 (s, 1H), 8.06 (s, 0.5H rotamer), 8.02 (s, 0.5H rotamer), 7.81 (s, 0.5H rotamer), 7.73 (s, 0.5H rotamer), 7.52 (s, 1H), 7.03 (d, J=7.8 Hz, 0.5H rotamer), 6.79 (d, J=7.8 Hz, 0.5H rotamer), 6.48 (d, J=1.5 Hz, 0.5H rotamer), 6.46 (s, 0.5H rotamer), 6.32 (s, 0.5H rotamer), 6.27 (s, 0.5H rotamer), 5.54 (d, J=8.7 Hz, 0.5H rotamer), 5.19 (d, J=9.0 Hz, 0.5H rotamer), 4.43-4.33 (m, 0.5H rotamer), 4.29-4.14 (m, 0.5H rotamer), 1.41-0.81 (m, 4H).

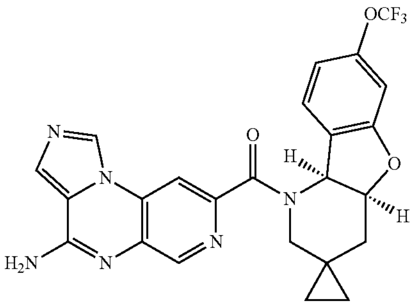 [SMILES: Nc1nc2cnc(C(=O)N3CC4(CC4)C[C@@H]4Oc5cc(OC(F)(F)F)ccc5[C@@H]43)cc2n2cncc12]

Example Fg-61: (4-aminoimidazo[1,5-a]pyrido[3,4-e]pyrazin-8-yl)((4aS,9bS)-7-(trifluoromethoxy)-4a,9b-dihydro-2H-spiro[benzofuro[3,2-b]pyridine-3,1'-cyclopropan]-1(4H)-yl)methanone. Prepared following general procedure VII-F starting with 4-aminoimidazo[1,5-a]pyrido[3,4-e]pyrazine-8-carboxylic acid hydrochloride Ak-5 and (4aS,9bS)-7-(trifluoromethoxy)-1,4,4a,9b-tetrahydro-2H-spiro[benzofuro[3,2-b]pyridine-3,1'-cyclopropane] Ebs-4. ES/MS: m/z=497.2 $[M+H]^+$. $^1H$ NMR (400 MHz, Methanol-d4) δ 9.36 (s, 0.5H rotamer), 9.35 (s, 0.5H rotamer), 8.86 (s, 0.5H rotamer), 8.79 (s, 0.5H rotamer), 8.63 (s, 0.5H rotamer), 8.53 (s, 0.5H rotamer), 8.32 (s, 0.5H rotamer), 8.30 (s, 0.5H rotamer), 7.68 (d, J=8.2 Hz, 0.5H rotamer), 7.50 (d, J=8.2 Hz, 0.5H rotamer), 6.90 (s, 0.5H rotamer), 6.88 (s, 0.5H rotamer), 6.81 (s, 0.5H rotamer), 6.74 (s, 0.5H rotamer), 6.46 (d, J=8.7 Hz, 0.5H rotamer), 6.07 (d, J=8.9 Hz, 0.5H rotamer), 5.33-5.23 (m, 0.5H rotamer), 5.17-5.07 (m, 0.5H rotamer), 4.13 (d, J=13.6 Hz, 0.5H rotamer), 3.38-3.34 (m, 0.5H rotamer), 3.18 (d, J=13.6 Hz, 0.5H rotamer), 2.85 (d, J=13.5 Hz, 0.5H rotamer), 2.21-2.06 (m, 1H), 1.84 (dd, J=14.8, 4.8 Hz, 0.5H rotamer), 1.72 (dd, J=14.7, 4.3 Hz, 0.5H rotamer), 0.64-0.17 (m, 4H).

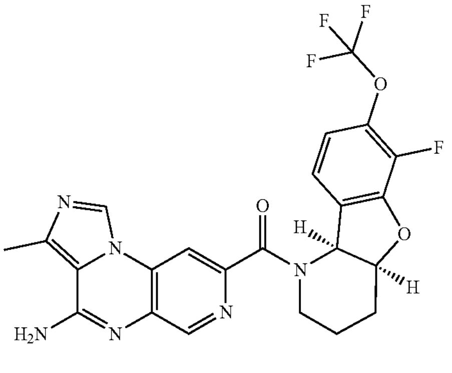 [SMILES: Cc1ncn2c1c(N)nc1cnc(C(=O)N3CCC[C@@H]4Oc5c(ccc(OC(F)(F)F)c5F)[C@@H]43)cc12]

Example Fg-62: (4-amino-3-methylimidazo[1,5-a]pyrido[3,4-e]pyrazin-8-yl)((4aS,9bS)-6-fluoro-7-(trifluoromethoxy)-3,4,4a,9b-tetrahydrobenzofuro[3,2-b]pyridin-1(2H)-yl)methanone. Prepared following general procedure VII-F starting with 7-amino-5-methyl-2,4,8,11-tetrazatricyclo[7.4.0.02,6]trideca-1(13),3,5,7,9,11-hexaene-12-carboxylic acid hydrochloride Ak-4 and (4aS,9bS)-6-fluoro-7-(trifluoromethoxy)-1,2,3,4,4a,9b-hexahydrobenzofuro[3,2-b]pyridine hydrochloride Ew-11. ES/MS: m/z=503.0 $[M+H]^+$. $^1$H NMR (400 MHz, MeOD) δ 9.26 (s, 1H), 8.93-8.76 (m, 1H), 8.61-8.43 (m, 1H), 7.58 (d, J=8.3 Hz, 0.4H, minor rotamer), 7.33 (d, J=8.3 Hz, 0.6H, major rotamer), 7.01 (t, J=7.3 Hz, 1H), 6.35 (d, J=8.6 Hz, 0.6H, major rotamer), 6.03 (d, J=9.0 Hz, 0.4H, minor rotamer), 5.31 (s, 0.6H, major rotamer), 5.14 (s, 0.4H, minor rotamer), 4.42 (s, 0.4H, minor rotamer), 3.78 (s, 0.6H, major rotamer), 3.11-2.93 (m, 1H), 2.81 (s, 3H), 2.35-1.62 (m, 4H).

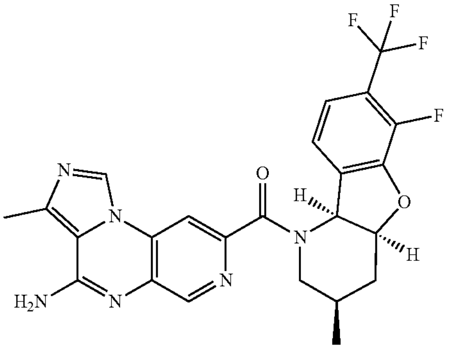 [SMILES: Cc1ncn2c1c(N)nc1cnc(C(=O)N3C[C@H](C)C[C@@H]4Oc5c(ccc(C(F)(F)F)c5F)[C@@H]43)cc12]

Example Fg-63: (4-amino-3-methylimidazo[1,5-a]pyrido[3,4-e]pyrazin-8-yl)((3R,4aS,9bS)-6-fluoro-3-methyl-7-(trifluoromethyl)-3,4,4a,9b-tetrahydrobenzofuro[3,2-b]pyridin-1(2H)-yl)methanone. Prepared following general procedure VII-F starting with 7-amino-5-methyl-2,4,8,11-tetrazatricyclo[7.4.0.02,6]trideca-1(13),3,5,7,9,11-hexaene-12-carboxylic acid hydrochloride Ak-4 and (3R,4aS,9bS)-6-fluoro-3-methyl-7-(trifluoromethyl)-1,2,3,4,4a,9b-hexahydrobenzofuro[3,2-b]pyridine hydrochloride Ew-17. ES/MS: m/z=501.0 $[M+H]^+$. $^1$H NMR (400 MHz, MeOD) δ 9.26 (d, J=2.0 Hz, 1H), 8.84-8.73 (m, 1H), 8.56 (s, 0.4H, minor rotamer), 8.49 (s, 0.6H, major rotamer), 7.67 (d, J=7.8 Hz, 0.4H, minor rotamer), 7.38 (d, J=7.8 Hz, 0.6H, major rotamer), 7.35-7.25 (m, 1H), 6.38 (d, J=8.3 Hz, 0.6H, major rotamer), 6.04 (d, J=8.3 Hz, 0.4H, minor rotamer), 5.32-5.23 (m, 0.6H, major rotamer), 5.07 (td, J=7.9, 5.5 Hz, 0.4H, minor rotamer), 4.54 (dd, J=13.3, 5.0 Hz, 0.4H, minor rotamer), 3.84 (dd, J=13.8, 5.4 Hz, 0.6H, major rotamer), 3.17 (ddt, J=8.0, 5.0, 2.6 Hz, 0.4H, minor rotamer), 2.80 (d, J=1.7 Hz, 3H), 2.57 (dd, J=13.7, 11.2 Hz, 0.6H, major rotamer), 2.37-2.16 (m, 2H), 1.78-1.48 (m, 1H), 1.06 (d, J=6.7 Hz, 1.2H, minor rotamer), 0.93 (d, J=6.7 Hz, 1.8H, major rotamer).

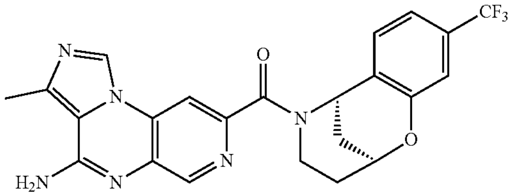 [SMILES: Cc1ncn2c1c(N)nc1cnc(C(=O)N3CC[C@H]4C[C@@H]3c3ccc(C(F)(F)F)cc3O4)cc12]

Example Fg-64: (4-amino-3-methylimidazo[1,5-a]pyrido[3,4-e]pyrazin-8-yl)((2S,6R)-9-(trifluoromethyl)-3,4-dihydro-2H-2,6-methanobenzo[b][1,5]oxazocin-5(6H)-yl)methanone. Prepared following general procedure VII-F starting with 7-amino-5-methyl-2,4,8,11-tetrazatricyclo[7.4.0.02,6]trideca-1(13),3,5,7,9,11-hexaene-12-carboxylic acid hydrochloride Ak-4 and (2S,6R)-9-(trifluoromethyl)-3,4,5,6-tetrahydro-2H-2,6-methanobenzo[b][1,5]oxazocine Ebi-1. ES/MS: m/z=469.0 $[M+H]^+$. $^1$H NMR (400 MHz, MeOD) δ 9.28 (s, 0.4H, minor rotamer), 9.21 (s, 0.6H, major rotamer), 8.91 (s, 0.4H, minor rotamer), 8.74 (s, 0.6H, major rotamer), 8.51 (s, 0.4H, minor rotamer), 8.38 (s, 0.6H, major rotamer), 7.48 (d, J=7.9 Hz, 0.6H, major rotamer), 7.36 (d, J=7.8 Hz, 0.4H, minor rotamer), 7.25-7.06 (m, 2H), 6.05 (s, 0.6H, major rotamer), 5.38 (s, 0.4H, minor rotamer), 4.51 (dd, J=14.1, 6.3 Hz, 0.4H, minor rotamer), 3.88-3.79 (m, 0.6H, major rotamer), 3.08 (ddd, J=14.1, 11.2, 6.0 Hz, 0.6H, major rotamer), 2.84-2.72 (m, 3.4H), 2.42 (d, J=13.7 Hz, 0.4H, minor rotamer), 2.33 (d, J=13.9 Hz, 0.6H, major rotamer), 2.22 (d, J=12.9 Hz, 1H), 2.13-1.97 (m, 2H).

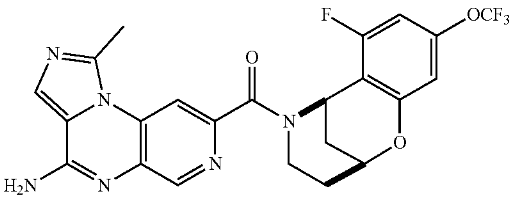

Example Fg-65: Rac-(4-amino-1-methylimidazo[1,5-a]pyrido[3,4-e]pyrazin-8-yl)((2S,6R)-7-fluoro-9-(trifluoromethoxy)-3,4-dihydro-2H-2,6-methanobenzo[b][1,5]oxazocin-5(6H)-yl)methanone. Prepared using general procedure VII-F starting with 4-aminoimidazo[1,5-a]pyrido[3,4-e]pyrazine-8-carboxylic acid hydrochloride Ak-5 and rac-(2S,6R)-7-fluoro-9-(trifluoromethoxy)-3,4,5,6-tetrahydro-2H-2,6-methanobenzo[b][1,5]oxazocine Ebi-13. ES/MS: m/z=503.2 $[M+H]^+$. $^1$H NMR (400 MHz, DMSO-$d_6$) δ 8.77 (s, 0.5H rotamer), 8.64 (s, 0.5H rotamer), 8.28 (s, 0.5H rotamer), 8.23 (s, 0.5H rotamer), 8.21 (brs, 2H), 8.06 (s, 1H), 6.94 (d, J=9.2 Hz, 0.5H rotamer), 6.88-6.73 (m, 1H+0.5H rotamer), 6.13 (s, 0.5H rotamer), 5.72 (s, 0.5H rotamer), 4.98-4.84 (m, 1H), 4.32 (dd, J=14.1, 6.2 Hz, 0.5H rotamer), 3.01 (s, 1.5H rotamer), 3.00 (s, 1.5H rotamer), 2.73-2.58 (m, 0.5H rotamer), 2.44-1.85 (m, 5H).

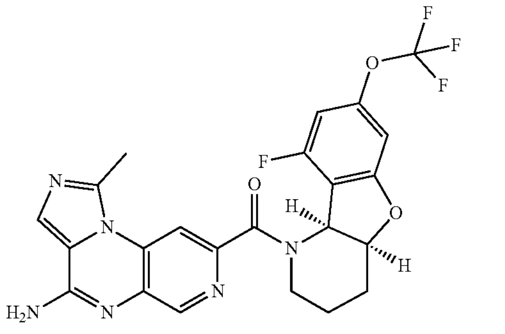 [SMILES: Cc1ncc2c(N)nc3cnc(C(=O)N4CCC[C@@H]5Oc6cc(OC(F)(F)F)cc(F)c6[C@@H]54)cc3n12]

Example Fg-66: (4-amino-1-methylimidazo[1,5-a]pyrido[3,4-e]pyrazin-8-yl)((4aS,9bS)-9-fluoro-7-(trifluoromethoxy)-3,4,4a,9b-tetrahydrobenzofuro[3,2-b]867yridine-1(2H)-yl)methanone. Prepared using general procedure VII-F starting with 4-amino-7-chloro-3-methylimidazo[1,5-a]quinoxaline-8-carboxylic acid hydrochloride Ak-3 and (4aS,9bS)-9-fluoro-7-(trifluoromethoxy)-1,2,3,4,4a,9b-hexahydrobenzofuro[3,2-b]pyridine hydrochloride Ew-24. ES/MS: m/z=503.2 $[M+H]^+$. $^1H$ NMR (400 MHz, DMSO-$d_6$) δ 8.73 (s, 1H), 8.41 (brs, 2H), 8.22 (s, 1H), 8.11 (s, 1H), 6.87 (brs, 2H), 6.54 (d, J=9.0 Hz, 1H), 5.27 (brs, 1H), 3.78 (brs, 1H), 3.01 (s, 3H), 2.93-2.65 (m, 1H), 2.13-1.50 (m, 4H).

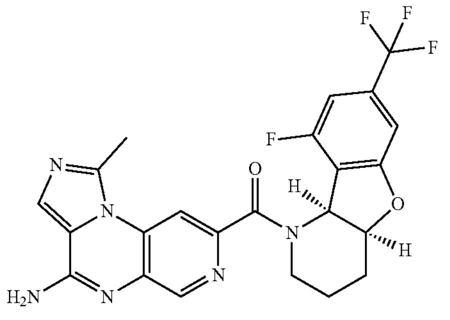 [SMILES: Cc1ncc2c(N)nc3cnc(C(=O)N4CCC[C@@H]5Oc6cc(C(F)(F)F)cc(F)c6[C@@H]54)cc3n12]

Example Fg-67: (4-amino-1-methylimidazo[1,5-a]pyrido[3,4-e]pyrazin-8-yl)((4aS,9bS)-9-fluoro-7-(trifluoromethyl)-3,4,4a,9b-tetrahydrobenzofuro[3,2-b]pyridin-1(2H)-yl)methanone. Prepared using general procedure VII-F starting with 4-amino-7-chloro-3-methylimidazo[1,5-a]quinoxaline-8-carboxylic acid hydrochloride Ak-3 and (4aS,9bS)-9-fluoro-7-(trifluoromethyl)-1,2,3,4,4a,9b-hexahydrobenzofuro[3,2-b]pyridine hydrochloride Ew-23. ES/MS: m/z=487.2 $[M+H]^+$. $^1H$ NMR (400 MHz, DMSO-$d_6$) δ 8.71 (s, 1H), 8.22 (brs, 3H), 8.06 (s, 1H), 7.31-7.03 (m, 2H), 6.63 (d, J=9.0 Hz, 1H), 5.29 (brs, 1H), 4.30 (brs, 1H), 3.17 (s, 1H), 3.00 (s, 3H), 2.98-2.61 (m, 1H), 2.07-1.52 (m, 4H).

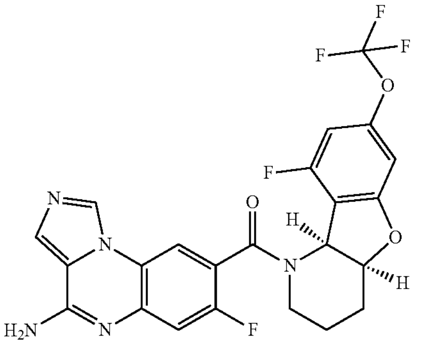 [SMILES: Nc1nc2cc(F)c(C(=O)N3CCC[C@@H]4Oc5cc(OC(F)(F)F)cc(F)c5[C@@H]43)cc2n2cncc12]

Example Fg-68: (4-amino-7-fluoroimidazo[1,5-a]quinoxalin-8-yl)((4aS,9bS)-9-fluoro-7-(trifluoromethoxy)-3,4,4a,9b-tetrahydrobenzofuro[3,2-b]pyridin-1(2H)-yl)methanone. Prepared following general procedure VII-F starting with 4-amino-7-fluoroimidazo[1,5-a]quinoxaline-8-carboxylic acid hydrochloride Ak-1 and (4aS,9bS)-9-fluoro-7-(trifluoromethoxy)-1,2,3,4,4a,9b-hexahydrobenzofuro[3,2-b]pyridine Ew-24. ES/MS: m/z=506.0 $[M+H]^+$. 1H NMR (400 MHz, Methanol-d4) δ 9.40-9.28 (m, 1H), 8.60-8.32 (m, 2H), 7.66-7.30 (m, 1H), 6.85-6.50 (m, 2H), 5.77 (s, 0.5H, rotamer), 5.43-5.16 (m, 1H), 4.45 (s, 0.5H, rotamer), 3.57-3.43 (m, 0.5H, rotamer), 3.19-2.99 (m, 1H), 2.88 (s, 0.5H, rotamer), 2.28-2.06 (m, 2H), 2.06-1.89 (m, 1H), 1.89-1.65 (m, 1H).

Example A: Cell Viability Assay

Cytotoxicity assay was performed using HCT116 WT (Horizon Discovery, Cat no. HD PAR-034) and HCT116 MTAP-deleted cell lines (Horizon Discovery, Cat no. HD R02-033) to demonstrate enhanced killing of MTAP-deleted cell in the presence of potent compounds. Control compounds were analyzed in parallel each time for quality control.

In Brief, on Day −1, a serial dilution of stock compounds in DMSO was performed using BioMek liquid handlers and dispensed using Echo acoustic dispenser into 384 well plates. Both tool compounds and sample compounds were spotted in the same plate for a dose response of PRMT5 inhibitors. Compound plates were stored as frozen until the cells were ready for seeding.

On Day 0, 100 HCT WT or HCT116 MTAP-deleted cells were seeded in compound-containing 384 well plates (50 μl per well) in RPMI 1640 media supplemented with 10% heat inactivated fetal bovine serum, Glutamax and penicillin streptomycin using EL460 liquid dispenser 5 μl cassette (BioTek, part no. 7170011). After equilibrating the plate in room temperature, the cells were incubated for 7 days inside the sealed incubator set at 37° C. with 90% humidity and 5% $CO_2$.

On Day 7, the viability of cells was measured using a CTG assay kit (CellTitre-Glo;Promega cat no. G7573). Shortly, 40 μl per well of luminescent cell viability assay reagent were dispensed using EL460 liquid dispenser 5 μl cassette. CTG luminescence signal was measured using an EnVision plate reader (PerkinElmer) in accordance with manufacturer's instruction. The $CC_{50}$ values for each compound after 7 days of treatment were calculated using 4 parameter non-linear logistical curve fit.

For the cell viability assay i.e. $CC_{50}$ shown in Table 3A: A: $CC_{50}$≤100 nM; B: 100 nM<CC50≤1 μM and C: CC50>1

μM. Selectivity with * is artificially high due to limited solubility of the compound hampering accurate measurement of WT CC50.

Example A1: In Vitro Cell Viability Assay for Various Cell Lines

Some Compounds of the Disclosure were tested in Calu-6 (Vendor: ATCC; Cat #HTB-56; Description: lung, adenocarcinoma), LU99 (Vendor: JCRB; Cat #JCRB0080; Description: lung, giant cell carcinoma), SW780 (Vendor: ATCC; Cat #CRL-2169; Description: bladder, urothelial carcinoma), and BxPC-3 (Vendor: ATCC; Cat #CRL-1687; Description: pancreas, adenocarcinoma) cellular viability assays according to the general protocol. Seeded cells into 96-well plate and incubated overnight. Seeded an additional 10 wells per cell line in an additional 96-well plate for assessing Time Zero luminescence and incubated overnight. To treatment plates, added compounds into each well using Tecan D300e dispenser (nine three-fold dilutions starting at 10 M) and incubated for 9 days. Time Zero (no compound treatment, luminescence assessed on day 1) and 9-day treatment (luminescence assessed on day 10) plates were assessed using the same CellTiter-Glo® substrate protocol. Thawed CellTiter-Glo® Buffer and lyophilized CellTiter-Glo® substrate and equilibrated to room temperature prior to use. Transferred 100 ml CellTiter-Glo® Buffer into amber bottle containing CellTiter-Glo® substrate to reconstitute the lyophilized enzyme/substrate mixture. For Time Zero and 9-day treatment plates, removed all plating media. Added 100 μl fresh media/well. Added 100 μl CellTiter-Glo® Reagent per well. Mixed contents for 10 min on an orbital shaker to lyse cells. Recorded luminescence with Perkin Elmer Envision 2105 machine. Analyzed the data with GraphPad software. Results are provided in Table 3C.

Example B: Symmetric Di-Methyl Arginine Image-Based High Content Screen Assay (SDMA Assay)

Symmetric di-methyl arginine image-based high content screen assay (SDMA assay) was performed in HCT116 WT and HCT116 MTAP-deleted cell lines to measure Symmetric Di-methyl Arginine (SDMA) signal reduction after selective PRMT5 inhibition in the MTAP-deleted cells. Control compounds were analyzed in parallel each time for quality control.

Briefly, the same compound plates were generated as mentioned in the previous section of Cell viability assay on Day −1. On Day 0, 800 HCT WT or HCT116 MTAP-deleted cell were seeded in compound-containing 384 well plates (50 μl per well) in RPMI 1640 media supplemented with 10% heat inactivated fetal bovine serum, Glutamax and penicillin streptomycin using EL460 liquid dispenser 5 μl cassette (BioTek, part no. 7170011). After equilibrating the plate at room temperature, the cells were incubated for 3 days inside the sealed incubator set at 37° C. with 90% humidity and 5% C02.

On Day 3, the cells were fixed by adding 45 μl of 8% neutralized formalin solution to each well using EL460 liquid dispenser 5 μl cassette and the cells were incubated for 30 minutes at room temperature. The formalin solution was washed off with depleted phosphate buffered saline (dPBS), the 0.1% Triton X-100 solution in dPBS was used to permeabilize the cells for 15 minutes at room temperature. The triton solution was aspirated, 50 μl of Odyssey Blocking buffer +0.05% Tween20 was added and the plate was incubated at room temperature for 30 minutes.

The blocking solution was removed, a 20 μl of SDMA antibody (Cell Signaling Technology, Cat no. 13222) diluted 1:500 in Odyssey Blocking buffer +0.05% Tween20 was added and the plate was incubated at 4° C. overnight. Next day, the primary SDME antibody solution was washed from each well three times with 0.05% Tween20 in dPBS (PBST).

A 30 μl of the secondary antibody, a Goat anti-Rabbit Alexa Fluor Plus 488 (Invitrogen, Cat no. PIA32731) was diluted 1:500 in Odyssey Blocking buffer +0.05% Tween20 and the plate was incubated for 1.5 hours in dark at room temperature. The secondary antibody solution was removed, 30 μl of 5 mg/ml DAPI solution diluted 1:2000 in dPBS was added and the plate was incubated for 30 minutes in dark at room temperature. The DAPI solution was aspirated and the wells were washed six times with dPBS.

The SDMA signal and DAPI signal per cell were counted using a Cellomics CX7 LZR instrument reading under 488 and 405 nm laser, respectively. The SDMA signal was quantified by mean average intensity per cell from Alexa Fluor Plus 488 after the cell was defined with DAPI. The $EC_{50}$ values for each compound after 3 days of treatment were calculated using 4 parameter non-linear logistical curve fit.

For the SDMA assay i.e. $EC_{50}$ shown in Table 3A: A: EC50≤1 nM, B: 1 nM<EC50≤5 nM, C: EC50>5 nM.

Example C: hERG Assay

Cell lines and cell culture: The HEK293 cell line stably expressing the hERG ion channel was provided from Charles River laboratories. Cells were maintained in tissue culture incubators per Charles River Laboratories SOP. Stocks were maintained in cryogenic storage. HEK293 cells were stably transfected with hERG cDNA.

Automated Patch Clamp Procedures: In preparation for a recording session, intracellular solution was loaded into the intracellular compartments of the QPlate and cell suspension was pipetted into the extracellular compartments. After establishment of a whole-cell configuration, membrane currents were recorded using up to 48 parallel patch clamp amplifiers in the QPatch HT® system. The current records were sampled at 2000 Hz and low-pass Bessel filtered at 400 Hz.

Valid whole-cell recordings met the following criteria:

1. Membrane resistance ≥200 MΩ.
2. Leak current 25% channel current or subtracted.

hERG Test Procedures: Onset and block of hERG current was measured using a stimulus voltage pattern consisting of a 500 ms prepulse to −40 mV (leakage subtraction), a 2-second activating pulse to +40 mV followed by a 2-second test pulse to −40 mV. The pulse pattern was repeated continuously at 10 s intervals from a holding potential of −80 mV. Peak tail current was measured during the −40 mV test pulse. Leakage current was calculated from the current amplitude evoked by the −40 mV prepulse and subtracted from the total membrane current record.

Data Analysis: Data acquisition and analysis were performed using the QPatch Assay Software (Sophion Bioscience A/S, Denmark). Steady state was defined by the limiting constant rate of change with time (linear time dependence). The steady state before and after test article application were used to calculate the percentage of current inhibited at each concentration. Run down, a time-dependent reduction of current amplitude, may be compensated for in the QPatch Assay Software using standard system tools. Concentration-response data was fit to an equation of the following form:

$$\% \text{ Block} = \{1 - 1/[1 + ([\text{Test}]/IC_{50})^N]\} * 100\%$$

Where [Test] is the concentration of test compound, $IC_{50}$ is the concentration of the test compound producing half-maximal inhibition, N is the Hill coefficient and % Block is the percentage of current inhibited at each concentration of the test article. Nonlinear least squares fits will be solved with the Solver add-in for Excel 2000 or later (Microsoft, Redmond, WA). If the test compound produces greater than 50% block at the highest concentration and less than 50% block at the lowest concentration with three or more test concentrations, the $IC_{50}$ was calculated and included in the report.

Example D: Plasma Protein Binding Assay

D.1 Instrument and Reagents for Dialysis

Instrument: HTD96b equilibrium dialyzer

Reagents:

Plasma in K2 EDTA: Bioreclamation or equivalent.

Plasma (not pH-adjusted) is stored at −80□C. Thawed at room temperature before use.

CCM: Various.

Buffer: 133 mM phosphate buffer with added dextran.

D.2 Stock Solutions and Quench

Test compound: 200 μM in DMSO: Take 1 μL of 10 mM stock, add 49 μL of DMSO.

Quench solution: 50 nM Labetalol in 90% ACN 10% Methanol

D.3 Test Compound Solutions in Plasma and CCM

2 μM test compound in plasma

Add 2 μL of 200 μM stock solution to 198 μL blank plasma.

2 μM test compound in CCM

Add 2 μL of the 200 μM stock solution to 198 μL CCM.

D.4. Equilibrium Dialysis Procedure

HTD 96b Dialyzer:

Add 100 μL plasma with 2 μM test compound into one side of the well.

Add 100 μL buffer (for plasma) into another side of the well.

Add 100 μL CCM with 2 μM test compound into one side of the well.

Add 100 μL buffer (for CCM) into another side of the well.

Do replicates for each compound.

Cover the 96-well plate using the adhesive sealing film.

Incubate for 24 hours at 37° C. under slow rotation.

D.5 Sample Preparation for Analysis

Take 60 μL plasma sample into a 96 well plate. Add 60 μL buffer

Take 60 μL buffer into a 96 well plate. Add 60 μL blank plasma

Treat the CCM sample same as above

Add 180 μL of quench solution

Seal the plate and shake vigorously for 5 minutes.

Centrifuge for 20 minutes at 3000 RPM

Transfer 200 μL of supernatant into a clean plate. Dilute with 200 μL of millipored water.

Analyze samples by LC/MS

D.6 Liquid Chromatography—Mass Spectrometry: Quantification of test compounds was performed by analyte/internal standard peak area ratio (PAR) values measured on a Thermo Q-Exactive mass spectrometer coupled to a Dionex UltiMate 3000 HPLC with a Leap Technologies HTC PAL autosampler. The column used for analysis of test compounds was a Thermo Hypersil GOLD (1.9 m particle size, 2.1×50 mm). Mobile phase A consisted of 0.1% (v/v) formic acid in water. Mobile phase B consisted of 0.1% (v/v) formic acid in acetonitrile. Elution of analytes was achieved by a series of linear gradients varying the proportions of A and B. The mass spectrometer was calibrated on a weekly basis and mass tolerance of 5 ppm was used.

Example E: Pharmacokinetics of Compounds in Cassette in Male Sprague-Dawley Rats for Kp Measurement E.1 Test Animal: Male Sprague-Dawley Rats (225-300 g) with Indwelling Bilateral Jugular Vain Cannula (JVC/JVC) or Single Jugular Vein Cannula (JVC)

E.2 Pharmaceutical Formulation and Administration

Test compound was dissolved in the vehicle of 10% DMSO, 10% ethanol, 40% polyethylene glycol 300, and 40% propylene glycol to get 1 mg/mL test compound solution. The compound was administered by intravenous administration at a dose of 1 mL/kg. Fasting was not required.

E.3 Sample Collection

| Serial blood collection time | Tissue collection time (Brain & CSF) |
|---|---|
| 0.5 hours following the start of the infusion | 0.5 hours post dose |
| 2 hours following the start of the infusion | 2 hours post dose |
| 4 hours following the start of the infusion | 4 hours post dose |

Anticoagulant: $K_2$EDTA

Volume: approximately 225 μL blood at each bleed

Jugula vein via syringe and needle or another method (non-terminal samples) or exsanguination (cardiac puncture) under isoflurane (or $CO_2$ inhalation if isoflurane is unavailable) anesthesia (terminal time points). Blood samples were collected into $K_2$EDTA tubes Tissue collection and processing: following the terminal blood collection, the brain and CSF were collected from each animal.

Example F: Pharmacokinetics of Compounds in Cassette in Male Cynomolgus Monkeys for Kp Measurement F.1 Test Animal: Cynomolgus Monkeys from Labcorp 8298417 Maintained at Labcorp-Madison F.2 Pharmaceutical Formulation and Administration Test compound was dissolved in the vehicle of 10% DMSO, 10% ethanol, 40% polyethylene glycol 300, and 40% propylene glycol to get 0.5 mg/mL test compound solution. The compound was administered by intravenous administration at a dose of 1 mL/kg. The intravenous dose was administered as a bolus injection followed by an approximately 2-hour infusion via an indwelling catheter in a saphenous or cephalic vein. Fasting was not required.

F.3 Sample Collection

Collection time:

PK for Plasma: Predose, 0.25, 1, 1.5 and 2 hours postdose (based on start of infusion)

PK for Whole Blood: 1.5 hour postdose

Anticogulant: $K_2$EDTA

Volume:

PK for Plasma: Approximately 0.5 mL

PK for Whole Blood: Approximately 0.1 mL

Collection Site: Femoral vein; saphenous or cephalic vein

Example G1: Brain Tissue Binding Equilibrium Dialysis Protocol 1 mL Teflon dialysis cells from Harvard Apparatus were used in these experiments. Brain tissue homogenate was prepared with 1:4 (tissue: phosphate buffer, w/w) with 0.133 M phosphate buffer. Rat brain tissue homogenate was generated with at least 3 donors and Cyno monkey brain tissue homogenate was generated with single donor.

Dialysis membrane was soaked for approximately one hour in 0.133 M phosphate buffer, pH 7.4. Test compound was spiked to a final concentration of 2 μM in the tissue homogenate, and no compound was spiked to buffer. 1 mL aliquots of tissue homogenate and 1 mL buffer were placed into opposite sides of the assembled dialysis cells. After the 5-hour equilibration period in a 37° C. water bath, samples from each side of the cell were removed and added to the appropriate vials containing either 1 mL of tissue homogenate as appropriate for the species, or buffer. A 100 μL aliquot was removed and added to 400 μL quenching solution containing 50 nM internal standard. Samples were vortexed and centrifuged for 15 minutes at 12000×G. 200 μL of the supernatant was removed and placed into a new 96 well plate which contain of 100 μL water to generate the proper final concentration samples for analyzing. The plate was then vortexed and subjected to LC-MS analysis. Quantification was by analyte/internal standard peak area ratio (PAR).

The binding ratio for an analyte in brain 20% (w/v) tissue homogenate vs. buffer was calculated using the following equation:

$$\%\text{ Tissue Homogenate }(fu) = \left(C_{buffer}/C_{tissue\ homogenate}\right)\cdot 100\%$$

where $C_{tissue\ homogenate}$, and $C_{buffer}$ are the post-dialysis tissue homogenate, and buffer concentrations, respectively.

The free fraction in 100% tissue was calculated from the free fraction in 20% (w/v) tissue homogenate and the dilution factor (D=0.2).

Example G2: MDR1/BCRP Assay cPgp-KO-MDCK-WT, cPgp-KO-MDR1-KI, and cPgp-KO—BCRP—KI cells (all from Sigma) were cultured in Dulbecco's Modification of Eagle's Medium (DMEM) with 4.5 g/L glucose, sodium pyruvate, and GlutaMAX (Gibco) supplemented with 1% Pen/Strep and 10% fetal bovine serum. The cells were maintained in an incubator at 37° C., 90% humidity, and 5% $CO_2$ until reaching confluence over 5 days in 96-well transwell plates. Experiments were conducted using an HBSS donor buffer (Invitrogen) containing 10 mM HEPES and 15 mM glucose, adjusted to pH 7.4. The receiver well contained HBSS buffer supplemented with 1% BSA, 10 mM HEPES, and 15 mM glucose, and the pH was adjusted to 7.4. TEER values were measured to assess membrane integrity after an initial equilibration with BSA-free transport buffer for 15 minutes. The experiment was started by adding dosing solutions containing test compounds at 1 μM. Cells were dosed on the apical (A) side or basolateral (B) side at 100 μl and 200 μl, respectively, to determine forward (A to B) and reverse (B to A) permeability. At the 2-hour time point, 50 μl samples were collected from the receiver compartment. Each compound was tested in 2 separate replicate wells for each condition. All samples were immediately collected into plates, and 50 μL of acetonitrile was added. Subsequently, 350 μl of 30:70 methanol: acetonitrile containing internal standard was added to precipitate proteins and stabilize the test compounds. To test for non-specific binding and compound instability, the total amount of the drug was quantified at the end of the experiment and compared to the material present in the original dosing solution as a percentage of the recovery. All samples were analyzed by LC-MS/MS using electrospray ionization.

The apparent permeability, $P_{app}$, and % recovery were calculated as follows:

$$P_{app} = \left(d_R/d_t\right)\times V_r/(A\times D_0)$$

$$\%\text{ Recovery} = 100\times((V_r\times R_{120}) + (V_d\times D_{120}))/(V_d\times D_0)$$

Where, $d_R/d_t$ is the slope of the cumulative concentration in the receiver compartment versus time in μM/s based on receiver concentrations measured at 120 minutes.

$V_r$ and $V_d$ are the receiver and donor compartment volumes in $cm^3$, respectively.

A is the area of the cell monolayer (0.143 $cm^2$).

$D_0$ and $D_{120}$ are the measured donor concentrations at the experiment's beginning and end, respectively.

$R_{120}$ is the receiver concentration at the end of the experiment (120 minutes).

Efflux ratio (ER) is defined as $P_{app}$ (B-to-A)/$P_{app}$ (A-to-B).

Example H: PBS Solubility

Buffer Preparation: 1×PBS, 7.4: Phosphate Buffered Saline solution 10×, PBS (Fisher Bioreagent, part number BP399-500) 50 mL was added to approximately 450 mL HPLC grade H2O. The volume of the solution was then adjusted to 500 mL for a total dilution factor of 1:10 and a final PBS concentration of 1×. The pH of the final solution was measured and found to be 7.4.

Kinetic Solubility from DMSO Stocks: 100-fold dilutions of each DMSO stock solution were prepared in singleton by combining 3 μL of DMSO stock with 297 μL of the appropriate media in a Millipore solubility filter plate with 0.45 μM polycarbonate filter membrane using Hamilton Starlet liquid handling. The final DMSO Concentration is 1.0% and maximum theoretical compound concentration is 100 μM (assuming stock concentration of 10 mM). The filter plate was sealed. Following 24-hour incubation at ambient temperature (20.8-24.0° C.), the samples were vacuum filtered, and the filtrates were collected in a 96 well polypropylene plate for analysis. The collection plate was sealed for analysis. Filtrates were injected into the nitrogen detector for quantification on Analiza's Automated Discovery Workstation. The results are reported here in both μM and μg/mL.

Calculation of Results: The equimolar nitrogen response of the detector is calibrated using standards which span the dynamic range of the instrument from 0.08 to 4500 μg/ml nitrogen. The filtrates were quantified with respect to this calibration curve. The calculated solubility values are corrected for background nitrogen present in the DMSO, and the media used to prepare the samples. All reported values for compounds containing adjacent nitrogen atoms in a ring structure should be increased by ~25%. A comments field contains notes pertinent to the assay of each compound, such as, measured solubility is greater than 75% of the dose concentration, actual solubility may be higher. The solubility results presented assume that the samples were free of nitrogen containing impurities and are stable under the assay conditions. Results are provided in Table 6.

Example I: Hepatocyte Stability Assay

I.1 Reagents

BioreclamationIVT (Baltimore, MD) provided the cryopreserved hepatocytes, hepatocyte thawing (HT) medium, and Krebs-Henseleit buffer (KHB) medium. The stock solution concentration was 1 M in DMSO and was then diluted further in acetonitrile/water (1:1 v/v). All other chemicals were purchased from Sigma-Aldrich (St. Louis, MO) or Thermo Fisher Scientific (Waltham, MA).

The quench solution used to stop reactions in the hepatocyte incubations was comprised of 100% (v/v) acetonitrile. Internal Standard/Quench (IS/Q) solution used to stop reactions with the positive control also contained 200 nM Labetalol.

I.2 Assays

Metabolic Stability in Cryopreserved Hepatocytes: Test compounds, or the positive control metabolic substrate, was incubated in suspensions of cryopreserved hepatocytes at a final concentration of 1 μM. Vials containing cryopreserved hepatocytes were removed from liquid nitrogen and immediately immersed in a 37° C. water bath. The vials were swirled gently until the contents had thawed. They were then immediately emptied into 48 mL of pre-warmed thawing medium in a 50 mL conical tube. Cells remaining in the vial were re-suspended with 1.0 mL of pre-warmed thawing medium and added to the conical tube. The tube was capped and then gently inverted several times to re-suspend the hepatocytes. The cell suspension was centrifuged at 500×g for 10 minutes at room temperature and the supernatant discarded. The cell pellet was loosened by gently swirling the centrifuge tube. Non-supplemented KHB medium was added to obtain the appropriate target cell density. The viabilities of all cell preparations were ≥85%, assessed by Trypan blue dye exclusion.

For incubations, aliquots of hepatocyte suspension (250 μL containing a cell concentration of $2\times10^6$ cells/mL) were added to 250 μL of 2 μM substrate (test compound or positive control) in supplemented KHB in duplicate wells in a 24-well plate. Final concentration in the incubations were $1\times10^6$ cells/mL and 1 μM substrate. A cell-free control incubation (KHB only) was also included. The incubations were carried out with gentle shaking in a 37° C. incubator under a humid atmosphere of 95% air/5% $CO_2$ (v/v). Aliquots (100 μL) were removed after 0, 1, 3, and 6 hours and added to 200 μL quenching solution. The samples were then placed on a shaker for 10 min followed by centrifugation at 3000×g for 20 min. The supernatant was transferred to a new plate and diluted with 100 μL of water to reduce the organic content and then placed on a shaker for 10 mins. Samples were injected and analyzed with methods described below.

Liquid Chromatography: Quantification of positive control and test compound was performed by analyte/internal standard peak area ratios (PAR) measured on a Thermo Scientific™ Q Exactive™ Hybrid Quadrupole-Orbitrap Mass Spectrometer MS/MS with an electrospray interface operating in positive ion mode. The mass spectrometer was coupled to a Dionex Ultimate® 3000 HPLC system. Samples (10 μL aliquots) were injected with a Leap Technologies HTC PAL autosampler. For positive control, the column used was a Thermo Scientific™ Hypersil GOLD™ HPLC column (1.9 m particle size, 50×2.1 mm). Mobile phase A consisted of 95% (v/v) water, 5% (v/v) acetonitrile, and contained 0.1% (v/v) formic acid (FA). Mobile phase B consisted of 95% (v/v) acetonitrile, 5% (v/v) water, and contained 0.1% (v/v) FA. Elution was achieved, at a flow rate of 0.5 mL/min, by a series of linear gradients: initial condition was 5% B at 0 min, isocratic for 20 seconds; then linear gradient to 95% B over 90 seconds, followed by isocratic for 60 seconds at 95% B, and re-equilibrated to initial conditions over 70 seconds.

I.3. Data Analysis

Metabolic stabilities of positive control and test compound were determined by measuring the rates of disappearance of the parent with time by determining the % of parent remaining at time t ($C_t$) {Obach 1997}.

Data (% of parent remaining) were plotted on a semi-log scale and fitted using an exponential fit:

$$C_t = C_0 \times e^{-k \times t},$$

where $C_t$% of parent remaining at time=t $C_0$% of parent remaining at time=0 t time k First order elimination rate constant

In vitro half-life (T½) was calculated as ln2/k.

The intrinsic hepatic clearance was calculated as follows:

$$CL_{int} = \frac{k \times V \times Y}{P},$$

where $CL_{int}$ Intrinsic hepatic clearance (L/hr/kg body weight)

V Incubation volume (L)

Y hepatocyte yield (millions of hepatocytes/kg body weight)

P Number of hepatocytes ($\times10^6$) in the incubation

Predicted hepatic extraction was then calculated by comparison of predicted hepatic clearance to hepatic blood flow. Values used for calculation of the predicted hepatic clearance are shown in Table below:

Values Used for Calculation of the Predicted Hepatic Clearance from Hepatocyte Stability

| | Hepatocytes | | | |
|---|---|---|---|---|
| Species | V (L) | P (million) | Y (million/kg) | $Q_h$ (L/hr/kg) |
| Rat | 0.0005 | 0.5 | 4800 | 4.2 |
| Beagle Dog | 0.0005 | 0.5 | 3840 | 1.8 |
| Cynomolgus Monkey | 0.0005 | 0.5 | 2160 | 1.6 |
| Rhesus Monkey | 0.0005 | 0.5 | 3600 | 2.6 |
| Human | 0.0005 | 0.5 | 3086 | 1.3 |

Tables

Tables 1A-1D provide some examples disclosed herein. The Examples listed in Tables 1A-1D were prepared according to the procedures described herein and/or indicated in Table 2. Cell viability assay data and SDMA assay data for some examples are provided in Tables 3A-3C. Table 4 provides permeability data for some compounds disclosed herein. Table 5 provides brain penetration data for some compounds disclosed herein. Table 6 provides hERG IC50 and PBS solubility date for some compounds disclosed herein. Table 7 provides human predicted clearance data for some compounds disclosed herein. Tables 8A-8I provides PK data for some compounds disclosed herein. Results in Table 3B rely on assay protocols presented in Examples A and D. Results presented in Table 4 rely on assay protocols presented in Example G2. Results presented in Table 5 rely on assay protocols presented in Examples D, E and G1. Results presented in Table 6 rely on assay protocols presented in Examples C and H. Results presented in Table 7 rely on assay protocol presented in Example I. Results presented in Tables 8A-8I rely on assay protocols presented in Example I.

TABLE 1A

| Compounds | |
|---|---|
| Example | Structure |
| Fa-1 | 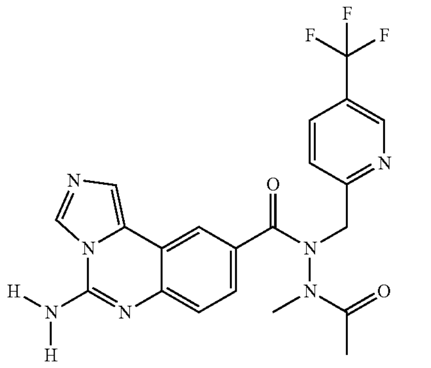 [SMILES: CC(=O)N(C)N(Cc1ccc(C(F)(F)F)cn1)C(=O)c1ccc2nc(N)n3cncc3c2c1] |

TABLE 1A-continued

| Compounds | |
|---|---|
| Example | Structure |
| Fa-2 | 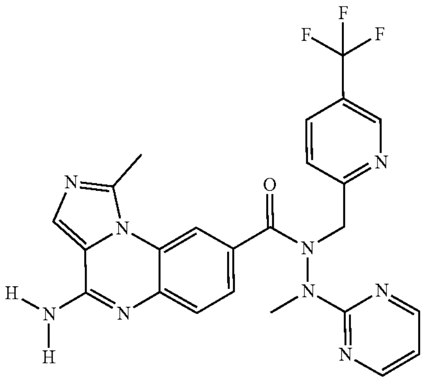 [SMILES: Cc1ncc2c(N)nc3ccc(C(=O)N(Cc4ccc(C(F)(F)F)cn4)N(C)c4ncccn4)cc3n12] |
| Fa-3 | 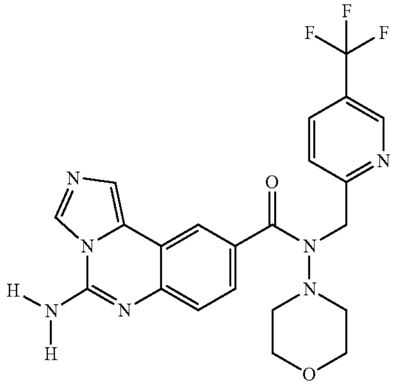 [SMILES: Nc1nc2ccc(C(=O)N(Cc3ccc(C(F)(F)F)cn3)N3CCOCC3)cc2c2cncn12] |
| Fa-4 | 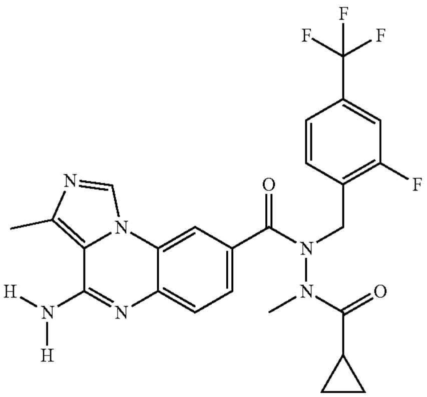 [SMILES: Cc1ncn2c1c(N)nc1ccc(C(=O)N(Cc3ccc(C(F)(F)F)cc3F)N(C)C(=O)C3CC3)cc12] |

TABLE 1A-continued
| Compounds | |
|---|---|
| Example | Structure |
| Fa-5 | 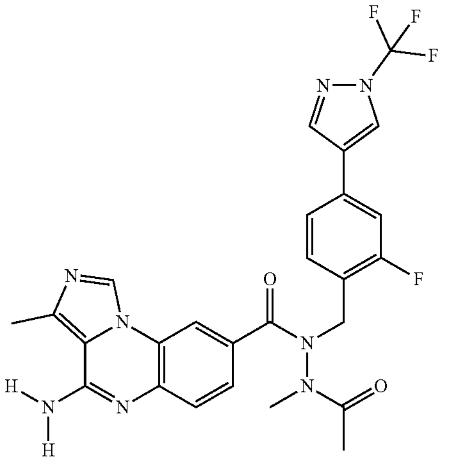 [SMILES: CC(=O)N(C)N(Cc1ccc(-c2cnn(C(F)(F)F)c2)cc1F)C(=O)c1ccc2nc(N)c3c(C)ncn3c2c1] |
| Fa-6 | 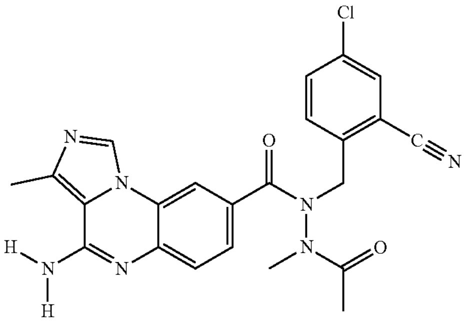 [SMILES: CC(=O)N(C)N(Cc1ccc(Cl)cc1C#N)C(=O)c1ccc2nc(N)c3c(C)ncn3c2c1] |
| Fa-7 | 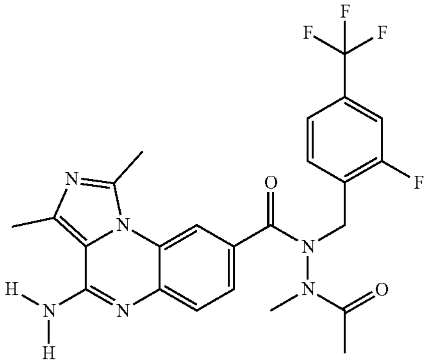 [SMILES: CC(=O)N(C)N(Cc1ccc(C(F)(F)F)cc1F)C(=O)c1ccc2nc(N)c3c(C)nc(C)n3c2c1] |
| Fa-8 | 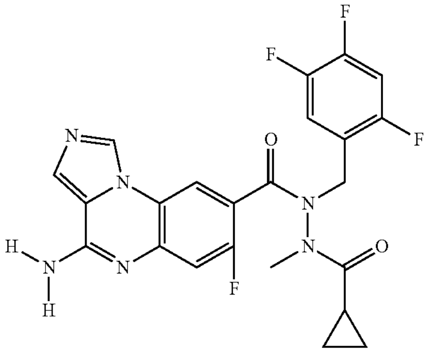 [SMILES: CN(C(=O)C1CC1)N(Cc1cc(F)c(F)cc1F)C(=O)c1cc2c(cc1F)nc(N)c1cncn12] |
TABLE 1A-continued
| Compounds | |
|---|---|
| Example | Structure |
| Fb-1 | 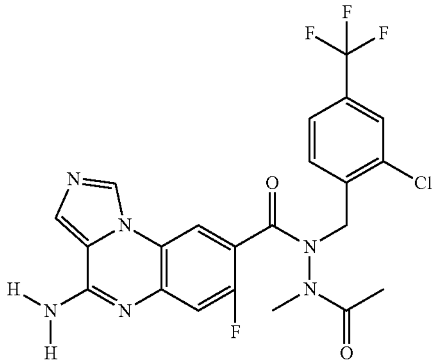 [SMILES: CC(=O)N(C)N(Cc1ccc(C(F)(F)F)cc1Cl)C(=O)c1cc2c(cc1F)nc(N)c1cncn12] |
| Fb-2 | 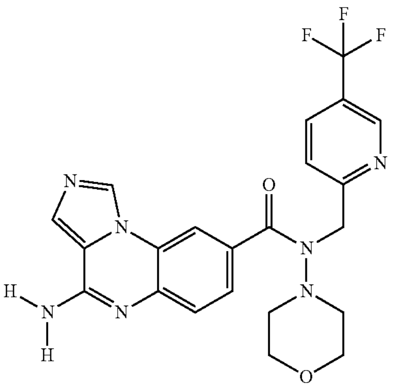 [SMILES: Nc1nc2ccc(C(=O)N(Cc3ccc(C(F)(F)F)cn3)N3CCOCC3)cc2n2cncc12] |
| Fb-3 | 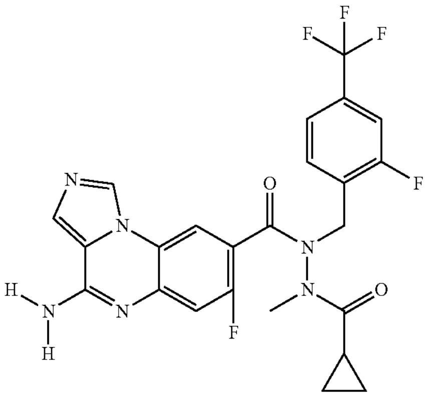 [SMILES: CN(C(=O)C1CC1)N(Cc1ccc(C(F)(F)F)cc1F)C(=O)c1cc2c(cc1F)nc(N)c1cncn12] |
| Fb-4 | 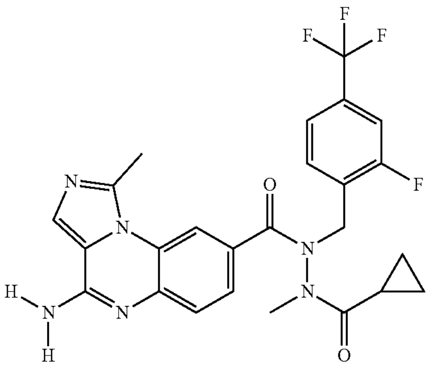 [SMILES: Cc1ncc2c(N)nc3ccc(C(=O)N(Cc4ccc(C(F)(F)F)cc4F)N(C)C(=O)C4CC4)cc3n12] |

TABLE 1A-continued
| Compounds | |
|---|---|
| Example | Structure |
| Fb-5 | 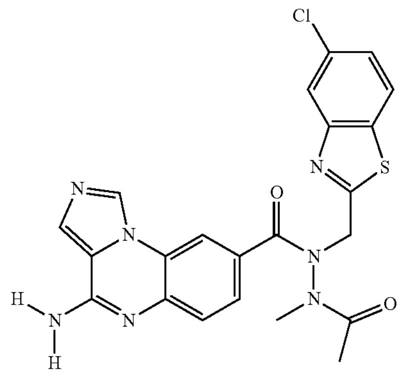 [SMILES: CC(=O)N(C)N(Cc1nc2cc(Cl)ccc2s1)C(=O)c1ccc2nc(N)c3cncn3c2c1] |
| Fb-6 | 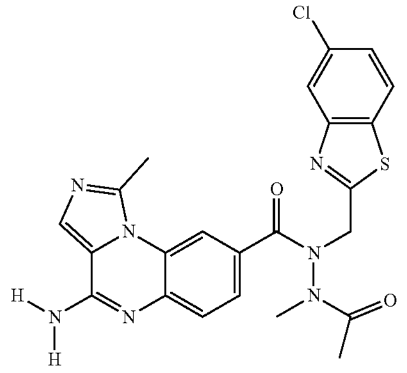 [SMILES: CC(=O)N(C)N(Cc1nc2cc(Cl)ccc2s1)C(=O)c1ccc2nc(N)c3cnc(C)n3c2c1] |
| Fb-7 | 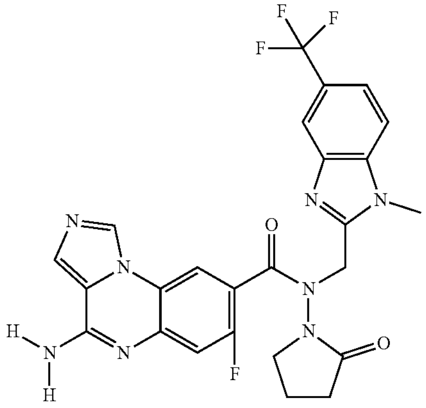 [SMILES: Cn1c(CN(C(=O)c2cc3c(cc2F)nc(N)c2cncn23)N2CCCC2=O)nc2cc(C(F)(F)F)ccc21] |
| Fb-16 | 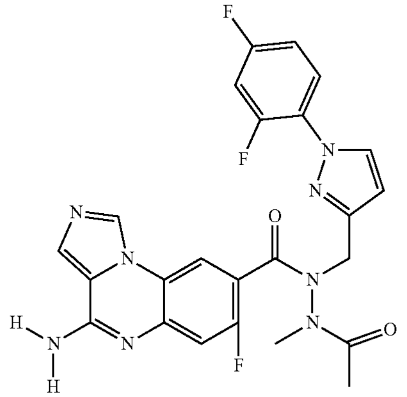 [SMILES: CC(=O)N(C)N(Cc1ccn(-c2ccc(F)cc2F)n1)C(=O)c1cc2c(cc1F)nc(N)c1cncn12] |
TABLE 1A-continued
| Compounds | |
|---|---|
| Example | Structure |
| Fb-17 | 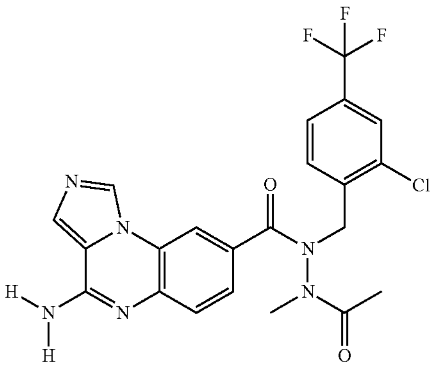 [SMILES: CC(=O)N(C)N(Cc1ccc(C(F)(F)F)cc1Cl)C(=O)c1ccc2nc(N)c3cncn3c2c1] |
| Fc-1 | 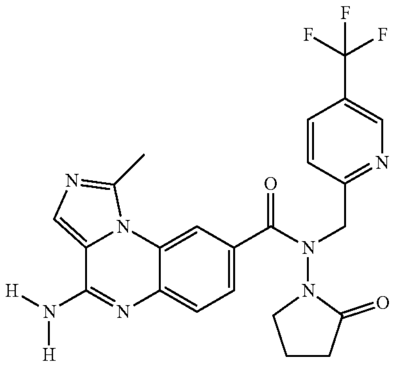 [SMILES: Cc1ncc2c(N)nc3ccc(C(=O)N(Cc4ccc(C(F)(F)F)cn4)N4CCCC4=O)cc3n12] |
| Fc-2 | 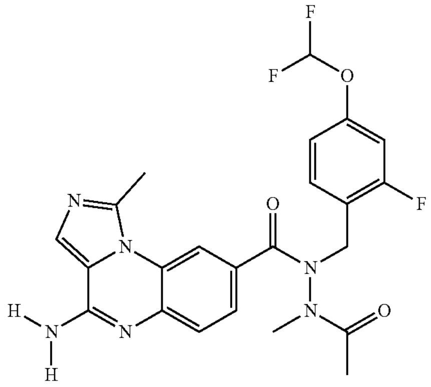 [SMILES: CC(=O)N(C)N(Cc1ccc(OC(F)F)cc1F)C(=O)c1ccc2nc(N)c3cnc(C)n3c2c1] |
| Fd-1 | 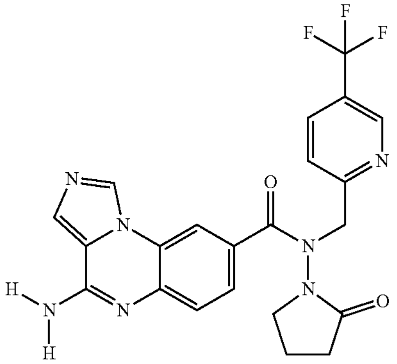 [SMILES: Nc1nc2ccc(C(=O)N(Cc3ccc(C(F)(F)F)cn3)N3CCCC3=O)cc2n2cncc12] |

TABLE 1B
| Compounds | |
|---|---|
| Example | Structure |
| Fb-8 | 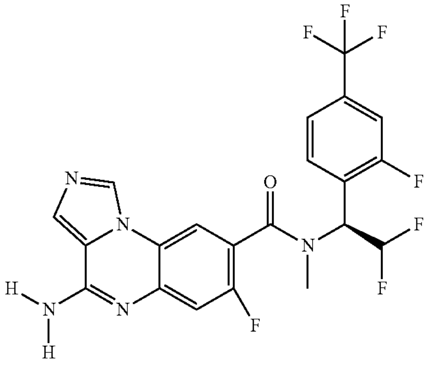 [SMILES: CN(C(=O)c1cc2c(cc1F)nc(N)c1cncn12)[C@@H](c1ccc(C(F)(F)F)cc1F)C(F)F] |
| Fb-9 | 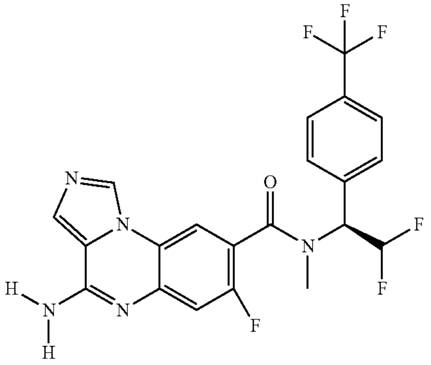 [SMILES: CN(C(=O)c1cc2c(cc1F)nc(N)c1cncn12)[C@@H](c1ccc(C(F)(F)F)cc1)C(F)F] |
| Fb-10 | 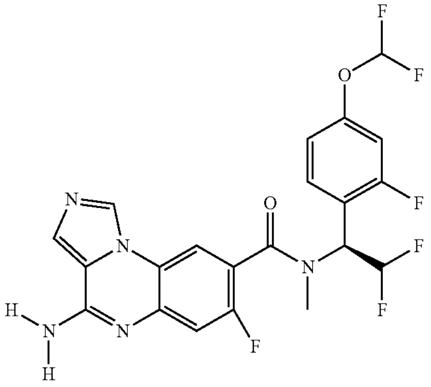 [SMILES: CN(C(=O)c1cc2c(cc1F)nc(N)c1cncn12)[C@@H](c1ccc(OC(F)F)cc1F)C(F)F] |
| Fb-11 | 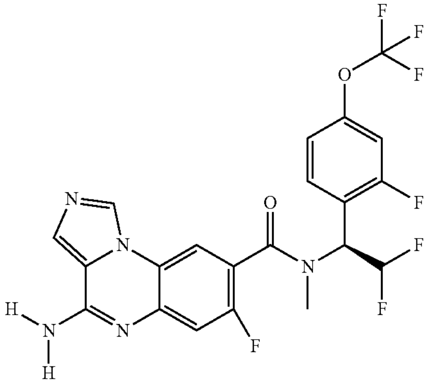 [SMILES: CN(C(=O)c1cc2c(cc1F)nc(N)c1cncn12)[C@@H](c1ccc(OC(F)(F)F)cc1F)C(F)F] |

TABLE 1B-continued
| Compounds | |
|---|---|
| Example | Structure |
| Fb-12 | 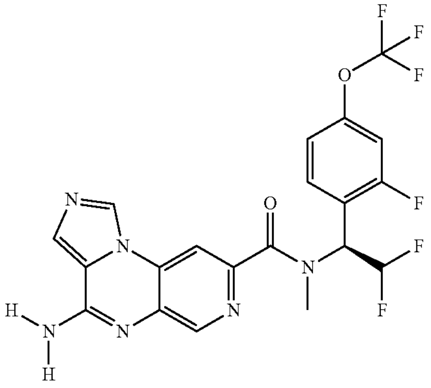 [SMILES: CN(C(=O)c1cc2c(cn1)nc(N)c1cncn12)[C@@H](c1ccc(OC(F)(F)F)cc1F)C(F)F] |
| Fb-13 | 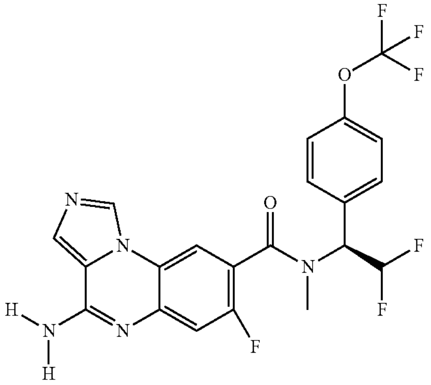 [SMILES: CN(C(=O)c1cc2c(cc1F)nc(N)c1cncn12)[C@@H](c1ccc(OC(F)(F)F)cc1)C(F)F] |
| Fb-14 | 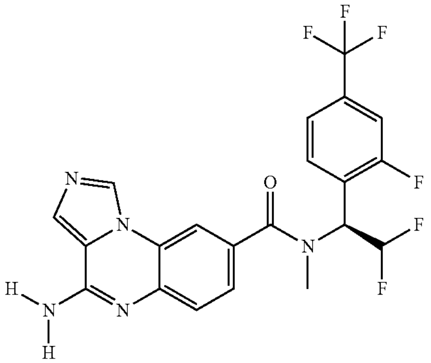 [SMILES: CN(C(=O)c1ccc2nc(N)c3cncn3c2c1)[C@@H](c1ccc(C(F)(F)F)cc1F)C(F)F] |
| Fb-15 | 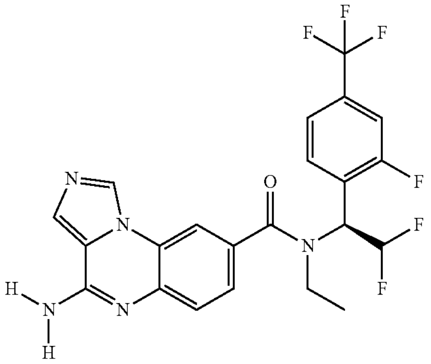 [SMILES: CCN(C(=O)c1ccc2nc(N)c3cncn3c2c1)[C@@H](c1ccc(C(F)(F)F)cc1F)C(F)F] |

TABLE 1B-continued
| Compounds | |
|---|---|
| Example | Structure |
| Fb-18 | 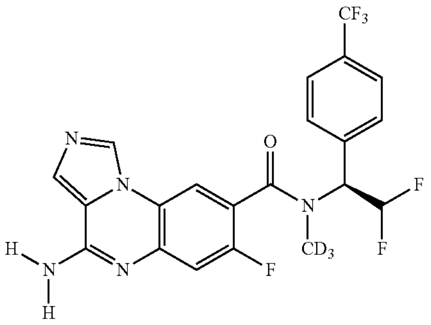 [SMILES: [2H]C([2H])([2H])N(C(=O)c1cc2c(cc1F)nc(N)c1cncn12)[C@@H](c1ccc(C(F)(F)F)cc1)C(F)F] |
| Fe-1 | 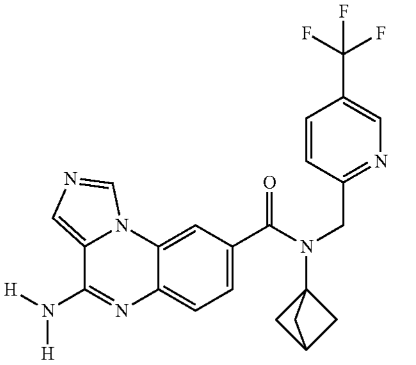 [SMILES: Nc1nc2ccc(C(=O)N(Cc3ccc(C(F)(F)F)cn3)C34CC(C3)C4)cc2n2cncc12] |
| Fe-2 | 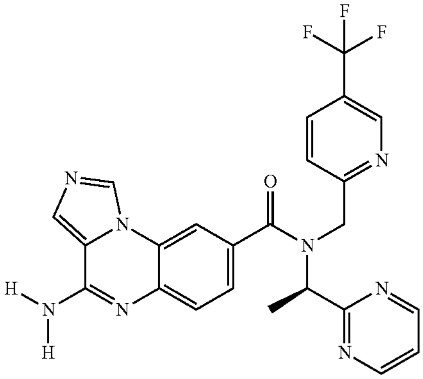 [SMILES: C[C@H](c1ncccn1)N(Cc1ccc(C(F)(F)F)cn1)C(=O)c1ccc2nc(N)c3cncn3c2c1] |
| Ff-1 | 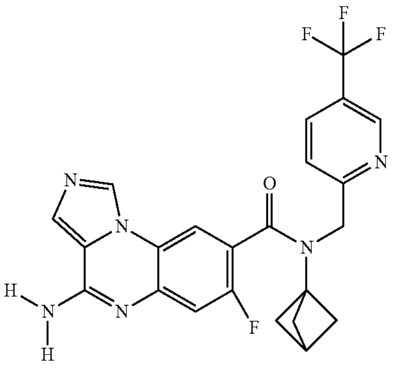 [SMILES: Nc1nc2cc(F)c(C(=O)N(Cc3ccc(C(F)(F)F)cn3)C34CC(C3)C4)cc2n2cncc12] |

TABLE 1B-continued
| Compounds | |
|---|---|
| Example | Structure |
| Ff-2 | 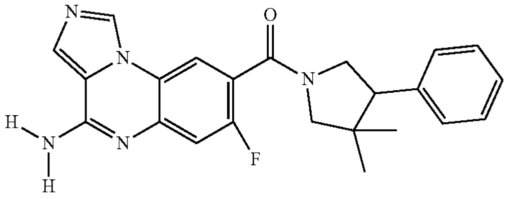 [SMILES: CC1(C)CN(C(=O)c2cc3c(cc2F)nc(N)c2cncn23)CC1c1ccccc1] |
| Ff-3 | 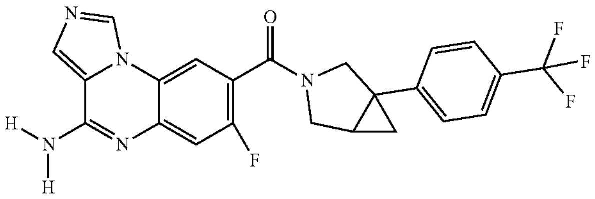 [SMILES: Nc1nc2cc(F)c(C(=O)N3CC4CC4(c4ccc(C(F)(F)F)cc4)C3)cc2n2cncc12] |
| Ff-4 | 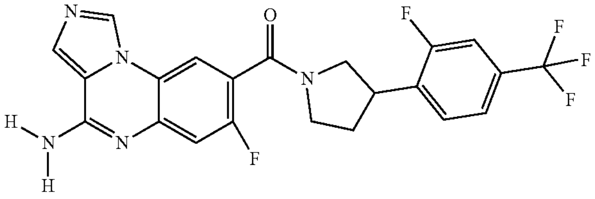 [SMILES: Nc1nc2cc(F)c(C(=O)N3CCC(c4ccc(C(F)(F)F)cc4F)C3)cc2n2cncc12] |
| Ff-5 | 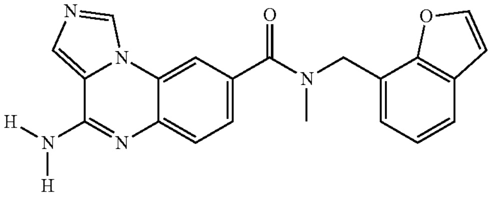 [SMILES: CN(Cc1cccc2ccoc12)C(=O)c1ccc2nc(N)c3cncn3c2c1] |
| Ff-6 | 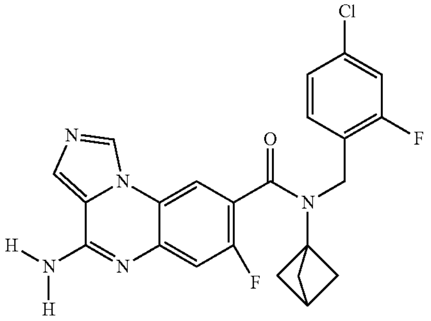 [SMILES: Nc1nc2cc(F)c(C(=O)N(Cc3ccc(Cl)cc3F)C34CC(C3)C4)cc2n2cncc12] |
| Ff-7 | 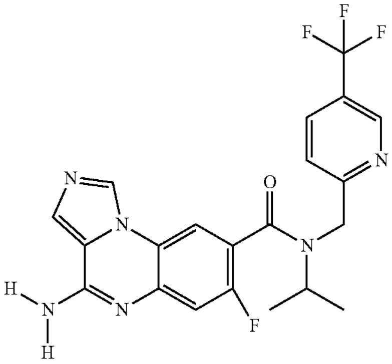 [SMILES: CC(C)N(Cc1ccc(C(F)(F)F)cn1)C(=O)c1cc2c(cc1F)nc(N)c1cncn12] |

TABLE 1B-continued
| Compounds | |
|---|---|
| Example | Structure |
| Ff-8 | 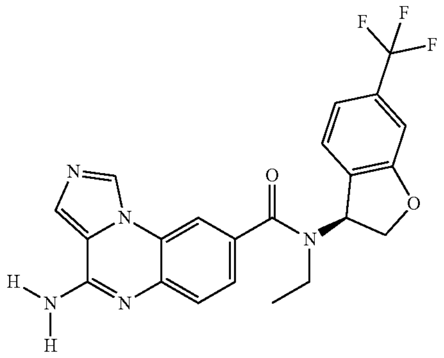 [SMILES: CCN(C(=O)c1ccc2nc(N)c3cncn3c2c1)[C@@H]1COc2cc(C(F)(F)F)ccc21] |
| Ff-9 | 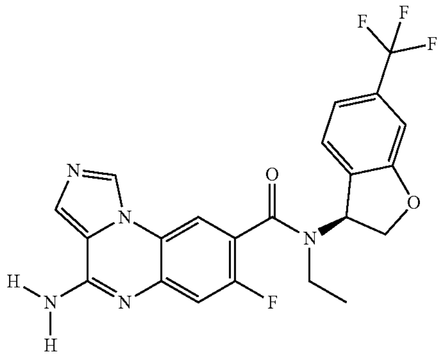 [SMILES: CCN(C(=O)c1cc2c(cc1F)nc(N)c1cncn12)[C@@H]1COc2cc(C(F)(F)F)ccc21] |
| Ff-10 | 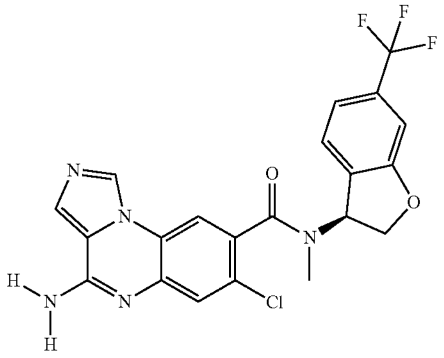 [SMILES: CN(C(=O)c1cc2c(cc1Cl)nc(N)c1cncn12)[C@@H]1COc2cc(C(F)(F)F)ccc21] |
| Ff-11 | 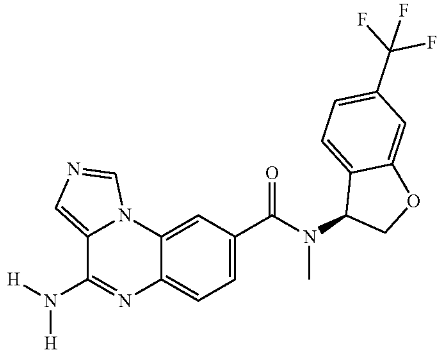 [SMILES: CN(C(=O)c1ccc2nc(N)c3cncn3c2c1)[C@@H]1COc2cc(C(F)(F)F)ccc21] |

TABLE 1B-continued
| Compounds | |
|---|---|
| Example | Structure |
| Ff-12 | 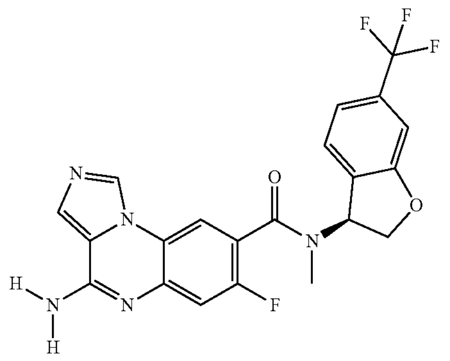 [SMILES: CN(C(=O)c1cc2c(cc1F)nc(N)c1cncn12)[C@@H]1COc2cc(C(F)(F)F)ccc21] |
| Ff-13 | 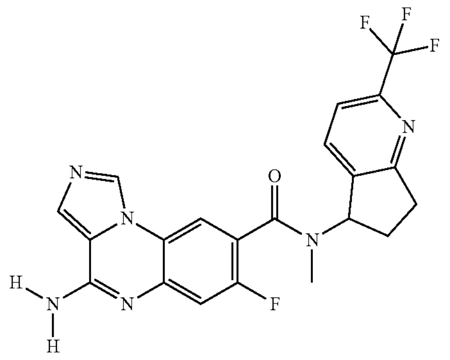 [SMILES: CN(C(=O)c1cc2c(cc1F)nc(N)c1cncn12)C1CCc2nc(C(F)(F)F)ccc21] |
| Ff-14 | 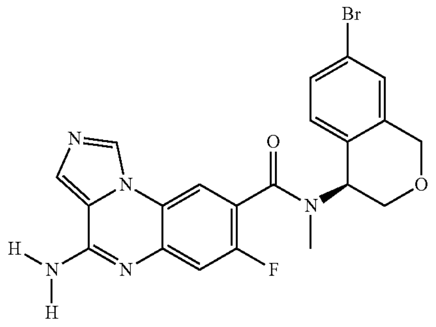 [SMILES: CN(C(=O)c1cc2c(cc1F)nc(N)c1cncn12)[C@@H]1COCc2cc(Br)ccc21] |
| Ff-15 | 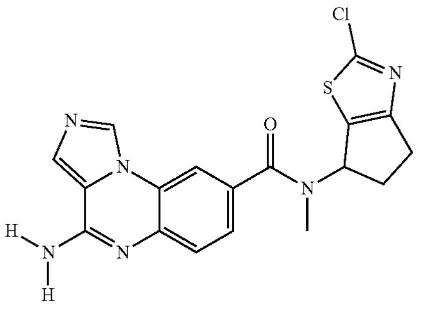 [SMILES: CN(C(=O)c1ccc2nc(N)c3cncn3c2c1)C1CCc2nc(Cl)sc21] |

TABLE 1B-continued
| Compounds | |
| --- | --- |
| Example | Structure |
| Ff-16 | 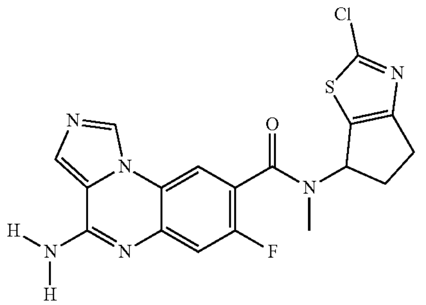 [SMILES: CN(C(=O)c1cc2c(cc1F)nc(N)c1cncn12)C1CCc2nc(Cl)sc21] |
| Ff-17 | 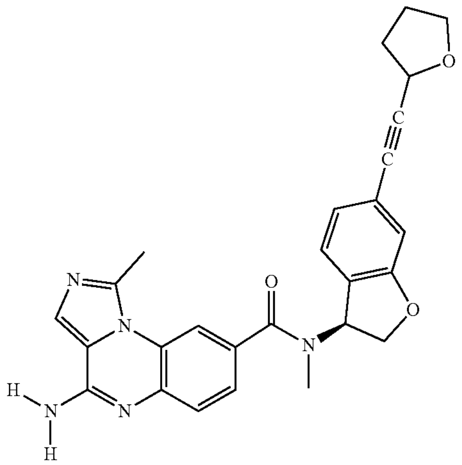 [SMILES: Cc1ncc2c(N)nc3ccc(C(=O)N(C)[C@@H]4COc5cc(C#CC6CCCO6)ccc54)cc3n12] |
| Ff-18 | 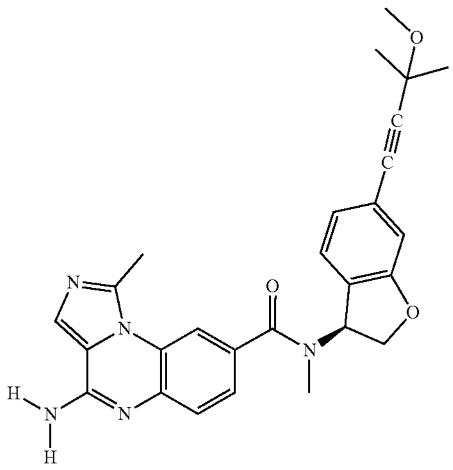 [SMILES: COC(C)(C)C#Cc1ccc2c(c1)OC[C@H]2N(C)C(=O)c1ccc2nc(N)c3cnc(C)n3c2c1] |

TABLE 1B-continued
| Compounds | |
|---|---|
| Example | Structure |
| Ff-19 | 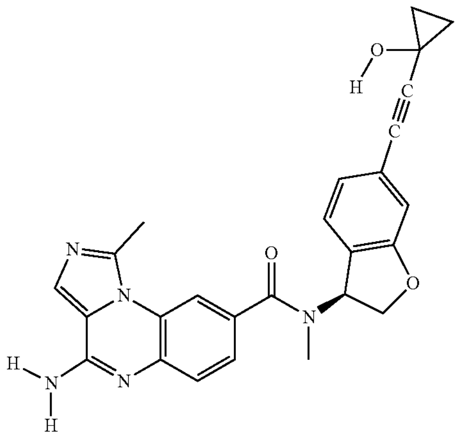 [SMILES: Cc1ncc2c(N)nc3ccc(C(=O)N(C)[C@@H]4COc5cc(C#CC6(O)CC6)ccc54)cc3n12] |
| Ff-20 | 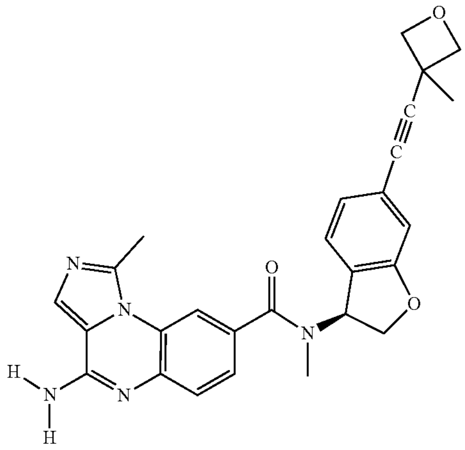 [SMILES: Cc1ncc2c(N)nc3ccc(C(=O)N(C)[C@@H]4COc5cc(C#CC6(C)COC6)ccc54)cc3n12] |
| Ff-21 | 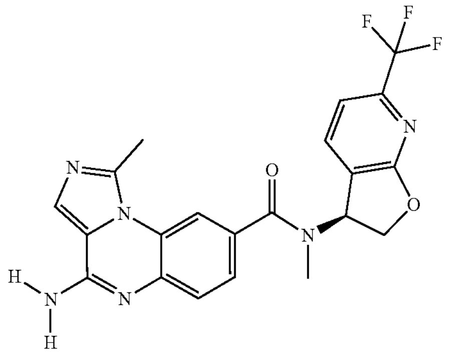 [SMILES: Cc1ncc2c(N)nc3ccc(C(=O)N(C)[C@@H]4COc5nc(C(F)(F)F)ccc54)cc3n12] |

TABLE 1B-continued
| Compounds | |
|---|---|
| Example | Structure |
| Ff-22 | 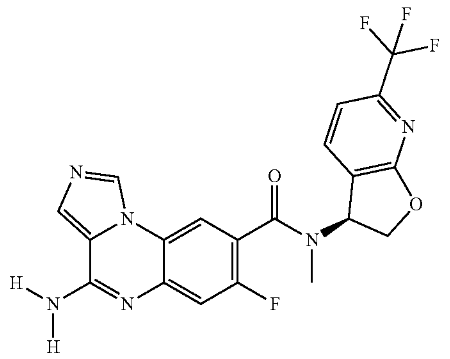 [SMILES: CN(C(=O)c1cc2c(cc1F)nc(N)c1cncn12)[C@@H]1COc2nc(C(F)(F)F)ccc21] |
| Ff-23 | 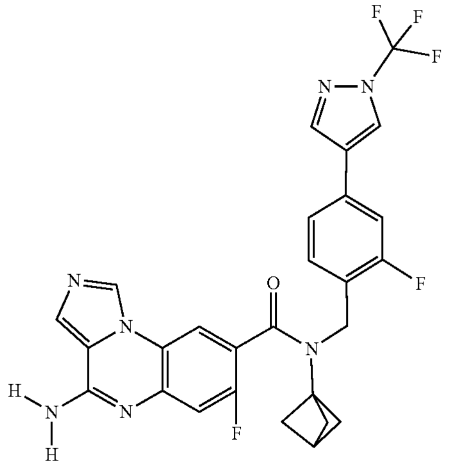 [SMILES: Nc1nc2cc(F)c(C(=O)N(Cc3ccc(-c4cnn(C(F)(F)F)c4)cc3F)C34CC(C3)C4)cc2n2cncc12] |
| Ff-24 | 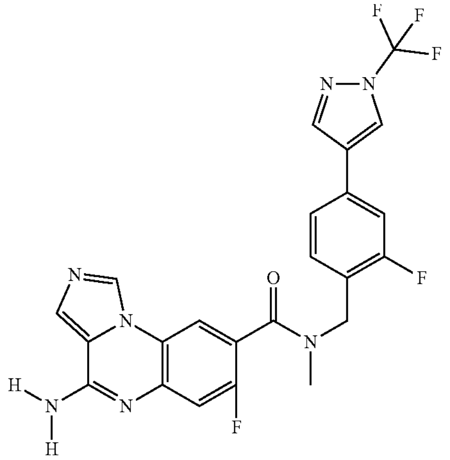 [SMILES: CN(Cc1ccc(-c2cnn(C(F)(F)F)c2)cc1F)C(=O)c1cc2c(cc1F)nc(N)c1cncn12] |

TABLE 1B-continued
| Compounds | |
|---|---|
| Example | Structure |
| Ff-25 | 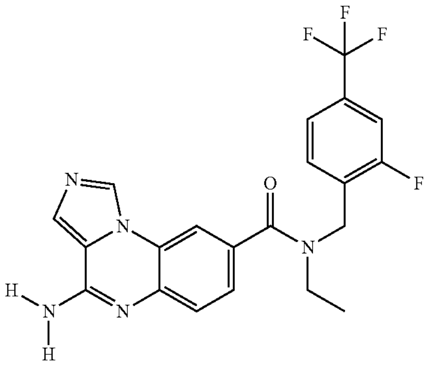 [SMILES: CCN(Cc1ccc(C(F)(F)F)cc1F)C(=O)c1ccc2nc(N)c3cncn3c2c1] |
| Ff-26 | 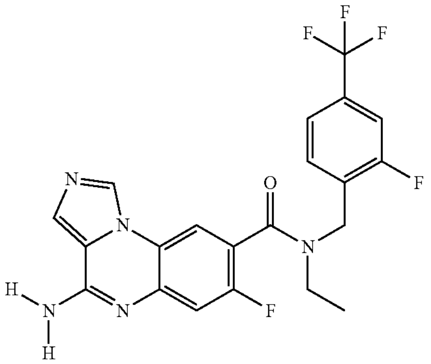 [SMILES: CCN(Cc1ccc(C(F)(F)F)cc1F)C(=O)c1cc2c(cc1F)nc(N)c1cncn12] |
| Ff-27 | 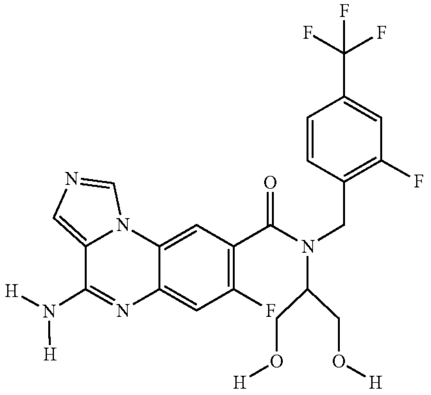 [SMILES: Nc1nc2cc(F)c(C(=O)N(Cc3ccc(C(F)(F)F)cc3F)C(CO)CO)cc2n2cncc12] |
| Ff-30 | 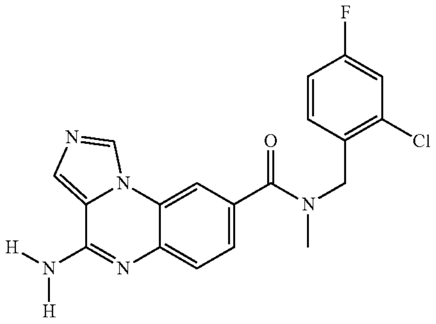 [SMILES: CN(Cc1ccc(F)cc1Cl)C(=O)c1ccc2nc(N)c3cncn3c2c1] |

TABLE 1B-continued
| Compounds | |
|---|---|
| Example | Structure |
| Ff-31 | 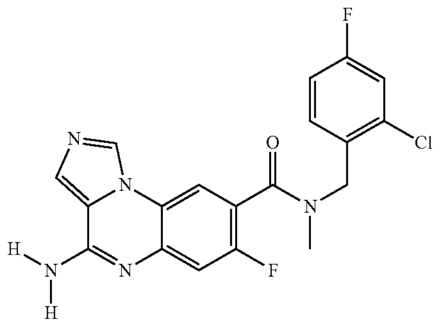 [SMILES: CN(Cc1ccc(F)cc1Cl)C(=O)c1cc2c(cc1F)nc(N)c1cncn12] |
| Ff-32 | 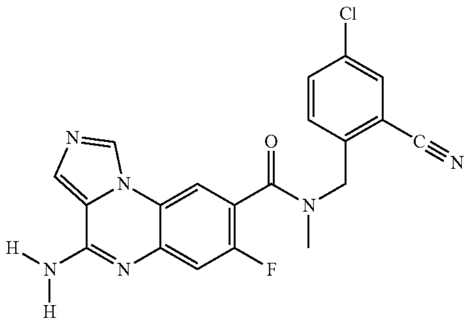 [SMILES: CN(Cc1ccc(Cl)cc1C#N)C(=O)c1cc2c(cc1F)nc(N)c1cncn12] |
| Ff-38 | 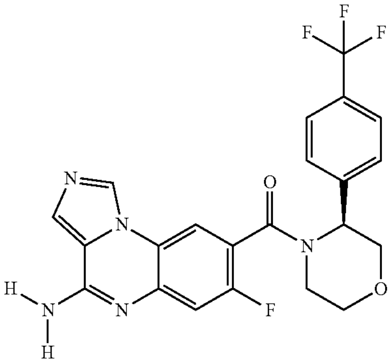 |
| Ff-39 | 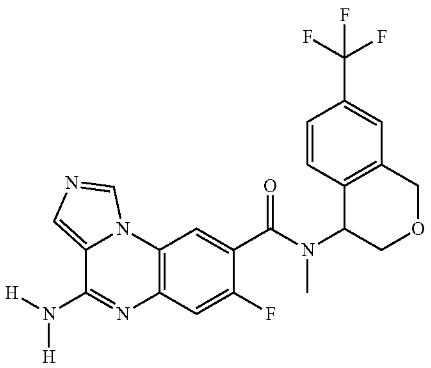 |

TABLE 1B-continued
| Compounds | |
|---|---|
| Example | Structure |
| Ff-40 | 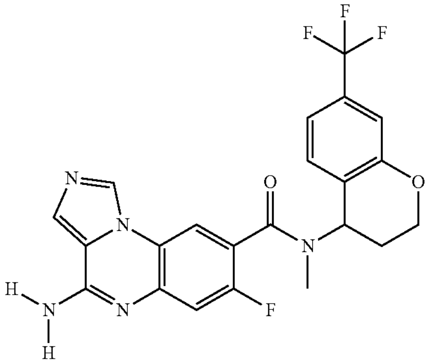 [SMILES: CN(C(=O)c1cc2c(cc1F)nc(N)c1cncn12)C1CCOc2cc(C(F)(F)F)ccc21] |
| Ff-41 | 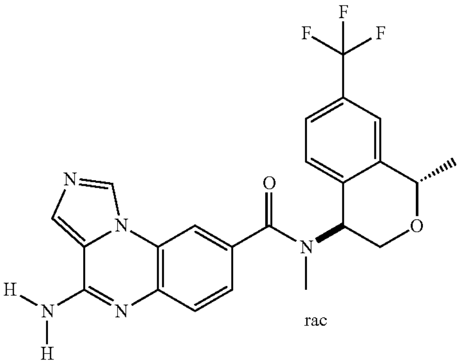 [SMILES: C[C@@H]1OC[C@@H](N(C)C(=O)c2ccc3nc(N)c4cncn4c3c2)c2ccc(C(F)(F)F)cc21] rac |
| Ff-42 | 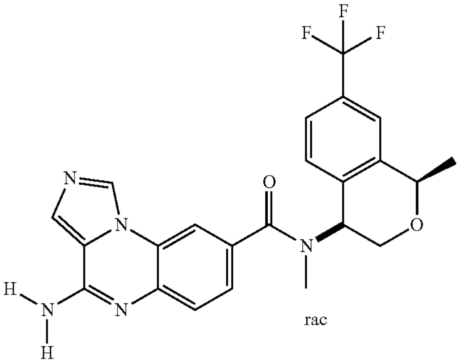 [SMILES: C[C@H]1OC[C@@H](N(C)C(=O)c2ccc3nc(N)c4cncn4c3c2)c2ccc(C(F)(F)F)cc21] rac |
| Ff-45 | 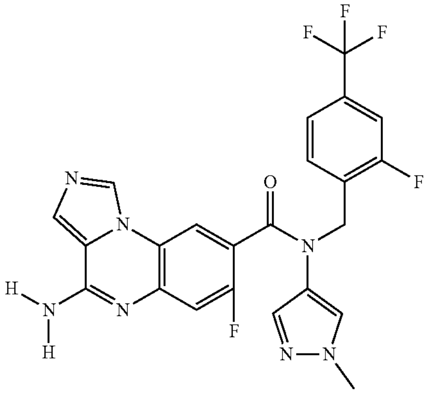 [SMILES: Cn1cc(N(Cc2ccc(C(F)(F)F)cc2F)C(=O)c2cc3c(cc2F)nc(N)c2cncn23)cn1] |

TABLE 1B-continued
| Compounds | |
| --- | --- |
| Example | Structure |
| Ff-46 | 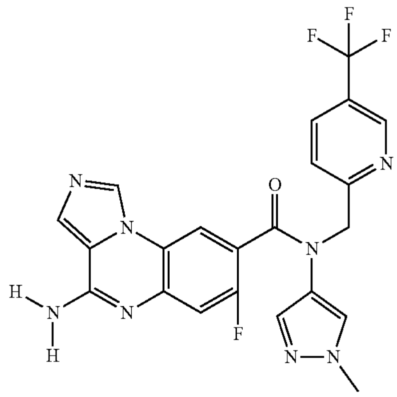 [SMILES: Cn1cc(N(Cc2ccc(C(F)(F)F)cn2)C(=O)c2cc3c(cc2F)nc(N)c2cncn23)cn1] |
| Ff-47 | 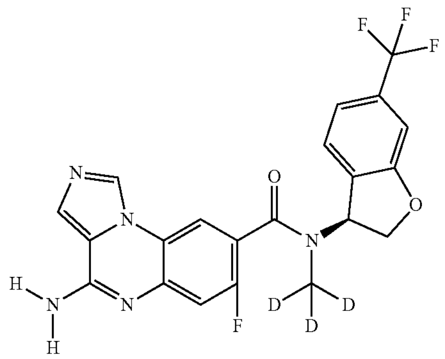 [SMILES: [2H]C([2H])([2H])N(C(=O)c1cc2c(cc1F)nc(N)c1cncn12)[C@@H]1COc2cc(C(F)(F)F)ccc21] |
| Ff-48 | 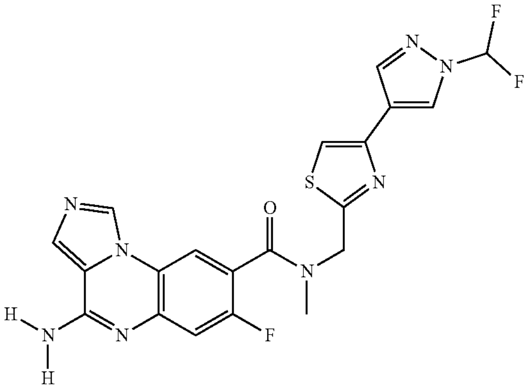 [SMILES: CN(Cc1nc(-c2cnn(C(F)F)c2)cs1)C(=O)c1cc2c(cc1F)nc(N)c1cncn12] |
| Ff-49 | 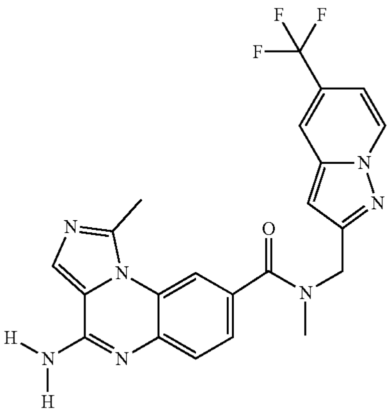 [SMILES: Cc1ncc2c(N)nc3ccc(C(=O)N(C)Cc4cc5cc(C(F)(F)F)ccn5n4)cc3n12] |

TABLE 1B-continued
| Compounds | |
|---|---|
| Example | Structure |
| Ff-50 | 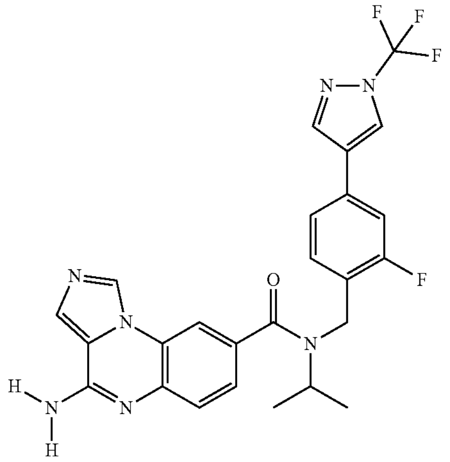 [SMILES: CC(C)N(Cc1ccc(-c2cnn(C(F)(F)F)c2)cc1F)C(=O)c1ccc2nc(N)c3cncn3c2c1] |
| Ff-51 | 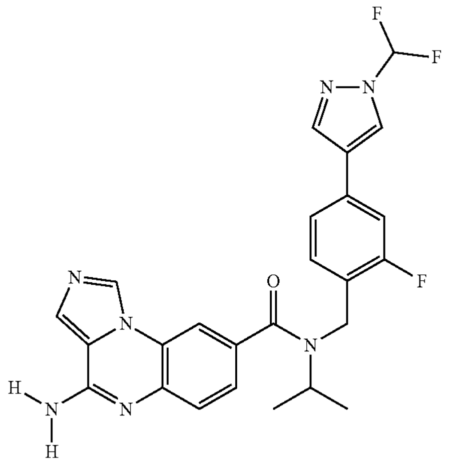 [SMILES: CC(C)N(Cc1ccc(-c2cnn(C(F)F)c2)cc1F)C(=O)c1ccc2nc(N)c3cncn3c2c1] |
| Ff-52 | 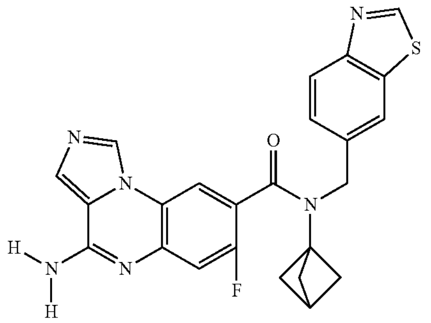 [SMILES: Nc1nc2cc(F)c(C(=O)N(Cc3ccc4ncsc4c3)C34CC(C3)C4)cc2n2cncc12] |

TABLE 1B-continued
| Compounds | |
|---|---|
| Example | Structure |
| Ff-53 | 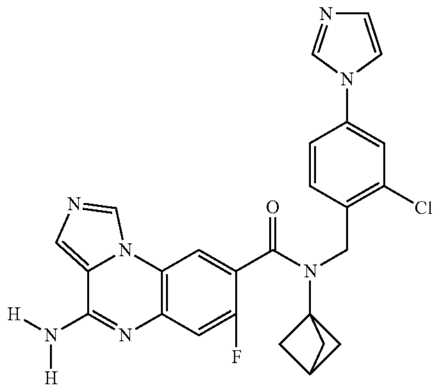 [SMILES: Nc1nc2cc(F)c(C(=O)N(Cc3ccc(-n4ccnc4)cc3Cl)C34CC(C3)C4)cc2n2cncc12] |
| Ff-54 | 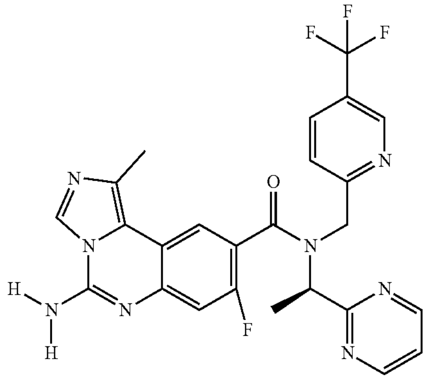 [SMILES: Cc1ncn2c(N)nc3cc(F)c(C(=O)N(Cc4ccc(C(F)(F)F)cn4)[C@H](C)c4ncccn4)cc3c12] |
| Ff-57 | 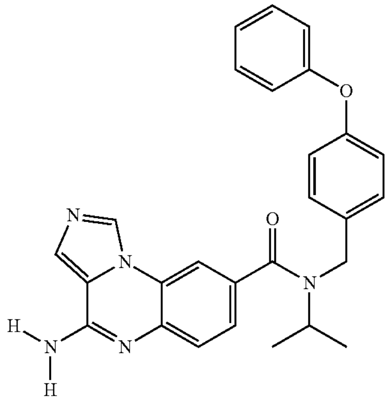 [SMILES: CC(C)N(Cc1ccc(Oc2ccccc2)cc1)C(=O)c1ccc2nc(N)c3cncn3c2c1] |
| Ff-58 | 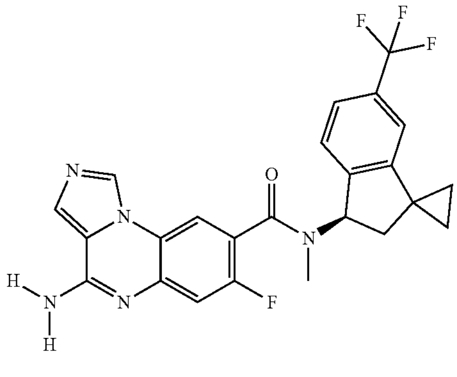 [SMILES: CN(C(=O)c1cc2c(cc1F)nc(N)c1cncn12)[C@@H]1CC2(CC2)c2cc(C(F)(F)F)ccc21] |

TABLE 1B-continued
| Compounds | |
|---|---|
| Example | Structure |
| Ff-59 | 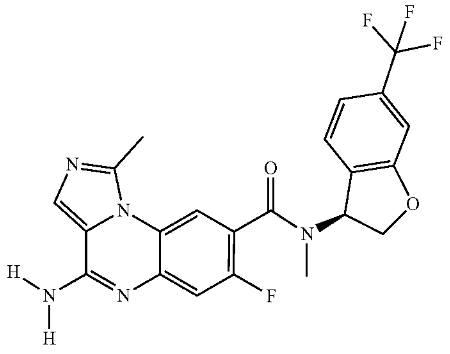 [SMILES: Cc1ncc2c(N)nc3cc(F)c(C(=O)N(C)[C@@H]4COc5cc(C(F)(F)F)ccc54)cc3n12] |
| Ff-63 | 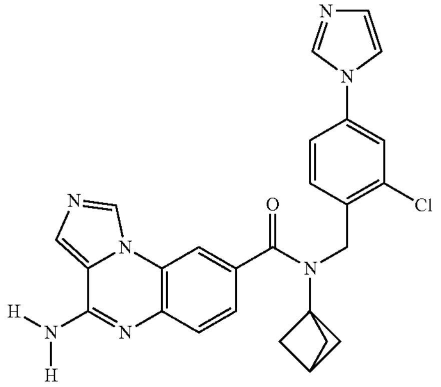 [SMILES: Nc1nc2ccc(C(=O)N(Cc3ccc(-n4ccnc4)cc3Cl)C34CC(C3)C4)cc2n2cncc12] |
| Ff-68 | 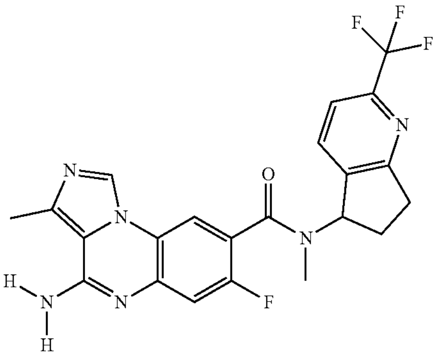 [SMILES: Cc1ncn2c1c(N)nc1cc(F)c(C(=O)N(C)C3CCc4nc(C(F)(F)F)ccc43)cc12] |
| Ff-69 | 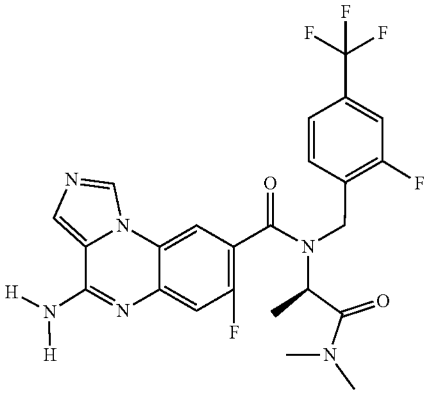 [SMILES: C[C@H](C(=O)N(C)C)N(Cc1ccc(C(F)(F)F)cc1F)C(=O)c1cc2c(cc1F)nc(N)c1cncn12] |

TABLE 1B-continued
| Compounds | |
|---|---|
| Example | Structure |
| Ff-70 | 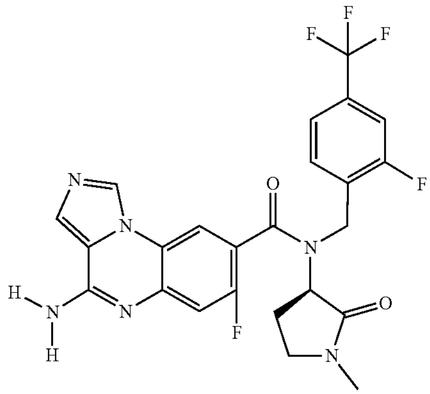 [SMILES: CN1CC[C@@H](N(Cc2ccc(C(F)(F)F)cc2F)C(=O)c2cc3c(cc2F)nc(N)c2cncn23)C1=O] |
| Ff-71 | 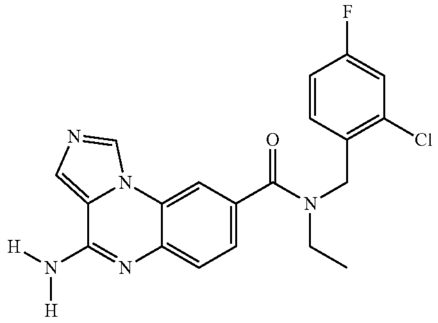 [SMILES: CCN(Cc1ccc(F)cc1Cl)C(=O)c1ccc2nc(N)c3cncn3c2c1] |
| Ff-72 | 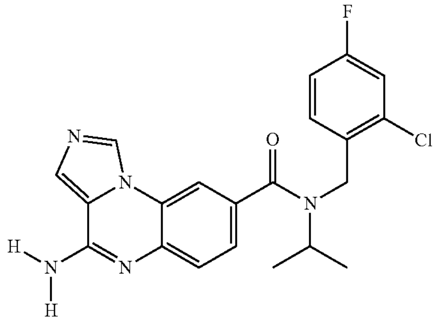 [SMILES: CC(C)N(Cc1ccc(F)cc1Cl)C(=O)c1ccc2nc(N)c3cncn3c2c1] |
| Ff-73 | 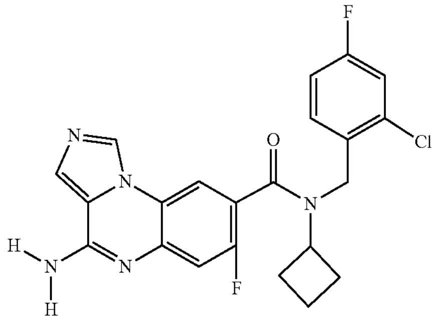 [SMILES: Nc1nc2cc(F)c(C(=O)N(Cc3ccc(F)cc3Cl)C3CCC3)cc2n2cncc12] |

TABLE 1B-continued
| Compounds | |
|---|---|
| Example | Structure |
| Ff-84 | 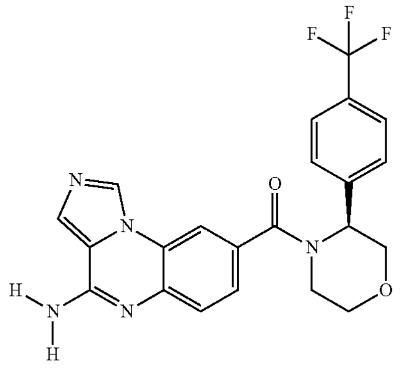 |
| Ff-86 | 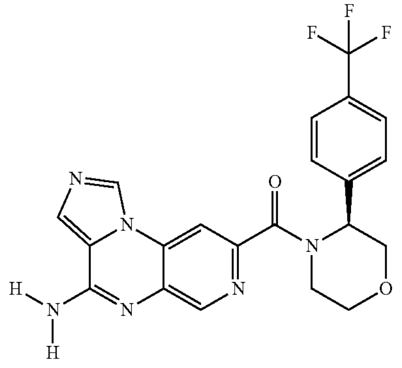 |
| Ff-87 | 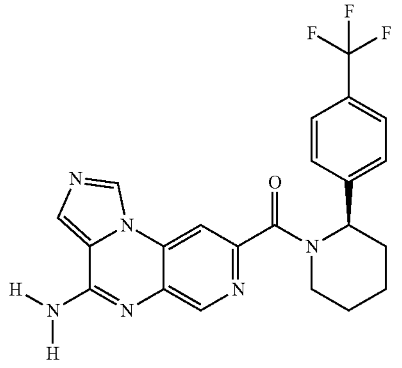 [SMILES: Nc1nc2cnc(C(=O)N3CCOC[C@@H]3c3ccc(C(F)(F)F)cc3)cc2n2cncc12] |
| Ff-92 | 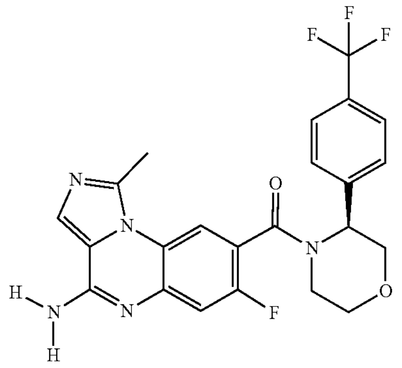 [SMILES: Cc1ncc2c(N)nc3cc(F)c(C(=O)N4CCOC[C@@H]4c4ccc(C(F)(F)F)cc4)cc3n12] |

TABLE 1B-continued
| Compounds | |
|---|---|
| Example | Structure |
| Ff-94 | 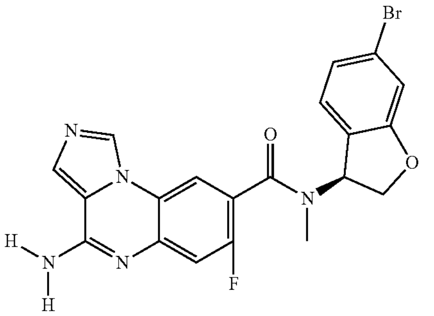 [SMILES: CN(C(=O)c1cc2c(cc1F)nc(N)c1cncn12)[C@@H]1COc2cc(Br)ccc21] |
| Ff-95 | 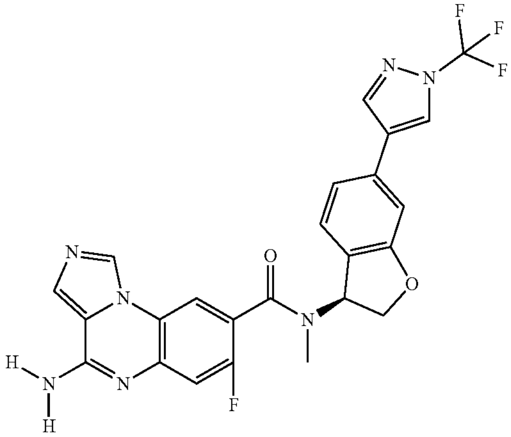 [SMILES: CN(C(=O)c1cc2c(cc1F)nc(N)c1cncn12)[C@@H]1COc2cc(-c3cnn(C(F)(F)F)c3)ccc21] |
| Ff-103 | 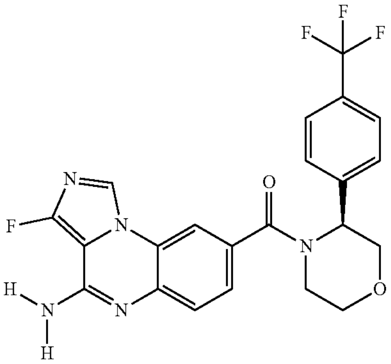 [SMILES: Nc1nc2ccc(C(=O)N3CCOC[C@@H]3c3ccc(C(F)(F)F)cc3)cc2n2cnc(F)c12] |
| Ff-114 | 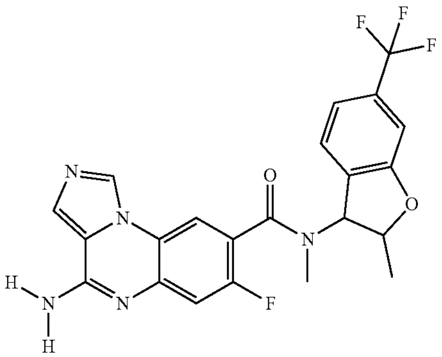 [SMILES: CC1Oc2cc(C(F)(F)F)ccc2C1N(C)C(=O)c1cc2c(cc1F)nc(N)c1cncn12] |

TABLE 1B-continued
| Compounds | |
|---|---|
| Example | Structure |
| Ff-123 | 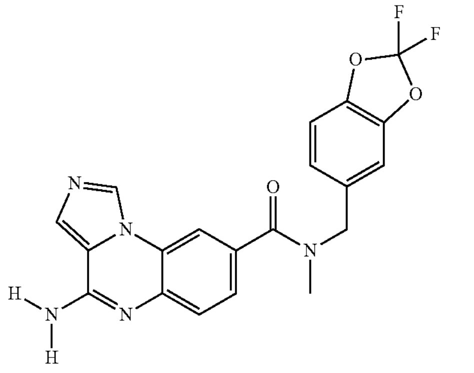 [SMILES: CN(Cc1ccc2c(c1)OC(F)(F)O2)C(=O)c1ccc2nc(N)c3cncn3c2c1] |
| Ff-124 | 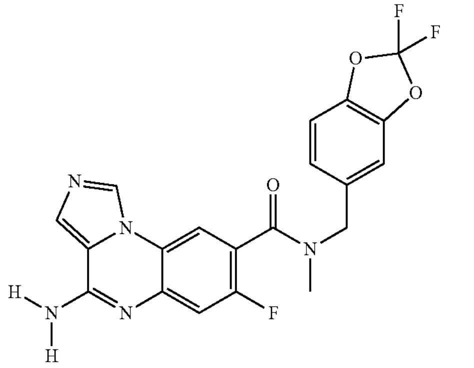 [SMILES: CN(Cc1ccc2c(c1)OC(F)(F)O2)C(=O)c1cc2c(cc1F)nc(N)c1cncn12] |
| Ff-125 | 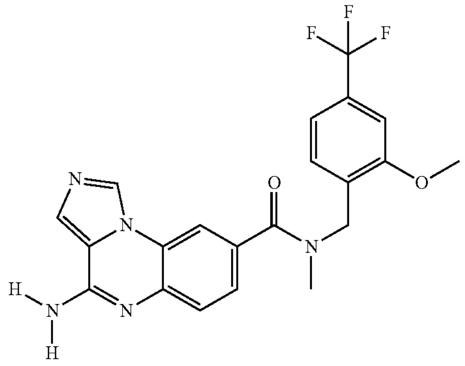 [SMILES: COc1cc(C(F)(F)F)ccc1CN(C)C(=O)c1ccc2nc(N)c3cncn3c2c1] |
| Ff-126 | 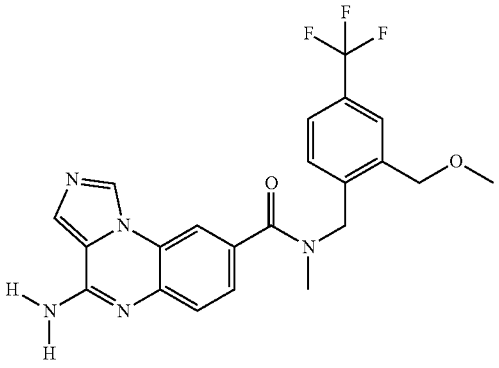 [SMILES: COCc1cc(C(F)(F)F)ccc1CN(C)C(=O)c1ccc2nc(N)c3cncn3c2c1] |

TABLE 1B-continued
| Compounds | |
|---|---|
| Example | Structure |
| Ff-127 | 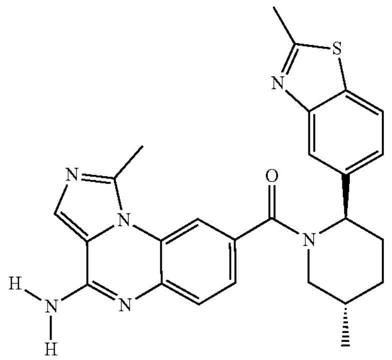 [SMILES: Cc1nc2cc([C@H]3CC[C@H](C)CN3C(=O)c3ccc4nc(N)c5cnc(C)n5c4c3)ccc2s1] |
| Ff-128 | 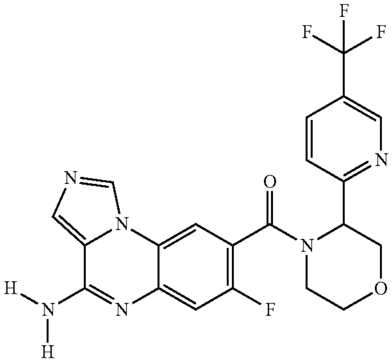 [SMILES: Nc1nc2cc(F)c(C(=O)N3CCOCC3c3ccc(C(F)(F)F)cn3)cc2n2cncc12] |
| Ff-129 | 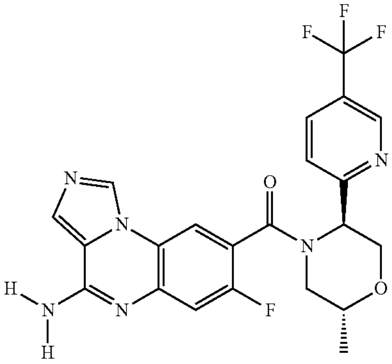 [SMILES: C[C@@H]1CN(C(=O)c2cc3c(cc2F)nc(N)c2cncn23)[C@@H](c2ccc(C(F)(F)F)cn2)CO1] |
| Ff-130 | 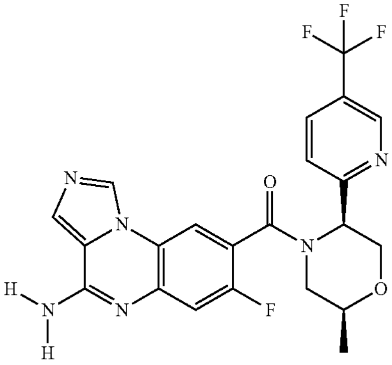 [SMILES: C[C@H]1CN(C(=O)c2cc3c(cc2F)nc(N)c2cncn23)[C@@H](c2ccc(C(F)(F)F)cn2)CO1] |

TABLE 1B-continued
| Compounds | |
|---|---|
| Example | Structure |
| Ff-131 | 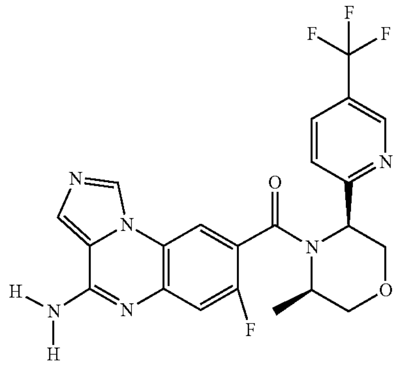 [SMILES: C[C@@H]1COC[C@H](c2ccc(C(F)(F)F)cn2)N1C(=O)c1cc2c(cc1F)nc(N)c1cncn12] |
| Ff-132 | 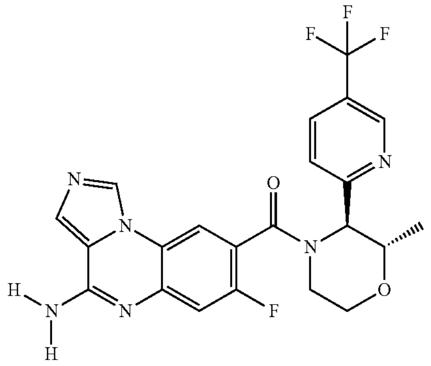 [SMILES: C[C@@H]1OCCN(C(=O)c2cc3c(cc2F)nc(N)c2cncn23)[C@H]1c1ccc(C(F)(F)F)cn1] |
| Ff-133 | 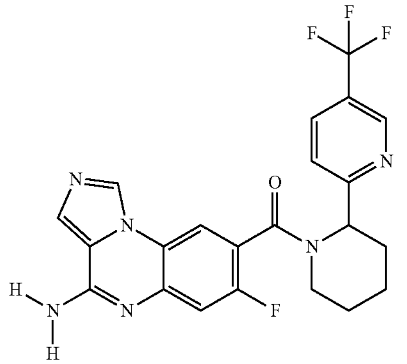 [SMILES: Nc1nc2cc(F)c(C(=O)N3CCCCC3c3ccc(C(F)(F)F)cn3)cc2n2cncc12] |
| Ff-134 | 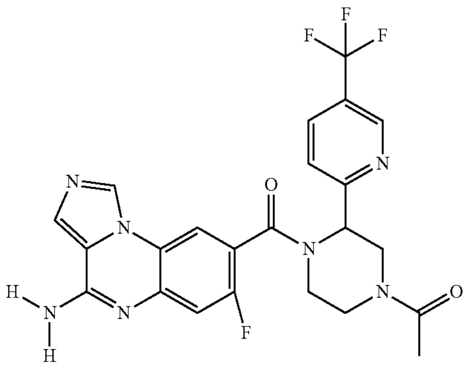 [SMILES: CC(=O)N1CCN(C(=O)c2cc3c(cc2F)nc(N)c2cncn23)C(c2ccc(C(F)(F)F)cn2)C1] |

TABLE 1B-continued
| Compounds | |
|---|---|
| Example | Structure |
| Ff-135 | 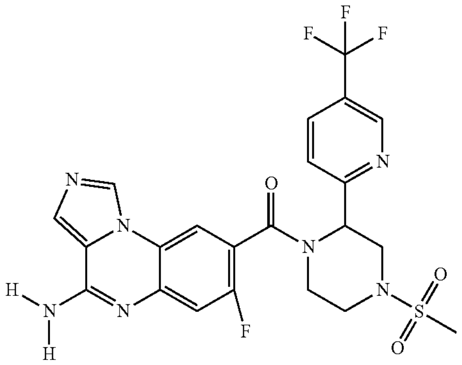 [SMILES: CS(=O)(=O)N1CCN(C(=O)c2cc3c(cc2F)nc(N)c2cncn23)C(c2ccc(C(F)(F)F)cn2)C1] |
| Ff-136 | 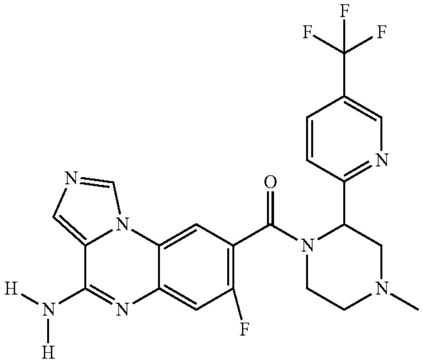 [SMILES: CN1CCN(C(=O)c2cc3c(cc2F)nc(N)c2cncn23)C(c2ccc(C(F)(F)F)cn2)C1] |
| Ff-137 | 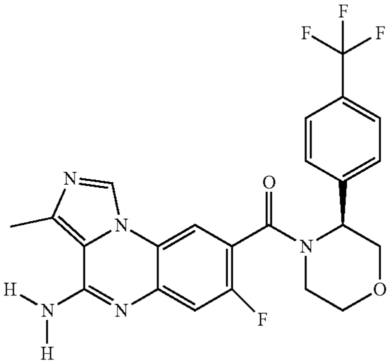 [SMILES: Cc1ncn2c1c(N)nc1cc(F)c(C(=O)N3CCOC[C@@H]3c3ccc(C(F)(F)F)cc3)cc12] |
| Ff-138 | 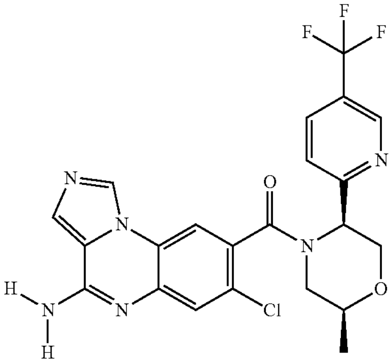 [SMILES: C[C@H]1CN(C(=O)c2cc3c(cc2Cl)nc(N)c2cncn23)[C@@H](c2ccc(C(F)(F)F)cn2)CO1] |

TABLE 1B-continued
| Compounds | |
|---|---|
| Example | Structure |
| Ff-139 | 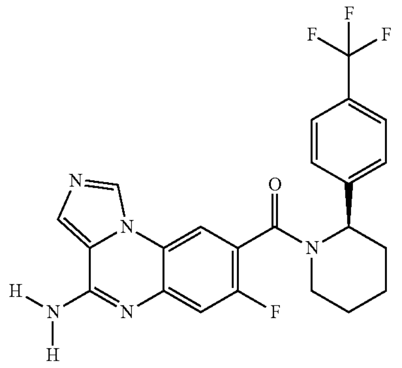 |
| Ff-140 | 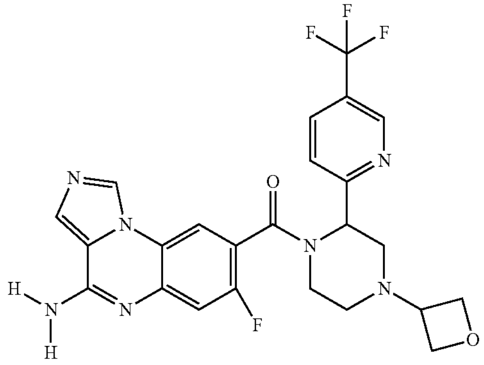 [SMILES: Nc1nc2cc(F)c(C(=O)N3CCN(C4COC4)CC3c3ccc(C(F)(F)F)cn3)cc2n2cncc12] |
| Ff-141 | 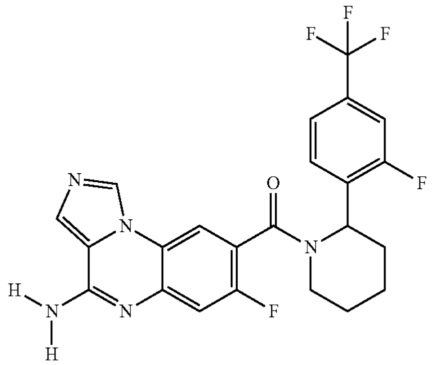 [SMILES: Nc1nc2cc(F)c(C(=O)N3CCCCC3c3ccc(C(F)(F)F)cc3F)cc2n2cncc12] |
| Ff-142 | 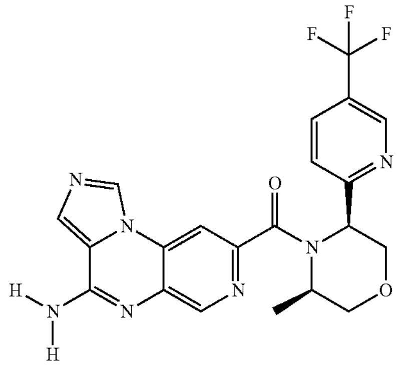 [SMILES: C[C@@H]1COC[C@H](c2ccc(C(F)(F)F)cn2)N1C(=O)c1cc2c(cn1)nc(N)c1cncn12] |

TABLE 1B-continued
| Compounds | |
| --- | --- |
| Example | Structure |
| Ff-143 | 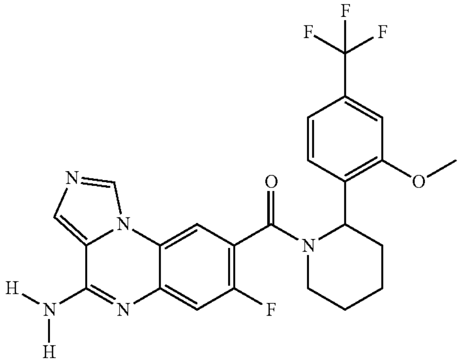 [SMILES: COc1cc(C(F)(F)F)ccc1C1CCCCN1C(=O)c1cc2c(cc1F)nc(N)c1cncn12] |
| Ff-144 | 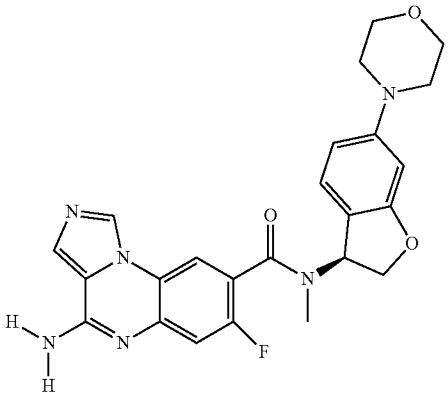 [SMILES: CN(C(=O)c1cc2c(cc1F)nc(N)c1cncn12)[C@@H]1COc2cc(N3CCOCC3)ccc21] |
| Ff-145 | 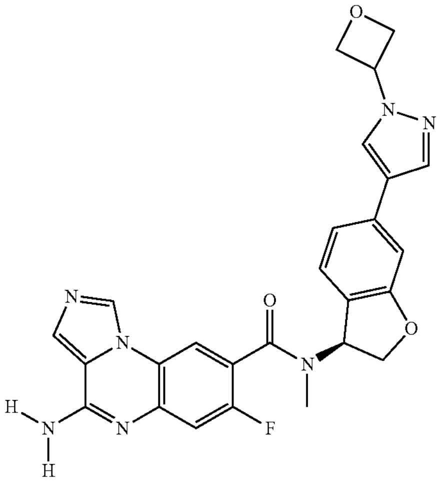 [SMILES: CN(C(=O)c1cc2c(cc1F)nc(N)c1cncn12)[C@@H]1COc2cc(-c3cnn(C4COC4)c3)ccc21] |

TABLE 1B-continued
| Compounds | |
|---|---|
| Example | Structure |
| Ff-146 | 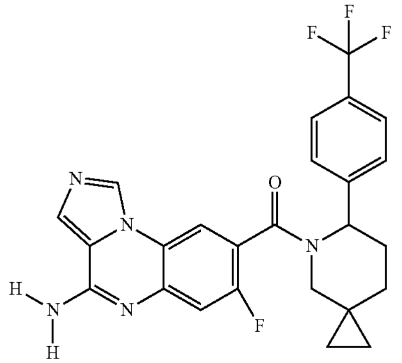 [SMILES: Nc1nc2cc(F)c(C(=O)N3CC4(CCC3c3ccc(C(F)(F)F)cc3)CC4)cc2n2cncc12] |
| Ff-147 | 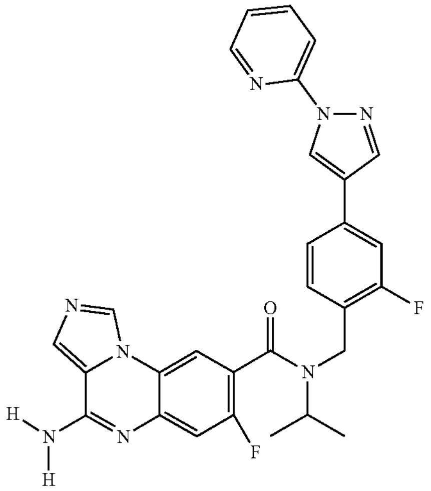 [SMILES: CC(C)N(Cc1ccc(-c2cnn(-c3ccccn3)c2)cc1F)C(=O)c1cc2c(cc1F)nc(N)c1cncn12] |
| Ff-148 | 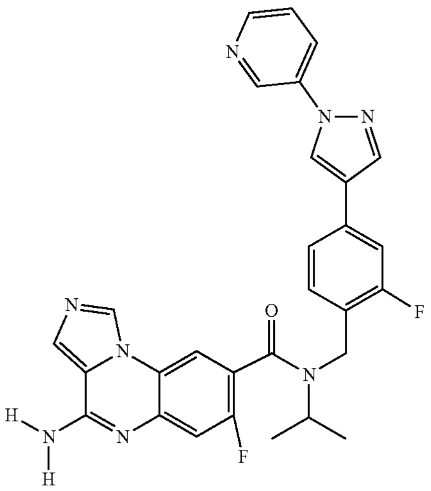 [SMILES: CC(C)N(Cc1ccc(-c2cnn(-c3cccnc3)c2)cc1F)C(=O)c1cc2c(cc1F)nc(N)c1cncn12] |

TABLE 1B-continued
| Compounds | |
|---|---|
| Example | Structure |
| Ff-149 | 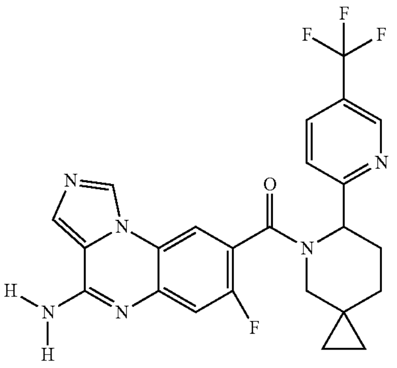 [SMILES: Nc1nc2cc(F)c(C(=O)N3CC4(CCC3c3ccc(C(F)(F)F)cn3)CC4)cc2n2cncc12] |
| Ff-150 | 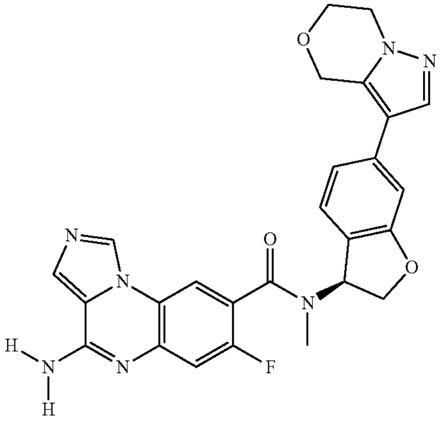 [SMILES: CN(C(=O)c1cc2c(cc1F)nc(N)c1cncn12)[C@@H]1COc2cc(-c3cnn4c3COCC4)ccc21] |
| Ff-151 | 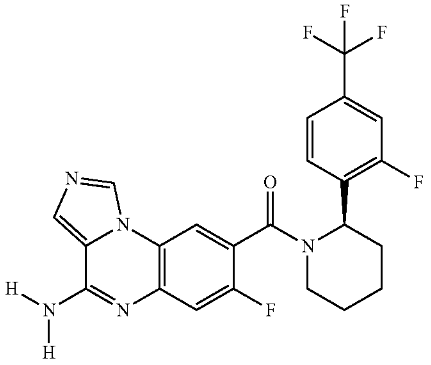 [SMILES: Nc1nc2cc(F)c(C(=O)N3CCCC[C@@H]3c3ccc(C(F)(F)F)cc3F)cc2n2cncc12] |
| Ff-152 | 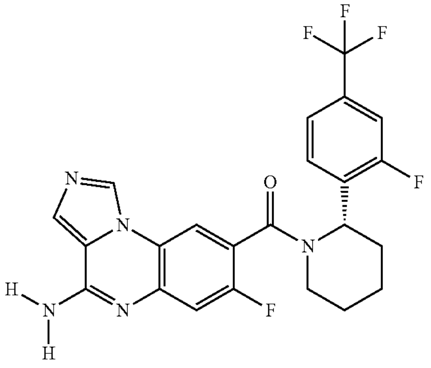 [SMILES: Nc1nc2cc(F)c(C(=O)N3CCCC[C@H]3c3ccc(C(F)(F)F)cc3F)cc2n2cncc12] |

TABLE 1B-continued
| Compounds | |
|---|---|
| Example | Structure |
| Ff-153 | 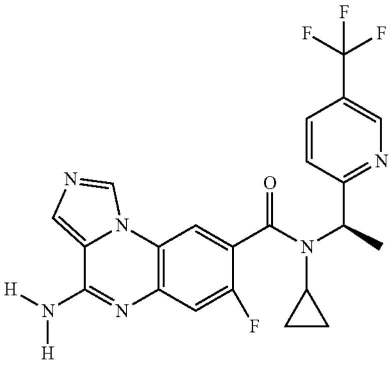 [SMILES: C[C@H](c1ccc(C(F)(F)F)cn1)N(C(=O)c1cc2c(cc1F)nc(N)c1cncn12)C1CC1] |
| Ff-154 | 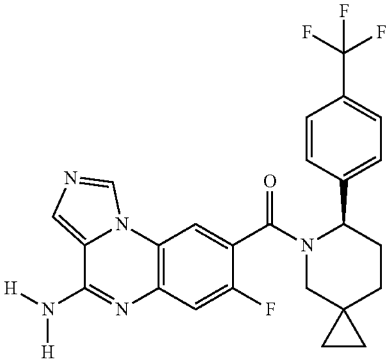 [SMILES: Nc1nc2cc(F)c(C(=O)N3CC4(CC[C@@H]3c3ccc(C(F)(F)F)cc3)CC4)cc2n2cncc12] |
| Ff-155 | 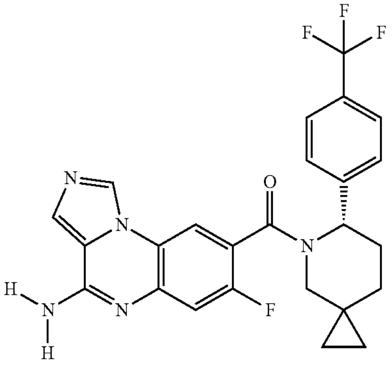 [SMILES: Nc1nc2cc(F)c(C(=O)N3CC4(CC[C@H]3c3ccc(C(F)(F)F)cc3)CC4)cc2n2cncc12] |
| Ff-156 | 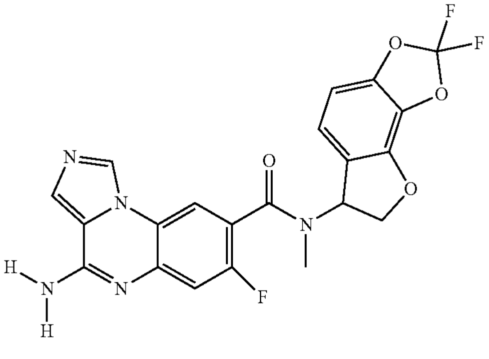 [SMILES: CN(C(=O)c1cc2c(cc1F)nc(N)c1cncn12)C1COc2c1ccc1c2OC(F)(F)O1] |

TABLE 1B-continued
| Compounds | |
|---|---|
| Example | Structure |
| Ff-158 | 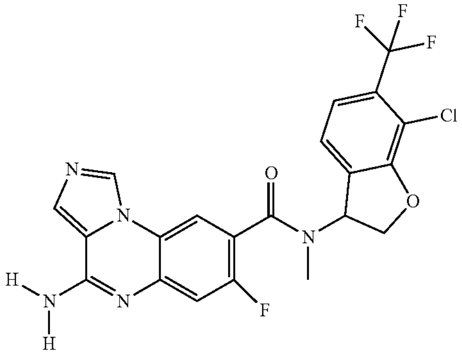 [SMILES: CN(C(=O)c1cc2c(cc1F)nc(N)c1cncn12)C1COc2c1ccc(C(F)(F)F)c2Cl] |
| Ff-166 | 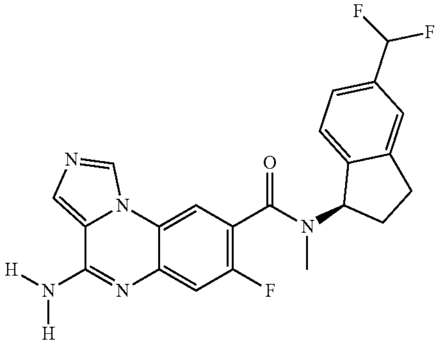 [SMILES: CN(C(=O)c1cc2c(cc1F)nc(N)c1cncn12)[C@@H]1CCc2cc(C(F)F)ccc21] |
| Ff-202 | 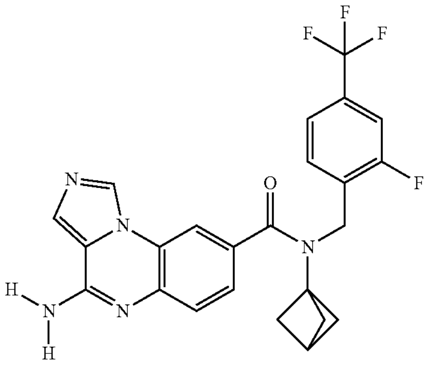 [SMILES: Nc1nc2ccc(C(=O)N(Cc3ccc(C(F)(F)F)cc3F)C34CC(C3)C4)cc2n2cncc12] |
| Ff-203 | 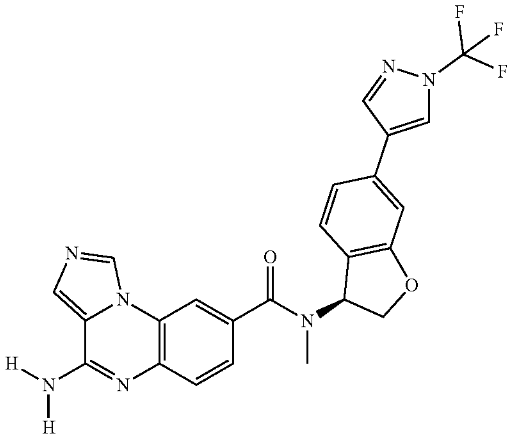 [SMILES: CN(C(=O)c1ccc2nc(N)c3cncn3c2c1)[C@@H]1COc2cc(-c3cnn(C(F)(F)F)c3)ccc21] |

TABLE 1B-continued
| Compounds | |
|---|---|
| Example | Structure |
| Ff-204 | 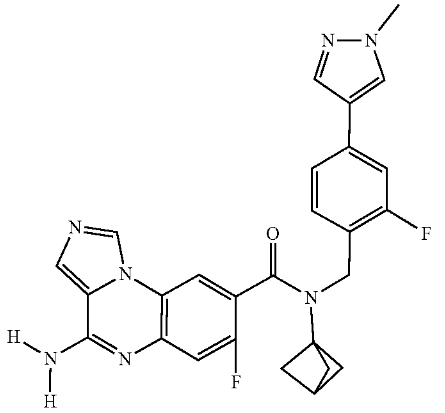 [SMILES: Cn1cc(-c2ccc(CN(C(=O)c3cc4c(cc3F)nc(N)c3cncn34)C34CC(C3)C4)c(F)c2)cn1] |
| Ff-205 | 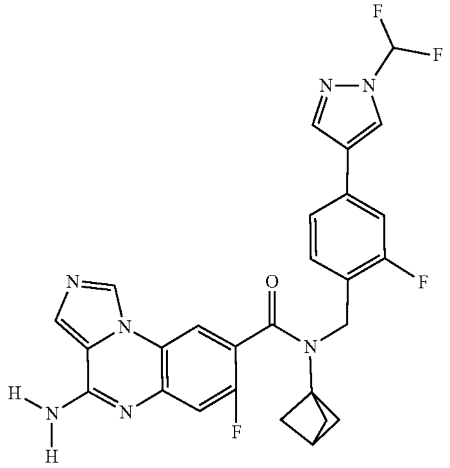 [SMILES: Nc1nc2cc(F)c(C(=O)N(Cc3ccc(-c4cnn(C(F)F)c4)cc3F)C34CC(C3)C4)cc2n2cncc12] |
| Ff-208 | 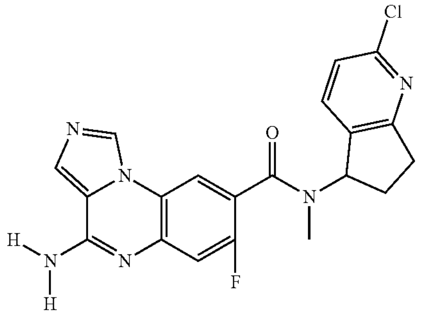 [SMILES: CN(C(=O)c1cc2c(cc1F)nc(N)c1cncn12)C1CCc2nc(Cl)ccc21] |
| Ff-209 | 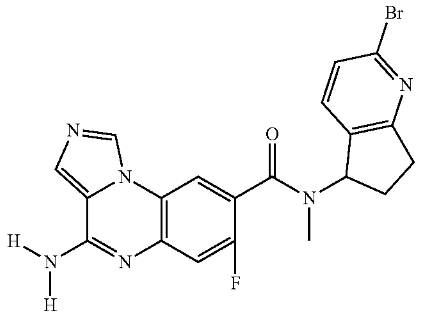 [SMILES: CN(C(=O)c1cc2c(cc1F)nc(N)c1cncn12)C1CCc2nc(Br)ccc21] |

TABLE 1B-continued
| Compounds | |
|---|---|
| Example | Structure |
| Ff-210 | 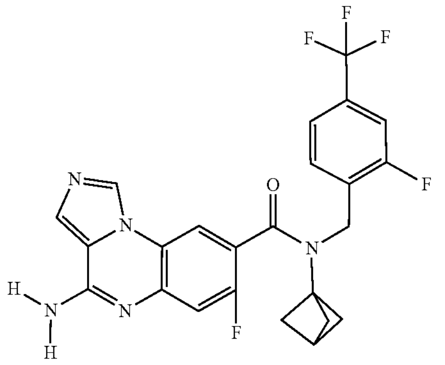 [SMILES: Nc1nc2cc(F)c(C(=O)N(Cc3ccc(C(F)(F)F)cc3F)C34CC(C3)C4)cc2n2cncc12] |
| Ff-211 | 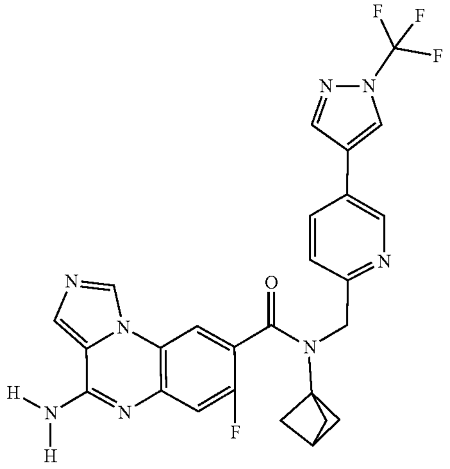 [SMILES: Nc1nc2cc(F)c(C(=O)N(Cc3ccc(-c4cnn(C(F)(F)F)c4)cn3)C34CC(C3)C4)cc2n2cncc12] |
| Ff-212 | 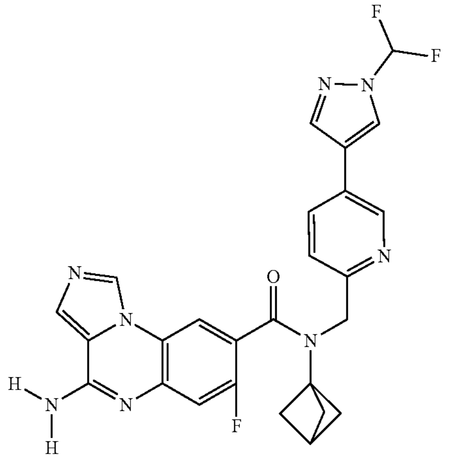 [SMILES: Nc1nc2cc(F)c(C(=O)N(Cc3ccc(-c4cnn(C(F)F)c4)cn3)C34CC(C3)C4)cc2n2cncc12] |

TABLE 1B-continued
| Compounds | |
|---|---|
| Example | Structure |
| Ff-213 | 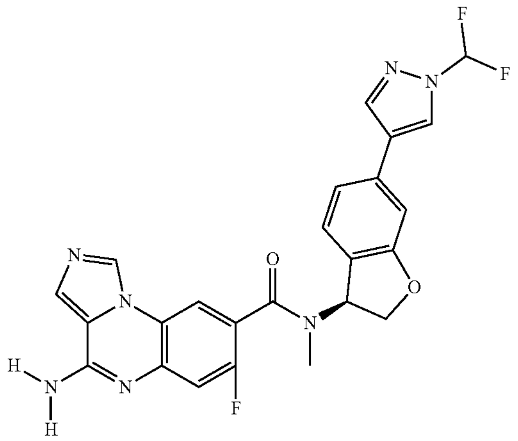 [SMILES: CN(C(=O)c1cc2c(cc1F)nc(N)c1cncn12)[C@@H]1COc2cc(-c3cnn(C(F)F)c3)ccc21] |
| Ff-214 | 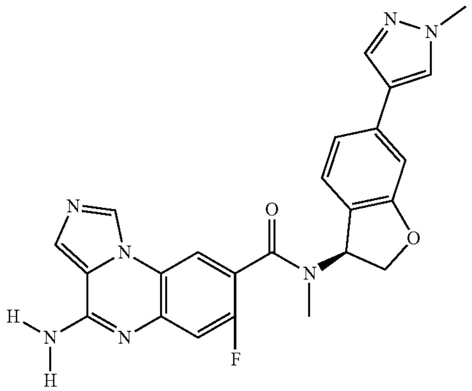 [SMILES: CN(C(=O)c1cc2c(cc1F)nc(N)c1cncn12)[C@@H]1COc2cc(-c3cnn(C)c3)ccc21] |
| Ff-215 | 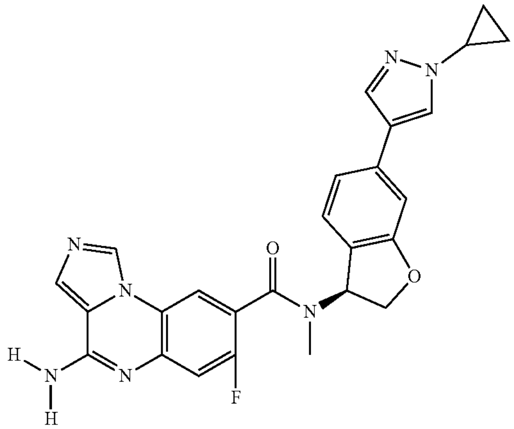 [SMILES: CN(C(=O)c1cc2c(cc1F)nc(N)c1cncn12)[C@@H]1COc2cc(-c3cnn(C4CC4)c3)ccc21] |

TABLE 1B-continued
| Compounds | |
|---|---|
| Example | Structure |
| Ff-216 | 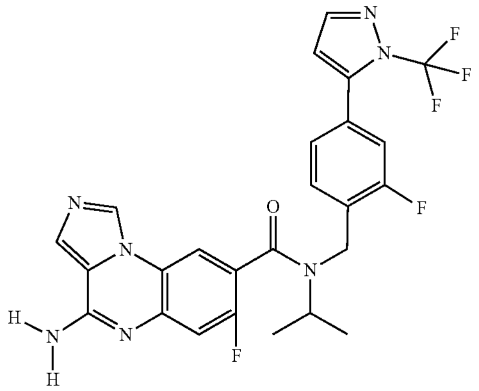 [SMILES: CC(C)N(Cc1ccc(-c2ccnn2C(F)(F)F)cc1F)C(=O)c1cc2c(cc1F)nc(N)c1cncn12] |
| Ff-217 | 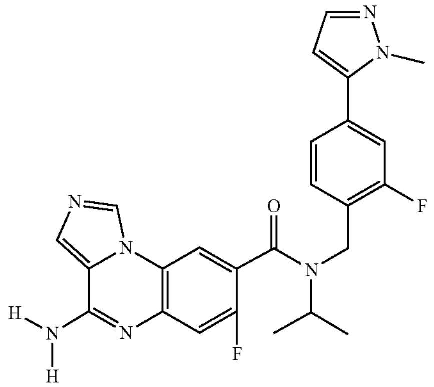 [SMILES: CC(C)N(Cc1ccc(-c2ccnn2C)cc1F)C(=O)c1cc2c(cc1F)nc(N)c1cncn12] |
| Ff-218 | 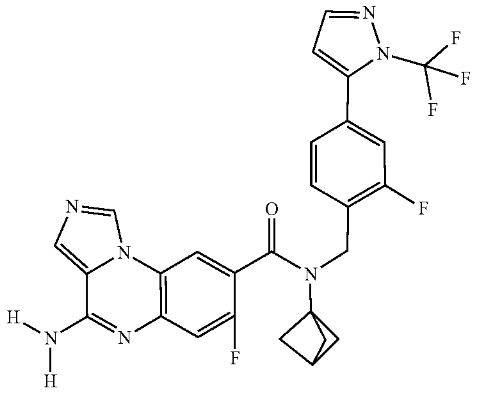 [SMILES: Nc1nc2cc(F)c(C(=O)N(Cc3ccc(-c4ccnn4C(F)(F)F)cc3F)C34CC(C3)C4)cc2n2cncc12] |
| Ff-219 | 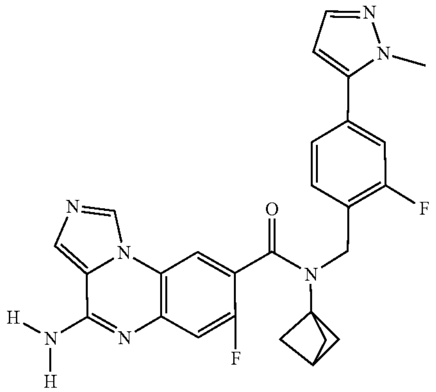 [SMILES: Cn1nccc1-c1ccc(CN(C(=O)c2cc3c(cc2F)nc(N)c2cncn23)C23CC(C2)C3)c(F)c1] |

TABLE 1B-continued
| Compounds | |
|---|---|
| Example | Structure |
| Ff-220 | 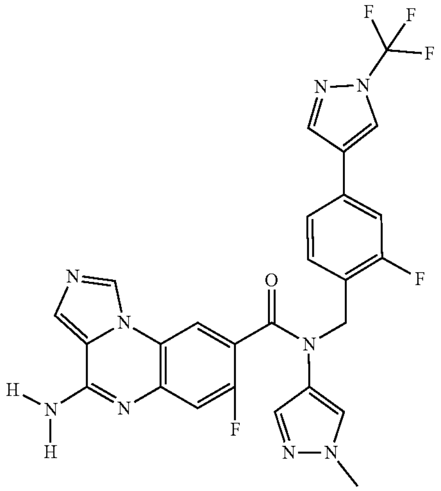 [SMILES: Cn1cc(N(Cc2ccc(-c3cnn(C(F)(F)F)c3)cc2F)C(=O)c2cc3c(cc2F)nc(N)c2cncn23)cn1] |
| Ff-221 | 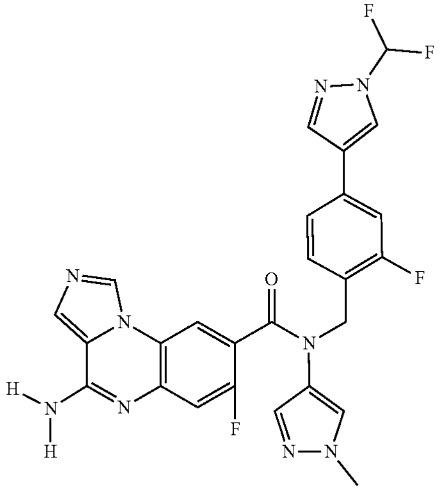 [SMILES: Cn1cc(N(Cc2ccc(-c3cnn(C(F)F)c3)cc2F)C(=O)c2cc3c(cc2F)nc(N)c2cncn23)cn1] |
| Ff-222 | 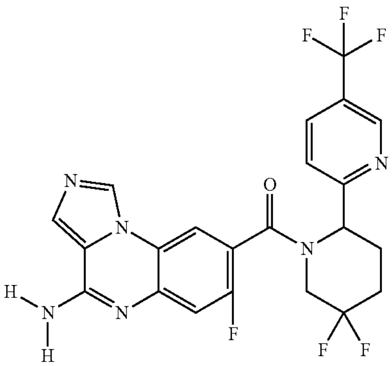 [SMILES: Nc1nc2cc(F)c(C(=O)N3CC(F)(F)CCC3c3ccc(C(F)(F)F)cn3)cc2n2cncc12] |

TABLE 1B-continued
| Compounds | |
|---|---|
| Example | Structure |
| Ff-223 | 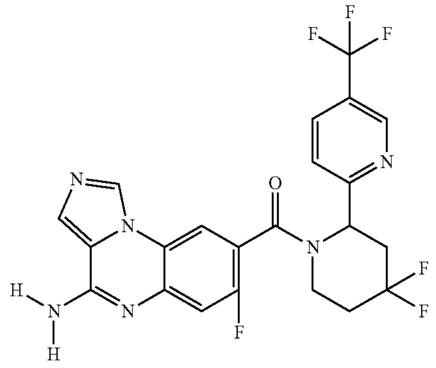 [SMILES: Nc1nc2cc(F)c(C(=O)N3CCC(F)(F)CC3c3ccc(C(F)(F)F)cn3)cc2n2cncc12] |
| Ff-224 | 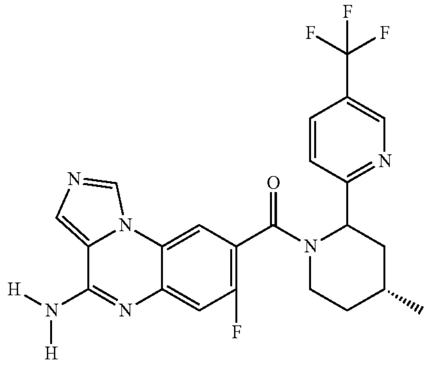 [SMILES: C[C@@H]1CCN(C(=O)c2cc3c(cc2F)nc(N)c2cncn23)C(c2ccc(C(F)(F)F)cn2)C1] |
| Ff-225 | 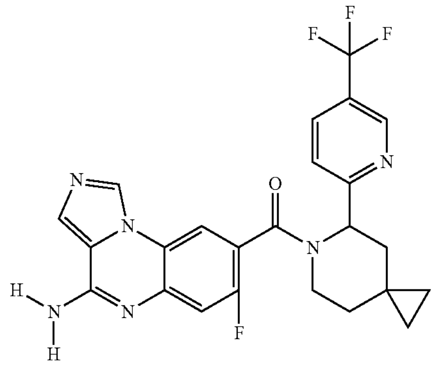 [SMILES: Nc1nc2cc(F)c(C(=O)N3CCC4(CC4)CC3c3ccc(C(F)(F)F)cn3)cc2n2cncc12] |
| Ff-226 | 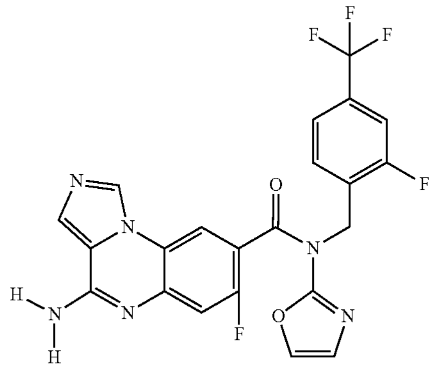 [SMILES: Nc1nc2cc(F)c(C(=O)N(Cc3ccc(C(F)(F)F)cc3F)c3ncco3)cc2n2cncc12] |

TABLE 1B-continued
| Compounds | |
|---|---|
| Example | Structure |
| Ff-227 | 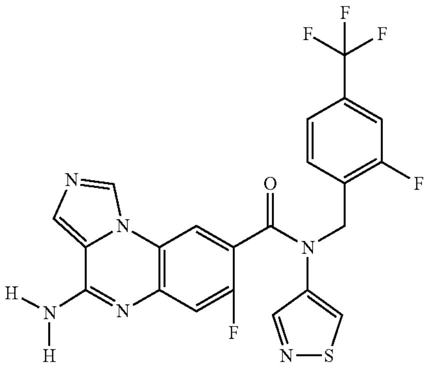 [SMILES: Nc1nc2cc(F)c(C(=O)N(Cc3ccc(C(F)(F)F)cc3F)c3cnsc3)cc2n2cncc12] |
| Ff-228 | 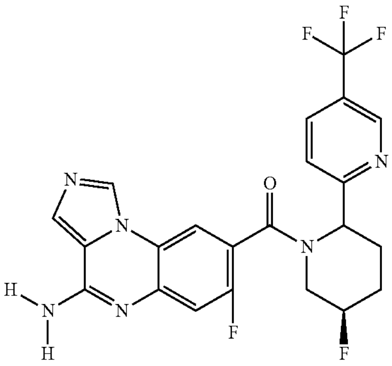 |
| Ff-229 | 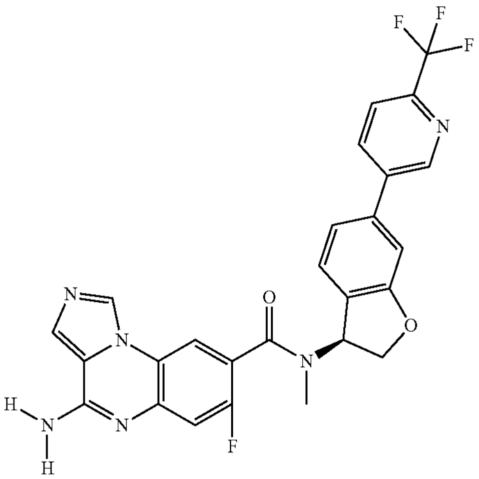 [SMILES: CN(C(=O)c1cc2c(cc1F)nc(N)c1cncn12)[C@@H]1COc2cc(-c3ccc(C(F)(F)F)nc3)ccc21] |

TABLE 1B-continued
| Compounds | |
|---|---|
| Example | Structure |
| Ff-230 | 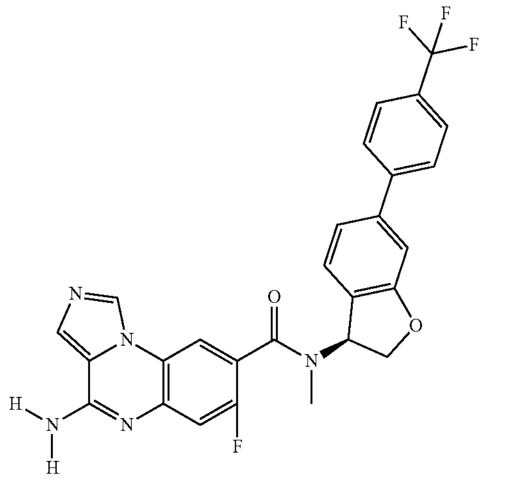 [SMILES: CN(C(=O)c1cc2c(cc1F)nc(N)c1cncn12)[C@@H]1COc2cc(-c3ccc(C(F)(F)F)cc3)ccc21] |
| Ff-231 | 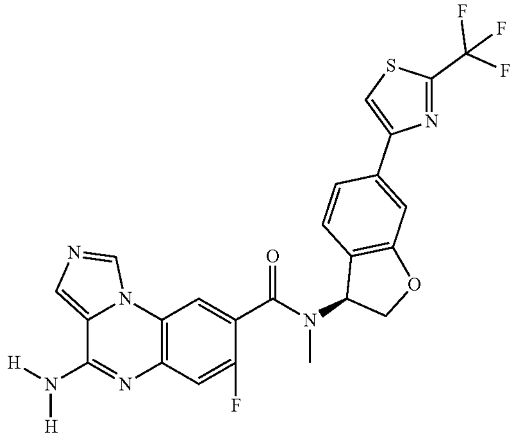 [SMILES: CN(C(=O)c1cc2c(cc1F)nc(N)c1cncn12)[C@@H]1COc2cc(-c3csc(C(F)(F)F)n3)ccc21] |
| Ff-232 | 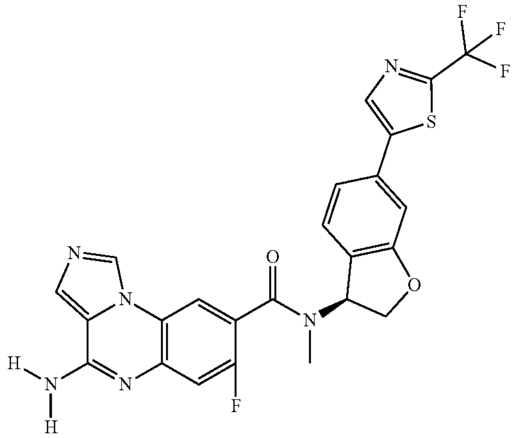 [SMILES: CN(C(=O)c1cc2c(cc1F)nc(N)c1cncn12)[C@@H]1COc2cc(-c3cnc(C(F)(F)F)s3)ccc21] |

TABLE 1B-continued
| Compounds | |
|---|---|
| Example | Structure |
| Ff-233 | 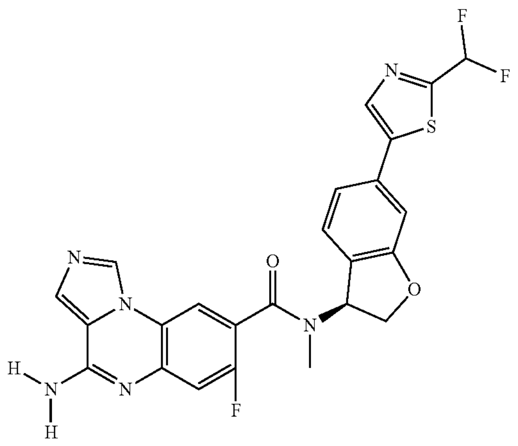 [SMILES: CN(C(=O)c1cc2c(cc1F)nc(N)c1cncn12)[C@@H]1COc2cc(-c3cnc(C(F)F)s3)ccc21] |
| Ff-237 | 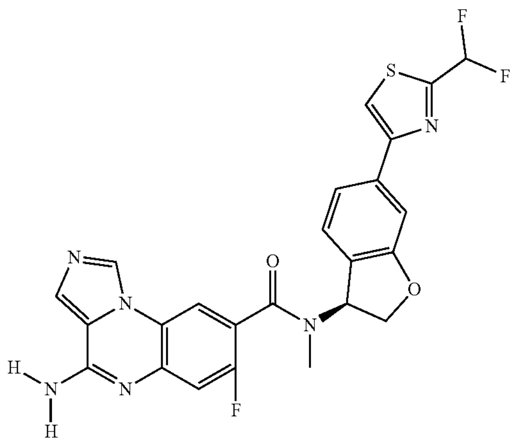 [SMILES: CN(C(=O)c1cc2c(cc1F)nc(N)c1cncn12)[C@@H]1COc2cc(-c3csc(C(F)F)n3)ccc21] |
| Ff-238 | 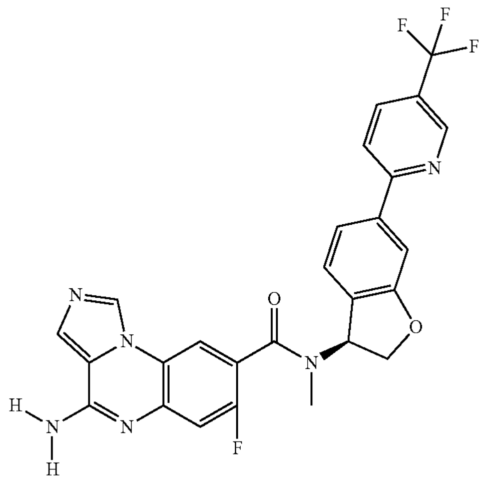 [SMILES: CN(C(=O)c1cc2c(cc1F)nc(N)c1cncn12)[C@@H]1COc2cc(-c3ccc(C(F)(F)F)cn3)ccc21] |

TABLE 1B-continued
| Compounds | |
|---|---|
| Example | Structure |
| Ff-241 | 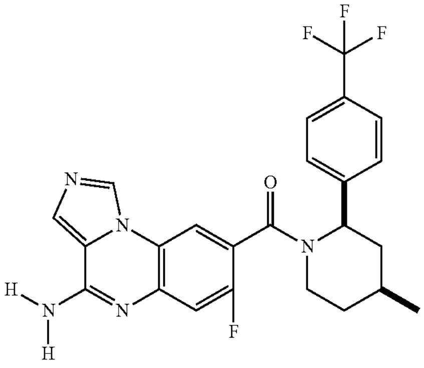 (±) |
| Ff-242 | 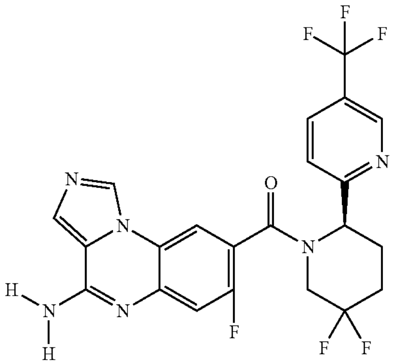 [SMILES: Nc1nc2cc(F)c(C(=O)N3CC(F)(F)CC[C@@H]3c3ccc(C(F)(F)F)cn3)cc2n2cncc12] |
| Ff-243 | 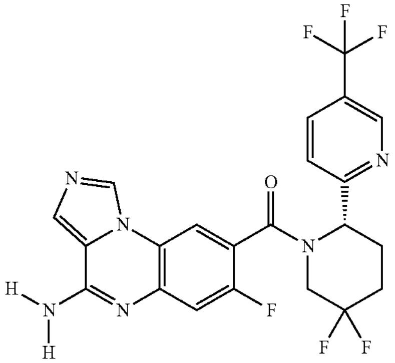 [SMILES: Nc1nc2cc(F)c(C(=O)N3CC(F)(F)CC[C@H]3c3ccc(C(F)(F)F)cn3)cc2n2cncc12] |
| Ff-244 | 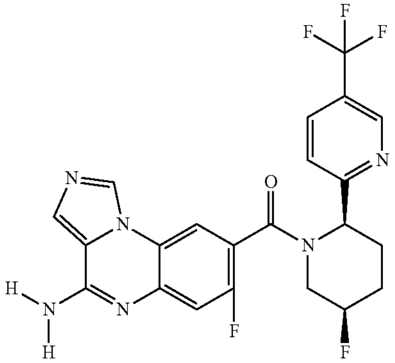 [SMILES: Nc1nc2cc(F)c(C(=O)N3C[C@H](F)CC[C@@H]3c3ccc(C(F)(F)F)cn3)cc2n2cncc12] |

TABLE 1B-continued
| Compounds | |
|---|---|
| Example | Structure |
| Ff-245 | 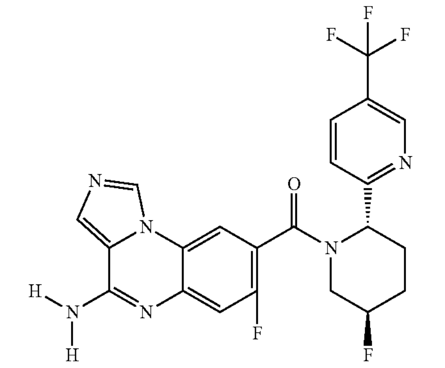 [SMILES: Nc1nc2cc(F)c(C(=O)N3C[C@H](F)CC[C@H]3c3ccc(C(F)(F)F)cn3)cc2n2cncc12] |
| Ff-253 | 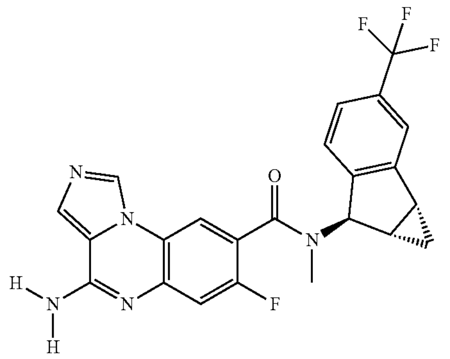 [SMILES: CN(C(=O)c1cc2c(cc1F)nc(N)c1cncn12)[C@H]1c2ccc(C(F)(F)F)cc2[C@@H]2C[C@@H]21] |
| Ff-254 | 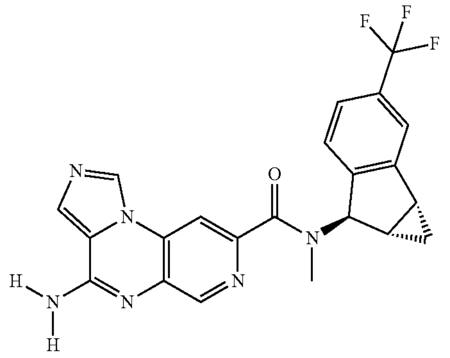 [SMILES: CN(C(=O)c1cc2c(cn1)nc(N)c1cncn12)[C@H]1c2ccc(C(F)(F)F)cc2[C@@H]2C[C@@H]21] |
| Ff-255 | 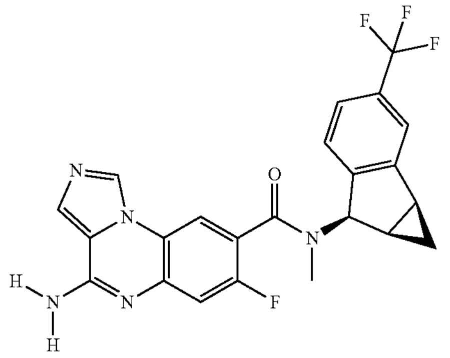 [SMILES: CN(C(=O)c1cc2c(cc1F)nc(N)c1cncn12)[C@H]1c2ccc(C(F)(F)F)cc2[C@H]2C[C@H]21] |

TABLE 1B-continued
| Compounds | |
|---|---|
| Example | Structure |
| Ff-256 | 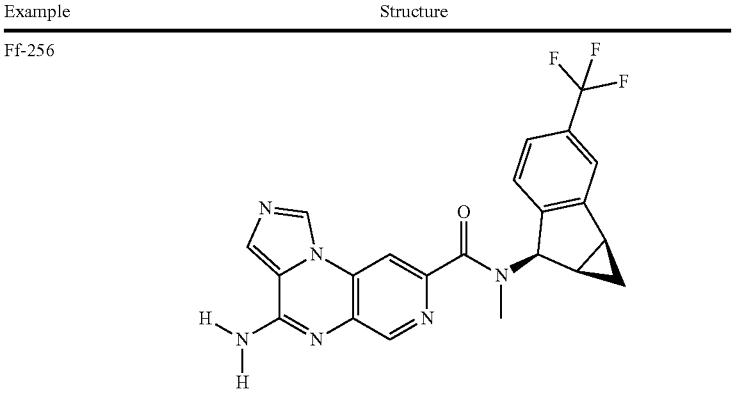 |
| Ff-263 | 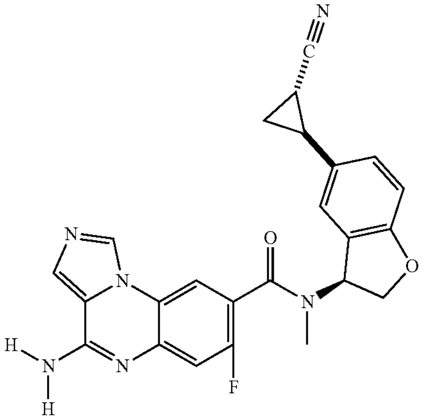 [SMILES: CN(C(=O)c1cc2c(cc1F)nc(N)c1cncn12)[C@@H]1COc2ccc([C@H]3C[C@@H]3C#N)cc21] |
| Ff-264 | 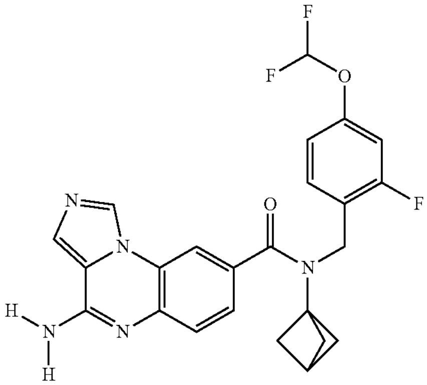 [SMILES: Nc1nc2ccc(C(=O)N(Cc3ccc(OC(F)F)cc3F)C34CC(C3)C4)cc2n2cncc12] |
| Ff-265 | 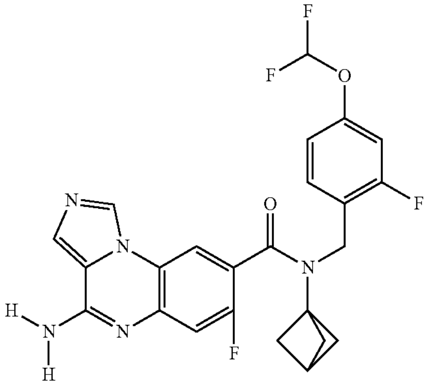 [SMILES: Nc1nc2cc(F)c(C(=O)N(Cc3ccc(OC(F)F)cc3F)C34CC(C3)C4)cc2n2cncc12] |

TABLE 1B-continued
| Compounds | |
|---|---|
| Example | Structure |
| Ff-266 | 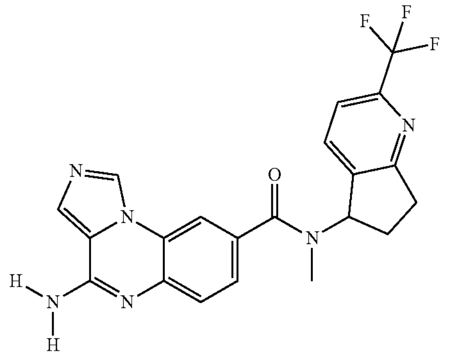 [SMILES: CN(C(=O)c1ccc2nc(N)c3cncn3c2c1)C1CCc2nc(C(F)(F)F)ccc21] |
| Ff-267 | 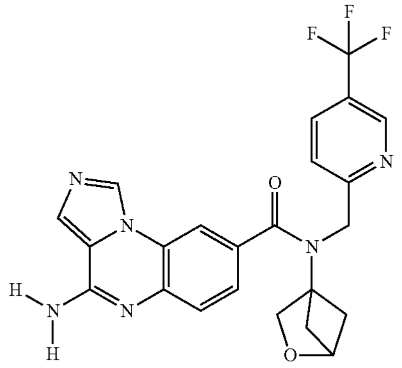 [SMILES: Nc1nc2ccc(C(=O)N(Cc3ccc(C(F)(F)F)cn3)C34COC(C3)C4)cc2n2cncc12] |
| Ff-268 | 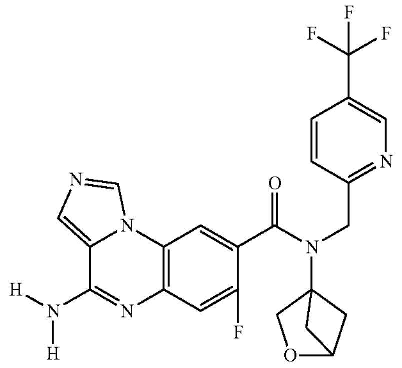 [SMILES: Nc1nc2cc(F)c(C(=O)N(Cc3ccc(C(F)(F)F)cn3)C34COC(C3)C4)cc2n2cncc12] |
| Ff-269 | 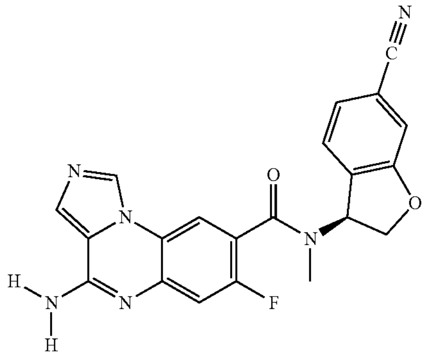 [SMILES: CN(C(=O)c1cc2c(cc1F)nc(N)c1cncn12)[C@@H]1COc2cc(C#N)ccc21] |

TABLE 1B-continued
| Compounds | |
|---|---|
| Example | Structure |
| Ff-270 | 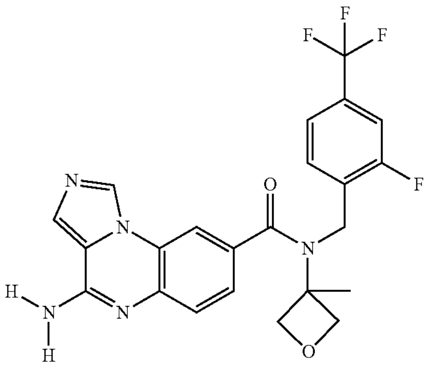 [SMILES: CC1(N(Cc2ccc(C(F)(F)F)cc2F)C(=O)c2ccc3nc(N)c4cncn4c3c2)COC1] |
| Ff-271 | 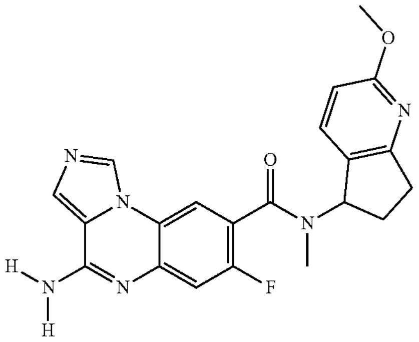 [SMILES: COc1ccc2c(n1)CCC2N(C)C(=O)c1cc2c(cc1F)nc(N)c1cncn12] |
| Ff-272 | 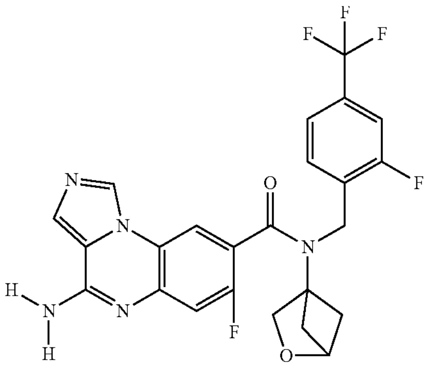 [SMILES: Nc1nc2cc(F)c(C(=O)N(Cc3ccc(C(F)(F)F)cc3F)C34COC(C3)C4)cc2n2cncc12] |
| Ff-273 | 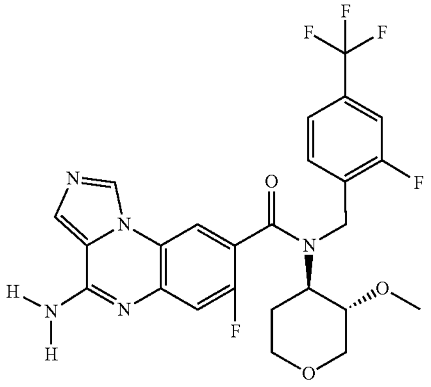 [SMILES: CO[C@@H]1COCC[C@H]1N(Cc1ccc(C(F)(F)F)cc1F)C(=O)c1cc2c(cc1F)nc(N)c1cncn12] |

TABLE 1B-continued
| Compounds | |
| --- | --- |
| Example | Structure |
| Ff-274 | 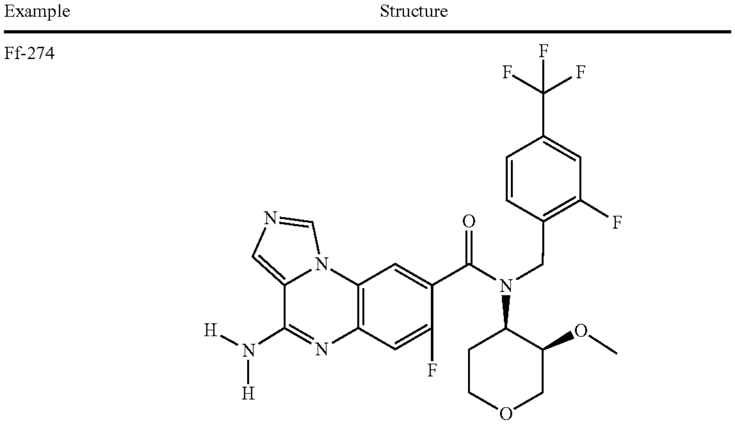 |
| Ff-275 | 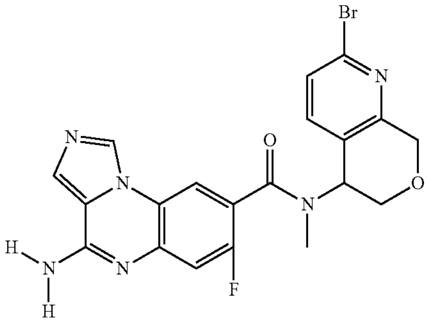 [SMILES: CN(C(=O)c1cc2c(cc1F)nc(N)c1cncn12)C1COCc2nc(Br)ccc21] |
| Ff-276 | 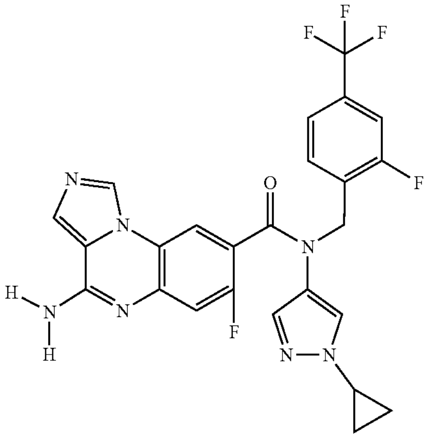 [SMILES: Nc1nc2cc(F)c(C(=O)N(Cc3ccc(C(F)(F)F)cc3F)c3cnn(C4CC4)c3)cc2n2cncc12] |
| Ff-277 | 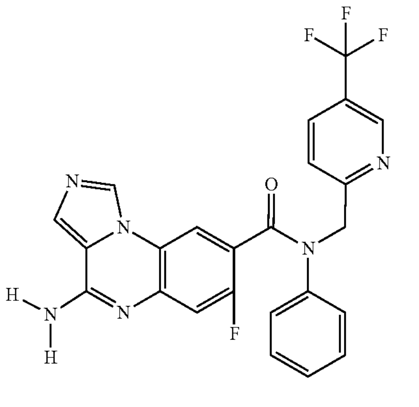 [SMILES: Nc1nc2cc(F)c(C(=O)N(Cc3ccc(C(F)(F)F)cn3)c3ccccc3)cc2n2cncc12] |

TABLE 1B-continued
| Compounds | |
|---|---|
| Example | Structure |
| Ff-278 | 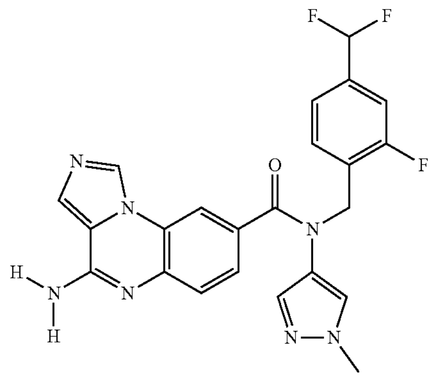 [SMILES: Cn1cc(N(Cc2ccc(C(F)F)cc2F)C(=O)c2ccc3nc(N)c4cncn4c3c2)cn1] |
| Ff-279 | 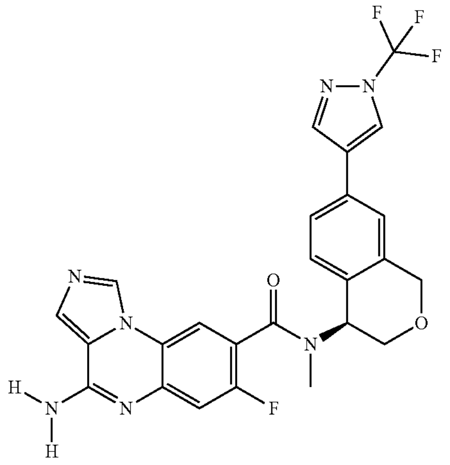 [SMILES: CN(C(=O)c1cc2c(cc1F)nc(N)c1cncn12)[C@@H]1COCc2cc(-c3cnn(C(F)(F)F)c3)ccc21] |
| Ff-280 | 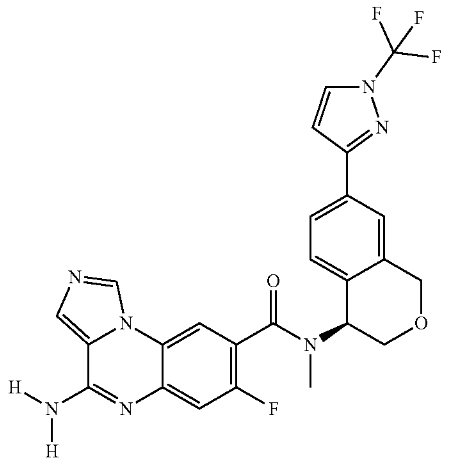 [SMILES: CN(C(=O)c1cc2c(cc1F)nc(N)c1cncn12)[C@@H]1COCc2cc(-c3ccn(C(F)(F)F)n3)ccc21] |

TABLE 1B-continued
| Compounds | |
|---|---|
| Example | Structure |
| Ff-281 | 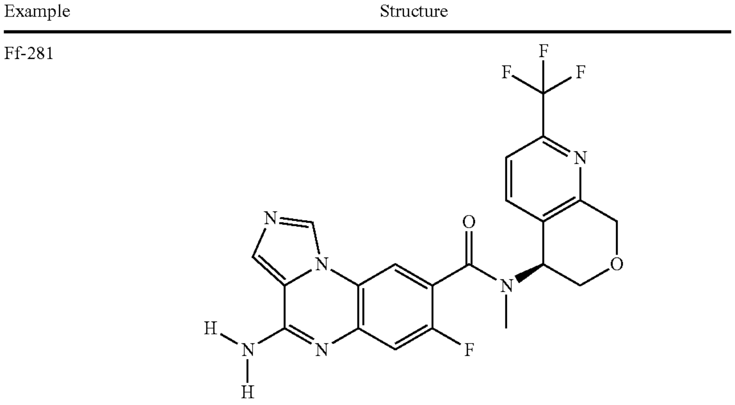 |
| Ff-282 | 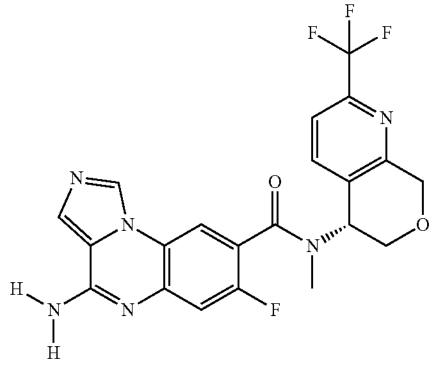 |
| Ff-283 | 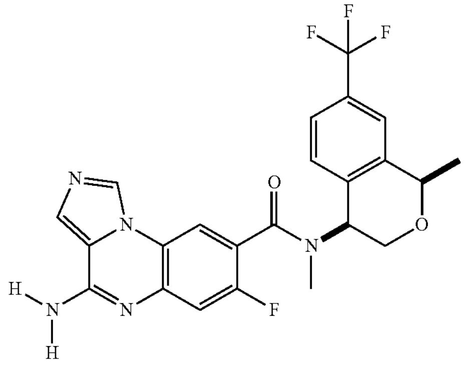 (±) |
| Ff-284 | 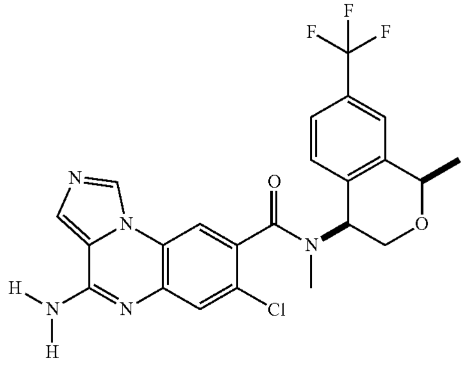 (±) |

TABLE 1B-continued
| Compounds | |
|---|---|
| Example | Structure |
| Ff-285 | 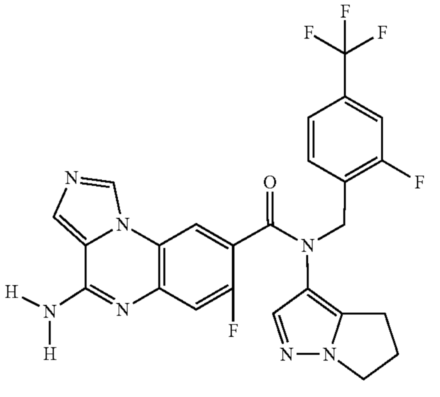 [SMILES: Nc1nc2cc(F)c(C(=O)N(Cc3ccc(C(F)(F)F)cc3F)c3cnn4c3CCC4)cc2n2cncc12] |
| Ff-286 | 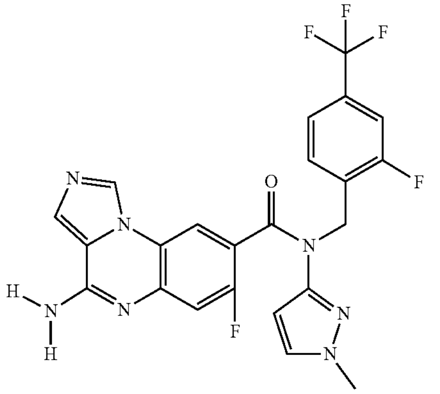 [SMILES: Cn1ccc(N(Cc2ccc(C(F)(F)F)cc2F)C(=O)c2cc3c(cc2F)nc(N)c2cncn23)n1] |
| Ff-287 | 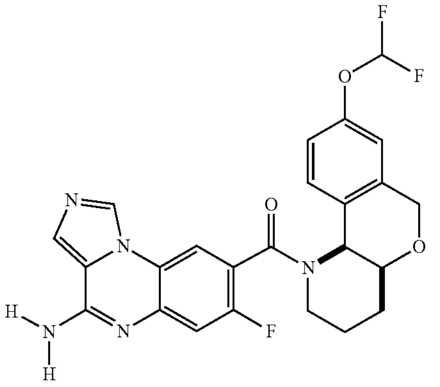 (±) |

TABLE 1B-continued
| Compounds | |
|---|---|
| Example | Structure |
| Ff-288 | 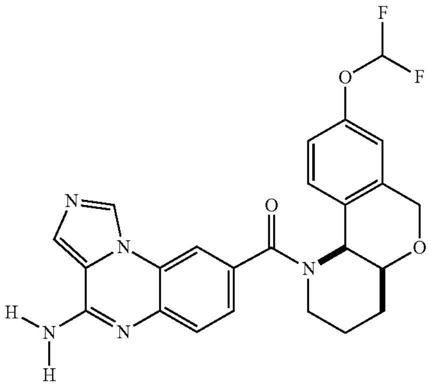 (±) |
| Ff-289 | 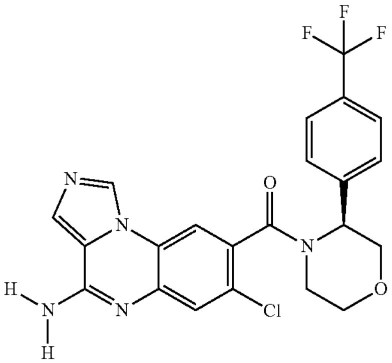 |
| Ff-290 | 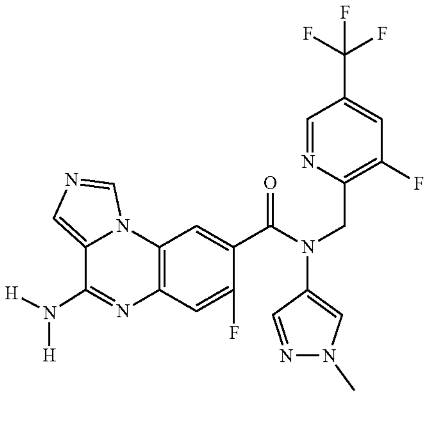 [SMILES: Cn1cc(N(Cc2ncc(C(F)(F)F)cc2F)C(=O)c2cc3c(cc2F)nc(N)c2cncn23)cn1] |

TABLE 1B-continued
| Compounds | |
|---|---|
| Example | Structure |
| Ff-291 | 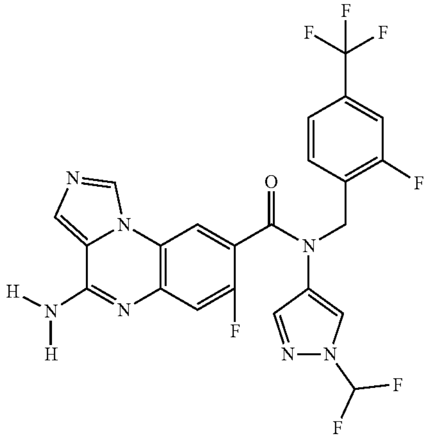 [SMILES: Nc1nc2cc(F)c(C(=O)N(Cc3ccc(C(F)(F)F)cc3F)c3cnn(C(F)F)c3)cc2n2cncc12] |
| Ff-292 | 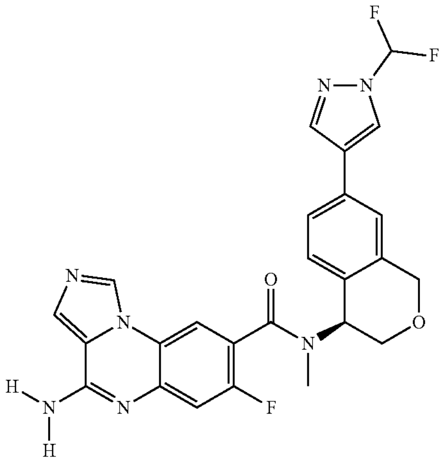 [SMILES: CN(C(=O)c1cc2c(cc1F)nc(N)c1cncn12)[C@@H]1COCc2cc(-c3cnn(C(F)F)c3)ccc21] |
| Ff-302 | 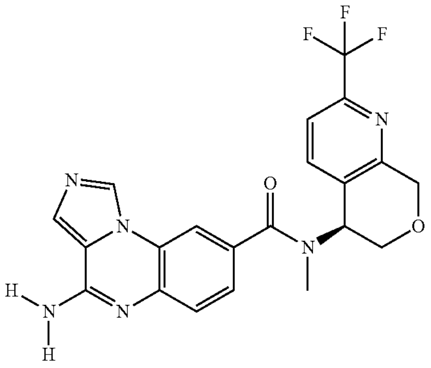 [SMILES: CN(C(=O)c1ccc2nc(N)c3cncn3c2c1)[C@@H]1COCc2nc(C(F)(F)F)ccc21] |

TABLE 1B-continued
| Compounds | |
|---|---|
| Example | Structure |
| Ff-303 | 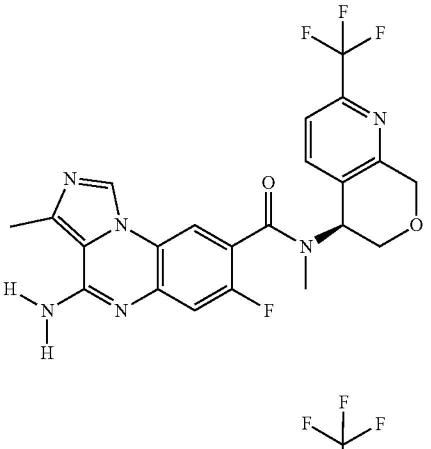 |
| Ff-304 | 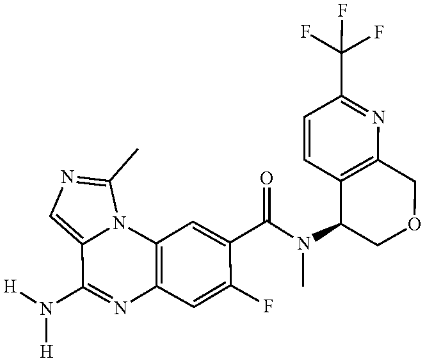 [SMILES: Cc1ncc2c(N)nc3cc(F)c(C(=O)N(C)[C@@H]4COCc5nc(C(F)(F)F)ccc54)cc3n12] |
| Ff-305 | 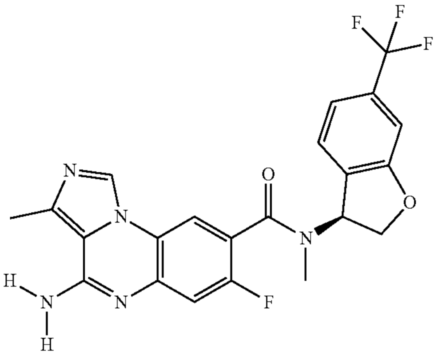 [SMILES: Cc1ncn2c1c(N)nc1cc(F)c(C(=O)N(C)[C@@H]3COc4cc(C(F)(F)F)ccc43)cc12] |
| Ff-306 | 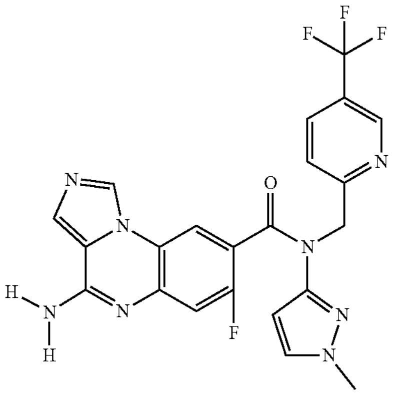 [SMILES: Cn1ccc(N(Cc2ccc(C(F)(F)F)cn2)C(=O)c2cc3c(cc2F)nc(N)c2cncn23)n1] |

TABLE 1B-continued
| Compounds | |
|---|---|
| Example | Structure |
| Ff-307 | 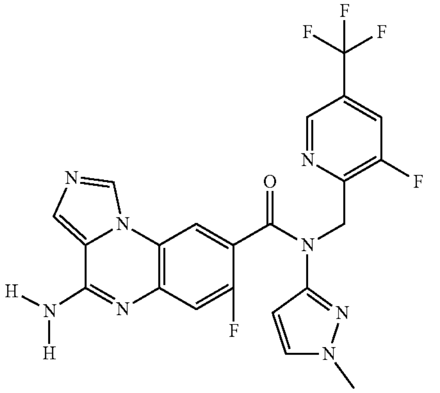 [SMILES: Cn1ccc(N(Cc2ncc(C(F)(F)F)cc2F)C(=O)c2cc3c(cc2F)nc(N)c2cncn23)n1] |
| Ff-308 | 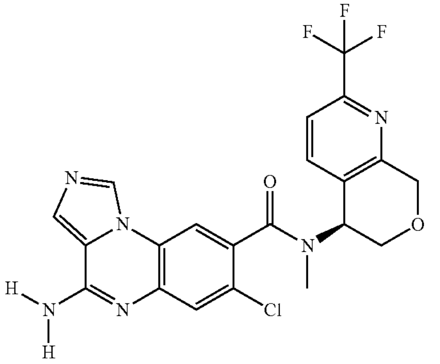 [SMILES: CN(C(=O)c1cc2c(cc1Cl)nc(N)c1cncn12)[C@@H]1COCc2nc(C(F)(F)F)ccc21] |
| Ff-309 | 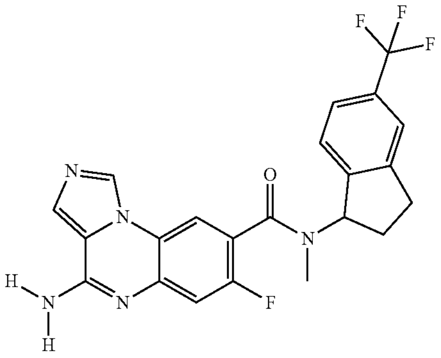 [SMILES: CN(C(=O)c1cc2c(cc1F)nc(N)c1cncn12)C1CCc2cc(C(F)(F)F)ccc21] |
| Ff-311 | 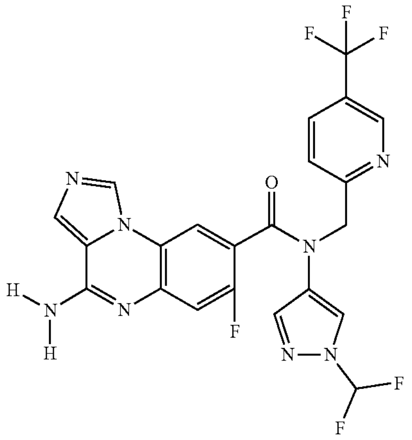 [SMILES: Nc1nc2cc(F)c(C(=O)N(Cc3ccc(C(F)(F)F)cn3)c3cnn(C(F)F)c3)cc2n2cncc12] |

TABLE 1B-continued
| Compounds | |
|---|---|
| Example | Structure |
| Ff-312 | 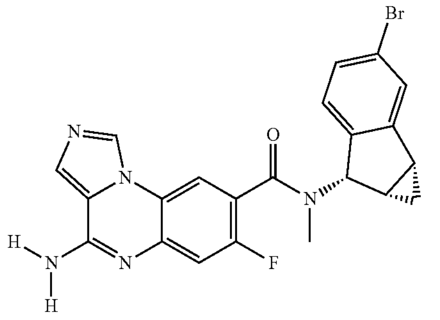 [SMILES: CN(C(=O)c1cc2c(cc1F)nc(N)c1cncn12)[C@@H]1c2ccc(Br)cc2[C@@H]2C[C@H]12] |
| Ff-313 | 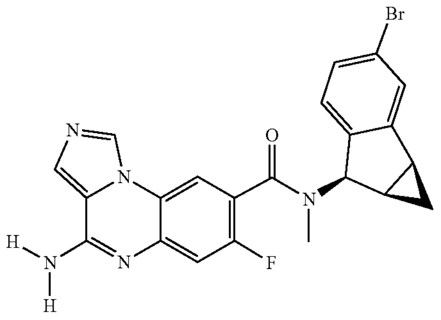 [SMILES: CN(C(=O)c1cc2c(cc1F)nc(N)c1cncn12)[C@H]1c2ccc(Br)cc2[C@H]2C[C@H]21] |
| Ff-315 | 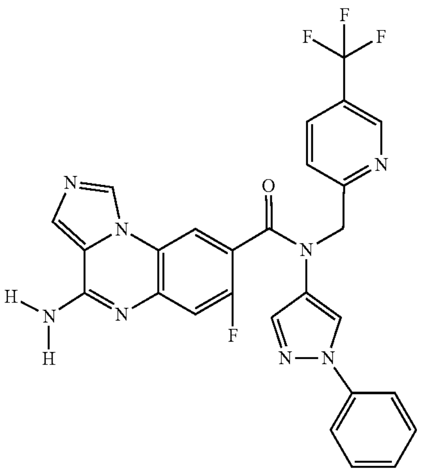 [SMILES: Nc1nc2cc(F)c(C(=O)N(Cc3ccc(C(F)(F)F)cn3)c3cnn(-c4ccccc4)c3)cc2n2cncc12] |
| Ff-316 | 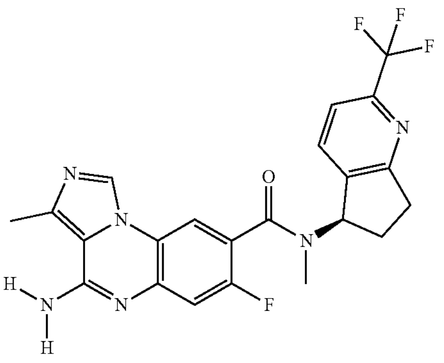 [SMILES: Cc1ncn2c1c(N)nc1cc(F)c(C(=O)N(C)[C@@H]3CCc4nc(C(F)(F)F)ccc43)cc12] |

TABLE 1B-continued
| Compounds | |
|---|---|
| Example | Structure |
| Ff-317 | 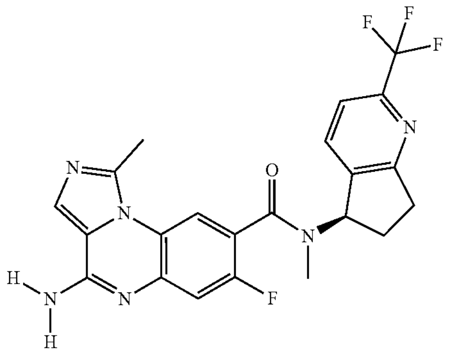 [SMILES: Cc1ncc2c(N)nc3cc(F)c(C(=O)N(C)[C@@H]4CCc5nc(C(F)(F)F)ccc54)cc3n12] |
| Ff-318 | 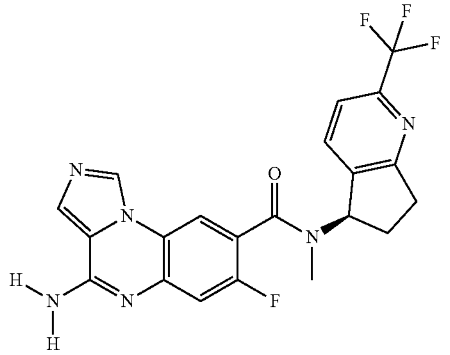 [SMILES: CN(C(=O)c1cc2c(cc1F)nc(N)c1cncn12)[C@@H]1CCc2nc(C(F)(F)F)ccc21] |
| Ff-324 | 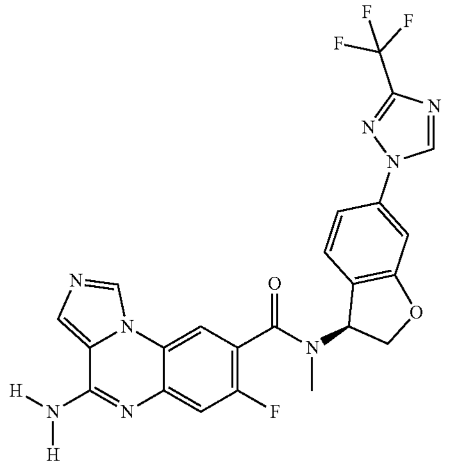 [SMILES: CN(C(=O)c1cc2c(cc1F)nc(N)c1cncn12)[C@@H]1COc2cc(-n3cnc(C(F)(F)F)n3)ccc21] |

TABLE 1B-continued
| Compounds | |
|---|---|
| Example | Structure |
| Ff-325 | 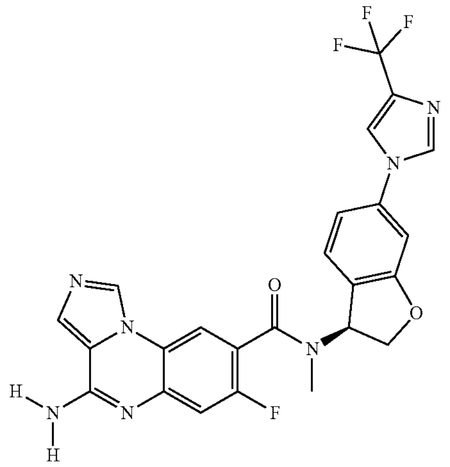 [SMILES: CN(C(=O)c1cc2c(cc1F)nc(N)c1cncn12)[C@@H]1COc2cc(-n3cnc(C(F)(F)F)c3)ccc21] |
| Ff-330 | 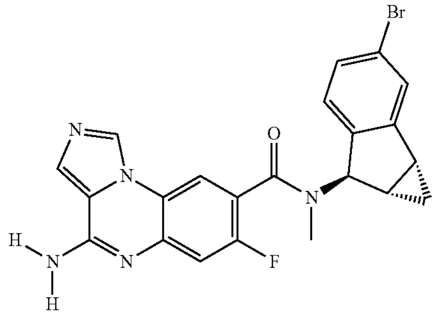 [SMILES: CN(C(=O)c1cc2c(cc1F)nc(N)c1cncn12)[C@H]1c2ccc(Br)cc2[C@@H]2C[C@@H]21] |
| Ff-337 | 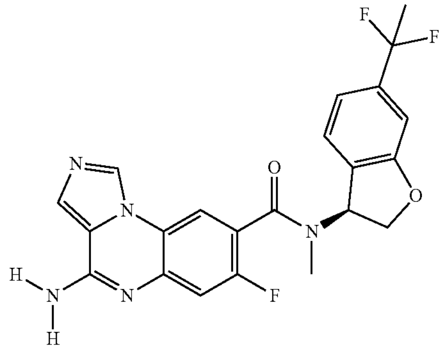 [SMILES: CN(C(=O)c1cc2c(cc1F)nc(N)c1cncn12)[C@@H]1COc2cc(C(C)(F)F)ccc21] |
| Ff-342 | 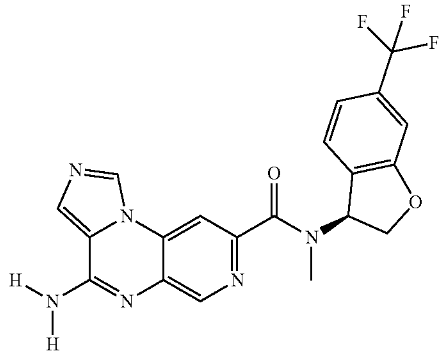 [SMILES: CN(C(=O)c1cc2c(cn1)nc(N)c1cncn12)[C@@H]1COc2cc(C(F)(F)F)ccc21] |

TABLE 1B-continued
| Compounds | |
|---|---|
| Example | Structure |
| Ff-352 | 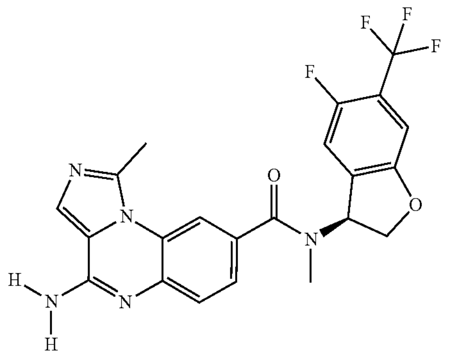 [SMILES: Cc1ncc2c(N)nc3ccc(C(=O)N(C)[C@@H]4COc5cc(C(F)(F)F)c(F)cc54)cc3n12] |
| Ff-353 | 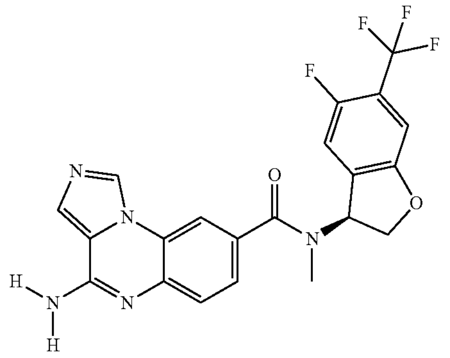 [SMILES: CN(C(=O)c1ccc2nc(N)c3cncn3c2c1)[C@@H]1COc2cc(C(F)(F)F)c(F)cc21] |
| Ff-354 | 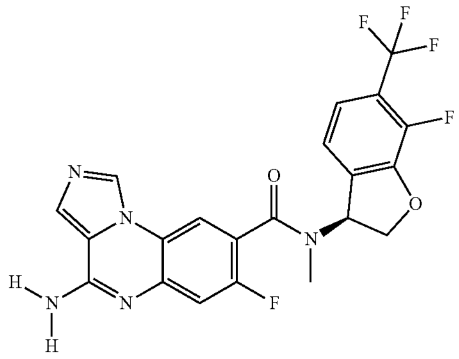 [SMILES: CN(C(=O)c1cc2c(cc1F)nc(N)c1cncn12)[C@@H]1COc2c1ccc(C(F)(F)F)c2F] |
| Ff-355 | 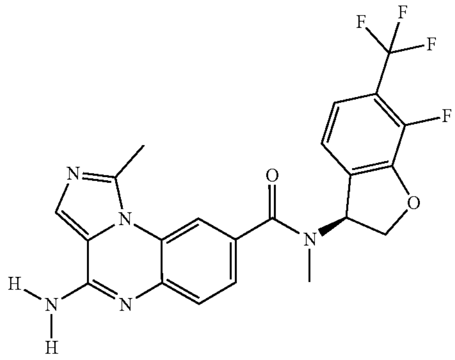 [SMILES: Cc1ncc2c(N)nc3ccc(C(=O)N(C)[C@@H]4COc5c4ccc(C(F)(F)F)c5F)cc3n12] |

TABLE 1B-continued
| Compounds | |
|---|---|
| Example | Structure |
| Ff-356 | 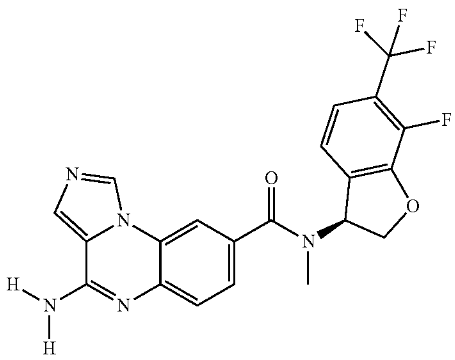 [SMILES: CN(C(=O)c1ccc2nc(N)c3cncn3c2c1)[C@@H]1COc2c1ccc(C(F)(F)F)c2F] |
| Ff-382 | 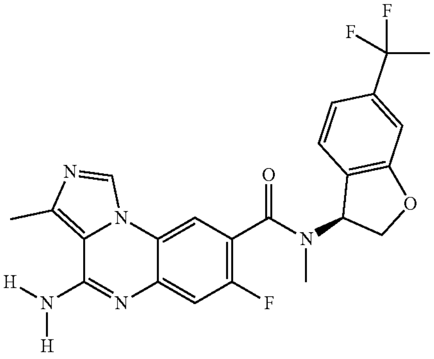 [SMILES: Cc1ncn2c1c(N)nc1cc(F)c(C(=O)N(C)[C@@H]3COc4cc(C(C)(F)F)ccc43)cc12] |
| Ff-398 | 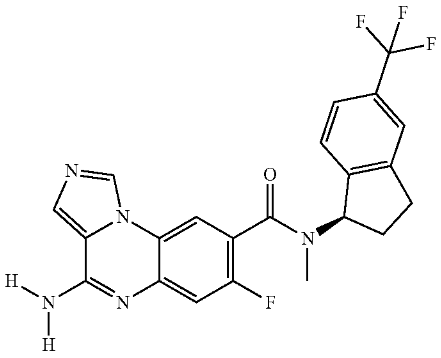 [SMILES: CN(C(=O)c1cc2c(cc1F)nc(N)c1cncn12)[C@@H]1CCc2cc(C(F)(F)F)ccc21] |
| Ff-401 | 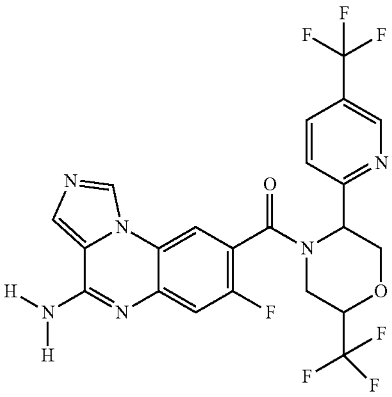 [SMILES: Nc1nc2cc(F)c(C(=O)N3CC(C(F)(F)F)OCC3c3ccc(C(F)(F)F)cn3)cc2n2cncc12] |

TABLE 1B-continued
| Compounds | |
|---|---|
| Example | Structure |
| Ff-402 | 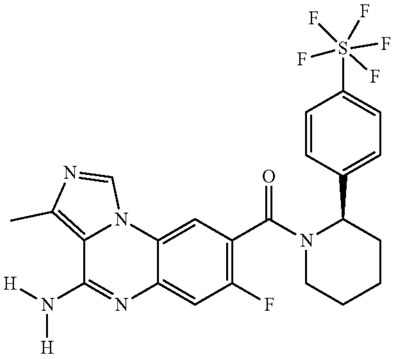 [SMILES: Cc1ncn2c1c(N)nc1cc(F)c(C(=O)N3CCCC[C@@H]3c3ccc(S(F)(F)(F)(F)F)cc3)cc12] |
| Ff-403 | 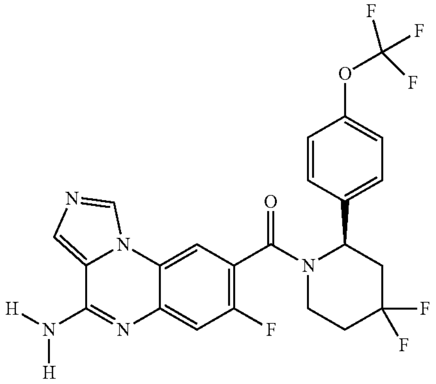 [SMILES: Nc1nc2cc(F)c(C(=O)N3CCC(F)(F)C[C@@H]3c3ccc(OC(F)(F)F)cc3)cc2n2cncc12] |
| Ff-404 | 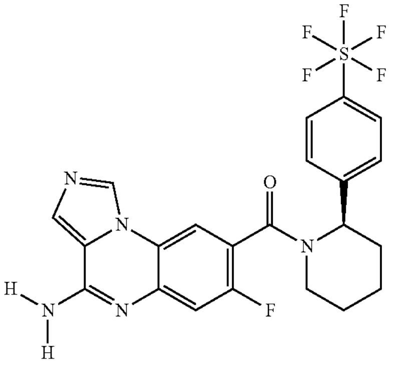 [SMILES: Nc1nc2cc(F)c(C(=O)N3CCCC[C@@H]3c3ccc(S(F)(F)(F)(F)F)cc3)cc2n2cncc12] |
| Ff-405 | 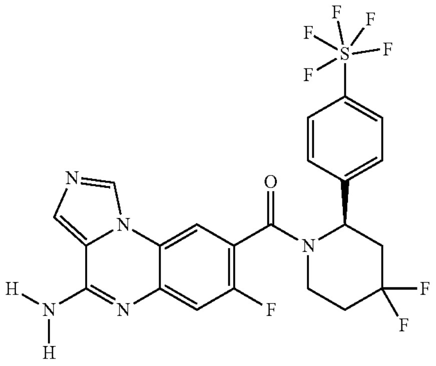 [SMILES: Nc1nc2cc(F)c(C(=O)N3CCC(F)(F)C[C@@H]3c3ccc(S(F)(F)(F)(F)F)cc3)cc2n2cncc12] |

TABLE 1B-continued
| Compounds | |
|---|---|
| Example | Structure |
| Ff-407 | 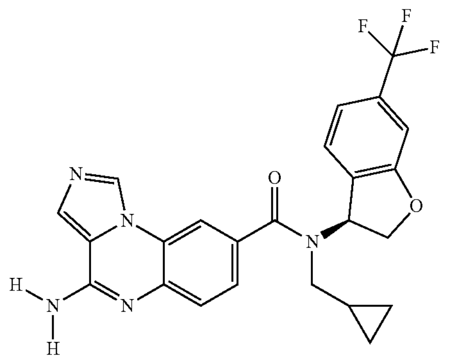 [SMILES: Nc1nc2ccc(C(=O)N(CC3CC3)[C@@H]3COc4cc(C(F)(F)F)ccc43)cc2n2cncc12] |
| Ff-408 | 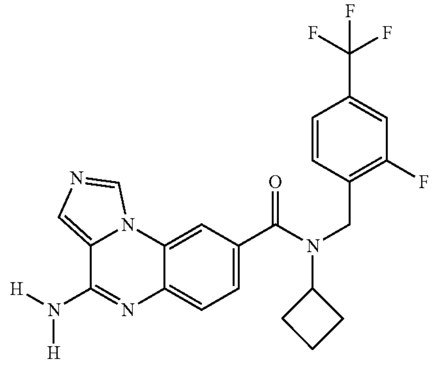 [SMILES: Nc1nc2ccc(C(=O)N(Cc3ccc(C(F)(F)F)cc3F)C3CCC3)cc2n2cncc12] |
| Ff-409 | 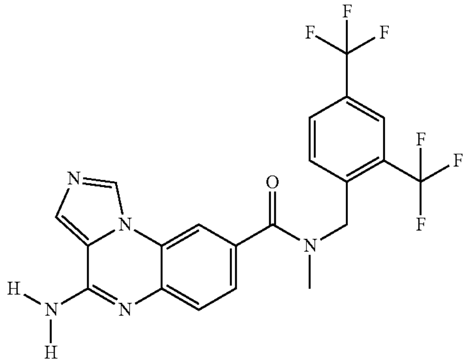 [SMILES: CN(Cc1ccc(C(F)(F)F)cc1C(F)(F)F)C(=O)c1ccc2nc(N)c3cncn3c2c1] |
| Ff-410 | 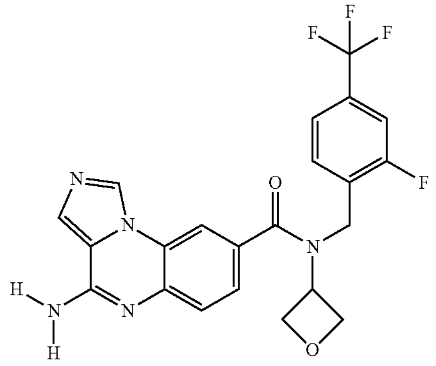 |

TABLE 1B-continued
| Compounds | |
|---|---|
| Example | Structure |
| Ff-411 | 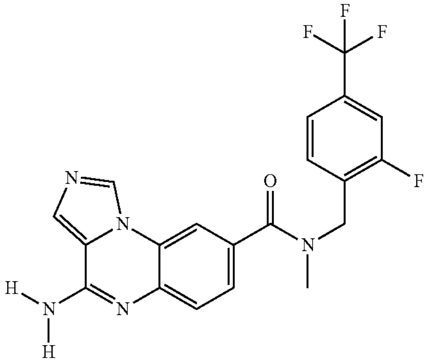 [SMILES: CN(Cc1ccc(C(F)(F)F)cc1F)C(=O)c1ccc2nc(N)c3cncn3c2c1] |
| Ff-412 | 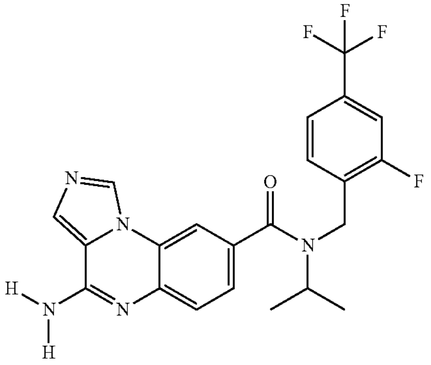 [SMILES: CC(C)N(Cc1ccc(C(F)(F)F)cc1F)C(=O)c1ccc2nc(N)c3cncn3c2c1] |
| Ff-413 | 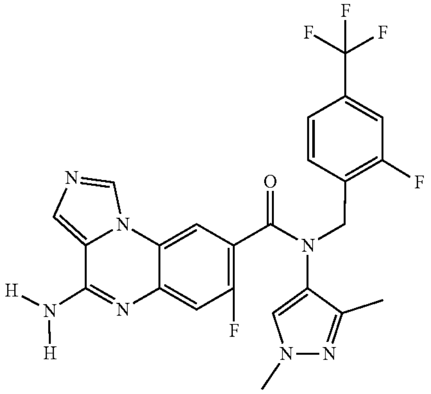 [SMILES: Cc1nn(C)cc1N(Cc1ccc(C(F)(F)F)cc1F)C(=O)c1cc2c(cc1F)nc(N)c1cncn12] |
| Ff-414 | 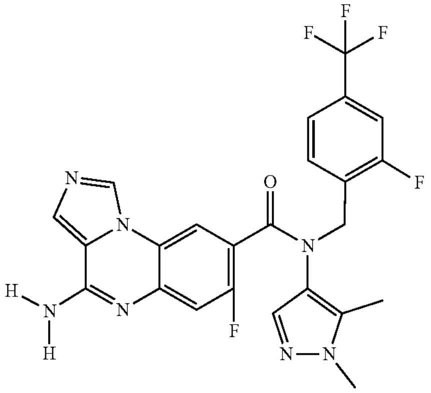 [SMILES: Cc1c(N(Cc2ccc(C(F)(F)F)cc2F)C(=O)c2cc3c(cc2F)nc(N)c2cncn23)cnn1C] |

TABLE 1B-continued
| Compounds | |
|---|---|
| Example | Structure |
| Ff-415 | 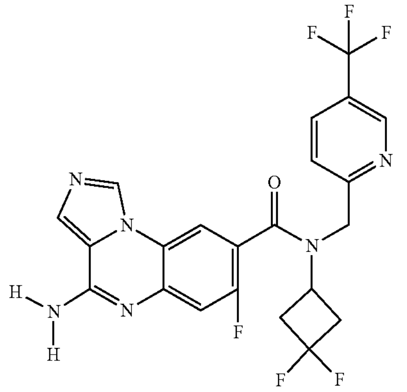 [SMILES: Nc1nc2cc(F)c(C(=O)N(Cc3ccc(C(F)(F)F)cn3)C3CC(F)(F)C3)cc2n2cncc12] |
| Ff-416 | 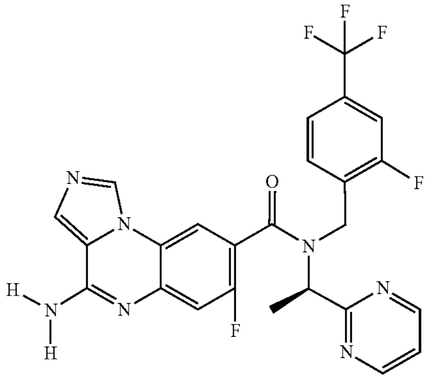 [SMILES: C[C@H](c1ncccn1)N(Cc1ccc(C(F)(F)F)cc1F)C(=O)c1cc2c(cc1F)nc(N)c1cncn12] |
| Ff-417 | 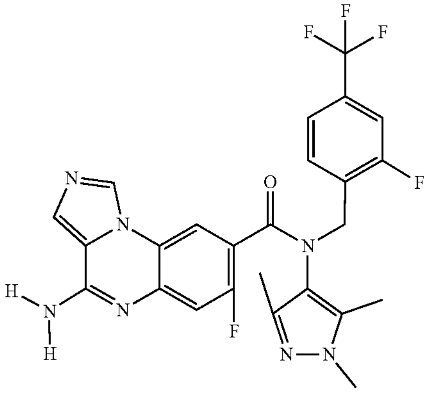 [SMILES: Cc1nn(C)c(C)c1N(Cc1ccc(C(F)(F)F)cc1F)C(=O)c1cc2c(cc1F)nc(N)c1cncn12] |
| Ff-418 | 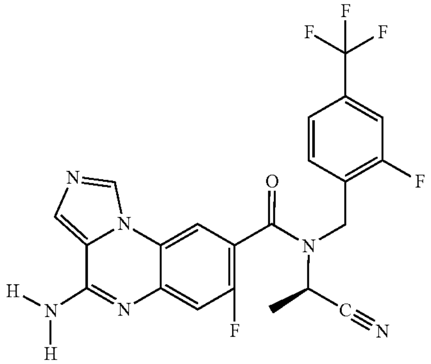 [SMILES: C[C@H](C#N)N(Cc1ccc(C(F)(F)F)cc1F)C(=O)c1cc2c(cc1F)nc(N)c1cncn12] |

TABLE 1B-continued
| Compounds | |
|---|---|
| Example | Structure |
| Ff-419 | 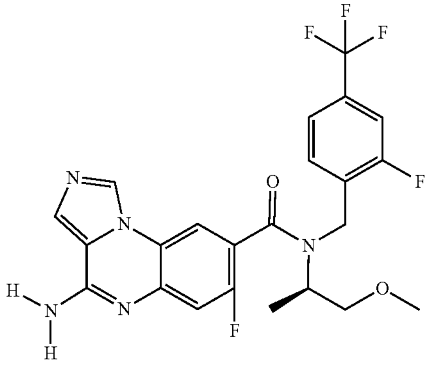 [SMILES: COC[C@@H](C)N(Cc1ccc(C(F)(F)F)cc1F)C(=O)c1cc2c(cc1F)nc(N)c1cncn12] |
| Ff-420 | 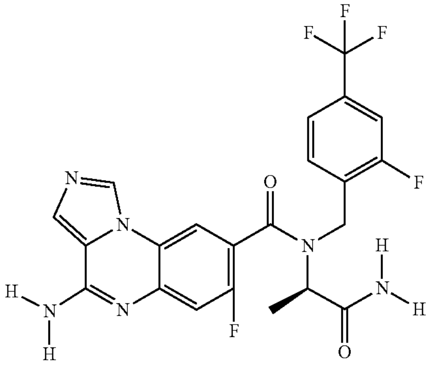 [SMILES: C[C@H](C(N)=O)N(Cc1ccc(C(F)(F)F)cc1F)C(=O)c1cc2c(cc1F)nc(N)c1cncn12] |
| Ff-421 | 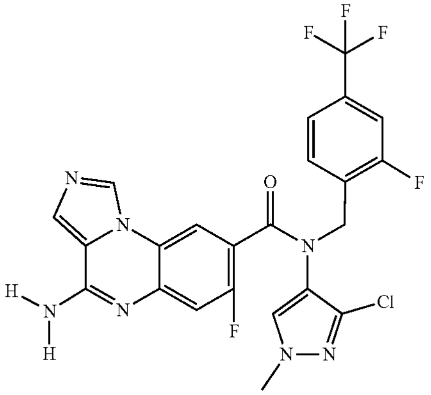 [SMILES: Cn1cc(N(Cc2ccc(C(F)(F)F)cc2F)C(=O)c2cc3c(cc2F)nc(N)c2cncn23)c(Cl)n1] |
| Ff-422 | 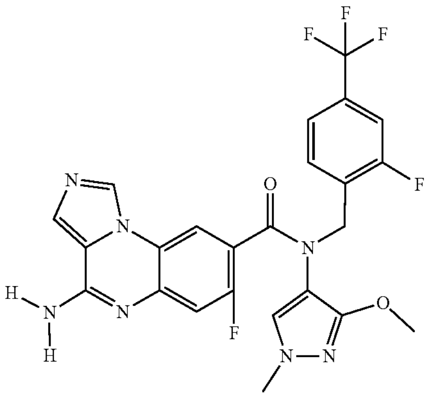 [SMILES: COc1nn(C)cc1N(Cc1ccc(C(F)(F)F)cc1F)C(=O)c1cc2c(cc1F)nc(N)c1cncn12] |

TABLE 1B-continued
| Compounds | |
|---|---|
| Example | Structure |
| Ff-423 | 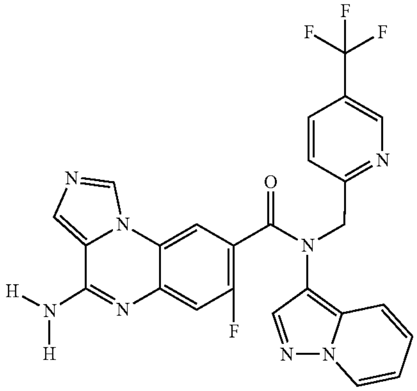 [SMILES: Nc1nc2cc(F)c(C(=O)N(Cc3ccc(C(F)(F)F)cn3)c3cnn4ccccc34)cc2n2cncc12] |
| Ff-424 | 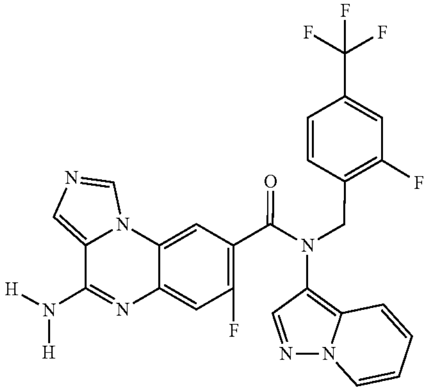 [SMILES: Nc1nc2cc(F)c(C(=O)N(Cc3ccc(C(F)(F)F)cc3F)c3cnn4ccccc34)cc2n2cncc12] |
| Ff-425 | 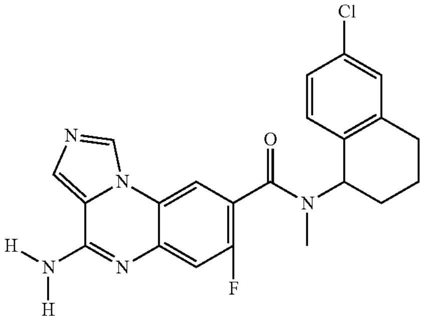 [SMILES: CN(C(=O)c1cc2c(cc1F)nc(N)c1cncn12)C1CCCc2cc(Cl)ccc21] |
| Ff-426 | 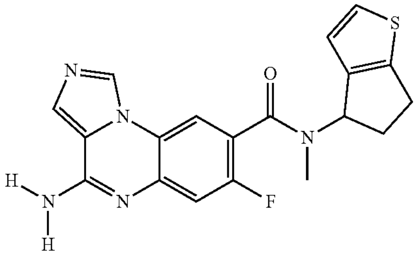 [SMILES: CN(C(=O)c1cc2c(cc1F)nc(N)c1cncn12)C1CCc2sccc21] |

TABLE 1B-continued
| Compounds | |
|---|---|
| Example | Structure |
| Ff-428 | 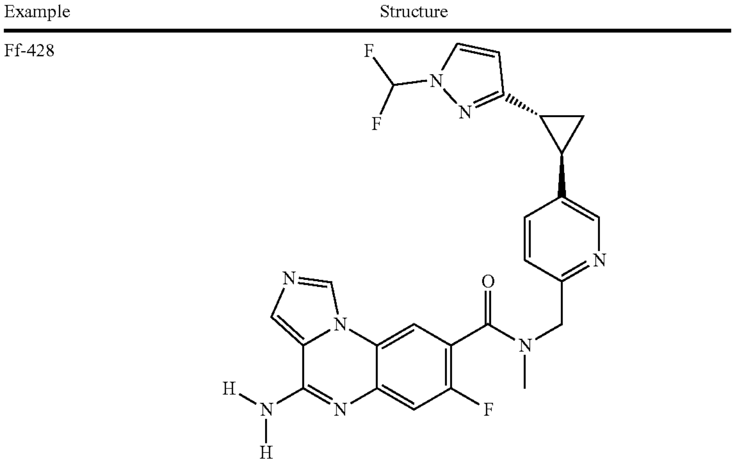 |
| Ff-429 | 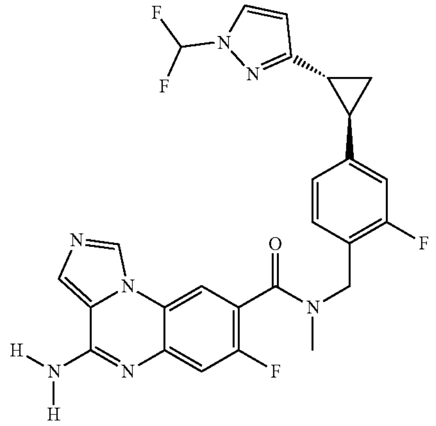 [SMILES: CN(Cc1ccc([C@@H]2C[C@H]2c2ccn(C(F)F)n2)cc1F)C(=O)c1cc2c(cc1F)nc(N)c1cncn12] |
| Ff-430 | 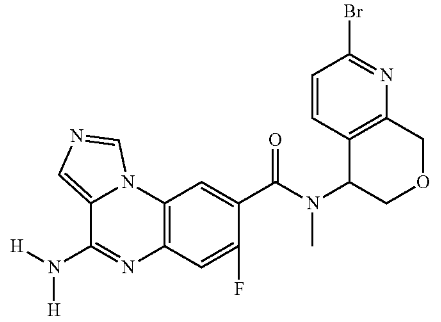 [SMILES: CN(C(=O)c1cc2c(cc1F)nc(N)c1cncn12)C1COCc2nc(Br)ccc21] |
| Ff-431 | 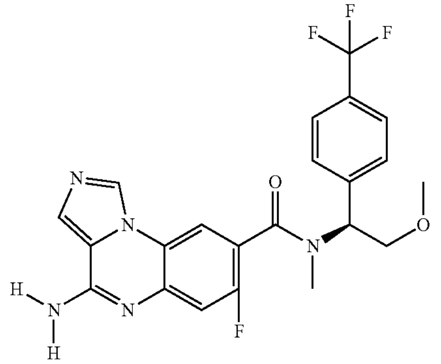 [SMILES: COC[C@H](c1ccc(C(F)(F)F)cc1)N(C)C(=O)c1cc2c(cc1F)nc(N)c1cncn12] |

TABLE 1B-continued
| Compounds | |
|---|---|
| Example | Structure |
| Ff-433 | 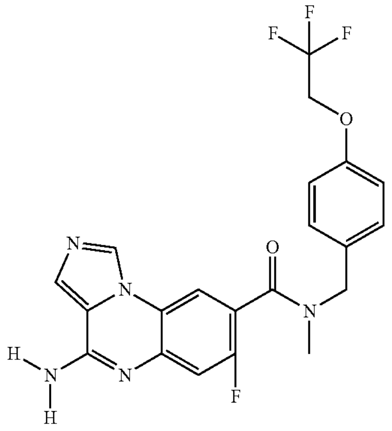 [SMILES: CN(Cc1ccc(OCC(F)(F)F)cc1)C(=O)c1cc2c(cc1F)nc(N)c1cncn12] |
| Ff-434 | 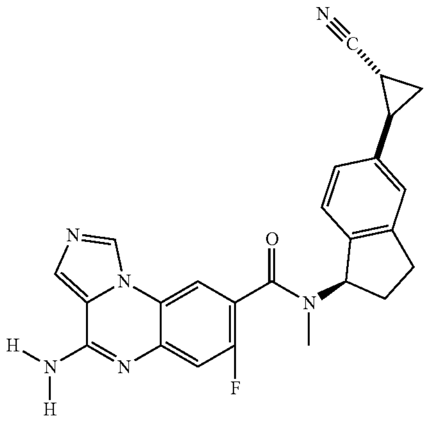 [SMILES: CN(C(=O)c1cc2c(cc1F)nc(N)c1cncn12)[C@@H]1CCc2cc([C@@H]3C[C@H]3C#N)ccc21] |
| Ff-435 | 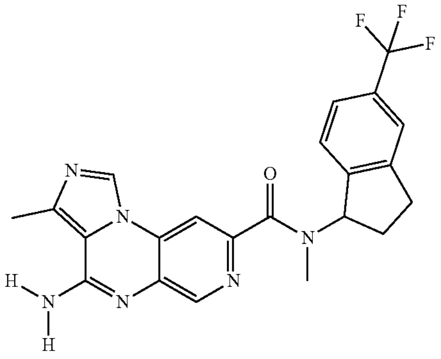 [SMILES: Cc1ncn2c1c(N)nc1cnc(C(=O)N(C)C3CCc4cc(C(F)(F)F)ccc43)cc12] |
| Ff-436 | 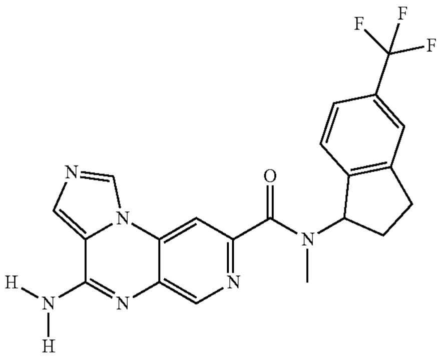 [SMILES: CN(C(=O)c1cc2c(cn1)nc(N)c1cncn12)C1CCc2cc(C(F)(F)F)ccc21] |

TABLE 1B-continued
| Compounds | |
|---|---|
| Example | Structure |
| Ff-437 | 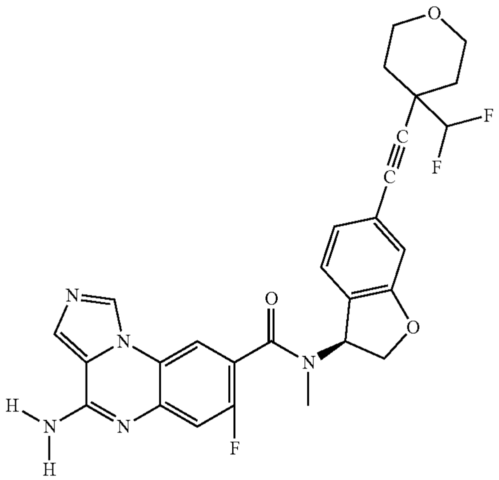 [SMILES: CN(C(=O)c1cc2c(cc1F)nc(N)c1cncn12)[C@@H]1COc2cc(C#CC3(C(F)F)CCOCC3)ccc21] |
| Ff-438 | 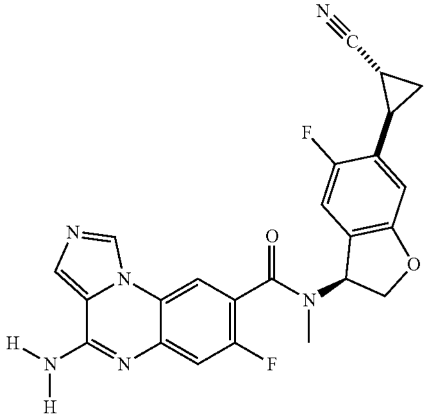 [SMILES: CN(C(=O)c1cc2c(cc1F)nc(N)c1cncn12)[C@@H]1COc2cc([C@@H]3C[C@H]3C#N)c(F)cc21] |
| Ff-439 | 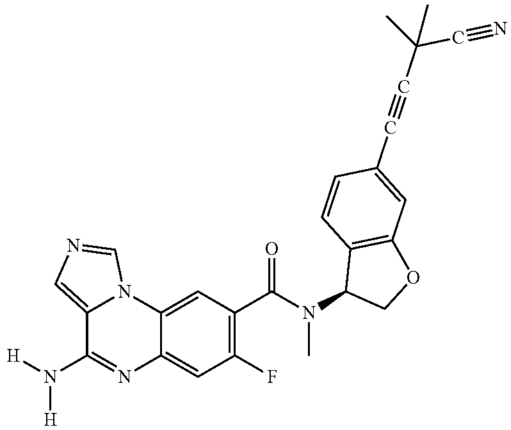 [SMILES: CN(C(=O)c1cc2c(cc1F)nc(N)c1cncn12)[C@@H]1COc2cc(C#CC(C)(C)C#N)ccc21] |

TABLE 1B-continued
| Compounds | |
|---|---|
| Example | Structure |
| Ff-440 | 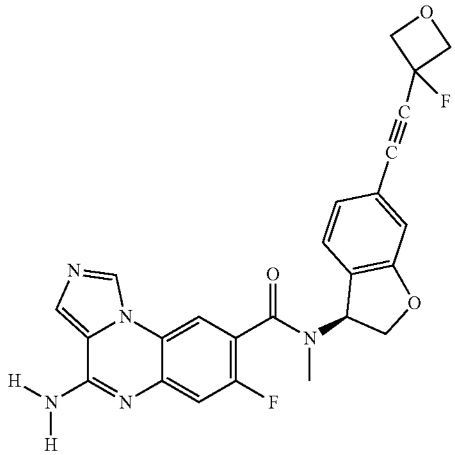 [SMILES: CN(C(=O)c1cc2c(cc1F)nc(N)c1cncn12)[C@@H]1COc2cc(C#CC3(F)COC3)ccc21] |
| Ff-441 | 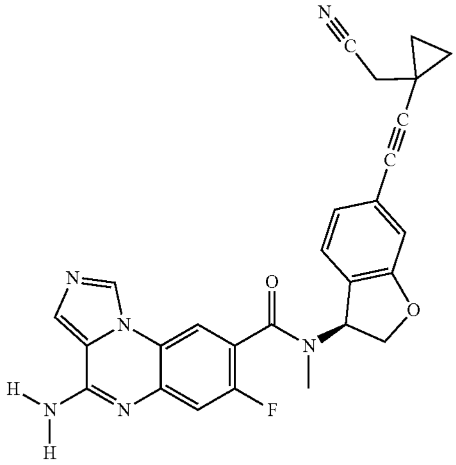 [SMILES: CN(C(=O)c1cc2c(cc1F)nc(N)c1cncn12)[C@@H]1COc2cc(C#CC3(CC#N)CC3)ccc21] |
| Ff-442 | 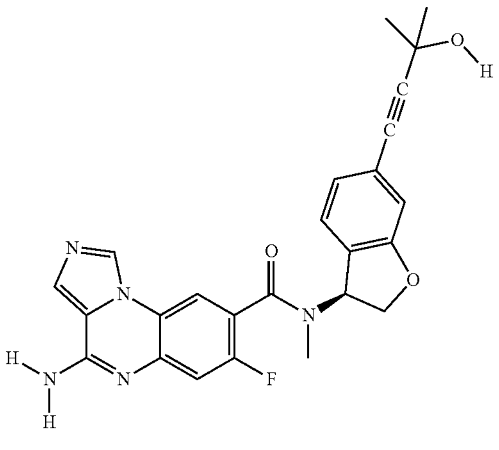 [SMILES: CN(C(=O)c1cc2c(cc1F)nc(N)c1cncn12)[C@@H]1COc2cc(C#CC(C)(C)O)ccc21] |

TABLE 1B-continued
| Compounds | |
|---|---|
| Example | Structure |
| Ff-443 | 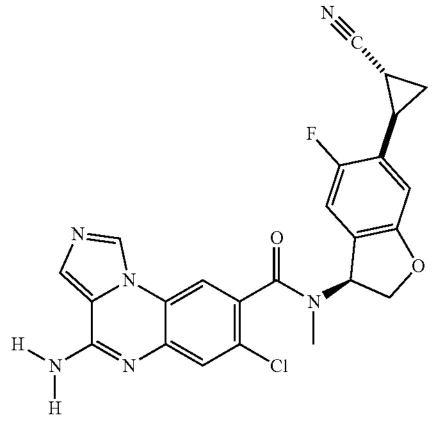 [SMILES: CN(C(=O)c1cc2c(cc1Cl)nc(N)c1cncn12)[C@@H]1COc2cc([C@@H]3C[C@H]3C#N)c(F)cc21] |
| Ff-444 | 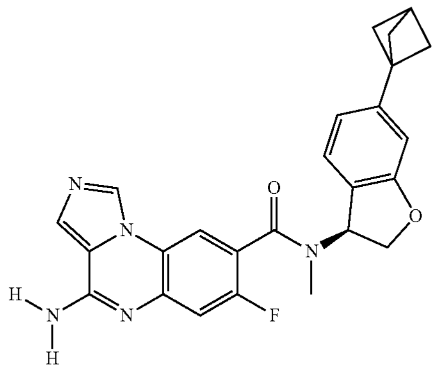 [SMILES: CN(C(=O)c1cc2c(cc1F)nc(N)c1cncn12)[C@@H]1COc2cc(C34CC(C3)C4)ccc21] |
| Ff-445 | 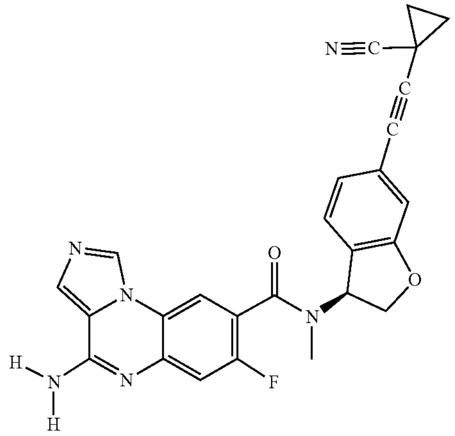 [SMILES: CN(C(=O)c1cc2c(cc1F)nc(N)c1cncn12)[C@@H]1COc2cc(C#CC3(C#N)CC3)ccc21] |

TABLE 1B-continued
| Compounds | |
| --- | --- |
| Example | Structure |
| Ff-446 | 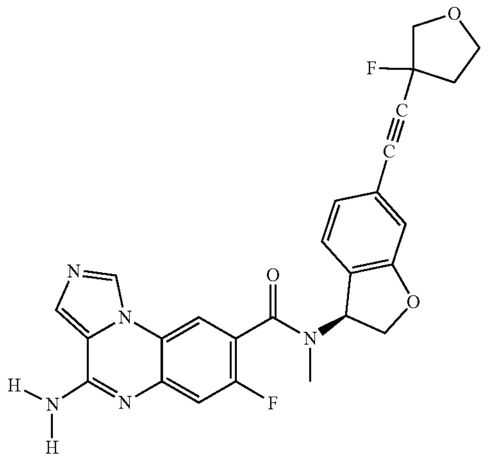 [SMILES: CN(C(=O)c1cc2c(cc1F)nc(N)c1cncn12)[C@@H]1COc2cc(C#CC3(F)CCOC3)ccc21] |
| Ff-447 | 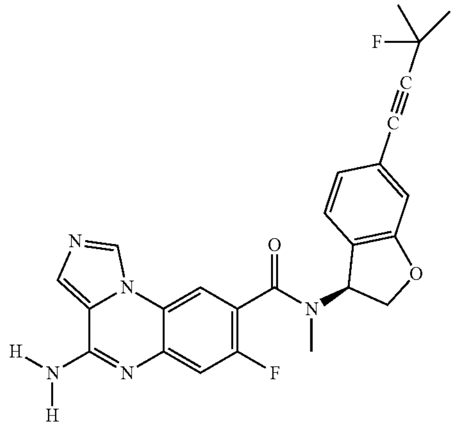 [SMILES: CN(C(=O)c1cc2c(cc1F)nc(N)c1cncn12)[C@@H]1COc2cc(C#CC(C)(C)F)ccc21] |
| Ff-449 | 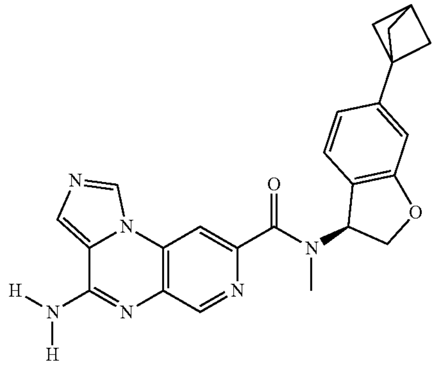 [SMILES: CN(C(=O)c1cc2c(cn1)nc(N)c1cncn12)[C@@H]1COc2cc(C34CC(C3)C4)ccc21] |

TABLE 1B-continued
| Compounds | |
|---|---|
| Example | Structure |
| Ff-450 | 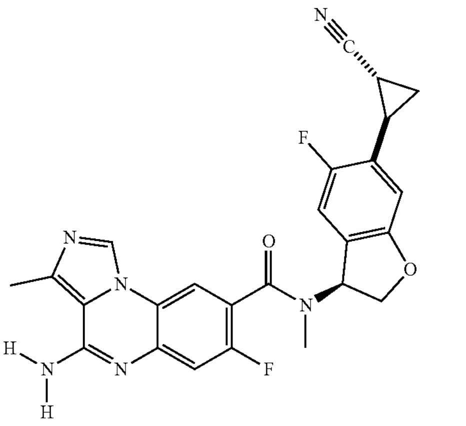 [SMILES: Cc1ncn2c1c(N)nc1cc(F)c(C(=O)N(C)[C@@H]3COc4cc([C@@H]5C[C@H]5C#N)c(F)cc43)cc12] |
| Ff-451 | 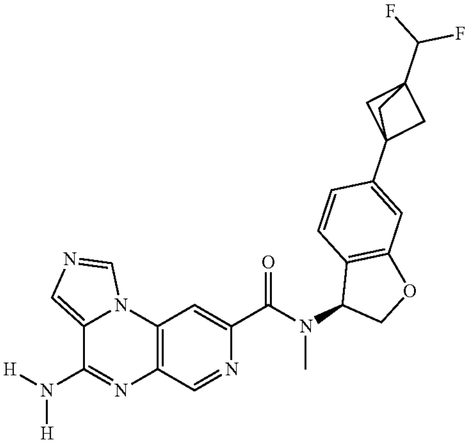 [SMILES: CN(C(=O)c1cc2c(cn1)nc(N)c1cncn12)[C@@H]1COc2cc(C34CC(C(F)F)(C3)C4)ccc21] |
| Ff-452 | 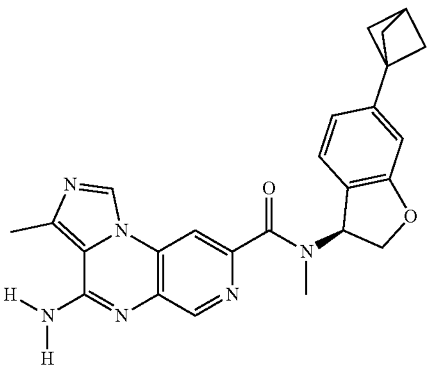 [SMILES: Cc1ncn2c1c(N)nc1cnc(C(=O)N(C)[C@@H]3COc4cc(C56CC(C5)C6)ccc43)cc12] |

TABLE 1B-continued
| Compounds | |
| --- | --- |
| Example | Structure |
| Ff-453 | 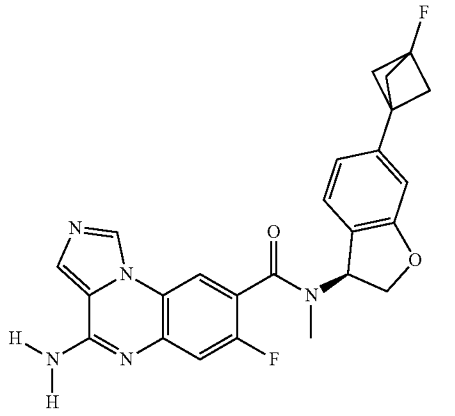 [SMILES: CN(C(=O)c1cc2c(cc1F)nc(N)c1cncn12)[C@@H]1COc2cc(C34CC(F)(C3)C4)ccc21] |
| Ff-454 | 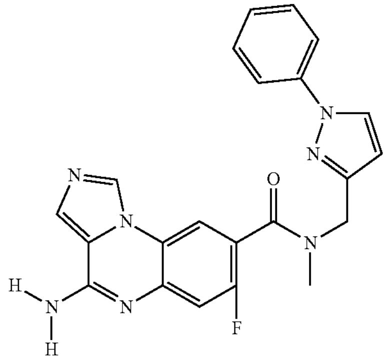 [SMILES: CN(Cc1ccn(-c2ccccc2)n1)C(=O)c1cc2c(cc1F)nc(N)c1cncn12] |
| Ff-455 | 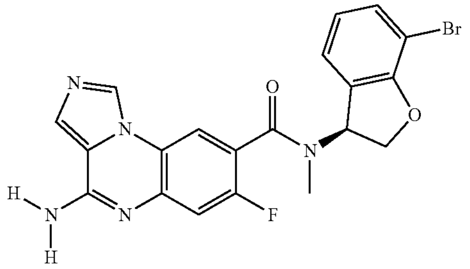 [SMILES: CN(C(=O)c1cc2c(cc1F)nc(N)c1cncn12)[C@@H]1COc2c(Br)cccc21] |
| Ff-456 | 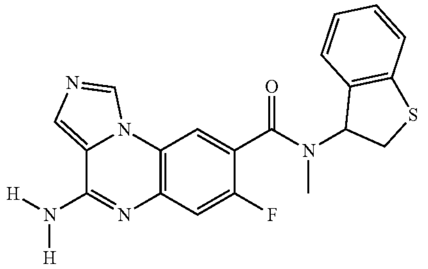 [SMILES: CN(C(=O)c1cc2c(cc1F)nc(N)c1cncn12)C1CSc2ccccc21] |

TABLE 1B-continued
| Compounds | |
|---|---|
| Example | Structure |
| Ff-457 | 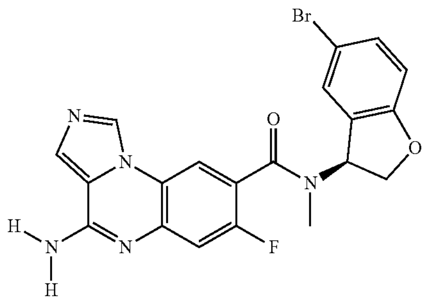 [SMILES: CN(C(=O)c1cc2c(cc1F)nc(N)c1cncn12)[C@@H]1COc2ccc(Br)cc21] |
| Ff-458 | 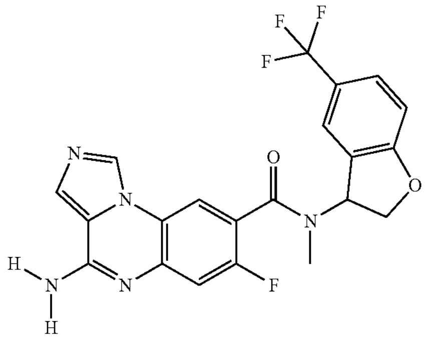 [SMILES: CN(C(=O)c1cc2c(cc1F)nc(N)c1cncn12)C1COc2ccc(C(F)(F)F)cc21] |
| Ff-459 | 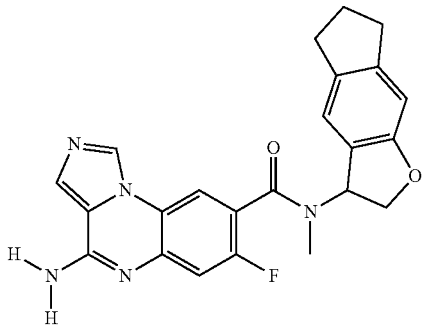 [SMILES: CN(C(=O)c1cc2c(cc1F)nc(N)c1cncn12)C1COc2cc3c(cc21)CCC3] |
| Ff-460 | 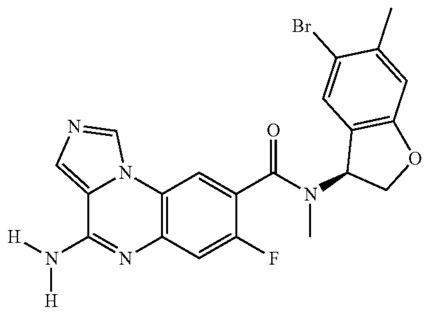 [SMILES: Cc1cc2c(cc1Br)[C@H](N(C)C(=O)c1cc3c(cc1F)nc(N)c1cncn13)CO2] |

TABLE 1B-continued
| Compounds | |
|---|---|
| Example | Structure |
| Ff-465 | 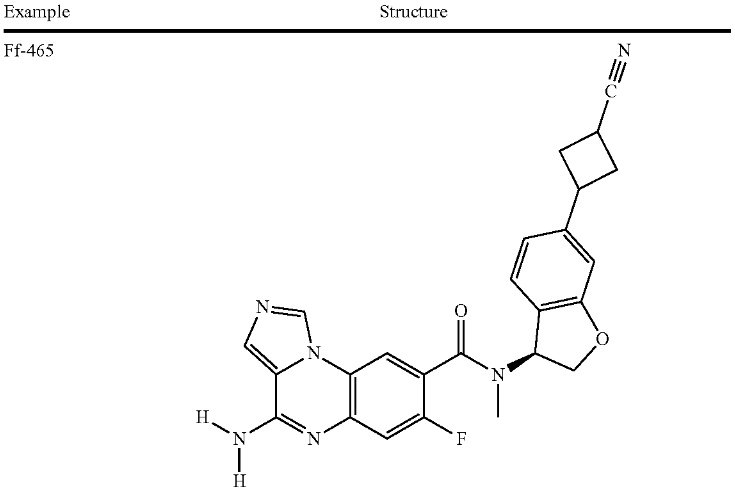 |
| Ff-466 | 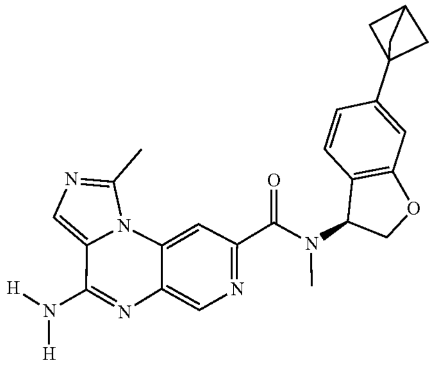 [SMILES: Cc1ncc2c(N)nc3cnc(C(=O)N(C)[C@@H]4COc5cc(C67CC(C6)C7)ccc54)cc3n12] |
| Ff-468 | 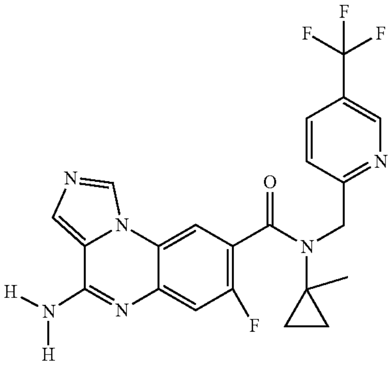 [SMILES: CC1(N(Cc2ccc(C(F)(F)F)cn2)C(=O)c2cc3c(cc2F)nc(N)c2cncn23)CC1] |
| Ff-470 | 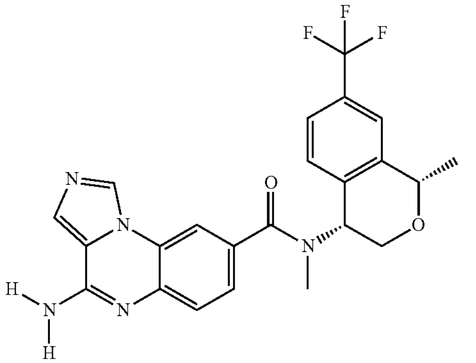 [SMILES: C[C@@H]1OC[C@H](N(C)C(=O)c2ccc3nc(N)c4cncn4c3c2)c2ccc(C(F)(F)F)cc21] |

TABLE 1B-continued
| Compounds | |
|---|---|
| Example | Structure |
| Ff-471 | 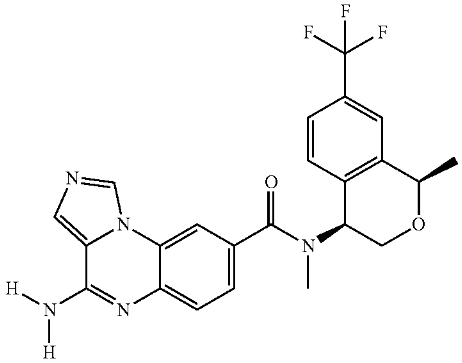 [SMILES: C[C@H]1OC[C@@H](N(C)C(=O)c2ccc3nc(N)c4cncn4c3c2)c2ccc(C(F)(F)F)cc21] |
| Ff-472 | 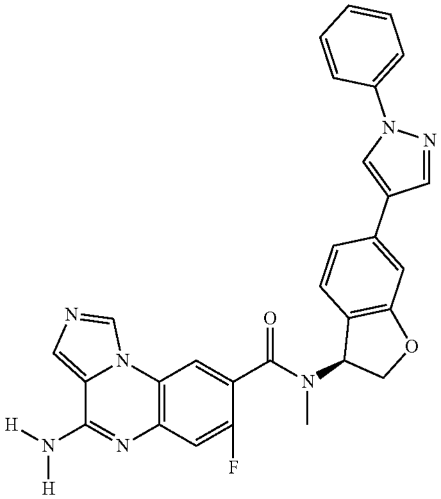 [SMILES: CN(C(=O)c1cc2c(cc1F)nc(N)c1cncn12)[C@@H]1COc2cc(-c3cnn(-c4ccccc4)c3)ccc21] |
| Ff-473 | 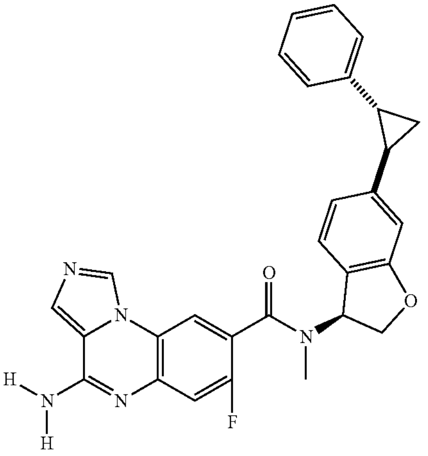 (±) |

TABLE 1B-continued
| Compounds | |
|---|---|
| Example | Structure |
| Ff-474 | 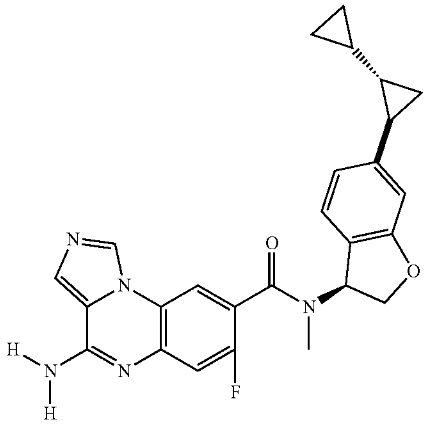 (±) |
| Ff-475 | 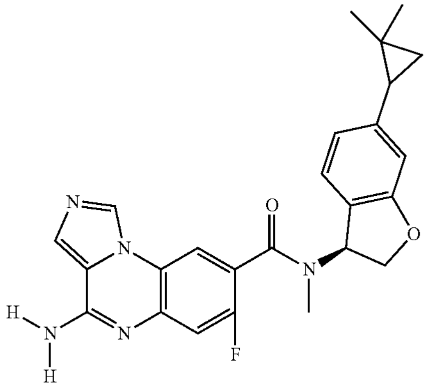 [SMILES: CN(C(=O)c1cc2c(cc1F)nc(N)c1cncn12)[C@@H]1COc2cc(C3CC3(C)C)ccc21] |
| Ff-476 | 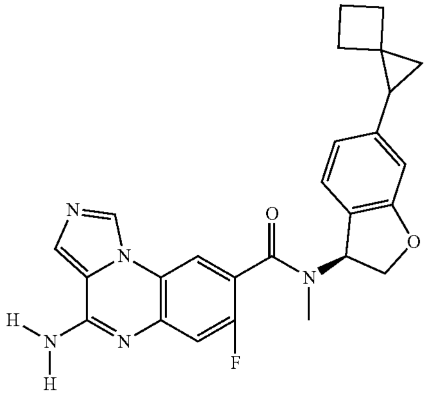 [SMILES: CN(C(=O)c1cc2c(cc1F)nc(N)c1cncn12)[C@@H]1COc2cc(C3CC34CCC4)ccc21] |

TABLE 1B-continued
| Compounds | |
|---|---|
| Example | Structure |
| Ff-477 | 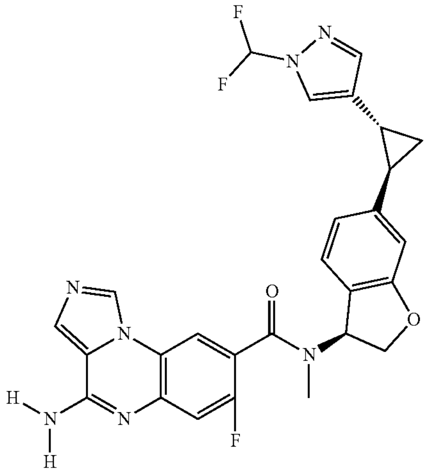 [SMILES: CN(C(=O)c1cc2c(cc1F)nc(N)c1cncn12)[C@@H]1COc2cc([C@@H]3C[C@H]3c3cnn(C(F)F)c3)ccc21] |
| Ff-478 | 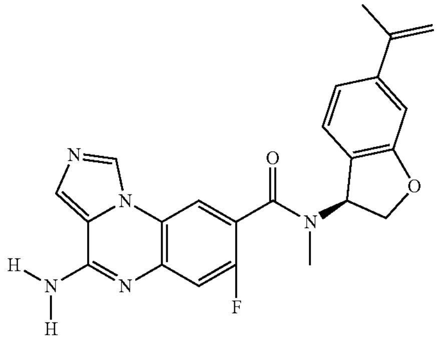 [SMILES: C=C(C)c1ccc2c(c1)OC[C@H]2N(C)C(=O)c1cc2c(cc1F)nc(N)c1cncn12] |
| Ff-479 | 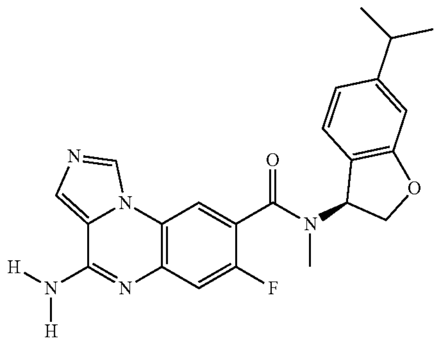 [SMILES: CC(C)c1ccc2c(c1)OC[C@H]2N(C)C(=O)c1cc2c(cc1F)nc(N)c1cncn12] |

TABLE 1B-continued
| Compounds | |
|---|---|
| Example | Structure |
| Ff-480 | 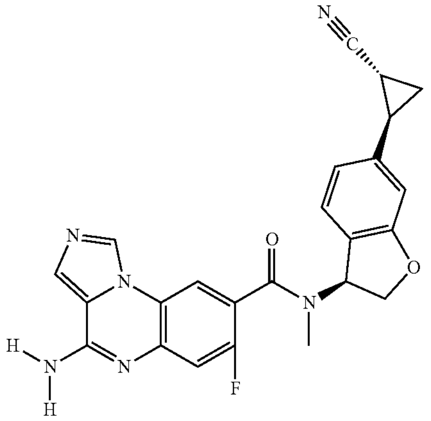 [SMILES: CN(C(=O)c1cc2c(cc1F)nc(N)c1cncn12)[C@@H]1COc2cc([C@@H]3C[C@H]3C#N)ccc21] |
| Ff-481 | 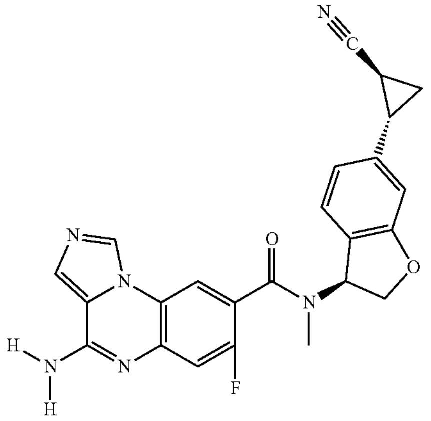 [SMILES: CN(C(=O)c1cc2c(cc1F)nc(N)c1cncn12)[C@@H]1COc2cc([C@H]3C[C@@H]3C#N)ccc21] |
| Ff-482 | 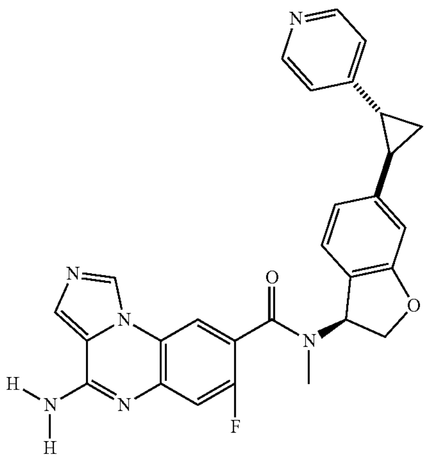 [SMILES: CN(C(=O)c1cc2c(cc1F)nc(N)c1cncn12)[C@@H]1COc2cc([C@@H]3C[C@H]3c3ccncc3)ccc21] |

TABLE 1B-continued
| Compounds | |
|---|---|
| Example | Structure |
| Ff-483 | 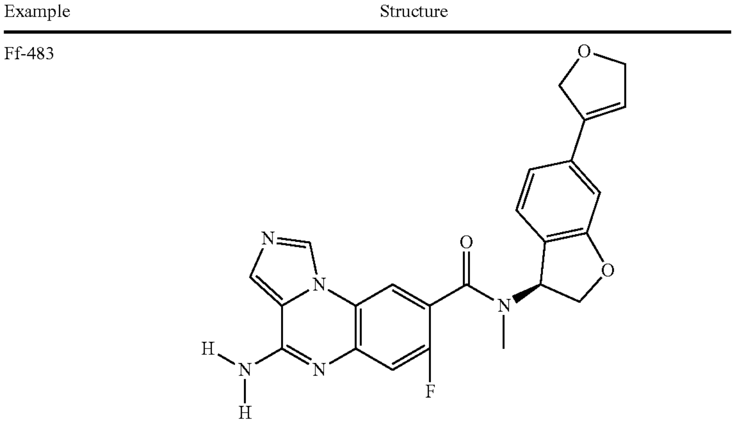 |
| Ff-484 | 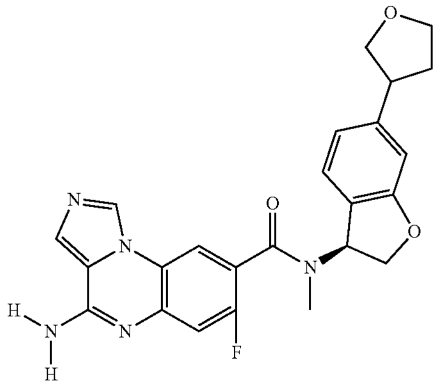 [SMILES: CN(C(=O)c1cc2c(cc1F)nc(N)c1cncn12)[C@@H]1COc2cc(C3CCOC3)ccc21] |
| Ff-485 | 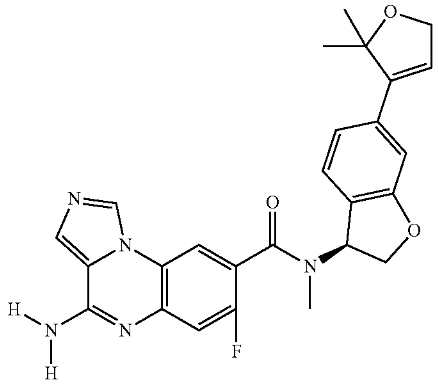 [SMILES: CN(C(=O)c1cc2c(cc1F)nc(N)c1cncn12)[C@@H]1COc2cc(C3=CCOC3(C)C)ccc21] |
| Ff-486 | 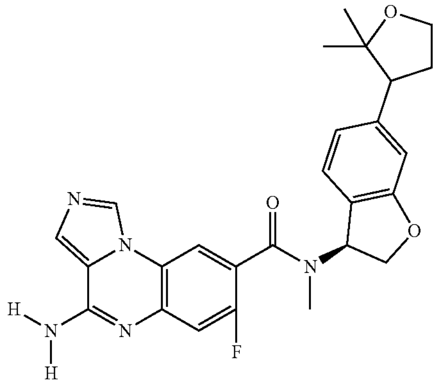 [SMILES: CN(C(=O)c1cc2c(cc1F)nc(N)c1cncn12)[C@@H]1COc2cc(C3CCOC3(C)C)ccc21] |

TABLE 1B-continued
| Compounds | |
|---|---|
| Example | Structure |
| Ff-490 | 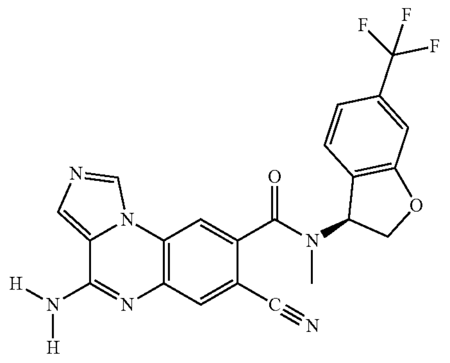 [SMILES: CN(C(=O)c1cc2c(cc1C#N)nc(N)c1cncn12)[C@@H]1COc2cc(C(F)(F)F)ccc21] |
| Ff-492 | 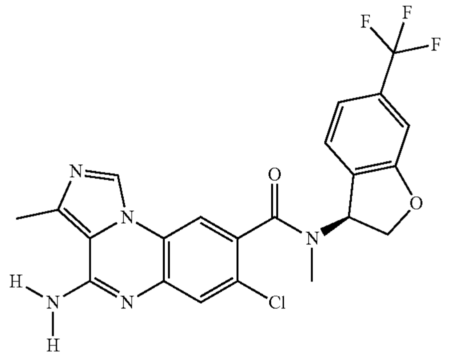 [SMILES: Cc1ncn2c1c(N)nc1cc(Cl)c(C(=O)N(C)[C@@H]3COc4cc(C(F)(F)F)ccc43)cc12] |
| Ff-493 | 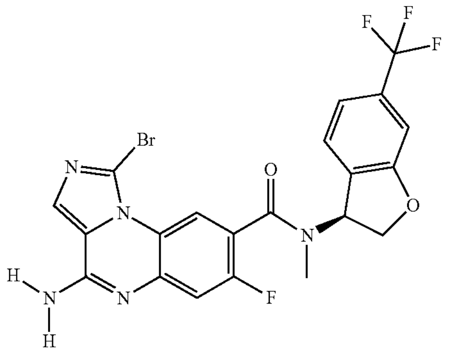 [SMILES: CN(C(=O)c1cc2c(cc1F)nc(N)c1cnc(Br)n12)[C@@H]1COc2cc(C(F)(F)F)ccc21] |
| Ff-494 | 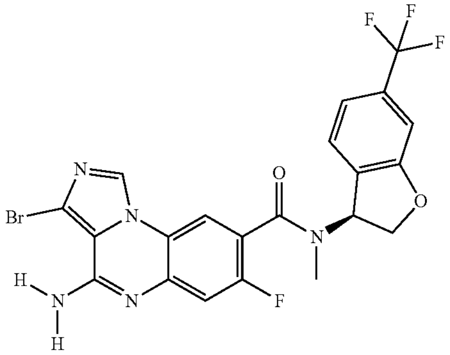 [SMILES: CN(C(=O)c1cc2c(cc1F)nc(N)c1c(Br)ncn12)[C@@H]1COc2cc(C(F)(F)F)ccc21] |

TABLE 1B-continued
| Compounds | |
|---|---|
| Example | Structure |
| Ff-497 | 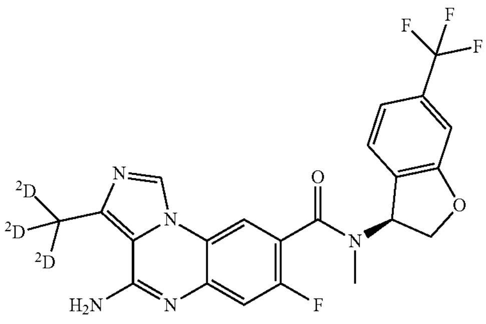 [SMILES: [2H]C([2H])([2H])c1ncn2c1c(N)nc1cc(F)c(C(=O)N(C)[C@@H]3COc4cc(C(F)(F)F)ccc43)cc12] |
| Ff-502 | 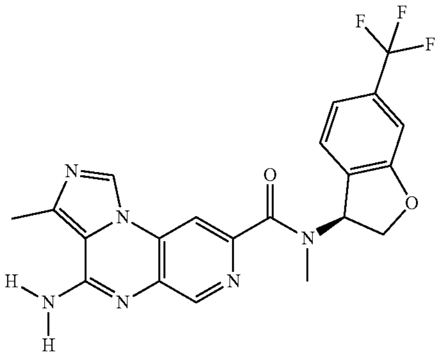 [SMILES: Cc1ncn2c1c(N)nc1cnc(C(=O)N(C)[C@@H]3COc4cc(C(F)(F)F)ccc43)cc12] |
| Ff-503 | 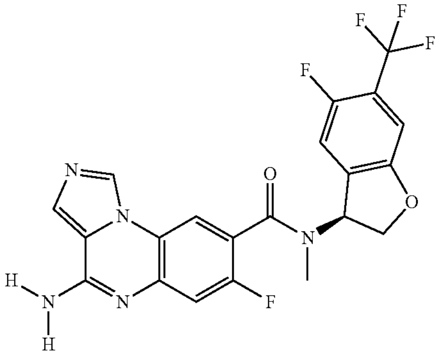 [SMILES: CN(C(=O)c1cc2c(cc1F)nc(N)c1cncn12)[C@@H]1COc2cc(C(F)(F)F)c(F)cc21] |
| Ff-504 | 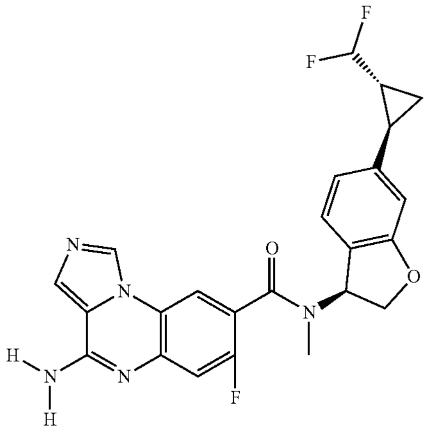 [SMILES: CN(C(=O)c1cc2c(cc1F)nc(N)c1cncn12)[C@@H]1COc2cc([C@@H]3C[C@H]3C(F)F)ccc21] |

TABLE 1B-continued
| Compounds | |
|---|---|
| Example | Structure |
| Ff-505 | 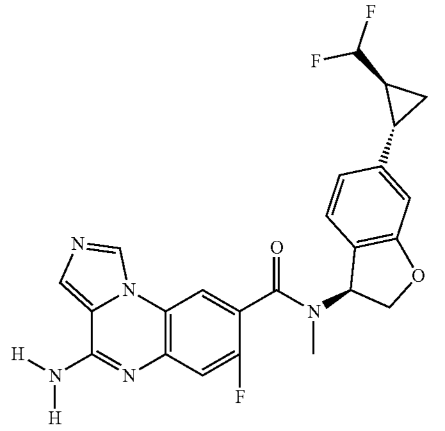 [SMILES: CN(C(=O)c1cc2c(cc1F)nc(N)c1cncn12)[C@@H]1COc2cc([C@H]3C[C@@H]3C(F)F)ccc21] |
| Ff-506 | 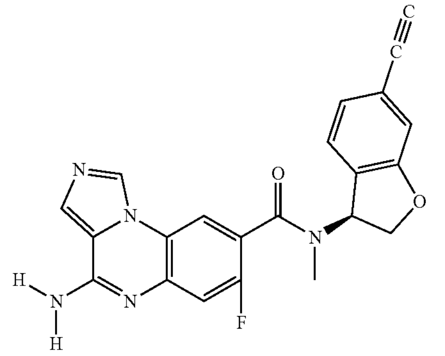 |
| Ff-508 | 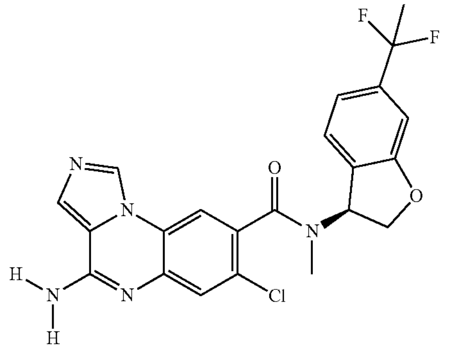 [SMILES: CN(C(=O)c1cc2c(cc1Cl)nc(N)c1cncn12)[C@@H]1COc2cc(C(C)(F)F)ccc21] |
| Ff-509 | 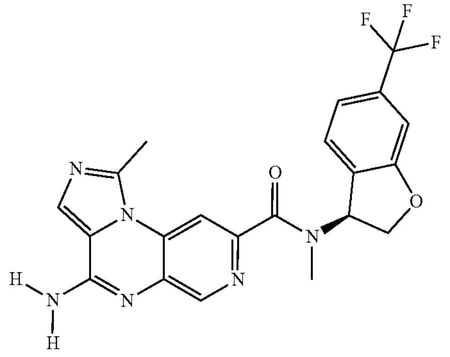 [SMILES: Cc1ncc2c(N)nc3cnc(C(=O)N(C)[C@@H]4COc5cc(C(F)(F)F)ccc54)cc3n12] |

TABLE 1B-continued
| Compounds | |
| --- | --- |
| Example | Structure |
| Ff-511 | 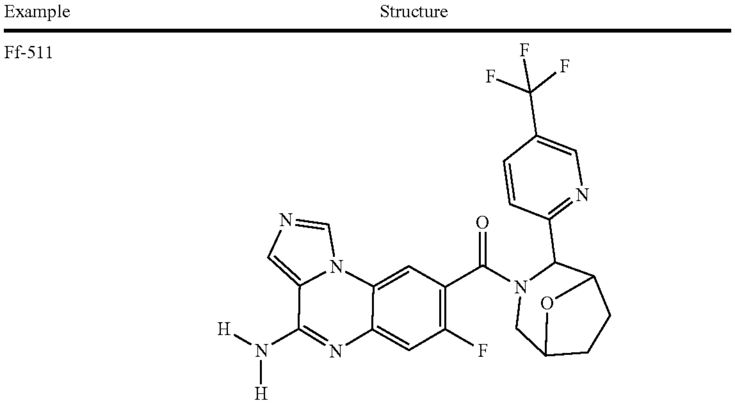 |
| Ff-512 | 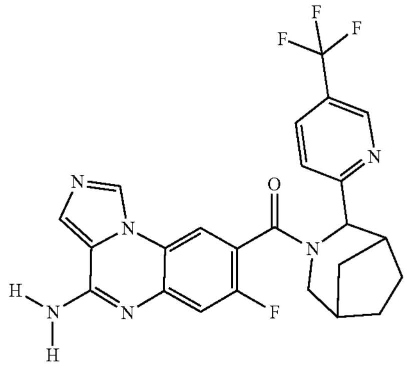 [SMILES: Nc1nc2cc(F)c(C(=O)N3CC4CCC(C4)C3c3ccc(C(F)(F)F)cn3)cc2n2cncc12] |
| Ff-513 | 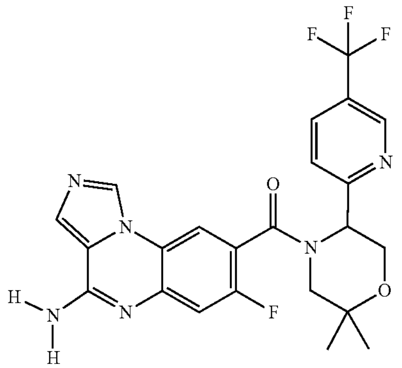 [SMILES: CC1(C)CN(C(=O)c2cc3c(cc2F)nc(N)c2cncn23)C(c2ccc(C(F)(F)F)cn2)CO1] |
| Ff-514 | 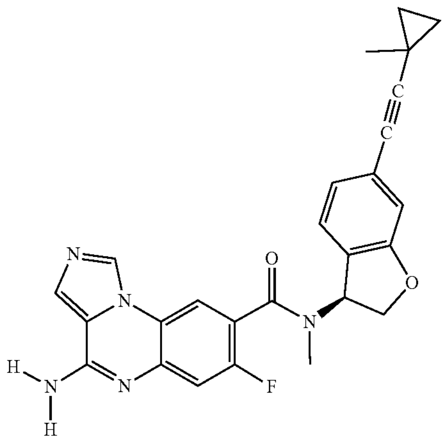 [SMILES: CN(C(=O)c1cc2c(cc1F)nc(N)c1cncn12)[C@@H]1COc2cc(C#CC3(C)CC3)ccc21] |

TABLE 1B-continued
| Compounds | |
|---|---|
| Example | Structure |
| Ff-515 | 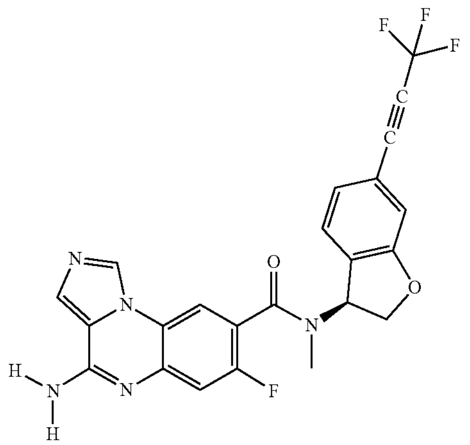 [SMILES: CN(C(=O)c1cc2c(cc1F)nc(N)c1cncn12)[C@@H]1COc2cc(C#CC(F)(F)F)ccc21] |
| Ff-516 | 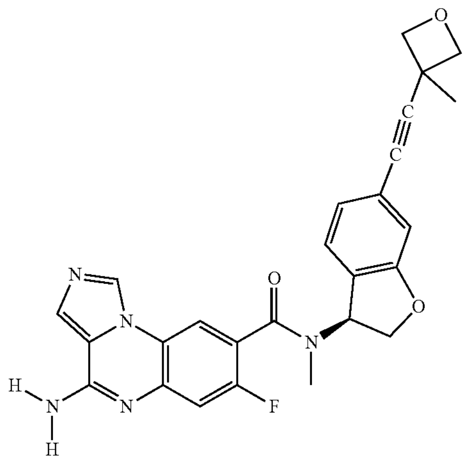 [SMILES: CN(C(=O)c1cc2c(cc1F)nc(N)c1cncn12)[C@@H]1COc2cc(C#CC3(C)COC3)ccc21] |
| Ff-517 | 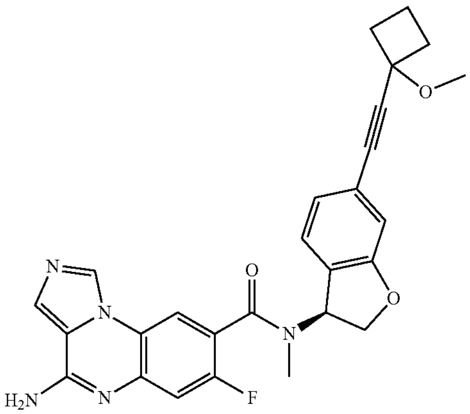 [SMILES: COC1(C#Cc2ccc3c(c2)OC[C@H]3N(C)C(=O)c2cc3c(cc2F)nc(N)c2cncn23)CCC1] |

TABLE 1B-continued
| Compounds | |
| --- | --- |
| Example | Structure |
| Ff-518 | 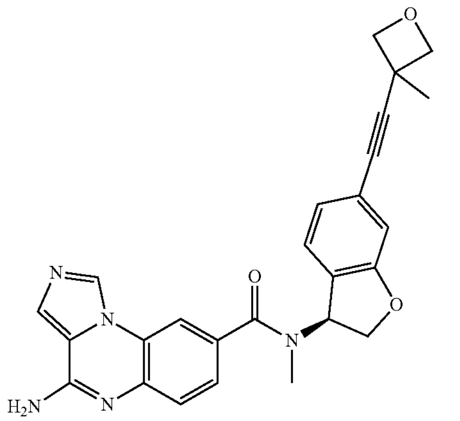 [SMILES: CN(C(=O)c1ccc2nc(N)c3cncn3c2c1)[C@@H]1COc2cc(C#CC3(C)COC3)ccc21] |
| Ff-519 | 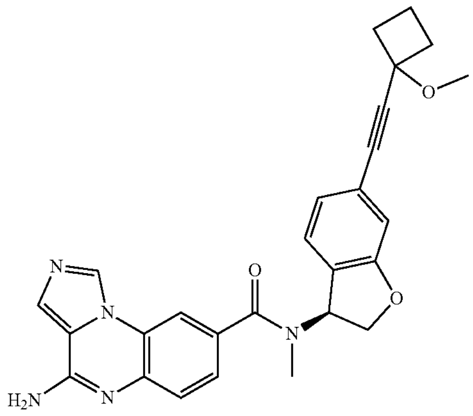 [SMILES: COC1(C#Cc2ccc3c(c2)OC[C@H]3N(C)C(=O)c2ccc3nc(N)c4cncn4c3c2)CCC1] |
| Ff-520 | 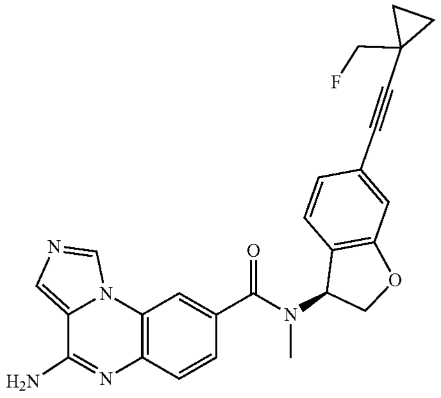 [SMILES: CN(C(=O)c1ccc2nc(N)c3cncn3c2c1)[C@@H]1COc2cc(C#CC3(CF)CC3)ccc21] |

TABLE 1B-continued
| Compounds | |
|---|---|
| Example | Structure |
| Ff-521 | 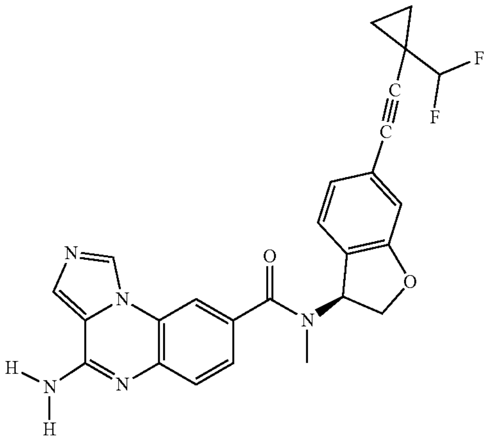 [SMILES: CN(C(=O)c1ccc2nc(N)c3cncn3c2c1)[C@@H]1COc2cc(C#CC3(C(F)F)CC3)ccc21] |
| Ff-522 | 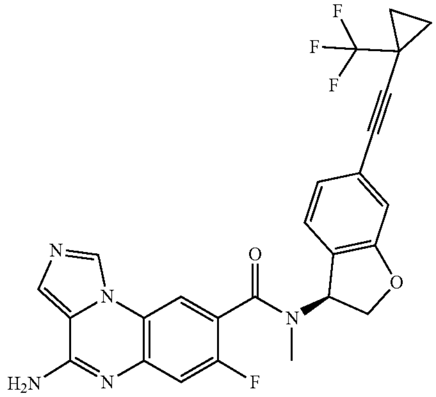 [SMILES: CN(C(=O)c1cc2c(cc1F)nc(N)c1cncn12)[C@@H]1COc2cc(C#CC3(C(F)(F)F)CC3)ccc21] |
| Ff-523 | 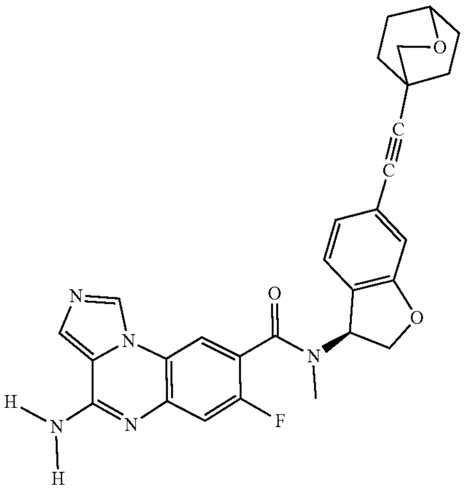 [SMILES: CN(C(=O)c1cc2c(cc1F)nc(N)c1cncn12)[C@@H]1COc2cc(C#CC34CCC(CC3)OC4)ccc21] |

TABLE 1B-continued
| Compounds | |
|---|---|
| Example | Structure |
| Ff-524 | 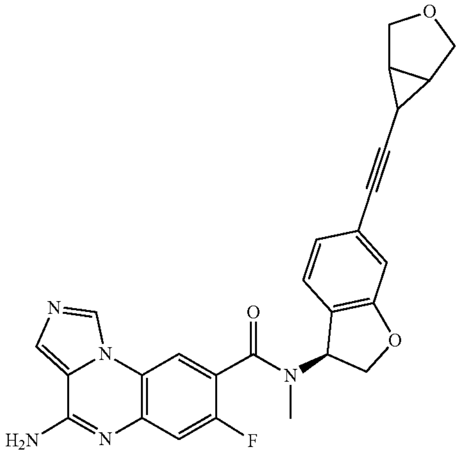 [SMILES: CN(C(=O)c1cc2c(cc1F)nc(N)c1cncn12)[C@@H]1COc2cc(C#CC3C4COCC34)ccc21] |
| Ff-525 | 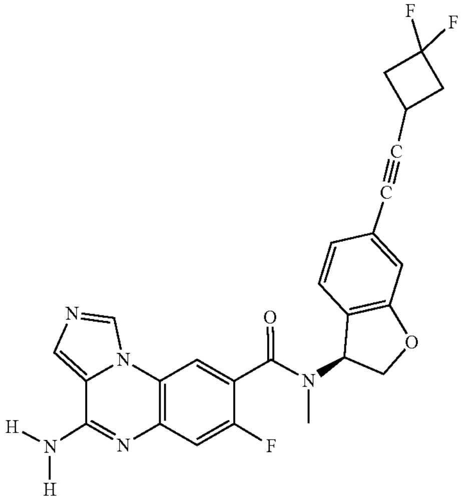 [SMILES: CN(C(=O)c1cc2c(cc1F)nc(N)c1cncn12)[C@@H]1COc2cc(C#CC3CC(F)(F)C3)ccc21] |
| Ff-526 | 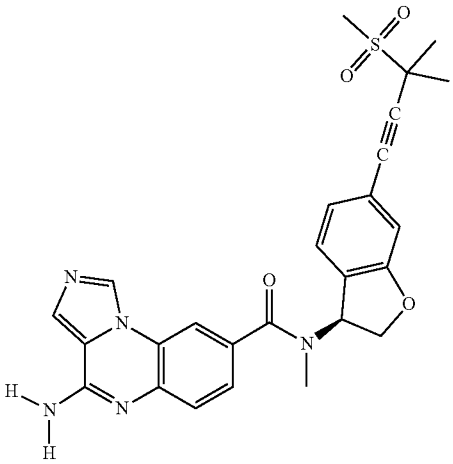 [SMILES: CN(C(=O)c1ccc2nc(N)c3cncn3c2c1)[C@@H]1COc2cc(C#CC(C)(C)S(C)(=O)=O)ccc21] |

TABLE 1B-continued
| Compounds | |
|---|---|
| Example | Structure |
| Ff-527 | 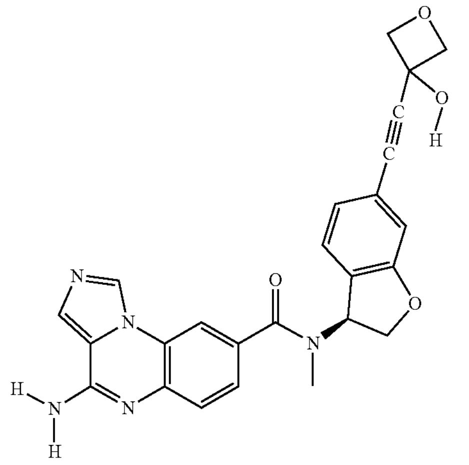 [SMILES: CN(C(=O)c1ccc2nc(N)c3cncn3c2c1)[C@@H]1COc2cc(C#CC3(O)COC3)ccc21] |
| Ff-528 | 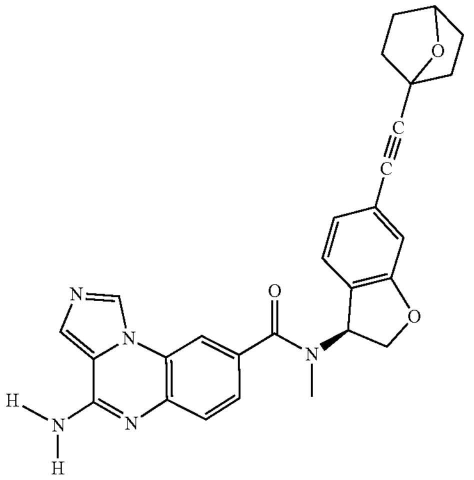 [SMILES: CN(C(=O)c1ccc2nc(N)c3cncn3c2c1)[C@@H]1COc2cc(C#CC34CCC(CC3)O4)ccc21] |
| Ff-529 | 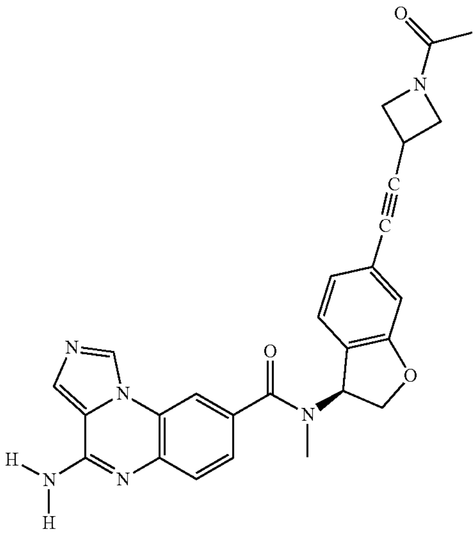 [SMILES: CC(=O)N1CC(C#Cc2ccc3c(c2)OC[C@H]3N(C)C(=O)c2ccc3nc(N)c4cncn4c3c2)C1] |

TABLE 1B-continued
| Compounds | |
|---|---|
| Example | Structure |
| Ff-530 | 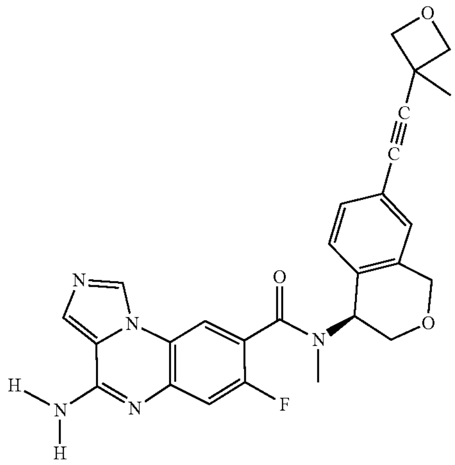 [SMILES: CN(C(=O)c1cc2c(cc1F)nc(N)c1cncn12)[C@@H]1COCc2cc(C#CC3(C)COC3)ccc21] |
| Ff-531 | 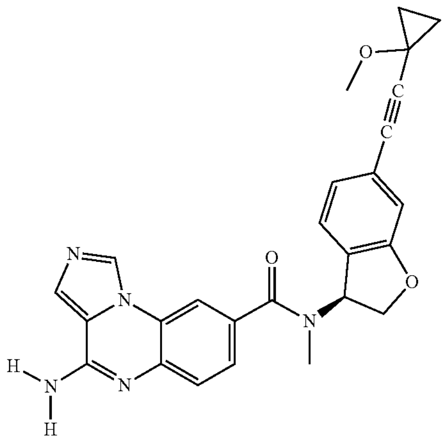 [SMILES: COC1(C#Cc2ccc3c(c2)OC[C@H]3N(C)C(=O)c2ccc3nc(N)c4cncn4c3c2)CC1] |
| Ff-532 | 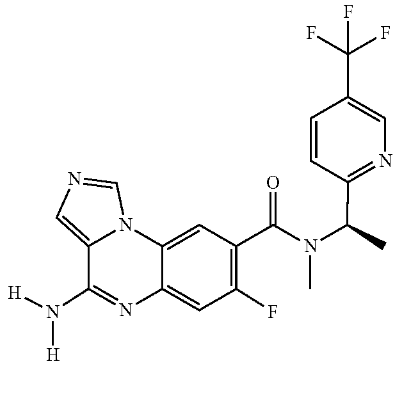 |

TABLE 1B-continued
| Compounds | |
|---|---|
| Example | Structure |
| Ff-533 | 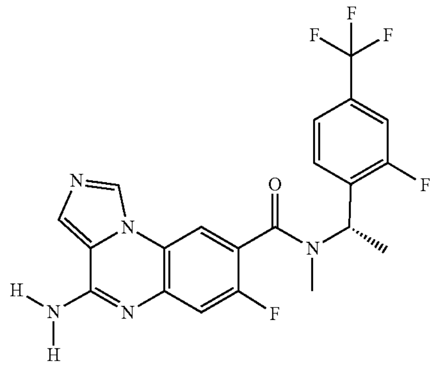 [SMILES: C[C@@H](c1ccc(C(F)(F)F)cc1F)N(C)C(=O)c1cc2c(cc1F)nc(N)c1cncn12] |
| Ff-534 | 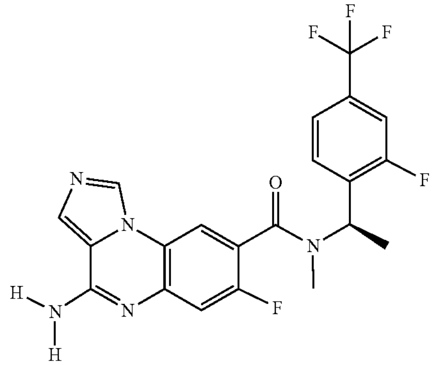 [SMILES: C[C@H](c1ccc(C(F)(F)F)cc1F)N(C)C(=O)c1cc2c(cc1F)nc(N)c1cncn12] |
| Ff-535 | 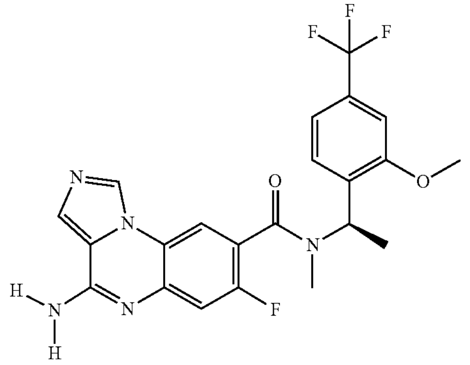 [SMILES: COc1cc(C(F)(F)F)ccc1[C@@H](C)N(C)C(=O)c1cc2c(cc1F)nc(N)c1cncn12] |
| Ff-536 | 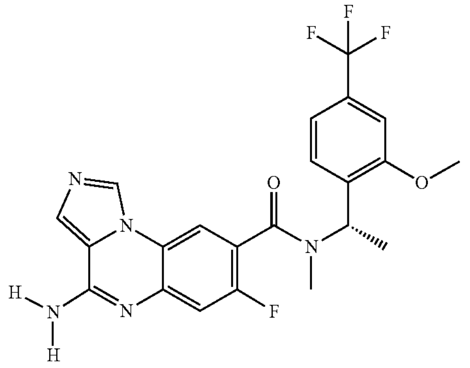 [SMILES: COc1cc(C(F)(F)F)ccc1[C@H](C)N(C)C(=O)c1cc2c(cc1F)nc(N)c1cncn12] |

TABLE 1B-continued
| Compounds | |
|---|---|
| Example | Structure |
| Ff-537 | 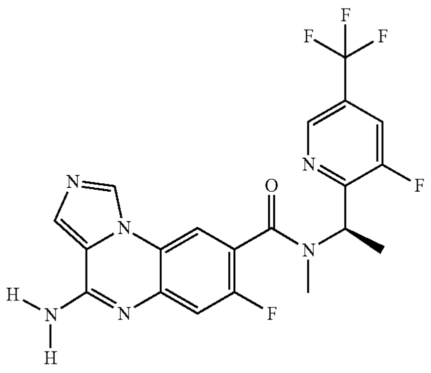 [SMILES: C[C@H](c1ncc(C(F)(F)F)cc1F)N(C)C(=O)c1cc2c(cc1F)nc(N)c1cncn12] |
| Ff-538 | 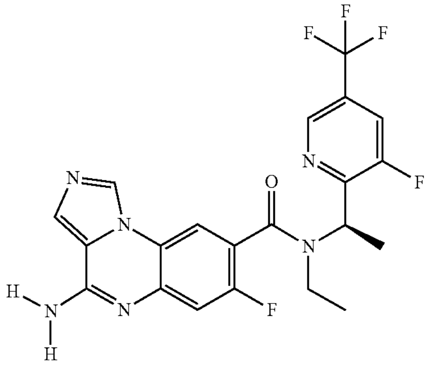 [SMILES: CCN(C(=O)c1cc2c(cc1F)nc(N)c1cncn12)[C@H](C)c1ncc(C(F)(F)F)cc1F] |
| Ff-541 | 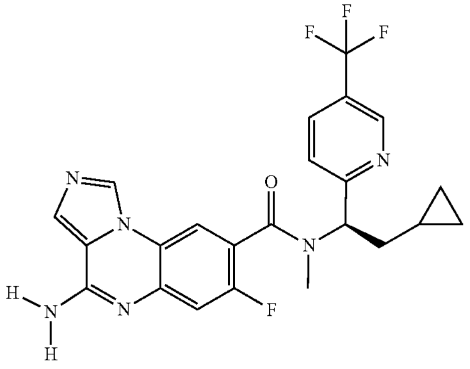 [SMILES: CN(C(=O)c1cc2c(cc1F)nc(N)c1cncn12)[C@H](CC1CC1)c1ccc(C(F)(F)F)cn1] |
| Ff-542 | 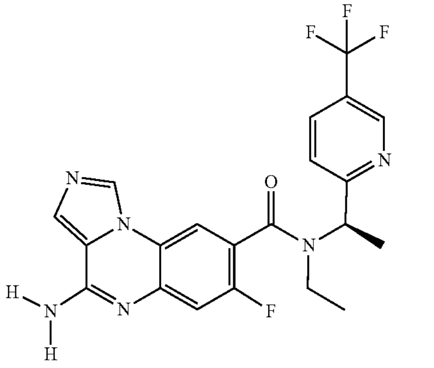 [SMILES: CCN(C(=O)c1cc2c(cc1F)nc(N)c1cncn12)[C@H](C)c1ccc(C(F)(F)F)cn1] |

TABLE 1B-continued
| Compounds | |
| --- | --- |
| Example | Structure |
| Ff-543 | 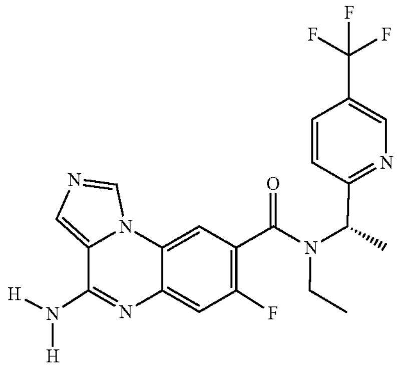 [SMILES: CCN(C(=O)c1cc2c(cc1F)nc(N)c1cncn12)[C@@H](C)c1ccc(C(F)(F)F)cn1] |
| Ff-544 | 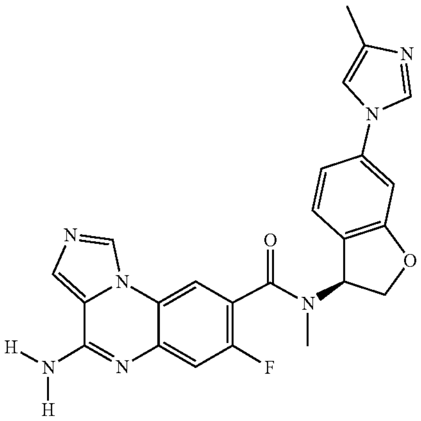 [SMILES: Cc1cn(-c2ccc3c(c2)OC[C@H]3N(C)C(=O)c2cc3c(cc2F)nc(N)c2cncn23)cn1] |
| Ff-545 | 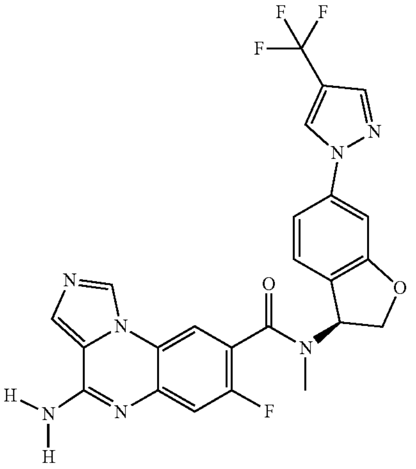 [SMILES: CN(C(=O)c1cc2c(cc1F)nc(N)c1cncn12)[C@@H]1COc2cc(-n3cc(C(F)(F)F)cn3)ccc21] |

TABLE 1B-continued
| Compounds | |
|---|---|
| Example | Structure |
| Ff-546 | 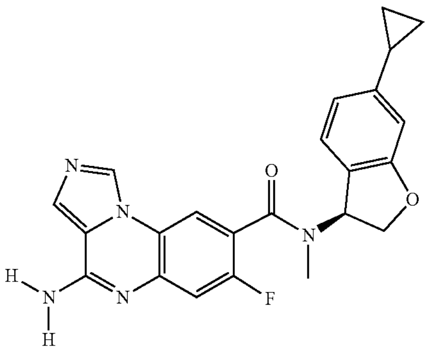 [SMILES: CN(C(=O)c1cc2c(cc1F)nc(N)c1cncn12)[C@@H]1COc2cc(C3CC3)ccc21] |
| Ff-547 | 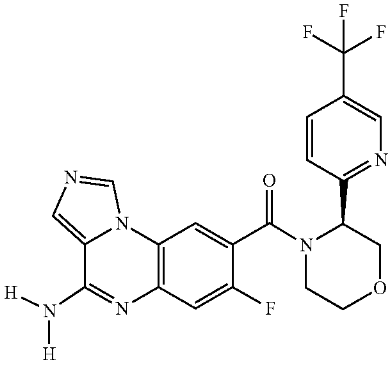 [SMILES: Nc1nc2cc(F)c(C(=O)N3CCOC[C@@H]3c3ccc(C(F)(F)F)cn3)cc2n2cncc12] |
| Ff-548 | 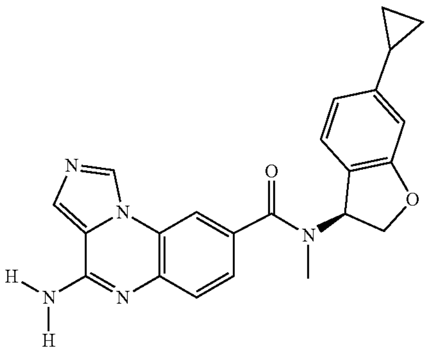 [SMILES: CN(C(=O)c1ccc2nc(N)c3cncn3c2c1)[C@@H]1COc2cc(C3CC3)ccc21] |
| Ff-550 | 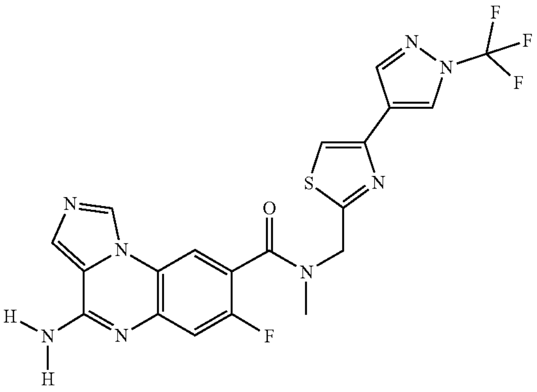 [SMILES: CN(Cc1nc(-c2cnn(C(F)(F)F)c2)cs1)C(=O)c1cc2c(cc1F)nc(N)c1cncn12] |

TABLE 1B-continued
| Compounds | |
|---|---|
| Example | Structure |
| Ff-551 | 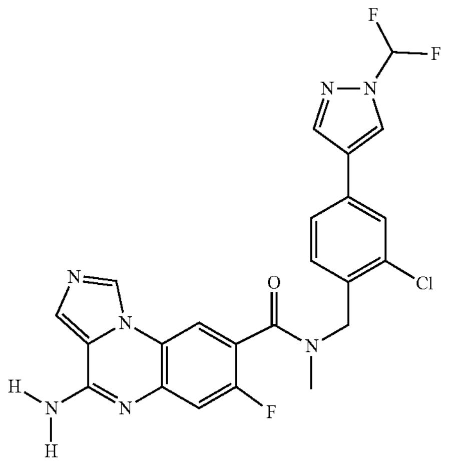 [SMILES: CN(Cc1ccc(-c2cnn(C(F)F)c2)cc1Cl)C(=O)c1cc2c(cc1F)nc(N)c1cncn12] |
| Ff-552 | 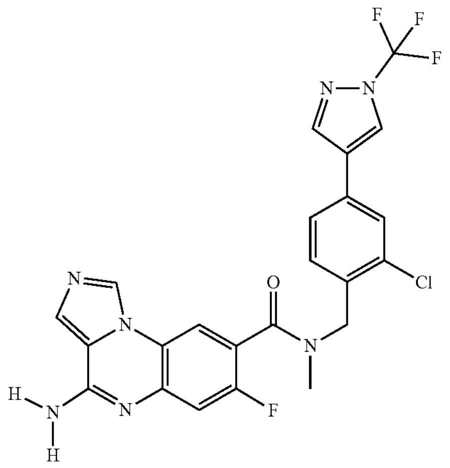 [SMILES: CN(Cc1ccc(-c2cnn(C(F)(F)F)c2)cc1Cl)C(=O)c1cc2c(cc1F)nc(N)c1cncn12] |
| Ff-553 | 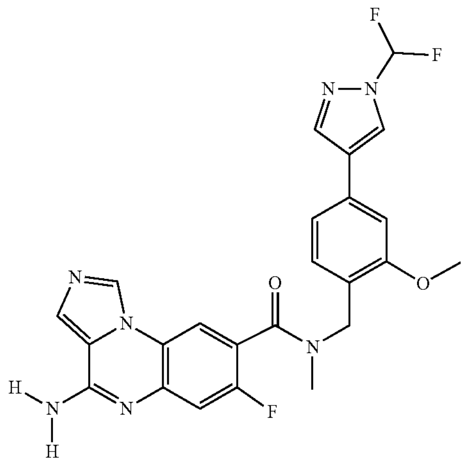 [SMILES: COc1cc(-c2cnn(C(F)F)c2)ccc1CN(C)C(=O)c1cc2c(cc1F)nc(N)c1cncn12] |

TABLE 1B-continued
| Compounds | |
|---|---|
| Example | Structure |
| Ff-554 | 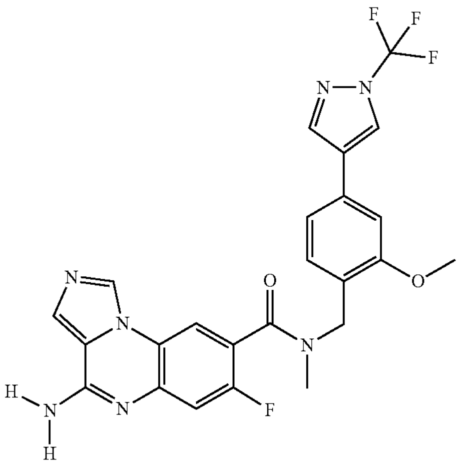 [SMILES: COc1cc(-c2cnn(C(F)(F)F)c2)ccc1CN(C)C(=O)c1cc2c(cc1F)nc(N)c1cncn12] |
| Ff-555 | 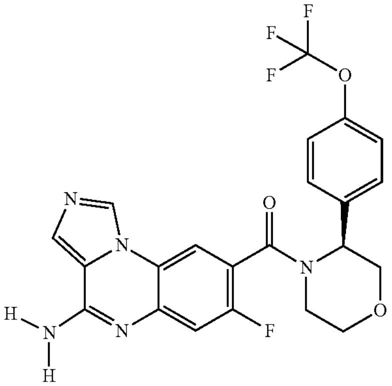 [SMILES: Nc1nc2cc(F)c(C(=O)N3CCOC[C@@H]3c3ccc(OC(F)(F)F)cc3)cc2n2cncc12] |
| Ff-556 | 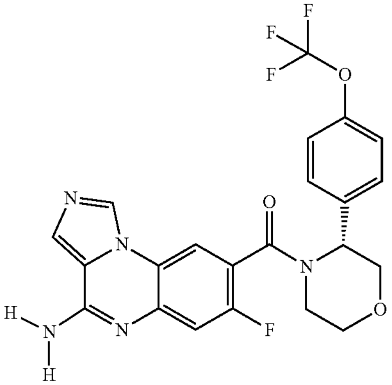 [SMILES: Nc1nc2cc(F)c(C(=O)N3CCOC[C@H]3c3ccc(OC(F)(F)F)cc3)cc2n2cncc12] |

TABLE 1B-continued
| Compounds | |
|---|---|
| Example | Structure |
| Ff-557 | 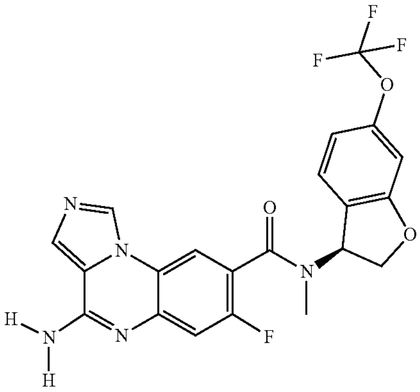 [SMILES: CN(C(=O)c1cc2c(cc1F)nc(N)c1cncn12)[C@@H]1COc2cc(OC(F)(F)F)ccc21] |
| Ff-558 | 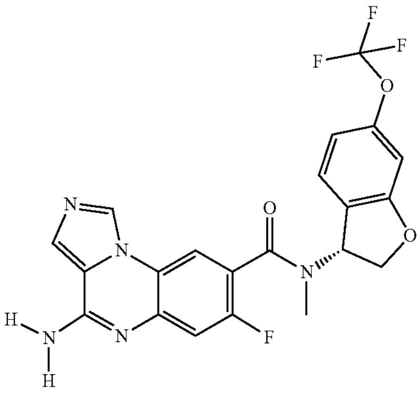 [SMILES: CN(C(=O)c1cc2c(cc1F)nc(N)c1cncn12)[C@H]1COc2cc(OC(F)(F)F)ccc21] |
| Ff-559 | 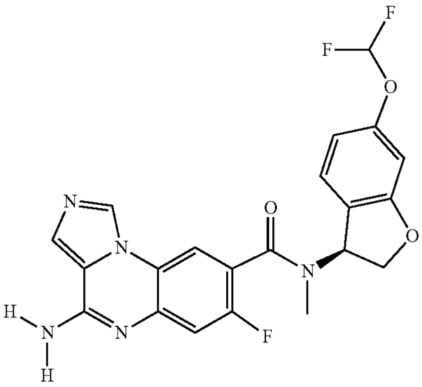 [SMILES: CN(C(=O)c1cc2c(cc1F)nc(N)c1cncn12)[C@@H]1COc2cc(OC(F)F)ccc21] |
| Ff-560 | 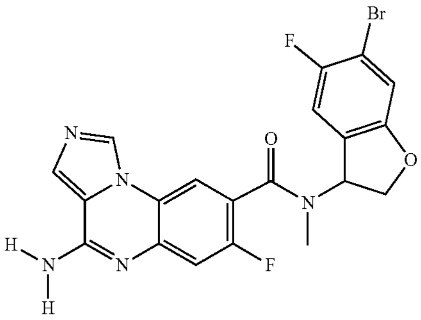 [SMILES: CN(C(=O)c1cc2c(cc1F)nc(N)c1cncn12)C1COc2cc(Br)c(F)cc21] |

TABLE 1B-continued
| Compounds | |
|---|---|
| Example | Structure |
| Ff-561 | 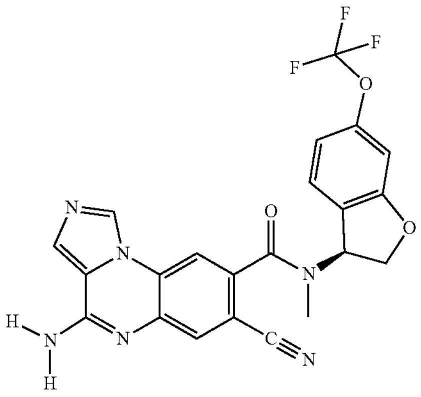 [SMILES: CN(C(=O)c1cc2c(cc1C#N)nc(N)c1cncn12)[C@@H]1COc2cc(OC(F)(F)F)ccc21] |
| Ff-562 | 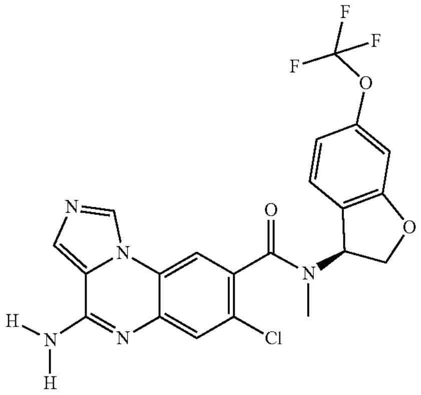 [SMILES: CN(C(=O)c1cc2c(cc1Cl)nc(N)c1cncn12)[C@@H]1COc2cc(OC(F)(F)F)ccc21] |
| Ff-563 | 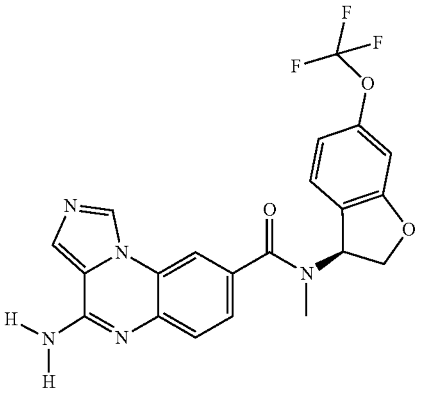 |

TABLE 1B-continued
| Compounds | |
|---|---|
| Example | Structure |
| Ff-564 | 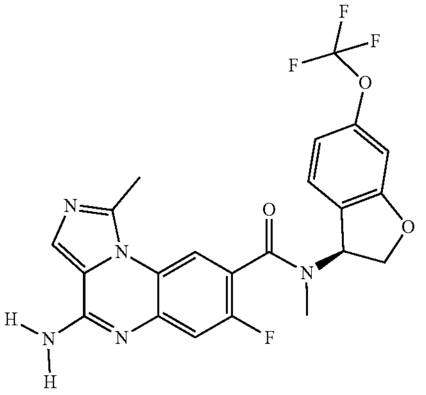 [SMILES: Cc1ncc2c(N)nc3cc(F)c(C(=O)N(C)[C@@H]4COc5cc(OC(F)(F)F)ccc54)cc3n12] |
| Ff-565 | 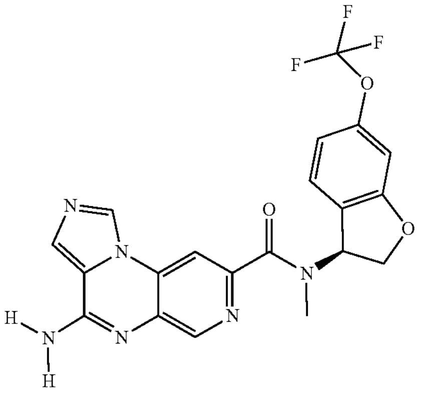 [SMILES: CN(C(=O)c1cc2c(cn1)nc(N)c1cncn12)[C@@H]1COc2cc(OC(F)(F)F)ccc21] |
| Ff-566 | 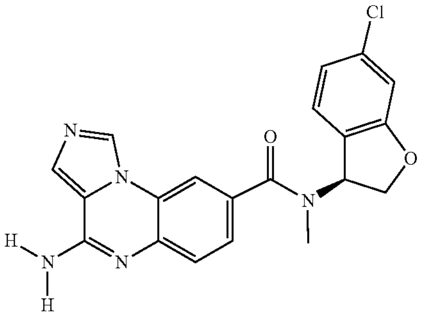 |
| Ff-567 | 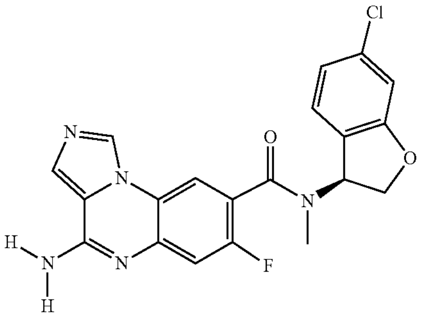 [SMILES: CN(C(=O)c1cc2c(cc1F)nc(N)c1cncn12)[C@@H]1COc2cc(Cl)ccc21] |

TABLE 1B-continued
| Compounds | |
|---|---|
| Example | Structure |
| Ff-568 | 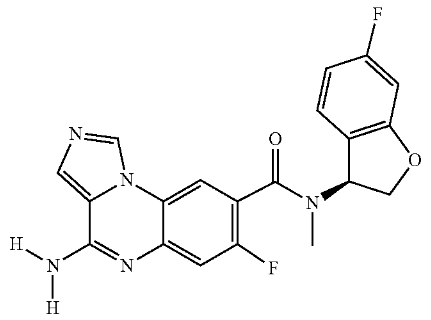 [SMILES: CN(C(=O)c1cc2c(cc1F)nc(N)c1cncn12)[C@@H]1COc2cc(F)ccc21] |
| Ff-569 | 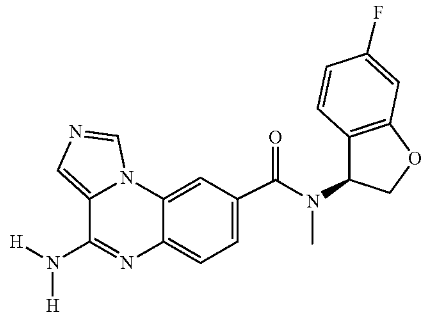 [SMILES: CN(C(=O)c1ccc2nc(N)c3cncn3c2c1)[C@@H]1COc2cc(F)ccc21] |
| Ff-570 | 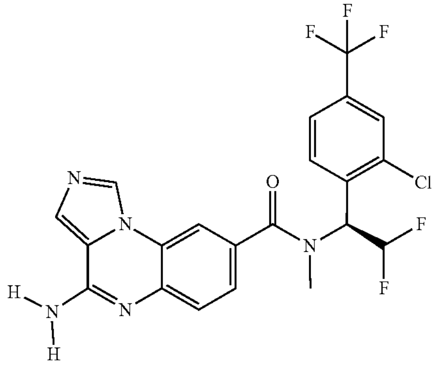 [SMILES: CN(C(=O)c1ccc2nc(N)c3cncn3c2c1)[C@@H](c1ccc(C(F)(F)F)cc1Cl)C(F)F] |
| Ff-571 | 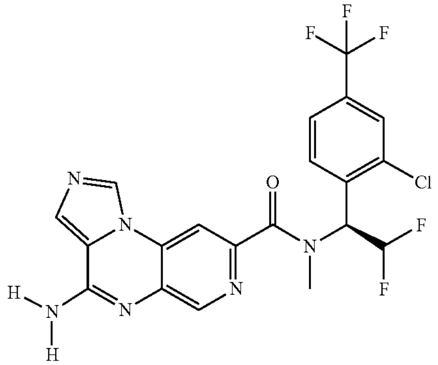 [SMILES: CN(C(=O)c1cc2c(cn1)nc(N)c1cncn12)[C@@H](c1ccc(C(F)(F)F)cc1Cl)C(F)F] |

TABLE 1B-continued
| Compounds | |
| --- | --- |
| Example | Structure |
| Ff-572 | 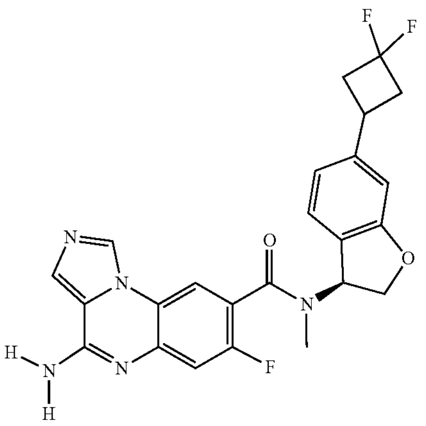 [SMILES: CN(C(=O)c1cc2c(cc1F)nc(N)c1cncn12)[C@@H]1COc2cc(C3CC(F)(F)C3)ccc21] |
| Ff-573 | 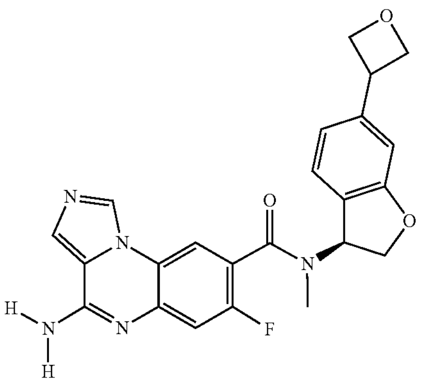 [SMILES: CN(C(=O)c1cc2c(cc1F)nc(N)c1cncn12)[C@@H]1COc2cc(C3COC3)ccc21] |
| Ff-574 | 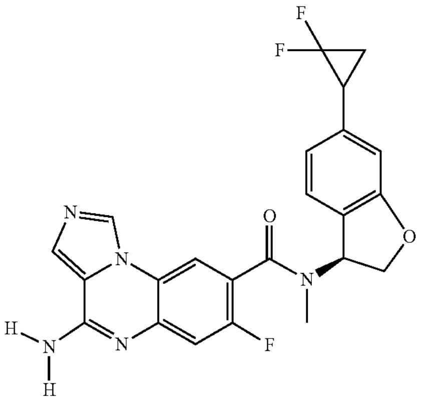 [SMILES: CN(C(=O)c1cc2c(cc1F)nc(N)c1cncn12)[C@@H]1COc2cc(C3CC3(F)F)ccc21] |

TABLE 1B-continued
| Compounds | |
|---|---|
| Example | Structure |
| Ff-575 | 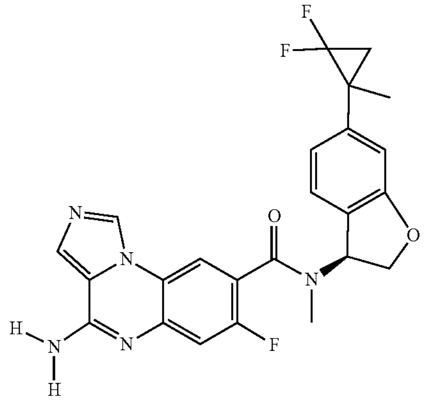 |
| Ff-576 | 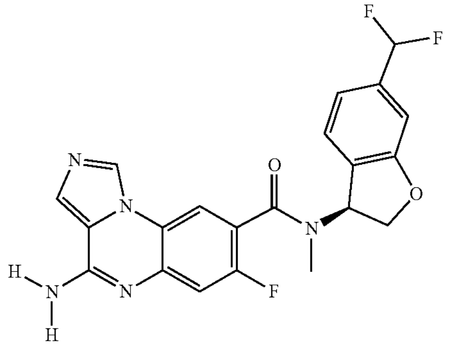 [SMILES: CN(C(=O)c1cc2c(cc1F)nc(N)c1cncn12)[C@@H]1COc2cc(C(F)F)ccc21] |
| Ff-577 | 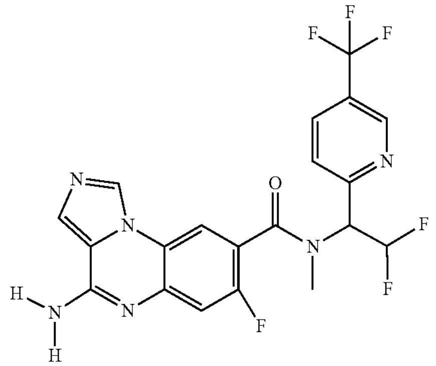 [SMILES: CN(C(=O)c1cc2c(cc1F)nc(N)c1cncn12)C(c1ccc(C(F)(F)F)cn1)C(F)F] |
| Ff-579 | 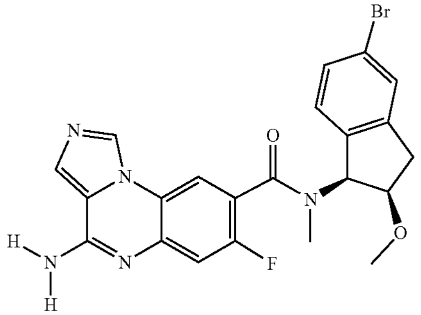 [SMILES: CO[C@@H]1Cc2cc(Br)ccc2[C@@H]1N(C)C(=O)c1cc2c(cc1F)nc(N)c1cncn12] |

TABLE 1B-continued
| Compounds | |
|---|---|
| Example | Structure |
| Ff-580 | 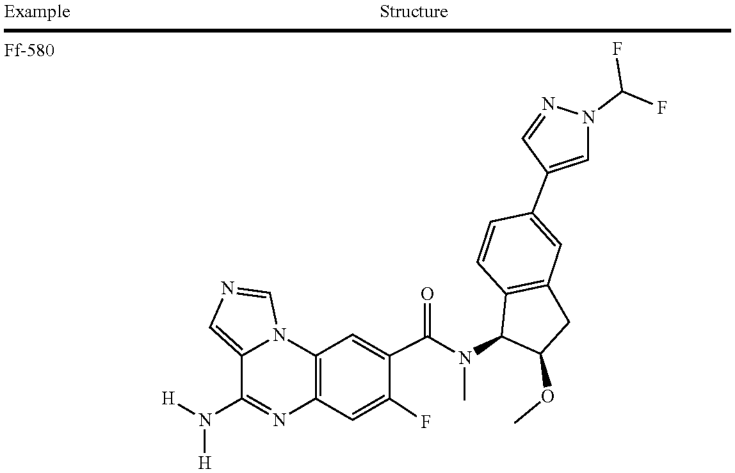 |
| Ff-581 | 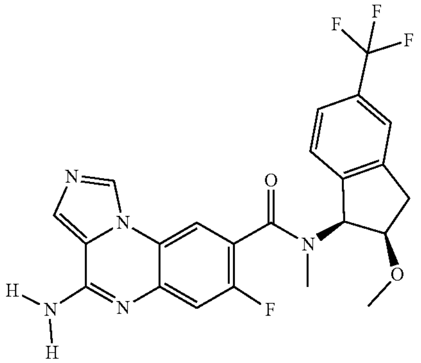 [SMILES: CO[C@@H]1Cc2cc(C(F)(F)F)ccc2[C@@H]1N(C)C(=O)c1cc2c(cc1F)nc(N)c1cncn12] |
| Ff-582 | 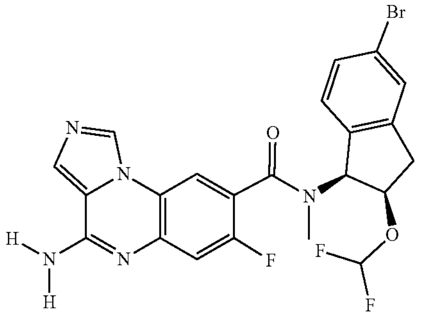 [SMILES: CN(C(=O)c1cc2c(cc1F)nc(N)c1cncn12)[C@H]1c2ccc(Br)cc2C[C@H]1OC(F)F] |
| Ff-583 | 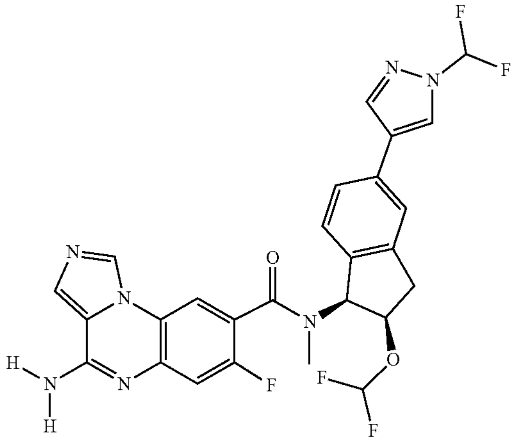 [SMILES: CN(C(=O)c1cc2c(cc1F)nc(N)c1cncn12)[C@H]1c2ccc(-c3cnn(C(F)F)c3)cc2C[C@H]1OC(F)F] |

TABLE 1B-continued
| Compounds | |
| --- | --- |
| Example | Structure |
| Ff-584 | 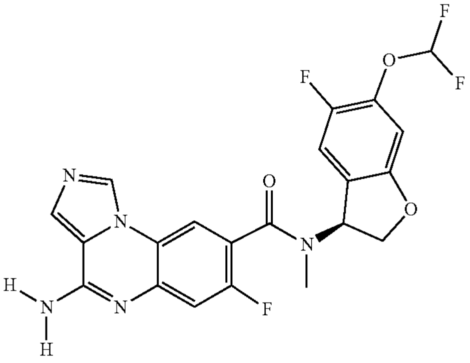 [SMILES: CN(C(=O)c1cc2c(cc1F)nc(N)c1cncn12)[C@@H]1COc2cc(OC(F)F)c(F)cc21] |
| Ff-585 | 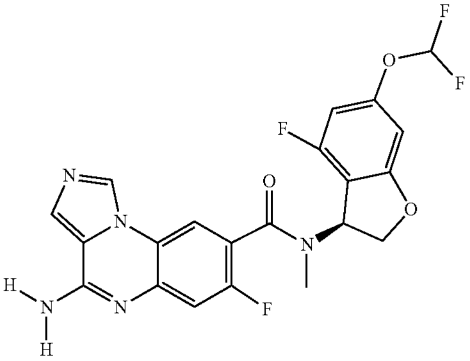 [SMILES: CN(C(=O)c1cc2c(cc1F)nc(N)c1cncn12)[C@@H]1COc2cc(OC(F)F)cc(F)c21] |
| Ff-589 | 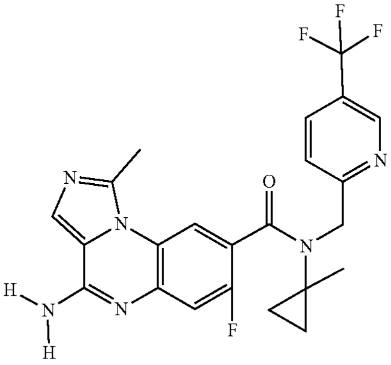 [SMILES: Cc1ncc2c(N)nc3cc(F)c(C(=O)N(Cc4ccc(C(F)(F)F)cn4)C4(C)CC4)cc3n12] |
| Ff-590 | 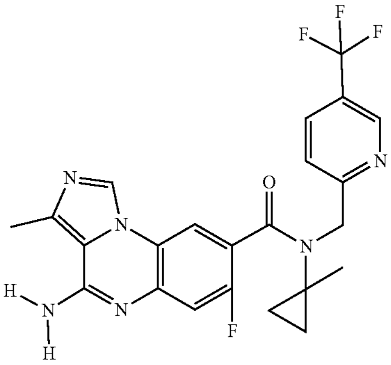 [SMILES: Cc1ncn2c1c(N)nc1cc(F)c(C(=O)N(Cc3ccc(C(F)(F)F)cn3)C3(C)CC3)cc12] |

TABLE 1B-continued
| Compounds | |
|---|---|
| Example | Structure |
| Ff-591 | 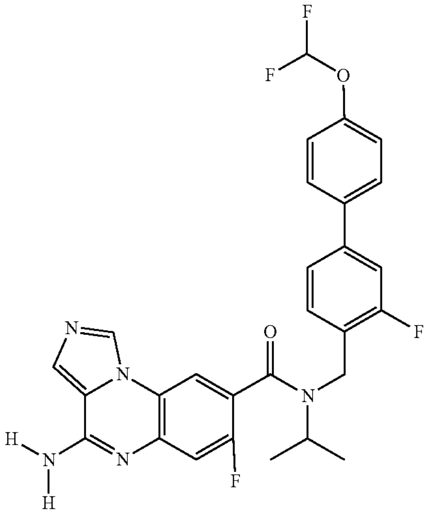 [SMILES: CC(C)N(Cc1ccc(-c2ccc(OC(F)F)cc2)cc1F)C(=O)c1cc2c(cc1F)nc(N)c1cncn12] |
| Ff-592 | 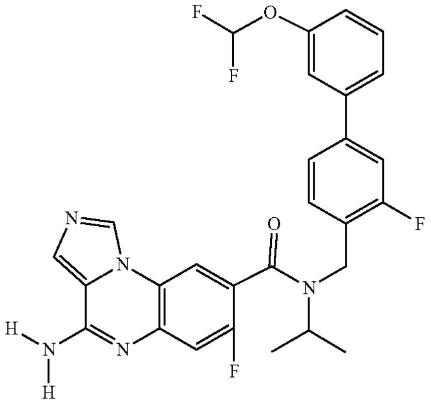 [SMILES: CC(C)N(Cc1ccc(-c2cccc(OC(F)F)c2)cc1F)C(=O)c1cc2c(cc1F)nc(N)c1cncn12] |
| Ff-593 | 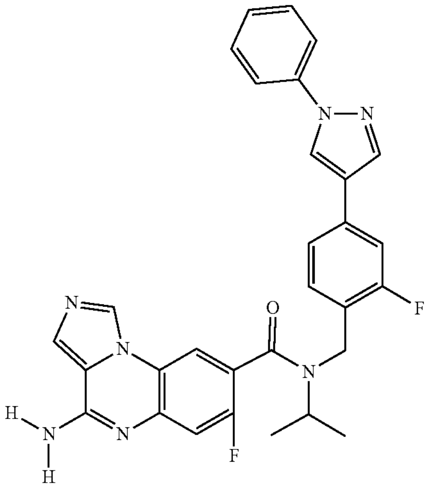 [SMILES: CC(C)N(Cc1ccc(-c2cnn(-c3ccccc3)c2)cc1F)C(=O)c1cc2c(cc1F)nc(N)c1cncn12] |

TABLE 1B-continued
| Compounds | |
|---|---|
| Example | Structure |
| Ff-594 | 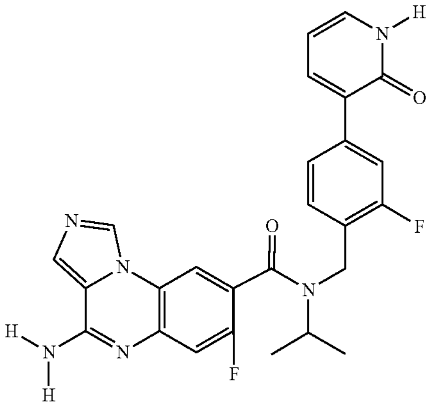 [SMILES: CC(C)N(Cc1ccc(-c2ccc[nH]c2=O)cc1F)C(=O)c1cc2c(cc1F)nc(N)c1cncn12] |
| Ff-596 | 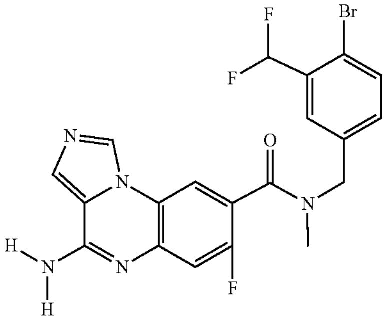 [SMILES: CN(Cc1ccc(Br)c(C(F)F)c1)C(=O)c1cc2c(cc1F)nc(N)c1cncn12] |
| Ff-597 | 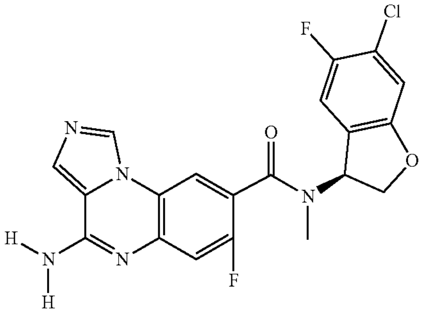 [SMILES: CN(C(=O)c1cc2c(cc1F)nc(N)c1cncn12)[C@@H]1COc2cc(Cl)c(F)cc21] |
| Ff-600 | 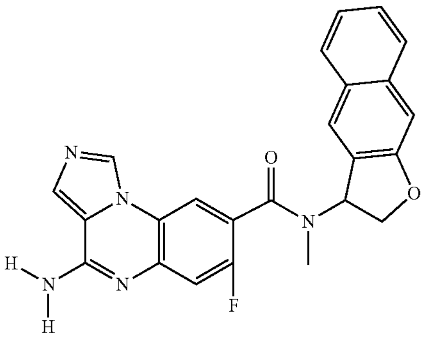 [SMILES: CN(C(=O)c1cc2c(cc1F)nc(N)c1cncn12)C1COc2cc3ccccc3cc21] |

TABLE 1B-continued
| Compounds | |
|---|---|
| Example | Structure |
| Ff-601 | 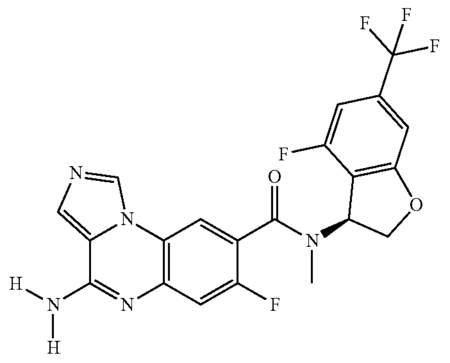 [SMILES: CN(C(=O)c1cc2c(cc1F)nc(N)c1cncn12)[C@@H]1COc2cc(C(F)(F)F)cc(F)c21] |
| Ff-604 | 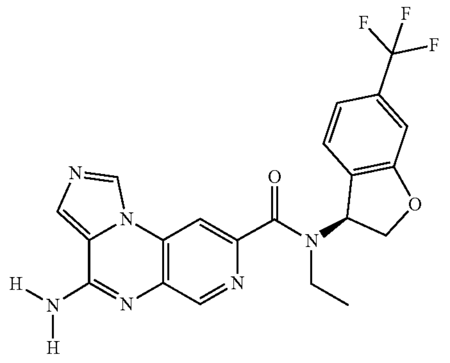 [SMILES: CCN(C(=O)c1cc2c(cn1)nc(N)c1cncn12)[C@@H]1COc2cc(C(F)(F)F)ccc21] |
| Ff-605 | 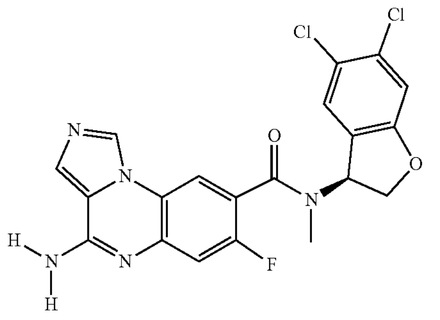 [SMILES: CN(C(=O)c1cc2c(cc1F)nc(N)c1cncn12)[C@@H]1COc2cc(Cl)c(Cl)cc21] |
| Ff-606 | 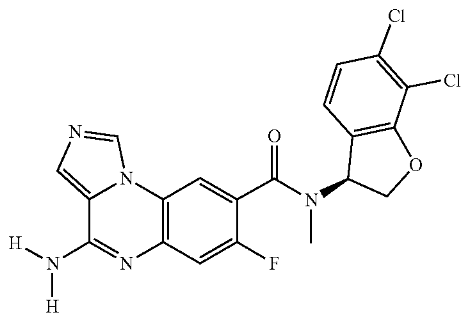 [SMILES: CN(C(=O)c1cc2c(cc1F)nc(N)c1cncn12)[C@@H]1COc2c1ccc(Cl)c2Cl] |

TABLE 1B-continued
| Compounds | |
|---|---|
| Example | Structure |
| Ff-607 | 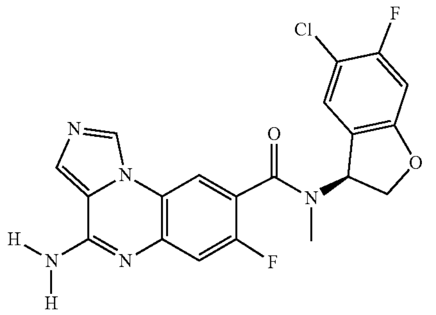 [SMILES: CN(C(=O)c1cc2c(cc1F)nc(N)c1cncn12)[C@@H]1COc2cc(F)c(Cl)cc21] |
| Ff-608 | 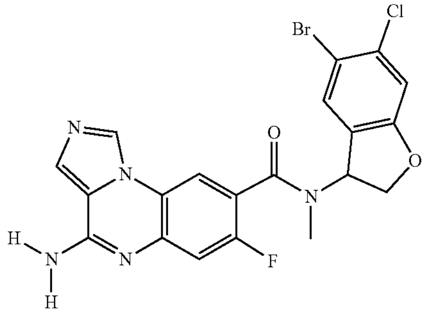 [SMILES: CN(C(=O)c1cc2c(cc1F)nc(N)c1cncn12)C1COc2cc(Cl)c(Br)cc21] |
| Ff-609 | 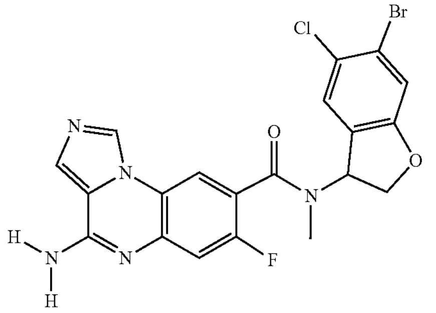 [SMILES: CN(C(=O)c1cc2c(cc1F)nc(N)c1cncn12)C1COc2cc(Br)c(Cl)cc21] |
| Ff-610 | 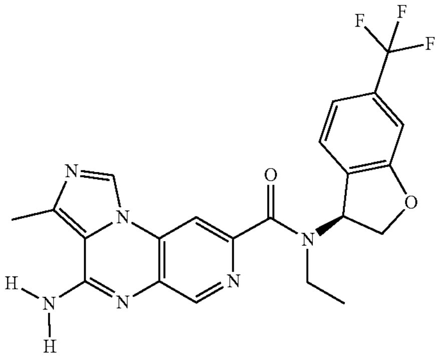 |

TABLE 1B-continued
| Compounds | |
|---|---|
| Example | Structure |
| Ff-613 | 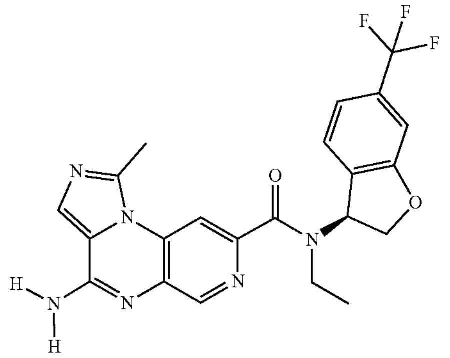 [SMILES: CCN(C(=O)c1cc2c(cn1)nc(N)c1cnc(C)n12)[C@@H]1COc2cc(C(F)(F)F)ccc21] |
| Ff-614 | 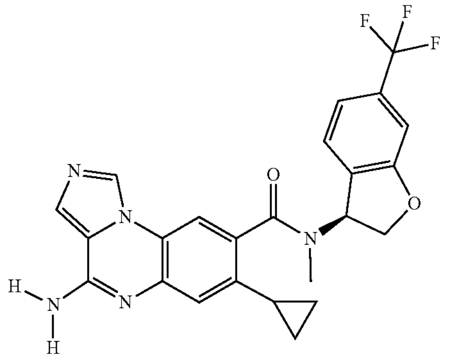 [SMILES: CN(C(=O)c1cc2c(cc1C1CC1)nc(N)c1cncn12)[C@@H]1COc2cc(C(F)(F)F)ccc21] |
| Ff-641 | 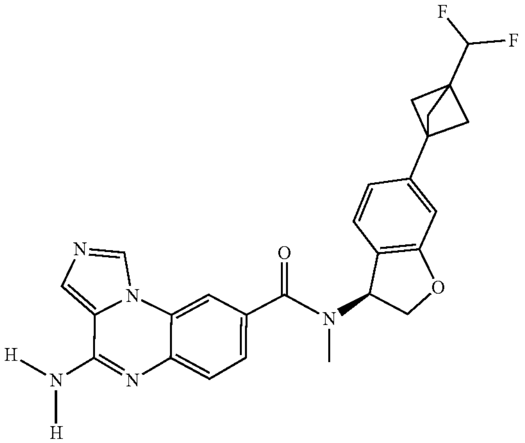 [SMILES: CN(C(=O)c1ccc2nc(N)c3cncn3c2c1)[C@@H]1COc2cc(C34CC(C(F)F)(C3)C4)ccc21] |

TABLE 1B-continued
| Compounds | |
|---|---|
| Example | Structure |
| Ff-642 | 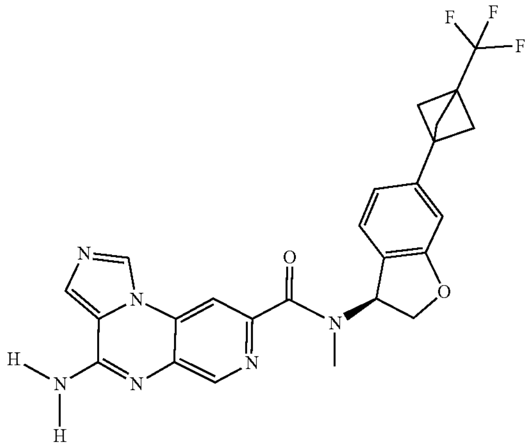 [SMILES: CN(C(=O)c1cc2c(cn1)nc(N)c1cncn12)[C@@H]1COc2cc(C34CC(C(F)(F)F)(C3)C4)ccc21] |
| Ff-652 | 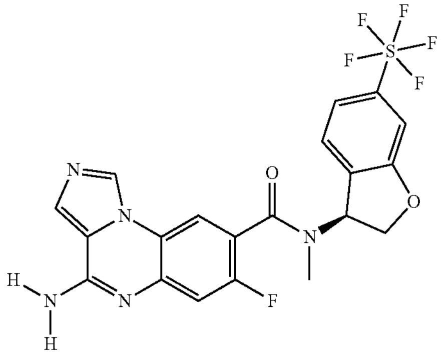 [SMILES: CN(C(=O)c1cc2c(cc1F)nc(N)c1cncn12)[C@@H]1COc2cc(S(F)(F)(F)(F)F)ccc21] |
| Ff-653 | 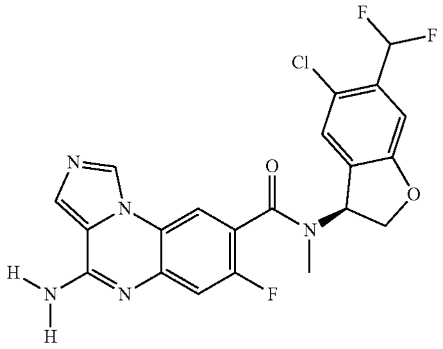 [SMILES: CN(C(=O)c1cc2c(cc1F)nc(N)c1cncn12)[C@@H]1COc2cc(C(F)F)c(Cl)cc21] |
| Ff-654 | 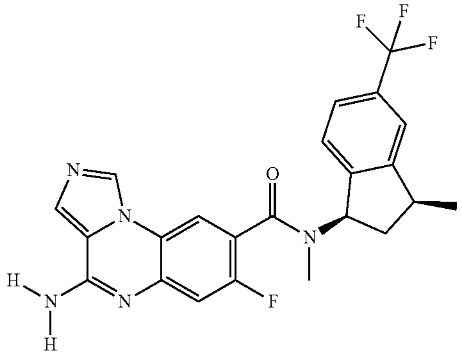 [SMILES: C[C@H]1C[C@@H](N(C)C(=O)c2cc3c(cc2F)nc(N)c2cncn23)c2ccc(C(F)(F)F)cc21] |

TABLE 1B-continued
| Compounds | |
|---|---|
| Example | Structure |
| Ff-668 | 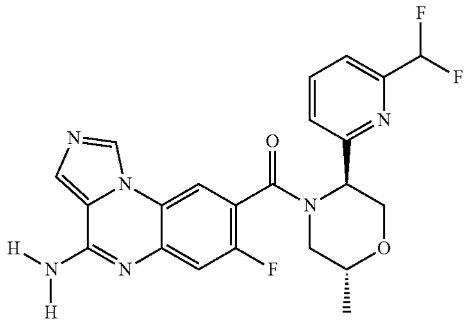 [SMILES: C[C@@H]1CN(C(=O)c2cc3c(cc2F)nc(N)c2cncn23)[C@@H](c2cccc(C(F)F)n2)CO1] |
| Ff-671 | 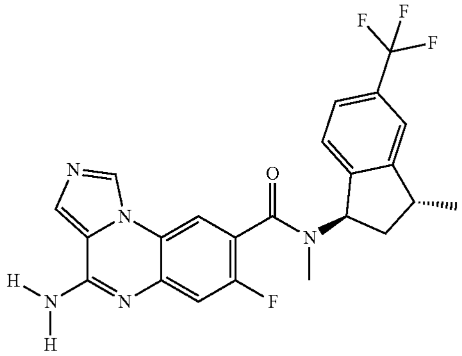 [SMILES: C[C@@H]1C[C@@H](N(C)C(=O)c2cc3c(cc2F)nc(N)c2cncn23)c2ccc(C(F)(F)F)cc21] |
| Ff-672 | 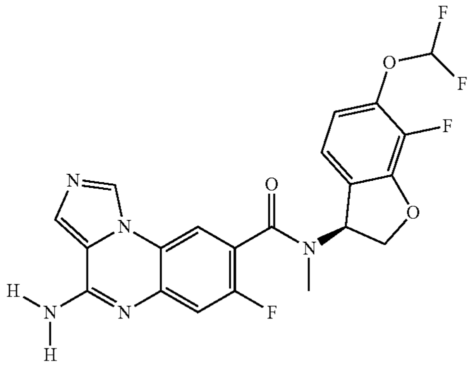 [SMILES: CN(C(=O)c1cc2c(cc1F)nc(N)c1cncn12)[C@@H]1COc2c1ccc(OC(F)F)c2F] |
| Ff-673 | 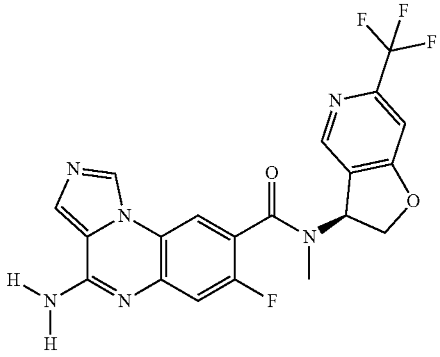 [SMILES: CN(C(=O)c1cc2c(cc1F)nc(N)c1cncn12)[C@@H]1COc2cc(C(F)(F)F)ncc21] |

TABLE 1B-continued
| Compounds | |
|---|---|
| Example | Structure |
| Ff-674 | 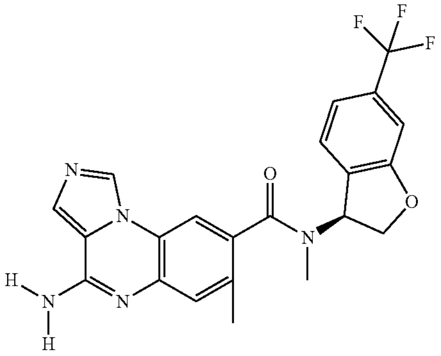 [SMILES: Cc1cc2nc(N)c3cncn3c2cc1C(=O)N(C)[C@@H]1COc2cc(C(F)(F)F)ccc21] |
| Fg-1 | 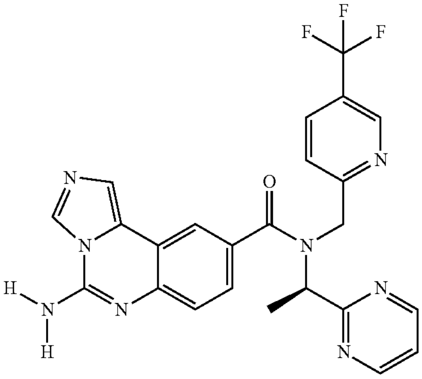 [SMILES: C[C@H](c1ncccn1)N(Cc1ccc(C(F)(F)F)cn1)C(=O)c1ccc2nc(N)n3cncc3c2c1] |
| Fg-2 | 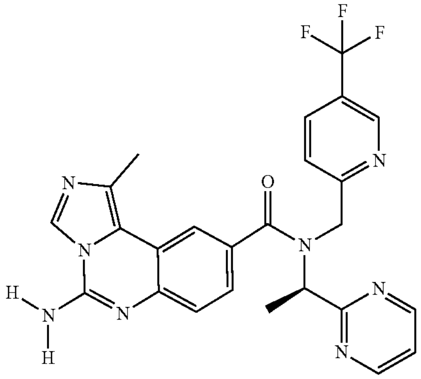 [SMILES: Cc1ncn2c(N)nc3ccc(C(=O)N(Cc4ccc(C(F)(F)F)cn4)[C@H](C)c4ncccn4)cc3c12] |
| Fg-3 | 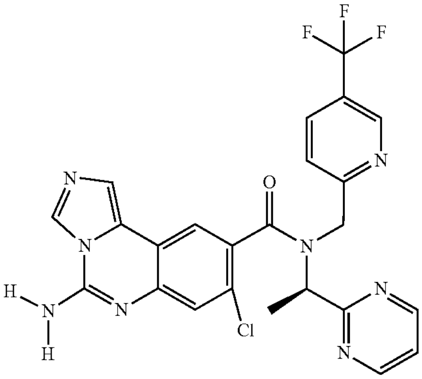 |

TABLE 1B-continued
| Compounds | |
|---|---|
| Example | Structure |
| Fg-4 | 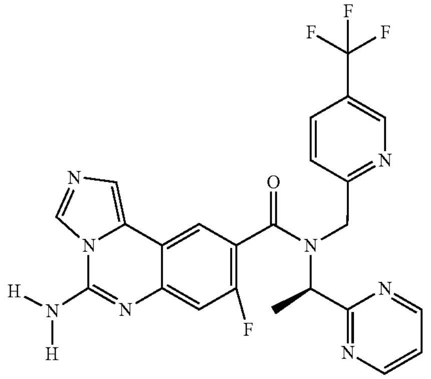 [SMILES: C[C@H](c1ncccn1)N(Cc1ccc(C(F)(F)F)cn1)C(=O)c1cc2c(cc1F)nc(N)n1cncc21] |
| Fg-5 | 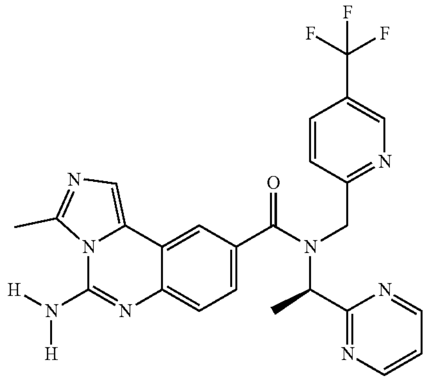 [SMILES: Cc1ncc2c3cc(C(=O)N(Cc4ccc(C(F)(F)F)cn4)[C@H](C)c4ncccn4)ccc3nc(N)n12] |
| Fg-6 | 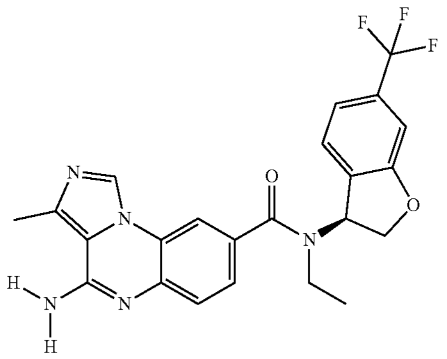 [SMILES: CCN(C(=O)c1ccc2nc(N)c3c(C)ncn3c2c1)[C@@H]1COc2cc(C(F)(F)F)ccc21] |
| Fg-7 | 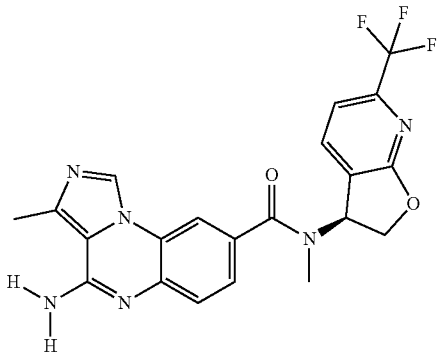 [SMILES: Cc1ncn2c1c(N)nc1ccc(C(=O)N(C)[C@@H]3COc4nc(C(F)(F)F)ccc43)cc12] |

TABLE 1B-continued
| Compounds | |
|---|---|
| Example | Structure |
| Fg-8 | 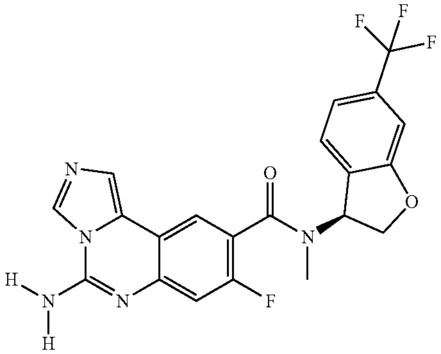 [SMILES: CN(C(=O)c1cc2c(cc1F)nc(N)n1cncc21)[C@@H]1COc2cc(C(F)(F)F)ccc21] |
| Fg-9 | 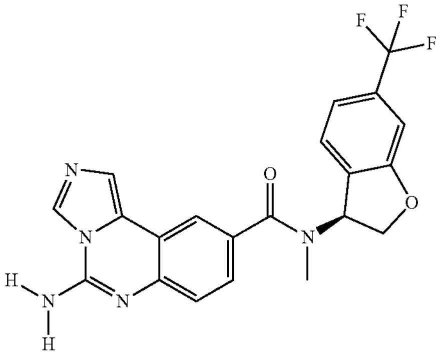 [SMILES: CN(C(=O)c1ccc2nc(N)n3cncc3c2c1)[C@@H]1COc2cc(C(F)(F)F)ccc21] |
| Fg-10 | 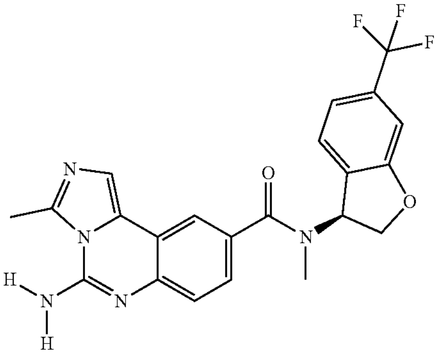 [SMILES: Cc1ncc2c3cc(C(=O)N(C)[C@@H]4COc5cc(C(F)(F)F)ccc54)ccc3nc(N)n12] |
| Fg-11 | 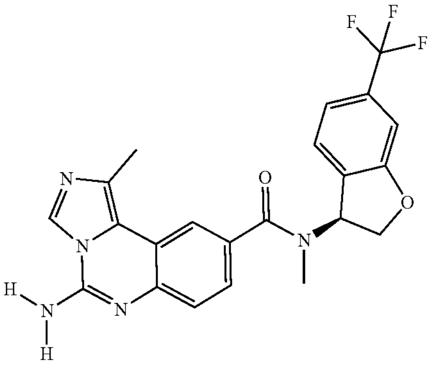 [SMILES: Cc1ncn2c(N)nc3ccc(C(=O)N(C)[C@@H]4COc5cc(C(F)(F)F)ccc54)cc3c12] |

TABLE 1B-continued
| Compounds | |
|---|---|
| Example | Structure |
| Fg-12 | 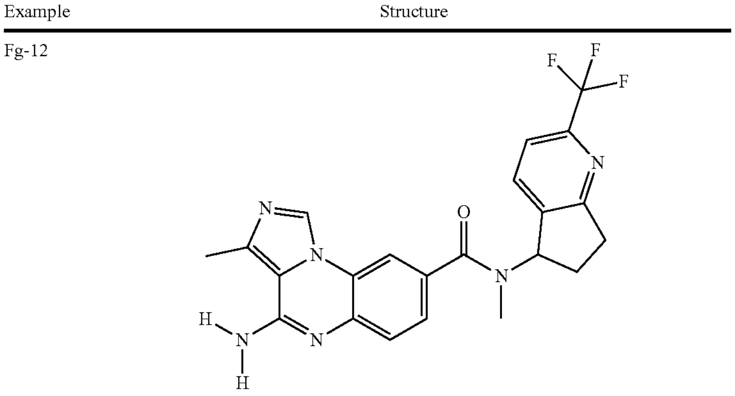 |
| Fg-13 | 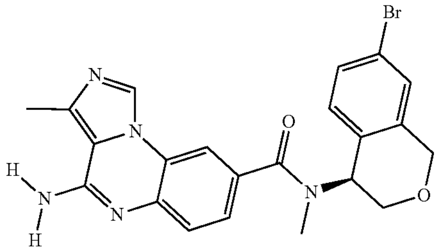 [SMILES: Cc1ncn2c1c(N)nc1ccc(C(=O)N(C)[C@@H]3COCc4cc(Br)ccc43)cc12] |
| Fg-14 | 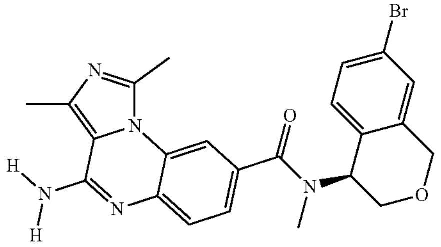 [SMILES: Cc1nc(C)n2c1c(N)nc1ccc(C(=O)N(C)[C@@H]3COCc4cc(Br)ccc43)cc12] |
| Fg-15 | 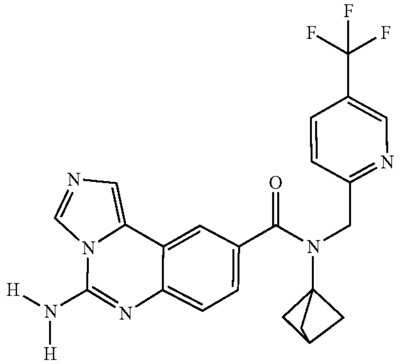 [SMILES: Nc1nc2ccc(C(=O)N(Cc3ccc(C(F)(F)F)cn3)C34CC(C3)C4)cc2c2cncn12] |
| Fg-16 | 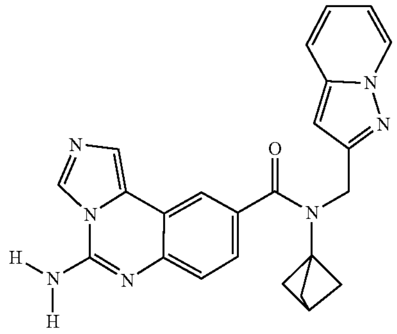 [SMILES: Nc1nc2ccc(C(=O)N(Cc3cc4ccccn4n3)C34CC(C3)C4)cc2c2cncn12] |

TABLE 1B-continued
| Compounds | |
| --- | --- |
| Example | Structure |
| Fg-17 | 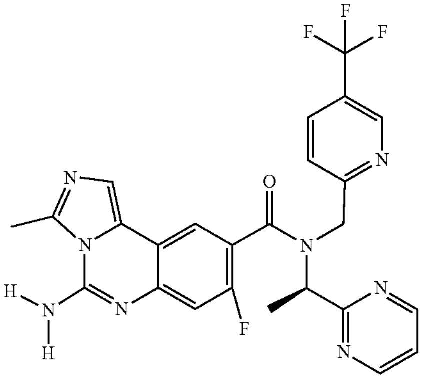 [SMILES: Cc1ncc2c3cc(C(=O)N(Cc4ccc(C(F)(F)F)cn4)[C@H](C)c4ncccn4)c(F)cc3nc(N)n12] |
| Fg-18 | 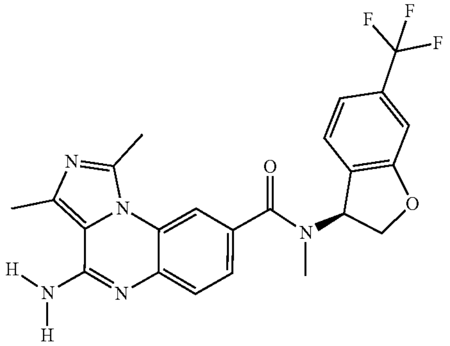 [SMILES: Cc1nc(C)n2c1c(N)nc1ccc(C(=O)N(C)[C@@H]3COc4cc(C(F)(F)F)ccc43)cc12] |
| Fg-48 | 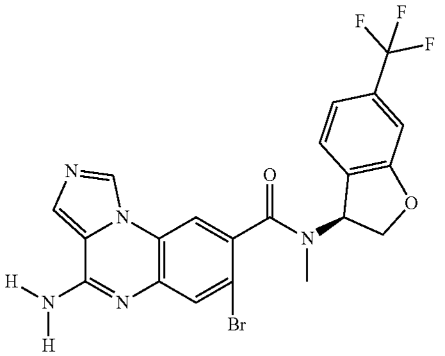 [SMILES: CN(C(=O)c1cc2c(cc1Br)nc(N)c1cncn12)[C@@H]1COc2cc(C(F)(F)F)ccc21] |
| Fg-49 | 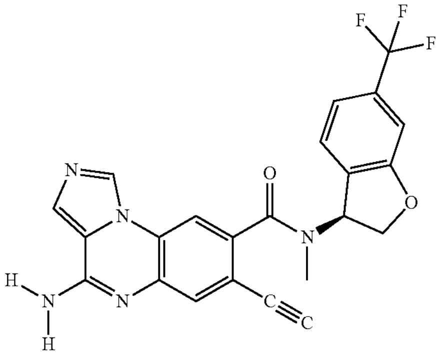 |

TABLE 1B-continued
| Compounds | |
|---|---|
| Example | Structure |
| Fg-51 | 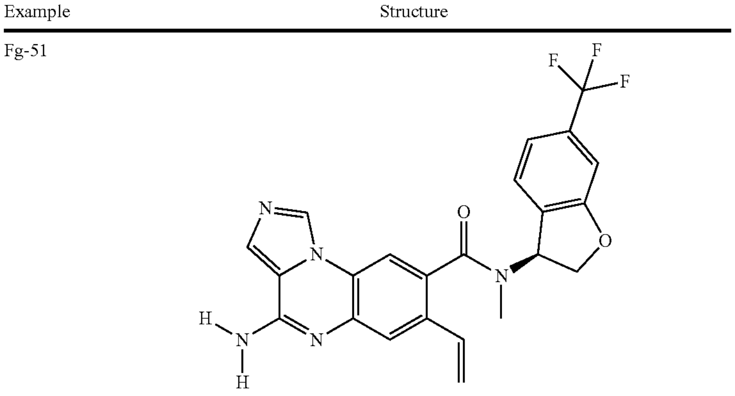 |
| Fg-52 | 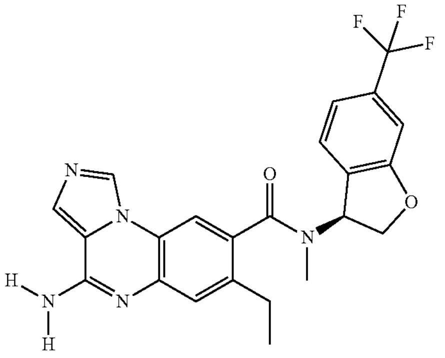 [SMILES: CCc1cc2nc(N)c3cncn3c2cc1C(=O)N(C)[C@@H]1COc2cc(C(F)(F)F)ccc21] |
TABLE 1C
| Compounds | |
|---|---|
| Example | Structure |
| Ff-81 | 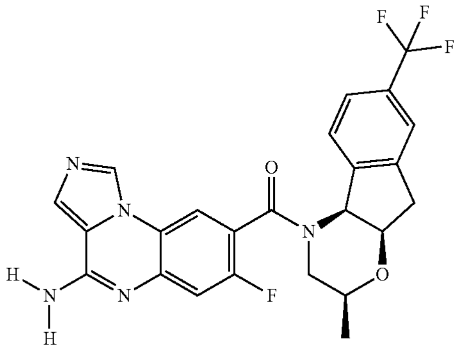 [SMILES: C[C@H]1CN(C(=O)c2cc3c(cc2F)nc(N)c2cncn23)[C@H]2c3ccc(C(F)(F)F)cc3C[C@H]2O1] |

TABLE 1C-continued
| Compounds | |
|---|---|
| Example | Structure |
| Ff-104 | 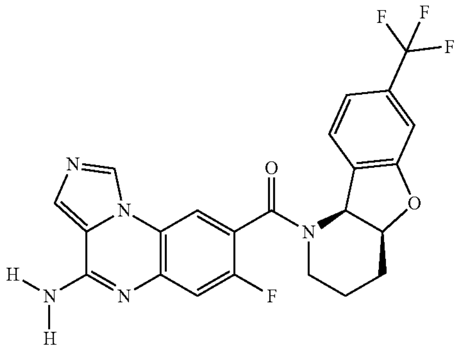 [SMILES: Nc1nc2cc(F)c(C(=O)N3CCC[C@@H]4Oc5cc(C(F)(F)F)ccc5[C@@H]43)cc2n2cncc12] |
| Ff-110 | 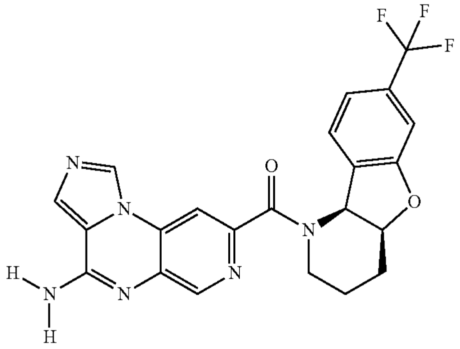 |
| Ff-111 | 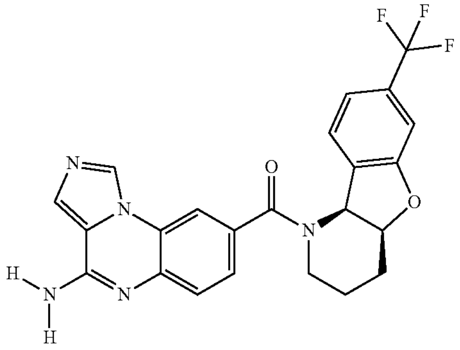 |
| Ff-183 | 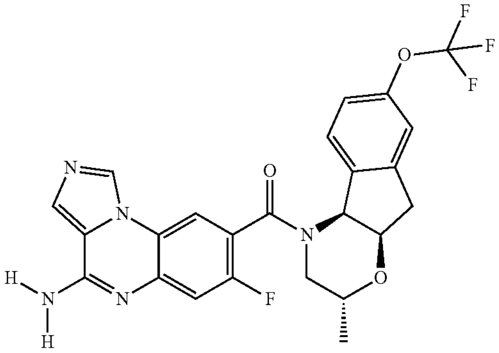 [SMILES: C[C@@H]1CN(C(=O)c2cc3c(cc2F)nc(N)c2cncn23)[C@H]2c3ccc(OC(F)(F)F)cc3C[C@H]2O1] |

TABLE 1C-continued
| Compounds | |
|---|---|
| Example | Structure |
| Ff-197 | 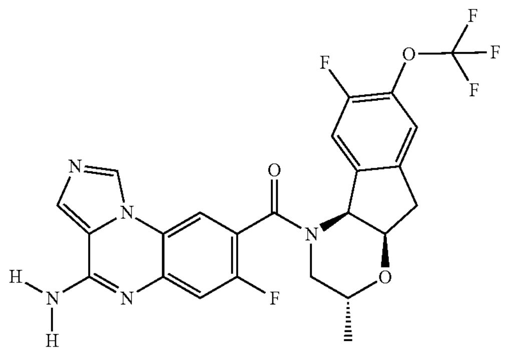 [SMILES: C[C@@H]1CN(C(=O)c2cc3c(cc2F)nc(N)c2cncn23)[C@H]2c3cc(F)c(OC(F)(F)F)cc3C[C@H]2O1] |
| Ff-340 | 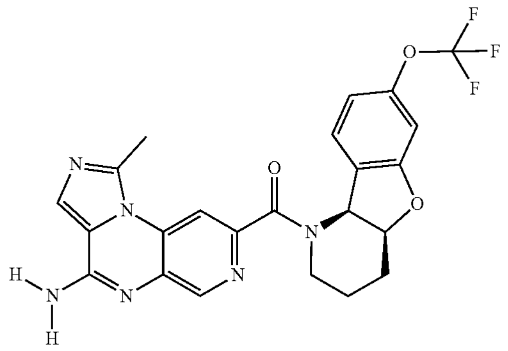 [SMILES: Cc1ncc2c(N)nc3cnc(C(=O)N4CCC[C@@H]5Oc6cc(OC(F)(F)F)ccc6[C@@H]54)cc3n12] |
| Ff-341 | 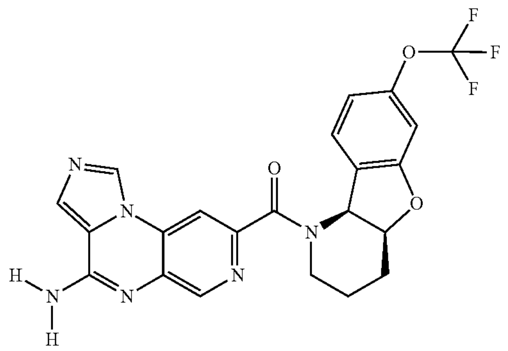 [SMILES: Nc1nc2cnc(C(=O)N3CCC[C@@H]4Oc5cc(OC(F)(F)F)ccc5[C@@H]43)cc2n2cncc12] |
| Ff-367 | 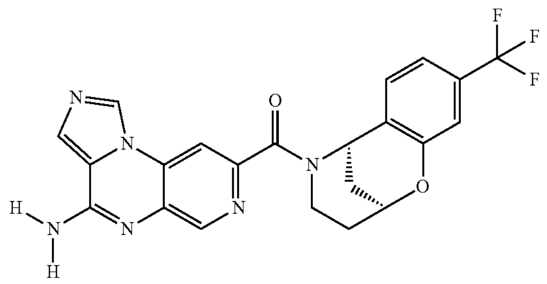 [SMILES: Nc1nc2cnc(C(=O)N3CC[C@H]4C[C@@H]3c3ccc(C(F)(F)F)cc3O4)cc2n2cncc12] |

TABLE 1C-continued
| Compounds | |
|---|---|
| Example | Structure |
| Ff-648 | 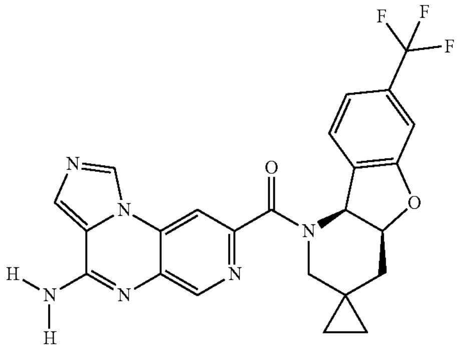 [SMILES: Nc1nc2cnc(C(=O)N3CC4(CC4)C[C@@H]4Oc5cc(C(F)(F)F)ccc5[C@@H]43)cc2n2cncc12] |
| Ff-685 | 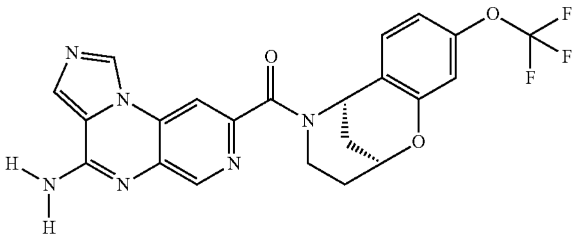 [SMILES: Nc1nc2cnc(C(=O)N3CC[C@H]4C[C@@H]3c3ccc(OC(F)(F)F)cc3O4)cc2n2cncc12] |
| Ff-692 | 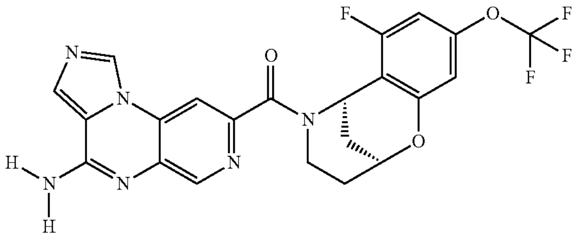 [SMILES: Nc1nc2cnc(C(=O)N3CC[C@H]4C[C@@H]3c3c(F)cc(OC(F)(F)F)cc3O4)cc2n2cncc12] |
| Ff-694 | 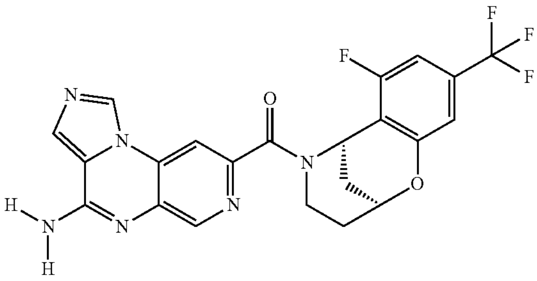 [SMILES: Nc1nc2cnc(C(=O)N3CC[C@H]4C[C@@H]3c3c(F)cc(C(F)(F)F)cc3O4)cc2n2cncc12] |
| Fg-53 | 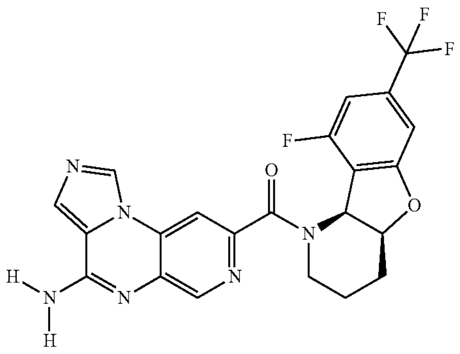 [SMILES: Nc1nc2cnc(C(=O)N3CCC[C@@H]4Oc5cc(C(F)(F)F)cc(F)c5[C@@H]43)cc2n2cncc12] |

TABLE 1C-continued
| Compounds | |
|---|---|
| Example | Structure |
| Fg-55 | 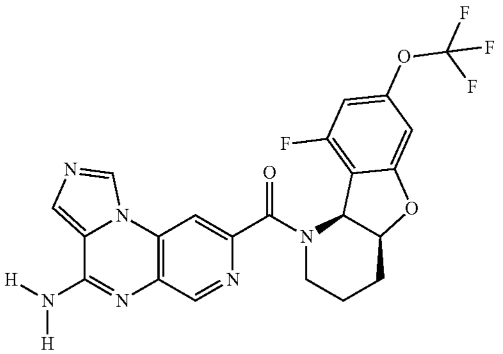 [SMILES: Nc1nc2cnc(C(=O)N3CCC[C@@H]4Oc5cc(OC(F)(F)F)cc(F)c5[C@@H]43)cc2n2cncc12] |
TABLE 1D
| Compounds | |
|---|---|
| Example | Structure |
| Ff-28 | 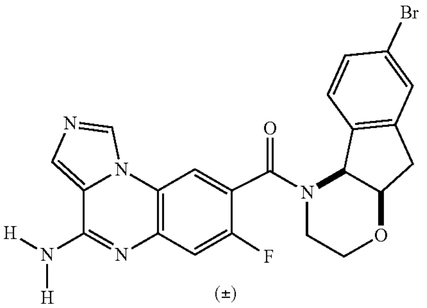 [SMILES: Nc1nc2cc(F)c(C(=O)N3CCO[C@@H]4Cc5cc(Br)ccc5[C@@H]43)cc2n2cncc12] (±) |
| Ff-29 | 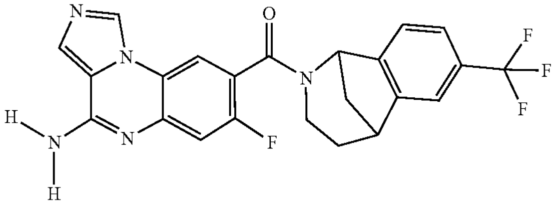 [SMILES: Nc1nc2cc(F)c(C(=O)N3CCC4CC3c3ccc(C(F)(F)F)cc34)cc2n2cncc12] |
| Ff-33 | 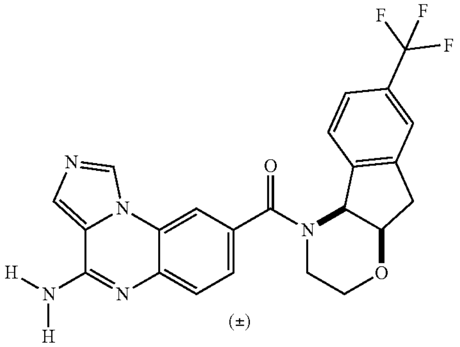 [SMILES: Nc1nc2ccc(C(=O)N3CCO[C@@H]4Cc5cc(C(F)(F)F)ccc5[C@@H]43)cc2n2cncc12] (±) |

TABLE 1D-continued
| Compounds | |
|---|---|
| Example | Structure |
| Ff-34 | 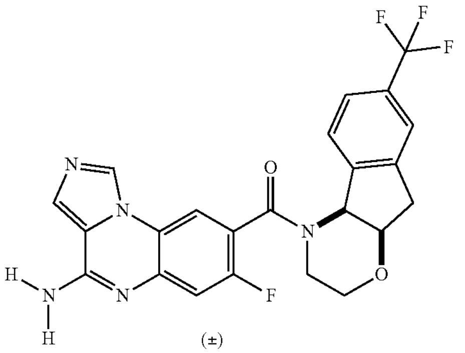 [SMILES: Nc1nc2cc(F)c(C(=O)N3CCO[C@@H]4Cc5cc(C(F)(F)F)ccc5[C@@H]43)cc2n2cncc12] (±) |
| Ff-35 | 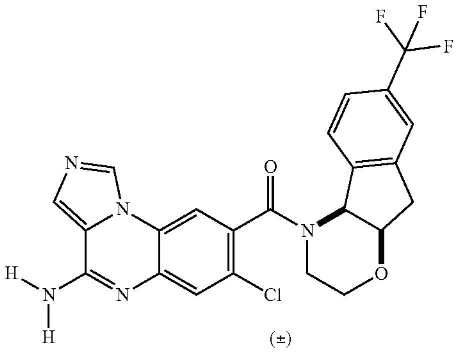 [SMILES: Nc1nc2cc(Cl)c(C(=O)N3CCO[C@@H]4Cc5cc(C(F)(F)F)ccc5[C@@H]43)cc2n2cncc12] (±) |
| Ff-36 | 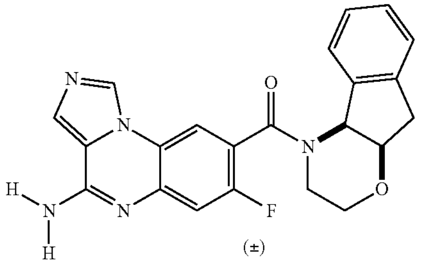 [SMILES: Nc1nc2cc(F)c(C(=O)N3CCO[C@@H]4Cc5ccccc5[C@@H]43)cc2n2cncc12] (±) |
| Ff-37 | 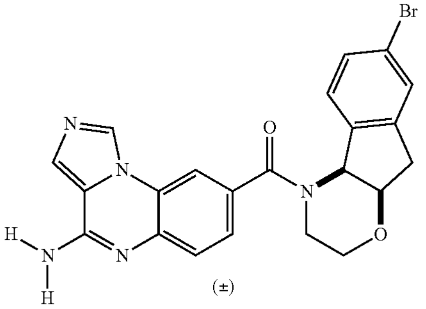 [SMILES: Nc1nc2ccc(C(=O)N3CCO[C@@H]4Cc5cc(Br)ccc5[C@@H]43)cc2n2cncc12] (±) |

TABLE 1D-continued
| Compounds | |
|---|---|
| Example | Structure |
| Ff-43 | 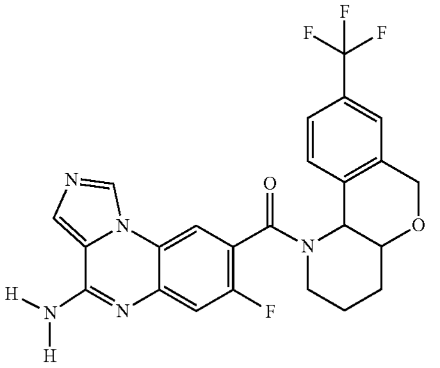 [SMILES: Nc1nc2cc(F)c(C(=O)N3CCCC4OCc5cc(C(F)(F)F)ccc5C43)cc2n2cncc12] |
| Ff-44 | 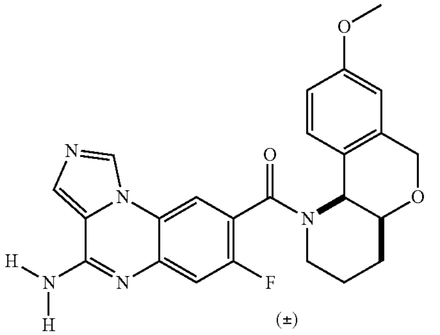 [SMILES: COc1ccc2c(c1)CO[C@H]1CCCN(C(=O)c3cc4c(cc3F)nc(N)c3cncn34)[C@@H]21]<br>(±) |
| Ff-55 | 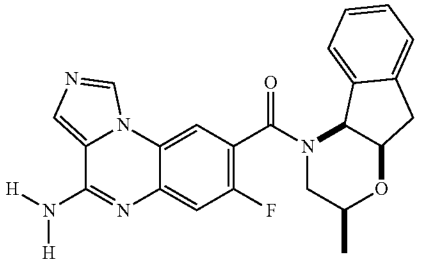<br>(±) |
| Ff-56 | 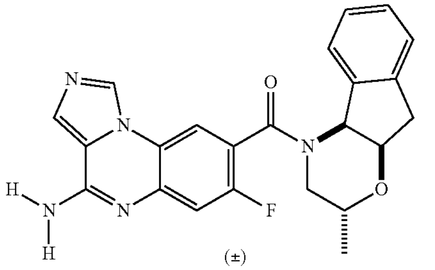 [SMILES: C[C@@H]1CN(C(=O)c2cc3c(cc2F)nc(N)c2cncn23)[C@H]2c3ccccc3C[C@H]2O1]<br>(±) |

TABLE 1D-continued
| Compounds | |
| --- | --- |
| Example | Structure |
| Ff-60 | 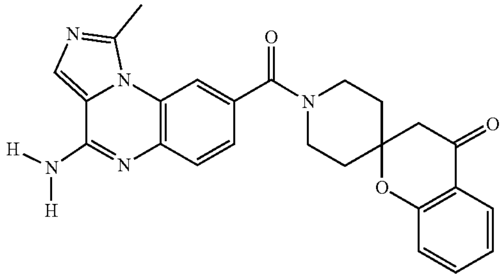 [SMILES: Cc1ncc2c(N)nc3ccc(C(=O)N4CCC5(CC4)CC(=O)c4ccccc4O5)cc3n12] |
| Ff-61 | 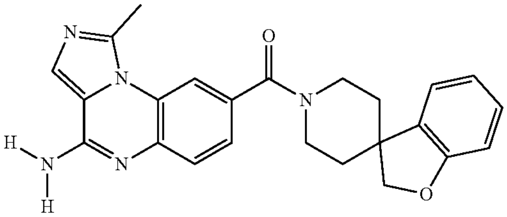 [SMILES: Cc1ncc2c(N)nc3ccc(C(=O)N4CCC5(CC4)COc4ccccc45)cc3n12] |
| Ff-62 | 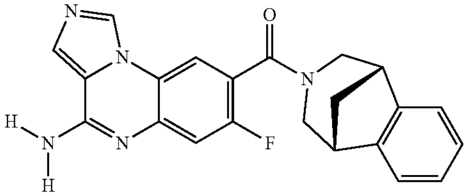 [SMILES: Nc1nc2cc(F)c(C(=O)N3C[C@H]4C[C@@H](C3)c3ccccc34)cc2n2cncc12] |
| Ff-64 | 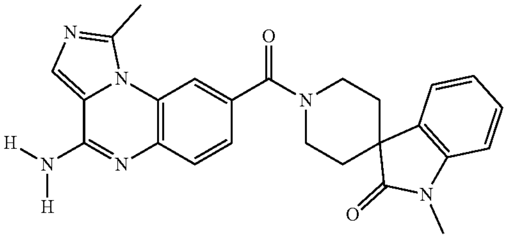 [SMILES: Cc1ncc2c(N)nc3ccc(C(=O)N4CCC5(CC4)C(=O)N(C)c4ccccc45)cc3n12] |
| Ff-65 | 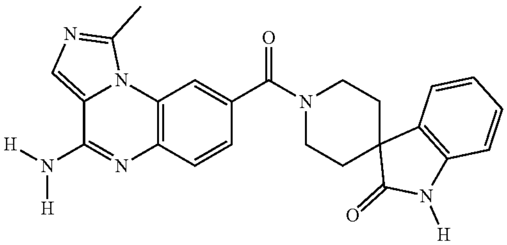 [SMILES: Cc1ncc2c(N)nc3ccc(C(=O)N4CCC5(CC4)C(=O)Nc4ccccc45)cc3n12] |

TABLE 1D-continued
| Compounds | |
|---|---|
| Example | Structure |
| Ff-66 | 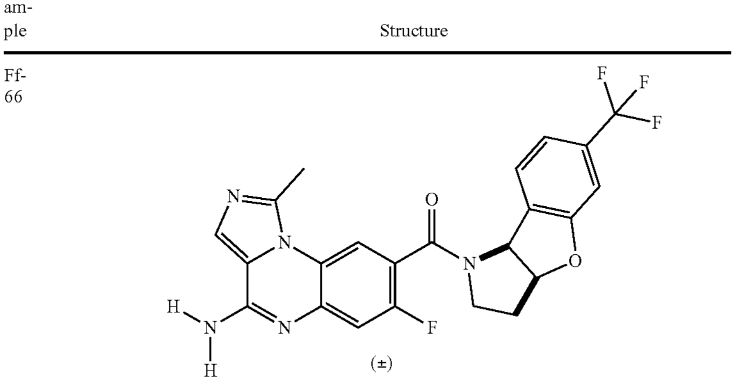 (±) |
| Ff-67 | 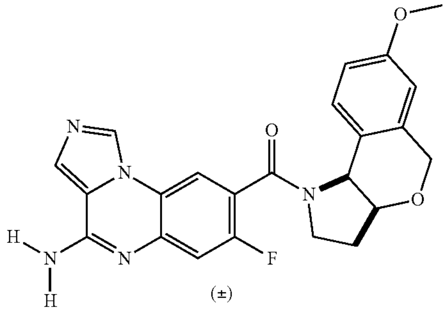 (±) |
| Ff-74 | 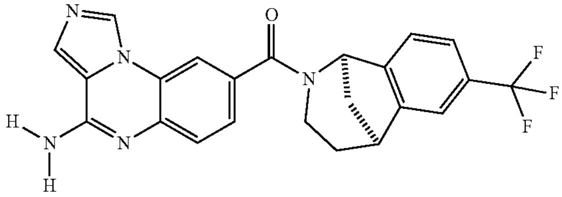 [SMILES: Nc1nc2ccc(C(=O)N3CC[C@H]4C[C@@H]3c3ccc(C(F)(F)F)cc34)cc2n2cncc12] |
| Ff-75 | 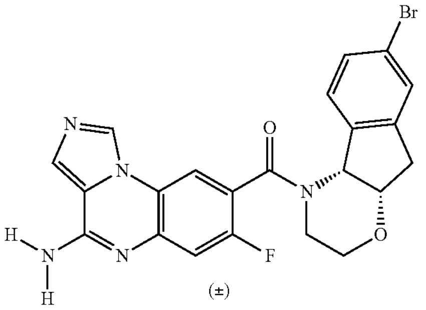 [SMILES: Nc1nc2cc(F)c(C(=O)N3CCO[C@H]4Cc5cc(Br)ccc5[C@H]43)cc2n2cncc12] (±) |
| Ff-76 | 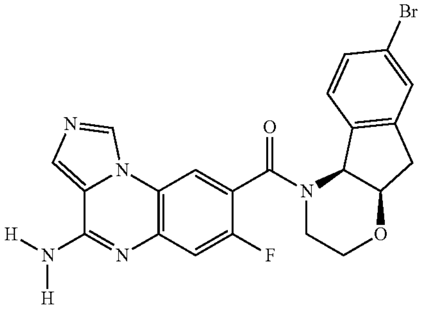 |

TABLE 1D-continued
| Compounds | |
|---|---|
| Example | Structure |
| Ff-77 | 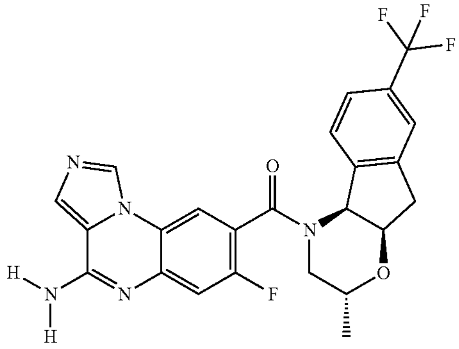 [SMILES: C[C@@H]1CN(C(=O)c2cc3c(cc2F)nc(N)c2cncn23)[C@H]2c3ccc(C(F)(F)F)cc3C[C@H]2O1] |
| Ff-78 | 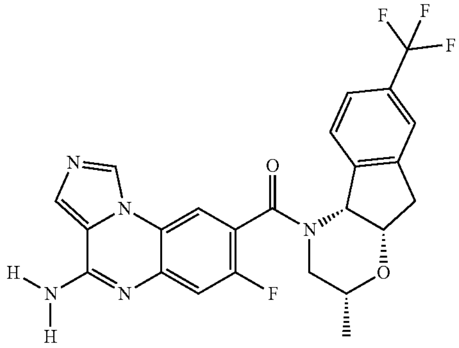 [SMILES: C[C@@H]1CN(C(=O)c2cc3c(cc2F)nc(N)c2cncn23)[C@@H]2c3ccc(C(F)(F)F)cc3C[C@@H]2O1] |
| Ff-80 | 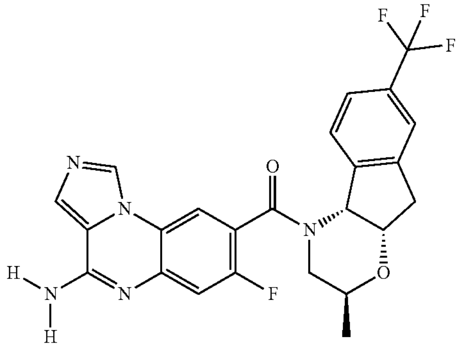 [SMILES: C[C@H]1CN(C(=O)c2cc3c(cc2F)nc(N)c2cncn23)[C@@H]2c3ccc(C(F)(F)F)cc3C[C@@H]2O1] |
| Ff-81 | 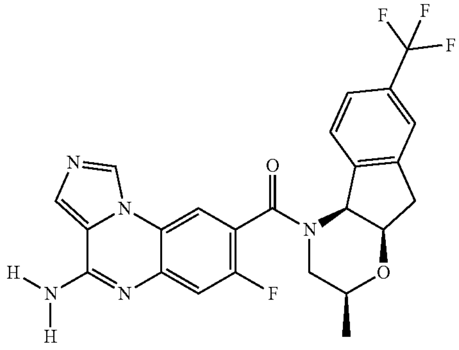 [SMILES: C[C@H]1CN(C(=O)c2cc3c(cc2F)nc(N)c2cncn23)[C@H]2c3ccc(C(F)(F)F)cc3C[C@H]2O1] |

TABLE 1D-continued
| Compounds | |
|---|---|
| Example | Structure |
| Ff-82 | 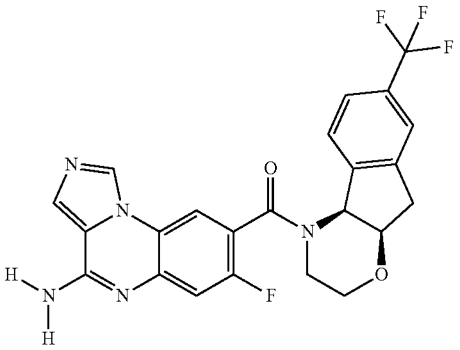 [SMILES: Nc1nc2cc(F)c(C(=O)N3CCO[C@@H]4Cc5cc(C(F)(F)F)ccc5[C@@H]43)cc2n2cncc12] |
| Ff-83 | 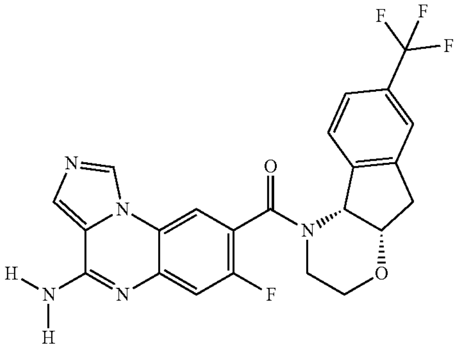 [SMILES: Nc1nc2cc(F)c(C(=O)N3CCO[C@H]4Cc5cc(C(F)(F)F)ccc5[C@H]43)cc2n2cncc12] |
| Ff-85 | 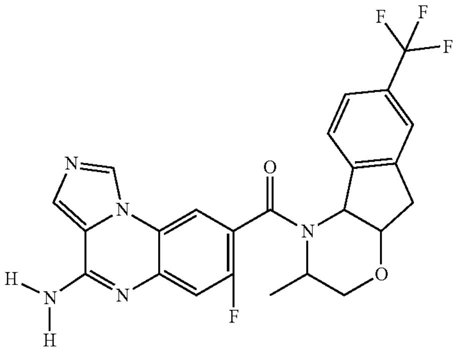 [SMILES: CC1COC2Cc3cc(C(F)(F)F)ccc3C2N1C(=O)c1cc2c(cc1F)nc(N)c1cncn12] |
| Ff-88 | 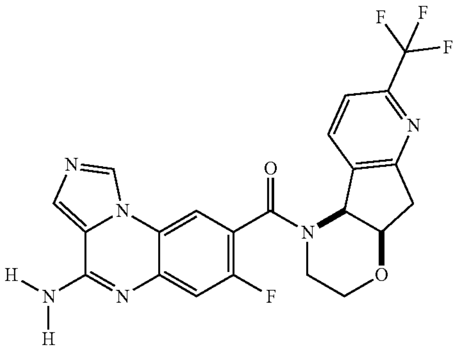 (±) |

TABLE 1D-continued
| Compounds | |
|---|---|
| Example | Structure |
| Ff-89 | 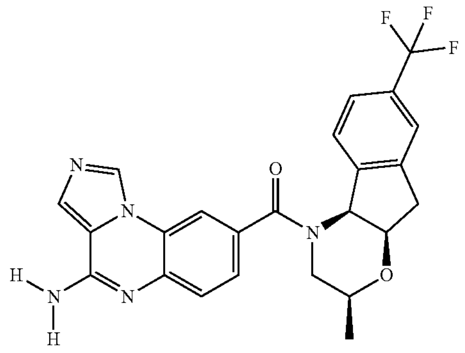 [SMILES: C[C@H]1CN(C(=O)c2ccc3nc(N)c4cncn4c3c2)[C@H]2c3ccc(C(F)(F)F)cc3C[C@H]2O1] |
| Ff-90 | 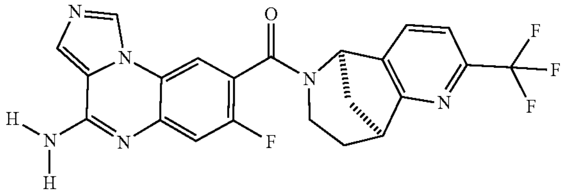<br>(±) |
| Ff-91 | 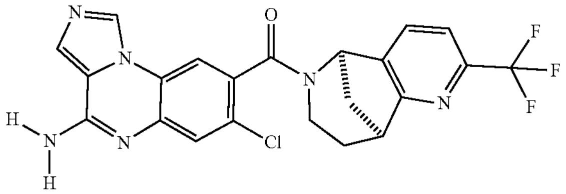<br>(±) |
| Ff-93 | 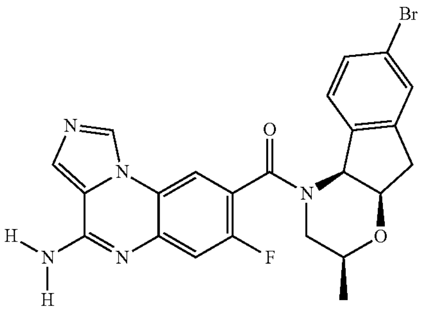 [SMILES: C[C@H]1CN(C(=O)c2cc3c(cc2F)nc(N)c2cncn23)[C@H]2c3ccc(Br)cc3C[C@H]2O1] |

TABLE 1D-continued
| Compounds | |
|---|---|
| Example | Structure |
| Ff-96 | 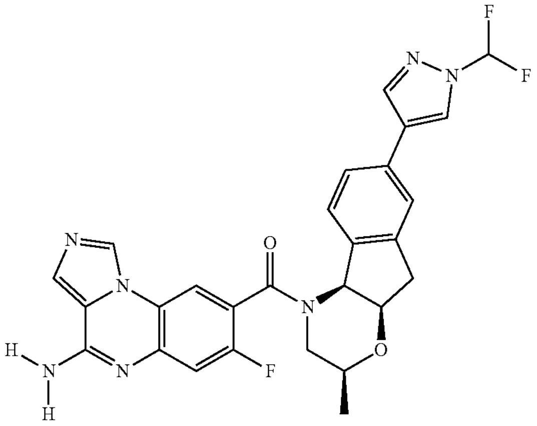 [SMILES: C[C@H]1CN(C(=O)c2cc3c(cc2F)nc(N)c2cncn23)[C@H]2c3ccc(-c4cnn(C(F)F)c4)cc3C[C@H]2O1] |
| Ff-97 | 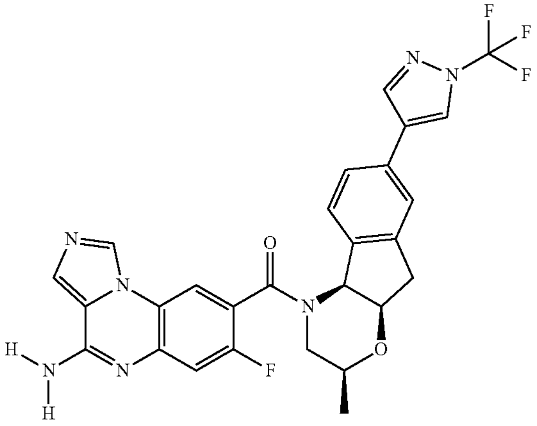 [SMILES: C[C@H]1CN(C(=O)c2cc3c(cc2F)nc(N)c2cncn23)[C@H]2c3ccc(-c4cnn(C(F)(F)F)c4)cc3C[C@H]2O1] |
| Ff-98 | 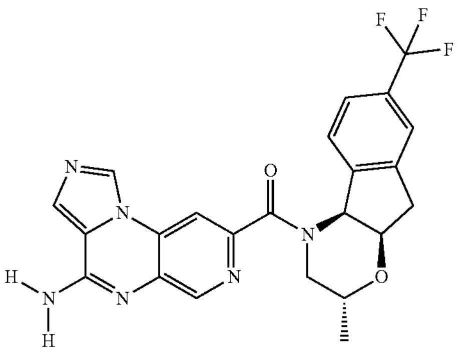 [SMILES: C[C@@H]1CN(C(=O)c2cc3c(cn2)nc(N)c2cncn23)[C@H]2c3ccc(C(F)(F)F)cc3C[C@H]2O1] |

TABLE 1D-continued
| Compounds | |
|---|---|
| Example | Structure |
| Ff-99 | 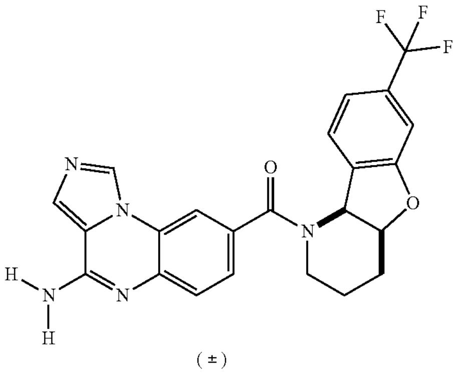 (±) |
| Ff-100 | 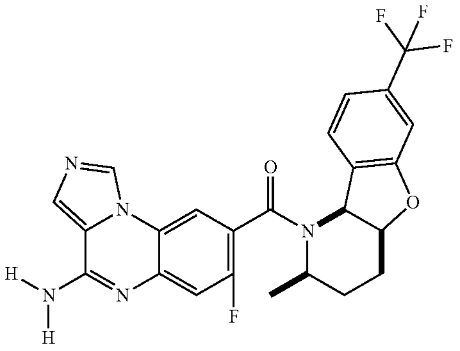 (±) |
| Ff-101 | 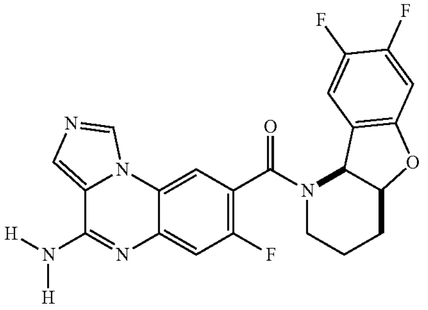 (±) |
| Ff-102 | 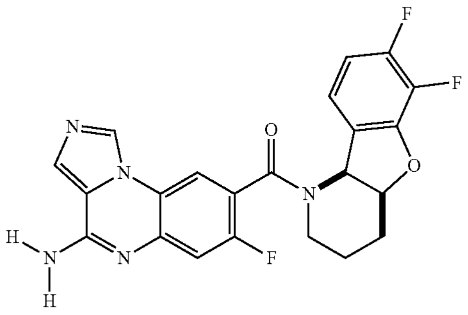 (±) |

TABLE 1D-continued
| Compounds | |
|---|---|
| Example | Structure |
| Ff-104 | 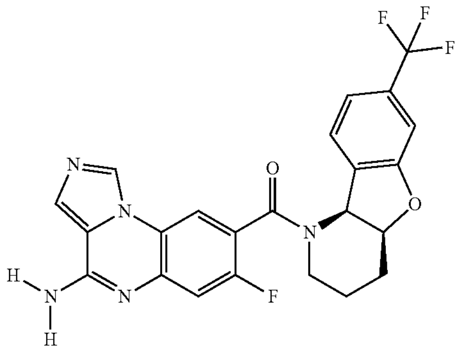 [SMILES: Nc1nc2cc(F)c(C(=O)N3CCC[C@@H]4Oc5cc(C(F)(F)F)ccc5[C@@H]43)cc2n2cncc12] |
| Ff-105 | 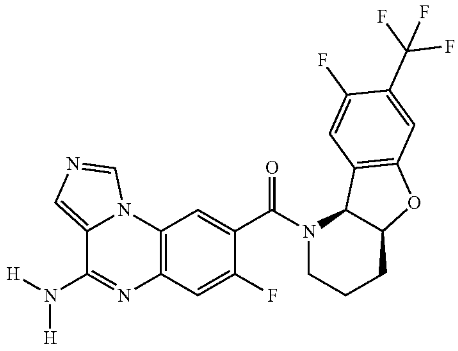 [SMILES: Nc1nc2cc(F)c(C(=O)N3CCC[C@@H]4Oc5cc(C(F)(F)F)c(F)cc5[C@@H]43)cc2n2cncc12] |
| Ff-106 | 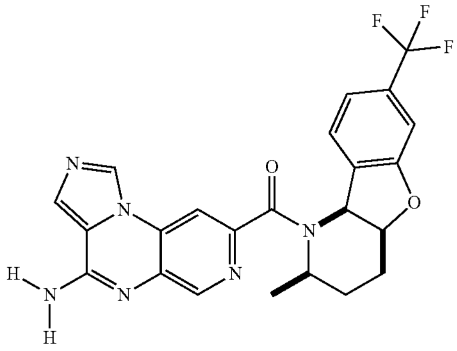 (±) |
| Ff-107 | 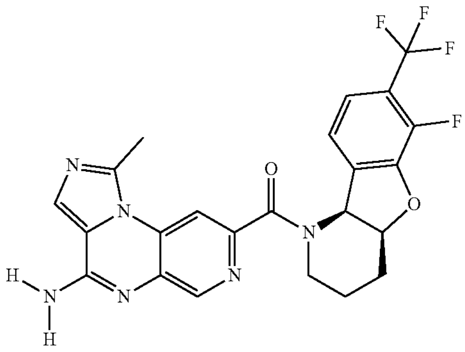 [SMILES: Cc1ncc2c(N)nc3cnc(C(=O)N4CCC[C@@H]5Oc6c(ccc(C(F)(F)F)c6F)[C@@H]54)cc3n12] |

TABLE 1D-continued
| Compounds | |
|---|---|
| Example | Structure |
| Ff-108 | 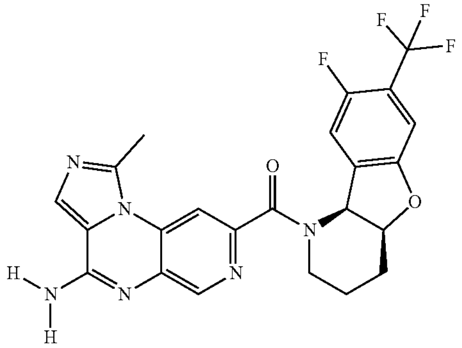 [SMILES: Cc1ncc2c(N)nc3cnc(C(=O)N4CCC[C@@H]5Oc6cc(C(F)(F)F)c(F)cc6[C@@H]54)cc3n12] |
| Ff-109 | 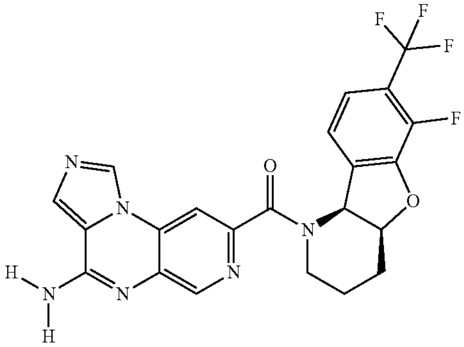 [SMILES: Nc1nc2cnc(C(=O)N3CCC[C@@H]4Oc5c(ccc(C(F)(F)F)c5F)[C@@H]43)cc2n2cncc12] |
| Ff-110 | 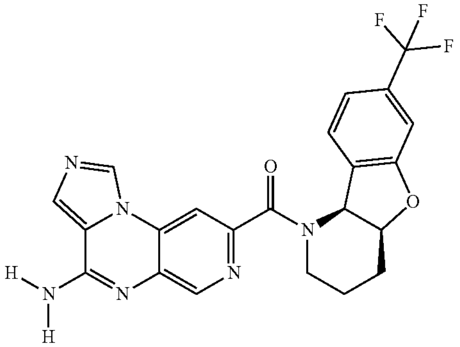 [SMILES: Nc1nc2cnc(C(=O)N3CCC[C@@H]4Oc5cc(C(F)(F)F)ccc5[C@@H]43)cc2n2cncc12] |
| Ff-111 | 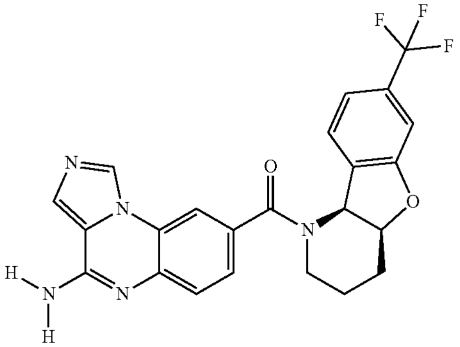 [SMILES: Nc1nc2ccc(C(=O)N3CCC[C@@H]4Oc5cc(C(F)(F)F)ccc5[C@@H]43)cc2n2cncc12] |

TABLE 1D-continued
| Compounds | |
|---|---|
| Example | Structure |
| Ff-112 | 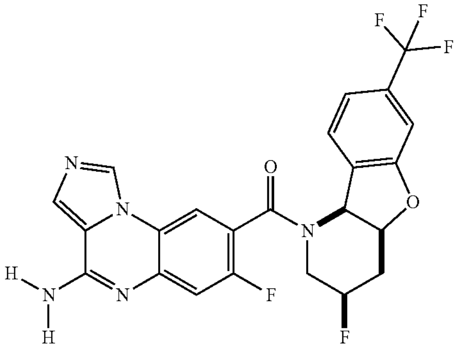 (±) |
| Ff-113 | 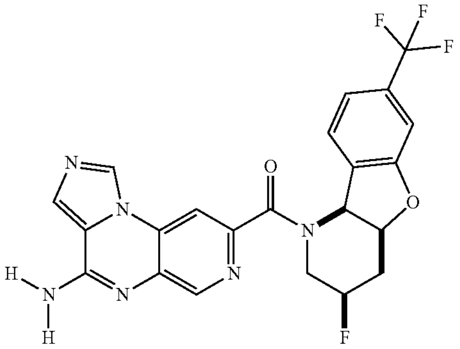 (±) |
| Ff-115 | 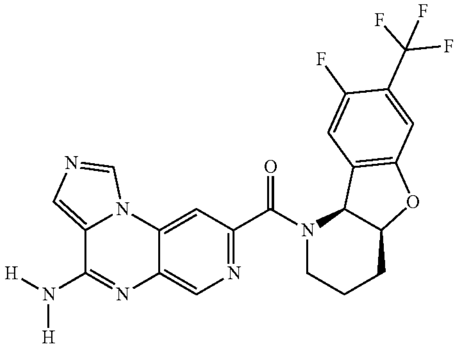 [SMILES: Nc1nc2cnc(C(=O)N3CCC[C@@H]4Oc5cc(C(F)(F)F)c(F)cc5[C@@H]43)cc2n2cncc12] |
| Ff-116 | 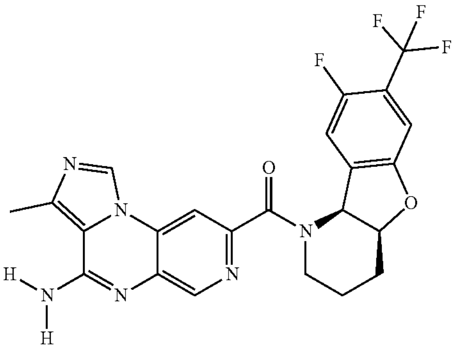 [SMILES: Cc1ncn2c1c(N)nc1cnc(C(=O)N3CCC[C@@H]4Oc5cc(C(F)(F)F)c(F)cc5[C@@H]43)cc12] |

TABLE 1D-continued
| Compounds | |
|---|---|
| Example | Structure |
| Ff-117 | 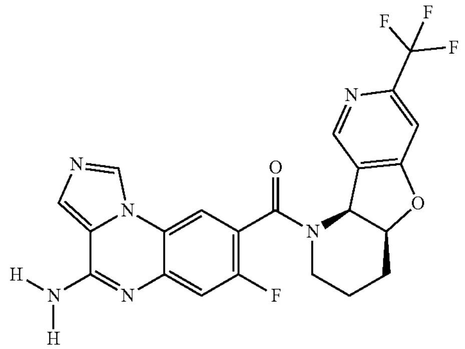 [SMILES: Nc1nc2cc(F)c(C(=O)N3CCC[C@@H]4Oc5cc(C(F)(F)F)ncc5[C@@H]43)cc2n2cncc12] |
| Ff-118 | 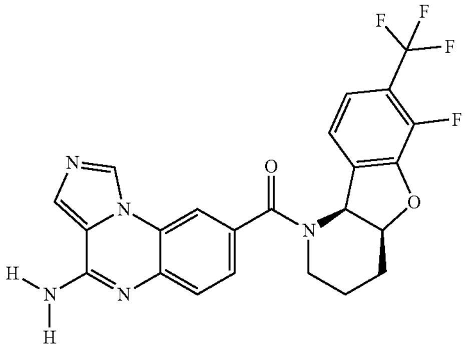 |
| Ff-119 | 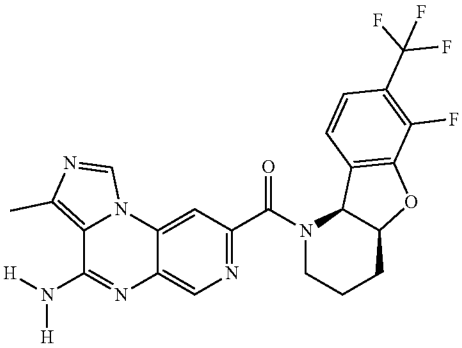 [SMILES: Cc1ncn2c1c(N)nc1cnc(C(=O)N3CCC[C@@H]4Oc5c(ccc(C(F)(F)F)c5F)[C@@H]43)cc12] |
| Ff-120 | 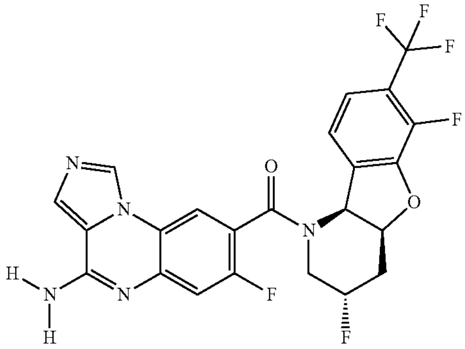 [SMILES: Nc1nc2cc(F)c(C(=O)N3C[C@@H](F)C[C@@H]4Oc5c(ccc(C(F)(F)F)c5F)[C@@H]43)cc2n2cncc12] |

TABLE 1D-continued
| Compounds | |
|---|---|
| Example | Structure |
| Ff-121 | 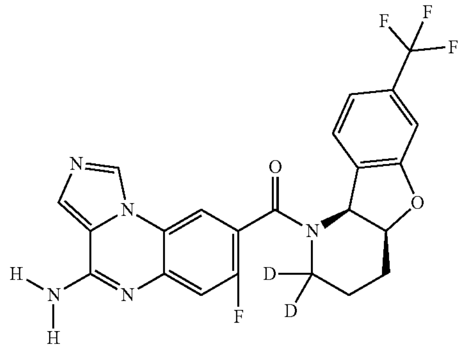 [SMILES: [2H]C1([2H])CC[C@@H]2Oc3cc(C(F)(F)F)ccc3[C@@H]2N1C(=O)c1cc2c(cc1F)nc(N)c1cncn12] |
| Ff-122 | 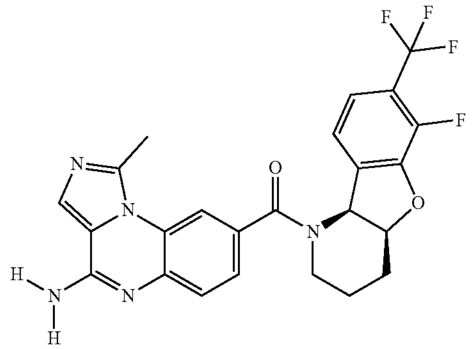 [SMILES: Cc1ncc2c(N)nc3ccc(C(=O)N4CCC[C@@H]5Oc6c(ccc(C(F)(F)F)c6F)[C@@H]54)cc3n12] |
| Ff-157 | 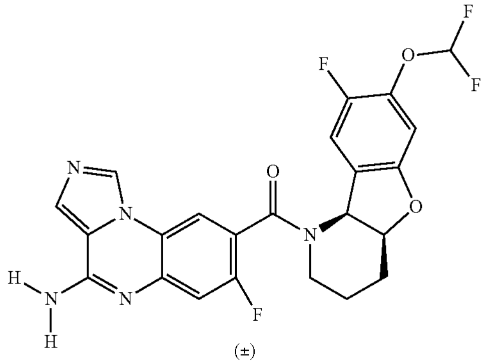 [SMILES: Nc1nc2cc(F)c(C(=O)N3CCC[C@@H]4Oc5cc(OC(F)F)c(F)cc5[C@@H]43)cc2n2cncc12] (±) |
| Ff-159 | 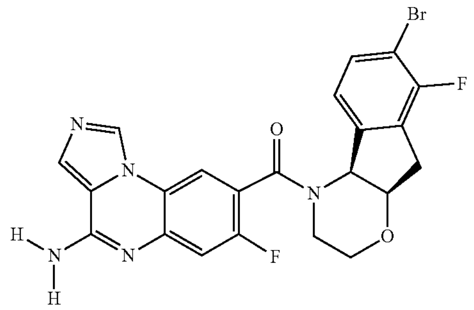 [SMILES: Nc1nc2cc(F)c(C(=O)N3CCO[C@@H]4Cc5c(ccc(Br)c5F)[C@@H]43)cc2n2cncc12] |

TABLE 1D-continued
| Compounds | |
|---|---|
| Example | Structure |
| Ff-160 | 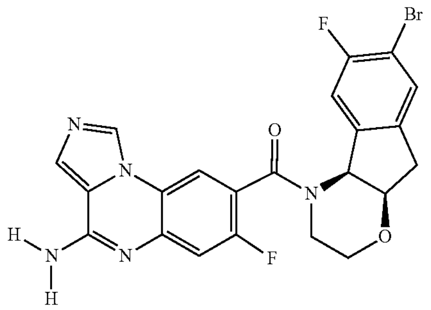 [SMILES: Nc1nc2cc(F)c(C(=O)N3CCO[C@@H]4Cc5cc(Br)c(F)cc5[C@@H]43)cc2n2cncc12] |
| Ff-161 | 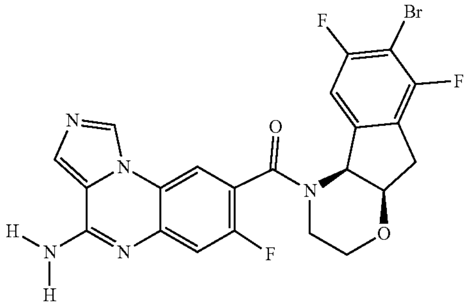 [SMILES: Nc1nc2cc(F)c(C(=O)N3CCO[C@@H]4Cc5c(cc(F)c(Br)c5F)[C@@H]43)cc2n2cncc12] |
| Ff-162 | 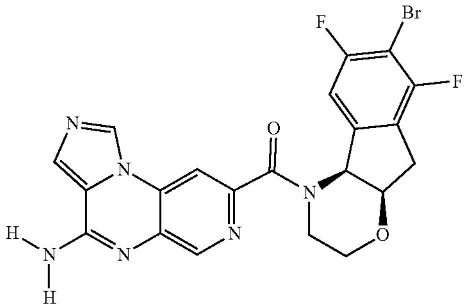 [SMILES: Nc1nc2cnc(C(=O)N3CCO[C@@H]4Cc5c(cc(F)c(Br)c5F)[C@@H]43)cc2n2cncc12] |
| Ff-163 | 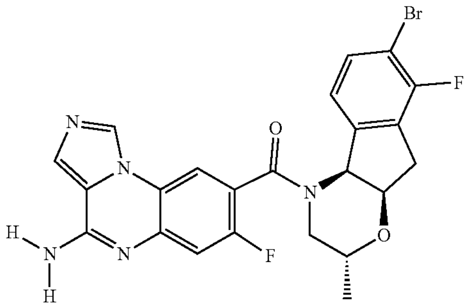 [SMILES: C[C@@H]1CN(C(=O)c2cc3c(cc2F)nc(N)c2cncn23)[C@H]2c3ccc(Br)c(F)c3C[C@H]2O1] |

TABLE 1D-continued
| Compounds | |
|---|---|
| Ex-<br>am-<br>ple | Structure |
| Ff-<br>164 | 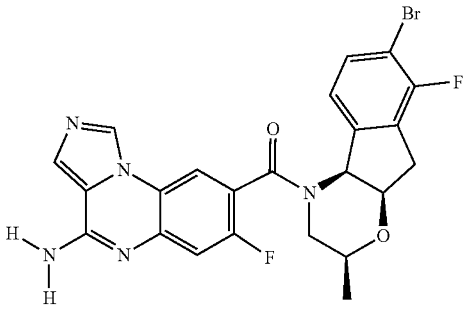 [SMILES: C[C@H]1CN(C(=O)c2cc3c(cc2F)nc(N)c2cncn23)[C@H]2c3ccc(Br)c(F)c3C[C@H]2O1] |
| Ff-<br>165 | 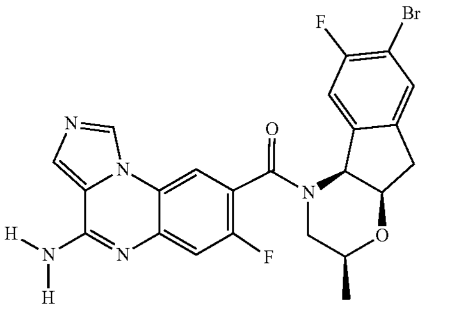 [SMILES: C[C@H]1CN(C(=O)c2cc3c(cc2F)nc(N)c2cncn23)[C@H]2c3cc(F)c(Br)cc3C[C@H]2O1] |
| Ff-<br>167 | 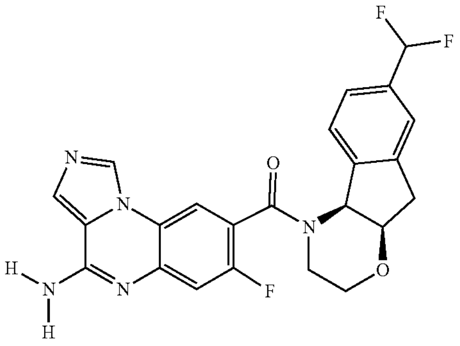 [SMILES: Nc1nc2cc(F)c(C(=O)N3CCO[C@@H]4Cc5cc(C(F)F)ccc5[C@@H]43)cc2n2cncc12] |
| Ff-<br>168 | 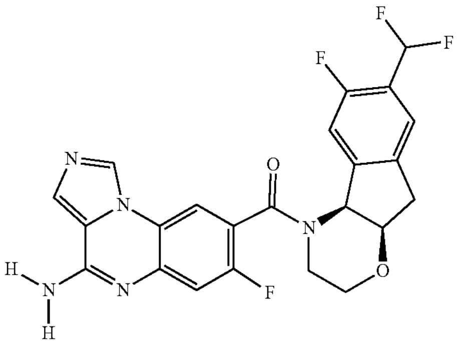 [SMILES: Nc1nc2cc(F)c(C(=O)N3CCO[C@@H]4Cc5cc(C(F)F)c(F)cc5[C@@H]43)cc2n2cncc12] |

TABLE 1D-continued
| Compounds | |
|---|---|
| Example | Structure |
| Ff-169 | 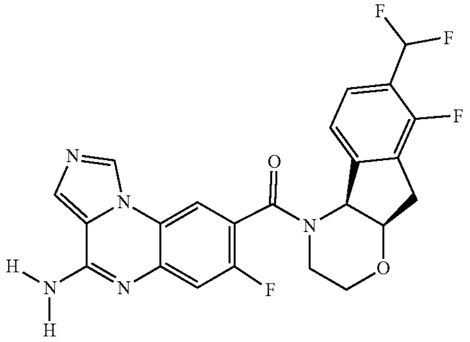 [SMILES: Nc1nc2cc(F)c(C(=O)N3CCO[C@@H]4Cc5c(ccc(C(F)F)c5F)[C@@H]43)cc2n2cncc12] |
| Ff-170 | 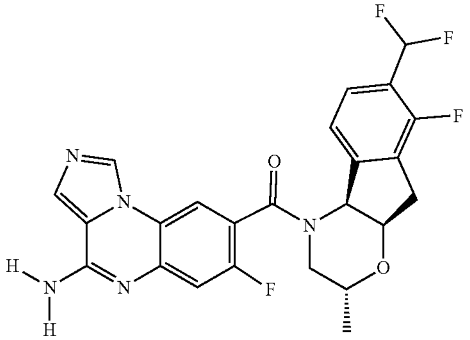 [SMILES: C[C@@H]1CN(C(=O)c2cc3c(cc2F)nc(N)c2cncn23)[C@H]2c3ccc(C(F)F)c(F)c3C[C@H]2O1] |
| Ff-171 | 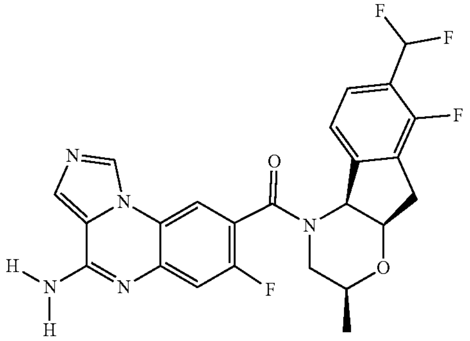 [SMILES: C[C@H]1CN(C(=O)c2cc3c(cc2F)nc(N)c2cncn23)[C@H]2c3ccc(C(F)F)c(F)c3C[C@H]2O1] |
| Ff-172 | 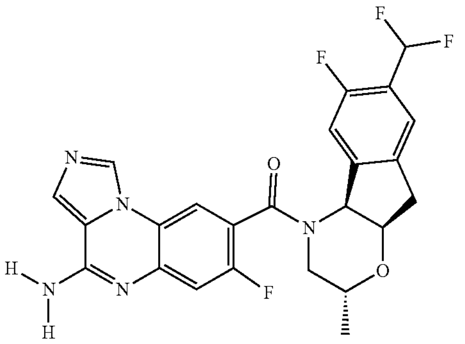 [SMILES: C[C@@H]1CN(C(=O)c2cc3c(cc2F)nc(N)c2cncn23)[C@H]2c3cc(F)c(C(F)F)cc3C[C@H]2O1] |

TABLE 1D-continued
| Compounds | |
|---|---|
| Example | Structure |
| Ff-173 | 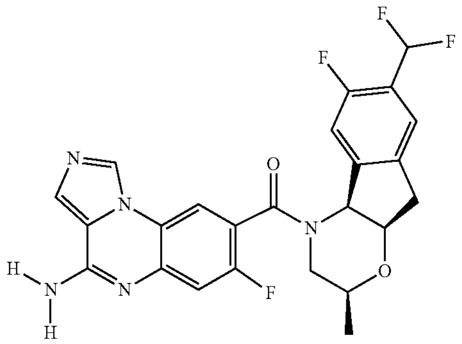 [SMILES: C[C@H]1CN(C(=O)c2cc3c(cc2F)nc(N)c2cncn23)[C@H]2c3cc(F)c(C(F)F)cc3C[C@H]2O1] |
| Ff-174 | 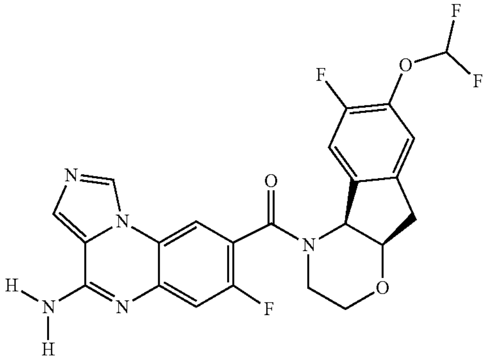 [SMILES: Nc1nc2cc(F)c(C(=O)N3CCO[C@@H]4Cc5cc(OC(F)F)c(F)cc5[C@@H]43)cc2n2cncc12] |
| Ff-175 | 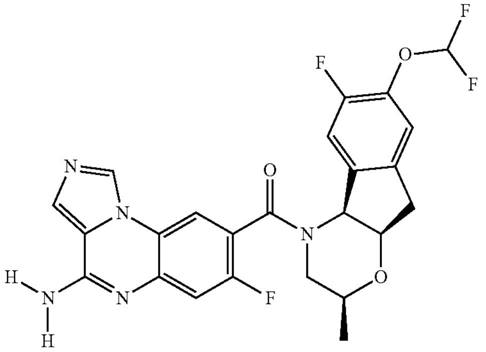 [SMILES: C[C@H]1CN(C(=O)c2cc3c(cc2F)nc(N)c2cncn23)[C@H]2c3cc(F)c(OC(F)F)cc3C[C@H]2O1] |
| Ff-176 | 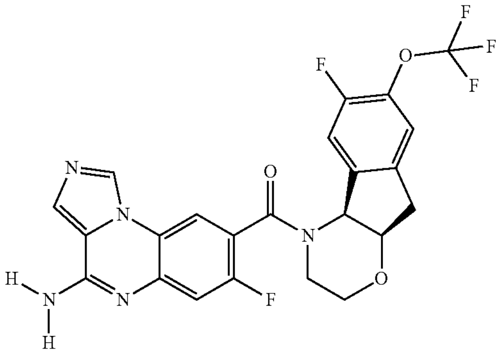 [SMILES: Nc1nc2cc(F)c(C(=O)N3CCO[C@@H]4Cc5cc(OC(F)(F)F)c(F)cc5[C@@H]43)cc2n2cncc12] |

TABLE 1D-continued
| Compounds | |
|---|---|
| Example | Structure |
| Ff-177 | 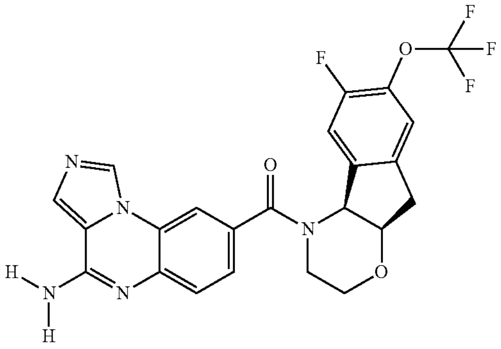 [SMILES: Nc1nc2ccc(C(=O)N3CCO[C@@H]4Cc5cc(OC(F)(F)F)c(F)cc5[C@@H]43)cc2n2cncc12] |
| Ff-178 | 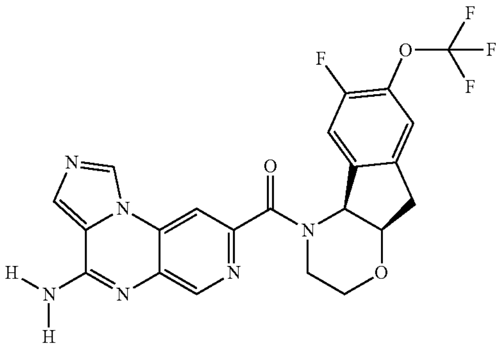 |
| Ff-179 | 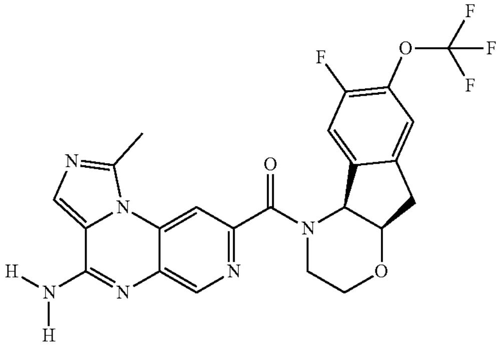 [SMILES: Cc1ncc2c(N)nc3cnc(C(=O)N4CCO[C@@H]5Cc6cc(OC(F)(F)F)c(F)cc6[C@@H]54)cc3n12] |
| Ff-180 | 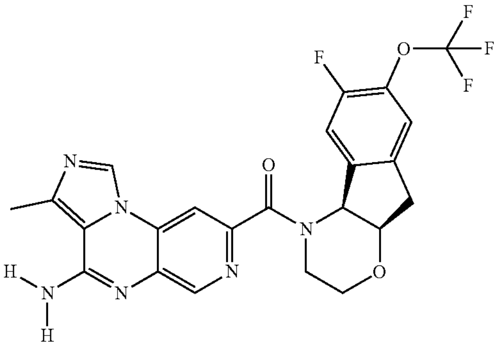 [SMILES: Cc1ncn2c1c(N)nc1cnc(C(=O)N3CCO[C@@H]4Cc5cc(OC(F)(F)F)c(F)cc5[C@@H]43)cc12] |

TABLE 1D-continued
| Compounds | |
|---|---|
| Example | Structure |
| Ff-181 | 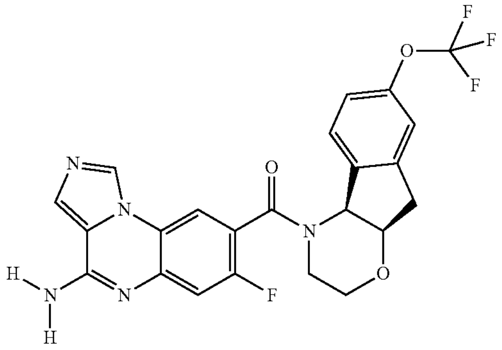 [SMILES: Nc1nc2cc(F)c(C(=O)N3CCO[C@@H]4Cc5cc(OC(F)(F)F)ccc5[C@@H]43)cc2n2cncc12] |
| Ff-182 | 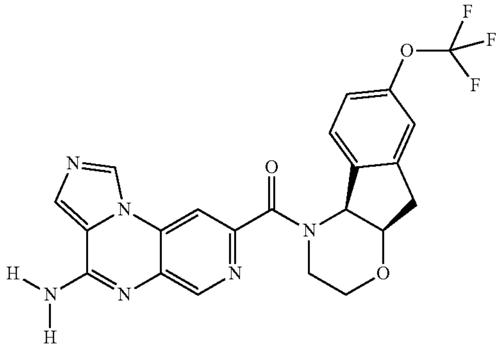 [SMILES: Nc1nc2cnc(C(=O)N3CCO[C@@H]4Cc5cc(OC(F)(F)F)ccc5[C@@H]43)cc2n2cncc12] |
| Ff-183 | 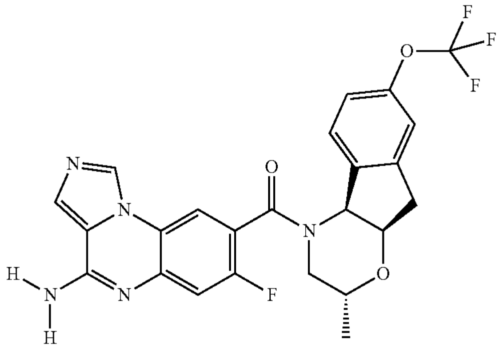 [SMILES: C[C@@H]1CN(C(=O)c2cc3c(cc2F)nc(N)c2cncn23)[C@H]2c3ccc(OC(F)(F)F)cc3C[C@H]2O1] |
| Ff-184 | 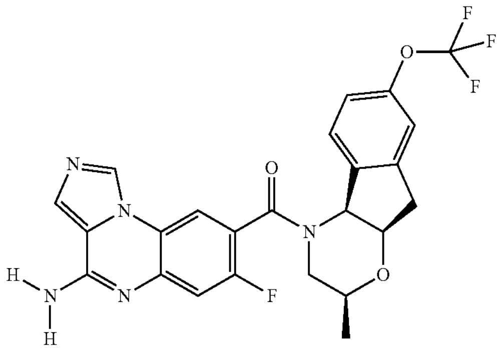 [SMILES: C[C@H]1CN(C(=O)c2cc3c(cc2F)nc(N)c2cncn23)[C@H]2c3ccc(OC(F)(F)F)cc3C[C@H]2O1] |

TABLE 1D-continued
| Compounds | |
|---|---|
| Example | Structure |
| Ff-185 | 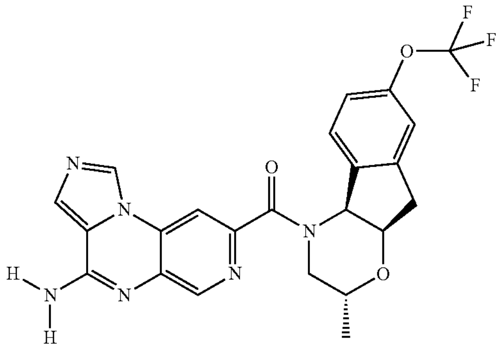 [SMILES: C[C@@H]1CN(C(=O)c2cc3c(cn2)nc(N)c2cncn23)[C@H]2c3ccc(OC(F)(F)F)cc3C[C@H]2O1] |
| Ff-186 | 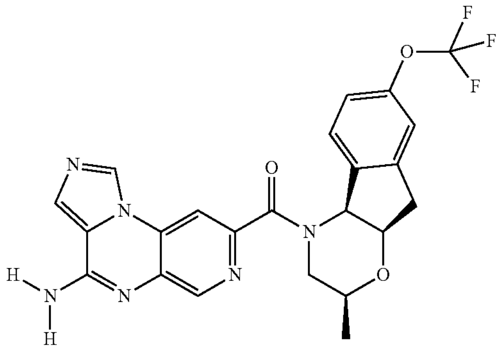 [SMILES: C[C@H]1CN(C(=O)c2cc3c(cn2)nc(N)c2cncn23)[C@H]2c3ccc(OC(F)(F)F)cc3C[C@H]2O1] |
| Ff-187 | 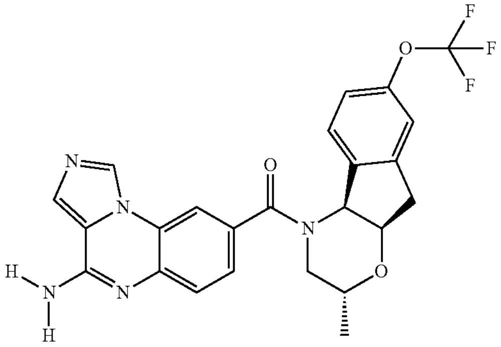 [SMILES: C[C@@H]1CN(C(=O)c2ccc3nc(N)c4cncn4c3c2)[C@H]2c3ccc(OC(F)(F)F)cc3C[C@H]2O1] |
| Ff-188 | 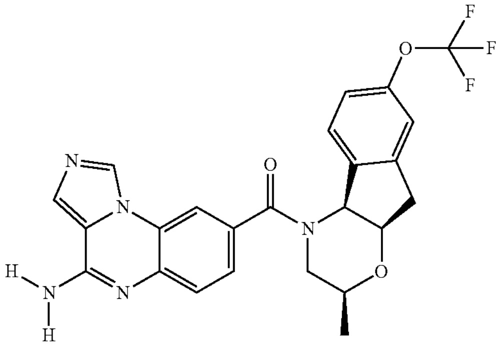 [SMILES: C[C@H]1CN(C(=O)c2ccc3nc(N)c4cncn4c3c2)[C@H]2c3ccc(OC(F)(F)F)cc3C[C@H]2O1] |

TABLE 1D-continued
| Compounds | |
|---|---|
| Example | Structure |
| Ff-189 | 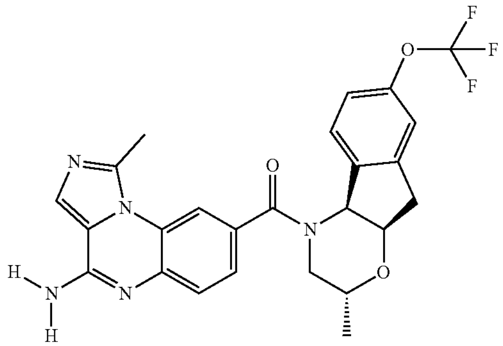 [SMILES: Cc1ncc2c(N)nc3ccc(C(=O)N4C[C@@H](C)O[C@@H]5Cc6cc(OC(F)(F)F)ccc6[C@@H]54)cc3n12] |
| Ff-190 | 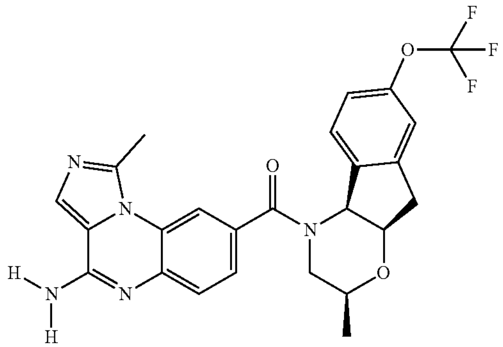 [SMILES: Cc1ncc2c(N)nc3ccc(C(=O)N4C[C@H](C)O[C@@H]5Cc6cc(OC(F)(F)F)ccc6[C@@H]54)cc3n12] |
| Ff-191 | 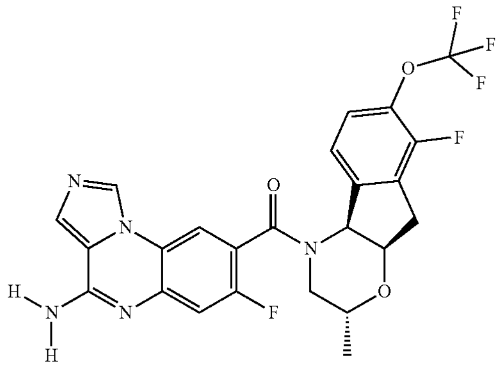 [SMILES: C[C@@H]1CN(C(=O)c2cc3c(cc2F)nc(N)c2cncn23)[C@H]2c3ccc(OC(F)(F)F)c(F)c3C[C@H]2O1] |
| Ff-192 | 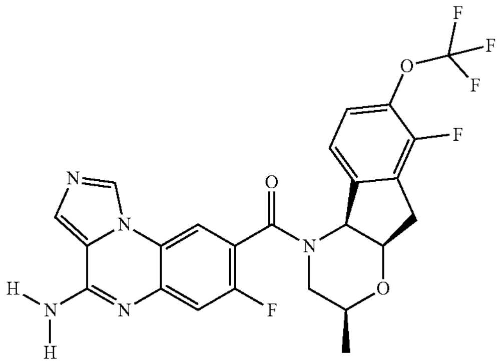 [SMILES: C[C@H]1CN(C(=O)c2cc3c(cc2F)nc(N)c2cncn23)[C@H]2c3ccc(OC(F)(F)F)c(F)c3C[C@H]2O1] |

TABLE 1D-continued
| Compounds | |
|---|---|
| Example | Structure |
| Ff-193 | 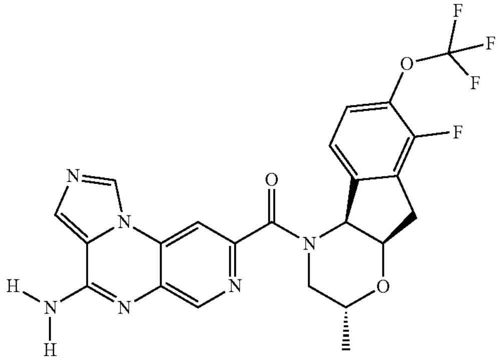 [SMILES: C[C@@H]1CN(C(=O)c2cc3c(cn2)nc(N)c2cncn23)[C@H]2c3ccc(OC(F)(F)F)c(F)c3C[C@H]2O1] |
| Ff-194 | 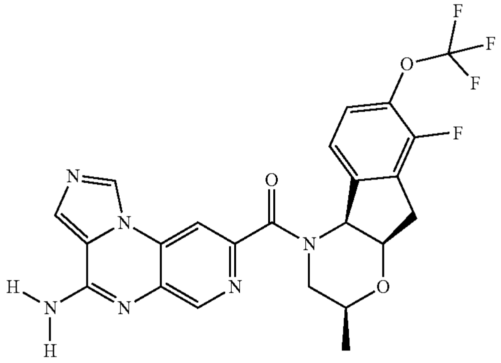 [SMILES: C[C@H]1CN(C(=O)c2cc3c(cn2)nc(N)c2cncn23)[C@H]2c3ccc(OC(F)(F)F)c(F)c3C[C@H]2O1] |
| Ff-195 | 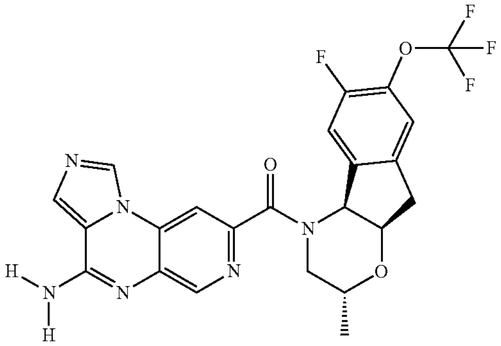 |
| Ff-196 | 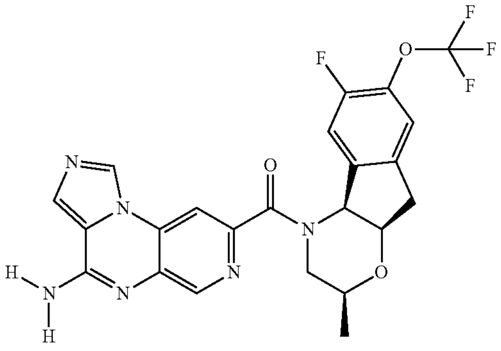 [SMILES: C[C@H]1CN(C(=O)c2cc3c(cn2)nc(N)c2cncn23)[C@H]2c3cc(F)c(OC(F)(F)F)cc3C[C@H]2O1] |

TABLE 1D-continued
| Compounds | |
|---|---|
| Example | Structure |
| Ff-197 | 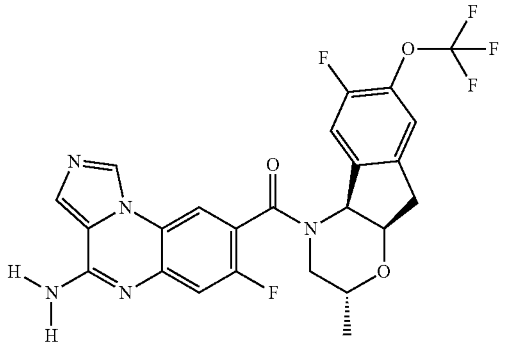 |
| Ff-198 | 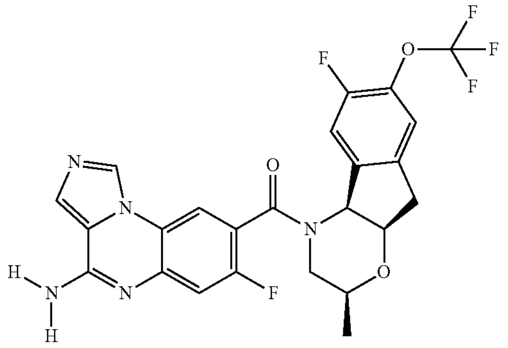 [SMILES: C[C@H]1CN(C(=O)c2cc3c(cc2F)nc(N)c2cncn23)[C@H]2c3cc(F)c(OC(F)(F)F)cc3C[C@H]2O1] |
| Ff-199 | 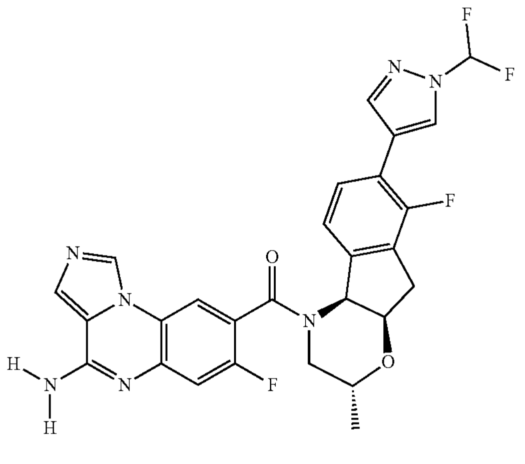 [SMILES: C[C@@H]1CN(C(=O)c2cc3c(cc2F)nc(N)c2cncn23)[C@H]2c3ccc(-c4cnn(C(F)F)c4)c(F)c3C[C@H]2O1] |

TABLE 1D-continued
| Compounds | |
|---|---|
| Example | Structure |
| Ff-200 | 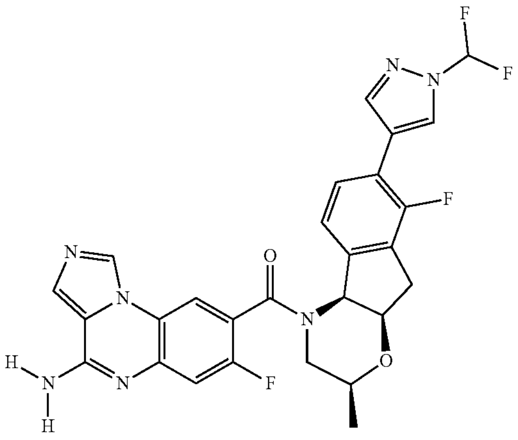 [SMILES: C[C@H]1CN(C(=O)c2cc3c(cc2F)nc(N)c2cncn23)[C@H]2c3ccc(-c4cnn(C(F)F)c4)c(F)c3C[C@H]2O1] |
| Ff-201 | 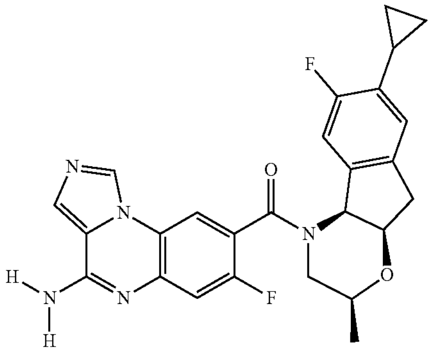 [SMILES: C[C@H]1CN(C(=O)c2cc3c(cc2F)nc(N)c2cncn23)[C@H]2c3cc(F)c(C4CC4)cc3C[C@H]2O1] |
| Ff-234 | 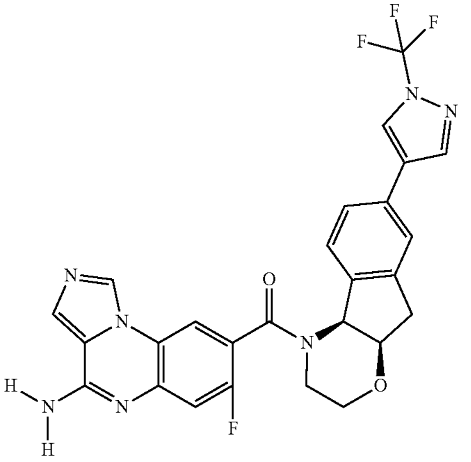 [SMILES: Nc1nc2cc(F)c(C(=O)N3CCO[C@@H]4Cc5cc(-c6cnn(C(F)(F)F)c6)ccc5[C@@H]43)cc2n2cncc12] |

TABLE 1D-continued
| Compounds | |
|---|---|
| Example | Structure |
| Ff-235 | 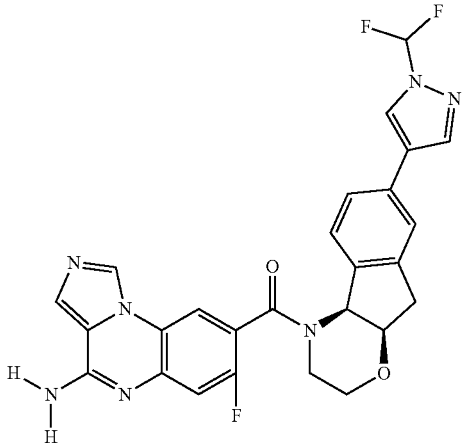 [SMILES: Nc1nc2cc(F)c(C(=O)N3CCO[C@@H]4Cc5cc(-c6cnn(C(F)F)c6)ccc5[C@@H]43)cc2n2cncc12] |
| Ff-236 | 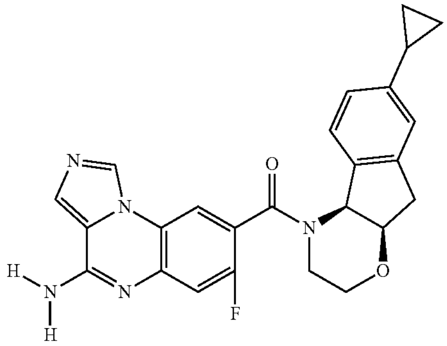 [SMILES: Nc1nc2cc(F)c(C(=O)N3CCO[C@@H]4Cc5cc(C6CC6)ccc5[C@@H]43)cc2n2cncc12] |
| Ff-239 | 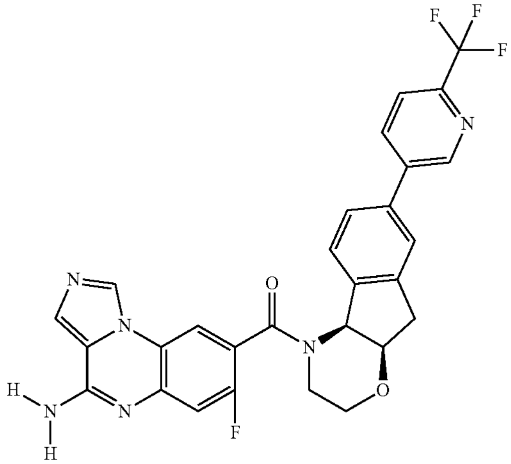 [SMILES: Nc1nc2cc(F)c(C(=O)N3CCO[C@@H]4Cc5cc(-c6ccc(C(F)(F)F)nc6)ccc5[C@@H]43)cc2n2cncc12] |

TABLE 1D-continued
| Compounds | |
|---|---|
| Example | Structure |
| Ff-240 | 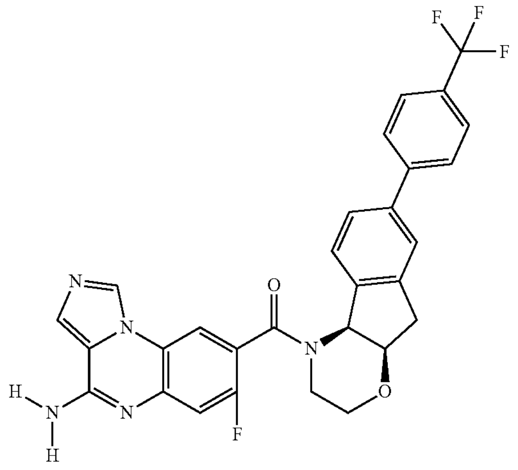 [SMILES: Nc1nc2cc(F)c(C(=O)N3CCO[C@@H]4Cc5cc(-c6ccc(C(F)(F)F)cc6)ccc5[C@@H]43)cc2n2cncc12] |
| Ff-246 | 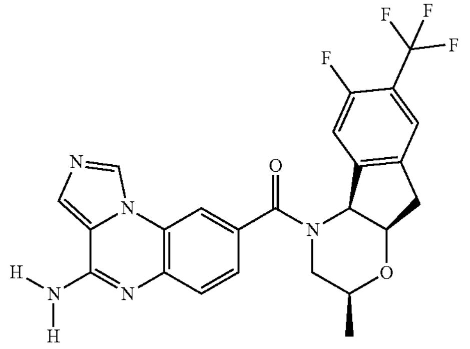 [SMILES: C[C@H]1CN(C(=O)c2ccc3nc(N)c4cncn4c3c2)[C@H]2c3cc(F)c(C(F)(F)F)cc3C[C@H]2O1] |
| Ff-247 | 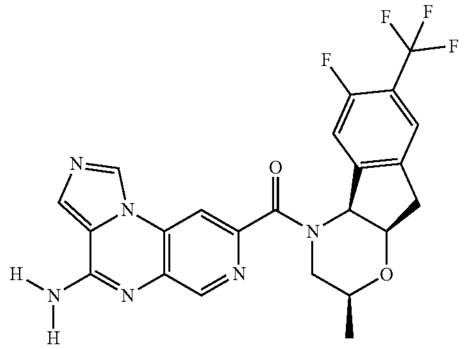 [SMILES: C[C@H]1CN(C(=O)c2cc3c(cn2)nc(N)c2cncn23)[C@H]2c3cc(F)c(C(F)(F)F)cc3C[C@H]2O1] |
| Ff-248 | 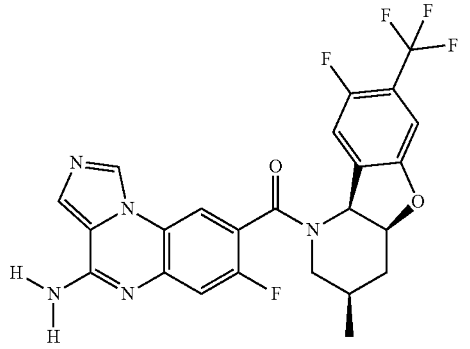 [SMILES: C[C@@H]1C[C@@H]2Oc3cc(C(F)(F)F)c(F)cc3[C@@H]2N(C(=O)c2cc3c(cc2F)nc(N)c2cncn23)C1] |

TABLE 1D-continued
| Example | Structure |
|---|---|
| Ff-249 | 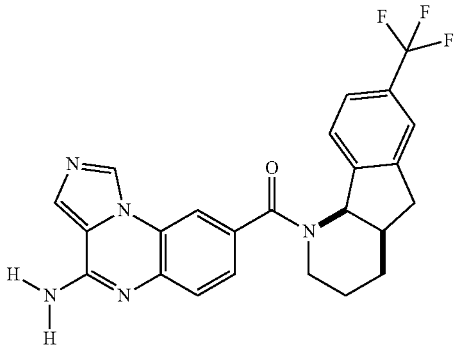 (±) |
| Ff-250 | 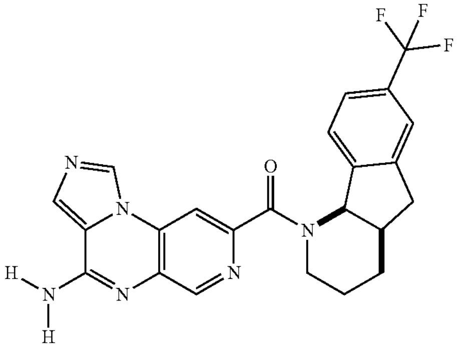 (±) |
| Ff-251 | 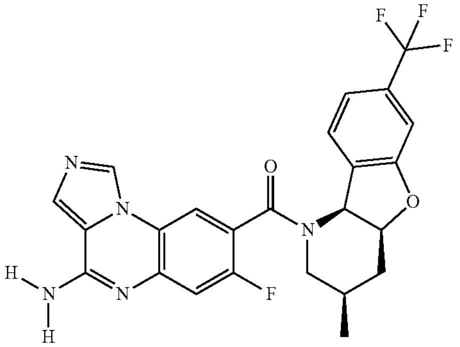 [SMILES: C[C@@H]1C[C@@H]2Oc3cc(C(F)(F)F)ccc3[C@@H]2N(C(=O)c2cc3c(cc2F)nc(N)c2cncn23)C1] |
| Ff-252 | 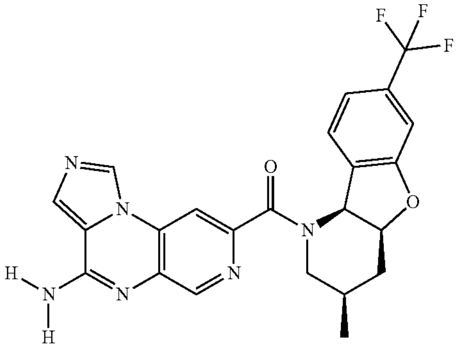 [SMILES: C[C@@H]1C[C@@H]2Oc3cc(C(F)(F)F)ccc3[C@@H]2N(C(=O)c2cc3c(cn2)nc(N)c2cncn23)C1] |

TABLE 1D-continued
| Compounds | |
|---|---|
| Example | Structure |
| Ff-257 | 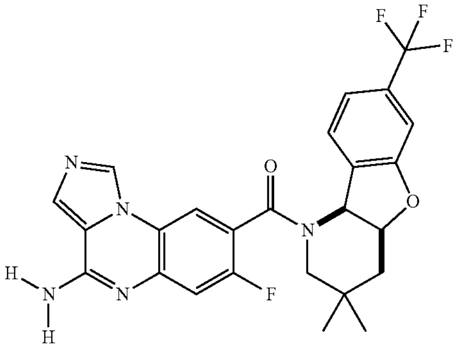 (±) |
| Ff-58 | 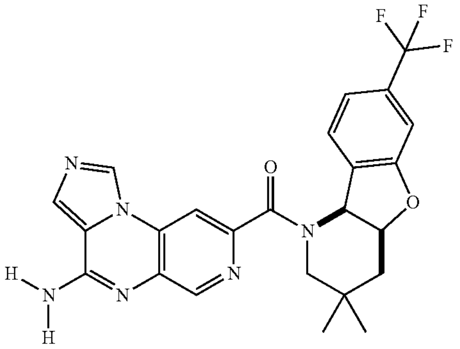 (±) |
| Ff-259 | 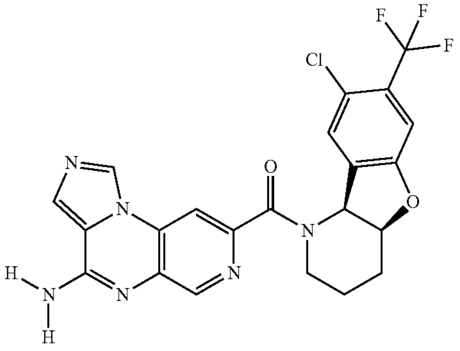 [SMILES: Nc1nc2cnc(C(=O)N3CCC[C@@H]4Oc5cc(C(F)(F)F)c(Cl)cc5[C@@H]43)cc2n2cncc12] |
| Ff-260 | 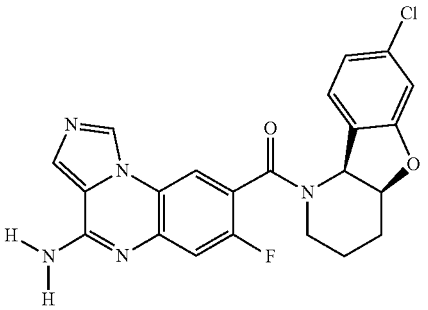 |

TABLE 1D-continued
| Compounds | |
|---|---|
| Example | Structure |
| Ff-261 | 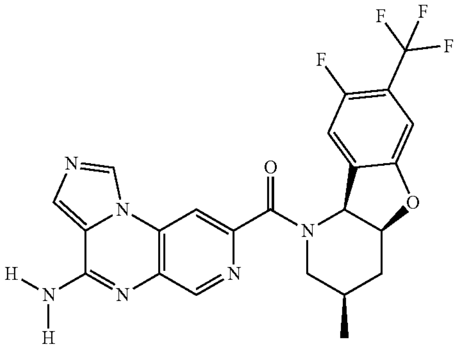 [SMILES: C[C@@H]1C[C@@H]2Oc3cc(C(F)(F)F)c(F)cc3[C@@H]2N(C(=O)c2cc3c(cn2)nc(N)c2cncn23)C1] |
| Ff-262 | 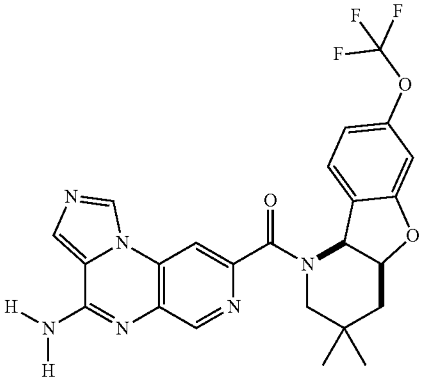 (±) |
| Ff-293 | 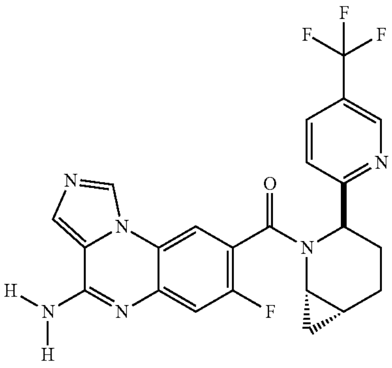 (±) |

TABLE 1D-continued
| Compounds | |
|---|---|
| Example | Structure |
| Ff-294 | 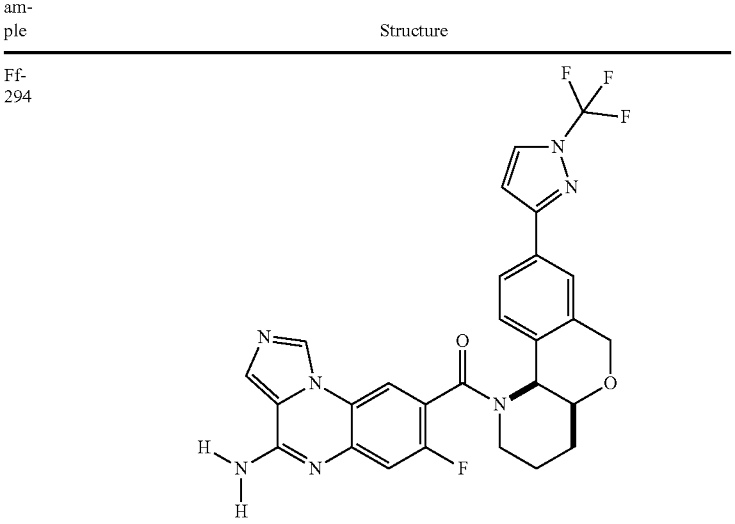 (±) |
| Ff-295 | 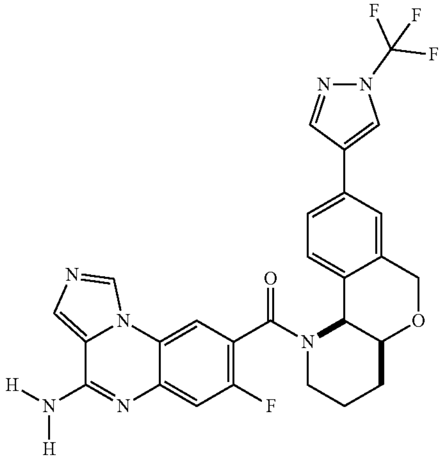 (±) |
| Ff-296 | 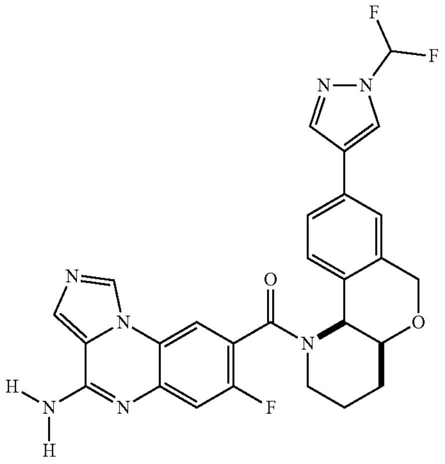 (±) |

TABLE 1D-continued
| Compounds | |
|---|---|
| Example | Structure |
| Ff-297 | 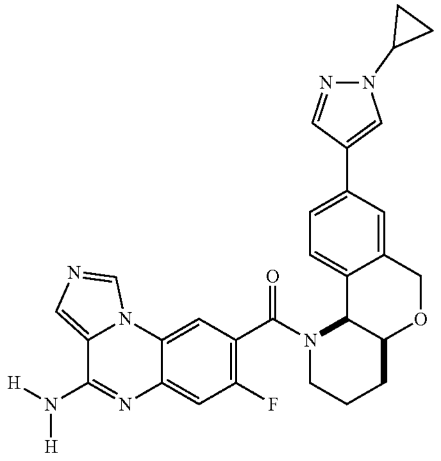 (±) |
| Ff-298 | 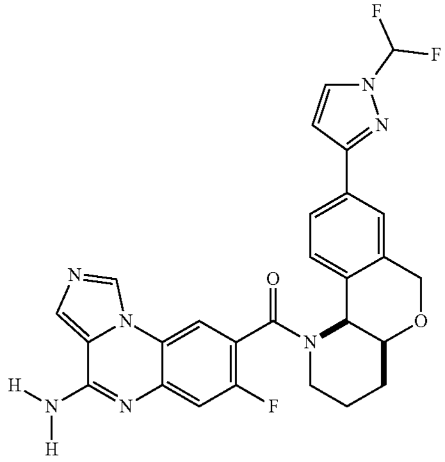 (±) |
| Ff-299 | 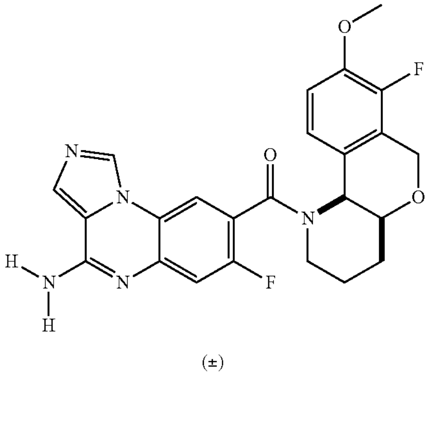 (±) |

TABLE 1D-continued
| Compounds | |
|---|---|
| Ex-<br>am-<br>ple | Structure |
| Ff-<br>300 | 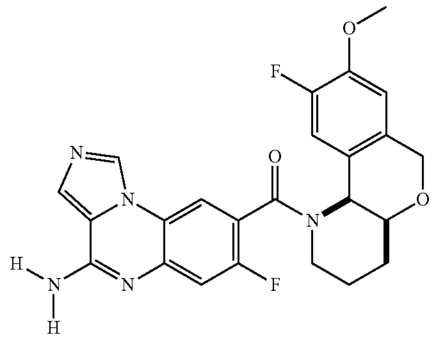<br>(±) |
| Ff-<br>301 | 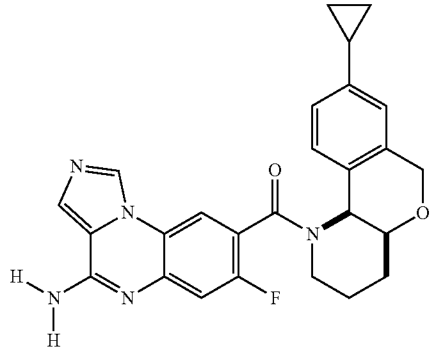<br>(±) |
| Ff-<br>310 | 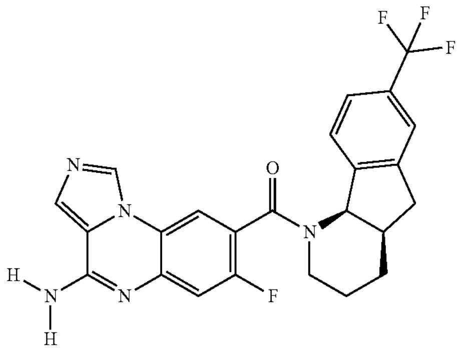 |
| Ff-<br>314 | 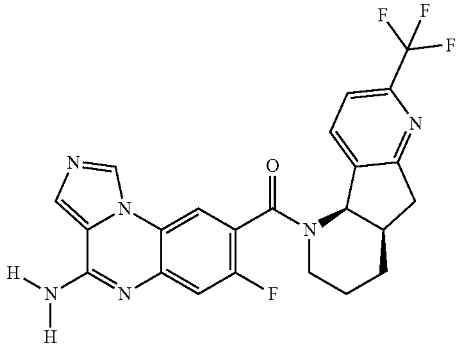 [SMILES: Nc1nc2cc(F)c(C(=O)N3CCC[C@@H]4Cc5nc(C(F)(F)F)ccc5[C@@H]43)cc2n2cncc12] |

TABLE 1D-continued
| Compounds | |
|---|---|
| Example | Structure |
| Ff-319 | 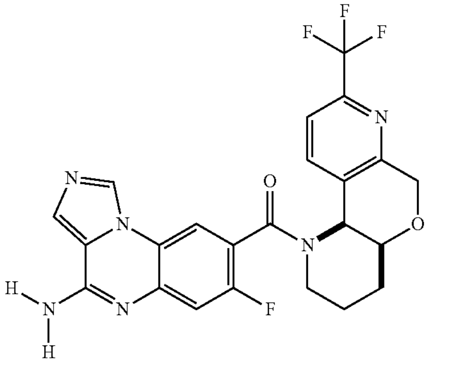 (±) |
| Ff-320 | 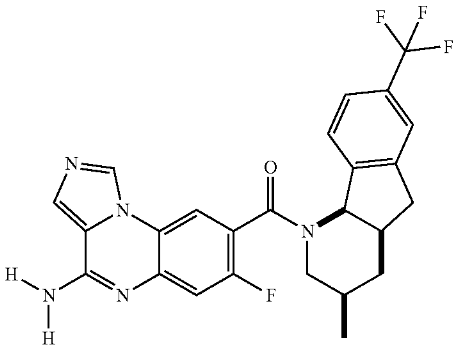 (±) |
| Ff-321 | 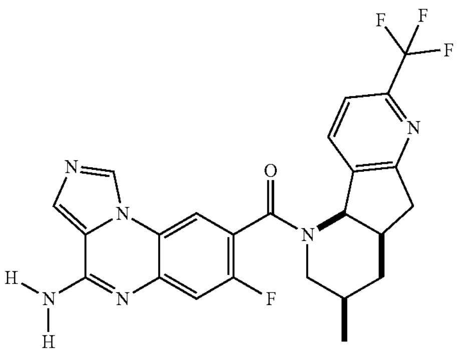 (±) |

TABLE 1D-continued
| Compounds | |
|---|---|
| Example | Structure |
| Ff-322 | 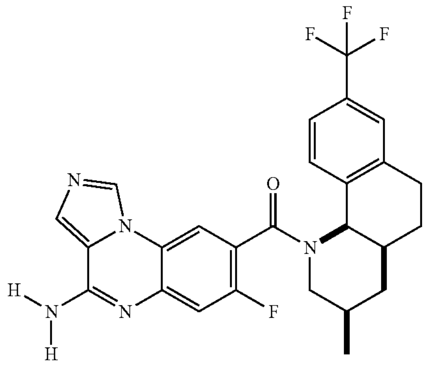 (±) |
| Ff-323 | 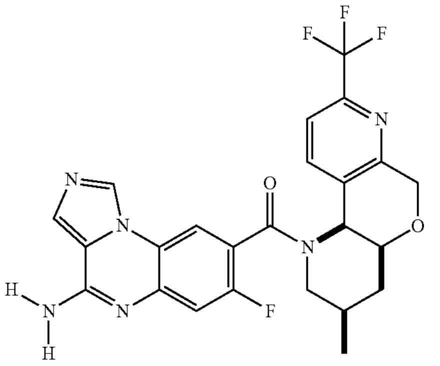 (±) |
| Ff-326 | 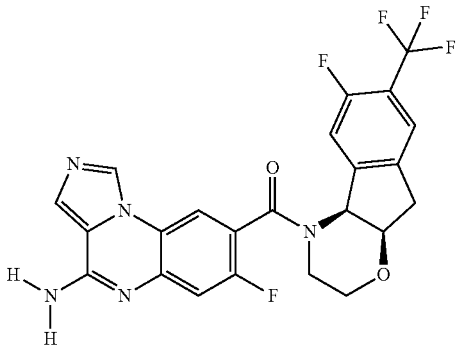 |
| Ff-327 | 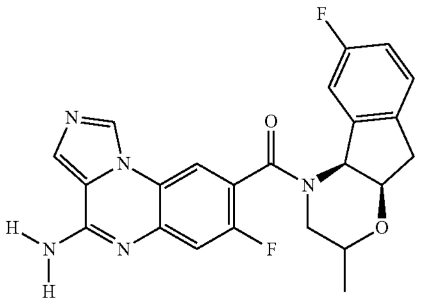 |

TABLE 1D-continued
| Compounds | |
| --- | --- |
| Example | Structure |
| Ff-328 | 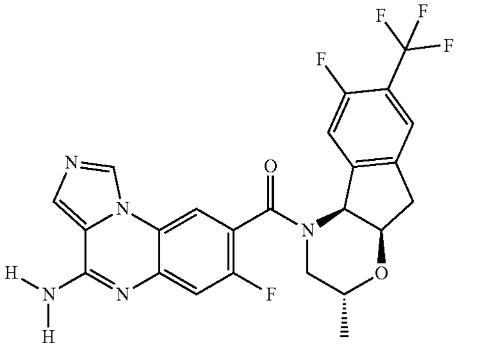 [SMILES: C[C@@H]1CN(C(=O)c2cc3c(cc2F)nc(N)c2cncn23)[C@H]2c3cc(F)c(C(F)(F)F)cc3C[C@H]2O1] |
| Ff-329 | 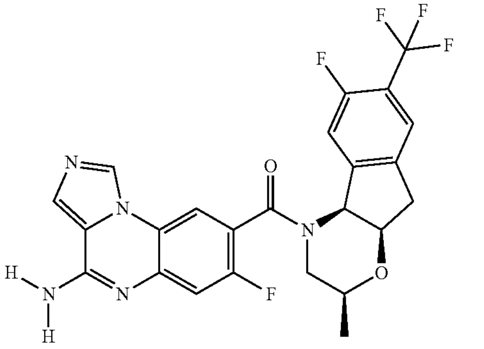 [SMILES: C[C@H]1CN(C(=O)c2cc3c(cc2F)nc(N)c2cncn23)[C@H]2c3cc(F)c(C(F)(F)F)cc3C[C@H]2O1] |
| Ff-331 | 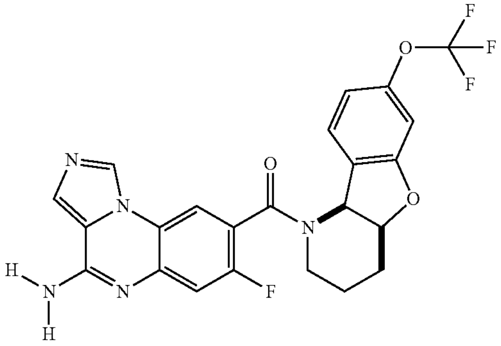<br>(±) |
| Ff-332 | 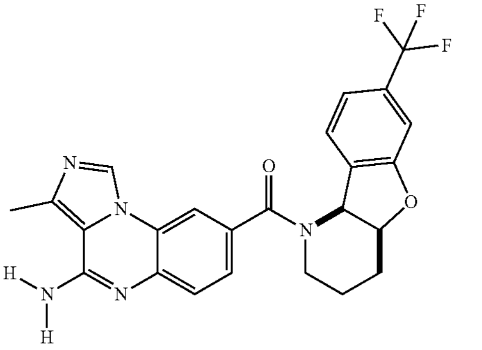<br>(±) |

TABLE 1D-continued
| Compounds | |
|---|---|
| Example | Structure |
| Ff-333 | 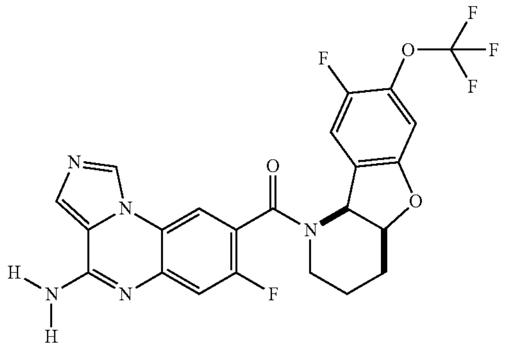 (±) |
| Ff-334 | 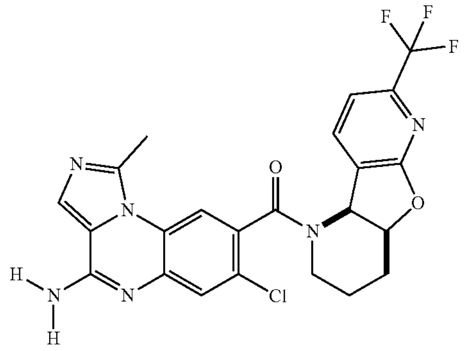 (±) |
| Ff-335 | 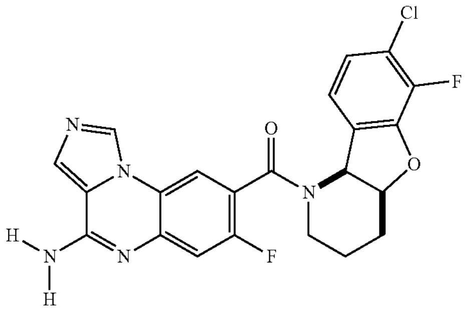 (±) |
| Ff-336 | 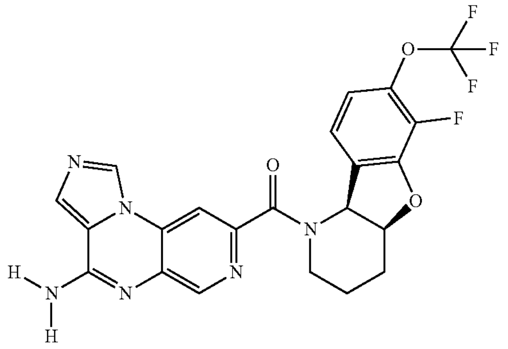 [SMILES: Nc1nc2cnc(C(=O)N3CCC[C@@H]4Oc5c(ccc(OC(F)(F)F)c5F)[C@@H]43)cc2n2cncc12] |

TABLE 1D-continued
| Compounds | |
|---|---|
| Example | Structure |
| Ff-338 | 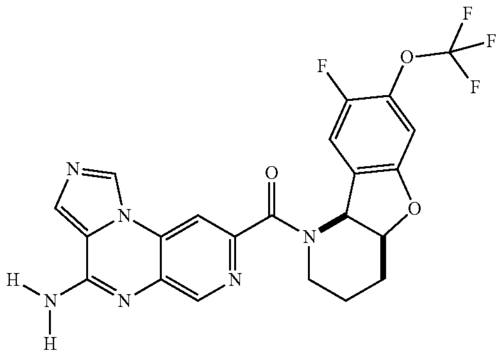 (±) |
| Ff-339 | 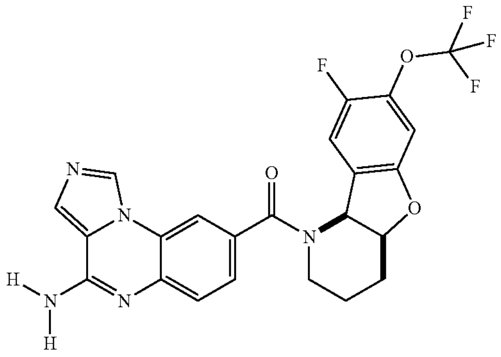 (±) |
| Ff-340 | 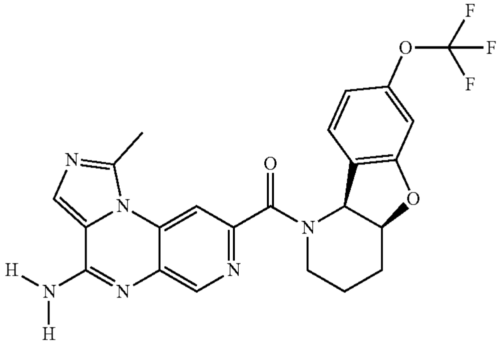 [SMILES: Cc1ncc2c(N)nc3cnc(C(=O)N4CCC[C@@H]5Oc6cc(OC(F)(F)F)ccc6[C@@H]54)cc3n12] |
| Ff-341 | 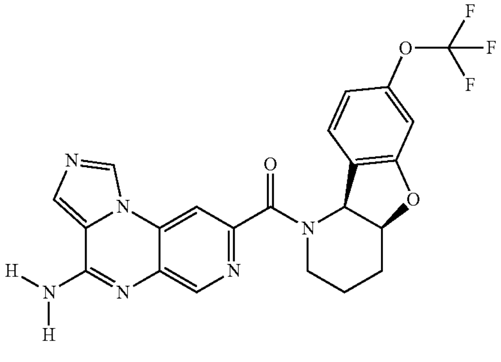 [SMILES: Nc1nc2cnc(C(=O)N3CCC[C@@H]4Oc5cc(OC(F)(F)F)ccc5[C@@H]43)cc2n2cncc12] |

TABLE 1D-continued
| Compounds | |
|---|---|
| Example | Structure |
| Ff-343 | 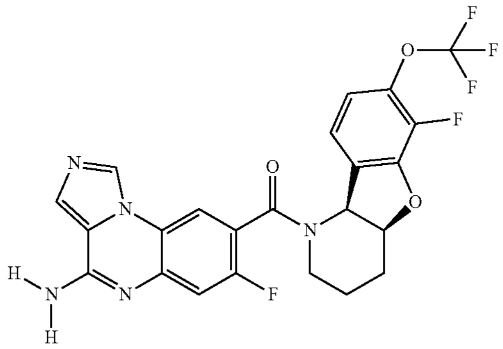 [SMILES: Nc1nc2cc(F)c(C(=O)N3CCC[C@@H]4Oc5c(ccc(OC(F)(F)F)c5F)[C@@H]43)cc2n2cncc12] |
| Ff-344 | 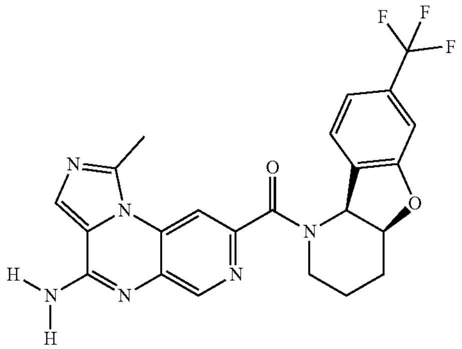 [SMILES: Cc1ncc2c(N)nc3cnc(C(=O)N4CCC[C@@H]5Oc6cc(C(F)(F)F)ccc6[C@@H]54)cc3n12] |
| Ff-345 | 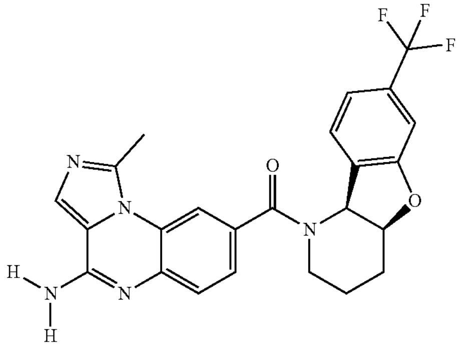 [SMILES: Cc1ncc2c(N)nc3ccc(C(=O)N4CCC[C@@H]5Oc6cc(C(F)(F)F)ccc6[C@@H]54)cc3n12] |
| Ff-346 | 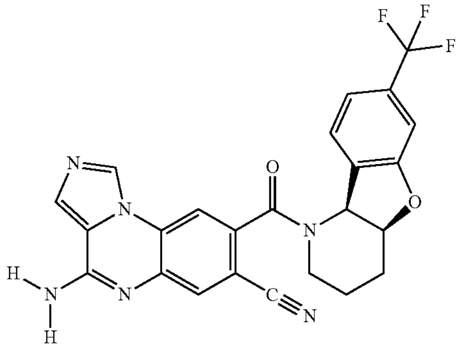 [SMILES: N#Cc1cc2nc(N)c3cncn3c2cc1C(=O)N1CCC[C@@H]2Oc3cc(C(F)(F)F)ccc3[C@@H]21] |

TABLE 1D-continued
| Compounds | |
|---|---|
| Example | Structure |
| Ff-347 | 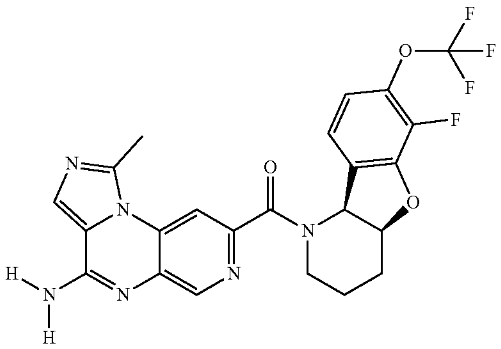 [SMILES: Cc1ncc2c(N)nc3cnc(C(=O)N4CCC[C@@H]5Oc6c(ccc(OC(F)(F)F)c6F)[C@@H]54)cc3n12] |
| Ff-348 | 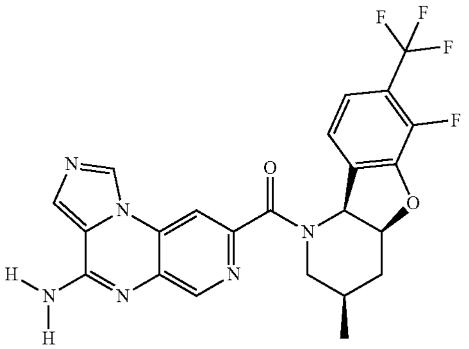 [SMILES: C[C@@H]1C[C@@H]2Oc3c(ccc(C(F)(F)F)c3F)[C@@H]2N(C(=O)c2cc3c(cn2)nc(N)c2cncn23)C1] |
| Ff-349 | 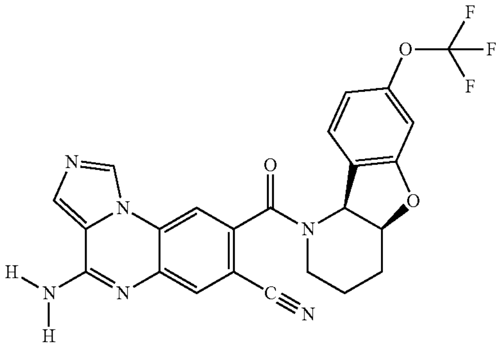 [SMILES: N#Cc1cc2nc(N)c3cncn3c2cc1C(=O)N1CCC[C@@H]2Oc3cc(OC(F)(F)F)ccc3[C@@H]21] |
| Ff-350 | 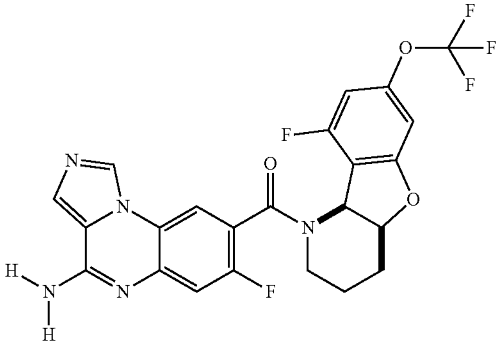 (±) |

TABLE 1D-continued
| Compounds | |
|---|---|
| Example | Structure |
| Ff-351 | 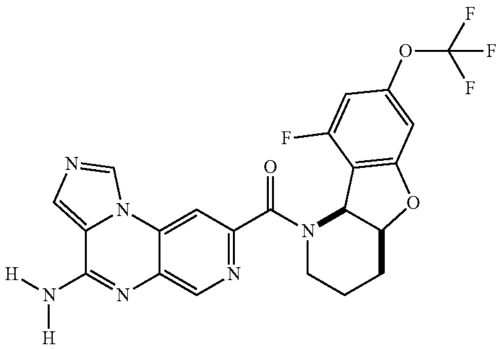 |
| Ff-357 | 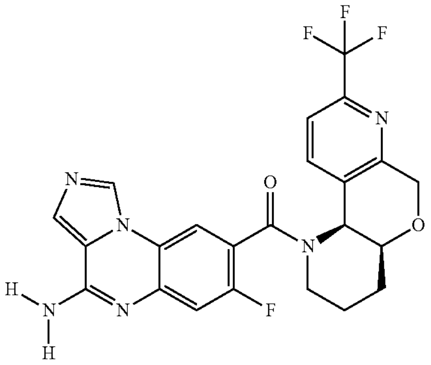 [SMILES: Nc1nc2cc(F)c(C(=O)N3CCC[C@@H]4OCc5nc(C(F)(F)F)ccc5[C@@H]43)cc2n2cncc12] |
| Ff-358 | 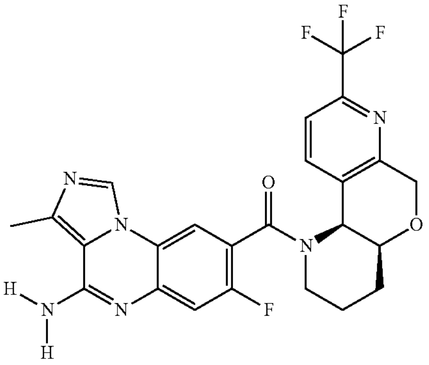 [SMILES: Cc1ncn2c1c(N)nc1cc(F)c(C(=O)N3CCC[C@@H]4OCc5nc(C(F)(F)F)ccc5[C@@H]43)cc12] |
| Ff-359 | 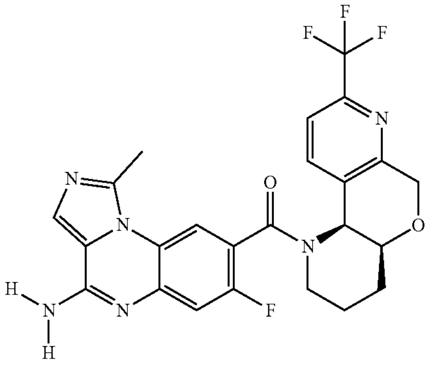 [SMILES: Cc1ncc2c(N)nc3cc(F)c(C(=O)N4CCC[C@@H]5OCc6nc(C(F)(F)F)ccc6[C@@H]54)cc3n12] |

TABLE 1D-continued
| Compounds | |
|---|---|
| Example | Structure |
| Ff-360 | 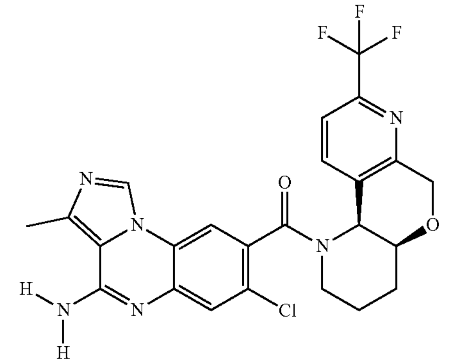 [SMILES: Cc1ncn2c1c(N)nc1cc(Cl)c(C(=O)N3CCC[C@@H]4OCc5nc(C(F)(F)F)ccc5[C@@H]43)cc12] |
| Ff-361 | 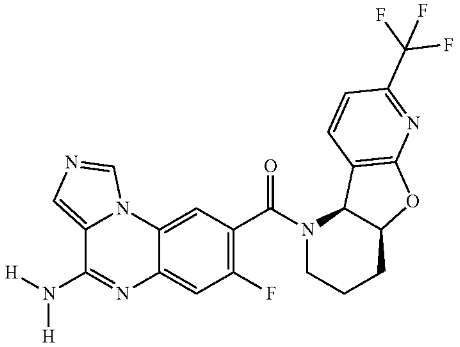 [SMILES: Nc1nc2cc(F)c(C(=O)N3CCC[C@@H]4Oc5nc(C(F)(F)F)ccc5[C@@H]43)cc2n2cncc12] |
| Ff-362 | 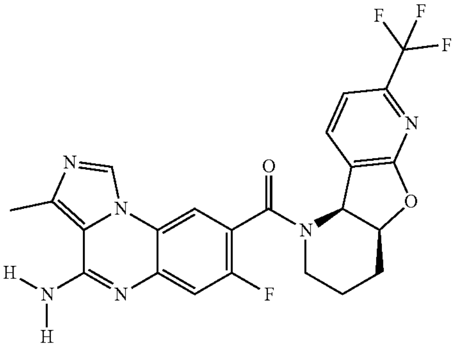 |
| Ff-363 | 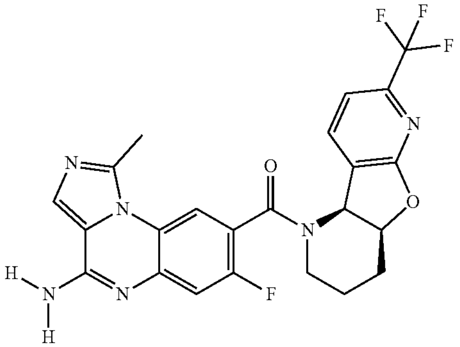 [SMILES: Cc1ncc2c(N)nc3cc(F)c(C(=O)N4CCC[C@@H]5Oc6nc(C(F)(F)F)ccc6[C@@H]54)cc3n12] |

TABLE 1D-continued
| Compounds | |
|---|---|
| Example | Structure |
| Ff-364 | 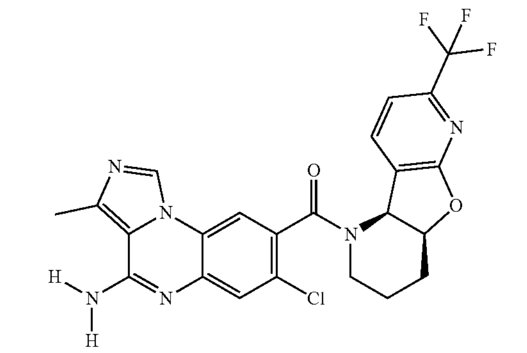 |
| Ff-365 | 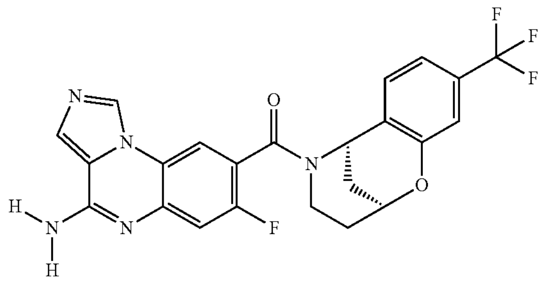 [SMILES: Nc1nc2cc(F)c(C(=O)N3CC[C@H]4C[C@@H]3c3ccc(C(F)(F)F)cc3O4)cc2n2cncc12] |
| Ff-366 | 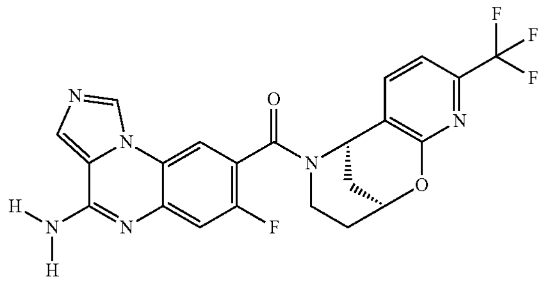 [SMILES: Nc1nc2cc(F)c(C(=O)N3CC[C@H]4C[C@@H]3c3ccc(C(F)(F)F)nc3O4)cc2n2cncc12] |
| Ff-367 | 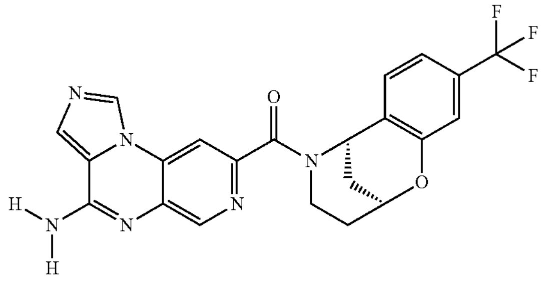 [SMILES: Nc1nc2cnc(C(=O)N3CC[C@H]4C[C@@H]3c3ccc(C(F)(F)F)cc3O4)cc2n2cncc12] |

TABLE 1D-continued
| Compounds | |
|---|---|
| Example | Structure |
| Ff-368 | 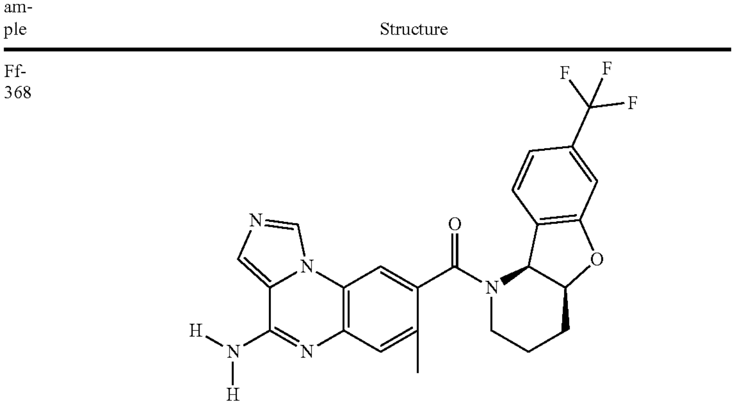 |
| Ff-369 | 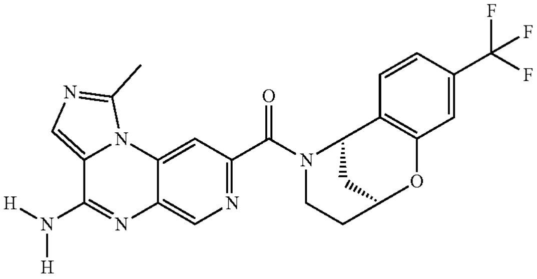 [SMILES: Cc1ncc2c(N)nc3cnc(C(=O)N4CC[C@H]5C[C@@H]4c4ccc(C(F)(F)F)cc4O5)cc3n12] |
| Ff-370 | 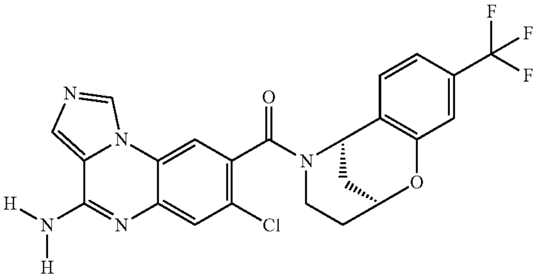 [SMILES: Nc1nc2cc(Cl)c(C(=O)N3CC[C@H]4C[C@@H]3c3ccc(C(F)(F)F)cc3O4)cc2n2cncc12] |
| Ff-371 | 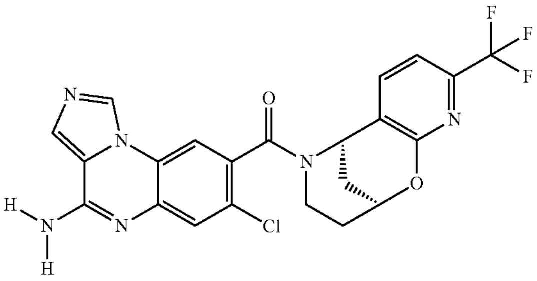 [SMILES: Nc1nc2cc(Cl)c(C(=O)N3CC[C@H]4C[C@@H]3c3ccc(C(F)(F)F)nc3O4)cc2n2cncc12] |
| Ff-372 | 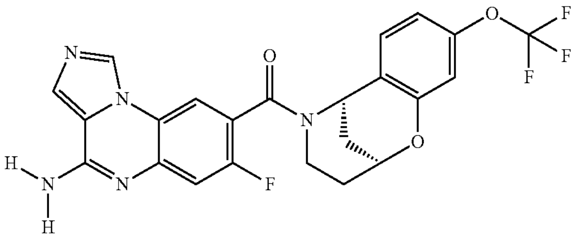<br>(±) |

TABLE 1D-continued
| Compounds | |
|---|---|
| Example | Structure |
| Ff-373 | 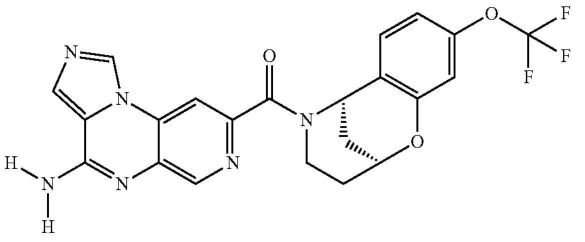 (±) |
| Ff-374 | 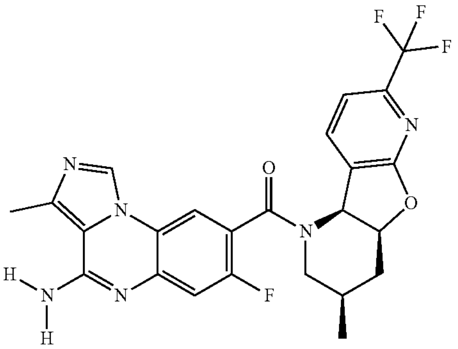 [SMILES: Cc1ncn2c1c(N)nc1cc(F)c(C(=O)N3C[C@H](C)C[C@@H]4Oc5nc(C(F)(F)F)ccc5[C@@H]43)cc12] |
| Ff-375 | 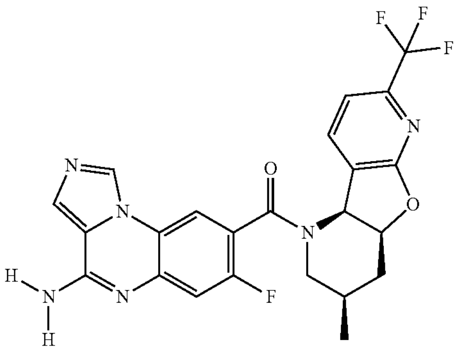 |
| Ff-376 | 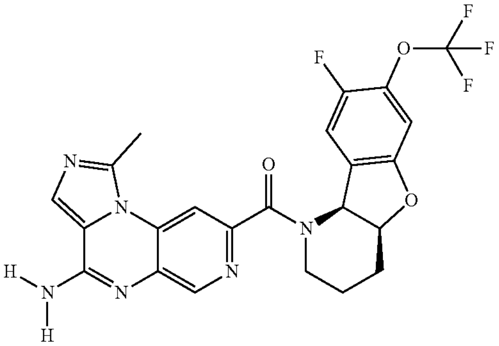 [SMILES: Cc1ncc2c(N)nc3cnc(C(=O)N4CCC[C@@H]5Oc6cc(OC(F)(F)F)c(F)cc6[C@@H]54)cc3n12] |

TABLE 1D-continued
| Compounds | |
| --- | --- |
| Example | Structure |
| Ff-377 | 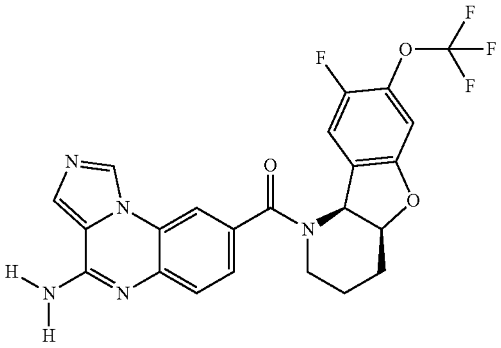 [SMILES: Nc1nc2ccc(C(=O)N3CCC[C@@H]4Oc5cc(OC(F)(F)F)c(F)cc5[C@@H]43)cc2n2cncc12] |
| Ff-378 | 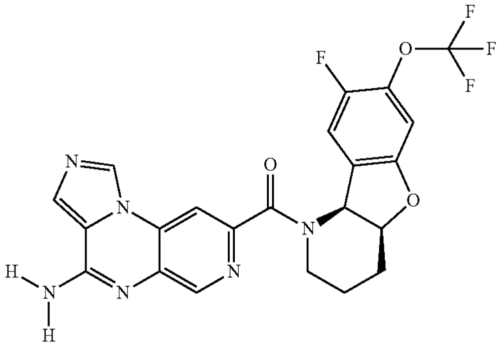 [SMILES: Nc1nc2cnc(C(=O)N3CCC[C@@H]4Oc5cc(OC(F)(F)F)c(F)cc5[C@@H]43)cc2n2cncc12] |
| Ff-379 | 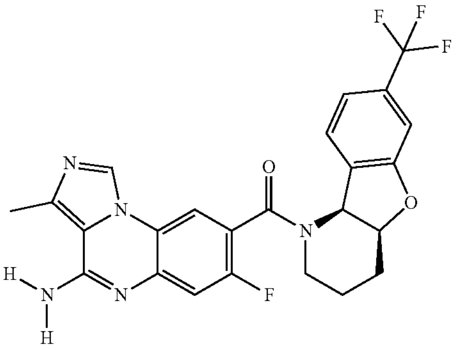 |
| Ff-380 | 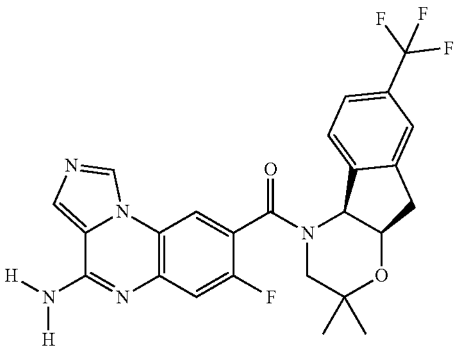 [SMILES: CC1(C)CN(C(=O)c2cc3c(cc2F)nc(N)c2cncn23)[C@H]2c3ccc(C(F)(F)F)cc3C[C@H]2O1] |

TABLE 1D-continued
| Compounds | |
|---|---|
| Example | Structure |
| Ff-381 | 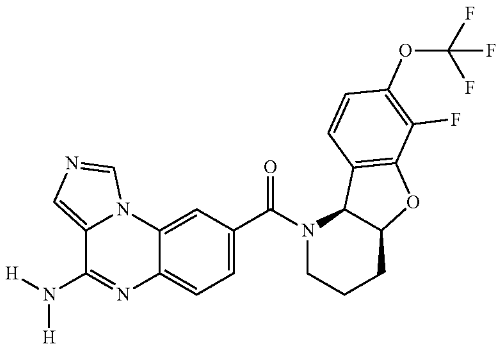 [SMILES: Nc1nc2ccc(C(=O)N3CCC[C@@H]4Oc5c(ccc(OC(F)(F)F)c5F)[C@@H]43)cc2n2cncc12] |
| Ff-383 | 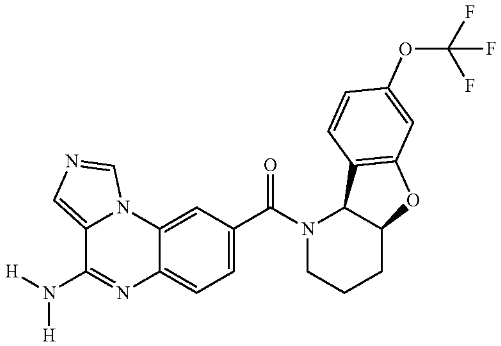 [SMILES: Nc1nc2ccc(C(=O)N3CCC[C@@H]4Oc5cc(OC(F)(F)F)ccc5[C@@H]43)cc2n2cncc12] |
| Ff-384 | 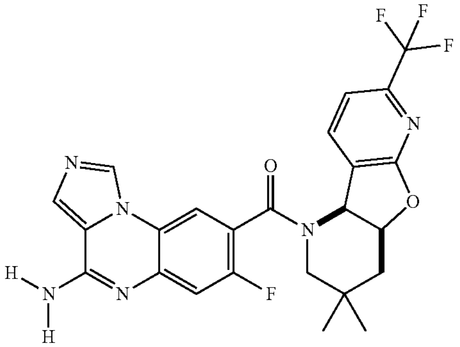 |
| Ff-385 | 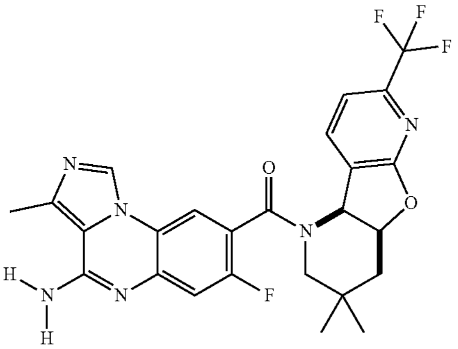 (±) |

TABLE 1D-continued
| Compounds | |
|---|---|
| Example | Structure |
| Ff-386 | 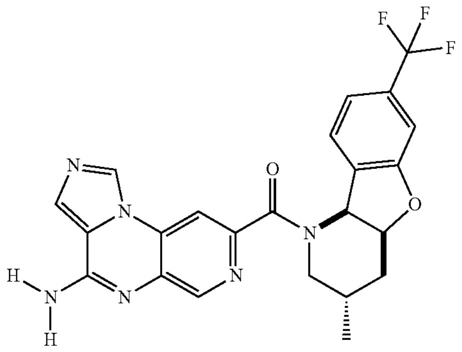 |
| Ff-387 | 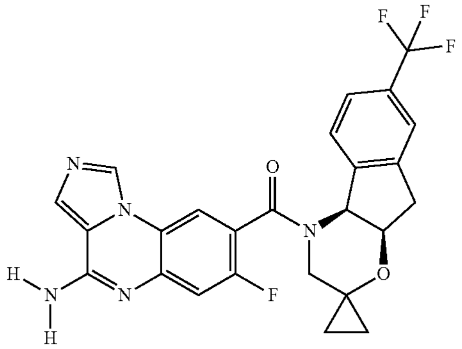 [SMILES: Nc1nc2cc(F)c(C(=O)N3CC4(CC4)O[C@@H]4Cc5cc(C(F)(F)F)ccc5[C@@H]43)cc2n2cncc12] |
| Ff-388 | 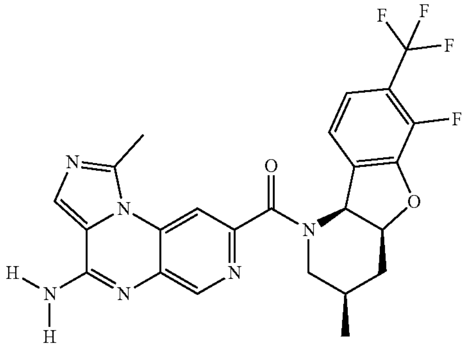 [SMILES: Cc1ncc2c(N)nc3cnc(C(=O)N4C[C@H](C)C[C@@H]5Oc6c(ccc(C(F)(F)F)c6F)[C@@H]54)cc3n12] |
| Ff-389 | 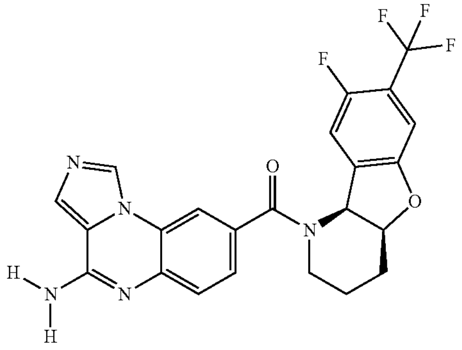 [SMILES: Nc1nc2ccc(C(=O)N3CCC[C@@H]4Oc5cc(C(F)(F)F)c(F)cc5[C@@H]43)cc2n2cncc12] |

TABLE 1D-continued
| Compounds | |
|---|---|
| Example | Structure |
| Ff-390 | 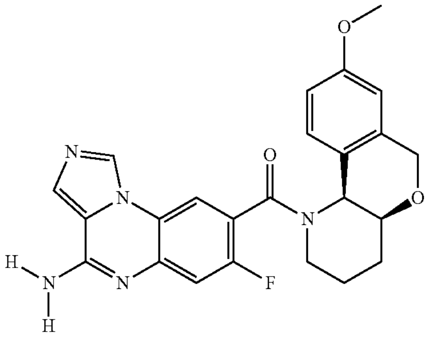 [SMILES: COc1ccc2c(c1)CO[C@H]1CCCN(C(=O)c3cc4c(cc3F)nc(N)c3cncn34)[C@@H]21] |
| Ff-391 | 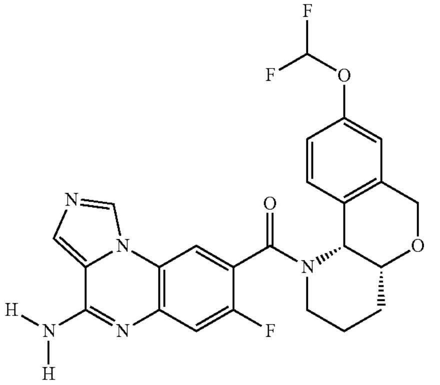 [SMILES: Nc1nc2cc(F)c(C(=O)N3CCC[C@H]4OCc5cc(OC(F)F)ccc5[C@H]43)cc2n2cncc12] |
| Ff-392 | 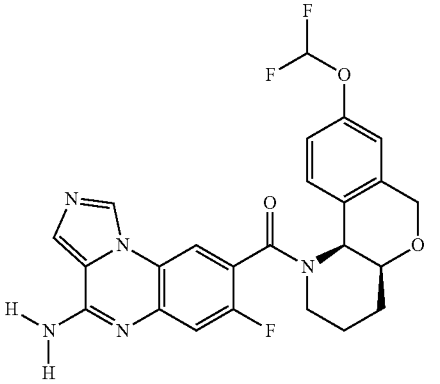 [SMILES: Nc1nc2cc(F)c(C(=O)N3CCC[C@@H]4OCc5cc(OC(F)F)ccc5[C@@H]43)cc2n2cncc12] |
| Ff-393 | 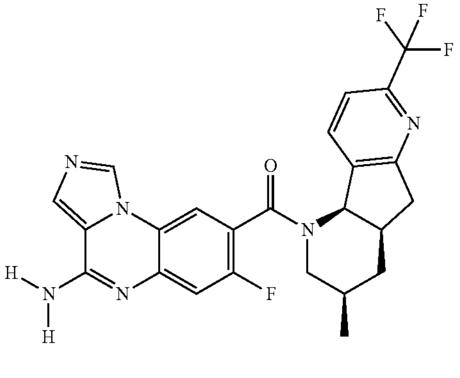 [SMILES: C[C@@H]1C[C@@H]2Cc3nc(C(F)(F)F)ccc3[C@@H]2N(C(=O)c2cc3c(cc2F)nc(N)c2cncn23)C1] |

TABLE 1D-continued
| Compounds | |
|---|---|
| Example | Structure |
| Ff-394 | 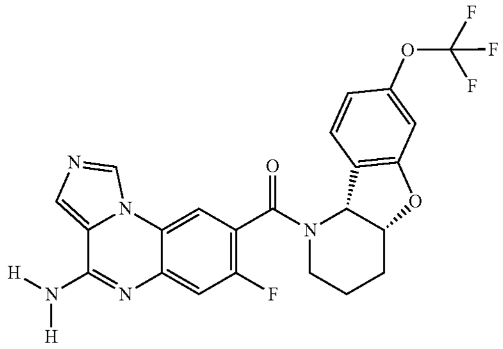 [SMILES: Nc1nc2cc(F)c(C(=O)N3CCC[C@H]4Oc5cc(OC(F)(F)F)ccc5[C@H]43)cc2n2cncc12] |
| Ff-395 | 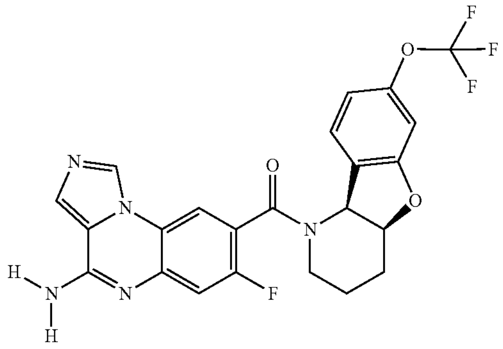 [SMILES: Nc1nc2cc(F)c(C(=O)N3CCC[C@@H]4Oc5cc(OC(F)(F)F)ccc5[C@@H]43)cc2n2cncc12] |
| Ff-396 | 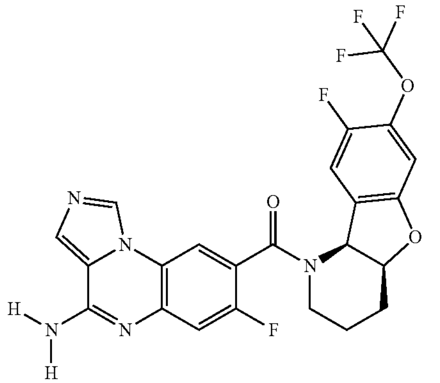 [SMILES: Nc1nc2cc(F)c(C(=O)N3CCC[C@@H]4Oc5cc(OC(F)(F)F)c(F)cc5[C@@H]43)cc2n2cncc12] |
| Ff-397 | 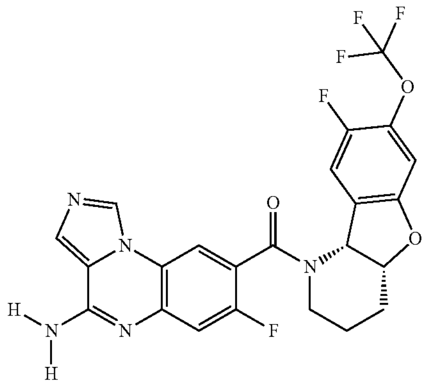 [SMILES: Nc1nc2cc(F)c(C(=O)N3CCC[C@H]4Oc5cc(OC(F)(F)F)c(F)cc5[C@H]43)cc2n2cncc12] |

TABLE 1D-continued
| Compounds | |
|---|---|
| Example | Structure |
| Ff-399 | 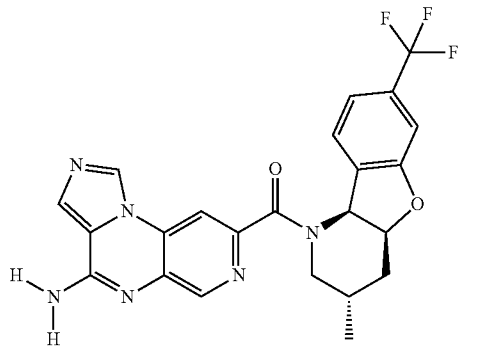 [SMILES: C[C@H]1C[C@@H]2Oc3cc(C(F)(F)F)ccc3[C@@H]2N(C(=O)c2cc3c(cn2)nc(N)c2cncn23)C1] |
| Ff-400 | 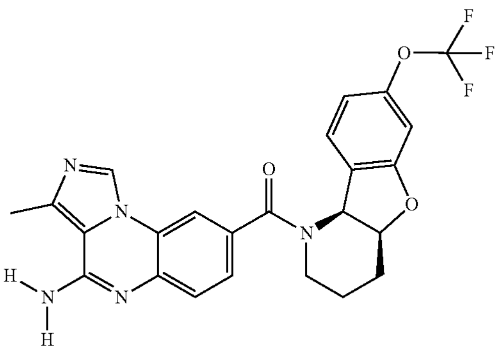 [SMILES: Cc1ncn2c1c(N)nc1ccc(C(=O)N3CCC[C@@H]4Oc5cc(OC(F)(F)F)ccc5[C@@H]43)cc12] |
| Ff-406 | 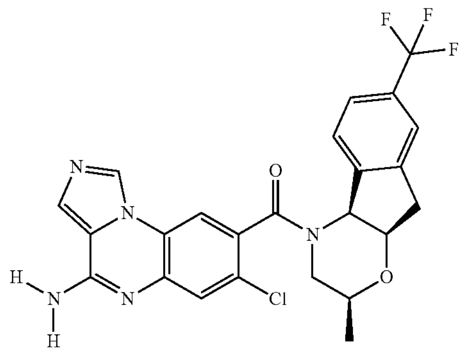 [SMILES: C[C@H]1CN(C(=O)c2cc3c(cc2Cl)nc(N)c2cncn23)[C@H]2c3ccc(C(F)(F)F)cc3C[C@H]2O1] |
| Ff-427 | 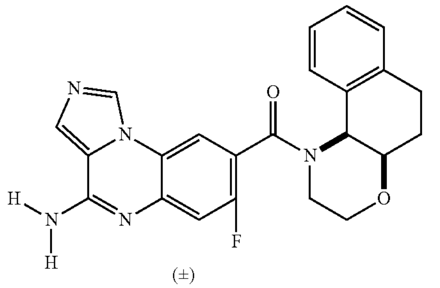 [SMILES: Nc1nc2cc(F)c(C(=O)N3CCO[C@@H]4CCc5ccccc5[C@@H]43)cc2n2cncc12] (±) |

TABLE 1D-continued
| Compounds | |
|---|---|
| Example | Structure |
| Ff-432 | 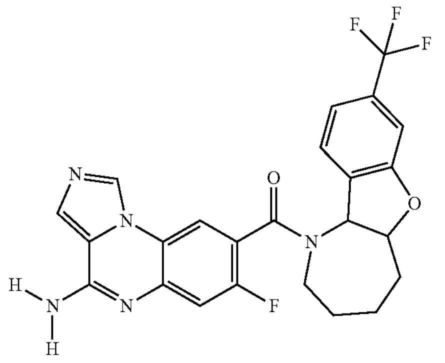 [SMILES: Nc1nc2cc(F)c(C(=O)N3CCCCC4Oc5cc(C(F)(F)F)ccc5C43)cc2n2cncc12] |
| Ff-448 | 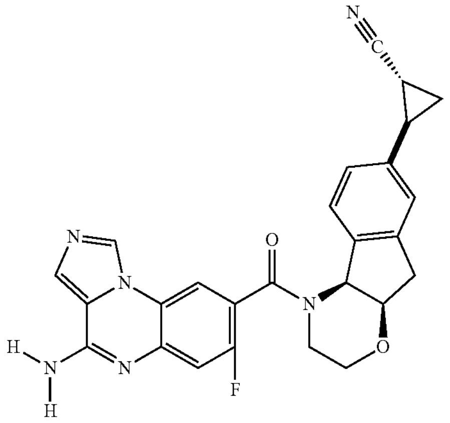 [SMILES: N#C[C@@H]1C[C@H]1c1ccc2c(c1)C[C@H]1OCCN(C(=O)c3cc4c(cc3F)nc(N)c3cncn34)[C@@H]21] |
| Ff-461 | 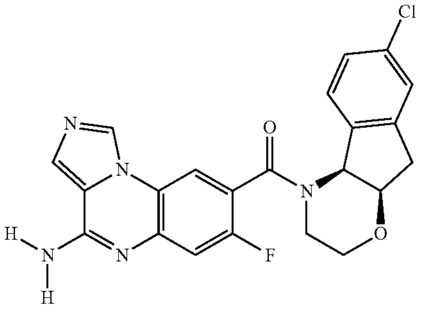 |
| Ff-462 | 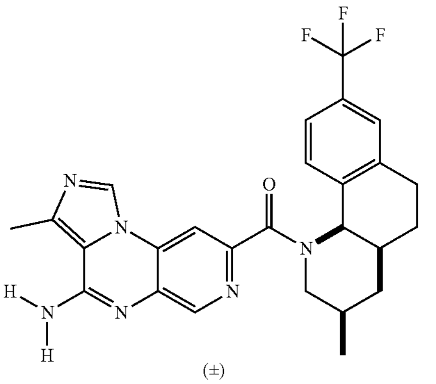 [SMILES: Cc1ncn2c1c(N)nc1cnc(C(=O)N3C[C@H](C)C[C@@H]4CCc5cc(C(F)(F)F)ccc5[C@@H]43)cc12] (±) |

TABLE 1D-continued
| Compounds | |
|---|---|
| Example | Structure |
| Ff-463 | 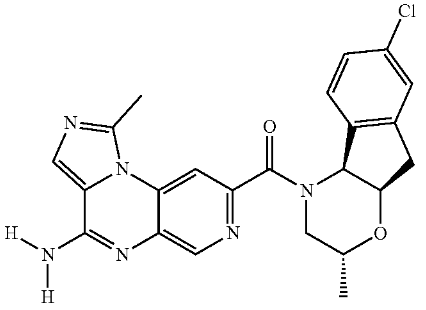 [SMILES: Cc1ncc2c(N)nc3cnc(C(=O)N4C[C@@H](C)O[C@@H]5Cc6cc(Cl)ccc6[C@@H]54)cc3n12] |
| Ff-464 | 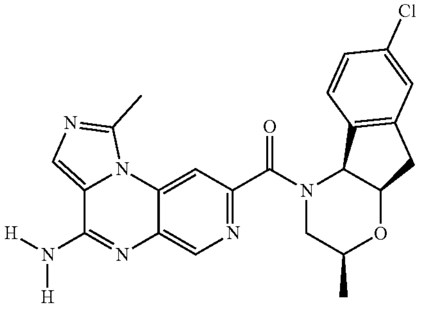 [SMILES: Cc1ncc2c(N)nc3cnc(C(=O)N4C[C@H](C)O[C@@H]5Cc6cc(Cl)ccc6[C@@H]54)cc3n12] |
| Ff-467 | 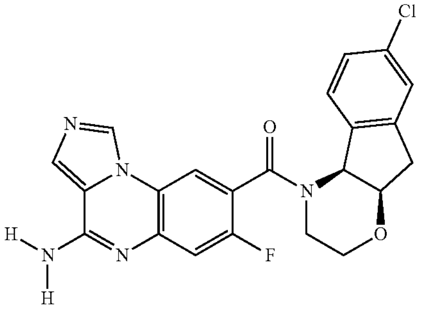 |
| Ff-487 | 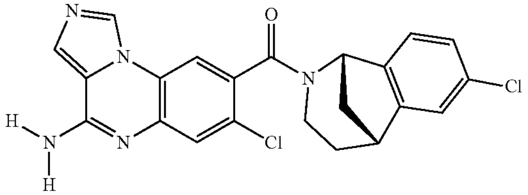 [SMILES: Nc1nc2cc(Cl)c(C(=O)N3CC[C@@H]4C[C@H]3c3ccc(Cl)cc34)cc2n2cncc12] |
| Ff-488 | 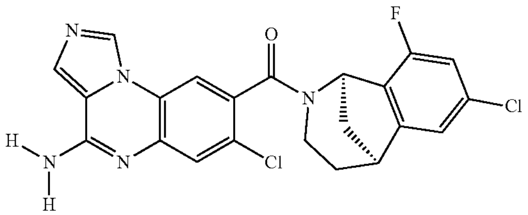 [SMILES: Nc1nc2cc(Cl)c(C(=O)N3CC[C@H]4C[C@@H]3c3c(F)cc(Cl)cc34)cc2n2cncc12] |

TABLE 1D-continued
| Example | Compounds Structure |
| --- | --- |
| Ff-489 | 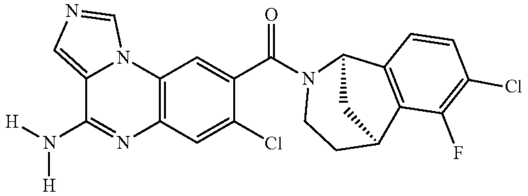 [SMILES: Nc1nc2cc(Cl)c(C(=O)N3CC[C@H]4C[C@@H]3c3ccc(Cl)c(F)c34)cc2n2cncc12] |
| Ff-491 | 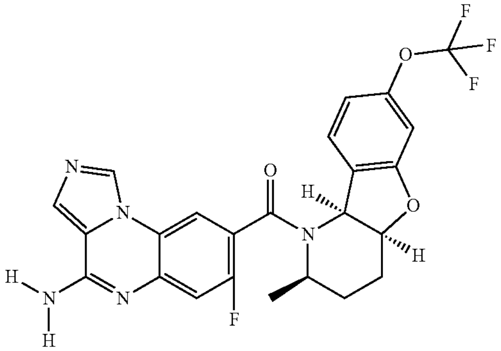 [SMILES: C[C@@H]1CC[C@@H]2Oc3cc(OC(F)(F)F)ccc3[C@@H]2N1C(=O)c1cc2c(cc1F)nc(N)c1cncn12] |
| Ff-495 | 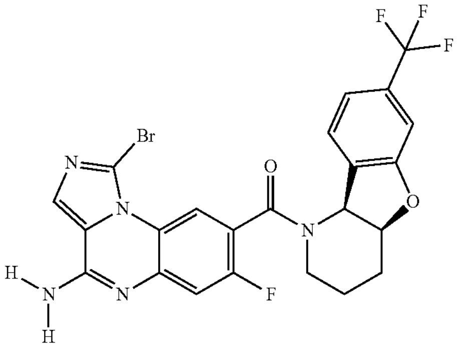 [SMILES: Nc1nc2cc(F)c(C(=O)N3CCC[C@@H]4Oc5cc(C(F)(F)F)ccc5[C@@H]43)cc2n2c(Br)ncc12] |
| Ff-496 | 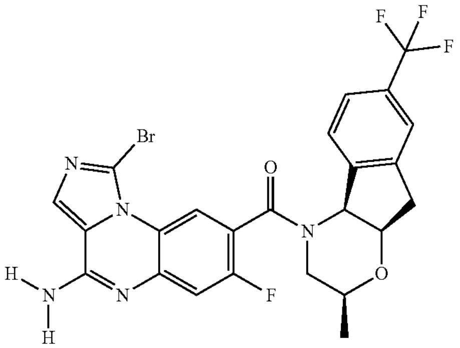 [SMILES: C[C@H]1CN(C(=O)c2cc3c(cc2F)nc(N)c2cnc(Br)n23)[C@H]2c3ccc(C(F)(F)F)cc3C[C@H]2O1] |

TABLE 1D-continued
| Compounds | |
|---|---|
| Example | Structure |
| Ff-498 | 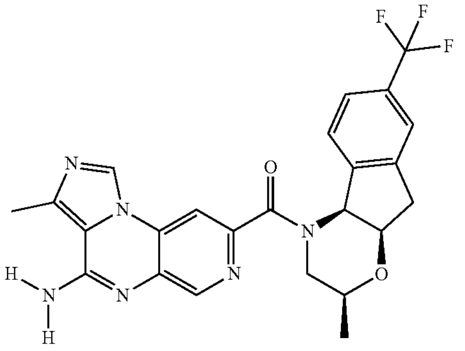 [SMILES: Cc1ncn2c1c(N)nc1cnc(C(=O)N3C[C@H](C)O[C@@H]4Cc5cc(C(F)(F)F)ccc5[C@@H]43)cc12] |
| Ff-499 | 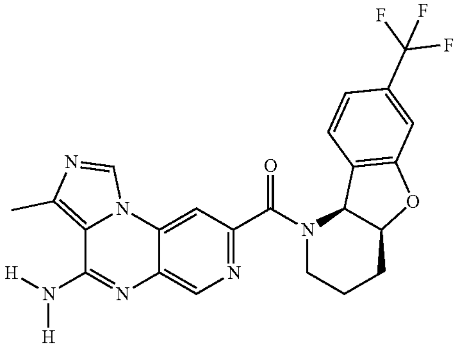 [SMILES: Cc1ncn2c1c(N)nc1cnc(C(=O)N3CCC[C@@H]4Oc5cc(C(F)(F)F)ccc5[C@@H]43)cc12] |
| Ff-500 | 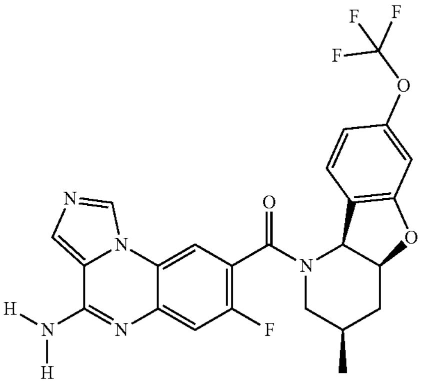 [SMILES: C[C@@H]1C[C@@H]2Oc3cc(OC(F)(F)F)ccc3[C@@H]2N(C(=O)c2cc3c(cc2F)nc(N)c2cncn23)C1] |
| Ff-501 | 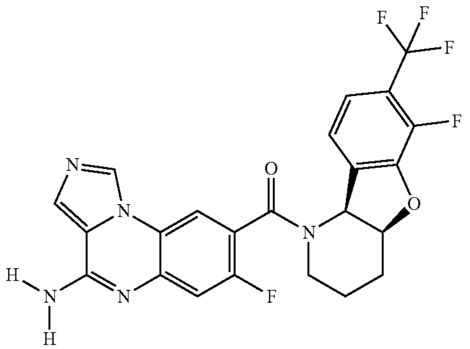 [SMILES: Nc1nc2cc(F)c(C(=O)N3CCC[C@@H]4Oc5c(ccc(C(F)(F)F)c5F)[C@@H]43)cc2n2cncc12] |

TABLE 1D-continued
| Compounds | |
|---|---|
| Example | Structure |
| Ff-507 | 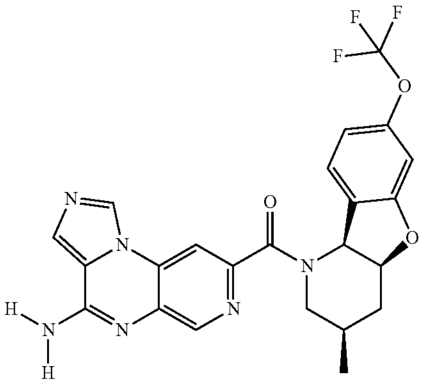 [SMILES: C[C@@H]1C[C@@H]2Oc3cc(OC(F)(F)F)ccc3[C@@H]2N(C(=O)c2cc3c(cn2)nc(N)c2cncn23)C1] |
| Ff-510 | 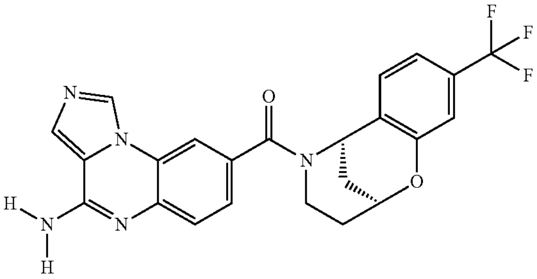 [SMILES: Nc1nc2ccc(C(=O)N3CC[C@H]4C[C@@H]3c3ccc(C(F)(F)F)cc3O4)cc2n2cncc12] |
| Ff-539 | 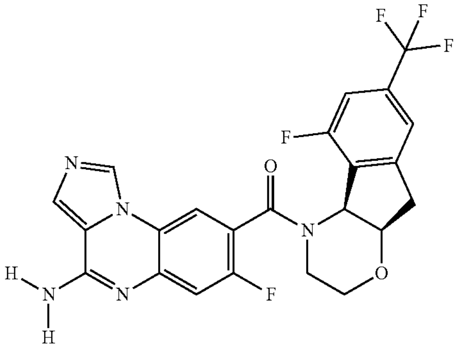 [SMILES: Nc1nc2cc(F)c(C(=O)N3CCO[C@@H]4Cc5cc(C(F)(F)F)cc(F)c5[C@@H]43)cc2n2cncc12] |
| Ff-540 | 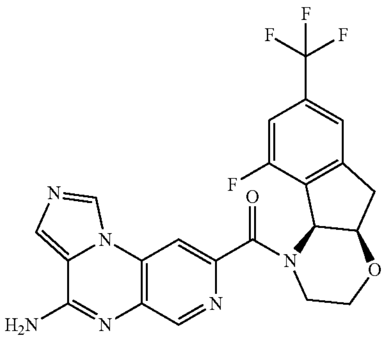 |

TABLE 1D-continued
| Compounds | |
|---|---|
| Example | Structure |
| Ff-578 | 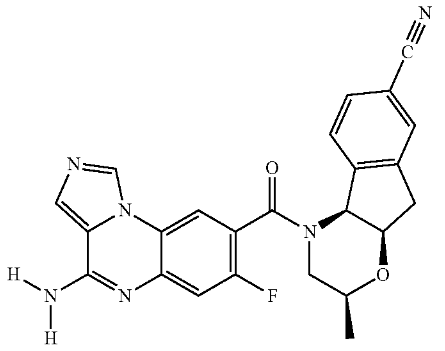 [SMILES: C[C@H]1CN(C(=O)c2cc3c(cc2F)nc(N)c2cncn23)[C@H]2c3ccc(C#N)cc3C[C@H]2O1] |
| Ff-586 | 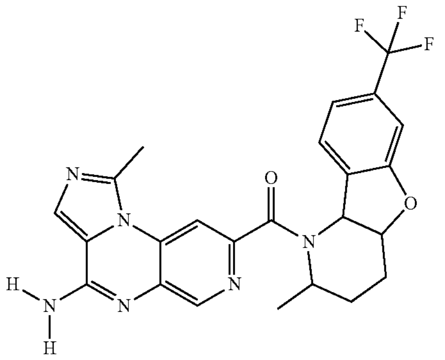 [SMILES: Cc1ncc2c(N)nc3cnc(C(=O)N4C(C)CCC5Oc6cc(C(F)(F)F)ccc6C54)cc3n12] |
| Ff-587 | 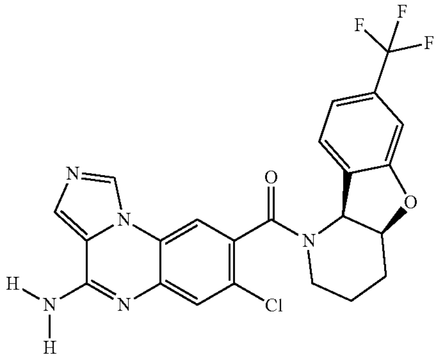 [SMILES: Nc1nc2cc(Cl)c(C(=O)N3CCC[C@@H]4Oc5cc(C(F)(F)F)ccc5[C@@H]43)cc2n2cncc12] |
| Ff-588 | 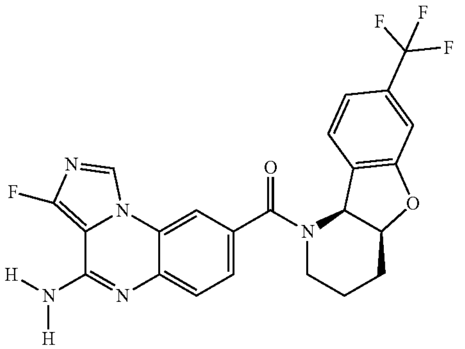 [SMILES: Nc1nc2ccc(C(=O)N3CCC[C@@H]4Oc5cc(C(F)(F)F)ccc5[C@@H]43)cc2n2cnc(F)c12] |

TABLE 1D-continued
| Example | Compounds Structure |
|---|---|
| Ff-595 | 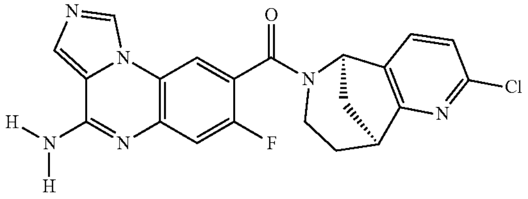 [SMILES: Nc1nc2cc(F)c(C(=O)N3CC[C@H]4C[C@@H]3c3ccc(Cl)nc34)cc2n2cncc12] |
| Ff-598 | 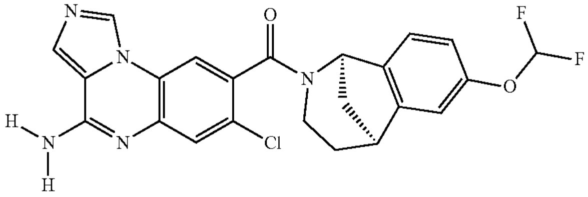 [SMILES: Nc1nc2cc(Cl)c(C(=O)N3CC[C@H]4C[C@@H]3c3ccc(OC(F)F)cc34)cc2n2cncc12] |
| Ff-599 | 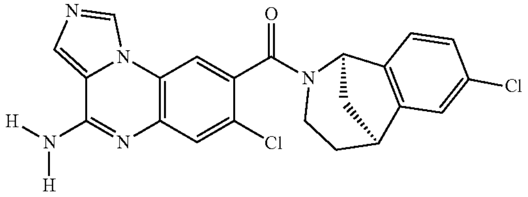 [SMILES: Nc1nc2cc(Cl)c(C(=O)N3CC[C@H]4C[C@@H]3c3ccc(Cl)cc34)cc2n2cncc12] |
| Ff-602 | 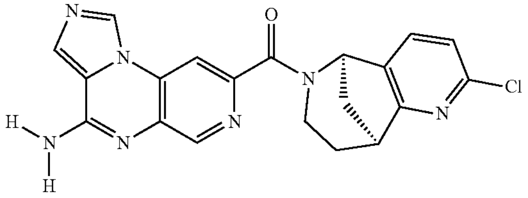 [SMILES: Nc1nc2cnc(C(=O)N3CC[C@H]4C[C@@H]3c3ccc(Cl)nc34)cc2n2cncc12] |
| Ff-603 | 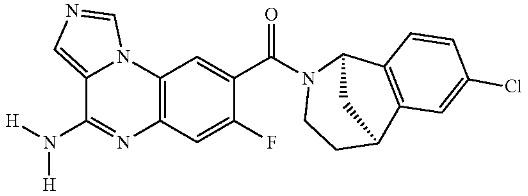 [SMILES: Nc1nc2cc(F)c(C(=O)N3CC[C@H]4C[C@@H]3c3ccc(Cl)cc34)cc2n2cncc12] |
| Ff-611 | 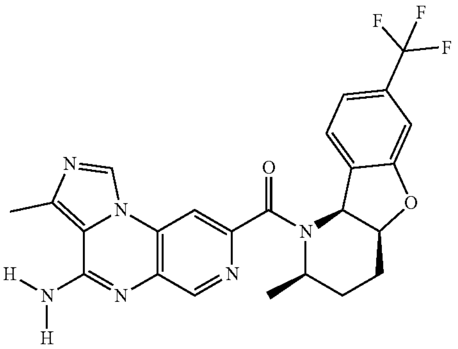 [SMILES: Cc1ncn2c1c(N)nc1cnc(C(=O)N3[C@H](C)CC[C@@H]4Oc5cc(C(F)(F)F)ccc5[C@@H]43)cc12] |

TABLE 1D-continued
| Compounds | |
|---|---|
| Example | Structure |
| Ff-612 | 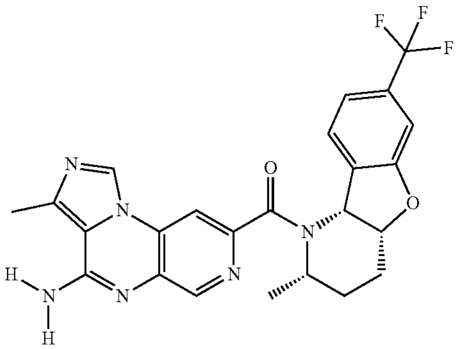 [SMILES: Cc1ncn2c1c(N)nc1cnc(C(=O)N3[C@@H]4c5ccc(C(F)(F)F)cc5O[C@@H]4CC[C@@H]3C)cc12] |
| Ff-615 | 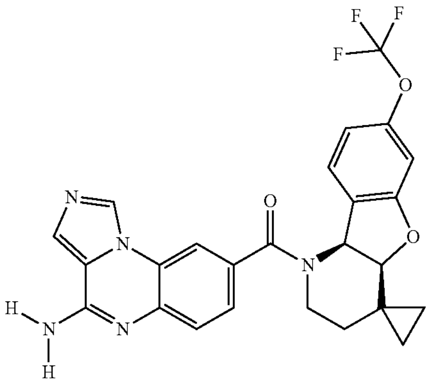 [SMILES: Nc1nc2ccc(C(=O)N3CCC4(CC4)[C@@H]4Oc5cc(OC(F)(F)F)ccc5[C@@H]43)cc2n2cncc12] |
| Ff-616 | 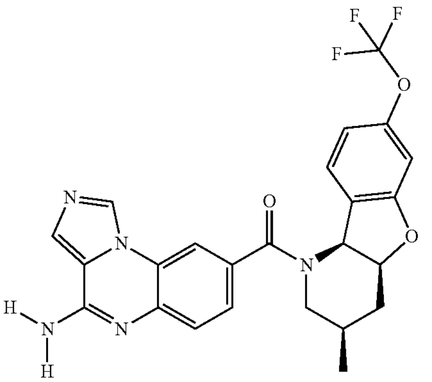 [SMILES: C[C@@H]1C[C@@H]2Oc3cc(OC(F)(F)F)ccc3[C@@H]2N(C(=O)c2ccc3nc(N)c4cncn4c3c2)C1] |
| Ff-617 | 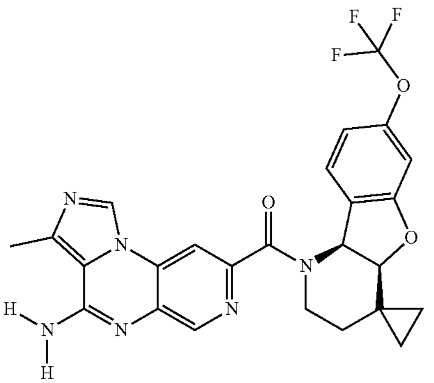 [SMILES: Cc1ncn2c1c(N)nc1cnc(C(=O)N3CCC4(CC4)[C@@H]4Oc5cc(OC(F)(F)F)ccc5[C@@H]43)cc12] |

TABLE 1D-continued
| Example | Compounds Structure |
|---|---|
| Ff-618 | 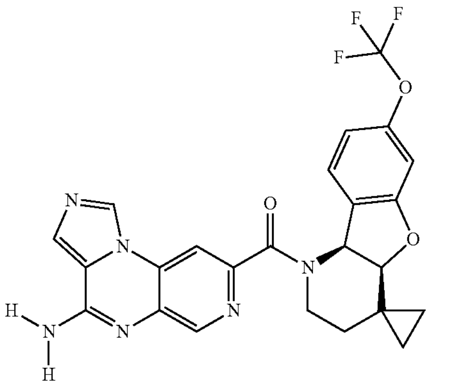 [SMILES: Nc1nc2cnc(C(=O)N3CCC4(CC4)[C@@H]4Oc5cc(OC(F)(F)F)ccc5[C@@H]43)cc2n2cncc12] |
| Ff-619 | 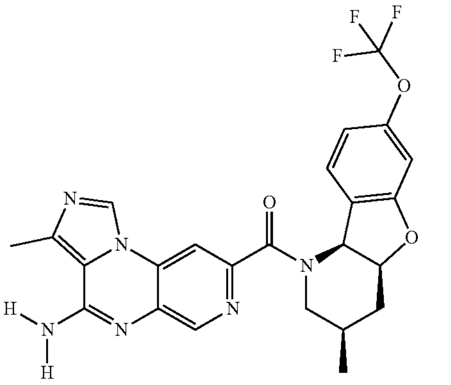 [SMILES: Cc1ncn2c1c(N)nc1cnc(C(=O)N3C[C@H](C)C[C@@H]4Oc5cc(OC(F)(F)F)ccc5[C@@H]43)cc12] |
| Ff-620 | 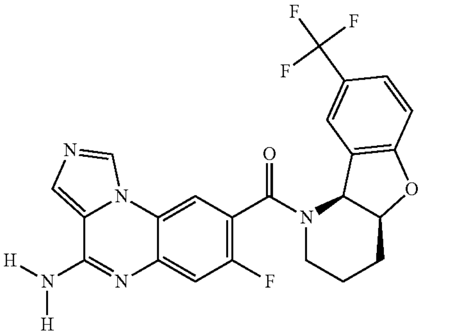 [SMILES: Nc1nc2cc(F)c(C(=O)N3CCC[C@@H]4Oc5ccc(C(F)(F)F)cc5[C@@H]43)cc2n2cncc12] |
| Ff-621 | 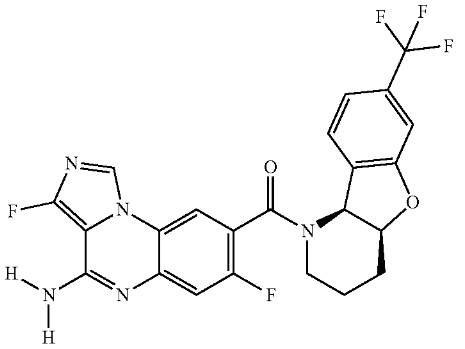 [SMILES: Nc1nc2cc(F)c(C(=O)N3CCC[C@@H]4Oc5cc(C(F)(F)F)ccc5[C@@H]43)cc2n2cnc(F)c12] |

TABLE 1D-continued
| Compounds | |
|---|---|
| Example | Structure |
| Ff-622 | 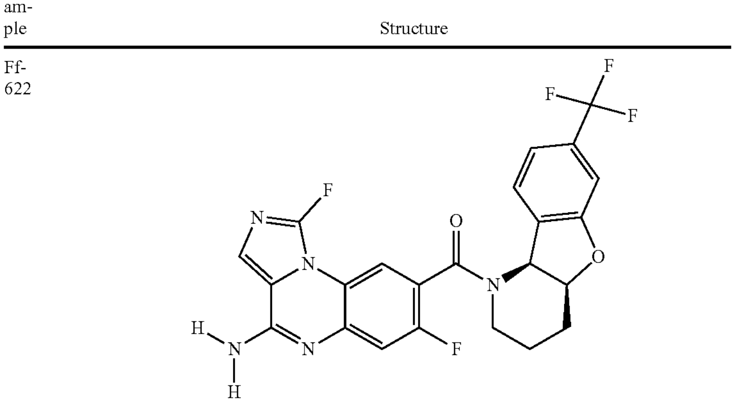 |
| Ff-623 | 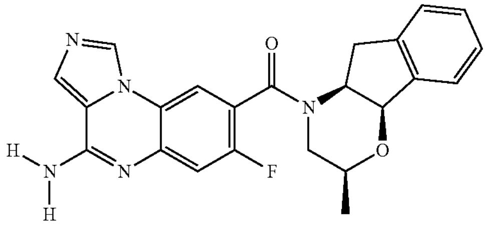 [SMILES: C[C@H]1CN(C(=O)c2cc3c(cc2F)nc(N)c2cncn23)[C@H]2Cc3ccccc3[C@H]2O1] |
| Ff-624 | 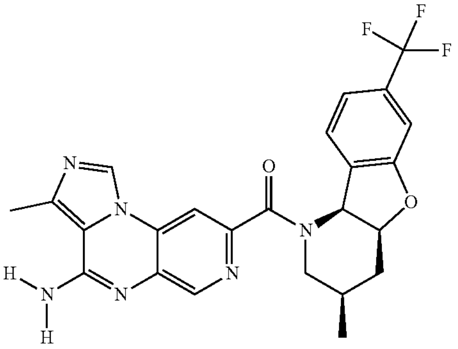 [SMILES: Cc1ncn2c1c(N)nc1cnc(C(=O)N3C[C@H](C)C[C@@H]4Oc5cc(C(F)(F)F)ccc5[C@@H]43)cc12] |
| Ff-625 | 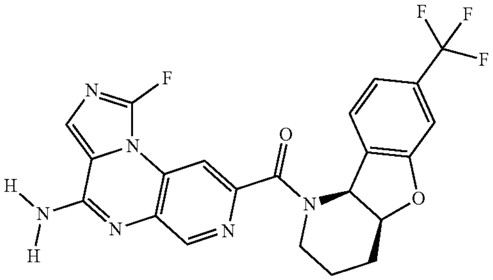 [SMILES: Nc1nc2cnc(C(=O)N3CCC[C@@H]4Oc5cc(C(F)(F)F)ccc5[C@@H]43)cc2n2c(F)ncc12] |
| Ff-626 | 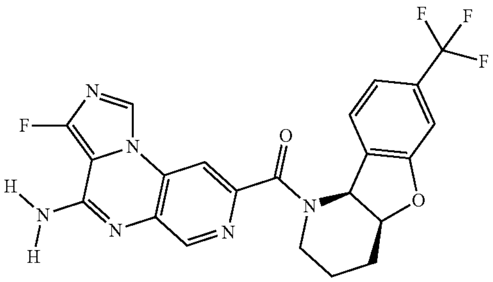 [SMILES: Nc1nc2cnc(C(=O)N3CCC[C@@H]4Oc5cc(C(F)(F)F)ccc5[C@@H]43)cc2n2cnc(F)c12] |

TABLE 1D-continued
| Compounds | |
|---|---|
| Ex-am-ple | Structure |
| Ff-627 | 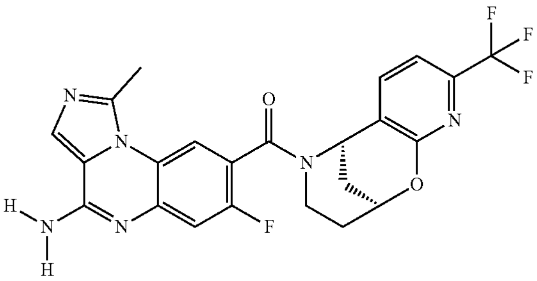 [SMILES: Cc1ncc2c(N)nc3cc(F)c(C(=O)N4CC[C@H]5C[C@@H]4c4ccc(C(F)(F)F)nc4O5)cc3n12] |
| Ff-628 | 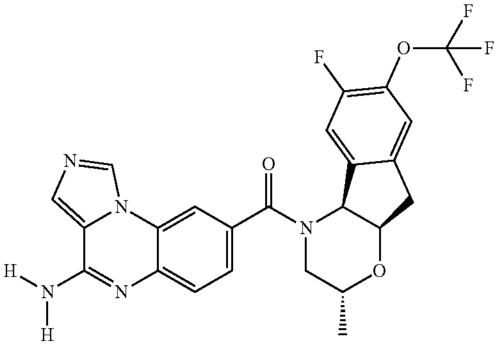 [SMILES: C[C@@H]1CN(C(=O)c2ccc3nc(N)c4cncn4c3c2)[C@H]2c3cc(F)c(OC(F)(F)F)cc3C[C@H]2O1] |
| Ff-629 | 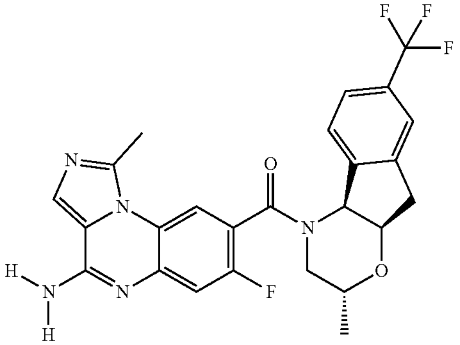 [SMILES: Cc1ncc2c(N)nc3cc(F)c(C(=O)N4C[C@@H](C)O[C@@H]5Cc6cc(C(F)(F)F)ccc6[C@@H]54)cc3n12] |
| Ff-630 | 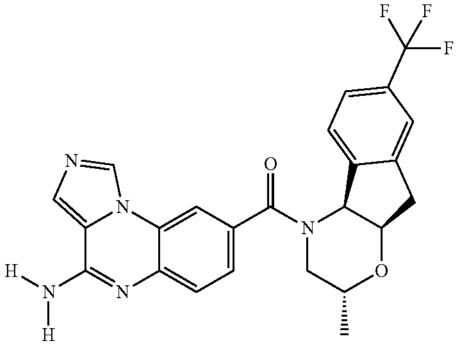 [SMILES: C[C@@H]1CN(C(=O)c2ccc3nc(N)c4cncn4c3c2)[C@H]2c3ccc(C(F)(F)F)cc3C[C@H]2O1] |

TABLE 1D-continued
| Compounds | |
| --- | --- |
| Example | Structure |
| Ff-631 | 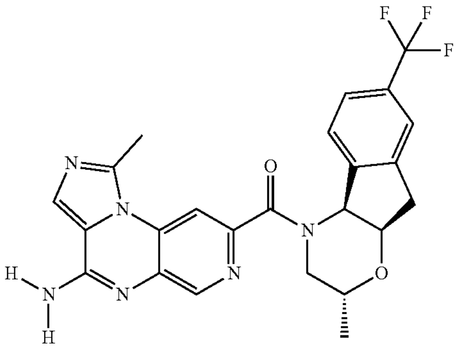 [SMILES: Cc1ncc2c(N)nc3cnc(C(=O)N4C[C@@H](C)O[C@@H]5Cc6cc(C(F)(F)F)ccc6[C@@H]54)cc3n12] |
| Ff-632 | 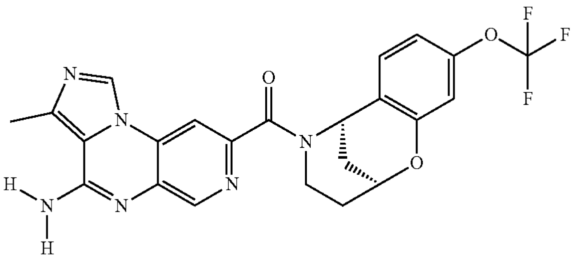 [SMILES: Cc1ncn2c1c(N)nc1cnc(C(=O)N3CC[C@H]4C[C@@H]3c3ccc(OC(F)(F)F)cc3O4)cc12] |
| Ff-633 | 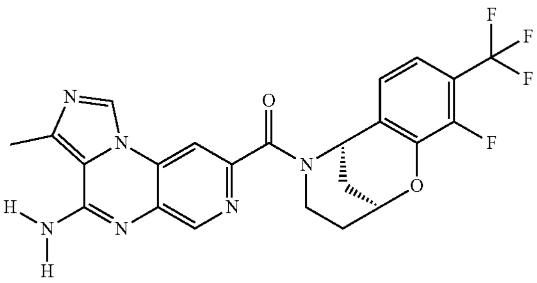 |
| Ff-634 | 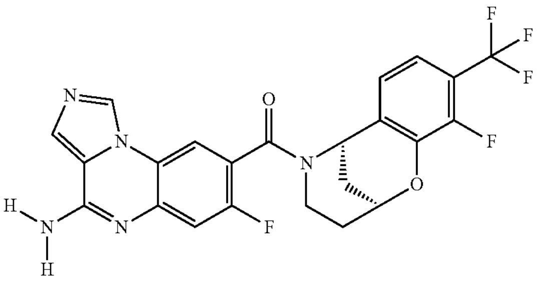 |
| Ff-635 | 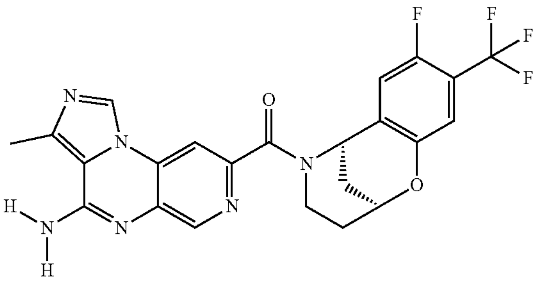 [SMILES: Cc1ncn2c1c(N)nc1cnc(C(=O)N3CC[C@H]4C[C@@H]3c3cc(F)c(C(F)(F)F)cc3O4)cc12] |

TABLE 1D-continued
| Compounds | |
|---|---|
| Example | Structure |
| Ff-636 | 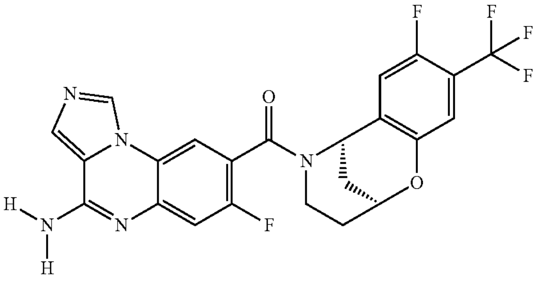 [SMILES: Nc1nc2cc(F)c(C(=O)N3CC[C@H]4C[C@@H]3c3cc(F)c(C(F)(F)F)cc3O4)cc2n2cncc12] |
| Ff-637 | 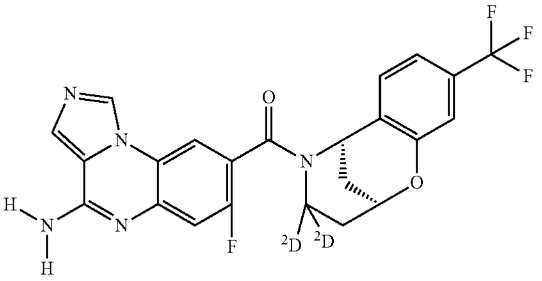 [SMILES: [2H]C1([2H])C[C@H]2C[C@H](c3ccc(C(F)(F)F)cc3O2)N1C(=O)c1cc2c(cc1F)nc(N)c1cncn12] |
| Ff-638 | 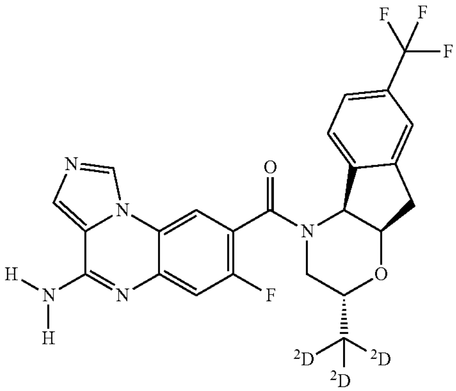 [SMILES: [2H]C([2H])([2H])[C@@H]1CN(C(=O)c2cc3c(cc2F)nc(N)c2cncn23)[C@H]2c3ccc(C(F)(F)F)cc3C[C@H]2O1] |
| Ff-639 | 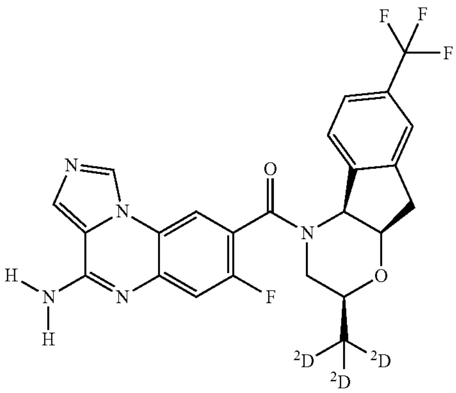 [SMILES: [2H]C([2H])([2H])[C@H]1CN(C(=O)c2cc3c(cc2F)nc(N)c2cncn23)[C@H]2c3ccc(C(F)(F)F)cc3C[C@H]2O1] |

TABLE 1D-continued
| Compounds | |
|---|---|
| Example | Structure |
| Ff-640 | 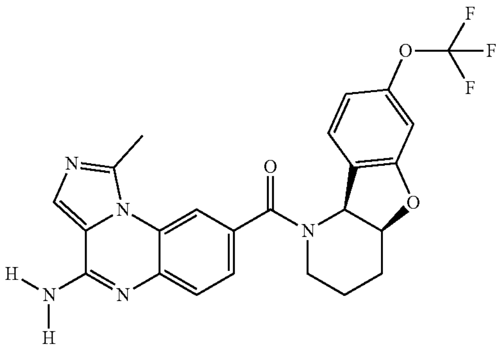 |
| Ff-643 | 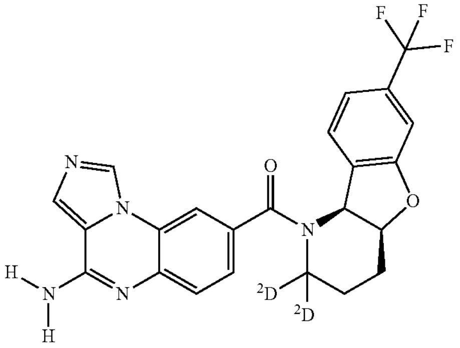 [SMILES: [2H]C1([2H])CC[C@@H]2Oc3cc(C(F)(F)F)ccc3[C@@H]2N1C(=O)c1ccc2nc(N)c3cncn3c2c1] |
| Ff-644 | 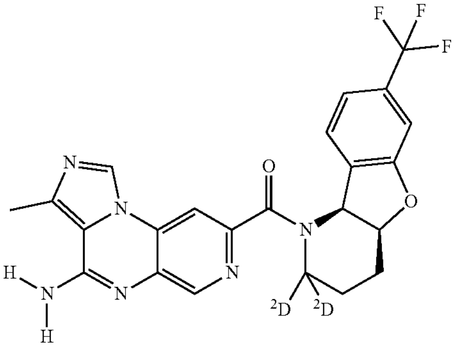 [SMILES: [2H]C1([2H])CC[C@@H]2Oc3cc(C(F)(F)F)ccc3[C@@H]2N1C(=O)c1cc2c(cn1)nc(N)c1c(C)ncn12] |
| Ff-646 | 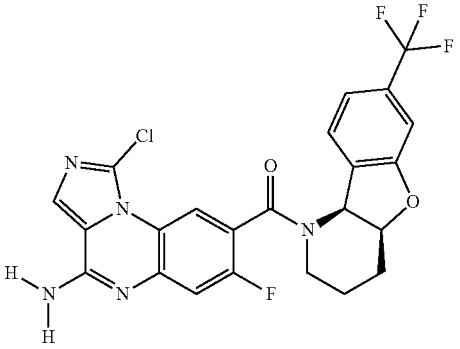 [SMILES: Nc1nc2cc(F)c(C(=O)N3CCC[C@@H]4Oc5cc(C(F)(F)F)ccc5[C@@H]43)cc2n2c(Cl)ncc12] |

TABLE 1D-continued
| Compounds | |
|---|---|
| Example | Structure |
| Ff-647 | 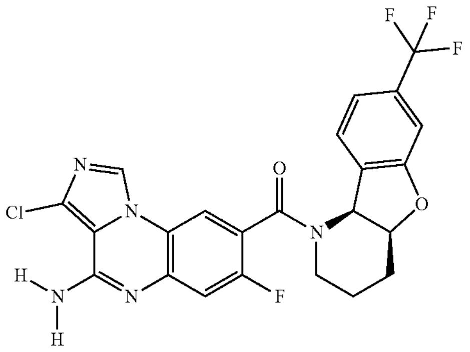 [SMILES: Nc1nc2cc(F)c(C(=O)N3CCC[C@@H]4Oc5cc(C(F)(F)F)ccc5[C@@H]43)cc2n2cnc(Cl)c12] |
| Ff-648 | 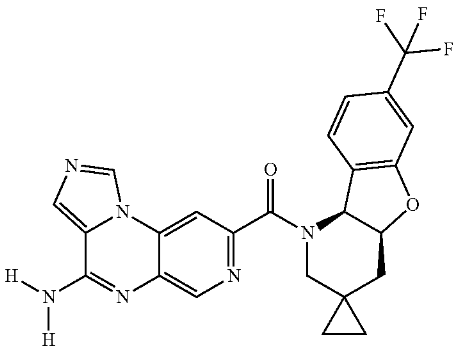 [SMILES: Nc1nc2cnc(C(=O)N3CC4(CC4)C[C@@H]4Oc5cc(C(F)(F)F)ccc5[C@@H]43)cc2n2cncc12] |
| Ff-649 | 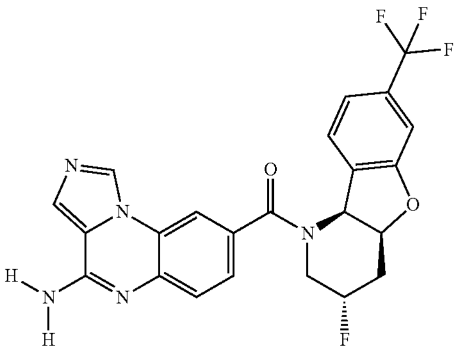 |
| Ff-650 | 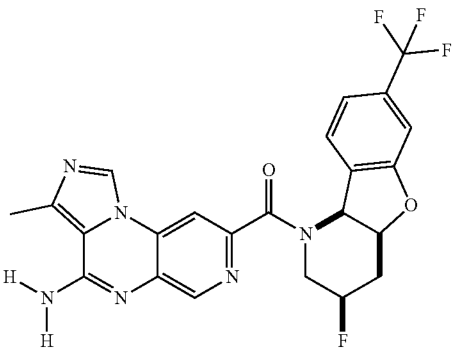 (±) |

TABLE 1D-continued
| Example | Compounds<br>Structure |
| --- | --- |
| Ff-651 | 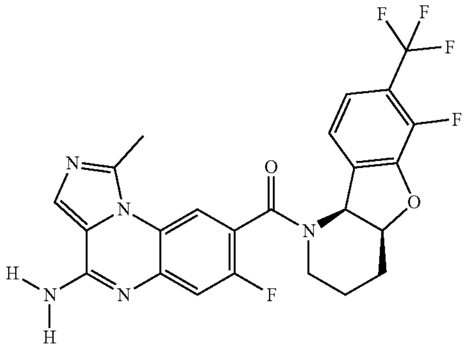 [SMILES: Cc1ncc2c(N)nc3cc(F)c(C(=O)N4CCC[C@@H]5Oc6c(ccc(C(F)(F)F)c6F)[C@@H]54)cc3n12] |
| Ff-655 | 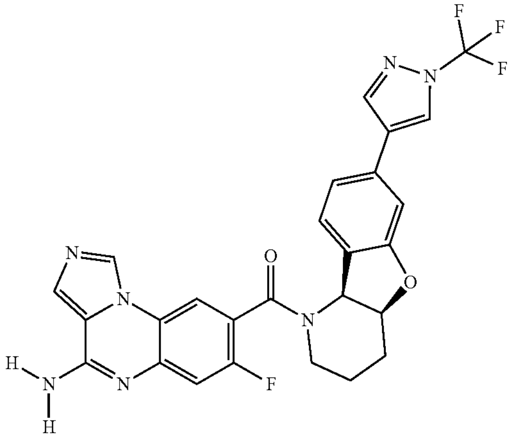 [SMILES: Nc1nc2cc(F)c(C(=O)N3CCC[C@@H]4Oc5cc(-c6cnn(C(F)(F)F)c6)ccc5[C@@H]43)cc2n2cncc12] |
| Ff-656 | 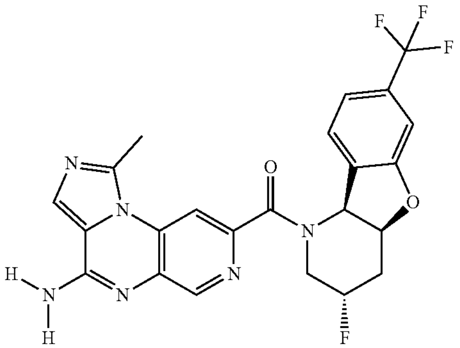 [SMILES: Cc1ncc2c(N)nc3cnc(C(=O)N4C[C@@H](F)C[C@@H]5Oc6cc(C(F)(F)F)ccc6[C@@H]54)cc3n12] |
| Ff-657 | 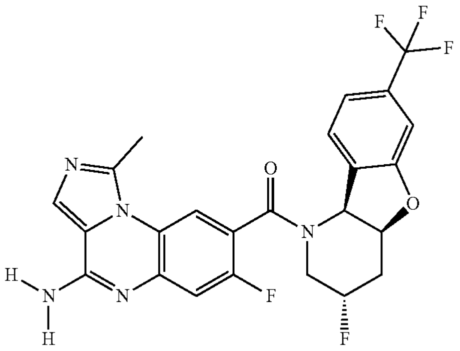 [SMILES: Cc1ncc2c(N)nc3cc(F)c(C(=O)N4C[C@@H](F)C[C@@H]5Oc6cc(C(F)(F)F)ccc6[C@@H]54)cc3n12] |

TABLE 1D-continued
| Compounds | |
|---|---|
| Example | Structure |
| Ff-658 | 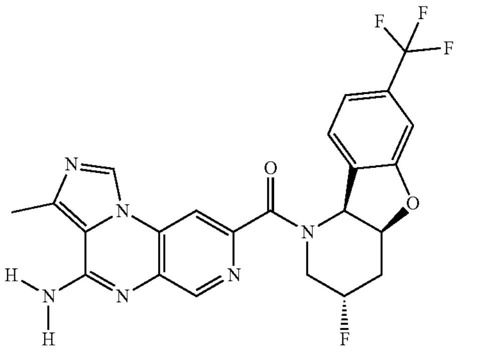 [SMILES: Cc1ncn2c1c(N)nc1cnc(C(=O)N3C[C@@H](F)C[C@@H]4Oc5cc(C(F)(F)F)ccc5[C@@H]43)cc12] |
| Ff-659 | 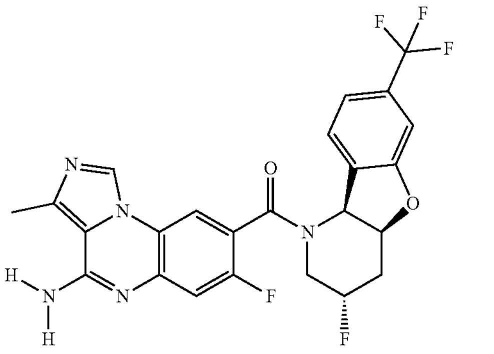 [SMILES: Cc1ncn2c1c(N)nc1cc(F)c(C(=O)N3C[C@@H](F)C[C@@H]4Oc5cc(C(F)(F)F)ccc5[C@@H]43)cc12] |
| Ff-660 | 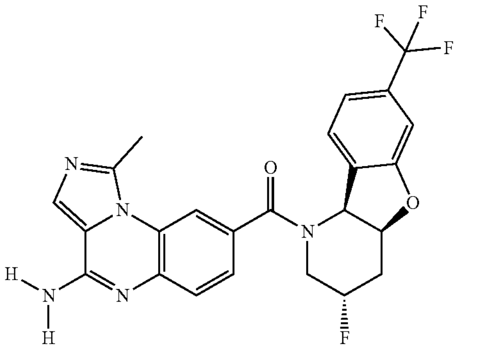 [SMILES: Cc1ncc2c(N)nc3ccc(C(=O)N4C[C@@H](F)C[C@@H]5Oc6cc(C(F)(F)F)ccc6[C@@H]54)cc3n12] |
| Ff-661 | 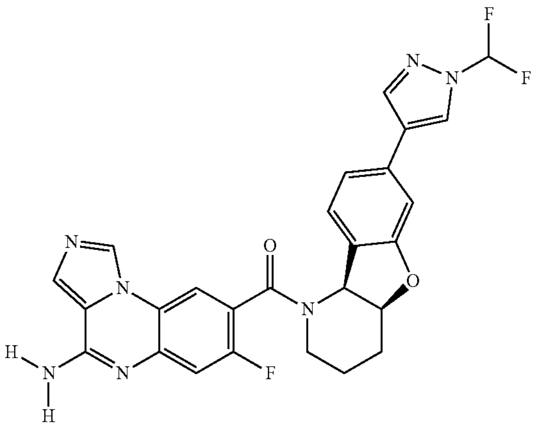 [SMILES: Nc1nc2cc(F)c(C(=O)N3CCC[C@@H]4Oc5cc(-c6cnn(C(F)F)c6)ccc5[C@@H]43)cc2n2cncc12] |

TABLE 1D-continued
| Compounds | |
|---|---|
| Example | Structure |
| Ff-662 | 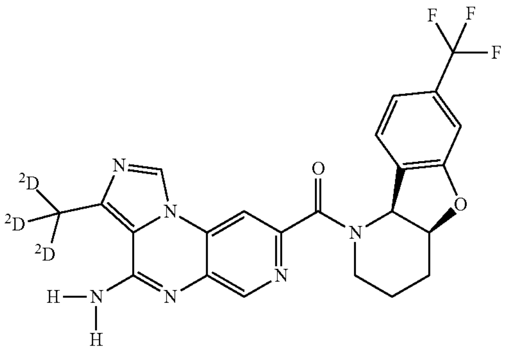 [SMILES: [2H]C([2H])([2H])c1ncn2c1c(N)nc1cnc(C(=O)N3CCC[C@@H]4Oc5cc(C(F)(F)F)ccc5[C@@H]43)cc12] |
| Ff-663 | 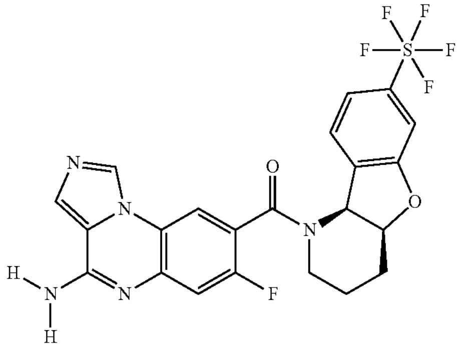 [SMILES: Nc1nc2cc(F)c(C(=O)N3CCC[C@@H]4Oc5cc(S(F)(F)(F)(F)F)ccc5[C@@H]43)cc2n2cncc12] |
| Ff-664 | 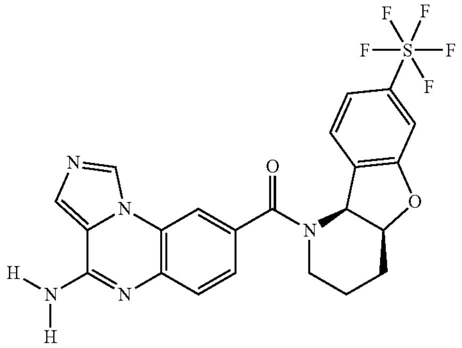 [SMILES: Nc1nc2ccc(C(=O)N3CCC[C@@H]4Oc5cc(S(F)(F)(F)(F)F)ccc5[C@@H]43)cc2n2cncc12] |
| Ff-665 | 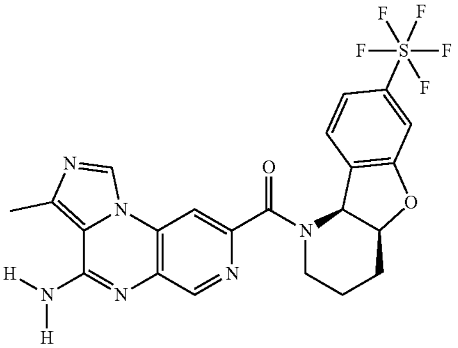 [SMILES: Cc1ncn2c1c(N)nc1cnc(C(=O)N3CCC[C@@H]4Oc5cc(S(F)(F)(F)(F)F)ccc5[C@@H]43)cc12] |

TABLE 1D-continued
| Compounds | |
|---|---|
| Example | Structure |
| Ff-666 | 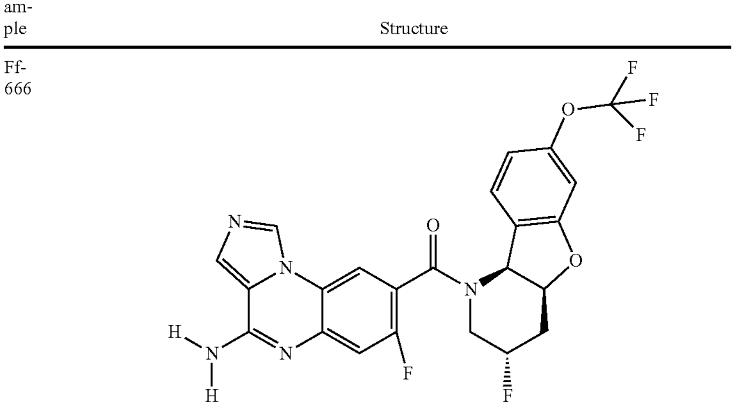 |
| Ff-667 | 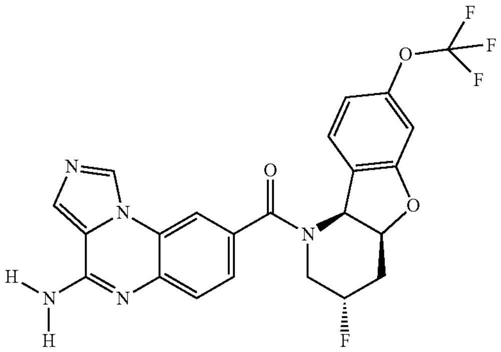 [SMILES: Nc1nc2ccc(C(=O)N3C[C@@H](F)C[C@@H]4Oc5cc(OC(F)(F)F)ccc5[C@@H]43)cc2n2cncc12] |
| Ff-669 | 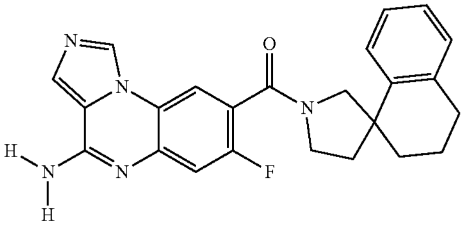 [SMILES: Nc1nc2cc(F)c(C(=O)N3CCC4(CCCc5ccccc54)C3)cc2n2cncc12] |
| Ff-670 | 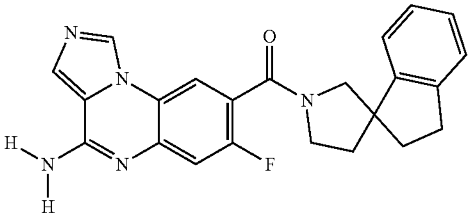 [SMILES: Nc1nc2cc(F)c(C(=O)N3CCC4(CCc5ccccc54)C3)cc2n2cncc12] |
| Ff-675 | 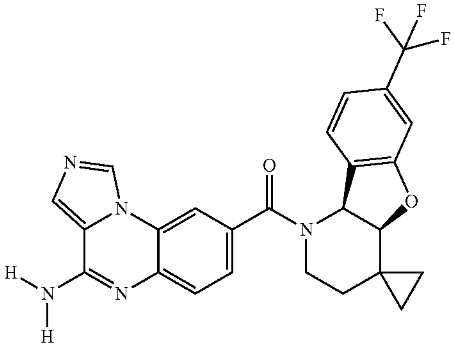 [SMILES: Nc1nc2ccc(C(=O)N3CCC4(CC4)[C@@H]4Oc5cc(C(F)(F)F)ccc5[C@@H]43)cc2n2cncc12] |

TABLE 1D-continued
| Compounds | |
|---|---|
| Example | Structure |
| Ff-676 | 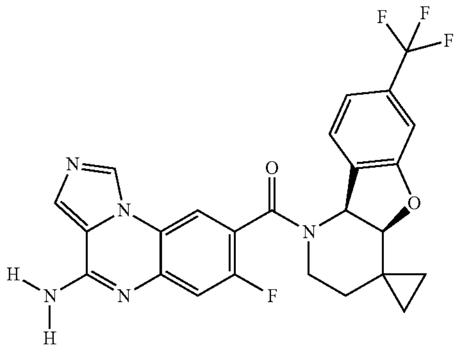 [SMILES: Nc1nc2cc(F)c(C(=O)N3CCC4(CC4)[C@@H]4Oc5cc(C(F)(F)F)ccc5[C@@H]43)cc2n2cncc12] |
| Ff-677 | 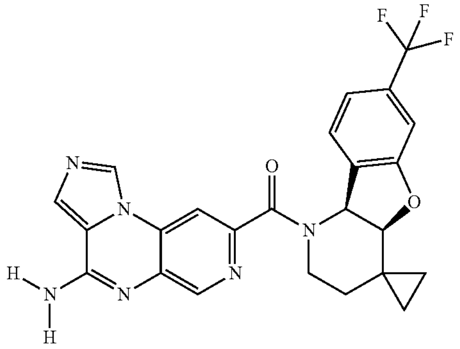 [SMILES: Nc1nc2cnc(C(=O)N3CCC4(CC4)[C@@H]4Oc5cc(C(F)(F)F)ccc5[C@@H]43)cc2n2cncc12] |
| Ff-678 | 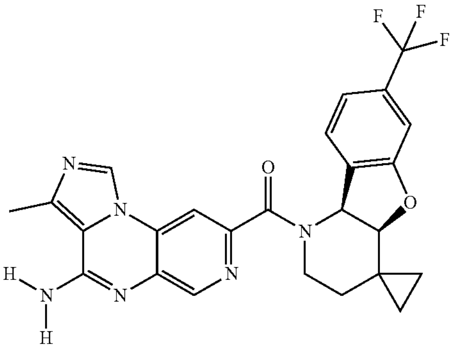 [SMILES: Cc1ncn2c1c(N)nc1cnc(C(=O)N3CCC4(CC4)[C@@H]4Oc5cc(C(F)(F)F)ccc5[C@@H]43)cc12] |
| Ff-679 | 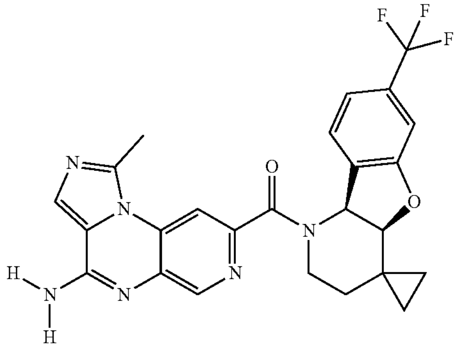 [SMILES: Cc1ncc2c(N)nc3cnc(C(=O)N4CCC5(CC5)[C@@H]5Oc6cc(C(F)(F)F)ccc6[C@@H]54)cc3n12] |

TABLE 1D-continued
| Compounds | |
|---|---|
| Example | Structure |
| Ff-680 | 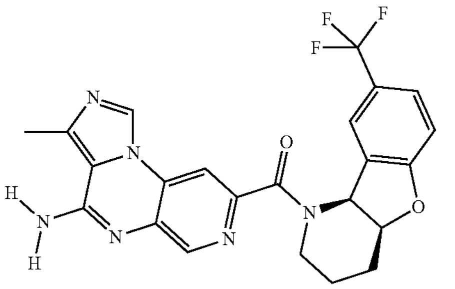 [SMILES: Cc1ncn2c1c(N)nc1cnc(C(=O)N3CCC[C@@H]4Oc5ccc(C(F)(F)F)cc5[C@@H]43)cc12] |
| Ff-681 | 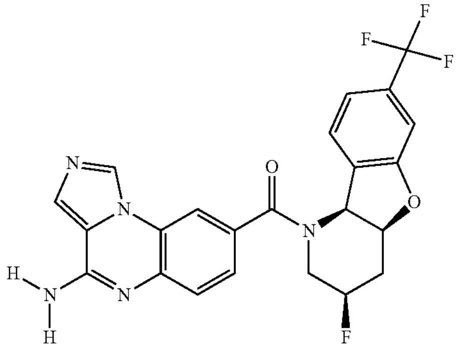 [SMILES: Nc1nc2ccc(C(=O)N3C[C@H](F)C[C@@H]4Oc5cc(C(F)(F)F)ccc5[C@@H]43)cc2n2cncc12] |
| Ff-682 | 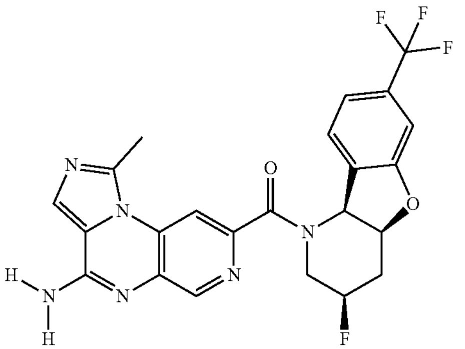 [SMILES: Cc1ncc2c(N)nc3cnc(C(=O)N4C[C@H](F)C[C@@H]5Oc6cc(C(F)(F)F)ccc6[C@@H]54)cc3n12] |
| Ff-683 | 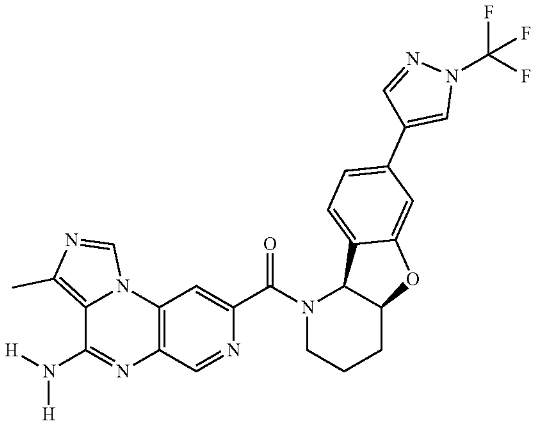 [SMILES: Cc1ncn2c1c(N)nc1cnc(C(=O)N3CCC[C@@H]4Oc5cc(-c6cnn(C(F)(F)F)c6)ccc5[C@@H]43)cc12] |

TABLE 1D-continued
| Compounds | |
|---|---|
| Example | Structure |
| Ff-684 | 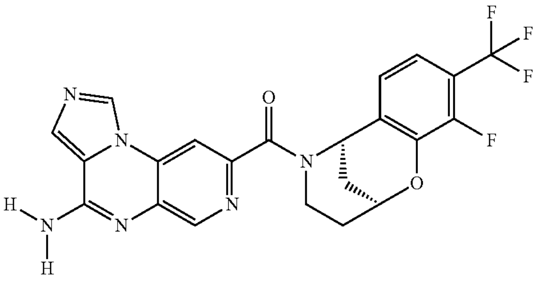 [SMILES: Nc1nc2cnc(C(=O)N3CC[C@H]4C[C@@H]3c3ccc(C(F)(F)F)c(F)c3O4)cc2n2cncc12] |
| Ff-685 | 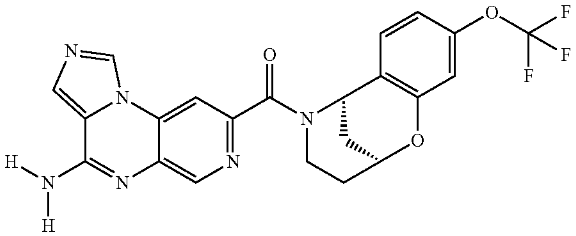 [SMILES: Nc1nc2cnc(C(=O)N3CC[C@H]4C[C@@H]3c3ccc(OC(F)(F)F)cc3O4)cc2n2cncc12] |
| Ff-687 | 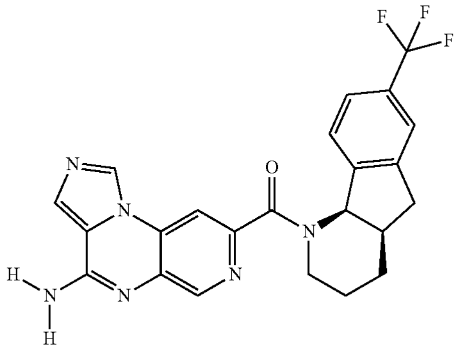 |
| Ff-88 | 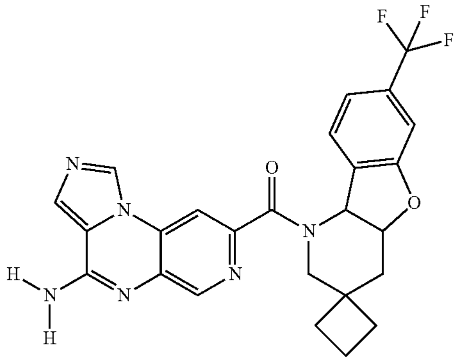 [SMILES: Nc1nc2cnc(C(=O)N3CC4(CCC4)CC4Oc5cc(C(F)(F)F)ccc5C43)cc2n2cncc12] |

TABLE 1D-continued
| Example | Structure |
| --- | --- |
| Ff-689 | 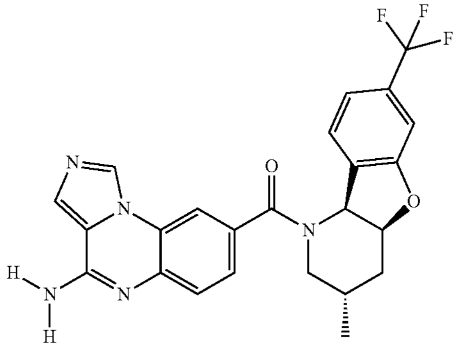 [SMILES: C[C@H]1C[C@@H]2Oc3cc(C(F)(F)F)ccc3[C@@H]2N(C(=O)c2ccc3nc(N)c4cncn4c3c2)C1] |
| Ff-690 | 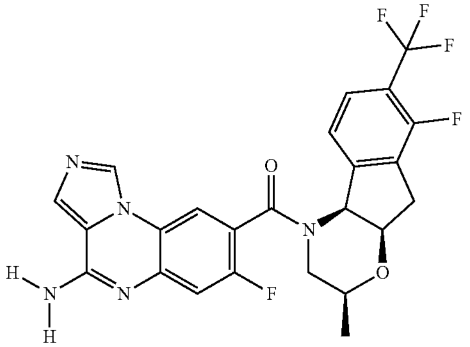 [SMILES: C[C@H]1CN(C(=O)c2cc3c(cc2F)nc(N)c2cncn23)[C@H]2c3ccc(C(F)(F)F)c(F)c3C[C@H]2O1] |
| Ff-691 | 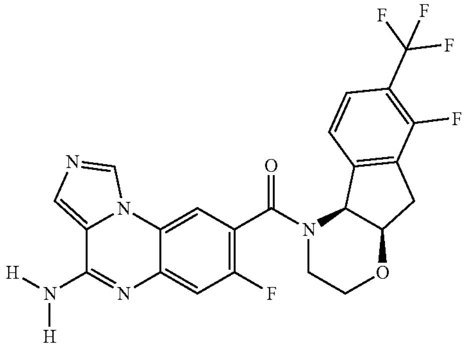 [SMILES: Nc1nc2cc(F)c(C(=O)N3CCO[C@@H]4Cc5c(ccc(C(F)(F)F)c5F)[C@@H]43)cc2n2cncc12] |
| Ff-692 | 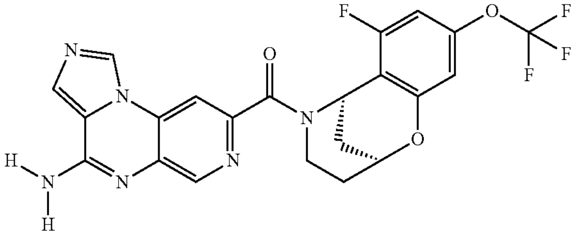 [SMILES: Nc1nc2cnc(C(=O)N3CC[C@H]4C[C@@H]3c3c(F)cc(OC(F)(F)F)cc3O4)cc2n2cncc12] |

TABLE 1D-continued
| Compounds | |
|---|---|
| Ex-am-ple | Structure |
| Ff-693 | 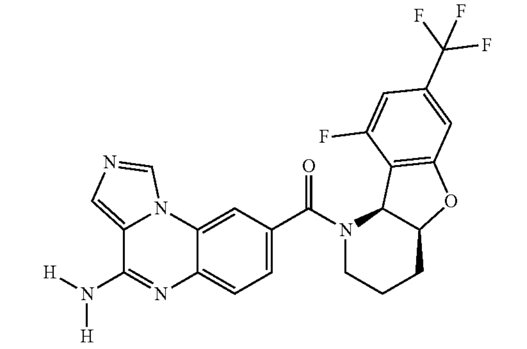 [SMILES: Nc1nc2ccc(C(=O)N3CCC[C@@H]4Oc5cc(C(F)(F)F)cc(F)c5[C@@H]43)cc2n2cncc12] |
| Ff-694 | 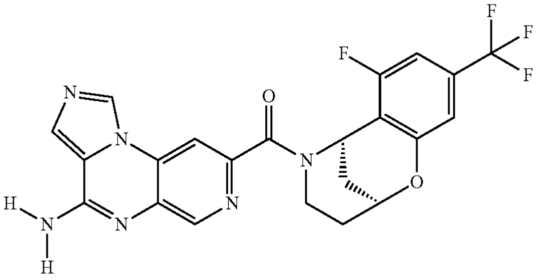 [SMILES: Nc1nc2cnc(C(=O)N3CC[C@H]4C[C@@H]3c3c(F)cc(C(F)(F)F)cc3O4)cc2n2cncc12] |
| Ff-695 | 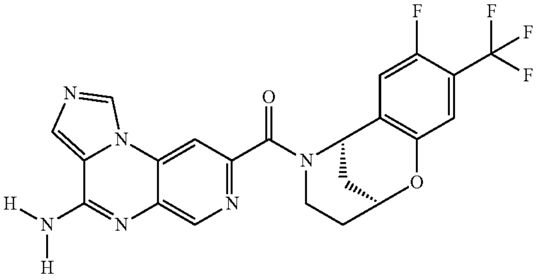 [SMILES: Nc1nc2cnc(C(=O)N3CC[C@H]4C[C@@H]3c3cc(F)c(C(F)(F)F)cc3O4)cc2n2cncc12] |
| Ff-696 | 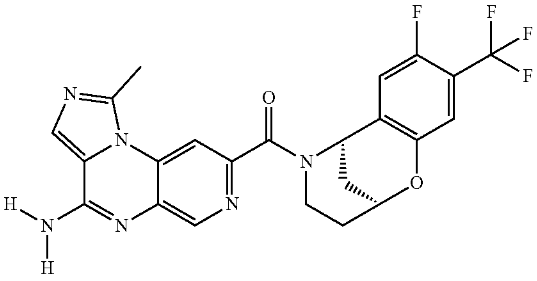 [SMILES: Cc1ncc2c(N)nc3cnc(C(=O)N4CC[C@H]5C[C@@H]4c4cc(F)c(C(F)(F)F)cc4O5)cc3n12] |

TABLE 1D-continued
| Compounds | |
|---|---|
| Example | Structure |
| Ff-697 | 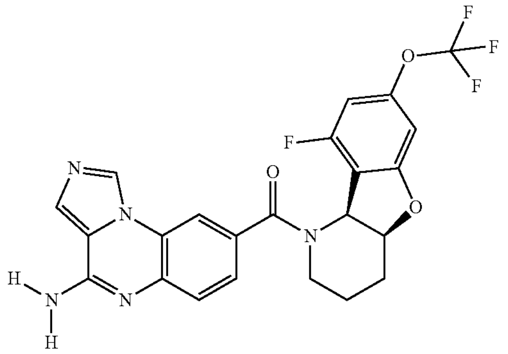 [SMILES: Nc1nc2ccc(C(=O)N3CCC[C@@H]4Oc5cc(OC(F)(F)F)cc(F)c5[C@@H]43)cc2n2cncc12] |
| Ff-698 | 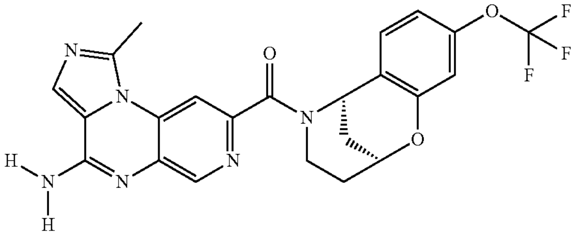 |
| Ff-699 | 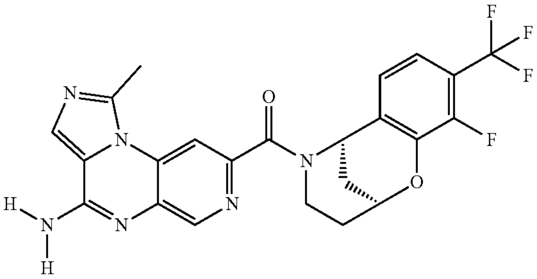 |
| Ff-700 | 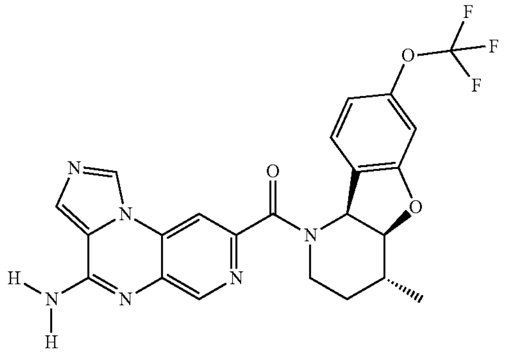 [SMILES: C[C@@H]1CCN(C(=O)c2cc3c(cn2)nc(N)c2cncn23)[C@H]2c3ccc(OC(F)(F)F)cc3O[C@@H]12] |

TABLE 1D-continued
| Example | Structure |
|---|---|
| Ff-701 | 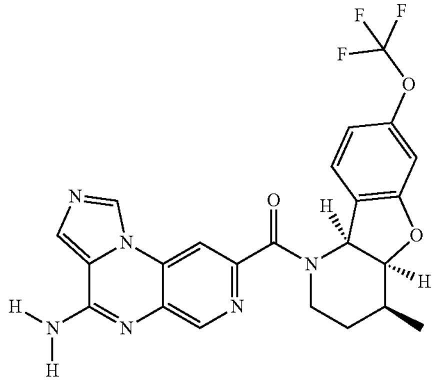 [SMILES: C[C@H]1CCN(C(=O)c2cc3c(cn2)nc(N)c2cncn23)[C@H]2c3ccc(OC(F)(F)F)cc3O[C@@H]12] |
| Ff-702 | 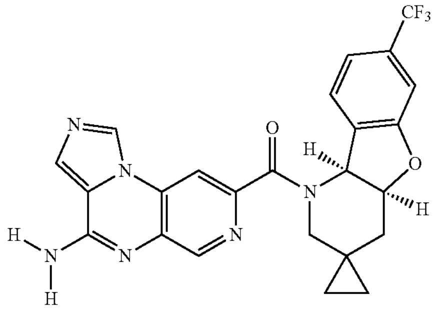 [SMILES: Nc1nc2cnc(C(=O)N3CC4(CC4)C[C@@H]4Oc5cc(C(F)(F)F)ccc5[C@@H]43)cc2n2cncc12] |
| Ff-703 | 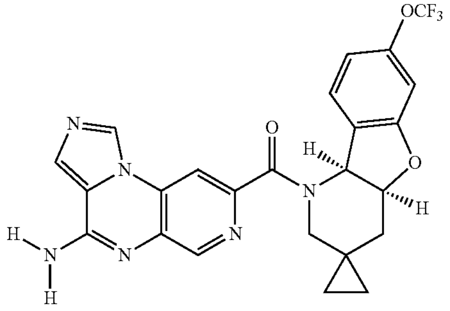 [SMILES: Nc1nc2cnc(C(=O)N3CC4(CC4)C[C@@H]4Oc5cc(OC(F)(F)F)ccc5[C@@H]43)cc2n2cncc12] |
| Fg-19 | 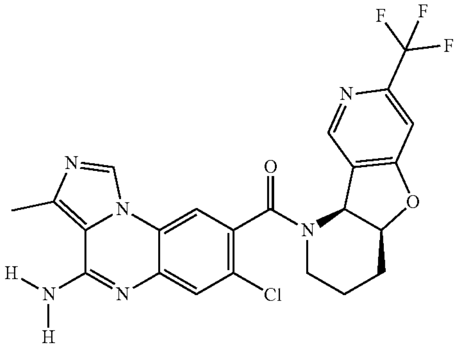 |

TABLE 1D-continued
| Compounds | |
|---|---|
| Example | Structure |
| Fg-20 | 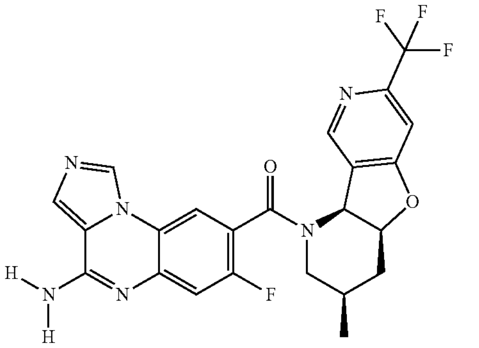 [SMILES: C[C@@H]1C[C@@H]2Oc3cc(C(F)(F)F)ncc3[C@@H]2N(C(=O)c2cc3c(cc2F)nc(N)c2cncn23)C1] |
| Fg-21 | 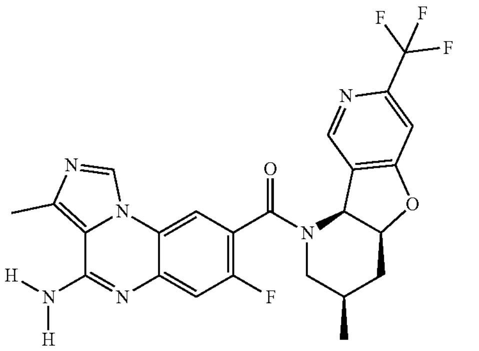 [SMILES: Cc1ncn2c1c(N)nc1cc(F)c(C(=O)N3C[C@H](C)C[C@@H]4Oc5cc(C(F)(F)F)ncc5[C@@H]43)cc12] |
| Fg-22 | 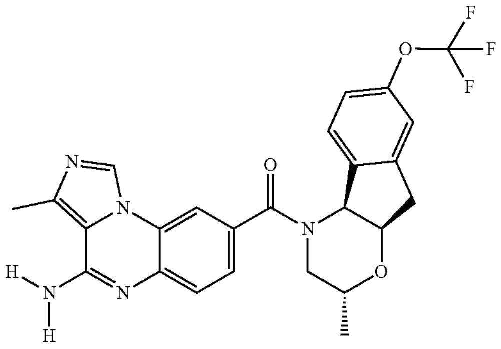 [SMILES: Cc1ncn2c1c(N)nc1ccc(C(=O)N3C[C@@H](C)O[C@@H]4Cc5cc(OC(F)(F)F)ccc5[C@@H]43)cc12] |
| Fg-23 | 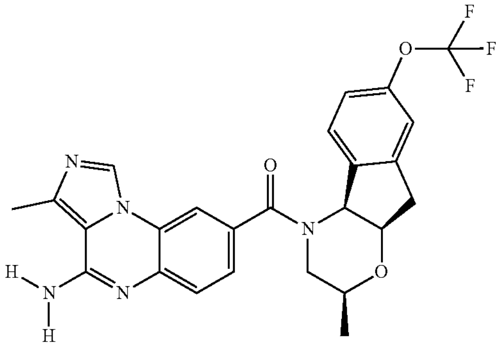 [SMILES: Cc1ncn2c1c(N)nc1ccc(C(=O)N3C[C@H](C)O[C@@H]4Cc5cc(OC(F)(F)F)ccc5[C@@H]43)cc12] |

TABLE 1D-continued
| Compounds | |
|---|---|
| Ex-am-ple | Structure |
| Fg-24 | 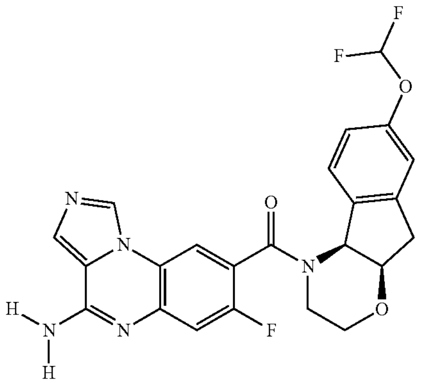 [SMILES: Nc1nc2cc(F)c(C(=O)N3CCO[C@@H]4Cc5cc(OC(F)F)ccc5[C@@H]43)cc2n2cncc12] |
| Fg-25 | 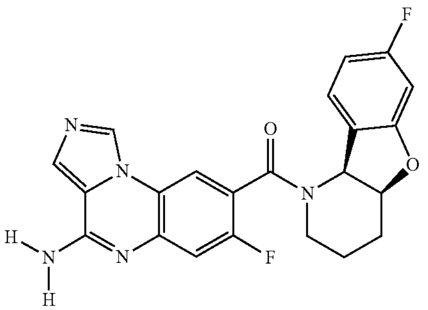 [SMILES: Nc1nc2cc(F)c(C(=O)N3CCC[C@@H]4Oc5cc(F)ccc5[C@@H]43)cc2n2cncc12] |
| Fg-26 | 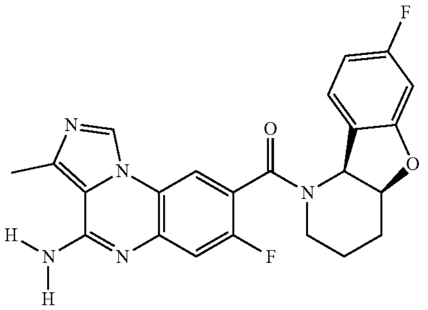 [SMILES: Cc1ncn2c1c(N)nc1cc(F)c(C(=O)N3CCC[C@@H]4Oc5cc(F)ccc5[C@@H]43)cc12] |
| Fg-27 | 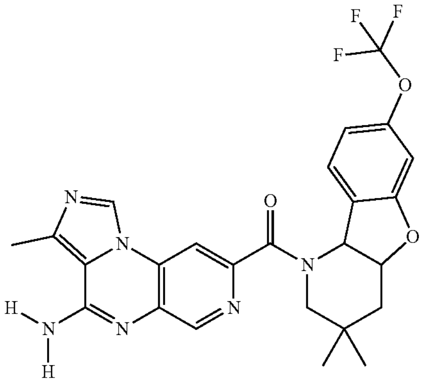 [SMILES: Cc1ncn2c1c(N)nc1cnc(C(=O)N3CC(C)(C)CC4Oc5cc(OC(F)(F)F)ccc5C43)cc12] |

TABLE 1D-continued
| Compounds | |
|---|---|
| Example | Structure |
| Fg-28 | 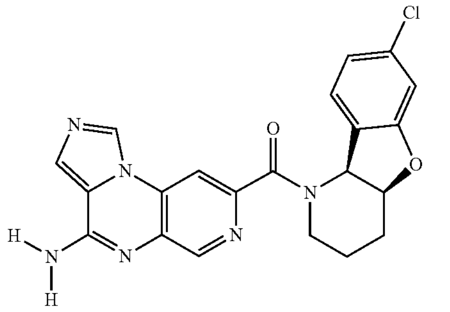 [SMILES: Nc1nc2cnc(C(=O)N3CCC[C@@H]4Oc5cc(Cl)ccc5[C@@H]43)cc2n2cncc12] |
| Fg-29 | 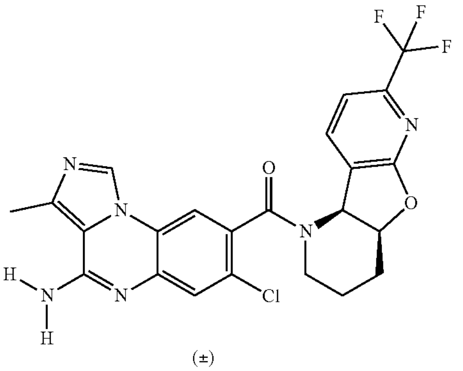 [SMILES: Cc1ncn2c1c(N)nc1cc(Cl)c(C(=O)N3CCC[C@@H]4Oc5nc(C(F)(F)F)ccc5[C@@H]43)cc12] (±) |
| Fg-30 | 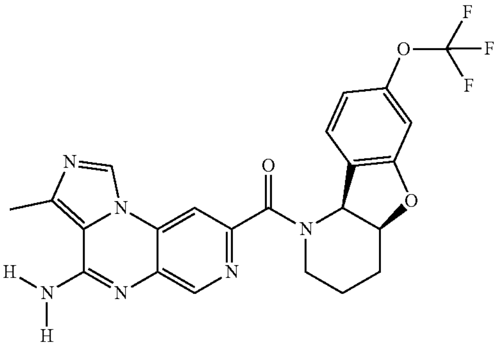 [SMILES: Cc1ncn2c1c(N)nc1cnc(C(=O)N3CCC[C@@H]4Oc5cc(OC(F)(F)F)ccc5[C@@H]43)cc12] |
| Fg-31 | 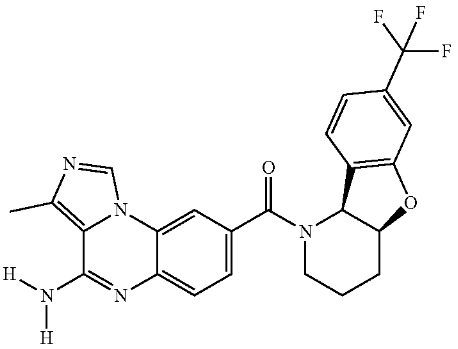 [SMILES: Cc1ncn2c1c(N)nc1ccc(C(=O)N3CCC[C@@H]4Oc5cc(C(F)(F)F)ccc5[C@@H]43)cc12] |

TABLE 1D-continued
| Compounds | |
|---|---|
| Example | Structure |
| Fg-32 | 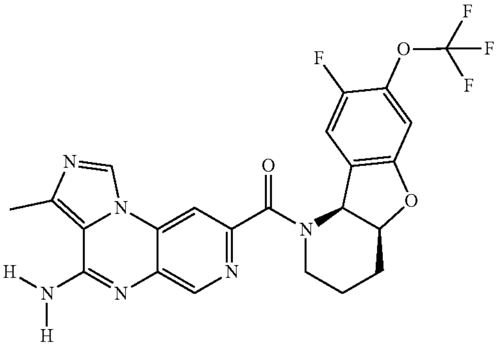 [SMILES: Cc1ncn2c1c(N)nc1cnc(C(=O)N3CCC[C@@H]4Oc5cc(OC(F)(F)F)c(F)cc5[C@@H]43)cc12] |
| Fg-33 | 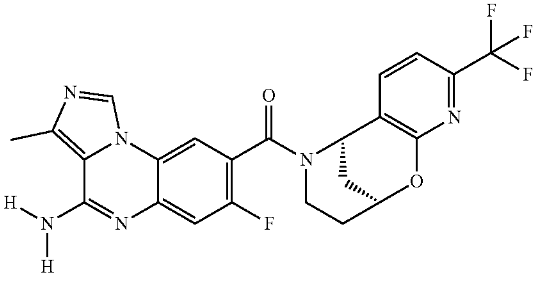 [SMILES: Cc1ncn2c1c(N)nc1cc(F)c(C(=O)N3CC[C@H]4C[C@@H]3c3ccc(C(F)(F)F)nc3O4)cc12] |
| Fg-34 | 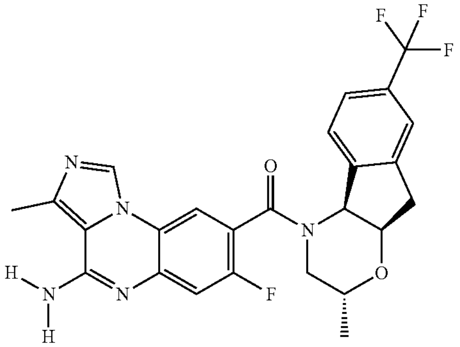 [SMILES: Cc1ncn2c1c(N)nc1cc(F)c(C(=O)N3C[C@@H](C)O[C@@H]4Cc5cc(C(F)(F)F)ccc5[C@@H]43)cc12] |
| Fg-35 | 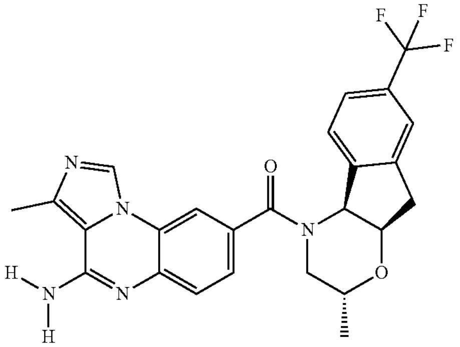 [SMILES: Cc1ncn2c1c(N)nc1ccc(C(=O)N3C[C@@H](C)O[C@@H]4Cc5cc(C(F)(F)F)ccc5[C@@H]43)cc12] |

TABLE 1D-continued
| Compounds | |
|---|---|
| Example | Structure |
| Fg-36 | 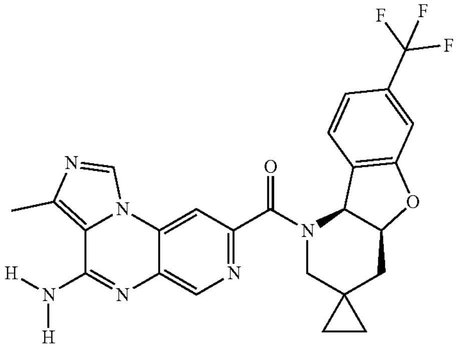 [SMILES: Cc1ncn2c1c(N)nc1cnc(C(=O)N3CC4(CC4)C[C@@H]4Oc5cc(C(F)(F)F)ccc5[C@@H]43)cc12] |
| Fg-37 | 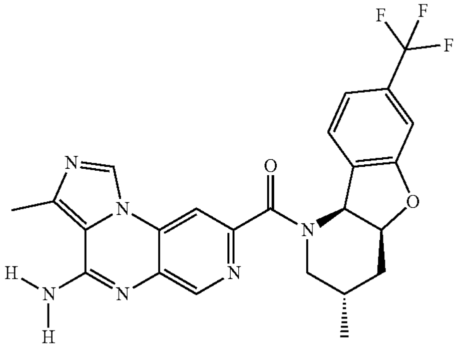 [SMILES: Cc1ncn2c1c(N)nc1cnc(C(=O)N3C[C@@H](C)C[C@@H]4Oc5cc(C(F)(F)F)ccc5[C@@H]43)cc12] |
| Fg-38 | 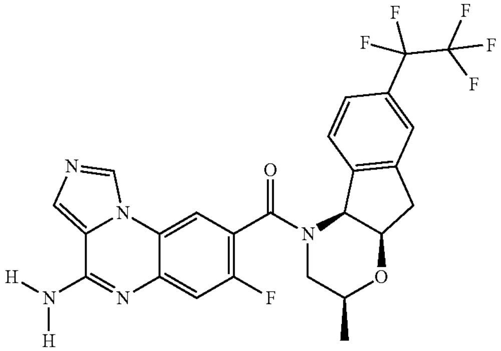 [SMILES: C[C@H]1CN(C(=O)c2cc3c(cc2F)nc(N)c2cncn23)[C@H]2c3ccc(C(F)(F)C(F)(F)F)cc3C[C@H]2O1] |
| Fg-39 | 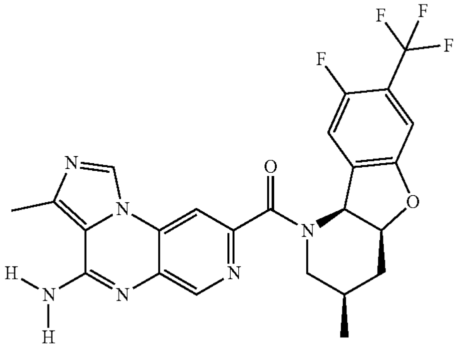 [SMILES: Cc1ncn2c1c(N)nc1cnc(C(=O)N3C[C@H](C)C[C@@H]4Oc5cc(C(F)(F)F)c(F)cc5[C@@H]43)cc12] |

TABLE 1D-continued
| Compounds | |
|---|---|
| Example | Structure |
| Fg-40 | 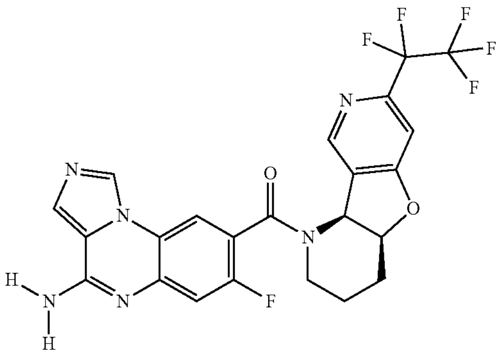 [SMILES: Nc1nc2cc(F)c(C(=O)N3CCC[C@@H]4Oc5cc(C(F)(F)C(F)(F)F)ncc5[C@@H]43)cc2n2cncc12] |
| Fg-41 | 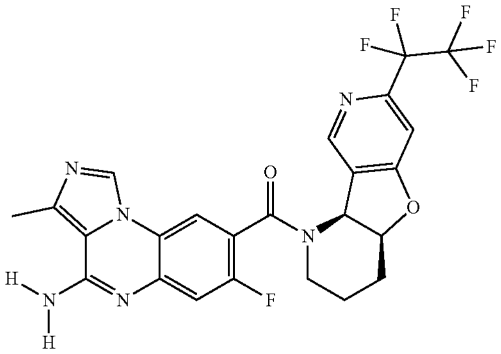 [SMILES: Cc1ncn2c1c(N)nc1cc(F)c(C(=O)N3CCC[C@@H]4Oc5cc(C(F)(F)C(F)(F)F)ncc5[C@@H]43)cc12] |
| Fg-42 | 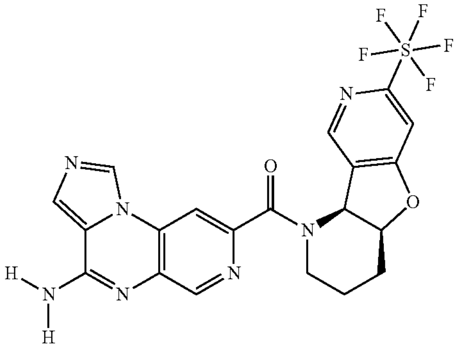 [SMILES: Nc1nc2cnc(C(=O)N3CCC[C@@H]4Oc5cc(S(F)(F)(F)(F)F)ncc5[C@@H]43)cc2n2cncc12] |
| Fg-43 | 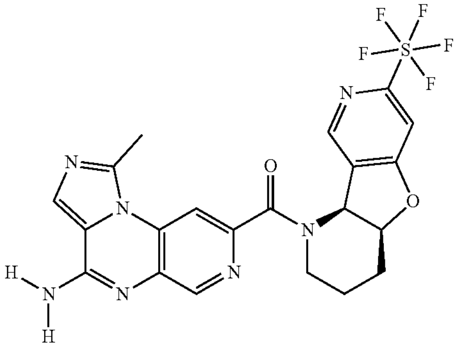 [SMILES: Cc1ncc2c(N)nc3cnc(C(=O)N4CCC[C@@H]5Oc6cc(S(F)(F)(F)(F)F)ncc6[C@@H]54)cc3n12] |

TABLE 1D-continued
| Compounds | |
|---|---|
| Example | Structure |
| Fg-44 | 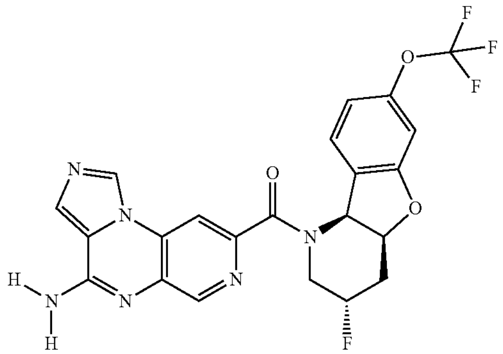 [SMILES: Nc1nc2cnc(C(=O)N3C[C@@H](F)C[C@@H]4Oc5cc(OC(F)(F)F)ccc5[C@@H]43)cc2n2cncc12] |
| Fg-45 | 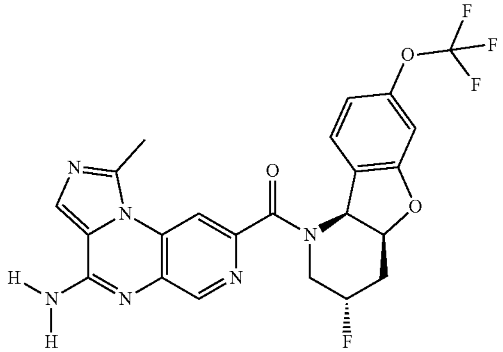 [SMILES: Cc1ncc2c(N)nc3cnc(C(=O)N4C[C@@H](F)C[C@@H]5Oc6cc(OC(F)(F)F)ccc6[C@@H]54)cc3n12] |
| Fg-46 | 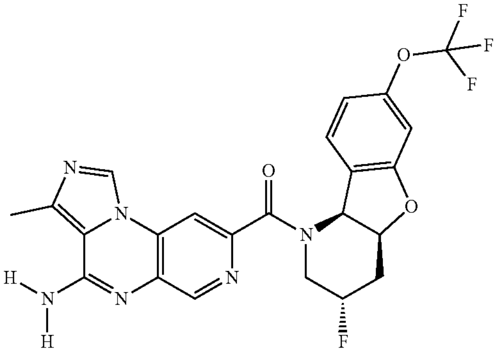 [SMILES: Cc1ncn2c1c(N)nc1cnc(C(=O)N3C[C@@H](F)C[C@@H]4Oc5cc(OC(F)(F)F)ccc5[C@@H]43)cc12] |
| Fg-47 | 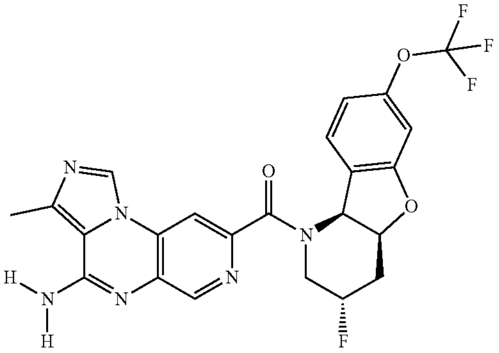 [SMILES: Cc1ncn2c1c(N)nc1cnc(C(=O)N3C[C@@H](F)C[C@@H]4Oc5cc(OC(F)(F)F)ccc5[C@@H]43)cc12] |

TABLE 1D-continued
| Compounds | |
| --- | --- |
| Example | Structure |
| Fg-50 | 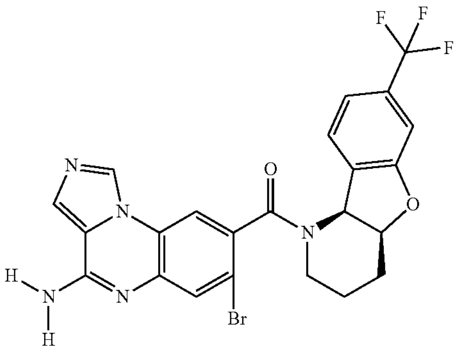 [SMILES: Nc1nc2cc(Br)c(C(=O)N3CCC[C@@H]4Oc5cc(C(F)(F)F)ccc5[C@@H]43)cc2n2cncc12] |
| Fg-53 | 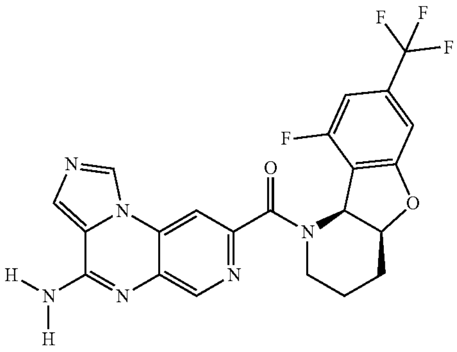 |
| Fg-54 | 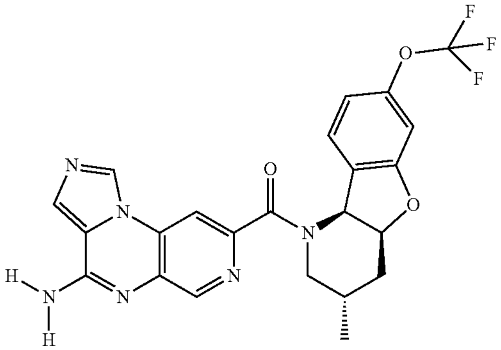 [SMILES: C[C@H]1C[C@@H]2Oc3cc(OC(F)(F)F)ccc3[C@@H]2N(C(=O)c2cc3c(cn2)nc(N)c2cncn23)C1] |
| Fg-55 | 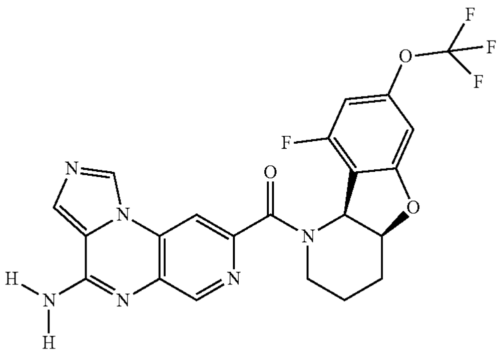 [SMILES: Nc1nc2cnc(C(=O)N3CCC[C@@H]4Oc5cc(OC(F)(F)F)cc(F)c5[C@@H]43)cc2n2cncc12] |

TABLE 1D-continued
| Compounds | |
|---|---|
| Example | Structure |
| Fg-56 | 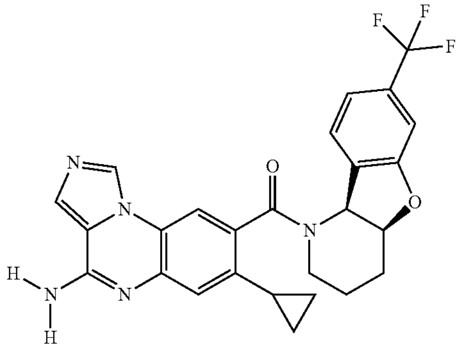 [SMILES: Nc1nc2cc(C3CC3)c(C(=O)N3CCC[C@@H]4Oc5cc(C(F)(F)F)ccc5[C@@H]43)cc2n2cncc12] |
| Fg-57 | 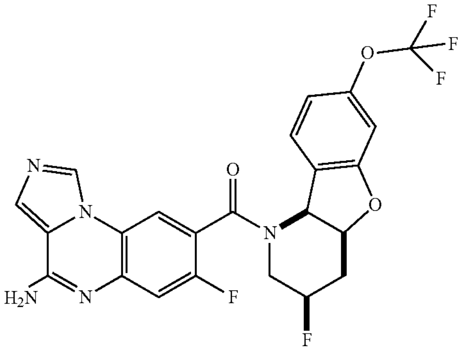 (±) |
| Fg-58 | 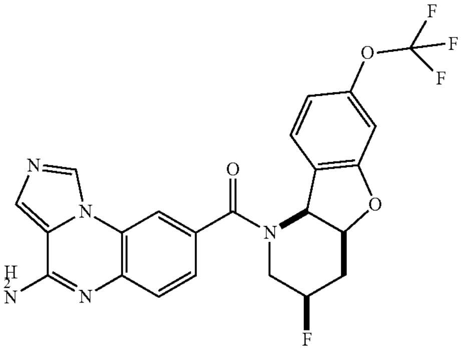 (±) |
| Fg-59 | 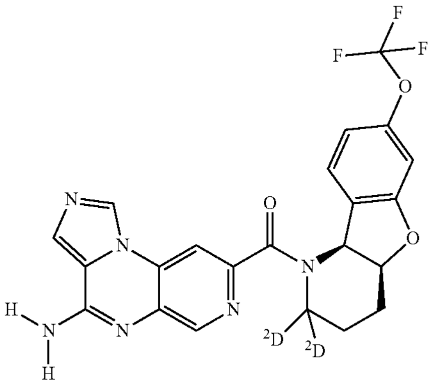 [SMILES: [2H]C1([2H])CC[C@@H]2Oc3cc(OC(F)(F)F)ccc3[C@@H]2N1C(=O)c1cc2c(cn1)nc(N)c1cncn12] |

TABLE 1D-continued
| Compounds | |
|---|---|
| Example | Structure |
| Fg-60 | 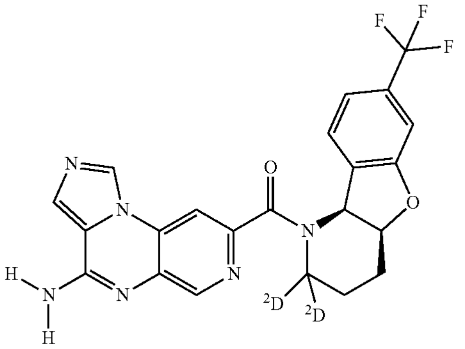 [SMILES: [2H]C1([2H])CC[C@@H]2Oc3cc(C(F)(F)F)ccc3[C@@H]2N1C(=O)c1cc2c(cn1)nc(N)c1cncn12] |
| Fg-61 | 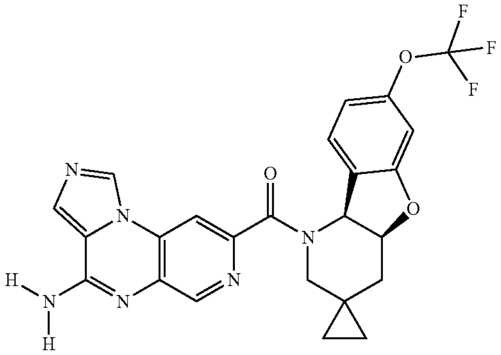 [SMILES: Nc1nc2cnc(C(=O)N3CC4(CC4)C[C@@H]4Oc5cc(OC(F)(F)F)ccc5[C@@H]43)cc2n2cncc12] |
| Fg-62 | 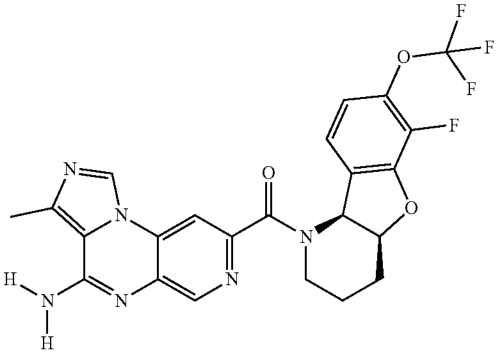 [SMILES: Cc1ncn2c1c(N)nc1cnc(C(=O)N3CCC[C@@H]4Oc5c(ccc(OC(F)(F)F)c5F)[C@@H]43)cc12] |
| Fg-63 | 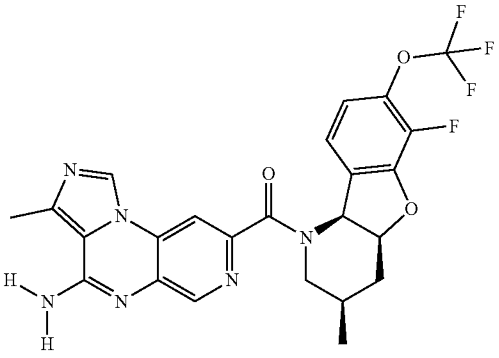 [SMILES: Cc1ncn2c1c(N)nc1cnc(C(=O)N3C[C@H](C)C[C@@H]4Oc5c(ccc(OC(F)(F)F)c5F)[C@@H]43)cc12] |

TABLE 1D-continued
| Compounds | |
|---|---|
| Example | Structure |
| Fg-64 | 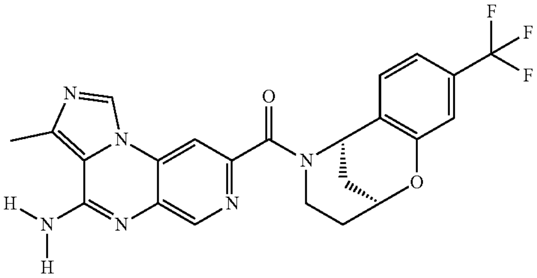 [SMILES: Cc1ncn2c1c(N)nc1cnc(C(=O)N3CC[C@H]4C[C@@H]3c3ccc(C(F)(F)F)cc3O4)cc12] |
| Fg-65 | 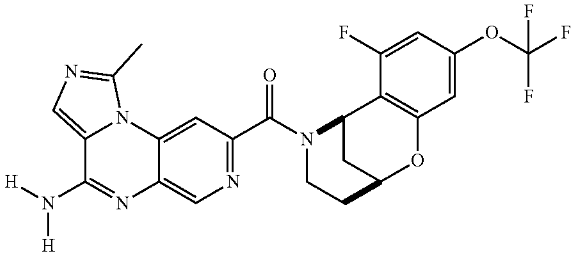 (±) |
| Fg-66 | 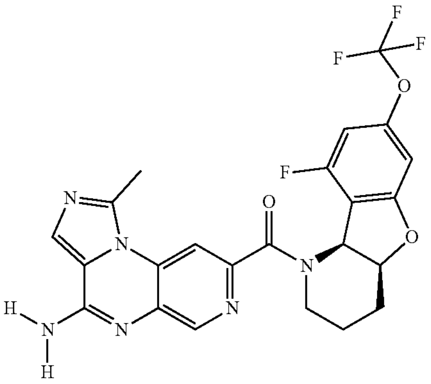 [SMILES: Cc1ncc2c(N)nc3cnc(C(=O)N4CCC[C@@H]5Oc6cc(OC(F)(F)F)cc(F)c6[C@@H]54)cc3n12] |
| Fg-67 | 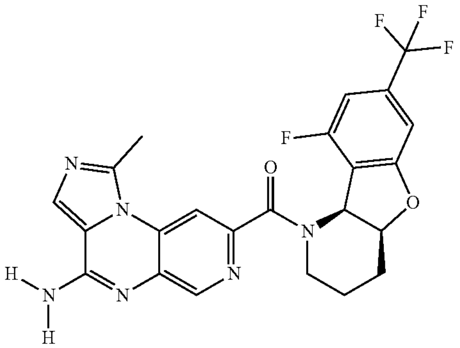 [SMILES: Cc1ncc2c(N)nc3cnc(C(=O)N4CCC[C@@H]5Oc6cc(C(F)(F)F)cc(F)c6[C@@H]54)cc3n12] |

TABLE 1D-continued

| Compounds | |
|---|---|
| Example | Structure |
| Fg-68 | 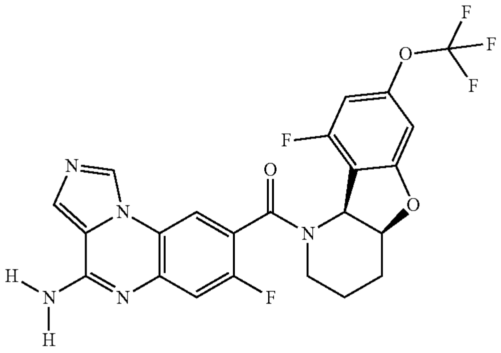 [SMILES: Nc1nc2cc(F)c(C(=O)N3CCC[C@@H]4Oc5cc(OC(F)(F)F)cc(F)c5[C@@H]43)cc2n2cncc12] |

TABLE 2

Synthetic procedure for some examples disclosed herein

| Example | Coupling Procedure | Core Intermediate | Tail Intermediate |
|---|---|---|---|
| Fa-1 | I-F | Ba-1 | Dd-1 |
| Fa-2 | I-F | Ac-2 | Da-4 |
| Fa-3 | I-F | Ba-1 | Da-3 |
| Fa-4 | I-F | Ba-2 | Db-1 |
| Fa-5 | I-F | Aa-1 | Dc-1 + 4-(4,4,5,5-tetramethyl-1,3,2-dioxaborolan-2-yl)-1-(trifluoromethyl)-1H-pyrazole |
| Fa-6 | I-F | Aa-1 | Dc-4 |
| Fa-7 | I-F | Ab-1 | Da-7 |
| Fa-8 | I-F | Af-1 | De-1 |
| Fb-1 | II-F | Af-1 | Dc-2 |
| Fb-2 | II-F | Ae-1 | Da-3 |
| Fb-3 | II-F | Af-1 | Db-1 |
| Fb-4 | II-F | Af-3 | Db-1 |
| Fb-5 | II-F | Ae-1 | Dc-3 |
| Fb-6 | II-F | Af-3 | Dc-3 |
| Fb-7 | II-F | Af-1 | Da-6 |
| Fb-8 | II-F | Af-1 | Eal-1 |
| Fb-9 | II-F | Af-1 | Eal-2 |
| Fb-10 | II-F | Af-1 | Eal-3 |
| Fb-11 | II-F | Af-1 | Eal-4 |
| Fb-12 | II-F | Af-6 | Eal-4 |
| Fb-13 | II-F | Af-1 | Eal-5 |
| Fb-14 | II-F | Ae-1 | Eal-1 |
| Fb-15 | II-F | Ae-1 | Eaq-1 |
| Fb-16 | II-F | Af-1 | Dc-5 |
| Fb-17 | II-F | Ae-1 | Dc-2 |
| Fb-18 | II-F | Af-1 | Eal-7 |
| Fc-1 | III-F | Ac-1 | Da-1 |
| Fc-2 | III-F | Ac-1 | Da-2 |
| Fd-1 | IV-F | Ad-1 | Da-1 |
| Fe-1 | V-F | Ad-1 | Ec-1 |
| Fe-2 | V-F | Ae-1 | Ec-2 |
| Ff-1 | VI-F | Af-1 | Ec-1 |
| Ff-2 | VI-F | Af-1 | 3,3-dimethyl-4-phenylpyrrolidine |
| Ff-3 | VI-F | Af-1 | 1-(4-(trifluoromethyl)phenyl)-3-azabicyclo[3.1.0]hexane |
| Ff-4 | VI-F | Af-1 | 3-(2-fluoro-4-(trifluoromethyl)phenyl) pyrrolidine |
| Ff-5 | VI-F | Ae-1 | Ed-3 |
| Ff-6 | VI-F | Af-1 | Ec-5 |
| Ff-7 | VI-F | Af-1 | Ed-1 |
| Ff-8 | VI-F | Ae-1 | Eh-2 |
| Ff-9 | VI-F | Af-1 | Eh-2 |
| Ff-10 | VI-F | Af-2 | Eh-1 |
| Ff-11 | VI-F | Ae-1 | Eh-1 |
| Ff-12 | VI-F | Af-1 | Eh-1 |
| Ff-13 | VI-F | Af-1 | Eh-3 |

TABLE 2-continued

| Synthetic procedure for some examples disclosed herein | | | |
|---|---|---|---|
| Example | Coupling Procedure | Core Intermediate | Tail Intermediate |
| Ff-14 | VI-F | Af-1 | Eh-4 |
| Ff-15 | VI-F | Ae-1 | Eg-1 |
| Ff-16 | VI-F | Af-1 | Eg-1 |
| Ff-17 | VI-F + Sonogashira | Af-3 | Eh-5 + 2-ethynyltetrahydrofuran |
| Ff-18 | VI-F + Sonogashira | Af-3 | Eh-5 + 3-methoxy-3-methylbut-1-yne |
| Ff-19 | VI-F + Sonogashira | Af-3 | Eh-5 + 1-ethynylcyclopropan-1-ol |
| Ff-20 | VI-F + Sonogashira | Af-3 | Eh-5 + 3-ethynyl-3-methyloxetane |
| Ff-21 | VI-F | Af-3 | Eh-6 |
| Ff-22 | VI-F | Af-1 | Eh-6 |
| Ff-23 | VI-F + Suzuki | Af-1 | Ec-3 + 4-(4,4,5,5-tetramethyl-1,3,2-dioxaborolan-2-yl)-1-(trifluoromethyl)-1H-pyrazole |
| Ff-24 | VI-F + Suzuki | Af-1 | Ed-2 + 4-(4,4,5,5-tetramethyl-1,3,2-dioxaborolan-2-yl)-1-(trifluoromethyl)-1H-pyrazole |
| Ff-25 | VI-F | Ae-1 | Ed-5 |
| Ff-26 | VI-F | Af-1 | Ed-5 |
| Ff-27 | VI-F | Af-1 | Ed-4 |
| Ff-28 | VI-F | Af-1 | Ee-1 |
| Ff-29 | VI-F | Af-1 | Ef-1 |
| Ff-30 | VI-F | Ae-1 | Eb-1 |
| Ff-31 | VI-F | Af-1 | Eb-1 |
| Ff-32 | VI-F | Af-1 | Ea-1 |
| Ff-33 | VI-F | Ae-1 | Ee-3 |
| Ff-34 | VI-F | Af-1 | Ee-3 |
| Ff-35 | VI-F | Af-2 | Ee-3 |
| Ff-36 | VI-F | Af-1 | Ee-2 |
| Ff-37 | VI-F | Ae-1 | Ee-1 |
| Ff-38 | VI-F | Af-1 | (S)-3-(4-(trifluoromethyl)phenyl) morpholine |
| Ff-39 | VI-F | Af-1 | Ej-1 |
| Ff-40 | VI-F | Af-1 | Ej-2 |
| Ff-41 | VI-F | Ae-1 | (±)-Ei-1 |
| Ff-42 | VI-F | Ae-1 | (±)-Ei-2 |
| Ff-43 | VI-F | Af-1 | Ek-1 |
| Ff-44 | VI-F | Af-1 | E1-1 |
| Ff-45 | VI-F | Af-1 | Ed-6 |
| Ff-46 | VI-F | Af-1 | Ed-7 |
| Ff-47 | VI-F | Af-1 | Eh-7 |
| Ff-48 | VI-F + Suzuki | Af-1 | Ed-8 + 4-(4,4,5,5-tetramethyl-1,3,2-dioxaborolan-2-yl)-1-(difluoromethyl)-1H-pyrazole |
| Ff-49 | VI-F + Suzuki | Af-3 | Em-1 |
| Ff-50 | VI-F + Suzuki | Ae-1 | Ed-9 + 4-(4,4,5,5-tetramethyl-1,3,2-dioxaborolan-2-yl)-1-(trifluoromethyl)-1H-pyrazole |
| Ff-51 | VI-F | Ae-1 | Ed-9 + 1-(difluoromethyl)-4-(4,4,5,5-tetramethyl-1,3,2-dioxaborolan-2-yl)-1H-pyrazole |
| Ff-52 | VI-F | Af-1 | Ec-6 |
| Ff-53 | VI-F | Af-1 | Ec-7 |
| Ff-54 | VI-F | Bb-2 | Ec-2 |
| Ff-55 | VI-F | Af-1 | En-1 |
| Ff-56 | VI-F | Af-1 | En-1 |
| Ff-57 | VI-F | Ae-1 | Ed-10 |
| Ff-58 | VI-F | Af-1 | Eo-1 |
| Ff-59 | VI-F | Af-5 | Eh-1 |
| Ff-60 | VI-F | Af-3 | spiro[chromane-2,4'-piperidin]-4-one |
| Ff-61 | VI-F | Af-3 | 2H-spiro[benzofuran-3,4'-piperidine] |
| Ff-62 | VI-F | Af-1 | 2,3,4,5-Tetrahydro-1h-1,5-methanobenzo[d]azepine hydrochloride |
| Ff-63 | VI-F | Ae-1 | Ec-7 |
| Ff-64 | VI-F | Af-3 | 1-methylspiro[indoline-3,4'-piperidin]-2-one |
| Ff-65 | VI-F | Af-3 | spiro[indoline-3,4'-piperidin]-2-one. |
| Ff-66 | VI-F | Af-1 | Ep-1 |
| Ff-67 | VI-F | Af-1 | E1-2 |
| Ff-68 | VI-F | Af-4 | Eh-3 |
| Ff-69 | VI-F | Af-1 | Ec-8 |
| Ff-70 | VI-F | Af-1 | Ec-9 |
| Ff-71 | VI-F | Ae-1 | Eb-2 |
| Ff-72 | VI-F | Ae-1 | Eb-3 |
| Ff-73 | VI-F | Af-1 | Eb-4 |
| Ff-74 | VI-F | Ae-1 | Ef-1 |

TABLE 2-continued

| Synthetic procedure for some examples disclosed herein | | | |
|---|---|---|---|
| Example | Coupling Procedure | Core Intermediate | Tail Intermediate |
| Ff-75 | Chiral separation of Example Ff-28 | Af-1 | Ee-1 |
| Ff-76 | Chiral separation of Example Ff-28 | Af-1 | Ee-1 |
| Ff-77 | VI-F | Af-1 | Eu-2 |
| Ff-78 | VI-F | Af-1 | Eu-2 |
| Ff-80 | VI-F | Af-1 | Eu-1 |
| Ff-81 | VI-F | Af-1 | Eu-1 |
| Ff-82 | Chiral separation of Example Ff-34 | Af-1 | Ee-3 |
| Ff-83 | Chiral separation of Example Ff-34 | Af-1 | Ee-3 |
| Ff-84 | VI-F | Ae-1 | commercial (3S)-3-[4-(trifluoromethyl)phenyl]morpholine |
| Ff-85 | VI-F | Af-1 | Ez-1 |
| Ff-86 | VI-F | Af-7 | commercial (3S)-3-[4-(trifluoromethyl)phenyl]morpholine |
| Ff-87 | VI-F | Af-7 | commercial (2R)-2-[4-(trifluoromethyl)phenyl]piperidine hydrochloride |
| Ff-88 | VI-F | Af-1 | Eu-3 |
| Ff-89 | VI-F | Ae-1 | Eu-1 |
| Ff-90 | VI-F | Af-1 | Ef-2 |
| Ff-91 | VI-F | Af-2 | Ef-2 |
| Ff-92 | VI-F | Af-5 | commercial (3S)-3-[4-(trifluoromethyl)phenyl]morpholine |
| Ff-93 | VI-F | Af-1 | Et-2 |
| Ff-94 | VI-F | Af-1 | Eh-5 |
| Ff-95 | VI-F + Suzuki | Af-1 | Eh-5 + 4-(4,4,5,5-tetramethyl-1,3,2-dioxaborolan-2-yl)-1-(trifluoromethyl)-1H-pyrazole |
| Ff-96 | VI-F + Suzuki | Af-1 | Et-2 + 1-(difluoromethyl)-4-(4,4,5,5-tetramethyl-1,3,2-dioxaborolan-2-yl)pyrazole |
| Ff-97 | VI-F + Suzuki | Af-1 | Et-2 + 4-(4,4,5,5-tetramethyl-1,3,2-dioxaborolan-2-yl)-1-(trifluoromethyl)-1H-pyrazole |
| Ff-98 | VI-F | Af-7 | Eu-2 |
| Ff-99 | VI-F | Af-5 | Ev-1 |
| Ff-100 | VI-F | Af-1 | Ev-4 |
| Ff-101 | VI-F | Af-1 | Ev-2 |
| Ff-102 | VI-F | Af-1 | Ev-3 |
| Ff-103 | VI-F | Ah-1 | commercial (3S)-3-[4-(trifluoromethyl)phenyl]morpholine |
| Ff-104 | VI-F | Af-1 | Ew-1 |
| Ff-105 | VI-F | Af-1 | Ew-2 |
| Ff-106 | VI-F | Af-6 | Ev-4 |
| Ff-107 | VI-F | Ag-1 | Ew-3 |
| Ff-108 | VI-F | Ag-1 | Ew-2 |
| Ff-109 | VI-F | Af-6 | Ew-3 |
| Ff-110 | VI-F | Af-6 | Ew-1 |
| Ff-111 | VI-F | Ae-1 | Ew-1 |
| Ff-112 | VI-F | Af-1 | Ev-5 |
| Ff-113 | VI-F | Af-6 | Ev-5 |
| Ff-114 | VI-F | Af-1 | Eaa-1 |
| Ff-115 | VI-F | Af-6 | Ew-2 |
| Ff-116 | VI-F | Ag-2 | Ew-2 |
| Ff-117 | VI-F | Af-1 | Ew-4 |
| Ff-118 | VI-F | Ae-1 | Ew-3 |
| Ff-119 | VI-F | Ag-2 | Ew-3 |
| Ff-120 | VI-F | Af-1 | Ex-1 |
| Ff-121 | VI-F | Af-1 | Ey-1 |
| Ff-122 | VI-F | Af-3 | Ew-3 |
| Ff-123 | VI-F | Ae-1 | Ed-11 |
| Ff-124 | VI-F | Af-1 | Ed-11 |
| Ff-125 | VI-F | Ae-1 | Ed-12 |
| Ff-126 | VI-F | Ae-1 | Ed-13 |
| Ff-127 | VI-F | Ae-1 | Ear-1 |
| Ff-128 | VI-F | Af-1 | Eai-10 |
| Ff-129 | VI-F | Af-1 | Eai-11 |
| Ff-130 | VI-F | Af-1 | Eai-8 |
| Ff-131 | VI-F | Af-1 | Eai-2 |
| Ff-132 | VI-F | Af-1 | Eai-3 |
| Ff-133 | VI-F | Af-1 | Eai-4 |
| Ff-134 | VI-F | Af-1 | Eai-5 |
| Ff-135 | VI-F | Af-1 | Eai-6 |

TABLE 2-continued

Synthetic procedure for some examples disclosed herein

| Example | Coupling Procedure | Core Intermediate | Tail Intermediate |
|---|---|---|---|
| Ff-136 | VI-F | Af-1 | Eai-7 |
| Ff-137 | VI-F | Af-4 | commercial (S)-3-(4-(trifluoromethyl)phenyl)morpholine |
| Ff-138 | VI-F | Af-2 | Eai-8 |
| Ff-139 | VI-F | Af-1 | Commerical (R)-2-(4-(trifluoromethyl)phenyl)piperidine hydrochloride |
| Ff-140 | VI-F | Af-1 | Eaj-1 |
| Ff-141 | VI-F | Af-1 | Eak-1 |
| Ff-142 | VI-F | Af-6 | Eai-2 |
| Ff-143 | VI-F | Af-1 | Eak-2 |
| Ff-144 | VI-F | Af-1 | Eap-1 |
| Ff-145 | VI-F + suzuki | Af-1 | Eh-5 + 1-(oxetan-3-yl)-4-(4,4,5,5-tetramethyl-1,3,2-dioxaborolan-2-yl)pyrazole |
| Ff-146 | VI-F | Af-1 | Eak-3 |
| Ff-147 | VI-F + Suzuki | Af-1 | Ed-9 + 2-[4-(4,4,5,5-tetramethyl-1,3,2-dioxaborolan-2-yl)pyrazol-1-yl]pyridine |
| Ff-148 | VI-F + Suzuki | Af-1 | Ed-9 + 3-[4-(4,4,5,5-tetramethyl-1,3,2-dioxaborolan-2-yl)pyrazol-1-yl]pyridine |
| Ff-149 | VI-F | Af-1 | Eak-4 |
| Ff-150 | VI-F + Suzuki | Af-1 | Eh-5 + 3-(4,4,5,5-tetramethyl-1,3,2-dioxaborolan-2-yl)-6,7-dihydro-4H-pyrazolo[5,1-c][1,4]oxazine |
| Ff-151 | VI-F | Af-1 | Eak-1 |
| Ff-152 | VI-F | Af-1 | Eak-1 |
| Ff-153 | VI-F | Af-1 | Eah-2 |
| Ff-154 | VI-F | Af-1 | Eak-3 |
| Ff-155 | VI-F | Af-1 | Eak-3 |
| Ff-156 | VI-F | Af-1 | Ean-1 |
| Ff-157 | VI-F | Af-1 | Ev-6 |
| Ff-158 | VI-F | Af-1 | Eam-1 |
| Ff-159 | VI-F | Af-1 | Et-4 |
| Ff-160 | VI-F | Af-1 | Et-3 |
| Ff-161 | VI-F | Af-1 | Et-5 |
| Ff-162 | VI-F | Af-6 | Et-5 |
| Ff-163 | VI-F | Af-1 | Eas-1 |
| Ff-164 | VI-F | Af-1 | Eas-1 |
| Ff-165 | VI-F | Af-1 | Et-6 |
| Ff-166 | VI-F | Af-1 | Ebb-2 |
| Ff-167 | VI-F | Af-1 | Eau-1 |
| Ff-168 | VI-F | Af-1 | Eau-2 |
| Ff-169 | VI-F | Af-1 | Eau-3 |
| Ff-170 | VI-F | Af-1 | Eau-4 |
| Ff-171 | VI-F | Af-1 | Eau-4 |
| Ff-172 | VI-F | Af-1 | Eau-5 |
| Ff-173 | VI-F | Af-1 | Eau-5 |
| Ff-174 | VI-F | Af-1 | Eav-1 |
| Ff-175 | VI-F | Af-1 | Eav-2 |
| Ff-176 | VI-F | Af-1 | Eaw-1 |
| Ff-177 | VI-F | Ae-1 | Eaw-1 |
| Ff-178 | VI-F | Af-6 | Eaw-1 |
| Ff-179 | VI-F | Ag-1 | Eaw-1 |
| Ff-180 | VI-F | Ag-2 | Eaw-1 |
| Ff-181 | VI-F | Af-1 | Eaw-2 |
| Ff-182 | VI-F | Af-6 | Eaw-2 |
| Ff-183 | VI-F | Af-1 | Eaw-3 |
| Ff-184 | VI-F | Af-1 | Eaw-3 |
| Ff-185 | VI-F | Af-6 | Eaw-3 |
| Ff-186 | VI-F | Af-6 | Eaw-3 |
| Ff-187 | VI-F | Ae-1 | Eaw-3 |
| Ff-188 | VI-F | Ae-1 | Eaw-3 |
| Ff-189 | VI-F | Af-3 | Eaw-3 |
| Ff-190 | VI-F | Af-3 | Eaw-3 |
| Ff-191 | VI-F | Af-1 | Eaw-5 |
| Ff-192 | VI-F | Af-1 | Eaw-5 |
| Ff-193 | VI-F | Af-6 | Eaw-5 |
| Ff-194 | VI-F | Af-6 | Eaw-5 |
| Ff-195 | VI-F | Af-6 | Eaw-4 |
| Ff-196 | VI-F | Af-6 | Eaw-4 |
| Ff-197 | VI-F | Af-1 | Eaw-4 |
| Ff-198 | VI-F | Af-1 | Eaw-4 |
| Ff-199 | VI-F + suzuki | Af-1 | Eas-1 + 1-(difluoromethyl)-4-(4,4,5,5-tetramethyl-1,3,2-dioxaborolan-2-yl)pyrazole |

TABLE 2-continued

Synthetic procedure for some examples disclosed herein

| Example | Coupling Procedure | Core Intermediate | Tail Intermediate |
|---|---|---|---|
| Ff-200 | VI-F + suzuki | Af-1 | Eas-1 + 1-(difluoromethyl)-4-(4,4,5,5-tetramethyl-1,3,2-dioxaborolan-2-yl)pyrazole |
| Ff-201 | VI-F | Af-1 | Et-6 + cyclopropylboronic acid |
| Ff-202 | VI-F | Ae-1 | Ec-10 |
| Ff-203 | VI-F + suzuki | Ae-1 | Eh-5 + 4-(4,4,5,5-tetramethyl-1,3,2-dioxaborolan-2-yl)-1-(trifluoromethyl)-1H-pyrazole |
| Ff-204 | VI-F + suzuki | Af-1 | Ec-3 + 1-methyl-4-(4,4,5,5-tetramethyl-1,3,2-dioxaborolan-2-yl)pyrazole |
| Ff-205 | VI-F + suzuki | Af-1 | Ec-3 + 1-(difluoromethyl)-4-(3,3,4,4-tetramethyl-1lambda3,2,5-bromadioxolan-1-yl)pyrazole |
| Ff-208 | VI-F | Af-1 | Ej-3 |
| Ff-209 | VI-F | Af-1 | Ej-4 |
| Ff-210 | VI-F | Af-1 | Ec-10 |
| Ff-211 | VI-F + suzuki | Af-1 | Ec-11 + 4-(4,4,5,5-tetramethyl-1,3,2-dioxaborolan-2-yl)-1-(trifluoromethyl)pyrazole |
| Ff-212 | VI-F + suzuki | Af-1 | Ec-11 + 1-(difluoromethyl)-4-(4,4,5,5-tetramethyl-1,3,2-dioxaborolan-2-yl)pyrazole |
| Ff-213 | VI-F + suzuki | Af-1 | Eh-5 + 1-(difluoromethyl)-4-(4,4,5,5-tetramethyl-1,3,2-dioxaborolan-2-yl)pyrazole |
| Ff-214 | VI-F + suzuki | Af-1 | Eh-5 + 1-methyl-4-(4,4,5,5-tetramethyl-1,3,2-dioxaborolan-2-yl)pyrazole |
| Ff-215 | VI-F + suzuki | Af-1 | Eh-5 + 1-cyclopropyl-4-(4,4,5,5-tetramethyl-1,3,2-dioxaborolan-2-yl)pyrazole |
| Ff-216 | VI-F + suzuki | Af-1 | Ed-9 + 5-(4,4,5,5-tetramethyl-1,3,2-dioxaborolan-2-yl)-1-(trifluoromethyl)pyrazole |
| Ff-217 | VI-F + suzuki | Af-1 | Ed-9 + (2-methylpyrazol-3-yl)boronic acid |
| Ff-218 | VI-F + suzuki | Af-1 | Ec-3 + 5-(4,4,5,5-tetramethyl-1,3,2-dioxaborolan-2-yl)-1-(trifluoromethyl)pyrazole |
| Ff-219 | VI-F + suzuki | Af-1 | Ec-3 + (2-methylpyrazol-3-yl)boronic acid |
| Ff-220 | VI-F + suzuki | Af-1 | Ed-15 + 4-(4,4,5,5-tetramethyl-1,3,2-dioxaborolan-2-yl)-1-(trifluoromethyl)pyrazole |
| Ff-221 | VI-F + suzuki | Af-1 | Ed-15 + 1-(difluoromethyl)-4-(4,4,5,5-tetramethyl-1,3,2-dioxaborolan-2-yl)pyrazole |
| Ff-222 | VI-F | Af-1 | Eai-12 |
| Ff-223 | VI-F | Af-1 | Eai-13 |
| Ff-224 | VI-F | Af-1 | Eai-14 |
| Ff-225 | VI-F | Af-1 | Eai-15 |
| Ff-226 | VI-F | Af-1 | Ed-16 |
| Ff-227 | VI-F | Af-1 | Ec-12 |
| Ff-228 | VI-F | Af-1 | Eai-16 |
| Ff-229 | VI-F + suzuki | Af-1 | Eh-5 + 5-(4,4,5,5-tetramethyl-1,3,2-dioxaborolan-2-yl)-2-(trifluoromethyl)pyridine |
| Ff-230 | VI-F + suzuki | Af-1 | Eh-5 + [4-(trifluoromethyl)phenyl]boronic acid |
| Ff-231 | VI-F + borylation + suzuki | Af-1 | Eh-5 + 4-bromo-2-(trifluoromethyl)thiazole |
| Ff-232 | VI-F + borylation + suzuki | Af-1 | Eh-5 + 5-bromo-2-(trifluoromethyl)thiazole |
| Ff-233 | VI-F + borylation + suzuki | Af-1 | Eh-5 + 5-bromo-2-(difluoromethyl)thiazole |
| Ff-234 | VI-F + suzuki | Af-1 | Et-1 + 4-(4,4,5,5-tetramethyl-1,3,2-dioxaborolan-2-yl)-1-(trifluoromethyl)pyrazole |
| Ff-235 | VI-F + suzuki | Af-1 | Et-1 + 1-(difluoromethyl)-4-(4,4,5,5-tetramethyl-1,3,2-dioxaborolan-2-yl)pyrazole |
| Ff-236 | VI-F + suzuki | Af-1 | Et-1 + cyclopropylboronic acid |
| Ff-237 | VI-F + borylation + suzuki | Af-1 | Eh-5 + 4-bromo-2-(difluoromethyl)thiazole |
| Ff-238 | VI-F + suzuki | Af-1 | Eh-5 + [5-(trifluoromethyl)-2-pyridyl]boronic acid |
| Ff-239 | VI-F + suzuki | Af-1 | Et-1 + 5-(4,4,5,5-tetramethyl-1,3,2-dioxaborolan-2-yl)-2-(trifluoromethyl)pyridine |
| Ff-240 | VI-F + suzuki | Af-1 | Et-1 + [4-(trifluoromethyl)phenyl]boronic acid |
| Ff-241 | VI-F | Af-1 | Eay-1 |
| Ff-242 | VI-F + SFC | Af-1 | Eai-12 |
| Ff-243 | VI-F + SFC | Af-1 | Eai-12 |
| Ff-244 | VI-F + SFC | Af-1 | Eai-16 |
| Ff-245 | VI-F + SFC | Af-1 | Eai-16 |
| Ff-246 | VI-F | Ae-1 | Eaz-2 |
| Ff-247 | VI-F | Af-6 | Eaz-2 |
| Ff-248 | VI-F | Af-1 | Ew-6 |
| Ff-249 | VI-F | Ae-1 | Eax-1 |
| Ff-250 | VI-F | Af-6 | Eax-1 |
| Ff-251 | VI-F | Af-1 | Ew-7 |
| Ff-252 | VI-F | Af-6 | Ew-7 |

TABLE 2-continued

Synthetic procedure for some examples disclosed herein

| Example | Coupling Procedure | Core Intermediate | Tail Intermediate |
|---|---|---|---|
| Ff-253 | VI-F | Af-1 | Eab-2 |
| Ff-254 | VI-F | Af-6 | Eab-2 |
| Ff-255 | VI-F | Af-1 | Eab-1 |
| Ff-256 | VI-F | Af-6 | Eab-1 |
| Ff-257 | VI-F | Af-1 | Eba-1 |
| Ff-258 | VI-F | Af-6 | Eba-1 |
| Ff-259 | VI-F | Af-6 | Ew-8 |
| Ff-260 | VI-F | Af-1 | Ew-9 |
| Ff-261 | VI-F | Af-6 | Ew-6 |
| Ff-262 | VI-F | Af-6 | Eba-2 |
| Ff-263 | VI-F + suzuki | Af-1 | Ebb-1 + 2-(trifluoro-14-boraneyl)cyclopropane-1-carbonitrile |
| Ff-264 | VI-F | Ae-1 | Ec-13 |
| Ff-265 | VI-F | Af-1 | Ec-13 |
| Ff-266 | VI-F | Ae-1 | Eh-3 |
| Ff-267 | VI-F | Ae-1 | Ec-14 |
| Ff-268 | VI-F | Af-1 | Ec-14 |
| Ff-269 | VI-F | Af-1 | Eh-5 + $Zn(CN)_2$ |
| Ff-270 | VI-F | Ae-1 | Ed-17 |
| Ff-271 | VI-F | Af-1 | Ej-5 |
| Ff-272 | VI-F | Af-1 | Ec-15 |
| Ff-273 | VI-F | Af-1 | Ed-18 |
| Ff-274 | VI-F | Af-1 | Ed-19 |
| Ff-275 | VI-F | Af-1 | Ec-16 |
| Ff-276 | VI-F | Af-1 | Ed-20 |
| Ff-277 | VI-F | Af-1 | Ed-21 |
| Ff-278 | VI-F | Ae-1 | Ed-6 |
| Ff-279 | VI-F + Suzuki | Af-1 | Eh-4 + 4-(4,4,5,5-tetramethyl-1,3,2-dioxaborolan-2-yl)-1-(trifluoromethyl)pyrazole |
| Ff-280 | VI-F + Suzuki | Af-1 | Eh-4 + 3-(4,4,5,5-tetramethyl-1,3,2-dioxaborolan-2-yl)-1-(trifluoromethyl)pyrazole |
| Ff-281 | VI-F | Af-1 | Ei-3 |
| Ff-282 | VI-F | Af-1 | Ei-4 |
| Ff-283 | VI-F | Af-1 | (±)-Ei-2 |
| Ff-284 | VI-F | Af-2 | (±)-Ei-2 |
| Ff-285 | VI-F | Af-1 | Ed-22 |
| Ff-286 | VI-F | Af-1 | Ed-23 |
| Ff-287 | VI-F | Af-1 | Ebc-1 |
| Ff-288 | VI-F | Ae-1 | Ebc-1 |
| Ff-289 | VI-F | Af-2 | Commercial (3S)-3-[4-(trifluoromethyl)phenyl] morpholine |
| Ff-290 | VI-F | Af-1 | Ed-24 |
| Ff-291 | VI-F | Af-1 | Ed-25 |
| Ff-292 | VI-F | Af-1 | Eh-4 + 1-(difluoromethyl)-4-(4,4,5,5-tetramethyl-1,3,2-dioxaborolan-2-yl)pyrazole |
| Ff-293 | VI-F | Af-1 | Eai-17 |
| Ff-294 | VI-F | Af-1 | Ebd-1 |
| Ff-295 | VI-F | Af-1 | Ebd-2 |
| Ff-296 | VI-F | Af-1 | Ebd-3 |
| Ff-297 | VI-F | Af-1 | Ebd-4 |
| Ff-298 | VI-F | Af-1 | Ebd-5 |
| Ff-299 | VI-F | Af-1 | E1-3 |
| Ff-300 | VI-F | Af-1 | E1-4 |
| Ff-301 | VI-F | Af-1 | E1-5 |
| Ff-302 | VI-F | Ae-1 | Ei-3 |
| Ff-303 | VI-F | Af-4 | Ei-3 |
| Ff-304 | VI-F | Af-5 | Ei-3 |
| Ff-305 | VI-F | Af-4 | Eh-1 |
| Ff-306 | VI-F | Af-1 | Ed-26 |
| Ff-307 | VI-F | Af-1 | Ed-24 |
| Ff-308 | VI-F | Af-2 | Ei-3 |
| Ff-309 | VI-F | Af-1 | Ej-6 |
| Ff-310 | VI-F | Af-1 | Eax-1 |
| Ff-311 | VI-F | Af-1 | Ed-28 |
| Ff-312 | VI-F | Af-1 | Eab-8 |
| Ff-313 | VI-F | Af-1 | Eab-5 |
| Ff-314 | VI-F | Af-1 | Eax-2 |
| Ff-315 | VI-F | Af-1 | Ed-29 |
| Ff-316 | VI-F | Af-4 | Eh-8 |
| Ff-317 | VI-F | Af-5 | Eh-8 |
| Ff-318 | VI-F | Af-1 | Eh-8 |
| Ff-319 | VI-F | Af-1 | Eax-3 |
| Ff-320 | VI-F | Af-1 | Eax-4 |
| Ff-321 | VI-F | Af-1 | Eax-5 |
| Ff-322 | VI-F | Af-1 | Eax-6 |

TABLE 2-continued

Synthetic procedure for some examples disclosed herein

| Example | Coupling Procedure | Core Intermediate | Tail Intermediate |
|---|---|---|---|
| Ff-323 | VI-F | Af-1 | Eax-7 |
| Ff-324 | VI-F | Af-1 | Eaf-2 |
| Ff-325 | VI-F | Af-1 | Eag-1 |
| Ff-326 | VI-F | Af-1 | Eaz-3 |
| Ff-327 | VI-F | Af-1 | Eaz-5 |
| Ff-328 | VI-F | Af-1 | Eaz-4 |
| Ff-329 | VI-F | Af-1 | Eaz-4 |
| Ff-330 | VI-F | Af-1 | Eab-6 |
| Ff-331 | VI-F | Af-1 | Ev-7 |
| Ff-332 | VI-F | Aa-1 | Ev-1 |
| Ff-333 | VI-F | Af-1 | Eba-3 |
| Ff-334 | VI-F | Ai-1 | Eat-1 |
| Ff-335 | VI-F | Af-1 | Ebe-4 |
| Ff-336 | VI-F | Af-6 | Ew-11 |
| Ff-337 | VI-F | Af-1 | Eae-1 |
| Ff-338 | VI-F | Af-6 | Eba-3 |
| Ff-339 | VI-F | Ae-1 | Eba-3 |
| Ff-340 | VI-F | Ag-1 | Ew-12 |
| Ff-341 | VI-F | Af-6 | Ew-12 |
| Ff-342 | VI-F | Af-6 | Eh-1 |
| Ff-343 | VI-F | Af-1 | Ew-11 |
| Ff-344 | VI-F | Ag-1 | Ew-1 |
| Ff-345 | VI-F | Af-3 | Ew-1 |
| Ff-346 | VI-F | Al-1 | Ew-1 |
| Ff-347 | VI-F | Ag-1 | Ew-11 |
| Ff-348 | VI-F | Af-6 | Ew-17 |
| Ff-349 | VI-F | Al-1 | Ew-12 |
| Ff-350 | VI-F | Af-1 | Eba-4 |
| Ff-351 | VI-F | Af-6 | Eba-4 |
| Ff-352 | VI-F | Af-3 | Ebg-1 |
| Ff-353 | VI-F | Ae-1 | Ebg-1 |
| Ff-354 | VI-F | Af-1 | Ebg-2 |
| Ff-355 | VI-F | Af-3 | Ebg-2 |
| Ff-356 | VI-F | Ae-1 | Ebg-2 |
| Ff-357 | VI-F | Af-1 | Ebh-1 |
| Ff-358 | VI-F | Af-4 | Ebh-1 |
| Ff-359 | VI-F | Af-5 | Ebh-1 |
| Ff-360 | VI-F | Aj-1 | Ebh-1 |
| Ff-361 | VI-F | Af-1 | Ew-14 |
| Ff-362 | VI-F | Af-4 | Ew-14 |
| Ff-363 | VI-F | Af-5 | Ew-14 |
| Ff-364 | VI-F | Aj-1 | Ew-14 |
| Ff-365 | VI-F | Af-1 | Ebi-1 |
| Ff-366 | VI-F | Af-1 | Ebi-3 |
| Ff-367 | VI-F | Af-6 | Ebi-1 |
| Ff-368 | VI-F | Am-1 | Ew-1 |
| Ff-369 | VI-F | Ag-1 | Ebi-1 |
| Ff-370 | VI-F | Af-2 | Ebi-1 |
| Ff-371 | VI-F | Af-2 | Ebi-3 |
| Ff-372 | VI-F | Af-1 | Ebi-5 |
| Ff-373 | VI-F | Af-6 | Ebi-5 |
| Ff-374 | VI-F | Af-4 | Ew-15 |
| Ff-375 | VI-F | Af-1 | Ew-15 |
| Ff-376 | VI-F | Ag-1 | Ew-16 |
| Ff-377 | VI-F | Ae-1 | Ew-16 |
| Ff-378 | VI-F | Af-6 | Ew-16 |
| Ff-379 | VI-F | Af-4 | Ew-1 |
| Ff-380 | VI-F | Af-1 | Eby-3 |
| Ff-381 | VI-F | Ae-1 | Ew-11 |
| Ff-382 | VI-F | Af-4 | Eae-1 |
| Ff-383 | VI-F | Ae-1 | Ew-12 |
| Ff-384 | VI-F | Af-1 | Eba-5 |
| Ff-385 | VI-F | Af-4 | Eba-5 |
| Ff-386 | VI-F | Af-6 | Eba-6 |
| Ff-387 | VI-F | Af-1 | Eby-1 |
| Ff-388 | VI-F | Ag-1 | Ew-17 |
| Ff-389 | VI-F | Ae-1 | Ew-2 |
| Ff-390 | VI-F + SFC separation | Af-1 | El-1 |
| Ff-391 | VI-F + SFC separation | Af-1 | Ebc-1 |
| Ff-392 | VI-F + SFC separation | Af-1 | Ebc-1 |
| Ff-393 | VI-F + SFC separation | Af-1 | Eax-5 |
| Ff-394 | VI-F + SFC separation | Af-1 | Ev-7 |
| Ff-395 | VI-F + SFC separation | Af-1 | Ev-7 |
| Ff-396 | VI-F + SFC separation | Af-1 | Eba-3 |
| Ff-397 | VI-F + SFC separation | Af-1 | Eba-3 |

TABLE 2-continued

Synthetic procedure for some examples disclosed herein

| Example | Coupling Procedure | Core Intermediate | Tail Intermediate |
|---|---|---|---|
| Ff-398 | VI-F + SFC separation | Af-1 | Ej-6 |
| Ff-399 | VI-F + SFC separation | Af-6 | Eba-6 |
| Ff-400 | VI-F + SFC separation | Aa-1 | Ev-7 |
| Ff-401 | VI-F | Af-1 | Eai-19 |
| Ff-402 | VI-F | Af-4 | Ebl-1 |
| Ff-403 | VI-F | Af-1 | Ebk-1 |
| Ff-404 | VI-F | Af-1 | Ebl-1 |
| Ff-405 | VI-F | Af-1 | Ebz-1 |
| Ff-406 | VI-F | Af-2 | Eaz-1 |
| Ff-407 | VI-F | Ae-1 | Eh-9 |
| Ff-408 | VI-F | Ae-1 | Ed-30 |
| Ff-409 | VI-F | Ae-1 | Ed-31 |
| Ff-410 | VI-F | Ae-1 | Ed-4 |
| Ff-411 | VI-F | Ae-1 | Ed-33 |
| Ff-412 | VI-F | Ae-1 | Ed-34 |
| Ff-413 | VI-F | Af-1 | Ec-17 |
| Ff-414 | VI-F | Af-1 | Ed-35 |
| Ff-415 | VI-F | Af-1 | Ec-18 |
| Ff-416 | VI-F | Af-1 | Ed-37 |
| Ff-417 | VI-F | Af-1 | Ed-38 |
| Ff-418 | VI-F | Af-1 | Ed-39 |
| Ff-419 | VI-F | Af-1 | Ed-40 |
| Ff-420 | VI-F | Af-1 | Ec-20 |
| Ff-421 | VI-F | Af-1 | Ed-41 |
| Ff-422 | VI-F | Af-1 | Ec-19 |
| Ff-423 | VI-F | Af-1 | Ed-42 |
| Ff-424 | VI-F | Af-1 | Ed-32 |
| Ff-425 | VI-F | Af-1 | Eh-14 |
| Ff-426 | VI-F | Af-1 | Eh-10 |
| Ff-427 | VI-F | Af-1 | Ee-4 |
| Ff-428 | VI-F | Af-1 | Ebm-1 |
| Ff-429 | VI-F | Af-1 | Ebm-2 |
| Ff-430 | VI-F | Af-1 | Eh-11 |
| Ff-431 | VI-F | Af-1 | Eh-12 |
| Ff-432 | VI-F | Af-1 | Ebe-5 |
| Ff-433 | VI-F | Af-1 | commercial N-methyl-1-(4-(2,2,2-trifluoroethoxy)phenyl)methanamine |
| Ff-434 | VI-F + LXV-E | Af-1 | commercial (R)-5-bromo-N-methyl-2,3-dihydro-1H-inden-1-amine + trans-potassium (2-cyanocyclopropyl)trifluoroborate |
| Ff-435 | VI-F | Ag-2 | Eh-13 |
| Ff-436 | VI-F | Af-6 | Eh-13 |
| Ff-437 | VI-F + sonogashira | Af-1 | Eh-16 + 4-(difluoromethyl)-4-ethynyl-tetrahydropyran |
| Ff-438 | VI-F | Af-1 | Ebm-3 |
| Ff-439 | VI-F + sonogashira | Af-1 | Eh-16 + 2,2-dimethylbut-3-ynenitrile |
| Ff-440 | VI-F + sonogashira | Af-1 | Eh-16 + 3-ethynyl-3-fluoro-oxetane |
| Ff-441 | VI-F + sonogashira | Af-1 | Eh-16 + 2-(1-ethynylcyclopropyl)acetonitrile |
| Ff-442 | VI-F + sonogashira | Af-1 | Eh-16 + 2-methylbut-3-yn-2-ol |
| Ff-443 | VI-F | Af-2 | Ebm-3 |
| Ff-444 | VI-F + reductive coupling | Af-1 | Eh-16 + 1-bromobicyclo[1.1.1]pentane |
| Ff-445 | VI-F + sonogashira | Af-1 | Eh-16 + 1-ethynylcyclopropanecarbonitrile |
| Ff-446 | VI-F + sonogashira | Af-1 | Eh-16 + 3-ethynyl-3-fluoro-tetrahydrofuran |
| Ff-447 | VI-F + sonogashira | Af-1 | Eh-16 + 3-fluoro-3-methyl-but-1-yne |
| Ff-448 | VI-F + LXV-E | Af-1 | Et-1 + trans-potassium (2-cyanocyclopropyl) trifluoroborate |
| Ff-449 | VI-F + reductive coupling | Af-6 | Eh-16 + 1-bromobicyclo[1.1.1]pentane |
| Ff-450 | VI-F | Af-1 | Ebm-3 |
| Ff-451 | VI-F + reductive coupling | Af-6 | Eh-16 + 1-(difluoromethyl)-3-iodo-bicyclo[1.1.1]pentane |
| Ff-452 | VI-F + reductive coupling | Ag-2 | Eh-16 + 1-bromobicyclo[1.1.1]pentane |
| Ff-453 | VI-F + reductive coupling | Af-1 | Eh-16 + 1-fluoro-3-iodo-bicyclo[1.1.1]pentane |
| Ff-454 | VI-F | Af-1 | commercial N-methyl-1-(1-phenyl-1H-pyrazol-3-yl)methanamine |
| Ff-455 | VI-F | Af-1 | Eh-17 |
| Ff-456 | VI-F | Af-1 | Eh-18 |
| Ff-457 | VI-F | Af-1 | Eh-19 |
| Ff-458 | VI-F | Af-1 | Eh-20 |
| Ff-459 | VI-F | Af-1 | Eh-21 |
| Ff-460 | VI-F | Af-1 | Eh-15 |
| Ff-461 | VI-F | Af-1 | Eas-4 |

TABLE 2-continued

| Synthetic procedure for some examples disclosed herein | | | |
|---|---|---|---|
| Example | Coupling Procedure | Core Intermediate | Tail Intermediate |
| Ff-462 | VI-F | Ag-2 | Eax-6 |
| Ff-463 | VI-F | Ag-1 | Eas-5 |
| Ff-464 | VI-F | Ag-1 | Eas-5 |
| Ff-465 | VI-F + reductive coupling | Af-1 | Eh-16 + 3-bromocyclobutane-1-carbonitrile |
| Ff-466 | VI-F + reductive coupling | Ag-1 | Eh-16 + 1-bromobicyclo[1.1.1]pentane |
| Ff-467 | VI-F + SFC | Af-1 | Et-7 |
| Ff-468 | VI-F | Af-1 | Ec-21 |
| Ff-470 | VI-F + SFC | Ae-1 | (±)-Ei-2 |
| Ff-471 | VI-F + SFC | Ae-1 | (±)-Ei-2 |
| Ff-472 | VI-F + Suzuki | Af-1 | Eh-5 + (1-phenylpyrazol-4-yl)boronic acid |
| Ff-473 | VI-F + LXV-E | Af-1 | Eh-5 + trans-4,4,5,5-tetramethyl-2-(2-phenylcyclopropyl)-1,3,2-dioxaborolane |
| Ff-474 | VI-F + LXV-E | Af-1 | Eh-5 + trans ¬-2-([1,1'-bi(cyclopropan)]-2-yl)-4,4,5,5-tetramethyl-1,3,2-dioxaborolane |
| Ff-475 | VI-F + LXV-E | Af-1 | Eh-5 + 2-(2,2-dimethylcyclopropyl)-4,4,5,5-tetramethyl-1,3,2-dioxaborolane |
| Ff-476 | VI-F + LXV-E | Af-1 | Eh-5 + 4,4,5,5-tetramethyl-2-(spiro[2.3]hexan-1-yl)-1,3,2-dioxaborolane |
| Ff-477 | VI-F + LXV-E | Af-1 | Eh-5 + 1-(difluoromethyl)-3-((1R,2R)-2-(4,4,5,5-tetramethyl-1,3,2-dioxaborolan-2-yl)cyclopropyl)-1H-pyrazole. |
| Ff-478 | VI-F + suzuki | Af-1 | Eh-5 + potassium isopropenyltrifluoroborate |
| Ff-479 | VI-F + suzuki + hydrogenation | Af-1 | Eh-5 + potassium isopropenyltrifluoroborate |
| Ff-480 | VI-F + LXV-E + SFC | Af-1 | Eh-5 + trans-2-(trifluoro-14-boraneyl) cyclopropane-1-carbonitrile |
| Ff-481 | VI-F + LXV-E + SFC | Af-1 | Eh-5 + trans-2-(trifluoro-14-boraneyl) cyclopropane-1-carbonitrile |
| Ff-482 | VI-F + LXV-E | Af-1 | Eh-5 + trans-2-(2-(4,4,5,5-tetramethyl-1,3,2-dioxaborolan-2-yl)cyclopropyl)pyridine |
| Ff-483 | VI-F+suzuki | Af-1 | Eh-5 + 2-(2,5-dihydrofuran-3-yl)-4,4,5,5-tetramethyl-1,3,2-dioxaborolane |
| Ff-484 | VI-F + suzuki + hydrogenation | Af-1 | Eh-5 + 2-(2,5-dihydrofuran-3-yl)-4,4,5,5-tetramethyl-1,3,2-dioxaborolane |
| Ff-485 | VI-F + suzuki | Af-1 | Eh-5 + 2-(2,2-dimethyl-2,5-dihydrofuran-3-yl)-4,4,5,5-tetramethyl-1,3,2-dioxaborolane |
| Ff-486 | VI-F + suzuki + hydrogenation | Af-1 | Eh-5 + 2-(2,2-dimethyl-2,5-dihydrofuran-3-yl)-4,4,5,5-tetramethyl-1,3,2-dioxaborolane |
| Ff-487 | VI-F | Af-2 | Ef-3 |
| Ff-488 | VI-F | Af-2 | Ef-10 |
| Ff-489 | VI-F | Af-2 | Ef-5 |
| Ff-490 | VI-F | Al-1 | Eh-1 |
| Ff-491 | VI-F + SFC | Af-1 | Ev-9 |
| Ff-492 | VI-F | Aj-1 | Eh-1 |
| Ff-493 | VI-F + NBS | Af-1 | Eh-1 |
| Ff-494 | VI-F + NBS | Af-1 | Eh-1 |
| Ff-495 | VI-F + NBS | Af-1 | Ew-1 |
| Ff-496 | VI-F + NBS | Af-1 | Eu-1 |
| Ff-497 | VI-F + NBS + Negishi | Af-1 | Eh-1 + $CD_3ZnCl$ |
| Ff-498 | VI-F | Ag-2 | Eaz-1 |
| Ff-499 | VI-F | Ag-2 | Ew-1 |
| Ff-500 | VI-F | Af-1 | Ew-18 |
| Ff-501 | VI-F | Af-1 | Ew-3 |
| Ff-502 | VI-F | Ag-2 | Eh-1 |
| Ff-503 | VI-F | Af-1 | Ebg-1 |
| Ff-504 | VI-F + LXV-E + SFC | Af-1 | Eh-5 + trans-2-(2-(difluoromethyl)cyclopropyl)-4,4,5,5-tetramethyl-1,3,2-dioxaborolane |
| Ff-505 | VI-F + LXV-E + SFC | Af-1 | Eh-5 + trans-2-(2-(difluoromethyl)cyclopropyl)-4,4,5,5-tetramethyl-1,3,2-dioxaborolane |
| Ff-506 | VI-F + sonogashira | Af-1 | Eh-5 + trimethylsilylacetylene |
| Ff-507 | VI-F | Af-6 | Ew-18 |
| Ff-508 | VI-F | Af-2 | Eae-1 |
| Ff-509 | VI-F | Ag-1 | Eh-1 |
| Ff-510 | VI-F | Ae-1 | Ebi-1 |
| Ff-511 | VI-F | Af-1 | Eai-20 |
| Ff-512 | VI-F | Af-1 | Eai-21 |
| Ff-513 | VI-F | Af-1 | Eai-22 |
| Ff-514 | VI-F | Af-1 | Eh-5 + 1-ethynyl-1-methylcyclopropane |
| Ff-515 | VI-F + sonogashira | Af-1 | Eh-5 + 3,3,3-trifluoroprop-1-yne |
| Ff-516 | VI-F + sonogashira | Af-1 | Eh-5 + 3-ethynyl-3-methyloxetane |
| Ff-517 | VI-F + sonogashira | Af-1 | Eh-5 + 1-ethynyl-1-methoxycyclobutane |
| Ff-518 | VI-F + sonogashira | Ae-1 | Eh-5 + 3-ethynyl-3-methyloxetane |
| Ff-519 | VI-F + sonogashira | Ae-1 | Eh-5 + 1-ethynyl-1-methoxycyclobutane |

TABLE 2-continued

Synthetic procedure for some examples disclosed herein

| Example | Coupling Procedure | Core Intermediate | Tail Intermediate |
|---|---|---|---|
| Ff-520 | VI-F + sonogashira | Ae-1 | Eh-5 + 1-ethynyl-1-(fluoromethyl)cyclopropane |
| Ff-521 | VI-F + sonogashira | Ae-1 | Eh-5 + 1-(difluoromethyl)-1-ethynylcyclopropane |
| Ff-522 | VI-F + sonogashira | Af-1 | Eh-5 + 1-ethynyl-1-(trifluoromethyl)cyclopropane |
| Ff-523 | VI-F + sonogashira | Af-1 | Eh-5 + 4-ethynyl-2-oxabicyclo[2.2.2]octane |
| Ff-524 | VI-F + sonogashira | Af-1 | Eh-5 + 6-ethynyl-3-oxabicyclo[3.1.0]hexane |
| Ff-525 | VI-F + sonogashira | Af-1 | Eh-5 + 3-ethynyl-1,1-difluorocyclobutan |
| Ff-526 | VI-F + sonogashira | Ae-1 | Eh-5 + 3-methyl-3-(methylsulfonyl)but-1-yne |
| Ff-527 | VI-F + sonogashira | Ae-1 | Eh-5 + 3-ethynyloxetan-3-ol |
| Ff-528 | VI-F + sonogashira | Ae-1 | Eh-5 + 1-ethynyl-7-oxabicyclo[2.2.1]heptane |
| Ff-529 | VI-F + sonogashira | Ae-1 | Eh-5 + 1-(3-ethynylazetidin-1-yl)ethan-1-one |
| Ff-530 | VI-F + sonogashira | Af-1 | Eh-4 + 1-(3-ethynylazetidin-1-yl)ethan-1-one |
| Ff-531 | VI-F + sonogashira | Ae-1 | Eh-4 + 1-ethynyl-1-methoxycyclopropane |
| Ff-532 | VI-F | Af-1 | Ebj-1 |
| Ff-533 | VI-F | Af-1 | Ebj-3 |
| Ff-534 | VI-F | Af-1 | Ebj-4 |
| Ff-535 | VI-F | Af-1 | Ebj-6 |
| Ff-536 | VI-F | Af-1 | Ebj-5 |
| Ff-537 | VI-F | Af-1 | Ebj-7 |
| Ff-538 | VI-F | Af-1 | Ebj-8 |
| Ff-539 | VI-F | Af-1 | Eaz-8 |
| Ff-540 | VI-F | Af-6 | Eaz-8 |
| Ff-541 | VI-F | Af-1 | Ebj-9 |
| Ff-542 | VI-F | Af-1 | Ebj-10 |
| Ff-543 | VI-F | Af-1 | Ebj-11 |
| Ff-544 | VI-F | Af-1 | Eag-2 |
| Ff-545 | VI-F | Af-1 | Eaf-1 |
| Ff-546 | VI-F + suzuki | Af-1 | Eh-5 + cyclopropylboronic acid monohydrate |
| Ff-547 | VI-F + SFC | Af-1 | Eai-1 |
| Ff-548 | VI-F + suzuki | Ae-1 | Eh-5 + cyclopropylboronic acid monohydrate |
| Ff-550 | VI-F + suzuki | Af-1 | Ed-8 + 4-(4,4,5,5-tetramethyl-1,3,2-dioxaborolan-2-yl)-1-(trifluoromethyl)-1H-pyrazole |
| Ff-551 | VI-F + suzuki | Af-1 | Ed-44 + 4-(4,4,5,5-tetramethyl-1,3,2-dioxaborolan-2-yl)-1-(difluoromethyl)-1H-pyrazole |
| Ff-552 | VI-F + Suzuki | Af-1 | Ed-44 + 4-(4,4,5,5-tetramethyl-1,3,2-dioxaborolan-2-yl)-1-(trifluoromethyl)-1H-pyrazole |
| Ff-553 | VI-F + suzuki | Af-1 | Ed-45 + 4-(4,4,5,5-tetramethyl-1,3,2-dioxaborolan-2-yl)-1-(difluoromethyl)-1H-pyrazole |
| Ff-554 | VI-F + suzuki | Af-1 | Ed-45 + 4-(4,4,5,5-tetramethyl-1,3,2-dioxaborolan-2-yl)-1-(trifluoromethyl)-1H-pyrazole |
| Ff-555 | VI-F + SFC | Af-1 | commercial (5-(trifluoromethmethoxy)phenyl) morpholine |
| Ff-556 | VI-F + SFC | Af-1 | commercial (5-(trifluoromethmethoxy)phenyl) morpholine |
| Ff-557 | VI-F + SFC | Af-1 | Eam-2 |
| Ff-558 | VI-F + SFC | Af-1 | Eam-2 |
| Ff-559 | VI-F | Af-1 | Eam-3 |
| Ff-560 | VI-F | Af-1 | Eam-4 |
| Ff-561 | VI-F | Al-1 | Eh-22 |
| Ff-562 | VI-F | Af-2 | Eh-22 |
| Ff-563 | VI-F | Ae-1 | Eh-22 |
| Ff-564 | VI-F | Af-5 | Eh-22 |
| Ff-565 | VI-F | Af-6 | Eh-22 |
| Ff-566 | VI-F | Ae-1 | Eh-23 |
| Ff-567 | VI-F | Af-1 | Eh-23 |
| Ff-568 | VI-F | Af-1 | Eh-24 |
| Ff-569 | VI-F | Ae-1 | Eh-24 |
| Ff-570 | VI-F | Ae-1 | Eal-6 |
| Ff-571 | VI-F | Af-6 | Eal-6 |
| Ff-572 | VI-F + reductive coupling | Af-1 | Eh-5 + 3-bromo-1,1-difluoro-cyclobutane |
| Ff-573 | VI-F + reductive coupling | Af-1 | Eh-5 + 3-iodooxetane |
| Ff-574 | VI-F | Af-1 | Ebn-1 |
| Ff-575 | VI-F | Af-1 | Ebn-2 |
| Ff-576 | VI-F | Af-1 | Eau-6 |
| Ff-577 | VI-F | Af-1 | Ebq-1 |
| Ff-578 | VI-F + cyanation | Af-1 | Et-2 + $Zn(CN)_2$ |
| Ff-579 | VI-F | Af-1 | Ebo-1 |
| Ff-580 | VI-F + suzuki | Af-1 | Ebo-1 + 1-(difluoromethyl)-4-(4,4,5,5-tetramethyl-1,3,2-dioxaborolan-2-yl)-1H-pyrazole |
| Ff-581 | VI-F | Af-1 | Eaz-9 |
| Ff-582 | VI-F | Af-1 | Ebp-1 |
| Ff-583 | VI-F + suzuki | Af-1 | Ebp-1 + 1-(difluoromethyl)-4-(4,4,5,5-tetramethyl-1,3,2-dioxaborolan-2-yl)-1H-pyrazole |

TABLE 2-continued

Synthetic procedure for some examples disclosed herein

| Example | Coupling Procedure | Core Intermediate | Tail Intermediate |
|---|---|---|---|
| Ff-584 | VI-F | Af-1 | Ead-1 |
| Ff-585 | VI-F | Af-1 | Eac-1 |
| Ff-586 | VI-F | Ag-1 | Ev-4 |
| Ff-587 | VI-F | Af-2 | Ew-1 |
| Ff-588 | VI-F | Ah-1 | Ew-1 |
| Ff-589 | VI-F | Af-5 | Ec-21 |
| Ff-590 | VI-F | Af-4 | Ec-21 |
| Ff-591 | VI-F + suzuki | Af-1 | Ed-9 + (4-(difluoromethoxy)phenyl)boronic acid |
| Ff-592 | VI-F + suzuki | Af-1 | Ed-9 + (3-(difluoromethoxy)phenyl)boronic acid |
| Ff-593 | VI-F + suzuki | Af-1 | Ed-9 + (1-phenyl-1H-pyrazol-4-yl)boronic acid |
| Ff-594 | VI-F + suzuki | Af-1 | Ed-9 + (2-oxo-1,2-dihydropyridin-3-yl)boronic acid |
| Ff-595 | VI-F | Af-1 | Ef-11 |
| Ff-596 | VI-F | Af-1 | Ed-46 |
| Ff-597 | VI-F | Af-1 | Eam-5 |
| Ff-598 | VI-F | Af-2 | Ef-7 |
| Ff-599 | VI-F | Af-2 | Ef-4 |
| Ff-600 | VI-F | Af-1 | Eh-25 |
| Ff-601 | VI-F + SFC | Af-1 | Eam-6 |
| Ff-602 | VI-F | Af-6 | Ef-11 |
| Ff-603 | VI-F | Af-1 | Ef-4 |
| Ff-604 | VI-F | Af-6 | Eh-2 |
| Ff-605 | VI-F + SCF | Af-1 | Eam-7 |
| Ff-606 | VI-F + SFC | Af-1 | Eam-8 |
| Ff-607 | VI-F + SFC | Af-1 | Eam-9 |
| Ff-608 | VI-F | Af-1 | Eam-10 |
| Ff-609 | VI-F | Af-1 | Eam-11 |
| Ff-610 | VI-F | Ag-2 | Eh-2 |
| Ff-611 | VI-F | Ag-2 | Ev-4 |
| Ff-612 | VI-F | Ag-2 | Ev-4 |
| Ff-613 | VI-F | Ag-1 | Eh-2 |
| Ff-614 | VI-F + suzuki | Af-2 + cyclopropylboronic acid | Eh-1 |
| Ff-615 | VI-F | Ae-1 | Ew-19 |
| Ff-616 | VI-F | Ae-1 | Ew-18 |
| Ff-617 | VI-F | Ag-2 | Ew-19 |
| Ff-618 | VI-F | Af-6 | Ew-19 |
| Ff-619 | VI-F | Ag-2 | Ew-18 |
| Ff-620 | VI-F | Af-1 | Ew-20 |
| Ff-621 | VI-F | An-1 | Ew-1 |
| Ff-622 | VI-F | An-2 | Ew-1 |
| Ff-623 | VI-F | Af-1 | Et-8 |
| Ff-624 | VI-F | Ag-2 | Ew-7 |
| Ff-625 | VI-F + Selectfluor | Af-6 | Ew-1 |
| Ff-626 | VI-F + Selectfluor | Af-6 | Ew-1 |
| Ff-627 | VI-F | Af-5 | Ebi-3 |
| Ff-628 | VI-F | Ae-1 | Eaw-4 |
| Ff-629 | VI-F | Af-5 | Eaz-10 |
| Ff-630 | VI-F | Ae-1 | Eaz-10 |
| Ff-631 | VI-F | Af-3 | Eaz-10 |
| Ff-632 | VI-F | Ag-2 | Ebi-6 |
| Ff-633 | VI-F | Ag-2 | Ebi-8 |
| Ff-634 | VI-F | Af-1 | Ebi-8 |
| Ff-635 | VI-F | Ag-2 | Ebi-11 |
| Ff-636 | VI-F | Af-1 | Ebi-11 |
| Ff-637 | VI-F | Af-1 | Ey-2 |
| Ff-638 | VI-F | Af-1 | Ebr-1 |
| Ff-639 | VI-F | Af-1 | Ebr-1 |
| Ff-640 | VI-F | Af-3 | Ew-12 |
| Ff-641 | VI-F + reductive coupling | Ae-1 | Eh-5 + 1-(difluoromethyl)-3-iodobicyclo[1.1.1] pentane |
| Ff-642 | VI-F + reductive coupling | Af-6 | Eh-5 + 1-iodo-3-(trifluoromethyl)bicyclo[1.1.1] pentane |
| Ff-643 | VI-F | Ae-1 | Ey-1 |
| Ff-644 | VI-F | Ag-2 | Ey-1 |
| Ff-646 | VI-F + NCS | Af-1 | Ew-1 |
| Ff-647 | VI-F + NCS | Af-1 | Ew-1 |
| Ff-648 | VI-F | Af-6 | Ebs-2 |
| Ff-649 | VI-F | Ae-1 | Ex-1 |
| Ff-650 | VI-F | Ag-2 | Ev-5 |
| Ff-651 | VI-F | Af-5 | Ew-3 |
| Ff-652 | VI-F | Af-1 | Eam-12 |
| Ff-653 | VI-F | Af-1 | Ebu-1 |
| Ff-654 | VI-F | Af-1 | Ebw-1 |
| Ff-655 | VI-F | Af-1 | Ebd-6 |

TABLE 2-continued

| Synthetic procedure for some examples disclosed herein | | | |
|---|---|---|---|
| Example | Coupling Procedure | Core Intermediate | Tail Intermediate |
| Ff-656 | VI-F | Ag-1 | Ex-1 |
| Ff-657 | VI-F | Af-5 | Ex-1 |
| Ff-658 | VI-F | Ag-2 | Ex-1 |
| Ff-659 | VI-F | Af-4 | Ex-1 |
| Ff-660 | VI-F | Af-3 | Ex-1 |
| Ff-661 | VI-F | Af-1 | Ebd-7 |
| Ff-662 | VI-F + NBS + suzuki | Af-1 | Ew-1 + $CD_3ZnCl$ |
| Ff-663 | VI-F | Af-1 | Ew-21 |
| Ff-664 | VI-F | Ae-1 | Ew-21 |
| Ff-665 | VI-F | Ag-2 | Ew-21 |
| Ff-666 | VI-F | Af-1 | Ex-2 |
| Ff-667 | VI-F | Ae-1 | Ex-2 |
| Ff-668 | VI-F | Af-1 | Eai-18 |
| Ff-669 | VI-F | Af-1 | commercial spiro[pyrrolidine-3,1'-tetralin] hydrochloride |
| Ff-670 | VI-F | Af-1 | commercial spiro[indane-1,3'-pyrrolidine] hydrochloride |
| Ff-671 | VI-F | Af-1 | Ebw-2 |
| Ff-672 | VI-F | Af-1 | Ean-2 |
| Ff-673 | VI-F | Af-1 | Ebv-1 |
| Ff-674 | VI-F | Am-1 | Eh-1 |
| Ff-675 | VI-F | Ae-1 | Ew-22 |
| Ff-676 | VI-F | Af-1 | Ew-22 |
| Ff-677 | VI-F | Af-6 | Ew-22 |
| Ff-678 | VI-F | Ag-2 | Ew-22 |
| Ff-679 | VI-F | Ag-1 | Ew-22 |
| Ff-680 | VI-F | Ag-2 | Ew-20 |
| Ff-681 | VI-F + SFC | Ae-1 | Ev-5 |
| Ff-682 | VI-F | Ag-1 | Ev-5 |
| Ff-683 | VI-F | Ag-2 | Ebd-6 |
| Ff-684 | VI-F | Af-6 | Ebi-8 |
| Ff-685 | VI-F | Af-6 | Ebi-6 |
| Ff-687 | VI-F + SFC | Af-6 | Eax-1 |
| Ff-688 | VI-F | Af-6 | Eba-7 |
| Ff-689 | VI-F + SFc | Ae-1 | Eba-6 |
| Ff-690 | VI-F | Af-1 | Eaz-7 |
| Ff-691 | VI-F | Af-1 | Eaz-6 |
| Fg-1 | VII-F | Ba-1 | Ec-2 |
| Fg-2 | VII-F | Bb-1 | Ec-2 |
| Fg-3 | VII-F | Bc-2 | Ec-2 |
| Fg-4 | VII-F | Bc-1 | Ec-2 |
| Fg-5 | VII-F | Ba-2 | Ec-2 |
| Fg-6 | VII-F | Ba-2 | Eh-2 |
| Fg-7 | VII-F | Aa-1 | Eh-6 |
| Fg-8 | VII-F | Bc-1 | Eh-1 |
| Fg-9 | VII-F | Ba-1 | Eh-1 |
| Fg-10 | VII-F | Ba-2 | Eh-1 |
| Fg-11 | VII-F | Bb-1 | Eh-1 |
| Fg-12 | VII-F | Aa-1 | Eh-3 |
| Fg-13 | VII-F | Aa-1 | Eh-4 |
| Fg-14 | VII-F | Ab-1 | Eh-4 |
| Fg-15 | VII-F | Ba-1 | Ec-1 |
| Fg-16 | VII-F | Ba-1 | Ec-4 |
| Fg-17 | VII-F | Bc-3 | Ec-2 |
| Fg-18 | VII-F | Ab-1 | Eh-1 |
| Fg-19 | VII-F | Aj-2 | Ew-4 |
| Fg-20 | VII-F | Ak-1 | Ew-5 |
| Fg-21 | VII-F | Ak-2 | Ew-5 |
| Fg-22 | VII-F | Aa-1 | Eaw-3 |
| Fg-23 | VII-F | Aa-1 | Eaw-3 |
| Fg-24 | VII-F | Ak-1 | Eav-3 |
| Fg-25 | VII-F | Ak-1 | Ew-10 |
| Fg-26 | VII-F | Ak-2 | Ew-10 |
| Fg-27 | VII-F | Ak-4 | Eba-2 |
| Fg-28 | VII-F | Ak-5 | Ew-9 |
| Fg-29 | VII-F | Aj-2 | Eat-1 |
| Fg-30 | VII-F | Ak-4 | Ew-12 |
| Fg-31 | VII-F | Aa-1 | Ew-1 |
| Fg-32 | VII-F | Ak-4 | Ew-16 |
| Fg-33 | VII-F | Ak-2 | Ebi-3 |
| Fg-34 | VII-F | Ak-2 | Eaz-10 |
| Fg-35 | VII-F | Aa-1 | Eaz-10 |
| Fg-36 | VII-F | Ak-4 | Ebs-2 |
| Fg-37 | VII-F | Ak-4 | Ebs-1 |
| Fg-38 | VII-F | Ak-1 | Eaz-11 |

TABLE 2-continued

| Synthetic procedure for some examples disclosed herein | | | |
|---|---|---|---|
| Example | Coupling Procedure | Core Intermediate | Tail Intermediate |
| Fg-39 | VII-F | Ak-4 | Ew-6 |
| Fg-40 | VII-F | Ak-1 | Ebt-1 |
| Fg-41 | VII-F | Ak-2 | Ebt-1 |
| Fg-42 | VII-F | Ak-5 | Ew-21 |
| Fg-43 | VII-F | Ak-3 | Ew-21 |
| Fg-44 | VII-F | Ak-5 | Ex-2 |
| Fg-45 | VII-F | Ak-3 | Ex-2 |
| Fg-46 | VII-F | Ak-4 | Ex-2 |
| Fg-47 | VII-F | Aa-1 | Ex-2 |
| Fg-48 | VII-F | Ao-1 | Eh-1 |
| Fg-49 | VII-F + sonogshira | Ao-1 + trimethyl-silylacetylene | Eh-1 |
| Fg-50 | VII-F | Ao-1 | Ew-1 |
| Fg-51 | VII-F + suzuki | Ao-1 + potassium vinyltrifluoroborate | Eh-1 |
| Fg-52 | VII-F + suzuki + hydrogenation | Ao-1 + potassium vinyltrifluoroborate | Eh-1 |
| Fg-53 | VII-F | Ak-5 | Ebx-1 |
| Fg-54 | VII-F | Ak-5 | Ebs-3 |
| Fg-55 | VII-F | Ak-5 | Eba-4 |
| Fg-56 | VII-F + suzuki | Ao-1 + cyclopro-pyl boronic acid | Ew-1 |
| Fg-57 | VII-F | Ak-1 | Ev-10 |
| Fg-58 | VII-F | Ak-6 | Ev-10 |
| Fg-59 | VII-F | Ak-5 | Ey-3 |
| Fg-60 | VII-F | Ak-5 | Ey-1 |
| Fg-61 | VII-F | Ak-5 | Ebs-4 |
| Fg-62 | VI-F | Ak-4 | Ew-11 |
| Fg-63 | VI-F | Ak-4 | Ew-17 |
| Fg-64 | VI-F | Ak-4 | Ebi-1 |

TABLE 3A

| Cell viability assay Data and SDMA assay Data (Examples A and B) | | | | |
|---|---|---|---|---|
| Example | CC50 | CC50 selectivity | EC50 | EC50 selectivity |
| Fa-1 | C | not measured | C | 152 |
| Fa-2 | A | 35 | A | 17 |
| Fa-3 | C | not measured | C | 22 |
| Fa-4 | A | 53 | B | 74 |
| Fa-5 | A | 104 | B | 101 |
| Fa-6 | A | 73 | B | 129 |
| Fa-7 | B | 74 | C | 159 |
| Fa-8 | A | 55 | | |
| Fb-1 | A | 48 | | |
| Fb-2 | A | 18 | B | 48 |
| Fb-3 | A | 20 | A | 32 |
| Fb-4 | B | 99 | B | 249 |
| Fb-5 | B | 72 | C | 320 |
| Fb-6 | B | 117 | C | 390 |
| Fb-7 | A | 42 | | |
| Fb-8 | A | 114 | A | 224 |
| Fb-9 | A | 54 | | |
| Fb-10 | A | 107 | | |
| Fb-11 | A | 101 | | |
| Fb-12 | B | 69 | | |
| Fb-13 | A | 54 | | |
| Fb-14 | A | 155 | | |
| Fb-15 | A | 109 | | |
| Fb-16 | B | 23 | | |
| Fb-17 | A | 85 | | |
| Fb-18 | A | 193 | | |
| Fc-1 | B | 94 | B | 171 |
| Fc-2 | B | 162 | B | 431 |
| Fd-1 | B | 39 | B | 54 |
| Fe-1 | A | 23 | B | 62 |
| Fe-2 | A | 11 | A | 5 |
| Ff-1 | A | 36 | A | 37 |
| Ff-2 | B | 34 | | |
| Ff-3 | C | 8 | | |
| Ff-4 | B | 97 | C | 2956 |

TABLE 3A-continued

| Cell viability assay Data and SDMA assay Data (Examples A and B) | | | | |
|---|---|---|---|---|
| Example | CC50 | CC50 selectivity | EC50 | EC50 selectivity |
| Ff-5 | C | 15 | C | 334 |
| Ff-6 | B | 32 | C | 71 |
| Ff-7 | A | 39 | A | 33 |
| Ff-8 | A | 133 | A | 299 |
| Ff-9 | A | 64 | A | 106 |
| Ff-10 | A | 91 | A | 88 |
| Ff-11 | A | 226 | A | 352 |
| Ff-12 | A | 166 | A | 196 |
| Ff-13 | A | 156 | A | 176 |
| Ff-14 | A | 113 | A | 241 |
| Ff-15 | C | 43 | | |
| Ff-16 | B | 58 | | |
| Ff-17 | B | 120 | B | 253 |
| Ff-18 | B | 197 | C | 447 |
| Ff-19 | B | 60 | C | 129 |
| Ff-20 | A | 175 | B | 382 |
| Ff-21 | B | 135 | B | 874 |
| Ff-22 | A | 142 | B | 587 |
| Ff-23 | A | 36 | B | 48 |
| Ff-24 | B | 390 | B | 1985 |
| Ff-25 | A | 39 | B | 312 |
| Ff-26 | A | 45 | A | 210 |
| Ff-27 | C | 16 | C | 51 |
| Ff-28 | A | 463* | B | 256 |
| Ff-29 | B | 77 | B | 308 |
| Ff-30 | C | 37 | | |
| Ff-31 | B | 92 | | |
| Ff-32 | B | 379 | B | 346 |
| Ff-33 | B | 397* | | |
| Ff-34 | A | 1067* | | |
| Ff-35 | A | 107 | | |
| Ff-36 | B | 18 | | |
| Ff-37 | B | 56 | | |
| Ff-38 | A | 93 | | |
| Ff-39 | A | 82 | | |

TABLE 3A-continued

| Cell viability assay Data and SDMA assay Data (Examples A and B) | | | | |
|---|---|---|---|---|
| Example | CC50 | CC50 selectivity | EC50 | EC50 selectivity |
| Ff-40 | B | 38 | | |
| Ff-41 | A | 156 | | |
| Ff-42 | A | 82 | | |
| Ff-43 | A | 94 | | |
| Ff-44 | A | 92 | B | 73 |
| Ff-45 | A | 60 | | |
| Ff-46 | A | 51 | | |
| Ff-47 | A | 139 | | |
| Ff-48 | B | 78 | | |
| Ff-49 | C | >11 | | |
| Ff-50 | A | 84 | | |
| Ff-51 | B | 106 | | |
| Ff-52 | B | 29 | | |
| Ff-53 | A | 30 | | |
| Ff-54 | A | 100 | B | 95 |
| Ff-55 | A | 61 | | |
| Ff-56 | B | 12 | | |
| Ff-57 | B | 13 | | |
| Ff-58 | A | 63 | B | 166 |
| Ff-59 | A | 142 | B | 65 |
| Ff-60 | B | 51 | C | 371 |
| Ff-61 | C | 18 | | |
| Ff-62 | C | 50 | C | 178 |
| Ff-63 | B | 19 | | |
| Ff-64 | B | 65 | | |
| Ff-65 | C | 19 | | |
| Ff-66 | B | 117 | | |
| Ff-67 | B | 135 | | |
| Ff-68 | A | 122 | | |
| Ff-69 | B | 42 | | |
| Ff-70 | A | 77 | | |
| Ff-71 | B | 96 | | |
| Ff-72 | B | 57 | | |
| Ff-73 | B | 49 | | |
| Ff-74 | B | 89 | | |
| Ff-75 | B | 111 | | |
| Ff-76 | A | 86 | | |
| Ff-77 | A | 55 | | |
| Ff-78 | A | 60 | | |
| Ff-80 | A | 39 | | |
| Ff-81 | A | 72 | | |
| Ff-82 | A | 76 | | |
| Ff-83 | B | 61 | | |
| Ff-84 | B | 77 | | |
| Ff-85 | A | 58 | | |
| Ff-86 | A | 64 | | |
| Ff-87 | A | 122 | | |
| Ff-88 | B | 49 | | |
| Ff-89 | A | 113 | | |
| Ff-90 | B | 80 | | |
| Ff-91 | A | 95 | | |
| Ff-92 | A | 127 | | |
| Ff-93 | A | 44 | | |
| Ff-94 | A | 366 | | |
| Ff-95 | A | 154 | | |
| Ff-96 | A | 156 | | |
| Ff-97 | B | 19 | | |
| Ff-98 | A | 106 | | |
| Ff-99 | A | 165 | | |
| Ff-100 | A | 60 | | |
| Ff-101 | B | 49 | | |
| Ff-102 | B | 82 | | |
| Ff-103 | B | 41 | | |
| Ff-104 | A | 92 | | |
| Ff-105 | A | 72 | | |
| Ff-106 | A | 38 | | |
| Ff-107 | A | 106 | | |
| Ff-108 | A | 70 | | |
| Ff-109 | A | 91 | | |
| Ff-110 | A | 61 | A | 118 |
| Ff-111 | A | 99 | A | 258 |
| Ff-112 | A | 96 | | |
| Ff-113 | A | 86 | | |
| Ff-114 | A | 83 | | |
| Ff-115 | A | 47 | | |
| Ff-116 | A | 70 | | |

TABLE 3A-continued

| Cell viability assay Data and SDMA assay Data (Examples A and B) | | | | |
|---|---|---|---|---|
| Example | CC50 | CC50 selectivity | EC50 | EC50 selectivity |
| Ff-117 | A | 65 | | |
| Ff-118 | A | 168 | | |
| Ff-119 | A | 88 | | |
| Ff-120 | A | 44 | | |
| Ff-121 | A | 133 | | |
| Ff-122 | A | 120 | | |
| Ff-123 | B | 54 | | |
| Ff-124 | B | 50 | | |
| Ff-125 | B | 140 | | |
| Ff-126 | B | 78 | | |
| Ff-127 | B | 108 | | |
| Ff-128 | A | 75 | | |
| Ff-129 | A | 60 | | |
| Ff-130 | A | 62 | | |
| Ff-131 | A | 50 | | |
| Ff-132 | A | 71 | | |
| Ff-133 | A | 71 | | |
| Ff-134 | B | 105 | | |
| Ff-135 | B | 76 | | |
| Ff-136 | B | 120 | | |
| Ff-137 | A | 93 | | |
| Ff-138 | A | 69 | A | 20 |
| Ff-139 | A | 63 | | |
| Ff-140 | B | 75 | | |
| Ff-141 | A | 111 | | |
| Ff-142 | A | 36 | | |
| Ff-143 | B | 24 | | |
| Ff-144 | A | 137 | B | 157 |
| Ff-145 | A | 264* | | |
| Ff-146 | A | 30 | | |
| Ff-147 | A | 296* | | |
| Ff-148 | A | 29 | | |
| Ff-149 | A | 44 | | |
| Ff-150 | A | 645* | | |
| Ff-151 | A | 66 | | |
| Ff-152 | B | 19 | | |
| Ff-153 | A | 80 | | |
| Ff-154 | A | 45 | | |
| Ff-155 | B | 20 | | |
| Ff-156 | B | 59 | | |
| Ff-157 | A | 81 | | |
| Ff-158 | A | 77 | | |
| Ff-159 | A | 48 | | |
| Ff-160 | A | 77 | | |
| Ff-161 | B | 9 | | |
| Ff-162 | B | 80 | | |
| Ff-163 | A | 68 | B | 64 |
| Ff-164 | A | 63 | | |
| Ff-165 | A | 78 | A | 43 |
| Ff-166 | A | 74 | | |
| Ff-167 | A | 83 | B | 44 |
| Ff-168 | A | 344* | | |
| Ff-169 | A | 266* | | |
| Ff-170 | A | 73 | | |
| Ff-171 | A | 57 | | |
| Ff-172 | A | 53 | | |
| Ff-173 | A | 63 | | |
| Ff-174 | A | 64 | | |
| Ff-175 | A | 62 | | |
| Ff-176 | A | 84 | | |
| Ff-177 | A | 38 | | |
| Ff-178 | A | 75 | | |
| Ff-179 | A | 106 | | |
| Ff-180 | A | 84 | | |
| Ff-181 | A | 59 | | |
| Ff-182 | A | 72 | | |
| Ff-183 | A | 60 | A | 117 |
| Ff-184 | A | 55 | | |
| Ff-185 | A | 565* | | |
| Ff-186 | A | 78 | | |
| Ff-187 | A | 119 | | |
| Ff-188 | A | 95 | | |
| Ff-189 | B | 104 | | |
| Ff-190 | B | 68 | | |
| Ff-191 | A | 69 | | |
| Ff-192 | A | 48 | | |

TABLE 3A-continued

Cell viability assay Data and SDMA assay Data (Examples A and B)

| Example | CC50 | CC50 selectivity | EC50 | EC50 selectivity |
|---|---|---|---|---|
| Ff-193 | B | 82 | | |
| Ff-194 | B | 60 | | |
| Ff-195 | A | 513* | | |
| Ff-196 | A | 69 | | |
| Ff-197 | A | 54 | | |
| Ff-198 | A | 51 | | |
| Ff-199 | A | 41 | | |
| Ff-200 | A | 81 | | |
| Ff-201 | A | 56 | B | 58 |
| Ff-202 | B | 39 | | |
| Ff-203 | A | 173 | | |
| Ff-204 | A | 35 | | |
| Ff-205 | A | 38 | | |
| Ff-208 | B | 80 | | |
| Ff-209 | B | 109 | | |
| Ff-210 | A | 45 | A | 45 |
| Ff-211 | A | 21 | | |
| Ff-212 | A | 16 | | |
| Ff-213 | A | 361* | B | 153 |
| Ff-214 | A | 216 | | |
| Ff-215 | A | 209 | B | 224 |
| Ff-216 | A | 57 | | |
| Ff-217 | A | 53 | | |
| Ff-218 | A | 22 | | |
| Ff-219 | A | 25 | | |
| Ff-220 | A | 37 | | |
| Ff-221 | A | 55 | | |
| Ff-222 | A | 47 | | |
| Ff-223 | B | 47 | | |
| Ff-224 | B | 47 | | |
| Ff-225 | B | 70 | | |
| Ff-226 | A | 127 | | |
| Ff-227 | A | 21 | | |
| Ff-228 | A | 75 | | |
| Ff-229 | A | 743* | | |
| Ff-230 | B | 57 | | |
| Ff-231 | B | 73 | | |
| Ff-232 | A | 132 | | |
| Ff-233 | A | 133 | | |
| Ff-234 | B | 37 | | |
| Ff-235 | A | 90 | | |
| Ff-236 | B | 40 | | |
| Ff-237 | A | 100 | | |
| Ff-238 | A | 571* | | |
| Ff-239 | A | 1483* | | |
| Ff-240 | B | 14 | | |
| Ff-241 | B | 28 | | |
| Ff-242 | A | 47 | | |
| Ff-243 | B | 23 | | |
| Ff-244 | A | 54 | | |
| Ff-245 | B | 53 | | |
| Ff-246 | A | 49 | | |
| Ff-247 | A | 61 | | |
| Ff-248 | A | 70 | | |
| Ff-249 | B | 103 | | |
| Ff-250 | A | 657* | | |
| Ff-251 | A | 46 | | |
| Ff-252 | A | 40 | | |
| Ff-253 | B | 41 | | |
| Ff-254 | B | 78 | | |
| Ff-255 | B | 54 | | |
| Ff-256 | B | 110 | | |
| Ff-257 | A | 15 | | |
| Ff-258 | A | 90 | | |
| Ff-259 | A | 39 | | |
| Ff-260 | A | 128 | | |
| Ff-261 | A | 66 | | |
| Ff-262 | B | 86 | | |
| Ff-263 | B | 83 | | |
| Ff-264 | B | 29 | | |
| Ff-265 | A | 41 | | |
| Ff-266 | B | 86 | | |
| Ff-267 | B | 20 | | |
| Ff-268 | A | 18 | | |
| Ff-269 | A | 94 | | |
| Ff-270 | B | 43 | | |

TABLE 3A-continued

Cell viability assay Data and SDMA assay Data (Examples A and B)

| Example | CC50 | CC50 selectivity | EC50 | EC50 selectivity |
|---|---|---|---|---|
| Ff-271 | B | 51 | | |
| Ff-272 | A | 31 | | |
| Ff-273 | A | 9 | | |
| Ff-274 | A | 21 | | |
| Ff-275 | A | 85 | | |
| Ff-276 | A | 55 | | |
| Ff-277 | A | 26 | | |
| Ff-278 | A | 80 | B | 47 |
| Ff-279 | A | 136 | A | 60 |
| Ff-280 | A | 128 | B | 118 |
| Ff-281 | A | 75 | | |
| Ff-282 | B | 69 | | |
| Ff-283 | A | 60 | | |
| Ff-284 | A | 27 | | |
| Ff-285 | A | 48 | | |
| Ff-286 | A | 90 | | |
| Ff-287 | A | 74 | | |
| Ff-288 | A | 74 | | |
| Ff-289 | A | 120 | A | 88 |
| Ff-290 | A | 40 | | |
| Ff-291 | A | 91 | | |
| Ff-292 | A | 80 | | |
| Ff-293 | B | 37 | | |
| Ff-294 | A | 60 | | |
| Ff-295 | A | 675* | | |
| Ff-296 | A | 101 | | |
| Ff-297 | A | 101 | | |
| Ff-298 | A | 61 | | |
| Ff-299 | A | 104 | | |
| Ff-300 | A | 71 | | |
| Ff-301 | A | 105 | | |
| Ff-302 | A | 161 | | |
| Ff-303 | A | 124 | | |
| Ff-304 | A | 302* | B | 127 |
| Ff-305 | A | 75 | | |
| Ff-306 | A | 53 | | |
| Ff-307 | A | 66 | | |
| Ff-308 | A | 65 | | |
| Ff-309 | A | 81 | | |
| Ff-310 | A | 64 | | |
| Ff-311 | A | 32 | | |
| Ff-312 | B | 11 | | |
| Ff-313 | B | 40 | | |
| Ff-314 | A | 48 | | |
| Ff-315 | A | 29 | | |
| Ff-316 | A | 96 | | |
| Ff-317 | B | 185 | | |
| Ff-318 | A | 70 | | |
| Ff-319 | A | 92 | B | 42 |
| Ff-320 | A | 59 | B | 26 |
| Ff-321 | A | 52 | B | 67 |
| Ff-322 | A | 78 | | |
| Ff-323 | A | 46 | | |
| Ff-324 | A | 96 | B | 53 |
| Ff-325 | A | 190 | A | 447 |
| Ff-326 | A | 72 | | |
| Ff-327 | A | 28 | | |
| Ff-328 | A | 54 | | |
| Ff-329 | A | 64 | | |
| Ff-330 | B | 32 | | |
| Ff-331 | A | 84 | | |
| Ff-332 | A | 84 | | |
| Ff-333 | A | 68 | | |
| Ff-334 | A | 87 | | |
| Ff-335 | A | 74 | | |
| Ff-336 | A | 108 | | |
| Ff-337 | A | 110 | | |
| Ff-338 | A | 41 | | |
| Ff-339 | A | 77 | | |
| Ff-340 | A | 105 | A | 135 |
| Ff-341 | A | 80 | A | 145 |
| Ff-342 | A | 93 | | |
| Ff-343 | A | 124 | | |
| Ff-344 | A | 123 | | |
| Ff-345 | A | 113 | | |
| Ff-346 | A | 49 | | |

TABLE 3A-continued

| Cell viability assay Data and SDMA assay Data (Examples A and B) | | | | |
|---|---|---|---|---|
| Example | CC50 | CC50 selectivity | EC50 | EC50 selectivity |
| Ff-347 | A | 108 | | |
| Ff-348 | A | 78 | | |
| Ff-349 | A | 73 | | |
| Ff-350 | A | 108 | | |
| Ff-351 | A | 92 | | |
| Ff-352 | A | 119 | | |
| Ff-353 | A | 81 | | |
| Ff-354 | A | 76 | | |
| Ff-355 | B | 105 | | |
| Ff-356 | A | 89 | | |
| Ff-357 | A | 47 | | |
| Ff-358 | A | 37 | | |
| Ff-359 | A | 85 | | |
| Ff-360 | A | 28 | | |
| Ff-361 | A | 73 | | |
| Ff-362 | A | 81 | | |
| Ff-363 | A | 128 | | |
| Ff-364 | A | 56 | | |
| Ff-365 | A | 111 | | |
| Ff-366 | A | 75 | | |
| Ff-367 | A | 80 | | |
| Ff-368 | A | 52 | A | 47 |
| Ff-369 | A | 51 | | |
| Ff-370 | A | 84 | | |
| Ff-371 | A | 59 | | |
| Ff-372 | A | 85 | | |
| Ff-373 | A | 82 | | |
| Ff-374 | A | 58 | | |
| Ff-375 | A | 74 | | |
| Ff-376 | A | 85 | | |
| Ff-377 | A | 63 | | |
| Ff-378 | A | 86 | A | 106 |
| Ff-379 | A | 54 | | |
| Ff-380 | A | 55 | | |
| Ff-381 | A | 112 | | |
| Ff-382 | A | 110 | | |
| Ff-383 | A | 164 | | |
| Ff-384 | A | 44 | | |
| Ff-385 | A | 26 | | |
| Ff-386 | A | 40 | | |
| Ff-387 | A | 46 | | |
| Ff-388 | A | 89 | | |
| Ff-389 | A | 80 | | |
| Ff-390 | A | 100 | | |
| Ff-391 | A | 41 | B | 26 |
| Ff-392 | A | 69 | A | 68 |
| Ff-393 | A | 85 | | |
| Ff-394 | B | 18 | | |
| Ff-395 | A | 71 | | |
| Ff-396 | A | 80 | | |
| Ff-397 | B | 38 | | |
| Ff-398 | A | 112 | | |
| Ff-399 | A | 61 | A | 47 |
| Ff-400 | A | 152 | | |
| Ff-401 | B | 95 | | |
| Ff-402 | A | 22 | | |
| Ff-403 | B | 56 | | |
| Ff-404 | A | 30 | | |
| Ff-405 | A | 69 | | |
| Ff-406 | A | 47 | | |
| Ff-407 | A | 78 | A | 65 |
| Ff-408 | A | 41 | | |
| Ff-409 | B | >131 | | |
| Ff-410 | B | 49 | C | 453 |
| Ff-411 | B | >248 | | |
| Ff-412 | A | 53 | A | 252 |
| Ff-413 | A | 14 | | |
| Ff-414 | A | 25 | | |
| Ff-415 | A | 40 | | |
| Ff-416 | A | 34 | | |
| Ff-417 | A | 16 | | |
| Ff-418 | B | 61 | | |
| Ff-419 | A | 16 | | |
| Ff-420 | B | >176 | | |
| Ff-421 | A | 4 | | |
| Ff-422 | A | 10 | | |

TABLE 3A-continued

| Cell viability assay Data and SDMA assay Data (Examples A and B) | | | | |
|---|---|---|---|---|
| Example | CC50 | CC50 selectivity | EC50 | EC50 selectivity |
| Ff-423 | A | 21 | | |
| Ff-424 | A | 16 | | |
| Ff-425 | B | 4 | | |
| Ff-426 | B | 44 | | |
| Ff-427 | B | 4 | | |
| Ff-428 | B | 75 | | |
| Ff-429 | A | 61 | | |
| Ff-430 | B | 55 | | |
| Ff-431 | B | 105 | | |
| Ff-432 | A | 33 | | |
| Ff-433 | B | 50 | | |
| Ff-434 | A | 76 | | |
| Ff-435 | B | 127 | | |
| Ff-436 | A | 113 | | |
| Ff-437 | A | 87 | | |
| Ff-438 | A | 88 | | |
| Ff-439 | A | 95 | | |
| Ff-440 | A | 132 | | |
| Ff-441 | A | 126 | | |
| Ff-442 | A | 119 | | |
| Ff-443 | A | 74 | | |
| Ff-444 | A | 116 | | |
| Ff-445 | A | 99 | | |
| Ff-446 | A | 82 | | |
| Ff-447 | A | 82 | | |
| Ff-448 | A | 97 | | |
| Ff-449 | A | 115 | | |
| Ff-450 | A | 93 | | |
| Ff-451 | A | 149 | | |
| Ff-452 | A | 127 | | |
| Ff-453 | A | 111 | | |
| Ff-454 | B | 48 | | |
| Ff-455 | B | 81 | | |
| Ff-456 | B | 51 | | |
| Ff-457 | A | 89 | | |
| Ff-458 | A | 70 | | |
| Ff-459 | A | 136 | | |
| Ff-460 | A | 119 | | |
| Ff-461 | A | 43 | | |
| Ff-462 | B | 68 | | |
| Ff-463 | B | 83 | | |
| Ff-464 | B | 65 | | |
| Ff-465 | A | 145 | | |
| Ff-466 | A | 117 | | |
| Ff-467 | A | 741* | | |
| Ff-468 | A | 31 | | |
| Ff-470 | A | 73 | | |
| Ff-471 | A | 60 | | |
| Ff-472 | A | 252 | | |
| Ff-473 | A | 128 | | |
| Ff-474 | A | 57 | | |
| Ff-475 | A | 336* | | |
| Ff-476 | B | 63 | | |
| Ff-477 | A | 218 | | |
| Ff-478 | A | 117 | | |
| Ff-479 | A | 208* | | |
| Ff-480 | A | 91 | | |
| Ff-481 | A | 149 | | |
| Ff-482 | A | 120 | | |
| Ff-483 | A | 149 | | |
| Ff-484 | A | 147 | | |
| Ff-485 | A | 149 | | |
| Ff-486 | A | 146 | | |
| Ff-487 | B | 17 | | |
| Ff-488 | B | 43 | | |
| Ff-489 | B | 39 | | |
| Ff-490 | A | 136 | | |
| Ff-491 | A | 60 | | |
| Ff-492 | A | 60 | | |
| Ff-493 | B | 41 | | |
| Ff-494 | B | 34 | | |
| Ff-495 | B | 37 | | |
| Ff-496 | B | 16 | | |
| Ff-497 | A | 65 | | |
| Ff-498 | A | 110 | | |
| Ff-499 | A | 74 | | |

TABLE 3A-continued

Cell viability assay Data and SDMA assay Data (Examples A and B)

| Example | CC50 | CC50 selectivity | EC50 | EC50 selectivity |
|---|---|---|---|---|
| Ff-500 | A | 45 | | |
| Ff-501 | A | 108 | A | 115 |
| Ff-502 | A | 61 | B | 112 |
| Ff-503 | A | 85 | | |
| Ff-504 | A | 112 | | |
| Ff-505 | A | 116 | | |
| Ff-506 | A | 142 | | |
| Ff-507 | A | 40 | | |
| Ff-508 | A | 76 | | |
| Ff-509 | A | 127 | | |
| Ff-510 | A | 75 | | |
| Ff-511 | B | 62 | | |
| Ff-512 | B | 80 | | |
| Ff-513 | A | 53 | | |
| Ff-514 | B | 25 | | |
| Ff-515 | B | 3 | | |
| Ff-516 | A | 199 | B | 337 |
| Ff-517 | B | 82 | | |
| Ff-518 | A | 122 | | |
| Ff-519 | B | 61 | | |
| Ff-520 | B | 81 | | |
| Ff-521 | B | 62 | | |
| Ff-522 | B | 46 | | |
| Ff-523 | B | 106 | | |
| Ff-524 | A | 144 | | |
| Ff-525 | B | 74 | | |
| Ff-526 | B | 82 | | |
| Ff-527 | B | 91 | | |
| Ff-528 | B | 67 | | |
| Ff-529 | B | 139 | | |
| Ff-530 | A | 127 | | |
| Ff-531 | B | 127 | | |
| Ff-532 | A | 132 | | |
| Ff-533 | B | 50 | | |
| Ff-534 | A | 128 | | |
| Ff-535 | B | 31 | | |
| Ff-536 | B | 70 | | |
| Ff-537 | A | 105 | | |
| Ff-538 | A | 92 | | |
| Ff-539 | A | 74 | | |
| Ff-540 | B | 115 | | |
| Ff-541 | B | 102 | | |
| Ff-542 | A | 55 | | |
| Ff-543 | A | 83 | | |
| Ff-544 | A | 72 | B | 109 |
| Ff-545 | A | 218 | B | 157 |
| Ff-546 | A | 139 | | |
| Ff-547 | A | 104 | | |
| Ff-548 | B | 182 | B | 102 |
| Ff-550 | B | 60 | | |
| Ff-551 | B | 34 | | |
| Ff-552 | B | 300* | | |
| Ff-553 | B | 80 | | |
| Ff-554 | B | 374* | | |
| Ff-555 | A | 115 | | |
| Ff-556 | B | 48 | | |
| Ff-557 | A | 156 | | |
| Ff-558 | B | 25 | | |
| Ff-559 | A | 178 | | |
| Ff-560 | A | 70 | | |
| Ff-561 | A | 148 | | |
| Ff-562 | A | 93 | | |
| Ff-563 | A | 84 | | |
| Ff-564 | A | 139 | | |
| Ff-565 | B | 74 | | |
| Ff-566 | B | 98 | B | 497 |
| Ff-567 | A | 138 | A | 707 |
| Ff-568 | B | 90 | C | 457 |
| Ff-569 | B | 117 | | |
| Ff-570 | B | 45 | | |
| Ff-571 | B | 42 | | |
| Ff-572 | A | 129 | | |
| Ff-573 | B | 109 | | |
| Ff-574 | A | 125 | | |
| Ff-575 | A | 101 | | |
| Ff-576 | B | 112 | | |

TABLE 3A-continued

Cell viability assay Data and SDMA assay Data (Examples A and B)

| Example | CC50 | CC50 selectivity | EC50 | EC50 selectivity |
|---|---|---|---|---|
| Ff-577 | B | 11 | | |
| Ff-578 | A | 74 | | |
| Ff-579 | A | 169 | | |
| Ff-580 | B | 93 | | |
| Ff-581 | B | 86 | | |
| Ff-582 | B | 88 | | |
| Ff-583 | B | 123 | | |
| Ff-584 | A | 110 | | |
| Ff-585 | A | 68 | | |
| Ff-586 | A | 44 | | |
| Ff-587 | A | 61 | | |
| Ff-588 | A | 55 | | |
| Ff-589 | A | 143 | | |
| Ff-590 | A | 39 | | |
| Ff-591 | A | 47 | | |
| Ff-592 | A | 41 | | |
| Ff-593 | A | 1919* | | |
| Ff-594 | B | 52 | | |
| Ff-595 | B | 70 | | |
| Ff-596 | B | 224* | | |
| Ff-597 | A | 121 | | |
| Ff-598 | A | 83 | | |
| Ff-599 | A | 52 | | |
| Ff-600 | A | 528* | | |
| Ff-601 | A | 117 | | |
| Ff-602 | B | 80 | | |
| Ff-603 | B | 44 | | |
| Ff-604 | A | 51 | | |
| Ff-605 | A | 82 | | |
| Ff-606 | B | 75 | | |
| Ff-607 | A | 138 | | |
| Ff-608 | A | 102 | | |
| Ff-609 | A | 76 | | |
| Ff-610 | A | 83 | | |
| Ff-611 | A | 41 | | |
| Ff-612 | B | 34 | | |
| Ff-613 | A | 159 | | |
| Ff-614 | A | 131 | | |
| Ff-615 | A | 147 | A | 158 |
| Ff-616 | A | 69 | A | 162 |
| Ff-617 | A | 130 | B | 274 |
| Ff-618 | A | 119 | B | 294 |
| Ff-619 | A | 56 | B | 58 |
| Ff-620 | A | 49 | | |
| Ff-621 | B | 51 | | |
| Ff-622 | A | 78 | | |
| Ff-623 | B | 33 | | |
| Ff-624 | B | 38 | C | 27 |
| Ff-625 | B | 35 | C | 315 |
| Ff-626 | A | 37 | B | 143 |
| Ff-627 | A | 93 | | |
| Ff-628 | A | 95 | | |
| Ff-629 | A | 43 | | |
| Ff-630 | A | 68 | | |
| Ff-631 | B | 47 | | |
| Ff-632 | A | 92 | | |
| Ff-633 | A | 104 | B | 82 |
| Ff-634 | A | 88 | A | 171 |
| Ff-635 | A | 97 | | |
| Ff-636 | A | 66 | | |
| Ff-637 | A | 89 | A | 182 |
| Ff-638 | A | 38 | | |
| Ff-639 | A | 64 | | |
| Ff-640 | A | 121 | B | 415 |
| Ff-641 | A | 77 | A | 389 |
| Ff-642 | B | 52 | | |
| Ff-643 | A | 134 | A | 155 |
| Ff-644 | A | 71 | A | 92 |
| Ff-646 | A | 107 | | |
| Ff-647 | A | 55 | | |
| Ff-648 | A | 84 | A | 50 |
| Ff-649 | A | 51 | | |
| Ff-650 | A | 95 | | |
| Ff-651 | A | 120 | | |
| Ff-652 | A | 99 | | |
| Ff-653 | A | 94 | | |

TABLE 3A-continued

| Cell viability assay Data and SDMA assay Data (Examples A and B) | | | | |
|---|---|---|---|---|
| Example | CC50 | CC50 selectivity | EC50 | EC50 selectivity |
| Ff-654 | A | 57 | | |
| Ff-655 | A | 90 | | |
| Ff-656 | A | 77 | | |
| Ff-657 | A | 35 | | |
| Ff-658 | A | 92 | B | 124 |
| Ff-659 | A | 21 | | |
| Ff-660 | A | 106 | A | 122 |
| Ff-661 | A | 134 | A | 147 |
| Ff-662 | A | 69 | B | 70 |
| Ff-663 | A | 26 | A | 23 |
| Ff-664 | A | 79 | A | 79 |
| Ff-665 | A | 31 | A | 39 |
| Ff-666 | A | 43 | | |
| Ff-667 | A | 84 | A | 115 |
| Ff-668 | B | 61 | | |
| Ff-669 | B | 42 | B | 485 |
| Ff-670 | B | 36 | | |
| Ff-671 | A | 68 | | |
| Ff-672 | A | 130 | | |
| Ff-673 | A | 71 | B | 197 |
| Ff-674 | A | 163 | A | 85 |
| Ff-675 | A | 103 | A | 107 |
| Ff-676 | A | 25 | | |
| Ff-677 | A | 120 | | |
| Ff-678 | A | 129 | B | 263 |
| Ff-679 | A | 102 | | |
| Ff-680 | A | 61 | | |
| Ff-681 | A | 123 | A | 313 |
| Ff-682 | A | 215* | B | 128 |
| Ff-683 | A | 96 | | |
| Ff-684 | A | 92 | A | 121 |
| Ff-685 | A | 71 | B | 108 |
| Ff-687 | A | 1625* | A | 325 |
| Ff-688 | A | 80 | | |
| Ff-689 | A | 36 | A | 59 |
| Ff-690 | A | 55 | | |
| Ff-691 | B | 40 | | |
| Fg-1 | B | 19 | B | 50 |
| Fg-2 | A | 72 | B | 39 |
| Fg-3 | B | 10 | C | 16 |
| Fg-4 | B | 19 | B | 23 |
| Fg-5 | A | 40 | B | 19 |
| Fg-6 | A | 184 | B | 88 |
| Fg-7 | B | 172 | B | 496 |
| Fg-8 | C | 16 | C | 275 |
| Fg-9 | C | 12 | C | 255 |
| Fg-10 | C | 20 | C | 307 |
| Fg-11 | B | 23 | C | 225 |
| Fg-12 | A | 150 | A | 168 |
| Fg-13 | A | 120 | A | 207 |
| Fg-14 | B | 146 | B | 158 |
| Fg-15 | C | 11 | C | 8 |
| Fg-16 | C | 10 | C | 6 |
| Fg-17 | A | 27 | | |
| Fg-18 | B | 81 | B | 275 |
| Fg-19 | A | 48 | | |
| Fg-20 | A | 60 | | |
| Fg-21 | A | 73 | | |
| Fg-22 | A | 111 | | |
| Fg-23 | A | 81 | | |
| Fg-24 | A | 50 | | |
| Fg-25 | A | 56 | | |
| Fg-26 | A | 81 | | |
| Fg-27 | B | 47 | | |
| Fg-28 | A | 110 | | |
| Fg-29 | A | 71 | | |
| Fg-30 | A | 75 | | |
| Fg-31 | A | 115 | | |
| Fg-32 | A | 52 | | |
| Fg-33 | A | 71 | | |
| Fg-34 | A | 27 | | |
| Fg-35 | A | 96 | B | 151 |
| Fg-36 | A | 78 | | |
| Fg-37 | A | 39 | | |
| Fg-38 | A | 34 | B | 31 |
| Fg-39 | A | 95 | | |
| Fg-40 | A | 58 | A | 92 |
| Fg-41 | A | 56 | B | 42 |
| Fg-42 | A | 38 | A | 57 |
| Fg-43 | A | 57 | | |
| Fg-44 | A | 86 | A | 119 |
| Fg-45 | A | 80 | | |
| Fg-46 | A | 72 | A | 273 |
| Fg-47 | A | 85 | | |
| Fg-48 | A | 110 | A | 94 |
| Fg-49 | A | 76 | A | 70 |
| Fg-50 | A | 79 | A | 47 |
| Fg-51 | A | 115 | B | 319 |
| Fg-52 | A | 132 | | |
| Fg-53 | A | 59 | A | 85 |
| Fg-54 | A | 44 | A | 69 |
| Fg-55 | A | 89 | A | 114 |
| Fg-56 | B | 40 | | |
| Fg-57 | A | 63 | A | 137 |
| Fg-58 | A | 69 | B | 345 |
| Fg-59 | A | 54 | A | 208 |
| Fg-60 | A | 130 | A | 87 |
| Fg-61 | A | 54 | | |
| Fg-62 | A | 48 | | |
| Fg-63 | A | 98 | | |
| Fg-64 | A | 116 | | |

TABLE 3B

| Cell viability assay Data of some compouds (Examples A and D) | | | | |
|---|---|---|---|---|
| Example | CC50-HCT116-MTAP$^{del}$ [nM] | CC50-HCT116$^{WT}$ [nM] | paCC50-HCT116-MTAP$^{del}$ [nM] | Selectivity |
| Ff-81 | 19 | 1350 | 591* | 71 |
| Ff-82 | 27 | 2068 | 408 | 77 |
| Ff-104 | 5 | 470 | 139* | 94 |
| Ff-109 | 15 | 1377 | 276 | 92 |
| Ff-110 | 6 | 516 | 100 | 86 |
| Ff-111 | 10 | 1100 | 139 | 110 |
| Ff-113 | 30 | 2574 | | 86 |
| Ff-115 | 10 | 478 | 202 | 48 |
| Ff-117 | 18 | 1249 | 269 | 69 |
| Ff-121 | 3 | 459 | 106 | 153 |
| Ff-173 | 35 | 2247 | 1163 | 64 |
| Ff-174 | 36 | 2283 | | 63 |
| Ff-183 | 15 | 853 | 257 | 57 |
| Ff-197 | 15 | 712 | 217 | 47 |
| Ff-252 | 13 | 534 | 269 | 41 |
| Ff-340 | 23 | 2465 | 298 | 107 |
| Ff-341 | 9 | 710 | 150 | 79 |
| Ff-344 | 27 | 2297 | 476 | 85 |
| Ff-345 | 32 | 3619 | | 113 |
| Ff-346 | 6 | 305 | 155 | 51 |
| Ff-363 | 16 | 2037 | 196 | 127 |
| Ff-366 | 29 | 2166 | 206 | 75 |
| Ff-367 | 12 | 925 | 199 | 77 |
| Ff-368 | 3 | 178 | | 59 |
| Ff-379 | 13 | 730 | | 56 |
| Ff-402 | 30 | 2522 | 40 | 84 |
| Ff-499 | 13 | 897 | 168 | 69 |
| Ff-587 | 5 | 274 | 329 | 55 |
| Ff-620 | 31 | 1547 | | 50 |
| Ff-632 | 18 | 1680 | 270 | 93 |
| Ff-633 | 20 | 2085 | | 104 |
| Ff-648 | 9 | 650 | 262 | 72 |
| Ff-684 | 14 | 1308 | 465 | 93 |
| Ff-685 | 16 | 1130 | 357 | 71 |
| Ff-692 | 14 | 969 | 139 | 69 |
| Ff-693 | 15 | 1876 | 247 | 125 |
| Ff-694 | 10 | 723 | 120 | 72 |
| Ff-696 | 17 | 1408 | 198 | 83 |
| Ff-697 | 25 | 4986 | 289 | 199 |

TABLE 3B-continued

Cell viability assay Data of some compouds (Examples A and D)

| Example | CC50-HCT116-MTAP$^{del}$ [nM] | CC50-HCT116$^{WT}$ [nM] | paCC50-HCT116-MTAP$^{del}$ [nM] | Selectivity |
|---|---|---|---|---|
| Ff-698 | 15 | 1443 | 295 | 96 |
| Ff-699 | 15 | 1107 | 237 | 74 |
| Fg-31 | 19 | 2140 | 312 | 113 |
| Fg-53 | 6 | 503 | 139* | 84 |
| Fg-55 | 9 | 799 | 190* | 89 |
| Fg-60 | 7 | 683 | | 98 |
| Fg-66 | 72 | 8368 | 788 | 116 |
| Fg-67 | 38 | 4263 | 402 | 112 |
| Fg-68 | 8 | 708 | 130 | 89 |

*Calculated using Low throughput hEQDS paCC50-HCT116-MTAP$^{del}$ = CC50-HCT116-MTAP$^{del}$
* (% free CCM/% free human plasma)

TABLE 3C

Cell viability assay Data of some compounds for various cell lines (Example A1)

| | MTAP-Deleted | | | MTAP-WT |
|---|---|---|---|---|
| GI50 (μM) | LU99 | SW780 | BxPC-3 | Calu-6 |
| Example Ff-81 | 0.019 | 0.025 | — | >10 |
| Example Ff-104 | 0.004 | 0.005 | — | 2.15 |
| Example Ff-110 | 0.007 | 0.12 | 0.007 | 1.55 |
| Example Ff-111 | 0.008 | 0.011 | 0.010 | >6.4 |
| Example Ff-183 | 0.011 | 0.019 | 0.012 | 2.15 |
| Example Ff-340 | 0.017 | 0.023 | 0.023 | 2.95 |
| Example Ff-341 | 0.013 | 0.010 | 0.014 | 2.44 |
| Example Ff-648 | 0.009 | 0.012 | 0.008 | 1.66 |
| Example Fg-53 | 0.006 | 0.009 | 0.007 | 1.26 |
| Example Fg-55 | 0.010 | 0.023 | 0.011 | 2.51 |

TABLE 4

Permeability data (Example G2)

| Example No. | cPgp-KO-MDCK-WT $P_{app}$ (A-to-B) [x10$^{-6}$ cm/s] | cPgp-KO-BCRP-KI (ER) |
|---|---|---|
| Ff-81 | 10.5 | 1.5 |
| Ff-82 | 8.8 | 6.1 |
| Ff-109 | 12.2 | 8.8 |
| Ff-110 | 12.1 | 3.6 |
| Ff-111 | 15.3 | 4.6 |
| Ff-113 | 12.3 | 7.7 |
| Ff-115 | 7.6 | 4.5 |
| Ff-117 | 11.3 | 15.2 |
| Ff-121 | 15.1 | 1.3 |
| Ff-173 | 14.3 | 2.9 |
| Ff-174 | 17.8 | 15.2 |
| Ff-183 | 10.3 | 2.3 |
| Ff-197 | 16 | 1.7 |
| Ff-252 | 13.6 | 2.6 |
| Ff-340 | 16.3 | 2.9 |
| Ff-341 | 10.3 | 3.5 |
| Ff-344 | 14.7 | 5.2 |
| Ff-345 | 10.2 | 5.6 |
| Ff-346 | 10.8 | 13.8 |
| Ff-363 | 13.4 | 26.6 |
| Ff-366 | 9 | 18.3 |
| Ff-367 | 13.7 | 6.1 |
| Ff-379 | 10 | 0.8 |
| Ff-499 | 17.8 | 1.2 |
| Ff-587 | 7.4 | 1.2 |
| Ff-648 | 10.9 | 7.8 |
| Ff-684 | 10.7 | 16.2 |
| Ff-685 | 11.2 | 7.1 |
| Ff-693 | 12.6 | 4.7 |

TABLE 4-continued

Permeability data (Example G2)

| Example No. | cPgp-KO-MDCK-WT $P_{app}$ (A-to-B) [x10$^{-6}$ cm/s] | cPgp-KO-BCRP-KI (ER) |
|---|---|---|
| Ff-694 | 19.7 | 1.7 |
| Ff-696 | 21 | 5.4 |
| Ff-698 | 11.4 | 5.3 |
| Ff-699 | 10.9 | 13.5 |
| Fg-31 | 10.3 | 2.2 |
| Fg-53 | 16.6 | 2.7 |
| Fg-55 | 9.5 | 4 |
| Fg-60 | 7 | 12.4 |
| Fg-66 | 19.3 | 3.5 |
| Fg-67 | 18.5 | 3.2 |

TABLE 5

Brain penetration data (Examples D, E and G1)

| Example No. | Rat brain Kp | Rat brain $Kp_{u,u}$ | Cyno brain Kp | Cyno brain $Kp_{u,u}$ |
|---|---|---|---|---|
| Ff-81 | 0.17 | 0.04 | 0.96 | 0.13 |
| Ff-82 | 0.15 | 0.02 | | |
| Ff-104 | 0.39 | 0.07 | 1.78 | 0.19 |
| Ff-109 | 0.1 | 0.02 | | |
| Ff-110 | 0.48 | 0.06 | 0.76 | 0.1 |
| Ff-111 | 0.4 | 0.06 | 1.1 | 0.23 |
| Ff-173 | 0.12 | 0.03 | | |
| Ff-183 | 0.41 | 0.06 | | |
| Ff-197 | 0.22 | 0.06 | 1.2 | 0.28 |
| Ff-340 | 0.2 | 0.06 | 1.1 | 0.32 |
| Ff-341 | 0.37 | 0.11 | | |
| Ff-367 | 0.32 | | | |
| Ff-499 | 0.67 | 0.15 | 2.4 | 0.51 |
| Ff-587 | 0.52 | 0.06 | | |
| Ff-694 | 0.29 | | | |
| Fg-31 | 0.76 | 0.13 | | |
| Fg-53 | 0.29 | 0.05 | 0.99 | 0.16 |
| Fg-55 | 0.2 | 0.05 | 0.95 | 0.12 |

brain Kp = [brain]/[plasma];
brain $Kp_{u,u}$ = Kp * (plasma free/rat brain free)

TABLE 6 hERG IC50 and PBS solubility (Example C and H)

| Example No. | hERG $IC_{50}$ (μM) | PBS solubility (μM) |
|---|---|---|
| Ff-81 | 27.7* | 18.5 |
| Ff-82 | >30* | 17.9 |
| Ff-104 | 14.2* | <1 |
| Ff-109 | | 2.3 |
| Ff-110 | 8.47 | 1.7 |
| Ff-111 | 6.7 | 1.1 |
| Ff-113 | | 1.1 |
| Ff-115 | | <1 |
| Ff-117 | | 54.7 |
| Ff-121 | | 4 |
| Ff-173 | | 9.9 |
| Ff-174 | | <1 |
| Ff-183 | | 1.6 |
| Ff-197 | 11.9* | <1 |
| Ff-252 | | <1 |
| Ff-340 | | <1 |
| Ff-341 | | 1.7 |
| Ff-344 | | <1 |
| Ff-345 | | <1 |
| Ff-346 | | 4.2 |
| Ff-363 | | 21.8 |
| Ff-366 | | 25.2 |
| Ff-367 | | 34.9 |

TABLE 6-continued

| hERG IC50 and PBS solubility (Example C and H) | | |
|---|---|---|
| Example No. | hERG $IC_{50}$ (μM) | PBS solubility (μM) |
| Ff-379 | | <1 |
| Ff-402 | | 18.3 |
| Ff-499 | 17.5* | <1 |
| Ff-587 | | <1 |
| Ff-620 | | 1.2 |
| Ff-648 | 30* | 5.1 |
| Ff-684 | | 28.4 |
| Ff-685 | | 16.1 |
| Ff-692 | | 18.6 |
| Ff-694 | 16.2 | 50.2 |
| Ff-696 | | 2.9 |
| Ff-697 | | 2.5 |
| Ff-698 | | <1 |
| Ff-699 | | 2.6 |
| Fg-31 | | 1.6 |
| Fg-53 | 9.95 | 19.9 |
| Fg-55 | 6.2 | 13.7 |
| Fg-66 | | <1 |
| Fg-67 | | 1.7 |
| Fg-68 | | <1 |

*Accurate hERG measurement may be limited by compound solubility

TABLE 7

| Human predicted clearance (Example I) | |
|---|---|
| Example No. | Human Predicted Hepatocyte CL (L/h/Kg) |
| Ff-81 | 0.18 |
| Ff-82 | 0.26 |
| Ff-104 | 0.5 |
| Ff-109 | 0.14 |
| Ff-110 | 0.22 |
| Ff-111 | 0.35 |
| Ff-117 | 0.05 |
| Ff-121 | 0.48 |
| Ff-173 | 0.18 |
| Ff-183 | 0.18 |
| Ff-197 | 0.25 |
| Ff-340 | 0.3 |
| Ff-341 | 0.22 |
| Ff-344 | 0.07 |
| Ff-366 | 0.05 |
| Ff-367 | 0.16 |
| Ff-499 | 0.25 |
| Ff-648 | 0.34 |
| Ff-684 | 0.16 |
| Ff-685 | 0.29 |
| Ff-693 | 0.31 |
| Ff-694 | 0.21 |
| Ff-696 | 0.27 |
| Ff-697 | 0.4 |
| Fg-53 | 0.17 |
| Fg-55 | 0.24 |
| Fg-60 | 0.21 |
| Fg-66 | 0.28 |
| Fg-67 | 0.24 |

TABLE 8A

| PK data of Example Ff-81 | | | | | | |
|---|---|---|---|---|---|---|
| Species | Predicted Hepatocyte CL (L/h/Kg) | Mode of administration and dose | Observed CL (L/h/Kg) | T1/2 (h) | Vss (L/Kg) | % F |
| Sprague-Dawley Rat | 1.1 | IV 1 mg/Kg | 0.24 | 4.7 | 1.65 | |
| Sprague-Dawley Rat | | PO 1.66 mg/Kg | | | | |
| Beagle Dog | 0.21 | IV 0.5 mg/Kg | 0.26 | 7.9 | | |
| Beagle Dog | | PO 0.5 mg/Kg | | | | 134 |
| Cynomolgus monkey | 0.15 | IV 0.5 mg/Kg | 0.18 | 16 | 1.77 | |
| Cynomolgus monkey | | PO 0.5 mg/Kg | | | | 123 |

TABLE 8B

| PK data of Example Ff-104 | | | | | | |
|---|---|---|---|---|---|---|
| Species | Predicted Hepatocyte CL (L/h/Kg) | Mode of administration and dose | Observed CL (L/h/Kg) | T1/2 (h) | Vss (L/Kg) | % F |
| Sprague-Dawley Rat | 1.66 | IV 0.33 mg/Kg | 0.56 | 3.7 | 2.82 | |
| Sprague-Dawley Rat | | PO 1.66 mg/Kg | | | | 67 |
| Beagle Dog | 0.38 | IV 0.5 mg/Kg | 0.19 | 8.7 | 2 | |
| Beagle Dog | | PO 0.5 mg/Kg | | | | 68 |
| Cynomolgus monkey | 0.29 | IV 0.5 mg/Kg | 0.19 | 11 | 1.7 | |
| Cynomolgus monkey | | PO 0.5 mg/Kg | | | | 108 |

TABLE 8C

| PK data of Example Ff-104 | | | | | | |
|---|---|---|---|---|---|---|
| Species | Predicted Hepatocyte CL (L/h/Kg) | Mode of administration and dose | Observed CL (L/h/Kg) | T1/2 (h) | Vss (L/Kg) | % F |
| Sprague-Dawley Rat | 1.24 | IV 0.33 mg/Kg | 0.22 | 3.77 | 1.3 | |
| Sprague-Dawley Rat | | PO 1.66 mg/Kg | | | | 98 |
| Beagle Dog | 0.67 | IV 0.25 mg/Kg | 0.39 | 3.9 | 1.78 | |
| Cynomolgus monkey | 0.28 | IV 0.25 mg/Kg | 0.1 | 10.4 | 1.47 | |

TABLE 8D

| PK data of Example Ff-111 | | | | | |
|---|---|---|---|---|---|
| Species | Predicted Hepatocyte CL (L/h/Kg) | Mode of administration and dose | Observed CL (L/h/Kg) | T1/2 (h) | Vss (L/Kg) |
| Sprague-Dawley Rat | 1.67 | IV 0.33 mg/Kg | 0.15 | 5.9 | 1.29 |
| Beagle Dog | 0.74 | | | | |
| Cynomolgus monkey | 0.28 | IV 0.33 mg/Kg | 0.15 | 5.9 | 1.29 |

TABLE 8E

| PK data of Example Ff-340 | | | | | |
|---|---|---|---|---|---|
| Species | Predicted Hepatocyte CL (L/h/Kg) | Mode of administration and dose | Observed CL (L/h/Kg) | T1/2 (h) | Vss (L/Kg) |
| Sprague-Dawley Rat | 1.19 | IV 0.33 mg/Kg | 0.53 | 5.3 | 3.2 |
| Beagle Dog | 0.72 | | | | |
| Cynomolgus monkey | 0.2 | IV 0.33 mg/Kg | 0.24 | 5.8 | 1.9 |

TABLE 8F

| PK data of Example Ff-341 | | | | | | |
|---|---|---|---|---|---|---|
| Species | Predicted Hepatocyte CL (L/h/Kg) | Mode of administration and dose | Observed CL (L/h/Kg) | T1/2 (h) | Vss (L/Kg) | % F |
| Sprague-Dawley Rat | 0.96 | IV 0.25 mg/Kg | 0.21 | 4.6 | 1.45 | |
| Sprague-Dawley Rat | | PO 1.25 mg/Kg | | | | 99 |
| Beagle Dog | 0.74 | | | | | |
| Cynomolgus monkey | 0.34 | IV 0.25 mg/Kg | 0.2 | 8 | 2.15 | |

TABLE 8G

| PK data of Example Ff-499 | | | | | | |
|---|---|---|---|---|---|---|
| Species | Predicted Hepatocyte CL (L/h/Kg) | Mode of administration and dose | Observed CL (L/h/Kg) | T1/2 (h) | Vss (L/Kg) | % F |
| Sprague-Dawley Rat | 2.23 | IV 0.33 mg/Kg | 0.49 | 3.1 | 1.72 | |
| Beagle Dog | 0.92 | | | | | |
| Cynomolgus monkey | 0.92 | IV 0.33 mg/Kg | 1.47 | 1.39 | 1.93 | |

TABLE 8H

| PK data of Example Fg-53 | | | | | | |
|---|---|---|---|---|---|---|
| Species | Predicted Hepatocyte CL (L/h/Kg) | Mode of administration and dose | Observed CL (L/h/Kg) | T1/2 (h) | Vss (L/Kg) | % F |
| Sprague-Dawley Rat | 1.12 | IV 0.33 mg/Kg | 0.44 | 4.6 | 2.45 | |
| Sprague-Dawley Rat | | PO 1.66 mg/Kg | | | | 120 |
| Beagle Dog | 0.61 | IV 0.25 mg/Kg | 0.38 | 3.8 | 1.97 | |
| Beagle Dog | | PO 0.5 mg/Kg | | | | 73 |
| Cynomolgus monkey | 0.18 | IV 0.25 mg/Kg | 0.12 | 15.4 | 2.53 | |
| Cynomolgus monkey | | PO 0.5 mg/Kg | | | | 84 |

TABLE 81I

| PK data of Example Fg-55 | | | | | | |
|---|---|---|---|---|---|---|
| Species | Predicted Hepatocyte CL (L/h/Kg) | Mode of administration and dose | Observed CL (L/h/Kg) | T1/2 (h) | Vss (L/Kg) | % F |
| Sprague-Dawley Rat | 0.93 | IV 0.33 mg/Kg | 0.21 | 6 | 1.73 | |
| Sprague-Dawley Rat | | PO 1.66 mg/Kg | | | | 99 |
| Beagle Dog | 0.75 | IV 0.25 mg/Kg | 0.26 | 6 | 1.8 | |
| Cynomolgus monkey | 0.25 | IV 0.25 mg/Kg | 0.13 | 10.7 | 2 | |

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound of Formula (I)

(I)

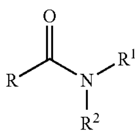

or a pharmaceutically acceptable salt thereof, wherein

R is

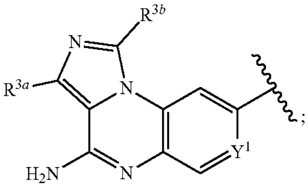

$R^{3a}$ is H;

$R^{3b}$ is H or $CH_3$;

$Y^1$ is N, CH, or CF;

$—NR^1R^2$ is

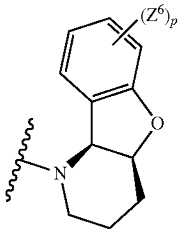

or

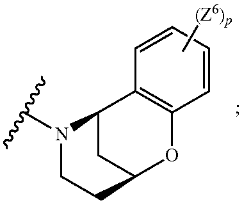

;

each $Z^6$ is independently F, $—CH_3$, $—CF_3$, $—C_2F_5$, or $—OCF_3$; and p is 1 or 2.

2. The compound or pharmaceutically acceptable salt thereof of claim 1, wherein R is

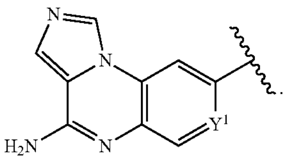

3. The compound or pharmaceutically acceptable salt thereof of claim 1, wherein $Y^1$ is N.

4. The compound or pharmaceutically acceptable salt thereof of claim 1, wherein $Y^1$ is CF.

5. The compound or pharmaceutically acceptable salt thereof of claim 1, wherein
—$NR^1R^2$ is
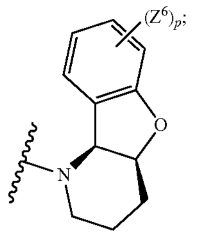
$Z^6$ is F, $OCF_3$ or $CF_3$; and
p is 1 or 2.
6. The compound or pharmaceutically acceptable salt thereof of claim 1, wherein
—$NR^1R^2$ is
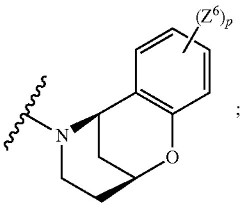
;
$Z^6$ is F, $OCF_3$ or $CF_3$; and
p is 1 or 2.
7. A compound is
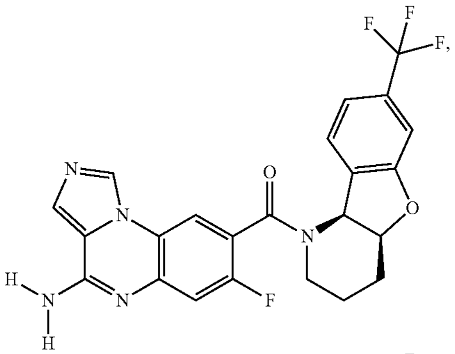
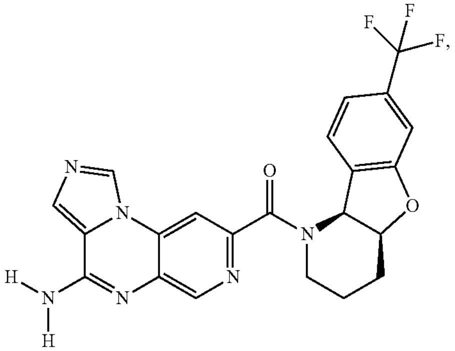
-continued
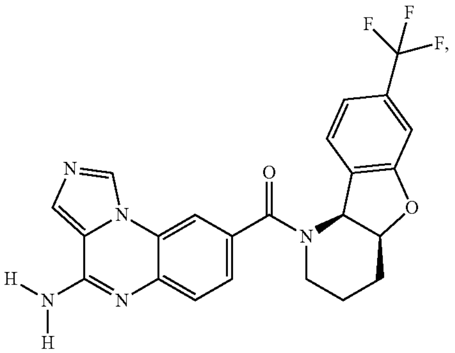
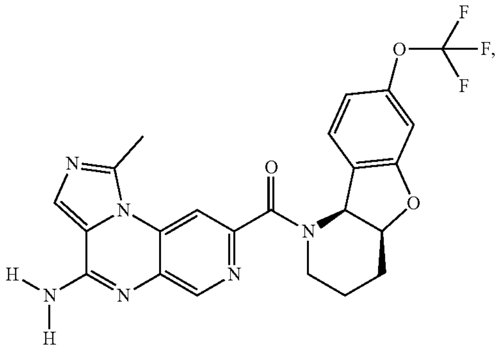
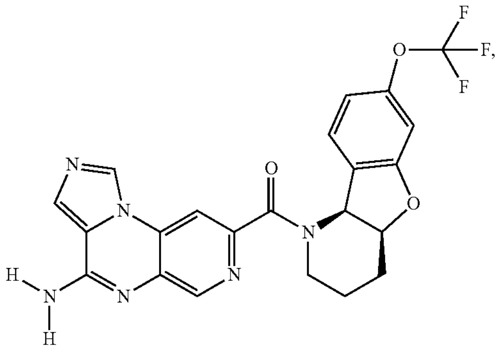
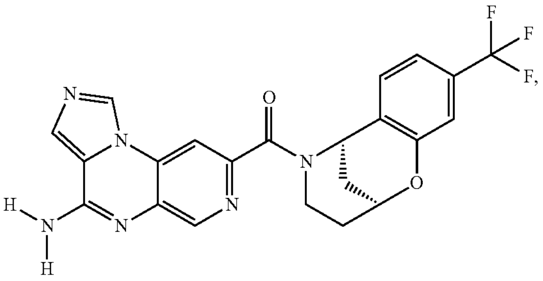
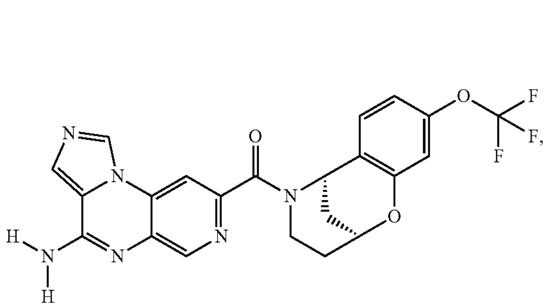

-continued
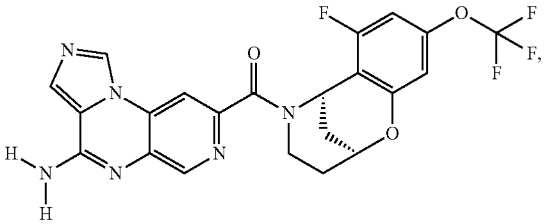
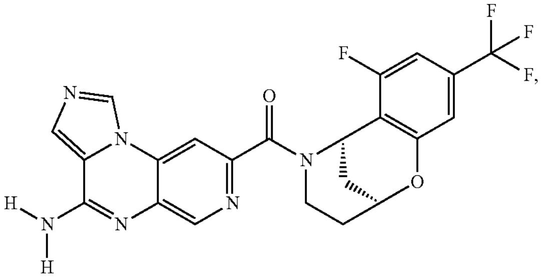
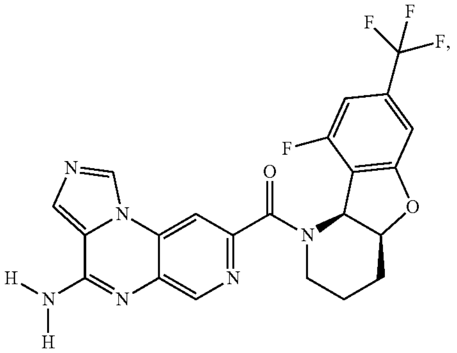
or
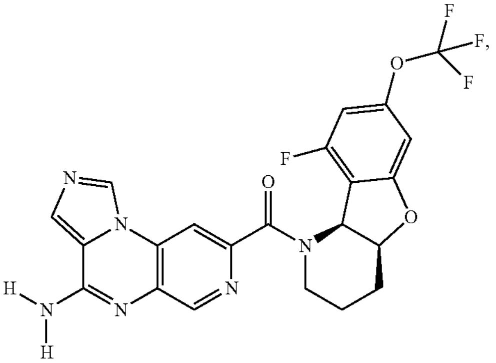
or a pharmaceutically acceptable salt thereof.
8. The compound or pharmaceutically acceptable salt thereof of claim 7, wherein the compound is
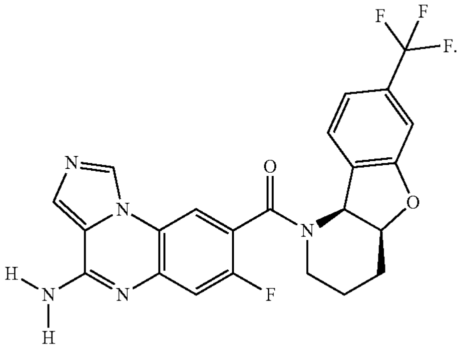 [SMILES: Nc1nc2cc(F)c(C(=O)N3CCC[C@@H]4Oc5cc(C(F)(F)F)ccc5[C@@H]43)cc2n2cncc12]
9. The compound or pharmaceutically acceptable salt thereof of claim 7, wherein the compound is
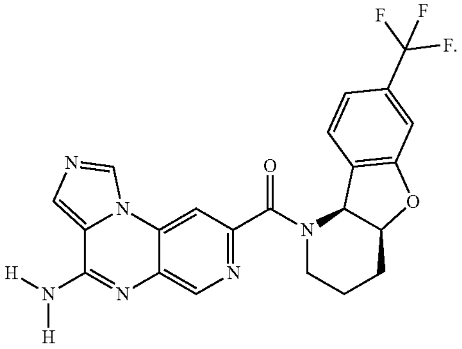 [SMILES: Nc1nc2cnc(C(=O)N3CCC[C@@H]4Oc5cc(C(F)(F)F)ccc5[C@@H]43)cc2n2cncc12]
10. The compound or pharmaceutically acceptable salt thereof of claim 7, wherein the compound is
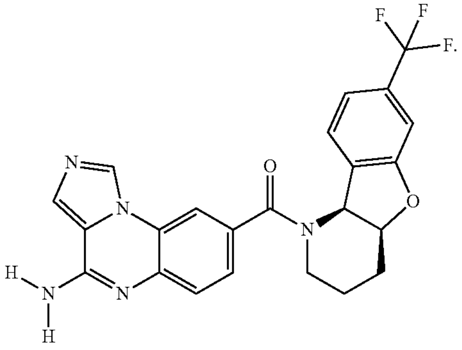 [SMILES: Nc1nc2ccc(C(=O)N3CCC[C@@H]4Oc5cc(C(F)(F)F)ccc5[C@@H]43)cc2n2cncc12]

11. The compound or pharmaceutically acceptable salt thereof of claim 7,
wherein the compound is

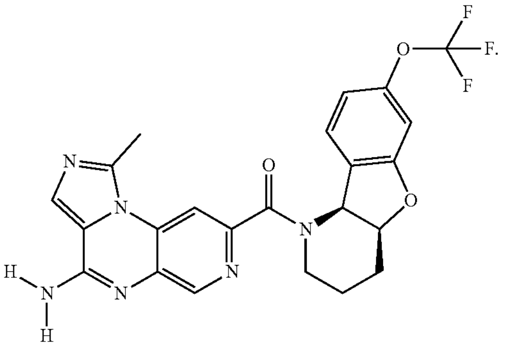 [SMILES: Cc1ncc2c(N)nc3cnc(C(=O)N4CCC[C@@H]5Oc6cc(OC(F)(F)F)ccc6[C@@H]54)cc3n12]

12. The compound or pharmaceutically acceptable salt thereof of claim 7, wherein the compound is

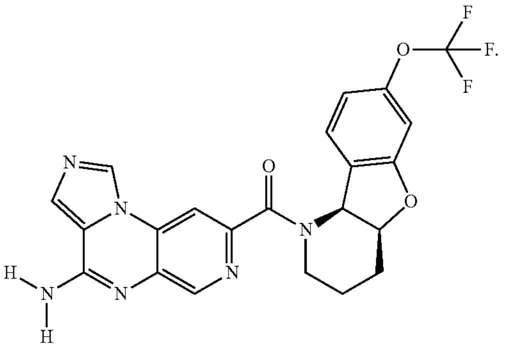 [SMILES: Nc1nc2cnc(C(=O)N3CCC[C@@H]4Oc5cc(OC(F)(F)F)ccc5[C@@H]43)cc2n2cncc12]

13. The compound or pharmaceutically acceptable salt thereof of claim 7, wherein the compound is

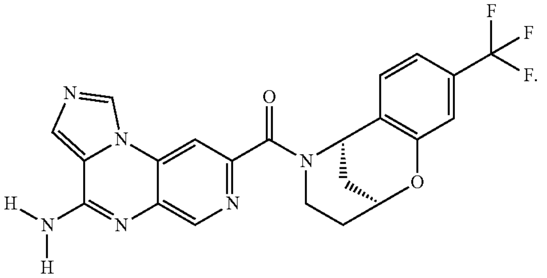 [SMILES: Nc1nc2cnc(C(=O)N3CC[C@H]4C[C@@H]3c3ccc(C(F)(F)F)cc3O4)cc2n2cncc12]

14. The compound or pharmaceutically acceptable salt thereof of claim 7, wherein the compound is

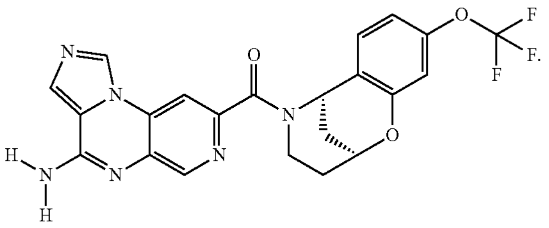 [SMILES: Nc1nc2cnc(C(=O)N3CC[C@H]4C[C@@H]3c3ccc(OC(F)(F)F)cc3O4)cc2n2cncc12]

15. The compound or pharmaceutically acceptable salt thereof of claim 7, wherein the compound is

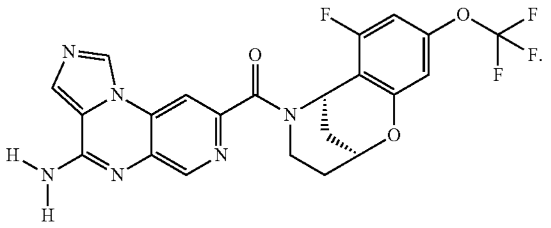 [SMILES: Nc1nc2cnc(C(=O)N3CC[C@H]4C[C@@H]3c3c(F)cc(OC(F)(F)F)cc3O4)cc2n2cncc12]

16. The compound or pharmaceutically acceptable salt thereof of claim 7, wherein the compound is

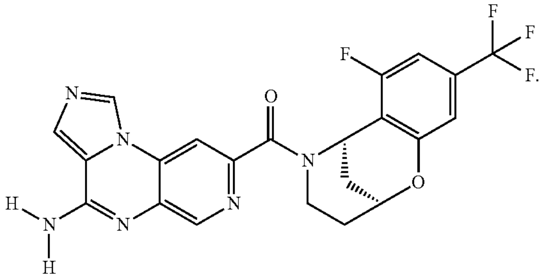 [SMILES: Nc1nc2cnc(C(=O)N3CC[C@H]4C[C@@H]3c3c(F)cc(C(F)(F)F)cc3O4)cc2n2cncc12]

17. The compound or pharmaceutically acceptable salt thereof of claim 7, wherein the compound is

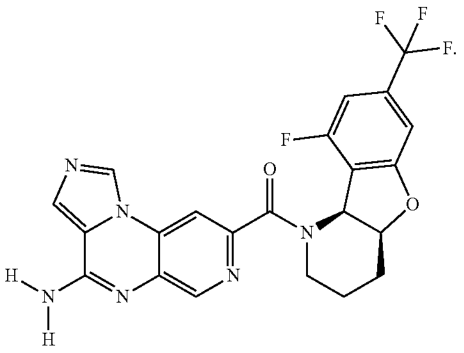 [SMILES: Nc1nc2cnc(C(=O)N3CCC[C@@H]4Oc5cc(C(F)(F)F)cc(F)c5[C@@H]43)cc2n2cncc12]

18. The compound or pharmaceutically acceptable salt thereof of claim 7, wherein the compound is
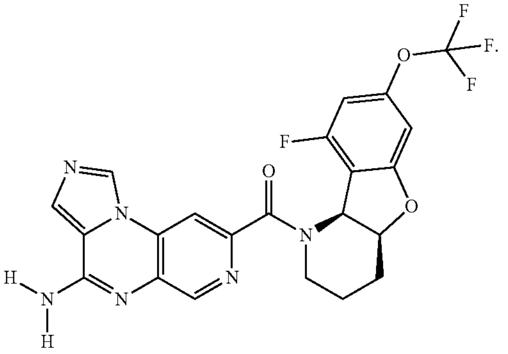 [SMILES: Nc1nc2cnc(C(=O)N3CCC[C@@H]4Oc5cc(OC(F)(F)F)cc(F)c5[C@@H]43)cc2n2cncc12]
* * * * *